United States Patent
Ahmed et al.

(10) Patent No.: US 8,148,391 B2
(45) Date of Patent: Apr. 3, 2012

(54) FUSED BICYCLIC DERIVATIVES OF 2,4-DIAMINOPYRIMIDINE AS ALK AND C-MET INHIBITORS

(75) Inventors: Gulzar Ahmed, Voorhees, NJ (US); Henry Joseph Breslin, Lansdale, PA (US); Jason Burke, Charlottesville, VA (US); Matthew A. Curry, Coatesville, PA (US); James L. Diebold, Eagleville, PA (US); Bruce Dorsey, Ambler, PA (US); Benjamin J. Dugan, Glen Mills, PA (US); Daming Feng, East Windsor, NJ (US); Diane E. Gingrich, Downingtown, PA (US); Tao Guo, Dayton, NJ (US); Keith S. Learn, Perkiomenville, PA (US); Joseph G. Lisko, Glenmoore, PA (US); Rong-Qiang Liu, Kendall Park, NJ (US); Eugen Florin Mesaros, Philadelphia, PA (US); Karen Milkiewicz, Exton, PA (US); Gregory R. Ott, Media, PA (US); Jay P. Theroff, West Chester, PA (US); Tho V. Thieu, Ambler, PA (US); Rabindranath Tripathy, Churchville, PA (US); Theodore L. Underiner, Malvern, PA (US); Gregory J. Wells, West Chester, PA (US); Craig A. Zificsak, Downingtown, PA (US)

(73) Assignee: Cephalon, Inc., Frazer, PA (US)

( * ) Notice: Subject to any disclaimer, the term of this patent is extended or adjusted under 35 U.S.C. 154(b) by 375 days.

(21) Appl. No.: 12/162,851

(22) PCT Filed: Oct. 23, 2007

(86) PCT No.: PCT/US2007/022496
§ 371 (c)(1),
(2), (4) Date: Jan. 13, 2009

(87) PCT Pub. No.: WO2008/051547
PCT Pub. Date: May 2, 2008

(65) Prior Publication Data
US 2009/0221555 A1   Sep. 3, 2009

Related U.S. Application Data

(60) Provisional application No. 60/853,562, filed on Oct. 23, 2006.

(51) Int. Cl.
*A61K 31/505* (2006.01)
*C07D 239/02* (2006.01)
(52) U.S. Cl. ........................ 514/275; 544/330
(58) Field of Classification Search .................. None
See application file for complete search history.

(56) References Cited

U.S. PATENT DOCUMENTS

| | | | |
|---|---|---|---|
| 6,239,138 B1 | 5/2001 | Ku | |
| 6,593,326 B1 | 7/2003 | Bradbury et al. | |
| 6,838,464 B2 | 1/2005 | Pease et al. | |
| 6,906,067 B2 | 6/2005 | Moriarty et al. | |
| 2003/0125346 A1 | 7/2003 | Buchanan et al. | |
| 2003/0134838 A1 | 7/2003 | Bornemann et al. | |
| 2003/0139435 A1 | 7/2003 | Ahmed et al. | |
| 2003/0171359 A1 | 9/2003 | Dahmann et al. | |
| 2003/0181474 A1 | 9/2003 | Pease et al. | |
| 2003/0187026 A1 | 10/2003 | Li et al. | |
| 2004/0002496 A1 | 1/2004 | Bebbington et al. | |
| 2004/0009974 A1 | 1/2004 | Bebbington et al. | |
| 2004/0009981 A1 | 1/2004 | Bebbington et al. | |
| 2004/0029902 A1 | 2/2004 | Singh et al. | |
| 2004/0063705 A1 | 4/2004 | Harmange et al. | |
| 2004/0102630 A1 | 5/2004 | Brumby et al. | |
| 2004/0180914 A1 | 9/2004 | Batchelor et al. | |
| 2004/0224966 A1 | 11/2004 | Brumby et al. | |
| 2005/0026914 A1 | 2/2005 | Buchanan et al. | |
| 2005/0038243 A1 | 2/2005 | Singh et al. | |
| 2005/0090486 A1 | 4/2005 | Bornemann et al. | |
| 2005/0090515 A1 | 4/2005 | Pease et al. | |
| 2005/0113398 A1 | 5/2005 | Argade et al. | |
| 2005/0192301 A1 | 9/2005 | Li | |
| 2005/0209221 A1 | 9/2005 | Nunes et al. | |

(Continued)

FOREIGN PATENT DOCUMENTS

EP   1 518 855   3/2005

(Continued)

*Primary Examiner* — Noble Jarrell

(57) ABSTRACT

The present invention provides a compound of formula I or II or a pharmaceutically acceptable salt form thereof, wherein $R^1$, $R^2$, $R^3$, $R^4$, $R^5$, $A^1$, $A^2$, $A^3$, $A^4$, and $A^5$, are as defined herein. The compounds of formula I or II have ALK and/or c-Met inhibitory activity, and may be used to treat proliferative disorders.

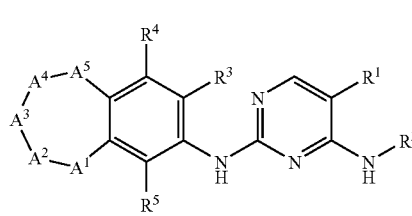

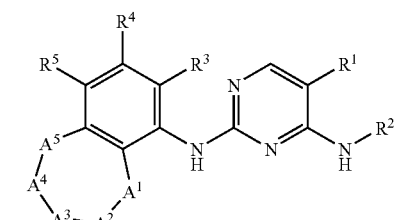

8 Claims, No Drawings

U.S. PATENT DOCUMENTS

| | | |
|---|---|---|
| 2005/0209224 A1 | 9/2005 | Singh et al. |
| 2005/0209230 A1 | 9/2005 | Singh et al. |
| 2005/0234049 A1 | 10/2005 | Singh et al. |
| 2005/0239770 A1 | 10/2005 | Moriarty et al. |
| 2005/0256111 A1 | 11/2005 | Kath et al. |
| 2005/0256125 A1 | 11/2005 | Kath et al. |
| 2005/0261295 A1 | 11/2005 | Stadtmueller et al. |
| 2005/0272753 A1 | 12/2005 | Nagashima et al. |
| 2006/0025410 A1 | 2/2006 | Singh et al. |
| 2006/0035891 A1 | 2/2006 | Li et al. |
| 2006/0035916 A1 | 2/2006 | Singh et al. |
| 2006/0058292 A1 | 3/2006 | Singh et al. |
| 2006/0063789 A1 | 3/2006 | Freyne et al. |
| 2006/0100211 A1 | 5/2006 | Dahmann et al. |
| 2006/0135543 A1 | 6/2006 | Singh et al. |
| 2006/0148800 A1 | 7/2006 | Stadtmueller et al. |
| 2006/0160812 A1 | 7/2006 | Schubert et al. |
| 2006/0167249 A1 | 7/2006 | Argade et al. |
| 2006/0293311 A1 | 12/2006 | Li et al. |
| 2007/0032514 A1 | 2/2007 | Zahn et al. |
| 2007/0060603 A1 | 3/2007 | Singh et al. |
| 2007/0207999 A1 | 9/2007 | Stadtmueller et al. |
| 2007/0225321 A1 | 9/2007 | Singh et al. |
| 2008/176881 A1 | 7/2008 | Michellys et al. |

FOREIGN PATENT DOCUMENTS

| | | |
|---|---|---|
| WO | WO 01/64656 | 9/2001 |
| WO | WO 03/026664 | 4/2003 |
| WO | WO 03/026665 | 4/2003 |
| WO | WO 03/026666 | 4/2003 |
| WO | WO 03/030909 | 4/2003 |
| WO | WO 03/032994 | 4/2003 |
| WO | WO 03/032997 | 4/2003 |
| WO | WO 03/055489 | 7/2003 |
| WO | WO 03/063794 | 8/2003 |
| WO | WO 03/078404 | 9/2003 |
| WO | WO 2004/014382 | 2/2004 |
| WO | WO 2004/046118 | 6/2004 |
| WO | WO 2004/080980 | 9/2004 |
| WO | WO 2005/006945 | 1/2005 |
| WO | WO 2005/012294 | 2/2005 |
| WO | WO 2005/016893 | 2/2005 |
| WO | WO 2005/016894 | 2/2005 |
| WO | WO 2005/026130 | 3/2005 |
| WO | WO 2005/026158 | 3/2005 |
| WO | WO 2005/118544 | 12/2005 |
| WO | WO 2006/021454 | 3/2006 |
| WO | WO 2006/021457 | 3/2006 |
| WO | WO 2006/021544 | 3/2006 |
| WO | WO 2006/055561 | 5/2006 |
| WO | WO 2006/074057 | 7/2006 |
| WO | WO 2006/128129 | 11/2006 |
| WO | WO 2006/133426 | 12/2006 |
| WO | WO 2007/006926 | 1/2007 |
| WO | WO 2007/018325 | 2/2007 |
| WO | WO 2007/028445 | 3/2007 |
| WO | WO 2007/053452 | 5/2007 |
| WO | WO 2007/072158 | 6/2007 |
| WO | WO 2007/085833 | 8/2007 |
| WO | WO 2007/089768 | 8/2007 |
| WO | WO 2008/003766 | 1/2008 |
| WO | WO 2008/073687 | 6/2008 |

FUSED BICYCLIC DERIVATIVES OF 2,4-DIAMINOPYRIMIDINE AS ALK AND C-MET INHIBITORS

BACKGROUND OF THE INVENTION

Anaplastic Lymphoma Kinase (ALK) is a cell membrane-spanning receptor tyrosine kinase, which belongs to the insulin receptor subfamily. The most abundant expression of ALK occurs in the neonatal brain, suggesting a possible role for ALK in brain development (Duyster, J. et al., *Oncogene*, 2001, 20, 5623-5637).

ALK is also implicated in the progression of certain tumors. For example, approximately sixty percent of anaplastic large cell lymphomas (ALCL) are associated with a chromosome mutation that generates a fusion protein consisting of nucleophosmin (NPM) and the intracellular domain of ALK. (Armitage, J. O. et al., *Cancer: Principle and Practice of Oncology*, 6th edition, 2001, 2256-2316; Kutok J. L. & Aster J. C., *J. Clin. Oncol.*, 2002, 20, 3691-3702). This mutant protein, NPM-ALK, possesses a constitutively active tyrosine kinase domain that is responsible for its oncogenic property through activation of downstream effectors. (Falini, B. et al., *Blood*, 1999, 94, 3509-3515; Morris, S. W. et al., *Brit. J. Haematol.*, 2001, 113, 275-295; Duyster et al.; Kutok & Aster). In addition, the transforming EML4-ALK fusion gene has been identified in non-small-cell lung cancer (NSCLC) patients (Soda, M., et al., *Nature*, 2007, 448, 561-566) and represents another in a list of ALK fusion proteins that are promising targets for ALK inhibitor therapy. Experimental data have demonstrated that the aberrant expression of constitutively active ALK is directly implicated in the pathogenesis of ALCL and that inhibition of ALK can markedly impair the growth of ALK+ lymphoma cells (Kuefer, Mu et al. Blood, 1997, 90, 2901-2910; Bai, R. Y. et al., *Mol. Cell. Biol.*, 1998, 18, 6951-6961; Bai, R. Y. et al., *Blood*, 2000, 96, 4319-4327; Ergin, M. et al., *Exp. Hematol.*, 2001, 29, 1082-1090; Slupianek, A. et al., *Cancer Res.*, 2001, 61, 2194-2199; Turturro, F. et al., *Clin. Cancer Res.*, 2002, 8, 240-245). The constitutively activated chimeric ALK has also been demonstrated in about 60% of inflammatory myofibroblastic tumors (IMTs), a slow-growing sarcoma that mainly affects children and young adults. (Lawrence, B. et al., *Am. J. Pathol.*, 2000, 157, 377-384; Duyster et al.).

In addition, ALK and its putative ligand, pleiotrophin, are overexpressed in human glioblastomas (Stoica, G. et al., *J. Biol. Chem.*, 2001, 276, 16772-16779). In mouse studies, depletion of ALK reduced glioblastoma tumor growth and prolonged animal survival (Powers, C. et al., *J. Biol. Chem.*, 2002, 277, 14153-14158; Mentlein, R. et al, *J. Neurochem.*, 2002, 83, 747-753).

An ALK inhibitor would be expected to either permit durable cures when combined with current chemotherapy for ALCL, IMT, proliferative disorders, glioblastoma and possible other solid tumors, or, as a single therapeutic agent, could be used in a maintenance role to prevent cancer recurrence in those patients. Various ALK inhibitors have been reported, such as indazoloisoquinolines (WO 2005/009389), thiazole amides and oxazole amides (WO 2005/097765), pyrrolopyrimidines (WO 2005080393), and pyrimidinediamines (WO 2005/016894).

c-Met is a member of the tyrosine kinase growth factor receptor family. c-Met expression occurs in endothelial, epithelial, and mesenchymal cells. Binding to c-Met of the endogenous ligand, hepatocyte growth factor (HGF), promotes cell migration, proliferation, and invasion.

c-Met is implicated in the progression of certain tumors. c-Met overexpression has been shown in numerous tumor types including colon, breast, renal, lung, hemangiomas, squamous cell myeloid leukemia, melanomas, glioblastomas, and astrocytomas. (Maulik et al., *Cytokine & Growth Factor Reviews*, 2002, 13, 41-59; Funakoshi et al., *Clinica Chimica Acta*, 2003, 1-23; Longati et al., *Curr. Drug Targets*, 2001, 2, 41-55). Activation of tumor cell c-Met receptors enhances tumor cell proliferation, invasion/metastasis, and resistance to apoptosis and cytotoxic therapies.

A c-Met inhibitor would be expected to have potent anti-tumor effects in many cancers and proliferative disorders through multiple complimentary mechanisms including increased sensitivity to conventional cytotoxic therapies. Various c-Met inhibitors have been reported, such as amino-heteroaryl compounds (WO 2004/076412; WO 2005/082411; US 2005/0009840), 5-6 bicyclic heterocycles (WO 2005/028475), monocyclic heterocycles (US 2005/0245530), bicyclic heterocycles (US 2005/0239820), triazolotriazine compounds (WO 2005/010005; US 2005/0075340), triarylimidazoles (US 2005/0085473), indolinone hydrazides (WO 2005/005378), tetracyclic compounds (WO 2005/004808), imidazole derivatives (WO 2005/040154), quinolines and quinazolines (WO 2005/030140), and quinolinoxynaphthalenes (WO 2005/070891). (See also Sattler, M., et al., *Cancer Res.*, 2003, 63, 5462-5469; Christensen, J. G., et al., *Cancer Res.*, 2003, 63, 7345-7355).

A need exists for ALK and c-Met inhibitors for use as pharmaceutical agents.

SUMMARY OF THE INVENTION

The present invention provides a compound of formula I or II

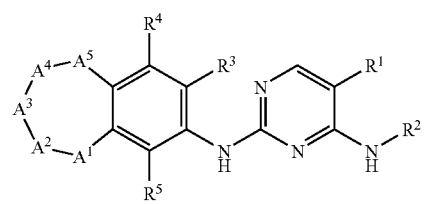

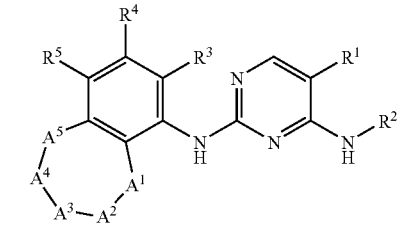

or a pharmaceutically acceptable salt form thereof, wherein $R^1$, $R^2$, $R^3$, $R^4$, $R^5$, $A^1$, $A^2$, $A^3$, $A^4$, and $A^5$, are as defined herein.

The compounds of formula I and II have ALK and/or c-Met inhibitory activity, and may be used to treat ALK- or c-Met-mediated disorders or conditions.

The present invention further provides a pharmaceutical composition comprising at least one compound of the present invention together with at least one pharmaceutically acceptable carrier, diluent, or excipient therefor.

In another aspect, the present invention provides a method of treating a subject suffering from an ALK- or c-Met-mediated disorder or condition comprising: administering to the subject the pharmaceutical composition of the present invention.

The present invention further provides a method of treating a proliferative disorder in a subject, comprising administering to the subject a therapeutically effective amount of a compound of the present invention.

DETAILED DESCRIPTION OF THE INVENTION

I. Definitions

As used herein, the following terms have the meanings ascribed to them unless specified otherwise.

"Alkyl" or "alkyl group" includes both straight and branched chain aliphatic hydrocarbon groups. Examples of straight-chain alkyl groups include, but are not limited to, methyl, ethyl, n-propyl, n-butyl, n-pentyl, n-hexyl, n-heptyl, n-octyl, n-nonyl, n-decyl, etc. Examples of branched-chain alkyl groups include, but are not limited to, isopropyl, tert-butyl, isobutyl, etc. Alkyl groups typically contain 1-10 carbon atoms, such as 1-6 carbon atoms.

The term "$C_{x-y}$" indicates the number of carbon atoms in a group. For example, a "$C_{1-6}$-alkyl" is an alkyl group having from one (1) to six (6) carbon atoms. In some instances, x=0, i.e., "$C_{0-y}$". The term "$C_{0-y}$" indicates that the group may be absent or present, and if present, defines the number of carbon atoms in the group. For example, "$C_{0-6}$-alkyl" indicates that an alkyl group may be absent (x=0) or present (x=1-6), and if present contains from one (1) to six (6) carbon atoms. For example, "—$C_{0-6}$-alkyl-C(=O)—$C_{0-6}$-alkyl-" includes —C(=O)—, —$C_{1-6}$-alkyl-C(=O)—, and —$C_{1-6}$-alkyl-C(=O)—$C_{1-6}$-alkyl-. Examples of —$C_{0-6}$-alkyl-C(=O)—$C_{0-6}$-alkyl- include, but are not limited to, —C(=O)—, —$CH_2CH_2$—C(=O)—, and —$CH(CH_3)CH_2CH_2$—C(=O)—$CH_2$—.

The term "alkyl-$(R)_x$", wherein "x is chosen from 0, 1, 2, 3, 4, 5, and 6" refers to an alkyl group that is substituted at any position(s) by 0, 1, 2, 3, 4, 5, or 6 identical or different "R" substituents. For example, in the group —$CH_2CF_2CH_3$, R=F and x=2. In the group —$CH_2CH(OH)CF_3$, R=F, —OH and x=4. In the group —$CH_2CH_2CH_3$, x=0.

"Alkenyl" or "alkenyl group" includes straight and branched chain unsaturated alkyl groups which have two (2) or more carbon atoms and at least one double bond. Examples include, but are not limited to, ethenyl, 3-buten-1-yl, 2-ethenylbutyl, and 3-hexen-1-yl.

"Alkynyl" or "alkynyl group" includes straight and branched chain unsaturated alkyl groups which have two (2) or more carbon atoms and at least one triple bond. Examples include, but are not limited to, ethynyl, 3-butyn-1-yl, propynyl, 2-butyn-1-yl, and 3-pentyn-1-yl.

"Haloalkyl" or "haloalkyl group" refers to alkyl groups in which one or more hydrogen atoms are replaced by halogen atoms. Haloalkyl includes both saturated alkyl groups and unsaturated alkenyl and alkynyl groups, such as for example —$CF_3$, —$CHF_2$, —$CH_2F$, —$CF_2CF_3$, —$CHFCF_3$, —$CH_2CF_3$, —$CF_2CH_3$, —$CHFCH_3$, —$CF_2CF_2CF_3$, —$CF_2CH_2CH_3$, —CF=$CF_2$, —CCl=$CH_2$, —CBr=$CH_2$, —CI=$CH_2$, —C≡C—$CF_3$, —$CHFCH_2CH_3$ and —$CHFCH_2CF_3$.

"Halogen" includes fluorine, chlorine, bromine and iodine atoms.

"Pseudohalogen" refers to —OCN, —SCN, —$CF_3$, and —CN.

"Cycloalkyl" or "cycloalkyl group" includes monocyclic, bicyclic, tricyclic, bridged bicyclic and bridged tricyclic non-aromatic carbocyclic rings, which may be saturated or unsaturated. Examples include, but are not limited to, cyclopropyl, cyclopropenyl, cyclobutyl, cyclobutenyl, cyclopentyl, cyclopentenyl, cyclohexyl, cyclohexenyl, norbornyl, norbornenyl, bicyclo[2.2.1]hexane, bicyclo[2.2.1]heptane, bicyclo[2.2.1]heptene, bicyclo[3.1.1]heptane, bicyclo[3.2.1]octane, bicyclo[2.2.2]octane, bicyclo[3.2.2]nonane, bicyclo[3.3.1]nonane, and bicyclo[3.3.2]decane.

Preferably, the cycloalkyl group contains from 3 to 10 ring atoms. More preferably, the cycloalkyl group contains from 3 to 7 ring atoms, such as 3 ring atoms, 5 ring atoms, 6 ring atoms, or 7 ring atoms.

A cycloalkyl group can also include ring systems substituted on ring carbons with one or more —OH functional groups (which may further tautomerize to give a ring C=O group).

"Heterocycloalkyl" or "heterocycloalkyl group" includes 3-15 membered monocyclic, bicyclic, and tricyclic non-aromatic rings, which may be saturated or unsaturated, and which contain, in addition to carbon atom(s), at least one heteroatom, such as nitrogen, oxygen or sulfur. Examples include, but are not limited to, tetrahydrofuranyl, pyrrolidinyl, pyrrolinyl, imidazolidinyl, imidazolinyl, pyrazolidinyl, pyrazolinyl, piperidyl, piperazinyl, indolinyl, isoindolinyl, morpholinyl, thiomorpholinyl, homomorpholinyl, homopiperidyl, homopiperazinyl, thiomorpholinyl-5-oxide, thiomorpholinyl-S,S-dioxide, pyrrolidinyl, tetrahydropyranyl, piperidinyl, tetrahydrothienyl, homopiperidinyl, homothiomorpholinyl-S,S-dioxide, oxazolidinonyl, dihydropyrazolyl, dihydropyrrolyl, dihydropyrazinyl, dihydropyridinyl, dihydropyrimidinyl, dihydrofuryl, dihydropyranyl, tetrahydrothienyl-5-oxide, tetrahydrothienyl-S,S-dioxide, homothiomorpholinyl-5-oxide, quinuclidinyl, 2-oxa-5-azabicyclo[2.2.1]heptane, 8-oxa-3-aza-bicyclo[3.2.1]octane, 3,8-diaza-bicyclo[3.2.1]octane, 2,5-diaza-bicyclo[2.2.1]heptane, 3,8-diaza-bicyclo[3.2.1]octane, 3,9-diaza-bicyclo[4.2.1]nonane and 2,6-diaza-bicyclo[3.2.2]nonane.

Preferably, the heterocycloalkyl group contains from 3 to 10 ring atoms. More preferably, the heterocycloalkyl group contains from 3 to 7 ring atoms. More preferably, the heterocycloalkyl group contains from 5 to 7 ring atoms, such as 5 ring atoms, 6 ring atoms, or 7 ring atoms.

Unless otherwise indicated, the foregoing heterocycloalkyl groups can be C-attached or N-attached where such is possible and results in the creation of a stable structure. For example, piperidinyl can be piperidin-1-yl (N-attached) or piperidin-4-yl (C-attached).

A heterocycloalkyl group can also include ring systems substituted on ring carbons with one or more —OH functional groups (which may further tautomerize to give a ring C=O group) and/or substituted on a ring sulfur atom by one (1) or two (2) oxygen atoms to give S=O or $SO_2$ groups, respectively.

"Aryl" or "aryl group" includes phenyl and 7-15 membered bicyclic or tricyclic hydrocarbon ring systems in which at least one of the rings is aromatic. Examples include, but are not limited to, naphthyl, indanyl, 1,2,3,4-tetrahydronaphthalenyl, 6,7,8,9-tetrahydro-5H-benzocycloheptenyl, and 6,7,8,9-tetrahydro-5H-benzocycloheptenyl.

Preferably, the aryl group contains 6 (i.e., phenyl) or 9 to 15 ring atoms. More preferably, the aryl group contains 6 (i.e., phenyl), 9 or 10 ring atoms.

An aryl group can also include ring systems substituted on ring carbons with one or more —OH functional groups (which may further tautomerize to give a ring C=O group).

"Heteroaryl" or "heteroaryl group" includes (a) 5 and 6 membered monocyclic aromatic rings, which contain, in addition to carbon atom(s), at least one heteroatom, such as nitrogen, oxygen or sulfur, and (b) 7-15 membered bicyclic and tricyclic rings, which contain, in addition to carbon atom(s), at least one heteroatom, such as nitrogen, oxygen or sulfur, and in which at least one of the rings is aromatic. Examples include, but are not limited to, 2,3-dihydrobenzofuranyl, 1,2-dihydroquinolinyl, 3,4-dihydroisoquinolinyl, 1,2,3,4-tetrahydroisoquinolinyl, 1,2,3,4-tetrahydroquinolinyl, benzoxazinyl, benzthiazinyl, chromanyl, furanyl, 2-furanyl, 3-furanyl, imidazolyl, isoxazolyl, isothiazolyl, oxadiazolyl, oxazolyl, pyridinyl, 2-, 3-, or 4-pyridinyl, pyrimidinyl, 2-, 4-, or 5-pyrimidinyl, pyrazolyl, pyrrolyl, 2- or 3-pyrrolyl, pyrazinyl, pyridazinyl, 3- or 4-pyridazinyl, 2-pyrazinyl, thienyl, 2-thienyl, 3-thienyl, tetrazolyl, thiazolyl, thiadiazolyl, triazinyl, triazolyl, pyridin-2-yl, pyridin-4-yl, pyrimidin-2-yl, pyridazin-4-yl, pyrazin-2-yl, naphthyridinyl, pteridinyl, phthalazinyl, purinyl, alloxazinyl, benzimidazolyl, benzofuranyl, benzofurazanyl, 2H-1-benzopyranyl, benzothiadiazine, benzothiazinyl, benzothiazolyl, benzothiophenyl, benzoxazolyl, cinnolinyl, furopyridinyl, indolinyl, indolizinyl, indolyl, or 2-, 3-, 4-, 5-, 6-, or 7-indolyl, 3H-indolyl, quinazolinyl, quinoxalinyl, isoindolyl, isoquinolinyl, 10-aza-tricyclo[6.3.1.0*2,7*]dodeca-2(7),3,5-trienyl, 12-oxa-10-aza-tricyclo[6.3.1.0*2,7*]dodeca-2(7),3,5-trienyl, 12-aza-tricyclo[7.2.1.0*2,7*]dodeca-2(7),3,5-trienyl, 10-aza-tricyclo[6.3.2.0*2,7*]trideca-2(7),3,5-trienyl, 2,3,4,5-tetrahydro-1H-benzo[d]azepinyl, 1,3,4,5-tetrahydro-benzo[d]azepin-2-onyl, 1,3,4,5-tetrahydro-benzo[b]azepin-2-onyl, 2,3,4,5-tetrahydro-benzo[c]azepin-1-onyl, 1,2,3,4-tetrahydro-benzo[e][1,4]diazepin-5-onyl, 2,3,4,5-tetrahydro-1H-benzo[e][1,4]diazepinyl, 5,6,8,9-tetrahydro-7-oxa-benzocycloheptenyl, 2,3,4,5-tetrahydro-1H-benzo[b]azepinyl, 1,2,4,5-tetrahydro-benzo[e][1,3]diazepin-3-onyl, 3,4-dihydro-2H-benzo[b][1,4]dioxepinyl, 3,4-dihydro-2H-benzo[f][1,4]oxazepin-5-onyl, 6,7,8,9-tetrahydro-5-thia-8-aza-benzocycloheptenyl, 5,5-dioxo-6,7,8,9-tetrahydro-5-thia-8-aza-benzocycloheptenyl, and 2,3,4,5-tetrahydro-benzo[f][1,4]oxazepinyl.

Preferably, the heteroaryl group contains 5, 6, or 8-15 ring atoms. More preferably, the heteroaryl group contains 5 to 10 ring atoms, such as 5, 6, 9, or 10 ring atoms.

A heteroaryl group can also include ring systems substituted on ring carbons with one or more —OH or C=O functional groups and/or substituted on a ring sulfur atom by one (1) or two (2) oxygen atoms to give S=O or $SO_2$ groups, respectively.

"Chemically stable" or "stable" refers to a compound that is sufficiently robust to be isolated to a useful degree of purity from a reaction mixture, and then incorporated into a pharmaceutical composition. The present invention is directed only to stable compounds.

"Pharmaceutical composition" refers to a composition suitable for administration in medical or veterinary use.

When lists of alternative substituents include members which, owing to valency requirements, chemical stability, or other reasons, cannot be used to substitute a particular group, the list is intended to be read in context to include those members of the list that are suitable for substituting the particular group. For example, when $R^2$ is substituted by a group of formula $C_{1-6}$-alkyl-$(R^{25})_x$, and the $C_{1-6}$-alkyl group is methyl, then the variable "x" cannot be 4, 5, or 6.

"Functionalized derivative" refers to a compound that contains at least one additional functional group as compared to a reference compound. An example of a functionalized derivative of benzene is bromobenzene. An example of a functionalized derivative of bromobenzene is 2-bromophenol. Functional groups include, but are not limited to, halogen, nitro, hydroxy, alkoxy, aryloxy, ketone, ester, amide, amino, alkylamino, alkyl, double bond, triple bond, alkoxyalkyl, aminoalkyl, haloalkyl, alkenyl, alkynyl, aryl, heteroaryl, cycloalkyl, heterocycloalkyl, pseudohalogen, alkylthio, sulfonyl, alkylsulfonyl, alkylaminosulfonyl, alkylcarbonyloxy, aminocarbonyloxy, alkylaminocarbonyloxy, alkylcarbonylamino, alkoxycarbonylamino, alkylsulfonylamino, aminocarbonylamino, and alkylaminocarbonylamino functional group, and derivatives of these and other functional groups in which a heteroatom is derivatized with a removable protecting group.

"Pharmaceutically acceptable" refers to physiologically tolerable materials, which do not typically produce an allergic or other untoward reaction, such as gastric upset, dizziness and the like, when administered to a mammal.

"Therapeutically effective amount" refers to an amount of a compound, or a pharmaceutically acceptable salt thereof, sufficient to inhibit, halt, or cause an improvement in a disorder or condition being treated in a particular subject or subject population. For example in a human or other mammal, a therapeutically effective amount can be determined experimentally in a laboratory or clinical setting, or may be the amount required by the guidelines of the United States Food and Drug Administration, or equivalent foreign agency, for the particular disease and subject being treated.

It should be appreciated that determination of proper dosage forms, dosage amounts, and routes of administration is within the level of ordinary skill in the pharmaceutical and medical arts, and is described below.

"Subject" refers to a member of the class Mammalia. Examples of mammals include, without limitation, humans, primates, chimpanzees, rodents, mice, rats, rabbits, horses, livestock, dogs, cats, sheep, and cows.

"Treatment" refers to the acute or prophylactic diminishment or alleviation of at least one symptom or characteristic associated or caused by a disorder being treated. For example, treatment can include diminishment of several symptoms of a disorder or complete eradication of a disorder.

"Administering" refers to the method of contacting a compound with a subject. Modes of "administering" include, but are not limited to, methods that involve contacting the compound intravenously, intraperitoneally, intranasally, transdermally, topically, via implantation, subcutaneously, parentally, intramuscularly, orally, systemically, and via adsorption.

II. Compounds

In one embodiment, the present invention provides a compound of formula I or II

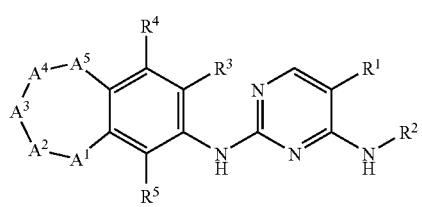

I

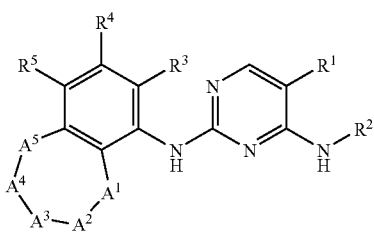

or a pharmaceutically acceptable salt form thereof,
wherein
- $R^1$ is H, halogen, $-NO_2$, $-OR^{10}$, $-C(=O)R^{10}$, $-C(=O)OR^{10}$, $-C(=O)NR^{12}R^{13}$, $-NR^{10}R^{11}$, $C_{1-6}$-alkyl, $-C_{1-6}$-alkyl-$OR^{10}$, $-C_{1-6}$-alkyl-$NR^{12}R^{13}$, $C_{1-6}$-haloalkyl, $C_{2-6}$-alkenyl, $C_{2-6}$-alkynyl, $C_{6-15}$-aryl, 5-15 membered heteroaryl, $C_{3-10}$ cycloalkyl, 3-15 membered heterocycloalkyl, pseudohalogen, $-S(=O)_nR^{10}$, $-S(=O)_2NR^{12}R^{13}$, $-OCH_2F$, $-OCHF_2$, $-OCF_3$, $-NHOH$, $-OC(=O)R^{10}$, $-OC(=O)NR^{12}R^{13}$, $-NR^{10}C(=O)R^{11}$, $-NR^{10}C(=O)OR^{11}$, $-NR^{10}S(=O)_2R^{11}$, $-NR^{10}C(=O)NR^{12}R^{13}$, $-NR^{10}S(=O)_2NR^{12}R^{13}$, or $-SCF_3$;
- $R^2$ is a group chosen from $C_{1-6}$-alkyl, $C_{2-6}$-alkenyl, $C_{2-6}$-alkynyl, $C_{6-15}$-aryl, $C_{3-10}$-cycloalkyl, 3-15 membered heterocycloalkyl, and 5-15 membered heteroaryl,
    wherein the $R^2$ group is optionally substituted by one or more members independently chosen from halogen, $-NO_2$, $-OR^{20}$, $=O$, $-C(=O)R^{20}$, $-C(=O)OR^{20}$, $-C(=O)NR^{22}R^{23}$, $-NR^{20}R^{21}$, $C_{1-6}$-alkyl-$(R^{25})_x$, $C_{6-15}$-aryl-$(R^{25})_x$, 5-15 membered heteroaryl-$(R^{25})_x$, $C_{3-10}$ cycloalkyl-$(R^{25})_x$, 3-15 membered heterocycloalkyl-$(R^{25})_x$, pseudohalogen, $-S(=O)_nR^{20}$, $-S(=O)_2NR^{22}R^{23}$, $-OCH_2F$, $-OCHF_2$, $-OCF_3$, $-NHOH$, $-OC(=O)R^{20}$, $-OC(=O)NR^{22}R^{23}$, $-NR^{20}C(=O)R^{21}$, $-NR^{20}C(=O)OR^{21}$, $-NR^{20}S(=O)_2R^{21}$, $-NR^{20}C(=O)NR^{22}R^{23}$, $-NR^{20}S(=O)_2NR^{22}R^{23}$, and $-SCF_3$;
- $R^3$, $R^4$, and $R^5$ are independently chosen from H, halogen, $-NO_2$, $-OR^{30}$, $-C(=O)R^{30}$, $-C(=O)OR^{30}$, $-C(=O)NR^{32}R^{33}$, $-NR^{30}R^{31}$, $C_{1-6}$-alkyl-$(R^{35})_x$, $C_{6-15}$-aryl-$(R^{35})_x$, 5-15 membered heteroaryl-$(R^{35})_x$, $C_{3-10}$ cycloalkyl-$(R^{35})_x$, 3-15 membered heterocycloalkyl-$(R^{35})_x$, pseudohalogen, $-S(=O)_nR^{30}$, $-S(=O)_2NR^{32}R^{33}$, $-OCH_2F$, $-OCHF_2$, $-OCF_3$, $-NHOH$, $-OC(=O)R^{30}$, $-OC(=O)NR^{32}R^{33}$, $-NR^{30}C(=O)R^{31}$, $-NR^{30}C(=O)OR^{31}$, $-NR^{30}S(=O)_2R^{31}$, $-NR^{30}C(=O)NR^{32}R^{33}$, $-NR^{30}S(=O)_2NR^{32}R^{33}$, and $-SCF_3$;
- $A^1$, $A^2$, $A^3$, $A^4$, and $A^5$ are each independently $-CZ^1Z^2-$, $-(CZ^1Z^2)_2-$, $-C(=O)-$, $-NZ^3-$, $-S-$, $-S(=O)-$, $-S(=O)_2-$, or $-O-$, with the proviso that at most one of $A^1$, $A^2$, $A^3$, $A^4$, and $A^5$ is $-(CZ^1Z^2)_2-$, wherein:
    (a) when any two of $Z^1$, $Z^2$, and $Z^3$ are located on adjacent atoms, they may form a bond between the atoms,
    (b) any of $Z^1$, $Z^2$, and $Z^3$ may be independently chosen from H, halogen, $-NO_2$, $-OR^{40}$, $-C(=O)R^{40}$, $-C(=O)OR^{40}$, $-C(=O)NR^{42}R^{43}$, $-NR^{40}R^{41}$, $C_{1-6}$ alkyl-$(R^{45})_x$, $C_{6-15}$-aryl-$(R^{45})_x$, 5-15 membered heteroaryl-$(R^{45})_x$, $C_{3-10}$ cycloalkyl-$(R^{45})_x$, 3-15 membered heterocycloalkyl-$(R^{45})_x$, $C_{2-6}$-alkenyl-$(R^{45})_x$, $C_{2-6}$-alkynyl-$(R^{45})_x$, pseudohalogen, $-S(=O)_nR^{40}$, $-S(=O)_2NR^{42}R^{43}$, $-OCH_2F$, $-OCHF_2$, $-OCF_3$, $-NHOH$, $-OC(=O)R^{40}$, $-OC(=O)NR^{42}R^{43}$, $-NR^{40}C(=O)R^{41}$, $-NR^{40}C(=O)OR^{41}$, $-NR^{40}S(=O)_2R^{41}$, $-NR^{40}C(=O)NR^{42}R^{43}$, $-NR^{40}S(=O)_2NR^{42}R^{43}$, and $-SCF_3$, and
    (c) any two of $Z^1$, $Z^2$, and $Z^3$ may together form a group of formula $-A^6-A^7-A^8-A^9-A^{10}-$,
        wherein $A^6$, $A^7$, $A^8$, $A^9$, and $A^{10}$ are independently chosen from a bond, $-CZ^4Z^5-$, $-C(=O)-$, $-NZ^6-$, $-S-$, $-S(=O)-$, $-S(=O)_2-$, or $-O-$, wherein:
        (i) when any two of $Z^1$, $Z^2$, $Z^3$, $Z^4$, $Z^5$, and $Z^6$ are located on adjacent atoms, they may form a bond between the atoms, and
        (ii) any of $Z^4$, $Z^5$, and $Z^6$ may be independently chosen from H, halogen, $-NO_2$, $-OR^{50}$, $-C(=O)R^{50}$, $-C(=O)OR^{50}$, $-C(=O)NR^{52}R^{53}$, $-NR^{50}R^{51}$, $C_{1-6}$-alkyl-$(R^{55})_x$, $C_{6-15}$-aryl-$(R^{55})_x$, 5-15 membered heteroaryl-$(R^{55})_x$, $C_{3-10}$ cycloalkyl-$(R^{55})_x$, 3-15 membered heterocycloalkyl-$(R^{55})_x$, pseudohalogen, $-S(=O)_nR^{50}$, $-S(=O)_2NR^{52}R^{53}$, $-OCH_2F$, $-OCHF_2$, $-OCF_3$, $-NHOH$, $-OC(=O)R^{50}$, $-OC(=O)NR^{52}R^{53}$, $-NR^{50}C(=O)R^{51}$, $-NR^{50}C(=O)OR^{51}$, $-NR^{50}S(=O)_2R^{51}$, $-NR^{50}C(=O)NR^{52}R^{53}$, $-NR^{50}S(=O)_2NR^{52}R^{53}$, and $-SCF_3$;
- $R^{25}$, $R^{35}$, $R^{45}$, and $R^{55}$ at each occurrence are independently chosen from halogen, $-NO_2$, $-OR^{60}$, $=O$, $-C(=O)R^{60}$, $-C(=O)OR^{60}$, $-C(=O)NR^{62}R^{63}$, $-NR^{60}R^{61}$, $C_{1-6}$-alkyl, $-C_{1-6}$-alkyl-$O-C_{1-6}$-alkyl, $C_{1-6}$-haloalkyl, $C_{2-6}$-alkenyl, $C_{2-6}$-alkynyl, $C_{6-15}$-aryl, 5-15 membered heteroaryl, $C_{3-10}$ cycloalkyl, 3-15 membered heterocycloalkyl, pseudohalogen, $-S(=O)_nR^{60}$, $-S(=O)_2NR^{62}R^{63}$, $-OCH_2F$, $-OCHF_2$, $-OCF_3$, $-NHOH$, $-OC(=O)R^{60}$, $-OC(=O)NR^{62}R^{63}$, $-OP(=O)(OH)_2$, $-NR^{60}C(=O)R^{61}$, $-NR^{60}C(=O)OR^{61}$, $-NR^{60}S(=O)_2R^{61}$, $-NR^{60}C(=O)NR^{62}R^{63}$, $-NR^{60}S(=O)_2NR^{62}R^{63}$, and $-SCF_3$, in which said $C_{1-6}$-alkyl, $C_{1-6}$-haloalkyl, $C_{2-6}$-alkenyl, $C_{2-6}$-alkynyl, $C_{6-15}$-aryl, 5-15 membered heteroaryl, $C_{3-10}$ cycloalkyl, and 3-15 membered heterocycloalkyl groups are optionally substituted by one or more substituents independently chosen from $C_{1-6}$-alkyl, $C_{2-6}$-alkenyl, $C_{2-6}$-alkynyl, halogen, cyano, $C_{3-10}$ cycloalkyl, phenyl, 5-10 membered heteroaryl-$(R^{79})_x$, 3-10 membered heterocycloalkyl, $-N(R^{76})_2$, $-C(=O)OR^{76}$, $-C(=O)N(R^{76})_2$, $=O$, and $-OR^{76}$;
- $R^{10}$, $R^{11}$, $R^{20}$, $R^{21}$, $R^{30}$, $R^{31}$, $R^{40}$, $R^{41}$, $R^{50}$, $R^{51}$, $R^{60}$, $R^{61}$ at each occurrence are independently chosen from H, $C_{1-6}$-alkyl, $C_{2-6}$-alkynyl, $C_{1-6}$-haloalkyl, $C_{6-15}$-aryl, 5-15 membered heteroaryl, $C_{3-10}$ cycloalkyl, and 3-15 membered heterocycloalkyl, in which said $C_{1-6}$-alkyl, $C_{2-6}$-alkynyl, $C_{1-6}$-haloalkyl, $C_{6-15}$-aryl, 5-15 membered heteroaryl, $C_{3-10}$ cycloalkyl, and 3-15 membered heterocycloalkyl groups are optionally substituted by one or more substituents independently chosen from $C_{1-6}$-alkyl, $C_{2-6}$-alkenyl, $C_{2-6}$-alkynyl, halogen, cyano, phenyl, 5-10 membered heteroaryl-$(R^{79})_x$, 3-10 membered heterocycloalkyl, $-N(R^{76})_2$, $-C(=O)OR^{76}$, $-C(=O)N(R^{76})_2$, $=O$, and $-OR^{76}$;
- $R^{12}$, $R^{13}$, $R^{22}$, $R^{23}$, $R^{32}$, $R^{33}$, $R^{42}$, $R^{43}$, $R^{52}$, $R^{53}$, $R^{62}$, and $R^{63}$ at each occurrence are independently chosen from H, $C_{1-6}$-alkyl, $C_{2-6}$-alkynyl, $C_{1-6}$-haloalkyl, $C_{6-15}$-aryl, 5-15 membered heteroaryl, $C_{3-10}$ cycloalkyl, and 3-15 membered heterocycloalkyl, in which said $C_{1-6}$-alkyl, $C_{2-6}$-alkynyl, $C_{1-6}$-haloalkyl, $C_{6-15}$-aryl, 5-15 membered heteroaryl, $C_{3-10}$ cycloalkyl, and 3-15 membered heterocycloalkyl groups are optionally substituted by one or more substitutents independently chosen from $C_{1-6}$-alkyl, halogen, $C_{3-10}$ cycloalkyl, 3-10 membered heterocycloalkyl-$(R^{87})_x$, —$N(R^{86})_2$, cyano, $C_{2-6}$-alkynyl, =O, and —$OR^{86}$;

or $R^{12}$ and $R^{13}$, $R^{22}$ and $R^{23}$, $R^{32}$ and $R^{33}$, $R^{42}$ and $R^{43}$, $R^{52}$ and $R^{53}$, or $R^{62}$ and $R^{63}$ may form, together with the nitrogen atom to which they are attached, a 3-15 membered heterocycloalkyl group or a 5-15 membered heteroaryl group, in which said 3-15 membered heterocycloalkyl group or 5-15 membered heteroaryl group is optionally substituted by one or more substituents independently chosen from $C_{1-6}$-alkyl, halogen, and —OH;

$R^{76}$ and $R^{86}$ at each occurrence are independently chosen from H, $C_{1-6}$-alkyl-$(R^{78})_x$, and —C(=O)—$C_{1-6}$-alkyl;

$R^{78}$ at each occurrence is independently chosen from =O and phenyl; $R^{79}$ at each occurrence is =O;

$R^{87}$ at each occurrence is independently chosen from $C_{1-6}$-alkyl;

n at each occurrence is independently chosen from 0, 1, and 2; and x at each occurrence is independently chosen from 0, 1, 2, 3, 4, 5, and 6;

with the proviso that the compound is not:

(a)

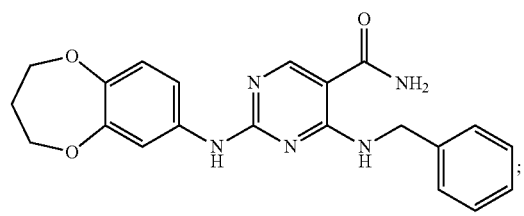

(b)

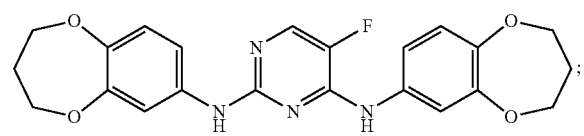

(c)

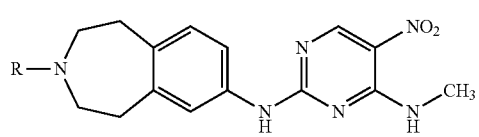

wherein R=H or —C(=O)CF$_3$;

(d)

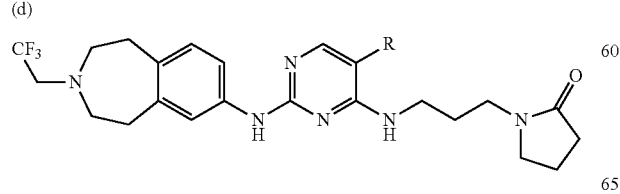

wherein R=Br, Cl, CH$_3$, or CF$_3$;

(e)

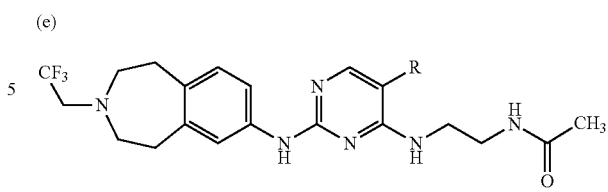

wherein R=Br, Cl, or CH$_3$;

(f)

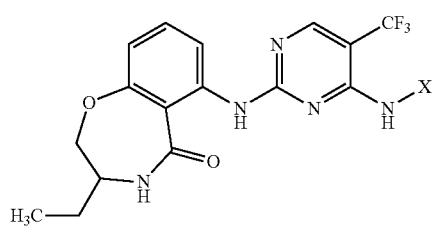

wherein X=

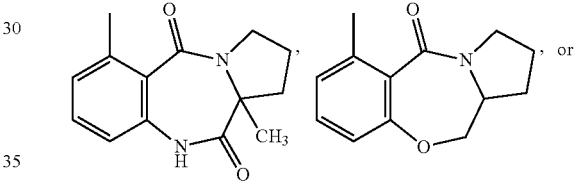

(g)

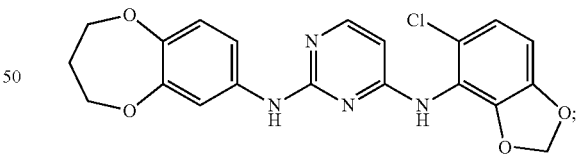

(h)

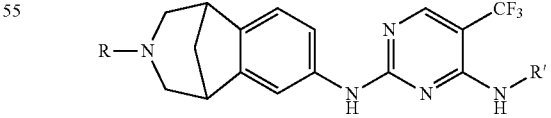

wherein
R=H, ethyl, —C(=O)CH$_3$, —C(=O)CH(CH$_3$)$_2$, —C(=O)CH$_2$OCH$_3$, —C(=O)NHCH(CH$_3$)$_2$, —C(=O)CH$_2$NHC(=O)CH$_3$, —C(=O)CHF$_2$, —C(=O)CF$_3$, —C(=O)NHCH$_2$CH$_3$, —C(=O)CH$_2$N(CH$_3$)$_2$,

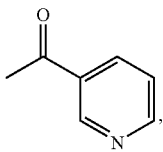

2-pyridyl, or S(=O)$_2$CH$_3$,
and
R'=cyclopropyl, cyclobutyl, —CH$_2$-cyclopropyl, ethyl, —CH(CH$_3$)$_2$, propyl, methyl,

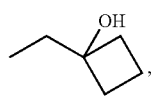

—(CH$_2$)$_2$OCH$_3$, or

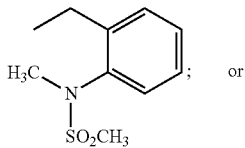

or (i)

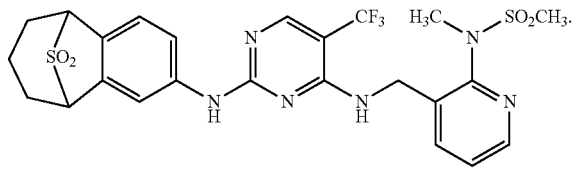

In another embodiment, the compound is a compound of formula I or a pharmaceutically acceptable salt thereof. In another embodiment, the compound is a compound of formula II or a pharmaceutically acceptable salt thereof.

In another embodiment, R$^1$ is H, halogen, —NO$_2$, —OR$^{10}$, —C(=O)R$^{10}$, —C(=O)OR$^{10}$, —C(=O)NR$^{12}$R$^{13}$, —NR$^{10}$R$^{11}$, C$_{1-6}$-alkyl, —C$_{1-6}$-alkyl-OR$^{10}$, —C$_{1-6}$-alkyl-NR$^{12}$R$^{13}$, C$_{1-6}$-haloalkyl, C$_{2-6}$-alkenyl, C$_{2-6}$-alkynyl, C$_{6-15}$-aryl, 5-15 membered heteroaryl, C$_{3-10}$ cycloalkyl, 3-15 membered heterocycloalkyl, pseudohalogen, —S(=O)$_n$R$^{10}$, —S(=O)$_2$NR$^{12}$R$^{13}$, —OCH$_2$F, —OCHF$_2$, —OCF$_3$, —NHOH, —OC(=O)R$^{10}$, —OC(=O)NR$^{12}$R$^{13}$, —NR$^{10}$C(=O)R$^{11}$, —NR$^{10}$C(=O)OR$^{11}$, —NR$^{10}$S(=O)$_2$R$^{11}$, or —SCF$_3$. In another embodiment, R$^1$ is H, halogen, nitro, —OR$^{10}$, —NR$^{10}$R$^{11}$, C$_{1-6}$-alkyl, —C$_{1-6}$-alkyl-OR$^{10}$, —C$_{1-6}$-alkyl-NR$^{12}$R$^{13}$, C$_{1-6}$-haloalkyl, C$_{2-6}$-alkenyl, C$_{2-6}$-alkynyl, 5-6 membered heteroaryl, cyclopropyl, 3-6 membered heterocycloalkyl, pseudohalogen, —S(=O)$_n$R$^{10}$, —S(=O)$_2$NR$^{12}$R$^{13}$, —OCH$_2$F, —OCHF$_2$, —OCF$_3$, —NHOH, —NR$^{10}$C(=O)R$^{11}$, —NR$^{10}$C(=O)OR$^{11}$, —NR$^{10}$S(=O)$_2$R$^{11}$, or —SCF$_3$. In another embodiment, R$^1$ is H, halogen, nitro, C$_{1-6}$-alkyl, C$_{1-6}$-haloalkyl, pseudohalogen, —S(=O)$_n$R$^{10}$, or —OCF$_3$. In another embodiment, R$^1$ is H, halogen, nitro, C$_{1-6}$-alkyl, C$_{1-6}$-haloalkyl, cyano, —S(=O)$_n$R$^{10}$, or —OCF$_3$. In another embodiment, R$^1$ is halogen, nitro, C$_{1-6}$-alkyl, C$_{1-6}$-haloalkyl, or pseudohalogen. In another embodiment, R$^1$ is halogen, nitro, C$_{1-6}$-alkyl, C$_{1-6}$-haloalkyl, or cyano. In another embodiment, R$^1$ is halogen, nitro, C$_{1-4}$-alkyl, C$_{1-4}$-fluoroalkyl, or cyano. In another embodiment, R$^1$ is halogen or C$_{1-4}$-fluoroalkyl. In another embodiment, R$^1$ is fluoro, chloro, bromo, nitro, methyl, trifluoromethyl, or cyano. In another embodiment, R$^1$ is trifluoromethyl or chloro. In another embodiment, R$^1$ is chloro.

In another embodiment, R$^1$ is as defined in any of the above embodiments, except that R$^1$ is not H. In another embodiment, R$^1$ is as defined in any of the above embodiments, except that R$^1$ is not —C(=O)NR$^{10}$R$^{11}$. In another embodiment, R$^1$ is as defined in any of the above embodiments, except that R$^1$ is not —CN. In another embodiment, R$^1$ is as defined in any of the above embodiments except that R$^1$ is not —NO$_2$, —C(=O)R$^{10}$, —C(=O)OR$^{10}$, —C(=O)NR$^{12}$R$^{13}$, —NR$^{10}$R$^{11}$, —C$_{1-6}$-alkyl-OR$^{10}$, —C$_{1-6}$-alkyl-NR$^{12}$R$^{13}$, 5-15 membered heteroaryl, 4-7 membered alkyleneimino, —CN, —S(=O)$_2$NR$^{12}$R$^{13}$, —NR$^{10}$C(=O)R$^{11}$, —NR$^{10}$C(=O)OR$^{11}$, or —NR$^{10}$S(=O)$_2$R$^{11}$. In another embodiment, R$^1$ is as defined in any of the above embodiments, except that R$^1$ is not H, halogen, —NO$_2$, —C(=O)O—C$_{1-6}$-alkyl, —N(X)$_2$, C$_{1-6}$-alkyl, dihalomethyl, trihalomethyl, or —N(X)C(=O)—C$_{1-6}$-alkyl, wherein X at each occurrence is independently chosen from H and C$_{1-6}$-alkyl. In another embodiment, R$^1$ is as defined in any of the above embodiments, except that R$^1$ is not H, halogen, C$_{1-6}$-alkyl, —C$_{1-6}$-alkyl-OX, —C$_{1-6}$-alkyl-NR$^{12}$R$^{13}$, C$_{1-6}$-haloalkyl, C$_{2-6}$-alkenyl, C$_{2-6}$-alkynyl, C$_{3-8}$ cycloalkyl, or —CN, wherein X is independently chosen from H and C$_{1-6}$-alkyl. In another embodiment, R$^1$ is as defined in any of the above embodiments, except that R$^1$ is not H, halogen, —NO$_2$, —OX, —C(=O)R$^{10}$, —C$_{1-6}$-alkyl-OX, alkyl, phenyl, C$_{3-10}$-cycloalkyl, —SC$_{1-6}$-alkyl, —OCF$_3$, or —SCF$_3$, wherein X at each occurrence is independently chosen from H, phenyl, and C$_{1-6}$-alkyl.

In another embodiment, R$^{10}$ and R$^{11}$ at each occurrence are independently chosen from H, C$_{1-6}$-alkyl, C$_{2-6}$-alkynyl, C$_{1-6}$-haloalkyl, C$_{6-15}$-aryl, 5-15 membered heteroaryl, C$_{3-10}$ cycloalkyl, and 3-15 membered heterocycloalkyl, in which said C$_{1-6}$-alkyl, C$_{2-6}$-alkynyl, C$_{1-6}$-haloalkyl, C$_{6-15}$-aryl, 5-15 membered heteroaryl, C$_{3-10}$ cycloalkyl, and 3-15 membered heterocycloalkyl groups are optionally substituted by one or more substituents independently chosen from C$_{1-6}$-alkyl, halogen, and —OH. In another embodiment, R$^{10}$ and R$^{11}$ at each occurrence are independently chosen from H, C$_{1-6}$-alkyl optionally substituted by —OH, C$_{2-6}$-alkynyl, C$_{1-6}$-haloalkyl, C$_{6-15}$-aryl, 5-15 membered heteroaryl, C$_{3-10}$cycloalkyl, and 3-15 membered heterocycloalkyl optionally substituted by C$_{1-6}$-alkyl or —OH. In another embodiment, R$^{10}$ and R$^{11}$ at each occurrence are independently chosen from H, C$_{1-6}$-alkyl optionally substituted by —OH, C$_{1-6}$-haloalkyl, 5-15 membered heteroaryl, C$_{3-10}$ cycloalkyl, and 3-15 membered heterocycloalkyl optionally substituted by C$_{1-6}$-alkyl or —OH. In another embodiment, R$^{10}$ and R$^{11}$ at each occurrence are independently chosen from H, C$_{1-6}$-alkyl optionally substituted by —OH, C$_{1-6}$-haloalkyl, and 3-15 membered heterocycloalkyl optionally substituted by C$_{1-6}$-alkyl or —OH. In another embodiment, R$^{10}$ and R$^{11}$ at each occurrence are independently chosen from H, C$_{1-6}$-alkyl optionally substituted by —OH, C$_{1-6}$-haloalkyl, and 3-15 membered heterocycloalkyl. In another embodiment, R$^{10}$ and R$^{11}$ at each occurrence are independently chosen from H and C$_{1-6}$-alkyl.

In another embodiment, R$^{12}$ and R$^{13}$ at each occurrence are independently chosen from H, C$_{1-6}$-alkyl, C$_{2-6}$-alkynyl, C$_{1-6}$-haloalkyl, C$_{6-15}$-aryl, 5-15 membered heteroaryl, C$_{3-10}$-cycloalkyl, and 3-15 membered heterocycloalkyl, in which said C$_{1-6}$-alkyl, C$_{2-6}$-alkynyl, C$_{1-6}$-haloalkyl, C$_{6-15}$-aryl, 5-15 membered heteroaryl, C$_{3-10}$ cycloalkyl, and 3-15 membered heterocycloalkyl groups are optionally substituted by one or more substituents independently chosen from C$_{1-6}$-alkyl, halogen, and —OH; or R$^{12}$ and R$^{13}$ may form, together with the nitrogen atom to which they are attached, a 3-15 membered heterocycloalkyl group or a 5-15 membered heteroaryl group, in which said 3-15 membered heterocycloalkyl group or 5-15 membered heteroaryl group is optionally substituted by one or more substituents independently chosen from $C_{1-6}$-alkyl, halogen, and —OH. In another embodiment, $R^{12}$ and $R^{13}$ at each occurrence are independently chosen from H, $C_{1-6}$-alkyl optionally substituted by —OH, $C_{2-6}$-alkynyl, $C_{1-6}$-haloalkyl, $C_{6-15}$-aryl, 5-15 membered heteroaryl, $C_{3-10}$ cycloalkyl, and 3-15 membered heterocycloalkyl optionally substituted by —OH; or $R^{12}$ and $R^{13}$ may form, together with the nitrogen atom to which they are attached, a 3-15 membered heterocycloalkyl group or a 5-15 membered heteroaryl group, in which the heterocycloalkly group or 5-15 membered heteroaryl group may optionally be substituted by one or more members selected from $C_{1-6}$-alkyl. In another embodiment, $R^{12}$ and $R^{13}$ at each occurrence are independently chosen from H, $C_{1-6}$-alkyl optionally substituted by —OH, $C_{1-6}$-haloalkyl, 5-15 membered heteroaryl, $C_{3-10}$ cycloalkyl, and 3-15 membered heterocycloalkyl optionally substituted by —OH; or $R^{12}$ and $R^{13}$ may form, together with the nitrogen atom to which they are attached, a 3-15 membered heterocycloalkyl group or a 5-15 membered heteroaryl group, in which the heterocycloalkly group or 5-15 membered heteroaryl group may optionally be substituted by one or more members selected from $C_{1-6}$-alkyl. In another embodiment, $R^{2}$ and $R^{13}$ at each occurrence are independently chosen from H, $C_{1-6}$-alkyl optionally substituted by —OH, $C_{1-6}$-haloalkyl, and 3-15 membered heterocycloalkyl; or $R^{12}$ and $R^{13}$ may form, together with the nitrogen atom to which they are attached, a 3-15 membered heterocycloalkyl group or a 5-15 membered heteroaryl group. In another embodiment, $R^{12}$ and $R^{13}$ at each occurrence are independently chosen from H, $C_{1-6}$-alkyl optionally substituted by —OH, $C_{1-6}$-haloalkyl, and 3-15 membered heterocycloalkyl. In another embodiment, $R^{12}$ and $R^{13}$ at each occurrence are independently chosen from H, $C_{1-6}$-alkyl optionally substituted by —OH, $C_{2-6}$-alkynyl, $C_{1-6}$-haloalkyl, $C_{6-15}$-aryl, 5-15 membered heteroaryl, $C_{3-10}$ cycloalkyl, and 3-15 membered heterocycloalkyl optionally substituted by —OH. In another embodiment, $R^{12}$ and $R^{13}$ at each occurrence are independently chosen from H and $C_{1-6}$-alkyl.

In another embodiment, $R^{2}$ is a group chosen from $C_{1-6}$-alkyl, $C_{2-6}$-alkynyl, $C_{6-10}$-aryl, $C_{3-7}$-cycloalkyl, 5-7 membered heterocycloalkyl, and 5-11 membered heteroaryl, wherein the $R^{2}$ group is optionally substituted. In another embodiment, $R^{2}$ is a group chosen from $C_{6-10}$-aryl, $C_{3-7}$-cycloalkyl, 5-7 membered heterocycloalkyl, and 5-11 membered heteroaryl, wherein the $R^{2}$ group is optionally substituted. In another embodiment, $R^{2}$ is a group chosen from $C_{1-6}$-alkyl, $C_{2-6}$-alkynyl, $C_{6-10}$-aryl, $C_{5-7}$-cycloalkyl, 5-7 membered heterocycloalkyl, and 5-10 membered heteroaryl, wherein the $R^{2}$ group is optionally substituted. In another embodiment, $R^{2}$ is a group chosen from $C_{1-6}$-alkyl, $C_{2-6}$-alkenyl, $C_{2-6}$-alkynyl, $C_{6-15}$-aryl, $C_{3-10}$-cycloalkyl, and 3-15 membered heterocycloalkyl, wherein the $R^{2}$ group is optionally substituted. In another embodiment, $R^{2}$ is a group chosen from $C_{1-6}$-alkyl, $C_{2-6}$-alkynyl, $C_{6-10}$-aryl, $C_{5-7}$-cycloalkyl, and 5-7 membered heterocycloalkyl, wherein the $R^{2}$ group is optionally substituted. In another embodiment, $R^{2}$ is a group chosen from $C_{1-6}$-alkyl, $C_{2-6}$-alkynyl, $C_{6-10}$-aryl, $C_{3-7}$-cycloalkyl, 7 membered heterocycloalkyl, and 5-11 membered heteroaryl, wherein the $R^{2}$ group is optionally substituted. In another embodiment, $R^{2}$ is a group chosen from $C_{1-6}$-alkyl, $C_{2-6}$-alkynyl, phenyl, $C_{9}$-aryl, $C_{3-7}$-cycloalkyl, 7 membered heterocycloalkyl, and 5-11 membered heteroaryl, wherein the $R^{2}$ group is optionally substituted. In another embodiment, $R^{2}$ is a group chosen from $C_{1-6}$-alkyl, $C_{2-6}$-alkynyl, $C_{6-10}$-aryl, $C_{5-7}$-cycloalkyl, and 7 membered heterocycloalkyl, wherein the $R^{2}$ group is optionally substituted. In another embodiment, $R^{2}$ is a group chosen from $C_{6-10}$-aryl, $C_{3-7}$-cycloalkyl, 7 membered heterocycloalkyl, and 5-11 membered heteroaryl, wherein the $R^{2}$ group is optionally substituted. In another embodiment, $R^{2}$ is a group chosen from phenyl, $C_{9}$-aryl, $C_{3-7}$-cycloalkyl, 7 membered heterocycloalkyl, and 5-11 membered heteroaryl, wherein the $R^{2}$ group is optionally substituted. In another embodiment, $R^{2}$ is a group chosen from $C_{6-10}$-aryl, $C_{5-7}$-cycloalkyl, and 7 membered heterocycloalkyl, wherein the $R^{2}$ group is optionally substituted. In another embodiment, $R^{2}$ is a group chosen from ethyl, propyl, isopropyl, isobutyl, t-butyl, propynyl, phenyl, indanyl, [2.2.1]-bicycloheptenyl, cyclohexyl, cyclopentyl, cyclopropyl, [2.2.1]-bicycloheptanyl, tetrahydroazepinonyl, 2,3,4,5-tetrahydrobenzazepinyl, 2,3,4,5-tetrahydro-1H-benzo[e][1,4]diazepinyl, 2,3,4,5-tetrahydrobenzodiazepinyl, 1,2,3,4-tetrahydrobenzo[e][1,4]diazepine-5-onyl, 1,2,3,4-tetrahydrobenzodiazepin-5-onyl, 6,7,8,9-tetrahydro-5-thia-8-aza-benzocycloheptenyl, isoxindolyl, pyrazolyl, benzimidazollyl, 2-hydroxy-3-pyridinyl, pyridinyl, thienyl, benzodioxolyl, indazolyl, and isoxazolyl, wherein the $R^{2}$ group is optionally substituted. In another embodiment, $R^{2}$ is a group chosen from ethyl, propyl, isopropyl, isobutyl, t-butyl, propynyl, phenyl, indanyl, [2.2.1]-bicycloheptenyl, cyclohexyl, cyclopentyl, [2.2.1]-bicycloheptanyl, and tetrahydroazepinonyl, wherein the $R^{2}$ group is optionally substituted. In another embodiment, $R^{2}$ is a group chosen from propynyl, phenyl, indanyl, [2.2.1]-bicycloheptenyl, cyclohexyl, cyclopentyl, cyclopropyl, [2.2.1]-bicycloheptanyl, tetrahydroazepinonyl, 2,3,4,5-tetrahydro-3-benzazepinyl, 2,3,4,5-tetrahydro-1H-benzo[e][1,4]diazepinyl, 1,2,3,4-tetrahydrobenzo[e][1,4]diazepine-5-onyl, 6,7,8,9-tetrahydro-5-thia-8-aza-benzocycloheptenyl, isoxindolyl, pyrazolyl, benzimidazollyl, 2-hydroxy-3-pyridinyl, pyridinyl, thienyl, benzodioxolyl, indazolyl, and isoxazolyl, wherein the $R^{2}$ group is optionally substituted. In another embodiment, $R^{2}$ is a group chosen from phenyl, indanyl, [2.2.1]-bicycloheptenyl, cyclohexyl, cyclopentyl, [2.2.1]-bicycloheptanyl, and tetrahydroazepinonyl, wherein the $R^{2}$ group is optionally substituted. In another embodiment, $R^{2}$ is a group chosen from phenyl, [2.2.1]-bicycloheptenyl, and cyclohexyl, wherein the $R^{2}$ group is optionally substituted.

In another embodiment, the $R^{2}$ group is optionally substituted by one or more members independently chosen from halogen, —$NO_2$, —$OR^{20}$, —$C(=O)R^{20}$, —$C(=O)OR^{20}$, —$C(=O)NR^{22}R^{23}$, —$NR^{20}R^{21}$, $C_{1-6}$-alkyl-$(R^{25})_x$, $C_{6-15}$-aryl-$(R^{25})_x$, 5-15 membered heteroaryl-$(R^{25})_x$, $C_{3-10}$ cycloalkyl-$(R^{25})_x$, 3-15 membered heterocycloalkyl-$(R^{25})_x$, pseudohalogen, —$S(=O)_nR^{20}$, —$S(=O)_2NR^{22}R^{23}$, —$OCH_2F$, —$OCHF_2$, —$OCF_3$, —NHOH, —$OC(=O)R^{20}$, —$OC(=O)NR^{22}R^{23}$, —$NR^{20}C(=O)R^{21}$, —$NR^{20}C(=O)OR^{21}$, —$NR^{20}S(=O)_2R^{21}$, —$NR^{20}C(=O)NR^{22}R^{23}$, —$NR^{20}S(=O)_2NR^{22}R^{23}$, and —$SCF_3$. In another embodiment, the $R^{2}$ group is optionally substituted by one or more members independently chosen from halogen, —$NO_2$, —$OR^{20}$, —$C(=O)R^{20}$, —$C(=O)OR^{20}$, —$C(=O)NR^{22}R^{23}$, —$C(=O)N(C_{1-6}$-alkyl-OH)$R^{20}$, —$NR^{20}R^{21}$, $C_{1-6}$-alkyl, —$C_{1-6}$-alkyl-$OR^{20}$, —$C_{1-6}$-alkyl-$NR^{22}R^{23}$, $C_{1-6}$-haloalkyl, $C_{6-15}$-aryl, $C_{3-10}$ cycloalkyl, 3-15 membered heterocycloalkyl, -3-15 membered heterocycloalkyl-$OR^{20}$, pseudohalogen, —$S(=O)_nR^{20}$, —$S(=O)_2NR^{22}R^{23}$, —$OCH_2F$, —$OCHF_2$, —$OCF_3$, —NHOH, —$OC(=O)R^{20}$, —$OC(=O)NR^{22}R^{23}$, —$NR^{20}C(=O)R^{21}$, —$NR^{20}C(=O)OR^{21}$, —$NR^{20}S(=O)_2R^{21}$, —$NR^{20}C(=O)NR^{22}R^{23}$, —$NR^{20}S(=O)_2NR^{22}R^{23}$, —$SCF_3$, and 5-15 membered heteroaryl optionally substituted by one or more members chosen from $C_{1-6}$-alkyl and —$C_{1-6}$-alkyl-O—$C_{1-6}$-alkyl. In another embodiment, the $R^2$ group is optionally substituted by one or more members independently chosen from halogen, —$NO_2$, —$OR^{20}$, —C(=O)$R^{20}$, —C(=O)O$R^{20}$, —C(=O)N$R^{22}R^{23}$, —C(=O)N($C_{1-6}$-alkyl-OH)$R^{20}$, —$NR^{20}R^{21}$, $C_{1-6}$-alkyl, —$C_{1-6}$-alkyl-O$R^{20}$, —$C_{1-6}$-alkyl-N$R^{22}R^{23}$, $C_{1-6}$-haloalkyl, $C_{6-15}$-aryl, 5-15 membered heteroaryl, $C_{3-10}$ cycloalkyl, 3-15 membered heterocycloalkyl, -3-15 membered heterocycloalkyl-O$R^{20}$, pseudohalogen, —S(=O)$_n$$R^{20}$, —S(=O)$_2$N$R^{22}R^{23}$, —OCH$_2$F, —OCHF$_2$, —OCF$_3$, —NHOH, —C(=O)$R^{20}$, —OC(=O)N$R^{22}R^{23}$, —N$R^{20}$C(=O)$R^{21}$, —N$R^{20}$C(=O)O$R^{21}$, —N$R^{20}$S(=O)$_2$$R^{21}$, and —SCF$_3$. In another embodiment, the $R^2$ group is optionally substituted by one or more members independently chosen from halogen, —O$R^{20}$, —C(=O)$R^{20}$, —C(=O)O$R^{20}$, —C(=O)N$R^{22}R^{23}$, —C(=O)N($C_{1-6}$-alkyl-OH)$R^{20}$, —N$R^{20}R^{21}$, $C_{1-6}$-alkyl, —$C_{1-6}$-alkyl-O$R^{20}$, $C_{1-6}$-haloalkyl, $C_{6-15}$-aryl, $C_{3-10}$ cycloalkyl, 3-15 membered heterocycloalkyl, —S(=O)$_n$$R^{20}$, —S(=O)$_2$N$R^{22}R^{23}$, —OCF$_3$, —OC(=O)$R^{20}$, —OC(=O)N$R^{22}R^{23}$, —N$R^{20}$C(=O)$R^{21}$, —N$R^{20}$C(=O)O$R^{21}$, —N$R^{20}$S(=O)$_2$$R^{21}$, —N$R^{20}$C(=O)N$R^{22}R^{23}$, —SCF$_3$, and 5-15 membered heteroaryl optionally substituted by one or more members chosen from $C_{1-6}$-alkyl and —$C_{1-6}$-alkyl-O—$C_{1-6}$-alkyl. In another embodiment, the $R^2$ group is optionally substituted by one or more members independently chosen from halogen, —$NO_2$, —O$R^{20}$, =O, —C(=O)$R^{20}$, —C(=O)O$R^{20}$, —C(=O)N$R^{22}R^{23}$, —N$R^{20}R^{21}$, $C_{1-6}$-alkyl-($R^{25}$)$_x$, phenyl-($R^{25}$)$_x$, 5-10 membered heteroaryl-($R^{25}$)$_x$, 5-7 membered heterocycloalkyl-($R^{25}$)$_x$, pseudohalogen, —S(=O)$_2$$R^{20}$, —S(=O)$_2$N$R^{22}R^{23}$, —OCF$_3$, —N$R^{20}$C(=O)$R^{21}$, —N$R^{20}$S(=O)$_2$$R^{21}$, and —N$R^{20}$C(=O)N$R^{22}R^{23}$. In another embodiment, the $R^2$ group is optionally substituted by one or more members independently chosen from halogen, —O$R^{20}$, —C(=O)$R^{20}$, —C(=O)O$R^{20}$, —C(=O)N$R^{22}R^{23}$, —C(=O)N($C_{1-6}$-alkyl-OH)$R^{20}$, —N$R^{20}R^{21}$, $C_{1-6}$-alkyl, 3-15 membered heterocycloalkyl, —S(=O)$_2$N$R^{22}R^{23}$, —N$R^{20}$C(=O)$R^{21}$, —N$R^{20}$S(=O)$_2$$R^{21}$, —N$R^{20}$C(=O)N$R^{22}R^{23}$, —SCF$_3$, and 5-15 membered heteroaryl optionally substituted by one or more members chosen from $C_{1-6}$-alkyl and —$C_{1-6}$-alkyl-O—$C_{1-6}$-alkyl. In another embodiment, the $R^2$ group is optionally substituted by one or more members independently chosen from halogen, —$NO_2$, —O$R^{20}$, =O, —C(=O)—$C_{1-6}$-alkyl, —C(=O)O—$C_{1-6}$-alkyl, —C(=O)O—$C_{1-6}$-alkyl-O—$C_{1-6}$-alkyl, —C(=O)N$R^{22}R^{23}$, —$NH_2$, —NH$C_{1-6}$-alkyl, —N($C_{1-6}$-alkyl)$_2$, —N($C_{1-6}$-alkyl)$C_{1-6}$-alkyl-C≡N, $C_{1-6}$-alkyl, $C_{1-6}$-alkyl-$R^{25}$, phenyl, phenyl-C≡N, 5-11 membered heteroaryl-($R^{25}$)$_x$, 5-7 membered heterocycloalkyl-($R^{25}$)$_x$, —C≡N, —S(=O)$_2$$R^{20}$, —S(=O)$_2$NH$C_{1-6}$-alkyl, —S(=O)$_2$N($C_{1-6}$-alkyl)$_2$, —S(=O)$_2$N($C_{2-6}$-alkynyl)$C_{1-6}$-alkyl, —OCF$_3$, —NHC(=O)$C_{1-6}$-alkyl, —NHC(=O)$C_{1-6}$-haloalkyl, —N$R^{20}$S(=O)$_2$$R^{21}$, and —NHC(=O)N($C_{1-6}$-alkyl)$_2$. In another embodiment, the $R^2$ group is optionally substituted by one or more members independently chosen from halogen, —O$R^{20}$, —C(=O)$R^{20}$, —C(=O)O$R^{20}$, —C(=O)N$R^{22}R^{23}$, —C(=O)N($C_{1-6}$-alkyl-OH)$R^{20}$, —N$R^{20}R^{21}$, $C_{1-6}$-alkyl, 5-10 membered heterocycloalkyl, —S(=O)$_2$N$R^{22}R^{23}$, —NHC(=O)$R^{21}$, —NHS(=O)$_2$$R^{21}$, —NHC(=O)N$R^{22}R^{23}$, and 5-15 membered heteroaryl optionally substituted by one or more members chosen from $C_{1-6}$-alkyl and —$C_{1-6}$-alkyl-O—$C_{1-6}$-alkyl, and wherein $R^{20}$, $R^{21}$, $R^{22}$, and $R^{23}$ at each occurrence are independently chosen from H, $C_{1-6}$-alkyl, $C_{1-6}$-fluoroalkyl, $C_{2-6}$-alkynyl, and $C_{3-6}$-cycloalkyl. In another embodiment, the $R^2$ group is optionally substituted by one or more members independently chosen from halogen, —$NO_2$, —OH, —O$C_{1-6}$-alkyl, —O$C_{1-6}$-haloalkyl, —O$C_{1-6}$-alkyl-$R^{20a}$, —O$C_{1-6}$-alkyl-(OH)$_2$, —O$C_{2-6}$-alkenyl, —O$C_{2-6}$-alkynyl, —O(5-6 membered heterocycloalkyl), =O, —C(=O)—$C_{1-6}$-alkyl, —C(=O)O—$C_{1-6}$-alkyl, —C(=O)—$C_{1-6}$-alkyl-O—$C_{1-6}$-alkyl, —C(=O)$NH_2$, —C(=O)NH$C_{1-6}$-alkyl, —C(=O)NH$C_{2-6}$-alkynyl, —C(=O)N($C_{1-6}$-alkyl)$_2$, —C(=O)NH$C_{1-6}$-alkyl-$R^{20b}$, —$NH_2$, —NH$C_{1-6}$-alkyl, —N($C_{1-6}$-alkyl)$_2$, —N($C_{1-6}$-alkyl)$C_{1-6}$-alkyl-C≡N, $C_{1-6}$-alkyl, $C_{1-6}$-alkyl-C(=O)$NH_2$, $C_{1-6}$-alkyl-C≡N, $C_{1-6}$-alkyl-N$R^{20c}R^{20d}$, phenyl, phenyl-C≡N, 5-9 membered heteroaryl-($R^{25a}$)$_x$, 5-7 membered heterocycloalkyl-($R^{25b}$)$_y$, —C≡N, —S(=O)$_2$$C_{1-6}$-alkyl, —S(=O)$_2$(5-6 membered heterocycloalkyl), —S(=O)$_2$(5-6 membered heterocycloalkyl-$R^{20e}$), —S(=O)$_2$NH$C_{1-6}$-alkyl, —S(=O)$_2$N($C_{1-6}$-alkyl)$_2$, —S(=O)$_2$N($C_{2-6}$-alkynyl)$C_{1-6}$-alkyl, —OCF$_3$, —NHC(=O)$C_{1-6}$-alkyl, —NHC(=O)$C_{1-6}$-haloalkyl, —N$R^{20f}$S(=O)$_2$$R^{20g}$, and —NHC(=O)N($C_{1-6}$-alkyl)$_2$, wherein $R^{20a}$ is chosen from —C≡N, —C(=O)OH, —C(=O)O$C_{1-6}$-alkyl, 5-6 membered heterocycloalkyl, —OH, —O$C_{1-6}$-alkyl, —OCH$_2$-phenyl, —C(=O)$NH_2$, —$NH_2$, and —NHC(=O)$C_{1-6}$-alkyl, $R^{20b}$ is chosen from —OH, —O$C_{1-6}$-alkyl, cyclopropyl, —C≡N, —N($C_{1-6}$-alkyl)$_2$, and 5-6 membered heterocycloalkyl optionally substituted by $C_{1-6}$-alkyl, $R^{20c}$ and $R^{20d}$ are each independently chosen from H, $C_{1-6}$-alkyl, $C_{1-6}$-alkyl-OH, and —C(=O)$C_{1-6}$-alkyl, x is 0, 1 or 2, each $R^{25a}$ is independently chosen from $C_{1-6}$-alkyl, $C_{1-6}$-haloalkyl, $C_{1-6}$-alkyl-O—$C_{1-6}$-alkyl, —NH$C_{1-6}$-alkyl, —OH, and —O$C_{1-6}$-alkyl, y is 0 or 1, $R^{25b}$ is chosen from $C_{1-6}$-alkyl, —C(=O)OH, and 6 membered heterocycloalkyl substituted by $C_{1-6}$-alkyl, $R^{20e}$ is chosen from —OH, $C_{1-6}$-alkyl, and —N($C_{1-6}$-alkyl)$_2$, $R^{20f}$ is chosen from H, $C_{1-6}$-alkyl, and $C_{1-6}$-alkyl-C≡N, and $R^{20g}$ is chosen from $C_{1-6}$-alkyl, $C_{1-6}$-haloalkyl, and cyclopropyl. In another embodiment, the $R^2$ group is optionally substituted by one or more members independently chosen from halogen, —OH, —O$C_{1-6}$-alkyl, —C(=O)$C_{1-6}$-alkyl, —C(=O)O$C_{1-6}$-alkyl, —C(=O)$NH_2$, —C(=O)NH($C_{1-6}$-alkyl), —C(=O)NH($C_{1-6}$-alkyl-OH), —C(=O)NH($C_{3-6}$-cycloalkyl), —$NH_2$, $C_{1-6}$-alkyl, 6-membered heterocycloalkyl, —S(=O)$_2$NH($C_{1-6}$-alkyl), —S(=O)$_2$N($C_{2-6}$-alkynyl)($C_{1-6}$-alkyl), —NHC(=O)$C_{1-6}$-alkyl, —NHC(=O)$C_{1-6}$-fluoroalkyl, —NHS(=O)$_2$($C_{1-6}$-alkyl), —NHS(=O)$_2$($C_{1-6}$-fluoroalkyl), —NHS(=O)$_2$($C_{3-6}$-cycloalkyl), —NHC(=O)N($C_{1-6}$-alkyl)($C_{1-6}$-alkyl), and 5-15 membered heteroaryl optionally substituted by one or more members chosen from $C_{1-6}$-alkyl and —$C_{1-6}$-alkyl-O—$C_{1-6}$-alkyl. In another embodiment, the $R^2$ group is optionally substituted by one or more members independently chosen from halogen, —$NO_2$, —OH, —O$C_{1-6}$-alkyl, —O$C_{1-6}$-haloalkyl, —O$C_{1-6}$-alkyl-$R^{20a}$, —O$C_{1-6}$-alkyl-(OH)$_2$, —O$C_{2-6}$-alkenyl, —O$C_{2-6}$-alkynyl, —O(5-6 membered heterocycloalkyl), =O, —C(=O)—$C_{1-6}$-alkyl, —C(=O)O—$C_{1-6}$-alkyl, —C(=O)O—$C_{1-6}$-alkyl-O—$C_{1-6}$-alkyl, —C(=O)$NH_2$, —C(=O)NH$C_{1-6}$-alkyl, —C(=O)NH$C_{2-6}$-alkynyl, —C(=O)N($C_{1-6}$-alkyl)$_2$, —C(=O)NH$C_{1-6}$-alkyl-$R^{20b}$, —$NH_2$, —NH$C_{1-6}$-alkyl, —N($C_{1-6}$-alkyl)$_2$, —N($C_{1-6}$-alkyl)$C_{1-6}$-alkyl-C≡N, $C_{1-6}$-alkyl, $C_{1-6}$-alkyl-C(=O)$NH_2$, $C_{1-6}$-alkyl-C≡N, $C_{1-6}$-alkyl-NH$C_{1-6}$-alkyl, $C_{1-6}$-alkyl-N$R^{20c}R^{20d}$, phenyl, phenyl-C≡N, 5-9 membered heteroaryl, 5-6 membered heteroaryl-$R^{25a}$, 5-6 membered heteroaryl-(OH)$_2$, 6-7 membered heterocycloalkyl, 6-7 membered heterocycloalkyl-$R^{25b}$, —C≡N, —S(=O)$_2$$C_{1-6}$-alkyl, —S(=O)$_2$(5-6 membered heterocycloalkyl), —S(=O)$_2$(5-6 membered heterocycloalkyl-$R^{20e}$), —S(=O)$_2$NH$C_{1-6}$-alkyl, —S(=O)$_2$N($C_{1-6}$-alkyl)$_2$, —S(=O)$_2$N($C_{2-6}$-alkynyl)$C_{1-6}$-alkyl, —OCF$_3$, —NHC(=O)$C_{1-6}$-alkyl, —NHC(=O)$C_{1-6}$-haloalkyl, —N($C_{1-6}$-alkyl)S(=O)$_2$$C_{1-6}$-alkyl, —N($C_{1-6}$-alkyl-C≡N)S $-(=O)_2C_{1-6}$-alkyl, $-NHS(=O)_2R^{20f}$, and $-NHC(=O)N(C_{1-6}$-alkyl$)_2$, wherein $R^{20a}$ is chosen from $-C\equiv N$, $-C(=O)OH$, $-C(=O)OC_{1-6}$-alkyl, 5-6 membered heterocycloalkyl, $-OH$, $-OC_{1-6}$-alkyl, $-OCH_2$phenyl, $-C(=O)NH_2$, $-NH_2$, and $-NHC(=O)C_{1-6}$-alkyl, $R^{20b}$ is chosen from $-OH$, $-OC_{1-6}$-alkyl, cyclopropyl, $-C\equiv N$, $-N(C_{1-6}$-alkyl$)_2$, and 5-6 membered heterocycloalkyl optionally substituted by $C_{1-6}$-alkyl, $R^{20c}$ is chosen from H and $C_{1-6}$-alkyl, $R^{20d}$ is chosen from $C_{1-6}$-alkyl-OH, and $-C(=O)C_{1-6}$-alkyl, $R^{25a}$ is chosen from $C_{1-6}$-alkyl, $C_{1-6}$-haloalkyl, $C_{1-6}$-alkyl-O—$C_{1-6}$-alkyl, $-NHC_{1-6}$-alkyl, and $-OC_{1-6}$-alkyl, $R^{25b}$ is chosen from $C_{1-6}$-alkyl, $-C(=O)OH$, and 6 membered heterocycloalkyl substituted by $C_{1-6}$-alkyl, $R^{20e}$ is chosen from $-OH$, $C_{1-6}$-alkyl, and $-N(C_{1-6}$-alkyl$)_2$, and $R^{20f}$ is chosen from $C_{1-6}$-alkyl, $C_{1-6}$-haloalkyl, and cyclopropyl. In another embodiment, the $R^2$ group is optionally substituted by one or more members independently chosen from $-OC_{1-6}$-alkyl, $-C(=O)NH_2$, $-C(=O)NH(C_{1-6}$-alkyl), $-C(=O)NH(C_{1-6}$-alkyl-OH), $-C(=O)NH(C_{3-6}$-cycloalkyl), 6-membered heterocycloalkyl, $-S(=O)_2NH(C_{1-6}$-alkyl), $-NHS(=O)_2(C_{1-6}$-alkyl), $-NHS(=O)_2(C_{1-6}$-fluoroalkyl), and $-NHS(=O)_2(C_{3-6}$-cycloalkyl). In another embodiment, the $R^2$ group is optionally substituted by one or more members independently chosen from halogen, $-NO_2$, $-OH$, $-OC_{1-4}$-alkyl, $-OC_{1-4}$-haloalkyl, $-OC_{1-4}$-alkyl-$R^{20a}$, $-OC_{1-4}$-alkyl-$(OH)_2$, $-OC_{2-4}$-alkenyl, $-OC_{2-4}$-alkynyl, $-O(5-6$ membered heterocycloalkyl), $=O$, $-C(=O)-C_{1-4}$-alkyl, $-C(=O)O-C_{1-4}$-alkyl, $-C(=O)O-C_{1-4}$-alkyl-O—$C_{1-4}$-alkyl, $-C(=O)NH_2$, $-C(=O)NHC_{1-4}$-alkyl, $-C(=O)NHC_{2-4}$-alkynyl, $-C(=O)N(C_{1-4}$-alkyl$)_2$, $-C(=O)NHC_{1-4}$-alkyl-$R^{20b}$, $-NH_2$, $-NHC_{1-4}$-alkyl, $-N(C_{1-4}$-alkyl$)_2$, $-N(C_{1-4}$-alkyl$)C_{1-4}$-alkyl-$C\equiv N$, $C_{1-4}$-alkyl, $C_{1-4}$-alkyl-$C(=O)NH_2$, $C_{1-4}$-alkyl-$C\equiv N$, $C_{1-4}$-alkyl-$NHC_{1-4}$-alkyl, $C_{1-4}$-alkyl-$NR^{20c}R^{20d}$, phenyl, phenyl-$C\equiv N$, 5-9 membered heteroaryl, 5-6 membered heteroaryl-$R^{25a}$, 5-6 membered heteroaryl-$(OH)_2$, 6-7 membered heterocycloalkyl, 6-7 membered heterocycloalkyl-$R^{25b}$, $-C\equiv N$, $-S(=O)_2C_{1-4}$-alkyl, $-S(=O)_2(5-6$ membered heterocycloalkyl), $-S(=O)_2(5-6$ membered heterocycloalkyl-$R^{20e}$), $-S(=O)_2NHC_{1-4}$-alkyl, $-S(=O)_2N(C_{1-4}$-alkyl$)_2$, $-S(=O)_2N(C_{2-4}$-alkynyl$)C_{1-4}$-alkyl, $-OCF_3$, $-NHC(=O)C_{1-4}$-alkyl, $-NHC(=O)C_{1-3}$-haloalkyl, $-N(C_{1-4}$-alkyl$)S(=O)_2C_{1-4}$-alkyl, $-N(C_{1-4}$-alkyl-$C\equiv N)S(=O)_2C_{1-4}$-alkyl, $-NHS(=O)_2R^{20f}$, and $-NHC(=O)N(C_{1-4}$-alkyl$)_2$, wherein $R^{20a}$ is chosen from $-C\equiv N$, $-C(=O)OH$, $-C(=O)OC_{1-4}$-alkyl, 5-6 membered heterocycloalkyl, $-OH$, $-OC_{1-4}$-alkyl, $-OCH_2$phenyl, $-C(=O)NH_2$, $-NH_2$, and $-NHC(=O)C_{1-4}$-alkyl, $R^{20b}$ is chosen from $-OH$, $-OC_{1-4}$-alkyl, cyclopropyl, $-C\equiv N$, $-N(C_{1-4}$-alkyl$)_2$, and 5-6 membered heterocycloalkyl optionally substituted by $C_{1-4}$-alkyl, $R^{20c}$ is chosen from H and $C_{1-4}$-alkyl, $R^{20d}$ is chosen from $C_{1-4}$-alkyl-OH, and $-C(=O)C_{1-4}$-alkyl, $R^{25a}$ is chosen from $C_{1-4}$-alkyl, $C_{1-3}$-haloalkyl, $C_{1-4}$-alkyl-O—$C_{1-4}$-alkyl, $-NHC_{1-4}$-alkyl, and $-OC_{1-4}$-alkyl, $R^{25b}$ is chosen from $C_{1-4}$-alkyl, $-C(=O)OH$, and 6 membered heterocycloalkyl substituted by $C_{1-4}$-alkyl, $R^{20e}$ is chosen from $-OH$, $C_{1-4}$-alkyl, and $-N(C_{1-4}$-alkyl$)_2$, and $R^{20f}$ is chosen from $C_{1-4}$-alkyl, $C_{1-3}$-haloalkyl, and cyclopropyl. In another embodiment, the $R^2$ group is optionally substituted by one or more members independently chosen from $-OC_{1-6}$-alkyl, $-C(=O)NH_2$, $-C(=O)NH(C_{1-6}$-alkyl), 6-membered heterocycloalkyl, $-S(=O)_2NH(C_{1-6}$-alkyl), $-NHS(=O)_2(C_{1-6}$-alkyl), $-NHS(=O)_2(C_{1-6}$-fluoroalkyl), and $-NHS(=O)_2(C_{3-6}$-cycloalkyl). In another embodiment, the $R^2$ group is optionally substituted by one or more members independently chosen from $-C(=O)NH_2$, $-C(=O)NH(C_{1-6}$-alkyl), and 6-membered heterocycloalkyl. In another embodiment, the $R^2$ group is optionally substituted by one or more members independently chosen from F, Cl, Br, $-NO_2$, $-OH$, $-OCF_3$, $-OCH_2C\equiv N$, $-OCH_2CH_2C\equiv N$, $-OCH_3$, $-OCH_2CH_3$, $-OCH_2C(=O)OCH_3$, $-OCH_2CH(OH)CH_2OH$, $-O(CH_2)_2$-morpholinyl, $-O(CH_2)_2OH$, $-O(CH_2)_2OCH_3$, $-OCH_2C(=O)NH_2$, $-OCH_2C(=O)OH$, $-OCH_2C\equiv CH$, $-OCH_2C=CH_2$, $-O(CH_2)_2NH_2$, $-O(CH_2)_2NHC(=O)CH_3$, $-O$-tetrahydrofuranyl, $-OCH_2$-tetrahydrofuranyl, $-O$-tetrahydropyranyl, $-O(CH_2)_3O$-benzyl, $=O$, $-C(=O)-CH_3$, $-C(=O)OCH(CH_3)_2$, $-C(=O)O(CH_2)_2OCH_3$, $-C(=O)OCH_3$, $-C(=O)OCH_2CH_3$, $-C(=O)NH_2$, $-C(=O)NHCH_3$, $-C(=O)NH(CH_2)_2OH$, $-C(=O)N(CH_3)_2$, $-C(=O)NH(CH_2)_2$-pyrrolidinyl, $-C(=O)NHCH_2$-cyclopropyl, $-C(=O)NH(CH_2)_2$-N-methylpiperazinyl, $-C(=O)NH(CH_2)_2C\equiv N$, $-C(=O)N(CH_3)(CH_2)_2C\equiv N$, $-C(=O)NHCH_2C\equiv N$, $-C(=O)NHCH_2C\equiv CH$, $-C(=O)N(CH_3)CH_2C\equiv CH$, $-C(=O)NH(CH_2)_2CH_3$, $-C(=O)NHCH_2CH(CH_3)_2$, $-C(=O)NH(CH_2)_3CH_3$, $-C(=O)NHCH(CH_3)_2$, $-C(=O)NHCH_2CH_3$, $-C(=O)NH(CH_2)_2N(CH_3)_2$, $-C(=O)NHCH_2$-cyclopropyl, $-C(=O)NH(CH_2)_2OCH_3$, $-C(=O)NH(CH_2)_3OCH_3$, $-C(=O)NH(CH_2)_4N(CH_3)_2$, $-C(=O)NH(CH_2)_3N(CH_3)_2$, $-NH_2$, $-N(CH_3)_2$, $-NHCH_3$, $-N(CH_3)(CH_2)_2C\equiv N$, methyl, ethyl, t-butyl, $-CF_3$, $-CH_2C(=O)NH_2$, $-CH_2N(Et)(CH_2)_2OH$, $-CH_2NHCH_3$, $-CH_2N(CH_3)C(=O)CH_3$, $-CH_2NHC(=O)CH_3$, $-CH_2NH(CH_2)_2OH$, $-CH_2CH_2C\equiv N$, $-CH_2C\equiv N$, phenyl, phenyl-$C\equiv N$, 2-thiazolyl, 5-oxazolyl, N-methoxyethyl-2-imidazolyl, pyrazolyl, 5-methyl-1,3,4-thiadiazol-2-yl, 2-pyrazinyl, 3-methyl-5-(1,3,4-oxadiazolyl), 3-ethylamino-5-(1,3,4-oxadiazolyl), 3-methyl-5-(1,2,4-oxadiazolyl), 3-methyl-1,2,4-triazol-5-yl, 1-methyl-4-pyrazolyl, 5-methyl-2-(1,3,4-thiadiazolyl), 5-methyloxazol-2-yl, 2-pyrimidinyl, 2,4-dihydroxypyrimidinyl, 3-pyridyl, 2-pyridyl, 3-methyl-2-pyridyl, 4-methyl-2-pyridyl, 5-methyl-2-pyridyl, 6-methyl-2-pyridyl, 3-methoxy-2-pyridyl, 3-trifluoromethyl-2-pyridyl, 4-trifluoromethyl-2-imidazolyl, 1-methyl-2-imidazolyl, 2-imidazolyl, 1-ethoxymethyl-2-imidazolyl, benzimidazolyl, piperidinyl, morpholinyl, 2-oxa-5-aza-bicyclo[2.2.1]hept-5-yl, 5-ethyl-2,5-diaza-bicyclo[2.2.1]hept-2-yl, piperidine-4-carboxylic acid, 4-methylpiperazin-1-yl, 4-isopropyl-piperazin-1-yl, 4-(4-methyl-piperazin-1-yl)-piperidin-1-yl, 4-(1-methyl-piperidin-4-yl)-piperazin-1-yl, $-C\equiv N$, $-SO_2CH(CH_3)_2$, $-SO_2(3$-hydroxypyrrolidin-1-yl), $-SO_2CH_3$, $-SO_2$-morpholin-4-yl, $-SO_2(4$-methylpiperazin-1-yl), $-SO_2$-pyrrolidin-1-yl, $-SO_2(3$-(dimethylamino)pyrrolidin-1-yl), $-SO_2(3$-methylpyrrolidin-1-yl), $-SO_2NHCH_3$, $-SO_2N(CH_3)_2$, $-SO_2N($propynyl$)CH_3$, $-OCF_3$, $-NHC(=O)CH_3$, $-NHC(=O)CF_3$, $-NHSO_2CH_2CF_3$, $-NHSO_2CH_3$, $-N(CH_2C\equiv N)SO_2CH_3$, $-N(CH_3)SO_2CH_3$, $-N(CH_2CH_3)SO_2CH_3$, $-NHSO_2CH_2CH_3$, $-NHSO_2$-cyclopropyl, $-NHSO_2CH(CH_3)_2$, and $-NHC(=O)N(CH_3)_2$. In another embodiment, the $R^2$ group is optionally substituted by one or more members independently chosen from F, Cl, $-OH$, $-OCH_3$, $-C(=O)CH_3$, $-C(=O)OCH(CH_3)_2$, $-C(=O)NH_2$, $-C(=O)NHCH_3$, $-C(=O)NH(CH_2)_2OH$, $-C(=O)NHCH(CH_3)_2$, $-C(=O)NHCH_2CH_3$, $-C(=O)NH($cyclopropyl$)$, $-NH_2$, methyl, 1-methyl-2-imidazolyl, benzazepinyl, pyrazolyl, 2-imidazolyl, 1-ethoxymethyl-2-imidazolyl, 2-pyridyl, morpholinyl, piperidinyl, $-SO_2NHCH_3$, $-SO_2N($propynyl$)CH_3$, $-NHC(=O)CH_3$, $-NHC(=O)CF_3$, $-NHSO_2CH_3$, $-NHSO_2CH_2CF_3$, $-NHSO_2CH_2CH_3$, $-NHSO_2($cyclopropyl$)$, $-NHSO_2CH(CH_3)_2$, and $-NHC(=O)N(CH_3)_2$. In another embodiment, the $R^2$ group is optionally substituted by one or more members independently chosen from —OCH$_3$, —C(=O)NH$_2$, —C(=O)NHCH$_3$, —C(=O)NH(CH$_2$)$_2$OH, —C(=O)NHCH(CH$_3$)$_2$, —C(=O)NHCH$_2$CH$_3$, —C(=O)NH(cyclopropyl), morpholinyl, —SO$_2$NHCH$_3$, —SO$_2$N(propynyl)CH$_3$, —NHSO$_2$CH$_3$, —NHSO$_2$CH$_2$CF$_3$, —NHSO$_2$CH$_2$CH$_3$, —NHSO$_2$(cyclopropyl), and —NHSO$_2$CH(CH$_3$)$_2$. In another embodiment, the R$^2$ group is optionally substituted by one or more members independently chosen from —C(=O)NH$_2$, —C(=O)NHCH$_3$, —C(=O)NHCH(CH$_3$)$_2$, —C(=O)NHCH$_2$CH$_3$, and morpholinyl.

In another embodiment, R$^2$ is as defined in any of the above embodiments, except that R$^2$ is not:
(a) 5-15 membered heteroaryl containing at least one O or S ring atom, or
(b) 5-15 membered heteroaryl containing at least one O or S ring atom, wherein said 5-15 membered heteroaryl is substituted by 1-4 members independently selected from the group consisting of halogen, —NO$_2$, —OR$^{20}$, —C(=O)R$^{20}$, —C(=O)OR$^{20}$, —C(=O)NR$^{22}$R$^{23}$, —NR$^{20}$R$^{21}$, C$_{1-6}$-alkyl, —C$_{1-6}$-alkyl-OR$^{20}$, C$_{1-6}$-alkyl-NR$^{22}$R$^{23}$, C$_{1-6}$-haloalkyl, C$_{6-15}$-aryl, 5-15 membered heteroaryl, C$_{3-10}$ cycloalkyl, 3-15 membered heterocycloalkyl, -3-15 membered heterocycloalkyl-C$_{1-6}$-alkyl, -3-15 membered heterocycloalkyl-OR$^{20}$, pseudohalogen, —S(=O)$_n$R$^{20}$, —S(=O)$_2$NR$^{22}$R$^{23}$, —OC(=O)R$^{20}$, —NR$^{20}$C(=O)R$^{21}$, —NR$^{20}$C(=O)OR$^{21}$, —NR$^{20}$S(=O)$_2$R$^{21}$, —NR$^{20}$C(=O)NR$^{22}$R$^{23}$, and —NR$^{20}$S(=O)$_2$NR$^{22}$R$^{23}$.

In another embodiment, R$^2$ is chosen from:
(a) C$_{1-6}$-alkyl, and
(b) mono- or polysubstituted C$_{1-6}$ alkyl, wherein each substituent is selected from the group consisting of halogen, —NO$_2$, —OR$^{20}$, —(=O)X$^0$, —C(=O)OX$^0$, —C(=O)NX$^0$X$^1$, —C(=O)N(C$_{1-6}$-alkyl-OH)X$^0$, —NX$^0$X$^1$, pseudohalogen, —S(=O)$_n$X$^0$, —S(=O)$_2$NX$^0$X$^1$, —OCH$_2$F, —OCHF$_2$, —OCF$_3$, —NHOH, —OC(=O)X$^0$, —OC(=O)NX$^0$X$^1$, —NR$^{20}$C(=O)X$^1$, —NR$^{20}$C(=O)OX$^1$, —NR$^{20}$S(=O)$_2$X$^1$, —NR$^{20}$C(=O)NX$^0$X$^1$, —NR$^{20}$S(=O)$_2$NX$^0$X$^1$, and —SCF$_3$, wherein X$^0$ and X$^1$ at each occurrence are independently selected from the group consisting of hydrogen and C$_{1-6}$-alkyl.

In another embodiment, R$^2$ is as defined in any of the above embodiments, except that R$^2$ is not:
(a) a fused bicyclic unsaturated C$_{9-10}$ cycloalkyl group,
(b) a mono or polysubstituted fused bicyclic unsaturated C$_{9-10}$ cycloalkyl group, wherein each substituent is independently selected from the group consisting of halogen, —NO$_2$, —OR$^{20}$, —C(=O)R$^{20}$, —C(=O)OR$^{20}$, —C(=O)NR$^{22}$R$^{23}$, —C(=O)N(C$_{1-6}$-alkyl-OH)R$^{20}$, —NR$^{20}$R$^{21}$, C$_{1-6}$-alkyl, —C$_{1-6}$-alkyl-OR$^{20}$, —C$_{1-6}$-alkyl-NR$^{22}$R$^{23}$, C$_{1-6}$-fluoroalkyl, —CN, —SR$^{20}$, —S(=O)$_2$R$^{20}$, —S(=O)$_2$NR$^{22}$R$^{23}$, —OCH$_2$F, —OCHF$_2$, —OCF$_3$, —NR$^{20}$C(=O)R$^{21}$, —NR$^{20}$C(=O)OR$^{21}$, —NR$^{20}$S(=O)$_2$R$^{21}$, —NR$^{20}$C(=O)NR$^{22}$R$^{23}$, —NR$^{20}$S(=O)$_2$NR$^{22}$R$^{23}$, and —SCF$_3$,
(c) a fused bicyclic unsaturated 9-10 membered heterocycloalkyl group containing 1-4 heteroatoms selected from the group consisting of N, S, and O,
(d) a mono or polysubstituted fused bicyclic unsaturated 9-10 membered heterocycloalkyl group containing 1-4 heteroatoms selected from the group consisting of N, S, and O, wherein each substituent is independently selected from the group consisting of halogen, —NO$_2$, —OR$^{20}$, —C(=O)R$^{20}$, —C(=O)OR$^{20}$, —C(=O)NR$^{22}$R$^{23}$, —C(=O)N(C$_{1-6}$-alkyl-OH)R$^{20}$, —NR$^{20}$R$^{21}$, C$_{1-6}$-alkyl, —C$_{1-6}$-alkyl-OR$^{20}$, —C$_{1-6}$-alkyl-NR$^{22}$R$^{23}$, C$_{1-6}$-fluoroalkyl, —CN, —SR$^{20}$, —S(=O)$_2$R$^{20}$, —S(=O)$_2$NR$^{22}$R$^{23}$, —OCH$_2$F, —OCHF$_2$, —OCF$_3$, —NR$^{20}$C(=O)R$^{21}$, —NR$^{20}$C(=O)OR$^{21}$, —NR$^{20}$S(=O)$_2$R$^{21}$, —NR$^{20}$C(=O)NR$^{22}$R$^{23}$, —NR$^{20}$S(=O)$_2$NR$^{22}$R$^{23}$, and —SCF$_3$,
(e) a fused bicyclic C$_{9-10}$ aryl group,
(f) a mono or polysubstituted fused bicyclic C$_{9-10}$ aryl group, wherein each substituent is independently selected from the group consisting of halogen, —NO$_2$, —OR$^{20}$, —C(=O)R$^{20}$, —C(=O)OR$^{20}$, —C(=O)NR$^{22}$R$^{23}$, —C(=O)N(C$_{1-6}$-alkyl-OH)R$^{20}$, —NR$^{20}$R$^{21}$, C$_{1-6}$-alkyl, —C$_{1-6}$-alkyl-OR$^{20}$, —C$_{1-6}$-alkyl-NR$^{22}$R$^{23}$, C$_{1-6}$-fluoroalkyl, —CN, —SR$^{20}$, —S(=O)$_2$R$^{20}$, —S(=O)$_2$NR$^{22}$R$^{23}$, —OCH$_2$F, —OCHF$_2$, —OCF$_3$, —NR$^{20}$C(=O)R$^{21}$, —NR$^{20}$C(=O)OR$^{21}$, —NR$^{20}$S(=O)$_2$R$^{21}$, —NR$^{20}$C(=O)NR$^{22}$R$^{23}$, —NR$^{20}$S(=O)$_2$NR$^{22}$R$^{23}$, and —SCF$_3$,
(g) a fused bicyclic 9-10 membered heteroaryl group,
(h) a mono or polysubstituted fused bicyclic 9-10 membered heteroaryl group, wherein each substituent is independently selected from the group consisting of halogen, —NO$_2$, —OR$^{20}$, —C(=O)R$^{20}$, —C(=O)OR$^{20}$, —C(=O)NR$^{22}$R$^{23}$, —C(=O)N(C$_{1-6}$-alkyl-OH)R$^{20}$, —NR$^{20}$R$^{21}$, C$_{1-6}$-alkyl, —C$_{1-6}$-alkyl-OR$^{20}$, —C$_{1-6}$-alkyl-NR$^{22}$R$^{23}$, C$_{1-6}$-fluoroalkyl, —CN, —SR$^{20}$, —S(=O)$_2$R$^{20}$, —S(=O)$_2$NR$^{22}$R$^{23}$, —OCH$_2$F, —OCHF$_2$, —OCF$_3$, —NR$^{20}$C(=O)R$^{21}$, —NR$^{20}$C(=O)OR$^{21}$, —NR$^{20}$S(=O)$_2$R$^{21}$, —NR$^{20}$C(=O)NR$^{22}$R$^{23}$, —NR$^{20}$S(=O)$_2$NR$^{22}$R$^{23}$, and —SCF$_3$.

In another embodiment, R$^2$ is as defined in any of the above embodiments, except that R$^2$ is none of the following:
(a) indolyl;
(b) mono or polysubstituted indolyl, wherein each substituent is independently selected from the group consisting of C$_{1-6}$-alkyl, C$_{1-6}$-alkyl-OR, C$_{1-6}$-alkyl-NR$_2$, and dimethyldioxolanyl, wherein R at each occurrence is independently chosen from H and C$_{1-3}$-alkyl;
(c) benzotriazolyl;
(d) mono or disubstituted benzotriazolyl, wherein each substituent is independently selected from the group consisting of C$_{1-6}$-alkyl groups;
(e) phenyl having the following substitution pattern:
  (i) ortho positions independently chosen from H, halogen, and —CF$_3$,
  (ii) meta positions independently chosen from H, halogen, ethynyl, —O(C$_{1-6}$-alkyl), —C(=O)(C$_{1-3}$-alkyl), and pyrazolyl, and
  (iii) para position chosen from halogen, —O(C$_{1-6}$-alkyl), —O(phenyl), —C(=O)(C$_{1-3}$-alkyl), C$_{1-6}$-alkyl, CF$_3$, pyrazolyl, morpholinyl, piperazinyl, and —S(=O)$_2$NH$_2$; or
(f) phenyl having the following substitution pattern:
  (i) ortho positions independently chosen from H, halogen, and —CF$_3$,
  (ii) meta positions independently chosen from halogen, ethynyl, —O(C$_{1-6}$-alkyl), —C(=O)(C$_{1-3}$-alkyl), and pyrazolyl, and
  (iii) para position chosen from H, halogen, —O(C$_{1-6}$-alkyl), —O(phenyl), —C(=O)(C$_{1-3}$-alkyl), C$_{1-6}$-alkyl, CF$_3$, pyrazolyl, morpholinyl, piperazinyl, and —S(=O)$_2$NH$_2$.

In another embodiment, R$^2$ is as defined in any of the above embodiments, except that R$^2$ is not C$_{1-2}$-alkyl substituted by any of the following:
(a) indolyl;
(b) mono or polysubstituted indolyl, wherein each substituent is independently selected from the group consisting of $C_{1-6}$-alkyl, $C_{1-6}$-alkyl-OR, $C_{1-6}$-alkyl-$NR_2$, and dimethyldioxolanyl, wherein R at each occurrence is independently chosen from H and $C_{1-3}$-alkyl;
(c) benzotriazolyl;
(d) mono or disubstituted benzotriazolyl, wherein each substituent is independently selected from the group consisting of $C_{1-6}$-alkyl groups;
(e) phenyl having the following substitution pattern:
  (i) ortho positions independently chosen from H, halogen, and —$CF_3$,
  (ii) meta positions independently chosen from H, halogen, ethynyl, —O($C_{1-6}$-alkyl), —C(=O)($C_{1-3}$-alkyl), and pyrazolyl, and
  (iii) para position chosen from halogen, —O($C_{1-6}$-alkyl), —O(phenyl), —C(=O)($C_{1-3}$-alkyl), $C_{1-6}$-alkyl, $CF_3$, pyrazolyl, morpholinyl, piperazinyl, and —S(=O)$_2NH_2$; or
(f) phenyl having the following substitution pattern:
  (i) ortho positions independently chosen from H, halogen, and —$CF_3$,
  (ii) meta positions independently chosen from halogen, ethynyl, —O($C_{1-6}$-alkyl), —C(=O)($C_{1-3}$-alkyl), and pyrazolyl, and
  (iii) para position chosen from H, halogen, —O($C_{1-6}$-alkyl), —O(phenyl), —C(=O)($C_{1-3}$-alkyl), $C_{1-6}$-alkyl, $CF_3$, pyrazolyl, morpholinyl, piperazinyl, and —S(=O)$_2NH_2$.

In another embodiment, $R^2$ is as defined in any of the above embodiments, except that $R^2$ is none of the following:
(a) mono or polysubstituted $C_{1-6}$ alkyl, wherein each substituent is independently selected from the group consisting of:
  (i) —OR,
  (ii) —C(=O)-4-7 membered heterocycloalkyl optionally substituted by 1-4 $C_{1-6}$-alkyl groups,
  (iii) —C(=O)OR,
  (iv) —C(=O)$NR_2$,
  (v) —C(=O)N($C_{2-4}$-alkyl-OH)H,
  (vi) —$NX_2$,
  (vii) pyrrolyl,
  (viii) imidazolyl,
  (ix) pyrazolyl,
  (x) pyridyl,
  (xi) pyrimidinyl,
  (xii) pyrazinyl,
  (xiii) indolyl,
  (xiv) benzimidazolyl,
  (xv) quinuclidinyl,
  (xvi) 3-hydroxy-1,3-dihydroindol-2-on-3-yl,
  (xvii) 4-7 membered heterocycloalkyl unsubstituted or substituted by no substituent other than —OR or $C_{1-6}$-alkyl,
  (xviii) cyano,
  (xix) —S(=O)$_n$R,
  (xx) —OC(=O)R,
  (xxi) —NRC(=O)R,
  (xxii) —NRC(=O)OR,
  (xxiii) —NRS(=O)$_2$R,
  (xxiv) —NXC(=O)$NX_2$, and
  (xxv) —$NXSO_2NX_2$,
  wherein R at each occurrence is independently chosen from H, $C_{1-6}$-alkyl and $C_{6-15}$-aryl, and wherein X at each occurrence is independently chosen from H, $C_{1-6}$-alkyl, $C_{6-15}$-aryl, and pyridyl;

(b) a group of formula Q

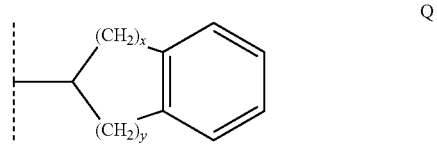

mono or polysubstituted in the $C_{6-15}$-aryl ring, wherein each substituent is independently selected from the group consisting of —C(=O)OR and —C(=O)$NR_2$, wherein R at each occurrence is independently chosen from H and $C_{1-6}$-alkyl, and
optionally additionally mono or disubstituted in the alkylene moiety, wherein each substituent is independently selected from the group consisting of $C_{1-6}$-alkyl groups,
wherein
x and y in formula X are independently 0, 1, or 2, and x+y≧2;
(c) mono or polysubstituted cyclopropyl, wherein each substituent is independently selected from the group consisting of —C(=O)-4-7 membered heterocycloalkyl optionally substituted by 1-4 $C_{1-6}$-alkyl groups, —C(=O)OR, and —C(=O)$NR_2$, wherein R at each occurrence is independently chosen from H and $C_{1-6}$-alkyl;
(d) mono or polysubstituted $C_{4-10}$ cycloalkyl, wherein each substituent is independently selected from the group consisting of:
  (i) —OR,
  (ii) —C(=O)OR,
  (iii) —$NR_2$,
  (iv) $C_{1-6}$-alkyl, and
  (v) $C_{1-6}$-alkyl-OR,
  wherein R at each occurrence is independently selected from the group consisting of H, $C_{1-6}$-alkyl and $C_{6-15}$-aryl;
(e) $C_{5-7}$ cycloalkyl in which at least one methylene group in the cycloalkyl moiety is replaced by a carbonyl group;
(f) $C_{5-7}$ cycloalkyl in which at least one methylene group in the cycloalkyl moiety is replaced by a carbonyl group, wherein the $C_{5-7}$ cycloalkyl is substituted by one or more members independently selected from the group consisting of $C_{1-6}$-alkyl;
(g) 4-7 membered heterocycloalkyl;
(h) mono or polysubstituted 4-7 membered heterocycloalkyl, wherein each substituent is independently selected from the group consisting of
  (i) —OR,
  (ii) —C(=O)-4-7 membered heterocycloalkyl optionally substituted by 1-4 $C_{1-6}$-alkyl groups,
  (iii) —C(=O)OR,
  (iv) —C(=O)$NR_2$,
  (v) —$NR_2$,
  (vi) $C_{1-6}$-alkyl,
  (vii) —$C_{1-6}$-alkyl-OR,
  (viii) —$C_{1-6}$-alkyl-$NR_2$,
  (ix) —$C_{1-6}$-alkyl-3-15 membered heterocycloalkyl, wherein said 3-15 membered heterocycloalkyl is optionally substituted by 1-4 $C_{1-6}$-alkyl groups,
  (x) 3,4-dihydro-1H-quinazolin-2-on-3-yl optionally substituted by —OR,
  (xi) 1H-benzimidazol-2-on-1-yl optionally substituted by —OR,
  (xii) 4-7 membered heterocycloalkyl optionally substituted by $C_{1-6}$-alkyl or —OR, (xiii) cyano,
(xiv) —S(=O)$_n$R,
(xv) —OC(=O)R,
(xvi) —NRC(=O)R,
(xvii) —NRC(=O)OR,
(xviii) —NRS(=O)$_2$R,
(xix) —NXC(=O)NX$_2$, and
(xx) —NXSO$_2$NX$_2$,
  wherein R at each occurrence is independently selected from the group consisting of H, C$_{1-6}$-alkyl and C$_{6-15}$-aryl, and wherein X at each occurrence is independently chosen from H, C$_{1-6}$-alkyl, C$_{6-15}$-aryl, and pyridyl; or
(i) quinuclidinyl.

In another embodiment, R$^2$ is as defined in any of the above embodiments, except that R$^2$ is not mono or polysubstituted C$_{4-10}$ cycloalkyl, wherein each substituent is independently selected from the group consisting of:
(i) —OR,
(ii) —C(=O)-4-7 membered heterocycloalkyl optionally substituted by 1-4 C$_{1-6}$-alkyl groups,
(iii) —C(=O)OR,
(iv) —C(=O)NR$_2$,
(v) —NR$_2$,
(vi) C$_{1-6}$-alkyl,
(vii) —C$_{1-6}$-alkyl-OR,
(viii) —C$_{1-6}$-alkyl-NR$_2$,
(ix) —C$_{1-6}$-alkyl-3-15 membered heterocycloalkyl, wherein said 3-15 membered heterocycloalkyl is optionally substituted by 1-4 C$_{1-6}$-alkyl groups,
(x) 3,4-dihydro-1H-quinazolin-2-on-3-yl optionally substituted by —OR,
(xi) 1H-benzimidazol-2-on-1-yl optionally substituted by —OR,
(xii) 4-7 membered heterocycloalkyl optionally substituted by C$_{1-6}$-alkyl or —OR,
(xiii) cyano,
(xiv) —S(=O)$_n$R,
(xv) —OC(=O)R,
(xvi) —NRC(=O)R,
(xvii) —NRC(=O)OR,
(xviii) —NRS(=O)$_2$R,
(xix) —NXC(=O)NX$_2$, and
(xx) —NXSO$_2$NX$_2$,
  wherein R at each occurrence is independently selected from the group consisting of H, C$_{1-6}$-alkyl and C$_{6-15}$-aryl, and wherein X at each occurrence is independently chosen from H, C$_{1-6}$-alkyl, C$_{6-15}$-aryl, and pyridyl.

In another embodiment, R$^2$ is as defined in any of the above embodiments, except that R$^2$ is none of the following:
(a) C$_{1-6}$-alkyl;
(b) mono or polysubstituted C$_{1-6}$-alkyl, wherein each substituent is independently selected from the group consisting of:
  (i) —OR,
  (ii) —C(=O)OR,
  (iii) —NR$_2$,
  (iv) 4-7 membered heterocycloalkyl optionally substituted by 1-2 C$_{1-6}$-alkyl groups,
  (v) C$_{6-15}$-aryl,
  (vi) cyano,
  (vii) —NRC(=O)R,
  (viii) —NRS(=O)$_2$X, and
  (ix) —NR$^{20}$C(=O)NR$^{22}$R$^{23}$,
    wherein R at each occurrence is independently selected from the group consisting of H and C$_{1-6}$-alkyl,
  and wherein X is selected from the group consisting of H, C$_{1-6}$-alkyl, and C$_{1-6}$-perfluoroalkyl;
(c) methyl substituted by fluoromethyl, chloromethyl, bromomethyl, difluoromethyl, or trifluoromethyl;
(d) C$_{3-7}$ cycloalkyl;
(e) C$_{3-5}$ alkenyl; or
(f) C$_{3-5}$ alkynyl.

In another embodiment, R$^2$ is as defined in any of the above embodiments, except that R$^2$ is not mono or polysubstituted C$_{1-6}$-alkyl, in which each substituent is independently selected from the group consisting of:
(i) —OR,
(ii) —C(=O)-4-7 membered heterocycloalkyl optionally substituted by 1-2 C$_{1-6}$-alkyl groups,
(iii) —C(=O)OR,
(iv) —C(=O)NR$_2$,
(v) —NR$_2$,
(vi) C$_{3-7}$ cycloalkyl,
(vii) 4-7 membered heterocycloalkyl optionally substituted by 1-4 C$_{1-6}$-alkyl groups,
(viii) C$_{6-15}$-aryl,
(ix) cyano,
(x) —S(=O)$_n$R,
(xi) —OC(=O)R,
(xii) —NRC(=O)R,
(xiii) —NRC(=O)OR,
(xiv) —NRS(=O)$_2$X,
(xv) —NR$^{20}$C(=O)NR$^{22}$R$^{23}$, and
(xvi) —NR$^{20}$SO$_2$NR$^{22}$R$^{23}$,
  wherein R at each occurrence is independently selected from the group consisting of H and C$_{1-6}$-alkyl,
  and wherein X is selected from the group consisting of H, C$_{1-6}$-alkyl, and C$_{1-6}$-perfluoroalkyl;

In another embodiment, R$^2$ is as defined in any of the above embodiments, except that R$^2$ is none of the following:
(a) C$_{1-6}$-alkyl;
(b) monosubstituted C$_{1-6}$-alkyl, wherein the substituent is selected from the group consisting of C$_{6-15}$-aryl, 5-15 membered heteroaryl optionally substituted by C$_{1-6}$-alkyl, 3-15 membered heterocycloalkyl optionally substituted by C$_{1-6}$-alkyl, and C$_{5-10}$ fused bicyclic or tricyclic cycloalkyl;
(c) C$_{6-15}$-aryl;
(d) mono, di, or trisubstituted C$_{6-15}$-aryl, wherein each substituent is independently selected from the group consisting of C$_{1-6}$-alkyl, —C$_{1-6}$-alkyl-3-15 membered heterocycloalkyl optionally substituted by C$_{1-6}$-alkyl, —C$_{1-6}$-alkyl-5-15 membered heteroaryl optionally substituted by C$_{1-6}$-alkyl, 3-15 membered heterocycloalkyl optionally substituted by C$_{1-6}$-alkyl, C$_{6-15}$-aryl, 5-15 membered heteroaryl, and C$_{3-7}$ cycloalkyl;
(e) 5-15 membered heteroaryl;
(f) mono, di, or trisubstituted 5-15 membered heteroaryl, wherein each substituent is independently selected from the group consisting of C$_{1-6}$-alkyl, —C$_{1-6}$-alkyl-3-15 membered heterocycloalkyl optionally substituted by C$_{1-6}$-alkyl, —C$_{1-6}$-alkyl-5-15 membered heteroaryl optionally substituted by C$_{1-6}$-alkyl, 3-15 membered heterocycloalkyl optionally substituted by C$_{1-6}$-alkyl, C$_{6-15}$-aryl, 5-15 membered heteroaryl, and C$_{3-7}$ cycloalkyl;
(g) 3-15 membered heterocycloalkyl;
(h) mono, di, or trisubstituted 3-15 membered heterocycloalkyl, wherein each substituent is independently selected from the group consisting of C$_{1-6}$-alkyl, —C$_{1-6}$-alkyl-3-15 membered heterocycloalkyl optionally substituted by C$_{1-6}$-alkyl, —C$_{1-6}$-alkyl-5-15 membered heteroaryl optionally substituted by $C_{1-6}$-alkyl, 3-15 membered heterocycloalkyl optionally substituted by $C_{1-6}$-alkyl, $C_{6-15}$-aryl, 5-15 membered heteroaryl, and $C_{3-7}$ cycloalkyl;

(i) $C_{5-10}$ fused bicyclic or tricyclic cycloalkyl; or (j) mono, di, or trisubstituted $C_{5-10}$ fused bicyclic or tricyclic cycloalkyl, wherein each substituent is independently selected from the group consisting of $C_{1-6}$-alkyl, —$C_{1-6}$-alkyl-3-15 membered heterocycloalkyl optionally substituted by $C_{1-6}$-alkyl, —$C_{1-6}$-alkyl-5-15 membered heteroaryl optionally substituted by $C_{1-6}$-alkyl, 3-15 membered heterocycloalkyl optionally substituted by $C_{1-6}$-alkyl, $C_{6-15}$-aryl, 5-15 membered heteroaryl, and $C_{3-7}$ cycloalkyl.

In another embodiment, $R^{12}$ is as defined in any of the above embodiments, except that $R^2$ is not monosubstituted phenyl, wherein the substituent is selected from the group consisting of —$C(=O)NR^{22}R^{23}$.

In another embodiment, $R^2$ is as defined in any of the above embodiments, except that $R^2$ is not a group of formula

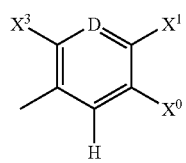

wherein

D is $=CX^2$— or $=N$—;

each of $X^0$, $X^1$, $X^2$, and $X^3$ are independently selected from the group consisting of hydrogen, hydroxy, $C_{1-6}$-alkyl, —$C_{1-6}$-alkyl-OH, —$C_{1-6}$-alkyl-O—$C_{1-6}$-alkyl, and $C_{3-8}$ cycloalkyl;

or each of $X^1$, $X^2$, and $X^3$ are independently selected from the group consisting of halogen, —$NO_2$, —O—$C_{1-6}$-alkyl, —O—$C_{1-6}$-alkynyl, —O—$C_{1-6}$-haloalkyl, —$C(=O)$—$C_{2-6}$-alkyl, —$C(=O)O$—$C_{2-6}$-alkyl, —$C(=O)OH$, —$C(=O)NR^{22}R^{23}$, —$C(=O)N(C_{1-6}$-alkyl-OH)$R^{20}$, —$NR^{20}R^{21}$, $C_{1-6}$-haloalkyl, —$C_{1-4}$-alkyl-5-15 membered heteroaryl optionally substituted by $C_{1-6}$-alkyl, $C_{6-15}$-aryl, 5-15 membered heteroaryl, 5-10 membered heterocycloalkyl, —$S(=O)_2NR^{22}R^{23}$, —$OCH_2F$, —$OCHF_2$, —$OCF_3$, —NHOH, and —$N(C_{1-6}$-alkyl)$C(=O)$—$C_{1-6}$-alkyl;

or $X^1$ and $X^2$ form together with the C-atoms to which they are attached $C_{6-15}$-aryl or a 5-10 membered heteroaryl residue comprising one or two heteroatoms selected from N, O and S;

or $X^1$ and $X^2$ form together with the C-atoms to which they are attached a 5-15 membered non-aromatic carbocyclic or heterocyclic residue, wherein the heterocyclic residue comprises 1-5 heteroatoms selected from N, O and S;

or $X^1$ and $X^2$ together form a residue of formula —$C(CH_3)$=CH—O—, —CH=CH—NH—, or —N=$C(CH_3)$—$C(CH_3)$=N—;

or $X^1$ and $X^2$ together form a residue of formula —CH=N—NH— and $X^3$ is —$SO_2NR^{22}R^{23}$.

In another embodiment, $R^2$ is as defined in any of the above embodiments, except that $R^2$ is not a group of formula

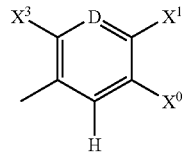

wherein

D is $=CX^2$— or $=N$—;

each of $X^0$, $X^1$, $X^2$, and $X^3$ are independently selected from the group consisting of hydrogen, hydroxy, $C_{1-6}$-alkyl, —$C_{1-6}$-alkyl-OH, —$C_{1-6}$-alkyl-O—$C_{1-6}$-alkyl, —$C_{1-6}$-alkyl-$NR^{22}R^{23}$, $C_{1-6}$-haloalkyl, and $C_{3-8}$ cycloalkyl;

or each of $X^1$, $X^2$, and $X^3$ are independently selected from the group consisting of halogen, —$NO_2$, —O—$C_{1-6}$-alkyl, —O—$C_{1-6}$-alkynyl, —O—$C_{1-6}$-haloalkyl, —$C(=O)$—$C_{2-6}$-alkyl, —$C(=O)O$—$C_{2-6}$-alkyl, —$C(=O)OH$, —$C(=O)NR^{22}R^{23}$, —$C(=O)N(C_{1-6}$-alkyl-OH)$R^{20}$, —$NR^{20}R^{21}$, $C_{1-6}$-haloalkyl, —$C_{1-4}$-alkyl-5-15 membered heteroaryl optionally substituted by $C_{1-6}$-alkyl, $C_{6-15}$-aryl, 5-15 membered heteroaryl, 5-10 membered heterocycloalkyl, 3-15 membered heterocycloalkyl-$C_{1-6}$-alkyl, 3-15 membered heterocycloalkyl-OH, 3-15 membered heterocycloalkyl-O—$C_{1-6}$-alkyl, —$S(=O)_2NR^{22}R^{23}$, —$OCH_2F$, —$OCHF_2$, —$OCF_3$, —NHOH, and —$N(C_{1-6}$-alkyl)$C(=O)$—$C_{1-6}$-alkyl;

or $X^1$ and $X^2$ form together with the C-atoms to which they are attached $C_{6-15}$-aryl or a 5-10 membered heteroaryl residue comprising one or two heteroatoms selected from N, O and S, wherein the $C_{6-15}$-aryl or 5-10 membered heteroaryl residue is optionally substituted by one or more substituents independently selected from the group consisting of halogen, —OH, $C_{1-6}$-alkyl, —O—$C_{1-6}$-alkyl, —$NO_2$, —CN, —COOH, —$C(=O)NH_2$, —$NR^{20}R^{21}$, $C_{3-6}$-cycloalkyl, 3-7 membered heterocycloalkyl, phenyl, and 5-6 membered heteroaryl;

or $X^1$ and $X^2$ form together with the C-atoms to which they are attached a 5-15 membered non-aromatic carbocyclic or heterocyclic residue, wherein the heterocyclic residue comprises 1-5 heteroatoms selected from N, O and S, and wherein the carbocyclic or heterocyclic residue is optionally substituted by one or more substituents independently selected from the group consisting of halogen, —OH, $C_{1-6}$-alkyl, —O—$C_{1-6}$-alkyl, —$NO_2$, —CN, —COOH, —$C(=O)NH_2$, —$NR^{20}R^{21}$, $C_{3-6}$-cycloalkyl, 3-7 membered heterocycloalkyl, phenyl, and 5-6 membered heteroaryl;

or $X^1$ and $X^2$ together form a residue of formula —$C(CH_3)$=CH—O—, —CH=CH—NH—, or —N=$C(CH_3)$—$C(CH_3)$=N—;

or $X^1$ and $X^2$ together form a residue of formula —CH=N—NH— and $X^3$ is —$SO_2NR^{22}R^{23}$.

In another embodiment, $R^2$ is $C_{6-15}$-aryl or 5-15 membered heteroaryl.

In another embodiment, $R^{20}$ and $R^{21}$ at each occurrence are independently chosen from H, $C_{1-6}$-alkyl, $C_{2-6}$-alkynyl, $C_{1-6}$-haloalkyl, $C_{6-15}$-aryl, 5-15 membered heteroaryl, $C_{3-10}$ cycloalkyl, and 3-15 membered heterocycloalkyl, in which said $C_{1-6}$-alkyl, $C_{2-6}$-alkynyl, $C_{1-6}$-haloalkyl, $C_{6-15}$-aryl, 5-15 membered heteroaryl, $C_{3-10}$ cycloalkyl, and 3-15 membered heterocycloalkyl groups are optionally substituted by one or more substituents independently chosen from $C_{1-6}$-alkyl, halogen, and —OH. In another embodiment, $R^{20}$ and $R^{21}$ at each occurrence are independently chosen from H, $C_{1-6}$-alkyl optionally substituted by —OH, $C_{2-6}$-alkynyl, $C_{1-6}$-haloalkyl, $C_{6-15}$-aryl, 5-15 membered heteroaryl, $C_{3-10}$ cycloalkyl, and 3-15 membered heterocycloalkyl optionally substituted by $C_{1-6}$-alkyl or —OH. In another embodiment, $R^{20}$ and $R^{21}$ at each occurrence are independently chosen from H, $C_{1-6}$-alkyl, $C_{1-6}$-alkyl-$R^{20a}$, $C_{1-6}$-alkyl-(OH)$_2$, $C_{2-6}$-alkenyl, $C_{2-6}$-alkynyl, $C_{1-6}$-haloalkyl, $C_{3-6}$ cycloalkyl, 5-6 membered heterocycloalkyl, and 5-6 membered heterocycloalkyl-$R^{20e}$, wherein $R^{20a}$ is chosen from —C≡N, —C(=O)OH, —C(=O)O$C_{1-6}$-alkyl, 5-6 membered heterocycloalkyl, —OH, —O$C_{1-6}$-alkyl, —OCH$_2$phenyl, —C(=O)NH$_2$, —NH$_2$, and —NHC(=O)$C_{1-6}$-alkyl, and $R^{20e}$ is chosen from —OH, $C_{1-6}$-alkyl, and —N($C_{1-6}$-alkyl)$_2$. In another embodiment, $R^{20}$ and $R^{21}$ at each occurrence are independently chosen from H, —CF$_3$, —CH$_2$CF$_3$, —CH$_2$C≡N, —CH$_2$CH$_2$C≡N, —CH$_3$, —CH$_2$CH$_3$, —CH(CH$_3$)$_2$, —CH$_2$C(=O)OCH$_3$, —CH$_2$CH(OH)CH$_2$OH, —(CH$_2$)$_2$-morpholinyl, —(CH$_2$)$_2$OH, —(CH$_2$)$_2$OCH$_3$, —CH$_2$C(=O)NH$_2$, —CH$_2$C(=O)OH, —CH$_2$C≡CH, —CH$_2$C=CH$_2$, —(CH$_2$)$_2$NH$_2$, —(CH$_2$)$_2$NHC(=O)CH$_3$, tetrahydrofuranyl, —CH$_2$-tetrahydrofuranyl, tetrahydropyranyl, —(CH$_2$)$_3$O-benzyl, 3-hydroxypyrrolidin-1-yl, morpholin-4-yl, 4-methylpiperazin-1-yl, pyrrolidin-1-yl, 3-(dimethylamino)pyrrolidin-1-yl, 3-methylpyrrolidin-1-yl, and cyclopropyl. In another embodiment, $R^{20}$ and $R^{21}$ at each occurrence are independently chosen from H, $C_{1-6}$-alkyl optionally substituted by —OH, $C_{1-6}$-haloalkyl, 5-15 membered heteroaryl, $C_{3-10}$ cycloalkyl, and 3-15 membered heterocycloalkyl optionally substituted by $C_{1-6}$-alkyl or —OH. In another embodiment, $R^{20}$ and $R^{21}$ at each occurrence are independently chosen from H, $C_{1-6}$-alkyl optionally substituted by —OH, $C_{1-6}$-haloalkyl, and 3-15 membered heterocycloalkyl optionally substituted by $C_{1-6}$-alkyl or —OH. In another embodiment, $R^{20}$ and $R^{21}$ at each occurrence are independently chosen from H, $C_{1-6}$-alkyl optionally substituted by —OH, $C_{1-6}$-haloalkyl, and 3-15 membered heterocycloalkyl. In another embodiment, $R^{20}$ and $R^{21}$ at each occurrence are independently chosen from H, $C_{1-6}$-alkyl, $C_{1-6}$-fluoroalkyl, and $C_{3-6}$-cycloalkyl. In another embodiment, $R^{20}$ and $R^{21}$ at each occurrence are independently chosen from H and $C_{1-6}$-alkyl.

In another embodiment, $R^{22}$ and $R^{23}$ at each occurrence are independently chosen from H, $C_{1-6}$-alkyl, $C_{2-6}$-alkynyl, $C_{1-6}$-haloalkyl, $C_{6-15}$-aryl, 5-15 membered heteroaryl, $C_{3-10}$ cycloalkyl, and 3-15 membered heterocycloalkyl, in which said $C_{1-6}$-alkyl, $C_{2-6}$-alkynyl, $C_{1-6}$-haloalkyl, $C_{6-15}$-aryl, 5-15 membered heteroaryl, $C_{3-10}$ cycloalkyl, and 3-15 membered heterocycloalkyl groups are optionally substituted by one or more substituents independently chosen from $C_{1-6}$-alkyl, halogen, and —OH; or $R^{22}$ and $R^{23}$ may form, together with the nitrogen atom to which they are attached, a 3-15 membered heterocycloalkyl group or a 5-15 membered heteroaryl group, in which said 3-15 membered heterocycloalkyl group or 5-15 membered heteroaryl group is optionally substituted by one or more substituents independently chosen from $C_{1-6}$-alkyl, halogen, and —OH. In another embodiment, $R^{22}$ and $R^{23}$ at each occurrence are independently chosen from H, $C_{1-6}$-alkyl optionally substituted by —OH, $C_{2-6}$-alkynyl, $C_{1-6}$-haloalkyl, $C_{6-15}$-aryl, 5-15 membered heteroaryl, $C_{3-10}$ cycloalkyl, and 3-15 membered heterocycloalkyl optionally substituted by —OH; or $R^{22}$ and $R^{23}$ may form, together with the nitrogen atom to which they are attached, a 3-15 membered heterocycloalkyl group or a 5-15 membered heteroaryl group, in which the heterocycloalkly group or 5-15 membered heteroaryl group may optionally be substituted by one or more members selected from $C_{1-6}$-alkyl. In another embodiment, $R^{22}$ and $R^{23}$ at each occurrence are independently chosen from H, $C_{1-6}$-alkyl, $C_{1-6}$-alkyl-$R^{20b}$, and $C_{2-6}$-alkynyl, wherein $R^{20b}$ is chosen from —OH, —O$C_{1-6}$-alkyl, cyclopropyl, —C≡N, —N($C_{1-6}$-alkyl)$_2$, and 5-6 membered heterocycloalkyl optionally substituted by $C_{1-6}$-alkyl. In another embodiment, $R^{22}$ and $R^{23}$ at each occurrence are independently chosen from H, —CH$_3$, —(CH$_2$)$_2$OH, —(CH$_2$)$_2$-pyrrolidinyl, —CH$_2$-cyclopropyl, —(CH$_2$)$_2$—N-methylpiperazinyl, —(CH$_2$)$_2$C≡N, —CH$_2$C≡N, —CH$_2$C≡CH, —(CH$_2$)$_2$CH$_3$, —CH$_2$CH(CH$_3$)$_2$, —(CH$_2$)$_3$CH$_3$, —CH$_2$CH$_3$, —(CH$_2$)$_2$N(CH$_3$)$_2$, —(CH$_2$)$_2$OCH$_3$, —(CH$_2$)$_3$OCH$_3$, —(CH$_2$)$_4$N(CH$_3$)$_2$, and —(CH$_2$)$_3$N(CH$_3$)$_2$. In another embodiment, $R^{22}$ and $R^{23}$ at each occurrence are independently chosen from H, $C_{1-6}$-alkyl optionally substituted by —OH, $C_{1-6}$-haloalkyl, 5-15 membered heteroaryl, $C_{3-10}$ cycloalkyl, and 3-15 membered heterocycloalkyl optionally substituted by —OH; or $R^{22}$ and $R^{23}$ may form, together with the nitrogen atom to which they are attached, a 3-15 membered heterocycloalkyl group or a 5-15 membered heteroaryl group, in which the heterocycloalkly group or 5-15 membered heteroaryl group may optionally be substituted by one or more members selected from $C_{1-6}$-alkyl. In another embodiment, $R^{22}$ and $R^{23}$ at each occurrence are independently chosen from H, $C_{1-6}$-alkyl optionally substituted by —OH, $C_{1-6}$-haloalkyl, and 3-15 membered heterocycloalkyl; or $R^{22}$ and $R^{23}$ may form, together with the nitrogen atom to which they are attached, a 3-15 membered heterocycloalkyl group or a 5-15 membered heteroaryl group. In another embodiment, $R^{22}$ and $R^{23}$ at each occurrence are independently chosen from H, $C_{1-6}$-alkyl optionally substituted by —OH, $C_{1-6}$-haloalkyl, and 3-15 membered heterocycloalkyl. In another embodiment, $R^{22}$ and $R^{23}$ at each occurrence are independently chosen from H, $C_{1-6}$-alkyl optionally substituted by —OH, $C_{2-6}$-alkynyl, $C_{1-6}$-haloalkyl, $C_{6-15}$-aryl, 5-15 membered heteroaryl, $C_{3-10}$ cycloalkyl, and 3-15 membered heterocycloalkyl optionally substituted by —OH. In another embodiment, $R^{22}$ and $R^{23}$ at each occurrence are independently chosen from H, $C_{1-6}$-alkyl, $C_{2-6}$-alkynyl, and $C_{3-6}$-cycloalkyl. In another embodiment, $R^{22}$ and $R^{23}$ at each occurrence are independently chosen from H and $C_{1-6}$-alkyl.

In another embodiment, $R^{25}$ at each occurrence are independently chosen from halogen, —NO$_2$, —OR$^{60}$, =O, —C(=O)R$^{60}$, —C(=O)OR$^{60}$, —C(=O)NR$^{62}$R$^{63}$, —NR$^{60}$R$^{61}$, $C_{1-6}$-alkyl, —$C_{1-6}$-alkyl-O—$C_{1-6}$-alkyl, $C_{1-6}$-haloalkyl, $C_{2-6}$-alkenyl, $C_{2-6}$-alkynyl, $C_{6-15}$-aryl-(R$^{77}$)$_x$, 5-15 membered heteroaryl-(R$^{77}$)$_x$, $C_{3-10}$ cycloalkyl-(R$^{77}$)$_x$, 3-15 membered heterocycloalkyl-(R$^{77}$)$_x$, pseudohalogen, —S(=O)$_n$R$^{60}$, —S(=O)$_2$NR$^{62}$R$^{63}$, —OCH$_2$F, —OCHF$_2$, —OCF$_3$, —NHOH, —OC(=O)R$^{60}$, —OC(=O)NR$^{62}$R$^{63}$, —OP(=O)(OH)$_2$, —NR$^{60}$C(=O)R$^{61}$, —NR$^{60}$C(=O)OR$^{61}$, —NR$^{60}$S(=O)$_2$R$^{61}$, —NR$^{60}$C(=O)NR$^{62}$R$^{63}$, —NR$^{60}$S(=O)$_2$NR$^{62}$R$^{63}$, and —SCF$_3$, wherein R$^{77}$ at each occurrence is independently chosen from $C_{1-6}$-alkyl. In another embodiment, $R^{25}$ at each occurrence is independently chosen from halogen, —NO$_2$, —OR$^{60}$, —C(=O)R$^{60}$, —C(=O)OR$^{60}$, —C(=O)NR$^{62}$R$^{63}$, —NR$^{60}$R$^{61}$, $C_{1-6}$-alkyl, —$C_{1-6}$-alkyl-O—$C_{1-6}$-alkyl, $C_{1-6}$-haloalkyl, $C_{2-6}$-alkenyl, $C_{2-6}$-alkynyl, $C_{6-15}$-aryl, 5-15 membered heteroaryl, $C_{3-10}$ cycloalkyl, 3-15 membered heterocycloalkyl, pseudohalogen, —S(=O)$_n$R$^{60}$, —S(=O)$_2$NR$^{62}$R$^{63}$, —OCH$_2$F, —OCHF$_2$, —OCF$_3$, —NHOH, —OC(=O)R$^{60}$, —OC(=O)NR$^{62}$R$^{63}$, —NR$^{60}$C(=O)R$^{61}$, —NR$^{60}$C(=O)OR$^{61}$, —NR$^{60}$S(=O)$_2$R$^{61}$, —NR$^{60}$C(=O)NR$^{62}$R$^{63}$, —NR$^{60}$S(=O)$_2$NR$^{62}$R$^{63}$, and —SCF$_3$. In another embodiment, $R^{25}$ at each occurrence is independently chosen from halogen, —NO$_2$, —OR$^{60}$, —C(=O)R$^{60}$, —C(=O)OR$^{60}$, —C(=O)NR$^{62}$R$^{63}$, —NR$^{60}$R$^{61}$, $C_{1-6}$-alkyl, —$C_{1-6}$alkyl-O—$C_{1-6}$-alkyl, $C_{1-6}$-haloalkyl, $C_{6-15}$-aryl, 5-15 membered heteroaryl, $C_{3-10}$ cycloalkyl, 3-15 membered heterocycloalkyl, —CN, —S(=O)$_2$R$^{60}$, —S(=O)$_2$NR$^{62}$R$^{63}$, —OCF$_3$, —OC(=O) R$^{60}$, —OC(=O)NR$^{62}$R$^{63}$, —NR$^{60}$C(=O)R$^{61}$, —NR$^{60}$C (=O)OR$^{61}$, —NR$^{60}$S(=O)$_2$R$^{61}$, and —NR$^{60}$C(=O) NR$^{62}$R$^{63}$. In another embodiment, R$^{25}$ at each occurrence is independently chosen from halogen, —C(=O)NH$_2$, —C≡N, —NHC$_{1-6}$-alkyl, —NR$^{20c}$R$^{20d}$, —OH, C$_{1-6}$-alkyl, C$_{1-6}$-haloalkyl, C$_{1-6}$-alkyl-O—C$_{1-6}$-alkyl, —OC$_{1-6}$-alkyl, —C(=O)OH, and 5-6 membered heterocycloalkyl optionally substituted by C$_{1-6}$-alkyl, wherein R$^{20c}$ is chosen from H and C$_{1-6}$-alkyl, R$^{20d}$ is chosen from C$_{1-6}$-alkyl-OH, and —C(=O)C$_{1-6}$-alkyl. In another embodiment, R$^{25}$ at each occurrence is independently chosen from halogen, —C(=O) NH$_2$, —C≡N, —NHC$_{1-6}$-alkyl, —NR$^{20c}$R$^{20d}$, —OH, C$_{1-6}$-alkyl, C$_{1-6}$-haloalkyl, C$_{1-6}$-alkyl-O—C$_{1-6}$-alkyl, —OC$_{1-6}$-alkyl, —C(=O)OH, and 6 membered heterocycloalkyl substituted by C$_{1-6}$-alkyl, wherein R$^{20c}$ is chosen from H and C$_{1-6}$-alkyl, R$^{20d}$ is chosen from C$_{1-6}$-alkyl-OH, and —C(=O)C$_{1-6}$-alkyl. In another embodiment, R$^{25}$ at each occurrence is independently chosen from F, —C(=O)NH$_2$, —N(Et)(CH$_2$)$_2$OH, —NHCH$_3$, —N(CH$_3$)C(=O)CH$_3$, —NHC(=O)CH$_3$, —NH(CH$_2$)$_2$OH, —C≡N, —(CH$_2$)$_2$OCH$_3$, —CH$_3$, —NHCH$_2$CH$_3$, —OH, —OCH$_3$, —CF$_3$, —CH$_2$OCH$_2$CH$_3$, —OCH$_2$CH$_3$, —C(=O)OH, —CH (CH$_3$)$_2$, 4-methyl-piperazin-1-yl, and 1-methyl-piperidin-4-yl. In another embodiment, R$^{25}$ at each occurrence is independently chosen from halogen, —OR$^{60}$, —C(=O)R$^{60}$, —C(=O)OR$^{60}$, —C(=O)NR$^{62}$R$^{63}$, —NR$^{60}$R$^{61}$, C$_{1-6}$-alkyl, —C$_{1-6}$-alkyl-O—C$_{1-6}$-alkyl, C$_{1-6}$-haloalkyl, C$_{6-15}$-aryl, 5-15 membered heteroaryl, 3-15 membered heterocycloalkyl, —CN, —S(=O)$_2$R$^{60}$, —S(=O)$_2$NR$^{62}$R$^{63}$, —OCF$_3$, —NR$^{60}$C(=O)R$^{61}$, —NR$^{60}$C(=O)OR$^{61}$, and —NR$^{60}$S (=O)$_2$R$^{61}$. In another embodiment, R$^{25}$ at each occurrence is independently chosen from halogen, —OR$^{60}$, —C(=O)R$^{60}$, —C(=O)NR$^{62}$R$^{63}$, —NR$^{60}$R$^{61}$, C$_{1-6}$-alkyl, —C$_{1-6}$-alkyl-O—C$_{1-6}$-alkyl, C$_{1-6}$-haloalkyl, 5-15 membered heteroaryl, 3-15 membered heterocycloalkyl, —S(=O)$_2$R$^{60}$, —S(=O)$_2$NR$^{62}$R$^{63}$, —NR$^{60}$C(=O)R$^{61}$, and —NR$^{60}$S (=O)$_2$R$^{61}$. In another embodiment, R$^{25}$ at each occurrence is independently chosen from —OR$^{60}$, —NR$^{60}$R$^{61}$, C$_{1-6}$-alkyl, and —C$_{1-6}$-alkyl-O—C$_{1-6}$-alkyl.

In another embodiment, R$^3$, R$^4$, and R$^5$ are independently chosen from H, halogen, —NO$_2$, —OR$^{30}$, —C(=O)R$^{30}$, —C(=O)OR$^{30}$, —C(=O)NR$^{32}$R$^{33}$, —NR$^{30}$R$^{31}$, C$_{1-6}$-alkyl, —C$_{1-6}$-alkyl-OR$^{30}$, —C$_{1-6}$-alkyl-NR$^{32}$R$^{33}$, —C$_{1-6}$-alkyl-C (=O)OR$^{30}$, —C$_{1-6}$-alkyl-CN, C$_{1-6}$-haloalkyl, C$_{2-6}$-alkenyl, C$_{2-6}$-alkynyl, C$_{6-15}$-aryl, 5-15 membered heteroaryl, C$_{3-10}$ cycloalkyl, 3-15 membered heterocycloalkyl, pseudohalogen, —S(=O)$_n$R$^{30}$, —S(=O)$_2$NR$^{32}$R$^{33}$, —OCH$_2$F, —OCHF$_2$, —OCF$_3$, —NHOH, —OC(=O)R$^{30}$, —OC(=O) NR$^{32}$R$^{33}$, —NR$^{30}$C(=O)R$^{31}$, —NR$^{30}$C(=O)OR$^{31}$, —NR$^{30}$S(=O)$_2$R$^{31}$, and —SCF$_3$. In another embodiment, R$^3$, R$^4$, and R$^5$ are independently chosen from H, halogen, —NO$_2$, —OR$^{30}$, —C(=O)R$^{30}$, —C(=O)OR$^{30}$, —C(=O) NR$^{32}$R$^{33}$, —NR$^{30}$R$^{31}$, C$_{1-6}$-alkyl, C$_{1-6}$-haloalkyl, 5-15 membered heteroaryl, 3-15 membered heterocycloalkyl, pseudohalogen, —S(=O)$_n$R$^{30}$, —S(=O)$_2$NR$^{32}$R$^{33}$, —OCF$_3$, —NHOH, —OC(=O)R$^{30}$, —OC(=O)NR$^{32}$R$^{33}$, —NR$^{30}$C(=O)R$^{31}$, —NR$^{30}$C(=O)OR$^{31}$, —NR$^{30}$ S(=O)$_2$R$^{31}$, —NR$^{30}$C(=O)NR$^{32}$R$^{33}$, and —NR$^{30}$ S(=O)$_2$NR$^{32}$R$^{33}$. In another embodiment, R$^3$, R$^4$, and R$^5$ are independently chosen from H, halogen, —NO$_2$, —OR$^{30}$, —C(=O)R$^{30}$, —C(=O)NR$^{32}$R$^{33}$, —NR$^{30}$R$^{31}$, C$_{1-6}$-alkyl, C$_{1-6}$-haloalkyl, pseudohalogen, —S(=O)R$^{30}$, —S(=O)$_2$NR$^{32}$R$^{33}$, —OCF$_3$, —OC(=O)R$^{30}$, —OC(=O) NR$^{32}$R$^{33}$, —NR$^{30}$C(=O)R$^{31}$, —NR$^{30}$C(=O)OR$^{31}$, —NR$^{30}$S(=O)$_2$R$^{31}$, and —NR$^{30}$C(=O)NR$^{32}$R$^{33}$. In another embodiment, R$^3$, R$^4$, and R$^5$ are independently chosen from H, halogen, —OR$^{30}$, —C(=O)R$^{30}$, —NR$^{30}$R$^{31}$, C$_{1-6}$-alkyl, and C$_{1-6}$-haloalkyl. In another embodiment, R$^3$, R$^4$, and R$^5$ are independently chosen from H, halogen, —OR$^{30}$, —C(=O)R$^{30}$, and —NR$^{30}$R$^{31}$. In another embodiment, R$^3$, R$^4$, and R$^5$ are independently chosen from H, halogen, —OC$_{1-6}$-alkyl, —OC$_{1-6}$-fluoroalkyl, —C(=O)C$_{1-6}$-alkyl, and —NH$_2$. In another embodiment, R$^3$, R$^4$, and R$^5$ are independently chosen from H, halogen, and —OC$_{1-6}$-alkyl. In another embodiment, R$^3$ is chosen from H, halogen, —OC$_{1-6}$-alkyl, and —OC$_{1-6}$-fluoroalkyl, R$^4$ is chosen from H, halogen, —C(=O)C$_{1-6}$-alkyl, and —NH$_2$, and R$^5$ is chosen from H, halogen, and —OC$_{1-6}$-alkyl. In another embodiment, R$^3$ is chosen from H, F, Cl, —OCH$_3$, and —OCH$_2$CF$_3$, R$^4$ is chosen from H, F, —C(=O)CH$_3$, and —NH$_2$, and R$^5$ is chosen from H, Cl, Br, and —OCH$_3$.

In another embodiment, R$^3$, R$^4$, and R$^5$ are defined as in any of the above embodiments, except that at least one of R$^3$, R$^4$, and R$^5$ is not hydrogen. In another embodiment, the compound is a compound of Formula I, and R$^3$ is defined as in any of the above embodiments, except that R$^3$ is not hydrogen or halogen when both of the following are simultaneously true:

(a) R$^4$ is hydrogen, C$_{1-6}$-alkyl, —O—C$_{1-6}$-alkyl, or halogen, and (b) R$^5$ is hydrogen.

In another embodiment, R$^{30}$ and R$^{31}$ at each occurrence are independently chosen from H, C$_{1-6}$-alkyl, C$_{2-6}$-alkynyl, C$_{1-6}$-haloalkyl, C$_{6-15}$-aryl, 5-15 membered heteroaryl, C$_{3-10}$ cycloalkyl, and 3-15 membered heterocycloalkyl, in which said C$_{1-6}$-alkyl, C$_{2-6}$-alkynyl, C$_{1-6}$-haloalkyl, C$_{6-15}$-aryl, 5-15 membered heteroaryl, C$_{3-10}$ cycloalkyl, and 3-15 membered heterocycloalkyl groups are optionally substituted by one or more substituents independently chosen from C$_{1-6}$-alkyl, halogen, and —OH. In another embodiment, R$^{30}$ and R$^{31}$ at each occurrence are independently chosen from H, C$_{1-6}$-alkyl optionally substituted by —OH, C$_{2-6}$-alkynyl, C$_{1-6}$-haloalkyl, C$_{6-15}$-aryl, 5-15 membered heteroaryl, C$_{3-10}$ cycloalkyl, and 3-15 membered heterocycloalkyl optionally substituted by C$_{1-6}$-alkyl or —OH. In another embodiment, R$^{30}$ and R$^{31}$ at each occurrence are independently chosen from H, C$_{1-6}$-alkyl optionally substituted by —OH, C$_{1-6}$-haloalkyl, 5-15 membered heteroaryl, C$_{3-10}$ cycloalkyl, and 3-15 membered heterocycloalkyl optionally substituted by C$_{1-6}$-alkyl or —OH. In another embodiment, R$^{30}$ and R$^{31}$ at each occurrence are independently chosen from H, C$_{1-6}$-alkyl optionally substituted by —OH, C$_{1-6}$-haloalkyl, and 3-15 membered heterocycloalkyl optionally substituted by C$_{1-6}$-alkyl or —OH. In another embodiment, R$^{30}$ and R$^{31}$ at each occurrence are independently chosen from H, C$_{1-6}$-alkyl optionally substituted by —OH, C$_{1-6}$-haloalkyl, and 3-15 membered heterocycloalkyl. In another embodiment, R$^{30}$ and R$^{31}$ at each occurrence are independently chosen from H, C$_{1-6}$-alkyl, and C$_{1-6}$-fluoroalkyl. In another embodiment, R$^{30}$ and R$^{31}$ at each occurrence are independently chosen from H and C$_{1-6}$-alkyl.

In another embodiment, R$^{32}$ and R$^{33}$ at each occurrence are independently chosen from H, C$_{1-6}$-alkyl, C$_{2-6}$-alkynyl, C$_{1-6}$-haloalkyl, C$_{6-15}$-aryl, 5-15 membered heteroaryl, C$_{3-10}$ cycloalkyl, and 3-15 membered heterocycloalkyl, in which said C$_{1-6}$-alkyl, C$_{2-6}$-alkynyl, C$_{1-6}$-haloalkyl, C$_{6-15}$-aryl, 5-15 membered heteroaryl, C$_{3-10}$ cycloalkyl, and 3-15 membered heterocycloalkyl groups are optionally substituted by one or more substituents independently chosen from C$_{1-6}$-alkyl, halogen, and —OH; or R$^{32}$ and R$^{33}$ may form, together with the nitrogen atom to which they are attached, a 3-15 membered heterocycloalkyl group or a 5-15 membered heteroaryl group, in which said 3-15 membered heterocycloalkyl group or 5-15 membered heteroaryl group is optionally substituted by one or more substituents independently chosen from $C_{1-6}$-alkyl, halogen, and —OH. In another embodiment, $R^{32}$ and $R^{33}$ at each occurrence are independently chosen from H, $C_{1-6}$-alkyl optionally substituted by —OH, $C_{2-6}$-alkynyl, $C_{1-6}$-haloalkyl, $C_{6-15}$-aryl, 5-15 membered heteroaryl, $C_{3-10}$ cycloalkyl, and 3-15 membered heterocycloalkyl optionally substituted by —OH; or $R^{32}$ and $R^{33}$ may form, together with the nitrogen atom to which they are attached, a 3-15 membered heterocycloalkyl group or a 5-15 membered heteroaryl group, in which the heterocycloalkly group or 5-15 membered heteroaryl group may optionally be substituted by one or more members selected from $C_{1-6}$-alkyl. In another embodiment, $R^{32}$ and $R^{33}$ at each occurrence are independently chosen from H, $C_{1-6}$-alkyl optionally substituted by —OH, $C_{1-6}$-haloalkyl, 5-15 membered heteroaryl, $C_{3-10}$ cycloalkyl, and 3-15 membered heterocycloalkyl optionally substituted by —OH; or $R^{32}$ and $R^{33}$ may form, together with the nitrogen atom to which they are attached, a 3-15 membered heterocycloalkyl group or a 5-15 membered heteroaryl group, in which the heterocycloalkly group or 5-15 membered heteroaryl group may optionally be substituted by one or more members selected from $C_{1-6}$-alkyl. In another embodiment, $R^{32}$ and $R^{33}$ at each occurrence are independently chosen from H, $C_{1-6}$-alkyl optionally substituted by —OH, $C_{1-6}$-haloalkyl, and 3-15 membered heterocycloalkyl; or $R^{32}$ and $R^{33}$ may form, together with the nitrogen atom to which they are attached, a 3-15 membered heterocycloalkyl group or a 5-15 membered heteroaryl group. In another embodiment, $R^{32}$ and $R^{33}$ at each occurrence are independently chosen from H, $C_{1-6}$-alkyl optionally substituted by —OH, $C_{2-6}$-alkynyl, $C_{1-6}$-haloalkyl, $C_{6-15}$-aryl, 5-15 membered heteroaryl, $C_{3-10}$ cycloalkyl, and 3-15 membered heterocycloalkyl optionally substituted by —OH. In another embodiment, $R^{32}$ and $R^{33}$ at each occurrence are independently chosen from H and $C_{1-6}$-alkyl.

In another embodiment, $R^{35}$ at each occurrence are independently chosen from halogen, —$NO_2$, —$OR^{60}$, =O, —C(=O)$R^{60}$, —C(=O)O$R^{60}$, —C(=O)N$R^{62}R^{63}$, —N$R^{60}R^{61}$, $C_{1-6}$-alkyl, —$C_{1-6}$-alkyl-O—$C_{1-6}$-alkyl, $C_{1-6}$-haloalkyl, $C_{2-6}$-alkenyl, $C_{2-6}$-alkynyl, $C_{6-15}$-aryl-$(R^{77})_x$, 5-15 membered heteroaryl-$(R^{77})_x$, $C_{3-10}$ cycloalkyl-$(R^{77})_x$, 3-15 membered heterocycloalkyl-$(R^{77})_x$, pseudohalogen, —S(=O)$_n R^{60}$, —S(=O)$_2$N$R^{62}R^{63}$, —$OCH_2F$, —$OCHF_2$, —$OCF_3$, —NHOH, —OC(=O)$R^{60}$, —OC(=O)N$R^{62}R^{63}$, —OP(=O)(OH)$_2$, —N$R^{60}$C(=O)$R^{61}$, —N$R^{60}$C(=O)O$R^{61}$, —N$R^{60}$S(=O)$_2 R^{61}$, —N$R^{60}$C(=O)N$R^{62}R^{63}$, —N$R^{60}$S(=O)$_2$N$R^{62}R^{63}$, and —$SCF_3$, wherein $R^{77}$ at each occurrence is independently chosen from $C_{1-6}$-alkyl. In another embodiment, $R^{35}$ at each occurrence is independently chosen from halogen, —$NO_2$, —$OR^{60}$, —C(=O)$R^{60}$, —C(=O)O$R^{60}$, —C(=O)N$R^{62}R^{63}$, —N$R^{60}R^{61}$, $C_{1-6}$-alkyl, —$C_{1-6}$-alkyl-O—$C_{1-6}$-alkyl, $C_{1-6}$-haloalkyl, $C_{2-6}$-alkenyl, $C_{2-6}$-alkynyl, $C_{6-15}$-aryl, 5-15 membered heteroaryl, $C_{3-10}$ cycloalkyl, 3-15 membered heterocycloalkyl, pseudohalogen, —S(=O)$_n R^{60}$, —S(=O)$_2$N$R^{62}R^{63}$, —$OCH_2F$, —$OCHF_2$, —$OCF_3$, —NHOH, —OC(=O)$R^{60}$, —OC(=O)N$R^{62}R^{63}$, —N$R^{60}$C(=O)$R^{61}$, —N$R^{60}$C(=O)O$R^{61}$, —N$R^{60}$S(=O)$_2 R^{61}$, —N$R^{60}$C(=O)N$R^{62}R^{63}$, —N$R^{60}$S(=O)$_2$N$R^{62}R^{63}$, and —$SCF_3$. In another embodiment, $R^{35}$ at each occurrence is independently chosen from halogen, —$NO_2$, —$OR^{60}$, —C(=O)$R^{60}$, —C(=O)O$R^{60}$, —C(=O)N$R^{62}R^{63}$, —N$R^{60}R^{61}$, $C_{1-6}$-alkyl, $C_{1-6}$-alkyl-O—$C_{1-6}$-alkyl, $C_{1-6}$-haloalkyl, $C_{6-15}$-aryl, 5-15 membered heteroaryl, $C_{3-10}$ cycloalkyl, 3-15 membered heterocycloalkyl, —CN, —S(=O)$_n R^{60}$, —S(=O)$_2$N$R^{62}R^{63}$, —$OCF_3$, —OC(=O)$R^{60}$, —OC(=O)N$R^{62}R^{63}$, —N$R^{60}$C(=O)$R^{61}$, —N$R^{60}$C(=O)O$R^{61}$, —N$R^{60}$S(=O)$_2 R^{61}$, and —N$R^{60}$C(=O)N$R^{62}R^{63}$. In another embodiment, $R^{35}$ at each occurrence is independently chosen from halogen, —$OR^{60}$, —C(=O)$R^{60}$, —C(=O)O$R^{60}$, —C(=O)N$R^{62}R^{63}$, —N$R^{60}R^{61}$, $C_{1-6}$-alkyl, $C_{1-6}$-haloalkyl, $C_{6-15}$-aryl, 5-15 membered heteroaryl, 3-15 membered heterocycloalkyl, —CN, —S(=O)$_2 R^{60}$, —S(=O)$_2$N$R^{62}R^{63}$, —$OCF_3$, —N$R^{60}$C(=O)$R^{61}$, —N$R^{60}$C(=O)O$R^{61}$, and —N$R^{60}$S(=O)$_2 R^{61}$. In another embodiment, $R^{35}$ at each occurrence is independently chosen from halogen, —$OR^{60}$, —C(=O)$R^{60}$, —C(=O)N$R^{62}R^{63}$, —N$R^{60}R^{61}$, $C_{1-6}$-alkyl, $C_{1-6}$-haloalkyl, 5-15 membered heteroaryl, 3-15 membered heterocycloalkyl, —S(=O)$_2 R^{60}$, —S(=O)$_2$N$R^{62}R^{63}$, —N$R^{60}$C(=O)$R^{61}$, and —N$R^{60}$S(=O)$_2 R^{61}$. In another embodiment, $R^{35}$ at each occurrence is independently chosen from halogen, $C_{1-6}$-alkyl, and —OH.

In another embodiment, $A^1$, $A^2$, $A^3$, $A^4$, and $A^5$ are independently chosen from —$CZ^1Z^2$—, —C(=O)—, —$NZ^3$—, —S—, —S(=O)—, —S(=O)$_2$—, and —O—. In another embodiment, $A^1$, $A^2$, $A^3$, $A^4$, and $A^5$ are independently chosen from —$CZ^1Z^2$—, —C(=O)—, —$NZ^3$—, —S—, —S(=O)$_2$—, and —O—. In another embodiment, $A^1$, $A^2$, $A^3$, and $A^5$ are independently chosen from —$CZ^1Z^2$—, —C(=O)—, —$NZ^3$—, —S—, —S(=O)—, —S(=O)$_2$—, and —O—, and $A^4$ is chosen from —$CZ^1Z^2$—, —(CZ$^1$Z$^2$)$_2$—, —C(=O)—, —$NZ^3$—, —S—, —S(=O)—, —S(=O)$_2$—, and —O—. In another embodiment, $A^1$, $A^2$, and $A^3$ are independently chosen from —$CZ^1Z^2$—, —C(=O)—, —$NZ^3$—, and —O—, $A^4$ is chosen from —$CZ^1Z^2$—, —(CZ$^1$Z$^2$)$_2$—, —C(=O)—, and —$NZ^3$—, and $A^5$ is chosen from —$CZ^1Z^2$—, —C(=O)—, —$NZ^3$—, —S—, —S(=O)$_2$—, and —O—. In another embodiment, $A^1$, $A^2$, and $A^3$ are independently chosen from —$CZ^1Z^2$—, —C(=O)—, —$NZ^3$—, and —O—, $A^4$ is chosen from —$CZ^1Z^2$—, —C(=O)—, and —$NZ^3$—, and $A^5$ is chosen from —$CZ^1Z^2$—, —C(=O)—, —$NZ^3$—, —S—, —S(=O)$_2$—, and —O—. In another embodiment, -$A^1$-$A^2$-$A^3$-$A^4$-$A^5$- is a group of formula —$CZ^1Z^2$—$CZ^1Z^2$—$CZ^1Z^2$—$CZ^1Z^2$—$CZ^1Z^2$—, —$CZ^1Z^2$—$CZ^1Z^2$—$CZ^1Z^2$—$CZ^1Z^2$—$NZ^3$—, —$CZ^1Z^2$—$CZ^1Z^2$—$CZ^1Z^2$—C(=O)—$NZ^3$—, —$CZ^1Z^2$—$CZ^1Z^2$—$CZ^1Z^2$—$NZ^3$—C(=O)—, —$CZ^1Z^2$—$CZ^1Z^2$—C(=O)—$CZ^1Z^2$—$CZ^1Z^2$—, —$CZ^1Z^2$—$CZ^1Z^2$—C(=O)—$NZ^3$—$CZ^1Z^2$—, —$CZ^1Z^2$—$CZ^1Z^2$—$NZ^3$—$CZ^1Z^2$—$CZ^1Z^2$—, —$CZ^1Z^2$—$CZ^1Z^2$—$CZ^1Z^2$—O—$CZ^1Z^2$—$CZ^1Z^2$—, —$CZ^1Z^2$—$CZ^1Z^2$—O—C(=O)—$NZ^3$—, —$CZ^1Z^2$—$CZ^1Z^2$—$NZ^3$—C(=O)—$CZ^1Z^2$—, —$CZ^1Z^2$—C(=O)—$NZ^3$—$CZ^1Z^2$—$CZ^1Z^2$—, —$CZ^1Z^2$—$NZ^3$—$CZ^1Z^2$—$CZ^1Z^2$—$NZ^3$—, —$CZ^1Z^2$—O—$CZ^1Z^2$—$CZ^1Z^2$—$NZ^3$—, —$CZ^1Z^2$—$NZ^3$—$CZ^1Z^2$—$CZ^1Z^2$—O—, —$CZ^1Z^2$—$NZ^3$—$CZ^1Z^2$—$CZ^1Z^2$—S—, —$CZ^1Z^2$—$NZ^3$—$CZ^1Z^2$—$CZ^1Z^2$—$SO_2$—, —$CZ^1Z^2$—$NZ^3$—$CZ^1Z^2$—C(=O)—$NZ^3$—, —$CZ^1Z^2$—$NZ^3$—C(=O)—$CZ^1Z^2$—$CZ^1Z^2$—, —$CZ^1Z^2$—$NZ^3$—C(=O)—$NZ^3$—$CZ^1Z^2$—, —C(=O)—$CZ^1Z^2$—$CZ^1Z^2$—$CZ^1Z^2$—$CZ^1Z^2$—, —C(=O)—$NZ^3$—$CZ^1Z^2$—$CZ^1Z^2$—$CZ^1Z^2$—, —C(=O)—$NZ^3$—$CZ^1Z^2$—$CZ^1Z^2$—O—, —C(=O)—$NZ^3$—$CZ^1Z^2$—$CZ^1Z^2$—$NZ^3$—, —$NZ^3$—$CZ^1Z^2$—$CZ^1Z^2$—$CZ^1Z^2$—$CZ^1Z^2$—, —$NZ^3$—$CZ^1Z^2$—$CZ^1Z^2$—$CZ^1Z^2$—O—, —$NZ^3$—$CZ^1Z^2$—$CZ^1Z^2$—$NZ^3$—$CZ^1Z^2$—, —$NZ^3$—$CZ^1Z^2$—$CZ^1Z^2$—$NZ^3$—C(=O)—, —$NZ^3$—$CZ^1Z^2$—C(=O)—$NZ^3$—$CZ^1Z^2$—, —$NZ^3$—C(=O)—$CZ^1Z^2$—$CZ^1Z^2$—$CZ^1Z^2$—, —$NZ^3$—C(=O)—$CZ^1Z^2$—$CZ^1Z^2$—, —$NZ^3$—C(=O)—$CZ^1Z^2$—$NZ^3$—$CZ^1Z^2$—, —$NZ^3$—C(=O)—O—$CZ^1Z^2$—$CZ^1Z^2$—, —O—$CZ^1Z^2$—$CZ^1Z^2$—$CZ^1Z^2$—$CZ^1Z^2$—, —O—$CZ^1Z^2$—$CZ^1Z^2$—$CZ^1Z^2$—O—, —O—$CZ^1Z^2$—$CZ^1Z^2$—$CZ^1Z^2$—$NZ^3$—, —O—$CZ^1Z^2$—$CZ^1Z^2$—O—, —$CZ^1Z^2$—$NZ^3$—C (=O)—CZ$^1$Z$^2$—CZ$^1$Z$^2$—NZ$^3$—, —CZ$^1$Z$^2$—NZ$^3$—CZ$^1$Z$^2$—CZ$^1$Z$^2$—CZ$^1$Z$^2$—, or —NZ$^3$—CZ$^1$Z$^2$—C(=O)—CZ$^1$Z$^2$—O—. In another embodiment, -A$^1$-A$^2$-A$^3$-A$^4$-A$^5$- is a group of formula —CZ$^1$Z$^2$—CZ$^1$Z$^2$—CZ$^1$Z$^2$—CZ$^1$Z$^2$—CZ$^1$Z$^2$—, —CZ$^1$Z$^2$CZ$^1$Z$^2$—CZ$^1$Z$^2$—CZ$^1$Z$^2$—NZ$^3$—, —CZ$^1$Z$^2$CZ$^1$Z$^2$—CZ$^1$Z$^2$—C(=O)—NZ$^3$—, —CZ$^1$Z$^2$—CZ$^1$Z$^2$—CZ$^1$Z$^2$—NZ$^3$—C(=O)—, —CZ$^1$Z$^2$—CZ$^1$Z$^2$—C(=O)—CZ$^1$Z$^2$—CZ$^1$Z$^2$—, —CZ$^1$Z$^2$—CZ$^1$Z$^2$—NZ$^3$—CZ$^1$Z$^2$—CZ$^1$Z$^2$—, —CZ$^1$Z$^2$—CZ$^1$Z$^2$—O—CZ$^1$Z$^2$—CZ$^1$Z$^2$—, —CZ$^1$Z$^2$—CZ$^1$Z$^2$—NZ$^3$—C(=O)—CZ$^1$Z$^2$—, —CZ$^1$Z$^2$—NZ$^3$—CZ$^1$Z$^2$—CZ$^1$Z$^2$—NZ$^3$—, —CZ$^1$Z$^2$—O—CZ$^1$Z$^2$—CZ$^1$Z$^2$—NZ$^3$—, —CZ$^1$Z$^2$—NZ$^3$—CZ$^1$Z$^2$—CZ$^1$Z$^2$—O—, —CZ$^1$Z$^2$—NZ$^3$—CZ$^1$Z$^2$—CZ$^1$Z$^2$—S—, —CZ$^1$Z$^2$—NZ$^3$—CZ$^1$Z$^2$—CZ$^1$Z$^2$—SO$_2$—, —CZ$^1$Z$^2$—NZ$^3$—C(=O)—NZ$^3$—CZ$^1$Z$^2$—, —C(=O)—NZ$^3$—CZ$^1$Z$^2$—CZ$^1$Z$^2$—CZ$^1$Z$^2$—, —C(=O)—NZ$^3$—CZ$^1$Z$^2$—CZ$^1$Z$^2$—NZ$^3$—, —NZ$^3$—CZ$^1$Z$^2$—CZ$^1$Z$^2$—NZ$^3$—CH$_2$—, —NZ$^3$—CZ$^1$Z$^2$—CZ$^1$Z$^2$—NZ$^3$—C(=O)—, —NZ$^3$—C(=O)—CZ$^1$Z$^2$—CZ$^1$Z$^2$—CZ$^1$Z$^2$—, —O—CZ$^1$Z$^2$—CZ$^1$Z$^2$—NZ$^3$—C(=O)—, or —O—CZ$^1$Z$^2$—CZ$^1$Z$^2$—CZ$^1$Z$^2$—O—. In another embodiment, -A$^1$-A$^2$-A$^3$-A$^4$-A$^5$- is a group of formula —CH$_2$—CZ$^1$Z$^2$—CH$_2$—CH$_2$—CH$_2$—, —CH$_2$—CH$_2$—CZ$^1$Z$^2$—CH$_2$—CH$_2$—, —CH$_2$—CH$_2$—CZ$^1$Z$^2$—CH$_2$—, —CZ$^1$Z$^2$—CH$_2$—CH$_2$—CH$_2$—NZ$^3$—, —CZ$^1$Z$^2$—CH$_2$—CZ$^1$Z$^2$—C(=O)—NZ$^3$—, —CH$_2$—CH$_2$—CH$_2$—NZ$^3$—C(=O)—, —CH$_2$—CH$_2$—C(=O)—CH$_2$—CH$_2$—, —CH$_2$—CH$_2$—C(=O)—NZ$^1$—CZ$^1$Z$^2$—, —CH$_2$—CH$_2$—NZ$^3$—CH$_2$—CH$_2$—, —CH$_2$—CH$_2$—O—CH$_2$—CH$_2$—, —CH$_2$—CH$_2$—O—C(=O)—NZ$^3$—, —CH$_2$—CH$_2$—NZ$^3$—C(=O)—CZ$^1$Z$^2$—, —CH$_2$—C(=O)—NZ$^3$—CH$_2$—CH$_2$—, —CH$_2$—NZ$^3$—CH$_2$—CH$_2$—NZ$^3$—, —CH$_2$—O—CH$_2$—CH$_2$—NZ$^3$—, —CH$_2$—NZ$^3$—CH$_2$—CH$_2$—O—, —CH$_2$—NZ$^3$—CH$_2$—CH$_2$—S—, —CH$_2$—NZ$^3$—CH$_2$—CH$_2$—SO$_2$—, —CH$_2$—NZ$^3$—CH$_2$—C(=O)—NZ$^3$—, —CZ$^1$Z$^2$—NZ$^3$—C(=O)—CH$_2$—CH$_2$—, —CH$_2$—NZ$^3$—C(=O)—CH=CH—, —CH$_2$—NZ$^3$—C(=O)—NZ$^3$—CH$_2$—, —C(=O)—CH$_2$—CZ$^1$Z$^2$—CH$_2$—CH$_2$—, —C(=O)—NZ$^3$—CH$_2$—CH$_2$—CH$_2$—, —C(=O)—NZ$^3$—CH$_2$—CH$_2$—O—, —C(=O)—NZ$^3$—CZ$^1$Z$^2$—CZ$^1$Z$^2$—NZ$^3$—, —NZ$^3$—CH$_2$—CZ$^1$Z$^2$—CH$_2$—CZ$^1$Z$^2$—, —NZ$^3$—CH$_2$—CZ$^1$Z$^2$—CH$_2$—O—, —NZ$^3$—CH$_2$—CH$_2$—NZ$^3$—CH$_2$—, —NZ$^3$—CH$_2$—CH$_2$—NZ$^3$—C(=O)—, —NZ$^3$—CH$_2$—C(=O)—NZ$^3$—CH$_2$—, —NZ$^3$—C(=O)—CH$_2$—CH$_2$—CZ$^1$Z$^2$—, —NZ$^3$—C(=O)—CH$_2$—CH$_2$—O—, —NZ$^3$—C(=O)—CH$_2$—NZ$^3$—CZ$^1$Z$^2$—, —NZ$^3$—C(=O)—O—CH$_2$—CH$_2$—, —O—CH$_2$—CH$_2$—CH$_2$—CZ$^1$Z$^2$—, —O—CH$_2$—CH$_2$—NZ$^3$—C(=O)—, —O—CH$_2$—CZ$^1$Z$^2$—CH$_2$—NZ$^3$—, —O—CH$_2$—CH$_2$—CH$_2$—O—, —CH$_2$—NZ$^3$—C(=O)—CH$_2$—CH$_2$—NZ$^3$—, —CZ$^1$Z$^2$—NZ$^3$—CH$_2$—CH$_2$—CH$_2$—, —NZ$^3$—CZ$^1$Z$^2$—C(=O)—CH$_2$—O—, —NZ$^3$—CZ$^1$Z$^2$—CH=CH—O—, —NZ$^3$—CZ$^1$Z$^2$—CH$_2$—CH$_2$—CZ$^1$Z$^2$—, or —NZ$^3$—CZ$^1$Z$^2$—CH$_2$—NZ$^3$—CH$_2$—. In another embodiment, -A$^1$-A$^2$-A$^3$-A$^4$-A$^5$- is a group of formula —CH$_2$—CHZ$^1$—CH$_2$—CH$_2$—CH$_2$—, —CH$_2$—CH$_2$—CHZ$^1$—CH$_2$—CH$_2$—, —CH$_2$—CH$_2$—CH$_2$—CHZ$^1$—CH$_2$—, —CZ$^1$Z$^2$—CH$_2$—CH$_2$—CH$_2$—NZ$^3$—, —CZ$^1$Z$^2$—CH$_2$—CZ$^1$Z$^2$—C(=O)—NZ$^3$—, —CH$_2$—CH$_2$—CH$_2$—NZ$^3$—C(=O)—, —CH$_2$—C(=O)—CH$_2$—CH$_2$—, —CH$_2$—CH$_2$—C(=O)—NZ$^3$—CZ$^1$Z$^2$—, —CH$_2$—CH$_2$—NZ$^3$—CH$_2$—CH$_2$—, —CH$_2$—CH$_2$—O—CH$_2$—CH$_2$—, —CH$_2$—CH$_2$—O—C(=O)—NZ$^3$—, —CH$_2$—CH$_2$—NZ$^3$—C(=O)—CHZ$^1$—, —CH$_2$—C(=O)—NZ$^3$—CH$_2$—CH$_2$—, —CH$_2$—NZ$^3$—CH$_2$—CH$_2$—NZ$^3$—, —CH$_2$—O—CH$_2$—CH$_2$—NZ$^3$—, —CH$_2$—NZ$^3$—CH$_2$—CH$_2$—O—, —CH$_2$—NZ$^3$—CH$_2$—CH$_2$—S—, —CH$_2$—NH—CH$_2$—CH$_2$—SO$_2$—, —CH$_2$—NZ$^3$—CH$_2$—C(=O)—NH—, —CZ$^1$Z$^2$—NZ$^3$—C(=O)—CH$_2$—CH$_2$—, —CH$_2$—NZ$^3$—C(=O)—CH=CH—, —CH$_2$—NH—C(=O)—NH—CH$_2$—, —C(=O)—CH$_2$—CHZ$^1$—CH$_2$—CH$_2$—, —C(=O)—NZ$^3$—CH$_2$—CH$_2$—, —C(=O)—NH—CH$_2$—CH$_2$—O—, —C(=O)—NZ$^3$—CHZ$^1$—CHZ$^1$—NZ$^3$—, —NH—CH$_2$—CHZ$^1$—CH$_2$—CZ$^1$Z$^2$—, —NZ$^3$—CH$_2$—CZ$^1$Z$^2$—CH$_2$—O—, —NZ$^3$—CH$_2$—CH$_2$—NZ$^3$—CH$_2$—, —NZ$^3$—CH$_2$—CH$_2$—NZ$^3$—C(=O)—, —NZ$^3$—CH$_2$—C(=O)—NH—CH$_2$—, —NZ$^3$—C(=O)—CHZ$^1$—CH$_2$—CZ$^1$Z$^2$—, —NH—C(=O)—CH$_2$—CH$_2$—O—, —NZ$^3$—C(=O)—CH$_2$—NZ$^3$—CZ$^1$Z$^2$—, —NZ$^3$—C(=O)—O—CH$_2$—CH$_2$—, —O—CH$_2$—CH$_2$—CZ$^1$Z$^2$—, —O—CH$_2$—CH$_2$—NZ$^3$—C(=O)—, —O—CH$_2$—CZ$^1$Z$^2$—CH$_2$—NZ$^3$—, —O—CH$_2$—CH$_2$—CH$_2$—O—, —CH$_2$—NH—C(=O)—CH$_2$—CH$_2$—NZ$^3$—, —CZ$^1$Z$^2$—NZ$^3$—CH$_2$—CH$_2$—CH$_2$—, —NZ$^3$—CZ$^1$Z$^2$—C(=O)—CH$_2$—O—, —NZ$^3$—CZ$^1$Z$^2$—CH=CH—O—, —NZ$^3$—CZ$^1$Z$^2$—CH$_2$—CH$_2$—CZ$^1$Z$^2$—, or —NZ$^3$—CZ$^1$Z$^2$—CH$_2$—NH—CH$_2$—. In another embodiment, -A$^1$-A$^2$-A$^3$-A$^4$-A$^5$- is a group of formula —CH$_2$—CH$_2$—CZ$^1$Z$^2$—CH$_2$—CH$_2$—, —CZ$^1$Z$^2$—CH$_2$—CH$_2$—CH$_2$—NZ$^3$—, —CZ$^1$Z$^2$—CH$_2$—CZ$^1$Z$^2$—C(=O)—NZ$^3$—, —CH$_2$—CH$_2$—CH$_2$—NZ$^3$—C(=O)—, —CH$_2$—CH$_2$—C(=O)—CH$_2$—CH$_2$—, —CH$_2$—CH$_2$—NZ$^3$—CH$_2$—CH$_2$—, —CH$_2$—CH$_2$—O—CH$_2$—CH$_2$—, —CH$_2$—CH$_2$—NZ$^3$—C(=O)—CZ$^1$Z$^2$—, —CH$_2$—NZ$^3$—CH$_2$—CH$_2$—NZ$^3$—, —CH$_2$—O—CH$_2$—CH$_2$—NZ$^3$—, —CH$_2$—NH—CH$_2$—CH$_2$—O—, —CH$_2$—NZ$^3$—CH$_2$—CH$_2$—S—, —CH$_2$—NH—CH$_2$—CH$_2$—SO$_2$—, —CH$_2$—NH—C(=O)—NH—CH$_2$—, —C(=O)—NZ$^3$—CH$_2$—CH$_2$—CH$_2$—, —C(=O)—NZ$^3$—CZ$^1$Z$^2$—CZ$^1$Z$^2$—NZ$^3$—, —NZ$^3$—CH$_2$—CZ$^1$Z$^2$—CH$_2$—O—, —NZ$^3$—CH$_2$—CH$_2$—NZ$^3$—C(=O)—, —NZ$^3$—C(=O)—CH$_2$—CH$_2$—CH$_2$—, —O—CH$_2$—

$CH_2$—$NZ^3$—$C(=O)$—, —O—$CH_2$—$CH_2$—$CH_2$—O—, —$CHZ^1$—$CH_2$—$CH_2$—$CHZ^1$—$CH_2$—, —$CHZ^1$—$CH_2$—$NZ^3$—$CH_2$—$CHZ^1$—, —$CH_2$—O—$CH_2$—$CHZ^1$—$NZ^3$—, or —$CH_2$—$CHZ^1$—$CH_2$—$CH_2$—$CHZ^1$—. In another embodiment, -$A^1$-$A^2$-$A^3$-$A^4$-$A^5$- is a group of formula —$CH_2$—$CZ^1Z^2$—$CH_2$—$CH_2$—$CH_2$—, —$CH_2$—$CH_2$—$CZ^1Z^2$—$CH_2$—$CH_2$—, —$CH_2$—$CH_2$—$CH_2$—$CZ^1Z^2$—$CH_2$—, —$CZ^1Z^2$—$CH_2$—$CH_2$—$CH_2$—$NZ^3$—, —$CZ^1Z^2$—$CH_2$—$CZ^1Z^2$—$C(=O)$—$NZ^3$—, —$CH_2$—$CH_2$—$CH_2$—$NZ^3$—$C(=O)$—, —$CH_2$—$CH_2$—$C(=O)$—$CH_2$—$CH_2$—, —$CH_2$—$CH_2$—$C(=O)$—$NZ^3$—$CZ^1Z^2$—, —$CH_2$—$CH_2$—$NZ^3$—$CH_2$—$CH_2$—, —$CH_2$—$CH_2$—O—$CH_2$—$CH_2$—, —$CH_2$—$CH_2$—O—$C(=O)$—$NZ^3$—, —$CH_2$—$CH_2$—$NZ^3$—$C(=O)$—$CZ^1Z^2$—, —$CH_2$—$C(=O)$—$NZ^3$—$CH_2$—$CH_2$—, —$CH_2$—$NZ^3$—$CH_2$—$CH_2$—$NZ^3$—, —$CH_2$—O—$CH_2$—$CH_2$—$NZ^3$—, —$CH_2$—$NZ^3$—$CH_2$—$CH_2$—O—, —$CH_2$—$NZ^3$—$CH_2$—$CH_2$—S—, —$CH_2$—$NZ^3$—$CH_2$—$CH_2$—$SO_2$—, —$CH_2$—$NZ^3$—$CH_2$—$C(=O)$—$NZ^3$—, —$CZ^1Z^2$—$NZ^3$—$C(=O)$—$CH_2$—$CH_2$—, —$CH_2$—$NZ^3$—$C(=O)$—$CH$=$CH$—, —$CH_2$—$NZ^3$—$C(=O)$—$NZ^3$—$CH_2$—, —$C(=O)$—$CH_2$—$CZ^1Z^2$—$CH_2$—$CH_2$—, —$C(=O)$—$NZ^3$—$CH_2$—$CH_2$—$CH_2$—, —$C(=O)$—$NZ^3$—$CH_2$—$CH_2$—O—, —$C(=O)$—$NZ^3$—$CZ^1Z^2$—$CZ^1Z^2$—$NZ^3$—, —$NZ^3$—$CH_2$—$CZ^1Z^2$—$CH_2$—$CZ^1Z^2$—, —$NZ^3$—$CH_2$—$CZ^1Z^2$—$CH_2$—O—, —$NZ^3$—$CH_2$—$CH_2$—$NZ^3$—$CH_2$—, —$NZ^3$—$CH_2$—$NZ^3$—$C(=O)$—, —$NZ^3$—$CH_2$—$C(=O)$—$NZ^3$—$CH_2$—, —$NZ^3$—$C(=O)$—$CZ^1Z^2$—$CH_2$—$CZ^1Z^2$—, —$NZ^3$—$C(=O)$—$CH_2$—$CH_2$—O—, —$NZ^3$—$C(=O)$—$CH_2$—$NZ^3$—$CZ^1Z^2$—, —$NZ^3$—$C(=O)$—O—$CH_2$—$CH_2$—, —O—$CH_2$—$CH_2$—$CH_2$—$CZ^1Z^2$—, —O—$CH_2$—$CH_2$—$NZ^3$—$C(=O)$—, —O—$CH_2$—$CZ^1Z^2$—$CH_2$—$NZ^3$—, —O—$CH_2$—$CH_2$—$CH_2$—O—, —$CH_2$—$NZ^3$—$C(=O)$—$CH_2$—$CH_2$—$NZ^3$—, —$CZ^1Z^2$—$NZ^3$—$CH_2$—$CH_2$—$CH_2$—, —$NZ^3$—$CZ^1Z^2$—$C(=O)$—$CH_2$—O—, —$NZ^3$—$CZ^1Z^2$—$CH$=$CH$—O—, —$NZ^3$—$CZ^1Z^2$—$CH_2$—$CH_2$—$CZ^1Z^2$—, or —$NZ^3$—$CZ^1Z^2$—$CH_2$—$NZ^3$—$CH_2$—, wherein any two $Z^1$, $Z^2$, and $Z^3$ that are located on adjacent atoms may together form a bond between the atoms, each $Z^1$ and $Z^2$ may independently be chosen from H, halogen, $C_{1-6}$-alkyl, —$C_{1-6}$-alkyl-$OR^{73}$, —$NR^{40}R^{41}$, —$OR^{76}$, 5-7 membered heterocycloalkyl, 5-7 membered heterocycloalkyl-$R^{45}$, —$N(R^{76})C(=O)C_{1-6}$-alkyl, —$N(R^{76})C(=O)C_{1-6}$-haloalkyl, —$N(R^{76})C(=O)C_{1-6}$-alkyl-$N(R^{76})_2$, —$N(R^{76})C(=O)C_{1-6}$-alkyl-$OR^{76}$, —$N(R^{76})C(=O)$-(5-7 membered heterocycloalkyl), —$N(R^{76})C(=O)$—($C_{3-6}$-cycloalkyl), and —$N(R^{76})C(=O)OC_{1-6}$-alkyl, $R^{40}$ and $R^{41}$ are independently chosen from H, $C_{1-6}$-alkyl, $C_{1-4}$-haloalkyl, —$C_{1-6}$-alkyl-$OR^{76}$, —$C_{1-6}$-alkyl-$N(R^{76})_2$, and $C_{3-6}$-cycloalkyl, $R^{45}$ is chosen from —$OR^{76}$, $C_{1-6}$-alkyl, 5-7 membered heterocycloalkyl, and 5-7 membered heterocycloalkyl-$C_{1-6}$-alkyl, each $R^{76}$ is independently chosen from H and $C_{1-6}$-alkyl, $Z^3$ may be chosen from H, $C_{1-6}$-alkyl, —$C_{1-6}$-alkyl-$R^{45a}$, —$C_{1-6}$-alkyl-(O—$C_{1-6}$-alkyl)$_2$, —$C(=O)C_{1-6}$-alkyl, —$C(=O)C_{1-6}$-alkyl-$R^{45b}$, —$C(=O)C_{1-6}$-haloalkyl, —$C(=O)$-(5-7 membered heterocycloalkyl), —$C(=O)$-(5-7 membered heteroaryl), $C_{1-6}$-haloalkyl, —$C(=O)OC_{1-6}$-alkyl, —$C(=O)OC_{1-6}$-alkyl-$R^{45c}$, —$C(=O)$O-(5-7-membered heterocycloalkyl-$C_{1-6}$-alkyl), —$C(=O)N(R^{62})_2$, —$C_{1-6}$-haloalkyl-$OR^2$, $C_{2-6}$-alkenyl, $C_{2-6}$-alkynyl, and —$S(=O)_2$—$C_{1-6}$-alkyl, $R^{45a}$ is chosen from —$OR^{62}$, 5-7 membered heterocycloalkyl, $C_{3-6}$-cycloalkyl, 5-6 membered heteroaryl, 5-6 membered heteroaryl-$C_{1-6}$-alkyl, phenyl, —$SO_2$—$C_{1-6}$-alkyl, —$C(=O)NR^{62}R^{63}$, —$C(=O)OC_{1-6}$-alkyl-O—$C_{1-4}$-alkyl, —$C(=O)OR^{62}$, —$C(=O)$-(4-7 membered heterocycloalkyl), —$C(=O)$-(5-7 membered heterocycloalkyl-$C_{1-6}$-alkyl), —$OC(=O)C_{1-6}$-alkyl, —$OC(=O)C_{1-6}$-alkyl-$N(R^{62})_2$, —$OP(=O)(OH)_2$, —$N(R^{62})C(=O)$—$C_{1-6}$-alkyl, —$N(R^{62})_2$, phenyl, and —$C≡N$, $R^{45b}$ is chosen from —$OR^{62}$, 5-7 membered heterocycloalkyl, 5-10 membered heteroaryl-$(R^{79})_x$, and —$N(R^{62})_2$, $R^{45c}$ is chosen from —$OR^{62}$, phenyl, and —$N(R^{62})_2$, each $R^{62}$ and $R^{63}$ is independently chosen from H and $C_{1-6}$-alkyl, each $R^{79}$ is =O, and x is 0, 1, or 2. In another embodiment, -$A^1$-$A^2$-$A^3$-$A^4$-$A^5$- is a group of formula —$CH_2$—$CHZ^1$—$CH_2$—$CH_2$—$CH_2$—, —$CH_2$—$CH_2$—$CHZ^1$—$CH_2$—$CH_2$—, —$CH_2$—$CH_2$—$CHZ^1$—$CH_2$—, —$CZ^1Z^2$—$CH_2$—$CH_2$—$CH_2$—$NZ^3$—, —$CZ^1Z^2$—$CH_2$—$CZ^1Z^2$—$C(=O)$—$NZ^3$—, —$CH_2$—$CH_2$—$CH_2$—$NZ^3$—$C(=O)$—, —$CH_2$—$CH_2$—$C(=O)$—$CH_2$—$CH_2$—, —$CH_2$—$CH_2$—$C(=O)$—$NZ^3$—$CZ^1Z^2$—, —$CH_2$—$CH_2$—$NZ^3$—$CH_2$—$CH_2$—, —$CH_2$—$CH_2$—O—$CH_2$—$CH_2$—, —$CH_2$—$CH_2$—O—$C(=O)$—$NZ^3$—, —$CH_2$—$CH_2$—$NZ^3$—$C(=O)$—$CHZ^1$—, —$CH_2$—$C(=O)$—$NZ^3$—$CH_2$—$CH_2$—, —$CH_2$—$NZ^3$—$CH_2$—$CH_2$—$NZ^3$—, —$CH_2$—O—$CH_2$—$CH_2$—$NZ^3$—, —$CH_2$—$NZ^3$—$CH_2$—$CH_2$—O—, —$CH_2$—$NZ^3$—$CH_2$—$CH_2$—S—, —$CH_2$—$NZ^3$—$CH_2$—$CH_2$—$SO_2$—, —$CH_2$—$NZ^3$—$CH_2$—$C(=O)$—$NZ^3$—, —$CZ^1Z^2$—$NZ^3$—$C(=O)$—$CH_2$—$CH_2$—, —$CH_2$—$NZ^3$—$C(=O)$—$CH$=$CH$—, —$CH_2$—$NZ^3$—$C(=O)$—$NZ^3$—$CH_2$—, —$C(=O)$—$CH_2$—$CHZ^1$—$CH_2$—$CH_2$—, —$C(=O)$—$NZ^3$—$CH_2$—$CH_2$—$CH_2$—, —$C(=O)$—$NZ^3$—$CH_2$—$CH_2$—O—, —$C(=O)$—$NZ^3$—$CHZ^1$—$CHZ^1$—$NZ^3$—, —$NZ^3$—$CH_2$—$CHZ^1$—$CH_2$—$CZ^1Z^2$—, —$NZ^3$—$CH_2$—$CZ^1Z^2$—$CH_2$—O—, —$NZ^3$—$CH_2$—$CH_2$—$NZ^3$—$CH_2$—, —$NZ^3$—$CH_2$—$CH_2$—$NZ^3$—$C(=O)$—, —$NZ^3$—$CH_2$—$C(=O)$—$NZ^3$—$CH_2$—, —$NZ^3$—$C(=O)$—$CHZ^1$—$CH_2$—$CZ^1Z^2$—, —$NZ^3$—$C(=O)$—$CH_2$—$CH_2$—O—, —$NZ^3$—$C(=O)$—$CH_2$—$NZ^3$—$CZ^1Z^2$—, —$NZ^3$—$C(=O)$—O—$CH_2$—$CH_2$—, —O—$CH_2$—$CH_2$—$CH_2$—$CZ^1Z^2$—, —O—$CH_2$—$CH_2$—$NZ^3$—$C(=O)$—, —O—$CH_2$—$CZ^1Z^2$—$CH_2$—$NZ^3$—, —O—$CH_2$—$CH_2$—$CH_2$—O—, —$CH_2$—$NZ^3$—$C(=O)$—$CH_2$—$CH_2$—$NZ^3$—, —$CZ^1Z^2$—$NZ^3$—$CH_2$—$CH_2$—$CH_2$—, —$NZ^3$—$CZ^1Z^2$—$C(=O)$—$CH_2$—O—, —$NZ^3$—$CZ^1Z^2$—$CH$=$CH$—O—, —$NZ^3$—$CZ^1Z^2$—$CH_2$—$CH_2$—$CZ^1Z^2$—, or —$NZ^3$—$CZ^1Z^2$—$CH_2$—$NZ^3$—$CH_2$—, wherein any two $Z^1$, $Z^2$, and $Z^3$ that are located on adjacent atoms may together form a bond between the atoms, each $Z^1$ and $Z^2$ may independently be chosen from H, halogen, $C_{1-6}$-alkyl, —$C_{1-6}$-alkyl-$OR^{76}$, —$NR^{40}R^{41}$, —$OR^{76}$, 5-7 membered heterocycloalkyl, 5-7 membered heterocycloalkyl-$R^{45}$, —$N(R^{76})C(=O)C_{1-6}$-alkyl, —$N(R^{76})C(=O)C_{1-6}$-haloalkyl, —$N(R^{76})C(=O)C_{1-6}$-alkyl-$N(R^{76})_2$, —$N(R^{76})C(=O)C_{1-6}$-alkyl-$OR^{76}$, —$N(R^{76})C(=O)$-(5-7 membered heterocycloalkyl), —$N(R^{76})C(=O)$—($C_{3-6}$-cycloalkyl), and —$N(R^{76})C(=O)OC_{1-6}$-alkyl, $R^{40}$ and $R^{41}$ are independently chosen from H, $C_{1-6}$-alkyl, $C_{1-4}$-haloalkyl, —$C_{1-6}$-alkyl-$OR^{76}$, —$C_{1-6}$-alkyl-$N(R^{76})_2$, and $C_{3-6}$-cycloalkyl, $R^{45}$ is chosen from —$OR^{76}$, $C_{1-6}$-alkyl, 5-7 membered heterocycloalkyl, and 5-7 membered heterocycloalkyl-$C_{1-6}$-alkyl, each $R^{76}$ is independently chosen from H and $C_{1-6}$-alkyl, $Z^3$ may be chosen from H, $C_{1-6}$-alkyl, —$C_{1-6}$-alkyl-$R^{45a}$, —$C_{1-6}$-alkyl-(O—$C_{1-6}$-alkyl)$_2$, —$C(=O)C_{1-6}$-alkyl, —$C(=O)C_{1-6}$-alkyl-$R^{45b}$, —$C(=O)C_{1-6}$-haloalkyl, —$C(=O)$-(5-7 membered heterocycloalkyl), —$C(=O)$-(5-7 membered heteroaryl), $C_{1-6}$-haloalkyl, —$C(=O)OC_{1-6}$-alkyl, —$C(=O)OC_{1-6}$-alkyl-$R^{45c}$, —$C(=O)$O-(5-7-membered heterocycloalkyl-$C_{1-6}$-alkyl), —$C(=O)N(R^{62})_2$, —$C_{1-6}$-haloalkyl-$OR^{62}$, $C_{2-6}$-alkenyl, $C_{2-6}$-alkynyl, and —$S(=O)_2$—$C_{1-6}$-alkyl, $R^{45a}$ is chosen from —$OR^{62}$, 5-7 membered heterocycloalkyl, $C_{3-6}$-cycloalkyl, 5-6 membered heteroaryl, 5-6 membered heteroaryl-$C_{1-6}$-alkyl, phenyl, —$SO_2$—$C_{1-6}$-alkyl, —$C(=O)NR^{62}R^{63}$, —$C(=O)OC_{1-6}$-alkyl-O—$C_{1-4}$-alkyl, —$C(=O)OR^{62}$, —$C(=O)$-(4-7 membered heterocycloalkyl), —C(═O)-(5-7 membered heterocycloalkyl-$C_{1-6}$-alkyl), —OC(═O)$C_{1-6}$-alkyl, —OC(═O)$C_{1-6}$-alkyl-N($R^{62}$)$_2$, —OP(═O)(OH)$_2$, —N($R^{62}$)C(═O)—$C_{1-6}$-alkyl, —N($R^{62}$)$_2$, phenyl, and —C≡N, $R^{45b}$ is chosen from —O$R^{62}$, 5-7 membered heterocycloalkyl, 5-10 membered heteroaryl-($R^{79}$)$_x$, and —N($R^{62}$)$_2$, $R^{45c}$ is chosen from —O$R^{62}$, phenyl, and —N($R^{62}$)$_2$, each $R^{62}$ and $R^{63}$ is independently chosen from H and $C_{1-6}$-alkyl, each $R^{79}$ is ═O, and x is 0, 1, or 2. In another embodiment, -$A^1$-$A^2$-$A^3$-$A^4$-$A^5$- is a group of formula —CH$_2$—CHZ$^1$—CH$_2$—CH$_2$—CH$_2$—, —CH$_2$—CH$_2$—CHZ$^1$—CH$_2$—CH$_2$—, —CH$_2$—CH$_2$—CH$_2$—CHZ$^1$—CH$_2$—, —CZ$^1$Z$^2$—CH$_2$—CH$_2$—CH$_2$—NZ$^3$—, —CZ$^1$Z$^2$—CH$_2$—CZ$^1$Z$^2$—C(═O)—NZ$^3$—, —CH$_2$—CH$_2$—CH$_2$—NZ$^3$—C(═O)—, —CH$_2$—CH$_2$—C(═O)—CH$_2$—CH$_2$—, —CH$_2$—CH$_2$—C(═O)—NH—CZ$^1$Z$^2$—, —CH$_2$—CH$_2$—NZ$^3$—CH$_2$—CH$_2$—, —CH$_2$—CH$_2$—O—CH$_2$—CH$_2$—, —CH$_2$—CH$_2$—O—C(═O)—NZ$^3$—, —CH$_2$—CH$_2$—NZ$^3$—C(═O)—CHZ$^1$—, —CH$_2$—C(═O)—NZ$^3$—CH$_2$—CH$_2$—, —CH$_2$—NZ$^3$—CH$_2$—CH$_2$—NZ$^3$—, —CH$_2$—O—CH$_2$—CH$_2$—NZ$^3$—, —CH$_2$—NZ$^3$—CH$_2$—CH$_2$—O—, —CH$_2$—NZ$^3$—CH$_2$—CH$_2$—S—, —CH$_2$—NH—CH$_2$—CH$_2$—SO$_2$—, —CH$_2$—NZ$^3$—CH$_2$—C(═O)—NH—, —CZ$^1$Z$^2$—NZ$^3$—C(═O)—CH$_2$—CH$_2$—, —CH$_2$—NZ$^3$—C(═O)—CH═CH—, —CH$_2$—NH—C(═O)—NH—CH$_2$—, —C(═O)—CH$_2$—CHZ$^1$—CH$_2$—CH$_2$—, —C(═O)—NZ$^3$—CH$_2$—CH$_2$—CH$_2$—, —C(═O)—NH—CH$_2$—CH$_2$—O—, —C(═O)—NZ$^3$—CHZ$^1$—CHZ$^1$—NZ$^3$—, —NH—CH$_2$—CHZ$^1$—CH$_2$—CZ$^1$Z$^2$—, —NZ$^3$—CH$_2$—CZ$^1$Z$^2$—CH$_2$—O—, —NZ$^3$—CH$_2$—CH$_2$—NZ$^3$—CH$_2$—, —NZ$^3$—CH$_2$—CH$_2$—NZ$^3$—C(═O)—, —NZ$^3$—CH$_2$—C(═O)—NH—CH$_2$—, —NZ$^3$—C(═O)—CHZ$^1$—CH$_2$—CZ$^1$Z$^2$—, —NH—C(═O)—CH$_2$—CH$_2$—O—, —NZ$^3$—C(═O)—CH$_2$—NZ$^3$—CZ$^1$Z$^2$—, —NZ$^3$—C(═O)—O—CH$_2$—CH$_2$—, —O—CH$_2$—CH$_2$—CH$_2$—CZ$^1$Z$^2$—, —O—CH$_2$—CH$_2$—NZ$^3$—C(═O)—, —O—CH$_2$—CZ$^1$Z$^2$—CH$_2$—NZ$^3$—, —O—CH$_2$—CH$_2$—CH$_2$—O—, —CH$_2$—NH—C(═O)—CH$_2$—CH$_2$—NZ$^3$—, —CZ$^1$Z$^2$—NZ$^3$—CH$_2$—CH$_2$—, —NZ$^3$—CZ$^1$Z$^2$—C(═O)—CH$_2$—O—, —NZ$^3$—CZ$^1$Z$^2$—CH═CH—O—, —NZ$^3$—CZ$^1$Z$^2$—CH$_2$—CH$_2$—CZ$^1$Z$^2$—, or —NZ$^3$—CZ$^1$Z$^2$—CH$_2$—NH—CH$_2$—, wherein any two $Z^1$, $Z^2$, and $Z^3$ that are located on adjacent atoms may together form a bond between the atoms, each $Z^1$ and $Z^2$ may independently be chosen from H, halogen, $C_{1-6}$-alkyl, —$C_{1-6}$-alkyl-O$R^{76}$, —N$R^{40}R^{41}$, —O$R^{76}$, 5-7 membered heterocycloalkyl, 5-7 membered heterocycloalkyl-$R^{45}$, —N($R^{76}$)C(═O)$C_{1-6}$-alkyl, —N($R^{76}$)C(═O)$C_{1-6}$-haloalkyl, —N($R^{76}$)C(═O)$C_{1-6}$-alkyl-N($R^{76}$)$_2$, —N($R^{76}$)C(═O)$C_{1-6}$-alkyl-O$R^{76}$, —N($R^{76}$)C(═O)-(5-7 membered heterocycloalkyl), —N($R^{76}$)C(═O)—($C_{3-6}$-cycloalkyl), and —N($R^{76}$)C(═O)O$C_{1-6}$-alkyl, $R^{40}$ and $R^{41}$ are independently chosen from H, $C_{1-6}$-alkyl, $C_{1-4}$-haloalkyl, —$C_{1-6}$-alkyl-O$R^{76}$, —$C_{1-6}$-alkyl-N($R^{76}$)$_2$, and $C_{3-6}$-cycloalkyl, $R^{45}$ is chosen from —O$R^{76}$, $C_{1-6}$-alkyl, 5-7 membered heterocycloalkyl, and 5-7 membered heterocycloalkyl-$C_{1-6}$-alkyl, each $R^{76}$ is independently chosen from H and $C_{1-6}$-alkyl, $Z^3$ may be chosen from H, $C_{1-6}$-alkyl, —$C_{1-6}$-alkyl-$R^{45a}$, —$C_{1-6}$-alkyl-(O—$C_{1-6}$-alkyl)$_2$, —C(═O)$C_{1-6}$-alkyl, —C(═O)$C_{1-6}$-alkyl-$R^{45b}$, —C(═O)$C_{1-6}$-haloalkyl, —C(═O)-(5-7 membered heterocycloalkyl), —C(═O)-(5-7 membered heteroaryl), $C_{1-6}$-haloalkyl, —C(═O)O$C_{1-6}$-alkyl, —C(═O)O$C_{1-6}$-alkyl-$R^{45c}$, —C(═O)O-(5-7-membered heterocycloalkyl-$C_{1-6}$-alkyl), —C(═O)N($R^{62}$)$_2$, —$C_{1-6}$-haloalkyl-O$R^{62}$, $C_{2-6}$-alkenyl, $C_{2-6}$-alkynyl, and —S(═O)$_2$—$C_{1-6}$-alkyl, $R^{45a}$ is chosen from —O$R^{62}$, 5-7 membered heterocycloalkyl, $C_{3-6}$-cycloalkyl, 5-6 membered heteroaryl, 5-6 membered heteroaryl-$C_{1-6}$-alkyl, phenyl, —SO$_2$—$C_{1-6}$-alkyl, —C(═O)N$R^{62}R^{63}$, —C(═O)O$C_{1-6}$-alkyl-O—$C_{1-4}$-alkyl, —C(═O)O$R^{62}$, —C(═O)-(4-7 membered heterocycloalkyl), —C(═O)-(5-7 membered heterocycloalkyl-$C_{1-6}$-alkyl), —OC(═O)$C_{1-6}$-alkyl, —OC(═O)$C_{1-6}$-alkyl-N($R^{62}$)$_2$, —OP(═O)(OH)$_2$, —N($R^{62}$)C(═O)—$C_{1-6}$-alkyl, —N($R^{62}$)$_2$, phenyl, and —C≡N, $R^{45b}$ is chosen from —O$R^{62}$, 5-7 membered heterocycloalkyl, 5-10 membered heteroaryl-($R^{79}$)$_x$, and —N($R^{62}$)$_2$, $R^{45c}$ is chosen from —O$R^{62}$, phenyl, and —N($R^{62}$)$_2$, each $R^{62}$ and $R^{63}$ is independently chosen from H and $C_{1-6}$-alkyl, each $R^{79}$ is ═O, and x is 0, 1, or 2.

In another embodiment, -$A^1$-$A^2$-$A^3$-$A^4$-$A^5$- is a group of formula —CH$_2$—CZ$^1$Z$^2$—CH$_2$—CH$_2$—CH$_2$—, —CH$_2$—CH$_2$—CZ$^1$Z$^2$—CH$_2$—CH$_2$—, —CH$_2$—CH$_2$—CH$_2$—CZ$^1$Z$^2$—CH$_2$—, —CZ$^1$Z$^2$—CH$_2$—CH$_2$—CH$_2$—NZ$^3$—, —CZ$^1$Z$^2$—CH$_2$—CZ$^1$Z$^2$—C(═O)—NZ$^3$—, —CH$_2$—CH$_2$—NZ$^3$—C(═O)—, —CH$_2$—CH$_2$—C(═O)—CH$_2$—CH$_2$—, —CH$_2$—CH$_2$—C(═O)—NZ$^3$—CZ$^1$Z$^2$—, —CH$_2$—CH$_2$—NZ$^3$—CH$_2$—CH$_2$—, —CH$_2$—CH$_2$—O—CH$_2$—CH$_2$—, —CH$_2$—CH$_2$—O—C(═O)—NZ$^3$—, —CH$_2$—CH$_2$—NZ$^3$—C(═O)—CZ$^1$Z$^2$—, —CH$_2$—C(═O)—NZ$^3$—CH$_2$—CH$_2$—, —CH$_2$—NZ$^3$—CH$_2$—CH$_2$—NZ$^3$—, —CH$_2$—O—CH$_2$—CH$_2$—NZ$^3$—, —CH$_2$—NZ$^3$—CH$_2$—CH$_2$—O—, —CH$_2$—NZ$^3$—CH$_2$—CH$_2$—S—, —CH$_2$—NZ$^3$—CH$_2$—CH$_2$—SO$_2$—, —CH$_2$—NZ$^3$—CH$_2$—C(═O)—NZ$^3$—, —CZ$^1$Z$^2$—NZ$^3$—C(═O)—CH$_2$—CH$_2$—, —CH$_2$—NZ$^3$—C(═O)—CH═CH—, —CH$_2$—NZ$^3$—C(═O)—NZ$^3$—CH$_2$—, —C(═O)—CZ$^1$Z$^2$—CH$_2$—CH$_2$—CH$_2$—, —C(═O)—NZ$^3$—CH$_2$—CH$_2$—CH$_2$—, —C(═O)—NZ$^3$—CH$_2$—CH$_2$—O—, —C(═O)—NZ$^3$—CZ$^1$Z$^2$—CZ$^1$Z$^2$—NZ$^3$—, —NZ$^3$—CH$_2$—CZ$^1$Z$^2$—CH$_2$—CZ$^1$Z$^2$—, —NZ$^3$—CH$_2$—CZ$^1$Z$^2$—CH$_2$—O—, —NZ$^3$—CH$_2$—CH$_2$—NZ$^3$—CH$_2$—, —NZ$^3$—CH$_2$—CH$_2$—NZ$^3$—C(═O)—, —NZ$^3$—CH$_2$—C(═O)—NZ$^3$—CH$_2$—, —NZ$^3$—C(═O)—CZ$^1$Z$^2$—CH$_2$—CZ$^1$Z$^2$—, —NZ$^3$—C(═O)—CH$_2$—CH$_2$—O—, —NZ$^3$—C(═O)—CH$_2$—NZ$^3$—CZ$^1$Z$^2$—, —NZ$^3$—C(═O)—O—CH$_2$—CH$_2$—, —O—CH$_2$—CH$_2$—CH$_2$—CZ$^1$Z$^2$—, —O—CH$_2$—CH$_2$—NZ$^3$—C(═O)—, —O—CH$_2$—CZ$^1$Z$^2$—CH$_2$—NZ$^3$—, —O—CH$_2$—CH$_2$—CH$_2$—O—, —CH$_2$—NZ$^3$—C(═O)—CH$_2$—CH$_2$—NZ$^3$—, —CZ$^1$Z$^2$—NZ$^3$—CH$_2$—CH$_2$—CH$_2$—, —NZ$^3$—CZ$^1$Z$^2$—C(═O)—CH$_2$—O—, —NZ$^3$—CZ$^1$Z$^2$—CH═CH—O—, —NZ$^3$—CZ$^1$Z$^2$—CH$_2$—CH$_2$—CZ$^1$Z$^2$—, or —NZ$^3$—CZ$^1$Z$^2$—CH$_2$—NZ$^3$—CH$_2$—, wherein each $Z^1$ and $Z^2$ is independently chosen from H, halogen, $C_{1-6}$-alkyl, —$C_{1-6}$-alkyl-O$R^{76}$, —N$R^{40}R^{41}$, —O$R^{76}$, 5-7 membered heterocycloalkyl, 5-7 membered heterocycloalkyl-$R^{45}$, —N($R^{76}$)C(═O)$C_{1-6}$-alkyl, —N($R^{76}$)C(═O)$C_{1-6}$-haloalkyl, —N($R^{76}$)C(═O)$C_{1-6}$-alkyl-N($R^{76}$)$_2$, —N($R^{76}$)C(═O)$C_{1-6}$-alkyl-O$R^{76}$, —N($R^{76}$)C(═O)-(5-7 membered heterocycloalkyl), —N($R^{76}$)C(═O)—($C_{3-6}$-cycloalkyl), and —N($R^{76}$)C(═O)O$C_{1-6}$-alkyl, $R^{40}$ and $R^{41}$ are independently chosen from H, $C_{1-6}$-alkyl, $C_{1-4}$-haloalkyl, and —$C_{1-6}$-alkyl-O$R^{76}$, $R^{45}$ is chosen from —O$R^{76}$, $C_{1-6}$-alkyl, 5-7 membered heterocycloalkyl, and 5-7 membered heterocycloalkyl-$C_{1-6}$-alkyl, each $R^{76}$ is independently chosen from H and $C_{1-6}$-alkyl, $Z^3$ is chosen from H, $C_{1-6}$-alkyl, $C_{1-6}$-haloalkyl, $C_{1-6}$-haloalkyl-O$R^{62}$, —$C_{1-6}$-alkyl-$R^{45a}$, —$C_{1-6}$-alkyl-(O—$C_{1-6}$-alkyl)$_2$, —C(═O)$C_{1-6}$-alkyl, —C(═O)$C_{1-6}$-alkyl-$R^{45b}$, —C(═O)$C_{1-6}$-haloalkyl, —C(═O)-(5-7 membered heterocycloalkyl), —C(═O)-(5-7 membered heteroaryl), —C(═O)O$C_{1-6}$-alkyl, —C(═O)O$C_{1-6}$-alkyl-$R^{45c}$, —C(═O)O-(5-7-membered heterocycloalkyl-$C_{1-6}$-alkyl), —C(═O)N($R^{62}$)$_2$, $C_{2-6}$-alkenyl, $C_{2-6}$-alkynyl, and —SO$_2$$C_{1-6}$-alkyl, $R^{45a}$ is chosen from —O$R^{62}$, 5-7 membered heterocycloalkyl, $C_{3-6}$-cycloalkyl, 5-6 membered heteroaryl, 5-6 membered heteroaryl-$C_{1-6}$-alkyl, phenyl, —$SO_2C_{1-6}$-alkyl, —C(=O)N$R^{62}R^{63}$, —C(=O)O$C_{1-6}$-alkyl-O—$C_{1-4}$-alkyl, —C(=O)O$R^{62}$, —C(=O)-(4-7 membered heterocycloalkyl), —C(=O)-(5-7 membered heterocycloalkyl-$C_{1-6}$-alkyl), —OC(=O)$C_{1-6}$-alkyl, —OC(=O)$C_{1-6}$-alkyl-N($R^{62}$)$_2$, —OP(=O)(OH)$_2$, —N($R^{62}$)C(=O)—$C_{1-6}$-alkyl, —N($R^{62}$)$_2$, and —C≡N, $R^{45b}$ is chosen from —O$R^{62}$, 5-7 membered heterocycloalkyl, 5-10 membered heteroaryl-($R^{79}$)$_x$, and —N($R^{62}$)$_2$, $R^{45c}$ is chosen from —O$R^{62}$, phenyl, and —N($R^{62}$)$_2$, each $R^{62}$ and $R^{63}$ is independently chosen from H and $C_{1-6}$-alkyl, each $R^{79}$ is =O, and x is 0, 1, or 2. In another embodiment, -$A^1$-$A^2$-$A^3$-$A^4$-$A^5$- is a group of formula —$CH_2$—CH$Z^1$—$CH_2$—$CH_2$—$CH_2$—, —$CH_2$—$CH_2$—CH$Z^1$—$CH_2$—$CH_2$—, —$CH_2$—$CH_2$—$CH_2$—CH$Z^1$—$CH_2$—, —C$Z^1Z^2$—$CH_2$—$CH_2$—$CH_2$—N$Z^3$—, —C$Z^1Z^2$—$CH_2$—C$Z^1Z^2$—C(=O)—N$Z^3$—, —$CH_2$—$CH_2$—$CH_2$—N$Z^3$—C(=O)—, —$CH_2$—$CH_2$—C(=O)—$CH_2$—$CH_2$—, —$CH_2$—$CH_2$—C(=O)—N$Z^3$—C$Z^1Z^2$—, —$CH_2$—$CH_2$—N$Z^3$—$CH_2$—$CH_2$—, —$CH_2$—$CH_2$—O—$CH_2$—$CH_2$—, —$CH_2$—$CH_2$—O—C(=O)—N$Z^3$—, —$CH_2$—$CH_2$—N$Z^3$—C(=O)—CH$Z^1$—, —$CH_2$—C(=O)—N$Z^3$—$CH_2$—$CH_2$—, —$CH_2$—N$Z^3$—$CH_2$—$CH_2$—N$Z^3$—, —$CH_2$—O—$CH_2$—$CH_2$—N$Z^3$—, —$CH_2$—N$Z^3$—$CH_2$—$CH_2$—O—, —$CH_2$—N$Z^3$—$CH_2$—$CH_2$—S—, —$CH_2$—N$Z^3$—$CH_2$—$CH_2$—$SO_2$—, —$CH_2$—N$Z^3$—$CH_2$—C(=O)—N$Z^3$—, —C$Z^1Z^2$—N$Z^3$—C(=O)—$CH_2$—$CH_2$—, —$CH_2$—N$Z^3$—C(=O)—CH=CH—, —$CH_2$—N$Z^3$—C(=O)—N$Z^3$—$CH_2$—, —C(=O)—$CH_2$—CH$Z^1$—$CH_2$—$CH_2$—, —C(=O)—N$Z^3$—$CH_2$—$CH_2$—$CH_2$—, —C(=O)—N$Z^3$—$CH_2$—$CH_2$—O—, —C(=O)—N$Z^3$—CH$Z^1$—CH$Z^1$—N$Z^3$—, —N$Z^3$—$CH_2$—CH$Z^1$—$CH_2$—C$Z^1Z^2$—, —N$Z^3$—$CH_2$—C$Z^1Z^2$—$CH_2$—O—, —N$Z^3$—$CH_2$—$CH_2$—N$Z^3$—$CH_2$—, —N$Z^3$—$CH_2$—$CH_2$—N$Z^3$—C(=O)—, —N$Z^3$—$CH_2$—C(=O)—N$Z^3$—$CH_2$—, —N$Z^3$—$CH_2$—C(=O)—CH$Z^1$—$CH_2$—C$Z^1Z^2$—, —N$Z^3$—C(=O)—$CH_2$—$CH_2$—O—, —N$Z^3$—C(=O)—$CH_2$—N$Z^3$—C$Z^1Z^2$—, —N$Z^3$—C(=O)—O—$CH_2$—$CH_2$—, —O—$CH_2$—$CH_2$—$CH_2$—C$Z^1Z^2$—, —O—$CH_2$—$CH_2$—N$Z^3$—C(=O)—, —O—$CH_2$—C$Z^1Z^2$—$CH_2$—N$Z^3$—, —O—$CH_2$—$CH_2$—$CH_2$—O—, —$CH_2$—N$Z^3$—C(=O)—$CH_2$—$CH_2$—N$Z^3$—, —C$Z^1Z^2$—N$Z^3$—$CH_2$—$CH_2$—$CH_2$—, —N$Z^3$—C$Z^1Z^2$—C(=O)—$CH_2$—O—, —N$Z^3$—C$Z^1Z^2$—CH=CH—O—, —N$Z^3$—C$Z^1Z^2$—$CH_2$—$CH_2$—C$Z^1Z^2$—, or —N$Z^3$—C$Z^1Z^2$—$CH_2$—N$Z^3$—$CH_2$—, wherein each $Z^1$ and $Z^2$ is independently chosen from H, halogen, $C_{1-6}$-alkyl, —$C_{1-6}$-alkyl-O$R^{76}$, —N$R^{40}R^{41}$, —O$R^{76}$, 5-7 membered heterocycloalkyl, 5-7 membered heterocycloalkyl-$R^{45}$, —N($R^{76}$)C(=O)$C_{1-6}$-alkyl, —N($R^{76}$)C(=O)$C_{1-6}$-haloalkyl, —N($R^{76}$)C(=O)$C_{1-6}$-alkyl-N($R^{76}$)$_2$, —N($R^{76}$)C(=O)$C_{1-6}$-alkyl-O$R^{76}$, —N($R^{76}$)C(=O)-(5-7 membered heterocycloalkyl), —N($R^{76}$)C(=O)—($C_{3-6}$-cycloalkyl), and —N($R^{76}$)C(=O)O$C_{1-6}$-alkyl, $R^{40}$ and $R^{41}$ are independently chosen from H, $C_{1-6}$-alkyl, $C_{1-4}$-haloalkyl, and —$C_{1-6}$-alkyl-O$R^{76}$, $R^{45}$ is chosen from —O$R^{76}$, $C_{1-6}$-alkyl, 5-7 membered heterocycloalkyl, and 5-7 membered heterocycloalkyl-$C_{1-6}$-alkyl, each $R^{76}$ is independently chosen from H and $C_{1-6}$-alkyl, $Z^3$ is chosen from H, $C_{1-6}$-alkyl, $C_{1-6}$-haloalkyl, $C_{1-6}$-haloalkyl-O$R^{62}$, —$C_{1-6}$-alkyl-$R^{45a}$, —$C_{1-6}$-alkyl-(O—$C_{1-6}$-alkyl)$_2$, —C(=O)$C_{1-6}$-alkyl, —C(=O)$C_{1-6}$-alkyl-$R^{45b}$, —C(=O)$C_{1-6}$-haloalkyl, —C(=O)-(5-7 membered heterocycloalkyl), —C(=O)-(5-7 membered heteroaryl), —C(=O)O$C_{1-6}$-alkyl, —C(=O)O$C_{1-6}$-alkyl-$R^{45c}$, —C(=O)O-(5-7-membered heterocycloalkyl-$C_{1-6}$-alkyl), —C(=O)N($R^{62}$)$_2$, $C_{2-6}$-alkenyl, $C_{2-6}$-alkynyl, and —$SO_2C_{1-6}$-alkyl, $R^{45a}$ is chosen from —O$R^{62}$, 5-7 membered heterocycloalkyl, $C_{3-6}$-cycloalkyl, 5-6 membered heteroaryl, 5-6 membered heteroaryl-$C_{1-6}$-alkyl, phenyl, —$SO_2C_{1-6}$-alkyl, —C(=O)N$R^{62}R^{63}$, —C(=O)O$C_{1-6}$-alkyl-O—$C_{1-4}$-alkyl, —C(=O)O$R^{62}$, —C(=O)-(4-7 membered heterocycloalkyl), —C(=O)-(5-7 membered heterocycloalkyl-$C_{1-6}$-alkyl), —OC(=O)$C_{1-6}$-alkyl, —OC(=O)$C_{1-6}$-alkyl-N($R^{62}$)$_2$, —OP(=O)(OH)$_2$, —N($R^{62}$)C(=O)—$C_{1-6}$-alkyl, —N($R^{62}$)$_2$, and —C≡N, $R^{45b}$ is chosen from —O$R^{62}$, 5-7 membered heterocycloalkyl, 5-10 membered heteroaryl-($R^{79}$)$_x$, and —N($R^{62}$)$_2$, $R^{45c}$ is chosen from —O$R^{62}$, phenyl, and —N($R^{62}$)$_2$, each $R^{62}$ and $R^{63}$ is independently chosen from H and $C_{1-6}$-alkyl, each $R^{79}$ is =O, and x is 0, 1, or 2. In another embodiment, -$A^1$-$A^2$-$A^3$-$A^4$-$A^5$- is a group of formula —$CH_2$—CH$Z^1$—$CH_2$—$CH_2$—$CH_2$—, —$CH_2$—$CH_2$—CH$Z^1$—$CH_2$—$CH_2$—, —$CH_2$—$CH_2$—$CH_2$—CH$Z^1$—$CH_2$—, —C$Z^1Z^2$—$CH_2$—$CH_2$—$CH_2$—N$Z^3$—, —C$Z^1Z^2$—$CH_2$—C$Z^1Z^2$—C(=O)—N$Z^3$—, —$CH_2$—$CH_2$—$CH_2$—N$Z^3$—C(=O)—, —$CH_2$—$CH_2$—C(=O)—$CH_2$—$CH_2$—, —$CH_2$—$CH_2$—C(=O)—NH—CH$Z^1Z^2$—, —$CH_2$—$CH_2$—N$Z^3$—$CH_2$—$CH_2$—, —$CH_2$—$CH_2$—O—$CH_2$—$CH_2$—, —$CH_2$—$CH_2$—O—C(=O)—N$Z^3$—, —$CH_2$—$CH_2$—N$Z^3$—C(=O)—CH$Z^1$—, —$CH_2$—C(=O)—N$Z^3$—$CH_2$—$CH_2$—, —$CH_2$—N$Z^3$—$CH_2$—$CH_2$—N$Z^3$—, —$CH_2$—O—$CH_2$—$CH_2$—N$Z^3$—, —$CH_2$—N$Z^3$—$CH_2$—$CH_2$—O—, —$CH_2$—N$Z^3$—$CH_2$—$CH_2$—S—, —$CH_2$—NH—$CH_2$—$CH_2$—$SO_2$—, —$CH_2$—N$Z^3$—$CH_2$—C(=O)—NH—, —C$Z^1Z^2$—N$Z^3$—C(=O)—$CH_2$—$CH_2$—, —$CH_2$—N$Z^3$—C(=O)—CH=CH—, —$CH_2$—NH—C(=O)—NH—$CH_2$—, —C(=O)—$CH_2$—CH$Z^1$—$CH_2$—$CH_2$—, —C(=O)—N$Z^3$—$CH_2$—$CH_2$—$CH_2$—, —C(=O)—NH—$CH_2$—$CH_2$—O—, —C(=O)—N$Z^3$—CH$Z^1$—CH$Z^1$—N$Z^3$—, —NH—$CH_2$—CH$Z^1$—$CH_2$—C$Z^1Z^2$—, —N$Z^3$—$CH_2$—C$Z^1Z^2$—$CH_2$—O—, —N$Z^3$—$CH_2$—$CH_2$—N$Z^3$—$CH_2$—, —N$Z^3$—$CH_2$—N$Z^3$—C(=O)—, —N$Z^3$—$CH_2$—C(=O)—NH—$CH_2$—, —N$Z^3$—C(=O)—CH$Z^1$—$CH_2$—C$Z^1Z^2$—, —NH—C(=O)—$CH_2$—$CH_2$—O—, —N$Z^3$—C(=O)—$CH_2$—N$Z^3$—C$Z^1Z^2$—, —N$Z^3$—C(=O)—O—$CH_2$—$CH_2$—, —O—$CH_2$—$CH_2$—$CH_2$—C$Z^1Z^2$—, —O—$CH_2$—$CH_2$—N$Z^3$—C(=O)—, —O—$CH_2$—C$Z^1Z^2$—$CH_2$—N$Z^3$—, —O—$CH_2$—$CH_2$—$CH_2$—O—, —$CH_2$—NH—C(=O)—$CH_2$—$CH_2$—N$Z^3$—, —C$Z^1Z^2$—N$Z^3$—$CH_2$—$CH_2$—$CH_2$—, —N$Z^3$—C$Z^1Z^2$—C(=O)—$CH_2$—O—, —N$Z^3$—C$Z^1Z^2$—CH=CH—O—, —N$Z^3$—C$Z^1Z^2$—$CH_2$—$CH_2$—C$Z^1Z^2$—, or —N$Z^3$—C$Z^1Z^2$—$CH_2$—NH—$CH_2$—, wherein each $Z^1$ and $Z^2$ is independently chosen from H, halogen, $C_{1-6}$-alkyl, —$C_{1-6}$-alkyl-O$R^{76}$, —N$R^{40}R^{41}$, —O$R^{76}$, 5-7 membered heterocycloalkyl, 5-7 membered heterocycloalkyl-$R^{45}$, —N($R^{76}$)C(=O)$C_{1-6}$-alkyl, —N($R^{76}$)C(=O)$C_{1-6}$-haloalkyl, —N($R^{76}$)C(=O)$C_{1-6}$-alkyl-N($R^{76}$)$_2$, —N($R^{76}$)C(=O)$C_{1-6}$-alkyl-O$R^{76}$, —N($R^{76}$)C(=O)-(5-7 membered heterocycloalkyl), —N($R^{76}$)C(=O)—($C_{3-6}$-cycloalkyl), and —N($R^{76}$)C(=O)O$C_{1-6}$-alkyl, $R^{40}$ and $R^{41}$ are independently chosen from H, $C_{1-6}$-alkyl, $C_{1-4}$-haloalkyl, and —$C_{1-6}$-alkyl-O$R^{76}$, $R^{45}$ is chosen from —O$R^{76}$, $C_{1-6}$-alkyl, 5-7 membered heterocycloalkyl, and 5-7 membered heterocycloalkyl-$C_{1-6}$-alkyl, each $R^{76}$ is independently chosen from H and $C_{1-6}$-alkyl, $Z^3$ is chosen from H, $C_{1-6}$-alkyl, $C_{1-6}$-haloalkyl, $C_{1-6}$-haloalkyl-O$R^{62}$, —$C_{1-6}$-alkyl-$R^{45a}$, —$C_{1-6}$-alkyl-(O—$C_{1-6}$-alkyl)$_2$, —C(=O)$C_{1-6}$-alkyl, —C(=O)$C_{1-6}$-alkyl-$R^{45b}$, —C(=O)$C_{1-6}$-haloalkyl, —C(=O)-(5-7 membered heterocycloalkyl), —C(=O)-(5-7 membered heteroaryl), —C(=O)O$C_{1-6}$-alkyl, —C(=O)O$C_{1-6}$-alkyl-$R^{45c}$, —C(=O)O-(5-7-membered heterocycloalkyl-$C_{1-6}$-alkyl), —C(=O)N($R^{62}$)$_2$, $C_{2-6}$-alkenyl, $C_{2-6}$-alkynyl, and —$SO_2C_{1-6}$-alkyl, $R^{45a}$ is chosen from —O$R^{62}$, 5-7 membered heterocycloalkyl, $C_{3-6}$-cycloalkyl, 5-6 membered heteroaryl, 5-6 membered heteroaryl-$C_{1-6}$-alkyl, phenyl, —$SO_2C_{1-6}$-alkyl, —C(=O)N$R^{62}R^{63}$, —C(=O)O$C_{1-6}$- alkyl-O—$C_{1-4}$-alkyl, —C(=O)O$R^{62}$, —C(=O)-(4-7 membered heterocycloalkyl), —C(=O)-(5-7 membered heterocycloalkyl-$C_{1-6}$-alkyl), —OC(=O)$C_{1-6}$-alkyl, —OC(=O)$C_{1-6}$-alkyl-N($R^{62}$)$_2$, —OP(=O)(OH)$_2$, —N($R^{62}$)C(=O)—$C_{1-6}$-alkyl, —N($R^{62}$)$_2$, and —C≡N, $R^{45b}$ is chosen from —O$R^{62}$, 5-7 membered heterocycloalkyl, 5-10 membered heteroaryl-($R^{79}$)$_x$, and —N($R^{62}$)$_2$, $R^{45c}$ is chosen from —O$R^{62}$, phenyl, and —N($R^{62}$)$_2$, each $R^{62}$ and $R^{63}$ is independently chosen from H and $C_{1-6}$-alkyl, each $R^{79}$ is =O, and x is 0, 1, or 2. In another embodiment, -$A^1$-$A^2$-$A^3$-$A^4$-$A^5$- is a group of formula —CH$_2$—CH$_2$—C$Z^1Z^2$—CH$_2$—CH$_2$—, —C$Z^1Z^2$—CH$_2$—CH$_2$—CH$_2$—N$Z^3$—, —C$Z^1Z^2$—CH$_2$—C$Z^1Z^2$—C(=O)—N$Z^3$—, —CH$_2$—CH$_2$—CH$_2$—N$Z^3$—C(=O)—, —CH$_2$—CH$_2$—C(=O)—CH$_2$—CH$_2$—, —CH$_2$—CH$_2$—N$Z^3$—CH$_2$—CH$_2$—, —CH$_2$—CH$_2$—O—CH$_2$—CH$_2$—, —CH$_2$—CH$_2$—N$Z^3$—C(=O)—C$Z^1Z^2$—, —CH$_2$—N$Z^3$—CH$_2$—CH$_2$—N$Z^3$—, —CH$_2$—O—CH$_2$—CH$_2$—N$Z^3$—, —CH$_2$—NH—CH$_2$—CH$_2$—O—, —CH$_2$—N$Z^3$—CH$_2$—CH$_2$—S—, —CH$_2$—NH—CH$_2$—CH$_2$—SO$_2$—, —CH$_2$—NH—C(=O)—NH—CH$_2$—, —C(=O)—N$Z^3$—CH$_2$—CH$_2$—CH$_2$—, —C(=O)—N$Z^3$—C$Z^1Z^2$C$Z^1Z^2$—N$Z^3$—, —N$Z^3$—CH$_2$—CH$_2$—N$Z^3$—CH$_2$—, —N$Z^3$—CH$_2$—CH$_2$—N$Z^3$—C(=O)—, —N$Z^3$—C(=O)—CH$_2$—CH$_2$—CH$_2$—, —O—CH$_2$—CH$_2$—N$Z^3$—C(=O)—, —O—CH$_2$—CH$_2$—CH$_2$—O—, —CH$Z^1$—CH$_2$—CH$_2$—CH$Z^1$—CH$_2$—, —CH$Z^1$—CH$_2$—N$Z^3$—CH$_2$—CH$Z^1$—, —CH$_2$—O—CH$_2$—CH$Z^1$—N$Z^3$—, or —CH$_2$—CH$Z^1$—CH$_2$—CH$_2$—CH$Z^1$—, wherein any two $Z^1$, $Z^2$, and $Z^3$ that are located on adjacent atoms may together form a bond between the atoms, each $Z^1$ and $Z^2$ may independently be chosen from H, halogen, $C_{1-6}$-alkyl, —$C_{1-6}$-alkyl-O$R^{76}$, —N$R^{40}R^{41}$, —O$R^{76}$, 5-7 membered heterocycloalkyl, 5-7 membered heterocycloalkyl-$R^{45}$, —N($R^{76}$)C(=O)$C_{1-6}$-alkyl, —N($R^{76}$)C(=O)$C_{1-6}$-haloalkyl, —N($R^{76}$)C(=O)$C_{1-6}$-alkyl-N($R^{76}$)$_2$, —N($R^{76}$)C(=O)$C_{1-6}$-alkyl-O$R^{76}$, —N($R^{76}$)C(=O)-(5-7 membered heterocycloalkyl), —N($R^{76}$)C(=O)—($C_{3-6}$-cycloalkyl), and —N($R^{76}$)C(=O)OC$_{1-6}$-alkyl, $R^{40}$ and $R^{41}$ are independently chosen from H, $C_{1-6}$-alkyl, $C_{1-4}$-haloalkyl, —$C_{1-6}$-alkyl-O$R^{76}$, —$C_{1-6}$-alkyl-N($R^{76}$)$_2$, and $C_{3-6}$-cycloalkyl, $R^{45}$ is chosen from —O$R^{76}$, $C_{1-6}$-alkyl, 5-7 membered heterocycloalkyl, and 5-7 membered heterocycloalkyl-$C_{1-6}$-alkyl, each $R^{76}$ is independently chosen from H and $C_{1-6}$-alkyl, $Z^3$ may be chosen from H, $C_{1-6}$-alkyl, —$C_{1-6}$-alkyl-$R^{45a}$, —$C_{1-6}$-alkyl-(O—$C_{1-6}$-alkyl)$_2$, —C(=O)$C_{1-6}$-alkyl, —C(=O)$C_{1-6}$-alkyl-$R^{45b}$, —C(=O)$C_{1-6}$-haloalkyl, —C(=O)-(5-7 membered heterocycloalkyl), —C(=O)-(5-7 membered heteroaryl), $C_{1-6}$-haloalkyl, —C(=O)O$C_{1-6}$-alkyl, —C(=O)O$C_{1-6}$-alkyl-$R^{45c}$, —C(=O)O-(5-7-membered heterocycloalkyl-$C_{1-6}$-alkyl), —C(=O)N($R^{62}$)$_2$, —$C_{1-6}$-haloalkyl-O$R^{62}$, $C_{2-6}$-alkenyl, $C_{2-6}$-alkynyl, and —S(=O)$_2$—$C_{1-6}$-alkyl, $R^{45a}$ is chosen from —O$R^{62}$, 5-7 membered heterocycloalkyl, $C_{3-6}$-cycloalkyl, 5-6 membered heteroaryl, 5-6 membered heteroaryl-$C_{1-6}$-alkyl, phenyl, —SO$_2$—$C_{1-6}$-alkyl, —C(=O)N$R^{62}R^{63}$, —C(=O)O$C_{1-6}$-alkyl-O—$C_{1-4}$-alkyl, —C(=O)O$R^{62}$, —C(=O)-(4-7 membered heterocycloalkyl), —C(=O)-(5-7 membered heterocycloalkyl-$C_{1-6}$-alkyl), —OC(=O)$C_{1-6}$-alkyl, —OC(=O)$C_{1-6}$-alkyl-N($R^{62}$)$_2$, —OP(=O)(OH)$_2$, —N($R^{62}$)C(=O)—$C_{1-6}$-alkyl, —N($R^{62}$)$_2$, phenyl, and —C≡N, $R^{45b}$ is chosen from —O$R^{62}$, 5-7 membered heterocycloalkyl, 5-10 membered heteroaryl-($R^{79}$)$_x$, and —N($R^{62}$)$_2$, $R^{45c}$ is chosen from —O$R^{62}$, phenyl, and —N($R^{62}$)$_2$, each $R^{62}$ and $R^{63}$ is independently chosen from H and $C_{1-6}$-alkyl, each $R^{79}$ is =O, and x is 0, 1, or 2.

In another embodiment, -$A^1$-$A^2$-$A^3$-$A^4$-$A^5$- is a group of formula —CH$_2$—CH$_2$—C$Z^1Z^2$—CH$_2$—CH$_2$—, —C$Z^1Z^2$—CH$_2$—CH$_2$—CH$_2$—N$Z^3$—, —C$Z^1Z^2$—CH$_2$—C$Z^1Z^2$—C(=O)—N$Z^3$—, —CH$_2$—CH$_2$—CH$_2$—N$Z^3$—C(=O)—, —CH$_2$—CH$_2$—C(=O)—CH$_2$—CH$_2$—, —CH$_2$—CH$_2$—N$Z^3$—CH$_2$—CH$_2$—, —CH$_2$—CH$_2$—O—CH$_2$—CH$_2$—, —CH$_2$—CH$_2$—N$Z^3$—C(=O)—C$Z^1Z^2$—, —CH$_2$—N$Z^3$—CH$_2$—CH$_2$—N$Z^3$—, —CH$_2$—O—CH$_2$—CH$_2$—N$Z^3$—, —CH$_2$—NH—CH$_2$—CH$_2$—O—, —CH$_2$—N$Z^3$—CH$_2$—CH$_2$—S—, —CH$_2$—NH—CH$_2$—CH$_2$—SO$_2$—, —CH$_2$—NH—C(=O)—NH—CH$_2$—, —C(=O)—N$Z^3$—CH$_2$—CH$_2$—CH$_2$—, —C(=O)—N$Z^3$—C$Z^1Z^2$CZ$^1Z^2$—N$Z^3$—, —N$Z^3$—CH$_2$—CH$_2$—N$Z^3$—CH$_2$—, —N$Z^3$—CH$_2$—CH$_2$—N$Z^3$—C(=O)—, —N$Z^3$—C(=O)—CH$_2$—CH$_2$—CH$_2$—, —O—CH$_2$—CH$_2$—N$Z^3$—C(=O)—, —O—CH$_2$—CH$_2$—CH$_2$—O—, —CH$Z^1$—CH$_2$—CH$_2$—CH$Z^1$—CH$_2$—, —CH$Z^1$—CH$_2$—N$Z^3$—CH$_2$—CH$Z^1$—, —CH$_2$—O—CH$_2$—CH$Z^1$—N$Z^3$—, or —CH$_2$—CH$Z^1$—CH$_2$—CH$_2$—CH$Z^1$—, wherein each $Z^1$ and $Z^2$ is independently chosen from H, halogen, $C_{1-6}$-alkyl, —$C_{1-6}$-alkyl-O$R^{76}$, —N$R^{40}R^{41}$, —O$R^{76}$, 5-7 membered heterocycloalkyl, 5-7 membered heterocycloalkyl-$R^{45}$, —N($R^{76}$)C(=O)$C_{1-6}$-alkyl, —N($R^{76}$)C(=O)$C_{1-6}$-haloalkyl, —N($R^{76}$)C(=O)$C_{1-6}$-alkyl-N($R^{76}$)$_2$, —N($R^{76}$)C(=O)$C_{1-6}$-alkyl-O$R^{76}$, —N($R^{76}$)C(=O)-(5-7 membered heterocycloalkyl), —N($R^{76}$)C(=O)—($C_{3-6}$-cycloalkyl), and —N($R^{76}$)C(=O)OC$_{1-6}$-alkyl, $R^{40}$ and $R^{41}$ are independently chosen from H, $C_{1-6}$-alkyl, $C_{1-4}$-haloalkyl, and —$C_{1-6}$-alkyl-O$R^{76}$, $R^{45}$ is chosen from —O$R^{76}$, $C_{1-6}$-alkyl, 5-7 membered heterocycloalkyl, and 5-7 membered heterocycloalkyl-$C_{1-6}$-alkyl, each $R^{76}$ is independently chosen from H and $C_{1-6}$-alkyl, $Z^3$ is chosen from H, $C_{1-6}$-alkyl, $C_{1-6}$-haloalkyl, $C_{1-6}$-haloalkyl-O$R^{62}$, —$C_{1-6}$-alkyl-$R^{45a}$, —$C_{1-6}$-alkyl-(O—$C_{1-6}$-alkyl)$_2$, —C(=O)$C_{1-6}$-alkyl-Rb, —C(=O)$C_{1-6}$-haloalkyl, —C(=O)-(5-7 membered heterocycloalkyl), —C(=O)-(5-7 membered heteroaryl), —C(=O)O$C_{1-6}$-alkyl, —C(=O)O$C_{1-6}$-alkyl-$R^{45c}$, —C(=O)O-(5-7-membered heterocycloalkyl-$C_{1-6}$-alkyl), —C(=O)N($R^{62}$)$_2$, $C_{2-6}$-alkenyl, $C_{2-6}$-alkynyl, and —SO$_2$C$_{1-6}$-alkyl, $R^{45a}$ is chosen from —O$R^{62}$, 5-7 membered heterocycloalkyl, $C_{3-6}$-cycloalkyl, 5-6 membered heteroaryl, 5-6 membered heteroaryl-$C_{1-6}$-alkyl, phenyl, —SO$_2$C$_{1-6}$-alkyl, —C(=O)N$R^{62}R^{63}$, —C(=O)O$C_{1-6}$-alkyl-O—$C_{1-4}$-alkyl, —C(=O)O$R^{62}$, —C(=O)-(4-7 membered heterocycloalkyl), —C(=O)-(5-7 membered heterocycloalkyl-$C_{1-6}$-alkyl), —OC(=O)$C_{1-6}$-alkyl, —OC(=O)$C_{1-6}$-alkyl-N($R^{62}$)$_2$, —OP(=O)(OH)$_2$, —N($R^{62}$)C(=O)—$C_{1-6}$-alkyl, —N($R^{62}$)$_2$, and —C≡N, $R^{45b}$ is chosen from —O$R^{62}$, 5-7 membered heterocycloalkyl, 5-10 membered heteroaryl-($R^{79}$)$_x$, and —N($R^{62}$)$_2$, $R^{45c}$ is chosen from —O$R^{62}$, phenyl, and —N($R^{62}$)$_2$, each $R^{62}$ and $R^{63}$ is independently chosen from H and $C_{1-6}$-alkyl, each $R^{79}$ is =O, and x is 0, 1, or 2. In another embodiment, -$A^1$-$A^2$-$A^3$-$A^4$-$A^5$- is a group of formula:
(a) —CH$_2$—C$Z^1Z^2$—CH$_2$—CH$_2$—CH$_2$—,
(b) —CH$_2$—CH$_2$—C$Z^1Z^2$—CH$_2$—CH$_2$—,
(c) —CH$_2$—CH$_2$—CH$_2$—C$Z^1Z^2$—CH$_2$—,
(d) —C$Z^1Z^2$—CH$_2$—CH$_2$—CH$_2$—N$Z^3$—,
(e) —C$Z^1Z^2$—CH$_2$—C$Z^1Z^2$—C(=O)—N$Z^3$—,
(f) —CH$_2$—CH$_2$—CH$_2$—N$Z^3$—C(=O)—,
(h) —CH$_2$—CH$_2$—C(=O)—N$Z^3$—C$Z^1Z^2$—,
(i) —CH$_2$—CH$_2$—N$Z^3$—CH$_2$—CH$_2$—,
(j) —CH$_2$—CH$_2$—O—CH$_2$—CH$_2$—,
(k) —CH$_2$—CH$_2$—O—C(=O)—N$Z^3$—,
(l) —CH$_2$—CH$_2$—N$Z^3$—C(=O)—C$Z^1Z^2$—,
(m) —CH$_2$—C(=O)—N$Z^3$—CH$_2$—CH$_2$—,
(n) —CH$_2$—N$Z^3$—CH$_2$—CH$_2$—N$Z^3$—,
(o) —CH$_2$—O—CH$_2$—CH$_2$—N$Z^3$—,
(p) —CH$_2$—N$Z^3$—CH$_2$—CH$_2$—O—,
(q) —CH$_2$—N$Z^3$—CH$_2$—CH$_2$—S—, (r) —CH$_2$—NZ$^3$—CH$_2$—CH$_2$—SO$_2$—,
(s) —CH$_2$—NZ$^3$—CH$_2$—C(=O)—NZ$^3$—,
(t) —CZ$^1$Z$^2$—NZ$^3$—C(=O)—CH$_2$—CH$_2$—,
(u) —CH$_2$—NZ$^3$—C(=O)—CH=CH—,
(v) —CH$_2$—NZ$^3$—C(=O)—NZ$^3$—CH$_2$—,
(w) —C(=O)—CH$_2$—CZ$^1$Z$^2$—CH$_2$—CH$_2$—,
(x) —C(=O)—NZ$^3$—CH$_2$—CH$_2$—CH$_2$—,
(y) —C(=O)—NZ$^3$—CH$_2$—CH$_2$—O—,
(z) —C(=O)—NZ$^3$—CZ$^1$Z$^2$CZ$^1$Z$^2$—NZ$^3$—,
(aa) —NZ$^3$—CH$_2$—CZ$^1$Z$^2$—CH$_2$—CZ$^1$Z$^2$—,
(bb) —NZ$^3$—CH$_2$—CZ$^1$Z$^2$—CH$_2$—O—,
(cc) —NZ$^3$—CH$_2$—CH$_2$—NZ$^3$—CH$_2$—,
(dd) —NZ$^3$—CH$_2$—CH$_2$—NZ$^3$—C(=O)—,
(ee) —NZ$^3$—CH$_2$—C(=O)—NZ$^3$—CH$_2$—,
(ff) —NZ$^3$—C(=O)—CZ$^1$Z$^2$—CH$_2$—CZ$^1$Z$^2$—,
(gg) —NZ$^3$—C(=O)—CH$_2$—CH$_2$—O—,
(hh) —NZ$^3$—C(=O)—CH$_2$—NZ$^3$—CZ$^1$Z$^2$—,
(ii) —NZ$^3$—C(=O)—O—CH$_2$—CH$_2$—,
(jj) —O—CH$_2$—CH$_2$—CH$_2$—CZ$^1$Z$^2$—,
(kk) —O—CH$_2$—CH$_2$—NZ$^3$—C(=O)—,
(ll) —O—CH$_2$—CZ$^1$Z$^2$—CH$_2$—NZ$^3$—,
(mm) —O—CH$_2$—CH$_2$—CH$_2$—O—,
(nn) —CH$_2$—NZ$^3$—C(=O)—CH$_2$—CH$_2$—NZ$^3$—,
(oo) —CH—N—CH$_2$—CH$_2$—CH$_2$—
          |__X__|, wherein X, combined with the atoms to which it is attached, is an imidazolyl group, (pp)
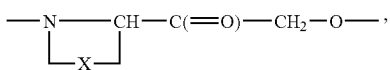

wherein X, combined with the atoms to which it is attached, is a pyrrolyl group, (qq)
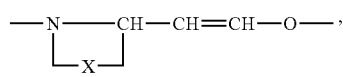

wherein X, combined with the atoms to which it is attached, is a pyrrolyl group, (rr)
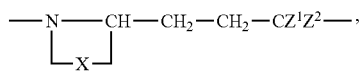

wherein X, combined with the atoms to which it is attached, is an imidazolyl group optionally substituted by C$_{1-6}$-alkyl, (ss)
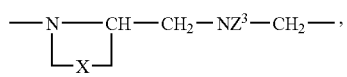

wherein X, combined with the atoms to which it is attached, is an imidazolyl group, (tt)
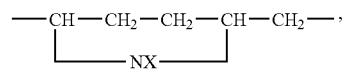

wherein X is chosen from H, C$_{1-6}$-alkyl, —C$_{1-6}$-alkyl-C$_{3-6}$-cycloalkyl, —C$_{1-6}$-alkyl-O—C$_{1-6}$-alkyl, —C(=O)C$_{3-6}$-cycloalkyl, —C(=O)OC$_{1-6}$-alkyl, C$_{2-6}$-alkynyl, and —S(=O)$_2$—C$_{1-6}$-alkyl, (uu)
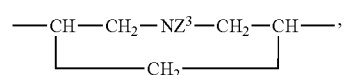

(vv)
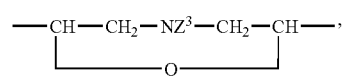

(ww)
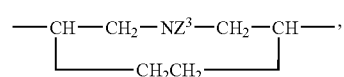

(xx)
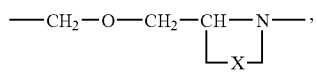

wherein X is chosen from C$_{1-6}$-alkyl, or (yy)
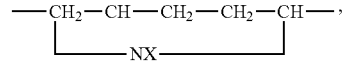

wherein X is —C(=O)OC$_{1-6}$-alkyl,
wherein each Z$^1$ and Z$^2$ is independently chosen from H, halogen, C$_{1-6}$-alkyl, —C$_{1-6}$-alkyl-OR$^{76}$, —NR$^{40}$R$^{41}$, —OR$^{76}$, 5-7 membered heterocycloalkyl, 5-7 membered heterocycloalkyl-R$^{45}$, —N(R$^{76}$)C(=O)C$_{1-6}$-alkyl, —N(R$^{76}$)C(=O)C$_{1-6}$-haloalkyl, —N(R$^{76}$)C(=O)C$_{1-6}$-alkyl-N(R$^{76}$)$_2$, —N(R$^{76}$)C(=O)C$_{1-6}$-alkyl-OR$^{76}$, —N(R$^{76}$)C(=O)-(5-7 membered heterocycloalkyl), —N(R$^{76}$)C(=O)—(C$_{3-6}$-cycloalkyl), and —N(R$^{76}$)C(=O)OC$_{1-6}$-alkyl, R$^{40}$ and R$^{41}$ are independently chosen from H, C$_{1-6}$-alkyl, C$_{1-4}$-haloalkyl, —C$_{1-6}$-alkyl-OR$^{76}$, —C$_{1-6}$-alkyl-N(R$^{76}$)$_2$, and C$_{3-6}$-cycloalkyl, R$^{45}$ is chosen from —OR$^{76}$, C$_{1-6}$-alkyl, 5-7 membered heterocycloalkyl, and 5-7 membered heterocycloalkyl-C$_{1-6}$-alkyl, each R$^{76}$ is independently chosen from H and C$_{1-6}$-alkyl, Z$^3$ is chosen from H, C$_{1-6}$-alkyl, —C$_{1-6}$-alkyl-R$^{45a}$, —C$_{1-6}$-alkyl-(O—C$_{1-6}$-alkyl)$_2$, —C(=O)C$_{1-6}$-alkyl, —C(=O)C$_{1-6}$-alkyl-R$^{45b}$, —C(=O)C$_{1-6}$-haloalkyl, —C(=O)-(5-7 membered heterocycloalkyl), —C(=O)-(5-7 membered heteroaryl), C$_{1-6}$-haloalkyl, —C(=O)OC$_{1-6}$-alkyl, —C(=O)OC$_{1-6}$-alkyl-R$^{45c}$, —C(=O)O-(5-7-membered heterocycloalkyl-C$_{1-6}$-alkyl), —C(=O)N(R$^{62}$)$_2$, —C$_{1-6}$-haloalkyl-OR$^{62}$, C$_{2-6}$-alkenyl, C$_{2-6}$-alkynyl, and —S(=O)$_2$—C$_{1-6}$-alkyl, wherein R$^{45a}$ is chosen from —OR$^{62}$, 5-7 membered heterocycloalkyl, C$_{3-6}$-cycloalkyl, 5-6 membered heteroaryl, 5-6 membered heteroaryl-C$_{1-6}$-alkyl, phenyl, —SO$_2$—C$_{1-6}$-alkyl, —C(=O)NR$^{62}$R$^{63}$, —C(=O)OC$_{1-6}$-alkyl-O—C$_{1-4}$-alkyl, —C(=O)OR$^{62}$, —C(=O)-(4-7 membered heterocycloalkyl), —C(=O)-(5-7 membered heterocycloalkyl-C$_{1-6}$-alkyl), —OC(=O)C$_{1-6}$- alkyl, —OC(=O)$C_{1-6}$-alkyl-N($R^{62}$)$_2$, —OP(=O)(OH)$_2$, —N($R^{62}$)C(=O)—$C_{1-6}$-alkyl, —N($R^{62}$)$_2$, phenyl, and —C≡N, $R^{45b}$ is chosen from —O$R^{62}$, 5-7 membered heterocycloalkyl, 5-10 membered heteroaryl-($R^{79}$)$_x$, and —N($R^{62}$)$_2$, $R^{45c}$ is chosen from —O$R^{62}$, phenyl, and —N($R^{62}$)$_2$, each $R^{62}$ and $R^{63}$ is independently chosen from H and $C_{1-6}$-alkyl, each $R^{79}$ is =O, and x is 0, 1, or 2.

In another embodiment, -$A^1$-$A^2$-$A^3$-$A^4$-$A^5$- is a group of formula:

(a) —$CH_2$—$CZ^1Z^2$—$CH_2$—$CH_2$—$CH_2$—,
(b) —$CH_2$—$CH_2$—$CZ^1Z^2$—$CH_2$—$CH_2$—,
(c) —$CH_2$—$CH_2$—$CH_2$—$CZ^1Z^2$—$CH_2$—,
(d) —$CZ^1Z^2$—$CH_2$—$CH_2$—$CH_2$—$NZ^3$—,
(e) —$CZ^1Z^2$—$CH_2$—$CZ^1Z^2$—C(=O)—$NZ^3$—,
(f) —$CH_2$—$CH_2$—$CH_2$—$NZ^3$—C(=O)—,
(h) —$CH_2$—$CH_2$—C(=O)—$NZ^3$—$CZ^1Z^2$—,
(i) —$CH_2$—$CH_2$—$NZ^3$—$CH_2$—$CH_2$—,
(j) —$CH_2$—$CH_2$—O—$CH_2$—$CH_2$—,
(k) —$CH_2$—$CH_2$—O—C(=O)—$NZ^3$—,
(l) —$CH_2$—$CH_2$—$NZ^3$—C(=O)—$CZ^1Z^2$—,
(m) —$CH_2$—C(=O)—$NZ^3$—$CH_2$—$CH_2$—,
(n) —$CH_2$—$NZ^3$—$CH_2$—$CH_2$—$NZ^3$—,
(o) —$CH_2$—O—$CH_2$—$CH_2$—$NZ^3$
(p) —$CH_2$—$NZ^3$—$CH_2$—$CH_2$—O—,
(q) —$CH_2$—$NZ^3$—$CH_2$—$CH_2$—S—,
(r) —$CH_2$—$NZ^3$—$CH_2$—$CH_2$—$SO_2$—,
(s) —$CH_2$—$NZ^3$—$CH_2$—C(=O)—$NZ^3$—,
(t) —$CZ^1Z^2$—$NZ^3$—C(=O)—$CH_2$—$CH_2$—,
(u) —$CH_2$—$NZ^3$—C(=O)—CH=CH—,
(v) —$CH_2$—$NZ^3$—C(=O)—$NZ^3$—$CH_2$—,
(w) —C(=O)—$CH_2$—$CZ^1Z^2$—$CH_2$—$CH_2$—,
(x) —C(=O)—$NZ^3$—$CH_2$—$CH_2$—$CH_2$—,
(y) —C(=O)—$NZ^3$—$CH_2$—$CH_2$—O—,
(z) —C(=O)—$NZ^3$—$CZ^1Z^2$—$CZ^1Z^2$—$NZ^3$—,
(aa) —$NZ^3$—$CH_2$—$CZ^1Z^2$—$CH_2$—$CZ^1Z^2$—,
(bb) —$NZ^3$—$CH_2$—$CZ^1Z^2$—$CH_2$—O—,
(cc) —$NZ^3$—$CH_2$—$CH_2$—$NZ^3$—$CH_2$—,
(dd) —$NZ^3$—$CH_2$—$CH_2$—$NZ^3$—C(=O)—,
(ee) —$NZ^3$—$CH_2$—C(=O)—NH—$CH_2$—,
(ff) —$NZ^3$—C(=O)—$CZ^1Z^2$—$CH_2$—$CZ^1Z^2$—,
(gg) —$NZ^3$—C(=O)—$CH_2$—$CH_2$—O—,
(hh) —$NZ^3$—C(=O)—$CH_2$—$NZ^3$—$CZ^1Z^2$—,
(ii) —$NZ^3$—C(=O)—O—$CH_2$—$CH_2$—,
(jj) —O—$CH_2$—$CH_2$—$CH_2$—$CZ^1Z^2$—,
(kk) —O—$CH_2$—$CH_2$—$NZ^3$—C(=O)—,
(ll) —O—$CH_2$—$CZ^1Z^2$—$CH_2$—$NZ^3$—,
(mm) —O—$CH_2$—$CH_2$—$CH_2$—O—,
(nn) —$CH_2$—$NZ^3$—C(=O)—$CH_2$—$CH_2$—$NZ^3$—, (oo)
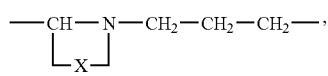

wherein X, combined with the atoms to which it is attached, is an imidazolyl group, (pp)
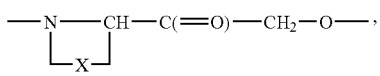

wherein X, combined with the atoms to which it is attached, is a pyrrolyl group, (qq)
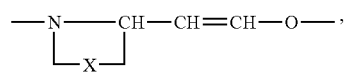

wherein X, combined with the atoms to which it is attached, is a pyrrolyl group, (rr)
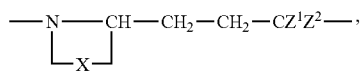

wherein X, combined with the atoms to which it is attached, is an imidazolyl group optionally substituted by $C_{1-6}$-alkyl, (ss)
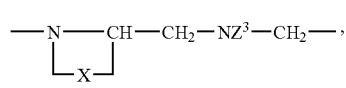

wherein X, combined with the atoms to which it is attached, is an imidazolyl group, (tt)
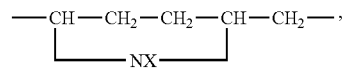

wherein X is chosen from H, $C_{1-6}$-alkyl, —$C_{1-6}$-alkyl-$C_{3-6}$-cycloalkyl, —$C_{1-6}$-alkyl-O—$C_{1-6}$-alkyl, —C(=O)$C_{3-6}$-cycloalkyl, —C(=O)O$C_{1-6}$-alkyl, $C_{2-6}$-alkynyl, and —S(=O)$_2$—$C_{1-6}$-alkyl, (uu)
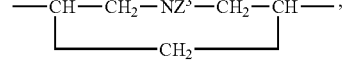

(vv)
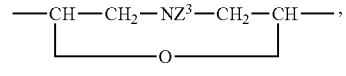

(ww)
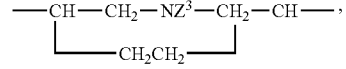

(xx)
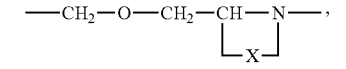

wherein X is chosen from $C_{1-6}$-alkyl, or (yy)
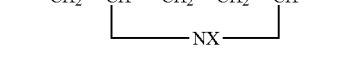

wherein X is —C(=O)O$C_{1-6}$-alkyl, wherein each $Z^1$ and $Z^2$ is independently chosen from H, halogen, $C_{1-6}$-alkyl, —$C_{1-6}$-alkyl-OH, —N$R^{40}R^{41}$, —OH, 6 membered heterocycloalkyl, 6 membered heterocycloalkyl-$R^{45}$, —NHC(=O)$C_{1-6}$-alkyl, —NHC(=O)$C_{1-6}$-haloalkyl, —NHC(=O)$C_{1-6}$-alkyl-N($C_{1-6}$-alkyl)$_2$, —NHC(=O)$C_{1-6}$- alkyl-O—C$_{1-4}$-alkyl, —NHC(═O)-(5 membered heterocycloalkyl), —NHC(═O)-(cyclopropyl), and —NHC(═O) OC$_{1-6}$-alkyl, R$^{40}$ and R$^{41}$ are independently chosen from H, C$_{1-6}$-alkyl, C$_{1-4}$-haloalkyl, —C$_{1-6}$-alkyl-OH, and —C$_{1-6}$-alkyl-O—C$_{1-4}$-alkyl, R$^{45}$ is chosen from —OH, C$_{1-6}$-alkyl, and 6 membered heterocycloalkyl-C$_{1-6}$-alkyl, Z$^3$ is chosen from H, C$_{1-6}$-alkyl, —C$_{1-6}$-alkyl-R$^{45a}$, —C$_{1-6}$-alkyl-(O—C$_{1-6}$-alkyl)$_2$, —C(═O)C$_{1-6}$-alkyl, —C(═O)C$_{1-6}$-alkyl-O—C$_{1-4}$-alkyl, —C(═O)C$_{1-6}$-haloalkyl, —C(═O)-(5-6-membered heterocycloalkyl), —C(═O)C$_{1-6}$-alkyl-(5-6-membered heterocycloalkyl), —C(═O)-(5-membered heteroaryl), —C(═O)C$_{1-6}$-alkyl-(5-membered heteroaryl), —C(═O)C$_{1-6}$-alkyl-(9-membered heteroaryl-(R$^{79}$)$_2$), —C(═O)C$_{1-6}$-alkyl-NH$_2$, —C(═O)C$_{1-6}$-alkyl-N(C$_{1-6}$-alkyl)$_2$, C$_{1-6}$-haloalkyl, —C(═O)OC$_{1-6}$-alkyl, —C(═O)OC$_{1-6}$-alkyl-phenyl, —C(═O)OC$_{1-6}$-alkyl-N(C$_{1-6}$-alkyl)$_2$, —C(═O)OC$_{1-6}$-alkyl-O—C$_{1-4}$-alkyl, —C(═O)O-(6-membered heterocycloalkyl-C$_{1-6}$-alkyl), —C(═O)N(C$_{1-6}$alkyl)$_2$, —C$_{1-6}$-haloalkyl-OH, —C$_{1-6}$-haloalkyl-O—C$_{1-6}$-alkyl, C$_{2-6}$-alkenyl, C$_{2-6}$-alkynyl, and —S(═O)$_2$—C$_{1-6}$-alkyl, wherein R$^{45a}$ is chosen from —OH, —O—C$_{1-6}$-alkyl, 5-6 membered heterocycloalkyl, C$_{3-6}$-cycloalkyl, 5 membered heteroaryl, 5 membered heteroaryl-C$_{1-6}$-alkyl, phenyl, —SO$_2$—C$_{1-6}$-alkyl, —C(═O)NR$^{62}$R$^{63}$, —C(═O)OC$_{1-6}$-alkyl, —C(═O)OC$_{1-6}$-alkyl-O—C$_{1-4}$-alkyl, —C(═O)O—C$_{1-6}$-alkyl, —C(═O)-(4-6 membered heterocycloalkyl), —C(═O)-(6 membered heterocycloalkyl-C$_{1-6}$-alkyl), —OC(═O)C$_{1-6}$-alkyl, —OC(═O)C$_{1-6}$-alkyl-NH$_2$, —OP(═O)(OH)$_2$, —NHC(═O)—C$_{1-6}$-alkyl, —N(C$_{1-6}$-alkyl)$_2$, phenyl, and —C≡N, wherein R$^{62}$ and R$^{63}$ are each independently chosen from H and C$_{1-6}$alkyl, and each R$^{79}$ is ═O.

In another embodiment, -A$^1$-A$^2$-A$^3$-A$^4$-A$^5$- is a group of formula:

(a) —CH$_2$—CZ$^1$Z$^2$—CH$_2$—CH$_2$—CH$_2$—, wherein Z$^1$ and Z$^2$ are each independently chosen from H and 6-membered heterocycloalkyl, (b) —CH$_2$—CH$_2$—CZ$^1$Z$^2$—CH$_2$—CH$_2$—, wherein Z$^1$ and Z$^2$ are each independently chosen from H, halogen, —NR$^{40}$R$^{41}$, 6 membered heterocycloalkyl, and 6 membered heterocycloalkyl-R$^{45}$, wherein R$^{40}$ and R$^{41}$ are independently chosen from H, C$_{1-6}$-alkyl, —C$_{1-6}$-alkyl-OH, —C$_{1-6}$-alkyl-O—C$_{1-4}$-alkyl, and C$_{1-4}$ haloalkyl, and R$^{45}$ is chosen from —OH, C$_{1-6}$-alkyl, and 6 membered heterocycloalkyl-C$_{1-6}$-alkyl, (c) —CH$_2$—CH$_2$—CH$_2$—CZ$^1$Z$^2$—CH$_2$—, wherein Z$^1$ and Z$^2$ are each independently chosen from H, 6 membered heterocycloalkyl, and —NR$^{40}$R$^{41}$, wherein R$^{40}$ and R$^{41}$ are independently chosen from H, and —C$_{1-6}$-alkyl-O—C$_{1-4}$-alkyl, (d) —CZ$^1$Z$^2$—CH$_2$—CH$_2$—CH$_2$—NZ$^3$—, wherein Z$^1$, Z$^2$, and Z$^3$ are each independently chosen from H and C$_{1-6}$-alkyl, (e) —CZ$^1$Z$^2$—CH$_2$—CZ$^1$Z$^2$—C(═O)—NZ$^3$—, wherein Z$^1$ and Z$^2$ are each independently chosen from H, C$_{1-6}$-alkyl, —NR$^{40}$R$^{41}$, and 6 membered heterocycloalkyl, and Z$^3$ is chosen from H, C$_{1-6}$-alkyl, —C$_{1-6}$-alkyl-C(═O)OC$_{1-6}$-alkyl, —C$_{1-6}$-alkyl-C(═O)OH, —C$_{1-6}$-alkyl-C(═O)-(6-membered heterocycloalkyl-C$_{1-6}$-alkyl), and —C$_{1-6}$-alkyl-O—C$_{1-4}$-alkyl, wherein R$^{40}$ and R$^{41}$ are independently chosen from H, C$_{1-6}$-alkyl, —C(═O)C$_{1-6}$-alkyl-N(C$_{1-6}$-alkyl)$_2$, —C(═O)C$_{3-6}$-cycloalkyl, —C(═O)C$_{1-4}$-haloalkyl, and —C(═O)C$_{1-6}$-alkyl-O—C$_{1-4}$-alkyl, (f) —CH$_2$—CH$_2$—CH$_2$—NZ$^3$—C(═O)—, wherein Z$^3$ is chosen from H and C$_{1-6}$-alkyl, (g) —CH$_2$—CH$_2$—C(═O)—CH$_2$—CH$_2$—, (h) —CH$_2$—CH$_2$—C(═O)—NZ$^3$—CZ$^1$Z$^2$—, wherein Z$^1$, Z$^2$, and Z$^3$ are each independently chosen from H and C$_{1-6}$-alkyl, (i) —CH$_2$—CH$_2$—NZ$^3$—CH$_2$—CH$_2$—, wherein Z$^3$ is chosen from H, C$_{1-6}$-alkyl, —C$_{1-6}$-alkyl-(O—C$_{1-6}$-alkyl)$_2$, —C$_{1-6}$-alkyl-R$^{45}$, —C(═O)C$_{1-6}$-haloalkyl, —C(═O)-(6-membered heterocycloalkyl), —C(═O)C$_{1-6}$-alkyl-(6-membered heterocycloalkyl), —C(═O)—C$_{1-6}$-alkyl-NH$_2$, —C(═O)—C$_{1-6}$-alkyl-N(C$_{1-6}$-alkyl)$_2$, C$_{1-6}$-haloalkyl, —C(═O)N(C$_{1-6}$alkyl)$_2$, —C$_{1-6}$-fluoroalkyl-OH, —C$_{1-6}$-haloalkyl-O—C$_{1-6}$-alkyl, C$_{2-6}$-alkynyl, and —S(═O)$_2$—C$_{1-6}$-alkyl, wherein R$^{45}$ is chosen from —OH, —OC$_{1-6}$-alkyl, 6 membered heterocycloalkyl, C$_{3-6}$-cycloalkyl, 5 membered heteroaryl, 5 membered heteroaryl-C$_{1-6}$-alkyl, —SO$_2$—C$_{1-6}$-alkyl, —C(═O)NR$^{62}$R$^{63}$, —C(═O)OC$_{1-6}$-alkyl, —C(═O)-(4-6 membered heterocycloalkyl), —C(═O)-(6 membered heterocycloalkyl-C$_{1-6}$-alkyl), —OC(═O)C$_{1-6}$-alkyl, —OC(═O)C$_{1-6}$-alkyl-NH$_2$, —OP(═O)(OH)$_2$, and —NHC(═O)—C$_{1-6}$-alkyl, wherein R$^{62}$ and R$^{63}$ are each independently chosen from H and C$_{1-6}$-alkyl, (j) —CH$_2$—CH$_2$—O—CH$_2$—CH$_2$—, (k) —CH$_2$—CH$_2$—O—C(═O)—NZ$^3$—, wherein Z$^3$ is chosen from H and C$_{1-6}$-alkyl, (l) —CH$_2$—CH$_2$—NZ$^3$—C(═O)—CZ$^1$Z$^2$—, wherein Z$^1$ and Z$^2$ are each independently chosen from H and C$_{1-6}$-alkyl, and Z$^3$ is chosen from H, C$_{1-6}$-alkyl, —C$_{1-6}$-alkyl-N(C$_{1-6}$-alkyl)$_2$, and —C$_{1-6}$-alkyl-(6-membered heterocycloalkyl), (m) —CH$_2$—C(═O)—NZ$^3$—CH$_2$—CH$_2$—, wherein Z$^3$ is chosen from H and C$_{1-6}$-alkyl, (n) —CH$_2$—NZ$^3$—CH$_2$—CH$_2$—NZ$^3$—, wherein each Z$^3$ is independently chosen from H, C$_{1-6}$-alkyl, —C(═O)—C$_{1-6}$-alkyl, and —C$_{1-6}$-alkyl-O—C$_{1-4}$-alkyl, (o) —CH$_2$—O—CH$_2$—CH$_2$—NZ$^3$—, wherein Z$^3$ is chosen from H and C$_{1-6}$-alkyl, (p) —CH$_2$—NZ$^3$—CH$_2$—CH$_2$—O—, wherein Z$^3$ is chosen from H, C$_{1-6}$-alkyl, and —C$_{1-6}$-alkyl-O—C$_{1-4}$-alkyl, (q) —CH$_2$—NZ$^3$—CH$_2$—CH$_2$—S—, wherein Z$^3$ is chosen from H, C$_{1-6}$-alkyl, —C$_{1-6}$-alkyl-O—C$_{1-4}$-alkyl, —C$_{1-6}$-alkyl-OH, and —C$_{1-6}$-alkyl-OC(═O)—C$_{1-6}$-alkyl, (r) —CH$_2$—NZ$^3$—CH$_2$—CH$_2$—SO$_2$—, wherein Z$^3$ is chosen from H and C$_{1-6}$-alkyl, (s) —CH$_2$—NZ$^3$—CH$_2$—C(═O)—NZ$^3$—, wherein each Z$^3$ is independently chosen from H, C$_{1-6}$-alkyl, and C$_{1-6}$-alkyl-phenyl, (t) —CZ$^1$Z$^2$—NZ$^3$—C(═O)—CH$_2$—CH$_2$—, wherein Z$^1$, Z$^2$, and Z$^3$ are each independently chosen from H and C$_{1-6}$-alkyl, (u) —CH$_2$—NZ$^3$—C(═O)—CH═CH—, wherein Z$^3$ is chosen from H and C$_{1-6}$-alkyl, (v) —CH$_2$—NZ$^3$—C(═O)—NZ$^3$—CH$_2$—, wherein each Z$^3$ is independently chosen from H and C$_{1-6}$-alkyl, (w) —C(═O)—CH$_2$—CZ$^1$Z$^2$—CH$_2$—CH$_2$—, wherein Z$^1$ and Z$^2$ are independently chosen from H and —NHC(═O)C$_{1-6}$-alkyl, (x) —C(═O)—NZ$^3$—CH$_2$—CH$_2$—CH$_2$—, wherein Z$^3$ is chosen from H and C$_{1-6}$-alkyl, (y) —C(═O)—NZ$^3$—CH$_2$—CH$_2$—O—, wherein Z$^3$ is chosen from H and C$_{1-6}$-alkyl, (z) —C(═O)—NZ$^3$—CZ$^1$Z$^2$—CZ$^1$Z$^2$—NZ$^3$—, wherein each Z$^1$ and Z$^2$ is independently chosen from H and C$_{1-6}$-alkyl, and each Z$^3$ is independently chosen from H, C$_{1-6}$-alkyl, and —C(=O)—C$_{1-6}$-haloalkyl, (aa) —NZ$^3$—CH$_2$—CZ$^1$Z$^2$—CH$_2$—CZ$^1$Z$^2$—, wherein each Z$^1$ and Z$^2$ is independently chosen from H, C$_{1-6}$-alkyl, and —NH—C$_{1-6}$-alkyl-O—C$_{1-4}$-alkyl, and Z$^3$ is chosen from H, C$_{1-6}$-alkyl, —C(=O)—C$_{1-6}$-alkyl, and —C$_{1-6}$-alkyl-N(C$_{1-6}$-alkyl)$_2$, (bb) —NZ$^3$—CH$_2$—CZ$^1$Z$^2$—CH$_2$—O—, wherein Z$^1$ and Z$^2$ are each independently chosen from H, —OH, C$_{1-6}$-alkyl-OH, and 6 membered heterocycloalkyl, and Z$^3$ is chosen from H, C$_{1-6}$-alkyl, —C(=O)—C$_{1-6}$-alkyl, —C(=O)—C$_{1-6}$-alkyl-(5-membered heteroaryl), and —C(=O)O—C$_{1-6}$-alkyl, (cc) —NZ$^3$—CH$_2$—CH$_2$—NZ$^3$—CH$_2$—, wherein each Z$^3$ is independently chosen from H, C$_{1-6}$-alkyl, —C(=O)—C$_{1-6}$-alkyl, —C$_{1-6}$-alkyl-OC(=O)C$_{1-6}$-alkyl, —C$_{1-6}$-alkyl-C(=O)C$_{1-6}$-alkyl, —SO$_2$—C$_{1-6}$-alkyl, —C$_{1-6}$-alkyl-OH, —C$_{1-6}$-alkyl-O—C$_{1-4}$-alkyl, -alkyl-C$_{3-6}$-cycloalkyl, C$_{2-6}$-alkynyl, —C(=O)-(5-membered heteroaryl), —C(=O)N(C$_{1-6}$-alkyl)$_2$, —C$_{1-6}$-haloalkyl-OH, and —C$_{1-6}$-alkyl-C(=O)N(C$_{1-6}$-alkyl)$_2$, (dd) —NZ$^3$—CH$_2$—CH$_2$—NZ$^3$—C(=O)—, wherein each Z$^3$ is independently chosen from H, C$_{1-6}$-alkyl, —C$_{1-6}$-alkyl-N(C$_{1-6}$-alkyl)$_2$, —C$_{2-6}$-alkenyl, and —C$_{1-6}$-alkyl-C(=O)O—C$_{1-6}$-alkyl-O—C$_{1-4}$-alkyl, (ee) —NZ$^3$—CH$_2$—C(=O)—NZ$^3$—CH$_2$—, wherein each Z$^3$ is independently chosen from H, C$_{1-6}$-alkyl, and —C(=O)—C$_{1-6}$-alkyl, (ff) —NZ$^3$—C(=O)—CZ$^1$Z$^2$—CH$_2$—CZ$^1$Z$^2$—, wherein each Z$^1$ and Z$^2$ is independently chosen from H, C$_{1-6}$-alkyl, —NHC(=O)C$_{1-6}$-haloalkyl, —NH$_2$, —NHC(=O)C$_{1-6}$-alkyl-N(C$_{1-6}$-alkyl)$_2$, 6 membered heterocycloalkyl, —NHC(=O)C$_{1-6}$-alkyl, —NHC(=O)C$_{1-6}$-alkyl-O—C$_{1-4}$-alkyl, —NHC(=O)-(5 membered heterocycloalkyl), —NHC(=O)OC$_{1-6}$-alkyl, and —NHC$_{1-6}$-alkyl-O—C$_{1-4}$-alkyl, Z$^3$ is chosen from H, C$_{1-6}$-alkyl, —C$_{1-6}$-alkyl-O—C$_{1-4}$-alkyl, —C(=O)C$_{1-6}$-alkyl, —C(=O)C$_{1-6}$-alkyl-(5-membered heterocycloalkyl), —C$_{1-6}$-alkyl-(5-membered heterocycloalkyl), —C(=O)—C$_{1-6}$-alkyl-(9-membered heteroaryl-(R$^{79}$)$_2$), —C(=O)C$_{1-6}$-alkyl-N(R$^{76}$)$_2$, and —C(=O)-(5-membered heterocycloalkyl), each R$^{76}$ is independently chosen from H and C$_{1-6}$-alkyl, and each R$^{79}$ is =O, (gg) —NZ$^3$—C(=O)—CH$_2$—CH$_2$—O—, wherein Z$^3$ is chosen from H and C$_{1-6}$-alkyl, (hh) —NZ$^3$—C(=O)—CH$_2$—NZ$^3$—CZ$^1$Z$^2$—, wherein Z$^1$ and Z$^2$ are each independently chosen from H and C$_{1-6}$-alkyl, and each Z$^3$ is independently chosen from H, C$_{1-6}$-alkyl, —C$_{1-6}$-alkyl-O—C$_{1-4}$-alkyl, —C$_{1-6}$-alkyl-C(=O)N(C$_{1-6}$-alkyl)$_2$, —C$_{1-6}$-alkyl-C≡N, —C$_{1-6}$-alkyl-C$_{3-6}$-cycloalkyl, —C(=O)C$_{1-6}$-alkyl, —C(=O)C$_{1-6}$-haloalkyl, —C(=O)OC$_{1-6}$-alkyl-phenyl, -alkyl-phenyl, —SO$_2$C$_{1-6}$-alkyl, C$_{1-6}$-haloalkyl, C$_{1-6}$-alkyl-OH, and —C(=O)OC$_{1-6}$-alkyl, (ii) —NZ$^3$—C(=O)—O—CH$_2$—CH$_2$—, wherein Z$^3$ is chosen from H and C$_{1-6}$-alkyl, (jj) —O—CH$_2$—CH$_2$—CH$_2$—CZ$^1$Z$^2$—, wherein Z$^1$ and Z$^2$ are each independently chosen from H and C$_{1-6}$-alkyl, (kk) —O—CH$_2$—CH$_2$—NZ$^3$—C(=O)—, wherein Z$^3$ is chosen from H and C$_{1-6}$-alkyl, (ll) —O—CH$_2$—CZ$^1$Z$^2$—CH$_2$—NZ$^3$—, wherein Z$^1$ and Z$^2$ are each independently chosen from H, C$_{1-6}$-alkyl, C$_{1-6}$-alkyl-OH, and —OH, and Z$^3$ is chosen from H, C$_{1-6}$-alkyl, —C(=O)OC$_{1-6}$-alkyl, —C(=O)OC$_{1-6}$-alkyl-N(C$_{1-6}$-alkyl)$_2$, —C(=O)C$_{1-6}$-alkyl-(5-membered heterocycloalkyl), —C$_{1-6}$-alkyl-(5-membered heterocycloalkyl), —C(=O)OC$_{1-6}$-alkyl-O—C$_{1-4}$-alkyl, —C(=O)O-(6-membered heterocycloalkyl-C$_{1-6}$-alkyl), —C(=O)C$_{1-6}$-alkyl, and —C(=O)C$_{1-6}$-alkyl-O—C$_{1-4}$-alkyl, (mm) —O—CH$_2$—CH$_2$—CH$_2$—O—, (nn) —CH$_2$—NZ$^3$—C(=O)—CH$_2$—CH$_2$—NZ$^3$—, wherein each Z$^3$ is independently chosen from H, —C(=O)C$_{1-6}$-alkyl, and —C(=O)C$_{1-6}$-haloalkyl, (oo) —CH—N—CH$_2$—CH$_2$—CH$_2$—
$\lfloor X \rfloor$, wherein X, combined with the atoms to which it is attached, is an imidazolyl group, (pp) 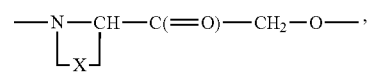

wherein X, combined with the atoms to which it is attached, is a pyrrolyl group, (qq) 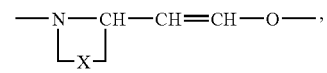

wherein X, combined with the atoms to which it is attached, is a pyrrolyl group, (rr) 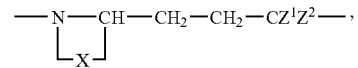

wherein X, combined with the atoms to which it is attached, is an imidazolyl group optionally substituted by C$_{1-6}$-alkyl, and Z$^1$ and Z$^2$ are each independently chosen from H and C$_{1-6}$-alkyl, (ss) 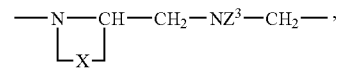

wherein X, combined with the atoms to which it is attached, is an imidazolyl group, and Z$^3$ is chosen from H and C$_{1-6}$-alkyl, (tt) 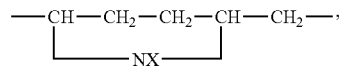

wherein X is chosen from H, C$_{1-6}$-alkyl, —C$_{1-6}$-alkyl-C$_{3-6}$-cycloalkyl, —C$_{1-6}$-alkyl-O—C$_{1-6}$-alkyl, —C(=O)C$_{3-6}$-cycloalkyl, —C(=O)OC$_{1-6}$-alkyl, C$_{2-6}$-alkynyl, and —S(=O)$_2$—C$_{1-6}$-alkyl, (uu) 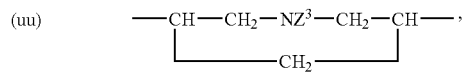

wherein $Z^3$ is chosen from $C_{1-6}$-alkyl, —$C_{1-6}$-alkyl-O—$C_{1-6}$-alkyl, and —S(=O)$_2$—$C_{1-6}$-alkyl, (vv) 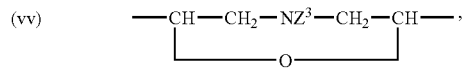

wherein $Z^3$ is chosen from H, $C_{1-6}$-alkyl, $C_{2-6}$-alkynyl, and —S(=O)$_2$—$C_{1-6}$-alkyl, (ww) 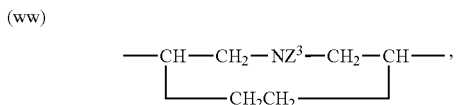

wherein $Z^3$ is chosen from H, $C_{1-6}$-alkyl, —C(=O)$C_{1-6}$-alkyl, —$C_{1-6}$-alkyl-CN, —C(=O)$C_{1-6}$-haloalkyl, $C_{1-6}$-haloalkyl, —$C_{1-6}$-alkyl-O—$C_{1-6}$-alkyl, $C_{2-6}$-alkynyl, and —S(=O)$_2$—$C_{1-6}$-alkyl, (xx) 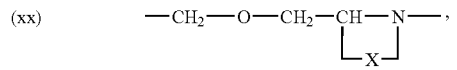

wherein X is chosen from —CH$_2$—CH$_2$—CH$_2$— and —CH$_2$—CH$_2$—CH$_2$—CH$_2$—, or (yy) 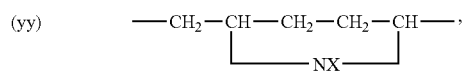

wherein X is —C(=O)O$C_{1-6}$-alkyl.

In another embodiment, -A$^1$-A$^2$-A$^3$-A$^4$-A$^5$- is a group of formula:
(a) —CH$_2$—CH$_2$—CZ$^1$Z$^2$—CH$_2$—CH$_2$—, wherein $Z^1$ and $Z^2$ are independently chosen from H, halogen, and 6-membered heterocycloalkyl,
(b) —CZ$^1$Z$^2$—CH$_2$—CH$_2$—CH$_2$—NZ$^3$—, wherein $Z^1$, $Z^2$, and $Z^3$ are independently chosen from H and $C_{1-6}$-alkyl,
(c) —CZ$^1$Z$^2$—CH$_2$—CZ$^1$Z$^2$—C(=O)—NZ$^3$—, wherein $Z^1$ and $Z^2$ are independently chosen from H and $C_{1-6}$-alkyl, and $Z^3$ is chosen from H, $C_{1-6}$-alkyl, —$C_{1-6}$-alkyl-C(=O)OH, —$C_{1-6}$-alkyl-C(=O)O—$C_{1-6}$-alkyl, —$C_{1-6}$-alkyl-C(=O)-6 membered heterocycloalkyl-$C_{1-6}$-alkyl, and —$C_{1-6}$-alkyl-O—$C_{1-6}$-alkyl,
(d) —CH$_2$—CH$_2$—CH$_2$—NZ$^3$—C(=O)—, wherein $Z^3$ is chosen from H and $C_{1-6}$-alkyl,
(e) —CH$_2$—CH$_2$—C(=O)—CH$_2$—CH$_2$—,
(f) —CH$_2$—CH$_2$—NZ$^3$—CH$_2$—CH$_2$—, wherein $Z^3$ is chosen from H, $C_{1-6}$-alkyl, —C(=O)$C_{1-6}$-fluoroalkyl, —C(=O)N($C_{1-6}$alkyl)($C_{1-6}$-alkyl), —$C_{1-6}$-alkyl-O—$C_{1-6}$-alkyl, —$C_{1-6}$-alkyl-C(=O)N($C_{1-6}$alkyl)($C_{1-6}$-alkyl), —$C_{1-6}$-alkyl-NHC(=O)—$C_{1-6}$-alkyl, $C_{1-6}$-fluoroalkyl, —$C_{1-6}$-fluoroalkyl-OH, —$C_{1-6}$-fluoroalkyl-O—$C_{1-6}$-alkyl, $C_{2-6}$-alkynyl, and —S(=O)$_2$—$C_{1-6}$-alkyl,
(g) —CH$_2$—CH$_2$—O—CH$_2$—CH$_2$—,
(h) —CH$_2$—CH$_2$—NZ$^3$—C(=O)—CZ$^1$Z$^2$—, wherein $Z^1$, $Z^2$, and $Z^3$ are independently chosen from H and $C_{1-6}$-alkyl,
(i) —CH$_2$—NZ$^3$—CH$_2$—CH$_2$—NZ$^{3a}$—, wherein $Z^3$ is chosen from H, —C(=O)$C_{1-6}$-alkyl, and —$C_{1-6}$-alkyl-O—$C_{1-6}$-alkyl, and $Z^{3a}$ is chosen from H and $C_{1-6}$-alkyl,
(j) —CH$_2$—O—CH$_2$—CH$_2$—NZ$^3$—, wherein $Z^3$ is $C_{1-6}$-alkyl,
(k) —CH$_2$—NH—CH$_2$—CH$_2$—O—,
(l) —CH$_2$—NZ$^3$—CH$_2$—CH$_2$—S—, wherein $Z^3$ is chosen from H, $C_{1-6}$-alkyl, —$C_{1-6}$-alkyl-OH, —$C_{1-6}$-alkyl-O—$C_{1-6}$-alkyl, and —$C_{1-6}$-alkyl-OC(=O)—$C_{1-6}$-alkyl,
(m) —CH$_2$—NH—CH$_2$—CH$_2$—SO$_2$—,
(n) —CH$_2$—NH—C(=O)—NH—CH$_2$—,
(o) —C(=O)—NZ$^3$—CH$_2$—CH$_2$—CH$_2$—, wherein $Z^3$ is chosen from H and $C_{1-6}$-alkyl,
(p) —C(=O)—NZ$^3$—CZ$^1$Z$^2$—CZ$^1$Z$^2$—NZ$^{3a}$—, wherein $Z^1$, $Z^2$, and $Z^3$ are independently chosen from H and $C_{1-6}$-alkyl, and $Z^{3a}$ is chosen from H, $C_{1-6}$-alkyl, and —C(=O)$C_{1-6}$-haloalkyl,
(q) —NZ$^3$—CH$_2$—CH$_2$—NZ$^{3a}$—CH$_2$—, wherein $Z^3$ is $C_{1-6}$-alkyl, and $Z^{3a}$ is chosen from H, $C_{1-6}$-alkyl, —C(=O)N($C_{1-6}$alkyl)($C_{1-6}$-alkyl), —$C_{1-6}$-alkyl-$C_{3-6}$-cycloalkyl, —$C_{1-6}$-alkyl-OH, —$C_{1-6}$-alkyl-O—$C_{1-6}$-alkyl, —$C_{1-6}$-alkyl-OC(=O)—$C_{1-6}$-alkyl, —C(=O)-5-membered heteroaryl, —$C_{1-6}$-alkyl-C(=O)O—$C_{1-6}$-alkyl, —$C_{1-6}$-fluoroalkyl-OH, $C_{2-6}$-alkynyl, and —S(=O)$_2$—$C_{1-6}$-alkyl,
(r) —NZ$^3$—CH$_2$—CH$_2$—NZ$^3$—, C(=O)—, wherein $Z^3$ is chosen from H, $C_{1-6}$-alkyl, —$C_{1-6}$-alkyl-N($C_{1-6}$alkyl)($C_{1-6}$-alkyl), and $C_{2-6}$-alkenyl, and $Z^{3a}$ is chosen from H and $C_{1-6}$-alkyl,
(s) —NZ$^3$—C(=O)—CH$_2$—CH$_2$—CH$_2$—, wherein $Z^3$ is chosen from H, $C_{1-6}$-alkyl, and —$C_{1-6}$-alkyl-O—$C_{1-6}$-alkyl,
(t) —O—CH$_2$—CH$_2$—NZ$^3$—C(=O)—, wherein $Z^3$ is chosen from H and $C_{1-6}$-alkyl,
(u) —O—CH$_2$—CH$_2$—CH$_2$—O—, (v) 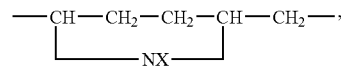

wherein X is chosen from H, $C_{1-6}$-alkyl, —$C_{1-6}$-alkyl-$C_{3-6}$-cycloalkyl, —$C_{1-6}$-alkyl-O—$C_{1-6}$-alkyl, —C(=O)$C_{3-6}$-cycloalkyl, —C(=O)O$C_{1-6}$-alkyl, $C_{2-6}$-alkynyl, and —S(=O)$_2$—$C_{1-6}$-alkyl, (w) 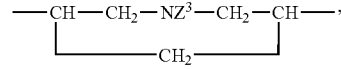

wherein $Z^3$ is chosen from $C_{1-6}$-alkyl, —$C_{1-6}$-alkyl-O—$C_{1-6}$-alkyl, and —S(=O)$_2$—$C_{1-6}$-alkyl, (x) 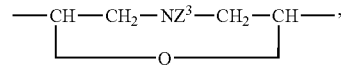

wherein $Z^3$ is chosen from H, $C_{1-6}$-alkyl, $C_{2-6}$-alkynyl, and —S(=O)$_2$—$C_{1-6}$-alkyl, (y) 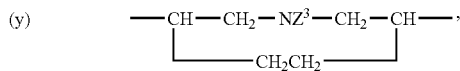

wherein $Z^3$ is chosen from H, $C_{1-6}$-alkyl, —C(═O)$C_{1-6}$-alkyl, —$C_{1-6}$-alkyl-CN, —C(═O)$C_{1-6}$-haloalkyl, $C_{1-6}$-haloalkyl, —$C_{1-6}$-alkyl-O—$C_{1-6}$-alkyl, $C_{2-6}$-alkynyl, and —S(═O)$_2$—$C_{1-6}$-alkyl, (z) 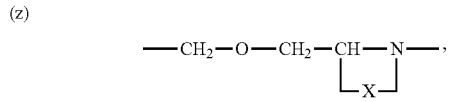

wherein X is chosen from —CH$_2$—CH$_2$—CH$_2$— and —CH$_2$—CH$_2$—CH$_2$—CH$_2$—, or (aa) 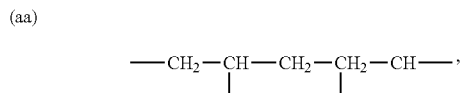

wherein X is —C(═O)O$C_{1-6}$-alkyl.

In another embodiment, -$A^1$-$A^2$-$A^3$-$A^4$-$A^5$- is a group of formula:
- (a) —CH$_2$—CHZ$^1$—CH$_2$—CH$_2$—CH$_2$—, wherein $Z^1$ is chosen from H and 4-morpholinyl,
- (b) —CH$_2$—CH$_2$—CZ$^1$Z$^2$—CH$_2$—CH$_2$—, wherein $Z^1$ is chosen from H and F, and $Z^2$ is chosen from H, F, —OH, —NHCH$_2$CF$_3$, —NHCH$_2$CHF$_2$, —NH(CH$_2$)$_2$OCH$_3$, —NH(CH$_2$)$_2$OH, —N(CH$_3$)(CH$_2$)$_2$OCH$_3$, 4-(4-methylpiperazin-1-yl)piperidin-1-yl, 4-methylpiperazin-1-yl, and 3-hydroxypiperidin-1-yl,
- (c) —CH$_2$—CH$_2$—CH$_2$—CHZ$^1$—CH$_2$—, wherein $Z^1$ is chosen from H, 4-morpholinyl, and —NHCH$_2$CH$_2$OCH$_3$,
- (d) —CZ$^1$Z$^2$—CH$_2$—CH$_2$—CH$_2$—NZ$^3$—, wherein $Z^1$, $Z^2$, and $Z^3$ are each independently chosen from H and methyl,
- (e) —CZ$^1$Z$^2$—CH$_2$—CZ$^{1a}$Z$^{2a}$—C(═O)—NZ$^3$—, wherein $Z^1$ and $Z^2$ are independently chosen from H and —CH$_3$, $Z^{1a}$ and $Z^{2a}$ are both H or —CH$_3$, or $Z^{1a}$ is H and $Z^{2a}$ is chosen from H, methyl, —NHC(═O)CH$_2$N(CH$_3$)$_2$, —NHC(═O)cyclopropyl, —NHC(═O)CF$_3$, —NH$_2$, 4-morpholinyl, —N(CH$_3$)$_2$, and —NHC(═O)CH$_2$OCH$_3$, and $Z^3$ is chosen from H, —CH$_3$, —CH$_2$CH$_3$, —CH$_2$CO$_2$Me, —CH$_2$CO$_2$H, —CH$_2$C(═O)(4-methylpiperazinyl), —(CH$_2$)$_2$OCH$_3$, and —CH(CH$_3$)$_2$,
- (f) —CH$_2$—CH$_2$—CH$_2$—NZ$^3$—C(═O)—, wherein $Z^3$ is chosen from H and —CH$_3$,
- (g) —CH$_2$—CH$_2$—C(═O)—CH$_2$—CH$_2$—,
- (h) —CH$_2$—CH$_2$—C(═O)—NH—CZ$^1$Z$^2$—, wherein $Z^1$ and $Z^2$ are independently chosen from H and —CH$_3$,
- (i) —CH$_2$—CH$_2$—NZ$^3$—CH$_2$—CH$_2$—, wherein $Z^3$ is chosen from H, —CH$_3$, —CH$_2$CH$_3$, —CH$_2$CH$_2$CH$_3$, —CH$_2$CF$_3$, —CH$_2$CH$_2$F, —C(═O)CF$_3$, —SO$_2$CH$_3$, —CH(CH$_3$)$_2$, —CH$_2$CH$_2$OCH$_3$, —CH$_2$CF(CH$_3$)$_2$, —CH$_2$C≡CH, —C(═O)N(CH$_3$)$_2$, —CH$_2$CH(OH)CF$_3$, —CH$_2$CH$_2$NHC(═O)CH$_3$, —CH$_2$CH(OCH$_3$)CF$_3$, —CH$_2$C(═O)N(CH$_3$)$_2$, —C(═O)(1,4-dioxan-2-yl), —CH$_2$(1,4-dioxan-2-yl), —CH$_2$CHF$_2$, —CH$_2$CH$_2$SO$_2$CH$_3$, —CH$_2$-cyclopropyl, —CH$_2$CF$_2$CH$_3$, —CH$_2$C(═O)NHCH$_3$, —CH$_2$C(═O)NH$_2$, —CH$_2$C(═O)OCH(CH$_3$)$_2$, —CH(CH$_2$OCH$_3$)$_2$, —CH$_2$CH$_2$OH, —CH$_2$C(═O)-(4-morpholinyl), —CH$_2$C(═O)-(4-methylpiperazin-1-yl), —C(═O)CH$_2$N(CH$_3$)$_2$, —CH$_2$C(═O)—(1-pyrrolidinyl), —CH$_2$-(2-oxazolyl), —CH$_2$-(1-methylimidazol-2-yl), —C(═O)CH$_2$-(4-morpholinyl), —CH$_2$C(═O)-(1-azetidinyl), —CH(CH$_2$CH$_2$F)$_2$, —(CH$_2$)$_2$-(4-morpholinyl), —(CH$_2$)$_2$C(═O)CH$_2$NH$_2$, —(CH$_2$)$_2$C(═O)CH(NH$_2$)CH(CH$_3$)$_2$, —(CH$_2$)$_2$OP(═O)(OH)$_2$, —(CH$_2$)$_2$C(═O)CH$_2$CH$_3$, —CH$_2$CH(OH)CH$_3$, —C(═O)C(NH$_2$)(CH$_3$)$_2$, and —CH$_2$C(OH)(CH$_3$)$_2$,
- (j) —CH$_2$—CH$_2$—O—CH$_2$—CH$_2$—,
- (k) —CH$_2$—CH$_2$—O—C(═O)—NZ$^3$—, wherein $Z^3$ is chosen from H, —CH$_3$, and —CH$_2$CH$_3$,
- (l) —CH$_2$—CH$_2$—NZ$^3$—C(═O)—CHZ$^1$—, wherein $Z^1$ is chosen from H and —CH$_2$CH$_3$, and $Z^3$ is chosen from H, —CH$_2$CH$_3$, —(CH$_2$)$_3$N(CH$_3$)$_2$, —(CH$_2$)$_3$-(4-morpholinyl), and —(CH$_2$)$_2$-(4-morpholinyl),
- (m) —CH$_2$—C(═O)—NZ$^3$—CH$_2$—CH$_2$—, wherein $Z^3$ is chosen from H, —CH$_3$, and —CH$_2$CH$_3$,
- (n) —CH$_2$—NZ$^3$—CH$_2$—CH$_2$—NZ$^{3a}$—, wherein $Z^3$ is chosen from H, —C(═O)CH$_3$, and —CH$_2$CH$_2$—O—CH$_3$, and $Z^{3a}$ is chosen from H and —CH$_3$,
- (o) —CH$_2$—O—CH$_2$—CH$_2$—NZ$^3$—, wherein $Z^3$ is chosen from H and —CH$_3$,
- (p) —CH$_2$—NZ$^3$—CH$_2$—CH$_2$—O—, wherein $Z^3$ is chosen from H and —CH$_2$CH$_2$—O—CH$_3$,
- (q) —CH$_2$—NZ$^3$—CH$_2$—CH$_2$—S—, wherein $Z^3$ is chosen from H, —CH$_2$CH$_3$, —CH$_2$CH$_2$—O—CH$_3$, —CH$_2$CH$_2$OH, —CH$_2$CH$_2$—OC(═O)CH$_3$,
- (r) —CH$_2$—NH—CH$_2$—CH$_2$—SO$_2$—,
- (s) —CH$_2$—NZ$^3$—CH$_2$—C(═O)—NH—, wherein $Z^3$ is chosen from H and —CH$_2$-phenyl,
- (t) —CZ$^1$Z$^2$—NZ$^3$—C(═O)—CH$_2$—CH$_2$—, wherein $Z^1$, $Z^2$, and $Z^3$ are each independently chosen from H and —CH$_3$,
- (u) —CH$_2$—NZ$^3$—C(═O)—CH═CH—, wherein $Z^3$ is chosen from H and —CH$_3$,
- (v) —CH$_2$—NH—C(═O)—NH—CH$_2$—,
- (w) —C(═O)—CH$_2$—CHZ$^1$—CH$_2$—CH$_2$—, wherein $Z^1$ is chosen from H and —NHC(═O)CH$_3$,
- (x) —C(═O)—NZ$^3$—CH$_2$—CH$_2$—CH$_2$—, wherein $Z^3$ is chosen from H and —CH$_3$,
- (y) —C(═O)—NH—CH$_2$—CH$_2$—O—,
- (z) —C(═O)—NZ$^3$—CHZ$^1$—CHZ$^2$—NZ$^{3a}$—, wherein $Z^1$ and $Z^2$ are independently chosen from H and —CH$_3$, $Z^3$ is chosen from H and —CH$_3$, and $Z^{3a}$ is chosen from H, —CH$_3$, and —C(═O)CF$_3$,
- (aa) —NZ$^3$—CH$_2$—CHZ$^1$—CH$_2$—CZ$^2$Z$^2$—, wherein $Z^1$ is chosen from H and —NH—(CH$_2$)$_2$—O—CH$_3$, each $Z^2$ is independently chosen from H and —CH$_3$, and $Z^3$ is chosen from H, —C(═O)—CH$_3$, and —(CH$_2$)$_2$N(CH$_3$)$_2$,
- (bb) —NZ$^3$—CH$_2$—CZ$^1$Z$^2$—CH$_2$—O—, wherein $Z^1$ and $Z^2$ are both H, or $Z^1$ is —OH and $Z^2$ is —CH$_2$OH, or $Z^1$ is H and $Z^2$ is 4-morpholinyl, and $Z^3$ is chosen from H, —CH$_3$, —CH$_2$CH$_3$, —CH(CH$_3$)$_2$, —C(═O)CH$_3$, —C(═O)CH$_2$-(pyrrolidin-1-yl), and —C(═O)OCH$_3$,
- (cc) —NZ$^{3a}$—CH$_2$—CH$_2$—NZ$^{3b}$—CH$_2$—, wherein $Z^{3a}$ is chosen from H, —CH$_3$, —CH$_2$CH$_3$, and —C(═O)CH$_3$, and $Z^{3b}$ is chosen from H, —CH$_3$, —CH$_2$CH$_3$, —(CH$_2$)$_2$C(═O)CH$_3$, —CH$_2$C(═O)OCH$_3$, —SO$_2$CH$_3$, —CH$_2$CH$_2$OCH$_3$, —CH$_2$CH$_2$OH, —CH$_2$- cyclopropyl, —CH$_2$C≡CH, —C(=O)-(1-imidazolyl), —C(=O)N(CH$_3$)$_2$, —CH$_2$CH(OH)CF$_3$, and —CH$_2$C(=O)N(CH$_3$)$_2$, (dd) —NZ$^{3a}$—CH$_2$—CH$_2$—NZ$^{3b}$—C(=O)—, wherein Z$^{3a}$ is chosen from H, —CH$_3$, —CH$_2$CH$_3$, —CH(CH$_3$)$_2$, —CH$_2$CH$_2$N(CH$_2$CH$_2$)$_2$, and —CH$_2$CH=CH$_2$, and Z$^{3b}$ is chosen from H, —CH$_3$, —CH$_2$CH$_3$, and —CH$_2$C(=O)O(CH$_2$)$_2$OCH$_3$, (ee) —NZ$^3$—CH$_2$—C(=O)—NH—CH$_2$—, wherein Z$^3$ is chosen from H and —C(=O)CH$_3$, (ff) —NZ$^3$—C(=O)—CHZ$^1$—CH$_2$—CZ$^2$Z$^2$—, wherein Z$^1$ is chosen from H, —NHC(=O)CF$_3$, —NH$_2$, 4-morpholinyl, —NHC(=O)CH$_3$, —NHC(=O)CH$_2$OCH$_3$, —NHC(=O)-(1-pyrrolidinyl), —NHC(=O)OCH$_3$, —NH(CH$_2$)$_2$OCH$_3$, —NHC(=O)CH$_2$N(CH$_3$)$_2$, —NHC(=O)CH$_2$OCH$_3$, —NHC(=O)CF$_3$, and —NHC(=O)CH$_3$, each Z$^2$ is independently chosen from H and —CH$_3$, and Z$^3$ is chosen from H, —CH$_3$, —CH$_2$CH$_3$, —CH(CH$_3$)$_2$, —CH$_2$CH$_2$—O—CH$_3$, —CH$_2$CH(CH$_3$)$_2$, —C(=O)CH$_3$, —C(=O)CH$_2$-(1-pyrrolidinyl), —(CH$_2$)$_2$-(1-pyrrolidinyl), —C(=O)CH$_2$-(2-phthalimidyl), —C(=O)CH$_2$NH$_2$, —C(=O)-(1-pyrrolidinyl), and —C(=O)CH$_2$N(CH$_3$)$_2$, (gg) —NH—C(=O)—CH$_2$—CH$_2$—O—, (hh) —NZ$^{3a}$—C(=O)—CH$_2$—NZ$^{3b}$—CZ$^1$Z$^2$—, wherein Z$^1$ and Z$^2$ are each independently chosen from H and —CH$_3$, Z$^{3a}$ is chosen from H, —CH$_3$, —CH$_2$CH$_3$, —C(=O)CH$_3$, and —CH$_2$C(=O)N(CH$_3$)$_2$, and Z$^{3b}$ is chosen from H, —CH$_3$, —CH$_2$CH$_3$, —CH$_2$CH$_2$OCH$_3$, —CH$_2$C(=O)N(CH$_3$)$_2$, —CH$_2$C≡N, —CH$_2$-cyclopropyl, —C(=O)CH$_3$, —C(=O)CF$_3$, —C(=O)O—CH$_2$-phenyl, —CH$_2$-phenyl, —SO$_2$CH$_3$, —CH$_2$CH$_2$CF$_3$, —CH$_2$CH$_2$OH, —CH$_2$C(=O)N(CH$_3$)$_2$, and —C(=O)OCH$_2$CH$_3$, (ii) —NZ$^3$—C(=O)—O—CH$_2$—CH$_2$—, wherein Z$^3$ is chosen from H, —CH$_3$, and —CH$_2$CH$_3$, (jj) —O—CH$_2$—CH$_2$—CH$_2$—CZ$^1$Z$^2$—, wherein Z$^1$ and Z$^2$ are each independently chosen from H and —CH$_3$, (kk) —O—CH$_2$—CH$_2$—NZ$^3$—C(=O)—, wherein Z$^3$ is chosen from H, —CH$_3$, and —CH$_2$CH$_3$, (ll) —O—CH$_2$—CZ$^1$Z$^2$—CH$_2$—NZ$^3$—, wherein Z$^1$ and Z$^2$ are both H, or Z$^1$ is —OH and Z$^2$ is —CH$_2$OH, and Z$^3$ is chosen from H, —CH$_2$CH$_3$, —C(=O)OCH$_2$CH$_3$, —C(=O)O(CH$_2$)$_3$N(CH$_3$)$_2$, —C(=O)OCH$_3$, —C(=O)OCH(CH$_3$)$_2$, —C(=O)CH$_2$-(1-pyrrolidinyl), —(CH$_2$)$_2$-(1-pyrrolidinyl), —C(=O)O(CH$_2$)$_2$OCH$_3$, —C(=O)O-(1-methylpiperidin-3-yl), and —C(=O)CH$_2$OCH$_3$, (mm) —O—CH$_2$—CH$_2$—CH$_2$—O—, (nn) —CH$_2$—NH—C(=O)—CH$_2$—CH$_2$—NZ$^3$—, wherein Z$^3$ is chosen from H, —C(=O)CH$_3$, and —C(=O)CF$_3$, (oo)

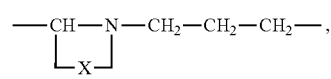

wherein X is a group of formula =N—CH=CH—, which combined with the atoms to which it is attached, forms an imidazolyl group, (pp)

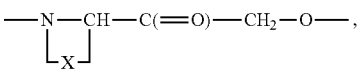

wherein X is a group of formula —CH=CH—CH=, which combined with the atoms to which it is attached, forms a pyrrolyl group, (qq)

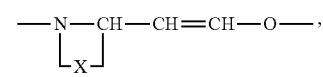

wherein X is a group of formula —CH=CH—CH=, which combined with the atoms to which it is attached, forms a pyrrolyl group, (rr)

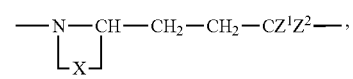

wherein X is a group of formula —CH=CH—N= or —C(CH$_3$)=CH—N=, which combined with the atoms to which it is attached, forms an imidazolyl group or a methylimidazolyl group, and Z$^1$ and Z$^2$ are each independently chosen from H and —CH$_3$, (ss)

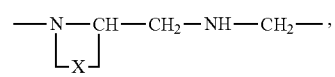

wherein X is a group of formula —CH=CH—N=, which combined with the atoms to which it is attached, forms an imidazolyl group, (tt)

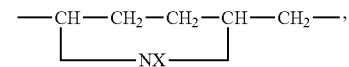

wherein X is chosen from H, —CH$_2$CH$_3$, —CH(CH$_3$)$_2$, —CH(CH$_3$)CH$_2$CH$_3$, —CH$_2$C(CH$_3$)$_3$, —CH$_2$-cyclopropyl, —CH$_2$CH$_2$OCH$_3$, —C(=O)cyclopropyl, —CO$_2$CH$_2$CH$_3$, —CH$_2$C≡CH, and —S(=O)$_2$CH$_3$, (uu)

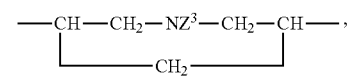

wherein Z$^3$ is chosen from H, —CH$_2$CH$_3$, —CH(CH$_3$)$_2$, —CH$_2$CH$_2$OCH$_3$, and —S(=O)$_2$CH$_3$, (vv)

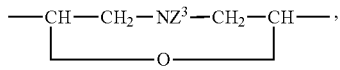

wherein $Z^3$ is chosen from H, —CH$_2$CH$_3$, —CH(CH$_3$)$_2$, —CH$_2$C≡CH, and —S(=O)$_2$CH$_3$, (ww)

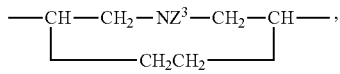

wherein $Z^3$ is chosen from H, —CH$_2$CH$_3$, —CH(CH$_3$)$_2$, —C(=O)CH$_3$, —CH$_2$CN, —C(=O)CF$_3$, —CH$_2$CH$_2$F, —CH$_2$CH$_2$OCH$_3$, —CH$_2$C≡CH, and —S(=O)$_2$CH$_3$, (xx)

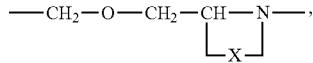

wherein X is chosen from —CH$_2$—CH$_2$—CH$_2$— and —CH$_2$—CH$_2$—CH$_2$—CH$_2$—, or (yy)

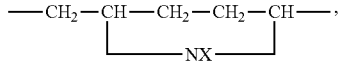

wherein X is —C(=O)OCH$_2$CH$_3$.

In another embodiment, -A$^1$-A$^2$-A$^3$-A$^4$-A$^5$- is a group of formula:
- (a) —CH$_2$—CHZ$^1$—CH$_2$—CH$_2$—CH$_2$—, wherein Z$^1$ is 4-morpholinyl,
- (b) —CH$_2$—CH$_2$—CZ$^1$Z$^2$—CH$_2$—CH$_2$—, wherein Z$^1$ is chosen from H and F, and Z$^2$ is chosen from F, —OH, —NHCH$_2$CF$_3$, —NHCH$_2$CHF$_2$, —NH(CH$_2$)$_2$OCH$_3$, —NH(CH$_2$)$_2$OH, —N(CH$_3$)(CH$_2$)$_2$OCH$_3$, 4-(4-methylpiperazin-1-yl)piperidin-1-yl, 4-methylpiperazin-1-yl, and 3-hydroxypiperidin-1-yl,
- (c) —CH$_2$—CH$_2$—CH$_2$—CHZ$^1$—CH$_2$—, wherein Z$^1$ is chosen from 4-morpholinyl, and —NHCH$_2$CH$_2$OCH$_3$,
- (d) —CZ$^1$Z$^2$—CH$_2$—CH$_2$—CH$_2$—NZ$^3$—, wherein Z$^1$ and Z$^2$ are both H or both are —CH$_3$, and Z$^3$ is independently chosen from H and —CH$_3$,
- (e) —CZ$^1$Z$^2$—CH$_2$—CZ$^{1a}$Z$^{2a}$—C(=O)—NZ$^3$—, wherein Z$^1$ and Z$^2$ are both H or both are —CH$_3$, Z$^{1a}$ and Z$^{2a}$ are both —CH$_3$, or Z$^{1a}$ is H and Z$^{2a}$ is chosen from H, —NHC(=O)CH$_2$N(CH$_3$)$_2$, —NHC(=O)cyclopropyl, —NHC(=O)CF$_3$, —NH$_2$, 4-morpholinyl, —N(CH$_3$)$_2$, and —NHC(=O)CH$_2$OCH$_3$, and Z$^3$ is chosen from H, —CH$_3$, —CH$_2$CH$_3$, —CH$_2$CO$_2$Me, —CH$_2$CO$_2$H, —CH$_2$C(=O)(4-methylpiperazinyl), —(CH$_2$)$_2$OCH$_3$, and —CH(CH$_3$)$_2$,
- (f) —CH$_2$—CH$_2$—CH$_2$—NZ$^3$—C(=O)—, wherein Z$^3$ is chosen from H and —CH$_3$,
- (g) —CH$_2$—CH$_2$—C(=O)—CH$_2$—CH$_2$—,
- (h) —CH$_2$—CH$_2$—C(=O)—NH—CZ$^1$Z$^2$—, wherein Z$^1$ and Z$^2$ are both —CH$_3$,
- (i) —CH$_2$—CH$_2$—NZ$^3$—CH$_2$—CH$_2$—, wherein Z$^3$ is chosen from H, —CH$_3$, —CH$_2$CH$_3$, —CH$_2$CH$_2$CH$_3$, —CH$_2$CF$_3$, —CH$_2$CH$_2$F, —C(=O)CF$_3$, —SO$_2$CH$_3$, —CH(CH$_3$)$_2$, —CH$_2$CH$_2$OCH$_3$, —CH$_2$CF(CH$_3$)$_2$, —CH$_2$C≡CH, —C(=O)N(CH$_3$)$_2$, —CH$_2$CH(OH)CF$_3$, —CH$_2$CH$_2$NHC(=O)CH$_3$, —CH$_2$CH(OCH$_3$)CF$_3$, —CH$_2$C(=O)N(CH$_3$)$_2$, —C(=O)(1,4-dioxan-2-yl), —CH$_2$(1,4-dioxan-2-yl), —CH$_2$CHF$_2$, —CH$_2$CH$_2$SO$_2$CH$_3$, —CH$_2$-cyclopropyl, —CH$_2$CF$_2$CH$_3$, —CH$_2$C(=O)NHCH$_3$, —CH$_2$C(=O)NH$_2$, —CH$_2$C(=O)OCH(CH$_3$)$_2$, —CH(CH$_2$OCH$_3$)$_2$, —CH$_2$CH$_2$OH, —CH$_2$C(=O)-(4-morpholinyl), —CH$_2$C(=O)-(4-methylpiperazin-1-yl), —C(=O)CH$_2$N(CH$_3$)$_2$, —CH$_2$C(=O)-(1-pyrrolidinyl), —CH$_2$-(2-oxazolyl), —CH$_2$-(1-methylimidazol-2-yl), —C(=O)CH$_2$-(4-morpholinyl), —CH$_2$C(=O)-(1-azetidinyl), —CH(CH$_2$CH$_2$F)$_2$, —(CH$_2$)$_2$-(4-morpholinyl), —(CH$_2$)$_2$C(=O)CH$_2$NH$_2$, —(CH$_2$)$_2$C(=O)CH(NH$_2$)CH(CH$_3$)$_2$, —(CH$_2$)$_2$OP(=O)(OH)$_2$, —(CH$_2$)$_2$C(=O)CH$_2$CH$_3$, —CH$_2$CH(OH)CH$_3$, —C(=O)C(NH$_2$)(CH$_3$)$_2$, and —CH$_2$C(OH)(CH$_3$)$_2$,
- (j) —CH$_2$—CH$_2$—O—CH$_2$—CH$_2$—,
- (k) —CH$_2$—CH$_2$—O—C(=O)—NZ$^3$—, wherein Z$^3$ is chosen from —CH$_3$ and —CH$_2$CH$_3$,
- (l) —CH$_2$—CH$_2$—NZ$^3$—C(=O)—CHZ$^1$—, wherein Z$^1$ is chosen from H and —CH$_2$CH$_3$, and Z$^3$ is chosen from H, —CH$_2$CH$_3$, —(CH$_2$)$_3$N(CH$_3$)$_2$, —(CH$_2$)$_3$-(4-morpholinyl), and —(CH$_2$)$_2$-(4-morpholinyl),
- (m) —CH$_2$—C(=O)—NZ$^3$—CH$_2$—CH$_2$—, wherein Z$^3$ is chosen from H, —CH$_3$, and —CH$_2$CH$_3$,
- (n) —CH$_2$—NZ$^3$—CH$_2$—CH$_2$—NZ$^{3a}$—, wherein Z$^3$ is chosen from H, —C(=O)CH$_3$, and —CH$_2$CH$_2$—O—CH$_3$, and Z$^{3a}$ is chosen from H and —CH$_3$,
- (o) —CH$_2$—O—CH$_2$—CH$_2$—NZ$^3$—, wherein Z$^3$ is —CH$_3$,
- (p) —CH$_2$—NZ$^3$—CH$_2$—CH$_2$—O—, wherein Z$^3$ is chosen from H and —CH$_2$CH$_2$—O—CH$_3$,
- (q) —CH$_2$—NZ$^3$—CH$_2$—CH$_2$—S—, wherein Z$^3$ is chosen from H, —CH$_2$CH$_3$, —CH$_2$CH$_2$—O—CH$_3$, —CH$_2$CH$_2$OH, —CH$_2$CH$_2$—OC(=O)CH$_3$,
- (r) —CH$_2$—NH—CH$_2$—CH$_2$—SO$_2$—,
- (s) —CH$_2$—NZ$^3$—CH$_2$—C(=O)—NH—, wherein Z$^3$ is —CH$_2$-phenyl,
- (t) —CZ$^1$Z$^2$—NZ$^3$—C(=O)—CH$_2$—CH$_2$—, wherein Z$^1$ and Z$^2$ are both H or both are —CH$_3$, and Z$^3$ is independently chosen from H and —CH$_3$,
- (u) —CH$_2$—NZ$^3$—C(=O)—CH=CH—, wherein Z$^3$ is —CH$_3$,
- (v) —CH$_2$—NH—C(=O)—NH—CH$_2$—,
- (w) —C(=O)—CH$_2$—CHZ$^1$—CH$_2$—CH$_2$—, wherein Z$^1$ is —NHC(=O)CH$_3$,
- (x) —C(=O)—NZ$^3$—CH$_2$—CH$_2$—CH$_2$—, wherein Z$^3$ is chosen from H and —CH$_3$,
- (y) —C(=O)—NH—CH$_2$—CH$_2$—O—,
- (z) —C(=O)—NZ$^3$—CHZ$^1$—CHZ$^2$—NZ$^{3a}$—, wherein Z$^1$ and Z$^2$ are independently chosen from H and —CH$_3$, Z$^3$ is chosen from H and —CH$_3$, and Z$^{3a}$ is chosen from H, —CH$_3$, and —C(=O)CF$_3$,
- (aa) —NZ$^3$—CH$_2$—CHZ$^1$—CH$_2$—CZ$^2$Z$^{2a}$—, wherein Z$^1$ is chosen from H and —NH—(CH$_2$)$_2$—O—CH$_3$, Z$^2$ and Z$^{2a}$ are both H or both are —CH$_3$, and Z$^3$ is chosen from H, —C(=O)—CH$_3$, and —(CH$_2$)$_2$N(CH$_3$)$_2$,
- (bb) —NZ$^3$—CH$_2$—CZ$^1$Z$^2$—CH$_2$—O—, wherein Z$^1$ and Z$^2$ are both H, or Z$^1$ is —OH and Z$^2$ is —CH$_2$OH, or Z$^1$ is H and Z$^2$ is 4-morpholinyl, and Z$^3$ is chosen from H, —CH$_3$, —CH$_2$CH$_3$, —CH(CH$_3$)$_2$, —C(=O)CH$_3$, —C(=O)CH$_2$— (pyrrolidin-1-yl), and —C(=O)OCH$_2$CH$_3$, (cc) —NZ$^{3a}$—CH$_2$—CH$_2$—NZ$^{3b}$—CH$_2$—, wherein Z$^{3a}$ is chosen from —CH$_3$, —CH$_2$CH$_3$, and —C(=O)CH$_3$, and Z$^{3b}$ is chosen from H, —CH$_3$, —CH$_2$CH$_3$, —(CH$_2$)$_2$C(=O)CH$_3$, —CH$_2$C(=O)OCH$_3$, —SO$_2$CH$_3$, —CH$_2$CH$_2$OCH$_3$, —CH$_2$CH$_2$OH, —CH$_2$-cyclopropyl, —CH$_2$C≡CH, —C(=O)-(1-imidazolyl), —C(=O)N(CH$_3$)$_2$, —CH$_2$CH(OH)CF$_3$, and —CH$_2$C(=O)N(CH$_3$)$_2$, (dd) —NZ$^{3a}$—CH$_2$—CH$_2$—NZ$^{3b}$—C(=O)—, wherein Z$^{3a}$ is chosen from H, —CH$_3$, —CH$_2$CH$_3$, —CH(CH$_3$)$_2$, —CH$_2$CH$_2$N(CH$_2$CH$_2$)$_2$, and —CH$_2$CH=CH$_2$, and Z$^{3b}$ is chosen from H, —CH$_3$, —CH$_2$CH$_3$, and —CH$_2$C(=O)O(CH$_2$)$_2$OCH$_3$, (ee) —NZ$^3$—CH$_2$—C(=O)—NH—CH$_2$—, wherein Z$^3$ is —C(=O)CH$_3$, (ff) —NZ$^3$—C(=O)—CHZ$^1$—CH$_2$—CZ$^2$Z$^{2a}$—, wherein Z$^1$ is chosen from H, —NHC(=O)CF$_3$, —NH$_2$, 4-morpholinyl, —NHC(=O)CH$_3$, —NHC(=O)CH$_2$OCH$_3$, —NHC(=O)-(1-pyrrolidinyl), —NHC(=O)OCH$_3$, —NH(CH$_2$)$_2$OCH$_3$, —NHC(=O)CH$_2$N(CH$_3$)$_2$, —NHC(=O)CH$_2$OCH$_3$, —NHC(=O)CF$_3$, and —NHC(=O)CH$_3$, Z$^2$ and Z$^{2a}$ are both H or both are —CH$_3$, and Z$^3$ is chosen from H, —CH$_3$, —CH$_2$CH$_3$, —CH(CH$_3$)$_2$, —CH$_2$CH$_2$—O—CH$_3$—CH$_2$CH(CH$_3$)$_2$, —C(=O)CH$_3$, —C(=O)CH$_2$-(1-pyrrolidinyl), —(CH$_2$)$_2$-(1-pyrrolidinyl), —C(=O)CH$_2$-(2-phthalimidyl), —C(=O)CH$_2$NH$_2$, —C(=O)—(1-pyrrolidinyl), and —C(=O)CH$_2$N(CH$_3$)$_2$, (gg) —NH—C(=O)—CH$_2$—CH$_2$—O—, (hh) —NZ$^{3a}$—C(=O)—CH$_2$—NZ$^{3b}$—CZ$^1$Z$^2$—, wherein Z$^1$ and Z$^2$ are both H or both are —CH$_3$, Z$^{3a}$ is chosen from H, —CH$_3$, —CH$_2$CH$_3$, —C(=O)CH$_3$, and —CH$_2$C(=O)N(CH$_3$)$_2$, and Z$^{3b}$ is chosen from H, —CH$_3$, —CH$_2$CH$_3$, —CH$_2$CH$_2$OCH$_3$, —CH$_2$C(=O)N(CH$_3$)$_2$, —CH$_2$C≡N, —CH$_2$-cyclopropyl, —C(=O)CH$_3$, —C(=O)CF$_3$, —C(=O)O—CH$_2$-phenyl, —CH$_2$-phenyl, —SO$_2$CH$_3$, —CH$_2$CH$_2$CF$_3$, —CH$_2$CH$_2$OH, —CH$_2$C(=O)N(CH$_3$)$_2$, and —C(=O)OCH$_2$CH$_3$, (ii) —NZ$^3$—C(=O)—O—CH$_2$—CH$_2$—, wherein Z$^3$ is chosen from —CH$_3$ and —CH$_2$CH$_3$, (jj) —O—CH$_2$—CH$_2$—CH$_2$—CZ$^1$Z$^2$—, wherein Z$^1$ and Z$^2$ are both H or both are —CH$_3$, (kk) —O—CH$_2$—CH$_2$—NZ$^3$—C(=O)—, wherein Z$^3$ is chosen from —CH$_3$, and —CH$_2$CH$_3$, (ll) —O—CH$_2$—CZ$^1$Z$^2$—CH$_2$—NZ$^3$—, wherein Z$^1$ and Z$^2$ are both H, or Z$^1$ is —OH and Z$^2$ is —CH$_2$OH, and Z$^3$ is chosen from H, —CH$_2$CH$_3$, —C(=O)OCH$_2$CH$_3$, —C(=O)O(CH$_2$)$_3$N(CH$_3$)$_2$, —C(=O)OCH$_3$, —C(=O)OCH(CH$_3$)$_2$, —C(=O)CH$_2$-(1-pyrrolidinyl), —(CH$_2$)$_2$-(1-pyrrolidinyl), —C(=O)O(CH$_2$)$_2$OCH$_3$, —C(=O)O-(1-methylpiperidin-3-yl), and —C(=O)CH$_2$OCH$_3$, (mm) —O—CH$_2$—CH$_2$—CH$_2$—O—, (nn) —CH$_2$—NH—C(=O)—CH$_2$—CH$_2$—NZ$^3$—, wherein Z$^3$ is chosen from H, —C(=O)CH$_3$, and —C(=O)CF$_3$, (oo) 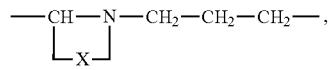

(pp) wherein X is a group of formula =N—CH=CH—, which combined with the atoms to which it is attached, forms an imidazolyl group,

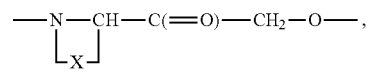

(qq) wherein X is a group of formula —CH=CH—CH=, which combined with the atoms to which it is attached, forms a pyrrolyl group,

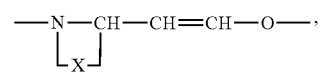

(rr) wherein X is a group of formula —CH=CH—CH=, which combined with the atoms to which it is attached, forms a pyrrolyl group,

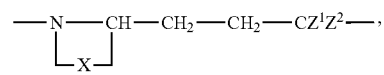

(ss) wherein X is a group of formula —CH=CH—N= or —C(CH$_3$)=CH—N=, which combined with the atoms to which it is attached, forms an imidazolyl group or a methylimidazolyl group, and Z$^1$ and Z$^2$ are both H or both are —CH$_3$,

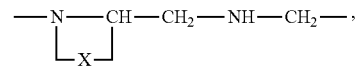

(tt) wherein X is a group of formula —CH=CH—N=, which combined with the atoms to which it is attached, forms an imidazolyl group,

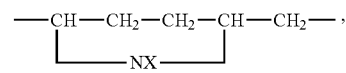

wherein X is chosen from H, —CH$_2$CH$_3$, —CH(CH$_3$)$_2$, —CH(CH$_3$)CH$_2$CH$_3$, —CH$_2$C(CH$_3$)$_3$, —CH$_2$-cyclopropyl, —CH$_2$CH$_2$OCH$_3$, —C(=O)cyclopropyl, —CO$_2$CH$_2$CH$_3$, —CH$_2$C≡CH, and —S(=O)$_2$CH$_3$, (uu)

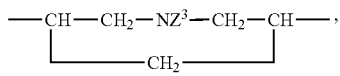

wherein $Z^3$ is chosen from —CH$_2$CH$_3$, —CH(CH$_3$)$_2$, —CH$_2$CH$_2$OCH$_3$, and —S(=O)$_2$CH$_3$, (vv)

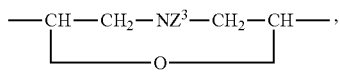

wherein $Z^3$ is chosen from H, —CH$_2$CH$_3$, —CH(CH$_3$)$_2$, —CH$_2$C≡CH, and —S(=O)$_2$CH$_3$, (ww)

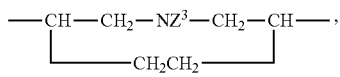

wherein $Z^3$ is chosen from H, —CH$_2$CH$_3$, —CH(CH$_3$)$_2$, —C(=O)CH$_3$, —CH$_2$CN, —C(=O)CF$_3$, —CH$_2$CH$_2$F, —CH$_2$CH$_2$OCH$_3$, —CH$_2$C≡CH, and —S(=O)$_2$CH$_3$, (xx)

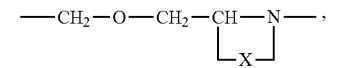

wherein X is chosen from —CH$_2$—CH$_2$—CH$_2$— and —CH$_2$—CH$_2$—CH$_2$—CH$_2$—, or (yy)

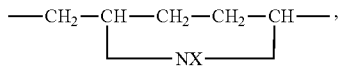

wherein X is —C(=O)OCH$_2$CH$_3$.

In another embodiment, -A$^1$-A$^2$-A$^3$-A$^4$-A$^5$- is a group of formula:

(a) —CH$_2$—CH$_2$—CZ$^1$Z$^2$—CH$_2$—CH$_2$—, wherein $Z^1$ and $Z^2$ are independently chosen from H, fluoro, and 4-morpholinyl, (b) —CZ$^1$Z$^2$—CH$_2$—CH$_2$—CH$_2$—NZ$^3$—, wherein $Z^1$, $Z^2$, and $Z^3$ are independently chosen from H and methyl, (c) —CZ$^1$Z$^2$—CH$_2$—CZ$^1$Z$^2$—C(=O)—NZ$^3$—, wherein $Z^1$ and $Z^2$ are independently chosen from H and methyl, and $Z^3$ is chosen from H, methyl, ethyl, —CH$_2$C(=O)OH, —CH$_2$C(=O)OCH$_3$, —CH$_2$C(=O)-4-methylpiperazinyl, and —CH$_2$CH$_2$OCH$_3$, (d) —CH$_2$—CH$_2$—CH$_2$—NZ$^3$—C(=O)—, wherein $Z^3$ is chosen from H and methyl, (e) —CH$_2$—CH$_2$—C(=O)—CH$_2$—CH$_2$—, (f) —CH$_2$—CH$_2$—NZ$^3$—CH$_2$—CH$_2$—, wherein $Z^3$ is chosen from H, methyl, ethyl, isopropyl, —C(=O)CF$_3$, —C(=O)N(CH$_3$)$_2$, —CH$_2$CH$_2$OCH$_3$, —CH$_2$C(=O)N(CH$_3$)$_2$, —CH$_2$CH$_2$NHC(=O)CH$_3$, —CH$_2$CF$_3$, —CH$_2$CH$_2$F, —CH$_2$CF(CH$_3$)$_2$, —CH$_2$CH(OH)CF$_3$, —CH$_2$CH(OCH$_3$)CF$_3$, —CH$_2$C≡CH, and —S(=O)$_2$CH$_3$, (g) —CH$_2$—CH$_2$—O—CH$_2$—CH$_2$—, (h) —CH$_2$—CH$_2$—NZ$^3$—C(=O)—CZ$^1$Z$^2$—, wherein $Z^1$, $Z^2$, and $Z^3$ are independently chosen from H and ethyl, (i) —CH$_2$—NZ$^3$—CH$_2$—CH$_2$—NZ$^{3a}$—, wherein $Z^3$ is chosen from H, —C(=O)CH$_3$, and —CH$_2$CH$_2$OCH$_3$, and $Z^{3a}$ is chosen from H and methyl, (j) —CH$_2$—O—CH$_2$—CH$_2$—NZ$^3$—, wherein $Z^3$ is methyl, (k) —CH$_2$—NH—CH$_2$—CH$_2$—O—, (l) —CH$_2$—NZ$^3$—CH$_2$—CH$_2$—S—, wherein $Z^3$ is chosen from H, ethyl, —CH$_2$CH$_2$OH, —CH$_2$CH$_2$OCH$_3$, and —CH$_2$CH$_2$OC(=O)CH$_3$, (m) —CH$_2$—NH—CH$_2$—CH$_2$—SO$_2$—, (n) —CH$_2$—NH—C(=O)—NH—CH$_2$—, (o) —C(=O)—NZ$^3$—CH$_2$—CH$_2$—CH$_2$—, wherein $Z^3$ is chosen from H and methyl, (p) —C(=O)—NZ$^3$—CZ$^1$Z—CZ$^1$Z$^2$—NZ$^{3a}$—, wherein $Z^1$, $Z^2$, and $Z^3$ are independently chosen from H and methyl, and $Z^{3a}$ is chosen from H, methyl, and —C(=O)CF$_3$, (q) —NZ$^3$—CH$_2$—CH$_2$—NZ$^{3a}$—CH$_2$—, wherein $Z^3$ is methyl or ethyl, and $Z^{3a}$ is chosen from H, methyl, ethyl, —C(=O)N(CH$_3$)$_2$, —CH$_2$-cyclopropyl, —CH$_2$CH$_2$OH, —CH$_2$CH$_2$OCH$_3$, —(CH$_2$)$_2$C(=O)CH$_3$, —C(=O)imidazolyl, —CH$_2$CO$_2$CH$_3$, —CH$_2$CH(OH)CF$_3$, —CH$_2$C≡CH, and —SO$_2$CH$_3$, (r) —NZ$^3$—CH$_2$—CH$_2$—NZ$^{3a}$—C(=O)—, wherein $Z^3$ is chosen from H, methyl, ethyl, isopropyl, —CH$_2$CH$_2$N(CH$_2$CH$_3$)$_2$, and —CH$_2$C≡CH$_2$, and $Z^{3a}$ is chosen from H, methyl, and ethyl, (s) —NZ$^3$—C(=O)—CH$_2$—CH$_2$—CH$_2$—, wherein $Z^3$ is chosen from H, methyl, ethyl, and —CH$_2$CH$_2$OCH$_3$, (t) —O—CH$_2$—CH$_2$—NZ$^3$—C(=O)—, wherein $Z^3$ is chosen from H, methyl, and ethyl, (u) —O—CH$_2$—CH$_2$—CH$_2$—O—, (v)

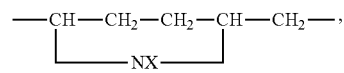

wherein X is chosen from H, ethyl, isopropyl, sec-butyl, —CH$_2$C(CH$_3$)$_3$, —CH$_2$-cyclopropyl, —CH$_2$CH$_2$OCH$_3$, —C(=O)cyclopropyl, —CO$_2$CH$_2$CH$_3$, —CH$_2$C≡CH, and —S(=O)$_2$CH$_3$, (w)

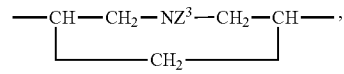

wherein $Z^3$ is chosen from ethyl, isopropyl, —CH$_2$CH$_2$OCH$_3$, and —S(=O)$_2$CH$_3$, (x)

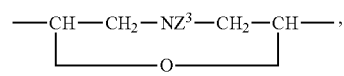

wherein $Z^3$ is chosen from H, ethyl, isopropyl, —CH$_2$C≡CH, and —S(=O)$_2$CH$_3$, (y)

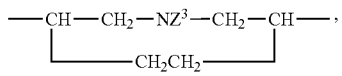

wherein $Z^3$ is chosen from H, ethyl, isopropyl, —C(=O)CH$_3$, —CH$_2$CN, —C(=O)CF$_3$, —CH$_2$CH$_2$F, —CH$_2$CH$_2$OCH$_3$, —CH$_2$C≡CH, and —S(=O)$_2$CH$_3$, (z)

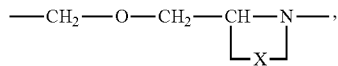

wherein X is chosen from —CH$_2$—CH$_2$—CH$_2$— and —CH$_2$—CH$_2$—CH$_2$—CH$_2$—, or (aa)

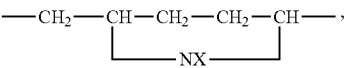

wherein X is —C(=O)OCH$_2$CH$_3$. In another embodiment, $Z^1$, $Z^2$, and $Z^3$ are defined as follows:

(a) when any two of $Z^1$, $Z^2$, and $Z^3$ are located on adjacent atoms, they may form a bond between the atoms, (b) any of $Z^1$, $Z^2$, and $Z^3$ may be independently chosen from H, halogen, —NO$_2$, —OR$^{40}$, —C(=O)R$^{40}$, —C(=O)OR$^{40}$, —C(=O)NR$^{42}$R$^{43}$, —NR$^{40}$R$^{41}$, C$_{1-6}$-alkyl, —C$_{1-6}$-alkyl-R$^{40}$, —C$_{1-6}$-alkyl-OR$^{40}$, —C$_{1-6}$-alkyl-OC(=O)R$^{40}$, —C$_{1-6}$-alkyl-C(=O)R$^{40}$, —C$_{1-6}$-alkyl-C(=O)OR$^{40}$, —C$_{1-6}$-alkyl-C(=O)NR$^{42}$R$^{43}$, —C$_{1-6}$-alkyl-NR$^{42}$R$^{43}$, —C$_{1-6}$-alkyl-NHC(=O)R$^{40}$, —C$_{1-6}$-alkyl-CN, C$_{1-6}$-haloalkyl, —C$_{1-6}$-haloalkyl-OR$^{40}$, C$_{2-6}$-alkenyl, C$_{2-6}$-alkynyl, C$_{6-15}$-aryl, 5-15 membered heteroaryl, C$_{3-10}$ cycloalkyl, 3-15 membered heterocycloalkyl, pseudohalogen, —S(=O)$_n$R$^{40}$, —S(=O)$_2$NR$^{42}$R$^{43}$, —OCH$_2$F, —OCHF$_2$, —OCF$_3$, —NHOH, —OC(=O)R$^{40}$, —OC(=O)NR$^{42}$R$^{43}$, —NR$^{40}$C(=O)R$^{41}$, —NR$^{40}$C(=O)OR$^{41}$, —NR$^{40}$S(=O)$_2$R$^{41}$, —NR$^{40}$C(=O)NR$^{42}$R$^{43}$, —NR$^{40}$S(=O)$_2$NR$^{42}$R$^{43}$, and —SCF$_3$, and (c) any two of $Z^1$, $Z^2$, and $Z^3$ may together form a group of formula -A$^6$-A$^7$-A$^8$-A$^9$-A$^{10}$-.

In another embodiment, $Z^1$, $Z^2$, and $Z^3$ are defined as follows:

(a) any of $Z^1$, $Z^2$, and $Z^3$ may be independently chosen from H, halogen, —NO$_2$, —OR$^{40}$, —C(=O)R$^{40}$, —C(=O)OR$^{40}$, —C(=O)NR$^{42}$R$^{43}$, —NR$^{40}$R$^{41}$, C$_{1-6}$-alkyl, —C$_{1-6}$-alkyl-R$^{40}$, —C$_{1-6}$-alkyl-OR$^{40}$, —C$_{1-6}$-alkyl-OC(=O)R$^{40}$, —C$_{1-6}$-alkyl-C(=O)R$^{40}$, —C$_{1-6}$-alkyl-C(=O)OR$^{40}$, —C$_{1-6}$-alkyl-C(=O)NR$^{42}$R$^{43}$, —C$_{1-6}$-alkyl-NR$^{42}$R$^{43}$, —C$_{1-6}$-alkyl-NHC(=O)R$^{40}$, —C$_{1-6}$-alkyl-CN, C$_{1-6}$-haloalkyl, —C$_{1-6}$-haloalkyl-OR$^{40}$, C$_{2-6}$-alkenyl, C$_{2-6}$-alkynyl, C$_{6-15}$-aryl, 5-15 membered heteroaryl, C$_{3-10}$ cycloalkyl, 3-15 membered heterocycloalkyl, pseudohalogen, —S(=O)$_n$R$^{40}$, —S(=O)$_2$NR$^{42}$R$^{43}$, —OCH$_2$F, —OCHF$_2$, —OCF$_3$, —NHOH, —OC(=O)R$^{41}$, —OC(=O)NR$^{42}$R$^{43}$, —NR$^{40}$C(=O)R$^{41}$, —NR$^{40}$C(=O)OR$^{41}$, —NR$^{40}$S(=O)$_2$R$^{41}$, and —SCF$_3$, and (b) any two of $Z^1$, $Z^2$, and $Z^3$ may together form a group of formula -A$^6$-A$^7$-A$^8$-A$^9$-A$^{10}$-.

In another embodiment, $Z^1$, $Z^2$, and $Z^3$ are defined as follows:

(a) any of $Z^1$, $Z^2$, and $Z^3$ may be independently chosen from H, halogen, —NO$_2$, —OR$^{40}$, —C(=O)R$^{40}$, —C(=O)OR$^{40}$, —C(=O)NR$^{42}$R$^{43}$, —NR$^{40}$R$^{41}$, C$_{1-6}$-alkyl, —C$_{1-6}$-alkyl-R$^{40}$, —C$_{1-6}$-alkyl-OR$^{40}$, —C$_{1-6}$-alkyl-OC(=O)R$^{40}$, —C$_{1-6}$-alkyl-C(=O)R$^{40}$, —C$_{1-6}$-alkyl-C(=O)OR$^{40}$, —C$_{1-6}$-alkyl-C(=O)NR$^{42}$R$^{43}$, —C$_{1-6}$-alkyl-NR$^{42}$R$^{43}$, —C$_{1-6}$-alkyl-NHC(=O)R$^{40}$, —C$_{1-6}$-alkyl-CN, C$_{1-6}$-haloalkyl, —C$_{1-6}$-haloalkyl-OR$^{40}$, C$_{2-6}$-alkenyl, C$_{2-6}$-alkynyl, C$_{6-15}$-aryl, 5-15 membered heteroaryl, 3-15 membered heterocycloalkyl, pseudohalogen, —S(=O)$_2$R$^{40}$, —S(=O)$_2$NR$^{42}$R$^{43}$, —NR$^{40}$C(=O)R$^{41}$, —NR$^{40}$C(=O)OR$^{41}$, and —NR$^{40}$S(=O)$_2$R$^{41}$, and (b) any two of $Z^1$, $Z^2$, and $Z^3$ may together form a group of formula -A$^6$-A$^7$-A$^8$-A$^9$-A$^{10}$-.

In another embodiment, $Z^1$, $Z^2$, and $Z^3$ are defined as follows:

(a) any $Z^1$, $Z^2$, and $Z^3$ may be independently chosen from H, halogen, —C(=O)R$^{40}$, —C(=O)NR$^{42}$R$^{43}$, C$_{1-6}$-alkyl, —C$_{1-6}$-alkyl-R$^{40}$, —C$_{1-6}$-alkyl-OR$^{40}$, —C$_{1-6}$-alkyl-OC(=O)R$^{40}$, —C$_{1-6}$-alkyl-C(=O)R$^{40}$, —C$_{1-6}$-alkyl-C(=O)OR$^{40}$, —C$_{1-6}$-alkyl-C(=O)NR$^{42}$R$^{43}$, —C$_{1-6}$-alkyl-NR$^{42}$R$^{43}$, —C$_{1-6}$-alkyl-NHC(=O)R$^{40}$, —C$_{1-6}$-alkyl-CN, C$_{1-6}$-haloalkyl, —C$_{1-6}$-haloalkyl-OR$^{40}$, C$_{2-6}$-alkenyl, C$_{2-6}$-alkynyl, 3-15 membered heterocycloalkyl, and —S(=O)$_2$R$^{40}$, and (b) any two of $Z^1$, $Z^2$, and $Z^3$ may together form a group of formula -A$^6$-A$^7$-A$^8$-A$^9$-A$^{10}$-, wherein A$^6$ is —CZ$^4$Z$^5$—, —NZ$^6$—, or —O—, A$^7$, A$^8$, and A$^9$ are independently a bond or —CZ$^4$Z$^5$—, and A$^{10}$ is a bond.

In another embodiment, $Z^1$, $Z^2$, and $Z^3$ are independently chosen from H, halogen, —C(=O)R$^{40}$, —C(=O)NR$^{42}$R$^{43}$, C$_{1-6}$-alkyl, —C$_{1-6}$-alkyl-R$^{40}$, —C$_{1-6}$-alkyl-OR$^{40}$, —C$_{1-6}$-alkyl-OC(=O)R$^{40}$, —C$_{1-6}$-alkyl-C(=O)R$^{40}$, —C$_{1-6}$-alkyl-C(=O)OR$^{40}$, —C$_{1-6}$-alkyl-C(=O)NR$^{42}$R$^{43}$, —C$_{1-6}$-alkyl-NR$^{42}$R$^{43}$, —C$_{1-6}$-alkyl-NHC(=O)R$^{40}$, —C$_{1-6}$-alkyl-CN, C$_{1-6}$-haloalkyl, —C$_{1-6}$-haloalkyl-OR$^{40}$, C$_{2-6}$-alkenyl, C$_{2-6}$-alkynyl, 3-15 membered heterocycloalkyl, and —S(=O)$_2$R$^{40}$. In another embodiment, two (2) of $Z^1$, $Z^2$, and $Z^3$ together form a group of formula -A$^6$-A$^7$-A$^8$-A$^9$-A$^{10}$-. In another embodiment, two of $Z^1$, $Z^2$, and $Z^3$ together form a group of formula -A$^6$-A$^7$-A$^8$-A$^9$-A$^{10}$-, wherein A$^6$ is —CZ$^4$Z$^5$—, —NZ$^6$—, or —O—, A$^7$, A$^8$, and A$^9$ are independently a bond or —CZ$^1$Z$^2$—, and A$^{10}$ is a bond.

In another embodiment, $Z^1$, $Z^2$, and $Z^3$ are defined as follows:

(a) any $Z^1$, $Z^2$, and $Z^3$ may be independently chosen from H, halogen, —C(=O)C$_{1-6}$-alkyl, —C(=O)-5-membered heteroaryl, —C(=O)C$_{1-6}$-haloalkyl, —C(=O)N(C$_{1-6}$alkyl)(C$_{1-6}$-alkyl), C$_{1-6}$-alkyl, —C$_{1-6}$-alkyl-C$_{3-10}$-cycloalkyl, —C$_{1-6}$-alkyl-OH, —C$_{1-6}$-alkyl-O—C$_{1-6}$-alkyl, —C$_{1-6}$-alkyl-OC(=O)—C$_{1-6}$-alkyl, —C$_{1-6}$-alkyl-C(=O)-6 membered heterocycloalkyl-C$_{1-6}$-alkyl, —C$_{1-6}$-alkyl-C(=O)OH, —C$_{1-6}$-alkyl-C(=O)O—C$_{1-6}$-alkyl, —C$_{1-6}$-alkyl-C(=O)N(C$_{1-6}$alkyl)(C$_{1-6}$-alkyl), —C$_{1-6}$-alkyl-N(C$_{1-6}$alkyl)(C$_{1-6}$-alkyl), —C$_{1-6}$-alkyl-NHC(=O)—C$_{1-6}$-alkyl, —C$_{1-6}$-alkyl-CN, C$_{1-6}$-haloalkyl, —C$_{1-6}$-haloalkyl-OH, —C$_{1-6}$-haloalkyl-O—C$_{1-6}$-alkyl, C$_{2-6}$-alkenyl, C$_{2-6}$-alkynyl, 6 membered heterocycloalkyl, and —S(=O)$_2$—C$_{1-6}$-alkyl, and (b) any two of $Z^1$, $Z^2$, and $Z^3$ may together form a group of formula -A$^6$-A$^7$-A$^8$-A$^9$-A$^{10}$-, wherein A$^6$ is —CH$_2$—, —$NZ^6$—, or —O—, $A^7$, $A^8$, and $A^9$ are independently a bond or —$CH_2$—, and $A^{10}$ is a bond.

In another embodiment, $Z^1$, $Z^2$, and $Z^3$ cannot together form a group of formula -$A^6$-$A^7$-$A^8$-$A^9$-$A^{10}$-.

In another embodiment, $Z^1$, $Z^2$, and $Z^3$ are defined as follows:
  (a) when any two of $Z^1$, $Z^2$, and $Z^3$ are located on adjacent atoms, they may form a bond between the atoms, and
  (b) any of $Z^1$, $Z^2$, and $Z^3$ may be independently chosen from H, halogen, —$NO_2$, —$OR^{40}$, —C(=O)$R^{40}$, —C(=O)O$R^{40}$, —C(=O)N$R^{42}R^{43}$, —N$R^{40}R^{41}$, $C_{1-6}$-alkyl-$(R^{45})_x$, $C_{6-15}$-aryl-$(R^{45})_x$, 5-15 membered heteroaryl-$(R^{45})_x$, $C_{3-10}$ cycloalkyl-$(R^{45})_x$, 3-15 membered heterocycloalkyl-$(R^{45})_x$, $C_{2-6}$-alkenyl-$(R^{45})_x$, $C_{2-6}$-alkynyl-$(R^{45})_x$, pseudohalogen, —S(=O)$_nR^{40}$, —S(=O)$_2$N$R^{42}R^{43}$, —$OCH_2F$, —$OCHF_2$, —$OCF_3$, —NHOH, —OC(=O)$R^{40}$, —OC(=O)N$R^{42}R^{43}$, —N$R^{40}$C(=O)$R^{41}$, —N$R^{40}$C(=O)O$R^{41}$, —N$R^{40}$S(=O)$_2R^{41}$, —N$R^{40}$C(=O)N$R^{42}R^{43}$, —N$R^{40}$S(=O)$_2$N$R^{42}R^{43}$, and —$SCF_3$.

In another embodiment, $Z^1$, $Z^2$, and $Z^3$ are defined as follows:
  (a) when any two of $Z^1$, $Z^2$, and $Z^3$ are located on adjacent atoms, they may form a bond between the atoms, and
  (b) any of $Z^1$, $Z^2$, and $Z^3$ may be independently chosen from H, —$OR^{40}$, —C(=O)$R^{40}$, —C(=O)O$R^{40}$, —C(=O)N$R^{42}R^{43}$, —N$R^{40}R^{41}$, $C_{1-6}$-alkyl-$(R^{45})_x$, 5-10 membered heteroaryl-$(R^{45})_x$, $C_{3-10}$ cycloalkyl-$(R^{45})_x$, 3-10 membered heterocycloalkyl-$(R^{45})_x$, $C_{2-6}$-alkenyl-$(R^{45})_x$, $C_{2-6}$-alkynyl-$(R^{45})_x$, —S(=O)$_2$N$R^{42}R^{43}$, —N$R^{40}$C(=O)$R^{41}$, —N$R^{40}$C(=O)O$R^{41}$, —N$R^{40}$S(=O)$_2R^{41}$, —N$R^{40}$C(=O)N$R^{42}R^{43}$, and —N$R^{40}$S(=O)$_2$N$R^{42}R^{43}$.

In another embodiment, $Z^1$, $Z^2$, and $Z^3$ are defined as follows:
  (a) when any two of $Z^1$, $Z^2$, and $Z^3$ are located on adjacent atoms, they may form a bond between the atoms,
  (b) any of $Z^1$ and $Z^2$ may be independently chosen from H, halogen, —$OR^{40}$, —N$R^{40}R^{41}$, $C_{1-6}$-alkyl-$(R^{45})_x$, 3-15 membered heterocycloalkyl-$(R^{45})_x$, —N$R^{40}$C(=O)$R^{41}$, —N$R^{40}$C(=O)O$R^{41}$, —N$R^{40}$S(=O)$_2R^{41}$, —N$R^{40}$C(=O)N$R^{42}R^{43}$, and —N$R^{40}$S(=O)$_2$N$R^{42}R^{43}$,
  (c) any $Z^3$ may be independently chosen from H, —C(=O)$R^{40}$, —C(=O)O$R^{40}$, —C(=O)N$R^{42}R^{43}$, $C_{1-6}$-alkyl-$(R^{45})_x$, $C_{2-6}$-alkenyl-$(R^{45})_x$, $C_{2-6}$-alkynyl-$(R^{45})_x$, and —S(=O)$_nR^{40}$, and
  (d) any two of $Z^1$, $Z^2$, and $Z^3$ may together form a group of formula -$A^6$-$A^7$-$A^8$-$A^9$-$A^{10}$-.

In another embodiment, $Z^1$, $Z^2$, and $Z^3$ are defined as follows:
  (a) when any two of $Z^1$, $Z^2$, and $Z^3$ are located on adjacent atoms, they may form a bond between the atoms,
  (b) any of $Z^1$ and $Z^2$ may be independently chosen from H, halogen, —$OR^{40}$, —N$R^{40}R^{41}$, $C_{1-6}$-alkyl-$(R^{45})_x$, 3-15 membered heterocycloalkyl-$(R^{45})_x$, —N$R^{40}$C(=O)$R^{41}$, —N$R^{40}$C(=O)O$R^{41}$, —N$R^{40}$S(=O)$_2R^{41}$, —N$R^{40}$C(=O)N$R^{42}R^{43}$, and —N$R^{40}$S(=O)$_2$N$R^{42}R^{43}$, and
  (c) any $Z^3$ may be independently chosen from H, —C(=O)$R^{40}$, —C(=O)O$R^{40}$, —C(=O)N$R^{42}R^{43}$, $C_{1-6}$-alkyl-$(R^{45})_x$, $C_{2-6}$-alkenyl-$(R^{45})_x$, $C_{2-6}$-alkynyl-$(R^{45})_x$, and —S(=O)$_nR^{40}$.

In another embodiment, $Z^1$, $Z^2$, and $Z^3$ are defined as follows:
  (a) when any two of $Z^1$, $Z^2$, and $Z^3$ are located on adjacent atoms, they may form a bond between the atoms, (b) any of $Z^1$, $Z^2$, and $Z^3$ may be independently chosen from H, halogen, —$OR^{40}$, —C(=O)$R^{40}$, —C(=O)O$R^{40}$, —C(=O)N$R^{42}R^{43}$, —N$R^{40}R^{41}$, $C_{1-6}$-alkyl-$(R^{45})_x$, 3-15 membered heterocycloalkyl-$(R^{45})_x$, $C_{2-6}$-alkenyl-$(R^{45})_x$, $C_{2-6}$-alkynyl-$(R^{45})_x$, —S(=O)$_nR^{40}$, —N$R^{40}$C(=O)$R^{41}$, and —N$R^{40}$C(=O)O$R^{41}$, and
  (c) any two of $Z^1$, $Z^2$, and $Z^3$ may together form a group of formula -$A^6$-$A^7$-$A^8$-$A^9$-$A^{10}$-.

In another embodiment, $Z^1$, $Z^2$, and $Z^3$ are defined as follows:
  (a) when any two of $Z^1$, $Z^2$, and $Z^3$ are located on adjacent atoms, they may form a bond between the atoms,
  (b) any of $Z^1$ and $Z^2$ may be independently chosen from H, halogen, —$OR^{40}$, —N$R^{40}R^{41}$, $C_{1-6}$-alkyl-$(R^{45})_x$, 3-15 membered heterocycloalkyl-$(R^{45})_x$, —N$R^{40}$C(=O)$R^{41}$, and —N$R^{40}$C(=O)O$R^{41}$,
  (c) any $Z^3$ may be independently chosen from H, —C(=O)$R^{40}$, —C(=O)O$R^{40}$, —C(=O)N$R^{42}R^{43}$, $C_{1-6}$-alkyl-$(R^{45})_x$, $C_{2-6}$-alkenyl-$(R^{45})_x$, $C_{2-6}$-alkynyl-$(R^{45})_x$, and —S(=O)$_nR^{40}$, and
  (d) any two of $Z^1$, $Z^2$, and $Z^3$ may together form a group of formula -$A^6$-$A^7$-$A^8$-$A^9$-$A^{10}$-.

In another embodiment, $Z^1$, $Z^2$, and $Z^3$ are defined as follows:
  (a) when any two of $Z^1$, $Z^2$, and $Z^3$ are located on adjacent atoms, they may form a bond between the atoms, and
  (b) any of $Z^1$, $Z^2$, and $Z^3$ may be independently chosen from H, halogen, —$OR^{40}$, —C(=O)$R^{40}$, —C(=O)O$R^{40}$, —C(=O)N$R^{42}R^{43}$, —N$R^{40}R^{41}$, $C_{1-6}$-alkyl-$(R^{45})_x$, 3-15 membered heterocycloalkyl-$(R^{45})_x$, $C_{2-6}$-alkenyl-$(R^{45})_x$, $C_{2-6}$-alkynyl-$(R^{45})_x$, —S(=O)$_nR^{40}$, —N$R^{40}$C(=O)$R^{41}$, and —N$R^{40}$C(=O)O$R^{41}$.

In another embodiment, $Z^1$, $Z^2$, and $Z^3$ are defined as follows:
  (a) when any two of $Z^1$, $Z^2$, and $Z^3$ are located on adjacent atoms, they may form a bond between the atoms,
  (b) any of $Z^1$ and $Z^2$ may be independently chosen from H, halogen, —$OR^{40}$, —N$R^{40}R^{41}$, $C_{1-6}$-alkyl-$(R^{45})_x$, 3-15 membered heterocycloalkyl-$(R^{45})_x$, —N$R^{40}$C(=O)$R^{41}$, and —N$R^{40}$C(=O)O$R^{41}$, and
  (c) any $Z^3$ may be independently chosen from H, —C(=O)$R^{40}$, —C(=O)O$R^{40}$, —C(=O)N$R^{42}R^{43}$, $C_{1-6}$-alkyl-$(R^{45})_x$, $C_{2-6}$-alkenyl-$(R^{45})_x$, $C_{2-6}$-alkynyl-$(R^{45})_x$, and —S(=O)$_nR^{40}$.

In another embodiment, $Z^1$, $Z^2$, and $Z^3$ are defined as follows:
  (a) when any two of $Z^1$, $Z^2$, and $Z^3$ are located on adjacent atoms, they may form a bond between the atoms,
  (b) any of $Z^1$ and $Z^2$ may be independently chosen from H, halogen, —$OR^{40}$, —$NHR^{40}$, $C_{1-6}$-alkyl-$(R^{45})_x$, 3-15 membered heterocycloalkyl-$(R^{45})_x$, —NHC(=O)$R^{41}$, and —NHC(=O)O$R^{41}$,
  (c) any $Z^3$ may be independently chosen from H, —C(=O)$R^{40}$, —C(=O)O$R^{40}$, —C(=O)N$R^{42}R^{43}$, $C_{1-6}$-alkyl-$(R^{45})_x$, $C_{2-6}$-alkenyl-$(R^{45})_x$, $C_{2-6}$-alkynyl-$(R^{45})_x$, and —S(=O)$_nR^{40}$, and
  (d) any two of $Z^1$, $Z^2$, and $Z^3$ may together form a group of formula -$A^6$-$A^7$-$A^8$-$A^9$-$A^{10}$-.

In another embodiment, $Z^1$, $Z^2$, and $Z^3$ are defined as follows:
  (a) when any two of $Z^1$, $Z^2$, and $Z^3$ are located on adjacent atoms, they may form a bond between the atoms,
  (b) any of $Z^1$ and $Z^2$ may be independently chosen from H, halogen, —$OR^{40}$, —$NHR^{40}$, $C_{1-6}$-alkyl-$(R^{45})_x$, 3-15 membered heterocycloalkyl-$(R^{45})_x$, —NHC(=O)$R^{41}$, and —NHC(=O)O$R^{41}$, and (c) any $Z^3$ may be independently chosen from H, —C(=O)$R^{40}$, —C(=O)O$R^{40}$, —C(=O)N$R^{42}R^{43}$, $C_{1-6}$-alkyl-$(R^{45})_x$, $C_{2-6}$-alkenyl-$(R^{45})_x$, $C_{2-6}$-alkynyl-$(R^{45})_x$, and —S(=O)$_n R^{40}$.

In another embodiment, each $Z^1$ and $Z^2$ is independently chosen from H, halogen, $C_{1-6}$-alkyl, —$C_{1-6}$-alkyl-O$R^{40}$, —N$R^{40}R^{41}$, —O$R^{40}$, 5-7 membered heterocycloalkyl, 5-7 membered heterocycloalkyl-$(R^{45})_x$, —N($R^{76}$)C(=O)$C_{1-6}$-alkyl, —N($R^{76}$)C(=O)$C_{1-6}$-haloalkyl, —N($R^{76}$)C(=O)$C_{1-6}$-alkyl-N($R^{76}$)$_2$, —N($R^{76}$)C(=O)$C_{1-6}$-alkyl-O$R^{76}$, —N($R^{76}$)C(=O)-(5-7 membered heterocycloalkyl), —N($R^{76}$)C(=O)—($C_{3-7}$-cycloalkyl), and —N($R^{76}$)C(=O)O$C_{1-6}$-alkyl, and each $Z^3$ is independently chosen from H, $C_{1-6}$-alkyl, —$C_{1-6}$-alkyl-$(R^{45})_x$, —C(=O)$R^{40}$, $C_{1-6}$-haloalkyl, —C(=O)O$R^{40}$, —C(=O)N$R^{42}R^{43}$, —$C_{1-6}$-haloalkyl-O$R^{76}$, $C_{2-6}$-alkynyl, and —S(=O)$_2$—$C_{1-6}$-alkyl, each $R^{76}$ is independently chosen from H and $C_{1-6}$-alkyl, and x is 0, 1, or 2.

In another embodiment, each $Z^1$, $Z^2$, and $Z^3$ is independently chosen from H, halogen, —C(=O)$C_{1-6}$-alkyl, —C(=O)-5-membered heteroaryl, —C(=O)$C_{1-6}$-haloalkyl, —C(=O)N($C_{1-6}$alkyl)($C_{1-6}$-alkyl), $C_{1-6}$-alkyl, —$C_{1-6}$-alkyl-$C_{3-10}$-cycloalkyl, —$C_{1-6}$-alkyl-OH, —$C_{1-6}$-alkyl-O—$C_{1-6}$-alkyl, —$C_{1-6}$-alkyl-OC(=O)—$C_{1-6}$-alkyl, —$C_{1-6}$-alkyl-C(=O)-6 membered heterocycloalkyl-$C_{1-6}$-alkyl, —$C_{1-6}$-alkyl-C(=O)OH, —$C_{1-6}$-alkyl-C(=O)O—$C_{1-6}$-alkyl, —$C_{1-6}$-alkyl-C(=O)N($C_{1-6}$alkyl)($C_{1-6}$-alkyl), —$C_{1-6}$-alkyl-N($C_{1-6}$alkyl)($C_{1-6}$-alkyl), —$C_{1-6}$-alkyl-NHC(=O)—$C_{1-6}$-alkyl, —$C_{1-6}$-alkyl-CN, $C_{1-6}$-haloalkyl, —$C_{1-6}$-haloalkyl-OH, —$C_{1-6}$-haloalkyl-O—$C_{1-6}$-alkyl, $C_{2-6}$-alkenyl, $C_{2-6}$-alkynyl, 6 membered heterocycloalkyl, and —S(=O)$_2$—$C_{1-6}$-alkyl.

In another embodiment, $Z^1$, $Z^2$, and $Z^3$ are independently chosen from H, halogen, —C(=O)$C_{1-6}$-alkyl, —C(=O)-5-membered heteroaryl, —C(=O)$C_{1-6}$-haloalkyl, —C(=O)N($C_{1-6}$alkyl)($C_{1-6}$-alkyl), $C_{1-6}$-alkyl, —$C_{1-6}$-alkyl-$C_{3-10}$-cycloalkyl, —$C_{1-6}$-alkyl-OH, —$C_{1-6}$-alkyl-O—$C_{1-6}$-alkyl, —$C_{1-6}$-alkyl-OC(=O)—$C_{1-6}$-alkyl, —$C_{1-6}$-alkyl-C(=O)-6 membered heterocycloalkyl-$C_{1-6}$-alkyl, —$C_{1-6}$-alkyl-C(=O)OH, —$C_{1-6}$-alkyl-C(=O)O—$C_{1-6}$-alkyl, —$C_{1-6}$-alkyl-C(=O)N($C_{1-6}$alkyl)($C_{1-6}$-alkyl), —$C_{1-6}$-alkyl-N($C_{1-6}$alkyl)($C_{1-6}$-alkyl), —$C_{1-6}$-alkyl-NHC(=O)—$C_{1-6}$-alkyl, —$C_{1-6}$-alkyl-CN, $C_{1-6}$-haloalkyl, —$C_{1-6}$-haloalkyl-OH, —$C_{1-6}$-haloalkyl-O—$C_{1-6}$-alkyl, $C_{2-6}$-alkenyl, $C_{2-6}$-alkynyl, 6 membered heterocycloalkyl, and —S(=O)$_2$—$C_{1-6}$-alkyl. In another embodiment, two (2) of $Z^1$, $Z^2$, and $Z^3$ together form a group of formula -$A^6$-$A^7$-$A^8$-$A^9$-$A^{10}$-, wherein $A^6$ is —CH$_2$—, —N$Z^6$—, or —O—, $A^7$, $A^8$, and $A^9$ are independently a bond or —CH$_2$—, and $A^{10}$ is a bond.

In another embodiment, $Z^1$, $Z^2$, and $Z^3$ are defined as follows:

(a) any $Z^1$, $Z^2$, and $Z^3$ may be independently chosen from H, F, —C(=O)CH$_3$, —C(=O)imidazolyl, —C(=O)CF$_3$, —C(=O)N(CH$_3$)$_2$, —CH$_3$, —CH$_2$CH$_3$, isopropyl, —CH$_2$-cyclopropyl, —(CH$_2$)$_2$—OH, —(CH$_2$)$_2$—OCH$_3$, —(CH$_2$)$_2$—OC(=O)CH$_3$, —CH$_2$C(=O)(4-methylpiperazinyl), —CH$_2$C(=O)OH, —CH$_2$C(=O)OCH$_3$, —CH$_2$—C(=O)N(CH$_3$)$_2$, —(CH$_2$)$_2$—N(ethyl)$_2$, —(CH$_2$)$_2$—NHC(=O)CH$_3$, —CH$_2$CN, —CH$_2$CF$_3$, —CH$_2$CH$_2$F, —CH$_2$—CF(CH$_3$)$_2$, —CH$_2$—CHOH—CF$_3$, —CH$_2$—CH(OCH$_3$)—CF$_3$, —CH$_2$C=CH$_2$, —CH$_2$C≡CH, 4-morpholinyl, and —SO$_2$CH$_3$, and (b) any two of $Z^1$, $Z^2$, and $Z^3$ may together form a group of formula -$A^6$-$A^7$-$A^8$-$A^9$-$A^{10}$-, wherein -$A^6$-$A^7$-$A^8$-$A^9$-$A^{10}$- is a group of formula —CH$_2$—CH$_2$—CH$_2$—CH$_2$—, —CH$_2$—CH$_2$—CH$_2$—, —CH$_2$—CH$_2$—, —CH$_2$—, —O—, —N$Z^6$—.

In another embodiment, $Z^1$, $Z^2$, and $Z^3$ are independently chosen from H, F, —C(=O)CH$_3$, —C(=O)imidazolyl, —C(=O)CF$_3$, —C(=O)N(CH$_3$)$_2$, —CH$_3$, —CH$_2$CH$_3$, isopropyl, —CH$_2$-cyclopropyl, —(CH$_2$)$_2$—OH, —(CH$_2$)$_2$—OCH$_3$, —(CH$_2$)$_2$—OC(=O)CH$_3$, —CH$_2$C(=O)(4-methylpiperazinyl), —CH$_2$C(=O)OH, —CH$_2$C(=O)OCH$_3$, —CH$_2$—C(=O)N(CH$_3$)$_2$, —(CH$_2$)$_2$—N(ethyl)$_2$, —(CH$_2$)$_2$—NHC(=O)CH$_3$, —CH$_2$CN, —CH$_2$CF$_3$, —CH$_2$CH$_2$F, —CH$_2$—CF(CH$_3$)$_2$, —CH$_2$—CHOH—CF$_3$, —CH$_2$—CH(OCH$_3$)—CF$_3$, —CH$_2$C=CH$_2$, —CH$_2$C≡CH, 4-morpholinyl, and —SO$_2$CH$_3$. In another embodiment, two (2) of $Z^1$, $Z^2$, and $Z^3$ together form a group of formula -$A^6$-$A^7$-$A^8$-$A^9$-$A^{10}$-, wherein -$A^6$-$A^7$-$A^8$-$A^9$-$A^{10}$- is a group of formula —CH$_2$—CH$_2$—CH$_2$—CH$_2$—, —CH$_2$—CH$_2$—CH$_2$—, —CH$_2$—CH$_2$—, —CH$_2$—, —O—, —N$Z^6$—.

In another embodiment, any two $Z^1$, $Z^2$, and $Z^3$ that are located on adjacent atoms may together form a bond between the atoms, any $Z^1$ and $Z^2$ may be independently chosen from H, halogen, $C_{1-6}$-alkyl, —$C_{1-6}$-alkyl-O$R^{76}$, —N$R^{40}R^{41}$, —O$R^{76}$, 5-7 membered heterocycloalkyl, 5-7 membered heterocycloalkyl-$R^{45}$, —N($R^{76}$)C(=O)$C_{1-6}$-alkyl, —N($R^{76}$)C(=O)$C_{1-6}$-haloalkyl, —N($R^{76}$)C(=O)$C_{1-6}$-alkyl-N($R^{76}$)$_2$, —N($R^{76}$)C(=O)$C_{1-6}$-alkyl-O$R^{76}$, —N($R^{76}$)C(=O)-(5-7 membered heterocycloalkyl), —N($R^{76}$)C(=O)—($C_{3-6}$-cycloalkyl), and —N($R^{76}$)C(=O)O$C_{1-6}$-alkyl, $R^{40}$ and $R^{41}$ are independently chosen from H, $C_{1-6}$-alkyl, $C_{1-4}$-haloalkyl, —$C_{1-6}$-alkyl-O$R^{76}$, —$C_{1-6}$-alkyl-N($R^{76}$)$_2$, and $C_{3-6}$-cycloalkyl, $R^{45}$ is chosen from —O$R^{76}$, $C_{1-6}$-alkyl, 5-7 membered heterocycloalkyl, and 5-7 membered heterocycloalkyl-$C_{1-6}$-alkyl, each $R^{76}$ is independently chosen from H and $C_{1-6}$-alkyl, any $Z^3$ may be chosen from H, $C_{1-6}$-alkyl, —$C_{1-6}$-alkyl-$R^{45a}$, —$C_{1-6}$-alkyl-(O—$C_{1-6}$-alkyl)$_2$, —C(=O)$C_{1-6}$-alkyl, —C(=O)$C_{1-6}$-alkyl-$R^{45b}$, —C(=O)$C_{1-6}$-haloalkyl, —C(=O)-(5-7 membered heterocycloalkyl), —C(=O)-(5-7 membered heteroaryl), $C_{1-6}$-haloalkyl, —C(=O)O$C_{1-6}$-alkyl, —C(=O)O$C_{1-6}$-alkyl-$R^{45c}$, —C(=O)O-(5-7-membered heterocycloalkyl-$C_{1-6}$-alkyl), —C(=O)N($R^{62}$)$_2$, —$C_{1-6}$-haloalkyl-O$R^{62}$, $C_{2-6}$-alkenyl, $C_{2-6}$-alkynyl, and —S(=O)$_2$—$C_{1-6}$-alkyl, $R^{45a}$ is chosen from —O$R^{62}$, 5-7 membered heterocycloalkyl, $C_{3-6}$-cycloalkyl, 5-6 membered heteroaryl, 5-6 membered heteroaryl-$C_{1-6}$-alkyl, phenyl, —SO$_2$—$C_{1-6}$-alkyl, —C(=O)N$R^{62}R^{63}$, —C(=O)O$C_{1-6}$-alkyl-O—$C_{1-4}$-alkyl, —C(=O)O$R^{62}$, —C(=O)-(4-7 membered heterocycloalkyl), —C(=O)-(5-7 membered heterocycloalkyl-$C_{1-6}$-alkyl), —OC(=O)$C_{1-6}$-alkyl, —OC(=O)$C_{1-6}$-alkyl-N($R^{62}$)$_2$, —OP(=O)(OH)$_2$, —N($R^{62}$)C(=O)—$C_{1-6}$-alkyl, —N($R^{62}$)$_2$, phenyl, and —C≡N, $R^{45b}$ is chosen from —O$R^{62}$, 5-7 membered heterocycloalkyl, 5-10 membered heteroaryl-$(R^{79})_x$, and —N($R^{62}$)$_2$, $R^{45c}$ is chosen from —O$R^{62}$, phenyl, and —N($R^{62}$)$_2$, each $R^{62}$ and $R^{63}$ is independently chosen from H and $C_{1-6}$-alkyl, each $R^{79}$ is =O, and x is 0, 1, or 2.

In another embodiment, each $Z^1$ and $Z^2$ is independently chosen from H, halogen, $C_{1-6}$-alkyl, —$C_{1-6}$-alkyl-OH, —N$R^{40}R^{41}$, —OH, 6 membered heterocycloalkyl, 6 membered heterocycloalkyl-$R^{45}$, —NHC(=O)$C_{1-6}$-alkyl, —NHC(=O)$C_{1-6}$-haloalkyl, —NHC(=O)$C_{1-6}$-alkyl-N($C_{1-6}$-alkyl)$_2$, —NHC(=O)$C_{1-6}$-alkyl-O—$C_{1-4}$-alkyl, —NHC(=O)-(5 membered heterocycloalkyl), and —NHC(=O)O$C_{1-6}$-alkyl, each $R^{40}$ and $R^{41}$ is independently chosen from H, $C_{1-6}$-alkyl, $C_{1-4}$-haloalkyl, —$C_{1-6}$-alkyl-OH, —$C_{1-6}$-alkyl-O—$C_{1-4}$-alkyl, —C(=O)$C_{1-6}$-alkyl-N($C_{1-6}$-alkyl)$_2$, —C(=O)$C_{3-6}$-cycloalkyl, —C(=O)$C_{1-4}$-haloalkyl, and —C(═O)C$_{1-6}$-alkyl-O—C$_{1-4}$-alkyl, each R$^{45}$ is independently chosen from —OH, C$_{1-6}$-alkyl, and 6 membered heterocycloalkyl-C$_{1-6}$-alkyl, each Z$^3$ is independently chosen from H, C$_{1-6}$-alkyl, —C$_{1-6}$-alkyl-R$^{45a}$, —C$_{1-6}$-alkyl-(O—C$_{1-6}$-alkyl)$_2$, —C(═O)C$_{1-6}$-alkyl, —C(═O)C$_{1-6}$-alkyl-O—C$_{1-4}$-alkyl, —C(═O)C$_{1-6}$-haloalkyl, —C(═O)-(5-6-membered heterocycloalkyl), —C(═O)C$_{1-6}$-alkyl-(5-6-membered heterocycloalkyl), —C(═O)-(5-membered heteroaryl), —C(═O)C$_{1-6}$-alkyl-(9-membered heteroaryl-(R$^{79}$)$_2$), —C(═O)C$_{1-6}$-alkyl-(5-membered heteroaryl), —C(═O)C$_{1-6}$-alkyl-NH$_2$, —C(═O)C$_{1-6}$-alkyl-N(C$_{1-6}$-alkyl)$_2$, C$_{1-6}$-haloalkyl, —C(═O)OC$_{1-6}$-alkyl, —C(═O)OC$_{1-6}$-alkyl-phenyl, —C(═O)OC$_{1-6}$-alkyl-N(C$_{1-6}$-alkyl)$_2$, —C(═O)OC$_{1-6}$-alkyl-O—C$_{1-4}$-alkyl, —C(═O)O-(6-membered heterocycloalkyl-C$_{1-6}$-alkyl), —C(═O)N(C$_{1-6}$alkyl)$_2$, —C$_{1-6}$-haloalkyl-OH, —C$_{1-6}$-haloalkyl-O—C$_{1-6}$-alkyl, C$_{2-6}$-alkynyl, and —S(═O)$_2$—C$_{1-6}$-alkyl, each R$^{45a}$ is independently chosen from —OH, —O—C$_{1-6}$-alkyl, 5-6 membered heterocycloalkyl, C$_{3-6}$-cycloalkyl, 5 membered heteroaryl, 5 membered heteroaryl-C$_{1-6}$-alkyl, phenyl, —SO$_2$—C$_{1-6}$-alkyl, —C(═O)NR$^{62}$R$^{63}$, —C(═O)OC$_{1-6}$-alkyl, —C(═O)OC$_{1-6}$-alkyl-O—C$_{1-4}$-alkyl, —C(═O)OH, —C(═O)C$_{1-6}$-alkyl, —C(═O)-(4-6 membered heterocycloalkyl), —C(═O)-(6 membered heterocycloalkyl-C$_{1-6}$-alkyl), —OC(═O)C$_{1-6}$-alkyl, —OC(═O)C$_{1-6}$-alkyl-NH$_2$, —OP(═O)(OH)$_2$, —NHC(═O)—C$_{1-6}$-alkyl, —N(C$_{1-6}$-alkyl)$_2$, phenyl, and —C≡N, each R$^{62}$ and R$^{63}$ is independently chosen from H and C$_{1-6}$alkyl, and each R$^{79}$ is ═O.

In another embodiment, Z$^1$, Z$^2$, and Z$^3$ are defined as follows:

(a) any two Z$^1$, Z$^2$, and Z$^3$ that are located on adjacent atoms may together form a bond between the atoms, (b) any Z$^1$ and Z$^2$ may be independently chosen from H, —CH$_3$, —CH$_2$CH$_3$, —CH$_2$OH, F, —OH, —NH$_2$, —N(CH$_3$)$_2$, —NHCH$_2$CF$_3$, —NHCH$_2$CHF$_2$, —NH(CH$_2$)$_2$OCH$_3$, —NH(CH$_2$)$_2$OH, —N(CH$_3$)(CH$_2$)$_2$OCH$_3$, —NHC(═O)CH$_2$N(CH$_3$)$_2$, —NHC(═O)CH$_3$, —NHC(═O)CF$_3$, —NHC(═O)CH$_2$OCH$_3$, —NHC(═O)cyclopropyl, —NHC(═O)-(1-pyrrolidinyl), —NHC(═O)OCH$_3$, 4-morpholinyl, 4-(4-methylpiperazin-1-yl)piperidin-1-yl, 4-methylpiperazin-1-yl, and 3-hydroxypiperidin-1-yl, (c) any Z$^3$ may be independently chosen from H, —CH$_3$, —CH$_2$CH$_3$, —CH$_2$CH$_2$CH$_3$, —CH(CH$_3$)$_2$, —CH$_2$CH(CH$_3$)$_2$, —CH$_2$CF$_3$, —CH$_2$CH$_2$CF$_3$, —CH$_2$CH$_2$F, —CH$_2$CHF$_2$, —CH$_2$CF$_2$CH$_3$, —CH$_2$CF(CH$_3$)$_2$, —CH(CH$_2$CH$_2$F)$_2$, —CH$_2$CH(OH)CF$_3$, —CH$_2$CH(OCH$_3$)CF$_3$, —CH$_2$CH$_2$OH, —CH$_2$CH$_2$OCH$_3$, —CH$_2$CH(OH)CH$_3$, —CH$_2$C(OH)(CH$_3$)$_2$, —CH(CH$_2$OCH$_3$)$_2$, —(CH$_2$)$_2$OCH$_3$, —CH$_2$C≡N, —(CH$_2$)$_2$N(CH$_3$)$_2$, —(CH$_2$)$_3$N(CH$_3$)$_2$, —CH$_2$CH$_2$N(CH$_2$CH$_2$)$_2$, —CH$_2$-cyclopropyl, —CH$_2$-phenyl, —(CH$_2$)$_3$-(4-morpholinyl), —(CH$_2$)$_2$-(4-morpholinyl), —(CH$_2$)$_2$-(1-pyrrolidinyl), —CH$_2$-(2-oxazolyl), —CH$_2$-(1-methylimidazol-2-yl), —CH$_2$(1,4-dioxan-2-yl), —CH$_2$CH$_2$NHC(═O)CH$_3$, —CH$_2$C(═O)N(CH$_3$)$_2$, —CH$_2$C(═O)NHCH$_3$, —CH$_2$C(═O)NH$_2$, —CH$_2$C(═O)-(4-methylpiperazinyl), —CH$_2$C(═O)-(4-morpholinyl), —CH$_2$C(═O)-(4-methylpiperazin-1-yl), —CH$_2$C(═O)-(1-pyrrolidinyl), —CH$_2$C(═O)-(1-azetidinyl), —CH$_2$CO$_2$H, —CH$_2$CO$_2$Me, —CH$_2$C(═O)OCH(CH$_3$)$_2$, —CH$_2$C(═O)O(CH$_2$)$_2$OCH$_3$, —CH$_2$CH$_2$—OC(═O)CH$_3$, —(CH$_2$)$_2$C(═O)CH$_2$NH$_2$, —(CH$_2$)$_2$C(═O)CH(NH$_2$)CH(CH$_3$)$_2$, —(CH$_2$)$_2$OP(═O)(OH)$_2$, —(CH$_2$)$_2$C(═O)CH$_2$CH$_3$, —CH$_2$CH$_2$SO$_2$CH$_3$, —CH$_2$CH═CH$_2$, —CH$_2$C≡CH, —C(═O)CH$_3$, —C(═O)CF$_3$, —C(═O)CH$_2$OCH$_3$, —C(═O)CH$_2$NH$_2$, —C(═O)CH$_2$N(CH$_3$)$_2$, —C(═O)C(NH$_2$)(CH$_3$)$_2$, —C(═O)CH$_2$-(1-pyrrolidinyl), —C(═O)CH$_2$-(4-morpholinyl), —C(═O)CH$_2$-(2-phthalimidyl), —C(═O)(1,4-dioxan-2-yl), —C(═O)-(1-imidazolyl), —C(═O)-(1-pyrrolidinyl), —C(═O)OCH$_3$, —C(═O)OCH$_2$CH$_3$, —C(═O)OCH(CH$_3$)$_2$, —C(═O)O(CH$_2$)$_2$OCH$_3$, —C(═O)O—CH$_2$-phenyl, —C(═O)O(CH$_2$)$_2$N(CH$_3$)$_2$, —C(═O)O-(1-methylpiperidin-3-yl), —C(═O)N(CH$_3$)$_2$, and —SO$_2$CH$_3$, (d) any Z$^1$ and Z$^3$ on adjacent atoms may together form a group of formula ═N—CH═CH—, —CH═CH—CH═, —CH═CH—N═ or —C(CH$_3$)═CH—N═, (e) any Z$^1$ and Z$^2$ may together form a group of formula —NZ$^6$—, wherein Z$^6$ is chosen from H, —CH$_2$CH$_3$, —CH(CH$_3$)$_2$, —CH(CH$_3$)CH$_2$CH$_3$, —CH$_2$C(CH$_3$)$_3$, —CH$_2$-cyclopropyl, —CH$_2$CH$_2$OCH$_3$, —C(═O)cyclopropyl, —CO$_2$CH$_2$CH$_3$, —CH$_2$C≡CH, and —S(═O)$_2$CH$_3$, and (f) any Z$^1$ and Z$^2$ may together form a group of formula —CH$_2$—, —CH$_2$CH$_2$—, —CH$_2$—CH$_2$—CH$_2$—, —CH$_2$—CH$_2$—CH$_2$—CH$_2$—, or —O—.

In another embodiment, Z$^1$, Z$^2$, and Z$^3$ are defined as follows:

(a) any two Z$^1$, Z$^2$, and Z$^3$ that are located on adjacent atoms may together form a bond between the atoms, (b) any Z$^1$ and Z$^2$ may be independently chosen from H, —CH$_3$, —CH$_2$CH$_3$, —CH$_2$OH, F, —OH, —NH$_2$, —N(CH$_3$)$_2$, —NHCH$_2$CF$_3$, —NHCH$_2$CHF$_2$, —NH(CH$_2$)$_2$OCH$_3$, —NH(CH$_2$)$_2$OH, —N(CH$_3$)(CH$_2$)$_2$OCH$_3$, —NHC(═O)CH$_2$N(CH$_3$)$_2$, —NHC(═O)CH$_3$, —NHC(═O)CF$_3$, —NHC(═O)CH$_2$OCH$_3$, —NHC(═O)cyclopropyl, —NHC(═O)-(1-pyrrolidinyl), —NHC(═O)OCH$_3$, 4-morpholinyl, 4-(4-methylpiperazin-1-yl)piperidin-1-yl, 4-methylpiperazin-1-yl, and 3-hydroxypiperidin-1-yl, (c) any Z$^3$ may be independently chosen from H, —CH$_3$, —CH$_2$CH$_3$, —CH$_2$CH$_2$CH$_3$, —CH(CH$_3$)$_2$, —CH$_2$CH(CH$_3$)$_2$, —CH$_2$CF$_3$, —CH$_2$CH$_2$CF$_3$, —CH$_2$CH$_2$F, —CH$_2$CHF$_2$, —CH$_2$CF$_2$CH$_3$, —CH$_2$CF(CH$_3$)$_2$, —CH(CH$_2$CH$_2$F)$_2$, —CH$_2$CH(OH)CF$_3$, —CH$_2$CH(OCH$_3$)CF$_3$, —CH$_2$CH$_2$OH, —CH$_2$CH$_2$OCH$_3$, —CH$_2$CH(OH)CH$_3$, —CH$_2$C(OH)(CH$_3$)$_2$, —CH(CH$_2$OCH$_3$)$_2$, —(CH$_2$)$_2$OCH$_3$, —CH$_2$C≡N, —(CH$_2$)$_2$N(CH$_3$)$_2$, —(CH$_2$)$_3$N(CH$_3$)$_2$, —CH$_2$CH$_2$N(CH$_2$CH$_2$)$_2$, —CH$_2$-cyclopropyl, —CH$_2$-phenyl, —(CH$_2$)$_3$-(4-morpholinyl), —(CH$_2$)$_2$-(4-morpholinyl), —(CH$_2$)$_2$-(1-pyrrolidinyl), —CH$_2$-(2-oxazolyl), —CH$_2$-(1-methylimidazol-2-yl), —CH$_2$(1,4-dioxan-2-yl), —CH$_2$CH$_2$NHC(═O)CH$_3$, —CH$_2$C(═O)N(CH$_3$)$_2$, —CH$_2$C(═O)NHCH$_3$, —CH$_2$C(═O)NH$_2$, —CH$_2$C(═O)(4-methylpiperazinyl), —CH$_2$C(═O)-(4-morpholinyl), —CH$_2$C(═O)-(4-methylpiperazin-1-yl), —CH$_2$C(═O)-(1-pyrrolidinyl), —CH$_2$C(═O)-(1-azetidinyl), —CH$_2$CO$_2$H, —CH$_2$CO$_2$Me, —CH$_2$C(═O)OCH(CH$_3$)$_2$, —CH$_2$C(═O)O(CH$_2$)$_2$OCH$_3$, —CH$_2$CH$_2$—OC(═O)CH$_3$, —(CH$_2$)$_2$C(═O)CH$_2$NH$_2$, —(CH$_2$)$_2$C(═O)CH(NH$_2$)CH(CH$_3$)$_2$, —(CH$_2$)$_2$OP(═O)(OH)$_2$, —(CH$_2$)$_2$C(═O)CH$_2$CH$_3$, —CH$_2$CH$_2$SO$_2$CH$_3$, —CH$_2$CH═CH$_2$, —CH$_2$C≡CH, —C(═O)CH$_3$, —C(═O)CF$_3$, —C(═O)CH$_2$OCH$_3$, —C(═O)CH$_2$NH$_2$, —C(═O)CH$_2$N(CH$_3$)$_2$, —C(═O)C(NH$_2$)(CH$_3$)$_2$, —C(═O)CH$_2$-(1-pyrrolidinyl), —C(═O)CH$_2$-(4-morpholinyl), —C(═O)CH$_2$-(2-phthalimidyl), —C(═O)(1,4-dioxan-2-yl), —C(═O)-(1-imidazolyl), —C(═O)-(1-pyrrolidinyl), —C(═O)OCH$_3$, —C(═O)OCH$_2$CH$_3$, —C(═O)OCH(CH$_3$)$_2$, —C(═O)O(CH$_2$)$_2$OCH$_3$, —C(═O)O—CH$_2$-phenyl, —C(=O)O(CH$_2$)$_3$N(CH$_3$)$_2$, —C(=O)O-(1-methylpi-peridin-3-yl), —C(=O)N(CH$_3$)$_2$, and —SO$_2$CH$_3$,
(d) when -A$^1$-A$^2$-A$^3$-A$^4$-A$^5$- is —CHZ$^1$—NZ$^3$—CH$_2$—CH$_2$—CH$_2$—, Z$^1$ and Z$^3$ may together form a group of formula =N—CH=CH—,
(e) when -A$^1$-A$^2$-A$^3$-A$^4$-A$^5$- is —NZ$^3$—CHZ$^1$—C(=O)—CH$_2$—O—, Z$^1$ and Z$^3$ may together form a group of formula —CH=CH—CH=,
(f) when -A$^1$-A$^2$-A$^3$-A$^4$-A$^5$- is —NZ$^3$—CHZ$^1$—CH=CH—O—, Z$^1$ and Z$^3$ may together form a group of formula —CH=CH—CH=,
(g) when -A$^1$-A$^2$-A$^3$-A$^4$-A$^5$- is —NZ$^3$—CHA$^1$—CH$_2$—CH$_2$—CZ$^{1a}$Z$^{2a}$—, Z$^1$ and Z$^3$ may together form a group of formula —CH=CH—N= or —C(CH$_3$)=CH—N=, wherein Z$^{1a}$ and Z$^{2a}$ are both H or both are —CH$_3$,
(h) when -A$^1$-A$^2$-A$^3$-A$^4$-A$^5$- is —NZ$^3$—CHZ$^1$—CH$_2$—NH—CH$_2$—, Z$^1$ and Z$^3$ may together form a group of formula —CH=CH—N=,
(i) when -A$^1$-A$^2$-A$^3$-A$^4$-A$^5$- is —CHZ$^1$—CH$_2$—CH$_2$—CHZ$^2$—CH$_2$—, Z$^1$ and Z$^2$ may together form a group of formula —NZ$^6$—, wherein Z$^6$ is chosen from H, —CH$_2$CH$_3$, —CH(CH$_3$)$_2$, —CH(CH$_3$)CH$_2$CH$_3$, —CH$_2$C(CH$_3$)$_3$, —CH$_2$-cyclopropyl, —CH$_2$CH$_2$OCH$_3$, —C(=O)cyclopropyl, —CO$_2$CH$_2$CH$_3$, —CH$_2$C≡CH, and —S(=O)$_2$CH$_3$,
(j) when -A$^1$-A$^2$-A$^3$-A$^4$-A$^5$- is —CHZ$^1$—CH$_2$—NZ$^{3a}$—CH$_2$—CHZ$^2$—, Z$^1$ and Z$^2$ may together form a group of formula —CH$_2$—, wherein Z$^{3a}$ is chosen from H, —CH$_2$CH$_3$, —CH(CH$_3$)$_2$, —CH$_2$CH$_2$OCH$_3$, and —S(=O)$_2$CH$_3$,
(k) when -A$^1$-A$^2$-A$^3$-A$^4$-A$^5$- is —CHZ$^1$—CH$_2$—NZ$^{3a}$—CH$_2$—CHZ$^2$—, Z$^1$ and Z$^2$ may together form a group of formula —O—, wherein Z$^{3a}$ is chosen from H, —CH$_2$CH$_3$, —CH(CH$_3$)$_2$, —CH$_2$C≡CH, and —S(=O)$_2$CH$_3$,
(l) when -A$^1$-A$^2$-A$^3$-A$^4$-A$^5$- is —CHZ$^1$—CH$_2$—NZ$^{3a}$—CH$_2$—CHZ$^1$—, Z$^1$ and Z$^2$ may together form a group of formula —CH$_2$CH$_2$—, wherein Z$^{3a}$ is chosen from H, —CH$_2$CH$_3$, —CH(CH$_3$)$_2$, —C(=O)CH$_3$, —CH$_2$CN, —C(=O)CF$_3$, —CH$_2$CH$_2$F, —CH$_2$CH$_2$OCH$_3$, —CH$_2$C≡CH, and —S(=O)$_2$CH$_3$,
(m) when -A$^1$-A$^2$-A$^3$-A$^4$-A$^5$- is —CH$_2$—O—CH$_2$—CHZ$^1$—NZ$^3$—, Z$^1$ and Z$^3$ may together form a group of formula —CH$_2$—CH$_2$—CH$_2$— or —CH$_2$—CH$_2$—CH$_2$—, and
(n) when -A$^1$-A$^2$-A$^3$-A$^4$-A$^5$- is —CH$_2$—CHZ$^1$—CH$_2$—CH$_2$—CHZ$^2$—, Z$^1$ and Z$^2$ may together form a group of formula —NZ$^6$—, wherein Z$^6$ is —C(=O)OCH$_2$CH$_3$.

In another embodiment, Z$^1$, Z$^2$, and Z$^3$ are defined as follows:
(a) any Z$^1$ and Z$^2$ may be independently chosen from H, —CH$_3$, —CH$_2$CH$_3$, —CH$_2$OH, F, —OH, —NH$_2$, —N(CH$_3$)$_2$, —NHCH$_2$CF$_3$, —NHCH$_2$CHF$_2$, —NH(CH$_2$)$_2$OCH$_3$, —NH(CH$_2$)$_2$OH, —N(CH$_3$)(CH$_2$)$_2$OCH$_3$, —NHC(=O)CH$_2$N(CH$_3$)$_2$, —NHC(=O)CH$_3$, —NHC(=O)CF$_3$, —NHC(=O)CH$_2$OCH$_3$, —NHC(=O)cyclopropyl, —NHC(=O)-(1-pyrrolidinyl), —NHC(=O)OCH$_3$, 4-morpholinyl, 4-(4-methylpiperazin-1-yl)piperidin-1-yl, 4-methylpiperazin-1-yl, and 3-hydroxypiperidin-1-yl,
(b) any Z$^3$ may be independently chosen from H, —CH$_3$, —CH$_2$CH$_3$, —CH$_2$CH$_2$CH$_3$, —CH(CH$_3$)$_2$, —CH$_2$CH(CH$_3$)$_2$, —CH$_2$CF$_3$, —CH$_2$CH$_2$CF$_3$, —CH$_2$CH$_2$F, —CH$_2$CHF$_2$, —CH$_2$CF$_2$CH$_3$, —CH$_2$CF(CH$_3$)$_2$, —CH(CH$_2$CH$_2$F)$_2$, —CH$_2$CH(OH)CF$_3$, —CH$_2$CH(OCH$_3$)CF$_3$, —CH$_2$CH$_2$OH, —CH$_2$CH$_2$OCH$_3$, —CH$_2$CH(OH)CH$_3$, —CH$_2$C(OH)(CH$_3$)$_2$, —CH(CH$_2$OCH$_3$)$_2$, —(CH$_2$)$_2$OCH$_3$, —CH$_2$C≡N, —(CH$_2$)$_2$N(CH$_3$)$_2$, —(CH$_2$)$_3$N(CH$_3$)$_2$, —CH$_2$CH$_2$N(CH$_2$CH$_2$)$_2$, —CH$_2$-cyclopropyl, —CH$_2$-phenyl, —(CH$_2$)$_3$-(4-morpholinyl), —(CH$_2$)$_2$-(4-morpholinyl), —(CH$_2$)$_2$-(1-pyrrolidinyl), —CH$_2$-(2-oxazolyl), —CH$_2$-(1-methylimidazol-2-yl), —CH$_2$(1,4-dioxan-2-yl), —CH$_2$CH$_2$NHC(=O)CH$_3$, —CH$_2$C(=O)N(CH$_3$)$_2$, —CH$_2$C(=O)NHCH$_3$, —CH$_2$C(=O)NH$_2$, —CH$_2$C(=O)(4-methylpiperazinyl), —CH$_2$C(=O)-(4-morpholinyl), —CH$_2$C(=O)-(4-methylpiperazin-1-yl), —CH$_2$C(=O)-(1-pyrrolidinyl), —CH$_2$C(=O)-(1-azetidinyl), —CH$_2$CO$_2$H, —CH$_2$CO$_2$Me, —CH$_2$C(=O)OCH(CH$_3$)$_2$, —CH$_2$C(=O)O(CH$_2$)$_2$OCH$_3$, —CH$_2$CH$_2$—OC(=O)CH$_3$, —(CH$_2$)$_2$C(=O)CH$_2$NH$_2$, —(CH$_2$)$_2$C(=O)CH(NH$_2$)CH(CH$_3$)$_2$, —(CH$_2$)$_2$OP(=O)(OH)$_2$, —(CH$_2$)$_2$C(=O)CH$_2$CH$_3$, —CH$_2$CH$_2$SO$_2$CH$_3$, —CH$_2$CH=CH$_2$, —CH$_2$C≡CH, —C(=O)CH$_3$, —C(=O)CF$_3$, —C(=O)CH$_2$OCH$_3$, —C(=O)CH$_2$NH$_2$, —C(=O)CH$_2$N(CH$_3$)$_2$, —C(=O)C(NH$_2$)(CH$_3$)$_2$, —C(=O)CH$_2$-(1-pyrrolidinyl), —C(=O)CH$_2$-(4-morpholinyl), —C(=O)CH$_2$-(2-phthalimidyl), —C(=O)(1,4-dioxan-2-yl), —C(=O)-(1-imidazolyl), —C(=O)-(1-pyrrolidinyl), —C(=O)OCH$_3$, —C(=O)OCH$_2$CH$_3$, —C(=O)OCH(CH$_3$)$_2$, —C(=O)O(CH$_2$)$_2$OCH$_3$, —C(=O)O—CH$_2$-phenyl, —C(=O)O(CH$_2$)$_3$N(CH$_3$)$_2$, —C(=O)O-(1-methylpi-peridin-3-yl), —C(=O)N(CH$_3$)$_2$, and —SO$_2$CH$_3$,
(c) any Z$^1$ and Z$^3$ on adjacent atoms may together form a group of formula =N—CH=CH—, —CH=CH—CH=, —CH=CH—N= or —C(CH$_3$)=CH—N=,
(d) any Z$^1$ and Z$^2$ may together form a group of formula —NZ$^6$—, wherein Z$^6$ is chosen from H, —CH$_2$CH$_3$, —CH(CH$_3$)$_2$, —CH(CH$_3$)CH$_2$CH$_3$, —CH$_2$C(CH$_3$)$_3$, —CH$_2$-cyclopropyl, —CH$_2$CH$_2$OCH$_3$, —C(=O)cyclopropyl, —CO$_2$CH$_2$CH$_3$, —CH$_2$C≡CH, and —S(=O)$_2$CH$_3$, and
(e) any Z$^1$ and Z$^2$ may together form a group of formula —CH$_2$—, —CH$_2$CH$_2$—, —CH$_2$—CH$_2$—CH$_2$—, —CH$_2$—CH$_2$—CH$_2$—CH$_2$—, or —O—.

In another embodiment, Z$^1$, Z$^2$, and Z$^3$ are defined as follows:
(a) any Z$^1$ and Z$^2$ may be independently chosen from H, —CH$_3$, —CH$_2$CH$_3$, —CH$_2$OH, F, —OH, —NH$_2$, —N(CH$_3$)$_2$, —NHCH$_2$CF$_3$, —NHCH$_2$CHF$_2$, —NH(CH$_2$)$_2$OCH$_3$, —NH(CH$_2$)$_2$OH, —N(CH$_3$)(CH$_2$)$_2$OCH$_3$, —NHC(=O)CH$_2$N(CH$_3$)$_2$, —NHC(=O)CH$_3$, —NHC(=O)CF$_3$, —NHC(=O)CH$_2$OCH$_3$, —NHC(=O)cyclopropyl, —NHC(=O)-(1-pyrrolidinyl), —NHC(=O)OCH$_3$, 4-morpholinyl, 4-(4-methylpiperazin-1-yl)piperidin-1-yl, 4-methylpiperazin-1-yl, and 3-hydroxypiperidin-1-yl,
(b) any Z$^3$ may be independently chosen from H, —CH$_3$, —CH$_2$CH$_3$, —CH$_2$CH$_2$CH$_3$, —CH(CH$_3$)$_2$, —CH$_2$CH(CH$_3$)$_2$, —CH$_2$CF$_3$, —CH$_2$CH$_2$CF$_3$, —CH$_2$CH$_2$F, —CH$_2$CHF$_2$, —CH$_2$CF$_2$CH$_3$, —CH$_2$CF(CH$_3$)$_2$, —CH(CH$_2$CH$_2$F)$_2$, —CH$_2$CH(OH)CF$_3$, —CH$_2$CH(OCH$_3$)CF$_3$, —CH$_2$CH$_2$OH, —CH$_2$CH$_2$OCH$_3$, —CH$_2$CH(OH)CH$_3$, —CH$_2$C(OH)(CH$_3$)$_2$, —CH(CH$_2$OCH$_3$)$_2$, —(CH$_2$)$_2$OCH$_3$, —CH$_2$C≡N, —(CH$_2$)$_2$N(CH$_3$)$_2$, —(CH$_2$)$_3$N(CH$_3$)$_2$, —CH$_2$CH$_2$N(CH$_2$CH$_2$)$_2$, —CH$_2$-cyclopropyl, —CH$_2$-phenyl, —(CH$_2$)$_3$-(4-morpholinyl), —(CH$_2$)$_2$-(4-morpholinyl), —(CH$_2$)$_2$-(1-pyrrolidinyl), —CH$_2$-(2-oxazolyl), —CH$_2$-(1-methylimidazol-2-yl), —CH$_2$(1,4-dioxan-2-yl), —CH$_2$CH$_2$NHC(=O)CH$_3$, —CH$_2$C(=O)N(CH$_3$)$_2$, —CH$_2$C(=O)NHCH$_3$, —CH$_2$C(=O)NH$_2$, —CH$_2$C(=O)(4-methylpiperazinyl), —CH$_2$C(=O)-(4-morpholinyl), —CH$_2$C(=O)-(4-methylpiperazin-1-yl), —CH$_2$C(=O)-(1-pyrrolidinyl), —CH$_2$C(=O)-(1-azetidinyl), —CH$_2$CO$_2$H, —CH$_2$CO$_2$Me, —CH$_2$C(=O)OCH(CH$_3$)$_2$, —CH$_2$C(=O)O(CH$_2$)$_2$OCH$_3$, —CH$_2$CH$_2$—OC(=O)CH$_3$, —(CH$_2$)$_2$C(=O)CH$_2$NH$_2$, —(CH$_2$)$_2$C(=O)CH(NH$_2$)CH(CH$_3$)$_2$, —(CH$_2$)$_2$OP(=O)(OH)$_2$, —(CH$_2$)$_2$C(=O)CH$_2$CH$_3$, —CH$_2$CH$_2$SO$_2$CH$_3$, —CH$_2$CH=CH$_2$, —CH$_2$C≡CH, —C(=O)CH$_3$, —C(=O)CF$_3$, —C(=O)CH$_2$OCH$_3$, —C(=O)CH$_2$NH$_2$, —C(=O)CH$_2$N(CH$_3$)$_2$, —C(=O) C(NH$_2$)(CH$_3$)$_2$, —C(=O)CH$_2$-(1-pyrrolidinyl), —C(=O)CH$_2$-(4-morpholinyl), —C(=O)CH$_2$-(2-phthalimidyl), —C(=O)(1,4-dioxan-2-yl), —C(=O)-(1-imidazolyl), —C(=O)-(1-pyrrolidinyl), —C(=O) OCH$_3$, —C(=O)OCH$_2$CH$_3$, —C(=O)OCH(CH$_3$)$_2$, —C(=O)O(CH$_2$)$_2$OCH$_3$, —C(=O)O—CH$_2$-phenyl, —C(=O)O(CH$_2$)$_3$N(CH$_3$)$_2$, —C(=O)O-(1-methylpiperidin-3-yl), —C(=O)N(CH$_3$)$_2$, and —SO$_2$CH$_3$, (c) when -A$^1$-A$^2$-A$^3$-A$^4$-A$^5$- is —CHZ$^1$—NZ$^3$—CH$_2$—CH$_2$—CH$_2$—, Z$^1$ and Z$^3$ may together form a group of formula =N—CH=CH—, (d) when -A$^1$-A$^2$-A$^3$-A$^4$-A$^5$- is —NZ$^3$—CHZ$^1$—C(=O)—CH$_2$—O—, Z$^1$ and Z$^3$ may together form a group of formula —CH=CH—CH=, (e) when -A$^1$-A$^2$-A$^3$-A$^4$-A$^5$- is —NZ$^3$—CHZ$^1$—CH=CH—O—, Z$^1$ and Z$^3$ may together form a group of formula —CH=CH—CH=, (f) when -A$^1$-A$^2$-A$^3$-A$^4$-A$^5$- is —NZ$^3$—CHA$^1$-CH$_2$—CH$_2$—CZ$^{1a}$Z$^{2a}$—, Z$^1$ and Z$^3$ may together form a group of formula —CH=CH—N= or —C(CH$_3$)=CH—N=, wherein Z$^{1a}$ and Z$^{2a}$ are both H or both are —CH$_3$, (g) when -A$^1$-A$^2$-A$^3$-A$^4$-A$^5$- is —NZ$^3$—CHZ$^1$—CH$_2$—NH—CH$_2$—, Z$^1$ and Z$^3$ may together form a group of formula —CH=CH—N=, (h) when -A$^1$-A$^2$-A$^3$-A$^4$-A$^5$- is —CHZ$^1$—CH$_2$—CH$_2$—CHZ$^2$—CH$_2$—, Z$^1$ and Z$^2$ may together form a group of formula —NZ$^6$—, wherein Z$^6$ is chosen from H, —CH$_2$CH$_3$, —CH(CH$_3$)$_2$, —CH(CH$_3$)CH$_2$CH$_3$, —CH$_2$C(CH$_3$)$_3$, —CH$_2$-cyclopropyl, —CH$_2$CH$_2$OCH$_3$, —C(=O)cyclopropyl, —CO$_2$CH$_2$CH$_3$, —CH$_2$C≡CH, and —S(=O)$_2$CH$_3$, (i) when -A$^1$-A$^2$-A$^3$-A$^4$-A$^5$- is —CHZ$^1$—CH$_2$—NZ$^{3a}$—CH$_2$—CHZ$^2$—, Z$^1$ and Z$^2$ may together form a group of formula —CH$_2$—, wherein Z$^{3a}$ is chosen from H, —CH$_2$CH$_3$, —CH(CH$_3$)$_2$, —CH$_2$CH$_2$OCH$_3$, and —S(=O)$_2$CH$_3$, (j) when -A$^1$-A$^2$-A$^3$-A$^4$-A$^5$- is —CHZ$^1$—CH$_2$—NZ$^{3a}$—CH$_2$—CHZ$^2$—, Z$^1$ and Z$^2$ may together form a group of formula —O—, wherein Z$^{3a}$ is chosen from H, —CH$_2$CH$_3$, —CH(CH$_3$)$_2$, —CH$_2$C≡CH, and —S(=O)$_2$CH$_3$, (k) when -A$^1$-A$^2$-A$^3$-A$^4$-A$^5$- is —CHZ$^1$—CH$_2$—NZ$^{3a}$—CH$_2$—CHZ$^2$—, Z$^1$ and Z$^2$ may together form a group of formula —CH$_2$CH$_2$—, wherein Z$^{3a}$ is chosen from H, —CH$_2$CH$_3$, —CH(CH$_3$)$_2$, —C(=O)CH$_3$, —CH$_2$CN, —C(=O)CF$_3$, —CH$_2$CH$_2$F, —CH$_2$CH$_2$OCH$_3$, —CH$_2$C≡CH, and —S(=O)$_2$CH$_3$, (l) when -A$^1$-A$^2$-A$^3$-A$^4$-A$^5$- is —CH$_2$—O—CH$_2$—CHZ$^1$—NZ$^3$—, Z$^1$ and Z$^3$ may together form a group of formula —CH$_2$—CH$_2$—CH$_2$— or —CH$_2$—CH$_2$—CH$_2$—, and (m) when -A$^1$-A$^2$-A$^3$-A$^4$-A$^5$- is —CH$_2$—CHZ$^1$—CH$_2$—CH$_2$—CHZ$^1$—, Z$^1$ and Z$^2$ may together form a group of formula —NZ$^6$—, wherein Z$^6$ is —C(=O)OCH$_2$CH$_3$.

In another embodiment, A$^1$, A$^2$, A$^3$, A$^4$, and A$^5$ are defined as in any of the above embodiments, except that when two of R$^3$, R$^4$, and R$^5$ are hydrogen, and the other is selected from the group consisting of hydrogen, halogen, —NO$_2$, —OH, —O(C$_{4-7}$-cycloalkyl), —O(C$_{6-15}$-aryl), —C(=O)R$^{30}$, —C(=O)OR$^{30}$, —C(=O)NR$^{32}$R$^{33}$, —NR$^{30}$R$^{31}$, C$_{1-2}$-alkyl, —C$_{1-2}$-alkyl-OR$^{30}$, —C$_{1-2}$-alkyl-NR$^{32}$R$^{33}$, C$_{1-4}$-fluoroalkyl, C$_{2-5}$-alkenyl, C$_{2-5}$-alkynyl, C$_{6-15}$-aryl, C$_{3-7}$ cycloalkyl, N-containing 3-15 membered heterocycloalkyl, —CN, —S(=O)$_n$R$^{30}$, —S(=O)$_2$NR$^{32}$R$^{33}$, —OCH$_2$F, —OCHF$_2$, and —OCF$_3$, then at least one of A$^1$, A$^2$, A$^3$, A$^4$, or A$^5$ is not selected from the group consisting of:

(a) —CX$^1$X$^2$—, wherein X$^1$ and X$^2$ are independently selected from the group consisting of hydrogen and C$_{1-6}$-alkyl,
(b) —O—,
(c) —S—,
(d) —S(O)—,
(e) —S(O)$_2$—,
(f) —N(C(=O)C$_{1-6}$-alkyl)-,
(g) —N(C(=O)C$_{6-5}$-aryl)-,
(h) —N(SO$_2$C$_{1-6}$-alkyl)-, and
(i) —N(S(O)$_2$aryl)-.

In another embodiment, A$^1$, A$^2$, A$^3$, A$^4$, and A$^5$ are defined as in any of the above embodiments, except that when two of R$^3$, R$^4$, and R$^5$ are hydrogen, and the other is selected from the group consisting of hydrogen, halogen, —NO$_2$, —OH, —O(C$_{4-7}$-cycloalkyl), —O(C$_{6-15}$-aryl), —C(=O)R$^{30}$, —C(=O)OR$^{30}$, —C(=O)NR$^{32}$R$^{33}$, —NR$^{30}$R$^{31}$, C$_{1-2}$-alkyl, —C$_{1-2}$-alkyl-OR$^{30}$, —C$_{1-2}$-alkyl-NR$^{32}$R$^{33}$, C$_{1-4}$-fluoroalkyl, C$_{2-5}$-alkenyl, C$_{2-5}$-alkynyl, C$_{6-15}$-aryl, C$_{3-7}$ cycloalkyl, N-containing 3-15 membered heterocycloalkyl, —CN, —S(=O)$_n$R$^{30}$, —S(=O)$_2$NR$^{32}$R$^{33}$, —OCH$_2$F, —OCHF$_2$, and —OCF$_3$, then A$^1$, A$^2$, A$^3$, A$^4$, and A$^5$ do not form a group of formula —(CH$_2$)$_m$—N(X)—(CH$_2$)$_n$—, wherein:

(a) the methylene groups of the —(CH$_2$)$_m$—N(X)—(CH$_2$)$_n$— moiety are independently optionally substituted by one or two groups independently selected from C$_{1-6}$-alkyl,
(b) X is selected from the group consisting of C$_{1-6}$-alkyl, C$_{1-6}$-haloalkyl, and C$_{6-15}$-aryl,
(c) m and n are independently selected from 0, 1, 2, 3, and 4, provided that m+n=4, and
(d) any methylene group in the —(CH$_2$)$_m$—N(X)—(CH$_2$)$_n$— moiety that is adjacent to the nitrogen atom of the —(CH$_2$)$_m$—N(X)—(CH$_2$)$_n$— moiety may be replaced by a carbonyl group.

In another embodiment, A$^1$, A$^2$, A$^3$, A$^4$, and A$^5$ are defined as in any of the above embodiments, except that when two of R$^3$, R$^4$, and R$^5$ are independently hydrogen, fluorine, or chlorine, and the other is selected from the group consisting of hydrogen, halogen, —NO$_2$, —OR$^{30}$, —C(=O)R$^{30}$, —C(=O)OR$^{30}$, —C(=O)NR$^{32}$R$^{33}$, —NR$^{30}$R$^{31}$, C$_{1-6}$-alkyl, —C$_{1-6}$-alkyl-OR$^{30}$, —C$_{1-6}$-alkyl-NR$^{32}$R$^{33}$, C$_{1-2}$-haloalkyl, C$_{2-5}$-alkenyl, C$_{2-5}$-alkynyl, C$_{6-15}$-aryl, C$_{3-7}$ cycloalkyl, N-containing 3-15 membered heterocycloalkyl, —CN, —S(=O)$_n$R$^{30}$, —S(=O)$_2$NR$^{32}$R$^{33}$, —OCH$_2$F, —OCHF$_2$, —OCF$_3$, —NR$^{30}$C(=O)R$^{31}$, —NR$^{30}$C(=O)OR$^{31}$, and —NR$^{30}$S(=O)$_2$R$^{31}$, then at least one of A$^1$, A$^2$, A$^3$, A$^4$, or A$^5$ is not:

(a) —CX$^1$X$^2$-, wherein X$^1$ and X$^2$ are independently selected from the group consisting of hydrogen and C$_{1-6}$-alkyl,
(b) —O—,
(c) —S—,
(d) —S(O)—,
(e) —S(O)$_2$—, or
(f) —N(X$^3$)—, wherein X$^3$ is H, C$_{1-6}$-alkyl, —C(=O)H, —C(=O)C$_{1-6}$-alkyl, —CN, —C(=O)O—C$_{1-6}$-alkyl, —S(O)$_2$—C$_{1-6}$-alkyl, or —C(=O)CF$_3$, (g) —N(C(=O)C$_{6-15}$-aryl)-,
(h) —N(SO$_2$C$_{1-6}$-alkyl)-, or
(i) —N(S(O)$_2$aryl-)-.

In another embodiment, A$^1$, A$^2$, A$^3$, A$^4$, and A$^5$ are defined as in any of the above embodiments, except that none of A$^1$, A$^2$, A$^3$, A$^4$, and A$^5$ is —O— when either of the following (a) or (b) is true:

(a) R$^3$ and R$^5$ are hydrogen, and R$^4$ is selected from the group consisting of hydrogen, —OR$^{40}$, —C(=O)OR$^{40}$, —C(=O)NR$^{42}$R$^{43}$, —NR$^{40}$R$^{41}$, C$_{1-6}$-alkyl, —C$_{1-6}$-alkyl-OR$^{40}$, —C$_{1-6}$-alkyl-NR$^{42}$R$^{43}$, C$_{1-6}$-haloalkyl, C$_{2-6}$-alkenyl, 5-15 membered heteroaryl, C$_{3-8}$ cycloalkyl, 3-15 membered heterocycloalkyl, —S(=O)$_2$NR$^{42}$R$^{43}$, —OCH$_2$F, —OCHF$_2$, —OCF$_3$, —NHOH, —NR$^{20}$C(=O)alkyl, and —N(C$_{1-6}$-alkyl)C(=O)NR$^{42}$R$^{43}$, or (b) R$^3$ and R$^5$ are hydrogen, R$^4$ is selected from the group consisting of hydrogen, halogen, —OR$^{40}$, —C(=O)OR$^{40}$, —C(=O)NR$^{42}$R$^{43}$, —NR$^{40}$R$^{41}$, C$_{1-6}$-alkyl, —C$_{1-6}$-alkyl-OR$^{40}$, —C$_{1-6}$-alkyl-NR$^{42}$R$^{43}$, C$_{1-6}$-haloalkyl, C$_{2-6}$-alkenyl, 5-15 membered heteroaryl, C$_{3-8}$ cycloalkyl, 3-15 membered heterocycloalkyl, —S—C$_{1-6}$-alkyl, —S(=O)$_2$NR$^{42}$R$^{43}$, —OCH$_2$F, —OCHF$_2$, —OCF$_3$, —NHOH, —NR$^{20}$C(=O)alkyl, and —N(C$_{1-6}$-alkyl)C(=O)NR$^{42}$R$^{43}$, and R$^2$ is a group of formula

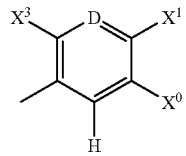

having substituents as defined in either of the following (i) or (ii):

(i) D is =CX$^2$—, and any of the following (A)-(D) is true:

(A) X$^1$ and X$^2$ form together with the C-atoms to which they are attached a 5 to 15 membered non-aromatic carbocyclic or heterocyclic residue, wherein the heterocyclic residue comprises 1 to 5 heteroatoms selected from N, O and S, or (B) X$^1$ and X$^2$ together form a residue of formula —C(CH$_3$)=CH—O—, —CH=CH—NH—, or —N=C(CH$_3$)—C(CH$_3$)=N—, or (C) X$^1$ and X$^2$ together form a residue of formula —CH=N—NH— and X$^3$ is —SO$_2$NR$^{22}$R$^{23}$, or (D) X$^2$ is —O—C$_{1-5}$-fluoroalkyl comprising 2 to 5 fluorine atoms, —N(CH$_3$)$_2$, or —O—C$_{1-4}$-alkyl, or (ii) D is =N—, and any of the following (A)-(D) is true:

(A) each of X$^0$, X$^1$, X$^2$, and X$^3$ are independently selected from the group consisting of hydrogen, hydroxy, C$_{1-6}$-alkyl, —C$_{1-6}$-alkyl-OH, —C$_{1-6}$-alkyl-O—C$_{1-6}$-alkyl, —C$_{1-6}$-alkyl-NR$^{22}$R$^{23}$, C$_{1-6}$-haloalkyl, and C$_{3-8}$ cycloalkyl, or (B) each of X$^1$, X$^2$, and X$^3$ are independently selected from the group consisting of halogen, —NO$_2$, —O—C$_{1-6}$-alkyl, —O—C$_{1-6}$-alkynyl, —O—C$_{1-6}$-haloalkyl, —C(=O)—C$_{2-6}$-alkyl, —C(=O)O—C$_{2-6}$-alkyl, —C(=O)OH, —C(=O)NR$^{22}$R$^{23}$, —C(=O)N(C$_{1-6}$-alkyl-OH)R$^{20}$, —NR$^{20}$R$^{21}$, —C$_{1-6}$-alkyl-NR$^{22}$R$^{23}$, C$_{1-6}$-haloalkyl, C$_{6-15}$-aryl, 5-15 membered heteroaryl, 5-10 membered heterocycloalkyl, 3-15 membered heterocycloalkyl-C$_{1-6}$-alkyl, 3-15 membered heterocycloalkyl-OH, 3-15 membered heterocycloalkyl-O—C$_{1-6}$-alkyl, —S(=O)$_2$NR$^{22}$R$^{23}$, —OCH$_2$F, —OCHF$_2$, —OCF$_3$, —NHOH, and —N(C$_{1-6}$-alkyl)C(=O)—C$_{1-6}$-alkyl, or (C) X$^1$ and X$^2$ form together with the C-atoms to which they are attached C$_{6-15}$-aryl or a 5-10 membered heteroaryl residue comprising one or two heteroatoms selected from N, O and S, wherein the C$_{6-15}$-aryl or 5-10 membered heteroaryl residue is optionally substituted by one or more substituents independently selected from the group consisting of halogen, —OH, C$_{1-6}$-alkyl, —O—C$_{1-6}$-alkyl, —NO$_2$, —CN, —COOH, —C(=O)NH$_2$, —NR$^{20}$R$^{21}$, C$_{3-6}$-cycloalkyl, 3-7 membered heterocycloalkyl, phenyl, and 5-6 membered heteroaryl, or (D) X$^1$ and X$^2$ form together with the C-atoms to which they are attached a 5-15 membered non-aromatic carbocyclic or heterocyclic residue, wherein the heterocyclic residue comprises 1-5 heteroatoms selected from N, O and S, and wherein the carbocyclic or heterocyclic residue is optionally substituted by one or more substituents independently selected from the group consisting of halogen, —OH, C$_{1-6}$-alkyl, —O—C$_{1-6}$-alkyl, —NO$_2$, —CN, —COOH, —C(=O)NH$_2$, —NR$^{20}$R$^{21}$, C$_{3-6}$-cycloalkyl, 3-7 membered heterocycloalkyl, phenyl, and 5-6 membered heteroaryl.

In another embodiment, both of the following (a) and (b) are true:

(a) two of Z$^1$, Z$^2$, and Z$^3$ together form a group of formula -A$^6$-A$^7$-A$^8$-A$^9$-A$^{10}$-; and (b) at least one of A$^6$, A$^7$, A$^8$, A$^9$, and A$^{10}$ is not a bond.

In another embodiment, A$^1$, A$^2$, A$^3$, A$^4$, and A$^5$ are defined as in any of the above embodiments, except that when R$^3$, R$^4$, and R$^5$ are hydrogen, then A$^1$, A$^2$, A$^3$, A$^4$, and A$^5$ do not together form a group of formula —O—CH$_2$—CH$_2$—CH$_2$—O—. In another embodiment, A$^1$, A$^2$, A$^3$, A$^4$, and A$^5$ are defined as in any of the above embodiments, except that A$^1$, A$^2$, A$^3$, A$^4$, and A$^5$ do not together form a group of formula —O—CH$_2$—CH$_2$—CH$_2$—O—. In another embodiment, A$^1$, A$^2$, A$^3$, A$^4$, and A$^5$ are defined as in any of the above embodiments, except that at least one of A$^1$, A$^2$, A$^3$, A$^4$, and A$^5$ is —S(=O)—. In another embodiment, Z$^1$, Z$^2$, and Z$^3$ are defined as in any of the above embodiments, except that at least one of Z$^1$, Z$^2$, or Z$^3$ is —NO$_2$, —C$_{1-6}$-alkyl-NR$^{42}$R$^{43}$, —C$_{1-6}$-alkyl-CN, C$_{1-6}$-haloalkyl, C$_{2-6}$-alkynyl, 5-15 membered heteroaryl, 3-15 membered heterocycloalkyl, —OCH$_2$F, —OCHF$_2$, —OCF$_3$, —NHOH, —OC(=O)R$^{40}$, —OC(=O)NR$^{42}$R$^{43}$, —NR$^{40}$C(=O)R$^{41}$, —NR$^{40}$C(=O)OR$^{41}$, —NR$^{40}$S(=O)$_2$R$^{41}$, —NR$^{40}$C(=O)NR$^{42}$R$^{43}$, —NR$^{40}$SO$_2$NR$^{42}$R$^{43}$, or —SCF$_3$.

In another embodiment, R$^{40}$ and R$^{41}$ at each occurrence are independently chosen from H, C$_{1-6}$-alkyl, C$_{2-6}$-alkynyl, C$_{1-6}$-haloalkyl, C$_{6-15}$-aryl, 5-15 membered heteroaryl, C$_{3-10}$ cycloalkyl, and 3-15 membered heterocycloalkyl, in which said C$_{1-6}$-alkyl, C$_{2-6}$-alkynyl, C$_{1-6}$-haloalkyl, C$_{6-15}$-aryl, 5-15 membered heteroaryl, C$_{3-10}$ cycloalkyl, and 3-15 membered heterocycloalkyl groups are optionally substituted by one or more substituents independently chosen from C$_{1-6}$-alkyl, halogen, and —OH. In another embodiment, R$^{40}$ and R$^{41}$ at each occurrence are independently chosen from H, C$_{1-6}$-alkyl, C$_{1-6}$-haloalkyl, 5-15 membered heteroaryl, C$_{3-10}$ cycloalkyl, and 3-15 membered heterocycloalkyl, in which said C$_{1-6}$-alkyl, C$_{1-6}$-haloalkyl, 5-15 membered heteroaryl, $C_{3-10}$ cycloalkyl, and 3-15 membered heterocycloalkyl groups are optionally substituted by one or more substituents independently chosen from $C_{1-6}$-alkyl, phenyl, 5-10 membered heteroaryl-$(R^{79})_x$, 3-10 membered heterocycloalkyl, —$N(R^{76})_2$, and —$OR^{76}$. In another embodiment, $R^{40}$ and $R^{41}$ at each occurrence are independently chosen from H, $C_{1-6}$-alkyl, $C_{1-6}$-haloalkyl, 5-15 membered heteroaryl, $C_{3-10}$ cycloalkyl, and 3-15 membered heterocycloalkyl, in which said $C_{1-6}$-alkyl, $C_{1-6}$-haloalkyl, 5-15 membered heteroaryl, $C_{3-10}$ cycloalkyl, and 3-15 membered heterocycloalkyl groups are optionally substituted by one or more substituents independently chosen from $C_{1-6}$-alkyl, phenyl, 5-10 membered heteroaryl-$(R^{79})_2$, 3-10 membered heterocycloalkyl, —$N(R^{76})_2$, and —$OR^{76}$, wherein each $R^{76}$ is independently chosen from H and $C_{1-6}$-alkyl, $R^{79}$ is =O, and x is 0, 1, or 2. In another embodiment, $R^{40}$ and $R^{41}$ at each occurrence are independently chosen from H, $C_{1-6}$-alkyl, $C_{1-6}$-haloalkyl, 5-15 membered heteroaryl, $C_{3-10}$ cycloalkyl, and 3-15 membered heterocycloalkyl, in which said $C_{1-6}$-alkyl, $C_{1-6}$-haloalkyl, 5-15 membered heteroaryl, $C_{3-10}$ cycloalkyl, and 3-15 membered heterocycloalkyl groups are optionally substituted by one or more substituents independently chosen from $C_{1-6}$-alkyl, phenyl, 5-10 membered heteroaryl-$(R^{79})_2$, 3-10 membered heterocycloalkyl, —$N(R^{76})_2$, and —$OR^{76}$, wherein each $R^{76}$ is independently chosen from H and $C_{1-6}$-alkyl, and $R^{79}$ is =O. In another embodiment, $R^{40}$ and $R^{41}$ at each occurrence are independently chosen from H, $C_{1-6}$-alkyl optionally substituted by —OH, $C_{2-6}$-alkynyl, $C_{1-6}$-haloalkyl, $C_{6-15}$-aryl, 5-15 membered heteroaryl, $C_{3-10}$ cycloalkyl, and 3-15 membered heterocycloalkyl optionally substituted by $C_{1-6}$-alkyl or —OH. In another embodiment, $R^{40}$ and $R^{41}$ at each occurrence are independently chosen from H, $C_{1-6}$-alkyl optionally substituted by —OH, $C_{1-6}$-haloalkyl, 5-15 membered heteroaryl, $C_{3-10}$ cycloalkyl, and 3-15 membered heterocycloalkyl optionally substituted by $C_{1-6}$-alkyl or —OH. In another embodiment, $R^{40}$ and $R^{41}$ at each occurrence are independently chosen from H, $C_{1-6}$-alkyl optionally substituted by —OH, $C_{1-6}$-haloalkyl, and 3-15 membered heterocycloalkyl optionally substituted by $C_{1-6}$-alkyl or —OH. In another embodiment, $R^{40}$ and $R^{41}$ at each occurrence are independently chosen from H, $C_{1-6}$-alkyl optionally substituted by —OH, $C_{1-6}$-haloalkyl, and 3-15 membered heterocycloalkyl. In another embodiment, $R^{40}$ and $R^{41}$ at each occurrence are independently chosen from H, $C_{1-6}$-alkyl, and $C_{1-6}$-fluoroalkyl. In another embodiment, $R^{40}$ and $R^{41}$ at each occurrence are independently chosen from H, $C_{1-6}$-alkyl, 5-15 membered heteroaryl, $C_{1-6}$-haloalkyl, 3-15 membered heterocycloalkyl-$C_{1-6}$-alkyl, and 3-15 membered heterocycloalkyl. In another embodiment, $R^{40}$ and $R^{41}$ at each occurrence are independently chosen from H, $C_{1-6}$-alkyl, 5-10 membered heteroaryl, $C_{1-6}$-haloalkyl, 5-10 membered heterocycloalkyl-$C_{1-6}$-alkyl, and 5-10 membered heterocycloalkyl. In another embodiment, $R^{40}$ and $R^{41}$ at each occurrence are independently chosen from H, $C_{1-6}$-alkyl, 5-membered heteroaryl, $C_{1-6}$-haloalkyl, 6-membered heterocycloalkyl-$C_{1-6}$-alkyl, and 6-membered heterocycloalkyl. In another embodiment, $R^{40}$ and $R^{41}$ at each occurrence are independently chosen from H, —$CH_3$, —$CH_2CH_3$, —$CH(CH_3)_2$, —$CF_3$, —$CH_2CF_3$, —$CH_2CHF_2$, —$(CH_2)_2OH$, —$CH_2OCH_3$, —$(CH_2)_2OCH_3$, —$(CH_2)_2OCH_3$, —$CH_2NH_2$, —$CH_2N(CH_3)_2$, —$C(NH_2)(CH_3)_2$, —$(CH_2)_3N(CH_3)_2$, —$CH_2$-(pyrrolidinyl), —$CH_2$-(morpholinyl), —$CH_2$—(phthalimidyl), —$CH_2$-phenyl, -cyclopropyl, pyrrolidinyl, 1,4-dioxanyl, pyrrolidinyl, 1-methylpiperidinyl, imidazolyl, and —$OCH_3$. In another embodiment, $R^{40}$ and $R^{41}$ at each occurrence are independently chosen from H, —$CH_3$, —$CH_2CH_3$, —$CH(CH_3)_2$, —$CF_3$, —$CH_2CF_3$, —$CH_2CHF_2$, —$(CH_2)_2OH$, —$CH_2OCH_3$, —$(CH_2)_2OCH_3$, —$(CH_2)_2OCH_3$, —$CH_2NH_2$, —$CH_2N(CH_3)_2$, —$C(NH_2)(CH_3)_2$, —$(CH_2)_3N(CH_3)_2$, —$CH_2$-(1-pyrrolidinyl), —$CH_2$-(4-morpholinyl), —$CH_2$-(2-phthalimidyl), —$CH_2$-phenyl, -cyclopropyl, 1-pyrrolidinyl, 1,4-dioxan-2-yl, 1-pyrrolidinyl, 1-methylpiperidin-3-yl, 1-imidazolyl, and —$OCH_3$. In another embodiment, $R^{40}$ and $R^{41}$ at each occurrence are independently chosen from H, methyl, imidazolyl, —$CF_3$, cyclopropyl, (4-methylpiperazinyl), and 4-morpholinyl. In another embodiment, $R^{40}$ and $R^{41}$ at each occurrence are independently chosen from H and $C_{1-6}$-alkyl.

In another embodiment, $R^{42}$ and $R^{43}$ at each occurrence are independently chosen from H, $C_{1-6}$-alkyl, $C_{2-6}$-alkynyl, $C_{1-6}$-haloalkyl, $C_{6-15}$-aryl, 5-15 membered heteroaryl, $C_{3-10}$ cycloalkyl, and 3-15 membered heterocycloalkyl, in which said $C_{1-6}$-alkyl, $C_{2-6}$-alkynyl, $C_{1-6}$-haloalkyl, $C_{6-15}$-aryl, 5-15 membered heteroaryl, $C_{3-10}$ cycloalkyl, and 3-15 membered heterocycloalkyl groups are optionally substituted by one or more substituents independently chosen from $C_{1-6}$-alkyl, halogen, and —OH; or $R^{42}$ and $R^{43}$ may form, together with the nitrogen atom to which they are attached, a 3-15 membered heterocycloalkyl group or a 5-15 membered heteroaryl group, in which said 3-15 membered heterocycloalkyl group or 5-15 membered heteroaryl group is optionally substituted by one or more substituents independently chosen from $C_{1-6}$-alkyl, halogen, and —OH. In another embodiment, $R^{42}$ and $R^{43}$ at each occurrence are independently chosen from H, $C_{1-6}$-alkyl optionally substituted by —OH, $C_{2-6}$-alkynyl, $C_{1-6}$-haloalkyl, $C_{6-15}$-aryl, 5-15 membered heteroaryl, $C_{3-10}$ cycloalkyl, and 3-15 membered heterocycloalkyl optionally substituted by —OH; or $R^{42}$ and $R^{43}$ may form, together with the nitrogen atom to which they are attached, a 3-15 membered heterocycloalkyl group or a 5-15 membered heteroaryl group, in which the heterocycloalkly group or 5-15 membered heteroaryl group may optionally be substituted by one or more members selected from $C_{1-6}$-alkyl. In another embodiment, $R^{42}$ and $R^{43}$ at each occurrence are independently chosen from H, $C_{1-6}$-alkyl optionally substituted by —OH, $C_{1-6}$-haloalkyl, 5-15 membered heteroaryl, $C_{3-10}$ cycloalkyl, and 3-15 membered heterocycloalkyl optionally substituted by —OH; or $R^{42}$ and $R^{43}$ may form, together with the nitrogen atom to which they are attached, a 3-15 membered heterocycloalkyl group or a 5-15 membered heteroaryl group, in which the heterocycloalkly group or 5-15 membered heteroaryl group may optionally be substituted by one or more members selected from $C_{1-6}$-alkyl. In another embodiment, $R^{42}$ and $R^{43}$ at each occurrence are independently chosen from H, $C_{1-6}$-alkyl optionally substituted by —OH, $C_{1-6}$-haloalkyl, and 3-15 membered heterocycloalkyl; or $R^{42}$ and $R^{43}$ may form, together with the nitrogen atom to which they are attached, a 3-15 membered heterocycloalkyl group or a 5-15 membered heteroaryl group. In another embodiment, $R^{42}$ and $R^{43}$ at each occurrence are independently chosen from H, $C_{1-6}$-alkyl optionally substituted by —OH, $C_{2-6}$-alkynyl, $C_{1-6}$-haloalkyl, $C_{6-15}$-aryl, 5-15 membered heteroaryl, $C_{3-10}$ cycloalkyl, and 3-15 membered heterocycloalkyl optionally substituted by —OH. In another embodiment, $R^{42}$ and $R^{43}$ at each occurrence are independently chosen from H and $C_{1-6}$-alkyl. In another embodiment, $R^{42}$ and $R^{43}$ at each occurrence are independently chosen from $C_{1-6}$-alkyl.

In another embodiment, $R^{45}$ at each occurrence are independently chosen from halogen, —$NO_2$, —$OR^{60}$, =O, —$C(=O)R^{61}$, —$C(=O)OR^{60}$, —$C(=O)NR^{62}R^{63}$, —$NR^{60}R^{61}$, $C_{1-6}$-alkyl, —$C_{1-6}$-alkyl-O—$C_{1-6}$-alkyl, $C_{1-6}$-haloalkyl, $C_{2-6}$-alkenyl, $C_{2-6}$-alkynyl, $C_{6-15}$-aryl-$(R^{77})$, 5-15 membered heteroaryl-$(R^{77})_x$, $C_{3-10}$ cycloalkyl-$(R^{77})_x$, 3-15 membered heterocycloalkyl-($R^{77}$)$_x$, pseudohalogen, —S(=O)$_n$$R^{60}$, —S(=O)$_2$$NR^{62}R^{63}$, —OCH$_2$F, —OCHF$_2$, —OCF$_3$, —NHOH, —OC(=O)$R^{60}$, —OC(=O)$NR^{62}R^{63}$, —OP(=O)(OH)$_2$, —$NR^{60}$C(=O)$R^{61}$, —$NR^{60}$C(=O)$OR^{61}$, —$NR^{60}$S(=O)$_2$$R^{61}$, —$NR^{60}$C(=O)$NR^{62}R^{63}$, —$NR^{60}$S(=O)$_2$$NR^{62}R^{63}$, and —SCF$_3$, wherein $R^{77}$ at each occurrence is independently chosen from C$_{1-6}$-alkyl. In another embodiment, $R^{45}$ at each occurrence is independently chosen from halogen, —NO$_2$, —$OR^{60}$, —C(=O)$R^{60}$, —C(=O)$OR^{60}$, —C(=O)$NR^{62}R^{63}$, —$NR^{60}R^{61}$, C$_{1-6}$-alkyl, —C$_{1-6}$-alkyl-O—C$_{1-6}$-alkyl, C$_{1-6}$-haloalkyl, C$_{2-6}$-alkenyl, C$_{2-6}$-alkynyl, C$_{6-15}$-aryl, 5-15 membered heteroaryl, C$_{3-10}$ cycloalkyl, 3-15 membered heterocycloalkyl, pseudohalogen, —S(=O)$_n$$R^{60}$, —S(=O)$_2$$NR^{62}R^{63}$, —OCH$_2$F, —OCHF$_2$, —OCF$_3$, —NHOH, —OC(=O)$R^{60}$, —OC(=O)$NR^{62}R^{63}$, —$NR^{60}$C(=O)$R^{61}$, —$NR^{60}$C(=O)$OR^{61}$, —$NR^{60}$S(=O)$R^{61}$, —$NR^{60}$C(=O)$NR^{62}R^{63}$, —$NR^{60}$S(=O)$_2$$NR^{62}R^{63}$, and —SCF$_3$, wherein $R^{77}$ at each occurrence is independently chosen from C$_{1-6}$-alkyl. In another embodiment, $R^{45}$ at each occurrence is independently chosen from halogen, —$OR^{60}$, —C(=O)$R^{60}$, —C(=O)$OR^{60}$, —C(=O)$NR^{62}R^{63}$, —$NR^{60}R^{61}$, C$_{1-6}$-alkyl, C$_{6-15}$-aryl-($R^{77}$)$_x$, 5-15 membered heteroaryl-($R^{77}$)$_x$, C$_{3-10}$ cycloalkyl-($R^{77}$)$_x$, 3-15 membered heterocycloalkyl-($R^{77}$)$_x$, pseudohalogen, —S(=O)$_n$$R^{60}$, —OC(=O)$R^{60}$, —OP(=O)(OH)$_2$, and —$NR^{60}$C(=O)$R^{61}$, wherein $R^{77}$ at each occurrence is independently chosen from C$_{1-6}$-alkyl. In another embodiment, $R^{45}$ at each occurrence is independently chosen from halogen, —OH, —OC$_{1-6}$-alkyl, —C(=O)(4-10 membered heterocycloalkyl), —C(=O)(4-10 membered heterocycloalkyl)-C$_{1-6}$-alkyl, —CO$_2$$R^{62a}$, —CO$_2$C$_{1-6}$-alkyl-O—C$_{1-6}$-alkyl, —C(=O)$NR^{62a}R^{63a}$, —$NR^{62a}R^{63a}$, C$_{1-6}$-alkyl, phenyl, 5-6 membered heteroaryl-(C$_{1-6}$-alkyl)$_x$, C$_{3-6}$ cycloalkyl, 3-10 membered heterocycloalkyl-(C$_{1-6}$-alkyl), —C≡N, —S(=O)$_2$C$_{1-6}$-alkyl, —OC(=O)C$_{1-6}$-alkyl, —OC(=O)C$_{1-6}$-alkyl-$NR^{62a}R^{63a}$, —OP(=O)(OH)$_2$ and —NHC(=O)C$_{1-6}$-alkyl, wherein each $R^{62a}$ and $R^{63a}$ is independently selected from H and C$_{1-6}$-alkyl, and each x is independently chosen from 0 and 1. In another embodiment, $R^{45}$ at each occurrence is independently chosen from halogen, —OH, —OC$_{1-6}$-alkyl, —C(=O)(4-6 membered heterocycloalkyl), —C(=O)(6 membered heterocycloalkyl)-C$_{1-6}$-alkyl, —CO$_2$$R^{62a}$, —CO$_2$C$_{1-6}$-alkyl-O—C$_{1-6}$-alkyl, —C(=O)$NR^{62a}R^{63a}$, —N(C$_{1-6}$-alkyl)$_2$, C$_{1-6}$-alkyl phenyl, 5 membered heteroaryl-(C$_{1-6}$-alkyl)$_x$, C$_{3-6}$ cycloalkyl, 5-6 membered heterocycloalkyl-(C$_{1-6}$-alkyl)$_x$, —C≡N, —S(=O)$_2$C$_{1-6}$-alkyl, —OC(=O)C$_{1-6}$-alkyl, —OC(=O)C$_{1-6}$-alkyl-NH$_2$, —OP(=O)(OH)$_2$, and —NHC(=O)C$_{1-6}$-alkyl, wherein each $R^{62a}$ and $R^{63a}$ is independently selected from H and C$_{1-6}$-alkyl, and each x is independently chosen from 0 and 1. In another embodiment, $R^{45}$ at each occurrence is independently chosen from halogen, —NO$_2$, —$OR^{60}$, —C(=O)$R^{60}$, —C(=O)$OR^{60}$, —C(=O)$NR^{62}R^{63}$, —$NR^{60}R^{61}$, C$_{1-6}$-alkyl, —C$_{1-6}$-alkyl-O—C$_{1-6}$-alkyl, C$_{1-6}$-haloalkyl, C$_{6-15}$-aryl, 5-15 membered heteroaryl, C$_{3-10}$-cycloalkyl, 3-15 membered heterocycloalkyl, —CN, —S(=O)$_n$$R^{60}$, —S(=O)$_2$$NR^{62}R^{63}$, —OCF$_3$, —OC(=O)$R^{60}$, —OC(=O)$NR^{62}R^{63}$, —$NR^{60}$C(=O)$R^{61}$, —$NR^{60}$C(=O)$OR^{61}$, —$NR^{60}$S(=O)$_2$$R^{61}$, and —$NR^{60}$C(=O)$NR^{62}R^{63}$. In another embodiment, $R^{45}$ at each occurrence is independently chosen from halogen, —$OR^{60}$, —C(=O)$R^{60}$, —C(=O)$OR^{60}$, —C(=O)$NR^{62}R^{63}$, —$NR^{60}R^{61}$, C$_{1-6}$-alkyl, C$_{1-6}$-haloalkyl, phenyl, 5-6 membered heteroaryl, C$_{3-6}$-cycloalkyl, 5-6 membered heterocycloalkyl, —CN, —S(=O)$_n$$R^{60}$, —S(=O)$_2$$NR^{62}R^{63}$, —OCF$_3$, —$NR^{60}$C(=O)$R^{61}$, —$NR^{60}$C(=O)$OR^{61}$, and —$NR^{60}$S(=O)$_2$$R^{61}$. In another embodiment, $R^{45}$ at each occurrence is independently chosen from halogen, —$OR^{60}$, —C(=O)$R^{60}$, —C(=O) $OR^{60}$, —C(=O)$NR^{62}R^{63}$, —$NR^{60}R^{61}$, C$_{1-6}$-alkyl, C$_{1-6}$-haloalkyl, 5-6 membered heteroaryl, cyclopropyl, 5-6 membered heterocycloalkyl, —CN, —S(=O)$_2$$NR^{62}R^{63}$, —OC(=O)$R^{60}$, —$NR^{60}$C(=O)$R^{61}$, and —$NR^{60}$S(=O)$_2$$R^{61}$. In another embodiment, $R^{45}$ at each occurrence is independently chosen from —$OR^{60}$, —C(=O)$R^{60}$, —C(=O)$OR^{60}$, —C(=O)$NR^{62}R^{63}$, —$NR^{60}R^{61}$ cyclopropyl, —CN, and —OC(=O)$R^{60}$. In another embodiment, $R^{45}$ at each occurrence is independently chosen from —CH$_3$, F, —OH, —OCH$_3$, —C≡N, —N(CH$_3$)$_2$, —N(CH$_2$CH$_2$)$_2$, cyclopropyl, phenyl, morpholinyl, pyrrolidinyl, 4-methylpiperazinyl, oxazolyl, 1-methylimidazolyl, 1,4-dioxanyl, —NHC(=O)CH$_3$, —C(=O)N(CH$_3$)$_2$, —C(=O)NHCH$_3$, —C(=O)NH$_2$, —C(=O)-(4-morpholinyl), —C(=O)-(4-methylpiperazinyl), —C(=O)-(pyrrolidinyl), —C(=O)-(azetidinyl), —CO$_2$H, —CO$_2$Me, —C(=O)OCH(CH$_3$)$_2$, —C(=O)O(CH$_2$)$_2$OCH$_3$, —OC(=O)CH$_3$, —OC(=O)CH$_2$NH$_2$, —OC(=O)CH(NH$_2$)CH(CH$_3$)$_2$, —OP(=O)(OH)$_2$, —OC(=O)CH$_2$CH$_3$, and —SO$_2$CH$_3$. In another embodiment, $R^{45}$ at each occurrence is independently chosen from —CH$_3$, F, —OH, —OCH$_3$, —C≡N, —N(CH$_3$)$_2$, —N(CH$_2$CH$_2$)$_2$, cyclopropyl, phenyl, 4-morpholinyl, 1-pyrrolidinyl, 4-methylpiperazin-1-yl, 2-oxazolyl, 1-methylimidazol-2-yl, 1,4-dioxan-2-yl, —NHC(=O)CH$_3$, —C(=O)N(CH$_3$)$_2$, —C(=O)NHCH$_3$, —C(=O)NH$_2$, —C(=O)-(4-morpholinyl), —C(=O)-(4-methylpiperazin-1-yl), —C(=O)-(1-pyrrolidinyl), —C(=O)-(1-azetidinyl), —CO$_2$H, —CO$_2$Me, —C(=O)OCH(CH$_3$)$_2$, —C(=O)O(CH$_2$)$_2$OCH$_3$, —OC(=O)CH$_3$, —OC(=O)CH$_2$NH$_2$, —OC(=O)CH(NH$_2$)CH(CH$_3$)$_2$, —OP(=O)(OH)$_2$, —OC(=O)CH$_2$CH$_3$, and —SO$_2$CH$_3$. In another embodiment, $A^6$, $A^7$, $A^8$, $A^9$, and $A^{10}$ are independently chosen from a bond, —$CZ^4Z^5$—, —$NZ^6$—, and —O—. In another embodiment, $A^6$ is —$CZ^4Z^5$—, —$NZ^6$—, or —O—, $A^7$, $A^8$, and $A^9$ are independently a bond or —$CZ^1Z^1$—, and $A^{10}$ is a bond. In another embodiment, $A^6$ is —CH$_2$—, —$NZ^6$—, or —O—, $A^7$, $A^8$, and $A^9$ are independently a bond or —CH$_2$—, and $A^{10}$ is a bond. In another embodiment, -$A^6$-$A^7$-$A^8$-$A^9$-$A^{10}$- is a group of formula —$NZ^6$—$CZ^4Z^5$—$CZ^4Z^5$—, —$CZ^4Z^5$—$CZ^4Z^5$—$NZ^6$—, —$CZ^4Z^5$—, —$CZ^4Z^5$—$CZ^4Z^5$—, —$CZ^4Z^5$—$CZ^4Z^5$—$CZ^4Z^5$—, —$CZ^4Z^5$—$CZ^4Z^5$—, —$CZ^4Z^5$—$CZ^4Z^5$—, —O—, or —$NZ^6$—. In another embodiment, -$A^6$-$A^7$-$A^8$-$A^9$-$A^{10}$- is a group of formula —$CZ^4Z^5$—$CZ^4Z^5$—$CZ^4Z^5$—$CZ^4Z^5$—, $Z^4Z^5$—$CZ^4Z^5$—$CZ^4Z^5$—, —$CZ^4Z^5$—$CZ^4Z^5$—, —$CZ^4Z^5$—, —O—, or —$NZ^6$—. In another embodiment, -$A^6$-$A^7$-$A^8$-$A^9$-$A^{10}$- is a group of formula =N—CH=CH—, —CH=CH—CH=, —CH=CH—N=, —C(CH$_3$)=CH—N=, —CH$_2$—, —CH$_2$CH$_2$—, —CH$_2$—CH$_2$—CH$_2$—, —CH$_2$—CH$_2$—CH$_2$—CH$_2$—, —O—, or —$NZ^6$—, wherein $Z^6$ is chosen from H, —CH$_2$CH$_3$, —CH(CH$_3$)$_2$, —CH(CH$_3$)CH$_2$CH$_3$, —CH$_2$C(CH$_3$)$_3$, —CH$_2$-cyclopropyl, —CH$_2$CH$_2$OCH$_3$, —C(=O)cyclopropyl, —C(=O)OCH$_2$CH$_3$, —CH$_2$C≡CH, and —S(=O)$_2$CH$_3$. In another embodiment, -$A^6$-$A^7$-$A^8$-$A^9$-$A^{10}$- is a group of formula —CH$_2$—CH$_2$—CH$_2$—CH$_2$—, —CH$_2$—CH$_2$—CH$_2$—, —CH$_2$—CH$_2$—, —CH$_2$—, —O—, or —$NZ^6$—.

In another embodiment, $Z^4$, $Z^5$, and $Z^6$ are defined as follows:
(i) when any two of $Z^1$, $Z^2$, $Z^3$, $Z^4$, $Z^5$, and $Z^6$ are located on adjacent atoms, they may form a bond between the atoms, and
(ii) any of $Z^4$, $Z^5$, and $Z^6$ may be independently chosen from H, halogen, —NO$_2$, —$OR^{50}$, —C(=O)$R^{50}$, —C(=O)$OR^{50}$, —C(=O)$NR^{52}R^{53}$, —$NR^{50}R^{51}$, C$_{1-6}$-alkyl, —C$_{1-6}$-alkyl-$R^{50}$, —C$_{1-6}$-alkyl-$OR^{50}$, —C$_{1-6}$- alkyl-C(=O)OR$^{50}$, —C$_{1-6}$-alkyl-NR$^{52}$R$^{53}$, —C$_{1-6}$-alkyl-CN, C$_{1-6}$-haloalkyl, C$_{2-6}$-alkenyl, C$_{2-6}$-alkynyl, C$_{6-15}$-aryl, 5-15 membered heteroaryl, C$_{3-10}$ cycloalkyl, 3-15 membered heterocycloalkyl, pseudohalogen, —S(=O)$_n$R$^{50}$, —S(=O)$_2$NR$^{52}$R$^{53}$, —OCH$_2$F, —OCHF$_2$, —OCF$_3$, —NHOH, —OC(=O)R$^{50}$, —OC(=O)NR$^{52}$R$^{53}$, —NR$^{50}$C(=O)R$^{51}$, —NR$^{50}$C(=O)OR$^{51}$, —NR$^{50}$S(=O)$_2$R$^{51}$, —NR$^{50}$C(=O)NR$^{52}$R$^{53}$, —NR$^{50}$S(=O)$_2$NR$^{52}$R$^{53}$, and —SCF$_3$.

In another embodiment, Z$^4$, Z$^5$, and Z$^6$ are defined as follows:
(i) when any two of Z$^1$, Z$^2$, Z$^3$, Z$^4$, Z$^5$, and Z$^6$ are located on adjacent atoms, they may form a bond between the atoms, and
(ii) any of Z$^4$, Z$^5$, and Z$^6$ may be independently chosen from H, halogen, —NO$_2$, —OR$^{50}$, —C(=O)R$^{50}$, —C(=O)OR$^{50}$, —C(=O)NR$^{52}$R$^{53}$, —NR$^{50}$R$^{51}$, C$_{1-6}$-alkyl, —C$_{1-6}$-alkyl-R$^{50}$, —C$_{1-6}$-alkyl-OR$^{50}$, C$_{1-6}$-haloalkyl, C$_{2-6}$-alkynyl, C$_{6-15}$-aryl, 5-15 membered heteroaryl, C$_{3-10}$ cycloalkyl, 3-15 membered heterocycloalkyl, pseudohalogen, —S(=O)$_n$R$^{50}$, —S(=O)$_2$NR$^{52}$R$^{53}$, —NHOH, —OC(=O)R$^{50}$, —OC(=O)NR$^{52}$R$^{53}$, —NR$^{50}$C(=O)R$^{51}$, —NR$^{50}$C(=O)OR$^{51}$, —NR$^{50}$S(=O)$_2$R$^{51}$, and —NR$^{50}$C(=O)NR$^{52}$R$^{53}$.

In another embodiment, Z$^4$, Z$^5$, and Z$^6$ are defined as follows:
(i) when any two of Z$^1$, Z$^2$, Z$^3$, Z$^4$, Z$^5$ and Z$^6$ are located on adjacent atoms, they may form a bond between the atoms, and
(ii) any of Z$^4$, Z$^5$, and Z$^6$ may be independently chosen from H, halogen, —NO$_2$, —OR$^{50}$, —C(=O)R$^{50}$, —C(=O)OR$^{50}$, —C(=O)NR$^{52}$R$^{53}$, —NR$^{50}$R$^{51}$, C$_{1-6}$-alkyl, —C$_{1-6}$-alkyl-R$^{50}$, —C$_{1-6}$-alkyl-OR$^{50}$, C$_{1-6}$-haloalkyl, C$_{2-6}$-alkynyl, C$_{6-15}$-aryl, 5-15 membered heteroaryl, 3-15 membered heterocycloalkyl, pseudohalogen, —S(=O)$_n$R$^{50}$, —S(=O)$_2$NR$^{52}$R$^{53}$, —NR$^{50}$C(=O)R$^{51}$, —NR$^{50}$C(=O)OR$^{51}$, and —NR$^{50}$S(=O)$_2$R$^{51}$.

In another embodiment, Z$^4$, Z$^5$, and Z$^6$ are defined as follows:
(i) when any two of Z$^1$, Z$^2$, Z$^3$, Z$^4$, Z$^5$, and Z$^6$ are located on adjacent atoms, they may form a bond between the atoms, and
(ii) any Z$^4$, Z$^5$, and Z$^6$ may be independently chosen from H, —C(=O)R$^{50}$, —C(=O)OR$^{50}$, C$_{1-6}$-alkyl, —C$_{1-6}$-alkyl-R$^{50}$, —C$_{1-6}$-alkyl-OR$^{50}$, C$_{2-6}$-alkynyl, and —S(=O)$_n$R$^{50}$.

In another embodiment, Z$^4$, Z$^5$, and Z$^6$ are defined as follows:
(i) when any two of Z$^1$, Z$^2$, Z$^3$, Z$^4$, Z$^5$, and Z$^6$ are located on adjacent atoms, they may form a bond between the atoms,
(ii) any Z$^4$ and Z$^5$ may be independently chosen from H and C$_{1-6}$-alkyl, and
(iii) any Z$^6$ may be independently chosen from H, —C(=O)R$^{50}$, —C(=O)OR$^{50}$, C$_{1-6}$-alkyl, —C$_{1-6}$-alkyl-R$^{50}$, —C$_{1-6}$-alkyl-OR$^{50}$, C$_{2-6}$-alkynyl, and —S(=O)$_n$R$^{50}$.

In another embodiment, Z$^4$, Z$^5$, and Z$^6$ are defined as follows:
(i) when any two of Z$^1$, Z$^2$, Z$^3$, Z$^4$, Z$^1$, and Z$^6$ are located on adjacent atoms, they may form a bond between the atoms, and
(ii) any Z$^4$, Z$^5$, and Z$^6$ may be independently chosen from H, —C(=O)—(C$_{3-6}$-cycloalkyl), —C(=O)OC$_{1-6}$-alkyl, C$_{1-6}$-alkyl, —C$_{1-6}$-alkyl-(C$_{3-6}$-cycloalkyl), —C$_{1-6}$-alkyl-O—C$_{1-6}$-alkyl, C$_{2-6}$-alkynyl, and —S(=O)$_2$C$_{1-6}$-alkyl.

In another embodiment, Z$^4$, Z$^5$, and Z$^6$ are defined as follows:
(i) when any two of Z$^1$, Z$^2$, Z$^3$, Z$^4$, Z$^5$, and Z$^6$ are located on adjacent atoms, they may form a bond between the atoms,
(ii) any Z$^4$ and Z$^5$ may be independently chosen from H and C$_{1-6}$-alkyl, and
(iii) any Z$^6$ may be independently chosen from H, —C(=O)—(C$_{3-6}$-cycloalkyl), —C(=O)OC$_{1-6}$-alkyl, C$_{1-6}$-alkyl, —C$_{1-6}$-alkyl-(C$_{3-6}$-cycloalkyl), —C$_{1-6}$-alkyl-O—C$_{1-6}$-alkyl, C$_{2-6}$-alkynyl, and —S(=O)$_2$C$_{1-6}$-alkyl.

In another embodiment, Z$^4$, Z$^5$, and Z$^6$ are defined as follows:
(i) when any two of Z$^1$, Z$^2$, Z$^1$, Z$^4$, Z$^5$, and Z$^6$ are located on adjacent atoms, they may form a bond between the atoms, and
(ii) any Z$^4$, Z$^5$, and Z$^6$ may be independently chosen from H, —CH$_2$CH$_3$, —CH(CH$_3$)$_2$, —CH(CH$_3$)CH$_2$CH$_3$, —CH$_2$C(CH$_3$)$_3$, —CH$_2$-cyclopropyl, —CH$_2$CH$_2$OCH$_3$, —C(=O)cyclopropyl, —C(=O)OCH$_2$CH$_3$, —CH$_2$C≡CH, and —S(=O)$_2$CH$_3$.

In another embodiment, Z$^4$, Z$^5$, and Z$^6$ are defined as follows:
(i) when any two of Z$^1$, Z$^2$, Z$^3$, Z$^4$, Z$^5$, and Z$^6$ are located on adjacent atoms, they may form a bond between the atoms,
(ii) any Z$^4$ and Z$^5$ may be independently chosen from H and —CH$_3$, and
(iii) any Z$^6$ may be independently chosen from H, —CH$_2$CH$_3$, —CH(CH$_3$)$_2$, —CH(CH$_3$)CH$_2$CH$_3$, —CH$_2$C(CH$_3$)$_3$, —CH$_2$-cyclopropyl, —CH$_2$CH$_2$OCH$_3$, —C(=O)cyclopropyl, —C(=O)OCH$_2$CH$_3$, —CH$_2$C≡CH, and —S(=O)$_2$CH$_3$.

In another embodiment, Z$^4$, Z$^5$, and Z$^6$ are independently chosen from H, —C(=O)R$^{50}$, —C(=O)OR$^{50}$, C$_{1-6}$-alkyl, —C$_{1-6}$-alkyl-R$^{50}$, —C$_{1-6}$-alkyl-OR$^{50}$, C$_{2-6}$-alkynyl, and —S(=O)$_2$R$^{50}$. In another embodiment, Z$^4$, Z$^5$, and Z$^6$ are independently chosen from H, —C(=O)C$_{3-6}$-cycloalkyl, —C(=O)O—C$_{1-6}$-alkyl, C$_{1-6}$-alkyl, —C$_{1-6}$-alkyl-C$_{3-6}$-cycloalkyl, —C$_{1-6}$-alkyl-O—C$_{1-6}$-alkyl, C$_{2-6}$-alkynyl, and —S(=O)$_2$—C$_{1-6}$-alkyl. In another embodiment, Z$^4$, Z$^5$, and Z$^6$ are independently chosen from H, —C(=O)cyclopropyl, —CO$_2$CH$_2$CH$_3$, ethyl, isopropyl, sec-butyl, —CH$_2$C(CH$_3$)$_3$, —CH$_2$-cyclopropyl, —CH$_2$CH$_2$OCH$_3$, —CH$_2$C≡CH, and —S(=O)$_2$CH$_3$. In another embodiment, Z$^4$ and Z$^5$ are H, and Z$^6$ is chosen from H, —C(=O)R$^{50}$, —C(=O)OR$^{50}$, C$_{1-6}$-alkyl, —C$_{1-6}$-alkyl-R$^{50}$, —C$_{1-6}$-alkyl-OR$^{50}$, C$_{2-6}$-alkynyl, and —S(=O)$_2$R$^{50}$. In another embodiment, Z$^4$ and Z$^5$ are H, and Z$^6$ is chosen from H, —C(=O)C$_{3-6}$-cycloalkyl, —C(=O)O—C$_{1-6}$-alkyl, C$_{1-6}$-alkyl, —C$_{1-6}$-alkyl-C$_{3-6}$-cycloalkyl, —C$_{1-6}$-alkyl-O—C$_{1-6}$-alkyl, C$_{2-6}$-alkynyl, and —S(=O)$_2$—C$_{1-6}$-alkyl. In another embodiment, Z$^4$ and Z$^5$ are H, and Z$^6$ is chosen from H, —C(=O)cyclopropyl, —CO$_2$CH$_2$CH$_3$, ethyl, isopropyl, sec-butyl, —CH$_2$C(CH$_3$)$_3$, —CH$_2$-cyclopropyl, —CH$_2$CH$_2$OCH$_3$, —CH$_2$C≡CH, and —S(=O)$_2$CH$_3$.

In another embodiment, A$^6$, A$^7$, A$^8$, A$^9$, and A$^{10}$ are defined as in any of the above embodiments, except that at least one of A$^6$, A$^7$, A$^8$, A$^9$, and A$^{10}$ is not a bond.

In another embodiment, R$^{50}$ and R$^{51}$ at each occurrence are independently chosen from C$_{1-6}$-alkyl and C$_{3-10}$ cycloalkyl. In another embodiment, R$^{50}$ and R$^{51}$ at each occurrence are independently chosen from C$_{1-6}$-alkyl and C$_{3-6}$ cycloalkyl. In another embodiment, $R^{50}$ and $R^{51}$ at each occurrence are independently chosen from $C_{1-6}$-alkyl and cyclopropyl. In another embodiment, $R^{50}$ and $R^{51}$ at each occurrence are independently chosen from H, $C_{1-6}$-alkyl optionally substituted by —OH, $C_{2-6}$-alkynyl, $C_{1-6}$-haloalkyl, $C_{6-15}$-aryl, 5-15 membered heteroaryl, $C_{3-10}$ cycloalkyl, and 3-15 membered heterocycloalkyl optionally substituted by $C_{1-6}$-alkyl or —OH. In another embodiment, $R^{50}$ and $R^{51}$ at each occurrence are independently chosen from H, $C_{1-6}$-alkyl optionally substituted by —OH, $C_{1-6}$-haloalkyl, 5-15 membered heteroaryl, $C_{3-10}$ cycloalkyl, and 3-15 membered heterocycloalkyl optionally substituted by $C_{1-6}$-alkyl or —OH. In another embodiment, $R^{50}$ and $R^{51}$ at each occurrence are independently chosen from H, $C_{1-6}$-alkyl optionally substituted by —OH, $C_{1-6}$-haloalkyl, and 3-15 membered heterocycloalkyl optionally substituted by $C_{1-6}$-alkyl or —OH. In another embodiment, $R^{50}$ and $R^{51}$ at each occurrence are independently chosen from H, $C_{1-6}$-alkyl optionally substituted by —OH, $C_{1-6}$-haloalkyl, and 3-15 membered heterocycloalkyl. In another embodiment, $R^{50}$ and $R^{51}$ at each occurrence are independently chosen from H, $C_{1-6}$-alkyl, and $C_{1-6}$-fluoroalkyl. In another embodiment, $R^{50}$ and $R^{51}$ at each occurrence are independently chosen from H, $C_{1-6}$-alkyl, 5-15 membered heteroaryl, $C_{1-6}$-haloalkyl, 3-15 membered heterocycloalkyl-$C_{1-6}$-alkyl, and 3-15 membered heterocycloalkyl. In another embodiment, $R^{50}$ and $R^{51}$ at each occurrence are independently chosen from H, $C_{1-6}$-alkyl, 5-10 membered heteroaryl, $C_{1-6}$-haloalkyl, 5-10 membered heterocycloalkyl-$C_{1-6}$-alkyl, and 5-10 membered heterocycloalkyl. In another embodiment, $R^{50}$ and $R^{51}$ at each occurrence are independently chosen from H and $C_{1-6}$-alkyl. In another embodiment, $R^{50}$ and $R^{51}$ at each occurrence are independently chosen from —$CH_3$, —$CH_2CH_3$, and cyclopropyl.

In another embodiment, $R^{52}$ and $R^{53}$ at each occurrence are independently chosen from H, $C_{1-6}$-alkyl optionally substituted by —OH, $C_{2-6}$-alkynyl, $C_{1-6}$-haloalkyl, $C_{6-15}$-aryl, 5-15 membered heteroaryl, $C_{3-10}$ cycloalkyl, and 3-15 membered heterocycloalkyl optionally substituted by —OH; or $R^{52}$ and $R^{53}$ may form, together with the nitrogen atom to which they are attached, a 3-15 membered heterocycloalkyl group or a 5-15 membered heteroaryl group, in which the heterocycloalkly group or 5-15 membered heteroaryl group may optionally be substituted by one or more members selected from $C_{1-6}$-alkyl. In another embodiment, $R^{52}$ and $R^{53}$ at each occurrence are independently chosen from H, $C_{1-6}$-alkyl optionally substituted by —OH, $C_{1-6}$-haloalkyl, 5-15 membered heteroaryl, $C_{3-10}$ cycloalkyl, and 3-15 membered heterocycloalkyl optionally substituted by —OH; or $R^{52}$ and $R^{53}$ may form, together with the nitrogen atom to which they are attached, a 3-15 membered heterocycloalkyl group or a 5-15 membered heteroaryl group, in which the heterocycloalkly group or 5-15 membered heteroaryl group may optionally be substituted by one or more members selected from $C_{1-6}$-alkyl. In another embodiment, $R^{52}$ and $R^{53}$ at each occurrence are independently chosen from H, $C_{1-6}$-alkyl optionally substituted by —OH, $C_{1-6}$-haloalkyl, and 3-15 membered heterocycloalkyl; or $R^{52}$ and $R^{53}$ may form, together with the nitrogen atom to which they are attached, a 3-15 membered heterocycloalkyl group or a 5-15 membered heteroaryl group. In another embodiment, $R^{52}$ and $R^{53}$ at each occurrence are independently chosen from H, $C_{1-6}$-alkyl optionally substituted by —OH, $C_{2-6}$-alkynyl, $C_{1-6}$-haloalkyl, $C_{6-15}$-aryl, 5-15 membered heteroaryl, $C_{3-10}$ cycloalkyl, and 3-15 membered heterocycloalkyl optionally substituted by —OH. In another embodiment, $R^{52}$ and $R^{53}$ at each occurrence are independently chosen from H, $C_{1-6}$-alkyl, and $C_{3-8}$-cycloalkyl. In another embodiment, $R^{52}$ and $R^{53}$ at each occurrence are independently chosen from H and $C_{1-6}$-alkyl. In another embodiment, $R^{52}$ and $R^{53}$ at each occurrence are independently chosen from H, $C_{1-6}$-alkyl, and cyclopropyl.

In another embodiment, $R^{55}$ at each occurrence are independently chosen from halogen, —$NO_2$, —$OR^{60}$, =O, —C(=O)$R^{60}$, —C(=O)O$R^{60}$, —C(=O)N$R^{62}R^{63}$, —N$R^{60}R^{61}$, $C_{1-6}$-alkyl, —$C_{1-6}$-alkyl-O—$C_{1-6}$-alkyl, $C_{1-6}$-haloalkyl, $C_{2-6}$-alkenyl, $C_{2-6}$-alkynyl, $C_{6-15}$-aryl-($R^{77}$)$_x$, 5-15 membered heteroaryl-($R^{77}$)$_x$, $C_{3-10}$ cycloalkyl-($R^{77}$)$_x$, 3-15 membered heterocycloalkyl-($R^{77}$)$_x$, pseudohalogen, —S(=O)$_n R^{60}$, —S(=O)$_2$N$R^{62}R^{63}$, —O$CH_2$F, —OCH$F_2$, —OC$F_3$, —NHOH, —OC(=O)$R^{60}$, —OC(=O)N$R^{62}R^{63}$, —OP(=O)(OH)$_2$, —N$R^{60}$C(=O)$R^{61}$, —N$R^{60}$C(=O)O$R^{61}$, —N$R^{60}$S(=O)$_2 R^{61}$, —N$R^{60}$C(=O)N$R^{62}R^{63}$, —N$R^{60}$S(=O)$_2$N$R^{62}R^{63}$, and —SC$F_3$, wherein $R^{77}$ at each occurrence is independently chosen from $C_{1-6}$-alkyl. In another embodiment, $R^{55}$ at each occurrence is independently chosen from halogen, —$NO_2$, —$OR^{60}$, —C(=O)$R^{60}$, —C(=O)O$R^{60}$, —C(=O)N$R^{62}R^{63}$, —N$R^{60}R^{61}$, $C_{1-6}$-alkyl, —$C_{1-6}$-alkyl-O—$C_{1-6}$-alkyl, $C_{1-6}$-haloalkyl, $C_{6-15}$-aryl, 5-15 membered heteroaryl, $C_{3-10}$-cycloalkyl, 3-15 membered heterocycloalkyl, —CN, —S(=O)$_n R^{60}$, —S(=O)$_2$N$R^{62}R^{63}$, —OC$F_3$, —OC(=O)$R^{60}$, —OC(=O)N$R^{62}R^{63}$, —N$R^{60}$C(=O)$R^{61}$, —N$R^{60}$C(=O)O$R^{61}$, —N$R^{60}$S(=O)$_2 R^{61}$, and —N$R^{60}$C(=O)N$R^{62}R^{63}$. In another embodiment, $R^{55}$ at each occurrence is independently chosen from halogen, —$OR^{60}$, —C(=O)$R^{60}$, —C(=O)N$R^{62}R^{63}$, —N$R^{60}R^{61}$, $C_{1-6}$-alkyl, $C_{1-6}$-haloalkyl, phenyl, 5-6 membered heteroaryl, $C_{3-6}$-cycloalkyl, 5-6 membered heterocycloalkyl, —CN, —S(=O)$_2 R^{60}$, —S(=O)$_2$N$R^{62}R^{63}$, —OC$F_3$, —N$R^{60}$C(=O)$R^{61}$, —N$R^{60}$C(=O)O$R^{61}$, and —N$R^{60}$S(=O)$_2 R^{61}$. In another embodiment, $R^{55}$ at each occurrence is independently chosen from halogen, —$OR^{60}$, $C_{1-6}$-alkyl, $C_{1-6}$-haloalkyl, and cyclopropyl. In another embodiment, $R^{55}$ at each occurrence is independently chosen from —$OR^{60}$ and cyclopropyl.

In another embodiment, $R^{60}$ and $R^{61}$ at each occurrence are independently chosen from H, $C_{1-6}$-alkyl, $C_{2-6}$-alkynyl, $C_{1-6}$-haloalkyl, $C_{6-15}$-aryl, 5-15 membered heteroaryl, $C_{3-10}$ cycloalkyl, and 3-15 membered heterocycloalkyl, in which said $C_{1-6}$-alkyl, $C_{2-6}$-alkynyl, $C_{1-6}$-haloalkyl, $C_{6-15}$-aryl, 5-15 membered heteroaryl, $C_{3-10}$ cycloalkyl, and 3-15 membered heterocycloalkyl groups are optionally substituted by one or more substituents independently chosen from $C_{1-6}$-alkyl, halogen, and —OH. In another embodiment, $R^{60}$ and $R^{61}$ at each occurrence are independently chosen from H, $C_{1-6}$-alkyl, and 3-15 membered heterocycloalkyl, in which said $C_{1-6}$-alkyl and 3-15 membered heterocycloalkyl groups are optionally substituted by one or more substituents independently chosen from $C_{1-6}$-alkyl, —N($R^{76}$)$_2$, and —O$R^{76}$. In another embodiment, $R^{60}$ and $R^{61}$ at each occurrence are independently chosen from H, $C_{1-6}$-alkyl, and 4-6 membered heterocycloalkyl, in which said $C_{1-6}$-alkyl and 3-15 membered heterocycloalkyl groups are optionally substituted by one or more substituents independently chosen from $C_{1-6}$-alkyl, —$NH_2$, —OH, and —O$C_{1-6}$-alkyl. In another embodiment, $R^{60}$ and $R^{61}$ at each occurrence are independently chosen from H, $C_{1-6}$-alkyl, $C_{1-6}$-alkyl-OH, $C_{1-6}$-alkyl-O—$C_{1-6}$-alkyl, $C_{1-6}$-alkyl-$NH_2$, 4-6 membered heterocycloalkyl, and 4-6 membered heterocycloalkyl-$C_{1-6}$-alkyl. In another embodiment, $R^{60}$ and $R^{61}$ at each occurrence are independently chosen from H, $C_{1-6}$-alkyl, $C_{1-6}$-alkyl-OH, $C_{1-6}$-alkyl-O—$C_{1-6}$-alkyl, $C_{1-6}$-alkyl-$NH_2$, 4-6 membered heterocycloalkyl, and 6 membered heterocycloalkyl-$C_{1-6}$-alkyl. In another embodiment, $R^{60}$ and $R^{61}$ at each occurrence are independently chosen from H, $C_{1-6}$-alkyl optionally substituted by —OH, $C_{2-6}$-alkynyl, $C_{1-6}$-haloalkyl, $C_{6-15}$-aryl, 5-15 membered heteroaryl, $C_{3-10}$ cycloalkyl, and 3-15 membered heterocycloalkyl optionally substituted by $C_{1-6}$-alkyl or —OH. In another embodiment, $R^{60}$ and $R^{61}$ at each occurrence are independently chosen from H, $C_{1-6}$-alkyl optionally substituted by —OH, $C_{1-6}$-haloalkyl, 5-15 membered heteroaryl, $C_{3-10}$ cycloalkyl, and 3-15 membered heterocycloalkyl optionally substituted by $C_{1-6}$-alkyl or —OH. In another embodiment, $R^{60}$ and $R^{61}$ at each occurrence are independently chosen from H, $C_{1-6}$-alkyl optionally substituted by —OH, $C_{1-6}$-haloalkyl, and 3-15 membered heterocycloalkyl optionally substituted by $C_{1-6}$-alkyl or —OH. In another embodiment, $R^{60}$ and $R^{61}$ at each occurrence are independently chosen from H, $C_{1-6}$-alkyl optionally substituted by —OH, $C_{1-6}$-haloalkyl, and 3-15 membered heterocycloalkyl. In another embodiment, $R^{60}$ and $R^{61}$ at each occurrence are independently chosen from H, $C_{1-6}$-alkyl, and $C_{1-6}$-fluoroalkyl. In another embodiment, $R^{60}$ and $R^{61}$ at each occurrence are independently chosen from H, $C_{1-6}$-alkyl, 5-15 membered heteroaryl, $C_{1-6}$-haloalkyl, 3-15 membered heterocycloalkyl-$C_{1-6}$-alkyl, and 3-15 membered heterocycloalkyl. In another embodiment, $R^{60}$ and $R^{61}$ at each occurrence are independently chosen from H, $C_{1-6}$-alkyl, 5-10 membered heteroaryl, $C_{1-6}$-haloalkyl, 5-10 membered heterocycloalkyl-$C_{1-6}$-alkyl, and 5-10 membered heterocycloalkyl. In another embodiment, $R^{60}$ and $R^{61}$ at each occurrence are independently chosen from H and $C_{1-6}$-alkyl. In another embodiment, $R^{60}$ and $R^{61}$ at each occurrence are independently chosen from H, —CH$_3$, —CH$_2$CH$_3$, —CH$_2$CH$_2$OH, 4-morpholinyl, 4-methylpiperazin-1-yl, 1-pyrrolidinyl, 1-azetidinyl, —CH(CH$_3$)$_2$, —(CH$_2$)$_2$OCH$_3$, —CH$_2$NH$_2$, and —CH(NH$_2$)CH(CH$_3$)$_2$.

In another embodiment, $R^{62}$ and $R^{63}$ at each occurrence are independently chosen from H, $C_{1-6}$-alkyl, $C_{2-6}$-alkynyl, $C_{1-6}$-haloalkyl, $C_{6-15}$-aryl, 5-15 membered heteroaryl, $C_{3-10}$ cycloalkyl, and 3-15 membered heterocycloalkyl, in which said $C_{1-6}$-alkyl, $C_{2-6}$-alkynyl, $C_{1-6}$-haloalkyl, $C_{6-15}$-aryl, 5-15 membered heteroaryl, $C_{3-10}$ cycloalkyl, and 3-15 membered heterocycloalkyl groups are optionally substituted by one or more substituents independently chosen from $C_{1-6}$-alkyl, halogen, and —OH; or $R^{62}$ and $R^{63}$ may form, together with the nitrogen atom to which they are attached, a 3-15 membered heterocycloalkyl group or a 5-15 membered heteroaryl group, in which said 3-15 membered heterocycloalkyl group or 5-15 membered heteroaryl group is optionally substituted by one or more substituents independently chosen from $C_{1-6}$-alkyl, halogen, and —OH. In another embodiment, $R^{62}$ and $R^{63}$ at each occurrence are independently chosen from H, $C_{1-6}$-alkyl optionally substituted by —OH, $C_{2-6}$-alkynyl, $C_{1-6}$-haloalkyl, $C_{6-15}$-aryl, 5-15 membered heteroaryl, $C_{3-10}$ cycloalkyl, and 3-15 membered heterocycloalkyl optionally substituted by —OH; or $R^{62}$ and $R^{63}$ may form, together with the nitrogen atom to which they are attached, a 3-15 membered heterocycloalkyl group or a 5-15 membered heteroaryl group, in which the heterocycloalkly group or 5-15 membered heteroaryl group may optionally be substituted by one or more members selected from $C_{1-6}$-alkyl. In another embodiment, $R^{62}$ and $R^{63}$ at each occurrence are independently chosen from H, $C_{1-6}$-alkyl optionally substituted by —OH, $C_{1-6}$-haloalkyl, 5-15 membered heteroaryl, $C_{3-10}$ cycloalkyl, and 3-15 membered heterocycloalkyl optionally substituted by —OH; or $R^{62}$ and $R^{63}$ may form, together with the nitrogen atom to which they are attached, a 3-15 membered heterocycloalkyl group or a 5-15 membered heteroaryl group, in which the heterocycloalkly group or 5-15 membered heteroaryl group may optionally be substituted by one or more members selected from $C_{1-6}$-alkyl. In another embodiment, $R^{62}$ and $R^{63}$ at each occurrence are independently chosen from H, $C_{1-6}$-alkyl optionally substituted by —OH, $C_{1-6}$-haloalkyl, and 3-15 membered heterocycloalkyl; or $R^{62}$ and $R^{63}$ may form, together with the nitrogen atom to which they are attached, a 3-15 membered heterocycloalkyl group or a 5-15 membered heteroaryl group. In another embodiment, $R^{62}$ and $R^{63}$ at each occurrence are independently chosen from H, $C_{1-6}$-alkyl optionally substituted by —OH, $C_{2-6}$-alkynyl, $C_{1-6}$-haloalkyl, $C_{6-15}$-aryl, 5-15 membered heteroaryl, $C_{3-10}$ cycloalkyl, and 3-15 membered heterocycloalkyl optionally substituted by —OH. In another embodiment, $R^{62}$ and $R^{63}$ at each occurrence are independently chosen from H, $C_{1-6}$-alkyl, and $C_{3-8}$-cycloalkyl. In another embodiment, $R^{62}$ and $R^{63}$ at each occurrence are independently chosen from H and $C_{1-6}$-alkyl. In another embodiment, $R^{62}$ and $R^{63}$ at each occurrence are independently chosen from H and —CH$_3$. In another embodiment, $R^{62}$ and $R^{63}$ at each occurrence are independently chosen from H, $C_{1-6}$-alkyl, and cyclopropyl.

In another embodiment, $R^{10}$, $R^{11}$, $R^{20}$, $R^{21}$, $R^{30}$, $R^{31}$, $R^{40}$, $R^{41}$, $R^{50}$, $R^{51}$, $R^{60}$, and $R^{61}$ at each occurrence are independently chosen from H, $C_{1-6}$-alkyl optionally substituted by —OH, $C_{2-6}$-alkynyl, $C_{1-6}$-haloalkyl, $C_{6-15}$-aryl, 5-15 membered heteroaryl, $C_{3-10}$ cycloalkyl, and 3-15 membered heterocycloalkyl optionally substituted by $C_{1-6}$-alkyl or —OH. In another embodiment, $R^{10}$, $R^{11}$, $R^{20}$, $R^{21}$, $R^{30}$, $R^{31}$, $R^{40}$, $R^{41}$, $R^{50}$, $R^{51}$, $R^{60}$, and $R^{61}$ at each occurrence are independently chosen from H, $C_{1-6}$-alkyl optionally substituted by —OH, $C_{1-6}$-haloalkyl, 5-15 membered heteroaryl, $C_{3-10}$ cycloalkyl, and 3-15 membered heterocycloalkyl optionally substituted by $C_{1-6}$-alkyl or —OH. In another embodiment, $R^{10}$, $R^{11}$, $R^{20}$, $R^{21}$, $R^{30}$, $R^{31}$, $R^{40}$, $R^{41}$, $R^{50}$, $R^{51}$, $R^{60}$, and $R^{61}$ at each occurrence are independently chosen from H, $C_{1-6}$-alkyl optionally substituted by —OH, $C_{1-6}$-haloalkyl, and 3-15 membered heterocycloalkyl optionally substituted by $C_{1-6}$-alkyl or —OH. In another embodiment, $R^{10}$, $R^{11}$, $R^{20}$, $R^{21}$, $R^{30}$, $R^{31}$, $R^{40}$, $R^{41}$, $R^{50}$, $R^{51}$, $R^{60}$, and $R^{61}$ at each occurrence are independently chosen from H, $C_{1-6}$-alkyl optionally substituted by —OH, $C_{1-6}$-haloalkyl, and 3-15 membered heterocycloalkyl. In another embodiment, $R^{10}$, $R^{11}$, $R^{20}$, $R^{21}$, $R^{30}$, $R^{31}$, $R^{40}$, $R^{41}$, $R^{50}$, $R^{51}$, $R^{60}$, and $R^{61}$ at each occurrence are independently chosen from H and $C_{1-6}$-alkyl.

In another embodiment, $R^{12}$, $R^{13}$, $R^{22}$, $R^{23}$, $R^{32}$, $R^{33}$, $R^{42}$, $R^{43}$, $R^{52}$, $R^{53}$, $R^{62}$, and $R^{63}$, at each occurrence are independently chosen from H, $C_{1-6}$-alkyl optionally substituted by —OH, $C_{2-6}$-alkynyl, $C_{1-6}$-haloalkyl, $C_{6-15}$-aryl, 5-15 membered heteroaryl, $C_{3-10}$ cycloalkyl, and 3-15 membered heterocycloalkyl optionally substituted by —OH; or $R^{12}$ and $R^{13}$, $R^{22}$ and $R^{23}$, $R^{32}$ and $R^{33}$, $R^{42}$ and $R^{43}$, $R^{52}$ and $R^{53}$, or $R^{62}$ and $R^{63}$ may form, together with the nitrogen atom to which they are attached, a 3-15 membered heterocycloalkyl group or a 5-15 membered heteroaryl group, in which the heterocycloalkly group or 5-15 membered heteroaryl group may optionally be substituted by one or more members selected from $C_{1-6}$-alkyl. In another embodiment, $R^{12}$, $R^{13}$, $R^{22}$, $R^{23}$, $R^{32}$, $R^{33}$, $R^{42}$, $R^{43}$, $R^{52}$, $R^{53}$, $R^{62}$, and $R^{63}$, at each occurrence are independently chosen from H, $C_{1-6}$-alkyl optionally substituted by —OH, $C_{1-6}$-haloalkyl, 5-15 membered heteroaryl, $C_{3-10}$ cycloalkyl, and 3-15 membered heterocycloalkyl optionally substituted by —OH; or $R^{12}$ and $R^{13}$, $R^{22}$ and $R^{23}$, $R^{32}$ and $R^{33}$, $R^{42}$ and $R^{43}$, $R^{52}$ and $R^{53}$, or $R^{62}$ and $R^{63}$ may form, together with the nitrogen atom to which they are attached, a 3-15 membered heterocycloalkyl group or a 5-15 membered heteroaryl group, in which the heterocycloalkly group or 5-15 membered heteroaryl group may optionally be substituted by one or more members selected from $C_{1-6}$-alkyl. In another embodiment, $R^{12}$, $R^{13}$, $R^{22}$, $R^{23}$, $R^{32}$, $R^{33}$, $R^{42}$, $R^{52}$, $R^{53}$, $R^{62}$, and $R^{63}$, at each occurrence are independently chosen from H, $C_{1-6}$-alkyl optionally substituted by —OH, $C_{1-6}$-haloalkyl, and 3-15 membered heterocycloalkyl; or $R^{12}$ and $R^{13}$, $R^{22}$ and $R^{23}$, $R^{32}$ and $R^{33}$, $R^{42}$ and $R^{43}$, $R^{52}$ and $R^{53}$, or $R^{62}$ and $R^{63}$ may form, together with the nitrogen atom to which they are attached, a 3-15 membered heterocycloalkyl group or a 5-15 membered heteroaryl group. In another embodiment, $R^{12}$, $R^{13}$, $R^{22}$, $R^{23}$, $R^{32}$, $R^{33}$, $R^{42}$, $R^{43}$, $R^{52}$, $R^{53}$, $R^{62}$, and $R^{63}$, at each occurrence are independently chosen from H, $C_{1-6}$-alkyl optionally substituted by —OH, $C_{1-6}$-haloalkyl, and 3-15 membered heterocycloalkyl. In another embodiment, $R^{12}$, $R^{13}$, $R^{22}$, $R^{23}$, $R^{32}$, $R^{33}$, $R^{42}$, $R^{43}$, $R^{52}$, $R^{53}$, $R^{62}$, and $R^{63}$, at each occurrence are independently chosen from H and $C_{1-6}$-alkyl.

In another embodiment, n at each occurrence is independently chosen from 0 and 2. In another embodiment, n is 2.

In another embodiment, x at each occurrence is independently chosen from 0, 1, 2, 3, and 4. In another embodiment, x at each occurrence is independently chosen from 0, 1, 2, and 3. In another embodiment, x at each occurrence is independently chosen from 0, 1, and 2. In another embodiment, x at each occurrence is independently chosen from 0 and 1. In another embodiment, x is 0. In another embodiment, x is 1.

According to the present invention, any combination of the above-recited embodiments may be combined to define the variables $R^1$, $R^2$, $R^3$, $R^4$, $R^5$, $R^6$, $R^{10}$, $R^{11}$, $R^{12}$, $R^{13}$, $R^{20}$, $R^{21}$, $R^{22}R^{23}$, $R^{25}$, $R^{30}$, $R^{31}$, $R^{32}$, $R^{33}$, $R^{35}R^{40}$, $R^{41}$, $R^{42}$, $R^{43}$, $R^{45}$, $R^{50}$, $R^{51}$, $R^{52}$, $R^{53}$, $R^{55}$, $R^{60}$, $R^{61}$, $R^{62}$, $R^{63}$, $A^1$, $A^2$, $A^3$, $A^4$, $A^5$, $A^6$, $A^7$, $A^8$, $A^9$, $A^{10}$, $Z^1$, $Z^2$, $Z^3$, $Z^4$, $Z^5$, $Z^6$, n and x in the compound of formula I or II. Therefore, the present invention provides a compound of formula I or II and pharmaceutically acceptable salts thereof in which $R^1$, $R^2$, $R^3$, $R^4$, $R^5$, $R^6$, $R^{10}$, $R^{11}$, $R^{12}$, $R^{13}$, $R^{20}$, $R^{21}$, $R^{22}$, $R^{23}$, $R^{25}$, $R^{30}$, $R^{31}$, $R^{32}$, $R^{33}$, $R^{35}$, $R^{40}$, $R^{41}$, $R^{42}$, $R^{43}$, $R^{45}$, $R^{50}$, $R^{51}$, $R^{52}$, $R^{53}$, $R^{55}$, $R^{60}$, $R^{61}$, $R^{62}$, $R^{63}$, $A^1$, $A^2$, $A^3$, $A^4$, $A^5$, $A^6$, $A^7$, $A^8$, $A^9$, $A^{10}$, $Z^1$, $Z^2$, $Z^3$, $Z^4$, $Z^5$, $Z^6$, n and x are independently selected from any of the above-recited embodiments. In other words, the present invention includes a compound of formula I or II and pharmaceutically acceptable salts thereof in which $R^1$, $R^2$, $R^3$, $R^4$, $R^5$, $R^6$, $R^{10}$, $R^{11}$, $R^{12}$, $R^{13}$, $R^{20}$, $R^{21}$, $R^{22}$, $R^{23}$, $R^{25}$, $R^{30}$, $R^{31}$, $R^{32}$, $R^{33}$, $R^{35}$, $R^{40}$, $R^{41}$, $R^{42}$, $R^{43}$, $R^{45}$, $R^{50}$, $R^{51}$, $R^{52}$, $R^{53}$, $R^{55}$, $R^{60}$, $R^{61}$, $R^{62}$, $R^{63}$, $A^1$, $A^2$, $A^3$, $A^4$, $A^5$, $A^6$, $A^7$, $A^8$, $A^9$, $A^{10}$, $Z^1$, $Z^2$, $Z^3$, $Z^4$, $Z^5$, $Z^6$, n and x are defined by any combination of the broader and narrower definitions of these variables as recited in any of the above embodiments. For example, included within the scope of the present invention are compounds of formula I or II and pharmaceutically acceptable salts thereof in which $R^1$ is H, halogen, —$NO_2$, —$OR^{10}$, —$C(=O)R^{10}$, —$C(=O)OR^{10}$, —$C(=O)NR^{12}R^{13}$, —$NR^{10}R^{11}$, $C_{1-6}$-alkyl, —$C_{1-6}$-alkyl-$OR^{10}$, —$C_{1-6}$-alkyl-$NR^{12}R^{13}$, $C_{1-6}$-haloalkyl, $C_{2-6}$-alkenyl, $C_{2-6}$-alkynyl, $C_{6-15}$-aryl, 5-15 membered heteroaryl, $C_{3-10}$ cycloalkyl, 3-15 membered heterocycloalkyl, pseudohalogen, —$S(=O)_nR^{10}$, —$S(=O)_2NR^{12}R^{13}$, —$OCH_2F$, —$OCHF_2$, —$OCF_3$, —NHOH, —$OC(=O)R^{10}$, —$OC(=O)NR^{12}R^{13}$, —$NR^{10}C(=O)R^{11}$, —$NR^{10}C(=O)OR^{11}$, —$NR^{10}S(=O)_2R^{11}$, —$NR^{10}C(=O)NR^{12}R^{13}$, —$NR^{10}S(=O)_2NR^{12}R^{13}$, or —$SCF_3$;

$R^2$ is a group chosen from $C_{1-6}$-alkyl, $C_{2-6}$-alkenyl, $C_{2-6}$-alkynyl, $C_{6-15}$-aryl, $C_{3-10}$-cycloalkyl, 3-15 membered heterocycloalkyl, and 5-15 membered heteroaryl, wherein the $R^2$ group is optionally substituted by one or more members independently chosen from halogen, —$NO_2$, —$OR^{20}$, —$C(=O)R^{20}$, —$C(=O)OR^{20}$, —$C(=O)NR^{22}R^{23}$, —$NR^{20}R^{21}$, $C_{1-6}$-alkyl-$(R^{25})_x$, $C_{6-15}$-aryl-$(R^{25})_x$, 5-15 membered heteroaryl-$(R^{25})_x$, $C_{3-10}$ cycloalkyl-$(R^{25})_x$, 3-15 membered heterocycloalkyl-$(R^{25})_x$, pseudohalogen, —$S(=O)_nR^{20}$, —$S(=O)_2NR^{22}R^{23}$, —$OCH_2F$, —$OCHF_2$, —$OCF_3$, —NHOH, —$OC(=O)R^{20}$, —$OC(=O)NR^{22}R^{23}$, —$NR^{20}C(=O)R^{21}$, —$NR^{20}C(=O)OR^{21}$, —$NR^{20}S(=O)_2R^{21}$, —$NR^{20}C(=O)NR^{22}R^{23}$, —$NR^{20}S(=O)_2NR^{22}R^{23}$, and —$SCF_3$;

$R^3$, $R^4$, and $R^5$ are independently chosen from H, halogen, —$NO_2$, —$OR^{30}$, —$C(=O)R^{30}$, —$C(=O)OR^{30}$, —$C(=O)NR^{32}R^{33}$, —$NR^{30}R^{31}$, $C_{1-6}$-alkyl-$(R^{35})_x$, $C_{6-15}$-aryl-$(R^{35})_x$, 5-15 membered heteroaryl-$(R^{35})_x$, $C_{3-10}$ cycloalkyl-$(R^{35})_x$, 3-15 membered heterocycloalkyl-$(R^{35})_x$, pseudohalogen, —$S(=O)_nR^{30}$, —$S(=O)_2NR^{32}R^{33}$, —$OCH_2F$, —$OCHF_2$, —$OCF_3$, —NHOH, —$OC(=O)R^{30}$, —$C(=O)NR^{32}R^{33}$, —$NR^{30}C(=O)R^{31}$, —$NR^{30}C(=O)OR^{31}$, —$NR^{30}S(=O)_2R^{31}$, —$NR^{30}C(=O)NR^{32}R^{33}$, —$NR^{30}S(=O)_2NR^{32}R^{33}$, and —$SCF_3$;

$A^1$, $A^2$, $A^3$, $A^4$, and $A^5$ are each independently —$CZ^1Z^2$—, —$C(=O)$—, —$NZ^3$—, —S—, —$S(=O)$—, —$S(=O)_2$—, or —O—, wherein:

(a) when any two of $Z^1$, $Z^2$, and $Z^3$ are located on adjacent atoms, they may form a bond between the atoms, (b) any of $Z^1$, $Z^2$, and $Z^3$ may be independently chosen from H, halogen, —$NO_2$, —$OR^{40}$, —$C(=O)R^{40}$, —$C(=O)OR^{40}$, —$C(=O)NR^{42}R^{43}$, —$NR^{40}R^{41}$, $C_{1-6}$-alkyl-$(R^{45})_x$, $C_{6-15}$-aryl-$(R^{45})_x$, 5-15 membered heteroaryl-$(R^{45})_x$, $C_{3-10}$ cycloalkyl-$(R^{45})_x$, 3-15 membered heterocycloalkyl-$(R^{45})$, pseudohalogen, —$S(=O)_nR^{40}$, —$S(=O)_2NR^{42}R^{43}$, —$OCH_2F$, —$OCHF_2$, —$OCF_3$, —NHOH, —$OC(=O)R^{40}$, —$OC(=O)NR^{42}R^{43}$, —$NR^{40}C(=O)R^{41}$, —$NR^{40}C(=O)OR^{41}$, —$NR^{40}S(=O)_2R^{41}$, —$NR^{40}C(=O)NR^{42}R^{43}$, —$NR^{40}S(=O)_2NR^{42}R^{43}$, and —$SCF_3$, and (c) any two of $Z^1$, $Z^2$, and $Z^3$ may together form a group of formula -$A^6$-$A^7$-$A^8$-$A^9$-$A^{10}$-, wherein $A^6$, $A^7$, $A^8$, $A^9$, and $A^{10}$ are independently chosen from a bond, —$CZ^4Z^5$—, —$C(=O)$—, —$NZ^6$—, —S—, —$S(=O)$—, —$S(=O)_2$—, or —O—, wherein:

(i) when any two of $Z^1$, $Z^1$, $Z^3$, $Z^4$, $Z^5$, and $Z^6$ are located on adjacent atoms, they may form a bond between the atoms, and (ii) any of $Z^4$, $Z^5$, and $Z^6$ may be independently chosen from H, halogen, —$NO_2$, —$OR^{50}$, —$C(=O)R^{50}$, —$C(=O)OR^{50}$, —$C(=O)NR^{52}R^{53}$, —$NR^{50}R^{51}$, $C_{1-6}$-alkyl-$(R^{55})_x$, $C_{6-15}$-aryl-$(R^{55})_x$, 5-15 membered heteroaryl-$(R^{55})_x$, $C_{3-10}$ cycloalkyl-$(R^{55})_x$, 3-15 membered heterocycloalkyl-$(R^{55})_x$, pseudohalogen, —$S(=O)_nR^{50}$, —$S(=O)_2NR^{52}R^{53}$, —$OCH_2F$, —$OCHF_2$, —$OCF_3$, —NHOH, —$OC(=O)R^{50}$, —$OC(=O)NR^{52}R^{53}$, —$NR^{50}C(=O)R^{51}$, —$NR^{50}C(=O)OR^{51}$, —$NR^{50}S(=O)_2R^{51}$, —$NR^{50}C(=O)NR^{52}R^{53}$, —$NR^{50}S(=O)_2NR^{52}R^{53}$, and —$SCF_3$;

$R^{25}$, $R^{35}$, $R^{45}$, and $R^{55}$ at each occurrence are independently chosen from halogen, —$NO_2$, —$OR^{60}$, —$C(=O)R^{60}$, —$C(=O)OR^{60}$, —$C(=O)NR^{62}R^{63}$, —$NR^{60}R^{61}$, $C_{1-6}$-alkyl, —$C_{1-6}$-alkyl-O—$C_{1-6}$-alkyl, $C_{1-6}$-haloalkyl, $C_{2-6}$-alkenyl, $C_{2-6}$-alkynyl, $C_{6-15}$-aryl, 5-15 membered heteroaryl, $C_{3-10}$ cycloalkyl, 3-15 membered heterocycloalkyl, pseudohalogen, —$S(=O)_nR^{60}$, —$S(=O)_2NR^{62}R^{63}$, —$OCH_2F$, —$OCHF_2$, —$OCF_3$, —NHOH, —$OC(=O)R^{60}$, —$OC(=O)NR^{62}R^{63}$, —$NR^{60}C(=O)R^{61}$, —$NR^{60}C(=O)OR^{61}$, —$NR^{60}S(=O)_2R^{61}$, —$NR^{60}C(=O)NR^{62}R^{63}$, —$NR^{60}S(=O)_2NR^{62}R^{63}$, and —$SCF_3$;

$R^{10}$, $R^{11}$, $R^{20}$, $R^{21}$, $R^{30}$, $R^{31}$, $R^{40}$, $R^{41}$, $R^{50}$, $R^{51}$, $R^{60}$, and $R^{61}$ at each occurrence are independently chosen from H, $C_{1-6}$-alkyl, $C_{2-6}$-alkynyl, $C_{1-6}$-haloalkyl, $C_{6-15}$-aryl, 5-15 membered heteroaryl, $C_{3-10}$ cycloalkyl, and 3-15 membered heterocycloalkyl, in which said $C_{1-6}$-alkyl, $C_{2-6}$-alkynyl, $C_{1-6}$-haloalkyl, $C_{6-15}$-aryl, 5-15 membered heteroaryl, $C_{3-10}$ cycloalkyl, and 3-15 membered heterocycloalkyl groups are optionally substituted by one or substituents independently chosen from $C_{1-6}$-alkyl, halogen, and —OH;

$R^{12}$, $R^{13}$, $R^{22}$, $R^{23}$, $R^{32}$, $R^{33}$, $R^{42}$, $R^{43}$, $R^{52}$, $R^{53}$, $R^{62}$, and $R^{63}$ at each occurrence are independently chosen from H, $C_{1-6}$-alkyl, $C_{2-6}$-alkynyl, $C_{1-6}$-haloalkyl, $C_{6-15}$-aryl, 5-15 membered heteroaryl, $C_{3-10}$ cycloalkyl, and 3-15 membered heterocycloalkyl, in which said $C_{1-6}$-alkyl, $C_{2-6}$-alkynyl, $C_{1-6}$-haloalkyl, $C_{6-15}$-aryl, 5-15 membered heteroaryl, $C_{3-10}$ cycloalkyl, and 3-15 membered heterocycloalkyl groups are optionally substituted by one or more substituents independently chosen from $C_{1-6}$-alkyl, halogen, and —OH; or $R^{12}$ and $R^{13}$, $R^{22}$ and $R^{23}$, $R^{32}$ and $R^{33}$, $R^{42}$ and $R^{43}$, $R^{52}$ and $R^{53}$, or $R^{62}$ and $R^{63}$ may form, together with the nitrogen atom to which they are attached, a 3-15 membered heterocycloalkyl group or a 5-15 membered heteroaryl group, in which said 3-15 membered heterocycloalkyl group or 5-15 membered heteroaryl group is optionally substituted by one or more substituents independently chosen from $C_{1-6}$-alkyl, halogen, and —OH;

n at each occurrence is independently chosen from 0, 1, and 2; and x at each occurrence is independently chosen from 0, 1, 2, 3, 4, 5, and 6;

with the proviso that the compound is not:

(a)
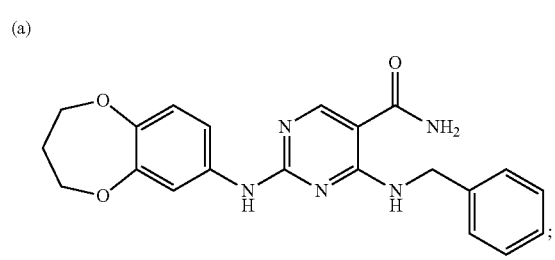
;

(b)
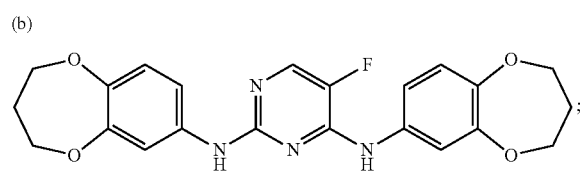
;

(c)
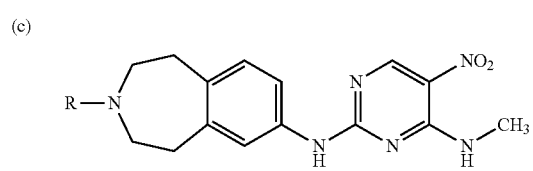

wherein R=H or —C(=O)CF$_3$;

(d)
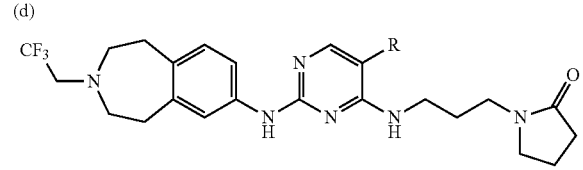

wherein R=Br, Cl, CH$_3$, or CF$_3$;

(e)
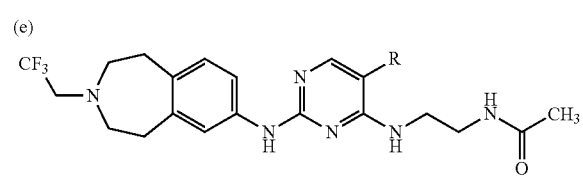

wherein R=Br, Cl, or CH$_3$;

(f)
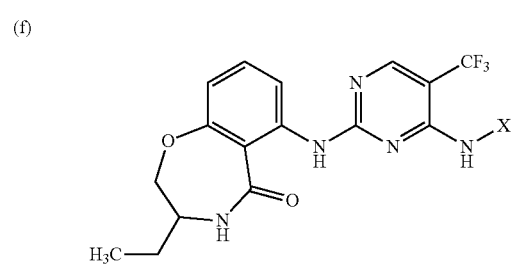

wherein X=

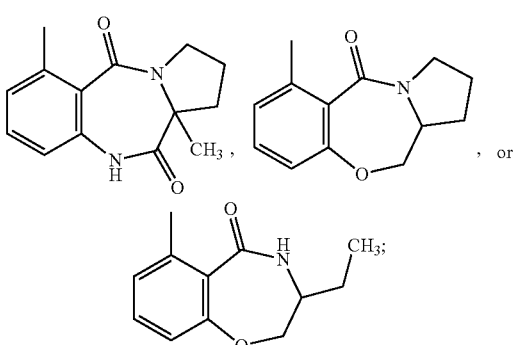

(g)
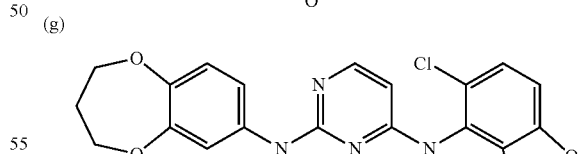

(h)
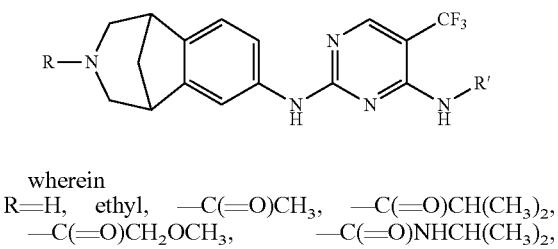

wherein
R=H, ethyl, —C(=O)CH$_3$, —C(=O)CH(CH$_3$)$_2$, —C(=O)CH$_2$OCH$_3$, —C(=O)NHCH(CH$_3$)$_2$,

—C(═O)CH₂NHC(═O)CH₃, —C(═O)CHF₂, —C(═O)CF₃, —C(═O)NHCH₂CH₃, —C(═O)CH₂N(CH₃)₂,

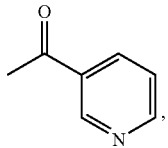

2-pyridyl, or S(═O)₂CH₃, and

R'=cyclopropyl, cyclobutyl, —CH₂-cyclopropyl, ethyl, —CH(CH₃)₂, propyl, methyl,

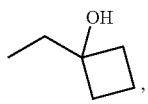

—(CH₂)₂OCH₃, or

(i)

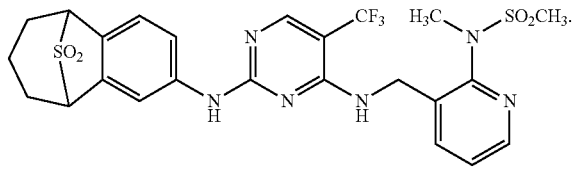

As another example, also included within the scope of the present invention are compounds of formula I or II and pharmaceutically acceptable salts thereof in which R¹ is halogen, nitro, C₁₋₆-alkyl, C₁₋₆-haloalkyl, or cyano; R² is a group chosen from C₁₋₆-alkyl, C₂₋₆-alkynyl, C₆₋₁₀-aryl, C₅₋₇-cycloalkyl, and 5-7 membered heterocycloalkyl, wherein the R² group is optionally substituted by one or more members independently chosen from halogen, —OR²⁰, —C(═O)R²⁰, —C(═O)OR²⁰, —C(═O)NR²²R²³, —C(═O)N(C₁₋₆-alkyl-OH)R²⁰, —NR²⁰R²¹, C₂₋₆-alkyl, 5-15 membered heteroaryl optionally substituted by one or more members chosen from C₁₋₆-alkyl and —C₁₋₆-alkyl-O—C₁₋₆-alkyl, 5-10 membered heterocycloalkyl, —S(═O)₂NR²²R²³, —NHC(═O)R²¹, —NHS(═O)₂R²¹, and —NHC(═O)NR²²R²³; R²⁰, R²¹, R²², and R²³ at each occurrence are independently chosen from H, C₁₋₆-alkyl, C₁₋₆-fluoroalkyl, C₂₋₆-alkynyl, and C₃₋₆-cycloalkyl; R³, R⁴, and R⁵ are independently chosen from H, halogen, —OR³⁰, —C(═O)R³⁰, and —NR³⁰R³¹; R³⁰ and R³¹ at each occurrence are independently chosen from H, C₁₋₆-alkyl, and C₁₋₆-fluoroalkyl; and -A¹-A²-A³-A⁴-A⁵- is a group of formula:

(a) —CH₂—CH₂—CZ¹Z²—CH₂—CH₂—, wherein Z¹ and Z² are independently chosen from H, halogen, and 6-membered heterocycloalkyl, (b) —CZ¹Z²—CH₂—CH₂—CH₂—NZ³—, wherein Z¹, Z², and Z³ are independently chosen from H and C₁₋₆-alkyl, (c) —CZ¹Z²—CH₂—CZ¹Z²—C(═O)—NZ³—, wherein Z¹ and Z² are independently chosen from H and C₁₋₆-alkyl, and Z³ is chosen from H, C₁₋₆-alkyl, —C₁₋₆-alkyl-C(═O)OH, —C₁₋₆-alkyl-C(═O)O—C₁₋₆-alkyl, —C₁₋₆-alkyl-C(═O)-6 membered heterocycloalkyl-C₁₋₆-alkyl, and —C₁₋₆-alkyl-O—C₁₋₆-alkyl, (d) —CH₂—CH₂—CH₂—NZ³—C(═O)—, wherein Z³ is chosen from H and C₁₋₆-alkyl, (e) —CH₂—CH₂—C(═O)—CH₂—CH₂—, (f) —CH₂—CH₂—NZ³—CH₂—CH₂—, wherein Z³ is chosen from H, C₁₋₆-alkyl, —C(═O)C₁₋₆-fluoroalkyl, —C(═O)N(C₁₋₆alkyl)(C₁₋₆-alkyl), —C₁₋₆-alkyl-O—C₁₋₆-alkyl, —C₁₋₆-alkyl-C(═O)N(C₁₋₆alkyl)(C₁₋₆-alkyl), —C₁₋₆-alkyl-NHC(═O)—C₁₋₆-alkyl, C₁₋₆-fluoroalkyl, —C₁₋₆-fluoroalkyl-OH, —C₁₋₆-fluoroalkyl-O—C₁₋₆-alkyl, C₂₋₆-alkynyl, and —S(═O)₂—C₁₋₆-alkyl, (g) —CH₂—CH₂—O—CH₂—CH₂—, (h) —CH₂—CH₂—NZ³—C(═O)—CZ¹Z²—, wherein Z¹, Z², and Z³ are independently chosen from H and C₁₋₆-alkyl, (i) —CH₂—NZ³—CH₂—CH₂—NZ³ᵃ—, wherein Z³ is chosen from H, —C(═O)C₁₋₆-alkyl, and —C₁₋₆-alkyl-O—C₁₋₆-alkyl, and Z³ᵃ is chosen from H and C₁₋₆-alkyl, (j) —CH₂—O—CH₂—CH₂—NZ³—, wherein Z³ is C₁₋₆-alkyl, (k) —CH₂—NH—CH₂—CH₂—O—, (l) —CH₂—NZ³—CH₂—CH₂—S—, wherein Z³ is chosen from H, C₁₋₆-alkyl, —C₁₋₆-alkyl-OH, —C₁₋₆-alkyl-O—C₁₋₆-alkyl, and —C₁₋₆-alkyl-OC(═O)—C₁₋₆-alkyl, (m) —CH₂—NH—CH₂—CH₂—SO₂—, (n) —CH₂—NH—C(═O)—NH—CH₂—, (o) —C(═O)—NZ³—CH₂—CH₂—CH₂—, wherein Z³ is chosen from H and C₁₋₆-alkyl, (p) —C(═O)—NZ³—CZ¹Z²—CZ¹Z²—NZ³ᵃ—, wherein Z¹, Z², and Z³ are independently chosen from H and C₁₋₆-alkyl, and Z³ᵃ is chosen from H, C₁₋₆-alkyl, and —C(═O)C₁₋₆-haloalkyl, (q) —NZ³—CH₂—CH₂—NZ³ᵃ—CH₂—, wherein Z³ is C₁₋₆-alkyl, and Z³ᵃ is chosen from H, C₁₋₆-alkyl, —C(═O)N(C₁₋₆alkyl)(C₁₋₆-alkyl), —C₁₋₆-alkyl-C₃₋₆-cycloalkyl, —C₁₋₆-alkyl-OH, —C₁₋₆-alkyl-O—C₁₋₆-alkyl, —C₁₋₆-alkyl-OC(═O)—C₁₋₆-alkyl, —C(═O)-5-membered heteroaryl, —C₁₋₆-alkyl-C(═O)O—C₁₋₆-alkyl, —C₁₋₆-fluoroalkyl-OH, C₂₋₆-alkynyl, and —S(═O)₂—C₁₋₆-alkyl, (r) —NZ³—CH₂—CH₂—NZ³ᵃ—C(═O)—, wherein Z³ is chosen from H, C₁₋₆-alkyl, —C₁₋₆-alkyl-N(C₁₋₆alkyl)(C₁₋₆-alkyl), and C₂₋₆-alkenyl, and Z³ᵃ is chosen from H and C₁₋₆-alkyl, (s) —NZ³—C(═O)—CH₂—CH₂—CH₂—, wherein Z³ is chosen from H, C₁₋₆-alkyl, and —C₁₋₆-alkyl-O—C₁₋₆-alkyl, (t) —O—CH₂—CH₂—NZ³—C(═O)—, wherein Z³ is chosen from H and C₁₋₆-alkyl, (u) —O—CH₂—CH₂—CH₂—O—, (v)

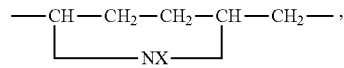

wherein X is chosen from H, C₁₋₆-alkyl, —C₁₋₆-alkyl-C₃₋₆-cycloalkyl, —C₁₋₆-alkyl-O—C₁₋₆-alkyl, —C(=O)C$_{3-6}$-cycloalkyl, —C(=O)OC$_{1-6}$-alkyl, C$_{2-6}$-alkynyl, and —S(=O)$_2$—C$_{1-6}$-alkyl, (w)
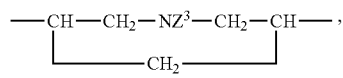

wherein Z$^1$ is chosen from C$_{1-6}$-alkyl, —C$_{1-6}$-alkyl-O—C$_{1-6}$-alkyl, and —S(=O)$_2$—C$_{1-6}$-alkyl, (x)
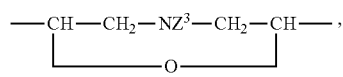

wherein Z$^1$ is chosen from H, C$_{1-6}$-alkyl, C$_{2-6}$-alkynyl, and —S(=O)$_2$—C$_{1-6}$-alkyl, (y)
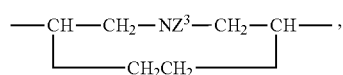

wherein Z$^1$ is chosen from H, C$_{1-6}$-alkyl, —C(=O)C$_{1-6}$-alkyl, —C$_{1-6}$-alkyl-CN, —C(=O)C$_{1-6}$-haloalkyl, C$_{1-6}$-haloalkyl, —C$_{1-6}$-alkyl-O—C$_{1-6}$-alkyl, C$_{2-6}$-alkynyl, and —S(=O)$_2$—C$_{1-6}$-alkyl, (z)
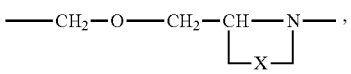

wherein X is chosen from —CH$_2$—CH$_2$—CH$_2$— and —CH$_2$—CH$_2$—CH$_2$—CH$_2$—, or (aa)
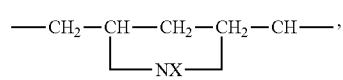

wherein X is —C(=O)OC$_{1-6}$-alkyl;
with the proviso that the compound is not:

(a)
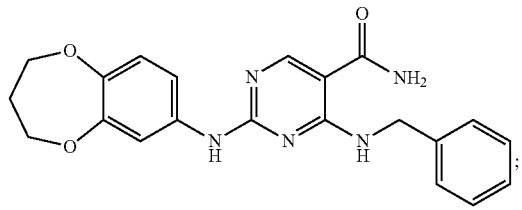

-continued (b)
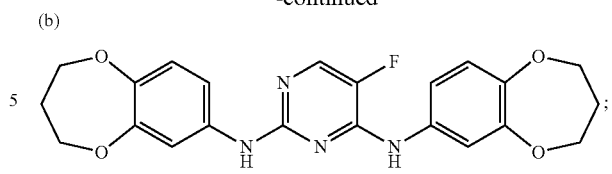

(c)
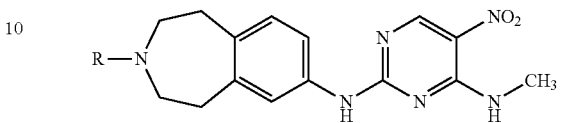

wherein R=H or —C(=O)CF$_3$;

(d)
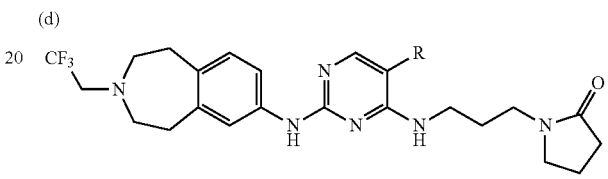

wherein R=Br, Cl, CH$_3$, or CF$_3$;

(e)
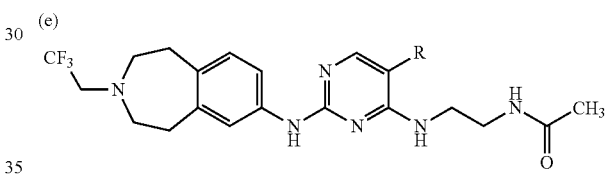

wherein R=Br, Cl, or CH$_3$;

(f)
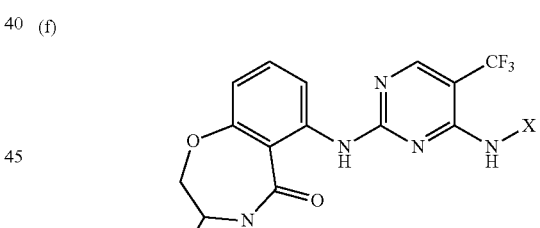

wherein X=

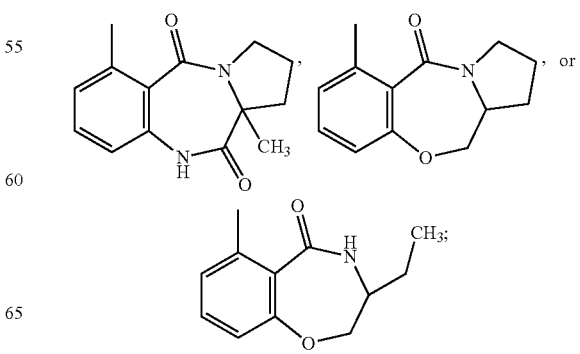

-continued (g)
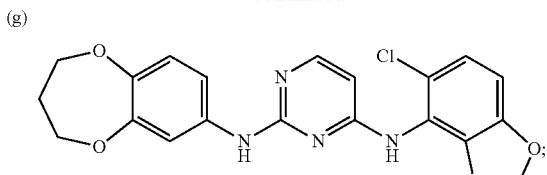

(h)
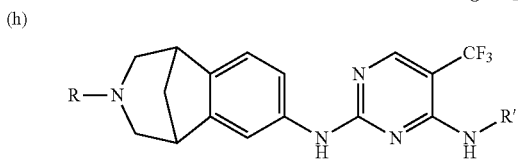

wherein
R=H, ethyl, —C(=O)CH$_3$, —C(=O)CH(CH$_3$)$_2$, —C(=O)CH$_2$OCH$_3$, —C(=O)NHCH(CH$_3$)$_2$, —C(=O)CH$_2$NHC(=O)CH$_3$, —C(=O)CHF$_2$, —C(=O)CF$_3$, —C(=O)NHCH$_2$CH$_3$, —C(=O)CH$_2$N(CH$_3$)$_2$,

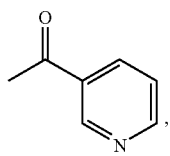

2-pyridyl, or S(=O)$_2$CH$_3$,
and
R'=cyclopropyl, cyclobutyl, —CH$_2$-cyclopropyl, ethyl, —CH(CH$_3$)$_2$, propyl, methyl,

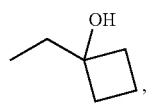

—(CH$_2$)$_2$OCH$_3$, or

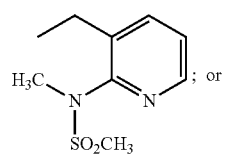

(i)
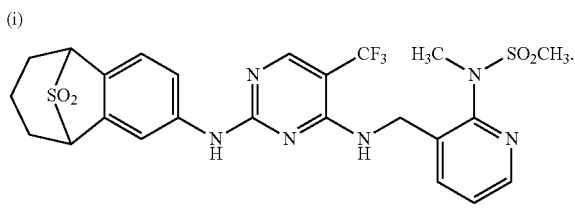

As another example, also included within the scope of the present invention are compounds of formula I or II and pharmaceutically acceptable salts thereof in which R$^1$ is halogen, nitro, C$_{1-6}$-alkyl, C$_{1-6}$-haloalkyl, or pseudohalogen; R$^2$ is a group chosen from C$_{1-6}$-alkyl, C$_{2-6}$-alkynyl, C$_{6-10}$-aryl, C$_{5-7}$-cycloalkyl, 5-7 membered heterocycloalkyl, and 5-10 membered heteroaryl, wherein the R$^2$ group is optionally substituted by one or more members independently chosen from halogen, —OR$^{20}$, —C(=O)R$^{20}$, —C(=O)OR$^{20}$, —C(=O)NR$^{22}$R$^{23}$, —C(=O)N(C$_{1-6}$-alkyl-OH)R$^{20}$, —NR$^{20}$R$^{21}$, C$_{1-6}$-alkyl, 5-15 membered heteroaryl optionally substituted by one or more members chosen from C$_{1-6}$-alkyl and —C$_{1-6}$-alkyl-O—C$_{1-6}$-alkyl, 5-10 membered heterocycloalkyl, —S(=O)$_2$NR$^{22}$R$^{23}$, —NHC(=O)R$^{21}$, —NHS(=O)$_2$R$^{21}$, and —NHC(=O)NR$^{22}$R$^{23}$; R$^{20}$, R$^{21}$, R$^{22}$, and R$^{23}$ at each occurrence are independently chosen from H, C$_{1-6}$-alkyl, C$_{1-6}$-fluoroalkyl, C$_{2-6}$-alkynyl, and C$_{3-6}$-cycloalkyl; R$^3$, R$^4$, and R$^5$ are independently chosen from H, halogen, —OR$^{30}$, —C(=O)R$^{30}$, —NR$^{30}$R$^{31}$, C$_{1-6}$-alkyl, and C$_{1-6}$-haloalkyl; R$^{30}$ and R$^{31}$ at each occurrence are independently chosen from H, C$_{1-6}$-alkyl, and C$_{1-6}$-fluoroalkyl; A$^1$, A$^2$, and A$^3$ are independently chosen from —CZ$^1$Z$^2$—, —C(=O)—, —NZ$^3$—, and —O—; A$^4$ is chosen from —CZ$^1$Z$^2$—, —C(=O)—, and —NZ$^3$—; A$^5$ is chosen from —CZ$^1$Z$^2$—, —C(=O)—, —NZ$^3$—, —S—, —S(=O)$_2$—, and —O—; Z$^1$, Z$^2$, and Z$^3$ are defined as follows:

(a) any Z$^1$, Z$^2$, and Z$^3$ may be independently chosen from H, halogen, —C(=O)R$^{40}$, —C(=O)NR$^{42}$R$^{43}$, C$_{1-6}$-alkyl, —C$_{1-6}$-alkyl-R$^{40}$, —C$_{1-6}$-alkyl-OR$^{40}$, —C$_{1-6}$-alkyl-OC(=O)R$^{40}$, —C$_{1-6}$-alkyl-C(=O)R$^{40}$, —C$_{1-6}$-alkyl-C(=O)OR$^{40}$, —C$_{1-6}$-alkyl-C(=O)NR$^{42}$R$^{43}$, —C$_{1-6}$-alkyl-NR$^{42}$R$^{43}$, —C$_{1-6}$-alkyl-NHC(=O)R$^{40}$, —C$_{1-6}$-alkyl-CN, C$_{1-6}$-haloalkyl, —C$_{1-6}$-haloalkyl-OR$^{40}$, C$_{2-6}$-alkenyl, C$_{2-6}$-alkynyl, 3-15 membered heterocycloalkyl, and —S(=O)$_2$R$^{40}$, and (b) any two of Z$^1$, Z$^2$, and Z$^3$ may together form a group of formula -A$^6$-A$^7$-A$^8$-A$^9$-A$^{10}$-, wherein A$^6$ is —CZ$^4$Z$^5$—, —NZ$^6$—, or —O—, A$^7$, A$^8$, and A$^9$ are independently a bond or —CZ$^4$Z$^5$—, and A$^{10}$ is a bond;

R$^{40}$ at each occurrence is independently chosen from H, C$_{1-6}$-alkyl, 5-membered heteroaryl, C$_{1-6}$-haloalkyl, 6-membered heterocycloalkyl-C$_{1-6}$-alkyl, and 6-membered heterocycloalkyl; R$^{42}$ and R$^{43}$ at each occurrence are independently chosen from H, C$_{1-6}$-alkyl optionally substituted by —OH, C$_{2-6}$-alkynyl, C$_{1-6}$-haloalkyl, C$_{6-15}$-aryl, 5-15 membered heteroaryl, C$_{3-10}$ cycloalkyl, and 3-15 membered heterocycloalkyl optionally substituted by —OH; Z$^4$ and Z$^5$ are H; and Z$^6$ is chosen from H, —C(=O)C$_{3-6}$-cycloalkyl, —C(=O)O—C$_{1-6}$-alkyl, C$_{1-6}$-alkyl, —C$_{1-6}$-alkyl-C$_{3-6}$-cycloalkyl, —C$_{1-6}$-alkyl-O—C$_{1-6}$-alkyl, C$_{2-6}$-alkynyl, and —S(=O)$_2$—C$_{1-6}$-alkyl; with the proviso that the compound is not:

(a)
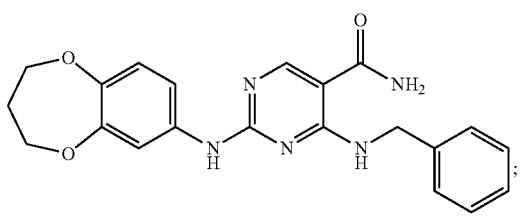

(b)
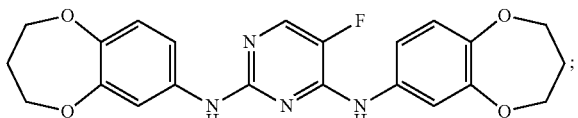

(c)

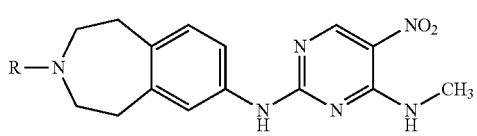

wherein R=H or —C(=O)CF₃;

(d)

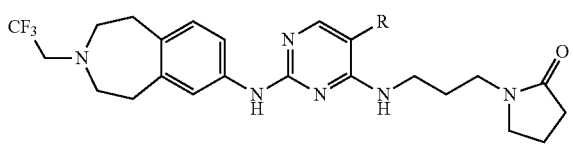

wherein R=Br, Cl, CH₃, or CF₃;

(e)

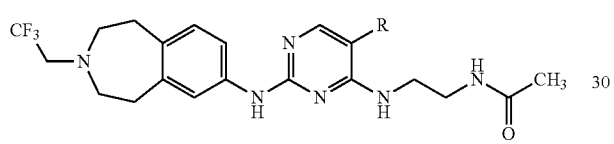

wherein R=Br, Cl, or CH₃;

(f)

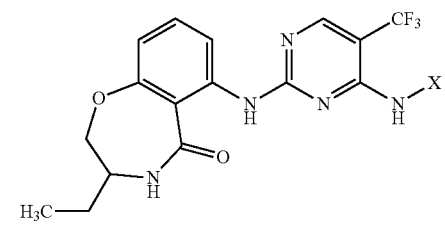

wherein X=

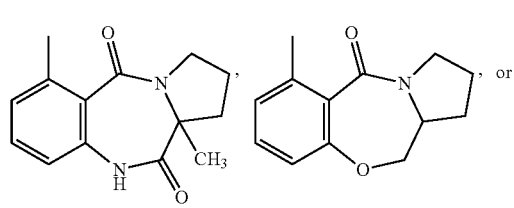

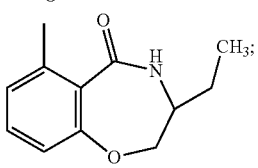

(g)

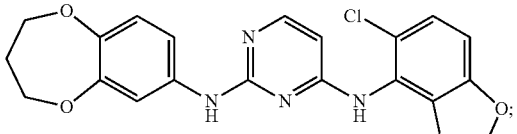

(h)

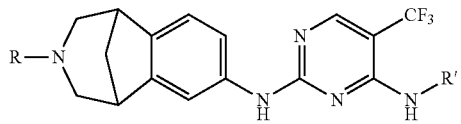

wherein
R=H, ethyl, —C(=O)CH₃, —C(=O)CH(CH₃)₂, —C(=O)CH₂OCH₃, —C(=O)NHCH(CH₃)₂, —C(=O)CH₂NHC(=O)CH₃, —C(=O)CHF₂, —C(=O)CF₃, —C(=O)NHCH₂CH₃, —C(=O)CH₂N(CH₃)₂,

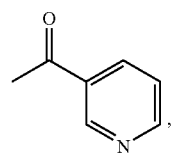

2-pyridyl, or S(=O)₂CH₃,
and
R'=cyclopropyl, cyclobutyl, —CH₂-cyclopropyl, ethyl, —CH(CH₃)₂, propyl, methyl,

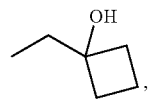

—(CH₂)₂OCH₃, or

; or (i)

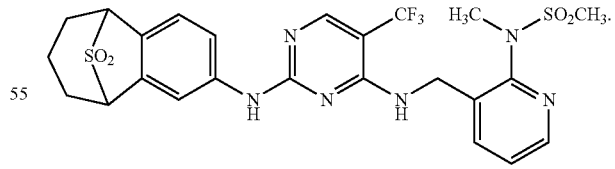

As another example, also included within the scope of the present invention are compounds of formula I or II and pharmaceutically acceptable salts thereof in which $R^1$ is halogen, nitro, $C_{1-6}$-alkyl, $C_{1-6}$-haloalkyl, or pseudohalogen; $R^2$ is a group chosen from $C_{1-6}$-alkyl, $C_{2-6}$-alkynyl, $C_{6-10}$-aryl, $C_{5-7}$-cycloalkyl, 5-7 membered heterocycloalkyl, and 5-10 membered heteroaryl, wherein the $R^2$ group is optionally substituted by one or more members independently chosen from halogen, —OR²⁰, —C(=O)R²⁰, —C(=O)OR²⁰, —C(=O)

$NR^{22}R^{23}$, $-C(=O)N(C_{1-6}\text{-alkyl-OH})R^{20}$, $-NR^{20}R^{21}$, $C_{1-6}$-alkyl, 5-15 membered heteroaryl optionally substituted by one or more members chosen from $C_{1-6}$-alkyl and $-C_{1-6}\text{-alkyl-O}-C_{1-6}\text{-alkyl}$, 5-10 membered heterocycloalkyl, $-S(=O)_2NR^{22}R^{23}$, $-NHC(=O)R^{21}$, $-NHS(=O)_2R^{21}$, and $-NHC(=O)NR^{22}R^{23}$; $R^{20}$, $R^{21}$, $R^{22}$, and $R^{23}$ at each occurrence are independently chosen from H, $C_{1-6}$-alkyl, $C_{1-6}$-fluoroalkyl, $C_{2-6}$-alkynyl, and $C_{3-6}$-cycloalkyl; $R^3$, $R^4$, and $R^5$ are independently chosen from H, halogen, $-OR^{30}$, $-C(=O)R^{30}$, $-NR^{30}R^{31}$, $C_{1-6}$-alkyl, and $C_{1-6}$-haloalkyl; $R^3$, $R^4$, and $R^5$ are independently chosen from H, halogen, $-OR^{30}$, $-C(=O)R^{30}$, and $-NR^{30}R^{31}$; $R^{30}$ and $R^{31}$ at each occurrence are independently chosen from H, $C_{1-6}$-alkyl, and $C_{1-6}$-fluoroalkyl; $A^1$, $A^2$, $A^3$, $A^4$, and $A^5$ are independently chosen from $-CZ^1Z^2-$, $-C(=O)-$, $-NZ^3-$, $-S-$, $-S(=O)_2-$, and $-O-$; $Z^1$, $Z^2$, and $Z^3$ are defined as follows:

(a) any of $Z^1$, $Z^2$, and $Z^3$ may be independently chosen from H, halogen, $-NO_2$, $-OR^{40}$, $-C(=O)R^{40}$, $-C(=O)OR^{40}$, $-C(=O)NR^{42}R^{43}$, $-NR^{40}R^{41}$, $C_{1-6}$-alkyl, $-C_{1-6}\text{-alkyl-}R^{40}$, $-C_{1-6}\text{-alkyl-}OR^{40}$, $-C_{1-6}\text{-alkyl-OC}(=O)R^{40}$, $-C_{1-6}\text{-alkyl-C}(=O)R^{40}$, $-C_{1-6}\text{-alkyl-C}(=O)OR^{40}$, $-C_{1-6}\text{-alkyl-C}(=O)NR^{42}R^{43}$, $-C_{1-6}\text{-alkyl-}NR^{42}R^{43}$, $-C_{1-6}\text{-alkyl-NHC}(=O)R^{40}$, $-C_{1-6}\text{-alkyl-CN}$, $C_{1-6}$-haloalkyl, $-C_{1-6}\text{-haloalkyl-}OR^{40}$, $C_{2-6}$-alkenyl, $C_{2-6}$-alkynyl, $C_{6-15}$-aryl, 5-15 membered heteroaryl, $C_{3-10}$ cycloalkyl, 3-15 membered heterocycloalkyl, pseudohalogen, $-S(=O)_nR^{40}$, $-S(=O)_2NR^{42}R^{43}$, $-OCH_2F$, $-OCHF_2$, $-OCF_3$, $-NHOH$, $-OC(=O)R^{40}$, $-OC(=O)NR^{42}R^{43}$, $-NR^{40}C(=O)R^{41}$, $-NR^{40}C(=O)OR^{41}$, $-NR^{40}S(=O)_2R^{41}$, and $-SCF_3$, and (b) any two of $Z^1$, $Z^2$, and $Z^3$ may together form a group of formula $-A^6-A^7-A^8-A^9-A^{10}-$;

$R^{40}$ and $R^{41}$ at each occurrence are independently chosen from H, $C_{1-6}$-alkyl, 5-membered heteroaryl, $C_{1-6}$-haloalkyl, 6-membered heterocycloalkyl-$C_{1-6}$-alkyl, and 6-membered heterocycloalkyl; $R^{42}$ and $R^{43}$ at each occurrence are independently chosen from H, $C_{1-6}$-alkyl optionally substituted by $-OH$, $C_{2-6}$-alkynyl, $C_{1-6}$-haloalkyl, $C_{6-15}$-aryl, 5-15 membered heteroaryl, $C_{3-10}$ cycloalkyl, and 3-15 membered heterocycloalkyl optionally substituted by $-OH$; $A^6$, $A^7$, $A^8$, $A^9$, and $A^{10}$ are independently chosen from a bond, $-CZ^4Z^5-$, $-NZ^6-$, and $-O-$; $Z^4$ and $Z^5$ are H; and $Z^6$ is chosen from H, $-C(=O)C_{3-6}$-cycloalkyl, $-C(=O)O-C_{1-6}$-alkyl, $C_{1-6}$-alkyl, $-C_{1-6}\text{-alkyl-}C_{3-6}$-cycloalkyl, $-C_{1-6}\text{-alkyl-O}-C_{1-6}$-alkyl, $C_{2-6}$-alkynyl, and $-S(=O)_2-C_{1-6}$-alkyl; and wherein $R^2$ is not $C_{1-2}$-alkyl substituted by any of the following:

(a) indolyl;
(b) mono or polysubstituted indolyl, wherein each substituent is independently selected from the group consisting of $C_{1-6}$-alkyl, $C_{1-6}$-alkyl-OR, $C_{1-6}$-alkyl-$NR_2$, and dimethyldioxolanyl, wherein R at each occurrence is independently chosen from H and $C_{1-3}$-alkyl;
(c) benzotriazolyl;
(d) mono or disubstituted benzotriazolyl, wherein each substituent is independently selected from the group consisting of $C_{1-6}$-alkyl groups;
(e) phenyl having the following substitution pattern:
  (i) ortho positions independently chosen from H, halogen, and $-CF_3$,
  (ii) meta positions independently chosen from H, halogen, ethynyl, $-O(C_{1-6}\text{-alkyl})$, $-C(=O)(C_{1-3}\text{-alkyl})$, and pyrazolyl, and
  (iii) para position chosen from halogen, $-O(C_{1-6}\text{-alkyl})$, $-O(\text{phenyl})$, $-C(=O)(C_{1-3}\text{-alkyl})$, $C_{1-6}$-alkyl, $CF_3$, pyrazolyl, morpholinyl, piperazinyl, and $-S(=O)_2NH_2$; or (f) phenyl having the following substitution pattern:
  (i) ortho positions independently chosen from H, halogen, and $-CF_3$,
  (ii) meta positions independently chosen from halogen, ethynyl, $-O(C_{1-6}\text{-alkyl})$, $-C(=O)(C_{1-3}\text{-alkyl})$, and pyrazolyl, and
  (iii) para position chosen from H, $-O(C_{1-6}\text{-alkyl})$, $-O(\text{phenyl})$, $-C(=O)(C_{1-3}\text{-alkyl})$, $C_{1-6}$-alkyl, $CF_3$, pyrazolyl, morpholinyl, piperazinyl, and $-S(=O)_2NH_2$;

with the proviso that the compound is not:

(a)
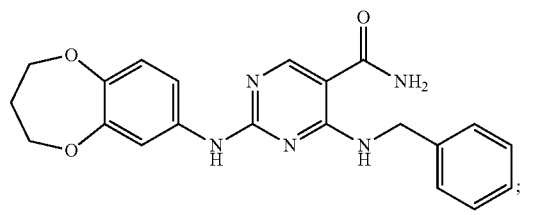

(b)
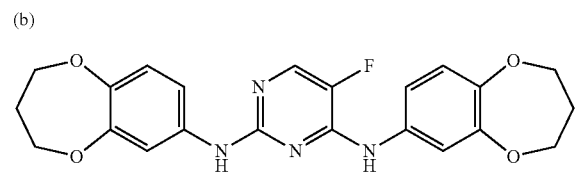

(c)
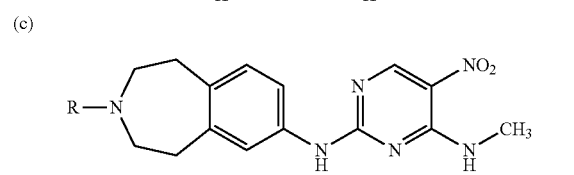

wherein R=H or $-C(=O)CF_3$;

(d)
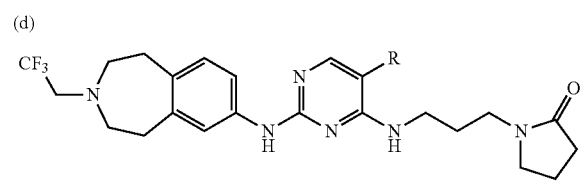

wherein R=Br, Cl, $CH_3$, or $CF_3$;

(e)
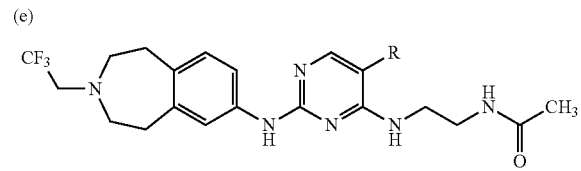

wherein R=Br, Cl, or $CH_3$;

(f)

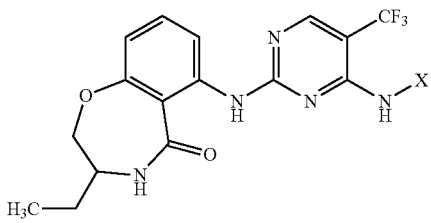

wherein X=

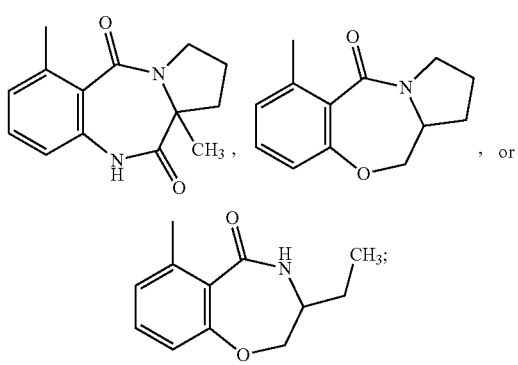

(g)

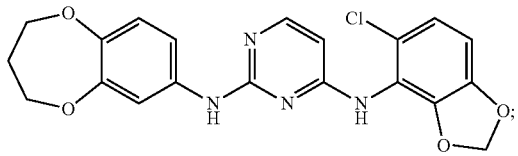

(h)

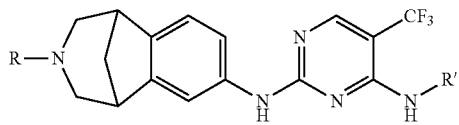

wherein

R=H, ethyl, —C(=O)CH₃, —C(=O)CH(CH₃)₂, —C(=O)CH₂OCH₃, —C(=O)NHCH(CH₃)₂, —C(=O)CH₂NHC(=O)CH₃, —C(=O)CHF₂, —C(=O)CF₃, —C(=O)NHCH₂CH₃, —C(=O)CH₂N(CH₃)₂,

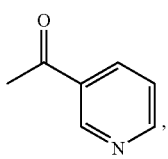

2-pyridyl, or S(=O)₂CH₃,
and
R'=cyclopropyl, cyclobutyl, —CH₂-cyclopropyl, ethyl, —CH(CH₃)₂, propyl, methyl,

—(CH₂)₂OCH₃, or

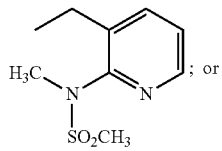

; or (i)

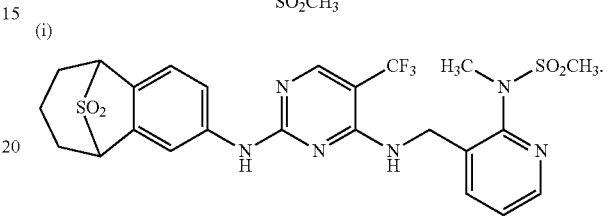

In one embodiment, the present invention provides one or more of the following compounds of formula I:

2-[5-Chloro-2-(1-methyl-2-oxo-2,3,4,5-tetrahydro-1H-benzo[b]azepin-7-ylamino)pyrimidin-4-ylamino]-N-methyl-benzamide;

2-[5-Chloro-2-(2-oxo-2,3,4,5-tetrahydro-1H-benzo[b]azepin-7-ylamino)-pyrimidin-4-ylamino]-N-methyl-benzamide;

2-[5-Chloro-2-(6-methoxy-2-oxo-2,3,4,5-tetrahydro-1H-benzo[b]azepin-7-ylamino)-pyrimidin-4-ylamino]-N-methyl-benzamide;

2-[5-Chloro-2-(1-methyl-2-oxo-2,3,4,5-tetrahydro-1H-benzo[b]azepin-7-ylamino)-pyrimidin-4-ylamino]-N-methyl-benzenesulfonamide;

2-[5-Chloro-2-(2-oxo-2,3,4,5-tetrahydro-1H-benzo[b]azepin-7-ylamino)-pyrimidin-4-ylamino]-N-methyl-benzenesulfonamide;

2-[5-Chloro-2-(1-methyl-2-oxo-2,3,4,5-tetrahydro-1H-benzo[b]azepin-7-ylamino)-pyrimidin-4-ylamino]-N-(2-hydroxy-ethyl)-benzamide;

2-[5-Chloro-2-(1-methyl-2-oxo-2,3,4,5-tetrahydro-1H-benzo[b]azepin-7-ylamino)-pyrimidin-4-ylamino]-benzamide;

{7-[5-Chloro-4-(2-methylsulfamoyl-phenylamino)-pyrimidin-2-ylamino]-2-oxo-2,3,4,5-tetrahydro-benzo[b]azepin-1-yl}-acetic acid methyl ester;

{7-[5-Chloro-4-(2-methylsulfamoyl-phenylamino)-pyrimidin-2-ylamino]-2-oxo-2,3,4,5-tetrahydro-benzo[b]azepin-1-yl}-acetic acid;

2-(5-Chloro-2-{1-[2-(4-methyl-piperazin-1-yl)-2-oxo-ethyl]-2-oxo-2,3,4,5-tetrahydro-1H-benzo[b]azepin-7-ylamino}-pyrimidin-4-ylamino)-N-methyl-benzenesulfonamide;

2-[5-Chloro-2-(1-oxo-2,3,4,5-tetrahydro-1H-benzo[c]azepin-7-ylamino)-pyrimidin-4-ylamino]-N-methyl-benzamide;

2-{5-Chloro-2-[(S)-(2,3,3a,4-tetrahydro-1H,6H-5-oxa-10b-aza-benzo[e]azulen-8-yl)amino]-pyrimidin-4-ylamino}-N-methyl-benzamide;

2-{5-Chloro-2-[(S)-(2,3,3a,4-tetrahydro-1H,6H-5-oxa-10b-aza-benzo[e]azulen-8-yl)amino]-pyrimidin-4-ylamino}-N-methyl-benzenesulfonamide;

2-[5-Chloro-2-(7,7a,8,9,10,11-hexahydro-5H-6-oxa-11a-aza-dibenzo[a,c]cyclohepten-3-ylamino)-pyrimidin-4-ylamino]-N-methyl-benzamide;
2-[5-Chloro-2-(1-methyl-1,2,3,5-tetrahydro-benzo[e][1,4]oxazepin-7-ylamino)-pyrimidin-4-ylamino]-N-methyl-benzamide;
2-[5-Chloro-2-(1-methyl-1,2,3,5-tetrahydro-benzo[e][1,4]oxazepin-7-ylamino)-pyrimidin-4-ylamino]-N-(2-hydroxy-ethyl)-benzamide;
2-{2-[5-Chloro-2-(1-methyl-1,2,3,5-tetrahydro-benzo[e][1,4]oxazepin-7-ylamino)-pyrimidin-4-ylamino]-phenyl}-oxazolidin-2-ol;
2-[5-Chloro-2-(1-methyl-1,2,3,5-tetrahydro-benzo[e][1,4]oxazepin-7-ylamino)-pyrimidin-4-ylamino]-N-methyl-benzenesulfonamide;
(2-exo,3-exo)-3-[5-Chloro-2-(1-methyl-2-oxo-2,3,4,5-tetrahydro-1H-benzo[b]azepin-7-ylamino)-pyrimidin-4-ylamino]-bicyclo[2.2.1]hept-5-ene-2-carboxamide;
2-[5-Chloro-2-(1-methyl-2-oxo-2,3,4,5-tetrahydro-1H-benzo[b]azepin-7-ylamino)-pyrimidin-4-ylamino]-cyclohexanecarboxylic acid amide;
2-[5-Chloro-2-(3-ethyl-2,3,4,5-tetrahydro-1H-benzo[d]azepin-7-ylamino)-pyrimidin-4-ylamino]-N-methyl-benzamide;
2-[5-Chloro-2-(3-ethyl-2,3,4,5-tetrahydro-1H-benzo[d]azepin-7-ylamino)-pyrimidin-4-ylamino]-N-methyl-benzenesulfonamide;
4-Chloro-2-[5-chloro-2-(3-ethyl-2,3,4,5-tetrahydro-1H-benzo[d]azepin-7-ylamino)-pyrimidin-4-ylamino]-N-methyl-benzamide;
2-{5-Chloro-2-[3-(2-methoxy-ethyl)-2,3,4,5-tetrahydro-1H-benzo[d]azepin-7-ylamino]-pyrimidin-4-ylamino}-N-methyl-benzamide;
2-{5-Chloro-2-[3-(2-methoxy-ethyl)-2,3,4,5-tetrahydro-1H-benzo[d]azepin-7-ylamino]-pyrimidin-4-ylamino}-N-methyl-benzenesulfonamide;
N-((1R,2R)-2-{5-Chloro-2-[3-(2-methoxy-ethyl)-2,3,4,5-tetrahydro-1H-benzo[d]azepin-7-ylamino]-pyrimidin-4-ylamino}-cyclohexyl)-methanesulfonamide;
N-(2-{5-Chloro-2-[3-(2-methoxy-ethyl)-2,3,4,5-tetrahydro-1H-benzo[d]azepin-7-ylamino]-pyrimidin-4-ylamino}-phenyl)-methanesulfonamide;
2-{5-Chloro-2-[3-(2-fluoro-ethyl)-2,3,4,5-tetrahydro-1H-benzo[d]azepin-7-ylamino]-pyrimidin-4-ylamino}-N-methyl-benzamide;
2-{5-Chloro-2-[3-(2-fluoro-2-methyl-propyl)-2,3,4,5-tetrahydro-1H-benzo[d]azepin-7-ylamino]-pyrimidin-4-ylamino}-N-methyl-benzamide;
N-((1R,2R)-2-{5-Chloro-2-[3-(2-fluoro-2-methyl-propyl)-2,3,4,5-tetrahydro-1H-benzo[d]azepin-7-ylamino]-pyrimidin-4-ylamino}-cyclohexyl)-methanesulfonamide;
2-{5-Chloro-2-[3-(2,2,2-trifluoro-ethyl)-2,3,4,5-tetrahydro-1H-benzo[d]azepin-7-ylamino]-pyrimidin-4-ylamino}-N-methyl-benzamide;
2-[5-Chloro-2-(3-methanesulfonyl-2,3,4,5-tetrahydro-1H-benzo[d]azepin-7-ylamino)-pyrimidin-4-ylamino]-N-methyl-benzamide;
2-[5-Chloro-2-(3-methanesulfonyl-2,3,4,5-tetrahydro-1H-benzo[d]azepin-7-ylamino)-pyrimidin-4-ylamino]-N-methyl-benzenesulfonamide;
2-{5-Chloro-2-[3-(2,2,2-trifluoro-acetyl)-2,3,4,5-tetrahydro-1H-benzo[d]azepin-7-ylamino]-pyrimidin-4-ylamino}-N-methyl-benzamide;
2-[5-Chloro-2-(2,3,4,5-tetrahydro-1H-benzo[d]azepin-7-ylamino)-pyrimidin-4-ylamino]-N-methyl-benzamide;
2-[5-Chloro-2-(3-methyl-2,3,4,5-tetrahydro-1H-benzo[d]azepin-7-ylamino)-pyrimidin-4-ylamino]-N-methyl-benzamide;
2-[5-Chloro-2-(3-isopropyl-2,3,4,5-tetrahydro-1H-benzo[d]azepin-7-ylamino)-pyrimidin-4-ylamino]-N-methyl-benzamide;
2-[5-Chloro-2-(3-ethyl-8-methoxy-2,3,4,5-tetrahydro-1H-benzo[d]azepin-7-ylamino)-pyrimidin-4-ylamino]-N-methyl-benzamide;
2-[2-(9-Amino-3-ethyl-8-methoxy-2,3,4,5-tetrahydro-1H-benzo[d]azepin-7-ylamino)-5-chloro-pyrimidin-4-ylamino]-N-methyl-benzamide;
2-[5-Chloro-2-(5,6,8,9-tetrahydro-7-oxa-benzocyclohepten-2-ylamino)-pyrimidin-4-ylamino]-N-methyl-benzamide;
2-[5-Chloro-2-(10-ethyl-12-oxa-10-aza-tricyclo[6.3.1.0*2,7*]dodeca-2,4,6-trien-4-ylamino)-pyrimidin-4-ylamino]-N-methyl-benzamide;
2-[5-Chloro-2-(10-isopropyl-12-oxa-10-aza-tricyclo[6.3.1.0*2,7*]dodeca-2,4,6-trien-4-ylamino)-pyrimidin-4-ylamino]-N-methyl-benzamide;
2-[5-Chloro-2-(10-prop-2-ynyl-12-oxa-10-aza-tricyclo[6.3.1.0*2,7*]dodeca-2,4,6-trien-4-ylamino)-pyrimidin-4-ylamino]-N-methyl-benzamide;
2-[5-Chloro-2-(10-methanesulfonyl-12-oxa-10-aza-tricyclo[6.3.1.0*2,7*]dodeca-2(7),3,5-trien-4-ylamino)-pyrimidin-4-ylamino]-N-methyl-benzamide;
2-[5-Chloro-2-(12-oxa-10-aza-tricyclo[6.3.1.0*2,7*]dodeca-2(7),3,5-trien-4-ylamino)-pyrimidin-4-ylamino]-N-methyl-benzamide;
2-[5-Chloro-2-(10-ethyl-12-oxa-10-aza-tricyclo[6.3.1.0*2,7*]dodeca-2(7),3,5-trien-4-ylamino)-pyrimidin-4-ylamino]-N-methyl-benzenesulfonamide;
4-[5-Chloro-4-(2-methylcarbamoyl-phenylamino)-pyrimidin-2-ylamino]-12-aza-tricyclo[7.2.1.0*2,7*]dodeca-2(7),3,5-triene-12-carboxylic acid ethyl ester;
2-{5-Chloro-2-[12-(2-methoxy-ethyl)-12-aza-tricyclo[7.2.1.0*2,7*]dodeca-2(7),3,5-trien-4-ylamino]-pyrimidin-4-ylamino}-N-methyl-benzamide;
2-[5-Chloro-2-(12-prop-2-ynyl-12-aza-tricyclo[7.2.1.0*2,7*]dodeca-2(7),3,5-trien-4-ylamino)-pyrimidin-4-ylamino]-N-methyl-benzamide;
2-[5-Chloro-2-(12-cyclopropanecarbonyl-12-aza-tricyclo[7.2.1.0*2,7*]dodeca-2(7),3,5-trien-4-ylamino)-pyrimidin-4-ylamino]-N-methyl-benzamide;
N-{(1R,2R)-2-[5-Chloro-2-(12-ethyl-12-aza-tricyclo[7.2.1.0*2,7*]dodeca-2(7),3,5-trien-4-ylamino)-pyrimidin-4-ylamino]-cyclohexyl}-methanesulfonamide;
N-{2-[5-Chloro-2-(12-ethyl-12-aza-tricyclo[7.2.1.0*2,7*]dodeca-2(7),3,5-trien-4-ylamino)-pyrimidin-4-ylamino]-phenyl}-methanesulfonamide;
2-[5-Chloro-2-(3-chloro-12-ethyl-12-aza-tricyclo[7.2.1.0*2,7*]dodeca-2(7),3,5-trien-4-ylamino)-pyrimidin-4-ylamino]-N-methyl-benzamide;
5-Chloro-4-[5-chloro-4-(2-methylcarbamoyl-phenylamino)-pyrimidin-2-ylamino]-12-aza-tricyclo[7.2.1.0*2,7*]dodeca-2(7),3,5-triene-12-carboxylic acid ethyl ester;
3-Chloro-4-[5-chloro-4-(2-methylcarbamoyl-phenylamino)-pyrimidin-2-ylamino]-12-aza-tricyclo[7.2.1.0*2,7*]dodeca-2(7),3,5-triene-12-carboxylic acid ethyl ester;
N-(2-{5-Chloro-2-[12-(2-methoxy-ethyl)-12-aza-tricyclo[7.2.1.0*2,7*]dodeca-2(7),3,5-trien-4-ylamino]-pyrimidin-4-ylamino}-phenyl)-methanesulfonamide;
N-((1R,2R)-2-{5-Chloro-2-[12-(2-methoxy-ethyl)-12-aza-tricyclo[7.2.1.0*2,7*]dodeca-2(7),3,5-trien-4-ylamino]-pyrimidin-4-ylamino}-cyclohexyl)-methanesulfonamide;

2-[2-(12-Aza-tricyclo[7.2.1.0*2,7*]dodeca-2(7),3,5-trien-4-ylamino)-5-chloro-pyrimidin-4-ylamino]-N-methyl-benzamide;
2-[5-Chloro-2-(12-isopropyl-12-aza-tricyclo[7.2.1.0*2,7*]dodeca-2(7),3,5-trien-4-ylamino)-pyrimidin-4-ylamino]-N-methyl-benzamide;
2-[5-Chloro-2-(3-chloro-12-aza-tricyclo[7.2.1.0*2,7*]dodeca-2(7),3,5-trien-4-ylamino)-pyrimidin-4-ylamino]-N-methyl-benzamide;
N-{(1R,2R)-2-[2-(12-Aza-tricyclo[7.2.1.0*2,7*]dodeca-2(7),3,5-trien-4-ylamino)-5-chloro-pyrimidin-4-ylamino]-cyclohexyl}-methanesulfonamide;
N-{(1R,2R)-2-[5-Chloro-2-(12-isopropyl-12-aza-tricyclo[7.2.1.0*2,7*]dodeca-2(7),3,5-trien-4-ylamino)-pyrimidin-4-ylamino]-cyclohexyl}-methanesulfonamide;
N-{(1R,2R)-2-[2-(12-sec-Butyl-12-aza-tricyclo[7.2.1.0*2,7*]dodeca-2(7),3,5-trien-4-ylamino)-5-chloro-pyrimidin-4-ylamino]-cyclohexyl}-methanesulfonamide;
N-{(1R,2R)-2-[2-(12-sec-Butyl-12-aza-tricyclo[7.2.1.0*2,7*]dodeca-2(7),3,5-trien-4-ylamino)-5-chloro-pyrimidin-4-ylamino]-cyclohexyl}-methanesulfonamide;
2-[5-Chloro-2-(3-chloro-12-isopropyl-12-aza-tricyclo[7.2.1.0*2,7*]dodeca-2(7),3,5-trien-4-ylamino)-pyrimidin-4-ylamino]-N-methyl-benzamide;
2-{5-Chloro-2-[3-chloro-12-(2-methoxy-ethyl)-12-aza-tricyclo[7.2.1.0*2,7*]dodeca-2(7),3,5-trien-4-ylamino]-pyrimidin-4-ylamino}-N-methyl-benzamide;
2-{5-Chloro-2-[5-chloro-12-(2-methoxy-ethyl)-12-aza-tricyclo[7.2.1.0*2,7*]dodeca-2(7),3,5-trien-4-ylamino]-pyrimidin-4-ylamino}-N-methyl-benzamide;
N-{(1R,2R)-2-[2-(12-sec-Butyl-12-aza-tricyclo[7.2.1.0*2,7*]dodeca-2(7),3,5-trien-4-ylamino)-5-chloro-pyrimidin-4-ylamino]-cyclohexyl}-methanesulfonamide;
2-[2-(12-Aza-tricyclo[7.2.1.0*2,7*]dodeca-2(7),3,5-trien-4-ylamino)-5-chloro-pyrimidin-4-ylamino]-3-chloro-N-methyl-benzamide;
3-Chloro-2-{5-chloro-2-[12-(2-methoxy-ethyl)-12-aza-tricyclo[7.2.1.0*2,7*]dodeca-2(7),3,5-trien-4-ylamino]-pyrimidin-4-ylamino}-N-methyl-benzamide;
N-{(1R,2R)-2-[5-Chloro-2-(3-methoxy-12-aza-tricyclo[7.2.1.0*2,7*]dodeca-2(7),3,5-trien-4-ylamino)-pyrimidin-4-ylamino]-cyclohexyl}-methanesulfonamide;
N-{(1R,2R)-2-[5-Chloro-2-(12-ethyl-3-methoxy-12-aza-tricyclo[7.2.1.0*2,7*]dodeca-2(7),3,5-trien-4-ylamino)-pyrimidin-4-ylamino]-cyclohexyl}-methanesulfonamide;
(+/-)-2-[5-Chloro-2-(12-ethyl-12-aza-tricyclo[7.2.1.0*2,7*]dodeca-2(7),3,5-trien-4-ylamino)-pyrimidin-4-ylamino]-N-methyl-benzamide;
(+/-)-2-[5-Chloro-2-(12-methanesulfonyl-12-aza-tricyclo[7.2.1.0*2,7*]dodeca-2(7),3,5-trien-4-ylamino)-pyrimidin-4-ylamino]-N-methyl-benzamide;
2-[5-Chloro-2-(1-methyl-2,3,4,5-tetrahydro-1H-benzo[b]azepin-7-ylamino)-pyrimidin-4-ylamino]-N-methyl-benzamide;
N-{(1R,2R)-2-[5-Chloro-2-(1-methyl-2,3,4,5-tetrahydro-1H-benzo[b]azepin-7-ylamino)-pyrimidin-4-ylamino]-cyclohexyl}-methanesulfonamide;
5-Chloro-N*4*-(2-methoxy-4-morpholin-4-yl-phenyl)-N*2*-(1-methyl-2,3,4,5-tetrahydro-1H-benzo[b]azepin-7-yl)-pyrimidine-2,4-diamine;
N-{2-[5-Chloro-2-(1-methyl-2,3,4,5-tetrahydro-1H-benzo[b]azepin-7-ylamino)-pyrimidin-4-ylamino]-phenyl}-methanesulfonamide;
2-[5-Chloro-2-(8-methoxy-2-methyl-1-oxo-2,3,4,5-tetrahydro-1H-benzo[c]azepin-7-ylamino)-pyrimidin-4-ylamino]-N-methyl-benzamide;
2-[5-Chloro-2-(1-methyl-2-oxo-2,3,4,5-tetrahydro-1H-benzo[b]azepin-8-ylamino)-pyrimidin-4-ylamino]-N-methyl-benzamide;
N-{(1R,2R)-2-[5-Chloro-2-(1-methyl-2-oxo-2,3,4,5-tetrahydro-1H-benzo[b]azepin-8-ylamino)-pyrimidin-4-ylamino]-cyclohexyl}-methanesulfonamide;
(2-exo, 3-exo)-3-[5-Chloro-2-(1-methyl-2-oxo-2,3,4,5-tetrahydro-1H-benzo[b]azepin-8-ylamino)pyrimidin-4-ylamino]-bicyclo[2.2.1]hept-5-ene-2-carboxylic acid amide;
N-((1R,2R)-2-{5-Chloro-2-[8-methoxy-3-(2-methoxy-ethyl)-2,3,4,5-tetrahydro-1H-benzo[d]azepin-7-ylamino]-pyrimidin-4-ylamino}-cyclohexyl)-methanesulfonamide;
(2-exo, 3-exo)-3-{5-Chloro-2-[8-methoxy-3-(2-methoxy-ethyl)-2,3,4,5-tetrahydro-1H-benzo[d]azepin-7-ylamino]-pyrimidin-4-ylamino}-bicyclo[2.2.1]hept-5-ene-2-carboxylic acid amide;
5-Chloro-N*2*-[8-methoxy-3-(2-methoxy-ethyl)-2,3,4,5-tetrahydro-1H-benzo[d]azepin-7-yl]-N*4*-(2-methoxy-4-morpholin-4-yl-phenyl)-pyrimidine-2,4-diamine;
(2-exo, 3-exo)-3-[5-Chloro-2-(6-methoxy-1-methyl-2-oxo-2,3,4,5-tetrahydro-1H-benzo[b]azepin-7-ylamino)-pyrimidin-4-ylamino]-bicyclo[2.2.1]hept-5-ene-2-carboxylic acid amide;
2-[5-Chloro-2-(6-methoxy-1-methyl-2-oxo-2,3,4,5-tetrahydro-1H-benzo[b]azepin-7-ylamino)-pyrimidin-4-ylamino]-N-methyl-benzamide;
7-[5-Chloro-4-(2-methoxy-4-morpholin-4-yl-phenylamino)-pyrimidin-2-ylamino]-6-methoxy-1-methyl-1,3,4,5-tetrahydro-benzo[b]azepin-2-one;
N-{(1R,2R)-2-[5-Chloro-2-(6-methoxy-1-methyl-2-oxo-2,3,4,5-tetrahydro-1H-benzo[b]azepin-7-ylamino)-pyrimidin-4-ylamino]-cyclohexyl}-methanesulfonamide;
7-[5-Chloro-4-(2-methoxy-4-morpholin-4-yl-phenylamino)-pyrimidin-2-ylamino]-1-ethyl-6-methoxy-1,3,4,5-tetrahydro-benzo[b]azepin-2-one;
N-{(1R,2R)-2-[5-Chloro-2-(1-ethyl-6-methoxy-2-oxo-2,3,4,5-tetrahydro-1H-benzo[b]azepin-7-ylamino)-pyrimidin-4-ylamino]-cyclohexyl}-methanesulfonamide;
(2-exo, 3-exo)-3-[5-Chloro-2-(1-ethyl-6-methoxy-2-oxo-2,3,4,5-tetrahydro-1H-benzo[b]azepin-7-ylamino)-pyrimidin-4-ylamino]-bicyclo[2.2.1]hept-5-ene-2-carboxylic acid amide;
2-[5-Chloro-2-(1-ethyl-6-methoxy-2-oxo-2,3,4,5-tetrahydro-1H-benzo[b]azepin-7-ylamino)-pyrimidin-4-ylamino]-N-methyl-benzamide;
2-{5-Chloro-2-[6-methoxy-1-(2-methoxy-ethyl)-2-oxo-2,3,4,5-tetrahydro-1H-benzo[b]azepin-7-ylamino]-pyrimidin-4-ylamino}-N-methyl-benzamide;
7-[5-Chloro-4-(2-methoxy-4-morpholin-4-yl-phenylamino)-pyrimidin-2-ylamino]-6-methoxy-1-(2-methoxy-ethyl)-1,3,4,5-tetrahydro-benzo[b]azepin-2-one;
(2-exo, 3-exo)-3-{5-Chloro-2-[6-methoxy-1-(2-methoxy-ethyl)-2-oxo-2,3,4,5-tetrahydro-1H-benzo[b]azepin-7-ylamino]-pyrimidin-4-ylamino}-bicyclo[2.2.1]hept-5-ene-2-carboxylic acid amide;
(2-exo, 3-exo)-3-[5-Chloro-2-(1-ethyl-6-methoxy-2-oxo-2,3,4,5-tetrahydro-1H-benzo[b]azepin-7-ylamino)-pyrimidin-4-ylamino]-bicyclo[2.2.1]heptane-2-carboxylic acid amide;
N-{(1R,2R)-2-[5-Chloro-2-(1-ethyl-8-methoxy-2-oxo-2,3,4,5-tetrahydro-1H-benzo[b]azepin-7-ylamino)-pyrimidin-4-ylamino]-cyclohexyl}-methanesulfonamide;

(2-exo, 3-exo)-3-[5-Chloro-2-(1-ethyl-8-methoxy-2-oxo-2,3,4,5-tetrahydro-1H-benzo[b]azepin-7-ylamino)-pyrimidin-4-ylamino]-bicyclo[2.2.1]hept-5-ene-2-carboxylic acid amide;

(1R,2R,3S,4S)-3-[5-Chloro-2-(1-ethyl-6-methoxy-2-oxo-2,3,4,5-tetrahydro-1H-benzo[b]azepin-7-ylamino)-pyrimidin-4-ylamino]-bicyclo[2.2.1]hept-5-ene-2-carboxylic acid amide;

(1S,2S,3R,4R)-3-[5-Chloro-2-(1-ethyl-6-methoxy-2-oxo-2,3,4,5-tetrahydro-1H-benzo[b]azepin-7-ylamino)-pyrimidin-4-ylamino]-bicyclo[2.2.1]hept-5-ene-2-carboxylic acid amide;

2-[5-Chloro-2-(1-ethyl-8-methoxy-2-oxo-2,3,4,5-tetrahydro-1H-benzo[b]azepin-7-ylamino)-pyrimidin-4-ylamino]-N-methyl-benzamide;

7-[5-Chloro-4-(2-methoxy-4-morpholin-4-yl-phenylamino)-pyrimidin-2-ylamino]-1-ethyl-8-methoxy-1,3,4,5-tetrahydro-benzo[b]azepin-2-one;

(2-exo,3-exo)-3-[5-Chloro-2-(1-ethyl-8-methoxy-2-oxo-2,3,4,5-tetrahydro-1H-benzo[b]azepin-7-ylamino)-pyrimidin-4-ylamino]-bicyclo[2.2.1]heptane-2-carboxylic acid amide;

7-[5-Chloro-4-(5-chloro-2-methoxy-phenylamino)-pyrimidin-2-ylamino]-1-ethyl-8-methoxy-1,3,4,5-tetrahydro-benzo[b]azepin-2-one;

2-[5-Chloro-2-(1-ethyl-8-methoxy-2-oxo-2,3,4,5-tetrahydro-1H-benzo[b]azepin-7-ylamino)-pyrimidin-4-ylamino]-3-fluoro-N-methyl-benzamide;

(2-exo,3-exo)-3-[5-Chloro-2-(6-methoxy-2-oxo-2,3,4,5-tetrahydro-1H-benzo[b]azepin-7-ylamino)-pyrimidin-4-ylamino]-bicyclo[2.2.1]hept-5-ene-2-carboxylic acid amide;

7-[5-Chloro-4-(2-methoxy-4-morpholin-4-yl-phenylamino)-pyrimidin-2-ylamino]-6-methoxy-1,3,4,5-tetrahydro-benzo[b]azepin-2-one;

7-[5-Chloro-4-(2-methoxy-4-morpholin-4-yl-phenylamino)-pyrimidin-2-ylamino]-1-ethyl-6-methoxy-3,3-dimethyl-1,3,4,5-tetrahydro-benzo[b]azepin-2-one;

(2-exo, 3-exo)-3-[5-Chloro-2-(1-ethyl-6-methoxy-3,3-dimethyl-2-oxo-2,3,4,5-tetrahydro-1H-benzo[b]azepin-7-ylamino)-pyrimidin-4-ylamino]-bicyclo[2.2.1]hept-5-ene-2-carboxylic acid amide;

N-{(1R,2R)-2-[5-Chloro-2-(1-ethyl-6-methoxy-3,3-dimethyl-2-oxo-2,3,4,5-tetrahydro-1H-benzo[b]azepin-7-ylamino)-pyrimidin-4-ylamino]-cyclohexyl}-methanesulfonamide;

2-[5-Chloro-2-(1-ethyl-6-methoxy-3,3-dimethyl-2-oxo-2,3,4,5-tetrahydro-1H-benzo[b]azepin-7-ylamino)-pyrimidin-4-ylamino]-N-methyl-benzamide;

5-Chloro-N*2*-[3-(2-methoxy-ethyl)-2,3,4,5-tetrahydro-1H-benzo[d]azepin-7-yl]-N*4*-(2-methoxy-phenyl)-pyrimidine-2,4-diamine;

5-Chloro-N*4*-(5-chloro-2-methoxy-phenyl)-N*2*-[3-(2-methoxy-ethyl)-2,3,4,5-tetrahydro-1H-benzo[d]azepin-7-yl]-pyrimidine-2,4-diamine;

N-{(1R,2R)-2-[5-Chloro-2-(1,3-diethyl-8-methoxy-2-oxo-2,3,4,5-tetrahydro-1H-benzo[d]azepin-7-ylamino)-pyrimidin-4-ylamino]-cyclohexyl-methanesulfonamide;

2-[5-Chloro-2-(1,3-diethyl-6-methoxy-2-oxo-2,3,4,5-tetrahydro-1H-benzo[d]azepin-7-ylamino)-pyrimidin-4-ylamino]-N-methyl-benzamide;

5-Chloro-N*2*-(3-ethyl-2,3,4,5-tetrahydro-1H-benzo[d]azepin-7-yl)-N*4*-prop-2-ynyl-pyrimidine-2,4-diamine;

2-[5-Chloro-2-(10-ethyl-10-aza-tricyclo[6.3.1.0*2,7*]dodeca-2,4,6-trien-4-ylamino)-pyrimidin-4-ylamino]-N-methyl-benzamide;

2-[5-Chloro-2-(10-ethyl-10-aza-tricyclo[6.3.1.0*2,7*]dodeca-2,4,6-trien-4-ylamino)-pyrimidin-4-ylamino]-N-methyl-benzenesulfonamide;

2-[5-chloro-2-(10-isopropyl-10-aza-tricyclo[6.3.1.0*2,7*]dodeca-2,4,6-trien-4-ylamino)-pyrimidin-4-ylamino]-N-methyl-benzamide;

2-[5-Chloro-2-(10-isopropyl-10-aza-tricyclo[6.3.1.0*2,7*]dodeca-2,4,6-trien-4-ylamino)-pyrimidin-4-ylamino]-N-methyl-benzenesulfonamide;

(2-exo,3-exo)-3-[5-Chloro-2-(10-ethyl-10-aza-tricyclo[6.3.1.0*2,7*]dodeca-2,4,6-trien-4-ylamino)-pyrimidin-4-ylamino]-bicyclo[2.2.1]hept-5-ene-2-carboxylic acid amide;

2-{5-Chloro-2-[10-(2-methoxy-ethyl)-10-aza-tricyclo[6.3.1.0*2,7*]dodeca-2,4,6-trien-4-ylamino]-pyrimidin-4-ylamino}-N-methyl-benzamide;

2-{5-Chloro-2-[10-(2-methoxy-ethyl)-10-aza-tricyclo[6.3.1.0*2,7*]dodeca-2,4,6-trien-4-ylamino]-pyrimidin-4-ylamino}-N-methyl-benzenesulfonamide;

2-[5-Chloro-2-(10-methanesulfonyl-10-aza-tricyclo[6.3.1.0*2,7*]dodeca-2,4,6-trien-4-ylamino)-pyrimidin-4-ylamino]-N-methyl-benzenesulfonamide;

2-[5-Chloro-2-(10-methanesulfonyl-10-aza-tricyclo[6.3.1.0*2,7*]dodeca-2,4,6-trien-4-ylamino)-pyrimidin-4-ylamino]-N-methyl-benzamide;

N-{(1R,2R)-2-[5-Chloro-2-(10-isopropyl-10-aza-tricyclo[6.3.1.0*2,7*]dodeca-2,4,6-trien-4-ylamino)-pyrimidin-4-ylamino]-cyclohexyl}-methanesulfonamide;

3-[5-Chloro-2-(3-ethyl-2,3,4,5-tetrahydro-1H-benzo[d]azepin-7-ylamino)-pyrimidin-4-ylamino]-azepan-2-one;

2-[5-Chloro-2-(7-oxo-6,7,8,9-tetrahydro-5H-benzocyclohepten-2-ylamino)-pyrimidin-4-ylamino]-N-methyl-benzamide;

(2-exo,3-exo)-3-[5-Chloro-2-(7-oxo-6,7,8,9-tetrahydro-5H-benzocyclo-hepten-2-ylamino)-pyrimidin-4-ylamino]-bicyclo[2.2.1]hept-5-ene-2-carboxylic acid amide;

N-{(1R,2R)-2-[5-Chloro-2-(7-oxo-6,7,8,9-tetrahydro-5H-benzocyclohepten-2-ylamino)-pyrimidin-4-ylamino]-cyclohexyl}-methanesulfonamide;

2-[5-Chloro-4-(2-methoxy-4-morpholin-4-yl-phenylamino)-pyrimidin-2-ylamino]-5,6,8,9-tetrahydro-benzocyclohepten-7-one;

Cis-2-[5-Chloro-2-(3-ethyl-2,3,4,5-tetrahydro-1H-benzo[d]-azepin-7-ylamino)-pyrimidin-4-ylamino]-cyclopentanecarboxylic acid amide;

(2-exo,3-exo)-3-{5-Chloro-2-[3-(2-methoxy-ethyl)-2,3,4,5-tetrahydro-1H-benzo[d]azepin-7-ylamino]-pyrimidin-4-ylamino}-bicyclo[2.2.1]heptane-2-carboxylic acid amide;

2-[5-Chloro-2-(7-morpholin-4-yl-6,7,8,9-tetrahydro-5H-benzocyclohepten-2-ylamino)-pyrimidin-4-ylamino]-N-methyl-benzamide;

N-{(1R,2R)-2-[5-Chloro-2-(7-morpholin-4-yl-6,7,8,9-tetrahydro-5H-benzocyclohepten-2-ylamino)-pyrimidin-4-ylamino]-cyclohexyl}-methanesulfonamide;

2-[5-Chloro-2-(7,7-difluoro-6,7,8,9-tetrahydro-5H-benzocyclohepten-2-ylamino)-pyrimidin-4-ylamino]-N-methyl-benzamide;

N-{(1R,2R)-2-[5-Chloro-2-(7,7-difluoro-6,7,8,9-tetrahydro-5H-benzocyclohepten-2-ylamino)-pyrimidin-4-ylamino]-cyclohexyl}-methanesulfonamide;

5-Chloro-N*2*-(7,7-difluoro-6,7,8,9-tetrahydro-5H-benzocyclohepten-2-yl)-N*4*-(2-methoxy-4-morpholin-4-yl-phenyl)-pyrimidine-2,4-diamine;

2-[5-Chloro-2-(10-methanesulfonyl-12-oxa-10-aza-tricyclo[6.3.1.0*2,7*]dodeca-2(7),3,5-trien-4-ylamino)-pyrimidin-4-ylamino]-N-methyl-benzamide;

2-[2-(3-Ethyl-2,3,4,5-tetrahydro-1H-benzo[d]azepin-7-ylamino)-5-methyl-pyrimidin-4-ylamino]-N-methyl-benzamide;
2-[2-(3-Ethyl-2,3,4,5-tetrahydro-1H-benzo[d]azepin-7-ylamino)-5-bromo-pyrimidin-4-ylamino]-N-methyl-benzamide;
2-[2-(3-Ethyl-2,3,4,5-tetrahydro-1H-benzo[d]azepin-7-ylamino)-5-nitro-pyrimidin-4-ylamino]-N-methyl-benzamide;
2-[2-(3-Ethyl-2,3,4,5-tetrahydro-1H-benzo[d]azepin-7-ylamino)-5-cyano-pyrimidin-4-ylamino]-N-methyl-benzamide;
2-[2-(3-Ethyl-2,3,4,5-tetrahydro-1H-benzo[d]azepin-7-ylamino)-5-trifluoromethyl-pyrimidin-4-ylamino]-N-methyl-benzamide;
2-[2-(3-Ethyl-2,3,4,5-tetrahydro-1H-benzo[d]azepin-7-ylamino)-5-fluoro-pyrimidin-4-ylamino]-N-methyl-benzamide;
2-[5-Bromo-2-(1-methyl-2-oxo-2,3,4,5-tetrahydro-1H-benzo[b]azepin-7-ylamino)-pyrimidin-4-ylamino]-N-methyl-benzamide;
2-{5-Bromo-2-[8-methoxy-3-(2-methoxy-ethyl)-2,3,4,5-tetrahydro-1H-benzo[d]azepin-7-ylamino]-pyrimidin-4-ylamino}-N-methyl-benzamide;
5-Chloro-N*2*,N*4*-bis-(3-ethyl-2,3,4,5-tetrahydro-1H-benzo[d]azepin-7-yl)-pyridine-2,4-diamine;
cis-2-[5-Chloro-2-(3-ethyl-2,3,4,5-tetrahydro-1H-benzo[d]azepin-7-ylamino)-pyrimidin-4-ylamino]-cyclohexanecarboxylic acid methylamide;
3-[5-Chloro-2-(3-ethyl-2,3,4,5-tetrahydro-1H-benzo[d]azepin-7-ylamino)-pyrimidin-4-ylamino]-N-methyl-propionamide;
4-[5-Chloro-2-(3-ethyl-2,3,4,5-tetrahydro-1H-benzo[d]azepin-7-ylamino)-pyrimidin-4-ylamino]-N-methyl-butyramide;
5-Chloro-N*2*-(3-ethyl-2,3,4,5-tetrahydro-1H-benzo[d]azepin-7-yl)-N*4*-[2-(1-methyl-1H-imidazol-2-yl)-phenyl]-pyrimidine-2,4-diamine;
2-{5-Chloro-4-[2-(1-methyl-1H-imidazol-2-yl)-phenylamino]-pyrimidin-2-ylamino}-5,6,8,9-tetrahydro-benzocyclohepten-7-one;
5-Chloro-N*4*-[2-(1-methyl-1H-imidazol-2-yl)-phenyl]-N*2*-(7-morpholin-4-yl-6,7,8,9-tetrahydro-5H-benzocyclohepten-2-yl)-pyrimidine-2,4-diamine;
5-Chloro-N*2*-(7,7-difluoro-6,7,8,9-tetrahydro-5H-benzocyclohepten-2-yl)-N*4*-[2-(1-methyl-1H-imidazol-2-yl)-phenyl]-pyrimidine-2,4-diamine;
7-{5-Chloro-4-[2-(1H-imidazol-2-yl)-phenylamino]-pyrimidin-2-ylamino}-5,5-dimethyl-1,3,4,5-tetrahydro-benzo[b]azepin-2-one;
5-Chloro-N*4*-[2-(1H-imidazol-2-yl)-phenyl]-N*2*-[3-(2-methoxy-ethyl)-2,3,4,5-tetrahydro-1H-benzo[d]azepin-7-yl]-pyrimidine-2,4-diamine;
5-Chloro-N*4*-[2-(1-ethoxymethyl-1H-imidazol-2-yl)-phenyl]-N*2*-[3-(2-methoxy-ethyl)-2,3,4,5-tetrahydro-1H-benzo[d]azepin-7-yl]-pyrimidine-2,4-diamine;
7-[5-Chloro-4-(2-pyridin-2-yl-phenylamino)-pyrimidin-2-ylamino]-5,5-dimethyl-1,3,4,5-tetrahydro-benzo[b]azepin-2-one;
5-Chloro-N*2*-[3-(2-methoxy-ethyl)-2,3,4,5-tetrahydro-1H-benzo[d]azepin-7-yl]-N*4*-(2-pyridin-2-yl-phenyl)-pyrimidine-2,4-diamine;
N-{2-[5-Chloro-2-(3-oxo-2,3,4,5-tetrahydro-1H-benzo[e][1,3]diazepin-7-ylamino)-pyrimidin-4-ylamino]-phenyl}-methanesulfonamide;
N-{(1R,2R)-2-[5-Chloro-2-(3-oxo-2,3,4,5-tetrahydro-1H-benzo[e][1,3]diazepin-7-ylamino)-pyrimidin-4-ylamino]-cyclohexyl}-methanesulfonamide;
2-[5-Chloro-2-(3-oxo-2,3,4,5-tetrahydro-1H-benzo[e][1,3]diazepin-7-ylamino)-pyrimidin-4-ylamino]-N-methyl-benzamide;
(2-exo,3-exo)-3-[5-Chloro-2-(3-oxo-2,3,4,5-tetrahydro-1H-benzo[e][1,3]diazepin-7-ylamino)-pyrimidin-4-ylamino]-bicyclo[2.2.1]hept-5-ene-2-carboxylic acid amide;
N-{(1R,2R)-2-[5-Chloro-2-(3-ethyl-6-methoxy-2,3,4,5-tetrahydro-1H-benzo[d]azepin-7-ylamino)-pyrimidin-4-ylamino]-cyclohexyl}-methanesulfonamide;
N-{2-[5-Chloro-2-(3-ethyl-6-methoxy-2,3,4,5-tetrahydro-1H-benzo[d]azepin-7-ylamino)-pyrimidin-4-ylamino]-7-phenyl}-methanesulfonamide;
2-[5-Chloro-2-(3-ethyl-6-methoxy-2,3,4,5-tetrahydro-1H-benzo[d]azepin-7-ylamino)-pyrimidin-4-ylamino]-N-methyl-benzamide;
(1R,2S)-1-[5-Chloro-2-(3-ethyl-2,3,4,5-tetrahydro-1H-benzo[d]azepin-7-ylamino)-pyrimidin-4-ylamino]-indan-2-ol;
2-{5-Chloro-2-[8-methoxy-3-(2-methoxy-ethyl)-2,3,4,5-tetrahydro-1H-benzo[d]azepin-7-ylamino]-pyrimidin-4-ylamino}-N-methyl-benzamide;
N-(2-{5-Chloro-2-[8-methoxy-3-(2-methoxy-ethyl)-2,3,4,5-tetrahydro-1H-benzo[d]azepin-7-ylamino]-pyrimidin-4-ylamino}-phenyl)-methanesulfonamide;
5-Chloro-N*4*-(5-chloro-2-methoxy-phenyl)-N*2*-[8-methoxy-3-(2-methoxy-ethyl)-2,3,4,5-tetrahydro-1H-benzo[d]azepin-7-yl]-pyrimidine-2,4-diamine;
N-((1R,2R)-2-{5-Chloro-2-[8-methoxy-3-(2,2,2-trifluoro-acetyl)-2,3,4,5-tetrahydro-1H-benzo[d]azepin-7-ylamino]-pyrimidin-4-ylamino}-cyclohexyl)-methanesulfonamide;
N-((1R,2R)-2-{5-Chloro-2-[8-methoxy-3-(2,2,2-trifluoro-ethyl)-2,3,4,5-tetrahydro-1H-benzo[d]azepin-7-ylamino]-pyrimidin-4-ylamino}-cyclohexyl)-methanesulfonamide;
5-Chloro-N*4*-(2-methoxy-4-morpholin-4-yl-phenyl)-N*2*-[8-methoxy-3-(2,2,2-trifluoro-ethyl)-2,3,4,5-tetrahydro-1H-benzo[d]azepin-7-yl]-pyrimidine-2,4-diamine;
(2-exo, 3-exo)-3-{5-Chloro-2-[8-methoxy-3-(2,2,2-trifluoro-ethyl)-2,3,4,5-tetrahydro-1H-benzo[d]azepin-7-ylamino]-pyrimidin-4-ylamino}-bicyclo[2.2.1]hept-5-ene-2-carboxylic acid amide;
N-{(1R,2R)-2-[5-Chloro-2-(3-ethyl-8-methoxy-2-oxo-2,3,4,5-tetrahydro-1H-benzo[d]azepin-7-ylamino)-pyrimidin-4-ylamino]-cyclohexyl}-methanesulfonamide;
(2-exo, 3-exo)-3-[5-Chloro-2-(3-ethyl-8-methoxy-2-oxo-2,3,4,5-tetrahydro-1H-benzo[d]azepin-7-ylamino)-pyrimidin-4-ylamino]-bicyclo[2.2.1]hept-5-ene-2-carboxylic acid amide;
2-[5-Chloro-2-(3-ethyl-8-methoxy-2-oxo-2,3,4,5-tetrahydro-1H-benzo[d]azepin-7-ylamino)-pyrimidin-4-ylamino]-N-methyl-benzamide;
7-[5-Chloro-4-(2-methoxy-4-morpholin-4-yl-phenylamino)-pyrimidin-2-ylamino]-3-ethyl-8-methoxy-1,3,4,5-tetrahydro-benzo[d]azepin-2-one;
2-[5-Chloro-2-(3-ethyl-8-methoxy-2-oxo-2,3,4,5-tetrahydro-1H-benzo[d]azepin-7-ylamino)-pyrimidin-4-ylamino]-N-ethyl-benzamide;
N-(2-{7-[5-Chloro-4-((1R,2R)-2-methanesulfonylamino-cyclohexylamino)-pyrimidin-2-ylamino]-8-methoxy-1,2,4,5-tetrahydro-benzo[d]azepin-3-yl}-ethyl)-acetamide;

N-(2-{7-[5-Chloro-4-(2-methoxy-4-morpholin-4-yl-phenylamino)-pyrimidin-2-ylamino]-8-methoxy-1,2,4,5-tetrahydro-benzo[d]azepin-3-yl}-ethyl)-acetamide;
2-{7-[5-Chloro-4-((1R,2R)-2-methanesulfonylamino-cyclohexylamino)-pyrimidin-2-ylamino]-8-methoxy-1,2,4,5-tetrahydro-benzo[d]azepin-3-yl}-N,N-dimethyl-acetamide;
2-[5-Chloro-2-(3-dimethylcarbamoylmethyl-8-methoxy-2,3,4,5-tetrahydro-1H-benzo[d]azepin-7-ylamino)-pyrimidin-4-ylamino]-N-methyl-benzamide;
(2-exo, 3-exo)-3-[5-Chloro-2-(3-dimethylcarbamoylmethyl-8-methoxy-2,3,4,5-tetrahydro-1H-benzo[d]azepin-7-ylamino)-pyrimidin-4-ylamino]-bicyclo[2.2.1]hept-5-ene-2-carboxylic acid amide;
2-{7-[5-Chloro-4-(2-methoxy-4-morpholin-4-yl-phenylamino)-pyrimidin-2-ylamino]-8-methoxy-1,2,4,5-tetrahydro-benzo[d]azepin-3-yl}-N,N-dimethyl-acetamide;
2-[5-Chloro-2-(3-dimethylcarbamoylmethyl-8-methoxy-2,3,4,5-tetrahydro-1H-benzo[d]azepin-7-ylamino)-pyrimidin-4-ylamino]-N-ethyl-benzamide;
N-{(1R,2R)-2-[5-Chloro-2-(8-methoxy-2-oxo-2,3,4,5-tetrahydro-1H-benzo[d]azepin-7-ylamino)-pyrimidin-4-ylamino]-cyclohexyl}-methanesulfonamide;
2-[5-Chloro-2-(8-methoxy-2-oxo-2,3,4,5-tetrahydro-1H-benzo[d]azepin-7-ylamino)-pyrimidin-4-ylamino]-N-methyl-benzamide;
2-[5-Chloro-2-(8-methoxy-2-oxo-2,3,4,5-tetrahydro-1H-benzo[d]azepin-7-ylamino)-pyrimidin-4-ylamino]-N-ethyl-benzamide;
2-[5-Chloro-2-(10-ethyl-10-aza-tricyclo[6.3.2.0*2,7*]trideca-2,4,6-trien-4-ylamino)-pyrimidin-4-ylamino]-N-methyl-benzamide;
2-[5-Chloro-2-(10-ethyl-10-aza-tricyclo[6.3.2.0*2,7*]trideca-2,4,6-trien-4-ylamino)-pyrimidin-4-ylamino]-N-methyl-benzenesulfonamide;
2-[5-Chloro-2-(10-isopropyl-10-aza-tricyclo[6.3.2.0*2,7*]trideca-2,4,6-trien-4-ylamino)-pyrimidin-4-ylamino]-N-methyl-benzamide;
2-[5-Chloro-2-(10-isopropyl-10-aza-tricyclo[6.3.2.0*2,7*]trideca-2,4,6-trien-4-ylamino)-pyrimidin-4-ylamino]-N-methyl-benzenesulfonamide;
2-[5-Chloro-2-(10-cyanomethyl-10-aza-tricyclo[6.3.2.0*2,7*]trideca-2,4,6-trien-4-ylamino)-pyrimidin-4-ylamino]-N-methyl-benzenesulfonamide;
2-{5-Chloro-2-[10-(2,2,2-trifluoro-acetyl)-10-aza-tricyclo[6.3.2.0*2,7*]trideca-2,4,6-trien-4-ylamino]-pyrimidin-4-ylamino}-N-methyl-benzamide;
2-[2-(10-Aza-tricyclo[6.3.2.0*2,7*]trideca-2,4,6-trien-4-ylamino)-5-chloro-pyrimidin-4-ylamino]-N-methyl-benzamide;
2-[5-Chloro-2-(10-methanesulfonyl-10-aza-tricyclo[6.3.2.0*2,7*]trideca-2,4,6-trien-4-ylamino)-pyrimidin-4-ylamino]-N-methyl-benzamide;
2-[5-Chloro-2-(10-prop-2-ynyl-10-aza-tricyclo[6.3.2.0*2,7*]trideca-2,4,6-trien-4-ylamino)-pyrimidin-4-ylamino]-N-methyl-benzamide;
2-{5-Chloro-2-[10-(2-fluoro-ethyl)-10-aza-tricyclo[6.3.2.0*2,7*]trideca-2,4,6-trien-4-ylamino]-pyrimidin-4-ylamino}-N-methyl-benzamide;
2-[5-Chloro-2-(10-cyanomethyl-10-aza-tricyclo[6.3.2.0*2,7*]trideca-2,4,6-trien-4-ylamino)-pyrimidin-4-ylamino]-N-methyl-benzamide;
2-{5-Chloro-2-[10-(2-methoxy-ethyl)-10-aza-tricyclo[6.3.2.0*2,7*]trideca-2,4,6-trien-4-ylamino]-pyrimidin-4-ylamino}-N-methyl-benzamide;
2-[2-(10-Acetyl-10-aza-tricyclo[6.3.2.0*2,7*]trideca-2,4,6-trien-4-ylamino)-5-chloro-pyrimidin-4-ylamino]-N-methyl-benzamide;
2-{5-Chloro-2-[10-(2,2,2-trifluoro-acetyl)-10-aza-tricyclo[6.3.2.0*2,7*]trideca-2,4,6-trien-4-ylamino]-pyrimidin-4-ylamino}-N-methyl-benzenesulfonamide;
2-[2-(10-Aza-tricyclo[6.3.2.0*2,7*]trideca-2,4,6-trien-4-ylamino)-5-chloro-pyrimidin-4-ylamino]-N-methyl-benzenesulfonamide;
2-[5-Chloro-2-(10-methanesulfonyl-10-aza-tricyclo[6.3.2.0*2,7*]trideca-2,4,6-trien-4-ylamino)-pyrimidin-4-ylamino]-N-methyl-benzenesulfonamide;
2-[5-Chloro-2-(10-prop-2-ynyl-10-aza-tricyclo[6.3.2.0*2,7*]trideca-2,4,6-trien-4-ylamino)-pyrimidin-4-ylamino]-N-methyl-benzenesulfonamide;
2-[5-Chloro-2-(10-prop-2-ynyl-10-aza-tricyclo[6.3.2.0*2,7*]trideca-2,4,6-trien-4-ylamino)-pyrimidin-4-ylamino]-N-methyl-N-prop-2-ynyl-benzenesulfonamide;
2-[2-(10-Acetyl-10-aza-tricyclo[6.3.2.0*2,7*]trideca-2,4,6-trien-4-ylamino)-5-chloro-pyrimidin-4-ylamino]-N-methyl-benzenesulfonamide;
2-{4-[5-Chloro-4-(2-methoxy-4-morpholin-4-yl-phenylamino)-pyrimidin-2-ylamino]-10-aza-tricyclo[6.3.2.0*2,7*]trideca-2,4,6-trien-10-yl}-2,2,2-trifluoro-ethanone;
N-(2-{5-Chloro-2-[10-(2,2,2-trifluoro-acetyl)-10-aza-tricyclo[6.3.2.0*2,7*]trideca-2,4,6-trien-4-ylamino]-pyrimidin-4-ylamino}-phenyl)-methanesulfonamide;
N-((1R,2R)-2-{5-Chloro-2-[(1R,8S)-10-(2,2,2-trifluoro-acetyl)-10-aza-tricyclo[6.3.2.0*2,7*]trideca-2,4,6-trien-4-ylamino]-pyrimidin-4-ylamino}-cyclohexyl)-methanesulfonamide;
N-((1R,2R)-2-{5-Chloro-2-[(1S,8R)-10-(2,2,2-trifluoro-acetyl)-10-aza-tricyclo[6.3.2.0*2,7*]trideca-2,4,6-trien-4-ylamino]-pyrimidin-4-ylamino}-cyclohexyl)-methanesulfonamide;
N-{(1R,2R)-2-[2-(10-Aza-tricyclo[6.3.2.0*2,7*]trideca-2,4,6-trien-4-ylamino)-5-chloro-pyrimidin-4-ylamino]-cyclohexyl}-methanesulfonamide;
N-{(1R,2R)-2-[5-Chloro-2-(10-methanesulfonyl-10-aza-tricyclo[6.3.2.0*2,7*]trideca-2,4,6-trien-4-ylamino)-pyrimidin-4-ylamino]-cyclohexyl}-methanesulfonamide;
N-{(1R,2R)-2-[2-(10-Acetyl-10-aza-tricyclo[6.3.2.0*2,7*]trideca-2,4,6-trien-4-ylamino)-5-chloro-pyrimidin-4-ylamino]-cyclohexyl}-methanesulfonamide;
N-{(1R,2R)-2-[5-Chloro-2-(10-Isopropyl-10-aza-tricyclo[6.3.2.0*2,7*]trideca-2,4,6-trien-4-ylamino)-pyrimidin-4-ylamino]-cyclohexyl}-methanesulfonamide;
2-{2-[3-Bromo-10-(2,2,2-trifluoro-acetyl)-10-aza-tricyclo[6.3.2.0*2,7*]trideca-2,4,6-trien-4-ylamino]-5-chloro-pyrimidin-4-ylamino}-N-methyl-benzamide;
N-{2-[5-Chloro-2-(3-ethyl-2,3,4,5-tetrahydro-1H-benzo[d]azepin-7-ylamino)-pyrimidin-4-ylamino]-ethyl}-methanesulfonamide;
N-(2-{5-Chloro-2-[3-(2-methoxy-ethyl)-2,3,4,5-tetrahydro-1H-benzo[d]azepin-7-ylamino]-pyrimidin-4-ylamino}-ethyl)-methanesulfonamide;
N-{2-[5-Chloro-2-(3-ethyl-2,3,4,5-tetrahydro-1H-benzo[d]azepin-7-ylamino)-pyrimidin-4-ylamino]-1-methyl-ethyl}-methanesulfonamide;
N-(2-{5-Chloro-2-[3-(2-methoxy-ethyl)-2,3,4,5-tetrahydro-1H-benzo[d]azepin-7-ylamino]-pyrimidin-4-ylamino}-1-methyl-ethyl)-methanesulfonamide;
N-{2-[5-Chloro-2-(3-ethyl-2,3,4,5-tetrahydro-1H-benzo[d]azepin-7-ylamino)-pyrimidin-4-ylamino]-propyl}-methanesulfonamide;

N-(2-{5-Chloro-2-[3-(2-methoxy-ethyl)-2,3,4,5-tetrahydro-1H-benzo[d]azepin-7-ylamino]-pyrimidin-4-ylamino}-propyl)-methanesulfonamide;

N-{2-[5-Chloro-2-(3-ethyl-2,3,4,5-tetrahydro-1H-benzo[d]azepin-7-ylamino)-pyrimidin-4-ylamino]-1,1-dimethyl-ethyl}-methanesulfonamide;

N-(2-{5-Chloro-2-[3-(2-methoxy-ethyl)-2,3,4,5-tetrahydro-1H-benzo[d]azepin-7-ylamino]-pyrimidin-4-ylamino}-1,1-dimethyl-ethyl)-methanesulfonamide;

N-(2-{5-Chloro-2-[3-(2-methoxy-ethyl)-2,3,4,5-tetrahydro-1H-benzo[d]azepin-7-ylamino]-pyrimidin-4-ylamino}-2-methyl-propyl)-methanesulfonamide;

N-{2-[5-Chloro-2-(3-ethyl-2,3,4,5-tetrahydro-1H-benzo[d]azepin-7-ylamino)-pyrimidin-4-ylamino]-2-methyl-propyl}-methanesulfonamide;

2-{5-Chloro-2-[3-(2-methoxy-ethyl)-2,3,4,5-tetrahydro-1H-benzo[d]azepin-7-ylamino]-pyrimidin-4-ylamino}-5,N-dimethyl-benzamide;

5-Chloro-N*2*-[3-(2-methoxy-ethyl)-2,3,4,5-tetrahydro-1H-benzo[d]azepin-7-yl]-N*4*-(2-methoxy-4-morpholin-4-yl-phenyl)-pyrimidine-2,4-diamine;

(2-exo,3-exo)-3-{5-Chloro-2-[3-(2-methoxy-ethyl)-2,3,4,5-tetrahydro-1H-benzo[d]azepin-7-ylamino]-pyrimidin-4-ylamino}-bicyclo[2.2.1]hept-5-ene-2-carboxylic acid amide;

2-{5-Chloro-2-[3-(2-methoxy-ethyl)-2,3,4,5-tetrahydro-1H-benzo[d]azepin-7-ylamino]-pyrimidine-4-ylamino}-3-fluoro-N-methyl-benzamide;

3-Chloro-2-{5-chloro-2-[3-(2-methoxy-ethyl)-2,3,4,5-tetrahydro-1H-benzo[d]azepin-7-ylamino]-pyrimidine-4-ylamino}-N-methyl-benzamide;

2-{5-Chloro-2-[3-(2-methoxy-ethyl)-2,3,4,5-tetrahydro-1H-benzo[d]azepin-7-ylamino]-pyrimidin-4-ylamino}-3,N-dimethyl-benzamide;

3,5-Dichloro-2-{5-chloro-2-[3-(2-methoxy-ethyl)-2,3,4,5-tetrahydro-1H-benzo[d]azepin-7-ylamino]-pyrimidin-4-ylamino}-N-methyl-benzamide;

2-{5-Chloro-2-[3-(2-methoxy-ethyl)-2,3,4,5-tetrahydro-1H-benzo[d]azepin-7-ylamino]-pyrimidin-4-ylamino}-3-methoxy-N-methyl-benzamide;

5-Chloro-N*2*-[3-(2-methoxy-ethyl)-2,3,4,5-tetrahydro-1H-benzo[d]azepin-7-yl]-N*4*-(2-pyrazol-1-yl-phenyl)-pyrimidine-2,4-diamine;

2-{5-Chloro-2-[3-(2-methoxy-ethyl)-2,3,4,5-tetrahydro-1H-benzo[d]azepin-7-ylamino]-pyrimidin-4-ylamino}-3,5,N-trimethyl-benzamide;

trans-2-{5-Chloro-2-[3-(2-methoxy-ethyl)-2,3,4,5-tetrahydro-1H-benzo[d]azepin-7-ylamino]-pyrimidin-4-ylamino}-cyclohexanol;

trans-2-[5-Chloro-2-(3-ethyl-2,3,4,5-tetrahydro-1H-benzo[d]azepin-7-ylamino)-pyrimidin-4-ylamino]-cyclohexanol;

5-Chloro-N*2*-(3-methanesulfonyl-2,3,4,5-tetrahydro-1H-benzo[d]azepin-7-yl]-N*4*-(2-methoxy-4-morpholin-4-yl-phenyl)-pyrimidine-2,4-diamine;

(2-exo, 3-exo)-3-[5-Chloro-2-(3-methanesulfonyl-2,3,4,5-tetrahydro-1H-benzo[d]azepin-7-ylamino)-pyrimidin-4-ylamino]-bicyclo[2.2.1]hept-5-ene-2-carboxylic acid amide;

2-[5-Chloro-2-(3-prop-2-ynyl-2,3,4,5-tetrahydro-1H-benzo[d]azepin-7-ylamino)-pyrimidin-4-ylamino]-N-methyl-benzamide;

(2-exo, 3-exo)-3-[5-Chloro-2-(3-prop-2-ynyl-2,3,4,5-tetrahydro-1H-benzo[d]azepin-7-ylamino)-pyrimidin-4-ylamino]-bicyclo[2.2.1]hept-5-ene-2-carboxylic acid amide;

5-Chloro-N*4*-(2-methoxy-4-morpholin-4-yl-phenyl)-N*2*-(3-prop-2-ynyl-2,3,4,5-tetrahydro-1H-benzo[d]azepin-7-yl)-pyrimidine-2,4-diamine;

N-{(1R,2R)-2-[5-Chloro-2-(3-prop-2-ynyl-2,3,4,5-tetrahydro-1H-benzo[d]azepin-7-ylamino)-pyrimidin-4-ylamino]-cyclohexyl}-methanesulfonamide;

N-{2-[5-Chloro-2-(3-prop-2-ynyl-2,3,4,5-tetrahydro-1H-benzo[d]azepin-7-ylamino)-pyrimidin-4-ylamino]-phenyl}-methanesulfonamide;

7-[5-Chloro-4-(2-methylcarbamoyl-phenylamino)-pyrimidin-2-ylamino]-1,2,4,5-tetrahydro-benzo[d]azepine-3-carboxylic acid dimethylamide;

2-{5-Chloro-2-[3-((S)-3,3,3-trifluoro-2-hydroxy-propyl)-2,3,4,5-tetrahydro-1H-benzo[d]azepin-7-ylamino]-pyrimidin-4-ylamino}-N-methyl-benzamide;

N-((1R,2R)-2-{5-Chloro-2-[3-((S)-3,3,3-trifluoro-2-hydroxy-propyl)-2,3,4,5-tetrahydro-1H-benzo[d]azepin-7-ylamino]-pyrimidin-4-ylamino}-cyclohexyl)-methanesulfonamide;

(S)-3-{7-[5-Chloro-4-(2-methoxy-4-morpholin-4-yl-phenylamino)-pyrimidin-2-ylamino]-1,2,4,5-tetrahydro-benzo[d]azepin-3-yl}-1,1,1-trifluoro-propan-2-ol;

(2-exo, 3-exo)-3-{5-Chloro-2-[3-((S)-3,3,3-trifluoro-2-hydroxy-propyl)-2,3,4,5-tetrahydro-1H-benzo[d]azepin-7-ylamino]-pyrimidin-4-ylamino}-bicyclo[2.2.1]heptane-2-carboxylic acid amide;

2-{5-Chloro-2-[3-((R)-3,3,3-trifluoro-2-hydroxy-propyl)-2,3,4,5-tetrahydro-1H-benzo[d]azepin-7-ylamino]-pyrimidin-4-ylamino}-3-fluoro-N-methyl-benzamide;

(R)-3-{7-[5-Chloro-4-(2-methoxy-4-morpholin-4-yl-phenylamino)-pyrimidin-2-ylamino]-1,2,4,5-tetrahydro-benzo[d]azepin-3-yl}-1,1,1-trifluoro-propan-2-ol;

(2-exo, 3-exo)-3-{5-Chloro-2-[3-((R)-3,3,3-trifluoro-2-hydroxy-propyl)-2,3,4,5-tetrahydro-1H-benzo[d]azepin-7-ylamino]-pyrimidin-4-ylamino}-bicyclo[2.2.1]hept-5-ene-2-carboxylic acid amide;

2-{5-Chloro-2-[3-((S)-3,3,3-trifluoro-2-methoxy-propyl)-2,3,4,5-tetrahydro-1H-benzo[d]azepin-7-ylamino]-pyrimidin-4-ylamino}-N-methyl-benzamide;

N-((1R,2R)-2-{5-Chloro-2-[3-((S)-3,3,3-trifluoro-2-methoxy-propyl)-2,3,4,5-tetrahydro-1H-benzo[d]azepin-7-ylamino]-pyrimidin-4-ylamino}-cyclohexyl)-methanesulfonamide;

5-Chloro-N*4*-(2-methoxy-4-morpholin-4-yl-phenyl)-N*2*-[-((S)-3,3,3-trifluoro-2-methoxy-propyl)-2,3,4,5-tetrahydro-1H-benzo[d]azepin-7-yl]-pyrimidine-2,4-diamine;

(2-exo, 3-exo)-3-{5-Chloro-2-[3-((S)-3,3,3-trifluoro-2-methoxy-propyl)-2,3,4,5-tetrahydro-1H-benzo[d]azepin-7-ylamino]-pyrimidin-4-ylamino}-bicyclo[2.2.1]hept-5-ene-2-carboxylic acid amide;

2-[5-Chloro-2-(5,5-dimethyl-2-oxo-2,3,4,5-tetrahydro-1H-benzo[d]azepin-7-ylamino)-pyrimidin-4-ylamino]-N-ethyl-benzamide;

2-[5-Chloro-2-(5,5-dimethyl-2-oxo-2,3,4,5-tetrahydro-1H-benzo[d]azepin-7-ylamino)-pyrimidin-4-ylamino]-N-isopropyl-benzamide;

2-[5-Chloro-2-(5,5-dimethyl-2-oxo-2,3,4,5-tetrahydro-1H-benzo[d]azepin-7-ylamino)-pyrimidin-4-ylamino]-N-cyclopropyl-benzamide;

2-{5-Chloro-2-[3-(2-methoxy-ethyl)-2,3,4,5-tetrahydro-1H-benzo[d]azepin-7-ylamino]-pyrimidin-4-ylamino}-N-isopropyl-benzamide;

2-{5-Chloro-2-[3-(2-methoxy-ethyl)-2,3,4,5-tetrahydro-1H-benzo[d]azepin-7-ylamino]-pyrimidin-4-ylamino}-N-ethyl-benzamide;

2-{5-Chloro-2-[3-(2-methoxy-ethyl)-2,3,4,5-tetrahydro-1H-benzo[d]azepin-7-ylamino]-pyrimidin-4-ylamino}-N-cyclopropyl-benzamide;

7-[4-(2-Acetyl-phenylamino)-5-chloro-pyrimidin-2-ylamino]-1-methyl-1,3,4,5-tetrahydro-benzo[b]azepin-2-one;

3-Chloro-2-[5-chloro-2-(1-methyl-2-oxo-2,3,4,5-tetrahydro-1H-benzo[b]azepin-7-ylamino)-pyrimidin-4-ylamino]-N-methyl-benzamide;

trans-2-[5-Chloro-2-(1-methyl-2-oxo-2,3,4,5-tetrahydro-1H-benzo[b]azepin-7-ylamino)-pyrimidin-4-ylamino]-cyclohexanecarboxylic acid amide;

2-[5-Chloro-2-(1-methyl-2-oxo-2,3,4,5-tetrahydro-1H-benzo[b]azepin-7-ylamino)-pyrimidin-4-ylamino]-5-piperidin-1-yl-benzamide;

2-[5-Chloro-2-(1-methyl-2-oxo-2,3,4,5-tetrahydro-1H-benzo[b]azepin-7-ylamino)pyrimidin-4-ylamino]-5-morpholin-4-yl-benzamide;

2-{5-Chloro-2-[1-(2-methoxy-ethyl)-2-oxo-2,3,4,5-tetrahydro-1H-benzo[b]azepin-7-ylamino]-pyrimidin-4-ylamino}-3-fluoro-N-methyl-benzamide;

3-Chloro-2-{5-chloro-2-[1-(2-methoxy-ethyl)-2-oxo-2,3,4,5-tetrahydro-1H-benzo[b]azepin-7-ylamino]-pyrimidin-4-ylamino}-N-methyl-benzamide;

2-[5-Chloro-2-(1-ethyl-2-oxo-2,3,4,5-tetrahydro-1H-benzo[b]azepin-8-ylamino)pyrimidin-4-ylamino]-3-fluoro-N-methyl-benzamide;

2-[5-Bromo-2-(1-ethyl-2-oxo-2,3,4,5-tetrahydro-1H-benzo[b]azepin-8-ylamino)-pyrimidin-4-ylamino]-3-fluoro-N-methyl-benzamide;

2-[5-Chloro-2-(1-ethyl-2-oxo-2,3,4,5-tetrahydro-1H-benzo[b]azepin-8-ylamino)-pyrimidin-4-ylamino]-3,N-dimethyl-benzamide;

2-{5-Chloro-2-[1-(2-methoxy-ethyl)-2-oxo-2,3,4,5-tetrahydro-1H-benzo[b]azepin-8-ylamino]-pyrimidin-4-ylamino}-3,N-dimethyl-benzamide;

2-{5-Chloro-2-[1-(2-methoxy-ethyl)-2-oxo-2,3,4,5-tetrahydro-1H-benzo[b]azepin-8-ylamino]-pyrimidin-4-ylamino}-3-fluoro-N-methyl-benzamide;

N-(trans-2-{5-Chloro-2-[3-(2-methoxy-ethyl)-2,3,4,5-tetrahydro-1H-benzo[d]azepin-7-ylamino]-pyrimidin-4-ylamino}-cyclopentyl)-methanesulfonamide;

cis-2-{5-Chloro-2-[3-(2-methoxy-ethyl)-2,3,4,5-tetrahydro-1H-benzo[d]azepin-7-ylamino]-pyrimidin-4-ylamino}-cyclopentanecarboxylic acid methylamide;

cis-2-[5-Chloro-2-(1-ethyl-6-methoxy-2-oxo-2,3,4,5-tetrahydro-1H-benzo[b]azepin-7-ylamino)-pyrimidin-4-ylamino]-cyclopentanecarboxylic acid methylamide;

N-{trans-2-[5-Chloro-2-(1-ethyl-6-methoxy-2-oxo-2,3,4,5-tetrahydro-1H-benzo[b]azepin-7-ylamino)-pyrimidin-4-ylamino]-cyclopentyl}-methanesulfonamide;

cis-2-[5-Chloro-2-(3-dimethylcarbamoylmethyl-8-methoxy-2,3,4,5-tetrahydro-1H-benzo[d]azepin-7-ylamino)-pyrimidin-4-ylamino]-cyclopentanecarboxylic acid methylamide;

2-[5-Bromo-2-(3-dimethylcarbamoylmethyl-8-methoxy-2,3,4,5-tetrahydro-1H-benzo[d]azepin-7-ylamino)-pyrimidin-4-ylamino]-N-methyl-benzamide;

2-[5-Chloro-2-(5,5-dimethyl-2-oxo-2,3,4,5-tetrahydro-1H-benzo[b]azepin-7-ylamino)-pyrimidin-4-ylamino]-N-methyl-benzamide;

3-Chloro-2-[5-chloro-2-(5,5-dimethyl-2-oxo-2,3,4,5-tetrahydro-1H-benzo[b]azepin-7-ylamino)-pyrimidin-4-ylamino]-N-methyl-benzamide;

N-{(1R,2R)-2-[5-Chloro-2-(5,5-dimethyl-2-oxo-2,3,4,5-tetrahydro-1H-benzo[b]azepin-7-ylamino)-pyrimidin-4-ylamino]-cyclohexyl}-methanesulfonamide;

2-[5-Chloro-2-(1,5,5-trimethyl-2-oxo-2,3,4,5-tetrahydro-1H-benzo[b]azepin-7-ylamino)-pyrimidin-4-ylamino]-N-methyl-benzamide;

N-{(1R,2R)-2-[5-Chloro-2-(1,5,5-trimethyl-2-oxo-2,3,4,5-tetrahydro-1H-benzo[b]azepin-7-ylamino)-pyrimidin-4-ylamino]-cyclohexyl}-methanesulfonamide;

(2-exo, 3-exo)-3-[5-Chloro-2-(1,5,5-trimethyl-2-oxo-2,3,4,5-tetrahydro-1H-benzo[b]azepin-7-ylamino)-pyrimidin-4-ylamino]-bicyclo[2.2.1]hept-5-ene-2-carboxylic acid amide;

2-[5-Chloro-2-(1-ethyl-5,5-dimethyl-2-oxo-2,3,4,5-tetrahydro-1H-benzo[b]azepin-7-ylamino)-pyrimidin-4-ylamino]-N-methyl-benzamide;

N-{(1R,2R)-2-[5-Chloro-2-(1-ethyl-5,5-dimethyl-2-oxo-2,3,4,5-tetrahydro-1H-benzo[b]azepin-7-ylamino)-pyrimidin-4-ylamino]-cyclohexyl}-methanesulfonamide;

3-Chloro-2-[5-chloro-2-(1-ethyl-5,5-dimethyl-2-oxo-2,3,4,5-tetrahydro-1H-benzo[b]azepin-7-ylamino)-pyrimidin-4-ylamino]-N-methyl-benzamide;

2-[5-Chloro-2-(1-ethyl-5,5-dimethyl-2-oxo-2,3,4,5-tetrahydro-1H-benzo[b]azepin-7-ylamino)-pyrimidin-4-ylamino]-3-fluoro-N-methyl-benzamide;

7-[5-Chloro-4-(2-methoxy-4-morpholin-4-yl-phenylamino)-pyrimidin-2-ylamino]-1-ethyl-5,5-dimethyl-1,3,4,5-tetrahydro-benzo[b]azepin-2-one;

N-{(1R,2R)-2-[5-Chloro-2-(5,5-dimethyl-2,3,4,5-tetrahydro-1H-benzo[b]azepin-7-ylamino)-pyrimidin-4-ylamino]-cyclohexyl}-methanesulfonamide;

7-[5-Chloro-4-(2-methoxy-4-morpholin-4-yl-phenylamino)-pyrimidin-2-ylamino]-1-ethyl-5,5-dimethyl-1,3,4,5-tetrahydro-benzo[b]azepin-2-one;

(2-exo, 3-exo)-3-[5-Chloro-2-(5,5-dimethyl-2-oxo-2,3,4,5-tetrahydro-1H-benzo[b]azepin-7-ylamino)-pyrimidin-4-ylamino]-bicyclo[2.2.1]hept-5-ene-2-carboxylic acid amide;

N-{(1R,2R)-2-[5-Chloro-2-(5,5-dimethyl-2-oxo-2,3,4,5-tetrahydro-1H-benzo[b]azepin-7-ylamino)-pyrimidin-4-ylamino]-cyclohexyl}-acetamide;

2-[5-Chloro-2-(5,5-dimethyl-2-oxo-2,3,4,5-tetrahydro-1H-benzo[b]azepin-7-ylamino)-pyrimidin-4-ylamino]-3-fluoro-N-methyl-benzamide;

7-{5-Chloro-4-[2-(1-methyl-1H-imidazol-2-yl)-phenylamino]-pyrimidin-2-ylamino}-5,5-dimethyl-1,3,4,5-tetrahydro-benzo[b]azepin-2-one;

7-[5-Chloro-4-(2-pyrazol-1-yl-phenylamino)-pyrimidin-2-ylamino]-5,5-dimethyl-1,3,4,5-tetrahydro-benzo[b]azepin-2-one;

2-[5-Chloro-2-(5,5-dimethyl-2-oxo-2,3,4,5-tetrahydro-1H-benzo[b]azepin-7-ylamino)-pyrimidin-4-ylamino]-3,N-dimethyl-benzamide;

2-[5-Chloro-2-(1-oxo-2,3,4,5-tetrahydro-1H-benzo[c]azepin-8-ylamino)-pyrimidin-4-ylamino]-3-fluoro-N-methyl-benzamide;

2-[5-Chloro-2-(1-oxo-2,3,4,5-tetrahydro-1H-benzo[c]azepin-8-ylamino)-pyrimidin-4-ylamino]-3,N-dimethyl-benzamide;

2-[5-Chloro-2-(5-oxo-2,3,4,5-tetrahydro-1H-benzo[e][1,4]diazepin-8-ylamino)-pyrimidin-4-ylamino]-N-methyl-benzamide;

2-[5-Chloro-2-(4-methyl-5-oxo-2,3,4,5-tetrahydro-1H-benzo[e][1,4]diazepin-8-ylamino)-pyrimidin-4-ylamino]-N-methylbenzamide;

2-[5-Chloro-2-(1,4-dimethyl-5-oxo-2,3,4,5-tetrahydro-1H-benzo[e][1,4]diazepin-8-ylamino)-pyrimidin-4-ylamino]-N-methylbenzamide;

2-[5-Chloro-2-(1-methyl-5-oxo-2,3,4,5-tetrahydro-1H-benzo[e][1,4]diazepin-8-ylamino)-pyrimidin-4-ylamino]-N-methylbenzamide;
2-{5-Chloro-2-[1-(2-diethylamino-ethyl)-5-oxo-2,3,4,5-tetrahydro-1H-benzo[e][1,4]diazepin-8-ylamino]-pyrimidin-4-ylamino}-N-methylbenzamide;
2-[5-Chloro-2-(1,4-dimethyl-5-oxo-2,3,4,5-tetrahydro-1H-benzo[e][1,4]diazepin-8-ylamino)-pyrimidin-4-ylamino]-N-methylbenzamide;
2-[5-Chloro-2-(1-methyl-2,3,4,5-tetrahydro-1H-benzo[e][1,4]diazepin-8-ylamino)-pyrimidin-4-ylamino]-N-methylbenzamide;
2-[5-Chloro-2-(1,4-diethyl-5-oxo-2,3,4,5-tetrahydro-1H-benzo[e][1,4]diazepin-8-ylamino)-pyrimidin-4-ylamino]-N-methylbenzamide;
2-[5-Chloro-2-(1,4-diethyl-2,3,4,5-tetrahydro-1H-benzo[e][1,4]diazepin-8-ylamino)-pyrimidin-4-ylamino]-N-methylbenzamide;
2-[5-Chloro-2-(1-methyl-2,3,4,5-tetrahydro-1H-benzo[e][1,4]diazepin-7-ylamino)-pyrimidin-4-ylamino]-N-methylbenzamide;
N-{2-[5-Chloro-2-(1-methyl-2,3,4,5-tetrahydro-1H-benzo[e][1,4]diazepin-7-ylamino)-pyrimidin-4-ylamino]-phenyl}-methanesulfonamide;
N-{(1R,2R)-2-[5-Chloro-2-(1-methyl-2,3,4,5-tetrahydro-1H-benzo[e][1,4]diazepin-7-ylamino)-pyrimidin-4-ylamino]-cyclohexyl}-methanesulfonamide;
N-{2-[5-Chloro-2-(1,4-diethyl-5-oxo-2,3,4,5-tetrahydro-1H-benzo[e][1,4]diazepin-8-ylamino)-pyrimidin-4-ylamino]-phenyl}-methanesulfonamide;
N-{(1R,2R)-2-[5-Chloro-2-(1,4-diethyl-5-oxo-2,3,4,5-tetrahydro-1H-benzo[e][1,4]diazepin-8-ylamino)-pyrimidin-4-ylamino]-cyclohexyl}-methanesulfonamide;
N-{2-[5-Chloro-2-(1,4-diethyl-2,3,4,5-tetrahydro-1H-benzo[e][1,4]diazepin-8-ylamino)-pyrimidin-4-ylamino]-phenyl}-methanesulfonamide;
N-{(1R,2R)-2-[5-Chloro-2-(1,4-diethyl-2,3,4,5-tetrahydro-1H-benzo[e][1,4]diazepin-8-ylamino)-pyrimidin-4-ylamino]-cyclohexyl}-methanesulfonamide;
N-{(1R,2R)-2-[5-Chloro-2-(7-chloro-1,4-diethyl-2,3,4,5-tetrahydro-1H-benzo[e][1,4]diazepin-8-ylamino)-pyrimidin-4-ylamino]-cyclohexyl}-methanesulfonamide;
2-[5-Chloro-2-(1-methyl-5-oxo-2,3,4,5-tetrahydro-1H-benzo[e][1,4]diazepin-7-ylamino)-pyrimidin-4-ylamino]-N-methylbenzamide;
N-(2-{5-Chloro-2-[4-(2-methoxy-ethyl)-1-methyl-2,3,4,5-tetrahydro-1H-benzo[e][1,4]diazepin-7-ylamino]-pyrimidin-4-ylamino}-phenyl)-methanesulfonamide;
N-((1R,2R)-2-{5-Chloro-2-[4-(2-methoxy-ethyl)-1-methyl-2,3,4,5-tetrahydro-1H-benzo[e][1,4]diazepin-7-ylamino]-pyrimidin-4-ylamino}-cyclohexyl)-methanesulfonamide;
N-{2-[5-Chloro-2-(7-chloro-1,4-diethyl-2,3,4,5-tetrahydro-1H-benzo[e][1,4]diazepin-8-ylamino)-pyrimidin-4-ylamino]-phenyl}-methanesulfonamide;
2-{5-Chloro-2-[4-(2-methoxy-ethyl)-1-methyl-2,3,4,5-tetrahydro-1H-benzo[e][1,4]diazepin-7-ylamino]-pyrimidin-4-ylamino}-N-methyl-benzamide;
N-{(1R,2R)-2-[5-Chloro-2-(3-ethyl-2,3,4,5-tetrahydro-1H-benzo[d]azepin-7-ylamino)-pyrimidin-4-ylamino]-cyclohexyl}methanesulfonamide;
5-Chloro-N*2*-(3-ethyl-2,3,4,5-tetrahydro-1H-benzo[d]azepin-7-yl)-N*4*-(2-methoxy-4-morpholin-4-yl-phenyl)-pyrimidine-2,4-diamine;
5-Chloro-N*2*-(3-ethyl-2,3,4,5-tetrahydro-1H-benzo[d]azepin-7-yl)-N*4*-(4-morpholin-4-yl-phenyl)-pyrimidine-2,4-diamine;
5-Chloro-N*2*-(3-ethyl-2,3,4,5-tetrahydro-1H-benzo[d]azepin-7-yl)-N*4*-(3-morpholin-4-yl-phenyl)-pyrimidine-2,4-diamine;
N-{(1R,2R)-2-[5-Chloro-2-(3-ethyl-2,3,4,5-tetrahydro-1H-benzo[d]azepin-7-ylamino)-pyrimidin-4-ylamino]-cyclohexyl}-acetamide;
N-{(1R,2R)-2-[5-Chloro-2-(3-ethyl-2,3,4,5-tetrahydro-1H-benzo[d]azepin-7-ylamino)-pyrimidin-4-ylamino]-cyclohexyl}-2,2,2-trifluoro-acetamide;
3-{(1R,2R)-2-[5-Chloro-2-(3-ethyl-2,3,4,5-tetrahydro-1H-benzo[d]azepin-7-ylamino)-pyrimidin-4-ylamino]-cyclohexyl}-1,1-dimethyl-urea;
2-{5-Chloro-2-[3-((R)-3,3,3-trifluoro-2-hydroxy-propyl)-2,3,4,5-tetrahydro-1H-benzo[d]azepin-7-ylamino]-pyrimidin-4-ylamino}-N-methyl-benzamide;
N-((1R,2R)-2-{5-Chloro-2-[3-((R)-3,3,3-trifluoro-2-hydroxy-propyl)-2,3,4,5-tetrahydro-1H-benzo[d]azepin-7-ylamino]-pyrimidin-4-ylamino}-cyclohexyl)-methanesulfonamide;
N-((1R,2R)-2-{5-Chloro-2-[3-(2-methoxy-ethyl)-2,3,4,5-tetrahydro-1H-benzo[d]azepin-7-ylamino]-pyrimidin-4-ylamino}-cyclohexyl)-2,2,2-trifluoro-acetamide;
N*4*-((1R,2R)-2-Amino-cyclohexyl)-5-chloro-N*2*-[3-(2-methoxy-ethyl)-2,3,4,5-tetrahydro-1H-benzo[d]azepin-7-yl]-pyrimidine-2,4-diamine;
2,2,2-Trifluoro-ethanesulfonic acid ((1R,2R)-2-{5-chloro-2-[3-(2-methoxy-ethyl)-2,3,4,5-tetrahydro-1H-benzo[d]azepin-7-ylamino]-pyrimidin-4-ylamino}-cyclohexyl)-amide;
Ethanesulfonic acid ((1R,2R)-2-{5-chloro-2-[3-(2-methoxy-ethyl)-2,3,4,5-tetrahydro-1H-benzo[d]azepin-7-ylamino]-pyrimidin-4-ylamino}-cyclohexyl)-amide;
Cyclopropanesulfonic acid ((1R,2R)-2-{5-chloro-2-[3-(2-methoxy-ethyl)-2,3,4,5-tetrahydro-1H-benzo[d]azepin-7-ylamino]-pyrimidin-4-ylamino}-cyclohexyl)-amide;
Propane-2-sulfonic acid ((1R,2R)-2-{5-chloro-2-[3-(2-methoxy-ethyl)-2,3,4,5-tetrahydro-1H-benzo[d]azepin-7-ylamino]-pyrimidin-4-ylamino}-cyclohexyl)-amide;
2-{5-Chloro-2-[12-(2-methoxy-ethyl)-12-aza-tricyclo[7.2.1.0(2,7)]dodeca-2(7),3,5-trien-4-ylamino]-pyrimidin-4-ylamino}-3-fluoro-N-methyl-benzamide;
2-{5-Chloro-2-[12-(2-methoxy-ethyl)-12-aza-tricyclo[7.2.1.0(2,7)]dodeca-2(7),3,5-trien-4-ylamino]-pyrimidin-4-ylamino}-3-fluoro-benzoic acid isopropyl ester;
(2-endo,3-endo)-3-{5-Chloro-2-[3-(2-methoxy-ethyl)-2,3,4,5-tetrahydro-1H-benzo[d]azepin-7-ylamino]-pyrimidin-4-ylamino}-bicyclo[2.2.1]hept-5-ene-2-carboxylic acid ethyl ester;
(2-endo,3-endo)-3-{5-Chloro-2-[3-(2-methoxy-ethyl)-2,3,4,5-tetrahydro-1H-benzo[d]azepin-7-ylamino]-pyrimidin-4-ylamino}-bicyclo[2.2.1]hept-5-ene-2-carboxylic acid amide;
3-Chloro-2-[5-chloro-2-(1-methyl-2,3,4,5-tetrahydro-1H-benzo[e][1,4]diazepin-8-ylamino)-pyrimidin-4-ylamino]-N-methyl-benzamide;
N-((1R,2R)-2-{5-Chloro-2-[8-methoxy-3-((S)-3,3,3-trifluoro-2-hydroxy-propyl)-2,3,4,5-tetrahydro-1H-benzo[d]azepin-7-ylamino]-pyrimidin-4-ylamino}-cyclohexyl)-methanesulfonamide;
(S)-3-{7-[5-Chloro-4-(2-methoxy-4-morpholin-4-yl-phenylamino)-pyrimidin-2-ylamino]-8-methoxy-1,2,4,5-tetrahydro-benzo[d]azepin-3-yl}-1,1,1-trifluoro-propan-2-ol;
N-{2-[5-Chloro-2-(1-methyl-2,3,4,5-tetrahydro-1H-benzo[e][1,4]diazepin-8-ylamino)-pyrimidin-4-ylamino]-phenyl}-methanesulfonamide;

{8-[5-Chloro-4-(2-methanesulfonylamino-phenylamino)-pyrimidin-2-ylamino]-1-methyl-1,2,3,5-tetrahydro-benzo[e][1,4]diazepin-4-yl}-acetic acid methyl ester;

Acetic acid 2-{8-[5-chloro-4-(2-methanesulfonylamino-phenylamino)-pyrimidin-2-ylamino]-1-methyl-1,2,3,5-tetrahydro-benzo[e][1,4]diazepin-4-yl}-ethyl ester;

N-{2-[5-Chloro-2-(4-methanesulfonyl-1-methyl-2,3,4,5-tetrahydro-1H-benzo[e][1,4]diazepin-8-ylamino)-pyrimidin-4-ylamino]-phenyl}-methanesulfonamide;

N-{(1R,2R)-2-[5-Chloro-2-(1-methyl-2,3,4,5-tetrahydro-1H-benzo[e][1,4]diazepin-8-ylamino)-pyrimidin-4-ylamino]-cyclohexyl}-methanesulfonamide;

Acetic acid 2-{8-[5-chloro-4-((1R,2R)-2-methanesulfonylamino-cyclohexylamino)-pyrimidin-2-ylamino]-1-methyl-1,2,3,5-tetrahydro-benzo[e][1,4]diazepin-4-yl}-ethyl ester;

N-{(1R,2R)-2-[5-Chloro-2-(4-methanesulfonyl-1-methyl-2,3,4,5-tetrahydro-1H-benzo[e][1,4]diazepin-8-ylamino)-pyrimidin-4-ylamino]-cyclohexyl}-methanesulfonamide;

N-((1R,2R)-2-{5-Chloro-2-[4-(2-hydroxy-ethyl)-1-methyl-2,3,4,5-tetrahydro-1H-benzo[e][1,4]diazepin-8-ylamino]-pyrimidin-4-ylamino}-cyclohexyl)-methanesulfonamide;

N-{(1R,2R)-2-[5-Chloro-2-(4-cyclopropylmethyl-1-methyl-2,3,4,5-tetrahydro-1H-benzo[e][1,4]diazepin-8-ylamino)-pyrimidin-4-ylamino]-cyclohexyl}-methanesulfonamide;

N-{(1R,2R)-2-[5-Chloro-2-(1-methyl-4-prop-2-ynyl-2,3,4,5-tetrahydro-1H-benzo[e][1,4]diazepin-8-ylamino)-pyrimidin-4-ylamino]-cyclohexyl}-methanesulfonamide;

8-[5-Chloro-4-((1R,2R)-2-methanesulfonylamino-cyclohexylamino)-pyrimidin-2-ylamino]-1-methyl-1,2,3,5-tetrahydro-benzo[e][1,4]diazepine-4-carboxylic acid dimethylamide;

N-((1R,2R)-2-{5-Chloro-2-[4-(imidazole-1-carbonyl)-1-methyl-2,3,4,5-tetrahydro-1H-benzo[e][1,4]diazepin-8-ylamino]-pyrimidin-4-ylamino}-cyclohexyl)-methanesulfonamide;

2-[5-Chloro-2-(4-methanesulfonyl-1-methyl-2,3,4,5-tetrahydro-1H-benzo[e][1,4]diazepin-8-ylamino)-pyrimidin-4-ylamino]-N-methyl-benzamide;

2-{5-Chloro-2-[4-(2-methoxy-ethyl)-1-methyl-2,3,4,5-tetrahydro-1H-benzo[e][1,4]diazepin-8-ylamino]-pyrimidin-4-ylamino}-N-methyl-benzamide;

2-{5-Chloro-2-[4-(2-hydroxy-ethyl)-1-methyl-2,3,4,5-tetrahydro-1H-benzo[e][1,4]diazepin-8-ylamino]-pyrimidin-4-ylamino}-N-methyl-benzamide;

2-{5-Chloro-2-[4-(imidazole-1-carbonyl)-1-methyl-2,3,4,5-tetrahydro-1H-benzo[e][1,4]diazepin-8-ylamino]-pyrimidin-4-ylamino}-N-methyl-benzamide;

2-[5-Chloro-2-(1-methyl-4-prop-2-ynyl-2,3,4,5-tetrahydro-1H-benzo[e][1,4]diazepin-8-ylamino)-pyrimidin-4-ylamino]-N-methyl-benzamide;

2-[5-Chloro-2-(1-methyl-4-prop-2-ynyl-2,3,4,5-tetrahydro-1H-benzo[e][1,4]diazepin-8-ylamino)-pyrimidin-4-ylamino]-N-methyl-N-prop-2-ynyl-benzamide;

8-[5-Chloro-4-(2-methylcarbamoyl-phenylamino)-pyrimidin-2-ylamino]-1-methyl-1,2,3,5-tetrahydro-benzo[e][1,4]diazepine-4-carboxylic acid dimethylamide;

N-((1R,2R)-2-{5-Chloro-2-[7-methoxy-4-(2-methoxy-ethyl)-1-methyl-2,3,4,5-tetrahydro-1H-benzo[e][1,4]diazepin-8-ylamino]-pyrimidin-4-ylamino}-cyclohexyl)-methanesulfonamide;

(2-exo,3-exo)-3-{5-Chloro-2-[7-methoxy-4-(2-methoxy-ethyl)-1-methyl-2,3,4,5-tetrahydro-1H-benzo[e][1,4]diazepin-8-ylamino]-pyrimidin-4-ylamino}-bicyclo[2.2.1]heptane-2-carboxylic acid amide;

N-((1R,2R)-2-{5-Chloro-2-[7-methoxy-1-methyl-4-((R)-3,3,3-trifluoro-2-hydroxy-propyl)-2,3,4,5-tetrahydro-1H-benzo[e][1,4]diazepin-8-ylamino]-pyrimidin-4-ylamino}-cyclohexyl)-methanesulfonamide;

5-Chloro-N*2*-(7-methoxy-1-methyl-2,3,4,5-tetrahydro-1H-benzo[e][1,4]diazepin-8-yl)-N*4*-(2-methoxy-4-morpholin-4-yl-phenyl)-pyrimidine-2,4-diamine;

5-Chloro-N*2*-(4-methanesulfonyl-7-methoxy-1-methyl-2,3,4,5-tetrahydro-1H-benzo[e][1,4]diazepin-8-yl)-N*4*-(2-methoxy-4-morpholin-4-yl-phenyl)-pyrimidine-2,4-diamine;

5-Chloro-N*2*-[7-methoxy-4-(2-methoxy-ethyl)-1-methyl-2,3,4,5-tetrahydro-1H-benzo[e][1,4]diazepin-8-yl]-N*4*-(2-methoxy-4-morpholin-4-yl-phenyl)-pyrimidine-2,4-diamine;

(R)-3-{8-[5-Chloro-4-(2-methoxy-4-morpholin-4-yl-phenylamino)-pyrimidin-2-ylamino]-7-methoxy-1-methyl-1,2,3,5-tetrahydro-benzo[e][1,4]diazepin-4-yl}-1,1,1-trifluoro-propan-2-ol;

N-((1R,2R)-2-{5-Chloro-2-[1-methyl-7-(2,2,2-trifluoro-ethoxy)-2,3,4,5-tetrahydro-1H-benzo[e][1,4]diazepin-8-ylamino]-pyrimidin-4-ylamino}-cyclohexyl)-methanesulfonamide;

N-((1R,2R)-2-{5-Chloro-2-[1-methyl-7-(2,2,2-trifluoro-ethoxy)-4-((R)-3,3,3-trifluoro-2-hydroxy-propyl)-2,3,4,5-tetrahydro-1H-benzo[e][1,4]diazepin-8-ylamino]-pyrimidin-4-ylamino}-cyclohexyl)-methanesulfonamide;

N-{(1R,2R)-2-[5-Chloro-2-(1-isopropyl-5-oxo-2,3,4,5-tetrahydro-1H-benzo[e][1,4]diazepin-8-ylamino)-pyrimidin-4-ylamino]-cyclohexyl}-methanesulfonamide;

2-[5-Chloro-2-(3,4-dihydro-2H-benzo[b][1,4]dioxepin-2-ylamino)-pyrimidin-4-ylamino]-N-methyl-benzamide;

2-[5-Chloro-2-(5-oxo-2,3,4,5-tetrahydro-benzo[f][1,4]oxazepin-8-ylamino)-pyrimidin-4-ylamino]-N-methyl-benzamide;

2-[5-Chloro-2-(2-oxo-2,3,4,5-tetrahydro-1H-benzo[b]azepin-8-ylamino)-pyrimidin-4-ylamino]-N-methyl benzamide;

2-[5-chloro-2-(4-methyl-5-oxo-2,3,4,5-tetrahydro-benzo[f][1,4]oxazepin-8-ylamino)-pyrimidin-4-ylamino]-N-methyl-benzamide;

2-[5-Chloro-2-(4-ethyl-5-oxo-2,3,4,5-tetrahydro-benzo[f][1,4]oxazepin-8-ylamino)-pyrimidin-4-ylamino]-N-methyl-benzamide;

2-[5-Chloro-2-(6,7,8,9-tetrahydro-5-thia-aza-benzocyclohepten-2-ylamino)-pyrimidin-4-ylamino]-N-methyl-benzamide;

2-[5-Chloro-2-(8-ethyl-6,7,8,9-tetrahydro-5-thia-aza-benzocyclohepten-2-ylamino)-pyrimidin-4-ylamino]-N-methyl-benzamide;

N-{2-[3-Chloro-2-(6,7,8,9-tetrahydro-5-thia-8-aza-benzocyclohepten-2-ylamino)-pyrimidin-4-ylamino]-phenyl}-methanesulfonamide;

N-{(1R,2R)-2-[5-Chloro-2-(6,7,8,9-tetrahydro-5-thia-8-aza-benzocyclohepten-2-ylamino)-pyrimidin-4-ylamino]-cyclohexyl}-methanesulfonamide;

N-{(1R,2R)-2-[5-Chloro-2-(5,5-dioxo-6,7,8,9-tetrahydro-5H-5lambda*6*-thia-8aza-benzoylcyclohepten-2-ylamino)-pyrimidin-4-ylamino]-cyclohexyl}-methanesulfonamide;

N-((1R,2R)-2-{5-Chloro-2-[8-(2-methoxy-ethyl)-6,7,8,9-tetrahydro-5-thia-8-aza-benzocyclohepten-2-ylamino]pyrimidin-4-ylamino}-cyclohexyl)-methanesulfonamide;

2-{5-Chloro-2-[8-(2-methoxy-ethyl)-6,7,8,9-tetrahydro-5-thia-8-aza-benzocyclohepten-2-ylamino]-pyrimidin-4-ylamino}-N-methyl-benzamide;

N-{2-[5-Chloro-2(5,5-dioxo-6,7,8,9-tetrahydro-5H-5lambda*6*-thia-8-aza-benzocyclohepten-2-ylamino)-pyrimidin-4-ylamino]-phenyl}-methanesulfonamide;
N-{(1R,2R)-2[5-Chloro-2-(2,3,4,5-tetrahydro-benzo[f]oxazepin-7-ylamino)-pyrimidin-4-ylamino]-cyclohexyl}-methanesulfonamide;
N-((1R,2R)-2-{-5-Chloro-2-[8-(2-hydroxy-ethyl)-6,7,8,9-tetrahydro-5-thia-8-azabenzo-cyclohepten-2-ylamino]-pyrimidin-4-ylamino}cyclohexyl)-methanesulfonamide;
Acetic acid 2-{2-[5-chloro-4-((1R,2R)-2-methanesulfonylamino-cyclohexylamino)-pyrimidin-2-ylamino]-6,7-dihydro-9H-5-thia-8-aza-benzocyclohepten-8-yl}-ethyl ester;
Acetic acid 2-{2-[5-Chloro-4-(2-methylcarbamoyl-phenylamino)-pyrimidin-2-ylamino]-6,7-dihydro-9H-5-thia-8-aza-benzoylcyclohepten-8-yl}-ethyl ester;
2-{5-Chloro-2-[8-(hydroxyl-ethyl)-6,7,8,9-tetrahydro-5-thia-8-aza-benzoylcyclohepten-2-ylamnio]-pyrimidin-4-ylamino}-N-methyl-benzamide;
(2-exo-3-exo)-3-[5-Chloro-2-(1-ethyl-6-methoxy-2-oxo-2,3,4,5-tetrahydro-1H-benzo[b]azepin-7-ylamino)-pyrimidin-4-ylamino]-bicyclo[2.2.1]hept-5-ene-2-carboxylic acid methylamide;
(2-exo-3-exo)-3-[5-Chloro-2-(1-ethyl-6-methoxy-2-oxo-2,3,4,5-tetrahydro-1H-benzo[b]azepin-7-ylamino)-pyrimidin-4-ylamino]-bicyclo[2.2.1]hept-5-ene-2-carboxylic acid dimethylamide;
(2-exo-3-exo)-3-[5-Chloro-2-(1-ethyl-6-methoxy-2-oxo-2,3,4,5-tetrahydro-1H-benzo[b]azepin-7-ylamino)-pyrimidin-4-ylamino]-bicyclo[2.2.1]hept-5-ene-2-carboxylic acid isopropylamide;
(2-exo-3-exo)-3-{5-Chloro-2-[8-methoxy-3-(2-methoxyethyl)-2,3,4,5-tetrahydro-1H-benzo[d]azepin-7-ylamino]-pyrimidin-4-ylamino}-bicyclo[2.2.1]hept-5-ene-2-carboxylic acid methylamide;
(2-exo-3-exo)-3-{5-Chloro-2-[8-methoxy-3-(2-methoxyethyl)-2,3,4,5-tetrahydro-1H-benzo[d]azepin-7-ylamino]-pyrimidin-4-ylamino}-bicyclo[2.2.1]hept-5-ene-2-carboxylic acid isopropylamide;
(2-exo-3-exo)-3-{5-Chloro-2-[8-methoxy-3-(2-methoxyethyl)-2,3,4,5-tetrahydro-1H-benzo[d]azepin-7-ylamino]-pyrimidin-4-ylamino}-bicyclo[2.2.1]hept-5-ene-2-carboxylic acid dimethylamide;
2-[5-Chloro-2-(1-ethyl-6-methoxy-2-oxo-2,3,4,5-tetrahydro-1H-benzo[b]azepin-7-ylamino)-pyrimidin-4-ylamino]-5-methoxy-N-methyl-benzamide;
2-[5-Chloro-2-(1-ethyl-6-methoxy-2-oxo-2,3,4,5-tetrahydro-1H-benzo[b]azepin-7-ylamino)-pyrimidin-4-ylamino]-5-methoxy-benzoic acid isopropyl ester;
2-[5-Chloro-2-(5,5-dimethyl-2-oxo-2,3,4,5-tetrahydro-1H-benzo[b]azepin-7-ylamino)-pyrimidin-4-ylamino]-5-methoxy-N-methyl-benzamide;
N*4*-[(2-exo-3-exo)-3-(1H-Benzoimidazol-2-yl)-bicyclo[2.2.1]hept-5-en-2-yl]-5-chloro-N*2*-[8-methoxy-3-(2-methoxy-ethyl)-2,3,4,5-tetrahydro-1H-benzo[d]azepin-7-yl]-pyrimidine-2,4-diamine;
7-[5-Chloro-4-(4-methoxy-2-pyrazol-1-yl-phenylamino)-pyrimidin-2-ylamino]-5,5-dimethyl-1,3,4,5-tetrahydro-benzo[b]azepin-2-one;
5-Chloro-N*2*-[8-methoxy-3-(2-methoxy-ethyl)-2,3,4,5-tetrahydro-1H-benzo[d]azepin-7-yl]-N*4*-(4-methoxy-2-pyrazol-1-yl-phenyl)-pyrimidine-2,4-diamine;
7-[5-Chloro-4-(4-methoxy-2-pyrazol-1-yl-phenylamino)-pyrimidin-2-ylamino]-1-ethyl-6-methoxy-1,3,4,5-tetrahydro-benzo[b]azepin-2-one;
7-[5-Chloro-4-(4-methoxy-2-pyrazol-1-yl-phenylamino)-pyrimidin-2-ylamino]-1-ethyl-8-methoxy-1,3,4,5-tetrahydro-benzo[b]azepin-2-one;
(2-exo-3-exo)-3-{5-Chloro-2-[3-(2-methoxy-ethyl)-2,3,4,5-tetrahydro-1H-benzo[d]azepin-7-ylamino]-pyrimidin-4-ylamino}-bicyclo[2.2.1]hept-5-ene-2-carboxylic acid methylamide;
2-{7-[5-Chloro-4-(4-methoxy-2-pyrazol-1-yl-phenylamino)-pyrimidin-2-ylamino]-8-methoxy-1,2,4,5-tetrahydro-benzo[d]azepin-3-yl}-N,N-dimethyl-acetamide;
2-[5-Chloro-2-(3-dimethylcarbamoylmethyl-8-methoxy-2,3,4,5-tetrahydro-1H-benzo[d]azepin-7-ylamino)-pyrimidin-4-ylamino]-5-methoxy-N-methyl-benzamide;
2-{5-Chloro-2-[3-(2-methoxy-ethyl)-2,3,4,5-tetrahydro-1H-benzo[d]azepin-7-ylamino]-pyrimidin-4-yl amino}-5-methoxy-N-methyl-benzamide;
7-[5-Chloro-4-(4-methoxy-2-pyrazol-1-yl-phenylamino)-pyrimidin-2-ylamino]-1,5,5-trimethyl-1,3,4,5-tetrahydro-benzo[b]azepin-2-one;
(2-exo-3-exo)-3-[5-Chloro-2-(5,5-dimethyl-2-oxo-2,3,4,5-tetrahydro-1H-benzo[b]azepin-7-ylamino)-pyrimidin-4-ylamino]-bicyclo[2.2.1]hept-5-ene-2-carboxylic acid methylamide;
2-{5-Chloro-2-[8-methoxy-3-(2-methoxy-ethyl)-2,3,4,5-tetrahydro-1H-benzo[d]azepin-7-ylamino]-pyrimidin-4-ylamino}-5-methoxy-N-methyl-benzamide;
5-Chloro-N*4*-(4-methoxy-2-pyrazol-1-yl-phenyl)-N*2*-(7-morpholin-4-yl-6,7,8,9-tetrahydro-5H-benzocyclohepten-2-yl)-pyrimidine-2,4-diamine;
2-[5-Chloro-4-(4-methoxy-2-pyrazol-1-yl-phenylamino)-pyrimidin-2-ylamino]-6,7,8,9-tetrahydro-5H-benzocyclohepten-7-ol;
(2-exo-3-exo)-3-[5-Chloro-2-(7-morpholin-4-yl-6,7,8,9-tetrahydro-5H-benzocyclohepten-2-ylamino)-pyrimidin-4-ylamino]-bicyclo[2.2.1]hept-5-ene-2-carboxylic acid methylamide;
(2-exo-3-exo)-3-[5-Chloro-2-(7-hydroxy-6,7,8,9-tetrahydro-5H-benzocyclohepten-2-ylamino)-pyrimidin-4-ylamino]-bicyclo[2.2.1]hept-5-ene-2-carboxylic acid methylamide;
2-{7-[5-Chloro-4-(4-morpholin-4-yl-2-pyrazol-1-yl-phenylamino)-pyrimidin-2-ylamino]-8-methoxy-1,2,4,5-tetrahydro-benzo[d]azepin-3-yl}-N,N-dimethyl-acetamide;
7-[5-Chloro-4-(4-morpholin-4-yl-2-pyrazol-1-yl-phenylamino)-pyrimidin-2-ylamino]-5,5-dimethyl-1,3,4,5-tetrahydro-benzo[b]azepin-2-one;
7-{5-Chloro-4-[4-(4-methyl-piperazin-1-yl)-2-pyrazol-1-yl-phenylamino]-pyrimidin-2-ylamino}-5,5-dimethyl-1,3,4,5-tetrahydro-benzo[b]azepin-2-one;
1-{4-[5-Chloro-2-(5,5-dimethyl-2-oxo-2,3,4,5-tetrahydro-1H-benzo[b]azepin-7-ylamino)-pyrimidin-4-ylamino]-3-pyrazol-1-yl-phenyl}-piperidine-4-carboxylic acid;
1-{4-[5-Chloro-2-(3-dimethylcarbamoylmethyl-8-methoxy-2,3,4,5-tetrahydro-1H-benzo[d]azepin-7-ylamino)-pyrimidin-4-ylamino]-3-pyrazol-1-yl-phenyl}-piperidine-4-carboxylic acid;
2-{7-[5-Chloro-4-(4-dimethylamino-2-pyrazol-1-yl-phenylamino)-pyrimidin-2-ylamino]-8-methoxy-1,2,4,5-tetrahydro-benzo[d]azepin-3-yl}-N,N-dimethyl-acetamide;
(1S,2S,3R,4R)-3-[2-((S)-7-Acetylamino-1-methoxy-9-oxo-6,7,8,9-tetrahydro-5H-benzocyclohepten-2-ylamino)-5-chloro-pyrimidin-4-ylamino]-bicyclo[2.2.1]hept-5-ene-2-carboxylic acid amid;
{7-[5-Chloro-4-(4-methoxy-2-pyrazol-1-yl-phenylamino)-pyrimidin-2-ylamino]-8-methoxy-1,2,4,5-tetrahydro-benzo[d]azepin-3-yl}-[1,4]dioxan-2-yl-methanone;

2-{5-Chloro-2-[3-([1,4]dioxane-2-carbonyl)-8-methoxy-2,3,4,5-tetrahydro-1H-benzo[d]azepin-7-ylamino]-pyrimidin-4-ylamino}-N,N-dimethyl-benzenesulfonamide;

(1S,2S,3R,4R)-3-{5-Chloro-2-[3-([1,4]dioxane-2-carbonyl)-8-methoxy-2,3,4,5-tetrahydro-1H-benzo[d]azepin-7-ylamino]-pyrimidin-4-ylamino}-bicyclo[2.2.1]hept-5-ene-2-carboxylic acid amide;

5-Chloro-N*2*-(3-[1,4]dioxan-2-ylmethyl-8-methoxy-2,3,4,5-tetrahydro-1H-benzo[d]azepin-7-yl)-N*4*-(4-methoxy-2-pyrazol-1-yl-phenyl)-pyrimidine-2,4-diamine;

2-[5-Chloro-2-(3-[1,4]dioxan-2-ylmethyl-8-methoxy-2,3,4,5-tetrahydro-1H-benzo[d]azepin-7-ylamino)-pyrimidin-4-ylamino]-N,N-dimethyl-benzenesulfonamide;

2-{5-Chloro-2-[3-([1,4]dioxane-2-carbonyl)-2,3,4,5-tetrahydro-1H-benzo[d]azepin-7-ylamino]-pyrimidin-4-ylamino}-N,N-dimethyl-benzenesulfonamide;

2-{5-Chloro-2-[3-([1,4]dioxane-2-carbonyl)-2,3,4,5-tetrahydro-1H-benzo[d]azepin-7-ylamino]-pyrimidin-4-ylamino}-3-fluoro-N-methyl-benzamide;

2-{5-Chloro-2-[3-([1,4]dioxane-2-carbonyl)-2,3,4,5-tetrahydro-1H-benzo[d]azepin-7-ylamino]-pyrimidin-4-ylamino}-3-fluoro-N-prop-2-ynyl-benzamide;

2-[5-Chloro-2-(3-[1,4]dioxan-2-ylmethyl-2,3,4,5-tetrahydro-1H-benzo[d]azepin-7-ylamino)-pyrimidin-4-ylamino]-N,N-dimethyl-benzenesulfonamide;

5-Chloro-N*2*-(3-[1,4]dioxan-2-ylmethyl-2,3,4,5-tetrahydro-1H-benzo[d]azepin-7-yl)-N*4*-(4-methoxy-2-pyrazol-1-yl-phenyl)-pyrimidine-2,4-diamine;

2-{5-Chloro-2-[7-(2,2,2-trifluoro-ethylamino)-6,7,8,9-tetrahydro-5H-benzocyclohepten-2-ylamino]-pyrimidin-4-ylamino}-N-methyl-benzamide;

5-Chloro-N*4*-(2-ethyl-4-morpholin-4-yl-phenyl)-N*2*-[7-(2,2,2-trifluoro-ethylamino)-6,7,8,9-tetrahydro-5H-benzocyclohepten-2-yl]-pyrimidine-2,4-diamine;

(1R,2R)-2-{5-Chloro-2-[7-(2,2,2-trifluoro-ethylamino)-6,7,8,9-tetrahydro-5H-benzocyclohepten-2-ylamino]-pyrimidin-4-ylamino-cyclohexanecarboxylic acid amide;

1S,2R,3S,4R)-3-{5-Chloro-2-[7-(2,2,2-trifluoro-ethylamino)-6,7,8,9-tetrahydro-5H-benzocyclohepten-2-ylamino]-pyrimidin-4-ylamino}-bicyclo[2.2.1]heptane-2-carboxylic acid amide;

5-Chloro-N*4*-[2-(1-methyl-1H-imidazol-2-yl)-phenyl]-N*2*-[7-(2,2,2-trifluoro-ethylamino)-6,7,8,9-tetrahydro-5H-benzocyclohepten-2-yl]-pyrimidine-2,4-diamine;

N-((1R,2R)-2-{5-Chloro-2-[7-(2,2,2-trifluoro-ethylamino)-6,7,8,9-tetrahydro-5H-benzocyclohepten-2-ylamino]-pyrimidin-4-ylamino}-cyclohexyl)-methanesulfonamide;

5-Chloro-N*4*-[2-(3-methyl-pyridin-2-yl)-phenyl]-N*2*-[7-(2,2,2-trifluoro-ethylamino)-6,7,8,9-tetrahydro-5H-benzocyclohepten-2-yl]-pyrimidine-2,4-diamine;

5-Chloro-N*4*-(2-methoxy-phenyl)-N*2*-[7-(2,2,2-trifluoro-ethylamino)-6,7,8,9-tetrahydro-5H-benzocyclohepten-2-yl]-pyrimidine-2,4-diamine;

5-Chloro-N*2*-[7-(2,2-difluoro-ethylamino)-6,7,8,9-tetrahydro-5H-benzocyclohepten-2-yl]-N*4*-(2-methoxy-4-morpholin-4-yl-phenyl)-pyrimidine-2,4-diamine;

2-{5-Chloro-2-[7-(2,2-difluoro-ethylamino)-6,7,8,9-tetrahydro-5H-benzocyclohepten-2-ylamino]-pyrimidin-4-ylamino}-N-methyl-benzamide;

5-Chloro-N*2*-[7-(2,2-difluoro-ethylamino)-6,7,8,9-tetrahydro-5H-benzocyclohepten-2-yl]-N*4*-[2-(1-methyl-1H-imidazol-2-yl)-phenyl]-pyrimidine-2,4-diamine;

N-((1R,2R)-2-{5-Chloro-2-[7-(2,2-difluoro-ethylamino)-6,7,8,9-tetrahydro-5H-benzocyclohepten-2-ylamino]-pyrimidin-4-ylamino}-cyclohexyl)-methanesulfonamide;

5-Chloro-N*2*-[7-(2,2-difluoro-ethylamino)-6,7,8,9-tetrahydro-5H-benzocyclohepten-2-yl]-N*4*-(2-methoxyphenyl)-pyrimidine-2,4-diamine;

2-{5-Chloro-2-[7-(2,2-difluoro-ethylamino)-6,7,8,9-tetrahydro-5H-benzocyclohepten-2-ylamino]-pyrimidin-4-ylamino}-3-fluoro-N-methyl-benzamide;

(1S,2S,3R,4R)-3-{5-Chloro-2-[7-(2,2-difluoro-ethylamino)-6,7,8,9-tetrahydro-5H-benzocyclohepten-2-ylamino]-pyrimidin-4-ylamino}-bicyclo[2.2.1]hept-5-ene-2-carboxylic;

7-[5-Chloro-4-(2-methoxy-4-morpholin-4-yl-phenylamino)-pyrimidin-2-ylamino]-1-isopropyl-1,3,4,5-tetrahydro-benzo[b]azepin-2-one;

N-{(1R,2R)-2-[5-Chloro-2-(1-isopropyl-2-oxo-2,3,4,5-tetrahydro-1H-benzo[b]azepin-7-ylamino)-pyrimidin-4-ylamino]-cyclohexyl}-methanesulfonamide;

3-[5-Chloro-2-(1-methyl-2-oxo-2,3,4,5-tetrahydro-1H-benzo[b]azepin-7-ylamino)-pyrimidin-4-ylamino]-N-methyl-benzamide;

3-[5-Chloro-2-(1-isopropyl-2-oxo-2,3,4,5-tetrahydro-1H-benzo[b]azepin-7-ylamino)-pyrimidin-4-ylamino]-bicyclo[2.2.1]hept-5-ene-2-carboxylic acid amide;

3-[5-Chloro-2-(1,5,5-trimethyl-2-oxo-2,3,4,5-tetrahydro-1H-benzo[b]azepin-7-ylamino)-pyrimidin-4-ylamino]-N-methyl-benzamide;

(1S,2S,3R,4R)-3-[5-Chloro-2-(7-morpholin-4-yl-6,7,8,9-tetrahydro-5H-benzocyclohepten-2-ylamino)-pyrimidin-4-ylamino]-bicyclo[2.2.1]hept-5-ene-2-carboxylic acid amide;

3-[5-Chloro-2-(5,5-dimethyl-2-oxo-2,3,4,5-tetrahydro-1H-benzo[b]azepin-7-ylamino)-pyrimidin-4-ylamino]-N-methyl-benzamide;

3-{5-Chloro-2-[3-(2-methoxy-ethyl)-2,3,4,5-tetrahydro-1H-benzo[d]azepin-7-ylamino]-pyrimidin-4-ylamino}-N-methyl-benzamide;

7-{5-Chloro-4-[2-methoxy-4-(4-methyl-piperazin-1-yl)-phenylamino]-pyrimidin-2-ylamino}-1-isopropyl-1,3,4,5-tetrahydro-benzo[b]azepin-2-one;

N-((1R,2R)-2-{5-Chloro-2-[7-(2,2-difluoro-ethylamino)-6,7,8,9-tetrahydro-5H-benzocyclohepten-2-ylamino]-pyrimidin-4-ylamino}-cyclohexyl)-methanesulfonamide;

N-((1R,2R)-2-{5-Chloro-2-[7-(2,2,2-trifluoro-ethylamino)-6,7,8,9-tetrahydro-5H-benzocyclohepten-2-ylamino]-pyrimidin-4-ylamino}-cyclohexyl)-methanesulfonamide;

(1S,2S,3R,4R)-3-{5-Chloro-2-[7-(2,2-difluoro-ethylamino)-6,7,8,9-tetrahydro-5H-benzocyclohepten-2-ylamino]-pyrimidin-4-ylamino}-bicyclo[2.2.1]hept-5-ene-2-carboxylic acid amide;

5-Chloro-N*2*-[7-(2,2-difluoro-ethylamino)-1-methoxy-6,7,8,9-tetrahydro-5H-benzocyclohepten-2-yl]-N*4*-methyl-N*4*-[2-(propane-2-sulfonyl)-phenyl]-pyrimidine-2,4-diamine;

(1S,2S,3R,4R)-3-{5-Chloro-2-[1-methoxy-7-(2,2,2-trifluoro-ethylamino)-6,7,8,9-tetrahydro-5H-benzocyclohepten-2-ylamino]-pyrimidin-4-ylamino}-bicyclo[2.2.1]hept-5-ene-2-carboxylic acid amide;

5-Chloro-N*2*-[1-methoxy-7-(2,2,2-trifluoro-ethylamino)-6,7,8,9-tetrahydro-5H-benzocyclohepten-2-yl]-N*4*-methyl-N*4*-[2-(propane-2-sulfonyl)-phenyl]-pyrimidine-2,4-diamine;

1S,2S,3R,4R)-3-[5-Chloro-2-(7-morpholin-4-yl-6,7,8,9-tetrahydro-5H-benzocyclohepten-2-ylamino)-pyrimidin-4-ylamino]-bicyclo[2.2.1]hept-5-ene-2-carboxylic acid amide;

1S,2S,3R,4R)-3-[5-Chloro-2-(7-morpholin-4-yl-6,7,8,9-tetrahydro-5H-benzocyclohepten-2-ylamino)-pyrimidin-4-ylamino]-bicyclo[2.2.1]hept-5-ene-2-carboxylic acid amide;

2-{5-Chloro-2-[7-(2,2-difluoro-ethylamino)-1-methoxy-6,7,8,9-tetrahydro-5H-benzocyclohepten-2-ylamino]-pyrimidin-4-ylamino}-N,N-dimethyl-benzenesulfonamide;

2-{5-Chloro-2-[1-methoxy-7-(2,2,2-trifluoro-ethylamino)-6,7,8,9-tetrahydro-5H-benzocyclohepten-2-ylamino]-pyrimidin-4-ylamino}-N,N-dimethyl-benzenesulfonamide;

N-((1R,2R)-2-{5-Chloro-2-[7-(2,2-difluoro-ethylamino)-6,7,8,9-tetrahydro-5H-benzocyclohepten-2-ylamino]-pyrimidin-4-ylamino}-cyclohexyl)-methanesulfonamide;

N-((1R,2R)-2-{5-Chloro-2-[7-(2,2-difluoro-ethylamino)-6,7,8,9-tetrahydro-5H-benzocyclohepten-2-ylamino]-pyrimidin-4-ylamino}-cyclohexyl)-methanesulfonamide;

N-((1R,2R)-2-{5-Chloro-2-[7-(2,2,2-trifluoro-ethylamino)-6,7,8,9-tetrahydro-5H-benzocyclohepten-2-ylamino]-pyrimidin-4-ylamino}-cyclohexyl)-methanesulfonamide;

N-((1R,2R)-2-{5-Chloro-2-[7-(2,2,2-trifluoro-ethylamino)-6,7,8,9-tetrahydro-5H-benzocyclohepten-2-ylamino]-pyrimidin-4-ylamino}-cyclohexyl)-methanesulfonamide;

25-Chloro-N*2*-[7-(2,2-difluoro-ethylamino)-1-methoxy-6,7,8,9-tetrahydro-5H-benzocyclohepten-2-yl]-N*4*-(2-pyrazol-1-yl-phenyl)-pyrimidine-2,4-diamine;

5-Chloro-N*2*-[1-methoxy-7-(2,2,2-trifluoro-ethylamino)-6,7,8,9-tetrahydro-5H-benzocyclohepten-2-yl]-N*4*-(2-pyrazol-1-yl-phenyl)-pyrimidine-2,4-diamine;

(1S,2S,3R,4R)-3-{5-Chloro-2-[1-methoxy-7-(2-methoxy-ethylamino)-6,7,8,9-tetrahydro-5H-benzocyclohepten-2-ylamino]-pyrimidin-4-ylamino}-bicyclo[2.2.1]hept-5-ene-2-carboxylic acid amide;

(1S,2S,3R,4R)-3-{5-Chloro-2-[1-methoxy-7-(2-methoxy-ethylamino)-6,7,8,9-tetrahydro-5H-benzocyclohepten-2-ylamino]-pyrimidin-4-ylamino}-bicyclo[2.2.1]hept-5-ene-2-carboxylic acid amide;

N-((1R,2R)-2-{5-Chloro-2-[1-methoxy-7-(2-methoxy-ethylamino)-6,7,8,9-tetrahydro-5H-benzocyclohepten-2-ylamino]-pyrimidin-4-ylamino}-cyclohexyl)-methanesulfonamide;

N-((1R,2R)-2-{5-Chloro-2-[1-methoxy-7-(2-methoxy-ethylamino)-6,7,8,9-tetrahydro-5H-benzocyclohepten-2-ylamino]-pyrimidin-4-ylamino}-cyclohexyl)-methanesulfonamide;

1-(2-{5-Chloro-2-[1-methoxy-7-(2-methoxy-ethylamino)-6,7,8,9-tetrahydro-5H-benzocyclohepten-2-ylamino]-pyrimidin-4-ylamino}-benzenesulfonyl)-pyrrolidin-3-ol;

1S,2S,3R,4R)-3-{5-Chloro-2-[7-(2-hydroxy-ethylamino)-1-methoxy-6,7,8,9-tetrahydro-5H-benzocyclohepten-2-ylamino]-pyrimidin-4-ylamino}-bicyclo[2.2.1]hept-5-ene-2-carboxylic acid amide;

(1S,2S,3R,4R)-3-{5-Chloro-2-[7-(2-hydroxy-ethylamino)-1-methoxy-6,7,8,9-tetrahydro-5H-benzocyclohepten-2-ylamino]-pyrimidin-4-ylamino}-bicyclo[2.2.1]hept-5-ene-2-carboxylic acid amide;

N-((1R,2R)-2-{5-Chloro-2-[7-(2-hydroxy-ethylamino)-1-methoxy-6,7,8,9-tetrahydro-5H-benzocyclohepten-2-ylamino]-pyrimidin-4-ylamino}-cyclohexyl)-methanesulfonamide;

N-((1R,2R)-2-{5-Chloro-2-[7-(2-hydroxy-ethylamino)-1-methoxy-6,7,8,9-tetrahydro-5H-benzocyclohepten-2-ylamino]-pyrimidin-4-ylamino}-cyclohexyl)-methanesulfonamide;

(1S,2S,3R,4R)-3-(5-Chloro-2-{1-methoxy-7-[(2-methoxy-ethyl)-methyl-amino]-6,7,8,9-tetrahydro-5H-benzocyclohepten-2-ylamino}-pyrimidin-4-ylamino)-bicyclo[2.2.1]hept-5-ene-2-carboxylic acid amide;

(1S,2S,3R,4R)-3-(5-Chloro-2-{1-methoxy-7-[(2-methoxy-ethyl)-methyl-amino]-6,7,8,9-tetrahydro-5H-benzocyclohepten-2-ylamino}-pyrimidin-4-ylamino)-bicyclo[2.2.1]hept-5-ene-2-carboxylic acid amide;

N-[(1R,2R)-2-(5-Chloro-2-{1-methoxy-7-[(2-methoxy-ethyl)-methyl-amino]-6,7,8,9-tetrahydro-5H-benzocyclohepten-2-ylamino}-pyrimidin-4-ylamino)-cyclohexyl]-methanesulfonamide;

1-(2-{5-Chloro-2-[7-(2-hydroxy-ethylamino)-1-methoxy-6,7,8,9-tetrahydro-5H-benzocyclohepten-2-ylamino]-pyrimidin-4-ylamino}-benzenesulfonyl)-pyrrolidin-3-ol;

2-(2-{5-Chloro-4-[2-(pyrrolidine-1-sulfonyl)-phenylamino]-pyrimidin-2-ylamino}-1-methoxy-6,7,8,9-tetrahydro-5H-benzocyclohepten-7-ylamino)-ethanol;

2-{2-[5-Chloro-4-(2-methoxy-4-morpholin-4-yl-phenylamino)-pyrimidin-2-ylamino]-1-methoxy-6,7,8,9-tetrahydro-5H-benzocyclohepten-7-ylamino}-ethanol;

N-((1R,2R)-2-{5-Chloro-2-[4-(2-methoxy-ethyl)-2,3,4,5-tetrahydro-benzo[f][1,4]oxazepin-7-ylamino]-pyrimidin-4-ylamino}-cyclohexyl)-methanesulfonamide;

5-Chloro-N*2*-(1,4-diethyl-2,3,4,5-tetrahydro-1H-benzo[e][1,4]diazepin-8-yl)-N*4*-(2-methoxy-4-morpholin-4-yl-phenyl)-pyrimidin-2,4-diamine;

2-[5-Chloro-2-(1,4-diethyl-2,3,4,5-tetrahydro-1H-benzo[e][1,4]diazepin-8-ylamino)-pyrimidin-4-ylamino]-benzoic acid 2-methoxy-ethylester;

(2-exo,3-exo)-3-[5-Chloro-2-(1,4-diethyl-2,3,4,5-tetrahydro-1H-benzo[e][1,4]diazepin-8-ylamino)-pyrimidin-4-ylamino]-bicyclo[2.2.1]hept-5-ene-2-carboxylic acid amide;

5-Chloro-N*2*-(1,4-diethyl-2,3,4,5-tetrahydro-1H-benzo[e][1,4]diazepin-8-yl)-N*4*-[2-(1-methyl-1H-imidazol-2-yl)-phenyl]-pyrimidine-2,4-diamine;

2-[5-Chloro-2-(1,4-diethyl-2,3,4,5-tetrahydro-1H-1,4-benzodiazepin-8-ylamino)-pyrimidin-4-ylamino]-3-fluoro-N-methyl-benzamide;

(2-exo,3-exo)-3-[5-Chloro-2-(1,4-diethyl-2,3,4,5-tetrahydro-1H-1,4-benzodiazepin-8-ylamino)-pyrimidin-4-ylamino]bicyclo[2.2.1]heptane-2-carboxylic acid amide;

2-[5-Chloro-2-(1,4-diethyl-2,3,4,5-tetrahydro-1H-1,4-benzodiazepin-8-ylamino)-pyrimidin-4-ylamino]-N-ethyl-benzamide;

5-Chloro-N*4*(5-chloro-2-methoxy-phenyl-N*2*-(1,4-diethyl-2,3,4,5-tetrahydro-1H-benzo[e][1,4]diazepin-8-yl)-pyrimidine)-2,4-diamine;

(1S,2S,3R,4R)-3[5-Chloro-2-(1,4-diethyl-2,3,4,5-tetrahydro-1H-1,4-benzodiazepin-8-ylamino)-pyrimidin-4-ylamino]-bicyclo[2.2.1]hept-5-ene-2-carboxylic acid amide;

5-Chloro-N*2*,N*4*-bis(1,4-diethyl-2,3,4,5-tetrahydro-1H-benzo[e][1,4]diazepin-8-yl)-pyrimidin-2,4-diamine;

8-[5-Chloro-2-(1,4-diethyl-2,3,4,5-tetrahydro-1H-benzo[e][1,4]diazepin-8-ylamino)-pyrimidin-4-ylamino]-1,4-diethyl-1,2,3,4-tetrahydro-benzo[e][1,4]diazepin-5-one;

2-{{7-[5-Chloro-4-[1,4-diethyl-2,3,4,5-tetrahydro-1H-benzo[e][1,4]diazepin-2-ylamino]-pyrimidin-2-ylamino}-8-methoxy-1,2,3,4-tetrahydro-benzo[d]azepin-3-yl-N,N-dimethyl-acetamide;

2-{7-[5-Chloro-4-(1,4-diethyl-5-oxo-2,3,4,5-tetrahydro-1H-benzo[e][1,4]diazepin-8-ylamino)-pyrimidin-2-ylamino]-8-methoxy-1,2,3,4-tetrahydro-benzo[d]azepin-3-yl}-N,N-dimethyl-acetamide;

5-Chloro-N(2)-(1,4-diethyl-2,3,4,5-tetrahydro-1H-benzo[e][1,4]diazepin-8-yl)-N(4)-(2-pyrazol-1-yl-phenyl)-pyrimidine-2,4-diamine;

8-[5-Chloro-4-(2-methoxy-4-morpholin-4-yl-phenylamino)-pyrimidin-2-ylamino]-1-ethyl-7-methoxy-4-(2-methoxy-ethyl)-1,3,4,5-tetrahydro-benzo[e][1,4]diazepin-2-one;

2-{8-[5-Chloro-4-(2-methoxy-4-morpholin-4-yl-phenylamino)-pyrimidin-2-ylamino]-1-ethyl-7-methoxy-2-oxo-1,2,3,5-tetrahydro-benzo[e][1,4]diazepin-4-yl}-N,N-dimethyl-acetamide;

5-Chloro-N(2)-(1,4-diethyl-2,3,4,5-tetrahydro-1H-benzo[e][1,4]diazepin-8-yl)-N(4)-[2-(propane-2-sulfonyl)-phenyl]-pyrimidine-2,4-diamine;

8-{5-Chloro-4-[2-(propane-2-sulfonyl)-phenylamino]-pyrimidin-2-ylamino}-1-ethyl-7-methoxy-1,3,4,5-tetrahydro-benzo[e][1,4]diazepin-2-one;

2-[5-Chloro-2-(1,4-diethyl-2,3,4,5-tetrahydro-1H-benzo[e][1,4]diazepin-8-ylamino)-pyrimidin-4-ylamino]-N,N-dimethyl-benzenesulfonamide;

{2-[5-Chloro-2-(1,4-diethyl-2,3,4,5-tetrahydro-1H-benzo[e][1,4]diazepin-8-ylamino)-pyrimidin-4-ylamino]-phenoxy}-acetonitrile;

5-Chloro-N(2)-(1,4-diethyl-2,3,4,5-tetrahydro-1H-benzo[e][1,4]diazepin-8-yl)-N(4)-(4-methoxy-2-pyrazol-1-yl-phenyl)-pyrimidine-2,4-diamine;

5-Chloro-N(2)-(1,4-diethyl-2,3,4,5-tetrahydro-1H-benzo[e][1,4]diazepin-8-yl)-N(4)-[8-(2-methoxy-ethyl)-6,7,8,9-tetrahydro-5-thia-8-aza-benzocyclohepten-2-yl]-pyrimidine-2,4-diamine;

2-({5-[5-Chloro-2-(1,4-diethyl-2,3,4,5-tetrahydro-1H-benzo[e][1,4]diazepin-8-ylamino)-pyrimidin-4-ylamino]-2-fluoro-benzyl}-ethyl-amino)-ethanol;

2-{7-[5-Chloro-4-(3-{[ethyl-(2-hydroxy-ethyl)-amino]-methyl}-4-fluoro-phenylamino)-pyrimidin-2-ylamino]-8-methoxy-1,2,4,5-tetrahydro-benzo[d]azepin-3-yl}-N,N-dimethyl-acetamide;

N,N-{(1R,2R)-2-[5-Chloro-2-(1,4-diethyl-7-methoxy-2-oxo-2,3,4,5-tetrahydro-1H-benzo[e][1,4]diazepin-8-ylamino)-pyrimidin-4-ylamino]-cyclohexyl}-methanesulfonamide;

8-[5-Chloro-4-(4-methoxy-2-pyrazol-1-yl-phenylamino)-pyrimidin-2-ylamino]-1,4-diethyl-7-methoxy-1,3,4,5-tetrahydro-benzo[e][1,4]diazepin-2-one;

2-[5-Chloro-2-(1,4-diethyl-7-methoxy-2-oxo-2,3,4,5-tetrahydro-1H-benzo[e][1,4]diazepin-8-ylamino)-pyrimidin-4-ylamino]-N,Ndimethyl-benzenesulfonamide;

(1S,2,3R,4R)-3-[5-Chloro-2-(1,4-diethyl-7-methoxy-2-oxo-2,3,4,5-tetrahydro-1H-benzo[e][1,4]diazepin-8-ylamino)-pyrimidin-4-ylamino]-bicyclo(2.2.1)hept-5-ene-2-carboxylic acid amide;

2-([5-[5-Chloro-2-(1-methoxy-7-morpholin-4-yl-6,7,8,9-tetrahydro-5H-benzocyclohepten-2-ylamino)-pyrimidin-4-ylamino]-2-fluoro-benzyl}-ethylamino)-ethanol;

(1S,2S,3R,4R)-3-[5-Chloro-2-(4-ethyl-7-methoxy-2-oxo-2,3,4,5-tetrahydro-1H-benzo[e][1,4]diazepin-8-ylamino]bicyclo[2.2.1]hept-5-ene-2-carboxylic acid amide;

8-[5-Chloro-4-(4-methoxy-2-pyrazol-1-yl-phenylamino)-pyrimidin-2-ylamino]-4-ethyl-7-methoxy-1-methyl-1,3,4,5-tetrahydro-benzo[e][1,4]diazepin-2-one;

(1S,2S,3R,4R)-3-[5-Chloro-2-(7-methoxy-1-methyl-2-oxo-2,3,4,5-tetrahydro-1H-benzo[e][1,4]diazepin-8-ylamino)-pyrimidin-4-ylamino]-bicyclo[2.2.1]hept-5-ene-2-carboxylic acid amide;

N-[(1R,2R)-2-[5-Chloro-2-(4-ethyl-7-methoxy-1-methyl-2-oxo-2,3,4,5-tetrahydro-1H-benzo[e][1,4]diazepin-8-ylamino)-pyrimidin-4-ylamino]-cyclohexyl}-methanesulfonamide;

(1S,2S,3R,4R)-3-[5-Chloro-2-(4-cyanomethyl-7-methoxy-1-methyl-2-oxo-2,3,4,5-tetrahydro-1H-benzo[e][1,4]diazepin-8-ylamino)-pyrimidin-4-ylamino]-bicyclo(2.2.1)hept-5-ene-2-carboxylic acid amide;

N-{(1R,2R)-2-[5-Chloro-2-(4-cyclopropylmethyl-7-methoxy-1-methyl-2-oxo-2,3,4,5-tetrahydro-1H-benzo[e][1,4]diazepin-8-ylamino)-pyrimidin-4-ylamino]-cyclohexyl}-methanesulfonamide;

(1S,2S,3R,4R)-3-[5-Chloro-2-[4-cyclopropylmethyl-7-methoxy-2,3,4,5-tetrahydro-1H-benzo[e][1,4]diazepin-8-ylamino)-pyrimidin-4-ylamino]-bicyclo(2.2.1)hept-5-ene-2-carboxylic acid amide;

8-[5-Chloro-4-(4-methoxy-2-pyrazol-1-yl-phenylamino)-pyrimidin-2-ylamino]-cyclopropylmethyl-7-methoxy-1-methyl-1,3,4,5-tetrahydro-benzo[e][1,4]diazepin-2-one;

8-(5-Chloro-4-{3-[(2-hydroxy-ethylamino)-methyl]-4-methoxy-phenylamino}-pyrimidin-2-ylamino)-4-ethyl-7-methoxy-1-methyl-1,3,4,5-tetrahydro-benzo[e][1,4]diazepin-2-one;

6-{5-Chloro-2-[3-methoxy-7-(2-methoxy-ethylamino)-6,7,8,9-tetrahydro-5H-benzocyclohepten-2-ylamino]-pyrimidin-4-ylamino}-4-methanesulfonyl-7-methoxy-1,3,4,5-tetrahydro-benzo[e][1,4]diazepin-2-one;

2-{7-[5-Chloro-4-(4-methanesulfonyl-7-methoxy-2-oxo-2,3,4,5-tetrahydro-1H-benzo[e][1,4]diazepin-6-ylamino)-pyrimidin-2-ylamino]-8-methoxy-1,2,4,5-tetrahydro-benzo[d]azepin-3-yl}-N,Ndimethyl-acetamide;

5-Chloro-N*2*-[3-(2,2-difluoro-ethyl)-8-methoxy-2,3,4,5-tetrahydro-1H-benzo[d]azepin-7-yl]-N*4*-(2-methoxy-4-morpholin-4-yl-phenyl)-pyrimidine-2,4-diamine;

N-((1R,2R)-2-{5-Chloro-2-[3-(2,2-difluoro-ethyl)-8-methoxy-2,3,4,5-tetrahydro-1H-benzo[d]azepin-7-ylamino]-pyrimidin-4-ylamino}-cyclohexyl)-methanesulfonamide;

(2-exo,3-exo)-3-{5-Chloro-2-[3-(2,2-difluoro-ethyl)-8-methoxy-2,3,4,5-tetrahydro-1H-benzo[d]azepin-7-ylamino]-pyrimidin-4-ylamino}-bicyclo[2.2.1]hept-5-ene-2-carboxylic acid amide;

5-Chloro-N*2*-[3-(2,2-difluoro-ethyl)-8-methoxy-2,3,4,5-tetrahydro-1H-benzo[d]azepin-7-yl]-N*4*-[2-methoxy-4-(4-methyl-piperazin-1-yl)-phenyl]-pyrimidine-2,4-diamine;

5-Chloro-N*2*-[3-(2,2-difluoro-ethyl)-8-methoxy-2,3,4,5-tetrahydro-1H-benzo[d]azepin-7-yl]-N*4*-[3-methyl-4-(4-methyl-piperazin-1-yl)-phenyl]-pyrimidine-2,4-diamine;

2-{5-Chloro-2-[3-(2,2-difluoro-ethyl)-8-methoxy-2,3,4,5-tetrahydro-1H-benzo[d]azepin-7-ylamino]-pyrimidin-4-ylamino}-N-methyl-benzamide;

2-{5-Chloro-2-[3-(2,2-difluoro-ethyl)-8-methoxy-2,3,4,5-tetrahydro-1H-benzo[d]azepin-7-ylamino]-pyrimidin-4-ylamino}-N-ethyl-benzamide;

5-Chloro-N*4*-(5-chloro-2-methoxy-phenyl)-N*2*-[3-(2,2-difluoro-ethyl)-8-methoxy-2,3,4,5-tetrahydro-1H-benzo[d]azepin-7-yl]-pyrimidine-2,4-diamine;

(2-exo,3-exo)-3-{2-[3-(2,2-Difluoro-ethyl)-8-methoxy-2,3,4,5-tetrahydro-1H-benzo[d]azepin-7-ylamino]-5-fluoro-pyrimidin-4-ylamino}-bicyclo[2.2.1]hept-5-ene-2-carboxylic acid amide;

2-(7-{5-Chloro-4-[2-methoxy-4-(4-methyl-piperazin-1-yl)-phenylamino]-pyrimidin-2-ylamino}-8-methoxy-1,2,4,5-tetrahydro-benzo[d]azepin-3-yl)-N,N-dimethyl-acetamide;

5-Chloro-N*2*-[3-(2-methanesulfonyl-ethyl)-8-methoxy-2,3,4,5-tetrahydro-1H-benzo[d]azepin-7-yl]-N*4*-[2-methoxy-4-(4-methyl-piperazin-1-yl)-phenyl]-pyrimidine-2,4-diamine;

7-{5-Chloro-4-[2-methoxy-4-(4-methyl-piperazin-1-yl)-phenylamino]-pyrimidin-2-ylamino}-3-ethyl-8-methoxy-1,3,4,5-tetrahydro-benzo[d]azepin-2-one;

(1S,2S,3R,4R)-3-[5-Chloro-2-(3-ethyl-8-methoxy-2,3,4,5-tetrahydro-1H-benzo[d]azepin-7-ylamino)-pyrimidin-4-ylamino]-bicyclo[2.2.1]hept-5-ene-2-carboxylic acid amide;

(1S,2S,3R,4R)-3-[5-Chloro-2-(8-methoxy-3-propyl-2,3,4,5-tetrahydro-1H-benzo[d]azepin-7-ylamino)-pyrimidin-4-ylamino]-bicyclo[2.2.1]hept-5-ene-2-carboxylic acid amide;

(1S,2S,3R,4R)-3-[5-Chloro-2-(3-cyclopropylmethyl-8-methoxy-2,3,4,5-tetrahydro-1H-benzo[d]azepin-7-ylamino)-pyrimidin-4-ylamino]-bicyclo[2.2.1]hept-5-ene-2-carboxylic acid amide;

(1S,2S,3R,4R)-3-[5-Chloro-2-(3-isopropyl-8-methoxy-2,3,4,5-tetrahydro-1H-benzo[d]azepin-7-ylamino)-pyrimidin-4-ylamino]-bicyclo[2.2.1]hept-5-ene-2-carboxylic acid amide;

2-{5-Chloro-2-[3-(2,2-difluoro-ethyl)-8-methoxy-2,3,4,5-tetrahydro-1H-benzo[d]azepin-7-ylamino]-pyrimidin-4-ylamino}-N-ethyl-3-fluoro-benzamide;

7-{5-Chloro-4-[2-methoxy-4-(4-methyl-piperazin-1-yl)-phenylamino]-pyrimidin-2-ylamino}-8-methoxy-1,3,4,5-tetrahydro-benzo[d]azepin-2-one;

5-Chloro-N*2*-[3-(2,2-difluoro-propyl)-8-methoxy-2,3,4,5-tetrahydro-1H-benzo[d]azepin-7-yl]-N*4*-[3-methyl-4-(4-methyl-piperazin-1-yl)-phenyl]-pyrimidine-2,4-diamine;

5-Chloro-N*2*-[3-(2,2-difluoro-propyl)-8-methoxy-2,3,4,5-tetrahydro-1H-benzo[d]azepin-7-yl]-N*4*-(2-methoxy-4-morpholin-4-yl-phenyl)-pyrimidine-2,4-diamine;

5-Chloro-N*2*-[3-(2,2-difluoro-propyl)-8-methoxy-2,3,4,5-tetrahydro-1H-benzo[d]azepin-7-yl]-N*4*-[2-methoxy-4-(4-methyl-piperazin-1-yl)-phenyl]-pyrimidine-2,4-diamine;

(1S,2S,3R,4R)-3-{5-Chloro-2-[3-(2,2-difluoro-propyl)-8-methoxy-2,3,4,5-tetrahydro-1H-benzo[d]azepin-7-ylamino]-pyrimidin-4-ylamino}-bicyclo[2.2.1]hept-5-ene-2-carboxylic acid amide;

2-(7-{5-Chloro-4-[2-methoxy-4-(4-methyl-piperazin-1-yl)-phenylamino]-pyrimidin-2-ylamino}-8-methoxy-1,2,4,5-tetrahydro-benzo[d]azepin-3-yl)-N-methyl-acetamide;

N-((1R,2R)-2-{5-Chloro-2-[3-(2,2-difluoro-propyl)-8-methoxy-2,3,4,5-tetrahydro-1H-benzo[d]azepin-7-ylamino]-pyrimidin-4-ylamino}-cyclohexyl)-methanesulfonamide;

5-Chloro-N*4*-(5-chloro-2-methoxy-phenyl)-N*2*-[3-(2,2-difluoro-propyl)-8-methoxy-2,3,4,5-tetrahydro-1H-benzo[d]azepin-7-yl]-pyrimidine-2,4-diamine;

2-{5-Chloro-2-[3-(2,2-difluoro-propyl)-8-methoxy-2,3,4,5-tetrahydro-1H-benzo[d]azepin-7-ylamino]-pyrimidin-4-ylamino}-N-methyl-benzamide;

2-{5-Chloro-2-[3-(2,2-difluoro-propyl)-8-methoxy-2,3,4,5-tetrahydro-1H-benzo[d]azepin-7-ylamino]-pyrimidin-4-ylamino}-N-ethyl-benzamide;

2-{5-Chloro-2-[3-(2,2-difluoro-propyl)-8-methoxy-2,3,4,5-tetrahydro-1H-benzo[d]azepin-7-ylamino]-pyrimidin-4-ylamino}-N-ethyl-3-fluoro-benzamide;

5-Chloro-N*2*-[8-methoxy-3-(2-methoxy-ethyl)-2,3,4,5-tetrahydro-1H-benzo[d]azepin-7-yl]-N*4*-[2-methoxy-4-(4-methyl-piperazin-1-yl)-phenyl]-pyrimidine-2,4-diamine;

2-(7-{5-Chloro-4-[3-methyl-4-(4-methyl-piperazin-1-yl)-phenylamino]-pyrimidin-2-ylamino}-8-methoxy-1,2,4,5-tetrahydro-benzo[d]azepin-3-yl)-N,N-dimethyl-acetamide;

2-(7-{5-Fluoro-4-[2-methoxy-4-(4-methyl-piperazin-1-yl)-phenylamino]-pyrimidin-2-ylamino}-8-methoxy-1,2,4,5-tetrahydro-benzo[d]azepin-3-yl)-N,N-dimethyl-acetamide;

2-(7-{5-Chloro-4-[2-methoxy-4-(2-oxa-5-aza-bicyclo[2.2.1]hept-5-yl)-phenylamino]-pyrimidin-2-ylamino}-8-methoxy-1,2,4,5-tetrahydro-benzo[d]azepin-3-yl)-N,N-dimethyl-acetamide;

2-(7-{5-Chloro-4-[4-(5-ethyl-2,5-diaza-bicyclo[2.2.1]hept-2-yl)-2-methoxy-phenylamino]-pyrimidin-2-ylamino}-8-methoxy-1,2,4,5-tetrahydro-benzo[d]azepin-3-yl)-N,N-dimethyl-acetamide;

2-{7-[5-Chloro-4-(3-methyl-4-morpholin-4-yl-phenylamino)-pyrimidin-2-ylamino]-8-methoxy-1,2,4,5-tetrahydro-benzo[d]azepin-3-yl}-N,N-dimethyl-acetamide;

2-(7-{5-Fluoro-4-[2-methoxy-4-(4-methyl-piperazin-1-yl)-phenylamino]-pyrimidin-2-ylamino}-8-methoxy-1,2,4,5-tetrahydro-benzo[d]azepin-3-yl)-N-methyl-acetamide;

2-(7-{5-Chloro-4-[3-methyl-4-(4-methyl-piperazin-1-yl)-phenylamino]-pyrimidin-2-ylamino}-8-methoxy-1,2,4,5-tetrahydro-benzo[d]azepin-3-yl)-N-methyl-acetamide;

2-{7-[5-Chloro-4-(2-methoxy-4-morpholin-4-yl-phenylamino)-pyrimidin-2-ylamino]-8-methoxy-1,2,4,5-tetrahydro-benzo[d]azepin-3-yl}-acetamide;

{7-[5-Chloro-4-(2-methoxy-4-morpholin-4-yl-phenylamino)-pyrimidin-2-ylamino]-8-methoxy-1,2,4,5-tetrahydro-benzo[d]azepin-3-yl}-acetic acid isopropyl ester;

2-{7-[5-Chloro-4-(2-methyl-4-morpholin-4-yl-phenylamino)-pyrimidin-2-ylamino]-8-methoxy-1,2,4,5-tetrahydro-benzo[d]azepin-3-yl}-N,N-dimethyl-acetamide;

2-(7-{5-Chloro-4-[2-methyl-4-(4-methyl-piperazin-1-yl)-phenylamino]-pyrimidin-2-ylamino}-8-methoxy-1,2,4,5-tetrahydro-benzo[d]azepin-3-yl)-N,N-dimethyl-acetamide;

2-{7-[5-Chloro-4-(3-methoxy-4-morpholin-4-yl-phenylamino)-pyrimidin-2-ylamino]-8-methoxy-1,2,4,5-tetrahydro-benzo[d]azepin-3-yl}-N,N-dimethyl-acetamide;

2-(7-{5-Chloro-4-[3-methoxy-4-(4-methyl-piperazin-1-yl)-phenylamino]-pyrimidin-2-ylamino}-8-methoxy-1,2,4,5-tetrahydro-benzo[d]azepin-3-yl)-N,N-dimethyl-acetamide;

5-Fluoro-N*2*-[3-(2-methanesulfonyl-ethyl)-8-methoxy-2,3,4,5-tetrahydro-1H-benzo[d]azepin-7-yl]-N*4*-[2-methoxy-4-(4-methyl-piperazin-1-yl)-phenyl]-pyrimidine-2,4-diamine;

(1S,2S,3R,4R)-3-{5-Chloro-2-[3-(2,2-difluoro-ethyl)-8-methoxy-2,3,4,5-tetrahydro-1H-benzo[d]azepin-7-ylamino]-pyrimidin-4-ylamino}-bicyclo[2.2.1]hept-5-ene-2-carboxylic acid amide;

2-(7-{5-Chloro-4-[2-methoxy-4-(4-methyl-piperazin-1-yl)-phenylamino]-pyrimidin-2-ylamino}-8-methoxy-1,2,4,5-tetrahydro-benzo[d]azepin-3-yl)-acetamide;

2-{7-[5-Fluoro-4-(2-methoxy-4-morpholin-4-yl-phenylamino)-pyrimidin-2-ylamino]-8-methoxy-1,2,4,5-tetrahydro-benzo[d]azepin-3-yl}-N,N-dimethyl-acetamide;

2-{7-[5-Fluoro-4-(2-methoxy-4-morpholin-4-yl-phenylamino)-pyrimidin-2-ylamino]-8-methoxy-1,2,4,5-tetrahydro-benzo[d]azepin-3-yl}-N-methyl-acetamide;

2-{7-[5-Fluoro-4-(2-methoxy-4-morpholin-4-yl-phenylamino)-pyrimidin-2-ylamino]-8-methoxy-1,2,4,5-tetrahydro-benzo[d]azepin-3-yl}-acetamide;

{7-[5-Fluoro-4-(2-methoxy-4-morpholin-4-yl-phenylamino)-pyrimidin-2-ylamino]-8-methoxy-1,2,4,5-tetrahydro-benzo[d]azepin-3-yl}-acetic acid isopropyl ester;

2-{7-[5-Chloro-4-(2,4-dimethoxy-phenylamino)-pyrimidin-2-ylamino]-8-methoxy-1,2,4,5-tetrahydro-benzo[d]azepin-3-yl}-N,N-dimethyl-acetamide;

(1S,2S,3R,4R)-3-[2-(3-Carbamoylmethyl-8-methoxy-2,3,4,5-tetrahydro-1H-benzo[d]azepin-7-ylamino)-5-chloro-pyrimidin-4-ylamino]-bicyclo[2.2.1]hept-5-ene-2-carboxylic acid amide;

5-Chloro-N*2*-[8-methoxy-3-(2-methoxy-1-methoxymethyl-ethyl)-2,3,4,5-tetrahydro-1H-benzo[d]azepin-7-yl]-N*4*-(2-methoxy-4-morpholin-4-yl-phenyl)-pyrimidine-2,4-diamine;

(1S,2S,3R,4R)-3-{5-Chloro-2-[8-methoxy-3-(2-methoxy-1-methoxymethyl-ethyl)-2,3,4,5-tetrahydro-1H-benzo[d]azepin-7-ylamino]-pyrimidin-4-ylamino}-bicyclo[2.2.1]hept-5-ene-2-carboxylic acid amide;

N-((1R,2R)-2-{5-Chloro-2-[8-methoxy-3-(2-methoxy-1-methoxymethyl-ethyl)-2,3,4,5-tetrahydro-1H-benzo[d]azepin-7-ylamino]-pyrimidin-4-ylamino}-cyclohexyl)-methanesulfonamide;

5-Chloro-N*2*-[8-methoxy-3-(2-methoxy-1-methoxymethyl-ethyl)-2,3,4,5-tetrahydro-1H-benzo[d]azepin-7-yl]-N*4*-[2-(propane-2-sulfonyl)-phenyl]-pyrimidine-2,4-diamine;

2-{5-Chloro-2-[8-methoxy-3-(2-methoxy-1-methoxymethyl-ethyl)-2,3,4,5-tetrahydro-1H-benzo[d]azepin-7-ylamino]-pyrimidin-4-ylamino}-N,N-dimethyl-benzenesulfonamide;

2-[7-(5-Chloro-4-{2-methoxy-4-[4-(4-methyl-piperazin-1-yl)-piperidin-1-yl]-phenylamino}-pyrimidin-2-ylamino)-8-methoxy-1,2,4,5-tetrahydro-benzo[d]azepin-3-yl]-N,N-dimethyl-acetamide;

2-{7-[5-Chloro-4-(2-dimethylsulfamoyl-4-methoxy-phenylamino)-pyrimidin-2-ylamino]-8-methoxy-1,2,4,5-tetrahydro-benzo[d]azepin-3-yl}-N,N-dimethyl-acetamide;

2-{7-[5-Chloro-4-(2-methanesulfonylamino-4-methoxy-phenylamino)-pyrimidin-2-ylamino]-8-methoxy-1,2,4,5-tetrahydro-benzo[d]azepin-3-yl}-N,N-dimethyl-acetamide;

2-{5-Chloro-2-[3-(2,2-difluoro-ethyl)-8-methoxy-2,3,4,5-tetrahydro-1H-benzo[d]azepin-7-ylamino]-pyrimidin-4-ylamino}-N,N-dimethyl-benzenesulfonamide;

5-Chloro-N*2*-[3-(2,2-difluoro-ethyl)-8-methoxy-2,3,4,5-tetrahydro-1H-benzo[d]azepin-7-yl]-N*4*-(2-pyrazol-1-yl-phenyl)-pyrimidine-2,4-diamine;

2-{5-Chloro-2-[3-(2,2-difluoro-propyl)-8-methoxy-2,3,4,5-tetrahydro-1H-benzo[d]azepin-7-ylamino]-pyrimidin-4-ylamino}-N,N-dimethyl-benzenesulfonamide;

5-Chloro-N*2*-[3-(2,2-difluoro-propyl)-8-methoxy-2,3,4,5-tetrahydro-1H-benzo[d]azepin-7-yl]-N*4*-(2-pyrazol-1-yl-phenyl)-pyrimidine-2,4-diamine;

2-{7-[5-Chloro-4-(2-dimethylamino-4-methoxy-phenylamino)-pyrimidin-2-ylamino]-8-methoxy-1,2,4,5-tetrahydro-benzo[d]azepin-3-yl}-N,N-dimethyl-acetamide;

5-Chloro-N*2*-[3-(2,2-difluoro-ethyl)-8-methoxy-2,3,4,5-tetrahydro-1H-benzo[d]azepin-7-yl]-N*4*-[2-(propane-2-sulfonyl)-phenyl]-pyrimidine-2,4-diamine;

5-Chloro-N*2*-[3-(2,2-difluoro-propyl)-8-methoxy-2,3,4,5-tetrahydro-1H-benzo[d]azepin-7-yl]-N*4*-[2-(propane-2-sulfonyl)-phenyl]-pyrimidine-2,4-diamine;

2-{7-[5-Chloro-4-(4-methoxy-2-morpholin-4-yl-phenylamino)-pyrimidin-2-ylamino]-8-methoxy-1,2,4,5-tetrahydro-benzo[d]azepin-3-yl}-N,N-dimethyl-acetamide;

2-{7-[5-Chloro-4-(2-dimethylsulfamoyl-4-methyl-phenylamino)-pyrimidin-2-ylamino]-8-methoxy-1,2,4,5-tetrahydro-benzo[d]azepin-3-yl}-N,N-dimethyl-acetamide;

2-{7-[5-Chloro-4-(2-dimethylsulfamoyl-4-fluoro-phenylamino)-pyrimidin-2-ylamino]-8-methoxy-1,2,4,5-tetrahydro-benzo[d]azepin-3-yl}-N,N-dimethyl-acetamide;

2-{7-[5-Chloro-4-(4-chloro-2-dimethylsulfamoyl-phenylamino)-pyrimidin-2-ylamino]-8-methoxy-1,2,4,5-tetrahydro-benzo[d]azepin-3-yl}-N,N-dimethyl-acetamide;

2-{7-[5-Chloro-4-(4-dimethylamino-2-dimethylsulfamoyl-phenylamino)-pyrimidin-2-ylamino]-8-methoxy-1,2,4,5-tetrahydro-benzo[d]azepin-3-yl}-N,N-dimethyl-acetamide;

2-{7-[5-Chloro-4-(2-dimethylsulfamoyl-4-morpholin-4-yl-phenylamino)-pyrimidin-2-ylamino]-8-methoxy-1,2,4,5-tetrahydro-benzo[d]azepin-3-yl}-N,N-dimethyl-acetamide;

2-[7-(5-Chloro-4-{2-methoxy-4-[4-(1-methyl-piperidin-4-yl)-piperazin-1-yl]-phenylamino}-pyrimidin-2-ylamino)-8-methoxy-1,2,4,5-tetrahydro-benzo[d]azepin-3-yl]-N,N-dimethyl-acetamide;

2-(7-{5-Chloro-4-[2-(morpholine-4-sulfonyl)-phenylamino]-pyrimidin-2-ylamino}-8-methoxy-1,2,4,5-tetrahydro-benzo[d]azepin-3-yl)-N,N-dimethyl-acetamide;

2-(7-{5-Chloro-4-[2-(4-methyl-piperazine-1-sulfonyl)-phenylamino]-pyrimidin-2-ylamino}-8-methoxy-1,2,4,5-tetrahydro-benzo[d]azepin-3-yl)-N,N-dimethyl-acetamide;

5-Chloro-2-{5-chloro-2-[8-methoxy-3-(2-methoxy-1-methoxymethyl-ethyl)-2,3,4,5-tetrahydro-1H-benzo[d]azepin-7-ylamino]-pyrimidin-4-ylamino}-N,N-dimethyl-benzenesulfonamide;

5-Chloro-2-{5-chloro-2-[8-methoxy-3-(2-methoxy-ethyl)-2,3,4,5-tetrahydro-1H-benzo[d]azepin-7-ylamino]-pyrimidin-4-ylamino}-N,N-dimethyl-benzenesulfonamide;

5-Chloro-2-{5-chloro-2-[3-(2-hydroxy-ethyl)-8-methoxy-2,3,4,5-tetrahydro-1H-benzo[d]azepin-7-ylamino]-pyrimidin-4-ylamino}-N,N-dimethyl-benzenesulfonamide;

5-Chloro-2-{5-chloro-2-[8-methoxy-3-(2-morpholin-4-yl-2-oxo-ethyl)-2,3,4,5-tetrahydro-1H-benzo[d]azepin-7-ylamino]-pyrimidin-4-ylamino}-N,N-dimethyl-benzenesulfonamide;

5-Chloro-2-(5-chloro-2-{8-methoxy-3-[2-(4-methyl-piperazin-1-yl)-2-oxo-ethyl]-2,3,4,5-tetrahydro-1H-benzo[d]azepin-7-ylamino}-pyrimidin-4-ylamino)-N,N-dimethyl-benzenesulfonamide;

2-{7-[5-Chloro-4-(2-dimethylsulfamoyl-4-trifluoromethyl-phenylamino)-pyrimidin-2-ylamino]-8-methoxy-1,2,4,5-tetrahydro-benzo[d]azepin-3-yl}-N,N-dimethyl-acetamide;

5-Chloro-N*2*-[8-methoxy-3-(2-methoxy-1-methoxymethyl-ethyl)-2,3,4,5-tetrahydro-1H-benzo[d]azepin-7-yl]-N*4*-[2-(pyrrolidine-1-sulfonyl)-phenyl]-pyrimidine-2,4-diamine;

2-(7-{5-Chloro-4-[2-((R)-3-dimethylamino-pyrrolidine-1-sulfonyl)-phenylamino]-pyrimidin-2-ylamino}-8-methoxy-1,2,4,5-tetrahydro-benzo[d]azepin-3-yl)-N,N-dimethyl-acetamide;

2-(7-{5-Chloro-4-[2-((S)-3-dimethylamino-pyrrolidine-1-sulfonyl)-phenylamino]-pyrimidin-2-ylamino}-8-methoxy-1,2,4,5-tetrahydro-benzo[d]azepin-3-yl)-N,N-dimethyl-acetamide;

2-{1-[5-Chloro-2-(3-dimethylcarbamoylmethyl-8-methoxy-2,3,4,5-tetrahydro-1H-benzo[d]azepin-7-ylamino)-pyrimidin-4-ylamino]-cyclohexyl}-acetamide;

2-(1-{5-Chloro-2-[8-methoxy-3-(2-methoxy-1-methoxymethyl-ethyl)-2,3,4,5-tetrahydro-1H-benzo[d]azepin-7-ylamino]-pyrimidin-4-ylamino}-cyclohexyl)-acetamide;

2-(1-{5-Chloro-2-[3-(2-hydroxy-ethyl)-8-methoxy-2,3,4,5-tetrahydro-1H-benzo[d]azepin-7-ylamino]-pyrimidin-4-ylamino}-cyclohexyl)-acetamide;

2-[5-Chloro-2-(1-ethyl-5,5-dimethyl-2-oxo-2,3,4,5-tetrahydro-1H-benzo[b]azepin-8-ylamino)-pyrimidin-4-ylamino]-5-dimethylamino-N,N-dimethyl-benzenesulfonamide;

2-[5-Chloro-2-(1-ethyl-5,5-dimethyl-2-oxo-2,3,4,5-tetrahydro-1H-benzo[b]azepin-8-ylamino)-pyrimidin-4-ylamino]-N,N-dimethyl-5-morpholin-4-yl-benzenesulfonamide;

2-{5-Chloro-2-[3-(2-methoxy-ethyl)-2,3,4,5-tetrahydro-1H-benzo[d]azepin-7-ylamino]-pyrimidin-4-ylamino}-5-dimethylamino-N,N-dimethyl-benzenesulfonamide;

2-{5-Chloro-2-[3-(2-methoxy-ethyl)-2,3,4,5-tetrahydro-1H-benzo[d]azepin-7-ylamino]-pyrimidin-4-ylamino}-N,N-dimethyl-5-morpholin-4-yl-benzenesulfonamide;

5-Chloro-N(2)-[8-methoxy-3-(2-methoxy-ethyl)-2,3,4,5-tetrahydro-1H-benzo[d]azepin-7-yl]-N(4)-[2-((S)-3-methyl-pyrrolidine-1-sulfonyl)-phenyl]-pyrimidine-2,4-diamine;

2-(7-{5-Chloro-4-[2-((S)-3-methyl-pyrrolidine-1-sulfonyl)-phenylamino]-pyrimidin-2-ylamino}-8-methoxy-1,2,4,5-tetrahydro-benzo[d]azepin-3-yl)-ethanol;

2-(7-{5-Chloro-4-[2-((S)-3-methyl-pyrrolidine-1-sulfonyl)-phenylamino]-pyrimidin-2-ylamino}-8-methoxy-1,2,4,5-tetrahydro-benzo[d]azepin-3-yl)-N,N-dimethyl-acetamide;

5-Chloro-N*4*-(2-methoxy-4-morpholin-4-yl-phenyl)-N*2*-(7-morpholin-4-yl-6,7,8,9-tetrahydro-5H-benzocyclohepten-2-yl)-pyrimidine-2,4-diamine;

2-[5-Chloro-2-(7-morpholin-4-yl-6,7,8,9-tetrahydro-5H-benzocyclohepten-2-ylamino)-pyrimidin-4-ylamino]-N-ethyl-benzamide;

3-[5-Chloro-2-(7-morpholin-4-yl-6,7,8,9-tetrahydro-5H-benzocyclohepten-2-ylamino)-pyrimidin-4-ylamino]-bicyclo[2.2.1]hept-5-ene-2-carboxylic acid amide;

2-[5-Chloro-2-(1-methoxy-7-oxo-6,7,8,9-tetrahydro-5H-benzocyclohepten-2-ylamino)-pyrimidin-4-ylamino]-N-methyl-benzamide;

(1S,2S,3R,4R)-3-[5-Chloro-2-(1-methoxy-7-oxo-6,7,8,9-tetrahydro-5H-benzocyclohepten-2-ylamino)-pyrimidin-4-ylamino]-bicyclo[2.2.1]hept-5-ene-2-carboxylic acid amide;

2-[5-Chloro-2-(1-methyl-2-oxo-2,3,4,5-tetrahydro-1H-benzo[b]azepin-7-ylamino)-pyrimidin-4-ylamino]-N-(2-cyano-ethyl)-benzamide;

(1S,2S,3R,4R)-3-[5-Chloro-2-((R)-1-methoxy-7-morpholin-4-yl-6,7,8,9-tetrahydro-5H-benzocyclohepten-2-ylamino)-pyrimidin-4-ylamino]-bicyclo[2.2.1]hept-5-ene-2-carboxylic acid amide;

(1S,2S,3R,4R)-3-[5-Chloro-2-((S)-1-methoxy-7-morpholin-4-yl-6,7,8,9-tetrahydro-5H-benzocyclohepten-2-ylamino)-pyrimidin-4-ylamino]-bicyclo[2.2.1]hept-5-ene-2-carboxylic acid amide;

5-Chloro-N*2*-(1-methoxy-7-morpholin-4-yl-6,7,8,9-tetrahydro-5H-benzocyclohepten-2-yl)-N*4*-[2-(propane-2-sulfonyl)-phenyl]-pyrimidine-2,4-diamine;

N-{(1R,2R)-2-[5-Chloro-2-(1-methoxy-7-morpholin-4-yl-6,7,8,9-tetrahydro-5H-benzocyclohepten-2-ylamino)-pyrimidin-4-ylamino]-cyclohexyl}-methanesulfonamide;

N-[(1R,2R)-2-(5-Chloro-2-{7-[4-(4-methyl-piperazin-1-yl)-piperidin-1-yl]-6,7,8,9-tetrahydro-5H-benzocyclohepten-2-ylamino}-pyrimidin-4-ylamino)-cyclohexyl]-methanesulfonamide;

(1S,2S,3R,4R)-3-(5-Chloro-2-{7-[4-(4-methyl-piperazin-1-yl)-piperidin-1-yl]-6,7,8,9-tetrahydro-5H-benzocyclohepten-2-ylamino}-pyrimidin-4-ylamino)-bicyclo[2.2.1]hept-5-ene-2-carboxylic acid amide;

N-((1R,2R)-2-{5-Chloro-2-[7-(4-methyl-piperazin-1-yl)-6,7,8,9-tetrahydro-5H-benzocyclohepten-2-ylamino]-pyrimidin-4-ylamino}-cyclohexyl)-methanesulfonamide;

2-[5-Chloro-2-(1-methoxy-7-morpholin-4-yl-6,7,8,9-tetrahydro-5H-benzocyclohepten-2-ylamino)-pyrimidin-4-ylamino]-N,N-dimethyl-benzenesulfonamide;

2-{5-Chloro-2-[7-(4-methyl-piperazin-1-yl)-6,7,8,9-tetrahydro-5H-benzocyclohepten-2-ylamino]-pyrimidin-4-ylamino}-N,N-dimethyl-benzenesulfonamide;

5-Chloro-N*4*-(2-methoxy-phenyl)-N*2*-[7-(4-methyl-piperazin-1-yl)-6,7,8,9-tetrahydro-5H-benzocyclohepten-2-yl]-pyrimidine-2,4-diamine;

(1S,2S,3R,4R)-3-{5-Chloro-2-[7-(4-methyl-piperazin-1-yl)-6,7,8,9-tetrahydro-5H-benzocyclohepten-2-ylamino]-pyrimidin-4-ylamino}-bicyclo[2.2.1]hept-5-ene-2-carboxylic acid amide;

(2-{5-Chloro-2-[7-(4-methyl-piperazin-1-yl)-6,7,8,9-tetrahydro-5H-benzocyclohepten-2-ylamino]-pyrimidin-4-ylamino}-phenoxy)-acetonitrile;

5-Chloro-N*4*-(2-methoxy-4-morpholin-4-yl-phenyl)-N*2*-(1-methoxy-7-morpholin-4-yl-6,7,8,9-tetrahydro-5H-benzocyclohepten-2-yl)-pyrimidine-2,4-diamine;

N-((1R,2R)-2-{5-Chloro-2-[3-methoxy-7-(2-methoxy-ethylamino)-6,7,8,9-tetrahydro-5H-benzocyclohepten-2-ylamino]-pyrimidin-4-ylamino}-cyclohexyl)-methanesulfonamide;

N-((1R,2R)-2-{5-Chloro-2-[3-methoxy-7-(2-methoxy-ethylamino)-6,7,8,9-tetrahydro-5H-benzocyclohepten-2-ylamino]-pyrimidin-4-ylamino}-cyclohexyl)-methanesulfonamide;

(1S,2S,3R,4R)-3-{5-Chloro-2-[3-methoxy-7-(2-methoxy-ethylamino)-6,7,8,9-tetrahydro-5H-benzocyclohepten-2-ylamino]-pyrimidin-4-ylamino}-bicyclo[2.2.1]hept-5-ene-2-carboxylic acid amide;

(1S,2S,3R,4R)-3-{5-Chloro-2-[3-methoxy-7-(2-methoxy-ethylamino)-6,7,8,9-tetrahydro-5H-benzocyclohepten-2-ylamino]-pyrimidin-4-ylamino}-bicyclo[2.2.1]hept-5-ene-2-carboxylic acid amide;

2-{5-Chloro-2-[7-(4-methyl-piperazin-1-yl)-6,7,8,9-tetrahydro-5H-benzocyclohepten-2-ylamino]-pyrimidin-4-ylamino}-3-fluoro-N-methyl-benzamide;

5-Chloro-N*2*-(1-methoxy-7-morpholin-4-yl-6,7,8,9-tetrahydro-5H-benzocyclohepten-2-yl)-N*4*-[2-(pyrrolidine-1-sulfonyl)-phenyl]-pyrimidine-2,4-diamine;

5-Chloro-N*2*-(1-methoxy-7-morpholin-4-yl-6,7,8,9-tetrahydro-5H-benzocyclohepten-2-yl)-N*4*-(2-pyrazol-1-yl-phenyl)-pyrimidine-2,4-diamine;

3-[5-Chloro-2-(1-methoxy-7-morpholin-4-yl-6,7,8,9-tetrahydro-5H-benzocyclohepten-2-ylamino)-pyrimidin-4-ylamino]-azepan-2-one;

(1S,3R,4R)-3-[5-Chloro-2-((S)-1-methoxy-7-morpholin-4-yl-6,7,8,9-tetrahydro-5H-benzocyclohepten-2-ylamino)-pyrimidin-4-ylamino]-bicyclo[2.2.1]hept-5-ene-2-carboxylic acid 2-methoxy-ethyl ester;

(1S,3R,4R)-3-[5-Chloro-2-((S)-1-methoxy-7-morpholin-4-yl-6,7,8,9-tetrahydro-5H-benzocyclohepten-2-ylamino)-pyrimidin-4-ylamino]-bicyclo[2.2.1]hept-5-ene-2-carboxylic acid 2-methoxy-ethyl ester;

1-{2-[5-Chloro-2-(1-methoxy-7-morpholin-4-yl-6,7,8,9-tetrahydro-5H-benzocyclohepten-2-ylamino)-pyrimidin-4-ylamino]-benzenesulfonyl}-pyrrolidin-3-ol;

2-{5-Chloro-2-[7-(3-hydroxy-piperidin-1-yl)-1-methoxy-6,7,8,9-tetrahydro-5H-benzocyclohepten-2-ylamino]-pyrimidin-4-ylamino}-N,N-dimethyl-benzenesulfonamide;

1-(2-{5-Chloro-4-[2-(pyrrolidine-1-sulfonyl)-phenylamino]-pyrimidin-2-ylamino}-1-methoxy-6,7,8,9-tetrahydro-5H-benzocyclohepten-7-yl)-piperidin-3-ol;

(1S,2S,3R,4R)-3-{5-Chloro-2-[7-(3-hydroxy-piperidin-1-yl)-1-methoxy-6,7,8,9-tetrahydro-5H-benzocyclohepten-2-ylamino]-pyrimidin-4-ylamino}-bicyclo[2.2.1]hept-5-ene-2-carboxylic acid amide;

(1S,2S,3R,4R)-3-{5-Chloro-2-[7-(3-hydroxy-piperidin-1-yl)-1-methoxy-6,7,8,9-tetrahydro-5H-benzocyclohepten-2-ylamino]-pyrimidin-4-ylamino}-bicyclo[2.2.1]hept-5-ene-2-carboxylic acid amide;

2-{5-Chloro-2-[1-methoxy-7-(4-methyl-piperazin-1-yl)-6,7,8,9-tetrahydro-5H-benzocyclohepten-2-ylamino]-pyrimidin-4-ylamino}-N,N-dimethyl-benzenesulfonamide;

2-{5-Chloro-2-[1-methoxy-7-(4-methyl-piperazin-1-yl)-6,7,8,9-tetrahydro-5H-benzocyclohepten-2-ylamino]-pyrimidin-4-ylamino}-N,N-dimethyl-benzenesulfonamide;

1-{2-[5-Chloro-4-(2-methoxy-4-morpholin-4-yl-phenylamino)-pyrimidin-2-ylamino]-1-methoxy-6,7,8,9-tetrahydro-5H-benzocyclohepten-7-yl}-piperidin-3-ol;

5-Chloro-N*2*-[1-methoxy-7-(4-methyl-piperazin-1-yl)-6,7,8,9-tetrahydro-5H-benzocyclohepten-2-yl]-N*4*-[2-(propane-2-sulfonyl)-phenyl]-pyrimidine-2,4-diamine;

2-[5-Chloro-2-(1-methoxy-7-morpholin-4-yl-6,7,8,9-tetrahydro-5H-benzocyclohepten-2-ylamino)-pyrimidin-4-ylamino]-N-methyl-benzamide;

30  (1S,2S,3R,4R)-3-{5-Chloro-2-[1-methoxy-7-(4-methyl-piperazin-1-yl)-6,7,8,9-tetrahydro-5H-benzocyclohepten-2-ylamino]-pyrimidin-4-ylamino}-bicyclo[2.2.1]hept-5-ene-2-carboxylic acid amide;

(1S,2S,3R,4R)-3-{5-Chloro-2-[1-methoxy-7-(4-methyl-piperazin-1-yl)-6,7,8,9-tetrahydro-5H-benzocyclohepten-2-ylamino]-pyrimidin-4-ylamino}-bicyclo[2.2.1]hept-5-ene-2-carboxylic acid amide;

2-{2-[1-(2-Methoxy-ethyl)-2-oxo-2,3,4,5-tetrahydro-1H-benzo[b]azepin-7-ylamino]-5-trifluoromethyl-pyrimidin-4-ylamino}-N-methyl-benzamide;

2-{2-[3-(2-Methoxyethyl)-2,3,4,5-tetrahydro-1H-benzo[d]azepin-7-ylamino]-5-trifluoromethylpyrimidin-4-ylamino}-3,N-dimethylbenzamide;

N-Methyl-2-[2-(7-morpholin-4-yl-6,7,8,9-tetrahydro-5H-benzocyclohepten-2-ylamino)-5-trifluoromethyl-pyrimidin-4-ylamino]-benzamide;

N(2)-(3-Ethyl-2,3,4,5-tetrahydro-1H-benzo[d]azepin-7-yl)-N(4)-(2-methoxy-4-morpholin-4-yl-phenyl)-5-trifluoromethylpyrimidine-2,4-diamine;

3-Fluoro-2-{2-[1-(2-methoxy-ethyl)-2-oxo-2,3,4,5-tetrahydro-1H-benzo[b]azepin-8-ylamino]-5-trifluoromethyl-pyrimidin-4-ylamino}-N-methyl-benzamide;

{3-[5-Chloro-2-(3-ethyl-2,3,4,5-tetrahydro-1H-benzo[d]azepin-7-ylamino)-pyrimidin-4-ylamino]-phenoxy}-acetonitrile;

{2-[5-Chloro-2-(3-ethyl-2,3,4,5-tetrahydro-1H-benzo[d]azepin-7-ylamino)-pyrimidin-4-ylamino]-phenoxy}-acetonitrile;

4-[5-Chloro-2-(7-morpholin-4-yl-6,7,8,9-tetrahydro-5H-benzocyclohepten-2-ylamino)-pyrimidin-4-ylamino]-3-methoxy-N-propyl-benzamide;

{2-[5-Chloro-2-(5,5-dimethyl-2-oxo-2,3,4,5-tetrahydro-1H-1-benzazepin-8-ylamino)-pyrimidin-4-ylamino]-3-fluoro-phenoxy}-acetonitrile;

(2-{5-Chloro-2-[3-(2-methoxy-ethyl)-2,3,4,5-tetrahydro-1H-3-benzazepin-7-ylamino]-pyrimidin-4-ylamino}-3-fluoro-phenoxy)-acetonitrile;

2-(7-Methoxy-8-{4-[2-(propane-2-sulfonyl)-phenylamino]-5-trifluoromethyl-pyrimidin-2-ylamino}-1,2,4,5-tetrahydro-3-benzazepin-3-yl)-N,N-dimethyl-acetamide;

(1S,2S,3R,4R)-3-[2-(3-Dimethylcarbamoylmethyl-8-methoxy-2,3,4,5-tetrahydro-1H-3-benzazepin-7-ylamino)-5-trifluoromethyl-pyrimidin-4-ylamino]-bicyclo[2.2.1]hept-5-ene-2-carboxylic acid amide;

(1S,2S,3R,4R)-3-{2-[3-(2-Methoxy-ethyl)-2,3,4,5-tetrahydro-1H-3-benzazepin-7-ylamino]-5-trifluoromethyl-pyrimidin-4-ylamino}-bicyclo[2.2.1]hept-5-ene-2-carboxylic acid amide;

(1S,2S,3R,4R)-3-[2-(7-Morpholin-4-yl-6,7,8,9-tetrahydro-5H-benzocyclohepten-2-ylamino)-5-trifluoromethyl-pyrimidin-4-ylamino]-bicyclo[2.2.1]hept-5-ene-2-carboxylic acid amide;

7-{5-Chloro-2-[3-(2-methoxy-ethyl)-2,3,4,5-tetrahydro-1H-3-benzazepin-7-ylamino]-pyrimidin-4-ylamino}-4-methoxy-2-methyl-2,3-dihydro-isoindol-1-one;

2-{7-[5-Chloro-4-(7-methoxy-2-methyl-3-oxo-2,3-dihydro-1H-isoindol-4-ylamino)-pyrimidin-2-ylamino]-8-methoxy-1,2,4,5-tetrahydro-3-benzazepin-3-yl}-N,N-dimethyl-acetamide;

7-[5-Chloro-2-(7-hydroxy-6,7,8,9-tetrahydro-5H-benzocyclohepten-2-ylamino)-pyrimidin-4-ylamino]-4-methoxy-2-methyl-2,3-dihydro-isoindol-1-one;

7-[5-Chloro-2-(7-morpholin-4-yl-6,7,8,9-tetrahydro-5H-benzocyclohepten-2-ylamino)-pyrimidin-4-ylamino]-4-methoxy-2-methyl-2,3-dihydro-isoindol-1-one;

(1S,2S,3R,4R)-3-[5-Chloro-2-(1-methoxy-6-morpholin-4-yl-6,7,8,9-tetrahydro-5H-benzocyclohepten-2-ylamino)-pyrimidin-4-ylamino]-bicyclo[2.2.1]hept-5-ene-2-carboxylic acid amide;

(1S,2S,3R,4R)-3-[5-Chloro-2-(1-methoxy-6-morpholin-4-yl-6,7,8,9-tetrahydro-5H-benzocyclohepten-2-ylamino)-pyrimidin-4-ylamino]-bicyclo[2.2.1]hept-5-ene-2-carboxylic acid amide;

2-[5-Chloro-2-(1-methoxy-6-morpholin-4-yl-6,7,8,9-tetrahydro-5H-benzocyclohepten-2-ylamino)-pyrimidin-4-ylamino]-N,N-dimethyl-benzenesulfonamide;

5-Chloro-N(2)-(1-methoxy-6-morpholin-4-yl-6,7,8,9-tetrahydro-5H-benzocyclohepten-2-yl)-N(4)-[2-(propane-2-sulfonyl)-phenyl]-pyrimidine-2,4-diamine;

2-[5-Chloro-2-(1-methoxy-6-morpholin-4-yl-6,7,8,9-tetrahydro-5H-benzocyclohepten-2-ylamino)-pyrimidin-4-ylamino]-benzoic acid isopropyl ester;

N-{(1R,2R)-2-[5-Chloro-2-(1-methoxy-6-morpholin-4-yl-6,7,8,9-tetrahydro-5H-benzocyclohepten-2-ylamino)-pyrimidin-4-ylamino]-cyclohexyl}-methanesulfonamide;

7-{5-Chloro-2-[3-(2-methoxy-ethyl)-2,3,4,5-tetrahydro-1H-3-benzazepin-7-ylamino]-pyrimidin-4-ylamino}-4-(4-isopropyl-piperazin-1-yl)-2-methyl-2,3-dihydro-isoindol-1-one;

2-(7-{5-Chloro-4-[7-(4-isopropyl-piperazin-1-yl)-2-methyl-3-oxo-2,3-dihydro-1H-isoindol-4-ylamino]-pyrimidin-2-ylamino}-8-methoxy-1,2,4,5-tetrahydro-3-benzazepin-3-yl)-N,N-dimethyl-acetamide;

5-Chloro-N(4)-(2-methoxy-4-morpholin-4-yl-phenyl)-N(2)-(1-methoxy-6-morpholin-4-yl-6,7,8,9-tetrahydro-5H-benzocyclohepten-2-yl)-pyrimidine-2,4-diamine;

7-{5-Chloro-2-[3-(2-hydroxy-ethyl)-8-methoxy-2,3,4,5-tetrahydro-1H-3-benzazepin-7-ylamino]-pyrimidin-4-ylamino}-4-(4-isopropyl-piperazin-1-yl)-2-methyl-2,3-dihydro-isoindol-1-one;

5-{5-Chloro-2-[3-(2-methoxy-ethyl)-2,3,4,5-tetrahydro-1H-3-benzazepin-7-ylamino]-pyrimidin-4-ylamino}-1H-pyrazole-3-carboxylic acid amide;

5-Chloro-N(2)-[3-(2-methoxy-ethyl)-2,3,4,5-tetrahydro-1H-3-benzazepin-7-yl]-N(4)-(5-methyl-2H-pyrazol-3-yl)-pyrimidine-2,4-diamine;

(1S,2S,3R,4R)-3-{5-Chloro-2-[1-methoxy-6-(2-methoxy-ethylamino)-6,7,8,9-tetrahydro-5H-benzocyclohepten-2- ylamino]-pyrimidin-4-ylamino}-bicyclo[2.2.1]hept-5-ene-2-carboxylic acid amide;

2-{5-Chloro-2-[1-methoxy-6-(2-methoxy-ethylamino)-6,7,8,9-tetrahydro-5H-benzocyclohepten-2-ylamino]-pyrimidin-4-ylamino}-N,N-dimethyl-benzenesulfonamide;

N-((1R,2R)-2-{5-Chloro-2-[1-methoxy-6-(2-methoxy-ethylamino)-6,7,8,9-tetrahydro-5H-benzocyclohepten-2-ylamino]-pyrimidin-4-ylamino}-cyclohexyl)-methanesulfonamide;

5-Chloro-N(2)-[1-methoxy-6-(2-methoxy-ethylamino)-6,7,8,9-tetrahydro-5H-benzocyclohepten-2-yl]-N(4)-[2-(propane-2-sulfonyl)-phenyl]-pyrimidine-2,4-diamine;

(1S,2S,3R,4R)-3-{5-Chloro-2-[6-(2-hydroxy-ethylamino)-1-methoxy-6,7,8,9-tetrahydro-5H-benzocyclohepten-2-ylamino]-pyrimidin-4-ylamino}-bicyclo[2.2.1]hept-5-ene-2-carboxylic acid amide;

2-(2-{5-Chloro-4-[2-(propane-2-sulfonyl)-phenylamino]-pyrimidin-2-ylamino}-1-methoxy-6,7,8,9-tetrahydro-5H-benzocyclohepten-6-ylamino)-ethanol;

(R)-1-(2-{5-Chloro-2-[6-(2-hydroxy-ethylamino)-1-methoxy-6,7,8,9-tetrahydro-5H-benzocyclohepten-2-ylamino]-pyrimidin-4-ylamino}-benzenesulfonyl)-pyrrolidin-3-ol;

(S)-1-(2-{5-Chloro-2-[6-(2-hydroxy-ethylamino)-1-methoxy-6,7,8,9-tetrahydro-5H-benzocyclohepten-2-ylamino]-pyrimidin-4-ylamino}-benzenesulfonyl)-pyrrolidin-3-ol;

2-(2-{5-Chloro-4-[2-(pyrrolidine-1-sulfonyl)-phenylamino]-pyrimidin-2-ylamino}-1-methoxy-6,7,8,9-tetrahydro-5H-benzocyclohepten-6-ylamino)-ethanol;

N-((1R,2R)-2-{5-Chloro-2-[6-(2-hydroxy-ethylamino)-1-methoxy-6,7,8,9-tetrahydro-5H-benzocyclohepten-2-ylamino]-pyrimidin-4-ylamino}-cyclohexyl)-methanesulfonamide;

7-{5-Chloro-4-[2-(3-methyl-pyridin-2-yl)-phenylamino]-pyrimidin-2-ylamino}-5,5-dimethyl-1,3,4,5-tetrahydro-benzo[b]azepin-2-one;

5-Chloro-N*2*-[3-(2-methoxy-ethyl)-2,3,4,5-tetrahydro-1H-benzo[d]azepin-7-yl]-N*4*-[2-(3-methyl-pyridin-2-yl)-phenyl]-pyrimidine-2,4-diamine;

7-{5-Chloro-4-[2-(5-methyl-[1,3,4]thiadiazol-2-yl)-phenylamino]-pyrimidin-2-ylamino}-5,5-dimethyl-1,3,4,5-tetrahydro-benzo[b]azepin-2-one;

5-Chloro-N*2*-[3-(2-methoxy-ethyl)-2,3,4,5-tetrahydro-1H-benzo[d]azepin-7-yl]-N*4*-[2-(5-methyl-[1,3,4]thiadiazol-2-yl)-phenyl]-pyrimidine-2,4-diamine;

7-[5-Chloro-4-(2-pyrazin-2-yl-phenylamino)-pyrimidin-2-ylamino]-5,5-dimethyl-1,3,4,5-tetrahydro-benzo[b]azepin-2-one;

7-[5-Chloro-4-(2-pyrimidin-2-yl-phenylamino)-pyrimidin-2-ylamino]-5,5-dimethyl-1,3,4,5-tetrahydro-benzo[b]azepin-2-one;

1-Chloro-N*2*-[3-(2-methoxy-ethyl)-2,3,4,5-tetrahydro-1H-benzo[d]azepin-7-yl]-N*4*-(2-pyrimidin-2-yl-phenyl)-pyrimidine-2,4-diamine;

7-[5-Chloro-4-(2-thiazol-2-yl-phenylamino)-pyrimidin-2-ylamino]-5,5-dimethyl-1,3,4,5-tetrahydro-benzo[b]azepin-2-one;

5-Chloro-N*2*-[3-(2-methoxy-ethyl)-2,3,4,5-tetrahydro-1H-benzo[d]azepin-7-yl]-N*4*-(2-thiazol-2-yl-phenyl)-pyrimidine-2,4-diamine;

7-(5-Chloro-4-{2-[1-(2-methoxy-ethyl)-1H-imidazol-2-yl]-phenylamino}-pyrimidin-2-ylamino)-5,5-dimethyl-1,3,4,5-tetrahydro-benzo[b]azepin-2-one;

5-Chloro-N*4*-{2-[1-(2-methoxy-ethyl)-1H-imidazol-2-yl]-phenyl}-N*2*-[3-(2-methoxy-ethyl)-2,3,4,5-tetrahydro-1H-benzo[d]azepin-7-yl]-pyrimidine-2,4-diamine;

5-Chloro-N*2*-[3-(2-methoxy-ethyl)-2,3,4,5-tetrahydro-1H-benzo[d]azepin-7-yl]-N*4*-(2-oxazol-5-yl-phenyl)-pyrimidine-2,4-diamine;

7-{5-Chloro-4-[2-(1-methyl-1H-imidazol-2-yl)-phenylamino]-pyrimidin-2-ylamino}-1-ethyl-6-methoxy-1,3,4,5-tetrahydro-benzo[b]azepin-2-one;

7-{5-Chloro-4-[2-(3-methyl-pyridin-2-yl)-phenylamino]-pyrimidin-2-ylamino}-1-ethyl-6-methoxy-1,3,4,5-tetrahydro-benzo[b]azepin-2-one;

7-[5-Chloro-4-(2-oxazol-5-yl-phenylamino)-pyrimidin-2-ylamino]-5,5-dimethyl-1,3,4,5-tetrahydro-benzo[b]azepin-2-one;

5-Chloro-N*2*-[8-methoxy-3-(2-methoxy-ethyl)-2,3,4,5-tetrahydro-1H-benzo[d]azepin-7-yl]-N*4*-[2-(1-methyl-1H-imidazol-2-yl)-phenyl]-pyrimidine-2,4-diamine;

5-Chloro-N*2*-[8-methoxy-3-(2-methoxy-ethyl)-2,3,4,5-tetrahydro-1H-benzo[d]azepin-7-yl]-N*4*-[2-(3-methyl-pyridin-2-yl)-phenyl]-pyrimidine-2,4-diamine;

6-{2-[5-Chloro-2-(5,5-dimethyl-2-oxo-2,3,4,5-tetrahydro-1H-benzo[b]azepin-7-ylamino)-pyrimidin-4-ylamino]-phenyl}-1H-pyrimidine-2,4-dione;

7-{5-Chloro-4-[2-(3-methoxy-pyridin-2-yl)-phenylamino]-pyrimidin-2-ylamino}-5,5-dimethyl-1,3,4,5-tetrahydro-benzo[b]azepin-2-one;

5-Chloro-N*2*-[3-(2-methoxy-ethyl)-2,3,4,5-tetrahydro-1H-benzo[d]azepin-7-yl]-N*4*-[2-(3-methoxy-pyridin-2-yl)-phenyl]-pyrimidine-2,4-diamine;

7-{5-Chloro-4-[2-(3-trifluoromethyl-pyridin-2-yl)-phenylamino]-pyrimidin-2-ylamino}-5,5-dimethyl-1,3,4,5-tetrahydro-benzo[b]azepin-2-one;

5-Chloro-N*2*-[3-(2-methoxy-ethyl)-2,3,4,5-tetrahydro-1H-benzo[d]azepin-7-yl]-N*4*-[2-(3-trifluoromethyl-pyridin-2-yl)-phenyl]-pyrimidine-2,4-diamine;

7-[5-Chloro-4-(3-pyridin-3-yl-phenylamino)-pyrimidin-2-ylamino]-5,5-dimethyl-1,3,4,5-tetrahydro-benzo[b]azepin-2-one;

7-{5-Chloro-4-[2-(1-methyl-1H-imidazol-2-yl)-phenylamino]-pyrimidin-2-ylamino}-1,3,4,5-tetrahydro-benzo[b]azepin-2-one;

7-{5-Chloro-4-[2-(1-methyl-1H-imidazol-2-yl)-phenylamino]-pyrimidin-2-ylamino}-1-methyl-1,3,4,5-tetrahydro-benzo[b]azepin-2-one;

7-{5-Chloro-4-[2-(1-methyl-1H-imidazol-2-yl)-phenylamino]-pyrimidin-2-ylamino}-1-ethyl-8-methoxy-1,3,4,5-tetrahydro-benzo[b]azepin-2-one;

7-[5-Chloro-4-(2-oxazol-5-yl-phenylamino)-pyrimidin-2-ylamino]-1,3,4,5-tetrahydro-benzo[b]azepin-2-one;

2-(7-{5-Chloro-4-[2-(1-methyl-1H-imidazol-2-yl)-phenylamino]-pyrimidin-2-ylamino}-8-methoxy-1,2,4,5-tetrahydro-benzo[d]azepin-3-yl)-N,N-dimethyl-acetamide;

2-(7-{5-Chloro-4-[2-(3-methyl-pyridin-2-yl)-phenylamino]-pyrimidin-2-ylamino}-8-methoxy-1,2,4,5-tetrahydro-benzo[d]azepin-3-yl)-N,N-dimethyl-acetamide;

7-{5-Chloro-4-[2-(4-methyl-pyridin-2-yl)-phenylamino]-pyrimidin-2-ylamino}-5,5-dimethyl-1,3,4,5-tetrahydro-benzo[b]azepin-2-one;

7-{5-Chloro-4-[2-(4-methyl-pyridin-2-yl)-phenylamino]-pyrimidin-2-ylamino}-1-methyl-1,3,4,5-tetrahydro-benzo[b]azepin-2-one;

7-{5-Chloro-4-[2-(5-methyl-pyridin-2-yl)-phenylamino]-pyrimidin-2-ylamino}-5,5-dimethyl-1,3,4,5-tetrahydro-benzo[b]azepin-2-one;

7-{5-Chloro-4-[2-(5-methyl-pyridin-2-yl)-phenylamino]-pyrimidin-2-ylamino}-1-methyl-1,3,4,5-tetrahydro-benzo[b]azepin-2-one;

7-[5-Chloro-4-(1-methyl-1H-benzoimidazol-4-ylamino)-pyrimidin-2-ylamino]-5,5-dimethyl-1,3,4,5-tetrahydro-benzo[b]azepin-2-one;

5-Chloro-N*2*-[3-(2-methoxy-ethyl)-2,3,4,5-tetrahydro-1H-benzo[d]azepin-7-yl]-N*4*-(1-methyl-1H-benzoimidazol-4-yl)-pyrimidine-2,4-diamine;

7-[5-Chloro-4-(1-methyl-1H-benzoimidazol-4-ylamino)-pyrimidin-2-ylamino]-1-methyl-1,3,4,5-tetrahydro-benzo[b]azepin-2-one;

7-{5-Chloro-4-[2-(6-methyl-pyridin-2-yl)-phenylamino]-pyrimidin-2-ylamino}-5,5-dimethyl-1,3,4,5-tetrahydro-benzo[b]azepin-2-one;

5-Chloro-N*2*-[3-(2-methoxy-ethyl)-2,3,4,5-tetrahydro-1H-benzo[d]azepin-7-yl]-N*4*-[2-(6-methyl-pyridin-2-yl)-phenyl]-pyrimidine-2,4-diamine;

7-{5-Chloro-4-[2-(4-trifluoromethyl-1H-imidazol-2-yl)-phenylamino]-pyrimidin-2-ylamino}-5,5-dimethyl-1,3,4,5-tetrahydro-benzo[b]azepin-2-one;

5-Chloro-N*2*-[3-(2-methoxy-ethyl)-2,3,4,5-tetrahydro-1H-benzo[d]azepin-7-yl]-N*4*-[2-(4-trifluoromethyl-1H-imidazol-2-yl)-phenyl]-pyrimidine-2,4-diamine;

7-{5-Chloro-4-[2-(4-trifluoromethyl-1H-imidazol-2-yl)-phenylamino]-pyrimidin-2-ylamino}-1,3,4,5-tetrahydro-benzo[b]azepin-2-one;

7-{5-Chloro-4-[2-(4-trifluoromethyl-1H-imidazol-2-yl)-phenylamino]-pyrimidin-2-ylamino}-1-methyl-1,3,4,5-tetrahydro-benzo[b]azepin-2-one;

7-[5-Chloro-4-(2-trifluoromethyl-1H-benzoimidazol-5-ylamino)-pyrimidin-2-ylamino]-5,5-dimethyl-1,3,4,5-tetrahydro-benzo[b]azepin-2-one;

5-Chloro-N*2*-[3-(2-methoxy-ethyl)-2,3,4,5-tetrahydro-1H-benzo[d]azepin-7-yl]-N*4*-(2-trifluoromethyl-1H-benzoimidazol-5-yl)-pyrimidine-2,4-diamine;

7-[5-Chloro-4-(2-trifluoromethyl-1H-benzoimidazol-5-ylamino)-pyrimidin-2-ylamino]-1-methyl-1,3,4,5-tetrahydro-benzo[b]azepin-2-one;

(1S,2S,3R,4R)-3-[5-Chloro-2-(7-hydroxy-6,7,8,9-tetrahydro-5H-benzocyclohepten-2-ylamino)-pyrimidin-4-ylamino]-bicyclo[2.2.1]hept-5-ene-2-carboxylic acid amide;

5-Chloro-N*4*-[2-(3-methoxy-pyridin-2-yl)-phenyl]-N*2*-(7-morpholin-4-yl-6,7,8,9-tetrahydro-5H-benzocyclohepten-2-yl)-pyrimidine-2,4-diamine;

2-{5-Chloro-4-[2-(3-methoxy-pyridin-2-yl)-phenylamino]-pyrimidin-2-ylamino}-6,7,8,9-tetrahydro-5H-benzocyclohepten-7-ol;

5-Chloro-N*4*-[2-(3-methyl-pyridin-2-yl)-phenyl]-N*2*-(7-morpholin-4-yl-6,7,8,9-tetrahydro-5H-benzocyclohepten-2-yl)-pyrimidine-2,4-diamine;

2-{5-Chloro-4-[2-(3-methyl-pyridin-2-yl)-phenylamino]-pyrimidin-2-ylamino}-6,7,8,9-tetrahydro-5H-benzocyclohepten-7-ol;

2-[5-Chloro-2-(5,5-dimethyl-2-oxo-2,3,4,5-tetrahydro-1H-benzo[b]azepin-7-ylamino)-pyrimidin-4-ylamino]-N-propyl-benzamide;

2-{5-Chloro-2-[3-(2-methoxy-ethyl)-2,3,4,5-tetrahydro-1H-benzo[d]azepin-7-ylamino]-pyrimidin-4-ylamino}-N-propyl-benzamide;

2-[5-Chloro-2-(2-oxo-2,3,4,5-tetrahydro-1H-benzo[b]azepin-7-ylamino)-pyrimidin-4-ylamino]-N-propyl-benzamide;

2-[5-Chloro-2-(1-methyl-2-oxo-2,3,4,5-tetrahydro-1H-benzo[b]azepin-7-ylamino)-pyrimidin-4-ylamino]-N-propyl-benzamide;

2-{5-Chloro-2-[8-methoxy-3-(2-methoxy-ethyl)-2,3,4,5-tetrahydro-1H-benzo[d]azepin-7-ylamino]-pyrimidin-4-ylamino}-N-propyl-benzamide;

N-Butyl-2-[5-chloro-2-(5,5-dimethyl-2-oxo-2,3,4,5-tetrahydro-1H-benzo[b]azepin-7-ylamino)-pyrimidin-4-ylamino]-benzamide;

N-Butyl-2-{5-chloro-2-[3-(2-methoxy-ethyl)-2,3,4,5-tetrahydro-1H-benzo[d]azepin-7-ylamino]-pyrimidin-4-ylamino}-benzamide;

N-Butyl-2-[5-chloro-2-(2-oxo-2,3,4,5-tetrahydro-1H-benzo[b]azepin-7-ylamino)-pyrimidin-4-ylamino]-benzamide;

N-Butyl-2-[5-chloro-2-(1-methyl-2-oxo-2,3,4,5-tetrahydro-1H-benzo[b]azepin-7-ylamino)-pyrimidin-4-ylamino]-benzamide;

N-Butyl-2-{5-chloro-2-[8-methoxy-3-(2-methoxy-ethyl)-2,3,4,5-tetrahydro-1H-benzo[d]azepin-7-ylamino]-pyrimidin-4-ylamino}-benzamide;

2-[5-Chloro-2-(7-morpholin-4-yl-6,7,8,9-tetrahydro-5H-benzocyclohepten-2-ylamino)-pyrimidin-4-ylamino]-N,N-dimethyl-benzenesulfonamide;

2-[5-Chloro-2-(7-hydroxy-6,7,8,9-tetrahydro-5H-benzocyclohepten-2-ylamino)-pyrimidin-4-ylamino]-N,N-dimethyl-benzenesulfonamide;

5-Chloro-N*2*-(7-morpholin-4-yl-6,7,8,9-tetrahydro-5H-benzocyclohepten-2-yl)-N*4*-(2-pyrazol-1-yl-phenyl)-pyrimidine-2,4-diamine;

2-[5-Chloro-4-(2-pyrazol-1-yl-phenylamino)-pyrimidin-2-ylamino]-6,7,8,9-tetrahydro-5H-benzocyclohepten-7-ol;

5-Chloro-N*2*-(7-morpholin-4-yl-6,7,8,9-tetrahydro-5H-benzocyclohepten-2-yl)-N*4*-[2-(propane-2-sulfonyl)-phenyl]-pyrimidine-2,4-diamine;

2-{5-Chloro-4-[2-(propane-2-sulfonyl)-phenylamino]-pyrimidin-2-ylamino}-6,7,8,9-tetrahydro-5H-benzocyclohepten-7-ol;

2-[5-Chloro-2-(5,5-dimethyl-2-oxo-2,3,4,5-tetrahydro-1H-benzo[b]azepin-7-ylamino)-pyrimidin-4-ylamino]-N-cyanomethyl-3-methyl-benzamide;

2-[5-Chloro-2-(1-methyl-2-oxo-2,3,4,5-tetrahydro-1H-benzo[b]azepin-7-ylamino)-pyrimidin-4-ylamino]-N-cyanomethyl-3-methyl-benzamide;

2-{5-Chloro-2-[3-(2-methoxy-ethyl)-2,3,4,5-tetrahydro-1H-benzo[d]azepin-7-ylamino]-pyrimidin-4-ylamino}-N-cyanomethyl-3-methyl-benzamide;

2-[5-Chloro-2-(5,5-dimethyl-2-oxo-2,3,4,5-tetrahydro-1H-benzo[b]azepin-7-ylamino)-pyrimidin-4-ylamino]-N-(2-cyano-ethyl)-3-fluoro-benzamide;

2-[5-Chloro-2-(1-methyl-2-oxo-2,3,4,5-tetrahydro-1H-benzo[b]azepin-7-ylamino)-pyrimidin-4-ylamino]-N-(2-cyano-ethyl)-3-fluoro-benzamide;

2-{5-Chloro-2-[3-(2-methoxy-ethyl)-2,3,4,5-tetrahydro-1H-benzo[d]azepin-7-ylamino]-pyrimidin-4-ylamino}-N-(2-cyano-ethyl)-3-fluoro-benzamide;

2-[5-Chloro-2-(5,5-dimethyl-2-oxo-2,3,4,5-tetrahydro-1H-benzo[b]azepin-7-ylamino)-pyrimidin-4-ylamino]-N-cyanomethyl-3-fluoro-benzamide;

2-[5-Chloro-2-(1-methyl-2-oxo-2,3,4,5-tetrahydro-1H-benzo[b]azepin-7-ylamino)-pyrimidin-4-ylamino]-N-cyanomethyl-3-fluoro-benzamide;

2-[5-Chloro-2-(2-oxo-2,3,4,5-tetrahydro-1H-benzo[b]azepin-7-ylamino)-pyrimidin-4-ylamino]-N-cyanomethyl-3-fluoro-benzamide;

(1S,2S,3R,4R)-3-[5-Chloro-2-(3-methoxy-7-morpholin-4-yl-6,7,8,9-tetrahydro-5H-benzocyclohepten-2-ylamino)-pyrimidin-4-ylamino]-bicyclo[2.2.1]hept-5-ene-2-carboxylic acid amide;

(1S,2S,3R,4R)-3-[5-Chloro-2-(3-methoxy-7-morpholin-4-yl-6,7,8,9-tetrahydro-5H-benzocyclohepten-2-ylamino)-pyrimidin-4-ylamino]-bicyclo[2.2.1]hept-5-ene-2-carboxylic acid amide;

2-[5-Chloro-2-(3-methoxy-7-morpholin-4-yl-6,7,8,9-tetrahydro-5H-benzocyclohepten-2-ylamino)-pyrimidin-4-ylamino]-N,N-dimethyl-benzenesulfonamide;

5-Chloro-N*2*-(3-methoxy-7-morpholin-4-yl-6,7,8,9-tetrahydro-5H-benzocyclohepten-2-yl)-N*4*-[2-(propane-2-sulfonyl)-phenyl]-pyrimidine-2,4-diamine;

N-{(1R,2R)-2-[5-Chloro-2-(3-methoxy-7-morpholin-4-yl-6,7,8,9-tetrahydro-5H-benzocyclohepten-2-ylamino)-pyrimidin-4-ylamino]-cyclohexyl}-methanesulfonamide;

5-Chloro-N*2*-(3-methoxy-7-morpholin-4-yl-6,7,8,9-tetrahydro-5H-benzocyclohepten-2-yl)-N*4*-(2-pyrazol-1-yl-phenyl)-pyrimidine-2,4-diamine;

(1S,2S,3R,4R)-3-{5-Chloro-2-[7-(2,2-difluoro-ethylamino)-3-methoxy-6,7,8,9-tetrahydro-5H-benzocyclohepten-2-ylamino]-pyrimidin-4-ylamino}-bicyclo[2.2.1]hept-5-ene-2-carboxylic acid amide;

(1S,2S,3R,4R)-3-{5-Chloro-2-[7-(2,2-difluoro-ethylamino)-3-methoxy-6,7,8,9-tetrahydro-5H-benzocyclohepten-2-ylamino]-pyrimidin-4-ylamino}-bicyclo[2.2.1]hept-5-ene-2-carboxylic acid amide;

2-{5-Chloro-2-[7-(2,2-difluoro-ethylamino)-3-methoxy-6,7,8,9-tetrahydro-5H-benzocyclohepten-2-ylamino]-pyrimidin-4-ylamino}-N,N-dimethyl-benzenesulfonamide;

5-Chloro-N*2*-[7-(2,2-difluoro-ethylamino)-3-methoxy-6,7,8,9-tetrahydro-5H-benzocyclohepten-2-yl]-N*4*-[2-(propane-2-sulfonyl)-phenyl]-pyrimidine-2,4-diamine;

N-((1R,2R)-2-{5-Chloro-2-[7-(2,2-difluoro-ethylamino)-3-methoxy-6,7,8,9-tetrahydro-5H-benzocyclohepten-2-ylamino]-pyrimidin-4-ylamino}-cyclohexyl)-methanesulfonamide;

N-((1R,2R)-2-{5-Chloro-2-[7-(2,2-difluoro-ethylamino)-3-methoxy-6,7,8,9-tetrahydro-5H-benzocyclohepten-2-ylamino]-pyrimidin-4-ylamino}-cyclohexyl)-methanesulfonamide;

5-Chloro-N*2*-[7-(2,2-difluoro-ethylamino)-3-methoxy-6,7,8,9-tetrahydro-5H-benzocyclohepten-2-yl]-N*4*-(2-pyrazol-1-yl-phenyl)-pyrimidine-2,4-diamine;

2-{5-Chloro-2-[3-(2-methoxy-ethyl)-2,3,4,5-tetrahydro-1H-benzo[d]azepin-7-ylamino]-pyrimidin-4-ylamino}-N-(2-cyano-ethyl)-3-methoxy-benzamide;

2-[5-Chloro-2-(5,5-dimethyl-2-oxo-2,3,4,5-tetrahydro-1H-benzo[b]azepin-7-ylamino)-pyrimidin-4-ylamino]-N-(2-cyano-ethyl)-3-methoxy-benzamide;

2-[5-Chloro-2-(1-methyl-2-oxo-2,3,4,5-tetrahydro-1H-benzo[b]azepin-7-ylamino)-pyrimidin-4-ylamino]-N-(2-cyano-ethyl)-3-methoxy-benzamide;

2-{5-Chloro-2-[3-(2-methoxy-ethyl)-2,3,4,5-tetrahydro-1H-benzo[d]azepin-7-ylamino]-pyrimidin-4-ylamino}-N-cyanomethyl-3-methoxy-benzamide;

2-[5-Chloro-2-(5,5-dimethyl-2-oxo-2,3,4,5-tetrahydro-1H-benzo[b]azepin-7-ylamino)-pyrimidin-4-ylamino]-N-cyanomethyl-3-methoxy-benzamide;

2-[5-Chloro-2-(1-methyl-2-oxo-2,3,4,5-tetrahydro-1H-benzo[b]azepin-7-ylamino)-pyrimidin-4-ylamino]-N-cyanomethyl-3-methoxy-benzamide;

2-{5-Chloro-2-[3-(2-methoxy-ethyl)-2,3,4,5-tetrahydro-1H-benzo[d]azepin-7-ylamino]-pyrimidin-4-ylamino}-N-cyanomethyl-3-fluoro-benzamide;

2-[5-Chloro-2-(5,5-dimethyl-2-oxo-2,3,4,5-tetrahydro-1H-benzo[b]azepin-8-ylamino)-pyrimidin-4-ylamino]-N-cyanomethyl-3-fluoro-benzamide;

5-Chloro-N*2*-[3-methoxy-7-(2-methoxy-ethylamino)-6,7,8,9-tetrahydro-5H-benzocyclohepten-2-yl]-N*4*-[2-(pyrrolidine-1-sulfonyl)-phenyl]-pyrimidine-2,4-diamine;

1-(2-{5-Chloro-2-[3-methoxy-7-(2-methoxy-ethylamino)-6,7,8,9-tetrahydro-5H-benzocyclohepten-2-ylamino]-pyrimidin-4-ylamino}-benzenesulfonyl)-pyrrolidin-3-ol;

2-{5-Chloro-2-[3-methoxy-7-(2-methoxy-ethylamino)-6,7,8,9-tetrahydro-5H-benzocyclohepten-2-ylamino]-pyrimidin-4-ylamino}-N,N-dimethyl-benzenesulfonamide;

5-Chloro-N*2*-[3-methoxy-7-(2-methoxy-ethylamino)-6,7,8,9-tetrahydro-5H-benzocyclohepten-2-yl]-N*4*-[2-(propane-2-sulfonyl)-phenyl]-pyrimidine-2,4-diamine;

5-Chloro-N*2*-[3-methoxy-7-(2-methoxy-ethylamino)-6,7,8,9-tetrahydro-5H-benzocyclohepten-2-yl]-N*4*-(2-pyrazol-1-yl-phenyl)-pyrimidine-2,4-diamine;

2-{5-Chloro-2-[3-methoxy-7-(2-methoxy-ethylamino)-6,7,8,9-tetrahydro-5H-benzocyclohepten-2-ylamino]-pyrimidin-4-ylamino}-N-methyl-benzamide;

2-(2-{5-Chloro-4-[2-(pyrrolidine-1-sulfonyl)-phenylamino]-pyrimidin-2-ylamino}-3-methoxy-6,7,8,9-tetrahydro-5H-benzocyclohepten-7-ylamino)-ethanol;

1-(2-{5-Chloro-2-[7-(2-hydroxy-ethylamino)-3-methoxy-6,7,8,9-tetrahydro-5H-benzocyclohepten-2-ylamino]-pyrimidin-4-ylamino}-benzenesulfonyl)-pyrrolidin-3-ol;

2-{5-Chloro-2-[7-(2-hydroxy-ethylamino)-3-methoxy-6,7,8,9-tetrahydro-5H-benzocyclohepten-2-ylamino]-pyrimidin-4-ylamino}-N,N-dimethyl-benzenesulfonamide;

2-(2-{5-Chloro-4-[2-(propane-2-sulfonyl)-phenylamino]-pyrimidin-2-ylamino}-3-methoxy-6,7,8,9-tetrahydro-5H-benzocyclohepten-7-ylamino)-ethanol;

2-{2-[5-Chloro-4-(2-pyrazol-1-yl-phenylamino)-pyrimidin-2-ylamino]-3-methoxy-6,7,8,9-tetrahydro-5H-benzocyclohepten-7-ylamino}-ethanol;

2-{5-Chloro-2-[7-(2-hydroxy-ethylamino)-3-methoxy-6,7,8,9-tetrahydro-5H-benzocyclohepten-2-ylamino]-pyrimidin-4-ylamino}-N-methyl-benzamide;

2-{5-Chloro-2-[7-(2-hydroxy-ethylamino)-3-methoxy-6,7,8,9-tetrahydro-5H-benzocyclohepten-2-ylamino]-pyrimidin-4-ylamino}-benzoic acid 2-methoxy-ethyl ester;

N-((1R,2R)-2-{5-Chloro-2-[7-(2-hydroxy-ethylamino)-3-methoxy-6,7,8,9-tetrahydro-5H-benzocyclohepten-2-ylamino]-pyrimidin-4-ylamino}-cyclohexyl)-methanesulfonamide;

N-((1R,2R)-2-{5-Chloro-2-[7-(2-hydroxy-ethylamino)-3-methoxy-6,7,8,9-tetrahydro-5H-benzocyclohepten-2-ylamino]-pyrimidin-4-ylamino}-cyclohexyl)-methanesulfonamide;

(1S,2S,3R,4R)-3-{5-Chloro-2-[7-(2-hydroxy-ethylamino)-3-methoxy-6,7,8,9-tetrahydro-5H-benzocyclohepten-2-ylamino]-pyrimidin-4-ylamino}-bicyclo[2.2.1]hept-5-ene-2-carboxylic acid amide;

(1S,2S,3R,4R)-3-{5-Chloro-2-[7-(2-hydroxy-ethylamino)-3-methoxy-6,7,8,9-tetrahydro-5H-benzocyclohepten-2-ylamino]-pyrimidin-4-ylamino}-bicyclo[2.2.1]hept-5-ene-2-carboxylic acid amide;

1-(2-{5-Chloro-2-[3-methoxy-7-(4-methyl-piperazin-1-yl)-6,7,8,9-tetrahydro-5H-benzocyclohepten-2-ylamino]-pyrimidin-4-ylamino}-benzenesulfonyl)-pyrrolidin-3-ol;

2-{5-Chloro-2-[3-methoxy-7-(4-methyl-piperazin-1-yl)-6,7,8,9-tetrahydro-5H-benzocyclohepten-2-ylamino]-pyrimidin-4-ylamino}-N,N-dimethyl-benzenesulfonamide;

5-Chloro-N*2*-[3-methoxy-7-(4-methyl-piperazin-1-yl)-6,7,8,9-tetrahydro-5H-benzocyclohepten-2-yl]-N*4*-[2-(propane-2-sulfonyl)-phenyl]-pyrimidine-2,4-diamine;

N-((1R,2R)-2-{5-Chloro-2-[3-methoxy-7-(4-methyl-piperazin-1-yl)-6,7,8,9-tetrahydro-5H-benzocyclohepten-2-ylamino]-pyrimidin-4-ylamino}-cyclohexyl)-methanesulfonamide;

N-((1R,2R)-2-{5-Chloro-2-[3-methoxy-7-(4-methyl-piperazin-1-yl)-6,7,8,9-tetrahydro-5H-benzocyclohepten-2-ylamino]-pyrimidin-4-ylamino}-cyclohexyl)-methanesulfonamide;

(1S,2S,3R,4R)-3-{5-Chloro-2-[3-methoxy-7-(4-methyl-piperazin-1-yl)-6,7,8,9-tetrahydro-5H-benzocyclohepten-2-ylamino]-pyrimidin-4-ylamino}-bicyclo[2.2.1]hept-5-ene-2-carboxylic acid amide;

(1S,2S,3R,4R)-3-{5-Chloro-2-[3-methoxy-7-(4-methyl-piperazin-1-yl)-6,7,8,9-tetrahydro-5H-benzocyclohepten-2-ylamino]-pyrimidin-4-ylamino}-bicyclo[2.2.1]hept-5-ene-2-carboxylic acid amide;

2-{5-Chloro-2-[3-(3-dimethylamino-propyl)-8-methoxy-2-oxo-2,3,4,5-tetrahydro-1H-benzo[d]azepin-7-ylamino]pyrimidin-4-ylamino}-benzoic acid isopropyl ester;

2-{7-[5-Chloro-4-((1R,2R)-2-methanesulfonylamino-cyclohexylamino)-pyrimidin-2-ylamino]-8-methoxy-1,2,4,5-tetrahydro-benzo[d]azepin-3-yl}-N-methyl-acetamide;

2-{7-[5-Chloro-4-(2-methoxy-4-morpholin-4-yl-phenylamino)-pyrimidin-2-ylamino]-8-methoxy-1,2,4,5-tetrahydro-benzo[d]azepin-3-yl}-N-methyl-acetamide;

2-[5-Chloro-2-(8-methoxy-3-methylcarbamoylmethyl-2,3,4,5-tetrahydro-1H-benzo[d]azepin-7-ylamino)-pyrimidin-4-ylamino]-N-methyl-benzamide;

2-[5-Chloro-2-(8-methoxy-3-methylcarbamoylmethyl-2,3,4,5-tetrahydro-1H-benzo[d]azepin-7-ylamino)-pyrimidin-4-ylamino]-N-ethyl-benzamide;

2-[5-Chloro-2-(8-methoxy-3-methylcarbamoylmethyl-2,3,4,5-tetrahydro-1H-benzo[d]azepin-7-ylamino)-pyrimidin-4-ylamino]-3-fluoro-N-methyl-benzamide;

(2-exo,3-exo)-3-[5-Chloro-2-(8-methoxy-3-methylcarbamoylmethyl-2,3,4,5-tetrahydro-1H-benzo[d]azepin-7-ylamino)-pyrimidin-4-ylamino]-bicyclo[2.2.1]hept-5-ene-2-carboxylic acid amide;

2-{7-[5-Chloro-4-(5-chloro-2-methoxy-phenylamino)-pyrimidin-2-ylamino]-8-methoxy-1,2,4,5-tetrahydro-benzo[d]azepin-3-yl}-N-methyl-acetamide;

2-[5-Chloro-2-(3-dimethylcarbamoylmethyl-8-methoxy-2,3,4,5-tetrahydro-1H-benzo[d]azepin-7-ylamino)-pyrimidin-4-ylamino]-N-ethyl-3-fluoro-benzamide;

5-Chloro-N*2*-[3-(2-methanesulfonyl-ethyl)-8-methoxy-2,3,4,5-tetrahydro-1H-benzo[d]azepin-7-yl]-N*4*-(2-methoxy-4-morpholin-4-yl-phenyl)-pyrimidine-2,4-diamine;

1-{7-[5-Chloro-4-(2-methoxy-4-morpholin-4-yl-phenylamino)-pyrimidin-2-ylamino]-8-methoxy-1,2,4,5-tetrahydro-benzo[d]azepin-3-yl}-2-dimethylamino-ethanone;

N-((1R,2R)-2-{5-Chloro-2-[3-(2-methanesulfonyl-ethyl)-8-methoxy-2,3,4,5-tetrahydro-1H-benzo[d]azepin-7-ylamino]-pyrimidin-4-ylamino}-cyclohexyl)-methanesulfonamide;

(1S,2S,3R,4R)-3-[5-Chloro-2-(3-dimethylcarbamoylmethyl-8-methoxy-2,3,4,5-tetrahydro-1H-benzo[d]azepin-7-ylamino)-pyrimidin-4-ylamino]-bicyclo[2.2.1]hept-5-ene-2-carboxylic acid amide;

(1S,2S,3R,4R)-3-[5-Chloro-2-(8-methoxy-3-methylcarbamoylmethyl-2,3,4,5-tetrahydro-1H-benzo[d]azepin-7-ylamino)-pyrimidin-4-ylamino]-bicyclo[2.2.1]hept-5-ene-2-carboxylic acid amide;

N-((1R,2R)-2-{5-Chloro-2-[3-(2-dimethylamino-acetyl)-8-methoxy-2,3,4,5-tetrahydro-1H-benzo[d]azepin-7-ylamino]-pyrimidin-4-ylamino}-cyclohexyl)-methanesulfonamide;

2-{5-Chloro-2-[8-methoxy-3-(3-morpholin-4-yl-propyl)-2-oxo-2,3,4,5-tetrahydro-1H-benzo[d]azepin-7-ylamino]-pyrimidin-4-ylamino}-N-methyl-benzamide;

2-{7-[5-Chloro-4-(2-methoxy-4-morpholin-4-yl-phenylamino)-pyrimidin-2-ylamino]-1,2,4,5-tetrahydro-benzo[d]azepin-3-yl}-N-methyl-acetamide;

(1S,2S,3R,4R)-3-{5-Chloro-2-[3-(2-methanesulfonyl-ethyl)-8-methoxy-2,3,4,5-tetrahydro-1H-benzo[d]azepin-7-ylamino]-pyrimidin-4-ylamino}-bicyclo[2.2.1]hept-5-ene-2-carboxylic acid amide;

5-Chloro-N*2*-(3-ethyl-8-methoxy-2,3,4,5-tetrahydro-1H-benzo[d]azepin-7-yl)-N*4*-(2-methoxy-4-morpholin-4-yl-phenyl)-pyrimidine-2,4-diamine;

2-{7-[5-Chloro-4-(2-methoxy-phenylamino)-pyrimidin-2-ylamino]-8-methoxy-1,2,4,5-tetrahydro-benzo[d]azepin-3-yl}-N,N-dimethyl-acetamide;

1-{7-[5-Chloro-4-(2-methoxy-phenylamino)-pyrimidin-2-ylamino]-8-methoxy-1,2,4,5-tetrahydro-benzo[d]azepin-3-yl}-2-dimethylamino-ethanone;

5-Chloro-N*2*-[3-(2-methanesulfonyl-ethyl)-8-methoxy-2,3,4,5-tetrahydro-1H-benzo[d]azepin-7-yl]-N*4*-(2-methoxy-phenyl)-pyrimidine-2,4-diamine;

2-{7-[5-Chloro-4-(2-methoxy-phenylamino)-pyrimidin-2-ylamino]-8-methoxy-1,2,4,5-tetrahydro-benzo[d]azepin-3-yl}-N-methyl-acetamide;

3-[5-Chloro-2-(3-dimethylcarbamoylmethyl-8-methoxy-2,3,4,5-tetrahydro-1H-benzo[d]azepin-7-ylamino)-pyrimidin-4-ylamino]-4-methoxy-benzamide;

3-{5-Chloro-2-[3-(2-methanesulfonyl-ethyl)-8-methoxy-2,3,4,5-tetrahydro-1H-benzo[d]azepin-7-ylamino]-pyrimidin-4-ylamino}-4-methoxy-benzamide;

3-[5-Chloro-2-(8-methoxy-3-methylcarbamoylmethyl-2,3,4,5-tetrahydro-1H-benzo[d]azepin-7-ylamino)-pyrimidin-4-ylamino]-4-methoxy-benzamide;

3-{5-Chloro-2-[3-(2-dimethylamino-acetyl)-8-methoxy-2,3,4,5-tetrahydro-1H-benzo[d]azepin-7-ylamino]-pyrimidin-4-ylamino}-4-methoxy-benzamide;

3-{5-Chloro-2-[8-methoxy-3-(2-methoxy-ethyl)-2,3,4,5-tetrahydro-1H-benzo[d]azepin-7-ylamino]-pyrimidin-4-ylamino}-4-methoxy-benzamide;

2-{7-[5-Chloro-4-(2-dimethylsulfamoyl-phenylamino)-pyrimidin-2-ylamino]-8-methoxy-1,2,4,5-tetrahydro-benzo[d]azepin-3-yl}-N,N-dimethyl-acetamide;

2-{7-[5-Chloro-4-(2-methanesulfonyl-phenylamino)-pyrimidin-2-ylamino]-8-methoxy-1,2,4,5-tetrahydro-benzo[d]azepin-3-yl}-N,N-dimethyl-acetamide;

2-{7-[5-Chloro-4-(2-methanesulfonyl-phenylamino)-pyrimidin-2-ylamino]-8-methoxy-1,2,4,5-tetrahydro-benzo[d]azepin-3-yl}-acetamide;

2-{7-[5-Chloro-4-(2-ethoxy-phenylamino)-pyrimidin-2-ylamino]-8-methoxy-1,2,4,5-tetrahydro-benzo[d]azepin-3-yl}-N,N-dimethyl-acetamide;

2-{7-[5-Chloro-4-(3-morpholin-4-yl-phenylamino)-pyrimidin-2-ylamino]-8-methoxy-1,2,4,5-tetrahydro-benzo[d]azepin-3-yl}-N,N-dimethyl-acetamide;

4-[5-Chloro-2-(3-dimethylcarbamoylmethyl-8-methoxy-2,3,4,5-tetrahydro-1H-benzo[d]azepin-7-ylamino)-pyrimidin-4-ylamino]-3-methoxy-benzamide;

2-{7-[5-Chloro-4-(2-cyanomethoxy-phenylamino)-pyrimidin-2-ylamino]-8-methoxy-1,2,4,5-tetrahydro-benzo[d]azepin-3-yl}-N,N-dimethyl-acetamide;

5-Chloro-N*2*-[3-(2-methanesulfonyl-ethyl)-8-methoxy-2,3,4,5-tetrahydro-1H-benzo[d]azepin-7-yl]-N*4*-(2-methanesulfonyl-phenyl)-pyrimidine-2,4-diamine;

2-{7-[5-Chloro-4-(5-cyano-2-methoxy-phenylamino)-pyrimidin-2-ylamino]-8-methoxy-1,2,4,5-tetrahydro-benzo[d]azepin-3-yl}-N,N-dimethyl-acetamide;

2-{7-[5-Chloro-4-(4-morpholin-4-yl-phenylamino)-pyrimidin-2-ylamino]-8-methoxy-1,2,4,5-tetrahydro-benzo[d]azepin-3-yl}-N,N-dimethyl-acetamide;

2-(7-{5-Chloro-4-[2-(propane-2-sulfonyl)-phenylamino]-pyrimidin-2-ylamino}-8-methoxy-1,2,4,5-tetrahydro-benzo[d]azepin-3-yl)-N,N-dimethyl-acetamide;
2-{5-Chloro-2-[3-(2-methanesulfonyl-ethyl)-8-methoxy-2,3,4,5-tetrahydro-1H-benzo[d]azepin-7-ylamino]-pyrimidin-4-ylamino}-N,N-dimethyl-benzenesulfonamide;
4-{5-Chloro-2-[8-methoxy-3-(2-methoxy-1-methoxymethyl-ethyl)-2,3,4,5-tetrahydro-1H-benzo[d]azepin-7-ylamino]-pyrimidin-4-ylamino}-3-methoxy-benzamide;
2-{7-[5-Chloro-4-(5-cyano-2-methoxy-phenylamino)-pyrimidin-2-ylamino]-8-methoxy-1,2,4,5-tetrahydro-benzo[d]azepin-3-yl}-acetamide;
2-{7-[5-Chloro-4-(2-methoxy-4-morpholin-4-yl-phenylamino)-pyrimidin-2-ylamino]-8-methoxy-1,2,4,5-tetrahydro-benzo[d]azepin-3-yl}-1-pyrrolidin-1-yl-ethanone;
4-{5-Chloro-2-[8-methoxy-3-(2-methoxy-ethyl)-2,3,4,5-tetrahydro-1H-benzo[d]azepin-7-ylamino]-pyrimidin-4-ylamino}-3-methoxy-benzamide;
2-{5-Chloro-2-[8-methoxy-3-(2-oxo-2-pyrrolidin-1-yl-ethyl)-2,3,4,5-tetrahydro-1H-benzo[d]azepin-7-ylamino]-pyrimidin-4-ylamino}-N,N-dimethyl-benzenesulfonamide;
2-(7-{5-Chloro-4-[2-(propane-2-sulfonyl)-phenylamino]-pyrimidin-2-ylamino}-8-methoxy-1,2,4,5-tetrahydro-benzo[d]azepin-3-yl)-1-pyrrolidin-1-yl-ethanone;
(1S,2S,3R,4R)-3-{5-Chloro-2-[8-methoxy-3-(2-oxo-2-pyrrolidin-1-yl-ethyl)-2,3,4,5-tetrahydro-1H-benzo[d]azepin-7-ylamino]-pyrimidin-4-ylamino}-bicyclo[2.2.1]hept-5-ene-2-carboxylic acid amide;
N-((1R,2R)-2-{5-Chloro-2-[8-methoxy-3-(2-oxo-2-pyrrolidin-1-yl-ethyl)-2,3,4,5-tetrahydro-1H-benzo[d]azepin-7-ylamino]-pyrimidin-4-ylamino}-cyclohexyl)-methanesulfonamide;
4-{5-Chloro-2-[3-(2-methanesulfonyl-ethyl)-8-methoxy-2,3,4,5-tetrahydro-1H-benzo[d]azepin-7-ylamino]-pyrimidin-4-ylamino}-3-methoxy-benzamide;
2-(7-{5-Chloro-4-[4-methoxy-2-(propane-2-sulfonyl)-phenylamino]-pyrimidin-2-ylamino}-8-methoxy-1,2,4,5-tetrahydro-benzo[d]azepin-3-yl)-N,N-dimethyl-acetamide;
2-{7-[5-Chloro-4-(4-cyano-2-methoxy-phenylamino)-pyrimidin-2-ylamino]-8-methoxy-1,2,4,5-tetrahydro-benzo[d]azepin-3-yl}-N,N-dimethyl-acetamide;
5-Chloro-N*2*-[3-(2-methanesulfonyl-ethyl)-8-methoxy-2,3,4,5-tetrahydro-1H-benzo[d]azepin-7-yl]-N*4*-[2-(propane-2-sulfonyl)-phenyl]-pyrimidine-2,4-diamine;
2-{5-Chloro-2-[8-methoxy-3-(2-methoxy-ethyl)-2,3,4,5-tetrahydro-1H-benzo[d]azepin-7-ylamino]-pyrimidin-4-ylamino}-N,N-dimethyl-benzenesulfonamide;
2-{7-[5-Chloro-4-(4-dimethylamino-2-methoxy-phenylamino)-pyrimidin-2-ylamino]-8-methoxy-1,2,4,5-tetrahydro-benzo[d]azepin-3-yl}-N,N-dimethyl-acetamide;
5-Chloro-N*4*-(4-dimethylamino-2-methoxy-phenyl)-N*2*-[3-(2-methanesulfonyl-ethyl)-8-methoxy-2,3,4,5-tetrahydro-1H-benzo[d]azepin-7-yl]-pyrimidine-2,4-diamine;
5-Chloro-N*2*-[3-(2-methanesulfonyl-ethyl)-8-methoxy-2,3,4,5-tetrahydro-1H-benzo[d]azepin-7-yl]-N*4*-[2-methoxy-4-(2-methoxy-ethoxy)-phenyl]-pyrimidine-2,4-diamine;
2-(7-{5-Chloro-4-[2-methoxy-4-(2-methoxy-ethoxy)-phenylamino]-pyrimidin-2-ylamino}-8-methoxy-1,2,4,5-tetrahydro-benzo[d]azepin-3-yl)-N,N-dimethyl-acetamide;
2-[5-Chloro-2-(8-methoxy-3-oxazol-2-ylmethyl-2,3,4,5-tetrahydro-1H-benzo[d]azepin-7-ylamino)-pyrimidin-4-ylamino]-N,N-dimethyl-benzenesulfonamide;
2-{5-Chloro-2-[8-methoxy-3-(1-methyl-1H-imidazol-2-ylmethyl)-2,3,4,5-tetrahydro-1H-benzo[d]azepin-7-ylamino]-pyrimidin-4-ylamino}-N,N-dimethyl-benzenesulfonamide;
5-Chloro-N*4*-(4-dimethylamino-2-methoxy-phenyl)-N*2*-(8-methoxy-3-oxazol-2-ylmethyl-2,3,4,5-tetrahydro-1H-benzo[d]azepin-7-yl)-pyrimidine-2,4-diamine;
5-Chloro-N*4*-(4-dimethylamino-2-methoxy-phenyl)-N*2*-[8-methoxy-3-(1-methyl-1H-imidazol-2-ylmethyl)-2,3,4,5-tetrahydro-1H-benzo[d]azepin-7-yl]-pyrimidine-2,4-diamine;
5-Chloro-N*4*-[2-methoxy-4-(2-methoxy-ethoxy)-phenyl]-N*2*-(8-methoxy-3-oxazol-2-ylmethyl-2,3,4,5-tetrahydro-1H-benzo[d]azepin-7-yl)-pyrimidine-2,4-diamine;
5-Chloro-N*4*-[2-methoxy-4-(2-methoxy-ethoxy)-phenyl]-N*2*-[8-methoxy-3-(1-methyl-1H-imidazol-2-ylmethyl)-2,3,4,5-tetrahydro-1H-benzo[d]azepin-7-yl]-pyrimidine-2,4-diamine;
4-[5-Chloro-2-(3-dimethylcarbamoylmethyl-8-methoxy-2,3,4,5-tetrahydro-1H-benzo[d]azepin-7-ylamino)-pyrimidin-4-ylamino]-3-methoxy-N-methyl-benzamide;
4-{5-Chloro-2-[8-methoxy-3-(2-methoxy-1-methoxymethyl-ethyl)-2,3,4,5-tetrahydro-1H-benzo[d]azepin-7-ylamino]-pyrimidin-4-ylamino}-3-methoxy-N-methyl-benzamide;
5-Chloro-N*2*-[3-(2-methanesulfonyl-ethyl)-8-methoxy-2,3,4,5-tetrahydro-1H-benzo[d]azepin-7-yl]-N*4*-[2-(pyrrolidine-1-sulfonyl)-phenyl]-pyrimidine-2,4-diamine;
(1S,2S,3R,4R)-3-[5-Chloro-2-(8-methoxy-3-oxazol-2-ylmethyl-2,3,4,5-tetrahydro-1H-benzo[d]azepin-7-ylamino)-pyrimidin-4-ylamino]-bicyclo[2.2.1]hept-5-ene-2-carboxylic acid amide;
5-Chloro-N*4*-(2-methoxy-4-morpholin-4-yl-phenyl)-N*2*-(8-methoxy-3-oxazol-2-ylmethyl-2,3,4,5-tetrahydro-1H-benzo[d]azepin-7-yl)-pyrimidine-2,4-diamine;
2-(7-{5-Chloro-4-[2-(pyrrolidine-1-sulfonyl)-phenylamino]-pyrimidin-2-ylamino}-8-methoxy-1,2,4,5-tetrahydro-benzo[d]azepin-3-yl)-N,N-dimethyl-acetamide;
4-[5-Chloro-2-(8-methoxy-3-oxazol-2-ylmethyl-2,3,4,5-tetrahydro-1H-benzo[d]azepin-7-ylamino)-pyrimidin-4-ylamino]-3-methoxy-N-methyl-benzamide;
2-{5-Chloro-2-[8-methoxy-3-(3-morpholin-4-yl-propyl)-2-oxo-2,3,4,5-tetrahydro-1H-benzo[d]azepin-7-ylamino]-pyrimidin-4-ylamino}-N,N-dimethyl-benzenesulfonamide;
2-[7-(5-Chloro-4-{2-[(2-methoxy-ethyl)-methyl-sulfamoyl]-phenylamino}-pyrimidin-2-ylamino)-8-methoxy-1,2,4,5-tetrahydro-benzo[d]azepin-3-yl]-N,N-dimethyl-acetamide;
2-[5-Chloro-2-(3-dimethylcarbamoylmethyl-8-methoxy-2,3,4,5-tetrahydro-1H-benzo[d]azepin-7-ylamino)-pyrimidin-4-ylamino]-5-dimethylamino-N-methyl-benzamide;
2-{7-[5-Chloro-4-(2-oxo-1,2-dihydro-pyridin-3-ylamino)-pyrimidin-2-ylamino]-8-methoxy-1,2,4,5-tetrahydro-benzo[d]azepin-3-yl}-N,N-dimethyl-acetamide;
2-(7-{5-Chloro-4-[4-dimethylamino-2-(propane-2-sulfonyl)-phenylamino]-pyrimidin-2-ylamino}-8-methoxy-1,2,4,5-tetrahydro-benzo[d]azepin-3-yl)-N,N-dimethyl-acetamide;
2-(7-{5-Chloro-4-[2-(3-hydroxy-pyrrolidine-1-sulfonyl)-phenylamino]-pyrimidin-2-ylamino}-8-methoxy-1,2,4,5-tetrahydro-benzo[d]azepin-3-yl)-N,N-dimethyl-acetamide;

2-(7-{5-Chloro-4-[4-(2-methoxy-ethoxy)-2-(propane-2-sulfonyl)-phenylamino]-pyrimidin-2-ylamino}-8-methoxy-1,2,4,5-tetrahydro-benzo[d]azepin-3-yl)-N,N-dimethyl-acetamide;
2-{7-[5-Chloro-4-(2-methoxy-pyridin-3-ylamino)-pyrimidin-2-ylamino]-8-methoxy-1,2,4,5-tetrahydro-benzo[d]azepin-3-yl}-N,N-dimethyl-acetamide;
5-Chloro-N*2*-(8-methoxy-3-oxazol-2-ylmethyl-2,3,4,5-tetrahydro-1H-benzo[d]azepin-7-yl)-N*4*-[2-(pyrrolidine-1-sulfonyl)-phenyl]-pyrimidine-2,4-diamine;
2-{5-Chloro-2-[8-methoxy-3-(2-morpholin-4-yl-acetyl)-2,3,4,5-tetrahydro-1H-benzo[d]azepin-7-ylamino]-pyrimidin-4-ylamino}-N,N-dimethyl-benzenesulfonamide;
7-{5-Chloro-4-[2-(3-hydroxy-pyrrolidine-1-sulfonyl)-phenylamino]-pyrimidin-2-ylamino}-8-methoxy-1,3,4,5-tetrahydro-benzo[d]azepin-2-one;
2-[5-Chloro-2-(8-methoxy-2-oxo-2,3,4,5-tetrahydro-1H-benzo[d]azepin-7-ylamino)-pyrimidin-4-ylamino]-N,N-dimethyl-benzenesulfonamide;
2-{5-Chloro-2-[8-methoxy-3-(2-morpholin-4-yl-ethyl)-2-oxo-2,3,4,5-tetrahydro-1H-benzo[d]azepin-7-ylamino]-pyrimidin-4-ylamino}-N,N-dimethyl-benzenesulfonamide;
1-{5-Chloro-2-[8-methoxy-3-(2-methoxy-ethyl)-2,3,4,5-tetrahydro-1H-benzo[d]azepin-7-ylamino]-pyrimidin-4-ylamino}-cyclopropanecarboxylic acid methylamide;
1-{5-Chloro-2-[8-methoxy-3-(2-methoxy-ethyl)-2,3,4,5-tetrahydro-1H-benzo[d]azepin-7-ylamino]-pyrimidin-4-ylamino}-cyclopropanecarboxylic acid cyanomethyl-amide;
1-[5-Chloro-2-(3-dimethylcarbamoylmethyl-8-methoxy-2,3,4,5-tetrahydro-1H-benzo[d]azepin-7-ylamino)-pyrimidin-4-ylamino]-cyclopropanecarboxylic acid methylamide;
1-[5-Chloro-2-(3-dimethylcarbamoylmethyl-8-methoxy-2,3,4,5-tetrahydro-1H-benzo[d]azepin-7-ylamino)-pyrimidin-4-ylamino]-cyclopropanecarboxylic acid cyanomethyl-amide;
2-{7-[5-Chloro-4-(2,6-dimethoxy-pyridin-3-ylamino)-pyrimidin-2-ylamino]-8-methoxy-1,2,4,5-tetrahydro-benzo[d]azepin-3-yl}-N,N-dimethyl-acetamide;
2-{2-[3-(2-Azetidin-1-yl-2-oxo-ethyl)-8-methoxy-2,3,4,5-tetrahydro-1H-benzo[d]azepin-7-ylamino]-5-chloro-pyrimidin-4-ylamino}-N,N-dimethyl-benzenesulfonamide;
1-[5-Chloro-2-(3-dimethylcarbamoylmethyl-8-methoxy-2,3,4,5-tetrahydro-1H-benzo[d]azepin-7-ylamino)-pyrimidin-4-ylamino]-cyclopentanecarboxylic acid isopropyl ester;
1-[5-Chloro-2-(3-dimethylcarbamoylmethyl-8-methoxy-2,3,4,5-tetrahydro-1H-benzo[d]azepin-7-ylamino)-pyrimidin-4-ylamino]-cyclopentanecarboxylic acid methylamide;
(1S,2S,3R,4R)-3-[5-Chloro-2-(1-methoxy-8-morpholin-4-yl-6,7,8,9-tetrahydro-5H-benzocyclohepten-2-ylamino)-pyrimidin-4-ylamino]-bicyclo[2.2.1]hept-5-ene-2-carboxylic acid amide;
2-(7-{5-Chloro-4-[2-((R)-3-hydroxy-pyrrolidine-1-sulfonyl)-phenylamino]-pyrimidin-2-ylamino}-8-methoxy-1,2,4,5-tetrahydro-benzo[d]azepin-3-yl)-N,N-dimethyl-acetamide;
2-(7-{5-Chloro-4-[2-((S)-3-hydroxy-pyrrolidine-1-sulfonyl)-phenylamino]-pyrimidin-2-ylamino}-8-methoxy-1,2,4,5-tetrahydro-benzo[d]azepin-3-yl)-N,N-dimethyl-acetamide;
2-{2-[3-(2-Amino-2-methyl-propionyl)-8-methoxy-2,3,4,5-tetrahydro-1H-benzo[d]azepin-7-ylamino]-5-chloro-pyrimidin-4-ylamino}-N,N-dimethyl-benzenesulfonamide;
2-{7-[5-Chloro-4-(6-methoxy-2-methylamino-pyridin-3-ylamino)-pyrimidin-2-ylamino]-8-methoxy-1,2,4,5-tetrahydro-benzo[d]azepin-3-yl}-N,N-dimethyl-acetamide;
2-{7-[5-Chloro-4-(2-methylamino-6-morpholin-4-yl-pyridin-3-ylamino)-pyrimidin-2-ylamino]-8-methoxy-1,2,4,5-tetrahydro-benzo[d]azepin-3-yl}-N,N-dimethyl-acetamide;
2-[5-Chloro-2-(1-methoxy-8-morpholin-4-yl-6,7,8,9-tetrahydro-5H-benzocyclohepten-2-ylamino)-pyrimidin-4-ylamino]-N,N-dimethyl-benzenesulfonamide;
2-[5-Chloro-2-(8-oxo-6,7,8,9-tetrahydro-5-oxa-9-aza-benzocyclohepten-2-ylamino)-pyrimidin-4-ylamino]-3-fluoro-N-methyl-benzamide;
2-[5-Chloro-2-(5-oxo-2,3,4,5-tetrahydro-1,4-benzoxazepin-7-ylamino)-pyrimidin-4-ylamino]-3-fluoro-N-methyl-benzamide;
3-{3-[5-Chloro-2-(1-ethyl-2-oxo-2,3,4,5-tetrahydro-1H-1-benzazepin-8-ylamino)-pyrimidin-4-ylamino]-phenyl}-propionitrile;
2-[2-(1-Acetyl-4-oxo-1,2,3,4,5,6-hexahydro-benzo[b][1,5]diazocin-8-ylamino)-5-chloro-pyrimidin-4-ylamino]-3-fluoro-N-methyl-benzamide;
{4-[5-Chloro-2-(1-ethyl-2-oxo-2,3,4,5-tetrahydro-1H-1-benzazepin-8-ylamino)-pyrimidin-4-ylamino]-phenyl}-acetonitrile;
{4-[5-Chloro-2-(1-ethyl-2-oxo-2,3,4,5-tetrahydro-1H-1-benzazepin-8-ylamino)-pyrimidin-4-ylamino]-phenoxy}-acetonitrile;
2-{5-Chloro-2-[3-(2-methoxy-ethyl)-2,3,4,5-tetrahydro-1H-3-benzazepin-7-ylamino]-pyrimidin-4-ylamino}-3-hydroxy-N-methyl-benzamide;
2-[2-(1-Acetyl-4-oxo-1,2,3,4,5,6-hexahydro-benzo[b][1,5]diazocin-8-ylamino)-5-chloro-pyrimidin-4-ylamino]-N-ethyl-3-fluoro-benzamide;
{3-[5-Chloro-2-(1-ethyl-2-oxo-2,3,4,5-tetrahydro-1H-1-benzazepin-8-ylamino)-pyrimidin-4-ylamino]-phenyl}-acetonitrile;
{2-[5-Chloro-2-(1-ethyl-2-oxo-2,3,4,5-tetrahydro-1H-1-benzazepin-8-ylamino)-pyrimidin-4-ylamino]-phenoxy}-acetonitrile;
[C] {2-[2-(1-Acetyl-4-oxo-1,2,3,4,5,6-hexahydro-benzo[b][1,5]diazocin-8-ylamino)-5-chloro-pyrimidin-4-ylamino]-phenoxy}-acetonitrile;
3-{2-[5-Chloro-2-(1-ethyl-2-oxo-2,3,4,5-tetrahydro-1H-1-benzazepin-8-ylamino)-pyrimidin-4-ylamino]-phenyl}-propionitrile;
3-{2-[2-(1-Acetyl-4-oxo-1,2,3,4,5,6-hexahydro-benzo[b][1,5]diazocin-8-ylamino)-5-chloro-pyrimidin-4-ylamino]-phenyl}-propionitrile;
8-[5-Chloro-4-(2-methoxy-4-morpholin-4-yl-phenylamino)-pyrimidin-2-ylamino]-5,5-dimethyl-1,3,4,5-tetrahydro-1-benzazepin-2-one;
2-[5-Chloro-2-(5,5-dimethyl-2-oxo-2,3,4,5-tetrahydro-1H-1-benzazepin-7-ylamino)-pyrimidin-4-ylamino]-N-methyl-4-nitro-benzamide;
(1S,2S,3R,4R)-3-[5-Chloro-2-(5,5-dimethyl-2-oxo-2,3,4,5-tetrahydro-1H-1-benzazepin-8-ylamino)-pyrimidin-4-ylamino]-bicyclo[2.2.1]hept-5-ene-2-carboxylic acid amide;
3-{2-[2-(1-Acetyl-4-oxo-1,2,3,4,5,6-hexahydro-1,5-benzodiazepin-8-ylamino)-5-chloro-pyrimidin-4-ylamino]-phenoxy}-propionitrile;
3-{2-[5-Chloro-2-(5,5-dimethyl-2-oxo-2,3,4,5-tetrahydro-1H-1-benzazepin-8-ylamino)-pyrimidin-4-ylamino]-phenoxy}-propionitrile;

4-Amino-2-[5-chloro-2-(5,5-dimethyl-2-oxo-2,3,4,5-tetrahydro-1H-1-benzazepin-7-ylamino)-pyrimidin-4-ylamino]-N-methyl-benzamide;
(2-{5-Chloro-2-[3-(2-methoxy-ethyl)-2,3,4,5-tetrahydro-1H-3-benzazepin-7-ylamino]-pyrimidin-4-ylamino}-phenoxy)-acetonitrile;
2-(2-{5-Chloro-2-[3-(2-methoxy-ethyl)-2,3,4,5-tetrahydro-1H-3-benzazepin-7-ylamino]-pyrimidin-4-ylamino}-phenoxy)-acetamide;
(2-{5-Chloro-2-[3-(2-methoxy-ethyl)-2,3,4,5-tetrahydro-1H-3-benzazepin-7-ylamino]-pyrimidin-4-ylamino}-phenoxy)-acetic acid;
8-{5-Chloro-4-[2-(propane-2-sulfonyl)-phenylamino]-pyrimidin-2-ylamino}-1-ethyl-5,5-dimethyl-1,3,4,5-tetrahydro-1-benzazepin-2-one;
4-Acetylamino-2-[5-chloro-2-(5,5-dimethyl-2-oxo-2,3,4,5-tetrahydro-1H-1-benzazepin-7-ylamino)-pyrimidin-4-ylamino]-N-methyl-benzamide;
(2-{5-Chloro-2-[3-(2-methoxy-ethyl)-2,3,4,5-tetrahydro-1H-3-benzazepin-7-ylamino]-pyrimidin-4-ylamino}-3-methyl-phenoxy)-acetonitrile;
{2-[2-(1-Acetyl-4-oxo-1,2,3,4,5,6-hexahydro-benzo[b][1,5]diazocin-8-ylamino)-5-chloro-pyrimidin-4-ylamino]-3-methyl-phenoxy}-acetonitrile;
(2-{5-Chloro-2-[1-(2-methoxy-ethyl)-5,5-dimethyl-2-oxo-2,3,4,5-tetrahydro-1H-1-benzazepin-8-ylamino]-pyrimidin-4-ylamino}-3-methyl-phenoxy)-acetonitrile;
8-[5-Chloro-4-(2-methanesulfonyl-phenylamino)-pyrimidin-2-ylamino]-1-ethyl-5,5-dimethyl-1,3,4,5-tetrahydro-1-benzazepin-2-one;
5-Chloro-N(4)-(2-methanesulfonyl-phenyl)-N(2)-[3-(2-methoxy-ethyl)-2,3,4,5-tetrahydro-1H-3-benzazepin-7-yl]-pyrimidine-2,4-diamine;
7-[5-Chloro-4-(2-methanesulfonyl-phenylamino)-pyrimidin-2-ylamino]-1,5,5-trimethyl-1,3,4,5-tetrahydro-1-benzazepin-2-one;
8-{5-Chloro-4-[2-fluoro-6-(propane-2-sulfonyl)-phenylamino]-pyrimidin-2-ylamino}-5,5-dimethyl-1,3,4,5-tetrahydro-1-benzazepin-2-one;
8-{5-Chloro-4-[2-fluoro-6-(propane-2-sulfonyl)-phenylamino]-pyrimidin-2-ylamino}-1-ethyl-5,5-dimethyl-1,3,4,5-tetrahydro-1-benzazepin-2-one;
5-Chloro-N(4)-[2-fluoro-6-(propane-2-sulfonyl)-phenyl]-N(2)-[3-(2-methoxy-ethyl)-2,3,4,5-tetrahydro-1H-3-benzazepin-7-yl]-pyrimidine-2,4-diamine;
7-{5-Chloro-4-[2-fluoro-6-(propane-2-sulfonyl)-phenylamino]-pyrimidin-2-ylamino}-5,5-dimethyl-1,3,4,5-tetrahydro-1-benzazepin-2-one;
8-{5-Chloro-4-[2-fluoro-6-(propane-2-sulfonyl)-phenylamino]-pyrimidin-2-ylamino}-1,3,4,5-tetrahydro-1-benzazepin-2-one;
2-[5-Chloro-2-(2-oxo-2,3,4,5-tetrahydro-1H-1-benzazepin-8-ylamino)-pyrimidin-4-ylamino]-3-fluoro-benzamide;
2-{5-Chloro-2-[3-(2-methoxy-ethyl)-2,3,4,5-tetrahydro-1H-3-benzazepin-7-ylamino]-pyrimidin-4-ylamino}-3-fluoro-benzamide;
2-{5-Chloro-2-[3-(2-methoxy-ethyl)-2,3,4,5-tetrahydro-1H-3-benzazepin-7-ylamino]-pyrimidin-4-ylamino}-3-fluoro-benzamide;
8-[5-Chloro-4-(2-fluoro-6-methanesulfonyl-phenylamino)-pyrimidin-2-ylamino]-1-ethyl-5,5-dimethyl-1,3,4,5-tetrahydro-1-benzazepin-2-one;
7-[5-Chloro-4-(2-fluoro-6-methanesulfonyl-phenylamino)-pyrimidin-2-ylamino]-5,5-dimethyl-1,3,4,5-tetrahydro-1-benzazepin-2-one;
8-[5-Chloro-4-(2-fluoro-6-methanesulfonyl-phenylamino)-pyrimidin-2-ylamino]-1,3,4,5-tetrahydro-1-benzazepin-2-one;
5-Chloro-N(4)-(2-fluoro-6-methanesulfonyl-phenyl)-N(2)-[3-(2-methoxy-ethyl)-2,3,4,5-tetrahydro-1H-3-benzazepin-7-yl]-pyrimidine-2,4-diamine;
3-({2-[5-Chloro-2-(5,5-dimethyl-2-oxo-2,3,4,5-tetrahydro-1H-1-benzazepin-8-ylamino)-pyrimidin-4-ylamino]-3-fluoro-phenyl}-methyl-amino)-propionitrile;
3-({2-[5-Chloro-2-(1-ethyl-5,5-dimethyl-2-oxo-2,3,4,5-tetrahydro-1H-1-benzazepin-8-ylamino)-pyrimidin-4-ylamino]-3-fluoro-phenyl}-methyl-amino)-propionitrile;
3-[(2-{5-Chloro-2-[3-(2-methoxy-ethyl)-2,3,4,5-tetrahydro-1H-3-benzazepin-7-ylamino]-pyrimidin-4-ylamino}-3-fluoro-phenyl)-methyl-amino]-propionitrile;
3-({2-[5-Chloro-2-(5,5-dimethyl-2-oxo-2,3,4,5-tetrahydro-1H-1-benzazepin-7-ylamino)-pyrimidin-4-ylamino]-3-fluoro-phenyl}-methyl-amino)-propionitrile;
3-({2-[5-Chloro-2-(5,5-dimethyl-2-oxo-2,3,4,5-tetrahydro-1H-1-benzazepin-7-ylamino)-pyrimidin-4-ylamino]-3-fluoro-phenyl}-methyl-amino)-propionitrile;
2-[5-Chloro-2-(4-oxo-4,5-dihydro-6-oxa-10b-aza-benz[e]azulen-9-ylamino)-pyrimidin-4-ylamino]-3-fluoro-N-methyl-benzamide;
2-[5-Chloro-2-(6-oxa-10b-aza-benz[e]azulen-9-ylamino)-pyrimidin-4-ylamino]-3-fluoro-N-methyl-benzamide;
2-[5-Chloro-2-(6,6-dimethyl-5,6-dihydro-4H-3,10b-diaza-benz[e]azulen-9-ylamino)-pyrimidin-4-ylamino]-3-fluoro-N-methyl-benzamide;
2-{5-Chloro-2-[5,5-dimethyl-2-oxo-3-(2,2,2-trifluoro-acetylamino)-2,3,4,5-tetrahydro-1H-1-benzazepin-8-ylamino]-pyrimidin-4-ylamino}-3-fluoro-N-methyl-benzamide;
2-[2-(3-Amino-5,5-dimethyl-2-oxo-2,3,4,5-tetrahydro-1H-1-benzazepin-8-ylamino)-5-chloro-pyrimidin-4-ylamino]-3-fluoro-N-methyl-benzamide;
8-{5-Chloro-4-[2-fluoro-6-(tetrahydro-furan-3-yloxy)-phenylamino]-pyrimidin-2-ylamino}-1,3,4,5-tetrahydro-1-benzazepin-2-one;
5-Chloro-N(4)-[2-fluoro-6-(tetrahydro-furan-3-yloxy)-phenyl]-N(2)-[3-(2-methoxy-ethyl)-2,3,4,5-tetrahydro-1H-3-benzazepin-7-yl]-pyrimidine-2,4-diamine;
5-Chloro-N(4)-[2-fluoro-6-(tetrahydro-furan-3-ylmethoxy)-phenyl]-N(2)-[3-(2-methoxy-ethyl)-2,3,4,5-tetrahydro-1H-3-benzazepin-7-yl]-pyrimidine-2,4-diamine;
8-{5-Chloro-4-[2-fluoro-6-(tetrahydro-furan-3-ylmethoxy)-phenylamino]-pyrimidin-2-ylamino}-1,3,4,5-tetrahydro-1-benzazepin-2-one;
2-{5-Chloro-2-[3-(2-methoxy-ethyl)-2,3,4,5-tetrahydro-1H-3-benzazepin-7-ylamino]-pyrimidin-4-ylamino}-3,5-difluoro-N-methyl-benzamide;
2-[5-Chloro-2-(2-oxo-2,3,4,5-tetrahydro-1H-1-benzazepin-8-ylamino)-pyrimidin-4-ylamino]-3,5-difluoro-N-methyl-benzamide;
2-{5-Chloro-2-[5,5-dimethyl-2-oxo-3-(2,2,2-trifluoro-acetylamino)-2,3,4,5-tetrahydro-1H-1-benzazepin-8-ylamino]-pyrimidin-4-ylamino}-3-fluoro-N-prop-2-ynyl-benzamide;
2-[2-(3-Amino-5,5-dimethyl-2-oxo-2,3,4,5-tetrahydro-1H-1-benzazepin-8-ylamino)-5-chloro-pyrimidin-4-ylamino]-3-fluoro-N-prop-2-ynyl-benzamide;
8-{5-Chloro-4-[2-fluoro-6-(tetrahydro-pyran-4-yloxy)-phenylamino]-pyrimidin-2-ylamino}-1,3,4,5-tetrahydro-1-benzazepin-2-one;
5-Chloro-N(4)-[2-fluoro-6-(tetrahydro-pyran-4-yloxy)-phenyl]-N(2)-[3-(2-methoxy-ethyl)-2,3,4,5-tetrahydro-1H-3-benzazepin-7-yl]-pyrimidine-2,4-diamine;

8-{4-[2-(3-Benzyloxy-propoxy)-6-fluoro-phenylamino]-5-chloro-pyrimidin-2-ylamino}-1,3,4,5-tetrahydro-1-benzazepin-2-one;

N(4)-[2-(3-Benzyloxy-propoxy)-6-fluoro-phenyl]-5-chloro-N(2)-[3-(2-methoxy-ethyl)-2,3,4,5-tetrahydro-1H-3-benzazepin-7-yl]-pyrimidine-2,4-diamine;

2-{5-Chloro-2-[3-(2-dimethylamino-acetylamino)-5,5-dimethyl-2-oxo-2,3,4,5-tetrahydro-1H-1-benzazepin-8-ylamino]-pyrimidin-4-ylamino}-3-fluoro-N-methyl-benzamide;

8-[5-Chloro-4-(2,4-difluoro-6-morpholin-4-yl-phenylamino)-pyrimidin-2-ylamino]-1,3,4,5-tetrahydro-1-benzazepin-2-one;

5-Chloro-N(4)-(2,4-difluoro-6-morpholin-4-yl-phenyl)-N(2)-[3-(2-methoxy-ethyl)-2,3,4,5-tetrahydro-1H-3-benzazepin-7-yl]-pyrimidine-2,4-diamine;

2-[5-Chloro-2-(5,5-dimethyl-3-morpholin-4-yl-2-oxo-2,3,4,5-tetrahydro-1H-1-benzazepin-8-ylamino)-pyrimidin-4-ylamino]-3-fluoro-N-methyl-benzamide;

2-[2-(3-Acetylamino-5,5-dimethyl-2-oxo-2,3,4,5-tetrahydro-1H-1-benzazepin-8-ylamino)-5-chloro-pyrimidin-4-ylamino]-3-fluoro-N-methyl-benzamide;

2-[2-(3-Acetylamino-5,5-dimethyl-2-oxo-2,3,4,5-tetrahydro-1H-1-benzazepin-8-ylamino)-5-chloro-pyrimidin-4-ylamino]-3-fluoro-N-prop-2-ynyl-benzamide;

3-[2-(3-Acetylamino-5,5-dimethyl-2-oxo-2,3,4,5-tetrahydro-1H-1-benzazepin-8-ylamino)-5-chloro-pyrimidin-4-ylamino]-thiophene-2-carboxylic acid methyl amide;

2-{5-Chloro-2-[3-(2-methoxy-acetylamino)-5,5-dimethyl-2-oxo-2,3,4,5-tetrahydro-1H-1-benzazepin-8-ylamino]-pyrimidin-4-ylamino}-3-fluoro-N-methyl-benzamide;

2-{5-Chloro-2-[3-(2-methoxy-acetylamino)-5,5-dimethyl-2-oxo-2,3,4,5-tetrahydro-1H-1-benzazepin-8-ylamino]-pyrimidin-4-ylamino}-3-fluoro-N-prop-2-ynyl-benzamide;

2-{5-Chloro-2-[3-(2-methoxy-ethylamino)-5,5-dimethyl-2,3,4,5-tetrahydro-1H-1-benzazepin-8-ylamino]-pyrimidin-4-ylamino}-3-fluoro-N-methyl-benzamide;

Pyrrolidine-1-carboxylic acid {8-[5-chloro-4-(2-fluoro-6-methylcarbamoyl-phenylamino)-pyrimidin-2-ylamino]-5,5-dimethyl-2-oxo-2,3,4,5-tetrahydro-1H-1-benzazepin-3-yl}-amide;

Pyrrolidine-1-carboxylic acid {8-[5-chloro-4-(2-fluoro-6-prop-2-ynylcarbamoyl-phenylamino)-pyrimidin-2-ylamino]-5,5-dimethyl-2-oxo-2,3,4,5-tetrahydro-1H-1-benzazepin-3-yl}-amide;

2-{5-Chloro-2-[(S)-5,5-dimethyl-2-oxo-3-(2,2,2-trifluoro-acetylamino)-2,3,4,5-tetrahydro-1H-1-benzazepin-8-ylamino]-pyrimidin-4-ylamino}-3-fluoro-N-methyl-benzamide;

2-{5-Chloro-2-[(R)-5,5-dimethyl-2-oxo-3-(2,2,2-trifluoro-acetylamino)-2,3,4,5-tetrahydro-1H-1-benzazepin-8-ylamino]-pyrimidin-4-ylamino}-3-fluoro-N-methyl-benzamide;

{8-[5-Chloro-4-(2-fluoro-6-methylcarbamoyl-phenylamino)-pyrimidin-2-ylamino]-5,5-dimethyl-2-oxo-2,3,4,5-tetrahydro-1H-1-benzazepin-3-yl}-carbamic acid methyl ester;

2-{5-Chloro-4-[2-fluoro-6-(tetrahydro-furan-3-yloxy)-phenylamino]-pyrimidin-2-ylamino}-5-methyl-8,9-dihydro-5H-7-oxa-5-aza-benzocyclohepten-6-one;

2-{5-Chloro-2-[4-oxo-1-(2,2,2-trifluoro-acetyl)-1,2,3,4,5,6-hexahydro-benzo[b][1,5]diazocin-8-ylamino]-pyrimidin-4-ylamino}-N-methyl-benzamide;

2-[5-Chloro-2-(4-oxo-1,2,3,4,5,6-hexahydro-benzo[b][1,5]diazocin-8-ylamino)-pyrimidin-4-ylamino]-N-methyl-benzamide;

2-{5-Chloro-2-[4-oxo-1-(2,2,2-trifluoro-acetyl)-1,2,3,4,5,6-hexahydro-benzo[b][1,5]diazocin-8-ylamino]-pyrimidin-4-ylamino}-N-methyl-benzenesulfonamide;

2-[5-Chloro-2-(4-oxo-1,2,3,4,5,6-hexahydro-benzo[b][1,5]diazocin-8-ylamino)-pyrimidin-4-ylamino]-N-methyl-benzenesulfonamide;

2-[2-(1-Acetyl-4-oxo-1,2,3,4,5,6-hexahydro-benzo[b][1,5]diazocin-8-ylamino)-5-chloro-pyrimidin-4-ylamino]-N-methyl-benzamide;

2-{5-Chloro-4-[2-fluoro-6-(tetrahydro-furan-3-yloxy)-phenoxy]-pyrimidin-2-ylamino}-5-methyl-8,9-dihydro-5H-7-oxa-5-aza-benzocyclohepten-6-one;

{5-Chloro-4-[2-fluoro-6-(tetrahydro-furan-3-yloxy)-phenoxy]-pyrimidin-2-yl}-[3-(2-methoxy-ethyl)-2,3,4,5-tetrahydro-1H-3-benzazepin-7-yl]-amine;

7-{5-Chloro-4-[2-methoxy-4-(4-methyl-piperazin-1-yl)-phenylamino]-pyrimidin-2-ylamino}-1-ethyl-6-methoxy-1,3,4,5-tetrahydro-benzo[b]azepin-2-one;

(1S,2S,3R,4R)-3-[5-Chloro-2-(8-methoxy-5,5-dimethyl-2-oxo-2,3,4,5-tetrahydro-1H-benzo[b]azepin-7-ylamino-pyrimidin-4-ylamino]-bicyclo[2.2.1]hept-5-ene-2-carboxylic acid amide;

(1S,2S,3R,4R)-3-[5-Chloro-2-(8-methoxy-1,5,5-trimethyl-2-oxo-2,3,4,5-tetrahydro-1H-benzo[b]azepin-7-ylamino)-pyrimidin-4-ylamino]-bicyclo[2.2.1]hept-5-ene-2-carboxylic acid amide;

(1S,2S,3R,4R)-3-[5-Chloro-2-(1-ethyl-8-methoxy-5,5-dimethyl-2-oxo-2,3,4,5-tetrahydro-1H-benzo[b]azepin-7-ylamino)-pyrimidin-4-ylamino]-bicyclo[2.2.1]hept-5-ene-2-carboxylic acid amide;

(1S,2S,3R,4R)-3-{5-Chloro-2-[8-methoxy-3-(2-methoxy-ethyl)-2,3,4,5-tetrahydro-1H-benzo[d]azepin-7-ylamino]-pyrimidin-4-ylamino}-bicyclo[2.2.1]hept-5-ene-2-carboxylic acid amide;

(1S,2S,3R,4R)-3-[5-Chloro-2-(1-ethyl-8-methoxy-2-oxo-2,3,4,5-tetrahydro-1H-benzo[b]azepin-7-ylamino)-pyrimidin-4-ylamino]-bicyclo[2.2.1]hept-5-ene-2-carboxylic acid amide;

7-[5-Chloro-4-(2-pyrazol-1-yl-phenylamino)-pyrimidin-2-ylamino]-1-ethyl-8-methoxy-1,3,4,5-tetrahydro-benzo[b]azepin-2-one;

7-[5-Chloro-4-(2-methoxy-phenylamino)-pyrimidin-2-ylamino]-1-ethyl-8-methoxy-1,3,4,5-tetrahydro-benzo[b]azepin-2-one;

7-[5-Chloro-4-(2-pyrazol-1-yl-phenylamino)-pyrimidin-2-ylamino]-1-ethyl-6-methoxy-1,3,4,5-tetrahydro-benzo[b]azepin-2-one;

2-{7-[5-Chloro-4-(2-pyrazol-1-yl-phenylamino)-pyrimidin-2-ylamino]-8-methoxy-1,2,4,5-tetrahydro-benzo[d]azepin-3-yl}-N,N-dimethyl-acetamide;

5-Chloro-N*2*-[8-methoxy-3-(2-methoxy-ethyl)-2,3,4,5-tetrahydro-1H-benzo[d]azepin-7-yl]-N*4*-(2-pyrazol-1-yl-phenyl)-pyrimidine-2,4-diamine;

(1R,2R,3S,4S)-3-{5-Chloro-2-[8-methoxy-3-(2-methoxy-ethyl)-2,3,4,5-tetrahydro-1H-benzo[d]azepin-7-ylamino]-pyrimidin-4-ylamino}-bicyclo[2.2.1]hept-5-ene-2-carboxylic acid amide;

7-[5-Chloro-4-(2-pyrazol-1-yl-phenylamino)-pyrimidin-2-ylamino]-1,5,5-trimethyl-1,3,4,5-tetrahydro-benzo[b]azepin-2-one;

2-[5-Chloro-2-(1-ethyl-8-methoxy-2-oxo-2,3,4,5-tetrahydro-1H-benzo[b]azepin-7-ylamino)-pyrimidin-4-ylamino]-N,N-dimethyl-benzenesulfonamide;

2-[5-Chloro-2-(1,5,5-trimethyl-2-oxo-2,3,4,5-tetrahydro-1H-benzo[b]azepin-7-ylamino)-pyrimidin-4-ylamino]-N,N-dimethyl-benzenesulfonamide;

2-[5-Chloro-2-(1-ethyl-6-methoxy-2-oxo-2,3,4,5-tetrahydro-1H-benzo[b]azepin-7-ylamino)-pyrimidin-4-ylamino]-N,N-dimethyl-benzenesulfonamide;

7-{5-Chloro-4-[2-(propane-2-sulfonyl)-phenylamino]-pyrimidin-2-ylamino}-1-ethyl-8-methoxy-1,3,4,5-tetrahydro-benzo[b]azepin-2-one;

7-{5-Chloro-4-[2-(propane-2-sulfonyl)-phenylamino]-pyrimidin-2-ylamino}-1-ethyl-6-methoxy-1,3,4,5-tetrahydro-benzo[b]azepin-2-one;

7-{5-Chloro-4-[2-(propane-2-sulfonyl)-phenylamino]-pyrimidin-2-ylamino}-1,5,5-trimethyl-1,3,4,5-tetrahydro-benzo[b]azepin-2-one;

(1S,2S,3R,4R)-3-{5-Chloro-2-[1-ethyl-6-methoxy-2-oxo-3-(2,2,2-trifluoro-acetylamino)-2,3,4,5-tetrahydro-1H-benzo[b]azepin-7-ylamino]-pyrimidin-4-ylamino}-bicyclo[2.2.1]hept-5-ene-2-carboxylic acid amide;

(1S,2S,3R,4R)-3-[2-(3-Amino-1-ethyl-6-methoxy-2-oxo-2,3,4,5-tetrahydro-1H-benzo[b]azepin-7-ylamino)-5-chloro-pyrimidin-4-ylamino]-bicyclo[2.2.1]hept-5-ene-2-carboxylic acid amide;

(1S,2S,3R,4R)-3-[2-(3-Amino-1-ethyl-6-methoxy-2-oxo-2,3,4,5-tetrahydro-1H-benzo[b]azepin-7-ylamino)-5-chloro-pyrimidin-4-ylamino]-bicyclo[2.2.1]hept-5-ene-2-carboxylic acid amide;

N-(7-{5-Chloro-4-[2-(propane-2-sulfonyl)-phenylamino]-pyrimidin-2-ylamino}-1-ethyl-6-methoxy-2-oxo-2,3,4,5-tetrahydro-1H-benzo[b]azepin-3-yl)-2,2,2-trifluoro-acetamide;

N-{7-[5-Chloro-4-(2-dimethylsulfamoyl-phenylamino)-pyrimidin-2-ylamino]-1-ethyl-6-methoxy-2-oxo-2,3,4,5-tetrahydro-1H-benzo[b]azepin-3-yl}-2,2,2-trifluoro-acetamide;

N-{7-[5-Chloro-4-((1R,2R)-2-methanesulfonylamino-cyclohexylamino)-pyrimidin-2-ylamino]-1-ethyl-6-methoxy-2-oxo-2,3,4,5-tetrahydro-1H-benzo[b]azepin-3-yl}-2,2,2-trifluoro-acetamide;

2-[2-(3-Amino-1-ethyl-6-methoxy-2-oxo-2,3,4,5-tetrahydro-1H-benzo[b]azepin-7-ylamino)-5-chloro-pyrimidin-4-ylamino]-N,N-dimethyl-benzenesulfonamide;

3-Amino-7-{5-chloro-4-[2-(propane-2-sulfonyl)-phenylamino]-pyrimidin-2-ylamino}-1-ethyl-6-methoxy-1,3,4,5-tetrahydro-benzo[b]azepin-2-one;

N-{(1R,2R)-2-[2-(3-Amino-1-ethyl-6-methoxy-2-oxo-2,3,4,5-tetrahydro-1H-benzo[b]azepin-7-ylamino)-5-chloro-pyrimidin-4-ylamino]-cyclohexyl}-methanesulfonamide;

7-[5-Chloro-4-(4-dimethylamino-2-methoxy-phenylamino)-pyrimidin-2-ylamino]-1-ethyl-6-methoxy-1,3,4,5-tetrahydro-benzo[b]azepin-2-one;

7-[5-Chloro-4-(4-dimethylamino-2-methoxy-phenylamino)-pyrimidin-2-ylamino]-1-ethyl-8-methoxy-1,3,4,5-tetrahydro-benzo[b]azepin-2-one;

N-{7-[5-Chloro-4-(4-dimethylamino-2-methoxy-phenylamino)-pyrimidin-2-ylamino]-1-ethyl-6-methoxy-2-oxo-2,3,4,5-tetrahydro-1H-benzo[b]azepin-3-yl}-2,2,2-trifluoro-acetamide;

7-[5-Chloro-4-(4-dimethylamino-2-methoxy-phenylamino)-pyrimidin-2-ylamino]-1,5,5-trimethyl-1,3,4,5-tetrahydro-benzo[b]azepin-2-one;

3-Amino-7-[5-chloro-4-(4-dimethylamino-2-methoxy-phenylamino)-pyrimidin-2-ylamino]-1-ethyl-6-methoxy-1,3,4,5-tetrahydro-benzo[b]azepin-2-one;

(1S,2S,3R,4R)-3-[5-Chloro-2-((R)-1-ethyl-6-methoxy-3-morpholin-4-yl-2-oxo-2,3,4,5-tetrahydro-1H-benzo[b]azepin-7-ylamino)-pyrimidin-4-ylamino]-bicyclo[2.2.1]hept-5-ene-2-carboxylic acid amide;

(1S,2S,3R,4R)-3-[5-Chloro-2-((S)-1-ethyl-6-methoxy-3-morpholin-4-yl-2-oxo-2,3,4,5-tetrahydro-1H-benzo[b]azepin-7-ylamino)-pyrimidin-4-ylamino]-bicyclo[2.2.1]hept-5-ene-2-carboxylic acid amide;

(1S,2S,3R,4R)-3-[5-Chloro-2-((R)-3-dimethylamino-1-ethyl-6-methoxy-2-oxo-2,3,4,5-tetrahydro-1H-benzo[b]azepin-7-ylamino)-pyrimidin-4-ylamino]-bicyclo[2.2.1]hept-5-ene-2-carboxylic acid amide;

(1S,2S,3R,4R)-3-[5-Chloro-2-((S)-3-dimethylamino-1-ethyl-6-methoxy-2-oxo-2,3,4,5-tetrahydro-1H-benzo[b]azepin-7-ylamino)-pyrimidin-4-ylamino]-bicyclo[2.2.1]hept-5-ene-2-carboxylic acid amide;

2-[5-Chloro-2-(3-dimethylamino-1-ethyl-6-methoxy-2-oxo-2,3,4,5-tetrahydro-1H-benzo[b]azepin-7-ylamino)-pyrimidin-4-ylamino]-N,N-dimethyl-benzenesulfonamide;

7-[5-Chloro-4-(2-pyrazol-1-yl-phenylamino)-pyrimidin-2-ylamino]-3-dimethylamino-1-ethyl-6-methoxy-1,3,4,5-tetrahydro-benzo[b]azepin-2-one;

(1S,2S,3R,4R)-3-{5-Chloro-2-[(R)-1-ethyl-6-methoxy-3-(2-methoxy-acetylamino)-2-oxo-2,3,4,5-tetrahydro-1H-benzo[b]azepin-7-ylamino]-pyrimidin-4-ylamino}-bicyclo[2.2.1]hept-5-ene-2-carboxylic acid amide;

(1S,2S,3R,4R)-3-{5-Chloro-2-[(S)-1-ethyl-6-methoxy-3-(2-methoxy-acetylamino)-2-oxo-2,3,4,5-tetrahydro-1H-benzo[b]azepin-7-ylamino]-pyrimidin-4-ylamino}-bicyclo[2.2.1]hept-5-ene-2-carboxylic acid amide;

N-{7-[5-Chloro-4-(2-dimethylsulfamoyl-phenylamino)-pyrimidin-2-ylamino]-1-ethyl-6-methoxy-2-oxo-2,3,4,5-tetrahydro-1H-benzo[b]azepin-3-yl}-2-methoxy-acetamide;

(1S,2S,4R)-3-{5-Chloro-2-[3-(2-dimethylamino-acetylamino)-1-ethyl-6-methoxy-2-oxo-2,3,4,5-tetrahydro-1H-benzo[b]azepin-7-ylamino]-pyrimidin-4-ylamino}-bicyclo[2.2.1]hept-5-ene-2-carboxylic acid amide;

(1S,2S,3R,4R)-3-{5-Chloro-2-[(R)-3-(2-dimethylamino-acetylamino)-1-ethyl-6-methoxy-2-oxo-2,3,4,5-tetrahydro-1H-benzo[b]azepin-7-ylamino]-pyrimidin-4-ylamino}-bicyclo[2.2.1]hept-5-ene-2-carboxylic acid amide;

(1S,2S,3R,4R)-3-{5-Chloro-2-[(S)-3-(2-dimethylamino-acetylamino)-1-ethyl-6-methoxy-2-oxo-2,3,4,5-tetrahydro-1H-benzo[b]azepin-7-ylamino]-pyrimidin-4-ylamino}-bicyclo[2.2.1]hept-5-ene-2-carboxylic acid amide;

N-{7-[5-Chloro-4-(2-dimethylsulfamoyl-phenylamino)-pyrimidin-2-ylamino]-1-ethyl-6-methoxy-2-oxo-2,3,4,5-tetrahydro-1H-benzo[b]azepin-3-yl}-2-dimethylamino-acetamide;

(1S,2S,3R,4R)-3-{5-Chloro-2-[(R)-3-(cyclopropanecarbonyl-amino)-1-ethyl-6-methoxy-2-oxo-2,3,4,5-tetrahydro-1H-benzo[b]azepin-7-ylamino]-pyrimidin-4-ylamino}-bicyclo[2.2.1]hept-5-ene-2-carboxylic acid amide;

(1S,2S,3R,4R)-3-{5-Chloro-2-[(S)-3-(cyclopropanecarbonyl-amino)-1-ethyl-6-methoxy-2-oxo-2,3,4,5-tetrahydro-1H-benzo[b]azepin-7-ylamino]-pyrimidin-4-ylamino}-bicyclo[2.2.1]hept-5-ene-2-carboxylic acid amide;

Cyclopropanecarboxylic acid {7-[5-chloro-4-(2-dimethylsulfamoyl-phenylamino)-pyrimidin-2-ylamino]-1-ethyl-6-methoxy-2-oxo-2,3,4,5-tetrahydro-1H-benzo[b]azepin-3-yl}-amide;

2-{5-Chloro-2-[3-((R)-3,3,3-trifluoro-2-methoxy-propyl)-2,3,4,5-tetrahydro-1H-benzo[d]azepin-7-ylamino]-pyrimidin-4-ylamino}-3-fluoro-N-methyl-benzamide;

3-{5-Chloro-2-[3-(2-methoxy-ethyl)-2,3,4,5-tetrahydro-1H-benzo[d]azepin-7-ylamino]-pyrimidin-4-ylamino}-4-methyl-thiophene-2-carboxylic acid methylamide;

2-{5-Chloro-2-[3-(2-methoxy-ethyl)-2,3,4,5-tetrahydro-1H-benzo[d]azepin-7-ylamino]-pyrimidin-4-ylamino}-N-ethyl-3-fluoro-benzamide;

2-[5-Chloro-2-(8-methoxy-3-methylcarbamoylmethyl-2,3,4,5-tetrahydro-1H-benzo[d]azepin-7-ylamino)-pyrimidin-4-ylamino]-N-ethyl-3-fluoro-benzamide;
2-[5-Chloro-2-(5,5-dimethyl-2-oxo-2,3,4,5-tetrahydro-1H-benzo[b]azepin-7-ylamino)-pyrimidin-4-ylamino]-N-ethyl-3-fluoro-benzamide;
2-[5-Chloro-2-(1,5,5-trimethyl-2-oxo-2,3,4,5-tetrahydro-1H-benzo[b]azepin-7-ylamino)-pyrimidin-4-ylamino]-N-ethyl-3-fluoro-benzamide;
2-[5-Chloro-2-(3-dimethylcarbamoylmethyl-2,3,4,5-tetrahydro-1H-benzo[d]azepin-7-ylamino)-pyrimidin-4-ylamino]-N-ethyl-3-fluoro-benzamide;
2-{7-[5-Chloro-4-(2-methoxy-4-morpholin-4-yl-phenylamino)-pyrimidin-2-ylamino]-1,2,4,5-tetrahydro-benzo[d]azepin-3-yl}-N,N-dimethyl-acetamide;
2-[5-Chloro-2-(3-dimethylcarbamoylmethyl-2,3,4,5-tetrahydro-1H-benzo[d]azepin-7-ylamino)-pyrimidin-4-ylamino]-3-fluoro-N-methyl-benzamide;
3-Chloro-2-[5-chloro-2-(3-dimethylcarbamoylmethyl-2,3,4,5-tetrahydro-1H-benzo[d]azepin-7-ylamino)-pyrimidin-4-ylamino]-N-methyl-benzamide;
2-{7-[5-Chloro-4-((1R,2R)-2-methanesulfonylamino-cyclohexylamino)-pyrimidin-2-ylamino]-1,2,4,5-tetrahydro-benzo[d]azepin-3-yl}-N,N-dimethyl-acetamide;
2-[5-Chloro-2-(3-methylcarbamoylmethyl-2,3,4,5-tetrahydro-1H-benzo[d]azepin-7-ylamino)-pyrimidin-4-ylamino]-N-ethyl-3-fluoro-benzamide;
3-Chloro-2-[5-chloro-2-(3-methylcarbamoylmethyl-2,3,4,5-tetrahydro-1H-benzo[d]azepin-7-ylamino)-pyrimidin-4-ylamino]-N-methyl-benzamide;
2-{7-[5-Chloro-4-((1R,2R)-2-methanesulfonylamino-cyclohexylamino)-pyrimidin-2-ylamino]-1,2,4,5-tetrahydro-benzo[d]azepin-3-yl}-N-methyl-acetamide;
2-[5-Chloro-2-(2-oxo-2,3,4,5-tetrahydro-1H-benzo[b]azepin-8-ylamino)-pyrimidin-4-ylamino]-3-fluoro-N-methyl-benzamide;
5-Chloro-N(4)-(2-chloro-phenyl)-N(2)-[3-(2-methoxy-ethyl)-2,3,4,5-tetrahydro-1H-benzo[d]azepin-7-yl]-pyrimidine-2,4-diamine;
5-Chloro-N(4)-cyclohexyl-N(2)-[3-(2-methoxy-ethyl)-2,3,4,5-tetrahydro-1H-benzo[d]azepin-7-yl]-pyrimidine-2,4-diamine;
trans-N-(4-{5-Chloro-2-[3-(2-methoxy-ethyl)-2,3,4,5-tetrahydro-1H-benzo[d]azepin-7-ylamino]-pyrimidin-4-ylamino}-cyclohexyl)-methanesulfonamide;
rel-N-((1R,3R)-3-{5-Chloro-2-[3-(2-methoxy-ethyl)-2,3,4,5-tetrahydro-1H-benzo[d]azepin-7-ylamino]-pyrimidin-4-ylamino}-cyclohexyl)-methanesulfonamide;
rel-N-((1S,3R)-3-{5-Chloro-2-[3-(2-methoxy-ethyl)-2,3,4,5-tetrahydro-1H-benzo[d]azepin-7-ylamino]-pyrimidin-4-ylamino}-cyclohexyl)-methanesulfonamide;
cis-N-(4-{5-Chloro-2-[3-(2-methoxy-ethyl)-2,3,4,5-tetrahydro-1H-benzo[d]azepin-7-ylamino]-pyrimidin-4-ylamino}-cyclohexyl)-methanesulfonamide;
rel-N-((1R,3R)-3-{5-Chloro-2-[3-(2-methoxy-ethyl)-2,3,4,5-tetrahydro-1H-benzo[d]azepin-7-ylamino]-pyrimidin-4-ylamino}-cyclohexyl)-N-cyanomethyl-methanesulfonamide;
N-((1R,2R)-2-{5-Chloro-2-[3-(2-methoxy-ethyl)-2,3,4,5-tetrahydro-1H-benzo[d]azepin-7-ylamino]-pyrimidin-4-ylamino}-cyclohexyl)-N-cyanomethyl-methanesulfonamide;
cis-N-(4-{5-Chloro-2-[3-(2-methoxy-ethyl)-2,3,4,5-tetrahydro-1H-benzo[d]azepin-7-ylamino]-pyrimidin-4-ylamino}-cyclohexyl)-N-cyanomethyl-methanesulfonamide;
trans-N-(4-{5-Chloro-2-[3-(2-methoxy-ethyl)-2,3,4,5-tetrahydro-1H-benzo[d]azepin-7-ylamino]-pyrimidin-4-ylamino}-cyclohexyl)-N-cyanomethyl-methanesulfonamide;
rel-N-((1S,3R)-3-{5-Chloro-2-[3-(2-methoxy-ethyl)-2,3,4,5-tetrahydro-1H-benzo[d]azepin-7-ylamino]-pyrimidin-4-ylamino}-cyclohexyl)-N-cyanomethyl-methanesulfonamide;
2-{5-Chloro-2-[3-(2-methoxy-ethyl)-2,3,4,5-tetrahydro-1H-benzo[d]azepin-7-ylamino]-pyrimidin-4-ylamino}-N-prop-2-ynyl-benzamide;
2-[5-Chloro-2-(1-methyl-2-oxo-2,3,4,5-tetrahydro-1H-benzo[b]azepin-7-ylamino)-pyrimidin-4-ylamino]-N-prop-2-ynyl-benzamide;
2-{5-Chloro-2-[3-(2-methoxy-ethyl)-2,3,4,5-tetrahydro-1H-benzo[d]azepin-7-ylamino]-pyrimidin-4-ylamino}-N-methyl-N-prop-2-ynyl-benzamide;
2-[5-Chloro-2-(1-methyl-2-oxo-2,3,4,5-tetrahydro-1H-benzo[b]azepin-7-ylamino)-pyrimidin-4-ylamino]-N-methyl-N-prop-2-ynyl-benzamide;
5-Chloro-N(2)-[3-(2-fluoro-1-fluoromethyl-ethyl)-8-methoxy-2,3,4,5-tetrahydro-1H-benzo[d]azepin-7-yl]-N(4)-(2-methoxy-4-morpholin-4-yl-phenyl)-pyrimidine-2,4-diamine;
N-((1R,2R)-2-{5-Chloro-2-[3-(2-fluoro-1-fluoromethyl-ethyl)-8-methoxy-2,3,4,5-tetrahydro-1H-benzo[d]azepin-7-ylamino]-pyrimidin-4-ylamino}-cyclohexyl)-methanesulfonamide;
2-{5-Chloro-2-[3-(2-fluoro-1-fluoromethyl-ethyl)-8-methoxy-2,3,4,5-tetrahydro-1H-benzo[d]azepin-7-ylamino]-pyrimidin-4-ylamino}-N,N-dimethyl-benzenesulfonamide;
5-Chloro-N(2)-[3-(2-fluoro-1-fluoromethyl-ethyl)-8-methoxy-2,3,4,5-tetrahydro-1H-benzo[d]azepin-7-yl]-N(4)-[2-(propane-2-sulfonyl)-phenyl]-pyrimidine-2,4-diamine;
2-{5-Chloro-2-[3-(2-methoxy-ethyl)-2,3,4,5-tetrahydro-1H-benzo[d]azepin-7-ylamino]-pyrimidin-4-ylamino}-benzoic acid ethyl ester;
2-{5-Chloro-2-[3-(2-methoxy-ethyl)-2,3,4,5-tetrahydro-1H-benzo[d]azepin-7-ylamino]-pyrimidin-4-ylamino}-N-isobutyl-benzamide;
2-{5-Chloro-2-[3-(2-methoxy-ethyl)-2,3,4,5-tetrahydro-1H-benzo[d]azepin-7-ylamino]-pyrimidin-4-ylamino}-N-(2-dimethylamino-ethyl)-benzamide;
2-{5-Chloro-2-[3-(2-methoxy-ethyl)-2,3,4,5-tetrahydro-1H-benzo[d]azepin-7-ylamino]-pyrimidin-4-ylamino}-N-(2-methoxy-ethyl)-benzamide;
2-{5-Chloro-2-[3-(2-methoxy-ethyl)-2,3,4,5-tetrahydro-1H-benzo[d]azepin-7-ylamino]-pyrimidin-4-ylamino}-N-(3-methoxy-propyl)-benzamide;
2-{5-Chloro-2-[3-(2-methoxy-ethyl)-2,3,4,5-tetrahydro-1H-benzo[d]azepin-7-ylamino]-pyrimidin-4-ylamino}-N-(4-dimethylamino-butyl)-benzamide;
2-{5-Chloro-2-[3-(2-methoxy-ethyl)-2,3,4,5-tetrahydro-1H-benzo[d]azepin-7-ylamino]-pyrimidin-4-ylamino}-N-(3-dimethylamino-propyl)-benzamide;
2-{5-Chloro-2-[3-(2-methoxy-ethyl)-2,3,4,5-tetrahydro-1H-benzo[d]azepin-7-ylamino]-pyrimidin-4-ylamino}-N-[2-(4-methyl-piperazin-1-yl)-ethyl]-benzamide;
2-{5-Chloro-2-[3-(2-methoxy-ethyl)-2,3,4,5-tetrahydro-1H-benzo[d]azepin-7-ylamino]-pyrimidin-4-ylamino}-3-fluoro-N-prop-2-ynyl-benzamide;
2-[5-Chloro-2-(2-oxo-2,3,4,5-tetrahydro-1H-benzo[b]azepin-8-ylamino)-pyrimidin-4-ylamino]-3-fluoro-N-prop-2-ynyl-benzamide;

2-[5-Chloro-2-(1-ethyl-5,5-dimethyl-2-oxo-2,3,4,5-tetrahydro-1H-benzo[b]azepin-8-ylamino)-pyrimidin-4-ylamino]-3-fluoro-N-prop-2-ynyl-benzamide;
2-[5-Chloro-2-(5,5-dimethyl-2-oxo-2,3,4,5-tetrahydro-1H-benzo[b]azepin-8-ylamino)-pyrimidin-4-ylamino]-3-fluoro-N-prop-2-ynyl-benzamide;
2-[5-Chloro-2-(9-ethyl-6,7,8,9-tetrahydro-5-oxa-9-aza-benzocyclohepten-3-ylamino)-pyrimidin-4-ylamino]-3-fluoro-N-prop-2-ynyl-benzamide;
2-{5-Chloro-2-[3-(2-methoxy-ethyl)-2,3,4,5-tetrahydro-1H-benzo[d]azepin-7-ylamino]-pyrimidin-4-ylamino}-benzoic acid methyl ester;
3-[5-Chloro-2-(9-ethyl-6,7,8,9-tetrahydro-5-oxa-9-aza-benzocyclohepten-3-ylamino)-pyrimidin-4-ylamino]-thiophene-2-carboxylic acid methylamide;
2-[5-Chloro-4-(2-fluoro-6-methylcarbamoyl-phenylamino)-pyrimidin-2-ylamino]-7,8-dihydro-6H-5-oxa-9-aza-benzocycloheptene-9-carboxylic acid ethyl ester;
2-[5-Chloro-4-(2-methylcarbamoyl-thiophen-3-ylamino)-pyrimidin-2-ylamino]-7,8-dihydro-6H-5-oxa-9-aza-benzocycloheptene-9-carboxylic acid ethyl ester;
2-[5-Chloro-2-(2-oxo-2,3,4,5-tetrahydro-1H-benzo[b]azepin-8-ylamino)-pyrimidin-4-ylamino]-5-dimethylamino-N-methyl-benzamide;
2-{5-Chloro-2-[3-(2-methoxy-ethyl)-2,3,4,5-tetrahydro-1H-benzo[d]azepin-7-ylamino]-pyrimidin-4-ylamino}-5-dimethylamino-N-methyl-benzamide;
5-Bromo-2-[5-chloro-2-(2-oxo-2,3,4,5-tetrahydro-1H-benzo[b]azepin-8-ylamino)-pyrimidin-4-ylamino]-3-fluoro-N-methyl-benzamide;
5-Bromo-2-{5-chloro-2-[3-(2-methoxy-ethyl)-2,3,4,5-tetrahydro-1H-benzo[d]azepin-7-ylamino]-pyrimidin-4-ylamino}-3-fluoro-N-methyl-benzamide;
2-{5-Chloro-2-[3-(2-methoxy-ethyl)-2,3,4,5-tetrahydro-1H-benzo[d]azepin-7-ylamino]-pyrimidin-4-ylamino}-N-(2-pyrrolidin-1-yl-ethyl)-benzamide;
3-[5-Chloro-4-(2-fluoro-6-methylcarbamoyl-phenylamino)-pyrimidin-2-ylamino]-7,8-dihydro-6H-5-oxa-9-aza-benzocycloheptene-9-carboxylic acid ethyl ester;
3-[5-Chloro-4-(2-methylcarbamoyl-thiophen-3-ylamino)-pyrimidin-2-ylamino]-7,8-dihydro-6H-5-oxa-9-aza-benzocycloheptene-9-carboxylic acid ethyl ester;
3-[5-Chloro-4-(2-methylcarbamoyl-phenylamino)-pyrimidin-2-ylamino]-7,8-dihydro-6H-5-oxa-9-aza-benzocycloheptene-9-carboxylic acid ethyl ester;
4-[5-Chloro-2-(2-oxo-2,3,4,5-tetrahydro-1H-benzo[b]azepin-8-ylamino)-pyrimidin-4-ylamino]-4'-cyano-5-fluoro-biphenyl-3-carboxylic acid methylamide;
2-{5-Chloro-2-[3-(2-methoxy-ethyl)-2,3,4,5-tetrahydro-1H-benzo[d]azepin-7-ylamino]-pyrimidin-4-ylamino}-N-cyclopropylmethyl-benzamide;
2-[5-Chloro-2-(2-oxo-2,3,4,5-tetrahydro-1H-benzo[b]azepin-8-ylamino)-pyrimidin-4-ylamino]-3-fluoro-N-methyl-5-(1-methyl-1H-pyrazol-4-yl)-benzamide;
2-{5-Chloro-2-[3-(2-methoxy-ethyl)-2,3,4,5-tetrahydro-1H-benzo[d]azepin-7-ylamino]-pyrimidin-4-ylamino}-3-fluoro-N-methyl-5-(1-methyl-1H-pyrazol-4-yl)-benzamide;
2-[2-(9-Acetyl-6,7,8,9-tetrahydro-5-oxa-9-aza-benzocyclohepten-2-ylamino)-5-chloro-pyrimidin-4-ylamino]-3-fluoro-N-methyl-5-(1-methyl-1H-pyrazol-4-yl)-benzamide;
2-[5-Chloro-2-(9-ethyl-6,7,8,9-tetrahydro-5-oxa-9-aza-benzocyclohepten-2-ylamino)-pyrimidin-4-ylamino]-3-fluoro-N-methyl-5-(1-methyl-1H-pyrazol-4-yl)-benzamide;
3-[5-Chloro-4-(2-fluoro-6-methylcarbamoyl-phenylamino)-pyrimidin-2-ylamino]-7,8-dihydro-6H-5-oxa-9-aza-benzocycloheptene-9-carboxylic acid 3-dimethylamino-propyl ester;
3-[5-Chloro-4-(2-fluoro-6-prop-2-ynylcarbamoyl-phenylamino)-pyrimidin-2-ylamino]-7,8-dihydro-6H-5-oxa-9-aza-benzocycloheptene-9-carboxylic acid 3-dimethylamino-propyl ester;
3-[5-Chloro-4-(2-methylcarbamoyl-thiophen-3-ylamino)-pyrimidin-2-ylamino]-7,8-dihydro-6H-5-oxa-9-aza-benzocycloheptene-9-carboxylic acid 3-dimethylamino-propyl ester;
3-[5-Chloro-4-(2-prop-2-ynylcarbamoyl-thiophen-3-ylamino)-pyrimidin-2-ylamino]-7,8-dihydro-6H-5-oxa-9-aza-benzocycloheptene-9-carboxylic acid 3-dimethylamino-propyl ester;
3-[5-Chloro-4-(2-fluoro-6-prop-2-ynylcarbamoyl-phenylamino)-pyrimidin-2-ylamino]-7,8-dihydro-6H-5-oxa-9-aza-benzocycloheptene-9-carboxylic acid methyl ester;
3-[5-Chloro-4-(2-fluoro-6-methylcarbamoyl-phenylamino)-pyrimidin-2-ylamino]-7,8-dihydro-6H-5-oxa-9-aza-benzocycloheptene-9-carboxylic acid methyl ester;
3-[5-Chloro-4-(2-fluoro-6-methylcarbamoyl-phenylamino)-pyrimidin-2-ylamino]-7,8-dihydro-6H-5-oxa-9-aza-benzocycloheptene-9-carboxylic acid isopropyl ester;
3-[5-Chloro-4-(2-fluoro-6-prop-2-ynylcarbamoyl-phenylamino)-pyrimidin-2-ylamino]-7,8-dihydro-6H-5-oxa-9-aza-benzocycloheptene-9-carboxylic acid isopropyl ester;
3-{5-Chloro-4-[2-fluoro-6-methylcarbamoyl-4-(1-methyl-1H-pyrazol-4-yl)-phenylamino]-pyrimidin-2-ylamino}-7,8-dihydro-6H-5-oxa-9-aza-benzocycloheptene-9-carboxylic acid methyl ester;
3-[5-Chloro-4-(2-methylcarbamoyl-thiophen-3-ylamino)-pyrimidin-2-ylamino]-7,8-dihydro-6H-5-oxa-9-aza-benzocycloheptene-9-carboxylic acid isopropyl ester;
3-[5-Chloro-4-(2-fluoro-6-methylcarbamoyl-phenylamino)-pyrimidin-2-ylamino]-7,8-dihydro-6H-5-oxa-9-aza-benzocycloheptene-9-carboxylic acid 2-methoxy-ethyl ester;
3-[5-Chloro-4-(2-fluoro-6-prop-2-ynylcarbamoyl-phenylamino)-pyrimidin-2-ylamino]-7,8-dihydro-6H-5-oxa-9-aza-benzocycloheptene-9-carboxylic acid 2-methoxy-ethyl ester;
3-[5-Chloro-4-(2-fluoro-6-methylcarbamoyl-phenylamino)-pyrimidin-2-ylamino]-7,8-dihydro-6H-5-oxa-9-aza-benzocycloheptene-9-carboxylic acid 1-methyl-piperidin-3-yl ester;
3-[5-Chloro-4-(2-fluoro-6-prop-2-ynylcarbamoyl-phenylamino)-pyrimidin-2-ylamino]-7,8-dihydro-6H-5-oxa-9-aza-benzocycloheptene-9-carboxylic acid 1-methyl-piperidin-3-yl ester;
3-[5-Chloro-4-(2-methylcarbamoyl-thiophen-3-ylamino)-pyrimidin-2-ylamino]-7,8-dihydro-6H-5-oxa-9-aza-benzocycloheptene-9-carboxylic acid 1-methyl-piperidin-3-yl ester;
N-{(1R,2R)-2-[5-Chloro-2-(1-ethyl-5-oxo-2,3,4,5-tetrahydro-1H-benzo[e][1,4]diazepin-8-ylamino)-pyrimidin-4-ylamino]-cyclohexyl}-methanesulfonamide;
2-[5-Chloro-2-(1-ethyl-5-oxo-2,3,4,5-tetrahydro-1H-benzo[e][1,4]diazepin-8-ylamino)-pyrimidin-4-ylamino]-N-methyl-benzamide;
8-{5-Chloro-4-[2-(1-methyl-1H-imidazol-2-yl)-phenylamino]-pyrimidin-2-ylamino}-1-ethyl-1,2,3,4-tetrahydro-benzo[e][1,4]diazepin-5-one;
2-[5-Chloro-2-(4-ethyl-5-oxo-2,3,4,5-tetrahydro-1H-benzo[e][1,4]diazepin-8-ylamino)-pyrimidin-4-ylamino]-3-fluoro-N-methyl-benzamide;

8-{5-Chloro-4-[2-(2-morpholin-4-yl-ethoxy)-phenylamino]-pyrimidin-2-ylamino}-1-ethyl-1,2,3,4-tetrahydro-benzo[e][1,4]diazepin-5-one;

N-{(1R,2R)-2-[5-Chloro-2-(1,4-diethyl-7-methoxy-2,3,4,5-tetrahydro-1H-benzo[e][1,4]diazepin-8-ylamino)-pyrimidin-4-ylamino]-cyclohexyl}-methanesulfonamide;

{8-[4-((1R,2S,3R,4S)-3-Carbamoyl-bicyclo[2.2.1]hept-2-ylamino)-5-chloro-pyrimidin-2-ylamino]-1-ethyl-5-oxo-1,2,3,5-tetrahydro-benzo[e][1,4]diazepin-4-yl}-acetic acid 2-methoxy-ethyl ester;

{8-[5-Chloro-4-(2-fluoro-6-methylcarbamoyl-phenylamino)-pyrimidin-2-ylamino]-1-ethyl-5-oxo-1,2,3,5-tetrahydro-benzo[e][1,4]diazepin-4-yl}-acetic acid 2-methoxy-ethyl ester;

{8-[5-Chloro-4-(2-methylcarbamoyl-phenylamino)-pyrimidin-2-ylamino]-1-ethyl-5-oxo-1,2,3,5-tetrahydro-benzo[e][1,4]diazepin-4-yl}-acetic acid 2-methoxy-ethyl ester;

(1S,2S,3R,4R)-3-[5-Chloro-2-(1-ethyl-7-methoxy-2,3,4,5-tetrahydro-1H-benzo[e][1,4]diazepin-8-ylamino)-pyrimidin-4-ylamino]-bicyclo[2.2.1]hept-5-ene-2-carboxylic acid amide;

2-{8-[5-Chloro-4-((1R,2R)-2-methanesulfonylamino-cyclohexylamino)-pyrimidin-2-ylamino]-1-ethyl-7-methoxy-1,2,3,5-tetrahydro-benzo[e][1,4]diazepin-4-yl}-N,N-dimethyl-acetamide;

N-((1R,2R)-2-{5-Chloro-2-[7-methoxy-5,5-dimethyl-2-oxo-4-(2,2,2-trifluoro-acetyl)-2,3,4,5-tetrahydro-1H-benzo[e][1,4]diazepin-8-ylamino]-pyrimidin-4-ylamino}-cyclohexyl)-methanesulfonamide;

8-{5-Chloro-4-[2-(2-morpholin-4-yl-ethoxy)-phenylamino]-pyrimidin-2-ylamino}-1,3,4,5-tetrahydro-benzo[b]azepin-2-one;

5-Chloro-N*2*-[3-(2-methoxy-ethyl)-2,3,4,5-tetrahydro-1H-enzo[d]azepin-7-yl]-N*4*-[2-(2-morpholin-4-yl-ethoxy)-phenyl]-pyrimidine-2,4-diamine;

2-[5-Chloro-2-(5,6-dihydro-4H-3,5,10b-triaza-benzo[e]azulen-9-ylamino)-pyrimidin-4-ylamino]-3-fluoro-N-methyl-benzamide;

2-{5-Bromo-2-[3-(2-methoxy-ethyl)-2,3,4,5-tetrahydro-1H-benzo[d]azepin-7-ylamino]-pyrimidin-4-ylamino}-3-fluoro-N-methyl-benzamide;

2-{5-Bromo-2-[1-(2-methoxy-ethyl)-2-oxo-2,3,4,5-tetrahydro-1H-benzo[b]azepin-7-ylamino]-pyrimidin-4-ylamino}-3-fluoro-N-methyl-benzamide;

2-{5-Bromo-2-[1-(2-methoxy-ethyl)-2-oxo-2,3,4,5-tetrahydro-1H-benzo[b]azepin-8-ylamino]-pyrimidin-4-ylamino}-3-fluoro-N-methyl-benzamide;

2-[5-Chloro-2-(1-isopropyl-2-oxo-2,3,4,5-tetrahydro-1H-benzo[b]azepin-8-ylamino)-pyrimidin-4-ylamino]-3-fluoro-N-methyl-benzamide;

2-[5-Chloro-2-(1-isopropyl-2-oxo-2,3,4,5-tetrahydro-1H-benzo[b]azepin-8-ylamino)-pyrimidin-4-ylamino]-3-methyl-benzamide;

2-[5-Chloro-2-(5,5-dimethyl-2-oxo-2,3,4,5-tetrahydro-1H-benzo[b]azepin2-[5-Chloro-2-(5,5-dimethyl-2-oxo-2,3,4,5-tetrahydro-1H-benzo[b]azepin-7-ylamino)-pyrimidin-4-ylamino]-3-methyl-benzamide;

3-[5-Chloro-2-(2-oxo-2,3,4,5-tetrahydro-1H-benzo[b]azepin-8-ylamino)-pyrimidin-4-ylamino]-thiophene-2-carboxylic acid methylamide;

3-{5-Chloro-2-[1-(2-methoxy-ethyl)-2-oxo-2,3,4,5-tetrahydro-1H-benzo[b]azepin-8-ylamino]-pyrimidin-4-ylamino}-thiophene-2-carboxylic acid methylamide;

4-[5-Chloro-2-(1-methyl-2-oxo-2,3,4,5-tetrahydro-1H-benzo[b]azepin-7-ylamino)-pyrimidin-4-ylamino]-benzo[1,3]dioxole-5-carboxylic acid methylamide;

4-{5-Chloro-2-[3-(2-methoxy-ethyl)-2,3,4,5-tetrahydro-1H-benzo[d]azepin-7-ylamino]-pyrimidin-4-ylamino}-benzo[1,3]dioxole-5-carboxylic acid methylamide;

4-[5-Chloro-2-(5,5-dimethyl-2-oxo-2,3,4,5-tetrahydro-1H-benzo[b]azepin-8-ylamino)-pyrimidin-4-ylamino]-benzo[1,3]dioxole-5-carboxylic acid methyl amide;

4-[5-Chloro-2-(2-oxo-2,3,4,5-tetrahydro-1H-benzo[b]azepin-8-ylamino)-pyrimidin-4-ylamino]-benzo[1,3]dioxole-5-carboxylic acid methylamide;

[2-(5-Chloro-2-{7-[4-(4-methyl-piperazin-1-yl)-piperidin-1-yl]-6,7,8,9-tetrahydro-5H-benzocyclohepten-2-ylamino}-pyrimidin-4-ylamino)-3-fluoro-phenoxy]-acetonitrile;

2-{5-Chloro-2-[3-(2-methoxy-ethyl)-2,3,4,5-tetrahydro-1H-benzo[d]azepin-7-ylamino]-pyrimidin-4-ylamino}-thiophene-3-carboxylic acid methylamide;

2-[5-Chloro-2-(2-oxo-2,3,4,5-tetrahydro-1H-benzo[b]azepin-8-ylamino)-pyrimidin-4-ylamino]-thiophene-3-carboxylic acid methylamide;

2-[5-Chloro-2-(5,5-dimethyl-2-oxo-2,3,4,5-tetrahydro-1H-benzo[b]azepin-8-ylamino)-pyrimidin-4-ylamino]-thiophene-3-carboxylic acid methylamide;

2-[5-Chloro-2-(1-methyl-2-oxo-2,3,4,5-tetrahydro-1H-benzo[b]azepin-7-ylamino)-pyrimidin-4-ylamino]-thiophene-3-carboxylic acid methylamide;

3-Chloro-2-(5-chloro-2-{7-[4-(4-methyl-piperazin-1-yl)-piperidin-1-yl]-6,7,8,9-tetrahydro-5H-benzocyclohepten-2-ylamino}-pyrimidin-4-ylamino)-N-methyl-benzamide;

2-[2-(1-Acetyl-2,3,4,5-tetrahydro-1H-benzo[b]azepin-8-ylamino)-5-chloro-pyrimidin-4-ylamino]-3-fluoro-N-methyl-benzamide;

2-[2-(1-Acetyl-2,3,4,5-tetrahydro-1H-benzo[b]azepin-8-ylamino)-5-chloro-pyrimidin-4-ylamino]-3-fluoro-N-prop-2-ynyl-benzamide;

2-[5-Chloro-2-(3-morpholin-4-yl-2-oxo-2,3,4,5-tetrahydro-1H-benzo[b]azepin-8-ylamino)-pyrimidin-4-ylamino]-3-fluoro-N-methyl-benzamide;

1-(2-{5-Chloro-2-[3-(2-methoxy-ethyl)-2,3,4,5-tetrahydro-1H-benzo[d]azepin-7-ylamino]-pyrimidin-4-ylamino}-benzenesulfonyl)-pyrrolidin-3-ol;

8-{5-Chloro-4-[2-(3-hydroxy-pyrrolidine-1-sulfonyl)-phenylamino]-pyrimidin-2-ylamino}-1,3,4,5-tetrahydro-benzo[b]azepin-2-one;

2-{5-Chloro-4-[2-(5-methyl-[1,3,4]thiadiazol-2-yl)-phenylamino]-pyrimidin-2-ylamino}-5-methyl-8,9-dihydro-5H-7-oxa-5-aza-benzocyclohepten-6-one;

2-{5-Chloro-2-[3-(2-methoxy-ethylamino)-2-oxo-2,3,4,5-tetrahydro-1H-benzo[b]azepin-8-ylamino]-pyrimidin-4-ylamino}-3-fluoro-N-methyl-benzamide;

2-{5-Chloro-2-[3-(2-dimethylamino-acetylamino)-1-ethyl-2-oxo-2,3,4,5-tetrahydro-1H-benzo[b]azepin-8-ylamino]-pyrimidin-4-ylamino}-3-fluoro-N-methyl-benzamide;

2-{5-Chloro-2-[3-(2-dimethylamino-acetylamino)-1-ethyl-2-oxo-2,3,4,5-tetrahydro-1H-benzo[b]azepin-8-ylamino]-pyrimidin-4-ylamino}-3-fluoro-N-prop-2-ynyl-benzamide;

2-{5-Chloro-2-[1-ethyl-3-(2-methoxy-acetylamino)-2-oxo-2,3,4,5-tetrahydro-1H-benzo[b]azepin-8-ylamino]-pyrimidin-4-ylamino}-3-fluoro-N-methyl-benzamide;

2-{5-Chloro-2-[1-ethyl-3-(2-methoxy-acetylamino)-2-oxo-2,3,4,5-tetrahydro-1H-benzo[b]azepin-8-ylamino]-pyrimidin-4-ylamino}-3-fluoro-N-prop-2-ynyl-benzamide;

N-((cis)-2-{5-Chloro-2-[3-(2-methoxy-ethyl)-2,3,4,5-tetrahydro-1H-benzo[d]azepin-7-ylamino]-pyrimidin-4-ylamino}-cyclopentyl)-methanesulfonamide;

(1S,2S)-2-[5-Chloro-2-(3-ethyl-2,3,4,5-tetrahydro-1H-benzo[d]azepin-7-ylamino)-pyrimidin-4-ylamino]-cyclohexanecarboxylic acid amide;

N-{(1R,2R)-2-[5-Chloro-2-(3-methoxy-5-methyl-6-oxo-5,6,8,9-tetrahydro-7-oxa-5-aza-benzocyclohepten-2-ylamino)-pyrimidin-4-ylamino]-cyclohexyl}-methanesulfonamide;

2-[5-Chloro-2-(3-methoxy-5-methyl-6-oxo-5,6,8,9-tetrahydro-7-oxa-5-aza-benzocyclohepten-2-ylamino)-pyrimidin-4-ylamino]-N-methyl-benzamide;

2-[5-Chloro-4-(2-methoxy-4-morpholin-4-yl-phenylamino)-pyrimidin-2-ylamino]-3-methoxy-5-methyl-8,9-dihydro-5H-7-oxa-5-aza-benzocyclohepten-6-one;

2-[5-Bromo-2-(3-methoxy-5-methyl-6-oxo-5,6,8,9-tetrahydro-7-oxa-5-aza-benzocyclohepten-2-ylamino)-pyrimidin-4-ylamino]-N-methyl-benzamide;

2-[5-Chloro-4-(2-methoxy-phenylamino)-pyrimidin-2-ylamino]-3-methoxy-5-methyl-8,9-dihydro-5H-7-oxa-5-aza-benzocyclohepten-6-one;

(1R,2R,3S,4S)-3-[5-Chloro-2-(3-methoxy-5-methyl-6-oxo-5,6,8,9-tetrahydro-7-oxa-5-aza-benzocyclohepten-2-ylamino)-pyrimidin-4-ylamino]-bicyclo[2.2.1]hept-5-ene-2-carboxylic acid amide;

{3-[5-Chloro-2-(3-methoxy-5-methyl-6-oxo-5,6,8,9-tetrahydro-7-oxa-5-aza-benzocyclohepten-2-ylamino)-pyrimidin-4-ylamino]-phenoxy}-acetonitrile;

2-[5-Chloro-2-(2-methoxy-5-methyl-6-oxo-5,6,8,9-tetrahydro-7-oxa-5-aza-benzocyclohepten-3-ylamino)-pyrimidin-4-ylamino]-N-methyl-benzamide;

2-[5-Bromo-2-(2-methoxy-5-methyl-6-oxo-5,6,8,9-tetrahydro-7-oxa-5-aza-benzocyclohepten-3-ylamino)-pyrimidin-4-ylamino]-N-methyl-benzamide;

2-[2-(3-Methoxy-5-methyl-6-oxo-5,6,8,9-tetrahydro-7-oxa-5-aza-benzocyclohepten-2-ylamino)-5-trifluoromethyl-pyrimidin-4-ylamino]-N-methyl-benzamide;

3-Methoxy-2-[4-(2-methoxy-4-morpholin-4-yl-phenylamino)-5-trifluoromethyl-pyrimidin-2-ylamino]-5-methyl-8,9-dihydro-5H-7-oxa-5-aza-benzocyclohepten-6-one;

{2-[5-Chloro-2-(3-methoxy-5-methyl-6-oxo-5,6,8,9-tetrahydro-7-oxa-5-aza-benzocyclohepten-2-ylamino)-pyrimidin-4-ylamino]-phenoxy}-acetonitrile;

2-Methoxy-3-[4-(2-methoxy-4-morpholin-4-yl-phenylamino)-5-trifluoromethyl-pyrimidin-2-ylamino]-5-methyl-8,9-dihydro-5H-7-oxa-5-aza-benzocyclohepten-6-one;

{2-[5-Chloro-2-(1-ethyl-5,5-dimethyl-2-oxo-2,3,4,5-tetrahydro-1H-benzo[b]azepin-8-ylamino)-pyrimidin-4-ylamino]-3-fluoro-phenoxy}-acetonitrile;

(2-{5-Chloro-2-[1-(2-methoxy-ethyl)-5,5-dimethyl-2-oxo-2,3,4,5-tetrahydro-1H-benzo[b]azepin-8-ylamino]-pyrimidin-4-ylamino}-3-fluoro-phenoxy)-acetonitrile;

2-{5-Chloro-2-[8-methoxy-3-(2-morpholin-4-yl-ethyl)-2,3,4,5-tetrahydro-1H-benzo[d]azepin-7-ylamino]-pyrimidin-4-ylamino}-N,N-dimethyl-benzenesulfonamide;

5-Chloro-N*2*-[8-methoxy-3-(2-morpholin-4-yl-ethyl)-2,3,4,5-tetrahydro-1H-benzo[d]azepin-7-yl]-N*4*-(2-methoxy-4-morpholin-4-yl-phenyl)-pyrimidine-2,4-diamine;

2-{5-Chloro-2-[8-methoxy-3-(2-morpholin-4-yl-ethyl)-2,3,4,5-tetrahydro-1H-benzo[d]azepin-7-ylamino]-pyrimidin-4-ylamino}-N-methyl-benzamide;

2-{5-Chloro-2-[8-methoxy-3-(2-morpholin-4-yl-2-oxo-ethyl)-2,3,4,5-tetrahydro-1H-benzo[d]azepin-7-ylamino]-pyrimidin-4-ylamino}-N,N-dimethyl-benzenesulfonamide;

2-{7-[5-Chloro-4-(2-methoxy-4-morpholin-4-yl-phenylamino)-pyrimidin-2-ylamino]-8-methoxy-1,2,4,5-tetrahydro-benzo[d]azepin-3-yl}-1-morpholin-4-yl-ethanone;

(1S,2S,3R,4R)-3-{5-Chloro-2-[8-methoxy-3-(2-morpholin-4-yl-2-oxo-ethyl)-2,3,4,5-tetrahydro-1H-benzo[d]azepin-7-ylamino]-pyrimidin-4-ylamino}-bicyclo[2.2.1]hept-5-ene-2-carboxylic acid amide;

N-((1R,2R)-2-{5-Chloro-2-[8-methoxy-3-(2-morpholin-4-yl-2-oxo-ethyl)-2,3,4,5-tetrahydro-1H-benzo[d]azepin-7-ylamino]-pyrimidin-4-ylamino}-cyclohexyl)-methanesulfonamide;

(1S,2S,3R,4R)-3-{5-Chloro-2-[8-methoxy-3-(2-morpholin-4-yl-ethyl)-2,3,4,5-tetrahydro-1H-benzo[d]azepin-7-ylamino]-pyrimidin-4-ylamino}-bicyclo[2.2.1]hept-5-ene-2-carboxylic acid amide;

2-{5-Chloro-2-[3-(2-hydroxy-ethyl)-8-methoxy-2,3,4,5-tetrahydro-1H-benzo[d]azepin-7-ylamino]-pyrimidin-4-ylamino}-N,N-dimethyl-benzenesulfonamide;

N-((1R,2R)-2-{5-Chloro-2-[3-(2-hydroxy-ethyl)-8-methoxy-2,3,4,5-tetrahydro-1H-benzo[d]azepin-7-ylamino]-pyrimidin-4-ylamino}-cyclohexyl)-methanesulfonamide;

(1S,2S,3R,4R)-3-{5-Chloro-2-[3-(2-hydroxy-ethyl)-8-methoxy-2,3,4,5-tetrahydro-1H-benzo[d]azepin-7-ylamino]-pyrimidin-4-ylamino}-bicyclo[2.2.1]hept-5-ene-2-carboxylic acid amide;

N-((1R,2R)-2-{5-Chloro-2-[8-methoxy-3-(2-morpholin-4-yl-ethyl)-2,3,4,5-tetrahydro-1H-benzo[d]azepin-7-ylamino]-pyrimidin-4-ylamino}-cyclohexyl)-methanesulfonamide;

5-Chloro-N*2*-[8-methoxy-3-(2-morpholin-4-yl-ethyl)-2,3,4,5-tetrahydro-1H-benzo[d]azepin-7-yl]-N*4*-[2-(propane-2-sulfonyl)-phenyl]-pyrimidine-2,4-diamine;

2-(7-{5-Chloro-4-[2-(propane-2-sulfonyl)-phenylamino]-pyrimidin-2-ylamino}-8-methoxy-1,2,4,5-tetrahydro-benzo[d]azepin-3-yl)-ethanol;

2-(7-{5-Chloro-4-[2-(propane-2-sulfonyl)-phenylamino]-pyrimidin-2-ylamino}-8-methoxy-1,2,4,5-tetrahydro-benzo[d]azepin-3-yl)-1-morpholin-4-yl-ethanone;

5-Chloro-N*4*-(4-dimethylamino-2-methoxy-phenyl)-N*2*-[8-methoxy-3-(2-morpholin-4-yl-ethyl)-2,3,4,5-tetrahydro-1H-benzo[d]azepin-7-yl]-pyrimidine-2,4-diamine;

2-(5-Chloro-2-{8-methoxy-3-[2-(4-methyl-piperazin-1-yl)-2-oxo-ethyl]-2,3,4,5-tetrahydro-1H-benzo[d]azepin-7-ylamino}-pyrimidin-4-ylamino)-N,N-dimethyl-benzenesulfonamide;

(1S,2S,3R,4R)-3-(5-Chloro-2-{8-methoxy-3-[2-(4-methyl-piperazin-1-yl)-2-oxo-ethyl]-2,3,4,5-tetrahydro-1H-benzo[d]azepin-7-ylamino}-pyrimidin-4-ylamino)-bicyclo[2.2.1]hept-5-ene-2-carboxylic acid amide;

2-{7-[5-Chloro-4-(4-dimethylamino-2-methoxy-phenylamino)-pyrimidin-2-ylamino]-8-methoxy-1,2,4,5-tetrahydro-benzo[d]azepin-3-yl}-1-(4-methyl-piperazin-1-yl)-ethanone;

2-(7-{5-Chloro-4-[2-(propane-2-sulfonyl)-phenylamino]-pyrimidin-2-ylamino}-8-methoxy-1,2,4,5-tetrahydro-benzo[d]azepin-3-yl)-1-(4-methyl-piperazin-1-yl)-ethanone;

Amino-acetic acid 2-{7-[5-chloro-4-(2-dimethylsulfamoyl-phenylamino)-pyrimidin-2-ylamino]-8-methoxy-1,2,4,5-tetrahydro-benzo[d]azepin-3-yl}-ethyl ester;

2-(7-{5-Chloro-4-[2-(pyrrolidine-1-sulfonyl)-phenylamino]-pyrimidin-2-ylamino}-8-methoxy-1,2,4,5-tetrahydro-benzo[d]azepin-3-yl)-ethanol;

(S)-2-Amino-3-methyl-butyric acid 2-{7-[5-chloro-4-(2-dimethylsulfamoyl-phenylamino)-pyrimidin-2-ylamino]-8-methoxy-1,2,4,5-tetrahydro-benzo[d]azepin-3-yl}-ethyl ester;

Phosphoric acid mono-(2-{7-[5-chloro-4-(2-dimethylsulfamoyl-phenylamino)-pyrimidin-2-ylamino]-8-methoxy-1,2,4,5-tetrahydro-benzo[d]azepin-3-yl}-ethyl) ester;

Propionic acid 2-{7-[5-chloro-4-(2-dimethylsulfamoyl-phenylamino)-pyrimidin-2-ylamino]-8-methoxy-1,2,4,5-tetrahydro-benzo[d]azepin-3-yl}-ethyl ester;

2-{5-Chloro-2-[3-(2-hydroxy-propyl)-8-methoxy-2,3,4,5-tetrahydro-1H-benzo[d]azepin-7-ylamino]-pyrimidin-4-ylamino}-N,N-dimethyl-benzenesulfonamide;

(1S,2S,3R,4R)-3-{5-Chloro-2-[3-(2-hydroxy-propyl)-8-methoxy-2,3,4,5-tetrahydro-1H-benzo[d]azepin-7-ylamino]-pyrimidin-4-ylamino}-bicyclo[2.2.1]hept-5-ene-2-carboxylic acid amide;

2-{5-Chloro-2-[3-(2-hydroxy-ethyl)-8-methoxy-2,3,4,5-tetrahydro-1H-benzo[d]azepin-7-ylamino]-pyrimidin-4-ylamino}-benzoic acid 2-methoxy-ethyl ester;

2-{5-Chloro-2-[3-(2-hydroxy-propyl)-8-methoxy-2,3,4,5-tetrahydro-1H-benzo[d]azepin-7-ylamino]-pyrimidin-4-ylamino}-benzoic acid 2-methoxy-ethyl ester;

1-(2-{5-Chloro-2-[3-(2-hydroxy-ethyl)-8-methoxy-2,3,4,5-tetrahydro-1H-benzo[d]azepin-7-ylamino]-pyrimidin-4-ylamino}-benzenesulfonyl)-pyrrolidin-3-ol;

1-(2-{5-Chloro-2-[3-(2-hydroxy-propyl)-8-methoxy-2,3,4,5-tetrahydro-1H-benzo[d]azepin-7-ylamino]-pyrimidin-4-ylamino}-benzenesulfonyl)-pyrrolidin-3-ol;

1-(7-{5-Chloro-4-[2-(pyrrolidine-1-sulfonyl)-phenylamino]-pyrimidin-2-ylamino}-8-methoxy-1,2,4,5-tetrahydro-benzo[d]azepin-3-yl)-propan-2-ol;

(R)-1-(2-{5-Chloro-2-[3-((S)-2-hydroxy-propyl)-8-methoxy-2,3,4,5-tetrahydro-1H-benzo[d]azepin-7-ylamino]-pyrimidin-4-ylamino}-benzenesulfonyl)-pyrrolidin-3-ol;

(S)-1-(2-{5-Chloro-2-[3-((S)-2-hydroxy-propyl)-8-methoxy-2,3,4,5-tetrahydro-1H-benzo[d]azepin-7-ylamino]-pyrimidin-4-ylamino}-benzenesulfonyl)-pyrrolidin-3-ol;

(S)-1-(2-{5-Chloro-2-[3-((R)-2-hydroxy-propyl)-8-methoxy-2,3,4,5-tetrahydro-1H-benzo[d]azepin-7-ylamino]-pyrimidin-4-ylamino}-benzenesulfonyl)-pyrrolidin-3-ol;

(R)-1-(2-{5-Chloro-2-[3-((R)-2-hydroxy-propyl)-8-methoxy-2,3,4,5-tetrahydro-1H-benzo[d]azepin-7-ylamino]-pyrimidin-4-ylamino}-benzenesulfonyl)-pyrrolidin-3-ol;

(1S,2S,3R,4R)-3-{5-Chloro-2-[3-((S)-2-hydroxy-propyl)-8-methoxy-2,3,4,5-tetrahydro-1H-benzo[d]azepin-7-ylamino]-pyrimidin-4-ylamino}-bicyclo[2.2.1]hept-5-ene-2-carboxylic acid amide;

(1S,2S,3R,4R)-3-{5-Chloro-2-[3-((R)-2-hydroxy-propyl)-8-methoxy-2,3,4,5-tetrahydro-1H-benzo[d]azepin-7-ylamino]-pyrimidin-4-ylamino}-bicyclo[2.2.1]hept-5-ene-2-carboxylic acid amide;

(1S,2S,3R,4R)-3-{5-Chloro-2-[3-(2-hydroxy-2-methyl-propyl)-8-methoxy-2,3,4,5-tetrahydro-1H-benzo[d]azepin-7-ylamino]-pyrimidin-4-ylamino}-bicyclo[2.2.1]hept-5-ene-2-carboxylic acid amide;

(R)-1-(2-{5-Chloro-2-[3-(2-hydroxy-2-methyl-propyl)-8-methoxy-2,3,4,5-tetrahydro-1H-benzo[d]azepin-7-ylamino]-pyrimidin-4-ylamino}-benzenesulfonyl)-pyrrolidin-3-ol;

(S)-1-(2-{5-Chloro-2-[3-(2-hydroxy-2-methyl-propyl)-8-methoxy-2,3,4,5-tetrahydro-1H-benzo[d]azepin-7-ylamino]-pyrimidin-4-ylamino}-benzenesulfonyl)-pyrrolidin-3-ol;

2-{5-Chloro-2-[3-(2-hydroxy-2-methyl-propyl)-8-methoxy-2,3,4,5-tetrahydro-1H-benzo[d]azepin-7-ylamino]-pyrimidin-4-ylamino}-N,N-dimethyl-benzenesulfonamide;

(1S,2S,3R,4R)-3-[5-Chloro-2-(1,5,5-trimethyl-2-oxo-2,3,4,5-tetrahydro-1H-benzo[b]azepin-7-ylamino)-pyrimidin-4-ylamino]-bicyclo[2.2.1]hept-5-ene-2-carboxylic acid amide;

3-[5-Chloro-2-(5,5-dimethyl-2-oxo-2,3,4,5-tetrahydro-1H-benzo[b]azepin-7-ylamino)-pyrimidin-4-ylamino]-4-methyl-thiophene-2-carboxylic acid methylamide;

7-[5-Chloro-4-(2-methoxy-4-morpholin-4-yl-phenylamino)-pyrimidin-2-ylamino]-1,5,5-trimethyl-1,3,4,5-tetrahydro-benzo[b]azepin-2-one;

2-[5-Chloro-2-(5,5-dimethyl-2-oxo-2,3,4,5-tetrahydro-1H-benzo[b]azepin-8-ylamino)-pyrimidin-4-ylamino]-3-fluoro-N-methyl-benzamide;

2-[5-Chloro-2-(5,5-dimethyl-2-oxo-2,3,4,5-tetrahydro-1H-benzo[b]azepin-8-ylamino)-pyrimidin-4-ylamino]-N-ethyl-3-fluoro-benzamide;

2-[5-Chloro-2-(1-ethyl-5,5-dimethyl-2-oxo-2,3,4,5-tetrahydro-1H-benzo[b]azepin-8-ylamino)-pyrimidin-4-ylamino]-3-fluoro-N-methyl-benzamide;

2-[5-Chloro-2-(5,5-dimethyl-2-oxo-2,3,4,5-tetrahydro-1H-benzo[b]azepin-8-ylamino)-pyrimidin-4-ylamino]-3-methyl-benzamide;

{2-[5-Chloro-2-(5,5-dimethyl-2-oxo-2,3,4,5-tetrahydro-1H-benzo[b]azepin-8-ylamino)-pyrimidin-4-ylamino]-phenoxy}-acetonitrile;

2-[5-Chloro-2-(1-ethyl-5,5-dimethyl-2-oxo-2,3,4,5-tetrahydro-1H-benzo[b]azepin-8-ylamino)-pyrimidin-4-ylamino]-N-ethyl-3-fluoro-benzamide;

{2-[5-Chloro-2-(1-ethyl-5,5-dimethyl-2-oxo-2,3,4,5-tetrahydro-1H-benzo[b]azepin-8-ylamino)-pyrimidin-4-ylamino]-phenoxy}-acetonitrile;

2-{5-Chloro-2-[1-(2-methoxy-ethyl)-5,5-dimethyl-2-oxo-2,3,4,5-tetrahydro-1H-benzo[b]azepin-8-ylamino]-pyrimidin-4-ylamino}-3-fluoro-N-methyl-benzamide;

(2-{5-Chloro-2-[1-(2-methoxy-ethyl)-5,5-dimethyl-2-oxo-2,3,4,5-tetrahydro-1H-benzo[b]azepin-8-ylamino]-pyrimidin-4-ylamino}-phenoxy)-acetonitrile;

(1S,2S,3R,4R)-3-{5-Chloro-2-[1-(2-methoxy-ethyl)-5,5-dimethyl-2-oxo-2,3,4,5-tetrahydro-1H-benzo[b]azepin-8-ylamino]-pyrimidin-4-ylamino}-bicyclo[2.2.1]hept-5-ene-2-carboxylic acid amide;

8-[5-Chloro-4-(2-methoxy-4-morpholin-4-yl-phenylamino)-pyrimidin-2-ylamino]-1-(2-methoxy-ethyl)-5,5-dimethyl-1,3,4,5-tetrahydro-benzo[b]azepin-2-one;

2-{5-Chloro-2-[1-(2-methoxy-ethyl)-5,5-dimethyl-2-oxo-2,3,4,5-tetrahydro-1H-benzo[b]azepin-8-ylamino]-pyrimidin-4-ylamino}-N-methyl-benzamide;

(1S,2S,3R,4R)-3-[5-Chloro-2-(1-ethyl-5,5-dimethyl-2-oxo-2,3,4,5-tetrahydro-1H-benzo[b]azepin-8-ylamino)-pyrimidin-4-ylamino]-bicyclo[2.2.1]hept-5-ene-2-carboxylic acid amide;

8-[5-Chloro-4-(2-methoxy-4-morpholin-4-yl-phenylamino)-pyrimidin-2-ylamino]-1-ethyl-5,5-dimethyl-1,3,4,5-tetrahydro-benzo[b]azepin-2-one;

2-[5-Chloro-2-(1-isopropyl-5,5-dimethyl-2-oxo-2,3,4,5-tetrahydro-1H-benzo[b]azepin-8-ylamino)-pyrimidin-4-ylamino]-3-fluoro-N-methyl-benzamide;

2-[5-Chloro-2-(1-ethyl-5,5-dimethyl-2-oxo-2,3,4,5-tetrahydro-1H-benzo[b]azepin-8-ylamino)-pyrimidin-4-ylamino]-N-methyl-benzamide;

(1S,2S,3R,4R)-3-[5-Chloro-2-(1-isopropyl-5,5-dimethyl-2-oxo-2,3,4,5-tetrahydro-1H-benzo[b]azepin-8-ylamino)-pyrimidin-4-ylamino]-bicyclo[2.2.1]hept-5-ene-2-carboxylic acid amide;

8-[5-Chloro-4-(2-methoxy-4-morpholin-4-yl-phenylamino)-pyrimidin-2-ylamino]-1-isopropyl-5,5-dimethyl-1,3,4,5-tetrahydro-benzo[b]azepin-2-one;

2-[5-Chloro-2-(1-isobutyl-5,5-dimethyl-2-oxo-2,3,4,5-tetrahydro-1H-benzo[b]azepin-8-ylamino)-pyrimidin-4-ylamino]-3-fluoro-N-methyl-benzamide;
(1S,2S,3R,4R)-3-[5-Chloro-2-(1-isobutyl-5,5-dimethyl-2-oxo-2,3,4,5-tetrahydro-1H-benzo[b]azepin-8-ylamino)-pyrimidin-4-ylamino]-bicyclo[2.2.1]hept-5-ene-2-carboxylic acid amide;
8-[5-Chloro-4-(2-methoxy-4-morpholin-4-yl-phenylamino)-pyrimidin-2-ylamino]-1-isobutyl-5,5-dimethyl-1,3,4,5-tetrahydro-benzo[b]azepin-2-one;
2-[5-Chloro-2-(1-ethyl-5,5-dimethyl-2-oxo-2,3,4,5-tetrahydro-1H-benzo[b]azepin-8-ylamino)-pyrimidin-4-ylamino]-N,N-dimethyl-benzenesulfonamide;
2-[2-(1-Acetyl-5,5-dimethyl-2,3,4,5-tetrahydro-1H-benzo[b]azepin-8-ylamino)-5-chloro-pyrimidin-4-ylamino]-3-fluoro-N-methyl-benzamide;
3-[5-Chloro-2-(1-ethyl-5,5-dimethyl-2-oxo-2,3,4,5-tetrahydro-1H-benzo[b]azepin-8-ylamino)-pyrimidin-4-ylamino]-thiophene-2-carboxylic acid methyl amide;
1-{8-[5-Chloro-4-(2-methoxy-4-morpholin-4-yl-phenylamino)-pyrimidin-2-ylamino]-5,5-dimethyl-2,3,4,5-tetrahydro-benzo[b]azepin-1-yl}-ethanone;
2-{5-Chloro-2-[1-(2-methoxy-ethyl)-5,5-dimethyl-2,3,4,5-tetrahydro-1H-benzo[b]azepin-8-ylamino]-pyrimidin-4-ylamino}-3-fluoro-N-methyl-benzamide;
(1S,2S,3R,4R)-3-{5-Chloro-2-[1-(2-methoxy-ethyl)-5,5-dimethyl-2,3,4,5-tetrahydro-1H-benzo[b]azepin-8-ylamino]-pyrimidin-4-ylamino}-bicyclo[2.2.1]hept-5-ene-2-carboxylic acid amide;
5-Chloro-N*2*-[1-(2-methoxy-ethyl)-5,5-dimethyl-2,3,4,5-tetrahydro-1H-benzo[b]azepin-8-yl]-N*4*-(2-methoxy-4-morpholin-4-yl-phenyl)-pyrimidine-2,4-diamine;
2-[2-(1-Acetyl-5,5-dimethyl-2,3,4,5-tetrahydro-1H-benzo[b]azepin-8-ylamino)-5-chloro-pyrimidin-4-ylamino]-3-fluoro-N-prop-2-ynyl-benzamide;
2-{5-Chloro-2-[5,5-dimethyl-1-(2-pyrrolidin-1-yl-acetyl)-2,3,4,5-tetrahydro-1H-benzo[b]azepin-8-ylamino]-pyrimidin-4-ylamino}-3-fluoro-N-methyl-benzamide;
2-{5-Chloro-2-[5,5-dimethyl-1-(2-pyrrolidin-1-yl-acetyl)-2,3,4,5-tetrahydro-1H-benzo[b]azepin-8-ylamino]-pyrimidin-4-ylamino}-3-fluoro-N-prop-2-ynyl-benzamide;
2-{5-Chloro-2-[5,5-dimethyl-1-(2-pyrrolidin-1-yl-ethyl)-2,3,4,5-tetrahydro-1H-benzo[b]azepin-8-ylamino]-pyrimidin-4-ylamino}-3-fluoro-N-methyl-benzamide;
(1S,2S,3R,4R)-3-{5-Chloro-2-[5,5-dimethyl-1-(2-pyrrolidin-1-yl-ethyl)-2,3,4,5-tetrahydro-1H-benzo[b]azepin-8-ylamino]-pyrimidin-4-ylamino}-bicyclo[2.2.1]hept-5-ene-2-carboxylic acid amide;
(1S,2S,3R,4R)-3-{5-Chloro-2-[5,5-dimethyl-1-(2-pyrrolidin-1-yl-acetyl)-2,3,4,5-tetrahydro-1H-benzo[b]azepin-8-ylamino]-pyrimidin-4-ylamino}-bicyclo[2.2.1]hept-5-ene-2-carboxylic acid amide;
2-[2-(1-Acetyl-5,5-dimethyl-2,3,4,5-tetrahydro-1H-benzo[b]azepin-8-ylamino)-5-chloro-pyrimidin-4-ylamino]-3,5-difluoro-N-methyl-benzamide;
2-{5-Chloro-2-[5,5-dimethyl-1-(2-pyrrolidin-1-yl-ethyl)-2,3,4,5-tetrahydro-1H-benzo[b]azepin-8-ylamino]-pyrimidin-4-ylamino}-3-fluoro-N-prop-2-ynyl-benzamide;
5-Chloro-N*2*-[5,5-dimethyl-1-(2-pyrrolidin-1-yl-ethyl)-2,3,4,5-tetrahydro-1H-benzo[b]azepin-8-yl]-N*4*-(2-methoxy-4-morpholin-4-yl-phenyl)-pyrimidine-2,4-diamine;
2-[5-Chloro-2-(5,5-dimethyl-2,3,4,5-tetrahydro-1H-benzo[b]azepin-8-ylamino)-pyrimidin-4-ylamino]-3-fluoro-N-methyl-benzamide;
2-[5-Chloro-2-(5,5-dimethyl-2,3,4,5-tetrahydro-1H-benzo[b]azepin-8-ylamino)-pyrimidin-4-ylamino]-3-fluoro-N-prop-2-ynyl-benzamide;
(1S,2S,3R,4R)-3-[5-Chloro-2-(5,5-dimethyl-2,3,4,5-tetrahydro-1H-benzo[b]azepin-8-ylamino)-pyrimidin-4-ylamino]-bicyclo[2.2.1]hept-5-ene-2-carboxylic acid amide;
5-Chloro-N*2*-(5,5-dimethyl-2,3,4,5-tetrahydro-1H-benzo[b]azepin-8-yl)-N*4*-(2-methoxy-4-morpholin-4-yl-phenyl)-pyrimidine-2,4-diamine;
2-[5-Chloro-2-(1-ethyl-5,5-dimethyl-2-oxo-2,3,4,5-tetrahydro-1H-benzo[b]azepin-8-ylamino)-pyrimidin-4-ylamino]-3,5-difluoro-N-methyl-benzamide;
2-(5-Chloro-2-{1-[2-(1,3-dioxo-1,3-dihydro-isoindol-2-yl)-acetyl]-5,5-dimethyl-2,3,4,5-tetrahydro-1H-benzo[b]azepin-8-ylamino}-pyrimidin-4-ylamino)-3-fluoro-N-methyl-benzamide;
2-{2-[1-(2-Amino-acetyl)-5,5-dimethyl-2,3,4,5-tetrahydro-1H-benzo[b]azepin-8-ylamino]-5-chloro-pyrimidin-4-ylamino}-3-fluoro-N-methyl-benzamide;
2-(5-Chloro-2-{1-[2-(1,3-dioxo-1,3-dihydro-isoindol-2-yl)-acetyl]-5,5-dimethyl-2,3,4,5-tetrahydro-1H-benzo[b]azepin-8-ylamino}-pyrimidin-4-ylamino)-3-fluoro-N-prop-2-ynyl-benzamide;
2-{2-[1-(2-Amino-acetyl)-5,5-dimethyl-2,3,4,5-tetrahydro-1H-benzo[b]azepin-8-ylamino]-5-chloro-pyrimidin-4-ylamino}-3-fluoro-N-prop-2-ynyl-benzamide;
2-{5-Chloro-2-[5,5-dimethyl-1-(pyrrolidine-1-carbonyl)-2,3,4,5-tetrahydro-1H-benzo[b]azepin-8-ylamino]-pyrimidin-4-ylamino}-3-fluoro-N-methyl-benzamide;
8-{5-Chloro-4-[2-(3-hydroxy-pyrrolidine-1-sulfonyl)-phenylamino]-pyrimidin-2-ylamino}-5,5-dimethyl-1,3,4,5-tetrahydro-benzo[b]azepin-2-one;
2-{5-Chloro-2-[5,5-dimethyl-1-(pyrrolidine-1-carbonyl)-2,3,4,5-tetrahydro-1H-benzo[b]azepin-8-ylamino]-pyrimidin-4-ylamino}-3,5-difluoro-N-prop-2-ynyl-benzamide;
3-[5-Chloro-2-(5,5-dimethyl-2-oxo-2,3,4,5-tetrahydro-1H-benzo[b]azepin-8-ylamino)-pyrimidin-4-ylamino]-thiophene-2-carboxylic acid prop-2-ynylamide;
2-[5-Chloro-2-(5,5-dimethyl-2-oxo-2,3,4,5-tetrahydro-1H-benzo[b]azepin-8-ylamino)-pyrimidin-4-ylamino]-3-fluoro-N-methyl-5-(1-methyl-1H-pyrazol-4-yl)-benzamide;
8-{5-Chloro-4-[2-((R)-3-dimethylamino-pyrrolidine-1-sulfonyl)-phenylamino]-pyrimidin-2-ylamino}-5,5-dimethyl-1,3,4,5-tetrahydro-benzo[b]azepin-2-one;
2-[5-Chloro-2-(1-isopropyl-5,5-dimethyl-2,3,4,5-tetrahydro-1H-benzo[b]azepin-8-ylamino)-pyrimidin-4-ylamino]-3-fluoro-N-methyl-benzamide;
2-[5-Chloro-2-(1-isopropyl-5,5-dimethyl-2,3,4,5-tetrahydro-1H-benzo[b]azepin-8-ylamino)-pyrimidin-4-ylamino]-3-fluoro-N-prop-2-ynyl-benzamide;
(1S,2S,3R,4R)-3-[5-Chloro-2-(1-isopropyl-5,5-dimethyl-2,3,4,5-tetrahydro-1H-benzo[b]azepin-8-ylamino)-pyrimidin-4-ylamino]-bicyclo[2.2.1]hept-5-ene-2-carboxylic acid amide;
5-Chloro-N*2*-(1-isopropyl-5,5-dimethyl-2,3,4,5-tetrahydro-1H-benzo[b]azepin-8-yl)-N*4*-(2-methoxy-4-morpholin-4-yl-phenyl)-pyrimidine-2,4-diamine;
2-{5-Chloro-2-[1-(2-dimethylamino-acetyl)-5,5-dimethyl-2,3,4,5-tetrahydro-1H-benzo[b]azepin-8-ylamino]-pyrimidin-4-ylamino}-3-fluoro-N-methyl-benzamide;
2-{5-Chloro-2-[1-(2-dimethylamino-acetyl)-5,5-dimethyl-2,3,4,5-tetrahydro-1H-benzo[b]azepin-8-ylamino]-pyrimidin-4-ylamino}-3-fluoro-N-prop-2-ynyl-benzamide;

2-[5-Chloro-2-(1-ethyl-5,5-dimethyl-2,3,4,5-tetrahydro-1H-benzo[b]azepin-8-ylamino)-pyrimidin-4-ylamino]-3-fluoro-N-methyl-benzamide;

2-[5-Chloro-2-(1-ethyl-5,5-dimethyl-2,3,4,5-tetrahydro-1H-benzo[b]azepin-8-ylamino)-pyrimidin-4-ylamino]-3-fluoro-N-prop-2-ynyl-benzamide;

(1S,2S,3R,4R)-3-[5-Chloro-2-(1-ethyl-5,5-dimethyl-2,3,4,5-tetrahydro-1H-benzo[b]azepin-8-ylamino)-pyrimidin-4-ylamino]-bicyclo[2.2.1]hept-5-ene-2-carboxylic acid amide;

5-Chloro-N*2*-(1-ethyl-5,5-dimethyl-2,3,4,5-tetrahydro-1H-benzo[b]azepin-8-yl)-N*4*-(2-methoxy-4-morpholin-4-yl-phenyl)-pyrimidine-2,4-diamine;

2-[2-(3-Acetylamino-5,5-dimethyl-2-oxo-2,3,4,5-tetrahydro-1H-benzo[b]azepin-8-ylamino)-5-chloro-pyrimidin-4-ylamino]-N-cyanomethyl-3-fluoro-Benzamide;

2-{5-Chloro-2-[3-(2-methoxy-acetylamino)-5,5-dimethyl-2-oxo-2,3,4,5-tetrahydro-1H-benzo[b]azepin-8-ylamino]-pyrimidin-4-ylamino}-N-cyanomethyl-3-fluoro-benzamide;

2-{5-Chloro-2-[1-(2-dimethylamino-ethyl)-5,5-dimethyl-2,3,4,5-tetrahydro-1H-benzo[b]azepin-8-ylamino]-pyrimidin-4-ylamino}-3-fluoro-N-methyl-benzamide;

2-{5-Chloro-2-[1-(2-dimethylamino-ethyl)-5,5-dimethyl-2,3,4,5-tetrahydro-1H-benzo[b]azepin-8-ylamino]-pyrimidin-4-ylamino}-3-fluoro-N-prop-2-ynyl-benzamide;

(1S,2S,3R,4R)-3-{5-Chloro-2-[1-(2-dimethylamino-ethyl)-5,5-dimethyl-2,3,4,5-tetrahydro-1H-benzo[b]azepin-8-ylamino]-pyrimidin-4-ylamino}-bicyclo[2.2.1]hept-5-ene-2-carboxylic acid amide;

5-Chloro-N*2*-[1-(2-dimethylamino-ethyl)-5,5-dimethyl-2,3,4,5-tetrahydro-1H-benzo[b]azepin-8-yl]-N*4*-(2-methoxy-4-morpholin-4-yl-phenyl)-pyrimidine-2,4-diamine;

2-{5-Chloro-2-[1-ethyl-5,5-dimethyl-2-oxo-3-(2,2,2-trifluoro-acetylamino)-2,3,4,5-tetrahydro-1H-benzo[b]azepin-8-ylamino]-pyrimidin-4-ylamino}-3-fluoro-N-methyl-benzamide;

2-[2-(3-Acetylamino-1-ethyl-5,5-dimethyl-2-oxo-2,3,4,5-tetrahydro-1H-benzo[b]azepin-8-ylamino)-5-chloro-pyrimidin-4-ylamino]-3-fluoro-N-methyl-benzamide;

2-{5-Chloro-2-[1-ethyl-3-(2-methoxy-acetylamino)-5,5-dimethyl-2-oxo-2,3,4,5-tetrahydro-1H-benzo[b]azepin-8-ylamino]-pyrimidin-4-ylamino}-3-fluoro-N-methyl-benzamide;

N-{(1R,2R)-2-[2-(4-Benzyl-7-methoxy-2-oxo-2,3,4,5-tetrahydro-1H-benzo[e][1,4]diazepin-8-ylamino)-5-chloro-pyrimidin-4-ylamino]-cyclohexyl}-methanesulfonamide;

3-[2-(4-Benzyl-7-methoxy-2-oxo-2,3,4,5-tetrahydro-1H-benzo[e][1,4]diaz-epin-8-ylamino)-5-chloro-pyrimidin-4-ylamino]-bicyclo[2.2.1]hept-5-ene-2-carboxylic acid amide;

2-[2-(4-Benzyl-7-methoxy-2-oxo-2,3,4,5-tetrahydro-1H-benzo[e][1,4]diazepin-8-ylamino)-5-chloro-pyrimidin-4-ylamino]-N-ethyl-benzamide;

N-{(1R,2R)-2-[5-Chloro-2-(7-methoxy-2-oxo-2,3,4,5-tetrahydro-1H-benzo[e][1,4]diazepin-8-ylamino)-pyrimidin-4-ylamino]-cyclohexyl}-methanesulfonamide;

2-{8-[5-Chloro-4-(2-dimethylsulfamoyl-phenylamino)-pyrimidin-2-ylamino]-1-dimethylcarbamoylmethyl-7-methoxy-2-oxo-1,2,3,5-tetrahydro-benzo[e][1,4]diazepin-4-yl}-N,N-dimethyl-acetamide;

N7. N-{(1R,2R)-2-[2-(4-Acetyl-7-methoxy-2-oxo-2,3,4,5-tetrahydro-1H-benzo[e][1,4]di-azepin-8-ylamino)-5-chloro-pyrimidin-4-ylamino]-cyclohexyl}-methanesulfonamide;

N-{(1R,2R)-2-[5-Chloro-2-(4-ethyl-7-methoxy-2-oxo-2,3,4,5-tetrahydro-1H-benzo[e][1,4]diazepin-8-ylamino)-pyrimidin-4-ylamino]-cyclohexyl}-methane-sulfonamide;

2-[5-Chloro-2-(4-ethyl-7-methoxy-2-oxo-2,3,4,5-tetrahydro-1H-benzo[e][1,4]diazepin-8-ylamino)-pyrimidin-4-ylamino]-N,N-dimethyl-benzenesulfonamide;

8-{5-Chloro-4-[2-(propane-2-sulfonyl)-phenylamino]-pyrimidin-2-ylamino}-4-ethyl-7-methoxy-1,3,4,5-tetrahydro-benzo[e][1,4]diazepin-2-one;

8-[5-Chloro-4-(2-methoxy-4-morpholin-4-yl-phenylamino)-pyrimidin-2-ylamino]-4-ethyl-7-methoxy-1,3,4,5-tetrahydro-benzo[e][1,4]diazepin-2-one;

8-[5-Chloro-4-(4-methoxy-2-pyrazol-1-yl-phenylamino)-pyrimidin-2-ylamino]-4-ethyl-7-methoxy-1,3,4,5-tetrahydro-benzo[e][1,4]diazepin-2-one;

(1S,2S,3R,4R)-3-[5-Chloro-2-(4-ethyl-7-methoxy-2-oxo-2,3,4,5-tetrahydro-1H-benzo[e][1,4]diazepin-8-ylamino)-pyrimidin-4-ylamino]-bicyclo-[2.2.1]hept-5-ene-2-carboxylic acid amide;

N-(1R,2R)-(2-{5-Chloro-2-[7-methoxy-4-(2-methoxy-ethyl)-2-oxo-2,3,4,5-tetrahydro-1H-benzo[e][1,4]diazepin-8-ylamino]-pyrimidin-4-ylamino}-cyclohexyl)-methanesulfonamide;

(1S,2S,3R,4R)-3-{5-Chloro-2-[7-methoxy-4-(2-methoxy-ethyl)-2-oxo-2,3,4,5-tetrahydro-1H-benzo[e][1,4]diazepin-8-ylamino]-pyrimidin-4-ylamino}-bicyclo[2.2.1]hept-5-ene-2-carboxylic acid amide;

N-(1R,2R)-{2-[5-Chloro-2-(4-cyclopropylmethyl-7-methoxy-2-oxo-2,3,4,5-tetrahydro-1H-benzo[e][1,4]diazepin-8-ylamino)-pyrimidin-4-ylamino]-cyclohexyl}-methane-sulfonamide;

(1S,2S,3R,4R)-3-[5-Chloro-2-(4-cyclopropylmethyl-7-methoxy-2-oxo-2,3,4,5-tetrahydro-1H-benzo[e][1,4]diazepin-8-ylamino)-pyrimidin-4-ylamino]-bicyclo[2.2.1]hept-5-ene-2-carboxylic acid amide;

8-{5-Chloro-4-[2-(pyrrolidine-1-sulfonyl)-phenylamino]-pyrimidin-2-ylamino}-4-cyclopropylmethyl-7-methoxy-1,3,4,5-tetrahydro-benzo[e][1,4]diazepin-2-one;

2-[5-Chloro-2-(8-methoxy-5,5-dimethyl-2-oxo-2,3,4,5-tetrahydro-1H-benzo[b]azepin-7-ylamino)-pyrimidin-4-ylamino]-N-methyl-benzamide;

7-[5-Chloro-4-(2-methoxy-4-morpholin-4-yl-phenylamino)-pyrimidin-2-ylamino]-8-methoxy-5,5-dimethyl-1,3,4,5-tetrahydro-benzo[b]azepin-2-one;

(1S,2S,3R,4R)-3-{5-Chloro-2-[8-methoxy-3-((S)-3,3,3-trifluoro-2-hydroxy-propyl)-2,3,4,5-tetrahydro-1H-benzo[d]azepin-7-ylamino]-pyrimidin-4-ylamino}-bicyclo[2.2.1]hept-5-ene-2-carboxylic acid amide;

N-{(1R,2R)-2-[5-Chloro-2-(5,5-dimethyl-2-oxo-2,3,4,5-tetrahydro-1H-benzo[b]azepin-7-ylamino)-pyrimidin-4-ylamino]-cyclohexyl}-N-methyl-methanesulfonamide;

N-{(1R,2R)-2-[5-Chloro-2-(5,5-dimethyl-2-oxo-2,3,4,5-tetrahydro-1H-benzo[b]azepin-7-ylamino)-pyrimidin-4-ylamino]-cyclohexyl}-N-ethyl-methanesulfonamide;

N-((1R,2R)-2-{5-Chloro-2-[8-methoxy-3-(2-methoxy-ethyl)-2,3,4,5-tetrahydro-1H-benzo[d]azepin-7-ylamino]-pyrimidin-4-ylamino}-cyclohexyl)-N-methyl-methanesulfonamide;

N-((1R,2R)-2-{5-Chloro-2-[8-methoxy-3-(2-methoxy-ethyl)-2,3,4,5-tetrahydro-1H-benzo[d]azepin-7-ylamino]-pyrimidin-4-ylamino}-cyclohexyl)-N-ethyl-methanesulfonamide;

N-{(1R,2R)-2-[5-Chloro-2-(1-ethyl-8-methoxy-2-oxo-2,3,4,5-tetrahydro-1H-benzo[b]azepin-7-ylamino)-pyrimidin-4-ylamino]-cyclohexyl}-N-methyl-methanesulfonamide;

N-{(1R,2R)-2-[5-Chloro-2-(1-ethyl-6-methoxy-2-oxo-2,3,4,5-tetrahydro-1H-benzo[b]azepin-7-ylamino)-pyrimidin-4-ylamino]-cyclohexyl}-N-methyl-methanesulfonamide;
N-{(1R,2R)-2-[5-Chloro-2-(1,5,5-trimethyl-2-oxo-2,3,4,5-tetrahydro-1H-benzo[b]azepin-7-ylamino)-pyrimidin-4-ylamino]-cyclohexyl}-N-methyl-methanesulfonamide;
N-{(1R,2R)-2-[5-Chloro-2-(7-morpholin-4-yl-6,7,8,9-tetrahydro-5H-benzocyclohepten-2-ylamino)-pyrimidin-4-ylamino]-cyclohexyl}-N-methyl-methanesulfonamide;
2-[5-Chloro-2-(1-methyl-2-oxo-2,3,4,5-tetrahydro-1H-benzo[b]azepin-7-ylamino)-pyrimidin-4-ylamino]-N-(2-cyano-ethyl)-N-methyl-benzamide;
5-Chloro-N*2-[3-(2-methoxy-ethyl)-2,3,4,5-tetrahydro-1H-benzo[d]azepin-7-yl]-N*4*-[2-(propane-2-sulfonyl)-phenyl]-pyrimidine-2,4-diamine;
2-{5-Chloro-2-[3-(2-methoxy-ethyl)-2,3,4,5-tetrahydro-1H-benzo[d]azepin-7-ylamino]-pyrimidin-4-ylamino}-N,N-dimethyl-benzenesulfonamide;
N-{(1R,2R)-2-[5-Chloro-2-(9-ethyl-2-fluoro-6,7,8,9-tetrahydro-5-oxa-9-aza-benzocyclohepten-3-ylamino)-pyrimidin-4-ylamino]-cyclohexyl}-methanesulfonamide;
5-Chloro-N*2*-(9-ethyl-2-fluoro-6,7,8,9-tetrahydro-5-oxa-9-aza-benzocyclohepten-3-yl)-N*4*-(2-methoxy-4-morpholin-4-yl-phenyl)-pyrimidine-2,4-diamine;
3-(2-{5-Chloro-2-[3-(2-methoxy-ethyl)-2,3,4,5-tetrahydro-1H-benzo[d]azepin-7-ylamino]-pyrimidin-4-ylamino}-5-morpholin-4-yl-phenoxy)-propionitrile;
3-{2-[5-Chloro-2-(5,5-dimethyl-2-oxo-2,3,4,5-tetrahydro-1H-benzo[b]azepin-8-ylamino)-pyrimidin-4-ylamino]-5-morpholin-4-yl-phenoxy}-propionitrile;
2-[5-Chloro-2-(9-ethyl-2-fluoro-6,7,8,9-tetrahydro-5-oxa-9-aza-benzocyclohepten-3-ylamino)-pyrimidin-4-ylamino]-3-fluoro-N-methyl-benzamide;
2-[5-Chloro-2-(9-ethyl-6,7,8,9-tetrahydro-5-oxa-9-aza-benzocyclohepten-3-ylamino)-pyrimidin-4-ylamino]-3-fluoro-N-methyl-benzamide;
N-{(1R,2R)-2-[5-Chloro-2-(9-ethyl-6,7,8,9-tetrahydro-5-oxa-9-aza-benzocyclohepten-3-ylamino)-pyrimidin-4-ylamino]-cyclohexyl}-methanesulfonamide;
5-Chloro-N*2*-(9-ethyl-6,7,8,9-tetrahydro-5-oxa-9-aza-benzocyclohepten-3-yl)-N*4*-(2-methoxy-4-morpholin-4-yl-phenyl)-pyrimidine-2,4-diamine;
8-{5-Chloro-4-[2-fluoro-6-(2-methoxy-ethoxy)-phenylamino]-pyrimidin-2-ylamino}-1,3,4,5-tetrahydro-benzo[b]azepin-2-one;
5-Chloro-N*4*-[2-fluoro-6-(2-methoxy-ethoxy)-phenyl]-N*2*-[3-(2-methoxy-ethyl)-2,3,4,5-tetrahydro-1H-benzo[d]azepin-7-yl]-pyrimidine-2,4-diamine;
2-[5-Chloro-2-(9-ethyl-6,7,8,9-tetrahydro-5-oxa-9-aza-benzocyclohepten-2-ylamino)-pyrimidin-4-ylamino]-3-fluoro-N-methyl-benzamide;
3-[5-Chloro-2-(9-ethyl-6,7,8,9-tetrahydro-5-oxa-9-aza-benzocyclohepten-2-ylamino)-pyrimidin-4-ylamino]-thiophene-2-carboxylic acid methylamide;
(1R,2S,3R,4S,5S,6R)-3-[5-Chloro-2-(1-ethyl-6-methoxy-2-oxo-2,3,4,5-tetrahydro-1H-benzo[b]azepin-7-ylamino)-pyrimidin-4-ylamino]-5,6-dihydroxy-bicyclo[2.2.1]heptane-2-carboxylic acid amide;
2-[4-(2-Allyloxy-6-fluoro-4-morpholin-4-yl-phenylamino)-5-chloro-pyrimidin-2-ylamino]-5-methyl-8,9-dihydro-5H-7-oxa-5-aza-benzocyclohepten-6-one;
2-[2-(9-Acetyl-6,7,8,9-tetrahydro-5-oxa-9-aza-benzocyclohepten-2-ylamino)-5-chloro-pyrimidin-4-ylamino]-3-fluoro-N-methyl-benzamide;
2-[2-(9-Acetyl-6,7,8,9-tetrahydro-5-oxa-9-aza-benzocyclohepten-2-ylamino)-5-chloro-pyrimidin-4-ylamino]-3-fluoro-N-methyl-benzamide;
2-[2-(9-Acetyl-6,7,8,9-tetrahydro-5-oxa-9-aza-benzocyclohepten-2-ylamino)-5-chloro-pyrimidin-4-ylamino]-N-methyl-benzamide;
2-{5-Chloro-2-[9-(2-pyrrolidin-1-yl-acetyl)-6,7,8,9-tetrahydro-5-oxa-9-aza-benzocyclohepten-2-ylamino]-pyrimidin-4-ylamino}-3-fluoro-N-methyl-benzamide;
3-{5-Chloro-2-[9-(2-pyrrolidin-1-yl-acetyl)-6,7,8,9-tetrahydro-5-oxa-9-aza-benzocyclohepten-2-ylamino]-pyrimidin-4-ylamino}-thiophene-2-carboxylic acid methylamide;
2-{5-Chloro-2-[9-(2-pyrrolidin-1-yl-acetyl)-6,7,8,9-tetrahydro-5-oxa-9-aza-benzocyclohepten-2-ylamino]-pyrimidin-4-ylamino}-N-methyl-benzamide;
2-[5-Chloro-2-(9-methyl-6,7,8,9-tetrahydro-5-oxa-9-aza-benzocyclohepten-2-ylamino)-pyrimidin-4-ylamino]-3-fluoro-N-methyl-benzamide;
2-[5-Chloro-2-(9-methyl-6,7,8,9-tetrahydro-5-oxa-9-aza-benzocyclohepten-2-ylamino)-pyrimidin-4-ylamino]-N-methyl-benzamide;
2-[4-(2-Allyloxy-4-dimethylamino-6-fluoro-phenylamino)-5-chloro-pyrimidin-2-ylamino]-5-methyl-8,9-dihydro-5H-7-oxa-5-aza-benzocyclohepten-6-one;
N*4*-(2-Allyloxy-4-dimethylamino-6-fluoro-phenyl)-5-chloro-N*2*-[3-(2-methoxy-ethyl)-2,3,4,5-tetrahydro-1H-benzo[d]azepin-7-yl]-pyrimidine-2,4-diamine;
2-{5-Chloro-2-[3-(2-methoxy-ethyl)-2,3,4,5-tetrahydro-1H-benzo[d]azepin-7-ylamino]-pyrimidin-4-ylamino}-N-cyclopropylmethyl-3-fluoro-benzamide;
2-[5-Chloro-2-(2-oxo-2,3,4,5-tetrahydro-1H-benzo[b]azepin-8-ylamino)-pyrimidin-4-ylamino]-N-cyclopropylmethyl-3-fluoro-benzamide;
2-[2-(9-Acetyl-6,7,8,9-tetrahydro-5-oxa-9-aza-benzocyclohepten-2-ylamino)-5-chloro-pyrimidin-4-ylamino]-3-fluoro-N-prop-2-ynyl-benzamide;
2-{5-Chloro-2-[9-(2-pyrrolidin-1-yl-acetyl)-6,7,8,9-tetrahydro-5-oxa-9-aza-benzocyclohepten-3-ylamino]-pyrimidin-4-ylamino}-3-fluoro-N-methyl-benzamide;
3-{5-Chloro-2-[9-(2-pyrrolidin-1-yl-acetyl)-6,7,8,9-tetrahydro-5-oxa-9-aza-benzocyclohepten-3-ylamino]-pyrimidin-4-ylamino}-thiophene-2-carboxylic acid methylamide;
2-{5-Chloro-2-[9-(2-pyrrolidin-1-yl-acetyl)-6,7,8,9-tetrahydro-5-oxa-9-aza-benzocyclohepten-3-ylamino]-pyrimidin-4-ylamino}-3-fluoro-N-prop-2-ynyl-benzamide;
2-{5-Chloro-4-[2-(2,3-dihydroxy-propoxy)-6-fluoro-phenylamino]-pyrimidin-2-ylamino}-5-methyl-8,9-dihydro-5H-7-oxa-5-aza-benzocyclohepten-6-one;
2-{5-Chloro-2-[9-(2-pyrrolidin-1-yl-ethyl)-6,7,8,9-tetrahydro-5-oxa-9-aza-benzocyclohepten-3-ylamino]-pyrimidin-4-ylamino}-3-fluoro-N-methyl-benzamide;
2-{5-Chloro-2-[9-(2-pyrrolidin-1-yl-ethyl)-6,7,8,9-tetrahydro-5-oxa-9-aza-benzocyclohepten-3-ylamino]-pyrimidin-4-ylamino}-3-fluoro-N-prop-2-ynyl-benzamide;
2-[5-Chloro-2-(9-ethyl-7-hydroxy-7-hydroxymethyl-6,7,8,9-tetrahydro-5-oxa-9-aza-benzocyclohepten-2-ylamino)-pyrimidin-4-ylamino]-3-fluoro-N-methyl-benzamide;
2-[5-Chloro-2-(9-ethyl-7-hydroxy-7-hydroxymethyl-6,7,8,9-tetrahydro-5-oxa-9-aza-benzocyclohepten-2-ylamino)-pyrimidin-4-ylamino]-3-fluoro-N-prop-2-ynyl-benzamide;
2-[5-Chloro-2-(9-ethyl-7-morpholin-4-yl-6,7,8,9-tetrahydro-5-oxa-9-aza-benzocyclohepten-2-ylamino)-pyrimidin-4-ylamino]-3-fluoro-N-methyl-benzamide;

2-[5-Chloro-2-(6,7,8,9-tetrahydro-5-oxa-9-aza-benzocyclo-hepten-3-ylamino)-pyrimidin-4-ylamino]-3-fluoro-N-methyl-benzamide;

2-[2-(9-Acetyl-6,7,8,9-tetrahydro-5-oxa-9-aza-benzocyclo-hepten-3-ylamino)-5-chloro-pyrimidin-4-ylamino]-3-fluoro-N-methyl-benzamide;

2-[2-(9-Acetyl-6,7,8,9-tetrahydro-5-oxa-9-aza-benzocyclo-hepten-3-ylamino)-5-chloro-pyrimidin-4-ylamino]-3-fluoro-N-prop-2-ynyl-benzamide;

2-{5-Chloro-2-[9-(2-methoxy-acetyl)-6,7,8,9-tetrahydro-5-oxa-9-aza-benzocyclohepten-3-ylamino]-pyrimidin-4-ylamino}-3-fluoro-N-methyl-benzamide;

(2-{5-Chloro-2-[3-(2-methoxy-ethyl)-2,3,4,5-tetrahydro-1H-benzo[d]azepin-7-ylamino]-pyrimidin-4-ylamino}-3-fluoro-phenoxy)-acetic acid methyl ester;

2-{5-Chloro-2-[3-(2-methoxy-ethyl)-2,3,4,5-tetrahydro-1H-benzo[d]azepin-7-ylamino]-pyrimidin-4-ylamino}-3,5-difluoro-N-prop-2-ynyl-benzamide;

2-[5-Chloro-2-(2-oxo-2,3,4,5-tetrahydro-1H-benzo[b]azepin-8-ylamino)-pyrimidin-4-ylamino]-3,5-difluoro-N-prop-2-ynyl-benzamide;

5-Chloro-N*2*-[3-(2-methoxy-ethyl)-2,3,4,5-tetrahydro-1H-benzo[d]azepin-7-yl]-N*4*-[2-(pyrrolidine-1-sulfonyl)-phenyl]-pyrimidine-2,4-diamine;

8-{5-Chloro-4-[2-(pyrrolidine-1-sulfonyl)-phenylamino]-pyrimidin-2-ylamino}-1,3,4,5-tetrahydro-benzo[b]azepin-2-one;

2-{5-Chloro-4-[2-fluoro-6-(2-hydroxy-ethoxy)-phenylamino]-pyrimidin-2-ylamino}-5-methyl-8,9-dihydro-5H-7-oxa-5-aza-benzocyclohepten-6-one;

2-[5-Chloro-2-(9-isopropyl-6,7,8,9-tetrahydro-5-oxa-9-aza-benzocyclohepten-2-ylamino)-pyrimidin-4-ylamino]-3-fluoro-N-prop-2-ynyl-benzamide;

2-[5-Chloro-2-(9-isopropyl-6,7,8,9-tetrahydro-5-oxa-9-aza-benzocyclohepten-2-ylamino)-pyrimidin-4-ylamino]-3-fluoro-N-methyl-benzamide;

2-[5-Chloro-2-(9-ethyl-7-hydroxy-7-hydroxymethyl-6,7,8,9-tetrahydro-5-oxa-9-aza-benzocyclohepten-3-ylamino)-pyrimidin-4-ylamino]-3-fluoro-N-prop-2-ynyl-benzamide;

2-[5-Chloro-2-(9-ethyl-7-hydroxy-7-hydroxymethyl-6,7,8,9-tetrahydro-5-oxa-9-aza-benzocyclohepten-3-ylamino)-pyrimidin-4-ylamino]-3-fluoro-N-methyl-benzamide;

2-[5-Chloro-2-(5-methyl-6-oxo-5,6,8,9-tetrahydro-7-oxa-5-aza-benzocyclohepten-2-ylamino)-pyrimidin-4-ylamino]-N-methyl-benzamide;

2-[5-Chloro-2-(5-methyl-6-oxo-5,6,8,9-tetrahydro-7-oxa-5-aza-benzocyclohepten-2-ylamino)-pyrimidin-4-ylamino]-3-fluoro-N-methyl-benzamide;

3-Chloro-2-[5-chloro-2-(5-methyl-6-oxo-5,6,8,9-tetrahydro-7-oxa-5-aza-benzocyclohepten-2-ylamino)-pyrimidin-4-ylamino]-N-methyl-benzamide;

2-[5-Chloro-2-(5-methyl-6-oxo-5,6,8,9-tetrahydro-7-oxa-5-aza-benzocyclohepten-2-ylamino)-pyrimidin-4-ylamino]-3,N-dimethyl-benzamide;

2-[5-Chloro-2-(5-ethyl-6-oxo-5,6,8,9-tetrahydro-7-oxa-5-aza-benzocyclohepten-2-ylamino)-pyrimidin-4-ylamino]-N-methyl-benzamide;

2-[5-Chloro-2-(5-ethyl-6-oxo-5,6,8,9-tetrahydro-7-oxa-5-aza-benzocyclohepten-2-ylamino)-pyrimidin-4-ylamino]-3-fluoro-N-methyl-benzamide;

3-[5-Chloro-2-(5-methyl-6-oxo-5,6,8,9-tetrahydro-7-oxa-5-aza-benzocyclohepten-2-ylamino)-pyrimidin-4-ylamino]-thiophene-2-carboxylic acid methylamide;

{2-[5-Chloro-2-(5-methyl-6-oxo-5,6,8,9-tetrahydro-7-oxa-5-aza-benzocyclohepten-2-ylamino)-pyrimidin-4-ylamino]-phenoxy}-acetonitrile;

2-{5-Chloro-4-[2-(1-methyl-1H-imidazol-2-yl)-phenylamino]-pyrimidin-2-ylamino}-5-methyl-8,9-dihydro-5H-7-oxa-5-aza-benzocyclohepten-6-one;

2-[5-Chloro-2-(5-methyl-6-oxo-5,6,8,9-tetrahydro-7-oxa-5-aza-benzocyclohepten-2-ylamino)-pyrimidin-4-ylamino]-3,5,N-trimethyl-benzamide;

3-Bromo-2-[5-chloro-2-(5-methyl-6-oxo-5,6,8,9-tetrahydro-7-oxa-5-aza-benzocyclohepten-2-ylamino)-pyrimidin-4-ylamino]-N-methyl-benzamide;

2-[5-Chloro-2-(5-methyl-6-oxo-5,6,8,9-tetrahydro-7-oxa-5-aza-benzocyclohepten-2-ylamino)-pyrimidin-4-ylamino]-5-fluoro-N-methyl-benzamide;

2-[5-Chloro-2-(5-methyl-6-oxo-5,6,8,9-tetrahydro-7-oxa-5-aza-benzocyclohepten-2-ylamino)-pyrimidin-4-ylamino]-N-methyl-3-trifluoromethyl-benzamide;

2-[5-Chloro-2-(5-methyl-6-oxo-5,6,8,9-tetrahydro-7-oxa-5-aza-benzocyclohepten-2-ylamino)-pyrimidin-4-ylamino]-N-methyl-4-trifluoromethyl-benzamide;

2-[5-Chloro-2-(5-methyl-6-oxo-5,6,8,9-tetrahydro-7-oxa-5-aza-benzocyclohepten-2-ylamino)-pyrimidin-4-ylamino]-6,N-dimethyl-benzamide;

2-[5-Chloro-2-(5-methyl-6-oxo-5,6,8,9-tetrahydro-7-oxa-5-aza-benzocyclohepten-2-ylamino)-pyrimidin-4-ylamino]-6-fluoro-N-methyl-benzamide;

3,4-Dichloro-2-[5-chloro-2-(5-methyl-6-oxo-5,6,8,9-tetrahydro-7-oxa-5-aza-benzocyclohepten-2-ylamino)-pyrimidin-4-ylamino]-N-methyl-benzamide;

3-Chloro-2-[5-chloro-2-(5-methyl-6-oxo-5,6,8,9-tetrahydro-7-oxa-5-aza-benzocyclohepten-2-ylamino)-pyrimidin-4-ylamino]-5-fluoro-N-methyl-benzamide;

3-[5-Chloro-2-(5-methyl-6-oxo-5,6,8,9-tetrahydro-7-oxa-5-aza-benzocyclohepten-2-ylamino)-pyrimidin-4-ylamino]-4-methyl-thiophene-2-carboxylic acid methylamide;

3-[5-Chloro-2-(5-methyl-6-oxo-5,6,8,9-tetrahydro-7-oxa-5-aza-benzocyclohepten-2-ylamino)-pyrimidin-4-ylamino]-thiophene-2-carboxylic acid prop-2-ynylamide;

5-tert-Butyl-3-[5-chloro-2-(5-methyl-6-oxo-5,6,8,9-tetrahydro-7-oxa-5-aza-benzocyclohepten-2-ylamino)-pyrimidin-4-ylamino]-thiophene-2-carboxylic acid methylamide;

3-[5-Chloro-2-(5-methyl-6-oxo-5,6,8,9-tetrahydro-7-oxa-5-aza-benzocyclohepten-2-ylamino)-pyrimidin-4-ylamino]-4-methyl-5-phenyl-thiophene-2-carboxylic acid methyl ester;

(R)-2-[5-Chloro-2-(5-methyl-6-oxo-5,6,8,9-tetrahydro-7-oxa-5-aza-benzocyclohepten-2-ylamino)-pyrimidin-4-ylamino]-3-methyl-butyramide;

(S)-2-[5-Chloro-2-(5-methyl-6-oxo-5,6,8,9-tetrahydro-7-oxa-5-aza-benzocyclohepten-2-ylamino)-pyrimidin-4-ylamino]-3-methyl-butyramide;

2-{[5-Fluoro-2-(5-methyl-6-oxo-5,6,8,9-tetrahydro-7-oxa-5-aza-benzocyclohepten-2-ylamino)-pyrimidin-4-yl]-methyl-amino}-N-methyl-benzamide;

2-[5-Chloro-4-(2-pyrazol-1-yl-phenylamino)-pyrimidin-2-ylamino]-5-methyl-8,9-dihydro-5H-7-oxa-5-aza-benzocyclohepten-6-one;

2-{5-Chloro-4-[2-(1H-pyrazol-3-yl)-phenylamino]-pyrimidin-2-ylamino}-5-methyl-8,9-dihydro-5H-7-oxa-5-aza-benzocyclohepten-6-one;

2-[5-Chloro-4-(2,2-difluoro-benzo[1,3]dioxol-4-ylamino)-pyrimidin-2-ylamino]-5-methyl-8,9-dihydro-5H-7-oxa-5-aza-benzocyclohepten-6-one;

2-[5-Chloro-4-(1H-indazol-4-ylamino)-pyrimidin-2-ylamino]-5-methyl-8,9-dihydro-5H-7-oxa-5-aza-benzocyclohepten-6-one;

5-Chloro-3-[5-chloro-2-(5-methyl-6-oxo-5,6,8,9-tetrahydro-7-oxa-5-aza-benzocyclohepten-2-ylamino)-pyrimidin-4-ylamino]-4-methyl-thiophene-2-carboxylic acid methylamide;

5-Bromo-3-[5-chloro-2-(5-methyl-6-oxo-5,6,8,9-tetrahydro-7-oxa-5-aza-benzocyclohepten-2-ylamino)-pyrimidin-4-ylamino]-4-methyl-thiophene-2-carboxylic acid methylamide;

3-[5-Chloro-2-(5-methyl-6-oxo-5,6,8,9-tetrahydro-7-oxa-5-aza-benzocyclohepten-2-ylamino)-pyrimidin-4-ylamino]-4,5-dimethyl-thiophene-2-carboxylic acid methylamide;

2-[5-Chloro-2-(5-methyl-6-oxo-5,6,8,9-tetrahydro-7-oxa-5-aza-benzocyclohepten-2-ylamino)-pyrimidin-4-ylamino]-N-methyl-3-trifluoromethoxy-benzamide;

2,5-Dichloro-4-[5-chloro-2-(5-methyl-6-oxo-5,6,8,9-tetrahydro-7-oxa-5-aza-benzocyclohepten-2-ylamino)-pyrimidin-4-ylamino]-thiophene-3-carboxylic acid methylamide;

4-[5-Chloro-2-(5-methyl-6-oxo-5,6,8,9-tetrahydro-7-oxa-5-aza-benzocyclohepten-2-ylamino)-pyrimidin-4-ylamino]-5-methyl-isoxazole-3-carboxylic acid methylamide;

5-[5-Chloro-2-(5-methyl-6-oxo-5,6,8,9-tetrahydro-7-oxa-5-aza-benzocyclohepten-2-ylamino)-pyrimidin-4-ylamino]-1-methyl-1H-pyrazole-4-carboxylic acid methylamide;

2-{5-Chloro-4-[2-(2-methoxy-ethoxy)-phenylamino]-pyrimidin-2-ylamino}-5-methyl-8,9-dihydro-5H-7-oxa-5-aza-benzocyclohepten-6-one;

2-{5-Chloro-4-[2-fluoro-6-(2-methoxy-ethoxy)-phenylamino]-pyrimidin-2-ylamino}-5-methyl-8,9-dihydro-5H-7-oxa-5-aza-benzocyclohepten-6-one;

2-[5-Chloro-4-(2-fluoro-6-prop-2-ynyloxy-phenylamino)-pyrimidin-2-ylamino]-5-methyl-8,9-dihydro-5H-7-oxa-5-aza-benzocyclohepten-6-one;

2-[4-(2-Allyloxy-6-fluoro-phenylamino)-5-chloro-pyrimidin-2-ylamino]-5-methyl-8,9-dihydro-5H-7-oxa-5-aza-benzocyclohepten-6-one;

2-{4-[2-(2-Amino-ethoxy)-6-fluoro-phenylamino]-5-chloro-pyrimidin-2-ylamino}-5-methyl-8,9-dihydro-5H-7-oxa-5-aza-benzocyclohepten-6-one;

N-(2-{2-[5-Chloro-2-(5-methyl-6-oxo-5,6,8,9-tetrahydro-7-oxa-5-aza-benzocyclohepten-2-ylamino)-pyrimidin-4-ylamino]-3-fluoro-phenoxy}-ethyl)-acetamide;

2-{5-Chloro-4-[2-(5-ethylamino-[1,3,4]oxadiazol-2-yl)-phenylamino]-pyrimidin-2-ylamino}-5-methyl-8,9-dihydro-5H-7-oxa-5-aza-benzocyclohepten-6-one;

2-{5-Chloro-4-[2-(3-methyl-[1,2,4]oxadiazol-5-yl)-phenylamino]-pyrimidin-2-ylamino}-5-methyl-8,9-dihydro-5H-7-oxa-5-aza-benzocyclohepten-6-one;

2-{5-Chloro-4-[2-fluoro-6-(3-methyl-[1,2,4]oxadiazol-5-yl)-phenylamino]-pyrimidin-2-ylamino}-5-methyl-8,9-dihydro-5H-7-oxa-5-aza-benzocyclohepten-6-one;

2-{5-Chloro-4-[2-(5-methyl-[1,3,4]oxadiazol-2-yl)-phenylamino]-pyrimidin-2-ylamino}-5-methyl-8,9-dihydro-5H-7-oxa-5-aza-benzocyclohepten-6-one;

2-{5-Chloro-4-[2-fluoro-6-(5-methyl-[1,3,4]oxadiazol-2-yl)-phenylamino]-pyrimidin-2-ylamino}-5-methyl-8,9-dihydro-5H-7-oxa-5-aza-benzocyclohepten-6-one;

2-{5-Chloro-4-[2-(5-methyl-2H-[1,2,4]triazol-3-yl)-phenylamino]-pyrimidin-2-ylamino}-5-methyl-8,9-dihydro-5H-7-oxa-5-aza-benzocyclohepten-6-one;

2-{5-Chloro-4-[2-fluoro-6-(5-methyl-oxazol-2-yl)-phenylamino]-pyrimidin-2-ylamino}-5-methyl-8,9-dihydro-5H-7-oxa-5-aza-benzocyclohepten-6-one;

2-{5-Chloro-4-[2-(5-methyl-oxazol-2-yl)-thiophen-3-ylamino]-pyrimidin-2-ylamino}-5-methyl-8,9-dihydro-5H-7-oxa-5-aza-benzocyclohepten-6-one;

2-[5-Chloro-4-(2-methylaminomethyl-phenylamino)-pyrimidin-2-ylamino]-5-methyl-8,9-dihydro-5H-7-oxa-5-aza-benzocyclohepten-6-one;

N-{2-[5-Chloro-2-(5-methyl-6-oxo-5,6,8,9-tetrahydro-7-oxa-5-aza-benzocyclohepten-2-ylamino)-pyrimidin-4-ylamino]-benzyl}-N-methyl-acetamide;

N-{2-[5-Chloro-2-(5-methyl-6-oxo-5,6,8,9-tetrahydro-7-oxa-5-aza-benzocyclohepten-2-ylamino)-pyrimidin-4-ylamino]-benzyl}-acetamide;

2-[5-Chloro-2-(3-oxo-2,3,4,5-tetrahydro-1H-benzo[c]azepin-8-ylamino)-pyrimidin-4-ylamino]-N-methyl-benzamide;

3-[5-Chloro-2-(3-oxo-2,3,4,5-tetrahydro-1H-benzo[c]azepin-8-ylamino)-pyrimidin-4-ylamino]-4-methyl-thiophene-2-carboxylic acid methylamide;

3-Chloro-2-[5-chloro-2-(3-oxo-2,3,4,5-tetrahydro-1H-benzo[c]azepin-8-ylamino)-pyrimidin-4-ylamino]-N-methyl-benzamide;

(1R,2R,3S,4S)-3-[5-Chloro-2-(3-oxo-2,3,4,5-tetrahydro-1H-benzo[c]azepin-8-ylamino)-pyrimidin-4-ylamino]-bicyclo[2.2.1]hept-5-ene-2-carboxylic acid amide;

2-[5-Chloro-2-(2-methyl-3-oxo-2,3-dihydro-1H-benzo[c]azepin-8-ylamino)-pyrimidin-4-ylamino]-N-methyl-benzamide;

2-[5-Chloro-2-(2-methyl-3-oxo-2,3,4,5-tetrahydro-1H-benzo[c]azepin-8-ylamino)-pyrimidin-4-ylamino]-N-methyl-benzamide;

3-[5-Chloro-2-(2-methyl-3-oxo-2,3,4,5-tetrahydro-1H-benzo[c]azepin-8-ylamino)-pyrimidin-4-ylamino]-4-methyl-thiophene-2-carboxylic acid methylamide;

2-{[5-Fluoro-2-(2-methyl-3-oxo-2,3,4,5-tetrahydro-1H-benzo[c]azepin-8-ylamino)-pyrimidin-4-yl]-methyl-amino}-N-methyl-benzamide;

2-[5-Chloro-2-(2-methyl-3-oxo-2,3,4,5-tetrahydro-1H-benzo[c]azepin-8-ylamino)-pyrimidin-4-ylamino]-3,5,N-trimethyl-benzamide;

8-{5-Chloro-4-[2-(1-methyl-1H-imidazol-2-yl)-phenylamino]-pyrimidin-2-ylamino}-2-methyl-1,2,4,5-tetrahydro-benzo[c]azepin-3-one;

8-[5-Chloro-4-(2,2-difluoro-benzo[1,3]dioxol-4-ylamino)-pyrimidin-2-ylamino]-2-methyl-1,2,4,5-tetrahydro-benzo[c]azepin-3-one;

8-{5-Chloro-4-[2-(1H-pyrazol-3-yl)-phenylamino]-pyrimidin-2-ylamino}-2-methyl-1,2,4,5-tetrahydro-benzo[c]azepin-3-one;

3-Chloro-2-[5-chloro-2-(2-methyl-3-oxo-2,3,4,5-tetrahydro-1H-benzo[c]azepin-8-ylamino)-pyrimidin-4-ylamino]-N-methyl-benzamide;

2-[5-Chloro-2-(2-methyl-3-oxo-2,3,4,5-tetrahydro-1H-benzo[c]azepin-8-ylamino)-pyrimidin-4-ylamino]-3-fluoro-N-methyl-benzamide;

2,5-Dichloro-4-[5-chloro-2-(2-methyl-3-oxo-2,3,4,5-tetrahydro-1H-benzo[c]azepin-8-ylamino)-pyrimidin-4-ylamino]-thiophene-3-carboxylic acid methylamide;

8-[5-Chloro-4-(2-methylaminomethyl-phenylamino)-pyrimidin-2-ylamino]-2-methyl-1,2,4,5-tetrahydro-benzo[c]azepin-3-one;

2-[5-Chloro-2-(2-methyl-3-oxo-2,3,4,5-tetrahydro-1H-benzo[c]azepin-8-ylamino)-pyrimidin-4-ylamino]-5-fluoro-N-methyl-benzamide;

{2-[5-Chloro-2-(2-methyl-3-oxo-2,3,4,5-tetrahydro-1H-benzo[c]azepin-8-ylamino)-pyrimidin-4-ylamino]-phenoxy}-acetonitrile;

2-[5-Chloro-2-(4-oxo-2,3,4,5-tetrahydro-1H-benzo[d]
azepin-7-ylamino)-pyrimidin-4-ylamino]-N-methyl-benzamide;
3-[5-Chloro-2-(4-oxo-2,3,4,5-tetrahydro-1H-benzo[d]
azepin-7-ylamino)-pyrimidin-4-ylamino]-4-methyl-thiophene-2-carboxylic acid methylamide;
8-[5-Chloro-4-(2-pyrazol-1-yl-phenylamino)-pyrimidin-2-ylamino]-1,3,4,5-tetrahydro-benzo[d]azepin-2-one;
2-[5-Chloro-2-(4-oxo-2,3,4,5-tetrahydro-1H-benzo[d]
azepin-7-ylamino)-pyrimidin-4-ylamino]-3,5,N-trimethyl-benzamide;
2-[5-Chloro-2-(3-methyl-4-oxo-2,3,4,5-tetrahydro-1H-benzo[d]azepin-7-ylamino)-pyrimidin-4-ylamino]-N-methyl-benzamide;
3-[5-Chloro-2-(3-methyl-4-oxo-2,3,4,5-tetrahydro-1H-benzo[d]azepin-7-ylamino)-pyrimidin-4-ylamino]-4-methyl-thiophene-2-carboxylic acid methylamide;
3-Chloro-2-[5-chloro-2-(3-methyl-4-oxo-2,3,4,5-tetrahydro-1H-benzo[d]azepin-7-ylamino)-pyrimidin-4-ylamino]-N-methyl-benzamide;
2-[5-Chloro-2-(3-methyl-4-oxo-2,3,4,5-tetrahydro-1H-benzo[d]azepin-7-ylamino)-pyrimidin-4-ylamino]-3,5,N-trimethyl-benzamide;
8-[5-Chloro-4-(2-pyrazol-1-yl-phenylamino)-pyrimidin-2-ylamino]-3-methyl-1,3,4,5-tetrahydro-benzo[d]azepin-2-one;
3-[5-Chloro-2-(3-methyl-4-oxo-2,3,4,5-tetrahydro-1H-benzo[d]azepin-7-ylamino)-pyrimidin-4-ylamino]-pyridine-2-carboxylic acid methylamide;
5-[5-Chloro-2-(3-methyl-4-oxo-2,3,4,5-tetrahydro-1H-benzo[d]azepin-7-ylamino)-pyrimidin-4-ylamino]-1-methyl-1H-pyrazole-4-carboxylic acid methylamide;
(R)-2-[5-Chloro-2-(3-methyl-4-oxo-2,3,4,5-tetrahydro-1H-benzo[d]azepin-7-ylamino)-pyrimidin-4-ylamino]-3-methyl-butyramide;
(S)-2-[5-Chloro-2-(3-methyl-4-oxo-2,3,4,5-tetrahydro-1H-benzo[d]azepin-7-ylamino)-pyrimidin-4-ylamino]-3-methyl-butyramide;
2-{[5-Fluoro-2-(3-methyl-4-oxo-2,3,4,5-tetrahydro-1H-benzo[d]azepin-7-ylamino)-pyrimidin-4-yl]-methyl-amino}-N-methyl-benzamide;
8-{5-Chloro-4-[2-(1H-pyrazol-3-yl)-phenylamino]-pyrimidin-2-ylamino}-3-methyl-1,3,4,5-tetrahydro-benzo[d]azepin-2-one;
2-[5-Chloro-2-(1,1-dimethyl-3-oxo-2,3,4,5-tetrahydro-1H-benzo[c]azepin-7-ylamino)-pyrimidin-4-ylamino]-3-fluoro-N-methyl-benzamide;
2-[5-Chloro-2-(1,1-dimethyl-3-oxo-2,3,4,5-tetrahydro-1H-benzo[c]azepin-7-ylamino)-pyrimidin-4-ylamino]-N-methyl-benzamide;
3-Chloro-2-[5-chloro-2-(1,1-dimethyl-3-oxo-2,3,4,5-tetrahydro-1H-benzo[c]azepin-7-ylamino)-pyrimidin-4-ylamino]-N-methyl-benzamide;
3-[5-Chloro-2-(1,1-dimethyl-3-oxo-2,3,4,5-tetrahydro-1H-benzo[c]azepin-7-ylamino)-pyrimidin-4-ylamino]-4-methyl-thiophene-2-carboxylic acid methyl amide;
2-[5-Chloro-2-(1,1-dimethyl-3-oxo-2,3,4,5-tetrahydro-1H-benzo[c]azepin-7-ylamino)-pyrimidin-4-ylamino]-3,N-dimethyl-benzamide;
2-[5-Chloro-2-(1,1-dimethyl-3-oxo-2,3,4,5-tetrahydro-1H-benzo[c]azepin-8-ylamino)-pyrimidin-4-ylamino]-3-fluoro-N-methyl-benzamide;
(1R,2R,3S,4S)-3-[5-Chloro-2-(1,1-dimethyl-3-oxo-2,3,4,5-tetrahydro-1H-benzo[c]azepin-8-ylamino)-pyrimidin-4-ylamino]-bicyclo[2.2.1]hept-5-ene-2-carboxylic acid amide;

2-[5-Chloro-2-(1,1-dimethyl-3-oxo-2,3,4,5-tetrahydro-1H-benzo[c]azepin-8-ylamino)-pyrimidin-4-ylamino]-N-methyl-benzamide;
3-Chloro-2-[5-chloro-2-(1,1-dimethyl-3-oxo-2,3,4,5-tetrahydro-1H-benzo[c]azepin-8-ylamino)-pyrimidin-4-ylamino]-N-methyl-benzamide;
3-[5-Chloro-2-(1,1-dimethyl-3-oxo-2,3,4,5-tetrahydro-1H-benzo[c]azepin-8-ylamino)-pyrimidin-4-ylamino]-4-methyl-thiophene-2-carboxylic acid methylamide;
2-[5-Chloro-2-(5,6-dihydro-4H-3,10b-diaza-benzo[e]azulen-9-ylamino)-pyrimidin-4-ylamino]-N-methyl-benzamide;
2-[5-Chloro-2-(5,6-dihydro-4H-3,10b-diaza-benzo[e]azulen-9-ylamino)-pyrimidin-4-ylamino]-3-fluoro-N-methyl-benzamide;
3-[5-Chloro-2-(5,6-dihydro-4H-3,10b-diaza-benzo[e]azulen-9-ylamino)-pyrimidin-4-ylamino]-4-methyl-thiophene-2-carboxylic acid methylamide;
3-Chloro-2-[5-chloro-2-(5,6-dihydro-4H-3,10b-diaza-benzo[e]azulen-9-ylamino)-pyrimidin-4-ylamino]-N-methyl-benzamide;
3-[5-Chloro-2-(5,6-dihydro-4H-3,10b-diaza-benzo[e]azulen-9-ylamino)-pyrimidin-4-ylamino]-thiophene-2-carboxylic acid methylamide;
2-[5-Chloro-2-(5,6-dihydro-4H-3,10b-diaza-benzo[e]azulen-9-ylamino)-pyrimidin-4-ylamino]-5-fluoro-N-methyl-benzamide;
5-Chloro-N*2*-(5,6-dihydro-4H-3,10b-diaza-benzo[e]azulen-9-yl)-N*4*-[2-fluoro-6-(propane-2-sulfonyl)-phenyl]-pyrimidine-2,4-diamine;
2-[5-Chloro-2-(1-methyl-5,6-dihydro-4H-3,10b-diaza-benzo[e]azulen-9-ylamino)-pyrimidin-4-ylamino]-3-fluoro-N-methyl-benzamide;
2-[5-Chloro-2-(5,6-dihydro-4H-1,3a-diaza-benzo[e]azulen-9-ylamino)-pyrimidin-4-ylamino]-3-fluoro-N-methyl-benzamide;
3-Chloro-2-[5-chloro-2-(5,6-dihydro-4H-1,3a-diaza-benzo[e]azulen-9-ylamino)-pyrimidin-4-ylamino]-N-methyl-benzamide;
4-[5-Chloro-2-(5,6-dihydro-4H-1,3a-diaza-benzo[e]azulen-9-ylamino)-pyrimidin-4-ylamino]-5-methyl-thiophene-3-carboxylic acid methylamide;
2-[5-Chloro-2-(5,6-dihydro-4H-1,3a-diaza-benzo[e]azulen-9-ylamino)-pyrimidin-4-ylamino]-5-fluoro-N-methyl-benzamide;
2-[2-(4-Acetyl-2-oxo-2,3,4,5-tetrahydro-1H-benzo[e][1,4]diazepin-8-ylamino)-5-chloro-pyrimidin-4-ylamino]-3-fluoro-N-methyl-benzamide;
3-[2-(4-Acetyl-2-oxo-2,3,4,5-tetrahydro-1H-benzo[e][1,4]diazepin-8-ylamino)-5-chloro-pyrimidin-4-ylamino]-thiophene-2-carboxylic acid methylamide;
3-[2-(4-Acetyl-2-oxo-2,3,4,5-tetrahydro-1H-benzo[e][1,4]diazepin-8-ylamino)-5-chloro-pyrimidin-4-ylamino]-4-methyl-thiophene-2-carboxylic acid methylamide;
2-[2-(4-Acetyl-1-ethyl-2-oxo-2,3,4,5-tetrahydro-1H-benzo[e][1,4]diazepin-8-ylamino)-5-chloro-pyrimidin-4-ylamino]-3-fluoro-N-methyl-benzamide;
3-[2-(4-Acetyl-1-ethyl-2-oxo-2,3,4,5-tetrahydro-1H-benzo[e][1,4]diazepin-8-ylamino)-5-chloro-pyrimidin-4-ylamino]-4-methyl-thiophene-2-carboxylic acid methylamide;
3-[2-(4-Acetyl-1-ethyl-2-oxo-2,3,4,5-tetrahydro-1H-benzo[e][1,4]diazepin-8-ylamino)-5-chloro-pyrimidin-4-ylamino]-thiophene-2-carboxylic acid methylamide;
2-[2-(4-Acetyl-1-ethyl-2-oxo-2,3,4,5-tetrahydro-1H-benzo[e][1,4]diazepin-8-ylamino)-5-chloro-pyrimidin-4-ylamino]-3-chloro-N-methyl-benzamide;

2-[2-(4-Acetyl-1-ethyl-2-oxo-2,3,4,5-tetrahydro-1H-benzo[e][1,4]diazepin-8-ylamino)-5-chloro-pyrimidin-4-ylamino]-N-methyl-benzamide;

3-[5-Chloro-2-(1,4-diethyl-2-oxo-2,3,4,5-tetrahydro-1H-benzo[e][1,4]diazepin-8-ylamino)-pyrimidin-4-ylamino]-thiophene-2-carboxylic acid methylamide;

8-[5-Chloro-4-(2-fluoro-6-methylcarbamoyl-phenylamino)-pyrimidin-2-ylamino]-2-oxo-1,2,3,5-tetrahydro-benzo[e][1,4]diazepine-4-carboxylic acid benzyl ester;

2-[5-Chloro-2-(2-oxo-2,3,4,5-tetrahydro-1H-benzo[e][1,4]diazepin-8-ylamino)-pyrimidin-4-ylamino]-N-methyl-benzamide;

2-[2-(4-Benzyl-2-oxo-2,3,4,5-tetrahydro-1H-benzo[e][1,4]diazepin-8-ylamino)-5-chloro-pyrimidin-4-ylamino]-N-methyl-benzamide;

2-[5-Chloro-2-(4-methanesulfonyl-2-oxo-2,3,4,5-tetrahydro-1H-benzo[e][1,4]diazepin-8-ylamino)-pyrimidin-4-ylamino]-3-fluoro-N-methyl-benzamide;

2-{5-Chloro-2-[2-oxo-4-(3,3,3-trifluoro-propyl)-2,3,4,5-tetrahydro-1H-benzo[e][1,4]diazepin-8-ylamino]-pyrimidin-4-ylamino}-3-fluoro-N-methyl-benzamide;

2-{5-Chloro-2-[4-(2-methoxy-ethyl)-2-oxo-2,3,4,5-tetrahydro-1H-benzo[e][1,4]diazepin-8-ylamino]-pyrimidin-4-ylamino}-3-fluoro-N-methyl-benzamide;

2-[5-Chloro-2-(4-ethyl-2-oxo-2,3,4,5-tetrahydro-1H-benzo[e][1,4]diazepin-8-ylamino)-pyrimidin-4-ylamino]-3-fluoro-N-methyl-benzamide;

2-{5-Chloro-2-[4-(2-methoxy-ethyl)-2-oxo-2,3,4,5-tetrahydro-1H-benzo[e][1,4]diazepin-8-ylamino]-pyrimidin-4-ylamino}-N-methyl-benzamide;

3-[5-Chloro-2-(4-ethyl-2-oxo-2,3,4,5-tetrahydro-1H-benzo[e][1,4]diazepin-8-ylamino)-pyrimidin-4-ylamino]-4-methyl-thiophene-2-carboxylic acid methylamide;

3-{5-Chloro-2-[2-oxo-4-(2,2,2-trifluoro-acetyl)-2,3,4,5-tetrahydro-1H-benzo[e][1,4]diazepin-8-ylamino]-pyrimidin-4-ylamino}-4-methyl-thiophene-2-carboxylic acid methylamide;

2-[5-Chloro-2-(4-methyl-2-oxo-2,3,4,5-tetrahydro-1H-benzo[e][1,4]diazepin-8-ylamino)-pyrimidin-4-ylamino]-N-methyl-benzamide;

3-[5-Chloro-2-(4-methyl-2-oxo-2,3,4,5-tetrahydro-1H-benzo[e][1,4]diazepin-8-ylamino)-pyrimidin-4-ylamino]-4-methyl-thiophene-2-carboxylic acid methyl amide;

8-[5-Chloro-4-(2-fluoro-6-methylcarbamoyl-phenylamino)-pyrimidin-2-ylamino]-2-oxo-1,2,3,5-tetrahydro-benzo[e][1,4]diazepine-4-carboxylic acid ethyl ester;

2-[5-Chloro-2-(1,4-diethyl-2-oxo-2,3,4,5-tetrahydro-1H-benzo[e][1,4]diazepin-8-ylamino)-pyrimidin-4-ylamino]-3-fluoro-N-methyl-benzamide;

3-{5-Chloro-2-[1-ethyl-2-oxo-4-(3,3,3-trifluoro-propyl)-2,3,4,5-tetrahydro-1H-benzo[e][1,4]diazepin-8-ylamino]-pyrimidin-4-ylamino}-thiophene-2-carboxylic acid methylamide;

3-[5-Chloro-2-(1-ethyl-4-methanesulfonyl-2-oxo-2,3,4,5-tetrahydro-1H-benzo[e][1,4]diazepin-8-ylamino)-pyrimidin-4-ylamino]-thiophene-2-carboxylic acid methylamide;

2-{5-Chloro-2-[1-ethyl-4-(2-hydroxy-ethyl)-2-oxo-2,3,4,5-tetrahydro-1H-benzo[e][1,4]diazepin-8-ylamino]-pyrimidin-4-ylamino}-3-fluoro-N-methyl-benzamide;

3-[5-Chloro-2-(1,4-diethyl-2-oxo-2,3,4,5-tetrahydro-1H-benzo[e][1,4]diazepin-8-ylamino)-pyrimidin-4-ylamino]-4-methyl-thiophene-2-carboxylic acid methyl amide;

8-[5-Chloro-4-(2-fluoro-6-methylcarbamoyl-phenylamino)-pyrimidin-2-ylamino]-1-ethyl-2-oxo-1,2,3,5-tetrahydro-benzo[e][1,4]diazepine-4-carboxylic acid ethyl ester;

8-[5-Chloro-4-(2-fluoro-6-prop-2-ynylcarbamoyl-phenylamino)-pyrimidin-2-ylamino]-1-ethyl-2-oxo-1,2,3,5-tetrahydro-benzo[e][1,4]diazepine-4-carboxylic acid ethyl ester;

2-[2-(1-Acetyl-3-oxo-2,3,4,5-tetrahydro-1H-benzo[e][1,4]diazepin-8-ylamino)-5-chloro-pyrimidin-4-ylamino]-3-fluoro-N-methyl-benzamide;

3-[2-(1-Acetyl-3-oxo-2,3,4,5-tetrahydro-1H-benzo[e][1,4]diazepin-8-ylamino)-5-chloro-pyrimidin-4-ylamino]-thiophene-2-carboxylic acid methylamide;

2-[2-(1-Acetyl-4-ethyl-2,3,4,5-tetrahydro-1H-benzo[e][1,4]diazepin-8-ylamino)-5-chloro-pyrimidin-4-ylamino]-3-fluoro-N-methyl-benzamide;

2-[5-Chloro-2-(5-oxo-2,3,4,5-tetrahydro-benzo[f][1,4]oxazepin-7-ylamino)-pyrimidin-4-ylamino]-N-methyl-benzamide;

2-[5-Chloro-2-(5-ethyl-6-oxo-5,6,8,9-tetrahydro-7-oxa-5-aza-benzocyclohepten-3-ylamino)-pyrimidin-4-ylamino]-N-methyl-benzamide;

2-[5-Chloro-2-(5-ethyl-6-oxo-5,6,8,9-tetrahydro-7-oxa-5-aza-benzocyclohepten-3-ylamino)-pyrimidin-4-ylamino]-3-fluoro-N-methyl-benzamide; or 3-[5-Chloro-2-(5-ethyl-6-oxo-5,6,8,9-tetrahydro-7-oxa-5-aza-benzocyclohepten-3-ylamino)-pyrimidin-4-ylamino]-thiophene-2-carboxylic acid methylamide;

or a pharmaceutically acceptable salt form thereof.

In one embodiment, the present invention provides one or more of the following compounds of formula II:

2-[5-Chloro-2-(6-methoxy-2-oxo-2,3,4,5-tetrahydro-1H-benzo[b]azepin-9-ylamino)-pyrimidin-4-ylamino]-N-methyl-benzamide;

2-[5-Chloro-2-(3-ethyl-7-methoxy-2,3,4,5-tetrahydro-1H-benzo[d]azepin-6-ylamino)-pyrimidin-4-ylamino]-N-methyl-benzenesulfonamide;

6-[5-Chloro-4-(2-methylcarbamoyl-phenylamino)-pyrimidin-2-ylamino]-12-aza-tricyclo[7.2.1.0*2,7*]dodeca-2(7),3,5-triene-4,12-dicarboxylic acid 12-ethyl ester 4-methyl ester;

2-[5-Chloro-2-(8-methoxy-2-methyl-1-oxo-2,3,4,5-tetrahydro-1H-benzo[c]azepin-9-ylamino)-pyrimidin-4-ylamino]-N-methyl-benzamide;

2-[5-Chloro-2-(6-methoxy-1-methyl-2-oxo-2,3,4,5-tetrahydro-1H-benzo[b]azepin-9-ylamino)-pyrimidin-4-ylamino]-N-methyl-benzamide;

9-[5-Chloro-4-(2-methoxy-4-morpholin-4-yl-phenylamino)-pyrimidin-2-ylamino]-6-methoxy-1-methyl-1,3,4,5-tetrahydro-benzo[b]azepin-2-one;

9-[5-Chloro-4-(2-methoxy-4-morpholin-4-yl-phenylamino)-pyrimidin-2-ylamino]-1-ethyl-6-methoxy-1,3,4,5-tetrahydro-benzo[b]azepin-2-one;

2-[5-Chloro-2-(3-ethyl-9-methoxy-2,3,4,5-tetrahydro-1H-benzo[d]azepin-6-ylamino)-pyrimidin-4-ylamino]-N-methyl-benzamide;

N-{(1R,2R)-2-[5-Chloro-2-(3-ethyl-9-methoxy-2,3,4,5-tetrahydro-1H-benzo[d]azepin-6-ylamino)-pyrimidin-4-ylamino]-cyclohexyl}-methanesulfonamide;

2-[5-Chloro-2-(5-oxo-2,3,4,5-tetrahydro-1H-benzo[e][1,4]diazepin-6-ylamino)pyrimidin-4-ylamino]-N-methyl-benzenesulfonamide;

2-[5-Chloro-2-(1,4-dimethyl-5-oxo-2,3,4,5-tetrahydro-1H-benzo[e][1,4]diazepin-6-ylamino)-pyrimidin-4-ylamino]-N-methyl-benzamide;

N-{(1R,2R)-2-[5-Chloro-2-(1,4-dimethyl-5-oxo-2,3,4,5-tetrahydro-1H-benzo[e][1,4]diazepin-6-ylamino)-pyrimidin-4-ylamino]-cyclohexyl}-methanesulfonamide;

N-{2-[5-Chloro-2-(1,4-dimethyl-5-oxo-2,3,4,5-tetrahydro-1H-benzo[e][1,4]diazepin-6-ylamino)-pyrimidin-4-ylamino]-phenyl}-methanesulfonamide;

2-{5-Chloro-2-[3-methyl-5-oxo-1-(2,2,2-trifluoro-acetyl)-2,3,4,5-tetrahydro-1H-benzo[e][1,4]diazepin-6-ylamino]-pyrimidin-4-ylamino}-N-methyl-benzamide;

N-(2-{5-Chloro-2-[3-methyl-5-oxo-1-(2,2,2-trifluoro-acetyl)-2,3,4,5-tetrahydro-1H-benzo[e][1,4]diazepin-6-ylamino]-pyrimidin-4-ylamino}-phenyl)-methanesulfonamide;

N-(2-{5-Chloro-2-[2-methyl-5-oxo-1-(2,2,2-trifluoro-acetyl)-2,3,4,5-tetrahydro-1H-benzo[e][1,4]diazepin-6-ylamino]-pyrimidin-4-ylamino}-phenyl)-methanesulfonamide;

N-((1R,2R)-2-{5-Chloro-2-[2-methyl-5-oxo-1-(2,2,2-trifluoro-acetyl)-2,3,4,5-tetrahydro-1H-benzo[e][1,4]diazepin-6-ylamino]-pyrimidin-4-ylamino}-cyclohexyl)-methanesulfonamide;

2-[2-(4-Acetyl-2,3,4,5-tetrahydro-1H-benzo[e][1,4]diazepin-6-ylamino)-5-chloro-pyrimidin-4-ylamino]-N-methyl-benzamide;

N-((1R,2R)-2-{5-Chloro-2-[7-methoxy-3-(2-methoxy-ethyl)-2,3,4,5-tetrahydro-1H-benzo[d]azepin-6-ylamino]-pyrimidin-4-ylamino}-cyclohexyl)-methanesulfonamide;

(2-exo, 3-exo)-3-{5-Chloro-2-[7-methoxy-3-(2-methoxy-ethyl)-2,3,4,5-tetrahydro-1H-benzo[d]azepin-6-ylamino]-pyrimidin-4-ylamino}-bicyclo[2.2.1]hept-5-ene-2-carboxylic acid amide;

5-Chloro-N(2)-[7-methoxy-3-(2-methoxy-ethyl)-2,3,4,5-tetrahydro-1H-benzo[d]azepin-6-yl]-N(4)-(2-methoxy-4-morpholin-4-yl-phenyl)-pyrimidine-2,4-diamine;

2-[5-Chloro-2-(1,4-dimethyl-5-oxo-2,3,4,5-tetrahydro-1H-benzo[e][1,4]diazepin-9-ylamino)-pyrimidin-4-ylamino]-N-methyl-benzamide;

N-{(1R,2R)-2-[5-Chloro-2-(1,4-dimethyl-5-oxo-2,3,4,5-tetrahydro-1H-benzo[e][1,4]diazepin-9-ylamino)-pyrimidin-4-ylamino]-cyclohexyl}methanesulfonamide;

2-[5-Chloro-2-(1,4-dimethyl-5-oxo-2,3,4,5-tetrahydro-1H-benzo[e][1,4]diazepin-9-ylamino)-pyrimidin-4-ylamino]-N-methyl-benzenesulfonamide;

2-[5-Chloro-2-(1-methyl-5-oxo-2,3,4,5-tetrahydro-1H-benzo[e][1,4]diazepin-9-ylamino)pyrimidin-4-ylamino]-N-methyl-benzamide;

2-[2-(1-Allyl-5-oxo-2,3,4,5-tetrahydro-1H-benzo[e][1,4]diazepin-9-ylamino)-5-chloro-pyrimidin-4-ylamino]-N-methyl-benzamide;

(2-exo-3-exo)-3-[5-Chloro-2-(2,3,4,5-tetrahydro-benzo[b]oxepin-9-ylamino)-pyrimidin-4-ylamino]-bicyclo[2.2.1]hept-5-ene-2-carboxylic acid amide;

5-Chloro-N*4*-(2-methoxy-4-morpholin-4-yl-phenyl)-N*2*-(2,3,4,5-tetrahydrobenzo[b]oxepin-9-yl)pyrimidine-2,4-diamine;

N-{(1R,2R)-2-[5-Chloro-2-(2,3,4,5-tetrahydro-benzo[b]oxepin-9-ylamino)pyrimidin-4-ylamino]-cyclohexyl}-methanesulfonamide;

5-Chloro-N*4*-(2-methoxy-phenyl)-N*2*-(2,3,4,5-tetrahydrobenzo[b]oxepin-9-yl)-pyrimidine-2,4-diamine;

(1R,2R,3S,4S)-3-[5-Chloro-2-(5,5-dimethyl-2,3,4,5-tetrahydro-benzo[b]oxepin-9-ylamino)-pyrimidin-4-ylamino]-bicyclo[2.2.1]hept-5-ene-2-carboxylic acid amide;

5-Chloro-N*2*-(5,5-dimethyl-2,3,4,5-tetrahydro-benzo[b]oxepin-9-yl)-N*4*-[2-methoxy-4-(4-methyl-piperazin-1-yl)-phenyl]-pyrimidine-2,4-diamine;

2-[5-Chloro-2-(5,5-dimethyl-2,3,4,5-tetrahydro-benzo[b]oxepin-9-ylamino)-pyrimidin-4-ylamino]-N-ethyl-benzamide;

2-[5-Chloro-2-(5,5-dimethyl-2,3,4,5-tetrahydro-benzo[b]oxepin-9-ylamino)-pyrimidin-4-ylamino]-N-ethyl-3-fluoro-benzamide;

N-{(1R,2R)-2-[5-Chloro-2-(5,5-dimethyl-2,3,4,5-tetrahydro-benzo[b]oxepin-9-ylamino)-pyrimidin-4-ylamino]-cyclohexyl}-methanesulfonamide;

5-Chloro-N*2*-(5,5-dimethyl-2,3,4,5-tetrahydro-benzo[b]oxepin-9-yl)-N*4*-(2-methoxy-4-morpholin-4-yl-phenyl)-pyrimidine-2,4-diamine;

2-[5-Chloro-2-(5,5-dimethyl-2,3,4,5-tetrahydro-benzo[b]oxepin-9-ylamino)-pyrimidin-4-ylamino]-N-(2-cyano-ethyl)-benzamide;

5-Chloro-N*2*-(5,5-dimethyl-2,3,4,5-tetrahydro-benzo[b]oxepin-9-yl)-N*4*-[2-(propane-2-sulfonyl)-phenyl]-pyrimidine-2,4-diamine;

5-Chloro-N*2*-(5,5-dimethyl-2,3,4,5-tetrahydro-benzo[b]oxepin-9-yl)-N*4*-[2-(1-methyl-1H-imidazol-2-yl)-phenyl]-pyrimidine-2,4-diamine;

{2-[5-Chloro-2-(5,5-dimethyl-2,3,4,5-tetrahydro-benzo[b]oxepin-9-ylamino)-pyrimidin-4-ylamino]-phenoxy}-acetonitrile;

5-Chloro-N*2*-(5,5-dimethyl-2,3,4,5-tetrahydro-benzo[b]oxepin-9-yl)-N*4*-(2-pyrazol-1-yl-phenyl)-pyrimidine-2,4-diamine;

2-[5-Chloro-2-(4-methoxy-8-morpholin-4-yl-6,7,8,9-tetrahydro-5H-benzocyclohepten-1-ylamino)-pyrimidin-4-ylamino]-bicyclo[2.2.1]hept-5-ene-2-carboxylic acid amide;

2-[5-Chloro-2-(4-methoxy-8-morpholin-4-yl-6,7,8,9-tetrahydro-5H-benzocyclohepten-1-ylamino)-pyrimidin-4-ylamino]-N,N-dimethyl-benzenesulfonamide;

5-Chloro-N(2)-(4-methoxy-8-morpholin-4-yl-6,7,8,9-tetrahydro-5H-benzocyclohepten-1-yl)-N(4)-[2-(propane-2-sulfonyl)-phenyl]-pyrimidine-2,4-diamine;

9-{5-Chloro-4-[2-(1-methyl-1H-imidazol-2-yl)-phenylamino]-pyrimidin-2-ylamino}-8-methoxy-5,5-dimethyl-1,3,4,5-tetrahydro-benzo[b]azepin-2-one;

N-{(1R,2R)-2-[5-Chloro-2-(2-methoxy-7-morpholin-4-yl-6,7,8,9-tetrahydro-5H-benzocyclohepten-1-ylamino)-pyrimidin-4-ylamino]-cyclohexyl}-methanesulfonamide;

5-Chloro-N*2*-(2-methoxy-7-morpholin-4-yl-6,7,8,9-tetrahydro-5H-benzocyclohepten-1-yl)-N*4*-(2-pyrazol-1-yl-phenyl)-pyrimidine-2,4-diamine;

2-[5-Chloro-2-(2-methoxy-7-morpholin-4-yl-6,7,8,9-tetrahydro-5H-benzocyclohepten-1-ylamino)-pyrimidin-4-ylamino]-N,N-dimethyl-benzenesulfonamide;

2-[5-Chloro-2-(2-methoxy-7-morpholin-4-yl-6,7,8,9-tetrahydro-5H-benzocyclohepten-1-ylamino)-pyrimidin-4-ylamino]-N-methyl-benzamide;

N-((1R,2R)-2-{5-Chloro-2-[7-(2,2-difluoro-ethylamino)-2-methoxy-6,7,8,9-tetrahydro-5H-benzocyclohepten-1-ylamino]-pyrimidin-4-ylamino}-cyclohexyl)-methanesulfonamide;

N-((1R,2R)-2-{5-Chloro-2-[7-(2,2-difluoro-ethylamino)-2-methoxy-6,7,8,9-tetrahydro-5H-benzocyclohepten-1-ylamino]-pyrimidin-4-ylamino}-cyclohexyl)-methanesulfonamide;

5-Chloro-N*2*-[7-(2,2-difluoro-ethylamino)-2-methoxy-6,7,8,9-tetrahydro-5H-benzocyclohepten-1-yl]-N*4*-(2-pyrazol-1-yl-phenyl)-pyrimidine-2,4-diamine;

2-{5-Chloro-2-[7-(2,2-difluoro-ethylamino)-2-methoxy-6,7,8,9-tetrahydro-5H-benzocyclohepten-1-ylamino]-pyrimidin-4-ylamino}-N,N-dimethyl-benzenesulfonamide;

2-{5-Chloro-2-[7-(2,2-difluoro-ethylamino)-2-methoxy-6,7,8,9-tetrahydro-5H-benzocyclohepten-1-ylamino]-pyrimidin-4-ylamino}-N-methyl-benzamide;

9-[5-Chloro-4-(2-methoxy-4-morpholin-4-yl-phenylamino)-pyrimidin-2-ylamino]-3-ethyl-8-methoxy-1,3,4,5-tetrahydro-benzo[d]azepin-2-one;

2-[5-Chloro-2-(3-ethyl-7-methoxy-4-oxo-2,3,4,5-tetrahydro-1H-benzo[d]azepin-6-ylamino)-pyrimidin-4-ylamino]-N-ethyl-benzamide;

2-[5-Chloro-2-(2-methoxy-5-methyl-6-oxo-5,6,8,9-tetrahydro-7-oxa-5-aza-benzocyclohepten-1-ylamino)-pyrimidin-4-ylamino]-N-methyl-benzamide;

N-{(1R,2R)-2-[2-(4-Benzyl-7-methoxy-2-oxo-2,3,4,5-tetrahydro-1H-benzo[e][1,4]diazepin-6-ylamino)-5-chloro-pyrimidin-4-ylamino]-cyclohexyl}-methanesulfonamide;

N-{(1R,2R)-2-[5-Chloro-2-(7-fluoro-5-oxo-2,3,4,5-tetrahydro-benzo[f][1,4]oxazepin-9-ylamino)-pyrimidin-4-ylamino]-cyclohexyl}-methanesulfonamide; or 9-[5-Chloro-4-(2-methoxy-4-morpholin-4-yl-phenylamino)-pyrimidin-2-ylamino]-7-fluoro-3,4-dihydro-2H-benzo[f][1,4]oxazepin-5-one;

or a pharmaceutically acceptable salt form thereof.

In another embodiment, the present invention provides any of the compounds as described in the Examples.

In another embodiment, the present invention provides one or more of the following compounds:

(1S,2S,3R,4R)-3-[5-Chloro-2-(1-ethyl-6-methoxy-2-oxo-2,3,4,5-tetrahydro-1H-benzo[b]azepin-7-ylamino)-pyrimidin-4-ylamino]-bicyclo[2.2.1]hept-5-ene-2-carboxylic acid amide;

2-{7-[5-Chloro-4-(2-methoxy-4-morpholin-4-yl-phenylamino)-pyrimidin-2-ylamino]-8-methoxy-1,2,4,5-tetrahydro-benzo[d]azepin-3-yl}-N,N-dimethyl-acetamide;

N-{(1R,2R)-2-[5-Chloro-2-(1,4-diethyl-2,3,4,5-tetrahydro-1H-benzo[e][1,4]diazepin-8-ylamino)-pyrimidin-4-ylamino]-cyclohexyl}-methanesulfonamide;

(1S,2S,3R,4R)-3-[5-Chloro-2-((R)-1-methoxy-7-morpholin-4-yl-6,7,8,9-tetrahydro-5H-benzocyclohepten-2-ylamino)-pyrimidin-4-ylamino]-bicyclo[2.2.1]hept-5-ene-2-carboxylic acid amide;

(1S,2S,3R,4R)-3-[5-Chloro-2-((S)-1-methoxy-7-morpholin-4-yl-6,7,8,9-tetrahydro-5H-benzocyclohepten-2-ylamino)-pyrimidin-4-ylamino]-bicyclo[2.2.1]hept-5-ene-2-carboxylic acid amide;

2-{5-Chloro-2-[1-methoxy-7-(4-methyl-piperazin-1-yl)-6,7,8,9-tetrahydro-5H-benzocyclohepten-2-ylamino]-pyrimidin-4-ylamino}-N,N-dimethyl-benzenesulfonamide;

(1S,2S,3R,4R)-3-{5-Chloro-2-[6-(2-hydroxy-ethylamino)-1-methoxy-6,7,8,9-tetrahydro-5H-benzocyclohepten-2-ylamino]-pyrimidin-4-ylamino}-bicyclo[2.2.1]hept-5-ene-2-carboxylic acid amide;

(1S,2S,3R,4R)-3-[5-Chloro-2-(3-methoxy-7-morpholin-4-yl-6,7,8,9-tetrahydro-5H-benzocyclohepten-2-ylamino)-pyrimidin-4-ylamino]-bicyclo[2.2.1]hept-5-ene-2-carboxylic acid amide (Single Diastereomer A);

(1S,2S,3R,4R)-3-[5-Chloro-2-(3-methoxy-7-morpholin-4-yl-6,7,8,9-tetrahydro-5H-benzocyclohepten-2-ylamino)-pyrimidin-4-ylamino]-bicyclo[2.2.1]hept-5-ene-2-carboxylic acid amide (Single Diastereomer B);

2-{5-Chloro-2-[3-methoxy-7-(2-methoxy-ethylamino)-6,7,8,9-tetrahydro-5H-benzocyclohepten-2-ylamino]-pyrimidin-4-ylamino}-N-methyl-benzamide;

2-{5-Chloro-2-[5,5-dimethyl-2-oxo-3-(2,2,2-trifluoro-acetylamino)-2,3,4,5-tetrahydro-1H-1-benzazepin-8-ylamino]-pyrimidin-4-ylamino}-3-fluoro-N-methyl-benzamide;

2-{5-Chloro-2-[3-(2-methoxy-acetylamino)-5,5-dimethyl-2-oxo-2,3,4,5-tetrahydro-1H-1-benzazepin-8-ylamino]-pyrimidin-4-ylamino}-3-fluoro-N-methyl-benzamide;

Pyrrolidine-1-carboxylic acid {8-[5-chloro-4-(2-fluoro-6-methylcarbamoyl-phenylamino)-pyrimidin-2-ylamino]-5,5-dimethyl-2-oxo-2,3,4,5-tetrahydro-1H-1-benzazepin-3-yl}-amide;

3-[5-Chloro-4-(2-fluoro-6-methylcarbamoyl-phenylamino)-pyrimidin-2-ylamino]-7,8-dihydro-6H-5-oxa-9-aza-benzocycloheptene-9-carboxylic acid ethyl ester;

2-{5-Chloro-2-[3-(2-hydroxy-ethyl)-8-methoxy-2,3,4,5-tetrahydro-1H-3-benzazepin-7-ylamino]-pyrimidin-4-ylamino}-N,N-dimethyl-benzenesulfonamide;

(S)-1-(2-{5-Chloro-2-[3-((S)-2-hydroxy-propyl)-8-methoxy-2,3,4,5-tetrahydro-1H-3-benzazepin-7-ylamino]-pyrimidin-4-ylamino}-benzenesulfonyl)-pyrrolidin-3-ol;

(1S,2S,3R,4R)-3-{5-Chloro-2-[3-((S)-2-hydroxy-propyl)-8-methoxy-2,3,4,5-tetrahydro-1H-3-benzazepin-7-ylamino]-pyrimidin-4-ylamino}-bicyclo[2.2.1]hept-5-ene-2-carboxylic acid amide;

(1S,2S,3R,4R)-3-{5-Chloro-2-[3-((R)-2-hydroxy-propyl)-8-methoxy-2,3,4,5-tetrahydro-1H-3-benzazepin-7-ylamino]-pyrimidin-4-ylamino}-bicyclo[2.2.1]hept-5-ene-2-carboxylic acid amide;

(1S,2S,3R,4R)-3-{5-Chloro-2-[3-(2-hydroxy-2-methyl-propyl)-8-methoxy-2,3,4,5-tetrahydro-1H-3-benzazepin-7-ylamino]-pyrimidin-4-ylamino}-bicyclo[2.2.1]hept-5-ene-2-carboxylic acid amide; or 2-[5-Chloro-2-(9-ethyl-7-morpholin-4-yl-6,7,8,9-tetrahydro-5-oxa-9-aza-benzocyclohepten-2-ylamino)-pyrimidin-4-ylamino]-3-fluoro-N-methyl-benzamide;

or a pharmaceutically acceptable salt thereof.

The present invention provides pharmaceutically acceptable salts of compounds of formula I or II. Pharmaceutically acceptable acid addition salts of the compounds of formula I or II include, but are not limited to, salts derived from inorganic acids such as hydrochloric, nitric, phosphoric, sulfuric, hydrobromic, hydriodic, and phosphorus, as well as the salts derived from organic acids, such as aliphatic mono- and dicarboxylic acids, phenyl-substituted alkanoic acids, hydroxy alkanoic acids, alkanedioic acids, aromatic acids, and aliphatic and aromatic sulfonic acids. Such salts thus include, but are not limited to, sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, and methanesulfonate. Also contemplated are the salts of amino acids such as arginate, gluconate, galacturonate, and the like; see, for example, Berge et al., "Pharmaceutical Salts," J. of Pharmaceutical Science, 1977; 66:1-19.

The acid addition salts of the basic compounds may be prepared by contacting the free base form with a sufficient amount of the desired acid to produce the salt in the conventional manner. The free base form may be regenerated by contacting the salt form with a base and isolating the free base in the conventional manner. The free base forms differ from their respective salt forms somewhat in certain physical properties such as solubility in polar solvents, but otherwise the salts are in general equivalent to their respective free base for purposes of the present invention.

Pharmaceutically acceptable base addition salts of compounds of formula I are formed with metals or amines, such as alkali and alkaline earth metal hydroxides, or of organic amines. Examples of metals used as cations include, but are not limited to, sodium, potassium, magnesium, and calcium. Examples of suitable amines include, but are not limited to, N,N'-dibenzylethylenediamine, chloroprocaine, choline, diethanolamine, ethylenediamine (ethane-1,2-diamine), N-methylglucamine, and procaine; see, for example, Berge et al., supra., 1977.

The base addition salts of acidic compounds may be prepared by contacting the free acid form with a sufficient amount of the desired base to produce the salt in the conventional manner. The free acid form may be regenerated by contacting the salt form with an acid and isolating the free acid in a conventional manner. The free acid forms differ from their respective salt forms somewhat in certain physical properties such as solubility in polar solvents, but otherwise the salts are in general equivalent to their respective free acid for purposes of the present invention.

Some of the compounds in the present invention may exist as stereoisomers, including enantiomers, diastereomers, and geometric isomers. Geometric isomers include compounds of the present invention that have alkenyl groups, which may exist as entgegen or zusammen conformations, in which case all geometric forms thereof, both entgegen and zusammen, cis and trans, and mixtures thereof, are within the scope of the present invention. Some compounds of the present invention have cycloalkyl groups, which may be substituted at more than one carbon atom, in which case all geometric forms thereof, both cis and trans, and mixtures thereof, are within the scope of the present invention. All of these forms, including (R), (S), epimers, diastereomers, cis, trans, syn, anti, (E), (Z), tautomers, and mixtures thereof, are contemplated in the compounds of the present invention.

The compounds to be used in the present invention can exist in unsolvated forms as well as solvated forms, including hydrated forms. In general, the solvated forms, including hydrated forms, are equivalent to unsolvated forms and are intended to be encompassed within the scope of the present invention.

III. Pharmaceutical Compositions

The present invention further provides pharmaceutical compositions comprising a compound of the present invention (e.g., a compound of formula I or II or a pharmaceutically acceptable salt thereof), together with a pharmaceutically acceptable carrier, diluent, or excipient therefor. The pharmaceutical composition may contain two or more compounds of the present invention (i.e., two or more compounds of the present invention may be used together in the pharmaceutical composition). Preferably, the pharmaceutical composition contains a therapeutically effective amount of at least one compound of the present invention. In another embodiment, these compositions are useful in the treatment of an ALK- or c-Met-mediated disorder or condition. The compounds of the invention can also be combined in a pharmaceutical composition that also comprises compounds that are useful for the treatment of cancer or another ALK- or c-Met-mediated disorder.

A compound of the present invention can be formulated as a pharmaceutical composition in the form of a syrup, an elixir, a suspension, a powder, a granule, a tablet, a capsule, a lozenge, a troche, an aqueous solution, a cream, an ointment, a lotion, a gel, an emulsion, etc. Preferably, a compound of the present invention will cause a decrease in symptoms or a disease indicia associated with an ALK- or c-Met-mediated disorder as measured quantitatively or qualitatively.

For preparing a pharmaceutical composition from a compound of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, binders, preservatives, tablet disintegrating agents, or an encapsulating material.

In powders, the carrier is a finely divided solid which is in a mixture with the finely divided active component (i.e., compound of the present invention). In tablets, the active component is mixed with the carrier having the necessary binding properties in suitable proportions and compacted in the shape and size desired.

The powders and tablets contain from 1% to 95% (w/w) of the active compound (i.e., compound of the present invention). In another embodiment, the active compound ranges from 5% to 70% (w/w). Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogeneous mixture is then poured into convenient sized molds, allowed to cool, and thereby to solidify.

Liquid form preparations include solutions, suspensions, and emulsions, for example, water or water/propylene glycol solutions. For parenteral injection, liquid preparations can be formulated in solution in aqueous polyethylene glycol solution.

Aqueous solutions suitable for oral use can be prepared by dissolving the active component in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 0.1 mg to 1000 mg, preferably 1.0 mg to 100 mg, or from 1% to 95% (w/w) of a unit dose, according to the particular application and the potency of the active component. The composition can, if desired, also contain other compatible therapeutic agents.

Pharmaceutically acceptable carriers are determined in part by the particular composition being administered, as well as by the particular method used to administer the composition. Accordingly, there is a wide variety of suitable formulations of pharmaceutical compositions of the present invention (see, e.g., *Remington: The Science and Practice of Pharmacy,* 20th ed., Gennaro et al. Eds., Lippincott Williams and Wilkins, 2000).

A compound of the present invention, alone or in combination with other suitable components, can be made into aerosol formulations (i.e., they can be "nebulized") to be administered via inhalation. Aerosol formulations can be placed into pressurized acceptable propellants, such as dichlorodifluoromethane, propane, nitrogen, and the like.

Formulations suitable for parenteral administration, such as, for example, by intravenous, intramuscular, intradermal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and nonaqueous sterile suspensions that can include suspending agents, solubilizers, thickening agents, stabilizers, and preservatives. In the practice of this invention, compositions can be administered, for example, by intravenous infusion, orally, topically, intraperitoneally, intravesically or intrathecally. The formulations of compounds can be presented in unit-dose or multi-dose sealed containers, such as ampoules and vials. Injection solutions and suspensions can be prepared from sterile powders, granules, and tablets of the kind previously described.

The dose administered to a subject, in the context of the present invention should be sufficient to effect a beneficial therapeutic response in the subject over time. The dose will be determined by the efficacy of the particular compound employed and the condition of the subject, as well as the body weight or surface area of the subject to be treated. The size of the dose also will be determined by the existence, nature, and extent of any adverse side-effects that accompany the administration of a particular compound in a particular subject. In determining the effective amount of the compound to be administered in the treatment or prophylaxis of the disorder being treated, the physician can evaluate factors such as the circulating plasma levels of the compound, compound toxicities, and/or the progression of the disease, etc. In general, the dose equivalent of a compound is from about 1 µg/kg to 10 mg/kg for a typical subject. Many different administration methods are known to those of skill in the art.

For administration, compounds of the present invention can be administered at a rate determined by factors that can include, but are not limited to, the $LD_{50}$ of the compound, the pharmacokinetic profile of the compound, contraindicated drugs, and the side-effects of the compound at various concentrations, as applied to the mass and overall health of the subject. Administration can be accomplished via single or divided doses.

IV. Methods of Treatment

In another aspect, the present invention provides a method of treating a subject suffering from an ALK- or c-Met-mediated disorder or condition comprising: administering to the subject a therapeutically effective amount of a compound of formula I or II or a pharmaceutically acceptable salt form thereof. In another aspect, the present invention provides a compound of formula I or II or a pharmaceutically acceptable salt form thereof for use in treating a subject suffering from an ALK- or c-Met-mediated disorder or condition. Preferably, the compound of formula I or II or a pharmaceutically acceptable salt form thereof is administered to the subject in a pharmaceutical composition comprising a pharmaceutically acceptable carrier. In another aspect, the present invention provides a pharmaceutical composition comprising a compound of formula I or II or a pharmaceutically acceptable salt form thereof for use in treating a subject suffering from an ALK- or c-Met-mediated disorder or condition. In another embodiment, the ALK- or c-Met-mediated condition or disorder is cancer. In another embodiment, the ALK- or c-Met-mediated condition is selected from anaplastic large cell lymphoma, inflammatory myofibroblastic tumor, glioblastoma, and other solid tumors. In another embodiment, the ALK- or c-Met-mediated condition is selected from colon cancer, breast cancer, renal cancer, lung cancer, hemangioma, squamous cell myeloid leukemia, melanoma, glioblastoma, and astrocytoma.

The ALK- or c-Met-mediated disorder or condition can be treated prophylactically, acutely, and chronically using compounds of the present invention, depending on the nature of the disorder or condition. Typically, the host or subject in each of these methods is human, although other mammals can also benefit from the administration of a compound of the present invention.

In another embodiment, the present invention provides a method of treating a proliferative disorder in a subject, comprising administering to the subject a therapeutically effective amount of a compound of formula I or II or a pharmaceutically acceptable salt form thereof. In another aspect, the present invention provides a compound of formula I or II or a pharmaceutically acceptable salt form thereof for use in treating a proliferative disorder in a subject. Preferably, the compound of formula I or II or a pharmaceutically acceptable salt form thereof is administered to the subject in a pharmaceutical composition comprising a pharmaceutically acceptable carrier. In another aspect, the present invention provides a pharmaceutical composition comprising a compound of formula I or II or a pharmaceutically acceptable salt form thereof for use in treating a proliferative disorder in a subject. In certain embodiments, the proliferative disorder is ALK- or c-Met-mediated. In certain embodiments, the proliferative disorder is cancer. In certain embodiments, the proliferative disorder is selected from anaplastic large cell lymphoma, inflammatory myofibroblastic tumor, glioblastoma, and other solid tumors. In certain embodiments, the proliferative disorder is selected from colon cancer, breast cancer, renal cancer, lung cancer, hemangioma, squamous cell myeloid leukemia, melanoma, glioblastoma, and astrocytoma.

The proliferative disorder can be treated prophylactically, acutely, and chronically using compounds of the present invention, depending on the nature of the disorder or condition. Typically, the host or subject in each of these methods is human, although other mammals can also benefit from the administration of a compound of the present invention.

The compounds of formula I and II share a common utility in treating ALK- or c-Met-mediated disorders and a common core structure essential to that utility (i.e., the compounds of formula I and II are all derivatives of 2,4-diaminopyrimidine containing a 6/7 fused bicyclic ring system).

In therapeutic applications, the compounds of the present invention can be prepared and administered in a wide variety of oral and parenteral dosage forms. Thus, the compounds of the present invention can be administered by injection, that is, intravenously, intramuscularly, intracutaneously, subcutaneously, intraduodenally, or intraperitoneally. Also, the compounds described herein can be administered by inhalation, for example, intranasally. Additionally, the compounds of the present invention can be administered transdermally. In another embodiment, the compounds of the present invention are delivered orally. The compounds can also be delivered rectally, bucally or by insufflation.

The compounds utilized in the pharmaceutical method of the invention can be administered at the initial dosage of about 0.001 mg/kg to about 100 mg/kg daily. In another embodiment, the daily dose range is from about 0.1 mg/kg to about 10 mg/kg. The dosages, however, may be varied depending upon the requirements of the subject, the severity of the condition being treated, and the compound being employed. Determination of the proper dosage for a particular situation is within the skill of the practitioner. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day, if desired.

V. Chemistry

Unless otherwise indicated, all reagents and solvents were obtained from commercial sources and used as received. $^1$H NMRs were obtained on a Bruker Avance at 400 MHz in the solvent indicated with tetramethylsilane as an internal standard. Analytical HPLC was run using a Zorbax RX-C8, 5×150 mm column eluting with a mixture of acetonitrile and water containing 0.1% trifluoroacetic acid with a gradient of 10-100%. LCMS results were obtained on either of two instruments. First, in Examples that indicate LCMS retention times, analysis was performed on a Waters Aquity Ultra Performance LC with a 2.1 mm×50 mm Waters Aquity HPLC BEH C18 1.7 µm column. The target column temperature was 45° C., with a run time of two (2) minutes, a flow rate of 0.600 mL/min, and a solvent mixture of 5% (0.1% formic acid/water):95% (acetonitrile/0.1% formic acid). The mass spectrometry data was acquired on a Micromass LC-ZQ 2000 quadrupole mass spectrometer. Second, in Examples that do not indicate LCMS retention times, analysis was performed on a Bruker Esquire 200 ion trap. Automated column chromatography was performed on a CombiFlash Companion (ISCO, Inc.). Melting points were taken on a Mel-Temp apparatus and are uncorrected.

Synthesis

The compounds of the present invention can be prepared in a number of ways well known to one skilled in the art of organic synthesis. The compounds of the present invention can be synthesized using the methods described below as well as using methods known to one skilled in the art of organic chemistry or variations thereon as appreciated by those skilled in the art. The preferred methods include, but are not limited to or by, those described below.

The compounds of this invention may be prepared using the reactions and techniques described in this section. The reactions are performed in solvents appropriate to the reagents, and materials employed are suitable for the transformations being effected. Also, in the description of the synthetic methods below, it is to be understood that all proposed reaction conditions, including choice of solvent, reaction atmosphere, reaction temperature, duration of experiment and workup procedures are chosen to be conditions standard for that reaction which should be readily recognized by one skilled in the art of organic synthesis.

It is understood that the examples and embodiments described herein are for illustrative purposes only and that various modifications or changes in light thereof will be suggested to persons skilled in the art and are to be included within the spirit and purview of this application and the scope of the appended claims.

Compounds of formula I or II are available from a chloropyrimidine derivative such as a compound of formula 2 and an appropriate aniline (compounds of formula 1 or 3) using an appropriate acid in an alcoholic solvent using either thermal or microwave heating. Typical acids include, but are not limited to, hydrochloric acid, p-toluenesulfonic acid (p-TsOH) and camphorsulfonic acid. Solvents that are typically used include, but are not limited to, ethanol, isopropanol and methoxyethanol.

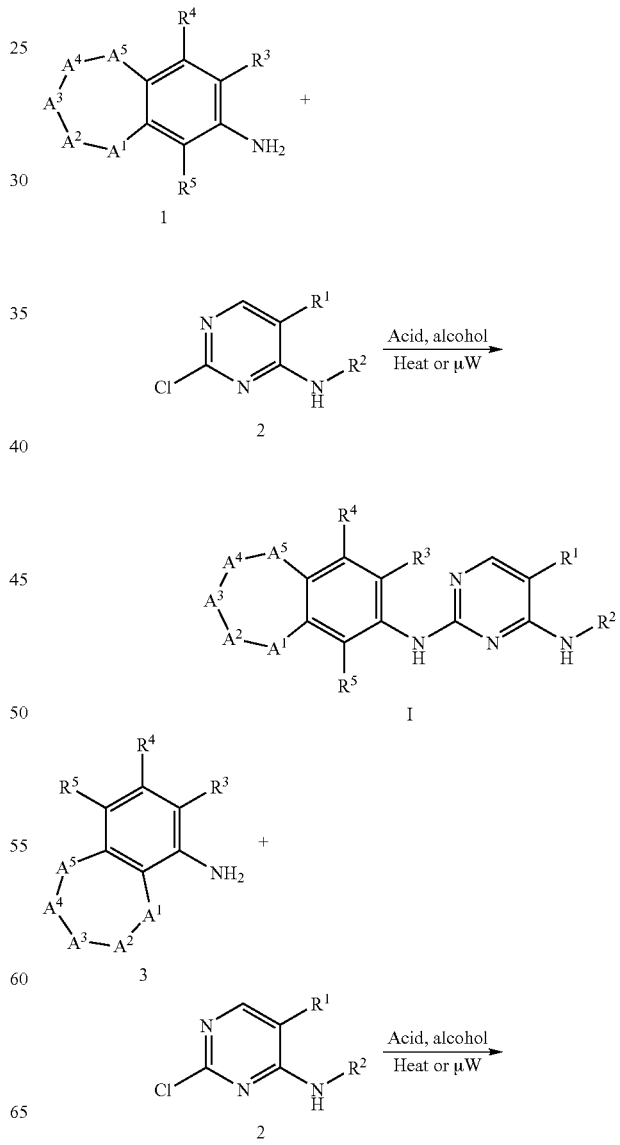

Scheme 1

-continued

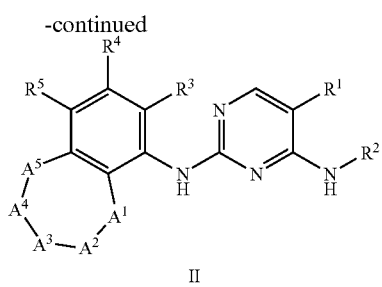

II

Anilines such as compounds of formula 1 or 3 (Scheme 2) can be prepared from an aromatic system such as compounds of formula 4 or 5 via a nitration protocol followed by reduction. Typical nitration conditions involve the use of reagents such as nitric acid/sulfuric acid or potassium nitrate/trifluoroacetic anhydride. Reduction can be effected by reagents such as hydrogen with a metal catalyst (Pt, Pd or Ni) or hydrazine in the presence of metal such as Pd, but is not limited to these conditions. Alternatively, the aniline may arise from an appropriately functionalized carboxylate (compounds of formula 6 and 7) via Curtius rearrangement. Typically, Curtius rearrangements can be effected by reagents such as diphenyl phosphoryl azide or isobutyl chloroformate/sodium azide followed in each instance by heating. Alternatively, instead of a carboxylate of formula 6 or 7, an analogous carboxamide can be transformed into an amine via Wolff rearrangements. These transformations listed above and below are well known to one skilled in the art of organic synthesis and can be found in references such as Synthetic Organic Methodology: Comprehensive Organic Transformations. A Guide to Functional Group Preparations. Larock, R. C. (1989), (VCH, Weinheim).

priately functionalized ring system. A Schmidt or Beckmann rearrangement of a tetralone system such as a compound of formula 8 or a functionalized derivative thereof affords the 1,3,4,5-tetrahydro-benzo[b]azepin-2-one of formula 9. Nitration gives 10, which is followed by functionalization of the amide nitrogen (in this scheme alkyl, but not limited to alkyl), and reduction of the nitro group. The regioisomeric, 2,3,4,5-tetrahydro-benzo[c]azepin-1-one (15) may be prepared following a similar sequence which may be functionalized appropriately.

Scheme 3

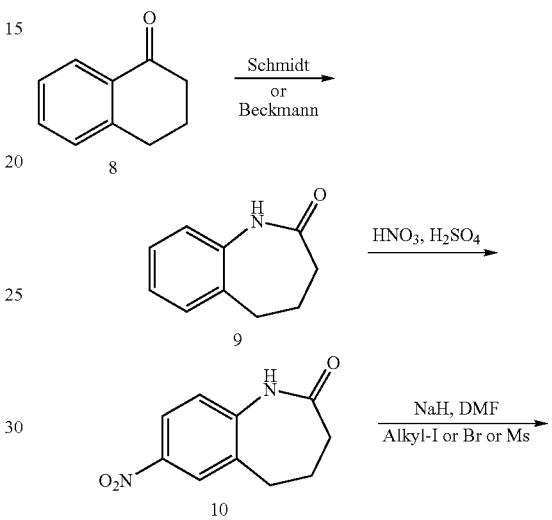

Compounds of the present invention with 6/7 fused aromatic ring systems such as compounds of formula 4-7 are available from a variety of synthetic methods known to those of ordinary skill in the art. The following methods describe synthesis of anilines of formula 1 and 3 which, in turn, can be used in methods described in Scheme 1 to give compounds of the present invention. For example, 1,3,4,5-tetrahydro-benzo[b]azepin-2-ones of formula 4 or 5 may be prepared by a synthetic sequence as outlined in Scheme 3 to form the appro- Scheme 2

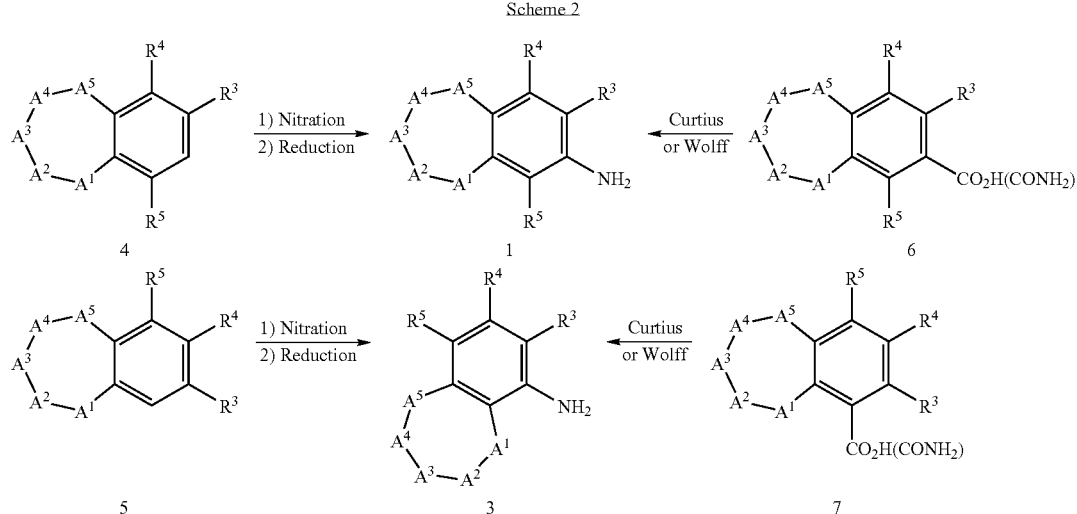

-continued

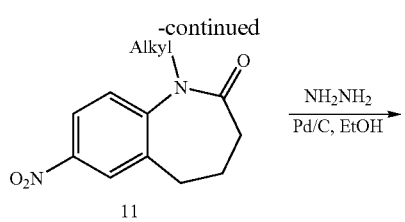

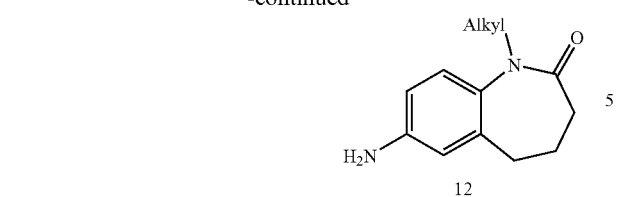

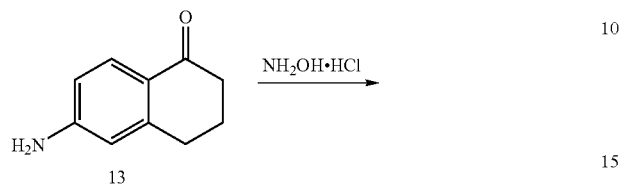

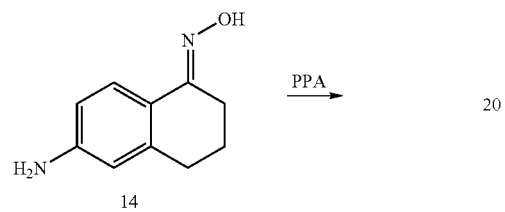

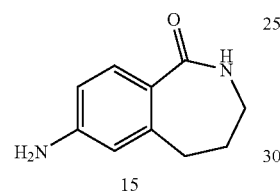

Tetralones with functional groups attached to the aromatic ring including, but not limited to, —OCH$_3$, —CH$_3$, ethyl, and —OCF$_3$, and/or appendages to the saturated portion including, but not limited to, methyl, dimethyl, and ethyl, can be prepared using analogous sequences. For example (Scheme 4), both 5-methoxy tetralone 16, and 4,4-dimethyltetralone, using this sequence, provided 20/21 and 25 respectively. Similarly 5-, 6-, 7- or 8-substituted tetralones may be used to prepare the appropriate aniline using a sequence such as that described in Scheme 4

Scheme 4

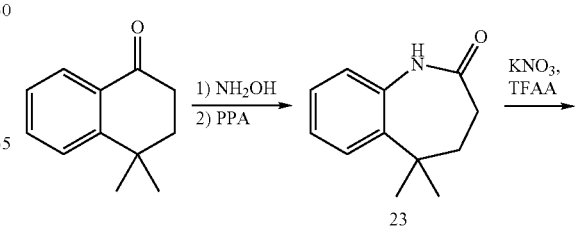

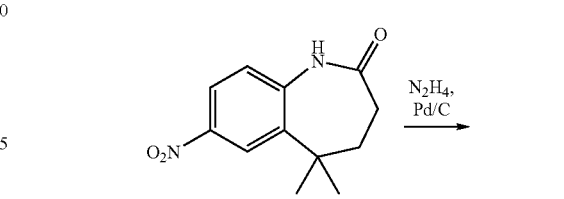

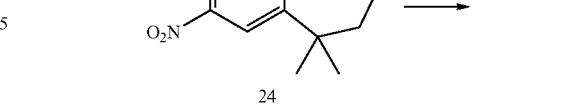

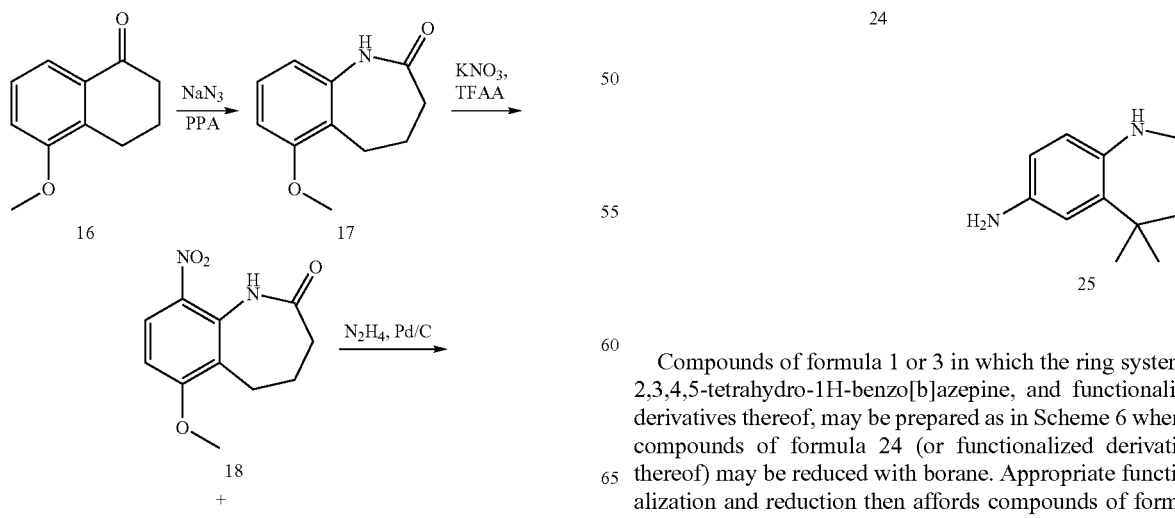

Compounds of formula 1 or 3 in which the ring system is 2,3,4,5-tetrahydro-1H-benzo[b]azepine, and functionalized derivatives thereof, may be prepared as in Scheme 6 wherein compounds of formula 24 (or functionalized derivatives thereof) may be reduced with borane. Appropriate functionalization and reduction then affords compounds of formula 27 and functionalized derivatives thereof.

193

Scheme 6

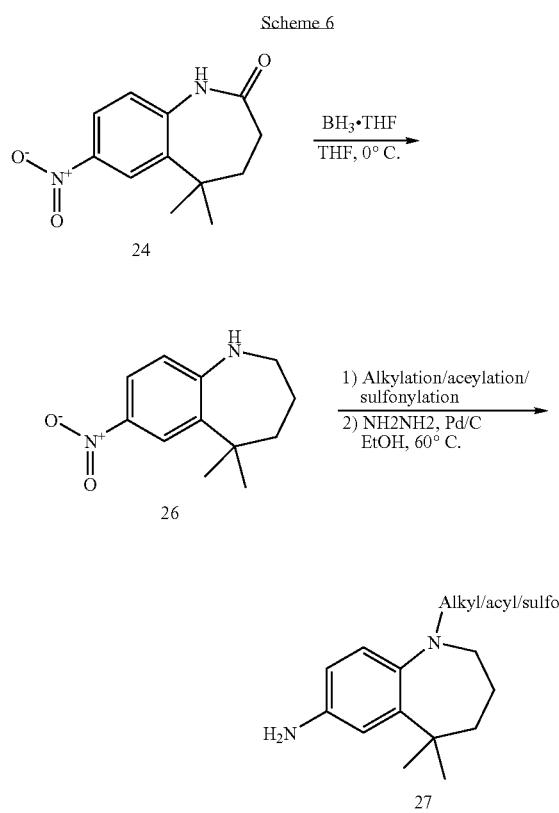

Anilines of formula 1 in which the ring system is 2,3,3a,4-tetrahydro-1H,6H-5-oxa-10b-aza-benzo[e]azulen-8-ylamine or 7,7a,8,9,10,11-hexahydro-5H-6-oxa-1,1a-aza-dibenzo[a,c]cyclohepten-3-ylamine, and functionalized derivatives thereof, can be prepared by adopting a similar procedure as described by Mueller, W. et al. in *Helvetica Chimica Acta*, 1982, 65, 2118. This gives compounds of formula 31 (Scheme 7) and functionalized derivatives thereof. The methodology can be extended from hydroxymethylpyrrolidine systems (i.e. 29 and functionalized derivatives thereof) to larger rings such as piperidines to give 7,7a,8,9,10,11-hexahydro-5H-6-oxa-11a-aza-dibenzo[a,c]cyclohepten-3-ylamines and functionalized derivatives thereof.

Scheme 7

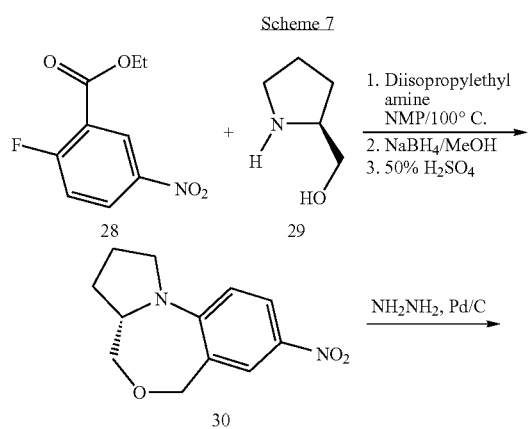

194

-continued

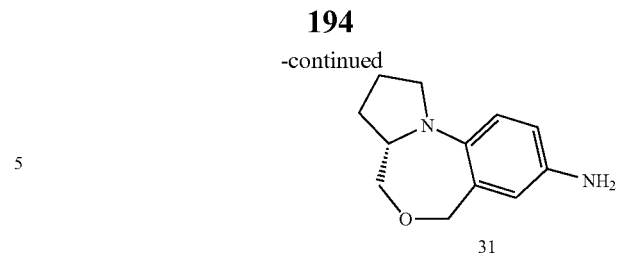

Compounds of formula 1 or 3 in which the ring system is 2,3,4,5-tetrahydro-1H-benzo[d]azepine, and functionalized derivatives thereof, can be prepared as in Scheme 8. The azepine ring is formed through a double displacement with ammonia of a dimesylate of formula 33, or a functionalized derivative thereof. Nitration and functionalization followed by reduction gives compounds of formula 36 and functionalized derivatives thereof.

Scheme 8

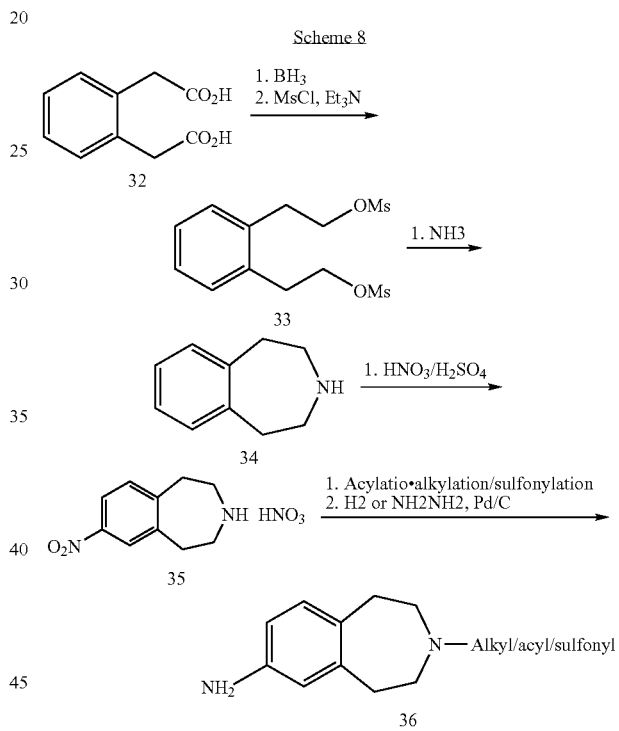

Functionalized derivatives of 2,3,4,5-tetrahydro-1H-benzo[d]azepine can be prepared using methods known to those of ordinary skill in the art. For example, compounds of the formula 41, and functionalized derivatives thereof, may be prepared following Scheme 9 using a Friedel-Crafts intramolecular acylation to give compounds of formula 39, and functionalized derivatives thereof, which can be reduced, nitrated and functionalized (for example, but not limited to: alkylation, acylation, sulfonylation) to give compounds of formula 41, and functionalized derivatives thereof. Compounds of formula 40, and functionalized derivatives thereof, may also be prepared using an alternative sequence, also outlined in Scheme 9 starting from (methoxyphenyl)acetic acid derivative 42, or a functionalized derivative thereof. Compounds of formula 43, and functionalized derivatives thereof, are available by procedures similar to that described by Reiffen, M. et al. in *J. Med. Chem.*, 1990, 33, 1496-1504. Compounds of formula 43, and functionalized derivatives thereof, can be reduced in two steps to compounds of formula 40, and functionalized derivatives thereof. Compounds of formula 1 or 3 in which the ring system is 8-methoxy-1,3-dihydro-benzo[d]azepin-2-one, and functionalized derivatives thereof, can be prepared from 43, or a functionalized derivative thereof, and transformed into compounds of formula 45, and functionalized derivatives thereof. Also, compounds of formula 43, and functionalized derivatives thereof, can be transformed into compounds of formula 47, and functionalized derivatives thereof.

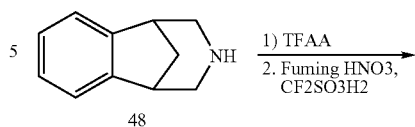

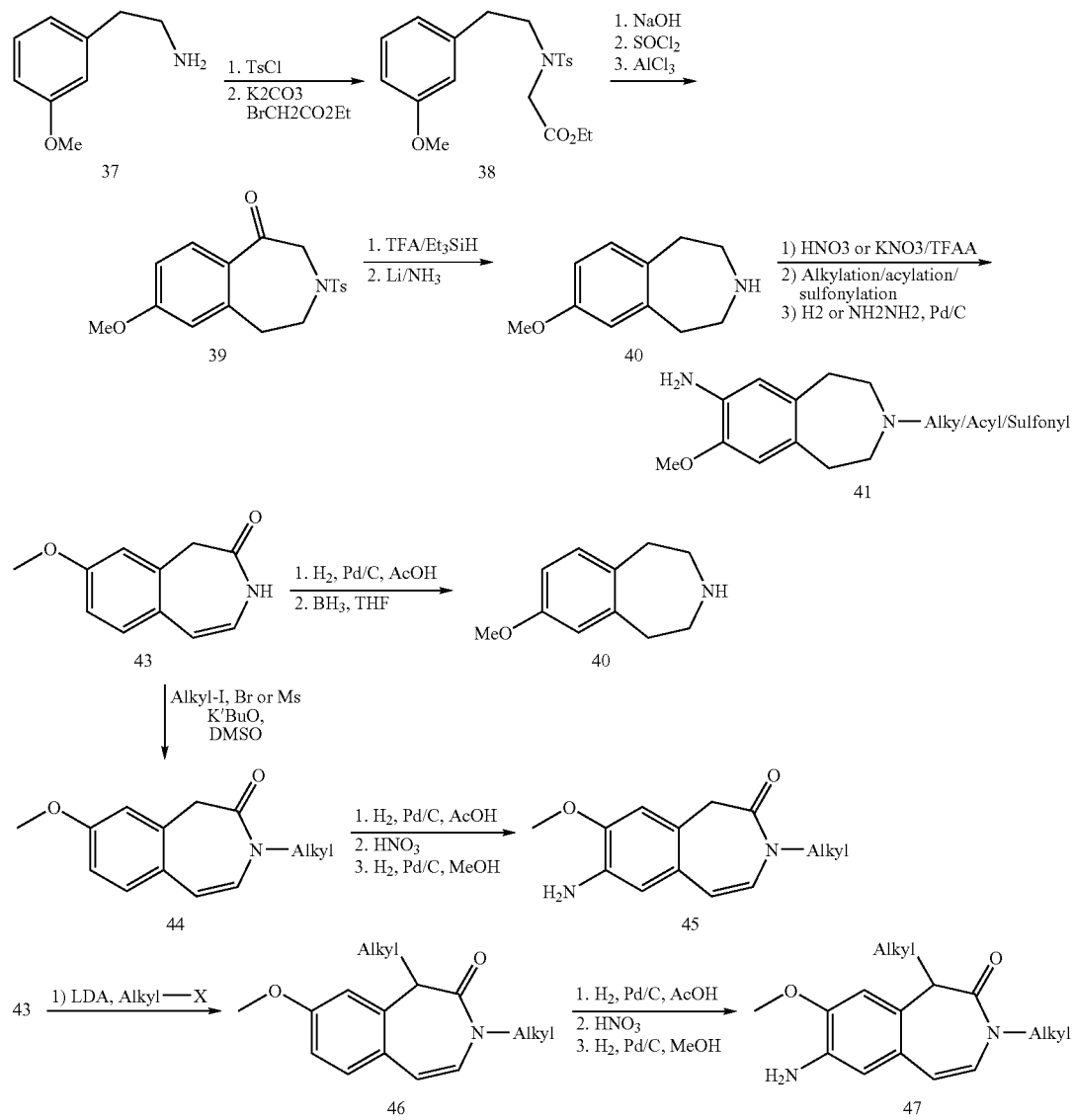

Compounds of formula 1 or 3 in which the ring system is 10-aza-tricyclo[6.3.1.0*2,7*]dodeca-2,4,6-trien-4-ylamine, and functionalized derivatives thereof, can be prepared starting from compounds of formula 48, and functionalized derivatives thereof (Scheme 10), which can be prepared by methods known in the literature (e.g., O'Donnell, Christopher J. et al., A General Route to the Synthesis of 1,5-Methano- and 1,5-Ethano-2,3,4,5-tetrahydro-1H-3-benzazepines. *J. Org. Chem.* 2004, 69, 5756-5759). Nitration, functionalization and reduction provides compounds of formula 50, and functionalized derivatives thereof.

-continued

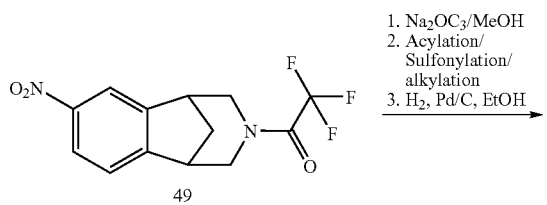

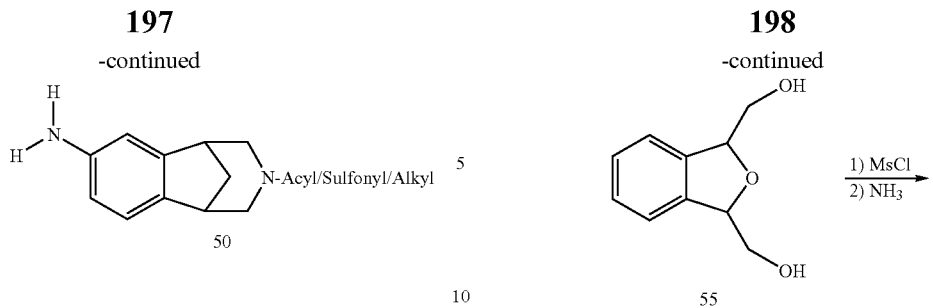

Compounds of formula 1 or 3 in which the ring system is 10-aza-tricyclo[6.3.2.0*2,7*]trideca-2,4,6-triene, and functionalized derivatives thereof, can be prepared starting from compounds of formula 51, or functionalized derivatives thereof (Scheme 11), which can be prepared by methods known in the literature (O'Donnell, Christopher J. et al., A General Route to the Synthesis of 1,5-Methano- and 1,5-Ethano-2,3,4,5-tetrahydro-1H-3-benzazepines. *J. Org. Chem.*, 2004, 69(17), 5756-5759). Further functionalization may be achieved, e.g., via the method of Coe, J. W. et al., *J. Med. Chem.*, 2005, 48, 3474-3477, which provides the 10-alkyl, 4-anilino derivatives of compounds of formula 53, and functionalized derivatives thereof.

Scheme 11

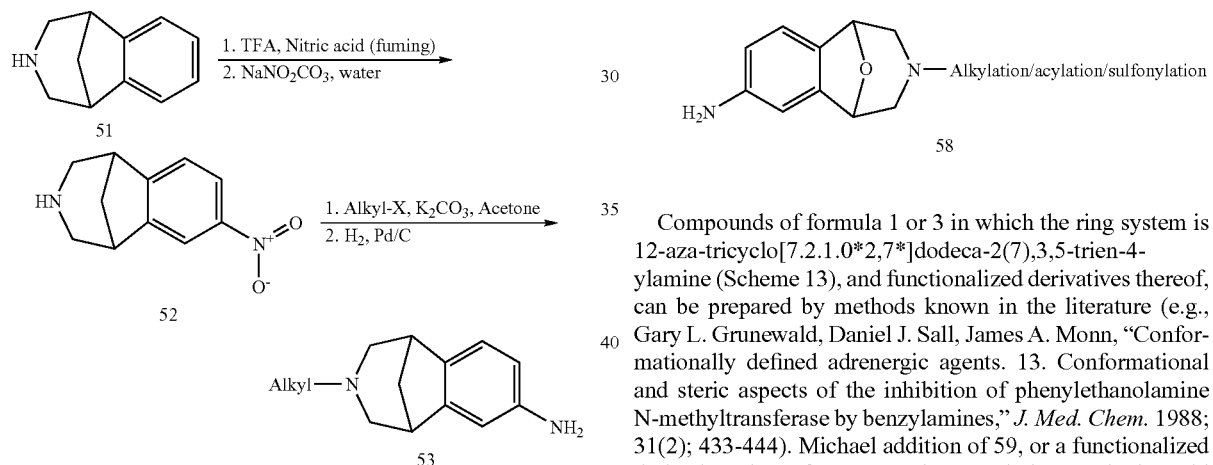

Compound of formula 1 or 3 in which the ring system is 12-oxa-10-aza-tricyclo[6.3.1.0*2,7*]dodeca-2,4,6-trien-4-ylamine (Scheme 12), and functionalized derivatives thereof, are available following a similar procedure to that outlined in Scheme 8 in which the azepine ring is cyclized via bis-mesylate displacement with ammonia. Likewise, cyclization of compounds of formula 55, and functionalized derivatives thereof, provides compounds of formula 56, and functionalized derivatives thereof. Nitration, functionalization and reduction provides compounds of formula 58, and functionalized derivatives thereof.

Scheme 12

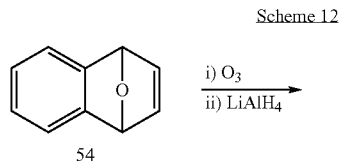

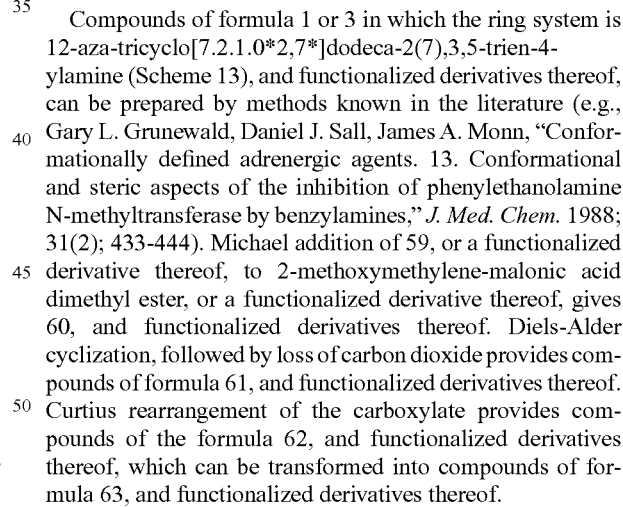

Compounds of formula 1 or 3 in which the ring system is 12-aza-tricyclo[7.2.1.0*2,7*]dodeca-2(7),3,5-trien-4-ylamine (Scheme 13), and functionalized derivatives thereof, can be prepared by methods known in the literature (e.g., Gary L. Grunewald, Daniel J. Sall, James A. Monn, "Conformationally defined adrenergic agents. 13. Conformational and steric aspects of the inhibition of phenylethanolamine N-methyltransferase by benzylamines," *J. Med. Chem.* 1988; 31(2); 433-444). Michael addition of 59, or a functionalized derivative thereof, to 2-methoxymethylene-malonic acid dimethyl ester, or a functionalized derivative thereof, gives 60, and functionalized derivatives thereof. Diels-Alder cyclization, followed by loss of carbon dioxide provides compounds of formula 61, and functionalized derivatives thereof. Curtius rearrangement of the carboxylate provides compounds of the formula 62, and functionalized derivatives thereof, which can be transformed into compounds of formula 63, and functionalized derivatives thereof.

Scheme 13

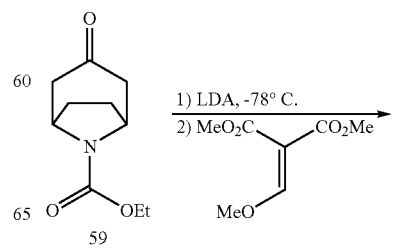

199

-continued

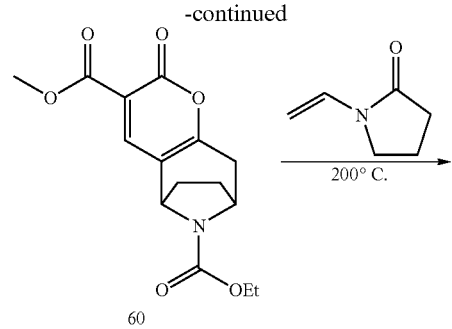

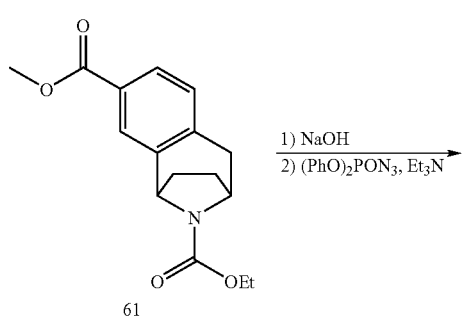

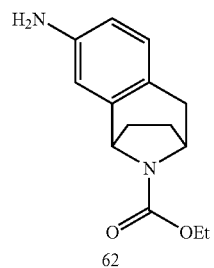

Scheme 14

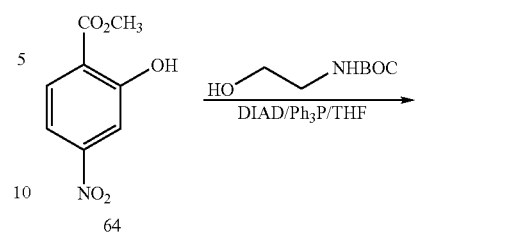

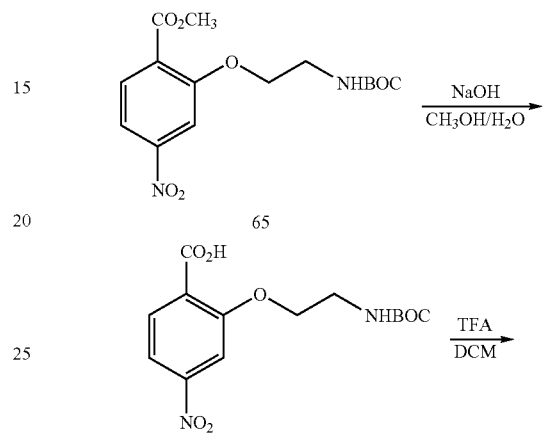

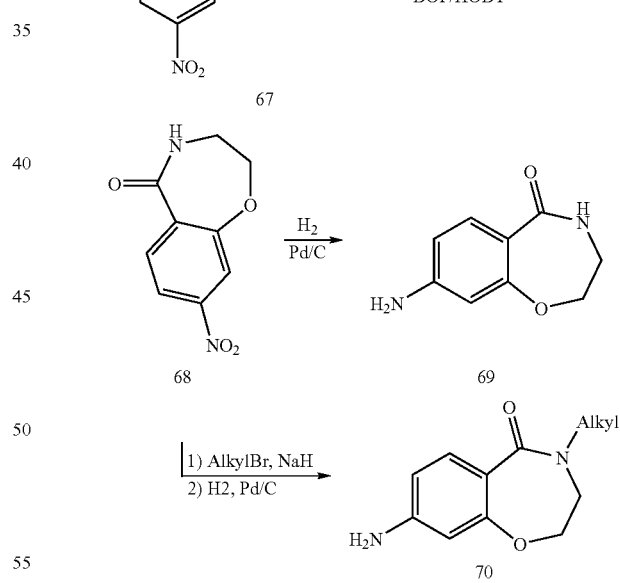

Compounds of formula 1 or 3 in which the ring system is 8-amino-3,4-dihydro-2H-benzo[f][1,4]oxazepin-5-one, and functionalized derivatives thereof, can be prepared according to Scheme 14. Mitsunobu alkylation of phenol 64, or a functionalized derivative thereof, followed by saponification of the ester gives the acid 67, and functionalized derivatives thereof. Deprotection of the primary amine gives the cyclization precursor which, using coupling with BOP/HOBt gives the 3,4-dihydro-2H-benzo[f][1,4]oxazepin-5-one ring system and functionalized derivatives thereof. Manipulation as previously described gives compounds of formula 69 and 70, and functionalized derivatives thereof.

Compounds of formula 1 or 3 in which the ring system is 2,3,4,5-tetrahydro-benzo[f][1,4]oxazepin-7-ylamine, and functionalized derivatives thereof, can be prepared according to Scheme 15. Reductive alkylation of ethanolamine with 71, or a functionalized derivative thereof, follow by cyclization with TBAF and subsequent manipulation gives compounds of formula 75, and functionalized derivatives thereof.

Scheme 15

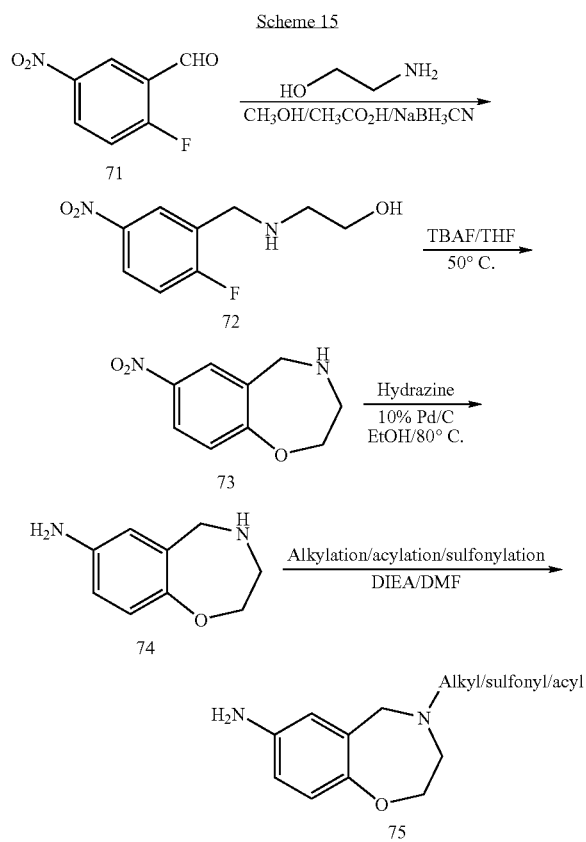

Similarly, outlined in Scheme 16, compounds of formula 1 or 3 in which the ring system is 6,7,8,9-tetrahydro-5-thia-8-aza-benzocyclohepten-2-ylamine (i.e. compounds of formula 80), and functionalized derivatives thereof, can be prepared.

Scheme 16

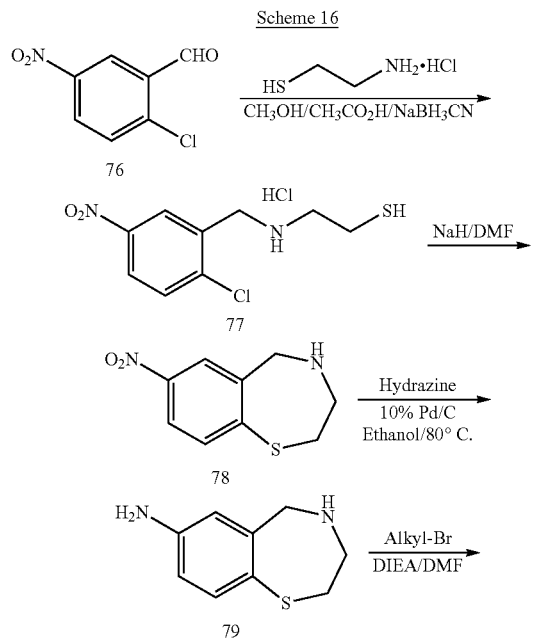

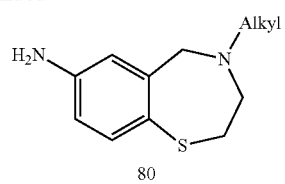

Compounds of formula 1 or 3 in which the ring system is 2,3,4,5-tetrahydro-1H-benzo[e][1,4]diazepin-8-ylamine (i.e. compounds of formula 84 and 88) and 8-Amino-1,2,3,4-tetrahydro-benzo[e][1,4]diazepin-5-one (i.e. compounds of formula 91), and functionalized derivatives thereof, can be prepared as outlined in Scheme 17. These compounds are prepared by adding an appropriately functionalized diamine to a fluoro-nitrobenzoic acid derivative (e.g, 81) to give 82, and functionalized derivatives thereof. The diamine can be functionalized with alkyl groups as shown but is not limited to such. An appropriately protected substrate is also effective for the building of these ring system. Compounds of the formula 91, and functionalized derivatives thereof, are available from 82 via functionalization and reduction. Compounds of formula 84, and functionalized derivatives thereof, are available by borane reduction and appropriate functional group manipulation. Substituted analogs of the formula 88, and functionalized derivatives thereof, are available following procedures known in the literature (e.g., Baudoin, O. et al., "Palladium-Catalyzed Borylation of Ortho-Substituted Phenyl Halides and Application to the One-Pot Synthesis of 2,2'-Disubstituted Biphenyls," *J. Org. Chem.*, 2000, 65(26), 9268-9271; Fang, Hao et al., "An efficient synthesis of sterically hindered arylboronic acids," *Tetrahedron Lett.*, 2005, 46(10), 1671-1674). For example, compounds of the formula 86, and functionalized derivatives thereof, can be brominated, followed by palladium catalyzed boronate ester formation. Oxidation of boronate compounds of the formula 87, and functionalized derivatives thereof, and appropriate functional group manipulation gives compounds of the formula 88, and functionalized derivatives thereof. Compounds of the formula 84 or 88, and functionalized derivatives thereof, can be added to an appropriate chloropyrimidine of the formula 2 and then functionalized at this stage as well to give compounds of the formula 90, and functionalized derivatives thereof.

Scheme 17

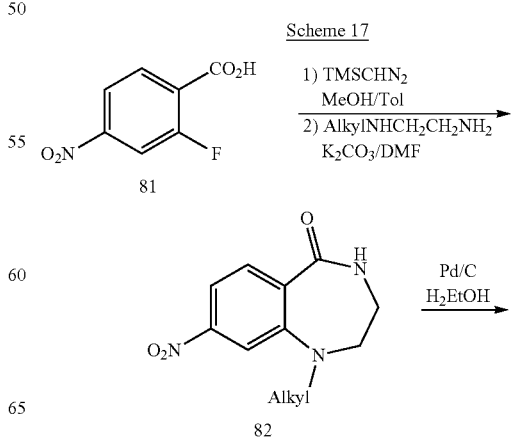

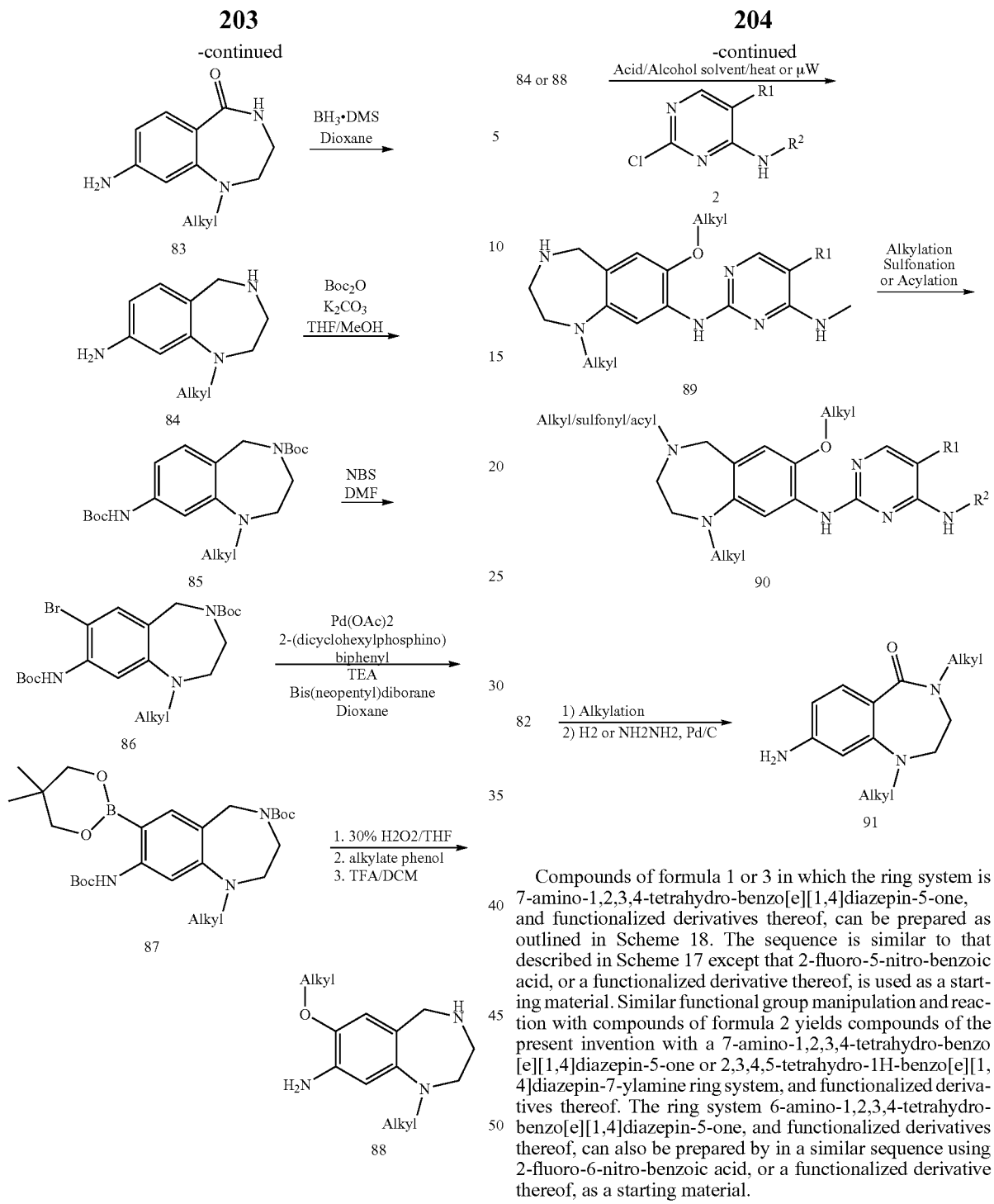

Compounds of formula 1 or 3 in which the ring system is 7-amino-1,2,3,4-tetrahydro-benzo[e][1,4]diazepin-5-one, and functionalized derivatives thereof, can be prepared as outlined in Scheme 18. The sequence is similar to that described in Scheme 17 except that 2-fluoro-5-nitro-benzoic acid, or a functionalized derivative thereof, is used as a starting material. Similar functional group manipulation and reaction with compounds of formula 2 yields compounds of the present invention with a 7-amino-1,2,3,4-tetrahydro-benzo[e][1,4]diazepin-5-one or 2,3,4,5-tetrahydro-1H-benzo[e][1,4]diazepin-7-ylamine ring system, and functionalized derivatives thereof. The ring system 6-amino-1,2,3,4-tetrahydro-benzo[e][1,4]diazepin-5-one, and functionalized derivatives thereof, can also be prepared by in a similar sequence using 2-fluoro-6-nitro-benzoic acid, or a functionalized derivative thereof, as a starting material.

Scheme 18

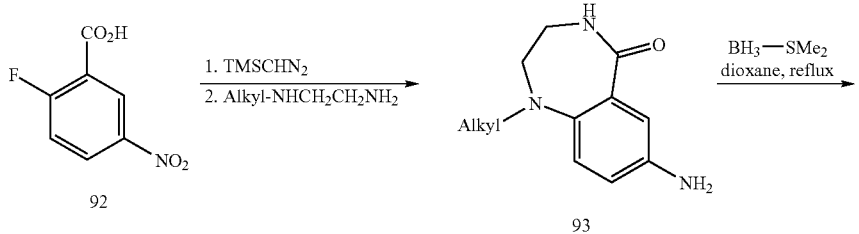

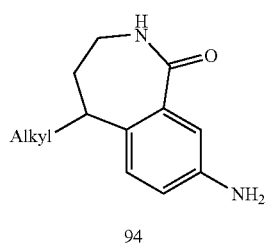

94

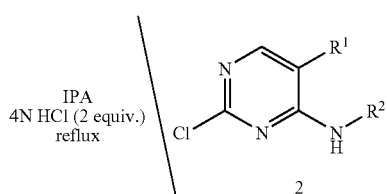

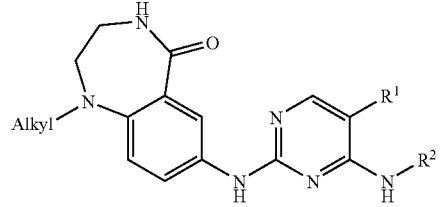

95

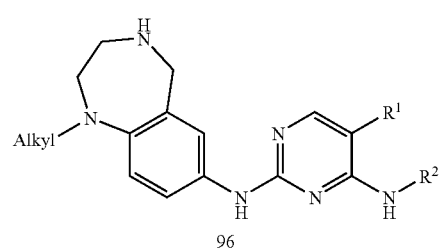

96

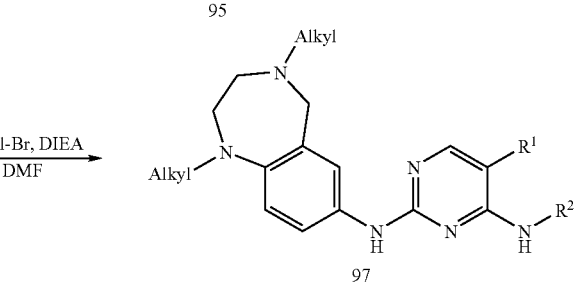

97

Compounds of formula 1 or 3 in which the ring system is 2-amino-5,6,8,9-tetrahydro-benzocyclohepten-7-one or 6,7,8,9-tetrahydro-5H-benzocycloheptene-2,7-diamine or 7,7-difluoro-6,7,8,9-tetrahydro-5H-benzocyclohepten-2-ylamine, and functionalized derivatives thereof, can be prepared using a sequence as outlined in Scheme 19. This is similar to sequences known in the literature (e.g., F. Yoshii, et al., *Helv. Chim. Acta,* 2001, 84, 2051-2063, and P. Belanger, et al., *J. Org. Chem.,* 1982, 47, 4329-4334). 1,2-Bis-bromomethyl-benzene, or a functionalized derivative thereof, can be displaced and decarboxylated to give compounds of formula 99, and functionalized derivatives thereof; nitration gives compounds of formula 100, and functionalized derivatives thereof. The ketone can be converted to the difluoro compound of formula 101, the keto derivative of formula 102, and functionalized derivatives thereof, or undergo reductive amination to compounds of formula 103, and functionalized derivatives thereof. The ketone of formula 100 can also be converted to a primary amine, and functionalized thereafter.

Scheme 19

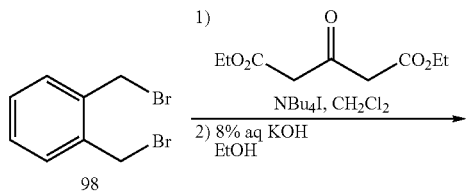

98

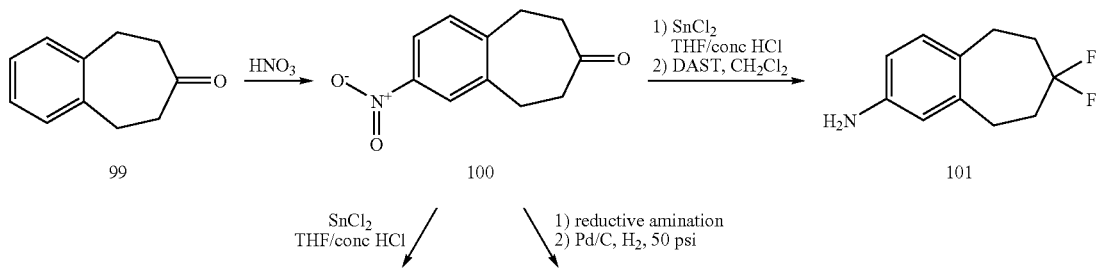

99   100   101

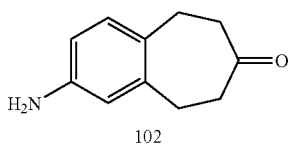
102

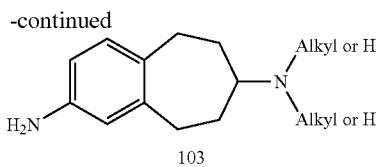
103

Compounds of formula 1 or 3 in which the ring system is 7-amino-1,2,4,5-tetrahydro-(2,4)-benzodiazepin-3-one, and functionalized derivatives thereof, can be prepared as described by Keenan et al. in *J. Med. Chem.*, 1999, 42, 545 (Scheme 20). The prepared intermediate is coupled to compounds of formula 2 to afford compounds of the present invention.

-continued

110

Compounds of formula 2 can be prepared in a variety of ways. For example, an $R^2$-amine of formula III can be coupled to a compound of formula 112 using an inorganic base, such as $K_2CO_3$, or an organic base, such as Hunig's base, in a variety of solvents, such as polar aprotic solvents such as THF, NMP or DMF (Scheme 21). This scheme is effective for amines in which $R^2$ is, for example, $C_{1-6}$-alkyl, $C_{2-6}$-alkenyl, $C_{2-6}$-alkynyl, $C_{6-15}$-aryl, $C_{3-10}$-cycloalkyl, heterocycloalkyl, and heteroaryl, and functionalized derivatives thereof in which $R^2$ group is substituted by one or more functional groups. Methods of preparing $R^2$-amines of formula III are well known to those of ordinary skill in the art.

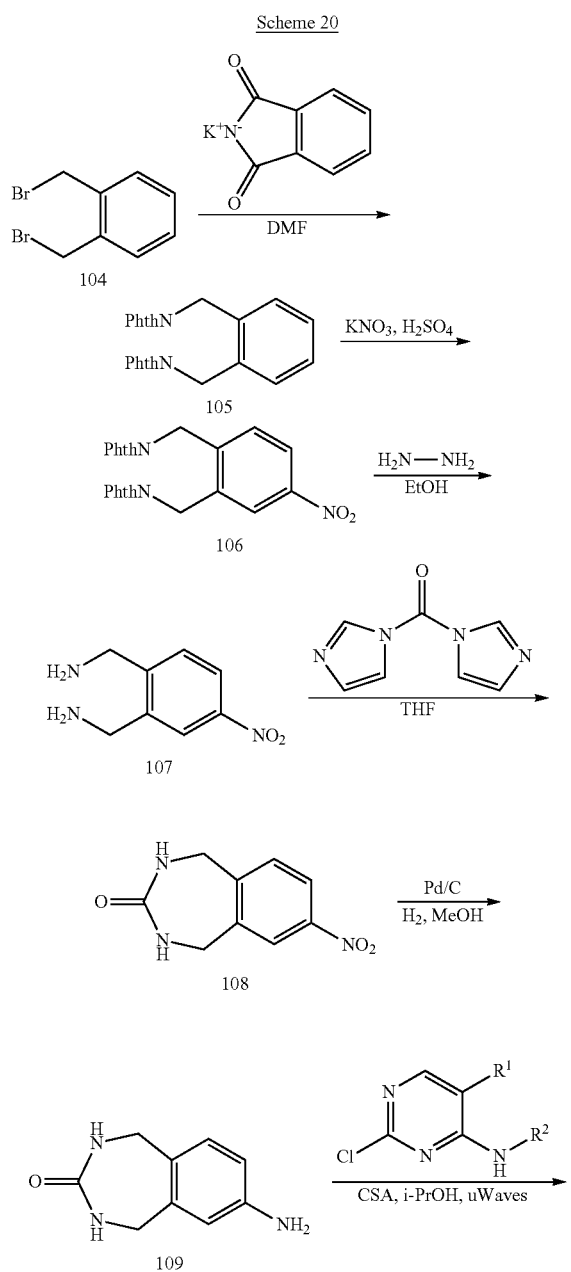

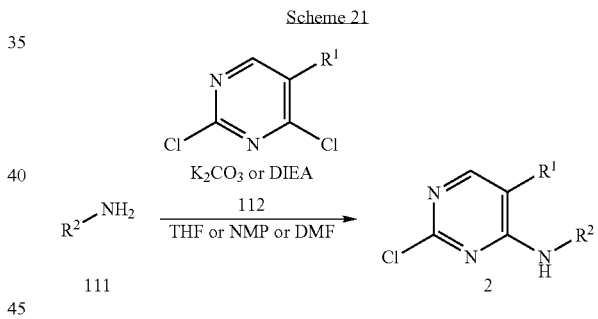

For example, compounds of formula 2 in which $R^2$ is a substituted benzamide can be prepared according to Scheme 22. Optionally functionalized isatoic anhydrides of formula 113 can be converted to 2-aminobenzamides of formula 114 with an amine ring opening reaction. These can be reacted with compounds of formula 112 to give compounds of formula 115.

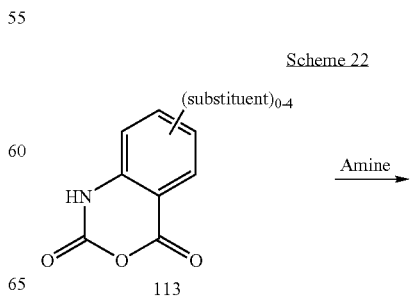

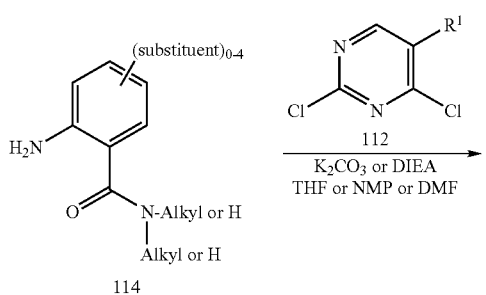

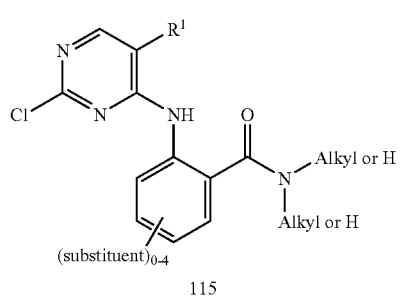

Compounds of formula 2 in which R² is a substituted carbocyclic ring or heterocyclic ring that is functionalized with a substituted amine or a carboxamide moiety can be prepared according to Scheme 23. The carbocyclic ring or heterocyclic ring of formula 116 or 117 may be partially or fully saturated, and/or bridged and/or fused to another ring and may encompass a variety of ring sizes from 3-15 membered rings and may be optionally substituted. Methods of preparing these compounds are well known to those of ordinary skill in the art.

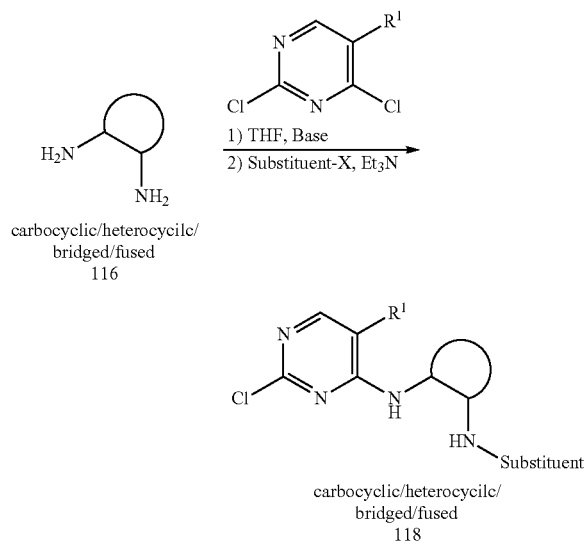

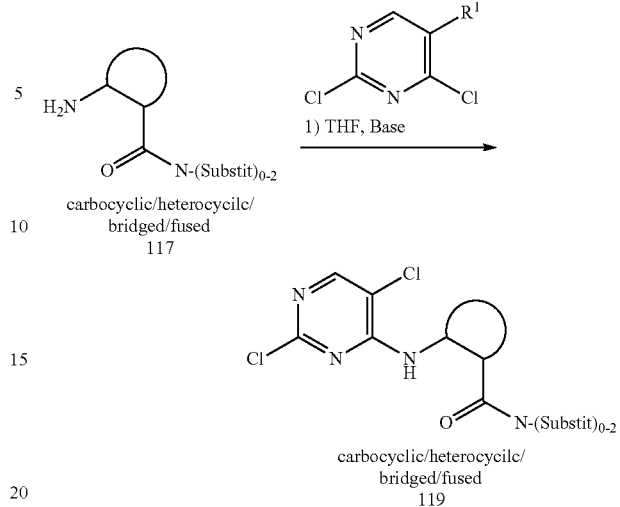

For example, methods for preparing single isomeric products of compounds of formula 116 and/or 117, and/or precursors thereof which are readily converted to compounds of formula 116 and/or 117, include, but are not limited to, methods described in (a) Bennani, Youssef L. & Hanessian, Stephen, "Trans-1,2-Diaminocyclohexane Derivatives As Chiral Reagents, Scaffolds, and Ligands for Catalysis: Applications in Asymmetric Synthesis and Molecular Recognition," *Chemical Reviews* 1997, 97, 3161-3195; (b) "Enantioselective Synthesis of -Amino Acids" E. Juaristi, Ed. (1997), Wiley-VCH, New York, N.Y.; (c) Chandrasekhar, Srivari et al., "Oligomers of cis-β-norbornene amino acid: Formation of β-strand mimetics," *Chemical Communications,* 2006, 14, 1548-1550, and (d) Davies, Stephen G. et al., "Asymmetric synthesis of (−)-(1R,2S)-cispentacin and related cis- and trans-2-amino cyclopentane- and cyclohexane-1-carboxylic acids," *Journal of the Chemical Society, Perkin Transactions 1: Organic and Bio-Organic Chemistry (1972-1999),* 1994, 11, 1411-15.

Compounds of formula 3, in which the ring system is 1,2,3,4-tetrahydro-benzo[e][1,4]diazepin-5-one, and functionalized derivatives thereof, can be prepared following a sequence outlined in Scheme 24.

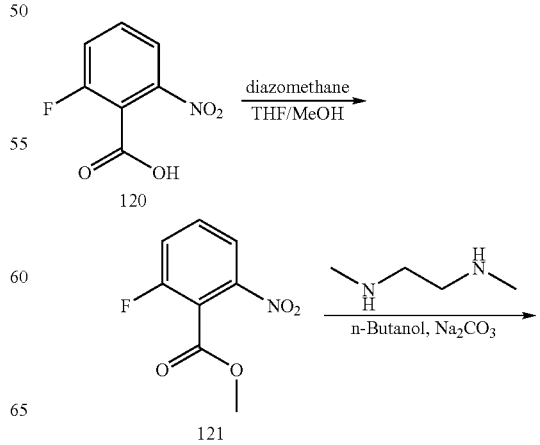

211
-continued

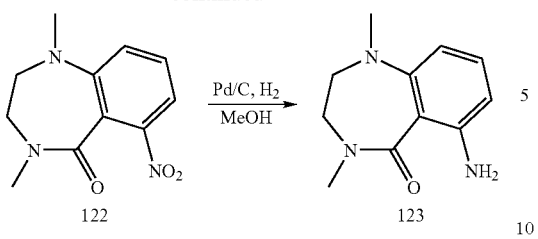

212
-continued

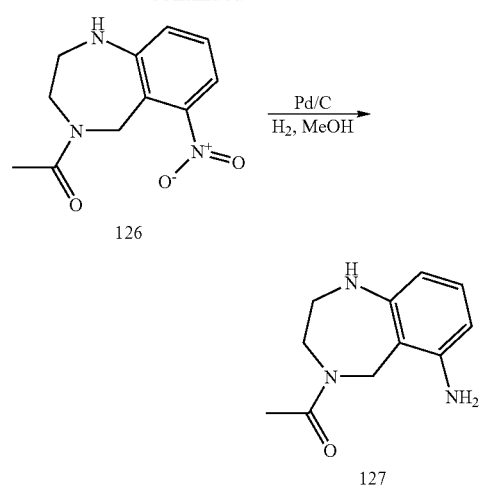

2-Fluoro-6-nitrobenzoic acid 120, or a functionalized derivative thereof, can be esterified in the presence of TMS-diazomethane to afford the desired ester of formula 121, and functionalized derivatives thereof. Cyclization can be effected by heating the product in the presence of N,N-dimethylethylene diamine to afford the desired nitro-benzazepinone of formula 122, and functionalized derivatives thereof. After reduction of the nitro group, the resulting aniline of formula 123, or a functionalized derivative thereof, is obtained and can be reacted with various dichloropyrimidine compounds to afford desired targets. In lieu of N,N-dimethylethylene diamine, other diamines can be substituted to give various substitution patterns on the 1,2,3,4-tetrahydro-benzo[e][1,4]diazepin-5-one ring system.

Compounds of formula 3, in which the ring system is 2,3,4,5-tetrahydro-1H-benzo[e][1,4]diazepin-6-ylamine, and functionalized derivatives thereof, can be prepared according to Scheme 25. Compounds of formula 120, and functionalized derivatives thereof, can be cyclized to compounds of formula 124, and functionalized derivatives thereof, which can be reduced to give compounds of formula 125, and functionalized derivatives thereof. Acylation and reduction gives compounds of formula 127, and functionalized derivatives thereof, with the 2,3,4,5-tetrahydro-1H-benzo[e][1,4]diazepin-6-ylamine ring structure.

Compounds of formula 3, in which the ring system is 2,3,4,5-tetrahydro-1H-benzo[d]azepin-6-ylamine, and functionalized derivatives thereof, can be prepared following the outline in Scheme 26. Claisen rearrangement of a compound of formula 128, or a functionalized derivative thereof, followed by triflate formation and Stille reaction with allyltributyltin gives compounds of formula 131, and functionalized derivatives thereof. Ozonolysis and reductive amination with ammonia (or equivalents) produces the desired ring system which can be reduced at the nitro group to provide compounds of formula 133, and functionalized derivatives thereof.

Scheme 25

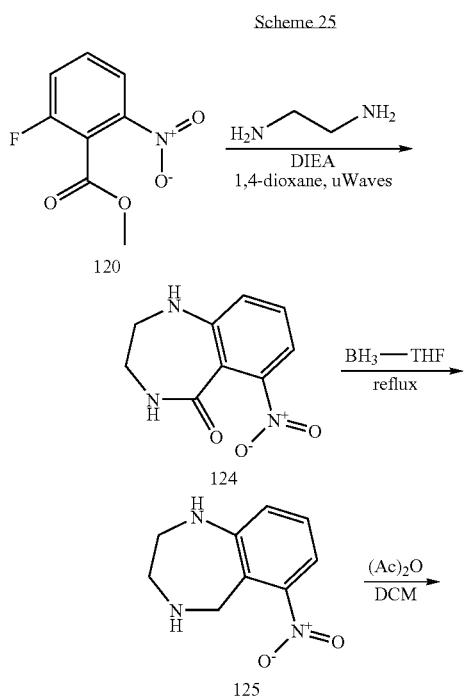

Scheme 26

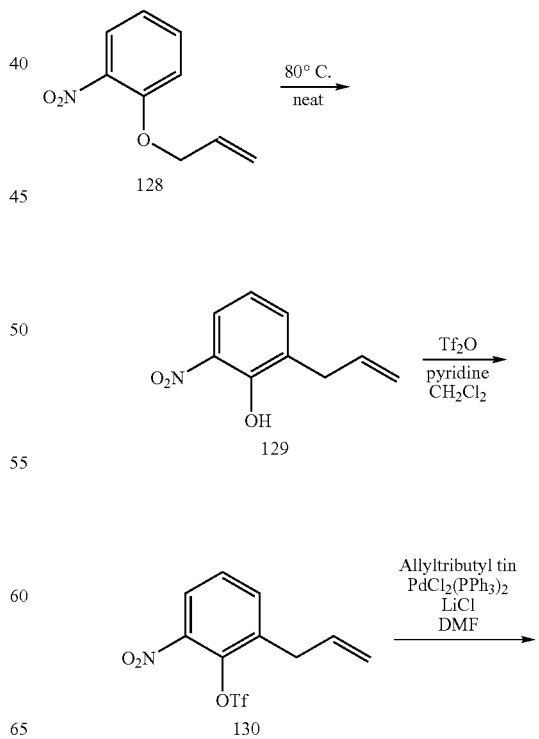

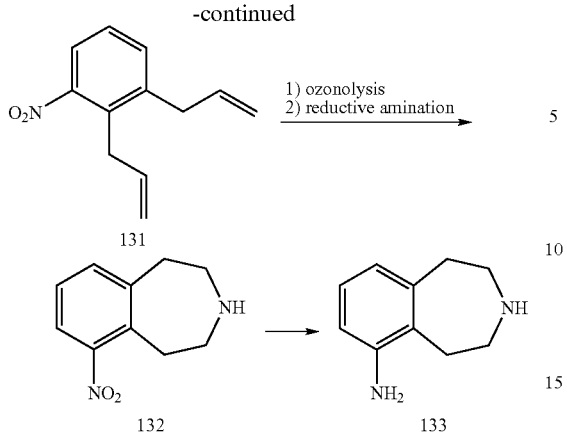

desired 6,7,8,9-tetrahydro-5H-benzocycloheptene-1,7-diamine of formula 145, and functionalized derivatives thereof. Compounds of formula 144, and functionalized derivatives thereof, can be treated with an amine under reductive conditions, a variety of which are known to one skilled in the art of organic synthesis, to provide the amine substituted compounds of formula 146, and functionalized derivatives thereof. Reduction then provides compounds of formula 147, and functionalized derivatives thereof.

Compounds of formula 3, in which the ring system is 2,3,4,5-tetrahydro-benzo[b]oxepin-9-ylamine, and functionalized derivatives thereof, can be prepared according to Scheme 27. Alkylation of a compound of formula 134, or a functionalized derivative thereof, provides compounds of formula 135, and functionalized derivatives thereof. Claisen rearrangement and allylation provide compounds of formula 137, and functionalized derivatives thereof. Cyclization using olefin metathesis provides compounds of formula 138, and functionalized derivatives thereof, which can undergo reduction of the nitro species to give compounds of the desired formula 139, and functionalized derivatives thereof.

Scheme 28

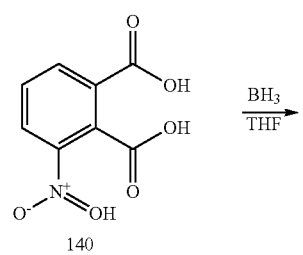

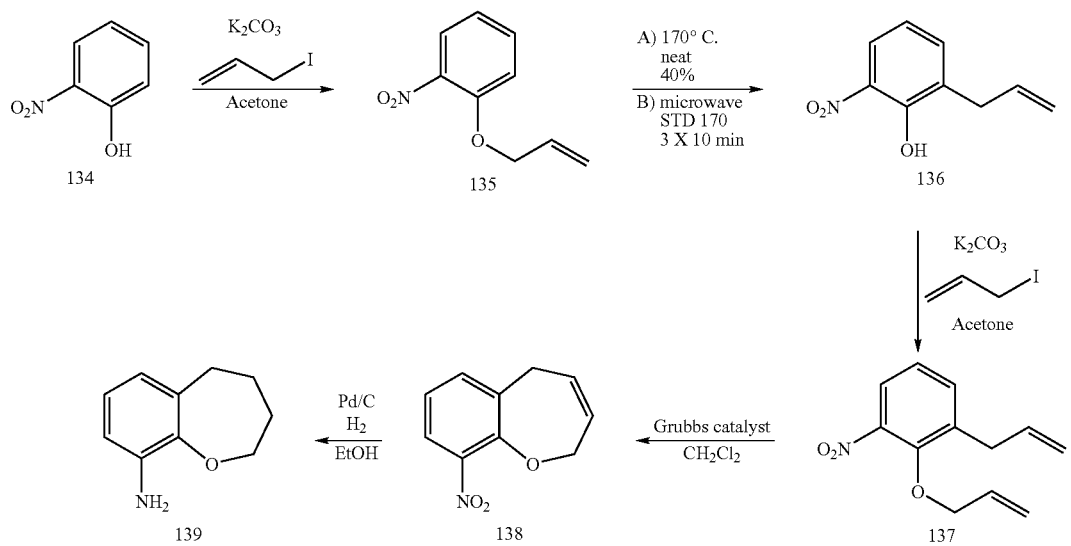

Compounds of formula 3, in which the ring system is 6,7,8,9-tetrahydro-5H-benzocycloheptene-1,7-diamine or 7-substituted-6,7,8,9-tetrahydro-5H-benzocycloheptene-1,7-diamine, and functionalized derivatives thereof, can be prepared as outlined in Scheme 28. Bis-reduction of a compound of formula 140, or a functionalized derivative thereof, will give the diol of formula 141, and functionalized derivatives thereof. Bis-bromonation and condensation with compounds of formula 143, or functionalized derivatives thereof, gives, following bis-decarboxylation, compounds of formula 144, and functionalized derivatives thereof. Reduction affords the -continued

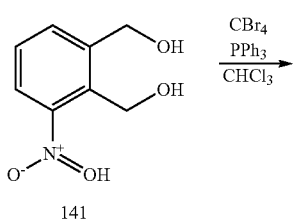

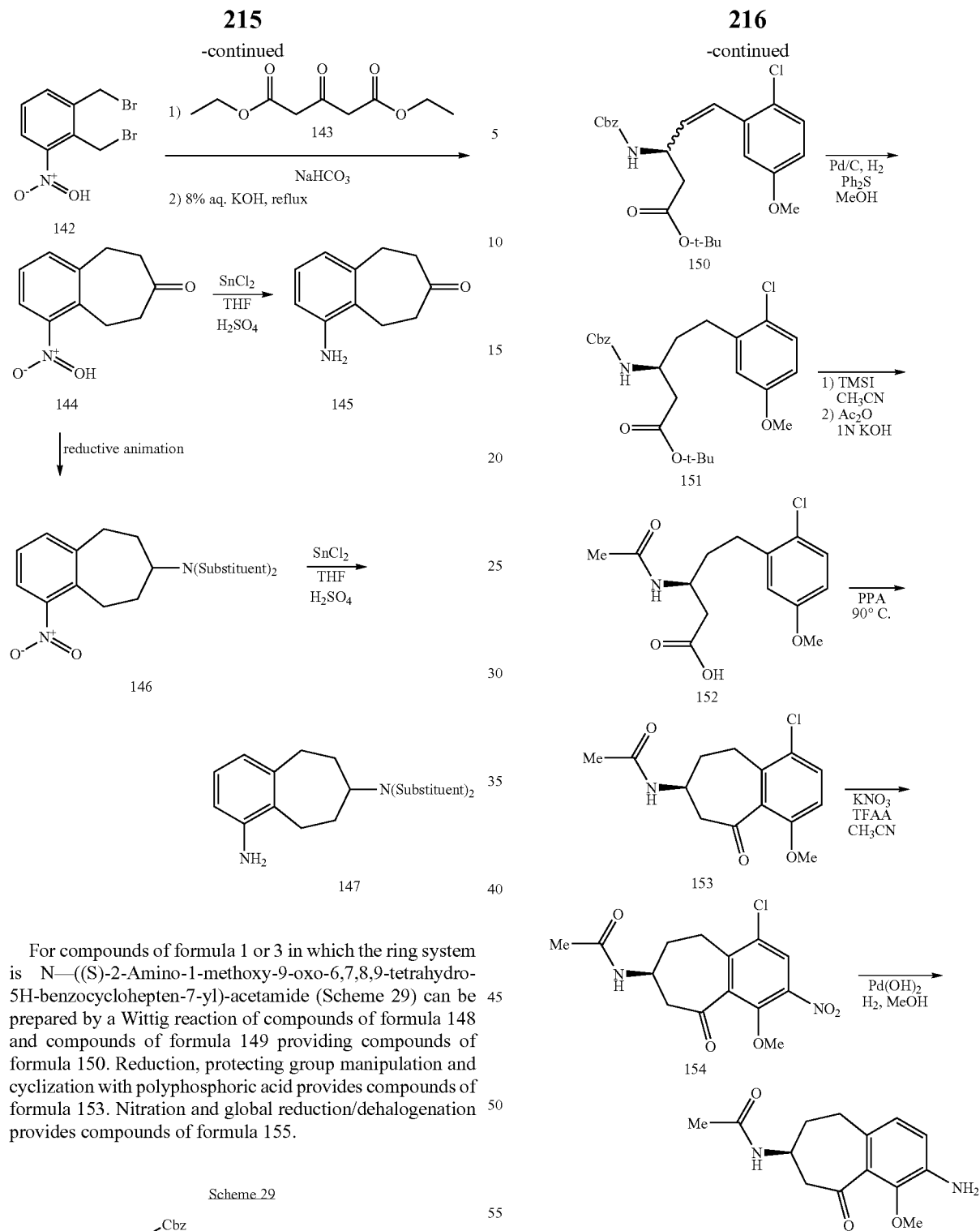

For compounds of formula 1 or 3 in which the ring system is N—((S)-2-Amino-1-methoxy-9-oxo-6,7,8,9-tetrahydro-5H-benzocyclohepten-7-yl)-acetamide (Scheme 29) can be prepared by a Wittig reaction of compounds of formula 148 and compounds of formula 149 providing compounds of formula 150. Reduction, protecting group manipulation and cyclization with polyphosphoric acid provides compounds of formula 153. Nitration and global reduction/dehalogenation provides compounds of formula 155.

Scheme 29

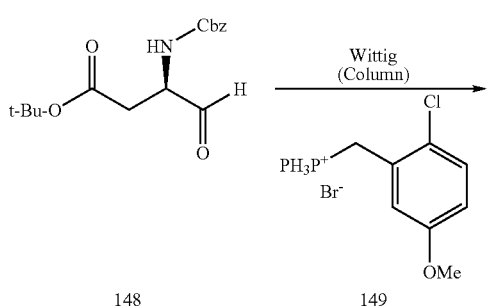

Compounds of formula 2 in which the ring system is [3-(1H-Benzoimidazol-2-yl)bicyclo[2.2.1]hept-5-en-2-yl]-(2,5-dichloro-pyrimidin-4-yl)-amine (Scheme 30) can be prepared from the protected derivative of formula 156. Condensation with phenylenediamine and deprotection provides compounds of formula 159, which in turn are reacted with trichloropyrimidine to provide compounds of formula 160.

Scheme 30

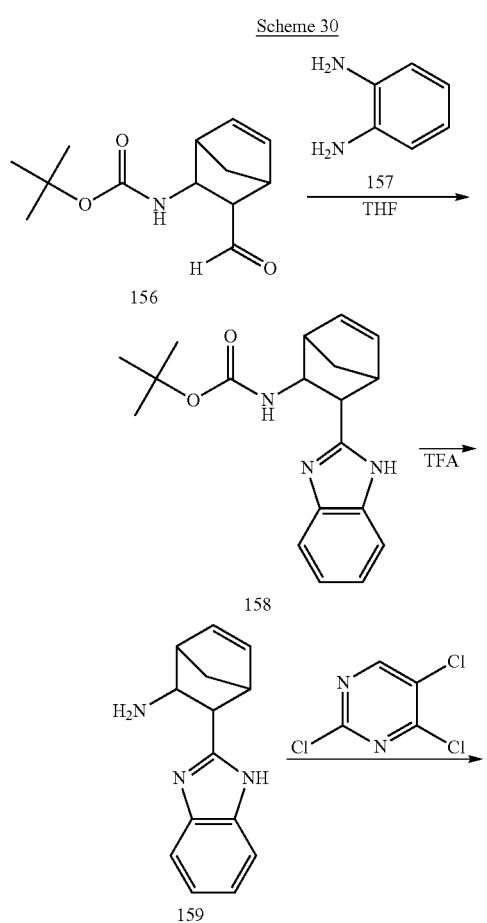

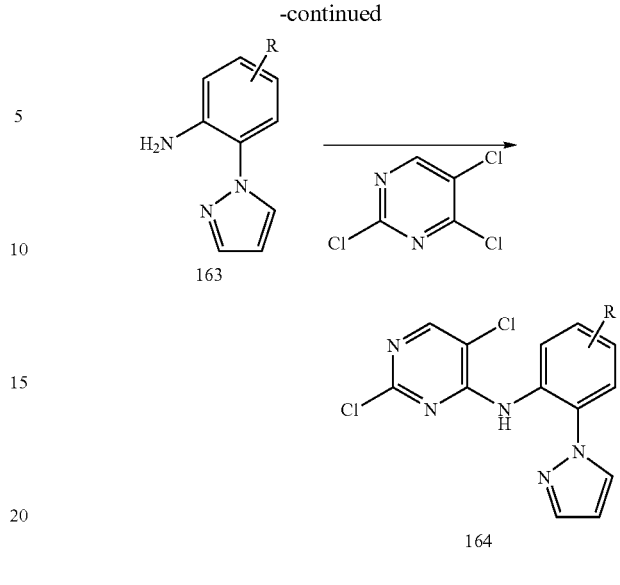

Compounds of formula 2 in which the ring systems is a substituted 2,5-Dichloro-pyrimidin-4-yl)-(2-pyrazol-1-yl-phenyl)-amine (Scheme 31) can be prepared by addition of pyrazole to a compound of formula 161. Reduction and addition to trichloropyrimidine provides compounds of formula 164.

Scheme 31

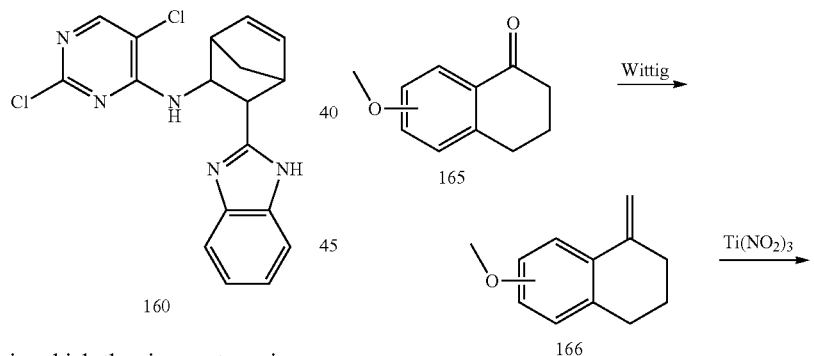

Compounds of formula 1 or 3 in which the ring system is 6,7,8,9-Tetrahydro-5H-benzocycloheptene-2,6-diamine or 6-Alkoxy-6,7,8,9-tetrahydro-5H-benzocyclohepten-2-ylamine can be constructed from an appropriately substituted tetralone of formula 165 via Wittig reaction and thallium mediated ring-expansion (*J. Med. Chem.*, 1981, 24, 429) to give compounds of formula 167. Following a nitration and functionalization, compounds of formula 169 and 170 can be prepared.

Scheme 32

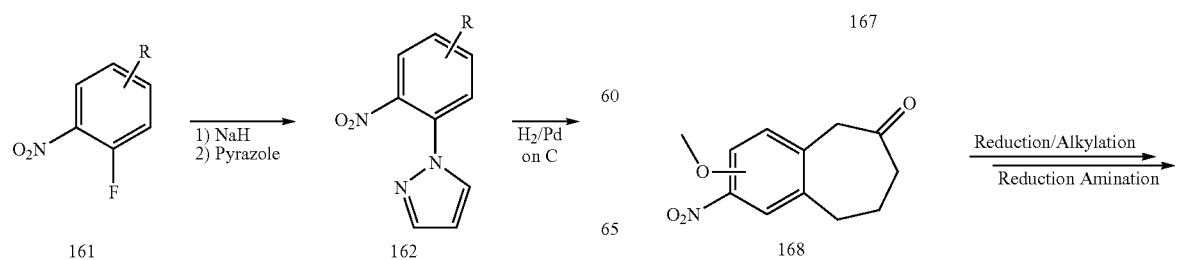

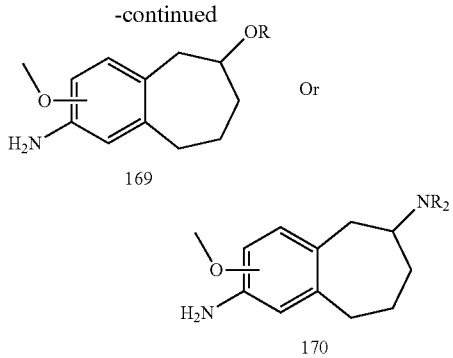

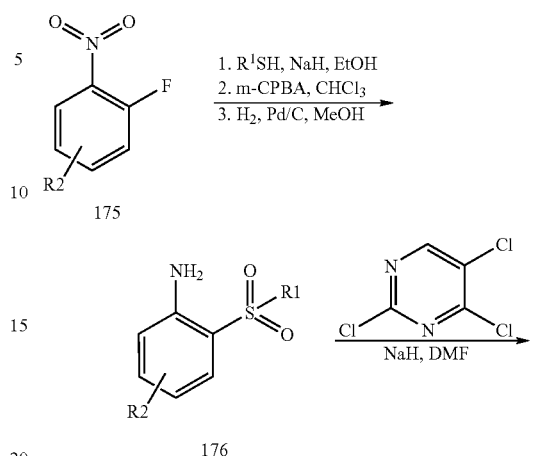

Compounds of formula 2 in which the ring system is 2-(2,5-Dichloro-pyrimidin-4-ylamino)-benzenesulfonamide (Scheme 33) can be prepared via addition of an appropriately substituted amine to compounds of formula 171. Reduction and addition to trichloropyrimidine gives compounds of formula 174.

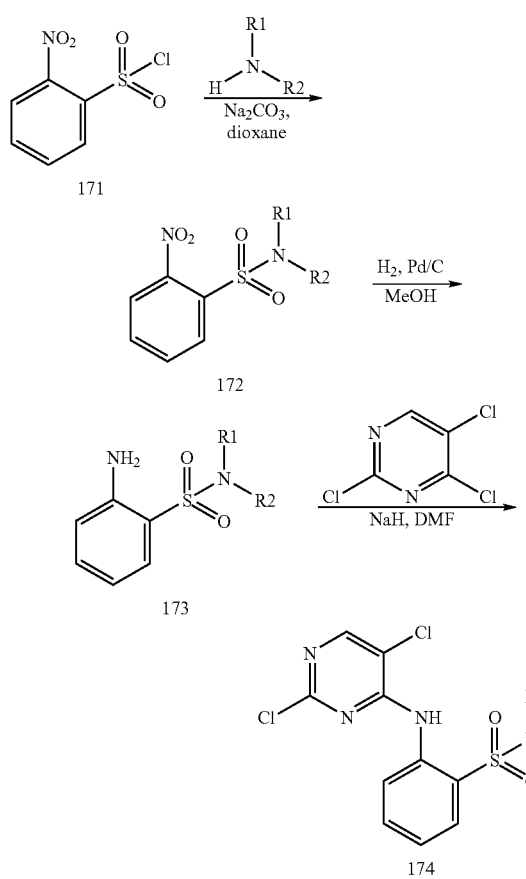

Compounds of formula 2 in which the ring system is (2,5-Dichloro-pyrimidin-4-yl)-(2-Alyklsulfonyl-phenyl)-amine can be prepared analogous to the sequence in Scheme 34. Displacement of compounds of formula 175 with an appropriate thiol, followed by oxidation to the sulfone, reduction and addition to trichloropyrimidine will give compounds of formula 177.

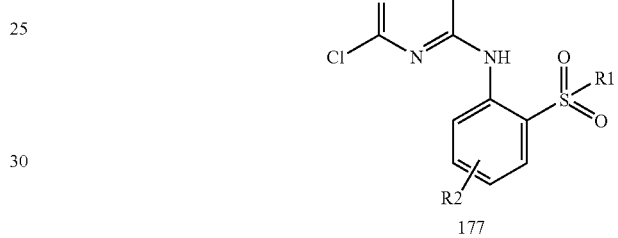

Compounds of formula 2 in which the ring system is a substituted (2,5-Dichloro-pyrimidin-4-yl)-pyridin-3-yl-amine can be prepared analogous to sequence outlined in Scheme 35. Displacement the chlorine in compounds of formula 178 with an appropriate nucleophile ($Nu^1H$) followed by reduction or another Nucleophile addition provides the aniline of formula 179 which upon addition to trichloropyrimidine gives compounds of formula 180.

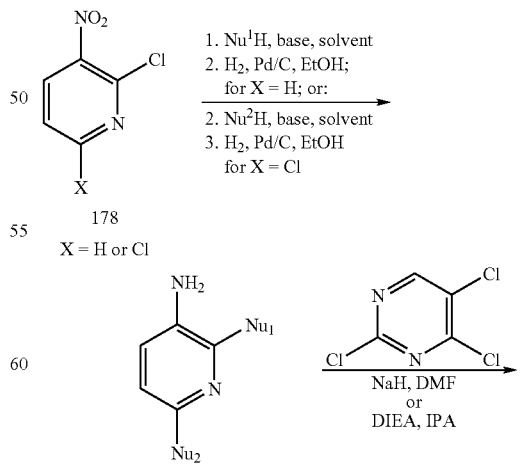

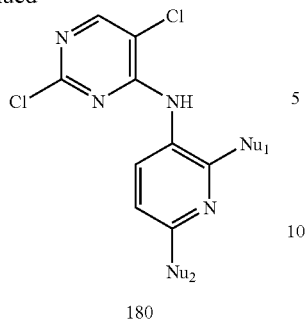

180

Compounds of formula 1 or 3 in which the ring system is 6,7-Dihydro-9H-5-oxa-9-aza-benzocyclohepten-8-one or 7-Methyl-3,4-dihydro-2H-benzo[f][1,4]oxazepin-5-one (Scheme 36) can be prepared from compounds of formula 181 by a Schmidt reaction and reduction to give compounds of formula 184 and 185. Appropriate substitution can be installed using methods to one skilled in the art.

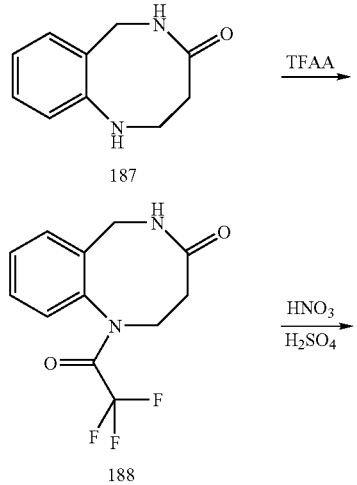

Scheme 36

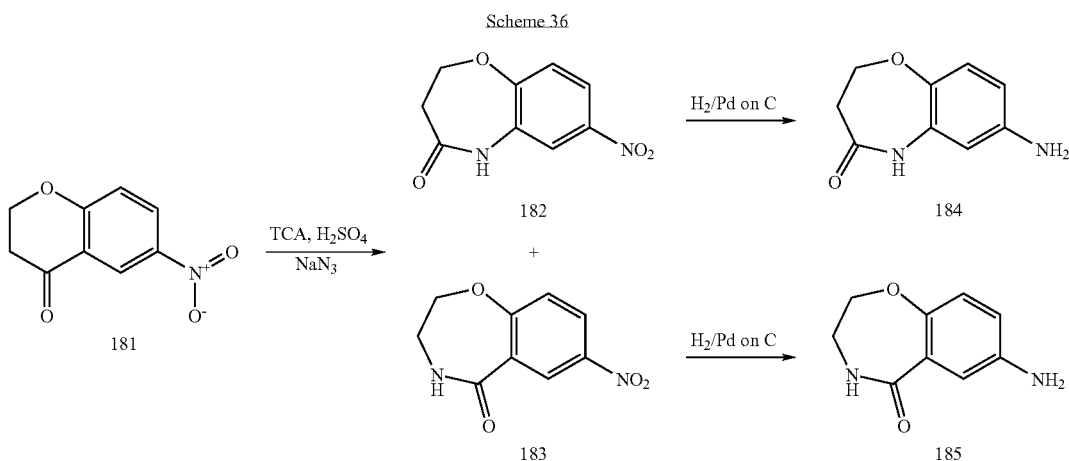

Compounds of formula 1 or 3 in which the ring system is 8-Amino-2,3,5,6-tetrahydro-1H-benzo[b][1,5]diazocin-4-one can be prepared analogous to a sequence in Scheme 37. Ring opening of azetidinone with compounds of formula 186 yields the 8-membered ring. Acylation, nitration and then deprotection, functionalization followed by reduction affords compounds of formula 191.

Scheme 37

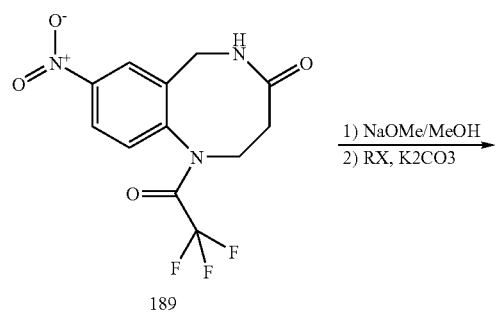

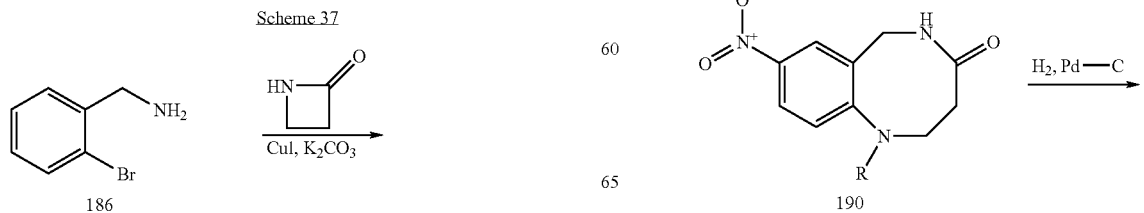

223
-continued

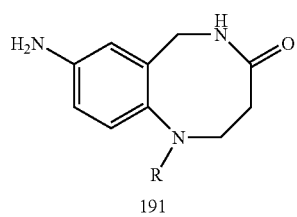

191

Compounds of formula 1 or 3 in which the ring system is 9-Amino-6-oxa-10b-aza-benzo[e]azulen-4-one or 4,5-Dihydro-6-oxa-10b-aza-benzo[e]azulen-9-ylamine can be prepared as outlined in Scheme 38. Protection of the aniline of compound of formula 192 as the pyrrole followed by alkylation and saponification provides compounds of formula 195. Cyclization with PCl$_5$ and reduction provides the compounds of formula 197 and 198.

Scheme 38

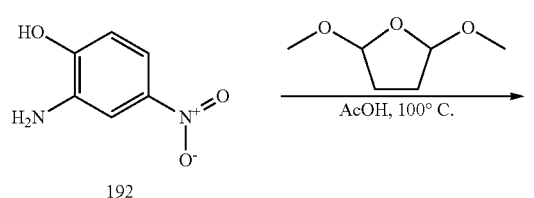

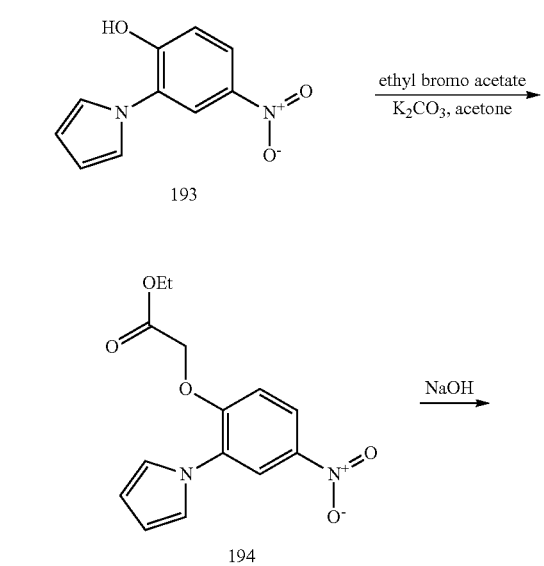

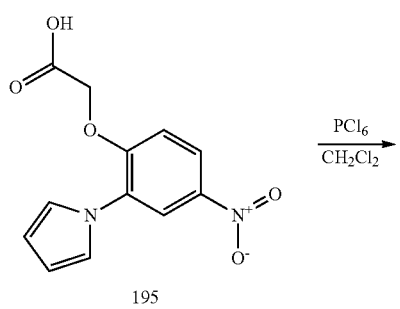

224
-continued

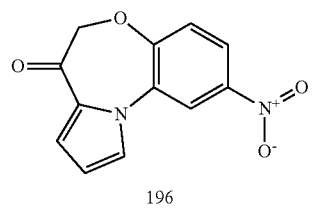 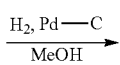

196

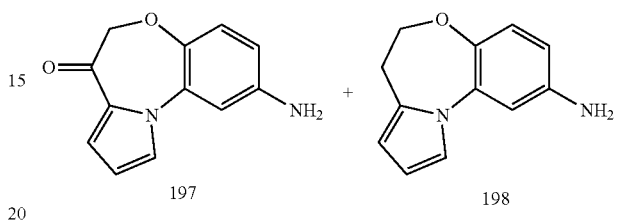

197    198

Compounds of formula 1 or 3 that have the ring system 3-Amino-1,3,4,5-tetrahydro-benzo[b]azepin-2-one (Scheme 39) can be prepared from compounds of formula 199 via iodination and displacement with Azide to give compounds of formula 201. Reduction and functionalization followed by nitro reduction gives compounds of formula 204.

Scheme 39

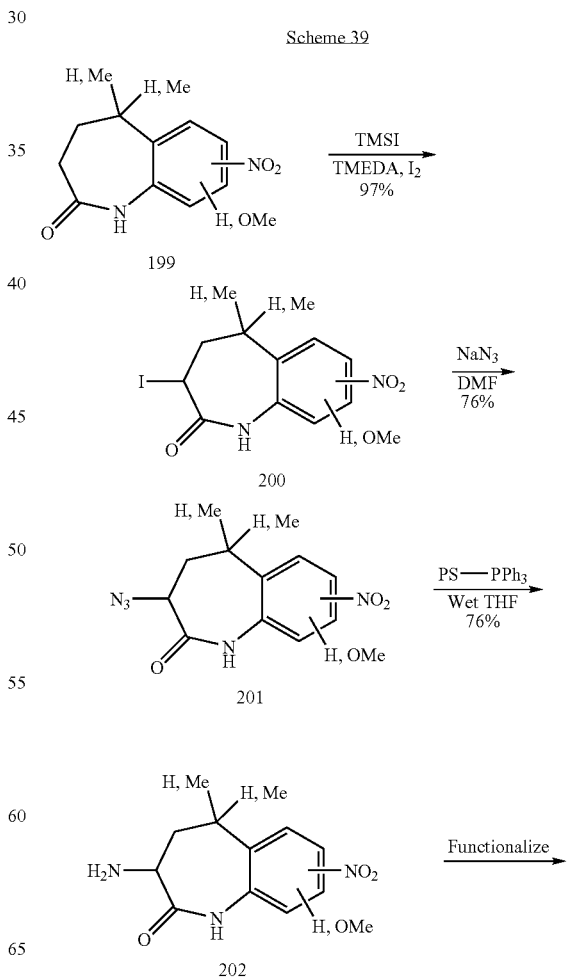

-continued

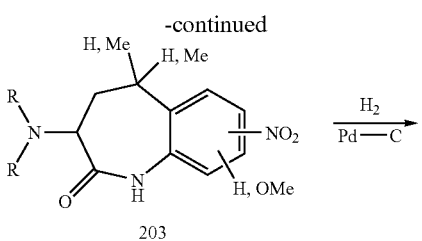

203

R = Acyl, H, Alkyl, Sulfonyl, carabamoyl, ureido, thioureido

204

Compounds of formula 1 or 3 containing the ring system 2-Amino-8,9-dihydro-5H-7-oxa-5-aza-benzocyclohepten-6-one (Scheme 40) can be prepared from compounds of formula 205, by ring formation with oxalyl chloride, nitration, functionalization and reduction to give compounds of formula 209.

Scheme 40

205

206

207

208

209

Compounds of formula 2 in which the ring system is a heteroarylamido system are outlined in Scheme 41. The carboxylate of formula 210 can be esterified and then nitrated to give compound of formula 212. Reduction and addition to trichloropyrimidine gives compounds of formula 214.

Scheme 41

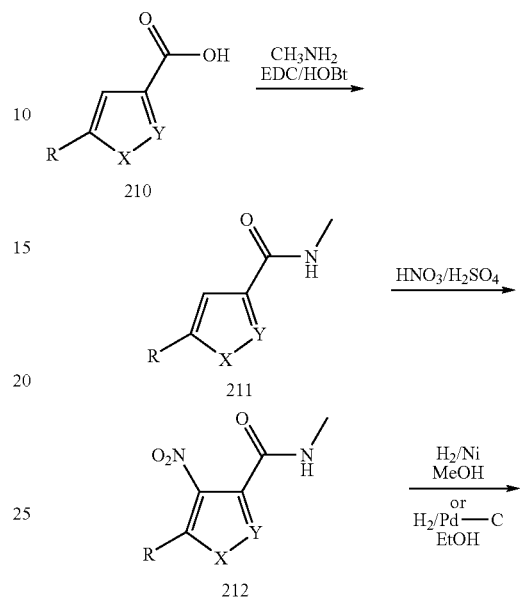

210

211

212

213

214

X = O, S, NAlkyl
Y = N, CH

Compounds of formula 1 or 3 in which the ring system is 5,6-Dihydro-4H-3,10b-diaza-benzo[e]azulene can be prepared from compounds of formula 215 by forming the BOC derivative, then the thioamide with Lawesson's reagent followed by S-alkylation. Condensation and cyclization provides compounds of formula 220.

Scheme 42

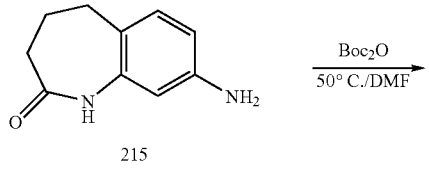

215

227
-continued

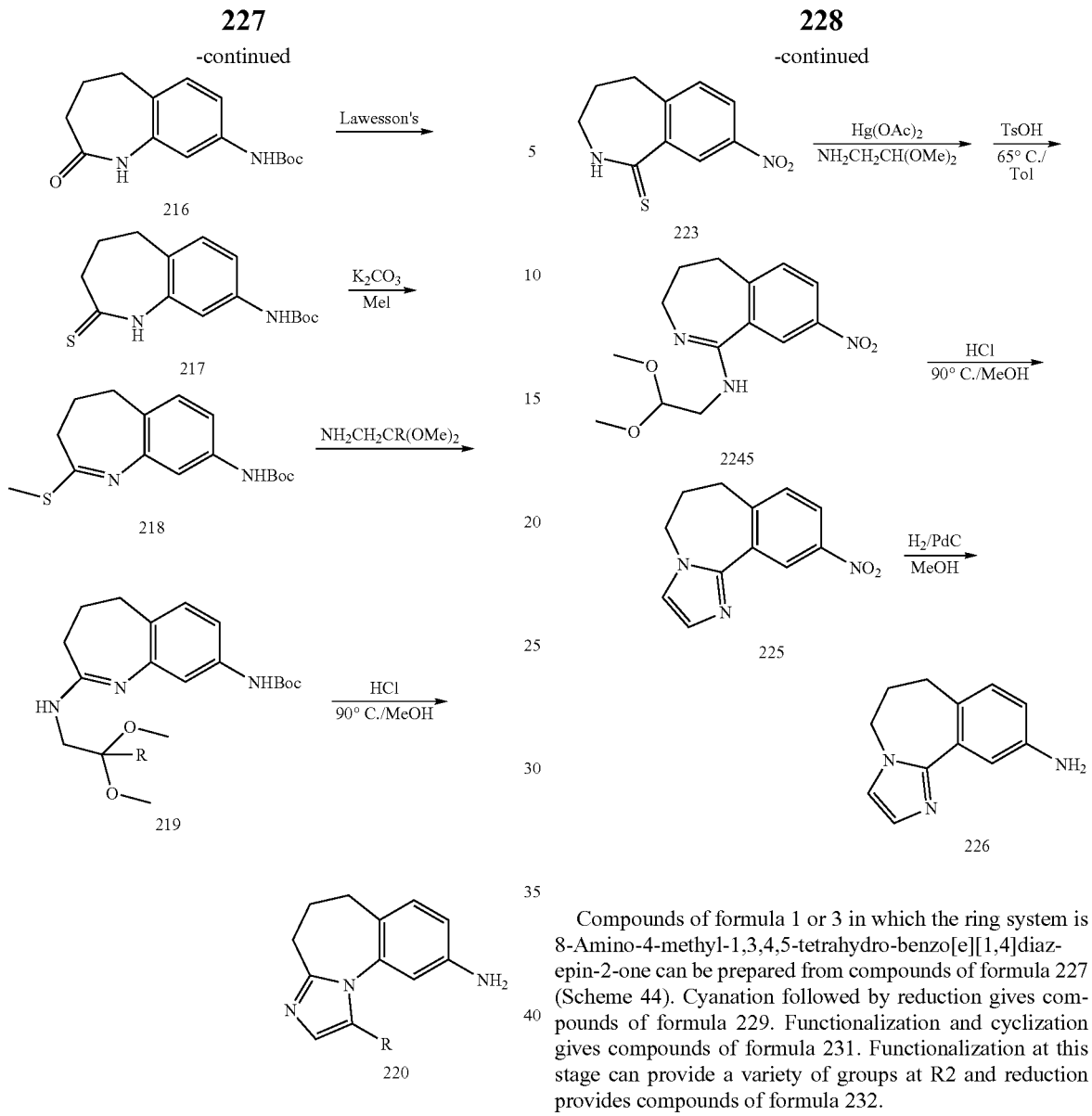

A similar sequence with the regioisomeric lactam of formula 221 can be used to prepare compounds of formula 226 with a 5,6-Dihydro-4H-1,3a-diaza-benzo[e]azulene ring system (Scheme 43) in the series of formula 1 or 3.

Scheme 43

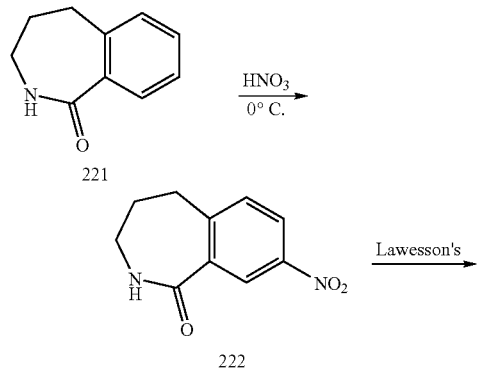

228
-continued

Compounds of formula 1 or 3 in which the ring system is 8-Amino-4-methyl-1,3,4,5-tetrahydro-benzo[e][1,4]diazepin-2-one can be prepared from compounds of formula 227 (Scheme 44). Cyanation followed by reduction gives compounds of formula 229. Functionalization and cyclization gives compounds of formula 231. Functionalization at this stage can provide a variety of groups at R2 and reduction provides compounds of formula 232.

Scheme 44

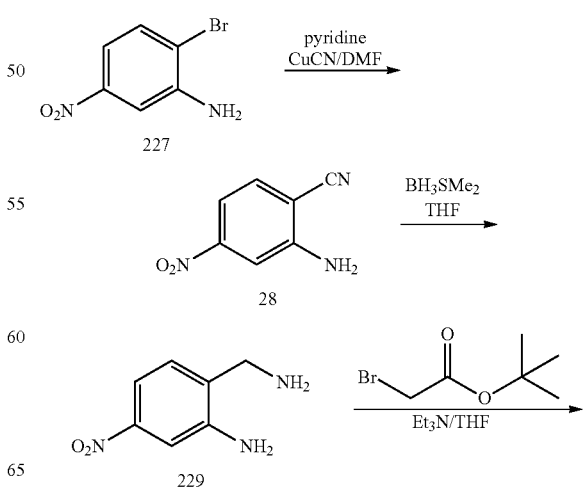

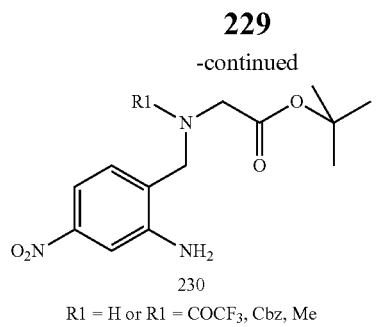
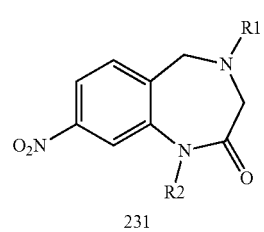
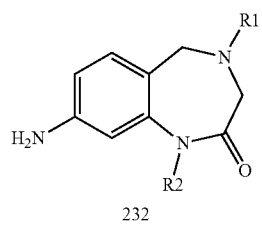

Compounds of formula 1 or 3 in which the ring system is 8-Amino-1,2,4,5-tetrahydro-benzo[e][1,4]diazepin-3-one (Scheme 45) can be prepared following the sequence from compounds of formula 233. Displacement with of the fluorine with glycine methylester followed by acylation, reduction and reductive cyclization gives compounds of formula 237.

Scheme 45

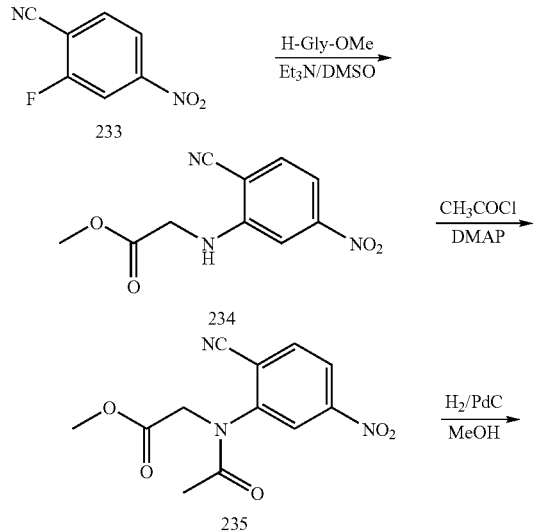

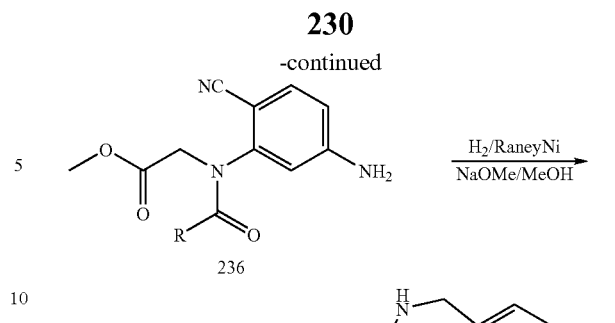

Compounds of formula 1 or 3 in which the ring system is 3-Amino-8,9-dihydro-5H-7-oxa-5-aza-benzocyclohepten-6-one can be prepared following the sequence outlined in Scheme 46 starting from compounds of formula 238. Esterification followed by homologation gives compounds of formula 239. Reduction of the nitro to the aniline and cyclization gives compounds of formula 242. Functionalization of the urethane nitrogen and a Curtius rearrangement yields the compounds of formula 246.

Scheme 46

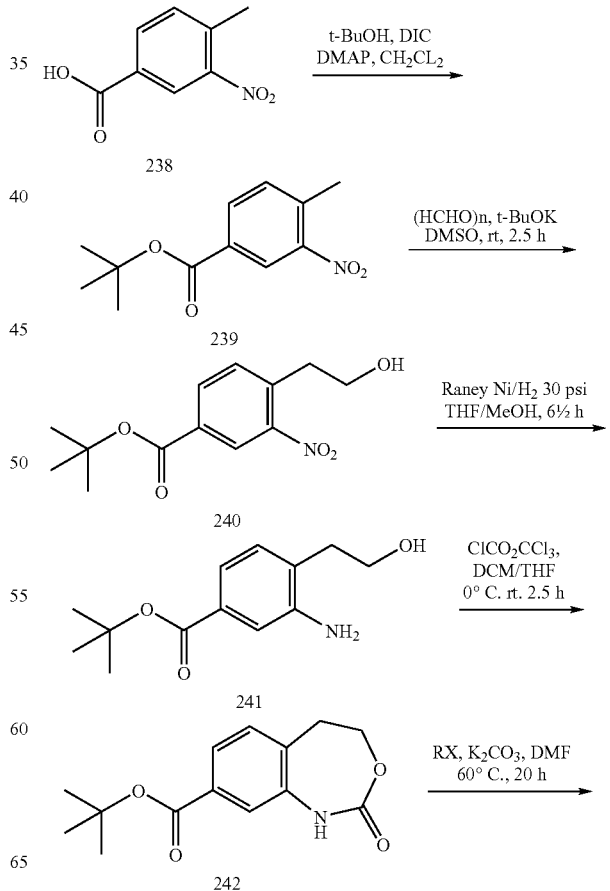

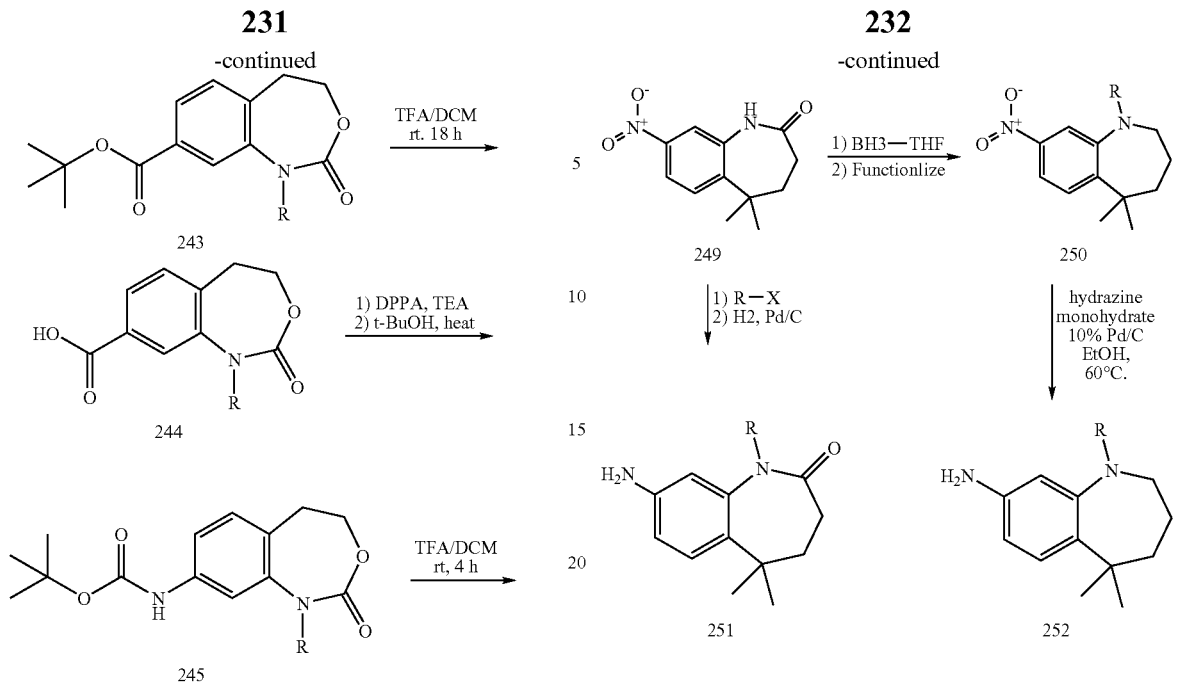

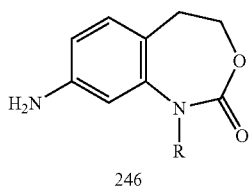

246

Compounds of formula 1 or 3 in which the ring system is 8-Amino-5,5-dimethyl-1,3,4,5-tetrahydro-benzo[b]azepin-2-one and 5,5-Dimethyl-2,3,4,5-tetrahydro-1H-benzo[b]azepin-8-ylamine can be prepared via nitration of tetralone of formula 247, followed by Beckman rearrangement to give the 7-membered lactam. Functionalization and reduction of the nitro gives compounds of formula X251 The lactam can be reduced to give compounds of formula 250 which follow a similar sequence to give compounds of formula 252.

Compounds of formula 1 or 3 in which the ring system is a methoxy substituted 1,3,4,5-Tetrahydro-benzo[e][1,4]diazepin-2-one can be prepared following a sequence outlined in Scheme 48. Reductive amination with compounds of formula 253, followed by saponification and cyclization compounds of formula 255. Schmidt ring expansion and nitration provides separable regioisomeric derivatives of formula 258 and 259 which can be manipulated through standard functional group transformations to give compounds of formula 260 and 261.

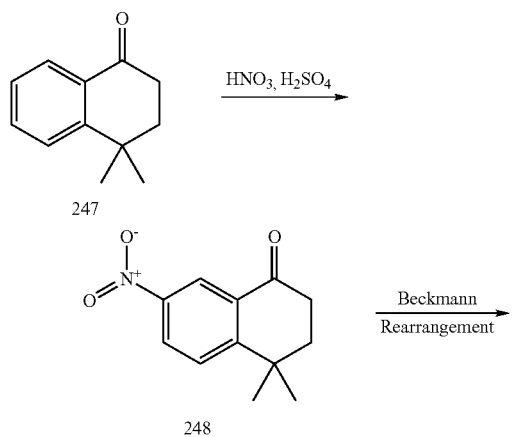

Scheme 47

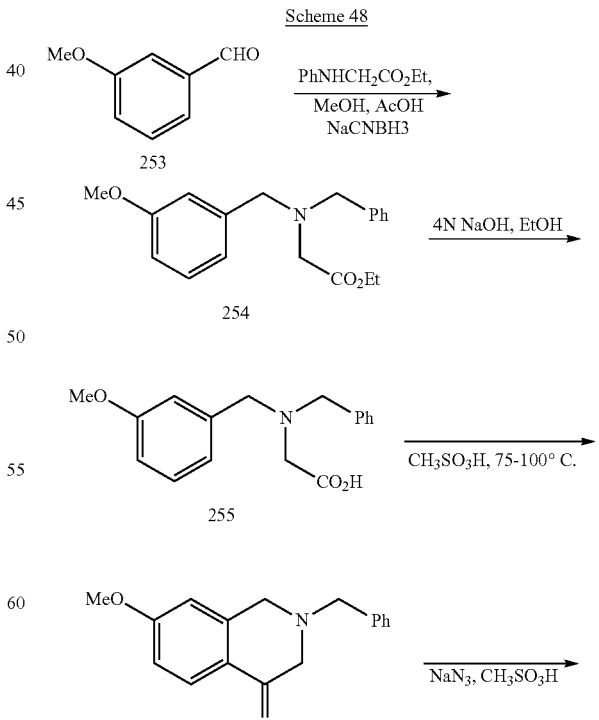

Scheme 48

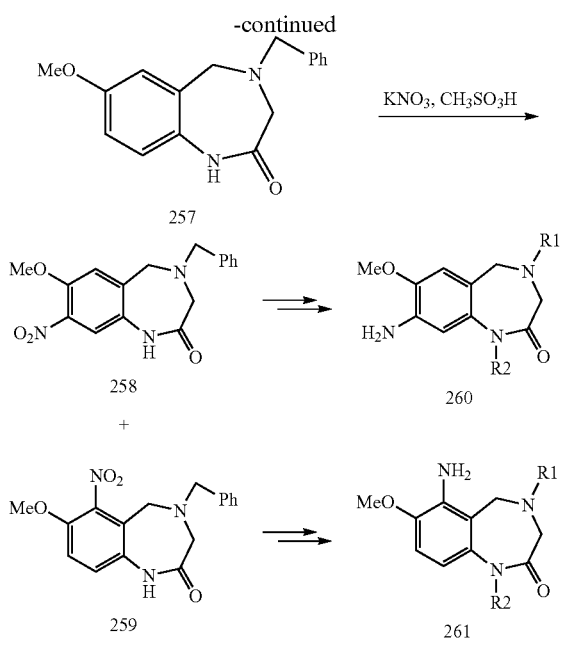

Compounds of formula 1 or 3 in which the ring system is substituted 6,7,8,9-Tetrahydro-5-oxa-9-aza-benzocycloheptene can be prepared from compounds of formula 262 via reduction and then Mitsunobu displacement and alkylative cyclization to give compounds of formula 264.

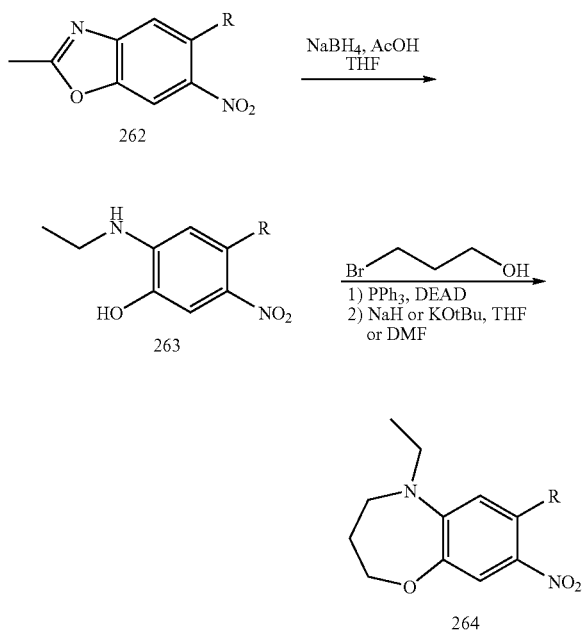

Compounds of formula 1 or 3 that contain the ring system 6,7,8,9-Tetrahydro-5-oxa-9-aza-benzocyclohepten-7-ylamine (Scheme 50) can be prepared by bis-alkylation of compounds of formula 265. Oxidative cleavage to the ketone and reductive amination gives compounds of formula 268 which after standard manipulation gives compounds of formula 269.

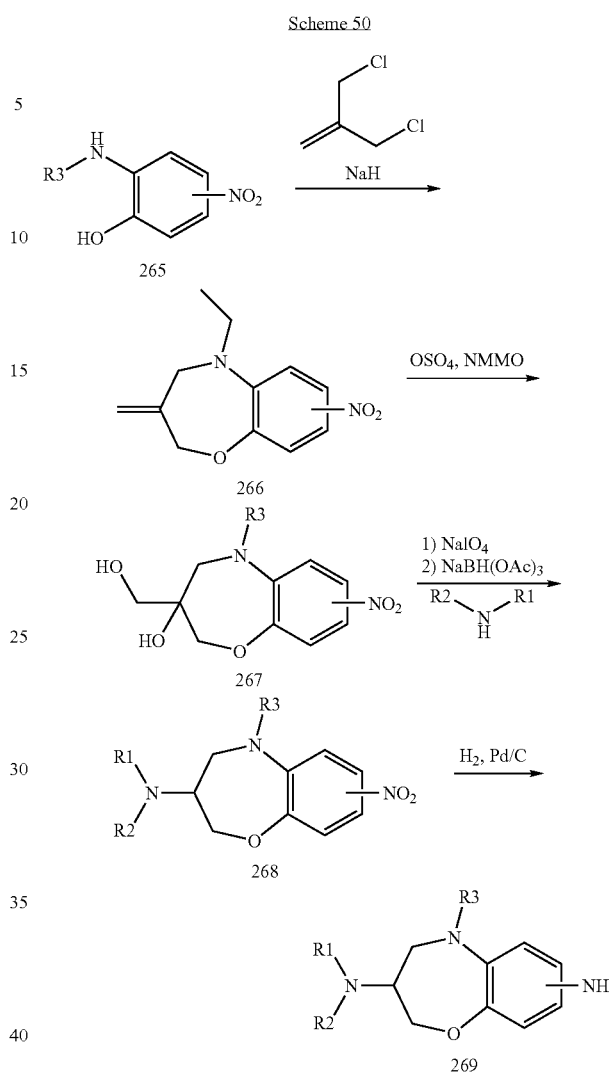

VI. Biology

ALK Kinase Assay

Example compounds were tested for their ability to inhibit the kinase activity of baculovirus-expressed ALK using a modification of the ELISA protocol reported for trkA in Angeles, T. S. et al., *Anal. Biochem.* 1996, 236, 49-55, which is incorporated herein by reference in its entirety. Phosphorylation of the substrate, phospholipase C-gamma (PLC-γ) generated as a fusion protein with glutathione S-transferase (GST) as reported in Rotin, D. et al., *EMBO J.* 1992, 11, 559-567, which is incorporated herein by reference in its entirety, was detected with a europium-labeled anti-phosphotyrosine antibody and measured by time-resolved fluorescence (TRF). Briefly, each 96-well plate was coated with 100 μL/well of 10 μg/mL substrate (phospholipase C-γ) in Tris-buffered saline (TBS). The assay mixture (total volume=100 μL/well) consisting of 20 mM HEPES (pH 7.2), 1 μM ATP ($K_m$ level), 5 mM $MnCl_2$, 0.1% BSA, 2.5% DMSO, and various concentrations of test compound was then added to the assay plate. The reaction was initiated by adding enzyme (30 ng/ml ALK) and was allowed to proceed at 37° C. for 15 minutes. Detection of the phosphorylated product was performed by adding 100 μl/well of Eu-N1 labeled PT66 antibody (Perkin Elmer # AD0041). Incubation at 37° C. then proceeded for one (1) hour, followed by addition of 100 μL enhancement solution (Wallac #1244-105). The plate was gently agitated and after thirty minutes, the fluorescence of the resulting solution was measured using the EnVision 2100 (or 2102) multilabel plate reader (Perkin Elmer).

Data analysis was performed using ActivityBase (IDBS, Guilford, UK). $IC_{50}$ values were calculated by plotting percent inhibition versus $log_{10}$ of the concentration of compound and fitting to the nonlinear regression sigmoidal dose-response (variable slope) equation in XLFit (IDBS, Guilford, UK).

c-Met Kinase Assay

The kinase activity of c-Met was evaluated using the same methods as for ALK, with the following modifications: Plates were coated with 20 μg/mL phospholipase C-γ and the assay mixture consisted of 50 mM HEPES (pH 7.2), 50 mM NaCl, 1 μM ATP ($K_m$ level), 4 mM $MnCl_2$, 0.01% TritonX-100, 0.02% BSA, 2.5% DMSO. Reactions were initiated with 10 ng/mL c-Met (cytoplasmic domain, Invitrogen Corporation #PV3143).

Results

Biological data for the Example compounds is presented in the following Table 1.

TABLE 1

ALK, c-Met Kinase Inhibition

| Example | ALK Activity | cMet Activity |
|---|---|---|
| 1 | ++++ | ++++ |
| 2 | ++++ | ++++ |
| 3 | ++++ | ++ |
| 4 | ++++ | ++++ |
| 5 | ++++ | ++++ |
| 6 | ++++ | ++++ |
| 7 | ++++ | ++++ |
| 8 | ++++ | ++++ |
| 9 | ++++ | ++++ |
| 10 | ++++ | ++++ |
| 11 | ++++ | ++++ |
| 12 | ++++ | ++++ |
| 13 | ++++ | ++ |
| 14 | ++++ | ++++ |
| 15 | ++++ | ++++ |
| 16 | ++++ | ++++ |
| 17 | ++++ | ++++ |
| 18 | ++++ | ++ |
| 19 | ++++ | ++++ |
| 20 | ++++ | +++ |
| 31 | ++++ | ++++ |
| 32 | ++++ | ++++ |
| 33 | ++++ | ++++ |
| 34 | ++++ | ++++ |
| 35 | ++++ | +++ |
| 36 | ++++ | ++ |
| 37 | ++++ | ++ |
| 38 | ++++ | ++++ |
| 39 | ++++ | +++ |
| 40 | ++++ | ++ |
| 41 | ++++ | ++++ |
| 42 | ++++ | ++++ |
| 43 | ++++ | ++++ |
| 44 | ++++ | ++++ |
| 45 | ++++ | ++++ |
| 46 | ++++ | ++++ |
| 47 | ++++ | ++++ |
| 48 | ++++ | ++ |
| 49 | ++++ | + |
| 50 | ++++ | + |
| 51 | ++++ | ++++ |
| 61 | ++++ | +++ |
| 62 | ++++ | +++ |
| 63 | +++ | ++++ |
| 64 | +++ | ++++ |
| 65 | +++ | +++ |
| 66 | ++++ | ++ |
| 67 | ++++ | ++++ |
| 68 | ++++ | ++++ |
| 69 | ++++ | ++++ |
| 70 | ++++ | ++++ |
| 71 | ++++ | +++ |
| 72 | ++++ | +++ |
| 73 | ++++ | +++ |
| 74 | +++ | + |
| 75 | ++++ | ++ |
| 76 | ++++ | +++ |
| 77 | ++++ | +++ |
| 78 | ++++ | +++ |
| 79 | ++++ | ++++ |
| 80 | ++++ | ++++ |
| 81 | ++++ | +++ |
| 82 | ++ | +++ |
| 83 | ++++ | +++ |
| 84 | ++++ | +++ |
| 85 | ++++ | +++ |
| 86 | ++++ | +++ |
| 87 | ++++ | +++ |
| 88 | ++++ | ++ |
| 89 | ++++ | +++ |
| 90 | +++ | ++++ |
| 91 | +++ | ++++ |
| 92 | ++ | + |
| 93 | + | + |
| 101 | ++++ | ++++ |
| 102 | ++++ | ++++ |
| 103 | ++++ | ++++ |
| 104 | ++++ | +++ |
| 105 | ++++ | + |
| 106 | ++++ | +++ |
| 107 | ++++ | +++ |
| 108 | ++++ | ++++ |
| 109 | ++++ | ++ |
| 110 | ++++ | +++ |
| 111 | ++++ | + |
| 112 | ++++ | + |
| 113 | ++++ | + |
| 114 | + | + |
| 115 | ++++ | + |
| 116 | ++++ | ++ |
| 117 | ++++ | + |
| 118 | ++++ | + |
| 119 | ++++ | + |
| 120 | ++++ | + |
| 121 | ++++ | + |
| 122 | ++++ | ++ |
| 123 | +++ | + |
| 124 | ++++ | + |
| 125 | ++++ | + |
| 126 | ++++ | ++ |
| 127 | ++++ | + |
| 128 | ++++ | + |
| 129 | ++++ | + |
| 130 | ++++ | + |
| 131 | ++++ | + |
| 132 | ++ | + |
| 133 | ++++ | + |
| 134 | ++++ | ++ |
| 135 | ++++ | + |
| 136 | ++++ | + |
| 137 | +++ | + |
| 138 | ++++ | ++ |
| 139 | ++++ | + |
| 140 | ++++ | + |
| 141 | +++ | + |
| 142 | ++++ | + |
| 143 | ++++ | + |

TABLE 1-continued

ALK, c-Met Kinase Inhibition

| Example | ALK Activity | cMet Activity |
|---|---|---|
| 144 | ++++ | ++ |
| 145 | ++++ | ++ |
| 146 | ++++ | +++ |
| 151 | ++++ | + |
| 152 | ++++ | ++ |
| 153 | ++ | ++ |
| 154 | +++ | + |
| 155 | ++++ | + |
| 156 | ++++ | ++++ |
| 157 | ++++ | ++ |
| 158 | ++++ | +++ |
| 159 | ++++ | +++ |
| 160 | +++ | ++ |
| 161 | ++++ | +++ |
| 162 | ++++ | ++ |
| 163 | ++++ | ++ |
| 164 | +++ | ++++ |
| 165 | +++ | ++ |
| 166 | ++++ | ++ |
| 171 | ++ | ++ |
| 172 | ++++ | ++++ |
| 173 | ++++ | +++ |
| 174 | ++++ | +++ |
| 175 | ++++ | ++ |
| 176 | +++ | ++ |
| 177 | ++++ | +++ |
| 178 | ++++ | ++++ |
| 179 | ++++ | +++ |
| 180 | ++++ | +++ |
| 181 | ++++ | ++ |
| 182 | +++ | + |
| 183 | ++++ | ++++ |
| 191 | ++++ | ++++ |
| 192 | ++++ | ++++ |
| 193 | ++++ | +++ |
| 194 | ++++ | +++ |
| 195 | ++++ | ++++ |
| 196 | ++++ | ++++ |
| 197 | ++++ | ++++ |
| 198 | ++++ | ++ |
| 199 | ++++ | ++ |
| 200 | ++++ | +++ |
| 211 | +++ | ++ |
| 212 | ++ | ++ |
| 213 | ++ | + |
| 214 | +++ | ++ |
| 215 | + | + |
| 216 | ++++ | +++ |
| 217 | ++++ | +++ |
| 218 | ++++ | +++ |
| 219 | +++ | + |
| 220 | ++++ | ++ |
| 221 | ++++ | +++ |
| 222 | ++++ | ++ |
| 223 | ++++ | + |
| 224 | ++++ | +++ |
| 225 | ++++ | ++ |
| 226 | ++++ | ++ |
| 227 | ++++ | ++++ |
| 228 | ++++ | +++ |
| 229 | + | + |
| 230 | ++++ | ++ |
| 231 | +++ | ++ |
| 232 | ++++ | + |
| 233 | ++++ | + |
| 234 | ++++ | + |
| 235 | ++++ | ++ |
| 236 | +++ | ++ |
| 241 | ++++ | +++ |
| 242 | ++++ | ++ |
| 243 | ++++ | + |
| 244 | ++ | + |
| 245 | ++ | + |
| 246 | ++ | + |
| 247 | ++++ | + |
| 248 | ++++ | + |
| 249 | ++++ | + |
| 250 | ++++ | + |
| 251 | ++++ | + |
| 252 | ++++ | + |
| 253 | ++++ | ++ |
| 254 | ++++ | + |
| 255 | ++++ | + |
| 256 | ++++ | + |
| 257 | ++++ | + |
| 258 | ++++ | + |
| 259 | ++++ | +++ |
| 260 | ++++ | + |
| 261 | ++++ | + |
| 262 | ++++ | ++ |
| 263 | ++++ | + |
| 264 | ++++ | ++ |
| 265 | ++++ | +++ |
| 271 | ++++ | ++++ |
| 272 | ++++ | +++ |
| 273 | ++++ | ++++ |
| 274 | ++++ | ++++ |
| 275 | ++++ | ++++ |
| 276 | +++ | ++++ |
| 277 | ++++ | ++++ |
| 278 | ++++ | ++++ |
| 279 | ++++ | ++++ |
| 280 | ++++ | ++++ |
| 281 | ++++ | ++++ |
| 282 | ++++ | ++++ |
| 283 | ++++ | ++++ |
| 284 | ++++ | +++ |
| 285 | ++++ | ++++ |
| 286 | ++++ | ++++ |
| 287 | ++++ | +++ |
| 288 | ++++ | +++ |
| 289 | ++++ | +++ |
| 290 | +++ | + |
| 291 | ++++ | ++ |
| 292 | ++++ | ++ |
| 293 | ++++ | ++ |
| 294 | ++++ | +++ |
| 295 | ++++ | +++ |
| 296 | ++++ | +++ |
| 297 | +++ | + |
| 298 | +++ | ++ |
| 299 | +++ | ++ |
| 300 | +++ | ++ |
| 301 | +++ | ++ |
| 302 | ++++ | ++ |
| 303 | +++ | ++ |
| 304 | +++ | ++ |
| 305 | +++ | + |
| 306 | +++ | + |
| 307 | ++ | + |
| 308 | ++++ | ++++ |
| 309 | ++++ | +++ |
| 310 | ++++ | +++ |
| 311 | ++++ | ++++ |
| 312 | +++ | ++++ |
| 313 | +++ | ++++ |
| 314 | +++ | ++++ |
| 315 | +++ | +++ |
| 316 | ++++ | +++ |
| 317 | +++ | +++ |
| 318 | ++ | + |
| 319 | +++ | + |
| 320 | ++++ | ++ |
| 321 | ++++ | +++ |
| 322 | ++++ | ++++ |
| 323 | ++++ | +++ |
| 324 | ++++ | ++ |
| 325 | ++++ | +++ |
| 326 | ++++ | +++ |
| 327 | ++++ | ++++ |

TABLE 1-continued

ALK, c-Met Kinase Inhibition

| Example | ALK Activity | cMet Activity |
|---|---|---|
| 328 | ++++ | ++++ |
| 329 | ++++ | ++ |
| 330 | ++++ | + |
| 331 | ++++ | +++ |
| 332 | ++++ | ++++ |
| 333 | ++++ | ++ |
| 334 | ++++ | +++ |
| 335 | ++++ | ++++ |
| 336 | ++++ | +++ |
| 337 | ++++ | + |
| 338 | ++++ | +++ |
| 339 | ++++ | ++++ |
| 340 | ++++ | +++ |
| 341 | ++++ | +++ |
| 342 | ++++ | +++ |
| 343 | ++++ | ++++ |
| 344 | ++++ | +++ |
| 345 | ++++ | ++++ |
| 351 | ++++ | ++++ |
| 352 | ++ | ++++ |
| 353 | ++ | ++ |
| 354 | ++++ | ++++ |
| 355 | ++++ | +++ |
| 356 | ++++ | ++++ |
| 357 | ++ | ++++ |
| 358 | ++++ | ++++ |
| 359 | ++++ | ++++ |
| 360 | ++ | ++++ |
| 361 | ++ | ++++ |
| 362 | ++++ | ++++ |
| 371 | +++ | ++ |
| 372 | ++++ | +++ |
| 373 | ++++ | + |
| 374 | +++ | + |
| 375 | ++++ | + |
| 376 | ++++ | ++ |
| 381 | ++++ | ++++ |
| 382 | +++ | +++ |
| 383 | ++++ | ++ |
| 384 | ++++ | ++++ |
| 385 | ++++ | +++ |
| 386 | ++++ | +++ |
| 387 | ++++ | ++++ |
| 388 | ++++ | ++ |
| 389 | +++ | +++ |
| 390 | ++++ | ++++ |
| 391 | ++++ | + |
| 392 | ++++ | ++ |
| 393 | ++++ | + |
| 394 | ++++ | +++ |
| 395 | ++++ | +++ |
| 396 | ++++ | ++++ |
| 397 | ++++ | +++ |
| 398 | ++++ | + |
| 399 | +++ | +++ |
| 400 | +++ | +++ |
| 401 | + | +++ |
| 411 | ++++ | ++++ |
| 412 | ++++ | ++++ |
| 413 | ++++ | ++++ |
| 414 | ++++ | ++++ |
| 415 | ++++ | +++ |
| 416 | ++++ | ++++ |
| 417 | ++++ | ++++ |
| 418 | ++++ | ++++ |
| 419 | ++++ | ++++ |
| 420 | ++++ | ++++ |
| 421 | ++++ | +++ |
| 422 | ++++ | ++ |
| 423 | ++++ | +++ |
| 424 | ++++ | ++ |
| 425 | ++++ | +++ |
| 426 | ++++ | +++ |
| 427 | ++++ | + |
| 428 | ++++ | ++++ |
| 429 | ++++ | +++ |
| 430 | ++++ | ++ |
| 431 | ++++ | ++ |
| 432 | ++++ | ++++ |
| 441 | ++++ | +++ |
| 442 | ++++ | ++ |
| 443 | ++++ | ++ |
| 444 | ++++ | ++ |
| 445 | ++++ | ++++ |
| 446 | ++++ | +++ |
| 447 | +++ | +++ |
| 448 | ++++ | ++++ |
| 449 | ++++ | +++ |
| 450 | ++++ | +++ |
| 451 | +++ | ++ |
| 452 | ++++ | ++ |
| 453 | ++++ | ++ |
| 454 | +++ | ++ |
| 455 | +++ | ++ |
| 456 | ++++ | ++++ |
| 457 | +++ | +++ |
| 459 | ++++ | ++ |
| 460 | +++ | ++++ |
| 461 | ++++ | + |
| 462 | ++++ | + |
| 471 | ++++ | ++ |
| 472 | ++++ | +++ |
| 473 | ++++ | +++ |
| 474 | ++++ | +++ |
| 475 | ++++ | ++ |
| 476 | ++++ | ++ |
| 477 | ++++ | ++ |
| 478 | ++++ | ++ |
| 479 | ++++ | ++ |
| 480 | ++++ | ++ |
| 481 | ++++ | ++ |
| 482 | ++++ | +++ |
| 483 | ++++ | ++++ |
| 484 | ++++ | ++++ |
| 485 | ++++ | ++++ |
| 486 | ++++ | ++++ |
| 487 | ++++ | ++++ |
| 488 | ++++ | ++++ |
| 489 | ++++ | ++++ |
| 490 | ++++ | + |
| 491 | ++++ | + |
| 492 | ++++ | + |
| 493 | ++++ | + |
| 494 | ++++ | + |
| 495 | ++++ | + |
| 496 | ++++ | + |
| 497 | +++ | ++ |
| 498 | +++ | + |
| 499 | +++ | +++ |
| 511 | ++++ | ++++ |
| 512 | ++++ | ++++ |
| 513 | ++++ | ++++ |
| 514 | ++++ | ++++ |
| 515 | ++++ | ++++ |
| 516 | ++++ | ++++ |
| 517 | ++++ | ++++ |
| 518 | ++++ | ++ |
| 519 | ++++ | ++ |
| 520 | +++ | ++ |
| 521 | ++++ | ++ |
| 522 | ++++ | +++ |
| 523 | +++ | ++ |
| 524 | ++++ | ++ |
| 525 | +++ | ++ |
| 526 | ++++ | ++ |
| 527 | ++++ | ++++ |
| 528 | ++++ | ++++ |
| 541 | +++ | + |
| 542 | ++++ | + |
| 543 | ++ | + |

TABLE 1-continued

ALK, c-Met Kinase Inhibition

| Example | ALK Activity | cMet Activity |
|---|---|---|
| 544 | ++++ | + |
| 545 | ++ | + |
| 601 | ++++ | + |
| 602 | +++ | + |
| 603 | +++ | + |
| 604 | ++++ | + |
| 605 | ++++ | + |
| 606 | ++++ | + |
| 607 | ++++ | ++ |
| 608 | ++ | + |
| 609 | ++++ | +++ |
| 610 | ++ | + |
| 611 | ++++ | ++ |
| 612 | ++++ | + |
| 613 | ++++ | + |
| 614 | ++++ | + |
| 615 | ++++ | +++ |
| 616 | ++++ | + |
| 617 | ++++ | ++ |
| 618 | ++++ | ++++ |
| 619 | ++++ | +++ |
| 620 | ++++ | +++ |
| 621 | ++++ | ++ |
| 622 | ++++ | ++ |
| 623 | ++++ | ++ |
| 624 | ++++ | +++ |
| 625 | ++++ | +++ |
| 626 | ++++ | + |
| 627 | ++++ | ++ |
| 628 | ++++ | ++ |
| 629 | ++++ | ++ |
| 630 | ++++ | + |
| 631 | ++++ | + |
| 632 | +++ | + |
| 633 | ++++ | + |
| 634 | ++++ | + |
| 635 | ++++ | + |
| 636 | ++++ | + |
| 637 | ++++ | ++ |
| 638 | ++++ | ++++ |
| 639 | ++++ | ++++ |
| 640 | +++ | ++++ |
| 641 | ++++ | ++++ |
| 642 | ++++ | +++ |
| 651 | ++++ | ++++ |
| 652 | ++++ | + |
| 653 | ++++ | +++ |
| 654 | ++++ | +++ |
| 655 | ++++ | +++ |
| 656 | ++++ | +++ |
| 657 | +++ | + |
| 658 | +++ | + |
| 659 | ++++ | + |
| 660 | ++++ | ++++ |
| 661 | +++ | +++ |
| 662 | ++++ | +++ |
| 663 | ++++ | ++ |
| 664 | ++++ | ++++ |
| 665 | ++++ | +++ |
| 666 | +++ | ++ |
| 667 | ++++ | +++ |
| 668 | +++ | ++ |
| 669 | ++++ | ++++ |
| 670 | ++++ | ++ |
| 671 | ++++ | ++++ |
| 672 | +++ | ++ |
| 673 | +++ | ++ |
| 674 | ++++ | ++ |
| 675 | ++++ | + |
| 676 | ++++ | + |
| 677 | ++++ | + |
| 678 | ++++ | + |
| 679 | ++++ | + |
| 680 | ++++ | + |
| 681 | ++++ | +++ |
| 682 | ++++ | +++ |
| 683 | ++++ | + |
| 684 | ++++ | + |
| 685 | ++++ | + |
| 686 | ++++ | + |
| 687 | ++++ | + |
| 688 | +++ | + |
| 689 | ++++ | + |
| 690 | +++ | + |
| 691 | ++++ | + |
| 692 | ++++ | ++ |
| 693 | ++++ | + |
| 694 | ++++ | + |
| 695 | ++++ | ++ |
| 696 | ++++ | + |
| 697 | ++++ | ++ |
| 698 | ++++ | + |
| 699 | ++++ | + |
| 700 | ++++ | + |
| 701 | ++++ | + |
| 702 | ++++ | + |
| 703 | ++++ | +++ |
| 704 | ++++ | +++ |
| 705 | ++++ | + |
| 711 | ++++ | +++ |
| 712 | ++++ | ++ |
| 713 | ++++ | ++ |
| 714 | ++++ | ++ |
| 715 | ++++ | +++ |
| 716 | ++++ | ++++ |
| 717 | ++++ | ++ |
| 718 | ++++ | ++++ |
| 719 | ++++ | ++ |
| 720 | ++++ | ++ |
| 721 | ++++ | + |
| 722 | +++ | + |
| 723 | ++++ | + |
| 724 | ++++ | + |
| 725 | ++++ | +++ |
| 726 | +++ | + |
| 727 | +++ | + |
| 728 | ++++ | +++ |
| 729 | ++++ | ++ |
| 730 | ++++ | ++++ |
| 731 | ++++ | +++ |
| 732 | ++++ | ++ |
| 733 | ++++ | ++ |
| 734 | ++++ | + |
| 735 | ++++ | + |
| 736 | +++ | + |
| 737 | ++++ | + |
| 738 | ++++ | + |
| 739 | +++ | + |
| 740 | ++++ | + |
| 741 | ++++ | + |
| 742 | ++++ | + |
| 743 | ++++ | + |
| 744 | +++ | + |
| 745 | +++ | + |
| 746 | +++ | + |
| 747 | ++++ | + |
| 748 | ++++ | + |
| 749 | +++ | + |
| 750 | ++ | + |
| 751 | ++ | + |
| 761 | ++++ | + |
| 762 | ++++ | + |
| 763 | ++++ | + |
| 764 | ++++ | + |
| 765 | ++++ | + |
| 766 | ++++ | ++ |
| 767 | ++++ | + |
| 768 | +++ | + |
| 769 | +++ | + |
| 770 | ++++ | + |

TABLE 1-continued

ALK, c-Met Kinase Inhibition

| Example | ALK Activity | cMet Activity |
|---|---|---|
| 771 | ++++ | + |
| 772 | ++++ | + |
| 773 | ++++ | + |
| 774 | ++++ | + |
| 775 | ++++ | + |
| 776 | ++++ | + |
| 777 | ++++ | ++ |
| 778 | ++++ | + |
| 779 | ++++ | + |
| 780 | +++ | + |
| 781 | ++++ | + |
| 782 | ++++ | + |
| 783 | ++++ | + |
| 784 | ++++ | + |
| 785 | +++ | + |
| 786 | ++++ | + |
| 788 | ++++ | + |
| 789 | ++++ | ++ |
| 790 | ++++ | + |
| 792 | ++++ | + |
| 793 | ++++ | + |
| 794 | ++++ | + |
| 795 | ++++ | ++ |
| 796 | ++++ | + |
| 797 | ++++ | + |
| 798 | ++++ | + |
| 799 | ++++ | + |
| 800 | ++++ | + |
| 801 | ++++ | + |
| 802 | ++++ | + |
| 803 | ++++ | + |
| 804 | ++++ | + |
| 805 | ++++ | + |
| 806 | ++++ | + |
| 807 | ++++ | + |
| 808 | ++++ | + |
| 809 | ++++ | + |
| 810 | ++++ | + |
| 811 | +++ | + |
| 812 | ++++ | + |
| 813 | ++++ | + |
| 814 | ++++ | + |
| 815 | ++++ | + |
| 816 | ++++ | + |
| 817 | ++++ | + |
| 818 | ++++ | + |
| 819 | ++++ | + |
| 820 | ++++ | + |
| 821 | ++++ | + |
| 822 | ++++ | + |
| 823 | ++++ | + |
| 824 | ++++ | + |
| 825 | +++ | + |
| 826 | ++++ | + |
| 827 | ++++ | + |
| 828 | ++++ | + |
| 829 | ++++ | + |
| 830 | ++++ | + |
| 831 | ++++ | + |
| 832 | ++++ | + |
| 833 | ++++ | + |
| 834 | ++++ | + |
| 835 | ++++ | + |
| 836 | ++++ | + |
| 837 | ++++ | + |
| 838 | ++++ | + |
| 839 | ++++ | + |
| 840 | ++++ | + |
| 841 | ++++ | + |
| 842 | ++++ | + |
| 843 | ++++ | + |
| 844 | ++++ | ++ |
| 845 | ++++ | + |
| 846 | ++++ | + |
| 847 | +++ | + |
| 848 | +++ | + |
| 849 | ++++ | + |
| 850 | ++++ | +++ |
| 851 | ++++ | ++ |
| 852 | ++++ | ++ |
| 853 | ++++ | ++ |
| 854 | ++++ | +++ |
| 855 | ++++ | +++ |
| 856 | ++++ | +++ |
| 861 | ++++ | + |
| 862 | ++++ | + |
| 863 | ++++ | + |
| 864 | ++ | + |
| 865 | ++++ | ++ |
| 866 | ++++ | ++++ |
| 867 | ++++ | +++ |
| 868 | ++++ | + |
| 869 | ++++ | + |
| 870 | +++ | + |
| 871 | ++++ | ++++ |
| 872 | ++++ | + |
| 873 | ++++ | + |
| 874 | +++ | + |
| 875 | ++++ | + |
| 876 | +++ | + |
| 877 | +++ | + |
| 878 | +++ | + |
| 879 | +++ | + |
| 880 | ++ | + |
| 881 | ++++ | + |
| 882 | ++++ | + |
| 883 | ++++ | ++ |
| 884 | ++++ | + |
| 885 | +++ | + |
| 886 | ++++ | ++ |
| 887 | ++++ | +++ |
| 888 | ++++ | ++ |
| 889 | ++++ | ++ |
| 890 | ++++ | +++ |
| 891 | ++++ | ++ |
| 892 | ++++ | ++ |
| 893 | ++++ | +++ |
| 894 | ++++ | + |
| 895 | ++++ | + |
| 896 | ++++ | + |
| 897 | ++++ | + |
| 898 | ++++ | + |
| 899 | ++++ | ++++ |
| 900 | ++++ | ++ |
| 901 | ++++ | ++ |
| 902 | +++ | + |
| 904 | ++ | + |
| 905 | +++ | + |
| 906 | ++++ | ++ |
| 907 | ++++ | + |
| 908 | ++++ | ++ |
| 909 | ++++ | ++ |
| 910 | ++++ | + |
| 911 | ++++ | ++ |
| 912 | ++++ | + |
| 913 | ++++ | + |
| 914 | ++++ | ++ |
| 915 | ++++ | ++ |
| 916 | ++++ | + |
| 917 | ++++ | ++ |
| 921 | ++++ | ++++ |
| 922 | +++ | ++++ |
| 923 | ++++ | ++++ |
| 924 | ++++ | +++ |
| 926 | ++++ | ++++ |
| 927 | ++++ | +++ |
| 928 | ++++ | ++++ |
| 929 | ++++ | + |
| 930 | ++++ | ++++ |
| 931 | ++++ | ++++ |

TABLE 1-continued

ALK, c-Met Kinase Inhibition

| Example | ALK Activity | cMet Activity |
|---|---|---|
| 932 | ++ | + |
| 933 | ++++ | ++ |
| 934 | ++++ | ++++ |
| 935 | ++++ | ++++ |
| 936 | ++++ | +++ |
| 937 | ++++ | + |
| 938 | +++ | ++ |
| 939 | ++++ | ++ |
| 940 | ++++ | + |
| 941 | ++++ | + |
| 942 | ++ | + |
| 943 | ++ | + |
| 944 | ++++ | + |
| 945 | ++ | + |
| 946 | +++ | + |
| 947 | ++++ | + |
| 948 | +++ | + |
| 949 | ++++ | + |
| 950 | ++++ | +++ |
| 951 | ++++ | + |
| 952 | ++++ | + |
| 953 | ++++ | + |
| 954 | +++ | +++ |
| 955 | +++ | ++ |
| 956 | ++++ | + |
| 957 | ++++ | + |
| 958 | ++++ | + |
| 959 | ++++ | + |
| 960 | ++++ | + |
| 961 | ++++ | + |
| 962 | ++++ | + |
| 963 | ++++ | ++ |
| 964 | ++++ | + |
| 965 | ++++ | + |
| 971 | ++++ | ++ |
| 972 | ++++ | +++ |
| 973 | +++ | ++ |
| 974 | +++ | +++ |
| 975 | ++++ | ++ |
| 976 | ++++ | + |
| 977 | ++++ | +++ |
| 978 | ++++ | + |
| 979 | ++++ | +++ |
| 980 | +++ | + |
| 981 | +++ | ++ |
| 982 | ++++ | +++ |
| 983 | ++++ | + |
| 984 | ++++ | + |
| 985 | ++++ | ++ |
| 986 | ++++ | + |
| 987 | ++++ | + |
| 988 | ++ | + |
| 989 | ++++ | +++ |
| 990 | ++++ | +++ |
| 991 | +++ | + |
| 992 | ++++ | ++ |
| 993 | +++ | ++ |
| 994 | ++++ | + |
| 995 | ++++ | +++ |
| 996 | ++++ | + |
| 997 | +++ | +++ |
| 998 | + | + |
| 999 | ++++ | + |
| 1000 | ++++ | + |
| 1001 | +++ | + |
| 1002 | +++ | +++ |
| 1003 | ++ | + |
| 1004 | ++ | ++ |
| 1005 | ++++ | +++ |
| 1006 | +++ | ++ |
| 1007 | +++ | +++ |
| 1008 | ++++ | ++ |
| 1009 | ++++ | +++ |
| 1010 | +++ | ++ |
| 1011 | ++++ | +++ |
| 1012 | +++ | +++ |
| 1013 | +++ | ++ |
| 1014 | ++++ | + |
| 1015 | +++ | ++ |
| 1016 | +++ | ++ |
| 1017 | ++++ | +++ |
| 1018 | ++++ | ++ |
| 1019 | +++ | +++ |
| 1020 | ++++ | ++ |
| 1021 | +++ | ++ |
| 1022 | ++++ | +++ |
| 1023 | ++++ | +++ |
| 1024 | ++++ | ++++ |
| 1025 | ++++ | ++++ |
| 1026 | ++++ | + |
| 1027 | ++++ | ++ |
| 1028 | ++++ | +++ |
| 1029 | +++ | ++ |
| 1030 | ++++ | +++ |
| 1031 | ++++ | + |
| 1032 | ++++ | +++ |
| 1033 | ++++ | +++ |
| 1034 | ++++ | +++ |
| 1035 | ++++ | +++ |
| 1036 | ++++ | +++ |
| 1037 | ++++ | +++ |
| 1038 | ++++ | +++ |
| 1039 | ++ | +++ |
| 1040 | +++ | +++ |
| 1041 | ++++ | +++ |
| 1042 | +++ | ++++ |
| 1043 | +++ | ++++ |
| 1044 | ++++ | ++++ |
| 1045 | ++++ | ++++ |
| 1046 | ++++ | ++++ |
| 1047 | ++++ | + |
| 1048 | ++++ | + |
| 1049 | ++++ | + |
| 1050 | ++++ | + |
| 1051 | ++++ | + |
| 1052 | ++++ | + |
| 1053 | ++++ | + |
| 1054 | ++++ | + |
| 1055 | ++++ | + |
| 1056 | ++++ | ++ |
| 1057 | ++++ | + |
| 1058 | ++++ | + |
| 1059 | ++++ | + |
| 1060 | ++ | ++ |
| 1061 | + | ++ |
| 1062 | + | ++ |
| 1063 | ++ | +++ |
| 1064 | ++ | ++ |
| 1065 | + | +++ |
| 1070 | +++ | + |
| 1071 | +++ | + |
| 1072 | +++ | + |
| 1073 | +++ | + |
| 1074 | +++ | + |
| 1075 | ++ | + |
| 1076 | +++ | + |
| 1077 | +++ | + |
| 1078 | +++ | + |
| 1079 | ++++ | ++++ |
| 1080 | ++++ | ++++ |
| 1081 | ++++ | ++ |
| 1082 | ++++ | ++ |
| 1083 | ++++ | ++ |
| 1084 | ++++ | ++ |
| 1085 | ++++ | + |
| 1086 | ++++ | +++ |
| 1087 | ++++ | ++ |
| 1088 | ++++ | ++ |
| 1089 | ++++ | ++ |
| 1090 | ++++ | ++ |

TABLE 1-continued

ALK, c-Met Kinase Inhibition

| Example | ALK Activity | cMet Activity |
|---|---|---|
| 1091 | ++++ | ++ |
| 1092 | ++++ | + |
| 1093 | ++++ | + |
| 1094 | ++++ | + |
| 1095 | ++++ | + |
| 1096 | ++++ | + |
| 1097 | ++++ | + |
| 1098 | ++++ | ++ |
| 1099 | ++++ | ++ |
| 1100 | ++++ | ++ |
| 1101 | ++++ | + |
| 1102 | ++++ | ++++ |
| 1103 | ++++ | + |
| 1104 | ++++ | + |
| 1111 | ++++ | + |
| 1112 | ++++ | + |
| 1113 | ++++ | + |
| 1114 | ++++ | ++ |
| 1115 | ++++ | ++ |
| 1116 | ++++ | ++ |
| 1117 | ++++ | + |
| 1118 | ++++ | + |
| 1119 | ++++ | ++ |
| 1120 | ++++ | + |
| 1121 | ++++ | + |
| 1122 | ++++ | + |
| 1123 | ++++ | + |
| 1124 | ++++ | + |
| 1125 | ++++ | + |
| 1126 | ++++ | + |
| 1127 | ++++ | ++ |
| 1128 | ++++ | + |
| 1129 | ++++ | + |
| 1130 | ++++ | + |
| 1131 | ++++ | + |
| 1132 | ++++ | + |
| 1133 | ++ | + |
| 1134 | + | + |
| 1135 | ++++ | + |
| 1136 | +++ | ++ |
| 1137 | +++ | + |
| 1138 | +++ | + |
| 1139 | ++ | + |
| 1140 | ++ | + |
| 1141 | ++++ | ++ |
| 1142 | ++++ | ++ |
| 1143 | ++++ | + |
| 1144 | ++++ | + |
| 1145 | ++++ | + |
| 1146 | ++++ | + |
| 1147 | ++++ | + |
| 1148 | ++++ | ++ |
| 1149 | ++++ | ++ |
| 1150 | ++++ | + |
| 1151 | ++++ | ++ |
| 1152 | ++++ | ++ |
| 1153 | ++++ | + |
| 1154 | ++++ | + |
| 1155 | ++++ | + |
| 1156 | ++++ | + |
| 1157 | ++++ | ++ |
| 1158 | ++++ | ++ |
| 1159 | ++++ | + |
| 1160 | ++++ | + |
| 1161 | ++++ | + |
| 1162 | ++++ | + |
| 1163 | ++++ | + |
| 1164 | ++++ | ++ |
| 1165 | ++++ | ++ |
| 1166 | ++++ | + |
| 1167 | ++++ | + |
| 1168 | ++++ | + |
| 1169 | ++++ | + |
| 1170 | ++++ | ++ |
| 1171 | ++++ | ++ |
| 1172 | ++++ | + |
| 1173 | ++++ | + |
| 1174 | ++++ | + |
| 1175 | ++++ | + |
| 1176 | ++++ | + |
| 1177 | ++++ | + |
| 1178 | ++++ | +++ |
| 1179 | ++++ | + |
| 1180 | ++++ | + |
| 1181 | ++++ | ++ |
| 1182 | ++++ | + |
| 1183 | ++++ | + |
| 1184 | ++++ | + |
| 1185 | ++++ | + |
| 1186 | ++++ | + |
| 1187 | ++++ | + |
| 1188 | ++++ | ++ |
| 1189 | ++++ | + |
| 1190 | ++++ | + |
| 1191 | ++++ | ++ |
| 1192 | ++++ | ++ |
| 1193 | ++++ | +++ |
| 1194 | ++++ | ++ |
| 1195 | ++++ | ++ |
| 1196 | ++ | + |
| 1197 | ++ | + |
| 1198 | ++++ | + |
| 1199 | +++ | + |
| 1200 | ++++ | ++ |
| 1201 | ++++ | + |
| 1202 | +++ | + |
| 1203 | +++ | + |
| 1204 | ++++ | + |
| 1205 | ++++ | ++ |
| 1206 | ++++ | ++ |
| 1207 | ++++ | ++ |
| 1208 | ++++ | + |
| 1209 | ++++ | + |
| 1210 | ++++ | ++ |
| 1221 | +++ | ++++ |
| 1222 | +++ | +++ |
| 1223 | +++ | +++ |
| 1224 | ++++ | ++++ |
| 1225 | +++ | ++ |
| 1226 | +++ | ++ |
| 1227 | +++ | +++ |
| 1228 | +++ | ++++ |
| 1229 | +++ | +++ |
| 1230 | ++++ | ++++ |
| 1231 | ++++ | ++++ |
| 1232 | +++ | ++ |
| 1233 | +++ | +++ |
| 1234 | ++++ | +++ |
| 1235 | ++++ | +++ |
| 1236 | ++++ | ++++ |
| 1237 | ++++ | +++ |
| 1238 | ++++ | ++++ |
| 1239 | ++++ | ++ |
| 1240 | ++++ | ++++ |
| 1241 | +++ | +++ |
| 1242 | ++++ | +++ |
| 1243 | ++++ | ++++ |
| 1244 | ++ | ++ |
| 1245 | +++ | +++ |
| 1246 | +++ | ++++ |
| 1247 | ++++ | +++ |
| 1248 | ++++ | ++++ |
| 1249 | ++++ | +++ |
| 1250 | ++++ | +++ |
| 1251 | +++ | ++ |
| 1252 | ++++ | ++ |
| 1253 | ++++ | ++ |
| 1254 | ++++ | ++ |
| 1255 | +++ | ++ |
| 1256 | +++ | ++ |

TABLE 1-continued

ALK, c-Met Kinase Inhibition

| Example | ALK Activity | cMet Activity |
|---|---|---|
| 1257 | ++++ | +++ |
| 1258 | +++ | ++ |
| 1259 | +++ | ++ |
| 1260 | ++++ | ++ |
| 1261 | ++ | + |
| 1262 | +++ | ++ |
| 1263 | +++ | ++ |
| 1264 | +++ | ++ |
| 1265 | +++ | ++ |
| 1266 | ++++ | ++ |
| 1267 | +++ | ++ |
| 1268 | +++ | ++++ |
| 1269 | +++ | ++++ |
| 1270 | +++ | ++++ |
| 1271 | +++ | ++++ |
| 1272 | ++++ | ++++ |
| 1273 | +++ | +++ |
| 1274 | +++ | +++ |
| 1275 | ++ | ++ |
| 1276 | +++ | +++ |
| 1277 | +++ | +++ |
| 1278 | ++++ | ++++ |
| 1279 | +++ | ++++ |
| 1280 | ++++ | ++++ |
| 1281 | +++ | ++ |
| 1282 | ++++ | ++ |
| 1283 | ++ | + |
| 1284 | +++ | ++ |
| 1285 | +++ | ++++ |
| 1286 | ++ | ++ |
| 1287 | +++ | ++ |
| 1288 | +++ | ++++ |
| 1289 | +++ | ++++ |
| 1290 | ++ | ++++ |
| 1291 | ++ | ++++ |
| 1292 | +++ | ++++ |
| 1293 | ++++ | ++++ |
| 1294 | ++++ | ++++ |
| 1295 | +++ | ++++ |
| 1296 | +++ | ++++ |
| 1297 | +++ | ++++ |
| 1298 | +++ | ++++ |
| 1299 | +++ | ++++ |
| 1300 | +++ | ++++ |
| 1301 | ++++ | ++++ |
| 1302 | ++++ | ++++ |
| 1303 | ++++ | ++++ |
| 1304 | ++++ | +++ |
| 1305 | ++++ | ++++ |
| 1307 | +++ | ++ |
| 1308 | +++ | ++ |
| 1311 | ++++ | + |
| 1312 | ++++ | + |
| 1313 | ++++ | + |
| 1314 | ++++ | + |
| 1315 | ++++ | + |
| 1316 | ++++ | + |
| 1317 | ++++ | + |
| 1318 | +++ | + |
| 1319 | ++++ | + |
| 1320 | ++++ | + |
| 1321 | ++++ | + |
| 1322 | ++ | + |
| 1323 | ++++ | +++ |
| 1324 | ++++ | ++ |
| 1325 | ++++ | +++ |
| 1326 | ++++ | ++ |
| 1327 | ++++ | ++ |
| 1328 | ++++ | ++ |
| 1329 | ++++ | ++++ |
| 1330 | ++++ | + |
| 1331 | ++++ | + |
| 1332 | ++++ | + |
| 1333 | ++++ | + |
| 1334 | ++++ | + |
| 1335 | ++++ | + |
| 1336 | ++++ | + |
| 1337 | ++++ | + |
| 1338 | +++ | + |
| 1339 | +++ | + |
| 1340 | ++++ | + |
| 1341 | ++++ | + |
| 1342 | ++++ | ++ |
| 1343 | ++++ | + |
| 1344 | ++++ | + |
| 1345 | ++++ | + |
| 1346 | ++++ | ++ |
| 1347 | ++++ | ++ |
| 1348 | ++++ | + |
| 1349 | ++++ | + |
| 1350 | ++++ | + |
| 1351 | ++++ | + |
| 1352 | ++++ | + |
| 1353 | ++++ | + |
| 1354 | ++++ | + |
| 1355 | ++++ | + |
| 1356 | ++++ | + |
| 1357 | ++++ | + |
| 1358 | ++++ | + |
| 1359 | ++++ | + |
| 1361 | ++++ | ++++ |
| 1362 | +++ | ++++ |
| 1363 | ++++ | ++++ |
| 1364 | ++++ | ++ |
| 1365 | ++++ | ++++ |
| 1366 | ++++ | ++++ |
| 1367 | ++++ | ++++ |
| 1368 | ++++ | ++ |
| 1369 | ++++ | ++++ |
| 1370 | +++ | ++++ |
| 1371 | ++++ | +++ |
| 1372 | ++++ | ++++ |
| 1373 | +++ | ++++ |
| 1374 | ++++ | +++ |
| 1375 | +++ | ++++ |
| 1376 | ++++ | +++ |
| 1377 | ++++ | +++ |
| 1378 | +++ | + |
| 1379 | ++ | ++ |
| 1380 | ++ | + |
| 1381 | +++ | ++ |
| 1382 | +++ | ++ |
| 1383 | +++ | ++ |
| 1384 | +++ | ++ |
| 1385 | +++ | ++ |
| 1386 | +++ | ++ |
| 1387 | ++++ | ++++ |
| 1388 | ++++ | ++++ |
| 1389 | ++++ | +++ |
| 1390 | ++++ | +++ |
| 1391 | ++++ | + |
| 1392 | ++++ | + |
| 1393 | ++++ | + |
| 1394 | ++++ | + |
| 1395 | ++++ | +++ |
| 1396 | ++++ | +++ |
| 1397 | +++ | +++ |
| 1398 | ++++ | ++ |
| 1399 | ++++ | ++ |
| 1400 | +++ | ++ |
| 1401 | +++ | +++ |
| 1402 | +++ | ++ |
| 1403 | ++++ | ++++ |
| 1404 | +++ | +++ |
| 1405 | +++ | ++++ |
| 1406 | +++ | ++++ |
| 1407 | +++ | ++++ |
| 1408 | ++++ | +++ |
| 1409 | +++ | +++ |
| 1410 | +++ | +++ |

TABLE 1-continued

ALK, c-Met Kinase Inhibition

| Example | ALK Activity | cMet Activity |
|---|---|---|
| 1411 | +++ | ++ |
| 1412 | +++ | +++ |
| 1413 | ++++ | +++ |
| 1414 | +++ | ++++ |
| 1415 | ++++ | ++++ |
| 1416 | +++ | +++ |
| 1417 | +++ | ++++ |
| 1418 | +++ | +++ |
| 1419 | ++++ | ++++ |
| 1420 | ++++ | +++ |
| 1421 | ++++ | ++ |
| 1422 | +++ | ++++ |
| 1423 | ++++ | ++++ |
| 1424 | +++ | ++++ |
| 1425 | ++++ | ++++ |
| 1426 | +++ | ++++ |
| 1427 | +++ | +++ |
| 1428 | +++ | +++ |
| 1429 | +++ | +++ |
| 1430 | +++ | ++++ |
| 1431 | +++ | ++++ |
| 1432 | +++ | ++++ |
| 1433 | +++ | +++ |
| 1434 | ++++ | ++++ |
| 1435 | +++ | +++ |
| 1436 | +++ | ++++ |
| 1437 | ++++ | +++ |
| 1438 | ++++ | ++++ |
| 1439 | +++ | +++ |
| 1440 | +++ | +++ |
| 1451 | ++++ | +++ |
| 1452 | ++++ | ++++ |
| 1453 | ++++ | +++ |
| 1454 | +++ | ++++ |
| 1455 | + | + |
| 1456 | ++++ | + |
| 1457 | ++++ | ++ |
| 1458 | +++ | ++++ |
| 1459 | ++++ | ++++ |
| 1460 | ++++ | + |
| 1461 | ++++ | + |
| 1463 | ++++ | + |
| 1464 | ++ | + |
| 1465 | + | + |
| 1466 | ++ | + |
| 1467 | ++ | ++ |
| 1471 | ++++ | ++++ |
| 1472 | ++++ | ++++ |
| 1473 | +++ | ++++ |
| 1474 | ++++ | +++ |
| 1475 | +++ | + |
| 1476 | +++ | ++ |
| 1477 | +++ | +++ |
| 1478 | +++ | ++++ |
| 1479 | +++ | ++ |
| 1480 | +++ | ++ |
| 1481 | +++ | +++ |
| 1482 | +++ | ++ |
| 1483 | ++++ | ++++ |
| 1484 | +++ | +++ |
| 1485 | ++ | +++ |
| 1486 | ++ | ++ |
| 1487 | +++ | +++ |
| 1488 | +++ | ++++ |
| 1489 | +++ | ++++ |
| 1490 | +++ | ++++ |
| 1491 | ++++ | ++++ |
| 1492 | ++++ | ++++ |
| 1493 | ++++ | ++++ |
| 1494 | +++ | ++++ |
| 1495 | ++ | +++ |
| 1496 | +++ | ++++ |
| 1497 | +++ | ++++ |
| 1498 | +++ | ++++ |
| 1499 | +++ | ++++ |
| 1501 | +++ | ++ |
| 1502 | +++ | + |
| 1503 | ++++ | + |
| 1505 | ++++ | ++ |
| 1506 | ++++ | + |
| 1507 | ++++ | +++ |
| 1508 | ++++ | + |
| 1509 | ++++ | + |
| 1510 | ++++ | + |
| 1511 | ++++ | ++ |
| 1512 | ++++ | ++ |
| 1513 | ++++ | +++ |
| 1514 | ++++ | + |
| 1516 | ++++ | ++ |
| 1517 | ++ | + |
| 1518 | +++ | ++ |
| 1520 | ++++ | ++++ |
| 1521 | ++++ | ++++ |
| 1522 | ++++ | ++ |
| 1523 | ++++ | + |
| 1524 | ++++ | ++ |
| 1525 | ++++ | + |
| 1526 | ++++ | + |
| 1527 | ++++ | + |
| 1528 | ++++ | + |
| 1529 | ++++ | + |
| 1530 | ++++ | ++ |
| 1531 | ++++ | + |
| 1532 | ++++ | + |
| 1533 | ++++ | + |
| 1534 | ++++ | + |
| 1535 | ++++ | ++ |
| 1536 | ++++ | + |
| 1537 | ++++ | + |
| 1538 | ++++ | ++ |
| 1539 | ++++ | + |
| 1540 | ++++ | + |
| 1541 | ++++ | + |
| 1542 | ++++ | ++ |
| 1543 | ++++ | ++ |
| 1544 | ++++ | ++ |
| 1545 | ++++ | ++ |
| 1546 | ++++ | ++ |
| 1547 | ++++ | ++ |
| 1548 | ++++ | + |
| 1549 | ++++ | + |
| 1550 | ++++ | + |
| 1551 | ++++ | +++ |
| 1552 | ++++ | ++ |
| 1553 | ++++ | +++ |
| 1554 | ++++ | +++ |
| 1555 | ++++ | +++ |
| 1556 | ++++ | ++ |
| 1557 | ++++ | + |
| 1558 | ++++ | + |
| 1559 | ++++ | + |
| 1560 | ++++ | + |
| 1561 | ++++ | ++ |
| 1562 | ++++ | +++ |
| 1563 | ++++ | ++ |
| 1571 | ++++ | +++ |
| 1572 | +++ | +++ |
| 1573 | ++++ | ++ |
| 1574 | +++ | ++++ |
| 1575 | ++++ | ++++ |
| 1576 | ++++ | ++++ |
| 1577 | ++ | +++ |
| 1578 | ++++ | +++ |
| 1579 | ++++ | ++++ |
| 1580 | ++++ | +++ |
| 1581 | ++++ | ++++ |
| 1582 | ++++ | +++ |
| 1583 | ++++ | +++ |
| 1584 | ++++ | ++ |
| 1585 | ++++ | +++ |

TABLE 1-continued

ALK, c-Met Kinase Inhibition

| Example | ALK Activity | cMet Activity |
|---|---|---|
| 1586 | ++++ | ++++ |
| 1587 | ++++ | ++ |
| 1588 | ++++ | +++ |
| 1589 | ++++ | ++++ |
| 1590 | ++++ | ++ |
| 1591 | ++++ | + |
| 1592 | ++++ | ++++ |
| 1593 | ++++ | ++ |
| 1594 | ++++ | + |
| 1595 | ++++ | ++++ |
| 1596 | +++ | ++++ |
| 1597 | ++ | ++ |
| 1598 | +++ | ++ |
| 1599 | ++++ | ++++ |
| 1600 | ++++ | +++ |
| 1601 | +++ | + |
| 1602 | +++ | ++++ |
| 1603 | +++ | +++ |
| 1604 | +++ | +++ |
| 1605 | ++++ | +++ |
| 1606 | ++++ | ++ |
| 1607 | ++++ | +++ |
| 1608 | +++ | ++++ |
| 1609 | ++++ | +++ |
| 1610 | ++++ | ++ |
| 1611 | +++ | ++++ |
| 1612 | +++ | +++ |
| 1613 | ++++ | +++ |
| 1614 | +++ | + |
| 1615 | ++++ | ++++ |
| 1616 | +++ | +++ |
| 1617 | +++ | ++++ |
| 1618 | + | ++++ |
| 1619 | +++ | ++++ |
| 1620 | +++ | +++ |
| 1621 | ++++ | ++++ |
| 1622 | ++ | +++ |
| 1623 | +++ | + |
| 1624 | ++++ | ++++ |
| 1625 | ++++ | ++ |
| 1626 | +++ | +++ |
| 1627 | ++ | ++ |
| 1628 | ++++ | + |
| 1629 | +++ | + |
| 1630 | +++ | +++ |
| 1631 | +++ | +++ |
| 1632 | +++ | +++ |
| 1633 | +++ | +++ |
| 1634 | ++++ | ++ |
| 1635 | +++ | + |
| 1636 | ++++ | ++++ |
| 1637 | ++++ | ++++ |
| 1638 | ++++ | ++++ |
| 1639 | ++++ | +++ |
| 1640 | ++++ | ++++ |
| 1641 | ++++ | ++ |
| 1642 | +++ | ++++ |
| 1643 | +++ | ++++ |
| 1644 | +++ | ++++ |
| 1651 | ++++ | + |
| 1652 | ++++ | + |
| 1653 | ++++ | ++ |
| 1654 | ++ | + |
| 1655 | ++++ | + |
| 1656 | +++ | + |
| 1657 | ++++ | + |
| 1658 | ++++ | + |
| 1659 | ++++ | + |
| 1660 | ++++ | + |
| 1661 | ++++ | + |
| 1662 | ++++ | + |
| 1663 | ++++ | + |
| 1664 | ++++ | + |
| 1665 | ++++ | + |
| 1666 | ++++ | + |
| 1667 | ++++ | + |
| 1668 | ++++ | ++ |
| 1671 | ++++ | ++ |
| 1672 | +++ | + |
| 1673 | ++++ | + |
| 1674 | ++++ | ++ |
| 1675 | ++++ | ++ |
| 1676 | ++++ | + |
| 1677 | ++++ | + |
| 1678 | ++++ | ++ |
| 1679 | +++ | + |
| 1680 | ++++ | +++ |
| 1681 | ++++ | ++ |
| 1682 | ++++ | +++ |
| 1683 | +++ | + |
| 1684 | ++++ | + |
| 1685 | ++++ | +++ |
| 1686 | ++++ | +++ |
| 1687 | ++++ | ++ |
| 1688 | +++ | + |
| 1689 | ++++ | ++ |
| 1690 | ++++ | ++ |
| 1691 | ++++ | ++++ |
| 1692 | ++++ | ++++ |
| 1693 | ++++ | +++ |
| 1694 | ++++ | ++ |
| 1695 | +++ | +++ |
| 1696 | ++++ | +++ |
| 1697 | +++ | +++ |
| 1698 | +++ | +++ |
| 1699 | +++ | + |
| 1700 | ++++ | ++ |
| 1701 | +++ | ++++ |
| 1702 | ++ | ++++ |
| 1703 | ++++ | ++++ |
| 1704 | ++ | +++ |
| 1705 | +++ | +++ |
| 1706 | +++ | +++ |
| 1707 | ++++ | ++++ |
| 1708 | ++++ | ++++ |
| 1709 | ++++ | +++ |
| 1710 | ++++ | +++ |
| 1711 | +++ | ++ |
| 1712 | ++ | ++ |
| 1713 | +++ | ++++ |
| 1714 | +++ | ++++ |
| 1715 | +++ | +++ |
| 1716 | +++ | ++++ |
| 1717 | ++ | ++++ |
| 1718 | ++++ | ++++ |
| 1719 | ++++ | ++++ |
| 1720 | ++++ | +++ |
| 1721 | +++ | +++ |
| 1722 | ++++ | ++++ |
| 1723 | +++ | ++++ |
| 1724 | +++ | ++++ |
| 1725 | ++++ | ++++ |
| 1726 | +++ | ++++ |
| 1727 | ++ | ++ |
| 1728 | +++ | ++++ |
| 1729 | ++ | +++ |
| 1730 | ++++ | ++++ |
| 1731 | ++++ | ++++ |
| 1732 | ++++ | ++++ |
| 1733 | ++++ | +++ |
| 1734 | ++++ | ++++ |
| 1735 | +++ | +++ |
| 1736 | +++ | ++++ |
| 1741 | ++++ | ++++ |
| 1742 | ++++ | ++++ |
| 1743 | ++ | ++++ |
| 1744 | ++ | ++++ |
| 1745 | ++++ | ++++ |
| 1746 | ++++ | ++++ |
| 1747 | +++ | ++++ |

TABLE 1-continued

ALK, c-Met Kinase Inhibition

| Example | ALK Activity | cMet Activity |
|---|---|---|
| 1748 | ++++ | ++++ |
| 1749 | ++++ | +++ |
| 1750 | ++ | ++++ |
| 1751 | ++ | ++++ |
| 1752 | ++++ | ++++ |
| 1753 | + | +++ |
| 1754 | +++ | +++ |
| 1755 | +++ | +++ |
| 1756 | ++++ | ++++ |
| 1757 | +++ | ++++ |
| 1758 | ++ | ++++ |
| 1759 | ++ | ++++ |
| 1760 | +++ | ++++ |
| 1761 | ++ | ++ |
| 1762 | + | + |
| 1763 | ++ | ++ |
| 1764 | ++ | + |
| 1765 | + | ++ |
| 1766 | ++++ | +++ |
| 1767 | + | ++ |
| 1768 | +++ | ++ |
| 1769 | +++ | +++ |
| 1770 | +++ | ++++ |
| 1771 | +++ | ++++ |
| 1772 | ++ | ++++ |
| 1773 | + | +++ |
| 1774 | ++ | +++ |
| 1775 | + | ++ |
| 1776 | ++ | +++ |
| 1777 | +++ | +++ |
| 1778 | +++ | +++ |
| 1779 | +++ | +++ |
| 1780 | ++++ | ++++ |
| 1781 | ++ | ++ |
| 1782 | ++ | ++ |
| 1783 | ++ | +++ |
| 1784 | ++ | ++ |
| 1785 | ++ | +++ |
| 1786 | +++ | ++++ |
| 1787 | ++ | +++ |
| 1788 | ++++ | ++++ |
| 1789 | +++ | +++ |
| 1790 | +++ | +++ |
| 1791 | ++ | ++ |
| 1792 | ++ | ++ |
| 1793 | +++ | ++ |
| 1794 | ++++ | ++++ |
| 1795 | ++ | ++++ |
| 1796 | +++ | ++++ |
| 1797 | ++++ | +++ |
| 1798 | ++++ | ++++ |
| 1799 | ++++ | ++++ |
| 1800 | ++ | ++++ |
| 1801 | ++ | + |
| 1802 | ++ | +++ |
| 1803 | ++++ | +++ |
| 1804 | ++++ | +++ |
| 1805 | ++++ | +++ |
| 1806 | ++ | ++++ |
| 1807 | ++++ | ++++ |
| 1808 | ++ | ++++ |
| 1809 | ++ | ++ |
| 1810 | ++++ | ++++ |
| 1811 | ++++ | ++++ |
| 1812 | ++++ | ++++ |
| 1813 | ++ | ++++ |
| 1814 | ++++ | +++ |
| 1815 | ++ | +++ |
| 1816 | ++++ | +++ |
| 1817 | ++ | +++ |
| 1818 | ++ | +++ |
| 1819 | ++ | ++ |
| 1820 | ++++ | ++ |
| 1821 | +++ | +++ |
| 1822 | ++ | ++ |
| 1823 | ++ | + |
| 1824 | ++ | + |
| 1825 | + | + |
| 1826 | ++ | ++ |
| 1827 | ++++ | ++++ |
| 1828 | ++++ | ++++ |
| 1829 | ++ | ++++ |
| 1830 | ++ | ++++ |
| 1831 | ++ | ++++ |
| 1832 | ++++ | ++++ |
| 1833 | ++++ | +++ |
| 1834 | ++++ | ++++ |
| 1835 | +++ | ++++ |
| 1836 | +++ | ++++ |
| 1837 | ++++ | ++++ |
| 1838 | +++ | ++++ |
| 1839 | ++ | +++ |
| 1840 | +++ | +++ |
| 1841 | ++ | +++ |
| 1842 | ++++ | ++++ |
| 1843 | +++ | ++ |
| 1844 | ++++ | ++++ |
| 1845 | +++ | +++ |
| 1846 | ++ | +++ |
| 1847 | ++ | +++ |
| 1848 | +++ | +++ |
| 1849 | +++ | ++++ |
| 1850 | +++ | +++ |
| 1851 | ++ | ++++ |
| 1852 | ++++ | ++++ |
| 1853 | ++ | ++++ |
| 1854 | +++ | ++++ |
| 1855 | ++ | ++++ |
| 1856 | ++++ | ++++ |
| 1857 | +++ | ++++ |
| 1858 | +++ | ++++ |
| 1859 | +++ | +++ |
| 1860 | ++++ | ++++ |
| 1861 | +++ | ++++ |
| 1862 | +++ | ++++ |
| 1863 | +++ | ++++ |
| 1864 | ++++ | ++++ |
| 1865 | +++ | +++ |
| 1866 | ++ | +++ |
| 1867 | ++ | ++++ |
| 1868 | +++ | ++++ |
| 1869 | ++ | +++ |
| 1870 | +++ | ++++ |
| 1871 | +++ | ++++ |
| 1872 | ++ | ++ |
| 1873 | +++ | ++++ |
| 1874 | +++ | ++++ |
| 1875 | ++ | ++++ |
| 1876 | +++ | ++++ |
| 1877 | ++++ | ++++ |
| 1878 | +++ | ++++ |
| 1879 | +++ | ++++ |
| 1880 | ++++ | ++++ |
| 1881 | +++ | +++ |
| 1882 | ++++ | ++++ |
| 1883 | ++++ | ++++ |
| 1884 | +++ | ++++ |

$IC_{50} > 10\ \mu M\ +$
$IC_{50}\ 10\ \mu M\text{-}1\ \mu M\ ++$
$IC_{50}\ 1\ \mu M\text{-}0.1\ \mu M\ +++$
$IC_{50} < 0.1\ \mu M\ ++++$ Preferably, a compound of the present invention (i.e., a compound of formula I or II or a pharmaceutically acceptable salt thereof) has an ALK kinase $IC_{50}$ of <10 μM. In one embodiment, a compound of the present invention has an ALK kinase $IC_{50}$ of 10 μM-1 μM. More preferably, a compound of the present invention has an ALK kinase $IC_{50}$ of <1 μM. In one embodiment, a compound of the present invention has an ALK kinase IC$_{50}$ of 1 μM-0.1 μM. More preferably, a compound of the present invention has an ALK kinase IC$_{50}$ of <0.1 μM.

Preferably, a compound of the present invention has a c-Met kinase IC$_{50}$ of <10 μM. In one embodiment, a compound of the present invention has a c-Met kinase IC$_{50}$ of 10 μM-1 μM. More preferably, a compound of the present invention has a c-Met kinase IC$_{50}$ of <1 μM. In one embodiment, a compound of the present invention has a c-Met kinase IC$_{50}$ of 1 μM-0.1 μM. More preferably, a compound of the present invention has a c-Met kinase IC$_{50}$ of <0.1 μM.

In one embodiment, a compound of the present invention has an ALK kinase IC$_{50}$ of <10 μM and a c-Met kinase IC$_{50}$ of <10 μM. In one embodiment, a compound of the present invention has an ALK kinase IC$_{50}$ of 10 μM-1 μM and a c-Met kinase IC$_{50}$ of 10 μM-1 μM. In one embodiment, a compound of the present invention has an ALK kinase IC$_{50}$ of <1 μM and a c-Met kinase IC$_{50}$ of <1 μM. In one embodiment, a compound of the present invention has an ALK kinase IC$_{50}$ of 1 μM-0.1 μM and a c-Met kinase IC$_{50}$ of 1 μM-0.1 μM. In one embodiment, a compound of the present invention has an ALK kinase IC$_{50}$ of <0.1 μM and a c-Met kinase IC$_{50}$ of <0.1 μM.

In one embodiment, a compound of formula I or II has an IC$_{50}$ in the ALK kinase assay of 10 μM-1 μM. In another embodiment, a compound of formula I or II has an IC$_{50}$ in the ALK kinase assay of 1 μM-0.1 μM. In another embodiment, a compound of formula I or II has an IC$_{50}$ in the ALK kinase assay of <0.1 μM.

In one embodiment, a compound of formula I or II has an IC$_{50}$ in the c-Met kinase assay of 10 μM-1 μM. In another embodiment, a compound of formula I or II has an IC$_{50}$ in the c-Met kinase assay of 1 μM-0.1 μM. In another embodiment, a compound of formula I or II has an IC$_{50}$ in the c-Met kinase assay of <0.1 μM.

EXAMPLES

Example 1

2-[5-Chloro-2-(1-methyl-2-oxo-2,3,4,5-tetrahydro-1H-benzo[b]azepin-7-ylamino)-pyrimidin-4-ylamino]-N-methyl-benzamide 1a) 1,3,4,5-Tetrahydro-benzo[b]azepin-2-one (406 mg, 2.52 mmol) was added to a cooled (0° C.) mixture of nitric acid (5 ml) and sulfuric acid (7 ml). The mixture was stirred at 0° C. for 15 minutes, then poured into water (50 ml) and extracted with ethyl acetate (50 ml). The organic phase was washed once with aqueous sodium bicarbonate and once with water, and concentrated to a yellow solid. Trituration with ether afforded 7-Nitro-1,3,4,5-tetrahydro-benzo[b]azepin-2-one as an off-white solid, 276 mg. (53% yield) $^1$H NMR (400 MHz, DMSO-d$_6$) δ 10.10 (s, 1H), 8.19 (s, 1H), 8.09-8.16 (m, 1H), 7.12-7.28 (m, 1H), 2.78-2.86 (m, 2H), 2.20-2.38 (m, 4H); MS (m/e) 207 (M+1).

1b) 7-Nitro-1,3,4,5-tetrahydro-benzo[b]azepin-2-one (200 mg, 0.97 mmol) was dissolved in anhydrous DMF (3 ml), and treated with sodium hydride (60% in mineral oil, 58 mg, 1.45 mmol) followed by methyl iodide (0.5 ml). The mixture was stirred 18 hours at room temperature, and then partitioned between ethyl acetate (30 ml) and water (30 ml). Washing once with water (30 ml), drying over anhydrous magnesium sulfate and concentration gave a yellow residue. Purification by preparative TLC (40% EtOAc/hexane) gave 1-Methyl-7-nitro-1,3,4,5-tetrahydrobenzo[b]azepin-2-one as a white solid, 185 mg. (87% yield) $^1$H NMR (400 MHz, DMSO-d$_6$) δ 8.14-8.24 (m, 2H), 7.52-7.60 (m, 1H), 3.40 (s, 3H), 2.75-2.82 (m, 2H), 2.06-2.25 (m, 4H); MS (m/e) 221 (M+1).

1c) 1-Methyl-7-nitro-1,3,4,5-tetrahydrobenzo[b]azepin-2-one (185 mg, 0.84 mmol) was dissolved in ethanol (3.5 ml). 10% palladium on carbon (50 mg) and hydrazine hydrate (1 ml) were then added, and the mixture was heated to reflux for 2 hours. After cooling to room temperature, the mixture was then filtered through Celite and concentrated to give 7-Amino-1-methyl-1,3,4,5-tetrahydrobenzo[b]azepin-2-one as a clear oil, 166 mg. $^1$H NMR (400 MHz, DMSO-d$_6$) δ 6.92-6.97 (m, 1H), 6.42-6.50 (m, 1H), 6.40 (s, 1H), 5.13 (s, 2H), 3.10 (s, 3H), 1.90-2.16 (m, 6H); MS (m/e) 221 (M+1).

1d) 2-Amino-N-methyl-benzamide (1.5 g, 10 mmol) and 2,4,5-Trichloro-pyrimidine (1.31 ew) were combined in DMF (30 mL). Potassium carbonate (1.3 eq) was added the mixture heated to 75° C. for 4.5 h and stirred at room temperature overnight. The mixture was poured into water and the white precipitate that ensued was filtered and dried to give 2-(2,5-dichloro-pyrimidin-4-ylamino)-N-methyl-benzamide (2.7 g, 92%): $^1$H NMR (400 MHz, DMSO-d$_6$) δ 12.19 (s, 1H), 8.86 (s, 1H), 8.54-8.48 (m, 2H), 7.81 (d, J=7.9 Hz, 1H), 7.61 (t, J=8.7 Hz, 1H), 7.23 (t, J=8.9 Hz, 1H), 2.50 (d, J=1.5 Hz, 3H).

1e) 7-Amino-1-methyl-1,3,4,5-tetrahydrobenzo[b]azepin-2-one (166 mg, 0.87 mmol) and 2-(2,5-dichloro-pyrimidin-4-ylamino)-N-methyl-benzamide (259 mg, 0.87 mmol) were suspended in 2-methoxyethanol (9 ml), and heated to 120° C. for 18 hours. Concentration afforded a brown residue. Purification by preparative TLC (5% MeOH/CH$_2$Cl$_2$) gave a slightly impure yellow oil which was then triturated with acetone to give the title compound as a white solid, 45 mg. (11% yield) $^1$H NMR (400 MHz, DMSO-d$_6$) δ 11.58 (s, 1H), 9.52 (s, 1H), 8.64-8.81 (m, 2H), 8.22 (s, 1H), 7.69-7.75 (m, 1H), 7.42-7.59 (m, 3H), 7.12-7.26 (m, 2H), 3.19 (s, 3H), 2.74-2.80 (m, 2H), 2.49-2.60 (m, 2H), 1.95-2.20 (m, 5H); MS (m/e) 451 (M+1); mp 244-246° C.

Example 2

2-[5-Chloro-2-(2-oxo-2,3,4,5-tetrahydro-1H-benzo[b]azepin-7-ylamino)-pyrimidin-4-ylamino]-N-methyl-benzamide 2a) Following a procedure analogous to 1c, 7-Nitro-1,3,4,5-tetrahydro-benzo[b]azepin-2-one was converted to 7-Amino-1-methyl-1,3,4,5-tetrahydrobenzo[b]azepin-2-one which, following a procedure analogous to 1e was converted to 2-[5-Chloro-2-(2-oxo-2,3,4,5-tetrahydro-1H-benzo[b]azepin-7-ylamino)-pyrimidin-4-ylamino]-N-methyl-benzamide. $^1$H NMR (400 MHz, DMSO-d$_6$) δ 11.56 (s, 1H), 9.42 (s, 1H), 9.33 (s, 1H), 8.69 (s, 1H), 8.21 (s, 1H), 7.75 (d, J=7.24 Hz, 1H), 7.57 (s, 1H), 7.25 (m, 2H), 7.14 (dd, J=7.13 and 7.15 Hz, 1H), 6.87 (d, J=8.54 Hz), 2.8° (d, J=4.33 Hz, 3H), 2.6 (m, 2H), 2.13 (m, 4H); MS (m/e) 437, 438 (M+H); mp 283° C.

Example 3

2-[5-Chloro-2-(6-methoxy-2-oxo-2,3,4,5-tetrahydro-1H-benzo[b]azepin-7-ylamino)-pyrimidin-4-ylamino]-N-methyl-benzamide 3a) Following a procedure analogous to 1a, 6-Methoxy-1,3,4,5-tetrahydro-benzo[b]azepin-2-one (synthesized according to the procedure in the literature: Dynamic and Static Conformational Analysis of Acylated Tetrahydrobenzazepines. Hassner, Alfred; Amit, Boaz; Marks, Vered; Gottlieb, Hugo E. Journal of Organic Chemistry (2003), 68(18), 6853-6858) was converted to 6-Methoxy-7-nitro-1,3,4,5-tetrahydro-benzo[b]azepin-2-one which, following a procedure analogous to 1c was converted to 7-amino-6-Methoxy-1,3,4,5-tetrahydro-benzo[b]azepin-2-one which was converted following a procedure analogous to 1e was converted to 2-[5-Chloro-2-(6-methoxy-2-oxo-2,3,4,5-tetrahydro-1H-benzo[b]azepin-7-ylamino)-pyrimidin-4-ylamino]-N-methyl-benzamide. $^1$H NMR (400 MHz, DMSO-d$_6$) δ 11.08 (s, 1H), 8.64 (d, J=8.25 Hz), 8.21 (d, J=8.64 Hz, 1H0, 8.13 (s, 1H), 7.50 (m, H), 7.11 (m, 2H), 6.70 (d, J=8.71 Hz, 1H0, 3.81 (s, 3H0, 3.04 (s, 3H), 2.89 (m, 2H), 2.38 (m, 2H), 2.25 (m, 2H); MS (m/e) 437, 438 (M+H);

Example 4

2-[5-Chloro-2-(1-methyl-2-oxo-2,3,4,5-tetrahydro-1H-benzo[b]azepin-7-ylamino)-pyrimidin-4-ylamino]-N-methyl-benzenesulfonamide 4a) A mixture of 2-amino-N-methyl-benzenesulfonamide (2.93, 15.75 mmol), 2,4,5 trichloropyrimidine (2.9 g, 15.84 mmol) and K$_2$CO$_3$ (4.5 g, 32.6 mmol) in dry DMF (25 mL) was stirred at 45° C. for 15 h. The solvent was removed and the residue was taken in water and was extracted twice from ethylacetate. Combined organic was washed with water and brine. After drying solvent was removed. Upon triturating with ether and filtration gave the product 2-(2,5-Dichloro-pyrimidin-4-ylamino)-N-methyl-benzenesulfonamide 7 as a white solid (2.6 g, 50%); $^1$H NMR (400 MHz, CDCl$_3$) δ9.61 (s, 1H), 8.6 (d=12.89 Hz, 1H), 8.53 (s, 1H), 8.27 (s, 1H), 7.68 (m, 1H), 7.27 (m, 1H0, 1.66 (br s, 1H0, 2.66 (s, 3H).

4b) 7-Amino-1-methyl-1,3,4,5-tetrahydrobenzo[b]azepin-2-one (160 mg, 0.84 mmol), 2-(2,5-Dichloro-pyrimidin-4-ylamino)-N-methyl-benzenesulfonamide (280 mg, 0.84 mmol) and 4N HCl in dioxane (0.21 ml, 0.84 mmol) were dissolved in 2-methoxyethanol (4 ml) and heated to 120° C. for 5 hours. The mixture was concentrated to a brown solid. Preparative TLC (5% MeOH/CH$_2$Cl$_2$) gave a brown residue which was triturated with MeOH/CH$_2$Cl$_2$ to 2-[5-Chloro-2-(1-methyl-2-oxo-2,3,4,5-tetrahydro-1H-benzo[b]azepin-7-ylamino)-pyrimidin-4-ylamino]-N-methyl-benzenesulfonamide as a white solid, 58 mg. (14% yield) $^1$H NMR (400 MHz, DMSO-d$_6$) δ 9.58 (s, 1H), 9.23 (s, 1H), 8.32-8.58 (m, 1H), 8.27 (s, 1H), 7.45-7.90 (m, 5H), 7.23-7.37 (m, 1H), 7.14-7.22 (m, 1H), 3.22 (s, 3H), 2.39-2.60 (m, 5H), 1.92-2.18 (m, 4H); MS (m/e) 487 (M+1); retention time 7.65 minute; mp 175-177° C.

Example 5

2-[5-Chloro-2-(2-oxo-2,3,4,5-tetrahydro-1H-benzo[b]azepin-7-ylamino)-pyrimidin-4-ylamino]-N-methyl-benzenesulfonamide 5a) Following a procure analogous to 4b, 7-Amino-1-methyl-1,3,4,5-tetrahydrobenzo[b]azepin-2-one and 2-(2,5-Dichloro-pyrimidin-4-ylamino)-N-methyl-benzenesulfonamide were converted to 2-[5-Chloro-2-(2-oxo-2,3,4,5-tetrahydro-1H-benzo[b]azepin-7-ylamino)-pyrimidin-4-ylamino]-N-methyl-benzenesulfonamide. $^1$H NMR (400 MHz, DMSO-d$_6$) δ9.47 (s, 1H), 9.32 (s, 1H), 9.24 (s, 1H), 8.47 (m, 1H), 8.27 (s, 1H), 7.82 (m, 2H), 7.63 (m, 1H), 7.52 (s, 1H), 7.42 (m, 1H), 7.31 (m, 1H), 6.84 (d, J=8.54 Hz, 1H), 3.29 (m, 3H), 2.55-2.43 (m along with solvent peak, 2H), 2.07 (m, 4H); MS (m/e) 473, 474 (M+H); mp 276-282° C.

Example 6

2-[5-Chloro-2-(1-methyl-2-oxo-2,3,4,5-tetrahydro-1H-benzo[b]azepin-7-ylamino)-pyrimidin-4-ylamino]-N-(2-hydroxy-ethyl)-benzamide 6a) Following a procedure analogous to 1d, 2-Amino-N-(2-hydroxy-ethyl)-benzamide (synthesized according to a procedure in the literature: 1,2,3-Benzotriazin-4(3H)-ones and related systems. Part 5. Thermolysis of 3-aryl- and 3-alkenyl-1,2,3-benzotriazin-4(3H)-ones. Barker, Alan J.; Paterson, Thomas McC.; Smalley, Robert K.; Suschitzky, Hans. Journal of the Chemical Society, Perkin Transactions 1: Organic and Bio-Organic Chemistry (1972-1999) (1979), (9), 2203-8) was converted to 2-(2,5-Dichloro-pyrimidin-4-ylamino)-N-(2-hydroxy-ethyl)-benzamide which, following a procedure analogous to 1e was converted to 2-[5-Chloro-2-(1-methyl-2-oxo-2,3,4,5-tetrahydro-1H-benzo[b]azepin-7-ylamino)-pyrimidin-4-ylamino]-N-(2-hydroxy-ethyl)-benzamide. $^1$H NMR (400 MHz, DMSO-d$_6$) δ 11.48 (s, 1H), 9.51 (s, 1H), 8.76-8.67 (overlapping d & t, 2H), 8.23 (s, 1H), 7.79 (d, J=7.80 Hz, 1H0, 7.59-7.47 (two m, 3H0, 7.21 (d, J=8.54 Hz, 1H), 7.14 (dd, J=7.73 Hz and 7.45 Hz, 1H), 4.75 (t, J=5.68 Hz, 1H), 3.54 (m, 2H), 3.55-3.33 (m, 2H), 3.31 (s, 3H), 2.55 (m, 2H), 2.14-2.01 (2m, 4H); MS (m/e) 481, 482 (M+H); mp 190-194° C.

Example 7

2-[5-Chloro-2-(1-methyl-2-oxo-2,3,4,5-tetrahydro-1H-benzo[b]azepin-7-ylamino)-pyrimidin-4-ylamino]-benzamide 7a) Following a procedure analogous to 1d and 1e, 2-Amino-benzamide was converted to 2-(2,5-Dichloro-pyrimidin-4-ylamino)-benzamide which was converted to 2-[5-Chloro-2-(1-methyl-2-oxo-2,3,4,5-tetrahydro-1H-benzo[b]azepin-7-ylamino)-pyrimidin-4-ylamino]-benzamide. $^1$H NMR (400 MHz, DMSO-d$_6$) δ 11.85 (s, 1H), 9.54 (s, 1H), 8.70-8.82 (m, 1H), 8.20-8.42 (m, 2H), 7.36-7.90 (m, 5H), 7.07-7.21 (m, 2H), 3.22 (s, 3H), 2.48-2.58 (m, 2H), 1.92-2.19 (m, 4H); MS (m/e) 437 (M+1);

Example 8

{7-[5-Chloro-4-(2-methylsulfamoyl-phenylamino)-pyrimidin-2-ylamino]-2-oxo-2,3,4,5-tetrahydro-benzo[b]azepin-1-yl}-acetic acid methyl ester 8a) 7-Nitro-1,3,4,5-tetrahydro-benzo[b]azepin-2-one (375 mg, 1.82 mmol) and methyl bromoacetate (417 mg, 2.73 mmol) were dissolved in anhydrous DMF. Sodium hydride (60% in mineral oil, 146 mg, 3.64 mmol) was added, and the mixture was heated to 60° C. for 2 hours. After cooling to room temperature, the mixture was partitioned between ethyl acetate and water, washed once with water, and concentrated to a brown oil. Preparative TLC (50% EtOAc/hexane) afforded (7-Nitro-2-oxo-2,3,4,5-tetrahydro-benzo[b]azepin-1-yl)-acetic acid methyl ester as a yellow solid, 454 mg. (90% yield) $^1$H NMR (400 MHz, DMSO-d$_6$) δ 8.23 (s, 1H), 8.12-8.18 (m, 1H), 7.51-7.56 (m, 1H), 4.60 (s, 2H), 3.62 (s, 3H), 2.93-3.00 (m, 2H), 2.05-2.20 (m, 4H); MS (m/e) 279 (M+1).

8b) 7-Nitro-2-oxo-2,3,4,5-tetrahydro-benzo[b]azepin-1-yl)-acetic acid methyl ester 9 (454 mg, 1.63 mmol), ammonium formate (400 mg), and 10% palladium on carbon (200 mg) were suspended in ethanol (8 ml) and heated to reflux 30 minutes. The heat was removed, and additional amounts of ammonium formate (400 mg) and 10% palladium on carbon (200 mg) were added. The mixture was refluxed an additional 30 minutes, cooled to room temperature, filtered through Celite, and concentrated. The resulting brown residue was partitioned between ethyl acetate and water, washed once with water, and concentrated. Preparative TLC (50% EtOAc/hexane) afforded (7-Amino-2-oxo-2,3,4,5-tetrahydro-benzo[b]azepin-1-yl)-acetic acid methyl ester as a white foam, 270 mg. (67% yield) $^1$H NMR (400 MHz, DMSO-d$_6$) δ 6.86-6.91 (m, 1H), 6.38-6.44 (m, 2H), 5.06 (s, 2H), 4.44 (s, 2H), 3.61 (s, 3H), 2.51-2.82 (m, 2H), 1.92-2.22 (m, 4H); MS (m/e) 249 (M+1).

8c) 7-Amino-2-oxo-2,3,4,5-tetrahydro-benzo[b]azepin-1-yl)-acetic acid methyl ester (270 mg, 1.09 mmol), 2-(2,5-Dichloro-pyrimidin-4-ylamino)-N-methyl-benzenesulfonamide (362 mg, 1.09 mmol) and 4N HCl in dioxane (0.273 ml, 1.09 mmol) were dissolved in 2-methoxyethanol (5 ml) and heated to 120° C. for 18 hours. The mixture was concentrated to a brown oil. Preparative TLC (5% MeOH/CH$_2$Cl$_2$) gave the title compound as a white solid, 327 mg. (55% yield) $^1$H NMR (400 MHz, DMSO-d$_6$) δ 9.58 (s, 1H), 9.23 (s, 1H), 8.38-8.50 (m, 1H), 8.29 (s, 1H), 7.72-7.87 (m, 2H), 7.60-7.68 (m, 1H), 7.54 (s, 1H), 7.46-7.51 (d, 1H), 7.28-7.35 (m, 1H), 7.22-7.29 (m, 1H), 4.48 (s, 2H), 3.63 (s, 3H), 2.53-2.84 (m, 2H), 2.44 (s, 3H), 1.96-2.26 (m, 4H); MS (m/e) 545 (M+1); retention time 8.28 minute; mp 237-239° C.

Example 9

{7-[5-Chloro-4-(2-methylsulfamoyl-phenylamino)-pyrimidin-2-ylamino]-2-oxo-2,3,4,5-tetrahydro-benzo[b]azepin-1-yl}-acetic acid 9a) {7-[5-Chloro-4-(2-methylsulfamoyl-phenylamino)-pyrimidin-2-ylamino]-2-oxo-2,3,4,5-tetrahydro-benzo[b]azepin-1-yl}-acetic acid methyl ester (67 mg, 0.123 mmol) was taken up in THF (1 ml). 1N NaOH (1 ml) was added, and the mixture was stirred 18 hours at room temperature. 10% citric acid was added to make the mixture acidic. It was washed with ethyl acetate, and the organic phase was then washed with water, concentrated, and triturated with dichloromethane. Filtration yielded the title compound as a tan solid, 44 mg. (69% yield) $^1$H NMR (400 MHz, DMSO-d$_6$) δ 12.69 (s, 1H), 9.57 (s, 1H), 9.27 (s, 1H), 8.40-8.52 (m, 1H), 8.29 (s, 1H), 7.70-7.86 (m, 2H), 7.42-7.68 (m, 3H), 7.24-7.32 (m, 1H), 7.09-7.15 (m, 1H), 4.36 (s, 2H), 2.58-2.85 (m, 2H), 2.35 (s, 3H), 1.95-2.23 (s, 4H); MS (m/e) 531 (M+1); mp 192-195° C.; retention time 6.97 minute.

Example 10

2-(5-Chloro-2-{1-[2-(4-methyl-piperazin-1-yl)-2-oxo-ethyl]-2-oxo-2,3,4,5-tetrahydro-1H-benzo[b]azepin-7-ylamino}-pyrimidin-4-ylamino)-N-methyl-benzenesulfonamide 10a) {7-[5-Chloro-4-(2-methylsulfamoyl-phenylamino)-pyrimidin-2-ylamino]-2-oxo-2,3,4,5-tetrahydro-benzo[b]azepin-1-yl}-acetic acid (227 mg, 0.43 mmol), N-methylpiperazine (48 μl, 0.43 mmol), 1-[3-(dimethylamino)propyl]3-ethylcarbodiimide hydrochloride (98 mg, 0.51 mmol), N-methylmorpholine (119 μl, 2.5 mmol), and hydroxybenzotriazole (69 mg, 0.51 mmol) were dissolved in anhydrous DMF, and the solution was stirred 18 hours at room temperature. It was then partitioned between ethyl acetate and water, and washed once with aqueous sodium bicarbonate and once with water. Concentration afforded a yellow foam. Preparative TLC (10% MeOH/CH$_2$Cl$_2$) gave 2-(5-Chloro-2-{1-[2-(4-methyl-piperazin-1-yl)-2-oxo-ethyl]-2-oxo-2,3,4,5-tetrahydro-1H-benzo[b]azepin-7-ylamino}-pyrimidin-4-ylamino)-N-methyl-benzenesulfonamide as a white solid, 147 mg. (56% yield) $^1$H NMR (400 MHz, DMSO-d$_6$) δ 9.51 (s, 1H), 9.27 (s, 1H), 8.43-8.51 (m, 1H), 8.23 (s, 1H), 7.70-7.83 (m, 2H), 7.58-7.64 (m, 1H), 7.41-7.48 (m, 2H), 7.23-7.30 (m, 1H), 7.08-7.12 (m, 1H), 4.58 (s, 2H), 3.34-3.43 (m, 4H), 2.62-3.10 (m, 2H), 2.39 (s, 3H), 1.96-2.32 (m, 11H); MS (m/e) 613 (M+1); retention time 5.99 minute; mp 148-151° C.

Example 11

2-[5-Chloro-2-(1-oxo-2,3,4,5-tetrahydro-1H-benzo[c]azepin-7-ylamino)-pyrimidin-4-ylamino]-N-methyl-benzamide 11a) 6-Aminotetralone (1.98 g, 12.3 mmol), hydroxylamine hydrochloride (0.85 g, 12.3 mmol), sodium acetate (2.52 g, 30.7 mmol), and water (3.3 ml) were dissolved in ethanol (10 ml), and the mixture was heated to reflux 4 hours. After cooling to room temperature, the mixture was diluted with water (20 ml), and the resulting precipitate was filtered to obtain 6-Amino-3,4-dihydro-2H-naphthalen-1-one oxime as a light brown solid, 1.80 g. (83% yield) $^1$H NMR (400 MHz, DMSO-d$_6$) δ 10.41 (s, 1H), 7.48-7.53 (m, 1H), 6.36-6.40 (m, 1H), 6.27 (s, 1H), 5.20 (s, 2H), 2.44-2.53 (m, 4H), 1.60-1.69 (m, 2H); MS (m/e) 177 (M+1).

11b) 6-Amino-3,4-dihydro-2H-naphthalen-1-one oxime (1.80 g, 10.2 mmol) and polyphosphoric acid (30 ml) were mixed together. The viscous mixture was heated to 100° C. with vigorous stirring as the mixture became homogeneous. After cooling to room temperature, the mixture was diluted with water (30 ml). 15% aqueous sodium hydroxide was added until the mixture became basic. Extraction with ethyl acetate (50 ml), drying over anhydrous magnesium sulfate, and concentration yielded a brown oil. Preparative TLC (5% MeOH/CH$_2$Cl$_2$) afforded 7-Amino-2,3,4,5-tetrahydro-benzo[c]azepin-1-one (Bioorganic & Medicinal Chem. Lett., 2003, 13 4197) as a light brown oil, 21 mg. $^1$H NMR (400 MHz, DMSO-d$_6$) δ 7.53 (s, 1H), 7.14-7.22 (m, 1H), 6.42-6.47 (m, 1H), 6.33 (s, 1H), 5.44 (s, 2H), 2.87-2.93 (m, 2H), 2.53-2.60 (m, 2H), 1.78-1.87 (m, 2H); MS (m/e) 177 (M+1).

11c) 7-Amino-2,3,4,5-tetrahydro-benzo[c]azepin-1-one (21 mg, 0.12 mmol) and 2-(2,5-dichloro-pyrimidin-4-ylamino)-N-methyl-benzamide (36 mg, 0.12 mmol) were suspended in 2-methoxyethanol (1 ml), and heated to 120° C. for 5 hours. Concentration afforded a yellow solid. Preparative TLC (5% MeOH/CH$_2$Cl$_2$) gave the title compound the desired as a white solid, 13 mg. (25% yield) $^1$H NMR (400 MHz, DMSO-d$_6$) δ 11.59 (s, 1H), 9.68 (s, 1H), 8.68-8.77 (m, 2H), 8.30 (s, 1H), 7.80-7.86 (m, 1H), 7.71-7.78 (m, 1H), 7.59 (s, 2H), 7.43-7.51 (m, 1H), 7.34-7.39 (m, 1H), 7.12-7.18 (m, 1H), 2.85-2.97 (m, 2H), 2.79 (s, 3H), 2.60-2.71 (m, 2H), 1.80-1.90 (m, 2H); MS (m/e) 437 (M+1).

Example 12

2-{5-Chloro-2-[(S)-(2,3,3a,4-tetrahydro-1H,6H-5-oxa-10b-aza-benzo[e]azulen-8-yl)amino]-pyrimidin-4-ylamino}-N-methyl-benzamide 12a) By adopting a similar procedure as described in "Mueller, W; Stauss, U.; Forschungsinst, W.; Bern, S. Helvetica Chimica Acta 1982, 65, 2118." (S)-8-Nitro-2,3,3a,4-tetrahydro-1H-5-oxa-10b-aza-benzo[e]azulen-6-one was prepared as follows. A mixture of 2-fluoro-5-nitro-benzoic acid ethyl ester (1.16 g, 5.44 mmol.), S-prolinol (638 mg, 6.31 mmol) and diisopropylethylamine (1.5 mL, 8.62 mmol) in dry NMP (20 mL) was stirred at 100° C. for 3 h. Solvent was removed and the mixture was partition between EtOAc and water. Organic layer was extracted two more times with EtOAc. Combined organic was washed successively with water (twice) and brine. After drying over magnesium sulfate, solvent was evaporated. The product, (S)-8-Nitro-2,3,3a,4-tetrahydro-1H-5-oxa-10b-aza-benzo[e]azulen-6-one was obtained as a solid (1.08 g, 80%).

12b) (S)-8-Nitro-2,3,3a,4-tetrahydro-1H-5-oxa-10b-aza-benzo[e]azulen-6-one (1 g, 4 mol) was taken in MeOH (50 mL) and was cooled to 0° C. Sodium borohydride (1 g, 26.43 mmol, 300 mg was added in portion in the first phase, 700 mg after 4 h at RT) was added and the cooling bath was removed. After stirring overnight at RT, the mixture was quenched with water. The mixture was treated with 1N $Na_2CO_3$ solution (100 mL) and dichloromethane (100 mL). The mixture was extracted from dichloromethane (twice). Combined organic was washed successively with water (twice) and brine. After drying over magnesium sulfate, solvent was evaporated. A gum was obtained which was taken in 50% $H_2SO_4$ (20 mL). The mixture was stirred at 120° C. for 45 minutes. The mixture was cooled to RT and was neutralized with NaHCO3 solution and was extracted from EtOAc. Combined organic was washed successively with water (twice) and brine. After drying over magnesium sulfate, solvent was evaporated. The crude product was purified by flash chromatography (hexane: EtOAc 3:1). The product (S)-8-Nitro-2,3,3a,4-tetrahydro-1H-5-oxa-10b-aza-benzo[e]azulen-6-one was obtained as an yellow solid (451 mg, 48% in two steps); $^1H$ NMR (400 MHz, DMSO-$d_6$) δ 8.02 (d, J=9.1 Hz, 1H), 8.00 (s, 1H), 6.75 (d, J=9.09 Hz, 1H0, 5.14 (d, J=14.14 Hz, 1H), 4.36 (d, J=13.89 Hz, 1H), 5.14 (d, J=14.14 Hz, 1H0, 4.36 (d, J=13.89 Hz, 1H), 4.07 (m, 1H0, 3.93 (m, 1H), 3.41 (m, 1H), 3.35-3.31 (2m, 2H), 2.17-1.89 (2m, 3H), 1.57 (m, 1H); MS (m/e) 235 (M#H).

12c) By following the procedure as described for the 7-Amino-1-methyl-1,3,4,5-tetrahydrobenzo[b]azepin-2-one) nitro group of S-8-Nitro-2,3,3a,4-tetrahydro-1H,6H-5-oxa-10b-aza-benzo[e]azulene was reduced (yield-97%). The product, (S)-(2,3,3a,4-Tetrahydro-1H,6H-5-oxa-10b-aza-benzo[e]azulen-8-yl)amine was used for the next step without further purification.

12d) As per the procedure described in Example 1, the reaction of 2-(2,5-dichloro-pyrimidin-4-ylamino)-N-methyl-benzamide and (S)-(2,3,3a,4-Tetrahydro-1H,6H-5-oxa-10b-aza-benzo[e]azulen-8-yl)amine gave 2-{5-Chloro-2-[(S)-(2, 3,3a,4-tetrahydro-1H,6H-5-oxa-10b-aza-benzo[e]azulen-8-yl)amino]-pyrimidin-4-ylamino}-N-methyl-benzamide, upon purification by flash chromatography (Dichloromethane:MeOH 98:2) followed by trituration with $Et_2O$: MeOH (9:1), as solid (21%); $^1H$ NMR (400 MHz, DMSO-$d_6$) δ11.59 (s, 1H), 9.24 (s, 1H), 8.74 (br s, 1H), 8.17 (s, 1H), 7.74 d, J=7.87 Hz, 1H), 7.48 (m, 2H), 7.36 (d, J=8.40 Hz, 1H0, 7.12 (m, 1H0, 6.83 (d, J=8.40 Hz, 1H0, 7.12 (m, 1H), 6.83 (d, J=8.71 Hz, 1H), 4.56 (d, J=13.03 Hz, 1H0, 4.30 (d, J=13.02 Hz, 1H), 3.89 (d, J=11.55 Hz, 1H), 3.31-3.2 (m, 4H), 2.90 (m, 1H), 2.81 (s, 3H), 2.12-1.45 (3m, 4H); MS (m/e) 465, 466 (M+H); mp 216-218° C.

Example 13

2-{5-Chloro-2-[(S)-(2,3,3a,4-tetrahydro-1H,6H-5-oxa-10b-aza-benzo[e]azulen-8-yl)amino]-pyrimidin-4-ylamino}-N-methyl-benzenesulfonamide 13a) Following an analogous procedure to that described in Example 5, the reaction of 2-(2,5-Dichloro-pyrimidin-4-ylamino)-N-methyl-benzenesulfonamide and (S)-(2,3,3a,4-Tetrahydro-1H,6H-5-oxa-10b-aza-benzo[e]azulen-8-yl) amine gave 2-{5-Chloro-2-[(S)-(2,3,3a,4-tetrahydro-1H,6H-5-oxa-10b-aza-benzo[e]azulen-8-yl)amino]-pyrimidin-4-ylamino}-N-methyl-benzenesulfonamide, upon purification by flash chromatography (Dichloromethane:MeOH 98:2) followed by trituration with $Et_2O$, as solid (32%)$_2$-{5-Chloro-2-[(S)-(2,3,3a,4-tetrahydro-1H,6H-5-oxa-10b-aza-benzo[e]azulen-8-yl)amino]-pyrimidin-4-ylamino}-N-methyl-benzenesulfonamide; $^1H$ NMR (400 MHz, DMSO-$d_6$) δ9.30 (s, 2H), 8.56 (m, 1H), 8.22 (s, 1H), 7.79 (m, 2H), 7.63 (m, 1H), 7.44 (s, 1H), 7.34 (m, 1H), 7.28 (m, 1H), 6.81 (d, J=8.71 Hz, 1H0, 4.53 (d, J=13.04 Hz, 1H), 4.27 (d, J=13.01 Hz, 1H), 3.88 (d, J=9.54 Hz, 1H), 3.31-3.19 (2m along with water peak, 2H), 2.88 (m, 1H), 2.43 (d, J=4.73 Hz, 3H), 2.07 (m, 1H), 1.84 (m, 1H), 1.47 (m, 1H); MS (m/e) 501, 502 (M+H); mp 187-188° C.

Example 14

2-[5-Chloro-2-(7,7a,8,9,10,11-hexahydro-5H-6-oxa-11a-aza-dibenzo[a,c]cyclohepten-3-ylamino)-pyrimidin-4-ylamino]-N-methyl-benzamide 14a) Following procedures analogous to Example 12, piperidin-2-yl-methanol was converted to 2-[5-Chloro-2-(7,7a, 8,9,10,11-hexahydro-5H-6-oxa-11a-aza-dibenzo[a,c]cyclohepten-3-ylamino)-pyrimidin-4-ylamino]-N-methyl-benzamide. $^1H$ NMR (400 MHz, DMSO-$d_6$) δ11.58 (s, 1H), 9.30 (s, 1H), 8.74 (d, J=7.77 Hz, 1H0, 7.53 (d, J=2.25 Hz, 1H), 7.46 (m, 2H), 7.12 (t, J=7.49 Hz, 1H), 6.84 (d, J=8.58 Hz, 1H), 4.81 (d, J=10.99 Hz, 1H), 4.42 (d, J=11.04 Hz, 1H), 3.63 (dd, J=12.94 Hz, 2.68 Hz, 1H), 2.81 ((d, J=4.44 Hz, 3H), 2.66 (d, J=8.07 Hz, 1H0, 1.87-1.44 (series of m, 6H); MS (m/e) 479, 480 (M+H); mp 220-221° C.

Example 15

2-[5-Chloro-2-(1-methyl-1,2,3,5-tetrahydro-benzo[e][1,4]oxazepin-7-ylamino)-pyrimidin-4-ylamino]-N-methyl-benzamide 15a) Following procedures analogous to Example 12, 2-methylamino-ethanol was converted 2-[5-Chloro-2-(1-methyl-1,2,3,5-tetrahydro-benzo[e][1,4]oxazepin-7-ylamino)-pyrimidin-4-ylamino]-N-methyl-benzamide $^1H$ NMR (400 MHz, DMSO-$d_6$) δ11.59 (s, 1H), 9.26 (s, 1H), 8.74 (br s, 2H), 8.17 (d, J=2.78, 1H), 7.74 (d, J=7.61, 1H), 7.52-7.46 (m, 2H), 7.38 (d, J=8.44 Hz, 1H), 7.12 (m, 1H), 6.87 (d, J=8.71 Hz, 1H), 4.43 (s, 2H), 3.76 (br s, 2H), 2.92 (br s, 2H), 2.85 (s, 3H), 2.81 (d, J=4.30 Hz, 3H); MS (m/e) 439, 440 (M+H); mp 216-217° C.

Example 16

2-[5-Chloro-2-(1-methyl-1,2,3,5-tetrahydro-benzo[e][1,4]oxazepin-7-ylamino)-pyrimidin-4-ylamino]-N-(2-hydroxy-ethyl)-benzamide and 2-{2-[5-Chloro-2-(1-methyl-1,2,3,5-tetrahydro-benzo[e][1,4]oxazepin-7-ylamino)-pyrimidin-4-ylamino]-phenyl}-oxazolidin-2-ol 16a) Following procedures analogous to Example 12a-c and 6,2-methylamino-ethanol was converted 2-[5-Chloro-2-(1-methyl-1,2,3,5-tetrahydro-benzo[e][1,4]oxazepin-7-ylamino)-pyrimidin-4-ylamino]-N-(2-hydroxy-ethyl)-benzamide and 2-{2-[5-Chloro-2-(1-methyl-1,2,3,5-tetrahydrobenzo[e][1,4]oxazepin-7-ylamino)-pyrimidin-4-ylamino]-phenyl}-oxazolidin-2-ol, equilibrium mixture by NMR $^1$H NMR (400 MHz, DMSO-d$_6$) δ11.49 9s, 0.75H), 11.3 (s, 0.25H0, 9.26 (s, 0.75H0, 8.73 (br s, 1.5H0, 8.17 (s, 0.75), 7.92 (d, J=8.12 Hz, 0.25H), 7.64-7.46 (2m & 1S, 2.75H), 7.38-7.1 (2m, 1.25H), 6.86 (d, J=8.26 Hz, 0.75H), 4.75 (m, 1H), 4.42 (s, 1.5H), 4.09-3.97 (2m, 1H), 3.76 (br s, 1.5ZH), 3.52 (m, 2H), 3.35 (m, 2H), 3.17 (d, J=5.01 Hz, 1H), 2.92 and 2.85 (2s, 4H). MS (m/e) 469, 470 (M+H); mp 239-241° C.

Example 17

2-[5-Chloro-2-(1-methyl-1,2,3,5-tetrahydro-benzo[e][1,4]oxazepin-7-ylamino)-pyrimidin-4-ylamino]-N-methyl-benzenesulfonamide 17a) Following procedures analogous to Example 12a-c and 13a, 2-methylamino-ethanol was converted to 2-[5-Chloro-2-(1-methyl-1,2,3,5-tetrahydro-benzo[e][1,4]oxazepin-7-ylamino)-pyrimidin-4-ylamino]-N-methyl-benzenesulfonamide $^1$H NMR (400 MHz, DMSO-d$_6$) δ9.31 (br s, 2H), 8.55 (m, 1H), 8.22 (s, 1H), 7.80 (m, 2H), 7.62 (m, 1H), 7.47 (s, 1H), 7.36 (m, 1H), 7.27 (m, 1H), 6.84 (d, J=8.62 Hz, 1H), 4.39 (s, 2H0, 3.75 (br s, 2H0, 2.90 (br s, 2.84 (s, 3H), 2.44 (s, 3H); MS (m/e) 475, 476 (M+H); mp 163-164° C.

Example 18

2-[5-Chloro-2-(6-methoxy-2-oxo-2,3,4,5-tetrahydro-1H-benzo[b]azepin-9-ylamino)-pyrimidin-4-ylamino]-N-methyl-benzamide 18a) 6-Methoxy-9-nitro-1,3,4,5-tetrahydro-benzo[b]azepin-2-one was prepared from using the method of Alfred, H., Boaz, A.; Marks, V.; Gottlieb, H. E.; *J. Org. Chem.* 2003, 68, 6853.

18b) 9-Amino-6-methoxy-1,3,4,5-tetrahydro-benzo[b]azepin-2-one was prepared from 6-methoxy-9-nitro-1,3,4,5-tetrahydro-benzo[b]azepin-2-one via reduction of the nitro group as described for the preparation of 7-Amino-1-methyl-1,3,4,5-tetrahydrobenzo[b]azepin-2-one. The crude product was purified by flash chromatography (EtOAc) and the product was obtained as a solid (36%); (400 MHz, DMSO-d$_6$) δ6.62 (d, J=8.84 Hz, 1H), 6.56 (d, J 8.84 Hz, 1H), 4.52 (br s, 1H), 3.66 (s, 3H), 3.16 (d, J=3.31 Hz, 2H), 2.64 (m, 2H), 2.04 (m, 2H), 1.97 (m, 2H); MS (m/e) 207 (M+H).

18c) Analogous to the procedure described in Example 1, the reaction of 2-(2,5-dichloro-pyrimidin-4-ylamino)-N-methyl-benzamide and 9-amino-6-methoxy-1,3,4,5-tetrahydro-benzo[b]azepin-2-one gave 2-[5-chloro-2-(6-methoxy-2-oxo-2,3,4,5-tetrahydro-1H-benzo[b]azepin-9-ylamino)-pyrimidin-4-ylamino]-N-methyl-benzamide, upon purification by flash chromatography (Dichloromethane:MeOH 97:3) followed by PLC (hexane:EtOAc 1:1), as solid (6%): $^1$H NMR (400 MHz, CD$_3$OD) δ8.3 (br s, 1H), 7.60 (dd, J=7.70 Hz, 1.44 Hz, 1H), 7.26 (d, J=8.78 Hz, 1H), 7.06 (m, 1H), 7.04 (m, 1H), 6.93 (d, J=8.83 Hz, 1H), 3.89 (s, 3H), 2.90 (s, 3H), 2.82 (m, 2H0, 2.06 (m, 4H); MS (m/e) 467, 468 (M+H);

Example 19

(2-exo,3-exo)-3-[5-Chloro-2-(1-methyl-2-oxo-2,3,4,5-tetrahydro-1H-benzo[b]azepin-7-ylamino)-pyrimidin-4-ylamino]-bicyclo[2.2.1]hept-5-ene-2-carboxamide 19a) A mixture of (2-exo,3-exo)3-amino-bicyclo[2.2.1]hept-5-ene-2-carboxamide (250 mg, 1.64 mmol), 2,4,5-trichloro-pyrimidine (366 mg, 1.99 mmol) and NaHCO$_3$ (280 mg, 3.33 mmol) in methanol (4 mL) and water (2 mL) was stirred at RT for 69 h. The mixture was diluted with water, extracted twice from EtOAc Combined organic was washed successively with water (twice) and brine. After drying over magnesium sulfate, solvent was evaporated. The product was triturated with diethyl ether, filtered and washed with diethyl ether. The product (2-exo,3-exo)-3-(2,5-dichloro-pyrimidin-4-ylamino)-bicyclo[2.2.1]hept-5-ene-2-carboxamide was isolated as a white solid (276 mg, 56%); (400 MHz, DMSO-d$_6$) δ 8.61 (d, J=7.32 Hz, 1H), 8.20 (s, 1H0, 7.86 (s, 1H), 7.32 (s, 1H), 6.33 (br s, 1H), 6.30 (br s, 1H), 3.99 (m, 1H), 2.88 (s, 1H), 2.75 (s, 1H), 2.04 (d, J=8.84 Hz, 1H), 1.40 (d, J=8.84 Hz, 1H); MS (m/e) 299, 300 (M+H).

19b) Following an analogous procedure to that described in Example 1, the reaction of 3-exo-(2,5-Dichloro-pyrimidin-4-ylamino)-bicyclo[2.2.1]hept-5-ene-2-exo-carboxamide and 7-Amino-1,3,4,5-tetrahydro-benzo[b]azepin-2-one gave 2-[5-chloro-2-(6-methoxy-2-oxo-2,3,4,5-tetrahydro-1H-benzo[b]azepin-9-ylamino)-pyrimidin-4-ylamino]-N-methyl-enzamide, upon purification by flash chromatography (dichloromethane:MeOH 97:3) followed by trituration in diethylether. The product 3-exo[5-Chloro-2-(1-methyl-2-oxo-2,3,4,5-tetrahydro-1H-benzo[b]azepin-7-ylamino)-pyrimidin-4-ylamino]-bicyclo[2.2.1]hept-5-ene-2-exo-carboxamide was isolated as a solid (35%); $^1$H NMR (400 MHz, DMSO-d$_6$) δ 9.33 (s, 1H), 7.97 (s, 1H), 7.78 (br s, 2H), 7.71 (m, 1H), 7.56 (s, 1H), 7.27 (s, 1H), 7.21 (d, J=8.68 Hz, 1H), 6.35 (br s, 1H), 6.29 (br s, 1H), 4.13 (m, 1H), 3.20 (s, 3H), 2.88 (br s, 1H), 2.78 (br s, 1H), 2.55 (m, 3H), 2.14-2.04 (2m, 5H), 1.41 (d, J=8.57 Hz, 1H); MS (m/e) 453, 454 (M+H); mp 266-267° C.

Example 20

2-[5-Chloro-2-(1-methyl-2-oxo-2,3,4,5-tetrahydro-1H-benzo[b]azepin-7-ylamino)-pyrimidin-4-ylamino]-cyclohexanecarboxylic acid amide 20a) Following an analogous procedure to Example 19, 7-Amino-1,3,4,5-tetrahydro-benzo[b]azepin-2-one and 2-(2,5-Dichloro-pyrimidin-4-ylamino)-cyclohexanecarboxylic acid amide (prepared in analogous fashion to 19a with 2-amino-cyclohexanecarboxylic acid amide and 2,4,5-trichloropyrimidine) were converted to 2-[5-Chloro-2-(1-methyl-2-oxo-2,3,4,5-tetrahydro-1H-benzo[b]azepin-7-ylamino)-pyrimidin-4-ylamino]-cyclohexanecarboxylic acid amide. $^1$H NMR (400 MHz, DMSO-d$_6$) δ 9.31 (s, 1H), 7.97 (s, 1H0, 7.69 (s, 1H0, 7.57 (d, J=8.37 Hz, 1H0, 7.69 (s, 1H0, 7.57 (d, J=8.37 Hz, 1H0, 7.48 (br s, 1H), 7.19 (d, J=8.66 Hz, 1H0, 7.06 (s, 1H), 6.83 (m, 1H), 4.01 (br s, 1H), 3.31 (br s, 1H), 3.31 (m with water peak, 4H), 2.71 (br s, 1H), 2.59 (m, 2H), 2.14-2.05 (2m, 6H), 1.62-1.2 (2m, 6H); MS (m/e) 443, 444 (M+H); mp 251-253° C.

Example 31

2-[5-Chloro-2-(3-ethyl-2,3,4,5-tetrahydro-1H-benzo[d]azepin-7-ylamino)-pyrimidin-4-ylamino]-N-methyl-benzamide 31a) (2-Carboxymethyl-phenyl)-acetic acid (5.0 g/25 mmol) was dissolved in THF (100 mL) and cooled to 0° C. Borane (1 M in THF, 100 mL/100 mmol) was then added dropwise while stirring (hydrogen evolution). The reaction was left to stir a 0° C. for four hours then carefully quenched by the addition of water (ca. 20 mL). The reaction was partitioned between diethyl ether (200 mL) and water (200 mL). The organic layer was extracted with an additional portion of ether (100 mL) and the combined organics washed with brine (100 mL), dried over magnesium sulfate, filtered and concentrated. To give 2-[2-(2-Hydroxy-ethyl)-phenyl]-ethanol (3.3 g/80%). $^1$H NMR (400 MHz, CDCl$_3$) δ 7.2 (m, 4H), 3.9 (t, J=6.8 Hz, 4H), 2.95 (t, J=6.8 Hz, 4H).

31b) 2-[2-(2-Hydroxy)-ethyl)-phenyl]-ethanol was dissolved in methylene chloride (100 mL) and cooled to 0° C. Triethylamine (11.0 mL, 80 mmol) was added followed by the dropwise addition of methanesulfonyl chloride (3.5 mL/44 mmol, exothermic). After 30 minutes, the reaction was poured into a separatory funnel and sequentially washed with 1 N hydrochloric acid (100 mL), water (100 mL) and aqueous sodium bicarbonate (100 mL). The organic solution was then dried over magnesium sulfate, filtered and concentrated to give methanesulfonic acid 2-[2-(2-methanesulfonyloxy-ethyl)-phenyl]-ethyl ester a yellow oil (6.0 g/quantitative) that solidified on standing. $^1$H NMR (400 MHz, CDCl$_3$) δ 7.2 (m, 4H), 4.4 (t, J=7.1 Hz, 4H), 3.15 (t, J=7.1 Hz, 4H), 2.9 (s, 6H).

31c) A 350 mL pressure vessel was charged with the methanesulfonic acid 2-[2-(2-methanesulfonyloxy-ethyl)-phenyl]-ethyl ester (3.2 g/10 mmol) in a 1:1 mixture of acetonitrile and ammonium hydroxide (100 mL total volume). The vessel was sealed and heated to 100° C. for one hour (pressure rises to ca. 40 psi) and then gradually allowed to cool. The reaction contents were poured into water and acidified to ca. pH 4 with concentrated hydrochloric acid. The aqueous solution was extracted with diethyl ether (100 mL), basified to pH 14 with 30% aqueous sodium hydroxide and finally extracted repeatedly with 10% methanol/methylene chloride (4×50 mL). The combined organic extracts are dried over magnesium sulfate, filtered and concentrated to afford 2,3,4,5-tetrahydro-1H-benzo[d]azepine as a pale yellow oil (1.2 g/81%) that solidifies on standing. $^1$H NMR (400 MHz, CDCl$_3$) δ 7.1 (m, 4H), 2.91 (m, 8H).

31d) 2,3,4,5-Tetrahydro-1H-benzo[d]azepine (535 mg/3.63 mmol, neat) was cooled to −10° C. (acetone/ice bath), treated with neat fuming nitric acid (ca. 10 mL, precooled to −10° C.), and allowed to stir for 30 minutes. The yellow solution was then poured onto ice with vigorous stirring. The resulting white solid was collected by filtration and washed with ice cold water and dried in vacuo to afford the nitrate salt of 7-Nitro-2,3,4,5-tetrahydro-1H-benzo[d]azepine as a white solid (650 mg/70%). The filtrate was basified with 1 N sodium hydroxide and extracted with methylene chloride (2×20 mL). The extracts were dried and concentrated to yield an additional 200 mg (25%) of the free base 7-Nitro-2,3,4,5-tetrahydro-1H-benzo[d]azepine. $^1$H NMR (400 MHz, DMSO-d$_6$) δ 8.87 (br s, 2H), 8.13 (s, 1H), 8.08 (dd, J=8.1 Hz, 1H), 7.51 (d, J=8.1 Hz, 1H), 3.21 (m, 8H).

31e) 7-Nitro-2,3,4,5-tetrahydro-1H-benzo[d]azepine nitrate salt (1.03 g/4 mmol) was suspended in acetone (10 mL). Potassium carbonate and iodoethane were added sequentially and the suspension was heated to reflux with vigorous stirring for 2 hours. The mixture was then filtered through a pad of celite (rinsing with acetone) and the filtrate concentrated onto silica gel. 3-Ethyl-7-nitro-2,3,4,5-tetrahydro-1H-benzo[d]azepine was isolated by column chromatography on silica gel (eluting with 0→10% methanol/methylene chloride) as a yellow/orange oil (600 mg/72%). $^1$H NMR (400 MHz, CDCl$_3$) δ 7.98 (m, 2H), 7.28 (m, 1H), 3.15 (s, 4H), 2.91 (s, 4H), 2.79 (q, J=7.1 Hz, 2H), 1.20 (t, J=7.1 Hz, 3H).

31f) 3-Ethyl-7-nitro-2,3,4,5-tetrahydro-1H-benzo[d]azepine (740 mg/3.4 mmol) was dissolved in anhydrous methanol (ca. 10 mL) and the solution added to a Parr flask. Palladium (10% on charcoal) was added carefully (WARNING: this addition should be done under a atmosphere of nitrogen to avoid ignition of methanol vapor in flask) and the mixture shaken under 40 psi of hydrogen for 2 hours. The mixture was then filtered and the colorless filtrate concentrated to afford 3-Ethyl-2,3,4,5-tetrahydro-1H-benzo[d]azepin-7-ylamine (yellows upon standing). The material was typically used without further purification (680 mg/quantitative). $^1$H NMR (400 MHz, CDCl$_3$) δ 6.9 (d, J=7.6 Hz, 1H), 6.4 (m, 2H), 2.9 (m, 4H), 2.7 (m, 6H), 1.1 (t, J=7.1 Hz, 3H).

31g) 2-(2,5-Dichloro-pyrimidin-4-ylamino)-N-methylbenzamide (650 mg/2.2 mmol), 3-Ethyl-2,3,4,5-tetrahydro-1H-benzo[d]azepin-7-ylamine (500 mg/2.6 mmol) and 4 N HCl in dioxane (650 μL/2.6 mmol) were suspended in 2-methoxyethanol (5 mL) and heated to 120° C. until judged complete by HPLC. The resulting tan solution was cooled to room temperature, diluted with methanol (2 mL) and treated with solid potassium carbonate (carbon dioxide evolves). The mixture was filtered and the filtrate concentrated onto silica gel and purified by column chromatography to afford 2-[5-Chloro-2-(3-ethyl-2,3,4,5-tetrahydro-1H-benzo[d]azepin-7-ylamino)-pyrimidin-4-ylamino]-N-methyl-benzamide as a tan solid (200 mg/20%). $^1$H NMR (400 MHz, CDCl$_3$) δ 11.02 (s, 1H), 8.68 (d, J=8.1 Hz, 1H), 8.06 (s, 1H), 7.52-7.40 (m, 2H), 7.33 (s, 1H), 7.23 (s, 1H), 7.09-6.98 (m, 2H), 6.87 (s, 1H), 6.20 (s, 1H), 3.05 (d, J=3.8 Hz, 3H), 2.91 (m, 4H), 2.60 (m, 6H), 1.11 (t, J=6.9 Hz, 3H). LC/MS found 451 (M+H). mp 201° C.

Example 32

2-[5-Chloro-2-(3-ethyl-2,3,4,5-tetrahydro-1H-benzo[d]azepin-7-ylamino)-pyrimidin-4-ylamino]-N-methyl-benzenesulfonamide 32a) Analogous to procedure 31g, 2-(2,5-Dichloro-pyrimidin-4-ylamino)-N-methyl-benzenesulfonamide was converted to 2-[5-Chloro-2-(3-ethyl-2,3,4,5-tetrahydro-1H-benzo[d]azepin-7-ylamino)-pyrimidin-4-ylamino]-N-methyl-benzenesulfonamide. $^1$H NMR (400 MHz, DMSO-d$_6$) δ 9.40 (s, 1H), 9.25 (br s, 1H), 8.50 (d, J=7.0 Hz, 1H), 8.25 (s, 1H), 7.82 (m, 2H), 7.62 (dd, J=8.0, 8.0 Hz, 1H), 7.40 (s, 1H), 7.31 (t, 1H), 6.96 (d, J=8.1 Hz, 1H), 2.82-2.71 (m, 4H), 2.53-2.40 (m, 9H), 1.02 (t, J=7.0 Hz, 3H). LC/MS found 487 (M+H). mp 175° C.

Example 33

4-Chloro-2-[5-chloro-2-(3-ethyl-2,3,4,5-tetrahydro-1H-benzo[d]azepin-7-ylamino)-pyrimidin-4-ylamino]-N-methyl-benzamide 3a) Analogous to procedure 31g, 4-Chloro-2-(2,5-dichloro-pyrimidin-4-ylamino)-N-methylbenzamide (prepared in analogous fashion to Example 1d with 2,4,5-trichloropyrimidine and 2-amino-4-Chloro-N-methylbenzamide) were converted to 4-Chloro-2-[5-chloro-2-(3-ethyl-2,3,4,5-tetrahydro-1H-benzo[d]azepin-7-ylamino)-pyrimidin-4-ylamino]-N-methyl-benzamide. $^1$H-NMR $^1$H NMR (400 MHz, DMSO-d$_6$) δ 11.76 (s, 1H), 9.31 (s, 1H), 8.83 (s, 1H), 8.72 (s, 1H), 8.22 (s, 1H), 7.76 (d, J=8.6 Hz, 1H), 7.41 (d, J=7.8 Hz, 1H), 7.29 (s, 1H), 7.19 (d, J=6.8 Hz, 1H), 7.02 (d, J=8.1 Hz, 1H), 2.88-2.71 (m, 7H), 2.58-2.42 (m, 6H), 1.02 (t, J=7.1 Hz, 3H). LC/MS found 485 (M+H). mp 223° C. (50%)

Example 34

2-{5-Chloro-2-[3-(2-methoxy-ethyl)-2,3,4,5-tetrahydro-1H-benzo[d]azepin-7-ylamino]-pyrimidin-4-ylamino}-N-methyl-benzamide 34a) Analogous to procedure 31e, 7-Nitro-2,3,4,5-tetrahydro-1H-benzo[d]azepine was converted to 3-(2-Methoxy-ethyl)-7-nitro-2,3,4,5-tetrahydro-1H-benzo[d]azepine (51%) 7.99 (m, 2H), 7.24 (d, J=8.8 Hz, 1H), 3.52 (t, J=5.5 Hz, 2H), 3.33 (s, 3H), 3.04 (m, 4H), 2.73 (m, 6H)

34b) Analogous to procedure 31f, 3-(2-Methoxy-ethyl)-7-nitro-2,3,4,5-tetrahydro-1H-benzo[d]azepine was converted to 3-(2-Methoxy-ethyl)-2,3,4,5-tetrahydro-1H-benzo[d]azepin-7-ylamine. (quantitative) $^1$H-NMR (400 MHz, CDCL3) δ 6.96 (d, J=7.8 Hz, 1H), 6.44 (m, 2H), 3.52 (t, J=5.8 Hz, 2H), 3.41 (s, 2H), 3.36 (s, 3H), 2.84 (m, 4H), 2.78-2.62 (m, 6H).

34c) Analogous to procedure 31g, 3-(2-Methoxy-ethyl)-2,3,4,5-tetrahydro-1H-benzo[d]azepin-7-ylamine was converted to 2-{5-Chloro-2-[3-(2-methoxy-ethyl)-2,3,4,5-tetrahydro-1H-benzo[d]azepin-7-ylamino]-pyrimidin-4-ylamino}-N-methyl-benzamide.

$^1$H NMR (400 MHz, CDCl$_3$) δ 11.11 (s, 1H), 8.61 (d, J=8.3 Hz, 1H), 8.10 (s, 1H), 7.53 (d, J=7.6 Hz, 1H), 7.48-7.40 (m, 2H), 7.25 (m, 1H), 7.13-7.04 (m, 2H), 6.95 (s, 1H), 6.33 (br s, 1H), 3.81 (br s, 1H), 3.35 (s, 3H), 3.15-3.02 (m, 11H). LC/MS found 469 (M+H). mp 178-183° C. (58%)

Example 35

2-{5-Chloro-2-[3-(2-methoxy-ethyl)-2,3,4,5-tetrahydro-1H-benzo[d]azepin-7-ylamino]-pyrimidin-4-ylamino}-N-methyl-benzenesulfonamide 35a) Analogous to procedure 31f-31g, 3-(2-Methoxy-ethyl)-7-nitro-2,3,4,5-tetrahydro-1H-benzo[d]azepine was converted to 2-{5-Chloro-2-[3-(2-methoxy-ethyl)-2,3,4,5-tetrahydro-1H-benzo[d]azepin-7-ylamino]-pyrimidin-4-ylamino}-N-methyl-benzenesulfonamide. $^1$H NMR (400 MHz, CDCl$_3$) δ 9.11 (s, 1H), 8.49 (d, J=8.3 Hz, 1H), 8.13 (s, 1H), 7.96 (d, J=8.1 Hz, 1H), 7.55 (m, 1H), 7.22 (m, 1H), 7.02 (d, J=8.1 Hz, 1H), 6.90 (s, 1H), 4.50 (br s, 1H), 3.35 (s, 3H), 2.98-2.69 (m, 12H), 2.62 (d, J=5.3 Hz, 3H). LC/MS found 517 (M+H). mp 102-108° C. (38%)

Example 36

N-((1R,2R)-2-{5-Chloro-2-[3-(2-methoxy-ethyl)-2,3,4,5-tetrahydro-1H-benzo[d]azepin-7-ylamino]-pyrimidin-4-ylamino}-cyclohexyl)-methanesulfonamide 36a) Analogous to procedure 31f-31g, 3-(2-Methoxy-ethyl)-7-nitro-2,3,4,5-tetrahydro-1H-benzo[d]azepine was converted to N-((1R,2R)-2-{5-Chloro-2-[3-(2-methoxy-ethyl)-2,3,4,5-tetrahydro-1H-benzo[d]azepin-7-ylamino]-pyrimidin-4-ylamino}-cyclohexyl)-methanesulfonamide.
$^1$H NMR (400 MHz, CDCl$_3$) δ 7.98-7.82 (m, 2H), 7.51 (br s, 1H), 7.19 (s, 1H), 6.97-6.88 (m, 2H), 6.45 (m, 1H), 5.88 (br s, 1H), 3.98-3.78 (m, 4H), 3.32 (s, 3H), 3.21 (m, 2H), 2.85 (s, 3H), 2.19-1.60 (m, 4H), 1.40-1.21 (m, 4H). LC/MS found 469 (M+H). mp 107-137° C. (dec.).

Example 37

N-(2-{5-Chloro-2-[3-(2-methoxy-ethyl)-2,3,4,5-tetrahydro-1H-benzo[d]azepin-7-ylamino]-pyrimidin-4-ylamino}-phenyl)-methanesulfonamide 37a) Analogous to procedure 31f-31g, 3-(2-Methoxy-ethyl)-7-nitro-2,3,4,5-tetrahydro-1H-benzo[d]azepine was converted to N-(2-{5-Chloro-2-[3-(2-methoxy-ethyl)-2,3,4,5-tetrahydro-1H-benzo[d]azepin-7-ylamino]-pyrimidin-4-ylamino}-phenyl)-methanesulfonamide. $^1$H NMR (400 MHz, CDCl$_3$) δ 8.09 (br s, 1H), 8.00 (s, 1H), 7.88 (s, 1H), 7.69 (m, 1H), 7.54 (m, 1H), 7.28-7.20 (m, 2H), 7.05 (d, J=7.3 Hz, 1H), 6.91 (m, 2H), 6.48 (m, 2H), 3.93 (m, 3H), 3.81-3.62 (m, 4H), 3.29 (m, 4H), 2.98 (s, 3H), 2.90-2.61 (m, 8H). (LC/MS found 469 (M+H). mp 93-127° C. (dec.).

Example 38

2-{5-Chloro-2-[3-(2-fluoro-ethyl)-2,3,4,5-tetrahydro-1H-benzo[d]azepin-7-ylamino]-pyrimidin-4-ylamino}-N-methyl-benzamide 38a) Analogous to procedure 31e, 7-Nitro-2,3,4,5-tetrahydro-1H-benzo[d]azepine was converted to 3-(2-Fluoro-ethyl)-7-nitro-2,3,4,5-tetrahydro-1H-benzo[d]azepine (76%). $^1$H NMR (400 MHz, CDCl$_3$) δ 7.95 (m, 2H), 7.22 (d, J=8.3 Hz, 1H), 4.58 (dt, J=47.5, 4.7 Hz, 2H), 3.02 (m, 4H), 2.82 (dt, J=27.5, 4.7 Hz, 2H), 2.73 (m, 4H)

38b) Analogous to procedure 31f-31g, 3-(2-Methoxy-ethyl)-7-nitro-2,3,4,5-tetrahydro-1H-benzo[d]azepine was converted to 3-(2-Fluoro-ethyl)-2,3,4,5-tetrahydro-1H-benzo[d]azepin-7-ylamine which was converted to 2-{5-Chloro-2-[3-(2-fluoro-ethyl)-2,3,4,5-tetrahydro-1H-benzo[d]azepin-7-ylamino]-pyrimidin-4-ylamino}-N-methyl-benzamide (30%) $^1$H NMR (400 MHz, CDCl$_3$) δ 11.03 (s, 1H), 8.65 (d, J=8.3 Hz, 1H), 8.10 (s, 1H), 7.52-7.43 (m, 2H), 7.32 (s, 1H), 7.25 (m, 1H), 7.12-7.01 (m, 2H), 6.87 (s, 1H), 6.20 (br s, 1H), 4.60 (dt, J=48.0, 4.5 Hz, 2H), 3.09 (d, J=4.5 Hz, 3H), 2.89-2.73 (m, 10H). LC/MS found 469 (M+H). mp 170-174° C.

Example 39

2-{5-Chloro-2-[3-(2-fluoro-2-methyl-propyl)-2,3,4,5-tetrahydro-1H-benzo[d]azepin-7-ylamino]-pyrimidin-4-ylamino}-N-methyl-benzamide 39a) Analogous to procedure 31e, 7-Nitro-2,3,4,5-tetrahydro-1H-benzo[d]azepine was converted to 3-(2,2-Difluoro-propyl)-7-nitro-2,3,4,5-tetrahydro-1H-benzo[d]azepine. (44%). $^1$H NMR (400 MHz, CDCl$_3$) δ 7.95 (m, 2H), 7.22 (d, J=8.8 Hz, 2H), 3.02 (m, 4H), 2.81 (m, 4H), 2.61 (d, J=21.5 Hz, 2H), 1.40 (d, J=21.5 Hz, 6H)

39b) Analogous to procedure 31f-31g, 3-(2,2-Difluoro-propyl)-7-nitro-2,3,4,5-tetrahydro-1H-benzo[d]azepine was converted to 3-(2-Fluoro-2-methyl-propyl)-2,3,4,5-tetrahydro-1H-benzo[d]azepin-7-ylamine which was converted to 2-{5-Chloro-2-[3-(2-fluoro-2-methyl-propyl)-2,3,4,5-tetrahydro-1H-benzo[d]azepin-7-ylamino]-pyrimidin-4-ylamino}-N-methyl-benzamide. 1H-NMR (CDCl$_3$) δ 11.03 (s, 1H), 8.73 (d, J=8.3 Hz, 1H), 8.09 (s, 1H), 7.52-7.41 (m, 2H), 7.31-7.21 (m, 2H), 7.10 (t, J=7.8 Hz, 1H), 7.02 (d, J=8.6 Hz, 1H), 6.85 (s, 1H), 6.19 (br s, 1H), 3.05 (d, J=4.5 Hz, 3H), 2.91-2.83 (m, 4H), 2.80-2.76 (m, 4H), 1.39 (d, J=21.2 Hz, 6H). LC/MS found 497 (M+H). mp 207-210° C.

Example 40

N-((1R,2R)-2-{5-Chloro-2-[3-(2-fluoro-2-methyl-propyl)-2,3,4,5-tetrahydro-1H-benzo[d]azepin-7-ylamino]-pyrimidin-4-ylamino}-cyclohexyl)-methanesulfonamide 40a) Analogous to procedure 31f-31g, 3-(2,2-Difluoropropyl)-7-nitro-2,3,4,5-tetrahydro-1H-benzo[d]azepine was converted to 3-(2-Fluoro-2-methyl-propyl)-2,3,4,5-tetrahydro-1H-benzo[d]azepin-7-ylamine which was converted to N-((1R,2R)-2-{5-Chloro-2-[3-(2-fluoro-2-methyl-propyl)-2,3,4,5-tetrahydro-1H-benzo[d]azepin-7-ylamino]-pyrimidin-4-ylamino}-cyclohexyl)-methanesulfonamide. $^1$H NMR (400 MHz, CDCl$_3$) δ 7.91 (s, 1H), 7.21 (m, 2H), 7.03 (d, J=7.8 Hz, 1H), 6.85 (br s, 1H), 5.40 (m, 2H), 3.85 (br s, 1H), 3.22 (br s, 1H), 2.91-2.72 (m, 10H), 2.60 (d, J=21.2 Hz, 1H), 2.20 (m, 2H), 1.80 (m, 2H), 1.66-1.51 (m, 2H), 1.42-1.31 (m, 8H). LC/MS found 539 (M+H). mp 122-151° C. (dec.).

Example 41

2-{5-Chloro-2-[3-(2,2,2-trifluoro-ethyl)-2,3,4,5-tetrahydro-1H-benzo[d]azepin-7-ylamino]-pyrimidin-4-ylamino}-N-methyl-benzamide 41a) Analogous to procedure 31e-31g, 7-Nitro-2,3,4,5-tetrahydro-1H-benzo[d]azepine was converted to 3-(2,2,2-Trifluoro-ethyl)-2,3,4,5-tetrahydro-1H-benzo[d]azepin-7-ylamine which was converted to 2-{5-Chloro-2-[3-(2,2,2-trifluoro-ethyl)-2,3,4,5-tetrahydro-1H-benzo[d]azepin-7-ylamino]-pyrimidin-4-ylamino}-N-methyl-benzamide. $^1$H NMR (400 MHz, CDCl$_3$) δ 11.07 (s, 1H), 8.65 (d, J=8.3 Hz, 1H), 7.49 (d, J=7.8 Hz, 1H), 7.44 (dd, J=7.8, 7.8 Hz, 1H), 7.35 (s, 1H, 7.25 (m, 1H), 7.11-7.00 (m, 3H). 6.20 (br s, 1H), 3.20 (q, J=9.6 Hz, 2H), 3.03 (d, J=4.8 Hz, 3H), 2.90-2.72 (m, 8H). LC/MS found 505 (M+H). mp 177-190° C.

Example 42

2-[5-Chloro-2-(3-methanesulfonyl-2,3,4,5-tetrahydro-1H-benzo[d]azepin-7-ylamino)-pyrimidin-4-ylamino]-N-methyl-benzamide 42a) 7-Nitro-2,3,4,5-tetrahydro-1H-benzo[d]azepine nitrate salt (515 mg/2 mmol) was suspended in methylene chloride (5 mL) and cooled to 0° C. Triethylamine (620 µL/4.4 mmol) was added followed by methanesulfonyl chloride (dropwise, 160 µL/2.1 mmol). After fifteen minutes the reaction was poured into 25 mL of 1 N hydrochloric acid and extracted with methylene chloride (20 mL). The organic layer was dried over magnesium sulfate, filtered and concentrated to give 3-Methanesulfonyl-7-nitro-2,3,4,5-tetrahydro-1H-benzo[d]azepine as a light brown solid (520 mg/quantitative). $^1$H NMR (400 MHz, CDCl$_3$) δ 8.05 (m, 2H), 7.3 (d, J=9.1 Hz, 1H), 3.45 (m 4H), 3.15 (m, 4H), 2.8 (s, 3H).

42b) Analogous to procedure 31f-31g, 3-Methanesulfonyl-7-nitro-2,3,4,5-tetrahydro-1H-benzo[d]azepine was converted to 3-Methanesulfonyl-2,3,4,5-tetrahydro-1H-benzo[d]azepin-7-ylamine which was converted to 2-[5-Chloro-2-(3-methanesulfonyl-2,3,4,5-tetrahydro-1H-benzo[d]azepin-7-ylamino)-pyrimidin-4-ylamino]-N-methyl-benzamide. $^1$H NMR (400 MHz, CDCl$_3$) δ 11.10 (s, 1H), 8.62 (d, J=8.3 Hz, 1H), 8.11 (s, 1H), 7.40 (d, J=8.1 Hz, 1H), 7.36-7.30 (m, 2H), 7.28 (m, 1H), 7.12-7.03 (m, 2H), 6.91 (s, 1H), 6.21 (br s, 1H), 3.41 (m, 4H), 3.09-2.91 (m, 7H), 2.78 (s, 3H). LC/MS found 469 (M+H). mp 251-256° C.

Example 43

2-[5-Chloro-2-(3-methanesulfonyl-2,3,4,5-tetrahydro-1H-benzo[d]azepin-7-ylamino)-pyrimidin-4-ylamino]-N-methyl-benzenesulfonamide 43a) Analogous to 31g, 3-Methanesulfonyl-2,3,4,5-tetrahydro-1H-benzo[d]azepin-7-ylamine was converted to 2-[5-Chloro-2-(3-methanesulfonyl-2,3,4,5-tetrahydro-1H-benzo[d]azepin-7-ylamino)-pyrimidin-4-ylamino]-N-methyl-benzenesulfonamide was prepared. $^1$H NMR (400 MHz, CDCl$_3$) δ 9.12 (s, 1H), 8.48 (d, J=7.8 Hz, 1H), 8.11 (s, 1H), 7.97 (dd, J=8.1, 1.5 Hz, 1H), 7.58 (m, 1H), 7.35-7.22 (m, 3H), 7.06 (d, J=8.1 Hz, 1H), 6.92 (s, 1H), 4.61 (m, 1H), 3.41 (m, 4H), 3.02-2.91 (m, 4H), 2.79 (s, 3H), 2.65 (d, J=5.3 Hz, 3H). LC/MS found 536 (M+H). mp 199-201° C.

Example 44

2-{5-Chloro-2-[3-(2,2,2-trifluoro-acetyl)-2,3,4,5-tetrahydro-1H-benzo[d]azepin-7-ylamino]-pyrimidin-4-ylamino}-N-methyl-benzamide 44a) Analogous to 42a and 31f, 7-Nitro-2,3,4,5-tetrahydro-1H-benzo[d]azepine nitrate salt was converted to 1-(7-Amino-1,2,4,5-tetrahydro-benzo[d]azepin-3-yl)-2,2,2-trifluoro-ethanone which was converted to 2-{5-Chloro-2-[3-(2,2,2-trifluoro-acetyl)-2,3,4,5-tetrahydro-1H-benzo[d]azepin-7-ylamino]-pyrimidin-4-ylamino}-N-methyl-benzamide. $^1$H NMR (400 MHz, CDCl$_3$) δ 11.59 (s, 1H), 9.42 (d, J=4.0 Hz, 1H), 8.79-8.66 (m, 2H), 8.22 (s, 1H), 7.75 (d, J=7.8 Hz, 1H), 7.52-7.32 (m, 3H), 7.18 (m, 1H), 7.09 (t, 1H), 3.66 (m, 4H), 2.92-2.79 (m, 7H). LC/MS found 519 (M+H). mp 192-194° C.

Example 45

2-[5-Chloro-2-(2,3,4,5-tetrahydro-1H-benzo[d]azepin-7-ylamino)-pyrimidin-4-ylamino]-N-methyl-benzamide 45a) 2-{5-Chloro-2-[3-(2,2,2-trifluoro-acetyl)-2,3,4,5-tetrahydro-1H-benzo[d]azepin-7-ylamino]-pyrimidin-4-ylamino}-N-methyl-benzamide (350 mg/0.67 mmol) was dissolved in methanol (5 mL) and treated with solid potassium carbonate (500 mg/3.2 mmol). The suspension was allowed to stir at room temperature overnight. The resulting opaque solution was concentrated and taken up in 10% methanol/methylene chloride. This mixture was filtered and concentrated to afford 2-[5-Chloro-2-(2,3,4,5-tetrahydro-1H-benzo[d]azepin-7-ylamino)-pyrimidin-4-ylamino]-N-methyl-benzamide as a yellow solid (200 mg/70%). $^1$H NMR (400 MHz, DMSO-d$_6$) δ 11.52 (br s, 1H), 9.31 (s, 1H), 8.82-8.61 (m, 2H), 8.20 (s, 1H), 7.75 (d, J=7.6 Hz, 1H), 7.49-7.41 (m, 2H), 7.31 (d, J=8.0 Hz, 1H), 7.12 (m, 1H), 6.97 (d, J=8.0 Hz, 1H), 2.82-2.68 (m, 11H). LC/MS found 423 (M+H). mp 162-190° C. (dec.).

Example 46

2-[5-Chloro-2-(3-methyl-2,3,4,5-tetrahydro-1H-benzo[d]azepin-7-ylamino)-pyrimidin-4-ylamino]-N-methyl-benzamide 46a) 2-[5-Chloro-2-(2,3,4,5-tetrahydro-1H-benzo[d]azepin-7-ylamino)-pyrimidin-4-ylamino]-N-methyl-benzamide was suspended in acetonitrile (5 mL). Aqueous formaldehyde (37%, 325 μL/4 mmol) and sodium cyanoborohydride (210 mg/3.3 mmol) were added sequentially and the reaction stirred at room temperature for two hours. The material was concentrated onto celite and the desired product was isolated by sequential column chromatography on silica gel (eluting with 0→50% methanol/methylene chloride) followed by basic alumina (eluting with 0→40% methanol/methylene chloride). Yield 50 mg/35%. $^1$H NMR (400 MHz, DMSO-d$_6$) δ 11.58 (s, 1H), 9.41 (s, 1H), 8.82-8.69 (m, 2H), 8.22 (s, 1H), 7.79 (d, J=7.8 Hz, 1H), 7.56-7.41 (m, 3H), 7.19 (dd, J=7.3, 7.3 Hz, 1H), 7.09 (d, J=8.1 Hz, 1H), 3.19-2.78 (m, 14H). LC/MS found 436 (M+H). mp 125-130° C. (dec.).

Example 47

2-[5-Chloro-2-(3-isopropyl-2,3,4,5-tetrahydro-1H-benzo[d]azepin-7-ylamino)-pyrimidin-4-ylamino]-N-methyl-benzamide 47a) Using analogous procedures to 46a, 2-[5-Chloro-2-(3-isopropyl-2,3,4,5-tetrahydro-1H-benzo[d]azepin-7-ylamino)-pyrimidin-4-ylamino]-N-methyl-benzamide was prepared (10%). $^1$H NMR (400 MHz, CDCl$_3$) δ 11.11 (s, 1H), 8.56 (d, J=8.1 Hz, 1H), 8.06 (s, 1H), 7.63 (s, 1H), 7.54-7.50 (m, 2H), 7.44 (dd, J=7.0, 7.0 Hz, 1H), 7.21 (dd, J=8.1, 2.2 Hz, 1H), 7.15 (dd, J=7.1, 7.1 Hz, 1H), 7.05 (d, J=8.1 Hz, 1H), 6.34 (s, 1H), 3.60 (m, 1H), 3.32-3.05 (br m, 8H), 3.05 (d, J=4.8 Hz, 3H), 1.37 (d, J=6.6 Hz, 6H). LC/MS found 465 (M+H). mp 140-158° C.

Example 48

2-[5-Chloro-2-(3-ethyl-8-methoxy-2,3,4,5-tetrahydro-1H-benzo[d]azepin-7-ylamino)-pyrimidin-4-ylamino]-N-methyl-benzamide 48a) 7-Methoxy-3-(toluene-4-sulfonyl)-2,3,4,5-tetrahydro-benzo[d]azepin-1-one (8.0 g/23 mmol; prepared in 4 steps as described by Kanao et al. *Chem. Pharm. Bull.*, 1982, 30, 180-188) was dissolved in trifluoroacetic acid (10 mL) and cooled to 0° C. Triethylsilane (ca. 20 mL/230 mmol) was then added via syringe (mild exotherm) and the reaction allowed to warm to room temperature overnight. The reaction was concentrated and the residue partitioned between diethyl ether and 1 M aqueous sodium hydroxide (100 mL). The organic layer was washed with brine (100 mL), dried (magnesium sulfate), filtered and concentrated onto silica gel. Chromatography on silica gel (eluting with 0→30% ethyl acetate/hexanes) afforded 7-Methoxy-3-(toluene-4-sulfonyl)-2,3,4,5-tetrahydro-1H-benzo[d]azepine as a white solid (4.0 g/55%). $^1$H NMR (400 MHz, CDCl$_3$) δ 7.62 (d, J=8.0 Hz, 2H), 7.25 (d, J=8.0 Hz, 2H), 6.98 (d, J=9.1 Hz, 1H), 6.68 (m, 2H), 3.78 (s, 3H), 3.28 (m, 4H), 2.94 (m, 4H), 2.39 (s, 3H).

48b) 7-Methoxy-3-(toluene-4-sulfonyl)-2,3,4,5-tetrahydro-1H-benzo[d]azepine (3.9 g/11.8 mmol) was placed in a round bottom flask and cooled to −78 C (external CO$_2$/acetone bath). Ammonia (ca. 20 mL) was condensed into the flask and freshly cut sodium (3 g) was carefully added in small pieces (dark blue color observed) and the reaction allowed to stir for one hour. The reaction was quenched by the addition of solid ammonium chloride followed by careful addition of diethyl ether (30 mL). The reaction was then allowed to warm to room temperature and the ammonia allowed to boil off. Water was then carefully added (50 mL) and the layers separated. The organic layer was extracted with 1 N hydrochloric acid (2×50 mL). The aqueous extracts were basified with 33% aqueous sodium hydroxide and extracted with 10% methanol/methylene chloride (3×50 mL). The combined organic extracts were dried (magnesium sulfate), filtered and concentrated to afford 7-Methoxy-2,3,4,5-tetrahydro-1H-benzo[d]azepine as a colorless oil (1.7 g/81%). $^1$H NMR (400 MHz, CDCl$_3$) δ 7.02 (d, J=8.0 Hz, 1H), 6.68-6.61 (m, 2H), 3.81 (s, 3H), 2.99-2.82 (m, 8H).

48c) 7-Methoxy-2,3,4,5-tetrahydro-1H-benzo[d]azepine (750 mg/4.2 mmol) was dissolved in a mixture of dry acetonitrile (3 mL) and trifluoroacetic anhydride (3 mL) and cooled to 0° C. (ice bath). The trifluoroacetyl amide of the benzazepine forms immediately (observed by HPLC). Potassium nitrate (450 mg/4.2 mmol) was added in one portion and the mixture allowed to warm to room temperature. After one hour the reaction was complete (HPLC); 33% sodium hydroxide (1 mL) was added via pipette (exotherm) and the mixture stirred for an additional two hours (to hydrolyze the TFA amide). The resulting mixture was partitioned between water (20 mL) and methylene chloride (20 mL). The aqueous layer was extracted with an additional portion of methylene chloride (20 mL) and the combined organics were dried over magnesium sulfate, filtered and concentrated to afford a 1.7:1 ratio of 7-Methoxy-8-nitro-2,3,4,5-tetrahydro-1H-benzo[d]azepine and 7-Methoxy-9-nitro-2,3,4,5-tetrahydro-1H-benzo[d]azepine as a yellow oil (770 mg/82%). The material was used without further purification. $^1$H NMR (400 MHz, CDCl$_3$) major isomer: δ 7.66 (s, 1H), 6.82 (s 1H); minor isomer: 7.14 (d, J=8.3 Hz, 1H), 6.76 (d, J=8.3 Hz, 1H).

48d) Analogous to procedure 31e, 7-Methoxy-8-nitro-2,3,4,5-tetrahydro-1H-benzo[d]azepine and 7-Methoxy-9-nitro-2,3,4,5-tetrahydro-1H-benzo[d]azepine were converted to 3-Ethyl-7-methoxy-8-nitro-2,3,4,5-tetrahydro-1H-benzo[d]azepine and 3-Ethyl-7-methoxy-8-nitro-2,3,4,5-tetrahydro-1H-benzo[d]azepine which were separated and taken on independently following a procedure analogous to 1f to 3-Ethyl-8-methoxy-2,3,4,5-tetrahydro-1H-benzo[d]azepin-7-ylamine. $^1$H NMR (400 MHz, CDCl$_3$) δ 6.56 (s, 1H), 6.48 (m, 2H), 3.82 (s, 3H), 3.65 (br s, 2H), 2.89-2.78 (m, 4H), 2.66-2.49 (m, 6H), 1.11 (t, J=7.1 Hz, 3H). and 3-Ethyl-8-methoxy-2,3,4,5-tetrahydro-1H-benzo[d]azepin-6-ylamine $^1$H NMR (400 MHz, CDCl$_3$) δ 6.60 (d, J=8.1 Hz, 1H), 6.55 (d, J=8.1 Hz, 1H), 3.84 (s, 3H), 3.51 (br s, 2H), 3.20-3.02 (m, 10H), 1.35 (t, J=7.3 Hz, 3H).

48e) Analogous to 31g, 3-Ethyl-8-methoxy-2,3,4,5-tetrahydro-1H-benzo[d]azepin-7-ylamine was converted to 2-[5-Chloro-2-(3-ethyl-8-methoxy-2,3,4,5-tetrahydro-1H-benzo[d]azepin-7-ylamino)-pyrimidin-4-ylamino]-N-methyl-benzamide (56%). $^1$H NMR (400 MHz, CDCl$_3$) 6 (CDCl$_3$) δ 11.12 (s, 1H), 8.57 (d, J=8.3 Hz, 1H), 8.15 (s, 1H), 8.07 (s, 1H), 7.63 (d, J=7.8 Hz, 1H), 7.47 (s, 1H), 7.37 (dd, J=7.3, 7.3 Hz, 1H), 7.07 (m, 1H), 6.62 (s, 1H), 3.85 (s, 3H), 3.41-3.01 (m, 13H), 1.41 (t, J=7.1 Hz, 3H). LC/MS found 481 (M+H). mp 195-211° C.

Example 49

2-[5-Chloro-2-(3-ethyl-7-methoxy-2,3,4,5-tetrahydro-1H-benzo[d]azepin-6-ylamino)-pyrimidin-4-ylamino]-N-methyl-benzenesulfonamide 49a) Following analogous procedures to 31g, 3-Ethyl-8-methoxy-2,3,4,5-tetrahydro-1H-benzo[d]azepin-6-ylamine was converted to 2-[5-Chloro-2-(3-ethyl-7-methoxy-2,3,4,5-tetrahydro-1H-benzo[d]azepin-6-ylamino)-pyrimidin-4-ylamino]-N-methyl-benzenesulfonamide (24%). 1H NMR (400 MHz, CDCl$_3$) δ (CDCl$_3$) δ 9.14 (s, 1H), 8.11 (s, 1H), 7.92 (d, J=8.1 Hz, 1H), 7.16 (m, 1H), 7.02 (d, J=8.3 Hz, 1H), 6.80 (d, J=8.3 Hz, 1H), 6.52 (br s, 1H), 3.83 (s, 3H), 3.08-2.61 (m, 13H), 1.40 (m, 3H). LC/MS found 517 (M+H). mp 171-188° C.

Example 50

2-[2-(9-Amino-3-ethyl-8-methoxy-2,3,4,5-tetrahydro-1H-benzo[d]azepin-7-ylamino)-5-chloro-pyrimidin-4-ylamino]-N-methyl-benzamide 50a) 7-Methoxy-2,3,4,5-tetrahydro-1H-benzo[d]azepine was cooled to 0° C. and treated with pre-cooled fuming nitric acid. After 15 minutes, the mixture was poured into water and basified to pH 14 by the addition of 33% sodium hydroxide and extracted with 10% methanol/methylene chloride (5×10 mL). The organic extracts were dried over magnesium sulfate, filtered and concentrated to afford 7-Methoxy-6,8-dinitro-2,3,4,5-tetrahydro-1H-benzo[d]azepine as a yellow oil (650 mg/48%). $^1$H NMR (400 MHz, CDCl$_3$) δ 7.84 (s, 1H), 3.99 (s, 3H), 3.09-2.81 (m, 8H), 1.91 (br s, 2H).

50b) Analogous to procedure 31e-31f, 7-Methoxy-6,8-dinitro-2,3,4,5-tetrahydro-1H-benzo[d]azepine was converted to 7-Methoxy-2,3,4,5-tetrahydro-1H-benzo[d]azepine-6,8-diamine, which was converted to 2-[2-(9-Amino-3-ethyl-8-methoxy-2,3,4,5-tetrahydro-1H-benzo[d]azepin-7-ylamino)-5-chloro-pyrimidin-4-ylamino]-N-methyl-benzamide (16%). 1H-NMR (CDCl$_3$) δ 9.07 (s, 1H), 8.52 (d, J=8.3 Hz, 1H), 8.17 (s, 1H), 7.98 (d, J=8.0 Hz, 1H), 7.59 (m, 1H), 7.41 (s, 1H), 7.35 (s, 1H), 7.25 (m, 1H), 4.50 (br s, 1H), 3.78 (m, 4H), 2.78-2.51 (m, 7H), 1.11 (t, J=7.1 Hz, 3H). LC/MS found 532 (M+H). mp 117-160° C.

Example 51

2-[5-Chloro-2-(5,6,8,9-tetrahydro-7-oxa-benzocyclohepten-2-ylamino)-pyrimidin-4-ylamino]-N-methyl-benzamide 51a) 2-[2-(2-Hydroxy-ethyl)-phenyl]-ethanol (6.77 g/40 mmol) was dissolved in methylene chloride (100 mL) and cooled to 0° C. Triethylamine (11.0 mL/80 mmol) and methanesulfonyl chloride (5.25 mL/65 mmol) were added sequentially via addition funnel (dropwise). After an hour the reaction was poured into a separatory funnel and sequentially washed with 1 N hydrochloric acid (100 mL), water (100 mL) and saturated aqueous sodium bicarbonate (100 mL). The resulting organic solution was dried over magnesium sulfate, filtered and concentrated. Column chromatography on silica gel (eluting with 0→10% methanol/methylene chloride afforded methanesulfonic acid 2-[2-(2-hydroxy-ethyl)-phenyl]-ethyl ester (2.25 g/23%). $^1$H NMR (400 MHz, CDCl$_3$) δ 7.25 (m, 4H), 4.42 (t, J=7.1 Hz, 2H), 3.88 (m, 2H), 3.15 (t, J=7.1 Hz, 2H), 2.93 (t, J=7.1 Hz, 2H), 2.85 (s, 3H).

51b) Methanesulfonic acid 2-[2-(2-hydroxy-ethyl)-phenyl]-ethyl ester (2.2 g/9.0 mmol) was dissolved in tetrahydrofuran (400 mL). Sodium hydride (540 mg/14.5 mmol) was added (hydrogen evolution) and the reaction allowed to stir at room temperature overnight. The reaction was quenched by the addition of water (10 mL) and the reaction concentrated to a volume of ca. 50 mL by rotary evaporation. The residue was partitioned between water (50 mL) and ethyl ether (50 mL). The aqueous layer was extracted with an additional portion of ethyl ether (50 mL) and the combined organics were washed with brine (100 mL), dried over magnesium sulfate, filtered and concentrated onto silica gel. Column chromatography on silica gel (eluting with 0→50% ethyl acetate/hexanes) afforded 5,6,8,9-Tetrahydro-7-oxa-benzocycloheptene as a colorless oil (240 mg/18%) along with a styrene by-product formed by mesylate elimination (600 mg/45%). Oxapene: $^1$H NMR (400 MHz, CDCl$_3$) δ 7.11 (m, 4H), 3.80 (m, 4H), 3.00 (m, 4H).

51c) 5,6,8,9-Tetrahydro-7-oxa-benzocycloheptene (200 mg/1.3 mmol) was cooled to −10° C. and nitric acid (2 mL, pre-cooled to −10° C.) was added dropwise. After 15 minutes the reaction was poured into ice and the mixture extracted with methylene chloride (2×20 mL). The combined organics were dried over magnesium sulfate, filtered and concentrated to 2-Nitro-5,6,8,9-tetrahydro-7-oxa-benzocycloheptene as a pale yellow solid. Yield: 270 mg/quantitative. $^1$H NMR (400 MHz, CDCl$_3$) δ 8.00 (m, 2H), 7.25 (m, 1H), 3.82 (m, 4H), 3.12 (m, 4H).

51d) 2-Nitro-5,6,8,9-tetrahydro-7-oxa-benzocycloheptene (270 mg/1.3 mmol) was dissolved in anhydrous methanol (ca. 10 mL) and the solution added to a Parr flask. Palladium (10% on charcoal) was added carefully and the mixture shaken under 40 psi of hydrogen for 2 hours. The mixture was then filtered and the colorless filtrate concentrated onto celite. Chromatography on an amine-bonded column (eluting with 0→60% ethyl acetate/hexanes) afforded 5,6,8,9-tetrahydro-7-oxa-benzocyclohepten-2-ylamine as a colorless solid (200 mg/quantitative). 1H NMR (400 MHz, CDCl$_3$) δ 6.89 (d, J=7.6 Hz, 1H), 6.42 (m, 2H), 3.78 (m, 4H), 3.55 (br s, 2H), 2.88 (m, 4H).

51e) Analogous to procedure 31g, 5,6,8,9-tetrahydro-7-oxa-benzocyclohepten-2-ylamine was converted to 2-[5-Chloro-2-(5,6,8,9-tetrahydro-7-oxa-benzocyclohepten-2-ylamino)-pyrimidin-4-ylamino]-N-methyl-benzamide. $^1$H-NMR (CDCl$_3$) δ 11.06 (s, 1H), 8.63 (d, J=8.3 Hz, 1H), 8.11 (s, 1H), 7.50 (m, 1H), 7.44 (dd, J=8.0, 8.0 Hz, 1H), 7.36 (s, 1H), 7.11-7.02 (m, 2H), 6.87 (s, 1H), 6.20 (br s, 1H), 3.79 (m, 4H), 3.08 (d, J=4.8 Hz, 3H), 2.95 (m, 4H). LC/MS found 424 (M+H). mp 185° C.

Example 61

2-[5-Chloro-2-(10-ethyl-12-oxa-10-aza-tricyclo[6.3.1.0*2,7*]dodeca-2,4,6-trien-4-ylamino)-pyrimidin-4-ylamino]-N-methyl-benzamide 61a) Methanesulfonic acid 3-methanesulfonyloxymethyl-1,3-dihydro-isobenzofuran-1-ylmethyl ester (12.1 g, 36 mmol) and conc. NH$_4$OH (50 mL) was dissolved in acetonitrile (100 mL) and heated at 100° C. in a sealed vessel for 2 h. The reaction was then cooled, adjusted to pH 5-6 with 1 N HCl and extracted with diethyl ether (100 mL). The aqueous layer was then basified with 10 N NaOH and extracted with diethyl ether (2×100 mL). The later organic layer was dried over MgSO$_4$, filtered, concentrated and purified with silica gel chromatography (0-15% MeOH in CH$_2$Cl$_2$) to obtain 12-Oxa-10-aza-tricyclo[6.3.1.0*2,7*]dodeca-2,4,6-triene as a brown, viscous oil (5.1 g, 88%). MS (m/e) 162 (M+1); HPLC (93%)

61b) Concentrated nitric acid (10 mL) was added to a mixture of 12-oxa-10-aza-tricyclo[6.3.1.0*2,7*]dodeca-2,4,6-triene (5.1 g, 32 mmol) and concentrated sulfuric acid (10 mL) at 0° C. The resulting solution was stirred at 0° C. for 30 min before pouring onto ice, adding 10 N NaOH slowly until basic, and extracting with CH$_2$Cl$_2$ (2×25 mL). The combined organic layers were dried over MgSO$_4$, filtered, concentrated and purified with silica gel chromatography (0-30% MeOH in CH$_2$Cl$_2$) to obtain 4-Nitro-12-oxa-10-aza-tricyclo[6.3.1.0*2,7*]dodeca-2,4,6-triene as a gummy, brown oil (4.2 g, 65%). MS (m/e) 207 (M+1).

61c) Sodium triacetoxyborohydride (530 mg, 2.5 mmol) was added to a solution of 4-nitro-12-oxa-10-aza-tricyclo [6.3.1.0*2,7*]dodeca-2,4,6-triene (200 mg, 0.97 mmol), acetaldehyde (0.15 mL, 2.5 mmol), acetic acid (0.1 mL) and dichloroethane (5 mL). The reaction was stirred at room temperature for 5 h. The reaction was then quenched with saturated aqueous NaHCO$_3$ (10 mL), extracted with CH$_2$Cl$_2$ (2×10 mL), dried over MgSO$_4$, filtered, and concentrated. The remaining residue was purified with silica gel chromatography (10-100% EtOAc in hexanes) to give 10-Ethyl-4-nitro-12-oxa-10-aza-tricyclo[6.3.1.0*2,7*]dodeca-2,4,6-triene as a yellow oil (115 mg, 51%). MS (m/e) 235 (M+1).

61d) Hydrogen was bubbled through a mixture of 10-ethyl-4-nitro-12-oxa-10-aza-tricyclo[6.3.1.0*2,7*]dodeca-2,4,6-triene (115 mg, 0.56 mmol) and 10% palladium on carbon (53 mg, 0.050 mmol) in ethanol (3 mL) and CH$_2$Cl$_2$ (3 mL) for 5 min. The reaction was then stirred under a hydrogen atmosphere for 18 h. Filtration through Celite and concentration gave 10-Ethyl-12-oxa-10-aza-tricyclo[6.3.1.0*2,7*]dodeca-2,4,6-trien-4-ylamine as an off-white foam (100 mg, 100%). MS (m/e) 205 (M+1.

61e) 10-Ethyl-12-oxa-10-aza-tricyclo[6.3.1.0*2,7*] dodeca-2,4,6-trien-4-ylamine (100 mg, 0.49 mmol) and 2-(2, 5-dichloro-pyrimidin-4-ylamino)-N-methyl-benzamide (200 mg, 0.67 mmol) were combined with 4 N HCl (0.14 mL, 0.56 mmol) in isopropanol (4 mL) and heated in a microwave at 120° C. for 20 min. The resulting mixture was diluted with saturated aqueous NaHCO$_3$ (3 mL), extracted with CH$_2$Cl$_2$ (3×5 mL), dried over MgSO$_4$, filtered, and concentrated. The remaining residue was purified with silica gel chromatography (0-10% MeOH in CH$_2$Cl$_2$) to obtain 2-[5-Chloro-2-(10-ethyl-12-oxa-10-aza-tricyclo[6.3.1.0*2,7*]dodeca-2,4,6-trien-4-ylamino)-pyrimidin-4-ylamino]-N-methyl-benzamide as a light yellow solid (61 mg, 27%). $^1$HNMR (400 MHz, DMSO-d$_6$) δ 11.5 (s, 1H), 9.5 (s, 1H), 8.8-8.7 (m, 2H), 8.2 (s, 1H), 7.8 (d, 1H, J=8.1 Hz), 7.6 (s, 1H), 7.5 (appt t, 1H, J=8.1 Hz), 7.4 (d, 1H, J=7.8 Hz), 7.2-7.1 (m, 2H), 5.0 (m, 2H), 2.8 (d, 3H, J=4.3 Hz), 2.7 (m, 2H), 2.4 (m, 2H), 2.3 (q, 2H, J=7.2 Hz), 0.8 (t, 3H, J=7.2 Hz); MS (m/e) 465 (M+1); mp 122-126° C.

Example 62

2-[5-Chloro-2-(10-isopropyl-12-oxa-10-aza-tricyclo [6.3.1.0*2,7*]dodeca-2,4,6-trien-4-ylamino)-pyrimidin-4-ylamino]-N-methyl-benzamide 62a) Following procedures analogous to 61c-61e, 4-nitro-12-oxa-10-aza-tricyclo[6.3.1.0*2,7*]dodeca-2,4,6-triene (200 mg, 0.97 mmol), and acetone Were converted to 10-Isopropyl-4-nitro-12-oxa-10-aza-tricyclo[6.3.1.0*2,7*]dodeca-2,4,6-triene, which was converted to 10-Isopropyl-12-oxa-10-aza-tricyclo[6.3.1.0*2,7*]dodeca-2,4,6-trien-4-ylamine which was relayed to 2-[5-Chloro-2-(10-isopropyl-12-oxa-10-aza-tricyclo[6.3.1.0*2,7*]dodeca-2,4,6-trien-4-ylamino)-pyrimidin-4-ylamino]-N-methyl-benzamide isolated as a as a yellow solid (13 mg). $^1$HNMR (400 MHz, DMSO-d$_6$) δ 11.6 (s, 1H), 9.5 (s, 1H), 8.8-8.7 (m, 2H), 8.2 (s, 1H), 7.8 (d, 1H, J=7.8 Hz), 7.6 (s, 1H), 7.5-7.4 (m, 2H), 7.2-7.1 (m, 2H), 5.0 (m, 2H), 2.8 (d, 3H, J=4.6 Hz), 2.7-2.4 (m, 5H), 0.8 (d, 6H, J=6.4 Hz); MS (m/e) 479 (M+1); mp 113-117° C.

Example 63

2-[5-Chloro-2-(10-prop-2-ynyl-12-oxa-10-aza-tricyclo[6.3.1.0*2,7*]dodeca-2,4,6-trien-4-ylamino)-pyrimidin-4-ylamino]-N-methyl-benzamide 63a) 4-Nitro-12-oxa-10-aza-tricyclo[6.3.1.0*2,7*] dodeca-2,4,6-triene (200 mg, 0.97 mmol), propargyl chloride (0.085 mL, 1.2 mmol), potassium carbonate (276 mg, 2.0 mmol) and THF (5 mL) were stirred together at 70° C. for 18 h. The reaction was then diluted with saturated aqueous NaHCO$_3$ (10 mL), extracted with CH$_2$Cl$_2$ (2×10 mL), dried over MgSO$_4$, filtered, and concentrated. The remaining residue was purified with silica gel chromatography (0-100% EtOAc in hexanes) to give 4-Nitro-10-prop-2-ynyl-12-oxa-10-aza-tricyclo[6.3.1.0*2,7*]dodeca-2,4,6-triene as a brown oil (120 mg, 51%). MS (m/e) 245 (M+1).

63b) 4-Nitro-10-prop-2-ynyl-12-oxa-10-aza-tricyclo [6.3.1.0*2,7*]dodeca-2,4,6-triene (120 mg, 0.49 mmol) and tin chloride dihydrate (554 mg, 2.45 mmol) were heated at reflux in EtOAc (10 mL) for 2 h. The resulting mixture was then diluted with saturated aqueous NaHCO$_3$ (10 mL), extracted with EtOAc (2×15 mL), dried over MgSO$_4$, filtered and concentrated to obtain 10-Prop-2-ynyl-12-oxa-10-aza-tricyclo[6.3.1.0*2,7*]dodeca-2,4,6-trien-4-ylamine as a brown, viscous oil (71 mg, 68%). MS (m/e) 215 (M+1)

63c) 10-Prop-2-ynyl-12-oxa-10-aza-tricyclo[6.3.1.0*2, 7*]dodeca-2,4,6-trien-4-ylamine (71 mg, 0.33 mmol) and 2-(2,5-dichloro-pyrimidin-4-ylamino)-N-methyl-benzamide (99 mg, 0.33 mmol) were combined with 4 N HCl (0.083 mL, 0.33 mmol) in isopropanol (2 mL) and heated in a microwave at 140° C. for 10 min. The resulting mixture was diluted with saturated aqueous NaHCO$_3$ (5 mL), extracted with CH$_2$Cl$_2$ (2×5 mL), dried over MgSO$_4$, filtered, and concentrated. The remaining residue was purified with silica gel chromatography (30-100% EtOAc in hexanes) to obtain 2-[5-Chloro-2-(10-prop-2-ynyl-12-oxa-10-aza-tricyclo[6.3.1.0*2,7*] dodeca-2,4,6-trien-4-ylamino)-pyrimidin-4-ylamino]-N-methyl-benzamide as a light yellow solid (79 mg, 50%). $^1$HNMR (400 MHz, CDCl$_3$) δ 11.0 (bs, 1H), 8.6 (d, 1H, J=8.7 Hz), 8.1 (s, 1H), 7.6 (s, 1H), 7.5 (d, 1H, J=7.8 Hz), 7.4 (appt t, 1H, J=8.7 Hz), 7.3 (d, 1H, J=7.8 Hz), 7.2 (d, 1H, J=7.8 Hz), 7.1 (appt t, 1H, J=7.6 Hz), 7.0 (bs, 1H), 6.2 (bs, 1H), 5.1 (s, 1H), 5.0 (s, 1H), 3.2 (d, 2H, J=2.4 Hz), 3.1-3.0 (m, 5H), 2.6 (t, 2H, J=9.5 Hz), 2.2 (t, 1H, J=2.4 Hz); MS (m/e) 475 (M+1); mp 117-121° C.

Example 64

2-[5-Chloro-2-(10-methanesulfonyl-12-oxa-10-aza-tricyclo[6.3.1.0*2,7*]dodeca-2(7),3,5-trien-4-ylamino)-pyrimidin-4-ylamino]-N-methyl-benzamide 64a) Methanesulfonyl chloride (133 mg, 1.16 mmol) was added to a solution of 4-nitro-12-oxa-10-aza-tricyclo [6.3.1.0*2,7*]dodeca-2,4,6-triene (200 mg, 0.55 mmol) and potassium carbonate (276 mg, 2.0 mmol) in THF (5 mL). The solution was stirred at 70° C. for 1 h. The reaction was then concentrated and purified with silica gel chromatography (0-100% EtOAc in hexanes) to give 10-Methanesulfonyl-4-nitro-12-oxa-10-aza-tricyclo[6.3.1.0*2,7*]dodeca-2,4,6-triene as a light tan solid (150 mg, 54%). MS (m/e) 285 (M+1).

64b) Following procedures analogous to 61e, 10-methanesulfonyl-4-nitro-12-oxa-10-aza-tricyclo[6.3.1.0*2,7*] dodeca-2,4,6-triene (150 mg, 0.49 mmol) was converted to 10-Methanesulfonyl-12-oxa-10-aza-tricyclo[6.3.1.0*2,7*] dodeca-2,4,6-trien-4-ylamine as an off-white foam (135 mg, 100%) MS (m/e) 255 (M+1) which was converted to 2-[5-Chloro-2-(10-methanesulfonyl-12-oxa-10-aza-tricyclo [6.3.1.0*2,7*]dodeca-2(7),3,5-trien-4-ylamino)-pyrimidin-4-ylamino]-N-methyl-benzamide as an off-white solid (79 mg, 29%). $^1$HNMR (400 MHz, DMSO-d$_6$) δ 11.6 (bs, 1H), 9.6 (s, 1H), 8.8-8.7 (m, 2H), 8.2 (s, 1H), 7.8-7.7 (m, 2H), 7.5

(m, 2H), 7.3 (d, 1H, J=8.1 Hz), 7.1 (appt t, 1H, J=7.3 Hz), 5.2 (m, 2H), 3.4-3.3 (m, 4H), 2.8 (d, 3H, J=4.6 Hz), 2.5 (s, 3H); MS (m/e) 515 (M+1); mp 154-158° C.

Example 65

2-[5-Chloro-2-(12-oxa-10-aza-tricyclo[6.3.1.0*2,7*]dodeca-2(7),3,5-trien-4-ylamino)-pyrimidin-4-ylamino]-N-methyl-benzamide 65a) 4-Nitro-12-oxa-10-aza-tricyclo[6.3.1.0*2,7*]dodeca-2,4,6-triene (169 mg, 0.82 mmol), di-tert-butyl dicarbonate (183 mg, 0.82 mmol) and triethylamine (0.22 mL, 1.6 mmol) were stirred at room temperature in tetrahydrofuran (5 mL) for 15 h. The reaction was then concentrated and 10% palladium on carbon (87 mg, 0.082 mmol) was added with ethanol (10 mL) and $CH_2Cl_2$ (1 mL). Hydrogen was bubbled through the resulting mixture for 5 min before letting stir under a hydrogen atmosphere for 15 h. Filtration through Celite and concentration gave 4-Amino-12-oxa-10-aza-tricyclo[6.3.1.0*2,7*]dodeca-2,4,6-triene-10-carboxylic acid tert-butyl ester as a gummy solid (220 mg, 97%). MS (m/e) 277 (M+1);

65b) 4-Amino-12-oxa-10-aza-tricyclo[6.3.1.0*2,7*]dodeca-2,4,6-triene-10-carboxylic acid tert-butyl ester (220 mg, 0.80 mmol) and 2-(2,5-dichloro-pyrimidin-4-ylamino)-N-methyl-benzamide (236 mg, 0.80 mmol) were combined in 2-methoxyethanol (3 mL) and heated at 120° C. for 6 h. The reaction was then diluted with saturated aqueous $NaHCO_3$ (3 mL), extracted with $CH_2Cl_2$ (3×5 mL), dried over $MgSO_4$, filtered, and concentrated. The resulting residue was purified with silica gel chromatography (0-30% MeOH in EtOAc) to obtain 2-[5-Chloro-2-(12-oxa-10-aza-tricyclo[6.3.1.0*2,7*]dodeca-2(7),3,5-trien-4-ylamino)-pyrimidin-4-ylamino]-N-methyl-benzamide as a tan solid (34 mg, 10%). $^1$HNMR (400 MHz, $CDCl_3$) δ 11.0 (bs, 1H), 8.6 (d, 1H, J=8.3 Hz), 8.0 (s, 1H), 7.6 (s, 1H), 7.5 (d, 1H, J=7.8 Hz), 7.4 (m, 2H), 7.3 (d, 1H, J=7.8 Hz), 7.1 (d, 1H, J=8.1 Hz), 7.0 (appt t, 1H, J=7.6 Hz), 6.5 (bs, 1H), 5.0 (s, 1H), 4.9 (s, 1H), 3.3 (t, 2H, J=13.5 Hz), 3.0 (d, 3H, J=4.8 Hz), 2.9 (bs, 1H), 2.6 (t, 2H, J=13.5 Hz); MS (m/e) 437 (M+1); mp 164-168° C.

Example 66

2-[5-Chloro-2-(10-ethyl-12-oxa-10-aza-tricyclo[6.3.1.0*2,7*]dodeca-2(7),3,5-trien-4-ylamino)-pyrimidin-4-ylamino]-N-methyl-benzenesulfonamide 66a) Following a procedure analogous to 61e, 10-Ethyl-12-oxa-10-aza-tricyclo[6.3.1.0*2,7*]dodeca-2,4,6-trien-4-ylamine hydrochloric acid salt (200 mg, 0.83 mmol) and 2-(2,5-dichloro-pyrimidin-4-ylamino)-N-methyl-benzenesulfonamidebenzamide (212 mg, 0.64 mmol) were converted to 2-[5-Chloro-2-(10-ethyl-12-oxa-10-aza-tricyclo[6.3.1.0*2,7*]dodeca-2(7),3,5-trien-4-ylamino)-pyrimidin-4-ylamino]-N-methyl-benzenesulfonamide as a white solid (11 mg, 3%). $^1$HNMR (400 MHz, DMSO-$d_6$) δ 9.5 (bs, 1H), 9.2 (bs, 1H), 8.5 (m, 1H), 8.3 (s, 1H), 7.8 (d, 1H, J=7.8 Hz), 7.7 (q, 1H, J=4.8 Hz), 7.6 (appt t, 1H, J=8.3 Hz), 7.5 (bs, 1H), 7.4-7.3 (m, 2H), 7.1 (d, 1H, J=7.8 Hz), 5.0 (s, 1H), 4.9 (s, 1H), 2.7 (d, 1H, J=9.9 Hz), 2.6 (d, 1H, J=10.6 Hz), 2.5-2.4 (m, 5H), 2.2 (q, 2H, J=7.2 Hz), 0.8 (t, 3H, J=7.2 Hz); MS (m/e) 501 (M+1); mp 130-134° C.

Example 67

4-[5-Chloro-4-(2-methylcarbamoyl-phenylamino)-pyrimidin-2-ylamino]-12-aza-tricyclo[7.2.1.0*2,7*]dodeca-2(7),3,5-triene-12-carboxylic acid ethyl ester 67a) 4-Amino-12-aza-tricyclo[7.2.1.0*2,7*]dodeca-2(7),3,5-triene-12-carboxylic acid ethyl ester (*J. Med. Chem.* 1988, 31, 433-444)(30 mg, 0.12 mmol) and 2-(2,5-dichloro-pyrimidin-4-ylamino)-N-methyl-benzamide (36 mg, 0.12 mmol) were combined with 4 N HCl (0.030 mL, 0.12 mmol) in isopropanol (1 mL). The resulting mixture was heated in a microwave at 140° C. for 30 min. The resulting mixture was then made basic with saturated aqueous $NaHCO_3$, extracted with $CH_2Cl_2$ (2×5 mL), dried over $MgSO_4$, filtered, and concentrated. The resulting residue was purified with silica gel chromatography (0-100% EtOAc in hexanes) to obtain 4-[5-Chloro-4-(2-methylcarbamoyl-phenylamino)-pyrimidin-2-ylamino]-12-aza-tricyclo[7.2.1.0*2,7*]dodeca-2(7),3,5-triene-12-carboxylic acid ethyl ester as a yellow solid (30 mg, 49%). $^1$HNMR (400 MHz, DMSO-$d_6$) δ 11.6 (s, 1H), 9.4 (s, 1H), 8.8 (d, 1H, J=4.6 Hz), 8.7 (d, 1H, J=8.1 Hz), 8.2 (s, 1H), 7.8 (d, 1H, J=7.1 Hz), 7.7-7.5 (m, 2H), 7.4 (m, 1H), 7.1 (t, 1H, J=7.1 Hz), 7.0 (d, 1H, J=8.3 Hz), 4.7 (m, 1H), 4.4 (m, 1H), 4.1-3.9 (m, 2H), 3.2 (d, 1H, J=14.1Hz), 2.8 (d, 3H, J=4.6 Hz), 2.2-2.0 (m, 2H), 1.7 (t, 1H, J=9.4 Hz), 1.6 (m, 1H), 1.2 (m, 1H), 1.2-1.0 (m, 3H); MS (m/e) 507 (M+1); mp 140-144° C.

Example 68

2-{5-Chloro-2-[12-(2-methoxy-ethyl)-12-aza-tricyclo[7.2.1.0*2,7*]dodeca-2(7),3,5-trien-4-ylamino]-pyrimidin-4-ylamino}-N-methyl-benzamide 68a) 12-Aza-tricyclo[7.2.1.0*2,7*]dodeca-2(7),3,5-trien-4-ylamine (*J. Med. Chem.* 1988, 31, 433-444) (150 mg, 0.86 mmol), 1-bromo-2-methoxy-ethane (120 mg, 0.86 mmol) and potassium carbonate (119 mg, 0.86 mmol) were stirred together in acetone (5 mL) at 50° C. for 6 h. The mixture was filtered and concentrated before purifying on silica gel chromatography (0-50% MeOH in $CH_2Cl_2$) to obtain 12-(2-Methoxy-ethyl)-12-aza-tricyclo[7.2.1.0*2,7*]dodeca-2(7),3,5-trien-4-ylamine as a clear oil (25 mg, 13%). MS (m/e) 233 (M+1).

68b) Following procedures analogous to 61e, 12-(2-Methoxy-ethyl)-12-aza-tricyclo[7.2.1.0*2,7*]dodeca-2(7),3,5-trien-4-ylamine (25 mg, 0.11 mmol) and 2-(2,5-dichloro-pyrimidin-4-ylamino)-N-methyl-benzamide (32 mg, 0.11 mmol) were converted to 2-{5-Chloro-2-[12-(2-methoxy-ethyl)-12-aza-tricyclo[7.2.1.0*2,7*]dodeca-2(7),3,5-trien-4-ylamino]-pyrimidin-4-ylamino}-N-methyl-benzamide as an ivory solid (19 mg, 35%). $^1$HNMR (400 MHz, DMSO-$d_6$) δ 11.6 (s, 1H), 9.3 (s, 1H), 8.8-8.7 (m, 2H, 8.2 (s, 1H), 7.8 (d, 1H, J=6.8 Hz), 7.5 (appt t, 1H, J=7.3 Hz), 7.4-7.3 (m, 2H), 7.1 (appt t, 1H, J=7.3 Hz), 6.9 (d, 1H, J=8.1 Hz), 3.8 (m, 1H), 3.6-3.4 (m, 3H), 3.2 (s, 3H), 3.0 (d, 1H, J=15.8 Hz), 2.8 (d, 3H, J=4.6 Hz), 2.6 (m, 1H), 2.3 (d, 1H, J=15.8), 2.1-2.0 (m, 2H), 1.6 (m, 1H), 1.5 (m, 1H), 1.2 (m, 1H); MS (m/e) 493 (M+1); mp 132-136° C.

Example 69

2-[5-Chloro-2-(12-prop-2-ynyl-12-aza-tricyclo[7.2.1.0*2,7*]dodeca-2(7),3,5-trien-4-ylamino)-pyrimidin-4-ylamino]-N-methyl-benzamide 69a) Following procedures analogous to 68a-68b, 12-Aza-tricyclo[7.2.1.0*2,7*]dodeca-2(7),3,5-trien-4-ylamine (150 mg, 0.86 mmol) and propargyl bromide (102 mg, 0.86 mmol) were converted to 12-Prop-2-ynyl-12-aza-tricyclo[7.2.1.0*2,7*]dodeca-2(7),3,5-trien-4-(60 mg, 33%). Which was converted to 2-[5-Chloro-2-(12-prop-2-ynyl-12-aza-tricyclo[7.2.1.0*2,7*]dodeca-2(7),3,5-trien-4-ylamino)-pyrimidin-4-ylamino]-N-methyl-benzamide as an ivory solid (35 mg, 27%). $^1$HNMR (400 MHz, DMSO-$d_6$) δ 11.5 (s, 1H), 9.4 (s, 1H), 8.8 (d, 1H, J=4.5 Hz), 8.7 (d, 1H, J=7.3 Hz), 8.2 (s, 1H), 7.8 (d, 1H, J=7.8 Hz), 7.5 (appt t, 1H, J=8.0 Hz), 7.4-7.3 (m, 2H), 7.1 (t, 1H, J=7.7 Hz), 6.9 (d, 1H, J=8.3 Hz), 3.8 (d, 1H, J=5.6 Hz), 3.5 (t, 1H, J=5.7 Hz), 3.2 (dd, 2H, J=8.3, 2.3 Hz), 3.1 (t, 1H, J=2.3 Hz), 3.0 (dd, 1H, J=16.8, 5.1 Hz), 2.8 (d, 3H, J=4.5 Hz), 2.3 (d, 1H, J=16.8 Hz), 2.2-2.0 (m, 2H), 1.1 (t, 1H, J=9.6 Hz), 1.0 (m, 1H); MS (m/e) 473 (M+1); mp 273-276° C.

Example 70

2-[5-Chloro-2-(12-cyclopropanecarbonyl-12-aza-tricyclo[7.2.1.0*2,7*]dodeca-2(7),3,5-trien-4-ylamino)-pyrimidin-4-ylamino]-N-methyl-benzamide 70a) Following procedures analogous to 64a-64b, 12-Aza-tricyclo[7.2.1.0*2,7*]dodeca-2(7),3,5-trien-4-ylamine (150 mg, 0.86 mmol) and cyclopropanecarbonyl chloride (90 mg, 0.86 mmol) were converted to (4-Amino-12-aza-tricyclo[7.2.1.0*2,7*]dodeca-2(7),3,5-trien-12-yl)-cyclopropyl-methanone isolated as the hydrochloride salt which was converted to 2-[5-Chloro-2-(12-cyclopropanecarbonyl-12-aza-tricyclo[7.2.1.0*2,7*]dodeca-2(7),3,5-trien-4-ylamino)-pyrimidin-4-ylamino]-N-methyl-benzamide as a white solid (18 mg, 13%). $^1$HNMR (400 MHz, DMSO-$d_6$) δ 11.5 (s, 1H), 9.4 (s, 1H), 8.8-8.6 (m, 2H), 8.2 (s, 1H), 7.8 (d, 1H, J=7.8 Hz), 7.6-7.4 (m, 3H), 7.1 (appt t, 1H, J=7.5 Hz), 7.0 (m, 1H), 5.2 (d, 0.5H, J=5.8 Hz), 5.1 (d, 0.5H, J=5.8 Hz), 4.8 (m, 0.5H), 4.7 (m, 0.5H), 3.2-3.1 (m, 1H), 2.8 (d, 3H, J=4.6 Hz), 2.7 (d, 1H, J=16.2 Hz), 2.3-2.2 (m, 1H), 2.1-1.6 (m, 4H), 0.8-0.3 (m, 4H); MS (m/e) 503 (M+1); mp 158-162° C.

Example 71

N-{(1R,2R)-2-[5-Chloro-2-(12-ethyl-12-aza-tricyclo[7.2.1.0*2,7*]dodeca-2(7),3,5-trien-4-ylamino)-pyrimidin-4-ylamino]-cyclohexyl}-methanesulfonamide 71a) Following procedures analogous to 68a-68b, 12-Aza-tricyclo[7.2.1.0*2,7*]dodeca-2(7),3,5-trien-4-ylamine (400 mg, 2.3 mmol) and ethyl iodide (359 mg, 2.3 mmol) were converted to 12-Ethyl-12-aza-tricyclo[7.2.1.0*2,7*]dodeca-2(7),3,5-trien-4-ylamine (396 mg, 85%), which was reacted with N-[(1R,2R)-2-(2,5-Dichloro-pyrimidin-4-ylamino)-cyclohexyl]-methanesulfonamide (see Example 441a for preparation) to N-{(1R,2R)-2-[5-Chloro-2-(12-ethyl-12-aza-tricyclo[7.2.1.0*2,7*]dodeca-2(7),3,5-trien-4-ylamino)-pyrimidin-4-ylamino]-cyclohexyl}-methanesulfonamide (mixture of diastereomers) isolated as a white solid (69 mg, 15%). $^1$HNMR (400 MHz, CDCl$_3$) δ 7.8 (s, 1H), 7.4-7.2 (m, 3H), 7.0 (d, 1H, J=8.1 Hz), 5.9-5.7 (m, 1H), 5.6 (m, 1H), 4.1 (m, 1H), 3.9 (m, 1H), 3.7 (m, 1H), 3.3-3.1 (m, 2H), 2.8 (d, 3H, J=5.0 Hz), 2.7-2.6 (m, 2H), 2.5-2.1 (m, 5H), 1.9-1.8 (m, 3H), 1.7 (m, 1H), 1.5-1.3 (m, 4H), 1.2 (t, 3H, J=6.8 Hz); MS (m/e) 505 (M+1); mp 150-154° C.

Example 72

N-{2-[5-Chloro-2-(12-ethyl-12-aza-tricyclo[7.2.1.0*2,7*]dodeca-2(7),3,5-trien-4-ylamino)-pyrimidin-4-ylamino]-phenyl}-methanesulfonamide 72a) Following procedures analogous to 61e, 12-Ethyl-12-aza-tricyclo[7.2.1.0*2,7*]dodeca-2(7),3,5-trien-4-ylamine (216 mg, 1.07 mmol) and N-[2-(2,5-dichloro-pyrimidin-4-ylamino)-phenyl]-methanesulfonamide (295 mg, 0.89 mmol) (prepared using a procedure analogous to Example 441 with 2,4,5-trichloropyrimidine, O-phenylenediamine and mesyl chloride) were converted to N-{2-[5-Chloro-2-(12-ethyl-12-aza-tricyclo[7.2.1.0*2,7*]dodeca-2(7),3,5-trien-4-ylamino)-pyrimidin-4-ylamino]-phenyl}-methanesulfonamide isolated as an off-white solid (91 mg, 21%). $^1$HNMR (400 MHz, DMSO-$d_6$) δ 9.3 (s, 1H), 9.2 (s, 1H), 8.6 (s, 1H), 8.1 (s, 1H), 7.9 (bs, 1H), 7.4 (d, 1H, J=6.8 Hz), 7.3-7.2 (m, 4H), 6.8 (d, 1H, J=8.3 Hz), 3.6 (m, 1H), 3.5 (m, 1H), 3.2 (d, 1H, J=1.2 Hz), 3.0 (dd, 1H, J=16.7, 4.6 Hz), 2.9 (s, 3H), 2.5-2.4 (m, 1H), 2.3 (d, 1H, J=2.8 Hz), 2.1-2.0 (m, 2H), 1.6-1.4 (m, 2H), 1.0 (t, 3H, J=7.1 Hz); MS (m/e) 499 (M+1); mp 236-240° C.

Example 73

2-[5-Chloro-2-(3-chloro-12-ethyl-12-aza-tricyclo[7.2.1.0*2,7*]dodeca-2(7),3,5-trien-4-ylamino)-pyrimidin-4-ylamino]-N-methyl-benzamide 73a) N-chlorosuccinimide (172 mg, 1.3 mmol) was added to a solution of 12-aza-tricyclo[7.2.1.0*2,7*]dodeca-2(7),3,5-trien-4-ylamine (150 mg, 0.86 mmol) in acetonitrile (10 mL) at 60° C. in one portion. The reaction was then heated at reflux for 5 h. The resulting mixture was concentrated, diluted with CH$_2$Cl$_2$ (10 mL), washed with 10% ammonium hydroxide (5 mL) and brine (5 mL) before drying over MgSO$_4$ and filtering. Concentration and purification with silica gel chromatography (0-20% MeOH in CH$_2$Cl$_2$) gave 3-Chloro-12-aza-tricyclo[7.2.1.0*2,7*]dodeca-2(7),3,5-trien-4-ylamine as a brown solid (27 mg, 16%). $^1$HNMR (400 MHz, CDCl$_3$) δ 6.8 (d, 1H, J=8.1 Hz), 6.6 (d, 1H, J=8.1 Hz), 4.7 (d, 1H, J=5.3 Hz), 4.0-3.8 (m, 4H), 3.2 (dd, 1H, J=16.5, 4.8 Hz), 2.5 (d, 1H, J=16.5 Hz), 2.2-2.1 (m, 2H), 1.9 (m, 1H), 1.6 (m, 1H); MS (m/e) 209 (M+1); mp 220-224° C.

73b) Following a procedure analogous to 68a-68b, 3-Chloro-12-aza-tricyclo[7.2.1.0*2,7*]dodeca-2(7),3,5-trien-4-ylamine (27 mg, 0.13 mmol), ethyl iodide (22 mg, 1.4 mmol) were converted to 3-Chloro-12-ethyl-12-aza-tricyclo[7.2.1.0*2,7*]dodeca-2(7),3,5-trien-4-ylamine (32 mg, 100%) which was converted to 2-[5-Chloro-2-(3-chloro-12-ethyl-2-aza-tricyclo[7.2.1.0*2,7*]dodeca-2(7),3,5-trien-4-ylamino)-pyrimidin-4-ylamino]-N-methyl-benzamide isolated as a orange-brown solid (13 mg, 19%). $^1$HNMR (400 MHz, CDCl$_3$) δ 11.1 (s, 1H), 8.6 (d, 1H, J=7.8 Hz), 8.1 (m, 2H), 7.5-7.4 (m, 2H), 7.3 (s, 1H), 7.1 (t, 1H, J=7.8 Hz), 6.9 (d, 1H, J=8.3 Hz), 6.2 (m, 1H), 4.5 (d, 1H, J=5.5 Hz), 3.6 (m, 1H), 3.2 (dd, 1H, J=16.9, 4.8 Hz), 3.0 (d, 3H, J=4.8 Hz), 2.6-2.5 (m, 2H), 2.4 (d, 1H, J=16.9 Hz), 2.3-2.2 (m, 2H), 1.8 (m, 1H), 1.5 (m, 1H), 1.1 (t, 3H, J=7.3 Hz); MS (m/e) 497 (M+1); mp 130-134° C.

Example 74

5-Chloro-4-[5-chloro-4-(2-methylcarbamoyl-phenylamino)-pyrimidin-2-ylamino]-12-aza-tricyclo[7.2.1.0*2,7*]dodeca-2(7),3,5-triene-12-carboxylic acid ethyl ester 74a) 5-Chloro-4-[5-chloro-4-(2-methylcarbamoyl-phenylamino)-pyrimidin-2-ylamino]-12-aza-tricyclo[7.2.1.0*2,7*]dodeca-2(7),3,5-triene-12-carboxylic acid ethyl ester was isolated as a minor side-product from Example 73a-b as an ivory solid (8 mg, 11%). $^1$HNMR (400 MHz, CDCl$_3$) δ 11.1 (bs, 0.5H), 10.9 (bs, 0.5H), 8.6-8.5 (m, 1H), 8.2 (m, 1H), 8.1 (s, 1H), 7.8-7.6 (m, 0.5H), 7.5 (d, 1H, J=7.8 Hz), 7.4 (s, 1H), 7.1-7.0 (m, 2H), 6.4-6.3 (m, 1H), 5.4 (m, 1H), 4.6-4.5 (m, 1H), 4.2-4.0 (m, 2H), 3.4-3.2 (m, 1H), 3.0 (d, 3H, J=4.8 Hz), 2.5 (d, 1H, J=16.4 Hz), 2.3-2.1 (m, 2H), 1.9-1.8 (m, 1H), 1.7-1.6 (m, 1H), 1.3-1.2 (m, 3H); MS (m/e) 541 (M+1); mp 126-130° C.

Example 75

3-Chloro-4-[5-chloro-4-(2-methylcarbamoyl-phenylamino)-pyrimidin-2-ylamino]-12-aza-tricyclo[7.2.1.0*2,7*]dodeca-2(7),3,5-triene-12-carboxylic acid ethyl ester 75a) 3-Chloro-4-[5-chloro-4-(2-methylcarbamoyl-phenylamino)-pyrimidin-2-ylamino]-12-aza-tricyclo[7.2.1.0*2,7*]dodeca-2(7),3,5-triene-12-carboxylic acid ethyl ester was isolated from Example 73a-b as an ivory solid (7 mg, 9%). $^1$HNMR (400 MHz, CDCl$_3$) δ 11.1 (s, 1H), 8.6 (d, 1H, J=8.3 Hz), 8.2 (d, 1H, J=8.3 Hz), 8.1 (s, 1H), 7.5-7.4 (m, 2H), 7.3 (s, 1H), 7.1 (t, 1H, J=7.7 Hz), 6.9 (d, 1H, J=8.3 Hz), 6.2 (m, 1H), 5.5-5.4 (m, 1H), 4.6-4.5 (m, 1H), 4.2-4.0 (m, 2H), 3.4-3.3 (m, 1H), 3.0 (d, 3H, J=5.1 Hz), 2.5 (d, 1H, J=16.4 Hz), 2.3-2.1 (m, 2H), 1.9-1.8 (m, 1H), 1.7-1.6 (m, 1H), 1.3-1.2 (m, 3H); MS (m/e) 541 (M+1); mp 138-142° C.

Example 76

N-(2-{5-Chloro-2-[12-(2-methoxy-ethyl)-12-aza-tricyclo[7.2.1.0*2,7*]dodeca-2(7),3,5-trien-4-ylamino]-pyrimidin-4-ylamino}-phenyl)-methanesulfonamide 76a) Following procedures analogous to 61e, 12-(2-Methoxy-ethyl)-12-aza-tricyclo[7.2.1.0*2,7*]dodeca-2(7),3,5-trien-4-ylamine (95 mg, 0.41 mmol) and N-[2-(2,5-dichloro-pyrimidin-4-ylamino)-phenyl]-methanesulfonamide (140 mg, 0.41 mmol) were converted to N-(2-{5-Chloro-2-[12-(2-methoxy-ethyl)-12-aza-tricyclo[7.2.1.0*2,7*]dodeca-2(7),3,5-trien-4-ylamino]-pyrimidin-4-ylamino}-phenyl)-methanesulfonamide as a pale yellow solid (137 mg, 63%). $^1$HNMR (400 MHz, CDCl$_3$) δ 8.0 (s, 1H), 7.6 (d, 1H, J=7.9 Hz), 7.5 (m, 2H), 7.4 (m, 2H), 7.1-7.0 (m, 3H), 6.8 (d, 1H, J=8.3 Hz), 3.7 (m, 1H), 3.6-3.5 (m, 3H), 3.4-3.3 (m, 4H), 3.1 (dd, 1H, J=14.4, 4.0 Hz), 3.0 (s, 3H), 2.8-2.6 (m, 2H), 2.3-2.1 (m, 3H), 1.7 (m, 1H), 1.6 (m, 1H); MS (m/e) 529 (M+1); mp 117-121° C.

Example 77

N-((1R,2R)-2-{5-Chloro-2-[12-(2-methoxy-ethyl)-12-aza-tricyclo[7.2.1.0*2,7*]dodeca-2(7),3,5-trien-4-ylamino]-pyrimidin-4-ylamino}-cyclohexyl)-methanesulfonamide 77a) Following procedures analogous to 61e, 12-(2-Methoxy-ethyl)-12-aza-tricyclo[7.2.1.0*2,7*]dodeca-2(7),3,5-trien-4-ylamine (95 mg, 0.41 mmol) and N-[(1R,2R)-2-(2,5-dichloro-pyrimidin-4-ylamino)-cyclohexyl]-methanesulfonamide (139 mg, 0.41 mmol) were converted to the title compound as a white solid (102 mg, 47%) %) isolated as a mixture of diastereomers. $^1$HNMR (400 MHz, CDCl$_3$) δ 7.9 (s, 1H), 7.3-7.2 (m, 2H), 7.0 (d, 1H, J=7.8 Hz), 6.8 (s, 1H), 5.4 (m, 1H), 5.3 (m, 1H), 4.0 (m, 1H), 3.9 (m, 1H), 3.7-3.5 (m, 3H), 3.3 (appt d, 3H), 3.2-3.1 (m, 1H), 2.9-2.7 (m, 5H), 2.4-2.2 (m, 4H), 1.9-1.8 (m, 3H), 1.7-1.5 (m, 3H), 1.4-1.3 (m, 3H); MS (m/e) 535 (M+1); mp 130-134° C.

Example 78

6-[5-Chloro-4-(2-methylcarbamoyl-phenylamino)-pyrimidin-2-ylamino]-12-aza-tricyclo[7.2.1.0*2,7*]dodeca-2(7),3,5-triene-4,12-dicarboxylic acid 12-ethyl ester 4-methyl ester 78a) Concentrated nitric acid (5 mL) was added dropwise to a mixture of concentrated sulfuric acid (5 mL), 12-aza-tricyclo[7.2.1.0*2,7*]dodeca-2(7),3,5-triene-3,12-dicarboxylic acid 12-ethyl ester 3-methyl ester (300 mg, 1.04 mmol) and CH$_2$Cl$_2$ (5 mL) at 0° C. The resulting brown solution was stirred at this temperature for 30 min before pouring onto ice-water and extracting with CH$_2$Cl$_2$ (2×5 mL). Drying over MgSO$_4$, filtering and concentration gave a brown residue that was purified with silica gel chromatography (0-20% EtOAc in hexanes) to give 6-Nitro-12-aza-tricyclo[7.2.1.0*2,7*]dodeca-2(7),3,5-triene-4,12-dicarboxylic acid 12-ethyl ester 4-methyl ester as a clear oil (81 mg, 23%) $^1$HNMR (400 MHz, CDCl$_3$) δ 8.5 (s, 1H), 8.0 (s, 1H), 5.2 (m, 1H), 4.7 (m, 1H), 4.1 (q, 2H, J=7.1 Hz), 4.0 (s, 3H), 3.6-3.5 (m, 1H), 3.0 (d, 1H, J=18.7), 2.3-2.2 (m, 2H), 1.9 (m, 1H), 1.7 (m, 1H), 1.3-1.2 (m, 3H); MS (m/e) 335 (M+1); and 5-Nitro-12-aza-tricyclo[7.2.1.0*2,7*]dodeca-2(7),3,5-triene-4,12-dicarboxylic acid 12-ethyl ester 4-methyl ester as a pale yellow solid (79 mg, 23%) as the 5-nitro compound. $^1$HNMR (400 MHz, CDCl$_3$) δ 7.6 (s, 1H), 7.4 (s, 1H), 5.1 (m, 1H), 4.6 (m, 1H), 4.1 (q, 2H, J=7.3 Hz), 3.9 (s, 3H), 3.5-3.4 (m, 1H), 2.7 (d, 1H, J=17.4), 2.3-2.2 (m, 2H), 1.9 (m, 1H), 1.7 (m, 1H), 1.3-1.2 (m, 3H); MS (m/e) 335 (M+1); The regioisomers were distinguished by NOE and $^1$H-$^1$H COSY 78b) Following procedures analogous top 61d-61e, 6-nitro-12-aza-tricyclo[7.2.1.0*2,7*]dodeca-2(7),3,5-triene-4,12-dicarboxylic acid 12-ethyl ester 4-methyl ester was converted to 6-Amino-12-aza-tricyclo[7.2.1.0*2,7*]dodeca-2(7),3,5-triene-4,12-dicarboxylic acid 12-ethyl ester 4-methyl ester as a yellow oil (52 mg, 71 which was converted to 6-[5-Chloro-4-(2-methylcarbamoyl-phenylamino)-pyrimidin-2-ylamino]-12-aza-tricyclo[7.2.1.0*2,7*]dodeca-2(7),3,5-triene-4,12-dicarboxylic acid 12-ethyl ester 4-methyl ester (18 mg, 19%). $^1$HNMR (400 MHz, CDCl$_3$) δ 11.2 (s, 1H), 8.5 (d, 1H, J=8.6 Hz), 8.4 (bs, 1H), 8.1 (s, 1H), 7.6 (bs, 1H), 7.4 (d, 1H, J=7.8 Hz), 7.3 (m, 1H), 7.0 (t, 1H, J=7.7 Hz), 6.5 (s, 1H), 6.2 (bs, 1H), 5.1-5.0 (m, 1H), 4.7-4.6 (m, 1H), 4.1-4.0 (m, 2H), 3.8 (s, 3H), 3.3-3.2 (m, 1H), 3.0 (d, 3H, J=5.5 Hz), 2.5 (d, 1H, J=16.9 Hz), 2.3-2.2 (m, 2H), 1.9 (t, 1H, J=8.3 Hz), 1.7-1.6 (m, 1H), 1.2 (t, 3H, J=7.1 Hz); MS (m/e) 565 (M+1); mp 140-144° C.

Example 79

2-[2-(12-Aza-tricyclo[7.2.1.0*2,7*]dodeca-2(7),3,5-trien-4-ylamino)-5-chloro-pyrimidin-4-ylamino]-N-methyl-benzamide 79a) Following a procedure analogous to 61e, 12-Aza-tricyclo[7.2.1.0*2,7*]dodeca-2(7),3,5-trien-4-ylamine (100 mg, 0.57 mmol) and 2-(2,5-dichloro-pyrimidin-4-ylamino)-N-methyl-benzamide (170 mg, 0.57 mmol) were converted to the title compound as an off-white solid (151 mg, 61%). $^1$HNMR (400 MHz, DMSO-d$_6$) δ 11.6 (s, 1H), 9.3 (s, 1H), 8.8-8.7 (m, 2H), 8.3 (s, 1H), 7.8 (d, 1H, J=7.8 Hz), 7.5 (t, 1H, J=7.6 Hz), 7.3-7.2 (m, 2H), 7.1 (t, 1H, J=7.6 Hz), 6.9 (d, 1H, J=7.8 Hz), 4.0 (m, 1H), 3.7 (m, 1H), 3.0 (dd, 1H, J=16.3, 4.8

Hz), 2.8 (d, 3H, J=4.0 Hz), 2.7-2.6 (bs, 1H), 2.4 (d, 1H, J=16.3 Hz), 1.9-1.8 (m, 2H), 1.7 (m, 1H), 1.5-1.4 (m, 1H); MS (m/e) 435 (M+1); mp 209-212° C.

Example 80

2-[5-Chloro-2-(12-isopropyl-12-aza-tricyclo [7.2.1.0*2,7*]dodeca-2(7),3,5-trien-4-ylamino)-pyrimidin-4-ylamino]-N-methyl-benzamide 80a) Sodium triacetoxyborohydride (100 mg, 0.47 mmol) was added to a solution of 2-[2-(12-aza-tricyclo[7.2.1.0*2, 7*]dodeca-2(7),3,5-trien-4-ylamino)-5-chloro-pyrimidin-4-ylamino]-N-methyl-benzamide (100 mg, 0.23 mmol), acetone (0.034 mL, 0.47 mmol), acetic acid (1 drop) and dichloroethane (5 mL). The reaction was stirred at room temperature for 18 h. The reaction was then quenched with saturated aqueous $NaHCO_3$ (5 mL), extracted with $CH_2Cl_2$ (2×5 mL), dried over $MgSO_4$, filtered, and concentrated to afford the title compound as off-white solid (89 mg, 82%). $^1$HNMR (400 MHz, DMSO-$d_6$) δ 11.6 (s, 1H), 9.3 (s, 1H), 8.8-8.7 (m, 2H), 8.2 (s, 1H), 7.8 (d, 1H, J=7.8 Hz), 7.5 (appt t, 1H, J=8.1 Hz), 7.4 (d, 1H, J=8.6), 7.3 (s, 1H), 7.1 (appt t, 1H, J=7.6 Hz), 6.9 (d, 1H, J=8.3 Hz), 3.9 (m, 1H), 3.6 (m, 1H), 3.0 (dd, 1H, J=17.2, 4.6 Hz), 2.8 (d, 3H, J=4.3 Hz), 2.4 (m, 1H), 2.2 (d, 1H, J=17.2 Hz), 2.1-2.0 (m, 2H), 1.6 (m, 1H), 1.5 (m, 1H), 1.1 (d, 3H, J=5.9 Hz), 0.9 (d, 3H, J=5.9 Hz); MS (m/e) 477 (M+1); mp 202-205° C.

Example 81

2-[5-Chloro-2-(3-chloro-12-aza-tricyclo[7.2.1.0*2, 7*]dodeca-2(7),3,5-trien-4-ylamino)-pyrimidin-4-ylamino]-N-methyl-benzamide 81a) Following a procedure analogous to 61e, 3-Chloro-12-aza-tricyclo[7.2.1.0*2,7*]dodeca-2(7),3,5-trien-4-ylamine (140 mg, 0.67 mmol) and 2-(2,5-dichloro-pyrimidin-4-ylamino)-N-methyl-benzamide (200 mg, 0.67 mmol) were converted to the title compound as a yellow solid (151 mg, 49%). $^1$HNMR (400 MHz, $CDCl_3$) δ 11.1 (s, 1H), 8.6 (d, 1H, J=8.6 Hz), 8.1 (s, 1H), 8.2 (d, 1H, J=8.3 Hz), 7.5-7.4 (m, 2H), 7.3 (s, 1H), 7.1 (t, 1H, J=7.6 Hz), 6.9 (d, 1H, J=8.3 Hz), 6.2 (bs, 1H), 4.7 (d, 1H, J=5.0 Hz), 3.9 (m, 1H), 3.1 (dd, 1H, J=16.5, 5.0 Hz), 3.0 (d, 3H, J=4.8 Hz), 2.5 (d, 1H, J=16.5 Hz), 2.2-2.1 (m, 2H), 1.9 (m, 1H), 1.7 (bs, 1H), 1.6 (m, 1H); MS (m/e) 438 (M−$NCH_3$); mp 132-136° C.

Example 82

N-{(1R,2R)-2-[2-(12-Aza-tricyclo[7.2.1.0*2,7*] dodeca-2(7),3,5-trien-4-ylamino)-5-chloro-pyrimidin-4-ylamino]-cyclohexyl}-methanesulfonamide 82a) Following a procedure analogous to 61e, 12-Aza-tricyclo[7.2.1.0*2,7*]dodeca-2(7),3,5-trien-4-ylamine (200 mg, 1.15 mmol) and N-[(1R,2R)-2-(2,5-dichloro-pyrimidin-4-ylamino)-cyclohexyl]-methanesulfonamide (389 mg, 1.15 mmol) were converted to the title compound isolated as an ivory solid (430 mg, 78%) %), isolated as a mixture of diastereomers. $^1$HNMR (400 MHz, DMSO-$d_6$) δ 9.1 (s, 1H), 7.9 (s, 1H), 7.5 (s, 0.5H), 7.4 (s, 0.5H), 7.3 (appt t, 1H, J=7.8 Hz), 7.2 (d, 0.5H, J=8.1 Hz), 7.1 (d, 0.5H, J=8.3 Hz), 6.9 (d, 1H, J=8.3 Hz), 6.7 (d, 1H, J=7.3 Hz), 4.1 (d, 0.5H, J=4.0 Hz), 4.0 (d, 0.5H, J=3.4 Hz), 3.9-3.8 (m, 1H), 3.7 (m, 1H), 3.4 (m, 1H), 3.0 (d, 1H, J=4.5 Hz), 2.9 (d, 3H, J=7.3 Hz), 2.5-2.4 (m, 2H), 2.1-2.0 (m, 2H), 1.9 (m, 2H), 1.8-1.6 (m, 3H), 1.5-1.2 (m, 5H); MS (m/e) 477 (M+1); mp 150-154° C.

Example 83

N-{(1R,2R)-2-[5-Chloro-2-(12-isopropyl-12-aza-tricyclo[7.2.1.0*2,7*]dodeca-2(7),3,5-trien-4-ylamino)-pyrimidin-4-ylamino]-cyclohexyl}-methanesulfonamide 83a) Following a procedure analogous to 80a, N-{(1R,2R)-2-[2-(12-aza-tricyclo[7.2.1.0*2,7*]dodeca-2(7),3,5-trien-4-ylamino)-5-chloro-pyrimidin-4-ylamino]-cyclohexyl}-methanesulfonamide (90 mg, 0.19 mmol), was converted to the title compound as off-white solid (77 mg, 79%): 1:1 mixture of diastereomers. $^1$HNMR (400 MHz, DMSO-$d_6$) δ 9.1 (s, 1H), 7.9 (s, 1H), 7.6 (s, 0.5H), 7.5 (s, 0.5H), 7.3 (m, 1H), 7.2 (d, 0.5H, J=8.6 Hz), 7.1 (d, 0.5H, J=8.3 Hz), 6.9 (d, 1H, J=8.3 Hz), 6.7 (d, 1H, J=8.1 Hz), 4.0 (m, 1H), 3.9-3.8 (m, 1H), 3.6 (m, 1H), 3.4 (m, 1H), 3.0 (m, 1H), 2.9 (d, 3H, J=7.1 Hz), 2.2 (d, 1H, J=17.1 Hz), 2.1-2.0 (m, 4H), 1.8-1.7 (m, 3H), 1.6-1.5 (m, 1H), 1.4 (m, 1H), 1.4-1.2 (m, 7H), 1.0-0.9 (m, 3H); MS (m/e) 519 (M+1); mp 140-144° C.

Example 84

N-{(1R,2R)-2-[2-(12-sec-Butyl-12-aza-tricyclo [7.2.1.0*2,7*]dodeca-2(7),3,5-trien-4-ylamino)-5-chloro-pyrimidin-4-ylamino]-cyclohexyl}-methanesulfonamide 84a) Following a procedure analogous to 80a, N-{(1R,2R)-2-[2-(12-aza-tricyclo[7.2.1.0*2,7*]dodeca-2(7),3,5-trien-4-ylamino)-5-chloro-pyrimidin-4-ylamino]-cyclohexyl}-methanesulfonamide (90 mg, 0.19 mmol) and 2-butanone were converted to the title compound as an off-white solid (96 mg, 95%): 1:1 mixture of diastereomers. $^1$HNMR (400 MHz, MeOD) δ7.9 (s, 1H), 7.5 (m, 2H), 7.1 (d, 1H, J=8.3 Hz), 4.6 (m, 1H), 4.2 (m, 1H), 4.0 (m, 1H), 3.3 (m, 1H), 2.9 (d, 3H, J=4.0 Hz), 2.8 (m, 1H), 2.7 (d, 1H, J=7.4 Hz), 2.4-2.3 (m, 2H), 2.2-2.0 (m, 3H), 1.9-1.8 (m, 3H), 1.6-1.2 (m, 10H), 1.0-0.9 (m, 3H); MS (m/e) 533 (M+1); mp 162-166° C.

Example 85

N-{(1R,2R)-2-[2-(12-sec-Butyl-12-aza-tricyclo [7.2.1.0*2,7*]dodeca-2(7),3,5-trien-4-ylamino)-5-chloro-pyrimidin-4-ylamino]-cyclohexyl}-methanesulfonamide 85a) Following a procedure analogous to 80a, N-{(1R,2R)-2-[2-(12-aza-tricyclo[7.2.1.0*2,7*]dodeca-2(7),3,5-trien-4-ylamino)-5-chloro-pyrimidin-4-ylamino]-cyclohexyl}-methanesulfonamide (90 mg, 0.19 mmol) and cyclopropanecarbaldehyde (0.056 mL, 0.75 mmol), were converted to the title compound as an off-white solid (69 mg, 69%): 1:1 mixture of diastereomers. $^1$HNMR (400 MHz, DMSO-$d_6$) δ 9.1 (s, 1H), 7.9 (s, 1H), 7.6 (s, 0.5H), 7.5 (s, 0.5H), 7.3 (m, 1H), 7.2 (d, 0.5H, J=8.6 Hz), 7.1 (d, 0.5H, J=8.3 Hz), 6.9 (d, 1H, J=8.3 Hz), 6.7 (d, 1H, J=8.3 Hz), 4.0 (m, 1H), 3.9-3.8 (m, 1H), 3.5 (m, 1H), 3.4-3.3 (m, 1H), 3.0-2.9 (m, 4H), 2.5-2.4 (m, 1H), 2.3 (d, 1H, J=16.9 Hz), 2.2-2.0 (m, 5H), 1.9 (m, 3H), 1.6-1.2 (m, 6H), 0.9-0.8 (m, 2H), 0.4 (m, 2H); MS (m/e) 531 (M+1); mp 120-124° C.

Example 86

2-[5-Chloro-2-(3-chloro-12-isopropyl-12-aza-tricyclo[7.2.1.0*2,7*]dodeca-2(7),3,5-trien-4-ylamino)-pyrimidin-4-ylamino]-N-methyl-benzamide 86a) Following a procedure analogous to 80a, 2-[5-chloro-2-(3-chloro-12-aza-tricyclo[7.2.1.0*2,7*]dodeca-2(7),3,5-trien-4-ylamino)-pyrimidin-4-ylamino]-N-methyl-benzamide (90 mg, 0.19 mmol) was converted to the title compound as a yellowish solid (49 mg, 51%). $^1$HNMR (400 MHz, DMSO-$d_6$) δ 11.7 (s, 1H), 8.8-8.7 (m, 2H), 8.4 (d, 1H, J=8.3 Hz), 8.2 (s, 1H), 7.7 (d, 1H, J=7.8 Hz), 7.4 (d, 1H, J=7.8 Hz), 7.2 (t, 1H, J=7.8 Hz), 7.1-7.0 (m, 2H), 4.5 (m, 1H), 3.7 (m, 1H), 3.1 (m, 1H), 2.8 (d, 3H, J=4.3 Hz), 2.5-2.3 (m, 2H), 2.1 (m, 2H), 1.6-1.5 (m, 2H), 1.2 (d, 3H, J=6.0 Hz), 0.9 (d, 3H, J=6.0 Hz); MS (m/e) 511 (M+1); mp 105-109° C.

Example 87

2-{5-Chloro-2-[3-chloro-12-(2-methoxy-ethyl)-12-aza-tricyclo[7.2.1.0*2,7*]dodeca-2(7),3,5-trien-4-ylamino]-pyrimidin-4-ylamino}-N-methyl-benzamide 87a) Analogous to 68a-b, 3-Chloro-12-aza-tricyclo[7.2.1.0*2,7*]dodeca-2(7),3,5-trien-4-ylamine (200 mg, 0.96 mmol), was converted to 3-Chloro-12-ethyl-12-aza-tricyclo[7.2.1.0*2,7*]dodeca-2(7),3,5-trien-4-ylamine which was converted to 2-{5-Chloro-2-[3-chloro-12-(2-methoxy-ethyl)-12-aza-tricyclo[7.2.1.0*2,7*]dodeca-2(7),3,5-trien-4-ylamino]-pyrimidin-4-ylamino}-N-methyl-benzamide as an ivory solid (6 mg, 3%). $^1$HNMR (400 MHz, DMSO-$d_6$) δ 11.7 (s, 1H), 8.8-8.7 (m, 2H), 8.4 (d, 1 Hz, J=7.8 Hz), 8.1 (s, 1H), 7.7 (d, 1H, J=7.8 Hz), 7.4 (d, 1H, J=7.8 Hz), 7.3 (t, 1H, J=7.1 Hz), 7.1-7.0 (m, 2H), 4.4 (m, 1H), 3.6 (m, 1H), 3.5-3.4 (m, 2H), 3.2 (s, 3H), 3.1 (m, 1H), 2.8 (d, 3H, J=4.3 Hz), 2.7-2.6 (m, 1H), 2.5-2.4 (m, 1H), 2.2-2.1 (m, 2H), 1.6-1.4 (m, 2H), 1.2 (m, 1H); MS (m/e) 527 (M+1); mp 81-85° C.

Example 88

2-{5-Chloro-2-[5-chloro-12-(2-methoxy-ethyl)-12-aza-tricyclo[7.2.1.0*2,7*]dodeca-2(7),3,5-trien-4-ylamino]-pyrimidin-4-ylamino}-N-methyl-benzamide 88a) The title compound was isolated as a minor side-product from the reaction in 87a as an white solid (1 mg, <1%). $^1$HNMR (400 MHz, DMSO-$d_6$) δ 11.7 (s, 1H), 8.8-8.7 (m, 2H), 8.4 (d, 1H, J=8.1 Hz), 8.2 (s, 1H), 7.7 (d, 1H, J=8.1 Hz), 7.3-7.2 (m, 3H), 7.0 (t, 1H, J=7.5), 3.9 (m, 1H), 3.5 (m, 1H), 3.4 (m, 2H), 3.2 (s, 3H), 3.1 (m, 1H), 2.8 (d, 3H, J=4.3 Hz), 2.7-2.6 (m, 1H), 2.5-2.4 (m, 1H), 2.1-2.0 (m, 2H), 1.6-1.4 (m, 2H), 1.3 (m, 1H); MS (m/e) 527 (M+1); mp 112-115° C.

Example 89

N-{(1R,2R)-2-[2-(12-sec-Butyl-12-aza-tricyclo[7.2.1.0*2,7*]dodeca-2(7),3,5-trien-4-ylamino)-5-chloro-pyrimidin-4-ylamino]-cyclohexyl}-methanesulfonamide 89a) Following a procedure analogous to 80a, N-{(1R,2R)-2-[2-(12-aza-tricyclo[7.2.1.0*2,7*]dodeca-2(7),3,5-trien-4-ylamino)-5-chloro-pyrimidin-4-ylamino]-cyclohexyl}-methanesulfonamide (40 mg, 0.084 mmol) and pivaldehyde were converted to the title compound isolated as give a white solid (5 mg, 11%) isolated as a mixture of diastereomers. $^1$HNMR (400 MHz, DMSO-$d_6$) δ 9.1 (s, 1H), 7.9 (s, 1H), 7.6 (s, 0.5H), 7.5 (s, 0.5H), 7.3 (m, 1H), 7.2 (m, 1H), 7.1 (m, 1H), 6.7 (m, 1H), 3.9 (m, 1H), 3.8 (m, 1H), 3.4 (m, 2H), 3.1 (m, 1H), 2.9 (s, 3H), 2.3-2.2 (m, 2H), 2.1-2.0 (m, 5H), 1.7-1.6 (m, 3H), 1.5-1.3 (m, 5H), 0.8 (s, 9H); MS (m/e) 547 (M+1); mp 117-120° C.

Example 90

2-[2-(12-Aza-tricyclo[7.2.1.0*2,7*]dodeca-2(7),3,5-trien-4-ylamino)-5-chloro-pyrimidin-4-ylamino]-3-chloro-N-methyl-benzamide 90a) Following a procedure analogous to 61e, 12-Aza-tricyclo[7.2.1.0*2,7*]dodeca-2(7),3,5-trien-4-ylamine hydrochloride salt (83 mg, 0.39 mmol) and 3-chloro-2-(2,5-dichloro-pyrimidin-4-ylamino)-N-methyl-benzamide (see Example 312a-b for preparation) (100 mg, 0.30 mmol) were converted to the title compound isolated as an ivory solid (85 mg, 18%). $^1$HNMR (400 MHz, DMSO-$d_6$) δ 9.2-9.0 (m, 2H), 8.4 (bs, 1H), 8.1 (s, 1H), 7.7 (d, 1H, J=7.3 Hz), 7.6 (d, 1H, J=7.6 Hz), 7.4 (m, 1H), 7.1 (s, 1H), 7.0 (d, 1H, J=7.6 Hz), 6.7 (d, 1H, J=8.1 Hz), 3.8-3.6 (m, 2H), 3.3 (bs, 1H), 2.9 (dd, 1H, J=16.2, 4.3 Hz), 2.6 (s, 3H), 2.3 (d, 1H, J=16.2 Hz), 1.9-1.8 (m, 2H), 1.6-1.4 (m, 2H); MS (m/e) 469 (M+1); mp 150-154° C.

Example 91

3-Chloro-2-{5-chloro-2-[12-(2-methoxy-ethyl)-12-aza-tricyclo[7.2.1.0*2,7*]dodeca-2(7),3,5-trien-4-ylamino]-pyrimidin-4-ylamino}-N-methyl-benzamide 91a) Following a procedure analogous to 68a, 2-[2-(12-Aza-tricyclo[7.2.1.0*2,7*]dodeca-2(7),3,5-trien-4-ylamino)-5-chloro-pyrimidin-4-ylamino]-3-chloro-N-methyl-benzamide (60 mg, 0.13 mmol), 1-bromo-2-methoxy-ethane (120 mg, 0.48 mmol) were converted to the title compound as a yellow solid (23 mg, 34%). $^1$HNMR (400 MHz, DMSO-$d_6$) δ 9.2 (bs, 1H), 9.0 (bs, 1H), 8.3 (m, 1H), 8.1 (s, 1H), 7.7 (d, 1H, J=7.6 Hz), 7.6 (d, 1H, J=7.3 Hz), 7.4 (t, 1H, J=8.1 Hz), 7.1 (s, 1H), 7.0 (m, 1H), 6.7 (m, 1H), 3.6-3.4 (m, 4H), 3.2 (s, 3H), 2.9 (m, 1H), 2.7 (d, 3H, J=4.3 Hz), 2.5-2.4 (m, 2H), 2.2 (m, 1H), 2.1-2.0 (m, 2H), 1.5-1.4 (m, 2H); MS (m/e) 527 (M+1); mp 240-244° C.

Example 92

N-{(1R,2R)-2-[5-Chloro-2-(3-methoxy-12-aza-tricyclo[7.2.1.0*2,7*]dodeca-2(7),3,5-trien-4-ylamino)-pyrimidin-4-ylamino]-cyclohexyl}-methanesulfonamide 92a) 12-Aza-tricyclo[7.2.1.0*2,7*]dodeca-2(7),3,5-trien-4-ylamine (572 mg, 3.3 mmol), di-tert-butyl dicarbonate (1.6 g, 7.2 mmol), triethylamine (1.0 mL, 7.2 mmol) were stirred at room temperature in tetrahydrofuran (20 mL) for 18 h. The reaction was then concentrated and purified with silica gel chromatography (0-30% EtOAc in hexanes) to obtain 4-tert-Butoxycarbonylamino-12-aza-tricyclo[7.2.1.0*2,7*]dodeca-2(7),3,5-triene-12-carboxylic acid tert-butyl ester as a white solid (1.1 g, 90%). MS (m/e) 375 (M+1).

92b) Tert-butyllithium (1.7M, 2.3 mL, 4.0 mmol) was added dropwise to a solution of 4-tert-butoxycarbonylamino-12-aza-tricyclo[7.2.1.0*2,7*]dodeca-2(7),3,5-triene-12-carboxylic acid tert-butyl ester (450 mg, 1.2 mmol) in THF (5 mL) at −78° C. The solution was then allowed to warm slowly to −20° C. and stir at that temperature for 1 h before cooling again to −78° C. and adding trimethyl borate (0.37 mL, 3.2 mmol) via syringe. The reaction was allowed to warm to room temperature slowly and stir overnight. The reaction was quenched with methanol (1 mL) and hydrogen peroxide (30% solution, 0.37 mL, 3.6 mmol) was added to the reaction and allowed to stir at room temperature for 2 h. The mixture was then adjusted to neutral pH with 1 N HCl, extracted with $CH_2Cl_2$ (3×10 mL), dried over $MgSO_4$, filtered and concentrated. The resulting residue was purified with silica gel chromatography (0-50% EtOAc in hexanes) to obtain 4-tert-Butoxycarbonylamino-3-hydroxy-12-aza-tricyclo[7.2.1.0*2,7*]dodeca-2(7),3,5-triene-12-carboxylic acid tert-butyl ester as a brown foam (260 mg, 55%). $^1$HNMR (400 MHz, $CDCl_3$) δ 7.7 (m, 1H), 7.5 (s, 1H), 7.1 (d, 1H, J=8.1 Hz), 6.9 (m, 1H), 4.5 (d, 1H, J=7.8 Hz), 4.1 (m, 1H), 3.1 (dd, 1H, J=14.4, 4.9 Hz), 2.9 (dd, 1H, J=14.4, 4.9 Hz), 2.7 (dd, 1H, J=18.2, 8.1 Hz), 2.6 (dd, 1H, J=18.2, 10.6 Hz), 2.2-2.1 (m, 1H), 1.5-1.3 (m, 19H); $^1$H-$^1$H COSY interactions between peak at 7.7 and 7.1 ppm; MS (m/e) 391 (M+1).

92c) 4-tert-Butoxycarbonylamino-3-hydroxy-12-aza-tricyclo[7.2.1.0*2,7*]dodeca-2(7),3,5-triene-12-carboxylic acid tert-butyl ester (260 mg, 0.67 mmol), dimethyl sulfate (0.13 mL, 1.3 mmol), cesium carbonate (430 mg, 1.3 mmol) and dioxane (3 mL) were stirred together at 90° C. for 20 h. The reaction mixture was then diluted with water (5 mL), extracted with $CH_2Cl_2$ (2×5 mL), dried over $MgSO_4$, filtered and concentrated. The resulting residue was purified with silica gel chromatography (0-50% EtOAc in hexanes) to obtain 4-tert-Butoxycarbonylamino-3-methoxy-12-aza-tricyclo[7.2.1.0*2,7*]dodeca-2(7),3,5-triene-12-carboxylic acid tert-butyl ester as a yellow, foamy residue (198 mg, 74%). $^1$HNMR (400 MHz, $CDCl_3$) δ 7.6 (s, 1H), 7.4 (d, 1H, J=8.0 Hz), 7.1 (d, 1H, J=8.0 Hz), 4.5 (m, 1H), 4.1 (m, 1H), 3.3 (s, 3H), 3.1 (dd, 1H, J=14.4, 4.8 Hz), 2.9 (dd, 1H, J=14.5, 5.0 Hz), 2.7 (dd, 1H, J=17.9, 7.8 Hz), 2.6 (dd, 1H, J=18.4, 10.4 Hz), 2.2 (m, 1H), 1.5-1.4 (m, 19H); MS (m/e) 349 (M-$C_4H_7$).

92d) Following a procedure analogous to 61e, 4-tert-Butoxycarbonylamino-3-methoxy-12-aza-tricyclo[7.2.1.0*2,7*]dodeca-2(7),3,5-triene-12-carboxylic acid tert-butyl ester (198 mg, 0.49 mmol) was stirred in 4 N HCl (5 mL) for 4 h and concentrated. The residue was then combined with N-[(1R,2R)-2-(2,5-dichloro-pyrimidin-4-ylamino)-cyclohexyl]-methanesulfonamide (166 mg, 0.49 mmol) and 4 N HCl (0.12 mL, 0.49 mmol) and converted to N-{(1R,2R)-2-[5-Chloro-2-(3-methoxy-12-aza-tricyclo[7.2.1.0*2,7*]dodeca-2(7),3,5-trien-4-ylamino)-pyrimidin-4-ylamino]-cyclohexyl}-methanesulfonamide isolated as a mixture of diastereomers as an ivory solid (32 mg, 13%). $^1$HNMR (400 MHz, $CDCl_3$) δ 7.9 (s, 1H), 7.8 (s, 0.5H), 7.7 (s, 0.5H), 7.3 (m, 1H), 7.2 (m, 1H), 5.9 (m, 0.5H), 5.7 (m, 0.5H), 5.1 (m, 1H), 3.7-3.6 (m, 2H), 3.5 (s, 3H), 3.1-2.9 (m, 3H), 2.8-2.7 (m, 1H), 2.6 (s, 3H), 2.5 (m, 1H), 2.1-2.0 (m, 8H), 1.8-1.7 (m, 3H), 1.1 (m, 1H); MS (m/e) 507 (M+1); mp 110-114° C.

Example 93

N-{(1R,2R)-2-[5-Chloro-2-(12-ethyl-3-methoxy-12-aza-tricyclo[7.2.1.0*2,7*]dodeca-2(7),3,5-trien-4-ylamino)-pyrimidin-4-ylamino]-cyclohexyl}-methanesulfonamide 93a) Following a procedure analogous to 68a, N-{(1R,2R)-2-[5-Chloro-2-(3-methoxy-12-aza-tricyclo[7.2.1.0*2,7*]dodeca-2(7),3,5-trien-4-ylamino)-pyrimidin-4-ylamino]-cyclohexyl}-methanesulfonamide (25 mg, 0.049 mmol), iodoethane were converted to the title compound as a light pink solid (6 mg, 23%), as a mixture of diastereomers. $^1$HNMR (400 MHz, $CDCl_3$) δ 7.9 (s, 1H), 7.7 (m, 1H), 7.4 (m, 1H), 7.2 (m, 1H), 5.7 (m, 1H), 3.8 (m, 1H), 3.7 (m, 1H), 3.5 (s, 3H), 3.3-3.0 (m, 3H), 2.9 (s, 3H), 2.8 (m, 1H), 2.6 (m, 1H), 2.2-1.8 (m, 9H), 1.7-1.6 (m, 3H), 1.4-1.2 (m, 1H), 1.1-1.0 (m, 4H); MS (m/e) 535 (M+1); mp 102-106° C.

Example 101

(+/−)-2-[5-Chloro-2-(12-ethyl-12-aza-tricyclo[7.2.1.0*2,7*]dodeca-2(7),3,5-trien-4-ylamino)-pyrimidin-4-ylamino]-N-methyl-benzamide 101a) A solution of (+/−)-12-Aza-tricyclo[7.2.1.0*2,7*]dodeca-2(7),3,5-trien-4-ylamine (150 mg, 0.86 mmol) in acetone (4 mL) was treated with ethyl iodide (0.07 mL, 0.86 mmol), potassium carbonate (237 mg, 1.72 mmol) and stirred for 1 h. The mixture was partitioned between dichloromethane and brine and the organic layer dried ($MgSO_4$), filtered and concentrated to give (+/−)-12-Ethyl-12-aza-tricyclo[7.2.1.0*2,7*]dodeca-2(7),3,5-trien-4-ylamine which was used without further purification.

101b) 2-methoxyethanol (8.6 mL), 4N HCl in p-dioxane (0.215 mL, 1.2 eq) and 2-(2,5-dichloro-pyrimidin-4-ylamino)-N-methyl-benzamide (129 mgs, 1 eq) and (+/−)-12-Ethyl-12-aza-tricyclo[7.2.1.0*2,7*]dodeca-2(7),3,5-trien-4-ylamine was heated to 120° C. for 2 h. The mixture cooled to room temp treated with 3 equivalents of MP-carbonate and stirred for 30 min. Filtration, followed by concentration and purification by ISCO chromatography (12 gram column, SiO2, gradient 20% EtOAc/hexane to 100% EtOAc) gave (+/−)-2-[5-Chloro-2-(12-ethyl-12-aza-tricyclo[7.2.1.0*2,7*]dodeca-2(7),3,5-trien-4-ylamino)-pyrimidin-4-ylamino]-N-methyl-benzamide (45 mg, 11%). MP: 218-221° C.; 1H-NMR ($CDCl_3$) δ 11.10 (s, 1H), 8.65 (d, J=8.1 Hz, 1H), 8.1 (s, 1H), 7.51-7.47 (m, 2H), 7.28-7.26 (m, 1H), 7.12-7.10 (m, 1H), 7.00 (s, 1H), 6.79 (d, J=7.8 Hz, 1H), 6.84 (d, J=8.0 Hz, 1H), 6.52-6.49 (m, 1H), 3.89-3.84 (m, 2H), 3.58-3.55 (m, 2H), 3.05-3.03 (m, 1H), 3.04 (d, J=5.1 Hz, 3H), 2.61-2.51 (m, 3H), 2.25-2.21 (m, 2H), 1.18-1.10 (m, 3H); LC/MS (ESI+): 463.34 (M+H).

Example 102

(+/−)-2-[5-Chloro-2-(12-methanesulfonyl-12-aza-tricyclo[7.2.1.0*2,7*]dodeca-2(7),3,5-trien-4-ylamino)-pyrimidin-4-ylamino]-N-methyl-benzamide 102a) Following the procedure in Example 101a-101b, (+/−)-12-Aza-tricyclo[7.2.1.0*2,7*]dodeca-2(7),3,5-trien-4-ylamine (150 mg, 0.86 mmol) and methanesulfonyl chloride (0.07 mL, 1 eq) were reacted and the crude product converted to (+/−)-2-[5-Chloro-2-(12-methanesulfonyl-12-aza-tricyclo[7.2.1.0*2,7*]dodeca-2(7),3,5-trien-4-ylamino)-pyrimidin-4-ylamino]-N-methyl-benzamide (31 mg, 7%). MP: 100-102° C.; $^1$H-NMR ($CDCl_3$) δ 11.05 (s, 1H), 8.58 (d, J=7.9 Hz, 1H), 8.10 (s, 1H), 7.54-7.49 (m, 2H), 7.29-7.23 (m, 2H), 7.13-7.04 (m, 3H), 6.61-6.52 (br s, 1H), 4.55-4.54 (m, 2H), 3.40-3.28 (m, 2H), 3.04-3.01 (m, 3H), 2.95-2.90 (m, 2H), 2.32-2.23 (m, 3H), 1.75-1.68 (m, 2H); LC/MS (ESI+): 513.29 (M+H).

Example 103

2-[5-Chloro-2-(1-methyl-2,3,4,5-tetrahydro-1H-benzo[b]azepin-7-ylamino)-pyrimidin-4-ylamino]-N-methyl-benzamide 103a) A solution of 7-Nitro-1,3,4,5-tetrahydro-benzo[b]azepin-2-one (0.34 g, 1.65 mmol) in THF (10 mL) was treated with borane-THF (5 mL, 4.95 mmol) and heated to 60° C. and stirred for 2 h. The mixture was poured in saturated aqueous sodium bicarbonate/ice. The mixture was extracted 2×EtOAc, the organic layers washed with brine and dried (MgSO$_4$), filtered and concentrated on SiO2. Purification by ISCO chromatography (40 gram column, SiO2, gradient 0% to 100% EtOAc in hexane) gave 7-Nitro-2,3,4,5-tetrahydro-1H-benzo[b]azepine (220 mg, 63%). MP: 73-75° C.; $^1$H-NMR (CDCl$_3$) δ 7.97 (s, 1H), 7.89 (dd, J=2.6, 8.7 Hz, 1H), 6.61 (d, J=8.7 Hz, 1H), 4.42 (br s, 1H), 2.88-2.84 (m, 2H), 1.89-1.78 (m, 4H); LC/MS (ESI+): 193.02 (M+H).

103b) A solution of 7-Nitro-2,3,4,5-tetrahydro-1H-benzo[b]azepine (192 mg, 1.0 mmol) in DMF (10 mL) was treated with potassium carbonate (345 mg, 2.5 eq), and iodomethane (0.08 mL, 1.25 eq) and stirred at room temperature for 30 min. Sodium hydride was added (1.5 eq) and the mixture stirred for 30 min, quenched with water and extracted with ether. The organic layers washed with brine and dried (MgSO$_4$), filtered and concentrated to give 1-Methyl-7-nitro-2,3,4,5-tetrahydro-1H-benzo[b]azepine (206 mg, 100%) as a yellow solid. MP: 52-54° C.; $^1$H-NMR (CDCl$_3$) δ 7.97 (s, 1H), 7.89 (dd, J=2.6, 8.7 Hz, 1H), 6.61 (d, J=8.7 Hz, 1H), 4.42 (br s, 1H), 2.88-2.84 (m, 2H), 1.89-1.78 (m, 4H); LC/MS (ESI+): 207.04 (M+H).

103c) 1-Methyl-7-nitro-2,3,4,5-tetrahydro-1H-benzo[b]azepine (135 mg, 0.66 mmol) in a solution of ethanol (4 mL) and hydrazine hydrate (1 mL) was treated with 10% palladium on carbon (40 mg) and heated at 60° C. for 2 h. The mixture was cooled to room temperature, filtered and concentrated to give 1-Methyl-2,3,4,5-tetrahydro-1H-benzo[b]azepin-7-ylamine (110 mgs, 96%) as a grayish oil. $^1$H-NMR (CDCl$_3$) δ 6.78-6.72 (m, 1H), 6.51 (s, 2H), 3.38 (br s, 2H), 2.82-2.74 (m, 7H), 2.21-2.15 (m, 2H), 1.75-1.68 (m, 2H), 1.57-1.52 (m, 2H); LC/MS (ESI+): 177.16 (M+H).

103d) Following the procedure of Example 101b, 1-Methyl-2,3,4,5-tetrahydro-1H-benzo[b]azepin-7-ylamine (33 mgs, 0.19 mmol) and 2-(2,5-dichloro-pyrimidin-4-ylamino)-N-methyl-benzamide (1.2 eq) were reacted except that following completion of the reaction a precipitate ensued. This mixture was diluted with ether and filtered. The resulting solid was treated with MP-carbonate (3 eq), stirred for 30 min, filtered and concentrated to give 2-[5-Chloro-2-(1-methyl-2,3,4,5-tetrahydro-1H-benzo[b]azepin-7-ylamino)-pyrimidin-4-ylamino]-N-methyl-benzamide as a off-white/yellow solid (39.01 mgs). MP=170-172° C. $^1$H-NMR (CDCl$_3$) δ 11.06 (s, 1H), 8.70 (d, J=8.3 Hz, 1H), 8.08 (s, 1H), 7.49 (d, J=7.8 Hz, 1H), 7.43 (t, J=7.6 Hz, 1H), 7.30-7.27 (m, 2H), 7.07 (t, J=7.6 Hz, 1H), 6.91 (d, J=8.1 Hz, 1H), 6.81 (s, 2H), 6.20 (br s, 1H), 3.05 (d, J=4.8 Hz, 3H), 2.83 (s, 5H), 2.77-2.73 (m, 2H), 1.84-1.75 (m, 2H), 1.64-1.55 (m, 2H); LC/MS (ESI+): 437.30 (M+H).

Example 104

N-{(1R,2R)-2-[5-Chloro-2-(1-methyl-2,3,4,5-tetrahydro-1H-benzo[b]azepin-7-ylamino)-pyrimidin-4-ylamino]-cyclohexyl}-methanesulfonamide 104a) Following the procedure of Example 103a, 1-Methyl-2,3,4,5-tetrahydro-1H-benzo[b]azepin-7-ylamine (33 mgs, 0.19 mmol) and N-[(1R,2R)-2-(2,5-Dichloro-pyrimidin-4-ylamino)-cyclohexyl]-methanesulfonamide (1.2 eq) were converted to N-{(1R,2R)-2-[5-Chloro-2-(1-methyl-2,3,4,5-tetrahydro-1H-benzo[b]azepin-7-ylamino)-pyrimidin-4-ylamino]-cyclohexyl}-methanesulfonamide (63.07 mgs) as an off-white/grey solid. MP=102-104° C. $^1$H-NMR (CDCl$_3$) δ 7.92 (s, 1H), 7.25-7.23 (m, 3H), 6.92-6.89 (m, 1H), 5.72-5.69 (m, 1H), 5.55-5.40 (m, 1H), 3.91-3.82 (m, 1H), 2.85-2.83 (m, 5H), 2.81-2.79 (m, 5H), 2.31-2.22 (m, 2H), 1.89-1.79 (m, 4H), 1.66-1.58 (m, 4H), 1.41-1.31 (m, 4H); LC/MS (ESI+): 479.29 (M+H).

Example 105

5-Chloro-N*4*-(2-methoxy-4-morpholin-4-yl-phenyl)-N*2*-(1-methyl-2,3,4,5-tetrahydro-1H-benzo[b]azepin-7-yl)-pyrimidine-2,4-diamine 105a) Following the procedure of Example 101b, 1-Methyl-2,3,4,5-tetrahydro-1H-benzo[b]azepin-7-ylamine (33 mgs, 0.19 mmol) and (2,5-Dichloro-pyrimidin-4-yl)-(2-methoxy-4-morpholin-4-yl-phenyl)-amine (1.2 eq) [prepared using a procedure analogous to Example 1d using 2,4,5-trichloropyrimidine and 2-Methoxy-4-morpholin-4-yl-phenylamine] were reacted except that the ISCO chromatography gradient was 0% to 5% MeOH/CH$_2$Cl$_2$ to give 5-Chloro-N*4*-(2-methoxy-4-morpholin-4-yl-phenyl)-N*2*-(1-methyl-2,3,4,5-tetrahydro-1H-benzo[b]azepin-7-yl)-pyrimidine-2,4-diamine (46.96 mgs) as an off-white/grey solid. MP=206-207° C. $^1$H-NMR (CDCl$_3$) δ 8.27 (d, J=8.9 Hz, 1H), 8.00 (s, 1H), 7.61 (s, 1H), 7.36 (s, 1H), 7.28-7.24 (m, 1H), 6.91 (d, J=9.1 Hz, 1H), 6.79 (s, 1H), 6.55 (s, 1H), 6.50 (d, J=8.4 Hz, 1H), 3.93 (s, 3H), 3.91-3.89 (m, 4H), 3.17-3.15 (m, 4H), 2.91-2.85 (m, 4H), 2.82-2.77 (m, 4H), 1.89-1.78 (m, 2H), 1.71-1.58 (m, 2H); LC/MS (ESI+): 495.29 (M+H).

Example 106

N-{2-[5-Chloro-2-(1-methyl-2,3,4,5-tetrahydro-1H-benzo[b]azepin-7-ylamino)-pyrimidin-4-ylamino]-phenyl}-methanesulfonamide 106a) Following the procedure of Example 101b, 1-Methyl-2,3,4,5-tetrahydro-1H-benzo[b]azepin-7-ylamine (48 mgs, 0.27 mmol) and N-[2-(2,5-Dichloro-pyrimidin-4-ylamino)-phenyl]-methanesulfonamide (0.9 eq) were reacted except that the ISCO chromatography gradient was 0% to 10% MeOH/CH$_2$Cl$_2$ and the final product was triturated from 4 mL of EtOAc with hexane to give N-{2-[5-Chloro-2-(1-methyl-2,3,4,5-tetrahydro-1H-benzo[b]azepin-7-ylamino)-pyrimidin-4-ylamino]-phenyl}-methanesulfonamide (30.6 mgs) as an off-white/grey solid. MP=170-172° C. $^1$H-NMR (CDCl$_3$) δ δ 7.88 (s, 1H), 7.50-7.48 (m, 1H), 7.36-7.33 (m, 1H), 7.23 (s, 1H), 7.17-7.13 (m, 2H), 6.95-6.89 (m, 3H), 6.68 (s, 1H), 6.63 (br s, 1H), 2.71-2.68 (m, 8H), 2.50-2.47 (m, 2H), 1.63-1.55 (m, 2H), 1.42-1.38 (m, 2H); LC/MS (ESI+): 273 (M+H).

Example 107

2-[5-Chloro-2-(8-methoxy-2-methyl-1-oxo-2,3,4,5-tetrahydro-1H-benzo[c]azepin-7-ylamino)-pyrimidin-4-ylamino]-N-methyl-benzamide 107a) A mixture of 8-Methoxy-2,3,4,5-tetrahydro-benzo[c]azepin-1-one (283 mgs, 1.48 mmol) in DMF (5 mL) was treated with NaH (60% dispersion in mineral oil, 75 mgs, 1.85 mmol) and stirred for 10 min. The mixture was quenched with water and extracted with ether. The organic layers were washed with brine and the organic layer dried (MgSO$_4$), filtered and concentrated to give 8-Methoxy-2-methyl-2,3,4,5-tetrahydro-benzo[c]azepin-1-one (227 mgs). $^1$H-NMR (CDCl$_3$) δ 7.14 (d, J=2.7 Hz, 1H), 6.96 (d, J=8.1 Hz, 1H), 6.83-6.81 (m, 1H), 3.74 (s, 3H), 3.14 (t, J=6.6 Hz, 2H), 3.10 (s, 3H), 2.64 (t, J=8.1 Hz, 2H), 1.97-1.91 (m, 2H); LC/MS (ESI+): 273 (M+H).

107b) A mixture of 8-Methoxy-2-methyl-2,3,4,5-tetrahydro-benzo[c]azepin-1-one (227 mgs, 1.1 mmol) in MeCN/TFAA (1:1, 2 mL) was cooled to 0° C. and treated with potassium nitrate (123 mg, 1.2 mmol), then warmed to room temperature and stirred for 2 h. Poured mixture in water, extracted (EtOAc), washed with brine and the organic layer dried (MgSO$_4$), filtered and concentrated. ISCO purification (0 to 100% EtOAc/hexane, 40 g SiO$_2$ column) provided 8-Methoxy-2-methyl-7-nitro-2,3,4,5-tetrahydro-benzo[c]azepin-1-one (40 mgs). $^1$H-NMR (CDCl$_3$) δ δ 7.63 (s, 1H), 7.41 (s, 1H), 3.98 (s, 3H), 3.24 (t, J=6.3 Hz, 2H), 3.19 (s, 3H), 2.78 (t, J=7.1 Hz, 2H), 2.10-2.04 (m, 2H); LC/MS (ESI+): 250.98 (M+H). The regioisomer 8-Methoxy-2-methyl-9-nitro-2,3,4,5-tetrahydro-benzo[c]azepin-1-one was also isolated as a mixture with 8-Methoxy-2-methyl-7-nitro-2,3,4,5-tetrahydro-benzo[c]azepin-1-one. $^1$H-NMR (CDCl$_3$) δ 7.22 (d, J=8.6 Hz, 1H), 7.02 (d, J=8.6 Hz, 1H), 3.90 (s, 3H), 3.32 (t, J=6.1 Hz, 2H), 3.15 (s, 3H), 2.72 (t, J=6.8 Hz, 2H), 2.06-1.99 (m, 2H); LC/MS (ESI+): 250.98 (M+H).

107c) Following the procedure of 103c, 8-Methoxy-2-methyl-7-nitro-2,3,4,5-tetrahydro-benzo[c]azepin-1-one (49 mgs) was converted to 7-Amino-8-methoxy-2-methyl-2,3,4,5-tetrahydro-benzo[c]azepin-1-one (29.61 mgs). $^1$H-NMR (CDCL3) δ 7.14 (s, 1H), 6.43 (s, 1H), 3.97 (br s, 3H), 3.86 (s, 3H), 3.22 (t, J=6.4 Hz, 2H), 3.15 (s, 3H), 2.63 (t, J=7.1 Hz, 2H), 2.02-1.96 (m, 2H); LC/MS (ESI+): 221.24 (M+H).

107d) Following the procedure 106a, 7-Amino-8-methoxy-2-methyl-2,3,4,5-tetrahydro-benzo[c]azepin-1-one (28 mgs, 0.112 mmol) and 2-(2,5-dichloro-pyrimidin-4-ylamino)-N-methyl-benzamide (1 eq) was converted to 2-[5-Chloro-2-(8-methoxy-2-methyl-1-oxo-2,3,4,5-tetrahydro-1H-benzo[c]azepin-7-ylamino)-pyrimidin-4-ylamino]-N-methyl-benzamide (12.69 mgs). MP: 152-154° C. $^1$H-NMR (CDCl$_3$) δ 11.03 (s, 1H), 8.64 (d, J=8.3 Hz, 1H), 8.21 (s, 1H), 8.14 (s, 1H), 7.68 (s, 1H), 7.51-7.45 (m, 2H), 7.21 (s, 1H), 7.08 (t, J=7.5 Hz, 1H), 6.30 (br s, 1H), 3.92 (s, 3H), 3.24 (t, J=6.3 Hz, 2H), 3.17 (s, 3H), 3.04 (d, J=4.7 Hz, 3H), 2.65 (t, J=7.0 Hz, 2H), 2.03-1.98 (m, 2H); LC/MS (ESI+): 481.36 (M+H).

Example 108

2-[5-Chloro-2-(1-methyl-2-oxo-2,3,4,5-tetrahydro-1H-benzo[b]azepin-8-ylamino)-pyrimidin-4-ylamino]-N-methyl-benzamide 108a) A mixture 8-Amino-1,3,4,5-tetrahydro-benzo[b]azepin-2-one (666 mgs, 3.87 mmol) was treated with 2,5-hexanedione (1.2 eq), p-TsOH.H2O (0.1 eq) in toluene (40 mL) and heated at 120° under Dean-stark conditions. Following evaporation 8-(2,5-Dimethyl-pyrrol-1-yl)-1,3,4,5-tetrahydro-benzo[b]azepin-2-one was isolated as an off-white solid (186 mgs). $^1$H-NMR (dmso-d6) δ 9.62 (s, 1H), 7.37 (d, J=8.1 Hz, 1H), 6.97-6.96 (m, 1H), 6.79 (s, 3H), 5.78 (s, 2H), 2.75 (t, J=7.1 Hz, 2H), 2.23-2.13 (m, 4H), 1.96 (s, 6H).

108b) Following the procedure of 107a, 8-(2,5-Dimethyl-pyrrol-1-yl)-1,3,4,5-tetrahydro-benzo[b]azepin-2-one was converted to 8-(2,5-Dimethyl-pyrrol-1-yl)-1-methyl-1,3,4,5-tetrahydro-benzo[b]azepin-2-one (175 mgs). $^1$H-NMR (CDCl$_3$) δ 7.26 (d, J=8.1 Hz, 1H), 7.02-6.99 (m, 2H), 5.91-5.89 (m, 2H), 3.34 (s, 3H), 2.79 (t, J=7.3 Hz, 2H), 2.41-2.35 (m, 2H), 2.28-2.21 (m, 2H), 2.06 (s, 6H).

108c) 8-(2,5-Dimethyl-pyrrol-1-yl)-1-methyl-1,3,4,5-tetrahydro-benzo[b]azepin-2-one (175 mgs, 0.065 mmol) was treated with hydroxylamine hydrochloride (20 eq), triethylamine (10 eq) in ethanol/water (4:1, 6 mL) and heated to 80° C. overnight. The mixture was concentrated, partitioned between EtOAc and water, dried (MgSO$_4$) filtered and concentrated. The mixture was stirred 2 h with excess 1N HCl, neutralized to pH 7 with 1 NaOH, partitioned between EtOAc and water, dried (MgSO4) filtered and concentrated to give 8-Amino-1-methyl-1,3,4,5-tetrahydro-benzo[b]azepin-2-one (110 mgs, 58%). 6.95 (d, J=7.8 Hz, 1H), 6.50-6.47 (m, 2H), 3.67 (br s, 2H), 3.30 (s, 3H), 2.61-2.57 (m, 2H), 2.32-2.28 (m, 2H), 2.11-2.08 (m, 2H).

108d) Following the procedure of 103d, 8-Amino-1-methyl-1,3,4,5-tetrahydro-benzo[b]azepin-2-one (35 mgs) and 2-(2,5-dichloro-pyrimidin-4-ylamino)-N-methyl-benzamide (0.83 eq) was converted to 2-[5-Chloro-2-(1-methyl-2-oxo-2,3,4,5-tetrahydro-1H-benzo[b]azepin-8-ylamino)-pyrimidin-4-ylamino]-N-methyl-benzamide (27.91 mgs). MP: 292-294° C. $^1$H-NMR (CDCl$_3$) δ 11.08 (s, 1H), 8.57 (d, J=8.3 Hz, 1H), 8.11 (s, 1H), 7.63 (d, J=1.7 Hz, 1H), 7.50 (d, J=7.9 Hz, 1H), 7.38 (t, J=7.3 Hz, 1H), 7.19-7.16 (m, 1H), 7.12-7.08 (m, 2H), 6.97 (s, 1H), 6.27 (s, 1H), 3.18 (s, 3H), 3.04 (d, J=4.8 Hz, 3H), 2.67 (t, J=7.3 Hz, 2H), 2.36 (t, J=6.8 Hz, 2H), 2.18-2.14 (m, 2H); LC/MS (ESI+): 451.40 (M+H).

Example 109

N-{(1R,2R)-2-[5-Chloro-2-(1-methyl-2-oxo-2,3,4,5-tetrahydro-1H-benzo[b]azepin-8-ylamino)-pyrimidin-4-ylamino]-cyclohexyl}-methanesulfonamide 109a) Following the procedure of 103d, 8-Amino-1-methyl-1,3,4,5-tetrahydro-benzo[b]azepin-2-one (33 mgs, 0.19 mmol) and N-[(1R,2R)-2-(2,5-Dichloro-pyrimidin-4-ylamino)-cyclohexyl]-methanesulfonamide (0.83 eq) were converted to N-{(1R,2R)-2-[5-Chloro-2-(1-methyl-2-oxo-2,3,4,5-tetrahydro-1H-benzo[b]azepin-8-ylamino)-pyrimidin-4-ylamino]-cyclohexyl}-methanesulfonamide (25.01 mgs) as off-white solid. MP=127-130° C. $^1$H-NMR (CDCl$_3$) δ 7.95 (s, 1H), 7.49 (s, 1H), 7.26-7.23 (m, 1H), 7.14 (d, J=8.3 Hz, 1H), 6.96 (s, 1H), 5.49 (d, J=7.0 Hz, 1H), 5.36 (d, J=7.0 Hz, 1H), 3.87-3.84 (m, 1H), 3.36 (s, 3H), 3.25-3.19 (m, 1H), 2.81 (s, 3H), 2.68 (t, J=6.8 Hz, 2H), 2.34 (t, J=7.3 Hz, 2H), 2.19-2.10 (m, 6H), 1.73-1.71 (m, 2H), 1.39-1.21 (m, 2H); LC/MS (ESI+): 493.03 (M+H).

Example 110

(2-exo,3-exo)-3-[5-Chloro-2-(1-methyl-2-oxo-2,3,4,5-tetrahydro-1H-benzo[b]azepin-8-ylamino)pyrimidin-4-ylamino]-bicyclo[2.2.1]hept-5-ene-2-carboxylic acid amide 110a) Following the procedure of 103d, 8-Amino-1-methyl-1,3,4,5-tetrahydro-benzo[b]azepin-2-one (35 mgs, 0.18 mmol) and (2-exo,3-exo)-3-(2,5-Dichloro-pyrimidin-4-ylamino)-bicyclo[2.2.1]hept-5-ene-2-carboxylic acid amide (0.83 eq) were converted to (2-exo, 3-exo)-3-[5-Chloro-2-(1-methyl-2-oxo-2,3,4,5-tetrahydro-1H-benzo[b]azepin-8-ylamino)pyrimidin-4-ylamino]-bicyclo[2.2.1]hept-5-ene-2-carboxylic acid amide (26.76 mgs) as white solid. MP=210-212° C. $^1$H-NMR (dmso-d6) δ 9.35 (s, 1H), 7.97 (s, 1H), 7.80-7.73 (m, 3H), 7.54 (d, J=9.3 Hz, 1H), 7.27 (s, 1H), 7.14 (d, J=8.1 Hz, 1H), 6.63 (br s, 1H), 6.19 (br s, 1H), 4.15-4.13 (m, 1H), 3.18 (s, 3H), 2.88 (s, 1H), 2.77 (s, 1H), 2.60-2.30 (m, 3H), 2.18-2.00 (m, 6H); LC/MS (ESI+): 453.27 (M+H).

Example 111

N-((1R,2R)-2-{5-Chloro-2-[8-methoxy-3-(2-methoxy-ethyl)-2,3,4,5-tetrahydro-1H-benzo[d]azepin-7-ylamino]-pyrimidin-4-ylamino}-cyclohexyl)-methanesulfonamide 111a) 8-Methoxy-3-(2-methoxy-ethyl)-2,3,4,5-tetrahydro-1H-benzo[d]azepin-7-ylamine (165 mg, 0.000659 mol), N-[(1R,2R)-2-(2,5-Dichloro-pyrimidin-4-ylamino)-cyclohexyl]-methanesulfonamide (220 mg, 0.00066 mol), 4 M of Hydrogen chloride in 1,4-Dioxane (200 uL) and Isopropyl alcohol (6.6 mL, 0.086 mol) were combined in a microwave vessel. Heat at 130° C. for 20 min. The mixture was treated with 500 mgs of MP-carbonate resin and stirred for 20 min. The mixture was filtered and concentrated and put on high vac overnight. The crude solid was dissolved in DCM and purified on an ISCO column (40 g, SiO2, 100% DCM to MeOH/DCM gradient) to afford N-((1R,2R)-2-{5-Chloro-2-[8-methoxy-3-(2-methoxy-ethyl)-2,3,4,5-tetrahydro-1H-benzo[d]azepin-7-ylamino]-pyrimidin-4-ylamino}-cyclohexyl)-methanesulfonam (99 mg, 48%). MP: 92-94° C. $^1$H-NMR (CDCl$_3$, 400 MHz): $^1$H-NMR (CDCL3) δ 7.96 (s, 1H), 7.32 (s, 1H), 6.67 (s, 1H), 5.37-5.31 (m, 2H), 3.99-3.95 (broad m, 1H), 3.88 (s, 1H), 3.56 (br s, 2H), 3.38 (s, 1H), 3.28-3.24 (m, 1H), 2.99-2.70 (complex series of m, 11H), 2.26-2.20 (m, 2H), 1.88-1.80 (m, 2H), 1.41-1.28 (m, 6H), 0.92-0.85 (m, 2H). LC/MS: 552.92 (M+H).

Example 112

(2-exo,3-exo)-3-{5-Chloro-2-[8-methoxy-3-(2-methoxy-ethyl)-2,3,4,5-tetrahydro-1H-benzo[d]azepin-7-ylamino]-pyrimidin-4-ylamino}-bicyclo[2.2.1]hept-5-ene-2-carboxylic acid amide 112a) Combine 8-Methoxy-3-(2-methoxy-ethyl)-2,3,4,5-tetrahydro-1H-benzo[d]azepin-7-ylamine (55 mg, 0.00022 mol), (2-exo,3-exo)-3-(2,5-Dichloro-pyrimidin-4-ylamino)-bicyclo[2.2.1]hept-5-ene-2-carboxylic acid amide (72 mg, 0.00024 mol), 4 M of Hydrogen chloride in 1,4-Dioxane (70 uL) and Isopropyl alcohol (2.2 mL, 0.029 mol) in microwave vessel. Heat at 130° C. for 10 min. Heat 10 min further at 130° C. Reaction proceeded no further. Cool to room temp. treat with 200 mgs of MP-carbonate and stir for ca. 30 min. The mixture was filtered and the filtrate concentrated. The material was purified by ISCO chromatography, (40 g, SiO2, 100% DCM to 5-10% MeOH/DCM gradient) provided (2-exo, 3-exo)-3-{5-Chloro-2-[8-methoxy-3-(2-methoxy-ethyl)-2,3,4,5-tetrahydro-1H-benzo[d]azepin-7-ylamino]-pyrimidin-4-ylamino}-bicyclo[2.2.1]hept-5-ene-2-carboxylic acid amide as an off-white solid (67 mgs, 59%). MP: 120-122° C. $^1$H-NMR (CDCl$_3$, 400 MHz): δ 8.19 (s, 1H), 7.91 (d, J=2.6 Hz, 1H), 7.40 (s, 1H), 6.65 (s, 1H), 6.56 (d, J=8.3 Hz, 1H), 6.32 (s, 2H), 5.60 (br s, 1H), 5.37 (br s, 1H), 4.47 (t, J=5.2 Hz, 1H), 3.88 (s, 3H), 3.58-3.55 (m, 2H), 3.39 (s, 3H), 3.08 (s, 1H), 2.88-2.76 (m, 7H), 2.54 (d, J=8.1 Hz, 1H), 2.28 (d, J=9.2 Hz), 1.67 (d, J=9.3 Hz, 1H), 1.32-1.27 (m, 2H), 0.99-0.85 (m, 2H); LC/MS: 512.97 (M+H).

Example 113

5-Chloro-N*2*-[8-methoxy-3-(2-methoxy-ethyl)-2,3,4,5-tetrahydro-1H-benzo[d]azepin-7-yl]-N*4*-(2-methoxy-4-morpholin-4-yl-phenyl)-pyrimidine-2,4-diamine 113a) Combined 8-Methoxy-3-(2-methoxy-ethyl)-2,3,4,5-tetrahydro-1H-benzo[d]azepin-7-ylamine (55 mg, 0.00022 mol), (2,5-Dichloro-pyrimidin-4-yl)-(2-methoxy-4-morpholin-4-yl-phenyl)-amine (86 mg, 0.00024 mol), 4 M of Hydrogen chloride in 1,4-Dioxane (70 uL) and Isopropyl alcohol (2.2 mL, 0.029 mol) in microwave vessel. Heat at 130° C. for 10 minutes. Heat for another 10 minutes. Cool to room temp. Solid precipitated out of solution. Filtered off solid. The filtrate was treated with MP-carbonate 250 mgs and stirred for 30 min. The mixture was concentrated and purified by ISCO chromatography (40 g SiO2 column, gradient 100% DCM to 10% MeOH/DCM. Isolated 5-Chloro-N*2*-[8-methoxy-3-(2-methoxy-ethyl)-2,3,4,5-tetrahydro-1H-benzo[d]azepin-7-yl]-N*4*-(2-methoxy-4-morpholin-4-yl-phenyl)-pyrimidine-2,4-diamine as an off-white solid (49 mgs, 39%) Melting point: 138-140° C. δ 8.30 (d, J=8.8 Hz, 1H), 8.12 (s, 1H), 8.03 (d, J=1.8 Hz, 1H), 7.57 (s, 1H), 7.45 (s, 1H), 6.65 (s, 1H), 6.57-6.52 (m, 2H), 3.94-3.88 (m, 10H), 3.36 (br s, 2H), 3.39 (d, J=1.7 Hz, 3H), 3.18-3.17 (m, 4H), 2.90-2.74 (m, 10H); LC/MS: 568.87 (M+H).

Example 114

2-[5-Chloro-2-(8-methoxy-2-methyl-1-oxo-2,3,4,5-tetrahydro-1H-benzo[c]azepin-9-ylamino)-pyrimidin-4-ylamino]-N-methyl-benzamide 114a) 7-Amino-8-methoxy-2-methyl-2,3,4,5-tetrahydro-benzo[c]azepin-1-one (110 mg, 0.50 mmol) and 9-Amino-8-methoxy-2-methyl-2,3,4,5-tetrahydro-benzo[c]azepin-1-one (prepared following the procedure of 7c) were added as an unseparated mixture with 4 M of Hydrogen chloride in 1,4-Dioxane (300 uL), 2-Methoxyethanol (10 mL, 100 mmol), and 2-(2,5-Dichloro-pyrimidin-4-ylamino)-N-methyl-benzamide (2 eq) charged into Radley tube. Heat 110° C. for about 3 hours, cooled to room temperature. Solid precipitated out and was filtered. This material was dissolved in dichloromethane/MeOH and treated with 3 eq. of MP-carbonate, stirred 30 min, filtered and concentrated to give 2-[5-Chloro-2-(8-methoxy-2-methyl-1-oxo-2,3,4,5-tetrahydro-1H-benzo[c]azepin-9-ylamino)-pyrimidin-4-ylamino]-N-methyl-benzamide as an orange solid (51 mgs, 21%). Melting point: 185-187° C. $^1$H-NMR (DMSO, 400 MHz): 8.67 (broad m, 1H), 8.67 (s, 1H), 8.47 (broad s, 1H), 8.00 (d, J=7.0 Hz, 1H), 7.47-7.43 (m, 1H), 708-7.03 (m, 2H), 6.82 (d, J=7.8 Hz, 1H), 3.81 (s, 3H), 3.17-3.07 (m, 2H), 2.85 (s, 3H), 2.69-2.65 (m, 2H) 2.50 (s, 3H), 1.78-1.71 (m, 2H); LC/MS: 481.37 (M+H).

Example 115

(2-exo, 3-exo)-3-[5-Chloro-2-(6-methoxy-1-methyl-2-oxo-2,3,4,5-tetrahydro-1H-benzo[b]azepin-7-ylamino)-pyrimidin-4-ylamino]-bicyclo[2.2.1]hept-5-ene-2-carboxylic acid amide 115a) 6-Methoxy-1,3,4,5-tetrahydro-benzo[b]azepin-2-one (prepared according to: Hassner, A.; Amit, B.; Marks, V.;

Gottlieb, Hugo E., *J. Org. Chem.* 2003, 68(18), 6853-6858.) (300 mg, 1.57 mmol) in 15 mL of DMF was cooled to 0° C. in an ice bath, and to the solution was added NaH (60% in mineral oil) (70 mg, 1.73 mmol). After 10 minutes of stirring at 0° C., Iodomethane (270 mg, 1.88 mmol) was added to the solution. The reaction was allowed to warm to room temperature and upon completion (after 30 minutes) was quenched with ice and water. The aqueous solution was extracted 3× with diethyl ether, and the organic layers were washed with water and brine, dried with MgSO$_4$, and concentrated to give 6-Methoxy-1-methyl-1,3,4,5-tetrahydro-benzo[b]azepin-2-one as a yellow oil (quantitative yield). $^1$H-NMR (CDCl$_3$) δ 7.22 (t, J=8.2 Hz, 1H), 6.80 (d, J=8.1 Hz, 1H), 6.75 (d, J=8.3 Hz, 1H), 3.84 (s, 3H), 3.33 (s, 3H), 2.52-3.09 (br pk, 2H), 2.29 (t, J=7.1 Hz, 2H), 2.12 (br s, 2H); LC/MS (ESI-pos) m/z 205.98 (M+H).

115b) To a solution of 6-Methoxy-1-methyl-1,3,4,5-tetrahydro-benzo[b]azepin-2-one (INT-1) (538 mg, 2.62 mmol) in acetonitrile brought to 0° C. in an ice bath was added 1.8 mL TFAA (2.7 g, 13.1 mmol), followed by KNO3 (320 mg, 3.14 mmol). After approximately 5 minutes, the reaction was allowed to warm to room temperature. Conversion of starting material to product was monitored by LC/MS. Upon completion, the reaction was cooled to 0° C. in an ice bath and quenched with sat. NaHCO3 (aq), 1N NaOH (aq), and ice until pH ~9-10 was achieved. The aqueous mixture was extracted 3× with EtOAc and the organic layers were washed with brine, dried with MgSO$_4$, and concentrated to give 6-Methoxy-1-methyl-7-nitro-1,3,4,5-tetrahydro-benzo[b] azepin-2-one (INT-2) as an orange solid (530 mg, 82%). By NMR, the product showed a 4:1 mixture of nitration products, 80% of which was the desired product. By TLC, the products appeared inseparable, so the material was taken on for reduction crude. Data for Major Isomer: 1H-NMR (CDCl$_3$) δ 7.83 (d, J=8.8 Hz, 1H), 7.04 (d, J=8.8 Hz, 1H), 3.94 (s, 3H), 3.37 (s, 3H), 2.87 (br m, 2H), 2.36 (t, J=7.1 Hz, 2H), 2.24 (m, 2H); LC/MS (ESI-pos) m/z 251.03 (M+H).

115c) 6-Methoxy-1-methyl-7-nitro-1,3,4,5-tetrahydrobenzo[b]azepin-2-one (530 mg, 2.12 mmol) in a 4:1 mixture of ethanol (17 mL) and hydrazine hydrate (4.5 mL) was heated to 60° C. and to it was added a ¼ mass equivalent of 10% Palladium/Carbon (50% H2O) (135 mg). The reaction was monitored by LC/MS to ensure that complete reduction occurred, and upon completion was cooled to room temperature. The Pd/C was filtered through celite, and the resulting filtrate concentrated to a minimal volume. This was then brought up in ~120 mL of CH$_2$Cl$_2$ and washed with ~25 mL of brine to remove excess hydrazine. The organic layer was then dried with MgSO4 and concentrated to give 7-Amino-6-methoxy-1-methyl-1,3,4,5-tetrahydro-benzo[b]azepin-2-one as a yellow gummy solid (432 mg, 93%). $^1$H-NMR (CDCl$_3$) δ 6.78 (d, J=8.6 Hz, 1H), 6.65 (d, J=8.6 Hz, 1H), 3.81 (br s, 2H), 3.75 (s, 3H), 3.28 (s, 3H), 2.35-2.75 (br pk, 2H), 2.30 (t, J=6.9 Hz, 2H), 2.15 (m, 2H); LC/MS (ESI-pos) m/z 221.13 (M+H).

115d) Following the procedure Example 101b, 7-Amino-6-methoxy-1-methyl-1,3,4,5-tetrahydro-benzo[b]azepin-2-one (50 mg, 0.227 mmol) and (2-exo,3-exo)-3-(2,5-Dichloropyrimidin-4-ylamino)-bicyclo[2.2.1]hept-5-ene-2-carboxylic acid amide (57 mg, 0.189 mmol) were converted to the desired product (10 mg, 11%), obtained by trituration in EtOAc. M.P.=171-173° C. $^1$H-NMR (CDCl$_3$) δ 8.39 (d, J=8.8 Hz, 1H), 7.92 (s, 1H), 7.40 (s, 1H), 7.17 (d, J=7.8 Hz, 1H), 6.93 (d, J=8.8 Hz, 1H), 6.34 (br s, 2H), 5.65 (br s, 1H), 5.43 (br s, 1H), 4.34 (t, J=7.8 Hz, 1H), 3.80 (s, 3H), 3.34 (s, 3H), 3.08 (s, 1H), 2.95 (s, 1H), 2.84 (m, 2H), 2.51 (d, J=8.1 Hz, 1H), 2.33 (t, J=6.8 Hz, 2H), 2.25 (d, J=9.1 Hz, 1H), 2.18 (m, 2H); LC/MS (ESI-pos) m/z 483.36 (M+H).

Example 116

2-[5-Chloro-2-(6-methoxy-1-methyl-2-oxo-2,3,4,5-tetrahydro-1H-benzo[b]azepin-7-ylamino)-pyrimidin-4-ylamino]-N-methyl-benzamide 116a) To a solution of 7-Amino-6-methoxy-1-methyl-1,3,4,5-tetrahydro-benzo[b]azepin-2-one (50 mg, 0.227 mmol) and 2-(2,5-Dichloro-pyrimidin-4-ylamino)-N-methyl-benzamide (56 mg, 0.189 mmol) in 2.27 mL of 2-methoxyethanol was added 57 µL of 4M HCl in Dioxane (0.227 mmol). The solution was heated to 110° C. for 5 hrs, followed by the addition of MP-Carbonate (135 mg, 0.43 mmol) at RT. The MP-Carbonate was filtered after 30 minutes and the resulting crude material was chromatographed (ISCO) to give 2-[5-Chloro-2-(6-methoxy-1-methyl-2-oxo-2,3,4,5-tetrahydro-1H-benzo[b]azepin-7-ylamino)-pyrimidin-4-ylamino]-N-methyl-benzamide (23 mg, 25%). $^1$H-NMR (CDCl$_3$) δ 11.12 (s, 1H), 8.66 (d, J=8.6 Hz, 1H), 8.26 (d, J=8.8 Hz, 1H), 8.14 (s, 1H), 7.51 (t, J=7.7 Hz, 2H), 7.43 (s, 1H), 7.12 (t, J=7.6 Hz, 1H), 6.90 (t, J=8.8 Hz, 1H), 6.26 (br s, 1H), 3.80 (s, 3H), 3.33 (s, 3H), 3.04 (s, 3H), 2.0-2.4 (m, 6H); LC/MS (ESI-pos) m/z 481.06 (M+H).

Example 117

7-[5-Chloro-4-(2-methoxy-4-morpholin-4-yl-phenylamino)-pyrimidin-2-ylamino]-6-methoxy-1-methyl-1,3,4,5-tetrahydro-benzo[b]azepin-2-one 117a) Following the procedure in Example 101b, 7-Amino-6-methoxy-1-methyl-1,3,4,5-tetrahydro-benzo[b] azepin-2-one (50 mg, 0.227 mmol) and (2,5-Dichloro-pyrimidin-4-yl)-(2-methoxy-4-morpholin-4-yl-phenyl)-amine (67 mg, 0.189 mmol) were converted to the 7-[5-Chloro-4-(2-methoxy-4-morpholin-4-yl-phenylamino)-pyrimidin-2-ylamino]-6-methoxy-1-methyl-1,3,4,5-tetrahydro-benzo[b] azepin-2-one (10 mg, 10%), obtained by trituration in EtOAc. MP: 197-199° C. $^1$H-NMR (CDCl$_3$) δ 8.26 (d, J=8.8 Hz, 1H), 8.22 (d, J=8.6 Hz, 1H), 8.05 (s, 1H), 7.57 (s, 1H), 7.37 (br s, 1H), 6.89 (d, J=8.8, 1H), 6.56 (s, 1H), 6.53 (s, 1H), 3.93 (s, 3H), 3.90 (t, J=5.3, 4H), 3.79 (s, 3H), 3.33 (s, 3H), 3.18 (t, J=4.7, 4H), 2.7-2.9 (br pk, 2H), 2.34 (m, 2H), 2.1-2.25 (br pk, 2H); LC/MS (ESI-pos) m/z 539.32 (M+H).

Example 118

N-{(1R,2R)-2-[5-Chloro-2-(6-methoxy-1-methyl-2-oxo-2,3,4,5-tetrahydro-1H-benzo[b]azepin-7-ylamino)-pyrimidin-4-ylamino]-cyclohexyl}-methanesulfonamide 118a) Following the procedure 11b, 7-Amino-6-methoxy-1-methyl-1,3,4,5-tetrahydro-benzo[b]azepin-2-one (50 mg, 0.227 mmol) and N-[(1R,2R)-2-(2,5-Dichloro-pyrimidin-4-ylamino)-cyclohexyl]-methanesulfonamide (64 mg, 0.189 mmol) were converted to N-{(1R,2R)-2-[5-Chloro-2-(6-methoxy-1-methyl-2-oxo-2,3,4,5-tetrahydro-1H-benzo[b] azepin-7-ylamino)-pyrimidin-4-ylamino]-cyclohexyl}-methanesulfonamide (15 mg, 15%), obtained by flash chromatography using 100% EtOAc. MP: Decomposition at 95° C. $^1$H-NMR (CDCl$_3$) δ 8.17 (d, J=9.1 Hz, 1H), 7.97 (s, 1H), 7.32 (s, 1H), 6.95 (d, J=8.8 Hz, 1H), 5.51 (d, J=7.8 Hz, 1H), 5.33 (d, J=7.1 Hz, 1H), 3.80 (s, 3H), 3.76 (d, J=4.3 Hz, 3H), 3.34 (s, 3H), 3.18 (m, 2H), 2.7-2.9 (br m, 5H), 2.0-2.4 (br m, 6H), 1.7-1.9 (m, 3H); LC/MS (ESI-pos) m/z 523.16 (M+H).

Example 119

7-[5-Chloro-4-(2-methoxy-4-morpholin-4-yl-phenylamino)-pyrimidin-2-ylamino]-1-ethyl-6-methoxy-1,3,4,5-tetrahydro-benzo[b]azepin-2-one 119a) Following the procedure for Example 101b, 7-Amino-1-ethyl-6-methoxy-1,3,4,5-tetrahydro-benzo[b]azepin-2-one (80 mg, 0.341 mmol) and (2,5-Dichloro-pyrimidin-4-yl)-(2-methoxy-4-morpholin-4-yl-phenyl)-amine (101 mg, 0.285 mmol) were converted to the 7-[5-Chloro-4-(2-methoxy-4-morpholin-4-yl-phenylamino)-pyrimidin-2-ylamino]-1-ethyl-6-methoxy-1,3,4,5-tetrahydro-benzo[b]azepin-2-one (23 mg, 15%), purified by ISCO chromatography. MP=210-212° C. $^1$H-NMR (CDCl$_3$) δ 8.26 (d, J=9.1 Hz, 1H), 8.21 (d, J=8.6, 1H), 8.05 (s, 1H), 7.56 (s, 1H), 7.38 (s, 1H), 6.92 (d, J=8.8 Hz, 1H), 6.55 (m, 2H), 3.92 (s, 3H), 3.90 (m, 4H), 3.79 (s, 3H), 3.17 (m, 4H), 2.30 (br m, 2H), 1.23 (m, 6H), 1.14 (t, J=7.2, 3H); LC/MS (ESI-pos) m/z 553.32 (M+H).

Example 120

N-{(1R,2R)-2-[5-Chloro-2-(1-ethyl-6-methoxy-2-oxo-2,3,4,5-tetrahydro-1H-benzo[b]azepin-7-ylamino)-pyrimidin-4-ylamino]-cyclohexyl}-methanesulfonamide 120a) Following a procedure analogous to Example 101b, 7-Amino-1-ethyl-6-methoxy-1,3,4,5-tetrahydro-benzo[b]azepin-2-one (80 mg, 0.341 mmol) and N-[(1R,2R)-2-(2,5-Dichloro-pyrimidin-4-ylamino)-cyclohexyl]-methanesulfonamide (97 mg, 0.285 mmol) were converted N-{(1R,2R)-2-[5-Chloro-2-(1-ethyl-6-methoxy-2-oxo-2,3,4,5-tetrahydro-1H-benzo[b]azepin-7-ylamino)-pyrimidin-4-ylamino]-cyclohexyl}-methanesulfonamide (12 mg, 8%), purified by ISCO chromatography. MP: dec. 98° C.; $^1$H-NMR (CDCl$_3$) δ 8.17 (d, J=8.6 Hz, 1H), 7.98 (s, 1H), 7.31 (br s, 1H), 6.98 (d, J=9.1 Hz, 1H), 5.49 (m, 1H), 5.32 (m, 1H), 3.90 (br m, 1H), 3.80 (s, 3H), 3.26 (br m, 1H), 2.82 (s, 3H), 2.25 (br m, 6H), 1.85 (br m, 2H), 1.40 (br m, 8H), 1.13 (t, J=7.1 Hz, 3H); LC/MS (ESI-pos) m/z 537.32 (M+H).

Example 121

(2-exo,3-exo)-3-[5-Chloro-2-(1-ethyl-6-methoxy-2-oxo-2,3,4,5-tetrahydro-1H-benzo[b]azepin-7-ylamino)-pyrimidin-4-ylamino]-bicyclo[2.2.1]hept-5-ene-2-carboxylic acid amide 121a) Following a procedure analogous to 10b, 7-Amino-1-ethyl-6-methoxy-1,3,4,5-tetrahydro-benzo[b]azepin-2-one (80 mg, 0.341 mmol) and (2-exo,3-exo)-3-(2,5-Dichloro-pyrimidin-4-ylamino)-bicyclo[2.2.1]hept-5-ene-2-carboxylic acid amide (85 mg, 0.285 mmol) were converted to (2-exo,3-exo)-3-[5-Chloro-2-(1-ethyl-6-methoxy-2-oxo-2,3,4,5-tetrahydro-1H-benzo[b]azepin-7-ylamino)-pyrimidin-4-ylamino]-bicyclo[2.2.1]hept-5-ene-2-carboxylic acid amide (15 mg, 11%), obtained by trituration in EtOAc. MP: 174-177° C. $^1$H-NMR (CDCl$_3$) δ 8.40 (d, J=8.8 Hz, 1H), 7.92 (s, 1H), 7.41 (s, 1H), 7.15 (d, J=7.8 Hz, 1H), 6.96 (d, J=8.8 Hz, 1H), 6.34 (br s, 2H), 5.64 (br s, 1H), 5.40 (br s, 1H), 3.80 (s, 3H), 3.73 (m, 2H), 3.08 (s, 1H), 2.95 (s, 1H), 2.29 (br s, 2H), 1.24 (m, 8H), 1.13 (t, J=7.0, 3H); LC/MS (ESI-pos) m/z 497.35 (M+H).

Example 122

2-[5-Chloro-2-(1-ethyl-6-methoxy-2-oxo-2,3,4,5-tetrahydro-1H-benzo[b]azepin-7-ylamino)-pyrimidin-4-ylamino]-N-methyl-benzamide 122a) Following a procedure analogous to Example 101b, 7-Amino-1-ethyl-6-methoxy-1,3,4,5-tetrahydro-benzo[b]azepin-2-one (80 mg, 0.341 mmol) and 2-(2,5-Dichloro-pyrimidin-4-ylamino)-N-methyl-benzamide (86 mg, 0.285 mmol) were converted 2-[5-Chloro-2-(1-ethyl-6-methoxy-2-oxo-2,3,4,5-tetrahydro-1H-benzo[b]azepin-7-ylamino)-pyrimidin-4-ylamino]-N-methyl-benzamide (8 mg, 6%), purified by ISCO chromatography. MP: 225-227° C. $^1$H-NMR (CDCl$_3$) δ 11.11 (s, 1H), 8.66 (d, J=8.6 Hz, 1H), 8.27 (d, J=8.8 Hz, 1H), 8.14 (s, 1H), 7.51 (t, J=7.0 Hz, 1H), 7.48 (d, J=8.1 Hz, 1H), 7.42 (s, 1H), 7.12 (t, J=7.6 Hz, 1H), 6.94 (d, J=8.8 Hz, 1H), 6.21 (br s, 1H), 3.80 (s, 3H), 3.05 (d, J=4.8 Hz, 3H), 2.30 (br m, 2H), 1.13 (t, J=7.1 Hz, 3H), 0.95-1.35 (br ms, 6H); LC/MS (ESI-pos) m/z 495.39 (M+H).

Example 123

2-[5-Chloro-2-(6-methoxy-1-methyl-2-oxo-2,3,4,5-tetrahydro-1H-benzo[b]azepin-9-ylamino)-pyrimidin-4-ylamino]-N-methyl-benzamide 123a) Analogous to procedure 107b, 6-Methoxy-1,3,4,5-tetrahydro-benzo[b]azepin-2-one (700 mg, 3.66 mmol) was converted to 6-Methoxy-7-nitro-1,3,4,5-tetrahydro-benzo[b]azepin-2-one (380 mg, 44%), purified by ISCO chromatography. $^1$H-NMR (CDCl$_3$) δ 8.12 (s, 1H), 7.79 (d, J=8.6 Hz, 1H). 6.85 (d, J=8.6 Hz, 1H), 3.95 (s, 3H), 2.95 (t, J=7.2 Hz, 2H), 2.44 (t, J=7.3 Hz, 2H), 2.31 (quint, J=7.2 Hz, 2H); LC/MS (ESI-pos) m/z 237.11 (M+H). Analogously, 6-Methoxy-9-nitro-1,3,4,5-tetrahydro-benzo[b]azepin-2-one was also isolated.

123b) Analogous to procedure for Example 107a, 6-Methoxy-9-nitro-1,3,4,5-tetrahydro-benzo[b]azepin-2-one (105 mg, 0.445 mmol) and iodomethane (76 mg, 0.535 mmol) were converted to 6-Methoxy-1-methyl-9-nitro-1,3,4,5-tetrahydro-benzo[b]azepin-2-one (87 mg, 78%). $^1$H-NMR (CDCl$_3$) δ 7.96 (d, J=9.4 Hz, 1H), 6.86 (d, J=9.1 Hz, 1H), 3.94 (s, 3H), 3.29 (m, 1H), 3.09 (s, 3H), 2.36 (m, 4H), 1.91 (m, 1H); LC/MS (ESI-pos) m/z 251.29 (M+H). M.P.=140-142° C.

123c) Analogous to procedure for Example 103c, 6-Methoxy-1-methyl-9-nitro-1,3,4,5-tetrahydro-benzo[b]azepin-2-one (87 mg, 0.348 mmol) was converted to 9-Amino-6-methoxy-1-methyl-1,3,4,5-tetrahydro-benzo[b]azepin-2-one (72 mg, 95%). $^1$H-NMR (CDCl$_3$) δ 6.73 (d, J=8.8 Hz, 1H), 6.64 (d, J=8.6 Hz, 1H), 3.76 (s, 3H), 3.44 (br s, 2H), 3.18 (s, 3H), 2.26 (m, 4H), 1.84 (m, 1H), 1.56 (br m, 1H); LC/MS (ESI-pos) m/z 221.07 (M+H). M.P.=142-144° C.

123d) Analogous to procedure for Example 101b, 9-Amino-6-methoxy-1-methyl-1,3,4,5-tetrahydro-benzo[b]azepin-2-one (40 mg, 0.182 mmol) and 2-(2,5-Dichloro-pyrimidin-4-ylamino)-N-methyl-benzamide (50 mg, 0.165 mmol) were converted to 2-[5-Chloro-2-(6-methoxy-1-methyl-2-oxo-2,3,4,5-tetrahydro-1H-benzo[b]azepin-9-ylamino)-pyrimidin-4-ylamino]-N-methyl-benzamide (6 mg, 8%), purified by ISCO chromatography. MP: 165-167° C. $^1$H-NMR (CDCl$_3$) δ 11.10 (s, 1H), 8.58 (d, J=8.6 Hz, 1H), 8.05 (s, 1H), 7.72 (d, J=8.8 Hz, 1H), 7.47 (d, J=7.6 Hz, 1H), 7.39 (t, J=8.2 Hz, 1H), 7.05 (t, J=7.7 Hz, 1H), 6.86 (d, J=9.1 Hz, 1H), 6.47 (s, 1H), 6.19 (br m, 1H), 3.85 (s, 3H), 3.15 (s, 3H), 3.04 (d, J=4.8 Hz, 3H), 2.25-2.4 (ms, 5H), 1.83 (m, 1H); LC/MS (ESI-pos) m/z 481.45 (M+H).

Example 124

9-[5-Chloro-4-(2-methoxy-4-morpholin-4-yl-phenylamino)-pyrimidin-2-ylamino]-6-methoxy-1-methyl-1,3,4,5-tetrahydro-benzo[b]azepin-2-one 124a) Analogous to procedure Example 101b, 9-Amino-6-methoxy-1-methyl-1,3,4,5-tetrahydro-benzo[b]azepin-2-one (40 mg, 0.182 mmol) and (2,5-Dichloro-pyrimidin-4-yl)-(2-methoxy-4-morpholin-4-yl-phenyl)-amine (60 mg, 0.165 mmol) were converted to -[5-Chloro-4-(2-methoxy-4-morpholin-4-yl-phenylamino)-pyrimidin-2-ylamino]-6-methoxy-1-methyl-1,3,4,5-tetrahydro-benzo[b]azepin-2-one (32 mg, 37%), purified by ISCO chromatography. MP: 230-232° C. $^1$H-NMR (CDCl$_3$) δ 8.15 (d, J=8.8 Hz, 1H), 7.96 (s, 1H), 7.73 (d, J=8.8 Hz, 1H), 7.60 (s, 1H), 6.86 (d, J=8.8 Hz, 1H), 6.52 (s, 1H), 6.46 (m, 2H), 3.91 (s, 3H), 3.88 (t, J=4.7 Hz, 4H), 3.85 (s, 3H), 3.16 (s, 3H), 3.14 (t, J=4.6 Hz, 4H), 2.15-2.4 (br m, 5H), 1.84 (br m, 1H); LC/MS (ESI-pos) m/z 539.36 (M+H).

Example 125

9-[5-Chloro-4-(2-methoxy-4-morpholin-4-yl-phenylamino)-pyrimidin-2-ylamino]-1-ethyl-6-methoxy-1,3,4,5-tetrahydro-benzo[b]azepin-2-one 125a) Analogous to procedure Example 101b, 9-Amino-1-ethyl-6-methoxy-1,3,4,5-tetrahydro-benzo[b]azepin-2-one (47 mg, 0.200 mmol) and (2,5-Dichloro-pyrimidin-4-yl)-(2-methoxy-4-morpholin-4-yl-phenyl)-amine (66 mg, 0.185 mmol) were converted to 9[5-Chloro-4-(2-methoxy-4-morpholin-4-yl-phenylamino)-pyrimidin-2-ylamino]-1-ethyl-6-methoxy-1,3,4,5-tetrahydro-benzo[b]azepin-2-one (43 mg, 42%), purified by ISCO chromatography. $^1$H-NMR (CDCl$_3$) δ 8.18 (d, J=8.8 Hz, 1H), 7.98 (s, 1H), 7.81 (d, J=9.1 Hz, 1H), 7.61 (s, 1H), 6.86 (d, J=9.1 Hz, 1H), 6.53 (s, 1H), 6.47 (m, 2H), 3.91 (s, 3H), 3.88 (t, J=4.6 Hz, 4H), 3.85 (s, 3H), 3.22 (m, 2H), 3.15 (t, J=4.2 Hz, 4H), 2.15-2.47 (m, 5H), 1.82 (br m, 1H) 1.58 (t, J=7.1 Hz, 3H); LC/MS (ESI-pos) m/z 553.36 (M+H). M.P.=218-220° C.

Example 126

2-{5-Chloro-2-[6-methoxy-1-(2-methoxy-ethyl)-2-oxo-2,3,4,5-tetrahydro-1H-benzo[b]azepin-7-ylamino]-pyrimidin-4-ylamino}-N-methyl-benzamide 126a) Analogous to a procedure for Example 107a and 103c, 6-Methoxy-7-nitro-1,3,4,5-tetrahydro-benzo[b]azepin-2-one (230 mg, 0.970 mmol) and 1-Bromo-2-methoxy-ethane (170 mg, 1.22 mmol) were converted to 7-Amino-6-methoxy-1-(2-methoxy-ethyl)-1,3,4,5-tetrahydro-benzo[b]azepin-2-one (INT-10) (140 mg, 55%). $^1$H-NMR (CDCl$_3$) δ 6.90 (d, J=8.6 Hz, 1H), 6.64 (d, J=8.3 Hz, 1H), 4.22 (br pk, 1H), 3.82 (br s, 2H), 3.75 (s, 3H), 3.52 (m, 2H), 3.28 (s, 3H), 3.04 (br pk, 1H), 2.51 (br pk, 1H), 2.33 (br pk, 1H), 2.28 (br s, 2H), 1.93 (br pk, 1H), 1.71 (br pk, 1H); LC/MS (ESI-pos) m/z 265.03 (M+H).

126b) Analogous to procedure Example 101b, 7-Amino-6-methoxy-1-(2-methoxy-ethyl)-1,3,4,5-tetrahydro-benzo[b]azepin-2-one (50 mg, 0.190 mmol) and 2-(2,5-Dichloro-pyrimidin-4-ylamino)-N-methyl-benzamide (55 mg, 0.185 mmol) were converted to the desired product 12x (26 mg, 27%), purified by ISCO chromatography. $^1$H-NMR (CDCl$_3$) δ 11.09 (s, 1H), 8.65 (d, J=8.3 Hz, 1H), 8.27 (d, J=8.8 Hz, 1H), 8.14 (s, 1H), 7.50 (m, 2H), 7.42 (s, 1H), 712 (t, J=7.5 Hz, 1H), 7.04 (d, J=8.8 Hz, 1H), 6.21 (br s, 1H), 3.80 (s, 3H), 3.54 (br m, 2H), 3.28 (s, 3H), 3.05 (d, J=5.0 Hz, 3H), 2.32 (br m, 2H), 1.0-2.5 (low, broad m's, 6H); LC/MS (ESI-pos) m/z 525.37 (M+H). M.P.=205-207° C.

Example 127

7-[5-Chloro-4-(2-methoxy-4-morpholin-4-yl-phenylamino)-pyrimidin-2-ylamino]-6-methoxy-1-(2-methoxy-ethyl)-1,3,4,5-tetrahydro-benzo[b]azepin-2-one 127a) Analogous to procedure Example 101b, 7-Amino-6-methoxy-1-(2-methoxy-ethyl)-1,3,4,5-tetrahydro-benzo[b]azepin-2-one (50 mg, 0.190 mmol) and (2,5-Dichloro-pyrimidin-4-yl)-(2-methoxy-4-morpholin-4-yl-phenyl)-amine (65 mg, 0.183 mmol) were converted to 7-[5-Chloro-4-(2-methoxy-4-morpholin-4-yl-phenylamino)-pyrimidin-2-ylamino]-6-methoxy-1-(2-methoxy-ethyl)-1,3,4,5-tetrahydro-benzo[b]azepin-2-one (33 mg, 31%), purified by ISCO chromatography. $^1$H-NMR (CDCl$_3$) δ 8.26 (d, J=8.8 Hz, 1H), 8.23 (d, J=8.1 Hz, 1H), 8.05 (s, 1H), 7.58 (s, 1H), 7.37 (s, 1H), 7.03 (d, J=8.3 Hz, 1H), 6.56 (m, 2H), 3.92 (s, 3H), 3.89 (m, 3H), 3.79 (s, 3H), 3.54 (br m, 2H), 3.28 (s, 3H), 3.17 (t, J=3.8 Hz, 4H), 2.32 (s, 2H), 1.0-2.5 (low, broad m's, 6H); LC/MS (ESI-pos) m/z 583.38 (M+H). M.P.=136-138° C.

Example 128

(2-exo,3-exo)-3-{5-Chloro-2-[6-methoxy-1-(2-methoxy-ethyl)-2-oxo-2,3,4,5-tetrahydro-1H-benzo[b]azepin-7-ylamino]-pyrimidin-4-ylamino}-bicyclo[2.2.1]hept-5-ene-2-carboxylic acid amide 128a) Analogous to procedure in Example 101b, 7-Amino-6-methoxy-1-(2-methoxy-ethyl)-1,3,4,5-tetrahydro-benzo[b]azepin-2-one (50 mg, 0.190 mmol) and (1R,2R,3S,4S)-3-(2,5-Dichloro-pyrimidin-4-ylamino)-bicyclo[2.2.1]hept-5-ene-2-carboxylic acid amide (55 mg, 0.184 mmol) were converted to (2-exo,3-exo)-3-{5-Chloro-2-[6-methoxy-1-(2-methoxy-ethyl)-2-oxo-2,3,4,5-tetrahydro-1H-benzo[b]azepin-7-ylamino]-pyrimidin-4-ylamino}-bicyclo[2.2.1]hept-5-ene-2-carboxylic acid amide (44 mg, 46%), purified by ISCO chromatography. $^1$H-NMR (CDCl$_3$) δ 8.41 (d, J=8.8 Hz, 1H), 7.92 (s, 1H), 7.41 (s, 1H), 7.16 (d, J=7.8 Hz, 1H), 7.08 (d, J=8.8 Hz, 1H), 6.35 (m, 2H), 5.62 (br s, 1H), 5.38 (br s, 1H), 4.35 (t, J=8.1 Hz, 1H), 3.80 (s, 3H), 3.55 (br s, 2H), 3.29 (s, 3H), 3.08 (s, 1H), 2.95 (s, 1H), 2.50 (d, J=8.3 Hz, 1H), 2.32 (br s, 2H), 2.25 (d, J=9.4 Hz, 1H), 1.64 (d, J=8.8 Hz, 1H), 1.0-1.25 (low, broad m's, 6H); LC/MS (ESI-pos) m/z 526.13 (M−H). M.P.=211-213° C.

Example 129

(2-exo, 3-exo)-3-[5-Chloro-2-(1-ethyl-6-methoxy-2-oxo-2,3,4,5-tetrahydro-1H-benzo[b]azepin-7-ylamino)-pyrimidin-4-ylamino]-bicyclo[2.2.1]heptane-2-carboxylic acid amide 129a) Analogous to procedure in Example 101b, 7-Amino-1-ethyl-6-methoxy-1,3,4,5-tetrahydro-benzo[b]azepin-2-one (140 mg, 0.598 mmol) and (2-exo,3-exo)-3-(2,5-Dichloro-pyrimidin-4-ylamino)-bicyclo[2.2.1]heptane-2-carboxylic acid amide (200 mg, 0.664 mmol) [for preparation see Example 177] were converted to (2-exo,3-exo)-3-[5-Chloro-2-(1-ethyl-6-methoxy-2-oxo-2,3,4,5-tetrahydro-1H-benzo[b]azepin-7-ylamino)-pyrimidin-4-ylamino]-bicyclo[2.2.1]heptane-2-carboxylic acid amide (125 mg, 42%), purified by ISCO chromatography. $^1$H-NMR (CDCl$_3$) δ 8.42 (d, J=8.8 Hz, 1H), 7.90, (s, 1H), 7.39 (s, 1H), 7.14 (d, J=7.6 Hz, 1H), 6.95 (d, J=8.8 Hz, 1H), 5.57 (br s, 1H), 5.34 (br s, 1H), 4.36 (t, J=8.1 Hz, 1H), 3.80 (s, 3H), 2.56 (d, J=8.3 Hz, 2H), 2.40 (br s, 1H), 2.29 (br s, 2H), 2.12 (m, 2H), 1.70 (m, 2H), 1.30 (m, 2H), 1.13 (t, J=7.1 Hz, 3H), 1.0-2.5 (low, broad m's, 6H); LC/MS (ESI-pos) m/z 499.36 (M+H). M.P.=136-138° C.

Example 130

N-{(1R,2R)-2-[5-Chloro-2-(1-ethyl-8-methoxy-2-oxo-2,3,4,5-tetrahydro-1H-benzo[b]azepin-7-ylamino)-pyrimidin-4-ylamino]-cyclohexyl}-methanesulfonamide 130a) Combined 7-Methoxy-1-tetralone (5.0 g, 0.028 mol) with Polyphosphoric acid (80 g, 0.7 mol) in 2-neck 500 ml Flask fit with overhead mechanical stirrer and septa under nitrogen flow. Sodium azide (2.2 g, 0.034 mol) added portionwise over 5 min and the reaction was heated to 55° C. Continue stirring overnight. The mixture was poured into water and a white precipitate ensued. The mixture was filtered and washed with water then hexane and dried over 60 h. 8-Methoxy-1,3,4,5-tetrahydro-benzo[b]azepin-2-one obtained as a white solid (3.34 g, 62%). MP: 103-104° C.; $^1$H-NMR (CDCl$_3$, 400 MHz) δ 7.45 (broad s, 1H), 7.13 (d, J=8.3 Hz, 1H), 6.72-6.69 (m, 1H), 6.54 (d, J=2.1 Hz, 1H), 3.81 (s, 3H), 2.76 (t, J=7.2 Hz, 2H), 2.38 (t, J=7.3 Hz, 2H), 2.25-2.18 (m, 2H); LC/MS: 192.07 (M+H).

130b) 8-Methoxy-1,3,4,5-tetrahydro-benzo[b]azepin-2-one (1.10 g, 0.00575 mol) was charged into RBF fit with stir bar, septum and under N2 atmosphere. Charged with N,N-Dimethylformamide (25 mL) and then Sodium Hydride (60% dispersion mineral oil) (0.25 g), gas evolution (H2) ensued. The mixture was stirred about 5 minutes and then treated with Iodoethane (0.63 mL, 0.0078 mol) and stirred at room temperature for 1.3 h. The mixture was quenched with ice/water and extracted with ether. The ether layer was washed with water, then with brine, dried (MgSO4), filtered and concentrated to give a 1-Ethyl-8-methoxy-1,3,4,5-tetrahydro-benzo[b]azepin-2-one as a clear oil (1.19 g, 94%). $^1$H-NMR (CDCl$_3$) δ 7.21 (t, J=8.2 Hz, 1H), 6.83 (d, J=8.1 Hz, 1H), 6.76 (d, J=8.4 Hz, 1H), 3.84 (s, 3H), 2.25 (s, 2H), 1.7-3.5 (br pk's, 6H), 1.13 (t, J=7.2 Hz, 3H); LC/MS (ESI-pos) m/z 220.09 (M+H). M.P.=Oil. LC/MS: 220.06 (M+H).

130c) Following the general procedure 107b-107c, 1-Ethyl-8-methoxy-1,3,4,5-tetrahydro-benzo[b]azepin-2-one (1.10 g, 5.02 mmol) was converted to 7-Amino-1-ethyl-8-methoxy-1,3,4,5-tetrahydro-benzo[b]azepin-2-one as a yellow waxy solid (640 mg). $^1$H-NMR (CDCl$_3$) δ 6.61 (s, 1H), 6.52 (s, 1H), 3.84 (s, 3H), 3.78 (br s, 2H), 2.54 (br m, 2H), 2.24 (br s, 2H), 2.10 (br m, 2H), 1.12 (t, J=7.1 Hz, 3H); LC/MS (ESI-pos) m/z 235.06 (M+H). Also using the procedures was 1-Ethyl-6-methoxy-9-nitro-1,3,4,5-tetrahydro-benzo[b]azepin-2-one (80 mg) was also obtained pure %). 1H-NMR (CDCl$_3$) δ 6.74 (d, J=8.6 Hz, 1H), 6.64 (d, J=8.8 Hz, 1H), 4.27 (sext, J=6.9 Hz, 1H), 3.77 (s, 3H), 3.42 (br s, 2H), 3.32 (sext, J=6.9 Hz, 1H), 3.19 (dd, J=6.3 Hz, 13.4 Hz, 1H), 2.37 (m, 1H), 2.23 (m, 3H), 1.82 (br m, 1H), 1.10 (t, J=7.1 Hz, 3H); LC/MS (ESI-pos) m/z 235.10 (M+H). M.P.=154-156° C.

130d) Combined 7-Amino-1-ethyl-8-methoxy-1,3,4,5-tetrahydro-benzo[b]azepin-2-one (124.8 mg, 0.0005327 mol), N-[(1R,2R)-2-(2,5-Dichloro-pyrimidin-4-ylamino)-cyclohexyl]-methanesulfonamide (180 mg, 0.00053 mol), 4 M of Hydrogen chloride in 1,4-Dioxane (200 uL) and heat in a Radley tube for 4.5 h at 110° C. Cool to RT and then treated with xs solid MP-carbonate resin and stirred for 30 min. Filtration, followed by concentration afforded a gummy solid that was put on high-vac overnight. The mixture was purified by ISCO chromatography (40 g SiO2, 30% EA/hexane to 100% EA) afforded N-{(1R,2R)-2-[5-Chloro-2-(1-ethyl-8-methoxy-2-oxo-2,3,4,5-tetrahydro-1H-benzo[b]azepin-7-ylamino)-pyrimidin-4-ylamino]-cyclohexyl}-methanesulfonamide as an off-white foam that was dried under high vac and broken into a powder (112.41 mg, 39%). MP: 120-128° C. $^1$H-NMR (DMSO, 400 MHz) δ 8.10 (s, 1H), 7.96 (d, J=1.1 Hz, 1H), 7.69 (s, 1H), 7.18 (d, J=8.3 Hz, 1H), 7.00 (s, 1H), 6.85 (d, J=7.9 Hz, 1H), 3.88-3.83 (m, 1H), 3.35-3.31 (m, 1H), 2.90 (s, 3H), 2.60 (broad s, 2H), 2.11-2.00 (m, 8H), 1.70-1.67 (m, 2H), 1.40-1.15 (m, 5H), 1.00 (t, J=6.9 Hz, 3H); LC/MS: 537.34 (M+H).

Example 131

(2-exo,3-exo)-3-[5-Chloro-2-(1-ethyl-8-methoxy-2-oxo-2,3,4,5-tetrahydro-1H-benzo[b]azepin-7-ylamino)-pyrimidin-4-ylamino]-bicyclo[2.2.1]hept-5-ene-2-carboxylic acid amide 131a) Combined (2-exo, 3-exo)-3-(2,5-Dichloro-pyrimidin-4-ylamino)-bicyclo[2.2.1]hept-5-ene-2-carboxylic acid amide (57 mg, 0.00019 mol), 7-Amino-1-ethyl-8-methoxy-1,3,4,5-tetrahydro-benzo[b]azepin-2-one (45 mg, 0.00019 mol), 4 M of Hydrogen chloride in 1,4-Dioxane (60 uL) and 2-Methoxyethanol (2.3 mL, 0.029 mol). Heat in a Radley tube for about 4.5 h at 110° C. Cool to RT and then treated with excess solid MP-carbonate resin and stirred for 30 min. Filtration, followed by concentration afforded a gummy solid that was put on high-vac overnight. The mixture was treated with ethyl acetylate and an off-white solid formed upon sonication and then standing. The solid was filtered off and dried under high vac to give (2-exo,3-exo)-3-[5-Chloro-2-(1-ethyl-8-methoxy-2-oxo-2,3,4,5-tetrahydro-1H-benzo[b]azepin-7-ylamino)-pyrimidin-4-ylamino]-bicyclo[2.2.1]hept-5-ene-2-carboxylic acid amide (58.01 mgs, 61%). MP: 222-223° C. 1H-NMR (dmso, 400 MHz); 8.04 (s, 1H), 7.97 (s, 1H), 7.76-7.75 (m, 2H), 7.70 (s, 1H), 7.25 (s, 1H), 7.01 (s, 1H), 6.34 (s, 1H), 6.19 (s, 1H), 4.06-4.00 (m, 2H), 3.88 (s, 3H), 3.85 (broad s, 1H), 2.87 (s, 1H), 2.73 (s, 1H), 2.54-2.50 (m, 4H), 2.12-2.10 (m, 4H), 1.42-1.40 (m, 1H)m 1.10 (t, J=7.0 Hz, 3H); LC/MS: 497.35.

Example 132 and Example 133

(1R,2R,3S,4S)-3-[5-Chloro-2-(1-ethyl-6-methoxy-2-oxo-2,3,4,5-tetrahydro-1H-benzo[b]azepin-7-ylamino)-pyrimidin-4-ylamino]-bicyclo[2.2.1]hept-5-ene-2-carboxylic acid amide and (1S,2S,3R,4R)-3-[5-Chloro-2-(1-ethyl-6-methoxy-2-oxo-2,3,4,5-tetrahydro-1H-benzo[b]azepin-7-ylamino)-pyrimidin-4-ylamino]-bicyclo[2.2.1]hept-5-ene-2-carboxylic acid amide 132a) A racemic mixture of (1S,2S,3R,4R)-3-[5-Chloro-2-(1-ethyl-6-methoxy-2-oxo-2,3,4,5-tetrahydro-1H-benzo[b]azepin-7-ylamino)-pyrimidin-4-ylamino]-bicyclo[2.2.1]hept-5-ene-2-carboxylic acid amide and (1S,2S,3R,4R)-3-

[5-Chloro-2-(1-ethyl-6-methoxy-2-oxo-2,3,4,5-tetrahydro-1H-benzo[b]azepin-7-ylamino)-pyrimidin-4-ylamino]-bicyclo[2.2.1]hept-5-ene-2-carboxylic acid amide {also known as (2-exo,3-exo)-3-[5-Chloro-2-(1-ethyl-6-methoxy-2-oxo-2,3,4,5-tetrahydro-1H-benzo[b]azepin-7-ylamino)-pyrimidin-4-ylamino]-bicyclo[2.2.1]hept-5-ene-2-carboxylic acid amide} (10 mg, 0.00002 mol) was separated using ChiralPak ASH 4.6×250 mm Daicel column and 40% MeOH Modifier with λ=220 nm, oven at 50° C., Pressure=100 psi, Flow=2.5 mL/min and 4 stacked injections. Peak A, Faster Eluting (2.02 mgs) and the Slower Eluting Peak B (2.95 mgs) were isolated. Peak A (Faster Eluting Enantiomer): $^1$H NMR (CDCl$_3$, 400 MHz): $^1$H-NMR (CDCl$_3$) δ8.40 (d, J=8.8 Hz, 1H), 7.92 (s, 1H), 7.41 (s, 1H), 7.15 (d, J=7.8 Hz, 1H), 6.96 (d, J=8.8 Hz, 1H), 6.34 (br s, 2H), 5.64 (br s, 1H), 5.40 (br s, 1H), 3.80 (s, 3H), 3.73 (m, 2H), 3.08 (s, 1H), 2.95 (s, 1H), 2.29 (br s, 2H), 1.24 (m, 8H), 1.13 (t, J=7.0, 3H); Peak B (Slower Eluting Enantiomer): 2.95 mgs isolated as a film: 1H NMR (CDCl$_3$, 400 MHz): $^1$H-NMR (CDCl$_3$) δ 8.40 (d, J=8.8 Hz, 1H), 7.92 (s, 1H), 7.41 (s, 1H), 7.15 (d, J=7.8 Hz, 1H), 6.96 (d, J=8.8 Hz, 1H), 6.34 (br s, 2H), 5.64 (br s, 1H), 5.40 (br s, 1H), 3.80 (s, 3H), 3.73 (m, 2H), 3.08 (s, 1H), 2.95 (s, 1H), 2.29 (br s, 2H), 1.24 (m, 8H), 1.13 (t, J=7.0, 3H).

Alternatively, the two enantiomers could be prepared as follows.

132b) A racemic mixture of (2-exo, 3-exo)-3-(2,5-Dichloro-pyrimidin-4-ylamino)-bicyclo[2.2.1]hept-5-ene-2-carboxylic acid amide (2 g) was separated using ChiralPak ASH 4.6×250 mm Daicel column and 40% MeOH Modifier with λ=220 nm, oven at 50° C., Pressure=100 psi, Flow=2.5 mL/min and 10 stacked injections. Peak A, Faster Eluting (900 mgs) (1R,2R,3S,4S)-3-(2,5-Dichloro-pyrimidin-4-ylamino)-bicyclo[2.2.1]hept-5-ene-2-carboxylic acid amide and the Slower Eluting Peak B (940 mg) (1S,2S,3R,4R)-3-(2,5-Dichloro-pyrimidin-4-ylamino)-bicyclo[2.2.1]hept-5-ene-2-carboxylic acid amide were isolated. The NMR spectra were equivalent to the racemic mixture.

132c) 7-Amino-1-ethyl-6-methoxy-1,3,4,5-tetrahydro-benzo[b]azepin-2-one (741 mg, 0.00316 mol), (1S,2S,3R,4R)-3-(2,5-Dichloro-pyrimidin-4-ylamino)-bicyclo[2.2.1]hept-5-ene-2-carboxylic acid amide (790 mg, 0.0026 mol) in 2-Methoxyethanol (26 mL, 0.33 mol) and then treat with 4 M of Hydrogen chloride in 1,4-Dioxane (800 uL) and heat to 110° C., for 3.5 h. The mixture was cooled to rt and treated with ≈1.5 grams of MP-carbonate to neutralize the HCl. The mixture was filtered and concentrated on rotovap to give an off-white/yellowish foamy solid. The mixture was purified by ISCO chromatography. Stripped down to give reddish oil. This oil was dissolved in minimal EtOAc and heated. Hexane was added to the mixture until cloudy and the product crystallized out as a tan solid. Filtered off and dried. The material was concentrated from DCM/MeOH and put on vac at 40° C. to remove residual CH2Cl2. Isolated (1S,2S,3R,4R)-3-[5-Chloro-2-(1-ethyl-6-methoxy-2-oxo-2,3,4,5-tetrahydro-1H-benzo[b]azepin-7-ylamino)-pyrimidin-4-ylamino]-bicyclo[2.2.1]hept-5-ene-2-carboxylic acid amide as a tan solid (830.54 mgs, 63%); MP: 204-206° C., $^1$H-NMR (CDCl$_3$) δ 8.40 (d, J=8.8 Hz, 1H), 7.92 (s, 1H), 7.41 (s, 1H), 7.15 (d, J=7.8 Hz, 1H), 6.96 (d, J=8.8 Hz, 1H), 6.34 (br s, 2H), 5.64 (br s, 1H), 5.40 (br s, 1H), 3.80 (s, 3H), 3.73 (m, 2H), 3.08 (s, 1H), 2.95 (s, 1H), 2.29 (br s, 2H), 1.24 (m, 8H), 1.13 (t, J=7.0, 3H); LC/MS: 497.35 (M+H).

132d) Following the procedure of 117c, 7-Amino-1-ethyl-6-methoxy-1,3,4,5-tetrahydro-benzo[b]azepin-2-one (34 mg, 0.00316 mol), (1R,2R,3S,4S)-3-(2,5-Dichloro-pyrimidin-4-ylamino)-bicyclo[2.2.1]hept-5-ene-2-carboxylic acid amide (39 mg) were converted to (1R,2R,3S,4S)-3-[5-Chloro-2-(1-ethyl-6-methoxy-2-oxo-2,3,4,5-tetrahydro-1H-benzo[b]azepin-7-ylamino)-pyrimidin-4-ylamino]-bicyclo[2.2.1]hept-5-ene-2-carboxylic acid amide (27 mg, 42%). MP: 212-213° C., $^1$H-NMR (CDCl$_3$) δ 8.40 (d, J=8.8 Hz, 1H), 7.92 (s, 1H), 7.41 (s, 1H), 7.15 (d, J=7.8 Hz, 1H), 6.96 (d, J=8.8 Hz, 1H), 6.34 (br s, 2H), 5.64 (br s, 1H), 5.40 (br s, 1H), 3.80 (s, 3H), 3.73 (m, 2H), 3.08 (s, 1H), 2.95 (s, 1H), 2.29 (br s, 2H), 1.24 (m, 8H), 1.13 (t, J=7.0, 3H); LC/MS (ESI-pos) m/z 497.35 (M+H). Alternatively (1S,2S,3R,4R)-3-(2,5-Dichloro-pyrimidin-4-ylamino)-bicyclo[2.2.1]hept-5-ene-2-carboxylic acid amide can be prepared according to the following procedures:

132e) In a 500 mL RBF, fit with dropping funnel and stir bar, under N2 was charged with Methylene chloride (100 mL) and 2,5-Norbornadiene (25 mL, 0.24 mol). The mixture was cooled in an ice/NaCl bath (ca. −5° C.). The dropping funnel was charged with Chlorosulfonyl Isocyanate (21.4 mL, 0.246 mol) and Methylene chloride and this mixture was added dropwise slowly to the reaction over about 1 hour. The mixture was held at −5° C. for about 1 hour further with stirring then warmed to room temp by removal of the ice bath. This warming occurred over about 2 h. The mixture was quenched with water (60 mL) and stirred for 10 min. The org layer was separated, washed with brine, dried (sodium sulfate) and concentrated to give a pale yellow oil. The pale yellow oil was dissolved in Methylene chloride (100 mL, 2 mol) and added dropwise to a −5° C. (Ice/NaCl bath) solution of Sodium sulfite (24.5 g, 0.194 mol), Methylene chloride (30 mL, 0.5 mol), and Water (70 mL, 4 mol) in a two neck 500 mL RBF. During the addition, the pH of the mixture was kept between 7 and 10 (monitor by pH paper) by addition of 10% NaOH. The addition took about 1 h. Following the complete addition, the pH was adjusted to 8.5 and the milky white solution was stirred for 1 h at −5° C. The mixture was diluted with about 400 mL of methylene chloride and the mixture stirred vigorously overnight. The stirred mixture was transferred to a 1 L separatory funnel and the layers separated. The aq was extracted 2× further with dichloromethane (200 mL each) and the combined organics washed with brine, dried (MgSO$_4$), filtered through a bed of Celite and concentrated to give 3-Aza-tricyclo[4.2.1.0(2,5)]non-7-en-4-one a white solid. (21.6 g) (65% yield); MP: 94-97° C.

132f) Combine 3-Aza-tricyclo[4.2.1.0(2,5)]non-7-en-4-one (37.2 g, 0.275 mol) and Tetrahydrofuran (300 mL, 3 mol) in RBF, cool to 0° C. Di-tert-Butyldicarbonate (0.060 kg, 0.28 mol) and 4-Dimethylaminopyridine (4.0 g, 0.033 mol) added. Stir at 0° C. for about 5 min, then warmed to room temperature. Stir overnight. Strip off THF, partition solid between EtOAc (500 mL) and water (300 mL), extract aqueous with EtOAc (300 mL). The combined organic layers were washed with brine, dried (MgSO4), filtered and concentrated to give 4-Oxo-3-aza-tricyclo[4.2.1.0(2,5)]non-7-ene-3-carboxylic acid tert-butyl ester an yellowish solid which was dried on high-vac (59.25 g)

132g) Combine 4-Oxo-3-aza-tricyclo[4.2.1.0(2,5)]non-7-ene-3-carboxylic acid tert-butyl ester (60.94 g, 0.2590 mol) and Tetrahydrofuran (800 mL, 10 mol) in 2 L Erlenmeyer flask. Addition of 1.00 M of Lithium hydroxide in Water (780 mL) gave a slight exotherm and the flask was cooled during addition of LiOH solution with an ice water bath. The mixture was then warmed to rt following addition and stirred at room temperature overnight. Cooled 0° C. in ice/water bath. Added conc HCl to pH 2. A milky white liquid ensued. The THF was mostly removed by rotovap to give a precipitated solid in the water. This aqueous/solid mixture was diluted with 700 mL of CH2Cl2 and stirred for two hours during which the solid completely dissolved in the organic layer. The aqueous was further extracted with 400 mL of CH2Cl2 and the combined organics were dried (MgSO4), filtered and concentrated to give 3-tert-Butoxycarbonylamino-bicyclo[2.2.1]hept-5-ene-2-carboxylic acid as an off-white solid, put on high vac at 40° C. to remove excess dichloromethane present in the solid sample. (60.40 g, 92%). $^1$H-NMR (CDCL3, 400 MHz): δ 12.0 (broad absorption, 1H) 6.97 (d, J=10.6 Hz, 1H), 6.20 (s, 1H); 3.96 (t, J=9.6 Hz, 1H), 2.99 (s, 1H), 2.74 (s, 1H), 2.60 (d, J=8.4 Hz, 1H), 2.09 (d, J=9.3 Hz, 1H), 1.66 (d, J=9.4 Hz, 1H), 1.47 (s, 9H).

132h) Combine 3-tert-Butoxycarbonylamino-bicyclo[2.2.1]hept-5-ene-2-carboxylic acid (67.2 g, 0.265 mol) in Ethyl acetate (1.0 L) and treat with (R)-α-Methylbenzenemethanamine (34.20 mL, 0.2653 mol) dropwise. Stir and white solid precipitated out of solution. Stir at room temperature for 64 h. The mixture was filtered on Buchner and air dried to give a white solid (59.16 g). The solid was diluted with ethyl acetate, heated and slowly cooled and the solid isolated. This was repeated until a constant optical rotation was obtained to give 14.5 grams of (1S,2S,3R,4R)-3-tert-Butoxycarbonylamino-bicyclo[2.2.1]hept-5-ene-2-carboxylic acid (R)-1-phenyl-ethylamine salt.

132i) (1S,2S,3R,4R)-3-tert-Butoxycarbonylamino-bicyclo[2.2.1]hept-5-ene-2-carboxylic acid (R)-1-phenyl-ethylamine salt (10.0 g, 26.7 mmol) in Ethyl acetate (200 mL, 2000 mmol) and Water (100 mL, 6000 mmol) was added 1 M of Hydrogen Chloride in Water (50 mL) via pipette to pH 2. The layers were separated and the aqueous was extracted (EtOAc), drying of combined organics (MgSO4) provided (1S,2S,3R,4R)-3-tert-Butoxycarbonylamino-bicyclo[2.2.1]hept-5-ene-2-carboxylic acid as a white foamy solid 6.74 grams $^1$H-NMR (CDCL3, 400 MHz): δ 12.30 (broad peak 1H)m 6.99 (d, J=9.6 Hz, 1H), 6.20 (vroad s, 2H), 3.97 (t, J=9.6 Hz, 1H), 3.05 (s, 1H), 2.74 (s, 1H), 2.60 (d, J=8.4 Hz, 1H), 2.09 (d, J=9.6 Hz, 1H), 1.66 (d, J=9.6 Hz, 1H), 1.46 (s, 9H).

132j) (1S,2S,3R,4R)-3-tert-Butoxycarbonylamino-bicyclo[2.2.1]hept-5-ene-2-carboxylic acid (6.66 g, 26.3 mmol), Di-tert-Butyldicarbonate (8.6 g, 39 mmol) and Pyridine (3.8 mL, 47 mmol) were added to 1,4-Dioxane (40 mL, 500 mmol) and the reaction stirred for 30 minutes at room temperature. Ammonium Bicarbonate (5.8 g, 74 mmol) was added, and the reaction mixture was stirred overnight. The reaction was quenched by addition of water. Extraction (2×) with EtOAc, washing 2× with 0.1 N HCl, and once w/ brine, drying (MgSO4), concentration, provided ((1R,2R,3S,4S)-3-Carbamoyl-bicyclo[2.2.1]hept-5-en-2-yl)-carbamic acid tert-butyl ester as a white solid (6.47 grams).

132k) Combine ((1R,2R,3S,4S)-3-Carbamoyl-bicyclo[2.2.1]hept-5-en-2-yl)-carbamic acid tert-butyl ester (38.41 g, 0.1522 mol), Methylene chloride (300 mL, 5 mol). Treat with Trifluoroacetic Acid (120 mL, 1.6 mol) at room temperature and stir for about 1 h. After 1 h the mixture was concentrated to a pale yellow oil (117 g) of crude product. This material was treated with Et2O (200 mL) to afford a white solid, which was filtered and rinsed with a small amount of Et2O, then dried over two days under high vacuum. After drying there remained 39.02 g (96%) of white solid label (1S,2S,3R,4R)-3-Amino-bicyclo[2.2.1]hept-5-ene-2-carboxylic acid amide trifluoro-acetic acid salt 132l) Combine (1S,2S,3R,4R)-3-Amino-bicyclo[2.2.1]hept-5-ene-2-carboxylic acid amide trifluoro-acetic acid (36.25 g, 0.1362 mol) in Water (300 mL, 20 mol) and Methanol (600 mL, 10 mol) with Sodium bicarbonate (30 g, 0.4 mol). 2,4,5-Trichloro-pyrimidine (24.20 g, 0.1319 mol) added dropwise at room temperature Then let reaction stir at RT overnight. After stirring an additional 16 h add an additional 0.70 g of (1S,2S,3R,4R)-3-Amino-bicyclo[2.2.1]hept-5-ene-2-carboxylic acid amide trifluoro-acetic acid as well as 1 g additional NaHCO3. Then let stir again overnight. Pour reaction mixture into 2.5 L of water and see solid crashes out. Filter and then wash resulting solid with 5:1 H2O:MeOH (~300 mL). The resulting solid was air dried to yield 30.87 g (78%) of white solid (1S,2S,3R,4R)-3-(2,5-Dichloro-pyrimidin-4-ylamino)-bicyclo[2.2.1]hept-5-ene-2-carboxylic acid amide. The NMR was equivalent to the racemic material.

Example 134

2-[5-Chloro-2-(1-ethyl-8-methoxy-2-oxo-2,3,4,5-tetrahydro-1H-benzo[b]azepin-7-ylamino)-pyrimidin-4-ylamino]-N-methyl-benzamide 134a) 2-(2,5-Dichloro-pyrimidin-4-ylamino)-N-methyl-benzamide (100 mg, 0.4 mmol), and 7-Amino-1-ethyl-8-methoxy-1,3,4,5-tetrahydro-benzo[b]azepin-2-one (104 mg, 0.444 mmol), 4 M of Hydrogen chloride in 1,4-Dioxane (100 uL), 2-Methoxyethanol (4.5 mL, 57 mmol) were charged into Radley tube. Heat 110° C. for about 3 hours, cooled to room temperature. The mixture was treated with excess MP-carbonate and stirred 30 min. Filtration followed by concentration gave a yellow film. Treatment with EtOAc and sonication provided an off-white solid. This material was stripped onto Celite and purified on ISCO column (40 g SiO2, gradient 50% EtOAc hexane to 100% EtOAc to 5% MeOH/EtOAc) gave 2-[5-Chloro-2-(1-ethyl-8-methoxy-2-oxo-2,3,4,5-tetrahydro-1H-benzo[b]azepin-7-ylamino)-pyrimidin-4-ylamino]-N-methyl-benzamide as a white solid (42.06 mg, 20%). MP: 232-233° C. $^1$H-NMR (dmso, 400 MHz) δ 11.56 (s, 1H), 8.74 (d, J=4.5 Hz, 1H), 8.53 (d, J=8.5 Hz, 1H), 8.23 (s, 1H), 8.20 (s, 1H), 7.73 (d J=7.8 Hz, 1H), 7.67 (s, 1H), 7.32 (t, J=7.8 Hz, 1H), 7.11 (t, J=7.6 Hz, 1H), 7.05 (s, 1H) 3.85-3.80 (broad m, 2H), 3.83 (s, 3H), 2.80 (d, J=4.2 Hz, 3H), 2.50-2.49 (m, 2H), 2.12-2.10 (m, 2H), 2.10-1.99 (m, 2H), 1.01 (t, J=7.0 Hz, 3H); LC/MS: 495.37 (M+H).

Example 135

7-[5-Chloro-4-(2-methoxy-4-morpholin-4-yl-phenylamino)-pyrimidin-2-ylamino]-1-ethyl-8-methoxy-1,3,4,5-tetrahydro-benzo[b]azepin-2-one 135a) Following an analogous procedure to in Example 101b, 7-Amino-1-ethyl-8-methoxy-1,3,4,5-tetrahydro-benzo[b]azepin-2-one (104 mg, 0.445 mmol) and (2,5-Dichloro-pyrimidin-4-yl)-(2-methoxy-4-morpholin-4-yl-phenyl)-amine (158 mg, 0.445 mmol) were converted to 7-[5-Chloro-4-(2-methoxy-4-morpholin-4-yl-phenylamino)-pyrimidin-2-ylamino]-1-ethyl-8-methoxy-1,3,4,5-tetrahydro-benzo[b]azepin-2-one (115 mg, 47%), obtained by trituration in EtOAc. $^1$H-NMR (DMSO) δ 9.25 (br s, 1H), 8.73 (br s, 1H), 8.29 (s, 1H), 7.60 (s, 1H), 7.28 (d, J=8.4 Hz, 1H), 7.00 (s, 1H), 6.70 (s, 1H), 6.53 (d, J=8.6, 1H), 3.85 (s, 3H), 3.75 (br s, 7H), 3.24 (m, 2H), 3.16 (m, 4H), 2.25 (br m, 2H), 2.05 (m, 2H), 1.91 (br m, 2H), 0.97 (t, J=6.8 Hz, 3H); LC/MS (ESI-pos) m/z 552.98 (M+H). M.P.=212-214° C.

Example 136

(2-exo,3-exo)-3-[5-Chloro-2-(1-ethyl-8-methoxy-2-oxo-2,3,4,5-tetrahydro-1H-benzo[b]azepin-7-ylamino)-pyrimidin-4-ylamino]-bicyclo[2.2.1]heptane-2-carboxylic acid amide 136a) Following an analogous procedure to in Example 110b, 7-Amino-1-ethyl-8-methoxy-1,3,4,5-tetrahydrobenzo[b]azepin-2-one (104 mg, 0.445 mmol) and (2-exo,3-exo)-3-(2,5-Dichloro-pyrimidin-4-ylamino)-bicyclo[2.2.1]heptane-2-carboxylic acid amide (134 mg, 0.445 mmol) were converted (2-exo,3-exo)-3-[5-Chloro-2-(1-ethyl-8-methoxy-2-oxo-2,3,4,5-tetrahydro-1H-benzo[b]azepin-7-ylamino)-pyrimidin-4-ylamino]bicyclo[2.2.1]heptane-2-carboxylic acid amide (50 mg, 23%), obtained by trituration in EtOAc. $^1$H-NMR (DMSO) δ 8.04 (s, 1H), 7.95 (s, 1H), 7.83 (d, J=6.8 Hz, 1H), 7.68 (s, 2H), 7.16 (s, 1H), 7.00 (s, 1H), 4.12 (t, J=7.6 Hz, 1H), 3.87 (s, 3H), 3.50-4.00 (br pk, 1H), 2.60 (m, 3H), 2.28 (s, 1H), 1.95-2.20 (br m's, 5H), 1.92 (d, J=9.1 Hz, 1H), 1.52 (m, 2H), 1.22 (m, 3H), 1.14 (d, J=10.4 Hz, 1H), 1.00 (t, J=6.9 Hz, 3H); LC/MS (ESI-pos) m/z 499.36 (M+H). M.P.=244-246° C.

Example 137

7-[5-Chloro-4-(5-chloro-2-methoxy-phenylamino)-pyrimidin-2-ylamino]-1-ethyl-8-methoxy-1,3,4,5-tetrahydro-benzo[b]azepin-2-one 137a) Following an analogous procedure to in Example 101b, 7-Amino-1-ethyl-8-methoxy-1,3,4,5-tetrahydro-benzo[b]azepin-2-one (104 mg, 0.445 mmol) and (5-Chloro-2-methoxy-phenyl)-(2,5-dichloro-pyrimidin-4-yl)-amine (136 mg, 0.445 mmol) [Prepared using an analogous procedure to Example 1d using 2,4,5-trichloropyrimidine and 5-Chloro-2-methoxy-phenylamine] were converted to 7-[5-Chloro-4-(5-chloro-2-methoxy-phenylamino)-pyrimidin-2-ylamino]-1-ethyl-8-methoxy-1,3,4,5-tetrahydro-benzo[b]azepin-2-one (112 mg, 50%), purified by ISCO chromatography. $^1$H-NMR (CDCl$_3$) δ 8.48 (s, 1H), 8.12 (s, 2H), 7.80 (s, 1H), 7.52 (s, 1H), 7.02 (d, J=9.0 Hz, 1H), 6.85 (d, J=8.8 Hz, 1H), 6.72 (s, 1H), 3.94 (s, 3H), 3.91 (s, 3H), 2.55-2.75 (br pk, 2H), 2.25 (br s, 2H), 2.00-2.20 (br pk, 4H), 1.14 (t, J=6.9 Hz, 3H); LC/MS (ESI-pos) m/z 502.54 (M+H). M.P.=194-196° C.

Example 138

2-[5-Chloro-2-(1-ethyl-8-methoxy-2-oxo-2,3,4,5-tetrahydro-1H-benzo[b]azepin-7-ylamino)-pyrimidin-4-ylamino]-3-fluoro-N-methyl-benzamide 138a) 7-Amino-1-ethyl-8-methoxy-1,3,4,5-tetrahydro-benzo[b]azepin-2-one (104 mg, 0.445 mmol) and 22-(2,5-Dichloro-pyrimidin-4-ylamino)-3-fluoro-N-methyl-benzamide (see Example 311b for preparation) (140 mg, 0.445 mmol) in 4.45 mL of 2-methoxyethanol was added 114 mg of Camphorsulfonic acid (0.490 mmol). The solution was heated to 110° C. for 7 hrs, followed by the addition of MP-Carbonate (280 mg, 0.892 mmol) at RT. The MP-Carbonate was filtered after 30 minutes and the resulting crude material was triturated in EtOAc to give 2-[5-Chloro-2-(1-ethyl-8-methoxy-2-oxo-2,3,4,5-tetrahydro-1H-benzo[b]azepin-7-ylamino)-pyrimidin-4-ylamino]-3-fluoro-N-methyl-benzamide (80 mg, 35%). $^1$H-NMR (CDCl$_3$) δ 8.88 (s, 1H), 8.11 (s, 1H), 7.91 (s, 1H), 7.54 (s, 1H), 7.36 (d, J=7.3 Hz, 1H), 7.28 (m, 2H), 6.64 (s, 1H), 6.19 (m, 1H), 3.85 (s, 3H), 2.95 (d, J=5.0 Hz, 3H), 2.21 (m, 2H), 1.65-2.65 (br pk, 6H), 1.10 (t, J=6.7 Hz, 3H); LC/MS (ESI-pos) m/z 513.33 (M+H). M.P.=254-256° C.

Example 139

(2-exo,3-exo)-3-[5-Chloro-2-(6-methoxy-2-oxo-2,3,4,5-tetrahydro-1H-benzo[b]azepin-7-ylamino)-pyrimidin-4-ylamino]-bicyclo[2.2.1]hept-5-ene-2-carboxylic acid amide 139a) Analogous to procedure 103c, 6-Methoxy-7-nitro-1,3,4,5-tetrahydro-benzo[b]azepin-2-one (380 mg, 1.61 mmol) was converted to the desired product 7-Amino-6-methoxy-1,3,4,5-tetrahydro-benzo[b]azepin-2-one (325 mg, 98%). $^1$H-NMR (DMSO) δ 9.09 (s, 1H), 6.51 (quart, J=8.2 Hz, 2H), 4.77 (s, 2H), 3.62 (s, 3H), 2.63 (t, J=6.6 Hz, 2H), 2.08 (m, 4H); LC/MS (ESI-pos) m/z 207.07 (M+H).

139b) (2-exo,3-exo)-3-(2,5-Dichloro-pyrimidin-4-ylamino)-bicyclo[2.2.1]hept-5-ene-2-carboxylic acid amide (144 mg, 0.000481 mol), 7-Amino-6-methoxy-1,3,4,5-tetrahydro-benzo[b]azepin-2-one (110 mg, 0.00053 mol) 4 M of Hydrogen chloride in 1,4-Dioxane (200 uL) and 2-Methoxyethanol (5.3 mL, 0.067 mol) were combined and heated in a Radley tube for about 4.5 h at 110° C. Cool to RT and a solid came out of solution, stirred over night. Filtration was followed by washing with 2-methoxyethanol to give a white powder. The powder was treated with saturated aq. bicarb, sonicated to break up solids and stirred for 1 h. The white solid was filtered and dried overnight. (2-exo,3-exo)-3-[5-Chloro-2-(6-methoxy-2-oxo-2,3,4,5-tetrahydro-1H-benzo[b]azepin-7-ylamino)-pyrimidin-4-ylamino]-bicyclo[2.2.1]hept-5-ene-2-carboxylic acid amide was isolated as a white solid (188.82 mgs, 84%); MP: 252-253° C. $^1$H-NMR (dmso, 400 MHz) δ 9.56 (s, 1H), 8.31 (s, 1H), 8.01 (s, 1H), 7.86 (s, 1H), 7.45 (s, 1H), 6.84 (d, J=8.6 Hz, 1H), 6.37 (s, 1H), 6.16 (s, 1H), 3.92 (t, J=7.1 Hz, 1H), 3.75 (s, 3H), 3.48 (t, J=5.1 Hz, 1H), 3.38 (t, J=4.6 Hz, 1H), 2.95 (s, 1H), 2.90 (s, 1H), 2.76-2.41 (m, 2H), 2.50-2.48 (m, 2H), 2.20-2.15 (m, 4H), 1.96 (d, J=8.6 Hz, 1H), 1.41 (d, J=8.8 Hz, 1H); LC/MS: 469.24 (M+H).

Example 140

7-[5-Chloro-4-(2-methoxy-4-morpholin-4-yl-phenylamino)-pyrimidin-2-ylamino]-6-methoxy-1,3,4,5-tetrahydro-benzo[b]azepin-2-one 140a) Combined 7-Amino-6-methoxy-1,3,4,5-tetrahydro-benzo[b]azepin-2-one (110 mg, 0.00053 mol) Isopropyl alcohol, (2,5-Dichloro-pyrimidin-4-yl)-(2-methoxy-4-morpholin-4-yl-phenyl)-amine (170 mg, 0.00048 mol), 4 M of Hydrogen chloride in 1,4-Dioxane (200 uL) and 2-Methoxyethanol (5.3 mL, 0.067 mol) in a Radley tube, heat to 110° C. for about 4.5 h. Cool to RT and a solid came out of solution, stirred over night Filtration was followed by washing with 2-methoxyethanol to give a yellow powder. The powder was treated with saturated aq. bicarb, sonicated to break up solids and stirred for 1 h. The yellow solid was filtered and dried overnight. Isolated C as a yellow solid (131.16 mgs, 52%); MP: 248-249° C.; $^1$H-NMR (dmso, 400 MHz) δ 9.60 (s, 1H), 9.38 (br s, 1H), 9.15 (br s, 1H), 8.32 (s, 1H), 7.50 (d, J=8.3 Hz, 1H), 7.32 (d, J=8.5 Hz, 1H), 6.70 (s, 1H), 6.53-6.48 (m, 2H), 3.80-3.78 (m, 4H), 3.77 (s, 3H), 3.70 (s, 3H), 3.25-3.19 (m, 6H), 2.70-2.68 (m 2H), 2.14-2.10 (m, 2H); LC/MS: 525.36 (M+H).

Example 141

7-[5-Chloro-4-(2-methoxy-4-morpholin-4-yl-phenylamino)-pyrimidin-2-ylamino]-1-ethyl-6-methoxy-3,3-dimethyl-1,3,4,5-tetrahydro-benzo[b]azepin-2-one 141a) 5-Methoxy-3,4-dihydro-2H-naphthalen-1-one (2.35 g, 13.3 mmol) in DMF (130 mL) was cooled to 0° C. in an ice bath, and to the solution was added NaH (60% in Silicon Oil) (1.60 g, 40.0 mmol). After 10 minutes of stirring at 0° C., Iodomethane (5.68 mg, 40.0 mmol) was added to the solution. After an additional 10 minutes, the reaction was allowed to warm to room temperature. Upon completion, the reaction was quenched with ice and water. The aqueous mixture was extracted 3× with diethyl ether, the organic layers were washed with brine, dried with MgSO₄, and concentrated to a yellow crude oil. Purified by ISCO chromatography to give the desired product 5-Methoxy-2,2-dimethyl-3,4-dihydro-2H-naphthalen-1-one (2.05 g, 75%), a clear oil. ¹H-NMR (CDCl₃) δ 7.65 (d, J=8.1 Hz, 1H), 7.27 (t, J=7.9 Hz, 1H), 7.00, (d, J=8.1 Hz, 1H), 3.87 (s, 3H), 2.88 (t, J=6.3 Hz, 2H), 1.96 (t, J=6.3 Hz, 2H), 1.20 (s, 6H); LC/MS (ESI-pos) m/z 205.08 (M+H).

141b) Following an analogous procedure to 130a-d, 5-Methoxy-2,2-dimethyl-3,4-dihydro-2H-naphthalen-1-one was converted to 7-Amino-1-ethyl-6-methoxy-3,3-dimethyl-1,3,4,5-tetrahydro-benzo[b]azepin-2-one (425 mg, 8%). ¹H-NMR (CDCl₃) δ 6.76 (d, J=8.6 Hz, 1H), 6.64 (d, J=8.6 Hz, 1H), 3.85 (br pk, 2H), 3.80 (br s, 2H), 3.76 (s, 3H), 2.73 (br s, 2H), 1.98 (br s, 2H), 1.14 (t, J=7.1 Hz, 3H), 0.95 (s, 6H); LC/MS (ESI-pos) m/z 263.18 (M+H).

141c) Following an analogous procedure to in Example 101b, 7-Amino-1-ethyl-6-methoxy-3,3-dimethyl-1,3,4,5-tetrahydro-benzo[b]azepin-2-one (110 mg, 0.419 mmol) and (2,5-Dichloro-pyrimidin-4-yl)-(2-methoxy-4-morpholin-4-yl-phenyl)-amine (135 mg, 0.380 mmol) were converted to 7-[5-Chloro-4-(2-methoxy-4-morpholin-4-yl-phenylamino)-pyrimidin-2-ylamino]-1-ethyl-6-methoxy-3,3-dimethyl-1,3,4,5-tetrahydro-benzo[b]azepin-2-one (80 mg, 36%), obtained by trituration in EtOAc. ¹H-NMR (DMSO) δ 8.24 (d, J=8.8 Hz, 1H), 8.20 (d, J=8.6 Hz, 1H), 8.05 (s, 1H), 7.56 (s, 1H), 7.37 (s, 1H), 6.89 (d, J=8.8 Hz, 1H), 6.55 (s, 1H), 6.51 (d, J=8.8 Hz, 1H), 3.92 (s, 3H), 3.90 (t, J=4.68 Hz, 4H), 3.79 (s, 3H), 3.7-4.0 (br pk, 2H), 3.16 (t, J=4.8 Hz, 4H), 2.78 (br m, 2H), 2.01 (br m, 2H), 1.17 (t, J=6.8 Hz, 3H), 0.97 (br s, 6H); LC/MS (ESI-pos) m/z 580.92 (M+H). M.P.=181-183° C.

Example 142

(2-exo, 3-exo)-3-[5-Chloro-2-(1-ethyl-6-methoxy-3,3-dimethyl-2-oxo-2,3,4,5-tetrahydro-1H-benzo[b]azepin-7-ylamino)-pyrimidin-4-ylamino]-bicyclo[2.2.1]hept-5-ene-2-carboxylic acid amide 142a) Following an analogous procedure to in Example 101b, 7-Amino-1-ethyl-6-methoxy-3,3-dimethyl-1,3,4,5-tetrahydro-benzo[b]azepin-2-one (110 mg, 0.419 mmol) and (2-exo,3-exo)-3-(2,5-Dichloro-pyrimidin-4-ylamino)-bicyclo[2.2.1]hept-5-ene-2-carboxylic acid amide (114 mg, 0.381 mmol) were converted to (2-exo,3-exo)-3-[5-Chloro-2-(1-ethyl-6-methoxy-3,3-dimethyl-2-oxo-2,3,4,5-tetrahydro-1H-benzo[b]azepin-7-ylamino)-pyrimidin-4-ylamino]-bicyclo[2.2.1]hept-5-ene-2-carboxylic acid amide (132 mg, 66%), purified by ISCO chromatography. ¹H-NMR (CDCl₃) δ 8.39 (d, J=8.8 Hz, 1H), 7.91 (s, 1H), 7.42 (s, 1H), 7.18 (d, J=7.8 Hz, 1H), 6.91 (d, J=8.8 Hz, 1H), 6.33 (br s, 2H), 5.87 (br s, 1H), 5.69 (br s, 1H), 4.34 (t, J=8.1 Hz, 1H), 3.91 (br m, 2H), 3.80 (s, 3H), 3.08 (s, 1H), 2.94 (s, 1H), 2.78 (br s, 2H), 2.53 (d, J=8.1 Hz, 1H), 2.24 (d, J=9.4 Hz, 1H), 2.01 (br s, 1H), 1.84 (br s, 1H), 1.63 (d, J=9.1 Hz, 1H), 1.16 (t, J=7.0 Hz, 3H), 0.96 (br s, 6H); LC/MS (ESI-pos) m/z 525.37 (M−H). M.P.=211-213° C.

Example 143

N-{(1R,2R)-2-[5-Chloro-2-(1-ethyl-6-methoxy-3,3-dimethyl-2-oxo-2,3,4,5-tetrahydro-1H-benzo[b]azepin-7-ylamino)-pyrimidin-4-ylamino]-cyclohexyl}-methanesulfonamide 143a) Following an analogous procedure to in Example 110b, 7-Amino-1-ethyl-6-methoxy-3,3-dimethyl-1,3,4,5-tetrahydro-benzo[b]azepin-2-one (110 mg, 0.419 mmol) and N-[(1R,2R)-2-(2,5-Dichloro-pyrimidin-4-ylamino)-cyclohexyl]-methanesulfonamide (129 mg, 0.380 mmol) were converted to N-{(1R,2R)-2-[5-Chloro-2-(1-ethyl-6-methoxy-3,3-dimethyl-2-oxo-2,3,4,5-tetrahydro-1H-benzo[b]azepin-7-ylamino)-pyrimidin-4-ylamino]-cyclohexyl}-methanesulfonamide (116 mg, 54%), purified by ISCO chromatography. ¹H-NMR (CDCl₃) δ 8.14 (d. J=8.8 Hz, 1H), 7.97 (s, 1H), 7.31 (s, 1H), 6.94 (d, J=8.8 Hz, 1H), 5.48 (d, J=7.1 Hz, 1H), 5.38 (d, J=6.6 Hz, 1H), 3.90 (br m, 3H), 3.80 (s, 3H), 3.23 (m, 1H), 2.81 (s, 5H), 2.21 (br s, 2H), 2.03 (br s, 2H), 1.84 (br s, 2H), 1.38 (m, 4H), 1.16 (t, J=6.8 Hz, 3H), 0.97 (br s, 6H); LC/MS (ESI-pos) m/z 565.34 (M+H). M.P.=123-126° C.

Example 144

2-[5-Chloro-2-(1-ethyl-6-methoxy-3,3-dimethyl-2-oxo-2,3,4,5-tetrahydro-1H-benzo[b]azepin-7-ylamino)-pyrimidin-4-ylamino]-N-methyl-benzamide 144a) Following an analogous procedure to in Example 101b, 7-Amino-1-ethyl-6-methoxy-3,3-dimethyl-1,3,4,5-tetrahydro-benzo[b]azepin-2-one (110 mg, 0.419 mmol) and 2-(2,5-Dichloro-pyrimidin-4-ylamino)-N-methyl-benzamide (113 mg, 0.380 mmol) were converted to -[5-Chloro-2-(1-ethyl-6-methoxy-3,3-dimethyl-2-oxo-2,3,4,5-tetrahydro-1H-benzo[b]azepin-7-ylamino)-pyrimidin-4-ylamino]-N-methyl-benzamide (26 mg, 13%), purified by ISCO chromatography, followed by recrystallization in a 1:1:5 ratio of DCM:EtOAc:Hexanes. ¹H-NMR (CDCl₃) δ 11.10 (s, 1H), 8.66 (d, J=8.6 Hz, 1H), 8.26 (d, J=8.8 Hz, 1H), 8.14 (s, 1H), 7.51 (d, J=7.6 Hz, 1H), 7.46 (t, J=7.8 Hz, 1H), 7.41 (s, 1H), 7.11 (t, J=7.4 Hz, 1H), 6.89 (d, J=8.8 Hz, 1H), 6.24 (br s, 1H), 3.92 (br m, 2H), 3.80 (s, 3H), 3.04 (d, J=4.6 Hz, 3H), 2.79 (br s, 2H), 2.03 (br s, 2H), 1.16 (t, J=6.8 Hz, 3H), 0.97 (br s, 6H); LC/MS (ESI-pos) m/z 523.35 (M+H). M.P.=226-228° C.

Example 145

5-Chloro-N*2*-[3-(2-methoxy-ethyl)-2,3,4,5-tetrahydro-1H-benzo[d]azepin-7-yl]-N*4*-(2-methoxyphenyl)-pyrimidine-2,4-diamine 145a) Analogous to procedure in Example 101b, 3-(2-Methoxy-ethyl)-2,3,4,5-tetrahydro-1H-benzo[d]azepin-7-ylamine (99 mg, 0.450 mmol) and (2,5-Dichloro-pyrimidin-4-yl)-(2-methoxy-phenyl)-amine [Prepared using an analogous procedure to Example 1d using 2,4,5-trichloropyrimidine and 2-methoxy-phenylamine] (121 mg, 0.450 mmol) were converted to 5-Chloro-N*2*-[3-(2-methoxy-ethyl)-2,3,4,5-tetrahydro-1H-benzo[d]azepin-7-yl]-N*4*-(2-methoxy-phenyl)-pyrimidine-2,4-diamine (150 mg, 74%), purified by ISCO chromatography. ¹H-NMR (CDCl₃) δ 8.44 (d, J=8.1 Hz, 1H), 8.05 (s, 1H), 7.85 (s, 1H), 7.38 (s, 1H), 7.23 (d, J=8.1 Hz, 1H), 7.05 (m, 2H), 6.95 (t, J=8.1 Hz, 2H), 6.88 (s, 1H), 3.94 (s, 3H), 3.55 (br m, 2H), 3.37 (s, 3H), 2.91 (br s, 4H), 2.73 (br s, 2H); LC/MS (ESI-pos) m/z 454.25 (M+H). M.P.=126-128° C.

Example 146

5-Chloro-N*4*-(5-chloro-2-methoxy-phenyl)-N*2*-[3-(2-methoxy-ethyl)-2,3,4,5-tetrahydro-1H-benzo[d]azepin-7-yl]-pyrimidine-2,4-diamine 146a) Analogous to procedure in Example 101b, 3-(2-Methoxy-ethyl)-2,3,4,5-tetrahydro-1H-benzo[d]azepin-7-ylamine (112 mg, 0.508 mmol) and (5-Chloro-2-methoxyphenyl)-(2,5-dichloro-pyrimidin-4-yl)-amine (155 mg, 0.508 mmol) were converted to 5-Chloro-N*4*-(5-chloro-2-methoxy-phenyl)-N*2*-[3-(2-methoxy-ethyl)-2,3,4,5-tetrahydro-1H-benzo[d]azepin-7-yl]-pyrimidine-2,4-diamine (148 mg, 60%), purified by ISCO chromatography. $^1$H-NMR (CDCl$_3$) δ 8.48 (s, 1H), 8.06 (s, 1H), 7.86 (s, 1H), 7.40 (d, J=8.1 Hz, 1H), 7.15 (s, 1H), 7.12 (d, J=7.8 Hz, 1H), 6.99 (d, J=8.8 Hz, 1H), 6.88 (s, 1H), 6.82 (d, J=8.6 Hz, 1H), 3.93 (s, 3H), 3.54 (t, J=5.4 Hz, 2H), 3.36 (s, 3H), 2.91 (br s, 4H), 2.74 (br s, 6H); LC/MS (ESI-pos) m/z 488.19 (M+H). M.P.=164-165° C.

Example 151

N-{(1R,2R)-2-[5-Chloro-2-(1,3-diethyl-8-methoxy-2-oxo-2,3,4,5-tetrahydro-1H-benzo[d]azepin-7-ylamino)-pyrimidin-4-ylamino]-cyclohexyl-methanesulfonamide 151a) Charge NaH (60% dispersion in mineral oil) to 100 ml RBF and wash with hexanes. Charge 10 ml anhydrous DMF and 1-Ethyl-8-methoxy-1,3,4,5-tetrahydro-benzo[d]azepin-2-one (0.500 g, 2.28 mmol). Stir 10 minutes at room temperature and then charge iodoethane (900 uL, 10 mmol) dropwise with syringe. Allow to stir overnight. Pour reaction into 75 ml water and extract with 3×30 ml EtOAc. Dry combined organic over MgSO$_4$, filter and evaporated to yield 1,3-Diethyl-8-methoxy-1,3,4,5-tetrahydro-benzo[d]azepin-2-one. The crude product was used in the next step.

151b) 1,3-Diethyl-8-methoxy-1,3,4,5-tetrahydro-benzo[d]azepin-2-one (564 mg, 2.28 mmol) was dissolved in 1 ml of anhydrous MeCN. The reaction was cooled to 0° C. and trifluoroacetic anhydride (3.00 mL, 21.2 mmol) and Potassium nitrate (230 mg, 2.28 mmol) were charged. The reaction was stirred for 1.5 h and then the reaction was basified with 1-2 ml of 30% NaOH solution and allowed to stir for 1 h. Pour reaction into 75 ml water and extract with 3×30 ml portions of methylene chloride. Dry the combined organic over magnesium sulfate and evaporate. Product is a yellow brown oil (625 mg). Crude material was chromatographed on a 40 g Isco column using 30-50% EtOAc in hexanes as the eluent to yield 1,3-diethyl-8-methoxy-7-nitro-1,3,4,5-tetrahydro-benzo[d]azepin-2-one (205 mg, 31%) as a tan waxy solid as a mixture of diastereomers.

$^1$H-NMR (CDCl$_3$) δ 7.65 (s, 1H), 6.85 (s, 1H), 4.09-3.90 (m, 5H), 3.60-3.35 (m, 3H), 3.30-3.04 (m, 2H), 2.25 (p, J=7 Hz, 1H), 1.86 (p, J=7 Hz, 1H), 1.15-1.00 (m, 6H). LC/MS (ESI+): 293 (M+H)

151c) 1,3-Diethyl-8-methoxy-7-nitro-1,3,4,5-tetrahydro-benzo[d]azepin-2-one (205 mg, 0.70 mmol) was charged to 10 ml EtOH in a Parr bottle and then 50 mg of 10% Pd/C was also charged. The resulting suspension was shaken under 40 psi hydrogen (g) for 2 h. The resulting suspension was filtered through celite and evaporated to yield 7-amino-1,3-diethyl-8-methoxy-1,3,4,5-tetrahydro-3-benzazepin-2-one (170 mg, 93%) which was used crude in the next reaction. $^1$H-NMR (CDCl$_3$) δ 6.58 (s, 1H), 6.44 (s, 1H), 3.92-3.77 (m, 5H), 3.70-3.40 (br s, 1H), 3.58-3.38 (m, 3H), 3.09 (p, J=7 Hz, 1H), 2.95 (p, J=7 Hz, 1H), 2.20 (p, J=7 Hz, 1H), 1.90 (p, J=7 Hz, 1H), 1.10 (t, J=7 Hz, 3H), 1.04 (t, J=7 Hz, 3H); LC/Ms (ESI+): 263 (M+H).

151d) 7-Amino-1,3-diethyl-8-methoxy-1,3,4,5-tetrahydro-3-benzazepin-2-one (85 mg, 0.32 mmol), N-[(1R,2R)-2-(2,5-dichloro-pyrimidin-4-ylamino)-cyclohexyl]-methanesulfonamide (120 mg, 0.36 mmol), and 10-camphorsulfonic acid (82.5 mg, 0.355 mmol) were charged to isopropyl alcohol (3 ml, 40 mmol) in a microwave reaction tube. The reaction was heated in microwave at 120° C. for 40 minutes. The resulting solution was poured into a mixture of 20 ml saturated sodium bicarbonate solution and 40 ml water and the aqueous solution was extracted with methylene chloride (4×10 ml portions). The combined organic extracts were dried over magnesium sulfate, filtered and evaporated under reduced pressure to yield a clear yellow oil. The oil was evaporated onto celite and the celite placed on silica gel (12 g Isco column) and eluted with 0-70% EtOAc in Hexanes to obtain N-{(1R,2R)-2-[5-Chloro-2-(1,3-diethyl-8-methoxy-2-oxo-2,3,4,5-tetrahydro-1H-benzo[d]azepin-7-ylamino)-pyrimidin-4-ylamino]-cyclohexyl}-methanesulfonamide as a beige powder. MP: 126-127° C.; $^1$H-NMR (CDCl$_3$) δ 8.01 (d, J=7.1 Hz, 1H), 7.35 (s, 1H), 6.72 (s, 1H), 5.35 (d, J=7.8 Hz, 1H), 5.29 (d, J=7.8 Hz, 1H), 4.00-3.82 (m, 5H), 3.57 (p, J=7 Hz, 1H), 3.45 (m, 2H), 3.28-3.07 (m, 3H), 2.80 (d, J=2.8 Hz, 3H), 2.30-2.10 (m, 3H), 1.98-1.80 (m, 3H), 1.47-1.30 (m, 4H), 1.10 (t, J=7 Hz, 3H), 1.03 (t, J=7 Hz, 3H); LC/MS (ESI+): 565 (M+H).

Example 152

2-[5-Chloro-2-(1,3-diethyl-6-methoxy-2-oxo-2,3,4,5-tetrahydro-1H-benzo[d]azepin-7-ylamino)-pyrimidin-4-ylamino]-N-methyl-benzamide 152a) Prepared in the same manner as Example 151 from 7-amino-1,3-diethyl-6-methoxy-1,3,4,5-tetrahydro-3-benzazepin-2-one (85 mg, 0.32 mmol) and 2-(2,5-dichloro-pyrimidin-4-ylamino)-N-methyl-benzamide (100 mg, 0.36 mmol) to yield 2-[5-Chloro-2-(1,3-diethyl-6-methoxy-2-oxo-2,3,4,5-tetrahydro-1H-benzo[d]azepin-7-ylamino)-pyrimidin-4-ylamino]-N-methyl-benzamide as a yellow powder. MP: 157-158° C.; $^1$H-NMR (CDCl$_3$) δ 11.01 (s, 1H), 8.65 (d, J=8.6 Hz, 1H), 8.09 (d, J=17.3 Hz, 2H), 7.50-7.35 (m, 3H), 7.08 (t, J=7.8 Hz, 1H), 6.69 (s, 1H), 6.28 (br s, 1H), 3.96-3.80 (m, 5H), 3.60-3.40 (m, 4H), 3.12-2.91 (m, 5H), 2.21 (p, J=7 Hz, 1H), 1.90 (p, J=7 Hz, 1H), 1.09 (m, 6H); LC/MS (ESI+): 523 (M+H).

Example 153

5-Chloro-N*2*-(3-ethyl-2,3,4,5-tetrahydro-1H-benzo[d]azepin-7-yl)-N*4*-prop-2-ynyl-pyrimidine-2,4-diamine 153a) 2,4,5-Trichloropyrimidine (500 mg, 2.7 mmol), propargyl amine (149 mg, 2.7 mmol), and potassium carbonate (373 mg, 2.7 mmol) were combined in a 30 ml reaction vial with 5 ml THF and stirred at room temperature overnight. The reaction was poured into 50 ml water and extracted with EtOAc (3×20 ml). The combined organic was dried over magnesium sulfate, filtered and concentrated under reduced pressure to yield (2,5-dichloro-pyrimidin-4-yl)-prop-2-ynyl-amine (488 mg, 90%) as a yellow oil that crystallizes upon standing. This was used crude in the next reaction.

153b) 3-Ethyl-2,3,4,5-tetrahydro-1H-benzo[d]azepin-7-ylamine (50 mg, 0.263 mmol) and (2,5-dichloro-pyrimidin-4-yl)-prop-2-ynyl-amine (53 mg, 0.263 mmol) were heated in 0.5 ml methoxyethanol to 110° C. in a sealed tube overnight. The resulting solution was poured into a mixture of 20 ml saturated sodium bicarbonate solution and 40 ml water and the aqueous solution was extracted with methylene chloride (4×10 ml portions). The combined organic extracts were dried over magnesium sulfate, filtered and evaporated under reduced pressure to a brown oil. The brown oil was purified via reverse phase chromatography on a C-18 (Higgins Analytical Clipeus) column using a 5-90% gradient of acetonitrile/0.1% TFA in water/0.1% TFA to yield 5-Chloro-N*2*-(3-ethyl-2,3,4,5-tetrahydro-1H-benzo[d]azepin-7-yl)-N*4*-prop-2-ynyl-pyrimidine-2,4-diamine TFA salt as a white powder. MP: 201-202° C.; $^1$H-NMR (dmso-$d_6$) δ 9.50 (s, 2H), 8.05 (s, 1H), 8.82 (br s, 1H), 8.72 (s, 1H), 7.5 (d, J=7.2 Hz, 1H), 7.09 (d, J=7.2 Hz, 1H), 4.18 (s, 2H), 1.65 (br s, 2H), 3.25-2.85 (m, 8H), 1.25 (t, J=7 Hz, 3H); LC/MS (ESI+): 356 (M+H of free base).

Example 154

2-[5-Chloro-2-(3-ethyl-9-methoxy-2,3,4,5-tetrahydro-1H-benzo[d]azepin-6-ylamino)-pyrimidin-4-ylamino]-N-methyl-benzamide 154a) Charge 3-ethyl-6-methoxy-9-nitro-2,3,4,5-tetrahydro-1H-benzo[d]azepine (321 mg, 1.28 mmol) and 200 mg 10% Pd/C to 10 ml EtOH in a Parr bottle. Hydrogenate on Parr shaker at 20-30 psi hydrogen (g) overnight. Filter the reaction through ¼" celite plug and evaporate ethanol. The residue was taken up in ethyl Acetate (50 ml) and washed with water (2×20 ml portions). The organic was dried over magnesium sulfate, filtered and evaporated. Pre treat a Phenomenex Strata cationic column with two 10 to 20 ml portions of methanol. Filter water layer through a Phenomenex acid cartridge. The 3-ethyl-9-methoxy-2,3,4,5-tetrahydro-1H-benzo[d]azepin-6-ylamine (100 mg, 40%) was eluted from the cartridge with ammonia in methanol. $^1$H-NMR (CDCl$_3$) δ 6.65 (d, J=8.6 Hz, 1H), 6.58 (d, J=8.6 Hz, 1H), 3.73 (s, 3H), 3.04 (m, 2H), 2.87 (m, 2H), 2.66-2.50 (m, 6H), 1.10 (t, J=7.3, 3H).

154b) 3-Ethyl-9-methoxy-2,3,4,5-tetrahydro-1H-benzo[d]azepin-6-ylamine (50.01 mg, 0.2270 mmol), 2-(2,5-Dichloro-pyrimidin-4-ylamino)-N-methyl-benzamide (67.4 mg, 0.227 mmol) and 10-camphorsulfonic acid (79.1 mg, 0.340 mmol) were charged to 2 ml IPA in a microwave tube. The reaction was heated to at 120° C. for 40 minutes. Pour reaction into water (50 ml) and saturated sodium bicarb (90 ml) and extract 3 times with 25 ml portions of methylene chloride. Dry combined organic over magnesium sulfate, filter and evaporate to a brown oil (102 mg). The crude reaction was purified on silica gel (12 g Isco column) using a gradient of 0-10% methanol in methylene chloride and then isocratic 20% methanol in methylene chloride to yield 2-[5-Chloro-2-(3-ethyl-9-methoxy-2,3,4,5-tetrahydro-1H-benzo[d]azepin-6-ylamino)-pyrimidin-4-ylamino]-N-methyl-benzamide as a beige foam. $^1$H-NMR (CDCl$_3$) δ 11.10 (br s, 1H), 8.42 (br s, 1H), 8.02 (s, 1H), 7.40 (d, J=7.6 Hz, 1H), 7.15 (d, J=8.6 Hz, 1H), 6.95 (m, 1H), 6.77 (d, J=8.6 Hz, 1H), 6.43 (s, 1H), 3.89 (s, 3H), 3.12 (br s, 1H), 3.03 (d, J=4.8 Hz, 3H), 2.93 (br s, 1H), 2.60-2.41 (m, 6H), 1.00 (m, 3H).

Example 155

N-{(1R,2R)-2-[5-Chloro-2-(3-ethyl-9-methoxy-2,3,4,5-tetrahydro-1H-benzo[d]azepin-6-ylamino)-pyrimidin-4-ylamino]-cyclohexyl}-methanesulfonamide 155a) 3-Ethyl-9-methoxy-2,3,4,5-tetrahydro-1H-benzo[d]azepin-6-ylamine (50.01 mg, 0.2270 mmol), N-[(1R,2R)-2-(2,5-Dichloro-pyrimidin-4-ylamino)-cyclohexyl]-methanesulfonamide (77.0 mg, 0.227 mmol) and 10-camphorsulfonic acid (79.1 mg, 0.340 mmol) were charged to 2 ml IPA in a microwave tube. The reaction was heated to at 120° C. for 40 minutes. Pour reaction into water (50 ml) and saturated sodium bicarb (90 ml) and extract 3 times with 25 ml portions of methylene chloride. Dry combined organic over magnesium sulfate, filter and evaporate to a brown oil (87 mg). The crude reaction was purified on silica gel (12 g Isco column) using a gradient of 0-20% methanol in methylene chloride and then isocratic 20% methanol in methylene chloride to yield N-{(1R,2R)-2-[5-Chloro-2-(3-ethyl-9-methoxy-2,3,4,5-tetrahydro-1H-benzo[d]azepin-6-ylamino)-pyrimidin-4-ylamino]-cyclohexyl}-methanesulfonamide as an off white foam. $^1$H-NMR (CDCl$_3$) δ 7.88 (s, 1H), 7.11 (d, J=8.6 Hz, 1H), 6.78 (d, J=8.6 Hz, 1H), 6.38 (s, 1H), 5.18 (br s, 1H), 3.81 (s, 3H), 3.10 (br s, 2H), 2.72 (s, 3H), 2.68-2.49 (m, 6H), 2.18-2.00 (m, 2H), 1.82-1.69 (m, 2H), 1.40-1.18 (m, 4H), 1.07 (t, J=7 Hz, 3H).

Example 156

2-[5-Chloro-2-(10-ethyl-10-aza-tricyclo[6.3.1.0*2,7*]dodeca-2,4,6-trien-4-ylamino)-pyrimidin-4-ylamino]-N-methyl-benzamide 156a) To a solution of 4-nitro-10-aza-tricyclo[6.3.1.0*2,7*]dodeca-2,4,6-triene (300 mg, 1.47 mmol) (prepared using the procedure detailed in *J. Med Chem*, 2005, 48, 3474-3477) in 5 ml acetone was added potassium carbonate (609 mg, 4.41 mmol) and then ethyl iodide (423 μl, 5.29 mmol). The solution was allowed to stir overnight. The reaction was evaporated under reduced pressure and partitioned between water and EtOAc. The water layer was extracted with 2×10 ml portions of EtOAc and the combined organics dried over magnesium sulfate, filtered and evaporated. The resulting brown oil was chromatographed on a 12 g Isco column using a gradient of 0-10% methanol in methylene chloride to yield 10-ethyl-4-nitro-10-aza-tricyclo[6.3.1.0*2,7*]dodeca-2,4,6-triene (280 mg, 82%) as a brown oil. $^1$H-NMR (CDCl$_3$) δ 8.07 (d, J=8.1 Hz, 1H), 7.96 (s, 1H), 7.24 (d, J=8.1 Hz, 1H), 3.17 (dd, J=5.5, 4.8 Hz, 2H), 2.87 (dd, J=5.5, 4.8 Hz, 2H); 2.40-2.20 (m, 5H), 1.75 (d, J=10.6 Hz), 0.85 (d, J=10.6 Hz, 3H).

156b) 10-ethyl-4-nitro-10-aza-tricyclo[6.3.1.0*2,7*]dodeca-2,4,6-triene (280 mg, 1.20 mmol) in 10 ml EtOH in a Parr bottle was treated with 50 mg 10% Pd/C and subjected to hydrogen (g) at 40 psi for 2 h. The suspension was filtered and the solvent removed under reduced pressure to yield 10-ethyl-10-aza-tricyclo[6.3.1.0*2,7*]dodeca-2,4,6-trien-4-ylamine (239 mg, 98%).

156c) 10-ethyl-10-aza-tricyclo[6.3.1.0*2,7*]dodeca-2,4,6-trien-4-ylamine (75 mg, 0.37 mmol), 2-(2,5-dichloro-pyrimidin-4-ylamino)-N-methyl-benzamide (120 mg, 0.41 mmol) and 4N HCl in dioxane (275 μl, 0.41 mmol) were combined in a microwave tube. The reaction was heated to at 120° C. for 40 minutes in the microwave. The reaction was poured into water (50 ml) and saturated sodium bicarb (90 ml) and extracted 3 times with 25 ml portions of methylene chloride. The combined organic was dried over magnesium sulfate, filtered and evaporated to a brown oil (87 mg). The crude reaction was purified on a 80 g Isco basic alumina column using 0-2% methanol in methylene chloride as the eluent to yield 2-[5-Chloro-2-(10-ethyl-10-aza-tricyclo[6.3.1.0*2,7*]dodeca-2,4,6-trien-4-ylamino)-pyrimidin-4-ylamino]-N-methyl-benzamide (133 mg, 78%) as a beige powder. MP: 220° dec.; $^1$H-NMR (CDCl$_3$) δ 10.97 (s, 1H), 8.66 (d, J=8.3, 1H), 8.09 (s, 1H), 7.50-7.38 (m, 3H), 7.21 (d, J=5 Hz, 1H), 7.08 (m, 2H), 6.91 (s, 1H), 6.20 (br s, 1H), 3.12-2.95 (m, 5H), 2.87 (br, s), 2.45-2.20 (m, 6H), 1.69 (d, J=10.1 Hz, 2H), 0.90 (t, J=7.1 Hz, 3H).

Example 157

2-[5-Chloro-2-(10-ethyl-10-aza-tricyclo[6.3.1.0*2,7*]dodeca-2,4,6-trien-4-ylamino)-pyrimidin-4-ylamino]-N-methyl-benzenesulfonamide 157a) 10-ethyl-10-aza-tricyclo[6.3.1.0*2,7*]dodeca-2,4,6-trien-4-ylamine (75 mg, 0.37 mmol), 22-(2,5-Dichloro-pyrimidin-4-ylamino)-N-methyl-benzenesulfonamide (136 mg, 0.41 mmol) and 4N HCl in dioxane (275 µl, 0.41 mmol) were combined in a microwave tube. The reaction was heated to at 120° C. for 40 minutes in the microwave. The reaction was poured into water (50 ml) and saturated sodium bicarb (90 ml) and extracted 3 times with 25 ml portions of methylene chloride. The combined organic was dried over magnesium sulfate, filtered and evaporated to a brown oil. The crude reaction was purified on a 80 g Isco basic alumina column using 0-2% methanol in methylene chloride as the eluent to yield 2-[5-Chloro-2-(10-ethyl-10-aza-tricyclo[6.3.1.0*2,7*]dodeca-2,4,6-trien-4-ylamino)-pyrimidin-4-ylamino]-N-methyl-benzenesulfonamide (158.59 mg, 86%) as an off white powder. MP: 143° C.; $^1$H-NMR (CDCl$_3$) δ 9.10 (s, 1H); 8.49 (d, J=8.3 Hz, 1H), 8.06 (s, 1H), 7.93 (d, J=7.8 Hz, 1H), 7.54 (t, J=7.8 Hz, 1H), 7.30 (d, J=7.1 Hz, 1H), 7.21 (d, J=7.1 Hz, 1H), 7.06 (d, J=6.7 Hz, 2H), 4.95 (br s, 1H), 3.06 (d, J=21.7 Hz, 2H), 2.88 (t, J=11.4 Hz, 2H), 2.61 (s, 3H), 2.48-2.20 (m, 5H), 1.70 (d, J=10.4 Hz, 1H), 0.85 (d, J=7 Hz, 6H); LC/MS (ESI+): 499 (M+H)

Example 158

2-[5-chloro-2-(10-isopropyl-10-aza-tricyclo[6.3.1.0*2,7*]dodeca-2,4,6-trien-4-ylamino)-pyrimidin-4-ylamino]-N-methyl-benzamide 158a) To a solution of 10-isopropyl-4-nitro-10-aza-tricyclo[6.3.1.0*2,7*]dodeca-2,4,6-triene (200 mg, 0.98 mmol) in 5 ml acetone was added potassium carbonate (406 mg, 2.94 mmol) and then isopropyl iodide (117 µl, 1.17 mmol). The solution was allowed to stir overnight. The reaction was evaporated under reduced pressure and partitioned between water and EtOAc. The water layer was extracted with 2×10 ml portions of EtOAc and the combined organics dried over magnesium sulfate, filtered and evaporated. The resulting brown oil was chromatographed on a 12 g Isco column using a gradient of 0-2% methanol in methylene chloride to yield 10-isopropyl-4-nitro-10-aza-tricyclo[6.3.1.0*2,7*]dodeca-2,4,6-triene (75.07 mg, 31%) as a brown oil. $^1$H-NMR (CDCl$_3$) δ 8.07 (d, J=7.8 Hz, 1H), 7.95 (s, 1H), 7.21 (d, J=8.1 Hz, 1H), 3.18 (d, J=11.4 Hz, 2H), 2.80-2.71 (m, 2H), 2.63 (d, J=9.6 Hz, 2H), 2.55 (p, J=6.6 Hz, 1H), 2.35-2.25 (m, 1H), 1.75 (d, 10.6 Hz, 1H), 0.85 (d, J=5.7 Hz, 6H).

158b) 10-Isopropyl-4-nitro-10-aza-tricyclo[6.3.1.0*2,7*]dodeca-2,4,6-triene (75 mg, 0.30 mmol) in 10 ml EtOH in a Parr bottle was treated with 50 mg 10% Pd/C and subjected to hydrogen (g) at 40 psi for 2 h. The suspension was filtered and the solvent removed under reduced pressure to yield 10-isopropyl-10-aza-tricyclo[6.3.1.0*2,7*]dodeca-2,4,6-trien-4-ylamine (239 mg, 98%). LC/MS (ESI+): 217 (M+H).

158c) 10-Isopropy-10-aza-tricyclo[6.3.1.0*2,7*]dodeca-2,4,6-trien-4-ylamine (30 mg, 0.14 mmol), 2-(2,5-dichloro-pyrimidin-4-ylamino)-N-methyl-benzamide (41 mg, 0.14 mmol) and 4N HCl in dioxane (28 µl, 0.15 mmol) were combined in a microwave tube. The reaction was heated to at 120° C. for 40 minutes in the microwave. The reaction was poured into water (50 ml) and saturated sodium bicarb (90 ml) and extracted 3 times with 25 ml portions of methylene chloride. The combined organic was dried over magnesium sulfate, filtered and evaporated to a brown oil. The crude reaction was purified on a 8 g Isco basic alumina column using 0-2% methanol in methylene chloride as the eluent to yield 2-[5-chloro-2-(10-isopropyl-10-aza-tricyclo[6.3.1.0*2,7*]dodeca-2,4,6-trien-4-ylamino)-pyrimidin-4-ylamino]-N-methyl-benzamide (23.2 mg, 35%) as a red orange foam. $^1$H-NMR (CDCl$_3$) δ 11.0 (s, 1H), 8.68 (d, J=8.3 Hz, 1H), 8.08 (s, 1H), 7.48 (d, J=7.8 Hz, 1H), 7.40 (t, J=7.3 Hz, 1H), 7.37 (s, 1H), 7.21 (s, 1H), 7.06 (dd, J=3.3, 6.8 Hz, 2H), 3.10-3.0 (m, 4H), 2.75 (m, 2H), 2.55 (m, 4H), 2.27 (m, 1H), 1.68 (d, J=10.1 Hz, 1H), 0.85 (d, J=6.6 Hz, 6H); LC/MS (ESI+): 477 (M+H).

Example 159

2-[5-Chloro-2-(10-isopropyl-10-aza-tricyclo[6.3.1.0*2,7*]dodeca-2,4,6-trien-4-ylamino)-pyrimidin-4-ylamino]-N-methyl-benzenesulfonamide 159a) 10-Isopropy-10-aza-tricyclo[6.3.1.0*2,7*]dodeca-2,4,6-trien-4-ylamine (30 mg, 0.14 mmol), 2-(2,5-dichloro-pyrimidin-4-ylamino)-N-methyl-benzenesulfonamide (45 mg, 0.14 mmol) and 4N HCl in dioxane (28 µl, 0.15 mmol) were combined in a microwave tube. The reaction was heated to at 120° C. for 40 minutes in the microwave. The reaction was poured into water (50 ml) and saturated sodium bicarb (90 ml) and extracted 3 times with 25 ml portions of methylene chloride. The combined organic was dried over magnesium sulfate, filtered and evaporated to a brown oil. The crude reaction was purified on a 8 g Isco basic alumina column using 0-2% methanol in methylene chloride as the eluent to yield 2-[5-Chloro-2-(10-isopropyl-10-aza-tricyclo[6.3.1.0*2,7*]dodeca-2,4,6-trien-4-ylamino)-pyrimidin-4-ylamino]-N-methyl-benzenesulfonamide (14.85 mg, 20%) as a beige foam. $^1$H-NMR (CDCl$_3$) δ 9.08 (s, 1H), 8.51 (d, J=7.8 Hz, 1H), 8.13 (s, 1H), 7.95 (d, J=7.8 Hz, 1H), 7.55 (t, J=7.8 Hz, 1H), 7.30 (s, 1H), 7.21 (m, 2H), 7.08 (d, J=7.8 Hz), 6.93 (s, 1H), 4.52 (d, J=2 Hz, 1H), 3.08 (br s, 1H), (3.02 br s, 1H), 2.71 (m, 2H), 2.63 (d, J=5.3 Hz, 3H), 2.56 (m, 3H), 2.30-2.20 (m, 1H), 1.67 (d, J=11.0 Hz, 1H), 0.87 (q, J=1.8, 6.6 Hz, 6H); LC/MS (ESI+): 513 (M+H).

Example 160

(2-exo,3-exo)-3-[5-Chloro-2-(10-ethyl-10-aza-tricyclo[6.3.1.0*2,7*]dodeca-2,4,6-trien-4-ylamino)-pyrimidin-4-ylamino]-bicyclo[2.2.1]hept-5-ene-2-carboxylic acid amide 160a) 10-Ethyl-10-aza-tricyclo[6.3.1.0*2,7*]dodeca-2,4,6-trien-4-ylamine (45 mg, 0.22 mmol), 3-(2,5-Dichloro-pyrimidin-4-ylamino)-bicyclo[2.2.1]hept-5-ene-2-carboxylic acid amide (73 mg, 0.24 mmol) and 4N HCl in dioxane (60 µl, 0.24 mmol) were combined in a microwave tube. The reaction was heated to at 120° C. for 40 minutes in the microwave. The reaction was poured into water (50 ml) and saturated sodium bicarb (90 ml) and extracted 3 times with 25 ml portions of methylene chloride. The combined organic was dried over magnesium sulfate, filtered and evaporated to a brown oil. The crude reaction was purified on a 12 g Isco silica gel column using 0-20% methanol in methylene chloride as the eluent to yield (2-exo,3-exo)-3-[5-Chloro-2-(10-ethyl-10-aza-tricyclo[6.3.1.0*2,7*]dodeca-2,4,6-trien-4-ylamino)-pyrimidin-4-ylamino]-bicyclo[2.2.1]hept-5-ene-2-carboxylic acid amide (59.61 mg, 58%) as a white powder as a mixture of diastereomers. MP: 163-164° C.; Unseparated mixture of stereoisomers $^1$H-NMR (CDCl$_3$) δ 7.87 (s, 1H), 7.49

(s, 0.5H), 7.36 (d, J=13.4 Hz, 0.5H), 7.32 (s, 0.5H), 7.21 (d, J=7.7 HZ, 0.5H), 7.09 (d, J=7.7 Hz, 1H), 6.89 (s, 1H), 6.62 (d, J=8.9 Hz, 0.5H), 6.36 (d, J=7.6 Hz, 0.5H), 6.29 (m, 2H0, 5.85 (br s, 0.5H), 5.58 (br s, 0.5H), 5.37 (br s, 0.5H), 5.24 (br s), 4.38 (q, J=13.8, 7.4 Hz, 1H), 3.5 q (13.4, 7.1 Hz, 1H), 3.09 (br s, 3.09, 2H), 3.04 (s, 1H), 2.38 (s, 3H), 2.47-2.30 (M, 7H), 1.60-1.45 (m, 2H), 1.28-1.95 (m, 2H), 0.98-0.83 (M, 3H). LC/MS (ESI+): 465 (M+H).

Example 161

2-{5-Chloro-2-[10-(2-methoxy-ethyl)-10-aza-tricyclo[6.3.1.0*2,7*]dodeca-2,4,6-trien-4-ylamino]-pyrimidin-4-ylamino}-N-methyl-benzamide 161a) To a solution of 10-(2-methoxy-ethyl)-4-nitro-10-aza-tricyclo[6.3.1.0*2,7*]dodeca-2,4,6-triene (100 mg, 0.49 mmol) in 5 ml acetone was added cesium carbonate (479 mg, 1.47 mmol) and then 2-bromomethoxy ethane (117 µl, 1.17 mmol). The solution was allowed to stir overnight. The reaction was evaporated under reduced pressure and partitioned between water and EtOAc. The water layer was extracted with 2×10 ml portions of EtOAc and the combined organics dried over magnesium sulfate, filtered and evaporated to yield 10-(2-methoxy-ethyl)-4-nitro-10-aza-tricyclo[6.3.1.0*2,7*]dodeca-2,4,6-triene (109 mg, 85%) as a yellow oil. Product used crude for next reaction. 1H-NMR (CDCl$_3$) δ 8.08 (d, J=8.1 Hz, 1H), 7.98 (s, 1H), 7.24 (d, J=7.8 Hz, 1H), 3.32 (t, J=5.8 Hz, 2H), 3.19 (s, 5H), 2.91 (br s, 2H), 2.61-2.49 (m, 4H), 2.30 (m, 1H), 1.8 (d, J=10.6 Hz, 1H); LC/MS (ESI+): 263 (M+H)

161b) 10-(2-Methoxy-ethyl)-4-nitro-10-aza-tricyclo[6.3.1.0*2,7*]dodeca-2,4,6-triene (75 mg, 0.30 mmol) in 8 ml EtOH and 2 ml methylene chloride in a Parr bottle was treated with 50 mg 10% Pd/C and subjected to hydrogen (g) at 40 psi for 2 h. The suspension was filtered and the solvent removed under reduced pressure to yield 10-(2-methoxy-ethyl)-10-aza-tricyclo[6.3.1.0*2,7*]dodeca-2,4,6-trien-4-ylamine (99 mg, 85%). LC/MS (ESI+): 233 (M+H)

161c) 10-(2-Methoxy-ethyl)-10-aza-tricyclo[6.3.1.0*2,7*]dodeca-2,4,6-trien-4-ylamine (45 mg, 0.19 mmol), 2-(2,5-dichloro-pyrimidin-4-ylamino)-N-methyl-benzamide (58 mg, 0.19 mmol) and 4N HCl in dioxane (53 µl, 0.21 mmol) were combined in a microwave tube. The reaction was heated to at 120° C. for 40 minutes in the microwave. The reaction was poured into water (50 ml) and saturated sodium bicarb (90 ml) and extracted 3 times with 25 ml portions of methylene chloride. The combined organic was dried over magnesium sulfate, filtered and evaporated to a brown oil. The crude reaction was purified on a 12 g Isco silica gel column using 0-15% methanol in methylene chloride as the eluent to yield 2-[5-Chloro-2-(10-(2-methoxy-ethyl)-10-aza-tricyclo[6.3.1.0*2,7*]dodeca-2,4,6-trien-4-ylamino)-pyrimidin-4-ylamino]-N-methyl-benzamide (43.6 mg, 43%) as a yellow foam. MP: 104.5-105.5° C.; $^1$H-NMR (CDCl$_3$) δ 9.68 (d, J=7.8 Hz, 1H), 8.12 (s, 1H), 7.49 (d, J=7.8 Hz, 1H), 7.42 (m, 2H), 7.21 (s, 1H), 7.08 (d, J=8.1 Hz, 2H), 6.91 (s, 1H), 6.20 (br s, 1H), 3.33 (t, J=5.8 Hz, 2H), 3.20 (s, 3H), 3.11-2.98 (m, 6H), 2.86 (br s, 2H), 2.59-2.46 (m, 4H), 2.39 (m, 1H), 1.73 (d, J=10.36, 1H); LC/MS (ESI+): 493 (M+H).

Example 162

2-{5-Chloro-2-[10-(2-methoxy-ethyl)-10-aza-tricyclo[6.3.1.0*2,7*]dodeca-2,4,6-trien-4-ylamino]-pyrimidin-4-ylamino}-N-methyl-benzenesulfonamide 162a) 10-(2-Methoxy-ethyl)-10-aza-tricyclo[6.3.1.0*2,7*]dodeca-2,4,6-trien-4-ylamine (45 mg, 0.19 mmol), 2-(2,5-dichloro-pyrimidin-4-ylamino)-N-methyl-benzenesulfonamide (65 mg, 0.19 mmol) and 4N HCl in dioxane (53 µl, 0.21 mmol) were combined in a microwave tube. The reaction was heated to at 120° C. for 40 minutes in the microwave. The reaction was poured into water (50 ml) and saturated sodium bicarb (90 ml) and extracted 3 times with 25 ml portions of methylene chloride. The combined organic was dried over magnesium sulfate, filtered and evaporated to a brown oil. The crude reaction was purified on a 12 g Isco silica gel column using 0-15% methanol in methylene chloride as the eluent to yield 2-[5-chloro-2-(10-(2-methoxy-ethyl)-10-aza-tricyclo[6.3.1.0*2,7*]dodeca-2,4,6-trien-4-ylamino)-pyrimidin-4-ylamino]-N-methyl-benzenesulfonamide (52.57 mg, 43%) as a white foam. MP: 92-94° C., $^1$H-NMR (CDCl$_3$) δ 9.10 (s, 1H), 8.50 (d, J=7.5 Hz, 1H), 8.13 (s, 1H), 7.96 (d, J=7.8 Hz, 1H), 7.58 (m, 1H), 7.35 (s, 1H), 7.21 (d, J=7.8 Hz, 1H), 7.08 (d, J=7.8 Hz, 1H), 6.95 (s, 1H), 4.61-4.53 (m, 1H), 3.36 (t, J=5.9 Hz, 2H), 3.29 (s, 3H), 3.08 (br s, 1H), 3.02 (br s, 1H), 2.85 (m, 2H), 2.64 (d, J=5.3 Hz, 3H), 2.57-2.45 (m, 4H), 2.27 (m, 1H), 1.71 (d, J=10.1 Hz, 1H).

Example 163

2-[5-Chloro-2-(10-methanesulfonyl-10-aza-tricyclo[6.3.1.0*2,7*]dodeca-2,4,6-trien-4-ylamino)-pyrimidin-4-ylamino]-N-methyl-benzenesulfonamide 163a) In a 30 ml reaction vial 4-nitro-10-aza-tricyclo[6.3.1.0*2,7*]dodeca-2,4,6-triene (195 mg, 0.955 mmol), Triethylamine (0.40 mL, 2.9 mmol) were charged to methylene chloride (10 mL, 200 mmol). The reaction was cooled to 0° C. and the methanesulfonyl chloride (81 uL, 1.0 mmol) added dropwise with a syringe. The reaction was allowed to stir at 0° C. for 30 minutes. The reaction was poured into water (20 ml) and saturated sodium bicarbonate solution (20 ml) and the layers separated. The aqueous was washed with another 2×10 ml portions of methylene chloride. The combined organic was dried over magnesium sulfate, filtered and evaporated to yield 10-methanesulfonyl-4-nitro-10-aza tricycle[6.3.1.0*2,7*]dodeca-2,4,6-triene (170 mg, 63%) as a brown oil that was used crude in the next reaction. $^1$H-NMR (CDCl$_3$) δ 8.17 (d, J=6.1 Hz, 1H), 8.13 (s, 1H), 7.39 (d, J=8.1 Hz, 1H), 3.77-3.68 (m, 2H), 3.41-3.28 (m, 4H), 2.52-2.42 (m, 1H), 2.30 (s, 3H), 1.92 (d, J=11.1 Hz), LC/MS (ESI+): 283 (M+H).

163b) 10-methanesulfonyl-4-nitro-10-aza-tricyclo[6.3.1.0*2,7*]dodeca-2,4,6-triene (170 mg, 0.60 mmol) in 8 ml EtOH and 2 ml methylene chloride in a Parr bottle was treated with 50 mg 10% Pd/C and subjected to hydrogen (g) at 40 psi for 2 h. The suspension was filtered and the solvent removed under reduced pressure to yield 10-methanesulfonyl-10-aza-tricyclo[6.3.1.0*2,7*]dodeca-2,4,6-trien-4-ylamine (157 mg, 99%). $^1$H-NMR (CDCl$_3$) δ 7.03, (d, J=7.8 Hz, 1H), 6.64 (s, 1H), 6.52 (dd, J=7.8, 2.3 Hz, 1H), 3.77-3.68 (m, 1H), 3.67-3.54 (m, 3H), 3.36 (dd, J=12.6, 6.8 Hz, 2H), 3.13-3.05 (m, 2H), 2.38-2.28 (m, 1H), 2.03 (s, 3H), 1.78 (d, J=10.9 Hz, 1H), 1.24 (t, J=7.0 Hz, 3H); LC/MS (ESI+): 253 (M+H).

163c) Into a microwave tube was dissolved 10-methanesulfonyl-10-aza-tricyclo[6.3.1.0*2,7*]dodeca-2(7),3,5-trien-4-ylamine (50 mg, 0.2 mmol) and 2-(2,5-dichloro-pyrimidin-4-ylamino)-N-methyl-benzenesulfonamide (64.5 mg, 0.194 mmol) in isopropyl alcohol (1 mL, 10 mmol). The tube was heated in the microwave at 130° C. for 20 minutes. The reaction solution was poured into saturated sodium bicarbonate solution and was extracted with methylene chloride (6×20 ml). The reaction was dried over magnesium sulfate filtered and was rotovaped to a clear oil. Upon addition of ethyl acetate and hexanes 2-[5-Chloro-2-(10-methanesulfonyl-10-aza-tricyclo[6.3.1.0*2,7*]dodeca-2,4,6-trien-4-ylamino)-pyrimidin-4-ylamino]-N-methyl-benzenesulfonamide crashed out as a white solid 63.03 mg, 60%). MP: 207° C. dec.; 1H-NMR (CDCl$_3$) δ 9.09 (s, 1H), 8.43 (d, J=8.3 Hz, 1H), 8.14 (s, 1H); 7.96 (d, J=7.8 Hz, 1H), 7.64-7.58 (m, 2H) 7.17 (d, J=7.8 Hz, 1H), 6.98 (m, 1H), 4.62 (br s, 1H), 3.67-3.53 (m, 2H), 3.38-3.39 (m, 2H), 3.20 (br s, 1H), 3.14 (br s, 1H), 2.66 (d, J=5.3 Hz, 3H), 2.42-2.35 (m, 1H), 2.03 (s, 3H), 1.84 (d, J=11.1 Hz, 1H), 1.57 (s, 3H), LC/MS (ESI+): 549 (M+H).

Example 164

2-[5-Chloro-2-(10-methanesulfonyl-10-aza-tricyclo[6.3.1.0*2,7*]dodeca-2,4,6-trien-4-ylamino)-pyrimidin-4-ylamino]-N-methyl-benzamide 164a) Into a microwave tube was dissolved 10-methane-sulfonyl-10-aza-tricyclo[6.3.1.0*2,7*]dodeca-2(7),3,5-trien-4-ylamine (50 mg, 0.2 mmol) and 2-(2,5-dichloro-pyrimidin-4-ylamino)-N-methyl-benzamide (58.0 mg, 0.194 mmol) in isopropyl alcohol (1 mL, 10 mmol). The tube was heated in the microwave at 130° C. for 20 minutes. The reaction solution was poured into saturated sodium bicarbonate solution and was extracted with methylene chloride (6×20 ml). The reaction was dried over magnesium sulfate filtered and was rotovaped to a clear oil. The crude product was chromatographed on silica gel (12 g Isco column) and eluted with a gradient of 0-15% methanol in methylene chloride to yield -[5-Chloro-2-(10-methanesulfonyl-10-aza-tricyclo[6.3.1.0*2,7*]dodeca-2,4,6-trien-4-ylamino)-pyrimidin-4-ylamino]-N-methyl-benzamide (31.0 mg, 31%) as a white powder. MP: 163.5-165.0° C.; $^1$H-NMR (CDCl$_3$) δ 10.97 (s, 1H), 8.45 (d, J=8.3 Hz, 1H), 8.03 (s, 1H), 7.65 (s, 1H), 7.55-7.42 (m, 2H), 7.21-7.09 (m, 3H), 6.40 (br s, 1H), 3.40-3.28 (m, 3H), 3.18 (br s, 1H) 3.10 (br s, 1H), 3.02 (dd, J=5.05, 3H), 2.42-2.30 (m, 1H), 2.08-2.00 (m, 1H), 1.90 (s, 3H), 1.81 (d, J=10.9 Hz, 1H), 1.32-1.21 (m, 2H), 0.90-0.81 (m, 2H).

Example 165

N-{(1R,2R)-2-[5-Chloro-2-(10-isopropyl-10-aza-tricyclo[6.3.1.0*2,7*]dodeca-2,4,6-trien-4-ylamino)-pyrimidin-4-ylamino]-cyclohexyl}-methanesulfonamide 165a) 10-Isopropy-10-aza-tricyclo[6.3.1.0*2,7*]dodeca-2,4,6-trien-4-ylamine (100 mg, 0.50 mmol), N-{(1R,2R)-2-[(2,5-Dichloro-pyrimidin-4-yl)-methyl-amino]-cyclohexyl-methane sulfonamide (163 mg, 0.50 mmol) and 4N HCl in dioxane (130 μl, 0.50 mmol) were combined in a microwave tube. The reaction was heated to at 120° C. for 40 minutes in the microwave. The reaction was poured into water (50 ml) and saturated sodium bicarb (90 ml) and extracted 3 times with 25 ml portions of methylene chloride. The combined organic was dried over magnesium sulfate, filtered and evaporated to a brown oil. The crude reaction was purified on a 40 g Isco silica gel column using 0-10% methanol in methylene chloride as the eluent to yield N-{(1R,2R)-2-[5-Chloro-2-(10-isopropyl-10-aza-tricyclo[6.3.1.0*2,7*]dodeca-2,4,6-trien-4-ylamino)-pyrimidin-4-ylamino]-cyclohexyl}-methanesulfonamide as a mixture of diastereomers (27.56 mg, 11%) as a light brown foam. MP: 113-118.5° C.; $^1$H-NMR (CDCl$_3$) δ 8.15-8.05 (m, 1H), 7.90 (s, 1H), 7.42 (br s, 1H), 7.18 (d, J=7.8 Hz, 1H), 7.14 (d, J=7.8 Hz, 1H), 6.95-6.84 (m, 1H), 5.83-5.68 (m, 1H), 5.45 (d, J=3 Hz, 1H), 3.98-3.86 (m, 1H), 3.25-3.05 (m, 4H), 2.98-2.85 (m, 2H), 2.78 (s, 3H), 2.70-2.50 (m, 4H), 2.29 (br s, 1H), 2.18 (br s, 1H), 1.85-1.60 (m, 5H), 1.48 (br s, 5H), 1.00 (br s, 5H), 0.85 (t, J=7 Hz, 3H); LC/MS (ESI+): 344 (M+H after loss of C$_7$H$_{14}$O$_2$NS)

Example 166

3-[5-Chloro-2-(3-ethyl-2,3,4,5-tetrahydro-1H-benzo[d]azepin-7-ylamino)-pyrimidin-4-ylamino]-azepan-2-one 166a) To a stirred solution of 2,4,5-trichloro-pyrimidine (2.1 g, 0.0117 mol) in DMF (20 mL) was added potassium carbonate (3.2 g, 0.234 mol) and 3-amino-azepan-2-one (1.5 g, 0.0117 mol). The reaction mixture was stirred at room temperature for 72 h then warmed to 50° C. for 2 h. The mixture was cooled to room temperature and concentrated in vacuo to a tan solid. The solid was triturated with water and collected by filtration to give the product (2.75 g, 86% yield). $^1$HNMR (400 MHz, DMSO-d6) δ 8.26 (s, 1H), 8.15 (t, 1H, J=6 Hz), 7.45 (d, 1H, J=6 Hz), 4.58 (m, 1H), 3.23-3.30 (m, 1H), 3.11 (m, 1H), 2.00 (m, 2H), 1.67-1.82 (m, 2H), 1.45 (q, 1H, J=12 Hz), 1.25 (q, 1H, J=12 Hz); MS (m/e) 274 (M+1).

166b) 3-Ethyl-2,3,4,5-tetrahydro-1H-benzo[d]azepin-7-ylamine (75 mg 0.20 mmol), 3-(2,5-Dichloro-pyrimidin-4-ylamino)-azepan-2-one (57 mg, 0.30 mmol) and 81 μl of 4N HCl in dioxanes were combined into 1 ml IPA in a microwave tube. The reaction was heated to 120° C. for 40 minutes in the microwave. The reaction was poured into water (50 ml) and saturated sodium bicarb (90 ml) and extracted 3 times with 25 ml portions of methylene chloride. The combined organic was dried over magnesium sulfate, filtered and evaporated to a brown oil. The crude reaction was purified on a 12 g Isco silica gel column using 0-20% methanol in methylene chloride as the eluent to yield 3-[5-Chloro-2-(3-ethyl-2,3,4,5-tetrahydro-1H-benzo[d]azepin-7-ylamino)-pyrimidin-4-ylamino]-azepan-2-one (22.33 mg, 19%). MP: 232-234° C.; $^1$H-NMR (CDCl$_3$) δ 7.99 (s, 1H), 7.47 (d, J=8 Hz, 1H), 7.16 (s, 1H), 7.08 (d, J=8 Hz, 1H), 6.97 (s, 1H), 6.83 (d, J=6 Hz, 1H), 6.30 (br s, 1H), 4.69 (q, J=9.9, 5.56 Hz, 1H), 3.32 (m, 2H), 2.92 (m, 4H), 2.72-2.52 (m, 6H), 2.25 (d, J=3.9 Hz, 1H), 2.05 (d, J=4.2 Hz, 1H), 1.95-1.65 (m, 2H), 1.60-1.40 (m, 2H), 1.08 (t, J=7 Hz, 3H); LC/MS (ESI+): 429 (M+H).

Example 171

2-[5-Chloro-2-(5-oxo-2,3,4,5-tetrahydro-1H-benzo[e][1,4]diazepin-6-ylamino)pyrimidin-4-ylamino]-N-methyl-benzenesulfonamide 171a) To a stirred solution of 2-fluoro-6-nitro-benzoic acid (2.15 g, 0.0116 mol) in THF (25 mL)/methanol (10 mL) under nitrogen was added diazomethane (5.8 mL) dropwise. The reaction mixture was stirred at room temperature overnight. HPLC indicated complete conversion to product. The reaction solvent was removed in vacuo to give a tannish yellow solid 2-Fluoro-6-nitro-benzoic acid methyl ester (2.2 g, 96% yield). $^1$H NMR (400 MHz, DMSO-d$_6$) δ 8.12 (d, 1H, J=7.6 Hz), 7.88 (m, 2H), 3.92 (s, 3H).

171b) To a stirred solution of 2-fluoro-6-nitro-benzoic acid methyl ester (0.35 g, 0.00176 mol) in DMF (8 mL) under nitrogen was added (2-amino-ethyl)-carbamic acid tertbutyl ester (0.28 g, 0.00176 mol) and potassium carbonate (0.49 g, 0.0035 mol). The reaction mixture was stirred at room temperature for 48 h. The reaction solvent was removed and the resulting oil redissolved in ethyl acetate and washed with water. The organic phase was dried over magnesium sulfate, filtered, and concentrated in vacuo. The reaction mixture was purified by ISCO chromatography on silica gel (20 g column) using 10-50% ethyl acetate-hexane to give 2-(2-tert-Butoxycarbonylamino-ethylamino)-6-nitro-benzoic acid methyl ester (0.59 g, 98% yield). $^1$H NMR (400 MHz, DMSO-$d_6$) δ 7.48 (t, 1H, J=8 Hz), 7.11 (m, 2H), 7.00 (m, 1H), 6.52 (m, 1H), 3.77 (s, 3H), 3.24 (m, 2H), 3.11 (m, 2H), 1.44 (s, 9H); MS (m/e) 340 (M+1).

171c) To a solution of 2-(2-tert-butoxycarbonylaminoethylamino)-6-nitro-benzoic acid methylester (0.26 g, 0.00077 mol) in THF-water (3:1, 20 mL) under nitrogen was added lithium hydroxide (0.14 g, 0.00326 mol) as a solid in one portion. The reaction mixture was heated at 50° C. for 5 h then cooled to room temperature overnight. The mixture was diluted with ethyl acetate (10 mL) and washed with 10% aqueous HCl, water, and brine. The organic phase was dried over magnesium sulfate, filtered and concentrated in vacuo to a yellow oil which was purified by ISCO chromatography on silica gel using 15-50% ethyl acetate-hexane to give product as a pale yellow oil 2-(2-tert-butoxycarbonylaminoethylamino)-6-nitro-benzoic acid (0.24 g, 96%). $^1$H NMR (400 MHz, CDCl$_3$) δ 11.8 (s, 1H), 7.57 (t, 1H, J=7.8 Hz), 7.05 (d, 1H, J=7.8 Hz), 6.81 (d, 1H, J=7.8 Hz), 6.73 (s, 1H), 4.5 (s, 1H), 3.47 (m, 2H), 3.19 (m, 2H), 1.47 (s, 9H); MS (m/e) 326 (M+1).

171d) To a stirred solution of 2-(2-tert-butoxycarbonylamino-ethylamino)-6-nitro-benzoic acid (0.22 g, 0.00068 mol) in THF at 0° C. was added 4N HCl in dioxane (0.68 mL). The reaction was stirred at 0° C. for 2 h then warmed to room temperature overnight. The reaction mixture was diluted with ethyl acetate and washed with water. The organic phase was dried over magnesium sulfate, filtered and concentrated in vacuo to give 2-(2-amino-ethylamino)-6-nitro-benzoic acid (0.12, 76% yield). $^1$H NMR (400 MHz, CDCl$_3$) δ 11.6 (s, 1H), 7.57 (t, 1H, J=7.6 Hz), 7.05 (d, 1H, J=7.8 Hz), 6.80 (d, 1H, J=7.8 Hz), 4.0 (broad s, 3H), 3.63 (m, 2H), 3.07 (m, 2H); MS (m/e) 226 (M+1).

171e) To a stirred solution of 2-(2-amino-ethylamino)-6-nitro-benzoic acid (0.35 g, 0.0013 mol) in DMF (10 mL) was added HOBt (0.22 g, 0.0016 mol), BOP (0.71 g, 0.0016 mol) and N-methylmorpholine (0.18 mL, 0.0016 mol) at 0° C. under nitrogen. The reaction was stirred for at 0° C. for 1 h then warmed to room temperature overnight. The reaction was diluted with ethyl acetate (20 mL) and washed with water, 10% aqueous HCl, water and brine. The organic phase was dried over magnesium sulfate, filtered and concentrated in vacuo. The product was purified by ISCO purification using 5-15% methanol-methylene chloride to give desired 6-Nitro-1,2,3,4-tetrahydro-benzo[e][1,4]diazepin-5-one (0.22 g, 82% yield). $^1$H NMR (400 MHz, CDCl$_3$) δ 9.9 (s, 1H), 7.41 (t, 1H, J=7.6 Hz), 7.12 (d, 1H, J=7.6 Hz), 6.95 (d, 1H, J=7.6 Hz), 3.92 (broad s, 1H), 3.25 (m, 2H), 2.73 (m, 2H); MS (m/e) 208 (M+1).

171f) To a solution of 6-nitro-1,2,3,4-tetrahydro-benzo[e][1,4]diazepin-5-one (0.2 g, 0.0011 mols) in methanol (8 mL) in a Parr bottle was added 10% palladium on carbon and the mixture subjected to hydrogen at 50 psi for 4 h. The reaction mixture was filtered through celite and washed with DMF and methanol. The filtrate was concentrated in vacuo to give 6-amino-1,2,3,4-tetrahydro-benzo[e][1,4]diazepin-5-one and carried on without purification. $^1$H NMR (400 MHz, DMSO-$d_6$) δ 9.61 (s, 1H), 6.87 (d, 1H, J=7.6 Hz), 6.75-6.88 (m, 2H), 3.59 (t, 2H, J=6 Hz), 2.46 (t, 2H, J=6 Hz); MS (m/e) 178 (M+1).

171g) To a stirred solution of 6-amino-1,2,3,4-tetrahydro-benzo[e][1,4]diazepin-5-one (0.27 g, 0.0015 mol) in methylene chloride (8 mL) at 0° C. was added trifluoroacetic anhydride (0.21 mL, 0.0015 mol) followed by pyridine (0.12 mL, 0.0015 mol). The reaction mixture was stirred at 0° C. for 2 h then warmed to room temperature overnight. The reaction was diluted with methylene chloride and washed with sat. aqueous sodium bicarbonate and water. The organic phase was dried over magnesium sulfate, filtered and concentrated in vacuo to give 6-amino-1-(2,2,2-trifluoro-acetyl)-1,2,3,4-tetrahydro-benzo[e][1,4]diazepin-5-one (0.19 g, 46% yield). $^1$H NMR (400 MHz, DMSO-$d_6$) δ 8.23 (t, 1H, J=6 Hz), 7.21 (t, 1H, J=8 Hz), 6.84 (d, 1H, J=8 Hz), 6.52 (d, 1H, J=7.6 Hz), 5.91 (s, 2H), 4.35 (m, 1H), 3.22-3.27 (m, 2H), 2.96-3.06 (m, 1H); MS (m/e) 274 (M+1).

171h) Into a microwave vial was placed 6-amino-1-(2,2,2-trifluoro-acetyl)-1,2,3,4-tetrahydro-benzo[e][1,4]diazepin-5-one (25 mg, 0.092 mmol) and 2-(2,5-dichloro-pyrimidin-4-ylamino)-N-methyl-benzenesulfonamide (27 mg, 0.082 mmol) in isopropyl alcohol (3 mL) with 4 M HCl in dioxane (~2 drops). The mixture was subjected to microwaves at 120° C. for 10 minutes. Trace starting materials were present so the reaction mixture was resubjected to the same microwave conditions. The resulting solid was collected by filtration and washed with cold methylene chloride and dried in a vacuum oven at 50° C. overnight to give product as an off-white solid 2-[5-Chloro-2-(5-oxo-2,3,4,5-tetrahydro-1H-benzo[e][1,4]diazepin-6-ylamino)pyrimidin-4-ylamino]-N-methylbenzene-sulfonamide (6 mg, 16% yield). $^1$H NMR (400 MHz, DMSO-$d_6$) δ 12.60 (s, 1H), 9.62 (s, 1H), 9.04 (d, 1H, J=8 Hz), 8.95-8.86 (m, 3H), 8.55 (s, 1H), 7.88-7.25 (m, 4H), 6.71 (d, 1H, J=7.8 Hz), 6.52 (s, 1H), 3.46 (m, 2H), 2.84 (d, 3H), 2.5 (m, 2H); MS (m/e) 474 (M+1)

Example 172

2-[5-Chloro-2-(7-oxo-6,7,8,9-tetrahydro-5H-benzocyclo-hepten-2-ylamino)-pyrimidin-4-ylamino]-N-methyl-benzamide 172a) To a stirred solution of α,α'-dibromo-o-xylene (1g, 0.0038 mol) in dichloromethane (10 ml) was added tetrabutylammonium iodide (0.84 g, 0.023 mol) and 5% aq. sodium bicarbonate (43 mL). To this mixture was added slowly diethyl 1,3-acetonedicarboxylate (1 g, 0.0049 mol). The reaction mixture was stirred vigorously for 24 h. Saturated aqueous ammonium chloride was added and the mixture extracted with ethyl acetate (3×40 ml), washed with water (1×40) and brine. The organic phase was dried over magnesium sulfate, filtered and concentrated in vacuo to a yellow green oil. The oil was dissolved in 8% aqueous potassium hydroxide solution (20 ml) and ethanol (30 ml) and heated to reflux for 2 h. HCl (1N) was added to the mixture and extracted with chloroform, washed with water and brine. The organic phase was dried over magnesium sulfate, filtered and concentrated in vacuo to a light green colored oil, 5,6,8,9-tetrahydro-benzocyclohepten-7-one. The oil was purified using ISCO chromatography on silica gel using 5-15% hexane-ethyl acetate to give a pale green oil which crystallized upon standing. $^1$H NMR (400 MHz, DMSO-$d_6$) δ 7.22 (s, 4H), 2.91 (m, 4H), 2.61 (m, 4H).

172b) A flask containing 90% nitric acid was cooled to at −35° C. using an acetonitrile-dry ice bath. 5,6,8,9-Tetrahydro-benzocyclohepten-7-one (0.5 g, 0.003 mol) was added in portions over 30 minutes. The mixture was warmed slightly to at −20° C. for 1.5 h until all of the material was dissolved. The mixture was poured over ice and water and the resulting precipitate was collected by filtration and washed with water. The solid was dried at under vacuum overnight to give a tan solid (0.58, 78%), 2-nitro-5,6,8,9-tetrahydrobenzocyclohepten-7-one. $^1$H NMR (400 MHz, DMSO-$d_6$) δ 8.12 (s, 1H), 8.09 (d, 1H, J=8.4 Hz), 7.40 (d, 1H, J=8.4 Hz), 3.03 (m, 4H), 2.65 (m, 4H), 172c) To a stirred solution of 2-nitro-5,6,8,9-tetrahydrobenzocyclohepten-7-one (0.5 g, 0.002 mol) in THF (125 mL) was added stannous chloride in conc. HCl (4 mL) over a 5 minute period. During this time the reaction mixture got very hot but not to reflux. The reaction mixture was stirred at room temperature for 2 h. The mixture continued to stir at room temperature overnight. HPLC showed no starting material remaining. The reaction mixture was concentrated in vacuo to remove all of the volatiles and the residue dissolved in water and made basic with 6N sodium hydroxide. The suspension was filtered through celite and washed well with chloroform. The organic layer was dried over magnesium sulfate, filtered and concentrated in vacuo to give 2-amino-5,6,8,9-tetrahydro-benzocyclohepten-7-one (0.32 g, 70% yield). $^1$HNMR (400 MHz, DMSO-$d_6$) δ 6.87 (d, 1H, J=8 Hz), 6.46 (s, 1H), 6.38 (d, 1H, J=8 Hz), 4.83 (s, 2H), 2.68 (m, 4H), 2.44 (m, 4H).

172d) Into a microwave vial was placed 2-(2,5-dichloro-pyrimidin-4-ylamino)-N-methyl-benzamide (50 mg, 0.0002 mol) and 2-amino-5,6,8,9-tetrahydro-benzocyclohepten-7-one (38 mg, 0.00022 mol) in isopropyl alcohol (5 mL, 0.06 mol) with 4 M HCl (3 drops). The mixture was subjected microwaves at 130° C. for 10 minutes. Trace starting materials were present so the reaction mixture was resubjected to the same microwave conditions. The resulting solid was collected by filtration and washed with cold methylene chloride and dried in a vacuum oven at 50° C. overnight to give 38 mg (50%) of an off-white solid 2-[5-Chloro-2-(7-oxo-6,7,8,9-tetrahydro-5H-benzocyclo-hepten-2-ylamino)-pyrimidin-4-ylamino]-N-methyl-benzamide. MP: 262-269° C.; $^1$HNMR (400 MHz, DMSO-$d_6$) δ 11.63 (s, 1H), 9.50 (s, 1H), 8.78 (d, 1H, J=5.3 Hz), 8.69 (d, 1H, J=8.08 Hz), 8.24 (s, 1H), 7.76 (d, 1H, J=7.58), 7.59 (s, 1H), 7.48 (t, 1H, J=7.58 Hz), 7.42 (d, 1H, J=7.58), 7.17 (t, 1H, J=8 Hz), 2.77-2.85 (m, 8H), 2.5 (d, 3H); MS (m/e) 436 (M+1).

Example 173

(2-exo,3-exo)-3-[5-Chloro-2-(7-oxo-6,7,8,9-tetrahydro-5H-benzocyclo-hepten-2-ylamino)-pyrimidin-4-ylamino]-bicyclo[2.2.1]hept-5-ene-2-carboxylic acid amide; hydrochloride Into a microwave vial was placed 2-amino-5,6,8,9-tetrahydro-benzocyclohepten-7-one (34 mg, 0.00019 mol) and (2-exo,3-exo)-3-(2,5-dichloro-pyrimidin-4-ylamino)-bicyclo[2.2.1]hept-5-ene-2-carboxylic acid amide (40 mg, 0.0001 mol) in isopropyl alcohol (4 mL, 0.06 mol) along with 3-4 drops of 4 M HCl in dioxane-water. The mixture was subjected microwaves at 130° C. for 10 minutes. Trace starting materials were present so the reaction mixture was resubjected to the same conditions (130° C. for 10 min.). The resulting solid was collected by filtration and washed with cold methylene chloride and dried in a vacuum oven at 50° C. overnight to give 58 mg of (2-exo,3-exo)-3-[5-chloro-2-(7-oxo-6,7,8,9-tetrahydro-5H-benzocyclo-hepten-2-ylamino)-pyrimidin-4-ylamino]-bicyclo[2.2.1]hept-5-ene-2-carboxylic acid amide; hydrochloride as off-white solid. MP: 258-262° C.; $^1$HNMR (400 MHz, DMSO-$d_6$) δ 9.93 (broad s, 1H), 9.0 (broad s, 1H), 8.13 (s, 1H), 7.92 (s, 1H), 7.55 (d, 1H, J=7.6), 7.46 (s, 1H), 7.38 (s, 1H), 7.24 (d, 1H, J=8.6 Hz), 6.38 (m, 1H), 6.23 (m, 1H), 4.04 (t, 1H, J=9 Hz), 2.92 (s, 1H), 2.86 (m, 4H), 2.45-2.53 (m, 6H), 2.03 (d, 1H, J=8.84), 1.42 (d, 1H, J=9 Hz); MS (m/e) 438 (M+1).

Example 174

N-{(1R,2R)-2-[5-Chloro-2-(7-oxo-6,7,8,9-tetrahydro-5H-benzocyclohepten-2-ylamino)-pyrimidin-4-ylamino]-cyclohexyl}-methanesulfonamide Into a microwave vial was placed N-[(1R,2R)-2-(2,5-dichloro-pyrimidin-4-ylamino)-cyclohexyl]-methanesulfonamide (50 mg, 0.0001 mol) and 2-amino-5,6,8,9-tetrahydro-benzocyclohepten-7-one (34 mg, 0.00019 mol) in isopropyl alcohol (5 mL, 0.06 mol) along with 3-4 drops of 4 M HCl in dioxane-water. The mixture was subjected microwaves at 130° C. for 10 minutes. The reaction mixture was resubjected to the same conditions for complete conversion of starting materials. The resulting solid was collected by filtration and washed with cold methylene chloride and dried in a vacuum oven at 50° C. overnight to give N-{(1R,2R)-2-[5-chloro-2-(7-oxo-6,7,8,9-tetrahydro-5H-benzocyclohepten-2-ylamino)-pyrimidin-4-ylamino]-cyclohexyl}-methanesulfonamide as an off-white solid (43 mg, 60%). MP: 146-153° C.; $^1$HNMR (400 MHz, DMSO-$d_6$) δ 9.34 (broad s, 1H), 7.98 (s, 1H), 7.65 (s, 1H), 7.44 (d, 1H, J=8.8 Hz), 7.18 (d, 1H, J=8 Hz), 7.14 (d, 1H, J=8 Hz), 6.99 (broad s, 1H), 3.85 (m, 1H), 3.57 (m, 1H), 2.94 (s, 3H), 2.84 (dd, 4H, J=7 Hz), 2.54 (m, 4H), 2.06 (m, 2H), 1.70 (d, 2H, J=11 Hz), 1.19-1.38 (m, 4H); MS (m/e) 478 (M+1).

Example 175

2-[5-Chloro-4-(2-methoxy-4-morpholin-4-yl-phenylamino)-pyrimidin-2-ylamino]-5,6,8,9-tetrahydro-benzocyclohepten-7-one Into a microwave vial was added (2,5-dichloro-pyrimidin-4-yl)-(2-methoxy-4-piperazin-1-yl-phenyl)-amine (60 mg, 0.0002 mol) and 2-amino-5,6,8,9-tetrahydro-benzocyclohepten-7-one (38 mg, 0.00022 mol) in isopropyl alcohol (5 mL, 0.06 mol) with 3-4 drops of 4M HCl in dioxane-water. The mixture was subjected to microwaves at 130° C. for 10 minutes. Trace starting materials were present so the reaction mixture was resubjected to the same conditions. The resulting solid was collected by filtration and washed with cold methylene chloride and dried in a vacuum oven at 50° C. overnight to give 50 mg of 2-[5-chloro-4-(2-methoxy-4-morpholin-4-yl-phenylamino)-pyrimidin-2-ylamino]-5,6,8,9-tetrahydro-benzocyclohepten-7-one as an off-white solid. MP: 212-215° C.; $^1$HNMR (400 MHz, DMSO-$d_6$) δ 9.19 (s, 1H), 8.11 (s, 1H), 8.04 (s, 1H), 7.54 (s, 1H), 7.50 (d, 1H, J=8 Hz), 7.25 (d, 1H, J=9, 17 Hz), 6.99 (d, 1H, J=8 Hz), 6.68 (d, 1H, J=9 Hz), 6.51 (d, 1H, J=9 Hz), 3.77 (s, 7H), 3.15 (m, 4H), 2.75 (m, 2H), 2.60 (m, 2H), 2.47 (m, 4H); MS (m/e) 494 (M+1).

Example 176

Cis-2-[5-Chloro-2-(3-ethyl-2,3,4,5-tetrahydro-1H-benzo[d]-azepin-7-ylamino)-pyrimidin-4-ylamino]-cyclopentanecarboxylic acid amide 176a) To a stirred solution of cis-2-amino-cyclopentanecarboxylic acid amide (1 g, 0.008 mol) in methanol (20 mL, 0.5 mol) and water (10 mL, 0.6 mol) at 0° C. in an ice bath was added 2,4,5-trichloropyrimidine (1.7 g, 0.0094 mol) followed by sodium bicarbonate (1 g, 0.02 mol). The reaction mixture was warmed to room and stirred at room temperature for 24 h.

The reaction mixture was diluted with water (25 mL) and washed with ethyl acetate (3×50 mL). The organic layers were dried over magnesium sulfate, filtered and concentrated in vacuo to give cis-2-(2,5-dichloro-pyrimidin-4-ylamino)-cyclopentanecarboxylic acid amide as a white solid (1.8 g, 80% yield). No further purification was needed. $^1$HNMR (400 MHz, CDCl$_3$) δ 7.99 (s, 1H), 6.73 (d, 1H, J=6.8 Hz), 5.56 (broad s, 1H), 5.44 (broad s, 1H), 4.66 (p, 1H, J=7.5 Hz), 2.97 (q, 1H, J=7.5 Hz), 2.05-2.15 (m, 3H), 1.83-1.98 (m, 2H), 1.70 (m, 1H).

176b) Into a microwave vial was added cis-2-(2,5-dichloro-pyrimidin-4-ylamino)-cyclopentane-carboxylic acid amide (80 mg, 0.0003 mol) and 3-ethyl-2,3,4,5-tetrahydro-1H-benzo[d]azepin-7-ylamine (61 mg, 0.00032 mol) in 2-methoxyethanol (4 mL, 0.06 mol). To this reaction mixture was added 4N HCl-dioxane (0.04 g, 0.0003 mol) and the contents subjected to microwaves at 120° C. for 10 min. HPLC indicated no starting material remaining. A solid had precipitated out of the reaction mixture and was collected by filtration. The white solid was dried in vacuum at 50° C. overnight to give cis-2-[5-Chloro-2-(3-ethyl-2,3,4,5-tetrahydro-1H-benzo[d]-azepin-7-ylamino)-pyrimidin-4-ylamino]-cyclopentanecarboxylic acid amide (30 mg, 20%). MP: 237-242° C.; $^1$HNMR (400 MHz, DMSO-d$_6$) δ 10.28 (s, 1H), 9.73 (s, 1H), 8.06 (s, 1H), 7.60 (s, 1H), 7.58 (d, 1H, J=), 7.46 (m, 1H), 7.16 (m, 2H), 4.43 (m, 1H), 3.62 (m, 5H), 3.18 (m, 2H), 2.87-2.98 (m, 4H), 1.59-1.75 (m, 5H), 1.59 (m, 1H), 1.27 (t, 3H, J=7.3 Hz); MS (m/e) 429 (M+1).

Example 177

(2-exo,3-exo)-3-{5-Chloro-2-[3-(2-methoxy-ethyl)-2,3,4,5-tetrahydro-1H-benzo[d]azepin-7-ylamino]-pyrimidin-4-ylamino}-bicyclo[2.2.1]heptane-2-carboxylic acid amide 177a) Into a round bottom flask was placed (2-exo, 3-exo)-3-amino-bicyclo[2.2.1]heptane-2-carboxylic acid amide (2 g, 0.01 mol) and 2,4,5-trichloropyrimidine (2.8 g, 0.016 mol) in Methanol (40 mL, 1 mol) and water (20 mL, 1 mol). Sodium bicarbonate (2 g, 0.02 mol) was added to the reaction mixture and the contents stirred at room temperature overnight. The reaction mixture was concentrated in vacuo to remove the methanol then extracted several times with ethyl acetate (3×50 mL). The organic layer was dried over magnesium sulfate, filtered and concentrated in vacuo to a white solid, (2-exo,3-exo)-3-(2,5-dichloro-pyrimidin-4-ylamino)-bicyclo[2.2.1]heptane-2-carboxylic acid amide. $^1$HNMR (400 MHz, DMSO-d$_6$) δ 8.66 (d, 1H, J=8 Hz), 8.18 (s, 1H), 7.78 (s, 1H), 7.22 (s, 1H), 4.05 (d, 1H, J=4 Hz), 2.63 (d, 1H, J=8 Hz), 2.30 (s, 1H), 2.15 (s, 1H), 1.87 (d, 1H, J=10 Hz), 1.55 (m, 2H), 1.26 (m, 2H), 1.18 (d, 1H, J=10 Hz).

177b) Into a microwave vial was placed 3-(2,5-dichloro-pyrimidin-4-ylamino)-bicyclo[2.2.1]heptane-2-carboxylic acid amide (90.0 mg, 0.000299 mol) and 3-(2-methoxy-ethyl)-2,3,4,5-tetrahydro-1H-benzo[d]azepin-7-ylamine (60 mg, 0.0003 mol) in isopropyl alcohol (6 mL, 0.08 mol). Several drops of 4M HCl were added to the reaction mixture and the contents subjected to microwave conditions (120° C., 20 min). Total reaction time was 150 min at 120° C. A solid had precipitated out of the reaction mixture overnight and was collected by filtration to give (2R,3S)-3-{5-Chloro-2-[3-(2-methoxy-ethyl)-2,3,4,5-tetrahydro-1H-benzo[d]azepin-7-ylamino]-pyrimidin-4-ylamino}-bicyclo[2.2.1]heptane-2-carboxylic acid amide; hydrochloride. $^1$HNMR (400 MHz, DMSO-d$_6$) δ 10.62 (broad s, 1H), 10.15 (broad s, 1H), 9.19 (broad s, 1H), 8.15 (s, 1H), 7.87 (s, 1H), 7.62 (dd, 1H, J=8.6, 18.7 Hz), 7.36 (d, 1H, J=6.6 Hz), 7.29 (s, 1H), 7.17 (d, 1H, J=8.6 Hz), 4.07 (q, 1H, J=8.6 Hz), 3.74 (m, 4H), 3.36 (m, 4H), 3.31 (s, 3H), 2.93-3.09 (m, 4H), 1.87 (d, 9.8 Hz), 1.55 (m, 2H), 1.28 (m, 2H), 1.18 (d, 1H, J=9.8 Hz); MS (m/e) 485 (M+1).

177c) The filtrate was diluted with methylene chloride and treated with 10% aqueous sodium bicarbonate. The organic phase was dried over magnesium sulfate, filtered and concentrated in vacuo to a greenish colored solid. The solid was triturated with methylene chloride and the solid collected by filtration to give (2R,3S)-3-{5-Chloro-2-[3-(2-methoxy-ethyl)-2,3,4,5-tetrahydro-1H-benzo[d]azepin-7-ylamino]-pyrimidin-4-ylamino}-bicyclo[2.2.1]heptane-2-carboxylic acid amide. $^1$HNMR (400 MHz, DMSO-d$_6$) δ 9.10 (s, 1H), 7.91 (s, 1H), 7.74 (d, 1H, J=7.3 Hz), 7.69 (s, 1H), 7.55 (d, 8.3 Hz), 7.36 (s, 1H), 6.95 (d, 1H, J=8.3 Hz), 4.13 (t, 1H, J=7.3 Hz), 3.44 (t, 2H, J=5.6 Hz), 3.23 (s, 3H), 2.76 (broad s, 4H), 2.62 (m, 7H), 2.33 (s, 1H), 2.29 (s, 1H), 1.92 (d, 1H, J=9.8 Hz), 1.55 (m, 2H), 1.27 (p, 2H, J=9.8 Hz), 1.14 (d, 1H, J=9.8 Hz); MS (m/e) 485 (M+1).

Example 178

2-[5-Chloro-2-(7-morpholin-4-yl-6,7,8,9-tetrahydro-5H-benzocyclohepten-2-ylamino)-pyrimidin-4-ylamino]-N-methyl-benzamide 178a) To a stirred solution of 2-nitro-5,6,8,9-tetrahydrobenzocyclohepten-7-one (500 mg, 0.002 mol) in 1,2-dichloroethane (20 mL, 0.2 mol) was added morpholine (0.23 mL, 0.0027 mol) and acetic acid (0.15 mL, 0.0027 mol). Sodium triacetoxyborohydride (670 mg, 0.0032 mol) was then added to the reaction mixture and the contents stirred at room temperature overnight. The reaction mixture was cooled to 0° C., diluted with methylene chloride (20 mL), quenched with aqueous ammonium chloride (5 mL) and washed with water and brine. The organic phase was dried over magnesium sulfate, filtered and concentrated in vacuo to a brown residue. The reaction mixture was purified by ISCO chromatography on silica gel (40 g column) using 10-30% ethyl acetate-hexane gradient. The major fractions corresponding to product as confirmed by LCMS were combined and concentrated in vacuo to give a light brown solid, 4-(2-nitro-6,7,8,9-tetrahydro-5H-benzocyclohepten-7-yl)-morpholine (450 mg, 70%). $^1$HNMR (400 MHz, CDCl$_3$) δ 8.05 (s, 1H), 7.98 (d, 1H, J=8 Hz), 7.44 (d, 1H, J=8 Hz), 3.62 (m, 4H), 3.37 (m, 1H), 3.04 (m, 4H), 2.77 (m, 4H), 2.05 (m, 2H), 1.4 (m, 2H); MS (m/e) 276 (M+1).

178b) Into a Parr pressure reactor was added 4-(2-nitro-6,7,8,9-tetrahydro-5H-benzocyclohepten-7-yl)-morpholine (200 mg, 0.0007 mol) in methanol (6 mL, 0.1 mol). The reaction was placed under 40 psi for 10 h. HPLC indicated no starting material remaining. The reaction mixture was filtered through celite. The celite was further washed with methanol and DMF. The filtrated was concentrated in vacuo to a tannish-brown solid which was confirmed as product by both 1HNMR and LCMS. Material was carried on without further purification to give 7-Morpholin-4-yl-6,7,8,9-tetrahydro-5H-benzocyclohepten-2-ylamine. $^1$HNMR (400 MHz, CDCl$_3$) δ 6.89 (d, 1H, J=7.8 Hz), 6.49 (s, 1H), 6.45 (d, 1H, J=7.8 Hz), 3.70 (broad s, 4H), 3.52 (broad s, 1H), 2.68-2.77 (m, 2H), 2.56 (broad s, 4H), 2.05 (m, 2H), 1.59 (broad s, 2H), 1.39 (m, 2H), 1.22 (m, 2H).

178c) Into a microwave vial was placed 7-morpholin-4-yl-6,7,8,9-tetrahydro-5H-benzocyclohepten-2-ylamine (66 mg, 0.00027 mol) and 2-(2,5-dichloro-pyrimidin-4-ylamino)-N-methyl-benzamide (70 mg, 0.0002 mol) in isopropyl alcohol (4 mL, 0.05 mol). To this mixture was added 4N HCl-dioxane (0.03 g, 0.0002 mol) and the contents subjected to microwaves at 120° C. for 10 min. HPLC showed starting materials remaining so the reaction mixture was subjected to an additional 10 min reaction time using the same conditions. A solid had precipitated out of solution and was collected by filtration. The solid was resuspended in methylene chloride and washed with aqueous sat. sodium bicarbonate followed by water. The organic phase was dried over magnesium sulfate, filtered and concentrated in vacuo to give 2-[5-Chloro-2-(7-morpholin-4-yl-6,7,8,9-tetrahydro-5H-benzocyclohepten-2-ylamino)-pyrimidin-4-ylamino]-N-methyl-benzamide as a pale yellow foam (46 mg, 40% yield). $^1$HNMR (400 MHz, DMSO-d$_6$) δ 11.57 (s, 1H), 9.32 (s, 1H), 7.73 (m, 2H), 8.20 (m, 2H), 7.75 (d, 1H, J=7.8 Hz), 7.49 (m, 2H), 7.33 (d, 1H, J=7.8 Hz), 7.15 (t, 1H, J=7.6), 7.01 (d, 1H, J=8.3), 3.55 (s, 4H), 2.81 (d, 3H), 2.76 (m, 1H), 2.60 (m, 3H), 2.47 (s, 4H), 1.98 (m, 2H), 1.32 (m, 3H); MS (m/e) 507 (M+1).

Example 179

N-{(1R,2R)-2-[5-Chloro-2-(7-morpholin-4-yl-6,7,8,9-tetrahydro-5H-benzocyclohepten-2-ylamino)-pyrimidin-4-ylamino]-cyclohexyl}-methanesulfonamide Into a microwave vial was placed N-[2-(2,5-dichloro-pyrimidin-4-ylamino)-cyclohexyl]-methanesulfonamide (1.0E2 mg, 0.00029 mol) and 7-morpholin-4-yl-6,7,8,9-tetrahydro-5H-benzocyclohepten-2-ylamine (0.080 g, 0.00032 mol) in isopropyl alcohol (4.0 g, 0.066 mol). To this mixture was added 4N HCl-dioxane (0.03 g, 0.0003 mol) and the contents subjected to microwaves at 120° C. for 10 min. The mixture was resubjected to the same conditions for an additional 15 min. for complete conversion of starting materials. A solid had precipitated out of solution and was redissolved in methylene chloride and washed with sat. aqueous sodium bicarbonate. The organic phase was dried over magnesium sulfate, filtered, and concentrated in vacuo to a tan foam. The solid was dried at 50° C. in a vacuum oven overnight to give N-{(1R,2R)-2-[5-Chloro-2-(7-morpholin-4-yl-6,7,8,9-tetrahydro-5H-benzocyclohepten-2-ylamino)-pyrimidin-4-ylamino]-cyclohexyl}-methanesulfonamide isolated as a mixture of diasteromers as a beige foam (72 mg, 44% yield). $^1$HNMR (400 MHz, DMSO-d$_6$) δ 9.06 (s, 1H), 7.92 (s, 1H), 7.54 (d, 1H, J=7.6 Hz), 7.35 (t, 1H, J=8.34), 7.18 (dd, 1H, J=5.05, 8.6 Hz), 6.97 (d, 1H, J=8.1 Hz), 6.69 (d, 1H, J=7.6 Hz), 3.84 (m, 1H), 3.55 (broad s, 4H), 3.37 (m, 1H), 2.94 (s, 3H), 2.43-2.78 (m, 9H), 1.96-2.09 (m, 4H), 1.70 (d, 2H, J=8.6 Hz), 1.18-1.36 (m, 6H); MS (m/e) 549 (M+1).

Example 180

2-[5-Chloro-2-(7,7-difluoro-6,7,8,9-tetrahydro-5H-benzocyclohepten-2-ylamino)-pyrimidin-4-ylamino]-N-methyl-benzamide 180a) To a stirred solution of 2-nitro-5,6,8,9-tetrahydrobenzocyclohepten-7-one (400 mg, 0.002 mol) in methylene chloride (7 mL, 0.1 mol) at 0° C. under nitrogen was added diethylaminosulfur trifluoride (0.5 mL, 0.004 mol) dropwise. The reaction mixture was allowed to slowly warm to room temperature overnight. HPLC indicated no starting material present so the reaction mixture was diluted with methylene chloride, washed with water, dried over magnesium sulfate and concentrated in vacuo. Crystals formed upon drying. The reaction mixture was purified by ISCO chromatography on silica gel using 5-10% ethylacetate/hexane to give 7,7-difluoro-2-nitro-6,7,8,9-tetrahydro-5H-benzocycloheptene as a pale tan solid (380 mg, 84% yield). $^1$HNMR (400 MHz, CDCl$_3$-d$_6$) δ 8.05 (s, 1H), 8.04 (d, 1H, J=7.6 Hz), 7.33 (d, 1H, J=7.6 Hz), 2.92 (m, 4H), 2.12 (m, 4H).

180b) To a Parr bottle was added 7,7-difluoro-2-nitro-6,7,8,9-tetrahydro-5H-benzocycloheptene (300 mg, 0.0013 mol) in methanol (10 mL) followed by 10% palladium on carbon (30 mg). The reaction was placed under 30 psi nitrogen for 4 h. The reaction mixture was filtered through celite and washed with methanol (20 mL) and DMF (20 mL). The filtrate was concentrated in vacuo to give 7,7-Difluoro-2-nitro-6,7,8,9-tetrahydro-5H-benzocycloheptene as a brown oil (225 mg, 88% yield). $^1$HNMR (400 MHz, DMSO-d$_6$) δ 7.62 (d, 1H, J=7.8 Hz), 7.39 (d, 1H, J=7.8 Hz), 7.28 (s, 1H) 3.04 (m, 4H), 1.67 (broad s, 2H), 1.18 (m, 4H); MS (m/e) 198 (M+1).

180c) Into a microwave vial was placed 7,7-difluoro-6,7,8,9-tetrahydro-5H-benzocyclohepten-2-ylamine (79 mg, 0.00040 mol) and 2-(2,5-dichloro-pyrimidin-4-ylamino)-N-methyl-benzamide (100 mg, 0.0003 mol) in isopropyl alcohol (4 mL, 0.05 mol). 4N HCl-dioxane (0.04 g, 0.0003 mol) was added to the reaction mixture and the contents subjected to microwaves at 120° C. for 10 min. The reaction mixture was resubjected to the same microwave conditions for an additional 10 min. A solid had precipitated out of the reaction mixture, was collected by filtration then redissolved in methylene chloride (6 mL) and washed with sat. aqueous sodium bicarbonate (1×5 mL) and water (2×5 mL). The organic phase was dried over magnesium sulfate, filtered and concentrated in vacuo to give 2-[5-Chloro-2-(7,7-difluoro-6,7,8,9-tetrahydro-5H-benzocyclohepten-2-ylamino)-pyrimidin-4-ylamino]-N-methyl-benzamide as a brown solid (38 mg, 29%). MP: 160-168° C.; $^1$HNMR (400 MHz, DMSO-d$_6$) δ 11.59 (s, 1H), 9.46 (s, 1H), 8.80 (d, 1H, J=4.5 Hz), 8.74 (d, 1H, J=7.6), 8.26 (s, 1H), 7.79 (d, 1H, J=7.8 Hz), 7.61 (s, 1H), 7.53 (t, 1H, J=7.6), 7.45 (d, 1H, J=7.8), 7.2 (t, 1H, J=7.3), 2.85 (d, 3H, J=4 Hz), 2.69-2.77 (m, 4H), 2.06 (m, 4H); MS (m/e) 458 (M+1).

Example 181

N-{(1R,2R)-2-[5-Chloro-2-(7,7-difluoro-6,7,8,9-tetrahydro-5H-benzocyclohepten-2-ylamino)-pyrimidin-4-ylamino]-cyclohexyl}-methanesulfonamide Into a microwave vial was placed 7,7-difluoro-6,7,8,9-tetrahydro-5H-benzocyclohepten-2-ylamine (79 mg, 0.00040 mol) and N-[(1R,2R)-2-(2,5-dichloro-pyrimidin-4-ylamino)-cyclohexyl]-methanesulfonamide (100 mg, 0.0003 mol) in isopropyl alcohol (4 mL, 0.05 mol) with 4N HCl-dioxane (0.04 g, 0.0003 mol). The reaction was subjected to microwaves at 120° C. for 10 min. HPLC and LCMS indicated trace starting material remaining. The reaction mixture was resubjected to microwaves for an additional 10 min. A tan solid had precipitated out of solution and was collected by filtration. The solid was redissolved in methylene chloride (5 mL) and washed with sat. sodium bicarbonate (1×5 mL) and water (2×5 mL). The organic phase was dried over magnesium sulfate, filtered and concentrated in vacuo to give N-{(1R,2R)-2-[5-Chloro-2-(7,7-difluoro-6,7,8,9-tetrahydro-5H-benzocyclohepten-2-ylamino)-pyrimidin-4-ylamino]-cyclohexyl}-methanesulfonamide as a brown solid (75 mg, 40%). MP: 118-128° C.; $^1$HNMR (400 MHz, DMSO-d$_6$) δ 9.16 (s, 1H), 7.93 (s, 1H), 7.62 (s, 1H), 7.46 (d, 1H, J=8 Hz), 7.18 (d, 1H, J=8 Hz), 7.07 (d, 1H, J=8 Hz), 6.71 (d, 1H, J=8

Hz), 3.84 (m, 1H), 2.94 (s, 3H), 2.70 (m, 4H), 1.99-2.09 (m, 6H), 1.71 (m, 2H), 1.18-1.39 (m, 5H); MS (m/e) 500 (M+1).

Example 182

5-Chloro-N*2*-(7,7-difluoro-6,7,8,9-tetrahydro-5H-benzocyclohepten-2-yl)-N*4*-(2-methoxy-4-morpholin-4-yl-phenyl)-pyrimidine-2,4-diamine Into a microwave vial was added 7,7-difluoro-6,7,8,9-tetrahydro-5H-benzocyclohepten-2-ylamine (55 mg, 0.00028 mol) and (2,5-dichloro-pyrimidin-4-yl)-(2-methoxy-4-morpholin-4-yl-phenyl)-amine (80 mg, 0.0002 mol) in isopropyl alcohol (4 mL, 0.05 mol). To this reaction mixture was added 4N HCl-dioxane (0.03 g, 0.0002 mol). The reaction was subjected to microwaves at 120° C. for 10 min. The reaction mixture was resubject to the microwave conditions (120° C. for 10 min). The reaction mixture was purified by prep HPLC using the Gilson system and a gradient of 30-50% acetonitrile-water. The peaks corresponding to product were combined extracted with methylene chloride and washed with bicarbonate and dried to give 5-Chloro-N*2*-(7,7-difluoro-6,7,8,9-tetrahydro-5H-benzocyclohepten-2-yl)-N*4*-(2-methoxy-4-morpholin-4-yl-phenyl)-pyrimidine-2,4-diamine a tan solid (34 mg, 30% yield). MP: 180-184° C.; $^1$HNMR (400 MHz, DMSO-d$_6$) δ 9.52 (s, 1H), 8.66 (broad s, 1H), 8.12 (s, 1H), 7.43 (s, 1H), 7.41 (d, 1H, J=8.84 Hz), 7.15 (d, 1H, J=8 Hz), 6.98 (d, 1H, 8 Hz), 6.71 (s, 1H), 6.54 (d, 1H, J=9 Hz), 3.78 (s, 7H), 3.18 (dd, 4H, J=5, 9 Hz), 2.65 (dd, 2H, J=5, 10 Hz), 1.97 (m, 4H); MS (m/e) 516 (M+1).

Example 183

2-[5-Chloro-2-(10-methanesulfonyl-12-oxa-10-azatricyclo[6.3.1.0*2,7*]dodeca-2(7),3,5-trien-4-ylamino)-pyrimidin-4-ylamino]-N-methyl-benzamide A racemic sample (1.8 mg) of the above compound was separated into the individual enantiomers using supercritical fluid chromatography on a chiralcel OJ-H column (250×4.6 mm, 5 μm) with 40% methanol. First eluting peak (0.58 mg, 98% purity) MS (m/e) 515 (M+1). Second eluting peak (0.51 mg, >98% purity) MS (m/e) 515 (M+1). Refer to racemate for $^1$H NMR.

Example 191

2-[2-(3-Ethyl-2,3,4,5-tetrahydro-1H-benzo[d]azepin-7-ylamino)-5-methyl-pyrimidin-4-ylamino]-N-methyl-benzamide 191a) 2,6-Dichloro-5-methylpyrimidine (245 mg, 1.5 mmol), 2-amino-N-methylbenzamide (225 mg, 1.5 mmol), and N,N-diisopropylethylamine (290 mg, 2.25 mmol) were combined in 3 mL isopropyl alcohol and subjected to microwave irradiation (CEM) at 180° C. for 60 minutes. A precipitate formed on cooling which was isolated by filtration and washed with 1 mL cold isopropyl alcohol. On drying, 158 mg (38%) of an off-white solid was obtained-2-(2-chloro-5-methyl-pyrimidin-4-ylamino)-N-methyl-benzamide. MS: 277.10 (M+H); $^1$H NMR (d6-dmso): δ 11.72 (s, 1H), δ 8.83 (br s, 1H), δ 8.64 (d, J=9 Hz, 1H), δ 8.18 (s, 1H), δ 7.80 (d, J=8 Hz, 1H), δ 7.58 (t, J=8 Hz, 1H), δ 7.17 (t, J=8 Hz, 1H), δ 2.81 (d, J=6 Hz, 3H), δ 2.08 (s, 3H).

191b) 2-(2-Chloro-5-methyl-pyrimidin-4-ylamino)-N-methyl-benzamide (32 mg, 0.12 mmol) and 3-ethyl-2,3,4,5-tetrahydro-1H-benzo[d]azepin-7-ylamine (24 mg, 0.13 mmol) were combined with 1 drop of a solution of 4N hydrochloric acid in dioxane and 2 mL isopropanol and subjected to microwave irradiation (CEP) at 170° C. for 150 minutes. The reaction mixture was concentrated and the organics were partitioned between dichloromethane and saturated sodium bicarbonate solution (100 mL each). The dichloromethane extract was separated, dried (sodium sulfate), and concentrated to afford a material which was purified on silica gel (methanol:dichloromethane gradient elution) to afford 20 mg (39%) of a white foam-2-[2-(3-ethyl-2,3,4,5-tetrahydro-1H-benzo[d]azepin-7-ylamino)-5-methyl-pyrimidin-4-ylamino]-N-methyl-benzamide. MS: 431.20 (M+H); $^1$H NMR (d6-dmso): δ 11.20 (s, 1H), δ 8.99 (s, 1H), δ 8.86 (d, J=8 Hz, 1H), δ 8.74 (d, J=4 Hz, 1H), δ 7.97 (s, 1H), δ 7.75 (d, J=8 Hz, 1H), δ 7.49 (s, 1H), δ 7.45 (t, J=8 Hz, 1H), δ 7.38 (d, J=8 Hz, 1H), δ 7.08 (t, J=8 Hz, 1H), δ 6.97 (d, J=8 Hz, 1H), δ 2.82 (d, J=6 Hz, 3H), δ 2.80 (m, 2H), δ 2.70-2.40 (m, 8H), δ 2.10 (s, 3H), δ 1.01 (t, J=8 Hz, 3H).

Example 192

2-[2-(3-Ethyl-2,3,4,5-tetrahydro-1H-benzo[d]azepin-7-ylamino)-5-bromo-pyrimidin-4-ylamino]-N-methyl-benzamide 192a) In a similar fashion as outlined in Example 191a, 2,6-dichloro-5-bromopyrimidine was reacted with 2-amino-N-methylbenzamide and N,N-diisopropylethylamine in isopropyl alcohol (microwave—120° C., 10 minutes) to afford 2-(2-chloro-5-bromo-pyrimidin-4-ylamino)-N-methyl-benzamide as a yellow solid in 76% yield. MS: 342.96 (M+H); $^1$H NMR (d6-dmso): δ 11.96 (s, 1H), δ 8.85 (br s, 1H), δ 8.57 (s, 1H), δ 8.47 (d, J=9 Hz, 1H), δ 7.79 (d, J=8 Hz, 1H), δ 7.57 (t, J=8 Hz, 1H), δ 7.22 (t, J=8 Hz, 1H), δ 2.78 (d, J=5 Hz, 3H).

192b) In a similar fashion as outlined in Example 191b, the product of Example 2a was reacted with 3-ethyl-2,3,4,5-tetrahydro-1H-benzo[d]azepin-7-ylamine, 4N hydrochloric acid in dioxane and methoxyethanol (no microwave, 110° C., 24 hours), to afford 2-[2-(3-ethyl-2,3,4,5-tetrahydro-1H-benzo[d]azepin-7-ylamino)-5-bromo-pyrimidin-4-ylamino]-N-methyl-benzamide as a yellow solid in 47% yield. Mp: 203-4° C.; MS: 494.75 (M+H); $^1$H NMR (d6-dmso): δ 11.32 (s, 1H), δ 9.33 (s, 1H), δ 8.73 (d, J=5 Hz, 1H), δ 8.66 (d, J=8 Hz, 1H), δ 8.27 (s, 1H), δ 7.73 (d, J=8 Hz, 1H), δ 7.45 (m, 2H), δ 7.34 (d, J=8 Hz, 1H), δ 7.15 (t, J=8 Hz, 1H), δ 6.99 (d, J=8 Hz, 1H), δ 2.82 (d, J=4 Hz, 3H), δ 2.77 (m, 2H), δ 2.64-2.40 (m, 8H), δ 1.13 (br t, 3H).

Example 193

2-[2-(3-Ethyl-2,3,4,5-tetrahydro-1H-benzo[d]azepin-7-ylamino)-5-nitro-pyrimidin-4-ylamino]-N-methyl-benzamide 193a) In a similar fashion as outlined in Example 191a, 2,6-dichloro-5-nitropyrimidine was reacted with 2-amino-N-methylbenzamide and N,N-diisopropylethylamine in ethyl ether (no microwave—20° C., 3 hours) to afford 2-(2-chloro-5-nitro-pyrimidin-4-ylamino)-N-methyl-benzamide as a yellow solid in 49% yield. Mp: 201-3° C. (dec); MS: 308.09 (M+H); $^1$H NMR (d6-dmso): δ 12.43 (s, 1H), δ 9.20 (s, 1H), δ 8.75 (br s, 1H), δ 8.19 (d, J=9 Hz, 1H), δ 7.71 (d, J=8 Hz, 1H), δ 7.58 (t, J=8 Hz, 1H), δ 7.33 (t, J=8 Hz, 1H), δ 2.78 (d, J=5 Hz, 3H).

193b) In a similar fashion as outlined in Example 191b, the product of Example 193a was reacted with 3-ethyl-2,3,4,5- tetrahydro-1H-benzo[d]azepin-7-ylamine, 4N hydrochloric acid in dioxane and isopropyl alcohol (microwave: 60° C., 10 minutes then 80° C., 10 minutes) to afford 2-[2-(3-ethyl-2,3,4,5-tetrahydro-1H-benzo[d]azepin-7-ylamino)-5-nitro-pyrimidin-4-ylamino]-N-methyl-benzamide as a yellow solid in 48% yield. Mp: 222-25° C.; MS: 462.13 (M+H); $^1$H NMR (d6-dmso): δ 12.07 (s, 1H), δ 10.46 (br s, 1H), δ 9.12 (s, 1H), δ 8.64 (br s, 1H), δ 8.15 (br s, 1H), δ 7.70 (br d, J=8 Hz, 1H), δ 7.56-7.25 (m, 4H), δ 7.06 (br s, 1H), δ 3.20 (m, 2H), δ 3.10-2.56 (m, 11H), δ 1.20 (m, 3H).

Example 194

2-[2-(3-Ethyl-2,3,4,5-tetrahydro-1H-benzo[d]azepin-7-ylamino)-5-cyano-pyrimidin-4-ylamino]-N-methyl-benzamide 194a) In a similar fashion as outlined in Example 191a, 2,6-dichloro-5-cyanopyrimidine was reacted with 2-amino-N-methylbenzamide and N,N-diisopropylethylamine in isopropyl alcohol (no microwave—20° C., 10 minutes) to afford 2-(2-chloro-5-cyano-pyrimidin-4-ylamino)-N-methyl-benzamide as a yellow solid. Mp: 228-32° C. (dec); MS: 288.26 (M+H); $^1$H NMR (chloroform-d): δ 12.49 (s, 1H), δ 8.69 (d, J=8 Hz, 1H), δ 8.50 (s, 1H), δ 7.57 (m, 2H), δ 7.22 (t, J=8 Hz, 1H), δ 6.31 (br s, 1H), δ 3.08 (d, J=5 Hz, 3H).

194b) In a similar fashion as outlined in Example 191b, the product of Example 194a was reacted with 3-ethyl-2,3,4,5-tetrahydro-1H-benzo[d]azepin-7-ylamine, 4N hydrochloric acid in dioxane and n-butanol (no microwave: 80° C., 24 hours) to afford 2-[2-(3-ethyl-2,3,4,5-tetrahydro-1H-benzo[d]azepin-7-ylamino)-5-cyano-pyrimidin-4-ylamino]-N-methyl-benzamide as a yellow solid in 40% yield. Mp: 164-70° C.; MS: 442.23 (M+H); $^1$H NMR (chloroform-d): δ 11.63 (s, 1H), δ 8.60 (d, J=8 Hz, 1H), δ 8.36 (s, 1H), δ 7.53 (d, J=8 Hz, 1H), δ 7.43 (br t, J=7 Hz, 1H), δ 7.37 (s, 1H), δ 7.26 (m, 2H), δ 7.13 (t, J=8 Hz, 1H), δ 7.08 (d, J=8 Hz, 1H), δ 6.30 (br d, J=4 Hz, 1H), δ 3.05 (d, J=4 Hz, 3H), δ 2.98 (m, 4H), δ 2.78-2.61 (m, 6H), δ 1.17 (t, J=8 Hz, 3H).

Example 195

2-[2-(3-Ethyl-2,3,4,5-tetrahydro-1H-benzo[d]azepin-7-ylamino)-5-trifluoromethyl-pyrimidin-4-ylamino]-N-methyl-benzamide 195a) In a similar fashion as outlined in Example 191a, 2,6-dichloro-5-trifluoromethylpyrimidine was reacted with 2-amino-N-methylbenzamide and N,N-diisopropylethylamine in isopropyl alcohol (no microwave—20° C., 2 days) to afford 2-(2-chloro-5-trifluoromethyl-pyrimidin-4-ylamino)-N-methyl-benzamide as a white solid in 8% yield. Mp: (209° C.); MS: 331.05 (M+H); $^1$H NMR (chloroform-d): δ 11.63 (br s, 1H), δ 8.59 (d, J=8 Hz, 1H), δ 8.47 (s, 1H), δ 7.59 (t, J=8 Hz, 1H), δ 7.52 (d, J=8 Hz, 1H), δ 7.19 (t, J=8 Hz, 1H), δ 6.20 (br s, 1H), δ 3.04 (d, J=5 Hz, 3H).

195b) In a similar fashion as outlined in Example 191b, the product of Example 195a was reacted with 3-ethyl-2,3,4,5-tetrahydro-1H-benzo[d]azepin-7-ylamine, camphorsulfonic acid (1.1 equivalent), and isopropyl alcohol (microwave: 120° C., 25 minutes) to afford 2-[2-(3-ethyl-2,3,4,5-tetrahydro-1H-benzo[d]azepin-7-ylamino)-5-trifluoromethyl-pyrimidin-4-ylamino]-N-methyl-benzamide as a white solid in 67% yield. Mp: 226° C.; MS: 484.99 (M+H); $^1$H NMR (chloroform-d): δ 10.84 (s, 1H), δ 8.47 (d, J=8 Hz, 1H), δ 8.36 (s, 1H), δ 7.49 (d, J=8 Hz, 1H), δ 7.41 (t, J=8 Hz, 1H), δ 7.34 (s, 1H), δ 7.29-7.21 (m, 2H), δ 7.11 (t, J=8 Hz, 1H), δ 7.03 (d, J=8 Hz, 1H), δ 6.21 (br d, J=4 Hz, 1H), δ 3.02 (d, J=5 Hz, 3H), δ 2.97-2.82 (m, 4H), δ 2.73-2.56 (m, 6H), δ 1.13 (t, J=7 Hz, 3H).

Example 196

2-[2-(3-Ethyl-2,3,4,5-tetrahydro-1H-benzo[d]azepin-7-ylamino)-5-fluoro-pyrimidin-4-ylamino]-N-methyl-benzamide 196a) In a similar fashion as outlined in Example 191a, 2,6-dichloro-5-fluoropyrimidine was reacted with 2-amino-N-methylbenzamide and N,N-diisopropylethylamine in isopropyl alcohol (no microwave—20° C., 24 hours) to afford 2-(2-chloro-5-fluoropyrimidin-4-ylamino)-N-methyl-benzamide as a white solid in 33% yield. Mp: 225° C. (dec); MS: 281.23 (M+H); $^1$H NMR (chloroform-d): δ 11.78 (br s, 1H), δ 8.80 (d, J=8 Hz, 1H), δ8.11 (s, 1H), δ 7.60 (t, J=8 Hz, 1H), δ 7.52 (d, J=8 Hz, 1H), δ 7.15 (t, J=8 Hz, 1H), δ 6.31 (br s, 1H), δ 3.06 (dd, J=2.5 Hz, 3H).

Example 197

2-[5-Bromo-2-(1-methyl-2-oxo-2,3,4,5-tetrahydro-1H-benzo[b]azepin-7-ylamino)-pyrimidin-4-ylamino]-N-methyl-benzamide 197a) 2-(2-chloro-5-bromo-pyrimidin-4-ylamino)-N-methyl-benzamide (52 mg, 0.15 mmol) and 7-amino-1-methyl-1,3,4,5-tetrahydrobenzo[b]azepin-2-one (29 mg, 0.15 mmol) were combined in 5 mL n-butanol. A drop of a solution of 4N hydrochloric acid in dioxane was added and the mixture was refluxed for five hours. The mixture was concentrated and triturated with ether. The remaining solid was partitioned between dichloromethane and saturated sodium bicarbonate solution (100 mL each). The organic layer was separated, was dried (sodium sulfate), and was concentrated to afford an oil which was purified on silica (methanol:dichloromethane gradient elution) to afford 36 mg (48%) of 2-[5-bromo-2-(1-methyl-2-oxo-2,3,4,5-tetrahydro-1H-benzo[b]azepin-7-ylamino)-pyrimidin-4-ylamino]-N-methyl-benzamide as an off-white solid. Mp: 238-40° C.; MS: 496.61 (M+H); $^1$H NMR (chloroform-d): δ 10.95 (s, 1H), δ 8.58 (d, J=8 Hz, 1H), δ 8.22 (s, 1H), δ 7.52 (d, J=8 Hz, 1H), δ 7.44 (m, 3H), δ 7.11 (t, J=8 Hz, 1H), δ 7.01 (s, 1H), δ 6.25 (br s, 1H), δ 3.35 (s, 3H), δ 3.06 (s, 3H), δ 2.67 (m, 2H), δ 2.33 (t, J=7 Hz, 2H), δ 2.16 (m, 2H).

Example 198

2-{5-Bromo-2-[8-methoxy-3-(2-methoxy-ethyl)-2,3,4,5-tetrahydro-1H-benzo[d]azepin-7-ylamino]-pyrimidin-4-ylamino}-N-methyl-benzamide 198a) 2-(2-chloro-5-bromo-pyrimidin-4-ylamino)-N-methyl-benzamide (52 mg, 0.15 mmol) and 8-methoxy-3-(2-methoxyethyl)-2,3,4,5-tetrahydro-1H-benzo[d]azepin-7-ylamine (48 mg, 0.19 mmol) were combined in 5 mL n-butanol. Two drops of a solution of 4N hydrochloric acid in dioxane was added and the mixture was refluxed for eight hours. The mixture was concentrated and the organics were partitioned between dichloromethane and saturated sodium bicarbonate solution (100 mL each). The organic layer was separated, was dried (sodium sulfate), and was concentrated to afford an oil which was purified on silica (methanol:dichloromethane gradient elution) to afford 2-{5-bromo-2-[8-methoxy-3-(2-methoxy-ethyl)-2,3,4,5-tetrahydro-1H-benzo[d]azepin-7-ylamino]-pyrimidin-4-ylamino}-N-methyl-benzamide as a tan foam (25%). Mp: 171-5° C.; MS: 556.78

(M+H); ¹H NMR (chloroform-d): δ 10.81 (s, 1H), δ 8.60 (d, J=8 Hz, 1H), δ 8.21 (s, 1H), δ 8.08 (s, 1H), δ 7.53-7.41 (m, 3H), δ 6.92 (t, J=8 Hz, 1H), δ 6.66 (s, 1H), δ 6.24 (br s, 1H), δ 3.78 (s, 3H), δ 3.57 (t, J=5 Hz, 35), δ 3.39 (s, 3H), δ 3.06 (dd, J=2.4 Hz, 2H), δ 2.91 (m, 2H), δ 2.82-2.67 (m, 8H).

Example 199

5-Chloro-N*2*,N*4*-bis-(3-ethyl-2,3,4,5-tetrahydro-1H-benzo[d]azepin-7-yl)-pyridine-2,4-diamine 199a) 2,5,6-trichloropyrimidine (200 mg, 0.15 mmol) and 3-ethyl-2,3,4,5-tetrahydro-1H-benzo[d]azepin-7-ylamine (209 mg, 1.10 mmol) were mixed with N,N-diisopropylethylamine (211 mg, 1.63 mmol) in 8 mL isopropyl alcohol and heated at 80° C. for 24 hours. The reaction was concentrated and the organics were partitioned between dichloromethane and saturated sodium bicarbonate solution. The organic layer was separated, was dried (sodium sulfate), and was concentrated. Chromatography on silica (1% to 20% methanol:dichloromethane gradient elution) afforded 273 mg (74%) of (2,5-dichloro-pyrimidin-4-yl)-(3-ethyl-2,3,4,5-tetrahydro-1H-benzo[d]azepin-7-yl)-amine as a tan foam. MS: 338.55 (M+H).

199b) (2,5-dichloro-pyrimidin-4-yl)-(3-ethyl-2,3,4,5-tetrahydro-1H-benzo[d]azepin-7-yl)-amine (50 mg, 0.15 mmol) and 3-ethyl-2,3,4,5-tetrahydro-1H-benzo[d]azepin-7-ylamine (29 mg, 0.15 mmol) were combined with camphorsulfonic acid (74 mg, 0.32 mmol) in 5 mL isopropyl alcohol and subjected to microwave irradiation at 120° C. for 80 minutes. 35 mg addition camphorsulfonic acid was added and microwave irradiation was continued for an additional hour. The mixture was concentrated and the organics were partitioned between dichloromethane and saturated sodium bicarbonate solution. The organic layer was separated, was dried (sodium sulfate), and was concentrated. The solid was obtained was triturated with ether. The ether was separated and concentrated and the solid obtained was purified by reverse phase chromatography (0% to 30% acetonitrile:water on C8) to afford 55 mg (76%) of 5-Chloro-N*2*,N*4*-bis-(3-ethyl-2,3,4,5-tetrahydro-1H-benzo[d]azepin-7-yl)-pyridine-2,4-diamine as a white solid. Mp: 132-4° C.; MS: 493.41 (M+2H); ¹H NMR (chloroform-d): δ 8.04 (s, 1H), δ 7.41 (d, J=8 Hz, 1H), δ 7.28 (m, 2H), δ 7.09 (d, J=8 Hz, 1H), δ 7.02 (m, 2H), δ 6.90 (br s, 1H), δ 3.00-2.85 (m, 8H), δ 2.76-2.54 (m, 12H), δ 1.17 (m, 6H).

Example 200 cis-2-[5-Chloro-2-(3-ethyl-2,3,4,5-tetrahydro-1H-benzo[d]azepin-7-ylamino)-pyrimidin-4-ylamino]-cyclohexanecarboxylic acid methylamide 200a) 2,5,6-trichloropyrimidine (368 mg, 2.0 mmol), cis-2-amino-cyclohexanecarboxylic acid methylamide (308 mg, 2.0 mmol), and N,N-diisopropylethylamine (387 mg, 3.0 mmol) were combined in 10 mL isopropyl alcohol and stirred at room temperature for 24 hours. The reaction was concentrated and the organics were partitioned between dichloromethane and saturated sodium bicarbonate solution (100 mL each). The organic layer was separated and was dried (sodium sulfate) to afford a solid which was purified on silica gel (1% to 3% methanol:dichloromethane gradient elution) to afford 502 mg (83%) of cis-2-(2,5-dichloro-pyrimidin-4-ylamino)-cyclohexanecarboxylic acid methylamide as a white foam. Mp: 108° C.

200b) cis-2-(2,5-dichloro-pyrimidin-4-ylamino)-cyclohexanecarboxylic acid methylamide (45 mg, 0.15 mmol) and 3-ethyl-2,3,4,5-tetrahydro-1H-benzo[d]azepin-7-ylamine (30 mg, 0.16 mmol) were combined with camphorsulfonic acid (60 mg, 0.25 mmol) in 3 mL isopropyl alcohol and subjected to microwave irradiation at 120° C. for 2 hours. Solid sodium bicarbonate (a pinch) was added and the mixture was stored in a freezer overnight. The mixture was subsequently concentrated and the organics were partitioned between dichloromethane and saturated sodium bicarbonate solution (100 mL each). The organic layer was separated and was dried (sodium sulfate) to afford a solid which was purified on amine functionalized silica (10% to 100% ethyl acetate:hexane gradient elution) to afford 32 mg (47%) of a white solid. Mp: 143° C.; MS: 458.59 (M+H); ¹H NMR (chloroform-d): δ 7.90 (s, 1H), δ 7.35-7.24 (m, 2H), δ 7.04 (d, J=8 Hz, 1H), δ 6.82 (s, 1H), δ 6.51 (d, J=7 Hz, 1H), δ 5.64 (br s, 1H), δ 4.34 (m, 1H), δ 2.97-2.54 (m, 6H), δ 2.79 (d, J=4 Hz, 3H), δ 2.36-0.78 (m, 13H), δ 1.12 (t, J=7 Hz, 3H).

Example 211

3-[5-Chloro-2-(3-ethyl-2,3,4,5-tetrahydro-1H-benzo[d]azepin-7-ylamino)-pyrimidin-4-ylamino]-N-methyl-propionamide 211a) (2-Methylcarbamoyl-ethyl)-carbamic acid tert-butyl ester. N-Boc-β-alanine (500 mg, 2.64 mmol) was dissolved in THF (35 mL) and the solution was treated with 2M methylamine in THF (1.32 mL, 2.64 mmol), 1-Ethyl-3-(3-dimethyllaminopropyl)carbodiimide hydrochloride (504 mg, 2.64 mmol) and 4-hydroxybenzotriazole (401 mg, 2.64 mmol). The reaction was allowed to stir overnight at room temperature. The solution was then poured over saturated sodium bicarbonate (50 mL) and organics were extracted with dichloromethane (3×50 mL). Combined organic extracts were dried over sodium sulfate, filtered and reduced en vacuo to afford (2-Methylcarbamoyl-ethyl)-carbamic acid tert-butyl ester. The crude material was used without further purification.

211b) (2-Methylcarbamoyl-ethyl)-carbamic acid tert-butyl ester (534 mg, 2.64 mmol) was dissolved in dichloromethane (10 mL) and the solution was treated with trifluoroacetic acid (3 mL). The reaction was allowed to stir overnight at room temperature. The solvent and excess TFA was then concentrated to afford 3-Amino-N-methyl-propionamide as a crude TFA salt. The crude material (270 mg) was used without further purification.

211c) 3-(2,5-Dichloro-pyrimidin-4-ylamino)-N-methyl-propionamide. 3-Amino-N-methyl-propionamide (270 mg, 2.64 mmol) was dissolved in DMF (20 mL) and the solution was treated with potassium carbonate (1.09 g, 7.92 mmol). The reaction were then stirred overnight at room temperature. Solvent was removed en vacuo and the residue was taken up in ethyl acetate (25 mL). The organic layer was then washed with saturated $NH_4Cl$ (50 mL). Combined organic extracts (3×25 mL) were dried over $Na_2SO_4$, filtered and reduced. Purification via flash column chromatography (0% ethyl acetate/hexanes-100% ethyl acetate/hexanes) afforded 100 mg of 3-(2,5-Dichloro-pyrimidin-4-ylamino)-N-methyl-propionamide. LC/MS (ESI)=249.14 (M+H).

211d) A solution of 3-(2,5-Dichloro-pyrimidin-4-ylamino)-N-methyl-propionamide (35 mg, 0.14 mmol) in isopropanol (3 mL) was treated 3-Ethyl-2,3,4,5-tetrahydro- 1H-benzo[d]azepin-7-ylamine (27 mg, 0.14 mmol) and 4N HCl/dioxane (0.035 mL, 0.14 mmol). The reaction was irradiated at 130° C. for a total of 20 minutes. A white precipitate formed in the reaction mixture, which was collected via vacuum filtration and triturated with acetonitrile (5 mL) to afford 3-[5-Chloro-2-(3-ethyl-2,3,4,5-tetrahydro-1H-benzo[d]azepin-7-ylamino)-pyrimidin-4-ylamino]-N-methyl-propionamide (13.5 mg) as the HCl salt. LC/MS (ESI)=403.02 (M+H), MP=206.1° C. $^1$H NMR (400 MHz, DMSO, $d_6$) δ 10.51 (m, 1H), 10.05 (m, 1H), 8.12 (s, 1H), 7.88 (m, 1H), 7.59 (s, 1H), 7.42 (m, 1H), 7.17 (d, 1H, J=8.34 Hz), 3.62 (m, 7H), 3.29 (m, 2H), 3.17 (m, 2H), 2.93 (m, 2H), 2.59 (s, 3H), 2.45 (m, 2H), 1.27 (m, 3H).

Example 212

4-[5-Chloro-2-(3-ethyl-2,3,4,5-tetrahydro-1H-benzo[d]azepin-7-ylamino)-pyrimidin-4-ylamino]-N-methyl-butyramide 212a) 4-[5-Chloro-2-(3-ethyl-2,3,4,5-tetrahydro-1H-benzo[d]azepin-7-ylamino)-pyrimidin-4-ylamino]-N-methyl-butyramide was made in an analogous fashion to Example 1 replacing N-Boc-β-alanine with N-Boc-γ-butyric acid. LC/MS (ESI)=417.36 (M+H), MP=135.0° C. $^1$H NMR (400 MHz, DMSO, $d_6$) δ 9.21 (s, 1H), 9.02 (s, 1H), 7.89 (s, 1H), 7.61 (m, 1H), 7.46 (s, 1H), 7.11 (m, 1H), 6.96 (d, 1H, J=8.09 Hz), 3.65 (m, 6H), 3.39 (m, 2H), 2.74 (m, 2H), 2.56 (s, 3H), 2.12 (m, 2H), 1.82 (m, 2H), 1.29 (m, 3H), 1.01 (m, 2H).

Example 213

2-[5-Chloro-2-(1,4-dimethyl-5-oxo-2,3,4,5-tetrahydro-1H-benzo[e][1,4]diazepin-6-ylamino)-pyrimidin-4-ylamino]-N-methyl-benzamide 213a) A solution of 2-fluoro-6-nitrobenzoic acid (10.3 g, 56 mmol) was dissolved in THF/MeOH (100 mL/40 mL) and the mixture was cooled to 0° C. 2M Trimethylsilyldiazomethane in ether (33.4 mL, 67 mmol) was then added dropwise. The reaction was allowed to stir overnight while gradually warming to room temperature. The reaction mixture was then reduced en vacuo to afford 11.1 grams of 2-fluoro-6-nitrobenzoic acid methyl ester as a light brown solid. $^1$H NMR (400 MHz, CDCl$_3$) δ 7.98 (d, 1H, J=7.32), 7.61 (m, 1H), 7.50 (m, 1H), 4.00 (s, 3H).

213b) 6-Amino-1,4-dimethyl-1,2,3,4-tetrahydro-benzo[e][1,4]diazepin-5-one. 2-fluoro-6-nitrobenzoic acid methyl ester (2.4 g, 12.1 mmol) was dissolved in n-butanol (100 mL) and the solution was treated with N,N-dimethylethylenediamine (1.06 mL, 12.1 mmol) and sodium carbonate (1.28 g, 12.1 mmol). The reaction mixture was then heated at 80° C. for 48 hours. The solution was poured over saturated NH$_4$Cl (100 mL) and organics were extracted with ethyl acetate (3×100 mL). Combined extracts were dried over Na$_2$SO$_4$, filtered and reduced. Purification via flash column (0% ethyl acetate/hexane-100% ethyl acetate hexane) afforded 300 mg of 6-Amino-1,4-dimethyl-1,2,3,4-tetrahydro-benzo[e][1,4]diazepin-5-one as a yellow oil.

213c) 6-Amino-1,4-dimethyl-1,2,3,4-tetrahydro-benzo[e][1,4]diazepin-5-one. A solution of 6-Amino-1,4-dimethyl-1,2,3,4-tetrahydro-benzo[e][1,4]diazepin-5-one (300 mg, 1.28 mmol) in methanol (10 mL) was added to roundbottom flask containing 10% Palladium/Carbon (250 mg) under nitrogen. The reaction was flushed under vacuum and was then charged with hydrogen (via balloon) at atmospheric pressure. The solution was then allowed to stir overnight at room temperature. The reaction mixture was filtered through a Celite pad and the filtrate was reduced en vacuo to afford 130 mg of 6-Amino-1,4-dimethyl-1,2,3,4-tetrahydro-benzo[e][1,4]diazepin-5-one as a light brown oil. The crude mixture was used without further purification.

213d) 2-[5-Chloro-2-(1,4-dimethyl-5-oxo-2,3,4,5-tetrahydro-1H-benzo[e][1,4]diazepin-6-ylamino)-pyrimidin-4-ylamino]-N-methyl-benzamide. A solution of 6-Amino-1,4-dimethyl-1,2,3,4-tetrahydro-benzo[e][1,4]diazepin-5-one (53 mg, 0.26 mmol) in isopropanol (3 mL) was treated with 2-(2,5-Dichloro-pyrimidin-4-ylamino)-N-methyl-benzamide (76 mg, 0.26 mmol) and 4N HCl/dioxane (0.065 mL, 0.26 mmol). The reaction was irradiated at 130° C. for a total of 20 minutes. A white precipitate formed in the reaction mixture, which was collected via vacuum filtration and triturated with acetonitrile (5 mL) to afford 2-[5-Chloro-2-(1,4-dimethyl-5-oxo-2,3,4,5-tetrahydro-1H-benzo[e][1,4]diazepin-6-ylamino)-pyrimidin-4-ylamino]-N-methyl-benzamide (52.5 mg) as the HCl salt. (m+H)=466.30, m.p.=203.9° C. $^1$H NMR (400 MHz, DMSO, $d_6$) δ 9.25 (s, 1H), 9.11 (s, 1H), 8.89 (m, 3H), 7.79 (d, 1H, J=8.34 Hz), 7.73 (t, 1H, J=7.83 Hz), 7.44 (t, 1H, J=7.58 Hz), 7.23 (d, 1H, J=7.83 Hz), 7.15 (d, 1H, J=8.33 Hz), 3.41 (m, 2H), 3.25 (m, 2H), 2.92 (s, 3H), 2.85 (s, 3H), 2.61 (s, 3H).

Example 214

N-{(1R,2R)-2-[5-Chloro-2-(1,4-dimethyl-5-oxo-2,3,4,5-tetrahydro-1H-benzo[e][1,4]diazepin-6-ylamino)-pyrimidin-4-ylamino]-cyclohexyl}-methanesulfonamide 214a) Analogous to Example 213, Example 214 was prepared using N-[(1R,2R)-2-(2,5-Dichloro-pyrimidin-4-ylamino)-cyclohexyl]-methanesulfonamide. LC/MS (ESI)=508.35 (M+H), MP=160.2° C. $^1$H NMR (400 MHz, DMSO, $d_6$) δ 9.18 (s, 1H), 8.01 (d, 1H, J=2.11 Hz), 7.92 (s, 1H), 7.30 (m, 1H), 7.17 (d, 1H, J=8.84 Hz), 6.79 (d, 1H, J=7.58 Hz), 6.64 (d, 1H, J=8.33 Hz), 3.80 (m, 1H), 3.39 (m, 2H), 3.16 (m, 2H), 3.11 (s, 3H), 2.93 (s, 3H), 2.73 (s, 3H), 1.99 (m, 3H), 1.69 (m, 2H), 1.19 (m, 4H).

Example 215

N-{2-[5-Chloro-2-(1,4-dimethyl-5-oxo-2,3,4,5-tetrahydro-1H-benzo[e][1,4]diazepin-6-ylamino)-pyrimidin-4-ylamino]-phenyl}-methanesulfonamide 215a) Prepared analogous to Example 213 using N-[2-(2,5-Dichloro-pyrimidin-4-ylamino)-phenyl]-methanesulfonamide. N-{2-[5-Chloro-2-(1,4-dimethyl-5-oxo-2,3,4,5-tetrahydro-1H-benzo[e][1,4]diazepin-6-ylamino)-pyrimidin-4-ylamino]-phenyl}-methanesulfonamide purified by prep HPLC and isolated as a foam. LC/MS (ESI)=502.24 (M+H). $^1$H NMR (400 MHz, DMSO, $d_6$) δ 9.49 (s, 1H), 9.15 (s, 1H), 8.34 (m, 1H), 7.61 (m, 1H), 7.51 (m, 1H), 7.42 (m, 1H), 7.39 (m, 1H), 7.07 (m, 3H), 3.30 (m, 4H), 3.05 (s, 3H), 2.89 (s, 3H), 2.68 (s, 3H).

Example 216

5-Chloro-N*2*-(3-ethyl-2,3,4,5-tetrahydro-1H-benzo[d]azepin-7-yl)-N*4*-[2-(1-methyl-1H-imidazol-2-yl)-phenyl]-pyrimidine-2,4-diamine 216a) [2-(1-Methyl-1H-imidazol-2-yl)-phenyl]-carbamic acid tert-butyl ester. THF (3 mL) was added to palladium acetate (35 mg, 0.12 mmol) and triphenylphosphine (126 mg, 0.48 mmol). The mixture was allowed to stir at room temperature under nitrogen for 5 minutes and 2-iodo-1-methyl-1H-imidazole (500 mg, 2.4 mmol) was added. After stirring an additional 5 minutes, a solution of 2-Boc-aminophenyl boronic acid (1.14 g, 4.01 mmol) in ethanol (5 mL) was added via syringe. The solution was then treated with saturated sodium carbonate (5 mL) and was heated to reflux. After stirring overnight at reflux, the reaction was cooled and poured over brine (25 mL). Organics were extracted with ether and combined extracts were dried over sodium sulfate, filtered and reduced. The compound was then purified via flash column chromatography (0% ethyl acetate/hexanes-60% ethyl acetate/hexanes) to afford 380 mg of [2-(1-Methyl-1H-imidazol-2-yl)-phenyl]-carbamic acid tert-butyl ester.

216b) 2-(1-Methyl-1H-imidazol-2-yl)-phenylamine. [2-(1-Methyl-1H-imidazol-2-yl)-phenyl]-carbamic acid tert-butyl ester (380 mg, 1.39 mmol) was dissolved in dichloromethane (5 mL) and the solution was treated with trifluoroacetic acid (1 mL). The reaction was allowed to stir overnight at room temperature. Volatiles were removed en vacuo and the resulting crude mixture was used without further purification, crude yield: 270 mg, theoretical yield 240 mg.

216c) (2,5-Dichloro-pyrimidin-4-yl)-[2-(1-methyl-1H-imidazol-2-yl)-phenyl]-amine. A solution of crude 2-(1-Methyl-1H-imidazol-2-yl)-phenylamine (220 mg, 1.27 mmol) in DMF (8 mL) was treated with 2,4,5-trichloropyrimidine (233 mg, 1.27 mmol) and potassium carbonate (526 mg, 3.81 mmol). The mixture was then heated to 80° C. and was allowed to stir overnight. The reaction mixture was then cooled and DMF was removed en vacuo. The residue was taken up in ethyl acetate (20 mL) and was poured over saturated $NH_4Cl$ (20 mL). The organics were then extracted with ethyl acetate (3×20 mL). Combined extracts were dried over sodium sulfate, filtered and reduced. The product was then isolated and purified by flash column chromatography (0% ethyl acetate/hexane-75% ethyl acetate hexane) to afford 140 mg of (2,5-Dichloro-pyrimidin-4-yl)-[2-(1-methyl-1H-imidazol-2-yl)-phenyl]-amine as an off white solid.

216d) A solution of (2,5-Dichloro-pyrimidin-4-yl)-[2-(1-methyl-1H-imidazol-2-yl)-phenyl]-amine (47 mg, 0.15 mmol) in 2-methoxyethanol (3 mL) was treated with 3-Ethyl-2,3,4,5-tetrahydro-1H-benzo[d]azepin-7-ylamine (28 mg, 0.15 mmol) and 4N HCl/Dioxane (0.074 mL, 0.29 mmol). The reaction mixture was heated to 120° C. and was allowed to stir for approximately 4 hours. The reaction mixture was then reduced en vacuo and the product was purified and isolated by prep HPLC to afford 44.5 mg of 5-Chloro-N*2*-(3-ethyl-2,3,4,5-tetrahydro-1H-benzo[d]azepin-7-yl)-N*4*-[2-(1-methyl-1H-imidazol-2-yl)-phenyl]-pyrimidine-2,4-diamine as the TFA salt. The product was isolated as a foam, LC/MS (ESI)=474.42 (M+H). $^1$H NMR (400 MHz, CDCl$_3$) δ 7.89 (t, 1H, J=7.58 Hz), 7.74 (m, 2H), 7.66 (d, 1H), 7.45 (d, 1H, J=7.83 Hz), 7.39 (s, 1H), 7.08 (s, 1H), 6.97 (m, 2H), 6.81 (d, 1H, J=8.08 Hz), 3.72 (m, 2H), 3.49 (m, 2H), 3.33 (m, 2H), 3.21 (s, 3H), 2.87 (m, 2H), 2.67 (m, 2H), 1.40 (t, 3H, J=7.07 Hz).

Example 217

2-{5-Chloro-4-[2-(1-methyl-1H-imidazol-2-yl)-phenylamino]-pyrimidin-2-ylamino}-5,6,8,9-tetrahydro-benzocyclohepten-7-one 217a) Example 217 was synthesized in a similar manner to Example 216 replacing 3-Ethyl-2,3,4,5-tetrahydro-1H-benzo[d]azepin-7-ylamine with 2-Amino-5,6,8,9-tetrahydro-benzocyclohepten-7-one to give 2-{5-Chloro-4-[2-(1-methyl-1H-imidazol-2-yl)-phenylamino]-pyrimidin-2-ylamino}-5,6,8,9-tetrahydro-benzocyclohepten-7-one. LC/MS (ESI)=459.37 (M+H), MP=149.2° C. $^1$H NMR (400 MHz, DMSO, d$_6$) δ 9.37 (s, 1H), 8.61 (s, 1H), 8.16 (s, 1H), 7.64 (m, 2H), 7.59 (m, 2H), 7.36 (m, 2H), 7.24 (m, 1H), 7.15 (m, 2H), 3.77 (s, 3H), 2.81 (m, 4H), 2.62 (m, 4H).

Example 218

5-Chloro-N*4*-[2-(1-methyl-1H-imidazol-2-yl)-phenyl]-N*2*-(7-morpholin-4-yl-6,7,8,9-tetrahydro-5H-benzocyclohepten-2-yl)-pyrimidine-2,4-diamine 218a) Example 218 was synthesized analogously to Example 216 replacing 3-Ethyl-2,3,4,5-tetrahydro-1H-benzo[d]azepin-7-ylamine with 7-Morpholin-4-yl-6,7,8,9-tetrahydro-5H-benzocyclohepten-2-ylamine to give 5-Chloro-N*4*-[2-(1-methyl-1H-imidazol-2-yl)-phenyl]-N*2*-(7-morpholin-4-yl-6,7,8,9-tetrahydro-5H-benzocyclohepten-2-yl)-pyrimidine-2,4-diamine. LC/MS (ESI)= 530.43 (M+H), MP=117.6° C. $^1$H NMR (400 MHz, DMSO, d$_6$) δ 9.27 (s, 1H), 8.60 (m, 1H), 8.14 (s, 1H), 7.65 (d, 1H, J=7.84), 7.42 (m, 2H), 7.33 (m, 2H), 7.22 (m, 1H), 7.17 (s, 1H), 7.00 (d, 1H, J=8.34 Hz), 3.77 (s, 3H), 3.55 (m, 4H), 2.64 (m, 1H), 2.58 (m, 4H), 2.48 (m, 4H), 1.96 (m, 2H), 1.31 (m, 2H).

Example 219

5-Chloro-N*2*-(7,7-difluoro-6,7,8,9-tetrahydro-5H-benzocyclohepten-2-yl)-N*4*-[2-(1-methyl-1H-imidazol-2-yl)-phenyl]-pyrimidine-2,4-diamine 219a) Example 219 was synthesized analogously to Example 216 replacing 3-Ethyl-2,3,4,5-tetrahydro-1H-benzo[d]azepin-7-ylamine with 7,7-Difluoro-6,7,8,9-tetrahydro-5H-benzocyclohepten-2-ylamine. 5-Chloro-N*2*-(7,7-difluoro-6,7,8,9-tetrahydro-5H-benzocyclohepten-2-yl)-N*4*-[2-(1-methyl-1H-imidazol-2-yl)-phenyl]-pyrimidine-2,4-diamine was isolated as a foam. LC/MS (ESI)=481.96 (M+H). $^1$H NMR (400 MHz, DMSO, d$_6$) δ 9.09 (m, 2H), 8.12 (s, 1H), 7.74 (m, 5H), 7.56 (m, 1H), 7.41 (s, 1H), 7.26 (m, 1H), 6.99 (d, 1H, J=8.09 Hz), 3.61 (s, 3H), 2.67 (m, 2H), 2.50 (m, 2H), 1.96 (m, 4H).

Example 220

7-{5-Chloro-4-[2-(1H-imidazol-2-yl)-phenylamino]-pyrimidin-2-ylamino}-5,5-dimethyl-1,3,4,5-tetrahydro-benzo[b]azepin-2-one Example 220 was synthesized analogously to Example 216 replacing 2-iodo-1-methyl-1H-imidazole with 1-Ethoxymethyl-2-iodo-1H-imidazole and 3-Ethyl-2,3,4,5-tetrahydro-1H-benzo[d]azepin-7-ylamine with 7-Amino-5,5-dimethyl-1,3,4,5-tetrahydro-benzo[b]azepin-2-one. The ethoxymethyl protecting group decomposed thermally to provide the unprotected imidazole. 7-{5-Chloro-4-[2-(1H-imidazol-2-yl)-phenylamino]-pyrimidin-2-ylamino}-5,5-dimethyl-1,3,4,5-tetrahydro-benzo[b]azepin-2-one was isolated as a foam. LC/MS (ESI)=474.22 (M+H). $^1$H NMR (400 MHz, MeOD, d$_4$) δ 8.01 (s, 1H), 7.77 (m, 1H), 7.70 (d, 1H, J=7.57 Hz), 7.60 (m, 1H), 7.49 (m, 3H), 7.32 (m, 1H), 7.21 (m, 1H), 6.85 (d, 1H, J=8.59 Hz), 2.32 (m, 2H), 2.07 (m, 2H), 1.36 (s, 6H).

Example 221

5-Chloro-N*4*-[2-(1H-imidazol-2-yl)-phenyl]-N*2*-[3-(2-methoxy-ethyl)-2,3,4,5-tetrahydro-1H-benzo[d]azepin-7-yl]-pyrimidine-2,4-diamine 221a) Example 221 was synthesized analogously to Example 216 replacing 2-iodo-1-methyl-1H-imidazole with 1-Ethoxymethyl-2-iodo-1H-imidazole and 3-Ethyl-2,3,4,5-tetrahydro-1H-benzo[d]azepin-7-ylamine with 3-(2-Methoxy-ethyl)-2,3,4,5-tetrahydro-1H-benzo[d]azepin-7-ylamine. The ethoxy-methyl protecting group decomposed thermally to provide the unprotected imidazole. 5-Chloro-N*4*-[2-(1H-imidazol-2-yl)-phenyl]-N*2*-[3-(2-methoxy-ethyl)-2,3,4,5-tetrahydro-1H-benzo[d]azepin-7-yl]-pyrimidine-2,4-diamine was isolated as a foam. LC/MS (ESI)=489.96 (M+H). $^1$H NMR (400 MHz, MeOD, d$_4$) δ 8.05 (s, 1H), 7.86 (s, 1H), 7.76 (m, 1H), 7.70 (m, 1H), 7.55 (m, 3H), 7.34 (m, 3H), 7.20 (d, 2H, J=8.08 Hz), 7.05 (d, 1H, J=8.08 Hz), 3.77 (m, 4H), 3.45 (s, 3H), 3.20 (m, 2H), 3.05 (m, 4H), 2.91 (m, 2H).

Example 222

5-Chloro-N*4*-[2-(1-ethoxymethyl-1H-imidazol-2-yl)-phenyl]-N*2*-[3-(2-methoxy-ethyl)-2,3,4,5-tetrahydro-1H-benzo[d]azepin-7-yl]-pyrimidine-2,4-diamine 222a) Example 222 was synthesized analogously to Example 216 replacing 2-iodo-1-methyl-1H-imidazole with 1-Ethoxymethyl-2-iodo-1H-imidazole and 3-Ethyl-2,3,4,5-tetrahydro-1H-benzo[d]azepin-7-ylamine with 3-(2-Methoxy-ethyl)-2,3,4,5-tetrahydro-1H-benzo[d]azepin-7-ylamine. A small amount of the protected imidazole was isolated by prep HPLC. 5-Chloro-N*4*-[2-(1-ethoxymethyl-1H-imidazol-2-yl)-phenyl]-N*2*-[3-(2-methoxy-ethyl)-2,3,4,5-tetrahydro-1H-benzo[d]azepin-7-yl]-pyrimidine-2,4-diamine was isolated as a foam. LC/MS (ESI)=548.00 (M+H). $^1$H NMR (400 MHz, MeOD, d$_4$) δ 8.02 (s, 1H), 7.80 (m, 4H), 7.61 (m, 2H), 7.33 (s, 1H), 7.23 (d, 1H, J=8.59 Hz), 7.04 (d, 1H, J=8.08 Hz), 3.76 (m, 4H), 3.50 (m, 2H), 3.45 (s, 3H), 3.30 (m, 4H), 3.15 (m, 4H), 2.86 (m, 2H), 1.09 (t, 3H, J=7.07 Hz).

Example 223

7-[5-Chloro-4-(2-pyridin-2-yl-phenylamino)-pyrimidin-2-ylamino]-5,5-dimethyl-1,3,4,5-tetrahydro-benzo[b]azepin-2-one 223a) Example 223 was synthesized analogously to Example 216 replacing 2-iodo-1-methyl-1H-imidazole with 2-bromopyridine and 3-Ethyl-2,3,4,5-tetrahydro-1H-benzo[d]azepin-7-ylamine with 7-Amino-5,5-dimethyl-1,3,4,5-tetrahydro-benzo[b]azepin-2-one. 7-[5-Chloro-4-(2-pyridin-2-yl-phenylamino)-pyrimidin-2-ylamino]-5,5-dimethyl-1,3,4,5-tetrahydro-benzo[b]azepin-2-one was isolated as a foam. LC/MS (ESI)=486.96 (M+H). $^1$H NMR (400 MHz, DMSO, d$_6$) δ 12.96 (s, 1H), 9.48 (s, 1H), 9.39 (s, 1H), 9.05 (d, 2H, J=4.91 Hz), 8.92 (m, 1H), 8.56 (d, 1H, J=7.99 Hz), 8.25 (s, 1H), 7.68 (d, 1H, J=8.45 Hz), 7.49 (m, 3H), 7.24 (t, 1H, J=7.39 Hz), 6.91 (d, 1H, J=8.59 Hz), 2.12 (t, 2H, J=7.17 Hz), 1.98 (t, 2H, J=6.96 Hz), 1.29 (s, 6H).

Example 224

5-Chloro-N*2*-[3-(2-methoxy-ethyl)-2,3,4,5-tetrahydro-1H-benzo[d]azepin-7-yl]-N*4*-(2-pyridin-2-yl-phenyl)-pyrimidine-2,4-diamine 224a) Example 224 was synthesized analogously to Example 216 replacing 2-iodo-1-methyl-1H-imidazole with 2-bromopyridine and 3-Ethyl-2,3,4,5-tetrahydro-1H-benzo[d]azepin-7-ylamine with 3-(2-Methoxy-ethyl)-2,3,4,5-tetrahydro-1H-benzo[d]azepin-7-ylamine. 5-Chloro-N*2*-[3-(2-methoxy-ethyl)-2,3,4,5-tetrahydro-1H-benzo[d]azepin-7-yl]-N*4*-(2-pyridin-2-yl-phenyl)-pyrimidine-2,4-diamine was isolated as a foam. (m+H)=503.02. $^1$H NMR (400 MHz, MeOD, d$_4$) δ 8.97 (d, 2H, J=4.94 Hz), 8.76 (m, 1H), 8.60 (d, 1H, J=7.82 Hz), 8.13 (s, 1H), 7.56 (s, 1H), 7.45 (m, 3H), 7.28 (m, 2H), 7.21 (d, 1H, J=8.13 Hz), 3.79 (m, 4H), 3.51 (m, 2H), 3.47 (s, 3H), 3.25 (m, 2H), 3.15 (m, 4H).

Example 225

N-{2-[5-Chloro-2-(3-oxo-2,3,4,5-tetrahydro-1H-benzo[e][1,3]diazepin-7-ylamino)-pyrimidin-4-ylamino]-phenyl}-methanesulfonamide 225a) α,α'-Dibromoxylene (5.05 g, 19.1 mmol) was dissolved in N,N-dimethylformamide (160 mL) and the solution was treated with potassium phthalimide (10.7 g, 57.6 mmol). The reaction was then heated to reflux and was allowed to stir overnight. The reaction was then poured over water and the precipitate was collected via vacuum filtration and was dried en vacuo to afford 4.6 g of Diphthalimidoyl-o-xylene as a white fluffy powder.

225b) A solution of potassium nitrate (1.41 g, 13.9 mmol) and concentrated sulfuric acid (50 mL) was cooled to 0° C. and Diphthalimidoyl-o-xylene (4.6 g, 11.6 mmol) was added portionwise. The reaction was allowed to stir overnight at room temperature. The solution was then carefully poured over ice-water (100 mL) and the precipitate that formed was collected via vacuum filtration to afford 5.1 g of 2-nitro-diphthalimidoyl-o-xylene as a white solid. 2-nitro-diphtalimidoyl-o-xylene was used without further purification.

225c) 2-nitro-diphtalimidoyl-o-xylene (5.1 g, 11.6 mmol) was suspended in ethanol (100 mL) and the solution was treated with hydrazine hydrate (2.88 mL, 57.6 mmol). The reaction was then allowed to stir overnight at room temperature. Solids were then filtered from the reaction and the filtrate was reduced en vacuo. The resulting residue was then triturated with chloroform for 1 hour. Solids were again removed via vacuum filtration and the filtrate was reduced en vacuo to afford 1.80 g of 2-aminomethyl-4-nitrobenzylamine as a brown oil. The crude material was used in further synthesis without additional purification.

225d) 2-aminomethyl-4-nitrobenzylamine (3.10 g, 17.1 mmol) was dissolved in tetrahydrofuran (300 mL) and a solution of N,N-carbonyldiimidazole (2.78 g, 17.1 mmol) in THF (40 mL) was added dropwise at room temperature over 30 minutes. The reaction was allowed to stir at room temperature for 72 hours. The solution was then poured over water (150 mL) and organics were extracted with ethyl acetate (3×100 mL). Combined organic extracts were dried over Na$_2$SO$_4$, filtered and reduced to afford 7-nitro-1,2,4,5-tetrahydro-benzo(e)(1,3)diazepin-3-one as a crude brown solid. Purification by flash column chromatography (0% MeOH/

DCM-10% MeOH/DCM) afforded 2.5 grams of 7-nitro-1,2,4,5-tetrahydro-benzo(e)(1,3)diazepin-3-one as a yellow solid. LC/MS (ESI)=208.42 (M+H).

225e) Compound 7-nitro-1,2,4,5-tetrahydro-benzo(e)(1,3)diazepin-3-one (2.00 g, 9.65 mmol) was dissolved in methanol (60 mL) and the solution was carefully added to a Parr shaker vessel containing 10% Palladium/Carbon (200 mg) under nitrogen. The reaction was then shaken under 50 psi of hydrogen until uptake of hydrogen had ceased (3 hours). Catalyst was then removed via filtration through a Celite pad. The filter cake was rinsed with methanol (3×50 mL) and the filtrate was reduced en vacuo to afford 1.20 g of 7-amino-1,2,4,5-tetrahydro-(2,4)-benzodiazepin-3-one as a white solid. LC/MS (ESI)=178.32 (M+H). $R_f$: (10% MeOH/DCM)=0.31.

225f) A solution of 7-amino-1,2,4,5-tetrahydro-(2,4)-benzodiazepin-3-one (75.0 mg, 0.42 mmol) in isopropanol (3 mL) was treated with N-[2-(2,5-Dichloro-pyrimidin-4-ylamino)-phenyl]-methanesulfonamide (140.2 mg, 0.42 mmol) and 4N HCl/Dioxane (0.106 mL, 0.50 mmol). The reaction mixture was irradiated at 130° C. for a total of 60 minutes. The reaction mixture was then reduced en vacuo and the product was purified and isolated flash column chromatography (0% MeOH/DCM-15% MeOH/DCM) to afford 1.98 mg of N-{2-[5-Chloro-2-(3-oxo-2,3,4,5-tetrahydro-1H-benzo[e][1,3]diazepin-7-ylamino)-pyrimidin-4-ylamino]-phenyl}-methanesulfonamide as the HCl salt. The compound was isolated as a foam, LC/MS (ESI)=480.35 (M+H). $^1$H NMR (400 MHz, MeOD, $d_4$) δ 7.68 (m, 2H), 7.46 (m, 1H), 7.29 (m, 2H), 7.06 (m, 4H), 6.62 (m, 1H), 4.31 (m, 2H), 4.19 (m, 2H), 3.47 (s, 1H), 3.12 (s, 1H), 2.92 (s, 3H).

Example 226

N-{(1R,2R)-2-[5-Chloro-2-(3-oxo-2,3,4,5-tetrahydro-1H-benzo[e][1,3]diazepin-7-ylamino)-pyrimidin-4-ylamino]-cyclohexyl}-methanesulfonamide 226a) Example 226 was synthesized in a similar manner as Example 225 replacing N-[2-(2,5-Dichloro-pyrimidin-4-ylamino)-phenyl]-methanesulfonamide with N-[(1R,2R)-2-(2,5-Dichloro-pyrimidin-4-ylamino)-cyclohexyl]-methanesulfonamide. N-{(1R,2R)-2-[5-Chloro-2-(3-oxo-2,3,4,5-tetrahydro-1H-benzo[e][1,3]diazepin-7-ylamino)-pyrimidin-4-ylamino]-cyclohexyl}-methanesulfonamide was isolated as a foam, LC/MS (ESI)=480.35 (M+H). $^1$H NMR (400 MHz, MeOD, $d_4$) δ 7.85 (s, 1H), 7.67 (s, 1H), 7.53 (m, 1H), 7.36 (m, 1H), 7.16 (m, 1H), 7.05 (m, 1H), 6.89 (m, 1H), 6.73 (m, 1H), 6.63 (m, 1H), 4.30 (m, 2H), 4.20 (s, 2H), 3.48 (m, 1H), 3.12 (m, 1H), 2.90 (s, 3H), 1.80 (m, 2H), 1.43 (m, 4H), 1.15 (m, 2H).

Example 227

2-[5-Chloro-2-(3-oxo-2,3,4,5-tetrahydro-1H-benzo[e][1,3]diazepin-7-ylamino)-pyrimidin-4-ylamino]-N-methyl-benzamide 227a) Example 227 was synthesized in a similar manner as Example 225 replacing N-[2-(2,5-Dichloro-pyrimidin-4-ylamino)-phenyl]-methanesulfonamide with 2-(2,5-Dichloro-pyrimidin-4-ylamino)-N-methyl-benzamide. 2-[5-Chloro-2-(3-oxo-2,3,4,5-tetrahydro-1H-benzo[e][1,3]diazepin-7-ylamino)-pyrimidin-4-ylamino]-N-methyl-benzamide was isolated as a foam, LC/MS (ESI)=438.31 (M+H). $^1$H NMR (400 MHz, DMSO, $d_6$) δ 8.74 (m, 2H), 8.24 (s, 1H), 7.77 (m, 1H), 7.60 (m, 1H), 7.51 (m, 2H), 7.14 (m, 2H), 6.40 (m, 2H), 4.09 (m, 2H), 3.98 (m, 2H), 2.80 (s, 3H), 2.67 (m, 1H), 2.33 (m, 1H).

Example 228

(2-exo,3-exo)-3-[5-Chloro-2-(3-oxo-2,3,4,5-tetrahydro-1H-benzo[e][1,3]diazepin-7-ylamino)-pyrimidin-4-ylamino]-bicyclo[2.2.1]hept-5-ene-2-carboxylic acid amide 228a) Example 228 was synthesized in a similar manner as Example 225 replacing N-[2-(2,5-Dichloro-pyrimidin-4-ylamino)-phenyl]-methanesulfonamide with (2-exo,3-exo)-3-(2,5-Dichloro-pyrimidin-4-ylamino)-bicyclo[2.2.1]hept-5-ene-2-carboxylic acid amide. (2-exo,3-exo)-3-[5-Chloro-2-(3-oxo-2,3,4,5-tetrahydro-1H-benzo[e][1,3]diazepin-7-ylamino)-pyrimidin-4-ylamino]-bicyclo[2.2.1]hept-5-ene-2-carboxylic acid amide was isolated as a foam., LC/MS (ESI)=440.31 (M+H). $^1$H NMR (400 MHz, MeOD, $d_4$) δ 7.84 (s, 1H), 7.69 (d, 1H, J=7.84 Hz), 7.48 (s, 1H), 7.17 (d, 1H, J=8.09 Hz), 6.33 (m, 2H), 4.31 (m, 4H), 2.95 (m, 1H), 2.86 (m, 1H), 2.62 (d, 1H, J=8.85 Hz), 2.22 (d, 1H, J=8.84 Hz), 2.02 (m, 1H), 1.88 (s, 1H), 1.56 (m, 1H), 0.87 (m, 2H).

Example 229

2-{5-Chloro-2-[3-methyl-5-oxo-1-(2,2,2-trifluoro-acetyl)-2,3,4,5-tetrahydro-1H-benzo[e][1,4]diazepin-6-ylamino]-pyrimidin-4-ylamino}-N-methyl-benzamide 229a) A solution of 2-fluoro-6-nitrobenzoic acid methyl ester (500 mg, 2.51 mmol) in 1,4-dioxane (3 mL) was treated with 1,2-diaminopropane (0.186 mL, 2.51 mmol) and diisopropylethylamine (0.874 mL, 2.51 mmol). The reaction was irradiated at 140° C. for 20 minutes. The reaction mixture was then reduced en vacuo and purified by flash column chromatography (0% ethyl acetate/hexanes-100% ethyl acetate/hexanes) to afford 370 mg of 3-Methyl-6-nitro-1,2,3,4-tetrahydro-benzo[e][1,4]diazepin-5-one and 2-Methyl-6-nitro-1,2,3,4-tetrahydro-benzo[e][1,4]diazepin-5-one (mixture of regioisomers) as a yellow oil.

229b) 1-Acetyl-3-methyl-6-nitro-1,2,3,4-tetrahydro-benzo[e][1,4]diazepin-5-one and 1-Acetyl-2-methyl-6-nitro-1,2,3,4-tetrahydro-benzo[e][1,4]diazepin-5-one.

A solution of 3-Methyl-6-nitro-1,2,3,4-tetrahydro-benzo[e][1,4]diazepin-5-one and 2-Methyl-6-nitro-1,2,3,4-tetrahydro-benzo[e][1,4]diazepin-5-one (350 mg, 1.58 mmol) was dissolved in dichloromethane (5 mL) and the solution was treated with diisopropylethylamine (0.330 mL, 1.89 mmol) and trifluoroacetic anhydride (332 mg, 1.58 mmol). The reactions were allowed to stir overnight at room temperature for approximately 3 hours. The mixture was then poured over saturated NH$_4$Cl (30 mL) and extracted with dichloromethane (3×15 mL). Combined organic extracts were dried over Na$_2$SO$_4$, filtered and reduced. The crude product was then isolated and purified by flash column chromatography (0% ethyl acetate/hexanes-75% ethyl acetate hexanes) to afford 370 mg of 1-Acetyl-3-methyl-6-nitro-1,2,3,4-tetrahydro-benzo[e][1,4]diazepin-5-one and 1-Acetyl-2-methyl-6-nitro-1,2,3,4-tetrahydro-benzo[e][1,4]diazepin-5-one as a yellow oil.

229c) 1-Acetyl-6-amino-3-methyl-1,2,3,4-tetrahydro-benzo[e][1,4]diazepin-5-one and 1-Acetyl-6-amino-2-methyl-1,2,3,4-tetrahydro-benzo[e][1,4]diazepin-5-one.

1-Acetyl-3-methyl-6-nitro-1,2,3,4-tetrahydro-benzo[e][1,4]

diazepin-5-one and 1-Acetyl-2-methyl-6-nitro-1,2,3,4-tetrahydro-benzo[e][1,4]diazepin-5-one (370 mg, 1.17 mmol) was dissolved in ethanol (10 mL) and the solution was treated with Raney Nickel (50% slurry in water) (2 mL) and hydrazine hydrate (0.584 mL, 11.7 mmol). The reaction was then allowed to stir overnight at room temperature. Catalyst was removed by filtering the reaction mixture through a Celite pad and washing the pad with methanol (3×25 mL). The filtrate was dried over $Na_2SO_4$, filtered and reduced to afford 140 mg of 1-Acetyl-6-amino-3-methyl-1,2,3,4-tetrahydro-benzo[e][1,4]diazepin-5-one and 1-Acetyl-6-amino-2-methyl-1,2,3,4-tetrahydro-benzo[e][1,4]diazepin-5-one as a clear oil. The crude mixture was used without further purification.

229d) 1-Acetyl-6-amino-3-methyl-1,2,3,4-tetrahydrobenzo[e][1,4]diazepin-5-one and 1-Acetyl-6-amino-2-methyl-1,2,3,4-tetrahydro-benzo[e][1,4]diazepin-5-one (47.0 mg, 0.162 mmol) was dissolved in 2-methoxyethanol (2 mL) and the solution was treated with 4N HCl/dioxane (0.02 mL, 0.2 mmol) and 2-(2,5-Dichloro-pyrimidin-4-ylamino)-N-methyl-benzamide (24.0 mg, 0.26 mmol). The reaction mixture was heated to 120° C. and was allowed to stir until HPLC showed consumption of starting materials (~3 hours). The reaction mixture was then reduced en vacuo and only the regioisomer 2-{5-Chloro-2-[3-methyl-5-oxo-1-(2,2,2-trifluoro-acetyl)-2,3,4,5-tetrahydro-1H-benzo[e][1,4]diazepin-6-ylamino]-pyrimidin-4-ylamino}-N-methyl-benzamide could be purified and isolated by prep HPLC. Purification afforded 2.41 mg of 2-{5-Chloro-2-[3-methyl-5-oxo-1-(2,2,2-trifluoro-acetyl)-2,3,4,5-tetrahydro-1H-benzo[e][1,4]diazepin-6-ylamino]-pyrimidin-4-ylamino}-N-methyl-benzamide as the TFA salt. 2-{5-Chloro-2-[3-methyl-5-oxo-1-(2,2,2-trifluoro-acetyl)-2,3,4,5-tetrahydro-1H-benzo[e][1,4]diazepin-6-ylamino]-pyrimidin-4-ylamino}-N-methyl-benzamide was isolated as a foam, LC/MS (ESI)=548.25 (M+H). $^1$H NMR (400 MHz, DMSO, $d_6$) δ 9.50 (d, 1H, J=8.34 Hz), 9.15 (m, 1H), 9.02 (m, 1H), 9.77 (m, 1H), 8.51 (m, 1H), 7.94 (d, 1H, J=8.59 Hz), 7.73 (m, 2H), 7.41 (m, 1H), 6.96 (m, 1H), 6.71 (m, 1H), 3.56 (m, 3H), 2.86 (s, 3H), 1.22 (d, 3H, J=6.56 Hz).

Example 230

N-(2-{5-Chloro-2-[3-methyl-5-oxo-1-(2,2,2-trifluoro-acetyl)-2,3,4,5-tetrahydro-1H-benzo[e][1,4]diazepin-6-ylamino]-pyrimidin-4-ylamino}-phenyl)-methanesulfonamide and N-(2-{5-Chloro-2-[2-methyl-5-oxo-1-(2,2,2-trifluoro-acetyl)-2,3,4,5-tetrahydro-1H-benzo[e][1,4]diazepin-6-ylamino]-pyrimidin-4-ylamino}-phenyl)-methanesulfonamide (Mixture of regioisomers)

230a) Example 230 was prepared in a similar manner to Example 229 replacing 2-(2,5-Dichloro-pyrimidin-4-ylamino)-N-methyl-benzamide with N-[2-(2,5-Dichloro-pyrimidin-4-ylamino)-phenyl]-methanesulfonamide. N-(2-{5-Chloro-2-[3-methyl-5-oxo-1-(2,2,2-trifluoro-acetyl)-2,3,4,5-tetrahydro-1H-benzo[e][1,4]diazepin-6-ylamino]-pyrimidin-4-ylamino}-phenyl)-methanesulfonamide and N-(2-{5-Chloro-2-[2-methyl-5-oxo-1-(2,2,2-trifluoro-acetyl)-2,3,4,5-tetrahydro-1H-benzo[e][1,4]diazepin-6-ylamino]-pyrimidin-4-ylamino}-phenyl)-methanesulfonamide (Mixture of regioisomers) was isolated as a foam, LC/MS (ESI)=584.30 (M+H). $^1$H NMR (400 MHz, DMSO, $d_6$) δ 9.47 (m, 2H), 9.29 (s, 1H), 9.12 (m, 2H), 8.55 (s, 1H), 8.15 (s, 1H), 8.02 (m, 1H), 7.62 (m, 2H), 7.45 (m, 4H), 7.34 (m, 2H), 6.78 (m, 4H), 6.65 (m, 1H), 6.41 (m, 1H), 3.57 (m, 4H), 3.03 (s, 3H), 2.96 (s, 3H), 2.75 (m, 1H), 2.62 (m, 1H), 1.21 (d, 3H, J=6.83 Hz), 1.07 (d, 3H, J=6.06 Hz).

Example 231

N-((1R,2R)-2-{5-Chloro-2-[2-methyl-5-oxo-1-(2,2,2-trifluoro-acetyl)-2,3,4,5-tetrahydro-1H-benzo[e][1,4]diazepin-6-ylamino]-pyrimidin-4-ylamino}-cyclohexyl)-methanesulfonamide 231a) Isolated as a foam, LC/MS (ESI)=590.36 (M+H). $^1$H NMR (400 MHz, DMSO, $d_6$) δ 9.47 (m, 1H), 9.17 (m, 1H), 8.97 (s, 1H), 8.43 (m, 1H), 7.65 (m, 1H), 7.21 (m, 1H), 6.79 (m, 1H), 6.67 (d, 1H, J=7.83 Hz), 3.57 (m, 4H), 2.94 (s, 3H), 2.04 (m, 1H), 1.90 (m, 1H), 1.73 (m, 2H), 1.34 (m, 2H), 1.21 (d, 3H, J=6.32 Hz).

Example 232

N-{(1R,2R)-2-[5-Chloro-2-(3-ethyl-6-methoxy-2,3,4,5-tetrahydro-1H-benzo[d]azepin-7-ylamino)-pyrimidin-4-ylamino]-cyclohexyl}-methanesulfonamide 232a) 3-Ethyl-6-methoxy-2,3,4,5-tetrahydro-1H-benzo[d]azepin-7-ylamine (50.0 mg, (0.23 mmol) was dissolved in isopropanol (3 mL) and the mixture was treated with N-[(1R,2R)-2-(2,5-Dichloro-pyrimidin-4-ylamino)-cyclohexyl]-methanesulfonamide (58 mg, 0.17 mmol) and 4N HCl/Dioxane (0.056 mL, 0.20 mmol). The reaction was then irradiated at 140° C. for 20 minutes. The solution was reduced en vacuo and the product was isolated and purified by flash column chromatography (0% MeOH/DCM-15% MeOH/DCM) to afford 3.83 mg of N-{(1R,2R)-2-[5-Chloro-2-(3-ethyl-6-methoxy-2,3,4,5-tetrahydro-1H-benzo[d]azepin-7-ylamino)-pyrimidin-4-ylamino]-cyclohexyl}-methanesulfonamide as a white foam, LC/MS (ESI)=523.39 (M+H). $^1$H NMR (400 MHz, DMSO, $d_6$) δ 7.93 (s, 1H), 7.82 (m, 2H), 7.07 (d, 1H, J=8.59), 6.86 (m, 1H), 6.77 (m, 1H), 3.71 (m, 2H), 3.62 (s, 3H), 2.89 (s, 3H), 2.67 (m, 4H), 2.59 (m, 1H), 2.53 (m, 2H), 2.42 (m, 2H), 2.34 (m, 1H), 2.04 (m, 2H), 1.70 (m, 2H), 1.35 (m, 2H), 1.23 (m, 2H), 1.03 (m, 3H).

Example 233 and Example 234 were prepared analogously replacing N-[(1R,2R)-2-(2,5-Dichloro-pyrimidin-4-ylamino)-cyclohexyl]-methanesulfonamide with N-[2-(2,5-Dichloro-pyrimidin-4-ylamino)-phenyl]-methanesulfonamide and 2-(2,5-Dichloro-pyrimidin-4-ylamino)-N-methyl-benzamide respectively.

Example 233

N-{2-[5-Chloro-2-(3-ethyl-6-methoxy-2,3,4,5-tetrahydro-1H-benzo[d]azepin-7-ylamino)-pyrimidin-4-ylamino]-phenyl}-methanesulfonamide 233a) Analogous to procedure to Example 232, N-{2-[5-Chloro-2-(3-ethyl-6-methoxy-2,3,4,5-tetrahydro-1H-benzo[d]azepin-7-ylamino)-pyrimidin-4-ylamino]-phenyl}-methanesulfonamide was isolated as a foam, LC/MS (ESI)=517.40 (M+H). $^1$H NMR (400 MHz, MeOD, $d_4$) δ 8.15 (s, 1H), 7.77 (m, 1H), 7.57 (d, 1H, J=8.34 Hz), 7.48 (m, 1H), 7.36 (m, 2H), 6.82 (d, 1H, J=8.34 Hz), 3.70 (s, 3H), 3.51 (m, 4H), 3.26 (m, 2H), 3.10 (m, 4H), 2.94 (s, 3H), 1.36 (t, 3H, J=7.07 Hz).

Example 234

2-[5-Chloro-2-(3-ethyl-6-methoxy-2,3,4,5-tetrahydro-1H-benzo[d]azepin-7-ylamino)-pyrimidin-4-ylamino]-N-methyl-benzamide 234a) Analogous to procedure to Example 232, 2-[5-Chloro-2-(3-ethyl-6-methoxy-2,3,4,5-tetrahydro-1H-benzo[d]azepin-7-ylamino)-pyrimidin-4-ylamino]-N-methyl-benzamide was isolated as a foam, LC/MS (ESI)=481.42 (M+H). $^1$H NMR (400 MHz, DMSO, d$_6$) δ 8.61 (m, 1H), 8.54 (m, 1H), 8.34 (s, 1H), 8.17 (s, 1H), 7.73 (d, 1H, J=7.83 Hz), 7.41 (m, 1H), 7.32 (m, 1H), 7.09 (m, 1H), 7.00 (m, 1H), 6.76 (m, 1H), 3.59 (s, 3H), 2.82 (m, 6H), 2.81 (s, 3H), 2.65 (m, 4H), 1.01 (m, 3H).

Example 235

(1R,2S)-1-[5-Chloro-2-(3-ethyl-2,3,4,5-tetrahydro-1H-benzo[d]azepin-7-ylamino)-pyrimidin-4-ylamino]-indan-2-ol 235a) (1R,2S)-1-(2,5-Dichloro-pyrimidin-4-ylamino)-indan-2-ol (78 mg, 0.26 mmol) was dissolved in isopropanol (3 mL) and the solution was treated with 3-Ethyl-2,3,4,5-tetrahydro-1H-benzo[d]azepin-7-ylamine (50 mg, 0.26 mmol) and 4N HCl/Dioxane (0.66 mL, 0.26 mmol). The reaction was then irradiated at 130° C. for a total of 30 minutes. The reaction mixture was reduced en vacuo and the crude product was isolated and purified by prep HPLC to afford 20.3 mg of (1R,2S)-1-[5-Chloro-2-(3-ethyl-2,3,4,5-tetrahydro-1H-benzo[d]azepin-7-ylamino)-pyrimidin-4-ylamino]-indan-2-ol as an off-white solid. LC/MS (ESI)=450.26 (M+H), MP=209.1° C. $^1$H NMR (400 MHz, DMSO, d$_6$) δ 9.41 (s, 1H), 8.08 (s, 1H), 7.91 (s, 1H), 7.40 (m, 1H), 7.29 (s, 1H), 7.26 (m, 2H), 7.13 (m, 1H), 7.03 (m, 1H), 6.59 (m, 1H), 3.62 (m, 4H), 3.40 (m, 2H), 3.25 (m, 3H), 2.90 (m, 3H), 2.37 (d, 2H, J=5.55 Hz).

Example 236

2-[2-(4-Acetyl-2,3,4,5-tetrahydro-1H-benzo[e][1,4]diazepin-6-ylamino)-5-chloro-pyrimidin-4-ylamino]-N-methyl-benzamide 236a) 2-fluoro-6-nitrobenzoic acid methyl ester (4.54 g, 22.8 mmol), ethylenediamine (1.50 mL, 22.4 mmol) and diisopropylethylamine (8.71 mL, 50 mmol) were dissolved in 1,4-dioxane (40 mL). The reaction mixture was then irradiated at 140° C. for 40 minutes. After cooling, the reaction mixture was poured over saturated ammonium chloride (50 mL), and organics were extracted with ethyl acetate (3×50 mL). The combined organic extracts were dried over Na$_2$SO$_4$, filtered and reduced. The residue was then purified by flash column chromatography (0% MeOH/DCM-20% MeOH/DCM over 35 minutes) to afford 1.2 grams of 6-Nitro-1,2,3,4-tetrahydro-benzo[e][1,4]diazepin-5-one as a yellow oil. LC/MS (ESI)=208.24 (M+H).

236b) 6-Nitro-1,2,3,4-tetrahydro-benzo[e][1,4]diazepin-5-one (1.20 g, 5.8 mmol) was dissolved in THF (50 mL) and the solution was treated with 1N Borane-THF (2.77 mL, 28.95 mmol). The reaction mixture was then refluxed overnight. Upon cooling, the solution was treated with methanol (50 mL) and was then reduced in vacuo. The residue was taken up in ethyl acetate (40 mL) and was washed with saturated NaHCO$_3$ (100 mL). Organics were extracted with ethyl acetate (3×40 mL) and were then dried over Na$_2$SO$_4$, filtered and reduced. The product was then purified and isolated by flash column chromatography (0% MeOH/DCM-30% MeOH/DCM) to afford 140 mg of 6-Nitro-2,3,4,5-tetrahydro-1H-benzo[e][1,4]diazepine as a yellow oil. LC/MS (ESI)=194.32 (M+H). $^1$H NMR (400 MHz, CDCl$_3$) δ 7.26 (m, 2H), 7.06 (d, 1H, J=8.08 Hz), 6.86 (d, 1H, J=8.34 Hz), 5.32 (s, 1H), 4.66 (s, 2H), 3.24 (t, 2H, J=5.05 Hz), 3.00 (t, 2H, J=5.05 Hz).

236c) 6-Nitro-2,3,4,5-tetrahydro-1H-benzo[e][1,4]diazepine (140 mg, 0.74 mmol) was dissolved in dichloromethane (5 mL) and the mixture was treated with acetic anhydride (0.16 mL, 1.68 mmol). The reaction was then allowed to stir overnight at room temperature. The reaction mixture was then poured over water (10 mL) and organics were extracted with dichloromethane (3×10 mL). Combined organics were dried over Na$_2$SO$_4$, filtered and reduced. The crude product was then isolated and purified by flash column chromatography (0% MeOH/DCM-10% MeOH/DCM) to afford 120 mg of 1-(6-Nitro-1,2,3,5-tetrahydro-benzo[e][1,4]diazepin-4-yl)-ethanone as a yellow oil. LC/MS (ESI)=236.30 (M+H). $^1$H NMR (400 MHz, CDCl$_3$) δ 7.26 (m, 2H), 7.07 (d, 1H, J=8.08 Hz), 6.86 (d, 1H, J=8.34 Hz), 5.95 (s, 1H), 4.64 (s, 2H), 3.55 (q, 2H, J=5.56 Hz), 3.33 (t, 2H, J=5.56 Hz), 1.97 (s, 3H).

236d) 1-(6-Amino-1,2,3,5-tetrahydro-benzo[e][1,4]diazepin-4-yl)-ethanone. 1-(6-Nitro-1,2,3,5-tetrahydro-benzo[e][1,4]diazepin-4-yl)-ethanone (120 mg, 0.51 mmol) was dissolved in methanol (20 mL) and was carefully added to a Parr shaker vessel containing 10% Palladium/Carbon (100 mg). The vessel was placed on a Parr hydrogenator and was shaken at 50 psi until uptake of hydrogen had ceased (~2 hours). The mixture was then filtered through a Celite pad and the filtrate was reduced to afford 95 mg of 1-(6-Amino-1,2,3,5-tetrahydro-benzo[e][1,4]diazepin-4-yl)-ethanone as a light brown solid. The compound was used without further purification. LC/MS (ESI)=206.30 (M+H).

236e) 1-(6-Amino-1,2,3,5-tetrahydro-benzo[e][1,4]diazepin-4-yl)-ethanone (35 mg, 0.17 mmol) was dissolved in 2-methoxyethanol (3 mL) and the mixture was treated with 2-(2,5-Dichloro-pyrimidin-4-ylamino)-N-methyl-benzamide (25 mg, 0.084 mmol) and 4N HCl/dioxane (0.05 mL, 0.17 mmol). The reaction was then irradiated at 140° C. for 20 minutes. The mixture was then reduced en vacuo and the crude mixture was purified by prep HPLC to afford 1.47 mg of 2-[2-(4-Acetyl-2,3,4,5-tetrahydro-1H-benzo[e][1,4]diazepin-6-ylamino)-5-chloro-pyrimidin-4-ylamino]-N-methyl-benzamide as a light brown foam. LC/MS (ESI)=466.37 (M+H). $^1$H NMR (400 MHz, MeOD, d$_4$) δ 8.80 (m, 1H), 8.29 (s, 1H), 8.04 (s, 1H), 7.79 (m, 3H), 7.64 (m, 3H), 7.35 (m, 1H), 6.97 (m, 1H), 6.49 (m, 1H), 3.64 (m, 2H), 3.35 (m, 2H), 3.21 (m, 2H), 2.98 (s, 3H), 1.94 (d, 3H, J=7.07 Hz).

Example 241

2-{5-Chloro-2-[8-methoxy-3-(2-methoxy-ethyl)-2,3,4,5-tetrahydro-1H-benzo[d]azepin-7-ylamino]-pyrimidin-4-ylamino}-N-methyl-benzamide 241a) A solution of (3-methoxy-phenyl)-acetyl chloride (40 g, 0.22 mol) in chloroform (100 mL) was added dropwise to a solution of 2,2-dimethoxy-ethylamine (25 mL, 0.23 mol) and triethylamine (34 mL, 1.1 eq) in chloroform (400 mL) at 0° C., and then the reaction mixture was stirred at room temperature overnight. The reaction mixture was washed with water, aqueous 1N HCl, and then again with water, dried (MgSO$_4$), filtered and concentrated to provide N-(2,2-dimethoxy-ethyl)-2-(3-methoxy-phenyl)-acetamide (53.8 g, 98%). $^1$H-NMR (CDCl$_3$) δ 7.27 (t, J=8.8 Hz, 1H), 6.84 (s, 1H), 6.81 (d, J=8.8 Hz, 2H), 5.66 (br s, 1H), 4.31 (t, J=5.2 Hz, 1H), 3.80 (s, 3H), 3.54 (s, 2H), 3.35 (t, J=5.2 Hz, 2H), 3.33 (s, 6H); LC/MS (ESI+): 222.15 [(M-MeOH)+H].

241b) A solution of N-(2,2-dimethoxy-ethyl)-2-(3-methoxy-phenyl)-acetamide (53.6 g, 0.21 mol) in acetic acid (140 mL) and aqueous 37% HCl (100 mL) was stirred at room temperature overnight. The reaction mixture was diluted with a ice/water mixture with vigorous stirring to yield a precipitate. The precipitate was filtered, rinsed with water, and then dissolved in dichloromethane, dried (MgSO$_4$), concentrated and dried in high vacuum to give 8-methoxy-1,3-dihydrobenzo[d]azepin-2-one (20.5 g, 51%) as a tan solid. 1H-NMR (CDCl$_3$) δ 8.23 (br s, 1H), 7.15 (d, J=8.3 Hz, 1H), 6.86 (d, J=8.6 Hz, 1H), 6.79, (s, 1H), 6.33 (d, J=9.1 Hz, 1H), 6.16 (dd, J=4.8, 9.3 Hz, 1H), 3.83 (s, 3H), 3.48 (s, 2H); LC/MS (ESI+): 190.05 (M+H).

241c) To a solution of 8-methoxy-1,3-dihydro-benzo[d]azepin-2-one (10.33 g, 0.055 mol) in acetic acid (200 mL) was added palladium 10% wt on Carbon (50% wet; 2 g). The mixture was shaken in a Parr apparatus under an atmosphere of hydrogen (50 PSI) overnight. Filtration through Celite and evaporation of solvent provided the crude product, which was triturated with a mixture of ether and DCM, filtered, and dried overnight in high vacuum to afford 8-methoxy-1,3,4,5-tetrahydro-benzo[d]azepin-2-one. $^1$H-NMR (CDCl$_3$) δ 7.03 (d, J=8.3 Hz, 1H), 6.76 (d, J=8.3 Hz, 1H), 6.69 (s, 1H), 6.17 (br s, 1H), 3.81 (s, 2H), 3.79 (s, 3H), 3.55 (q, J=5.1 Hz, 2H), 3.06 (t, J=5.8 Hz, 2H); LC/MS (ESI+): 192.07 (M+H).

241d) Into a 1-neck round-bottom flask, to 8-methoxy-1,3,4,5-tetrahydro-benzo[d]azepin-2-one (30.00 g, 0.16 mol) in tetrahydrofuran (200 mL) was added a 1 M solution of borane in tetrahydrofuran (450 mL) via cannula at 0° C., under an atmosphere of nitrogen. After 20 minutes the reaction was allowed to warm to room temperature and then the flask was equipped with a condenser and the reaction was heated at reflux overnight. The reaction was quenched by careful addition of concentrated aqueous HCl (37%). The tetrahydrofuran was removed in vacuo and to the aqueous reaction mixture was added an additional 50 mL of concentrated HCl and the resulting mixture was refluxed for 3 h, cooled and neutralized with 33% NaOH to pH 7-8 and further with saturated Na$_2$CO$_3$ to pH 11. The mixture was extracted three times with ethyl acetate, and the combined extracts were dried (MgSO$_4$), and concentrated. The crude product was passed through a short SiO$_2$ plug (MeOH/DCM 0-15%) to provide 7-methoxy-2,3,4,5-tetrahydro-1H-benzo[d]azepine (17 g, 55%). $^1$H-NMR (CDCl$_3$) δ 7.01 (d, J=8.3 Hz, 1H), 6.68 (d, J=2.5 Hz, 1H), 6.65 (dd, J=2.5, 8.1 Hz, 1H), 3.79 (s, 3H), 2.96 (m, 4H), 2.88 (m, 4H), 2.50 (br s, 1H); LC/MS (ESI+): 178.05 (M+H).

241e) Into a 1-neck round-bottom flask 7-methoxy-2,3,4,5-tetrahydro-1H-benzo[d]azepine (17.00 g, 0.096 mol) was dissolved in acetonitrile (100 mL). Trifluoroacetic anhydride (47.4 mL, 0.34 mol) was added at −20° C. After 10 minutes potassium nitrate (9.7 g, 0.096 mol) was added at the same temperature, and the reaction mixture was stirred for 1.5 hours. The reaction was quenched by addition of diluted NaHCO$_3$, and allowed to warm to room temperature. Partition between saturated aqueous Na$_2$CO$_3$ and dichloromethane, extraction, drying (MgSO4), filtration, and concentration, provided the crude product. Flash chromatography separation on SiO$_2$ with dichloromethane (100%) provided 2,2,2-trifluoro-1-(7-methoxy-8-nitro-1,2,4,5-tetrahydro-benzo[d]azepin-3-yl)-ethanone (11.5 g, 38%) and 2,2,2-trifluoro-1-(7-methoxy-6-nitro-1,2,4,5-tetrahydrobenzo[d]azepin-3-yl)-ethanone (7.5 g, 25%). 2,2,2-Trifluoro-1-(7-methoxy-8-nitro-1,2,4,5-tetrahydro-benzo[d]azepin-3-yl)-ethanone: $^1$H-NMR (CDCl$_3$; amide rotamers observed) δ 7.72(1H), 6.89 (1H), 3.95 (3H), 3.65-3.85 (4H), 2.95-3.07 (4H); LC/MS (ESI+): 319.20 (M+H). 2,2,2-Trifluoro-1-(7-methoxy-6-nitro-1,2,4,5-tetrahydro-benzo[d]azepin-3-yl)-ethanone: $^1$H-NMR (CDCl$_3$; amide rotamers observed) δ 7.24 (1H), 6.85 (1H), 3.88 (s, 3H), 3.65-3.81 (4H), 2.80-3.05 (4H).

241f) 2,2,2-Trifluoro-1-(7-methoxy-8-nitro-1,2,4,5-tetrahydro-benzo[d]azepin-3-yl)-ethanone (7.0 g, 0.022 mol) was dissolved in acetonitrile (150 mL). A 50% aqueous solution (70 mL) of sodium hydroxide was added at 0° C. After 10 minutes the reaction mixture allowed to warm to room temperature and stirred for 3 hours. The reaction mixture was partitioned between saturated Na$_2$CO$_3$ and dichloromethane, extracted, dried (MgSO4), filtered, and concentrated, to provide 7-methoxy-8-nitro-2,3,4,5-tetrahydro-1H-benzo[d]azepine (4.43 g, 89%). $^1$H-NMR (CDCl$_3$) δ 7.67 (s, 1H), 6.82 (s, 1H), 3.93 (s, 3H), 2.75-3.05 (m, 8H), 1.90 (br s, 1H); LC/MS (ESI+): 223.03 (M+H).

241g) Methoxy-8-nitro-2,3,4,5-tetrahydro-1H-benzo[d]azepine (3.4 g, 0.015 mol), 1-bromo-2-methoxyethane (2.82 mL, 0.030 mol), and potassium carbonate (6.2 g, 0.045 mol), were added to N,N-dimethylformamide (30 mL), and the reaction was stirred over night at room temperature. The reaction mixture was next partitioned between water and ethyl acetate, and the layers were separated. The aqueous phase was extracted twice with ethyl acetate and the combined organic extracts were dried (MgSO4), filtered, and concentrated. Flash chromatography on SiO$_2$ (MeOH/dichloromethane 0-7%) gave 7-methoxy-3-(2-methoxy-ethyl)-8-nitro-2,3,4,5-tetrahydro-1H-benzo[d]azepine (2.4 g, 55%). $^1$H-NMR (CDCl$_3$) δ 7.65 (s, 1H), 6.81 (s, 1H), 3.94 (s, 3H), 3.53 (t, J=5.6 Hz, 2H), 3.37 (s, 3H), 2.97 (m, 2H), 2.90 (m, 2H), 2.72 (m, 6H); LC/MS (ESI+): 281.10 (M+H).

241h) Into a 1-neck round-bottom flask was added 7-methoxy-3-(2-methoxy-ethyl)-8-nitro-2,3,4,5-tetrahydro-1H-benzo[d]azepine (2.4 g, 8.56 mmol), hydrazine monohydrate (20 mL, 0.4 mol), and palladium on carbon (10% wt, 50% wet; 400 mg), in methanol (80 mL). The reaction mixture was heated at 70° C. for 3 hours. The reaction mixture was filtered through Celite and was concentrated. The residue was partitioned between diluted NaHCO$_3$ and ethyl acetate. The aqueous phase was extracted with another portion of ethyl acetate, dried (MgSO4), and concentrated to afford 8-methoxy-3-(2-methoxy-ethyl)-2,3,4,5-tetrahydro-1H-benzo[d]azepin-7-ylamine (2.00 g, 93%). $^1$H-NMR (CDCl$_3$) δ 6.55 (s, 1H), 6.49 (s, 1H), 3.81 (s, 3H), 3.63 (br s, 2H), 3.53 (t, J=5.8 Hz, 2H), 3.36 (s, 3H), 2.60-2.90 (m, 10H); LC/MS (ESI+): 251.10 (M+H).

241i) 8-Methoxy-3-(2-methoxy-ethyl)-2,3,4,5-tetrahydro-1H-benzo[d]azepin-7-ylamine (55 mg, 0.22 mmol), 2-(2,5-dichloro-pyrimidin-4-ylamino)-N-methyl-benzamide (69 mg, 0.23 mmol), and a 4 M solution of hydrogen chloride in dioxane (0.06 mL, 1.1 eq), were added to isopropyl alcohol (2 mL). The reaction mixture was microwaved on 300 watts, at 130° C. for 40 minutes. The reaction mixture was partitioned between aqueous saturated Na$_2$CO$_3$ and dichloromethane, and the aqueous phase was extracted twice with dichloromethane. The combined organic extracts were dried (MgSO4), filtered, and then concentrated on SiO$_2$. Flash chromatography on SiO$_2$ (MeOH/dichloromethane 0-15%) gave 2-{5-Chloro-2-[8-methoxy-3-(2-methoxy-ethyl)-2,3,4,5-tetrahydro-1H-benzo[d]azepin-7-ylamino]-pyrimidin-4-ylamino}-N-methyl-benzamide as a white solid (47 mg, 42%). MP: 109-112° C.; $^1$H-NMR (CDCl$_3$) δ 10.98 (s, 1H), 8.65 (d, J=8.4 Hz, 1H), 8.10 (s, 1H), 8.09 (d, J=7.4 Hz, 1H), 7.40-7.54 (m, 3H), 7.07 (d, J=7.6 Hz, 1H), 6.64 (s, 1H), 6.20

(m, 1H), 3.86 (s, 3H), 3.70 (s, 3H), 3.57 (m, 2H), 3.37 (s, 3H), 3.03 (d, J=4.8 Hz, 3H), 2.60-2.98 (m, 10H); LC/MS (ESI+): 510.99 (M+H).

Example 242

N-(2-{5-Chloro-2-[8-methoxy-3-(2-methoxy-ethyl)-2,3,4,5-tetrahydro-1H-benzo[d]azepin-7-ylamino]-pyrimidin-4-ylamino}-phenyl)-methanesulfonamide Following a procedure similar to 241i, 8-methoxy-3-(2-methoxy-ethyl)-2,3,4,5-tetrahydro-1H-benzo[d]azepin-7-ylamine (55 mg, 0.22 mol) and N-[2-(2,5-dichloro-pyrimidin-4-ylamino)-phenyl]-methanesulfonamide (76.9 mg, 0.23 mol) were converted to N-(2-{5-chloro-2-[8-methoxy-3-(2-methoxy-ethyl)-2,3,4,5-tetrahydro-1H-benzo[d]azepin-7-ylamino]-pyrimidin-4-ylamino}-phenyl)-methanesulfonamide (84 mg, 66) as a white solid. MP: 107-112° C.; $^1$H-NMR (CDCl$_3$) δ 8.05 (s, 1H), 7.79 (s, 1H), 7.67 (t, J=4.4 Hz, 1H), 7.49 (s, 1H), 7.46 (t, j=4.0 Hz, 1H), 7.36 (s, 1H), 6.43 (s, 1H), 7.19-7.28 (m, 3H), 3.80 (s, 3H), 3.59 (t, J=4.8 Hz, 2H), 3.41 (s, 3H), 2.93 (s, 3H), 2.55-2.85 (m, 8H), 2.35 (br s, 2H); LC/MS (ESI+): 546.91 (M+H).

Example 243

5-Chloro-N*4*-(5-chloro-2-methoxy-phenyl)-N*2*-[8-methoxy-3-(2-methoxy-ethyl)-2,3,4,5-tetrahydro-1H-benzo[d]azepin-7-yl]-pyrimidine-2,4-diamine Following a procedure similar to 241i, 8-methoxy-3-(2-methoxy-ethyl)-2,3,4,5-tetrahydro-1H-benzo[d]azepin-7-ylamine (55 mg, 0.22 mmol) and (5-chloro-2-methoxy-phenyl)-(2,5-dichloro-pyrimidin-4-yl)-amine (70.3 mg, 0.023 mmol) were converted to 5-chloro-N*4*-(5-chloro-2-methoxy-phenyl)-N*2*-[8-methoxy-3-(2-methoxy-ethyl)-2,3,4,5-tetrahydro-1H-benzo[d]azepin-7-yl]-pyrimidine-2,4-diamine (57 mg, 49%) as a beige solid. MP: 123-128° C.; $^1$H-NMR (CDCl$_3$) δ 8.48 (s, 1H), 8.11 (s, 1H), 8.00 (s, 1H), 7.73 (s, 1H), 7.43 (s, 1H), 7.00 (d, J=8.7 Hz, 1H), 6.84 (d, J=8.6 Hz, 1H), 6.65 (s, 1H), 3.95 (s, 3H), 3.90 (s, 3H), 3.55 (t, J=5.6 Hz, 2H), 3.35 (s, 3H), 2.90 (m, 4H), 2.78 (m, 6H); LC/MS (ESI+): 518.00 (M+H).

Example 244

N-((1R,2R)-2-{5-Chloro-2-[7-methoxy-3-(2-methoxy-ethyl)-2,3,4,5-tetrahydro-1H-benzo[d]azepin-6-ylamino]-pyrimidin-4-ylamino}-cyclohexyl)-methanesulfonamide 244a) Following the procedures of 241f and 241g, 2,2,2-Trifluoro-1-(7-methoxy-6-nitro-1,2,4,5-tetrahydro-benzo[d]azepin-3-yl)-ethanone is converted to 7-methoxy-3-(2-methoxy-ethyl)-6-nitro-2,3,4,5-tetrahydro-1H-benzo[d]azepine. $^1$H-NMR (CDCl$_3$) δ 7.12 (d, j=8.4 Hz, 1H), 6.78 (d, J=8.4 Hz, 1H), 3.85 (s, 3H), 3.51 (t, J=5.6 Hz, 2H), 3.35 (s, 3H), 2.92 (m, 2H), 2.78 (m, 2H), 2.71 (m, 6H).

244b) Following the procedure of 241h, 7-methoxy-3-(2-methoxy-ethyl)-6-nitro-2,3,4,5-tetrahydro-1H-benzo[d]azepine (354 mg, 1.26 mmol) was converted to 8-methoxy-3-(2-methoxy-ethyl)-2,3,4,5-tetrahydro-1H-benzo[d]azepin-6-ylamine (293 mg, 93%). $^1$H-NMR (CDCl$_3$) δ 6.58 (d, J=8.0 Hz, 1H), 6.52 (d, J=8.0 Hz, 1H), 3.85 (s, 3H), 3.79 (br s, 2H), 3.52 (t, J=5.7 Hz, 2H), 1.35 (s, 3H), 2.85 (m, 4H), 2.70 (m, 6H).

244c) Following the procedure of 241i, except that the reaction was microwaved for 1.5 hours and chromatography elution gradient was MeOH/dichloromethane 0 to 7%, 8-methoxy-3-(2-methoxy-ethyl)-2,3,4,5-tetrahydro-1H-benzo[d]azepin-6-ylamine (57 mg, 0.23 mmol) and N-[(1R,2R)-2-(2,5-dichloro-pyrimidin-4-ylamino)-cyclohexyl]-methanesulfonamide (85 mg, 0.25 mmol) were converted to N-((1R,2R)-2-{5-chloro-2-[7-methoxy-3-(2-methoxy-ethyl)-2,3,4,5-tetrahydro-1H-benzo[d]azepin-6-ylamino]-pyrimidin-4-ylamino}-cyclohexyl)-methanesulfonamide (59 mg, 47%) as a white solid. MP: 93-100° C.; $^1$H-NMR (CDCl$_3$) δ 7.86 (s, 1H), 7.00 (d, J=8.0 Hz, 1H), 6.71 (d, J=8.00 Hz, 1H), 6.37 (s, 1H), 5.18 (br s, 2H), 3.77 (s, 3H), 3.68 (br s, 1H), 3.53 (t, J=5.5 Hz, 2H), 3.35 (s, 3H), 3.08 (br s, 1H), 2.95 (br s, 4H), 2.71 (s, 3H), 2.05 (m, 2H), 1.74 (m, 2H), 1.15-1.37 (m, 8H), 0.89 (m, 2H); LC/MS (ESI+): 552.99 (M+H).

Example 245

(2-exo,3-exo)-3-{5-Chloro-2-[7-methoxy-3-(2-methoxy-ethyl)-2,3,4,5-tetrahydro-1H-benzo[d]azepin-6-ylamino]-pyrimidin-4-ylamino}-bicyclo[2.2.1]hept-5-ene-2-carboxylic acid amide Following the procedure of 244c, 8-methoxy-3-(2-methoxy-ethyl)-2,3,4,5-tetrahydro-1H-benzo[d]azepin-6-ylamine (57 mg, 0.23 mmol) and (2-exo,3-exo)-3-(2,5-Dichloro-pyrimidin-4-ylamino)-bicyclo[2.2.1]hept-5-ene-2-carboxylic acid amide (78.5 mg, 0.25 mmol) were converted to (2-exo,3-exo)-3-{5-Chloro-2-[7-methoxy-3-(2-methoxy-ethyl)-2,3,4,5-tetrahydro-1H-benzo[d]azepin-6-ylamino]-pyrimidin-4-ylamino}-bicyclo[2.2.1]hept-5-ene-2-carboxylic acid amide (50 mg, 42%) as a white solid. MP: 90-100° C.; $^1$H-NMR (CDCl$_3$) δ 7.79 (s, 1H), 6.96 (d, J=8.0 Hz, 1H), 6.67 (d, J=8.0 Hz, 1H), 6.47 (s, 1H), 6.36 (s, 1H), 6.18 (s, 1H), 5.85 (s, 1H), 5.29 (s, 1H), 4.12 (s, 1H), 3.78 (s, 3H), 3.58 (m, 2H), 3.24 (s, 3H), 2.50-3.10 (m, 9H), 2.19 (d, J=9.4 Hz, 1H), 2.03 (s, 1H), 1.54 (d, J=8.6 Hz, 1H), 1.24 (m, 3H), 0.88 (t, J=6.7 Hz, 1H); LC/MS (ESI+): 513.22 (M+H).

Example 246

5-Chloro-N(2)-[7-methoxy-3-(2-methoxy-ethyl)-2,3,4,5-tetrahydro-1H-benzo[d]azepin-6-yl]-N(4)-(2-methoxy-4-morpholin-4-yl-phenyl)-pyrimidine-2,4-diamine Following the procedure of 244c, 7-methoxy-3-(2-methoxy-ethyl)-2,3,4,5-tetrahydro-1H-benzo[d]azepin-6-ylamine (57 mg, 0.23 mmol) and (2,5-Dichloro-pyrimidin-4-yl)-(2-methoxy-4-morpholin-4-yl-phenyl)-amine (89 mg, 0.25 mmol) were converted to 5-chloro-N(2)-[7-methoxy-3-(2-methoxy-ethyl)-2,3,4,5-tetrahydro-1H-benzo[d]azepin-6-yl]-N(4)-(2-methoxy-4-morpholin-4-yl-phenyl)-pyrimidine-2,4-diamine (45 mg, 34%). MP: 68-80° C.; $^1$H-NMR (CDCl$_3$) δ 7.95 (s, 1H), 7.59 (s, 1H), 7.05 (d, J=8.4 Hz, 1H), 6.75 (d, J=8.1 Hz, 1H), 6.48 (s, 1H), 6.40 (s, 1H), 6.23 (br s, 1H), 3.89 (s, 3H), 3.88 (t, J=4.7 Hz, 4H), 3.75 (s, 3H), 3.65 (br s, 2H), 3.32 (s, 3H), 3.10 (m, 4H), 2.45-3.20 (m, 8H), 1.67 (m, 3H); LC/MS (ESI+): 569.57 (M+H).

Example 247

N-((1R,2R)-2-{5-Chloro-2-[8-methoxy-3-(2,2,2-trifluoro-acetyl)-2,3,4,5-tetrahydro-1H-benzo[d]azepin-7-ylamino]-pyrimidin-4-ylamino}-cyclohexyl)-methanesulfonamide 247a) To a solution of 2,2,2-trifluoro-1-(7-methoxy-8-nitro-1,2,4,5-tetrahydro-benzo[d]azepin-3-yl)-ethanone in methanol was added palladium 10% wt on Carbon (50% wet). The mixture was shaken in a Parr apparatus under an atmosphere of Hydrogen (50 PSI) for 30 minutes. Filtration through Celite and evaporation of the solvent provided quantitatively 1-(7-amino-8-methoxy-1,2,4,5-tetrahydro-benzo[d]azepin-3-yl)-2,2,2-trifluoro-ethanone, which was used without further purification. $^1$H-NMR (CDCl$_3$; amide rotamers observed) δ 6.58 (1H), 6.53 (1H), 3.83 (s, 3H), 3.15-4.25 (br s, 2H), 3.60-3.78 (4H), 2.79-2.92 (4H); LC/MS (ESI+): 288.99 (M+H).

247b) Following a procedure similar to 241i, except that the reaction was microwaved for 1 h and chromatography elution gradient was MeOH/dichloromethane 0 to 5%, 1-(7-Amino-8-methoxy-1,2,4,5-tetrahydro-benzo[d]azepin-3-yl)-2,2,2-trifluoro-ethanone (50 mg, 0.17 mmol) and N-[(1R,2R)-2-(2,5-Dichloro-pyrimidin-4-ylamino)-cyclohexyl]-methanesulfonamide (64 mg, 0.19 mmol) were converted to N-((1R,2R)-2-{5-chloro-2-[8-methoxy-3-(2,2,2-trifluoro-acetyl)-2,3,4,5-tetrahydro-1H-benzo[d]azepin-7-ylamino]-pyrimidin-4-ylamino}-cyclohexyl)-methanesulfonamide (59 mg, 53%) as a white solid. MP: 98-107° C.; $^1$H-NMR (CDCl$_3$) δ 8.09 (d, J=11.9 Hz, 1H), 7.39 (m, 1H), 6.67 (d, J=12.0 Hz, 1H), 5.38 (m, 2H), 4.83 (m, 1H), 3.60-4.00 (m, 4H), 3.25 (m, 1H), 3.09 (m, 1H), 3.05 (s, 3H), 2.95 (m, 2H), 2.80 (s, 3H), 2.20 (m, 2H), 1.80 (m, 2H), 1.35 (m, 6H); LC/MS (ESI+): 591.16 (M+H).

Example 248

N-((1R,2R)-2-{5-Chloro-2-[8-methoxy-3-(2,2,2-trifluoro-ethyl)-2,3,4,5-tetrahydro-1H-benzo[d]azepin-7-ylamino]-pyrimidin-4-ylamino}-cyclohexyl)-methanesulfonamide 248a) Into a 1-neck round-bottom flask was added 7-methoxy-8-nitro-2,3,4,5-tetrahydro-1H-benzo[d]azepine (0.500 g, 2.2 mmol), trichloro-methanesulfonic acid 2,2,2-trifluoro-ethyl ester (0.45 mL, 2.9 mmol), and potassium carbonate (0.91 g, 6.61 mmol), in N,N-dimethylformamide (5 mL), and the reaction was stirred overnight at room temperature. The reaction mixture was partitioned between saturated aqueous Na$_2$CO$_3$ and dichloromethane. Extraction with another portion of dichloromethane, drying (MgSO4), concentration and flash chromatography isolation (on SiO$_2$, MeOH/dichloromethane 0-3%) provided 7-methoxy-8-nitro-3-(2,2,2-trifluoro-ethyl)-2,3,4,5-tetrahydro-1H-benzo[d]azepine (310 mg, 46%) as a yellow oil. $^1$H-NMR (CDCl$_3$) δ 7.65 (s, 1H), 6.83 (s, 1H), 3.74 (s, 3H), 3.19 (q, J=9.6 Hz, 2H), 2.95 (m, 4H), 2.88 (s, 4H); LC/MS (ESI+): 305.05 (M+H).

248b) Into a 1-neck round-bottom flask was added 7-methoxy-8-nitro-3-(2,2,2-trifluoro-ethyl)-2,3,4,5-tetrahydro-1H-benzo[d]azepine (310 mg, 1.0 mmol), hydrazine monohydrate (10 mL, 0.2 mol), palladium (10% wt on C, 50% wet; 100 mg, 0.9 mmol), in methanol (20 mL). The reaction mixture was heated at 70° C. for 3 hours. The reaction mixture was filtered through Celite and was concentrated. The resulting precipitate was partitioned between water and dichloromethane. The organic phase was washed with another portion of water, dried (MgSO4), and concentrated, to afford 8-methoxy-3-(2,2,2-trifluoro-ethyl)-2,3,4,5-tetrahydro-1H-benzo[d]azepin-7-ylamine (245 mg, 88%) as a waxy solid, which was used without further purification. m.p. ° C.; $^1$H-NMR (CDCl$_3$) δ 6.55 (s, 1H), 6.49 (s, 1H), 3.82 (s, 3H), 3.63 (br s, 2H), 3.15 (q, J=9.5 hz, 2H), 2.88 (m, 4H), 2.77 (m, 4H); LC/MS (ESI+): 275.07 (M+H).

248c) Following a procedure similar to 247b, 8-methoxy-3-(2,2,2-trifluoro-ethyl)-2,3,4,5-tetrahydro-1H-benzo[d]azepin-7-ylamine (49 mg, 0.18 mmol) and N-[(1R,2R)-2-(2,5-dichloro-pyrimidin-4-ylamino)-cyclohexyl]-methanesulfonamide (79 mg, 0.23 mmol) were converted to N-((1R,2R)-2-{5-chloro-2-[8-methoxy-3-(2,2,2-trifluoro-ethyl)-2,3,4,5-tetrahydro-1H-benzo[d]azepin-7-ylamino]-pyrimidin-4-ylamino}-cyclohexyl)-methanesulfonamide (38 mg, 35%) as a white solid. MP: 103-110° C.; $^1$H-NMR (CDCl$_3$) δ 7.99 (s, 1H), 7.95 (s, 1H), 7.32 (s, 1H), 6.65 (s, 1H), 5.37 (d, J=7.8 Hz, 1H), 5.30 (d, J=6.6 Hz, 1H), 3.95 (m, 1H), 3.88 (s, 3H), 3.20 (m, 3H), 2.93 (m, 7H), 2.79 (s, 3H), 2.22 (m, 2H), 1.85 (m, 2H), 1.35 (m, 3H), 0.85 (m, 2H); LC/MS (ESI+): 577.02 (M+H).

Example 249

5-Chloro-N*4*-(2-methoxy-4-morpholin-4-yl-phenyl)-N*2*-[8-methoxy-3-(2,2,2-trifluoro-ethyl)-2,3,4,5-tetrahydro-1H-benzo[d]azepin-7-yl]-pyrimidine-2,4-diamine Following a procedure similar to 247b, except that the reaction was microwaved for 20 minutes, 8-Methoxy-3-(2,2,2-trifluoro-ethyl)-2,3,4,5-tetrahydro-1H-benzo[d]azepin-7-ylamine (49 mg, 0.18 mmol) and (2,5-dichloro-pyrimidin-4-yl)-(2-methoxy-4-morpholin-4-yl-phenyl)-amine (69.80 mg, 0.197 mmol) were converted to 5-chloro-N*4*-(2-methoxy-4-morpholin-4-yl-phenyl)-N*2*-[8-methoxy-3-(2,2,2-trifluoro-ethyl)-2,3,4,5-tetrahydro-1H-benzo[d]azepin-7-yl]-pyrimidine-2,4-diamine (64 mg, 64%) as a white solid. MP: 230-235° C.; $^1$H-NMR (CDCl$_3$) δ 8.25 (d, J=8.6 Hz, 1H), 8.12 (s, 1H), 8.03 (s, 1H), 7.53 (s, 1H), 7.95 (s, 1H), 6.63 (s, 1H), 6.55 (s, 1H), 6.50 (d, J=8.8 Hz, 1H), 3.92 (s, 3H), 3.89 (m, 4H), 3.85 (s, 3H), 3.15 (m, 6H), 2.85 (m, 8H); LC/MS (ESI+): 593.14 (M+H).

Example 250

(2-exo, 3-exo)-3-{5-Chloro-2-[8-methoxy-3-(2,2,2-trifluoro-ethyl)-2,3,4,5-tetrahydro-1H-benzo[d]azepin-7-ylamino]-pyrimidin-4-ylamino}-bicyclo[2.2.1]hept-5-ene-2-carboxylic acid amide hydrochloride Following a procedure similar to 247b, except that the product precipitated from the reaction mixture in the hydrochloride salt form and was collected by filtration and washed with ether, 8-methoxy-3-(2,2,2-trifluoro-ethyl)-2,3,4,5-tetrahydro-1H-benzo[d]azepin-7-ylamine (49 mg, 0.18 mmol) and (2-exo,3-exo)-3-(2,5-dichloro-pyrimidin-4-ylamino)-bicyclo[2.2.1]hept-5-ene-2-carboxylic acid amide (58.79 mg, 0.197 mmol) were converted to (2-exo, 3-exo)-3-{5-chloro-2-[8-methoxy-3-(2,2,2-trifluoro-ethyl)-2,3,4,5-tetrahydro-1H-benzo[d]azepin-7-ylamino]-pyrimidin-4-ylamino}-bicyclo[2.2.1]hept-5-ene-2-carboxylic acid amide hydrochloride (80 mg, 80%) as a white solid. MP: 250-252° C.; 1H-NMR (DMSO-d$_6$) δ 9.80 (br s, 1H), 8.30 (s, 1H), 8.03 (s, 1H), 7.60 (s, 1H), 7.45 (s, 1H), 7.00 (s, 1H), 6.39 (s, 1H), 6.08 (s, 1H), 3.96 (t, J=7.1 Hz, 1H), 3.82 (s, 3H), 3.77, (br s, 1H) 2.70-3.20 (m, 13H), 2.54 (d, J=8.1 Hz, 1H), 1.98 (d, J=8.3 Hz, 1H), 1.40 (d, J=8.8 Hz, 1H); LC/MS (ESI+): 537.16 (M+H).

Example 251

N-{(1R,2R)-2-[5-Chloro-2-(3-ethyl-8-methoxy-2-oxo-2,3,4,5-tetrahydro-1H-benzo[d]azepin-7-ylamino)-pyrimidin-4-ylamino]-cyclohexyl}-methanesulfonamide 251a) Into a 1-neck round-bottom flask 8-methoxy-1,3-dihydro-benzo[d]azepin-2-one (2.5 g, 13.2 mmol) in dimethyl sulfoxide (14 mL) was treated with potassium tert-butoxide (1.8 g, 16.0 mmol) at room temperature. After 10 min the generated anion solution was added to a solution of iodoethane (1.3 mL, 16.0 mmol) in dimethyl sulfoxide (5 mL) at 0° C. The reaction was stirred at 0° C. for 15 minutes and then an ice/water mixture was added to the reaction mixture and stirring was continued until the product precipitated. The product was filtered and the cake was dissolved in dichloromethane, was heated at reflux with decolorizing carbon, filtered, washed with water, dried (MgSO4), and concentrated to generate 3-ethyl-8-methoxy-1,3-dihydro-benzo[d]azepin-2-one (2.24 g, 78%). $^1$H-NMR (CDCl$_3$) δ 7.18 (d, J=8.3 Hz, 1H), 6.85 (d, J=8.8 Hz, 1H), 6.81 (s, 1H), 6.38 (d, J=9.1 Hz, 1H), 6.18 (d, J=9.1 Hz, 1H), 3.80 (s, 3H), 3.59 (q, J=7.3 Hz, 2H), 3.49 (s, 2H), 1.10 (t, J=7.3 Hz, 3H); LC/MS (ESI+): 217.95 (M+H).

251b) To a solution of 3-ethyl-8-methoxy-1,3-dihydro-benzo[d]azepin-2-one (2.20 g, 0.010 mol) in acetic acid (30 mL) was added palladium 10% wt on carbon (50% wet; 200 mg). The mixture was shaken in a Parr apparatus under an atmosphere of hydrogen (50 PSI) for 1 day. The reaction mixture was filtered through Celite, concentrated, and subjected to flash chromatography on SiO$_2$ (ethyl acetate/hexanes 20-70%) to give 3-ethyl-8-methoxy-1,3,4,5-tetrahydro-benzo[d]azepin-2-one (1.33 g, 60%), as a white solid. m.p. ° C.; $^1$H-NMR (CDCl$_3$) δ 7.00 (d, J=8.3 Hz, 1H), 6.75 (d, J=8.6 Hz, 1H), 3.85 (s, 2H), 3.78 (s, 3H), 3.69 (t, J=6.1 Hz, 2H), 3.48 (q, J=7.3 HZ, 2H), 3.08 (t, J=5.8 Hz, 2H), 1.16 (t, J=7.3 Hz, 3H); LC/MS (ESI+): 220.06 (M+H).

251c) 3-Ethyl-8-methoxy-1,3,4,5-tetrahydro-benzo[d]azepin-2-one (1.25 g, 5.682 mmol) in acetonitrile (5 mL) was treated with 65% nitric acid (20 mL), followed by fuming nitric acid (3 mL) at 0° C. for 30 minutes. The reaction was quenched at 0° C. with saturated Na$_2$CO$_3$ to pH 9-10, extracted three times with ethyl acetate. The products were separated by flash chromatography on SiO$_2$ (ethyl acetate/hexanes 50-95%): 3-ethyl-8-methoxy-7-nitro-1,3,4,5-tetrahydro-benzo[d]azepin-2-one (435 mg, 26%, yellow solid), and 3-ethyl-8-methoxy-9-nitro-1,3,4,5-tetrahydro-benzo[d]azepin-2-one (540 mg, 31%, yellow solid). 3-Ethyl-8-methoxy-7-nitro-1,3,4,5-tetrahydro-benzo[d]azepin-2-one: $^1$H-NMR (CDCl$_3$) δ 7.67 (s, 1H), 6.82 (s, 1H), 3.93 (s, 3H), 3.74 (t, J=6.1 Hz, 2H), 3.49 (q, J=7.1 Hz, 2H), 3.12 (t, J=6.1 Hz, 2H), 1.15 (t, J=7.1 Hz, 3H); LC/MS (ESI+): 265.03 (M+H).

251d) To a solution of 3-ethyl-8-methoxy-7-nitro-1,3,4,5-tetrahydro-benzo[d]azepin-2-one (429 mg, 1.48 mol) in methanol (30 mL) was added palladium 10% wt on Carbon (50% wet; 100 mg). The mixture was shaken in a Parr apparatus under an atmosphere of hydrogen (50 PSI) for 30 minutes. Filtration through Celite and evaporation of the solvent provided 3-ethyl-8-methoxy-7-nitro-1,3,4,5-tetrahydro-benzo[d]azepin-2-one (312 mg, 89%) as a tan solid, which was used without further purification. $^1$H-NMR (CDCl$_3$/CF3CO$_2$D) δ 7.31 (s, 1H), 6.90 (s, 1H), 4.22 (s, 2H), 3.95 (m, 2H), 3.90 (s, 3H), 3.63 (q, J=6.8 Hz, 2H), 3.20 (br s, 2H), 1.29 (t, J=6.8 Hz, 3H); LC/MS (ESI+): 235.10 (M+H).

251e) Following a procedure similar to 247b, 7-amino-3-ethyl-8-methoxy-1,3,4,5-tetrahydro-benzo[d]azepin-2-one (46 mg, 0.18 mmol) was reacted with N-[(1R,2R)-2-(2,5-dichloro-pyrimidin-4-ylamino)-cyclohexyl]-methanesulfonamide (60.60 mg, 0.18 mmol), except that the product precipitated from the reaction mixture in the hydrochloride salt form, was collected by filtration, and then free-based by treatment of a solution of the salt in dichloromethane with aqueous saturated NaHCO$_3$. The organic solution was dried (MgSO$_4$), and concentrated to afford N-{(1R,2R)-2-[5-chloro-2-(3-ethyl-8-methoxy-2-oxo-2,3,4,5-tetrahydro-1H-benzo[d]azepin-7-ylamino)-pyrimidin-4-ylamino]-cyclohexyl}-methanesulfonamide (35 mg, 36%) as a white solid. MP: 139-150° C.; 1H-NMR (CDCl$_3$) δ 8.00 (s, 1H), 7.95 (s, 1H), 7.33 (s, 1H), 6.65 (s, 1H), 5.25-5.40 (m, 2H), 3.95 (m, 1H), 3.88 (s, 3H), 3.84 (s, 2H), 3.73 (t, J=5.8 Hz, 2H), 3.48 (q, J=7.1 Hz, 2H), 3.25 (m, 1H), 3.12 (t, J=5.6 Hz, 2H), 2.80 (s, 3H), 2.20 (m, 2H), 1.80 (br s, 2H), 1.40 (s, 4H), 1.17 (t, J=7.1 Hz, 3H); LC/MS (ESI+): 537.31 (M+H).

Example 252

(2-exo,3-exo)-3-[5-Chloro-2-(3-ethyl-8-methoxy-2-oxo-2,3,4,5-tetrahydro-1H-benzo[d]azepin-7-ylamino)-pyrimidin-4-ylamino]-bicyclo[2.2.1]hept-5-ene-2-carboxylic acid amide Following a procedure similar to 247b, 7-amino-3-ethyl-8-methoxy-1,3,4,5-tetrahydro-benzo[d]azepin-2-one (45 mg, 0.19 mmol) and (2-exo,3-exo)-3-(2,5-dichloro-pyrimidin-4-ylamino)-bicyclo[2.2.1]hept-5-ene-2-carboxylic acid amide (60.3 mg, 0.20 mmol) were converted to (2-exo,3-exo)-3-[5-chloro-2-(3-ethyl-8-methoxy-2-oxo-2,3,4,5-tetrahydro-1H-benzo[d]azepin-7-ylamino)-pyrimidin-4-ylamino]-bicyclo[2.2.1]hept-5-ene-2-carboxylic acid amide (33 mg, 35%) as a tan solid. MP: 150-154° C.; $^1$H-NMR (CDCl$_3$) δ 8.18 (s, 1H), 7.81 (s, 1H), 7.38 (s, 1H), 6.61 (s, 1H), 6.57 (d, J=8.4 Hz, 1H), 6.31 (m, 2H), 5.63 (s, 1H), 5.37 (s, 1H), 4.42 (t J=7.6 Hz, 1H), 3.87 (s, 3H), 3.82 (s, 2H), 3.71 (t, J=6.0 Hz, 2H), 3.48 (m, 4H), 3.08 (m, 2H), 2.88 (s, 1H), 2.51 (d, J=8.0 Hz, 1H), 2.26 (d, J=9.2 Hz, 1H), 1.18 (t J=6.8 Hz, 3H); LC/MS (ESI+): 497.37 (M+H).

Example 253

2-[5-Chloro-2-(3-ethyl-8-methoxy-2-oxo-2,3,4,5-tetrahydro-1H-benzo[d]azepin-7-ylamino)-pyrimidin-4-ylamino]-N-methyl-benzamide Following a procedure similar to 247b, 7-amino-3-ethyl-8-methoxy-1,3,4,5-tetrahydro-benzo[d]azepin-2-one (45 mg, 0.17 mmol) and 2-(2,5-dichloro-pyrimidin-4-ylamino)-N-methyl-benzamide (53.08 mg, 0.18 mmol) were converted to 2-[5-chloro-2-(3-ethyl-8-methoxy-2-oxo-2,3,4,5-tetrahydro-1H-benzo[d]azepin-7-ylamino)-pyrimidin-4-ylamino]-N-methyl-benzamide (37 mg, 42%) as a white solid. MP: 120-132° C.; $^1$H-NMR (CDCl$_3$) δ 11.03 (s, 1H), 8.65 (d, J=8.8 Hz, 1H), 8.11 (s, 1H), 8.07 (s, 1H), 7.50 (d, J=8.0 Hz, 1H), 7.43 (s, 2H), 7.07 (t, J=7.6 Hz, 1H), 6.61 (s, 1H), 6.24 (s, 1H), 3.88 (s, 3H), 3.83 (s, 2H), 3.68 (t, J=6.6 Hz, 2H), 3.48 (q, J=7.2 Hz, 2H), 3.04 (d, J=4.8 Hz, 3H), 2.99 (t, J=4.0 Hz, 2H), 1.18 (t, J=7.2 Hz, 3H); LC/MS (ESI+): 495.34 (M+H).

Example 254

7-[5-Chloro-4-(2-methoxy-4-morpholin-4-yl-phenylamino)-pyrimidin-2-ylamino]-3-ethyl-8-methoxy-1,3,4,5-tetrahydro-benzo[d]azepin-2-one Following a procedure similar to 247b, except that a 0 to 5% MeOH/ethyl acetate gradient was used for chromatography, 7-amino-3-ethyl-8-methoxy-1,3,4,5-tetrahydro-benzo[d]azepin-2-one (45 mg, 0.17 mmol) and (2,5-dichloro-pyrimidin-4-yl)-(2-methoxy-4-morpholin-4-yl-phenyl)-amine (65.2 mg, 0.18 mmol) were converted to 7-[5-chloro-4-(2-methoxy-4-morpholin-4-yl-phenylamino)-pyrimidin-2-ylamino]-3-ethyl-8-methoxy-1,3,4,5-tetrahydro-benzo[d]azepin-2-one (48 mg, 49%) as a beige solid. MP: 212-214° C.; $^1$H-NMR (CDCl$_3$) δ 8.21 (d, J=8.5 Hz, 1H), 8.09 (s, 1H), 8.03 (s, 1H), 7.52 (s, 1H), 7.43 (s, 1H), 6.63 (s, 1H), 6.57 (s, 1H), 6.54 (d, J=8.9 Hz, 1H), 3.95, (s, 3H), 3.90 (m, 4H), 3.88 (s, 3H), 3.85 (s, 2H), 3.69 (t, J=5.5 Hz, 2H), 3.48 (q, J=7.2 Hz, 2H), 3.25 (t, J=4.3 Hz, 4H), 3.02 (t, J=5.6 Hz, 2H), 1.18 (t, J=7.2 Hz, 3H); LC/MS (ESI+): 553.45 (M+H).

Example 255

2-[5-Chloro-2-(3-ethyl-8-methoxy-2-oxo-2,3,4,5-tetrahydro-1H-benzo[d]azepin-7-ylamino)-pyrimidin-4-ylamino]-N-ethyl-benzamide Following a procedure similar to 247b, except that a 0 to 7% MeOH/ethyl acetate gradient was used for chromatography, 7-amino-3-ethyl-8-methoxy-1,3,4,5-tetrahydro-benzo[d]azepin-2-one (50 mg, 0.2 mmol) and 2-(2,5-dichloro-pyrimidin-4-ylamino)-N-ethyl-benzamide (66.5 mg, 0.21 mmol) were converted to 2-[5-chloro-2-(3-ethyl-8-methoxy-2-oxo-2,3,4,5-tetrahydro-1H-benzo[d]azepin-7-ylamino)-pyrimidin-4-ylamino]-N-ethyl-benzamide (40 mg, 40%) as a light yellow solid. MP: 244-251° C.; $^1$H-NMR (CDCl$_3$) δ 11.00 (s, 1H), 8.64 (d, J=8.6 Hz, 1H), 8.12 (s, 1H), 8.07 (s, 1H), 7.50 (d, J=7.6 Hz, 1H), 7.44 (m, 2H), 7.08 (t, J=7.6 Hz, 1H), 6.62 (s, 1H), 6.17 (br s, 1H), 3.87 (s, 3H), 3.83 (s, 2H), 3.69 (t, J=5.7 Hz, 2H), 3.50 (m, 4H), 3.00 (t, J=5.7 Hz, 2H), 1.27 (t, J=7.3 Hz, 3H), 1.18 (t, J=7.1 Hz, 3H); LC/MS (ESI+): 509.38 (M+H).

Example 256

N-(2-{7-[5-Chloro-4-((1R,2R)-2-methanesulfonylamino-cyclohexylamino)-pyrimidin-2-ylamino]-8-methoxy-1,2,4,5-tetrahydro-benzo[d]azepin-3-yl}-ethyl)-acetamide 256a) Into a 1-neck round-bottom flask was added 7-methoxy-8-nitro-2,3,4,5-tetrahydro-1H-benzo[d]azepine (0.5 g, 2.20 mmol), N-(2-chloro-ethyl)-acetamide (0.45 mL, 4.41 mmol), potassium iodide (92 mg, 0.55 mmol), and potassium carbonate (900 mg, 7 mmol), in N-methylpyrrolidinone (5 mL), and the reaction was heated at 90 overnight. The reaction mixture was next partitioned between water and ethyl acetate, and the layers separated. The aqueous phase was extracted twice with ethyl acetate and the combined organic extracts were washed with water, dried (MgSO$_4$), filtered, and concentrated, and the product was isolated by flash chromatography on SiO$_2$ (MeOH/dichloromethane 0-20%) to give N-[2-(7-Methoxy-8-nitro-1,2,4,5-tetrahydro-benzo[d]azepin-3-yl)-ethyl]-acetamide (100 mg, 15%). $^1$H-NMR (CDCl$_3$) δ 7.67 (s, 1H), 6.84 (s, 1H), 6.11 (br s, 1H), 3.94 (s, 3H), 3.38 (m, 2H), 2.95 (m, 2H), 2.89 (m, 2H), 2.66 (m, 6H), 2.01 (s, 3H); LC/MS (ESI+): 308.02 (M+H).

256b) To a solution of N-[2-(7-methoxy-8-nitro-1,2,4,5-tetrahydro-benzo[d]azepin-3-yl)-ethyl]-acetamide (100 mg, 0.3 mmol) in methanol (20 mL) was added palladium 10% wt on Carbon (50% wet; 50 mg). The mixture was shaken in a Parr apparatus under an atmosphere of hydrogen (50 PSI) for 30 minutes. Filtration through Celite and evaporation of the solvent provided N-[2-(7-amino-8-methoxy-1,2,4,5-tetrahydro-benzo[d]azepin-3-yl)-ethyl]-acetamide (90 mg, 100%) as a yellow oil, which was used without further purification. $^1$H-NMR (CDCl$_3$) δ 6.59 (br s, 1H), 6.53 (s, 1H), 6.48 (s, 1H), 3.82 (s, 3H), 3.50-4.40 (br s, 2H), 3.40 (m, 2H), 2.65-2.93 (m, 10H), 2.02 (s, 3H); LC/MS (ESI+): 278.25 (M+H).

256c) Following a procedure similar to 247b, except that a 0 to 17% MeOH/dichloromethane gradient was used for chromatography, N-[2-(7-amino-8-methoxy-1,2,4,5-tetrahydro-benzo[d]azepin-3-yl)-ethyl]-acetamide (38 mg, 0.14 mmol) and N-[(1R,2R)-2-(2,5-dichloro-pyrimidin-4-ylamino)-cyclohexyl]-methanesulfonamide (46.5 mg, 0.14 mmol) were converted to N-(2-{7-[5-chloro-4-((1R,2R)-2-methanesulfonylamino-cyclohexylamino)-pyrimidin-2-ylamino]-8-methoxy-1,2,4,5-tetrahydro-benzo[d]azepin-3-yl}-ethyl)-acetamide (27 mg, 33%) as a tan solid. MP: 108-118° C.; $^1$H-NMR (CDCl$_3$) δ 8.00 (s, 1H), 7.94 (s, 1H), 7.33 (s, 1H), 6.65 (s, 1H), 6.12 (br s, 1H), 5.32 (m, 2H), 3.96, (m, 1H), 3.87, (s, 3H), 3.37 (m, 2H), 3.24 (m, 1H), 2.89 (br s, 4H), 2.78 (s, 3H), 2.65 (m, 6H), 2.23 (m, 2H), 2.01 (s, 3H), 1.84 (br s, 2H), 1.20-1.45 (m, 3H), 0.89 (m, 1H); LC/MS (ESI+): 580.43 (M+H).

Example 257

N-(2-{7-[5-Chloro-4-(2-methoxy-4-morpholin-4-yl-phenylamino)-pyrimidin-2-ylamino]-8-methoxy-1,2,4,5-tetrahydro-benzo[d]azepin-3-yl}-ethyl)-acetamide Following a procedure similar to 247b, except that a 0 to 10% MeOH/dichloromethane gradient was used for chromatography, N-[2-(7-amino-8-methoxy-1,2,4,5-tetrahydro-benzo[d]azepin-3-yl)-ethyl]-acetamide (38 mg, 0.14 mmol) and (2,5-dichloro-pyrimidin-4-yl)-(2-methoxy-4-morpholin-4-yl-phenyl)-amine (51.10 mg, 0.144 mmol) were converted to N-(2-{7-[5-chloro-4-(2-methoxy-4-morpholin-4-yl-phenylamino)-pyrimidin-2-ylamino]-8-methoxy-1,2,4,5-tetrahydro-benzo[d]azepin-3-yl}-ethyl)-acetamide (40 mg, 45%) as a brown solid. MP: 50-65° C.; $^1$H-NMR (CDCl$_3$) δ 8.25 (d, J=8.1 Hz, 1H), 8.13 (s, 1H), 8.02 (s, 1H), 7.54 (s, 1H), 7.43 (s, 1H), 6.64 (s, 1H), 6.56 (s, 1H), 6.53 (d, J=10.1 Hz, 1H), 6.20 (br s, 1H), 3.93 (s, 3H), 3.90 (t, J=4.8 Hz, 4H), 3.96 (s, 3H), 3.38 (m, 2H), 3.15 (t, J=4.3 Hz, 4H), 2.85 (m, 4H), 2.65 (m, 6H), 2.03 (s, 3H); LC/MS (ESI+): 596.45 (M+H).

Example 258

2-{7-[5-Chloro-4-((1R,2R)-2-methanesulfonylamino-cyclohexylamino)-pyrimidin-2-ylamino]-8-methoxy-1,2,4,5-tetrahydro-benzo[d]azepin-3-yl}-N,N-dimethyl-acetamide 258a) Into a 1-neck round-bottom flask was added 7-methoxy-8-nitro-2,3,4,5-tetrahydro-1H-benzo[d]azepine (0.5 g, 2.20 mmol), 2-chloro-N,N-dimethyl-acetamide (0.45 mL, 4.41 mmol), potassium iodide (0.18 g, 1.10 mmol), and cesium carbonate (2.16 g, 6.61 mmol), in acetonitrile (15 mL), and the reaction was stirred overnight at reflux. The reaction mixture was next partitioned between water and ethyl acetate, and the layers separated. The aqueous phase was extracted twice with ethyl acetate and the combined organic extracts were washed with water, dried (MgSO$_4$), filtered, and concentrated, and the product was isolated by flash chromatography on SiO$_2$ (MeOH/dichloromethane 0-10%) to give 2-(7-Methoxy-8-nitro-1,2,4,5-tetrahydro-benzo[d]azepin-3-yl)-N,N-dimethyl-acetamide (537 mg, 79%) as a yellow solid. $^1$H-NMR (CDCl$_3$) δ 7.67 (s, 1H), 6.82 (s, 1H), 3.95 (s, 3H), 3.30 (s, 2H), 3.09 (s, 3H), 2.98 (s, 3H), 2.85-3.05 (m, 4H), 2.73 (t, J=10.2 Hz, 4H); LC/MS (ESI+): 308.55 (M+H).

258b) To a solution of 2-(7-methoxy-8-nitro-1,2,4,5-tetrahydro-benzo[d]azepin-3-yl)-N,N-dimethyl-acetamide (767 mg, 1.75 mmol) in methanol (30 mL) was added palladium 10% wt on Carbon (50% wet; 100 mg). The mixture was shaken in a Parr apparatus under an atmosphere of hydrogen (50 PSI) for 30 minutes. Filtration through Celite and evaporation of the solvent provided the crude product, which was purified by flash chromatography on SiO$_2$ (MeOH/dichloromethane 0-6%) to give 2-(7-Amino-8-methoxy-1,2,4,5-tetrahydro-benzo[d]azepin-3-yl)-N,N-dimethyl-acetamide (332 mg, 69%) as a white solid. $^1$H-NMR (CDCl$_3$) δ 6.54 (s, 1H), 6.48 (s, 1H), 3.81 (s, 3H), 3.53 (br s, 2H), 3.23 (s, 2H), 3.13 (s, 3H), 2.96 (s, 3H), 2.80 (m, 4H), 2.65 (m, 4H); LC/MS (ESI+): 278.67 (M+H).

258c) Following a procedure similar to 247b, except that a 0 to 10% MeOH/ethyl acetate gradient was used for chromatography, 2-(7-amino-8-methoxy-1,2,4,5-tetrahydro-benzo[d]azepin-3-yl)-N,N-dimethyl-acetamide (50 mg, 0.2 mmol), and N-[(1R,2R)-2-(2,5-dichloro-pyrimidin-4-ylamino)-cyclohexyl]-methanesulfonamide (64.2 mg, 0.19 mmol) were converted to 2-{7-[5-chloro-4-((1R,2R)-2-methanesulfonylamino-cyclohexylamino)-pyrimidin-2-ylamino]-8-methoxy-1,2,4,5-tetrahydro-benzo[d]azepin-3-yl}-N,N-dimethyl-acetamide (70 mg, 60%) as a white solid. MP: 92-97° C.; $^1$H-NMR (CDCl$_3$) δ 7.95 (s, 1H), 7.93 (s, 1H), 7.33 (s, 1H), 6.62 (s, 1H), 5.30 (br s, 1H), 5.42 (d, J=7.6 Hz, 1H), 3.92 (m, 1H), 3.88 (s, 3H), 3.27 (m, 3H), 3.12 (s, 3H), 2.98 (s, 3H), 2.89 (m, 4H), 2.78 (s, 3H), 2.75 (m, 2H), 2.66 (m, 2H), 2.22 (br s, 2H), 1.22-1.45 (m, 6H); LC/MS (ESI+): 580.87 (M+H).

Example 259

2-[5-Chloro-2-(3-dimethylcarbamoylmethyl-8-methoxy-2,3,4,5-tetrahydro-1H-benzo[d]azepin-7-ylamino)-pyrimidin-4-ylamino]-N-methyl-benzamide Following a procedure similar to 247b, except that a 0 to 10% MeOH/ethyl acetate gradient was used for chromatography, 2-(7-amino-8-methoxy-1,2,4,5-tetrahydro-benzo[d]azepin-3-yl)-N,N-dimethyl-acetamide (50 mg, 0.2 mmol) and 2-(2,5-dichloro-pyrimidin-4-ylamino)-N-methyl-benzamide (53.1 mg, 0.18 mmol) were converted to 2-[5-chloro-2-(3-dimethylcarbamoylmethyl-8-methoxy-2,3,4,5-tetrahydro-1H-benzo[d]azepin-7-ylamino)-pyrimidin-4-ylamino]-N-methyl-benzamide (43 mg, 44%) as a light yellow solid. MP: 83-89° C.; $^1$H-NMR (CDCl$_3$) δ 10.99 (s, 1H), 8.65 (d, J=8.3 Hz, 1H), 8.11 (s, 1H), 8.07 (s, 1H), 7.45 (m, 3H), 7.09 (t, J=7.3 Hz, 1H), 6.65 (s, 1H), 6.23 (br s, 1H), 3.86 (s, 3H), 3.28 (s, 2H), 3.15 (s, 3H), 3.05 (d, J=4.8 Hz, 3H), 2.98 (s, 3H), 2.89 (m, 2H), 2.79 (m, 2H), 2.67 (m, 4H); LC/MS (ESI+): 538.05 (M+H).

Example 260

(2-exo,3-exo)-3-[5-Chloro-2-(3-dimethylcarbamoylmethyl-8-methoxy-2,3,4,5-tetrahydro-1H-benzo[d]azepin-7-ylamino)-pyrimidin-4-ylamino]-bicyclo[2.2.1]hept-5-ene-2-carboxylic acid amide Following a procedure similar to 247b, except that a 0 to 10% MeOH/ethyl acetate gradient was used for chromatography, 2-(7-amino-8-methoxy-1,2,4,5-tetrahydro-benzo[d]azepin-3-yl)-N,N-dimethyl-acetamide (50 mg, 0.2 mmol) and (2-exo,3-exo)-3-(2,5-dichloro-pyrimidin-4-ylamino)-bicyclo[2.2.1]hept-5-ene-2-carboxylic acid amide (56.6 mg, 0.19 mmol) were converted to (2-exo,3-exo)-3-[5-Chloro-2-(3-dimethylcarbamoylmethyl-8-methoxy-2,3,4,5-tetrahydro-1H-benzo[d]azepin-7-ylamino)-pyrimidin-4-ylamino]-bicyclo[2.2.1]hept-5-ene-2-carboxylic acid amide (47 mg, 43%) as a white solid. MP: 118-131° C.; $^1$H-NMR (CDCl$_3$) δ 8.18 (s, 1H), 7.88 (s, 1H), 7.40 (s, 1H), 6.63 (s, 1H), 6.57 (d J=8.1 Hz, 1H), 6.30 (s, 1H), 5.62 (br s, 1H), 5.33 (br s, 1H), 4.44 (t J=8.1 Hz, 1H), 3.86 (s, 3H), 3.28 (s, 2H), 3.14 (s, 3H), 3.06 (s, 1H), 2.97 (s, 3H), 2.87 (m, 6H), 2.69 (m, 4H), 2.52 (d, J=8.1 Hz, 1H), 2.26 (d, J=9.3 Hz, 1H), 1.65 (d, J=9.1 Hz, 1H); LC/MS (ESI+): 539.89 (M+H).

Example 261

2-{7-[5-Chloro-4-(2-methoxy-4-morpholin-4-yl-phenylamino)-pyrimidin-2-ylamino]-8-methoxy-1,2,4,5-tetrahydro-benzo[d]azepin-3-yl}-N,N-dimethyl-acetamide Following a procedure similar to 247b, except that a 0 to 10% MeOH/ethyl acetate gradient was used for chromatography, 2-(7-amino-8-methoxy-1,2,4,5-tetrahydro-benzo[d]azepin-3-yl)-N,N-dimethyl-acetamide (50 mg, 0.2 mmol), and (2,5-dichloro-pyrimidin-4-yl)-(2-methoxy-4-morpholin-4-yl-phenyl)-amine (70.4 mg, 0.2 mmol) were converted to 2-{7-[5-chloro-4-(2-methoxy-4-morpholin-4-yl-phenylamino)-pyrimidin-2-ylamino]-8-methoxy-1,2,4,5-tetrahydro-benzo[d]azepin-3-yl}-N,N-dimethyl-acetamide (64 mg, 52%) as a white solid. MP: 67-76° C.; $^1$H-NMR (CDCl$_3$) δ 8.24 (d, J=8.6 Hz, 1H), 8.09 (s, 1H), 8.01 (s, 1H), 7.52 (s, 1H), 7.45 (s, 1H), 6.64 (s, 1H), 6.53 (d, J=2.3 Hz, 1H), 6.50 (dd, J=2.2 Hz, 9.1 Hz, 1H), 3.95 (s, 3H), 3.90 (t, J=4.8 Hz, 4H), 3.86 (s, 3H), 3.27 (s, 2H), 3.15 (t, J=5.0 Hz, 4H), 3.13 (s, 3H), 2.98 (s, 3H), 2.85 (m, 4H), 2.69 (m, 4H); LC/MS (ESI+): 595.88 (M+H).

Example 262

2-[5-Chloro-2-(3-dimethylcarbamoylmethyl-8-methoxy-2,3,4,5-tetrahydro-1H-benzo[d]azepin-7-ylamino)-pyrimidin-4-ylamino]-N-ethyl-benzamide Following a procedure similar to 247b, except that a 0 to 10% MeOH/ethyl acetate gradient was used for chromatography, 2-(7-amino-8-methoxy-1,2,4,5-tetrahydro-benzo[d]azepin-3-yl)-N,N-dimethyl-acetamide (50 mg, 0.2 mmol) and 2-(2,5-dichloro-pyrimidin-4-ylamino)-N-ethyl-benzamide (61.7 mg, 0.2 mmol) were converted to 2-[5-chloro-2-(3-dimethylcarbamoylmethyl-8-methoxy-2,3,4,5-tetrahydro-1H-benzo[d]azepin-7-ylamino)-pyrimidin-4-ylamino]-N-ethyl-benzamide (38 mg, 32%) as a yellow solid. MP: 99-111° C.; $^1$H-NMR (CDCl$_3$) δ 10.92 (s, 1H), 8.65 (d, J=8.4 Hz, 1H), 8.12 (s, 1H), 8.08 (s, 1H), 7.47 (m, 3H), 7.09 (t, J=7.5 Hz, 1H), 6.63 (s, 1H), 6.17 (m, 1H), 3.88 (s, 3H), 3.51 (m, 2H), 3.28 (s, 2H), 3.14 (s, 3H), 2.98 (s, 3H), 2.89 (m, 2H), 2.79 (m, 2H), 2.67 (m, 4H), 1.28 (t, J=7.3 Hz, 3H); LC/MS (ESI+): 552.18 (M+H).

Example 263

N-{(1R,2R)-2-[5-Chloro-2-(8-methoxy-2-oxo-2,3,4,5-tetrahydro-1H-benzo[d]azepin-7-ylamino)-pyrimidin-4-ylamino]-cyclohexyl}-methanesulfonamide 263a) 8-methoxy-1,3,4,5-tetrahydro-benzo[d]azepin-2-one (1.5 g, 7.8 mmol) was treated with 65% nitric acid (25 mL, 0.39 mol) at 0° C. for 1 hour. The reaction was quenched at 0° C. with saturated Na$_2$CO$_3$ to pH 9-10, then extracted three times with dichloromethane. The organic extracts were dried (MgSO$_4$) and concentrated. The products (yellow solids) were separated by flash chromatography (SiO$_2$, ethyl acetate): 8-methoxy-7-nitro-1,3,4,5-tetrahydro-benzo[d] azepin-2-one (360 mg, 19%), and 8-methoxy-9-nitro-1,3,4, 5-tetrahydro-benzo[d]azepin-2-one (400 mg, 20%). $^1$H-NMR (CDCl$_3$) δ 7.69 (s, 1H), 6.87 (s, 1H), 6.05 (br s, 1H), 3.95 (s, 3H), 3.89 (s, 2H), 3.60 (q, J=6.3 Hz, 2H), 3.12 (t, J=6.3, 2H); LC/MS (ESI+): 237.05 (M+H).

263b) To a solution of 8-methoxy-7-nitro-1,3,4,5-tetrahydro-benzo[d]azepin-2-one (360 mg, 1.5 mmol) in methanol (30 mL) was added palladium 10% wt on Carbon (50% wet; 50 mg). The mixture was shaken in a Parr apparatus under an atmosphere of hydrogen (50 PSI) for 30 minutes. Filtration through Celite and evaporation of the solvent provided 7-amino-8-methoxy-1,3,4,5-tetrahydro-benzo[d]azepin-2-one (300 mg, 95%) as a tan solid. $^1$H-NMR (CDCl$_3$) δ 6.54 (s, 1H), 6.47 (s, 1H), 5.80 (br s, 1H), 3.82 (s, 3H), 3.73 (s, 2H), 3.71 (br s, 2H), 3.53 (q, J=6.3 Hz, 2H), 2.96 (t, J=6.1 Hz, 2H); LC/MS (ESI+): 207.13 (M+H).

263c) 7-Amino-8-methoxy-1,3,4,5-tetrahydro-benzo[d] azepin-2-one (50 mg, 0.2 mmol), N-[(1R,2R)-2-(2,5-dichloro-pyrimidin-4-ylamino)-cyclohexyl]-methanesulfonamide (90.5 mg, 0.27 mmol), and a 4 M solution of hydrogen chloride in dioxane (0.1 mL, 2 eq), were added to 2-methoxyethanol (2 mL), and the reaction mixture was heated for 6 hours at 120° C. The reaction mixture was partitioned between aqueous saturated Na$_2$CO$_3$ and dichloromethane, and the aqueous phase was extracted twice with dichloromethane. The combined organic extracts were dried (MgSO4), filtered, and then concentrated on SiO$_2$. Flash chromatography on SiO$_2$ (MeOH/dichloromethane 0-5%) gave N-{(1R,2R)-2-[5-Chloro-2-(8-methoxy-2-oxo-2,3,4,5-tetrahydro-1H-benzo[d]azepin-7-ylamino)-pyrimidin-4-ylamino]-cyclohexyl}-methanesulfonamide (47 mg, 30%) as a beige solid. MP: 109-115° C.; $^1$H-NMR (CDCl$_3$) δ 8.06 (s, 1H), 7.90 (s, 1H), 7.40 (s, 1H), 6.62 (s, 1H), 6.18 (m, 1H), 6.00 (d, J=6.5 Hz, 1H), 5.51 (d, J=7.8 Hz, 1H), 3.94 (m, 1H), 3.86 (s, 3H), 3.75 (m, 2H), 3.53 (m, 2H), 3.25 (m, 1H), 3.04 (t, J=6.1 Hz, 2H), 2.85 (s, 3H), 2.60 (s, 2H), 2.20 (m, 2H), 1.8 (m, 2H), 1.34 (m, 2H); LC/MS (ESI+): 509.28 (M+H).

Example 264

2-[5-Chloro-2-(8-methoxy-2-oxo-2,3,4,5-tetrahydro-1H-benzo[d]azepin-7-ylamino)-pyrimidin-4-ylamino]-N-methyl-benzamide Following a procedure similar to 263c, 7-amino-8-methoxy-1,3,4,5-tetrahydro-benzo[d]azepin-2-one (50 mg, 0.2 mmol) and 2-(2,5-dichloro-pyrimidin-4-ylamino)-N-methyl-benzamide (79.2 mg, 0.27 mmol) were converted to 2-[5-chloro-2-(8-methoxy-2-oxo-2,3,4,5-tetrahydro-1H-benzo[d]azepin-7-ylamino)-pyrimidin-4-ylamino]-N-methyl-benzamide (9.2 mg, 8%) as a white solid. m.p.>250° C.; $^1$H-NMR (CDCl$_3$) δ 11.03 (s, 1H), 8.65 (d, J=8.3 Hz, 1H), 8.13 (s, 1H), 8.11 (s, 1H), 7.38 (m, 3H), 7.08 (t, J=7.2 Hz, 1H), 6.65 (s, 1H), 6.20 (br s, 1H), 5.72 (br s, 1H), 3.88 (s, 3H), 3.79 (s, 2H), 3.55 (q, J=5.3 Hz, 2H), 3.05 (d, J=5.0 Hz, 3H), 3.00 (t, J=5.8 Hz, 2H); LC/MS (ESI+): 467.36 (M+H).

Example 265

2-[5-Chloro-2-(8-methoxy-2-oxo-2,3,4,5-tetrahydro-1H-benzo[d]azepin-7-ylamino)-pyrimidin-4-ylamino]-N-ethyl-benzamide Following a procedure similar to 263c, 7-amino-8-methoxy-1,3,4,5-tetrahydro-benzo[d]azepin-2-one (50 mg, 0.2 mmol) and 2-(2,5-dichloro-pyrimidin-4-ylamino)-N-ethyl-benzamide (82.98 mg, 0.0002667 mol) were converted to 2-[5-Chloro-2-(8-methoxy-2-oxo-2,3,4,5-tetrahydro-1H-benzo[d]azepin-7-ylamino)-pyrimidin-4-ylamino]-N-ethyl-benzamide (7.6 mg, 6%) as a white solid. m.p.>250° C.; $^1$H-NMR (CDCl$_3$) δ 10.99 (s, 1H), 8.65 (d, J=8.3 Hz, 1H), 8.13 (s, 1H), 8.11 (s, 1H), 7.49 (m, 3H), 6.99 (t, J=7.6 Hz, 1H), 6.65 (s, 1H), 6.15 (br s, 1H), 5.70 (br s, 1H), 3.88 (s, 3H), 3.80 (s, 2H), 3.55 (m, 4H), 2.98 (m, 2H), 1.28 (t, J=7.1 Hz, 3H); LC/MS (ESI+): 482.18 (M+H).

Example 271

2-[5-Chloro-2-(10-ethyl-10-aza-tricyclo[6.3.2.0*2, 7*]trideca-2,4,6-trien-4-ylamino)-pyrimidin-4-ylamino]-N-methyl-benzamide 271a) 10-Aza-tricyclo[6.3.2.0*2,7*]trideca-2(7),3,5-triene (O'Donnell, C. J. *J. Org. Chem.* 2004, 69, 5756) (5.0 g, 28.9 mmol) was cooled to −10° C. and fuming nitric acid (150 mL) at −10° C. was added over 5 minutes. The reaction was stirred at −10° C. for 1 hour. Ice was then added and the reaction was made basic with 10 N aqueous NaOH. The product was extracted into 3×EtOAc (200 mL) and the combined organic layers were dried (sodium sulfate), filtered, and concentrated under reduced pressure to obtain 4-nitro-1-aza-tricyclo[6.3.2.0*2,7*]trideca-2(7),3,5-triene as a brown amorphous solid (6.3 g, 85%). $^1$H-NMR (CDCl$_3$, 400 MHz) δ 8.06 (dd, 1H, J=2.3 and 8.2 Hz), 7.96 (d, 1H, J=2.3 Hz), 7.23 (d, 1H, J=8.1 Hz), 3.12-3.06 (m, 2H), 3.02-2.87 (m, 4H), 2.17-2.10 (m, 2H), 1.87-1.80 (m, 2H), 1.68 (bs, 1H).

271b) 4-Nitro-1-aza-tricyclo[6.3.2.0*2,7*]trideca-2(7),3, 5-triene (82 mg, 0.376 mmol) was dissolved in acetone (5 mL) and K$_2$CO$_3$ (104 mg, 0.752 mmol, 2.0 eq) and ethyl iodide (64.2 mg, 0.414 mmol, 32.9 μL, 1.1 eq) were added. The reaction was stirred at room temperature for 48 hours. The reaction was then concentrated under reduced pressure and the residue was taken up in CH$_2$Cl$_2$ (10 mL) and washed with water (10 mL). The organic layer was dried (sodium sulfate), filtered, and concentrated under reduced pressure. Purification by silica gel chromatography using a gradient of 0-20% MeOH/CH$_2$Cl$_2$ as the eluting solvent to obtain 10-ethyl-4-nitro-10-aza-tricyclo[6.3.2.0*2,7*]trideca-2(7), 3,5-triene as a pale orange oil (68 mg, 73%). LCMS (m/e) 247 (M+1); $^1$H-NMR (CDCl$_3$, 400 MHz) δ 8.03 (dd, 1H, J=2.3 and 8.1 Hz), 7.94 (d, 1H, J=2.3 Hz), 7.20 (d, 1H, J=8.1 Hz), 3.17-3.08 (m, 2H), 2.95-2.86 (m, 2H), 2.43 (q, 2H, J=7.1 Hz), 2.30-2.19 (m, 4H), 1.66-1.57 (m, 2H), 0.99 (t, 3H, J=7.1 Hz).

271c) 10-Ethyl-4-nitro-10-aza-tricyclo[6.3.2.0*2,7*] trideca-2(7),3,5-triene (68 mg, 0.276 mmol) was placed in methanol (4 mL) and 10% palladium on carbon (6.8 mg) was added. The reaction was hydrogenated at 15 psi for 30 minutes. The mixture was then filtered through celite and concentrated under reduced pressure to obtain 10-ethyl-10-aza-tricyclo[6.3.2.0*2,7*]trideca-2(7),3,5-trien-4-ylamine as a yellow oil (59.6 mg, 100%). LCMS (m/e) 217 (M+1); $^1$H-NMR (CDCl$_3$, 400 MHz) δ 6.85 (d, 1H, J=7.4 Hz), 6.50-6.45 (m, 2H), 3.52 (bs, 2H), 2.94-2.85 (m, 4H), 2.42 (q, 2H, J=7.1 Hz), 2.20-2.12 (m, 4H), 1.60-1.56 (m, 2H), 0.99 (t, 3H, J=7.1 Hz).

271d) 10-Ethyl-10-aza-tricyclo[6.3.2.0*2,7*]trideca-2(7), 3,5-trien-4-ylamine (29.8 mg, 0.138 mmol) and 2-(2,5-dichloro-pyrimidin-4-ylamino)-N-methyl-benzamide (45 mg, 0.152 mmol, 1.1 eq) were dissolved in IPA (1.5 mL). 4.0 M HCl in dioxane (38 μL, 0.152 mmol, 1.1 eq) was added and the reaction was heated at 130° C. in a microwave for 10 minutes. The reaction was then concentrated under reduced pressure and the residue was taken up in CH$_2$Cl$_2$ (10 mL) and washed with sat. NaHCO$_3$ (10 mL). The organic layer was dried (sodium sulfate), filtered, and concentrated under reduced pressure. Purification by basic alumina chromatography using a gradient of 0-5% MeOH/CH$_2$Cl$_2$ as the eluting solvent to obtain 2-[5-chloro-2-(10-ethyl-10-aza-tricyclo[6.3.2.0*2,7*]trideca-2,4,6-trien-4-ylamino)-pyrimidin-4-ylamino]-N-methyl-benzamide as a yellow solid (38 mg, 58%). m.p. dec. at 106° C.; LCMS (m/e) 477 (M+1); $^1$H-NMR (CDCl$_3$, 400 MHz) δ 11.02 (s, 1H), 8.67 (d, 1H, J=8.4 Hz), 8.09 (s, 1H), 7.50-7.40 (m, 2H), 7.34 (d, 1H, J=2.3 Hz), 7.30-7.20 (m, 1H), 7.02 (t, 1H, J=7.6 Hz), 7.00 (d, 1H, J=7.9 Hz), 6.87 (s, 1H), 6.19 (bs, 1H), 3.03 (d, 3H, 4.9 Hz), 3.00-2.90 (m, 4H), 2.44 (q, 2H, J=7.1 Hz), 2.21-2.16 (m, 4H), 1.64-1.60 (m, 2H), 1.00 (t, 3H, J=7.1 Hz).

Example 272

2-[5-Chloro-2-(10-ethyl-10-aza-tricyclo[6.3.2.0*2,7*]trideca-2,4,6-trien-4-ylamino)-pyrimidin-4-ylamino]-N-methyl-benzenesulfonamide 2-[5-Chloro-2-(10-ethyl-10-aza-tricyclo[6.3.2.0*2,7*]trideca-2,4,6-trien-4-ylamino)-pyrimidin-4-ylamino]-N-methyl-benzenesulfonamide was prepared from 10-ethyl-10-aza-tricyclo[6.3.2.0*2,7*]trideca-2,4,6-trien-4-ylamine and 2-(2,5-dichloro-pyrimidin-4-ylamino)-N-methyl-benzenesulfonamide in an analogous manner to Example 271. Product isolated as a clear thin film (13 mg, 18%). LCMS (m/e) 513 (M+1); $^1$H-NMR (CDCl$_3$, 400 MHz) δ 9.13 (s, 1H), 8.48 (d, 1H, J=8.4 Hz), 8.01 (s, 1H), 7.95 (d, 1H, J=7.9 Hz), 7.55 (t, 1H, J=7.7 Hz), 7.27-7.20 (m, 2H), 7.06 (s, 1H), 6.99 (d, 1H, J=8.5 Hz), 5.11 (bs, 1H), 3.00-2.80 (m, 4H), 2.63 (s, 3H), 2.44 (q, 2H, J=6.7 Hz), 2.30-2.10 (m, 4H), 1.62-1.58 (m, 2H), 1.01 (t, 3H, J=7.0 Hz).

Example 273

2-[5-Chloro-2-(10-isopropyl-10-aza-tricyclo[6.3.2.0*2,7*]trideca-2,4,6-trien-4-ylamino)-pyrimidin-4-ylamino]-N-methyl-benzamide 273a) 4-Nitro-1-aza-tricyclo[6.3.2.0*2,7*]trideca-2(7),3,5-triene (80 mg, 0.367 mmol) was placed in 1,2-dichloroethane (2 mL) and acetic acid (0.1 mL). Acetone (31.9 mg, 0.550 mmol, 40.4 μL, 1.5 eq) was added and the reaction was stirred for 5 minutes. Sodium borohydride (16.3 mg, 0.440 mmol, 1.2 eq) was added and the reaction was heated at 80° C. for 2 hours. The reaction was then diluted with CH$_2$Cl$_2$ (10 mL) and washed with water (10 mL). The organic layer was dried (sodium sulfate), filtered, and concentrated under reduced pressure. Purification by silica gel chromatography using a gradient of 0-15% MeOH/CH$_2$Cl$_2$ as the eluting solvent to obtain 10-isopropyl-4-nitro-10-aza-tricyclo[6.3.2.0*2,7*]trideca-2(7),3,5-triene as pale orange oil (62 mg, 65%). LCMS (m/e) 261 (M+1); $^1$H-NMR (CDCl$_3$, 400 MHz) δ 8.02 (dd, 1H, J=2.2 and 8.1 Hz), 7.93 (d, 1H, J=2.2 Hz), 7.19 (d, 1H, J=8.1 Hz), 3.15-3.08 (m, 2H), 2.90-2.75 (m, 3H), 2.35 (t, 2H, J=9.5 Hz), 2.21 (d, 2H, J=8.8 Hz), 1.60-1.55 (m, 2H), 0.93 (d, 6H, J=6.6 Hz).

273b) 10-Isopropyl-4-nitro-10-aza-tricyclo[6.3.2.0*2,7*]trideca-2(7),3,5-triene (62 mg, 0.238 mmol) was placed in methanol (4 mL) and 10% palladium on carbon (6.2 mg) was added. The reaction was hydrogenated at 15 psi for 30 minutes. The mixture was then filtered through celite and concentrated under reduced pressure to obtain 10-isopropyl-10-aza-tricyclo[6.3.2.0*2,7*]trideca-2(7),3,5-trien-4-ylamine as a yellow oil (54.7 mg, 100%). LCMS (m/e) 231 (M+1); $^1$H-NMR (CDCl$_3$, 400 MHz) δ 6.85 (dd, 1H, J=0.7 and 7.2 Hz), 6.50-6.45 (m, 2H), 3.52 (bs, 2H), 2.87-2.78 (m, 5H), 2.33-2.26 (m, 2H), 2.18-2.09 (m, 2H), 1.60-1.50 (m, 2H), 0.93 (d, 6H, J=6.6 Hz).

273c) 2-[5-Chloro-2-(10-isopropyl-10-aza-tricyclo[6.3.2.0*2,7*]trideca-2,4,6-trien-4-ylamino)-pyrimidin-4-ylamino]-N-methyl-benzamide was prepared from 10-isopropyl-10-aza-tricyclo[6.3.2.0*2,7*]trideca-2(7),3,5-trien-4-ylamine and 2-(2,5-dichloro-pyrimidin-4-ylamino)-N-methyl-benzamide in an analogous manner to Example 271d. Product isolated as a light brown foam (35 mg, 60%). LCMS (m/e) 491 (M+1); $^1$H-NMR (CDCl$_3$, 400 MHz) δ 11.02 (s, 1H), 8.67 (d, 1H, J=8.4 Hz), 8.09 (s, 1H), 7.47 (dd, 1H, J=1.3 and 7.8 Hz), 7.46-7.42 (m, 2H), 7.33 (d, 1H, J=2.2 Hz), 7.26-7.23 (m, 1H), 7.10-7.03 (m, 1H), 7.00 (d, 1H, J=7.9 Hz), 6.87 (s, 1H), 6.18 (bs, 1H), 3.03 (d, 3H, J=4.9 Hz), 2.98-2.91 (m, 1H), 2.91-2.79 (m, 4H), 2.35-2.30 (m, 2H), 2.18-2.15 (m, 2H), 1.60-1.55 (m, 2H), 0.95 (d, 6H, J=6.6 Hz).

Example 274

2-[5-Chloro-2-(10-isopropyl-10-aza-tricyclo[6.3.2.0*2,7*]trideca-2,4,6-trien-4-ylamino)-pyrimidin-4-ylamino]-N-methyl-benzenesulfonamide 2-[5-Chloro-2-(10-isopropyl-10-aza-tricyclo[6.3.2.0*2,7*]trideca-2,4,6-trien-4-ylamino)-pyrimidin-4-ylamino]-N-methyl-benzenesulfonamide was prepared from 10-isopropyl-10-aza-tricyclo[6.3.2.0*2,7*]trideca-2,4,6-trien-4-ylamine and 2-(2,5-dichloro-pyrimidin-4-ylamino)-N-methyl-benzenesulfonamide in an analogous manner to Example 273. Product isolated as a clear thin film (21 mg, 33%). LCMS (m/e) 527 (M+1); $^1$H-NMR (CDCl$_3$, 400 MHz) δ 9.13 (s, 1H), 8.48 (d, 1H, J=8.3 Hz), 7.99 (s, 1H), 7.94 (dd, 1H, J=1.5 and 8.0 Hz), 7.58-7.51 (m, 1H), 7.26-7.19 (m, 3H), 7.08 (s, 1H), 6.98 (dd, 1H, J=3.4 and 5.3 Hz), 5.21 (bs, 1H), 3.00-2.90 (m, 1H), 2.89-2.77 (m, 4H), 2.62 (d, 3H, J=2.7 Hz), 2.31 (d, 2H, J=1.0 Hz), 2.16 (d, 2H, J=8.1 Hz), 1.55 (d, 2H, J=8.2 Hz), 0.94 (d, 6H, J=6.6 Hz).

Example 275

2-[5-Chloro-2-(10-cyanomethyl-10-aza-tricyclo[6.3.2.0*2,7*]trideca-2,4,6-trien-4-ylamino)-pyrimidin-4-ylamino]-N-methyl-benzenesulfonamide 275a) 4-Nitro-1-aza-tricyclo[6.3.2.0*2,7*]trideca-2(7),3,5-triene (250 mg, 1.15 mmol) was placed in methanol (10 mL) and acetic acid (0.2 mL). 10% Palladium on carbon (6.8 mg) was then added. The reaction was hydrogenated at 50 psi for 3 hours. The mixture was then filtered through celite and concentrated under reduced pressure. The residue was taken up in toluene (20 mL) and concentrated under reduced pressure to obtain 10-aza-tricyclo[6.3.2.0*2,7*]trideca-2,4,6-trien-4-ylamine as a light brown oil (193 mg, 89%). LCMS (m/e) 189 (M+1); $^1$H-NMR (CDCl$_3$, 400 MHz) δ 6.89 (d, 1H, J=7.8 Hz), 6.53 (dd, 1H, J=2.4 and 7.8 Hz), 6.48 (d, 1H, J=2.3 Hz), 3.20-2.80 (m, 8H), 2.02 (d, 2H, J=8.7 Hz), 1.82 (d, 2H, J=10.7 Hz).

275b) 10-Aza-tricyclo[6.3.2.0*2,7*]trideca-2,4,6-trien-4-ylamine (193 mg, 1.02 mmol) was dissolved in acetone (20 mL) and Cs$_2$CO$_3$ (994 mg, 3.06 mmol, 3.0 eq) and bromoacetonitrile (134 mg, 1.13 mmol, 91 μL, 1.1 eq) were added. The reaction was stirred at room temperature for 2 hours and was then concentrated under reduced pressure. The residue was taken up in CH$_2$Cl$_2$ (10 mL) and washed with water (10 mL).

The organic layer was dried (sodium sulfate), filtered, and concentrated under reduced pressure. Purification by silica gel chromatography using a gradient of 0-10% MeOH/$CH_2Cl_2$ as the eluting solvent to obtain (4-amino-10-aza-tricyclo[6.3.2.0*2,7*]trideca-2,4,6-trien-10-yl)-acetonitrile as a brown oil (123 mg, 53%). LCMS (m/e) 227 (M+1); $^1$H-NMR (CDCl$_3$, 400 MHz) δ 6.87 (d, 1H, J=7.7 Hz), 6.50 (dd, 1H, J=2.4 and 7.7 Hz), 6.47 (d, 1H, J=2.3 Hz), 3.57 (bs, 2H), 3.52 (s, 2H), 3.00-2.90 (m, 2H), 2.99-2.80 (m, 2H), 2.61-2.50 (m, 2H), 2.20-2.05 (m, 2H), 1.70-1.63 (m, 2H).

275c) (4-Amino-10-aza-tricyclo[6.3.2.0*2,7*]trideca-2,4,6-trien-10-yl)-acetonitrile (30 mg, 0.132 mmol) and 2-(2,5-dichloro-pyrimidin-4-ylamino)-N-methyl-benzenesulfonamide (48.3 mg, 0.145 mmol, 1.1 eq) were dissolved in IPA (1.2 mL). 4.0 M HCl in dioxane (36 µL, 0.145 mmol, 1.1 eq) was added and the reaction was heated at 130° C. in a microwave for 20 minutes. The reaction was then concentrated under reduced pressure and the residue was taken up in $CH_2Cl_2$ (10 mL) and washed with sat. NaHCO$_3$ (10 mL). The organic layer was dried (sodium sulfate), filtered, and concentrated under reduced pressure. Purification by preparative HPLC using a gradient of 5-75% acetonitrile/water as the eluting solvent to obtain 2-[5-chloro-2-(10-cyanomethyl-10-aza-tricyclo[6.3.2.0*2,7*]trideca-2,4,6-trien-4-ylamino)-pyrimidin-4-ylamino]-N-methyl-benzenesulfonamide as an orange film (13 mg, 19%). LCMS (m/e) 524 (M+1); $^1$H-NMR (CDCl$_3$, 400 MHz) δ 9.11 (s, 1H), 8.48 (d, 1H, J=8.3 Hz), 8.07 (s, 1H), 7.95 (dd, 1H, J=1.5 and 8.0 Hz), 7.60-7.53 (m, 1H), 7.35-7.20 (m, 3H), 7.05-6.99 (m, 2H), 4.86 (bs, 1H), 3.55 (s, 2H), 3.10-3.01 (m, 1H), 2.99-2.91 (m, 1H), 2.91-2.83 (m, 2H), 2.64 (s, 3H), 2.58 (d, 2H, J=9.9 Hz), 2.15 (d, 2H, J=8.3 Hz), 1.68 (d, 2H, J=9.4 Hz).

Example 276

2-{5-Chloro-2-[10-(2,2,2-trifluoro-acetyl)-10-aza-tricyclo[6.3.2.0*2,7*]trideca-2,4,6-trien-4-ylamino]-pyrimidin-4-ylamino}-N-methyl-benzamide 276a) 4-Nitro-1-aza-tricyclo[6.3.2.0*2,7*]trideca-2(7),3,5-triene (949 mg, 4.35 mmol) was dissolved in dichloromethane (15 mL) and pyridine (800 mg, 10.12 mmol, 0.818 mL, 2.33 eq) and trifluoroacetic anhydride (1.06 g, 5.06 mmol, 0.702 mL, 1.16 eq) were added. The reaction was stirred at room temperature for 3 hours and then 1 N HCl (10 mL) was added. The layers were separated and the aqueous layer was extracted with dichloromethane (20 mL). The combined organic layers were dried (sodium sulfate), filtered, and concentrated under reduced pressure. Purification by silica gel chromatography using a gradient of 0-50% EtOAc/hex as the eluting solvent to obtain 2,2,2-trifluoro-1-(4-nitro-10-aza-tricyclo[6.3.2.0*2,7*]trideca-2,4,6-trien-10-yl)-ethanone as a yellow oil (1.227 g, 90%). LCMS (m/e) 315 (M+1); $^1$H-NMR (CDCl$_3$, 400 MHz) δ 8.16-8.09 (m, 1H), 8.03 (dd, 1H, J=2.3 and 7.9 Hz), 7.31 (dd, 1H, J=8.2 and 10.3 Hz), 4.21-4.15 (m, 1H), 3.95-3.85 (m, 1H), 3.65-3.43 (m, 2H), 3.41-3.30 (m, 2H), 2.17-2.08 (m, 2H), 1.85-1.75 (m, 2H).

276b) 2,2,2-Trifluoro-1-(4-nitro-10-aza-tricyclo[6.3.2.0*2,7*]trideca-2,4,6-trien-10-yl)-ethanone (1.227 g, 3.91 mmol) was placed in methanol (100 mL) and acetic acid (1 mL). 10% Palladium on carbon (6.8 mg) was then added. The reaction was hydrogenated at 20 psi for 30 minutes. The mixture was then filtered through celite and concentrated under reduced pressure to obtain 1-(4-amino-10-aza-tricyclo[6.3.2.0*2,7*]trideca-2,4,6-trien-10-yl)-2,2,2-trifluoro-ethanone as a brown oil (1.110 g, 100%). LCMS (m/e) 285 (M+1); $^1$H-NMR (CDCl$_3$, 400 MHz) δ 6.92 (dd, 1H, J=8.0 and 10.9 Hz), 6.60-6.50 (m, 2H), 4.23-4.10 (m, 1H), 3.90-3.75 (m, 1H), 3.46-3.25 (m, 2H), 3.15-3.00 (m, 2H), 2.03-1.91 (m, 2H), 1.80-1.70 (m, 2H).

276c) 1-(4-Amino-10-aza-tricyclo[6.3.2.0*2,7*]trideca-2,4,6-trien-10-yl)-2,2,2-trifluoro-ethanone (30 mg, 0.106 mmol) and 2-(2,5-dichloro-pyrimidin-4-ylamino)-N-methyl-benzamide (34.5 mg, 0.116 mmol, 1.1 eq) were dissolved in IPA (1.5 mL). 4.0 M HCl in dioxane (29 µL, 0.116 mmol, 1.1 eq) was added and the reaction was heated at 120° C. in a microwave for 20 minutes. The reaction was then concentrated under reduced pressure and the residue was taken up in $CH_2Cl_2$ (10 mL) and washed with sat. NaHCO$_3$ (10 mL). The organic layer was dried (sodium sulfate), filtered, and concentrated under reduced pressure. Purification by silica gel chromatography using a gradient of 0-75% EtOAc/hex as the eluting solvent to obtain 2-{5-chloro-2-[10-(2,2,2-trifluoro-acetyl)-10-aza-tricyclo[6.3.2.0*2,7*]trideca-2,4,6-trien-4-ylamino]-pyrimidin-4-ylamino}-N-methyl-benzamide as a yellow foam (45 mg, 78%). LCMS (m/e) 545 (M+1); $^1$H-NMR (CDCl$_3$, 400 MHz) major rotomer δ 11.01 (s, 1H), 8.61 (d, 1H, J=8.4 Hz), 8.10 (s, 1H), 7.53-7.40 (m, 3H), 7.36-7.26 (m, 1H), 7.13-6.95 (m, 3H), 6.22 (bs, 1H), 4.31-4.17 (m, 1H), 3.92-3.82 (m, 1H), 3.40-3.28 (m, 1H), 3.22-3.08 (m, 2H), 3.04 (d, 3H, J=4.5 Hz), 2.10-1.98 (m, 2H), 1.88-1.72 (m, 2H), 1.30-1.20 (m, 1H).

Example 277

2-[2-(10-Aza-tricyclo[6.3.2.0*2,7*]trideca-2,4,6-trien-4-ylamino)-5-chloro-pyrimidin-4-ylamino]-N-methyl-benzamide 2-{5-Chloro-2-[10-(2,2,2-trifluoro-acetyl)-10-aza-tricyclo[6.3.2.0*2,7*]trideca-2,4,6-trien-4-ylamino]-pyrimidin-4-ylamino}-N-methyl-benzamide (402 mg, 0.739 mmol) was dissolved in methanol (30 mL) and potassium carbonate (612 mg, 4.43 mmol, 6.0 eq) was added. The reaction was stirred at room temperature for 48 hours and then concentrated under reduced pressure. Water (10 mL) was added and the product was collected by filtration. 2-[2-(10-Aza-tricyclo[6.3.2.0*2,7*]trideca-2,4,6-trien-4-ylamino)-5-chloro-pyrimidin-4-ylamino]-N-methyl-benzamide was obtained as a yellow solid (330 mg, 99%). m.p. dec. at 230° C.; LCMS (m/e) 449 (M+1); $^1$H-NMR (CD$_3$OD, 400 MHz) δ 8.68 (d, 1H, J=8.3 Hz), 8.04 (s, 1H), 7.65 (d, 1H, J=7.8 Hz), 7.47-7.39 (m, 2H), 7.33 (dd, 1H, J=2.1 and 7.9 Hz), 7.23-7.17 (m, 1H), 7.16-7.08 (m, 3H), 7.04 (d, 1H, J=7.8 Hz), 3.34 (s, 1H), 3.03-2.98 (m, 1H), 2.97-2.80 (m, 8H), 2.11 (d, 2H, J=8.6 Hz), 1.86-1.79 (m, 2H).

Example 278

2-[5-Chloro-2-(10-methanesulfonyl-10-aza-tricyclo[6.3.2.0*2,7*]trideca-2,4,6-trien-4-ylamino)-pyrimidin-4-ylamino]-N-methyl-benzamide 2-[2-(10-Aza-tricyclo[6.3.2.0*2,7*]trideca-2,4,6-trien-4-ylamino)-5-chloro-pyrimidin-4-ylamino]-N-methyl-benzamide (30 mg, 0.0667 mmol) was placed in dichloromethane (3 mL) and triethylamine (20.3 mg, 0.201 mmol, 28.2 µL, 3.0 eq) was added followed by methanesulfonyl chloride (8.4 mg, 0.0734 mmol, 5.7 µL, 1.1 eq). The reaction was stirred for 5 minutes and then concentrated under reduced pressure. Purification by silica gel chromatography using a gradient of 0-8% MeOH/$CH_2Cl_2$ as the eluting solvent to obtain 2-[5-chloro-2-(10-methanesulfonyl-10-aza-tricyclo[6.3.2.0*2,7*]trideca-2,4,6-trien-4-ylamino)-pyrimidin-4-ylamino]-N-methyl-benzamide as a yellow foam (31 mg, 88%). LCMS (m/e) 527 (M+1); ¹H-NMR (CDCl₃, 400 MHz) δ 10.99 (s, 1H), 8.60 (d, 1H, J=7.8 Hz), 8.10 (s, 1H), 7.55-7.40 (m, 3H), 7.30-7.20 (m, 1H), 7.15-7.02 (m, 2H), 6.92 (s, 1H), 6.23 (bs, 1H), 3.87-3.77 (m, 2H), 3.20-3.05 (m, 4H), 3.03 (d, 3H, J=4.9 Hz), 2.47 (s, 3H), 2.20 (d, 2H, J=8.8 Hz), 1.81-1.70 (m, 2H).

Example 279

2-[5-Chloro-2-(10-prop-2-ynyl-10-aza-tricyclo [6.3.2.0*2,7*]trideca-2,4,6-trien-4-ylamino)-pyrimidin-4-ylamino]-N-methyl-benzamide 2-[2-(10-Aza-tricyclo[6.3.2.0*2,7*]trideca-2,4,6-trien-4-ylamino)-5-chloro-pyrimidin-4-ylamino]-N-methyl-benzamide (30 mg, 0.0667 mmol) was placed in acetone (3 mL) and cesium carbonate (65 mg, 0.200 mmol, 3.0 eq) was added followed by propargyl bromide (80% in toluene) (7.9 μL, 0.0734 mmol, 1.1 eq). The reaction was stirred at room temperature for 24 hours and was then concentrated under reduced pressure. The residue was taken up in CH₂Cl₂ (10 mL) and washed with water (10 mL). The organic layer was dried (sodium sulfate), filtered, and concentrated under reduced pressure. Purification by basic alumina chromatography using a gradient of 0-10% MeOH/CH₂Cl₂ as the eluting solvent to obtain 2-[5-chloro-2-(10-prop-2-ynyl-10-aza-tricyclo[6.3.2.0*2,7*]trideca-2,4,6-trien-4-ylamino)-pyrimidin-4-ylamino]-N-methyl-benzamide as an orange foam (30 mg, 92%). LCMS (m/e) 487 (M+1); ¹H-NMR (CDCl₃, 400 MHz) δ 11.03 (s, 1H), 8.66 (d, 1H, J=8.5 Hz), 8.08 (s, 1H), 7.51-7.40 (m, 2H), 7.37 (d, 1H, J=2.2 Hz), 7.30-7.20 (m, 1H), 7.10-7.0 (m, 2H), 6.92 (s, 1H), 6.18 (bs, 1H), 3.37 (d, 2H, J=2.3 Hz), 3.03 (d, 3H, 4.9 Hz), 3.03-2.98 (m, 1H), 2.97-2.87 (m, 3H), 2.52-2.45 (m, 2H), 2.23-2.15 (m, 2H), 2.14 (t, 1H, J=2.3 Hz), 1.70-1.62 (m, 2H).

Example 280

2-{5-Chloro-2-[10-(2-fluoro-ethyl)-10-aza-tricyclo [6.3.2.0*2,7*]trideca-2,4,6-trien-4-ylamino]-pyrimidin-4-ylamino}-N-methyl-benzamide 2-{5-Chloro-2-[10-(2-fluoro-ethyl)-10-aza-tricyclo [6.3.2.0*2,7*]trideca-2,4,6-trien-4-ylamino]-pyrimidin-4-ylamino}-N-methyl-benzamide was prepared from 2-[5-chloro-2-(10-prop-2-ynyl-10-aza-tricyclo[6.3.2.0*2,7*]trideca-2,4,6-trien-4-ylamino)-pyrimidin-4-ylamino]-N-methyl-benzamide and 1-bromo-2-fluoro-ethane in an analogous manner to Example 279. Product isolated as a yellow oil (22 mg, 66%). LCMS (m/e) 495 (M+1); ¹H-NMR (CDCl₃, 400 MHz) δ 11.03 (s, 1H), 8.65 (d, 1H, J=8.4 Hz), 8.08 (s, 1H), 7.50-7.45 (m, 1H), 7.45-7.39 (m, 1H), 7.36 (d, 1H, J=2.2 Hz), 7.30-7.20 (m, 1H), 7.10-6.95 (m, 3H), 6.53 (bs, 1H), 4.52 (dt, 2H, J=5.1 and 47.7 Hz), 3.02 (d, 3H, J=4.8 Hz), 3.02-2.93 (m, 3H), 2.93-2.89 (m, 1H), 2.74 (dt, 2H, J=5.1 and 27.3 Hz), 2.43-2.31 (m, 2H), 2.27-2.18 (m, 2H), 1.67-1.57 (m, 2H).

Example 281

2-[5-Chloro-2-(10-cyanomethyl-10-aza-tricyclo [6.3.2.0*2,7*]trideca-2,4,6-trien-4-ylamino)-pyrimidin-4-ylamino]-N-methyl-benzamide 2-[5-Chloro-2-(10-cyanomethyl-10-aza-tricyclo [6.3.2.0*2,7*]trideca-2,4,6-trien-4-ylamino)-pyrimidin-4-ylamino]-N-methyl-benzamide was prepared from 2-[5-chloro-2-(10-prop-2-ynyl-10-aza-tricyclo[6.3.2.0*2,7*] trideca-2,4,6-trien-4-ylamino)-pyrimidin-4-ylamino]-N-methyl-benzamide and bromo-acetonitrile in an analogous manner to Example 279. Product isolated as a yellow foam (83 mg, 76%). LCMS (m/e) 488 (M+1); ¹H-NMR (CDCl₃, 400 MHz) δ 11.02 (s, 1H), 8.64 (d, 1H, J=7.8 Hz), 8.09 (s, 1H), 7.52-7.40 (m, 2H), 7.39 (d, 1H, J=2.2 Hz), 7.32-7.25 (m, 1H), 7.11-7.00 (m, 2H), 6.92 (s, 1H), 6.21 (bs, 1H), 3.54 (s, 2H), 3.03 (d, 3H, J=4.9 Hz), 3.39-2.95 (m, 2H), 2.90-2.81 (m, 2H), 2.61-2.56 (m, 2H), 2.16-2.12 (m, 2H), 1.72-1.65 (m, 2H).

Example 282

2-{5-Chloro-2-[10-(2-methoxy-ethyl)-10-aza-tricyclo[6.3.2.0*2,7*]trideca-2,4,6-trien-4-ylamino]-pyrimidin-4-ylamino}-N-methyl-benzamide 2-[2-(10-Aza-tricyclo[6.3.2.0*2,7*]trideca-2,4,6-trien-4-ylamino)-5-chloro-pyrimidin-4-ylamino]-N-methyl-benzamide (30 mg, 0.0667 mmol) was placed in dimethylformamide (3 mL) and cesium carbonate (65 mg, 0.200 mmol, 3.0 eq) was added followed by 2-bromoethyl methyl ether (11.2 mg, 0.0804 mmol, 7.6 μL, 1.2 eq). The reaction was stirred at room temperature for 72 hours and was then concentrated under reduced pressure. The residue was taken up in CH₂Cl₂ (10 mL) and washed with water (10 mL). The organic layer was dried (sodium sulfate), filtered, and concentrated under reduced pressure. Purification by basic alumina chromatography using a gradient of 0-10% MeOH/CH₂Cl₂ as the eluting solvent to obtain 2-{5-chloro-2-[10-(2-methoxy-ethyl)-10-aza-tricyclo[6.3.2.0*2,7*]trideca-2,4,6-trien-4-ylamino]-pyrimidin-4-ylamino}-N-methyl-benzamide as a yellow foam (8.25 mg, 24%). LCMS (m/e) 507 (M+1); ¹H-NMR (CDCl₃, 400 MHz) δ 11.03 (s, 1H), 8.66 (d, 1H, J=8.0 Hz), 8.08 (s, 1H), 7.50-7.40 (m, 2H), 7.34 (d, 1H, J=2.1 Hz), 7.30-7.20 (m, 1H), 7.10-6.98 (m, 2H), 6.93 (s, 1H), 6.19 (bs, 1H), 3.48 (t, 2H, J=6.0 Hz), 3.33 (s, 3H), 3.03 (d, 3H, J=4.9 Hz), 3.0-2.93 (m, 3H), 2.92-2.86 (m, 1H), 2.61 (t, 2H, J=6.0 Hz), 2.35-2.26 (m, 2H), 2.24-2.17 (m, 2H), 1.63-1.57 (m, 2H).

Example 283

2-[2-(10-Acetyl-10-aza-tricyclo[6.3.2.0*2,7*] trideca-2,4,6-trien-4-ylamino)-5-chloro-pyrimidin-4-ylamino]-N-methyl-benzamide 2-[2-(10-Acetyl-10-aza-tricyclo[6.3.2.0*2,7*]trideca-2,4,6-trien-4-ylamino)-5-chloro-pyrimidin-4-ylamino]-N-methyl-benzamide was prepared from 2-[5-chloro-2-(10-prop-2-ynyl-10-aza-tricyclo[6.3.2.0*2,7*]trideca-2,4,6-trien-4-ylamino)-pyrimidin-4-ylamino]-N-methyl-benzamide and acetyl chloride in an analogous manner to Example 282. Product isolated as a yellow foam (30 mg, 91%). LCMS (m/e) 491 (M+1); ¹H-NMR (CDCl₃, 400 MHz) major rotomer δ 11.08 (s, 1H), 8.61 (d, 1H, J=8.4 Hz), 8.10 (s, 1H), 7.56-7.38 (m, 3H), 7.32-7.21 (m, 1H), 7.13-7.01 (m, 2H), 6.95 (s, 1H), 6.26 (bs, 1H), 4.34-4.20 (m, 1H), 3.80-3.69 (m, 1H), 3.43-3.30 (m, 1H), 3.28-3.18 (m, 1H), 3.15-2.99 (m, 2H), 3.03 (d, 3H, J=1.9 Hz), 2.07 (s, 3H), 2.02-1.92 (m, 2H), 1.84-1.67 (m, 2H).

Example 284

2-{5-Chloro-2-[10-(2,2,2-trifluoro-acetyl)-10-aza-tricyclo[6.3.2.0*2,7*]trideca-2,4,6-trien-4-ylamino]-pyrimidin-4-ylamino}-N-methyl-benzenesulfonamide 2-{5-Chloro-2-[10-(2,2,2-trifluoro-acetyl)-10-aza-tricyclo[6.3.2.0*2,7*]trideca-2,4,6-trien-4-ylamino]-pyrimidin-4-ylamino}-N-methyl-benzenesulfonamide was prepared from 1-(4-amino-10-aza-tricyclo[6.3.2.0*2,7*]trideca-2,4,6-trien-10-yl)-2,2,2-trifluoro-ethanone and 2-(2,5-dichloro-pyrimidin-4-ylamino)-N-methyl-benzenesulfonamide in an analogous manner to Example 276. Product isolated as an off-white solid (557 mg, 88%). m.p.=160-163° C.; LCMS (m/e) 581 (M+1); $^1$H-NMR (CDCl$_3$, 400 MHz) major rotamer δ 9.10 (s, 1H), 8.45 (d, 1H, J=8.3 Hz), 8.08 (s, 1H), 7.97 (t, 1H, J=2.0 Hz), 7.61-7.54 (m, 1H), 7.42-7.20 (m, 3H), 7.10-6.97 (m, 2H), 4.87-4.77 (m, 1H), 3.88-3.77 (m, 1H), 3.60-3.40 (m, 2H), 3.27-3.01 (m, 2H), 2.65 (s, 3H), 2.10-1.98 (m, 2H), 1.85-1.73 (m, 2H).

Example 285

2-[2-(10-Aza-tricyclo[6.3.2.0*2,7*]trideca-2,4,6-trien-4-ylamino)-5-chloro-pyrimidin-4-ylamino]-N-methyl-benzenesulfonamide 2-{5-Chloro-2-[10-(2,2,2-trifluoro-acetyl)-10-aza-tricyclo[6.3.2.0*2,7*]trideca-2,4,6-trien-4-ylamino]-pyrimidin-4-ylamino}-N-methyl-benzenesulfonamide (510 mg, 0.878 mmol) was dissolved in methanol (20 mL) and potassium carbonate (727 mg, 5.27 mmol, 6.0 eq) was added. The reaction was stirred at room temperature for 72 hours and then concentrated under reduced pressure. The residue was taken up in water (30 mL) and the product was extracted into EtOAc (3×30 mL). The combined organic layers were dried (sodium sulfate), filtered, and concentrated under reduced pressure. Purification by basic alumina chromatography using a gradient of 0-5% MeOH/CH$_2$Cl$_2$ as the eluting solvent to obtain 2-[2-(10-aza-tricyclo[6.3.2.0*2,7*]trideca-2,4,6-trien-4-ylamino)-5-chloro-pyrimidin-4-ylamino]-N-methyl-benzenesulfonamide as a white foam (300 mg, 70%). LCMS (m/e) 485 (M+1); $^1$H-NMR (CDCl$_3$, 400 MHz) δ 9.11 (bs, 1H), 8.49 (dd, 1H, J=1.0 and 8.4 Hz), 8.12 (s, 1H), 7.96 (dd, 1H, J=1.6 and 8.0 Hz), 7.60-7.52 (m, 1H), 7.33-7.19 (m, 3H), 7.00 (d, 1H, J=7.7 Hz), 6.95 (bs, 1H), 2.99-2.90 (m, 3H), 2.87-2.76 (m, 3H), 2.64 (s, 3H), 2.08-2.00 (m, 2H), 1.84-1.77 (m, 2H).

Example 286

2-[5-Chloro-2-(10-methanesulfonyl-10-aza-tricyclo[6.3.2.0*2,7*]trideca-2,4,6-trien-4-ylamino)-pyrimidin-4-ylamino]-N-methyl-benzenesulfonamide 2-[5-Chloro-2-(10-methanesulfonyl-10-aza-tricyclo[6.3.2.0*2,7*]trideca-2,4,6-trien-4-ylamino)-pyrimidin-4-ylamino]-N-methyl-benzenesulfonamide was prepared from 2-[2-(10-aza-tricyclo[6.3.2.0*2,7*]trideca-2,4,6-trien-4-ylamino)-5-chloro-pyrimidin-4-ylamino]-N-methyl-benzenesulfonamide and methanesulfonyl chloride in an analogous manner to Example 278. Product isolated as a white solid (29 mg, 83%). m.p.=135-139° C.; LCMS (m/e) 563 (M+1); $^1$H-NMR (CDCl$_3$, 400 MHz) δ 9.12 (s, 1H), 8.48 (d, 1H, J=8.3 Hz), 8.15 (s, 1H), 7.97 (dd, 1H, J=1.5 and 7.8 Hz), 7.61-7.55 (m, 1H), 2.65 (d, 1H, J=2.3 Hz), 7.35-7.22 (m, 2H), 7.05 (d, 1H, J=8.1 Hz), 6.94 (bs, 1H), 3.87 (m, 2H), 3.20-3.12 (m, 1H), 3.10-3.00 (m, 3H), 2.65 (d, 3H, J=5.3 Hz), 2.52 (s, 3H), 2.25-1.90 (m, 2H).

Example 287

2-[5-Chloro-2-(10-prop-2-ynyl-10-aza-tricyclo[6.3.2.0*2,7*]trideca-2,4,6-trien-4-ylamino)-pyrimidin-4-ylamino]-N-methyl-benzenesulfonamide 2-[2-(10-Aza-tricyclo[6.3.2.0*2,7*]trideca-2,4,6-trien-4-ylamino)-5-chloro-pyrimidin-4-ylamino]-N-methyl-benzenesulfonamide (30 mg, 0.0619 mmol) was placed in acetone (3 mL) and cesium carbonate (60.4 mg, 0.186 mmol, 3.0 eq) was added followed by propargyl bromide (80% in toluene) (7.28 μL, 0.0681 mmol, 1.1 eq). The reaction was stirred at room temperature for 24 hours and was then concentrated under reduced pressure. The residue was taken up in CH$_2$Cl$_2$ (10 mL) and washed with water (10 mL). The organic layer was dried (sodium sulfate), filtered, and concentrated under reduced pressure. Purification by silica gel chromatography using a gradient of 0-10% MeOH/CH$_2$Cl$_2$ as the eluting solvent. Further purification by prep-HPLC using a gradient of 10-90% acetonitrile/water to obtain 2-[5-chloro-2-(10-prop-2-ynyl-10-aza-tricyclo[6.3.2.0*2,7*]trideca-2,4,6-trien-4-ylamino)-pyrimidin-4-ylamino]-N-methyl-benzenesulfonamide as a thin yellow film (6.9 mg, 21%). LCMS (m/e) 523 (M+1); 1H-NMR (CDCl$_3$, 400 MHz) δ 9.10 (s, 1H), 8.49 (d, 1H, J=8.0 Hz), 8.09 (s, 1H), 7.95 (dd, 1H, J=1.6 and 8.0 Hz), 7.60-7.53 (m, 1H), 7.30-7.20 (m, 3H), 7.01 (d, 1H, J=7.9 Hz), 6.99 (bs, 1H), 4.76-4.67 (m, 1H), 3.36 (d, 2H, J=2.4 Hz), 3.05-3.00 (m, 1H), 2.95-2.84 (m, 3H), 2.63 (d, 3H, J=5.3 Hz), 2.51-2.43 (m, 2H), 2.21-2.15 (m, 2H), 2.14 (t, 1H, J=2.3 Hz), 1.70-1.60 (m, 2H).

Example 288

2-[5-Chloro-2-(10-prop-2-ynyl-10-aza-tricyclo[6.3.2.0*2,7*]trideca-2,4,6-trien-4-ylamino)-pyrimidin-4-ylamino]-N-methyl-N-prop-2-ynyl-benzenesulfonamide Product is isolated as a byproduct from synthesis of 2-[5-chloro-2-(10-prop-2-ynyl-10-aza-tricyclo[6.3.2.0*2,7*]trideca-2,4,6-trien-4-ylamino)-pyrimidin-4-ylamino]-N-methyl-benzenesulfonamide (Example 287). Material is isolated as a yellow foam (5.7 mg, 16%). LCMS (m/e) 561 (M+1); $^1$H-NMR (CDCl$_3$, 400 MHz) δ 9.29 (s, 1H), 8.52 (d, 1H, J=8.4 Hz), 8.13 (s, 1H), 7.91 (dd, 1H, J=1.5 and 8.0 Hz), 7.60-7.50 (m, 1H), 7.35-7.17 (m, 3H), 7.00 (d, 1H, J=7.9 Hz), 6.97 (bs, 1H), 4.06 (d, 2H, J=2.4 Hz), 3.36 (d, 2H, J=2.3 Hz), 3.50-2.99 (m, 1H), 2.97-2.89 (m, 3H), 2.85 (s, 3H), 2.53-2.44 (m, 2H), 2.22-2.16 (m, 2H), 2.14 (t, 1H, J=2.3 Hz), 1.97 (t, 1H, J=2.4 Hz), 1.70-1.59 (m, 2H).

Example 289

2-[2-(10-Acetyl-10-aza-tricyclo[6.3.2.0*2,7*]trideca-2,4,6-trien-4-ylamino)-5-chloro-pyrimidin-4-ylamino]-N-methyl-benzenesulfonamide 2-[2-(10-Acetyl-10-aza-tricyclo[6.3.2.0*2,7*]trideca-2,4,6-trien-4-ylamino)-5-chloro-pyrimidin-4-ylamino]-N-methyl-benzenesulfonamide was prepared from 2-[2-(10-aza-tricyclo[6.3.2.0*2,7*]trideca-2,4,6-trien-4-ylamino)-5-chloro-pyrimidin-4-ylamino]-N-methyl-benzenesulfonamide and acetyl chloride in an analogous manner to Example 282. Product isolated as a yellow oil (25.3 mg, 77%). LCMS (m/e) 527 (M+1); $^1$H-NMR (CDCl$_3$, 400 MHz) major rotamer δ 9.09 (s, 1H), (d, 1H, J=9.5 Hz), 8.11 (s, 1H), 8.00-7.94 (m, 1H), 7.63-7.53 (s, 1H), 7.42-7.20 (m, 3H), 7.18-6.92 (m, 1H), 4.80-4.67 (m, 1H), 4.26-4.10 (m, 1H), 3.80-3.70 (m, 1H), 3.45-3.22 (m, 3H), 3.18-2.92 (m, 2H), 2.65 (d, 3H, J=2.3 Hz), 2.04 (s, 3H), 2.04-1.90 (m, 2H), 1.82-1.62 (m, 2H).

Example 290

2-{4-[5-Chloro-4-(2-methoxy-4-morpholin-4-yl-phenylamino)-pyrimidin-2-ylamino]-10-aza-tricyclo[6.3.2.0*2,7*]trideca-2,4,6-trien-10-yl}-2,2,2-trifluoro-ethanone 1-(4-Amino-10-aza-tricyclo[6.3.2.0*2,7*]trideca-2,4,6-trien-10-yl)-2,2,2-trifluoro-ethanone (200 mg, 0.709 mmol) and (2,5-dichloro-pyrimidin-4-yl)-(2-methoxy-4-morpholin-4-yl-phenyl)-amine (275 mg, 0.775 mmol, 1.1 eq) were dissolved in IPA (15 mL). 4.0 M HCl in dioxane (194 µL, 0.775 mmol, 1.1 eq) was added and the reaction was heated at 120° C. in a microwave for 4 hours. The reaction was then concentrated under reduced pressure and the residue was taken up in $CH_2Cl_2$ (30 mL) and washed with sat. $NaHCO_3$ (30 mL). The organic layer was dried (sodium sulfate), filtered, and concentrated under reduced pressure. Purification by silica gel chromatography using a gradient of 0-85% EtOAc/hex as the eluting solvent to obtain 2-{4-[5-chloro-4-(2-methoxy-4-morpholin-4-yl-phenylamino)-pyrimidin-2-ylamino]-10-aza-tricyclo[6.3.2.0*2,7*]trideca-2,4,6-trien-10-yl}-2,2,2-trifluoro-ethanone as a white solid (282 mg, 66%). m.p.=221-223° C.; LCMS (m/e) 603 (M+1); $^1$H-NMR ($CDCl_3$, 400 MHz) major rotamer δ 8.16 (d, 1H, J=8.7 Hz), 8.02 (s, 1H), 7.55 (s, 1H), 7.54 (s, 1H), 7.21 (d, 1H, J=2.2 Hz), 7.05 (d, 1H, J=11.7 Hz), 6.91 (s, 1H), 6.55 (s, 1H), 6.53-6.45 (m, 1H), 4.36-4.20 (m, 1H), 3.91 (s, 3H), 3.96-3.83 (m, 5H), 3.50-3.42 (m, 1H), 3.39-3.22 (m, 1H), 3.21-3.07 (m, 6H), 2.10-1.95 (m, 2H), 1.83-1.73 (m, 2H).

Example 291

N-(2-{5-Chloro-2-[10-(2,2,2-trifluoro-acetyl)-10-aza-tricyclo[6.3.2.0*2,7*]trideca-2,4,6-trien-4-ylamino]-pyrimidin-4-ylamino}-phenyl)-methane-sulfonamide N-(2-{5-Chloro-2-[10-(2,2,2-trifluoro-acetyl)-10-aza-tricyclo[6.3.2.0*2,7*]trideca-2,4,6-trien-4-ylamino]-pyrimidin-4-ylamino}-phenyl)-methanesulfonamide was prepared from 1-(4-amino-10-aza-tricyclo[6.3.2.0*2,7*]trideca-2,4,6-trien-10-yl)-2,2,2-trifluoro-ethanone and N-[2-(2,5-dichloro-pyrimidin-4-ylamino)-phenyl]-methanesulfonamide in an analogous manner to Example 290. Product isolated as a pale yellow foam (263 mg, 64%). LCMS (m/e) 581 (M+1); $^1$H-NMR ($CDCl_3$, 400 MHz) major rotamer δ 7.96 (s, 1H), 7.70-62 (m, 1H), 7.55-7.45 (m, 2H), 7.40-7.31 (m, 2H), 7.25-7.05 (m, 3H), 7.00-6.90 (m, 1H), 4.30-4.10 (m, 1H), 3.90-3.79 (m, 1H), 3.50-3.39 (m, 1H), 3.37-3.27 (m, 1H), 3.20-3.10 (m, 1H), 2.96 (s, 1H), 2.96-2.90 (m, 1H), 2.10-1.95 (m, 2H), 1.80-1.70 (m, 2H).

Example 292

N-((1R,2R)-2-{5-Chloro-2-[10-(2,2,2-trifluoro-acetyl)-10-aza-tricyclo[6.3.2.0*2,7*]trideca-2,4,6-trien-4-ylamino]-pyrimidin-4-ylamino}-cyclohexyl)-methanesulfonamide N-((1R,2R)-2-{5-Chloro-2-[10-(2,2,2-trifluoro-acetyl)-10-aza-tricyclo[6.3.2.0*2,7*]trideca-2,4,6-trien-4-ylamino]-pyrimidin-4-ylamino}-cyclohexyl)-methanesulfonamide was prepared from 1-(4-amino-10-aza-tricyclo[6.3.2.0*2,7*]trideca-2,4,6-trien-10-yl)-2,2,2-trifluoro-ethanone and N-[(1R,2R)-2-(2,5-dichloro-pyrimidin-4-ylamino)-cyclohexyl]-methanesulfonamide in an analogous manner to Example 290. Product isolated as a white foam as a mixture of diastereomers (429 mg, 69%). LCMS (m/e) 587 (M+1); $^1$H-NMR ($CDCl_3$, 400 MHz) major rotamer δ 7.93 (s, 1H), 7.42-7.24 (m, 2H), 7.13-7.04 (m, 1H), 6.94-6.85 (m, 1H), 5.46-5.35 (m, 2H), 4.31-4.20 (m, 1H), 3.98-3.76 (m, 2H), 3.60-3.30 (m, 3H), 3.30-3.10 (m, 3H), 2.80 (s, 3H), 2.28-2.18 (m, 2H), 2.10-1.95 (m, 1H), 1.90-1.70 (m, 4H), 1.43-1.30 (m, 4H).

Example 293

N-{(1R,2R)-2-[2-(10-Aza-tricyclo[6.3.2.0*2,7*]trideca-2,4,6-trien-4-ylamino)-5-chloro-pyrimidin-4-ylamino]-cyclohexyl}-methanesulfonamide N-{(1R,2R)-2-[2-(10-Aza-tricyclo[6.3.2.0*2,7*]trideca-2,4,6-trien-4-ylamino)-5-chloro-pyrimidin-4-ylamino]-cyclohexyl}-methanesulfonamide was prepared from N-((1R,2R)-2-{5-chloro-2-[10-(2,2,2-trifluoro-acetyl)-10-aza-tricyclo[6.3.2.0*2,7*]trideca-2,4,6-trien-4-ylamino]-pyrimidin-4-ylamino}-cyclohexyl)-methanesulfonamide in an analogous manner to Example 285. Product isolated as a pale yellow foam (336 mg, 99%). LCMS (m/e) 491 (M+1); $^1$H-NMR ($CDCl_3$, 400 MHz) mixture of diastereomers δ 7.92 (s, 1H), 7.35-7.25 (m, 1H), 7.03 (d, 1H, J=7.8 Hz), 6.89 (s, 1H), 5.6-5.35 (m, 2H), 3.90-3.77 (m, 1H), 3.30-3.15 (m, 1H), 3.07-2.90 (m, 4H), 2.86-2.75 (m, 5H), 2.27-2.14 (m, 2H), 2.08-1.97 (m, 2H), 1.90-1.73 (m, 4H), 1.42-1.10 (m, 4H).

Example 294

N-{(1R,2R)-2-[5-Chloro-2-(10-methanesulfonyl-10-aza-tricyclo[6.3.2.0*2,7*]trideca-2,4,6-trien-4-ylamino)-pyrimidin-4-ylamino]-cyclohexyl}-methanesulfonamide N-{(1R,2R)-2-[5-Chloro-2-(10-methanesulfonyl-10-aza-tricyclo[6.3.2.0*2,7*]trideca-2,4,6-trien-4-ylamino)-pyrimidin-4-ylamino]-cyclohexyl}-methanesulfonamide was prepared from N-{(1R,2R)-2-[2-(10-aza-tricyclo[6.3.2.0*2,7*]trideca-2,4,6-trien-4-ylamino)-5-chloro-pyrimidin-4-ylamino]-cyclohexyl}-methanesulfonamide and methanesulfonyl chloride in an analogous manner to Example 278. Product isolated as a white foam as a mixture of diastereomers (14.79 mg, 42%). LCMS (m/e) 569 (M+1); $^1$H-NMR ($CDCl_3$, 400 MHz) δ 7.94 (s, 1H), 7.43-7.23 (m, 2H), 7.12-7.06 (m, 1H), 6.91-6.84 (m, 1H), 3.91-3.77 (m, 3H), 3.30-2.96 (m, 5H), 2.79 and 2.77 (diastereomeric singlets, 3H), 2.55 and 2.52 (diastereomeric singlets, 3H), 2.30-2.13 (m, 4H), 1.95-1.70 (m, 4H), 1.45-1.28 (m, 4H).

Example 295

N-{(1R,2R)-2-[2-(10-Acetyl-10-aza-tricyclo[6.3.2.0*2,7*]trideca-2,4,6-trien-4-ylamino)-5-chloro-pyrimidin-4-ylamino]-cyclohexyl}-methane-sulfonamide N-{(1R,2R)-2-[2-(10-Aza-tricyclo[6.3.2.0*2,7*]trideca-2,4,6-trien-4-ylamino)-5-chloro-pyrimidin-4-ylamino]-cyclohexyl}-methanesulfonamide (35 mg, 0.0713 mmol) was placed in dichloromethane (3 mL) and triethylamine (21.6 mg, 0.214 mmol, 30.0 µL, 3.0 eq) was added followed by acetyl chloride (6.67 mg, 0.0856 mmol, 6.04 µL, 1.2 eq). The reaction was stirred for 30 minutes and then concentrated under reduced pressure. Purification by basic alumina chromatography using a gradient of 0-6% MeOH/$CH_2Cl_2$ as the eluting solvent to obtain N-{(1R,2R)-2-[2-(10-acetyl-10-aza-tricyclo[6.3.2.0*2,7*]trideca-2,4,6-trien-4-ylamino)-5-chloro-pyrimidin-4-ylamino]-cyclohexyl}-methanesulfonamide as a white foam as a mixture of diastereomers (32.88 mg, 86%). LCMS (m/e) 533 (M+1); $^1$H-NMR (CDCl$_3$, 400 MHz) mixture of diasteromers δ 7.90 (s, 1H), 7.50-7.23 (m, 1H), 7.20-6.80 (m, 2H), 5.80-5.40 (m, 2H), 4.38-4.07 (m, 1H), 4.00-3.70 (m, 2H), 3.70-3.52 (m, 1H), 3.50-3.30 (m, 1H), 3.30-3.00 (m, 4H), 2.79 (s, 3H), 2.30-1.20 (m, 14H).

Example 296

N-{(1R,2R)-2-[5-Chloro-2-(10-Isopropyl-10-aza-tricyclo[6.3.2.0*2,7*]trideca-2,4,6-trien-4-ylamino)-pyrimidin-4-ylamino]-cyclohexyl}-methanesulfonamide N-{(1R,2R)-2-[2-(10-Aza-tricyclo[6.3.2.0*2,7*]trideca-2,4,6-trien-4-ylamino)-5-chloro-pyrimidin-4-ylamino]-cyclohexyl}-methanesulfonamide (77 mg, 0.157 mmol) was placed in 1,2-dichloroethane (5 mL) and acetic acid (0.25 mL). Acetone (13.6 mg, 0.235 mmol, 17.2 µL, 1.5 eq) was added and the reaction was stirred for 5 minutes. Sodium borohydride (7.0 mg, 0.188 mmol, 1.2 eq) was added and the reaction was heated at 80° C. overnight. The reaction was then diluted with CH$_2$Cl$_2$ (20 mL) and washed with water (20 mL). The organic layer was dried (sodium sulfate), filtered, and concentrated under reduced pressure. Purification by prep-HPLC using a gradient of 0-40% acetonitrile/water as the eluting solvent to obtain N-{(1R,2R)-2-[5-chloro-2-(10-Isopropyl-10-aza-tricyclo[6.3.2.0*2,7*]trideca-2,4,6-trien-4-ylamino)-pyrimidin-4-ylamino]-cyclohexyl}-methanesulfonamide as a mixture of diastereomers as an orange foam (14.63 mg, 17%). LCMS (m/e) 533 (M+1); $^1$H-NMR (CDCl$_3$, 400 MHz) δ 7.91 (s, 1H), 7.26-7.18 (m, 2H), 7.01 (d, 1H, J=6.7 Hz), 6.90 (bs, 1H), 5.49 (bs, 1H), 5.39-5.33 (m, 1H), 3.92-3.78 (m, 1H), 3.30-3.17 (m, 1H), 3.00-2.92 (m, 2H), 2.92-2.75 (m, 3H), 2.77 (s, 3H), 2.40-2.27 (m, 2H), 2.26-2.10 (m, 4H), 1.87-1.75 (m, 2H), 1.65-1.50 (m, 2H), 1.42-1.25 (m, 4H), 0.94 (d, 6H, J=6.5 Hz).

Example 297

2-{2-[3-Bromo-10-(2,2,2-trifluoro-acetyl)-10-aza-tricyclo[6.3.2.0*2,7*]trideca-2,4,6-trien-4-ylamino]-5-chloro-pyrimidin-4-ylamino}-N-methyl-benzamide 297a) 1-(4-Amino-10-aza-tricyclo[6.3.2.0*2,7*]trideca-2,4,6-trien-10-yl)-2,2,2-trifluoro-ethanone (20 mg, 0.0204 mmol) was placed in CH$_2$Cl$_2$ (3 mL) and acetic acid (0.1 mL). NBS was added. The reaction was stirred for 30 min. and then concentrated under reduced pressure. Purification by silica gel chromatography using a gradient of 0-8% MeOH/CH$_2$Cl$_2$ as the eluting solvent to obtain 1-(4-amino-3-bromo-10-aza-tricyclo[6.3.2.0*2,7*]trideca-2,4,6-trien-10-yl)-2,2,2-trifluoro-ethanone as a yellow film (14.82 mg, 58%). LCMS (m/e) 363 (M+1); $^1$H-NMR (CDCl$_3$, 400 MHz) δ 7.18 (d, 1H, J=10.6 Hz), 6.57 (d, 1H, J=8.34 Hz), 4.25-4.10 (m, 1H), 4.03 (bs, 2H), 3.90-3.78 (m, 1H), 3.50-3.40 (m, 1H), 3.40-3.26 (m, 1H), 3.12-3.00 (m, 2H), 2.30-1.90 (m, 2H), 1.80-1.65 (m, 2H).

297b) 1-(4-Amino-3-bromo-10-aza-tricyclo[6.3.2.0*2,7*]trideca-2,4,6-trien-10-yl)-2,2,2-trifluoro-ethanone (76 mg, 0.209 mmol) and 2-(2,5-dichloro-pyrimidin-4-ylamino)-N-methyl-benzamide (68.4 mg, 0.230 mmol, 1.1 eq) were dissolved in IPA (2 mL). 4.0 M HCl in dioxane (57.5 µL, 0.230 mmol, 1.1 eq) was added and the reaction was heated at 120° C. in a microwave for 4 hours. The reaction was then concentrated under reduced pressure and the residue was taken up in CH$_2$Cl$_2$ (20 mL) and washed with sat. NaHCO$_3$ (20 mL). The organic layer was dried (sodium sulfate), filtered, and concentrated under reduced pressure. Purification by silica gel chromatography using a gradient of 0-50% EtOAc/hex as the eluting solvent to obtain 2-{2-[3-bromo-10-(2,2,2-trifluoro-acetyl)-10-aza-tricyclo[6.3.2.0*2,7*]trideca-2,4,6-trien-4-ylamino]-5-chloro-pyrimidin-4-ylamino}-N-methyl-benzamide as a pale yellow foam (24.99 mg, 19%). LCMS (m/e) 623 (M+1); $^1$H-NMR (CDCl$_3$, 400 MHz) major rotomer δ 11.03 (s, 1H), 8.55 (d, 1H, J=8.4 Hz), 8.26 (s, 1H), 8.14 (s, 1H), 7.55-7.26 (m, 4H), 7.15-7.05 (m, 1H), 6.30-6.20 (m, 1H), 4.23 (dd, 1H, J=5.3 and 13.5 Hz), 3.95-3.83 (m, 1H), 3.47-3.38 (m, 1H), 3.30-3.20 (m, 1H), 3.20-3.09 (m, 1H), 3.04 (s, 3H), 3.06-2.97 (m, 1H), 2.10-1.97 (m, 2H), 1.87-1.70 (m, 2H).

Example 298

N-{2-[5-Chloro-2-(3-ethyl-2,3,4,5-tetrahydro-1H-benzo[d]azepin-7-ylamino)-pyrimidin-4-ylamino]-ethyl}-methanesulfonamide 298a) Ethylene diamine (2.99 g, 49.8 mmol, 2.05 mL, 1.5 eq.) in THF (200 mL) was cooled to 0° C. and 2,4,5-trichloropyrimidine (6.08 g, 33.2 mmol, 3.80 mL, 1.0 eq.) was added. A precipitate formed and the reaction was stirred for 5 minutes before NEt$_3$ and mesyl chloride were added simultaneously via two syringes. After 5 minutes, external cooling was removed and the reaction was stirred under a nitrogen atmosphere for 45 minutes. The reaction was then partitioned between CH$_2$Cl$_2$ (150 mL) and sat. NaHCO$_3$ (150 mL). The layers were separated and the aqueous layer was extracted with CH$_2$Cl$_2$ (100 mL). The combined organic layers were dried (sodium sulfate), filtered, and concentrated under reduced pressure onto silica gel. Purification by silica gel chromatography (dry loaded) using a gradient of 0-100% EtOAc/hex followed by 0-20% MeOH/EtOAc as the eluting solvent to obtain -[2-(2,5-dichloro-pyrimidin-4-ylamino)-ethyl]-methanesulfonamide as a white solid (763 mg, 8%). m.p.=186-187° C.; LCMS (m/e) 285 (M+1); $^1$H-NMR (d$_6$-DMSO, 400 MHz) δ 8.18 (s, 1H), 7.92 (t, 1H, J=5.3 Hz), 7.17 (t, 1H, J=5.7 Hz), 3.49 (dt, 2H, J=6.1 and 6.2 Hz), 3.16 (dt, 2H, J=6.2 and 6.3 Hz), 2.92 (s, 3H).

298b) 3-Ethyl-2,3,4,5-tetrahydro-1H-benzo[d]azepin-7-ylamine (90.9 mg, 0.478 mmol) and N-[2-(2,5-dichloro-pyrimidin-4-ylamino)-ethyl]-methanesulfonamide (150 mg, 0.526 mmol, 1.1 eq) were dissolved in IPA (3 mL). 4.0 M HCl in dioxane (132 µL, 0.526 mmol, 1.1 eq) was added and the reaction was heated at 150° C. in a microwave for 6 hours. The reaction was then concentrated under reduced pressure and the residue was taken up in CH$_2$Cl$_2$ (20 mL) and washed with sat. NaHCO$_3$ (20 mL). The organic layer was dried (sodium sulfate), filtered, and concentrated under reduced pressure. Purification by basic alumina chromatography using a gradient of 0-10% MeOH/CH$_2$Cl$_2$ as the eluting solvent to obtain N-{2-[5-chloro-2-(3-ethyl-2,3,4,5-tetrahydro-1H-benzo[d]azepin-7-ylamino)-pyrimidin-4-ylamino]-ethyl}-methanesulfonamide as a white solid (90 mg, 43%). m.p.=146° C.; LCMS (m/e) 439 (M+1); $^1$H-NMR (d$_6$-DMSO, 400 MHz) δ 9.06 (s, 1H), 7.93 (s, 1H), 7.45-7.40 (m, 2H), 7.18-7.08 (m, 2H), 6.97 (d, 1H, J=8.3 Hz), 3.58-3.50 (m, 2H), 3.25-3.14 (m, 2H), 2.89 (s, 3H), 2.82-2.73 (m, 4H), 2.57-2.40 (m, 6H) 1.00 (t, 3H, J=7.2 Hz).

Example 299

N-(2-{5-Chloro-2-[3-(2-methoxy-ethyl)-2,3,4,5-tetrahydro-1H-benzo[d]azepin-7-ylamino]-pyrimidin-4-ylamino}-ethyl)-methanesulfonamide N-(2-{5-Chloro-2-[3-(2-methoxy-ethyl)-2,3,4,5-tetrahydro-1H-benzo[d]azepin-7-ylamino]-pyrimidin-4-ylamino}-ethyl)-methanesulfonamide was prepared from 3-(2-methoxy-ethyl)-2,3,4,5-tetrahydro-1H-benzo[d]azepin-7-ylamine and N-[2-(2,5-dichloro-pyrimidin-4-ylamino)-ethyl]-methanesulfonamide in an analogous manner to Example 298. Product isolated as a white solid (34 mg, 21%). m.p.=92-95° C.; LCMS (m/e) 469 (M+1); $^1$H-NMR (d$_6$-DMSO, 400 MHz) δ 9.06 (s, 1H), 7.93 (s, 1H), 7.45-7.39 (m, 2H), 7.17-7.07 (m, 2H), 6.97 (d, 1H, J=8.6 Hz), 3.58-3.49 (m, 2H), 3.47-3.40 (m, 2H), 3.23 (s, 3H), 3.24-3.17 (m, 2H), 2.89 (s, 3H) 2.79-2.71 (m, 4H), 2.65-2.54 (m, 6H).

Example 300

N-{2-[5-Chloro-2-(3-ethyl-2,3,4,5-tetrahydro-1H-benzo[d]azepin-7-ylamino)-pyrimidin-4-ylamino]-1-methyl-ethyl}-methanesulfonamide 300a) 1,2-Diaminopropane (2.00 g, 27.03 mmol, 2.30 mL, 1.5 eq.) in THF (100 mL) was cooled to 0° C. and 2,4,5-trichloropyrimidine (3.30 g, 18.02 mmol, 2.06 mL, 1.0 eq.) was added. A precipitate formed and the reaction was stirred for 5 minutes before NEt$_3$ and mesyl chloride were added simultaneously via two syringes. After 5 minutes, external cooling was removed and the reaction was stirred under a nitrogen atmosphere for 45 minutes. The reaction was then partitioned between CH$_2$Cl$_2$ (100 mL) and sat. NaHCO$_3$ (100 mL). The layers were separated and the aqueous layer was extracted with CH$_2$Cl$_2$ (50 mL). The combined organic layers were dried (sodium sulfate), filtered, and concentrated under reduced pressure onto silica gel. Purification by silica gel chromatography (dry loaded) using a gradient of 0-10% MeOH/CH$_2$Cl$_2$ as the eluting solvent to obtain N-[2-(2,5-dichloro-pyrimidin-4-ylamino)-1-methyl-ethyl]-methanesulfonamide as a white solid (1.75 g, 32%). m.p.=160° C.; LCMS (m/e) 299 (M+1); $^1$H-NMR (d$_6$-DMSO, 400 MHz) δ 8.20 (s, 1H), 7.94-7.77 (m, 1H), 7.23-7.07 (m, 1H), 3.65 (m, 1H), 3.42-3.35 (m, 2H), 2.93 (s, 3H), 1.11 (d, 3H, J=6.5 Hz).

300b) 3-Ethyl-2,3,4,5-tetrahydro-1H-benzo[d]azepin-7-ylamine (86.7 mg, 0.456 mmol, 1.0 eq) and N-[2-(2,5-dichloro-pyrimidin-4-ylamino)-1-methyl-ethyl]-methanesulfonamide (150 mg, 0.502 mmol, 1.1 eq) were dissolved in IPA (3 mL). 4.0 M HCl in dioxane (126 µL, 0.502 mmol, 1.1 eq) was added and the reaction was heated at 140° C. in a microwave for 90 minutes. The reaction was then concentrated under reduced pressure and the residue was taken up in CH$_2$Cl$_2$ (20 mL) and washed with sat. NaHCO$_3$ (20 mL). The organic layer was dried (sodium sulfate), filtered, and concentrated under reduced pressure. Purification by amine capped silica gel chromatography using a gradient of 0-100% EtOAc/hex as the eluting solvent to obtain N-{2-[5-chloro-2-(3-ethyl-2,3,4,5-tetrahydro-1H-benzo[d]azepin-7-ylamino)-pyrimidin-4-ylamino]-1-methyl-ethyl}-methanesulfonamide as a white foam (45 mg, 22%). LCMS (m/e) 453 (M+1); $^1$H-NMR (CDCl$_3$, 400 MHz) δ 7.95 (s, 1H), 7.32 (d, 1H, J=8.6 Hz), 7.06 (d, 1H, J=8.2 Hz), 6.93 (s, 1H), 5.72-5.62 (m, 1H), 5.41-5.31 (m, 1H), 3.81-3.65 (m, 2H), 3.55-3.43 (m, 1H), 2.99-2.86 (m, 4H), 2.90 (s, 3H), 2.74-2.60 (m, 4H), 2.60 (q, 2H, J=6.9 Hz), 1.32 (d, 3H, J=6.6 Hz), 1.12 (t, 3H, J=6.9 Hz).

Example 301

N-(2-{5-Chloro-2-[3-(2-methoxy-ethyl)-2,3,4,5-tetrahydro-1H-benzo[d]azepin-7-ylamino]-pyrimidin-4-ylamino}-1-methyl-ethyl)-methanesulfonamide N-(2-{5-Chloro-2-[3-(2-methoxy-ethyl)-2,3,4,5-tetrahydro-1H-benzo[d]azepin-7-ylamino]-pyrimidin-4-ylamino}-1-methyl-ethyl)-methanesulfonamide was prepared from 3-(2-methoxy-ethyl)-2,3,4,5-tetrahydro-1H-benzo[d]azepin-7-ylamine and N-[2-(2,5-dichloro-pyrimidin-4-ylamino)-1-methyl-ethyl]-methanesulfonamide in an analogous manner to Example 300. Product isolated as a white solid (96 mg, 58%). LCMS (m/e) 483 (M+1); $^1$H-NMR (CDCl$_3$, 400 MHz) δ 7.95 (s, 1H), 7.35-7.23 (m, 2H), 7.05 (d, 1H, J=8.0 Hz), 6.93 (s, 1H), 5.70-5.62 (m, 1H), 5.40-5.31 (m, 1H), 3.55 (t, 2H, J=5.7 Hz), 3.53-3.43 (m, 1H), 3.39 (s, 3H), 2.97-2.87 (m, 4H) 2.90 (s, 3H), 2.80-2.69 (m, 6H), 1.31 (d, 3H, J=6.6 Hz).

Example 302

N-{2-[5-Chloro-2-(3-ethyl-2,3,4,5-tetrahydro-1H-benzo[d]azepin-7-ylamino)-pyrimidin-4-ylamino]-propyl}-methanesulfonamide 302a) 1,2-Diaminopropane (1.00 g, 13.5 mmol, 1.15 mL, 1.1 eq.) was placed in CH$_2$Cl$_2$ (30 mL) and cooled to 0° C. Mesyl chloride (1.40 g, 12.3 mmol, 0.95 mL, 1.0 eq.) was added over a period of five minutes followed by triethylamine (3.72 g, 36.9 mmol, 5.17 mL, 3.0 eq.). The reaction was stirred for 30 minutes and then concentrated under reduced pressure. Purification by basic alumina chromatography using a gradient of 0-15% MeOH/CH$_2$Cl$_2$ as the eluting solvent to obtain N-(2-amino-propyl)-methanesulfonamide as a clear, colorless oil (504 mg, 27%). $^1$H-NMR (CDCl$_3$, 400 MHz) δ 3.17-3.03 (m, 2H), 2.98 (s, 3H), 2.88-2.80 (m, 1H), 1.12 (d, 3H, J=6.3 Hz).

302b) N-(2-Amino-propyl)-methanesulfonamide (325 mg, 2.14 mmol, 1.5 eq.) in THF (20 mL) was cooled to 0 C and 2,4,5-trichloropyrimidine (261 mg, 1.43 mmol, 162 µL, 1.0 eq.) was added. The reaction was stirred for 5 minutes and then NEt$_3$ (711 mg, 7.04 mmol, 516 µL, 4.9 eq) was added. After 5 minutes, external cooling was removed and the reaction was stirred under a nitrogen atmosphere for 3 hours. The reaction was then partitioned between CH$_2$Cl$_2$ (30 mL) and sat. NaHCO$_3$ (30 mL). The layers were separated and the aqueous layer was extracted with CH$_2$Cl$_2$ (15 mL). The combined organic layers were dried (sodium sulfate), filtered, and concentrated under reduced pressure onto silica gel. Purification by silica gel chromatography (dry loaded) using a gradient of 0-10% MeOH/CH$_2$Cl$_2$ as the eluting solvent to obtain N-[2-(2,5-dichloro-pyrimidin-4-ylamino)-propyl]-methanesulfonamide as a white solid (365 mg, 85%). m.p.=160° C.; LCMS (m/e) 299 (M+1); $^1$H-NMR (d$_6$-DMSO, 400 MHz) δ 8.18 (s, 1H), 7.59-7.50 (m, 1H), 7.26-7.15 (m, 1H), 4.36-4.22 (m, 1H), 3.21-3.05 (m, 2H), 2.91 (s, 3H), 1.18 (d, 3H, J=6.6 Hz).

302c) N-{2-[5-Chloro-2-(3-ethyl-2,3,4,5-tetrahydro-1H-benzo[d]azepin-7-ylamino)-pyrimidin-4-ylamino]-propyl}-methanesulfonamide was prepared from 3-ethyl-2,3,4,5-tetrahydro-1H-benzo[d]azepin-7-ylamine and N-[2-(2,5- dichloro-pyrimidin-4-ylamino)-propyl]-methanesulfonamide in an analogous manner to Example 300b. Product isolated as a pale pink foam (84 mg, 41%). LCMS (m/e) 453 (M+1); $^1$H-NMR (CDCl$_3$, 400 MHz) δ 7.94 (s, 1H), 7.32 (d, 1H, J=7.7 Hz), 7.25 (s, 1H), 7.06 (d, 1H, J=8.0 Hz), 6.90 (s, 1H), 5.30-5.17 (m, 2H), 4.41-4.31 (m, 1H), 3.46-3.37 (m, 1H), 3.30-3.19 (m, 1H), 3.33-2.86 (m, 4H), 2.91 (s, 3H), 2.72-2.60 (m, 5H), 2.59 (q, 2H, J=6.9 Hz), 1.37 (d, 3H, J=5.9 Hz), 1.12 (t, 3H, J=6.9 Hz).

Example 303

N-(2-{5-Chloro-2-[3-(2-methoxy-ethyl)-2,3,4,5-tetrahydro-1H-benzo[d]azepin-7-ylamino]-pyrimidin-4-ylamino}-propyl)-methanesulfonamide N-(2-{5-Chloro-2-[3-(2-methoxy-ethyl)-2,3,4,5-tetrahydro-1H-benzo[d]azepin-7-ylamino]-pyrimidin-4-ylamino}-propyl)-methanesulfonamide was prepared from 3-(2-methoxy-ethyl)-2,3,4,5-tetrahydro-1H-benzo[d]azepin-7-ylamine and N-[2-(2,5-dichloro-pyrimidin-4-ylamino)-propyl]-methanesulfonamide in an analogous manner to Example 302. Product isolated as a white foam (117 mg, 71%). LCMS (m/e) 483 (M+1); $^1$H-NMR (CDCl$_3$, 400 MHz) δ 7.94 (s, 1H), 7.32 (d, 1H, J=8.0 Hz), 7.24 (s, 1H), 7.04 (d, 1H, J=8.0 Hz), 6.93 (s, 1H), 5.35-5.27 (m, 1H), 5.22 (d, 1H, J=7.0 Hz), 4.41-4.31 (m, 1H), 3.55 (t, 2H, J=5.7 Hz), 3.46-3.35 (m, 1H), 3.38 (s, 3H), 3.29-3.20 (m, 1H), 2.96-2.86 (m, 4H), 2.91 (s, 3H), 2.80-2.68 (m, 6H), 1.36 (d, 3H, J=6.7 Hz).

Example 304

N-{2-[5-Chloro-2-(3-ethyl-2,3,4,5-tetrahydro-1H-benzo[d]azepin-7-ylamino)-pyrimidin-4-ylamino]-1,1-dimethyl-ethyl}-methanesulfonamide 304a) 2-Methyl-propane-1,2-diamine (2.38 g, 27.03 mmol, 2.83 mL, 1.5 eq.) in THF (100 mL) was cooled to 0 C and 2,4,5-trichloropyrimidine (3.30 g, 18.02 mmol, 2.06 mL, 1.0 eq.) was added. The reaction was stirred for 5 minutes before NEt$_3$ (6.5 mL) and mesyl chloride (3.08 g, 27.03 mmol, 2.08 mL, 1.5 eq.) were added simultaneously via two syringes. After 5 minutes, external cooling was removed and the reaction was stirred under a nitrogen atmosphere for 45 minutes. The reaction was then partitioned between CH$_2$Cl$_2$ (100 mL) and sat. NaHCO$_3$ (100 mL). The layers were separated and the aqueous layer was extracted with CH$_2$Cl$_2$ (50 mL). The combined organic layers were dried (sodium sulfate), filtered, and concentrated under reduced pressure onto basic alumina. Purification by basic alumina chromatography (dry loaded) using a gradient of 0-50% EtOAc/hex as the eluting solvent to obtain N-[2-(2,5-dichloro-pyrimidin-4-ylamino)-1,1-dimethyl-ethyl]-methanesulfonamide as a pale yellow solid (3.60 g, 64%). m.p.=143-145° C.; LCMS (m/e) 313 (M+1); $^1$H-NMR (CDCl$_3$, 400 MHz) δ 8.06 (s, 1H), 6.43-6.32 (m, 1H), 4.82 (s, 1H), 3.74 (d, 2H, J=6.2 Hz), 3.10 (s, 3H), 1.44 (s, 6H).

304b) 3-Ethyl-2,3,4,5-tetrahydro-1H-benzo[d]azepin-7-ylamine (86.7 mg, 0.456 mmol, 1.0 eq), N-[2-(2,5-dichloro-pyrimidin-4-ylamino)-1,1-dimethyl-ethyl]-methanesulfonamide (157 mg, 0.502 mmol, 1.1 eq), and 10-camphorsulfonic acid (116 mg, 0.502 mmol, 1.1 eq) were dissolved in IPA (3 mL) and heated at 120° C. in a microwave for 60 minutes. The reaction was then concentrated under reduced pressure and the residue was taken up in CH$_2$Cl$_2$ (20 mL) and washed with sat. NaHCO$_3$ (20 mL). The organic layer was dried (sodium sulfate), filtered, and concentrated under reduced pressure. Purification by basic alumina chromatography using a gradient of 0-100% EtOAc/hex as the eluting solvent to obtain N-{2-[5-chloro-2-(3-ethyl-2,3,4,5-tetrahydro-1H-benzo[d]azepin-7-ylamino)-pyrimidin-4-ylamino]-1,1-dimethyl-ethyl}-methanesulfonamide as a pink solid (73 mg, 34%). m.p.=118-121° C.; LCMS (m/e) 467 (M+1); $^1$H-NMR (CDCl$_3$, 400 MHz) δ 7.95 (s, 1H), 7.34-7.26 (m, 2H), 7.05 (d, 1H, J=7.7 Hz), 6.98 (s 1H), 5.82-5.72 (m, 2H), 3.65 (d, 1H, J=6.4 Hz), 2.94 (s, 3H), 3.00-2.85 (m, 4H), 2.73-2.55 (m, 4H), 2.58 (q, 2H, J=6.6 Hz), 1.44 (s, 6H), 1.11 (t, 3H, J=7.1 Hz).

Example 305

N-(2-{5-Chloro-2-[3-(2-methoxy-ethyl)-2,3,4,5-tetrahydro-1H-benzo[d]azepin-7-ylamino]-pyrimidin-4-ylamino}-1,1-dimethyl-ethyl)-methanesulfonamide N-(2-{5-Chloro-2-[3-(2-methoxy-ethyl)-2,3,4,5-tetrahydro-1H-benzo[d]azepin-7-ylamino]-pyrimidin-4-ylamino}-1,1-dimethyl-ethyl)-methanesulfonamide was prepared from 3-(2-methoxy-ethyl)-2,3,4,5-tetrahydro-1H-benzo[d]azepin-7-ylamine and N-[2-(2,5-dichloro-pyrimidin-4-ylamino)-1,1-dimethyl-ethyl]-methanesulfonamide in an analogous manner to Example 304. Product isolated as a white foam (120 mg, 71%). LCMS (m/e) 497 (M+1); $^1$H-NMR (CDCl$_3$, 400 MHz) δ 7.95 (s, 1H), 7.34-7.26 (m, 2H), 7.04 (d, 1H, J=7.8 Hz), 6.96 (s 1H), 5.80-5.71 (m, 2H), 3.65 (d, 1H, J=6.4 Hz), 3.55 (d, 2H, J=5.7 Hz), 3.38 (s, 3H), 2.95 (s, 3H), 2.98-2.88 (m, 4H), 2.80-2.68 (m, 6H), 1.45 (s, 6H).

Example 306

N-(2-{5-Chloro-2-[3-(2-methoxy-ethyl)-2,3,4,5-tetrahydro-1H-benzo[d]azepin-7-ylamino]-pyrimidin-4-ylamino}-2-methyl-propyl)-methanesulfonamide 306a) 2-Methyl-propane-1,2-diamine (2.00 g, 22.7 mmol, 2.38 mL, 1.1 eq.) was placed in CH$_2$Cl$_2$ (100 mL). Mesyl chloride (2.35 g, 20.7 mmol, 1.59 mL, 1.0 eq.) was added over a period of five minutes followed by triethylamine (6.27 g, 62.1 mmol, 8.71 mL, 3.0 eq.). The reaction was stirred for 30 minutes and then concentrated under reduced pressure. Purification by basic alumina chromatography using a gradient of 0-15% MeOH/CH$_2$Cl$_2$ as the eluting solvent to obtain N-(2-amino-2-methyl-propyl)-methanesulfonamide as a white solid (1.15 g, 33%). LCMS (m/e) 167 (M+1); $^1$H-NMR (CDCl$_3$, 400 MHz) δ 2.98 (s, 3H), 2.95 (s, 2H), 1.17 (s, 3H), 1.16 (s, 3H).

306b) N-(2-Amino-2-methyl-propyl)-methanesulfonamide (1.15 g, 6.90 mmol, 1.2 eq.) in THF (20 mL) was cooled to 0° C. and 2,4,5-trichloropyrimidine (1.05 g, 5.75 mmol, 656 µL, 1.0 eq.) was added. The reaction was stirred for 5 minutes and then NEt$_3$ (2.07 mL) was added. After 5 minutes, external cooling was removed and the reaction was heated at 60° C. overnight under a nitrogen atmosphere. The reaction was then partitioned between CH$_2$Cl$_2$ (150 mL) and sat. NaHCO$_3$ (150 mL). The layers were separated and the aqueous layer was extracted with CH$_2$Cl$_2$ (75 mL). The combined organic layers were dried (sodium sulfate), filtered, and concentrated under reduced pressure onto basic alumina. Purification by basic alumina chromatography (dry loaded) using a gradient of 0-60% EtOAc/hex as the eluting solvent to obtain N-[2-(2,5-dichloro-pyrimidin-4-ylamino)-2-methyl-propyl]-methanesulfonamide as a white solid (868 mg, 48%).

m.p.=156-158° C.; LCMS (m/e) 313 (M+1); ¹H-NMR (CDCl₃, 400 MHz) δ 8.04 (s, 1H), 5.57 (bs, 1H), 5.25-5.16 (m, 1H), 3.54 (d, 2H, J=6.8 Hz), 3.00 (s, 3H), 1.53 (s, 6H).

306c) 3-(2-Methoxy-ethyl)-2,3,4,5-tetrahydro-1H-benzo[d]azepin-7-ylamine (76 mg, 0.34 mmol, 1.0 eq), N-[2-(2,5-dichloro-pyrimidin-4-ylamino)-2-methyl-propyl]-methanesulfonamide (119 mg, 0.38 mmol, 1.1 eq), and 10-camphorsulfonic acid (88 mg, 0.38 mmol, 1.1 eq) were dissolved in IPA (3 mL) and heated at 120° C. in a microwave for 40 minutes. The reaction was then concentrated under reduced pressure and the residue was taken up in CH₂Cl₂ (20 mL) and washed with sat. NaHCO₃ (20 mL). The organic layer was dried (sodium sulfate), filtered, and concentrated under reduced pressure. Purification by amine capped silica gel chromatography using a gradient of 0-100% EtOAc/hex as the eluting solvent to obtain N-(2-{5-chloro-2-[3-(2-methoxy-ethyl)-2,3,4,5-tetrahydro-1H-benzo[d]azepin-7-ylamino]-pyrimidin-4-ylamino}-2-methyl-propyl)-methanesulfonamide as a white foam (107 mg, 63%). LCMS (m/e) 497 (M+1); ¹H-NMR (CDCl₃, 400 MHz) δ 7.94 (s, 1H), 7.25-7.18 (m, 2H), 7.04 (d, 1H, J=7.9 Hz), 6.87 (s 1H), 5.93-5.79 (m, 1H), 5.13 (s, 1H), 3.55 (t, 2H, J=5.7 Hz), 3.47 (d, 2H, J=6.0 Hz), 3.38 (s, 3H), 2.99-2.88 (m, 4H), 2.78 (s, 3H), 2.81-2.68 (m, 6H), 1.50 (s, 6H).

Example 307

N-{2-[5-Chloro-2-(3-ethyl-2,3,4,5-tetrahydro-1H-benzo[d]azepin-7-ylamino)-pyrimidin-4-ylamino]-2-methyl-propyl}-methanesulfonamide N-{2-[5-Chloro-2-(3-ethyl-2,3,4,5-tetrahydro-1H-benzo[d]azepin-7-ylamino)-pyrimidin-4-ylamino]-2-methyl-propyl}-methanesulfonamide was prepared from 3-ethyl-2,3,4,5-tetrahydro-1H-benzo[d]azepin-7-ylamine and N-[2-(2,5-dichloro-pyrimidin-4-ylamino)-2-methyl-propyl]-methanesulfonamide in an analogous manner to Example 306. Product isolated as a white foam (22 mg, 10%). LCMS (m/e) 467 (M+1); ¹H-NMR (CDCl₃, 400 MHz) δ 7.93 (s, 1H), 7.26-7.18 (m, 2H), 7.05 (d, 1H, J=7.9 Hz), 6.93 (s 1H), 5.95-5.80 (m, 1H), 5.13 (s, 1H), 3.47 (d, 2H, J=5.8 Hz), 2.97-2.88 (m, 4H), 2.78 (s, 3H), 2.72-2.58 (m, 4H), 2.59 (q, 2H, J=7.1 Hz), 1.50 (s, 6H), 1.12 (t, 3H, J=7.1 Hz).

Example 308

2-{5-Chloro-2-[3-(2-methoxy-ethyl)-2,3,4,5-tetrahydro-1H-benzo[d]azepin-7-ylamino]-pyrimidin-4-ylamino}-5,N-dimethyl-benzamide 308a) 5-Methyl isatoic anhydride (10.1 g, 57.2 mmol) was dissolved in 100 mL THF and treated with a solution (aqueous or THF) of methylamine (120 mmol). The mixture was stirred for 2 hours and then concentrated in vacuo and azeotroped with benzene. Trituration from ether twice afforded 2-amino-5,N-dimethyl-benzamide (5.25 g, 56%). m.p.=122-123° C.; LCMS (m/e) 165 (M+1); ¹H-NMR (CDCl₃, 400 MHz) δ 8.10 (m, 1H), 6.94 (d, 1H, J=8.3 Hz), 6.59 (d, 1H, J=8.3 Hz), 6.15 (s, 2H), 2.71 (d, 3H, J=4.5 Hz), 2.15 (s, 3H).

308b) 2-Amino-5,N-dimethyl-benzamide (2.0 g, 12.2 mmol), potassium carbonate (2 eq) or diisopropylethylamine (2 eq) and 2,4,5-trichloropyrimidine (2.24 g, 12.2 mmol) were combined in DMF or NMP (25 mL) and heated at 50-100° C. until HPLC indicated consumption of the starting materials. The reaction can either be concentrated in vacuo or directly partitioned between water and dichloromethane. The product is extracted, dried and concentrated to afford the crude material, which is then chromatographed on silica gel (ethyl acetate:hexanes) to afford 2-(2,5-dichloro-pyrimidin-4-ylamino)-5,N-dimethyl-benzamide (5.25 g, 56%) as a light yellow solid. m.p.=192-210° C.; LCMS (m/e) 311 (M+1); ¹H-NMR (DMSO-d₆, 400 MHz) δ 12.02 (s, 1H), 8.82 (m, 1H), 8.45 (s, 1H), 8.38 (d, 1H, J=8.5 Hz), 7.63 (s, 1H), 7.42 (d, 1H, J=8.5 Hz), 2.80 (d, 3H, J=4.4 Hz), 2.34 (s, 3H).

308c) 3-(2-Methoxy-ethyl)-2,3,4,5-tetrahydro-1H-benzo[d]azepin-7-ylamine (76 mg, 0.34 mmol) and 2-(2,5-dichloro-pyrimidin-4-ylamino)-5,N-dimethyl-benzamide (120 mg, 0.38 mmol, 1.1 eq) were dissolved in IPA (3 mL). 4.0 M HCl in dioxane (95 μL, 0.38 mmol, 1.1 eq) was added and the reaction was heated at 130° C. in a microwave for 20 minutes. The reaction was then concentrated under reduced pressure and the residue was taken up in CH₂Cl₂ (20 mL) and washed with sat. NaHCO₃ (20 mL). The organic layer was dried (sodium sulfate), filtered, and concentrated under reduced pressure. Purification by basic alumina chromatography using a gradient of 0-100% EtOAc/hex as the eluting solvent to obtain 2-{5-chloro-2-[3-(2-methoxy-ethyl)-2,3,4,5-tetrahydro-1H-benzo[d]azepin-7-ylamino]-pyrimidin-4-ylamino}-5,N-dimethyl-benzamide as a yellow solid (99.4 mg, 59%). m.p.=210-212° C.; LCMS (m/e) 495 (M+1); ¹H-NMR (CDCl₃, 400 MHz) δ 10.87 (s, 1H), 8.51 (d, 1H, J=8.5 Hz), 8.05 (d, 1H, J=1.0 Hz), 7.35 (s, 1H), 7.30-7.15 (m, 3H), 7.01 (d, 1H, J=8.1 Hz), 6.86 (s, 1H), 6.23-6.10 (m, 1H), 3.54 (t, 2H, J=5.4 Hz), 3.37 (s, 3H), 3.02 (d, 3H, J=5.0 Hz), 2.96-2.84 (m, 5H), 2.80-2.66 (m, 6H), 2.36 (s, 3H).

Example 309

5-Chloro-N*2*-[3-(2-methoxy-ethyl)-2,3,4,5-tetrahydro-1H-benzo[d]azepin-7-yl]-N*4*-(2-methoxy-4-morpholin-4-yl-phenyl)-pyrimidine-2,4-diamine 5-Chloro-N*2*-[3-(2-methoxy-ethyl)-2,3,4,5-tetrahydro-1H-benzo[d]azepin-7-yl]-N*4*-(2-methoxy-4-morpholin-4-yl-phenyl)-pyrimidine-2,4-diamine was prepared from 3-(2-methoxy-ethyl)-2,3,4,5-tetrahydro-1H-benzo[d]azepin-7-ylamine and (2,5-dichloro-pyrimidin-4-yl)-(2-methoxy-4-morpholin-4-yl-phenyl)-amine in an analogous manner to Example 308c. Product isolated as an off-white solid (137 mg, 75%). m.p.=144-146° C.; LCMS (m/e) 539 (M+1); ¹H-NMR (CDCl₃, 400 MHz) δ 8.25 (d, 1H, J=8.8 Hz), 8.00 (s, 1H), 7.59 (s, 1H), 7.39 (s, 1H), 7.22-7.16 (m, 1H), 7.01 (d, 1H, J=8.0 Hz), 6.84 (s, 1H), 6.54 (bs, 1H), 6.52-6.46 (m, 1H), 3.92 (s, 3H), 3.92-3.86 (m, 4H), 3.54 (t, 2H, J=5.6 Hz), 3.36 (s, 3H), 3.19-3.13 (m, 4H), 2.94-2.87 (m, 4H), 2.78-2.68 (m, 6H).

Example 310

(2-exo,3-exo)-3-{5-Chloro-2-[3-(2-methoxy-ethyl)-2,3,4,5-tetrahydro-1H-benzo[d]azepin-7-ylamino]-pyrimidin-4-ylamino}-bicyclo[2.2.1]hept-5-ene-2-carboxylic acid amide (2-exo,3-exo)-3-{5-Chloro-2-[3-(2-methoxy-ethyl)-2,3,4,5-tetrahydro-1H-benzo[d]azepin-7-ylamino]-pyrimidin-4-ylamino}-bicyclo[2.2.1]hept-5-ene-2-carboxylic acid amide was prepared from 3-(2-methoxy-ethyl)-2,3,4,5-tetrahydro-1H-benzo[d]azepin-7-ylamine and (2-exo,3-exo)-3-(2,5-dichloro-pyrimidin-4-ylamino)-bicyclo[2.2.1]hept-5-ene-2-carboxylic acid amide in an analogous manner to Example 308c. Product isolated as an orange foam (144 mg, 87%). LCMS (m/e) 483 (M+1); ¹H-NMR (CDCl₃, 400 MHz) δ 7.87 (s, 1H), 7.39 (d, 1H, J=8.0 Hz), 7.01 (d, 1H, J=7.9 Hz), 6.84

(s, 1H), 6.80 (d, 1H, J=8.7 Hz), 6.36-6.27 (m, 2H), 5.56 (bs, 1H), 5.37 (bs, 1H), 4.40-4.32 (m, 1H), 3.54 (t, 2H, J=5.6 Hz), 3.37 (s, 3H), 3.10-3.03 (m, 1H), 2.95-2.83 (m, 5H), 2.80-2.65 (m, 6H), 2.50-2.43 (m, 1H), 2.28-2.20 (m, 1H), 1.65-1.55 (m, 3H).

Example 311

2-{5-Chloro-2-[3-(2-methoxy-ethyl)-2,3,4,5-tetrahydro-1H-benzo[d]azepin-7-ylamino]-pyrimidine-4-ylamino}-3-fluoro-N-methyl-benzamide 311a) Analagous to Example 308a, 2-amino-3-fluoro-N-methyl-benzamide was prepared from 3-fluoro isatoic anhydride in 90% yield. m.p.=94-97° C.; LCMS (m/e) 169 (M+1); $^1$H-NMR (DMSO-$d_6$, 400 MHz) δ 8.30 (s, 1H), 7.32 (d, 1H, J=8.0 Hz), 7.12 (m, 1H), 6.52 (m, 1H), 6.32 (s, 2H), 2.73 (d, 3H, J=4.5 Hz).

311b) Analagous to Example 308b, 2-(2,5-dichloro-pyrimidin-4-ylamino)-3-fluoro-N-methyl-benzamide was prepared in 36% yield. m.p.=226-228° C.; LCMS (m/e) 315 (M+1); $^1$H-NMR (DMSO-$d_6$, 400 MHz) δ 9.79 (s, 1H), 8.53 (m, 1H), 8.42 (s, 1H), 7.45 (m, 3H), 2.72 (d, 3H, J=4.5 Hz).

311c) 2-{5-Chloro-2-[3-(2-methoxy-ethyl)-2,3,4,5-tetrahydro-1H-benzo[d]azepin-7-ylamino]-pyrimidine-4-ylamino}-3-fluoro-N-methyl-benzamide was prepared from 3-(2-methoxy-ethyl)-2,3,4,5-tetrahydro-1H-benzo[d]azepin-7-ylamine and 2-(2,5-dichloro-pyrimidin-4-ylamino)-3-fluoro-N-methyl-benzamide in an analogous manner to Example 308c. Product isolated as a yellow foam (52 mg, 31%). LCMS (m/e) 499 (M+1); $^1$H-NMR (CDCl$_3$, 400 MHz) δ 8.70 (bs, 1H), 8.05 (s, 1H), 7.34-7.22 (m, 2H), 7.14 (s, 1H), 7.09 (d, 1H, J=8.1 Hz), 6.88 (d, 1H, J=8.1 Hz), 6.82 (s, 1H), 6.10-6.0 (m, 1H), 3.59-3.52 (m, 2H), 3.37 (s, 3H), 2.90 (d, 3H, J=4.8 Hz), 2.89-2.60 (m, 10H).

Example 312

3-Chloro-2-{5-chloro-2-[3-(2-methoxy-ethyl)-2,3,4,5-tetrahydro-1H-benzo[d]azepin-7-ylamino]-pyrimidine-4-ylamino}-N-methyl-benzamide 312a) Analagous to Example 308a, 2-amino-3-chloro-N-methyl-benzamide was prepared from 3-chloro isatoic anhydride in 31% yield. m.p.=148-152° C.; LCMS (m/e) 185 (M+1); $^1$H-NMR (DMSO-$d_6$, 400 MHz) δ 8.35 (m, 1H), 7.46 (d, 1H, J=8.0 Hz), 7.34 (d, 1H, J=7.9 Hz), 6.55 (m, 3H), 2.74 (d, 3H, J=4.5 Hz).

312b) Analagous to Example 308b, 3-chloro-2-(2,5-dichloro-pyrimidin-4-ylamino)-N-methyl-benzamide was prepared in 32% yield. m.p.=213-215° C.; LCMS (m/e) 331 (M+1); $^1$H-NMR (DMSO-$d_6$, 400 MHz) δ 9.62 (s, 1H), 8.39 (m, 2H), 7.70 (d, 1H, J=8.0 Hz), 7.54 (d, 1H, J=7.7 Hz), 7.44 (m, 1H), 2.67 (d, 3H, J=4.5 Hz).

312c) 3-Chloro-2-{5-chloro-2-[3-(2-methoxy-ethyl)-2,3,4,5-tetrahydro-1H-benzo[d]azepin-7-ylamino]-pyrimidine-4-ylamino}-N-methyl-benzamide was prepared from 3-(2-methoxy-ethyl)-2,3,4,5-tetrahydro-1H-benzo[d]azepin-7-ylamine and 2-(2,5-dichloro-pyrimidin-4-ylamino)-3-chloro-N-methyl-benzamide in an analogous manner to Example 308c. Product isolated as a yellow foam (25 mg, 14%). LCMS (m/e) 515 (M+1); $^1$H-NMR (CDCl$_3$, 400 MHz) δ 8.06 (s, 1H), 7.82 (s, 1H), 7.58 (d, 1H, J=8.0 Hz), 7.44 (d, 1H, J=7.7 Hz), 7.31-7.25 (m, 1H), 7.10 (s, 1H), 6.99 (d, 1H, J=8.0 Hz), 6.96 (s, 1H), 6.86 (d, 1H, J=8.0 Hz), 6.03-5.93 (m, 1H), 3.56-3.52 (m, 2H), 3.37 (s, 3H), 2.88-2.82 (m, 2H), 2.76-2.60 (m, 12H).

Example 313

2-{5-Chloro-2-[3-(2-methoxy-ethyl)-2,3,4,5-tetrahydro-1H-benzo[d]azepin-7-ylamino]-pyrimidin-4-ylamino}-3,N-dimethyl-benzamide 313a) Analagous to Example 308a, 2-amino-3,N-dimethyl-benzamide was prepared from 3-methyl isatoic anhydride in 47% yield. m.p.=128-131° C.; LCMS (m/e) 165 (M+1); $^1$H-NMR (DMSO-$d_6$, 400 MHz) δ 8.16 (m, 1H), 7.32 (d, 1H, J=8.0 Hz), 7.05 (d, 1H, J=7.1 Hz), 6.46 (m, 1H), 6.21 (s, 2H), 2.72 (d, 3H, J=4.5 Hz), 2.07 (s, 3H).

313b) Analagous to Example 308b, 2-(2,5-dichloro-pyrimidin-4-ylamino)-3,N-dimethyl-benzamide was prepared in 6% yield. m.p.=220-224° C.; LCMS (m/e) 311 (M+1); $^1$H-NMR (DMSO-$d_6$, 400 MHz) δ 9.58 (s, 1H), 8.30 (m, 2H), 7.41 (m, 2H), 7.32 (m, 1H), 2.72 (d, 3H, J=4.4 Hz), 2.07 (s, 3H).

313c) 3-(2-Methoxy-ethyl)-2,3,4,5-tetrahydro-1H-benzo[d]azepin-7-ylamine (76 mg, 0.34 mmol, 1.0 eq), 2-(2,5-dichloro-pyrimidin-4-ylamino)-3,N-dimethyl-benzamide (118 mg, 0.38 mmol, 1.1 eq), and 10-camphorsulfonic acid (88 mg, 0.38 mmol, 1.1 eq) were dissolved in IPA (3 mL) and heated at 120° C. in a microwave for 40 minutes. The reaction was then concentrated under reduced pressure and the residue was taken up in CH$_2$Cl$_2$ (20 mL) and washed with sat NaHCO$_3$ (20 mL). The organic layer was dried (sodium sulfate), filtered, and concentrated under reduced pressure. Purification by amine capped silica gel chromatography using a gradient of 0-100% EtOAc/hex as the eluting solvent to obtain 2-{5-chloro-2-[3-(2-methoxy-ethyl)-2,3,4,5-tetrahydro-1H-benzo[d]azepin-7-ylamino]-pyrimidin-4-ylamino}-3,N-dimethyl-benzamide as a pale yellow foam (50 mg, 30%). LCMS (m/e) 495 (M+1); $^1$H-NMR (CDCl$_3$, 400 MHz) δ 8.51 (s, 1H), 8.04 (s, 1H), 7.45-7.35 (m, 2H), 7.32-7.22 (m, 1H), 7.11 (s, 1H), 6.98 (d, 1H, J=8.1 Hz), 6.85 (d, 1H, J=7.9 Hz), 6.78 (s, 1H), 6.06-5.97 (m, 1H), 3.55 (t, 2H, J=5.7 Hz), 3.39 (s, 3H), 2.89 (d, 3H, J=4.9 Hz), 2.88-2.82 (m, 2H), 2.75 (t, 2H, J=5.7 Hz), 2.73-2.62 (m, 6H), 2.27 (s, 3H).

Example 314

3,5-Dichloro-2-{5-chloro-2-[3-(2-methoxy-ethyl)-2,3,4,5-tetrahydro-1H-benzo[d]azepin-7-ylamino]-pyrimidin-4-ylamino}-N-methyl-benzamide 314a) Analagous to Example 308a, 2-amino-3,5-dichloro-N-methyl-benzamide was prepared from 3,5-dichloro isatoic anhydride in 31% yield. m.p.=154-161° C.; LCMS (m/e) 218 (M+1); $^1$H-NMR (DMSO-$d_6$, 400 MHz) δ 8.49 (m, 1H), 7.55 (s, 1H), 7.50 (s, 1H), 6.65 (s, 2H), 2.74 (d, 3H, J=4.5 Hz).

314b) Analagous to Example 308b, 2-(2,5-dichloro-pyrimidin-4-ylamino)-3,5-dichloro-N-methyl-benzamide was prepared in 32% yield. m.p.=202-206° C.; LCMS (m/e) 365 (M+1); $^1$H-NMR (DMSO-$d_6$, 400 MHz) δ 9.62 (s, 1H), 8.47 (m, 1H), 8.40 (s, 1H), 7.92 (s, 1H), 7.62 (s, 1H), 2.66 (d, 3H, J=4.4 Hz).

314c) 3,5-Dichloro-2-{5-chloro-2-[3-(2-methoxy-ethyl)-2,3,4,5-tetrahydro-1H-benzo[d]azepin-7-ylamino]-pyrimidin-4-ylamino}-N-methyl-benzamide was prepared from 3-(2-methoxy-ethyl)-2,3,4,5-tetrahydro-1H-benzo[d]azepin-7-ylamine and 2-(2,5-dichloro-pyrimidin-4-ylamino)-3,5-dichloro-N-methyl-benzamide in an analogous manner to Example 303c. Product isolated as an off-white foam (47 mg, 25%). LCMS (m/e) 549 (M+1); $^1$H-NMR (CDCl$_3$, 400 MHz) δ 8.10 (s, 1H), 7.69 (s, 1H), 7.61 (s, 1H), 7.47 (s 1H), 7.15 (s, 1H), 7.01-6.89 (m, 2H), 6.87 (s, 1H), 6.01-5.92 (m, 1H), 3.56 (t, 2H, J=5.5 Hz), 3.39 (s, 3H), 2.92-2.84 (s, 2H), 2.81-2.65 (m, 8H), 2.75 (d, 3H, J=4.4 Hz).

Example 315

2-{5-Chloro-2-[3-(2-methoxy-ethyl)-2,3,4,5-tetrahydro-1H-benzo[d]azepin-7-ylamino]-pyrimidin-4-ylamino}-3-methoxy-N-methyl-benzamide 315a) Analagous to Example 308a, 2-amino-3-methoxy-N-methyl-benzamide was prepared from 3-chloro isatoic anhydride in 31% yield. m.p.=128-130° C.; LCMS (m/e) 180 (M+1); $^1$H-NMR (DMSO-d$_6$, 400 MHz) δ 8.12 (m, 1H), 7.11 (d, 1H, J=8.0 Hz), 6.88 (d, 1H, J=7.9 Hz), 6.51 (m, 1H), 6.12 (s, 2H), 3.79 (s, 3H), 2.74 (d, 3H, J=4.5 Hz).

315b) Analagous to Example 308b, 2-(2,5-dichloro-pyrimidin-4-ylamino)-3-methoxy-N-methyl-benzamide was prepared in 17% yield. m.p.=200-206° C.; LCMS (m/e) 327 (M+1); $^1$H-NMR (DMSO-d$_6$, 400 MHz) δ 9.38 (s, 1H), 8.31 (s, 2H), 7.45 (m, 1H), 7.30 (d, 1H, J=8.3 Hz), 7.17 (d, 1H, J=7.7 Hz), 3.79 (s, 3H), 2.69 (d, 3H, J=4.5 Hz).

315c) 2-{5-Chloro-2-[3-(2-methoxy-ethyl)-2,3,4,5-tetrahydro-1H-benzo[d]azepin-7-ylamino]-pyrimidin-4-ylamino}-3-methoxy-N-methyl-benzamide was prepared from 3-(2-methoxy-ethyl)-2,3,4,5-tetrahydro-1H-benzo[d]azepin-7-ylamine and 2-(2,5-dichloro-pyrimidin-4-ylamino)-3-methoxy-N-methyl-benzamide in an analogous manner to Example 313c. Product isolated as a yellow foam (64 mg, 37%). LCMS (m/e) 511 (M+1); $^1$H-NMR (CDCl$_3$, 400 MHz) δ 8.05 (s, 1H), 7.71 (s, 1H), 7.33-7.27 (m, 1H), 7.19 (d 1H, J=7.7 Hz), 7.13 (s, 1H), 7.10-7.04 (m, 2H), 6.89 (d, 1H, J=8.1 Hz), 6.85 (s, 1H), 6.04-5.96 (m, 1H), 3.84 (s, 3H), 3.55 (t, 2H, J=5.7 Hz), 3.39 (s, 3H), 2.90-2.84 (m, 2H), 2.79-2.63 (m, 8H), 2.75 (d, 3H, J=4.1 Hz).

Example 316

5-Chloro-N*2*-[3-(2-methoxy-ethyl)-2,3,4,5-tetrahydro-1H-benzo[d]azepin-7-yl]-N*4*-(2-pyrazol-1-yl-phenyl)-pyrimidine-2,4-diamine 5-Chloro-N*2*-[3-(2-methoxy-ethyl)-2,3,4,5-tetrahydro-1H-benzo[d]azepin-7-yl]-N*4*-(2-pyrazol-1-yl-phenyl)-pyrimidine-2,4-diamine was prepared from 2-(1H-pyrazol-1-yl)aniline, 2,4,5-trichloropyrimidine, and 3-(2-methoxy-ethyl)-2,3,4,5-tetrahydro-1H-benzo[d]azepin-7-ylamine in an analogous manner to Example 308. Product isolated as a white foam (108 mg, 65%). LCMS (m/e) 490 (M+1); $^1$H-NMR (CDCl$_3$, 400 MHz) δ 10.20 (s, 1H), 8.52 (d, 1H, J=8.3 Hz), 8.04 (d, 1H, J=1.6 Hz), 7.86 (s 1H), 7.81 (d, 1H, J=1.9 Hz), 7.41-7.14 (m, 5H), 7.10-6.90 (m, 2H), 6.54-6.50 (m, 1H), 3.69-3.54 (m, 2H), 3.39 (s, 3H), 2.96-2.86 (m, 4H), 2.80-2.69 (m, 6H).

Example 317

2-{5-Chloro-2-[3-(2-methoxy-ethyl)-2,3,4,5-tetrahydro-1H-benzo[d]azepin-7-ylamino]-pyrimidin-4-ylamino}-3,5,N-trimethyl-benzamide 2-{5-Chloro-2-[3-(2-methoxy-ethyl)-2,3,4,5-tetrahydro-1H-benzo[d]azepin-7-ylamino]-pyrimidin-4-ylamino}-3,5,N-trimethyl-benzamide was prepared from 3,5-dimethyl isotoic anhydride, 2,4,5-trichloropyrimidine, and 3-(2-methoxy-ethyl)-2,3,4,5-tetrahydro-1H-benzo[d]azepin-7-ylamine in an analogous manner to Example 308. Product isolated as a yellow foam (95 mg, 55%). LCMS (m/e) 509 (M+1); $^1$H-NMR (CDCl$_3$, 400 MHz) δ 8.26 (s, 1H), 8.03 (s, 1H), 7.22 (s, 1H), 7.21-7.16 (m 2H), 6.94 (d, 1H, J=8.0 Hz), 6.86 (d, 1H, J=8.0 Hz), 6.81 (s, 1H), 6.08-6.01 (m, 1H), 3.55 (t, 2H, J=5.7 Hz), 3.88 (s, 3H), 2.87 (d, 3H, J=4.9 Hz), 2.90-2.82 (m, 2H), 2.75 (t, 2H, J=5.7 Hz), 2.72-2.62 (m, 6H), 2.41 (s, 3H), 2.23 (s, 3H).

Example 318 trans-2-{5-Chloro-2-[3-(2-methoxy-ethyl)-2,3,4,5-tetrahydro-1H-benzo[d]azepin-7-ylamino]-pyrimidin-4-ylamino}-cyclohexanol 318a) Tetrahydrofuran (100 mL) was added to racemic trans-2-amino-cyclohexanol hydrochloride (4.28 g, 28.2 mmol) and potassium carbonate (12.1 g, 88 mmol). The mixture was cooled at 0° C. before 2,4,5-trichloropyrimidine (2 mL, 17.4 mmol) was added. After 3 hours, the mixture was partitioned between water and ethyl acetate, the aq. layer was extracted and the combined extracts were dried and conc. in vacuo. The crude product was taken up in ethyl acetate and washed with 10% w/v citric acid, then with sodium bicarbonate, dried over sodium sulfate and conc. in vacuo to give rel-(1R,2R)-2-(2,5-dichloro-pyrimidin-4-ylamino)-cyclohexanol (2.27 g, 50%) as a white solid. m.p.=139-142° C.; LCMS (m/e) 262 (M+1); $^1$H-NMR (DMSO-d$_6$, 400 MHz) δ 8.12 (s, 1H), 7.45 (m, 1H), 68 (m, 1H), 3.81 (m, 1H), 3.55 (m, 1H), 1.92 (m, 1H), 1.81 (m, 1H), 1.67 (m, 2H), 1.41 (m, 1H), 1.26 (m, 3H).

318b) 3-(2-Methoxy-ethyl)-2,3,4,5-tetrahydro-1H-benzo[d]azepin-7-ylamine (76 mg, 0.34 mmol) and trans-2-(2,5-dichloro-pyrimidin-4-ylamino)-cyclohexanol (100 mg, 0.38& mmol, 1.1 eq) were dissolved in IPA (3 mL). 4.0 M HCl in dioxane (95 μL, 0.38 mmol, 1.1 eq) was added and the reaction was heated at 140° C. in a microwave for 2.5 hours. The reaction was then concentrated under reduced pressure and the residue was taken up in CH$_2$Cl$_2$ (20 mL) and washed with sat. NaHCO$_3$ (20 mL). The organic layer was dried (sodium sulfate), filtered, and concentrated under reduced pressure. Purification by basic alumina chromatography using a gradient of 0-100% EtOAc/hex as the eluting solvent to obtain trans-2-{5-chloro-2-[3-(2-methoxy-ethyl)-2,3,4,5-tetrahydro-1H-benzo[d]azepin-7-ylamino]-pyrimidin-4-ylamino}-cyclohexanol as a pink foam (42 mg, 28%). LCMS (m/e) 446 (M+1); $^1$H-NMR (CDCl$_3$, 400 MHz) δ 7.93 (s, 1H), 7.35-7.22 (m, 2H), 7.04 (d, 1H, J=8.1 Hz), 6.78 (s, 1H), 5.17 (d, 1H, J=7.1 Hz), 3.96-3.85 (m, 1H), 3.60-3.54 (m, 2H), 3.38 (s, 3H), 3.00-2.85 (m, 4H), 2.81-2.65 (m, 6H), 2.20-2.10 (m, 2H), 1.85-1.77 (m, 2H), 1.45-1.10 (m, 5H).

Example 319 trans-2-[5-Chloro-2-(3-ethyl-2,3,4,5-tetrahydro-1H-benzo[d]azepin-7-ylamino)-pyrimidin-4-ylamino]-cyclohexanol Analagous to Example 318b, trans-2-{5-chloro-2-[3-(2-methoxy-ethyl)-2,3,4,5-tetrahydro-1H-benzo[d]azepin-7-ylamino]-pyrimidin-4-ylamino}-N-cyclopropyl-benzamide was prepared from 3-ethyl-2,3,4,5-tetrahydro-1H-benzo[d]azepin-7-ylamine and trans-2-(2,5-dichloro-pyrimidin-4-ylamino)-cyclohexanol in 35% yield as a foam. LCMS (m/e) 416 (M+1); $^1$H-NMR (CDCl$_3$, 400 MHz) δ 7.91 (s, 1H), 7.35 (s, 1H), 7.23 (m, 1H), 7.05 (m, 1H), 6.82 (s, 1H), 5.16 (m, 1H), 3.90 (m, 1H), 3.48 (m, 1H), 2.7-3.2 (m, 10H), 2.14 (m, 2H), 1.78 (m, 2H), 1.2-1.5 (m, 8H).

Example 320

5-Chloro-N*2*-(3-methanesulfonyl-2,3,4,5-tetrahydro-1H-benzo[d]azepin-7-yl]-N*4*-(2-methoxy-4-morpholin-4-yl-phenyl)-pyrimidine-2,4-diamine 5-Chloro-N*2*-(3-methanesulfonyl-2,3,4,5-tetrahydro-1H-benzo[d]azepin-7-yl]-N*4*-(2-methoxy-4-morpholin-4-yl-phenyl)-pyrimidine-2,4-diamine was prepared from 3-methanesulfonyl-2,3,4,5-tetrahydro-1H-benzo[d]azepin-7-ylamine and (2,5-dichloro-pyrimidin-4-yl)-(2-methoxy-4-morpholin-4-yl-phenyl)-amine in an analogous manner to Example 318b. Product isolated as a pale yellow solid (60 mg, 37%). m.p.=204-206° C.; LCMS (m/e) 559 (M+1); $^1$H-NMR (CDCl$_3$, 400 MHz) δ 8.17 (d, 1H, J=8.8 Hz), 8.01 (s, 1H), 7.54 (s, 1H), 7.44 (s, 1H), 7.04 (d, 1H, J=7.9 Hz), 6.88 (s, 1H), 6.54 (s, 1H), 6.49 (d, 1H, J=9.0 Hz), 3.91 (s, 3H), 3.91-3.87 (m, 4H), 3.47-3.40 (m, 4H), 3.19-3.13 (m, 4H), 3.03-2.95 (m, 4H), 2.77 (s, 3H).

Example 321

(2-exo, 3-exo)-3-[5-Chloro-2-(3-methanesulfonyl-2,3,4,5-tetrahydro-1H-benzo[d]azepin-7-ylamino)-pyrimidin-4-ylamino]-bicyclo[2.2.1]hept-5-ene-2-carboxylic acid amide (2-exo, 3-exo)-3-[5-Chloro-2-(3-methanesulfonyl-2,3,4,5-tetrahydro-1H-benzo[d]azepin-7-ylamino)-pyrimidin-4-ylamino]-bicyclo[2.2.1]hept-5-ene-2-carboxylic acid amide was prepared from 3-methanesulfonyl-2,3,4,5-tetrahydro-1H-benzo[d]azepin-7-ylamine and (2-exo, 3-exo)-3-(2,5-dichloro-pyrimidin-4-ylamino)-bicyclo[2.2.1]hept-5-ene-2-carboxylic acid amide in an analogous manner to Example 318b. Product isolated as a white solid (38 mg, 26%). m.p.=250-251° C.; LCMS (m/e) 503 (M+1); $^1$H-NMR (d$_6$-DMSO, 400 MHz) δ 9.22 (s, 1H), 7.95 (s, 1H), 7.82-7.73 (m, 2H), 7.62 (d, 1H, J=8.4 Hz), 7.44 (s, 1H), 7.30-7.23 (m, 1H), 7.06 (d, 1H, J=8.2 Hz), 6.40-6.35 (m, 1H), 6.31-6.25 (m, 1H), 4.17-4.05 (m, 1H), 3.37-3.25 (m, 4H), 3.20-3.19 (m, 1H), 2.93-2.83 (m, 5H), 2.86 (s, 3H), 2.82-2.76 (m, 1H), 2.15-2.07 (m, 1H), 1.45-1.37 (m, 1H).

Example 322

2-[5-Chloro-2-(3-prop-2-ynyl-2,3,4,5-tetrahydro-1H-benzo[d]azepin-7-ylamino)-pyrimidin-4-ylamino]-N-methyl-benzamide 322a) 7-Nitro-2,3,4,5-tetrahydro-1H-benzo[d]azepine nitric acid salt (1.0 g, 3.94 mmol) was dissolved in acetone (100 mL) followed by addition of Cs$_2$CO$_3$ (3.84 g, 11.82 mmol, 3.0 eq) and propargyl bromide (80% in toluene) (463 μL, 4.33 mmol, 1.1 eq). The reaction was stirred at room temperature for 24 hours. The solution was then concentrated under reduced pressure and the residue was taken up in CH$_2$Cl$_2$ (100 mL) and washed with water (100 mL). The organic layer was dried (sodium sulfate), filtered, and concentrated under reduced pressure. Purification by silica gel chromatography using a gradient of 0-10% MeOH/CH$_2$Cl$_2$ as the eluting solvent to obtain 7-nitro-3-prop-2-ynyl-2,3,4,5-tetrahydro-1H-benzo[d]azepine as a yellow solid (756 mg, 83%). m.p.=122-125° C.; LCMS (m/e) 231 (M+1); $^1$H-NMR (CDCl$_3$, 400 MHz) δ 8.05-7.98 (m, 2H), 7.30-7.23 (m, 1H), 3.49-3.43 (m, 2H), 3.13-3.02 (m, 4H), 2.84-2.71 (m, 4H), 2.26-2.22 (m, 1H).

322b) 7-Nitro-3-prop-2-ynyl-2,3,4,5-tetrahydro-1H-benzo[d]azepine (589 mg, 2.56 mmol) was dissolved in ethyl acetate (80 mL) and ethanol (30 mL). Tin (II) chloride dehydrate (2.88 g, 12.80 mmol, 5.0 eq) was added and the reaction was heated at reflux for 18 hours. The reaction was allowed to cool to room temperature and was then concentrated under reduced pressure. The residue was taken up in EtOAc (100 mL) and washed with 10% aqueous KF (70 mL). The organic layer was dried (sodium sulfate), filtered, and concentrated under reduced pressure to obtain 3-prop-2-ynyl-2,3,4,5-tetrahydro-1H-benzo[d]azepin-7-ylamine as a yellow solid (487 mg, 95%). An analytical sample was purified by prep-HPLC using a gradient of 0-30% acetonitrile/water. LCMS (m/e) 201 (M+1); $^1$H-NMR (CDCl$_3$, 400 MHz) δ 6.91 (d, 1H, J=7.7 Hz), 6.52-6.46 (m, 2H), 3.43 (d, 2H, J=2.3 Hz), 2.91-2.82 (m, 4H), 2.78-2.64 (m, 4H), 2.24-2.19 (m, 1H).

322c) 2-[5-Chloro-2-(3-prop-2-ynyl-2,3,4,5-tetrahydro-1H-benzo[d]azepin-7-ylamino)-pyrimidin-4-ylamino]-N-methyl-benzamide was prepared from 3-prop-2-ynyl-2,3,4,5-tetrahydro-1H-benzo[d]azepin-7-ylamine and 2-(2,5-dichloro-pyrimidin-4-ylamino)-N-methyl-benzamide in an analogous manner to Example 318b. Product isolated as a yellow solid (26 mg, 13%). m.p.=223-225° C.; LCMS (m/e) 461 (M+1); $^1$H-NMR (CDCl$_3$, 400 MHz) δ 11.07 (s, 1H), 8.67 (d, 1H, J=8.5 Hz), 8.11 (s, 1H), 7.58-7.45 (m, 2H), 7.38 (s, 1H), 7.15-7.05 (m, 2H), 6.89 (s, 1H), 6.30-6.15 (m, 1H), 3.46 (s, 2H), 3.05 (d, 3H, J=4.8 Hz), 2.98-2.87 (m, 4H), 2.80-2.70 (m, 4H), 2.24-2.20 (m, 1H), 2.20-2.17 (m, 1H).

Example 323

(2-exo, 3-exo)-3-[5-Chloro-2-(3-prop-2-ynyl-2,3,4,5-tetrahydro-1H-benzo[d]azepin-7-ylamino)-pyrimidin-4-ylamino]-bicyclo[2.2.1]hept-5-ene-2-carboxylic acid amide (2-exo, 3-exo)-3-[5-Chloro-2-(3-prop-2-ynyl-2,3,4,5-tetrahydro-1H-benzo[d]azepin-7-ylamino)-pyrimidin-4-ylamino]-bicyclo[2.2.1]hept-5-ene-2-carboxylic acid amide was prepared from 3-prop-2-ynyl-2,3,4,5-tetrahydro-1H-benzo[d]azepin-7-ylamine and (2-exo,3-exo)-3-(2,5-dichloro-pyrimidin-4-ylamino)-bicyclo[2.2.1]hept-5-ene-2-carboxylic acid amide in an analogous manner to Example 322. Product isolated as an orange foam (123 mg, 53%). LCMS (m/e) 463 (M+1); $^1$H-NMR (CDCl$_3$, 400 MHz) δ 7.89 (s, 1H), 7.44 (d, 1H, J=8.0 Hz), 8.7.35-7.23 (m, 1H), 7.05 (d, 1H, J=8.3 Hz), 6.89 (s, 1H), 6.83 (d, 1H, J=8.4 Hz), 6.38-6.26 (m, 2H), 5.62-5.55 (m, 1H), 5.45-5.37 (m, 1H), 4.44-4.34 (m, 1H), 3.45 (s, 2H), 3.12-3.05 (m, 1H), 2.98-2.86 (m, 4H), 2.80-2.68 (m, 4H), 2.49 (d, 1H, J=8.1 Hz), 2.26 (d, 1H, J=9.4 Hz), 2.22 (s, 1H), 1.70-1.55 (m, 2H).

Example 324

5-Chloro-N*4*-(2-methoxy-4-morpholin-4-yl-phenyl)-N*2*-(3-prop-2-ynyl-2,3,4,5-tetrahydro-1H-benzo[d]azepin-7-yl)-pyrimidine-2,4-diamine 5-Chloro-N*4*-(2-methoxy-4-morpholin-4-yl-phenyl)-N*2*-(3-prop-2-ynyl-2,3,4,5-tetrahydro-1H-benzo[d]azepin-7-yl)-pyrimidine-2,4-diamine was prepared from 3-prop-2-ynyl-2,3,4,5-tetrahydro-1H-benzo[d]azepin-7-ylamine and (2,5-dichloro-pyrimidin-4-yl)-(2-methoxy-4-morpholin-4-yl-phenyl)-amine in an analogous manner to Example 322. Product isolated as a pale yellow solid (120 mg, 46%). m.p.=151-152° C.; LCMS (m/e) 519 (M+1); $^1$H-NMR (CDCl$_3$, 400 MHz) δ 8.27 (d, 1H, J=8.7 Hz), 8.02 (s, 1H), 7.61 (s, 1H), 7.48 (s, 1H), 7.23-7.16 (m, 1H), 7.04 (d, 1H, J=8.0 Hz), 6.89 (s, 1H), 6.56 (s, 1H), 6.55-6.49 (m, 1H), 3.94 (s, 3H), 3.91 (m, 4H), 3.45 (s, 2H), 3.21-3.15 (m, 4H), 2.98-2.89 (m, 4H), 2.82-2.70 (m, 4H), 2.25-2.21 (m, 1H).

Example 325

N-{(1R,2R)-2-[5-Chloro-2-(3-prop-2-ynyl-2,3,4,5-tetrahydro-1H-benzo[d]azepin-7-ylamino)-pyrimidin-4-ylamino]-cyclohexyl}-methanesulfonamide N-{(1R,2R)-2-[5-Chloro-2-(3-prop-2-ynyl-2,3,4,5-tetrahydro-1H-benzo[d]azepin-7-ylamino)-pyrimidin-4-ylamino]-cyclohexyl}-methanesulfonamide was prepared from 3-prop-2-ynyl-2,3,4,5-tetrahydro-1H-benzo[d]azepin-7-ylamine and N-[(1R,2R)-2-(2,5-dichloro-pyrimidin-4-ylamino)-cyclohexyl]-methanesulfonamide in an analogous manner to Example 322. Product isolated as a pale yellow solid (90 mg, 36%). m.p.=193-196° C.; LCMS (m/e) 503 (M+1); $^1$H-NMR (CDCl$_3$, 400 MHz) δ 7.94 (s, 1H), 7.35-7.25 (m, 1H), 7.08 (d, 1H, J=7.8 Hz), 6.82 (s, 1H), 5.40 (d, 1H, J=7.5 Hz), 5.38-5.32 (m, 1H), 3.94-3.83 (m, 1H), 3.45 (d, 2H, J=2.0 Hz), 3.31-3.20 (m, 1H), 3.00-2.90 (m, 4H), 2.80 (s, 3H), 2.83-2.71 (m, 4H), 2.28-2.18 (m, 3H), 1.89-1.79 (m, 2H), 1.45-1.33 (m, 4H).

Example 326

N-{2-[5-Chloro-2-(3-prop-2-ynyl-2,3,4,5-tetrahydro-1H-benzo[d]azepin-7-ylamino)-pyrimidin-4-ylamino]-phenyl}-methanesulfonamide N-{2-[5-Chloro-2-(3-prop-2-ynyl-2,3,4,5-tetrahydro-1H-benzo[d]azepin-7-ylamino)-pyrimidin-4-ylamino]-phenyl}-methanesulfonamide was prepared from 3-prop-2-ynyl-2,3,4,5-tetrahydro-1H-benzo[d]azepin-7-ylamine and N-[2-(2,5-dichloro-pyrimidin-4-ylamino)-phenyl]-methanesulfonamide in an analogous manner to Example 322. Product isolated as an orange foam (55 mg, 22%). LCMS (m/e) 497 (M+1); $^1$H-NMR (CDCl$_3$, 400 MHz) δ 8.03 (s, 1H), 7.72-7.67 (m, 1H), 7.54-7.48 (m, 2H), 7.38-7.30 (m, 2H), 7.18-7.15 (m, 1H), 7.09-7.04 (m, 1H), 7.03 (s, 1H), 6.6.97-6.91 (m, 1H), 3.45 (s, 2H), 2.93 (s, 3H), 2.91-2.85 (m, 2H), 2.80-2.65 (m, 6H), 2.24 (s, 1H).

Example 327

7-[5-Chloro-4-(2-methylcarbamoyl-phenylamino)-pyrimidin-2-ylamino]-1,2,4,5-tetrahydro-benzo[d]azepine-3-carboxylic acid dimethylamide 327a) 7-Nitro-2,3,4,5-tetrahydro-1H-benzo[d]azepine nitric acid salt (100 mg, 0.394 mmol) was dissolved CH$_2$Cl$_2$ and triethylamine (119 mg, 166 μL, 1.182 mmol, 3.0 eq) followed by carbamoyl chloride (46.4 mg, 39.7 μL, 0.433 mmol, 1.1 eq) were added. The reaction was stirred at room temperature for 4 hours and then concentrated under reduced pressure. Purification by silica gel chromatography using a gradient of 0-5% MeOH/CH$_2$Cl$_2$ as the eluting solvent to obtain 7-nitro-1,2,4,5-tetrahydro-benzo[d]azepin-3-carboxylic acid dimethylamide as a light orange oil (88 mg, 85%). LCMS (m/e) 264 (M+1); $^1$H-NMR (CDCl$_3$, 400 MHz) δ 8.01-7.95 (m, 2H), 7.26 (d, 1H, J=9.3 Hz), 3.45-3.39 (m, 4H), 3.11-3.04 (m, 4H), 2.84 (s, 3H), 2.83 (s, 3H).

327b) 7-Nitro-1,2,4,5-tetrahydro-benzo[d]azepin-3-carboxylic acid dimethylamide (82 mg, 0.312 mmol) was placed in methanol (5 mL) and 10% palladium on carbon (8.2 mg) was added. The reaction was hydrogenated at 40 psi for 1 hour. The mixture was then filtered through celite and concentrated under reduced pressure to obtain 7-amino-1,2,4,5-tetrahydro-benzo[d]azepin-3-carboxylic acid dimethylamide as a clear thin film (72 mg, 100%). LCMS (m/e) 234 (M+1); $^1$H-NMR (CDCl$_3$, 400 MHz) δ 6.91 (d, 1H, J=7.6 Hz), 6.58-6.49 (m, 2H), 3.75 (bs, 2H), 3.42-3.34 (m, 4H), 2.93-2.82 (m, 4H), 2.85 (s, 3H), 2.84 (s, 3H).

327c) 7-Amino-1,2,4,5-tetrahydro-benzo[d]azepin-3-carboxylic acid dimethylamide (80 mg, 0.343 mmol, 1.0 eq) and 2-(2,5-dichloro-pyrimidin-4-ylamino)-N-methyl-benzamide (112 mg, 0.378 mmol, 1.1 eq) were dissolved in IPA (3 mL). 4.0 M HCl in dioxane (94.5 μL, 0.378 mmol, 1.1 eq) was added and the reaction was heated at 120° C. in a microwave for 10 minutes. The reaction was then concentrated under reduced pressure and the residue was taken up in CH$_2$Cl$_2$ (20 mL) and washed with sat. NaHCO$_3$ (20 mL). The organic layer was dried (sodium sulfate), filtered, and concentrated under reduced pressure. Purification by basic alumina chromatography using a gradient of 0-10% MeOH/CH$_2$Cl$_2$ as the eluting solvent to obtain 7-[5-chloro-4-(2-methylcarbamoyl-phenylamino)-pyrimidin-2-ylamino]-1,2,4,5-tetrahydro-benzo[d]azepine-3-carboxylic acid dimethylamide as a yellow foam (137 mg, 81%). LCMS (m/e) 494 (M+1); $^1$H-NMR (CDCl$_3$, 400 MHz) δ 11.08 (s, 1H), 8.66 (d, 1H, J=8.4 Hz), 8.11 (s, 1H), 7.51 (d, 1H, J=7.8 Hz), 7.50-7.40 (m, 1H), 7.40 (s, 1H), 7.30-7.25 (m, 1H), 7.14-7.02 (m, 2H), 6.93 (s, 1H), 6.32-6.21 (m, 1H), 3.46-3.38 (m, 4H), 3.05 (d, 3H, J=4.8 Hz), 2.98-2.90 (m, 4H), 2.87 (s, 3H), 2.86 (s, 3H).

Example 328

2-{5-Chloro-2-[3-((S)-3,3,3-trifluoro-2-hydroxy-propyl)-2,3,4,5-tetrahydro-1H-benzo[d]azepin-7-ylamino]-pyrimidin-4-ylamino}-N-methyl-benzamide 328a) 7-Nitro-2,3,4,5-tetrahydro-1H-benzo[d]azepine nitric acid salt (2.01 g, 7.88 mmol, 1.0 eq), was placed in THF (100 mL) and MP-carbonate (7.1 g) was added. The reaction was stirred in a sealable vessel for 1 hour and then (S)-2-trifluoromethyl-oxirane (1.30 g, 11.59 mmol, 1.00 mL, 1.47 eq) was added. The reaction vessel was sealed, stirred at room temperature for 1 hour, and then heated at 50° C. overnight. The reaction was then cooled to room temperature and filtered. The resin was washed with CH$_2$Cl$_2$ (150 mL) and the filtrate was concentrated under reduced pressure. Purification by silica gel chromatography using a gradient of 0-50% EtOAc/hex as the eluting solvent to obtain (S)-1,1,1-trifluoro-3-(7-nitro-1,2,4,5-tetrahydro-benzo[d]azepin-3-yl)-propan-2-ol as an orange solid (2.27 g, 95%). m.p.=82-85° C.; LCMS (m/e) 305 (M+1); $^1$H-NMR (CDCl3, 400 MHz) δ 8.06-7.99 (m, 2H), 7.31-7.26 (m, 1H), 4.16-4.02 (m, 2H), 3.15-2.97 (m, 4H), 2.96-2.81 (m, 3H), 2.81-2.67 (m, 3H).

The R enantiomer was similarly produced.

328b) (S)-1,1,1-Trifluoro-3-(7-nitro-1,2,4,5-tetrahydro-benzo[d]azepin-3-yl)-propan-2-ol (582 mg, 1.91 mmol, 1.0 eq) was placed in methanol (20 mL) and 10% palladium on carbon (58 mg) was added. The reaction was hydrogenated at 25 psi for 30 minutes. The mixture was then filtered through celite and concentrated under reduced pressure to obtain (S)-3-(7-amino-1,2,4,5-tetrahydro-benzo[d]azepin-3-yl)-1,1,1-trifluoro-propan-2-ol as a green amorphous solid (525 mg, 100%). $^1$H-NMR (CDCl$_3$, 400 MHz) δ 6.90 (d, 1H, J=8.2 Hz), 6.53-6.39 (m, 2H), 4.49-4.35 (m, 1H), 4.12-3.93 (m, 1H), 3.63-3.47 (m, 2H), 2.96-2.75 (m, 6H), 2.75-2.60 (m, 4H).

The R enantiomer was similarly produced.

328c) (S)-3-(7-Amino-1,2,4,5-tetrahydro-benzo[d]azepin-3-yl)-1,1,1-trifluoro-propan-2-ol (96 mg, 0.350 mmol, 1.0 eq), 2-(2,5-dichloro-pyrimidin-4-ylamino)-N-methyl-benzamide (115 mg, 0.385 mmol, 1.1 eq), and 10-camphorsulfonic acid (89 mg, 0.385 mmol, 1.1 eq) were dissolved in IPA (3 mL) and heated at 120° C. in a microwave for 40 minutes. The reaction was then concentrated under reduced pressure and the residue was taken up in $CH_2Cl_2$ (20 mL) and washed with sat. $NaHCO_3$ (20 mL). The organic layer was dried (sodium sulfate), filtered, and concentrated under reduced pressure. Purification by amine capped silica gel chromatography using a gradient of 0-100% EtOAc/hex as the eluting solvent to obtain 2-{5-chloro-2-[3-((S)-3,3,3-trifluoro-2-hydroxy-propyl)-2,3,4,5-tetrahydro-1H-benzo[d]azepin-7-ylamino]-pyrimidin-4-ylamino}-N-methyl-benzamide as a pale yellow solid (101 mg, 54%). LCMS (m/e) 535 (M+1); $^1$H-NMR (CDCl$_3$, 400 MHz) δ 11.09 (s, 1H), 8.67 (d, 1H, J=8.4 Hz), 8.11 (s, 1H), 7.51 (d, 1H, J=7.8 Hz), 7.48-7.42 (m, 1H), 7.40 (s, 1H), 7.31-7.26 (m, 1H), 7.14-7.08 (m, 1H), 7.05 (d, 1H, J=8.0 Hz), 6.91 (s, 1H), 6.21 (bs, 1H), 4.42 (bs, 1H), 4.10-4.02 (m, 1H), 3.05 (d, 3H, J=4.6 Hz), 3.00-2.80 (m, 7H), 2.78-2.64 (m, 3H).

Example 329

N-((1R,2R)-2-{5-Chloro-2-[3-((S)-3,3,3-trifluoro-2-hydroxy-propyl)-2,3,4,5-tetrahydro-1H-benzo[d]azepin-7-ylamino]-pyrimidin-4-ylamino}-cyclohexyl)-methanesulfonamide N-((1R,2R)-2-{5-Chloro-2-[3-((S)-3,3,3-trifluoro-2-hydroxy-propyl)-2,3,4,5-tetrahydro-1H-benzo[d]azepin-7-ylamino]-pyrimidin-4-ylamino}-cyclohexyl)-methanesulfonamide was prepared from (S)-3-(7-amino-1,2,4,5-tetrahydro-benzo[d]azepin-3-yl)-1,1,1-trifluoro-propan-2-ol and N-[(1R,2R)-2-(2,5-dichloro-pyrimidin-4-ylamino)-cyclohexyl]-methanesulfonamide in an analogous manner to Example 328. Product isolated as a pale yellow foam (88 mg, 44%). LCMS (m/e) 577 (M+1); $^1$H-NMR (CDCl$_3$, 400 MHz) δ 7.95 (s, 1H), 7.37-7.25 (m, 1H), 7.07 (d, 1H, J=8.0 Hz), 6.82 (s, 1H), 5.41 (d, 1H, J=7.8 Hz), 5.38-5.30 (m, 1H), 4.48-4.32 (m, 1H), 4.13-4.02 (m, 1H), 3.93-3.82 (m, 1H), 3.30-3.19 (m, 1H), 3.03-2.79 (m, 7H), 2.81 (s, 3H), 2.78-2.65 (m, 3H), 2.30-2.19 (m, 2H), 1.91-1.80 (m, 2H), 1.47-1.32 (m, 4H).

Example 330

(S)-3-{7-[5-Chloro-4-(2-methoxy-4-morpholin-4-yl-phenylamino)-pyrimidin-2-ylamino]-1,2,4,5-tetrahydro-benzo[d]azepin-3-yl}-1,1,1-trifluoro-propan-2-ol (S)-3-{7-[5-Chloro-4-(2-methoxy-4-morpholin-4-yl-phenylamino)-pyrimidin-2-ylamino]-1,2,4,5-tetrahydro-benzo[d]azepin-3-yl}-1,1,1-trifluoro-propan-2-ol was prepared from (S)-3-(7-amino-1,2,4,5-tetrahydro-benzo[d]azepin-3-yl)-1,1,1-trifluoro-propan-2-ol and (2,5-dichloro-pyrimidin-4-yl)-(2-methoxy-4-morpholin-4-yl-phenyl)-amine in an analogous manner to Example 328. Product isolated as a white solid (179 mg, 86%). m.p.=170-172° C.; LCMS (m/e) 593 (M+1); $^1$H-NMR (CDCl$_3$, 400 MHz) δ 8.24 (d, 1H, J=8.7 Hz), 8.03 (s, 1H), 7.59 (s, 1H), 7.38 (s, 1H), 7.32-7.26 (m, 1H), 7.04 (d, 1H, J=8.1 Hz), 6.87 (s, 1H), 6.57 (s, 1H), 6.51 (d, 1H, J=8.7 Hz), 4.50-4.32 (m, 1H), 4.10-4.00 (m, 1H), 3.94 (s, 3H), 3.93-3.89 (m, 4H), 3.21-3.15 (m, 4H), 2.97-2.79 (m, 7H), 2.77-2.67 (m, 3H).

Example 331

(2-exo,3-exo)-3-{5-Chloro-2-[3-((S)-3,3,3-trifluoro-2-hydroxy-propyl)-2,3,4,5-tetrahydro-1H-benzo[d]azepin-7-ylamino]-pyrimidin-4-ylamino}-bicyclo[2.2.1]heptane-2-carboxylic acid amide (2-exo, 3-exo)-3-{5-Chloro-2-[3-((S)-3,3,3-trifluoro-2-hydroxy-propyl)-2,3,4,5-tetrahydro-1H-benzo[d]azepin-7-ylamino]-pyrimidin-4-ylamino}-bicyclo[2.2.1]heptane-2-carboxylic acid amide was prepared from (S)-3-(7-amino-1,2,4,5-tetrahydro-benzo[d]azepin-3-yl)-1,1,1-trifluoro-propan-2-ol and (2-exo, 3-exo)-3-(2,5-dichloro-pyrimidin-4-ylamino)-bicyclo[2.2.1]heptane-2-carboxylic acid amide in an analogous manner to Example 328. Product isolated as a mixture of diastereomers as a white solid (60 mg, 32%). LCMS (m/e) 539 (M+1); $^1$H-NMR (CDCl$_3$, 400 MHz) mixture of diasteromers δ 7.88 (s, 1H), 7.48 (d, 1H, J=7.8 Hz), 7.05 (d, 1H, J=8.1 Hz), 6.92-6.83 (m, 2H), 5.56-5.48 (m, 1H), 5.36-5.27 (m, 1H), 4.38 (t, 2H, J=8.4 Hz), 4.13-4.01 (m, 1H), 3.03-2.80 (m, 7H), 2.80-2.64 (m, 3H), 2.60-2.52 (m, 2H), 2.37-2.35 (m, 1H), 2.17-2.10 (m, 1H), 1.78-1.60 (m, 2H), 1.44-1.25 (m, 4H).

Example 332

2-{5-Chloro-2-[3-((R)-3,3,3-trifluoro-2-hydroxy-propyl)-2,3,4,5-tetrahydro-1H-benzo[d]azepin-7-ylamino]-pyrimidin-4-ylamino}-3-fluoro-N-methyl-benzamide 2-{5-Chloro-2-[3-((R)-3,3,3-trifluoro-2-hydroxy-propyl)-2,3,4,5-tetrahydro-1H-benzo[d]azepin-7-ylamino]-pyrimidin-4-ylamino}-3-fluoro-N-methyl-benzamide was prepared from (R)-3-(7-amino-1,2,4,5-tetrahydro-benzo[d]azepin-3-yl)-1,1,1-trifluoro-propan-2-ol and 2-(2,5-dichloro-pyrimidin-4-ylamino)-3-fluoro-N-methyl-benzamide in an analogous manner to Example 328. Product isolated as a white foam (36 mg, 24%). LCMS (m/e) 553 (M+1); $^1$H-NMR (CDCl$_3$, 400 MHz) δ 8.78 (s, 1H), 8.09 (s, 1H), 7.38-7.26 (m, 3H), 7.19 (s, 1H), 7.15 (d, 1H, J=8.1 Hz), 6.92 (d, 1H, J=8.1 Hz), 6.86 (s, 1H), 6.15-6.05 (m, 1H), 4.40 (bs, 1H), 4.12-4.00 (m, 1H), 2.94 (d, 3H, J=4.9 Hz), 2.91-2.60 (m, 10H).

Example 333

(R)-3-{7-[5-Chloro-4-(2-methoxy-4-morpholin-4-yl-phenylamino)-pyrimidin-2-ylamino]-1,2,4,5-tetrahydro-benzo[d]azepin-3-yl}-1,1,1-trifluoro-propan-2-ol (R)-3-{7-[5-Chloro-4-(2-methoxy-4-morpholin-4-yl-phenylamino)-pyrimidin-2-ylamino]-1,2,4,5-tetrahydro-benzo[d]azepin-3-yl}-1,1,1-trifluoro-propan-2-ol was prepared from (R)-3-(7-amino-1,2,4,5-tetrahydro-benzo[d]azepin-3-yl)-1,1,1-trifluoro-propan-2-ol and (2,5-dichloro-pyrimidin-4-yl)-(2-methoxy-4-morpholin-4-yl-phenyl)-amine in an analogous manner to Example 328. Product isolated as a white solid (85 mg, 52%). m.p.=174-175° C.; LCMS (m/e) 593 (M+1); $^1$H-NMR (CDCl$_3$, 400 MHz) δ 8.24 (d, 1H, J=8.7 Hz), 8.03 (s, 1H), 7.59 (s, 1H), 7.38 (s, 1H), 7.32-7.26 (m, 1H), 7.04 (d, 1H, J=8.1 Hz), 6.87 (s, 1H), 6.57 (s, 1H), 6.51 (d, 1H, J=8.7 Hz), 4.50-4.32 (m, 1H), 4.10-4.00 (m, 1H), 3.94 (s, 3H), 3.93-3.89 (m, 4H), 3.21-3.15 (m, 4H), 2.97-2.79 (m, 7H), 2.77-2.67 (m, 3H).

Example 334

(2-exo, 3-exo)-3-{5-Chloro-2-[3-((R)-3,3,3-trifluoro-2-hydroxy-propyl)-2,3,4,5-tetrahydro-1H-benzo[d]azepin-7-ylamino]-pyrimidin-4-ylamino}-bicyclo[2.2.1]hept-5-ene-2-carboxylic acid amide (2-exo, 3-exo)-3-{5-Chloro-2-[3-((R)-3,3,3-trifluoro-2-hydroxy-propyl)-2,3,4,5-tetrahydro-1H-benzo[d]azepin-7-ylamino]-pyrimidin-4-ylamino}-bicyclo[2.2.1]hept-5-ene-2-carboxylic acid amide was prepared from (R)-3-(7-amino-1,2,4,5-tetrahydro-benzo[d]azepin-3-yl)-1,1,1-trifluoro-propan-2-ol and (2-exo, 3-exo)-3-(2,5-dichloro-pyrimidin-4-ylamino)-bicyclo[2.2.1]hept-5-ene-2-carboxylic acid amide in an analogous manner to Example 328. Product isolated as a mixture of diastereomers as a white solid (70 mg, 48%). m.p.=224-225° C.; LCMS (m/e) 537 (M+1); $^1$H-NMR (CDCl$_3$, 400 MHz) mixture of diasteromers δ 7.90 (s, 1H), 7.50 (d, 1H, J=7.8 Hz), 7.35-7.25 (m, 1H), 7.05 (d, 1H, J=7.9 Hz), 6.94-6.86 (m, 1H), 6.85-6.79 (m, 1H), 6.34 (s, 2H), 5.60-5.53 (m, 1H), 5.36-5.29 (m, 1H), 4.38 (t, 2H, J=8.4 Hz), 4.13-4.01 (m, 1H), 3.12-3.08 (m, 1H), 3.01-2.80 (m, 8H), 2.78-2.65 (m, 3H), 2.49 (d, 1H, J=7.6 Hz), 2.26 (d, 1H, J=9.9 Hz), 1.68-1.63 (m, 1H).

Example 335

2-{5-Chloro-2-[3-((S)-3,3,3-trifluoro-2-methoxy-propyl)-2,3,4,5-tetrahydro-1H-benzo[d]azepin-7-ylamino]-pyrimidin-4-ylamino}-N-methyl-benzamide 335a) (S)-3-(7-Amino-1,2,4,5-tetrahydro-benzo[d]azepin-3-yl)-1,1,1-trifluoro-propan-2-ol (238 mg, 0.783 mmol, 1.0 eq), was dissolved in THF (10 mL) and a 60% dispersion of NaH (68.9 mg, 1.72 mmol, 2.2 eq) was added. The reaction was stirred for 5 minutes and then methyl iodide (243 mg, 1.72 mmol, 107 µL, 2.2 eq) was added. The reaction was stirred at room temperature for 48 hours and then quenched with water (25 mL). The product was extracted into CH$_2$Cl$_2$ (25 mL) and the organic layer was dried (sodium sulfate), filtered, and concentrated under reduced pressure. Purification by silica gel chromatography using a gradient of 0-60% EtOAc/hex as the eluting solvent to obtain 7-nitro-3-((S)-3,3,3-trifluoro-2-methoxy-propyl)-2,3,4,5-tetrahydro-1H-benzo[d]azepine as a yellow oil (171 mg, 69%). LCMS (m/e) 319 (M+1); $^1$H-NMR (CDCl3, 400 MHz) δ 8.03-7.97 (m, 2H), 7.25 (d, 1H, J=7.8 Hz), 3.75-3.65 (m, 1H), 3.61 (s, 3H), 3.08-3.01 (m, 4H), 2.86-2.76 (m, 6H).

The R enantiomer was similarly produced.

335b) 7-Nitro-3-((S)-3,3,3-trifluoro-2-methoxy-propyl)-2,3,4,5-tetrahydro-1H-benzo[d]azepine (171 mg, 0.538 mmol, 1.0 eq) was placed in methanol (20 mL) and 10% palladium on carbon (17 mg) was added. The reaction was hydrogenated at 25 psi for 30 minutes. The mixture was then filtered through celite and concentrated under reduced pressure to obtain 3-((S)-3,3,3-trifluoro-2-methoxy-propyl)-2,3,4,5-tetrahydro-1H-benzo[d]azepin-7-ylamine as a green amorphous solid (113 mg, 73%). LCMS (m/e) 289 (M+1); $^1$H-NMR (CDCl$_3$, 400 MHz) δ 6.89 (d, 1H, J=7.5 Hz), 6.51-6.45 (m, 2H), 3.76-3.66 (m, 1H), 3.61 (s, 3H), 3.63-3.52 (m, 2H), 2.88-2.79 (m, 6H), 2.78-2.69 (m, 4H).

The R enantiomer was similarly produced.

335c) 2-{5-Chloro-2-[3-((S)-3,3,3-trifluoro-2-methoxy-propyl)-2,3,4,5-tetrahydro-1H-benzo[d]azepin-7-ylamino]-pyrimidin-4-ylamino}-N-methyl-benzamide was prepared from 3-((S)-3,3,3-trifluoro-2-methoxy-propyl)-2,3,4,5-tetrahydro-1H-benzo[d]azepin-7-ylamine and 2-(2,5-dichloro-pyrimidin-4-ylamino)-N-methyl-benzamide in an analogous manner to Example 328c. Product isolated as a yellow solid (57 mg, 26%). m.p.=160-162° C.; LCMS (m/e) 549 (M+1); $^1$H-NMR (CDCl$_3$, 400 MHz) δ 11.08 (s, 1H), 8.68 (d, 1H, J=8.5 Hz), 8.11 (s, 1H), 7.50 (d, 1H, J=7.9 Hz), 7.48-7.42 (m, 1H), 7.36 (s, 1H), 7.30-7.25 (m, 1H), 7.13-7.07 (m, 1H), 7.04 (d, 1H, J=8.0 Hz), 3.76-3.67 (m, 1H), 3.62 (s, 3H), 3.06 (d, 3H, J=4.7 Hz), 2.94-2.86 (m, 4H), 2.86-2.82 (m, 2H), 2.79-2.73 (m, 4H).

Example 336

N-((1R,2R)-2-{5-Chloro-2-[3-((S)-3,3,3-trifluoro-2-methoxy-propyl)-2,3,4,5-tetrahydro-1H-benzo[d]azepin-7-ylamino]-pyrimidin-4-ylamino}-cyclohexyl)-methanesulfonamide N-((1R,2R)-2-{5-Chloro-2-[3-((S)-3,3,3-trifluoro-2-methoxy-propyl)-2,3,4,5-tetrahydro-1H-benzo[d]azepin-7-ylamino]-pyrimidin-4-ylamino}-cyclohexyl)-methanesulfonamide was prepared from 3-((S)-3,3,3-trifluoro-2-methoxy-propyl)-2,3,4,5-tetrahydro-1H-benzo[d]azepin-7-ylamine and N-[(1R,2R)-2-(2,5-dichloro-pyrimidin-4-ylamino)-cyclohexyl]-methanesulfonamide in an analogous manner to Example 335. Product isolated as a pale yellow solid (53 mg, 27%). m.p.=175-177° C.; LCMS (m/e) 591 (M+1); $^1$H-NMR (CDCl$_3$, 400 MHz) δ 7.94 (s, 1H), 7.33-7.25 (m, 2H), 7.06 (d, 1H, J=7.8 Hz), 6.86 (s, 1H), 5.46-5.36 (m, 2H), 3.94-3.82 (m, 1H), 3.77-3.66 (m, 1H), 3.62 (s, 3H), 3.30-3.20 (m, 1H), 2.96-2.88 (m, 4H), 2.87-2.72 (m, 6H), 2.80 (s, 3H), 2.28-2.17 (m, 2H), 1.90-1.78 (m, 2H), 1.45-1.37 (m, 4H).

Example 337

5-Chloro-N*4*-(2-methoxy-4-morpholin-4-yl-phenyl)-N*2*-[-((S)-3,3,3-trifluoro-2-methoxy-propyl)-2,3,4,5-tetrahydro-1H-benzo[d]azepin-7-yl]-pyrimidine-2,4-diamine 5-Chloro-N*4*-(2-methoxy-4-morpholin-4-yl-phenyl)-N*2*-[-((S)-3,3,3-trifluoro-2-methoxy-propyl)-2,3,4,5-tetrahydro-1H-benzo[d]azepin-7-yl]-pyrimidine-2,4-diamine was prepared from 3-((S)-3,3,3-trifluoro-2-methoxy-propyl)-2,3,4,5-tetrahydro-1H-benzo[d]azepin-7-ylamine and (2,5-dichloro-pyrimidin-4-yl)-(2-methoxy-4-morpholin-4-yl-phenyl)-amine in an analogous manner to Example 335. Product isolated as a pale yellow solid (96 mg, 46%). m.p.=146° C.; LCMS (m/e) 607 (M+1); $^1$H-NMR (CDCl$_3$, 400 MHz) δ 8.26 (d, 1H, J=8.7 Hz), 8.03 (s, 1H), 7.60 (s, 1H), 7.40 (s, 1H), 7.27-7.22 (m, 1H), 7.03 (d, 1H, J=8.1 Hz), 6.87 (s, 1H), 6.57 (s, 1H), 6.54-6.49 (m, 1H), 3.94 (s, 3H), 3.93-3.88 (m, 4H), 3.77-2.67 (m, 1H), 3.61 (s, 3H), 3.20-3.15 (m, 4H), 2.95-2.88 (m, 4H), 2.87-2.82 (m, 2H), 2.82-2.73 (m, 4H).

Example 338

(2-exo, 3-exo)-3-{5-Chloro-2-[3-((S)-3,3,3-trifluoro-2-methoxy-propyl)-2,3,4,5-tetrahydro-1H-benzo[d]azepin-7-ylamino]-pyrimidin-4-ylamino}-bicyclo[2.2.1]hept-5-ene-2-carboxylic acid amide (2-exo, 3-exo)-3-{5-Chloro-2-[3-((S)-3,3,3-trifluoro-2-methoxy-propyl)-2,3,4,5-tetrahydro-1H-benzo[d]azepin-7-ylamino]-pyrimidin-4-ylamino}-bicyclo[2.2.1]hept-5-ene-2-carboxylic acid amide was prepared from 3-((S)-3,3,3- trifluoro-2-methoxy-propyl)-2,3,4,5-tetrahydro-1H-benzo[d]azepin-7-ylamine and (2-exo,3-exo)-3-(2,5-dichloro-pyrimidin-4-ylamino)-bicyclo[2.2.1]hept-5-ene-2-carboxylic acid amide in an analogous manner to Example 335. Product isolated as a mixture of diastereomers as a white solid (44 mg, 24%). m.p.=209-211° C.; LCMS (m/e) 551 (M+1); $^1$H-NMR (CDCl$_3$, 400 MHz) δ 7.89 (s, 1H), 7.43 (d, 1H, J=8.0 Hz), 7.04 (d, 1H, J=8.1 Hz), 6.89-6.80 (m, 2H), 6.38-6.30 (m, 2H), 5.61-5.53 (m, 1H), 5.42-5.32 (m, 1H), 4.38 (t, 1H, J=8.1 Hz), 3.77-3.66 (m, 1H), 3.62 (s, 3H), 3.12-3.05 (m, 1H), 2.96-2.87 (m, 4H), 2.87-2.80 (m, 2H), 2.80-2.72 (m, 4H), 2.49 (d, 1H, J=8.2 Hz), 2.26 (d, 1H, J=9.6 Hz), 1.65 (d, 1H, J=9.1 Hz).

Example 339

2-[5-Chloro-2-(5,5-dimethyl-2-oxo-2,3,4,5-tetrahydro-1H-benzo[d]azepin-7-ylamino)-pyrimidin-4-ylamino]-N-ethyl-benzamide 7-Amino-5,5-dimethyl-1,3,4,5-tetrahydro-benzo[b]azepin-2-one (50 mg, 0.245 mmol, 1.0 eq), 2-(2,5-dichloro-pyrimidin-4-ylamino)-N-ethyl-benzamide (84 mg, 0.270 mmol, 1.1 eq), and 10-camphorsulfonic acid (63 mg, 0.270 mmol, 1.1 eq) were dissolved in IPA (3 mL) and heated at 120° C. in a microwave for 1 hour. The reaction was then concentrated under reduced pressure and the residue was taken up in CH$_2$Cl$_2$ (20 mL) and washed with sat. NaHCO$_3$ (20 mL). The organic layer was dried (sodium sulfate), filtered, and concentrated under reduced pressure. Purification by silica gel chromatography using a gradient of 0-100% EtOAc/hex as the eluting solvent to obtain 2-[5-chloro-2-(5,5-dimethyl-2-oxo-2,3,4,5-tetrahydro-1H-benzo[d]azepin-7-ylamino)-pyrimidin-4-ylamino]-N-ethyl-benzamide as a yellow solid (87 mg, 74%). m.p.=261-262° C.; LCMS (m/e) 479 (M+1); $^1$H-NMR (d$_6$-DMSO, 400 MHz) δ 11.55 (s, 1H), 9.40 (s, 1H), 9.36 (s, 1H), 8.82-8.69 (m, 2H), 8.21 (s, 1H), 7.76 (d, 1H, J=8.1 Hz), 7.66 (d, 1H, J=8.3 Hz), 7.55-7.51 (m, 1H), 7.50-7.42 (m, 1H), 7.19-7.10 (m, 1H), 6.88 (d, 1H, J=8.6 Hz), 3.35-3.26 (m, 2H), 2.22-2.14 (m, 2H), 2.00-1.94 (m, 2H), 1.29 (s, 6H), 1.15 (t, 3H, J=7.1 Hz).

Example 340

2-[5-Chloro-2-(5,5-dimethyl-2-oxo-2,3,4,5-tetrahydro-1H-benzo[d]azepin-7-ylamino)-pyrimidin-4-ylamino]-N-isopropyl-benzamide 2-[5-Chloro-2-(5,5-dimethyl-2-oxo-2,3,4,5-tetrahydro-1H-benzo[d]azepin-7-ylamino)-pyrimidin-4-ylamino]-N-isopropyl-benzamide was prepared from 7-amino-5,5-dimethyl-1,3,4,5-tetrahydro-benzo[b]azepin-2-one and 2-(2,5-dichloro-pyrimidin-4-ylamino)-N-isopropyl-benzamide in an analogous manner to Example 339. Product isolated as a yellow solid (103 mg, 85%). m.p.=277-278° C.; LCMS (m/e) 493 (M+1); $^1$H-NMR (d$_6$-DMSO, 400 MHz) δ 11.42 (s, 1H), 9.40 (s, 1H), 9.36 (s, 1H), 8.76-8.67 (m, 1H), 8.54 (d, 1H, J=7.6 Hz), 8.21 (s, 1H), 7.76 (d, 1H, J=7.8 Hz), 7.66 (d, 1H, J=8.6 Hz), 7.56-7.50 (m, 1H), 7.49-7.43 (m, 1H), 7.17-7.11 (m, 2H), 6.87 (d, 1H, J=8.3 Hz), 4.18-4.07 (m, 1H), 2.22-2.14 (m, 2H), 2.01-1.95 (m, 2H), 1.29 (s, 6H), 1.19 (s, 3H), 1.18 (s, 3H).

Example 341

2-[5-Chloro-2-(5,5-dimethyl-2-oxo-2,3,4,5-tetrahydro-1H-benzo[d]azepin-7-ylamino)-pyrimidin-4-ylamino]-N-cyclopropyl-benzamide 2-[5-Chloro-2-(5,5-dimethyl-2-oxo-2,3,4,5-tetrahydro-1H-benzo[d]azepin-7-ylamino)-pyrimidin-4-ylamino]-N-cyclopropyl-benzamide was prepared from 7-amino-5,5-dimethyl-1,3,4,5-tetrahydro-benzo[b]azepin-2-one and N-cyclopropyl-2-(2,5-dichloro-pyrimidin-4-ylamino)-benzamide in an analogous manner to Example 339. Product isolated as a yellow solid (83 mg, 69%). m.p.=251-253° C.; LCMS (m/e) 491 (M+1); $^1$H-NMR (d$_6$-DMSO, 400 MHz) δ 11.52 (s, 1H), 9.40 (s, 1H), 9.36 (s, 1H), 8.78-8.68 (m, 2H), 8.22 (s, 1H), 7.71 (d, 1H, J=7.9 Hz), 7.66 (d, 1H, J=8.6 Hz), 7.56-7.50 (m, 1H), 7.49-7.43 (m, 1H), 7.17-7.10 (m, 1H), 6.87 (d, 1H, J=8.3 Hz), 2.94-2.85 (m, 1H), 2.22-2.14 (m, 2H), 2.01-1.94 (m, 2H), 1.28 (s, 6H), 0.77-0.70 (m, 2H), 0.64-0.59 (m, 2H).

Example 342

2-{5-Chloro-2-[3-(2-methoxy-ethyl)-2,3,4,5-tetrahydro-1H-benzo[d]azepin-7-ylamino]-pyrimidin-4-ylamino}-N-isopropyl-benzamide 342a) Analagous to Example 38a, 2-amino-N-isopropyl-benzamide was prepared from isatoic anhydride and isopropyl amine in 71% yield. m.p.=142-143° C.; LCMS (m/e) 179 (M+1); $^1$H-NMR (DMSO-d$_6$, 400 MHz) δ 7.93 (m, 1H), 7.45 (d, 1H, J=7.8 Hz), 7.22 (m, 1H), 6.66 (d, 1H, J=8.2 Hz), 6.50 (m, 1H), 6.32 (s, 2H), 4.04 (m, 1H), 1.13 (d, 6H, J=6.6 Hz).

342b) Analagous to Example 308b, 2-(2,5-dichloro-pyrimidin-4-ylamino)-N-isopropyl-benzamide was prepared in 48% yield. m.p.=206-209° C.; LCMS (m/e) 325 (M+1); 1H-NMR (CDCl$_3$, 400 MHz) δ 11.60 (m, 1H), 8.70 (d, 1H, J=8.4 Hz), 8.21 (s, 1H), 7.55 (m, 2H), 7.14 (m, 1H), 6.01 (s, 1H), 4.34 (m, 1H), 1.29 (d, 6H, J=6.6 Hz).

342c) Analagous to Example 308c, 2-{5-chloro-2-[3-(2-methoxy-ethyl)-2,3,4,5-tetrahydro-1H-benzo[d]azepin-7-ylamino]-pyrimidin-4-ylamino}-N-isopropyl-benzamide was prepared in 25% yield. m.p.=186-189° C.; LCMS (m/e) 509 (M+1); $^1$H-NMR (CDCl$_3$, 400 MHz) δ 10.94 (s, 1H), 8.62 (m, 1H), 8.05 (s, 1H), 6.9-7.5 (m, 7H), 6.00 (s, 1H), 4.29 (m, 1H), 3.4-3.6 (m, 5H), 2.6-3.0 (m, 9H), 1.95 (m, 1H), 1.27 (d, 6H, J=5.1 Hz).

Example 343

2-{5-Chloro-2-[3-(2-methoxy-ethyl)-2,3,4,5-tetrahydro-1H-benzo[d]azepin-7-ylamino]-pyrimidin-4-ylamino}-N-ethyl-benzamide 343a) Analagous to Example 308a, 2-amino-N-ethyl-benzamide was prepared from isatoic anhydride and ethyl amine in 64% yield. m.p.=102-103° C.; LCMS (m/e) 187 (M+23); $^1$H-NMR (DMSO-d$_6$, 400 MHz) δ 8.17 (m, 1H), 7.45 (d, 1H, J=7.9 Hz), 7.12 (m, 1H), 6.67 (d, 1H, J=8.2 Hz), 6.50 (m, 1H), 6.37 (s, 2H), 3.24 (m, 2H), 11.10 (d, 3H, J=7.2 Hz).

343b) Analagous to Example 308b, 2-(2,5-dichloro-pyrimidin-4-ylamino)-N-ethyl-benzamide was prepared in 53% yield. m.p.=182-186° C.; LCMS (m/e) 311 (M+1); 1H-NMR (CDCl$_3$, 400 MHz) δ 11.66 (m, 1H), 8.71 (d, 1H, J=8.4 Hz), 8.21 (s, 1H), 7.55 (m, 2H), 7.14 (m, 1H), 6.20 (s, 1H), 3.54 (m, 2H), 1.29 (d, 3H, J=7.3 Hz).

343c) Analagous to Example 308c, 2-{5-chloro-2-[3-(2-methoxy-ethyl)-2,3,4,5-tetrahydro-1H-benzo[d]azepin-7-ylamino]-pyrimidin-4-ylamino}-N-ethyl-benzamide was prepared in 38% yield. m.p.=150-184° C.; LCMS (m/e) 495 (M+1); $^1$H-NMR (CDCl$_3$, 400 MHz) δ 11.10 (s, 1H), 8.59 (d, 1H, J=7.9 Hz), 8.10 (s, 1H), 7.4-7.6 (m, 4H), 7.08-7.24 (m, 2H), 6.92 (s, 1H), 6.16 (m, 1H), 3.7-4.0 (m, 5H), 3.54 (m, 2H), 3.36 (s, 3H), 3.27 (m, 2H), 2.7-3.0 (m, 5H), 1.28 (t, 3H, J=7.3 Hz).

Example 344

2-{5-Chloro-2-[3-(2-methoxy-ethyl)-2,3,4,5-tetrahydro-1H-benzo[d]azepin-7-ylamino]-pyrimidin-4-ylamino}-N-cyclopropyl-benzamide 344a) Analagous to Example 308a, 2-amino-N-cyclopropyl-benzamide was prepared from isatoic anhydride and cyclopropylamine in 84% yield. m.p.=154-156° C.; LCMS (m/e) 199 (M+23); $^1$H-NMR (DMSO-$d_6$, 400 MHz) δ 8.14 (s, 1H), 7.40 (d, 1H, J=7.9 Hz), 7.12 (m, 1H), 6.66 (d, 1H, J=8.2 Hz), 6.44 (m, 1H), 6.38 (s, 2H), 2.79 (m, 1H), 0.66 (m, 2H), 0.54 (m, 2H).

344b) Analagous to Example 308b, 2-(2,5-dichloro-pyrimidin-4-ylamino)-N-cyclopropyl-benzamide was prepared in 68% yield. m.p.=203-207° C.; LCMS (m/e) 323 (M+1); $^1$H-NMR (CDCl$_3$, 400 MHz) δ 11.63 (s, 1H), 8.71 (d, 1H, J=8.5 Hz), 8.23 (s, 1H), 7.56 (m, 1H), 7.44 (d, 1H, J=7.8 Hz), 7.13 (m, 1H), 6.32 (s, 1H), 2.92 (m, 1H), 0.92 (m, 2H), 0.65 (m, 2H).

344c) Analagous to Example 308c, 2-{5-chloro-2-[3-(2-methoxy-ethyl)-2,3,4,5-tetrahydro-1H-benzo[d]azepin-7-ylamino]-pyrimidin-4-ylamino}-N-cyclopropyl-benzamide was prepared in 35% yield. m.p.=165-180° C.; LCMS (m/e) 507 (M+1); $^1$H-NMR (CDCl3, 400 MHz) δ 11.03 (s, 1H), 8.59 (d, 1H, J=8.2 Hz), 8.10 (s, 1H), 7.4-7.6 (m, 3H), 7.02-7.14 (m, 3H), 6.91 (s, 1H), 6.29 (s, 1H), 3.7-4.0 (m, 4H), 3.36 (s, 3H), 2.7-3.3 (m, 9H), 0.92 (m, 2H), 0.65 (m, 2H).

Example 345

N-((1R,2R)-2-{5-Chloro-2-[(1R,8S)-10-(2,2,2-trifluoro-acetyl)-10-aza-tricyclo[6.3.2.0*2,7*]trideca-2,4,6-trien-4-ylamino]-pyrimidin-4-ylamino}-cyclohexyl)-methanesulfonamide and N-((1R,2R)-2-{5-Chloro-2-[(1S,8R)-10-(2,2,2-trifluoro-acetyl)-10-aza-tricyclo[6.3.2.0*2,7*]trideca-2,4,6-trien-4-ylamino]-pyrimidin-4-ylamino}-cyclohexyl)-methanesulfonamide 345a) The products from Example 292, a mixture of diastereomers, were separated by chiral Supercritical Fluid CO$_2$ chromatography (20% MeOH, Chiralcel OD-H, Flow: 4 mL/Min, Pressure 100 psi) to obtain N-((1R,2R)-2-{5-chloro-2-[(1R,8S)-10-(2,2,2-trifluoro-acetyl)-10-aza-tricyclo[6.3.2.0*2,7*]trideca-2,4,6-trien-4-ylamino]-pyrimidin-4-ylamino}-cyclohexyl)-methanesulfonamide and N-((1R,2R)-2-{5-chloro-2-[(1S,8R)-10-(2,2,2-trifluoro-acetyl)-10-aza-tricyclo[6.3.2.0*2,7*]trideca-2,4,6-trien-4-ylamino]-pyrimidin-4-ylamino}-cyclohexyl)-methanesulfonamide. LCMS (m/e) 587 (M+1) for both diastereomers.

Example 351

7-[4-(2-Acetyl-phenylamino)-5-chloro-pyrimidin-2-ylamino]-1-methyl-1,3,4,5-tetrahydro-benzo[b]azepin-2-one 351a) 1-(2-Amino-phenyl)-ethanone hydrochloride (1.72 g, 1.0 mmol) and NaHCO$_3$ (3.4 g, 4 mmol) were slurried in a mixture of THF (4 mL) and EtOH (16 mL) prior to adding 2,4,5-trichloropyrimidine (1.84 g, 1.0 mmol). The reaction was stirred for 4 days, filtered and washed with water (10×10 mL) to afford -[2-(2,5-dichloro-pyrimidin-4-ylamino)-phenyl]-ethanone as a white solid that was used without further purification in the subsequent step.

351b) 1-[2-(2,5-Dichloro-pyrimidin-4-ylamino)-phenyl]-ethanone (37.0 mg, 0.132 mmol) and 7-amino-1-methyl-1,3,4,5-tetrahydro-benzo[b]azepin-2-one (27.7 mg, 0.146 mmol) were slurried in iPrOH (1.5 mL) prior to adding ~0.2 mL of 4N HCl in dioxane. This mixture was heated in a microwave reactor (sealed vessel) at 120° C. for 40 min. After quenching with saturated aqueous NaHCO$_3$ solution (2 mL), the resulting precipitate was collected by filtration, successively washed with iPrOH (2×2 mL) water (4×2 mL) and iPrOH (2×2 mL) to afford product (44.7 mg, 78%) as a white powder that had the following properties: m.p.=215-217° C.; LC/MS (ESI+): 436 (M+H); $^1$H-NMR (DMSO-$d_6$, 400 MHz): δ 11.79 (s, 1H), 9.60 (s, 1H), 8.90 (m, 1H), 8.30 (s, 1H), 8.13 (d, 1H, J=8.1), 7.65-7.59 (m, 2H), 7.57 (s, 1H), 7.25-7.20 (m, 2H), 3.22 (s, 3H), 2.70 (s, 3H), 2.58 (m, 2H), 2.16 (m, 2H), 2.04 (m, 2H).

Example 352

3-Chloro-2-[5-chloro-2-(1-methyl-2-oxo-2,3,4,5-tetrahydro-1H-benzo[b]azepin-7-ylamino)-pyrimidin-4-ylamino]-N-methyl-benzamide 3-Chloro-2-(2,5-dichloro-pyrimidin-4-ylamino)-N-methyl-benzamide (36.0 mg, 0.109 mmol) and 7-amino-1-methyl-1,3,4,5-tetrahydro-benzo[b]azepin-2-one (22.8 mg, 0.120 mmol) were slurried in iPrOH (1.5 mL) prior to adding ~0.2 mL of 4N HCl in dioxane. This mixture was heated in a microwave reactor (sealed vessel) at 120° C. for 40 min. The mixture was extracted into DCM, washed with saturated aqueous NaHCO$_3$ solution and the organic layer was dried by passing through a plug of Na$_2$SO$_4$. The resulting filtrate was evaporated and the residue purified by chromatography (silica gel, DCM/5% NH$_4$OH-MeOH gradient). The appropriate fractions were combined and evaporated to afford a solid that was triturated with ether (2×2 mL) and yielded product (37.1 mg, 70%) as a yellow foam that had the following properties: m.p.=145-160° C.; LC/MS (ESI+): 485 (M+H); $^1$H-NMR (CDCl$_3$, 400 MHz): δ 8.11 (s, 1H), 8.01 (s, 1H), 7.61 (d, 1H, J=8.1), 7.53 (d, 1H, J=8.1), 7.35-7.20 (m, 3H), 6.95 (m, 2H), 6.10 (br s, 1H), 3.38 (s, 3H), 2.83 (d, 3H, J=5.0), 2.55 (m, 2H), 2.24 (m, 2H), 2.09 (m, 2H).

Example 353 trans-2-[5-Chloro-2-(1-methyl-2-oxo-2,3,4,5-tetrahydro-1H-benzo[b]azepin-7-ylamino)-pyrimidin-4-ylamino]-cyclohexanecarboxylic acid amide 353a) trans-(2-Carbamoyl-cyclohexyl)-carbamic acid tert-butyl ester (246.5 mg, 1.02 mmol, J. Molec. Cat. B: Enzymatic, 2004, 29, 115-121) was dissolved in DCM and treated with TFA (5 mL). After 2 h, solvent was removed by rotary evaporation and the residue was repeated evaporated from CHCl$_3$ to remove any trace of TFA. To this residue was sequentially added MeOH (3 mL), water (1.5 mL), NaHCO$_3$ (171.2 mg, 2.04 mmol) and 2,4,5-trichloropyrimidine (224 mg, 1.22 mmol). After stirring for 40 h, addition of water (3 mL) gave a precipitate that was removed by filtration and washed with water (5×2 mL) and ether (2×2 mL) to afford 2-(2,5-dichloro-pyrimidin-4-ylamino)-trans-cyclohexanecarboxylic acid amide as a white solid that was used without further purification in the subsequent step.

353b) 2-(2,5-Dichloro-pyrimidin-4-ylamino)-trans-cyclohexanecarboxylic acid amide (50.1 mg, 0.173 mmol) and 7-amino-1-methyl-1,3,4,5-tetrahydro-benzo[b]azepin-2-one (35.9 mg, 0.190 mmol) were slurried in iPrOH (2.0 mL) prior to adding ~0.2 mL of 4N HCl in dioxane. This mixture was heated in a microwave reactor (sealed vessel) at 120° C. for 50 min. After quenching with saturated aqueous NaHCO$_3$ solution (2 mL), the resulting precipitate was collected by filtration, successively washed with iPrOH (1×1 mL), water (4×2 mL) and ether (2×2 mL) to afford product (63 mg, 82%) as a white powder that had the following properties: m.p.=280-283° C.; LC/MS (ESI+): 443 (M+H); $^1$H-NMR (DMSO-d$_6$, 400 MHz): δ 9.25 (s, 1H), 7.92 (s, 1H), 7.77 (s, 1H), 7.55 (d, 1H, J=8.6), 7.17 (d, 1H, J=8.3), 7.06 (s, 1H), 6.77 (s, 1H), 6.56 (d, 1H, J=8.6), 4.17 (m, 1H), 3.19 (s, 3H), 2.65 (m, 2H), 2.41 (m, 1H), 2.16 (m, 2H), 2.04 (m, 3H), 1.90-1.65 (m, 3H), 1.45 (m, 1H), 1.40-1.15 (m, 3H).

Example 354

2-[5-Chloro-2-(1-methyl-2-oxo-2,3,4,5-tetrahydro-1H-benzo[b]azepin-7-ylamino)-pyrimidin-4-ylamino]-5-piperidin-1-yl-benzamide 354a) To a solution of 2-amino-5-piperidin-1-yl-benzamide (1.05 g, 4.6 mmol, Heterocyclic Comm. 2001, 7, 473-480) in THF (10 mL) was added K$_2$CO$_3$ (0.76 g, 5.5 mmol) and 2,4,5-trichloropyrimidine (0.84 g, 4.6 mmol). After stirring for 72 h, addition of water (5 mL) gave a precipitate that was removed by filtration and washed with water (5×3 mL) and ether (3×2 mL) to afford 2-(2,5-dichloro-pyrimidin-4-ylamino)-5-piperidin-1-yl-benzamide as a yellow solid (0.99 g) that was used without further purification in the subsequent step.

354b) 2-(2,5-dichloro-pyrimidin-4-ylamino)-5-piperidin-1-yl-benzamide (50.1 mg, 0.137 mmol) and 7-amino-1-methyl-1,3,4,5-tetrahydro-benzo[b]azepin-2-one (28.7 mg, 0.151 mmol) were slurried in methoxyethanol (2.0 mL) prior to adding ~0.2 mL of 4N HCl in dioxane. This mixture was heated at 120° C. for 2 h. After quenching with saturated aqueous NaHCO$_3$ solution (2 mL), the resulting precipitate was collected by filtration, successively washed water (5×2 mL) and ether (2×1 mL) to afford product (15 mg, 21%) as a yellow powder that had the following properties: mp: 295-297° C.; LC/MS (ESI+): 520 (M+H); $^1$H-NMR (DMSO-d$_6$, 400 MHz): δ 11.20 (s, 1H), 9.45 (s, 1H), 8.42 (d, J=8.0, 1H), 8.28 (s, 1H), 8.15 (s, 1H), 7.65 (m, 2H), 7.52 (d, J=8.9, 1H), 7.30 (s, 1H), 7.20 (d, J=8.6, 1H), 7.05 (d, J=9.4, 1H), 3.20 (s, 3H), 3.18 (m, 4H), 2.65-2.20 (series of m, 6H), 1.65 (m, 4H), 1.55 (m, 2H).

Example 355

2-[5-Chloro-2-(1-methyl-2-oxo-2,3,4,5-tetrahydro-1H-benzo[b]azepin-7-ylamino)pyrimidin-4-ylamino]-5-morpholin-4-yl-benzamide 355a) A mixture of 2-amino-5-morpholin-4-yl-benzamide (820.0 mg, 3.71 mmol, Heterocyclic Comm. 2001, 7, 473-480), 2,4,5-trichloropyrimidine (679.8 mg, 3.71 mmol) and potassium carbonate (614.6 mg, 4.45 mol) in THF (10 mL) was stirred at 50° C. for 20 h and at RT for 6 days. The reaction was diluted with water (10 mL) and extracted into EtOAc. The organic layer was washed with NaHCO$_3$, brine and dried by passing through a funnel filled with MgSO$_4$. The filtrate was evaporated and the residue triturated with ether (5×3 mL) to afford 2-(2,5-dichloro-pyrimidin-4-ylamino)-5-morpholin-4-yl-benzamide as a yellow solid (0.75 g) that was used without further purification in the subsequent step.

355b) A microwave vessel was charged with 2-(2,5-dichloro-pyrimidin-4-ylamino)-5-morpholin-4-yl-benzamide (50.0 mg, 0.136 mmol), 7-amino-1-methyl-1,3,4,5-tetrahydro-1-benzazepin-2-one (31.6 mg, 0.166 mmol), 10-camphorsulfonic acid (3.5 mg, 0.015 mmol) and isopropyl alcohol (2 mL). This mixture was heated at 120° C. for 20 minutes in a microwave reactor (sealed vessel). After quenching with saturated aqueous NaHCO$_3$ solution (2 mL), the resulting precipitate was collected by filtration, successively washed water (5×2 mL) and ether (2×1 mL) to afford product as a yellow powder (49.5 mg, 70%) that had the following properties: mp: 288-290° C.; LC/MS (ESI+): 522 (M+H); $^1$H-NMR (DMSO-d$_6$, 400 MHz): δ 11.29 (s, 1H), 9.45 (s, 1H), 8.46 (d, J=8.0, 1H), 8.28 (s, 1H), 8.16 (s, 1H), 7.69 (s, 1H), 7.64 (s, 1H), 7.52 (d, J=8.9, 1H), 7.32 (s, 1H), 7.20 (d, J=8.6, 1H), 7.09 (d, J=9.4, 1H), 3.77 (m, 4H), 3.25 (s, 3H), 3.15 (m, 4H), 2.60 (m, 2H), 2.20-2.10 (m, 2H), 2.10-2.00 (m, 2H).

Example 356

2-{5-Chloro-2-[1-(2-methoxy-ethyl)-2-oxo-2,3,4,5-tetrahydro-1H-benzo[b]azepin-7-ylamino]-pyrimidin-4-ylamino}-3-fluoro-N-methyl-benzamide 356a) To a solution of 7-nitro-1,3,4,5-tetrahydro-benzo[b]azepin-2-one solid (566.6 mg, 2.75 mmol) in DMF (5 mL) was added NaH (200 mg, 60% dispersion in mineral oil, 5.0 mmol). After stirring for 15 min, 1-bromo-3-methoxy-propane (764 mg, 5.5 mmol) was added and the mixture stirred at room temperature for 1 hour prior to quenching with 10% aqueous NH$_4$Cl solution. Solvent was removed by rotary evaporation and the residue extracted into EtOAc, washed with water (2×), brine and dried by passing through a plug of MgSO$_4$. The resulting filtrate was evaporated onto Florisil and purified by chromatography (silica gel, DCM→15% EtOAc/DCM gradient). The appropriate fractions were combined and evaporated to afford 1-(2-methoxy-ethyl)-7-nitro-1,3,4,5-tetrahydro-benzo[b]azepin-2-one as an oil that was carried onto the next step.

356b) To a solution of the above 1-(2-methoxy-ethyl)-7-nitro-1,3,4,5-tetrahydro-benzo[b]azepin-2-one in EtOH (10 mL) was sequentially added 10% Pd/C (120 mg) and hydrazine-monohydrate (1 mL). The solution was warmed to reflux for 2.5 h, cooled, filtered through celite, and repeatedly evaporated from toluene to remove residual hydrazine. The residue was recrystallized from EtOAc/heptane to afford transparent prisms of 7-amino-1-(2-methoxy-ethyl)-1,3,4,5-tetrahydro-benzo[b]azepin-2-one (345 mg, 54%) that had the following properties: mp: 134-135° C.; LC/MS (ESI+): 235 (M+H); $^1$H-NMR (CDCl$_3$, 400 MHz): δ 7.08 (d, J=8.4, 1H), 6.60 (d, J=8.4, 1H), 6.51 (s, 1H), 4.20 (br s, 1H), 3.65 (m, 2H), 3.53 (m, 2H), 3.28 (s, 3H), 2.60 (br s, 1H), 2.27 (m, 2H), 1.58 (m, 3H).

356c) A microwave vessel was charged with 2-(2,5-dichloro-pyrimidin-4-ylamino)-3-fluoro-N-methyl-benzamide (50.0 mg, 0.159 mmol), 7-amino-1-(2-methoxy-ethyl)-1,3,4,5-tetrahydro-1-benzazepin-2-one (45 mg, 0.19 mmol), 10-camphorsulfonic acid (5.0 mg, 0.022 mmol) and isopropyl alcohol (2 mL) and heated at 120° C. for 30 minutes in a microwave reactor (sealed vessel). The reaction was diluted with water (10 mL) and extracted into EtOAc. The organic layer was washed with NaHCO$_3$ and dried by passing through a funnel filled with MgSO$_4$. The filtrate was evaporated and the residue purified by chromatography (silica gel, 5% NH$_4$OH in MeOH gradient with DCM). The appropriate fractions were combined and evaporated to afford a solid that was triturated with ether (2×2 mL) and yielded product (39.0 mg, 48%) as a white powder that had the following properties:

m.p.=146-147° C., bubbled, remelt at 184-187° C.; LC/MS (ESI+): 513 (M+H); $^1$H-NMR (CDCl$_3$, 400 MHz): δ 8.90 (s, 1H), 8.10 (s, 1H), 7.4-7.2 (m, 5H), 7.10 (d, J=8.5, 1H), 7.0 (s, 1H), 6.2, (s, 1H), 3.7-4.2 (m, 2H), 3.55-3.47 (m, 2H), 3.30 (s, 3H), 2.95 (d, J=4.9, 3H), 2.9-2.4 (m, 2H), 2.3-2.2 (m, 2H), 1.8-2.3 (m, 2H).

Example 357

3-Chloro-2-{5-chloro-2-[1-(2-methoxy-ethyl)-2-oxo-2,3,4,5-tetrahydro-1H-benzo[b]azepin-7-ylamino]-pyrimidin-4-ylamino}-N-methyl-benzamide A microwave vessel was charged with 3-chloro-2-(2,5-dichloro-pyrimidin-4-ylamino)-N-methyl-benzamide (50.00 mg, 0.1508 mmol), 7-amino-1-(2-methoxy-ethyl)-1,3,4,5-tetrahydro-1-benzazepin-2-one (39 mg, 0.16 mmol), 10-camphorsulfonic acid (6.0 mg, 0.026 mmol) and isopropyl alcohol (2 mL) and heated to at 120° C. for 70 minutes in a microwave reactor (sealed vessel). The reaction was diluted with water (10 mL) and saturated aqueous solution of NaHCO$_3$ before extracting into DCM. The organic layer was dried by passing through a filter funnel loaded with MgSO$_4$; the filtrate was evaporated onto celite prior to purification by chromatography (amine modified silica gel, 30% EtOAc/Hexane→80% EtOAc gradient). The appropriate fractions were combined, evaporated to afford a solid that was triturated with ether (2×2 mL) and yielded product (23.9 mg, 30%) as a white foam that had the following properties: m.p.=136-157° C., bubbled; LC/MS (ESI+): 529 (M+H); $^1$H-NMR (CDCl$_3$, 400 MHz): δ 8.12 (s, 1H), 8.03 (s, 1H), 7.62 (d, J=8.0, 1H), 7.52 (d, J=8.0, 1H), 7.31 (dd, J=8.0, 7.8, 1H), 7.27 (m, 1H), 7.220 (d, J=8.6, 1H), 7.09 (d, J=8.6, 1H), 6.98 (s, 1H), 6.10, (s, 1H), 3.7-4.2 (m, 2H), 3.55-3.47 (m, 2H), 3.30 (s, 3H), 2.95 (d, J=4.9, 3H), 2.9-2.4 (m, 2H), 2.3-2.2 (m, 2H), 1.8-2.3 (m, 2H).

Example 358

2-[5-Chloro-2-(1-ethyl-2-oxo-2,3,4,5-tetrahydro-1H-benzo[b]azepin-8-ylamino)pyrimidin-4-ylamino]-3-fluoro-N-methyl-benzamide 358a) To a solution of 1-ethyl-8-nitro-1,3,4,5-tetrahydro-benzo[b]azepin-2-one (920 mg, 3.9 mmol, WO2002100327A2) in EtOH (13 mL) was sequentially added 10% Pd/C (155 mg) and hydrazine-monohydrate (3 mL). The solution was warmed to reflux for 2.5 h, cooled, filtered through celite, and repeatedly evaporated from toluene to remove residual hydrazine to afford 8-amino-1-ethyl-1,3,4,5-tetrahydro-benzo[b]azepin-2-one (805 mg, 100%) that had the following properties: LC/MS (ESI+): 205 (M+H); $^1$H-NMR (CDCl$_3$, 400 MHz): δ 6.97 (d, J=7.8, 1H), 6.55 (s, 1H), 6.52 (d, J=7.8, 1H), 3.95 (br s, 2H), 3.67 (br s, 2H), 2.60 (br s, 2H), 2.29 (m, 2H), 2.11 (m, 2H), 1.15 (t, J=6.2, 3H).

358b) A microwave vessel was charged with 2-(2,5-dichloro-pyrimidin-4-ylamino)-3-fluoro-N-methyl-benzamide (57.5 mg, 0.182 mmol), 8-amino-1-ethyl-1,3,4,5-tetrahydro-1-benzazepin-2-one (44.7 mg, 0.219 mmol), 10-camphorsulfonic acid (5.0 mg, 0.022 mmol) and isopropyl alcohol (2 mL) and heated at 120° C. for 60 minutes in a microwave reactor (sealed vessel). The reaction mixture was quenched with a slurry of saturated, aqueous NaHCO$_3$ and stirred for 2 h. The resulting precipitate was filtered, washed with water (5×2 mL), ether (2×2 mL) and dried under vacuum to afford product 65.7 mg, 69%) as a tan solid that had the following properties: mp: 228-235° C.; LC/MS (ESI+): 483 (M+H); $^1$H-NMR (DMSO-d$_6$, 400 MHz): δ 9.38-9.35 (m, 2H), 8.53 (m, 1H), 8.19 (s, 1H), 7.48-7.45 (m, 2H), 7.36-7.26 (m, 3H), 6.98 (d, J=8.3, 1H), 3.55 (br s, 2H), 2.74 (d, J=4.1, 3H), 2.50 (m, 2H), 2.10-1.85 (m, 4H), 0.93 (t, J=7.0, 3H).

Example 359

2-[5-Bromo-2-(1-ethyl-2-oxo-2,3,4,5-tetrahydro-1H-benzo[b]azepin-8-ylamino)-pyrimidin-4-ylamino]-3-fluoro-N-methyl-benzamide 359a) A solution of 2-amino-3-fluoro-N-methyl-benzamide (625 mg, 3.72 mmol), 5-bromo-2,4-dichloro-pyrimidine (1025 mg, 4.498 mmol), and N,N-diisopropylethylamine (1250 uL, 7.18 mmol) in N-methylpyrrolidinone (10.0 mL) was heated at 100° C. overnight. Solvent was removed by rotary evaporation and the residue was triturated with DCM to afford 2-(5-bromo-2-chloro-pyrimidin-4-ylamino)-3-fluoro-N-methyl-benzamide as a yellow solid (381 mg, 28%) that had the following properties: $^1$H-NMR (DMSO-d$_6$, 400 MHz): δ 9.74 (s, 1H), 8.61 (m, 1H), 8.51 (s, 1H), 7.51-7.44 (m, 3H), 2.73 (d, J=4.4, 3H).

59b) A microwave vessel was charged with 8-amino-1-ethyl-1,3,4,5-tetrahydro-1-benzazepin-2-one (44.7 mg, 0.219 mmol), 2-(5-bromo-2-chloro-pyrimidin-4-ylamino)-3-fluoro-N-methyl-benzamide (65.6 mg, 0.182 mmol) 10-camphorsulfonic acid (4.2 mg, 0.018 mmol) and isopropyl alcohol (2.0 mL) and heated in a microwave at 120° C. for 60 minutes. The reaction mixture was quenched with a slurry of saturated, aqueous, NaHCO$_3$ and stirred for 2 h. This mixture was diluted with water (10 mL) and extracted into DCM. The organic layer was dried by passing through a funnel filled with Na$_2$SO$_4$, and the filtrate was evaporated onto celite prior to purification by chromatography (amine modified silica gel, 25% EtOAc/hexane→80% EtOAc gradient). The appropriate fractions were combined, evaporated to afford a solid that was triturated with ether (2×2 mL) and yielded product (47 mg, 46%) as a pale yellow powder that had the following properties: m.p: 231-232° C.; LC/MS (ESI+): 528/530 (M+H); $^1$H-NMR (DMSO-d$_6$, 400 MHz): δ 9.40 (s, 1H), 9.33 (s, 1H), 8.63 (m, 1H), 8.27 (s, 1H), 7.47 (d, J=7.0, 1H), 7.44 (s, 1H), 7.35-7.20 (m, 3H), 6.98 (d, J=8.2, 1H), 3.65 (br s, 2H), 2.75 (d, J=5.1, 3H), 2.50 (m, 2H), 2.10-1.85 (m, 4H), 0.93 (t, J=7.0, 3H).

Example 360

2-[5-Chloro-2-(1-ethyl-2-oxo-2,3,4,5-tetrahydro-1H-benzo[b]azepin-8-ylamino)-pyrimidin-4-ylamino]-3, N-dimethyl-benzamide A microwave vessel was charged with 8-amino-1-ethyl-1,3,4,5-tetrahydro-1-benzazepin-2-one (44.7 mg, 0.219 mmol), 2-(2,5-Dichloro-pyrimidin-4-ylamino)-3,N-dimethyl-benzamide (56.8 mg, 0.182 mmol) 10-camphorsulfonic acid (4.2 mg, 0.018 mmol) and isopropyl alcohol (2.0 mL) and heated in a microwave at 120° C. for 60 minutes. The reaction mixture was quenched with a slurry of saturated, aqueous, NaHCO$_3$ and stirred for 2 h. This mixture was diluted with water (10 mL) and extracted into DCM. The organic layer was dried by passing through a funnel filled with Na$_2$SO$_4$, and the filtrate was evaporated onto celite prior to purification by chromatography (amine modified silica gel, 25% EtOAc/hexane→80% EtOAc gradient). The appropriate fractions were combined, evaporated to afford a solid that was triturated with ether (2×2 mL) and yielded product (49.5 mg, 57%) as a white powder that had the following properties: m.p: 210-212° C.; LC/MS (ESI+): 479 (M+H); $^1$H-NMR (DMSO-d$_6$, 400 MHz): δ 9.29-9.20 (m, 2H), 8.30 (m, 1H), 8.14 (s, 1H), 7.48-7.40 (m, 2H), 7.36 (d, J=8.3, 1H), 7.29-7.20 (m, 2H), 6.93 (d, J=8.3, 1H), 3.55 (br s, 2H), 2.70 (d, J=4.1, 3H), 2.50 (m, 2H), 2.15 (s, 3H), 2.10-1.85 (m, 4H), 0.92 (t, J=7.0, 3H).

Example 361

2-{5-Chloro-2-[1-(2-methoxy-ethyl)-2-oxo-2,3,4,5-tetrahydro-1H-benzo[b]azepin-8-ylamino]-pyrimidin-4-ylamino}-3,N-dimethyl-benzamide 361a) To a mixture of 8-nitro-1,3,4,5-tetrahydro-1-benzazepin-2-one (1.000 g, 4.850 mmol) and cesium carbonate (3.160 g, 9.699 mmol) in N,N-dimethylformamide (20 mL) was added, 1-bromo-2-methoxyethane (0.9 mL, 9.7 mol). The reaction was heated to at 50° C. O/N. The reaction mixture was filtered and the filtrate evaporated to afford a residue that was extracted into DCM and washed with water, brine and dried by passing through a funnel filled with MgSO$_4$. The filtrate was evaporated and the residue purified by chromatography (silica gel eluted with 3:1 EtOAc:hexane) to provide 1-(2-methoxy-ethyl)-8-nitro-1,3,4,5-tetrahydro-benzo[b]azepin-2-one (1.004 g, 78%) as pale yellow crystals that had the following properties: $^1$H-NMR (CDCl$_3$, 400 MHz) δ 8.33 (s, 1H), 8.05 (d, J=8.3, 1H), 7.38 (d, J=8.3, 1H), 4.05 (br s, 2H), 3.62 (m, 2H), 3.32 (s, 3H). 2.86 (br s, 2H), 2.35 2.10 (m, 4H).

361b) To a solution of 1-(2-methoxy-ethyl)-8-nitro-1,3,4,5-tetrahydro-1-benzazepin-2-one (1.00 g, 3.9 mmol) in EtOH (13 mL) was sequentially added 10% Pd/C (155 mg) and hydrazine-monohydrate (3 mL). The solution was warmed to reflux for 2.5 h, cooled, filtered through celite, and repeatedly evaporated from toluene to remove residual hydrazine to afford 8-amino-1-ethyl-1,3,4,5-tetrahydro-benzo[b]azepin-2-one (901 mg, 98%) that had the following properties: LC/MS (ESI+): 235 (M+H); $^1$H-NMR (CDCl$_3$, 400 MHz): δ 6.95 (d, J=7.9, 1H), 6.68 (s, 1H), 6.51 (d, J=7.9, 1H), 3.95 (br s, 2H), 3.67 (br s, 2H), 3.56 (m, 2H), 3.32 (d, 3H, J=2.2), 2.75 (br s, 2H), 2.30 (m, 2H), 2.10 (m, 2H).

361c) A microwave vessel was charged with 8-amino-1-(2-methoxy-ethyl)-1,3,4,5-tetrahydro-1-benzazepin-2-one (51.3 mg, 0.219 mmol), 2-(2,5-dichloro-pyrimidin-4-ylamino)-3,N-dimethyl-benzamide (56.8 mg, 0.182 mmol), 10-camphorsulfonic acid (4.2 mg, 0.018 mmol) and isopropyl alcohol (2.0 mL) and heated at 120° C. for 60 minutes in a microwave reactor (sealed vessel). The reaction mixture was quenched with a slurry of saturated, aqueous NaHCO$_3$ and stirred for 2 h. This mixture was diluted with water (10 mL) and extracted into DCM. The organic layer was dried by passing through a funnel filled with Na$_2$SO$_4$, and the filtrate was evaporated onto celite prior to purification by chromatography (amine modified silica gel, 25% EtOAc/hexane→80% EtOAc gradient). The appropriate fractions were combined, evaporated to afford a solid that was triturated with ether (2×2 mL) and yielded product (50.0 mg, 54%) as a white powder that had the following properties: mp: 185-187° C.; LC/MS (ESI+): 509 (M+H); $^1$H-NMR (DMSO-d$_6$, 400 MHz): δ 9.30-9.17 (m, 2H), 8.29 (br s, 1H), 8.13 (s, 1H), 7.45-7.38 (m, 2H), 7.35 (m, 1H), 7.30-7.18 (m, 2H), 6.92 (d, J=7.9, 1H), 4.05 (br s, 2H), 3.28 (br s, 2H), 3.09 (s, 3H), 2.70 (d, 3H, J=4.3), 2.55 (m, 2H) 2.25 (2, 3H), 2.20-1.80 (series of m, 4H).

Example 362

2-{5-Chloro-2-[1-(2-methoxy-ethyl)-2-oxo-2,3,4,5-tetrahydro-1H-benzo[b]azepin-8-ylamino]-pyrimidin-4-ylamino}-3-fluoro-N-methyl-benzamide A microwave vessel was charged with 8-amino-1-(2-methoxy-ethyl)-1,3,4,5-tetrahydro-1-benzazepin-2-one (51.3 mg, 0.219 mmol), 2 2-(2,5-dichloro-pyrimidin-4-ylamino)-3-fluoro-N-methyl-benzamide, 10-camphorsulfonic acid (4.2 mg, 0.018 mmol) and isopropyl alcohol (2.0 mL) and heated at 120° C. for 60 minutes in a microwave reactor (sealed vessel). The reaction mixture was quenched with a slurry of saturated, aqueous, NaHCO$_3$ and stirred for 2 h. This mixture was diluted with water (10 mL) and extracted into DCM. The organic layer was dried by passing through a funnel filled with Na$_2$SO$_4$, and the filtrate was evaporated onto celite prior to purification by chromatography (amine modified silica gel, 25% EtOAc/hexane→80% EtOAc gradient). The appropriate fractions were combined, evaporated to afford a solid that was triturated with ether (2×2 mL) and yielded product (56.8 mg, 61%) as a white powder that had the following properties: mp: 199-204° C.; LC/MS (ESI+): 513 (M+H); $^1$H-NMR (DMSO-d$_6$, 400 MHz): δ 9.37 (s, 1H), 9.34 (s, 1H), 8.52 (m, 1H), 8.19 (s, 1H), 7.48-7.38 (m, 2H), 7.35-7.30 (m, 2H), 7.22 (d, 1H, J=8.2), 6.97 (d, J=8.2, 1H), 4.05 (br s, 2H), 3.27 (br s, 2H), 3.09 (s, 3H), 2.74 (d, 3H, J=4.0), 2.54 (m, 2H), 2.10-1.90 (series of m, 4H).

Example 371

N-(trans-2-{5-Chloro-2-[3-(2-methoxy-ethyl)-2,3,4,5-tetrahydro-1H-benzo[d]azepin-7-ylamino]-pyrimidin-4-ylamino}-cyclopentyl)-methanesulfonamide 371a) A mixture of trans-cyclopentane-1,2-diamine dihydrochloride (400 mg, 2.33 mmol) and triethylamine (1.95 mL, 13.98 mmol) was stirred in 20 mL of anhydrous THF at room temperature for 10 min. The reaction was cooled to 0° C. before adding 2,4,5-trichloropyrimidine (177 μL, 1.55 mmol). After an additional 10 min of stirring, methanesulfonyl chloride (451 μL, 5.83 mmol) was added to the reaction mixture. The reaction was stirred at 0° C. for 1 h before being quenched with saturated sodium bicarbonate solution. The solution was extracted with dichloromethane (2×50 mL) and the organic layer was washed with saturated sodium bicarbonate solution (1×50 mL). The organic phase was then dried over MgSO$_4$, filtered, and evaporated. The residue was purified by flash chromatography over silica using a gradient of 0-100% ethyl acetate in hexanes to afford 70 mg (9%) of a tan solid. Compound N-[trans-2-(2,5-dichloro-pyrimidin-4-ylamino)-cyclopentyl]-methanesulfonamide: MS (ES$^+$ calculated—324; found 325 M+H).

271b) N-[trans-2-(2,5-Dichloro-pyrimidin-4-ylamino)-cyclopentyl]-methanesulfonamide (60 mg, 0.185 mmol), 3-(2-methoxy-ethyl)-2,3,4,5-tetrahydro-1H-benzo[d]azepin-7-ylamine (40 mg, 0.185 mmol) and camphorsulfonic acid (64 mg, 0.278 mmol) were combined in 2 mL isopropanol and heated at 120° C. in microwave for a total of 90 min. The reaction was concentrated to be taken up in dichloromethane and washed with saturated sodium bicarbonate solution (2×30 mL). The organic layer was dried over MgSO$_4$ and filtered. The filtrate was chromatographed on a 4 g amine capped ISCO flash column using a gradient of 0-100% ethyl acetate in hexanes. The product was collected as a foam after concentrating to afford 71 mg (76%) of a pale yellow solid. Compound 1: mp 74° C.; MS (ES$^+$ calculated—508; found—

509 M+H). $^1$H NMR (400 MHz, CDCl$_3$) δ 7.95 (s, 1H), 7.06 (d, J=9 Hz, 1H), 6.96 (s, 1H), 6.38 (br s, 1H), 5.39 (d, J=6 Hz, 1H), 5.32 (s, 1H), 4.16 (m, 1H), 3.55 (t, J=6 Hz, 2H), 3.38 (s, 3H), 2.93 (m, 4H), 2.85 (s, 3H), 2.76 (m, 4H), 2.30 (m, 2H), 1.86 (m, 2H), 1.23 (t, 2H) ppm.

Example 372 cis-2-{5-Chloro-2-[3-(2-methoxy-ethyl)-2,3,4,5-tetrahydro-1H-benzo[d]azepin-7-ylamino]-pyrimidin-4-ylamino}-cyclopentanecarboxylic acid methylamide 372a) A solution of cis-2-amino-cyclopentanecarboxylic acid methylamide (2.265 g, 15.95 mmol) in isopropanol (100 mL) was stirred at 0° C. 2,4,5-Trichloro-pyrimidine (1.51 mL, 13.29 mmol) was then added dropwise via syringe. The reaction was allowed to stir at 0° C. for 20 min followed by room temperature for 2 h. The reaction was concentrated onto celite and purified by flash chromatography over silica using a gradient of 0-100% ethyl acetate in hexanes to afford 1.94 g (42%) of a white solid. Compound cis-2-(2,5-dichloro-pyrimidin-4-ylamino)-cyclopentanecarboxylic acid methylamide: MS (ES$^+$ calculated—288; found 289 M+H).

372b) cis-2-(2,5-Dichloro-pyrimidin-4-ylamino)-cyclopentanecarboxylic acid methylamide (60 mg, 0.208 mmol), 3-(2-methoxy-ethyl)-2,3,4,5-tetrahydro-1H-benzo[d]azepin-7-ylamine (46 mg, 0.208 mmol) and camphorsulfonic acid (72 mg, 0.312 mmol) were combined in 2 mL isopropanol and heated at 120° C. in microwave for a total of 75 min. The reaction was concentrated to be taken up in dichloromethane and washed with saturated sodium bicarbonate solution (2×30 mL). The organic layer was dried over MgSO$_4$ and filtered. The filtrate was chromatographed on an ISCO flash column from 0-100% ethyl acetate in hexanes. The product was collected as a foam after concentrating to afford 52 mg (53%) of a white foam. Compound 2: mp 176° C.; MS (ES$^+$ calculated—472; found—473 M+H). $^1$H NMR (400 MHz, CDCl$_3$) δ 7.86 (s, 1H), 7.39 (s, 1H), 7.30 (s, 1H), 7.17 (s, 1H), 7.03 (d, J=8 Hz, 1H), 6.21 (d, J=7, 1H), 5.52 (br s, 1H), 4.58 (t, J=7 Hz, 1H), 3.55 (t, J=5, 2H), 3.34 (s, 3H), 2.91 (br s, 6H), 2.75 (m, 4H), 2.72 (m, 4H), 2.15 (m, 2H), 1.96 (m, 4H), 1.64 (m, 1H) ppm.

Example 373 cis-2-[5-Chloro-2-(1-ethyl-6-methoxy-2-oxo-2,3,4,5-tetrahydro-1H-benzo[b]azepin-7-ylamino)-pyrimidin-4-ylamino]-cyclopentanecarboxylic acid methylamide 373a) cis-2-(2,5-Dichloro-pyrimidin-4-ylamino)-cyclopentanecarboxylic acid methylamide (60 mg, 0.208 mmol), 7-amino-1-ethyl-6-methoxy-1,3,4,5-tetrahydro-benzo[b]azepin-2-one (49 mg, 0.208 mmol) and camphorsulfonic acid (72 mg, 0.312 mmol) were combined in 3 mL isopropanol and heated at 120° C. in microwave for a total of 110 min. The reaction was concentrated to be taken up in dichloromethane and washed with saturated sodium bicarbonate solution (2×30 mL). The organic layer was dried over MgSO4 and filtered. The filtrate was chromatographed on a 4 g amine capped ISCO flash column from 0-100% ethyl acetate in hexanes. The product was collected as a foam after concentrating to afford 49 mg (49%) of a white solid. Compound 3: mp 231-235° C.; MS (ES$^+$ calculated—486; found—487 M+H). $^1$H NMR (400 MHz, CDCl$_3$) δ 8.37 (d, i=9, 1H), 7.93 (s, 1H), 7.36 (s, 1H), 6.99 (d, J=9, 1H), 6.40 (d, J=7 Hz, 1H), 5.58 (br s, 1H), 4.61 (t, J=4, 1H), 3.82 (s, 3H), 2.87 (q, J=7, 2H), 2.76 (d, J=5, 3H), 2.31 (s, 3H), 2.18-1.98 (m, 7H), 1.66 (m, 2H), 1.15 (t, J=7, 3H) ppm.

Example 374

N-{trans-2-[5-Chloro-2-(1-ethyl-6-methoxy-2-oxo-2,3,4,5-tetrahydro-1H-benzo[b]azepin-7-ylamino)-pyrimidin-4-ylamino]-cyclopentyl}-methanesulfonamide 374a) N-[trans-2-(2,5-Dichloro-pyrimidin-4-ylamino)-cyclopentyl]-methanesulfonamide (60 mg, 0.185 mmol), 7-amino-1-ethyl-6-methoxy-1,3,4,5-tetrahydro-benzo[b]azepin-2-one (43 mg, 0.185 mmol) and camphorsulfonic acid (64 mg, 0.278 mmol) were combined in 3 mL isopropanol and heated at 120° C. in microwave for a total of 110 min. The reaction was concentrated to be taken up in dichloromethane and washed with saturated sodium bicarbonate solution (2×30 mL). The organic layer was dried over MgSO4 and filtered. The filtrate was chromatographed on a 4 g amine capped ISCO flash column from 0-100% ethyl acetate in hexanes. The product was collected as a foam after concentrating to afford 39 mg (40%) of a white foam. Compound 4: mp 141° C.; MS (ES$^+$ calculated—523; found—524 M+H). $^1$H NMR (400 MHz, CDCl$_3$) δ 8.20 (d, J=8, 1H), 8.01 (s, 1H), 7.37 (s, 1H), 7.01 (d, J=8, 1H), 6.11 (s, 1H), 5.46 (d, 1H), 4.25 (m, 1H), 3.82 (s, 3H), 2.89 (m, 1H), 2.89 (s, 4H), 2.32 (br s, 6H), 1.89 (m, 2H), 1.73 (m, 1H), 1.59 (s, 3H), 1.15 (t, J=7, 4H) ppm.

Example 375 cis-2-[5-Chloro-2-(3-dimethylcarbamoylmethyl-8-methoxy-2,3,4,5-tetrahydro-1H-benzo[d]azepin-7-ylamino)-pyrimidin-4-ylamino]-cyclopentanecarboxylic acid methylamide cis-2-(2,5-Dichloro-pyrimidin-4-ylamino)-cyclopentanecarboxylic acid methylamide (46 mg, 0.160 mmol), 2-(7-amino-8-methoxy-1,2,4,5-tetrahydro-benzo[d]azepin-3-yl)-N,N-dimethyl-acetamide (44 mg, 0.160 mmol) and camphorsulfonic acid (56 mg, 0.240 mmol) were combined in 3 mL isopropanol and heated at 120° C. in microwave for a total of 90 min. The reaction was concentrated to be taken up in dichloromethane and washed with saturated sodium bicarbonate solution (2×30 mL). The organic layer was dried over MgSO4 and filtered. The filtrate was chromatographed on a 4 g amine capped ISCO flash column from 0-100% ethyl acetate in hexanes. The product was collected as a foam after concentrating to afford 43 mg (51%) of a white foam. Compound 5: mp 240° C.; MS (ES$^+$ calculated—529; found—530 M+H). $^1$H NMR (400 MHz, CDCl$_3$) δ 8.22 (s, 1H), 7.89 (s, 1H), 7.40 (s, 1H), 6.65 (s, 1H), 6.14 (d, J=7 Hz, 1H), 5.57 (br s, 1H), 4.61 (t, J=7 Hz, 1H), 3.88 (s, 3H), 3.29 (s, 2H), 3.15 (s, 3H), 2.99 (s, 3H), 2.89 (s, 4H), 2.71 (d, J=4 Hz, 6H), 2.17 (m, 1H), 2.08 (m, 1H), 1.98 (br s, 2H), 1.65 (m, 1H) ppm.

Example 376

2-[5-Bromo-2-(3-dimethylcarbamoylmethyl-8-methoxy-2,3,4,5-tetrahydro-1H-benzo[d]azepin-7-ylamino)-pyrimidin-4-ylamino]-N-methyl-benzamide 2-(5-Bromo-2-chloro-pyrimidin-4-ylamino)-N-methyl-benzamide (50 mg, 0.161 mmol), 2-(7-amino-8-methoxy-1, 2,4,5-tetrahydro-benzo[d]azepin-3-yl)-N,N-dimethyl-acetamide (44 mg, 0.161 mmol) and camphorsulfonic acid (56 mg, 0.241 mmol) were combined in 3 mL isopropanol and heated at 120° C. in microwave for a total of 90 min. The reaction was concentrated to be taken up in dichloromethane and washed with saturated sodium bicarbonate solution (2×30 mL). The organic layer was dried over MgSO4 and filtered. The filtrate was chromatographed on a 4 g amine capped ISCO flash column from 0-100% ethyl acetate in hexanes. The product was collected as a foam after concentrating to afford 43 mg (51%) of a yellow foam. Compound 6: mp 225° C.; MS (ES$^+$ calculated" 582; found: 583 M+H). $^1$H NMR (400 MHz, CDCl$_3$) δ 10.81 (s, 1H), 8.59 (d, J=8, 1H), 8.21 (s, 1H), 8.07 (s, 1H), 7.49 (m, 3H), 7.10 (t, J=7 Hz, 1H), 6.65 (s, 1H), 6.29 (s, 1H), 3.88 (s, 3H), 3.29 (s, 2H), 3.16 (s, 3H), 3.05 (d, J=4, 3H), 2.99 (s, 3H), 2.89 (s, 2H), 2.77 (s, 2H), 2.71 (s, 6H), 1.66 (br s, 1H) ppm.

Example 381

2-[5-Chloro-2-(5,5-dimethyl-2-oxo-2,3,4,5-tetrahydro-1H-benzo[b]azepin-7-ylamino)-pyrimidin-4-ylamino]-N-methyl-benzamide 381a) 5,5-Dimethyl-1,3,4,5-tetrahydrobenzo[b]azepin-2-one (514 mg, 2.716 mmol), WO 2005066165, was added to a 0° C. solution of 5 mL nitric acid and 5 mL sulfuric acid. The solution was stirred for 10 minutes at 0° C. ° C. The reaction was poured into a dilute NaOH/ice mixture. NaOH and sodium bicarbonate were added until the solution pH was neutral. A white precipitate formed, which was filtered off, washed with water and dried (485 mg, 76%) to yield 5,5-Dimethyl-7-nitro-1,3,4,5-tetrahydro-benzo[b]azepin-2-one. mp 208° C.; LCMS: m/z=235.03 (M+H$^+$), $^1$H NMR (400 MHz, CDCl$_3$) δ 8.38 (s, 1H), 8.35 (s, 1H), 8.10 (d, 1H, J=8.9 Hz), 7.06 (d, 1H, J=8.6 Hz), 2.50 (m, 2H), 2.17 (m, 2H° C.), 1.48 (s, 6H).

381b) Added 13 mL of ethanol, 10% Palladium on activated carbon (62 mg), and hydrazine monohydrate (171 ul) to 5,5-Dimethyl-7-nitro-1,3,4,5-tetrahydrobenzo[b]azepin-2-one (206 mg, 0.8793 mmol). Heated reaction to 60° C. overnight. Filtered reaction through Celite, and purified by normal phase silica gel chromatography eluting with 90/10/1 CH$_2$Cl$_2$/MeOH/NH$_4$OH to obtain an off-white solid to yield 7-Amino-5,5-dimethyl-1,3,4,5-tetrahydro-benzo[b]azepin-2-one. mp 168° C.; LCMS: m/z=205.12 (M+H$^+$), $^1$H NMR (400 MHz, CDCl$_3$) δ 8.35 (br s, 1H), 6.78 (d, 1H, J=8.3 Hz), 6.72 (s, 1H), 6.54 (d, 1H, J=8.3 Hz), 3.76 (br s, 2H), 2.32 (m, 2H), 2.06 (m, 2H), 1.35 (s, 6H).

381c) Combined 2-(2,5-Dichloro-pyrimidin-4-ylamino)-N-methyl-benzamide (69 mg, 0.2322 mmol), 7-Amino-5,5-dimethyl-1,3,4,5-tetrahydro-benzo[b]azepin-2-one (73 mg, 0.357 mmol), 4 N HCl in dioxane (70 ul) and 2-methoxyethanol (3 mL). Heated reaction to 120° C. for 1.5 hours. Let reaction cool to room temperature and a solid precipitated out, which was filtered off. Purified solid with normal phase chromatography to yield a white solid (33.6 mg, 31%), 2-[5-Chloro-2-(5,5-dimethyl-2-oxo-2,3,4,5-tetrahydro-1H-benzo[b]azepin-7-ylamino)-pyrimidin-4-ylamino]-N-methyl-benzamide. mp 295° C.; LCMS: m/z=465.41 (M+H$^+$), $^1$H NMR (400 MHz, MeOD) δ 8.76 (d, 1H, J=8.6 Hz), 8.13 (s, 1H), 7.69 (m, 2H), 7.59 (s, 1H), 7.48 (m, 1H), 7.15 (m, 1H), 6.97 (d, 1H, J=8.3 Hz), 2.95 (s, 3H), 2.34 (m, 2H), 2.12 (m, 2H), 1.38 (s, 6H).

Example 382

3-Chloro-2-[5-chloro-2-(5,5-dimethyl-2-oxo-2,3,4,5-tetrahydro-1H-benzo[b]azepin-7-ylamino)-pyrimidin-4-ylamino]-N-methyl-benzamide Combined 3-Chloro-2-(2,5-dichloro-pyrimidin-4-ylamino)-N-methyl-benzamide (100 mg, 0.3015 mmol), 7-Amino-5,5-dimethyl-1,3,4,5-tetrahydro-benzo[b]azepin-2-one (75 mg, 0.367 mmol), 4 N HCl in dioxane (76 ul) and 2-methoxyethanol (4 mL). Heated reaction to 120° C. for 1.5 hours. Let reaction cool to room temperature and evaporated off solvent. Purified with normal phase and reverse phase chromatography to yield a white solid, 3-Chloro-2-[5-chloro-2-(5,5-dimethyl-2-oxo-2,3,4,5-tetrahydro-1H-benzo[b]azepin-7-ylamino)-pyrimidin-4-ylamino]-N-methyl-benzamide. LCMS: m/z=499.59 (M+H$^+$), $^1$H NMR (400 MHz, CDCl$_3$) δ 8.11 (m, 2H), 7.98 (s, 1H), 7.60 (d, 1H, J=8.1 Hz), 7.52 (d, 1H, J=7.6 Hz), 7.43 (m, 2H), 7.21 (s, 1H), 6.70 (d, 1H, J=8.6 Hz), 6.10 (m, 1H), 4.70 (s, 1H), 2.82 (d, 3H, J=4.8 Hz), 2.35 (m, 2H), 2.06 (m, 2H), 1.32 (s, 6H).

Example 383

N-{(1R,2R)-2-[5-Chloro-2-(5,5-dimethyl-2-oxo-2,3,4,5-tetrahydro-1H-benzo[b]azepin-7-ylamino)-pyrimidin-4-ylamino]-cyclohexyl}-methanesulfonamide Combined N-[(1R,2R)-2-(2,5-Dichloro-pyrimidin-4-ylamino)-cyclohexyl]-methanesulfonamide (106 mg, 0.312 mmol), 7-Amino-5,5-dimethyl-1,3,4,5-tetrahydro-benzo[b]azepin-2-one (77 mg, 0.377 mmol), 4 N HCl in dioxane (94 ul) and 2-methoxyethanol (3 mL). Heated reaction to 120° C. for 2 hours. Let reaction cool to room temperature and evaporated off solvent. Purified with normal phase chromatography to yield a white solid (30 mg, 19%), N-{(1R,2R)-2-[5-Chloro-2-(5,5-dimethyl-2-oxo-2,3,4,5-tetrahydro-1H-benzo[b]azepin-7-ylamino)-pyrimidin-4-ylamino]-cyclohexyl}-methanesulfonamide. mp 170-185° C.; LCMS: m/z=507.33 (M+H$^+$), $^1$H NMR (400 MHz, CDCl$_3$) δ 7.84 (s, 1H), 7.58 (d, 1H, J=9.6 Hz), 7.30 (m, 4H), 6.87 (dd, 1H, J=8.6, 2.3 Hz), 5.79 (m, 1H), 3.80 (m, 1H), 3.27 (m, 1H), 2.78 (m, 3H), 2.31 (m, 2H), 2.13 (m, 4H), 1.78 (m, 2H), 1.36 (m, 10H).

Example 384

2-[5-Chloro-2-(1,5,5-trimethyl-2-oxo-2,3,4,5-tetrahydro-1H-benzo[b]azepin-7-ylamino)-pyrimidin-4-ylamino]-N-methyl-benzamide 384a) Combined 5,5-Dimethyl-7-nitro-1,3,4,5-tetrahydrobenzo[b]azepin-2-one (231 mg, 0.986 mmol), cesium carbonate (650 mg, 2 mmol), iodomethane (123 uL, 2 mmol) and DMF (6 mL). Stirred at room temp. for 1 hour. Evaporated off solvent, added water and extracted into methylene chloride. Dried organic layer over sodium sulfate, filtered and concentrated under reduced pressure to yield a yellow solid, 1,5,5-Trimethyl-7-nitro-1,3,4,5-tetrahydro-benzo[b]azepin-2-one. mp 115° C.; LCMS: m/z=249.07 (M+H$^+$), $^1$H NMR (400 MHz, CDCl$_3$) δ 8.32 (d, 1H, J=2.3 Hz), 8.19 (dd, 1H, J=8.7, 2.3 Hz), 7.34 (d, 1H, J=8.6 Hz), 3.37 (s, 3H), 2.34 (m, 2H), 2.14 (m, 2H), 1.43 (s, 6H).

384b) Added 16 mL of ethanol, 10% Palladium on activated carbon, 50% wet with water for safety (129 mg), and hydrazine monohydrate (200 ul) to 1,5,5-Trimethyl-7-nitro-1,3,4,5-tetrahydro-benzo[b]azepin-2-one (257 mg, 1.035 mmol). Heated reaction to 60° C. overnight. Filtered reaction through Celite, and concentrated under reduced pressure to obtain a colorless sticky solid, 7-Amino-1,5,5-trimethyl-1,3,4,5-tetrahydro-benzo[b]azepin-2-one (223 mg, 99%). LCMS: m/z=219.04 (M+H$^+$), $^1$H NMR (400 MHz, DMSO-d$_6$) δ 6.95 (d, 1H, J=8.3 Hz), 6.57 (d, 1H, J=1.5 Hz), 6.48 (dd, 1H, J=8.3, 1.3 Hz), 5.09 (s, 2H), 3.07 (s, 3H), 2.09 (m, 2H), 1.88 (m, 2H), 1.19 (s, 6H).

384c) Combined 2-(2,5-Dichloro-pyrimidin-4-ylamino)-N-methyl-benzamide (94 mg, 0.316 mmol), 7-Amino-1,5,5-trimethyl-1,3,4,5-tetrahydro-benzo[b]azepin-2-one (67 mg, 0.307 mmol), 4 N HCl in dioxane (100 ul) and 2-methoxyethanol (4 mL). Heated reaction to 120° C. for 1.5 hours. Filtered off solid, then purified the solid with normal phase chromatography eluting with 97/3/1 CH$_2$Cl$_2$/MeOH/NH$_4$OH to yield an off-white solid, 2-[5-Chloro-2-(1,5,5-trimethyl-2-oxo-2,3,4,5-tetrahydro-1H-benzo[b]azepin-7-ylamino)-pyrimidin-4-ylamino]-N-methyl-benzamide (53 mg, 35%). LCMS: m/z=479.42 (M+H$^+$), $^1$H NMR (400 MHz, CDCl$_3$) δ 11.15 (s, 1H), 8.66 (d, 1H, J=8.3 Hz), 8.14 (d, 1H, J=1.3 Hz), 7.72 (dd, 1H, J=8.7, 2.1 Hz), 7.52 (d, 1H, J=7.8 Hz), 7.45 (m, 1H), 7.33 (s, 1H), 7.11 (m, 2H), 6.97 (s, 1H), 6.23 (br s, 1H), 3.31 (s, 3H), 3.06 (d, 3H, J=4.8 Hz), 2.33 (m, 2H), 2.05 (m, 2H), 1.31 (s, 6H).

Example 385

N-{(1R,2R)-2-[5-Chloro-2-(1,5,5-trimethyl-2-oxo-2,3,4,5-tetrahydro-1H-benzo[b]azepin-7-ylamino)-pyrimidin-4-ylamino]-cyclohexyl}-methanesulfonamide Combined N-[(1R,2R)-2-(2,5-Dichloro-pyrimidin-4-ylamino)-cyclohexyl]-methanesulfonamide (85 mg, 0.251 mmol), 7-Amino-1,5,5-trimethyl-1,3,4,5-tetrahydro-benzo[b]azepin-2-one (80 mg, 0.251 mmol), 4 N HCl in dioxane (80 ul) and 2-methoxyethanol (3 mL). Heated reaction to 120° C. for 4 hours. Added CH$_2$Cl$_2$/MeOH/NH$_4$OH, evaporated off solvent and purified with normal phase chromatography eluting with 1% to 3% MeOH in CH$_2$Cl$_2$ to yield a yellow solid, N-{(1R,2R)-2-[5-Chloro-2-(1,5,5-trimethyl-2-oxo-2,3,4,5-tetrahydro-1H-benzo[b]azepin-7-ylamino)-pyrimidin-4-ylamino]-cyclohexyl}-methanesulfonamide (26 mg, 20%). mp 165° C.; LCMS: m/z=521.59 (M+H$^+$), $^1$H NMR (400 MHz, CDCl$_3$) δ 7.85 (s, 1H), 7.68 (m, 2H), 7.25 (s, 1H), 7.06 (d, 1H, J=8.6 Hz), 6.06 (d, 1H, J=6.6 Hz), 5.73 (d, 1H, J=7.3 Hz), 3.83 (m, 1H), 3.26 (s, 3H), 2.85 (s, 3H), 2.11 (m, 7H), 1.80 (s, 2H), 1.30 (m, 10H).

Example 386

(2-exo, 3-exo)-3-[5-Chloro-2-(1,5,5-trimethyl-2-oxo-2,3,4,5-tetrahydro-1H-benzo[b]azepin-7-ylamino)-pyrimidin-4-ylamino]-bicyclo[2.2.1]hept-5-ene-2-carboxylic acid amide Combined (2-exo,3-exo)-3-(2,5-Dichloro-pyrimidin-4-ylamino)-bicyclo[2.2.1]hept-5-ene-2-carboxylic acid amide (93 mg, 0.311 mmol), 7-Amino-1,5,5-trimethyl-1,3,4,5-tetrahydro-benzo[b]azepin-2-one (68 mg, 0.311 mmol), 4 N HCl in dioxane (100 ul) and 2-methoxyethanol (4 mL). Heated reaction to 120° C. for 1.5 hours. Evaporated off solvent and purified with normal phase chromatography eluting with 97/3/1 CH$_2$Cl$_2$/MeOH/NH$_4$OH to yield an orange solid, (2-exo,3-exo)-3-[5-Chloro-2-(1,5,5-trimethyl-2-oxo-2,3,4,5-tetrahydro-1H-benzo[b]azepin-7-ylamino)-pyrimidin-4-ylamino]-bicyclo[2.2.1]hept-5-ene-2-carboxylic acid amide (101 mg, 67%). LCMS: m/z=481.45 (M+H$^+$), $^1$H NMR (400 MHz, CDCl$_3$) δ 7.91 (d, 1H, J=1.3 Hz), 7.82 (d, 1H, J=8.6 Hz), 7.30 (s, 1H), 7.13 (d, 1H, J=8.6 Hz), 6.99 (m, 2H), 6.33 (d, 2H, J=1.3 Hz), 5.61 (br s, 1H), 5.44 (br s, 1H), 4.38 (m, 1H), 3.52 (m, 2H), 3.31 (s, 3H), 3.09 (s, 1H), 2.91 (s, 1H), 2.50 (d, 1H, J=8.1 Hz), 2.31 (m, 3H), 2.06 (m, 2H), 1.65 (m, 1H), 1.34 (s, 6H).

Example 387

2-[5-Chloro-2-(1-ethyl-5,5-dimethyl-2-oxo-2,3,4,5-tetrahydro-1H-benzo[b]azepin-7-ylamino)-pyrimidin-4-ylamino]-N-methyl-benzamide 387a) Combined 5,5-Dimethyl-7-nitro-1,3,4,5-tetrahydrobenzo[b]azepin-2-one (520 mg, 2.22 mmol), cesium carbonate (1.52 g, 4.7 mmol), iodoethane (355 uL, 4.44 mmol) and DMF (12 mL). Stirred at room temp. for 2.5 hours. Evaporated off solvent, added water and extracted into methylene chloride. Dried organic layer over sodium sulfate, filtered and concentrated under reduced pressure to yield a brown solid, 1-Ethyl-5,5-dimethyl-7-nitro-1,3,4,5-tetrahydro-benzo[b]azepin-2-one (553 mg, 95%). mp 67° C.; LCMS: m/z=263.08 (M+H$^+$), $^1$H NMR (400 MHz, CDCl$_3$) δ 8.31 (d, 1H, J=2.5 Hz), 8.17 (dd, 1H, J=8.7, 2.6 Hz), 7.38 (d, 1H, J=8.8 Hz), 3.89 (m, 2H), 2.31 (m, 2H), 2.12 (m, 2H), 1.42 (s, 6H), 1.33 (m, 3H).

387b) Added 30 mL of ethanol, 10% Palladium on activated carbon, 50% wet with water for safety (273 mg), and hydrazine monohydrate (400 ul) to 1-Ethyl-5,5-dimethyl-7-nitro-1,3,4,5-tetrahydro-benzo[b]azepin-2-one (537 mg, 2.047 mmol). Heated reaction to 60° C. for 24 hours. Filtered reaction through Celite, and concentrated under reduced pressure. Purified with normal phase silica gel chromatography eluting with 40% to 60% ethyl acetate in hexane to obtain a yellow sticky solid, 7-Amino-1-ethyl-5,5-dimethyl-1,3,4,5-tetrahydro-benzo[b]azepin-2-one (347 mg, 73%). LCMS: m/z=233.07 (M+H$^+$), $^1$H NMR (400 MHz, DMSO-d$_6$) δ 6.98 (d, 1H, J=8.9 Hz), 6.59 (d, 1H, J=1.8 Hz), 6.48 (dd, 1H, J=8.3, 1.5 Hz), 5.08 (s, 2H), 3.58 (m, 2H), 1.96 (m, 4H), 1.17 (m, 9H).

387c) Combined 2-(2,5-Dichloro-pyrimidin-4-ylamino)-N-methyl-benzamide (82 mg, 0.276 mmol), 7-Amino-1-ethyl-5,5-dimethyl-1,3,4,5-tetrahydro-benzo[b]azepin-2-one (61 mg, 0.263 mmol), 4 N HCl in dioxane (80 ul) and 2-methoxyethanol (3 mL). Heated reaction to 120° C. for 3.5 hours. Filtered off solid, then purified the solid with normal phase chromatography eluting with 9/1 methylene chloride/methanol. Washed product with saturated sodium bicarbonate solution and extracted into methylene chloride. Washed organic phase with brine, dried over magnesium sulfate, filtered and concentrated under reduced pressure to yield an off-white solid, 2-[5-Chloro-2-(1-ethyl-5,5-dimethyl-2-oxo-2,3,4,5-tetrahydro-1H-benzo[b]azepin-7-ylamino)-pyrimidin-4-ylamino]-N-methyl-benzamide (34 mg, 25%). LCMS: m/z=493.37 (M+H$^+$), $^1$H NMR (400 MHz, CDCl$_3$) δ 11.11 (s, 1H), 8.60 (d, 1H, J=8.3 Hz), 8.09 (s, 1H), 7.68 (dd, 1H, J=8.3, 2.3 Hz), 7.52 (d, 1H, J=7.3 Hz), 7.39 (m, 1H), 7.33 (d, 1H, J=2.3 Hz), 7.16 (d, 1H, J=8.8 Hz), 7.08 (m, 1H), 6.70 (br s, 1H), 3.79 (m, 2H), 3.40 (s, 1H), 3.01 (d, 3H, J=4.5 Hz), 2.38 (s, 2H), 2.27 (m, 2H), 1.29 (m, 9H).

Example 388

N-{(1R,2R)-2-[5-Chloro-2-(1-ethyl-5,5-dimethyl-2-oxo-2,3,4,5-tetrahydro-1H-benzo[b]azepin-7-ylamino)-pyrimidin-4-ylamino]-cyclohexyl}-methanesulfonamide Combined N-[(1R,2R)-2-(2,5-Dichloro-pyrimidin-4-ylamino)-cyclohexyl]-methanesulfonamide (114 mg, 0.336 mmol), 7-Amino-1-ethyl-5,5-dimethyl-1,3,4,5-tetrahydro-benzo[b]azepin-2-one (80 mg, 0.344 mmol), 4 N HCl in dioxane (103 ul) and 2-methoxyethanol (5 mL). Heated reaction to 120° C. for 2.5 hours. Evaporated off solvent and purified with normal phase chromatography to yield a white solid, N-{(1R,2R)-2-[5-Chloro-2-(1-ethyl-5,5-dimethyl-2-oxo-2,3,4,5-tetrahydro-1H-benzo[b]azepin-7-ylamino)-pyrimidin-4-ylamino]-cyclohexyl}-methanesulfonamide (69 mg, 38%). LCMS: m/z=535.34 (M+H$^+$), $^1$H NMR (400 MHz, CDCl$_3$) δ 7.98 (s, 1H), 7.65 (dd, 1H, J=8.6, 1.3 Hz), 7.36 (d, 1H, J=2.3 Hz), 7.21 (d, 1H, J=8.6 Hz), 6.91 (s, 1H), 5.44 (d, 1H, J=7.6 Hz), 5.36 (d, 1H, J=6.8 Hz), 3.87 (m, 3H), 3.24 (m, 1H), 2.82 (s, 3H), 2.17 (m, 6H), 1.84 (m, 2H), 1.37 (m, 13H).

Example 389

3-Chloro-2-[5-chloro-2-(1-ethyl-5,5-dimethyl-2-oxo-2,3,4,5-tetrahydro-1H-benzo[b]azepin-7-ylamino)-pyrimidin-4-ylamino]-N-methyl-benzamide Combined 3-Chloro-2-(2,5-dichloro-pyrimidin-4-ylamino)-N-methyl-benzamide (91 mg, 0.275 mmol), 7-Amino-1-ethyl-5,5-dimethyl-1,3,4,5-tetrahydro-benzo[b]azepin-2-one (64 mg, 0.275 mmol), DL-10-Camphorsulfonic acid (82 mg, 0.353 mmol) and 2-methoxyethanol (3 mL). Heated reaction to 120° C. for 2.5 hours. Evaporated off solvent, dissolved residue in methylene chloride and washed with saturated sodium bicarbonate solution, then brine. Dried with magnesium sulfate, filtered and purified with normal phase chromatography using basic alumina silica gel to yield a yellow solid, 3-Chloro-2-[5-chloro-2-(1-ethyl-5,5-dimethyl-2-oxo-2,3,4,5-tetrahydro-1H-benzo[b]azepin-7-ylamino)-pyrimidin-4-ylamino]-N-methyl-benzamide (15 mg, 10%). LCMS: m/z=527.54 (M+H$^+$), $^1$H NMR (400 MHz, CDCl$_3$) δ 8.12 (d, 1H, J=1.0 Hz), 8.02 (br s, 1H), 7.59 (d, 1H, J=8.1 Hz), 7.51 (m, 2H), 7.28 (m, 1H), 7.21 (m, 2H), 7.02 (d, 1H, J=8.6 Hz), 6.25 (d, 1H, J=4.6 Hz), 4.13 (m, 2H), 3.76 (m, 2H), 2.82 (d, 3H, J=4.3 Hz), 2.22 (m, 2H), 1.27 (m, 9H).

Example 390

2-[5-Chloro-2-(1-ethyl-5,5-dimethyl-2-oxo-2,3,4,5-tetrahydro-1H-benzo[b]azepin-7-ylamino)-pyrimidin-4-ylamino]-3-fluoro-N-methyl-benzamide Combined 2-(2,5-Dichloro-pyrimidin-4-ylamino)-3-fluoro-N-methyl-benzamide (77 mg, 0.244 mmol), 7-Amino-1-ethyl-5,5-dimethyl-1,3,4,5-tetrahydro-benzo[b]azepin-2-one (60 mg, 0.258 mmol), DL-10-Camphorsulfonic acid (70 mg, 0.301 mmol) and isopropanol (4 mL) in a microwave tube. Microwaved reaction at 120° C. for 30 minutes. Evaporated off solvent, dissolved residue in methylene chloride and washed with saturated sodium bicarbonate solution, then brine. Dried with magnesium sulfate, filtered and purified with normal phase chromatography eluting with hexane/ethyl acetate to yield a yellow solid, 2-[5-Chloro-2-(1-ethyl-5,5-dimethyl-2-oxo-2,3,4,5-tetrahydro-1H-benzo[b]azepin-7-ylamino)-pyrimidin-4-ylamino]-3-fluoro-N-methyl-benzamide (70 mg, 56%). LCMS: m/z=511.11 (M+H$^+$), $^1$H NMR (400 MHz, CDCl$_3$) δ 8.98 (s, 1H), 8.07 (s, 1H), 7.59 (d, 1H, J=8.6 Hz), 7.52 (s, 1H), 7.37 (d, 1H, J=6.8 Hz), 7.24 (m, 1H), 7.10 (s, 1H), 6.97 (d, 1H, J=8.8 Hz), 6.80 (d, 1H, J=3.8 Hz), 3.72 (m, 2H), 2.91 (d, 3H, J=4.3 Hz), 2.14 (m, 2H), 1.87 (m, 2H), 1.25 (m, 3H), 1.18 (s, 6H).

Example 391

7-[5-Chloro-4-(2-methoxy-4-morpholin-4-yl-phenylamino)-pyrimidin-2-ylamino]-1-ethyl-5,5-dimethyl-1,3,4,5-tetrahydro-benzo[b]azepin-2-one Combined (2,5-Dichloro-pyrimidin-4-yl)-(2-methoxy-4-morpholin-4-yl-phenyl)-amine (113 mg, 0.3185 mmol), 7-Amino-1-ethyl-5,5-dimethyl-1,3,4,5-tetrahydro-benzo[b]azepin-2-one (74 mg, 0.3185 mmol), 4 N HCl in dioxane (100 ul) and 2-methoxyethanol (4 mL). Heated reaction to 120° C. for 3 hours. Evaporated off solvent and purified with normal phase chromatography to yield a yellow solid, 7-[5-Chloro-4-(2-methoxy-4-morpholin-4-yl-phenylamino)-pyrimidin-2-ylamino]-1-ethyl-5,5-dimethyl-1,3,4,5-tetrahydro-benzo[b]azepin-2-one (162 mg, 92%). LCMS: m/z=551.00 (M+H$^+$), $^1$H NMR (400 MHz, CDCl$_3$) δ 8.21 (d, 1H, J=9.4 Hz), 8.04 (s, 1H), 7.69 (d, 1H, J=9.4 Hz), 7.60 (s, 1H), 7.34 (s, 1H), 7.19 (d, 1H, J=8.1 Hz), 6.92 (s, 1H), 6.56 (s, 1H), 6.49 (d, 1H, J=8.6 Hz), 3.94 (s, 3H), 3.90 (m, 4H), 3.82 (m, 2H), 3.16 (m, 4H), 2.32 (m, 2H), 2.06 (m, 2H), 1.33 (m, 9H).

Example 392

N-{(1R,2R)-2-[5-Chloro-2-(5,5-dimethyl-2,3,4,5-tetrahydro-1H-benzo[b]azepin-7-ylamino)-pyrimidin-4-ylamino]-cyclohexyl}-methanesulfonamide 392a) Combined 5,5-Dimethyl-7-nitro-1,3,4,5-tetrahydrobenzo[b]azepin-2-one (89 mg, 0.38 mmol), Borane-THF complex, 1M in THF (1.9 mL, 1.9 mmol) and 3 mL anhydrous THF. Heated reaction to reflux for 1 hour. Let reaction cool to room temperature, added methanol and concentrated under reduced pressure. Dissolved residue in methylene chloride and washed with saturated sodium bicarbonate solution. Purified with normal phase chromatography eluting with 10% ethyl acetate in hexane to yield a yellow solid, 5,5-Dimethyl-7-nitro-2,3,4,5-tetrahydro-1H-benzo[b]azepine (60 mg, 72%). mp 99° C.; LCMS: m/z=221.06 (M+H$^+$), $^1$H NMR (400 MHz, CDCl$_3$) δ 8.26 (d, 1H, J=2.3 Hz), 7.91 (dd, 1H, J=8.6, 2.5 Hz), 6.68 (d, 1H, J=8.8 Hz), 4.28 (br s, 1H), 3.16 (m, 2H), 1.91 (m, 2H), 1.72 (m, 2H), 1.41 (s, 6H).

392b) Added 6 mL of ethanol, 10% Palladium on activated carbon (50% wet with water for safety) (60 mg), and hydrazine monohydrate (89 ul) to 5,5-Dimethyl-7-nitro-2,3,4,5-tetrahydro-1H-benzo[b]azepine (101 mg, 0.459 mmol). Heated reaction to 60° C. for 22 hours. Filtered reaction through Celite, and concentrated under reduced pressure. Purified with normal phase silica gel chromatography eluting with 5% methylene chloride in methanol to obtain a brown oil, 5,5-Dimethyl-2,3,4,5-tetrahydro-1H-benzo[b]azepin-7-ylamine (79 mg, 91%). LCMS: m/z=190.99 (M+H$^+$), $^1$H NMR (400 MHz, CDCl$_3$) δ 6.73 (d, 1H, J=2.0 Hz), 6.55 (d, 1H, J=8.1 Hz), 6.43 (dd, 1H, J=8.1, 1.5 Hz), 3.40 (br s, 3H), 2.97 (m, 2H), 1.86 (m, 2H), 1.59 (m, 2H), 1.38 (s, 6H).

392c) Combined N-[(1R,2R)-2-(2,5-Dichloro-pyrimidin-4-ylamino)-cyclohexyl]-methanesulfonamide (112 mg, 0.330 mmol), 5,5-Dimethyl-2,3,4,5-tetrahydro-1H-benzo[b]azepin-7-ylamine (76 mg, 0.399 mmol), 4 N HCl in dioxane (99 ul) and 2-methoxyethanol (4 mL). Heated reaction to 120° C. for 24 hours. Concentrated under reduced pressure and purified with normal phase chromatography to yield a brown solid, N-{(1R,2R)-2-[5-Chloro-2-(5,5-dimethyl-2,3,4,5-tetrahydro-1H-benzo[b]azepin-7-ylamino)-pyrimidin-4- ylamino]-cyclohexyl}-methanesulfonamide (28 mg, 17%). LCMS: m/z=493.30 (M+H$^+$), $^1$H NMR (400 MHz, CDCl$_3$) δ 7.89 (s, 1H), 7.25 (m, 2H), 7.06 (br s, 1H), 6.68 (d, 1H, J=8.1 Hz), 5.76 (br s, 1H), 5.42 (m, 1H), 3.82 (m, 1H), 3.75 (m, 2H), 3.53 (m, 2H), 3.21 (m, 1H), 3.03 (m, 2H), 2.78 (s, 3H), 2.16 (m, 2H), 1.88 (m, 2H), 1.79 (m, 2H), 1.64 (m, 2H), 1.40 (m, 6H), 1.33 (m, 4H).

Example 393

7-[5-Chloro-4-(2-methoxy-4-morpholin-4-yl-phenylamino)-pyrimidin-2-ylamino]-1-ethyl-5,5-dimethyl-1,3,4,5-tetrahydro-benzo[b]azepin-2-one Combined (2,5-Dichloro-pyrimidin-4-yl)-(2-methoxy-4-morpholin-4-yl-phenyl)-amine (108 mg, 0.304 mmol), 7-Amino-5,5-dimethyl-1,3,4,5-tetrahydro-benzo[b]azepin-2-one (79 mg, 0.387 mmol), 4 N HCl in dioxane (100 ul) and 2-methoxyethanol (4 mL). Heated reaction to 120° C. for 2 hours. Evaporated off solvent and purified with normal phase chromatography to yield an off-white solid, 7-[5-Chloro-4-(2-methoxy-4-morpholin-4-yl-phenylamino)-pyrimidin-2-ylamino]-1-ethyl-5,5-dimethyl-1,3,4,5-tetrahydro-benzo[b]azepin-2-one (81 mg, 51%). mp 255° C.; LCMS: m/z=523.06 (M+H$^+$), $^1$H NMR (400 MHz, CDCl$_3$) δ 8.21 (d, 1H, J=7.6 Hz), 8.04 (d, 1H, J=1.5 Hz), 7.65 (d, 1H, J=8.3 Hz), 7.61 (s, 1H), 7.37 (s, 1H), 7.15 (s, 1H), 6.96 (s, 1H), 6.87 (d, 1H, J=8.6 Hz), 6.56 (s, 1H), 6.49 (d, 1H, J=8.8 Hz), 3.94 (s, 3H), 3.91 (m, 4H), 3.17 (m, 4H), 2.41 (m, 2H), 2.12 (m, 2H), 1.40 (s, 6H).

Example 394

(2-exo,3-exo)-3-[5-Chloro-2-(5,5-dimethyl-2-oxo-2,3,4,5-tetrahydro-1H-benzo[b]azepin-7-ylamino)-pyrimidin-4-ylamino]-bicyclo[2.2.1]hept-5-ene-2-carboxylic acid amide Combined (2-exo,3-exo)-3-(2,5-Dichloro-pyrimidin-4-ylamino)-bicyclo[2.2.1]hept-5-ene-2-carboxylic acid amide (97 mg, 0.324 mmol), 7-Amino-5,5-dimethyl-1,3,4,5-tetrahydro-benzo[b]azepin-2-one (81 mg, 0.397 mmol), 4 N HCl in dioxane (100 ul) and 2-methoxyethanol (4 mL). Heated reaction to 120° C. for 1 hour. Evaporated off solvent and purified with normal phase chromatography eluting with 97/3/1 CH$_2$Cl$_2$/MeOH/NH$_4$OH to yield an off-white solid, (2-exo,3-exo)-3-[5-Chloro-2-(5,5-dimethyl-2-oxo-2,3,4,5-tetrahydro-1H-benzo[b]azepin-7-ylamino)-pyrimidin-4-ylamino]-bicyclo[2.2.1]hept-5-ene-2-carboxylic acid amide (55 mg, 36%). mp 200° C.; LCMS: m/z=467.33 (M+H$^+$), $^1$H NMR (400 MHz, CDCl$_3$) δ 7.91 (s, 1H), 7.74 (d, 1H, J=9.8 Hz), 7.35 (s, 1H), 7.06 (s, 1H), 6.92 (m, 3H), 6.32 (s, 2H), 5.57 (s, 1H), 5.37 (s, 1H), 4.37 (m, 1H), 3.09 (s, 1H), 2.90 (s, 1H), 2.49 (d, 1H, J=7.8 Hz), 2.40 (m, 2H), 2.26 (d, 1H, J=9.4 Hz), 2.12 (m, 2H), 1.66 (m, 1H), 1.43 (s, 6H).

Example 395

N-{(1R,2R)-2-[5-Chloro-2-(5,5-dimethyl-2-oxo-2,3,4,5-tetrahydro-1H-benzo[b]azepin-7-ylamino)-pyrimidin-4-ylamino]-cyclohexyl}-acetamide Combined N-[(1R,2R)-2-(2,5-Dichloro-pyrimidin-4-ylamino)-cyclohexyl]-acetamide (96 mg, 0.317 mmol), 7-Amino-5,5-dimethyl-1,3,4,5-tetrahydro-benzo[b]azepin-2-one (81 mg, 0.397 mmol), 4 N HCl in dioxane (100 ul) and 2-methoxyethanol (4 mL). Heated reaction to 120° C. for 7 hours. Evaporated off solvent and purified with normal phase chromatography eluting with 97/3/1 CH$_2$Cl$_2$/MeOH/NH$_4$OH to yield an off-white solid, N-{(1R,2R)-2-[5-Chloro-2-(5,5-dimethyl-2-oxo-2,3,4,5-tetrahydro-1H-benzo[b]azepin-7-ylamino)-pyrimidin-4-ylamino]-cyclohexyl}-acetamide (54 mg, 36%). mp 227° C.; LCMS: m/z=471.38 (M+H$^+$), $^1$H NMR (400 MHz, CDCl$_3$) δ 7.83 (s, 1H), 7.71 (dd, 1H, J=8.6, 2.3 Hz), 7.32 (m, 1H), 6.91 (d, 1H, J=8.6 Hz), 6.81 (m, 1H), 6.13 (m, 1H), 3.79 (m, 2H), 3.20 (s, 1H), 2.35 (m, 2H), 2.25 (m, 1H), 2.11 (m, 2H), 2.04 (m, 1H), 1.81 (m, 8H), 1.36 (m, 8H).

Example 396

2-[5-Chloro-2-(5,5-dimethyl-2-oxo-2,3,4,5-tetrahydro-1H-benzo[b]azepin-7-ylamino)-pyrimidin-4-ylamino]-3-fluoro-N-methyl-benzamide Combined 2-(2,5-Dichloro-pyrimidin-4-ylamino)-3-fluoro-N-methyl-benzamide (73 mg, 0.232 mmol), 7-Amino-5,5-dimethyl-1,3,4,5-tetrahydro-benzo[b]azepin-2-one (57 mg, 0.279 mmol), DL-10-Camphorsulfonic acid (67 mg, 0.288 mmol) and isopropanol (4 mL) in a microwave tube. Microwaved reaction at 120° C. for 70 minutes. Evaporated off solvent and purified with normal phase chromatography to yield a yellow solid, 2-[5-Chloro-2-(5,5-dimethyl-2-oxo-2,3,4,5-tetrahydro-1H-benzo[b]azepin-7-ylamino)-pyrimidin-4-ylamino]-3-fluoro-N-methyl-benzamide (29 mg, 26%). mp 153° C.; LCMS: m/z=483.37 (M+H$^+$), $^1$H NMR (400 MHz, CDCl$_3$) δ 8.89 (s, 1H), 8.07 (s, 1H), 7.96 (s, 1H), 7.61 (s, 1H), 7.53 (d, 1H, J=8.6 Hz), 7.27 (m, 3H), 6.70 (m, 2H), 6.40 (m, 1H), 2.92 (d, 3H, J=4.8 Hz), 2.32 (m, 2H), 2.04 (m, 2H), 1.30 (s, 6H).

Example 397

7-{5-Chloro-4-[2-(1-methyl-1H-imidazol-2-yl)-phenylamino]-pyrimidin-2-ylamino}-5,5-dimethyl-1,3,4,5-tetrahydro-benzo[b]azepin-2-one Combined (2,5-Dichloro-pyrimidin-4-yl)-[2-(1-methyl-1H-imidazol-2-yl)-phenyl]-amine (82 mg, 0.256 mmol), 7-Amino-5,5-dimethyl-1,3,4,5-tetrahydro-benzo[b]azepin-2-one (63 mg, 0.308 mmol), 4 N HCl in dioxane (80 ul) and 2-methoxyethanol (4 mL). Heated reaction to 120° C. for 6 hours. Evaporated off solvent and purified with normal phase chromatography to yield a light brown solid, 7-{5-Chloro-4-[2-(1-methyl-1H-imidazol-2-yl)-phenylamino]-pyrimidin-2-ylamino}-5,5-dimethyl-1,3,4,5-tetrahydro-benzo[b]azepin-2-one (103 mg, 82%). mp 227° C.; LCMS: m/z=488.23 (M+H$^+$), $^1$H NMR (400 MHz, CDCl$_3$) δ 8.20 (m, 1H), 7.95 (s, 1H), 7.54 (dd, 1H, J=8.5, 2.4 Hz), 7.39 (m, 4H), 7.24 (m, 2H), 7.01 (d, 1H, J=1.3 Hz), 6.81 (d, 1H, J=8.6 Hz), 6.71 (m, 1H), 6.53 (dd, 1H, J=8.2, 2.7 Hz), 3.67 (s, 3H), 2.30 (m, 2H), 2.03 (m, 2H), 1.29 (s, 6H).

Example 398

7-[5-Chloro-4-(2-pyrazol-1-yl-phenylamino)-pyrimidin-2-ylamino]-5,5-dimethyl-1,3,4,5-tetrahydro-benzo[b]azepin-2-one Combined (2,5-Dichloro-pyrimidin-4-yl)-(2-pyrazol-1-yl-phenyl)-amine (82 mg, 0.268 mmol), 7-Amino-5,5-dimethyl-1,3,4,5-tetrahydro-benzo[b]azepin-2-one (70 mg, 0.343 mmol), 4 N HCl in dioxane (80 ul) and 2-methoxyethanol (4 mL). Heated reaction at 120° C. for 16 hours. Evaporated off solvent and purified with normal phase chromatography to yield a beige solid, 7-[5-Chloro-4-(2-pyrazol-1-yl-phenylamino)-pyrimidin-2-ylamino]-5,5-dimethyl-1,3,4,5-tetrahydro-benzo[b]azepin-2-one (104 mg, 82%). LCMS: m/z=474.34 (M+H$^+$), $^1$H NMR (400 MHz, CD$_3$OD) δ 8.41 (d, 1H, J=8.1 Hz), 8.02 (m, 2H), 7.84 (s, 1H), 7.60 (dd, 1H, J=8.3, 2.3 Hz), 7.52 (m, 2H), 7.42 (m, 1H), 7.30 (m, 1H), 6.91 (d, 1H, J=8.6 Hz), 6.55 (m, 1H), 4.59 (s, 1H), 2.32 (m, 2H), 2.11 (m, 2H), 1.35 (s, 6H).

Example 399

2-[5-Chloro-2-(5,5-dimethyl-2-oxo-2,3,4,5-tetrahydro-1H-benzo[b]azepin-7-ylamino)-pyrimidin-4-ylamino]-3,N-dimethyl-benzamide Combined 2-(2,5-Dichloro-pyrimidin-4-ylamino)-3,N-dimethyl-benzamide (90 mg, 0.289 mmol), 7-Amino-5,5-dimethyl-1,3,4,5-tetrahydro-benzo[b]azepin-2-one (62 mg, 0.304 mmol), DL-10-Camphorsulfonic acid (84 mg, 0.362 mmol) and isopropanol (3 mL) in a microwave tube. Microwaved reaction at 120° C. for 20 minutes. Evaporated off solvent and purified with normal phase chromatography to yield an off-white solid, 2-[5-Chloro-2-(5,5-dimethyl-2-oxo-2,3,4,5-tetrahydro-1H-benzo[b]azepin-7-ylamino)-pyrimidin-4-ylamino]-3,N-dimethyl-benzamide (4.2 mg, 3%). LCMS: m/z=479.37 (M+H$^+$), $^1$H NMR (400 MHz, CDCl$_3$) δ 8.67 (s, 1H), 8.06 (d, 1H, J=1.3 Hz), 7.39 (m, 4H), 7.27 (m, 1H), 7.18 (s, 1H), 7.14 (s, 1H), 6.66 (d, 1H, J=8.6 Hz), 6.10 (m, 1H), 2.92 (m, 3H), 2.34 (m, 2H), 2.25 (s, 3H), 2.05 (m, 2H), 1.30 (s, 6H).

Example 400

2-[5-Chloro-2-(1-oxo-2,3,4,5-tetrahydro-1H-benzo[c]azepin-8-ylamino)-pyrimidin-4-ylamino]-3-fluoro-N-methyl-benzamide 400a) 2,3,4,5-Tetrahydro-benzo[c]azepin-1-one (2.98 g, 18.5 mmol) was cooled to −20° C. and treated with 30 mL of a cold 1:1 mixture of conc. nitric and conc. sulfuric acid for 1 h, then allowed to warm to room temperature. After overnight stirring, the mixture was poured onto ice. The crude product precipitated from solution and was recrystallized from ethyl acetate/heptane to afford 8-Nitro-2,3,4,5-tetrahydro-benzo[c]azepin-1-one (2.17 g, 56%) as an off white solid. m.p.=177-180° C.; LCMS (m/e) 207 (M+1); $^1$H-NMR (CDCl$_3$, 400 MHz) δ 8.58 (s, 1H), 8.25 (m, 1H), 7.39 (d, 1H, J=8.3 Hz), 6.51 (s, 1H), 3.16 (m, 2H), 3.00 (t, 2H, J=7.1 Hz), 2.10 (m, 2H).

400b) Added 65 mL of ethanol, 10% Palladium on activated carbon (50% wet with water for safety) (513 mg), and hydrazine monohydrate (965 ul) to 8-Nitro-2,3,4,5-tetrahydro-benzo[c]azepin-1-one (1.024 g, 4.966 mmol). Heated reaction to 60° C. for 16 hours. Filtered reaction through Celite, and concentrated under reduced pressure. Purified with normal phase silica gel chromatography to obtain a white solid, 8-Amino-2,3,4,5-tetrahydro-benzo[c]azepin-1-one (799 mg, 91%). LCMS: m/z=177.03 (M+H$^+$), $^1$H NMR (400 MHz, CD$_3$OD) δ 7.00 (d, 1H, J=8.1 Hz), 6.96 (m, 1H), 6.80 (m, 1H), 3.33 (m, 3H), 3.06 (m, 2H), 2.71 (m, 2H), 1.96 (m, 2H).

400c) Combined 2-(2,5-Dichloro-pyrimidin-4-ylamino)-3-fluoro-N-methyl-benzamide (104 mg, 0.33 mmol), 8-Amino-2,3,4,5-tetrahydro-benzo[c]azepin-1-one (70 mg, 0.397 mmol), DL-10-Camphorsulfonic acid (82 mg, 0.353 mmol) and isopropanol (4 mL) in a microwave tube. Microwaved reaction at 120° C. for 30 minutes. Evaporated off solvent and purified with normal phase chromatography to yield a white solid, 2-[5-Chloro-2-(1-oxo-2,3,4,5-tetrahydro-1H-benzo[c]azepin-8-ylamino)-pyrimidin-4-ylamino]-3-fluoro-N-methyl-benzamide (23 mg, 15%). mp 200° C.; LCMS: m/z=455.37 (M+H$^+$), $^1$H NMR (400 MHz, CD$_3$OD) δ 8.06 (s, 1H), 7.66 (m, 1H), 7.43 (m, 2H), 7.03 (d, 1H, J=9.1 Hz), 3.03 (m, 2H), 2.84 (s, 3H), 2.75 (m, 2H), 1.98 (m, 2H).

Example 401

2-[5-Chloro-2-(1-oxo-2,3,4,5-tetrahydro-1H-benzo[c]azepin-8-ylamino)-pyrimidin-4-ylamino]-3,N-dimethyl-benzamide Combined 2-(2,5-Dichloro-pyrimidin-4-ylamino)-3,N-dimethyl-benzamide (100 mg, 0.321 mmol), 8-Amino-2,3,4,5-tetrahydro-benzo[c]azepin-1-one (69 mg, 0.392 mmol), DL-10-Camphorsulfonic acid (93 mg, 0.400 mmol) and isopropanol (4 mL) in a microwave tube. Microwaved reaction at 120° C. for 30 minutes. Evaporated off solvent and purified with normal phase chromatography to yield an off-white solid, 2-[5-Chloro-2-(1-oxo-2,3,4,5-tetrahydro-1H-benzo[c]azepin-8-ylamino)-pyrimidin-4-ylamino]-3,N-dimethyl-benzamide (25 mg, 17%). mp 259° C.; LCMS: m/z=451.36 (M+H$^+$), $^1$H NMR (400 MHz, CD$_3$OD) δ 8.02 (s, 1H), 7.69 (m, 1H), 7.58 (s, 1H), 7.42 (m, 2H), 7.37 (m, 1H), 7.30 (m, 1H), 6.97 (d, 1H, J=8.3 Hz), 4.24 (m, 1H), 3.50 (m, 1H), 3.15 (m, 1H), 3.02 (m, 2H), 2.82 (s, 3H), 2.73 (m, 2H), 2.24 (s, 3H), 1.97 (m, 2H).

Example 411

2-[5-Chloro-2-(5-oxo-2,3,4,5-tetrahydro-1H-benzo[e][1,4]diazepin-8-ylamino)-pyrimidin-4-ylamino]-N-methylbenzamide 411a) 2-(2-tert-Butoxycarbonylamino-ethylamino)-4-nitrobenzoic acid ethyl ester. A mixture of ethyl 2-fluoro-4-nitrobenzoate (500 mg, 2.4 mmol), N-(t-butoxycarbonyl)-ethylenediamine (450 mg, 2.8 mmol) and anhydrous granular potassium carbonate (1.0 gm) in DMF (20 mL) was stirred at 60° C. for 24 hrs., filtered and concentrated. The crude product was purified by flash chromatography (silica gel, 30% EtOAc/hexanes) to afford 600 mg (72%) of the title compound as a yellow solid; MS: m/z=354 (M+H)$^+$.

411b) 2-(2-tert-Butoxycarbonylamino-ethylamino)-4-nitrobenzoic acid. A solution of 2-(2-tert-Butoxycarbonylamino-ethylamino)-4-nitro-benzoic acid ethyl ester (285 mg, 0.81 mmol) in ethanol (12 mL) was treated with 2N NaOH (4 mL) and stirred while being warmed to 40° C. After 30 minutes the mixture was concentrated to an aqueous residue. A little water was added and the pH was adjusted to 3-4 (2N HCl). The resulting precipitate was filtered, washed with water and aid-dried to constant weight to give 230 mg (88%) of the title compound as a yellow-orange solid; MS: m/z=326 (M+H)$^+$.

411c) 2-(2-Amino-ethylamino)-4-nitrobenzoic acid trifluoroacetic acid salt. To a 50% (v/v) solution of TFA/DCM (25 mL) was added 2-(2-tert-Butoxycarbonylamino-ethylamino)-4-nitro-benzoic acid (225 mg, 0.69 mmol). After being stirred for 20 minutes at ambient temperature, hplc analysis showed the reaction to be complete. The mixture was concentrated and the residue was redissolved in DCM (25 mL) and concentrated thrice to remove residual TFA to afford 235 mg (100%) of the title compound which was used without further purification; MS: m/z=226 (M+H)$^+$.

411d) 8-Nitro-1,2,3,4-tetrahydro-benzo[e][1,4]diazepin-5-one. To a solution of 2-(2-amino-ethylamino)-4-nitrobenzoic acid trifluoroacetic acid salt (220 mg, 0.65 mmol) in DMF (20 mL) was added N-methylmorpholine (320 µL, 2.9 mmol), HOBt (131 mg, 0.97 mmol) and BOP (430 mg, 0.97 mmol). The mixture was stirred overnight at room temperature, then filtered and concentrated. The residue was stirred in 10% MeOH/DCM (10 mL) for several hours, filtered, and the filtrate was washed with several milliliters of 10% MeOH/DCM before being dried to constant weight to give 110 mg (82%) of the title compound; MS: m/z=208.

411e) 8-Amino-1,2,3,4-tetrahydro-benzo[e][1,4]diazepin-5-one. A solution of 8-nitro-1,2,3,4-tetrahydro-benzo[e][1,4]diazepin-5-one (100 mg, 0.48 mmol) in DMF (5 mL) and EtOAc (5 mL) was treated with 10% Pd/C and placed on a Paar apparatus under 40 psi $H_2$ and shaken for 18 hrs at room temperature. The mixture was filtered and concentrated. Purification by flash chromatography (silica gel, 20% MeOH/DCM) afforded 71 mg (82%) of the title compound; MS: m/z=178.

411 f) 2-[5-Chloro-2-(5-oxo-2,3,4,5-tetrahydro-1H-benzo[e][1,4]diazepin-8-ylamino)-pyrimidin-4-ylamino]benzamide (CEP-19626). A solution of 2-(2,5-dichloro-pyrimidin-4-ylamino)-N-methylbenzamide (58 mg, 0.20 mmol) and 8-amino-1,2,3,4-tetrahydro-benzo[e][1,4]diazepin-5-one (35 mg, 0.20 mmol) in 2-methoxyethanol (5 mL) was treated with 4N HCl in 50% $H_2O$/dioxane (50 µL, 1 equiv.) and the mixture was stirred and heated to 110° C. After 22 hrs. the mixture was cooled to room temperature, neutralized with triethylamine and concentrated. Flash chromatography (silica gel, 20% MeOH/DCM) gave 35 mg of the title compound as a pale amber solid; m.p. 232-237° C.; MS: m/z=438/440 (M+H)$^+$, Cl-isotope pattern; $^1$H-NMR (DMSO-d$_6$, δ): 11.69 (s, 1H), 9.43 (s, 1H), 8.84 (d, 8 Hz, 1H), 8.76 (s, 1H), 8.22 (s, 1H), 7.76 (d, 7 Hz, 2H), 7.67 (d, 8 Hz, 1H), 7.48 (m, 2H), 7.15 (t, 8 Hz, 1H), 7.03 (s, 1H), 6.90 (d, 9 Hz, 1H), 3.10 (m, 2H), 2.82 (s, 3H), 2.60 (m, 2H).

Example 412

2-[5-Chloro-2-(4-methyl-5-oxo-2,3,4,5-tetrahydro-1H-benzo[e][1,4]diazepin-8-ylamino)-pyrimidin-4-ylamino]-N-methylbenzamide 412a) 2-(2-tert-Butoxycarbonylamino-ethylamino)-4-nitro-benzoic acid ethyl ester. This compound was prepared according to Example 411a, From (2-aminoethyl)-methylcarbamic acid tert-butyl ester (385 mg, 2.2 mmol), ethyl 2-fluoro-4-nitrobenzoate (390 mg, 1.8 mmol) and anhydrous potassium carbonate (510 mg, 3.6 mmol) in DMF (10 mL) stirred at 50° C. over 48 hours was obtained 493 mg (75%) of the title compound following flash chromatography over silica gel (3% MeOH/DCM); MS: m/z=368 (M+H)$^+$.

412b) 2-[2-(tert-Butoxycarbonyl-methylamino)-ethylamino]-4-nitrobenzoic acid. This compound was prepared according to Example 411b. From 2-(2-tert-butoxycarbonylamino-ethylamino)-4-nitro-benzoic acid ethyl ester (485 mg, 1.3 mmol) was obtained 420 mg (94%) of the title compound as a yellow solid, used without further purification; MS: m/z=338 (M–H)$^+$.

412c) 2-(2-Methylamino-ethylamino)-4-nitrobenzoic acid trifluoroacetic acid salt. This compound was prepared according to Example 411c. From 2-[2-(tert-butoxycarbonyl-methylamino)-ethylamino]-4-nitrobenzoic acid (400 mg, 1.2 mmol) was obtained 420 mg (99%) of the title compound as a yellow solid, used without further purification; MS: m/z=240 (M+H)$^+$.

412d) 4-Methyl-8-nitro-1,2,3,4-tetrahydro-benzo[e][1,4]diazepin-5-one. This compound was prepared according to Example 411d. From 2-(2-methylamino-ethylamino)-4-nitrobenzoic acid trifluoroacetic acid salt (250 mg, 0.71 mmol), NMM (311 µL, 2.8 mmol), HOBt (143 mg, 1.1 mmol), and BOP (469 mg, 1.1 mmol) in DMF (25 mL) was obtained 50 mg (32%) of the title compound as a light orange-yellow solid; MS: m/z=222 (M+H)$^+$.

412e) 8-Amino-4-methyl-1,2,3,4-tetrahydro-benzo[e][1,4]diazepin-5-one. This compound was prepared according to Example 411e. From 4-methyl-8-nitro-1,2,3,4-tetrahydro-benzo[e][1,4]diazepin-5-one (45 mg, 0.20 mmol) was obtained 30 mg (75%) of the title compound as an off-white solid; MS: m/z=192.

412f) 2-[5-Chloro-2-(4-methyl-5-oxo-2,3,4,5-tetrahydro-1H-benzo[e][1,4]diazepin-8-ylamino)-pyrimidin-4-ylamino]-N-methylbenzamide. This compound was prepared according to Example 411f. From 8-amino-4-methyl-1,2,3,4-tetrahydro-benzo[e][1,4]diazepin-5-one (27 mg, 0.14 mmol) and 2-(2,5-dichloro-pyrimidin-4-ylamino)-N-methylbenzamide (42 mg, 0.14 mmol) was obtained 16 mg (25%) of the title compound as a pale yellow solid following flash chromatography over silica gel (20% MeOH/DCM); m.p. 272-277; MS: m/z=452/454 (M+H)$^+$, Cl-isotope pattern; $^1$H-NMR (DMSO-d$_6$, δ): 11.68 (s, 1H), 9.43 (s, 1H), 8.83 (d, 8 Hz, 1H), 8.75 (s, 1H), 8.22 (s, 1H), 7.75 (d, 7 Hz, 1H), 7.49 (m, 2H), 7.15 (t, 8 Hz, 1H), 7.04 (s, 1H), 6.94 (d, 9 Hz, 1H), 6.10 (s, 1H), 3.42 (m, 4H), 3.01 (s, 3H), 2.81 (s, 3H).

Example 413

2-[5-Chloro-2-(1,4-dimethyl-5-oxo-2,3,4,5-tetrahydro-1H-benzo[e][1,4]diazepin-8-ylamino)-pyrimidin-4-ylamino]-N-methylbenzamide 413a) 1,4-Dimethyl-8-nitro-1,2,3,4-tetrahydro-benzo[e][1,4]diazepin-5-one. This compound was prepared according to Example 411a. From ethyl 2-fluoro-4-nitrobenzoate (565 mg, 2.7 mmol), N,N'-dimethylethylenediamine (467 mg, 5.3 mmol) and anhydrous granular potassium carbonate (733 mg) in DMF (20 mL) at 50° C. was obtained 520 mg of the title compound as a yellow solid; MS: m/z=236 (M+H)$^+$.

413b) 8-Amino-1,4-dimethyl-1,2,3,4-tetrahydro-benzo[e][1,4]diazepin-5-one. This compound was prepared according to Example 411e. From 1,4-dimethyl-8-nitro-1,2,3,4-tetrahydro-benzo[e][1,4]diazepin-5-one (150 mg, 0.64 mmol) was obtained 130 mg (99%) of the title compound as yellow-orange solid; MS: m/z=206 (M+H)$^+$.

Part 3C. 2-[5-Chloro-2-(1,4-dimethyl-5-oxo-2,3,4,5-tetrahydro-1H-benzo[e][1,4]diazepin-8-ylamino)-pyrimidin-4-ylamino]-N-methylbenzamide. This compound was prepared according to Example 411f. From 8-amino-1,4-dimethyl-1,2,3,4-tetrahydro-benzo[e][1,4]diazepin-5-one (100 mg, 0.49 mmol) and 2-(2,5-dichloro-pyrimidin-4-ylamino)-N-methylbenzamide (144 mg, 0.49 mmol) was obtained 97 mg (43%) of the title compound following flash chromatography (silica gel, 20% MeOH/DCM); m.p. 243-247° C.; MS: m/z=466/468 (M+H)$^+$, Cl-isotope pattern; $^1$H-NMR (DMSO-d$_6$, δ): 11.64 (s, 1H), 9.57 (s, 1H), 8.76 (m, 2H), 8.27 (s, 1H), 7.76 (d, 8 Hz, 1H), 7.50 (t, 7 Hz, 1H), 7.40 (d, 7 Hz, 1H), 7.33 (d, 8 Hz, 1H), 7.20 (s, 1H), 7.15 (t, 7 Hz, 1H), 3.42 (t, 5 Hz, 2H), 3.25 (t, 5 Hz, 2H), 3.04 (s, 3H), 2.81 (s, 3H), 2.68 (s, 3H).

Example 414

2-[5-Chloro-2-(1-methyl-5-oxo-2,3,4,5-tetrahydro-1H-benzo[e][1,4]diazepin-8-ylamino)-pyrimidin-4-ylamino]-N-methylbenzamide 414a) 2,2,2-Trifluoro-N-(2-methylamino-ethyl)-acetamide. A solution of N-methyl-ethylenediamine (1.0 gm, 13.5 mmol) in THF (25 mL) was cooled in an ice-water bath and treated dropwise over 5 minutes with ethyl trifluoroacetate according to Xu et. al. (Tetrahedron Lett., (1995), 36(41), 7357-7360). After being stirred for an additional 30 minutes the mixture was concentrated in-vacuo to give 2.5 gm (100%) of the title compound as a viscous oil which slowly solidified on standing and was used without further purification; MS: m/z=293 (M+Na)$^+$.

414b) 2-{Methyl-[2-(2,2,2-trifluoro-acetylamino)-ethyl]-amino}-4-nitrobenzoic acid ethyl ester. This compound was prepared according to Example 411a. From ethyl 2-fluoro-4-nitrobenzoate (213 mg, 1.0 mmol) and 2,2,2-trifluoro-N-(2-methylamino-ethyl)-acetamide (170 mg, 1.0 mmol) was obtained 167 mg (67%) of the title compound following flash chromatography on silica gel (30% EtOAc/hexanes); MS: m/z=364 (M+H)$^+$.

414c) 1-Methyl-8-nitro-1,2,3,4-tetrahydro-benzo[e][1,4]diazepin-5-one. To a solution of 144 mg (0.40 mmol) in anhydrous methanol (15 mL) was added powdered sodium methoxide (88 mg, 1.6 mmol) and the mixture was stirred at room temperature overnight. The solvent was removed in-vacuo, water (5 mL) was added, and the pH was adjusted to about 4 (3N HCl). The precipitate was collected by vacuum filtration, washed with water and hexanes and dried to constant weight to afford 69 mg (79%) of the title compound as a yellow solid; MS: m/z=222 (M+H)$^+$.

414d) 8-Amino-1-methyl-1,2,3,4-tetrahydro-benzo[e][1,4]diazepin-5-one. This compound was prepared according to Example 411e. From 1-methyl-8-nitro-1,2,3,4-tetrahydro-benzo[e][1,4]diazepin-5-one (61 mg, 0.28 mmol) was obtained 54 mg (100%) of the title compound as an orange solid; MS: m/z=192 (M+H)$^+$.

Part 4E. 2-[5-Chloro-2-(1-methyl-5-oxo-2,3,4,5-tetrahydro-1H-benzo[e][1,4]diazepin-8-ylamino)-pyrimidin-4-ylamino]-N-methylbenzamide. This compound was prepared according to Example 411f. From 2-(2,5-dichloro-pyrimidin-4-ylamino)-N-methylbenzamide (78 mg, 0.26 mmol) and 8-amino-1-methyl-1,2,3,4-tetrahydro-benzo[e][1,4]diazepin-5-one (50 mg, 0.26 mmol) was obtained 57 mg (48%) of the title compound following flash chromatography on silica gel (20% MeOH/DCM); m.p. 210-215° C. (dec.); MS: m/z=452/454 (M+H)$^+$; Cl-isotope pattern; $^1$H-NMR (DMSO-d$_6$, δ): 11.65 (s, 1H), 9.57 (s, 1H), 8.75 (m, 2H), 8.27 (s, 1H), 8.01 (s, 1H), 7.76 (d, 7 Hz, 1H), 7.50 (t, 7 Hz, 1H), 7.38 (s, 2H), 7.21 (s, 1H), 7.16 (t, 8 Hz, 1H), 3.40 (s, 2H), 3.32 (s, 2H), 2.82 (s, 3H), 2.68 (s, 3H).

Example 415

2-{5-Chloro-2-[1-(2-diethylamino-ethyl)-5-oxo-2,3,4,5-tetrahydro-1H-benzo[e][1,4]diazepin-8-ylamino]-pyrimidin-4-ylamino}-N-methylbenzamide (415a) N-[2-(2-Diethylamino-ethylamino)-ethyl]-2,2,2-trifluoro-acetamide. This compound was prepared according to Example 414a. From N-(2-diethylamino-ethyl)-ethylenediamine (2.5 gm, 15.6 mmol) and ethyltrifluoroacetate (2.3 g, 16.5 mmol) was obtained 4.0 g (100%) of the title compound as an amber viscous oil; MS: m/z=256 (M+H)$^+$.

415b) 2-{(2-Diethylaminoethyl)-[2-(2,2,2-trifluoro-acetylamino)-ethyl]-amino}-4-nitrobenzoic acid ethyl ester. This compound was prepared according to Example 411a. From ethyl 2-fluoro-4-nitrobenzoate (500 mg, 2.3 mmol) and N-[2-(2-diethylamino-ethylamino)-ethyl]-2,2,2-trifluoro-acetamide (719 mg, 2.8 mmol) was obtained 650 mg (65%) of the title compound following flash chromatography on silica gel (30% MeOH/DCM); MS: m/z=449 (M+H)$^+$.

415c) 1-(2-Diethylaminoethyl)-8-nitro-1,2,3,4-tetrahydro-benzo[e][1,4]diazepin-5-one. This compound was prepared according to Example 414c. From 2-{(2-diethylamino-ethyl)-[2-(2,2,2-trifluoro-acetylamino)-ethyl]-amino}-4-nitrobenzoic acid ethyl ester (200 mg, 0.45 mmol) was obtained 71 mg (52%) of the title compound as a yellow-orange solid; MS: 307.

415d) 8-amino-1-(2-diethylaminoethyl)-1,2,3,4-tetrahydro-benzo[e][1,4]diazepin-5-one. This compound was prepared according to Example 411e. From 1-(2-diethylamino-ethyl)-8-nitro-1,2,3,4-tetrahydro-benzo[e][1,4]diazepin-5-one (63 mg, 0.21 mmol) was obtained 57 mg (100%) of the title compound as an off-white solid; MS: m/z=277 (M+H)$^+$.

415e) 2-{5-Chloro-2-[1-(2-diethylaminoethyl)-5-oxo-2,3,4,5-tetrahydro-1H-benzo[e][1,4]diazepin-8-ylamino]-pyrimidin-4-ylamino}-N-methylbenzamide. This compound was prepared according to Example 411f. From 2-(2,5-dichloro-pyrimidin-4-ylamino)-N-methylbenzamide (57 mg, 0.19 mmol) and 8-amino-1-(2-diethylaminoethyl)-1,2,3,4-tetrahydro-benzo[e][1,4]diazepin-5-one (53 mg, 0.19 mmol) was obtained 64 mg (62%) of the title compound following flash chromatography on silica gel (20% MeOH/DCM); m.p. 180-184° C. (dec.); MS: m/z=538/540 (M+H)$^+$; Cl-isotope pattern; $^1$H-NMR (DMSO-d$_6$, δ): 11.67 (s, 1H), 10.11 (s, 1H), 9.62 (s, 1H), 8.82 (d, 5 Hz, 1H), 8.75 (d, 8 Hz, 1H), 8.29 (s, 1H), 8.05 (s, 1H) 7.78 (d, 8 Hz, 1H), 7.52 (t, 7 Hz, 1H), 7.43 (s, 2H), 7.17 (t, 8 Hz, 1H), 3.46 (m, 2H), 3.25 (m, 2H), 3.18 (m, 4H), 3.12 (m, 4H), 2.81 (s, 3H), 1.14 (m, 6H).

Example 416

2-[5-Chloro-2-(1,4-dimethyl-5-oxo-2,3,4,5-tetrahydro-1H-benzo[e][1,4]diazepin-8-ylamino)-pyrimidin-4-ylamino]-N-methylbenzamide 416°) 8-Amino-1,4-dimethyl-1,2,3,4-tetrahydro-benzo[e][1,4]diazepin-5-one. A solution of 1,4-dimethyl-8-nitro-1,2,3,4-tetrahydro-benzo[e][1,4]diazepin-5-one (200 mg, 0.84 mmol) in 1,4-dioxane (10 mL) was treated with powdered LiAlH$_4$ (130 mg, 3.40 mmol) and heated to 65° C. After 20 hrs, the mixture was quenched by dropwise addition of ethyl acetate. Following concentration in-vacuo, the residue was partitioned between dichlormethane and water, the organic phase was washed with brine, dried over anhydrous magnesium sulfate, filtered and concentrated. Flash chromatography over silica gel (1% NH$_4$OH/20% MeOH/DCM) gave 47 mg (30%) of the title compound as a yellow-orange foam; MS: m/z=192.

416b) 2-[5-Chloro-2-(1,4-dimethyl-5-oxo-2,3,4,5-tetrahydro-1H-benzo[e][1,4]diazepin-8-ylamino)-pyrimidin-4-ylamino]-N-methylbenzamide. This compound was prepared according to Example 411f. From 2-(2,5-dichloro-pyrimidin-4-ylamino)-N-methylbenzamide (62 mg, 0.21 mmol) and 8-amino-1,4-dimethyl-1,2,3,4-tetrahydro-benzo[e][1,4]diazepin-5-one (40 mg, 0.21 mmol) was obtained 48 mg (50%) of the title compound following flash chromatography; MS: m/z=452/454 (M+H)$^+$, Cl-isotope pattern; $^1$H-NMR (DMSO-d$_6$, δ): 11.69 (s, 1H), 9.55 (s, 1H), 8.77 (m, 2H), 8.26 (s, 1H), 7.78 (d, 8 Hz, 1H), 7.45 (t, 7 Hz, 1H), 7.43 (d, 7 Hz, 1H), 7.29 (s, 1H), 7.23 (d, 8 Hz, 1H), 7.15 (t, 7 Hz, 1H), 3.38 (m, 2H), 3.06 (m, 2H), 2.83 (s, 2H), 2.80 (s, 3H), 2.77 (s, 3H), 2.73 (s, 3H).

Example 417

2-[5-Chloro-2-(1-methyl-2,3,4,5-tetrahydro-1H-benzo[e][1,4]diazepin-8-ylamino)-pyrimidin-4-ylamino]-N-methylbenzamide 417a) 1-Methyl-2,3,4,5-tetrahydro-1H-benzo[e][1,4]diazepin-8-ylamine. 1-Methyl-8-nitro-1,2,3,4-tetrahydro-benzo

[e][1,4]diazepin-5-one (540 mg, 2.8 mmol; obtained from the procedure for Example 414c) in anhydrous THF (35 mL) was treated with 1M BH$_3$-THF (14.1 mL, 5 equiv.) and heated to reflux. After four days the excess reagent was quenched by careful dropwise addition of methanol. The mixture was concentrated and treated with 3N HCl (25 mL) at reflux for one hour, then stirred at room temperature overnight. The pH was adjusted to about 9 (4N NaOH) and extracted into dichloromethane (3×25 mL). The combined organic phase was washed with saturated sodium bicarbonate, brine, dried (MgSO$_4$), filtered and concentrated. The residue was purified by flash chromatography on silica gel (1% NH$_4$OH/10% MeOH/DCM) to afford 74 mg (15%) of the title compound as a yellow-orange solid; MS: 178 (M+H)$^+$.

417b) 2-[5-Chloro-2-(1-methyl-2,3,4,5-tetrahydro-1H-benzo[e][1,4]diazepin-8-ylamino)-pyrimidin-4-ylamino]-N-methylbenzamide.

This compound was prepared according to Example 411f, with the modification of using 2 molar equivalents of 4N HCl. From 1-methyl-2,3,4,5-tetrahydro-1H-benzo[e][1,4]diazepin-8-ylamine (68 mg, 0.38 mmol) and 2-(2,5-dichloro-pyrimidin-4-ylamino)-N-methylbenzamide (106 mg, 0.36 mmol) was obtained 69 mg (43%) of the title compound as a mustard yellow solid; m.p. 210-220° C. (dec.); MS: m/z=438/440 (M+H)$^+$, Cl-isotope pattern; $^1$H-NMR (DMSO-d$_6$, δ): 11.65 (s, 1H), 9.35 (s, 1H), 8.80 (m, 2H), 8.22 (s, 1H), 7.78 (d, 8 Hz, 1H), 7.50 (t, 7 Hz, 1H), 7.31 (d, 7 Hz, 1H), 7.15 (m, 2H), 7.05 (d, 7 Hz, 1H), 3.78 (s, 2H), 2.92 (m, 4H), 2.82 (s, 3H), 2.70 (s, 3H).

Example 418

2-[5-Chloro-2-(1,4-diethyl-5-oxo-2,3,4,5-tetrahydro-1H-benzo[e][1,4]diazepin-8-ylamino)-pyrimidin-4-ylamino]-N-methylbenzamide 418a) 1,4-Diethyl-8-nitro-1,2,3,4-tetrahydro-benzo[e][1,4]diazepin-5-one. This compound was prepared according to the procedure for Example 413a. From ethyl 2-fluoro-4-nitrobenzoate (100 mg, 0.50 mmol), N,N'-diethylethylenediamine (88 mg, 0.75 mmol) and anhydrous granular potassium carbonate (280 mg) in DMF (3 mL) at 100° C. was obtained 140 mg of the title compound as a yellow solid; MS: m/z=264 (M+H)$^+$.

418b) 8-Amino-1,4-diethyl-1,2,3,4-tetrahydro-benzo[e][1,4]diazepin-5-one. This compound was prepared according to Example 411e. From 1,4-diethyl-8-nitro-1,2,3,4-tetrahydro-benzo[e][1,4]diazepin-5-one (3.5 g, 13.3 mmol) was obtained 2.9 g (94%) of the title compound; MS: 234 (M+H)$^+$.

418c) 2-[5-Chloro-2-(1,4-diethyl-5-oxo-2,3,4,5-tetrahydro-1H-benzo[e][1,4]diazepin-8-ylamino)-pyrimidin-4-ylamino]-N-methylbenzamide. This compound was prepared according to the procedure for Example 411f. From 8-amino-1,4-diethyl-1,2,3,4-tetrahydro-benzo[e][1,4]diazepin-5-one (110 mg, 0.47 mmol) and 2-(2,5-dichloro-pyrimidin-4-ylamino)-N-methylbenzamide (133 mg, 0.45 mmol) was obtained 83 mg (37%) of the title compound following flash chromatography on silica gel (10% MeOH/DCM); m.p. 183-186; MS: m/z=494/496 (M+H)$^+$, Cl-isotope pattern; $^1$H-NMR (DMSO-d$_6$, δ): 11.64 (s, 1H), 9.57 (s, 1H), 8.76 (m, 2H), 8.27 (s, 1H), 7.76 (d, 8 Hz, 1H), 7.50 (t, 7 Hz, 1H), 7.40 (d, 7 Hz, 1H), 7.33 (d, 8 Hz, 1H), 7.20 (s, 1H), 7.15 (t, 7 Hz, 1H), 3.49 (q, 7 Hz, 2H), 3.40 (t, 5 Hz, 2H), 3.24 (t, 5 Hz, 2H), 3.04 (t, 7 Hz, 2H), 2.81 (s, 3H), 1.10 (m, 6H).

Example 419

2-[5-Chloro-2-(1,4-diethyl-2,3,4,5-tetrahydro-1H-benzo[e][1,4]diazepin-8-ylamino)-pyrimidin-4-ylamino]-N-methylbenzamide 419a) 1,4-Diethyl-2,3,4,5-tetrahydro-1H-benzo[e][1,4]diazepin-8-ylamine. This compound was prepared according to Example 416a. From 1,4-diethyl-8-nitro-1,2,3,4-tetrahydro-benzo[e][1,4]diazepin-5-one (1.2 g, 4.6 mmol) was obtained 176 mg (18%) of the title compound following flash chromatography; MS: m/z=220.

419b) 2-[5-Chloro-2-(1,4-diethyl-2,3,4,5-tetrahydro-1H-benzo[e][1,4]diazepin-8-ylamino)-pyrimidin-4-ylamino]-N-methylbenzamide. This compound was prepared according to Example 416b). From 1,4-diethyl-2,3,4,5-tetrahydro-1H-benzo[e][1,4]diazepin-8-ylamine (68 mg, 0.31 mmol) and 2-(2,5-dichloro-pyrimidin-4-ylamino)-N-methylbenzamide (88 mg, 0.29 mmol) was obtained the title compound as a mustard yellow solid; m.p. 201-207° C. (dec.); MS: 480/482 (M+H)$^+$, Cl-isotope pattern; $^1$H-NMR (DMSO-d$_6$, δ): 11.69 (s, 1H), 9.55 (s, 1H), 8.77 (m, 2H), 8.26 (s, 1H), 7.78 (d, 8 Hz, 1H), 7.45 (t, 7 Hz, 1H), 7.43 (d, 7 Hz, 1H), 7.29 (s, 1H), 7.23 (d, 8 Hz, 1H), 7.15 (t, 7 Hz, 1H), 3.11-3.04 (m, 10H), 2.81 (s, 3H), 1.19 (m, 6H).

Example 420

2-[5-Chloro-2-(1-methyl-2,3,4,5-tetrahydro-1H-benzo[e][1,4]diazepin-7-ylamino)-pyrimidin-4-ylamino]-N-methylbenzamide 420°) 1-Methyl-7-nitro-1,2,3,4-tetrahydro-benzo[e][1,4]diazepin-5-one. This compound was prepared according to Example 411a. From methyl 2-fluoro-5-nitrobenzoate (4.0 g, 20.0 mmol) and N-methyl-ethylenediamine (1.6 g, 21.0 mmol) was obtained 1.4 g (32%) of the title compound as a yellow solid following flash chromatography over silica gel (10% MeOH/DCM); MS: m/z=222 (M+H)$^+$.

420b) 7-Amino-1-methyl-1,2,3,4-tetrahydro-benzo[e][1,4]diazepin-5-one. A solution of 1-methyl-7-nitro-1,2,3,4-tetrahydro-benzo[e][1,4]diazepin-5-one (1.3 g, 5.8 mmol) in ethanol (100 mL) was treated with 10% Pd/C (100 mg) and shaken on a Paar apparatus under 40-50 psi H$_2$ at room temperature. After 17 hours the mixture was filtered and concentrated to afford 1.1 g (100%) of the title compound which was used without further purification; MS: m/z=192 (M+H)$^+$.

420c) 1-Methyl-2,3,4,5-tetrahydro-1H-benzo[e][1,4]diazepin-7-ylamine. This compound was prepared according to the procedure described for Example 417a. From 7-amino-1-methyl-1,2,3,4-tetrahydro-benzo[e][1,4]diazepin-5-one (1.2 g, 6.2 mmol) was obtained 0.56 g (50%) of the title compound as a mustard yellow solid following flash chromatography over silica gel (1% NH$_4$OH/30% MeOH/DCM); MS: m/z=178 (M+H)$^+$.

420d) 2-[5-Chloro-2-(1-methyl-2,3,4,5-tetrahydro-1H-benzo[e][1,4]diazepin-7-ylamino)-pyrimidin-4-ylamino]-N-methylbenzamide. This compound was prepared according to the procedure for Example 417b. From 1-methyl-2,3,4,5-tetrahydro-1H-benzo[e][1,4]diazepin-7-ylamine (100 mg, 0.56 mmol) and 2-(2,5-dichloro-pyrimidin-4-ylamino)-N-methylbenzamide (168 mg, 0.56 mmol) was obtained 130 mg (53%) of the title compound following trituration of the crude isolate with ether; m.p. 145-149° C.; MS: m/z=438/440 (M+H)$^+$, Cl-isotope pattern; $^1$H-NMR (DMSO-d$_6$, δ): 11.60 (s, 1H), 9.22 (s, 1H), 8.75 (m, 2H), 8.20 (s, 1H), 7.76 (d, 7 Hz, 1H), 7.50-7.35 (m, 4H), 7.16 (t, 7 Hz, 1H), 6.85 (d, 7 Hz, 1H), 3.69 (s, 3H), 2.90 (m, 2H), 2.83 (m, 7H).

Example 421

N-{2-[5-Chloro-2-(1-methyl-2,3,4,5-tetrahydro-1H-benzo[e][1,4]diazepin-7-ylamino)-pyrimidin-4-ylamino]-phenyl}-methanesulfonamide 421a) N-{2-[5-Chloro-2-(1-methyl-2,3,4,5-tetrahydro-1H-benzo[e][1,4]diazepin-7-ylamino)-pyrimidin-4-ylamino]-phenyl}-methanesulfonamide. This compound was prepared according to Example 417b. From 1-methyl-2,3,4,5-tetrahydro-1H-benzo[e][1,4]diazepin-7-ylamine (64 mg, 0.36 mmol) and N-[2-(2,5-dichloro-pyrimidin-4-ylamino)-phenyl]-methanesulfonamide (120, 0.36 mmol) was obtained 118 mg (69%) of the title compound following trituration of the crude isolate with ether; m.p. 243-250° C. (dec.); MS: 474/476 (M+H)$^+$, Cl-isotope pattern; $^1$H-NMR (DMSO-d$_6$, δ): 9.90 (br, 1H), 9.40 (s, 1H), 9.18 (br, 2H), 8.29 (s, 1H), 7.78 (s, 1H), 7.50-7.35 (m, 5H), 7.88 (d, 8 Hz, 1H), 3.92 (s, 2H), 3.20 (m, 2H), 3.10 (m, 2H), 2.97 (s, 3H), 3.85 (s, 3H).

Example 422

N-{(1R,2R)-2-[5-Chloro-2-(1-methyl-2,3,4,5-tetrahydro-1H-benzo[e][1,4]diazepin-7-ylamino)-pyrimidin-4-ylamino]-cyclohexyl}-methanesulfonamide 422a) N-{(1R,2R)-2-[5-Chloro-2-(1-methyl-2,3,4,5-tetrahydro-1H-benzo[e][1,4]diazepin-7-ylamino)-pyrimidin-4-ylamino]-cyclohexyl}-methanesulfonamide hydrochloride. This compound was prepared according to Example 417b. From 1-methyl-2,3,4,5-tetrahydro-1H-benzo[e][1,4]diazepin-7-ylamine (62 mg, 0.35 mmol) and N-[(1R,2R)-2-(2,5-Dichloro-pyrimidin-4-ylamino)-cyclohexyl]-methanesulfonamide (119 mg, 0.35 mmol) was obtained 90 mg (54%) of the title compound following filtration of the cooled reaction mixture and washing with ether; m.p. 289-296° C. (dec.); MS: m/z=480/482 (M+H)$^+$, Cl-isotope pattern; $^1$H-NMR (DMSO-d$_6$, δ): 10.30 (br, 1H), 9.30 (br, 2H), 8.18 (s, 1H), 7.95 (br, 1H), 7.62 (s, 1H), 7.59 (d, 7 Hz, 1H), 7.20 (d, 7 Hz, 1H), 7.03 (d, 7 Hz, 1H), 4.19 (s, 2H), 3.87 (m, 1H), 3.41 (m, 1H), 3.24 (m, 2H), 3.16 (m, 2H), 2.97 (s, 3H), 2.89 (s, 3H), 2.07-1.94 (m, 2H), 1.75-1.67 (m, 2H), 1.50-1.35 (m, 2H), 1.33-1.12 (m, 2H).

Example 423

N-{2-[5-Chloro-2-(1,4-diethyl-5-oxo-2,3,4,5-tetrahydro-1H-benzo[e][1,4]diazepin-8-ylamino)-pyrimidin-4-ylamino]-phenyl}-methanesulfonamide 423a) N-{2-[5-Chloro-2-(1,4-diethyl-5-oxo-2,3,4,5-tetrahydro-1H-benzo[e][1,4]diazepin-8-ylamino)-pyrimidin-4-ylamino]-phenyl}-methanesulfonamide. This compound was prepared according to Example 417b. From 8-amino-1,4-diethyl-1,2,3,4-tetrahydro-benzo[e][1,4]diazepin-5-one (77 mg, 0.33 mmol) and N-[2-(2,5-Dichloro-pyrimidin-4-ylamino)-phenyl]-methanesulfonamide (110 mg, 0.33 mmol) was obtained 100 mg (57%) of the title compound following preparative tlc on silica gel (10% 7N NH$_3$-MeOH/DCM); m.p. 145-153° C.; MS: 530/532 (M+H)$^+$, Cl-isotope pattern; $^1$H-NMR (DMSO-d$_6$, δ): 9.48 (s, 1H), 9.28 (br, 1H), 8.60 (s, 1H), 8.22 (s, 1H), 7.92 (d, 7 Hz, 1H), 7.50-7.10 (m, 6H), 3.50-3.18 (m, 8H), 2.95 (s, 3H), 1.15-1.05 (m, 6H).

Example 424

N-{(1R,2R)-2-[5-Chloro-2-(1,4-diethyl-5-oxo-2,3,4,5-tetrahydro-1H-benzo[e][1,4]diazepin-8-ylamino)-pyrimidin-4-ylamino]-cyclohexyl}-methanesulfonamide 424a) Prepared according to Example 417b. From 8-amino-1,4-diethyl-1,2,3,4-tetrahydro-benzo[e][1,4]diazepin-5-one (80 mg, 0.34 mmol) and N-[(1R,2R)-2-(2,5-Dichloro-pyrimidin-4-ylamino)-cyclohexyl]-methanesulfonamide (116 mg, 0.34 mmol) was obtained 79 mg (43%) of the title compound following preparative tlc on silica gel (10% 7N NH$_3$-MeOH/DCM); m.p. 138-146° C.; MS: 536/538 (M+H)$^+$, Cl-isotope pattern; $^1$H-NMR (DMSO-d$_6$, δ): 9.30 (s, 1H), 8.00 (s, 1H), 7.58 (d, 7 Hz, 1H), 7.35 (d, 7 Hz, 1H), 7.17 (m, 2H), 6.78 (d, 7 Hz, 1H), 3.85 (m, 1H), 3.52 (m, 2H), 3.40 (m, 2H), 3.28 (m, 2H), 3.16 (m, 2H), 2.95 (s, 3H), 2.08 (m, 2H), 1.70 (m, 2H), 1.30 (m, 5H), 1.18 (m, 6H).

Example 425

N-{2-[5-Chloro-2-(1,4-diethyl-2,3,4,5-tetrahydro-1H-benzo[e][1,4]diazepin-8-ylamino)-pyrimidin-4-ylamino]-phenyl}-methanesulfonamide 425a) N-{2-[5-Chloro-2-(1,4-diethyl-2,3,4,5-tetrahydro-1H-benzo[e][1,4]diazepin-8-ylamino)-pyrimidin-4-ylamino]-phenyl}-methanesulfonamide. This compound was prepared according to Example 417b. From 1,4-diethyl-2,3,4,5-tetrahydro-1H-benzo[e][1,4]diazepin-8-ylamine (67 mg, 0.31 mmol) and N-[2-(2,5-dichloro-pyrimidin-4-ylamino)-phenyl]-methanesulfonamide (102 mg, 0.31 mmol) was obtained 96 mg (61%) of the title compound following preparative tlc on silica gel (10% 7N NH$_3$-MeOH/DCM); MS: 516/518 (M+H)$^+$, Cl-isotope pattern; $^1$H-NMR (DMSO-d$_6$, δ): 9.25 (m, 2H), 8.69 (s, 1H), 8.20 (s, 1H), 8.08 (m, 1H), 7.40 (d, 7 Hz, 1H), 7.20 (m, 3H), 7.10 (s, 1H), 6.93 (s, 1H), 3.67 (s, 2H), 3.00-2.90 (m+s, 7H), 2.82 (m, 4H), 1.10-1.00 (m, 6H).

Example 426

N-{(1R,2R)-2-[5-Chloro-2-(1,4-diethyl-2,3,4,5-tetrahydro-1H-benzo[e][1,4]diazepin-8-ylamino)-pyrimidin-4-ylamino]-cyclohexyl}-methanesulfonamide 426a) N-{(1R,2R)-2-[5-Chloro-2-(1,4-diethyl-2,3,4,5-tetrahydro-1H-benzo[e][1,4]diazepin-8-ylamino)-pyrimidin-4-ylamino]-cyclohexyl}-methanesulfonamide. This compound was prepared according to Example 417b. From 1,4-diethyl-2,3,4,5-tetrahydro-1H-benzo[e][1,4]diazepin-8-ylamine (61 mg, 0.28 mmol) and N-[(1R,2R)-2-(2,5-Dichloro-pyrimidin-4-ylamino)-cyclohexyl]-methanesulfonamide (94 mg, 0.28 mmol) was obtained 113 mg (78%) of the title compound following preparative tlc on silica gel (10% 7N NH$_3$-MeOH/DCM); m.p. 88-103° C.; MS: 522/524 (M+H)$^+$, Cl-isotope pattern; $^1$H-NMR (DMSO-d$_6$, δ): 9.02 (s, 1H), 7.95 (s, 1H), 7.35 (d, 7 Hz, 1H), 7.20 (s, 1H), 7.17 (s, 1H), 6.98 (d, 7 Hz, 1H), 6.68 (d, 7 Hz, 1H), 3.82 (m, 1H), 3.59 (m, 2H), 3.18 (m, 2H), 2.95 (m, 6H), 2.77 (m, 2H), 2.40 (m, 2H), 2.08 (m, 2H), 1.70 (m, 2H), 1.30 (m, 4H), 1.19 (t, 5 Hz, 3H), 1.05 (t, 5 Hz, 3H).

Example 427

N-{(1R,2R)-2-[5-Chloro-2-(7-chloro-1,4-diethyl-2,3,4,5-tetrahydro-1H-benzo[e][1,4]diazepin-8-ylamino)-pyrimidin-4-ylamino]-cyclohexyl}-methanesulfonamide 427a) 7-Chloro-1,4-diethyl-2,3,4,5-tetrahydro-1H-benzo[e][1,4]diazepin-8-ylamine. To a solution of 1,4-diethyl-2,3,4,5-tetrahydro-1H-benzo[e][1,4]diazepin-8-ylamine (119 mg, 0.54 mmol) in acetonitrile (25 mL) was added NCS (80 mg, 0.60 mmol) and the mixture was heated to reflux for three hours. The mixture was concentrated, the residue was dissolved in dichloromethane and washed with 10% aqueous sodium thiosulfate, water and brine, dried over anhydrous magnesium sulfate, filtered and concentrated to afford 115 mg (83%) of the title compound as a viscous amber oil which was used without further purification; MS: m/z=254/256 (M+H)$^+$, Cl-isotope pattern.

427b) N-{(1R,2R)-2-[5-Chloro-2-(7-chloro-1,4-diethyl-2,3,4,5-tetrahydro-1H-benzo[e][1,4]diazepin-8-ylamino)-pyrimidin-4-ylamino]-cyclohexyl}-methanesulfonamide. This compound was prepared according to the procedure for Example 417b. From 7-chloro-1,4-diethyl-2,3,4,5-tetrahydro-1H-benzo[e][1,4]diazepin-8-ylamine (70 mg, 0.28 mmol) and N-[(1R,2R)-2-(2,5-Dichloro-pyrimidin-4-ylamino)-cyclohexyl]-methanesulfonamide (94 mg, 0.28 mmol) was obtained 51 mg (33%) of the title compound following preparative tlc on silica gel (5% MeOH/DCM); m.p. 88-103° C.; MS: 556 (M+H)$^+$, 2Cl-isotope pattern; $^1$H-NMR (DMSO-d$_6$, δ): 8.09 (s, 1H), 7.91 (s, 1H), 7.49 (s, 1H), 7.23 (s, 1H), 7.10 (d, 7 Hz, 1H), 6.77 (d, 7 Hz, 1H), 3.82 (m, 1H), 3.63 (m, 2H), 3.18 (m, 2H), 2.98 (m, 2H), 2.90 (s, 3H), 2.80 (m, 3H), 2.42 (m, 2H), 1.98 (m, 2H), 1.65 (m, 2H), 1.30 (m, 4H), 1.15 (t, 5 Hz, 3H), 1.05 (t, 5 Hz, 3H).

Example 428

2-[5-Chloro-2-(1-methyl-5-oxo-2,3,4,5-tetrahydro-1H-benzo[e][1,4]diazepin-7-ylamino)-pyrimidin-4-ylamino]-N-methylbenzamide 428a) 2-[5-Chloro-2-(1-methyl-5-oxo-2,3,4,5-tetrahydro-1H-benzo[e][1,4]diazepin-7-ylamino)-pyrimidin-4-ylamino]-N-methylbenzamide. This compound was prepared according to the procedure for Example 417b. From 7-amino-1-methyl-1,2,3,4-tetrahydro-benzo[e][1,4]diazepin-5-one (75 mg, 0.39 mmol) and 2-(2,5-dichloro-pyrimidin-4-ylamino)-N-methylbenzamide (111 mg, 0.37 mmol) was obtained 48 mg (30%) of the title compound following preparative tlc (20% MeOH/DCM); m.p. 235-245° C. (dec.); MS: m/z/=452/454 (M+H)$^+$, Cl-isotope pattern; $^1$H-NMR (DMSO-d$_6$, δ): 11.64 (s, 1H), 9.36 (s, 1H), 8.75 (m, 2H), 8.19 (s, 2H), 7.76 (d, 7 Hz, 1H), 7.70 (m, 2H), 7.47 (t, 7 Hz, 1H), 7.11 (t, 7 Hz, 1H), 6.88 (d, 8 Hz, 1H), 3.13 (m, 4H), 2.79 (s, 3H), 2.75 (s, 3H).

Example 429

N-(2-{5-Chloro-2-[4-(2-methoxy-ethyl)-1-methyl-2,3,4,5-tetrahydro-1H-benzo[e][1,4]diazepin-7-ylamino]-pyrimidin-4-ylamino}-phenyl)-methanesulfonamide 429a) N-(2-{5-Chloro-2-[4-(2-methoxy-ethyl)-1-methyl-2,3,4,5-tetrahydro-1H-benzo[e][1,4]diazepin-7-ylamino]-pyrimidin-4-ylamino}-phenyl)-methanesulfonamide. To a solution of N-{2-[5-chloro-2-(1-methyl-2,3,4,5-tetrahydro-1H-benzo[e][1,4]diazepin-7-ylamino)-pyrimidin-4-ylamino]-phenyl}-methanesulfonamide (53 mg, 0.11 mmol) in DMF (2 mL) was added diisopropylethylamine (30 μL) and 1-bromo-2-methoxyethane (31 μL, 0.34 mmol). A few milligrams of KI was added and the mixture was allowed to stir at room temperature overnight. Preparative tlc (1% NH$_4$OH/10% MeOH/DCM) afforded 28 mg (47%) of the title compound; m.p. 203-210° C.; MS: m/z=531 (M–H)$^+$; 1H-NMR (CDCl$_3$, δ): 7.98 (s, 1H), 7.83 (m, 1H), 7.36 (d, 6 Hz, 1H), 7.28 (2, 2H), 7.22 (m, 1H), 7.14 (s, 1H), 6.73 (d, 8 Hz, 1H), 3.71 (s, 2H), 3.44 (t, 6 Hz, 2H), 3.30 (s, 3H), 2.94 (m, 6H), 2.88 (s, 3H), 2.83 (s, 3H).

Example 430

N-((1R,2R)-2-{5-Chloro-2-[4-(2-methoxy-ethyl)-1-methyl-2,3,4,5-tetrahydro-1H-benzo[e][1,4]diazepin-7-ylamino]-pyrimidin-4-ylamino}-cyclohexyl)-methanesulfonamide 430a) N-((1R,2R)-2-{5-Chloro-2-[4-(2-methoxy-ethyl)-1-methyl-2,3,4,5-tetrahydro-1H-benzo[e][1,4]diazepin-7-ylamino]-pyrimidin-4-ylamino}-cyclohexyl)-methanesulfonamide. This compound was prepared according to the procedure of Example 429a. From N-{(1R,2R)-2-[5-chloro-2-(1-methyl-2,3,4,5-tetrahydro-1H-benzo[e][1,4]diazepin-7-ylamino)-pyrimidin-4-ylamino]-cyclohexyl}-methanesulfonamide (17 mg, 0.04 mmol) and 1-bromo-2-methoxyethane (4 μL, 0.05 mmol) was obtained 10 mg (45%) of the title compound following preparative tlc (10% MeOH/DCM; m.p. 97-110° C.; $^1$H-NMR (CDCl$_3$, δ): 7.92 (s, 1H), 7.31 (m, 1H), 6.88 (d, 8 Hz, 1H), 6.75 (s, 1H), 5.53 (br, 1H), 5.35 (d, 7 Hz, 1H), 4.70 (s, 1H), 3.96 (s, 1H), 3.85 (m, 1H), 3.54 (t, 5 Hz, 2H), 3.38 (s, 3H), 3.22 (m, 1H), 3.07 (m, 2H), 2.98 (s, 3H), 2.90 (s, 3H), 2.79 (s, 3H), 2.68 (t, 5 Hz, 2H), 2.02 (m, 2H), 1.83 (m, 2H), 1.36 (m, 2H), 1.28 (m, 2H).

Example 431

N-{2-[5-Chloro-2-(7-chloro-1,4-diethyl-2,3,4,5-tetrahydro-1H-benzo[e][1,4]diazepin-8-ylamino)-pyrimidin-4-ylamino]-phenyl}-methanesulfonamide 431a) N-{2-[5-Chloro-2-(7-chloro-1,4-diethyl-2,3,4,5-tetrahydro-1H-benzo[e][1,4]diazepin-8-ylamino)-pyrimidin-4-ylamino]-phenyl}-methanesulfonamide. This compound was prepared according to the procedure for Example 417b. From 7-chloro-1,4-diethyl-2,3,4,5-tetrahydro-1H-benzo[e][1,4]diazepin-8-ylamine (24 mg, 0.09 mmol) and N-[2-(2,5-dichloro-pyrimidin-4-ylamino)-phenyl]-methanesulfonamide (32 mg, 0.09 mmol) was obtained 7 mg (14%) of the title compound following preparative tlc on silica gel (1% NH$_4$OH/10% MeOH/DCM); MS: m/z=551; $^1$H-NMR (DMSO-d$_6$, δ): 9.20 (m, 2H), 8.50 (s, 1H), 8.12 (s, 1H), 7.95 (d, 7 Hz, 1H), 7.49 (s, 1H), 7.20 (s, 1H), 7.19-7.10 (m, 3H), 3.70 (s, 2H), 3.00-2.90 (m, 7H), 2.75 (m, 4H), 1.10-1.00 (m, 6H).

Example 432

2-{5-Chloro-2-[4-(2-methoxy-ethyl)-1-methyl-2,3,4,5-tetrahydro-1H-benzo[e][1,4]diazepin-7-ylamino]-pyrimidin-4-ylamino}-N-methyl-benzamide 432a) 2-{5-Chloro-2-[4-(2-methoxy-ethyl)-1-methyl-2,3,4,5-tetrahydro-1H-benzo[e][1,4]diazepin-7-ylamino]-pyrimidin-4-ylamino}-N-methylbenzamide. This compound was prepared according to the procedure of Example 429a. From 2-[5-Chloro-2-(1-methyl-2,3,4,5-tetrahydro-1H-benzo[e][1,4]diazepin-7-ylamino)-pyrimidin-4-ylamino]-N-methylbenzamide (63 mg, 0.14 mmol) and 1-bromo-2-methoxyethane (14 μL, 0.15 mmol) was obtained 28 mg (41%) of the title compound following preparative tlc on silica gel (1% NH4OH/10% MeOH/DCM); MS: m/z=496/498, Cl-isotope pattern; $^1$H-NMR (DMSO-d$_6$, δ): 11.63 (s, 1H), 9.21 (s, 1H), 8.75 (m, 2H), 8.17 (s, 1H), 7.75 (d, 7 Hz, 1H), 7.47-7.35 (m, 3H), 7.12 (t, 7 Hz, 1H), 6.83 (d, 7 Hz, 1H), 3.65 (br, 2H), 3.41 (br, 2H), 3.32 (s, 3H), 3.20 (s, 3H), 2.86 (s, 3H), 2.81 (m, 6H).

Example 441

N-{(1R,2R)-2-[5-Chloro-2-(3-ethyl-2,3,4,5-tetrahydro-1H-benzo[d]azepin-7-ylamino)-pyrimidin-4-ylamino]-cyclohexyl}methanesulfonamide 441a) (1R,2R)-Cyclohexane-1,2-diamine (4.17 g, 36.5 mmol) was added into a round bottom flask and was dissolved in tetrahydrofuran (200 mL). The flask was cooled at 0° C., then 2,4,5-trichloropyrimidine (6.08 g, 33.1 mmol) was added. A precipitate formed, and the reaction was stirred 5 min before triethylamine (12 mL, 83 mmol) and methanesulfonyl chloride (4.00 mL, 51.7 mmol) were added simultaneously via two syringes. After 5 min, external cooling was removed, and the contents were stirred under an atmosphere of nitrogen. After 45 min, the contents were partitioned between dichloromethane (150 mL) and saturated sodium bicarbonate solution (150 mL). The layers were separated, and the aqueous phase extracted with dichloromethane (100 mL). The organic fractions were washed with brine (100 mL), dried (sodium sulfate) and were concentrated onto 37 g silica gel, and chromatographed on an ISCO cartridge (120 g SiO$_2$, 0-50% EA:Hex). N-[(1R,2R)-2-(2,5-Dichloro-pyrimidin-4-ylamino)-cyclohexyl]-methanesulfonamide was isolated as a white solid (4.8 g, 43%). m.p. 163-166° C.; LCMS (m/e) 339 (M+1); $^1$H-NMR (CDCl$_3$, 400 MHz) δ 8.04 (s, 1H), 5.91 (d, 1H, J=7.6 Hz), 5.91 (d, 1H, J=7.6 Hz), 5.91 (d, 1H, J=7.6 Hz), 3.32 (m, 1H), 3.91 (m, 1H), 2.92 (s, 3H), 2.25 (d, 1H, J=12 Hz), 2.13 (d, 1H, J=12 Hz), 1.83 (m, 2H), 1.25-1.48 (m, 4H).

441b) N-[(1R,2R)-2-(2,5-Dichloro-pyrimidin-4-ylamino)-cyclohexyl]-methanesulfonamide (99 mg, 0.29 mmol) was added into a vial, followed by a solution of 3-Ethyl-2,3,4,5-tetrahydro-1H-benzo[d]azepin-7-ylamine (55.0 mg, 0.289 mmol) in 2-Methoxyethanol (3 mL). 4 M of Hydrogen chloride in 1,4-Dioxane (0.10 mL) was added and the reaction was heated at 120° C. After overnight stirring, Macroporous carbonate resin (3.16 mmol/g loading; 150 mg, 0.474 mmol) was added and the reaction was cooled to room temperature, then was concentrated in vacuo onto Celite, and chromatographed (14 g ISCO Amine column, DCM) to isolate N-{(1R,2R)-2-[5-Chloro-2-(3-ethyl-2,3,4,5-tetrahydro-1H-benzo-[d]azepin-7-ylamino)-pyrimidin-4-ylamino]-cyclohexyl}methane-sulfonamide as a beige foam (40 mg, 28%). LCMS (m/e) 493 (M+1); $^1$H-NMR (CDCl$_3$, 400 MHz) δ 7.92 (s, 1H), 7.24 (m, 2H), 7.04 (d, 1H, J=8.8 Hz), 6.76 (s, 1H), 5.38 (d, 1H, J=7.6 Hz), 5.28 (s, 1H), 3.87 (m, 1H), 3.22 (m, 1H), 2.91 (m, 4H), 2.77 (s, 3H), 2.64 (m, 3H), 2.57 (t, 2H, J=7.0 Hz), 2.21 (m, 2H), 1.82 (m, 2H), 1.37 (m, 4H), 1.10 (t, 3H, J=7.0 Hz).

Example 442

5-Chloro-N*2*-(3-ethyl-2,3,4,5-tetrahydro-1H-benzo[d]azepin-7-yl)-N*4*-(2-methoxy-4-morpholin-4-yl-phenyl)-pyrimidine-2,4-diamine 442a) 2,4,5-Trichloropyrimidine (978 mg, 5.33 mmol) was dissolved in Tetrahydrofuran (30 mL), then Potassium carbonate (1.52 g, 11.0 mmol) was added. 2-Methoxy-4-morpholin-4-yl-phenylamine (1.030 g, 4.95 mmol) was added, and the reaction was stirred under an atmosphere of Nitrogen, overnight. The reaction was partitioned between 30 mL water, 30 mL dichloromethane and separated. The aq. layer was extracted once with 30 mL dichloromethane, the combined organics washed once with 50 mL brine, then dried over sodium sulfate. The contents were concentrated onto silica gel, and chromatographed on an ISCO cartridge (120 g SiO2, 0-40% EA:Hex). (2,5-Dichloro-pyrimidin-4-yl)-(2-methoxy-4-morpholin-4-yl-phenyl)-amine was isolated as a yellow solid (1.40 g, 80%). m.p.=156-160° C.; LCMS (m/e)=355 (M+1); $^1$H-NMR (CDCl$_3$, 400 MHz) δ 8.30 (d, 1H, J=8.8 Hz), 8.13 (s, 1H), 7.87 (s, 1H), 6.57 (d, 1H, J=8.8 Hz), 6.52 (s, 1H), 3.93 (s, 3H), 3.88 (t, 4H, J=4.8 Hz), 3.16 (t, 4H, J=4.8 Hz).

442b) (2,5-Dichloro-pyrimidin-4-yl)-(2-methoxy-4-morpholin-4-yl-phenyl)-amine (104 mg, 0.293 mmol) was added into a vial, followed by a solution of 3-Ethyl-2,3,4,5-tetrahydro-1H-benzo[d]azepin-7-ylamine (55.0 mg, 0.289 mmol) in 2-Methoxyethanol (3 mL). 4 M of Hydrogen chloride in 1,4-Dioxane (0.10 mL) was added and the reaction was heated at 120° C. After 6 h, Macroporous carbonate resin (3.16 mmol/g loading; 150 mg, 0.474 mmol) was added and the reaction was cooled to room temperature, stirred overnight, then was concentrated in vacuo onto Celite, and chromatographed (2×24 g ISCO Amine column, 0-0.5% MeOH:DCM). Product is ca. 75% pure; rechromatograph, (2×4 g ISCO Amine column, DCM) to isolate 5-Chloro-N*2*-(3-ethyl-2,3,4,5-tetrahydro-1H-benzo[d]azepin-7-yl)-N*4*-(2-methoxy-4-morpholin-4-yl-phenyl)-pyrimidine-2,4-diamine as a beige powder (25 mg, 17%). m.p.=157-162° C.; LCMS (m/e) 509 (M+1); $^1$H-NMR (CDCl$_3$, 400 MHz) δ 8.25 (d, 1H, J=8.8 Hz), 8.00 (s, 1H), 7.58 (s, 1H), 7.42 (s, 1H), 7.18 (m, 1H), 7.02 (m, 1H), 6.83 (s, 1H), 6.54 (s, 1H), 6.49 (d, 1H, J=9.1 Hz), 3.92 (s, 3H), 3.89 (t, 4H, J=4.8 Hz), 3.15 (t, 4H, J=4.8 Hz), 2.91 (m, 4H), 2.64 (m, 4H), 2.57 (q, 2H, J=7 Hz), 1.10 (t, 1H, J=7 Hz).

Example 443

5-Chloro-N*2*-(3-ethyl-2,3,4,5-tetrahydro-1H-benzo[d]azepin-7-yl)-N*4*-(4-morpholin-4-yl-phenyl)-pyrimidine-2,4-diamine 443a) 2,4,5-Trichloropyrimidine (1.05 g, 5.73 mmol) was dissolved in tetrahydrofuran (30 mL). Potassium carbonate (1.18 g, 8.55 mmol) was added, followed by 4-morpholinoaniline (1.017 g, 5.71 mmol). After stirring overnight, water (30 mL) and dichloromethane (30 mL) were added, the phases separated and the aqueous layer extracted once with dichloromethane (30 mL). The combined organic fractions were dried over sodium sulfate, concentrated onto silica gel and chromatographed (120 g SiO$_2$, 0-60% EA:Hex). (2,5-Dichloro-pyrimidin-4-yl)-(4-morpholin-4-yl-phenyl)-amine was isolated as a yellow solid (1.29 g, 70%). m.p.=168-172° C.; LCMS (m/e) 325 (M+1); $^1$H-NMR (DMSO-d$_6$, 400 MHz) δ 9.38 (s, 1H), 8.30 (s, 1H), 7.37 (d, 2H, J=9.0 Hz), 6.96 (d, 2H, J=9.0 Hz), 3.74 (t, 4H, J=4.9 Hz), 3.11 (t, 4H, J=4.9 Hz).

443b) (2,5-Dichloro-pyrimidin-4-yl)-(4-morpholin-4-yl-phenyl)-amine (96 mg, 0.29 mmol) was added into a vial, followed by a solution of 3-Ethyl-2,3,4,5-tetrahydro-1H-benzo[d]azepin-7-ylamine (52 mg, 0.27 mmol) in 2-Methoxyethanol (2.7 mL). 4 M of Hydrogen chloride in 1,4-Dioxane (0.10 mL) was added and the reaction was heated at 120° C. After 6 h, the reaction was cooled and Macroporous carbonate resin (3.16 mmol/g loading; 400 mg, 1.25 mmol) was added and the reaction was stirred overnight, then was concentrated in vacuo onto Celite, and chromatographed (24 g alumina column, DCM). 5-Chloro-N*2*-(3-ethyl-2,3,4,5-tetrahydro-1H-benzo[d]azepin-7-yl)-N*4*-(4-morpholin-4-yl-phenyl)-pyrimidine-2,4-diamine was isolated as a yellow powder (40 mg, 31%). m.p.=190-194° C.; LCMS (m/e) 479 (M+1); $^1$H-NMR (CDCl$_3$, 400 MHz) δ 8.04 (s, 1H), 7.23 (m, 1H), 7.16 (d, 1H, J=7.9 Hz), 7.04 (dd, 1H, J=2.1, 2.2 Hz), 7.00 (m, 2H), 6.82 (s, 1H), 6.72 (dd, 1H, J=2.2, 8.3 Hz), 3.81 (t, 4H, J=4.8 Hz), 3.12 (t, 4H, J=4.8 Hz), 2.89 (m, 4H), 2.62 (m, 4H), 2.57 (q, 2H, J=7 Hz), 1.09 (t, 1H, J=7 Hz).

Example 444

5-Chloro-N*2*-(3-ethyl-2,3,4,5-tetrahydro-1H-benzo[d]azepin-7-yl)-N*4*-(3-morpholin-4-yl-phenyl)-pyrimidine-2,4-diamine 444a) 2,4,5-Trichloropyrimidine (0.960 g, 5.2 mmol) was dissolved in tetrahydrofuran (20 mL). Potassium carbonate (1.20 g, 8.70 mmol) was added, followed by 3-morpholinoaniline (0.875 g, 4.90 mmol). After stirring overnight, water (30 mL) and dichloromethane (30 mL) were added, the phases separated and the aqueous layer extracted once with dichloromethane (30 mL). The combined organic fractions were dried over sodium sulfate, concentrated onto silica gel and chromatographed (120 g SiO$_2$, 0-50% EA:Hex). (2,5-Dichloro-pyrimidin-4-yl)-(3-morpholin-4-yl-phenyl)-amine was isolated as an off-white solid (1.16 g, 73%). m.p.=142-145° C.; LCMS (m/e) 325 (M+1); $^1$H-NMR (CDCl$_3$, 400 MHz) δ 8.20 (s, 1H), 7.38 (s, 1H), 7.28 (m, 1H), 7.21 (s, 1H), 7.01 (d, 1H, J=7.8 Hz), 6.75 (d, 1H, J=8.4 Hz), 3.88 (t, 4H, J=4.8 Hz), 3.21 (t, 4H, J=4.8 Hz).

444b) (2,5-Dichloro-pyrimidin-4-yl)-(3-morpholin-4-yl-phenyl)-amine (96 mg, 0.29 mmol) was added into a vial, followed by a solution of 3-Ethyl-2,3,4,5-tetrahydro-1H-benzo[d]azepin-7-ylamine (52 mg, 0.27 mmol) in 2-Methoxyethanol (2.7 mL). 4 M of Hydrogen chloride in 1,4-Dioxane (0.10 mL) was added and the reaction was heated at 120° C. After 6 h, the reaction was cooled and Macroporous carbonate resin (3.16 mmol/g loading; 400 mg, 1.25 mmol) was added and the reaction was stirred overnight, then was concentrated in vacuo onto Celite, and chromatographed (24 g alumina column, EtOAC-5% MeOH:EtOAC-5% MeOH:DCM). 5-Chloro-N*2*-(3-ethyl-2,3,4,5-tetrahydro-1H-benzo-[d]azepin-7-yl)-N*4*-(3-morpholin-4-yl-phenyl)-pyrimidine-2,4-diamine was isolated as a yellow foam (64 mg, 49%). LCMS (m/e) 479 (M+1); $^1$H-NMR (CDCl$_3$, 400 MHz) δ 8.01 (s, 1H), 7.47 (m, 2H), 7.37 (d, 1H, J=2.0 Hz), 7.14 (dd, 1H, J=2.3, 8.1 Hz), 6.96 (d, 1H, J=7.9 Hz), 6.92 (m, 3H), 6.82 (s, 1H), 3.89 (t, 4H, J=4.8 Hz), 3.16 (t, 4H, J=4.8 Hz), 2.85 (m, 4H), 2.63 (m, 4H), 2.57 (q, 2H, J=7 Hz), 1.10 (t, 1H, J=7 Hz).

Example 445

N-{(1R,2R)-2-[5-Chloro-2-(3-ethyl-2,3,4,5-tetrahydro-1H-benzo[d]azepin-7-ylamino)-pyrimidin-4-ylamino]-cyclohexyl}-acetamide 445a) (1R,2R)-Cyclohexane-1,2-diamine (1.10 g, 9.68 mmol) was added into a Round bottom flask and was dissolved in Tetrahydrofuran (50 mL). The flask was cooled at 0° C., then 2,4,5-Trichloropyrimidine (1.60 g, 8.72 mmol) was added. A precipitate formed, and the reaction was stirred 10 min before Triethylamine (3.00 mL, 21.5 mmol) and Acetic anhydride (1.20 mL, 12.7 mmol) were added simultaneously via syringes. After 15 min, external cooling was removed, and the contents was stirred under an atmosphere of Nitrogen. After 45 min, the contents were partitioned between 100 mL DCM and 100 mL sat'd. sodium bicarbonate solution. The layers were separated, and the aqueous phase extracted once with 100 mL DCM. The organic fractions were washed once with 100 mL brine, dried (sodium sulfate) and then were concentrated onto 8 g Celite and chromatographed on an ISCO cartridge (120 g, 0-100% EA:Hex), with product beginning to elute at 75%. N-[(1R,2R)-2-(2,5-Dichloro-pyrimidin-4-ylamino)-cyclohexyl]-acetamide was isolated as a white solid (1.08 g, 41%). m.p.=222-225° C.; LCMS (m/e) 303 (M+1); $^1$H-NMR (CDCl$_3$, 400 MHz) δ 7.99 (s, 1H), 6.30 (d, 1H, J=7 Hz), 5.69 (d, 1H, J=7.5 Hz), 3.83 (m, 2H), 2.25 (m, 1H), 2.04 (m, 1H), 1.90 (s, 3H), 1.80 (m, 2H), 1.33 (m, 4H).

445b) N-[(1R,2R)-2-(2,5-Dichloro-pyrimidin-4-ylamino)-cyclohexyl]-acetamide (170.0 mg, 0.5607 mmol) was added into a Vial, followed by a solution of 3-Ethyl-2,3,4,5-tetrahydro-1H-benzo[d]azepin-7-ylamine (103.0 mg, 0.5413 mmol) in 2-Methoxyethanol (7 mL, 90 mmol). 4 M of Hydrogen chloride in 1,4-Dioxane (0.20 mL) was added and the reaction was heated at 120° C. After 4.5 h, the reaction was cooled to room temperature, Macroporous carbonate resin (3.16 mmol/g loading; 530 mg, 1.68 mmol) was added and stirred 30 min. The polymer was filtered off, and the solvent removed in vacuo. The residue was dissolved in DCM, concentrated onto Celite, then chromatographed (2×12 g SiO2, ISCO, 0-10% (5% NH$_4$OH:MeOH):DCM) to afford N-{(1R,2R)-2-[5-Chloro-2-(3-ethyl-2,3,4,5-tetrahydro-1H-benzo[d]azepin-7-ylamino)-pyrimidin-4-ylamino]-cyclohexyl}-acetamide as a beige solid (170 mg, 69%). m.p.=248-250° C.; LCMS (m/e) 457 (M+1); $^1$H-NMR (CDCl$_3$, 400 MHz) δ 7.88 (s, 1H), 7.28 (m, 2H), 7.04 (d, 1H, J=7.5 Hz), 6.77 (s, 1H), 6.02 (s, 1H), 5.73 (s, 1H), 3.81 (m, 2H), 2.81-2.91 (m, 4H), 2.5-2.6 (m, 6H), 2.26 (m, 1H), 2.13 (m, 1H), 1.81 (m, 2H), 1.71 (s, 3H), 1.2-1.4 (m, 4H), 1.10 (t, 3H, J=7 Hz).

Example 446

N-{(1R,2R)-2-[5-Chloro-2-(3-ethyl-2,3,4,5-tetrahydro-1H-benzo[d]azepin-7-ylamino)-pyrimidin-4-ylamino]-cyclohexyl}-2,2,2-trifluoro-acetamide 446a) (1R,2R)-Cyclohexane-1,2-diamine (1.10 g, 9.68 mmol) was added into a Round bottom flask and was dissolved in Tetrahydrofuran (50 mL). The flask was cooled at 0° C., then 2,4,5-Trichloropyrimidine (1.60 g, 8.72 mmol) was added. A precipitate formed, and the reaction was stirred 10 min before Triethylamine (3.00 mL, 21.5 mmol) and Trifluoroacetic anhydride (1.8 mL, 12.9 mmol) were added simultaneously via syringes. After 15 min, external cooling was removed, and the contents was stirred under an atmosphere of Nitrogen. After 45 min, the contents were partitioned between 100 mL DCM and 100 mL sat'd. sodium bicarbonate solution. The layers were separated, and the aqueous phase extracted once with 100 mL DCM. The organic fractions were washed once with 100 mL brine, dried (sodium sulfate) and then were concentrated onto 8 g Celite and chromatographed on an ISCO cartridge (120 g, 0-100% EA:Hex), with product beginning to elute at 50%. A mixture of mono- and bis-trifluoroacetylation is observed. A single fraction was pure mono-acetylation, which was concentrated to afford N-[(1R,2R)-2-(2,5-Dichloro-pyrimidin-4-ylamino)-cyclohexyl]-2,2,2-trifluoro-acetamide (206 mg, 7%) as a white foam. LCMS (m/e) 357 (M+1); $^1$H-NMR (CDCl$_3$, 400 MHz) δ 8.06 (s, 1H), 7.15 (s, 1Hz), 5.53 (d, 1H, J=7.3 Hz), 4.05 (m, 1H), 3.82 (m, 1H), 2.21 (m, 1H), 2.15 (m, 1H), 1.88 (m, 2H), 1.42 (m, 4H).

446b) N-[(1R,2R)-2-(2,5-Dichloro-pyrimidin-4-ylamino)-cyclohexyl]-2,2,2-trifluoro-acetamide (204 mg, 0.571 mmol) was added into a Vial, followed by a solution of 3-Ethyl-2,3,4,5-tetrahydro-1H-benzo[d]azepin-7-ylamine (106 mg, 0.557 mmol) in 2-Methoxyethanol (7 mL). 4 M of Hydrogen chloride in 1,4-Dioxane (0.2 mL) was added and the reaction was heated at 120° C. After 7 h, the reaction was cooled to room temperature, Macroporous carbonate resin (3.16 mmol/g loading; 530 mg, 1.68 mmol) was added and stirred 30 min. The polymer was filtered off, and the solvent removed in vacuo. The residue was dissolved in DCM, then chromatographed (2×12 g SiO2, ISCO, 0-10% MeOH:DCM) to afford N-{(1R,2R)-2-[5-Chloro-2-(3-ethyl-2,3,4,5-tetrahydro-1H-benzo[d]azepin-7-ylamino)-pyrimidin-4-ylamino]-cyclohexyl}-2,2,2-trifluoro-acetamide (128 mg, 45%) as a beige solid. m.p.=165° C.; LCMS (m/e) 511 (M+1); $^1$H-NMR (CDCl$_3$, 400 MHz) δ 7.98 (s, 1H), 7.94 (s, 1H), 7.32 (m, 2H), 7.08 (d, 1H, J=8.1 Hz), 6.93 (s, 1H), 5.27 (d, 1H, J=7.4 Hz), 3.99 (m, 1H), 3.87 (m, 1H), 3.68 (m, 3H), 3.11 (m, 2H), 2.7-2.9 (m, 4H), 2.30 (d, 1H, J=11.4 Hz), 2.16 (d, 1H, J=11.7 Hz), 1.8-1.9 (m, 2H), 1.2-1.6 (m, 8H).

Example 447

3-{(1R,2R)-2-[5-Chloro-2-(3-ethyl-2,3,4,5-tetrahydro-1H-benzo[d]azepin-7-ylamino)-pyrimidin-4-ylamino]-cyclohexyl}-1,1-dimethyl-urea N-{(1R,2R)-2-[5-Chloro-2-(3-ethyl-2,3,4,5-tetrahydro-1H-benzo[d]azepin-7-ylamino)-pyrimidin-4-ylamino]-cyclohexyl}-2,2,2-trifluoro-acetamide (78 mg, 0.15 mmol) and Potassium carbonate (125 mg, 0.904 mmol) were combined in Methanol (10 mL), and were then heated at 45° C. After stirring 3.5 d, the reaction had reached ~60% completion. After an additional 3 d, the mixture had evaporated to dryness, but the reaction had gone to completion as determined by HPLC of resolubilized material (DCM:MeOH). The mixture was reconcentrated to dryness after filtering off the solids. 1,4-Dioxane (5 mL) was added followed by Triethylamine (0.2 mL, 1.4 mmol) and N,N-Dimethylcarbamoyl chloride (21 uL, 0.23 mmol), and the reaction was stirred under an atmosphere of Nitrogen. After O.N. stirring, 0.5 mL DMF was added, and the mixture was sonicated to aid in solubilizing all the contents. After an additional 24 h, N,N-Dimethylcarbamoyl chloride (50 uL, 0.5 mmol) was added and stirring was continued. After 24 h, N,N-Dimethylcarbamoyl chloride (50 uL, 0.5 mmol) was added along with 3 mL dichloromethane to aid in solubility and to rinse the sidewalls of the flask. After 5 h, the contents were concentrated onto Celite and chromatographed on an ISCO column, eluting with 10% (5% NH4OH:MeOH):DCM. The product elutes at 10% polar solvent mix, and was collected and concentrated to afford 3-{(1R,2R)-2-[5-Chloro-2-(3-ethyl-2,3,4,5-tetrahydro-1H-benzo[d]azepin-7-ylamino)-pyrimidin-4-ylamino]-cyclohexyl}-1,1-dimethyl-urea (52 mg, 70%) as a yellow film. LCMS (m/e) 486 (M+1); $^1$H-NMR (CDCl$_3$, 400 MHz) δ 7.85 (s, 1H), 7.28 (m, 2H), 7.03 (m, 2H), 6.08 (d, 1H, J=7.1 Hz), 4.85 (d, 1H, J=7.2 Hz), 3.82 (m, 1H), 3.71 (m, 1H), 2.94 (m, 5H), 2.68 (s, 6H), 2.62 (m, 7H), 2.28 (m, 1H), 2.15 (m, 1H), 1.80 (m, 2H), 1.2-1.4 (m, 5H), 1.12 (t, 3H, J=7.1 Hz).

Example 448

2-{5-Chloro-2-[3-((R)-3,3,3-trifluoro-2-hydroxy-propyl)-2,3,4,5-tetrahydro-1H-benzo[d]azepin-7-ylamino]-pyrimidin-4-ylamino}-N-methyl-benzamide (R)-3-(7-Amino-1,2,4,5-tetrahydro-benzo[d]azepin-3-yl)-1,1,1-trifluoro-propan-2-ol (82 mg, 0.30 mmol), 2-(2,5-Dichloro-pyrimidin-4-ylamino)-N-methyl-benzamide (81 mg, 0.27 mmol), and 4.00 M of Hydrogen chloride in 1,4-Dioxane (0.20 mL) were combined in 2-Methoxyethanol (2.5 mL) and heated at 120° C. After two hours, the mixture was cooled to room temperature, then diluted with 10 mL ethyl ether. A mixture of solids and gum formed, which was intractable, so the mixture was further diluted with 10 mL DCM and Macroporous carbonate resin (3.16 mmol/g loading; 0.64 g, 2.0 mmol) was added and stirred for 4 h, then filtered and concentrated in vacuo to afford a white solid, which was dissolved in DCM/MeOH, and chromatographed (ISCO, 2×12 g, 0-5% MeOH:DCM) to afford 2-{5-Chloro-2-[3-((R)-3,3,3-trifluoro-2-hydroxy-propyl)-2,3,4,5-tetrahydro-1H-benzo[d]azepin-7-ylamino]-pyrimidin-4-ylamino}-N-methyl-benzamide (72 mg, 49%) as a white solid. m.p.=188-191° C.; LCMS (m/e) 535 (M+1); $^1$H-NMR (CDCl$_3$, 400 MHz) δ 11.07 (s, 1H), 8.65 (d, 1H, J=8.4 Hz), 8.10 (s, 1H), 7.49 (d, 1H, J=7.8 Hz), 7.43 (dd, 1H, J=7.8, 8.0 Hz), 7.28 (m, 2H), 7.09 (dd, 1H, J=7.4, 7.7 Hz), 7.03 (d, 1H, J=8.1 Hz), 6.88 (s, 1H), 4.40 (br m, 1H), 4.05 (m, 1H), 3.04 (d, 3H, J=4.8 Hz), 2.85 (m, 8H), 2.7 (m, 3H).

Example 449

N-((1R,2R)-2-{5-Chloro-2-[3-((R)-3,3,3-trifluoro-2-hydroxy-propyl)-2,3,4,5-tetrahydro-1H-benzo[d]azepin-7-ylamino]-pyrimidin-4-ylamino}-cyclohexyl)-methanesulfonamide (R)-3-(7-Amino-1,2,4,5-tetrahydro-benzo[d]azepin-3-yl)-1,1,1-trifluoro-propan-2-ol (82 mg, 0.30 mmol), N-[(1R,2R)-2-(2,5-Dichloro-pyrimidin-4-ylamino)-cyclohexyl]-methanesulfonamide (95 mg, 0.28 mmol), and 4.00 M of Hydrogen chloride in 1,4-Dioxane (0.20 mL) were combined in 2-Methoxyethanol (2.5 mL) and heated at 120° C. After two hours, the mixture was cooled to room temperature, then diluted with 10 mL ethyl ether. A mixture of solids and gum formed, which was intractable, so the mixture was further diluted with 10 mL DCM and Macroporous carbonate resin (3.16 mmol/g loading; 0.75 g, 2.37 mmol) was added, stirred for 4 h then filtered and concentrated in vacuo to afford an oil, which was chromatographed (ISCO, 2×12 g, 0-5% MeOH:DCM). The product elutes with 5% MeOH, to give N-((1R,2R)-2-{5-Chloro-2-[3-((R)-3,3,3-trifluoro-2-hydroxy-propyl)-2,3,4,5-tetrahydro-1H-benzo[d]azepin-7-ylamino]-pyrimidin-4-ylamino}-cyclohexyl)-methanesulfonamide (145 mg, 90%) as an off white foam. LCMS (m/e) 577 (M+1); $^1$H-NMR (CDCl$_3$, 400 MHz) δ 7.92 (s, 1H), 7.29 (m, 1H), 7.05 (d, 1H, J=7.8 Hz), 6.88 (s, 1H), 5.42 (d, 1H, J=7.5 Hz), 5.41 (br s, 1H), 4.05 (m, 1H), 3.85 (m, 1H), 3.74 (t, 1H, J=4.5 Hz), 3.50 (t, 1H, J=4.5 Hz), 3.22 (m, 1H), 2.8-3.0 (m, 7H), 2.79 (s, 3H), 2.5-2.8 (m, 3H), 2.21 (m, 1H), 1.83 (m, 1H), 1.36 (m, 4H).

Example 450

N-((1R,2R)-2-{5-Chloro-2-[3-(2-methoxy-ethyl)-2,3,4,5-tetrahydro-1H-benzo[d]azepin-7-ylamino]-pyrimidin-4-ylamino}-cyclohexyl)-2,2,2-trifluoro-acetamide N-[(1R,2R)-2-(2,5-Dichloro-pyrimidin-4-ylamino)-cyclohexyl]-2,2,2-trifluoro-acetamide (776 mg, 2.17 mmol) was added into a Vial, followed by a solution of 3-(2-Methoxy-ethyl)-2,3,4,5-tetrahydro-1H-benzo[d]azepin-7-ylamine (447 mg, 2.03 mmol) in 2-Methoxyethanol (15 mL). 4.00 M of Hydrogen chloride in 1,4-Dioxane (1.1 mL) was added and the reaction was heated at 120° C. After 3 h, the reaction was cooled to room temperature, and 85 mL ether was added. The HCl salt formed as an oil, not a solid, so it was redissolved by adding MeOH and DCM. Macroporous carbonate resin (3.16 mmol/g loading; 2.45 g, 7.7 mmol) was then added and stirred for 1 h and filtered before concentration. The residue was dissolved in DCM, then chromatographed (2×12 g SiO2, ISCO, 0-10% MeOH:DCM) to afford N-((1R,2R)-2-{5-Chloro-2-[3-(2-methoxy-ethyl)-2,3,4,5-tetrahydro-1H-benzo[d]azepin-7-ylamino]-pyrimidin-4-ylamino}-cyclohexyl)-2,2,2-trifluoro-acetamide (414 mg, 38%) as a beige solid. m.p.=180-182° C.; LCMS (m/e) 541 (M+1); $^1$H-NMR (CDCl$_3$, 400 MHz) δ 7.92 (s, 1H), 7.88 (m, 1H), 7.23 (s, 1H), 7.22 (d, 1H, J=8.5 Hz), 7.04 (d, 1H, J=8.5 Hz), 6.81 (s, 1H), 5.22 (d, 1H, J=7.5 Hz), 4.0 (m, 1H), 3.68 (m, 1H), 3.54 (t, 1H, J=5.5 Hz), 3.36 (s, 3H), 2.92 (m, 4H), 2.74 (m, 4H), 2.28 (m, 1H), 2.15 (m, 1H), 1.80 (m, 4H), 1.2-1.5 (m, 4H).

Example 451

N*4*-((1R,2R)-2-Amino-cyclohexyl)-5-chloro-N*2*-[3-(2-methoxy-ethyl)-2,3,4,5-tetrahydro-1H-benzo[d]azepin-7-yl]-pyrimidine-2,4-diamine N-((1R,2R)-2-{5-Chloro-2-[3-(2-methoxy-ethyl)-2,3,4,5-tetrahydro-1H-benzo[d]azepin-7-ylamino]-pyrimidin-4-ylamino}-cyclohexyl)-2,2,2-trifluoro-acetamide (313 mg, 0.578 mmol) was dissolved in Methanol (10 mL) and 1.0 M of Potassium hydroxide in water (3.0 mL) was added. The reaction was heated at 60° C. for 7 h, at which time the reaction had reached completion by HPLC. The reaction was cooled then was poured into 30 mL satd. sodium bicarbonate-20 mL water, then extracted 4×50 mL DCM, dried over sodium sulfate and concentrated in vacuo to afford the amine as a off-white film (260 mg, 100%). LCMS (m/e) 445 (M+1); $^1$H-NMR (CDCl$_3$, 400 MHz) δ 7.89 (s, 1H), 7.28 (m, 2H), 7.01 (d, 1H, J=7.9 Hz), 6.79 (s, 1H), 5.14 (d, 1H, J=8.0 Hz), 3.75 (m, 1H), 3.53 (m, 2H), 3.37 (s, 3H), 2.91 (m, 4H), 2.75 (m, 6H), 2.58 (m, 1H), 2.16 (m, 1H), 2.04 (m, 1H), 1.78 (m, 2H), 1.32 (m, 6H).

Example 452

2,2,2-Trifluoro-ethanesulfonic acid ((1R,2R)-2-{5-chloro-2-[3-(2-methoxy-ethyl)-2,3,4,5-tetrahydro-1H-benzo[d]azepin-7-ylamino]-pyrimidin-4-ylamino}-cyclohexyl)-amide N*4*-((1R,2R)-2-Amino-cyclohexyl)-5-chloro-N*2*-[3-(2-methoxy-ethyl)-2,3,4,5-tetrahydro-1H-benzo[d]azepin-7-yl]-pyrimidine-2,4-diamine was dissolved in Methylene chloride (5 mL) and Triethylamine (0.15 mL, 1.1 mmol) was added, followed by 2,2,2-Trifluoroethanesulfonyl chloride (0.025 mL, 0.23 mmol). Stir under an atmosphere of Nitrogen at room temperature for 45 min, then partition between 10 mL satd. sodium bicarbonate and 10 mL DCM. Separate and extract the aqueous layer, 3×10 mL DCM. Dry the combined organics over sodium sulfate, filter and concentrate in vacuo. The resultant oil was purified on a sulfonic acid resin cartridge, washing with methanol, eluting with ammonia/methanol. Conc. in vacuo reconcentrating from DCM afforded an oil. Subsequent purification on silica gel (0-10% MeOH:DCM, 12 g SiO2) gave 2,2,2-Trifluoro-ethanesulfonic acid ((1R,2R)-2-{5-chloro-2-[3-(2-methoxy-ethyl)-2,3,4,5-tetrahydro-1H-benzo[d]azepin-7-ylamino]-pyrimidin-4-ylamino}-cyclohexyl)-amide (55 mg, 53%) as a colorless film. LCMS (m/e) 591 (M+1); $^1$H-NMR (CDCl$_3$, 400 MHz) δ 7.88 (s, 1H), 7.21 (d, 1H, J=7.9 Hz), 7.18 (s, 1H), 7.01 (d, 1H, J=7.9 Hz), 6.97 (s, 1H), 5.36 (d, 1H, J=7.5 Hz), 5.31 (s, 1H), 3.84 (m, 1H), 3.61 (q, 2H, J=9.0 Hz), 3.55 (t, 2H, J=5.4 Hz), 3.36 (s, 3H), 3.29 (m, 1H), 2.9 (m, 4H), 2.72 (m, 6H), 2.17 (m, 2H), 1.82 (m, 2H), 1.34 (m, 4H).

Examples 453-455 were prepared analogously to Example 452, substituting the trifluoroethanesulfonyl chloride with the appropriately substituted sulfonyl chloride.

Example 453

Ethanesulfonic acid ((1R,2R)-2-{5-chloro-2-[3-(2-methoxy-ethyl)-2,3,4,5-tetrahydro-1H-benzo[d]azepin-7-ylamino]-pyrimidin-4-ylamino}-cyclohexyl)-amide Isolated in 32% yield as a brown foam. LCMS (m/e) 537 (M+1)); $^1$H-NMR (CDCl$_3$, 400 MHz) δ 7.91 (s, 1H), 7.27 (m, 2H), 7.04 (d, 1H, J=8.0 Hz), 6.77 (s, 1H), 5.46 (d, 1H, J=7.9 Hz), 5.00 (m, 1H), 3.87 (m, 1H), 3.59 (m, 1H), 3.37 (s, 3H), 3.23 (m, 1H), 2.6-3.1 (m, 11H), 2.21 (m, 2H), 1.82 (m, 2H), 1.37 (m, 5H), 1.20 (t, 3H, J=7.3 Hz).

Example 454

Cyclopropanesulfonic acid ((1R,2R)-2-{5-chloro-2-[3-(2-methoxy-ethyl)-2,3,4,5-tetrahydro-1H-benzo[d]azepin-7-ylamino]-pyrimidin-4-ylamino}-cyclohexyl)-amide Isolated in 41% yield as an off-white foam. LCMS (m/e) 549 (M+1)); $^1$H-NMR (CDCl$_3$, 400 MHz) δ 7.91 (s, 1H), 7.25 (m, 2H), 7.04 (d, 1H, J=8.2 Hz), 6.77 (s, 1H), 5.39 (d, 1H, J=5.1 Hz), 5.30 (s, 1H), 3.87 (m, 1H), 3.54 (m, 2H), 3.38 (s, 3H), 3.23 (m, 1H), 2.92 (m, 4H), 2.75 (m, 6H), 2.24 (m, 3H), 1.81 (m, 2H), 1.39 (m, 4H), 1.19 (m, 1H), 0.90 (m, 2H), 0.72 (m, 1H).

Example 455

Propane-2-sulfonic acid ((1R,2R)-2-{5-chloro-2-[3-(2-methoxy-ethyl)-2,3,4,5-tetrahydro-1H-benzo[d]azepin-7-ylamino]-pyrimidin-4-ylamino}-cyclohexyl)-amide Isolated in 11% yield as a white film. LCMS (m/e) 551 (M+1)); $^1$H-NMR (CDCl$_3$, 400 MHz) δ 7.91 (s, 1H), 7.24 (m, 2H), 7.03 (d, 1H, J=7.5 Hz), 6.79 (s, 1H), 5.44 (d, 1H, J=7.7 Hz), 5.01 (d, 1H, J=7.0 Hz), 3.87 (m, 1H), 3.54 (t, 2H, J=5.6 Hz), 3.49 (s, 2H), 3.36 (s, 3H), 3.24 (m, 1H), 2.7-2.95 (m, 12H), 2.20 (m, 2H), 1.81 (m, 2H), 1.70 (m, 2H), 1.55 (m, 6H), 1.38 (m, 4H), 0.94 (t, 3H, J=7.4 Hz).

Examples 456 & 457

2-{5-Chloro-2-[12-(2-methoxy-ethyl)-12-aza-tricyclo[7.2.1.0(2,7)]dodeca-2(7),3,5-trien-4-ylamino]-pyrimidin-4-ylamino}-3-fluoro-N-methyl-benzamide & 2-{5-Chloro-2-[12-(2-methoxy-ethyl)-12-aza-tricyclo[7.2.1.0(2,7)]dodeca-2(7),3,5-trien-4-ylamino]-pyrimidin-4-ylamino}-3-fluoro-benzoic acid isopropyl ester 12-(2-Methoxy-ethyl)-12-aza-tricyclo[7.2.1.0(2,7)]dodeca-2(7),3,5-trien-4-ylamine (101 mg, 0.435 mmol), 2-(2,5-Dichloro-pyrimidin-4-ylamino)-3-fluoro-N-methyl-benzamide (0.140 g, 0.443 mmol), and 10-Camphorsulfonic acid (0.141 g, 0.607 mmol) were combined in Isopropyl alcohol (4 mL) and heated with microwave irradiation to 120° C. for a total of 1.5 h. The mixture was treated with Macroporous carbonate resin (3.16 mmol/g loading; 0.45 g, 1.4 mmol) and stirred for 30 min, concentrated in vacuo and chromatographed (ISCO 2×12 g SiO2, 0-10% MeOH:DCM). The amide product elutes with 10% MeOH, while the ester elutes before in ~8% MeOH. 2-{5-Chloro-2-[12-(2-methoxy-ethyl)-12-aza-tricyclo[7.2.1.0(2,7)]dodeca-2(7),3,5-trien-4-ylamino]-pyrimidin-4-ylamino}-3-fluoro-N-methyl-benzamide was isolated as a yellow solid (95 mg, 43%). m.p.=233-236° C.; LCMS (m/e) 511 (M+1); $^1$H-NMR (DMSO-$d_6$, 400 MHz) δ 9.30 (s, 1H), 9.22 (s, 1H), 8.53 (m, 1H), 8.17 (s, 1H), 7.51 (m, 2H), 7.42 (m, 1H), 7.15 (m, 1H), 6.77 (s, 1H), 3.59 (m, 1H), 3.41 (m, 3H), 3.28 (m, 1H), 3.23 (s, 3H), 2.95 (m, 1H), 2.75 (m, 3H), 2.55 (m, 1H), 2.25 (m, 1H), 2.04 (m, 2H), 1.45 (m, 2H).

2-{5-Chloro-2-[12-(2-methoxy-ethyl)-12-aza-tricyclo[7.2.1.0(2,7)]dodeca-2(7),3,5-trien-4-ylamino]-pyrimidin-4-ylamino}-3-fluoro-benzoic acid isopropyl ester was isolated as a yellow foam (15 mg, 6%). LCMS (m/e) 540 (M+1); $^1$H-NMR (CDCl$_3$, 400 MHz) δ 8.81 (s, 1H), 8.08 (s, 1H), 7.81 (d, 1H, J=7.8 Hz), 7.38 (dd, 1H, J=9.5, 10.1 Hz), 7.0-7.2 (m, 3H) 6.84 (m, 2H), 5.24 (sept, 1H, J=6.3 Hz), 3.75 (m, 1H), 3.53 (m, 3H), 3.34 (s, 4H), 3.09 (m, 1H), 2.2-2.3 (m, 3H), 1.72 (m, 1H), 1.33 (d, 6H, J=6.3 Hz).

Example 458

(2-endo, 3-endo)-3-{5-Chloro-2-[3-(2-methoxy-ethyl)-2,3,4,5-tetrahydro-1H-benzo[d]azepin-7-ylamino]-pyrimidin-4-ylamino}-bicyclo[2.2.1]hept-5-ene-2-carboxylic acid ethyl ester 458a) 2,4,5-Trichloropyrimidine (335 mg, 1.83 mmol), racemic Ethyl 3-endo-aminobicyclo[2.2.1]hept-5-ene-2-endo-carboxylate hydrochloride (335 mg, 1.54 mmol), and Potassium carbonate (712 mg, 5.15 mmol) were combined in Tetrahydrofuran (15 mL, 180 mmol) and stirred under an atmosphere of Nitrogen. After 45 h, the mixture was diluted with water (50 mL) then extracted 3×50 mL DCM. The organic extracts were washed with brine (80 mL) and dried over sodium sulfate. Conc. in vacuo and chromatography (ISCO 40 g SiO2, 0-15% EA:Hex) afforded (2-endo,3-endo)-3-(2,5-Dichloro-pyrimidin-4-ylamino)-bicyclo[2.2.1]hept-5-ene-2-carboxylic acid ethyl ester (276 mg, 55%) as a white solid. m.p.=100-102° C.; LCMS (m/e) 328 (M+1); $^1$H-NMR (CDCl$_3$, 400 MHz) δ 7.97 (s, 1H), 7.08 (d, 1H, J=7.4 Hz), 6.36 (m, 1H), 6.20 (m, 1H), 4.95 (m, 1H), 4.07 (m, 2H), 3.35 (s, 1H), 3.28 (m, 2H), 1.4-1.6 (m, 2H), 1.20 (t, 3H, J=7.1 Hz).

458b) (2-endo, 3-endo)-3-(2,5-Dichloro-pyrimidin-4-ylamino)-bicyclo[2.2.1]hept-5-ene-2-carboxylic acid ethyl ester (263 mg, 0.801 mmol) and 3-(2-Methoxy-ethyl)-2,3,4,5-tetrahydro-1H-benzo[d]azepin-7-ylamine (179 mg, 0.812 mmol) were combined into a Round bottom flask in 2-Methoxyethanol (10 mL), 4 M of Hydrogen chloride in 1,4-Dioxane (0.4 mL) was added and the mixture was heated at 115° C. for 3 h. The reaction was cooled, generating a solid, which was diluted with 50 mL anhyd. ether and the solids collected by filtration. The product was a gummy solid upon drying, so it was transferred to a RBF with 60 mL methanol, treated with Macroporous carbonate resin (0.5 g, 1.6 mmol), filtered and collected. Concentration in vacuo afforded (2-endo,3-endo)-3-{5-Chloro-2-[3-(2-methoxy-ethyl)-2,3,4,5-tetrahydro-1H-benzo[d]azepin-7-ylamino]-pyrimidin-4-ylamino}-bicyclo[2.2.1]hept-5-ene-2-carboxylic acid ethyl ester (316 mg, 77%) as an oily foam, ~85% purity by HPLC. LCMS (m/e) 512 (M+1); $^1$H-NMR (CDCl$_3$, 400 MHz) δ 7.86 (s, 1H), 7.52 (s, 1H), 7.32 (d, 1H, J=8.2 Hz), 7.06 (d, 1H, J=8.2 Hz), 6.96 (s, 1H), 6.58 (m, 1H), 6.41 (m, 1H), 6.22 (m, 1H), 4.95 (m, 1H), 4.07 (q, 2H, J=7.2 Hz), 3.90 (m, 1H), 3.74 (m, 1H), 3.52 (m, 1H), 3.40 (s, 2H), 3.35 (s, 4H), 3.32 (m, 1H), 3.25 (m, 4H), 1.63 (d, 1H, J=9.1 Hz), 1.46 (d, 1H, J=9.1 Hz), 1.16 (t, 3H, J=7.2 Hz).

Example 459

(2-endo, 3-endo)-3-{5-Chloro-2-[3-(2-methoxy-ethyl)-2,3,4,5-tetrahydro-1H-benzo[d]azepin-7-ylamino]-pyrimidin-4-ylamino}-bicyclo[2.2.1]hept-5-ene-2-carboxylic acid amide (2-endo, 3-endo)-3-{5-Chloro-2-[3-(2-methoxy-ethyl)-2,3,4,5-tetrahydro-1H-benzo[d]azepin-7-ylamino]-pyrimidin-4-ylamino}-bicyclo[2.2.1]hept-5-ene-2-carboxylic acid ethyl ester (316 mg, 0.617) was dissolved in Methanol (5 mL) and 1.0 M of Potassium hydroxide in water (1.0 mL) was added. After 4 h, the solution was acidified with 10% NH4Cl (10 mL) and extracted 4×20 mL DCM. HPLC and LCMS indicated a mixture of the acid and the methyl ester. The crude material was redissolved in 5 mL dioxane and 1 mL 1M KOH was added. After 5 h, HPLC showed complete hydrolysis. The material was poured into 20 mL 10% NH4Cl:20 mL DCM. The pH was adjusted to pH 6 with 1N HCl, giving an emulsion. Standing overnight afforded some partitioning, so the layers were separated and the aq. extracted 3×10 mL DCM. The organic layers, which had a sludgelike emulsion, were diluted with water (20 mL), but no partitioning occurred. The emulsion was concentrated in vacuo, azeotroping with toluene, affording 1.2 g of solids. One half of this product was used without purification for the next reaction. Crude (2-endo, 3-endo)-3-{5-Chloro-2-[3-(2-methoxy-ethyl)-2,3,4,5-tetrahydro-1H-benzo[d]azepin-7-ylamino]-pyrimidin-4-ylamino}-bicyclo[2.2.1]hept-5-ene-2-carboxylic acid (150 mg, 0.31 mmol) was suspended in DMF and 4-Methylmorpholine (0.50 mL, 4.5 mmol), cooled to 0° C. and 1.00 M of Isopropyl Chloroformate in Toluene (1.0 mL) was added. After 30 min, 2.00 M of Ammonia in Methanol (0.80 mL) was added, the reaction was stirred for 30 min, then aq. sodium bicarbonate was added (3 mL). The mixture was filtered over Celite and conc. in vacuo. Purification by RP-HPLC (7-27% acetonitrile:water) followed by formation of the free base with Macroporous carbonate resin to afford (2-endo,3-endo)-3-{5-Chloro-2-[3-(2-methoxy-ethyl)-2,3,4,5-tetrahydro-1H-benzo[d]azepin-7-ylamino]-pyrimidin-4-ylamino}-bicyclo[2.2.1]hept-5-ene-2-carboxylic acid amide (37 mg, 25%) as a white solid. m.p.=183-186° C.; LCMS (m/e) 483 (M+1); $^1$H-NMR (CD$_3$OD, 400 MHz) δ 7.76 (s, 1H), 7.54 (s, 1H), 7.26 (d, 1H, J=8.2 Hz), 7.00 (d, 1H, J=8.2 Hz), 6.31 (m, 1H), 6.13 (m, 1H), 3.55 (t, 2H, J=5.4 Hz), 3.1-3.4 (m, 13H), 2.90 (m, 4H), 2.72 (m, 6H), 1.50 (m, 2H).

Example 460

3-Chloro-2-[5-chloro-2-(1-methyl-2,3,4,5-tetrahydro-1H-benzo[e][1,4]diazepin-8-ylamino)-pyrimidin-4-ylamino]-N-methyl-benzamide 1-Methyl-2,3,4,5-tetrahydro-1H-benzo[e][1,4]diazepin-8-ylamine (271 mg, 1.53 mmol) and 3-Chloro-2-(2,5-dichloro-pyrimidin-4-ylamino)-N-methyl-benzamide (425 mg, 1.28 mmol) were combined in 2-Methoxyethanol (10 mL) and 4.00 M of Hydrogen chloride in 1,4-Dioxane (1.0 mL) was added. The reaction was warmed to 120° C. for 6 h, then the reaction was cooled to room temperature for 1 h before Macroporous carbonate resin (3.16 mmol/g loading; 2.2 g, 6.95 mmol) was added and stirred at r.t. for 1 h, filtered then conc. in vacuo to give an oil. The material was chromatographed on an ISCO column (40 g, 0-15% (5% NH$_4$OH: MeOH):DCM, celite dry load). Product eluted impure with 15% polar solvent, so it was purified by RP-HPLC (5-25% acetonitrile:water). Clean material concentrated followed by formation of the free base with Macroporous carbonate resin to afford 3-Chloro-2-[5-chloro-2-(1-methyl-2,3,4,5-tetrahydro-1H-benzo[e][1,4]diazepin-8-ylamino)-pyrimidin-4-ylamino]-N-methyl-benzamide (13 mg, 2%) as an orange film. LCMS (m/e) 472 (M+1); $^1$H-NMR (CDCl$_3$, 400 MHz) δ 8.06 (s, 1H), 7.82 (s, 1H), 7.57 (d, 1H, J=8.0 Hz), 7.45 (d, 1H, J=7.7 Hz), 7.04 (s, 1H), 6.91 (m, 3H), 6.07 (s, 1H), 3.88 (s, 2H), 3.48 (s, 2H), 3.06 (m, 2H), 2.94 (m, 2H), 2.72 (d, 3H, J=4.6 Hz), 2.68 (s, 3H).

Example 461

N-((1R,2R)-2-{5-Chloro-2-[8-methoxy-3-((S)-3,3,3-trifluoro-2-hydroxy-propyl)-2,3,4,5-tetrahydro-1H-benzo[d]azepin-7-ylamino]-pyrimidin-4-ylamino}-cyclohexyl)-methanesulfonamide 461a) 7-Methoxy-8-nitro-2,3,4,5-tetrahydro-1H-benzo[d]azepine (215 mg, 0.967 mmol) was placed into a sealable vial, suspended in Acetonitrile (10 mL) then (S)-2-Trifluoromethyl-oxirane (130 uL, 1.5 mmol) was added, followed by Macroporous carbonate resin (3.16 mmol/g loading; 0.810 g, 2.56 mmol). The reaction was stirred at room temperature for 24 h, filtered and concentrated in vacuo to afford (S)-1,1,1-Trifluoro-3-(7-methoxy-8-nitro-1,2,4,5-tetrahydro-benzo[d]azepin-3-yl)-propan-2-ol as an orange oil (316 mg, 97%), which was used without further purification. $^1$H-NMR (CDCl$_3$, 400 MHz) δ 7.67 (s, 1H), 6.83 (s, 1H), 4.05 (m, 1H), 3.95 (s, 3H), 2.6-3.0 (m, 10H); $^{19}$F-NMR (CDCl$_3$, 376 MHz) δ−78.7 (s).

461b) (S)-1,1,1-Trifluoro-3-(7-methoxy-8-nitro-1,2,4,5-tetrahydro-benzo[d]azepin-3-yl)-propan-2-ol (316 mg, 0.95 mmol) was dissolved in 10 mL methanol, 10% Pd/C, 50% wet (5:45:50, Palladium:carbon black:Water, 0.105 g) was added and the mixture was stirred under an atmosphere of Hydrogen (balloon) overnight. Filtration through Celite with methanol afforded (S)-3-(7-Amino-8-methoxy-1,2,4,5-tetrahydro-benzo[d]azepin-3-yl)-1,1,1-trifluoro-propan-2-ol (268 mg, 93%), which was used without further purification. (S)-3-(7-Amino-8-methoxy-1,2,4,5-tetrahydro-benzo[d]azepin-3-yl)-1,1,1-trifluoro-propan-2-ol (88 mg, 0.29 mmol), N-[(1R,2R)-2-(2,5-Dichloro-pyrimidin-4-ylamino)-cyclohexyl]-methanesulfonamide (101 mg, 0.298 mmol), and 10-Camphorsulfonic acid (0.10 g, 0.43 mmol) in 2-Methoxyethanol (4 mL) were heated in a microwave vial at 120° C. for a total of 4 h. The light brown solution was diluted with 3 mL satd. bicarbonate solution, resulting in a suspension, which was added to 12 mL satd. bicarbonate solution which was thoroughly mixed and then filtered to afford the product in ~80% purity by HPLC (93 mg). Trituration from ether gave an oil, so the material wash purified by RP-HPLC (10-30% acetonitrile:water) followed by formation of the free base with Macroporous carbonate resin to afford N-((1R,2R)-2-{5-Chloro-2-[8-methoxy-3-((S)-3,3,3-trifluoro-2-hydroxy-propyl)-2,3,4,5-tetrahydro-1H-benzo[d]azepin-7-ylamino}-pyrimidin-4-ylamino}-cyclohexyl)-methanesulfonamide as off white solids (81 mg, 46%). m.p.=122-127° C.; LCMS (m/e) 608 (M+1); $^1$H-NMR (CD$_3$OD, 400 MHz) δ 7.94 (s, 1H), 7.58 (s, 1H), 7.1-7.3 (m, 3H), 7.04 (s, 1H), 4.70 (m, 1H), 3.94 (m, 1H), 3.89 (s, 3H), 3.4-3.7 (m, 6H), 3.25 (m, 4H), 2.95 (s, 3H), 2.32 (s, 1H), 2.14 (m, 2H), 1.82 (m, 2H), 1.2-1.6 (m, 5H).

Example 462

(S)-3-{7-[5-Chloro-4-(2-methoxy-4-morpholin-4-yl-phenylamino)-pyrimidin-2-ylamino]-8-methoxy-1,2,4,5-tetrahydro-benzo[d]azepin-3-yl}-1,1,1-trifluoro-propan-2-ol (S)-3-(7-Amino-8-methoxy-1,2,4,5-tetrahydro-benzo[d]azepin-3-yl)-1,1,1-trifluoro-propan-2-ol (88 mg, 0.29 mmol), (2,5-Dichloro-pyrimidin-4-yl)-(2-methoxy-4-morpholin-4-yl-phenyl)-amine (0.104 g, 0.292 mmol), and 10-Camphorsulfonic acid (0.10 g, 0.43 mmol) were heated in a microwave vial at 120° C. for a total of 5 h then for 1.5 h at 140° C. The dark brown solution was added to a stirred satd. sodium bicarbonate solution (15 mL), stirred for 5 min then the supernatant was removed and the solids were stirred with 10 mL water. These solids were purified by RP-HPLC (10-30% acetonitrile:water) followed by formation of the free base with Macroporous carbonate resin to afford (S)-3-{7-[5-Chloro-4-(2-methoxy-4-morpholin-4-yl-phenylamino)-pyrimidin-2-ylamino]-8-methoxy-1,2,4,5-tetrahydro-benzo[d]azepin-3-yl}-1,1,1-trifluoro-propan-2-ol as yellow solids (64 mg, 36%). m.p.=95-102° C.; LCMS (m/e) 624 (M+1); $^1$H-NMR (CD$_3$OD, 400 MHz) δ 7.93 (m, 2H), 7.69 (d, 1H, J=8.7 Hz), 6.81 (s, 1H), 6.69 (s, 1H), 6.55 (m, 1H), 4.68 (m, 1H), 3.85 (m, 10H), 3.3-3.5 (m, 6H), 3.20 (m, 4H), 3.10 (m, 2H), 2.85 (m, 2H).

Example 471

N-{2-[5-Chloro-2-(1-methyl-2,3,4,5-tetrahydro-1H-benzo[e][1,4]diazepin-8-ylamino)-pyrimidin-4-ylamino]-phenyl}-methanesulfonamide hydrochloride 471a) Synthesis of Methyl 2-Fluoro-4-nitrobenzoate.

To a 500 ml round bottom flask, 2-fluoro-4-nitrobenzoic acid (11.68 g, 63.1 mmoles), toluene (200 ml) and methanol (30 ml) were added, respectively. Trimethylsilyldiazomethane (2M) in diethyl ether (38 ml, 76 mmoles) was then added dropwise at room temperature over 30 minutes. The solution was then stirred for 1 hour. The solvents were then removed under vacuum to afford a yellow solid. The residual solvent was co-evaporated with methanol (100 ml) to give 12.52 g of yellow solid (100% yield). NMR 1H-(DMSO)-δ-8.28 (d, 1H, J=7.58 Hz), 8.10-8.22 (m, 2H), 3.93 (s, 3H).

4711b) Synthesis of 8-Nitro-1-methyl-1,2,3,4-tetrahydrobenzo[e][1,4]diazepine-5-one.

To a 300 ml round bottom flask, methyl 2-fluoro-4-nitrobenzoate (12.52, 63 mmoles), N-methyl ethylenediamine (4.82 g, 65 mmoles), DMF (200 ml) and K2CO3 (10.49 g, 76 mmoles) were added, respectively. The reaction mixture was then heated to 900 C for 18 hours. The reaction was cooled to room temperature. The mixture was then poured over ice and stirred for one hour. The solid was then filtered and washed with water. The residual water was removed under vacuum overnight. The solid was partitioned with diethyl ether and methanol (9/1). The solid was filtered and washed to afford 9.20 g of bright yellow solid (41.6% yield). NMR 1H-(DMSO)-δ-8.50 (bs, 1H), 7.68 (s, 2H), 7.50 (s, 1H), 3.23.38 (m, 4H), 2.90 (s, 2H)

471c) Synthesis of 8-Amino-1-methyl-1,2,3,4-tetrahydrobenzo[e][1,4]diazepine-5-one.

To a 500 ml round bottom flask, 8-nitro-1-methyl-1,2,3,4-tetrahydrobenzo[e][1,4]diazepine-5-one (6.70 g/30.3 moles), 10% Pd/C (1.30 g, catalytic), and ethanol (300 ml) were added. The heterogenous mixture was evacuated under vacuum and charged with hydrogen via balloon. This protocol was repeated three times. The reaction was then stirred at room temperature under hydrogen balloon for 18 hours. DMF (300 ml) was added, The mixture was heated to 50 C for one hour. The content was then filtered through Celite, and washed with reflux methanol. The solvent was then removed under vacuum to afford 4.33 g of brown solid (75% yield). NMR 1H-(DMSO)-δ-7.69 (bs, 1H), 7.18 (d, 1H, J=10.34 Hz), 6.09 (dd, 1H, JJ=8.34, 2.02 Hz), 6.04 (d, 1H, J=2.02 Hz), 5.40 (s, 2H), 3.12 (bs, 4H), 2.70 (s, 3H)

471d) Synthesis of 8-Amino-1-methyl-1,2,3,4-tetrahydrobenzo[e][1,4]diazepine.

To 1-liter round bottom flask, 8-amino-1-methyl-1,2,3,4-tetrahydrobenzo[e][1,4]diazepine-5-one (4.33 g, 22.6 mmoles) and dioxane (300 ml) were added. The mixture was then heated to 600 C. 5M Borane dimethylsulfide complex in diethyl ether (40 ml, 200 mmoles) was the added dropwise over thirty minutes. The reaction was heated to reflux for 18 hours. Upon cooling to room temperature, the reaction content was added to a stirring methanol solution (300 ml), and stirred for one hour. The solvents were then removed under vacuum to afford a gummy residue. The residue was partitioned with methanol (20 ml), and added to 6N HCl (40 ml) at room temperature. The mixture was then heated to reflux for one hour. The mixture was cooled to room temperature and extracted with ethyl acetate (1×200 ml). The aqueous was basified to pH 8 with 50% NaOH, and extracted with ethyl acetate (2×250 ml). The combined organic was washed with Brine, dried over magnesium sulfate, filtered and stripped to dryness. The product (2.58 g, 64% yield) was isolated via column chromatography with dichloromethane and ammonia in methanol (2% to 25% ammonia in methanol) as eluant. NMR 1H-(CDCl3)-δ-6.90 (d, 1H, J=7.83 Hz), 6.30 9s, 1H), 6.21 (dd, 1H, JJ=7.83, 2.02) 3.83 (s, 2H), 3.47 (s, 2H) 3.03-3.08 (m, 2H), 2.90-2.95 (m, 2H), 2.85 (s, 3H).

471e) Synthesis of N,N-(2-nitrophenyl)-bis-methanesulfonamide

To a 500 ml round bottom flask, 2-nitroaniline (9.53 g, 67.6 mmoles) and pyridine (250 ml) were added. Methanesulfonyl chloride (27.5 ml, 338 mmoles) was added dropwise over 30 minutes under nitrogen. The reaction mixture was stirred at room temperature for 18 hours. The solvent was then removed under vacuum to give a brown solid. The solid was then dissolved in dichloromethane (500 ml). The dichloromethane solution was washed with 1NHCl (300 ml), water (300 ml) and Brine (200 ml). The organic was then dried over magnesium sulfate. The solid was filtered and washed with dichloromethane (150 ml). The solvent was stripped to afford dark solid (15.00 g, 84% yield).

NMR 1H-(DMSO)-δ-8.18 (d, 1H), 7.75-7.90 (m, 2H), 3.57 (s, 6H)

471f) Synthesis of N-(2-nitrophenyl)-methanesulfonamide. To a 500 ml round bottom flask, N,N-(2-nitrophenyl)-bis-methanesulfonamide (15.00 g, 56.7 mmoles) and THF (200 ml) were added. IM Tetrabutylammonium fluoride in THF (55 ml, 55 mmoles) was added under nitrogen. The reaction mixture was stirred at room temperature for 3 hours. The reaction was partitioned with ethyl acetate (500 ml) and water (200 ml). The organic layer was separated, washed with brine and dried over magnesium sulfate. The solid was filtered and washed with ethyl acetate. The organic was concentrated to dryness. The desired product (5.70 g, 47% yield) was isolated via column chromatography with hexane and ethyl acetate as eluant. NMR 1H-(CDCl3)-δ-9.83 (s, 1H), 8.04 (d, 1H), 7.70-7.80 (m, 1H), 7.65 (d, 1H), 7.35-7.44 (m, 1H), 3.24 (s, 3H)

471g) Synthesis of N-(2-Amino-phenyl)-methanesulfonamide. To a 500 ml round bottom flask, N-(2-nitro-phenyl)-methanesulfonamide (5.70 g, 26.4 mmoles), ethanol (250 ml), and 10% Pd/C (1.10 g) were added. The reaction was evacuated and charged with hydrogen via balloon three times. The mixture was stirred at room temperature for 18 hours. The solid was filtered through Celite and washed with methanol (200 ml). The solvent was removed under vacuum to afford a white solid (5.00 g, 100% yield). NMR 1H-(DMSO)-δ-8.70 (bs, 1H), 7.06 (d, 1H), 7.00 (t, 1H), 6.73 (d, 1H), 6.54 (t, 1H), 5.10 (bs, 2H), 2.90 (s, 3H)

471 h) Synthesis of N-[2-(2,5-Dichloro-pyrimidin-4-ylamino)-phenyl]-methanesulfonamide. To a 50 ml round bottom flask, N-(2-amino-phenyl)-methanesulfonamide (2.00 g, 10.7 mmoles), 2,4,5-trichloropyrimidine (6 g, 32.6 mmoles) was added. The reaction mixture was heated to 500 C for 3 hours. The reaction was partitioned with ethyl acetate and water. The organic layer was separated, washed with Brine and dried over magnesium under sulfate. The solid was filtered and washed with ethyl acetate. The solvent was removed under vacuum. The product (1.30 g, 36% yield) was isolated via column chromatography with hexanes and ethyl acetate as eluant. NMR 1H-(DMSO)-δ-9.30 (s, 1H), 9.07 (s, 1 h), 8.39 (s, 1H), 7.57-7.65 (m, 1H), 7.43-7.48 (m, 1H), 7.23-7.40 (m, 1H), 3.00 (s, 3H)

471i) Synthesis of N-{2-[5-Chloro-2-(1-methyl-2,3,4,5-tetrahydro-1H-benzo[e][1,4]diazepin-8-ylamino)-pyrimidin-4-ylamino]-phenyl}-methanesulfonamide hydrochloride: To 40 ml sure-seal reaction vial, 8-Amino-1-methyl-1,2,3,4-tetrahydrobenzo[e][1,4]diazepine (0.33 g, 2 mmoles), 2-methoxyethanol (6 ml), and N-[2-(2,5-Dichloro-pyrimidin-4-ylamino)-phenyl]-methanesulfonamide (0.60 g, 1.8 mmole), 4M HCl in dioxane (1 ml, 4 mmoles) were added. The reaction was heated to reflux for 3 hours. Upon cooling to room temperature, the solid was filtered and washed with cold 2-methoxyethanol to afford a white solid (0.60 g, 70% yield). NMR 1H-(DMSO)-δ-9.32 (s, 1H), 8.99 (bs, 2H), 8.90 (bs, 1H), 8.26 (s, 1H), 7.83 (d, 1H, J=6.82 Hz), 7.45 (d, 1H, 7.58 Hz), 7.25-7.38 (m, 2H), 7.20 (d, 1H, J=8.59 Hz), 7.12 (s, 1H), 7.08 (d, 1H, J=8.59), 4.05 (bs, 2H), 3.17 (bs, 2H), 3.10 (bs, 2H), 2.93 (s, 3H), 2.66 (s, 3H). LCMS (ESI+) 510.14 (M+H); MP=270-274° C.

Example 472

{8-[5-Chloro-4-(2-methanesulfonylamino-phenylamino)-pyrimidin-2-ylamino]-1-methyl-1,2,3,5-tetrahydro-benzo[e][1,4]diazepin-4-yl}-acetic acid methyl ester Synthesis of {8-[5-Chloro-4-(2-methanesulfonylamino-phenylamino)-pyrimidin-2-ylamino]-1-methyl-1,2,3,5-tetrahydro-benzo[e][1,4]diazepin-4-yl}-acetic acid methyl ester. To 40 ml sure-seal reaction vial, N-{2-[5-Chloro-2-(1-methyl-2,3,4,5-tetrahydro-1H-benzo[e][1,4]diazepin-8-ylamino)-pyrimidin-4-ylamino]-phenyl}-methanesulfonamide hydrochloride (53 mg, 0.11 mmole), methyl bromoacetate (0.010 ml, 0.11 mmole), tetrahydrofuran (5 ml), and Hunig's base (0.2 ml, 1.2 mmoles) were added. The reaction was then heated to 70 C for 5 hours. The solvent was then removed under vacuum. The product (25 mg, 41% yield) was isolated via column chromatography with dichloromethane and methanol as eluant. NMR 1H-(CDCl3)-δ-8.04 (s, 1H), 7.74 (d, 1H, J=7.33 Hz), 0 7.61 (s, 1H), 7.46 (d, 1H, J=7.08 Hz), 7.02-7.35 (m, 3H), 7.07 (s, 1H), 6.92 (d, 1H, J=8.34 Hz), 6.86 9d, 1H, J=8.08 Hz), 6.82 (s, 1H), 3.83 (s, 2H), 3.75 (s, 3H), 3.30 (s, 2H), 3.02 (bd, 2H, J=4.65 Hz), 2.96 (bd, 2H, J=5.31 Hz), 2.91 (s, 3H), 2.69 (s, 3H).
LCMS (ESI+) 546.31 (M+H); MP=106-124° C.

Example 473

Acetic acid 2-{8-[5-chloro-4-(2-methanesulfonylamino-phenylamino)-pyrimidin-2-ylamino]-1-methyl-1,2,3,5-tetrahydro-benzo[e][1,4]diazepin-4-yl}-ethyl ester Synthesis of Acetic acid 2-{8-[5-chloro-4-(2-methanesulfonylamino-phenylamino)-pyrimidin-2-ylamino]-1-methyl-1,2,3,5-tetrahydro-benzo[e][1,4]diazepin-4-yl}-ethyl ester. The product (15 mg, 24% yield) was isolated as described in example 472
NMR 1H-(CDCl3)-δ-8.09 (s, 1H), 7.83 (s, 1H), 7.74 (d, 1H, J=7.58 Hz), 7.51 (d, 1H, J=7.33 Hz), 7.25-7.35 (m, 2H), 7.20-7.25 (bs, 1H), 6.93-7.08 (m, 2H), 694 (s, 1H), 4.35-4.55 (m, 2H), 4.00-4.20 (m, 2H), 3.15-3.35 (m, 4H), 3.00-3.10 (m, 2H), 2.96 (s, 3H), 2.73 (s, 3H), 2.15 (s, 3H). LCMS (ESI+) 560.12 (M+H); MP=86-120° C.

Example 474

Synthesis of N-{2-[5-Chloro-2-(4-methanesulfonyl-1-methyl-2,3,4,5-tetrahydro-1H-benzo[e][1,4]diazepin-8-ylamino)-pyrimidin-4-ylamino]-phenyl}-methanesulfonamide Synthesis of N-{2-[5-Chloro-2-(4-methanesulfonyl-1-methyl-2,3,4,5-tetrahydro-1H-benzo[e][1,4]diazepin-8-ylamino)-pyrimidin-4-ylamino]-phenyl}-methanesulfonamide. The product (30 mg) was isolated as described in example 472. NMR 1H-(CDCl3)-δ-8.06 (s, 1H), 7.63-7.70 (m, 1H), 7.54 (s, 1H), 7.45-7.52 (m, 1H), 7.32-7.37 (m, 2H), 7.00-7.09 (m, 3H), 6.93 (s, 1H), 4.42 (s, 2H), 3.57-3.65 (m, 2H), 3.05-3.12 (m, 2H), 2.93 (s, 3H), 2.76 (s, 3H), 2.65 (s, 3H); LCMS (ESI+) 552.41 (M+H); MP=95-161° C. (foamed).

Example 475

N-{(1R,2R)-2-[5-Chloro-2-(1-methyl-2,3,4,5-tetrahydro-1H-benzo[e][1,4]diazepin-8-ylamino)-pyrimidin-4-ylamino]-cyclohexyl}-methanesulfonamide Synthesis of N-{(1R,2R)-2-[5-Chloro-2-(1-methyl-2,3,4,5-tetrahydro-1H-benzo[e][1,4]diazepin-8-ylamino)-pyrimidin-4-ylamino]-cyclohexyl}-methanesulfonamide. To 40 ml sure-seal reaction vial, 8-Amino-1-methyl-1,2,3,4-tetrahydrobenzo[e][1,4]diazepine (0.33 g, 2 mmoles), methoxy ethanol (6 ml), and N-[(1R,2R)-2-(2,5-Dichloro-pyrimidin-4-ylamino)-cyclohexyl]-methanesulfonamide (0.51 g, 1.1.5 mmole), 4M HCl in dioxane (1 ml, 4 mmoles) were added. The reaction was heated to reflux for 3 hours. Upon cooling to room temperature, the solvent was then removed under vacuum to afford a yellow solid. The product (0.53 g, 74% yield) was isolated via column chromatography with dichloromethane and ammonia in methanol (2% to 30% ammonia in methanol) as eluant. NMR 1H-(DMSO)-δ-9.02 (bs, 1H), 7.93 (s, 1H), 7.32 (d, 1H, J=8.59 Hz), 7.16 (bs, 2H), 6.93 (d, 1H, J=7.58), 6.67 (d, 1 h, J=7.58 Hz), 3.80-3.90 (bm, 1H), 3.64 (s, 2H), 3.30-3.40 (bm, 1H), 3.17 (d, 1H, 5.2 Hz), 2.92 (s, 3H), 2.83-2.90 (m, 4H), 2.82 (s, 3H), 1.95-2.12 (m, 2H), 1.65-1.75 (m, 2H), 1.15-1.48 (m, 4H). LCMS (ESI+) 480.13 (M+H); MP=153-206° C.

Example 476

Acetic acid 2-{8-[5-chloro-4-((1R,2R)-2-methanesulfonylamino-cyclohexylamino)-pyrimidin-2-ylamino]-1-methyl-1,2,3,5-tetrahydro-benzo[e][1,4]diazepin-4-yl}-ethyl ester Synthesis of Acetic acid 2-{8-[5-chloro-4-((1R,2R)-2-methanesulfonylamino-cyclohexylamino)-pyrimidin-2-ylamino]-1-methyl-1,2,3,5-tetrahydro-benzo[e][1,4]diazepin-4-yl}-ethyl ester. To 40 ml sure-seal reaction vial, N-{(1R,2R)-2-[5-chloro-2-(1-methyl-2,3,4,5-tetrahydro-1H-benzo[e][1,4]diazepin-8-ylamino)-pyrimidin-4-ylamino]-cyclohexyl}-methanesulfonamide (90 mg, 0.19 mmole), 2-bromoethyl acetate (36 mg, 0.21 mmole), triethylamine (0.3 ml, 2.1 mmoles), KI (10 mg, catalytic), and DMF (5 ml) were added. The reaction was heated to 70 C for 18 hours. The solvent was removed under vacuum to afford a brown solid. The desired product (64 mg, 54% yield) was isolated via column chromatography with dichloromethane and methanol as eluant. NMR 1H-(CDCl3)-δ-7.94 (s, 1H), 7.16 (d, 1H, J=7.58 Hz), 7.06 (d, 1H, J=8.08 Hz), 6.93 (s, 1H), 6.83 (s, 1H), 5.37 (d, 1H, J=7.58 Hz), 5.31 (d, 1H, J=7.58 Hz), 4.20 (t, 2H, J=5.81 Hz), 3.85-4.00 (m, 3H), 3.15-3.30 (m, 1H), 2.95-3.10 (m, 4H), 2.91 (s, 3H), 2.78 (s, 3H), 2.70 (t, 2H, J=6.13 Hz), 2.12-2.25 (m, 2H), 2.07 (s, 3H), 1.78-1.90 (m, 2H), 1.30-1.50 (m, 4H) LCMS (ESI+) 566.41 (M+H); MP=110-142° C.

Example 477

N-{(1R,2R)-2-[5-Chloro-2-(4-methanesulfonyl-1-methyl-2,3,4,5-tetrahydro-1H-benzo[e][1,4]diazepin-8-ylamino)-pyrimidin-4-ylamino]-cyclohexyl}-methanesulfonamide Synthesis of N-{(1R,2R)-2-[5-Chloro-2-(4-methanesulfonyl-1-methyl-2,3,4,5-tetrahydro-1H-benzo[e][1,4]diazepin-8-ylamino)-pyrimidin-4-ylamino]-cyclohexyl}-methanesulfonamide. The product (58 mg, 61% yield) was isolated as described in example 472. NMR 1H-(DMSO)-δ-9.14 (s, 1H), 7.94 (s, 1H), 7.40 (d, 1H, J=8.09 Hz), 7.26 (s, 1H), 7.17 (d, 1H, J=8.84 Hz, 7.01 (d, 1H, J=8.84 Hz), 6.72 (d, 1H, J=7.58 Hz), 4.26 (s, 2H), 3.80-3.90 (m, 1H), 3.40-3.50 (m, 2H), 3.07-3.15 (m, 2H), 2.87 (s, 3H), 2.76 (s, 3H), 2.73 (s, 3H), 1.95-2.12 (m, 2H), 1.65-1.80 (m, 2H), 1.20-1.45 (m, 4H)
LCMS (ESI+) 558.14 (M+H); MP=160-164° C.

Example 478

N-((1R,2R)-2-{5-Chloro-2-[4-(2-hydroxy-ethyl)-1-methyl-2,3,4,5-tetrahydro-1H-benzo[e][1,4]diazepin-8-ylamino]-pyrimidin-4-ylamino}-cyclohexyl)-methanesulfonamide Synthesis of N-((1R,2R)-2-{5-Chloro-2-[4-(2-hydroxy-ethyl)-1-methyl-2,3,4,5-tetrahydro-1H-benzo[e][1,4]diazepin-8-ylamino]-pyrimidin-4-ylamino}-cyclohexyl)-methanesulfonamide. To a 25 ml round bottom flask, acetic acid 2-{8-[5-chloro-4-((1R,2R)-2-methanesulfonylamino-cyclohexylamino)-pyrimidin-2-ylamino]-1-methyl-1,2,3,5-tetrahydro-benzo[e][1,4]diazepin-4-yl}-ethyl ester (50 mg, 0.09 mmole), dioxane (5 ml), and 1M LiOH (1 mL, 1 mmole) were added and stirred at room temperature for 18 hours. The reaction was then acidified to pH 2 with 1NHCl. The solvents were removed under vacuum to give a white solid. The desired product (10 mg, 21% yield) was isolated via column chromatography with dichloromethane and ammonia in methanol as eluant. NMR 1H-(CDCl3)-δ-7.93 (s, 1H), 7.15 (d, 1H, J=7.83 Hz), 7.04 (d, 1H, J=7.83 Hz), 6.93 (s, 1H), 6.89 (s, 1H), 5.38 (d, 1H, J=5.73 Hz), 5.29 (s, 1H), 3.82-3.95 (m, 1H), 3.80 (s, 2H), 3.61 (t, 2H, J=5.31 Hz), 3.15-3.30 (m, 1H), 2.99 (bs, 4H), 2.91 (s, 3H), 2.78 (s, 3H), 2.61 (t, 2H, J=5.30Hz), 2.10-2.30 (m, 2H), 1.75-1.90 (m, 2H), 1.30-1.50 (m, 4H)

LCMS (ESI+) 524.38 (M+H); MP=181-190° C.

Example 479

N-{(1R,2R)-2-[5-Chloro-2-(4-cyclopropylmethyl-1-methyl-2,3,4,5-tetrahydro-1H-benzo[e][1,4]diazepin-8-ylamino)-pyrimidin-4-ylamino]-cyclohexyl}-methanesulfonamide Synthesis of N-{(1R,2R)-2-[5-Chloro-2-(4-cyclopropylmethyl-1-methyl-2,3,4,5-tetrahydro-1H-benzo[e][1,4]diazepin-8-ylamino)-pyrimidin-4-ylamino]-cyclohexyl}-methanesulfonamide. The product (18 mg, 24% yield) was isolated as described in example 476. NMR 1H-(CDCl3)-δ-7.93 (s, 1H), 7.15 (d, 1H, J=8.34 Hz), 7.08 (d, 1H, J=8.09 Hz), 6.94 (s, 1H), 6.92 (s, 1H), 3.95 (s, 2H), 3.80-3.92 (m, 1H), 3.18-3.30 (m, 1H), 3.06 (bs, 4H), 2.98 (s, 3H), 2.78 (s, 3H), 2.47 (d, 2H, J=4.72 Hz), 2.15-2.28 (m, 2H), 1.60-1.85 (m, 2H), 1.30-1.50 (m, 4H), 0.70-0.90 (m, 1H), 0.59 (d, 2H, J=5.40 Hz), 0.19 (d, 2H, J=4.80Hz). LCMS (ESI+) 534.38 (M+H); MP=175-210° C.

Example 480

N-{(1R,2R)-2-[5-Chloro-2-(1-methyl-4-prop-2-ynyl-2,3,4,5-tetrahydro-1H-benzo[e][1,4]diazepin-8-ylamino)-pyrimidin-4-ylamino]-cyclohexyl}-methanesulfonamide Synthesis of N-{(1R,2R)-2-[5-Chloro-2-(1-methyl-4-prop-2-ynyl-2,3,4,5-tetrahydro-1H-benzo[e][1,4]diazepin-8-ylamino)-pyrimidin-4-ylamino]-cyclohexyl}-methanesulfonamide. The product (30 mg, 40% yield) was isolated following protocol as described in Example 472 as a foamy solid. NMR 1H-(CDCl3)-δ-7.95 (s, 1H), 7.18 (m, 1H), 7.08 (m, 1H), 6.94 (s, 1H), 6.92 (s, 1H), 3.95 (s, 2H), 3.80-3.92 (m, 1H), 3.18-3.30 (m, 1H), 3.06 (bs, 4H), 2.98 (s, 3H), 2.78 (m, 1H), 2.32 (s, 1H), 2.15-2.28 (m, 2H), 1.60-1.85 (m, 2H), 1.30-1.50 (m, 4H), LCMS (ESI+) 518.09 (M+H).

Example 481

8-[5-Chloro-4-((1R,2R)-2-methanesulfonylamino-cyclohexylamino)-pyrimidin-2-ylamino]-1-methyl-1,2,3,5-tetrahydro-benzo[e][1,4]diazepine-4-carboxylic acid dimethylamide Synthesis of 8-[5-Chloro-4-((1R,2R)-2-methanesulfonylamino-cyclohexylamino)-pyrimidin-2-ylamino]-1-methyl-1,2,3,5-tetrahydro-benzo[e][1,4]diazepine-4-carboxylic acid dimethylamide. The product (30 mg, 50% yield) was isolated following protocol as described in example 476. NMR 1H(CDCl3)-7.93 (s, 1H), 7.11 (bs, 2H), 6.94 (bs, 1H), 6.87 (bs, 1H), 5.35 (dd, 1H), 4.28 (s, 2H), 3.84-3.95 (m, 1H), 3.44-3.52 (m, 2H), 3.18-3.27 (m, 1H) 3.12-3.17 (m, 2H), 2.93 (s, 3H), 2.83 (s, 6H), 2.78 (s, 3H), 2.15-2.28 (m, 2H), 1.77-1.90 (m, 2H), 1.30-1.50 (m, 4H). LCMS (ESI+) 551.40 (M+H); MP=110-114° C.

Example 482

N-((1R,2R)-2-{5-Chloro-2-[4-(imidazole-1-carbonyl)-1-methyl-2,3,4,5-tetrahydro-1H-benzo[e][1,4]diazepin-8-ylamino]-pyrimidin-4-ylamino}-cyclohexyl)-methanesulfonamide Synthesis of N-((1R,2R)-2-{5-Chloro-2-[4-(imidazole-1-carbonyl)-1-methyl-2,3,4,5-tetrahydro-1H-benzo[e][1,4]diazepin-8-ylamino]-pyrimidin-4-ylamino}-cyclohexyl)-methanesulfonamide. The product (72 mg, 63% yield) was isolated following protocol as described in Example 472. NMR 1H-(CDCl3)-δ-7.96 (s, 1H), 7.88 (s, 1H), 7.24 (s, 1H), 7.20 (d, 1H, J=7.83 Hz), 7.12 (s, 1H), 7.05 (s, 1H), 6.95-7.03 (m, 1H), 6.93 (s, 1H), 5.48 (d, 1H, J=7.58 Hz), 5.35 (d, 1H, J=7.50Hz), 4.55 (s, 2H), 3.84-3.95 (m, 1H), 3.81 (bs, 2H), 3.18-3.32 (m, 3H), 2.98 (s, 3H), 2.82 (s, 3H), 2.16-2.32 (m, 2H), 1.76-1.93 (m, 2H), 1.35-1.50 (m, 4H). LCMS (ESI+) 574.40 (M+H); MP=112° C. (foamed)

Example 483

2-[5-Chloro-2-(4-methanesulfonyl-1-methyl-2,3,4,5-tetrahydro-1H-benzo[e][1,4]diazepin-8-ylamino)-pyrimidin-4-ylamino]-N-methyl-benzamide 483a) Synthesis of 2-[5-Chloro-2-(1-methyl-2,3,4,5-tetrahydro-1H-benzo[e][1,4]diazepin-8-ylamino)-pyrimidin-4-ylamino]-N-methyl-benzamide hydrochloride: To 40 ml sure-seal reaction vial, 8-amino-1-methyl-1,2,3,4-tetrahydrobenzo[e][1,4]diazepine (0.33 g, 2 mmoles), 2-methoxyethanol (6 ml), and 2-(2,5-dichloro-pyrimidin-4-ylamino)-N-methyl-benzamide (0.53 g, 1.8 mmole), 4M HCl in dioxane (1 ml, 4 mmoles) were added. The reaction was heated to reflux for 3 hours. Upon cooling to room temperature, the solid was filtered and washed with cold 2-methoxyethanol to afford a white solid (0.48 g, 56% yield). LCMS (ESI+) 438.10 (M+H).

483b) Synthesis of 2-[5-Chloro-2-(4-methanesulfonyl-1-methyl-2,3,4,5-tetrahydro-1H-benzo[e][1,4]diazepin-8-ylamino)-pyrimidin-4-ylamino]-N-methyl-benzamide. To 40 ml sure-seal reaction vial, N-{(1R,2R)-2-[5-Chloro-2-(1-methyl-2,3,4,5-tetrahydro-1H-benzo[e][1,4]diazepin-8-ylamino)-pyrimidin-4-ylamino]-cyclohexyl}-methanesulfonamide (70 mg, 0.15 mmole), methanesulfonyl chloride (21 mg, 0.21 mmole), triethylamine (0.3 ml, 2.1 mmoles), and THF (5 ml) were added the mixture was stirred at room temperature for 72 hours. The solvent was removed under vacuum. The product (20 mg, 26% yield) was isolated via column chromatography with dichloromethane and methanol as eluant. NMR 1H-(CDCl3)-δ-11.11 (s, 1H), 8.64 (d, 1H, J=8.59 Hz), 8.11 (s, 1H), 7.49 (d, 1H, J=8.83 Hz), 7.44 (t, 1H, J=8.08 Hz), 7.22 (d, 1H, J=8.34 Hz), 7.17 (d, 1H, J=7.33 Hz), 7.08 (t, 1H, J=7.83 Hz), 6.98 (s, 1H), 6.21 (bs, 1H), 4.45 (s, 2H), 3.64 (t, 2H, J=4.80Hz), 3.11 (t, 2H, J=4.80 Hz), 3.03 (d, 3H, J=5.20Hz), 2.85 (s, 3H), 2.66 (s, 3H). LCMS (ESI+) 516.10 (M+H); MP=200-207° C.

Example 484

2-{5-Chloro-2-[4-(2-methoxy-ethyl)-1-methyl-2,3,4,5-tetrahydro-1H-benzo[e][1,4]diazepin-8-ylamino]-pyrimidin-4-ylamino}-N-methyl-benzamide Synthesis of 2-{5-Chloro-2-[4-(2-methoxy-ethyl)-1-methyl-2,3,4,5-tetrahydro-1H-benzo[e][1,4]diazepin-8-ylamino]-pyrimidin-4-ylamino}-N-methyl-benzamide. The product (315 mg, 46% yield) was isolated following protocol as described in Example 483b. Followed procedure as described in Example 473 to afford 315 mg of desired product. NMR 1H-(CDCl3)-δ-11.07 (s, 1H), 8.69 (d, 1H, J=8.59 Hz, 7.40-7.53 (m, 2H), 7.14 (d, 1H, J=8.09 Hz), 7.05 (d, 2H, J=7.58 Hz), 6.97 (s, 1H), 3.86 (s, 2H), 3.52 9t, 2H, J=5.56 Hz), 3.38 (s, 3H), 2.92-3.07 (bm, 7H), 2.79 (s, 3H), 2.65 (t, 2H, J=5.53H)

LCMS (ESI+) 496.40 (M+H); MP=172-174° C.

Example 485

2-{5-Chloro-2-[4-(2-hydroxy-ethyl)-1-methyl-2,3,4, 5-tetrahydro-1H-benzo[e][1,4]diazepin-8-ylamino]-pyrimidin-4-ylamino}-N-methyl-benzamide 485a) Synthesis of Acetic acid 2-{8-[5-chloro-4-(2-methylcarbamoyl-phenylamino)-pyrimidin-2-ylamino]-1-methyl-1,2,3,5-tetrahydro-benzo[e][1,4]diazepin-4-yl}-ethyl ester: To 40 ml sure-seal reaction vial, 2-[5-chloro-2-(1-methyl-2,3,4,5-tetrahydro-1H-benzo[e][1,4]diazepin-8-ylamino)-pyrimidin-4-ylamino]-N-methyl-benzamide (105 mg, 0.19 mmole), 2-bromoethyl acetate (36 mg, 0.21 mmole), triethylamine (0.3 ml, 2.1 mmoles), KI (10 mg, catalytic), and DMF (5 ml) were added. The reaction was heated to 700 C for 18 hours. The solvent was removed under vacuum to afford a brown solid. The desired product (10 mg, 10%) was isolated via column chromatography with dichloromethane and methanol as eluant. LCMS (ESI+) 524.42 (M+H)

485b) Synthesis of 2-{5-Chloro-2-[4-(2-hydroxy-ethyl)-1-methyl-2,3,4,5-tetrahydro-1H-benzo[e][1,4]diazepin-8-ylamino]-pyrimidin-4-ylamino}-N-methyl-benzamide.

The product (2.4 mg 26% yield) was isolated as a foam following protocol as described in Example 478. NMR 1H-(CDC)l3)-δ-11.10 (s, 1H), 8.64 (d, 1H, J=8.34 Hz), 8.09 (s, 1H), 7.50 (d, 1H, J=7.83 Hz), 7.43 (t, 1H, J=7.58 Hz), 7.20 (d, 1H, J=8.08 Hz), 7.00-7.15 (m, 4H), 5.20-5.60 (bm, 1H), 4.67 (bs, 1H), 3.97 (s, 2H), 3.74 (t, 2H, J=4.05 Hz), 3.10 (bs, 4H), 3.04 (d, 3H, J=4.60Hz), 2.81 (s, 3H), 2.76 (t, 2H, J=4.05 Hz). LCMS (ESI+) 482.38

Example 486

2-{5-Chloro-2-[4-(imidazole-1-carbonyl)-1-methyl-2,3,4,5-tetrahydro-1H-benzo[e][1,4]diazepin-8-ylamino]-pyrimidin-4-ylamino}-N-methyl-benzamide Synthesis of 2-{5-Chloro-2-[4-(imidazole-1-carbonyl)-1-methyl-2,3,4,5-tetrahydro-1H-benzo[e][1,4]diazepin-8-ylamino]-pyrimidin-4-ylamino}-N-methyl-benzamide.

The product (22 mg, 28% yield) was isolated following protocol as described in example 483b. NMR 1H-(CDCl3)-δ-11.10 (s, 1H), 8.65 (d, 1H, J=8.08), 8.11 (s, 1H), 7.87 (s, 1H), 7.42-7.53 (m, 2H), 7.22 (s, 1H), 7.16 (d, 1H, J=8.08 Hz), 7.11 (s, 1H), 7.08 (d, 1H, J=7.58 Hz), 6.70-6.85 (m, 2H), 6.18-6.30 (m, 1H), 4.53 (s, 2H), 3.75-3.83n (m, 2H), 3.18-3.25 (m, 2H), 3.04 (d, 3H, J=4.60Hz), 2.87 (s, 3H). LCMS (ESI+) 532.40 (M+H); MP=104° C. (foam).

Example 487

2-[5-Chloro-2-(1-methyl-4-prop-2-ynyl-2,3,4,5-tetrahydro-1H-benzo[e][1,4]diazepin-8-ylamino)-pyrimidin-4-ylamino]-N-methyl-benzamide Synthesis of 2-[5-Chloro-2-(1-methyl-4-prop-2-ynyl-2,3,4,5-tetrahydro-1H-benzo[e][1,4]diazepin-8-ylamino)-pyrimidin-4-ylamino]-N-methyl-benzamide.

The product (48 mg, 48% yield)) was isolated following protocol as described in example 483b. NMR 1H-(CDCl3)-δ-11.07 (s, 1H), 8.66 (d, 1H, J=8.33 Hz), 8.09 (s, 1H), 7.40-7.55 (m, 2H), 7.02-7.20 (m, 3H), 6.99 (s, 2H), 6.24 (bs, 1H), 3.83 (s, 2H), 3.39 (bs, 2H), 2.95-3.10 (m, 7H), 2.80 (s, 3H), 2.30 (s, 1H). LCMS (ESI+) 476.40 (M+H); MP=181-185° C.

Example 488

2-[5-Chloro-2-(1-methyl-4-prop-2-ynyl-2,3,4,5-tetrahydro-1H-benzo[e][1,4]diazepin-8-ylamino)-pyrimidin-4-ylamino]-N-methyl-N-prop-2-ynyl-benzamide Synthesis of 2-[5-Chloro-2-(1-methyl-4-prop-2-ynyl-2,3,4,5-tetrahydro-1H-benzo[e][1,4]diazepin-8-ylamino)-pyrimidin-4-ylamino]-N-methyl-N-prop-2-ynyl-benzamide. The product (2.6 mg, 5% yield) was isolated as a foamy solid following protocol as described in example 483b. NMR 1H-(CDCl3)-δ-8.66 (d, 1H, J=8.33 Hz), 8.09 (s, 1H), 7.40-7.55 (m, 2H), 7.02-7.20 (m, 3H), 6.99 (s, 2H), 6.24 (bs, 1H), 3.83 (s, 2H), 3.39 (bs, 2H), 2.95-3.10 (m, 9H), 2.80 (s, 3H), 2.34 (s, 2H). LCMS (ESI+) 514.13 (M+H)

Example 489

8-[5-Chloro-4-(2-methylcarbamoyl-phenylamino)-pyrimidin-2-ylamino]-1-methyl-1,2,3,5-tetrahydro-benzo[e][1,4]diazepine-4-carboxylic acid dimethylamide Synthesis of 8-[5-Chloro-4-(2-methylcarbamoyl-phenylamino)-pyrimidin-2-ylamino]-1-methyl-1,2,3,5-tetrahydro-benzo[e][1,4]diazepine-4-carboxylic acid dimethylamide.

The product (78 mg, 95% yield) was isolated following protocol as described in example 483b. NMR 1H-(CDCl3)-δ-11.08 (s, 1H), 8.67 (d, 1H, J=8.33 Hz), 8.10 (s, 1H), 7.48 (d, 1H, J=7.83 Hz), 7.40 (t, 1H, J=8.33 Hz), 7.00-7.20 (m, 3H), 6.99 (s, 2H), 6.95 (s, 1H), 6.23 (bs, 1H), 4.28 (s, 2H), 3.49 (bs, 2H), 3.10-3.18 (m, 2H), 3.03 (d, 3H, J=4.53 Hz), 2.84 (s, 6H), 2.82 (s, 3H). LCMS (ESI+) 509.40 (M+H); MP=108° C. (foam).

Example 490

N-((1R,2R)-2-{5-Chloro-2-[7-methoxy-4-(2-methoxy-ethyl)-1-methyl-2,3,4,5-tetrahydro-1H-benzo[e][1,4]diazepin-8-ylamino]-pyrimidin-4-ylamino}-cyclohexyl)-methanesulfonamide 490a) Synthesis of 8-tert-Butoxycarbonylamino-1-methyl-1,2,3,5-tetrahydro-benzo[e][1,4]diazepine-4-carboxylic acid tert-butyl ester. To a 500 ml round bottom flask, 8-amino-1-methyl-1,2,3,4-tetrahydrobenzo[e][1,4]diazepine (1.50 g, 8.47 mmoles), di-tert-butyl dicarbonate (4.00 g, 18.6 mmoles), THF (50 ml), and potassium carbonate (3.50 g, 25.4 mmoles) were added, respectively. The mixture was stirred at room temperature overnight. The reaction was partitioned with water (100 ml), and extracted with ethyl acetate (3×100 ml). The combined organic was washed with Brine and dried over magnesium sulfate. The solid was then filtered and washed with ethyl acetate. The desired product (2.43 g, 98% yield) was isolated via column chromatography with hexane and ethyl acetate as eluant. NMR 1H-(DMSO)-δ-9.19 (bs, 1H), 7.12 (bs, 1H), 6.85-7.04 (m, 2H), 4.20 (bs, 2H), 3.50 (bs, 2H), 2.84-3.00 (bd, 2H, rot.), 2.79 (s, 3H), 1.48 (s, 9H), 1.34 (s, 9H)

490b) Synthesis of 7-Bromo-8-tert-butoxycarbonylamino-1-methyl-1,2,3,5-tetrahydro-benzo[e][1,4]diazepine-4-carboxylic acid tert-butyl ester. To a 200 ml round bottom flask, 8-tert-butoxycarbonylamino-1-methyl-1,2,3,5-tetrahydro-benzo[e][1,4]diazepine-4-carboxylic acid tert-butyl ester (5.00 g, 13.2 mmoles), and DMF were added. N-Bromosuccinimide (2.88 g, 16.2 mmoles) was added portion wise over 15 minutes. The reaction was stirred at room temperature overnight. Dichloromethane (500 ml) was added. The organic layer was washed with water (100 ml), and subsequently with Brine. The organic was dried over magnesium sulfate. The solid was filtered and washed with dichloromethane. The organic was then moved under vacuum to give a brown solid. The desired product (5.20 g, 86% yield) was isolated via column chromatography with hexanes and ethyl acetate as eluant. NMR 1H-(CDCl3)-δ-7.84 (bs, 1H), 7.40 (bs, 0.3H, rot), 7.26 (bs, 0.7H, rot.), 6.96 (bs, 1H), 4.33 (bs, 0.6H, rot.), 4.26 (s, 1.4H, rot.), 3.61 (bs, 2H), 2.92-3.03 (m, 5H), 1.53 (s, 9H), 1.43 (s, 9H).

490c) Synthesis of 7-tert-Butoxycarbonylamino-8-(5,5-dimethyl-[1,3,2]dioxaborinan-2-yl)-5-methyl-2,3,4,5-tetrahydro-benzo[b][1,4]diazepine-1-carboxylic acid tert-butyl ester. To a 25 ml round bottom flask with condensor, 7-bromo-8-tert-butoxycarbonylamino-1-methyl-1,2,3,5-tetrahydro-benzo[e][1,4]diazepine-4-carboxylic acid tert-butyl ester (478 mg, 11.0 mmole), palladium (II) acetate (12 mg, 0.05 mmole), 2-(dicyclohexylphosphino)biphenyl (70 mg, 0.2 mmole), and bis(neopentylglycolato)diboron (0.983 g, 4.3 mmoles) were added. The combined solid was purged with nitrogen for 10 minutes. Dioxane (8 ml) and triethylamine (0.6 ml, 4.3 mmoles) were added respectively. The reaction was then heated to reflux for one hour. Upon cooling to room temperature, the solvent was then removed under vacuum to give a brown solid. The desired product (400 mg, 87% yield) was isolated via column chromatography with hexanes and ethyl acetate as eluant. NMR 1H-(CDCl3)-δ-8.93 (bs, 1H), 7.87 (bs, 1H), 7.64 (bs, 0.5H, rot.), 7.57 (bs, 0.5H, rot.), 4.41 (bs, 0.5H, rot.), 4.31 (bs, 0.5H, rot.), 3.81 (bs, 4H), 3.58-3.65 (bm, 2H), 3.03-3.15 (m, 2H), 2.98 (s, 3H), 1.53 (s, 9H), 1.42 (s, 9H), 0.93 (s, 6H)

490d) Synthesis of 7-tert-Butoxycarbonylamino-8-hydroxy-5-methyl-2,3,4,5-tetrahydro-benzo[b][1,4]diazepine-1-carboxylic acid tert-butyl ester. To a 25 ml round bottom flask, 7-tert-butoxycarbonylamino-8-(5,5-dimethyl-[1,3,2]dioxaborinan-2-yl)-5-methyl-2,3,4,5-tetrahydro-benzo[b][1,4]diazepine-1-carboxylic acid tert-butyl ester (3.80 g, 7.8 mmole) and THF (100 ml) were added. 30% hydrogen peroxide (15 ml) was added at 00 C. The reaction was then stirred at room temperature for 3 hours. Dichloromethane (125 ml) was added. The organic layer was washed with 10% aqeuous Na2S2O3 (200 ml), and subsequently with Brine. The organic was dried over magnesium sulfate. The solid was filtered and washed with dichloromethane. The organic was then moved under vacuum to give a purple oil. The desired product (2.00 g, 65% yield) was isolated via column chromatography with hexanes and ethyl acetate as eluant. NMR 1H-(CDCl3)-δ-7.80 (bs, 05H, rot.), 7.0 (bs, 0.5H, rot.), 6.85 (bs, 1H) 6.0 (bs, 2H), 4.25 (s, 2H), 3.60 (s, 2H), 2.80-2.92 (m, 5H), 1.52 (s, 9H), 1.40 (s, 9H)

490e) Synthesis of 8-Methoxy-5-methyl-2,3,4,5-tetrahydro-1H-benzo[b][1,4]diazepin-7-ylamine. To a 25 ml round bottom flask, 7-tert-Butoxycarbonylamino-8-hydroxy-5-methyl-2,3,4,5-tetrahydro-benzo[b][1,4]diazepine-1-carboxylic acid tert-butyl ester (0.45 g, 1.15 mmole), dimethyl sulfate (0.2 ml), acetone (20 ml), water (1 ml), and potassium carbonate (0.47 g, 3.45 mmoles) were added. The reaction mixture was stirred at room temperature for 18 hours. The reaction mixture was partitioned with dichloromethane (150 ml) and water (50 ml). The organic layer was separated, washed with Brine and dried over magnesium sulfate. The solid was filtered and washed with ethyl acetate. The solvent was removed under vacuum to afford an off-white solid. The solid was dissolved in dichloromethane (3 ml). Trifluoroacetic acid (1.5 ml) was added, and stirred for 18 hours. The reaction was concentrated to dryness. The resulting solid was coevaporated with dichlormethane; (3×20m). The desired product (125 mg, 53% yield) was isolated via column chromatography with dichloromethane and ammonia in methanol as eluant. NMR 1H-(CDCl3)-δ-7.20 (s, 1H), 6.37 (s, 1H), 4.0-4.40 (m, 5H), 3.20-3.37 (m, 4H), 2.88 (s, 3H)

490f) 8-Methoxy-1-(2-methoxy-ethyl)-5-methyl-2,3,4,5-tetrahydro-1H-benzo[b][1,4]diazepin-7-ylamine. To a 25 ml round bottom flask, 8-methoxy-5-methyl-2,3,4,5-tetrahydro-1H-benzo[b][1,4]diazepin-7-ylamine (125 mg, 0.6 mmole), 2-bromoethyl methyl ether (200 mg, 1.5 mmole), acetone (20 ml), water (1 ml), and potassium carbonate (207 mg, 1.5 mmoles) were added. The reaction was stirred at room temperature for 24 hours. The solvent was removed under vacuum. The product (95 mg, 60% yield). LCMS (ESI+) 266.41 (M+H)

490 g) Synthesis of N-((1R,2R)-2-{5-Chloro-2-[7-methoxy-4-(2-methoxy-ethyl)-1-methyl-2,3,4,5-tetrahydro-1H-benzo[e][1,4]diazepin-8-ylamino]-pyrimidin-4-ylamino}-cyclohexyl)-methanesulfonamide. The product (28 mg, 29% yield) was isolated following protocol as described in example 475. NMR 1H-(CDCl3)-δ-7.98 (s, 1H), 7.96 (s, 1H), 7.37 (s, 1H), 6.72 (s, 1H), 5.25-5.35 (m, 2H), 4.00-4.10 (m, 1H), 3.90 (s, 2H), 3.87 (s, 3H), 3.55 (t, 2H, J=5.81 Hz), 3.39 (s, 3H), 3.16-3.28 (m, 1H), 3.04 (bs, 2H), 2.70-2.99 (m, 5H), 2.79 (s, 3H), 2.68 (t, 2H, J=5.45 Hz), 2.14-2.30 (m, 2H), 1.76-1.90 (m, 2H), 1.32-1.52 (m, 4H). LCMS (ESI+) 568.51; MP=89° C. (foam).

Example 491

(2-exo,3-exo)-3-{5-Chloro-2-[7-methoxy-4-(2-methoxy-ethyl)-1-methyl-2,3,4,5-tetrahydro-1H-benzo[e][1,4]diazepin-8-ylamino]-pyrimidin-4-ylamino}-bicyclo[2.2.1]heptane-2-carboxylic acid amide Synthesis of (2-exo,3-exo)-3-{5-Chloro-2-[7-methoxy-4-(2-methoxy-ethyl)-1-methyl-2,3,4,5-tetrahydro-1H-benzo[e][1,4]diazepin-8-ylamino]-pyrimidin-4-ylamino}-bicyclo[2.2.1]heptane-2-carboxylic acid amide. The product (21 mg, 29% yield) was isolated following protocol as described in example 475. NMR 1H-(CDCl3)-δ-7.72 (s, 1H), 7.17 (bs, 1H), 6.88 (s, 1H), 4.30-4.60 (m, 2H), 3.95-4.05 (m, 1H), 3.70-3.90 (m, 5H), 3.40-3.55 (m, 2H), 3.38 (s, 3H), 3.14-3.35 (m, 3H), 2.90 (s, 3H), 2.45-2.52 (m, 2H), 2.16 (bs, 1H), 1.95-2.10 (m, 1H), 1.18-1.34 (m, 4H). LCMS (ESI+) 530.09 (M+H)

Example 492

N-((1R,2R)-2-{5-Chloro-2-[7-methoxy-1-methyl-4-((R)-3,3,3-trifluoro-2-hydroxy-propyl)-2,3,4,5-tetrahydro-1H-benzo[e][1,4]diazepin-8-ylamino]-pyrimidin-4-ylamino}-cyclohexyl)-methanesulfonamide 492a) Synthesis of N-{(R)-2-[5-Chloro-2-(1-methyl-2,3,4,5-tetrahydro-1H-benzo[e][1,4]diazepin-8-ylamino)-pyrimidin-4-ylamino]-cyclohexyl}-methanesulfonamide. To 40 ml sure-seal reaction vial, 8-methoxy-5-methyl-2,3,4,5-tetrahydro-1H-benzo[b][1,4]diazepin-7-ylamine (0.21 g, 1 mmole), methoxy ethanol (6 ml), and N-[(1R,2R)-2-(2,5-Dichloro-pyrimidin-4-ylamino)-cyclohexyl]-methanesulfonamide (0.30 g, 0.9 mmole), 4M HCl in dioxane (1 ml, 4 mmoles) were added. The reaction was heated to reflux for 3 hours. Upon cooling to room temperature, the solvent was then removed under vacuum to afford a yellow solid. The product (0.14 g, 28% yield) was isolated via column chromatography with dichloromethane and ammonia in methanol (2% to 30% ammonia in methanol) as eluant.

LCMS (ESI+) 510.13 (M+H).

492b) Synthesis of N-((1R,2R)-2-{5-Chloro-2-[7-methoxy-1-methyl-4-((R)-3,3,3-trifluoro-2-hydroxy-propyl)-2,3,4,5-tetrahydro-1H-benzo[e][1,4]diazepin-8-ylamino]-pyrimidin-4-ylamino}-cyclohexyl)-methanesulfonamide. To 40 ml sure-seal reaction vial, N-{(R)-2-[5-Chloro-2-(1-methyl-2,3,4,5-tetrahydro-1H-benzo[e][1,4]diazepin-8-ylamino)-pyrimidin-4-ylamino]-cyclohexyl}-methanesulfonamide (62 mg, 0.12 mmole), (R)-2-trifluoromethyl oxirane (30 mg, 0.27 mmoles), 3.16 mmoles per gram loading MP-carbonate (80 mg, 0.25 mmole), and acetonitrile (10 ml) were added. The mixture was heated to 500 C for 18 hours. The solid was filtered and washed with methanol. The organic was concentrated to dryness. The desired product (18 mg, 24% yield) was isolated via reverse phase HPLC. NMR 1H-(DMSO)-δ-8.43 (s, 1H), 8.10 (s, 1H), 7.92 (s, 1H), 7.46 (s, 1H), 7.20 (s, 1H), 7.17 (s, 1H), 4.20-4.80 (m, 2H), 3.82-4.00 (m, 1H), 3.83 (s, 3H), 3.10-3.60 (m, 7H), 2.91 (s, 3H), 2.89 (s, 3H), 1.85-2.10 (m, 2H), 1.60-1.75 (m, 2H), 1.10-1.40 (m, 4H). LCMS (ESI+) 623.38 (M+H); MP=63-66° C. (foam).

Example 493

5-Chloro-N*2*-(7-methoxy-1-methyl-2,3,4,5-tetrahydro-1H-benzo[e][1,4]diazepin-8-yl)-N*4*-(2-methoxy-4-morpholin-4-yl-phenyl)-pyrimidine-2,4-diamine Synthesis of 5-Chloro-N*2*-(7-methoxy-1-methyl-2,3,4,5-tetrahydro-1H-benzo[e][1,4]diazepin-8-yl)-N*4*-(2-methoxy-4-morpholin-4-yl-phenyl)-pyrimidine-2,4-diamine. To 40 ml sure-seal reaction vial, 8-methoxy-5-methyl-2,3,4,5-tetrahydro-1H-benzo[b][1,4]diazepin-7-ylamine (0.21 g, 1 mmole), methoxy ethanol (6 ml), and (2,5-Dichloro-pyrimidin-4-yl)-(2-methoxy-4-morpholin-4-yl-phenyl)-amine (0.30 g, 0.8 mmole), DL-10_camphorsulfonic acid (0.47 g, 2 mmoles) were added. The reaction was heated to reflux for 3 hours. Upon cooling to room temperature, Methanol (10 ml) and MP-carbonate (0.70 g, 2.2 mmoles) were added. The reaction was stirred for one hour. The solid was filtered and washed with methanol. The solvent was removed under vacuum to afford a red solid. The product (0.18 g, 34% yield) was isolated via column chromatography with dichloromethane and ammonia in methanol (2% to 30% ammonia in methanol) as eluant. NMR 1H-(CDCl3)-δ-8.28 (d, 1H, J=8.08 Hz), 8.06 (s, 1H), 8.05 (bs, 1H), 7.57 (bs, 1H), 7.40 (bs, 1H), 6.72 (bs, 1H), 6.55 (bs, 1H), 6.54 (d, 1H, J=9.60Hz), 3.93 (s, 3H), 3.88-3.92 (m, 6H), 3.87 (s, 3H), 3.16 (t, 4H, J=4.55 Hz), 3.06-3.18 (m, 2H), 2.90-2.94 (m, 2H), 2.74 (s, 3H). LCMS (ESI+) 527.45 (M+H)

Example 494

5-Chloro-N*2*-(4-methanesulfonyl-7-methoxy-1-methyl-2,3,4,5-tetrahydro-1H-benzo[e][1,4]diazepin-8-yl)-N*4*-(2-methoxy-4-morpholin-4-yl-phenyl)-pyrimidine-2,4-diamine Synthesis of 5-Chloro-N*2*-(4-methanesulfonyl-7-methoxy-1-methyl-2,3,4,5-tetrahydro-1H-benzo[e][1,4]diazepin-8-yl)-N*4*-(2-methoxy-4-morpholin-4-yl-phenyl)-pyrimidine-2,4-diamine. The product (18 mg, 27% yield) was isolated following protocol as described in example 493b. NMR 1H-(DMSO)-δ-8.07 (s, 1H), 7.99 (s, 1H), 7.79 (s, 1H), 7.54-7.63 (m, 1H), 6.86 (s, 1H), 6.65 (s, 1H), 6.43 (d, 1H, J=9.35 Hz), 4.28 (s, 2H), 3.70-3.83 (m, 10H), 3.45-3.50 (m, 2H), 3.10-3.18 (m, 2H), 2.93-3.00 (m, 2H), 2.73 (s, 3H), 2.53 (s, 3H). LCMS (ESI+) 603.86 (M+H); MP=198-200° C.

Example 495

5-Chloro-N*2*-[7-methoxy-4-(2-methoxy-ethyl)-1-methyl-2,3,4,5-tetrahydro-1H-benzo[e][1,4]diazepin-8-yl]-N*4*-(2-methoxy-4-morpholin-4-yl-phenyl)-pyrimidine-2,4-diamine Synthesis of 5-Chloro-N*2*-[7-methoxy-4-(2-methoxy-ethyl)-1-methyl-2,3,4,5-tetrahydro-1H-benzo[e][1,4]diazepin-8-yl]-N*4*-(2-methoxy-4-morpholin-4-yl-phenyl)-pyrimidine-2,4-diamine. The product (20 mg, 30% yield) was isolated following protocol as described in example 476. NMR 1H-(CDCl3)-δ-8.27 (d, 1H, J=8.84 Hz), 8.06 (s, 1H), 8.03 (s, 1H), 7.57 (s, 1H), 7.40 (s, 1H), 6.70 (s, 1H), 6.55 (s, 1H), 6.52 (d, 1H, J=8.59 Hz), 3.93 (s, 3H), 3.87-3.92 (m, 6H), 3.86 (s, 3H), 3.57 (t, 2H, J=5.06 Hz), 3.39 (s, 3H), 3.01-3.08 (m, 4H), 2.92-2.99 (m, 4H), 2.65-2.75 (m, 5H). LCMS (ESI+) 584.16 (M+H); MP 68-82° C.

Example 496

(R)-3-{8-[5-Chloro-4-(2-methoxy-4-morpholin-4-yl-phenylamino)-pyrimidin-2-ylamino]-7-methoxy-1-methyl-1,2,3,5-tetrahydro-benzo[e][1,4]diazepin-4-yl}-1,1,1-trifluoro-propan-2-ol Synthesis of (R)-3-{8-[5-Chloro-4-(2-methoxy-4-morpholin-4-yl-phenylamino)-pyrimidin-2-ylamino]-7-methoxy-1-methyl-1,2,3,5-tetrahydro-benzo[e][1,4]diazepin-4-yl}-1,1,1-trifluoro-propan-2-ol. The product (6 mg) was isolated following protocol as described in example 492b. NMR 1H-(DMSO)-δ-8.32 (bs, 1H), 8.14 (s, 1H), 7.71 (bs, 1H), 7.52 (d, 1H), 7.35 (bs, 1H), 7.15 (bs, 1H), 6.66 (s, 1H), 6.47 (d, 1H), 4.20-4.6 (bm, 5H), 3.70-3.90 (m, 12H), 2.03-3.25 (m, 6H), 2.47 (s, 3H). LCMS (ESI+) 639.52 (M+H)

Example 497

N-((1R,2R)-2-{5-Chloro-2-[1-methyl-7-(2,2,2-trifluoro-ethoxy)-2,3,4,5-tetrahydro-1H-benzo[e][1,4]diazepin-8-ylamino]-pyrimidin-4-ylamino}-cyclohexyl)-methanesulfonamide 497a) Synthesis of 1-Methyl-7-(2,2,2-trifluoro-ethoxy)-2,3,4,5-tetrahydro-1H-benzo[e][1,4]diazepin-8-ylamine. To a 25 ml round bottom flask, 7-tert-Butoxycarbonylamino-8-hydroxy-5-methyl-2,3,4,5-tetrahydro-benzo[b][1,4]diazepine-1-carboxylic acid tert-butyl ester (0.20 g, 1.0 mmole), 2,2,2-Trifluorothyl-trichloromethylsulfonate (0.2 ml), methanol (15 ml) and potassium carbonate (0.28 g, 2.0 mmoles) were added. The reaction mixture was stirred at room temperature for 18 hours. The reaction mixture was partitioned with dichloromethane (150 ml) and water (50 ml). The organic layer was separated, washed with Brine and dried over magnesium sulfate. The solid was filtered and washed with ethyl acetate. The solvent was removed under vacuum to afford an off-white solid. The solid was dissolved in dichloromethane (3 ml). Trifluoroacetic acid (10.5 ml) was added, and stirred for 18 hours. The reaction was concentrated to dryness. The resulting solid was coevaporated with dichloromethane (3×20m). The desired product (55 mg, 20% yield) was isolated via column chromatography with dichloromethane and ammonia in methanol as eluant. NMR 1H-(CD3OD)-δ-9.34 (bs, 2H), 6.71 (s, 1H), 6.40 (s, 1H), 6.20 (bs, 0.5H, rot.), 5.75 (bs, 0.5H, rot.), 4.28 (q, 2H, JJ=16.42 Hz, 8.33 Hz), 4.10 (s, 2H), 3.18-3.31 (m, 2H), 3.05-3.14 (m, 2H), 2.84 (s, 3H).

497b) Synthesis of N-((1R,2R)-2-{5-Chloro-2-[1-methyl-7-(2,2,2-trifluoro-ethoxy)-2,3,4,5-tetrahydro-1H-benzo[e][1,4]diazepin-8-ylamino]-pyrimidin-4-ylamino}cyclohexyl)-methanesulfonamide. The product (56 mg, 47% yield) was isolated as described in example 475. NMR 1H-(CD3OD)-δ-7.97 (s, 1H), 7.64 (s, 1H), 7.243 (s, 1H), 4.64 (q, 2H), 4.80-5.00 (m, 2H), 3.90-4.02 (m, 1H), 3.35-3.45 (m, 3H), 3.22-3.28 (m, 2H), 3.02 (s, 3H), 2.93 (s, 3H), 2.08-2.20 (m, 2H), 1.73-1.88 (m, 2H), 1.23-1.60 (m, 4H) LCMS (ESI+) 578.39 (M+H)

Example 498

N-((1R,2R)-2-{5-Chloro-2-[1-methyl-7-(2,2,2-trifluoro-ethoxy)-4-((R)-3,3,3-trifluoro-2-hydroxy-propyl)-2,3,4,5-tetrahydro-1H-benzo[e][1,4]diazepin-8-ylamino]-pyrimidin-4-ylamino}-cyclohexyl)-methanesulfonamide Synthesis of N-((1R,2R)-2-{5-Chloro-2-[1-methyl-7-(2,2,2-trifluoro-ethoxy)-4-((R)-3,3,3-trifluoro-2-hydroxy-propyl)-2,3,4,5-tetrahydro-1H-benzo[e][1,4]diazepin-8-ylamino]-pyrimidin-4-ylamino}-cyclohexyl)-methanesulfonamide. The product (12 mg, 18% yield) was isolated following protocol as described in example 492b. NMR 1H-(DMSO)-δ-8.00 (s, 1H), 7.90 (s, 1H), 7.08-7.43 (m, 2), 3.72-5.10 (m, 9H), 2.98-3.40 (m, 4H), 2.80 (s, 3H), 1.90-2.10 (m, 2H), 1.60-1.72 (m, 2H), 1.10-1.35 (m, 4H). LCMS (ESI+) 689.76 (M+H)

Example 499

N-{(1R,2R)-2-[5-Chloro-2-(1-isopropyl-5-oxo-2,3,4,5-tetrahydro-1H-benzo[e][1,4]diazepin-8-ylamino)-pyrimidin-4-ylamino]-cyclohexyl}-methanesulfonamide 499a) Synthesis of 2-[(2-Amino-ethyl)-isopropyl-amino]-4-nitro-benzoic acid methyl ester. To a 250 ml round bottom flask, methyl 2-fluoro-4-nitrobenzoate (9.00 g, 45.2 mmoles), N-isopropyl ethylenediamine (10 ml), and DMF (10 ml) was added at room temperature (exotherm to 700 C). Upon cooling to room temperature, the content was poured into 300 ml ice water. The solid was filtered, washed with cold water, and subsequently washed with cold ethanol. The solid (6.10 g, 49% yield) was dried under vacuum. NMR 1H-(DMSO)-δ-13.42 (bs, 1H), 8.80 (bs, 1), 8.63 (s, 1H), 8.14 (d, 1H), 7.00 (bs, 1H), 4.87-4.20 (bm, 2H), 3.90 (s, 3H), 3.46-3.70 (m, 2H), 2.78-2.86 (m, 2H), 1.10 (d, 6H, J=6.30Hz)

499b) Synthesis of 2-[(2-tert-Butoxycarbonylamino-ethyl)-isopropyl-amino]-4-nitro-benzoic acid. To a 500 ml round bottom flask, 2-[(2-amino-ethyl)-isopropyl-amino]-4-nitro-benzoic acid methyl ester (6.30 g, 22.3 mmoles), di-tert-butyl dicarbonate (6.30 g, 28.6 mmoles), tetrahydrofuran (150 ml), potassium carbonate (8.10 g, 58.7 mmoles) and methanol (30 ml) were added. The reaction was stirred for three hours. The solid was filtered and washed with dichloromethane to give a yellow solid. The solid was suspended in dioxane (80 ml), and water (20 ml). Lithium hydroxide (1.03 g, 25.1 mmoles) was then added. The mixture was stirred at room temperature for 18 hours. The reaction was acidified with 6N HCl to pH 3, and extracted with ethyl acetate (3×200 ml). The organic was washed with Brine and dried over magnesium sulfate. The solid was filtered and washed with ethyl acetate. The organic was then removed under vacuum to afford 6.82 g of white solid. NMR 1H-(DMSO)-δ-13.42 (bs, 1H), 8.80 (bs, 1), 8.63 (s, 1H), 8.14 (d, 1H), 7.00 (bs, 1H), 4.87-4.20 (bm, 2H), 3.46-3.70 (m, 2H), 3.23-3.40 (m, 2H), 1.40 (s, 9H), 1.10 (d, 6H, J=6.83 Hz)

499c) Synthesis of 1-Isopropyl-8-nitro-1,2,3,4-tetrahydro-benzo[e][1,4]diazepin-5-one. To a 100 ml round bottom flask, 2-[(2-tert-butoxycarbonylamino-ethyl)-isopropyl-amino]-4-Nitro-benzoic acid (780 mg, 2.1 mmoles), and dichloromethane (6 ml) was added. Trifluoroacetic acid (3 ml) was added. The reaction was stirred at room temperature for 18 hours. The reaction was concentrated to dryness. The resulting solid was coevaporated with dichloro methane (3×10 ml). The solid was dissolved in DMF (8 ml), diisopropyl ethylamine (0.4 ml, 2.3 mmoles), BOP (1.13 g, 2.7 mmoles), HOBt (365 mg, 2.7 mmoles) were added. The reaction was stirred at room temperature for 18 hours. The solvent was removed under vacuum. The desired product (260 mg, 51% yield) was obtained via column chromatography with hexanes and ethyl acetate as eluant. NMR 1H-(DMSO)-δ-8.63 (s, 1H), 7.86-8.00 (bs, 2H), 6.77 (d, 1H), 4.85 (p, 1H), 3.47 (bs, 4H), 1.10 (d, 6H, J=6.55 Hz)

499d) Synthesis of 8-Amino-1-isopropyl-1,2,3,4-tetrahydro-benzo[e][1,4]diazepin-5-one To a 500 ml round bottom flask, 1-isopropyl-8-nitro-1,2,3,4-tetrahydro-benzo[e][1,4]diazepin-5-one (4.10 g, 16 mmoles), ethanol (300 ml), and palladium (320 mg) were added. The mixture was evacuated and charged with hydrogen (3 times). The reaction was stirred at room temperature under hydrogen balloon for the weekend (64 hrs). The solid was filtered through celite and washed with methanol. The solvent was then removed under vacuum to afford a brown oil. The desired product (2.15 g, 60% yield) was isolated via column chromatography with DCM and methanol as eluant (0 to 25% methanol). NMR 1H-(DMSO)-δ-7.32-7.52 (m, 1H), 7.00 (bs, 1H), 6.80 (bs, 1H), 4.80 (p, 1H), 3.40 (bs, 4H), 1.10 (d, 6H, J=6.58 Hz)

499e) Synthesis of N-{(1R,2R)-2-[5-Chloro-2-(1-isopropyl-5-oxo-2,3,4,5-tetrahydro-1H-benzo[e][1,4]diazepin-8-ylamino)-pyrimidin-4-ylamino]-cyclohexyl}-methanesulfonamide. The product (53 mg) was isolated following protocol as described in example 475. NMR 1H-(DMSO)-δ-8.07 (s, 1H), 8.02 (s, 1H), 7.36-7.50 (m, 1H), 7.06 (d, 1H, J=8.09 Hz), 6.84-6.98 (m, 1H), 4.82 (p, 1H), 3.82-3.95 9m, 1H), 3.30-3.50 (m, 5H), 2.92 (s, 3H), 1.87-2.08 (m, 2H), 1.58-1.73 (m, 2H), 1.15-1.50 (m, 4H), 1.35 (d, 6H, J=6.85 Hz). LCMS (ESI+) 523.39 (M+H); MP=189-91° C.

Example 511

2-[5-Chloro-2-(3,4-dihydro-2H-benzo[b][1,4]dioxepin-2-ylamino)-pyrimidin-4-ylamino]-N-methyl-benzamide 511a) A solution of 3,4-dihydro-2H-benz[b][1,4]dioxepin-ylamine (0.024 g, 0.00015 mol) and 2-(2,5-dichloro-pyrimidin-4-ylamino)-N-methylbenzamide (0.04 g, 0.00013 mol) in TFA (0.5 mL) was evaporated and then heated to 115° C. for 15 min. Purification by ISCO chromatography gave 2-[5-chloro-2-(3,4-dihydro-2H-benzo[b]1,4]dioxepin-2-ylamino)-pyrimidin-4-ylamino]-N-methyl-benzamide (0.036 g, 56%) vas a white solid. MP: 214-5° C.; ¹H-NMR (DMSO-d$_6$) δ 11.58 ((s, 1H), 9.36 (s, 1H), 8.74 (m, 2H), 8.20-1 (s, 1H), 7.74-6 (d, 1H), 7.50-2 (m, 1H), 7.42-8 (s, 1H), 7.14-6 (m, 2H), 6.86-8 (d, 1H), 4.05 (d, 2H), 4.09 (d, 2H), 2.81 (s, 3H), 2.07 (s, 2H); (LC/MS (ESI+): 426 (M+H).

Example 512

2-[5-Chloro-2-(5-oxo-2,3,4,5-tetrahydro-benzo[f][1,4]oxazepin-8-ylamino)-pyrimidin-4-ylamino]-N-methyl-benzamide 512a) To a solution of 2-hydroxy-4-nitrobenzoic acid (8.0 g, 0.0424 mol) in acetone (240 mL) and dimethyl sulfate (4.48 mL, 0.047 mol) was added potassium carbonate (5.85 g, 0.044 mol), stirred for 24 hrs. and evaporated. To the residue was added ethyl acetate and 2 N HCl (pH 3). The ethyl acetate extract was washed, dried (MgSO$_4$) and evaporated to give 2-hydroxy-4-nitro-benzoic acid methyl ester (8.27 g) as a yellow solid; $^1$H-NMR (DMSO-d$_6$) δ 11.62 (s, 1H), 9.74 (s, 1H), 8.76 (d, 2H), 8.70-2 (d, 2H), 8.29 (s, 1H), 8.11 (s, 1H), 7.71-7 (m, 2H), 7.55 (m, 2H), 8.33-5 (d, 1H), 7.15-9 (t, 1H), 4.27 (s, 2H), 2.80 (s, 3H); LC/MS (ESI+): 228 (M+2Na)

512b) To a solution of 2-hydroxy-4-nitro benzoic acid methyl ester (7.0 g, 0.035 mol), triphenylphosphine (9.31 g, 0.035 mol) and t-butyl N-(2-hydroxyethyl)carbamate (3.82 g, 0.023 mol) in anhydrous THF (400 mL) (stirring for 1 hr.) was added diisopropyl azodicarboxylate (7.03 mL, 0.035 mol) and stirred for 2 days. The reaction was evaporated and the residue purified by ISCO chromatography to give 2-(tert-butoxycarbonylamino-ethoxy)-4-nitro-benzoic acid methyl ester (9.0 g) as a white solid. $^1$H-NMR (DMSO-d$_6$) δ 7.90 (s, 1H), 7.86 (s, 2H), 6.86-92 (br, 1H), 4.18-9 d, 2H), 3.85 (s, 2H), 3.31 (d, 2H), 1.37 (s, 9H); LC/MS (ESI+): 363 (M+Na).

512c) A solution of 2-(2-tert-butoxy carbonyl amino-ethoxy)-4-benzoic acid methyl ester (9.0 g, 0.0264 mol), sodium h7ydroxide (1.58 g, 0.039 mol), methanol (50 mL) and water (5 mL) was stirred for 41 hrs. and evaporated. To the residue was added water (50 mL) and 2 N HCl (pH 5). The precipitate was extracted with ethyl acetate, washed, dried (MgSO$_4$) and evaporated to give 2-(2-tert-butoxycarbonyl amino-ethoxy)-4-nitro-benzoic acid (8.1 g) as a white solid. $^1$H-NMR (DMSO-d$_6$) δ 7.88 (s, 1H), 7.84 (s, 1H), 7.82 (s, 1H), 6.85-9 (br, 1H), 4.17-20 (d, 2H), 3.31-2 (d, 2H), 1.37 (s, 3H); LC/MS (ESI+): 349 (M+Na).

512d) To a solution of 2-(2-tert-butoxycarbonyl amino-ethoxy)-4-nitro-benzoic acid (0.18 g, 0.00055 mol) in DCM (5 mL) was added TFA (0.5 mL) and stirred 1 hr. and evaporated. The residue was treated with anhydrous DMF (1 mL), N-methyl morpholine (0.50 mL 0.0046 mL) and 1-hydroxybenzotriazole hydrate (0.12 g, 0.00088 mol) and stirred 10 min. Benzotriazole-1-yloxy)tris(dimethylamino)phosphonium hexafluorophosphate (0.39 g, 0.00088 mol) was added, stirred 15 hrs. and evaporated. The residue was purified by ISCO chromatography giving 8-nitro-3,4-dihydro-2H-benzo[f][1,4]oxazepin-5-one (0.032 g, 26%) as a white solid. MP: 208-9° C.; $^1$H-NMR (DMSO-d$_6$) δ 8.66 (s, 1H), 7.99-8.01 (d, 1H), 7.92-4 (d, 1H), 7.79-80 (d, 1H), 4.39-41 (m, 2H), 3.36-9 (m, 2H); LC/MS (ESI+): 209 (M+H).

512e) A solution of 8-nitro-3,4-dihydro-2H-benzo[f][1,4]oxazepin-5-one (0.23 g, 0.00096 mol), 10% palladium on carbon (0.02 g), DMF (10 mL), and ethanol (30 mL) was hydrogenated for 3 days. Filtration and evaporation gave an oil which was chromatographed on Al$_2$O$_3$ to give 8-amino-3,4-dihydro-2H-benzo[f][1,4]oxazepin-5-one (0.06 g, 35%) as a tan solid. MP: 151-2° C.; $^1$H-NMR (DMSO-d$_6$) δ 7.77 (s, 1H), 7.54-6 (d, 1H), 6.25-7 (d, 1H), 6.05 (s, 1H), 5.63 (s, 2H), 4.17-9 (m, 2H), 3.25-8 (m, 2H); LC/MS (ESI+): 179 (M+H).

512f) A mixture of 8-amino-3,4-dihydro-2H-benzo[f][1,4]oxazepin-5-one (0.092 g, 0.0003 mol), 2-(2,5-dichloro-pyrimidin-4-ylamino)-N-methyl-benzamide (0.05 g, 0.00028 mol), 4 N HCl in dioxane/water (0.07 mL, 0.00028 mol) was heated at 100° C. for 4 hrs. The slurry was evaporated and the residue treated with ethyl acetate and a 10% sodium carbonate solution. The insoluble solid was collected, washed, dried to give 2-[5-chloro-2-(5-oxo-2,3,4,5-tetrahydro-benzo[f][1,4]oxazepin-8-ylamino)-pyrimidin-4-ylamino]-N-methyl-benzamide (0.09 g, 74%) as a yellow solid. MP: 293-5° C.; $^1$H-NMR (DMSO-d$_6$) δ 11.62 (s, 1H), 9.74 (s, 1H), 8.72-6 (d, 1H), 8.70 (d, 1H) 8.29 (s, 1H) 8.11 (s, 1H), 7.77 (m, 2H), 7.51-3 (d, 2H), 7.33-5 (d, 1H), 7.15-9 (t, 1H), 4.27 (s, 1H); LC/MS (ESI+): 439 (M+H).

Example 513

2-[5-Chloro-2-(2-oxo-2,3,4,5-tetrahydro-1H-benzo[b]azepin-8-ylamino)-pyrimidin-4-ylamino]-N-methyl benzamide Following the procedure of 512f, 8-amino-1,3,4,5-tetrahydro-benzo[b]azepin-2-one (0.091 g, 0.0005 mol) and 2-(2,5-dichloro-pyrimidin-4-ylamino)-N-methyl benzamide (0.1 g, 0.00033 mol) were reacted. Purification by ISCO chromatography gave 2-[5-Chloro-2-(2-oxo-2,3,4,5-tetrahydro-1H-benzo[b]azepin-8-ylamino)-pyrimidin-4-ylamino]-N-methyl benzamide (0.026 g, 18%) as a tan solid. MP: 293-5° C.; $^1$H-NMR (DMSO-d$_6$) δ 11.63 (s, 1H), 9.45 (d, 2H), 8.74 (s, 2H), 8.22 (s, 1H), 7.74 (d, 1H), 7.43-7 (t, 1H), 7.37-9 (d, 1H), 7.34 (s, 1H), 7.12-3 (d, 2H), 4.12 (m, 1H), 3.50 (m, 1H), 3.25 (s, 1H), 2.80-1 (d, 9H), 2.61-4 (m, 2H); LC/MS (ESI+): 437 (M+H).

Example 514

2-[5-chloro-2-(4-methyl-5-oxo-2,3,4,5-tetrahydro-benzo[f][1,4]oxazepin-8-ylamino)-pyrimidin-4-ylamino]-N-methyl-benzamide 514a) A solution of 8-nitro-3,4-dihydro-2H-benzo[f][1,4]oxazepin-5-one (0.25 g, 0.0012 mol) in DMF (8 mL) at 5° C. under nitrogen, was treated with sodium hydride (0.058 g, 0.0015 mol). After stirring 15 hrs. at room temperature, the reaction was evaporated. The residue was treated with ethyl acetate and 1N HCl (pH 5), separated, washed, dried (MgSO$_4$) to give 4-methyl-8-nitro-3,4-dihydro-2H-benzo[f][1,4]oxazepin-5-one (0.2 g, 77%) as a tan solid. MP: 130-2° C.; $^1$H-NMR (DMSO-d$_6$) δ 7.90-8 (d, 1H), 7.88 (d, 1H), 7.80 (d, 1H), 4.46-8 (m, 2H), 3.56-9 (m, 2H), 3.11 (s, 3H); LC/MS (ESI+): 223 (M+H).

514b) 4-Methyl-8-nitro-3,4-dihydro-2H-benzo[f][1,4]oxazepin-5-one (0.16 g, 0.0072 mol) and 10% palladium on carbon in ethanol (70 mL) was hydrogenated. The reaction was filtered and evaporated. Purification by ISCO chromatography gave 8-amino-4-methyl-3,4-dihydro-2H-benzo[f][1,4]oxazepin-5-one (0.027 g, 84%) as a tan solid. MP: 169-170° C.; $^1$H-NMR (DMSO-d$_6$) δ 7.36 (d, 1H), 6.27-9 (d, 1H), 6.08 (s, 1H), 5.60 (s, 1H), 4.22-5 (m, 2H), 3.46-9 (m, 2H), 3.00 (s, 3H); LC/MS (ESI+): 193 (M+H).

514c) Following the procedure of 512f, 8-amino-4-methyl-3,4-dihdro-2H-benzi[f][1,4]oxazepin-5-one (0.04 g, 0.0002 mol) and 2-(2,5-dichloro-pyrimidin-4-ylamino)-N-methyl benzamide (0.062 g, 0.0002 mol) were reacted giving 2[5-chloro-2-(4-methyl-5-oxo-2,3,4,5-tetrahydro-benzo[f][1,4]oxazepin-8-ylamino)-pyrimidin-4-ylamino]-N-methyl-benzamide (0.037 g, 41%) as a white solid. MP: 288-9° C.;

$^1$H-NMR (DMSO-d$_6$) δ 11.62 (s, 1H), 9.74 (s, 1H), 8.78 (d, 1H), 8.70-2 (d, 1H), 8.29 9s, 1H), 7.75-7 (d, 1H), 7.53-8 (m, 3H), 7.35-8 (d, 1H), 7.17-9 (t, 1H), 4.32-4 (m, 2H), 3.06 (s, 3H), 2.80-1 (d, 3H); LC/MS (ESI+): 453 (M+H).

Example 515

2-[5-Chloro-2-(4-ethyl-5-oxo-2,3,4,5-tetrahydro-benzo[f][1,4]oxazepin-8-ylamino)-pyrimidin-4-ylamino]-N-methyl-benzamide 515a) Following the procedure of 514a, 8-nitro-3,4-dihydro-2H-benzo[f][1,4]oxazepin-5-one (0.3 g, 0.0014 mol) was reacted with sodium hydride (0.069 mol, 0.0017 mol) and ethyl iodide (0.15 mL, 0.0019 mol) to give 8-nitro-4-ethyl-3,4-2H-benzo[f][1,4]oxazepin-5-one (0.2 g, 65%) as a tan solid. MP: 50-2° C.; LC/MS (ESI+): 237 (M+H).

515b) Following the procedure of 514b, 8-nitro-4-ethyl-3,4-2H-benzo[f][1,4]oxazepin-5-one (0.19 g, 0.0008 mol) was hydrogenated. Purification by Al$_2$O$_3$ chromatography gave 8-amino-4-ethyl-3,4-2H-benzo[f][1,4]oxazepin-5-one (0.047 g, 29%) as a tan solid. MP: 187-9° C.; LC/MS (ESI+): 207 (M+H).

515c) Following the procedure of 512f, 8-amino-4-ethyl-3,4-2H-benzo[f][1,4]oxazepin-5-one (0.04 g, 0.00019 mol) and 2-(2,5-dichloro-pyrimidin-4-ylamino)-N-methyl benzamide (0.057 g, 0.00019 mol) were reacted to give 2-[5-chloro-2-(4-ethyl-5-oxo-2,3,4,5-tetrahydro-benzo[f][1,4]oxazepin-8-ylamino)-pyrimidin-4-ylamino]-N-methyl-benzamide (0.042 g, 47%) as a cream colored solid. MP: 215-20° C.; $^1$H-NMR (DMSO-d$_6$) δ 11.61 (s, 1H), 9.74 (s, 1H), 8.76 (d, 1H), 8.70-2 (d, 1H), 8.29 (s, 1H), 7.75-7 (d, 1H), 7.54-8 (m, 3H), 7.37-9(d, 1H), 7.15-7 (t, 1H), 4.29-32 (m, 2H), 3.51-3 (m, 4H), 2.80-1 (d, 3H), 1.10-3 (t, 3H); LC/MS (ESI+): 467 (M+H).

Example 516

2-[5-Chloro-2-(6,7,8,9-tetrahydro-5-thia-aza-benzo-cyclohepten-2-ylamino)-pyrimidin-4-ylamino]-N-methyl-benzamide 516a) T a slurry of 5-nitro-2-chloro-benzaldehyde (1.5 g, 0.0078 mol), 2-aminoethanethiol hydrochloride (2.73 g, 0.023 mol), sodium cyanoborohydride (0.49 g, 0.0078 mol) in anhydrous methanol (30 mL) was added acetic acid (5 mL) and stirred 24 hrs. The mixture was evaporated and the residue triturated with isopropanol giving 2-(2-chloro-5-nitro-benzylamino)-ethanethiol hydrochloride (0.87 g, 45%) as a white solid. MP: 228-231° C.; $^1$H-NMR (DMSO-d$_6$) δ 9.76-82 (br, 2H), 8.75 (s, 1H), 8.28-31 (d, 1H), 7.85-90 (d, 1H), 4.40 (s, 2H), 3.15-25 (m, 2H), 2.80-90 (m, 2H); LC/MS (ESI+): 247 (M+H).

516b) To a slurry of sodium hydride (1.06 g, 0.01 mol) in anhydrous DMF (175 mL) under nitrogen was added 2-(2-chloro-5-nitro-benzylamino)-ethanethiol hydrochloride (3.0 g, 0.01 mol), stirred 3 hrs. and evaporated. The residue was treated with water (15 mL) giving 2-nitro 6,7,8,9-tetrahydro-5-thia-8-aza-benzocycloheptene (1.05 g, 47%) as a tan solid. MP: 104-5° C.; $^1$H-NMR (DMSO-d$_6$) δ 8.13 (s, 1H), 7.97-8.00 (d, 1H), 7.69-7.10 (s, 1H), 4.04 (s, 2H), 3.12-20 (d, 2H), 2.82-8 (d, 2H), 2.54-65 (br, 1H); LC/MS (ESI+): 210 (M).

516c) To a mixture of 2-nitro 6,7,8,9-tetrahydro-5-thia-8-aza-benzocycloheptene (1.0 g, 0.0047 mol), hydrazine hydrate (10 mL) in ethanol (40 mL) was added 10% palladium on carbon (0.2 g) and refluxed 3 days, filtered and concentrated to give 6,7,8,9-tetrahydro-5-thia-8-aza-benzocyclohepten-2-ylamine (0.76 g, 90%) as a yellow solid. MP: 110-111° C.; $^1$H-NMR (DMSO-d$_6$) δ 7.08-15 (d, 1H), 6.45 (s, 1H), 6.25-33 (d, 1H), 5.15 (s, 2H), 3.78 (s, 2H), 3.10-20 (m, 2H), 2.50-60 (m, 2H), 2.00-22 (br, 1H); LC/MS (ESI+): 181 (M+H).

516d) Following the procedure of 512f, 6,7,8,9-tetrahydro-5-thia-8-aza-benzocyclohepten-2-ylamine (0.08 g, 0.00044 mol) and 2-(2,5-dichloro-pyrimidin-4-ylamino)-N-methyl benzamide (0.13 g, 0.00044 mol) were reacted except that purification was done by ISCO chromatography giving 2-[5-chloro-2-(6,7,8,9-tetrahydro-5-thia-aza-benzocyclohepten-2-ylamino)-pyrimidin-4-ylamino]-N-methyl-benzamide (0.019 g, 10%) as a tan solid. MP: 169-174° C.; $^1$H-NMR (DMSO-d$_6$) δ 11.59 (s, 1H), 9.55 (s, 1H), 8.75-7 (d, 1H), 8.68-70 (d, 1H), 8.24 (s, 1H), 7.75-7 (d, 1H), 7.67 (d, 1H), 7.53-5 (t, 1H), 7.41-4 (d, 1H), 7.14-8 (t, 1H), 3.85 (s, 2H), 3.18 (s, 2H), 2.80-1 (s, 3H), 2.66 (s, 2H); LC/MS (ESI+): 441 (M+H).

Example 517

2-[5-Chloro-2-(8-ethyl-6,7,8,9-tetrahydro-5-thia-aza-benzocyclohepten-2-ylamino)-pyrimidin-4-ylamino]-N-methyl-benzamide 517a) To a solution of 6,7,8,9-tetrahydro-5-thia-8-aza-benzocyclohepten-2-ylamine (0.07 g, 0.00039 mol) and N-ethyldiisopropylamine (0.066 g, 0.00047 mol) in DCM (4 mL) was added bromoethane (0.051 g, 0.00047 mol), stirred 20 h and evaporated to give 8-ethyl-6,7,8,9-tetrahydro-5-thia-8-aza-benzocyclohepten-2-ylamine (0.07 g) as an oil. MS (ESI+): 209 (M+H).

517b) Following the procedure of 512f, give 8-ethyl-6,7,8,9-tetrahydro-5-thia-8-aza-benzcyclohepten-2-ylamine (0.07 g, 0.00032 mol) and 2-(2,5-dichloro-pyrimidin-4-ylamino)-N-methyl benzamide (0.097 g, 0.00032 mol) were reacted. Purification by SiO$_2$ prep plate chromatography gave 2-[5-chloro-2-(8-ethyl-6,7,8,9-tetrahydro-5-thia-aza-benzocyclohepten-2-ylamino)-pyrimidin-4-ylamino]-N-methyl-benzamide (0.04 g, 27%) as a white solid. MP: 228-31° C.; $^1$H-NMR (DMSO-d$_6$) δ 11.61 (s, 1H), 9.52 (s, 1H), 8.75 (d, 1H), 8.70-1 (d, 1H), 8.24 (s, 1H), 7.75-7 (d, 1H), 7.60 (s, 1H), 7.51-7 (m, 3H), 7.35-7 (d, 1H), 7.14 (t, 1H), 3.96 (s, 1H), 3.25-7 (s, 2H), 2.80-1 (s, 3H), 2.67 (s, 2H), 2.29-34 (q, 2H), 0.93-6 (t, 3H); LC/MS (ESI+): 469 (M).

Example 518

N-{2-[3-Chloro-2-(6,7,8,9-tetrahydro-5-thia-8-aza-benzocyclohepten-2-ylamino)-pyrimidin-4-ylamino]-phenyl}-methanesulfonamide Following the procedure of 512f, 6,7,8,9-tetrahydro-5-thia-8-aza-benzocyclohepten-2-ylamine (0.07 g, 0.00039 mol) and N-[2-(2,5-dichloro-pyrimidin-4-ylamino)-phenyl]-methanesulfonamide (0.13 g, 0.00039 mol) were reacted giving N-{2-[3-Chloro-2-(6,7,8,9-tetrahydro-5-thia-8-aza-benzocyclohepten-2-ylamino)-pyrimidin-4-ylamino]-phenyl}-methanesulfonamide (0.15 g, 83%). MP: 141-3° C.; $^1$H-NMR (DMSO-d$_6$) 9.48 (s, 1H), 8.63 (s, 1H), 8.19 (s, 1H), 7.90 (d, 1H), 7.56 (s, 1H), 7.24-42 (m, 6H), 3.83 (s, 2H), 3.23 (s, 2H), 2.92-6 (s, 4H), 2.67 (s, 4H); LC/MS (ESI+): 477 (M).

Example 519

N-{(1R,2R)-2-[5-Chloro-2-(6,7,8,9-tetrahydro-5-thia-8-aza-benzocyclohepten-2-ylamino)-pyrimidin-4-ylamino]-cyclohexyl}-methanesulfonamide Following the procedure of 2f, 6,7,8,9-tetrahydro-5-thia-8-aza-benzocyclohepten-2-ylamine (0.07 g, 0.00039 mol)

and N-[(1S,2R)-2-(2,5-dichloro-pyrimidin-4-ylamino)-cyclohexyl]-methanesulfonamide (0.13 g, 0.00039 mol) were reacted giving N-{(1R,2R)-2-[5-chloro-2-(6,7,8,9-tetrahydro-5-thia-8-aza-benzocyclohepten-2-ylamino)-pyrimidin-4-ylamino]-cyclohexyl}-methanesulfonamide (0.16 g, 85%). MP: 141-3° C.; $^1$H-NMR (DMSO-d$_6$) 9.30 (s, 1H), 7.93-5 (s, 1H), 7.73-9 (s, 1H), 7.44-6 (d, 1H), 7.33-5 (d, 1H), 7.16-8 (d, 1H), 6.76-8 (d, 1H), 3.91 (s, 1H), 3.84-5 (m, 1H), 3.22-4 (m, 2H), 2.93 (s, 2H), 2.63-4 (m, 2H), 2.00-12 (m, 2H), 1.70 (m, 2H), 1.27-37 (m, 4H); LC/MS (ESI+): 483 (M).

Example 520

N-{(1R,2R)-2-[5-Chloro-2-(5,5-dioxo-6,7,8,9-tetrahydro-5H-5lambda*6*-thia-8-aza-benzoylcyclohepten-2-ylamino)-pyrimidin-4-ylamino]-cyclohexyl}-methanesulfonamide To a slurry of N-{(1R,2R)-2-[5-chloro-2-(6,7,8,9-tetrahydro-5-thia-8-aza-benzocyclohepten-2-ylamino)-pyrimidin-4-ylamino]-cyclohexyl}-methanesulfonamide (0.04 g, 0.000083 mol), 6 N HCl (0.028 mL, 0.00016 mol) in ethanol (5 mL) was added 30% hydrogen peroxide (0.5 mL), heated at 45° C. for 21 hrs and evaporated. The residue was treated with a sodium bicarbonate solution giving N-{(1R,2R)-2-[5-chloro-2-(5,5-dioxo-6,7,8,9-tetrahydro-5H-5lambda*6*-thia-8aza-benzoylcyclohepten-2-ylamino)-pyrimidin-4-ylamino]-cyclohexyl}-methanesulfonamide (0.025 g, 60%) as a white solid. MP: 175° C.; $^1$H-NMR (DMSO-d$_6$) 9.76 (s, 1H), 8.03 (s, 1H), 7.83 (s, 1H), 7.75 (s, 2H), 7.19-21 (d, 1H), 6.91 (d, 1H), 4.01 (s, 1H), 3.75-95 (m, 1H), 2.94 (s, 4H), 1.95-2.14 (m, 3H), 1.61-1.81 (m, 3H), 1.21-41 (m, 6H); LC/MS (ESI+): 515 (M).

Example 521

N-((1R,2R)-2-{5-Chloro-2-[8-(2-methoxy-ethyl)-6,7,8,9-tetrahydro-5-thia-8-aza-benzocyclohepten-2-ylamino]pyrimidin-4-ylamino}-cyclohexyl)-methanesulfonamide 521a) Following the procedure of 517a, 6,7,8,9-tetrahydro-5-thia-8-aza-benzocyclohepten-2-ylamine (0.18 g, 0.001 mol) and 2-bromomethylmethylether (0.16 g, 0.0011 mol) were reacted. The reaction was evaporated and the residue treated with ethyl acetate and a sodium carbonate solution, separated, washed, dried (MgSO$_4$) and evaporated to give 8-(2-methoxy-ethyl)-6,7,8,9-tetrahydro-5-thia-8-aza-benzocyclohepten-2-ylamine (0.073 g 88%) as an oil. MS (ESI+): 239 (M).

521b) Following the procedure of 512f, 8-(2-methoxy-ethyl)-6,7,8,9-tetrahydro-5-thia-8-aza-benzocyclohepten-2-ylamine (0.07 g, 0.00029 mol) and N-[(1S,2R)-2-(2,5-dichloro-pyrimidin-4-ylamino)-cyclohexyl]-methanesulfonamide (0.099 g, 0.00029 mol) were reacted. Purification was carried out by SiO$_2$ prep plate chromatography giving N-((1R,2R)-2-{5-chloro-2-[8-(2-methoxy-ethyl)-6,7,8,9-tetrahydro-5-thia-8-aza-benzocyclohepten-2-ylamino]pyrimidin-4-ylamino}-cyclohexyl)-methanesulfonamide (0.042 g, 28%) as a grey solid. MP: 140-3° C.; $^1$H-NMR (DMSO-d$_6$) 9.28 (s, 1H), 7.95 (s, 1H), 7.60-5 (s, 1H), 7.58 (d, 1H), 7.33-5 (d, 1H), 7.16-8 (d, 1H), 6.76-8 (d, 1H), 4.01 (s, 2H), 3.80-90 (m, 1H), 3.36-45 (m, 4H), 3.21 (m, 4H), 2.93 (s, 2H), 2.67 (s, 2H), 2.0010 (m, 2H), 1.65-80 (m, 2H), 1.20-45 (m, 4H); LC/MS (ESI+): 541 (M).

Example 522

2-{5-Chloro-2-[8-(2-methoxy-ethyl)-6,7,8,9-tetrahydro-5-thia-8-aza-benzocyclohepten-2-ylamino]-pyrimidin-4-ylamino}-N-methyl-benzamide Following the procedure of 512f, 8-(2-methoxy-ethyl)-6,7,8,9-tetrahydro-5-thia-8-aza-benzocyclohepten-2-ylamine (0.07 g, 0.00029 mol) and 2-(2,5-dichloro-pyrimidin-4-ylamino)-N-methyl benzamide (0.086 g, 0.00029 mol) were reacted. Purification was carried by SiO$_2$ prep plate chromatography giving 2-{5-chloro-2-[8-(2-methoxy-ethyl)-6,7,8,9-tetrahydro-5-thia-8-aza-benzocyclohepten-2-ylamino]-pyrimidin-4-ylamino}-N-methyl-benzamide (0.06 g, 43%) as a grey solid. MP: 176-7° C.; $^1$H-NMR (DMSO-d$_6$) 11.63 (s, 1H), 9.53 (s, 1H), 8.75 (d, 1H), 8.72 (d, 1H), 8.24 (s, 1H), 7.75-7 (d, 1H), 7.61 (s, 1H), 7.51-7 (m, 2H), 7.36-8 (d, 1H), 7.16-8 (t, 1H), 7.11-4 (d, 1H), 5.17 (s, 1H), 3.98 (s, 2H), 3.89 (s, 1H0, 2.80-1 (d, 2H), 2.67 (d, 2H); LC/MS (ESI+): 499 (M).

Example 523

N-{2-[5-Chloro-2(5,5dioxo-6,7,8,9-tetrahydro-5H-5lambda*6*-thia-8-aza-benzocyclohepten-2-ylamino)-pyrimidin-4-ylamino]-phenyl}-methanesulfonamide Following the procedure of 520, N-{2-[3-chloro-2-(6,7,8,9-tetrahydro-5-thia-8-aza-benzocyclohepten-2-ylamino)-pyrimidin-4-ylamino]-phenyl}-methanesulfonamide (0.04 g, 0.000083 mol) was oxidized. Purification by SiO$_2$ prep plate chromatography gave N-{2-[5-chloro-2(5,5dioxo-6,7,8,9-tetrahydro-5H-5lambda*6*-thia-8-aza-benzocyclohepten-2-ylamino)-pyrimidin-4-ylamino]-phenyl}-methanesulfonamide (0.004 g, 10%) as a grey solid. MP: 195-200° C.; $^1$H-NMR (DMSO-d$_6$) 9.86 (s, 1H), 8.25-7 (s, 2H), 7.33-82 (m, 8H), 3.29 (s, 2H), 2.93 (s, 3H); LC/MS (ESI+): 509 (M).

Example 524

N-{(1R,2R)-2[5-Chloro-2-(2,3,4,5-tetrahydro-benzo[f]oxazepin-7-ylamino)-pyrimidin-4-ylamino]-cyclohexyl}-methanesulfonamide 524a) A mixture of 2-fluoro-5-nitrobenzaldehyde (1.0 g, 0.0059 mol), aminoethanol (1.08 g, 0.017 mol), methanol (20 mL) and acetic acid (10 mL) was stirred 2.5 hr. Sodium cyanoborohydride (0.37 g, 0.0059 mol) was added, stirred 24 hrs. and evaporated. The residue was treated with water, ethyl acetate and adjusted to pH 10. The organic layer was separated washed, dried (MgSO$_4$) and evaporated. Trituration of the residue with hexane-diethylether (1-1) gave 2-(2-fluoro-5-nitro-benzaldehyde)ethanol (1.05 g, 83%) as a yellow solid. MP: 93-4° C.; $^1$H-NMR (DMSO-d$_6$) 8.39-40 (s, 1H), 8.18-21 (d, 1H), 7.43-8 (t, 1H), 4.50-3 (s, 1H), 3.83 (s, 2H), 3.45-50 (t, 2H), 2.60 (t, 2H); LC/MS (ESI+): 214 (M).

524b) To a solution of 2-(2-fluoro-5-nitro-benzaldehyde)ethanol (0.09 g, 0.0042 mol) in anhydrous DMF under nitrogen, was added sodium hydride (0.25 g, 0.0063 mol), stirred 3 days and evaporated. The residue was triturated with hexane, followed by water giving 2-nitro-2,3,4,5-tetrahydro-benzo[f][1,4]oxazepine (0.19 g, 23%) as a tan solid. MP: 210-1° C.; $^1$H-NMR (DMSO-d$_6$) 8.17-9 (d, 1H), 8.13-6 (d, 1H), 7.16-8 (d, 1H), 4.23-4 (s, 2H), 3.76 (s, 2H), 2.93 (s, 2H); LC/MS (ESI+): 195 (M+H).

524c) Following the procedure of 516c, 2-nitro-2,3,4,5-tetrahydro-benzo[f][1,4]oxazepine (0.17 g, 0.00087 mol) was reduced to 2,3,4,5-tetrahydro-benzo[f][1,4]oxazepin-7-ylamine (0.11 g, 79%) as a tan solid. LC/MS (ESI+): 164 (M).

524d) Following the procedure of 512f, 2,3,4,5-tetrahydro-benzo[f][1,4]oxazepin-7-ylamine (0.09 g, 0.00055 mol) and N-[(1S,2R)-2-(2,5-dichloro-pyrimidin-4-ylamino)cyclohexyl]methanesulfonamide (0.13 g, 0.00038 mol) were reacted. Purification by SiO$_2$ prep plate chromatography gave N-{2-[5-chloro-2(5,5dioxo-6,7,8,9-tetrahydro-5H-5lambda*6*-thia-8-aza-benzocyclohepten-2-ylamino)-pyrimidin-4-ylamino]-phenyl}-methanesulfonamide (0.02 g, 18%) as a tan solid. MP: 127-30° C.; $^1$H-NMR (DMSO-d$_6$) 9.08 (s, 1H), 7.91 (s, 1H), 7.57 (s, 1H), 7.36-8 (d, 1H), 7.15-7 (d, 1H), 6.83-5 (d, 1H), 6.69-71 (d, 1H), 3.89 (s, 2H), 3.76 (s, 2H), 3.01 (s, 2H), 2.93 (s, 3H), 2.00-10 (m, 2H), 1.69 (s, 2H), 1.23-35 (m, 5H); LC/MS (ESI+): 467 (M+H).

Example 525

N-((1R,2R)-2-{-5-Chloro-2-[8-(2-hydroxy-ethyl)-6,7,8,9-tetrahydro-5-thia-8-azabenzo-cyclohepten-2-ylamino]-pyrimidin-4-ylamino}cyclohexyl)-methanesulfonamide 525a) Following the procedure of 521a, 6,7,8,9-tetrahydro-5-thia-8-aza-benzocyclohepten-2-ylamine (0.28 g, 0.0015 mol) and 2-bromoethyl acetate (0.40 g, 0.0023 mol) were reacted to give acetic acid 2-(2-amino-6,7-dihydro-9H-5-thia-8-aza-benzocyclohepten-8-yl)-ethyl ester (0.34 g, 83%) as an oil. LC/MS (ESI+): 266 (M).

525b) Following the procedure of 512f, 2-(2-amino-6,7-dihydro-9H-5-thia-8-aza-benzocyclohepten-yl)-ethyl ester (0.09 g, 0.00033 mol) and N-[(1S,2R)-2-(2,5-dichloro-pyrimidin-4-ylamino)cyclohexyl]methanesulfonamide (0.11 g, 0.00033 mol) were reacted to give N-((1R,2R)-2-{-5-chloro-2-[8-(2-hydroxy-ethyl)-6,7,8,9-tetrahydro-5-thia-8-aza-benzo-cyclohepten-2-ylamino]-pyrimidin-4-ylamino}cyclohexyl)-methanesulfonamide (0.041 g) as a tan solid. MP: 76-86° C.; $^1$H-NMR (DMSO-d$_6$) 9.27 (s, 1H), 7.96 (s, 1H), 7.63 (d, 1H), 7.34-6 (d, 1H), 7.16 (d, 1H), 6.77 (d, 1H), 4.46 (m, 2H), 4.36 (m, 2H), 4.01 (s, 4H), 3.25 (m, 1H), 2.92 9 (s, 2H), 2.67 (m, 1H), 2.39 (m, 2H), 1.61-80 (m, 2H), 1.20-40 (m, 7H); LC/MS (ESI+): 527 (M).

Example 526

Acetic acid 2-{2-[5-chloro-4-((1R,2R)-2-methanesulfonylamino-cyclohexylamino)-pyrimidin-2-ylamino]-6,7-dihydro-9H-5-thia-8-aza-benzocyclohepten-8-yl}-ethyl ester Following the procedure of 525b, acetic acid 2-{2-[5-chloro-4-((1R,2R)-2-methanesulfonylamino-cyclohexylamino)-pyrimidin-2-ylamino]-6,7-dihydro-9H-5-thia-8-aza-benzocyclohepten-8-yl}-ethyl ester (0.035 g) was also isolated as a tan solid. MP: 85-90° C.; $^1$H-NMR (DMSO-d$_6$) 9.30 (s, 1H), 7.95 (s, 1H), 7.65 (s, 1H), 7.59-6 (d, 1H), 7.35 (d, 1H), 7.15-7 (d, 1H), 6.76-8 (d, 1H), 4.04-7 (m, 4H), 3.27-9 (d, 2H), 2.93 (s, 3H), 2.68 (s, 2H), 2.58 (m, 2H), 1.99 (m, 5H), 1.70 (m, 2H), 1.23-35 (m, 5H); LC/MS (ESI+): 569 (M).

Example 527

Acetic acid 2-{2-[5-Chloro-4-(2-methylcarbamoyl-phenylamino)-pyrimidin-2-ylamino]-6,7-dihydro-9H-5-thia-8-aza-benzoylcyclohepten-8-yl}-ethyl ester Following the procedure of 512f, acetic acid 2-(2-amino-6,7-dihydro-9H-5-thia-8-aza-benzocyclohepten-8-yl)-ethyl ester (0.09 g, 00033 mol) and 2-(2,5-dichloro-pyrimidin-4-ylamino)-N-methyl benzamide (0.1 g, 0.00033 mol) were reacted. Purification by SiO$_2$ prep plate chromatography gave acetic acid 2-{2-[5-chloro-4-(2-methylcarbamoyl-phenylamino)-pyrimidin-2-ylamino]-6,7-dihydro-9H-5-thia-8-aza-benzoylcyclohepten-8-yl}-ethyl ester (0.02 g, 12%) as a white solid. MP: 180-2° C.; $^1$H-NMR (DMSO-d$_6$) 11.63 (s, 1H), 9.54 (s, 1H), 8.74 (m, 2H), 8.24 (s, 1H), 7.75-7 (d, 1H), 7.58 (t, 1H), 7.53 (d, 1H), 7.37-9 (d, 1H), 7.14-8 (m, 1H), 4.03 (s, 4H), 2.80-1 (s, 3H), 2.67 (s, 2H), 1.97 (s, 3H); LC/MS (ESI+): 527 (M).

Example 528

2-{5-Chloro-2-[8-(hydroxyl-ethyl)-6,7,8,9-tetrahydro-5-thia-8-aza-benzoylcyclohepten-2-ylamino]-pyrimidin-4-ylamino}-N-methyl-benzamide Following the procedure of 527, acetic acid 2-{2-[5-chloro-4-(2-methylcarbamoyl-phenylamino)-pyrimidin-2-ylamino]-6,7-dihydro-9H-5-thia-8-aza-benzoylcyclohepten-8-yl}-ethyl ester (0.009 g, 6%) was also isolated as a white solid. MP: 168-170° C.; $^1$H-NMR (DMSO-d$_6$) 11.61 (s, 1H), 9.52 (s, 1H), 8.75 (m, 2H), 8.24 (d, 1H), 7.75-7 (d, 1H), 7.57 (t, 2H), 7.51 (t, 1H), 7.36-8 (d, 1H), 4.32 (s, 1H), 3.98 (s, 2H), 2.80 (s, 2H), 2.67 (s, 2H), 1.35 (s, 2H), 1.07-11 (t, 3H); LC/MS (ESI+): 485 (M).

Example 541

2-[5-Chloro-2-(1,4-dimethyl-5-oxo-2,3,4,5-tetrahydro-1H-benzo[e][1,4]diazepin-9-ylamino)-pyrimidin-4-ylamino]-N-methyl-benzamide 541a) 2-Chloro-3-nitro-benzoic acid methyl ester (500 mg, 2.32 mmol) was dissolved in n-butanol (2.5 ml). Na2CO3 (246 mg, 2.32 mmol) was added followed by N,N' dimethyl-ethylenediamine (250 µL, 2.32 mmol). The reaction mixture was heated to 80° C. for 16 h. The reaction mixture was cooled and diluted with water (50 ml). The resulting mixture was extracted with EtOAc (3×50 mL), dried over MgSO4, and concentrated. Silica gel chromatography (0-100% EtOAc in hexanes) afforded 1,4-Dimethyl-9-nitro-1,2,3,4-tetrahydro-benzo[e][1,4]diazepin-5-one as a yellow solid (326 mg, 60%). mp 146-147° C.; LCMS: m/z=236.23 (M+H+), 1H NMR (400 MHz, CDCl3) δ 7.80 (dd, J=8.1 Hz, 1.8 Hz, 1H), 7.77 (d, J=8.1 Hz, 1.8 Hz, 1H), 7.09 (dd, J=8.1 Hz, 1H), 3.54 (t, J=5.0 Hz, 2H), 3.42 (t, J=5.0 Hz, 2H), 3.22 (s, 3H), 2.71 (s, 3H).

541b) 1,4-Dimethyl-9-nitro-1,2,3,4-tetrahydro-benzo[e][1,4]diazepin-5-one (#) (300 mg, 1.27 mmol) was dissolved in MeOH (20 ml) and placed in a Parr bottle. Pd—C (10%, 30 mg) was added, and the resulting mixture was shaken under 20 psi H2 for 2 h. The reaction mixture was filtered through celite, washed with MeOH, and concentrated to afford 9-Amino-1,4-dimethyl-1,2,3,4-tetrahydro-benzo[e][1,4]diazepin-5-one as a light grey solid (253 mg, 99%). mp 165-166° C.; LCMS: m/z=206.29 (M+H+), 1H NMR (400 MHz, CDCl3) δ 7.06 (m, 2H), 6.86 (m, 1H), 3.34 (m, 4H), 3.19 (s, 3H), 2.79 (s, 3H).

541c) 9-Amino-1,4-dimethyl-1,2,3,4-tetrahydro-benzo[e][1,4]diazepin-5-one (#) (50 mg, 0.24 mmol) and 2-(2,5-Dichloro-pyrimidin-4-ylamino)-N-methyl-benzamide (#) (79 mg, 0.27 mmol) were combined in isopropanol (1 mL). 4 N HCl in dioxane (67 µL) was added, and the resulting mixture was heated to 110° C. in the microwave for 20 min. The resulting solution was diluted with CH2Cl2 (50 ml) washed with saturated aqueous NaHCO3 (2×50 ml), dried over MgSO4, filtered, and concentrated. The resulting residue was purified with silica gel chromatography (0-100% EtOAc in hexanes) to obtain 2-[5-Chloro-2-(1,4-dimethyl-5-oxo-2,3,4,5-tetrahydro-1H-benzo[e][1,4]diazepin-9-ylamino)-pyrimidin-4-ylamino]-N-methyl-benzamide as an off-white solid (47 mg, 41%). mp 243-244° C.; LCMS: m/z=466.16 (M+H+); 1H NMR (400 MHz, CDCl3) δ 11.00 (s, 1H), 8.54 (m, 3H), 8.12 (s, 1H), 7.51 (m, 2H), 7.26 (m, 1H), 7.19 (dd, J=7.8 Hz, 1H), 7.09 (dd, J=7.8 Hz, 1H), 6.42 (d, J=4.5 Hz, 1H), 3.36 (m, 4H), 3.21 (s, 3H), 3.03 (d, J=4.8 Hz, 3H), 2.82 (s, 3H).

Example 542

N-{(1R,2R)-2-[5-Chloro-2-(1,4-dimethyl-5-oxo-2,3,4,5-tetrahydro-1H-benzo[e][1,4]diazepin-9-ylamino)-pyrimidin-4-ylamino]-cyclohexyl} methanesulfonamide 542a) 9-Amino-1,4-dimethyl-1,2,3,4-tetrahydro-benzo[e][1,4]diazepin-5-one (50 mg, 0.24 mmol) and N-[(1R,2R)-2-(2,5-Dichloro-pyrimidin-4-ylamino)-cyclohexyl]-methane sulfonamide (90 mg, 0.27 mmol) were combined in isopropanol (1 mL). 4 N HCl in dioxane (67 µL) was added, and the resulting mixture was heated to 130° C. in the microwave for 30 min. The resulting solution was diluted with CH2Cl2 (50 ml) washed with saturated aqueous NaHCO3 (2×50 ml), dried over MgSO4, filtered, and concentrated. The resulting residue was purified with silica gel chromatography (0-100% EtOAc in hexanes followed by 0-20% MeOH in EtOAc) to obtain N-{(1R,2R)-2-[5-Chloro-2-(1,4-dimethyl-5-oxo-2,3,4,5-tetrahydro-1H-benzo[e][1,4]diazepin-9-ylamino)-pyrimidin-4-ylamino]-cyclohexyl} methanesulfonamide as a beige foam (27 mg, 22%). LCMS: m/z=510.20 (M+H+); 1H NMR (400 MHz, CDCl3) δ 8.48 (m, 2H), 7.96 (s, 1H), 7.27 (m, 2H), 5.60 (m, 2H), 3.95 (m, 1H), 3.34 (m, 5H), 3.20 (s, 3H), 2.86 (s, 3H), 2.78 (s, 3H), 2.24 (m, 2H0, 1.83 (m, 2H), 1.39 (m, 4H).

Example 543

2-[5-Chloro-2-(1,4-dimethyl-5-oxo-2,3,4,5-tetrahydro-1H-benzo[e][1,4]diazepin-9-ylamino)-pyrimidin-4-ylamino]-N-methyl-benzenesulfonamide 543a) 9-Amino-1,4-dimethyl-1,2,3,4-tetrahydro-benzo[e][1,4]diazepin-5-one (#) (50 mg, 0.24 mmol) and 2-(2,5-Dichloro-pyrimidin-4-ylamino)-N-methyl-benzenesulfonamide (#) (89 mg, 0.27 mmol) were combined in isopropanol (1 mL). 4 N HCl in dioxane (67 µL) was added, and the resulting mixture was heated to 120° C. in the microwave for 40 min. The resulting solution was diluted with CH2Cl2 (50 ml) washed with saturated aqueous NaHCO3 (2×50 ml), dried over MgSO4, filtered, and concentrated. The resulting residue was purified with silica gel chromatography (0-100% EtOAc in hexanes) to obtain 2-[5-Chloro-2-(1,4-dimethyl-5-oxo-2,3,4,5-tetrahydro-1H-benzo[e][1,4]diazepin-9-ylamino)-pyrimidin-4-ylamino]-N-methyl-benzenesulfonamide as a white foam (65 mg, 53%). LCMS: m/z=503.20 (M+H+), 1H NMR (400 MHz, CDCl3) δ 9.18 (s, 1H), 8.68 (s, 1H), 8.40 (t, J=7.1 Hz, 2H), 7.97 (m, 2H), 7.62 (t, 7.6 Hz, 1H), 7.27 (m, 2H), 7.14 (t, J=7.6 Hz, 1H), 5.88 (m, 1H), 3.38 (m, 4H), 3.21 (s, 3H), 2.82 (s, 3H), 2.67 (d, J=5.3 Hz, 3H).

Example 544

2-[5-Chloro-2-(1-methyl-5-oxo-2,3,4,5-tetrahydro-1H-benzo[e][1,4]diazepin-9-ylamino)pyrimidin-4-ylamino]-N-methyl-benzamide 544a) 2-Chloro-3-nitro-benzoic acid methyl ester (500 mg, 2.32 mmol) was dissolved in n-butanol (2.5 ml). Na2CO3 (246 mg, 2.32 mmol) was added followed by N, methylethylenediamine (204 µL, 2.32 mmol). The reaction mixture was heated to 80° C. for 16 h. The reaction mixture was cooled and diluted with water (50 ml). The resulting mixture was extracted with EtOAc (3×50 mL), dried over MgSO4, and concentrated. Silica gel chromatography (0-100% EtOAc in hexanes) afforded 1-Methyl-9-nitro-1,2,3,4-tetrahydro-benzo[e][1,4]diazepin-5-one as a bright orange solid (114 mg, 24%). Cmp 183-184° C.; LCMS: m/z=222.25 (M+H+) 1H NMR (400 MHz, CDCl3) δ 8.68 (bs, 1H), 8.32 (dd, J=8.4 Hz, 1.8 Hz, 1H), 8.15 (dd, J=7.8 Hz, 1.5 Hz, 1H), 6.78 (t, J=8.3 Hz, 1H), 3.79 (m, 2H), 3.63 (m, 2H), 3.20 (s, 3H).

544b) 1-Methyl-9-nitro-1,2,3,4-tetrahydro-benzo[e][1,4]diazepin-5-one (#) (100 mg, 0.45 mmol) was dissolved in MeOH (20 ml) and placed in a Parr bottle. Pd—C (10%, 10 mg) was added, and the resulting mixture was shaken under 20 psi H2 for 1.5 h. The reaction mixture was filtered through celite, washed with MeOH, and concentrated to afford 9-Amino-1-methyl-1,2,3,4-tetrahydro-benzo[e][1,4]diazepin-5-one as a brown solid (86 mg, 99%). mp 130-133° C.; LCMS: m/z=192.30 (M+H+); 1H NMR (400 MHz, CDCl3) δ 7.26 (m, 1H), 6.80 (m, 2H), 3.79 (bs, 2H), 3.45 (m, 4H), 3.16 (s, 3H).

544c) 9-Amino-1-methyl-1,2,3,4-tetrahydro-benzo[e][1,4]diazepin-5-one (#) (40 mg, 0.21 mmol) and 2-(2,5-Dichloro-pyrimidin-4-ylamino)-N-methyl-benzamide (#) (68 mg, 0.23 mmol) were combined in isopropanol (1 mL). 4 N HCl in dioxane (57 µL) was added, and the resulting mixture was heated to 110° C. in the microwave for 20 min. The resulting mixture was filtered, washed with CH2Cl2 and acetone. The ppt was dissolved in H2O, neutralized with NaHCO3, and extracted with EtOAc, dried over MgSO4, filtered, and concentrated. The resulting residue was purified with silica gel chromatography (0-10% MeOH in CH2Cl2) to obtain 2-[5-Chloro-2-(1-methyl-5-oxo-2,3,4,5-tetrahydro-1H-benzo[e][1,4]diazepin-9-ylamino)pyrimidin-4-ylamino]-N-methyl-benzamide as a white solid (6 mg, 5%). mp 282-284° C.; LCMS: m/z=452.22 (M+H+), 1H NMR (400 MHz, CDCl3) δ 11.30 (s, 1H), 8.41 (d, J=8.8 Hz, 1H), 8.06 (s, 1H), 7.73 (d, J=8.0 Hz, 1H), 7.49 (d, J=7.6 Hz, 1H), 7.42 (d, J=8.0 Hz, 1H), 7.26 (m, 1H), 7.06 (m, 1H), 6.88 (m, 1H), 6.69 (m, 1H), 6.21 (m, 1H), 4.43 (m, 1H), 3.55 (m, 2H), 3.42 (m, 2H), 3.18 (s, 3H), 3.02 (m, 3H).

Example 545

2-[2-(1-Allyl-5-oxo-2,3,4,5-tetrahydro-1H-benzo[e][1,4]diazepin-9-ylamino)-5-chloro-pyrimidin-4-ylamino]-N-methyl-benzamide 545a) 2-Chloro-3-nitro-benzoic acid methyl ester (2.00 g, 9.3 mmol) was dissolved in n-butanol (10 ml). Na2CO3 (986 mg, 9.3 mmol) was added followed by ethylenediamine (622 µL, 9.3 mmol). The reaction mixture was heated to 80° C. for 16 h. The reaction mixture was cooled, filtered, and washed with water (200 ml) to afford 9-Nitro-1,2,3,4-tetrahydrobenzo[e][1,4]diazepin-5-one as a bright orange solid (900 mg, 46%). mp 196-197° C.; LCMS: m/z=208.22 (M+H+); 1H NMR (400 MHz, DMSO-d6) δ 8.70 (m, 1H), 8.39 (m, 1H), 8.22 (dd, J=8.3 Hz, 1.8 Hz, 1H), 8.14 (dd, J=7.8 Hz, 1.8 Hz, 1H), 6.75 (t, J=7.8 Hz, 1H), 3.65 (m, 2H), 3.35 (m, 2H).

545b) 9-Nitro-1,2,3,4-tetrahydro-benzo[e][1,4]diazepin-5-one (763 mg, 3.67 mmol) was dissolved in anh DMF (10 ml). NaH (60% dispersion in mineral oil) (147 mg, 3.67 mmol) was added followed by allyl bromide (310 μL, 3.67 mmol). The resulting mixture was stirred at rt for 2 h. Reaction mixture was concentrated, diluted with CH2Cl2, and washed with H2O. The organic layer was dried over MgSO4, filtered, concentrated, and purified with silica gel chromatography (0-100% EtOAc in hexanes) to afford 1-Allyl-9-nitro-1,2,3,4-tetrahydro-benzo[e][1,4]diazepin-5-one as an orange solid (647 mg, 71%). mp 80-82° C.; LCMS: m/z=248.27 (M+H+); 1H NMR (400 MHz, CDCl3) δ 8.67 (m, 1H), 8.30 (dd, J=8.3 Hz, 1.5 Hz, 1H), 8.17 (dd, J=7.6 Hz, 1.5 Hz, 1H), 6.78 (t, J=7.8 Hz, 1H0, 5.85 (m, 1H), 5.29 (m, 2H), 4.22 (m, 2H), 3.74 (m, 2H), 3.58 (m, 2H).

545c) 1-Allyl-9-nitro-1,2,3,4-tetrahydro-benzo[e][1,4]diazepin-5-one (#) (300 mg, 1.21 mmol) and SnCl2.2H2O (928 mg, 4.11 mmol) were dissolved in EtOH (25 ml) and heated to 80° C. for 3 h. The reaction mixture was concentrated down onto celite and dry loaded onto a silica gel column running a gradient from 0-100% EtOAc in hexanes to recover 1-Allyl-9-amino-1,2,3,4-tetrahydro-benzo[e][1,4]diazepin-5-one as a white solid (74 mg, 27%). Compound X: mp 234 (dec); LCMS: m/z=218.28 (M+H+), 1H NMR (400 MHz, DMSO-d6) δ 6.85 (d, J=7.8 Hz, 1H), 6.69 (d, J=7.6 Hz, 1H), 6.54 (t, J=7.6 Hz, 1H), 5.83 (m, 1H), 5.19 (m, 2H), 4.76 (bs (2H), 4.66 (bs, 1H), 4.09 (d, J=5.6 Hz, 1H), 3.42 (m, 2H), 3.36 (m, 2H).

545d) 1-Allyl-9-amino-1,2,3,4-tetrahydro-benzo[e][1,4] diazepin-5-one (#) (68 mg, 0.31 mmol) and 2-(2,5-Dichloro-pyrimidin-4-ylamino)-N-methyl-benzamide (#) (102 mg, 0.34 mmol) were combined in isopropanol (1 mL). 4 N HCl in dioxane (85 μL) was added, and the resulting mixture was heated to 120° C. in the microwave for 50 min. The resulting solution was diluted with CH2Cl2, washed with NaHCO3, dried over MgSO4, filtered, and concentrated. The resulting residue was purified with silica gel chromatography (0-100% EtOAc in hexanes) to obtain 2-[2-(1-Allyl-5-oxo-2,3,4,5-tetrahydro-1H-benzo[e][1,4]diazepin-9-ylamino)-5-chloro-pyrimidin-4-ylamino]-N-methyl-benzamide as a white solid (7 mg, 3%). mp 186° C. (dec); LCMS: m/z=478.28 (M+H+), 1H NMR (400 MHz, CDCl3) δ 8.32 (m, 1H), 8.02 (s, 1H), 7.73 (m, 1H), 7.53 (m, 1H), 7.44 (m, 1H), 7.31 (m, 1H), 7.18 (m, 1H), 7.02 (m, 1H), 6.88 (m, 1H), 5.86 (m, 1H), 5.24 (m, 2H), 4.20 (m, 2H), 3.41 (m, 6H), 2.96 (d, J=4.5 Hz, 3H).

Example 601

(2-exo-3-exo)-3-[5-Chloro-2-(1-ethyl-6-methoxy-2-oxo-2,3,4,5-tetrahydro-1H-benzo[b]azepin-7-ylamino)-pyrimidin-4-ylamino]-bicyclo[2.2.1]hept-5-ene-2-carboxylic acid methylamide 601a) (2-exo-3-exo)-3-(2,5-Dichloro-pyrimidin-4-ylamino)-bicyclo[2.2.1]hept-5-ene-2-carboxylic acid methylamide was prepared by reacting (2-exo-3-exo)-3-Amino-bicyclo[2.2.1]hept-5-ene-2-carboxylic acid methylamide trifluoro-acetate with 2,4,5-trichloro-pyrimidine in an analogous manner as for the preparation of (2-exo,3-exo)-3-(2,5-dichloro-pyrimidin-4-ylamino)-bicyclo[2.2.1]hept-5-ene-2-carboxamide of Example 19. However rather than being stirred in a mixed solvent system at room temperature for 69 h, the reaction mixture was warmed in DMF at 80° C. for 16 h. After a typical workup the crude product oil was crystallized from CH3CN to yield a white solid (66%), mp 199-200° C.; $^1$H NMR (400 MHz, DMSO-$d_6$) δ 8.47 (d, J=7.31 Hz, 1H), 8.35 (d, J=4.32 Hz, 1H), 8.20 (s, 1H), 7.86 (s, 1H), 6.33 (br s, 1H), 6.30 (br s, 1H), 3.99 (m, 1H), 2.88 (s, 1H), 2.75 (s, 1H), 2.60 (d, J=3.5 Hz, 3H), 2.07 (d, J=8.73 Hz, 1H), 1.40 (d, J=8.07 Hz, 1H); MS (m/e) 313.02 (M+H).

601b) (2-exo-3-exo)-3-[5-Chloro-2-(1-ethyl-6-methoxy-2-oxo-2,3,4,5-tetrahydro-1H-benzo[b]azepin-7-ylamino)-pyrimidin-4-ylamino]-bicyclo[2.2.1]hept-5-ene-2-carboxylic acid methylamide was prepared in an analogous manner as Example 67 by reacting (2-exo-3-exo)-3-(2,5-Dichloro-pyrimidin-4-ylamino)-bicyclo[2.2.1]hept-5-ene-2-carboxylic acid methylamide with 7-Amino-1-ethyl-6-methoxy-1,3,4,5-tetrahydro-benzo[b]azepin-2-one. Other reaction variations from Example 67 included using (D,L)-camphorsulfonic acid as the acid catalyst rather than HCl, and running the reaction under microwave conditions at 120° C. for 1 h rather than at 140° C. for 30 minutes. The crude product was purified via preparative HPLC to yield desired product (2-exo-3-exo)-3-[5-Chloro-2-(1-ethyl-6-methoxy-2-oxo-2,3,4,5-tetrahydro-1H-benzo[b]azepin-7-ylamino)-pyrimidin-4-ylamino]-bicyclo[2.2.1]hept-5-ene-2-carboxylic acid methylamide as a lyophylate (20%); $^1$H NMR (400 MHz, DMSO-$d_6$) δ 9.0 (bs, 1H), 8.9 (bs, 1H), 8.41 (d, J=4.51 Hz, 1H), 8.19 (s, 1H), 8.01 (d, J=8.73 Hz, 1H), 7.21 (d, J=8.82 Hz, 1H), 6.35 (br s, 1H), 6.25 (br s, 1H), 3.99 (m, 1H), 3.73 (s, 3H), 2.88 (s, 2H), 2.75 (s, 1H), 2.63 (d, J=4.2 Hz, 3H), 2.15 (bs, 4H), 2.04 (d, J=8.48 Hz, 1H), 1.40 (d, J=8.59 Hz, 1H), 1.00 (m, 3H); MS (m/e) 511.21 (M+H).

Example 602

(2-exo-3-exo)-3-[5-Chloro-2-(1-ethyl-6-methoxy-2-oxo-2,3,4,5-tetrahydro-1H-benzo[b]azepin-7-ylamino)-pyrimidin-4-ylamino]-bicyclo[2.2.1]hept-5-ene-2-carboxylic acid dimethylamide (2-exo-3-exo)-3-(2,5-dichloro-pyrimidin-4-ylamino)-bicyclo[2.2.1]hept-5-ene-2-carboxylic acid dimethylamide, prepared in a similar manner as Example 601a, was reacted with 7-Amino-1-ethyl-6-methoxy-1,3,4,5-tetrahydro-benzo[b]azepin-2-one, in a similar manner as Example 601b, to yield desired product (2-Exo-3-exo)-3-[5-Chloro-2-(1-ethyl-6-methoxy-2-oxo-2,3,4,5-tetrahydro-1H-benzo[b]azepin-7-ylamino)-pyrimidin-4-ylamino]-bicyclo[2.2.1]hept-5-ene-2-carboxylic acid dimethylamide as a lyophylate (30%); $^1$H NMR (400 MHz, DMSO-$d_6$) δ 9.2 (bs, 1H), 8.9 (bs, 1H), 8.41 (d, J=4.51 Hz, 1H), 8.19 (s, 1H), 8.02 (m, 1H), 7.21 (d, J=8.88 Hz, 1H), 6.41 (br s, 1H), 6.28 (br s, 1H), 4.06 (m, 1H), 3.73 (s, 3H), 3.04 (s, 3H), 2.90 (m, 6H), 2.15 (bs, 4H), 1.99 (d, J=8.48 Hz, 1H), 1.44 (d, J=9.41 Hz, 1H), 1.00 (m, 3H); MS (m/e) 525.20 (M+H).

Example 603

(2-exo-3-exo)-3-[5-Chloro-2-(1-ethyl-6-methoxy-2-oxo-2,3,4,5-tetrahydro-1H-benzo[b]azepin-7-ylamino)-pyrimidin-4-ylamino]-bicyclo[2.2.1]hept-5-ene-2-carboxylic acid isopropylamide (2-exo-3-exo)-3-(2,5-Dichloro-pyrimidin-4-ylamino)-bicyclo[2.2.1]hept-5-ene-2-carboxylic acid isopropylamide, prepared in a similar manner as Example 601a, was reacted with 7-Amino-1-ethyl-6-methoxy-1,3,4,5-tetrahydro-benzo[b]azepin-2-one, in a similar manner as Example 601b, to yield desired product (2-exo-3-exo)-3-[5-Chloro-2-(1-ethyl- 6-methoxy-2-oxo-2,3,4,5-tetrahydro-1H-benzo[b]azepin-7-ylamino)-pyrimidin-4-ylamino]-bicyclo[2.2.1]hept-5-ene-2-carboxylic acid isopropylamide as a lyophylate (30%); $^1$H NMR (400 MHz, DMSO-$d_6$) δ 8.9 (bs, 1H), 8.8 (bs, 1H), 8.27 (d, J=7.45 Hz, 1H), 8.18 (s, 1H), 8.02 (d, J=8.68 Hz, 1H), 7.21 (d, J=8.86 Hz, 1H), 6.35 (br s, 1H), 6.25 (br s, 1H), 3.9-4.0 (m, 1H), 3.8-3.9 (m, 1H), 3.73 (s, 3H), 2.87 (s, 2H), 2.15 (bs, 4H), 2.06 (d, J=8.82 Hz, 1H), 1.41 (d, J=8.49 Hz, 1H), 1.0-1.5 (m, 9H); MS (m/e) 539.24 (M+H).

Example 604

(2-exo-3-exo)-3-{5-Chloro-2-[8-methoxy-3-(2-methoxy-ethyl)-2,3,4,5-tetrahydro-1H-benzo[d]azepin-7-ylamino]-pyrimidin-4-ylamino}-bicyclo[2.2.1]hept-5-ene-2-carboxylic acid methylamide (2-exo-3-exo)-3-(2,5-Dichloro-pyrimidin-4-ylamino)-bicyclo[2.2.1]hept-5-ene-2-carboxylic acid methylamide of Example 601a was reacted with 8-Methoxy-3-(2-methoxy-ethyl)-2,3,4,5-tetrahydro-1H-benzo[d]azepin-7-ylamine, in a similar manner as Example 601b, to yield desired product (2-exo-3-exo)-3-{5-Chloro-2-[8-methoxy-3-(2-methoxy-ethyl)-2,3,4,5-tetrahydro-1H-benzo[d]azepin-7-ylamino]-pyrimidin-4-ylamino}-bicyclo[2.2.1]hept-5-ene-2-carboxylic acid methylamide as a lyophylate (28%); $^1$H NMR (400 MHz, DMSO-$d_6$) δ 9.9 (bs, 1H), 8.8-8.5 (bs, 2H), 8.36 (bs, 1H), 8.10 (s, 1H), 7.81 (bs, 1H), 7.00 (s, 1H), 6.35 (br s, 1H), 6.14 (br s, 1H), 4.03 (m, 1H), 3.83 (s, 3H), 3.8-3.6 (bd, water+multiple H), 3.40 (s, 3H), 3.25-3.1 (m, 2H), 3.1-3.0 (bs, 2H), 2.95-2.80 (m, 2H), 2.77 (d, J=9.6 Hz, 1H), 2.62 (bs, 3H), 2.08 (m, 1H), 1.40 (bs, 1H); MS (m/e) 527.38 (M+H).

Example 605

(2-exo-3-exo)-3-{5-Chloro-2-[8-methoxy-3-(2-methoxy-ethyl)-2,3,4,5-tetrahydro-1H-benzo[d]azepin-7-ylamino]-pyrimidin-4-ylamino}-bicyclo[2.2.1]hept-5-ene-2-carboxylic acid isopropylamide (2-exo-3-exo)-3-(2,5-dichloro-pyrimidin-4-ylamino)-bicyclo[2.2.1]hept-5-ene-2-carboxylic acid dimethylamide of Example 603 was reacted with 8-Methoxy-3-(2-methoxy-ethyl)-2,3,4,5-tetrahydro-1H-benzo[d]azepin-7-ylamine, in a similar manner as Example 601b, to yield desired product (2-exo-3-exo)-3-{5-Chloro-2-[8-methoxy-3-(2-methoxy-ethyl)-2,3,4,5-tetrahydro-1H-benzo[d]azepin-7-ylamino]-pyrimidin-4-ylamino}-bicyclo[2.2.1]hept-5-ene-2-carboxylic acid isopropylamide as a lyophylate (26%); $^1$H NMR (400 MHz, DMSO-$d_6$) δ 9.85 (bs, 1H), 8.45 (bs, 1H), 8.18 (bs, 2H), 8.06 (s, 1H), 7.86 (bs, 1H), 6.99 (s, 1H), 6.34 (br s, 1H), 6.16 (br s, 1H), 4.4-3.9 (bd, water+H), 3.83 (s, 3H), 3.7-3.5 (bm, 6H), 3.40 (bs, 2H), 3.33 (s, 3H), 3.25-3.1 (m, 2H), 3.1-3.0 (bs, 3H), 3.0-2.85 (m, 2H), 2.77 (d, J=8.94 Hz, 1H), 2.62 (bs, 3H), 2.13 (m, 1H), 1.42 (bs, 1H), 1.06 (d, J=6.57 Hz, 3H), 0.98 (d, J=6.49 Hz, 3H); MS (m/e) 555.50 (M+H).

Example 606

(2-exo-3-exo)-3-{5-Chloro-2-[8-methoxy-3-(2-methoxy-ethyl)-2,3,4,5-tetrahydro-1H-benzo[d]azepin-7-ylamino]-pyrimidin-4-ylamino}-bicyclo[2.2.1]hept-5-ene-2-carboxylic acid dimethylamide (2-exo-3-exo)-3-(2,5-dichloro-pyrimidin-4-ylamino)-bicyclo[2.2.1]hept-5-ene-2-carboxylic acid dimethylamide of Example 602 was reacted with 8-Methoxy-3-(2-methoxy-ethyl)-2,3,4,5-tetrahydro-1H-benzo[d]azepin-7-ylamine, in a similar manner as Example 601b, to yield desired product (2-exo-3-exo)-3-{5-Chloro-2-[8-methoxy-3-(2-methoxy-ethyl)-2,3,4,5-tetrahydro-1H-benzo[d]azepin-7-ylamino]-pyrimidin-4-ylamino}-bicyclo[2.2.1]hept-5-ene-2-carboxylic acid dimethylamide as a lyophylate (41%); $^1$H NMR (400 MHz, DMSO-$d_6$) δ 9.85 (bs, 1H), 8.45 (bs, 1H), 8.07 (s, 1H), 7.86 (bs, 1H), 6.99 (s, 1H), 6.38 (br s, 1H), 6.17 (br s, 1H), 4.16 (m, 1H), 3.84 (s, 3H), 3.8-3.6 (bm, 4H), 3.40 (bs, 2H), 3.33 (s, 3H), 3.25-3.1 (bd, 2H), 3.1-2.8 (m, 10H), 2.79 (d, J=8.96 Hz, 1H), 2.03 (m, 1H), 1.44 (bs, 1H); MS (m/e) 541.48 (M+H).

Example 607

2-[5-Chloro-2-(1-ethyl-6-methoxy-2-oxo-2,3,4,5-tetrahydro-1H-benzo[b]azepin-7-ylamino)-pyrimidin-4-ylamino]-5-methoxy-N-methyl-benzamide 2-(2,5-Dichloro-pyrimidin-4-ylamino)-5-methoxy-N-methyl-benzamide, prepared in a similar manner as Example 601a from known 2-amino-5-methoxy-N-methyl-benzamide reacted with 2,4,5-trichloropyrimidine was reacted with 7-Amino-1-ethyl-6-methoxy-1,3,4,5-tetrahydro-benzo[b]azepin-2-one, in a similar manner as Example 601b, to yield crude product 2-[5-Chloro-2-(1-ethyl-6-methoxy-2-oxo-2,3,4,5-tetrahydro-1H-benzo[b]azepin-7-ylamino)-pyrimidin-4-ylamino]-5-methoxy-N-methyl-benzamide. The crude material was semi-purified by preparative HPLC, and the purest fractions were partitioned between NaHCO$_3$ and CH$_2$Cl$_2$. The organic phase was dried over Na$_2$SO$_4$, filtered and concentrated under reduced pressure to give a clear oil. This material was dissolved in Et$_2$O and treated with 1N ethereal HCl. The resulting solid was filtered, then dissolved in CH$_3$CN. A solid precipitated with scratching, which was filtered and rinsed with a small amount of ice cold CH$_3$CN to give desired product as a solid HCl salt (4%); $^1$H NMR (400 MHz, DMSO-$d_6$) δ 11.3 (bs, 1H), 8.74 (bs, 1H), 8.5 (bs, 1H), 8.42 (bd, 1H) 8.18 (s, 1H), 7.74 (d, J=8.84 Hz, 1H), 7.28 (s, 1H), 7.16 (d, J=9.85 Hz), 6.94 (d, J=11.12 Hz, 1H), 3.80 (s, 3H), 3.69 (s, 3H), 2.80 (bs, 3H), 2.23 (bs, 4H), 1.24 (bs, 2H), 1.0 (m, 3H); MS (m/e) 525.49 (M+H).

Example 608

2-[5-Chloro-2-(1-ethyl-6-methoxy-2-oxo-2,3,4,5-tetrahydro-1H-benzo[b]azepin-7-ylamino)-pyrimidin-4-ylamino]-5-methoxy-benzoic acid isopropyl ester 2-[5-Chloro-2-(1-ethyl-6-methoxy-2-oxo-2,3,4,5-tetrahydro-1H-benzo[b]azepin-7-ylamino)-pyrimidin-4-ylamino]-5-methoxy-benzoic acid isopropyl ester was also generated as a product from the reaction of Example 607, and was purified by preparative HPLC to yield the desired product as a lyophylate (3%); $^1$H NMR (400 MHz, DMSO-$d_6$) δ 10.49 (s, 1H), 8.6 (bs, 1H), 8.32 (d, J=9.40 Hz, 1H) 8.24 (s, 1H), 7.66 (d, J=8.63 Hz, 1H), 7.44 (s, 1H), 7.1 (m, 2H), 5.14 (m, 1H), 3.80 (s, 3H), 3.8-3.7 (bs, water+H), 3.68 (s, 3H), 2.15-1.95 (bm, 4H), 1.29 (s, 3H), 1.27 (s, 3H), 1.0 (m, 3H); MS (m/e) 554.50 (M+H).

Example 609

2-[5-Chloro-2-(5,5-dimethyl-2-oxo-2,3,4,5-tetrahydro-1H-benzo[b]azepin-7-ylamino)-pyrimidin-4-ylamino]-5-methoxy-N-methyl-benzamide 2-(2,5-Dichloro-pyrimidin-4-ylamino)-5-methoxy-N-methyl-benzamide of Example 607 was reacted with 7-amino- 5,5-dimethyl-1,3,4,5-tetrahydro-benzo[b]azepin-2-one, in a similar manner as Example 601b, to yield desired product 2-[5-Chloro-2-(5,5-dimethyl-2-oxo-2,3,4,5-tetrahydro-1H-benzo[b]azepin-7-ylamino)-pyrimidin-4-ylamino]-5-methoxy-N-methyl-benzamide as a lyophylate (22%); $^1$H NMR (400 MHz, DMSO-d$_6$) δ 11.27 (s, 1H), 9.39 (s, 1H), 8.77 (bs, 1H), 8.55 (bs, 1H) 8.17 (s, 1H), 7.63 (d, J=8.17 Hz, 1H), 7.49 (s, 1H), 7.31 (s, 1H), 7.03 (d, J=8.89 Hz, 1H), 6.87 (d, J=8.68 Hz, 1H), 3.82 (s, 3H), 2.80 (d, J=3.80 Hz, 3H), 2.50 (m, 2H), 2.16 (m, 2H), 1.27 (s, 6H); MS (m/e) 495.45 (M+H).

Example 610

N*4*-[(2-exo-3-exo)-3-(1H-Benzoimidazol-2-yl)-bicyclo[2.2.1]hept-5-en-2-yl]-5-chloro-N*2*-[8-methoxy-3-(2-methoxy-ethyl)-2,3,4,5-tetrahydro-1H-benzo[d]azepin-7-yl]-pyrimidine-2,4-diamine 610a) ((2-exo, 3-exo)-3-Formyl-bicyclo[2.2.1]hept-5-en-2-yl)-carbamic acid tert-butyl ester (95 mg, 0.40 mmol; Maring, C. J., et. al., U.S. Pat. No. 6,518,305 (2003)) and 1,2-Benzenediamine (43 mg, 0.40 mmol; TCI America) were combined in THF (3 mL) and warmed to reflux open to the air overnight. The reaction was concentrated under reduced pressure and the residual 177 mg was triturated with CH$_3$CN to give an off white solid precipitate. This material was filtered and rinsed with a small amount of CH$_3$CN, then Et$_2$O. After air drying there remained 58 mg (44%) of off white solid (2-exo-3-exo)-3-(1H-Benzimidazol-2-yl)-bicyclo[2.2.1]hept-5-en-2-yl]-carbamic acid tert-butyl ester; $^1$H NMR (400 MHz, CDCl$_3$) δ 11.65 (bs, 1H, exchangeable), 7.75 (bs, 1H), 7.5 (bs, 1H), 7.31 (s, 1H), 7.20 (m, 2H), 6.55 (bs, 1H), 6.05 (bs, 1H), 5.0 (bs, 1H, exchangeable), 3.75 (s, 1H), 3.65 (bs, 1H), 3.25 (s, 1H), 2.83 (s, 1H), 1.81 (s, 2H), 1.54 (s, 9H); MS (m/e) 326.08 (M+H).

610b) [(2-exo-3-exo)-3-(1H-Benzimidazol-2-yl)-bicyclo[2.2.1]hept-5-en-2-yl]-carbamic acid tert-butyl ester (100 mg, 0.3 mmol) dissolved in Methylene chloride (8 mL, 100 mmol) was treated with Trifluoroacetic Acid (3 mL, 40 mmol) at room temperature. After 1 hour the reaction was concentrated under reduced pressure and the residue was placed under high vacuum overnight. The resulting solid was treated with CH$_3$CN (4 mL). Most material dissolved, but then quickly crashed back out. The resulting suspension was cooled in an ice bath, then filtered and rinsed with a small amount of ice cold CH$_3$CN. After air drying there remained 85 mg (80%) of white solid product (2-exo-3-exo)-3-(1H-Benzimidazol-2-yl)-bicyclo[2.2.1]hept-5-en-2-ylamine; compound with trifluoro-acetic acid, mp 202-204° C.; $^1$H NMR (400 MHz, DMSO-d$_6$) δ 8.26 (s, 3H), 7.61 (s, 2H), 7.30 (s, 2H), 5.98 (s, 1H), 5.76 (s, 1H), 3.70 (s, 1H), 3.57 (s, 1H), 3.42 (s, 1H), 3.12 (s, 1H), 2.09 (m, 1H), 1.66 (d, J=9.07 Hz, 1H); MS (m/e) 226.03 (M+H).

610c) (2-exo-3-exo)-3-(1H-Benzimidazol-2-yl)-bicyclo[2.2.1]hept-5-en-2-ylamine; compound with trifluoro-acetic acid (68 mg, 0.20 mmol) and 2,4,5-Trichloro-pyrimidine (33 mg, 0.18 mmol) were treated in a similar manner as described in Example 19. Workup varied slightly; the desired product was isolated after 24 h simply by crashing out with water to yield 45 mg (67%) of [(2-exo-3-exo)-3-(1H-Benzimidazol-2-yl)-bicyclo[2.2.1]hept-5-en-2-yl]-(2,5-dichloro-pyrimidin-4-yl)-amine as a white solid, mp 200-202° C.; $^1$H NMR (400 MHz, DMSO-d$_6$) δ 12.10 (s, 1H), 8.22 (s, 1H), 7.97 (d, J=6.64 Hz, 1H), 7.50 (d, J=7.48 Hz, 1H), 7.40 (m, 1H), 7.15-7.05 (m, 2H), 6.29 (s, 1H), 5.98 (bs, 1H), 4.47 (bs, 1H), 4.0 (MeOH), 3.92 (s, 1H), 3.37 (s, 1H), 3.18 (MeOH; 0.75 eqvt), 2.90 (s, 1H), 2.01 (d, J=8.52 Hz, 1H), 1.60 (d, J=8.64 Hz, 1H); MS (m/e) 372.09 (M+H).

610d) [(2-exo-3-exo)-3-(1H-Benzimidazol-2-yl)-bicyclo[2.2.1]hept-5-en-2-yl]-(2,5-dichloro-pyrimidin-4-yl)-amine was reacted with 8-Methoxy-3-(2-methoxy-ethyl)-2,3,4,5-tetrahydro-1H-benzo[d]azepin-7-ylamine, in a similar manner as Example 601b, to yield desired product N*4*-[(2-exo-3-exo)-3-(1H-Benzoimidazol-2-yl)-bicyclo[2.2.1]hept-5-en-2-yl]-5-chloro-N*2*-[8-methoxy-3-(2-methoxy-ethyl)-2,3,4,5-tetrahydro-1H-benzo[d]azepin-7-yl]-pyrimidine-2,4-diamine as a lyophylate (62%); $^1$H NMR (400 MHz, DMSO-d$_6$) showed some Camphor sulfonic adduct, as well as probable TFA adduct from HPLC purification; as such, aliphatic region convaluted with apparent rotamers; key peaks notable are MeO-Ph and 2.2.1 bicycle-benzimidazole protons; aromatic assignments: δ 9.70 (bs, 1H), 8.06 (s, 1H), 7.95 (s, 1H), 7.71 (bs, 2H), 7.46 (bs, 2H), 6.86 (s, 1H), 6.34 (bs, 1H), 6.09 (bs, 1H), 3.66 (s, 3H), MS (m/e) 586.45 (M+H).

Example 611

7-[5-Chloro-4-(4-methoxy-2-pyrazol-1-yl-phenylamino)-pyrimidin-2-ylamino]-5,5-dimethyl-1,3,4,5-tetrahydro-benzo[b]azepin-2-one 611a) Over 3 minutes a solution of 1H-Pyrazole (0.714 g, 10.5 mmol; TCI-America) in THF (10 mL) was added to an ice cooled suspension of 0.43 g of 60% NaH (11 mmol) in THF (30 mL). Upon completion of addition an almost clear solution resulted. After stirring an additional 10 minutes 2-Fluoro-4-methoxy-1-nitro-benzene (1.71 g, 9.99 mmol; Combi-Blocks) in THF (10 mL) was added over 1 minute. The resulting solution was warmed to rt after 20 minutes and stirred overnight. The reaction mixture was then quenched with water and extracted with EtOAc (2×). The organics were combined, dried over MgSO$_4$, filtered and concentrated to yield an oil that was placed under high vacuum overnight. After drying there remained 2.26 g (103%) of orange solid product 1-(5-Methoxy-2-nitro-phenyl)-1H-pyrazole; $^1$H NMR (400 MHz, CDCl$_3$) δ 7.97 (d, J=9.08 Hz, 1H), 7.77 (s, 1H), 7.69 (d, J=2.39 Hz, 1H), 7.28 (s, 1H), 7.07 (d, J=2.61 Hz, 1H), 6.99 (m, 1H), 6.51 (s, 1H), 3.94 (s, 3H); MS (m/e) 220.09 (M+H).

611b) 1-(5-Methoxy-2-nitro-phenyl)-1H-pyrazole was treated under standard hydrogenation conditions (H2, EtOH, 10% Pd/C) to yield desired 4-Methoxy-2-pyrazol-1-yl-phenylamine as a crude solid, which was used for the subsequent reaction without further purification; TLC: 1:1 EtOAc/Hexane Rf 0.6, homogeneous; SM Rf 0.7; MS (m/e) 190.12 (M+H).

611c) 4-Methoxy-2-pyrazol-1-yl-phenylamine was reacted with 2,4,5-Trichloro-pyrimidine, in a similar manner as Example 601a, to yield desired product (2,5-Dichloro-pyrimidin-4-yl)-(4-methoxy-2-pyrazol-1-yl-phenyl)-amine as a white solid (44%), mp 209-210.5° C.; $^1$H NMR (400 MHz, DMSO-d$_6$) δ 10.24 (s, 1H), 8.30 (s, 1H), 8.26 (s, 1H), 7.84 (d, J=8.96 Hz, 1H), 7.78 (s, 1H), 7.22 (d, J=2.70 Hz, 1H), 7.05 (m, 1H), 6.51 (s, 1H), 3.86 (s, 3H); MS (m/e) 336.53 (M+H).

611d) (2,5-Dichloro-pyrimidin-4-yl)-(4-methoxy-2-pyrazol-1-yl-phenyl)-amine was reacted with 7-amino-5,5-dimethyl-1,3,4,5-tetrahydro-benzo[b]azepin-2-one, in a similar manner as Example 601b, to yield desired product 7-[5-Chloro-4-(4-methoxy-2-pyrazol-1-yl-phenylamino)-pyrimidin-2-ylamino]-5,5-dimethyl-1,3,4,5-tetrahydro-benzo[b]azepin-2-one as a lyophylate (20%); $^1$H NMR (400 MHz, DMSO-d$_6$) δ 9.91 (s, 1H), 9.37 (s, 2H), 8.26 (s, 1H), 8.12 (s, 1H), 8.03 (d, J=8.90 Hz, 1H), 7.84 (s, 1H), 7.55 (d, J=8.56 Hz, 1H), 7.40 (s, 1H), 7.22 (d, J=1.87 Hz, 1H), 6.98 (d, J=8.64 Hz, 1H), 6.78 (d, J=8.45 Hz, 1H), 6.55 (s, 1H), 3.86 (s, 3H), 2.16 (m, 2H), 1.95 (m, 2H), 1.24 (s, 6H); MS (m/e) 504.45 (M+H).

Example 612

5-Chloro-N*2*-[8-methoxy-3-(2-methoxy-ethyl)-2,3,4,5-tetrahydro-1H-benzo[d]azepin-7-yl]-N*4*-(4-methoxy-2-pyrazol-1-yl-phenyl)-pyrimidine-2,4-diamine (2,5-Dichloro-pyrimidin-4-yl)-(4-methoxy-2-pyrazol-1-yl-phenyl)-amine, of Example 611c, was reacted with 8-Methoxy-3-(2-methoxy-ethyl)-2,3,4,5-tetrahydro-1H-benzo[d]azepin-7-ylamine, in a similar manner as Example 601b, to yield desired product 7-[5-Chloro-4-(4-methoxy-2-pyrazol-1-yl-phenylamino)-pyrimidin-2-ylamino]-5,5-dimethyl-1,3,4,5-tetrahydro-benzo[b]azepin-2-one as a lyophylate (25%); $^1$H NMR (400 MHz, DMSO-d$_6$) δ 9.84 (s, 1H), 9.71 (bs, 1H), 8.21 (s, 1H), 8.11 (s, 1H), 7.95 (bs, 1H), 7.89 (d, J=8.71 Hz, 1H), 7.80 (s, 1H), 7.61 (s, 1H), 7.24 (d, J=2.64 Hz, 1H), 7.00 (m, 1H), 6.92 (s, 1H), 6.53 (s, 1H), 3.87 (s, 3H), 3.80 (s, 3H), 3.75-3.5 (m, 4H), 3.39 (bs, 2H), 3.35 (s, 3H), 3.2-2.9 (m, 4H), 2.7 (m, 1H); MS (m/e) 550.45 (M+H).

Example 613

7-[5-Chloro-4-(4-methoxy-2-pyrazol-1-yl-phenylamino)-pyrimidin-2-ylamino]-1-ethyl-6-methoxy-1,3,4,5-tetrahydro-benzo[b]azepin-2-one (2,5-Dichloro-pyrimidin-4-yl)-(4-methoxy-2-pyrazol-1-yl-phenyl)-amine, of Example 611c, was reacted with 7-Amino-1-ethyl-6-methoxy-1,3,4,5-tetrahydro-benzo[b]azepin-2-one, in a similar manner as Example 601b, to yield desired product 7-[5-Chloro-4-(4-methoxy-2-pyrazol-1-yl-phenylamino)-pyrimidin-2-ylamino]-1-ethyl-6-methoxy-1,3,4,5-tetrahydro-benzo[b]azepin-2-one as a lyophylate (22%); $^1$H NMR (400 MHz, DMSO-d$_6$) δ 10.20 (s, 1H), 8.61 (bs, 1H), 8.27 (s, 1H), 8.18 (s, 1H), 7.96 (d, J=9.06 Hz, 1H), 7.83 (s, 1H), 7.64 (d, J=8.83 Hz, 1H), 7.22 (s, 1H), 7.00 (d, J=8.98 Hz, 1H), 6.95 (d, J=9.09 Hz, 1H), 6.55 (s, 1H), 3.84 (s, 3H), 3.67 (s, 3H), 2.1-1.9 (m, 6H), 1.03 (m, 3H); MS (m/e) 534.47 (M+H).

Example 614

7-[5-Chloro-4-(4-methoxy-2-pyrazol-1-yl-phenylamino)-pyrimidin-2-ylamino]-1-ethyl-8-methoxy-1,3,4,5-tetrahydro-benzo[b]azepin-2-one (2,5-Dichloro-pyrimidin-4-yl)-(4-methoxy-2-pyrazol-1-yl-phenyl)-amine, of Example 611c, was reacted with 7-Amino-1-ethyl-8-methoxy-1,3,4,5-tetrahydro-benzo[b]azepin-2-one, in a similar manner as Example 601b, to yield desired product 7-[5-Chloro-4-(4-methoxy-2-pyrazol-1-yl-phenylamino)-pyrimidin-2-ylamino]-1-ethyl-8-methoxy-1,3,4,5-tetrahydro-benzo[b]azepin-2-one as a lyophylate (30%); $^1$H NMR (400 MHz, DMSO-d$_6$) δ 10.10 (s, 1H), 8.47 (bs, 1H), 8.21 (s, 1H), 8.17 (s, 1H), 7.79 (m, 2H), 7.56 (s, 1H), 7.23 (s, 1H), 7.01-6.95 (m, 2H), 6.51 (s, 1H), 3.84 (bs, 8H), 2.36 (bs, 2H), 2.05 (bs, 2H), 1.9 (bs, 2H), 1.03 (m, 3H); MS (m/e) 534.48 (M+H).

Example 615

(2-exo-3-exo)-3-{5-Chloro-2-[3-(2-methoxy-ethyl)-2,3,4,5-tetrahydro-1H-benzo[d]azepin-7-ylamino]-pyrimidin-4-ylamino}-bicyclo[2.2.1]hept-5-ene-2-carboxylic acid methylamide (2-exo-3-exo)-3-(2,5-Dichloro-pyrimidin-4-ylamino)-bicyclo[2.2.1]hept-5-ene-2-carboxylic acid methylamide, of Example 601a, was reacted with 3-(2-Methoxy-ethyl)-2,3,4,5-tetrahydro-1H-benzo[d]azepin-7-ylamine, in a similar manner as Example 601b, to yield desired product (2-exo-3-exo)-3-{5-Chloro-2-[3-(2-methoxy-ethyl)-2,3,4,5-tetrahydro-1H-benzo[d]azepin-7-ylamino]-pyrimidin-4-ylamino}-bicyclo[2.2.1]hept-5-ene-2-carboxylic acid methylamide as a lyophylate (30%); $^1$H NMR (400 MHz, DMSO-d$_6$) δ 9.7 (bs, 1H), 9.4 (bs, 1H), 8.29 (bs, 1H), 7.99 (s, 1H), 7.89 (bs, 1H), 7.75-7.6 (m, 1H), 7.42 (d, J=13.03 Hz, 1H), 7.13 (d, J=8.31 Hz, 1H), 6.36 (br s, 1H), 6.28 (br s, 1H), 4.09 (m, 1H), 3.7-3.6 (bm, 5H), 3.38 (bs, 2H), 3.34 (s, 3H), 3.3-2.75 (m, 8H), 2.62 (d, J=4.42 Hz, 3H), 2.12 (bs, 1H), 1.43 (bs, 1H); MS (m/e) 497.36 (M+H).

Example 616

2-{7-[5-Chloro-4-(4-methoxy-2-pyrazol-1-yl-phenylamino)-pyrimidin-2-ylamino]-8-methoxy-1,2,4,5-tetrahydro-benzo[d]azepin-3-yl}-N,N-dimethyl-acetamide (2,5-Dichloro-pyrimidin-4-yl)-(4-methoxy-2-pyrazol-1-yl-phenyl)-amine, of Example 611c, was reacted with 2-(7-Amino-8-methoxy-1,2,4,5-tetrahydro-benzo[d]azepin-3-yl)-N,N-dimethyl-acetamide, in a similar manner as Example 601b, to yield desired product {7-[5-Chloro-4-(4-methoxy-2-pyrazol-1-yl-phenylamino)-pyrimidin-2-ylamino]-8-methoxy-1,2,4,5-tetrahydro-benzo[d]azepin-3-yl}-N,N-dimethyl-acetamide as a lyophylate (38%); $^1$H NMR (400 MHz, DMSO-d$_6$) δ 9.80 (bm, 2H), 8.20 (s, 1H), 8.10 (s, 1H), 7.94 (s, 1H), 7.86 (d, J=9.07 Hz, 1H), 7.79 (s, 1H), 7.60 (s, 1H), 7.23 (d, J=2.06 Hz, 1H), 6.98 (d, J=8.92 Hz, 1H), 6.90 (s, 1H), 6.52 (s, 1H), 4.32 (s, 2H), 3.86 (s, 3H), 3.80 (s, 3H), 3.63 (bs, water+H), 3.4-2.95 (m, 6H), 2.95 (s, 6H); MS (m/e) 577.42 (M+H).

Example 617

2-[5-Chloro-2-(3-dimethylcarbamoylmethyl-8-methoxy-2,3,4,5-tetrahydro-1H-benzo[d]azepin-7-ylamino)-pyrimidin-4-ylamino]-5-methoxy-N-methyl-benzamide 2-(2,5-Dichloro-pyrimidin-4-ylamino)-5-methoxy-N-methyl-benzamide of Example 607 was reacted with 2-(7-Amino-8-methoxy-1,2,4,5-tetrahydro-benzo[d]azepin-3-yl)-N,N-dimethyl-acetamide, in a similar manner as Example 601b, to yield desired product 2-[5-Chloro-2-(3-dimethylcarbamoylmethyl-8-methoxy-2,3,4,5-tetrahydro-1H-benzo[d]azepin-7-ylamino)-pyrimidin-4-ylamino]-5-methoxy-N-methyl-benzamide as a lyophylate (29%); $^1$H NMR (400 MHz, DMSO-d$_6$) δ 11.30 (s, 1H, exchangeable), 9.85 (bs, 1H, exchangeable), 8.77 (d, J=4.72 Hz, 1H, exchangeable), 8.39 (d, J=8.84 Hz, 1H) 8.27 (s, 1H, exchangeable), 8.17 (s, 1H), 7.66 (s, 1H), 7.31 (s, 1H), 6.98 (m, 2H), 4.33 (s, 2H), 3.86 (s, 3H), 3.82 (s, 3H), 3.7-3.5 (m, 2H), 3.4-3.0 (m, 4H), 2.95 (s, 6H), 2.80 (d, J=4.30 hz, 3H); MS (m/e) 568.43 (M+H).

Example 618

2-{5-Chloro-2-[3-(2-methoxy-ethyl)-2,3,4,5-tetrahydro-1H-benzo[d]azepin-7-ylamino]-pyrimidin-4-ylamino}-5-methoxy-N-methyl-benzamide 2-(2,5-Dichloro-pyrimidin-4-ylamino)-5-methoxy-N-methyl-benzamide of Example 607 was reacted with 3-(2-Methoxy-ethyl)-2,3,4,5-tetrahydro-1H-benzo[d]azepin-7-ylamine, in a similar manner as Example 601b, to yield desired product 2-{5-Chloro-2-[3-(2-methoxy-ethyl)-2,3,4,5-tetrahydro-1H-benzo[d]azepin-7-ylamino]-pyrimidin-4-ylamino}-5-methoxy-N-methyl-benzamide as a lyophylate (29%); $^1$H NMR (400 MHz, DMSO-$d_6$) δ 11.22 (s, 1H), 9.71 (bs, 1H), 9.43 (s, 1H), 8.75 (bs, 1H), 8.54 (d, J=8.59 Hz, 1H), 8.18 (s, 1H), 7.53 (s, 1H), 7.42 (d, J=8.85 Hz, 1H), 7.32 (d, J=2.78 Hz, 1H), 7.12-7.06 (m, 2H), 3.83 (s, 3H), 3.8-3.6 (m, 6H), 3.45 (m, 2H), 3.34 (s, 3H), 3.25-2.9 (m, 4H), 2.9 (d, J=4.04 Hz, 3H); MS (m/e) 511.37 (M+H).

Example 619

7-[5-Chloro-4-(4-methoxy-2-pyrazol-1-yl-phenylamino)-pyrimidin-2-ylamino]-1,5,5-trimethyl-1,3,4,5-tetrahydro-benzo[b]azepin-2-one (2,5-Dichloro-pyrimidin-4-yl)-(4-methoxy-2-pyrazol-1-yl-phenyl)-amine, of Example 611c, was reacted with 7-Amino-1,5,5-trimethyl-1,3,4,5-tetrahydro-benzo[b]azepin-2-one, in a similar manner as Example 601b, to yield desired product 7-[5-Chloro-4-(4-methoxy-2-pyrazol-1-yl-phenylamino)-pyrimidin-2-ylamino]-1,5,5-trimethyl-1,3,4,5-tetrahydro-benzo[b]azepin-2-one as a lyophylate (60%); $^1$H NMR (400 MHz, DMSO-$d_6$) δ 9.96 (s, 1H), 9.48 (s, 1H), 8.26 (s, 1H), 8.14 (s, 1H), 8.04 (d, J=9.26 Hz, 1H), 7.84 (s, 1H), 7.65 (d, J=8.20 Hz, 1H), 7.41 (s, 1H), 7.22 (s, 1H), 7.13 (d, J=8.65 Hz, 1H), 7.00 (m, 1H), 6.55 (s, 1H), 3.85 (s, 3H), 3.17 (s, 3H), 2.12 (m, 2H), 1.90 (m, 2H), 1.16 (s, 6H); MS (m/e) 518.45 (M+H).

Example 620

(2-exo-3-exo)-3-[5-Chloro-2-(5,5-dimethyl-2-oxo-2,3,4,5-tetrahydro-1H-benzo[b]azepin-7-ylamino)-pyrimidin-4-ylamino]-bicyclo[2.2.1]hept-5-ene-2-carboxylic acid methylamide (2-exo-3-exo)-3-(2,5-Dichloro-pyrimidin-4-ylamino)-bicyclo[2.2.1]hept-5-ene-2-carboxylic acid methylamide, of Example 601a, was reacted with 7-amino-5,5-dimethyl-1,3,4,5-tetrahydro-benzo[b]azepin-2-one, in a similar manner as Example 601b, to yield desired product (2-exo-3-exo)-3-[5-Chloro-2-(5,5-dimethyl-2-oxo-2,3,4,5-tetrahydro-1H-benzo[b]azepin-7-ylamino)-pyrimidin-4-ylamino]-bicyclo[2.2.1]hept-5-ene-2-carboxylic acid methylamide as a lyophylate (50%); $^1$H NMR (400 MHz, DMSO-$d_6$) δ 9.64 (bs, 1H, exchangeable), 9.39 (s, 1H, exchangeable), 8.35 (bm, 2H, exchangeable), 8.06 (s, 1H), 7.74 (d, J=8.14 Hz, 1H), 7.44 (s, 1H), 6.93 (d, J=8.42 Hz, 1H), 6.35 (bs, 1H), 6.20 (bs, 1H), 4.09 (m, 1H), 2.87 (s, 1H), 2.81 (s, 1H), 2.62 (s, 3H), 2.20 (m, 2H), 2.07 (d, J=8.69 Hz, 1H), 1.97 (m, 2H), 1.41 (d, J=8.33 Hz, 1H), 1.32 (s, 6H); MS (m/e) 481.44 (M+H).

Example 621

2-{5-Chloro-2-[8-methoxy-3-(2-methoxy-ethyl)-2,3,4,5-tetrahydro-1H-benzo[d]azepin-7-ylamino]-pyrimidin-4-ylamino}-5-methoxy-N-methyl-benzamide 2-(2,5-Dichloro-pyrimidin-4-ylamino)-5-methoxy-N-methyl-benzamide of Example 607 was reacted with 8-Methoxy-3-(2-methoxy-ethyl)-2,3,4,5-tetrahydro-1H-benzo[d]azepin-7-ylamine, in a similar manner as Example 601b, to yield desired product 2-{5-Chloro-2-[8-methoxy-3-(2-methoxy-ethyl)-2,3,4,5-tetrahydro-1H-benzo[d]azepin-7-ylamino]-pyrimidin-4-ylamino}-5-methoxy-N-methyl-benzamide as a lyophylate (8%); $^1$H NMR (400 MHz, DMSO-$d_6$) δ 11.27 (s, 1H, exchangeable), 9.75 (bs, 1H, exchangeable), 8.74 (bs, 1H, exchangeable), 8.42 (d, J=9.35 Hz, 1H), 8.15 (s, 2H, 1 exchangeable), 7.68 (s, 1H), 7.31 (s, 1H), 7.00 (m, 2H), 3.83 (s, 3H), 3.80 (s, 3H), 3.70 (m, 2H), 3.6 (bs, water+H), 3.40 (m, 2H), 3.34 (s, 3H), 3.3-2.95 (m, 4H), 2.80 (d, J=4.04 Hz, 3H); MS (m/e) 541.37 (M+H).

Example 622

5-Chloro-N*4*-(4-methoxy-2-pyrazol-1-yl-phenyl)-N*2*-(7-morpholin-4-yl-6,7,8,9-tetrahydro-5H-benzocyclohepten-2-yl)-pyrimidine-2,4-diamine (2,5-Dichloro-pyrimidin-4-yl)-(4-methoxy-2-pyrazol-1-yl-phenyl)-amine, of Example 611c, was reacted with 7-Morpholin-4-yl-6,7,8,9-tetrahydro-5H-benzocyclohepten-2-ylamine, in a similar manner as Example 601b, to yield desired product 5-Chloro-N*4*-(4-methoxy-2-pyrazol-1-yl-phenyl)-N*2*-(7-morpholin-4-yl-6,7,8,9-tetrahydro-5H-benzocyclohepten-2-yl)-pyrimidine-2,4-diamine as a lyophylate (25%); $^1$H NMR (400 MHz, DMSO-$d_6$) δ 9.77 (s, 1H), 9.64 (bs, 1H), 9.33 (s, 1H), 8.75 (s, 1H), 8.11 (s, 1H), 8.00 (d, J=8.97 Hz, 1H), 7.83 (s, 1H), 7.41 (s, 1H), 7.25 (m, 2H), 7.1-6.95 (m, 2H), 6.54 (s, 1H), 4.00 (m, 2H), 3.88 (s, 3H), 3.8-3.7 (m, 2H), 3.6-3.5 (m, 1H), 3.4-3.1 (m, 4H), 2.8-2.6 (m, 4H), 2.29 (m, 2H), 1.42 (m, 2H); MS (m/e) 546.37 (M+H).

Example 623

2-[5-Chloro-4-(4-methoxy-2-pyrazol-1-yl-phenylamino)-pyrimidin-2-ylamino]-6,7,8,9-tetrahydro-5H-benzocyclohepten-7-ol The desired product was also isolated from Example 622, as starting material 7-Morpholin-4-yl-6,7,8,9-tetrahydro-5H-benzocyclohepten-2-ylamine of Example 622 was contaminated with a small amount of its respective alcohol, 2-Amino-6,7,8,9-tetrahydro-5H-benzocyclohepten-7-ol. The product 2-[5-Chloro-4-(4-methoxy-2-pyrazol-1-yl-phenylamino)-pyrimidin-2-ylamino]-6,7,8,9-tetrahydro-5H-benzocyclohepten-7-ol was isolated as a lyophylate (10%); $^1$H NMR (400 MHz, DMSO-$d_6$) δ 9.79 (s, 1H), 9.23 (s, 1H), 8.26 (s, 1H), 8.09 (s, 1H), 8.02 (d, J=8.62 Hz, 1H), 7.83 (s, 1H), 7.35 (s, 1H), 7.23 (s, 1H), 7.19 (d, J=7.95 Hz, 1H), 7.00 (d, J=8.98 Hz, 1H), 6.90 (d, J=8.20 Hz, 1H), 6.54 (s, 1H), 3.87 (s, 3H), 3.71 (bm, 1H), 2.68 (m, 1H), 2.5 (DMSO-d+H), 1.86 (m, 2H), 1.30 (m, 2H); MS (m/e) 477.43 (M+H).

Example 624

(2-exo-3-exo)-3-[5-Chloro-2-(7-morpholin-4-yl-6,7,8,9-tetrahydro-5H-benzocyclohepten-2-ylamino)-pyrimidin-4-ylamino]-bicyclo[2.2.1]hept-5-ene-2-carboxylic acid methylamide 2-(2,5-Dichloro-pyrimidin-4-ylamino)-5-methoxy-N-methyl-benzamide of Example 607 was reacted with 7-Morpholin-4-yl-6,7,8,9-tetrahydro-5H-benzocyclohepten-2-ylamine, in a similar manner as Example 601b, to yield desired product (2-exo-3-exo)-3-[5-Chloro-2-(7-morpholin- 4-yl-6,7,8,9-tetrahydro-5H-benzocyclohepten-2-ylamino)-pyrimidin-4-ylamino]-bicyclo[2.2.1]hept-5-ene-2-carboxylic acid methylamide as a lyophylate (25%); $^1$H NMR (400 MHz, DMSO-d$_6$) δ 9.60 (bs, 1H), 9.45 (s, 1H), 8.31 (d, J=4.29 Hz, 1H), 8.01 (s, 2H), 7.62 (d, J=7.07 Hz, 0.36H), 7.54 (d, J=8.14 Hz, 0.64H), 7.47 (s, 0.65H), 7.39 (s, 0.35H), 7.10 (d, J=7.96 Hz, 1H), 6.36 (bs, 1H), 6.28 (bs, 1H), 4.10 (m, 1H), 3.98 (m, 2H), 3.72 (m, 2H), 3.55 (m, 1H), 3.28-3.10 (m, 4H), 2.87-2.65 (m, 6H), 2.62 (d, J=4.29 Hz, 3H), 2.5 (DMSO+H), 2.33 (m, 2H), 2.12 (m, 1H), 1.42 (m, 3H); MS (m/e) 523.48 (M+H).

Example 625

(2-exo-3-exo)-3-[5-Chloro-2-(7-hydroxy-6,7,8,9-tetrahydro-5H-benzocyclohepten-2-ylamino)-pyrimidin-4-ylamino]-bicyclo[2.2.1]hept-5-ene-2-carboxylic acid methylamide The desired product was also isolated from Example 624, as starting material 7-Morpholin-4-yl-6,7,8,9-tetrahydro-5H-benzocyclohepten-2-ylamine of Example 624 was contaminated with a small amount of its respective alcohol, 2-Amino-6,7,8,9-tetrahydro-5H-benzocyclohepten-7-ol. The product (2-exo-3-exo)-3-[5-Chloro-2-(7-hydroxy-6,7,8,9-tetrahydro-5H-benzocyclohepten-2-ylamino)-pyrimidin-4-ylamino]-bicyclo[2.2.1]hept-5-ene-2-carboxylic acid methylamide was isolated as a lyophylate (10%); $^1$H NMR (400 MHz, DMSO-d$_6$) δ 9.45 (bs, 1H), 8.33 (bm, 2H), 8.02 (s, 1H), 7.42 (d, J=7.07 Hz, 1H), 7.38 (s, 1H), 7.04 (d, J=8.21 Hz, 1H), 6.35 (bs, 1H), 6.24 (bs, 1H), 4.08 (m, 1H), 3.74 (bs, H2O+2H), 3.17 (s, 1H), 2.86-2.65 (m, 4H), 2.5 (DMSO+H), 2.09 (d, J=8.34 Hz, 1H), 1.89 (bm, 2H), 1.42 (d, J=8.73 Hz, 1H), 1.3 (bm, 2H); MS (m/e) 454.44 (M+H).

Example 626

2-{7-[5-Chloro-4-(4-morpholin-4-yl-2-pyrazol-1-yl-phenylamino)-pyrimidin-2-ylamino]-8-methoxy-1,2,4,5-tetrahydro-benzo[d]azepin-3-yl}-N,N-dimethyl-acetamide 626a) Under N$_2$ a solution of 1-(5-Methoxy-2-nitro-phenyl)-1H-pyrazole (3.00 g, 13.7 mmol), of Example 611a, in Morpholine (100 mL, 1000 mmol; Acros) was warmed to 120° C. for 100 h. The reaction mixture was concentrated under reduced pressure and the residue partitioned between 10% Na$_2$CO$_3$ and EtOAc. The aqueous phase was washed with a second portion of EtOAc, then the organics were combined, dried over Na$_2$SO$_4$, filtered and concentrated to yield 1.46 g of crude product 4-(4-Nitro-3-pyrazol-1-yl-phenyl)-morpholine (26% by LC). An initial purification by normal phase chromatography eluting with a gradient of 100% CH$_2$Cl$_2$ to 10:1 CH$_2$Cl$_2$:MeOH met with limited success. The purest fractions were concentrated and rerun on another normal phase column eluting with a gradient of 10% EtOAc/Hexane to 65% EtOAc/Hexane. The purest fractions were combined and concentrated under reduced pressure to give 0.48 g of purer material. This material was crystallized from Et$_2$O and the resulting solid was filtered and rinsed with a small amount of Et$_2$O to yield 318 mg (9%) of 4-(4-Nitro-3-pyrazol-1-yl-phenyl)-morpholine, which was carried on without further purification.

$^1$H NMR (400 MHz, CDCl$_3$) δ 8.04 (d, J=9.25 Hz, 1H), 7.76 (s, 1H), 7.65 (d, J=1.95 Hz, 1H), 6.93 (d, J=2.21 Hz, 1H), 6.86 (m, 1H), 6.50 (s, 1H), 3.87 (m, 4H), 3.40 (m, 4H).

The original aqueous phase was cooled and acidified with 6 N HCl to pH 3, then extracted with EtOAc (2×). The organics were combined and dried over Na$_2$SO$_4$, filtered and concentrated under reduced pressure to yield 2.11 g of brown residue. This material was treated with 25 mL of water. The resulting solid was filtered and rinsed liberally with water. After air drying there remained 1.54 g (55%) of 4-Nitro-3-pyrazol-1-yl-phenol, which was also used in subsequent steps without further purification. $^1$H NMR (400 MHz, CDCl$_3$) δ 9.95 (bs, 1H), 8.00 (d, J=9.06 Hz, 1H), 7.84 (s, 1H), 7.68 (s, 1H), 7.07 (s, 1H), 6.87 (m, 1H), 6.56 (d, J=1.87H, 1H).

626b) 4-(4-Nitro-3-pyrazol-1-yl-phenyl)-morpholine was treated under standard hydrogenation conditions (H$_2$, EtOH, 10% Pd/C) to yield desired 4-Morpholin-4-yl-2-pyrazol-1-yl-phenylamine as a crude oil, which was used for the subsequent reaction without further purification; TLC: 10:1 CH$_2$Cl$_2$:MeOH Rf 0.6, homogeneous (SM Rf 0.7); MS (m/e) 245.17 (M+H).

626c) 4-Morpholin-4-yl-2-pyrazol-1-yl-phenylamine was reacted with 2,4,5-Trichloro-pyrimidine, in a similar manner as Example 601a, to yield desired product (2,5-Dichloro-pyrimidin-4-yl)-(4-morpholin-4-yl-2-pyrazol-1-yl-phenyl)-amine as a white solid upon trituration from CH$_3$CN (49%); TLC: 1:1 EtOAc/Hexane Rf 0.4, homogeneous; $^1$H NMR (400 MHz, CDCl$_3$) δ 10.35 (s, 1H), 8.34 (d, J=9.11 Hz, 1H), 8.12 (s, 1H), 7.84 (s, 1H), 7.81 (s, 1H), 7.01 (d, J=9.17 Hz, 1H), 6.88 (s, 1H), 6.52 (s, 1H), 3.90 (m, 4H), 3.22 (m, 4H); MS (m/e) 391.44 (M+H).

626d) (2,5-Dichloro-pyrimidin-4-yl)-(4-morpholin-4-yl-2-pyrazol-1-yl-phenyl)-amine was reacted with 2-(7-Amino-8-methoxy-1,2,4,5-tetrahydro-benzo[d]azepin-3-yl)-N,N-dimethyl-acetamide, in a similar manner as Example 601b, to yield desired product 2-{7-[5-Chloro-4-(4-morpholin-4-yl-2-pyrazol-1-yl-phenylamino)-pyrimidin-2-ylamino]-8-methoxy-1,2,4,5-tetrahydro-benzo[d]azepin-3-yl}-N,N-dimethyl-acetamide as a lyophylate (25%); $^1$H NMR (400 MHz, DMSO-d$_6$) δ 9.90 (m, 2H), 8.20 (m, 2H), 7.80 (m, 2H), 7.68 (s, 1H), 7.14 (s, 1H), 7.01 (m, 1H), 6.92 (s, 1H), 6.50 (s, 1H), 4.33 (s, 2H), 3.79 (m, 7H), 3.58 (bm, 2H), 3.35-3.15 (m, 5H), 3.15-3.07 (m, 4H), 2.99 (s, 6H), 2.50 (m, 1H); MS (m/e) 632.51 (M+H).

Example 627

7-[5-Chloro-4-(4-morpholin-4-yl-2-pyrazol-1-yl-phenylamino)-pyrimidin-2-ylamino]-5,5-dimethyl-1,3,4,5-tetrahydro-benzo[b]azepin-2-one (2,5-Dichloro-pyrimidin-4-yl)-(4-morpholin-4-yl-2-pyrazol-1-yl-phenyl)-amine was reacted with 7-amino-5,5-dimethyl-1,3,4,5-tetrahydro-benzo[b]azepin-2-one, in a similar manner as Example 601b, to yield desired product 7-[5-Chloro-4-(4-morpholin-4-yl-2-pyrazol-1-yl-phenylamino)-pyrimidin-2-ylamino]-5,5-dimethyl-1,3,4,5-tetrahydro-benzo[b]azepin-2-one as a lyophylate (7%); $^1$H NMR (400 MHz, DMSO-d$_6$) δ 9.80 (s, 1H), 9.39 (s, 1H), 9.31 (s, 1H), 8.25 (s, 1H), 8.09 (s, 1H), 7.98 (bd, 1H), 7.82 (s, 1H), 7.59 (d, J=8.08 Hz, 1H), 7.41 (s, 1H), 7.12 (s, 1H), 6.98 (d, J=11.11 Hz, 1H), 6.79 (d, J=8.59 Hz, 1H), 6.54 (s, 1H), 3.78 (m, 4H), 3.21 (m, 4H), 2.15 (m, 2H), 1.95 (m, 2H), 1.27 (s, 6H); MS (m/e) 559.54 (M+H).

Example 628

7-{5-Chloro-4-[4-(4-methyl-piperazin-1-yl)-2-pyrazol-1-yl-phenylamino]-pyrimidin-2-ylamino}-5,5-dimethyl-1,3,4,5-tetrahydro-benzo[b]azepin-2-one 628a) To a stirring −78° C. solution of 4-Nitro-3-pyrazol-1-yl-phenol (1.02 g, 5.00 mmol), of Example 626a, and Triethylamine (1.39 mL, 10.0 mmol) in Methylene chloride (25 mL, 390 mmol) was added a solution of Trifluoromethanesulfonic anhydride (1.48 g, 5.25 mmol; Acros) in Methylene chloride (5 mL, 80 mmol) over 5 minutes. After 15 minutes at −78° C., the reaction mixture was warmed to room temperature and partitioned between $CH_2Cl_2$ and saturated aqueous $NaHCO_3$. The aqueous phase was washed with a second portion of $CH_2Cl_2$, then the organics were combined, dried over $Na_2SO_4$, filtered and concentrated under reduced pressure to yield 1.60 g (95%) of orange/brown oil which crystallized upon sitting. TLC: 1:1 EtOAc:Hexane, Rf 0.85, homogeneous. This resulting Trifluoro-methanesulfonic acid 4-nitro-3-pyrazol-1-yl-phenyl ester was used without further purification.

628b) A solution of Trifluoro-methanesulfonic acid 4-nitro-3-pyrazol-1-yl-phenyl ester (502 mg, 1.49 mmol) in piperazine, 1-methyl- (10 mL, 90 mmol; Acros) was stirred at room temperature for 24 h. The reaction mixture was then concentrated under reduced pressure at 55° C. The residue was partitioned between water (100 mL) and $Et_2O$ (100 mL). The aqueous phase was re-extracted with additional $Et_2O$ (25 mL), then the $Et_2O$ extracts were combined, washed with brine, dried over $Na_2SO_4$, filtered and concentrated under reduced pressure. The residue was treated with 10 mL of ice cold $Et_2O$ to yield a solid precipitate. The resulting solid was filtered and rinsed with a small amount of $Et_2O$ to give 221 mg (51%) of desired product 1-Methyl-4-(4-nitro-3-pyrazol-1-yl-phenyl)-piperazine; TLC: 10:1 $CH_2Cl_2$:MeOH Rf 0.35, homogeneous; $^1H$ NMR (400 MHz, $CDCl_3$) δ 8.04 (d, J=9.30 Hz, 1H), 7.76 (s, 1H), 7.65 (s, 1H), 6.91 (s, 1H), 6.85 (m, 1H), 6.49 (s, 1H), 3.50 (m, 4H), 2.56 (m, 4H), 2.37 (s, 3H); MS (m/e) 288.24 (M+H).

628c) 1-Methyl-4-(4-nitro-3-pyrazol-1-yl-phenyl)-piperazine was treated under standard hydrogenation conditions ($H_2$, EtOH, 10% Pd/C) to yield desired 4-(4-Methyl-piperazin-1-yl)-2-pyrazol-1-yl-phenylamine as a crude oil, which was used for the subsequent reaction without further purification; LC/MS (m/e) 258.24 (M+H).

628d) 4-(4-Methyl-piperazin-1-yl)-2-pyrazol-1-yl-phenylamine was reacted with 2,4,5-Trichloro-pyrimidine, in a similar manner as Example 601a, to yield desired product (2,5-Dichloro-pyrimidin-4-yl)-[4-(4-methyl-piperazin-1-yl)-2-pyrazol-1-yl-phenyl]-amine as a clear glass after purification via preparative HPLC followed by free basing (5%); $^1H$ NMR (400 MHz, $CDCl_3$) δ 10.33 (s, 1H), 8.31 (d, J=9.12 Hz, 1H), 8.11 (s, 1H), 7.83 (s, 1H), 7.81 (d, J=2.15 Hz, 1H), 7.02 (m, 1H), 6.88 (d, J=2.24 Hz, 1H), 6.51 (s, 1H), 3.27 (m, 4H), 2.61 (m, 4H), 2.39 (s, 3H); MS (m/e) 404.47 (M+H).

628e) Dichloro-pyrimidin-4-yl)-[4-(4-methyl-piperazin-1-yl)-2-pyrazol-1-yl-phenyl]-amine amine was reacted with 7-amino-5,5-dimethyl-1,3,4,5-tetrahydro-benzo[b]azepin-2-one, in a similar manner as Example 601b, to yield desired product 7-{5-Chloro-4-[4-(4-methyl-piperazin-1-yl)-2-pyrazol-1-yl-phenylamino]-pyrimidin-2-ylamino}-5,5-dimethyl-1,3,4,5-tetrahydro-benzo[b]azepin-2-one as a lyophylate (59%); $^1H$ NMR (400 MHz, DMSO-$d_6$) δ 9.88 (m, 2H), 9.34 (s, 2H), 8.26 (s, 1H), 8.11 (s, 1H), 8.06 (d, J=9.09 Hz, 1H), 7.85 (s, 1H), 7.56 (d, J=8.59 Hz, 1H), 7.45 (s, 1H), 7.21 (s, 1H), 7.02 (d, J=8.84 Hz, 1H), 6.79 (d, J=8.59 Hz, 1H), 6.56 (s, 1H), 3.96 (m, 2H), 3.54 (m, 2H), 3.17-3.10 (m, 2H), 3.10-3.05 (m, 2H), 2.89 (s, 3H), 2.16 (m, 2H), 1.93 (m, 2H), 1.22 (s, 6H); MS (m/e) 572.44 (M+H).

Example 629

1-{4-[5-Chloro-2-(5,5-dimethyl-2-oxo-2,3,4,5-tetrahydro-1H-benzo[b]azepin-7-ylamino)-pyrimidin-4-ylamino]-3-pyrazol-1-yl-phenyl}-piperidine-4-carboxylic acid 629a) A solution of Trifluoro-methanesulfonic acid 4-nitro-3-pyrazol-1-yl-phenyl ester (405 mg, 1.20 mmol) and Ethyl piperidine-4-carboxylate (6 mL, 40 mmol) were stirred at room temperature for 4 hours. The reaction mixture was partitioned between water and $Et_2O$. The aqueous phase was washed with a second portion of $Et_2O$, after which the organic phases were combined, dried over $Na_2SO_4$, filtered and concentrated to yield >5 g of crude material. This material was partitioned between $Et_2O$ and 50 mL of 2N citric acid (aq). The organic phase was washed with brine, dried over $Na_2SO_4$, filtered and concentrated under high vacuum to give 250 mg (59%) of orange residue 1-(4-Nitro-3-pyrazol-1-yl-phenyl)-piperidine-4-carboxylic acid ethyl ester; TLC: 1:1 EtOAc/Hexane Rf 0.65, homogeneous, 10:1 $CH_2Cl_2$:MeOH Rf 0.8, homogeneous; $^1H$ NMR (400 MHz, $CDCl_3$) δ 8.03 (d, J=8.03 hz, 1H), 7.76 (s, 1H), 7.64 (d, J=2.32 Hz, 1H), 6.90 (d, J=2.63 Hz, 1H), 6.84 (m, 1H), 6.49 (s, 1H), 4.20 (m, 2H), 3.91 (m, 2H), 3.15 (m, 2H), 2.60 (m, 1H), 2.04 (m, 2H), 1.86 (m, 2H), 1.23 (m, 3H)); MS (m/e) 345.29 (M+H).

629b) 1-(4-Nitro-3-pyrazol-1-yl-phenyl)-piperidine-4-carboxylic acid ethyl ester was treated under standard hydrogenation conditions ($H_2$, EtOH, 10% Pd/C) to yield desired 1-(4-Amino-3-pyrazol-1-yl-phenyl)-piperidine-4-carboxylic acid ethyl ester as a glass, which was used for the subsequent reaction without further purification; TLC: 1:1 EtOAc/Hexane Rf 0.5, homogeneous; LC/MS (m/e) 315.28 (M+H).

629c) 1-(4-Amino-3-pyrazol-1-yl-phenyl)-piperidine-4-carboxylic acid ethyl ester was reacted with 2,4,5-Trichloro-pyrimidine, in a similar manner as Example 601a, to yield desired product 1-[4-(2,5-Dichloro-pyrimidin-4-ylamino)-3-pyrazol-1-yl-phenyl]-piperidine-4-carboxylic acid ethyl ester as an oil that solidified upon sitting, after purification via normal phase column chromatography eluting with an EtOAc/Hexane gradient system (47%); $^1H$ NMR (400 MHz, $CDCl_3$) δ 10.33 (s, 1H), 8.31 (d, J=9.14 Hz, 1H), 8.11 (s, 1H), 7.81 (m, 2H), 7.1 (m, 1H), 6.90 (d, J=2.67 Hz, 1H), 6.51 (m, 1H), 4.2 (m, 2H), 3.7 (m, 2H), 2.9 (m, 2H), 2.5 (m, 1H), 2.1 (m, 2H), 1.85 (m, 2H), 1.25 (m, 3H); MS (m/e) 461.47 (M+H).

629d) 1-[4-(2,5-Dichloro-pyrimidin-4-ylamino)-3-pyrazol-1-yl-phenyl]-piperidine-4-carboxylic acid ethyl ester was reacted with 7-amino-5,5-dimethyl-1,3,4,5-tetrahydro-benzo[b]azepin-2-one, in a similar manner as Example 601b, to yield desired product 1-{4-[5-Chloro-2-(5,5-dimethyl-2-oxo-2,3,4,5-tetrahydro-1H-1-benzazepin-7-ylamino)-pyrimidin-4-yl amino]-3-pyrazol-1-yl-phenyl}-piperidine-4-carboxylic acid ethyl ester; compound with trifluoro-acetic acid as a lyophylate (50%); $^1H$ NMR (400 MHz, DMSO-$d_6$) δ 9.99 (s, 1H), 9.51 (s, 1H), 9.42 (s, 1H), 8.23 (s, 1H), 8.13 (s, 1H), 7.91 (bd, 1H), 7.82 (s, 1H), 7.52 (d, J=8.41 Hz, 1H), 7.39 (s, 1H), 7.14 (s, 1H), 6.97 (d, J=8.28 Hz, 1H), 6.80 (d, J=8.49 Hz, 1H), 6.53 (s, 1H), 4.2 (m, 2H), 3.8 (H2O+2H), 2.9 (m, 2H), 2.6 (m, 1H), 2.15 (m, 2H), 1.95 (m, 4H), 1.7 (m, 2H), 1.2 (m, 9H); MS (m/e) 629.62 (M+H).

629e) To a room temperature solution of Lithium hydroxide (53 mg, 2.2 mmol) in Water (3 mL), was added 1-{4-[5-Chloro-2-(5,5-dimethyl-2-oxo-2,3,4,5-tetrahydro-1H-1-benzazepin-7-ylamino)-pyrimidin-4-ylamino]-3-pyrazol-1-yl-phenyl}-piperidine-4-carboxylic acid ethyl ester; compound with trifluoro-acetic acid (47 mg, 0.063 mmol)

followed by Methanol (12 mL). After 72 hours 1 N HCl (2 mL) was added to the reaction to neutralize the base, then the mixture was concentrated under reduced pressure. The residue was purified by preparative reverse phase HPLC to yield the desired 1-{4-[5-Chloro-2-(5,5-dimethyl-2-oxo-2,3,4,5-tetrahydro-1H-benzo[b]azepin-7-ylamino)-pyrimidin-4-ylamino]-3-pyrazol-1-yl-phenyl}-piperidine-4-carboxylic acid as a lyophylate (20%); $^1$H NMR (400 MHz, DMSO-d$_6$) δ 9.81 (s, 1H), 9.39 (s, 1H), 9.32 (s, 1H), 8.26 (s, 1H), 8.09 (s, 1H), 7.97 (m, 1H), 7.83 (s, 1H), 7.57 (d, J=7.07 Hz, 1H), 7.42 (s, 1H), 7.12 (s, 1H), 6.97 (d, J=9.86 Hz, 1H), 6.79 (d, J=8.34 Hz, 1H), 6.54 (s, 1H), 3.75 (m, 2H), 2.8 (m, 2H), 2.6 (m, 1H), 2.15 (m, 2H), 1.99 (m, 4H), 1.70 (m, 2H), 1.2 (s, 6H); MS (m/e) 601.56 (M+H).

Example 630

1-{4-[5-Chloro-2-(3-dimethylcarbamoylmethyl-8-methoxy-2,3,4,5-tetrahydro-1H-benzo[d]azepin-7-ylamino)-pyrimidin-4-ylamino]-3-pyrazol-1-yl-phenyl}-piperidine-4-carboxylic acid 1-{4-[5-Chloro-2-(3-dimethylcarbamoylmethyl-8-methoxy-2,3,4,5-tetrahydro-1H-benzo[d]azepin-7-ylamino)-pyrimidin-4-ylamino]-3-pyrazol-1-yl-phenyl}-piperidine-4-carboxylic acid was prepared in a similar manner as described for Example 629, after substituting 2-(7-Amino-8-methoxy-1,2,4,5-tetrahydro-benzo[d]azepin-3-yl)-N,N-dimethyl-acetamide for 7-amino-5,5-dimethyl-1,3,4,5-tetrahydro-benzo[b]azepin-2-one of Example 629d. 1-{4-[5-Chloro-2-(3-dimethylcarbamoylmethyl-8-methoxy-2,3,4,5-tetrahydro-1H-benzo[d]azepin-7-ylamino)-pyrimidin-4-ylamino]-3-pyrazol-1-yl-phenyl}-piperidine-4-carboxylic acid was isolated as a lyophylate (36%); $^1$H NMR (400 MHz, DMSO-d$_6$) δ 9.83 (bs, 1H), 9.70 (s, 1H), 8.19 (s, 1H), 8.10 (s, 1H), 7.79-7.72 (m, 3H), 7.14 (s, 1H), 7.00 (d, J=8.09 Hz, 1H), 6.90 (s, 1H), 6.49 (s, 1H), 4.32 (s, 2H), 3.82 (s, 3H), 3.75 (m, 2H), 3.56 (bs, H2O+2H), 3.3-3.0 (m, 6H), 2.95 (s, 6H), 2.83 (m, 2H), 2.51 (m, 1H), 1.95 (m, 2H), 1.69 (m, 2H); MS (m/e) 674.46 (M+H).

Example 631

2-{7-[5-Chloro-4-(4-dimethylamino-2-pyrazol-1-yl-phenylamino)-pyrimidin-2-ylamino]-8-methoxy-1,2,4,5-tetrahydro-benzo[d]azepin-3-yl}-N,N-dimethyl-acetamide 2-{7-[5-Chloro-4-(4-dimethylamino-2-pyrazol-1-yl-phenylamino)-pyrimidin-2-ylamino]-8-methoxy-1,2,4,5-tetrahydro-benzo[d]azepin-3-yl}-N,N-dimethyl-acetamide was prepared in a similar manner as described for 7-{5-Chloro-4-[4-(4-methyl-piperazin-1-yl)-2-pyrazol-1-yl-phenylamino]-pyrimidin-2-ylamino}-5,5-dimethyl-1,3,4,5-tetrahydro-benzo[b]azepin-2-one of Example 628. Variations included substituting dimethylamine for 1-Methyl-piperazine of Example 628b, and running this reaction in a pressure bottle at room temperature (so the dimethylamine would not evaporate). In addition, 2-(7-Amino-8-methoxy-1,2,4,5-tetrahydro-benzo[d]azepin-3-yl)-N,N-dimethyl-acetamide was substituted for 7-amino-5,5-dimethyl-1,3,4,5-tetrahydro-benzo[b]azepin-2-one of Example 628e. Desired product 2-{7-[5-Chloro-4-(4-dimethylamino-2-pyrazol-1-yl-phenylamino)-pyrimidin-2-ylamino]-8-methoxy-1,2,4,5-tetrahydro-benzo[d]azepin-3-yl}-N,N-dimethyl-acetamide was isolated as a lyophylate (50%); $^1$H NMR (400 MHz, DMSO-d$_6$) δ 9.91 (bs, 1H), 9.83 (s, 1H), 8.33 (bs, 1H), 8.17 (s, 1H), 8.10 (s, 1H), 7.73 (s, 1H), 7.63-7.60 (m, 2H), 6.91 (m, 2H), 6.79 (d, J=8.89 Hz, 1H), 6.46 (s, 1H), 4.32 (s, 2H), 3.81 (s, 3H), 3.58-3.51 (m, 2H), 3.3 (m, 1H), 3.1 (m, 2H), 3.0 (m, 14H), 2.6 (m, 1H); MS (m/e) 590.46 (M+H).

Example 632

(1S,2S,3R,4R)-3-[2-((S)-7-Acetylamino-1-methoxy-9-oxo-6,7,8,9-tetrahydro-5H-benzocyclohepten-2-ylamino)-5-chloro-pyrimidin-4-ylamino]-bicyclo[2.2.1]hept-5-ene-2-carboxylic acid amide 632a) (2-Chloro-5-methoxy-benzyl)-triphenyl-phosphonium; bromide [12.5 g, 25.2 mmol; (Schertl, S., et. al., *Archiv der Pharmazie*, 2001, 334, 125-137)] suspended in 0° C. Tetrahydrofuran (200 mL) was treated over 1 minute with Sodium hydride, 60% disp. in mineral oil (1.01 g; Aldrich). After 2 h, with reaction still at 0° C., a solution of (R)-3-Benzyloxycarbonylamino-4-oxo-butyric acid tert-butyl ester [7.59 g, 24.7 mmol; (prepared in identical manner as the previously reported (S)-3-Benzyloxycarbonylamino-4-oxo-butyric acid tert-butyl ester; Paris, M., et. al. *Tet. Lett.*, 1998, 39, 1341-1344)] in Tetrahydrofuran (90 mL) was added and the reaction was maintained at ice bath temperature for 5 h. The reaction mixture was then treated with 450 mL saturated aqueous NH$_4$Cl, after which the mixture was extracted with EtOAc (2×). The resulting combined organic phases were washed with brine, dried over MgSO$_4$, filtered and concentrated under reduced pressure leaving 18.01 g of slightly tinted oil. This residue was dissolved in a small amount of CH$_2$Cl$_2$, adsorbed on silica and further purified via normal phase chromatography, eluting with a gradient of 0-40% EtOAc/Hexane. The top running product, (Z)—(R)-3-Benzyloxycarbonylamino-5-(2-chloro-5-methoxy-phenyl)-pent-4-enoic acid tert-butyl ester, was isolated as a white solid (1.68 g; 15%); TLC: 25% EtOAc/Hexane Rf 0.5, homogeneous. The lower running product, (E)-(R)-3-Benzyloxycarbonylamino-5-(2-chloro-5-methoxy-phenyl)-pent-4-enoic acid tert-butyl ester, was isolated as an oil (2.79 g; 25%); TLC: 25% EtOAc/Hexane Rf 0.4, homogeneous.

632b) Following the selective reduction procedure of Mori, A., et. al. (*Tetrahedron*, 2006, 62, 11925-11932), a mixture of (Z)—(R)-3-Benzyloxycarbonylamino-5-(2-chloro-5-methoxy-phenyl)-pent-4-enoic acid tert-butyl ester (1.68 g, 3.77 mmol), (E)-(R)-3-Benzyloxycarbonylamino-5-(2-chloro-5-methoxy-phenyl)-pent-4-enoic acid tert-butyl ester (2.79 g, 6.26 mmol), Diphenyl sulfide (20.4 mg, 0.110 mmol), Palladium on Carbon 10% (450 mg) and MeOH (200 mL) was stirred at atmospheric pressure under a bed of hydrogen for 16 h. The reaction mixture was then filtered and concentrated under reduced pressure to give 4.54 g (100%) of clear oil (S)-3-Benzyloxycarbonylamino-5-(2-chloro-5-methoxy-phenyl)-pentanoic acid tert-butyl ester, which was used without further purification; TLC: 25% EtOAc/Hexane Rf 0.45, homogeneous; $^1$H NMR (400 MHz, CDCl$_3$) δ 7.38-7.31 (m, 5H), 7.22 (d, J=8.84 Hz, 1H), 6.79 (s, 1H), 6.70 (d, J=8.59 Hz, 1H), 5.34 (d, J=9.34 Hz, 1H), 5.13 (s, 2H), 4.04 (m, 1H), 3.78 (s, 3H), 2.84-2.67 (m, 2H), 2.55-2.47 (m, 2H), 1.88-1.82 (m, 2H), 1.44 (s, 9H).

632c) (S)-3-Benzyloxycarbonylamino-5-(2-chloro-5-methoxy-phenyl)-pentanoic acid tert-butyl ester (1870 mg, 4.17 mmol) was dissolved in Acetonitrile (91 mL) to which Iodotrimethylsilane (1.30 mL, 9.14 mmol) was added neat at rt. After 1 hour an additional portion of Iodotrimethylsilane (647 uL, 4.55 mmol) was added. After 2 hours the reaction was concentrated under reduced pressure. Et$_2$O was added to the residue to residue and the resulting mixture was extracted twice with 1 M of Potassium hydroxide in Water (90 mL and 45 mL respectively). The aqueous phases were combined, cooled to 0° C., and treated slowly with acetic anhydride until all intermediate (S)-3-Acetylamino-5-(2-chloro-5-methoxy-phenyl)-pentanoic acid had been converted to (S)-3-Acety-lamino-5-(2-chloro-5-methoxy-phenyl)-pentanoic acid, as monitored by HPLC. Then maintaining the reaction at 0° C., 12 N HCl was added slowly until pH 2.0 was attained. The resulting white solid precipitate was filtered and rinsed fairly liberally with ice cold water. After air drying there remained 940 mg (75%) of white solid (S)-3-Acetylamino-5-(2-chloro-5-methoxy-phenyl)-pentanoic acid, which was used without further purification; TLC: 10:1 $CH_2Cl_2$:MeOH Rf 0.25, homogeneous; MP: 145-148.5° C.; $^1$H NMR (400 MHz, $CDCl_3$) δ 7.23 (d, J=8.73 Hz, 1H), 6.78 (d, J=2.57 Hz, 1H), 6.71 (m, 1H), 6.11 (d, J=8.97 Hz, 1H), 4.33 (m, 1H), 3.80 (s, 3H), 2.85-2.55 (m, 4H), 2.03 (s, 3H), 1.94-1.90 (m, 2H); MS (m/e) 300.03 (M+H).

632d) Under $N_2$, (S)-3-Acetylamino-5-(2-chloro-5-methoxy-phenyl)-pentanoic acid (940 mg, 3.1 mmol) was combined with Polyphosphoric acid (19 g, 170 mmol) and placed into an oil bath warming between 95-100° C. After 80 minutes the reaction was removed from the heat and as cooling was treated with ~120 g of ice with vigorous stirring. The resulting mixture was extracted with EtOAc (2×). The organic extracts were combined, washed with saturated aqueous $NaHCO_3$, dried over $Na_2SO_4$, filtered and concentrated under reduced pressure to yield 700 mg (80%) of yellow tinted solid N—((S)-1-Chloro-4-methoxy-5-oxo-6,7,8,9-tetrahydro-5H-benzocyclohepten-7-yl)-acetamide, which was used without further purification; TLC: 10:1 $CH_2Cl_2$:MeOH Rf 0.35, homogeneous; $^1$H NMR (400 MHz, $CDCl_3$) δ 7.37 (d, J=8.93 Hz, 1H), 6.80 (d, J=8.93 Hz, 1H), 5.58 (d, J=6.63 Hz, 1H), 4.37-4.32 (m, 1H), 3.81 (s, 3H), 3.16-3.01 (m, 2H), 2.85-2.75 (m, 1H), 2.7-2.6 (m, 1H), 2.25-2.15 (m, 1H), 1.98 (s, 3H), 1.8-1.7 (m, 1H).

632f) To an ice cooled solution of N—((S)-1-Chloro-4-methoxy-5-oxo-6,7,8,9-tetrahydro-5H-benzocyclohepten-7-yl)-acetamide (690 mg, 2.4 mmol) in Acetonitrile (15 mL)/Trifluoroacetic anhydride (2.19 mL, 15.5 mmol) was added neat Potassium nitrate (277 mg, 2.74 mmol). After 30 minutes the ice cold reaction mixture was added to stirring, ice cold aqueous $NaHCO_3$ (~125 mL) over 2 minutes. The resulting mixture was extracted with EtOAc (2×). The organic phases were combined, dried over $MgSO_4$, filtered and concentrated to yield 920 mg of a yellow/tannish gum. This material was triturated with ice cold water (~30 mL). On scratching solid slowly formed over ~½ hour. The resulting solid was filtered and rinsed liberally with ice cold water. After air drying there remained 600 mg (75%) of tan solid N—((S)-4-Chloro-1-methoxy-2-nitro-9-oxo-6,7,8,9-tetrahydro-5H-benzocyclo-hepten-7-yl)-acetamide, which was used without further purification; TLC: 5:1 $CH_2Cl_2$:MeOH Rf 0.53 (SM Rf 0.50); $^1$H NMR (400 MHz, $CDCl_3$) δ 8.00 (s, 1H), 5.62 (bs, 1H), 4.37-4.35 (m, 1H), 3.94 (s, 3H), 3.18-3.11 (m, 2H), 2.94-2.91 (m, 1H), 2.76-2.71 (m, 1H), 2.25-2.15 (m, 1H), 2.02 (s, 3H), 1.9-1.8 (m, 1H); MS (m/e) 327.01.

632 g) N—((S)-4-Chloro-1-methoxy-2-nitro-9-oxo-6,7,8,9-tetrahydro-5H-benzocyclohepten-7-yl)-acetamide (100 mg, 0.3 mmol), 20% $Pd(OH)_2$/C (30 mg) and Methanol (20 mL) were placed under a blanket of Hydrogen at atmospheric pressure. After 24 h the reaction mixture was filtered and the filtrate concentrated under reduced pressure to yield 105 mg (100%) of N—((S)-2-Amino-1-methoxy-9-oxo-6,7,8,9-tetrahydro-5H-benzocyclohepten-7-yl)-acetamide; hydrochloride. TLC: 5:1 $CH_2Cl_2$:MeOH Rf 0.5 homogeneous; (SM A: Rf 0.55); $^1$H NMR (400 MHz, DMSO-$d_6$) δ 7.98 (d, J=8.09 Hz, 1H), 7.01 (m, 1H), 6.86 (d, J=8.09 Hz, 1H), 3.95 (m, 1H), 3.66 (s, 3H), 3.5 (bs, water+$NH_2$), 2.79-2.64 (m, 4H), 1.95-1.85 (m, 1H), 1.78 (s, 3H), 1.7-1.6 (m, 1H).

632 h) (1S,2S,3R,4R)-3-(2,5-Dichloro-pyrimidin-4-ylamino)-bicyclo[2.2.1]hept-5-ene-2-carboxylic acid amide was reacted with N—((S)-2-Amino-1-methoxy-9-oxo-6,7,8, 9-tetrahydro-5H-benzocyclohepten-7-yl)-acetamide; hydrochloride, in a similar manner as Example 601b, to yield desired product (1S,2S,3R,4R)-3-[2-((S)-7-Acetylamino-1-methoxy-9-oxo-6,7,8,9-tetrahydro-5H-benzocyclohepten-2-ylamino)-5-chloro-pyrimidin-4-ylamino]-bicyclo[2.2.1] hept-5-ene-2-carboxylic acid amide as a lyophylate (28%); $^1$H NMR (400 MHz, DMSO-$d_6$) δ 9.07 (bs, 1H), 8.83 (bs, 1H), 8.16 (s, 1H), 8.09 (d, J=8.33 Hz, 1H), 8.00 (d, J=7.58 Hz, 1H), 7.93 (s, 1H), 7.38 (s, 1H), 7.08 (d, J=8.34 Hz, 1H), 6.36 (bs, 1H), 6.26 (bs, 1H), 3.98-3.94 (m, 2H), 3.69 (s, 3H), 2.93-2.68 (m, 7H), 2.1-1.9 (m, 2H), 1.80 (s, 3H), 1.75-1.70 (m, 1H), 1.42 (d, J=9.10 Hz, 1H); MS (m/e) 525.15 (M+H).

Example 633

{7-[5-Chloro-4-(4-methoxy-2-pyrazol-1-yl-pheny-lamino)-pyrimidin-2-ylamino]-8-methoxy-1,2,4,5-tetrahydro-benzo[d]azepin-3-yl}-[1,4]dioxan-2-yl-methanone 633a) To a room temperature solution of 1,4-Dioxinane-2-carboxylic acid [264.2 mg, 2.000 mmol (Nelson, B. A. et. al. *J. Am. Chem. Soc.*, 1955, 77, 1695-96)], 7-Methoxy-8-nitro-2,3,4,5-tetrahydro-1H-benzo[d]azepine (444.5 mg, 2 mmol) and 1-Hydroxybenzotriazole (380 mg, 2.8 mmol) in N,N-Dimethylformamide (10 mL) was added neat N-(3-Dimethyl-aminopropyl)-N'-ethylcarbodiimide hydrochloride (518 mg, 2.7 mmol). After 6 hours the reaction mixture was concentrated under reduced pressure. The residue was partitioned between EtOAc and saturated aqueous $NaHCO_3$. The organic phase was then washed sequentially with 2N Citric acid and saturated aqueous $NaHCO_3$ once again. The organic phase was dried over $MgSO_4$, filtered and concentrated under reduced pressure yielding 950 mg of crude oil. The residue was treated with $Et_2O$ (15 mL) yielding a solid, which was filtered and rinsed with a small amount of $Et_2O$. After air drying there remained 513 mg (76%) of off white solid 1,4-Dioxinan-2-yl-(7-methoxy-8-nitro-1,2,4,5-tetrahydro-3-benzazepin-3-yl)-methanone; mp 150-152° C.; MS (m/e) 337.11.

633b) 1,4-Dioxinan-2-yl-(7-methoxy-8-nitro-1,2,4,5-tetrahydro-3-benzazepin-3-yl)-methanone was treated under standard hydrogenation conditions ($H_2$, EtOH, 10% Pd/C) to yield desired 7-Amino-8-methoxy-1,2,4,5-tetrahydro-3-benzazepin-3-yl)-1,4-dioxinan-2-yl-methanone as a crude oil, which was used for the subsequent reaction without further purification; LC/MS (m/e) 307.14 (M+H).

633c) (2,5-Dichloro-pyrimidin-4-yl)-(4-methoxy-2-pyrazol-1-yl-phenyl)-amine, of Example 611c, was reacted with 7-Amino-8-methoxy-1,2,4,5-tetrahydro-3-benzazepin-3-yl)-1,4-dioxinan-2-yl-methanone, in a similar manner as Example 601b, to yield desired product {7-[5-Chloro-4-(4-methoxy-2-pyrazol-1-yl-phenylamino)-pyrimidin-2-ylamino]-8-methoxy-1,2,4,5-tetrahydro-benzo[d]azepin-3-yl}-[1,4]dioxan-2-yl-methanone as a lyophylate (40%); $^1$H NMR (400 MHz, DMSO-$d_6$) δ 10.12 (s, 1H), 8.37 (bs, 1H), 8.18 (s, 2H), 7.83-7.79 (m, 2H), 7.50 (s, 1H), 7.25 (s, 1H), 7.00 (m, 1H), 6.88 (s, 1H), 6.52 (s, 1H), 4.38 (m, 1H), 3.90 (s, 1.5H), 3.87 (s, 1.5H), 3.80 (s, 3H), 3.8-3.3 (bs, H$_2$O+11H), 2.9 (m, 1H), 2.8 (m, 1H), 2.65 (m, 1H); MS (m/e) 606.23 (M+H).

Example 634

2-{5-Chloro-2-[3-([1,4]dioxane-2-carbonyl)-8-methoxy-2,3,4,5-tetrahydro-1H-benzo[d]azepin-7-ylamino]-pyrimidin-4-ylamino}-N,N-dimethyl-benzenesulfonamide 2-(2,5-Dichloro-pyrimidin-4-ylamino)-N,N-dimethylbenzenesulfonamide was reacted with 7-Amino-8-methoxy-1,2,4,5-tetrahydro-3-benzazepin-3-yl)-1,4-dioxinan-2-yl-methanone, in a similar manner as Example 601b, to yield desired product 2-{5-Chloro-2-[3-([1,4]dioxane-2-carbonyl)-8-methoxy-2,3,4,5-tetrahydro-1H-benzo[d]azepin-7-ylamino]-pyrimidin-4-ylamino}-N,N-dimethyl-benzenesulfonamide as a lyophylate (42%); $^1$H NMR (400 MHz, DMSO-d$_6$) δ 9.52 (s, 1H), 8.53 (d, J=12.29 Hz, 1H), 8.33-8.28 (m, 2H), 7.83 (d, 7.83 Hz, 1H), 7.64-7.60 (m, 1H), 7.43 (m, 2H), 6.90 (s, 1H), 4.41 (d, J=7.81 Hz, 1H), 3.8-3.35 (m, 13H), 2.92 (bm, 1H), 2.85-2.69 (m, 2H), 2.64 (s, 6H), 2.57 (m, 1H); MS (m/e) 617.19 (M+H).

Example 635

(1S,2S,3R,4R)-3-{5-Chloro-2-[3-([1,4]dioxane-2-carbonyl)-8-methoxy-2,3,4,5-tetrahydro-1H-benzo[d]azepin-7-ylamino]-pyrimidin-4-ylamino}-bicyclo[2.2.1]hept-5-ene-2-carboxylic acid amide (1S,2S,3R,4R)-3-(2,5-Dichloro-pyrimidin-4-ylamino)-bicyclo[2.2.1]hept-5-ene-2-carboxylic acid amide was reacted with 7-Amino-8-methoxy-1,2,4,5-tetrahydro-3-benzazepin-3-yl)-1,4-dioxinan-2-yl-methanone, in a similar manner as Example 601b, to yield desired product (1S,2S,3R,4R)-3-{5-Chloro-2-[3-([1,4]dioxane-2-carbonyl)-8-methoxy-2,3,4,5-tetrahydro-1H-benzo[d]azepin-7-ylamino]-pyrimidin-4-ylamino}-bicyclo[2.2.1]hept-5-ene-2-carboxylic acid amide as a lyophylate (31%); $^1$H NMR (400 MHz, DMSO-d$_6$) δ 9.21 (bs, 1H), 9.0 (bs, 1H), 8.13 (d, J=5.89 Hz, 1H), 7.92 (s, 1H), 7.70-7.60 (bd, 1H), 7.39 (s, 1H), 6.97 (s, 1H), 6.38 (bs, 1H), 6.12 (bs, 1H), 4.40 (m, 1H), 4.02 (m, 1H), 3.82 (s, 3H), 3.8-3.4 (bs, H$_2$O+10H), 2.96-2.65 (m, 6H), 2.62 (m, 1H), 2.01 (d, J=8.95 Hz, 1H), 1.41 (d, J=9.45 Hz, 1H); MS (m/e) 569.21 (M+H).

Example 636

5-Chloro-N*2*-(3-[1,4]dioxan-2-ylmethyl-8-methoxy-2,3,4,5-tetrahydro-1H-benzo[d]azepin-7-yl)-N*4*-(4-methoxy-2-pyrazol-1-yl-phenyl)-pyrimidine-2,4-diamine 636$^a$) 1,4-Dioxinan-2-yl-(7-methoxy-8-nitro-1,2,4,5-tetrahydro-3-benzazepin-3-yl)-methanone (315 mg, 0.936 mmol) was added neat slowly over 2 minutes to a 0° C. solution of 1 M of Borane-THF complex in Tetrahydrofuran (4.75 mL). Upon completion of addition the ice bath was removed and the reaction was warmed to 65° C. under an inert atmosphere. After 4 hours the reaction was re-cooled and treated slowly with 1N HCl (5 mL). The reaction was then re-heated to 65° C. for 1.5 hours. The reaction mixture was then again cooled to 0° C., then treated with 1N KOH until basic. The resulting solution was extracted 3× with Et$_2$O. The organics were combined, dried over Na$_2$SO$_4$, filtered and concentrated under reduced pressure to give 300 mg (100%) of a clear oil 3-1,4-Dioxinan-2-ylmethyl-7-methoxy-8-nitro-2,3,4,5-tetrahydro-1H-3-benzazepine; MS (m/e) 323.13 (M+H).

636b) 3-1,4-Dioxinan-2-ylmethyl-7-methoxy-8-nitro-2,3,4,5-tetrahydro-1H-3-benzazepine was treated under standard hydrogenation conditions (H$_2$, EtOH, 10% Pd/C) to yield desired 3-1,4-Dioxinan-2-ylmethyl-8-methoxy-2,3,4,5-tetrahydro-1H-3-benzazepin-7-ylamine as a crude oil, which was used for the subsequent reaction without further purification; LC/MS (m/e) 293.15 (M+H).

636c) (2,5-Dichloro-pyrimidin-4-yl)-(4-methoxy-2-pyrazol-1-yl-phenyl)-amine, of Example 611c, was reacted with 3-1,4-Dioxinan-2-ylmethyl-8-methoxy-2,3,4,5-tetra hydro-1H-3-benzazepin-7-ylamine, in a similar manner as Example 601b, to yield desired product 3-1,4-Dioxinan-2-ylmethyl-8-methoxy-2,3,4,5-tetrahydro-1H-3-benzazepin-7-ylamine as a lyophylate (40%); $^1$H NMR (400 MHz, DMSO-d$_6$) δ 9.91 (s, 2H), 8.20 (s, 1H), 8.13 (s, 1H), 8.09 (s, 1H), 7.87 (d, J=9.01 Hz, 1H), 7.80 (s, 1H), 7.59 (s, 1H), 7.24 (s, 1H), 6.99 (bs, 1H), 6.93 (s, 1H), 6.52 (s, 1H), 4.06 (m, 1H), 3.88 (s, 3H), 3.80 (s, 3H), 3.7-3.4 (H$_2$O+6H), 3.3-2.9 (m, 9H), 2.67 (m, 1H); MS (m/e) 592.24 (M+H).

Example 637

2-[5-Chloro-2-(3-[1,4]dioxan-2-ylmethyl-8-methoxy-2,3,4,5-tetrahydro-1H-benzo[d]azepin-7-ylamino)-pyrimidin-4-ylamino]-N,N-dimethyl-benzenesulfonamide 2-(2,5-Dichloro-pyrimidin-4-ylamino)-N,N-dimethylbenzenesulfonamide was reacted with 3-1,4-Dioxinan-2-ylmethyl-8-methoxy-2,3,4,5-tetrahydro-1H-3-benzazepin-7-ylamine, in a similar manner as Example 601b, to yield desired product 2-[5-Chloro-2-(3-[1,4]dioxan-2-ylmethyl-8-methoxy-2,3,4,5-tetrahydro-1H-benzo[d]azepin-7-ylamino)-pyrimidin-4-ylamino]-N,N-dimethyl-benzenesulfonamide as a lyophylate (18%); $^1$H NMR (400 MHz, DMSO-d$_6$) δ 9.82 (s, 1H), 9.35 (s, 1H), 8.45 (s, 1H), 8.32 (s, 1H), 8.25 (s, 1H), 7.82 (d, J=7.94 Hz, 1H), 7.61 (m, 1H), 7.55 (s, 1H), 7.36 (m, 1H), 6.96 (s, 1H), 4.03 (m, 1H), 3.83 (s, 3H), 3.7-3.51 (bm H2O+6H), 3.27-3.03 (m, 9H), 2.75 (m, 1H), 2.65 (s, 6H); MS (m/e) 603.20 (M+H).

Example 638

2-{5-Chloro-2-[3-([1,4]dioxane-2-carbonyl)-2,3,4,5-tetrahydro-1H-benzo[d]azepin-7-ylamino]-pyrimidin-4-ylamino}-N,N-dimethyl-benzenesulfonamide (7-Amino-1,2,4,5-tetrahydro-3-benzazepin-3-yl)-1,4-dioxinan-2-yl-methanone, prepared in a similar manner as 7-Amino-8-methoxy-1,2,4,5-tetrahydro-3-benzazepin-3-yl)-1,4-dioxinan-2-yl-methanone of Example 633b, was reacted with 2-(2,5-Dichloro-pyrimidin-4-ylamino)-N,N-dimethyl-benzenesulfonamide, in a similar manner as Example 601b, to yield desired product 2-{5-Chloro-2-[3-([1,4]dioxane-2-carbonyl)-2,3,4,5-tetrahydro-1H-benzo[d]azepin-7-ylamino]-pyrimidin-4-ylamino}-N,N-dimethyl-benzenesulfonamide as a lyophylate (25%); $^1$H NMR (400 MHz, DMSO-d$_6$) δ 9.53 (s, 1H), 9.33 (s, 1H), 8.49 (bs, 1H), 8.29 (s, 1H), 7.84 (d, J=7.97 Hz, 1H), 7.71 (m, 1H), 7.41-7.32 (m, 3H), 7.07-7.01 (m, 1H), 4.39 (m, 1H), 3.78-3.49 (m, 10H), 2.87-2.77 (m, 2H), 2.65 (s, 6H); MS (m/e) 587.15 (M+H).

Example 639

2-{5-Chloro-2-[3-([1,4]dioxane-2-carbonyl)-2,3,4,5-tetrahydro-1H-benzo[d]azepin-7-ylamino]-pyrimidin-4-ylamino}-3-fluoro-N-methyl-benzamide (7-Amino-1,2,4,5-tetrahydro-3-benzazepin-3-yl)-1,4-dioxinan-2-yl-methanone, prepared in a similar manner as 7-Amino-8-methoxy-1,2,4,5-tetrahydro-3-benzazepin-3-yl)-1,4-dioxinan-2-yl-methanone of Example 633b, was reacted with 2-(2,5-Dichloro-pyrimidin-4-ylamino)-3-fluoro-N-methyl-benzamide, in a similar manner as Example 601b, to yield desired product 2-{5-Chloro-2-[3-([1,4]dioxane-2-carbonyl)-2,3,4,5-tetrahydro-1H-benzo[d]azepin-7-ylamino]-pyrimidin-4-ylamino}-3-fluoro-N-methyl-benzamide as a lyophylate (31%); $^1$H NMR (400 MHz, DMSO-$d_6$) δ 9.39 (d, J=9.23 Hz, 1H), 9.33 (s, 1H), 8.55 (m, 1H), 8.18 (s, 1H), 7.51-7.43 (m, 3H), 7.26 (s, 1H), 7.17 (m, 1H), 6.89 (m, 1H), 4.39 (m, 1H), 3.74-3.4 (bm, $H_2O$+11H), 2.81 (m, 1H), 2.74 (d, J=4.55 Hz, 3H), 2.67 (m, 2H); MS (m/e) 555.14 (M+H).

Example 640

2-{5-Chloro-2-[3-([1,4]dioxane-2-carbonyl)-2,3,4,5-tetrahydro-1H-benzo[d]azepin-7-ylamino]-pyrimidin-4-ylamino}-3-fluoro-N-prop-2-ynyl-benzamide (7-Amino-1,2,4,5-tetrahydro-3-benzazepin-3-yl)-1,4-dioxinan-2-yl-methanone, prepared in a similar manner as 7-Amino-8-methoxy-1,2,4,5-tetrahydro-3-benzazepin-3-yl)-1,4-dioxinan-2-yl-methanone of Example 633b, was reacted with 2-(2,5-Dichloro-pyrimidin-4-ylamino)-3-fluoro-N-prop-2-ynyl-benzamide, in a similar manner as Example 601b, to yield desired product 2-{5-Chloro-2-[3-([1,4]dioxane-2-carbonyl)-2,3,4,5-tetrahydro-1H-benzo[d]azepin-7-ylamino]-pyrimidin-4-ylamino}-3-fluoro-N-prop-2-ynyl-benzamide as a lyophylate (18%); $^1$H NMR (400 MHz, DMSO-$d_6$) δ 9.30 (s, 1H), 9.19 (d, J=8.44 Hz, 1H), 8.97 (m, 1H), 8.17 (s, 1H), 7.52-7.45 (m, 3H), 7.25 (s, 1H), 7.15 (m, 1H), 6.87 (m, 1H), 4.38 (m, 1H), 4.01 (m, 2H), 3.84-3.3 (bm, $H_2O$+11H), 3.11 (s, 1H), 2.81 (m, 1H), 2.67 (m, 2H); MS (m/e) 579.16 (M+H).

Example 641

2-[5-Chloro-2-(3-[1,4]dioxan-2-ylmethyl-2,3,4,5-tetrahydro-1H-benzo[d]azepin-7-ylamino)-pyrimidin-4-ylamino]-N,N-dimethyl-benzenesulfonamide 3-1,4-Dioxinan-2-ylmethyl-2,3,4,5-tetrahydro-1H-3-benzazepin-7-ylamine, prepared in a similar manner as 3-1,4-Dioxinan-2-ylmethyl-8-methoxy-2,3,4,5-tetrahydro-1H-3-benzazepin-7-ylamine of Example 636b, was reacted with 2-(2,5-Dichloro-pyrimidin-4-ylamino)-N,N-dimethyl-benzenesulfonamide, in a similar manner as Example 601b, to yield desired product 2-[5-Chloro-2-(3-[1,4]dioxan-2-ylmethyl-2,3,4,5-tetrahydro-1H-benzo[d]azepin-7-ylamino)-pyrimidin-4-ylamino]-N,N-dimethyl-benzenesulfonamide as a lyophylate (38%); $^1$H NMR (400 MHz, DMSO-$d_6$) δ 9.82 (bs, 1H), 9.56 (s, 1H), 9.29 (s, 1H), 8.51 (bs, 1H), 8.29 (s, 1H), 7.84 (d, J=8.08 Hz, 1H), 7.71 (m, 1H), 7.46-7.37 (m, 3H), 7.08 (d, J=6.57 Hz, 1H), 4.07 (m, 1H), 3.82-3.60 (m, 6H), 3.48 (bs, 2H), 3.3-2.9 (m, 9H), 2.75 (m, 1H), 2.65 (s, 6H); MS (m/e) 573.16 (M+H).

Example 642

5-Chloro-N*2*-(3-[1,4]dioxan-2-ylmethyl-2,3,4,5-tetrahydro-1H-benzo[d]azepin-7-yl)-N*4*-(4-methoxy-2-pyrazol-1-yl-phenyl)-pyrimidine-2,4-diamine 3-1,4-Dioxinan-2-ylmethyl-2,3,4,5-tetrahydro-1H-3-benzazepin-7-ylamine, prepared in a similar manner as 3-1,4-Dioxinan-2-ylmethyl-8-methoxy-2,3,4,5-tetrahydro-1H-3-benzazepin-7-ylamine of Example 636b, was reacted with (2,5-Dichloro-pyrimidin-4-yl)-(4-methoxy-2-pyrazol-1-yl-phenyl)-amine, of Example 611c, in a similar manner as Example 601b to yield desired product 5-Chloro-N*2*-(3-[1,4]dioxan-2-ylmethyl-2,3,4,5-tetrahydro-1H-benzo[d]azepin-7-yl)-N*4*-(4-methoxy-2-pyrazol-1-yl-phenyl)-pyrimidine-2,4-diamine as a lyophylate (38%); $^1$H NMR (400 MHz, DMSO-$d_6$) δ 9.73 (bs, 1H), 9.36 (s, 1H), 8.24 (s, 1H), 8.10 (s, 1H), 7.96 (bd, 1H), 7.81 (s, 1H), 7.43 (s, 1H), 7.30-7.25 (m, 2H), 7.02-7.00 (m, 2H), 6.54 (s, 1H), 4.06 (m, 1H), 3.88 (s, 3H), 3.85-3.55 (m, 6H), 3.4-3.0 (m, 6H), 2.95 (m, 1H), 2.75 (m, 1H), MS (m/e) 562.15 (M+H).

Example 651

2-{5-Chloro-2-[7-(2,2,2-trifluoro-ethylamino)-6,7,8,9-tetrahydro-5H-benzocyclohepten-2-ylamino]-pyrimidin-4-ylamino}-N-methyl-benzamide 651a) Charge 2-nitro-5,6,8,9-tetrahydrobenzocyclohepten-7-one (750.00 mg, 3.66 mmol) to methylene chloride (20 mL, 300 mmol) and acetic acid (200 uL, 4 mmol). Allow to stir for 5 min. Charge 2,2,2-trifluorethylamine (0.292 ml, 3.65 mmol) and sodium triacetoxyborohydride (1.55 g, 7.31 mmol). Allow suspension to stir for 2.5 hours. HPLC at 2.5 hours conforms that starting ketone has been consumed. Pour reaction into 200 ml water and 100 ml saturated sodium bicarbonate solution and extract with 2×100 ml portions of methylene chloride. The combined organic was dried over magnesium sulfate, filtered and evaporated to a yellow oil (approximately 1.0 g). The resulting crude yellow oil was chromatographed on a 80 g Isco cartridge using a gradient of 0-35% yield EtOAc in hexanes as the eluent. 2-Nitro-6,7,8,9-tetrahydro-5H-benzocyclohepten-7-yl)-(2,2,2-trifluoro-ethyl)-amine was isolated as a beige oil (821 mg, 78% yield). $^1$H-NMR (CDCl$_3$) δ 7.95 (d, J=8.2 Hz, 2H), 7.25 (d, J=11.3 Hz, 2H), 3.24 (q, J=18.7, 9.4 Hz, 2H), 3.01 (m, 3H), 2.74 (m, 2H), 2.07 (m, 2H), 1.38 (m, 2H), LC/MS (ESI+)=288 (M+H).

651b) 2-Nitro-6,7,8,9-tetrahydro-5H-benzocyclohepten-7-yl)-(2,2,2-trifluoro-ethyl)-amine (821 mg, 2.83 mmol) was charged to 30 ml methanol and 400-800 mg 10% palladium on carbon was added. The suspension was hydrogenated at 30 psi hydrogen for 2.5 hours and followed by NMR. The reaction was filtered through a ¼" pad of celite and the pad washed with 4×10 ml portions of methanol. The resulting solution was clarified through a 45 micron frit to yield a yellow solution that was evaporated to yield N*7*-(2,2,2-trifluoro-ethyl)-6,7,8,9-tetrahydro-5H-benzocycloheptene-2,7-diamine (637 mg, 87% yield) as a white solid. $^1$H-NMR (CDCl$_3$) δ 6.88 (d, J=7.8 Hz, 1H), 6.48 (s, 1H), 6.44 (d, J=7.8 Hz, 1H), 3.22 (q, J=18.0, 8.7 Hz, 3H), 2.84 (m, 2H), 2.71 (m, 2H), 2.62 (m, 2H), 2.03 (m, 2H), 1.29 (m, 2H)

651c) 2-(2,5-Dichloro-pyrimidin-4-ylamino)-N-methyl-benzamide (86.3 mg, 0.290 mmol) and N*7*-(2,2,2-trifluoro-ethyl)-6,7,8,9-tetrahydro-5H-benzocycloheptene-2,7-diamine (75 mg, 0.290 mmol) were combined with DL-10-camphorsulfonic acid (101 mg, 0.436 mmol) in 2 ml IPA and heated in a microwave vial for 40 minutes at 120° C. for 40 minutes. The resulting reaction was poured into 25 ml saturated sodium bicarbonate solution and 50 ml water and extracted with 4×25 ml portions of methylene chloride. The combined organic was dried over magnesium sulfate, filtered and evaporated. The crude product was purified via reverse phase preparative chromatography (Luna C18, 5 μm, 100 mm×21.2 mm column) using a gradient of 0-35% MeCN in water (both containing 0.1% TFA). 2-{5-Chloro-2-[7-(2,2,2-trifluoro-ethylamino)-6,7,8,9-tetrahydro-5H-benzocyclohepten-2-ylamino]-pyrimidin-4-ylamino}-N-methyl-benzamide (11.18 mg, 7.4% yield) was isolated as an off white solid. $^1$H-NMR (CDCl$_3$) δ 11.07 (s, 1H), 8.66 (d, J=8.44 Hz, 1H), 7.45 (m, 2H), 7.35 (s, 1H), 7.04 (m, 2H), 6.91 (s, 1H), 6.18 (s, 1H), 3.24 (q, J=19.4, 9.8 Hz, 2H), 3.03 (d, J=4.8 Hz, 3H), 2.87 (m, 3H), 2.66 (m, 2H), 2.06 (m, 2H), 1.32 (m, 5H). LC/MS (ESI+)=519 (M+H). MP=202-203° C.

Example 652

5-Chloro-N*4*-(2-ethyl-4-morpholin-4-yl-phenyl)-N*2*-[7-(2,2,2-trifluoro-ethylamino)-6,7,8,9-tetrahydro-5H-benzocyclohepten-2-yl]-pyrimidine-2,4-diamine In an analogous procedure to Example 651, part c, N*7*-(2,2,2-Trifluoro-ethyl)-6,7,8,9-tetrahydro-5H-benzocycloheptene-2,7-diamine (75 mg, 0.290 mmol) was combined with DL-10-camphorsulfonic acid (101 mg, 0.436 mmol) and (2,5-Dichloro-pyrimidin-4-yl)-(2-methoxy-4-morpholin-4-yl-phenyl)-amine (103 mg, 0.290 mmol) to prepare 5-Chloro-N*4*-(2-ethyl-4-morpholin-4-yl-phenyl)-N*2*-[7-(2,2,2-trifluoro-ethylamino)-6,7,8,9-tetrahydro-5H-benzocyclohepten-2-yl]-pyrimidine-2,4-diamine (13.82 mg, 8.4% yield) as a yellow TFA salt. $^1$H-NMR (CDCl$_3$) δ 8.24 (dd, J=26.9, 8.81 Hz, 1H), 8.00 (m, 1H), 7.87 (br s, 1H), 7.47 (m, 1H), 6.95 (m, 1H), 6.53 (m, 3H), 3.89 (m, 7H), 3.16 (m, 4H), 2.84 (m, 2H), 2.69 (m, 2H), 2.04 (m, 2H), 1.29 (m, 2H). LC/MS (ESI+)=571 (M+H). MP=155° C.

Example 653

(1R,2R)-2-{5-Chloro-2-[7-(2,2,2-trifluoro-ethylamino)-6,7,8,9-tetrahydro-5H-benzocyclohepten-2-ylamino]-pyrimidin-4-ylamino-cyclohexanecarboxylic acid amide In an analogous procedure to Example 651, part c, N*7*-(2,2,2-Trifluoro-ethyl)-6,7,8,9-tetrahydro-5H-benzocycloheptene-2,7-diamine (75 mg, 0.290 mmol) was combined with DL-10-camphorsulfonic acid (101 mg, 0.436 mmol) and (1R,2R)-2-(2,5-Dichloro-pyrimidin-4-ylamino)-cyclohexanecarboxylic acid amide (87.4 mg, 0.290 mmol) to prepare (1R,2R)-2-{5-Chloro-2-[7-(2,2,2-trifluoro-ethylamino)-6,7,8,9-tetrahydro-5H-benzocyclohepten-2-ylamino]-pyrimidin-4-ylamino-cyclohexanecarboxylic acid amide (56.45 mg, 37% yield) as a white powder. $^1$H-NMR (CDCl$_3$) δ 7.85 (s, 1H), 7.42 (d, J=7.4 Hz, 1H), 7.03 (d, J=7.8 Hz, 1H), 6.80 (m, 2H), 5.48 (br s, 1H), 5.24 (br s, 1H), 4.37 (m, 1H), 3.24 (m, 2H), 2.82 (m, 3H), 2.67 (m, 2H), 2.53 (m, 2H), 2.35 (br s, 1H), 2.09 (m, 3H), 1.30 (m, 10H). LC/MS (ESI+)=523 (M+H). MP=242-243° C.

Example 654

(1S,2R,3S,4R)-3-{5-Chloro-2-[7-(2,2,2-trifluoro-ethylamino)-6,7,8,9-tetrahydro-5H-benzocyclohepten-2-ylamino]-pyrimidin-4-ylamino}-bicyclo[2.2.1]heptane-2-carboxylic acid amide In an analogous procedure to Example 651, part c, N*7*-(2,2,2-Trifluoro-ethyl)-6,7,8,9-tetrahydro-5H-benzocycloheptene-2,7-diamine (75 mg, 0.290 mmol) was combined with DL-10-camphorsulfonic acid (101 mg, 0.436 mmol) and (1S,2R,3S,4R)-3-(2,5-Dichloro-pyrimidin-4-ylamino)-bicyclo[2.2.1]heptane-2-carboxylic acid amide (86.9 mg, 0.290 mmol) to prepare (1S,2R,3S,4R)-3-{5-Chloro-2-[7-(2,2,2-trifluoro-ethylamino)-6,7,8,9-tetrahydro-5H-benzocyclohepten-2-ylamino]-pyrimidin-4-ylamino}-bicyclo[2.2.1]heptane-2-carboxylic acid amide (45.07 mg, 30% yield) as a white powder. Product was purified on a 12 g Isco cartridge using methelene chloride/methanol as the eluent. $^1$H-NMR (CDCl$_3$) δ 7.86 (s, 1H), 7.40 (d, J=8.2 Hz, 1H), 7.28 (s, 1H), 7.03 (d, J=8.1 Hz, 1H), 6.84 (m, 2H), 6.33 (m, 2H), 5.54 (br s, 1H), 5.32 (br s, 1H), 4.36 (t, J=7.8 Hz, 1H), 3.24 (q, J=18.9, 9.5 Hz, 2H), 3.06 (s, 1 h), 2.80 (m, 4H), 2.68 (m, 2H), 2.47 (d, J=8.5 Hz, 1H), 2.22 (d, J=9.5 Hz, 1H), 2.08 (m, 2H), 1.64 (m, 1H), 1.34 (m, 2H), 0.88 (m, 1H). LC/MS (ESI+)=521 (M+H). MP=217.5-218.5° C.

Example 655

5-Chloro-N*4*-[2-(1-methyl-1H-imidazol-2-yl)-phenyl]-N*2*-[7-(2,2,2-trifluoro-ethylamino)-6,7,8,9-tetrahydro-5H-benzocyclohepten-2-yl]-pyrimidine-2,4-diamine In an analogous procedure to Example 651, part c, N*7*-(2,2,2-Trifluoro-ethyl)-6,7,8,9-tetrahydro-5H-benzocycloheptene-2,7-diamine (75 mg, 0.290 mmol) was combined with DL-10-camphorsulfonic acid (101 mg, 0.436 mmol) and (2,5-Dichloro-pyrimidin-4-yl)-[2-(1-methyl-1H-imidazol-2-yl)-phenyl]-amine (93 mg, 0.290 mmol) to yield -Chloro-N*4*-[2-(1-methyl-1H-imidazol-2-yl)-phenyl]-N*2*-[7-(2,2,2-trifluoro-ethylamino)-6,7,8,9-tetrahydro-5H-benzocyclohepten-2-yl]-pyrimidine-2,4-diamine (52.73 mg, 47% yield) as a white powder. $^1$H-NMR (CDCl$_3$) δ 10.71 (s, 1H), 8.56 (d, J=8.7 Hz, 1H), 8.01 (s, 1H), 7.41 (m, 2H), 7.39 (s, 1H), 7.23 (m, 1H), 7.18 (m, 1H), 7.02 (m, 3H), 3.76 (s, 3H), 3.24 (q, J=9.4, 18.8 Hz, 2H), 2.82 (m, 3H), 2.68 (m, 2H), 2.05 (m, 2H), 1.31 (m, 2H). MP=154-156° C.

Example 656

N-((1R,2R)-2-{5-Chloro-2-[7-(2,2,2-trifluoro-ethylamino)-6,7,8,9-tetrahydro-5H-benzocyclohepten-2-ylamino]-pyrimidin-4-ylamino}-cyclohexyl)-methanesulfonamide In an analogous procedure to Example 651, part c, N*7*-(2,2,2-Trifluoro-ethyl)-6,7,8,9-tetrahydro-5H-benzocycloheptene-2,7-diamine) was combined with N-[(1R,2R)-2-(2,5-Dichloro-pyrimidin-4-ylamino)-cyclohexyl]-methanesulfonamide to yield N-((1R,2R)-2-{5-Chloro-2-[7-(2,2,2-trifluoro-ethylamino)-6,7,8,9-tetrahydro-5H-benzocyclohepten-2-ylamino]-pyrimidin-4-ylamino}-cyclohexyl)-methanesulfonamide (117 mg, 72% yield) as a white powder. $^1$H-NMR (CDCl$_3$) δ 7.91 (s, 1H), 7.24 (m, 2H), 7.05 (d, J=8.0 Hz, 1H), 6.84 (br s, 1H), 5.37 (m, 1H), 3.87 (m, 1H), 3.23 (q, J=18.6, 9.2 Hz, 3H), 2.83 (m, 6H), 2.69 (m, 2H), 2.20 (br s, 2H), 2.07 (br s, 2H), 1.82 (br s, 2H), 1.35 (br s, 6H). LC/MS (ESI+)=561 (M+H). MP=122° C. dec.

Example 657

5-Chloro-N*4*-[2-(3-methyl-pyridin-2-yl)-phenyl]-N*2*-[7-(2,2,2-trifluoro-ethylamino)-6,7,8,9-tetrahydro-5H-benzocyclohepten-2-yl]-pyrimidine-2,4-diamine In an analogous procedure to Example 651, part c, N*7*-(2,2,2-Trifluoro-ethyl)-6,7,8,9-tetrahydro-5H-benzocycloheptene-2,7-diamine) was combined with (2,5-Dichloro-pyrimidin-4-yl)-[2-(3-methyl-pyridin-2-yl)-phenyl]-amine to yield 5-Chloro-N*4*-[2-(3-methyl-pyridin-2-yl)-phenyl]-N*2*-[7-(2,2,2-trifluoro-ethylamino)-6,7,8,9-tetrahydro-5H-benzocyclohepten-2-yl]-pyrimidine-2,4-diamine (93.00 mg, 58% yield) as an off white powder. ¹H-NMR (CDCl₃) δ 9.45 (s, 1H), 8.58 (d, J=4.8 Hz, 1H), 8.39 (d, J=8.2 Hz, 1H), 7.95 (s, 1H), 7.68 (d, J=7.8 Hz, 1H), 7.38 (m, 3H), 7.24 (m, 2H), 7.02 (d, J=8.0 Hz, 1H) 6.87 (m, 1H), 3.24 (m, 7H), 2.34 (s, 3H), 1.31 (m, 3H). LC/MS (ESI+)=553 (M+H). MP=130.5° C.

Example 658

5-Chloro-N*4*-(2-methoxy-phenyl)-N*2*-[7-(2,2,2-trifluoro-ethylamino)-6,7,8,9-tetrahydro-5H-benzocyclohepten-2-yl]-pyrimidine-2,4-diamine In an analogous procedure to Example 651, part c, N*7*-(2,2,2-Trifluoro-ethyl)-6,7,8,9-tetrahydro-5H-benzocycloheptene-2,7-diamine) was combined with (2,5-Dichloro-pyrimidin-4-yl)-(2-methoxy-phenyl)-amine to yield 5-Chloro-N*4*-(2-methoxy-phenyl)-N*2*-[7-(2,2,2-trifluoro-ethylamino)-6,7,8,9-tetrahydro-5H-benzocyclohepten-2-yl]-pyrimidine-2,4-diamine (34.40 mg, 23% yield) as a white powder. ¹H-NMR (CDCl₃) δ 8.44 (d, J=7.8 Hz, 1H), 8.04 (s, 1H), 7.85 (s, 1H), 7.37 (s, 1H), 7.23 (m, 1H), 7.05 (m, 2H), 6.92 (m, 3H), 3.94 (s, 3H), 3.24 (q, J=18.8, 9.4 Hz, 2H), 2.83 (m, 3H), 2.67 (m, 2H), 2.07 (m, 2H), 1.33 (m, 2H). LC/MS (ESI+)=492 (M+H). MP=182-183.5° C.

Example 659

5-Chloro-N*2*-[7-(2,2-difluoro-ethylamino)-6,7,8,9-tetrahydro-5H-benzocyclohepten-2-yl]-N*4*-(2-methoxy-4-morpholin-4-yl-phenyl)-pyrimidine-2,4-diamine 659a) Charge 2-Nitro-5,6,8,9-tetrahydrobenzocyclohepten-7-one (750.00 mg, 3.6548 mmol) to Methylene chloride (20 mL, 300 mmol) and Acetic acid (200 uL, 4 mmol). Allow to stir for 5 min. Charge 2,2-difluorethylamine (0.292 ml, 3.65 mmol) and sodium triacetoxyborohydride (1.55 g, 7.31 mmol). Allow suspension to stir for 2.5 hours. LC at 2.5 hours conforms that starting ketone has been consumed. Pour reaction into 200 ml water and 100 ml saturated sodium bicarbonate solution and extract with 2×100 ml portions of methylene chloride. The combined organic was dried over magnesium sulfate, filtered and evaporated to a yellow oil (approximately 1.0 g). The resulting crude yellow oil was chromatographed on a 12 g Isco cartridge using a gradient of 0-60% EtOAc in hexanes as the eluent. (2,2-Difluoro-ethyl)-(2-nitro-6,7,8,9-tetrahydro-5H-benzocyclohepten-7-yl)-amine was isolated as a beige oil (625 mg, 63% yield). ¹H-NMR (CDCl₃) δ 7.98 (m, 2H), 7.24 (m, 1H), 5.82 (m, 1H), 3.02 (m, 4H), 2.88 (m, 1H), 2.76 (m, 2H), 2.08 (m, 2H), 1.38 (m, 2H). LC/MS (ESI+): 271 (M+H).

659b) (2,2-Difluoro-ethyl)-(2-nitro-6,7,8,9-tetrahydro-5H-benzocyclohepten-7-yl)-amine (625 mg, 2.31 mmol) was charged to 30 ml methanol and 200-400 mg 10% palladium on carbon was added. The suspension was hydrogenated at 30 psi hydrogen for 2.5 hours and followed by NMR. The reaction was filtered through a ¼" pad of celite and the pad washed with 4×10 ml portions of methanol. The resulting solution was clarified through a 45 micron frit to yield a yellow solution that was evaporated to yield N*7*-(2,2-Difluoro-ethyl)-6,7,8,9-tetrahydro-5H-benzocycloheptene-2,7-diamine (492 mg, 89% yield) as a white solid. ¹H-NMR (CDCl₃) δ 6.88 (m, 1H), 6.44 (m, 2H), 5.82 (m, 1H), 3.00 (m, 2H), 2.66 (m, 5H), 2.04 (m, 2H), 1.27 (m, 2H). LC/MS (ESI+)=241 (M+H).

659c) In an analogous procedure to Example 651, part c, N*7*-(2,2-Difluoro-ethyl)-6,7,8,9-tetrahydro-5H-benzocycloheptene-2,7-diamine was combined with (2,5-Dichloro-pyrimidin-4-yl)-(2-methoxy-4-morpholin-4-yl-phenyl)-amine to yield 5-Chloro-N*2*-[7-(2,2-difluoro-ethylamino)-6,7,8,9-tetrahydro-5H-benzocyclohepten-2-yl]-N*4*-(2-methoxy-4-morpholin-4-yl-phenyl)-pyrimidine-2,4-diamine (72.79 mg, 63% yield) as a white powder. ¹H-NMR (CDCl₃) δ 8.24 (d, J=8.81 Hz, 1H), 8.00 (s, 1H), 7.58 (s, 1H), 7.34 (s, 1H), 7.24 (m, 2H), 7.03 (d, J=8.16 Hz, 1H), 6.84 (s, 1H), 6.54 (s, 1H), 6.49 (d, J=9.0 Hz, 1H), 5.83 (m, 1H), 3.90 (m, 7H), 3.15 (m, 4H), 3.00 (m, 2H), 2.80 (m, 3H), 2.67 (m, 2H), 2.07 (m, 2H), 1.32 (m, 2H). LC/MS (ESI+)=559 (M+H). MP=181-183° C.

Example 660

2-{5-Chloro-2-[7-(2,2-difluoro-ethylamino)-6,7,8,9-tetrahydro-5H-benzocyclohepten-2-ylamino]-pyrimidin-4-ylamino}-N-methyl-benzamide In an analogous procedure to Example 651, part c, N*7*-(2,2-Difluoro-ethyl)-6,7,8,9-tetrahydro-5H-benzocycloheptene-2,7-diamine was combined with 2-(2,5-Dichloro-pyrimidin-4-ylamino)-N-methyl-benzamide to yield 2-{5-Chloro-2-[7-(2,2-difluoro-ethylamino)-6,7,8,9-tetrahydro-5H-benzocyclohepten-2-ylamino]-pyrimidin-4-ylamino}-N-methyl-benzamide (51.78 mg, 50% yield) as a white powder. ¹H-NMR (CDCl₃) δ 11.05 (s, 1H), 8.66 (d, J=8.4 Hz, 1H), 8.08 (s, 1H), 7.47 (m, 2H), 7.34 (s, 1H), 7.25 (s, 1H), 7.04 (m, 2H), 6.89 (s, 1H), 6.15 (br s, 1H), 5.84 (s, 1H), 3.03 (m, 6H), 2.80 (m, 3H), 2.67 (m, 3H), 2.04 (m, 2H), 1.31 (m, 2H). LC/MS (ESI+)=501 (M+H). MP=182-183° C.

Example 661

5-Chloro-N*2*-[7-(2,2-difluoro-ethylamino)-6,7,8,9-tetrahydro-5H-benzocyclohepten-2-yl]-N*4*-[2-(1-methyl-1H-imidazol-2-yl)-phenyl]-pyrimidine-2,4-diamine In an analogous procedure to Example 651, part c, N*7*-(2,2-Difluoro-ethyl)-6,7,8,9-tetrahydro-5H-benzocycloheptene-2,7-diamine was combined with (2,5-Dichloro-pyrimidin-4-yl)-[2-(1-methyl-1H-imidazol-2-yl)-phenyl]-amine to yield 5-Chloro-N*2*-[7-(2,2-difluoro-ethylamino)-6,7,8,9-tetrahydro-5H-benzocyclohepten-2-yl]-N*4*-[2-(1-methyl-1H-imidazol-2-yl)-phenyl]-pyrimidine-2,4-diamine (31.64 mg, 29% yield) as a beige foam. ¹H-NMR (CDCl₃) δ 10.68 (s, 1 h), 8.58 (d, J=8.68 Hz, 1H), 8.01 (s, 1H), 7.35 (m. 2H), 7.33 (s, 1H), 7.28 (m, 1H), 7.23 (m, 1H), 7.00 (m, 2H), 6.90 (s, 1H), 5.85 (m, 1H), 3.76 (s, 3H), 3.02 (t, J=9.4 Hz, 2H), 2.80 (m, 3H), 2.69 (m, 2H), 2.05 (m, 2H), 1.30 (m, 2H). LC/MS (ESI+)=523 (M+H).

Example 662

N-((1R,2R)-2-{5-Chloro-2-[7-(2,2-difluoro-ethylamino)-6,7,8,9-tetrahydro-5H-benzocyclohepten-2-ylamino]-pyrimidin-4-ylamino}-cyclohexyl)-methanesulfonamide In an analogous procedure to Example 651, part c, N*7*-(2,2-Difluoro-ethyl)-6,7,8,9-tetrahydro-5H-benzocycloheptene-2,7-diamine was combined with N-[(1R,2R)-2-(2,5-

Dichloro-pyrimidin-4-ylamino)-cyclohexyl]-methanesulfonamide to yield N-((1R,2R)-2-{5-Chloro-2-[7-(2,2-difluoro-ethylamino)-6,7,8,9-tetrahydro-5H-benzocyclohepten-2-ylamino]-pyrimidin-4-ylamino}-cyclohexyl)-methanesulfonamide (69.11 mg, 61% yield) as a beige foam. $^1$H-NMR (CDCl$_3$) δ 7.91 (s, 1H), 7.24 (m, 2H), 7.05 (d, J=7.7 Hz, 1H), 6.85 (s, 1H), 5.83 (m, 1H), 5.39 (m, 2H), 3.86 (m, 1H), 3.23 (m, 1H), 3.02 (m, 2H), 2.78 (m, 2H), 2.68 (m, 2H), 2.20 (br s, 2H), 2.07 (br s, 2H), 1.82 (br s, 2H), 1.36 (m, 7H). LC/MS (ESI+)=542 (M+H).

Example 663

5-Chloro-N*2*-[7-(2,2-difluoro-ethylamino)-6,7,8,9-tetrahydro-5H-benzocyclohepten-2-yl]-N*4*-(2-methoxy-phenyl)-pyrimidine-2,4-diamine In an analogous procedure to Example 651, part c, N*7*-(2,2-Difluoro-ethyl)-6,7,8,9-tetrahydro-5H-benzocycloheptene-2,7-diamine was combined with (2,5-Dichloro-pyrimidin-4-yl)-(2-methoxy-phenyl)-amine to yield 5-Chloro-N*2*-[7-(2,2-difluoro-ethylamino)-6,7,8,9-tetrahydro-5H-benzocyclohepten-2-yl]-N*4*-(2-methoxy-phenyl)-pyrimidine-2,4-diamine (2.93 mg, 61% yield) as a white powder. $^1$H-NMR (CDCl$_3$) δ 8.44 (d, J=7.8 Hz, 1H), 8.04 (s, 1H), 7.85 (s, 1H), 7.37 (s, 1H), 7.23 (m, 1H), 7.02 (m, 2H), 6.92 (m, 3H), 5.84 (m, 1H). 3.94 (s, 3H), 2.80 (m, 3H), 2.68 (m, 2H), 2.07 (m, 2H), 1.30 (m, 2H). LC/MS (ESI+)=474 (M+H). MP=191-193° C.

Example 664

2-{5-Chloro-2-[7-(2,2-difluoro-ethylamino)-6,7,8,9-tetrahydro-5H-benzocyclohepten-2-ylamino]-pyrimidin-4-ylamino}-3-fluoro-N-methyl-benzamide In an analogous procedure to Example 651, part c, N*7*-(2,2-Difluoro-ethyl)-6,7,8,9-tetrahydro-5H-benzocycloheptene-2,7-diamine was combined with 2-(2,5-Dichloro-pyrimidin-4-ylamino)-3-fluoro-N-methyl-benzamide to yield 2-{5-Chloro-2-[7-(2,2-difluoro-ethylamino)-6,7,8,9-tetrahydro-5H-benzocyclohepten-2-ylamino]-pyrimidin-4-ylamino}-3-fluoro-N-methyl-benzamide (15.43 mg, 14.3% yield) as a off white foam. $^1$H-NMR (CDCl$_3$) δ 8.69 (s, 1H), 8.05 (s, 1H), 7.24 (m, 2H), 7.14 (s, 1H), 7.09 (d, J=8.1 Hz, 1H), 6.85 (d, J=8.1 Hz, 1H), 6.83 (s, 1H), 6.05 (m, 1H), 5.83 (m, 1H), 5.83 (m, 1H), 3.01 (t, J=4.3 Hz, 1H), 2.90 (d, J=4.9 Hz, 1H), 2.77 (m, 2H), 2.60 (m, 3H), 2.02 (m, 2H), 1.25 (m, 2H). LC/MS (ESI+)=519 (M+H).

Example 665

(1S,2S,3R,4R)-3-{5-Chloro-2-[7-(2,2-difluoro-ethylamino)-6,7,8,9-tetrahydro-5H-benzocyclohepten-2-ylamino]-pyrimidin-4-ylamino}-bicyclo[2.2.1]hept-5-ene-2-carboxylic acid amide In an analogous procedure to Example 651, part c, N*7*-(2,2-Difluoro-ethyl)-6,7,8,9-tetrahydro-5H-benzocycloheptene-2,7-diamine was combined with (1S,2S,3R,4R)-3-(2,5-Dichloro-pyrimidin-4-ylamino)-bicyclo[2.2.1]hept-5-ene-2-carboxylic acid amide to yield (1S,2S,3R,4R)-3-{5-Chloro-2-[7-(2,2-difluoro-ethylamino)-6,7,8,9-tetrahydro-5H-benzocyclohepten-2-ylamino]-pyrimidin-4-ylamino}-bicyclo[2.2.1]hept-5-ene-2-carboxylic acid amide (54.09 mg, 51.7% yield) as a white powder. $^1$H-NMR (CDCl$_3$) δ 7.86 (s, 1H), 7.40 (d, J=8.2 Hz, 1H), 7.28 (m, 1H), 7.01 (d, J=8.1 Hz, 1H), 6.88 (s, 1H), 6.82 (t, J=8.9 Hz, 1H), 6.31 (m, 2H), 5.83 (m, 1H), 5.56 (br s, 1H), 5.40 (br s, 1H), 4.36 (m, 1H), 3.05 (m, 3H), 2.89 (s, 1H), 2.78 (m, 3H), 2.47 (d, J=8.1 Hz, 1H), 2.24 (d, J=9.3 Hz, 1H), 2.07 (m, 2H), 1.63 (d, J=9.4 Hz, 1H), 1.31 (m, 2H). LC/MS (ESI+)=503 (M+H). MP=166° C.

Example 666

7-[5-Chloro-4-(2-methoxy-4-morpholin-4-yl-phenylamino)-pyrimidin-2-ylamino]-1-isopropyl-1,3,4,5-tetrahydro-benzo[b]azepin-2-one 666a) 7-Nitro-1,3,4,5-tetrahydro-benzo[b]azepin-2-one (500 mg, 2.42 mmol) was dissolved in 10 ml anhydrous DMF and the reaction cooled to 0° C. Sodium hydride (140 mg, 3.6 mmol) was charged and the reaction allowed to stir at 0° C. until hydrogen evolution ceases. Isopropyl iodide (1.45 ml, 14.50 mmol) was charged and the reaction allowed to warm to room temperature over night. In the morning, a new peak matching the desired mass was determined by LC/MS. The reaction was poured into 50 ml water and extracted with 3×25 ml portions of methylene chloride. The combined organic was washed with 2×10 ml portions water and 10 ml brine, dried over magnesium sulfate, filtered and evaporated. The resulting crude product was purified via silica gel chromatography on a 40 g Isco cartridge using a gradient of 0-70% ethyl acetate in hexanes to yield 1-Isopropyl-7-nitro-1,3,4,5-tetrahydro-benzo[b]azepin-2-one (474 mg, 79% yield) as a white solid. $^1$H-NMR (CDCl$_3$) δ 8.16 (d, J=8.8 Hz, 1H), 8.11 (s, 1H), 7.34 (d, J=8.7 Hz, 1H), 4.78 (m, 1H), 2.78 (m, 1H), 2.78 (br s 2H), 2.32 (br s, 2H), 2.16 (br s, 1H), 1.98 (br s, 1H), 1.48 (br s, 2H), 1.14 (br s, 2H). LC/MS (ESI+)=249 (M+H).

666b) 1-Isopropyl-7-nitro-1,3,4,5-tetrahydro-benzo[b]azepin-2-one (474 mg, 1.91 mmol) was charged to 10 ml ethanol and 100-200 mg 10% palladium on carbon was added. The suspension was hydrogenated at 30 psi hydrogen for 2.5 hours and followed by NMR. The reaction was filtered through a ¼" pad of celite and the pad washed with 4×10 ml portions of methanol. The resulting solution was clarified through a 45 micron frit to yield 7-Amino-1-isopropyl-1,3,4,5-tetrahydro-benzo[b]azepin-2-one (346 mg, 83% yield) as a clear oil. $^1$H-NMR (CDCl$_3$) δ 6.96 (d, J=8.3 Hz, 1H), 6.56 (d, J=8.3 Hz, 1H), 6.51 (s, 1H), 4.80 (m, 1H), 3.67 (br s, 1H), 2.71 (m, 1H), 2.44 (m, 1H), 2.20 (m, 3H), 1.84 (m, 1H), 1.36 (d, J=6.8 Hz, 3H), 1.01 (d, J=6.8 Hz, 3H). LC/MS (ESI+)=219 (M+H).

666c) In an analogous procedure to Example 651, part c, 1-isopropyl-7-nitro-1,3,4,5-tetrahydro-benzo[b]azepin-2-one was combined with (2,5-dichloro-pyrimidin-4-yl)-(2-methoxy-4-morpholin-4-yl-phenyl)-amine to yield 7-[5-Chloro-4-(2-methoxy-4-morpholin-4-yl-phenylamino)-pyrimidin-2-ylamino]-1-isopropyl-1,3,4,5-tetrahydro-benzo[b]azepin-2-one (50.70 mg, 52% yield) as a beige powder. $^1$H-NMR (CDCl$_3$) δ 8.15 (d, J=8.8 Hz, 1H), 8.03 (s, 1H), 7.53 (s, 1H), 7.48 (s, 1H), 7.37 (d, J=8.5 Hz, 1H), 7.10 (d, J=8.6 Hz, 1H), 6.98 (s, 1H), 6.54 (s, 1H), 6.47 (d, J=8.9 Hz, 1H), 4.83 (m, 1H), 3.90 (m, 8H), 3.13 (m, 5H), 2.75 (m, 1H), 2.53 (m, 1H), 2.23 (m, 3H), 1.86 (m, 1H), 1.42 (d, J=6.7 Hz, 3H), 1.05 (d, J=6.9 Hz, 3H). LC/MS (ESI+)=537 (M+H). MP=153-154° C.

Example 667

N-{(1R,2R)-2-[5-Chloro-2-(1-isopropyl-2-oxo-2,3,4,5-tetrahydro-1H-benzo[b]azepin-7-ylamino)-pyrimidin-4-ylamino]-cyclohexyl}-methanesulfonamide In an analogous procedure to Example 651, part c, 1-isopropyl-7-nitro-1,3,4,5-tetrahydro-benzo[b]azepin-2-one was combined with N-[(1R,2R)-2-(2,5-Dichloro-pyrimidin-4-ylamino)-cyclohexyl]-methanesulfonamide to yield N-{(1R,2R)-2-[5-Chloro-2-(1-isopropyl-2-oxo-2,3,4,5-tetrahydro-1H-benzo[b]azepin-7-ylamino)-pyrimidin-4-ylamino]-cyclohexyl}-methanesulfonamide (66.83 mg, 61% yield) as a white powder. $^1$H-NMR (CDCl$_3$) δ 7.93 (s, 1H), 7.40 (m, 2H), 7.12 (d, J=8.3 Hz, 1H), 6.99 (br s, 1H), 5.49 (d, J=7.5 Hz, 1H), 5.44 (m, 1H), 4.82 (m, 1H), 3.85 (br s, 1H), 3.23 (br s, 1H), 2.82 (m, 4H), 2.56 (m, 1H), 2.22 (m, 5H), 1.89 (m, 3H), 1.42 (d, J=6.6 Hz, 3H), 1.36 (br s, 3H), 1.03 (d, J=6.6 Hz, 3H). LC/MS (ESI+)=523 (M+H), MP=141-143° C.

Example 668

3-[5-Chloro-2-(1-methyl-2-oxo-2,3,4,5-tetrahydro-1H-benzo[b]azepin-7-ylamino)-pyrimidin-4-ylamino]-N-methyl-benzamide In an analogous procedure to Example 651, part c, 7-Amino-1-methyl-1,3,4,5-tetrahydro-benzo[b]azepin-2-one and 3-(2,5-Dichloro-pyrimidin-4-ylamino)-N-methyl-benzamide were combined to yield 3-[5-Chloro-2-(1-methyl-2-oxo-2,3,4,5-tetrahydro-1H-benzo[b]azepin-7-ylamino)-pyrimidin-4-ylamino]-N-methyl-benzamide (53.36 mg, 47% yield) as a white powder. $^1$H-NMR (DMSO-d$_6$) δ 9.39 (s, 1H), 9.03 (s, 1H), 8.39 (d, J=4.4 Hz, 1H), 8.16 (s, 1H), 7.99 (s, 1H), 7.76 (d, J=7.8 Hz, 1H), 7.62 (d, J=7.1 Hz, 1H), 7.47 (m, 1H), 7.44 (br s, 1H), 7.03 (d, J=8.7 Hz, 1H), 3.15 (s, 3H), 2.75 (d, J=4.3 Hz, 3H), 2.39 (m, 2H), 2.08 (m, 2H), 1.94 (m, 2H). LC/MS (ESI+)=451 (M+H). Mp=215-217° C.

Example 669

3-[5-Chloro-2-(1-isopropyl-2-oxo-2,3,4,5-tetrahydro-1H-benzo[b]azepin-7-ylamino)-pyrimidin-4-ylamino]-bicyclo[2.2.1]hept-5-ene-2-carboxylic acid amide In an analogous procedure to Example 651, part c, 1-isopropyl-7-nitro-1,3,4,5-tetrahydro-benzo[b]azepin-2-one was combined with 3-(2,5-Dichloro-pyrimidin-4-ylamino)-bicyclo[2.2.1]hept-5-ene-2-carboxylic acid amide to yield 3-[5-Chloro-2-(1-isopropyl-2-oxo-2,3,4,5-tetrahydro-1H-benzo[b]azepin-7-ylamino)-pyrimidin-4-ylamino]-bicyclo[2.2.1]hept-5-ene-2-carboxylic acid amide (55.01 mg, 57% yield) as a white powder. $^1$H-NMR (DMSO-d$_6$) δ 9.35 (s, 1H), 7.77 (m, 2H), 7.62 (m, 2H), 7.27 (m, 1H), 7.12 (d, J=8.5 Hz, 1H), 6.36 (s, 1H), 6.24 (s, 1H), 4.60 (m, 1H), 4.15 (m, 1H), 2.88 (s, 1H), 2.87 (s, 1H), 2.64 (m, 1H), 2.55 (m, 1H), 2.10 (m, 4H), 1.82 (m, 1H), 1.41 (d, J=8.3 Hz, 1H), 1.32 (d, J=6.6 Hz, 3H), 0.99 (d, J=6.8 Hz, 3H). LC/MS (ESI+)=481 (M+H). MP=260° C.

Example 670

3-[5-Chloro-2-(1,5,5-trimethyl-2-oxo-2,3,4,5-tetrahydro-1H-benzo[b]azepin-7-ylamino)-pyrimidin-4-ylamino]-N-methyl-benzamide In an analogous procedure to Example 651, part c, 7-Amino-1,5,5-trimethyl-1,3,4,5-tetrahydro-benzo[b]azepin-2-one and 3-(2,5-Dichloro-pyrimidin-4-ylamino)-N-methyl-benzamide were combined to yield 3-[5-Chloro-2-(1,5,5-trimethyl-2-oxo-2,3,4,5-tetrahydro-1H-benzo[b]azepin-7-ylamino)-pyrimidin-4-ylamino]-N-methyl-benzamide (55.06 mg, 43% yield) as a white solid. $^1$H-NMR (DMSO-d$_6$) δ 9.39 (s, 1H), 9.02 (s, 1H), 8.37 (m, 1H), 8.17 (s, 1H), 8.01 (s, 1H), 7.77 (d, J=7.7 Hz, 1H), 7.71 (d, J=8.8 Hz, 1H), 7.42 (m, 2H), 7.00 (d, J=8.8 Hz, 1H), 3.12 (s, 3H), 2.75 (d, J=4.2 Hz, 3H), 2.09 (br s, 2H), 2.09 (br s, 2H), 1.87 (br s, 2H), 1.13 (m, 6H). LC/MS (ESI+)=479 (M+H). 263-263.5° C.

Example 671

(1S,2S,3R,4R)-3-[5-Chloro-2-(7-morpholin-4-yl-6,7,8,9-tetrahydro-5H-benzocyclohepten-2-ylamino)-pyrimidin-4-ylamino]-bicyclo[2.2.1]hept-5-ene-2-carboxylic acid amide In an analogous procedure to Example 651, part c, 7-Morpholin-4-yl-6,7,8,9-tetrahydro-5H-benzocyclohepten-2-ylamine and (1S,2S,3R,4R)-3-(2,5-Dichloro-pyrimidin-4-ylamino)-bicyclo[2.2.1]hept-5-ene-2-carboxylic acid amide were combined to yield 1S,2S,3R,4R)-3-[5-Chloro-2-(7-morpholin-4-yl-6,7,8,9-tetrahydro-5H-benzocyclohepten-2-ylamino)-pyrimidin-4-ylamino]-bicyclo[2.2.1]hept-5-ene-2-carboxylic acid amide as a white solid. $^1$H-NMR (CDCl$_3$) δ 9.12 (s, 1H), 7.93 (s, 1H), 7.78 (s, 1H), 7.70 (m, 1H), 7.52 (m, 1H), 7.46 (d, J=21.2 Hz, 1H), 7.26 (s, 1H), 7.00 (d, J=8.2 Hz, 1H), 6.35 (s, 1H), 6.27 (s, 1H), 4.13 (m, 1H), 3.31 (s, 3H), 2.87 (s, 1H), 2.77 (s, 1H), 2.56 (m, 6H), 2.45 (m, 4H), 2.10 (d, J=8.6 Hz, 1H), 1.95 (m, 2H), 1.40 (d, J=8.8 Hz, 1H), 1.31 (m, 2H). LC/MS (ESI+)=509 (M+H).

Example 672

3-[5-Chloro-2-(5,5-dimethyl-2-oxo-2,3,4,5-tetrahydro-1H-benzo[b]azepin-7-ylamino)-pyrimidin-4-ylamino]-N-methyl-benzamide In an analogous procedure to Example 651, part c, 7-Amino-5,5-dimethyl-1,3,4,5-tetrahydro-benzo[b]azepin-2-one and 3-(2,5-Dichloro-pyrimidin-4-ylamino)-N-methyl-benzamide were combined to yield 3-[5-Chloro-2-(5,5-dimethyl-2-oxo-2,3,4,5-tetrahydro-1H-benzo[b]azepin-7-ylamino)-pyrimidin-4-ylamino]-N-methyl-benzamide (19.47 mg, 19% yield) as a white amorphous solid. $^1$H-NMR (CDCl$_3$) δ 8.10 (s, 1H), 8.01 (s, 1H), 7.75 (d, J=7.8 Hz, 1H), 7.58 (d, J=8.60 Hz, 1H), 7.48 (m, 1H), 7.38 (m, 1H), 7.38 (m, 1H), 7.32 (s, 1H), 7.17 (d, J=14.9 Hz, 1H), 7.07 (s, 1H), 6.81 (d, J=7.8 Hz, 1H), 6.06 (br s, 1H), 2.97 (s, 3H), 2.37 (m, 2H), 2.07 (m, 2H), 1.33 (s, 6H). LC/MS (ESI+)=465 (M+H). MP=184.5° C.

Example 673

3-{5-Chloro-2-[3-(2-methoxy-ethyl)-2,3,4,5-tetrahydro-1H-benzo[d]azepin-7-ylamino]-pyrimidin-4-ylamino}-N-methyl-benzamide In an analogous procedure to Example 651, part c, 3-(2-Methoxy-ethyl)-2,3,4,5-tetrahydro-1H-benzo[d]azepin-7-ylamine and 3-(2,5-Dichloro-pyrimidin-4-ylamino)-N-methyl-benzamide were combined to yield 3-{5-Chloro-2-[3-(2-methoxy-ethyl)-2,3,4,5-tetrahydro-1H-benzo[d]azepin-7-ylamino]-pyrimidin-4-ylamino}-N-methyl-benzamide (29.56 mg, 38% yield) as a beige amorphous solid. $^1$H-NMR (CDCl$_3$) δ 8.07 (s, 1H), 7.97 (s, 1H), 7.75 (m, 1H), 7.52 (m, 1H), 7.40 (t, J=7.9 Hz, 1H), 7.22 (m, 1H), 6.97 (t, J=7.9 Hz, 1H), 5.99 (br s, 1H), 3.54 (m, 2H), 3.35 (s, 3H), 2.90 (m, 5H), 2.81 (m, 1H), 2.74 (m, 6H). LC/MS (ESI+)=481 (M+H). MP=102.5° C. dec.

Example 674

7-{5-Chloro-4-[2-methoxy-4-(4-methyl-piperazin-1-yl)-phenylamino]-pyrimidin-2-ylamino}-1-isopropyl-1,3,4,5-tetrahydro-benzo[b]azepin-2-one In an analogous procedure to Example 651, part c, 1-isopropyl-7-nitro-1,3,4,5-tetrahydro-benzo[b]azepin-2-one was combined with (2,5-Dichloro-pyrimidin-4-yl)-[2-methoxy-4-(4-methyl-piperazin-1-yl)-phenyl]-amine to yield 7-{5-Chloro-4-[2-methoxy-4-(4-methyl-piperazin-1-yl)-phenylamino]-pyrimidin-2-ylamino}-1-isopropyl-1,3,4,5-tetrahydro-benzo[b]azepin-2-one (39.63 mg, 42% yield) as a beige oil. $^1$H-NMR (CDCl$_3$) δ 8.12 (d, J=8.9 Hz, 1H), 8.02 (s, 1H), 7.50 (d, J=9.5 Hz, 1H), 7.35 (d, J=8.6 Hz, 1H), 7.10 (d, J=8.6 Hz, 1H), 6.92 (s, 1H), 6.56 (s, 1H), 6.49 (d, J=8.9 Hz, 1H), 4.83 (m, 1H), 3.90 (s, 3H), 3.19 (m, 4H), 2.76 (m, 1H), 2.59 (m, 3H), 2.50 (m, 1H), 2.37 (m, 3H), 2.23 (m, 2H), 1.87 (m, 1H), 1.42 (d, J=6.8 Hz, 3H), 1.05 (d, J=7.0 Hz, 3H). LC/MS (ESI+)=550 (M+H).

Example 675

N-((1R,2R)-2-{5-Chloro-2-[7-(2,2-difluoro-ethylamino)-6,7,8,9-tetrahydro-5H-benzocyclohepten-2-ylamino]-pyrimidin-4-ylamino}-cyclohexyl)-methanesulfonamide 675a) Charge 4-Bromo-1-methoxy-2-nitro-5,6,8,9-tetrahydro-benzocyclohepten-7-one-7-one (644.00 mg, 2.77 mmol) to methylene chloride (20 mL, 300 mmol) and acetic acid (200 uL, 4 mmol). Allow to stir for 5 min. Charge 2,2-difluorethylamine (222 mg, 2.77 mmol) and reflux overnight. In the morning charge sodium triacetoxyborohydride (1.16 g, 5.8 mmol). Allow suspension to stir for 2.5 hours. LC at 2.5 hours conforms that starting ketone has been consumed. Pour reaction into 200 ml water and 100 ml saturated sodium bicarbonate solution and extract with 2×100 ml portions of methylene chloride. The combined organic was dried over magnesium sulfate, filtered and evaporated to a yellow oil (approximately 1.0 g). The resulting crude yellow oil was chromatographed on a 40 g Isco cartridge using a gradient of 30-70% EtOAc in hexanes as the eluent. 4-Bromo-1-methoxy-2-nitro-6,7,8,9-tetrahydro-5H-benzocyclohepten-7-yl)-(2,2-difluoro-ethyl)-amine was isolated as a beige oil (821 mg, 99% yield). $^1$H-NMR (CDCl$_3$)$^-$ δ 7.59 (d, J=8.2 Hz, 1H), 6.98 (d, J=8.3 Hz, 1H), 5.83 (m, 1H), 3.85 (s, 3H), 3.31 (m, 1H), 3.03-2.88 (m, 4H), 2.73 (m, 1H), 2.53 (m, 1H), 2.10 (m, 2H), 1.33 (m, 2H). LC/MS (ESI+)=301 (M+H).

675b) 4-Bromo-1-methoxy-2-nitro-6,7,8,9-tetrahydro-5H-benzocyclohepten-7-yl)-(2,2-difluoro-ethyl)-amine (821 mg, 2.72 mmol) was charged to 30 ml ethanol and 200-300 mg 10% palladium on carbon was added. The suspension was hydrogenated at 45 psi hydrogen for 16 hours and followed by NMR. The reaction was filtered through a ¼" pad of celite and the pad washed with 4×10 ml portions of methanol. The resulting solution was clarified through a 45 micron frit to yield a yellow solution that was evaporated to yield N*7*-(2,2-Difluoro-ethyl)-1-methoxy-6,7,8,9-tetrahydro-5H-benzocycloheptene-2,7-diamine (754 mg, 99% yield) as a white solid. $^1$H-NMR (CDCl$_3$) δ 6.71 (d, J=8.1 Hz, 1H), 6.50 (d, J=7.9 Hz, 1H), 5.83 (m, 1H), 3.69 (s, 3H), 3.19 (m, 1H), 3.01 (t, J=7.8 Hz, 2H), 2.76 (m, 2H), 2.60 (m, 1H), 2.42 (m, 1H), 2.07 (m, 2H), 1.27 (m, 2H). LC/MS (ESI+)=271 (M+H).

675c) In an analogous procedure to Example 651, part c, N*7*-(2,2-Difluoro-ethyl)-1-methoxy-6,7,8,9-tetrahydro-5H-benzocycloheptene-2,7-diamine was combined with N-[(1R,2R)-2-(2,5-Dichloro-pyrimidin-4-ylamino)-cyclohexyl]-methanesulfonamide to yield N-((1R,2R)-2-{5-Chloro-2-[7-(2,2-difluoro-ethylamino)-6,7,8,9-tetrahydro-5H-benzocyclohepten-2-ylamino]-pyrimidin-4-ylamino}-cyclohexyl)-methanesulfonamide (382.94 mg, 60.7% yield) as a white foam. $^1$H-NMR (CDCl$_3$) δ 7.92 (m, 2H), 7.29 (m, 1H), 6.88 (d, J=8.17 Hz, 1H), 5.83 (m, 1H), 5.42 (m, 1H), 3.90 (m, 1H), 3.72 (s, 3H), 3.25 (m, 2H), 3.00 (t, J=15.0 Hz, 2H), 2.78 (m, 5H), 2.63 (m, 1H), 2.51 (m, 1H), 2.22 (m, 2H), 1.85 (m, 2H), 1.37 (m, 6H). LC/MS=573 (M+H).

Example 676

N-((1R,2R)-2-{5-Chloro-2-[7-(2,2,2-trifluoro-ethylamino)-6,7,8,9-tetrahydro-5H-benzocyclohepten-2-ylamino]-pyrimidin-4-ylamino}-cyclohexyl)-methanesulfonamide 676a) In an analagous manner to Experimental 675, part a, 4-Bromo-1-methoxy-2-nitro-5,6,8,9-tetrahydro-benzocyclohepten-7-one-7-one and 2,2,2-trifluoroethylamine were combined to yield (4-bromo-1-methoxy-2-nitro-6,7,8,9-tetrahydro-5H-benzocyclohepten-7-yl)-(2,2,2-trifluoro-ethyl)-amine as a beige oil. $^1$H-NMR (CDCl$_3$) δ 7.59 (d, J=8.2 Hz, 1H), 6.96 (d, J=8.2 Hz, 1H), 3.85 (s, 3H), 3.24 (m, 3H), 2.98 (m, 1H), 2.09 (m, 2H), 1.46-1.35 (m, 3H).

676b) In an analagous manner to Experimental 675, part b, (4-bromo-1-methoxy-2-nitro-6,7,8,9-tetrahydro-5H-benzocyclohepten-7-yl)-(2,2,2-trifluoro-ethyl)-amine yielded 1-methoxy-N*7*-(2,2,2-trifluoro-ethyl)-6,7,8,9-tetrahydro-5H-benzocycloheptene-2,7-diamine as a white solid. $^1$H-NMR (CDCl$_3$) δ 6.69 (d, J=7.9 Hz, 1H), 6.51 (d, J=7.9 Hz, 1H), 3.69 (s, 3H), 3.22 (m, 3H), 2.86 (m, 2H), 2.73 (m, 1H), 2.60 (m, 1H), 2.42 (m, 1H), 2.06 (m, 2H), 1.46-1.35 (m, 2H).

676c) In an analogous procedure to Example 651, part c, 1-methoxy-N*7*-(2,2,2-trifluoro-ethyl)-6,7,8,9-tetrahydro-5H-benzocycloheptene-2,7-diamine was combined with N-[(1R,2R)-2-(2,5-Dichloro-pyrimidin-4-ylamino)-cyclohexyl]-methanesulfonamide to yield N-((1R,2R)-2-{5-Chloro-2-[7-(2,2,2-trifluoro-ethylamino)-6,7,8,9-tetrahydro-5H-benzocyclohepten-2-ylamino]-pyrimidin-4-ylamino}-cyclohexyl)-methanesulfonamide (456.46, 70% yield) as a beige foam. $^1$H-NMR (CDCl$_3$) δ 7.92 (m, 2H), 7.27 (m, 1H), 6.88 (d, J=8.3 Hz, 1H), 5.40 (m, 2H), 3.90 (m, 1H), 3.72 (s, 3H), 3.24 (m, 4H), 2.81 (M, 4H), 2.66 (m, 1H), 2.49 (m, 1H), 2.22 (m, 2H), 2.08 (m, 2H), 1.36 (m, 6H). LC/MS (ESI+)=591 (M+H).

Example 677

(1S,2S,3R,4R)-3-{5-Chloro-2-[7-(2,2-difluoro-ethylamino)-6,7,8,9-tetrahydro-5H-benzocyclohepten-2-ylamino]-pyrimidin-4-ylamino}-bicyclo[2.2.1]hept-5-ene-2-carboxylic acid amide In an analogous procedure to Example 651, part c, N*7*-(2,2-Difluoro-ethyl)-1-methoxy-6,7,8,9-tetrahydro-5H-benzocycloheptene-2,7-diamine was combined with (1S,2S,3R,4R)-3-(2,5-Dichloro-pyrimidin-4-ylamino)-bicyclo[2.2.1]hept-5-ene-2-carboxylic acid amide to yield (1S,2S,3R,4R)-3-{5-Chloro-2-[7-(2,2-difluoro-ethylamino)-6,7,8,9-tetrahydro-5H-benzocyclohepten-2-ylamino]-pyrimidin-4-ylamino}-bicyclo[2.2.1]hept-5-ene-2-carboxylic acid amide (28.05 mg, 29% yield) as an off white amorphous solid. $^1$H-NMR (CDCl$_3$) δ 8.16 (d, J=8.2 Hz, 1H), 7.89 (s, 1H), 7.39 (s, 1H), 6.96 (m, 1H), 6.87 (d, J=8.3 Hz, 1H), 6.37 (br s, 1H), 6.32 (br s, 1H), 5.83 (m, 1H), 5.59 (br s, 1H), 5.37 (br s, 1H), 4.36 (m, 1H), 3.72 (s, 3H), 3.22 (m, 1H), 3.03 (m, 3H), 2.95 (s, 1H), 2.83 (m, 2H), 2.66 (m, 1H), 2.50 (m, 1H), 2.24 (d, J=9.4 Hz, 1H), 2.09 (m, 2H), 1.63 (d, J=9.0 Hz, 1H), 1.30 (m, 2H). LC/MS (ESI+)=553 (M+H). MP=127.5-128.5° C.

Example 678

5-Chloro-N*2*-[7-(2,2-difluoro-ethylamino)-1-methoxy-6,7,8,9-tetrahydro-5H-benzocyclohepten-2-yl]-N*4*-methyl-N*4*-[2-(propane-2-sulfonyl)-phenyl]-pyrimidine-2,4-diamine In an analogous procedure to Example 651, part c, N*7*-(2,2-Difluoro-ethyl)-1-methoxy-6,7,8,9-tetrahydro-5H-benzocycloheptene-2,7-diamine was combined with (2,5-Dichloro-pyrimidin-4-yl)-methyl-[2-(propane-2-sulfonyl)-phenyl]-amine to yield 5-Chloro-N*2*-[7-(2,2-difluoro-ethylamino)-1-methoxy-6,7,8,9-tetrahydro-5H-benzocyclohepten-2-yl]-N*4*-methyl-N*4*-[2-(propane-2-sulfonyl)-phenyl]-pyrimidine-2,4-diamine (4.71 mg, 4.4% yield) as a brown oil. $^1$H-NMR (CDCl$_3$) δ 9.57 (s, 1H), 8.59 (d, J=8.4 Hz, 1H), 8.16 (s, 1H), 7.98 (d, J=8.2 Hz, 1H), 7.92 (d, J=8.0 Hz, 1H), 7.65 (m, 1H), 7.47 (s, 1H), 7.27 (m, 1H), 6.83 (d, J=7.8 Hz, 1H), 5.83 (m, 1H), 3.73 (m, 3H), 3.22 (m, 2H), 3.02 (m, 2H), 2.83 (m, 2H), 2.67 (m, 1H), 2.49 (m, 1H), 2.11 (m, 2H), 1.32 (m, 10H). LC/MS (ESI+)=580 (M+H).

Example 679

(1S,2S,3R,4R)-3-{5-Chloro-2-[1-methoxy-7-(2,2,2-trifluoro-ethylamino)-6,7,8,9-tetrahydro-5H-benzocyclohepten-2-ylamino]-pyrimidin-4-ylamino}-bicyclo[2.2.1]hept-5-ene-2-carboxylic acid amide In an analogous procedure to Example 651, part c, 1-methoxy-N*7*-(2,2,2-trifluoro-ethyl)-6,7,8,9-tetrahydro-5H-benzocycloheptene-2,7-diamine was combined with (1S,2S,3R,4R)-3-(2,5-Dichloro-pyrimidin-4-ylamino)-bicyclo[2.2.1]hept-5-ene-2-carboxylic acid amide to yield (1S,2S,3R,4R)-3-{5-Chloro-2-[1-methoxy-7-(2,2,2-trifluoro-ethylamino)-6,7,8,9-tetrahydro-5H-benzocyclohepten-2-ylamino]-pyrimidin-4-ylamino}-bicyclo[2.2.1]hept-5-ene-2-carboxylic acid amide (3.14 g, 3.3% yield) as an off white amorphous solid. $^1$H-NMR (CDCl$_3$) δ 8.18 (d, J=8.2 Hz, 1H), 7.89 (s, 1H), 7.39 (s, 1H), 6.96 (m, 1H), 6.86 (d, J=8.3 Hz, 1H), 6.35 (m, 1H), 6.31 (m, 1H), 5.59 (br s, 1H), 5.35 (br s, 1H), 4.35 (m, 1H), 3.72 (s, 3H), 3.24 (m, 3H), 3.07 (s, 1H), 2.94-2.78 (m, 3H), 2.66 (m, 1H), 2.50 (m, 2H), 2.22 (d, J=9.6 Hz, 1H), 2.09 (m, 2H), 1.33 (m, 2H). LC/MS (ESI+)=551 (M+H).

Example 680

5-Chloro-N*2*-[1-methoxy-7-(2,2,2-trifluoro-ethylamino)-6,7,8,9-tetrahydro-5H-benzocyclohepten-2-yl]-N*4*-methyl-N*4*-[2-(propane-2-sulfonyl)-phenyl]-pyrimidine-2,4-diamine In an analogous procedure to Example 651, part c, 1-methoxy-N*7*-(2,2,2-trifluoro-ethyl)-6,7,8,9-tetrahydro-5H-benzocycloheptene-2,7-diamine was combined with (2,5-Dichloro-pyrimidin-4-yl)-[2-(propane-2-sulfonyl)-phenyl]-amine to yield 5-Chloro-N*2*-[1-methoxy-7-(2,2,2-trifluoro-ethylamino)-6,7,8,9-tetrahydro-5H-benzocyclohepten-2-yl]-N*4*-methyl-N*4*-[2-(propane-2-sulfonyl)-phenyl]-pyrimidine-2,4-diamine (39.10 mg, 36% yield) as a beige foam. $^1$H-NMR (CDCl$_3$) δ 9.76 (s, 1H), 8.51 (d, J=8.0 Hz, 1H), 8.16 (s, 1H), 7.91 (d, J=7.9 Hz, 1H), 7.81 (m, 1H), 7.59 (m, 1H), 7.24 (m, 1H), 6.83 (d, J=8.0 Hz, 1H), 3.74 (s, 3H), 3.23 (m, 6H), 2.99 (m, 1H), 2.87 (m, 2H), 2.71-2.49 (m, 4H), 2.14 (m, 4H), 1.31 (m, 1H), 1.06 (s, 1H), 0.83 (s, 2H). LC/MS (ESI+)=598 (M+H).

Example 681 & 682

(1S,2S,3R,4R)-3-[5-Chloro-2-(7-morpholin-4-yl-6,7,8,9-tetrahydro-5H-benzocyclohepten-2-ylamino)-pyrimidin-4-ylamino]-bicyclo[2.2.1]hept-5-ene-2-carboxylic acid amide and (1S,2S,3R,4R)-3-[5-Chloro-2-(7-morpholin-4-yl-6,7,8,9-tetrahydro-5H-benzocyclohepten-2-ylamino)-pyrimidin-4-ylamino]-bicyclo[2.2.1]hept-5-ene-2-carboxylic acid amide Separated by chiral HPLC into 2 enantiomers Example 681—1$^{st}$ eluting peak. $^1$H-NMR (CDCl$_3$) δ 9.12 (s, 1H), 7.93 (s, 1H), 7.78 (s, 1H), 7.70 (m, 1H), 7.52 (m, 1H), 7.46 (d, J=21.2 Hz, 1H), 7.26 (s, 1H), 7.00 (d, J=8.2 Hz, 1H), 6.35 (s, 1H), 6.27 (s, 1H), 4.13 (m, 1H), 3.31 (s, 3H), 2.87 (s, 1H), 2.77 (s, 1H), 2.56 (m, 6H), 2.45 (m, 4H), 2.10 (d, J=8.6 Hz, 1H), 1.95 (m, 2H), 1.40 (d, J=8.8 Hz, 1H), 1.31 (m, 2H). LC/MS (ESI+)=509 (M+H). Example 682—2nd eluting peak. $^1$H-NMR (CDCl$_3$) δ 9.12 (s, 1H), 7.93 (s, 1H), 7.78 (s, 1H), 7.70 (m, 1H), 7.52 (m, 1H), 7.46 (d, J=21.2 Hz, 1H), 7.26 (s, 1H), 7.00 (d, J=8.2 Hz, 1H), 6.35 (s, 1H), 6.27 (s, 1H), 4.13 (m, 1H), 3.31 (s, 3H), 2.87 (s, 1H), 2.77 (s, 1H), 2.56 (m, 6H), 2.45 (m, 4H), 2.10 (d, J=8.6 Hz, 1H), 1.95 (m, 2H), 1.40 (d, J=8.8 Hz, 1H), 1.31 (m, 2H). LC/MS (ESI+)=509 (M+H).

Example 683

2-{5-Chloro-2-[7-(2,2-difluoro-ethylamino)-1-methoxy-6,7,8,9-tetrahydro-5H-benzocyclohepten-2-ylamino]-pyrimidin-4-ylamino}-N,N-dimethyl-benzenesulfonamide In an analogous procedure to Example 651, part c, N*7*-(2,2-Difluoro-ethyl)-1-methoxy-6,7,8,9-tetrahydro-5H-benzocycloheptene-2,7-diamine was combined with 2-(2,5-Dichloro-pyrimidin-4-ylamino)-N,N-dimethyl-benzenesulfonamide to yield 2-{5-Chloro-2-[7-(2,2-difluoro-ethylamino)-1-methoxy-6,7,8,9-tetrahydro-5H-benzocyclohepten-2-ylamino]-pyrimidin-4-ylamino}-N,N-dimethyl-benzenesulfonamide (33.59 mg, 32% yield) as a beige powder. $^1$H-NMR (CDCl$_3$) δ 9.40 (s, 1H), 8.56 (d, J=8.4 Hz, 1H), 8.15 (s, 1H), 7.99 (d, J=8.4 Hz, 1H), 7.88 (d, J=8.0 Hz, 1H), 7.47 (s, 1H), 6.82 (d, J=8.2 Hz, 1H) 5.83 (m, 1H), 3.73 (s, 3H), 3.23 (m, 1H), 3.02 (m, 2H), 2.83 (m, 2H), 2.73 (s, 3H), 2.67 (m, 1H), 2.49 (m, 1H), 2.09 (m, 2H), 1.30 (m, 2H). LC/MS (ESI+)=581 (M+H). MP=118° C.

Example 684

2-{5-Chloro-2-[1-methoxy-7-(2,2,2-trifluoro-ethylamino)-6,7,8,9-tetrahydro-5H-benzocyclohepten-2-ylamino]-pyrimidin-4-ylamino}-N,N-dimethyl-benzenesulfonamide In an analogous procedure to Example 651, part c, 1-Methoxy-N*7*-(2,2,2-trifluoro-ethyl)-6,7,8,9-tetrahydro-5H-benzocycloheptene-2,7-diamine was combined with 2-(2,5-dichloro-pyrimidin-4-ylamino)-N,N-dimethyl-benzenesulfonamide to yield 2-{5-Chloro-2-[1-methoxy-7-(2,2,2-trifluoro-ethylamino)-6,7,8,9-tetrahydro-5H-benzocyclohepten-2-ylamino]-pyrimidin-4-ylamino}-N,N-dimethyl-benzenesulfonamide (36.29, 34.9% yield) as a beige foam. 9.40 (s, 1H), 8.56 (d, J=8.4 Hz, 1H), 8.14 (s, 1H), 7.99 (d, J=8.4 Hz, 1H), 7.88 (d, J=8.0 Hz, 1H), 7.61 (m, 1H), 7.47 (s, 1H), 6.82 (d, J=8.2 Hz, 1H), 3.73 (s, 3H), 3.25 (m, 3H), 2.87 (m, 2H), 2.75 (s, 6H), 2.66 (m, 1H), 2.50 (m, 1H), 2.10 (m, 2H), 1.54 (m, 2H).

Example 685 & Example 686

N-((1R,2R)-2-{5-Chloro-2-[7-(2,2-difluoro-ethylamino)-6,7,8,9-tetrahydro-5H-benzocyclohepten-2-ylamino]-pyrimidin-4-ylamino}-cyclohexyl)-methanesulfonamide The final product from Example 675 was separated into its enantiomers vial chiral HPLC. Example 685—1$^{st}$ eluting peak $^1$H-NMR (CDCl$_3$) δ 7.92 (m, 2H), 7.29 (m, 1H), 6.88 (d, J=8.17 Hz, 1H), 5.83 (m, 1H), 5.42 (m, 1H), 3.90 (m, 1H), 3.72 (s, 3H), 3.25 (m, 2H), 3.00 (t, J=15.0 Hz, 2H), 2.78 (m, 5H), 2.63 (m, 1H), 2.51 (m, 1H), 2.22 (m, 2H), 1.85 (m, 2H), 1.37 (m, 6H). LC/MS=573 (M+H). Example 686—2nd eluting peak. $^1$H-NMR (CDCl$_3$) δ 7.92 (m, 2H), 7.29 (m, 1H), 6.88 (d, J=8.17 Hz, 1H), 5.83 (m, 1H), 5.42 (m, 1H), 3.90 (m, 1H), 3.72 (s, 3H), 3.25 (m, 2H), 3.00 (t, J=15.0 Hz, 2H), 2.78 (m, 5H), 2.63 (m, 1H), 2.51 (m, 1H), 2.22 (m, 2H), 1.85 (m, 2H), 1.37 (m, 6H). LC/MS=573 (M+H).

Example 687 & Example 688

N-((1R,2R)-2-{5-Chloro-2-[7-(2,2,2-trifluoro-ethylamino)-6,7,8,9-tetrahydro-5H-benzocyclohepten-2-ylamino]-pyrimidin-4-ylamino}-cyclohexyl)-methanesulfonamide Example 687—1$^{st}$ eluting $^1$H-NMR (CDCl$_3$) δ 7.92 (m, 2H), 7.27 (m, 1H), 6.88 (d, J=8.3 Hz, 1H), 5.40 (m, 2H), 3.90 (m, 1H), 3.72 (s, 3H), 3.24 (m, 4H), 2.81 (M, 4H), 2.66 (m, 1H), 2.49 (m, 1H), 2.22 (m, 2H), 2.08 (m, 2H), 1.36 (m, 6H). LC/MS (ESI+)=591 (M+H). Example 688—2nd eluting. $^1$H-NMR (CDCl$_3$) δ 7.92 (m, 2H), 7.27 (m, 1H), 6.88 (d, J=8.3 Hz, 1H), 5.40 (m, 2H), 3.90 (m, 1H), 3.72 (s, 3H), 3.24 (m, 4H), 2.81 (M, 4H), 2.66 (m, 1H), 2.49 (m, 1H), 2.22 (m, 2H), 2.08 (m, 2H), 1.36 (m, 6H). LC/MS (ESI+)=591 (M+H).

Example 689

5-Chloro-N*2*-[7-(2,2-difluoro-ethylamino)-1-methoxy-6,7,8,9-tetrahydro-5H-benzocyclohepten-2-yl]-N*4*-(2-pyrazol-1-yl-phenyl)-pyrimidine-2,4-diamine In an analogous procedure to Example 651, part c, N*7*-(2,2-Difluoro-ethyl)-1-methoxy-6,7,8,9-tetrahydro-5H-benzocycloheptene-2,7-diamine was combined with (2,5-Dichloro-pyrimidin-4-yl)-(2-pyrazol-1-yl-phenyl)-amine to yield 5-Chloro-N*2*-[7-(2,2-difluoro-ethylamino)-1-methoxy-6,7,8,9-tetrahydro-5H-benzocyclohepten-2-yl]-N*4*-(2-pyrazol-1-yl-phenyl)-pyrimidine-2,4-diamine (57.74, 58% yield) as a red glass. $^1$H-NMR (CDCl$_3$) δ 10.17 (s, 1H), 8.52 (d, J=8.3 Hz, 1H), 8.02 (m, 2H), 7.82 (d, J=18.3 Hz, 2H), 7.38 (m, 3H), 7.19 (m, 1H), 6.82 (d, J=8.1 Hz, 1H), 6.60 (m, 1H), 6.52 (m, 1H), 5.82 (m, 1H), 3.70 (s, 3H), 3.21 (m, 2H), 3.02 (m, 2H), 2.98-2.30 (m, 6H), 2.06 (m, 2H), 1.23 (m, 2H).

Example 690

5-Chloro-N*2*-[1-methoxy-7-(2,2,2-trifluoro-ethylamino)-6,7,8,9-tetrahydro-5H-benzocyclohepten-2-yl]-N*4*-(2-pyrazol-1-yl-phenyl)-pyrimidine-2,4-diamine In an analogous procedure to Example 651, part c, 1-Methoxy-N*7*-(2,2,2-trifluoro-ethyl)-6,7,8,9-tetrahydro-5H-benzocycloheptene-2,7-diamine was combined with (2,5-dichloro-pyrimidin-4-yl)-(2-pyrazol-1-yl-phenyl)-amine to yield -Chloro-N*2*-[1-methoxy-7-(2,2,2-trifluoro-ethylamino)-6,7,8,9-tetrahydro-5H-benzocyclohepten-2-yl]-N*4*-(2-pyrazol-1-yl-phenyl)-pyrimidine-2,4-diamine (60.59 mg, 63% yield) as a red glass. $^1$H-NMR (CDCl$_3$) δ 10.17 (s, 1H), 8.52 (d, J=8.3 Hz, 1H), 8.05 (m, 2H), 7.82 (d, J=18.2 Hz, 2H), 7.41 (m, 3H), 7.21 (m, 1H), 6.82 (d, J=8.2 Hz, 1H), 6.69 (d, J=8.1 Hz, 1H), 6.51 (m, 2H), 3.71 (s, 3H), 3.23 (m, 3H), 2.87 (m, 1H), 2.62 (m, 2H), 2.45 (m, 1H), 2.09 (m, 2H), 1.29 (m, 2H).

Example 691

(1S,2S,3R,4R)-3-{5-Chloro-2-[1-methoxy-7-(2-methoxy-ethylamino)-6,7,8,9-tetrahydro-5H-benzocyclohepten-2-ylamino]-pyrimidin-4-ylamino}-bicyclo[2.2.1]hept-5-ene-2-carboxylic acid amide 691a) In an analagous manner to Experimental 675, part a, 4-Bromo-1-methoxy-2-nitro-5,6,8,9-tetrahydro-benzocyclohepten-7-one-7-one and 2-methoxyethylamine were combined to yield (4-Bromo-1-methoxy-2-nitro-6,7,8,9-tetrahydro-5H-benzocyclohepten-7-yl)-(2-methoxy-ethyl)-amine as a red oil. $^1$H-NMR (CDCl$_3$) δ 7.92 (s, 1H), 3.84 (s, 3H), 3.51 (m, 2H), 3.36 (s, 3H), 2.83 (m, 4H), 2.62 (m, 1H), 2.07 (m, 2H), 1.33 (m, 2H).

691b) In an analagous manner to Experimental 675, part b, 4-bromo-1-methoxy-2-nitro-6,7,8,9-tetrahydro-5H-benzocyclohepten-7-yl)-(2-methoxy-ethyl)-amine yielded 1-methoxy-N*7*-(2-methoxy-ethyl)-6,7,8,9-tetrahydro-5H-benzocycloheptene-2,7-diamine as a red solid. $^1$H-NMR (CDCl$_3$) δ 6.68 (d, J=7.9 Hz, 1H), 6.52 (d, J=7.9 Hz, 1H), 3.84 (m, 2H), 3.69 (s, 3H), 3.40 (s, 3H), 3.20 (m, 2H), 2.79 (m, 1H), 2.67 (m, 1H), 2.56 (m, 2H), 2.36 (m, 1H), 1.63 (m, 2H).

691c) 1-Methoxy-N*7*-(2-methoxy-ethyl)-6,7,8,9-tetrahydro-5H-benzocycloheptene-2,7-diamine 200 mg, 0.8 mmol) and (1S,2S,3R,4R)-3-(2,5-dichloro-pyrimidin-4-ylamino)-bicyclo[2.2.1]hept-5-ene-2-carboxylic acid amide (224 mg, 0.750 mmol) were dissolved in 5 ml 2-methoxyethanol in a reaction tube. 4N HCl in dioxane (0.4 ml, 1.6 mmol) was charged and the reaction heated to 130° C. The reaction was followed by HPLC. Upon completion, the reaction was poured into saturated sodium bicarbonate (50 ml) and extracted with methylene chloride (4×25 ml portions). The combined organic was dried over magnesium sulfate, filtered and evaporated. Purification was carried via preparative HPLC and the desired fractions neutralized and extracted to yield (1S,2S,3R,4R)-3-{5-Chloro-2-[1-methoxy-7-(2-methoxy-ethylamino)-6,7,8,9-tetrahydro-5H-benzocyclohepten-2-ylamino]-pyrimidin-4-ylamino}-bicyclo[2.2.1]hept-5-ene-2-carboxylic acid amide (58.19 mg, 27% yield) as the beige foam free base. Purification separated the compound into its corresponding enantiomers. $^1$H-NMR (CDCl$_3$) δ 8.17 (d, J=8.3 Hz, 1H), 7.88 (s, 1H), 7.39 (s, 1H), 6.94 (m, 1H), 6.86 (d, J=8.4 Hz, 1H), 6.37 (m, 1H), 6.31 (m, 1H), 5.61 (br s, 1H), 5.36 (br s, 1H), 4.37 (m, 1H), 3.72 (s, 3H), 3.51 (m, 2H), 3.26 (s, 3H), 3.23 (m, 1H), 3.06 (s, 1H), 2.94 (s, 1H), 2.85-2.70 (m, 6H), 2.49 (d, J=8.4 Hz, 2H), 2.24 (d, J=8.9 Hz, 1H), 2.09 (m, 2H), 1.63 (m, 2H), 1.26 (m, 4H). LC/MS (ESI+)=527 (M+H).

Example 692

(1S,2S,3R,4R)-3-{5-Chloro-2-[1-methoxy-7-(2-methoxy-ethylamino)-6,7,8,9-tetrahydro-5H-benzocyclohepten-2-ylamino]-pyrimidin-4-ylamino}-bicyclo[2.2.1]hept-5-ene-2-carboxylic acid amide This is the corresponding enantiomer of Example 691, isolated as a beige foam free base (45.27 mg, 23% yield). $^1$H-NMR (CDCl$_3$) δ 8.17 (d, J=8.3 Hz, 1H), 7.88 (s, 1H), 7.39 (s, 1H), 6.94 (m, 1H), 6.86 (d, J=8.4 Hz, 1H), 6.37 (m, 1H), 6.31 (m, 1H), 5.61 (br s, 1H), 5.36 (br s, 1H), 4.37 (m, 1H), 3.72 (s, 3H), 3.51 (m, 2H), 3.26 (s, 3H), 3.23 (m, 1H), 3.06 (s, 1H), 2.94 (s, 1H), 2.85-2.70 (m, 6H), 2.49 (d, J=8.4 Hz, 2H), 2.24 (d, J=8.9 Hz, 1H), 2.09 (m, 2H), 1.63 (m, 2H), 1.26 (m, 4H). LC/MS (ESI+)=527 (M+H).

Example 693

N-((1R,2R)-2-{5-Chloro-2-[1-methoxy-7-(2-methoxy-ethylamino)-6,7,8,9-tetrahydro-5H-benzocyclohepten-2-ylamino]-pyrimidin-4-ylamino}-cyclohexyl)-methanesulfonamide In an analogous manner to Experimental 691, part c, 1-methoxy-N*7*-(2-methoxy-ethyl)-6,7,8,9-tetrahydro-5H-benzocycloheptene-2,7-diamine and N-[(1R,2R)-2-(2,5-Dichloro-pyrimidin-4-ylamino)-cyclohexyl]-methanesulfonamide were combined to yield N-((1R,2R)-2-{5-Chloro-2-[1-methoxy-7-(2-methoxy-ethylamino)-6,7,8,9-tetrahydro-5H-benzocyclohepten-2-ylamino]-pyrimidin-4-ylamino}-cyclohexyl)-methanesulfonamide (21.60 mg, 10.1% yield) as a beige foam. Purification again separated the compound into its corresponding enantiomers. $^1$H-NMR (CDCl$_3$) δ 7.93 (s, 1H), 7.91 (d, J=8.2 Hz, 1H), 7.29 (s, 1H), 6.87 (d, J=8.2 Hz, 1H), 5.42 (d, J=7.4 Hz, 1H), 3.92 (m, 1H), 3.71 (s, 3H), 3.51 (t, J=4.8 Hz, 2H), 3.36 (s, 3H), 3.24 (m, 2H), 2.85 (m, 8H), 2.69 (m, 1H), 2.48 (m, 1H), 2.22 (d, J=10.4 Hz, 2H), 2.10 (m, 2H), 1.38 (m, 7H).

Example 694

N-((1R,2R)-2-{5-Chloro-2-[1-methoxy-7-(2-methoxy-ethylamino)-6,7,8,9-tetrahydro-5H-benzocyclohepten-2-ylamino]-pyrimidin-4-ylamino}-cyclohexyl)-methanesulfonamide This is the corresponding enantiomer of Example 693. $^1$H-NMR (CDCl$_3$) δ 7.93 (s, 1H), 7.91 (d, J=8.2 Hz, 1H), 7.29 (s, 1H), 6.87 (d, J=8.2 Hz, 1H), 5.42 (d, J=7.4 Hz, 1H), 3.92 (m, 1H), 3.71 (s, 3H), 3.51 (t, J=4.8 Hz, 2H), 3.36 (s, 3H), 3.24 (m, 2H), 2.85 (m, 8H), 2.69 (m, 1H), 2.48 (m, 1H), 2.22 (d, J=10.4 Hz, 2H), 2.10 (m, 2H), 1.38 (m, 7H).

Example 695

1-(2-{5-Chloro-2-[1-methoxy-7-(2-methoxy-ethylamino)-6,7,8,9-tetrahydro-5H-benzocyclohepten-2-ylamino]-pyrimidin-4-ylamino}-benzenesulfonyl)-pyrrolidin-3-ol In an analogous manner to Experimental 691, part c, 1-methoxy-N*7*-(2-methoxy-ethyl)-6,7,8,9-tetrahydro-5H-benzocycloheptene-2,7-diamine and 1-[2-(2,5-Dichloro-pyrimidin-4-ylamino)-benzenesulfonyl]-pyrrolidin-3-ol were combined to yield 1-(2-{5-Chloro-2-[1-methoxy-7-(2-methoxy-ethylamino)-6,7,8,9-tetrahydro-5H-benzocyclohepten-2-ylamino]-pyrimidin-4-ylamino}-benzenesulfonyl)-pyrrolidin-3-ol (12.27 mg, 7% yield) as a beige foam. $^1$H-NMR (CDCl$_3$) δ 9.36 (s, 1H), 8.50 (d, J=8.3 Hz, 1H), 8.15 (s, 1H), 7.96 (d, J=8.0 Hz, 1H), 7.59 (m, 1H), 7.46 (s, 1H), 6.80 (d, J=8.4 Hz, 1H), 4.35 (s, 1H), 3.72 (s, 3H), 3.45 (m, 2H), 3.38 (m, 5H), 3.28 (m, 2H), 2.80-2.75 (m, 4H), 2.68-2.45 (m, 2H), 2.13-1.85 (M, 4 h), 1.25 (M, 6 h). LC/MS (ESI+)=617 (M+H).

Example 696

(1S,2S,3R,4R)-3-{5-Chloro-2-[7-(2-hydroxy-ethylamino)-1-methoxy-6,7,8,9-tetrahydro-5H-benzocyclohepten-2-ylamino]-pyrimidin-4-ylamino}-bicyclo[2.2.1]hept-5-ene-2-carboxylic acid amide 696a) In an analogous manner to Experimental 675, part a, 4-Bromo-1-methoxy-2-nitro-5,6,8,9-tetrahydro-benzocyclohepten-7-one-7-one and ethanolamine were combined to yield 2-(4-Bromo-1-methoxy-2-nitro-6,7,8,9-tetrahydro-5H-benzocyclohepten-7-ylamino)-ethanol as a red oil. $^1$H-NMR (CDCl$_3$) δ 7.92 (s, 1H), 3.85 (s, 3H), 3.62 (m, 2H), 3.42 (s, 1H), 3.39 (m, 2H), 2.84 (m, 3H), 2.77 (m, 1H), 2.61 (m, 1H), 2.11 (m, 2H), 1.30 (m, 2H).

696b) In an analogous manner to Experimental 675, part b, 2-(4-Bromo-1-methoxy-2-nitro-6,7,8,9-tetrahydro-5H-benzocyclohepten-7-ylamino)-ethanol yielded 2-(2-Amino-1-methoxy-6,7,8,9-tetrahydro-5H-benzocyclohepten-7-ylamino)-ethanol as a red solid. $^1$H-NMR (CDCl$_3$) δ 6.68 (d, J=7.9 Hz, 1H), 6.52 (d, J=7.9 Hz, 1H), 4.02 (m, 2H), 3.69 (s, 3H), 3.40 (s, 2H), 3.20 (m, 2H), 2.80 (m, 1H), 2.69 (m, 1H), 2.56 (m, 4H), 0.88 (m, 2H).

696c) In an analogous manner to Experimental 691, part c, 2-(2-Amino-1-methoxy-6,7,8,9-tetrahydro-5H-benzocyclohepten-7-ylamino)-ethanol and (1S,2S,3R,4R)-3-(2,5-Dichloro-pyrimidin-4-ylamino)-bicyclo[2.2.1]hept-5-ene-2-carboxylic acid amide were combined to yield 1S,2S,3R,4R)-3-{5-Chloro-2-[7-(2-hydroxy-ethylamino)-1-methoxy-6,7,8,9-tetrahydro-5H-benzocyclohepten-2-ylamino]-pyrimidin-4-ylamino}-bicyclo[2.2.1]hept-5-ene-2-carboxylic acid amide (32.98 mg, 16.5% yield) as a beige foam. HPLC purification separated the final product into its corresponding enantiomers. $^1$H-NMR (CDCl$_3$) δ 8.18 (d, J=8.2 Hz, 1H), 7.89 (s, 1H), 7.40 (s, 1H), 6.96 (d, J=8.3 Hz, 1H), 6.86 (d, J=8.3 Hz, 1H), 6.37 (m, 1H), 6.31 (m, 1H), 5.63 (br s, 1H), 5.40 (br s, 1H), 4.36 (m, 1H), 3.72 (s, 3H), 3.63 (m, 2H), 3.23 (m, 1H), 3.06 (s, 1H), 2.94 (s, 1H), 2.85-2.52 (m, 5H). LC/MS (ESI+)=513 (M+H).

Example 697

(1S,2S,3R,4R)-3-{5-Chloro-2-[7-(2-hydroxy-ethylamino)-1-methoxy-6,7,8,9-tetrahydro-5H-benzocyclohepten-2-ylamino]-pyrimidin-4-ylamino}-bicyclo[2.2.1]hept-5-ene-2-carboxylic acid amide This is the corresponding enantiomer of Example 696 (61.28 mg 33% yield) as a brown foam. $^1$H-NMR (CDCl$_3$) δ 8.18 (d, J=8.2 Hz, 1H), 7.89 (s, 1H), 7.40 (s, 1H), 6.96 (d, J=8.3 Hz, 1H), 6.86 (d, J=8.3 Hz, 1H), 6.37 (m, 1H), 6.31 (m, 1H), 5.63 (br s, 1H), 5.40 (br s, 1H), 4.36 (m, 1H), 3.72 (s, 3H), 3.63 (m, 2H), 3.23 (m, 1H), 3.06 (s, 1H), 2.94 (s, 1H), 2.85-2.52 (m, 5H). LC/MS (ESI+)=513 (M+H).

Example 698

N-((1R,2R)-2-{5-Chloro-2-[7-(2-hydroxy-ethylamino)-1-methoxy-6,7,8,9-tetrahydro-5H-benzocyclohepten-2-ylamino]-pyrimidin-4-ylamino}-cyclohexyl)-methanesulfonamide In an analogous manner to Experimental 691, part c, 2-(2-Amino-1-methoxy-6,7,8,9-tetrahydro-5H-benzocyclohepten-7-ylamino)-ethanol and N-[(1R,2R)-2-(2,5-Dichloro-pyrimidin-4-ylamino)-cyclohexyl]-methanesulfonamide were combined to yield N-((1R,2R)-2-{5-Chloro-2-[7-(2-hydroxy-ethylamino)-1-methoxy-6,7,8,9-tetrahydro-5H-benzocyclohepten-2-ylamino]-pyrimidin-4-ylamino}-cyclohexyl)-methanesulfonamide (40.88 mg, 21% yield) as a beige foam. Purification separated the sample into its enantiomers. $^1$H-NMR (CDCl$_3$) δ 7.94 (s, 1H), 7.93 (d, J=8.52, 1H), 7.29 (s, 1H), 6.88 (d, J=8.1 Hz, 1H), 5.42 (d, J=7.4 Hz, 1H), 3.91 (m, 1H), 3.72 (s, 3H), 3.63 (m, 2H), 3.23 (m, 2H), 2.85 (m, 2H), 2.79 (s, 3H), 2.68 (m, 1H), 2.48 (m, 1H), 2.21 (m, 4H), 1.83 (m, 2H), 1.50-1.26 (m, 5H). LC/MS=553 (M+H).

Example 699

N-((1R,2R)-2-{5-Chloro-2-[7-(2-hydroxy-ethylamino)-1-methoxy-6,7,8,9-tetrahydro-5H-benzocyclohepten-2-ylamino]-pyrimidin-4-ylamino}-cyclohexyl)-methanesulfonamide This is the corresponding enantiomer of Example 698 (67.99 mg, 34% yield) isolated as a beige foam. $^1$H-NMR (CDCl$_3$) δ 7.94 (s, 1H), 7.93 (d, J=8.52, 1H), 7.29 (s, 1H), 6.88 (d, J=8.1 Hz, 1H), 5.42 (d, J=7.4 Hz, 1H), 3.91 (m, 1H), 3.72 (s, 3H), 3.63 (m, 2H), 3.23 (m, 2H), 2.85 (m, 2H), 2.79 (s, 3H), 2.68 (m, 1H), 2.48 (m, 1H), 2.21 (m, 4H), 1.83 (m, 2H), 1.50-1.26 (m, 5H). LC/MS=553 (M+H).

Example 700

(1S,2S,3R,4R)-3-(5-Chloro-2-{1-methoxy-7-[(2-methoxy-ethyl)-methyl-amino]-6,7,8,9-tetrahydro-5H-benzocyclohepten-2-ylamino}-pyrimidin-4-ylamino)-bicyclo[2.2.1]hept-5-ene-2-carboxylic acid amide 700a) In an analogous manner to Experimental 675, part a, 4-bromo-1-methoxy-2-nitro-5,6,8,9-tetrahydro-benzocyclohepten-7-one-7-one and (2-methoxy-ethyl)-methyl-amine were combined to yield (4-bromo-1-methoxy-2-nitro-6,7,8,9-tetrahydro-5H-benzocyclohepten-7-yl)-(2-methoxy-ethyl)-methyl-amine as yellow oil. $^1$H NMR (400 MHz, CDCl3) δ 7.60 (d, 1H, J=8.08 Hz), 6.99 (d, 1H, J=8.84 Hz), 3.86 (s, 3H), 3.57 (t, 1H, J=5.3 Hz), 3.45 (m, 1H), 3.35 (s, 3H), 3.08 (t, 1H, J=11.6 Hz), 2.91 (m, 1H), 2.72-2.80 (m, 3H), 2.39 (s, 3H), 2.26-2.42 (m, 2H), 1.34 (m, 2H).

700b) In an analogous manner to Experimental 675, part b, (4-Bromo-1-methoxy-2-nitro-6,7,8,9-tetrahydro-5H-benzocyclohepten-7-yl)-(2-methoxy-ethyl)-methyl-amine yielded 1-Methoxy-N*7*-(2-methoxyethyl)-N*7*-methyl-6,7,8,9-tetrahydro-5H-benzocycloheptene-2,7-diamine as a brown film. $^1$H NMR (CDCl3, 400 MHz) δ 6.71 (d, 1H, J=8.09 Hz), 6.52 (d, 1H, J=8.08 Hz), 3.70 (s, 3H), 3.57 (m, 2H), 3.35 (m, 4H), 3.12 (broad s, 2H), 2.99 (m, 2H), 2.79 (m, 2H), 2.72 (dd, 1H, J=8.33, 14.4 Hz), 2.63 (m, 1H), 2.39 (s, 3H), 2.16-2.33 (m, 2H), 1.32 (m, 2H).

700c) In an analogous manner to Experimental 691, part c, 1-Methoxy-N*7*-(2-methoxyethyl)-N*7*-methyl-6,7,8,9-tetrahydro-5H-benzocycloheptene-2,7-diamine and (1S,2S,3R,4R)-3-(2,5-Dichloro-pyrimidin-4-ylamino)-bicyclo[2.2.1]hept-5-ene-2-carboxylic acid amide were combined to yield 1S,2S,3R,4R)-3-(5-Chloro-2-{1-methoxy-7-[(2-methoxy-ethyl)-methyl-amino]-6,7,8,9-tetrahydro-5H-benzocyclohepten-2-ylamino}-pyrimidin-4-ylamino)-bicyclo[2.2.1]hept-5-ene-2-carboxylic acid amide (82.19 mg, 41% yield) as a beige foam. Purification separated the compound into its corresponding enantiomers. $^1$H-NMR (CDCl$_3$) δ 8.17 (d, J=8.0 Hz, 1H), 7.89 (s, 1H), 7.39 (s, 1H), 6.94 (d, J=7.7 Hz, 1H), 6.87 (d, J=8.4 Hz, 1H), 6.36 (m, 1H), 6.32 (m, 1H), 5.62 (br s, 1H), 5.36 (br s, 1H), 4.36 (m, 1H), 3.73 (s, 3H), 3.45 (m, 2H), 3.35 (m, 4H), 3.07 (br s, 1H), 2.94 (br s, 1H), 2.77 (m, 2H), 2.60 (m, 2H), 2.50 (d, J=8.16 Hz, 1H), 2.25 (m, 5H), 2.15 (m, 2H), 1.31 (m, 2H). LC/MS (ESI+)=541 (M+H).

Example 701

(1S,2S,3R,4R)-3-(5-Chloro-2-{1-methoxy-7-[(2-methoxy-ethyl)-methyl-amino]-6,7,8,9-tetrahydro-5H-benzocyclohepten-2-ylamino}-pyrimidin-4-ylamino)-bicyclo[2.2.1]hept-5-ene-2-carboxylic acid amide This is the corresponding enantiomer of Example 700 (76.22 mg, 38% yield) as a beige foam. $^1$H-NMR (CDCl$_3$) δ 8.17 (d, J=8.0 Hz, 1H), 7.89 (s, 1H), 7.39 (s, 1H), 6.94 (d, J=7.7 Hz, 1H), 6.87 (d, J=8.4 Hz, 1H), 6.36 (m, 1H), 6.32 (m, 1H), 5.62 (br s, 1H), 5.36 (br s, 1H), 4.36 (m, 1H), 3.73 (s, 3H), 3.45 (m, 2H), 3.35 (m, 4H), 3.07 (br s, 1H), 2.94 (br s, 1H), 2.77 (m, 2H), 2.60 (m, 2H), 2.50 (d, J=8.16 Hz, 1H), 2.25 (m, 5H), 2.15 (m, 2H), 1.31 (m, 2H). LC/MS (ESI+)=541 (M+H).

Example 702

N-[(1R,2R)-2-(5-Chloro-2-{1-methoxy-7-[(2-methoxy-ethyl)-methyl-amino]-6,7,8,9-tetrahydro-5H-benzocyclohepten-2-ylamino}-pyrimidin-4-ylamino)-cyclohexyl]-methanesulfonamide In an analogous manner to Experimental 691, part c, 1-methoxy-N*7*-(2-methoxyethyl)-N*7*-methyl-6,7,8,9-tetrahydro-5H-benzocycloheptene-2,7-diamine and N-[(1R,2R)-2-(2,5-Dichloro-pyrimidin-4-ylamino)-cyclohexyl]-methanesulfonamide were combined to yield N-[(1R,2R)-2-(5-Chloro-2-{1-methoxy-7-[(2-methoxy-ethyl)-methyl-amino]-6,7,8,9-tetrahydro-5H-benzocyclohepten-2-ylamino}-pyrimidin-4-ylamino)-cyclohexyl]-methanesulfonamide (185 mg, 42.5% yield) as a brown foam. $^1$H-NMR (CDCl$_3$) δ 7.94 (s, 1H), 7.89 (d, J=7.8 Hz, 1H), 6.88 (d, J=8.2 Hz, 1H), 5.41 (m, 1H), 3.91 (m, 1H), 3.73 (s, 1H), 3.45 (m, 2H), 3.32 (m, 5H), 2.78 (m, 7H), 2.30-2.08 (m, 7H), 1.83 (br s, 2H), 1.33 (m, 7H). LC/MS (ESI+)=581 (M+H).

Example 703

1-(2-{5-Chloro-2-[7-(2-hydroxy-ethylamino)-1-methoxy-6,7,8,9-tetrahydro-5H-benzocyclohepten-2-ylamino]-pyrimidin-4-ylamino}-benzenesulfonyl)-pyrrolidin-3-ol In an analogous manner to Experimental 691, part c, 2-(2-Amino-1-methoxy-6,7,8,9-tetrahydro-5H-benzocyclohepten-7-ylamino)-ethanol and 1-[2-(2,5-Dichloro-pyrimidin-4- ylamino)-benzenesulfonyl]-pyrrolidin-3-ol were combined to yield 1-(2-{5-Chloro-2-[7-(2-hydroxy-ethylamino)-1-methoxy-6,7,8,9-tetrahydro-5H-benzocyclohepten-2-ylamino]-pyrimidin-4-ylamino}-benzenesulfonyl)-pyrrolidin-3-ol (45.15 mg, 26% yield) as an off white foam. $^1$H-NMR (CDCl$_3$) δ 9.37 (s, 1H), 8.50 (d, J=8.2 Hz, 1H), 8.15 (s, 1H), 7.95 (m, 2H), 7.70-7.57 (m, 2H), 7.47 (s, 1H), 6.81-6.73 (m, 2H), 5.02 (br s, 1H), 4.35 (br s, 1H), 3.72 (s, 3H), 3.63 (s, 2H), 3.41 (m, 4H), 3.27 (m, 2H), 2.83 (m, 4H), 2.68 (m, 1H), 2.47 (m, 1H), 2.13 (m, 2H), 1.95 (m, 2H), 1.26 (m, 2H). LC/MS (ESI+)=603 (M+H).

Example 704

2-(2-{5-Chloro-4-[2-(pyrrolidine-1-sulfonyl)-phenylamino]-pyrimidin-2-ylamino}-1-methoxy-6,7,8,9-tetrahydro-5H-benzocyclohepten-7-ylamino)-ethanol In an analogous manner to Experimental 691, part c, 2-(2-amino-1-methoxy-6,7,8,9-tetrahydro-5H-benzocyclohepten-7-ylamino)-ethanol and (2,5-dichloro-pyrimidin-4-yl)-[2-(pyrrolidine-1-sulfonyl)-phenyl]-amine were combined to yield 2-(2-{5-Chloro-4-[2-(pyrrolidine-1-sulfonyl)-phenylamino]-pyrimidin-2-ylamino}-1-methoxy-6,7,8,9-tetrahydro-5H-benzocyclohepten-7-ylamino)-ethanol (105.68 mg, 27% yield) as a brown foam. $^1$H-NMR (CDCl$_3$) δ 9.75 (2s, 1H), 8.65 (dd, J=8.6 8.2 Hz, 1H), 8.15 (s, 1H), 7.96 (m, 2H), 7.58 (m, 1H), 7.48 (s, 1H), 7.23 (m, 1H), 6.82 (d, J=7.7 Hz, 1H), 5.30 (s, 1H), 3.73 (s, 3H), 3.26 (br s, 5H), 2.83 (m, 3H), 2.70 (m, 3H), 2.70 (m, 1H), 2.48 (m, 1H), 2.22 (m, 7H), 1.31 (m, 2H). LC/MS (ESI+)=587 (M+H).

Example 705

2-{2-[5-Chloro-4-(2-methoxy-4-morpholin-4-yl-phenylamino)-pyrimidin-2-ylamino]-1-methoxy-6,7,8,9-tetrahydro-5H-benzocyclohepten-7-ylamino}-ethanol In an analogous manner to Experimental 691, part c, 2-(2-amino-1-methoxy-6,7,8,9-tetrahydro-5H-benzocyclohepten-7-ylamino)-ethanol and (2,5-Dichloro-pyrimidin-4-yl)-(2-methoxy-4-morpholin-4-yl-phenyl)-amine were combined to yield 2-{2-[5-Chloro-4-(2-methoxy-4-morpholin-4-yl-phenylamino)-pyrimidin-2-ylamino]-1-methoxy-6,7,8,9-tetrahydro-5H-benzocyclohepten-7-ylamino}-ethanol (146.19 mg, 38% yield) as a beige foam. $^1$H-NMR (CDCl$_3$) δ 8.25 (d, J=7.5 Hz, 1H), 8.03 (m, 2H), 7.54 (s, 1H), 7.37 (s, 1H), 6.83 (d, J=6.9 Hz, 1H), 6.54 (m, 2H), 3.91 (br s, 6H), 3.72 (s, 3H), 3.63 (s, 2H), 3.17 (m, 5H), 2.85 (m, 4H), 2.68 (m, 1H), 2.47 (m, 1H), 2.14 (m, 2H), 1.31 (m, 3H). LC/MS (ESI+)=569 (M+H).

Example 711

N-((1R,2R)-2-{5-Chloro-2-[4-(2-methoxy-ethyl)-2,3,4,5-tetrahydro-benzo[f][1,4]oxazepin-7-ylamino]-pyrimidin-4-ylamino}-cyclohexyl)methanesulfonamide The title compound was prepared from 4-(2-Methoxy-ethyl)-2,3,4,5-tetrahydro-benzo[f][1,4]oxazepin-7-yl amine and N[(1S,1R)-2-(2,5-dichloro-pyrimidin-4-ylamino)cyclohexyl]methanesulfonamide in an analogous manner to example 2F. Product was isolated as a white solid (0.035 g, 23%). Mp 86-89° C., LCMS (m/e) 525 (M); 1H-NMR (DMSO, 400 MHz) δ 9.08 (s, 1H), 7.91 (s, 1H), 7.55 (s, 1H), 7.44-7.42 (d, 1H, J=8.3), 7.19-7.17 (d, 1H, J=7.58 Hz), 6.84-6.82 (d, 1H, J=7.83 Hz), 6.71-6.69 (d, 1H, J=8.08 Hz), 3.91 (m, 2H), 3.85-3.78 (m, 1H), 3.74 (s, 2H), 3.45-3.42 (t, 2H, J=5.56 Hz), 3.22 (s, 3H), 2.99 (m, 2H), 2.93 (s, 3H), 2.61-2.59 (t, 2H, J=5.56 Hz), 2.10-1.98 (m, 2H), 1.75-1.63 (m, 2H), 1.35 (s, 3H), 1.35-1.99 (m, 5H), 0.90-0.80 (m, 2H).

Example 712

5-Chloro-N*2*-(1,4-diethyl-2,3,4,5-tetrahydro-1H-benzo[e][1,4]diazepin-8-yl)-N*4*-(2-methoxy-4-morpholin-4-yl-phenyl)-pyrimidin-2,4-diamine 712a) A mixture of N,N-diethylenediamine (21.0 mL, 0.139 mol), 2-Fluoro-4-nitro-benzoic acid methyl ester (25.0 g, 0.126 mol), potassium carbonate (70.1 g, 0.507 mol) and DMF (700 mL) was mechanically stirred and heated at 100° C. for 18 hr and evaporated. To the residue was added ethyl acetate (400 mL) and water (150 mL), separated, washed, dried and evaporated to give a solid. This was triturated with hexane (300 mL) giving 1,4-Diethyl-8-nitro-1,2,3,4-tetrahydro-benzo[e][1,4]diazepin-5-one as an orange solid (26.1 g, 74%). Mp 79-80° C.; LCMS (m/e) 263 (M); $^1$H-NMR (DMSO, 400 MHz) δ 7.69 (s, 1H), 7.67 (s, 1H), 7.64 (s, 1H), 3.56-3.47 (q, 2H, J=6.79 Hz), 3.45-3.40 (t, 2H, J=5.55 Hz), 3.37-3.35 (t, 2H, J=4.80 Hz), 3.30-3.25 (q, 2H, J=7.83 Hz), 1.16-1.13 (t, 6H, J=6.82 Hz).

712b) To a solution of Diethyl-8-nitro-1,2,3,4-tetrahydro-benzo[e][1,4]diazepin-5-one (25.0 g, 0.095 mol) and 10% palladium on carbon (2.0 g) in ethanol (600 mL) was slowly added hydrazine hydrate (150 mL) and heated to 75° C. for 5 hr. After evaporation, toluene (50 mL) and ethanol (50 mL) were added and distilled leaving 8-Amino-1,4-diethyl-1,2,3,4-tetrahydro-benzo[e][1,4]diazepin-5-one as a yellow solid (22.75 g, 85%). Mp 140-141° C.; LCMS (m/e) 233 (M); $^1$H-NMR (DMSO, 400 MHz) δ 7.14-7.12 (d, 1H, J=8.85 Hz), 6.10-6.09 (d, 1H, J=6.82 Hz), 5.35 (s, 2H), 3.46-3.41 (q, 2H, 7.07 Hz), 3.19-3.16 (t, 2H, J=5.31 Hz), 3.09-3.03 (q, 2H, J=7.07 Hz), 1.12-1.06 (q, 6H, J=7.07 Hz).

712c) To a solution of 8-Amino-1,4-diethyl-1,2,3,4-tetrahydro-benzo[e][1,4]diazepin-5one (22.0 g, 0.0944 mol) in dioxane (400 mL) was added borane dimethyl sulfide complex solution (2 M in THF, 118 mL, 0.236 mol) and heated at 75° C. for 4 hr. The reaction was quenched with ethanol (100 mL) and stirred at room temperature for 18 hr., then evaporated. To the residue was added hydrazine hydrate (100 mL) and heated at 95° C. for 4 hr. After evaporation, toluene (50 mL) and ethanol (50 mL) were added, distilled and the reaction evaporated. The residue was extracted with DCM, evaporated, dissolved in ether, filtered and evaporated to give 1,4-Diethyl-2,3,4,5-tetrahydro-1H-benzo[e][1,4]diazepin-8-ylamine as an oil (16.0 g, 84%). LCMS (m/e) 220 (M+1); $^1$H-NMR (DMSO, 400 MHz) δ 6.79-6.71 (d, 1H, J=7.83 Hz), 6.49 (br, 1H), 6.01-5.99 (d, 1H, J=7.83 Hz), 4.79 (s, 2H), 3.07-3.02 (q, 2H, J=6.82 Hz), 2.85-2.83 (t, 2H, J=8.08 Hz), 2.70-2.68 (t, 2H, J=8.09 Hz), 1.13-1.10 (t, 3H, J=7.07 Hz), 1.00-0.97 (t, 3H, J=7.32 Hz), 712d) 5-Chloro-N*2*-(1,4-diethyl-2,3,4,5-tetrahydro-1H-benzo[e][1,4]diazepin-8-yl)-N*4*-(2-methoxy-4-morpholin-4-yl-phenyl)-pyrimidin-2,4-diamine was prepared from 1,4-Diethyl-2,3,4,5-tetrahydro-1H-benzo[e][1,4]diazepin-8-ylamine (0.068 g, 0.00023 mol) and (2,5-Dichloro-pyrimidin-4-yl)-(2-methoxy-4-morpholin-4-yl-phenyl)-amine (0.081 g, 0.00023 mol), camphorsulfonic acid (0.0187 g, 0.0008 mol) and methoxyethanol (10 mL). The mixture was heated at 95° C. for 18 hr. The reaction was evaporated and the residue treated with a 10% sodium carbonate solution and DCM, separated, washed, dried and evaporated to give a solid. This material was chromatographed on a silica gel prep plate with THF/methanol (10-1) giving the product as a tan solid (0.053 g, 43%). Mp 165-166° C. LCMS (m/e) 538 (M); $^1$H-NMR (DMSO, 400 MHz) δ 9.07 (s, 1H), 8.05 (s, 1H), 8.01 (s, 1H), 7.65 (d, 1H), 7.15-7.13 (d, 1H, J=8.33 Hz), 7.01 (s, 1H), 6.84-6.82 (d, 1H, J=8.08 Hz), 6.69 (s, 1H), 6.49-6.47 (d, 1H, J=8.59 Hz), 3.80 (s, 3H), 3.76 (t, 2H, J=4.05), 3.54 (s, 2H), 3.14 (t, 3H), 3.01-2.99 (q, 2H, J=7.07 Hz), 2.90-2.84 (m, 2H), 2.78-2.69 (m, 2H), 2.40-2.30 (m, 2H), 1.11-1.08 (t, 3H, J=6.57 Hz), 1.03-1.00 (t, 3H, J=7.33).

Example 713

2-[5-Chloro-2-(1,4-diethyl-2,3,4,5-tetrahydro-1H-benzo[e][1,4]diazepin-8-ylamino)-pyrimidin-4-ylamino]-benzoic acid 2-methoxy-ethyl ester The title compound was prepared from 1,4-Diethyl-2,3,4,5-tetrahydro-1H-benzo[e][1,4]diazepin-8-ylamine and 2-(2,5-Dichloro-pyrimidin-4-ylamino)-N-methyl-benzamide in an analogous manner to example 712. Product was isolated as a tan solid (0.020 g, 19%). LCMS (m/e) 525 (M); $^1$H-NMR (DMSO, 400 MHz) δ 11.50 (s, 1H), 9.40 (s, 1H), 9.00-8.90 (m, 1H), 8.27 (s, 1H), 8.06-8.04 (d, 1H, J=7.84 Hz), 7.63-7.59 (t, 1H, J=8.34 Hz), 7.25-7.17 (m, 2H), 7.14 (s, 1H), 7.03-7.01 (d, 1H, J=8.08 Hz), 6.87 (s, 1H), 6.64 (s, 1H), 4.47-4.42 (t, 2H, J=3.28 Hz), 3.71-3.66 (t, 2H, J=4.55H), 3.61 (s, 1H), 3.08-3.06 (q, 2H, J=6.57 Hz), 2.98-2.90 (m, 2H), 2.83-2.75 (m, 2H), 2.47-2.38 (m, 2H), 1.13-1.10 (t, 3H, J=6.83 Hz), 1.05-1.02 (t, 3H, J=7.07 HZ).

Example 714

(2-exo,3-exo)-3-[5-Chloro-2-(1,4-diethyl-2,3,4,5-tetrahydro-1H-benzo[e][1,4]diazepin-8-ylamino)-pyrimidin-4-ylamino]-bicyclo[2.2.1}hept-5-ene-2-carboxylic acid amide The title compound was prepared from 1,4-Diethyl-2,3,4,5-tetrahydro-1H-benzo[e][1,4]diazepin-8-ylamine and (1R,2R,3S,4S)-3-(2,5-Dichloro-pyrimidin-4-ylamino)-bicyclo[2.2.1]hept-5-ene-2-carboxylic acid amide in an analogous manner to example 712. Product was isolated as a tan solid (0.049 g, 50%). Mp 107-109° C. LCMS (m/e) 482 (M); $^1$H-NMR (DMSO, 400 HZ) δ 9.10 (s, 1H), 7.94 (s, 1H), 7.79 (s, 1H), 7.71-7.69 (d, 1H, J=7.32 Hz), 7.40-7.38 (d, 1H, J=7.37 Hz), 7.26 (s, 1H), 7.13 (s, 1H), 6.99-6.97 (d, 1H, J=7.80 Hz), 6.87 (s, 2H), 6.64 (s, 1H), 6.35 (m, 1H), 6.28 (m, 1H), 4.20-4.10 (m, 1H), 3.57 (s, 2H), 3.31 (s, 3H), 3.16-3.04 (q, 2H, J=6.06 Hz), 2.95-2.83 (m, 3H), 2.80-2.70 (m, 3H), 2.42-2.33 (q, 2H, J=7.58 Hz), 2.18 (s, 1H), 2.15-2.08 (d, 2H, J=8.34), 1.16-1.13 (t, 3H J=6.57 Hz), 1.03-0.99 (t, 3H, J=7.08 Hz).

Example 715

5-Chloro-N*2*-(1,4-diethyl-2,3,4,5-tetrahydro-1H-benzo[e][1,4]diazepin-8-yl)-N*4*-[2-(1-methyl-1H-imidazol-2-yl)-phenyl]-pyrimidine-2,4-diamine The title compound was prepared from 1,4-Diethyl-2,3,4,5-tetrahydro-1H-benzo[e][1,4]diazepin-8-ylamine and (2,5-Dichloro-pyrimidin-4-yl)-[2-(1-methyl-1H-imidazol-2-yl)-phenyl]-amine in a analogous manner to example 712. Product was isolated as a pink solid (0.122 g, 22%); Mp 58-62° C.; LCMS (m/e) 503 (M); $^1$H-NMR (DMSO, 400 MHz) δ 11.09 (s, 1H), 9.26 (s, 1H), 8.6-6.61 (d, 1H), 8.15 (s, 1H), 7.65-7.63 (d, 1H, J=7.83 Hz), 7.43-7.39 (t, 1H, J=7.58 Hz), 7.37 (s, 1H), 7.24-7.20 (t, 1H, J=7.83 Hz), 7.17 (s, 1H), 7.13 (s, 1H), 7.00-6.98 (d, 1H, J=7.83 Hz), 6.87 (s, 1H), 6.64 (s, 1H), 3.77 (s, 3H), 3.58 (s, 2H), 3.31 (s, 3H), 3.10-2.99 (q, 2H, J=7.33 Hz), 2.90 (m, 2H), 2.76 (m, 2H), 2.40-2.33 (q, 2H, J=7.08 Hz), 2.18 (s, 2H), 1.14-1.08 (t, 3H, J=6.79 Hz), 1.09-1.03 (t, 3H, J=7.07 Hz).

Example 716

2-[5-Chloro-2-(1,4-diethyl-2,3,4,5-tetrahydro-1H-1,4-benzodiazepin-8-ylamino)-pyrimidin-4-ylamino]-3-fluoro-N-methyl-benzamide The title compound was prepared from 1,4-Diethyl-2,3,4,5-tetrahydro-1H-benzo[e][1,4]diazepin-8-ylamine and 2-(2,5-Dichloro-pyrimidin-4-ylamino)-3-fluoro-N-methyl-benzamide in an analogous manner to 712. Product was isolated as a tan solid (0.026 g, 26%); Mp 111-117° C.; LCMS (m/e)-498 (M); 1H-NMR (DMSO, 400 MHz) δ 9.35 (s, 1H), 9.11 (s, 1H), 8.53 (d, 1H), 8.16 (s, 1H), 7.45-7.49 (t, 2H, J=7.07 Hz), 7.38-7.40 (q, 1H, J=6.57 Hz), 7.10-7.12 (d, 1H, J=8.33 Hz), 6.95 (s, 1H), 6.79-6.81 (d, 1H, J=8.08 Hz), 3.54 (s, 1H), 2.97-2.98 (q, 2H, J=6.83 Hz), 2.87 (s, 2H), 2.73-2.74 (s, 6H), 2.39 (m, 2H), 1.07-1.11 (t, 3H, J=6.82 Hz), 1.00-1.03 (t, 3H, J=6.82 Hz).

Example 717

(2-exo,3-exo)-3-[5-Chloro-2-(1,4-diethyl-2,3,4,5-tetrahydro-1H-1,4-benzodiazepin-8-ylamino)-pyrimidin-4-ylamino]bicyclo[2.2.1]heptane-2-carboxylic acid amide The title compound was prepared from 1,4-Diethyl-2,3,4,5-tetrahydro-1H-benzo[e][1,4]diazepin-8-ylamine and (1S,2R,3S,4R)-3-(2,5-Dichloro-pyrimidin-4-ylamino)-bicyclo[2.2.1]heptane-2-carboxylic acid amide in an analogous manner to example 712. Product was isolated as a tan solid (0.042 g, 43%); Mp 161-163° C.; LCMS (m/e) 484 (M); $^1$H-NMR DMSO, 400 MHz) δ 9.09 (s, 1H), 7.92 (s, 1H), 7.76-74 (d, 1H, J=7.58 Hz), 7.70 (s, 1H), 7.55-7.48 (d, 1H), 7.17 (s, 1H), 7.06 (s, 1H), 7.01-6.95 (d, 1H), 4.18-14 (t, 1H, J=7.83 Hz), 3.68-3.53 (br, 2H), 3.15-3.13 (q, 2H, J=7.32 Hz), 2.96-2.90 (br, 2H), 2.82-2.76 (br, 2H), 2.63-61 (d, 1H, J=8.09 Hz), 2.30 (s, 1H), 2.19 (s, 1H), 1.94-1.92 (d, 1H, J=9.85 Hz), 1.62-1.48 (m, 2H), 1.35-1.21 (m, 4H), 1.18-1.15 (m, 6H), 1.08-0.98 (t, 3H, J=6.80 Hz).

Example 718

2-[5-Chloro-2-(1,4-diethyl-2,3,4,5-tetrahydro-1H-1,4-benzodiazepin-8-ylamino)-pyrimidin-4-ylamino]-N-ethyl-benzamide The title compound was prepared from 1,4-Diethyl-2,3,4,5-tetrahydro-1H-benzo[e][1,4]diazepin-8-ylamine and 2-(2,5-Dichloro-pyrimidin-4-ylamino)-N-ethyl-benzamide in an analogous manner to example 712. Product was isolated as a tan solid (0.060 g, 53%); Mp 181-186° C.; LCMS (m/e) 494 (M); $^1$H-NMR (DMSO, 400 MHz) δ 11.56 (s, 1H), 9.30 (s, 1H), 8.81-8.74 (m, 2H), 8.21 (s, 1H), 7.75-7.77 (d, 1H, J=8.09 Hz), 7.44-7.48 (t, 1H, J=7.83 Hz), 7.23-7.25 (d, 1H, J=8.08 Hz), 7.14-7.16 (t, 2H, J=8.09 Hz), 6.99-7.01 (d, 1H, J=8.08 Hz), 3.60 (s, 2H), 3.05-3.07 (q, 2H, J=7.07 Hz), 2.92 (m, 2H), 2.77 (m, 2H), 2.39-2.41 (q, 2H, J=7.33 Hz), 1.18-1.09 (m, 6H), 1.06-1.00 (t, 3H, J=7.08 Hz).

Example 719

5-Chloro-N*4*(5-chloro-2-methoxy-phenyl-N*2*-(1,4-diethyl-2,3,4,5-tetrahydro-1H-benzo[e][1,4]diazepin-8-yl)-pyrimidine)-2,4-diamine The title compound was prepared from 1,4-Diethyl-2,3,4,5-tetrahydro-1H-benzo[e][1,4]diazepin-8-ylamine and (5-Chloro-2-methoxy-phenyl)-(2,5-dichloro-pyrimidin-4-yl)-amine in an analogous manner to example 712. Product was isolated as a tan solid (0.030 g, 31%). Mp 152-154° C.; LCMS (m/e) 487 (M); $^1$H-NMR (DMSO-400 MHz) δ 9.31 (s, 1H), 8.18 (s, 2H), 8.12 (s, 1H), 7.12-19 (m, 3H), 7.00 (s, 1H), 6.94-96 (d, 1H, J=7.83 Hz), 3.87 (s, 3H), 3.57 (s, 2H), 3.03-05 (q, 2H, J=6.82 Hz), 2.89-90 (m, 2H), 2.67 (m, 2H), 2.35-39 (q, 2H, J=6.83 Hz), 1.10-13 (t, 3H, J=6.82 Hz), 1.00-03 (t, 3H, J=6.82 Hz).

Example 720

(1S,2S,3R,4R)-3 [5-Chloro-2-(1,4-diethyl-2,3,4,5-tetrahydro-1H-1,4-benzodiazepin-8-ylamino)-pyrimidin-4ylamino]-bicyclo[2.2.1]hept-5-ene-2-carboxylic acid amide The title compound was prepared from 1,4-Diethyl-2,3,4,5-tetrahydro-1H-benzo[e][1,4]diazepin-8-ylamine and (1S,2S,3R,4R)-3-(2,5-Dichloro-pyrimidin-4-ylamino)-bicyclo[2.2.1]hept-5-ene-2-carboxylic acid amide in an analogous manner to example 712. Product was isolated as a tan solid (0.034 g, 35%). Mp 117-120° C.; LCMS (m/e) 482 (M); $^1$H-NMR (DMSO, 400 MHz) δ 9.11 (s, 1H), 7.94 (s, 1H), 7.72 (s, 1H), 7.70 (d, 1H, J=7.83 Hz), 7.39-41 (d, 1H, J=8.59 Hz), 7.26 (s, 1H), 7.14 (s, 1H), 6.99-7.01 (d, 1H, J=8.59 Hz), 6.38-6.34 (m, 1H), 6.30-5.97 (m, 1H), 4.15 (t, 1H, J=7.33 Hz), 3.59 (s, 2H), 3.10-12 (q, 2H, J=7.33 Hz), 2.91 (s, 1H), 2.88 (s, 1H), 2.77 (s, 3H), 2.40 (m, 2H), 2.10-12 (d, 1H, J=8.59 Hz), 1.39-42 (d, 1H, J=9.10 Hz), 1.13-17 (t, 3H, J=6.57 Hz), 1.01-04 (t, 3H, J=6.82 Hz).

Example 721

5-Chloro-N*2*,N*4*-bis(1,4-diethyl-2,3,4,5-tetrahydro-1H-benzo[e][1,4]diazepin-8-yl)-pyrimidin-2,4-diamine 721a) Into a Round bottom flask was added 2,4,5-Trichloro-pyrimidine (0.34 g, 0.0018 mol), 1,4-Diethyl-2,3,4,5-tetrahydro-1H-1,4-benzodiazepin-8-ylamine (0.40 g, 0.0018 mol) and Ethanol (25 mL, 0.43 mol) and was heated at 80° C. for 3 hour. The reaction was evaporated and the residue treated with a sodium carbonate solution, extracted with EtOAc, washed with water, dried and evaporated to give a solid. This was chromatographed on a SiO2 prep plate with DCM/10% ammonia/methanol (10-1) giving (2,5-Dichloro-pyrimidin-4-yl)-(1,4-diethyl-2,3,4,5-tetrahydro-1H-1,4-benzodiazepin-8-yl)-amine as a tan solid (0.43 g, 63%). Mp 69-73° C.; $^1$H-NMR (DMSO, 400 MHz) δ 9.39 (s, 1H), 8.36 (s, 1H), 7.19 (s, 1H), 7.13-7.11 (d, 1H, J=8.08 Hz), 7.05-7.03 (D, 1H, J=7.83 Hz), 3.62 (s, 2H), 3.20-3.15 (q, 3H, J=7.08 Hz), 3.02-2.95 (br, 2H), 2.84-2.76 (br (s, 2H), 2.49-2.40 (br, 2H), 1.20-1.16 (t, 3H, J=7.07 Hz), 1.06-1.02 (t, 3H, J=7.08 Hz).

721b) The title compound was prepared from 1,4-Diethyl-2,3,4,5-tetrahydro-1H-benzo[e][1,4]diazepin-8-ylamine and (2,5-Dichloro-pyrimidin-4-yl)-(1,4-diethyl-2,3,4,5-tetrahydro-1H-1,4-benzodiazepin-8-yl)-amine in an analogous manner to example 712.

Product was isolated as a tan solid (0.025 g, 16%). Mp 75-78° C.; LCMS (m/e) 549 (M); $^1$H-NMR (DMSO, 400 MHz) δ 9.12 (s, 1H), 8.67 (s, 1H), 8.09 (s, 1H), 7.25-7.19 (m, 4H), 7.04 (d, 2H, J=6.82 Hz), 6.90-6.83 (d, 1H, J=7.83 Hz), 3.63 (s, 2H), 3.56 (s, 2H), 3.09-3.00 (q, 2H, J=6.32 Hz), 2.92-2.83 (m, 4H), 2.80-2.70 (m, 3H), 2.47-2.31 (m, 4H), 1.09-1.02 (m, 12H).

Example 722

8-[5-Chloro-2-(1,4-diethyl-2,3,4,5-tetrahydro-1H-benzo[e][1,4]diazepin-8-ylamino)-pyrimidin-4-ylamino]-1,4-diethyl-1,2,3,4-tetrahydro-benzo[e][1,4]diazepin-5-one 722a) To a mixture of 2,4,5-Trichloro-pyrimidine (0.315 g, 0.00172 mol), 8-Amino-1,4-diethyl-1,2,3,4-tetrahydro-benzo[e][1,4]diazepin-5-one (0.40 g, 0.0017 mol) in anhydrous N,N-Dimethylformamide (10 mL, 0.1 mol) was added Potassium carbonate (0.35 g, 0.0025 mol) and heated at 80° C. for 17 hours. The reaction was evaporated, water added and tan solid collected. This was chromatographed on a SiO2 prep plates with hexane/acetonitrile (1-1) giving 8-(2,5-Dichloro-pyrimidin-4-ylamino)-1,4-diethyl-1,2,3,4-tetrahydro-benzo[e][1,4]diazepin-5-one as a cream colored solid (0.35 g, 54%); Mp 71-74° C.; LCMS (m/e) 380 (M); $^1$H-NMR (DMSO, 400 MHz) 9.50 (s, 1H), 8.42 (s, 1H), 7.45-7.43 (d, 1H, J=7.83 Hz), 7.35 (s, 1H), 7.21-7.19 (d, 1H, J=8.34 Hz), 3.54-3.48 (q, 2H, J=7.08 Hz), 3.43-3.41 (t, 2H, J=5.31 Hz), 3.32-3.28 (t, 2H, J=4.04 Hz), 3.21-3.16 (q, 2H, J=6.32 Hz), 1.16-1.11 (t, 3H, J=7.07 Hz), 1.20-1.18 (t, 3H, J=6.82 Hz).

722b) The title compound was prepared from 1,4-Diethyl-2,3,4,5-tetrahydro-1H-benzo[e][1,4]diazepin-8-ylamine and 8-(2,5-Dichloro-pyrimidin-4-ylamino)-1,4-diethyl-1,2,3,4-tetrahydro-benzo[e][1,4]diazepin-5-one in an analogous manner to example 712. Product was isolated as a tan solid (0.080 g, 40%). Mp 100-106° C.; LCMS (m/e) 563 (M); $^1$H-NMR (DMSO, 400 MHz) δ 9.27 (s, 1H), 8.90 (s, 1H), 8.23 (s, 1H), 7.52-49 (d, 1H, J=8.59 Hz), 7.46-44 (d, 1H, J=8.33 Hz), 7.31-23 (s, 2H), 7.20-18 (d, 1H, J=7.84 Hz), 7.01-6.96 (d, 1H, J=8.34 Hz), 3.67-60 (br, 1H), 3.60-55 (q, 1H, J=6.82 Hz), 3.48-42 (t, 1H, J=5.06 Hz), 3.38-31 (s, 2H), 3.31-29 (t, 1H, J=6.57 Hz), 3.16-06 (q, 1H, J=6.82 Hz), 3.10-2.96 (m, 3H), 2.84-80 (br, 1H), 2.56-40 (br, 2H), 1.21-16 (t, 3H, J=7.07 Hz), 1.18-08 (m, 9H).

Example 723

2-{{7-[5-Chloro-4-[1,4-d]ethyl-2,3,4,5-tetrahydro-1H-benzo[e][1,4]diazepin-2-ylamino]-pyrimidin-2-ylamino}-8-methoxy-1,2,3,4-tetrahydro-benzo[d]azepin-3-yl-N,N-dimethyl-acetamide The title compound was prepared from 2-(7-Amino-8-methoxy-1,2,4,5-tetrahydro-benzo[d]azepin-3-yl)-N,N-dimethyl-acetamide (0.068 g, 0.00024 mol) and (2,5-Dichloro-pyrimidin-4-yl)-(1,4-diethyl-2,3,4,5-tetrahydro-1H-benzo[e][1,4]diazepin-8-yl)-amine (0.090 g, 0.00024 mol), 4 M HCl in dioxane (0.19 mL, 0.0022 mol) and isopropyl alcohol (5 mL). The mixture was heated in a microwave at 130° C. for 1 hr. The reaction was evaporated and the residue treated with a 10% sodium carbonate solution. A solid was collected and then chromatographed on a silica gel prep plate with DCM/10% ammonia/methanol giving the product as a tan solid (0.064 g, 43%). Mp 85-90° C.; LCMS (m/e) 607 (M); $^1$H-NMR (DMSO, 400 MHz) δ 8.74 (s, 1H), 8.09 (s, 1H), 7.72 (s, 1H), 7.61 (s, 1H), 7.19-11 (d, 1H, J=7.58 Hz), 7.05-04 (d, 1H, J=8.34 Hz), 7.02-6.97 (s, 1H), 3.79 (s, 3H), 3.70-62 (br, 2H), 3.32 (s, 6H), 3.24 (s, 2H), 3.13-11 (m, 2H), 3.09-07 (s, 3H), 2.94-89 (br, 2H), 2.83 (s, 3H), 2.78-73 (br, 4H), 2.55-51 (s, 2H), 1.15-13 (t, 3H, J=6.57 Hz), 1.07-03 (t, 3H, J=7.08 Hz).

Example 724

2-{7-[5-Chloro-4-(1,4-diethyl-5-oxo-2,3,4,5-tetrahydro-1H-benzo[e][1,4]diazepin-8-ylamino)-pyrimidin-2-ylamino]-8-methoxy-1,2,3,4-tetrahydro-benzo[d]azepin-3-yl}-N,N-dimethyl-acetamide The title compound e was prepared from 2-(7-Amino-8-methoxy-1,2,4,5-tetrahydro-benzo[d]azepin-3-yl)-N,N-dimethyl-acetamide and 8-(2,5-Dichloro-pyrimidin-4-ylamino)-1,4-diethyl-1,2,3,4-tetrahydro-benzo[e][1,4]diazepin-5-one in a manner analogous to example 724. Product isolated as a tan solid (0.064 g, 45%). Mp 85-89° C.; LCMS (m/e) 621 (M); $^1$H-NMR (DMSO, 400 MHz) δ 8.87 (s, 1H), 8.14 (s, 1H), 7.96 (s, 1H), 7.75 (s, 1H), 7.68 (s, 1H), 7.34-7.30 (q, 2H, J=8.08 Hz), 7.16 (s, 1H), 6.80 (s, 1H), 3.78 (s, 3H), 3.51-3.48 (q, 2H, J=7.08 Hz), 3.46-3.40 (t, 2H, J=5.31 Hz), 3.29-3.25 (m, 4H), 3.19-3.09 (q, 2H, J=7.07 Hz), 3.08-3.05 (s, 3H), 2.95-2.89 (s, 2H), 2.82-2.78 (s, 3H), 2.78-2.73 (br, 2H), 2.67 (s, 2H), 2.67-2.56 (s, 3H), 1.15-1.11 (t, 6H, J=6.99 Hz).

Example 725

5-Chloro-N(2)-(1,4-diethyl-2,3,4,5-tetrahydro-1H-benzo[e][1,4]diazepin-8-yl)-N(4)-(2-pyrazol-1-yl-phenyl)-pyrimidine-2,4-diamine The title compound was prepared from 1,4-Diethyl-2,3,4,5-tetrahydro-1H-benzo[e][1,4]diazepin-8-ylamine and (2,5-Dichloro-pyrimidin-4-yl)-(2-pyrazol-1-yl-phenyl)-amine in an analogous manner to example 724. Product was isolated as a tan solid (0.023 g, 14%). Mp 77-82° C.; LCMS (m/e) 489 (M); $^1$H-NMR (DMSO, 400 MHz) δ 10.28 (s, 1H), 9.26 (s, 1H), 8.49-8.47 (d, 1H, J=8.34 Hz), 8.16 (s, 1H), 7.92 (s, 1H), 7.63-7.61 (d, 1H, J=7.89 Hz), 7.42-7.40 (t, 1H, J=7.83 Hz), 7.30-7.26 (t, 1H, J=7.58 Hz), 7.22-7.20 (d, 1H, J=8.33 Hz), 7.08 (s, 1H), 6.96-6.94 (d, 1H, J=7.85 Hz), 6.60 (s, 1H), 3.58-3.52 (s, 2H), 3.09-3.03 (q, 2H, J=6.57 Hz), 2.92-2.85 (s, 2H), 2.76-2.70 (s, 2H), 2.40-2.33 (m, 2H), 1.17-1.08 (t, 3H, J=6.57 Hz), 1.05-1.01 (t, 3H, J=6.82 Hz).

Example 726

8-[5-Chloro-4-(2-methoxy-4-morpholin-4-yl-phenylamino)-pyrimidin-2-ylamino]-1-ethyl-7-methoxy-4-(2-methoxy-ethyl)-1,3,4,5-tetrahydro-benzo[e][1,4]diazepin-2-one 726a) A mixture of 8-Amino-1-ethyl-7-methoxy-1,3,4,5-tetrahydro-benzo[e][1,4]diazepin-2-one (0.140 g, 0.000595 mol), Ethane, 1-bromo-2-methoxy (0.108 g, 0.000738 mol), Potassium carbonate (0.125 g, 0.000904 mol) in N,N-Dimethylformamide (6 mL, 0.08 mol) was heated at 50° C. for 18 hr. The reaction was evaporated and the residue taken up in water and ethyl acetate, separated, dried and evaporated to give a tan solid. This material was chromatographed on a silica gel prep plate with DCM/10% ammonia/methanol (10-1) giving 8-Amino-4-ethoxymethyl-1-ethyl-7-methoxy-1,3,4,5-tetrahydro-benzo[e][1,4]diazepin-2-one as a tan solid (0.04 g, 20%). LCMS (m/e) 294 (M).

726b) The title compound was prepared from 8-Amino-4-ethoxymethyl-1-ethyl-7-methoxy-1,3,4,5-tetrahydro-benzo[e][1,4]diazepin-2-one and (2,5-Dichloro-pyrimidin-4-yl)-(2-methoxy-4-morpholin-4-yl-phenyl)-amine in an analogous manner to example 724. Product was isolated as a tan solid (0.011 g, 15%). Mp 67-70° C.; LCMS (m/e) 612 (M); $^1$H-NMR (DMSO, 400 MHz) δ 8.09 (s, 1H), 8.07 (s, 1H), 7.95 (s, 1H), 7.82 (s, 1H), 7.54-7.52 (d, 1H, J=9.09 Hz), 7.02 (s, 1H), 6.76 (s, 1H), 6.61 (s, 1H), 6.36-6.34 (d, 1H, J=8.59 Hz), 4.87 (s, 1H), 3.86 (s, 3H), 3.79-3.77 (m, 8H), 3.52 (s, 3H), 3.47-3.42 (q, 8H, J=7.58 Hz), 3.24 (d, 8H, J=2.22), 3.11 (m, 3H), 2.96 (s, 2H), 2.92 (s, 2H), 2.71-66 (m, 3H), 0.90-0.86 (t, 3H, J=6.82 Hz).

Example 727

2-{8-[5-Chloro-4-(2-methoxy-4-morpholin-4-yl-phenylamino)-pyrimidin-2-ylamino]-1-ethyl-7-methoxy-2-oxo-1,2,3,5-tetrahydro-benzo[e][1,4]diazepin-4-yl}-N,N-dimethyl-acetamide 727a) A mixture of 8-Amino-1-ethyl-7-methoxy-1,3,4,5-tetrahydro-benzo[e][1,4]diazepin-2-one (0.140 g, 0.000595 mol), 2-Chloro-N,N-dimethyl-acetamide (0.094 g, 0.00077 mol), Cesium Carbonate (0.376 g, 0.00115 mol) and Sodium iodide (0.052 g, 0.00035 mol) in Acetonitrile (10 mL, 0.2 mol) was refluxed for 18 hrs. The reaction was evaporated and the residue taken up in water/ethyl acetate, separated, dried and evaporated to give a tan solid. This material was chromatographed twice on a silica gel prep plates with DCM/10% ammonia/methanol (10-1) giving 2-(8-Amino-1-ethyl-7-methoxy-2-oxo-1,2,3,5-tetrahydrobenzo[e][1,4]diazepin-4-yl)-N,N,dimethylacetamide as a tan solid (0.05 g, 30%). LCMS (m/e) 321 (M+1); $^1$H-NMR (DMSO, 400 MHz) δ 6.77 (s, 1H), 6.62 (s, 1H), 4.90 (s, 2H), 3.78 (s, 3H), 3.43 (s, 2H), 3.27 (s, 2H), 3.01 (s, 3H), 2.92 (s, 2H), 2.82 (s, 3H), 1.05-1.02 (t, 3H, J=7.33 Hz).

727b) The title compound was prepared from 2-(8-Amino-1-ethyl-7-methoxy-2-oxo-1,2,3,5-tetrahydro-benzo[e][1,4]diazepin-4-yl)-N,N-dimethyl-acetamide and (2,5-Dichloro-pyrimidin-4-yl)-(2-methoxy-4-morpholin-4-yl-phenyl)-amine in an analogous manner to example 724. Product was isolated as a tan solid (0.017 g, 18%). Mp 98-101° C.; LCMS (m/e) 639 (M); $^1$H-NMR (DMSO, 400 MHz) δ 8.10 (s, 1H), 8.08 (s, 1H), 7.97 (s, 1H), 7.82 (s, 1H), 7.54-7.52 (d, 1H, J=8.84 Hz, 6.99 (s, 1H), 6.61 (d, 1H), 6.37-6.34 (d, 1H, J=10.61 Hz), 3.86 (s, 3H), 3.80-3.74 (m, 8H), 3.53 (s, 3H), 3.12-3.11 (t, 4H, J=4.8 Hz), 3.02 (s, 3H), 2.97 (s, 2H), 2.83 (s, 4H), 1.19-1.18 (d, 1H, J=6.32 Hz), 0.90-0.86 (t, 3H, J=7.33 Hz).

Example 728

5-Chloro-N(2)-(1,4-diethyl-2,3,4,5-tetrahydro-1H-benzo[e][1,4]diazepin-8-yl)-N(4)-[2-(propane-2-sulfonyl)-phenyl]-pyrimidine-2,4-diamine The title compound was prepared from 1,4-Diethyl-2,3,4,5-tetrahydro-1H-benzo[e][1,4]diazepin-8-ylamine and (2,5-Dichloro-pyrimidin-4-yl)-[2-(propane-2-sulfonyl)-phenyl]-amine in an analogous manner to example 724. Product was isolated as a tan solid (0.024 g, 12%). Mp 90-94° C.; LCMS (m/e) 529 (M); $^1$H-NMR (DMSO, 400 MHz) δ 9.47 (s, 1H), 9.43 (s, 1H), 8.59 (m, 1H), 8.29 (s, 1H), 7.86-7.84 (d, 1H, J=7.83 Hz), 7.72 (t, 1H, J=8.08 Hz), 7.40-7.36 (t, 1H, J=7.83 Hz), 7.15 (s, 1H), 7.01-6.95 (d, 1H, J=8.33 Hz), 3.61-3.52 (m, 2H), 3.47-3.45 (q, 2H, J=6.32 Hz), 2.96-2.90 (m, 5H), 2.80-2.70 (m, 2H), 1.23-1.17 (d, 6H, J=6.82 Hz), 1.08-0.98 (t, 6H, J=6.82 Hz).

Example 729

8-{5-Chloro-4-[2-(propane-2-sulfonyl)-phenylamino]-pyrimidin-2-ylamino}-1-ethyl-7-methoxy-1,3,4,5-tetrahydro-benzo[e][1,4]diazepin-2-one 729a) To a solution of Sodium hydride (0.135 g, 0.00338 mol) and N,N-Dimethylformamide (40 mL, 0.5 mol) was added at 5° C. 7-Methoxy-8-nitro-2-oxo-1,2,3,5-tetrahydro-benzo[e][1,4]diazepine-4-carboxylic acid benzyl ester (1.00 g, 0.00269 mol) and stirred for 1 hour at room temperature. Iodoethane (0.286 mL, 0.00358 mol) was added and stirred for 3 hours. The solvent was evaporated and the residue taken up in water and ethyl acetate, separated, washed, dried and evaporated to a give a gum. Trituration with hexane gave 1-Ethyl-7-methoxy-8-nitro-2-oxo-1,2,3,5-tetrahydro-benzo[e][1,4]diazepine-4-carboxylic acid benzyl ester as a red solid (1.01 g). (94%). Mp 55-56° C. LCMS (m/e) 400 (M+1); $^1$H-NMR (DMSO, 400 MHz) δ 8.02 (s, 1H), 7.58 (s, 1H), 7.50-7.30, (br, 5H), 5.15 (s, 2H), 4.56-4.48 (br, 2H), 3.94 (s, 3H), 3.91-3.84 (m, 4H), 1.05-1.01 (t, 3H, J=7.07 Hz).

729b) A mixture of 1-Ethyl-7-methoxy-8-nitro-2-oxo-1,2,3,5-tetrahydro-benzo[e][1,4]diazepine-4-carboxylic acid benzyl ester (0.95 g, 0.0024 mol). and 10% Pd/C (10:90, Palladium:carbon black, 0.095 g) in Ethanol (100 mL, 2 mol) was hydrogenated on a Paar shaker for 1 day. The catalyst was filtered and the filtrate evaporated to give 8-Amino-1-ethyl-7-methoxy-1,3,4,5-tetrahydro-benzo-[e][1,4]diazepin-2-one as a tan solid (0.55 g). (98%). Mp 69-73° C.; LCMS (m/e) 236 (M+1); $^1$H-NMR (DMSO, 400 MHz) δ 6.75 (s, 1H), 6.61 (s, 1H), 4.83 (s, 2H), 3.76 (s, 3H), 3.74-68 (q, 2H, J=7.33 Hz), 3.58 (s, 2H), 2.97 (s, 2H), 1.05-02 (t, 3H, J=7.32 Hz).

729c) The title compound was prepared from 8-Amino-1-ethyl-7-methoxy-1,3,4,5-tetrahydro-benzo[e][1,4]diazepin-2-one (0.095 g, 0.0004 mol), (2,5-Dichloro-pyrimidin-4-yl)-[2-(propane-2-sulfonyl)-phenyl]-amine (0.127 g, 0.000367 mol), p-toluenesulfonic acid monohydrate (0.17 g, 0.00089 mol) and isopropyl alcohol (4 mL). The mixture was heated in a microwave at 130° C. for 30 min. The reaction was evaporated and the residue treated with a 10% sodium carbonate solution and DCM, separated, washed, dried and evaporated to give a solid. This material was chromatographed on a silica gel prep plate with DCM/10% ammonia/methanol (10-1) giving the product as tan solid (0.041 g, 19%). Mp 179-184° C.; LCMS (m/e) 545 (M); $^1$H-NMR (DMSO, 400 MHz) δ 9.43 (s, 1H), 8.40-8.36 (d, 1H), 8.33 (s, 1H), 8.30 (s, 1H), 7.83 (s, 1H), 7.82 (s, 1H), 7.55-7.48 (t, 1H, J=7.32 Hz), 7.32-7.29 (t, 1H, J=7.83 Hz), 7.04 (s, 1H), 3.83 (s, 3H), 3.70 (s, 2H), 3.55-3.40 (m, 3H), 3.03 (s, 2H), 1.23-1.14 (d, 6H, J=6.82 Hz), 0.90-0.86 (t, 3H, J=7.08 Hz).

Example 730

2-[5-Chloro-2-(1,4-diethyl-2,3,4,5-tetrahydro-1H-benzo[e][1,4]diazepin-8-ylamino)-pyrimidin-4-ylamino]-N,N-dimethyl-benzenesulfonamide The title compound was prepared from 1,4-Diethyl-2,3,4,5-tetrahydro-1H-benzo[e][1,4]diazepin-8-ylamine (0.105 g, 0.000407 mol), 2-(2,5-Dichloro-pyrimidin-4-ylamino)-N,N-dimethyl-benzenesulfonamide (0.140 g, 0.000403 mol), 10-camphorsulfonic acid (0.237 g, 0.0010 mol) and isopropyl alcohol (4 mL). The mixture was heated in a microwave at 100° C. for 20 min. After evaporation of the solvent, the residue was treated with a 10% sodium carbonate solution/DCM, separated, washed, dried and evaporated to give a solid. This material was chromatographed on a silica gel prep plate with DCM/10% ammonia/methanol (10-1) giving the product as a tan solid (0.084 g, 39%). Mp 88-91° C. LCMS (m/e) 530 (M); $^1$H-NMR (DMSO, 400 MHz) δ 9.41 (s, 1H), 9.31 (s, 1H), 8.68-8.56 (m, 1H), 7.82-7.80 (d, 1H, J=7.80 Hz), 7.70-7.66 (t, 1H, J=8.84 Hz), 7.37-7.33 (t, 1H, J=7.58 Hz), 7.14 (s, 2H), 7.00-6.98 (d, 1H, J=8.60 Hz), 3.59-3.42 (br, 2H), 3.06-2.89 (m, 5H), 2.76-2.68 (m, 2H), 2.65 (s, 4H), 2.47-2.38 (m, 4H), 1.09-1.03 (m, 6H).

Example 731

{2-[5-Chloro-2-(1,4-diethyl-2,3,4,5-tetrahydro-1H-benzo[e][1,4]diazepin-8-ylamino)-pyrimidin-4-ylamino]-phenoxy}-acetonitrile The title compound was prepared from 1,4-Diethyl-2,3,4,5-tetrahydro-1H-benzo[e][1,4]diazepin-8-ylamine and [2-(2,5-Dichloro-pyrimidin-4-ylamino)-phenoxy]-acetonitrile in an analogous manner to example 730. Product was isolated as a tan solid (0.044 g, 31%). Mp 80-83° C.; LCMS (m/e) 478 (M+1); $^1$H-NMR (DMSO, 400 MHz) δ 9.17 (s, 1H), 8.23 (s, 1H), 8.14 (s, 1H), 7.99-7.97 (d, 1H, J=8.36 Hz), 7.28-7.22 (m, 2H), 7.16-7.07 (q, 2H, J=8.31 Hz), 7.05 (s, 1H), 6.95-6.87 (d, 1H, J=7.56 Hz), 5.21 (s, 2H), 3.76-3.57 (br, 1H), 3.09-2.97 (q, 2H, J=7.08 Hz), 2.93-2.85 (m, 2H), 2.83-2.70 (m, 2H), 2.48-2.35 (br, 2H), 1.15-1.08 (t, 3H, J=7.08 Hz), 1.07-0.99 (t, 3H, J=6.82 Hz).

Example 732

5-Chloro-N(2)-(1,4-diethyl-2,3,4,5-tetrahydro-1H-benzo[e][1,4]diazepin-8-yl)-N(4)-(4-methoxy-2-pyrazol-1-yl-phenyl)-pyrimidine-2,4-diamine The title compound was prepared from 1,4-Diethyl-2,3,4,5-tetrahydro-1H-benzo[e][1,4]diazepin-8-ylamine and (2,5-Dichloro-pyrimidin-4-yl)-(4-methoxy-2-pyrazol-1-yl-phenyl)-amine in an analogous manner to example 730. Product was isolated as a tan solid (0.043 g, 39%). Mp 82-87° C. LCMS (m/e) 519 (M); $^1$H-NMR (DMSO, 400 MHz) δ 9.83 (s, 1H), 9.17 (s, 1H), 8.29 (s, 1H), 8.16-8.13 (d, 1H, J=8.59 Hz), 8.09 (s, 1H), 7.85 (s, 1H), 7.20 (s, 1H), 7.20-7.15 (br, 1H), 7.10-7.05 (br, 1H), 7.00-6.95 (q, 1H, J=7.08 Hz), 6.95-6.90 (br, 1H), 6.55 (s, 1H), 3.85 (s, 3H), 3.70-3.50 (br, 1H), 3.17-3.16 (d, 1H, J=5.30 Hz), 3.05-2.70 (m, 6H), 1.15-1.00 (m, 6H).

Example 733

5-Chloro-N(2)-(1,4-diethyl-2,3,4,5-tetrahydro-1H-benzo[e][1,4]diazepin-8-yl)-N(4)-[8-(2-methoxy-ethyl)-6,7,8,9-tetrahydro-5-thia-8-aza-benzocyclohepten-2-yl]-pyrimidine-2,4-diamine 733a) A mixture of 8-(2-Methoxy-ethyl)-6,7,8,9-tetrahydro-5-thia-8-aza-benzocyclohepten-2-ylamine (0.130 g, 0.000545 mol), 2,4,5-Trichloro-pyrimidine (0.10 g, 0.00054 mol) and Potassium carbonate (0.11 g, 0.00080 mol) in N,N-Dimethylformamide (5 mL, 0.07 mol) was heated at 80° C.

for 4 hours. The reaction was evaporated, taken up in DCM and water, separated, washed, dried and evaporated to give an oil (0.17 g). The crude product was dissolved in ether, filtered and the filtrate evaporated to give the product as a tacky solid (0.14 g, 67%). LCMS (m/e) 385 (M); $^1$H-NMR (DMSO, 400 MHz) δ 9.54 (s, 1H), 8.39 (s, 1H), 7.56 (s, 1H), 7.52-7.47 (d, 1H, J=6.57 Hz), 7.45-7.40 (d, 1H, J=8.33 Hz), 4.03 (s, 2H), 3.37-3.32 (t, 2H, J=5.81 Hz), 3.23 (s, 6H), 2.89 (s, 1H), 2.75-2.73 (s, 3H).

733b) The title compound was prepared from 1,4-Diethyl-2,3,4,5-tetrahydro-1H-benzo[e][1,4]diazepin-8-ylamine and (2,5-Dichloro-pyrimidin-4-yl)-[8-(2-methoxy-ethyl)-6,7,8,9-tetrahydro-5-thia-8-aza-benzocyclohepten-2-yl]-amine in an analogous manner to example 730. Product was isolated as a tan solid (0.040 g, 42%). Mp 62-66° C. LCMS (m/e) 568 (M); $^1$H-NMR (DMSO, 400 MHz) δ 9.17 (s, 1H), 8.80 (s, 1H), 8.13 (s, 1H), 7.62-57 (m, 2H), 7.41-39 (d, 1H, J=8.85 Hz), 7.13-08 (m, 2H), 6.95-89 (d, 1H, J=8.34 Hz), 3.99 (s, 2H), 3.65-55 (s, 2H), 3.48-3.40 (q, 1H, J=5.79 Hz), 3.38-32 (t, 2H, J=5.56 Hz), 3.28-20 (m, 2H), 2.95-85 (m, 6H), 2.82-62 (m, 6H), 2.49-43 (t, 2H, J=5.81 Hz), 2.43-35 (m, 2H), 1.10-0.98 (m, 6H).

Example 734

2-({5-[5-Chloro-2-(1,4-diethyl-2,3,4,5-tetrahydro-1H-benzo[e][1,4]diazepin-8-ylamino)-pyrimidin-4-ylamino]-2-fluoro-benzyl}-ethyl-amino)-ethanol The title compound was prepared from Diethyl-2,3,4,5-tetrahydro-1H-1,4-benzodiazepin-8-ylamine and 2-{[5-(2,5-Dichloro-pyrimidin-4-ylamino)-2-fluoro-benzyl]-ethyl-amino}-ethanol in an analogous manner to example 730. Product was isolated as a tan solid (0.048 g, 39%). Mp 56-59° C. LCMS (m/e) 542 (M). $^1$H-NMR (DMSO, 400 MHz) δ 9.11 (s, 1H), 8.85 (s, 1H), 8.11 (s, 1H), 7.64-7.53 (t, 2H), 7.11-7.05 (t, 3H), 6.90-6.88 (d, 1H, J=7.80 Hz), 4.32 (br, 1H), 3.58 (s, 4H), 3.48-3.40 (t, 2H, J=6.31 Hz), 3.10-00 (q, 1H, J=7.33 Hz), 2.98-2.85 (m, 4H), 2.85-2.70 (m, 2H), 2.48-2.35 (m, 4H), 1.10-0.97 (m, 6H), 0.97-0.90 (t, 3H, J=7.07 Hz).

Example 735

2-{7-[5-Chloro-4-(3-{[ethyl-(2-hydroxy-ethyl)-amino]-methyl}-4-fluoro-phenylamino)-pyrimidin-2-ylamino]-8-methoxy-1,2,4,5-tetrahydro-benzo[d]azepin-3-yl}-N,N-dimethyl-acetamide The title compound was prepared from 2-{[5-(2,5-Dichloro-pyrimidin-4-ylamino)-2-fluoro-benzyl]-ethyl-amino}-ethanol and 2-(7-Amino-8-methoxy-1,2,4,5-tetrahydro-benzo[d]azepin-3-yl)-N,N-dimethyl-acetamide in an analogous manner to example 730 (0.047 g, 43%). Mp 71-75° C. LCMS (m/e) 600 (M); $^1$H-NMR (DMSO, 400 MHz) δ 8.90 (s, 1H), 8.09 (s, 1H), 7.63 (s, 1H), 7.59 (s, 1H), 7.58-7.48 (m, 3H), 7.10-7.02 (t, 1H, J=9.09 Hz), 6.78 (s, 1H), 4.35-4.25 (t, 1H), 3.77 (s, 3H), 3.59 (s, 2H), 3.46-3.45 (q, 2H, J=6.06 Hz), 3.35-3.20 (br, 2H), 3.05 (s, 4H), 2.82 (s, 4H), 2.73 (br, 2H), 2.65-2.52 (m, 4H), 0.98-0.94 (t, 3H, J=7.08 Hz).

Example 736

N,N-{(1R,2R)-2-[5-Chloro-2-(1,4-diethyl-7-methoxy-2-oxo-2,3,4,5-tetrahydro-1H-benzo[e][1,4]diazepin-8-ylamino)-pyrimidin-4-ylamino]-cyclohexyl}-methanesulfonamide 736a) A slurry of 7-Methoxy-1,3,4,5-tetrahydro-benzo[e][1,4]diazepin-2-one (12.40 g, 0.06451 mol) in Acetonitrile (300 mL, 6 mol) was cooled to at 0° C. and treated with Trifluoroacetic anhydride (31.40 mL, 0.2223 mol). After 1 hr Potassium nitrate (13.70 g, 0.1355 mol) was added in 10 min. and stirred at 0° C. for 2 hrs and then at room temperature overnight. A solution of 10% sodium bicarbonate (100 mL) (pH 8.5-9) was added to the reaction mixture, precipitating the 6-nitro isomer, 7-Methoxy-6-nitro-4-(2,2,2-trifluoro-acetyl)-1,3,4,5-tetrahydro-benzo[e][1,4]diazepin-2-one, which was collected and washed. Mp 239-240° C.; LCMS (m/e) 334 (M+1); $^1$H-NMR (DMSO, 400 MHz) δ 10.51 (s, 0.5H), 10.43 (s, 0.5H), 7.38-32 (q, 2H, J=8.8/4 Hz), 4.72 (s, 0.5H), 4.65 (s, 1H), 4.41 (s, 1H), 4.32 (s, 0.5H), 3.88-86 (s, 3H).

736b) The aqueous solution was diluted with water to 1400 mL and extracted with 200 mL of ether and 100 mL of THF (3×). This extract was washed with brine, dried (MgSO4) and evaporated to give a solid (7.5 g). This was chromatographed on SiO2 (340 g) with (2-1) ethyl acetate-THF to give the 8-nitro isomer, 7-Methoxy-8-nitro-4-(2,2,2-trifluoro-acetyl)-1,3,4,5-tetrahydro-benzo[e][1,4]diazepin-2-one as a solid (5.55 g, 25%) Mp 204-205° C.; LCMS (m/e) 334 (M+1); $^1$H-NMR (DMSO, 400 MHz) δ 10.43 (s, 0.5H), 10.33 (s, 0.5H), 7.69-67 (d, 1H, J=9.34 Hz), 7.51 (s, 0.5H), 4.95 (s, 0.5H), 4.83 (s, 1H), 4.43-40 (d, 2H, J=9.86 Hz), 3.91-90 (d, 3H, J=5.31 Hz).

736c) A mixture of 7-Methoxy-8-nitro-4-(2,2,2-trifluoro-acetyl)-1,3,4,5-tetrahydro-benzo[e][1,4]diazepin-2-one (0.640 g, 0.00192 mol), Cesium fluoride (0.580 g, 0.00382 mol), Ethyl bromide (0.860 mL, 0.0116 mol) and Sodium iodide (0.0014 g, 0.0000093 mol) in Acetonitrile (15.0 mL, 0.287 mol) was heated at 45° C. for 8 hr. The reaction was evaporated, taken up in DCM/water, separated, washed, dried and evaporated to give 1-Ethyl-7-methoxy-8-nitro-4-(2,2,2-trifluoro-acetyl)-1,3,4,5-tetrahydro-benzo[e][1,4]diazepinone as a solid (0.59 g, 85%). Mp 128-129° C.; LCMS (m/e) 362 (M+1); $^1$H-NMR (DSMO, 400 MHz) δ 8.07 (d, 1H), 7.95 (s, 0.5H), 7.67 (s, 1H), 7.53 (s, 0.5H), 4.69 (s, 1H), 4.06 (s, 0.5H), 4.00 (s, 1H), 3.95 (s, 1H), 3.91-89 (q, 2H), 1.08-04 (t, 3H).

736d) A mixture of 1-Ethyl-7-methoxy-8-nitro-4-(2,2,2-trifluoro-acetyl)-1,3,4,5-tetrahydro-benzo[e][1,4]diazepin-2-one (0.59 g, 0.0016 mol) and 10% ammonia/methanol (30 mL) was stirred at room temperature for 2 hrs. The reaction was evaporated to give 1-Ethyl-7-methoxy-8-nitro-1,3,4,5-tetrahydro-benzo[e][1,4]diazepin-2-one as a tan solid (0.43 g, 97%). Mp 132-134° C.; LCMS (m/e) 266 (M+1); $^1$H-NMR (DMSO, 400 Mz) δ 8.76 (br, 0.5H), 8.48 (br, 0.5H), 7.93 (s, 1H), 7.42 (s, 1H), 3.94 (s, 3H), 3.94-80 (q, 2H, J=6.82 Hz), 3.78 (s, 2H), 3.05 (s, 2H), 1.04-00 (t, 3H, J=7.07 Hz).

731e) A mixture of 1-Ethyl-7-methoxy-8-nitro-1,3,4,5-tetrahydro-benzo[e][1,4]diazepin-2-one (0.42 g, 0.0016 mol), Ethyl bromide (0.244 mL, 0.00329 mol), Sodium iodide (0.0033 g, 0.000022 mol) and N,N-Diisopropylethylamine (1.14 mL, 0.00654 mol) in N,N-Dimethylformamide (4 mL, 0.05 mol) was stirred at room temperature for 22 hrs. The reaction was evaporated and the residue taken up in DCM/water, separated, washed, dried and evaporated to give 1,4-Diethyl-7-methoxy-8-nitro-1,3,4,5-tetrahydro-benzo[e][1,4]diazepin-2-one the product as a red oil. (0.44 g, 95%). LCMS (m/e) 294 (M+1); $^1$H-NMR (DMSO, 400 MHz) δ 7.95 (s, 1H), 7.45 (s, 1H), 3.95 (s, 3H), 3.87-81 (q, 2H, J=6.82 Hz), 3.61 (s, 2H), 2.98 (s, 2H), 2.89 (s, 1H), 2.73 (s, 1H), 2.59-52 (q, 2H, J=7.07 Hz), 1.08-1.00 (quin, 6H, J=7.07 Hz).

736f) 1,4-Diethyl-7-methoxy-8-nitro-1,3,4,5-tetrahydro-benzo[e][1,4]diazepin-2-one (0.50 g, 0.0017 mol) was hydrogenated in a solution of Ethanol (40 mL, 0.7 mol), Ethyl acetate (40 mL, 0.4 mol) and 10% Pd/C (10:90, Palladium:

carbon black, 0.05 g) for 12 hrs. The reaction was filtered and the filtrate evaporated to give an oil. This was chromatographed on Alumina (12 g) and eluded with DCM/EtOH (20-1) to give 8-Amino-1,4-diethyl-7-methoxy-1,3,4,5-tetrahydro-benzo[e][1,4]diazepin-2-one as an oil (0.33 g, 74%). LCMS (m/e) 264 (M+1); $^1$H-NMR (DMSO, 400 MHz) δ 6.76 (s, 1H), 6.61 (s, 1H), 5.75 (s, 1H), 4.86 (s, 2H), 3.77 (s, 3H), 3.72-70 (q, 2H, J=6.06 Hz), 3.38 (s, 2H), 2.89 (s, 2H), 1.05-01 (t, 3H, J=7.07 Hz).

736g) The title compound was prepared from 8-Amino-1,4-diethyl-7-methoxy-1,3,4,5-tetrahydro-benzo[e][1,4]diazepin-2-one and N-[(1R,2R)-2-(2,5-Dichloro-pyrimidin-4-ylamino)-cyclohexyl]-methanesulfonamide in an analogous manner to example 730 (0.039 g, 36%). Mp 137-140° C.; LCMS (m/e) 566 (M); $^1$H-NMR (DMSO, 400 MHz) δ 8.30 (s, 1H), 7.98 (s, 1H), 7.75 (s, 1H), 7.20 (d, 1H, J=8.84 Hz), 7.05 (s, 1H), 6.87 (d, 1H, J=7.83 Hz), 5.75 (s, 1H), 3.90 (s, 3H), 3.88-3.78 (m, 2H), 3.58-3.45 (q, 2H, J=5.30 Hz), 2.98-2.94 (m, 2H), 2.95-2.89 (s, 3H), 2.59-2.52 (m, 2H), 2.03-1.90 (m, 2H), 1.68-1.58 (m, 2H), 1.40-1.20 (m, 4H), 1.07-1.00 (quin, 6H).

Example 737

8-[5-Chloro-4-(4-methoxy-2-pyrazol-1-yl-phenylamino)-pyrimidin-2-ylamino]-1,4-diethyl-7-methoxy-1,3,4,5-tetrahydro-benzo[e][1,4]diazepin-2-one The title compound was prepared from 8-Amino-1,4-diethyl-7-methoxy-1,3,4,5-tetrahydro-benzo[e][1,4]diazepin-2-one and (2,5-Dichloro-pyrimidin-4-yl)-(4-methoxy-2-pyrazol-1-yl-phenyl)-amine in an analogous manner to example 730 (0.044 g, 36%). Mp 97-100° C. LCMS (m/e) 563 (M); $^1$H-NMR (DMSO, 400 MHz) δ 9.85 (s, 1H), 8.24 (S, 1H), 8.12 (s, 1H), 7.97-7.95 (d, 1H, J=8.84 Hz), 7.90 (s, 2H), 7.82 (s, 1H), 7.16 (s, 1H), 7.04 (s, 1H), 6.83-6.81 (d, 1H, J=8.59 Hz), 6.53 (s, 1H), 3.85 (s, 3H), 3.81 (s, 3H), 3.60-3.50 (m, 1H), 3.49 (s, 2H), 2.95 (s, 2H), 1.10-1.00 (t, 3H, J=7.32 Hz), 0.93-0.83 (t, 3H, J=6.82 Hz).

Example 738

2-[5-Chloro-2-(1,4-diethyl-7-methoxy-2-oxo-2,3,4,5-tetrahydro-1H-benzo[e][1,4]diazepin-8-ylamino)-pyrimidin-4-ylamino]-N,Ndimethyl-benzenesulfonamide The title compound was prepared from 8-Amino-1,4-diethyl-7-methoxy-1,3,4,5-tetrahydro-benzo[e][1,4]diazepin-2-one and 2-(2,5-Dichloro-pyrimidin-4-ylamino)-N,N-dimethyl-benzenesulfonamide in an analogous manner to example 730 (0.042 g, 34%). Mp 195-197° C.; LCMS (m/e) 574 (M); $^1$H-NMR (DMSO, 400 MHz) δ 9.27 (s, 1H), 8.30 (s, 2H), 7.86 (s, 1H), 7.80-7.78 (d, 1H, J=7.83 Hz), 7.50-7.43 (t, 1H, J=9.18 Hz), 7.30-7.26 (t, 1H, J=7.58 Hz), 7.07 (s, 1H), 3.84 (s, 1H), 3.51 (s, 3H), 2.96 (s, 2H), 2.65 (s, 1H), 2.59-2.53 (q, 2H, J=7.08 Hz), 1.08-1.05 (t, 3H, J=7.33 Hz), 0.90-0.86 (t, 3H, J=6.83 Hz).

Example 739

(1S,2,3R,4R)-3-[5-Chloro-2-(1,4-diethyl-7-methoxy-2-oxo-2,3,4,5-tetrahydro-1H-benzo[e][1,4]diazepin-8-ylamino)-pyrimidin-4-ylamino]-bicyclo(2.2.1)hept-5-ene-2-carboxylic acid amide The title compound was prepared from 8-Amino-1,4-diethyl-7-methoxy-1,3,4,5-tetrahydro-benzo[e][1,4]diazepin-2-one and (1S,2S,3R,4R)-3-(2,5-Dichloro-pyrimidin-4-ylamino)-bicyclo[2.2.1]hept-5-ene-2-carboxylic acid amide in an analogous manner to example 730 (0.037 g, 20%). Mp 142-144° C.; LCMS (m/e) 526 (M); $^1$H-NMR (DMSO, 400 MHz) δ 8.27 (s, 1H), 8.00 (s, 1H), 7.88-7.86 (d, 1H, J=7.83 Hz), 7.79 (s, 1H), 7.75 (s, 1H), 7.26 (s, 1H), 7.06 (s, 1H), 6.29 (m, 1H), 6.07 (m, 1H), 4.12-4.08 (t, 1H, J=8.09 Hz), 3.90 (s, 3H), 3.89-3.78 (m, 1H), 3.77-3.61 (m, 1H), 3.56-3.47 (q, 2H, J=12.63 Hz), 2.95 (s, 2H), 2.86 (s, 1H), 2.72 (s, 1H), 2.10-2.08 (d, 1H, J=8.10 Hz), 1.39-1.37 (d, 1H, J=8.33 Hz), 1.07-0.99 (m, 6H).

Example 740

2-([5-[5-Chloro-2-(1-methoxy-7-morpholin-4-yl-6,7,8,9-tetrahydro-5H-benzocyclohepten-2-ylamino)-pyrimidin-4-ylamino]-2-fluoro-benzyl}-ethylamino)-ethanol The title compound was prepared from 2-{[5-(2,5-Dichloro-pyrimidin-4-ylamino)-2-fluoro-benzyl]-ethylamino}-ethanol and 1-Methoxy-7-morpholin-4-yl-6,7,8,9-tetrahydro-5H-benzocyclohepten-2-ylamine in an analogous manner to example 730 (0.042 g, 34%). Mp 81-83° C.; LCMS (m/e) 599 (M); $^1$H-NMR (DMSO, 400 MHz) δ 8.88 (s, 1H), 8.10 (s, 1H), 7.87 (s, 1H), 7.61-7.60 (d, 1H, J=5.56 Hz), 7.57-7.55 (m, 1H, J=8.33 Hz), 7.08-7.03 (t, 1H, J=9.09 Hz), 6.76-6.73 (d, 1H, J=8.59 Hz), 4.28 (t, 1H, J=5.00 Hz), 3.59-3.58 (d, 6H, J=4.55 Hz), 3.55-3.41 (s, 2H), 3.46-3.41 (q, 2H, J=6.82 Hz), 3.19-3.13 (m, 1H), 2.76-2.67 (m, 1H), 2.61-2.55 (t, 2H, J=11.37 Hz), 2.46 (s, 6H), 2.36-2.29 (t, 1H, J=12.12 Hz), 2.08-1.97 (m, 2H), 1.31-1.23 (m, 2H), 0.97-0.93 (t, 3H, J=7.07 Hz).

Example 741

(1S,2S,3R,4R)-3-[5-Chloro-2-(4-ethyl-7-methoxy-2-oxo-2,3,4,5-tetrahydro-1H-benzo[e][1,4]diazepin-8-ylamino]bicyclo[2.2.1]hept-5-ene-2-carboxylic acid amide 741a) A mixture of 7-Methoxy-1-methyl-8-nitro-1,3,4,5-tetrahydro-benzo[e][1,4]diazepin-2-one (0.50 g, 0.0020 mol), Ethyl bromide (0.297 mL, 0.00401 mol), Sodium iodide (0.0029 g, 0.000019 mol) and N,N-Diisopropylethylamine (0.87 mL, 0.0050 mol) in N,N-Dimethylformamide (4 mL, 0.05 mol) was reacted in an analogous manner to example 743-C to give 4-Ethyl-7-methoxy-1-methyl-8-nitro-1,3,4,5-tetrahydro-benzo[e][1,4]diazepin-2-one as a tan solid (0.40 g, 72%). Mp 129-131° C. LCMS (m/e) 280 (M+1); $^1$H-NMR (DMSO, 400 MHz) δ 7.92 (s, 1H), 7.45 (s, 1H), 3.94 (s, 3H), 3.76 (s, 2H), 3.26 (s, 3H), 3.02 (s, 2H), 2.60-56 (q, 2H, J=7.32 Hz), 1.08-05 (t, 3H, J=7.33 Hz).

741b) 4-Ethyl-7-methoxy-1-methyl-8-nitro-1,3,4,5-tetrahydro-benzo[e][1,4]diazepin-2-one (0.38 g, 0.0014 mol) was hydrogenated in Ethanol (40 mL, 0.7 mol) and Ethyl acetate (40 mL, 0.4 mol) with 10% Pd/C (10:90, Palladium: carbon black, 0.076 g) in an analogous manner to example 6-E to give 8-Amino-4-ethyl-7-methoxy-1-methyl-1,3,4,5-tetrahydro-benzo[e][1,4]diazepin-2-one as a tan solid (0.33 g, 97%). Mp 130-135° C.; LCMS (m/e) 250 (M); The product was obtained as a tan solid. mp 130-135° C. $^1$H-NMR (DMSO, 400 MHz) 6.76 (s, 1H), 6.57 (s, 1H), 4.87 (s, 1H), 3.77 (s, 3H), 3.43 (s, 2H), 3.16 (s, 3H), 2.93 (s, 2H), 1.05-03 (t, 3H, J=7.32 Hz).

741c) The title compound was prepared from 8-Amino-1,4-diethyl-7-methoxy-1,3,4,5-tetrahydro-benzo[e][1,4]diazepin-2-one and (1S,2S,3R,4R)-3-(2,5-Dichloro-pyrimidin- 4-ylamino)-bicyclo[2.2.1]hept-5-ene-2-carboxylic acid amide in an analogous manner to example 730 (0.055 g, 31%). Mp 154-156° C. LCMS (m/e) 512 (M); ¹H-NMR (DMSO, 400 MHz) δ 8.25 (s, 1H), 8.00 (s, 1H), 7.83 (d, 1H, J=8.34 Hz), 7.78 (s, 1H), 7.75 (s, 1H), 7.25 (s, 1H), 7.05 (s, 1H), 6.30 (m, 1H), 6.07 (m, 1H), 5.75 (s, 1H), 4.16-4.12 (t, 1H, J=8.34 Hz), 3.89 (s, 3H), 3.55-3.46 (q, 2H, J=12.13 Hz), 3.19 (s, 3H), 3.00 (s, 2H), 2.86 (s, 1H), 2.72 (s, 1H), 2.11-2.09 (d, 1H, J=8.34 Hz), 1.40-1.38 (d, 1H, J=9.09 Hz), 1.08-1.04 (t, 3H, J=7.07 Hz).

Example 742

8-[5-Chloro-4-(4-methoxy-2-pyrazol-1-yl-phenylamino)-pyrimidin-2-ylamino]-4-ethyl-7-methoxy-1-methyl-1,3,4,5-tetrahydro-benzo[e][1,4]diazepin-2-one The title compound was prepared from 8-Amino-1,4-diethyl-7-methoxy-1,3,4,5-tetrahydro-benzo[e][1,4]diazepin-2-one and (2,5-Dichloro-pyrimidin-4-yl)-(4-methoxy-2-pyrazol-1-yl-phenyl)-amine in an analogous manner to example 730 (0.071 g, 48%). Mp 105-107° C.; LCMS (m/e) 549 (M); ¹H-NMR (DMSO, 400 MHz) δ 9.85 (s, 1H), 8.25 (s, 1H), 8.11 (s, 1H), 7.97-7.94 (d, 1H, J=9.10 Hz), 7.92 (s, 1H), 7.85 (s, 1H), 7.82 (s, 1H), 7.16 (m, 1H), 7.03 (s, 1H), 6.83-6.80 (d, 1H, J=9.34 Hz), 6.53 (s, 1H), 3.84 (s, 3H), 3.81 (s, 3H), 3.48 (s, 2H), 3.00 (s, 4H), 2.57-2.50 (q, 2H, J=6.82 Hz), 1.08-1.04 (t, 3H, J=8.03 Hz).

Example 743 and 744

(1S,2S3,R,4R)-3-[5-Chloro-2-(7-methoxy-1-methyl-2-oxo-2,3,4,5-tetrahydro-1H-benzo[e][1,4]diazepin-8-ylamino)-pyrimidin-4-ylamino]-bicyclo[2.2.1]hept-5-ene-2-carboxylic acid amide and (1S,2S,3R,4R)-3 [5-Chloro-2-(4-cyanomethyl-7-methoxy-1-methyl-2-oxo-2,3,4,5-tetrahydro-1H-benzo[e][1,4]diazepin-8-ylamino)-pyrimidin-4-ylamino]-bicyclo (2.2.1)hept-5-ene-2-carboxylic acid amide 743a) A mixture of 7-Methoxy-8-nitro-4-(2,2,2-trifluoroacetyl)-1,3,4,5-tetrahydro-benzo[e][1,4]diazepin-2-one (3.00 g, 0.00900 mol), Cesium fluoride (3.40 g, 0.022 mol), Acetonitrile (100 mL, 2 mol) and Methyl iodide (1.68 mL, 0.026 mol) were reacted in an analogous manner to example 736-C to give 7-Methoxy-1-methyl-6-nitro-4-(2,2,2-trifluoro-acetyl)-1,3,4,5-tetrahydro-benzo[e][1,4]diazepin-2-one as a tan solid (2.86 g, 91%). Mp 71-74° C.; LCMS (m/e) 348 (M+1); ¹H-NMR (DMSO, 400 MHz) δ 8.06 (s, 0.5H), 805 (s, 1H), 7.75 (s, 1H), 7.65 (s, 0.5H), 4.77 (s, 1H), 4.73 (s, 2H), 4.09 (s, 1H), 4.03 (s, 2H), 3.96-95 (s, 3H).

743b) A mixture of 7-Methoxy-1-methyl-8-nitro-4-(2,2,2-trifluoro-acetyl)-1,3,4,5-tetrahydro-benzo[e][1,4]diazepin-2-one (2.86 g, 0.00824 mol) and 7.0 M of Ammonia in Methanol (30 mL) were reacted in an analogous manner to example 736-D to give an oil. 7-Methoxy-1-methyl-8-nitro-1,3,4,5-tetrahydro-benzo[e][1,4]diazepin-2-one It was triturated with diethyl ether giving 7-Methoxy-1-methyl-8-nitro-1,3,4,5-tetrahydro-benzo[e][1,4]diazepin-2-one as a tan solid (1.61 g, 77%). Mp 145-149° C.; LCMS (m/e) 252 (M+1); ¹H-NMR (DMSO, 400 MHz) δ 7.91 (s, 1H), 7.41 (s, 1H), 3.94 (s, 2H), 3.79 (s, 1H), 3.31 (s, 3H), 3.25 (s, 2H).

743c) A mixture of 7-Methoxy-1-methyl-8-nitro-1,3,4,5-tetrahydro-benzo[e][1,4]diazepin-2-one (0.50 g, 0.0020 mol), Sodium iodide (0.0148 g, 0.0000987 mol), Bromoacetonitrile (0.276 mL, 0.00396 mol) and N,N-Diisopropylethylamine (1.04 mL, 0.00597 mol) in N,N-Dimethylformamide (6 mL, 0.08 mol) was reacted in an analogous manner to example 736-E to give 4-Ethyl-7-methoxy-1-methyl-8-nitro-1,3,4,5-tetrahydro-benzo[e][1,4]diazepin-2-one as a tan solid (0.51 g, 88%). Mp 129-131° C.; LCMS (m/e) 291 (M+1); ¹H-NMR (DMSO, 400 MHz) δ 7.96 (s, 1H), 7.51 (s, 1H), 3.93-92 (s, 3H), 3.86 (s, 2H), 3.82 (s, 2H), 3.27 (s, 3H), 3.16 (s, 2H).

743d) To a mixture of (7-Methoxy-1-methyl-8-nitro-2-oxo-1,2,3,5-tetrahydro-benzo[e][1,4]diazepin-4-yl)-acetonitrile (0.47 g, 0.0016 mol) and Hydrazine hydrate (2.00 mL, 0.0411 mol) in Ethanol (10 mL, 0.2 mol) was added 10% Pd/C (10:90, Palladium:carbon black, 0.047 g) and reacted in an analogous manner to example 712. The reaction was filtered and evaporated. This product was chromatographed on SiO2 (13 g) with (20-1) DCM/MeOH giving (8-Amino-7-methoxy-1-methyl-2-oxo-1,2,3,5-tetrahydro-benzo[e][1,4]diazepin-4-yl)-acetonitrile as a tan solid (0.067 g, 16%). Mp 128-132° C.; LCMS (m/e)) 261 (M+1); ¹H-NMR (DMSO, 400 MHz) δ 6.80 (s, 1H), 6.59 (s, 1H), 4.95 (s, 2H), 3.77 (s, 3H), 3.77-3.75 (d, 2H, J=9.35 Hz), 3.62 (s, 2H), 3.18 (s, 3H), 3.06 (s, 2H).

743e) the title compounds were prepared from (8-Amino-7-methoxy-1-methyl-2-oxo-1,2,3,5-tetrahydro-benzo[e][1,4]diazepin-4-yl)-acetonitrile and (1S,2S,3R,4R)-3-(2,5-Dichloro-pyrimidin-4-ylamino)-bicyclo[2.2.1]hept-5-ene-2-carboxylic acid amide in an analogous manner to example 730. two products B were isolated as tan solids. First product, Example 743 (0.005 g, 5%); Mp 179-181° C.; LCMS (m/e) 484 (M+1); ¹H-NMR (DMSO, 400 MHz) δ 8.24 (s, 1H), 7.99 (s, 1H), 7.83-7.78 (m, 2H), 7.74, (s, 1H), 7.26 (s, 1H), 7.03 (s, 1H), 6.48 (m, 1H), 6.19-6.07 (m, 1H), 5.75 (s, 1H), 4.16-4.12 (t, 1H, J=7.32 Hz), 3.89 (s, 3H), 3.70 (s, 2H), 3.18 (s, 3H), 3.08 (s, 2H), 2.86 (s, 1H), 2.79-2.51 (m, 2H), 2.09 (s, 1H), 1.46-1.34 (d, 1H, J=8.08), 1.23 (s, 1H).

Example 744

(0.008 g, 7%); Mp 212-214° C.; LCMS (m/e) 523 (M); ¹H-NMR (DMSO, 400 MHz) δ 8.29 (s, 1H), 8.01 (s, 1H), 7.84-7.822 (d, 1H, J=7.58 Hz), 7.78 (s, 2H), 7.25 (s, 1H), 7.10 (s, 1H), 6.31 (m, 1H), 6.08 (m, 1H), 5.75 (s, 1H), 4.17-4.13 (t, 1H, J=7.32 Hz), 3.90 (s, 3H), 3.81 (s, 2H), 3.70 (s, 2H), 3.14 (s, 3H), 3.10 (s, 2H), 2.87 (s, 1H), 2.72 (s, 1H), 2.11-2.09 (d, 1H, J=9.60 Hz), 1.40-1.38 (d, 1H, J=8.08 Hz), 1.23 (s, 1H).

Example 745

N-[(1R,2R)-2-[5-Chloro-2-(4-ethyl-7-methoxy-1-methyl-2-oxo-2,3,4,5-tetrahydro-1H-benzo[e][1,4]diazepin-8-ylamino)-pyrimidin-4-ylamino]-cyclohexyl}-methanesulfonamide The title compound was prepared from 8-Amino-4-ethyl-7-methoxy-1-methyl-1,3,4,5-tetrahydro-benzo[e][1,4]diazepin-2-one and N-[(1R,2R)-2-(2,5-Dichloro-pyrimidin-4-ylamino)-cyclohexyl]-methanesulfonamide in an analogous manner to example 730 (0.062 g, 46%) Mp 214-216° C.; LCMS (m/e) 552 (M); ¹H-NMR (DMSO, 400 MHz) δ 8.23 (s, 1H), 7.97 (s, 1H), 7.74 (s, 1H), 7.22-7.20 (d, 1H, J=8.84 Hz), 7.04 (s, 1H), 6.88-6.86 (d, 1H, J=8.34 Hz), 3.89 (s, 3H), 3.88-3.79 (m, 1H), 3.50 (s, 2H), 3.28 (s, 3H), 2.99 (s, 2H), 2.89 (s, 3H), 2.58-2.53 (q, 2H, J=6.82 Hz), 2.05-1.90 (m, 2H), 1.68-1.58 (m, 2H), 1.40-1.17 (m, 3H), 1.08-1.04 (t, 3H, J=7.33 Hz).

Example 746

N-{(1R,2R)-2-[5-Chloro-2-(4-cyclopropylmethyl-7-methoxy-1-methyl-2-oxo-2,3,4,5-tetrahydro-1H-benzo[e][1,4]diazepin-8-ylamino)-pyrimidin-4-ylamino]-cyclohexyl}-methanesulfonamide 746a) A mixture of 7-Methoxy-1-methyl-8-nitro-1,3,4,5-tetrahydro-benzo[e][1,4]diazepin-2-one (0.50 g, 0.0020 mol), [B] Cyclopropylmethyl bromide (0.55 mL, 0.0057 mol), Sodium iodide (0.003 g, 0.00002 mol) and N,N-Diisopropylethylamine (0.87 mL, 0.0050 mol) in N,N-Dimethylformamide (4 mL, 0.05 mol) was reacted in an analogous manner to example 743-C to give 4-Cyclopropylmethyl-7-methoxy-1-methyl-8-nitro-1,3,4,5-tetrahydro-benzo[e][1,4]diazepin-2-one as a red oil. (0.56 g, 92%). LCMS (m/e) 306 (M+1); $^1$H-NMR (DMSO, 400 MHz) δ 7.92 (s, 1H), 7.44 (s, 1H), 3.95 (s, 3H), 3.66 (s, 2H), 3.26 (s, 2H), 3.13 (s, 2H), 2.89 (s, 1H), 2.73 s, 1H), 2.44-2.42 (d, 2H, J=6.57 Hz), 1.30-1.20 (br, 1H), 0.95-0.87 (br, 2H), 0.50 (d, 2H, J=7.83 Hz), 0.18-0.16 (d, 2H, J=4.80 Hz).

746b) 4-Cyclopropylmethyl-7-methoxy-1-methyl-8-nitro-1,3,4,5-tetrahydro-benzo[e][1,4]diazepin-2-one (0.5 g, 0.002 mol) was hydrogenated in Ethanol (40 mL, 0.7 mol) and Ethyl acetate (40 mL, 0.4 mol) with 10% Pd/C (10:90, Palladium:carbon black, 0.082 g) in an analogous manner to example N26-F to give 8-Amino-4-cyclopropylmethyl-7-methoxy-1-methyl-1,3,4,5-tetrahydro-benzo[e][1,4]diazepin-2-one as an oil (0.43 g, 90%). LCMS (m/e) 276 (M+1); $^1$H-NMR (DMSO, 400 MHz) δ 6.76 (s, 1H), 6.57 (s, 1H), 4.88 (s, 2H), 3.77 (s, 3H), 3.44 (s, 2H), 3.05 (s, 3H), 2.89 (s, 2H), 2.38-2.37 (d, 2H, J=15.41 Hz), 1.26-1.24 (m, 1H), 0.85-0.75 (m, 2H), 0.49-0.47 (d, 2H, J=7.83 Hz), 0.16-0.15 (d, 2H, J=4.80 Hz).

746c) The title compound was prepared from 8-Amino-4-cyclopropylmethyl-7-methoxy-1-methyl-1,3,4,5-tetrahydro-benzo[e][1,4]diazepin-2-one and N-[(1R,2R)-2-(2,5-Dichloro-pyrimidin-4-ylamino)-cyclohexyl]-methanesulfonamide in an analogous manner to example 730 (0.062 g, 47%) Mp 131-132° C.; LCMS (m/e) 578 (M); $^1$H-NMR (DMSO, 400 MHz) δ 8.23 (s, 1H), 7.98 (s, 1H), 7.75 (s, 1H), 7.22-7.20 (d, 1H, J=8.59 Hz), 7.03 (s, 2H), 6.88-6.86 (d, 1H, J=7.83 Hz), 3.89 (s, 3H), 3.88-3.80 (m, 1H), 3.55 (d, 2H, J=3.03 Hz), 3.27 (s, 3H), 3.10-3.09 (d, 2H, J=3.82 Hz), 2.89 (s, 3H), 2.41-2.40 (d, 2H, J=6.82 Hz), 2.05-1.92 (m, 2H), 1.68-1.55 (m, 2H), 1.40-1.17 (m, 4H), 1.13-1.97 (m, 1H), 0.90-0.79 (m, 1H), 0.50-0.48 (d, 2H, J=7.83 Hz), 0.170-0.16 (d, 2H, J=4.55 Hz).

Example 747

(1S,2S,3R,4R)-3-[5-Chloro-2-[4-cyclopropylmethyl-7-methoxy-2,3,4,5-tetrahydro-1H-benzo[e][1,4]diazepin-8-ylamino)-pyrimidin-4-ylamino]-bicyclo(2.2.1)hept-5-ene-2-carboxylic acid amide The title compound was prepared from 8-Amino-4-cyclopropylmethyl-7-methoxy-1-methyl-1,3,4,5-tetrahydro-benzo[e][1,4]diazepin-2-one and (1S,2S,3R,4R)-3-(2,5-Dichloro-pyrimidin-4-ylamino)-bicyclo[2.2.1]hept-5-ene-2-carboxylic acid amide in an analogous manner to example 730 (0.058 g, 42%). Mp 149-151° C.; LCMS (m/e) 538 (M); $^1$H-NMR (DMSO, 400 MHz) δ 8.25 (s, 1H), 8.00 (s, 1H), 7.83 (d, 1H, J=7.58 Hz), 7.78 (s, 1H), 7.75 (s, 1H), 7.25 (s, 1H), 7.05 (s, 1H), 6.30 (t, 1H), 6.07 (t, 1H), 5.75 (s, 1H), 4.16-4.12 (t, 1H, J=8.08 Hz), 3.90 (s, 3H), 3.60-3.50 (q, 2H, J=11.87 Hz), 3.19 (s, 3H), 3.11 (s, 2H), 2.86 (s, 1H), 2.72 (s, 1H), 2.41-2.40 (d, 2H, J=6.57 Hz), 2.11-2.09 (d, 1H, J=8.84 Hz), 1.40-1.35 (d, 1H, J=8.84 Hz), 0.92-0.80 (m, 1H), 0.50-0.48 (d, 2H, J=7.83 Hz), 0.20-0.12 (m, 2H).

Example 748

8-[5-Chloro-4-(4-methoxy-2-pyrazol-1-yl-phenylamino)-pyrimidin-2-ylamino]-cyclopropylmethyl-7-methoxy-1-methyl-1,3,4,5-tetrahydro-benzo[e][1,4]diazepin-2-one The title compound was prepared from 8-Amino-4-cyclopropylmethyl-7-methoxy-1-methyl-1,3,4,5-tetrahydro-benzo[e][1,4]diazepin-2-one and (2,5-Dichloro-pyrimidin-4-yl)-(4-methoxy-2-pyrazol-1-yl-phenyl)-amine in an analogous manner to example 730 (0.064 g, 44%). Mp 94-96° C.; LCMS (m/e) 575 (M); $^1$H-NMR (DMSO, 400 MHz) δ 9.84 (s, 1H), 8.24 (s, 1H), 8.11 (s, 1H), 7.96-94 (d, 1H, J=8.84 Hz), 7.92 (s, 1H), 7.85 (s, 1H), 7.82 (s, 1H), 7.16-7.15 (d, 1H, J=1.77 Hz), 7.03 (s, 1H), 6.83-6.80 (m, 1H), 6.53 (s, 1H), 3.84 (s, 3H), 3.81 (s, 3H), 3.53 (s, 2H), 3.09 (s, 2H), 2.99 (s, 3H), 2.41-2.40 (d, 2H, J=6.57 Hz), 0.90-0.82 (m, 1H), 0.51-0.49 (d, 2H, J=8.08 Hz), 0.17-0.16 (d, 2H, J=4.80 Hz).

Example 749

8-(5-Chloro-4-{3-[(2-hydroxy-ethylamino)-methyl]-4-methoxy-phenylamino}-pyrimidin-2-ylamino)-4-ethyl-7-methoxy-1-methyl-1,3,4,5-tetrahydro-benzo[e][1,4]diazepin-2-one 749a) A mixture of benzaldehyde (1.0 g, 0.0059 mol), aminoethanol (1.08 g, 0.0177 mol), acetic acid (10 mL) and methanol (20 mL) was stirred for 2.5 hr. Sodium borohydride (7.04 g, 0.112 mol) was slowly added and stirred at room temperature for 20 hr. After the reaction was evaporated, water (10 mL), ethyl acetate (20 mL) and diethyl ether (10 mL) were added and the pH adjusted to 10. The solution was separated, washed with brine, dried and evaporated to give a solid. This was triturated with hexane-diethyl ether (1-1) giving 2-(2-Fluoro-5-nitro-benzylamino)-ethanol as a yellow solid (1.05 g, 83%). Mp 93-94° C.; LCMS (m/e) 214 (M); $^1$H-NMR (DMSO, 400 MHz) δ 8.42-8.38 (t, 1H, J=3.79 Hz), 8.22-8.17 (t, 1H, J=4.55 Hz), 7.50-7.43 (t1H, J=9.10 Hz), 4.54-4.49 (t, 1H, J=5.30 Hz), 3.83 (s, 2H), 4.54-4.49 (t, 1H, J=5.30 Hz), 3.51-3.45 (t, 2H, J=5.56 Hz), 2.62-2.57 (t, 2H, J=5.56 Hz).

749b) A mixture of 2-(2-Fluoro-5-nitro-benzylamino)-ethanol (6.00 g, 0.0280 mol), Ethane, isocyanato- (6.64 mL, 0.0839 mol) and N,N-Diisopropylethylamine (24.50 mL, 0.1406 mol) in Acetonitrile (50 mL, 1 mol) was heated at 40° C. for 18 hours. The reaction was evaporated and the residue taken up in DCM, washed with water, dried and evaporated to give Ethyl-carbamic acid 2-[3-ethyl-1-(2-fluoro-5-nitro-benzyl)-ureido]ethyl ester as a yellow oil (9.91 g, 80%) LCMS (m/e) 357 (M+1); $^1$H-NMR (DMSO, 400 MHz) δ 8.22-20 (m, 1H), 8.05-7.97 (m, 1H), 7.51-7.47 (t, 1H, J=9.10 Hz), 7.08-7.02 (t, 1H, J=5.06), 4.01-3.99 (t, 2H, J=5.05 Hz), 3.49-3.41 (t, 2H, J=5.31 Hz), 4.58 (s, 2H), 3.113-04 (quin, 2H, J=5.81 Hz), 2.95-2.93 (q, 2H, J=6.31 Hz), 1.04-0.95 (m, 6H).

749c) A mixture of Ethyl-carbamic acid 2-[3-ethyl-1-(2-fluoro-5-nitro-benzyl)-ureido]-ethyl ester (1.00 g, 0.00281 mol) and 0.5 M of Sodium methoxide in Methanol (22 mL, 0.011 mol) was heated at 55° C. overnight. The reaction was evaporated. The residue was acidified to pH 5, extracted with DCM and evaporated to give a solid (0.52 g, 40%). 0.03 g of product was chromatographed on SiO2 with (10-1) DCM- EtOH giving 3-Ethyl-1-(2-hydroxy-ethyl)-1-(2-methoxy-5-nitro-benzyl)-urea as a yellow solid (0.015 g). Mp 93-94° C.; LCMS (M/E) 298 (M+1); $^1$H-NMR (DMSO, 400 MHz) δ 8.20-17 (d, 1H, J=9.09 Hz), 7.83 (s, 1H), 7.23-7.21 (d, 1H, J=9.10 Hz), 6.46 (t, 1H, J=5.05 Hz), 4.83-4.81 (t, 1H, J=5.05 Hz), 4.46 (s, 2H), 3.95 (s, 3H), 3.49-7 (q, 2H, J=5.30 Hz), 3.29-3.27 (q, 2H, J=4.55 Hz), 3.07-3.02 (q, 2H, J=7.08 Hz), 1.07-1.01 (t, 3H, J=7.07 Hz).

749d) 3-Ethyl-1-(2-hydroxy-ethyl)-1-(2-methoxy-5-nitro-benzyl)-urea (0.43 g, 0.0014 mol) in Ethanol (50 mL, 0.8 mol) was hydrogenated with 10% Pd/C (10:90, Palladium:carbon black, 0.027 g) catalyst overnight. The reaction was filtered and the filtrate evaporated to give 1-(5-Amino-2-methoxy-benzyl)-3-ethyl-1-(2-hydroxy-ethyl)-urea as a yellow oil (0.40 g, 75%). 0.020 g was chromatographed on Alumina with DCM/IPA (20-1) giving 1-(5-Amino-2-methoxy-benzyl)-3-ethyl-1-(2-hydroxy-ethyl)-urea as an oil (0.010 g). LCMS (m/e) 268 (M+1); $^1$H-NMR (DMSO, 400 MHz) δ 6.68 (d, 1H, J=8.59 Hz), 6.44-6.39 (d, 1H, J=9.6 Hz), 6.32 (s, 1H), 6.26-6.23 (t, 1H, J=5.30 Hz), 4.79-4.76 (t, 1H, J=5.06 Hz), 4.59 (s, 2H), 4.15 (s, 2H), 3.65 (s, 3H), 3.47-3.43 (q, 2H, J=5.30 Hz), 3.20-3.17 (t, 2H, J=6.06 Hz), 3.08-3.00 (q, 2H, J=5.81 Hz), 1.07-0.98 (t, 3H, J=7.07 Hz).

749e) The title compound was prepared from 8-Amino-4-ethyl-7-methoxy-1-methyl-1,3,4,5-tetrahydro-benzo[e][1,4]diazepin-2-one and 1-[5-(2,5-Dichloro-pyrimidin-4-ylamino)-2-methoxy-benzyl]-3-ethyl-1-(2-hydroxy-ethyl)-urea in an analogous manner to example 730 (0.010 g, 9%). Mp 65-70° C.; LCMS (m/e) 556 (M); $^1$H-NMR (DMSO, 400 MHz) δ 8.87 (s, 1H), 8.12 (s, 1H), 7.99 (s, 1H), 7.76 (s, 1H), 7.41 (m, 2H), 7.01 (s, 1H), 6.86-6.84 (d, 1H, J=9.35 Hz), 4.54 (m, 1H), 4.34-4.43 (d, 1H, J=4.04 Hz), 3.86 (s, 3H), 3.78 (s, 4H), 3.68 (s, 2H), 3.45 (s, 4H), 2.97 (s, 2H), 2.80 (s, 2H), 2.63-2.58 (m, 2H), 1.07-1.05 (t, 3H, J=7.07 Hz).

Example 750

6-{5-Chloro-2-[3-methoxy-7-(2-methoxy-ethylamino)-6,7,8,9-tetrahydro-5H-benzocyclohepten-2-ylamino]-pyrimidin-4-ylamino}-4-methanesulfonyl-7-methoxy-1,3,4,5-tetrahydro-benzo[e][1,4]diazepin-2-one 750a) A mixture of 7-Methoxy-6-nitro-4-(2,2,2-trifluoro-acetyl)-1,3,4,5-tetrahydro-benzo[e][1,4]diazepin-2-one (1.70 g, 0.00510 mol) and 7.0 M of Ammonia in Methanol (30 mL) was stirred at room temperature for 22 hrs. The reaction was evaporated to give 7-Methoxy-6-nitro-1,3,4,5-tetrahydro-benzo[e][1,4]diazepin-2-one as a tan solid (1.10 g, 90%). Mp 220-222° C.; LCMS (m/e) 237 (M); $^1$H-NMR (DMSO, 400 MHz) δ $^1$H-NMR (DMSO, 400 MHz) δ 9.92 (s, 1H), 7.257-20 (q, 2H, J=3.79 Hz), 3.83 (s, 3H), 3.69 (d, 2H), 3.43 (d, 2H, J=4.29 Hz), 3.11 (br, 1H).

750b) To a mixture of 7-Methoxy-6-nitro-1,3,4,5-tetrahydro-benzo[e][1,4]diazepin-2-one (0.55 g, 0.0023 mol) and N,N,N',N'-Tetramethyl-1,8-naphthalenediamine (0.745 g, 0.00348 mol) in Acetonitrile (40 mL, 0.8 mol) was added 2 M of Methanesulphonic anhydride in Methylene chloride (1.50 mL) and stirred at room temperature for 3 hours. 1N HCl added, stirred and the solid collected. It was washed, dried and evaporated to give 4-Methanesulfonyl-7-methoxy-6-nitro-1,3,4,5-tetrahydro-benzo[e][1,4]diazepin-2-one as a grey solid. (0.58 g, 79%). Mp 222-226° C.; LCMS (m/e) 315 (M); $^1$H-NMR (DMSO, 400 MHz) δ 10.4 (s, 1H), 7.40-7.31 (q, 1H, J=9.10 Hz), 4.34 (s, 2H), 3.97 (s, 2H), 3.88 (s, 3H), 3.00 (s, 3H).

750c) 4-Methanesulfonyl-7-methoxy-6-nitro-1,3,4,5-tetrahydro-benzo[e][1,4]diazepin-2-one (0.57 g, 0.0018 mol) was hydrogenated in N,N-Dimethylformamide (40 mL, 0.5 mol) 10% Pd/C (10:90, Palladium:carbon black, 0.057 g) for 5 days. After the reaction was filtered and the filtrate evaporated. the residue was triturated with ether giving 6-Amino-4-methanesulfonyl-7-methoxy-1,3,4,5-tetrahydro-benzo[e][1,4]diazepin-2-one as a grey solid (0.50 g, 97%). Mp 232-233° C.; LCMS (m/e) 285 (M); $^1$H-NMR (DMSO, 400 MHz) 6 $^1$H-NMR (DMSO, 400 MHz) δ 9.93 (s, 1H), 6.84-6.82 (d, 1H, J=8.59 Hz), 6.38-6.36 (d, 2H, J=8.33 Hz), 4.85 (s, 2H), 4.35 (s, 2H), 3.77 (s, 3H), 3.68 (s, 2H), 2.98 (s, 3H).

750d) A mixture of 2,4,5-Trichloro-pyrimidine (1.5 g, 0.0084 mol), 6-Amino-4-methanesulfonyl-7-methoxy-1,3,4,5-tetrahydro-benzo[e][1,4]diazepin-2-one (0.400 g, 0.00140 mol) was heated at 120° C. for 48 hrs. The reaction was triturated with ethyl acetate and then with methanol giving 6-(2,5-Dichloro-pyrimidin-4-ylamino)-4-methanesulfonyl-7-methoxy-1,3,4,5-tetrahydro-benzo[e][1,4]diazepin-2-one the product as a gray solid (0.338 g, 51%). Mp 280-300d; LCMS (m/e)-432 (M); $^1$H-NMR (DMSO, 400 MHz) δ 10.23 (s, 1H), 9.34 (s, 1H), 8.34 (s, 1H), 7.20-7.17 (d, 1H, J=9.10 Hz), 7.14-7.11 (d, 1H, J=8.84 Hz), 4.40-4.30 (m, 1H), 4.25-4.10 (m, 1H), 3.83 (s, 3H), 2.88 (s, 3H).

750e) The title compound was prepared from 3-Methoxy-N*7*-(2-methoxy-ethyl)-6,7,8,9-tetrahydro-5H-benzocycloheptene-2,7-diamine and 6-(2,5-Dichloro-pyrimidin-4-ylamino)-4-methanesulfonyl-7-methoxy-1,3,4,5-tetrahydro-benzo[e][1,4]diazepin-2-one in an analogous manner to example 730 (0.017 g, 11%). Mp 110-114° C.; LCMS (m/e) 660 (M); $^1$H-NMR (DMSO, 400 MHz) δ 10.28 (br, 1H), 8.58 (s, 1H), 8.05 (s, 1H), 7.42 (s, 1H), 7.35 (s, 1H), 7.20-7.14 (q, 2H, J=5.81 Hz), 6.70 (s, 1H), 6.56 (s, 1H), 6.39 (s, 1H), 4.40-4.24 (br, 3H), 3.74 (s, 3H), 3.70 (s, 6H), 3.98-3.45 (q, 3H, J=5.05 Hz), 3.25 (s, 2H), 2.80 (s, 2H), 2.79-2.70 (br, 2H), 2.70-2.57 (br, 2H), 2.35-2.10 (br, 2H), 1.98-1.81 (br, 3H), 1.25-0.90 (br, 4H).

Example 751

2-{7-[5-Chloro-4-(4-methanesulfonyl-7-methoxy-2-oxo-2,3,4,5-tetrahydro-1H-benzo[e][1,4]diazepin-6-ylamino)-pyrimidin-2-ylamino]-8-methoxy-1,2,4,5-tetrahydro-benzo[d]azepin-3-yl}-N,Ndimethyl-acetamide The title compound was prepared from 2-(7-Amino-8-methoxy-1,2,4,5-tetrahydro-benzo[d]azepin-3-yl)-N,N-dimethyl-acetamide and 6-(2,5-Dichloro-pyrimidin-4-ylamino)-4-methanesulfonyl-7-methoxy-1,3,4,5-tetrahydro-benzo[e][1,4]diazepin-2-one in an analogous manner to example 730 (0.022 g, 12%). Mp 118-121° C.; LCMS (m/e) 673 (M); $^1$H-NMR (DMSO, 400 MHz) δ 10.25 (s, 1H), 8.57 (s, 1H), 8.05 (s, 1H), 7.95 (s, 1H), 7.43 (s, 1H), 7.30 (s, 1H), 7.19-7.11 (q, 2H, J=9.00 Hz), 6.70 (s, 1H), 5.75 (s, 1H), 4.42-4.40 (br, 2H), 4.40-4.25 (br, 2H), 3.74 (s, 3H), 3.70 (s, 3H), 3.70-3.63 (br, 2H), 3.24 (s, 2H), 3.06-3.05 (d, 3H, J=4.29 Hz), 2.89 (s, 2H), 2.83-2.81 (d, 3H, J=7.83 Hz), 2.78 (s, 2H), 2.73 (s, 2H), 2.73-2.60 (br, 2H), 2.40-2.30 (br, 2H).

Example 761

5-Chloro-N*2*-[3-(2,2-difluoro-ethyl)-8-methoxy-2,3,4,5-tetrahydro-1H-benzo[d]azepin-7-yl]-N*4*-(2-methoxy-4-morpholin-4-yl-phenyl)-pyrimidine-2,4-diamine The title compound was prepared from 3-(2,2-Difluoro-ethyl)-8-methoxy-2,3,4,5-tetrahydro-1H-benzo[d]azepin-7- ylamine and (2,5-Dichloro-pyrimidin-4-yl)-(2-methoxy-4-morpholin-4-yl-phenyl)-amine in an analogous manner to Example 61e. Product isolated as a pale yellow solid (0.0585 g, 52%). MP: 219° C. (dec.). $^1$H NMR (400 MHz, CDCl$_3$, δ, ppm): 8.27-8.22 (m, 1H), 8.13-8.10 (m, 1H), 8.02 (d, 1H, J=1.3 Hz), 7.53 (s, 1H), 7.43 (s, 1H), 6.63 (s, 1H), 6.56-6.53 (m, 1H), 6.52-6.47 (m, 1H), 6.07-5.75 (m, 1H), 3.92 (s, 3H), 3.91-3.87 (m, 4H), 3.86 (s, 3H), 3.18-3.12 (m, 4H), 2.97-2.75 (m, 10H). MS: 575 (MH)$^+$.

Example 762

N-((1R,2R)-2-{5-Chloro-2-[3-(2,2-difluoro-ethyl)-8-methoxy-2,3,4,5-tetrahydro-1H-benzo[d]azepin-7-ylamino]-pyrimidin-4-ylamino}-cyclohexyl)-methanesulfonamide The title compound was prepared from 3-(2,2-Difluoro-ethyl)-8-methoxy-2,3,4,5-tetrahydro-1H-benzo[d]azepin-7-ylamine and N-[(1R,2R)-2-(2,5-Dichloro-pyrimidin-4-ylamino)-cyclohexyl]-methanesulfonamide in a analogous manner to Example 61e. Product was isolated as a white solid (0.029 g, 27%). MP: 103-127° C. $^1$H NMR (400 MHz, CDCl$_3$, δ, ppm): 7.99 (s, 1H), 7.95 (s, 1H), 7.31 (s, 1H), 6.65 (s, 1H), 6.07-5.74 (m, 1H), 5.34 (d, 1H, J=8.1 Hz), 5.22 (d, 1H, J=7.1 Hz), 4.01-3.90 (m, 1H), 3.87 (s, 3H), 3.29-3.19 (m, 1H), 2.98-2.74 (m, 14H), 2.29-2.16 (m, 2H), 1.89-1.74 (m, 2H), 1.41-1.34 (m, 3H). MS: 559 (MH)$^+$.

Example 763

(2-exo,3-exo)-3-{5-Chloro-2-[3-(2,2-difluoro-ethyl)-8-methoxy-2,3,4,5-tetrahydro-1H-benzo[d]azepin-7-ylamino]-pyrimidin-4-ylamino}-bicyclo[2.2.1]hept-5-ene-2-carboxylic acid amide The title compound was prepared from 3-(2,2-Difluoro-ethyl)-8-methoxy-2,3,4,5-tetrahydro-1H-benzo[d]azepin-7-ylamine and (2-exo, 3-exo)-3-(2,5-Dichloro-pyrimidin-4-ylamino)-bicyclo[2.2.1]hept-5-ene-2-carboxylic acid amide in an analogous manner to Example 61e. Product isolated as a tan solid (0.066 g, 68%). MP: 107-132° C. $^1$H NMR (400 MHz, CDCl$_3$, δ, ppm): 8.19 (s, 1H), 7.90-7.88 (m, 1H), 7.39 (s, 1H), 6.64 (s, 1H), 6.59-6.52 (m, 1H), 6.33-6.29 (m, 2H), 6.07-5.74 (m, 1H), 5.59-5.47 (br s, 1H), 5.29-5.23 (br s, 1H), 4.44 (t, 1H, J=8.2 Hz), 3.87 (s, 3H), 3.08 (s, 1H), 2.98-2.76 (m, 11H), 2.51 (d, 1H, J=8.3 Hz), 2.26 (d, 1H, J=9.9 Hz), 1.66 (d, 1H, J=9.9 Hz). MS: 519 (MH)$^+$.

Example 764

5-Chloro-N*2*-[3-(2,2-difluoro-ethyl)-8-methoxy-2,3,4,5-tetrahydro-1H-benzo[d]azepin-7-yl]-N*4*-[2-methoxy-4-(4-methyl-piperazin-1-yl)-phenyl]-pyrimidine-2,4-diamine 4-Chloro-2-methoxy-1-nitro-benzene using 1-methyl-piperazine was converted in an analogous manner to Example 171b, to 1-(3-Methoxy-4-nitro-phenyl)-4-methyl-piperazine which was converted in an analogous manner to Example 31f, to 2-Methoxy-4-(4-methyl-piperazin-1-yl)-phenylamine, which was converted, using an analogous procedure to Example 1d, to (2,5-Dichloro-pyrimidin-4-yl)-[2-methoxy-4-(4-methyl-piperazin-1-yl)-phenyl]-amine which was converted to the title compound in an analogous manner to Example 61e using 3-(2,2-Difluoro-ethyl)-8-methoxy-2,3,4,5-tetrahydro-1H-benzo[d]azepin-7-ylamine. Product isolated as an off-white solid (0.027 g, 26%). MP: 162-165° C. $^1$H NMR (400 MHz, CDCl$_3$, δ, ppm): 8.24-8.19 (m, 1H), 8.13-8.10 (m, 1H), 8.01 (d, 1H, J=1.8 Hz), 7.51 (s, 1H), 7.43 (s, 1H), 6.64-6.61 (m, 1H), 6.58-6.55 (m, 1H), 6.54-6.49 (m, 1H), 6.08-5.75 (m, 1H), 3.91 (s, 3H), 3.86 (s, 3H), 3.24-3.18 (m, 4H), 2.97-2.76 (m, 10H), 2.64-2.58 (m, 4H), 2.38 (s, 3H). MS: 588 (MH)$^+$.

Example 765

5-Chloro-N*2*-[3-(2,2-difluoro-ethyl)-8-methoxy-2,3,4,5-tetrahydro-1H-benzo[d]azepin-7-yl]-N*4*-[3-methyl-4-(4-methyl-piperazin-1-yl)-phenyl]-pyrimidine-2,4-diamine 1-Fluoro-2-methyl-4-nitro-benzene using 1-methyl-piperazine was converted in an analogous manner to Example 171b, to 1-Methyl-4-(2-methyl-4-nitro-phenyl)-piperazine, which was converted in analogous manner to Example 31f, to 3-Methyl-4-(4-methyl-piperazin-1-yl)-phenylamine, which was converted, using an analogous procedure to Example 1d, to (2,5-Dichloro-pyrimidin-4-yl)-[3-methyl-4-(4-methyl-piperazin-1-yl)-phenyl]-amine which was converted to the title compound in an analogous manner to Example 61e using 3-(2,2-Difluoro-ethyl)-8-methoxy-2,3,4,5-tetrahydro-1H-benzo[d]azepin-7-ylamine. Product isolated as an off-white solid (0.018 g, 17%). MP: 221° C. (dec.). $^1$H NMR (400 MHz, CDCl$_3$, δ, ppm): 8.02 (s, 2H), 7.55-7.45 (m, 2H), 7.25-7.21 (m, 1H), 7.05 (d, 1H, J=8.3 Hz), 6.90 (s, 1H), 6.60 (s, 1H), 5.91 (tt, 1H, J=56.0 Hz and 4.2 Hz), 3.84 (s, 3H), 3.05-2.96 (m, 4H), 2.95-2.61 (m, 14H), 2.46 (s, 3H), 2.30 (s, 3H). MS: 572 (MH)$^+$.

Example 766

2-{5-Chloro-2-[3-(2,2-difluoro-ethyl)-8-methoxy-2,3,4,5-tetrahydro-1H-benzo[d]azepin-7-ylamino]-pyrimidin-4-ylamino}-N-methyl-benzamide The title compound was prepared from 3-(2,2-Difluoro-ethyl)-8-methoxy-2,3,4,5-tetrahydro-1H-benzo[d]azepin-7-ylamine and 2-(2,5-Dichloro-pyrimidin-4-ylamino)-N-methyl-benzamide in an analogous manner to Example 61e. Product isolated as an off-white solid (0.005 g, 5%). MP: 169-172° C. $^1$H NMR (400 MHz, CDCl$_3$, δ, ppm): 11.23 (br s, 1H), 8.58 (d, 1H, J=8.6 HZ), 8.06 (s, 1H), 7.97 (br s, 1H), 7.50 (d, 1H, J=7.8 Hz), 7.38 (t, 1H, J=7.8 Hz), 7.10 (t, 1H, J=7.6 Hz), 6.66 (s, 1H), 6.26 (br s, 1H), 6.20-5.87 (m, 1H), 3.86 (s, 3H), 3.15-2.75 (m, 14H). MS: 517 (MH)$^+$.

Example 767

2-{5-Chloro-2-[3-(2,2-difluoro-ethyl)-8-methoxy-2,3,4,5-tetrahydro-1H-benzo[d]azepin-7-ylamino]-pyrimidin-4-ylamino}-N-ethyl-benzamide The title compound was prepared from 3-(2,2-Difluoro-ethyl)-8-methoxy-2,3,4,5-tetrahydro-1H-benzo[d]azepin-7-ylamine and 2-(2,5-Dichloro-pyrimidin-4-ylamino)-N-ethyl-benzamide in a analogous manner to Example 61e. Product isolated as an off-white solid (0.013 g, 13%). MP: 170-175° C. $^1$H NMR (400 MHz, CDCl$_3$, δ, ppm): 10.95 (br s, 1H), 8.64 (d, 1H, J=8.3 Hz), 8.12-8.06 (m, 2H), 7.54-7.39 (m, 3H), 7.08 (t, 1H, J=7.6 Hz), 6.64 (s, 1H), 6.22-6.12 (m, 1H), 6.07-5.74 (m, 1H), 3.86 (s, 3H), 3.52 (p, 2H, J=6.8 Hz), 2.99-2.71 (m, 13H). MS: 531 (MH)$^+$.

Example 768

5-Chloro-N*4*-(5-chloro-2-methoxy-phenyl)-N*2*-[3-(2,2-difluoro-ethyl)-8-methoxy-2,3,4,5-tetrahydro-1H-benzo[d]azepin-7-yl]-pyrimidine-2,4-diamine The title compound was prepared from 3-(2,2-Difluoro-ethyl)-8-methoxy-2,3,4,5-tetrahydro-1H-benzo[d]azepin-7-ylamine and (5-Chloro-2-methoxy-phenyl)-(2,5-dichloro-pyrimidin-4-yl)-amine in an analogous manner to Example 61e. Product isolated as an off-white solid (0.053 g, 70%). MP: 172-178° C. $^1$H NMR (400 MHz, CDCl$_3$, δ, ppm): 8.47 (s, 1H), 8.11-8.09 (m, 1H), 8.01 (s, 1H), 7.77 (s, 1H), 7.43 (s, 1H), 7.03-6.98 (m, 1H), 6.86-6.82 (m, 1H), 6.65 (s, 1H), 6.07-5.74 (m, 1H), 3.93 (s, 3H), 3.88 (s, 3H), 2.97-2.74 (m, 10H). MS: 524 (MH)$^+$.

Example 769

(2-exo,3-exo)-3-{2-[3-(2,2-Difluoro-ethyl)-8-methoxy-2,3,4,5-tetrahydro-1H-benzo[d]azepin-7-ylamino]-5-fluoro-pyrimidin-4-ylamino}-bicyclo[2.2.1]hept-5-ene-2-carboxylic acid amide (2-exo, 3-exo)-3-Amino-bicyclo[2.2.1]hept-5-ene-2-carboxylic acid amide using 2,4-Dichloro-5-fluoropyrimidine was converted in an analogous manner to Example 1d, to (2-exo,3-exo)-3-(2-Chloro-5-fluoro-pyrimidin-4-ylamino)-bicyclo[2.2.1]hept-5-ene-2-carboxylic acid amide, which was converted, in an analogous manner to Example 61e, to title compound using 3-(2,2-Difluoro-ethyl)-8-methoxy-2,3,4,5-tetrahydro-1H-benzo[d]azepin-7-ylamine. Product isolated as an off-white solid (0.030 g, 41%). MP: 116-133° C. $^1$H NMR (400 MHz, CDCl$_3$, δ, ppm): 8.19 (s, 1H), 7.79-7.76 (m, 1H), 7.33 (s, 1H), 6.63 (s, 1H), 6.33-6.29 (m, 1H), 6.13-6.08 (m, 1H), 6.07-5.74 (m, 1H), 5.54 (br s, 1H), 5.35 (br s, 1H), 4.48-4.41 (m, 1H), 3.87 (s, 3H), 3.10-3.05 (m, 1H), 2.97-2.77 (m, 12H), 2.55-2.50 (m, 1H). MS: 502 (MH)$^+$.

Example 770

2-(7-{5-Chloro-4-[2-methoxy-4-(4-methyl-piperazin-1-yl)-phenylamino]-pyrimidin-2-ylamino}-8-methoxy-1,2,4,5-tetrahydro-benzo[d]azepin-3-yl)-N,N-dimethyl-acetamide The title compound was prepared from 2-(7-Amino-8-methoxy-1,2,4,5-tetrahydro-benzo[d]azepin-3-yl)-N,N-dimethyl-acetamide and (2,5-Dichloro-pyrimidin-4-yl)-[2-methoxy-4-(4-methyl-piperazin-1-yl)-phenyl]-amine in an analogous manner to Example 61e. Product isolated as an off-white foam (0.031 g, 37%). $^1$H NMR (400 MHz, CDCl$_3$, δ, ppm): 8.26-8.22 (m, 1H), 8.11 (s, 1H), 8.02-8.00 (m, 1H), 7.53 (s, 1H), 7.42 (s, 1H), 6.63 (s, 1H), 6.57-6.55 (m, 1H), 6.54-6.50 (m, 1H), 3.91 (s, 3H), 3.86 (s, 3H), 3.27 (s, 2H), 3.23-3.18 (m, 4H), 3.15 (s, 3H), 2.98 (s, 3H), 2.91-2.82 (m, 4H), 2.72-2.65 (m, 4H), 2.64-2.58 (m, 4H), 2.37 (s, 3H). MS: 609 (MH)$^+$.

Example 771

5-Chloro-N*2*-[3-(2-methanesulfonyl-ethyl)-8-methoxy-2,3,4,5-tetrahydro-1H-benzo[d]azepin-7-yl]-N*4*-[2-methoxy-4-(4-methyl-piperazin-1-yl)-phenyl]-pyrimidine-2,4-diamine The title compound was prepared from 3-(2-Methanesulfonyl-ethyl)-8-methoxy-2,3,4,5-tetrahydro-1H-benzo[d]azepin-7-ylamine and (2,5-Dichloro-pyrimidin-4-yl)-[2-methoxy-4-(4-methyl-piperazin-1-yl)-phenyl]-amine in an analogous manner to Example 61e. Product isolated as an off-white solid (0.052 g, 61%). MP: 138-145° C. $^1$H NMR (400, MHz, CDCl$_3$, δ, ppm): 8.18 (d, 1H, J=8.6 Hz), 8.11 (s, 1H), 8.01 (d, 1H, J=1.0 Hz), 7.48 (br s, 1H), 7.43 (br s, 1H), 6.62 (s, 1H), 6.58-6.56 (m, 1H), 6.54-6.50 (m, 1H), 3.91 (s, 3H), 3.86 (s, 3H), 3.23-3.13 (m, 6H), 3.07 (s, 3H), 3.01 (t, 3H, J=6.2 Hz), 2.88-2.83 (m, 2H), 2.81-2.77 (m, 2H), 2.71-2.64 (m, 2H), 2.64-2.58 (m, 4H), 2.38 (s, 3H). MS: 630 (MH)$^+$.

Example 772

7-{5-Chloro-4-[2-methoxy-4-(4-methyl-piperazin-1-yl)-phenylamino]-pyrimidin-2-ylamino}-3-ethyl-8-methoxy-1,3,4,5-tetrahydro-benzo[d]azepin-2-one The title compound was prepared from 7-Amino-3-ethyl-8-methoxy-1,3,4,5-tetrahydro-benzo[d]azepin-2-one and (2,5-Dichloro-pyrimidin-4-yl)-[2-methoxy-4-(4-methyl-piperazin-1-yl)-phenyl]-amine in an analogous manner to Example 61e. Product isolated as a tan solid (0.060 g, 65%). MP: 222-233° C. $^1$H NMR (400 MHz, CDCl$_3$, δ, ppm): 8.16 (d, 1H, J=8.6 Hz), 8.08 (s, 1H), 8.02 (s, 1H), 7.48 (s, 1H), 7.42 (s, 1H), 6.61 (s, 1H), 6.57 (d, 1H, J=2.5 Hz), 6.55-6.51 (m, 1H), 3.91 (s, 3H), 3.85 (s, 3H), 3.84-3.80 (m, 2H), 3.70-3.64 (m, 2H), 3.48 (q, 2H, J=7.2 Hz), 3.25-3.17 (m, 4H), 3.03-2.97 (m, 2H), 2.65-2.57 (m, 4H), 2.38 (s, 3H), 1.17 (t, 3H, J=7.1 Hz). MS: 566 (MH)$^+$.

Example 773

(1S,2S,3R,4R)-3-[5-Chloro-2-(3-ethyl-8-methoxy-2,3,4,5-tetrahydro-1H-benzo[d]azepin-7-ylamino)-pyrimidin-4-ylamino]-bicyclo[2.2.1]hept-5-ene-2-carboxylic acid amide 7-Methoxy-8-nitro-2,3,4,5-tetrahydro-1H-benzo[d]azepine was converted in an analogous manner to Example 31e, to 3-Ethyl-7-methoxy-8-nitro-2,3,4,5-tetrahydro-1H-benzo[d]azepine which was converted in an analogous manner to Example 31f, to 3-Ethyl-8-methoxy-2,3,4,5-tetrahydro-1H-benzo[d]azepin-7-ylamine which was converted to the title compound in an analogous manner to Example 61e using (1S,2S,3R,4R)-3-(2,5-Dichloro-pyrimidin-4-ylamino)-bicyclo[2.2.1]hept-5-ene-2-carboxylic acid amide. Product isolated as an off-white solid (0.032 g, 40%). MP: 126-138° C. $^1$H NMR (400 MHz, CDCl$_3$, δ, ppm): 8.19 (s, 1H), 7.89 (d, 1H, J=0.76 Hz), 7.34 (s, 1H), 6.65 (s, 1H), 6.51 (d, 1H, J=8.6 Hz), 6.34-6.27 (m, 2H), 5.54 (br s, 1H), 5.26 (br s, 1H), 4.49-4.43 (m, 1H), 3.87 (s, 3H), 3.07 (s, 1H), 2.92-2.84 (m, 5H), 2.70-2.55 (m, 6H), 2.52 (d, 1H, J=8.3 Hz), 2.26 (d, 1H, J=9.6 Hz), 1.68-1.63 (m, 1H), 1.11 (t, 3H, J=7.1 Hz). MS: 483 (MH)$^+$.

Example 774

(1S,2S,3R,4R)-3-[5-Chloro-2-(8-methoxy-3-propyl-2,3,4,5-tetrahydro-1H-benzo[d]azepin-7-ylamino)-pyrimidin-4-ylamino]-bicyclo[2.2.1]hept-5-ene-2-carboxylic acid amide 7-Methoxy-8-nitro-2,3,4,5-tetrahydro-1H-benzo[d]azepine using 1-Bromopropane was converted in an analogous manner to Example 31e, to 7-Methoxy-8-nitro-3-propyl-2,3,4,5-tetrahydro-1H-benzo[d]azepine which was converted in an analogous manner to Example 31f, to 8-Methoxy-3-propyl-2,3,4,5-tetrahydro-1H-benzo[d]azepin-7-ylamine which was converted to the title compound in an analogous manner to Example 61e using (1S,2S,3R,4R)-3-(2,5-Dichloro-pyrimidin-4-ylamino)-bicyclo[2.2.1]hept-5-ene-2-carboxylic acid amide. Product isolated as an off-white solid (0.031 g, 37%). MP: 124-138° C. $^1$H NMR (400 MHz, CDCl$_3$, δ, ppm): 8.18 (s, 1H), 7.89 (d, 1H, J=1.5 Hz), 7.34 (s, 1H), 6.64 (s, 1H), 6.50 (d, 1H, J=8.3 Hz), 6.34-6.29 (m, 2H), 5.54 (br s, 1H), 5.25 (br s, 1H), 4.49-4.43 (m, 1H), 3.86 (d, 3H, J=1.0 Hz), 3.09-3.05 (m, 1H), 2.91-2.82 (m, 5H), 2.71-2.58 (m, 4H), 2.55-2.50 (m, 1H), 2.48-2.42 (m, 2H), 2.29-2.23 (m, 1H), 1.69-1.64 (m, 1H), 1.57-1.49 (m, 2H), 0.91 (t, 3H, J=6.8 Hz). MS: 497 (MH)$^+$.

Example 775

(1S,2S,3R,4R)-3-[5-Chloro-2-(3-cyclopropylmethyl-8-methoxy-2,3,4,5-tetrahydro-1H-benzo[d]azepin-7-ylamino)-pyrimidin-4-ylamino]-bicyclo[2.2.1]hept-5-ene-2-carboxylic acid amide 7-Methoxy-8-nitro-2,3,4,5-tetrahydro-1H-benzo[d]azepine using Cyclopropylmethyl bromide was converted in an analogous manner to Example 31e, to 3-Cyclopropylmethyl-7-methoxy-8-nitro-2,3,4,5-tetrahydro-1H-benzo[d]azepine which was converted in an analogous manner to Example 31f, to 3-Cyclopropylmethyl-8-methoxy-2,3,4,5-tetrahydro-1H-benzo[d]azepin-7-ylamine which was converted, in an analogous manner to Example 61e to the title compound using (1S,2S,3R,4R)-3-(2,5-Dichloro-pyrimidin-4-ylamino)-bicyclo[2.2.1]hept-5-ene-2-carboxylic acid amide. Product isolated as an off-white solid (0.028 g, 33%). MP: 129-145° C. $^1$H NMR (400 MHz, CDCl$_3$, δ, ppm): 8.20 (s, 1H), 7.86 (d, 1H, J=1.3 Hz), 7.39 (s, 1H), 6.76 (d, 1H, J=8.3 Hz), 6.63 (s, 1H), 6.32-6.25 (m, 2H), 5.84 (br s, 1H), 5.59 (br s, 1H), 4.40 (t, 1H, J=8.0 Hz), 3.86 (s, 3H), 3.10-2.80 (m, 10H), 2.65 (d, 2H, J=5.8 Hz), 2.52 (d, 1H, J=8.1 Hz), 2.24 (d, 1H, J=9.1 Hz), 1.62 (d, 1H, J=8.8 Hz), 1.01-0.92 (m, 1H), 0.64-0.57 (m, 2H), 0.26-0.14 (m, 2H). MS: 509 (MH)$^+$.

Example 776

(1S,2S,3R,4R)-3-[5-Chloro-2-(3-isopropyl-8-methoxy-2,3,4,5-tetrahydro-1H-benzo[d]azepin-7-ylamino)-pyrimidin-4-ylamino]-bicyclo[2.2.1]hept-5-ene-2-carboxylic acid amide 776a) To a solution of 7-Methoxy-8-nitro-2,3,4,5-tetrahydro-1H-benzo[d]azepine (0.15 g, 0.00067 mol), Acetone (0.10 mL, 0.0014 mol), Acetic acid (0.1 mL, 0.002 mol) and Methanol (10 mL, 0.2 mol) was added Sodium cyanoborohydride (50 mg, 0.0008 mol). The mixture was stirred at room temperature for 4 hours. The reaction mixture was evaporated and the residue was partitioned between water (20 mL) and dichloromethane (20 mL). The organic layers were dried over magnesium sulfate, filtered and evaporated. The mixture was purified via silica gel chromatography using amine modified silica gel 10%→100% Ethyl Acetate:Hexane solvent gradient. 3-Isopropyl-7-methoxy-8-nitro-2,3,4,5-tetrahydro-1H-benzo[d]azepine isolated as a yellow oil.

776b) 3-Isopropyl-7-methoxy-8-nitro-2,3,4,5-tetrahydro-1H-benzo[d]azepine was converted in an analogous manner to Example 31f, to 3-Isopropyl-8-methoxy-2,3,4,5-tetrahydro-1H-benzo[d]azepin-7-ylamine which was converted to title compound in an analogous manner to Example 61e using (1S,2S,3R,4R)-3-(2,5-Dichloro-pyrimidin-4-ylamino)-bicyclo[2.2.1]hept-5-ene-2-carboxylic acid amide. Product isolated as an off-white solid (0.018 g, 20%). MP: 125-145° C. $^1$H NMR (400 MHz, CDCl$_3$, δ, ppm): 8.18 (s, 1H), 7.88 (d, 1H, J=1.3 HZ), 7.39 (s, 1H), 6.65 (s, 1H), 6.59 (d, 1H, J=8.3 Hz), 6.34-6.28 (m, 2H), 5.66 (br s, 1H), 5.50 (br s, 1H), 4.44 (t, 1H, J=8.2 Hz), 3.56 (s, 3H), 3.09-2.96 (m, 2H), 2.95-2.80 (m, 5H), 2.77-2.60 (m, 4H), 2.52 (d, 1H, J=8.1 Hz), 2.26 (d, 1H, J=9.1 Hz), 1.68-1.61 (m, 1H), 1.05 (d, 6H, J=6.6 Hz). MS: 497 (MH)$^+$.

Example 777

2-{5-Chloro-2-[3-(2,2-difluoro-ethyl)-8-methoxy-2,3,4,5-tetrahydro-1H-benzo[d]azepin-7-ylamino]-pyrimidin-4-ylamino}-N-ethyl-3-fluoro-benzamide The title compound was prepared from 3-(2,2-Difluoro-ethyl)-8-methoxy-2,3,4,5-tetrahydro-1H-benzo[d]azepin-7-ylamine and 2-(2,5-Dichloro-pyrimidin-4-ylamino)-N-ethyl-3-fluoro-benzamide in an analogous manner to Example 61e. Product isolated as an off-white solid (0.012 g, 14%). MP: 93-104° C. $^1$H NMR (400 MHz, CDCl$_3$, δ, ppm): 8.49 (s, 1H), 8.07 (s, 1H), 7.73 (s, 1H), 7.45 (s, 1H), 7.36-7.31 (m, 1H), 7.29-7.22 (m, 2H), 6.57 (s, 1H), 6.20-6.10 (m, 1H), 5.90 (tt, 1H, J=56.0 Hz and 3.9 Hz), 3.81 (s, 3H), 3.37 (p, 2H, J=6.7 Hz), 2.90 (dt, 2H, J=15.0 Hz and 4.1 Hz), 2.84-2.73 (m, 4H), 2.72-2.66 (m, 2H), 2.60-2.52 (m, 2H), 1.10 (t, 3H, J=7.3 Hz). MS: 549 (MH)$^+$.

Example 778

7-{5-Chloro-4-[2-methoxy-4-(4-methyl-piperazin-1-yl)-phenylamino]-pyrimidin-2-ylamino}-8-methoxy-1,3,4,5-tetrahydro-benzo[d]azepin-2-one The title compound was prepared from 7-Amino-8-methoxy-1,3,4,5-tetrahydro-benzo[d]azepin-2-one and (2,5-Dichloro-pyrimidin-4-yl)-[2-methoxy-4-(4-methyl-piperazin-1-yl)-phenyl]-amine in an analogous manner to Example 61e. Product isolated as an off-white solid (0.012 g, 15%). MP: 208-213° C. $^1$H NMR (400 MHz, CDCl$_3$, δ, ppm): 8.14-8.10 (m, 2H), 8.03-8.02 (m, 1H), 7.44 (s, 2H), 6.64-6.62 (m, 1H), 6.58-6.56 (m, 1H), 6.54-6.49 (m, 1H), 5.70 (br s, 1H), 3.90 (s, 3H), 3.86 (s, 3H), 3.78 (s, 3H), 3.56-3.50 (m, 2H), 3.23-3.18 (m, 4H), 3.00-2.96 (m, 2H), 2.64-2.59 (m, 4H), 2.38 (s, 3H). MS: 538 (MH)$^+$.

Example 779

5-Chloro-N*2*-[3-(2,2-difluoro-propyl)-8-methoxy-2,3,4,5-tetrahydro-1H-benzo[d]azepin-7-yl]-N*4*-[3-methyl-4-(4-methyl-piperazin-1-yl)-phenyl]-pyrimidine-2,4-diamine 779a) To mixture of 2,2-Difluoro-propan-1-ol (0.26 g, 0.0027 mol) and Pyridine (0.27 mL, 0.0034-mol) in Acetonitrile (25 mL, 0.48 mol) at 0-5° C. was added dropwise Trifluoromethanesulfonic anhydride (0.48 mL, 0.0028 mol). The mixture was stirred for 30 minutes then Potassium carbonate (0.37 g, 0.0027 mol) and 7-Methoxy-8-nitro-2,3,4,5-tetrahydro-1H-benzo[d]azepine (0.30 g, 0.0013 mol) were added. The reaction mixture was warmed to room temperature then heated to 50° C. for 18 hours. The mixture was evaporated. The residue was dissolved in dichloromethane (50 mL) and washed with water (50 mL), dried over magnesium sulfate, filtered and evaporated. The material was purified via silica gel chromatography using 0%→10% Methanol:Dichloromethane solvent gradient. 3-(2,2-Difluoropropyl)-7-methoxy-8-nitro-2,3,4,5-tetrahydro-1H-benzo[d]azepine isolated as a yellow solid (0.316 g, 78%).

779b) 3-(2,2-Difluoro-propyl)-7-methoxy-8-nitro-2,3,4,5-tetrahydro-1H-benzo[d]azepine was converted in an analogous manner to Example 31f, to 3-(2,2-Difluoro-propyl)-8-methoxy-2,3,4,5-tetrahydro-1H-benzo[d]azepin-7-ylamine which was converted to the title compound in an analogous manner to Example 61e using (2,5-Dichloro-pyrimidin-4-yl)-[3-methyl-4-(4-methyl-piperazin-1-yl)-phenyl]-amine. Product isolated as an off-white solid (0.011 g, 24%). MP: 224-227° C. $^1$H NMR (400 MHz, CDCl$_3$, δ, ppm): 8.02 (s, 2H), 7.53-7.46 (m, 2H), 7.24-7.19 (m, 1H), 7.05 (d, 1H, J=8.6 Hz), 6.90 (s, 1H), 6.60 (s, 1H), 3.84 (s, 3H), 3.00-2.93 (m, 4H), 2.87-2.71 (m, 8H), 2.69-2.55 (m, 6H), 2.40 (s, 3H), 2.30 (s, 3H), 1.68 (t, 3H, J=18.7 Hz). MS: 586 (MH)$^+$.

Example 780

5-Chloro-N*2*-[3-(2,2-difluoro-propyl)-8-methoxy-2,3,4,5-tetrahydro-1H-benzo[d]azepin-7-yl]-N*4*-(2-methoxy-4-morpholin-4-yl-phenyl)-pyrimidine-2,4-diamine The title compound was prepared from 3-(2,2-Difluoro-propyl)-8-methoxy-2,3,4,5-tetrahydro-1H-benzo[d]azepin-7-ylamine and (2,5-Dichloro-pyrimidin-4-yl)-(2-methoxy-4-morpholin-4-yl-phenyl)-amine in an analogous manner to Example 61e. Product isolated as an off-white solid (0.047 g, 57%). MP: 215-220° C. $^1$H NMR (400 MHz, CDCl$_3$, δ, ppm): 8.23 (d, 1H, J=8.8 Hz), 8.10 (s, 1H), 8.01 (s, 1H), 7.51 (s, 1H), 7.44 (s, 1H), 6.62 (s, 1H), 6.54 (d, 1H, J+2.3 Hz), 6.50 (dd, 1H, J=8.8 Hz and 2.0 Hz), 3.91 (s, 3H), 3.90-3.87 (m, 4H), 3.86 (s, 3H), 3.18-3.12 (m, 4H), 2.90-2.76 (m, 10H), 1.68 (t, 3H, J=18.7 Hz). MS: 589 (MH)$^+$.

Example 781

5-Chloro-N*2*-[3-(2,2-difluoro-propyl)-8-methoxy-2,3,4,5-tetrahydro-1H-benzo[d]azepin-7-yl]-N*4*-[2-methoxy-4-(4-methyl-piperazin-1-yl)-phenyl]-pyrimidine-2,4-diamine The title compound was prepared from 3-(2,2-Difluoro-propyl)-8-methoxy-2,3,4,5-tetrahydro-1H-benzo[d]azepin-7-ylamine and (2,5-Dichloro-pyrimidin-4-yl)-[2-methoxy-4-(4-methyl-piperazin-1-yl)-phenyl]-amine in an analogous manner to Example 61e. Product isolated as an off-white solid (0.030 g, 37%). MP: 165-167° C. $^1$H NMR (400 MHz, CDCl$_3$, δ, ppm): 8.21 (d, 1H, J=8.8 Hz), 8.10 (s, 1H), 8.01 (s, 1H), 7.51 (s, 1H), 7.43 (s, 1H), 6.62 (s, 1H), 6.58-6.55 (m, 1H), 6.54-6.50 (s, 1H), 3.91 (s, 3H), 3.85 (s, 3H), 3.24-3.18 (m, 4H), 2.90-2.77 (m, 10H), 2.64-2.57 (m, 4H), 2.37 (s, 3H), 1.68 (t, 3H, J=18.9 Hz). MS: 602 (MH)$^+$.

Example 782

(1S,2S,3R,4R)-3-{5-Chloro-2-[3-(2,2-difluoro-propyl)-8-methoxy-2,3,4,5-tetrahydro-1H-benzo[d]azepin-7-ylamino]-pyrimidin-4-ylamino}-bicyclo[2.2.1]hept-5-ene-2-carboxylic acid amide The title compound was prepared from 3-(2,2-Difluoro-propyl)-8-methoxy-2,3,4,5-tetrahydro-1H-benzo[d]azepin-7-ylamine and (1S,2S,3R,4R)-3-(2,5-Dichloro-pyrimidin-4-ylamino)-bicyclo[2.2.1]hept-5-ene-2-carboxylic acid amide in an analogous manner to Example 61e. Product isolated as an off-white solid (0.060 g, 67%). MP: 120-134° C. $^1$H NMR (400 MHz, CDCl$_3$, δ, ppm): 8.18 (s, 1H), 7.89 (s, 1H), 7.39 (s, 1H), 6.63 (s, 1H), 6.56-6.50 (m, 1H), 6.34-6.29 (m, 2H), 5.53 (br s, 1H), 5.26 (br s, 1H), 4.48-4.42 (m, 1H), 3.86 (s, 3H), 3.09-3.05 (m, 1H), 2.90 (m, 12H), 2.54-2.49 (m, 1H), 2.29-2.24 (m, 1H), 1.68 (t, 3H, J=18.7 Hz). MS: 533 (MH)$^+$.

Example 783

2-(7-{5-Chloro-4-[2-methoxy-4-(4-methyl-piperazin-1-yl)-phenylamino]-pyrimidin-2-ylamino}-8-methoxy-1,2,4,5-tetrahydro-benzo[d]azepin-3-yl)-N-methyl-acetamide The title compound was prepared from 2-(7-Amino-8-methoxy-1,2,4,5-tetrahydro-benzo[d]azepin-3-yl)-N-methyl-acetamide and (2,5-Dichloro-pyrimidin-4-yl)-[2-methoxy-4-(4-methyl-piperazin-1-yl)-phenyl]-amine in an analogous manner to Example 61e. Product isolated as an off-white solid (0.005 g, 10%). MP: 82-100° C. $^1$H NMR (400 MHz, CDCl$_3$, δ, ppm): 8.20 (d, 1H, J=8.8 Hz), 8.12 (s, 1H), 8.02 (s, 1H), 7.50 (s, 1H), 7.44 (s, 1H), 7.39-7.31 (m, 1H), 6.63 (s, 1H), 6.56 (d, 1H), J=2.0 Hz), 6.50 (dd, 1H, J=8.7 and 2.4 Hz), 3.91 (s, 3H), 3.86 (s, 3H), 3.23-3.16 (m, 4H), 3.11 (s, 2H), 2.90 (d, 3H, J=5.1 Hz), 2.88-2.83 (m, 2H), 2.83-2.78 (m, 2H), 2.72-2.65 (m, 4H), 2.65-2.58 (m, 4H), 2.38 (s, 3H). MS: 595 (MH)$^+$.

Example 784

N-((1R,2R)-2-{5-Chloro-2-[3-(2,2-difluoro-propyl)-8-methoxy-2,3,4,5-tetrahydro-1H-benzo[d]azepin-7-ylamino]-pyrimidin-4-ylamino}-cyclohexyl)-methanesulfonamide The title compound was prepared from 3-(2,2-Difluoro-propyl)-8-methoxy-2,3,4,5-tetrahydro-1H-benzo[d]azepin-7-ylamine and N-[(1R,2R)-2-(2,5-Dichloro-pyrimidin-4-ylamino)-cyclohexyl]-methanesulfonamide in a manner analogous to Example 61e. Product isolated as an off-white solid (0.011 g, 13%). MP: 94-115° C. $^1$H NMR (400 MHz, CDCl$_3$, δ, ppm): 7.97 (s, 1H), 7.94 (s, 1H), 7.33 (br s, 1H), 6.64 (s, 1H), 5.36 (d, 1H, J=7.6 Hz), 5.29 (d, 1H, J=7.1 Hz), 3.99-3.89 (m, 1H), 3.87 (s, 3H), 3.29-3.18 (m, 1H), 2.91-2.80 (m, 10H), 2.79 (s, 3H), 2.27-2.15 (m, 2H), 1.86-1.77 (m, 2H), 1.68 (t, 3H, J=18.8 Hz), 1.40-1.32 (m, 4H). MS: 573 (MH)$^+$.

Example 785

5-Chloro-N*4*-(5-chloro-2-methoxy-phenyl)-N*2*-[3-(2,2-difluoro-propyl)-8-methoxy-2,3,4,5-tetrahydro-1H-benzo[d]azepin-7-yl]-pyrimidine-2,4-diamine The title compound was prepared from 3-(2,2-Difluoro-propyl)-8-methoxy-2,3,4,5-tetrahydro-1H-benzo[d]azepin-7-ylamine and (5-Chloro-2-methoxy-phenyl)-(2,5-dichloro-pyrimidin-4-yl)-amine in an analogous manner to Example 61e. Product isolated as an off-white solid (0.063 g, 71%). MP: 170-173° C. $^1$H NMR (400 MHz, CDCl$_3$, δ, ppm): 8.48 (s, 1H), 8.09 (s, 1H), 8.00 (s, 1H), 7.78 (s, 1H), 7.42 (s, 1H), 7.03-6.98 (m, 1H), 6.86-6.82 (m, 1H), 6.65 (s, 1H), 3.93 (s, 3H), 3.88 (s, 3H), 2.89-2.78 (m, 10H), 1.68 (t, 3H, J=18.7 Hz). MS: 538 (MH)$^+$.

Example 786

2-{5-Chloro-2-[3-(2,2-difluoro-propyl)-8-methoxy-2,3,4,5-tetrahydro-1H-benzo[d]azepin-7-ylamino]-pyrimidin-4-ylamino}-N-methyl-benzamide The title compound was prepared from 3-(2,2-Difluoro-propyl)-8-methoxy-2,3,4,5-tetrahydro-1H-benzo[d]azepin-7-ylamine and 2-(2,5-Dichloro-pyrimidin-4-ylamino)-N-methyl-benzamide in an analogous manner to Example 61e. Product isolated as a pale yellow solid (0.019 g, 21%). MP: 162-165° C. $^1$H NMR (400 MHz, CDCl$_3$, δ, ppm): 11.00-10.97 (m, 1H), 8.68-8.64 (m, 1H), 8.11 (d, 1H, J=1.8 Hz), 8.09-8.07 (m, 1H), 7.54-7.39 (m, 3H), 7.11-7.06 (m, 1H), 6.64 (s, 1H), 6.18 (br s, 1H), 3.87 (d, 3H, J=1.5 Hz), 3.06-3.02 (m, 3H), 2.90-2.72 (m, 10H), 1.75-1.61 (m, 3H). MS: 531.17 (MH)$^+$.

Example 788

2-{5-Chloro-2-[3-(2,2-difluoro-propyl)-8-methoxy-2,3,4,5-tetrahydro-1H-benzo[d]azepin-7-ylamino]-pyrimidin-4-ylamino}-N-ethyl-benzamide The title compound was prepared from 3-(2,2-Difluoro-propyl)-8-methoxy-2,3,4,5-tetrahydro-1H-benzo[d]azepin-7-ylamine and 2-(2,5-Dichloro-pyrimidin-4-ylamino)-N-ethyl-benzamide in an analogous manner to Example 61e. Product isolated as a white solid (0.011 g, 11%). MP: 165-167° C. $^1$H NMR (400 MHz, CDCl$_3$, δ, ppm): 10.94 (s, 1H), 8.65 (d, 1H, J=8.6 Hz), 8.10 (d, 1H, J=1.5 Hz), 8.09-8.07 (m, 1H), 7.53-7.39 (m, 3H), 7.12-7.06 (m, 1H), 6.64 (s, 1H), 6.13 (br s, 1H), 3.86 (s, 3H), 3.57-3.48 (m, 2H), 2.90-2.73 (m, 10H), 1.69 (t, 3H, J=18.6 Hz), 1.30-1.24 (m, 3H). MS: 545.21 (MH)$^+$.

Example 789

2-{5-Chloro-2-[3-(2,2-difluoro-propyl)-8-methoxy-2,3,4,5-tetrahydro-1H-benzo[d]azepin-7-ylamino]-pyrimidin-4-ylamino}-N-ethyl-3-fluoro-benzamide The title compound was prepared from 3-(2,2-Difluoro-propyl)-8-methoxy-2,3,4,5-tetrahydro-1H-benzo[d]azepin-7-ylamine and 2-(2,5-Dichloro-pyrimidin-4-ylamino)-N-ethyl-3-fluoro-benzamide in an analogous manner to Example 61e. Product isolated as an off-white solid (0.038 g, 44%). MP: 85-93° C. $^1$H NMR (400 MHz, CDCl$_3$, δ, ppm): 8.45 (s, 1H), 8.08-8.06 (m, 1H), 7.72 (s, 1H), 7.45 (s, 1H), 7.36-7.31 (m, 1H), 7.30-7.25 (m, 2H), 6.57 (s, 1H), 6.14-6.06 (m, 1H), 3.82 (s, 3H), 3.41-3.33 (m, 2H), 2.89-2.76 (m, 6H), 2.75-2.70 (m, 2H), 2.57-2.50 (m, 2H), 1.69 (t, 3H, J=18.7 Hz), 1.13-1.06 (m, 3H). MS: 563.18 (MH)$^+$.

Example 790

5-Chloro-N*2*-[8-methoxy-3-(2-methoxy-ethyl)-2,3,4,5-tetrahydro-1H-benzo[d]azepin-7-yl]-N*4*-[2-methoxy-4-(4-methyl-piperazin-1-yl)-phenyl]-pyrimidine-2,4-diamine The title compound was prepared from 8-Methoxy-3-(2-methoxy-ethyl)-2,3,4,5-tetrahydro-1H-benzo[d]azepin-7-ylamine and (2,5-Dichloro-pyrimidin-4-yl)-[2-methoxy-4-(4-methyl-piperazin-1-yl)-phenyl]-amine in an analogous manner to Example 61e. Product isolated as tan solid (0.022 g, 23%). MP: 54-75° C. $^1$H NMR (400 MHz, CDCl$_3$, δ, ppm): 8.26 (d, 1H, J=8.8 Hz), 8.11 (s, 1H), 8.02-8.00 (m, 1H), 7.55 (s, 1H), 7.42 (s, 1H), 6.63 (s, 1H), 6.58-6.55 (m, 1H), 6.55-6.50 (m, 1H), 3.91 (s, 3H), 3.86 (s, 3 h), 3.57-3.51 (m, 2H), 3.37 (s, 3H), 3.24-3.16 (m, 4H), 2.92-2.83 (m, 4H), 2.77-2.67 (m, 6H), 2.64-2.58 (m, 4H), 2.37 (s, 3H). MS: 582.24 (MH)$^+$.

Example 792

2-(7-{5-Chloro-4-[3-methyl-4-(4-methyl-piperazin-1-yl)-phenylamino]-pyrimidin-2-ylamino}-8-methoxy-1,2,4,5-tetrahydro-benzo[d]azepin-3-yl)-N,N-dimethyl-acetamide The title compound was prepared from 2-(7-Amino-8-methoxy-1,2,4,5-tetrahydro-benzo[d]azepin-3-yl)-N,N-dimethyl-acetamide and (2,5-Dichloro-pyrimidin-4-yl)-[3-methyl-4-(4-methyl-piperazin-1-yl)-phenyl]-amine in an analogous manner to Example 61e. Product isolated as a pale yellow solid (0.020 g, 24%). MP: 172-178° C. $^1$H NMR (400 MHz, CDCl$_3$, δ, ppm): 8.04-8.01 (m, 2H), 7.54-7.49 (m, 1H), 7.47 (s, 1H), 7.24-7.21 (m, 1H), 7.07-7.02 (m, 1H), 6.90 (s, 1H), 6.61 (s, 1H), 3.84 (s, 3H), 3.26 (s, 2H), 3.14 (s, 3H), 3.01-2.92 (m, 8H), 2.88-2.83 (m, 2H), 2.75-2.59 (m, 9H), 2.44-2.36 (m, 3H), 2.30 (s, 3H). MS: 593.29 (MH)$^+$.

Example 793

2-(7-{5-Fluoro-4-[2-methoxy-4-(4-methyl-piperazin-1-yl)-phenylamino]-pyrimidin-2-ylamino}-8-methoxy-1,2,4,5-tetrahydro-benzo[d]azepin-3-yl)-N,N-dimethyl-acetamide 2-Methoxy-4-(4-methyl-piperazin-1-yl)-phenylamine using 2,4-Dichloro-5-fluoropyrimidine was converted in an analogous manner to Example 1d, to (2-Chloro-5-fluoro-pyrimidin-4-yl)-[2-methoxy-4-(4-methyl-piperazin-1-yl)-phenyl]-amine which was converted to the title compound in an analogous manner to Example 61e using 2-(7-Amino-8-methoxy-1,2,4,5-tetrahydro-benzo[d]azepin-3-yl)-N,N-dimethyl-acetamide. Product isolated as a pale yellow solid (0.025 g, 30%). MP: 54-80° C. $^1$H NMR (400 MHz, CDCl$_3$, δ, ppm): 8.32-8.28 (m, 1H), 8.13 (s, 1H), 7.92-7.89 (m, 1H), 7.39-7.36 (m, 1H), 7.22-7.19 (m, 1H), 6.63 (s, 1H), 6.58-6.51 (m, 2H), 3.91 (d, 3H, J=1.0 Hz), 3.86 (d, 3H, J=1.0 Hz), 3.27 (s, 2H), 3.23-3.17 (m, 4H), 3.15 (s, 3H), 2.98 (s, 3H), 2.91-2.85 (m, 4H), 2.72-2.66 (m, 4H), 2.64-2.58 (m, 4H), 2.37 (s, 3H). MS: 593.30 (MH)$^+$.

Example 794

2-(7-{5-Chloro-4-[2-methoxy-4-(2-oxa-5-aza-bicyclo[2.2.1]hept-5-yl)-phenylamino]-pyrimidin-2-ylamino}-8-methoxy-1,2,4,5-tetrahydro-benzo[d]azepin-3-yl)-N,N-dimethyl-acetamide 2-Methoxy-4-(2-oxa-5-aza-bicyclo[2.2.1]hept-5-yl)-phenylamine using 2,4,5-Trichloro-pyrimidine was converted in an analogous manner to Example 1d, to (2,5-Dichloro-pyrimidin-4-yl)-[2-methoxy-4-(2-oxa-5-aza-bicyclo[2.2.1]hept-5-yl)-phenyl]-amine which was converted to the title compound in an analogous manner to Example 61e using 2-(7-Amino-8-methoxy-1,2,4,5-tetrahydro-benzo[d]azepin-3-yl)-N,N-dimethyl-acetamide. Product Isolated as a pale yellow solid (0.029 g, 35%). MP: 94-110° C. $^1$H NMR (400 MHz, CDCl$_3$, δ, ppm): 8.17-8.09 (m, 2H), 7.99 (d, 1H, J=1.5 Hz), 7.43 (s, 1H), 7.39 (s, 1H), 6.62 (s, 1H), 6.21-6.16 (m, 2H), 4.67 (s, 1H), 4.40 (s, 1H), 3.96-3.92 (m, 1H), 3.91-3.84

(m, 7H), 3.59 (d, 1H, J=9.1 Hz), 3.26 (s, 2H), 3.18 (d, 1H, J=9.1 Hz), 3.14 (s, 3H), 2.97 (s, 3H), 2.90-2.79 (m, 4H), 2.72-2.64 (m, 4H), 2.08-2.03 (m, 1H), 2.00-1.95 (m, 1H). MS: 608.28 (MH)+.

Example 795

2-(7-{5-Chloro-4-[4-(5-ethyl-2,5-diaza-bicyclo[2.2.1]hept-2-yl)-2-methoxy-phenylamino]-pyrimidin-2-ylamino}-8-methoxy-1,2,4,5-tetrahydro-benzo[d]azepin-3-yl)-N,N-dimethyl-acetamide 4-(5-Ethyl-2,5-diaza-bicyclo[2.2.1]hept-2-yl)-2-methoxy-phenylamine using 2,4,5-Trichloro-pyrimidine was converted in an analogous manner to Example 1d, to (2,5-Dichloro-pyrimidin-4-yl)-[4-(5-ethyl-2,5-diaza-bicyclo[2.2.1]hept-2-yl)-2-methoxy-phenyl]-amine which was converted to the title compound in an analogous manner to Example 61e using 2-(7-Amino-8-methoxy-1,2,4,5-tetrahydro-benzo[d]azepin-3-yl)-N,N-dimethyl-acetamide. Product isolated as a pale yellow solid (0.030 g, 37%). MP: 88-100° C. $^1$H NMR (400 MHz, CDCl$_3$, δ, ppm): 8.13-8.08 (m, 2H), 7.98 (d, 1H, J=1.0 Hz), 7.42 (s, 1H), 7.39 (s, 1H), 6.62 (s, 1H), 6.18-6.13 (s, 2H), 4.22-4.18 (m, 1H), 3.89 (s, 3H), 3.85 (s, 3H), 3.65-3.61 (m, 1H), 3.44-3.38 (m, 1H), 3.36-3.31 (m, 1H), 3.26 (s, 3H), 3.14 (s, 3H), 3.07-3.01 (m, 1H), 2.97 (s, 3H), 2.90-2.82 (m, 4H), 2.71-2.64 (m, 4H), 2.63-2.59 (m, 1H), 2.58-2.50 (m, 2H), 2.03-1.97 (m, 1H), 1.96-1.90 (m, 1H), 1.09-1.03 (m, 3H). MS: 635.31 (MH)+.

Example 796

2-{7-[5-Chloro-4-(3-methyl-4-morpholin-4-yl-phenylamino)-pyrimidin-2-ylamino]-8-methoxy-1,2,4,5-tetrahydro-benzo[d]azepin-3-yl}-N,N-dimethyl-acetamide 1-Chloro-2-methyl-4-nitro-benzene using Morpholine was converted in an analogous manner to Example 171b, to 4-(2-Methyl-4-nitro-phenyl)-morpholine which was converted in an analogous manner to Example 31f, to 3-Methyl-4-morpholin-4-yl-phenylamine, which was converted, in an analogous manner to Example 1d, to (2,5-Dichloro-pyrimidin-4-yl)-(3-methyl-4-morpholin-4-yl-phenyl)-amine which was converted to the title compound in an analogous manner to Example 61e using 2-(7-Amino-8-methoxy-1,2,4,5-tetrahydro-benzo[d]azepin-3-yl)-N,N-dimethyl-acetamide. Product isolated as a white solid (0.041 g, 36%). MP: 252-256° C. $^1$H NMR (400 MHz, CDCl$_3$, δ, ppm): 8.04 (s, 2H), 7.57-7.53 (m, 1H), 7.48 (s, 1H), 7.24-7.21 (m, 1H), 7.03 (d, 1H, J=8.6 Hz), 6.91 (s, 1H), 6.61 (s, 1H), 3.89-3.85 (m, 4H), 3.85 (s, 3H), 3.26 (s, 2H), 3.13 (s, 3H), 2.94-2.89 (m, 4H), 2.89-2.83 (m, 2H), 2.76-2.60 (m, 6H), 2.31 (s, 3H). MS: 580.27 (MH)+.

Example 797

2-(7-{5-Fluoro-4-[2-methoxy-4-(4-methyl-piperazin-1-yl)-phenylamino]-pyrimidin-2-ylamino}-8-methoxy-1,2,4,5-tetrahydro-benzo[d]azepin-3-yl)-N-methyl-acetamide The title compound was prepared from 2-(7-Amino-8-methoxy-1,2,4,5-tetrahydro-benzo[d]azepin-3-yl)-N-methyl-acetamide and (2-Chloro-5-fluoro-pyrimidin-4-yl)-[2-methoxy-4-(4-methyl-piperazin-1-yl)-phenyl]-amine in an analogous manner to Example 61e. Product isolated as an off-white solid (0.041 g, 42%). MP: 95-136° C. $^1$H NMR (400 MHz, CDCl$_3$, δ, ppm): 8.27 (d, 1H, J=8.6 Hz), 8.15 (s, 1H), 7.92-7.89 (m, 1H), 7.39 (s, 1H), 7.38-7.32 (m, 1H), 7.20-7.17 (m, 1H), 6.63 (s, 1H), 6.58-6.55 (m, 1H), 6.54-6.49 (m, 1H), 3.90 (s, 3H), 3.86 (s, 3H), 3.22-3.16 (m, 4H), 3.11 (s, 2H), 2.90 (d, 3H, J=5.1 Hz), 2.88-2.82 (m, 4H), 2.72-2.66 (m, 4H), 2.63-2.57 (m, 4H), 2.37 (s, 3H). MS: 579.30 (MH)+.

Example 798

2-(7-{5-Chloro-4-[3-methyl-4-(4-methyl-piperazin-1-yl)-phenylamino]-pyrimidin-2-ylamino}-8-methoxy-1,2,4,5-tetrahydro-benzo[d]azepin-3-yl)-N-methyl-acetamide The title compound was prepared from 2-(7-Amino-8-methoxy-1,2,4,5-tetrahydro-benzo[d]azepin-3-yl)-N-methyl-acetamide and (2,5-Dichloro-pyrimidin-4-yl)-[3-methyl-4-(4-methyl-piperazin-1-yl)-phenyl]-amine in an analogous manner to Example 61e. Product isolated as an off-white solid (0.008 g, 8%). MP: 179-185° C. $^1$H NMR (400 MHz, CDCl$_3$, δ, ppm): 8.05 (s, 1H), 8.03 (s, 1H), 7.58-7.53 (m, 1H), 7.48 (s, 1H), 7.39-7.31 (m, 1H), 7.21-7.18 (m, 1H), 7.04 (d, 1H, J=8.8 Hz), 6.91 (s, 1H), 6.61 (s, 1H), 3.85 (s, 3H), 3.09 (s, 2H), 2.97-2.92 (m, 4H), 2.90 (d, 3H, J=4.8 Hz), 2.86-2.81 (m, 2H), 2.75-2.53 (m, 9H), 2.38 (s, 3H), 2.30 (s, 3H). MS: 579.29 (MH)+.

Example 799

2-{7-[5-Chloro-4-(2-methoxy-4-morpholin-4-yl-phenylamino)-pyrimidin-2-ylamino]-8-methoxy-1,2,4,5-tetrahydro-benzo[d]azepin-3-yl}-acetamide 7-Methoxy-8-nitro-2,3,4,5-tetrahydro-1H-benzo[d]azepine using Iodoacetamide was converted in an analogous manner to Example 31e, to 2-(7-Methoxy-8-nitro-1,2,4,5-tetrahydro-benzo[d]azepin-3-yl)-acetamide which was converted in an analogous manner to Example 31f, to 2-(7-Amino-8-methoxy-1,2,4,5-tetrahydro-benzo[d]azepin-3-yl)-acetamide, which was converted to the title compound in an analogous manner to Example 61e using (2,5-Dichloro-pyrimidin-4-yl)-(2-methoxy-4-morpholin-4-yl-phenyl)-amine. Product isolated as an off-white solid (0.027 g, 28%). MP: 105-139° C. $^1$H NMR (400 MHz, CDCl$_3$, δ, ppm): 8.20 (d, 1H, J=8.8 Hz), 8.12 (s, 1H), 8.02 (s, 1H), 7.49 (m, 2H), 7.24-7.18 (m, 1H), 6.63 (s, 1H), 6.56-6.53 (m, 1H), 6.52-6.47 (m, 1H), 5.75-5.63 (m, 1H), 3.94-3.84 (m, 10H), 3.17-3.12 (m, 4H), 3.11 (s, 2H), 2.90-2.85 (m, 2H), 2.83-2.78 (m, 2H), 2.75-2.67 (m, 4H). MS: 568.22 (MH)+.

Example 800

{7-[5-Chloro-4-(2-methoxy-4-morpholin-4-yl-phenylamino)-pyrimidin-2-ylamino]-8-methoxy-1,2,4,5-tetrahydro-benzo[d]azepin-3-yl}-acetic acid isopropyl ester The title compound was a byproduct isolated from Example 799 as an off-white solid (0.016 g, 15%). MP: 70-80° C. $^1$H NMR (400 MHz, CDCl$_3$, δ, ppm): 8.27 (d, 1H, J=8.6 Hz), 8.11 (s, 1H), 8.01 (s, 1H), 7.54 (s, 1H), 7.44 (s, 1H), 6.63 (s, 1H), 6.56-6.53 (m, 1H), 6.53-6.48 (m, 1H), 5.11-5.00 (m, 1H), 3.94-3.83 (m, 10H), 3.33 (s, 2H), 3.18-3.11 (m, 4H), 2.94-2.85 (m, 4H), 2.80-2.73 (m, 4H), 1.26 (s, 3H), 1.24 (s, 3H). MS: 611.27 (MH)+.

Example 801

2-{7-[5-Chloro-4-(2-methyl-4-morpholin-4-yl-phenylamino)-pyrimidin-2-ylamino]-8-methoxy-1,2,4,5-tetrahydro-benzo[d]azepin-3-yl}-N,N-dimethyl-acetamide 4-Fluoro-2-methyl-1-nitro-benzene using Morpholine was converted in an analogous manner to Example 171b, to 4-(3-Methyl-4-nitro-phenyl)-morpholine which was converted in an analogous manner to Example 31f, to 2-Methyl-4-morpholin-4-yl-phenylamine, which was converted in an analogous manner to Example 1d, to (2,5-Dichloro-pyrimidin-4-yl)-(2-methyl-4-morpholin-4-yl-phenyl)-amine which was converted to the title compound in an analogous manner to Example 61e using 2-(7-Amino-8-methoxy-1,2,4,5-tetrahydro-benzo[d]azepin-3-yl)-N,N-dimethyl-acetamide (54.0 mg, 0.000194 mol). Product isolated as an off-white solid (0.040 g, 39%). MP: 223-226° C. $^1$H NMR (400 MHz, CDCl$_3$, δ, ppm): 8.00 (d, 1H, J=1.0 Hz), 7.86 (s, 1H), 7.52-7.45 (m, 2H), 6.83-6.76 (m, 2H), 6.68 (s, 1H), 6.57 (s, 1H), 3.91-3.86 (m, 4H), 3.82 (s, 3H), 3.25 (s, 2H), 3.20-3.13 (m, 7H), 2.99 (s, 3H), 2.85-2.80 (m, 2H), 2.67-2.56 (m, 6H), 2.26 (s, 3H). MS: 580.29 (MH)$^+$.

Example 802

2-(7-{5-Chloro-4-[2-methyl-4-(4-methyl-piperazin-1-yl)-phenylamino]-pyrimidin-2-ylamino}-8-methoxy-1,2,4,5-tetrahydro-benzo[d]azepin-3-yl)-N,N-dimethyl-acetamide 4-Fluoro-2-methyl-1-nitro-benzene using 1-methyl-piperazine in an analogous manner to Example 171b was converted to 1-Methyl-4-(3-methyl-4-nitro-phenyl)-piperazine which was converted in an analogous manner to Example 31f, to 2-Methyl-4-(4-methyl-piperazin-1-yl)-phenylamine, which was converted, in an analogous procedure to Example 1d, to (2,5-Dichloro-pyrimidin-4-yl)-[2-methyl-4-(4-methyl-piperazin-1-yl)-phenyl]-amine, which was converted to the title compound in an analogous manner to Example 61e using 2-(7-Amino-8-methoxy-1,2,4,5-tetrahydro-benzo[d]azepin-3-yl)-N,N-dimethyl-acetamide. Product isolated as an white solid (0.025 g, 22%). MP: 220-227° C. $^1$H NMR (400 MHz, CDCl$_3$, δ, ppm): 8.00 (d, 1H, J=1.5 Hz), 7.89 (s, 1H), 7.50-7.46 (m, 2H), 6.84-6.78 (m, 2H), 6.68 (s, 1H), 6.57 (s, 1H), 3.82 (s, 3H), 3.27-3.20 (m, 6H), 3.15 (s, 3H), 2.98 (s, 3H), 2.84-2.79 (m, 2H), 2.66-2.56 (m, 10H), 2.37 (s, 3H), 2.25 (s, 3H). MS: 593.32 (MH)$^+$.

Example 803

2-{7-[5-Chloro-4-(3-methoxy-4-morpholin-4-yl-phenylamino)-pyrimidin-2-ylamino]-8-methoxy-1,2,4,5-tetrahydro-benzo[d]azepin-3-yl}-N,N-dimethyl-acetamide 1-Fluoro-2-methoxy-4-nitro-benzene using Morpholine was converted in an analogous manner to Example 171b, to 4-(2-Methoxy-4-nitro-phenyl)-morpholine, which was converted in an analogous manner to Example 31f, to 3-Methoxy-4-morpholin-4-yl-phenylamine, which was converted, in an analogous procedure to Example 1d, to (2,5-Dichloro-pyrimidin-4-yl)-(3-methoxy-4-morpholin-4-yl-phenyl)-amine, which was converted to the title compound in an analogous manner to Example 61e using 2-(7-Amino-8-methoxy-1,2,4,5-tetrahydro-benzo[d]azepin-3-yl)-N,N-dimethyl-acetamide (52 mg, 0.00018 mol). Product isolated as an off-white solid (0.053 g, 48%). MP: 203-206° C. $^1$H NMR (400 MHz, CDCl$_3$, δ, ppm): 8.07 (s, 1H), 8.05 (s, 1H), 7.49 (s, 1H), 7.16-7.12 (m, 1H), 7.12-7.09 (m, 1H), 6.95 (s, 1H), 6.90 (d, 1H, J=8.6 Hz), 6.61 (s, 1H), 3.93-3.89 (m, 4H), 3.85 (s, 3H), 3.80 (s, 3H), 3.26 (br s, 2H), 3.13 (s, 3H), 3.10-3.05 (m, 4H), 2.97 (s, 3H), 2.90-2.82 (m, 2H), 2.75-2.56 (m, 6H). MS: 596.24 (MH)$^+$.

Example 804

2-(7-{5-Chloro-4-[3-methoxy-4-(4-methyl-piperazin-1-yl)-phenylamino]-pyrimidin-2-ylamino}-8-methoxy-1,2,4,5-tetrahydro-benzo[d]azepin-3-yl)-N,N-dimethyl-acetamide 1-Fluoro-2-methoxy-4-nitro-benzene using 1-methyl-piperazine was converted in an analogous manner to Example 171b, to 1-(2-Methoxy-4-nitro-phenyl)-4-methyl-piperazine, which was converted in an analogous manner to Example 31f, to 3-Methoxy-4-(4-methyl-piperazin-1-yl)-phenylamine, which was converted to in an analogous manner to Example 1d, to (2,5-Dichloro-pyrimidin-4-yl)-[3-methoxy-4-(4-methyl-piperazin-1-yl)-phenyl]-amine, which was converted to the title compound in an analogous manner to Example 61e using 2-(7-Amino-8-methoxy-1,2,4,5-tetrahydro-benzo[d]azepin-3-yl)-N,N-dimethyl-acetamide (50 mg, 0.0002 mol). Product isolated as an off-white solid (0.016 g, 10%). MP: 82-100° C. $^1$H NMR (400 MHz, CDCl$_3$, δ, ppm): 8.07 (s, 1H), 8.04 (s, 1H), 7.48 (s, 1H), 7.15-7.09 (m, 2H), 6.96-6.90 (m, 2H), 6.61 (s, 1H), 3.84 (s, 3H), 3.79 (s, 3H), 3.25 (s, 2H), 3.18-3.06 (m, 7H), 2.97 (s, 3H), 2.88-2.82 (m, 2H), 2.75-2.58 (m, 10H), 2.39 (s, 3H). MS: 609.29 (MH)$^+$.

Example 805

5-Fluoro-N*2*-[3-(2-methanesulfonyl-ethyl)-8-methoxy-2,3,4,5-tetrahydro-1H-benzo[d]azepin-7-yl]-N*4*-[2-methoxy-4-(4-methyl-piperazin-1-yl)-phenyl]-pyrimidine-2,4-diamine The title compound was prepared from 3-(2-Methanesulfonyl-ethyl)-8-methoxy-2,3,4,5-tetrahydro-1H-benzo[d]azepin-7-ylamine and (2-Chloro-5-fluoro-pyrimidin-4-yl)-[2-methoxy-4-(4-methyl-piperazin-1-yl)-phenyl]-amine in an analogous manner to Example 61e. Product isolated as an off-white solid (0.029 g, 25%). MP: 90-127° C. $^1$H NMR (400 MHz, CDCl$_3$, δ, ppm): 8.25 (d, 1H, J=8.8 Hz), 8.14 (s, 1H), 7.92-7.90 (m, 1H), 7.39 (s, 1H), 7.18 (d, 1H, J=1.8 Hz), 6.63 (s, 1H), 6.57 (d, 1H, J=1.8 Hz), 6.53 (dd, 1H, J=9.0 Hz and 1.9 Hz), 3.91 (s, 3H), 3.86 (s, 3H), 3.23-3.14 (m, 6H), 3.07 (s, 3H), 3.02 (t, 2H, J=6.3 Hz), 2.88-2.81 (m, 4H), 2.72-2.66 (m, 4H), 2.65-2.59 (m, 4H), 2.38 (s, 3H). MS: 614.27 (MH)$^+$.

Example 806

(1S,2S,3R,4R)-3-{5-Chloro-2-[3-(2,2-difluoro-ethyl)-8-methoxy-2,3,4,5-tetrahydro-1H-benzo[d]azepin-7-ylamino]-pyrimidin-4-ylamino}-bicyclo[2.2.1]hept-5-ene-2-carboxylic acid amide The title compound was prepared from 3-(2,2-Difluoro-ethyl)-8-methoxy-2,3,4,5-tetrahydro-1H-benzo[d]azepin-7-ylamine and (1S,2S,3R,4R)-3-(2,5-Dichloro-pyrimidin-4-ylamino)-bicyclo[2.2.1]hept-5-ene-2-carboxylic acid amide in an analogous manner to Example 61e. Product isolated as an off-white solid (0.025 g, 48%). MP: 127-147° C. $^1$H NMR (400 MHz, CDCl$_3$, δ, ppm): 8.18 (s, 1H), 7.89 (s, 1H), 7.40 (s, 1H), 6.63 (s, 1H), 6.57 (d, 1H, J=8.3 Hz), 6.32-6.29 (m, 2H), 6.07-5.75 (m, 1H), 5.56 (s, 1H), 5.32 (s, 1H), 4.45 (t, 1H, J=8.3 Hz), 3.86 (s, 3H), 3.07 (s, 1H), 2.97-2.77 (m, 11H), 2.51 (d, 1H, J=8.0 Hz), 2.26 (d, 1H, J=9.1 Hz), 1.68-1.63 (m, 1H). MS: 519.18 (MH)$^+$.

Example 807

2-(7-{5-Chloro-4-[2-methoxy-4-(4-methyl-piper-azin-1-yl)-phenylamino]-pyrimidin-2-ylamino}-8-methoxy-1,2,4,5-tetrahydro-benzo[d]azepin-3-yl)-acetamide The title compound was prepared from 2-(7-Amino-8-methoxy-1,2,4,5-tetrahydro-benzo[d]azepin-3-yl)-acetamide and (2,5-Dichloro-pyrimidin-4-yl)-[2-methoxy-4-(4-methyl-piperazin-1-yl)-phenyl]-amine in an analogous manner to Example 61e. Product isolated as a pale yellow solid (0.010 g, 10%). MP: 219-221° C. $^1$H NMR (400 MHz, CDCl$_3$, δ, ppm): 8.16 (d, 1H, J=8.3 Hz), 8.13 (s, 1H), 8.01 (s, 1H), 7.47-7.43 (m, 2H), 7.26-7.20 (m, 1H), 6.63 (s, 1H), 6.58-6.55 (m, 1H), 6.53-6.49 (m, 1H), 5.55-5.49 (m, 1H), 3.91 (s, 3H), 3.86 (s, 3H), 3.32-3.27 (m, 1H), 3.22-3.17 (m, 4H), 3.11 (s, 2H), 2.96-2.90 (m, 1H), 2.89-2.85 (m, 2H), 2.81-2.87 (m, 2H), 2.74-2.67 (m, 4H), 2.64-2.58 (m, 4H), 2.38 (s, 3H). MS: 581.26 (MH)$^+$.

Example 808

2-{7-[5-Fluoro-4-(2-methoxy-4-morpholin-4-yl-phenylamino)-pyrimidin-2-ylamino]-8-methoxy-1,2,4,5-tetrahydro-benzo[d]azepin-3-yl}-N,N-dimethyl-acetamide The title compound was prepared from 2-(7-Amino-8-methoxy-1,2,4,5-tetrahydro-benzo[d]azepin-3-yl)-N,N-dimethyl-acetamide and (2-Chloro-5-fluoro-pyrimidin-4-yl)-(2-methoxy-4-morpholin-4-yl-phenyl)-amine in an analogous manner to Example 61e. Product isolated as a pale yellow solid (0.037 g, 39%). MP: 80-107° C. $^1$H NMR (400 MHz, CDCl$_3$, δ, ppm): 8.30 (d, 1H, J=8.6 Hz), 8.13 (s, 1H), 7.93-7.90 (m, 1H), 7.39 (s, 1H), 7.22-7.18 (m, 1H), 6.63 (s, 1H), 6.56-6.49 (m, 2H), 3.93-3.88 (m, 7H), 3.86 (s, 3H), 3.27 (s, 2H), 3.17-3.12 (m, 7H), 2.98 (s, 3H), 2.91-2.85 (m, 4H), 2.74-2.65 (m, 4H). MS: 580.32 (MH)$^+$.

Example 809

2-{7-[5-Fluoro-4-(2-methoxy-4-morpholin-4-yl-phenylamino)-pyrimidin-2-ylamino]-8-methoxy-1,2,4,5-tetrahydro-benzo[d]azepin-3-yl}-N-methyl-acetamide The title compound was prepared from 2-(7-Amino-8-methoxy-1,2,4,5-tetrahydro-benzo[d]azepin-3-yl)-N-methyl-acetamide and (2-Chloro-5-fluoro-pyrimidin-4-yl)-(2-methoxy-4-morpholin-4-yl-phenyl)-amine in an analogous manner to Example 61e. Product was isolated as a pale yellow solid (0.044 g, 48%). MP: 82-124° C. $^1$H NMR (400 MHz, CDCl$_3$, δ, ppm): 8.29 (d, 1H, J=8.6 Hz), 8.16 (s, 1H), 7.93-7.90 (m, 1H), 7.40 (s, 1H), 7.36-7.29 (m, 1H), 7.22-7.18 (m, 1H), 6.63 (s, 1H), 6.56-6.53 (m, 1H) 6.53-6.48 (m, 1H), 3.93-3.84 (m, 10H), 3.17-3.09 (m, 6H), 2.92-2.82 (m, 7H), 2.74-2.65 (m, 4H). MS: 566.30 (MH)$^+$.

Example 810

2-{7-[5-Fluoro-4-(2-methoxy-4-morpholin-4-yl-phenylamino)-pyrimidin-2-ylamino]-8-methoxy-1,2,4,5-tetrahydro-benzo[d]azepin-3-yl}-acetamide The title compound was prepared from 2-(7-Amino-8-methoxy-1,2,4,5-tetrahydro-benzo[d]azepin-3-yl)-acetamide and (2-Chloro-5-fluoro-pyrimidin-4-yl)-(2-methoxy-4-morpholin-4-yl-phenyl)-amine in an analogous manner to Example 61e. Product isolated as a pale yellow solid (0.013 g, 14%). MP: 98-140° C. $^1$H NMR (400 MHz, CDCl$_3$, δ, ppm): 8.27 (d, 1H, J=8.6 Hz), 8.16 (s, 1H), 7.92 (d, 1H, J=2.8 Hz), 7.40 (s, 1H), 7.25-7.17 (m, 2H), 6.64 (s, 1H), 6.56-6.54 (m, 1H), 6.53-6.49 (m, 1H), 5.52-5.41 (m, 1H), 3.93-3.84 (m, 10H, 3.16-3.10 (m, 6H), 2.90-2.82 (m, 4H), 2.76-2.68 (m, 4H). MS: 552.28 (MH)$^+$.

Example 811

{7-[5-Fluoro-4-(2-methoxy-4-morpholin-4-yl-phenylamino)-pyrimidin-2-ylamino]-8-methoxy-1,2,4,5-tetrahydro-benzo[d]azepin-3-yl}-acetic acid isopropyl ester The title compound was isolated as a byproduct from Example 810 as a pale yellow solid (0.008 g, 8%). MP: 94-110° C. $^1$H NMR (400 MHz, CDCl$_3$, δ, ppm): 8.33 (d, 1H, J=8.6 Hz), 8.13 (s, 1H), 7.92-7.89 (m, 1H), 7.39 (s, 1H), 7.24-7.20 (m, 1H), 6.64 (s, 1H), 6.56-6.49 (m, 2H), 5.11-5.00 (m, 1H), 3.92-3.85 (m, 10H), 3.32 (s, 2H), 3.17-3.12 (m, 4H), 2.94-2.88 (m, 4H), 2.80-2.73 (m, 4H), 1.25 (d, 6H, J=6.3 Hz). MS: 595.33 (MH)$^+$.

Example 812

2-{7-[5-Chloro-4-(2,4-dimethoxy-phenylamino)-pyrimidin-2-ylamino]-8-methoxy-1,2,4,5-tetrahydro-benzo[d]azepin-3-yl}-N,N-dimethyl-acetamide 2,4-Dimethoxy-phenylamine using 2,4,5-Trichloro-pyrimidine was converted in an analogous manner to Example 1d, to (2,5-Dichloro-pyrimidin-4-yl)-(2,4-dimethoxy-phenyl)-amine, which was converted to the title compound in an analogous manner to Example 61e using 2-(7-Amino-8-methoxy-1,2,4,5-tetrahydro-benzo[d]azepin-3-yl)-N,N-dimethyl-acetamide. Product isolated as an off-white solid (0.073 g, 74%). MP: 72-100° C. $^1$H NMR (400 MHz, CDCl$_3$, δ, ppm): 8.22 (d, 1H, J=8.8), 8.06 (s, 1H), 8.02 (s, 1H), 7.47 (s, 1H), 7.42 (s, 1H), 6.63 (s, 1H), 6.54 (d, 1H, J=2.0 Hz), 6.49 (dd, 1H, J=8.7 Hz and 2.1 Hz), 3.90 (s, 3H), 3.86 (s, 3H), 3.83 (s, 3H), 3.27 (s, 2H), 3.15 (s, 3H), 2.97 (s, 3H), 2.90-2.80 (m, 4H), 2.71-2.65 (m, 4H). MS: 541.18 (MH)$^+$.

Example 813

(1S,2S,3R,4R)-3-[2-(3-Carbamoylmethyl-8-methoxy-2,3,4,5-tetrahydro-1H-benzo[d]azepin-7-ylamino)-5-chloro-pyrimidin-4-ylamino]-bicyclo[2.2.1]hept-5-ene-2-carboxylic acid amide The title compound was prepared from 2-(7-Amino-8-methoxy-1,2,4,5-tetrahydro-benzo[d]azepin-3-yl)-N,N-dimethyl-acetamide and (2,5-Dichloro-pyrimidin-4-yl)-(2,4-dimethoxy-phenyl)-amine in an analogous manner to Example 61e. Product isolated as an off-white solid (0.073 g, 74%). MP: 72-100° C. $^1$H NMR (400 MHz, CDCl$_3$, δ, ppm):

8.22 (d, 1H, J=8.8), 8.06 (s, 1H), 8.02 (s, 1H), 7.47 (s, 1H), 7.42 (s, 1H), 6.63 (s, 1H), 6.54 (d, 1H, J=2.0 Hz), 6.49 (dd, 1H, J=8.7 Hz and 2.1 Hz), 3.90 (s, 3H), 3.86 (s, 3H), 3.83 (s, 3H), 3.27 (s, 2H), 3.15 (s, 3H), 2.97 (s, 3H), 2.90-2.80 (m, 4H), 2.71-2.65 (m, 4H). MS: 541.18 (MH)+.

Example 814

5-Chloro-N*2*-[8-methoxy-3-(2-methoxy-1-methoxymethyl-ethyl)-2,3,4,5-tetrahydro-1H-benzo[d]azepin-7-yl]-N*4*-(2-methoxy-4-morpholin-4-yl-phenyl)-pyrimidine-2,4-diamine 7-Methoxy-8-nitro-2,3,4,5-tetrahydro-1H-benzo[d]azepine using 1,3-Dimethoxy-propan-2-ol was converted in an analogous manner to Example 779a, to 7-Methoxy-3-(2-methoxy-1-methoxymethyl-ethyl)-8-nitro-2,3,4,5-tetrahydro-1H-benzo[d]azepine, which was converted in an analogous manner to Example 31f, to 8-Methoxy-3-(2-methoxy-1-methoxymethyl-ethyl)-2,3,4,5-tetrahydro-1H-benzo[d]azepin-7-ylamine, which was converted to the title compound in an analogous manner to Example 61e using (2,5-Dichloro-pyrimidin-4-yl)-(2-methoxy-4-morpholin-4-yl-phenyl)-amine. Product isolated as a tan solid (0.064 g, 62%). MP: 59-77° C. $^1$H NMR (400 MHz, CDCl$_3$, δ, ppm): 8.30 (d, 1H, J=8.3 Hz), 8.11 (s, 1H), 8.01 (s, 1H), 7.56 (s, 1H), 7.43 (s, 1H), 6.64 (s, 1H), 6.56-6.54 (m, 1H), 6.54-6.50 (m, 1H), 3.92 (s, 3H), 3.91-3.87 (m, 4H), 3.86 (s, 3H), 3.57-3.51 (m, 2H), 3.47-3.42 (m, 2H), 3.32 (s, 6H), 3.18-3.14 (m, 4H), 3.04-2.98 (m, 1H), 2.88-2.78 (m, 8H). MS: 613.49 (MH)+.

Example 815

(1S,2S,3R,4R)-3-{5-Chloro-2-[8-methoxy-3-(2-methoxy-1-methoxymethyl-ethyl)-2,3,4,5-tetrahydro-1H-benzo[d]azepin-7-ylamino]-pyrimidin-4-ylamino}-bicyclo[2.2.1]hept-5-ene-2-carboxylic acid amide The title compound was prepared from 8-Methoxy-3-(2-methoxy-1-methoxymethyl-ethyl)-2,3,4,5-tetrahydro-1H-benzo[d]azepin-7-ylamine and (1S,2S,3R,4R)-3-(2,5-Dichloro-pyrimidin-4-ylamino)-bicyclo[2.2.1]hept-5-ene-2-carboxylic acid amide in an analogous manner to Example 61e. Product isolated as an off-white solid (0.050 g, 49%). MP: 106-125° C. $^1$HNMR (400 MHz, CDCl$_3$, δ, ppm): 8.17 (s, 1H), 7.88 (s, 1H), 7.38 (s, 1H), 6.63 (s, 1H), 6.50 (d, 1H, J=8.6 Hz), 6.34-6.28 (m, 2H), 5.54 (br s, 1H), 5.26 (br s, 1H), 4.46 (t, 1H, J=8.3 Hz), 3.86 (s, 3H), 3.57-3.51 (m, 2H), 3.47-3.41 (m, 2H), 3.32 (s, 6H), 3.07 (s, 1H), 3.05-2.98 (m, 1H), 2.88-2.78 (m, 9H), 2.52 (d, 1H, J=8.1 Hz), 2.26 (d, 1H, J=9.1 Hz), 1.65 (d, 1H, J=9.1 Hz). MS: 557.46 (MH)+.

Example 816

N-((1R,2R)-2-{5-Chloro-2-[8-methoxy-3-(2-methoxy-1-methoxymethyl-ethyl)-2,3,4,5-tetrahydro-1H-benzo[d]azepin-7-ylamino]-pyrimidin-4-ylamino}-cyclohexyl)-methanesulfonamide The title compound was prepared from 8-Methoxy-3-(2-methoxy-1-methoxymethyl-ethyl)-2,3,4,5-tetrahydro-1H-benzo[d]azepin-7-ylamine and N-[(1R,2R)-2-(2,5-Dichloro-pyrimidin-4-ylamino)-cyclohexyl]-methanesulfonamide in an analogous manner to Example 61e. Product isolated as an off-white solid (0.044 g, 45%). MP: 167-172° C. $^1$H NMR (400 MHz, CDCl$_3$, δ, ppm): 7.96-7.92 (m, 2H), 7.30 (s, 1H), 6.65 (s, 1H), 5.37-5.30 (m, 2H), 3.98-3.87 (m, 1H), 3.86 (s, 3H), 3.57-3.51 (m, 2H), 3.47-3.41 (m, 2H), 3.32 (s, 6H), 3.30-3.19 (m, 1H), 3.06-2.98 (m, 1H), 2.90-2.75 (m, 11H), 2.25-2.15 (m, 2H), 1.86-1.75 (m, 2H), 1.42-1.30 (m, 4H). MS: 597.44 (MH)+.

Example 817

5-Chloro-N*2*-[8-methoxy-3-(2-methoxy-1-methoxymethyl-ethyl)-2,3,4,5-tetrahydro-1H-benzo[d]azepin-7-yl]-N*4*-[2-(propane-2-sulfonyl)-phenyl]-pyrimidine-2,4-diamine The title compound was prepared from 8-Methoxy-3-(2-methoxy-1-methoxymethyl-ethyl)-2,3,4,5-tetrahydro-1H-benzo[d]azepin-7-ylamine and (2,5-Dichloro-pyrimidin-4-yl)-[2-(propane-2-sulfonyl)-phenyl]-amine in an analogous manner to Example 61e. Product isolated as an off-white solid (0.022 g, 31%). MP: 52-76° C. $^1$HNMR (400 MHz, CDCl$_3$, δ, ppm): 9.50 (s, 1H), 8.56 (d, 1H, J=8.6 Hz), 8.15 (s, 1H), 7.96 (s, 1H), 7.92 (d, 1H, J=8.1 Hz), 7.63-7.57 (m, 1H), 7.48 (s, 1H), 7.28-7.22 (m, 1H), 6.65 (s, 1H), 3.87 (s, 3H), 3.57-3.51 (m, 2H), 3.47-3.42 (m, 2H), 3.33 (s, 6H), 3.31-3.20 (m, 1H), 3.06-2.99 (m, 1H), 2.88-2.68 (m, 8H), 1.32 (d, 6H, J=6.8 Hz). MS: 604.51 (MH)+.

Example 818

2-{5-Chloro-2-[8-methoxy-3-(2-methoxy-1-methoxymethyl-ethyl)-2,3,4,5-tetrahydro-1H-benzo[d]azepin-7-ylamino]-pyrimidin-4-ylamino}-N,N-dimethyl-benzenesulfonamide The title compound was prepared from 8-Methoxy-3-(2-methoxy-1-methoxymethyl-ethyl)-2,3,4,5-tetrahydro-1H-benzo[d]azepin-7-ylamine and 2-(2,5-Dichloro-pyrimidin-4-ylamino)-N,N-dimethyl-benzenesulfonamide in an analogous manner to Example 61e. Product isolated as an off-white solid (0.025 g, 35%). MP: 54-76° C. $^1$HNMR (400 MHz, CDCl$_3$, δ, ppm): 9.34 (s, 1H), 8.53 (d, 1H, J=8.6 Hz), 8.13 (s, 1H), 7.97 (s, 1H), 7.88 (d, 1H, J=7.8 Hz), 7.59-7.53 (m, 1H), 7.48 (s, 1H), 7.26-7.20 (m, 1H), 6.65 (s, 1H), 3.87 (s, 3H), 3.57-3.51 (m, 2H), 3.48-3.42 (m, 2H), 3.33 (s, 6H), 3.06-2.98 (m, 1H), 2.87-2.67 (m, 14H). MS: 605.50 (MH)+.

Example 819

2-[7-(5-Chloro-4-{2-methoxy-4-[4-(4-methyl-piperazin-1-yl)-piperidin-1-yl]-phenylamino}-pyrimidin-2-ylamino)-8-methoxy-1,2,4,5-tetrahydro-benzo[d]azepin-3-yl]-N,N-dimethyl-acetamide 2-Methoxy-4-[4-(4-methyl-piperazin-1-yl)-piperidin-1-yl]-phenylamine was converted in an analogous manner to Example 1d, to (2,5-Dichloro-pyrimidin-4-yl)-{2-methoxy-4-[4-(4-methyl-piperazin-1-yl)-piperidin-1-yl]-phenyl}-amine, which was converted to the title compound in an analogous manner to Example 61e using 2-(7-Amino-8-methoxy-1,2,4,5-tetrahydro-benzo[d]azepin-3-yl)-N,N-dimethyl-acetamide. Product isolated as a tan solid (0.017 g, 18%). MP: 65-92° C. $^1$H NMR (400 MHz, CDCl$_3$, δ, ppm): 8.24-8.19 (m, 1H), 8.12-8.10 (m, 1H), 8.01-7.99 (m, 1H), 7.53-7.51 (m, 1H), 7.42-7.40 (m, 1H), 6.63 (s, 1H), 6.58-6.55 (m, 1H), 6.53-6.49 (m, 1H), 3.90 (s, 3H), 3.86 (s, 3H), 3.72-3.65 (m, 2H), 3.26 (s, 2H), 3.13 (s, 3H), 2.97 (s, 3H), 2.90-

2.82 (m, 4H), 2.75-2.62 (m, 10H), 2.54-2.36 (m, 5H), 2.30 (s, 3H), 2.20-1.95 (m, 2H), 1.75-1.65 (m, 2H). MS: 692.53 (MH)+.

Example 820

2-{7-[5-Chloro-4-(2-dimethylsulfamoyl-4-methoxy-phenylamino)-pyrimidin-2-ylamino]-8-methoxy-1,2,4,5-tetrahydro-benzo[d]azepin-3-yl}-N,N-dimethyl-acetamide 820a) 2-Amino-5-methoxy-benzenesulfonic acid (10 g, 0.05 mol) was added to a stirred solution of Sodium bicarbonate (9.1 g, 0.11 mol) in Water (120 mL, 6.7 mol) at 0° C. A solution of 9-Fluorenylmethyl chloroformate (14 g, 0.054 mol) in 1,4-Dioxane (120 mL, 1.5 mol) was added dropwise. The mixture was stirred for 18 hours. The mixture was reduced in volume to remove volatiles, was made acidic by addition of 1N Hydrochloric acid and was extracted with ethyl acetate (3×200 mL). The acidic aqueous layer was evaporated to dryness. The recovered solid was triturated with warm ethyl acetate (500 mL), dried over sodium sulfate, filtered and evaporated. Recovered desired 2-(9H-Fluoren-9-ylmethoxycarbonylamino)-5-methoxy-benzenesulfonic acid as pink solid (19.5 g, 92%).

820b) To a suspension of 2-(9H-Fluoren-9-ylmethoxycarbonylamino)-5-methoxy-benzenesulfonic acid (1.00 g, 0.00235 mol) in Methylene chloride (50 mL, 0.8 mol) was added N,N-Dimethylformamide (20 uL, 0.0002 mol) followed by Oxalyl chloride (1.0 mL, 0.012 mol). The mixture was stirred and gas evolution was noted. The mixture was heated at the reflux for 1 hour. The mixture was cooled to room temperature and evaporated under reduced pressure to yield a yellow solid (1.20 g). Recovered s desired (2-Chlorosulfonyl-4-methoxy-phenyl)-carbamic acid 9H-fluoren-9-ylmethyl ester as a yellow solid (1.2 g, 100%).

820c) To a solution of (2-Chlorosulfonyl-4-methoxy-phenyl)-carbamic acid 9H-fluoren-9-ylmethyl ester (9.2 g, 0.021 mol) in Methylene chloride (100 mL, 2 mol) was added Triethylamine (4.3 mL, 0.031 mol) followed by 2.0 M of Dimethylamine in Tetrahydrofuran (31 mL). The mixture was stirred for 72 hours then evaporated under reduced pressure. The crude material was dissolved in ethyl acetate (150 mL) and rinsed with water (100 ml), 1N Hydrochloric acid (100 mL) then water (100 mL). The organic layer was dried over magnesium sulfate, filtered and evaporated. The oil was purified by silica gel chromatography using 5%→30% Ethyl Acetate:Hexane solvent gradient. Recovered desired 2-Amino-5-methoxy-N,N-dimethyl-benzenesulfonamide as a yellow oil (2.28 g, 48%).

820d) 2-Amino-5-methoxy-N,N-dimethyl-benzenesulfonamide was converted in an analogous manner to Example 1d, to 2-(2,5-Dichloro-pyrimidin-4-ylamino)-5-methoxy-N,N-dimethyl-benzenesulfonamide, which was converted to the title compound in an analogous manner to Example 61e using 2-(7-Amino-8-methoxy-1,2,4,5-tetrahydro-benzo[d]azepin-3-yl)-N,N-dimethyl-acetamide. Product isolated as a yellow foam (0.269 g, 67%). MP: 60-88° C. $^1$H NMR (400 MHz, CDCl$_3$, δ, ppm): 8.85 (s, 1H), 8.25 (d, 1H, J=9.1 Hz), 8.09 (s, 1H), 7.95 (s, 1H), 7.48 (s, 1H), 7.41-7.48 (m, 1H), 7.15-7.09 (m, 1H), 6.63 (s, 1H), 3.87 (s, 3H), 3.86 (s, 3H), 3.28 (s, 2H), 3.14 (s, 3H), 2.98 (s, 3H), 2.90-2.84 (m, 2H), 2.75-2.62 (m, 12H). MS: 618.58 (MH)+.

Example 821

2-{7-[5-Chloro-4-(2-methanesulfonylamino-4-methoxy-phenylamino)-pyrimidin-2-ylamino]-8-methoxy-1,2,4,5-tetrahydro-benzo[d]azepin-3-yl}-N,N-dimethyl-acetamide 821a) To a solution of 5-Methoxy-2-nitro-phenylamine (5.0 g, 0.030 mol) and Triethylamine (10.0 mL, 0.0717 mol) in Methylene chloride (100 mL, 2 mol) at 0° C. was added dropwise Methanesulfonyl chloride (5.1 mL, 0.065 mol). The mixture was stirred for 18 hours. The mixture was poured into 1N Hydrochloric Acid (200 mL). The aqueous was extracted with dichloromethane (3×100 mL). The combined organic layers were dried over magnesium sulfate, filtered and evaporated. The oil was purified by silica gel chromatography using 20%→100% Ethyl Acetate:Hexane solvent gradient. N-(5-Methoxy-2-nitro-phenyl)-N-(methylsulfonyl)methanesulfonamide isolated as a yellow solid (7.75 g, 80%).

821b) To a solution of N-(5-Methoxy-2-nitro-phenyl)-N-(methylsulfonyl)methanesulfonamide (7.70 g) in Tetrahydrofuran (200 mL, 2 mol) was added 1 M of Sodium hydroxide in Water (50 mL). The mixture was stirred for 18 hours. The mixture was poured into a separatory funnel and the aqueous layer (bottom layer) was separated. The aqueous layer was washed with Ethyl Acetate (100 mL). The organic layers were combined, dried over magnesium sulfate, filtered and evaporated. N-(5-Methoxy-2-nitro-phenyl)-methanesulfonamide isolated as an orange solid (5.59 g, 76%).

821c) N-(5-Methoxy-2-nitro-phenyl)-methanesulfonamide was converted in an analogous manner to Example 31f, to N-(2-Amino-5-methoxy-phenyl)-methanesulfonamide, which was converted, in an analogous procedure to Example 1d, to N-[2-(2,5-Dichloro-pyrimidin-4-ylamino)-5-methoxy-phenyl]-methanesulfonamide, which was converted to the title compound in an analogous manner to Example 61e using 2-(7-Amino-8-methoxy-1,2,4,5-tetrahydro-benzo[d]azepin-3-yl)-N,N-dimethyl-acetamide. Product isolated as a white solid (0.094 g, 70%). MP: 186-191° C. $^1$H NMR (400 MHz, DMSO-d$_6$, δ, ppm): 9.19 (s, 1H), 8.42 (s, 1H), 8.07 (s, 1H), 7.56-7.46 (m, 3H), 7.02-6.99 (m, 1H), 6.83-6.78 (m, 1H), 6.75 (s, 1H), 3.77 (s, 6H), 3.31-3.23 (m, 2H), 3.07 (s, 3H), 2.88 (s, 3H), 2.84 (s, 3H), 2.78-2.73 (m, 2H), 2.62-2.42 (m, 6H). MS: 604.46 (MH)+.

Example 822

2-{5-Chloro-2-[3-(2,2-difluoro-ethyl)-8-methoxy-2,3,4,5-tetrahydro-1H-benzo[d]azepin-7-ylamino]-pyrimidin-4-ylamino}-N,N-dimethyl-benzenesulfonamide The title compound was prepared from 3-(2,2-Difluoro-ethyl)-8-methoxy-2,3,4,5-tetrahydro-1H-benzo[d]azepin-7-ylamine and 2-(2,5-Dichloro-pyrimidin-4-ylamino)-N,N-dimethyl-benzenesulfonamide in an analogous manner to Example 61e. Product isolated as an off-white solid (0.043 g, 44%). MP: 61-70° C. $^1$HNMR (400 MHz, CDCl$_3$, δ, ppm): 9.33 (s, 1H), 8.52 (d, 1H, J=8.3 Hz), 8.14 (s, 1H), 8.00 (s, 1H), 7.88 (d, 1H, J=7.8 Hz), 7.55 (t, 1H, J=7.5 Hz), 7.50 (s, 1H), 7.26-7.21 (m, 1H), 6.65 (s, 1H), 5.91 (tt, 1H, J=56.1 Hz and 4.2 Hz), 3.87 (s, 3H), 2.97-2.69 (m, 16H). MS: 567.46 (MH)+.

Example 823

5-Chloro-N*2*-[3-(2,2-difluoro-ethyl)-8-methoxy-2,3,4,5-tetrahydro-1H-benzo[d]azepin-7-yl]-N*4*-(2-pyrazol-1-yl-phenyl)-pyrimidine-2,4-diamine The title compound was prepared from 3-(2,2-Difluoro-ethyl)-8-methoxy-2,3,4,5-tetrahydro-1H-benzo[d]azepin-7-ylamine and (2,5-Dichloro-pyrimidin-4-yl)-(2-pyrazol-1-ylphenyl)-amine in an analogous to Example 61e. Product isolated as an off-white solid (0.043 g, 42%). MP: 53-65° C. $^1$H NMR (400 MHz, CDCl$_3$, δ, ppm): 10.16 (s, 1H), 8.51 (d, 1H, J=8.3 Hz), 8.06 (s, 1H), 8.04 (s, 1H), 7.84 (s, 1H), 7.81 (s, 1H), 7.47 (s, 1H), 7.40-7.31 (m, 2H), 7.18 (t, 1H, J=7.6 Hz), 6.63 (s, 1H), 6.51 (s, 1H), 5.91 (tt, 1H, J=56.1 Hz and 4.0 Hz), 3.85 (s, 3H), 2.98-2.73 (m, 10H). MS: 526.40 (MH)$^+$.

Example 824

2-{5-Chloro-2-[3-(2,2-difluoro-propyl)-8-methoxy-2,3,4,5-tetrahydro-1H-benzo[d]azepin-7-ylamino]-pyrimidin-4-ylamino}-N,N-dimethyl-benzene-sulfonamide The title compound e was prepared from 3-(2,2-Difluoro-propyl)-8-methoxy-2,3,4,5-tetrahydro-1H-benzo[d]azepin-7-ylamine and 2-(2,5-Dichloro-pyrimidin-4-ylamino)-N,N-dimethyl-benzenesulfonamide in an analogous manner to Example 61e. Product isolated as an off-white foam (0.028 g, 28%). MP: 52-62° C. $^1$H NMR (400 MHz, CDCl$_3$, δ, ppm): 9.33 (s, 1H), 8.52 (d, 1H, J=8.6 Hz), 8.14 (s, 1H), 7.99 (s, 1H), 7.89 (d, 1H, J=8.1 Hz), 7.56 (t, 1H, J=7.8 Hz), 7.50 (s, 1H), 7.27-7.21 (m, 1H), 6.64 (s, 1H), 3.87 (s, 3H), 2.90-2.67 (m, 16H), 1.69 (t, 3H, J=18.9 Hz). MS: 581.48 (MH)$^+$.

Example 825

5-Chloro-N*2*-[3-(2,2-difluoro-propyl)-8-methoxy-2,3,4,5-tetrahydro-1H-benzo[d]azepin-7-yl]-N*4*-(2-pyrazol-1-yl-phenyl)-pyrimidine-2,4-diamine The title compound was prepared from 3-(2,2-Difluoro-propyl)-8-methoxy-2,3,4,5-tetrahydro-1H-benzo[d]azepin-7-ylamine and (2,5-Dichloro-pyrimidin-4-yl)-(2-pyrazol-1-yl-phenyl)-amine in an analogous manner to Example 61e. Product isolated as an off-white foam (0.029 g, 27%). MP: 114-121° C. $^1$H NMR (400 MHz, CDCl$_3$, δ, ppm): 10.15 (s, 1H), 8.52 (d, 1H, J=8.3 Hz), 8.06-8.04 (m, 2H), 7.85 (s, 1H), 7.82-7.80 (m, 1H), 7.46 (s, 1H), 7.40-7.32 (m, 2H), 7.19 (t, 1H, J=7.7 Hz), 6.63 (s, 1H), 6.52-6.50 (m, 1H), 3.86 (s, 3H), 2.90-2.73 (m, 10H), 1.69 (t, 3H). MS: 540.43 (H)$^+$.

Example 826

2-{7-[5-Chloro-4-(2-dimethylamino-4-methoxy-phenylamino)-pyrimidin-2-ylamino]-8-methoxy-1,2,4,5-tetrahydro-benzo[d]azepin-3-yl}-N,N-dimethyl-acetamide (5-Methoxy-2-nitro-phenyl)-dimethyl-amine, prepared in an analogous manner to Example 171b, was converted in an analogous manner to Example 31f, to 4-Methoxy-N*2*,N*2*-dimethyl-benzene-1,2-diamine, which was converted, in an analogous procedure to Example 1d, to N*1*-(2,5-Dichloro-pyrimidin-4-yl)-4-methoxy-N*2*,N*2*-dimethyl-benzene-1,2-diamine, which was converted to the title compound in an analogous manner to Example 61e using 2-(7-Amino-8-methoxy-1,2,4,5-tetrahydro-benzo[d]azepin-3-yl)-N,N-dimethyl-acetamide. Product isolated as a tan foam (0.064 g, 64%). MP: 58-74° C. $^1$H NMR (400 MHz, CDCl$_3$, δ, ppm): 8.31 (d, 1H, J=8.8 Hz), 8.17 (s, 1H), 8.13 (s, 1H), 8.02 (s, 1H), 7.43 (s, 1H), 6.75 (d, 1H, J=2.8 Hz), 6.65-6.61 (m, 2H), 3.86 (s, 3H), 3.82 (s, 3H), 3.28 (s, 2H), 3.15 (s, 3H), 2.97 (s, 3H), 2.91-2.84 (m, 4H), 2.73-2.66 (m, 10H). MS: 554.47 (MH)$^+$.

Example 827

5-Chloro-N*2*-[3-(2,2-difluoro-ethyl)-8-methoxy-2,3,4,5-tetrahydro-1H-benzo[d]azepin-7-yl]-N*4*-[2-(propane-2-sulfonyl)-phenyl]-pyrimidine-2,4-diamine The title compound was prepared from 3-(2,2-Difluoro-ethyl)-8-methoxy-2,3,4,5-tetrahydro-1H-benzo[d]azepin-7-ylamine and (2,5-Dichloro-pyrimidin-4-yl)-[2-(propane-2-sulfonyl)-phenyl]-amine in an analogous manner to Example 61e. Product isolated as an off-white foam (0.064 g, 65%). MP: 71-78° C. $^1$H NMR (400 MHz, CDCl$_3$, δ, ppm): 9.50 (s, 1H), 8.55 (d, 1H, J=8.3 Hz), 8.16 (s, 1H), 7.99 (s, 1H), 7.95-7.91 (m, 1H), 7.63-7.57 (m, 1H), 7.50 (s, 1H), 7.29-7.23 (m, 1H), 6.65 (s, 1H), 5.91 (tt, 1H, J=56.1 Hz and 4.2 Hz), 3.87 (s, 3H), 3.26 (sept, 1H, J=6.9 Hz), 2.97-2.70 (m, 10H, 1.32 (d, 6H, J=7.1 Hz). MS: 566.49 (MH)$^+$.

Example 828

5-Chloro-N*2*-[3-(2,2-difluoro-propyl)-8-methoxy-2,3,4,5-tetrahydro-1H-benzo[d]azepin-7-yl]-N*4*-[2-(propane-2-sulfonyl)-phenyl]-pyrimidine-2,4-diamine The title compound was prepared from 3-(2,2-Difluoro-propyl)-8-methoxy-2,3,4,5-tetrahydro-1H-benzo[d]azepin-7-ylamine and (2,5-Dichloro-pyrimidin-4-yl)-[2-(propane-2-sulfonyl)-phenyl]-amine in an analogous manner to Example 61e. Product isolated as an off-white foam (0.024 g, 24%). MP: 69-79° C. $^1$H NMR (400 MHz, CDCl$_3$, δ, ppm): 9.50 (s, 1H), 8.55 (d, 1H, J=8.3 Hz), 8.15 (s, 1H), 7.98 (s, 1H), 7.93 (d, 1H, J=7.8 Hz), 7.63-7.57 (m, 1H), 7.50 (s, 1H), 7.29-7.23 (m, 1H), 6.64 (s, 1H), 3.87 (s, 3H), 3.31-3.20 (m, 1H), 2.90-2.68 (m, 10H), 1.69 (t, 3H, J=18.7 Hz), 1.32 (d, 6H, J=6.8 Hz). MS: 580.48 (MH)$^+$.

Example 829

2-{7-[5-Chloro-4-(4-methoxy-2-morpholin-4-yl-phenylamino)-pyrimidin-2-ylamino]-8-methoxy-1,2,4,5-tetrahydro-benzo[d]azepin-3-yl}-N,N-dimethyl-acetamide 2-Fluoro-4-methoxy-1-nitro-benzene using Morpholine was converted in an analogous manner to Example 171b, to 4-(5-Methoxy-2-nitro-phenyl)-morpholine, which was converted in an analogous manner to Example 31f, to 4-Methoxy-2-morpholin-4-yl-phenylamine, which was converted, in an analogous procedure to Example 1d, to (2,5-Dichloro-pyrimidin-4-yl)-(4-methoxy-2-morpholin-4-yl-phenyl)-amine, which was converted to the title compound in an analogous manner to Example 61e using 2-(7-Amino-8-methoxy-1,2,4,5-tetrahydro-benzo[d]azepin-3-yl)-N,N-dimethyl-acetamide. Product isolated as a tan foam (0.047 g, 47%). MP: 86-96° C. $^1$H NMR (400 MHz, CDCl$_3$, δ, ppm): 8.42 (d, 1H, J=8.8 Hz), 8.37 (s, 1H), 8.12 (s, 1H), 8.04 (s, 1H), 7.42 (s, 1H), 6.78-6.75 (m, 1H), 6.71-6.67 (m, 1H), 6.65 (s, 1H), 3.93-3.88 (m, 4H), 3.87 (s, 3H), 3.82 (s, 3H), 3.28 (s, 2H), 3.15 (s, 3H), 2.98 (s, 3H), 2.94-2.85 (m, 8H), 2.74-2.68 (m, 4H). MS: 596.50 (MH)$^+$.

Example 830

2-{7-[5-Chloro-4-(2-dimethylsulfamoyl-4-methyl-phenylamino)-pyrimidin-2-ylamino]-8-methoxy-1,2,4,5-tetrahydro-benzo[d]azepin-3-yl}-N,N-dimethyl-acetamide 2-Amino-5-methyl-benzenesulfonic acid using 9-Fluorenylmethyl chloroformate was converted in an analogous manner to Example 820a, to 2-(9H-Fluoren-9-ylmethoxycarbonylamino)-5-methyl-benzenesulfonic acid, which was converted in an analogous manner to Example 820b, to (2-Chlorosulfonyl-4-methyl-phenyl)-carbamic acid 9H-fluoren-9-ylmethylester, which was converted in an analogous manner to Example 820c, to 2-Amino-5,N,N-trimethyl-benzenesulfonamide, which was converted, in an analogous procedure to Example 1d, to 2-(2,5-Dichloro-pyrimidin-4-ylamino)-5,N,N-trimethyl-benzenesulfonamide, which was converted to the title compound in an analogous manner to Example 61e using 2-(7-Amino-8-methoxy-1,2,4,5-tetrahydro-benzo[d]azepin-3-yl)-N,N-dimethyl-acetamide. Product isolated as a tan foam (0.027 g, 27%). MP: 67-79° C. $^1$H NMR (400 MHz, CDCl$_3$, δ, ppm): 9.13 (s, 1H), 8.32 (d, 1H, J=8.3 Hz), 8.11 (s, 1H), 7.98 (s, 1H), 7.69-7.67 (m, 1H), 7.48 (m, 1H), 7.39-7.34 (m, 1H), 6.64 (s, 1H), 3.86 (s, 3H), 3.30 (s, 2H), 3.14 (s, 3H), 2.98 (s, 3H), 2.91-2.86 (m, 2H), 2.76-2.64 (m, 12H), 2.41 (s, 3H). MS: 602.48 (MH)$^+$.

Example 831

2-{7-[5-Chloro-4-(2-dimethylsulfamoyl-4-fluoro-phenylamino)-pyrimidin-2-ylamino]-8-methoxy-1,2,4,5-tetrahydro-benzo[d]azepin-3-yl}-N,N-dimethyl-acetamide 831a) 2-(9H-Fluoren-9-ylmethoxycarbonylamino)-5-fluoro-benzenesulfonic acid was prepared from 2-Amino-5-fluoro-benzenesulfonic acid (5.0 g, 0.026 mol) (Suter, C. M.; Weston, A. W., J. Amer. Chem. Soc., 1940, 62, 604-606) and 9-Fluorenylmethyl chloroformate (7.4 g, 0.029 mol) in an analogous manner to Example 820a. Product isolated as a white solid (8.08 g, 74%). $^1$H NMR (400 MHz, DMF-d$_7$, δ, ppm): 10.25 (br s, 1H), 8.20-8.00 (m, 1H), 7.95 (d, 2H, J=7.3 Hz), 7.77 (d, 2H, J=7.3 Hz), 7.54 (dd, 1H, J=8.8 and 3.0 Hz), 7.45 (t, 2H, J=7.3 Hz), 7.38 (t, 2H, J=7.3 Hz), 7.21-7.12 (m, 1H), 4.70-4.10 (m, 4H).

831b) 2-(9H-Fluoren-9-ylmethoxycarbonylamino)-5-fluoro-benzenesulfonic acid was converted in an analogous manner to Example 820b, to (2-Chlorosulfonyl-4-fluoro-phenyl)-carbamic acid 9H-fluoren-9-ylmethyl ester, which was converted in an analogous manner to Example 820c, to 2-Amino-5-fluoro-N,N-dimethyl-benzenesulfonamide, which was converted, in an analogous procedure to Example 1d, to 2-(2,5-Dichloro-pyrimidin-4-ylamino)-5-fluoro-N,N-dimethyl-benzenesulfonamide, which was converted from the title compound in an analogous manner to Example 61e using 2-(7-Amino-8-methoxy-1,2,4,5-tetrahydro-benzo[d]azepin-3-yl)-N,N-dimethyl-acetamide. Product isolated as a yellow foam (0.043 g, 43%). MP: 81-92° C. $^1$H NMR (400 MHz, CDCl$_3$, δ, ppm): 9.08 (s, 1H), 8.44 (dd, 1H, J=9.1 Hz and 4.8 Hz), 8.13 (s, 1H), 7.91 (s, 1H), 7.60 (dd, 1H, J=8.1 Hz and 2.8 Hz), 7.47 (s, 1H), 7.30-7.24 (m, 1H), 6.65 (s, 1H), 3.87 (s, 3H), 3.30 (s, 2H), 3.15 (3H), 2.98 (s, 3H), 2.91-2.86 (m, 2H), 2.78-2.65 (m, 12H). MS: 606.47 (MH)$^+$.

Example 832

2-{7-[5-Chloro-4-(4-chloro-2-dimethylsulfamoyl-phenylamino)-pyrimidin-2-ylamino]-8-methoxy-1,2,4,5-tetrahydro-benzo[d]azepin-3-yl}-N,N-dimethyl-acetamide 2-Amino-5-chloro-benzenesulfonic acid was converted in an analogous manner to Example 820a, to 5-Chloro-2-(9H-fluoren-9-ylmethoxycarbonylamino)-benzenesulfonic acid, which was converted in an analogous manner to Example 820b, to (2-Chlorosulfonyl-4-chloro-phenyl)-carbamic acid 9H-fluoren-9-ylmethyl ester, which was converted in an analogous manner to Example 820c, to 2-Amino-5-chloro-N,N-dimethyl-benzenesulfonamide, which was converted, in an analogous procedure to Example 1d, to 5-Chloro-2-(2,5-dichloro-pyrimidin-4-ylamino)-N,N-dimethyl-benzenesulfonamide, which was converted to the title compound in an analogous manner to Example 61e using 2-(7-Amino-8-methoxy-1,2,4,5-tetrahydro-benzo[d]azepin-3-yl)-N,N-dimethyl-acetamide.

Product isolated as a tan foam (0.050 g, 51%). MP: 70-80° C. $^1$H NMR (400 MHz, CDCl$_3$, δ, ppm): 9.22 (s, 1H), 8.47 (d, 1H, J=8.8 Hz), 8.14 (s, 1H), 7.92 (s, 1H), 7.85 (s, 1H), 7.51-7.45 (m, 2H), 6.65 (s, 1H), 3.87 (s, 3H), 3.30 (s, 2H), 3.15 (s, 3H), 2.98 (s, 3H), 2.91-2.86 (m, 2H), 2.78-2.66 (m, 12H). MS: 622.58 (MH)$^+$.

Example 833

2-{7-[5-Chloro-4-(4-dimethylamino-2-dimethylsulfamoyl-phenylamino)-pyrimidin-2-ylamino]-8-methoxy-1,2,4,5-tetrahydro-benzo[d]azepin-3-yl}-N,N-dimethyl-acetamide 833a) To a solution of 5-Chloro-2-nitro-benzenesulfonyl chloride (2.0 g, 0.0078 mol) (Lebegue, N.; Gallet, S.; Flouquet, N.; Carato, P.; Pfeiffer, B.; Renard, P.; Leonce, S.; Pierre, A.; Chavatte, P.; Berthelot, P. J. Med. Chem. (2005), 48(23), 7363-7373) in Tetrahydrofuran (10 mL, 0.1 mol) was added 2.0 M of Dimethylamine in Tetrahydrofuran (7.8 mL). The mixture was stirred for 18 hours. The mixture was evaporated and water was added then agitated until a solid precipitated. The solid was filtered and dried. 5-Chloro-N,N-dimethyl-2-nitro-benzenesulfonamide isolated as yellow solid (1.87 g, 90%).

833b) To a suspension of 5-Chloro-N,N-dimethyl-2-nitro-benzenesulfonamide (1.8 g, 0.0068 mol) and Potassium carbonate (3.3 g, 0.024 mol) in N,N-Dimethylformamide (20 mL, 0.2 mol) was added Dimethylamine hydrochloride (0.83 g, 0.010 mol). The suspension was heated at 50° C. The mixture was cooled to room temperature and poured into water. The precipitate was filtered and rinsed with water then hexane. The recovered material was purified by silica gel chromatography using 0%→20% Methanol:Dichloromethane solvent gradient. 5-Dimethylamino-N,N-dimethyl-2-nitro-benzenesulfonamide isolated as a yellow solid (0.55 g, 30%).

833c) 5-Dimethylamino-N,N-dimethyl-2-nitro-benzenesulfonamide was converted in an analogous manner to Example 31f, to 2-Amino-5-dimethylamino-N,N-dimethyl-benzenesulfonamide, which was converted in a manner analogous to Example 1d, to 2-(2,5-Dichloro-pyrimidin-4-ylamino)-5-dimethylamino-N,N-dimethyl-benzenesulfonamide, which was converted to the title compound in an analogous manner to Example 61e using 2-(7-Amino-8-methoxy-1,2,4,5-tetrahydro-benzo[d]azepin-3-yl)-N,N-dimethyl-acetamide. Product isolated as a pale yellow foam (0.059 g, 46%). MP: 83-100° C. $^1$H NMR (400 MHz, CDCl$_3$, δ, ppm): 8.59 (s, 1H), 8.08-8.04 (m, 2H), 8.01 (s, 1H), 7.49 (s, 1H), 7.16 (d, 1H, J=2.8 Hz), 6.91 (dd, 1H, J=8.8 Hz and 3.0 Hz), 6.62 (s, 1H), 3.85 (s, 3H), 3.29 (s, 2H), 3.14 (s, 3H), 3.02 (s, 6H), 2.98 (s, 3H), 2.89-2.83 (m, 2H), 2.72-2.58 (m, 13H). MS: 631.21 (MH)$^+$.

Example 834

2-{7-[5-Chloro-4-(2-dimethylsulfamoyl-4-morpholin-4-yl-phenylamino)-pyrimidin-2-ylamino]-8-methoxy-1,2,4,5-tetrahydro-benzo[d]azepin-3-yl}-N,N-dimethyl-acetamide 5-Chloro-N,N-dimethyl-2-nitro-benzenesulfonamide using Morpholine was converted in an analogous manner to Example 171a, to N,N-Dimethyl-5-morpholin-4-yl-2-nitro-benzenesulfonamide, which was converted in an analogous manner to Example 31f, to 2-Amino-N,N-dimethyl-5-morpholin-4-yl-benzenesulfonamide, which was converted, in an analogous procedure to Example 1d, to 2-(2,5-Dichloro-pyrimidin-4-ylamino)-N,N-dimethyl-5-morpholin-4-yl-benzenesulfonamide, which was converted to the title compound in an analogous manner to Example 61e using 2-(7-Amino-8-methoxy-1,2,4,5-tetrahydro-benzo[d]azepin-3-yl)-N,N-dimethyl-acetamide. Product isolated as a pale yellow foam (0.040 g, 32%). MP: 94-120° C. $^1$H NMR (400 MHz, CDCl$_3$, δ, ppm): 8.83 (s, 1H), 8.24 (d, 1H, J=8.8 Hz), 8.08 (s, 1H), 8.01 (s, 1H), 7.49 (s, 1H), 7.37 (d, 1H, J=2.5 Hz), 7.10 (dd, 1H, J=8.8 Hz and 2.5 Hz), 6.63 (s, 1H), 3.92-3.87 (m, 4H), 3.86 (s, 3H), 3.27 (s, 2H), 3.22-3.18 (m, 4H), 3.13 (s, 3H), 2.98 (s, 3H), 2.90-2.85 (m, 2H), 2.74-2.63 (m, 13H). MS: 673.21 (MH)$^+$.

Example 835

2-[7-(5-Chloro-4-{2-methoxy-4-[4-(1-methyl-piperidin-4-yl)-piperazin-1-yl]-phenylamino}-pyrimidin-2-ylamino)-8-methoxy-1,2,4,5-tetrahydro-benzo[d]azepin-3-yl]-N,N-dimethyl-acetamide 4-Fluoro-2-methoxy-1-nitro-benzene using 1-(1-Methylpiperidin-4-yl)-piperazine was converted in an analogous manner to Example 171b, to 1-(3-Methoxy-4-nitro-phenyl)-4-(1-methyl-piperidin-4-yl)-piperazine, which was converted in an analogous manner to Example 31f, to 2-Methoxy-4-[4-(1-methyl-piperidin-4-yl)-piperazin-1-yl]-phenylamine, which was converted, in an analogous procedure to Example 1d, to (2,5-Dichloro-pyrimidin-4-yl)-{2-methoxy-4-[4-(1-methyl-piperidin-4-yl)-piperazin-1-yl]-phenyl}-amine, which was converted to the title compound in an analogous manner to Example 61e using 2-(7-Amino-8-methoxy-1,2,4,5-tetrahydro-benzo[d]azepin-3-yl)-N,N-dimethyl-acetamide. Product isolated as a tan foam (0.032 g, 21%). MP: 83-98° C. $^1$H NMR (400 MHz, CDCl$_3$, δ, ppm): 8.24 (d, 1H, J=8.8 Hz), 8.11 (s, 1H), 8.01 (s, 1H), 7.54 (s, 1H), 7.42 (s, 1H), 6.63 (s, 1H), 6.58-6.55 (m, 1H), 6.53-6.49 (m, 1H), 3.91 (s, 3H), 3.86 (s, 3H), 3.27 (s, 2H), 3.21-3.17 (m, 4H), 3.14 (s, 3H), 2.99-2.91 (m, 5H), 2.90-2.83 (m, 4H), 2.78-2.74 (m, 4H), 2.71-2.66 (m, 4H), 2.35-2.26 (m, 4H), 2.05-1.92 (m, 2H), 1.90-1.83 (m, 2H), 1.171-1.61 (m, 2H). MS: 692.38 (MH)$^+$.

Example 836

2-(7-{5-Chloro-4-[2-(morpholine-4-sulfonyl)-phenylamino]-pyrimidin-2-ylamino}-8-methoxy-1,2,4,5-tetrahydro-benzo[d]azepin-3-yl)-N,N-dimethyl-acetamide o-Nitrobenzenesulfonyl chloride using Morpholine was converted in an analogous manner to Example 833b, to 4-(2-Nitro-benzenesulfonyl)-morpholine, which was converted in an analogous manner to Example 31f, to 2-(Morpholine-4-sulfonyl)-phenylamine, which was converted, in an analogous procedure to Example 1d, to (2,5-Dichloro-pyrimidin-4-yl)-[2-(morpholine-4-sulfonyl)-phenyl]-amine, which was converted to the title compound in an analogous manner to Example 61e using 2-(7-Amino-8-methoxy-1,2,4,5-tetrahydro-benzo[d]azepin-3-yl)-N,N-dimethyl-acetamide. Product isolated as a pale yellow foam (0.064 g, 40%). MP: 88-108° C. $^1$H NMR (400 MHz, CDCl$_3$, δ, ppm): 9.26 (s, 1H), 8.55 (d, 1H, J=8.3 Hz), 8.15 (s, 1H), 7.96 (s, 1H), 7.86 (d, 1H, J=8.1 Hz), 7.58 (t, 1H, J=7.8 Hz), 7.50 (s, 1H), 7.26-7.22 (m, 1H), 6.65 (s, 1H), 3.88 (s, 3H), 3.68-3.64 (m, 4H), 3.29 (s, 2H), 3.14 (s, 3H), 3.10-3.16 (m, 4H), 2.98 (s, 3H), 2.92-2.87 (m, 2H), 2.78-2.64 (m, 6H). MS: 630.27 (MH)$^+$.

Example 837

2-(7-{5-Chloro-4-[2-(4-methyl-piperazine-1-sulfonyl)-phenylamino]-pyrimidin-2-ylamino}-8-methoxy-1,2,4,5-tetrahydro-benzo[d]azepin-3-yl)-N,N-dimethyl-acetamide o-Nitrobenzenesulfonyl chloride using 1-methyl-piperazine was converted, in an analogous manner to Example 833b, to 1-Methyl-4-(2-nitro-benzenesulfonyl)-piperazine, which was converted, in an analogous manner to Example 31f, to 2-(4-Methyl-piperazine-1-sulfonyl)-phenylamine, which was converted in an analogous manner to Example 1d, to (2,5-Dichloro-pyrimidin-4-yl)-[2-(4-methyl-piperazine-1-sulfonyl)-phenyl]-amine, which was converted to the title compound in an analogous manner to Example 61e using 2-(7-Amino-8-methoxy-1,2,4,5-tetrahydro-benzo[d]azepin-3-yl)-N,N-dimethyl-acetamide. Product isolated as a tan foam (0.020 g, 12%). MP: 81-96° C. $^1$HNMR (400 MHz, CDCl$_3$, δ, ppm): 9.29 (s, 1H), 8.53 (d, 1H, J=8.3 Hz), 8.14 (s, 1H), 7.97 (s, 1H), 7.86 (d, 1H, J=7.8 Hz), 7.57-7.51 (m, 1H), 7.51-7.48 (m, 1H), 7.25-7.19 (m, 1H), 6.65 (s, 1H), 3.88 (s, 3H), 3.29 (s, 2H), 3.16-3.11 (m, 7H), 2.99 (s, 3H), 2.91-2.87 (m, 2H), 2.78-2.64 (m, 6H), 2.40-2.36 (m, 4H), 2.19 (s, 3H). MS: 643.23 (MH)$^+$.

Example 838

5-Chloro-2-{5-chloro-2-[8-methoxy-3-(2-methoxy-1-methoxymethyl-ethyl)-2,3,4,5-tetrahydro-1H-benzo[d]azepin-7-ylamino]-pyrimidin-4-ylamino}-N,N-dimethyl-benzenesulfonamide The title compound was prepared from 8-Methoxy-3-(2-methoxy-1-methoxymethyl-ethyl)-2,3,4,5-tetrahydro-1H-benzo[d]azepin-7-ylamine and 5-Chloro-2-(2,5-dichloro-pyrimidin-4-ylamino)-N,N-dimethyl-benzenesulfonamide in an analogous manner to Example 61e. Product isolated as a tan foam (0.072 g, 54%). MP: 66-79° C. $^1$H NMR (400 MHz, CDCl$_3$, δ, ppm): 9.23 (s, 1H), 8.49 (d, 1H, J=8.8 Hz), 8.14 (s, 1H), 7.91 (s, 1H), 7.87-7.85 (m, 1H), 7.52-7.46 (m, 2H), 6.65 (s, 1H), 3.87 (s, 3H), 3.59-3.53 (m, 2H), 3.49-3.43 (m, 2H), 3.33 (s, 6H), 3.08-3.01 (m, 1H), 2.88-2.80 (m, 6H), 2.77 (s, 6H), 2.73-2.68 (m, 2H). MS: 639.19 (MH)$^+$.

Example 839

5-Chloro-2-{5-chloro-2-[8-methoxy-3-(2-methoxy-ethyl)-2,3,4,5-tetrahydro-1H-benzo[d]azepin-7-ylamino]-pyrimidin-4-ylamino}-N,N-dimethyl-benzenesulfonamide The title compound was prepared from 8-Methoxy-3-(2-methoxy-ethyl)-2,3,4,5-tetrahydro-1H-benzo[d]azepin-7-ylamine and 5-Chloro-2-(2,5-dichloro-pyrimidin-4- ylamino)-N,N-dimethyl-benzenesulfonamide in an analogous manner to Example 61e. Product isolated as a tan foam (0.061 g, 49%). MP: 59-79° C. $^1$H NMR (400 MHz, CDCl$_3$, ppm): 9.22 (s, 1H), 8.47 (d, 1H, J=8.8 Hz), 8.14 (s, 1H), 7.92 (s, 1H), 7.86-7.84 (m, 1H), 7.51-7.46 (m, 2H), 6.65 (s, 1H), 3.87 (s, 3H), 3.58-3.53 (m, 2H), 3.38 (s, 3H), 2.92-2.87 (m, 2H), 2.79-2.68 (m, 14H). MS: 595.17 (MH)$^+$.

Example 840

5-Chloro-2-{5-chloro-2-[3-(2-hydroxy-ethyl)-8-methoxy-2,3,4,5-tetrahydro-1H-benzo[d]azepin-7-ylamino]-pyrimidin-4-ylamino}-N,N-dimethyl-benzenesulfonamide The title compound was prepared from 2-(7-Amino-8-methoxy-1,2,4,5-tetrahydro-3-benzazepin-3-yl)-ethanol and 5-Chloro-2-(2,5-dichloro-pyrimidin-4-ylamino)-N,N-dimethyl-benzenesulfonamide in an analogous manner to Example 61e. Product isolated as a tan foam (0.058 g, 48%). MP: 194-199° C. $^1$H NMR (400 MHz, CDCl$_3$, δ, ppm): 9.22 (s, 1H), 8.47 (d, 1H, J=8.8 Hz), 8.15 (s, 1H), 7.95 (s, 1H), 7.87-7.85 (m, 1H), 7.53-7.47 (m, 2H), 6.66 (s, 1H), 3.88 (s, 3H), 3.67-3.62 (m, 2H), 2.91-2.86 (m, 2H), 2.77 (s, 6H), 2.75-2.65 (m, 8H). MS: 581.14 (MH)$^+$.

Example 841

5-Chloro-2-{5-chloro-2-[8-methoxy-3-(2-morpholin-4-yl-2-oxo-ethyl)-2,3,4,5-tetrahydro-1H-benzo[d]azepin-7-ylamino]-pyrimidin-4-ylamino}-N,N-dimethyl-benzenesulfonamide The title compound was prepared from 2-(7-Amino-8-methoxy-1,2,4,5-tetrahydro-3-benzazepin-3-yl)-1-morpholin-4-yl-ethanone and 5-Chloro-2-(2,5-dichloro-pyrimidin-4-ylamino)-N,N-dimethyl-benzenesulfonamide in an analogous manner to Example 61e. Product isolated as a tan foam (0.034 g, 24%). MP: 100-115° C. $^1$H NMR (400 MHz, CDCl$_3$, δ, ppm): 9.21 (s, 1H), 8.45 (d, 1H, J=8.8 Hz), 8.15 (s, 1H), 7.93 (s, 1H), 7.87-7.85 (m, 1H), 7.53-7.47 (m, 2H), 6.65 (s, 1H), 3.88 (s, 3H), 3.75-3.62 (m, 9H), 3.30 (s, 2H), 2.90-2.85 (m, 2H), 2.77 (s, 6H), 2.75-2.63 (m, 6H). MS: 664.19 (MH)$^+$.

Example 842

5-Chloro-2-(5-chloro-2-{8-methoxy-3-[2-(4-methyl-piperazin-1-yl)-2-oxo-ethyl]-2,3,4,5-tetrahydro-1H-benzo[d]azepin-7-ylamino}-pyrimidin-4-ylamino)-N,N-dimethyl-benzenesulfonamide The title compound was prepared from 2-(7-Amino-8-methoxy-1,2,4,5-tetrahydro-3-benzazepin-3-yl)-1-(4-methyl-piperazin-1-yl)-ethanone and 5-Chloro-2-(2,5-dichloro-pyrimidin-4-ylamino)-N,N-dimethyl-benzenesulfonamide in an analogous manner to Example 61e. Product isolated as a tan foam (0.025 g, 20%). MP: 137-150° C. $^1$H NMR (400 MHz, CDCl$_3$, δ, ppm): 9.21 (s, 1H), 8.46 (d, 1H, J=8.8 Hz), 8.15 (s, 1H), 7.93 (s, 1H), 7.86 (d, 1H, J=2.5 Hz), 7.51-7.47 (m, 2H), 6.65 (s, 1H), 3.87 (s, 3H), 3.75-3.63 (m, 4H), 3.30 (s, 2H), 2.91-2.86 (m, 2H), 2.77 (s, 6H), 2.76-2.63 (m, 6H), 2.49-2.38 (m, 4H), 2.33 (s, 3H). MS: 677.18 (MH)$^+$.

Example 843

2-{7-[5-Chloro-4-(2-dimethylsulfamoyl-4-trifluoromethyl-phenylamino)-pyrimidin-2-ylamino]-8-methoxy-1,2,4,5-tetrahydro-benzo[d]azepin-3-yl}-N,N-dimethyl-acetamide 843a) 2-Chloro-5-trifluoromethyl-benzenesulfonyl chloride using 2.0 M of Dimethylamine in Tetrahydrofuran was converted in an analogous manner to Example 833a, to 2-Chloro-N,N-dimethyl-5-trifluoromethyl-benzenesulfonamide. Product isolated as a yellow solid (2.10 g, 100%).

843b) A solution of 2-Chloro-N,N-dimethyl-5-trifluoromethyl-benzenesulfonamide (2.10 g, 0.00730 mol) in Benzylamine (5 mL, 0.04 mol) was heated at 100° C. for 5 hours. The benzylamine was evaporated under reduced pressure. The residue was partitioned between water (50 mL) and ethyl acetate (50 mL). The organic layer was washed with water (3×50 mL), dried over magnesium sulfate, filtered and evaporated. The material was purified via silica gel chromatography using 0% 25% Ethyl Acetate:Hexane solvent gradient. 2-Benzylamino-N,N-dimethyl-5-trifluoromethyl-benzenesulfonamide isolated as a pale yellow solid (1.84 g, 70%).

843c) 2-Benzylamino-N,N-dimethyl-5-trifluoromethyl-benzenesulfonamide was converted in an analogous manner to Example 31f, to 2-Amino-N,N-dimethyl-5-trifluoromethyl-benzenesulfonamide, which was converted, in an analogous procedure to Example 1d, to 2-(2,5-Dichloro-pyrimidin-4-ylamino)-N,N-dimethyl-5-trifluoromethyl-benzenesulfonamide, which was converted to the title compound in an analogous manner to Example 61e using 2-(7-Amino-8-methoxy-1,2,4,5-tetrahydro-benzo[d]azepin-3-yl)-N,N-dimethyl-acetamide. Product isolated as a pale yellow foam (0.056 g, 51%). MP: 86-95° C. $^1$H NMR (400 MHz, CDCl$_3$, δ, ppm): 9.59 (s, 1H), 8.79 (d, 1H, J=8.8 Hz), 8.20 (s, 1H), 8.12 (s, 1H), 7.93 (s, 1H), 7.78-7.74 (m, 1H), 7.49 (s, 1H), 6.67 (s, 1H), 3.88 (s, 3H), 3.30 (s, 2H), 3.14 (s, 3H), 2.98 (s, 3H), 2.92-2.88 (m, 2H), 2.80 (s, 6H), 2.79-2.64 (m, 6H). MS: 656.22 (MH)$^+$.

Example 844

5-Chloro-N*2*-[8-methoxy-3-(2-methoxy-1-methoxymethyl-ethyl)-2,3,4,5-tetrahydro-1H-benzo[d]azepin-7-yl]-N*4*-[2-(pyrrolidine-1-sulfonyl)-phenyl]-pyrimidine-2,4-diamine The title compound was prepared from 8-Methoxy-3-(2-methoxy-1-methoxymethyl-ethyl)-2,3,4,5-tetrahydro-1H-benzo[d]azepin-7-ylamine and (2,5-Dichloro-pyrimidin-4-yl)-[2-(pyrrolidine-1-sulfonyl)-phenyl]-amine in an analogous manner to Example 61e. Product isolated as an off-white foam (0.072 g, 61%). MP: 68-88° C. $^1$H NMR (400 MHz, CDCl$_3$, δ, ppm): 9.42 (s, 1H), 8.54 (d, 1H, J=8.3 Hz), 8.13 (s, 1H), 7.97 (s, 1H), 7.93 (d, 1H, J=7.8 Hz), 7.55 (t, 1H, J=7.7 Hz), 7.47 (s, 1H), 7.21 (t, 1H, J=7.7 Hz), 6.65 (s, 1H), 3.86 (s, 3H), 3.58-3.50 (m, 2H), 3.48-3.40 (m, 2H), 3.33 (s, 6H), 3.29-3.23 (m, 4H), 3.07-2.98 (m, 1H), 2.87-2.75 (m, 6H), 2.74-2.68 (m, 2H). MS: 631.25 (MH)$^+$.

Example 845

2-(7-{5-Chloro-4-[2-((R)-3-dimethylamino-pyrrolidine-1-sulfonyl)-phenylamino]-pyrimidin-2-ylamino}-8-methoxy-1,2,4,5-tetrahydro-benzo[d]azepin-3-yl)-N,N-dimethyl-acetamide o-Nitrobenzenesulfonyl chloride using Dimethyl-(R)-pyrrolidin-3-yl-amine was converted in an analogous manner to Example 833b, to Dimethyl-[(R)-1-(2-nitro-benzenesulfonyl)-pyrrolidin-3-yl]-amine, which was converted in an analogous manner to Example 31f, to [(R)-1-(2-Amino-benzenesulfonyl)-pyrrolidin-3-yl]-dimethyl-amine, which was converted, in an analogous procedure to Example 1d, to (2,5-Dichloro-pyrimidin-4-yl)-[2-((R)-3-dimethylamino-pyrrolidine-1-sulfonyl)-phenyl]-amine, which was converted to the title compound in an analogous manner to Example 61e using 2-(7-Amino-8-methoxy-1,2,4,5-tetrahydro-benzo[d]azepin-3-yl)-N,N-dimethyl-acetamide. Product isolated as a tan foam (0.033 g, 21%). MP: 74-102° C. $^1$H NMR (400 MHz, CDCl$_3$, δ, ppm): 9.33 (s, 1H), 8.53-8.49 (m, 1H), 8.15-8.13 (m, 1H), 7.99-7.97 (M, 1H), 7.94-7.90 (m, 1H), 7.58-7.49 (m, 2H), 7.26-7.20 (m, 1H), 6.65 (s, 1H), 3.87 (s, 3H), 3.56-3.50 (m, 1H), 3.44-3.37 (m, 1H), 3.32-3.22 (m, 3H), 3.17-3.09 (m, 4H), 3.04-2.94 (m, 4H), 2.92-2.87 (m, 2H), 2.78-2.60 (m, 6H), 2.07 (s, 1H), 2.03-1.92 (m, 1H), 1.72-1.63 (m, 1H). MS: 657.27 (MH)$^+$.

Example 846

2-(7-{5-Chloro-4-[2-((S)-3-dimethylamino-pyrrolidine-1-sulfonyl)-phenylamino]-pyrimidin-2-ylamino}-8-methoxy-1,2,4,5-tetrahydro-benzo[d]azepin-3-yl)-N,N-dimethyl-acetamide o-Nitrobenzenesulfonyl chloride using Dimethyl-(S)-pyrrolidin-3-yl-amine was converted in an analogous manner to Example 833b, to Dimethyl-[(S)-1-(2-nitro-benzenesulfonyl)-pyrrolidin-3-yl]-amine, which was converted in an analogous manner to Example 31, to [(S)-1-(2-Amino-benzenesulfonyl)-pyrrolidin-3-yl]-dimethyl-amine, which was converted, in an analogous procedure to Example 1d, (2,5-Dichloro-pyrimidin-4-yl)-[2-((S)-3-dimethylamino-pyrrolidine-1-sulfonyl)-phenyl]-amine, which was converted to the title compound in an analogous manner to Example 61e using 2-(7-Amino-8-methoxy-1,2,4,5-tetrahydro-benzo[d]azepin-3-yl)-N,N-dimethyl-acetamide. Product isolated as a tan foam (0.042 g, 27%). MP: 74-102° C. $^1$H NMR (400 MHz, CDCl$_3$, δ, ppm): 9.33 (s, 1H), 8.51 (d, 1H, J=8.1 Hz), 8.14 (s, 1H), 7.98 (s, 1H), 7.92 (d, 1H, J=7.8 Hz), 7.58-7.49 (m, 2H), 7.26-7.20 (m, 1H), 6.65 (s, 1H), 3.87 (s, 3H), 3.56-3.50 (m, 1H), 3.44-3.37 (m, 1H), 3.3-3.21 (m, 3H), 3.16-3.10 (m, 4H), 3.03-2.94 (m, 4H), 2.92-2.86 (m, 2H), 2.77-2.59 (m, 6H), 2.07 (s, 6H), 2.03-1.92 (m, 1H), 1.74-1.62 (m, 1H). MS: 657.27 (MH)$^+$.

Example 847

2-{1-[5-Chloro-2-(3-dimethylcarbamoylmethyl-8-methoxy-2,3,4,5-tetrahydro-1H-benzo[d]azepin-7-ylamino)-pyrimidin-4-ylamino]-cyclohexyl}-acetamide 847a) 2-[1-(2,5-Dichloro-pyrimidin-4-ylamino)-cyclohexyl]-acetamide was prepared from 2-(1-Amino-cyclohexyl)-acetamide (2.0 g, 0.013 mol) (Suzuki, T.; Imanishi, N. Itahana, H.; Watauki, S.; Ohta, M.; Mase, T., *Synthetic Communications*, 1988, 28(4), 701-712) and 2,4,5-Trichloro-pyrimidine (1.5 mL, 0.013 mol) in an analogous manner to Example 1d. Product isolated as a white solid (2.28 g, 59%). MP: 124-128° C. $^1$H NMR (400 MHz, DMSO-d$_6$, δ, ppm): 8.19 (s, 1H), 7.51 (br s, 1H), 7.34 (br s, 1H), 7.04 (br s, 1H), 2.62 (s, 2H), 2.58-2.52 (m, 2H), 1.55-1.30 (m, 8H). MS: 303.00 (MH)$^+$.

847b) The title compound was prepared from 2-(7-Amino-8-methoxy-1,2,4,5-tetrahydro-benzo[d]azepin-3-yl)-N,N-dimethyl-acetamide and 2-[1-(2,5-Dichloro-pyrimidin-4-ylamino)-cyclohexyl]-acetamide in an analogous manner to Example 61e. Product isolated as a pale yellow foam (0.064 g, 51%). MP: 90-107° C. $^1$H NMR (400 MHz, CDCl$_3$, δ, ppm): 7.92 (s, 1H), 7.87 (s, 1H), 7.17 (s, 1H), 6.65 (s, 1H), 5.43 (br s, 1H), 5.25 (s, 1H), 5.07 (br s, 1H), 3.85 (s, 3H), 3.29 (s, 2H), 3.14 (s, 3H), 2.98 (s, 3H), 2.92-2.86 (m, 6H), 2.72-2.67 (m, 4H), 2.38 (m, 2H), 1.70-1.58 (m, 5H), 1.50-1.40 (m, 3H). MS: 544.27 (MH)$^+$.

Example 848

2-(1-{5-Chloro-2-[8-methoxy-3-(2-methoxy-1-methoxymethyl-ethyl)-2,3,4,5-tetrahydro-1H-benzo[d]azepin-7-ylamino]-pyrimidin-4-ylamino}-cyclohexyl)-acetamide The title compound was prepared from 8-Methoxy-3-(2-methoxy-1-methoxymethyl-ethyl)-2,3,4,5-tetrahydro-1H-benzo[d]azepin-7-ylamine and 2-[1-(2,5-Dichloro-pyrimidin-4-ylamino)-cyclohexyl]-acetamide in an analogous manner to Example 61e. Product isolated as a pale yellow foam (0.064 g, 49%). MP: 71-83° C. $^1$H NMR (400 MHz, CDCl$_3$, δ, ppm): 7.92 (s, 1H), 7.84 (s, 1H), 7.14 (s, 1H), 6.64 (s, 1H), 5.40 (br s, 1H), 5.24 (s, 1H), 5.05 (br s, 1H), 3.85 (s, 3H), 3.57-3.51 (m, 2H), 3.47-3.41 (m, 2H), 3.32 (s, 6H), 3.06-2.98 (m, 1H), 2.90 (s, 2H), 2.87-2.77 (m, 8H), 2.37-2.29 (m, 2H), 1.71-1.29 (m, 8H). MS: 561.29 (MH)$^+$.

Example 849

2-(1-{5-Chloro-2-[3-(2-hydroxy-ethyl)-8-methoxy-2,3,4,5-tetrahydro-1H-benzo[d]azepin-7-ylamino]-pyrimidin-4-ylamino}-cyclohexyl)-acetamide The title compound was prepared from 2-(7-Amino-8-methoxy-1,2,4,5-tetrahydro-3-benzazepin-3-yl)-ethanol and 2-[1-(2,5-Dichloro-pyrimidin-4-ylamino)-cyclohexyl]-acetamide in an analogous manner to Example 61e. Product isolated as a pale yellow foam (0.064 g, 24%). MP: 84-96° C. $^1$H NMR (400 MHz, CDCl$_3$, δ, ppm): 7.93 (s, 1H), 7.89 (s, 1H), 7.18 (s, 1H), 6.66 (s, 1H), 5.44 (br s, 1H), 5.26 (s, 1H), 5.11 (br s, 1H), 3.86 (s, 3H), 3.66-3.61 (m, 2H), 2.93 (m, 6H), 2.73-2.64 (m, 6H), 2.37-2.29 (m, 2H), 1.72-1.29 (m, 9H). MS: 503.17 (MH)$^+$.

Example 850

2-[5-Chloro-2-(1-ethyl-5,5-dimethyl-2-oxo-2,3,4,5-tetrahydro-1H-benzo[b]azepin-8-ylamino)-pyrimidin-4-ylamino]-5-dimethylamino-N,N-dimethyl-benzenesulfonamide The title compound was prepared from 8-Amino-1-ethyl-5,5-dimethyl-1,3,4,5-tetrahydro-benzo[b]azepin-2-one and 2-(2,5-Dichloro-pyrimidin-4-ylamino)-5-dimethylamino-N,N-dimethyl-benzenesulfonamide in an analogous manner to Example 61e. Product isolated as a tan solid (0.077 g, 64%). MP: 240-243° C. $^1$H NMR (400 MHz, CDCl$_3$, δ, ppm): 8.90 (s, 1H), 8.15 (d, J=9.1 Hz, 1H), 8.07 (s, 1H), 7.66 (d, J=2.3 Hz, 1H), 7.30-7.19 (m, 2H), 7.14 (d, J=3.0 Hz, 1H), 6.93 (br s, 1H), 6.85 (dd, J=9.2 Hz and 2.9 Hz, 1H), 3.75-3.62 (m, 2H), 3.02 (s, 6H), 2.72 (s, 6H), 2.37-2.26 (m, 2H), 2.10-1.95 (m, 2H), 1.32 (s, 6H), 1.17 (t, J=7.1 Hz, 3H). MS: 586.24 (MH)$^+$.

Example 851

2-[5-Chloro-2-(1-ethyl-5,5-dimethyl-2-oxo-2,3,4,5-tetrahydro-1H-benzo[b]azepin-8-ylamino)-pyrimidin-4-ylamino]-N,N-dimethyl-5-morpholin-4-yl-benzenesulfonamide The title compound was prepared from 8-Amino-1-ethyl-5,5-dimethyl-1,3,4,5-tetrahydro-benzo[b]azepin-2-one and 2-(2,5-Dichloro-pyrimidin-4-ylamino)-N,N-dimethyl-5-morpholin-4-yl-benzenesulfonamide in an analogous manner to Example 61e. Product isolated as tan foam (0.076 g, 52%). MP: 130-151° C. $^1$H NMR (400 MHz, CDCl$_3$, δ, ppm): 9.06 (s, 1H), 8.28 (d, J=9.1 Hz, 1H), 8.10 (s, 1H), 7.68 (d, J=2.3 Hz, 1H), 7.35 (d, J=3.0 Hz, 1H), 7.29-7.26 (m, 1H), 7.18 (dd, J=8.7 Hz and 2.1 Hz, 1H), 7.04 (dd, J=9.2 Hz and 2.9 Hz, 1H), 6.94 (br s, 1H), 3.92-3.88 (m, 4H), 3.76-3.62 (m, 2H), 3.23-3.17 (m, 4H), 2.73 (s, 6H), 2.35-2.26 (m, 2H), 2.15-1.95 (m, 2H), 1.33 (s, 6H), 1.18 (t, J=7.2 Hz, 3H). MS: 628.25 (MH)$^+$.

Example 852

2-{5-Chloro-2-[3-(2-methoxy-ethyl)-2,3,4,5-tetrahydro-1H-benzo[d]azepin-7-ylamino]-pyrimidin-4-ylamino}-5-dimethylamino-N,N-dimethyl-benzenesulfonamide The title compound was prepared from 3-(2-Methoxyethyl)-2,3,4,5-tetrahydro-1H-benzo[d]azepin-7-ylamine and 2-(2,5-Dichloro-pyrimidin-4-ylamino)-5-dimethylamino-N,N-dimethyl-benzenesulfonamide in an analogous manner to Example 61e. Product isolated as a yellow foam (0.053 g, 45%). MP: 72-82° C. $^1$H NMR (400 MHz, CDCl$_3$, δ, ppm): 8.75 (s, 1H), 8.12 (d, J=8.8 Hz, 1H), 8.04 (s, 1H), 7.31 (d, J=2.0 Hz, 1H), 7.20 (dd, 1H, J=8.1 Hz and J=2.0 Hz, 1H), 7.15 (d, J=2.8 Hz, 1H), 6.97 (d, J=8.1 Hz, 1H), 6.91 (dd, J=9.1 Hz and J=3.0 Hz, 1H), 6.88 (s, 1H), 3.53 (t, J=5.7 Hz, 2H), 3.36 (s, 3H), 3.02 (s, 6H), 2.91-2.80 (m, 4H), 2.76-2.66 (m, 12H). MS: 574.17 (MH)$^+$.

Example 853

2-{5-Chloro-2-[3-(2-methoxy-ethyl)-2,3,4,5-tetrahydro-1H-benzo[d]azepin-7-ylamino]-pyrimidin-4-ylamino}-N,N-dimethyl-5-morpholin-4-yl-benzenesulfonamide The title compound was prepared from 3-(2-Methoxyethyl)-2,3,4,5-tetrahydro-1H-benzo[d]azepin-7-ylamine and 2-(2,5-Dichloro-pyrimidin-4-ylamino)-N,N-dimethyl-5-morpholin-4-yl-benzenesulfonamide in an analogous manner to Example 61e. Product isolated as a light brown foam (0.043 g, 30%). MP: 74-85° C. $^1$H NMR (400 MHz, CDCl$_3$, δ, ppm): 8.96 (s, 1H), 8.29 (d, J=9.1 Hz, 1H), 8.07 (s, 1H), 7.36 (d, J=3.0 Hz, 1H), 7.29 (d, J=1.8 Hz, 1H), 7.22 (dd, J=8.0 Hz and J=2.1 Hz, 1H), 7.10 (dd, J=9.2 Hz and J=2.9 Hz, 1H), 6.99 (d, J=7.8 Hz, 1H), 6.88 (s, 1H), 3.92-3.88 (m, 4H), 3.54 (t, J=5.6 Hz, 2H), 3.36 (s, 3H), 3.22-3.18 (m, 4H), 2.93-2.83 (m, 4H), 2.78-2.68 (m, 12H). MS: 616.18 (MH)$^+$.

Example 854

5-Chloro-N(2)-[8-methoxy-3-(2-methoxy-ethyl)-2,3,4,5-tetrahydro-1H-benzo[d]azepin-7-yl]-N(4)-[2-((S)-3-methyl-pyrrolidine-1-sulfonyl)-phenyl]-pyrimidine-2,4-diamine o-Nitrobenzenesulfonyl chloride using (S)-3-Methyl-pyrrolidine hydrochloride was converted in an analogous manner to Example 833b to, (S)-3-Methyl-1-(2-nitro-benzenesulfonyl)-pyrrolidine, which was converted in an analogous manner to Example 31f, to 2-((S)-3-Methyl-pyrrolidine-1-sulfonyl)-phenylamine, which was converted, in an analogous procedure to Example 1d, to (2,5-Dichloro-pyrimidin-4-yl)-[2-((S)-3-methyl-pyrrolidine-1-sulfonyl)-phenyl]-amine, which was converted to the title compound in an analogous manner to Example 61e using 8-Methoxy-3-(2-methoxy-ethyl)-2,3,4,5-tetrahydro-1H-benzo[d]azepin-7-ylamine. Product isolated as a pale yellow foam (0.057 g, 46%). MP: 55-66° C. $^1$H NMR (400 MHz, CDCl$_3$, δ, ppm): 9.36 (s, 1H), 8.49 (d, J=8.3 Hz, 1H), 8.14 (s, 1H), 7.97 (s, 1H), 7.93 (dd, J=8.0 Hz and 1.1 Hz, 1H), 7.56-7.51 (m, 1H), 7.49 (s, 1H), 7.21 (t, J=7.7 Hz, 1H), 6.64 (s, 1H), 3.87 (s, 1H), 3.55 (t, J=5.4 Hz, 2H), 3.43 (dd, J=9.5 Hz and 7.2 Hz, 1H), 3.39-3.33 (m, 4H), 3.29-3.22 (m, 1H), 2.91-2.86 (m, 2H), 2.82-2.65 (m, 9H), 2.24-2.10 (m, 1H), 1.95-1.87 (m, 1H), 1.43-1.33 (m, 1H), 0.86 (d, J=6.6 Hz, 3H). MS: 601.20 (MH)$^+$.

Example 855

2-(7-{5-Chloro-4-[2-((S)-3-methyl-pyrrolidine-1-sulfonyl)-phenylamino]-pyrimidin-2-ylamino}-8-methoxy-1,2,4,5-tetrahydro-benzo[d]azepin-3-yl)-ethanol The title compound was prepared from 2-(7-Amino-8-methoxy-1,2,4,5-tetrahydro-3-benzazepin-3-yl)-ethanol and (2,5-Dichloro-pyrimidin-4-yl)-[2-((S)-3-methyl-pyrrolidine-1-sulfonyl)-phenyl]-amine in an analogous manner to Example 61e. Product isolated as an off-white foam (0.035 g, 29%). MP: 65-85° C. $^1$H NMR (400 MHz, CDCl$_3$, δ, ppm): 9.37 (s, 1H), 8.49 (d, J=8.3 Hz, 1H), 8.15 (s, 1H), 8.01 (s, 1H), 7.94 (dd, J=8.0 Hz and 1.4 Hz, 1H), 7.57-7.50 (m, 2H), 7.25-7.20 (m, 1H), 6.65 (s, 1H), 3.87 (s, 3H), 3.64 (t, J=5.4 Hz, 2H), 3.43 (dd, J=9.5 Hz and 7.2 Hz, 1H), 3.40-3.34 (m, 1H), 3.30-3.22 (m, 1H), 2.90-2.86 (m, 2H), 2.80 (dd, J=9.5 Hz and 7.5 Hz, 1H), 2.24-2.11 (m, 1H), 1.96-1.87 (m, 1H), 1.43-1.33 (m, 1H), 0.86 (d, J=6.6 Hz, 3H). MS: 587.16 (MH)$^+$.

Example 856

2-(7-{5-Chloro-4-[2-((S)-3-methyl-pyrrolidine-1-sulfonyl)-phenylamino]-pyrimidin-2-ylamino}-8-methoxy-1,2,4,5-tetrahydro-benzo[d]azepin-3-yl)-N,N-dimethyl-acetamide The title compound was prepared from 2-(7-Amino-8-methoxy-1,2,4,5-tetrahydro-benzo[d]azepin-3-yl)-N,N-dimethyl-acetamide and (2,5-Dichloro-pyrimidin-4-yl)-[2-((S)-3-methyl-pyrrolidine-1-sulfonyl)-phenyl]-amine in an analogous manner to Example 61e. Product isolated as an off-white foam (0.061 g, 47%). MP: 79-89° C. $^1$H NMR (400 MHz, CDCl$_3$, δ, ppm): 9.36 (s, 1H), 8.49 (d, J=8.3 Hz, 1H), 8.14 (s, 1H), 7.97 (s, 1H), 7.93 (dd, J=8.0 Hz and 1.4 Hz, 1H), 7.56-7.49 (m, 2H), 7.25-7.20 (m, 2H), 6.64 (s, 1H), 3.87 (s, 3H), 3.43 (dd, J=9.6 Hz and 7.1 Hz, 1H), 3.40-3.33 (m, 1H), 3.30-3.22 (m, 3H), 3.14 (s, 3H), 2.98 (s, 3H), 2.91-2.86 (m, 2H), 2.79 (dd, J=9.5 Hz and 7.5 Hz, 1H), 2.74-2.63 (m, 6H), 2.25-2.10 (m, 1H), 1.95-1.87 (m, 1H), 1.43-1.33 (m, 1H), 0.86 (d, J=6.8 Hz, 3H). MS: 628.21 (MH)$^+$.

Example 861

(2-exo-3-exo)-3-[5-Chloro-2-(2,3,4,5-tetrahydro-benzo[b]oxepin-9-ylamino)-pyrimidin-4-ylamino]-bicyclo[2.2.1]hept-5-ene-2-carboxylic acid amide 861a) To a stirred solution of 2-nitrophenol (5.2 g, 0.037 mol) in acetone (100 mL, 1 mol) at 0° C. was added 3-iodo- 1-propene (3.8 mL, 0.041 mol) and potassium carbonate (5.7 g, 0.041 mol). The reaction mixture was stirred for 1 h at 0° C. then warmed to room temperature overnight. The reaction mixture was worked up by diluting the reaction with water and washing with dichloromethane. The organic phase was washed with a 10% HCl solution, water and brine then dried over magnesium sulfate, filtered and concentrated in vacuo to a greenish-brown oil. Purification of the reaction mixture was accomplished using ISCO chromatography on silica gel (350 g column) using hexane-ethyl acetate (0-100%). The major fractions were combined and concentrated in vacuo to give product, 1-allyloxy-2-nitrobenzene, as a light yellow-green oil (5.4 g, 81%). $^1$H NMR (CDCl3, 400 MHz) δ 7.83 (d, 1H, J=8.09 Hz), 7.51 (t, 1H, J=8.08 Hz), 7.08 (d, 1H, J=8.33 Hz), 7.03 (t, 1H, J=8.08 Hz), 6.04 (m, 1H), 5.49 (d, 1H, J=17.2 Hz), 5.32 (d, 1H, J=10.6 Hz), 4.69 (d, 2H, J=5.05 Hz).

861b) Into a microwave vial was placed 1-allyloxy-2-nitrobenzene (0.5 g, 0.003 mol). The yellow-green oil was heated neat in the microwave at 180° C. for 30 min producing a black solid. 1H NMR of the crude solid showed desired product plus impurities. The reaction mixture was purified by ISCO chromatography on silica gel using 5-20% ethyl acetate-hexane. Product, 2-allyl-6-nitrophenol, was isolated as a yellow oil (0.1 g, 20%). $^1$H NMR (CDCl$_3$, 400 MHz) δ 10.95 (s, 1H), 8.00 (d, 1H, J=8.59 Hz), 7.47 (d, 1H, J=7.58 Hz), 6.93 (t, 2H, J=8.59, 7.58 Hz), 5.97 (m, 1H), 5.12 (m, 2H), 3.49 (d, 2H, J=6.31 Hz), 861c) To a stirred solution of 2-allyl-6-nitrophenol (100 mg, 0.0006 mol) in acetone (4 mL, 0.06 mol) at 0° C. in an ice bath was added potassium carbonate (0.092 g, 0.00067 mol) followed by 3-iodo-1-propene (0.11 g, 0.00067 mol) under an atmosphere of nitrogen. The reaction mixture was stirred for 1 h at 0° C. then warmed to room temperature overnight. The reaction mixture was diluted with ethyl acetate and washed with 10% HCl, water, dried over magnesium sulfate and concentrated in vacuo. The reaction mixture was purified by ISCO chromatography on silica gel (12 g) using ethyl acetate-hexane (10%-50%) to give 1-allyl-2-allyloxy-3-nitrobenzene as a yellow oil (93 mg, 80%). $^1$H NMR (400 MHz, CDCl$_3$) δ 7.69 (d, 1H, J=8.0 Hz), 7.44 (d, 1H, J=7.8 Hz), 7.16 (t, 1H, J=8.08, 7.8 Hz), 5.90-6.13 (m, 2H), 5.40 (d, 1H, J=17 Hz), 5.29 (d, 1H, J=10 Hz), 5.15 (d, 1H, J=10 Hz), 5.09 (d, 1H, J=17 Hz), 4.50 (d, 2H, J=5.8 Hz), 3.49 (d, 2H, J=6.3 Hz).

861d) To a stirred solution of 1-allyl-2-allyloxy-3-nitrobenzene (100 mg, 0.0004 mol) in methylene chloride (6 mL, 0.09 mol) at room temperature was added benzylidenebis(tricyclohexylphosphine)dichlororuthenium (20 mg, 0.00002 mol). The reaction mixture was stirred at room temperature overnight. The reaction solvent was removed in vacuo leaving a dark solid which was purified by ISCO column chromatography on silica gel using hexane-methyl-t-butyl ether (3:1). The fractions corresponding to product were combined and concentrated in vacuo to give 9-nitro-2,5-dihydrobenzo[b]oxepine as a dark solid which was further purified to give product as an off-white solid (80 mg, 90%). $^1$H NMR (CDCl3, 400 MHz) δ 7.66 (d, 1H, J=8.09 Hz), 7.33 (d, 1H, J=7.32 Hz), 7.11 (dd, 1H, J=7.58, 8.09 Hz), 5.86 (m, 1H), 5.54 (d, 1H, J=11Hz), 4.79 (s, 2H), 3.54 (s, 2H);

861e) Into a Parr pressure reactor was placed 9-nitro-2,5-dihydro-benzo[b]oxepine (200 mg, 0.001 mol) in methanol (10 mL, 0.3 mol). To this solution was added palladium on carbon 10% (10 mg). The reaction was placed under 50 psi hydrogen and shaken overnight. Reaction mixture was filtered through celite, rinsed with methanol (3×10 mL) and concentrated in vacuo to give 2,3,4,5-tetrahydro-benzo[b]oxepin-9-ylamine as an off-white solid (142 mg, 83%).

861f) The title compound was prepared from 2,3,4,5-tetrahydrobenzo[b]oxepin-9-ylamine and (1R,4S)-3-(2,5-dichloro-pyrimidin-4-ylamino)bicyclo[2.2.1]hept-5-ene-2-carboxylic acid amide in an analogous manner to Example 179. Product isolated as a white solid (35 mg, 20%). LCMS (m/e) 426 (M+1); $^1$H NMR (DMSO-d6, 400 MHz) δ 9.63 (broad s, 1H), 9.27 (broad s, 1H), 8.29 (s, 1H), 8.06 (d, 1H, J=7.8 Hz), 8.00 (s, 1H), 7.44 (s, 1H), 7.03 (t, 1H, J=7.6 Hz), 6.97 (d, 1H, J=7.6 Hz), 6.40 (m, 1H), 6.27 (m, 1H), 3.99 (m, 3H), 2.95 (d, 2H, 11.9 Hz), 2.79 (m, 2H), 2.55 (d, 1H, J=7.8 Hz), 1.96 (m, 3H), 1.67 (m, 2H), 1.43 (d, 1H).

Example 862

5-Chloro-N*4*-(2-methoxy-4-morpholin-4-yl-phenyl)-N*2*-(2,3,4,5-tetrahydrobenzo[b]oxepin-9-yl)pyrimidine-2,4-diamine The title compound was prepared from 2,3,4,5-tetrahydrobenzo[b]oxepin-9-ylamine and (2,5-dichloro-pyrimidin-4-yl)-(2-methoxy-4-morpholin-4-yl-phenyl)-amine in an analogous manner to Example 179. Product was isolated as a light brown solid (51 mg, 40%). LCMS (m/e) 482 (M+H); $^1$H NMR (400 MHz, DMSO-d6) δ 8.88 (broad s, 1H), 8.43 (broad s, 1H), 8.28 (s, 1H), 7.66 (d, 1H, J=8 Hz), 7.37 (d, 1H, J=9 Hz), 6.80 (d, 1H, J=7.58 Hz), 6.71 (s, 1H), 6.67 (dd, 1H, J=7.58, 8 Hz), 6.54 (d, 1H, J=8 Hz), 3.94 (m, 2H), 3.78 (m, 6H), 3.18 (m, 5H), 2.70 (m, 2H), 1.89 (m, 2H), 1.62 (m, 2H).

Example 863

N-{(1R,2R)-2-[5-Chloro-2-(2,3,4,5-tetrahydro-benzo[b]oxepin-9-ylamino)pyrimidin-4-ylamino]-cyclohexyl}-methanesulfonamide The title compound was prepared from 2,3,4,5-tetrahydrobenzo[b]oxepin-9-ylamine and 2-(2,5-dichloro-pyrimidin-4-ylamino)-cyclohexanecarboxylic acid amide in an analogous manner to Example 179. Product was isolated as a tan solid (10 mg, 10%). LCMS (m/e) 466 (M+H); $^1$H NMR (400 MHz, CDCl$_3$) δ 8.17 (d, 1H, J=8.3 Hz), 7.95 (s, 1H), 7.67 (broad s, 1H), 6.97 (t, 1H, J=8 Hz), 6.77 (d, 1H, J=8 Hz), 4.06 (m, 2H), 3.94 (m, 1H), 3.28 (m, 1H), 2.83 (m, 2H), 2.82 (s, 3H), 2.25 (m, 2H), 2.01 (m, 2H), 1.83 (m, 2H), 1.73 (m, 2H), 1.39 (m, 4H).

Example 864

5-Chloro-N*4*-(2-methoxy-phenyl)-N*2*-(2,3,4,5-tetrahydrobenzo[b]oxepin-9-yl)-pyrimidine-2,4-diamine The title compound was prepared from 2,3,4,5-tetrahydrobenzo[b]oxepin-9-ylamine and (2,5-dichloro-pyrimidin-4-yl)-(2-methoxy-phenyl)-amine in analogous manner to Example 179. Product was isolated as a light pink solid (20 mg, 30%). LCMS (m/e) 397 (M+H); $^1$H NMR (DMSO-d6, 400 MHz) δ 8.27 (s, 1H), 8.13 (s, 1H), 8.00 (s, 1H), 7.86 (d, 1H, J=7.3 Hz), 7.72 (d, 1H, J=7.8 Hz), 7.19 (dd, 1H, J=7.3, 8.3 Hz), 7.12 (d, 1H, J=8.3 Hz), 6.94 (td, 1H, J=7.6 Hz), 6.76 (m, 2H), 3.94 (m, 2H), 3.82 (s, 3H), 2.72 (m, 2H), 1.88 (m, 2H), 1.62 (m, 2H).

Example 865

5-Chloro-N*4*-(2-methoxy-4-morpholin-4-yl-phenyl)-N*2*-(7-morpholin-4-yl-6,7,8,9-tetrahydro-5H-benzocyclohepten-2-yl)-pyrimidine-2,4-diamine The title compound was prepared from (2,5-dichloro-pyrimidin-4-yl)-(2-methoxy-4-morpholin-4-yl-phenyl)-amine and 7-Morpholin-4-yl-6,7,8,9-tetrahydro-5H-benzocyclohepten-2-ylamine in an analogous manner as Example 179. Product isolated as a white solid (46 mg, 60%). LCMS (m/e) 565 (M+H); $^1$H NMR (CDCl$_3$, 400 MHz) δ 8.27 (d, 1H, J=7.6 Hz), 8.00 (s, 1H), 7.59 (s, 1H), 7.38 (s, 1H), 7.35 (d, 1H, J=9.3 Hz), 7.04 (d, 1H, J=8.1 Hz), 6.84 (s, 1H), 6.55 (s, 1H), 6.51 (d, 1H, J=9.3 Hz), 3.92 (s, 3H), 3.90 (m, 5H), 3.69 (m, 4H), 3.16 (m, 4H), 2.81 (2H, m), 2.67 (2H, m), 2.55 (m, 4H), 2.08 (m, 2H), 1.44 (m, 2H).

Example 866

2-[5-Chloro-2-(7-morpholin-4-yl-6,7,8,9-tetrahydro-5H-benzocyclohepten-2-ylamino)-pyrimidin-4-ylamino]-N-ethyl-benzamide The title compound was prepared from 2-(2,5-dichloro-pyrimidin-4-ylamino)-N-ethyl-benzamide and 7-morpholin-4-yl-6,7,8,9-tetrahydro-5H-benzocyclohepten-2-ylamine in an analogous manner to Example 179. Product was isolated as a tan solid (30 mg, 40%). LCMS (m/e) 521 (M+H); $^1$H NMR (400 MHz, DMSO-d6) δ 11.04 (s, 1H), 8.65 (d, 1H, J=8.3 Hz), 8.04 (s, 1H), 7.52 (broad s, 1H), 7.50 (d, 1H, J=7.6 Hz), 7.43 (dd, 1H, J=8.1, 7.6 Hz), 7.37 (s, 1H), 7.29 (s, 1H), 7.09 (t, 1H, J=7.6), 7.04 (d, 1H, J=8.1 Hz), 6.16 (broad s, 1H), 3.71 (s, 4H), 3.52 (m, 3H), 2.63-2.85 (m, 4H), 2.58 (s, 4H), 2.8 (m, 2H), 1.42 (m, 2H), 1.27 (t, 3H, J=7.3 Hz).

Example 867

3-[5-Chloro-2-(7-morpholin-4-yl-6,7,8,9-tetrahydro-5H-benzocyclohepten-2-ylamino)-pyrimidin-4-ylamino]-bicyclo[2.2.1]hept-5-ene-2-carboxylic acid amide The title compound was prepared from 7-morpholin-4-yl-6,7,8,9-tetrahydro-5H-benzocyclohepten-2-ylamine and 3-(2,5-dichloro-pyrimidin-4-ylamino)-bicyclo[2.2.1]hept-5-ene-2-carboxylic acid amide in an analogous manner to Example 179. Product was isolated as a tan solid. LCMS (m/e) 510 (M+H); $^1$H NMR (400 MHz, DMSO-d6) δ 9.11 (s, 1H), 7.93 (s, 1H), 7.78 (s, 1H), 7.71 (d, 1H, J=6.8 Hz), 7.53 (d, 1H, 8.86 Hz), 7.41 (s, 1H), 7.26 (s, 1H), 7.00 (d, 1H, J=8.3 Hz), 6.31 (m, 1H), 6.28 (m, 1H), 4.13 (t, 1H, J=8 Hz), 3.54 (s, 4H), 2.88 (s, 1H), 2.46-2.78 (m, 11H), 2.11 (d, 1H, J=9 Hz), 1.95 (m, 2H), 1.41 (d, 1H, J=9 Hz), 1.31 (m, 2H).

Example 868

2-[5-Chloro-2-(1-methoxy-7-oxo-6,7,8,9-tetrahydro-5H-benzocyclohepten-2-ylamino)-pyrimidin-4-ylamino]-N-methyl-benzamide 868a) 1-Methoxy-2,3-dimethyl-benzene (40.00 g, 0.2937 mol) and N-bromosuccinimide (104.6 g, 0.5877 mol) and 2,2'-azo-bis-isobutyronitrile (2 g, 0.01 mol) were dissolved in carbon tetrachloride (800 mL, 8 mol). The reaction was heated to reflux and was allowed to stir overnight. The reaction mixture was cooled and the solids were filtered. The filtrate was then washed with saturated sodium bicarbonate and extracted with dichloromethane. Combined organic layers were dried over sodium sulfate filtered and concentrated in vacuo to give 1,2-Bis-bromomethyl-3-methoxybenzene (86 g, 99%) which was used without further purification. $^1$H NMR (400 MHz, CDCl$_3$) δ7.23 (t, 1H, J=8.05 Hz), 6.96 (d, 1H, J=7.64 Hz), 6.86 (d, 1H, J=8.36 Hz), 4.77 (s, 2H), 4.61 (s, 2H), 3.89 (s, 3H).

868b) To a 5 Liter flask was added tetra-n-butylammonium iodide (30 g, 0.09 mol) in 0.6 M of sodium bicarbonate in water (1250 mL) and methylene chloride (500 mL, 7 mol). The reaction mixture was cooled at 0° C. and a solution of 1,2-bis-bromomethyl-3-methoxybenzene (43.0 g, 0.146 mol) and 3-oxopentanedioic acid, diethyl ester (34.6 mL, 0.190 mol) in methylene chloride (120 mL, 1.9 mol) was added slowly dropwise via addition funnel to the reaction mixture. Following complete addition of the contents of the dropping funnel, the reaction mixture was stirred vigorously at room temperature overnight. The mixture was transferred in batches to a separatory funnel where the layers were separated. The aqueous layer was washed with additional methylene chloride, extracts combined, dried over magnesium sulfate, filtered and concentrated in vacuo to a dark oil. The oil was triturated with diethyl ether and a solid (tetrabutylammonium salts) precipitated out of solution and removed by filtration. The filtrate was concentrated in vacuo to 1-methoxy-7-oxo-6,7,8,9-tetrahydro-5H-benzocyclohepten-6,8-dicarboxylic acid diethyl ester as a dark oil which was used without purification.

868c) A stirred solution of 1-methoxy-7-oxo-6,7,8,9-tetrahydro-5H-benzocyclo-heptene-6,8-dicarboxylic acid diethyl ester (80 g, 0.2 mol) in ethanol (1500 mL, 26 mol) and aqueous potassium hydroxide (1M, 950 mL) was heated to reflux for 3 h. After 3 h, the mixture was cooled to room temperature, quenched with 1 N HCl and concentrated in batches to remove ethanol. The mixture was then extracted with methylene chloride, dried over magnesium sulfate, filtered and concentrated in vacuo to a dark brown-black oil. The product was purified by ISCO purification on silica gel using hexane-ethyl acetate. The product, 1-methoxy-5,6,8,9-tetrahydrobenzocyclohepten-7-one, was crystallized out of ethyl acetate-hexane as a yellow solid. $^1$H NMR (400 MHz, CDCl3) δ 7.16 (t, 1H, J=7.58 Hz), 6.83 (dd, 2H), 3.83 (s, 3H), 3.01 (m, 2H), 2.91 (m, 2H), 2.59 (m, 4H).

868d) To a stirred solution of 1-methoxy-5,6,8,9-tetrahydro-benzocyclohepten-7-one (0.80 g, 0.0042 mol) in acetonitrile (5 mL, 0.1 mol) at 0° C. was added trifluoroacetic anhydride (2 mL, 0.01 mol). Potassium nitrate (0.42 g, 0.0042 mol) was then added to the reaction mixture and the contents stirred at room temperature for 2 h. Two nitration products were observed. Workup involved diluted the reaction mixture with ethyl acetate and washing with water. The organic phase was dried over magnesium sulfate, filtered and concentrated in vacuo. Purification by ISCO chromatography on silica gel using hexane-ethyl acetate yielded both nitration products which were confirmed by NMR NOE studies. The desired product 1-methoxy-2-nitro-5,6,8,9-tetrahydrobenzocyclohepten-7-one was isolated as a white solid. $^1$H NMR (400 MHz; CDCl3) δ 2.64 (m, 4H), 2.99 (m, 2H), 3.07 (m, 2H), 3.90 (s, 3H), 7.13 (d, 1H, J=8.34 Hz), 7.71 (d, 1H, J=8.33 Hz).

868e) To a stirred solution of 1-methoxy-2-nitro-5,6,8,9-tetrahydro-benzocyclohepten-7-one (400 mg, 0.002 mol) in tetrahydrofuran (10 mL, 0.1 mol) was added dichlorodihydrostannane (600 mg, 0.003 mol) in 12 M of hydrogen chloride in water (8 mL) over 15 min. The mixture was stirred at room temperature for 36 h. The reaction mixture was concentrated in vacuo, diluted with water (4 mL) and made basic with 10 N NaOH. A solid precipitated out of solution and was removed by filtration through celite. The solid was washed with chloroform and the organic layer dried over magnesium sulfate, filtered and concentrated in vacuo to a yellow solid. The solid was triturated with diethyl ether and collected by filtration to give 2-amino-1-methoxy-5,6,8,9-tetrahydrobenzocyclohepten-7-one as a tan solid (200 mg, 60%). $^1$H NMR (400 MHz, CDCl3) δ 6.82 (d, 1H, J=7.8 Hz), 6.61 (d, 1H, J=7.8 Hz), 3.77 (broad s, 2H), 3.72 (s, 3H), 2.96 (m, 2H), 2.81 (m, 2H), 2.58 (m, 4H).

868f) The title compound was prepared from 2-amino-1-methoxy-5,6,8,9-tetrahydro-benzocyclohepten-7-one and 2-(2,5-dichloro-pyrimidin-4-ylamino)-N-methyl-benzamide in an analogous manner as Example 179. Product was isolated as an off-white solid (12 mg, 20%). LCMS (m/e) 466 (M+H); $^1$H NMR (400 MHz, DMSO-d6) δ 11.07 (s, 1H), 8.68 (d, 1H, J=8.8 Hz), 8.17 (d, 1H, J=8.34 Hz), 8.13 (s, 1H), 7.50 (m, 2H), 7.42 (s, 1H), 7.11 (t, 1H), 6.96 (d, 1H, J=8.34 Hz), 6.23 (broad s, 1H), 3.76 (s, 3H), 3.04 (d, 3H, J=4.8 Hz), 3.01 (m, 2H), 2.89 (m, 2H), 2.62 (m, 4H).

Example 869

(1S,2S,3R,4R)-3-[5-Chloro-2-(1-methoxy-7-oxo-6,7,8,9-tetrahydro-5H-benzocyclohepten-2-ylamino)-pyrimidin-4-ylamino]-bicyclo[2.2.1]hept-5-ene-2-carboxylic acid amide The title compound was prepared from 2-amino-1-methoxy-5,6,8,9-tetrahydro-benzocyclohepten-7-one and (1S,2S,3R,4R)-3-(2,5-dichloro-pyrimidin-4-ylamino)-bicyclo[2.2.1]hept-5-ene-2-carboxylic acid amide in an analogous manner to Example 179. Product was prepared as a white solid (18 mg, 30%). LCMS (m/e) 468 (M+H); $^1$H NMR (400 MHz, DMSO-d6) δ 8.05 (d, 1H, J=8.1 Hz), 7.96 (s, 1H), 7.93 (d, 1H, J=7.1), 7.82 (s, 1H), 7.81 (d, 1H), 7.281 (s, 1H), 7.04 (d, 1H, J=8.2 Hz), 6.35 (m, 1H), 6.29 (m, 1H), 4.03 (m, 1H), 3.67 (s, 3H), 3.29 (s, 2H), 2.95 (m, 2H), 2.89 (m, 4H), 2.67 (m, 1H), 2.53 (m, 2H), 2.09 (d, 1H, J=9 Hz), 1.40 (d, 1H, J=9 Hz).

Example 870

(1R,2R,3S,4S)-3-[5-Chloro-2-(5,5-dimethyl-2,3,4,5-tetrahydro-benzo[b]oxepin-9-ylamino)-pyrimidin-4-ylamino]-bicyclo[2.2.1]hept-5-ene-2-carboxylic acid amide 870a) 5,5-Dimethyl-2,3,4,5-tetrahydrobenzo[b]oxepin-9-ylamine was prepared from 4-bromo-2-methyl-2-butene and 2-nitrophenol in an analogous manner to Example 861. Product was isolated as a purple solid. $^1$H NMR (400 MHz, CDCl$_3$) δ 6.83 (t, 1H, J=7.8 Hz), 6.67 (d, 1H, J=7.8 Hz), 6.63 (d, 1H, J=7.8 Hz), 3.96 (m, 2H) 3.85 (broad s, 2H), 2.05 (m, 2H), 1.67 (m, 2H), 1.36 (s, 6H).

870b) The title compound was prepared from 5,5-dimethyl-2,3,4,5-tetrahydro-benzo[b]oxepin-9-ylamine and (2-exo, 3-exo)-3-(2,5-dichloro-pyrimidin-4-ylamino)-bicyclo[2.2.1]hept-5-ene-2-carboxylic acid amide in an analogous manner to Example 179. Product was isolated as a whitish-pink solid (18 mg, 20%). LCMS (m/e) 454 (M+H); $^1$H NMR (400 MHz, CDCl3) δ 8.40 (d, 1H, J=8 Hz), 7.90 (s, 1H), 7.77 (s, 1H), 6.94 (t, 1H, J=8 Hz), 6.91 (t, 1H, J=8 Hz), 6.37 (m, 1H), 6.31 (m, 1H), 5.62 (broad s, 1H), 5.42 (broad s, 1H), 4.38 (t, 1H, J=8 Hz), 4.02 (m, 2H), 3.06 (s, 1H), 2.94 (s, 1H), 2.50 (d, 1H, J=8 Hz), 2.24 (d, 1H, J=9 Hz), 2.07 (m, 2H), 1.69 (t, 2H, J=6 Hz), 1.62 (d, 2H, J=8 Hz), 1.39 (s, 6H).

Example 871

2-[5-Chloro-2-(1-methyl-2-oxo-2,3,4,5-tetrahydro-1H-benzo[b]azepin-7-ylamino)-pyrimidin-4-ylamino]-N-(2-cyano-ethyl)-benzamide The title compound was prepared from 7-amino-1-methyl-1,3,4,5-tetrahydro-1-benzazepin-2-one and N-(2-cyano-ethyl)-2-(2,5-dichloro-pyrimidin-4-ylamino)-benzamide in an analogous manner to Example 179. Product was isolated as a tan solid (20 mg, 30%). LCMS (m/e) 490 (M+H); $^1$H NMR (400 MHz, DMSO-d6) δ 11.36 (s, 1H), 9.53 (s, 1H), 9.14 (m, 1H), 8.72 (d, 1H, J=8.6 Hz), 8.25 (s, 1H), 7.79 (d, 1H, J=7.8 Hz), 7.59 (s, 1H), 7.30 (m, 2H), 7.53 (m, 1H), 7.20 m, 2H), 3.54 (q, 2H, J=6 Hz), 3.21 (s, 3H), 2.81 (t, 2H, J=6 Hz), 2.56 (m, 2H), 2.15 (m, 2H), 2.03 (m, 2H).

Example 872

5-Chloro-N*2*-(5,5-dimethyl-2,3,4,5-tetrahydro-benzo[b]oxepin-9-yl)-N*4*-[2-methoxy-4-(4-methyl-piperazin-1-yl)-phenyl]-pyrimidine-2,4-diamine The title compound was prepared from 5,5-dimethyl-2,3,4,5-tetrahydro-benzo[b]oxepin-9-ylamine and (2,5-dichloro-pyrimidin-4-yl)-[2-methoxy-4-(4-methyl-piperazin-1-yl)-phenyl]-amine in the analogous manner to Example 179. Product was isolated as a tan solid (12 mg, 10%). LCMS (m/e) 523 (M+H); $^1$H NMR δ 8.28 (d, 1H, J=7.8 Hz), 8.21 (d, 1H, J=9.1 Hz), 8.03 (s, 1H), 7.74 (s, 1H), 7.48 (s, 1H), 6.89-6.97 (m, 2H), 6.58 (s, 2H), 4.01 (m, 2H), 3.90 (s, 3H), 3.22 (m, 4H), 2.61 (m, 4H), 2.38 (s, 3H), 2.07 (m, 2H), 1.69 (m, 2H), 1.39 (s, 6H).

Example 873

2-[5-Chloro-2-(5,5-dimethyl-2,3,4,5-tetrahydro-benzo[b]oxepin-9-ylamino)-pyrimidin-4-ylamino]-N-ethyl-benzamide The title compound was prepared from 5,5-dimethyl-2,3,4,5-tetrahydro-benzo[b]oxepin-9-ylamine and 2-(2,5-dichloro-pyrimidin-4-ylamino)-N-ethyl-benzamide in an analogous manner to Example 179. The product was isolated as a light brown solid (40 mg, 40%). LCMS (m/e) 466 (M+H); $^1$H NMR (400 MHz, CDCl$_3$) δ 10.93 (s, 1H), 8.67 (d, 1H, J=8.6 Hz), 8.29 (d, 1H, J=7.8 Hz), 8.12 (s, 1H), 7.79 (s, 1H), 7.50 (m, 2H), 7.10 (t, 1H, J=7.6 Hz), 6.94 (m, 2H), 6.13 (m, 1H), 4.02 (t, 2H, J=4.5, 5.1 Hz), 3.52 (m, 2H), 2.08 (m, 2H), 1.70 (t, 2H, 5.6, 6.1 Hz), 1.39 (s, 6H) 1.27 (t, 3H, J=7.3 Hz).

Example 874

2-[5-Chloro-2-(5,5-dimethyl-2,3,4,5-tetrahydro-benzo[b]oxepin-9-ylamino)-pyrimidin-4-ylamino]-N-ethyl-3-fluoro-benzamide The title compound was prepared from 5,5-dimethyl-2,3,4,5-tetrahydro-benzo[b]oxepin-9-ylamine and 2-(2,5-dichloro-pyrimidin-4-ylamino)-N-ethyl-3-fluoro-benzamide in an analogous manner to Example 179. Product isolated as a tan solid (30 mg, 30%). LCMS (m/e) 484 (M+H); $^1$H NMR (400 MHz, CDCl3) δ 8.52 (s, 1H), 8.08 (s, 1H), 7.92 (d, 1H, J=8 Hz), 7.78 (s, 1H), 7.33 (m, 3H), 6.84 (d, 1H, J=7.8 Hz), 6.74 (t, 1H, J=8, 7.8 Hz), 6.05 (m, 1H), 3.96 (m, 2H), 3.38 (m, 2H), 2.04 (m, 2H), 1.66 (m, 2H) 1.34 (s, 6H), 1.11 (t, 3H, J=7.3 Hz).

Example 875

N-{(1R,2R)-2-[5-Chloro-2-(5,5-dimethyl-2,3,4,5-tetrahydro-benzo[b]oxepin-9-ylamino)-pyrimidin-4-ylamino]-cyclohexyl}-methanesulfonamide The title compound was prepared from 5,5-dimethyl-2,3,4,5-tetrahydro-benzo[b]oxepin-9-ylamine and N-[(1R,2R)-

2-(2,5-dichloro-pyrimidin-4-ylamino)-cyclohexyl]-methanesulfonamide in an analogous manner to Example 179. Product was isolated as a tan foam (51 mg, 50%). LCMS (m/e) 494 (M+H); $^1$H NMR (400 MHz, CDCl3) δ 8.22 (d, 1H, J=7.8 Hz), 7.96 (s, 1H), 7.72 (s, 1H), 7.01 (dd, 1H, J=7.8, 7.58 Hz), 6.93 (d, 1H, J=8 Hz), 5.42 (m, 1H), 5.24 (m, 1H), 4.02 (m, 2H), 3.93 (m, 1H), 3.27 (m, 1H), 2.80 (s, 3H), 2.24 (m, 2H), 2.08 (m, 2H), 1.84 (m, 2H), 1.69 (m, 2H), 1.39 (s, 9H).

Example 876

5-Chloro-N*2*-(5,5-dimethyl-2,3,4,5-tetrahydro-benzo[b]oxepin-9-yl)-N*4*-(2-methoxy-4-morpholin-4-yl-phenyl)-pyrimidine-2,4-diamine The title compound was prepared from 5,5-dimethyl-2,3,4,5-tetrahydro-benzo[b]oxepin-9-ylamine and (2,5-dichloro-pyrimidin-4-yl)-(2-methoxy-4-morpholin-4-yl-phenyl)-amine in an analogous manner to Example 179. Product was isolated as a tan solid (78 mg, 80%). LCMS (m/e) 510 (M+H); $^1$H NMR (400 MHz, DMSO-d6) δ 8.23 (s, 1H), 8.06 (s, 1H), 7.82 (m, 2H), 7.46 (dm, 1H, J=9 Hz), 6.84 (d, 1H, J=8 Hz), 6.75 (t, 1H, J=8 Hz), 6.68 (s, 1H), 6.52 (d, 1H, J=9 Hz), 3.91 (m, 2H), 3.77 (d, 7H), 3.16 (m, 4H), 1.96 (m, 2H), 1.60 (m, 2H), 1.30 (s, 6H).

Example 877

2-[5-Chloro-2-(5,5-dimethyl-2,3,4,5-tetrahydro-benzo[b]oxepin-9-ylamino)-pyrimidin-4-ylamino]-N-(2-cyano-ethyl)-benzamide The title compound was prepared from 5,5-dimethyl-2,3,4,5-tetrahydro-benzo[b]oxepin-9-ylamine and N-(2-cyano-ethyl)-2-(2,5-dichloro-pyrimidin-4-ylamino)-benzamide in an analogous manner to Example 179. Product was isolated as a golden brown solid (50 mg, 50%). LCMS (m/e) 491 (M+H); $^1$H NMR (400 MHz, CDCl3) δ 10.78 (s, 1H), 8.69 (d, 1H, J=8.6 Hz), 8.25 (d, 1H, J=7.8 Hz), 8.12 (s, 1H), 7.80 (s, 1H), 7.53 (m, 2H), 7.12 (t, 1H, J=7.8 Hz), 6.95 (m, 2H), 6.74 (m, 1H), 4.01 (t, 2H, J=5 Hz), 3.73 (dd, 2H, J=6, 12 Hz), 2.76 (t, 2H, J=6 Hz), 2.08 (m, 2H), 1.69 (t, 2H, J=6 Hz), 1.40 (s, 6H).

Example 878

5-Chloro-N*2*-(5,5-dimethyl-2,3,4,5-tetrahydro-benzo[b]oxepin-9-yl)-N*4*-[2-(propane-2-sulfonyl)-phenyl]-pyrimidine-2,4-diamine The title compound was prepared from 5,5-dimethyl-2,3,4,5-tetrahydro-benzo[b]oxepin-9-ylamine and (2,5-dichloro-pyrimidin-4-yl)-[2-(propane-2-sulfonyl)-phenyl]-amine in an analogous manner to Example 179. Product was isolated as a tan foam (42 mg, 70%). LCMS (m/e) 501 (M+H); $^1$H NMR (400 MHz, CDCl3) δ 9.53 (s, 1H), 8.58 (d, 1H, J=8.3 Hz), 8.20 (dd, 1H, J=5 Hz), 8.17 (s, 1H), 7.92 (d, 1H, J=7.8 Hz); 7.85 (s, 1H), 7.66 (dd, 1H, J=7.8, 8.6 Hz), 7.28 (m, 1H), 6.95 (m, 2H), 4.03 (t, 2H, J=5 Hz), 3.24 (m, 1H), 2.08 (m, 2H), 1.70 (m, 2H), 1.39 (s, 6H), 1.31 (d, 6H, J=6.8 Hz).

Example 879

5-Chloro-N*2*-(5,5-dimethyl-2,3,4,5-tetrahydro-benzo[b]oxepin-9-yl)-N*4*-[2-(1-methyl-1H-imidazol-2-yl)-phenyl]-pyrimidine-2,4-diamine The title compound was prepared from 5,5-dimethyl-2,3,4,5-tetrahydro-benzo[b]oxepin-9-ylamine and (2,5-dichloro-pyrimidin-4-yl)-[2-(1-methyl-1H-imidazol-2-yl)-phenyl]-amine in an analogous manner to Example 179 heating at 130° C. Product was isolated as a pink foam (42 mg, 57%). LCMS (m/e) 475 (M+H); $^1$H NMR (400 MHz, CDCl$_3$) δ 10.66 (s, 1H), 8.60 (d, 1H, J=8.3 Hz), 8.32 (d, 1H, J=7.8 Hz), 8.05 (s, 1H), 7.78 (s, 1H), 7.43 (m, 2H), 7.21 (m, 2H), 6.95 (m, 3H), 4.01 (m, 2H), 3.76 (s, 3H), 2.07 (m, 2H), 1.69 (m, 2H), 1.39 (s, 6H).

Example 880

{2-[5-Chloro-2-(5,5-dimethyl-2,3,4,5-tetrahydro-benzo[b]oxepin-9-ylamino)-pyrimidin-4-ylamino]-phenoxy}-acetonitrile The title compound was prepared from 5,5-dimethyl-2,3,4,5-tetrahydro-benzo[b]oxepin-9-ylamine and [2-(2,5-dichloro-pyrimidin-4-ylamino)-phenoxy]-acetonitrile in an analogous manner to Example 179 heating at 130° C. Product was isolated as a white solid (26 mg, 34%). LCMS (m/e) 450 (M+H); $^1$H NMR (400 MHz, CDCl3) δ 10.58 (broad s, 1H), 8.15 (s, 1H), 8.08 (d, 1H, J=8.1 Hz), 7.93 (s, 1H), 7.55 (d, 1H, J=7.6 Hz), 7.19 (m, 2H), 7.03 (d, 1H, J=8.34 Hz), 6.97 (m, 2H), 4.88 (s, 2H), 4.02 (m, 2H), 2.01 (m, 2H), 1.67 (m, 2H), 1.37 (s, 6H).

Example 881

(1S,2S,3R,4R)-3-[5-Chloro-2-((R)-1-methoxy-7-morpholin-4-yl-6,7,8,9-tetrahydro-5H-benzocyclohepten-2-ylamino)-pyrimidin-4-ylamino]-bicyclo[2.2.1]hept-5-ene-2-carboxylic acid amide 881a) To a stirred solution of 1-methoxy-2-nitro-5,6,8,9-tetrahydro-benzocyclohepten-7-one (236 mg, 0.00100 mol) in 1,2-dichloroethane (8 mL, 0.1 mol) at room temperature was added morpholine (0.23 mL, 0.0026 mol) followed by acetic acid (0.15 mL, 0.0026 mol) dropwise. The reaction mixture was stirred at room temperature for 2 h. The reaction mixture was cooled to 0° C. and sodium triacetoxyborohydride was added in one portion. The reaction mixture was stirred at 0° C. for 2 h then warmed to room temperature overnight. Workup involved addition of 1N NaOH to bring pH to ~10. The reaction mixture was extracted with ethyl acetate, washed with water and brine, dried over magnesium sulfate, filtered and concentrated in vacuo to a orange oil. Purification was accomplished using ISCO chromatography on silica gel using hexane-ethyl acetate and methylene chloride-methanol to give 4-(1-methoxy-2-nitro-6,7,8,9-tetrahydro-5H-benzocyclohepten-7-yl)-morpholine as a yellow solid (0.24 g, 78%). $^1$H NMR (400 MHz, CDl$_3$). δ 6.70 (s, 1H, J=7.92 Hz), 6.51 (d, 1H, J=7.88), 3.70 (m, 9H), 3.29 (q, 1H, J=14.41, 8 Hz), 2.74 (q, 1H, J=14.28, 7.48 Hz), 2.55 (m, 6H), 2.31 (m, 1H), 2.10 (m, 2H), 1.35 (m, 2H).

881b) 4-(1-Methoxy-2-nitro-6,7,8,9-tetrahydro-5H-benzocyclohepten-7-yl)-morpholine (0.24 g, 0.00078 mol) was dissolved in ethanol (40 mL, 0.7 mol) and placed in a Parr bottle. To this solution was added palladium on carbon (10 mg). The reaction mixture was placed under 50 psi of hydrogen and shaken overnight. The mixture was filtered through celite and washed with additional ethanol (40 mL). The filtrate was concentrated in vacuo. The film was triturated with diethyl ether to provide 1-methoxy-7-morpholin-4-yl-6,7,8,9-tetrahydro-5H-benzocyclohepten-2-ylamine as a solid (0.21 g, 97%). $^1$H NMR (400 MHz, CDCl$_3$) δ 6.71 (d, 1H, J=7.84 Hz), 6.51 (d, 1H, J=7.83 Hz), 3.70 (s, 7H), 3.31 (m, 1H), 2.75 (m, 1H), 2.60 (m, 2H), 2.55 (s, 4H), 2.31 (m, 1H), 2.0-2.16 (m, 2H), 1.37 (m, 2H).

881c) The title compound was prepared from 1-methoxy-7-morpholin-4-yl-6,7,8,9-tetrahydro-5H-benzocyclohepten-2-ylamine and (1S,2S,3R,4R)-3-(2,5-dichloro-pyrimidin-4-ylamino)-bicyclo[2.2.1]hept-5-ene-2-carboxylic acid amide in an analogous manner to Example 179. Product was isolated as tan solid (36 mg, 33%). LCMS (m/e) 539 (M+H), $^1$H NMR (CDCl$_3$, 400 MHz) δ 8.02 (d, 1H, J=8.3 Hz), 7.81 (s, 1H), 6.88 (d, 1H, J=8.3 Hz), 6.31 (m, 1H), 6.25 (m, 1H), 5.85 (s, 1H), 5.55 (s, 1H), 4.19 (t, 1H, J=7.3 Hz), 3.01 (s, 4H), 3.72 (s, 3H), 3.49 (m, 2H), 3.07-3.15 (m, 4H), 2.91 (m, 2H), 2.76 (m, 1H), 2.38-2.47 (m, 3H), 2.18 (d, 1H, J=9.6 Hz), 1.61 (d, 1H, J=9.3 Hz), 1.48 (m, 2H).

Example 882

(1S,2S,3R,4R)-3-[5-Chloro-2-((S)-1-methoxy-7-morpholin-4-yl-6,7,8,9-tetrahydro-5H-benzocyclohepten-2-ylamino)-pyrimidin-4-ylamino]-bicyclo[2.2.1]hept-5-ene-2-carboxylic acid amide 882a) The title compound was prepared from 1-methoxy-7-morpholin-4-yl-6,7,8,9-tetrahydro-5H-benzocyclohepten-2-ylamine and (1S,2S,3R,4R)-3-(2,5-dichloro-pyrimidin-4-ylamino)-bicyclo[2.2.1]hept-5-ene-2-carboxylic acid amide in an analogous manner to Example 881 heating at 140° C. Product was isolated as an off-white solid (43 mg, 39%). LCMS (m/e) 539 (M+H); $^1$H NMR (CDCl$_3$, 400 MHz) δ 8.16 (d, 1H, J=8.1 Hz), 7.86 (s, 1H), 7.41 (broad s, 1H), 6.88 (d, 1H, J=8.3 Hz), 6.31 (s, 2H), 5.81 (s, 1H), 5.62 (s, 1H), 4.27 (t, 1H, J=8.1 Hz), 3.97 (s, 4H), 3.72 (s, 3H), 3.39-3.54 (m, 2H), 3.08 (m, 4H), 2.88 (m, 2H), 2.75 (dd, 1H, J=11.9, 14.2 Hz), 2.49 (d, 1H, J=8.1 Hz), 2.42 (m, 3H), 2.20 (d, 1H, J=9.4 Hz), 1.61 (d, 1H, J=8.3 Hz), 1.50 (m, 2H).

Alternatively the title compound can be prepared from (S)-1-Methoxy-7-morpholin-4-yl-6,7,8,9-tetrahydro-5H-benzocyclohepten-2-ylamine using the procedures outlined above. (S)-1-Methoxy-7-morpholin-4-yl-6,7,8,9-tetrahydro-5H-benzocyclohepten-2-ylamine is prepared from racemic 1-methoxy-7-morpholin-4-yl-6,7,8,9-tetrahydro-5H-benzocyclohepten-2-ylamine by resolution using SFC chromatography on a Chiralcel OJ-H (2×25 cm) column using 12% isopropanol/CO2 (0.1% DEA) or by the following methods.

882b) N—((S)-4-Chloro-1-methoxy-2-nitro-9-oxo-6,7,8,9-tetrahydro-5H-benzocyclohepten-7-yl)-acetamide (100 mg; 0.3 mmol), of Example 632f, in Methanol (10 mL) was treated with Sodium tetrahydroborate (30 mg, 0.8 mmol) neat at rt. After 15 minutes, a second portion of Sodium tetrahydroborate (30 mg, 0.8 mmol) was added to the reaction mixture. After 30 minutes the reaction mixture was treated with water, then extract with Et$_2$O followed by CH$_2$Cl$_2$ (2×). The aqueous phase was treated with 1N KOH and re-extracted with CH$_2$Cl$_2$. The organics were combined, dried over MgSO$_4$, filtered and concentrated to give 210 mg (TW 100 mg) of whitish, crude N—((S)-4-Chloro-9-(R,S)-hydroxy-1-methoxy-2-nitro-6,7,8,9-tetrahydro-5H-benzocyclohepten-7-yl)-acetamide, which was used without further purification; MS (m/e) 328.97 (M+H).

882c) A mixture of the crude N—((S)-4-Chloro-9-(R,S)-hydroxy-1-methoxy-2-nitro-6,7,8,9-tetrahydro-5H-benzocyclohepten-7-yl)-acetamide and 6 M of Hydrogen Chloride in Water (15 mL) were warmed to 95° C. for 3 days. The reaction mixture was then cooled and treated slowly with 30% aqueous NaOH. When the pH proved >10, the reaction mixture was extracted with Et$_2$O (3×). The organic phases were combined, dried over Na$_2$SO$_4$, filtered and concentrated under reduced pressure. The resulting residue was dissolved in CH$_2$Cl$_2$, dried over Na$_2$SO$_4$, filtered, and then chromatographed on a normal phase column eluting with a gradient of 100% CH$_2$Cl$_2$ to 5:1 CH$_2$Cl$_2$:MeOH to give 42 mg (50% over two steps) of (S)-4-Chloro-1-methoxy-2-nitro-6,7-dihydro-5H-benzocyclohepten-7-ylamine as an oil, which was used for subsequent steps without further manipulation. $^1$H NMR (400 MHz, CDCl$_3$) δ 7.79 (s, 1H), 6.68 (d, J=12.37 Hz, 1H), 6.23-6.19 (dd, J=4.29 Hz, 11.98 Hz, 1H), 3.89 (s, 3H), 3.56 (m, 1H), 3.15 (m, 1H), 2.74-2.66 (m, 1H), 2.28 (m, 1H), 2.01 (m, 1H); MS (m/e) weak parent at 269 (M+H).

882d) Under N$_2$, a mixture of (S)-4-Chloro-1-methoxy-2-nitro-6,7-dihydro-5H-benzocyclohepten-7-ylamine (42.0 mg, 0.156 mmol), 1-Bromo-2-(2-bromo-ethoxy)-ethane (120 uL, 0.93 mmol) and Potassium carbonate (64.8 mg, 0.469 mmol) in Acetonitrile (6 mL) was warmed to 80° C. for 16 h. The reaction mixture was then adsorbed directly onto silica gel and chromatographed on a normal phase column eluting with a gradient system (1:1 EtOAc/Hexane-100% EtOAc). The purest fractions were collected and concentrated under reduced pressure to give 12 mg (23%) of clear oil 4-((S)-4-Chloro-1-methoxy-2-nitro-6,7-dihydro-5H-benzocyclohepten-7-yl)-morpholine, which was used directly in the subsequent reaction; $^1$H NMR (400 MHz, CDCl$_3$) δ 7.81 (s, 1H), 6.78 (d, J=11.66 Hz, 1H), 6.37-6.33 (dd, J=4.81 Hz, 11.62 Hz, 1H), 3.89 (s, 3H), 3.74 (s, 4H), 3.09-3.02 (m, 2H), 2.79-2.72 (m, 1H), 2.55 (s, 4H), 2.39-2.34 (m, 1H), 2.13-2.06 (m, 1H); MS (m/e) 339.01 (M+H).

882e) A mixture of 4-((S)-4-Chloro-1-methoxy-2-nitro-6,7-dihydro-5H-benzocyclohepten-7-yl)-morpholine (12 mg, 0.035 mmol) and 20% Pd(OH)$_2$/C (9 mg) in Methanol (4 mL), was placed under a blanket of Hydrogen at atmospheric pressure. After 16 h, the reaction was filtered and concentrated under reduced pressure to give (S)-1-Methoxy-7-morpholin-4-yl-6,7,8,9-tetrahydro-5H-benzocyclohepten-2-ylamine.

Example 883

5-Chloro-N*2*-(1-methoxy-7-morpholin-4-yl-6,7,8,9-tetrahydro-5H-benzocyclohepten-2-yl)-N*4*-[2-(propane-2-sulfonyl)-phenyl]-pyrimidine-2,4-diamine The title compound was prepared from 1-methoxy-7-morpholin-4-yl-6,7,8,9-tetrahydro-5H-benzocyclohepten-2-ylamine and (2,5-dichloro-pyrimidin-4-yl)-[2-(propane-2-sulfonyl)-phenyl]-amine in an analogous manner to Example 179 heating at 140° C. Product was isolated as a white foam (33 mg, 30%). LCMS (m/e) 586 (M+H); $^1$H NMR (400 MHz, CDCl$_3$) δ12.93 (broad s, 1H), 10.32 (broad s, 1H), 8.35 (d, 1H, J=8.34 Hz), 8.00 (s, 1H), 7.91 (d, 1H, J=8.08 Hz), 7.52 (d, 1H, J=8.08 Hz), 7.41 (t, 1H, J=7.58 Hz), 7.33 (t, 1H, J=7.58 Hz), 6.90 (d, 1H, J=8.09 Hz), 4.02 (m, 4H), 3.74 (s, 3H), 3.57 (m, 2H), 3.34 (d, 2H, J=10.9 Hz), 3.20 (m, 2H), 2.94-3.08 (m, 3H), 2.82 (m, 1H), 2.40-2.50 (m, 2H), 1.50 (m, 2H), 1.31 (t, 6H, J=6.31).

Example 884

N-{(1R,2R)-2-[5-Chloro-2-(1-methoxy-7-morpholin-4-yl-6,7,8,9-tetrahydro-5H-benzocyclohepten-2-ylamino)-pyrimidin-4-ylamino]-cyclohexyl}-methanesulfonamide The title compound was prepared from 1-methoxy-7-morpholin-4-yl-6,7,8,9-tetrahydro-5H-benzocyclohepten-2-ylamine and N-[(1R,2R)-2-(2,5-dichloro-pyrimidin-4-ylamino)-cyclohexyl]-methanesulfonamide in an analogous manner as Example 179 heating at 140° C. Product was isolated as a mixture of diastereomers (27 mg, 20%). LCMS (m/e) 579 (M+H); $^1$H NMR (400 MHz, CDCl$_3$) δ 12.40 (s, 1H), 12.2 (s, 1H), 10.8 (s, 1H), 10.6 (s, 1H), 7.92 (s, 1H), 7.88 (s, 1H), 7.48 (d, 1H, J=7.32 Hz), 7.00 (m, 1H), 6.90 (m, 2H), 6.74 (m, 1H), 6.32 (s, 1H), 6.20 (s, 1H), 4.03 (m, 8H), 3.30-3.76 (m, 16H), 2.92-3.08 (m, 13H), 2.76 (m, 2H), 2.33-2.59 (m, 6H), 2.08 (m, 4H), 1.86 (m, 2H), 1.76 (m, 2H), 1.12-1.58 (m, 12H).

Example 885

5-Chloro-N*2*-(5,5-dimethyl-2,3,4,5-tetrahydro-benzo[b]oxepin-9-yl)-N*4*-(2-pyrazol-1-yl-phenyl)-pyrimidine-2,4-diamine The title compound was prepared from (2,5-dichloro-pyrimidin-4-yl)-(2-pyrazol-1-yl-phenyl)-amine and 5,5-dimethyl-2,3,4,5-tetrahydro-benzo[b]oxepin-9-ylamine in an analogous manner to Example 179 heating at 140° C. Product was isolated as a white solid (46 mg, 52%). LCMS=461 (M+H); $^1$H NMR (400 MHz, DMSO-d6) δ 10.55 (s, 1H), 8.61 (s, 1H), 8.28 (s, 1H), 8.24 (s, 1H), 8.16 (d, 1H, J=7.83 Hz), 7.86 (s, 1H), 7.76 (d, 1H, J=7.58 Hz), 7.66 (d, 1H, J=7.83 Hz), 7.41 (m, 2H), 6.98 (d, 1H, J=8.09 Hz), 6.88 (t, 1H, J=8.33 Hz), 6.56 (s, 1H), 3.92 (m, 2H), 1.69 (m, 2H), 1.61 (m, 2H), 1.32 (s, 6H).

Example 886

N-[(1R,2R)-2-(5-Chloro-2-{7-[4-(4-methyl-piperazin-1-yl)-piperidin-1-yl]-6,7,8,9-tetrahydro-5H-benzocyclohepten-2-ylamino}-pyrimidin-4-ylamino)-cyclohexyl]-methanesulfonamide 886a) 1-Methyl-4-[1-(2-nitro-6,7,8,9-tetrahydro-5H-benzocyclohepten-7-yl)-piperidin-4-yl]-piperazine was prepared from 2-nitro-5,6,8,9-tetrahydrobenzocyclohepten-7-one and 1-methyl-4-piperidin-4-yl-piperazine in an analogous manner to Example 178a. Product was isolated as a tan solid. $^1$H NMR (CDCl$_3$, 400 MHz) δ 7.98 (s, 1H), 7.97 (d, 1H, J=8.08 Hz), 7.24 (d, 1H, J=8.08 Hz), 2.95 (dd, 2H, J=7.32, 12 Hz), 2.84 (d, 2H, J=12 Hz), 2.74 (m, 3H), 2.60 (broad s, 4H), 2.47 (m, 3H), 2.29 (s, 5H), 2.11 (m, 2H), 1.82 (d, 2H, J=12 Hz), 1.67 (m, 2H), 1.54 (m, 2H), 1.40 (m, 2H).

886b) 1-Methoxy-7-[4-(4-methyl-piperazin-1-yl)-piperidin-1-yl]-6,7,8,9-tetrahydro-5H-benzocyclohepten-2-ylamine was prepared from 1-Methyl-4-[1-(2-nitro-6,7,8,9-tetrahydro-5H-benzocyclohepten-7-yl)-piperidin-4-yl]-piperazine in an analogous manner to Example 178b. Product was isolated as a light brown solid. $^1$H NMR (CDCl$_3$, 400 MHz) δ 6.89 (d, 1H, J=7.83 Hz), 6.49 (s, 1H), 6.44 (d, 1H, J=7.83 Hz), 3.59 (s, 2H), 2.82 (d, 2H, J=11.4 Hz), 2.59-2.70 (m, 8H), 2.45 (m, 4H), 2.27 (m, 5H), 2.19 (m, 1H), 2.03 (m, 2H), 1.80 (d, 2H, J=11.8 Hz), 1.34 (m, 2H), 1.5.1 (m, 3H), 886c) The title compound was prepared from 7-[4-(4-Methyl-piperazin-1-yl)-piperidin-1-yl]-6,7,8,9-tetrahydro-5H-benzocyclohepten-2-ylamine and N-[2-(2,5-Dichloro-pyrimidin-4-ylamino)-cyclohexyl]-methanesulfonamide in an analogous manner to Example 179 heating at 140° C. Product was isolated as an off-white solid (10 mg, 9%). LCMS (m/e) 645 (M+1); $^1$H NMR (400 MHz, DMSO-d6) δ 9.32 (m, 2H), 7.97 (s, 1H), 7.57 (m, 1H), 7.42 (m, 1H), 7.19 (m, 1H), 7.06 (d, 1H, J=7.8 Hz), 6.95 (m, 1H), 3.38-2.82 (m, 8H), 2.94-3.02 (m, 8H), 2.67-2.77 (m, 8H), 2.33 (m, 2H), 1.95-2.06 (m, 4H), 1.72 (m, 4H), 1.15-1.44 (m, 8H).

Example 887

(1S,2S,3R,4R)-3-(5-Chloro-2-{7-[4-(4-methyl-piperazin-1-yl)-piperidin-1-yl]-6,7,8,9-tetrahydro-5H-benzocyclohepten-2-ylamino}-pyrimidin-4-ylamino)-bicyclo[2.2.1]hept-5-ene-2-carboxylic acid amide The title compound was prepared from 7-[4-(4-methyl-piperazin-1-yl)-piperidin-1-yl]-6,7,8,9-tetrahydro-5H-benzocyclohepten-2-ylamine and (1S,2S,3R,4R)-3-(2,5-Dichloro-pyrimidin-4-ylamino)-bicyclo[2.2.1]hept-5-ene-2-carboxylic acid amide in an analogous manner to Example 179 heating at 140° C. Product was isolated as a tan solid (33 mg, 40%). LCMS (m/e) 605 (M+1); $^1$H NMR (400 MHz, CDCl$_3$) δ 7.86 (s, 1H), 7.38 (dd, 1H, J=7.8 Hz), 7.30 (d, 1H, J=17 Hz), 7.04 (d, 1H, J=8.08 Hz), 6.87 (s, 1H), 6.79 (t, 1H, J=8.08 Hz), 6.33 (m, 1H), 6.30 (m, 1H), 5.59 (s, 1H), 5.43 (s, 1H), 4.37 (t, 1H, J=8.33 Hz), 3.06 (s, 1H), 3.00 (s, 1H), 2.90-2.60 (m, 12H), 2.49-2.38 (m, 5H), 2.27 (s, 4H), 2.19-2.26 (m, 2H), 2.06 (m, 2H), 1.79 (d, 2H, J=11 Hz), 1.63 (d, 1H, J=9.35 Hz), 1.51 (q, 2H, J=11 Hz), 1.38 (m, 2H).

Example 888

N-((1R,2R)-2-{5-Chloro-2-[7-(4-methyl-piperazin-1-yl)-6,7,8,9-tetrahydro-5H-benzocyclohepten-2-ylamino]-pyrimidin-4-ylamino}-cyclohexyl)-methanesulfonamide 888a) 1-Methyl-4-(2-nitro-6,7,8,9-tetrahydro-5H-benzocyclohepten-7-yl)-piper azine was prepared from 2-nitro-5,6,8,9-tetrahydrobenzocyclohepten-7-one and 1-methyl piperazine in a similar manner to Example 178a. Product was isolated as a brown solid.

888b) 7-(4-Methyl-piperazin-1-yl)-6,7,8,9-tetrahydro-5H-benzocyclohepten-2-ylamine was prepared from 1-Methyl-4-(2-nitro-6,7,8,9-tetrahydro-5H-benzocyclohepten-7-yl)-piperazine in a similar manner to Example 178b. Product was isolated as a dark oil that solidified. 1H NMR (CDCl3, 400 MHz) δ 6.91 (d, 1H, J=8.84 Hz), 6.49 (s, 1H), 6.44 (d, 1H, J=8.84 Hz), 3.63 (m, 1H), 2.54-2.75 (m, 6H), 2.31-2.45 (m, 5H), 2.31 (s, 3H), 2.05 (m, 2H), 1.61 (m, 1H), 1.37 (m, 2H).

888c) The title compound was prepared from 7-(4-methyl-piperazin-1-yl)-6,7,8,9-tetrahydro-5H-benzocyclohepten-2-ylamine and N-[(1R,2R)-2-(2,5-Dichloro-pyrimidin-4-ylamino)-cyclohexyl]-methanesulfonamide was prepared in an analogous manner to Example 179 heating to 140° C. Product was isolated as the TFA salt (19 mg, 15%). LCMS (m/e) 562 (M+H); $^1$H NMR (DMSO-d6, 400 MHz) δ 9.33 (s, 1H), 7.98 (s, 1H), 7.56 (d, 1H, J=15 Hz), 7.37 (m, 1H), 7.17 (m, 1H), 7.05 (d, 1H, J=8.33 Hz), 6.98 (broad s, 1H), 3.84 (m, 1H), 3.38 (m, 5H), 2.94 (s, 7H), 2.74 (s, 6H), 2.06 (m, 4H), 1.72 (m, 2H), 1.18-1.39 (m, 8H).

Example 889

2-[5-Chloro-2-(1-methoxy-7-morpholin-4-yl-6,7,8,9-tetrahydro-5H-benzocyclohepten-2-ylamino)-pyrimidin-4-ylamino]-N,N-dimethyl-benzenesulfonamide The title compound was prepared from 2-(2,5-Dichloro-pyrimidin-4-ylamino)-N,N-dimethyl-benzenesulfonamide and 1-methoxy-7-morpholin-4-yl-6,7,8,9-tetrahydro-5H- benzocyclohepten-2-ylamine in an analogous manner to Example 179. Product was isolated as a TFA salt (45 mg, 52%). LCMS (m/e) 587 (M+H); $^1$H NMR (CDCl$_3$, 400 MHz) δ 9.53 (broad s, 1H), 9.42 (s, 1H), 8.55 (d, 1H, J=8.84 Hz), 8.52 (s, 1H), 8.26 (s, 1H), 7.80 (d, 1H, J=7.83 Hz), 7.59 (t, 1H, J=8.34, 7.58 Hz), 7.51 (d, 1H, J=8.08 Hz), 7.33 (t, 1H, J=7.58, 7.83 Hz), 6.92 (d, 1H, J=7.83 Hz), 4.19 (broad s, 4H), 3.99 (d, 2H, J=11.1 Hz), 3.71 (t, 2H, J=11.9 Hz), 3.63 (s, 3H), 3.65 (m, 1H), 3.32 (m, 2H), 3.21 (m, 2H), 2.88 (dd, 1H, J=7.07, 14.1 Hz), 2.76 (t, 1H, J=12.8 Hz), 2.65 (s, 6H), 2.38 (dd, 4H, J=12.6 Hz), 1.46 (p, 2H, J=11.6 Hz).

Example 890

2-{5-Chloro-2-[7-(4-methyl-piperazin-1-yl)-6,7,8,9-tetrahydro-5H-benzocyclohepten-2-ylamino]-pyrimidin-4-ylamino}-N,N-dimethyl-benzenesulfonamide The title compound was prepared from 7-(4-methyl-piperazin-1-yl)-6,7,8,9-tetrahydro-5H-benzocyclohepten-2-ylamine and 2-(2,5-dichloro-pyrimidin-4-ylamino)-N,N-dimethyl-benzenesulfonamide in an analogous manner to Example 179. Product was isolated as a TFA salt (74.6 mg, 90%). $^1$H NMR (DMSO-d6, 400 MHz) δ11.90 (broad s, 2H), 9.65 (s, 1H), 9.38 (s, 1H), 8.42 (broad s, 1H), 8.31 (s, 1H), 7.86 (d, 1H, J=7.83 Hz), 7.73 (t, 1H, J=7.83 Hz), 7.50 (m, 1H), 7.44 (s, 1H), 7.25 (m, 1H), 7.04 (d, 1H, J=8.08 Hz), 3.94 (m, 6H), 3.61-3.72 (m, 4H), 2.92 (s, 4H), 2.69 (m, 2H), 2.65 (s, 6H), 2.43 (m, 2H), 1.44 (m, 2H).

Example 891

5-Chloro-N*4*-(2-methoxy-phenyl)-N*2*-[7-(4-methyl-piperazin-1-yl)-6,7,8,9-tetrahydro-5H-benzocyclohepten-2-yl]-pyrimidine-2,4-diamine The title compound was prepared from 7-(4-methyl-piperazin-1-yl)-6,7,8,9-tetrahydro-5H-benzocyclohepten-2-ylamine and (2,5-dichloro-pyrimidin-4-yl)-(2-methoxy-phenyl)-amine in an analogous manner to Example 179. Product was isolated as a TFA salt (38.2 mg, 42%). $^1$H NMR (CDCl$_3$, 400 MHz) δ11.87 (s, 1H), 8.43 (s, 1H), 8.15 (d, 1H, J=8.09 Hz), 7.82 (s, 1H), 7.44 (s, 1H), 7.37 (d, 1H, =7.83 Hz), 7.24 (m, 1H), 7.10 (d, 1H, J=8.34 Hz), 7.01 (d, 1H, J=8.33 Hz), 6.89 (t, 1H, J=7.83 Hz), 3.96 (s, 3H), 3.4-3.62 (m, 7H), 2.96 (m, 1H), 2.83 (s, 3H), 2.69-2.83 (m, 5H), 2.42 (m, 2H), 1.50 (m, 2H).

Example 892

(1S,2S,3R,4R)-3-{5-Chloro-2-[7-(4-methyl-piperazin-1-yl)-6,7,8,9-tetrahydro-5H-benzocyclohepten-2-ylamino]-pyrimidin-4-ylamino}-bicyclo[2.2.1] hept-5-ene-2-carboxylic acid amide The title compound was prepared from 7-(4-methyl-piperazin-1-yl)-6,7,8,9-tetrahydro-5H-benzocyclohepten-2-ylamine and (1S,2S,3R,4R)-3-(2,5-dichloro-pyrimidin-4-ylamino)-bicyclo[2.2.1]hept-5-ene-2-carboxylic acid amide in an analogous manner to Example 179. Product was isolated as a TFA salt. $^1$H NMR (CDCl$_3$, 400 MHz) δ 7.86 (s, 1H), 7.31-7.39 (m, 2H), 7.04 (d, 1H, J=7.83 Hz), 6.78-6.84 (m, 2H), 6.31 (d, 2H, J=8.84 Hz), 5.57 (s, 1H), 5.37 (s, 1H), 4.38 (t, 1H, J=8.84 Hz), 3.06 (s, 1H), 2.90 (s, 1H), 2.65-2.83 (m, 5H), 2.60 (m, 5H), 2.47 (m, 5H), 2.28 (s, 4H), 2.08 (m, 2H), 1.64 (d, 1H, J=9.1 Hz), 1.41 (m, 2H).

Example 893

(1S,2S,3R,4R)-3-{5-Chloro-2-[7-(4-methyl-piperazin-1-yl)-6,7,8,9-tetrahydro-5H-benzocyclohepten-2-ylamino]-pyrimidin-4-ylamino}-bicyclo[2.2.1] hept-5-ene-2-carboxylic acid amide The title compound was prepared from [2-(2,5-dichloro-pyrimidin-4-ylamino)-phenoxy]-acetonitrile and 1-methyl-4-(2-nitro-6,7,8,9-tetrahydro-5H-benzocyclohepten-7-yl)-piperazine in an analogous manner to Example 179, heating at 130° C. Product was isolated as a tan colored TFA salt (31 mg, 26%). LCMS (m/e) 518; $^1$H NMR (CDCl$_3$, 400 MHz) δ 8.26 (d, 1H, J=7.83 Hz), 7.97 (s, 1H), 7.84 (s, 1H), 7.36 (s, 1H), 7.24 (m, 3H), 7.06 (m, 3H), 4.09 (m, 1H), 3.31 (m, 2H), 3.14 (m, 6H), 2.59-2.90 (m, 11H), 2.26 (m, 2H), 1.43 (m, 2H).

Example 894

5-Chloro-N*4*-(2-methoxy-4-morpholin-4-yl-phenyl)-N*2*-(1-methoxy-7-morpholin-4-yl-6,7,8,9-tetrahydro-5H-benzocyclohepten-2-yl)-pyrimidine-2,4-diamine The title compound was prepared from (2,5-dichloro-pyrimidin-4-yl)-(2-methoxy-4-morpholin-4-yl-phenyl)-amine and 1-methoxy-7-morpholin-4-yl-6,7,8,9-tetrahydro-5H-benzocyclohepten-2-ylamine in an analogous manner to Example 179, heating at 130° C. Product was isolated as a greenish-brown foam (23.4, 18%). LCMS (m/e) 595 (M+H); $^1$H NMR (CDCl$_3$, 400 MHz) δ 8.26 (d, 1H, J=9.6 Hz), 8.05 (d, 1H, J=8.34 Hz), 8.03 (s, 1H), 7.55 (s, 1H), 7.38 (s, 1H), 6.84 (d, 1H, J=8.09 Hz), 6.54 (m, 2H), 3.90 (m, 7H), 3.72 (m, 7H), 3.33 (m, 1H), 3.17 (m, 4H), 2.84 (t, 1H, J=7.32 Hz), 2.58-2.69 (m, 6H), 2.37 (t, 1H, J=12.1 Hz), 2.13 (m, 2H), 1.41 (m, 2H).

Example 895

N-((1R,2R)-2-{5-Chloro-2-[3-methoxy-7-(2-methoxy-ethylamino)-6,7,8,9-tetrahydro-5H-benzocyclohepten-2-ylamino]-pyrimidin-4-ylamino}-cyclohexyl)-methanesulfonamide 895a) (2-Methoxyethyl)-(2-methoxy-3-nitro-6,7,8,9-tetrahydro-5H-benzocyclohepten-7-yl)amine was prepared from 2-methoxy-3-nitro-5,6,8,9-tetrahydrobenzocyclohepten-7-one and 2-methoxyethylamine in a analogous manner to Example 881a. Product was isolated as a brown film. 1H NMR (400 MHz, CDCl$_3$) δ 7.67 (s, 1H), 6.83 (s, 1H), 3.94 (s, 3H), 3.53 (t, 1H, J=14 Hz), 3.37 (s, 6H), 2.83-2.92 (m, 5H), 2.71 (m, 2H), 2.12 (m, 2H), 1.39 (m, 2H).

895b) 3-Methoxy-N*7*-(2-methoxy-ethyl)-6,7,8,9-tetrahydro-5H-benzocycloheptene-2,7-diamine was prepared from (2-methoxyethyl)-(2-methoxy-3-nitro-6,7,8,9-tetrahydro-5H-benzocyclohepten-7-yl)amine in an analogous manner to Example 881b.

895c) The title compound was prepared from N(7)-(2-methoxyethyl)-6,7,8,9-tetrahydro-5H-benzocycloheptene-2,7-diamine and N[(1R,2R)-2-(2,5-dichloropyrimidin-4-ylamino)-cyclohexyl]methanesulfonamide in an analogous manner to Example 179. Product was prepared as a TFA salt (16.6 mg, 21%). LCMS (m/e) 567 (M+H); $^1$H NMR (400 MHz, CDCl$_3$) 9.89 (broad s, 1H), 9.03 (broad s, 1H), 8.03 (s, 1H), 7.54 (broad s, 1H), 7.20 (s, 2H), 6.46 (s, 1H), 3.82 (s, 1H), 3.67 (s, 5H), 3.36 (m, 5H), 3.19 (s, 2H), 3.02 (s, 3H), 2.61-2.86 (m, 4H), 2.34 (m, 2H), 2.17 (m, 1H), 2.08 (d, 1H, J=11.37 Hz), 1.85 (d, 1H, J=12.3 Hz), 1.72 (m, 1H), 1.59 (m, 3H), 1.32 (m, 1H), 1.13 (m, 2H).

Example 896

N-((1R,2R)-2-{5-Chloro-2-[3-methoxy-7-(2-methoxy-ethylamino)-6,7,8,9-tetrahydro-5H-benzocyclohepten-2-ylamino]-pyrimidin-4-ylamino}-cyclohexyl)-methanesulfonamide The title compound was prepared from N(7)-(2-methoxy-ethyl)-6,7,8,9-tetrahydro-5H-benzocycloheptene-2,7-diamine and N-[(1R,2R)-2-(2,5-dichloro-pyrimidin-4-ylamino)-cyclohexyl]-methanesulfonamide in an analogous manner to Example 179. Product was isolated as a white TFA salt (17.8 mg, 23%). LCMS (m/e) 567 (M+H); $^1$H NMR (CDCl3, 400 MHz) δ 10.30 (s, 1H), 8.92 (broad s, 2H), 8.00 (s, 1H), 7.65 (s, 1H), 7.23 (s, 2H), 6.67 (s, 1H), 3.76 (s, 3H), 3.68 (s, 4H), 3.36 (s, 3H), 3.31-3.20 (m, 4H), 3.02 (s, 3H), 2.75 (m, 2H), 2.56 (m, 2H), 2.40 (m, 2H), 2.06 (m, 2H), 1.79 (d, 1H, J=11.6 Hz), 1.26-1.59 (m, 4H), 1.04 (m, 2H).

Example 897

(1S,2S,3R,4R)-3-{5-Chloro-2-[3-methoxy-7-(2-methoxy-ethylamino)-6,7,8,9-tetrahydro-5H-benzocyclohepten-2-ylamino]-pyrimidin-4-ylamino}-bicyclo[2.2.1]hept-5-ene-2-carboxylic acid amide The title compound was prepared from N(7)-(2-Methoxy-ethyl)-6,7,8,9-tetrahydro-5H-benzocycloheptene-2,7-diamine and (1S,2S,3R,4R)-3-(2,5-Dichloro-pyrimidin-4-ylamino)-bicyclo[2.2.1]hept-5-ene-2-carboxylic acid amide in an analogous manner to Example 179, heating at 130° C. Product was isolated as a white TFA salt (20.5 mg, 20%). LCMS (m/e) 527 (M+H); $^1$H NMR (CDCl$_3$, 400 MHz) δ 10.63 (broad s, 1H), 9.38 (broad s, 1H), 8.99 (d, 1H, J=8.08 Hz), 8.45 (broad s, 1H), 7.63 (s, 1H), 7.22 (s, 1H), 6.71 (s, 1H), 6.53 (s, 1H), 6.29 (s, 1H), 5.94 (s, 1H), 5.47 (s, 1H), 3.83 (s, 4H), 3.72 (m, 2H), 3.41 (s, 3H), 3.35 (m, 1H), 3.25 (m, 2H), 3.01 (s, 1H), 2.69-2.85 (m, 5H), 2.54 (d, 1H, J=7.58 Hz), 2.38 (m, 2H), 2.06 (d, 1H, J=9.09 Hz), 1.63 (m, 3H), 1.52 (d, 1H, J=9.09 Hz).

Example 898

(1S,2S,3R,4R)-3-{5-Chloro-2-[3-methoxy-7-(2-methoxy-ethylamino)-6,7,8,9-tetrahydro-5H-benzocyclohepten-2-ylamino]-pyrimidin-4-ylamino}-bicyclo[2.2.1]hept-5-ene-2-carboxylic acid amide The title compound was prepared from N(7)-(2-Methoxy-ethyl)-6,7,8,9-tetrahydro-5H-benzocycloheptene-2,7-diamine and (1S,2S,3R,4R)-3-(2,5-Dichloro-pyrimidin-4-ylamino)-bicyclo[2.2.1]hept-5-ene-2-carboxylic acid amide in Example 897. Product was isolated as a white TFA salt (18.9, 18%). LCMS (m/e) 527 (M+H); $^1$H NMR (CDCl$_3$, 400 MHz) δ 10.23 (broad s, 1H), 9.37 (broad s, 1H), 8.82 (s, 1H), 8.54 (s, 1H), 7.67 (s, 1H), 7.52 (s, 1H), 6.80 (s, 1H), 6.68 (s, 1H), 6.35 (s, 1H), 6.12 (s, 1H), 5.54 (s, 1H), 4.18 (m, 1H), 3.84 (s, 3H), 3.71 (m, 2H), 3.40 (m, 4H), 3.23 (m, 2H), 3.05 (m, 3H), 2.63-2.83 (m, 4H), 2.36 (m, 2H), 2.17 (d, 2H, J=8.59 Hz), 1.60 (m, 4H).

Example 899

2-{5-Chloro-2-[7-(4-methyl-piperazin-1-yl)-6,7,8,9-tetrahydro-5H-benzocyclohepten-2-ylamino]-pyrimidin-4-ylamino}-3-fluoro-N-methyl-benzamide The title compound was prepared from 2-(2,5-dichloro-pyrimidin-4-ylamino)-3-fluoro-N-methyl-benzamide and 7-(4-methyl-piperazin-1-yl)-6,7,8,9-tetrahydro-5H-benzocyclohepten-2-ylamine in an analogous manner to Example 179. Product was isolated as a racemic mixture as a TFA salt. (22.9 mg, 16%). LCMS (m/e) 538 (M+H); $^1$H NMR (DMSO-d6, 400 MHz) δ 9.29 (s, 1H), 9.23 (s, 1H), 8.52 (m, 1H), 8.16 (s, 1H), 7.48 (m, 1H), 7.43 (m, 1H), 7.28 (s, 1H), 7.17 (d, 1H, J=7.6 Hz), 6.87 (d, 1H, J=8.08 Hz), 3.92 (m, 5H), 2.93 (m, 2H), 2.75 (s, 3H), 2.74 (d, 3H), 2.69 (m, 2H), 2.60 (m, 8H), 2.06 (m, 2H), 1.29 (m, 2H).

Example 900

5-Chloro-N*2*-(1-methoxy-7-morpholin-4-yl-6,7,8,9-tetrahydro-5H-benzocyclohepten-2-yl)-N*4*-[2-(pyrrolidine-1-sulfonyl)-phenyl]-pyrimidine-2,4-diamine The title compound was prepared from 1-methoxy-7-morpholin-4-yl-6,7,8,9-tetrahydro-5H-benzocyclohepten-2-ylamine and (2,5-dichloro-pyrimidin-4-yl)-[2-(pyrrolidine-1-sulfonyl)-phenyl]-amine in an analogous manner to Example 179 heating at 140° C. Product was isolated as a TFA salt (41 mg, 46%). LCMS (m/e) 613 (M+H); $^1$H NMR (400 MHz, CDCl$_3$) δ 13.02 (broad s, 1H), 10.17 (s, 1H), 8.35 (d, 1H, J=8.34 Hz), 8.00 (s, 1H), 7.90 (d, 1H, J=7.83 Hz), 7.56 (d, 1H, J=8.08 Hz), 7.35 (t, 1H, J=7.32 Hz), 7.28 (t, 1H, J=7.33 Hz), 6.89 (d, 1H, J=8.09 Hz), 4.02 (m, 4H), 3.74 (s, 3H), 3.56 (m, 2H), 3.34 (m, 1H), 3.27 (m, 4H), 2.78-3.16 (m, 6H), 2.39-2.49 (m, 3H), 1.83 (m, 4H), 1.50 (m, 2H).

Example 901

5-Chloro-N*2*-(1-methoxy-7-morpholin-4-yl-6,7,8,9-tetrahydro-5H-benzocyclohepten-2-yl)-N*4*-(2-pyrazol-1-yl-phenyl)-pyrimidine-2,4-diamine The title compound was prepared from 1-methoxy-7-morpholin-4-yl-6,7,8,9-tetrahydro-5H-benzocyclohepten-2-ylamine and (2,5-dichloro-pyrimidin-4-yl)-(2-pyrazol-1-yl-phenyl)-amine in an analogous manner to Example 179. Product was isolated as a TFA salt (16 mg, 21%). LCMS (m/e) 546 (M+H); $^1$H NMR (400 MHz, CDCl$_3$) δ 12.5 (broad s, 1H), 11.7 (d, 1H), 10.9 (s, 1H), 8.19 (d, 1H, J=8.09 Hz), 7.85 (m, 3H), 7.44 (d, 1H, J=8.09 Hz), 7.40 (d, 1H, J=7.83 Hz), 7.27 (t, 1H, J=7.83), 7.07 (t, 1H, J=8.08 Hz), 6.90 (d, 1H, J=8.08 Hz), 6.54 (s, 1H), 4.02 (m, 3H), 3.72 (s, 3H), 3.58 (m, 3H), 3.35 (t, 2H, J=11 Hz), 2.94-3.18 (m, 2H), 2.83 (t, 1H, J=11 Hz), 2.38-2.53 (m, 3H), 1.41-1.59 (m, 2H).

Example 902

3-[5-Chloro-2-(1-methoxy-7-morpholin-4-yl-6,7,8,9-tetrahydro-5H-benzocyclohepten-2-ylamino)-pyrimidin-4-ylamino]-azepan-2-one The title compound was prepared from 1-methoxy-7-morpholin-4-yl-6,7,8,9-tetrahydro-5H-benzocyclohepten-2-ylamine and 3-(2,5-dichloro-pyrimidin-4-ylamino)-azepan-2-one in an analogous manner to Example 179 heating at 140°

C. Product was isolated as a mixture of diastereomers as the TFA salt (49 mg, 20%). LCMS (m/e) 515 (M+H); $^1$H NMR (CDCl$_3$, 400 MHz) 12.6 (broad s, 2H), 11.00 (s, 1H), 10.9 (s, 1H), 7.83 (m, 2H), 7.78 (s, 2H), 7.47 (m, 2H), 6.91 (m, 2H), 4.42 (m, 2H), 4.02 (broad s, 8H), 3.73 (s, 3H), 3.71 (s, 3H), 3.57 (m, 4H), 3.33 (m, 6H), 2.91-3.18 (m, 8H), 2.79 (t, 2H), 2.39 (m, 6H), 2.05 (m, 2H), 1.80-1.95 (4H), 1.21-1.55 (m, 10H).

Example 904

(1S,3R,4R)-3-[5-Chloro-2-((S)-1-methoxy-7-morpholin-4-yl-6,7,8,9-tetrahydro-5H-benzocyclohepten-2-ylamino)-pyrimidin-4-ylamino]-bicyclo[2.2.1]hept-5-ene-2-carboxylic acid 2-methoxy-ethyl ester The title compound was prepared as a by-product from a large scale preparation of Example 882. Product was isolated as a single diastereomer TFA salt (66 mg, 0.2%). LCMS (m/e) 598 (M+H); $^1$H NMR (CDCl$_3$, 400 MHz) δ 12.93 (broad s, 1H), 9.54 (d, 1H, J=7.33 Hz), 8.38 (s, 1H), 8.21 (d, 1H, J=8.34 Hz), 7.78 (s, 1H), 6.98 (d, 1H, J=8.34 Hz), 6.22 (s, 1H), 6.31 (s, 1H), 4.28 (t, 1H, J=8.09 Hz), 4.14 (m, 2H), 4.01 (s, 4H), 3.77 (s, 3H), 3.59 (t, 1H, J=11.6 Hz), 3.46 (m, 3H), 3.35 (t, 2H, J=10.6 Hz), 3.24 (s, 3H), 3.17 (s, 1H), 2.94-3.1 (m, 4H), 2.82 (d, 1H, J=11.6 Hz), 2.75 (d, 1H, J=8 Hz), 2.49 (m, 3H), 2.32 (d, 1H, J=9.85 Hz), 1.78 (d, 1H, J=9.6 Hz), 1.52 (septuplet, 2H, J=11 Hz).

Example 905

(1S,3R,4R)-3-[5-Chloro-2-((S)-1-methoxy-7-morpholin-4-yl-6,7,8,9-tetrahydro-5H-benzocyclohepten-2-ylamino)-pyrimidin-4-ylamino]-bicyclo[2.2.1]hept-5-ene-2-carboxylic acid 2-methoxy-ethyl ester The title compound was prepared as a by-product from a large scale preparation of Example 882. Product was isolated as a single diastereomer TFA (56 mg, 0.2%). LCMS (m/e) 598 (M+H); $^1$H NMR (CDCl$_3$, 400 MHz) δ 12.61 (broad s, 1H), 10.69 (s, 1H), 8.56 (d, 1H, J=7.07 Hz), 7.76 (s, 1H), 7.61 (d, 1H, J=8.34 Hz), 6.90 (d, 1H, J=8.08 Hz), 6.30 (m, 1H), 6.01 (m, 1H), 4.30 (m, 2H), 4.01 (m, 5H), 3.73 (s, 3H), 3.54-3.62 (m, 4H), 3.37 (s, 3H), 3.34 (m, 2H), 3.13-2.90 (m, 5H), 2.80 (t, 1H, J=11.6 Hz), 2.69 (d, 1H, J=7.8 Hz), 2.37-2.51 (m, 3H), 1.91 (d, 1H, J=9.34 Hz), 1.60 (d, 1H, J=9.6 Hz), 1.47 (m, 2H).

Example 906

1-{2-[5-Chloro-2-(1-methoxy-7-morpholin-4-yl-6,7,8,9-tetrahydro-5H-benzocyclohepten-2-ylamino)-pyrimidin-4-ylamino]-benzenesulfonyl}-pyrrolidin-3-ol The title compound was prepared from 1-methoxy-7-morpholin-4-yl-6,7,8,9-tetrahydro-5H-benzocyclohepten-2-yl amine and 1-[2-(2,5-dichloro-pyrimidin-4-ylamino)-benzenesulfonyl]-pyrrolidin-3-ol in an analogous manner to Example 179 heating at 130° C. Product was isolated as a mixture of diastereomers as TFA salts (98 mg, 68%). $^1$H NMR δ 12.54 (broad s, 2H), 10.74 (broad s, 1H), 10.70 (broad s, 1H), 10.10 (d, 2H, J=9.6 Hz), 8.144 (t, 2H, J=8.08 Hz), 7.96 (s, 2H), 7.91 (d, 2H, J=7.08 Hz), 7.39 (t, 2H, J=7.57 Hz), 7.29 (m, 4H), 6.88 (dd, 2H, J=3.28, 17.08 Hz), 4.40 (s, 2H), 3.99 (s, 10H), 3.71 (s, 3H), 3.70 (s, 3H), 3.55-3.39 (m, 8H), 3.33-3.17 (m, 6H), 3.18 (d, 2H, J=11.72 Hz), 3.1-2.92 (m, 6H), 2.80 (t, 2H, J=11.37 Hz), 2.34-2.49 (m, 6H), 1.98 (m, 2H), 1.87 (m, 2H), 1.50 (m, 2H), 1.39 (m, 2H).

Example 907

2-{5-Chloro-2-[7-(3-hydroxy-piperidin-1-yl)-1-methoxy-6,7,8,9-tetrahydro-5H-benzocyclohepten-2-ylamino]-pyrimidin-4-ylamino}-N,N-dimethyl-benzenesulfonamide 907a) To a stirred solution of 1-Methoxy-2,3-dimethylbenzene (10.00 g, 0.07343 mol) in carbon tetrachloride (100 mL, 1 mol) was added N-bromosuccinimide (39.2 g, 0.220 mol) and benzoyl peroxide (0.2 g, 0.0007 mol). The reaction mixture was heated to reflux overnight. HPLC indicated several new products forming (mono and di bromination products). Additional NBS (1 equiv.) and benzoyl peroxide (0.1 equiv) was added and the mixture heated at reflux. The reaction profile showed no starting material remaining however several products were present including the desired tribrominated product. The reaction mixture was cooled to room temperature and succinimide removed by filtration. The filtrate was concentrated in vacuo. 1H NMR of the crude reaction mixture showed 1-bromo-2,3-bis-bromomethyl-4-methoxy-benzene and impurities. Due to the difficulty of separating the product from other brominated species the crude mixture was carried forward. $^1$H NMR (DMSO-d6, 400 MHz) δ 7.66 (d, 1H, J=8.84 Hz), 1.06 (d, 1H, J=8.84 Hz), 4.81 (s, 2H), 4.77 (s, 2H), 3.88 (s, 3H). (Y. Goldberg et al, *J. Org. Chem.*, 1992, 57, 6374-6376)

907b) To a stirred suspension of tetra-n-butylammonium iodide (1.2 g, 0.0032 mol) in 0.6 M of sodium bicarbonate in water (43 mL) and methylene chloride (5 mL, 0.08 mol) was added a solution of 3-oxopentanedioic acid, diethyl ester (1.3 mL, 0.0070 mol) and 1-bromo-2,3-bis-bromomethyl-4-methoxy-benzene (2.01 g, 0.00539 mol) in methylene chloride (5 mL, 0.08 mol) dropwise. The biphasic reaction mixture was stirred vigorously overnight during which time the mixture changed colors from pale yellow to orange. The reaction mixture was quenched with ammonium chloride and extracted with methylene chloride (3×30 mL). The organic extracts were dried over magnesium sulfate, filtered and concentrated in vacuo to give mixture of diastereomers. Crude 1-bromo-4-methoxy-7-oxo-6,7,8,9-tetrahydro-5H-benzocycloheptene-6,8-dicarboxylic acid diethyl ester was taken on without purification to the next step.

907c) A stirred solution of 1-bromo-4-methoxy-7-oxo-6,7,8,9-tetrahydro-5H-benzocycloheptene-6,8-dicarboxylic acid diethyl ester (3) (102 g, 0.247 mol) in ethanol (2000 mL, 30 mol) and 1 M aqueous potassium hydroxide (1300 mL) was heated to reflux for 2 h. The reaction mixture was cooled to room temperature. HCl (1N) was added to quench the reaction and the product extracted with methylene chloride, washed with water and brine, dried over magnesium sulfate, filtered and concentrated in vacuo to give 1-Bromo-4-methoxy-5,6,8,9-tetrahydro-benzocyclohepten-7-one as a light orange-tan solid. The material was purified by ISCO chromatography using ethyl acetate-hexane (25-50%) to give desired product as a pale orange-tan solid (58 g, 87% yield); $^1$H NMR (CDCl$_3$, 400 MHz) δ 7.44 (d, 1H, J=8.84 Hz), 6.70 (d, 1H, J=9.09 Hz), 3.82 (s, 3H), 3.18 (m, 2H), 3.08 (m, 2H), 2.57 (m, 4H).

907d) To a stirred solution of 1-bromo-4-methoxy-5,6,8,9-tetrahydro-benzocyclohepten-7-one (20.0 g, 0.0743 mol) in sulfuric acid (200 mL, 4 mol) at 0° C. under an atmosphere of nitrogen was added potassium nitrate (7.89 g, 0.0780 mol) in portions. Note: When excess potassium nitrate is added, ipso substitution of the bromide is observed. After stirring for 15 min., an aliquot was removed and analyzed by HPLC indicating the completion of the reaction. Mixture was poured over ice water. A gummy solid formed which was dissolved in methylene chloride. The reaction mixture was transferred to a separatory funnel and the water layer removed. The organic phase was washed with saturated aqueous bicarbonate and water, dried over magnesium sulfate, filtered and concentrated in vacuo to an orange solid. Product was purified by ISCO chromatography on silica gel (350 g column) using ethyl acetate-hexane (10-100%). Fractions corresponding to product were combined and concentrated in vacuo to give 4-Bromo-1-Methoxy-2-nitro-5,6,8,9-tetrahydrobenzocyclohepten-7-one (18 g, 77%) as an orange solid. $^1$H NMR (CDCl$_3$, 400 MHz) 8.04 (s, 1H), 3.90 (s, 3H), 3.25 (m, 2H), 3.15 (m, 2H), 2.64 (m, 4H).

907e) To a stirred solution of 4-bromo-1-methoxy-2-nitro-5,6,8,9-tetrahydro-benzocyclohepten-7-one (2.00 g, 0.00637 mol) and piperidin-3-ol (6 g, 0.06 mol) in methylene chloride (100 mL, 2 mol) at room temperature was added acetic acid (4 mL, 0.06 mol) dropwise. Molecular sieves (2 mass equiv) were added to the reaction mixture and the contents heated at 40° C. overnight. The reaction mixture was cooled to room temperature then at 0° C. in an ice bath. Sodium triacetoxyborohydride (7 g, 0.03 mol) was added in one portion as a solid. The reaction mixture continued to stir at 0° C. for 1 h then warmed to room temperature for 4 h Workup involved quenching with water, adjusting the pH to 8-10 with 10 N NaOH (aq) and extracting with methylene chloride. The organic phase was dried over magnesium sulfate, filtered and concentrated in vacuo to a dark oil. Purification involved ISCO chromatography on silica gel (40 g column) using methylene chloride-methanol with 5% ammonium hydroxide. Fractions corresponding to product (polar fractions) were combined and concentration to give 1-(1-methoxy-2-nitro-6,7,8,9-tetrahydro-5H-benzocyclohepten-7-yl)-piperidin-3-ol as a brown oil. 1H NMR (400 MHz, CDCl3) δ 7.94 (s, 1H), 3.86 (s, 4H), 3.47 (m, 3H), 2.88 (t, 1H, J=11 Hz), 2.60-2.70 (m, 4H), 2.48-2.41 (m, 2H), 2.21 (m, 2H), 1.86 (m, 2H), 1.59 (m, 3H), 1.26-1.39 (m, 2H).

907f) The brown oil was dissolved in ethanol (40 mL, 0.7 mol) and placed in a Parr bottle which was filled with argon. Palladium on carbon 10% (100 mg) was carefully added to the flask and the contents evacuated and place under an atmosphere of hydrogen (50 psi). The reaction mixture was shaken for 54 h. Note: Nitro reduction is fast, debromination is slow. The mixture was filtered through celite, washing the celite cake with ethanol. The filtrate was concentrated in vacuo to give 1-(2-amino-1-methoxy-6,7,8,9-tetrahydro-5H-benzocyclohepten-7-yl)-piperidin-3-ol as a tan solid (1.4 g, 76%). 1H NMR (400 MHz, DMSO-d6) δ 6.63 (d, 1H, J=8.09 Hz), 6.45 (d, 1H, J=7.83 Hz), 5.42 (broad s, 1H), 4.68 (broad s, 2H), 4.03 (broad s, 1H), 3.58 (s, 3H), 3.16-3.36 (m, 8H), 2.55-2.70 (m, 2H), 2.2402.39 (m, 2H), 1.67 (m, 2H), 1.24-1.40 (m, 3H).

907 g) The title compound was prepared from [A] 1-(2-amino-1-methoxy-6,7,8,9-tetrahydro-5H-benzocyclohepten-7-yl)-piperidin-3-ol and 2-(2,5-dichloro-pyrimidin-4-ylamino)-N,N-dimethyl-benzenesulfonamide in an analogous manner to Example 179. Product was isolated as a mixture of diastereomers as the TFA salts (54.3 mg, 25%). LCMS (m/e) 601 (M+H); $^1$H NMR (CDCl$_3$, 400 MHz) δ 11.52 (s, 1H), 10.04 (m, 2H), 8.70 (d, 1H, J=8.09 Hz), 8.02 (s, 1H), 7.84 (d, 1H, J=7.58 Hz), 7.56 (d, 1H, J=7.83 Hz), 7.40 (t, 1H, J=7.58 Hz), 7.33 (t, 1H, J=7.33 Hz), 6.88 (d, 1H, J=8.08 Hz), 4.25 (m, 1H), 3.72 (s, 3H), 3.51 (m, 4H), 2.92 (m, 2H), 2.79 (m, 1H), 2.75 (s, 6H), 2.62 (m, 1H), 2.48 (m, 4H), 2.0 (m, 2H), 1.26-1.56 (m, 4H).

Example 908

1-(2-{5-Chloro-4-[2-(pyrrolidine-1-sulfonyl)-phenylamino]-pyrimidin-2-ylamino}-1-methoxy-6,7,8,9-tetrahydro-5H-benzocyclohepten-7-yl)-piperidin-3-ol The title compound was prepared from 1-(2-amino-1-methoxy-6,7,8,9-tetrahydro-5H-benzocyclohepten-7-yl)-piperidin-3-ol and (2,5-dichloro-pyrimidin-4-yl)-[2-(pyrrolidine-1-sulfonyl)-phenyl]-amine in an analogous manner as Example 179. Product was isolated as a mixture of diastereomers as the TFA salt (69.9, 70%). LCMS (m/e) 627 (M+H); $^1$H NMR (CDCl$_3$, 400 MHz) 10.02 (broad s, 2H), 10.91 (broad s, 1H), 10.41 (s, 1H), 8.28 (m, 1H), 7.98 (s, 1H), 7.89 (m, 1H), 7.41 (t, 1H, J=8.34 Hz), 7.30 (m, 2H), 6.91 (d, 1H, J=8.08 Hz), 4.19-4.28 (m, 1H), 3.73 (s, 3H), 3.44-3.61 (m, 4H), 3.25 (m, 4H), 2.78-2.98 (m, 4H), 2.45 (m, 3H), 2.01 (m, 2H), 1.85 (m, 5H), 1.40-1.60 (m, 3H).

Example 909

(1S,2S,3R,4R)-3-{5-Chloro-2-[7-(3-hydroxy-piperidin-1-yl)-1-methoxy-6,7,8,9-tetrahydro-5H-benzocyclohepten-2-ylamino]-pyrimidin-4-ylamino}-bicyclo[2.2.1]hept-5-ene-2-carboxylic acid amide The title compound was prepared from 1-(2-amino-1-methoxy-6,7,8,9-tetrahydro-5H-benzocyclohepten-7-yl)-piperidin-3-ol and (1S,2S,3R,4R)-3-(2,5-dichloro-pyrimidin-4-ylamino)-bicyclo[2.2.1]hept-5-ene-2-carboxylic acid amide in an analogous manner to Example 179 heating at 130° C. Product was isolated as a mixture of diastereomers as TFA salts (30 mg, 20%). LCMS (m/e) 553 (M+H); $^1$H NMR (400 MHz, DMSO-d6) δ 9.31 (broad s, 1H), 9.18 (broad s, 1H), 8.87 (broad s, 1H), 8.65 (broad s, 1H), 8.18 (s, 1H), 7.95 (s, 1H), 7.87 (d, 1H, J=8.08 Hz), 7.41 (s, 1H), 7.04 (d, 1H, J=8.08 Hz), 6.36 (m, 1H), 6.24 (m, 1H), 1.2-4.19 (complex m, 27H).

Example 910

(1S,2S,3R,4R)-3-{5-Chloro-2-[7-(3-hydroxy-piperidin-1-yl)-1-methoxy-6,7,8,9-tetrahydro-5H-benzocyclohepten-2-ylamino]-pyrimidin-4-ylamino}-bicyclo[2.2.1]hept-5-ene-2-carboxylic acid amide The title compound was prepared from 1-(2-amino-1-methoxy-6,7,8,9-tetrahydro-5H-benzocyclohepten-7-yl)-piperidin-3-ol and (1S,2S,3R,4R)-3-(2,5-dichloro-pyrimidin-4-ylamino)-bicyclo[2.2.1]hept-5-ene-2-carboxylic acid amide in an analogous manner to Example 179 heating at 130° C. Product was isolated as a mixture of diastereomers as TFA salts (23 mg, 16%). LCMS (m/e) 553 (M+H); $^1$H NMR (400 MHz, DMSO-d6) δ 9.92 (broad s, 1H), 8.64 (broad s, 1H), 8.14 (s, 1H), 7.92 (s, 2H), 7.39 (s, 1H), 7.02 (t, 1H, J=7.84 Hz), 6.37 (m, 1H), 6.25 (m, 1H), 3.97 (t, 1H, J=7.33 Hz), 3.67 (s, 3H), 3.12-3.34 (m, 4H), 3.02 (m, 1H), 2.86-2.93 (m, 4H), 2.64-2.78 (m, 2H), 2.2-2.54 (m, 6H), 2.02 (d, 1H, J=8.84 Hz), 1.82-1.92 (m, 2H), 1.28-1.68 (m, 5H).

Example 911

2-{5-Chloro-2-[1-methoxy-7-(4-methyl-piperazin-1-yl)-6,7,8,9-tetrahydro-5H-benzocyclohepten-2-ylamino]-pyrimidin-4-ylamino}-N,N-dimethyl-benzenesulfonamide 911a) 1-(1-Methoxy-2-nitro-6,7,8,9-tetrahydro-5H-benzocyclohepten-7-yl)-4-methyl-piperazine was prepared from 1-methoxy-2-nitro-5,6,8,9-tetrahydro-benzocyclohepten-7-one and 1-methylpiperazine in a similar manner to Example 907e. Product was isolated as a brown film.

911b) 1-Methoxy-7-(4-methyl-piperazin-1-yl)-6,7,8,9-tetrahydro-5H-benzocyclohepten-2-ylamine was prepared from 1-(1-Methoxy-2-nitro-6,7,8,9-tetrahydro-5H-benzocyclohepten-7-yl)-4-methyl-piperazine in an analogous manner to Example 907f. 1H NMR (CDCl3, 400 MHz) δ 6.71 (d, 1H, J=8.08 Hz), 6.53 (d, 1H, J=8.08 Hz), 3.69 (s, 3H), 3.66 (m, 2H), 3.50 (m, 2H), 3.36 (m, 3H), 3.01 (broad s, 5H), 2.76 (m, 1H), 2.63 (m, 1H), 2.45 (m, 4H), 2.33 (s, 3H), 2.31 (m, 1H), 1.38 (m, 2H), 911c) The title compound was prepared from 1-methoxy-7-piperazin-1-yl-6,7,8,9-tetrahydro-5H-benzocyclohepten-2-ylamine and 2-(2,5-dichloro-pyrimidin-4-ylamino)-N,N-dimethyl-benzenesulfonamide in an analogous manner to Example 179 heating to 130° C. Product was isolated as a TFA salt (97 mg, 31%). LCMS (m/e) 600 (M+H); $^1$H NMR (400 MHz, CDCl$_3$) δ 10.55 (s, 1H), 10.16 (s, 1H), 8.31 (d, 1H, J=8.34 Hz), 7.99 (s, 1H), 7.85 (d, 1H, J=7.58 Hz), 7.50 (d, 1H, J=8.33 Hz), 7.34 (m, 2H), 6.89 (d, 1H, J=8.09 Hz), 3.73 (s, 3H), 3.5-3.64 (m, 9H), 2.99 (m, 1H), 2.87 (s, 3H), 2.81 (m, 2H), 2.75 (s, 6H), 2.37-2.54 (m, 3H), 1.50 (m, 2H)

Example 912

2-{5-Chloro-2-[1-methoxy-7-(4-methyl-piperazin-1-yl)-6,7,8,9-tetrahydro-5H-benzocyclohepten-2-ylamino]-pyrimidin-4-ylamino}-N,N-dimethyl-benzenesulfonamide The title compound was prepared from 1-methoxy-7-(4-methyl-piperazin-1-yl)-6,7,8,9-tetrahydro-5H-benzocyclohepten-2-ylamine and N-[(1R,2R)-2-(2,5-dichloro-pyrimidin-4-ylamino)-cyclohexyl]-methanesulfonamide in an analogous manner as Example 179. Product was isolated as a mixture of diastereomers as the TFA salt. (28.8 mg, 10%). LCMS (m/e) 592 (M+H); $^1$H NMR (CDCl$_3$, 400 MHz) δ 10.36 (s, 1H), 8.01 (s, 1H), 7.63 (d, 1H, J=8.09 Hz), 7.05 (m, 1H), 6.88 (d, 1H, J=8.33 Hz), 6.72 (m, 2H), 3.80 (m, 1H), 3.66 (m, 4H), 3.53 (s, 3H), 3.46 (m, 3H), 3.00 (s, 3H), 2.93 (m, 1H), 2.86 (s, 3H), 2.72 (m, 2H), 2.30-2.42 (m, 3H), 2.03-2.11 (m, 4H), 1.87 (d, 1H, J=12.9 Hz), 1.74 (d, 1H, J=12.4 Hz), 1.17-1.57 (m, 7H).

Example 913

1-{2-[5-Chloro-4-(2-methoxy-4-morpholin-4-yl-phenylamino)-pyrimidin-2-ylamino]-1-methoxy-6,7,8,9-tetrahydro-5H-benzocyclohepten-7-yl}-piperidin-3-ol The title compound was prepared from 1-(2-Amino-1-methoxy-6,7,8,9-tetrahydro-5H-benzocyclohepten-7-yl)-piperidin-3-ol in an analogous manner to Example 179. Product was isolated as a mixture of diastereomers. Yellow-green TFA salt (64.4 mg, 20%). LCMS (m/e) 609 (M+H); $^1$H NMR (CDCl$_3$, 400 MHz) δ 11.2 (broad s, 1H), 10.78 (m, 2H), 8.41 (s, 1H), 7.93 (d, 1H, J=9.10 Hz), 7.85 (s, 1H), 7.46 (d, 1H, J=8.09 Hz), 6.92 (d, 1H, J=8.08 Hz), 6.63 (s, 1H), 6.34 (m, 1H), 4.15 (m, 1H), 3.94 (s, 8H), 3.71 (s, 3H), 3.43-3.59 (m, 4H), 3.23 (s, 3H), 2.77-3.00 (m, 4H), 2.36-2.54 (m, 4H), 1.98 (m, 2H), 1.38-1.55 (m, 4H).

Example 914

5-Chloro-N*2*-[1-methoxy-7-(4-methyl-piperazin-1-yl)-6,7,8,9-tetrahydro-5H-benzocyclohepten-2-yl]-N*4*-[2-(propane-2-sulfonyl)-phenyl]-pyrimidine-2,4-diamine The title compound was prepared from 1-methoxy-7-(4-methyl-piperazin-1-yl)-6,7,8,9-tetrahydro-5H-benzocyclohepten-2-ylamine and (2,5-dichloro-pyrimidin-4-yl)-[2-(propane-2-sulfonyl)-phenyl]-amine in an analogous manner to Example 179. Product was isolated as a racemate TFA salt. (79 mg, 26%). LCMS (m/e) 599 (M+H); $^1$H NMR (CDCl$_3$, 400 MHz) 10.57 (broad s, 1H), 10.39 (s, 1H), 8.33 (d, 1H, J=8.09 Hz), 8.01 (s, 1H), 7.92 (d, 1H, J=7.83 Hz), 7.49 (d, 1H, J=8.08 Hz), 7.41 (t, 1H, J=7.83 Hz), 7.34 (t, 1H, J=8.08 Hz), 6.90 (d, 1H, J=8.33 Hz), 3.73 (s, 3H), 3.66 (broad s, 7H), 3.55 (m, 3H), 3.20 (m, 1H, J=6.82 Hz), 2.99 (dd, 1H, J=7.07, 14.65 Hz), 2.88 (s, 3H), 2.78 (m, 1H), 2.38-2.52 (m, 3H), 1.51 (m, 2H), 1.31 (d, 6H, J=6.82 Hz).

Example 915

2-[5-Chloro-2-(1-methoxy-7-morpholin-4-yl-6,7,8,9-tetrahydro-5H-benzocyclohepten-2-ylamino)-pyrimidin-4-ylamino]-N-methyl-benzamide The title compound was prepared from 1-methoxy-7-morpholin-4-yl-6,7,8,9-tetrahydro-5H-benzocyclohepten-2-ylamine and 2-(2,5-dichloro-pyrimidin-4-ylamino)-N-methyl-benzamide in an analogous manner to Example 179. Product was isolated as a racemic mixture as a TFA salt (12.5 mg, 6%). LCMS (m/e) 537.12 (M+H); $^1$H NMR (CDCl$_3$, 400 MHz) δ 13.8 (broad s, 1H), 12.29 (s, 1H), 11.07 (s, 1H), 8.27 (m, 1H), 7.86 (s, 1H), 7.51 (m, 1H), 7.40 (d, 1H, J=8.09 Hz), 7.16 (m, 2H), 6.92 (d, 1H, J=8.08 Hz), 6.45 (s, 1H), 4.01 (m, 4H), 3.72 (s, 3H), 3.51-3.61 (m, 2H), 3.03 (d, 3H, J=4.8 Hz), 2.94-3.05 (m, 2H), 2.83 (m, 2H), 2.36-2.52 (m, 4H), 1.4-1.58 (m, 3H).

Example 916

(1S,2S,3R,4R)-3-{5-Chloro-2-[1-methoxy-7-(4-methyl-piperazin-1-yl)-6,7,8,9-tetrahydro-5H-benzocyclohepten-2-ylamino]-pyrimidin-4-ylamino}-bicyclo[2.2.1]hept-5-ene-2-carboxylic acid amide The title compound was prepared from 1-methoxy-7-(4-methyl-piperazin-1-yl)-6,7,8,9-tetrahydro-5H-benzocyclohepten-2-ylamine and (1S,2S,3R,4R)-3-(2,5-dichloro-pyrimidin-4-ylamino)-bicyclo[2.2.1]hept-5-ene-2-carboxylic acid amide was prepared in an analogous manner to Example 179. Product was isolated as a single diastereomer (21.7 mg, 7%). LCMS (m/e) 552 (M+H); $^1$H NMR (CDCl$_3$, 400 MHz) δ 11.74 (s, 1H), 9.13 (d, 1H, J=8.08 Hz), 7.71 (s, 1H), 7.62 (d, 1H, J=8.34), 6.90 (d, 1H, J=8.34 Hz), 6.30 (m, 1H), 6.10 (m, 1H), 5.91 (s, 1H), 5.53 (s, 1H), 4.00 (t, 1H, J=7.32 Hz), 3.72 (s, 3H), 3.42-3.58 (m, 8H), 3.08 (s, 1H), 2.90 (m, 1H), 2.88 (s, 1H), 2.83 (s, 3H), 2.75 (m, 2H), 2.35-2.45 (m, 6H), 2.10 (d, 1H, J=10 Hz), 1.59 (d, 1H, J=8.33 Hz), 1.49 (m, 2H).

Example 917

(1S,2S,3R,4R)-3-{5-Chloro-2-[1-methoxy-7-(4-methyl-piperazin-1-yl)-6,7,8,9-tetrahydro-5H-benzocyclohepten-2-ylamino]-pyrimidin-4-ylamino}-bicyclo[2.2.1]hept-5-ene-2-carboxylic acid amide The title compound was prepared from 1-methoxy-7-(4-methyl-piperazin-1-yl)-6,7,8,9-tetrahydro-5H-benzocyclohepten-2-ylamine and (1S,2S,3R,4R)-3-(2,5-dichloro-pyrimidin-4-ylamino)-bicyclo[2.2.1]hept-5-ene-2-carboxylic acid amide was prepared in the same preparation of Example 916 to provide a single diastereomer as a TFA salt (12.6 mg, 4%). LCMS (m/e) 552 (M+H); $^1$H NMR (CDCl$_3$, 400 MHz) δ 10.98 (s, 1H), 9.26 (d, 1H, J=7.07 Hz), 7.68 (s, 1H), 7.43 (d, 1H, J=8.09 Hz), 6.92 (d, 1H, J=8.08 Hz), 6.58 (s, 1H), 6.20 (m, 1H), 5.91 (m, 1H), 5.52 (s, 1H), 3.80 (m, 1H), 3.70 (s, 3H), 3.39-3.62 (m, *H), 3.03 (s, 1H), 2.93 (m, 2H), 2.85 (s, 3H), 2.77 (m, 2H), 2.38 (m, 5H), 1.53 (d, 1H, J=9.34 Hz), 1.45 (d, 1H, J=12.4 Hz), 1.27 (m, 2H).

Example 921

2-{2-[1-(2-Methoxyethyl)-2-oxo-2,3,4,5-tetrahydro-1H-benzo[b]azepin-7-ylamino]-5-trifluoromethylpyrimidin-4-ylamino}-N-methylbenzamide The title compound was prepared from 2-(2-chloro-5-trifluoromethyl-pyrimidin-4-ylamino)-N-methyl-benzamide and 7-amino-1-(2-methoxyethyl)-1,3,4,5-tetrahydrobenzo[b]azepin-2-one in an analogous manner to Example 195 (microwave: 120° C., 90 minutes) to afford a white solid (29 mg, 47%). Mp: 73-6° C. LCMS (m/e) 529 (M+1); $^1$H-NMR (CDCl$_3$, 400 MHz) δ 10.90 (s, 1H), 8.44 (d, J=9 Hz, 1H), 8.39 (s, 1H), 7.50-7.40 (m, 4H), 7.24 (m, 1H), 7.15 (m, 2H), 6.20 (br s, 1H), 4.00 (br m, 2H) 3.57 (t, 2H, J=5 Hz), 3.32 (s, 3H), 3.04 (d, J=5 Hz, 3H), 2.67 (br m, 2H), 2.31 (t, J=5 Hz, 2H), 2.13 (br m, 2H).

Example 922

2-{2-[3-(2-Methoxyethyl)-2,3,4,5-tetrahydro-1H-benzo[d]azepin-7-ylamino]-5-trifluoromethylpyrimidin-4-ylamino}-3,N-dimethylbenzamide The title compound was prepared from 2-(2-chloro-5-trifluoromethyl-pyrimidin-4-ylamino)-3,N-dimethyl-benzamide and 3-(2-methoxyethyl)-2,3,4,5-tetrahydro-1H-benzo[d]azepin-7-ylamine in an analogous manner to Example 195 to afford a white solid (29 mg, 47%). Mp: 73-6° C. LCMS (m/e) 529 (M+1); $^1$H-NMR (CDCl$_3$, 400 MHz) δ 8.40 (s, 1H), 8.30 (s, 1H), 7.39 (m, 2H), 7.31 (m, 1H), 7.10 (s, 1H), 6.99 (br s, 1H), 6.84 (br s, 1H), 6.00 (br s, 1H), 3.55 (t, 2H, J=5 Hz), 3.39 (s, 3H), 2.88 (d, J=5 Hz, 3H), 2.90 (m, 2H), 2.74 (t, J=5 Hz, 2H), 2.70-2.63 (m, 6H), 2.23 (s, 3H).

Example 923

N-Methyl-2-[2-(7-morpholin-4-yl-6,7,8,9-tetrahydro-5H-benzocyclohepten-2-ylamino)-5-trifluoromethyl-pyrimidin-4-ylamino]-benzamide The title compound was prepared from 2-(2-chloro-5-trifluoromethyl-pyrimidin-4-ylamino)-N-methyl-benzamide and 7-morpholin-4-yl-6,7,8,9-tetrahydro-5H-benzocyclohepten-2-ylamine in an analogous manner to Example 195 (microwave: 120° C., 60 minutes) to afford an off-white solid (35 mg, 86%). Mp: 158-62° C. LCMS (m/e) 541 (M+1); $^1$H-NMR (CDCl$_3$, 400 MHz) δ 10.85 (s, 1H), 8.45 (d, J=9 Hz, 1H), 8.36 (s, 1H), 7.50 (d, J=7 Hz, 1H), 7.47-7.37 (m, 2H), 7.30 (m, 1H), 7.25 (m, 2H), 7.10 (m, 1H), 6.27 (br s, 1H), 3.90-3.70 (m, 4H), 3.04 (s, 3H), 2.90-2.50 (m, 7H), 2.17 (m, 2H), 1.80-1.35 (m, 4H).

Example 924

N(2)-(3-Ethyl-2,3,4,5-tetrahydro-1H-benzo[d]azepin-7-yl)-N(4)-(2-methoxy-4-morpholin-4-yl-phenyl)-5-trifluoromethylpyrimidine-2,4-diamine 2,4-Dichloro-5-trifluoromethylpyrimidine (124 mg, 0.571 mmol), 2-methoxy-4-morpholin-4-yl-phenylamine (104 mg, 0.499 mmol), and N,N-diisopropylethylamine (97 mg, 0.75 mmol) were dissolved in 3 mL isopropyl alcohol and stirred at room temperature overnight. The reaction was concentrated and the organics dissolved in dichloromethane. The dichloromethane solution was washed with saturated sodium bicarbonate solution, was dried (sodium sulfate) and was concentrated. ISCO chromatography (0.75% MeOH: dichloromethane) afforded an inseparable mixture of both possible regioisomers (211 mg). This mixture (30 mg) was microwaved (130° C., 3 hours) with 3-ethyl-2,3,4,5-tetrahydro-1H-benzo[d]azepin-7-ylamine (16 mg, 0.084 mmol) and 10-camphorsulfonic acid 22 mg, 0.095 mmol) in isopropyl alcohol (3 mL). On cooling, the mixture was concentrated and the organics were extracted in dichloromethane. The dichloromethane solution was washed with saturated sodium bicarbonate solution, was dried (sodium sulfate), and was concentrated. ISCO chromatography (gradient elution: 1 to 10% MeOH:dichloromethane) affords the title compound—a white solid (20 mg, 50%). Mp: 167-70° C. LCMS (m/e) 543 (M+1); $^1$H-NMR (CDCl$_3$, 400 MHz) δ 8.30 (s, 1H), 8.06 (d, J=9 Hz, 1H), 7.55 (br s, 2H), 7.36 (s, 1H), 7.22 (br s, 1H), 7.10 (d, J=9 Hz, 1H), 6.78 (s, 1H), 6.50 (s, 1H), 6.38 (br s, 1H), 3.90 (m, 7H), 3.15 (m, 4H), 3.00 (m, 4H), 2.80-2.60 (m, 6H), 1.20 (d, J=7 Hz, 3H).

Example 926

3-Fluoro-2-{2-[1-(2-methoxy-ethyl)-2-oxo-2,3,4,5-tetrahydro-1H-benzo[b]azepin-8-ylamino]-5-trifluoromethyl-pyrimidin-4-ylamino}-N-methyl-benzamide The title compound was prepared from 2-(2-chloro-5-trifluoromethyl-pyrimidin-4-ylamino)-3-fluoro-N-methyl-benzamide and 8-amino-1-(2-methoxyethyl)-1,3,4,5-tetrahydrobenzo[b]azepin-2-one in an analogous manner to Example 195 (microwave: 120° C., 2 hours) to afford a white solid (30 mg, 50%). Mp: 142-4° C. LCMS (m/e) 547 (M+1); $^1$H-NMR (CDCl$_3$, 400 MHz) δ 9.03 (s, 1H), 8.35 (s, 1H), 7.56 (s, 1H), 7.47 (br s, 1H), 7.36 (m, 1H), 7.28 (m, 1H), 7.20 (m, 1H), 7.01 (br s, 2H), 3.40 (m, 2H), 3.26 (s, 3H), 2.94 (d, J=5 Hz, 3H), 2.66 (br m, 2H), 2.23 (br s, 2H).

Example 927

{3-[5-Chloro-2-(3-ethyl-2,3,4,5-tetrahydro-1H-benzo[d]azepin-7-ylamino)-pyrimidin-4-ylamino]-phenoxy}-acetonitrile The title compound was prepared from [3-(2,5-dichloro-pyrimidin-4-ylamino)-phenoxy]acetonitrile and 3-ethyl-2,3,4,5-tetrahydro-1H-benzo[d]azepin-7-ylamine in an analogous manner to Example 195 (microwave: 130° C., 2 hours) to afford a white foam (30 mg, 40%). Mp: 104-6° C. LCMS (m/e) 449 (M+1); $^1$H-NMR (CDCl$_3$, 400 MHz) δ 8.10 (s, 1H), 7.81 (s, 1H), 7.30 (m, 4H), 7.12 (s, 1H), 7.06 (m, 2H), 6.76 (d, J=6 Hz, 1H), 4.68 (s, 2H), 2.90 (m, 4H), 2.70-2.55 (m, 6H), 1.12 (t. J=7 Hz, 3H).

Example 928

{2-[5-Chloro-2-(3-ethyl-2,3,4,5-tetrahydro-1H-benzo[d]azepin-7-ylamino)-pyrimidin-4-ylamino]-phenoxy}-acetonitrile The title compound was prepared from [2-(2,5-dichloro-pyrimidin-4-ylamino)-phenoxy]acetonitrile and 3-ethyl-2,3,4,5-tetrahydro-1H-benzo[d]azepin-7-ylamine in an analogous manner to Example 927 (microwave: 120° C., 2 hours) to afford a white solid (17 mg, 22%). Mp: 153-6° C. LCMS (m/e) 449 (M+1); $^1$H-NMR (CDCl$_3$, 400 MHz) δ 8.46 (d, J=9 Hz, 1H), 8.10 (s, 1H), 7.63 (s, 1H), 7.35 (s, 1H), 7.23 (d. J=8 Hz, 1H), 7.15 (m, 2H), 7.06 (m, 2H), 6.94 (s, 1H), 4.90 (s, 2H), 2.92 (m, 4H), 2.71-2.55 (m, 6H), 1.14 (t. J=7 Hz, 3H).

Example 929

4-[5-Chloro-2-(7-morpholin-4-yl-6,7,8,9-tetrahydro-5H-benzocyclohepten-2-ylamino)-pyrimidin-4-ylamino]-3-methoxy-N-propyl-benzamide 2,4,5-Trichloropyrimidine (1.0 g, 5.4 mmol), 4-amino-3-methoxy-N-propylbenzamide (778 mg, 3.74 mmol), and N,N-diisopropylethylamine (1.19 g, 9.21 mmol) were combined in isopropanol (40 mL) and reacted in a microwave (120° C.) for 5½ hours. The 4-(2,5-dichloropyrimidin-4-ylamino)-3-methoxy-N-propylbenzamide that formed as a yellow solid (1.33 g, 71%) was isolated by filtration. A small amount of this material (50 mg, 0.10 mmol) was combined with 7-morpholin-4-yl-6,7,8,9-tetrahydro-5H-benzocyclohepten-2-ylamine (35 mg, 0.14 mmol) and 10-camphorsulfonic acid (36 mg, 0.15 mmol) in isopropanol (3 mL) to which had been added 0.05 mL water. The mixture was heated in a microwave (130° C.) for 3 hours and on cooling was concentrated. The organics were extracted into dichloromethane which was washed with saturated sodium bicarbonate solution and subsequently dried (sodium sulfate). Concentration followed by ISCO chromatography (gradient elution: 1 to 10% MeOH:dichloromethane) afforded 4-[5-Chloro-2-(7-morpholin-4-yl-6,7,8,9-tetrahydro-5H-benzocyclohepten-2-ylamino)-pyrimidin-4-ylamino]-3-methoxy-N-propyl-benzamide as a white solid (58 mg, 70%). Mp: 193-7° C. (dec). LCMS (m/e) 565 (M+1); $^1$H-NMR (CDCl$_3$, 400 MHz) δ 8.58 (d, J=8 Hz, 1H), 8.11 (s, 1H), 8.05 (m, 1H), 7.50 (s, 1H), 7.35 (s, 1H), 7.31 (m, 1H), 7.25 (m, 1H), 7.10 (d, J=8 Hz, 1H), 6.96 (s, 1H), 6.11 (m, 1H), 4.03 (s, 3H), 3.72 (m, 4H), 3.48 (m, 2H), 2.86 (m, 2H), 2.70 (m, 2H), 2.57 (s, 4H), 2.10 (m, 2H), 1.68 (m, 3H), 1.47 (m, 2H), 1.03 (t. J=7 Hz, 3H).

Example 930

{2-[5-Chloro-2-(5,5-dimethyl-2-oxo-2,3,4,5-tetrahydro-1H-1-benzazepin-8-ylamino)-pyrimidin-4-ylamino]-3-fluoro-phenoxy}-acetonitrile The title compound was prepared from [2-(2,5-dichloro-pyrimidin-4-ylamino)-3-fluorophenoxy]-acetonitrile and 8-amino-5,5-dimethyl-1,3,4,5-tetrahydrobenzo[b]azepin-2-one in an analogous manner to Example 927 to afford a yellow foam (37 mg, 48%). Mp: 142-8° C. LCMS (m/e) 481 (M+1); $^1$H-NMR (CDCl$_3$, 400 MHz) δ 8.10 (s, 1H), 7.52 (m, 1H), 7.38 (s, 1H), 7.32 (s, 1H), 7.28 (s, 1H), 7.21 (d. J=8 Hz, 1H), 7.08 (m, 1H), 6.96 (d, J=8 Hz, 1H), 6.82 (d, J=8 Hz, 1H), 6.55 (s, 1H), 4.79 (s, 2H), 2.37 (m, 2H), 2.10 (m, 2H), 1.36 (s, 6H).

Example 931

(2-{5-Chloro-2-[3-(2-methoxy-ethyl)-2,3,4,5-tetrahydro-1H-3-benzazepin-7-ylamino]-pyrimidin-4-ylamino}-3-fluoro-phenoxy)-acetonitrile The title compound was prepared from [2-(2,5-dichloro-pyrimidin-4-ylamino)-3-fluorophenoxy]-acetonitrile and 3-(2-methoxyethyl)-2,3,4,5-tetrahydro-1H-benzo[d]azepin-7-ylamine in an analogous manner to Example 930 to afford a yellow foam (48 mg, 55%). Mp: 68-74° C. LCMS (m/e) 497 (M+1); $^1$H-NMR (CDCl$_3$, 400 MHz) δ 8.07 (s, 1H), 7.35 (m, 1H), 7.14 (s, 1H), 7.09-6.94 (m, 3H), 6.90 (m, 1H), 6.51 (s, 1H), 4.71 (s, 2H), 3.58 (m, 2H), 3.38 (s, 3H), 2.87 (m, 2H), 2.80-2.65 (m, 8H).

Example 932

2-(7-Methoxy-8-{4-[2-(propane-2-sulfonyl)-phenylamino]-5-trifluoromethyl-pyrimidin-2-ylamino}-1,2,4,5-tetrahydro-3-benzazepin-3-yl)-N,N-dimethyl-acetamide 2,3-Dichloro-5-trifluoromethylpyrimidine (892 mg, 4.11 mmol), 2-(7-amino-8-methoxy-1,2,4,5-tetrahydro-benzo[d]azepin-3-yl)-N,N-dimethylacetamide (1.00 g, 3.6 mmol), and N,N-diisopropylethylamine (699 mg, 5.41 mmol) were combined in isopropanol (17 mL) and stirred at room temperature overnight. The reaction was concentrated and the organics were extracted into dichloromethane. The dichloromethane extract was washed with saturated sodium bicarbonate solution, was dried (sodium sulfate), and was concentrated. Reverse phase chromatography (Gilson) employing gradient elution (20-55% acetonitrile:water) afforded (in order of elution): 2-[7-(2-Chloro-5-trifluoromethylpyrimidin-4-ylamino)-8-methoxy-1,2,4,5-tetrahydro-3-benzazepin-3-yl]-N,N-dimethylacetamide (453 mg, 27%) and 2-[7-(4-Chloro-5-trifluoromethylpyrimidin-2-ylamino)-8-methoxy-1,2,4,5-tetrahydro-3-benzazepin-3-yl]-N,N-dimethylacetamide (458 mg, 28%). The latter compound (60 mg, 0.10 mmol) was combined with 2-(propane-2-sulfonyl)phenylamine (29 mg, 0.147 mmol) and 10-camphorsulfonic acid (48 mg, 0.207 mmol) in isopropanol (3 mL) to which had been added 0.01 mL water. The mixture was heated at 180° C. in a microwave for three hours. The reaction was permitted to cool and was concentrated. The organics were extracted into dichloromethane which was subsequently washed with saturated sodium bicarbonate solution, was dried (sodium sulfate), and was concentrated. ISCO chromatography (gradient elution: 1 to 5% MeOH:dichloromethane) afforded the title compound as a brown gum (4 mg, 4%). LCMS (m/e) 621 (M+1); $^1$H-NMR (CDCl$_3$, 400 MHz) δ 9.46 (s, 1H), 8.53 (d, J=8 Hz, 1H), 8.37 (s, 1H), 8.15 (s, 1H), 7.89 (d, J=8 Hz, 1H), 7.74 (s, 1H), 7.56 (m, 1H), 7.20 (m, 1H), 6.71 (s, 1H), 3.91 (s, 3H), 3.31 (m, 3H), 3.16 (s, 3H), 3.00 (s, 3H), 2.92 (m, 2H), 2.84 (m, 2H), 2.71 (m, 4H), 1.32 (d, J=7 Hz, 6H).

Example 933

(1S,2S,3R,4R)-3-[2-(3-Dimethylcarbamoylmethyl-8-methoxy-2,3,4,5-tetrahydro-1H-3-benzazepin-7-ylamino)-5-trifluoromethyl-pyrimidin-4-ylamino]-bicyclo[2.2.1]hept-5-ene-2-carboxylic acid amide (1S,2S,3R,4R)-3-Aminobicyclo[2.2.1]hept-5-ene-2-carboxylic acid amide trifluoroacetic acid salt (403 mg, 1.51 mmol) was combined with sodium bicarbonate (369 mg, 4.40 mmol) in a mixture of methanol (66 mL) and water (33 mL). 2,4-Dichloro-5-trifluoromethylpyrimidine (318 mg, 1.46 mmol) was added and the reaction was stirred for several minutes. Isopropanol (20 mL) was added to aid solubility and the reaction was stirred at room temperature for six hours. The reaction was concentrated and organics were extracted into dichloromethane. The dichloromethane extract was washed with saturated sodium bicarbonate solution, was dried (sodium sulfate), and was concentrated. Reverse phase chromatography (Gilson) employing gradient elution (30-60% acetonitrile:water) afforded two regioisomers (in order of elution): (1S,2S,3R,4R)-3-(2-Chloro-5-trifluoromethylpyrimidin-4-ylamino)-bicyclo[2.2.1]hept-5-ene-2-carboxylic acid amide (221 mg, 45%) and (1S,2S,3R,4R)-3-(4-Chloro-5-trifluoromethylpyrimidin-2-ylamino)-bicyclo[2.2.1]hept-5-ene-2-carboxylic acid amide (180 mg, 37%) both being isolated as white foams.

The former regioisomer (40 mg, 0.10 mmol) was combined with 2-(7-amino-8-methoxy-1,2,4,5-tetrahydrobenzo[d]azepin-3-yl)-N,N-dimethylacetamide (37 mg, 0.132 mmol) and p-toluenesulfonic acid monohydrate (25 mg, 0.132 mmol) in isopropanol (3 mL) and heated at 120° C. for one hour in a microwave. On cooling the reaction mixture was concentrated. The organics were extracted into dichloromethane. The dichloromethane extract was washed with saturated sodium bicarbonate solution, was dried (sodium sulfate), and was concentrated. ISCO chromatography on silica gel (gradient elution: 1-20% methanol:dichloromethane) followed by ISCO chromatography on amine-based silica gel (gradient elution: 1-3% methanol:dichloromethane) afforded the title compound as a white foam (52 mg, 80%). Mp: 133-5° C. LCMS (m/e) 574 (M+1); $^1$H-NMR (CDCl$_3$, 400 MHz) δ 8.18 (s, 1H), 8.16 (s, 1H), 7.61 (s, 1H), 6.82 (br s, 1H), 6.67 (s, 1H), 6.32 (m, 2H), 5.59 (br s, 1H), 5.39 (br s, 1H), 4.50 (m, 1H), 3.89 (s, 3H), 3.30 (m, 2H), 3.16 (s, 3H), 3.07 (s, 1H), 3.00 (s, 3H), 2.90 (m, 5H), 2.71 (m, 4H), 2.50 (d, J=8 Hz, 1H), 2.22 (d, J=9 Hz, 1H), 1.62 (m, 1H).

Example 934

(1S,2S,3R,4R)-3-{2-[3-(2-Methoxy-ethyl)-2,3,4,5-tetrahydro-1H-3-benzazepin-7-ylamino]-5-trifluoromethyl-pyrimidin-4-ylamino}-bicyclo[2.2.1]hept-5-ene-2-carboxylic acid amide The title compound was prepared from (1S,2S,3R,4R)-3-(2-Chloro-5-trifluoromethylpyrimidin-4-ylamino)-bicyclo[2.2.1]hept-5-ene-2-carboxylic acid amide and 3-(2-methoxyethyl)-2,3,4,5-tetrahydro-1H-benzo[d]azepin-7-ylamine in an analogous manner to Example 933 to afford a yellow solid (41 mg, 70%). Mp: 125-7° C. LCMS (m/e) 517 (M+1); $^1$H-NMR (CDCl$_3$, 400 MHz) δ 8.13 (s, 1H), 7.48 (d, J=8 Hz, 1H), 7.37-7.17 (m, 3H), 7.05 (d, J=8 Hz, 1H), 6.32 (m, 2H), 6.85 (br s, 1H), 6.63 (br s, 1H), 4.40 (m, 1H), 3.59 (m, 2H), 3.38 (s, 3H), 3.09 (s, 1H), 2.84 (m, 5H), 3.76 (m, 6H), 2.45 (d, J=8 Hz, 1H), 2.20 (d, J=8 Hz, 1H), 1.62 (d, J=8 Hz, 1H).

Example 935

(1S,2S,3R,4R)-3-[2-(7-Morpholin-4-yl-6,7,8,9-tetrahydro-5H-benzocyclohepten-2-ylamino)-5-trifluoromethyl-pyrimidin-4-ylamino]-bicyclo[2.2.1]hept-5-ene-2-carboxylic acid amide The title compound was prepared from (1S,2S,3R,4R)-3-(2-Chloro-5-trifluoromethylpyrimidin-4-ylamino)-bicyclo[2.2.1]hept-5-ene-2-carboxylic acid amide and 7-morpholin-4-yl-6,7,8,9-tetrahydro-5H-benzocyclohepten-2-ylamine in an analogous manner to Example 933 to afford a white solid (41 mg, 60%). Mp: 196-9° C. LCMS (m/e) 543 (M+1); $^1$H-NMR (CDCl$_3$, 400 MHz) δ 8.15 (s, 1H), 7.50 (m, 1H), 7.30 (m, 1H), 7.19-7.06 (m, 3H), 6.34 (m, 2H), 5.57 (br s, 1H), 5.51 (br s, 1H), 4.49 (m, 1H), 3.72 (m, 4H), 3.07 (s, 1H), 2.95 (s, 1H), 2.86 (m, 2H), 2.76-2.54 (m, 7H), 2.46 (d, J=8 Hz, 1H), 2.21 (d, J=9 Hz, 1H), 2.01 (m, 2H), 1.63 (d, J=9 Hz, 1H), 1.48 (m, 2H).

Example 936

7-{5-Chloro-2-[3-(2-methoxy-ethyl)-2,3,4,5-tetrahydro-1H-3-benzazepin-7-ylamino]-pyrimidin-4-ylamino}-4-methoxy-2-methyl-2,3-dihydro-isoindol-1-one 7-Amino-4-methoxy-2-methyl-2,3-dihydroisoindol-1-one (292 mg, 1.52 mmol) was combined with 2,4,5-trichloropyrimidine (279 mg, 1.52 mmol), and N,N-diisopropylethylamine (294 mg, 2.28 mmol) in isopropanol (5 mL) and microwaved at 120° C. for one hour. The yellow solid produced was isolated by filtration, was washed with clean isopropanol, and was dried in vacuo to afford 7-(2,5)-dichloropyrimidin-4-ylamino)-4-methoxy-2-methyl-2,3-dihydroisoindol-1-one (350 mg, 68%) as a yellow solid.

This material (50 mg, 0.1 mmol) was combined with 3-(2-methoxyethyl)-2,3,4,5-tetrahydro-1H-benzo[d]azepin-7-ylamine (34 mg, 0.155 mmol) and p-toluenesulfonic acid monohydrate (28 mg, 0.162 mmol) in isopropanol (3 mL) and microwaved at 120° C. for 90 minutes. The reaction was permitted to cool, was concentrated, and the organics were extracted into dichloromethane. The dichloromethane extract was washed with saturated sodium bicarbonate solution, was dried (sodium sulfate), and was concentrated. ISCO chromatography (gradient elution: 1 to 10% methanol:dichloromethane) afforded the title compound as a yellow solid (52 mg, 70%). Mp: 206-7° C. LCMS (m/e) 523 (M+1); $^1$H-NMR (CDCl$_3$, 400 MHz) δ 10.40 (s, 1H), 8.64 (d, J=9 Hz, 1H), 8.09 (s, 1H), 7.43 (s, 1H), 7.23 (d, J=7 Hz, 1H), 7.08 (d, J=8 Hz, 1H), 6.96 (s, 1H), 6.91 (d, J=9 Hz, 1H), 4.35 (s, 2H), 3.90 (s, 3H), 3.52 (m, 2H), 3.39 (s, 3H), 3.21 (s, 3H), 2.97 (m, 4H), 2.82-2.66 (m, 6H).

Example 937

2-{7-[5-Chloro-4-(7-methoxy-2-methyl-3-oxo-2,3-dihydro-1H-isoindol-4-ylamino)-pyrimidin-2-ylamino]-8-methoxy-1,2,4,5-tetrahydro-3-benzazepin-3-yl}-N,N-dimethyl-acetamide In an analogous manner to Example 936, 2-(7-amino-8-methoxy-1,2,4,5-tetrahydrobenzo[d]azepin-3-yl)-N,N-dimethylacetamide was coupled with 7-(2,5)-dichloropyrimidin- 4-ylamino)-4-methoxy-2-methyl-2,3-dihydroisoindol-1-one to afford the title compound as a white solid (50 mg, 60%). Mp: 202-3° C. LCMS (m/e) 581 (M+1); $^1$H-NMR (CDCl$_3$, 400 MHz) δ 10.36 (s, 1H), 8.69 (d, J=9 Hz, 1H), 8.10 (m, 2H), 7.39 (s, 1H), 7.29 (s, 1H), 6.94 (d, J=9 Hz, 1H), 6.69 (s, 1H), 5.31 (s, 2H), 4.34 (s, 2H), 3.90 (s, 6H), 3.21 (s, 3H), 3.15 (s, 3H), 2.98 (s, 3H), 2.94-2.56 (m, 8H).

Example 938 and Example 939

7-[5-Chloro-2-(7-hydroxy-6,7,8,9-tetrahydro-5H-benzocyclohepten-2-ylamino)-pyrimidin-4-ylamino]-4-methoxy-2-methyl-2,3-dihydro-isoindol-1-one and 7-[5-Chloro-2-(7-morpholin-4-yl-6,7,8,9-tetrahydro-5H-benzocyclohepten-2-ylamino)-pyrimidin-4-ylamino]-4-methoxy-2-methyl-2,3-dihydro-isoindol-1-one In an analagous manner to Example 936, 7-(2,5)-dichloropyrimidin-4-ylamino)-4-methoxy-2-methyl-2,3-dihydroisoindol-1-one was coupled with 7-morpholin-4-yl-6,7,8,9-tetrahydro-5H-benzocyclohepten-2-ylamine contaminated with (approximately twenty percent) 2-amino-6,7,8,9-tetrahydro-5H-benzocyclohepten-7-ol (a by-product of the previous reductive amination step) to afford two compounds listed in order of elution from silica gel:

7-[5-Chloro-2-(7-hydroxy-6,7,8,9-tetrahydro-5H-benzocyclohepten-2-ylamino)-pyrimidin-4-ylamino]-4-methoxy-2-methyl-2,3-dihydro-isoindol-1-one: (10 mg, 20%). Mp: 271-3° C. LCMS (m/e) 480 (M+1); $^1$H-NMR (CDCl$_3$, 400 MHz) δ 10.40 (s, 1H), 8.64 (d, J=9 Hz, 1H), 8.09 (s, 1H), 7.42 (s, 1H), 7.12 (d, J=8 Hz, 1H), 6.93 (d, J=9 Hz, 1H), 6.88 (s, 1H), 4.36 (s, 2H), 4.00 (m, 1H), 3.91 (s, 3H), 3.69 (m, 1H), 3.22 (s, 3H), 2.91 (m, 2H), 2.70 (m, 2H), 2.12 (m, 1H), 1.59 (m, 2H).

7-[5-Chloro-2-(7-morpholin-4-yl-6,7,8,9-tetrahydro-5H-benzocyclohepten-2-ylamino)-pyrimidin-4-ylamino]-4-methoxy-2-methyl-2,3-dihydro-isoindol-1-one: (42 mg, 70%). Mp: 275-7° C. LCMS (m/e) 549 (M+1); $^1$H-NMR (CDCl$_3$, 400 MHz) δ 10.40 (s, 1H), 8.66 (d, J=9 Hz, 1H), 8.09 (s, 1H), 7.42 (s, 1H), 7.11 (d, J=8 Hz, 1H), 6.94 (d, J=9 Hz, 1H), 6.86 (s, 1H), 4.36 (s, 2H), 3.91 (s, 3H), 3.72 (m, 4H), 3.23 (s, 3H), 2.90 (m, 2H), 2.69 (m, 3H), 2.58 (m, 4H), 2.10 (m, 2H), 1.49 (m, 2H).

Example 940 and Example 941

Diastereomers of (1S,2S,3R,4R)-3-[5-Chloro-2-(1-methoxy-6-morpholin-4-yl-6,7,8,9-tetrahydro-5H-benzocyclohepten-2-ylamino)-pyrimidin-4-ylamino]-bicyclo[2.2.1]hept-5-ene-2-carboxylic acid amide 1-Methoxy-5,7,8,9-tetrahydrobenzocyclohepten-6-one (5.29 g, 27.8 mmol) was combined with morpholine (2.66 g, 30.6 mmol) in tetrahydrofuran (200 mL) and stirred at room temperature for ten minutes. Sodium triacetoxyborohydride (8.25 g, 38.9 mmol) and acetic acid (1.58 mL, 27.8 mmol) were added and the mixture was stirred for two days. 10% additional morpholine, borohydride, and acetic acid were then added and stirring was continued for an additional 24 hours. The reaction was concentrated and the organics were extracted into dichloromethane. The dichloromethane extract as washed with saturated sodium bicarbonate solution followed by water. The organics were then concentrated and subjected to purification by ISCO chromatography (gradient elution: 1-10% methanol:dichloromethane) to afford a white solid (5.92 g, 81%)-4-(1-methoxy-6,7,8,9-tetrahydro-5H-benzocyclohepten-6-yl)-morpholine which was used in the next step without further purification.

The reductive amination product obtained above (5.46 g, 20.87 mmol) was dissolved in dry acetonitrile (35 mL) and trifluoroacetic acid (30 mL) and cooled to −5° C. Potassium nitrate (2.11 g, 20.9 mmol) was added in one portion and the mixture was stirred for three hours while warming to room temperature. The resulting mixture was poured in ice water was extracted with dichloromethane. The dichloromethane extract was washed with saturated sodium bicarbonate solution, was dried (sodium sulfate), and was concentrated. ISCO chromatography was effected in several batches (stepwise gradient: 35 to 40 to 45 to 50 to 55 to 60% followed by 100% ethyl acetate:dichloromethane) to afford two regioisomers in order of elution: 4-(1-Methoxy-4-nitro-6,7,8,9-tetrahydro-5H-benzocyclohepten-6-yl)-morpholine (2.41 g, 38%) and 4-(1-Methoxy-2-nitro-6,7,8,9-tetrahydro-5H-benzocyclohepten-6-yl)-morpholine (1.41 g, 22%). The latter nitro isomer, 4-(1-Methoxy-2-nitro-6,7,8,9-tetrahydro-5H-benzocyclohepten-6-yl)-morpholine (1.51 g, 4.939 mmol) was dissolved in ethanol (100 mL) and hydrogenated over 10% palladium on carbon (151 mg) at 50 psi using a Parr shaker for 3 hours. The palladium was removed by filtration and the ethanol was concentrated to afford a brown foam which was purified via ISCO chromatography (gradient elution: 2 to 8% methanol:dichloromethane) to afford 1-methoxy-6-morpholin-4-yl-6,7,8,9-tetrahydro-5H-benzocyclohepten-2-ylamine (830 mg, 61%) as a brown solid.

The product from the previous step (200 mg, 0.70 mmol) was combined with (1S,2S,3R,4R)-3-(2-Chloro-5-trifluoromethylpyrimidin-4-ylamino)-bicyclo[2.2.1]hept-5-ene-2-carboxylic acid amide (190 mg, 0.65 mmol), p-toluenesulfonic acid monohydrate (250 mg, 1.4 mmol), and isopropanol (5 mL) and heated in a microwave at 120° C. for 2 hours. After cooling, the reaction was concentrated and the crude products were purified sequentially by ISCO chromatography (gradient elution: 1 to 10% methanol:dichloromethane) followed by reverse phase chromatography (Gilson-gradient elution: 10-30% acetonitrile:water) and then a second ISCO chromatography employing the previous conditions to afford two diastereomers. Listed in order of their elution by reverse phase chromatography are the two diastereomers obtained. Absolute stereochemical configuration about the morpholine has not been determined.

Diastereomer 1: first product off of the Gilson—(1S,2S,3R,4R)-3-[5-Chloro-2-(1-methoxy-6-morpholin-4-yl-6,7,8,9-tetrahydro-5H-benzocyclohepten-2-ylamino)-pyrimidin-4-ylamino]-bicyclo[2.2.1]hept-5-ene-2-carboxylic acid amide—48 mg (14%) of a mauve solid. Mp: 146-8° C. LCMS (m/e) 539 (M+1); $^1$H-NMR (CDCl$_3$, 400 MHz) δ 8.21 (d, J=8 Hz, 1H), 7.91 (s, 1H), 7.42 (s, 1H), 7.01 (br s, 1H), 6.93 (d, J=8 Hz, 1H), 6.40 (m, 1H), 6.34 (m, 1H), 4.37 (t, J=8 Hz, 1H), 3.74 (m, 7H), 3.23 (m, 1H), 3.09 (s, H), 2.96 (s, 1H), 2.85 (m, 2H), 2.71 (m, 2H), 2.60 (m, 2H), 2.51 (d. J=8 Hz, 1H), 2.42 (m, 2H), 2.26 (d, J=9 Hz, 1H), 2.14 (m, 2H), 1.81 (m, 1H), 1.64 (d, J=9 Hz, 1H), 1.40 (m, 1H).

Diastereomer 2: second product off of the Gilson—(1S,2S,3R,4R)-3-[5-Chloro-2-(1-methoxy-6-morpholin-4-yl-6,7,8,9-tetrahydro-5H-benzocyclohepten-2-ylamino)-pyrimidin-4-ylamino]-bicyclo[2.2.1]hept-5-ene-2-carboxylic acid amide—65 mg (18%) of a white solid. Mp: 148-51° C. LCMS (m/e) 539 (M+1); $^1$H-NMR (CDCl$_3$, 400 MHz) δ 8.21 (d, J=8 Hz, 1H), 7.90 (s, 1H), 7.42 (s, 1H), 7.03 (d, J=8 Hz, 1H), 6.93 (d, J=8 Hz, 1H), 6.39 (m, 1H), 6.34 (m, 1H), 4.37 (t, J=8 Hz, 1H), 3.73 (m, 7H), 3.23 (m, 1H), 3.08 (s, H), 2.96 (s, 1H), 2.88 (m, 2H), 2.69 (m, 2H), 2.56 (m, 2H), 2.50 (d. J=8 Hz, 1H), 2.37 (m, 2H), 2.25 (d, J=9 Hz, 1H), 2.12 (m, 2H), 1.81 (m, 1H), 1.64 (d, J=9 Hz, 1H), 1.34 (m, 1H).

Example 942 and Example 943

Diastereomers of (1S,2S,3R,4R)-3-[5-Chloro-2-(4-methoxy-8-morpholin-4-yl-6,7,8,9-tetrahydro-5H-benzocyclohepten-1-ylamino)-pyrimidin-4-ylamino]-bicyclo[2.2.1]hept-5-ene-2-carboxylic acid amide 4-(1-Methoxy-4-nitro-6,7,8,9-tetrahydro-5H-benzocyclohepten-6-yl)-morpholine (1.51 g, 4.94 mmol) was dissolved in ethanol (100 mL) and hydrogenated over 10% palladium on carbon (151 mg) at 50 psi using a Parr shaker for 4 hours. The palladium was removed by filtration and the ethanol was concentrated to afford a brown foam which was purified via ISCO chromatography (gradient elution: 2 to 10% methanol: dichloromethane) to afford 4-methoxy-8-morpholin-4-yl-6,7,8,9-tetrahydro-5H-benzocyclohepten-1-ylamine (1.37 g, 99%) as a light brown solid.

This product (100 mg, 0.40 mmol) was combined with (1S,2S,3R,4R)-3-(2-Chloro-5-trifluoromethylpyrimidin-4-ylamino)-bicyclo[2.2.1]hept-5-ene-2-carboxylic acid amide (97 mg, 0.32 mmol), p-toluenesulfonic acid monohydrate (120 mg, 0.72 mmol), and isopropanol (3 mL) and heated in a microwave at 120° C. for 2 hours. After cooling, the reaction was concentrated and the crude products were purified by reverse phase chromatography (Gilson-gradient elution: 10-32% acetonitrile:water) and then a second ISCO chromatography employing the previous conditions to afford two diastereomers. Listed in order of their elution by reverse phase chromatography are the two diastereomers obtained. Absolute stereochemical configuration about the morpholine has not been determined.

Diastereomer 1: first product off of the Gilson—(1S,2S,3R,4R)-3-[5-Chloro-2-(4-methoxy-8-morpholin-4-yl-6,7,8,9-tetrahydro-5H-benzocyclohepten-1-ylamino)-pyrimidin-4-ylamino]-bicyclo[2.2.1]hept-5-ene-2-carboxylic acid amide—51 mg (29%) of an off-white foam. Mp: 133-5° C. LCMS (m/e) 539 (M+1); $^1$H-NMR (CDCl$_3$, 400 MHz) δ 7.81 (s, 1H), 7.18 (d, J=9 Hz, 1H), 6.77 (d, J=9 Hz, 1H), 6.56 (s, 1H), 6.48 (d, J=8 Hz, 1H), 6.24 (s, 1H), 6.17 (br s, 1H), 5.95 (br s, 1H), 5.46 (br s, 1H), 4.21 (br s, 1H), 3.82 (s, 3H), 3.69 (s, 4H), 3.38 (m, 1H), 3.22 (m, 1H), 3.01 (s, 1H), 2.71 (m, 3H), 2.52 (m, 1H), 2.40 (m, 4H), 2.21 (d. J=9 Hz, 1H), 2.03 (m, 2H), 1.78 (m, 1H), 1.59 (d, J=9 Hz, 1H), 1.40-1.20 (m, 2H).

Diastereomer 2: second product off of the Gilson—(1S,2S,3R,4R)-3-[5-Chloro-2-(4-methoxy-8-morpholin-4-yl-6,7,8,9-tetrahydro-5H-benzocyclohepten-1-ylamino)-pyrimidin-4-ylamino]-bicyclo[2.2.1]hept-5-ene-2-carboxylic acid amide—50 mg (28%) of an off-white foam. Mp: 132-5° C. LCMS (m/e) 539 (M+1); $^1$H-NMR (CDCl$_3$, 400 MHz) δ 7.79 (s, 1H), 7.21 (d, J=9 Hz, 1H), 6.77 (d, J=9 Hz, 1H), 6.55-6.40 (m, 2H), 6.26 (s, 1H), 6.22 (s, 1H), 5.64 (br s, 1H), 5.60 (br s, 1H), 4.25 (m, 1H), 3.82 (s, 3H), 3.66 (s, 4H), 3.40 (m, 1H), 3.24 (d, J=13 Hz, 1H), 3.04 (s, 1H), 2.79 (s, 1H), 2.56 (m, 3H), 2.38 (m, 4H), 2.22 (d, J=9 Hz, 1H), 2.0 (d, J=10 Hz, 2H), 1.78 (m, 1H), 1.60 (d, J=9 Hz, 1H), 1.30 (m, 2H).

Example 944

2-[5-Chloro-2-(1-methoxy-6-morpholin-4-yl-6,7,8,9-tetrahydro-5H-benzocyclohepten-2-ylamino)-pyrimidin-4-ylamino]-N,N-dimethyl-benzenesulfonamide The title compound was prepared from 1-methoxy-6-morpholin-4-yl-6,7,8,9-tetrahydro-5H-benzocyclohepten-2-ylamine (50 mg, 0.2 mmol) and 2-(2,5-dichloropyrimidin-4-ylamino)-N,N-dimethylbenzenesulfonamide (70 mg, 0.2 mmol) in an analogous manner to Example 936 to afford an off white foam (81 mg, 80%). Mp: 171-4° C. LCMS (m/e) 587 (M+1); $^1$H-NMR (CDCl$_3$, 400 MHz) δ 9.42 (s, 1H), 8.57 (d, J=8 Hz, 1H), 8.17 (s, 1H), 8.02 (d, J=8 Hz, 1H), 7.90 (d, J=8 Hz, 1H), 7.63 (m, 1H), 7.50 (s, 1H), 7.29 (m, 1H), 6.88 (d, J=8 Hz, 1H), 3.74 (s, 7H), 3.23 (m, 1H), 2.89 (m, 2H), 2.77 (s, 6H), 2.70 (m, 2H), 2.60 (m, 2H), 2.41 (m, 2H), 2.12 (d. J=1 Hz, 2H), 1.77 (m, 1H), 1.36 (m, 1H).

Example 945

2-[5-Chloro-2-(4-methoxy-8-morpholin-4-yl-6,7,8,9-tetrahydro-5H-benzocyclohepten-1-ylamino)-pyrimidin-4-ylamino]-N,N-dimethyl-benzenesulfonamide The title compound was prepared from 4-methoxy-8-morpholin-4-yl-6,7,8,9-tetrahydro-5H-benzocyclohepten-1-ylamine (50 mg, 0.2 mmol) and 2-(2,5-dichloropyrimidin-4-ylamino)-N,N-dimethylbenzenesulfonamide (70 mg, 0.2 mmol) in an analogous manner to Example 944 to afford a white foam (49 mg, 50%). Mp: 196-8° C. LCMS (m/e) 587 (M+1); $^1$H-NMR (CDCl$_3$, 400 MHz) δ 9.60 (s, 1H), 8.07 (m, 1H), 7.80 (d, J=8 Hz, 1H), 7.25 (m, 1H), 7.19 (d, J=9 Hz, 1H), 7.11 (m, 1H), 6.81 (d, J=9 Hz, 1H), 6.70 (br s, 1H), 3.86 (s, 3H), 3.60 (m, 4H), 3.42 (m, 1H), 3.22 (m, 1H), 2.75 (s, 6H), 2.59 (m, 3H), 2.33 (m, 4H), 2.00 (m, 3H), 1.72 (m, 1H).

Example 946

5-Chloro-N(2)-(4-methoxy-8-morpholin-4-yl-6,7,8,9-tetrahydro-5H-benzocyclohepten-1-yl)-N(4)-[2-(propane-2-sulfonyl)-phenyl]-pyrimidine-2,4-diamine The title compound was prepared from 4-methoxy-8-morpholin-4-yl-6,7,8,9-tetrahydro-5H-benzocyclohepten-1-ylamine (50 mg, 0.2 mmol) and (2,5-dichloropyrimidin-4-ylamino)-[2-(propane-2-sulfonyl)-phenyl]-amine (70 mg, 0.2 mmol) in an analogous manner to Example 945 to afford a white solid (61 mg, 60%). Mp: 199-201° C. LCMS (m/e) 586 (M+1); $^1$H-NMR (CDCl$_3$, 400 MHz) δ 9.74 (s, 1H), 8.40 (br s, 1H), 8.10 (s, 1H), 7.84 (d, J=8 Hz, 1H), 7.62 (m, 1H), 7.15 (m, 2H), 6.78 (m, 2H), 3.87 (s, 3H), 3.60 (m, 4H), 3.42 (m, 1H), 3.22 (m, 2H), 2.55 (m, 3H), 2.40-2.20 (m, 4H), 2.01 (m, 2H), 1.74 (m, 1H), 1.30 (m, 7H).

Example 947

5-Chloro-N(2)-(1-methoxy-6-morpholin-4-yl-6,7,8,9-tetrahydro-5H-benzocyclohepten-2-yl)-N(4)-[2-(propane-2-sulfonyl)-phenyl]-pyrimidine-2,4-diamine The title compound was prepared from 1-methoxy-6-morpholin-4-yl-6,7,8,9-tetrahydro-5H-benzocyclohepten-2-ylamine (50 mg, 0.2 mmol) and (2,5-dichloropyrimidin-4-ylamino)-[2-(propane-2-sulfonyl)-phenyl]-amine (70 mg, 0.2 mmol) in an analogous manner to Example 946 to afford a white foam (98 mg, 90%). Mp: 105-6° C. LCMS (m/e) 586 (M+1); $^1$H-NMR (CDCl$_3$, 400 MHz) δ 9.59 (s, 1H), 8.60 (d, J=8 Hz, 1H), 8.18 (s, 1H), 8.01 (d, J=8 Hz, 1H), 7.94 (d, J=8 Hz, 1H), 7.68 (t, J=8 Hz, 2H), 7.51 (br s, 1H), 7.32 (m, 1H), 6.89 (d, J=8 Hz, 1H), 3.75 (m, 7H), 3.22 (m, 2H), 2.89 (m, 2H), 2.71 (m, 2H), 2.60 (m, 2H), 2.45 (m, 2H), 2.13 (m, 2H), 1.81 (m, 1H), 1.40 (m, 1H), 1.33 (d, J=7 Hz, 6H).

Example 948

2-[5-Chloro-2-(1-methoxy-6-morpholin-4-yl-6,7,8,9-tetrahydro-5H-benzocyclohepten-2-ylamino)-pyrimidin-4-ylamino]-benzoic acid isopropyl ester The title compound was prepared from 1-methoxy-6-morpholin-4-yl-6,7,8,9-tetrahydro-5H-benzocyclohepten-2-ylamine (50 mg, 0.2 mmol) and 2-(2,5-dichloropyrimidin-4-ylamino)-N-methylbenzamide (60 mg, 0.2 mmol) in an analogous manner to Example 946 to afford a yellow foam (45 mg, 40%). Mp: 117-20° C. LCMS (m/e) 566 (M+1); $^1$H-NMR (CDCl$_3$, 400 MHz) δ 11.14 (s, 1H), 8.85 (d, J=8 Hz, 1H), 8.17 (s, 1H), 8.10 (d, J=8 Hz, 1H), 8.07 (d, J=8 Hz, 1H), 7.56 (t, J=8 Hz, 2H), 7.45 (s, 1H), 7.12 (t, J=8 Hz, 1H), 6.93 (d, J=8 Hz, 1H), 5.38 (m, 1H), 3.75 (m, 7H), 3.25 (m, 1H), 2.90 (m, 2H), 2.70 (m, 2H), 2.60 (m, 2H), 2.41 (m, 2H), 2.12 (m, 2H), 1.81 (m, 1H), 1.65 (m, 1H), 1.42 (d, J=6 Hz, 6H).

Example 949

N-{(1R,2R)-2-[5-Chloro-2-(1-methoxy-6-morpholin-4-yl-6,7,8,9-tetrahydro-5H-benzocyclohepten-2-ylamino)-pyrimidin-4-ylamino]-cyclohexyl}-methanesulfonamide The title compound was prepared from 1-methoxy-6-morpholin-4-yl-6,7,8,9-tetrahydro-5H-benzocyclohepten-2-ylamine (149 mg, 0.54 mmol) and N-[(1R,2R)-2-(2,5-dichloropyrimidin-4-ylamino)-cyclohexyl]-methanesulfonamide (204 mg, 0.60 mmol) in an analogous manner to Example 946 to afford a white foam (227 mg, 73%). Mp: 110-12° C. LCMS (m/e) 579 (M+1); $^1$H-NMR (CDCl$_3$, 400 MHz) δ 7.96 (m, 2H), 7.31 (d, J=9 Hz, 1H), 6.94 (d, J=8 Hz, 1H), 5.47-5.27 (m, 2H), 3.91 (m, 1H), 3.73 (m, 7H), 3.26 (m, 2H), 2.88 (m, 2H), 2.81 (s, 3H), 2.70 (m, 2H), 2.60 (m, 2H), 2.39 (m, 2H), 2.23 (m, 2H), 2.15 (m, 2H), 1.85 (m, 3H), 1.63 (br s, 1H), 1.42 (m, 4H).

Example 950

7-{5-Chloro-2-[3-(2-methoxy-ethyl)-2,3,4,5-tetrahydro-1H-3-benzazepin-7-ylamino]-pyrimidin-4-ylamino}-4-(4-isopropyl-piperazin-1-yl)-2-methyl-2,3-dihydro-isoindol-1-one The title compound was prepared from 3-(2-methoxyethyl)-2,3,4,5-tetrahydro-1H-benzo[d]azepin-7-ylamine (35 mg, 0.16 mmol) and 7-(2,5-dichloropyrimidin-4-ylamino)-4-(4-isopropylpiperazin-1-yl)-2-methyl-2,3-dihydroisoindol-1-one (70 mg, 0.2 mmol) in an analogous manner to Example 946 to afford a pale yellow solid (60 mg, 60%). Mp: 190-2° C. LCMS (m/e) 619 (M+1); $^1$H-NMR (CDCl$_3$, 400 MHz) δ 10.60 (s, 1H), 8.63 (d, J=8 Hz, 1H), 8.09 (s, 1H), 7.39 (s, 1H), 7.29 (m, 1H), 7.10 (m, 2H), 6.92 (s, 1H), 4.39 (s, 2H), 3.60 (m, 2H), 3.40 (s, 3H), 3.23 (s, 3H), 3.15-2.86 (m, 8H), 2.84-2.60 (m, 10H), 1.82 (m, 1H), 1.12 (d, J=6 Hz, 6H).

Example 951

2-(7-{5-Chloro-4-[7-(4-isopropyl-piperazin-1-yl)-2-methyl-3-oxo-2,3-dihydro-1H-isoindol-4-ylamino]-pyrimidin-2-ylamino}-8-methoxy-1,2,4,5-tetrahydro-3-benzazepin-3-yl)-N,N-dimethyl-acetamide The title compound was prepared from 2-(7-amino-8-methoxy-1,2,4,5-tetrahydrobenzo[d]azepin-3-yl)-N,N-dimethylacetamide (41 mg, 0.15 mmol) and 7-(2,5-dichloropyrimidin-4-ylamino)-4-(4-isopropylpiperazin-1-yl)-2-methyl-2,3-dihydroisoindol-1-one (60 mg, 0.1 mmol) in an analogous manner to Example 946 to afford a tan foam (79 mg, 80%). Mp: 78-80° C. LCMS (m/e) 676 (M+1); $^1$H-NMR (CDCl$_3$, 400 MHz) δ 10.58 (s, 1H), 8.68 (d, J=9 Hz, 1H), 8.10 (s, 2H), 7.39 (s, 1H), 7.09 (d, J=9 Hz, 1H), 6.68 (s, 1H), 4.40 (s, 2H), 3.91 (s, 3H), 3.54 (s, 3H), 3.35 (s, 2H), 3.24 (s, 3H), 3.20 (s, 3H), 3.11-2.88 (m, 6H), 2.80-2.65 (m, 8H), 1.82 (m, 1H), 1.12 (d, J=6 Hz, 6H).

Example 952

5-Chloro-N(4)-(2-methoxy-4-morpholin-4-yl-phenyl)-N(2)-(1-methoxy-6-morpholin-4-yl-6,7,8,9-tetrahydro-5H-benzocyclohepten-2-yl)-pyrimidine-2,4-diamine The title compound was prepared from 1-methoxy-6-morpholin-4-yl-6,7,8,9-tetrahydro-5H-benzocyclohepten-2-ylamine (50 mg, 0.2 mmol) and (2,5-dichloropyrimidin-4-yl)-(2-methoxy-4-morpholin-4-yl-phenyl)-amine (64 mg, 0.18 mmol) in an analogous manner to Example 946 to afford a white foam (95 mg, 88%). Mp: 122-4° C. LCMS (m/e) 595 (M+1); $^1$H-NMR (CDCl$_3$, 400 MHz) δ 8.28 (d, J=9 Hz, 1H), 8.10 (m, 2H), 7.58 (s, 1H), 7.40 (s, 1H), 6.91 (d, J=9 Hz, 1H), 3.94 (s, 6H), 3.75 (m, 7H), 3.22 (m, 5H), 2.90 (m, 2H), 2.70 (m, 2H), 2.60 (m, 2H), 2.40 (m, 2H), 2.11 (m, 2H), 1.79 (m, 2H), 1.37 (m, 1H).

Example 953

7-{5-Chloro-2-[3-(2-hydroxy-ethyl)-8-methoxy-2,3,4,5-tetrahydro-1H-3-benzazepin-7-ylamino]-pyrimidin-4-ylamino}-4-(4-isopropyl-piperazin-1-yl)-2-methyl-2,3-dihydro-isoindol-1-one The title compound was prepared from 2-(7-amino-8-methoxy-1,2,4,5-tetrahydro-3-benzazepin-3-yl)-ethanol (40 mg, 0.20 mmol) and 7-(2,5-dichloropyrimidin-4-ylamino)-4-(4-isopropylpiperazin-1-yl)-2-methyl-2,3-dihydroisoindol-1-one (74 mg, 0.17 mmol) in an analogous manner to Example 946 to afford an off-white solid (75 mg, 70%). Mp: 198-200° C. LCMS (m/e) 635 (M+1); $^1$H-NMR (CDCl$_3$, 400 MHz) δ 10.55 (s, 1H), 8.67 (d, J=9 Hz, 1H), 8.11 (s, 2H), 7.40 (s, 1H), 7.10 (d, J=9 Hz, 1H), 6.68 (s, 1H), 4.40 (s, 2H), 3.91 (s, 3H), 3.70 (m, 2H), 3.20 (s, 3H), 3.08 (m, 4H), 2.92 (m, 5H), 2.82-2.64 (m, 11H), 1.13 (d, J=6 Hz, 6H).

Example 954

5-{5-Chloro-2-[3-(2-methoxy-ethyl)-2,3,4,5-tetrahydro-1H-3-benzazepin-7-ylamino]-pyrimidin-4-ylamino}-1H-pyrazole-3-carboxylic acid amide The title compound was prepared from 5-(2,5-dichloropyrimidin-4-ylamino)-2H-pyrazole-3-carboxylic acid amide (70 mg, 0.2 mmol) and 3-(2-methoxyethyl)-2,3,4,5-tetrahydro-1H-benzo[d]azepin-7-ylamine (57 mg, 0.256 mmol) in an analogous manner to Example 946 to afford a tan solid (66 mg, 60%). Mp: 208-10° C. LCMS (m/e) 457 (M+1); $^1$H-NMR (d6-dmso, 400 MHz) δ 10.08 (s, 1H), 9.73 (m, 1H), 9.49 (s, 1H), 8.63 (br s, 1H), 8.15 (s, 1H), 7.80 (br s, 1H), 7.52 (m, 3H), 7.16 (d, J=8 Hz, 1H), 3.70 (m, 6H), 3.40 (m, 2H), 3.36 (s, 3H), 3.27-2.90 (m, 6H).

Example 955

5-Chloro-N(2)-[3-(2-methoxy-ethyl)-2,3,4,5-tetrahydro-1H-3-benzazepin-7-yl]-N(4)-(5-methyl-2H-pyrazol-3-yl)-pyrimidine-2,4-diamine The title compound was prepared from was prepared from (2,5-dichloropyrimidin-4-yl)-(5-methyl-2H-pyrazole-3-yl)amine (137 mg, 0.56 mmol) and 3-(2-methoxyethyl)-2,3,4,5-tetrahydro-1H-benzo[d]azepin-7-ylamine (124 mg, 0.56 mmol) in an analogous manner to Example 946 to afford a white solid (110 mg, 46%). Mp: 198-9° C. LCMS (m/e) 428 (M+1); $^1$H-NMR (CDCl$_3$, 400 MHz) δ 8.07 (s, 1H), 7.54 (s, 1H), 7.36 (s, 1H), 7.24 (d, J=8 Hz, 1H), 7.07 (d, J=8 Hz, 1H), 6.96 (s, 1H), 6.46 (br s, 1H), 3.56 (m, 2H), 3.38 (s, 3H), 2.93 (m, 4H), 2.82 (m, 7H), 2.33 (s, 3H).

Example 956

(1S,2S,3R,4R)-3-{5-Chloro-2-[1-methoxy-6-(2-methoxy-ethylamino)-6,7,8,9-tetrahydro-5H-benzocyclohepten-2-ylamino]-pyrimidin-4-ylamino}-bicyclo[2.2.1]hept-5-ene-2-carboxylic acid amide The title compound was prepared from 1-methoxy-N(6)-(2-methoxyethyl)-6,7,8,9-tetrahydro-5H-benzocyclohepten-2,6-diamine (200 mg, 0.8 mmol) and (1S,2S,3R,4R)-3-(2,5-dichloropyrimidin-4-ylamino)-bicyclo[2.2.1]hept-5-ene-2-carboxylic acid amide (290 mg, 0.76 mmol) in an analogous manner to Example 946 to afford a tan solid (30 mg, 8%). Mp: 98-99° C. LCMS (m/e) 527 (M+1); $^1$H-NMR (CDCl$_3$, 400 MHz) δ 8.20 (m, 1H), 7.92 (s, 1H), 7.43 (s, 1H), 7.00 (d, J=8 Hz, 1H), 6.91 (d, J=8 Hz, 1H), 6.40 (m, 1H), 6.35 (m, 1H), 5.70 (br s, 1H), 5.56 (br s, 1H), 4.37 (m, 1H), 3.73 (s, 3H), 3.52 (m, 2H), 3.37 (s, 3H), 3.10 (m, 2H), 2.96-2.82 (m, 5H), 2.62 (m, 2H), 2.51 (d, J=8 Hz, 1H), 2.25 (d, J=8 Hz, 1H), 2.10 (m, 1H), 1.96 (m, 1H), 1.77 (m, 2H), 1.64 (d, J=8 Hz, 1H), 1.50 (m, 1H).

Example 957

2-{5-Chloro-2-[1-methoxy-6-(2-methoxy-ethylamino)-6,7,8,9-tetrahydro-5H-benzocyclohepten-2-ylamino]-pyrimidin-4-ylamino}-N,N-dimethyl-benzenesulfonamide The title compound was prepared from 1-methoxy-N(6)-(2-methoxyethyl)-6,7,8,9-tetrahydro-5H-benzocyclohepten-2,6-diamine (60 mg, 0.2 mmol) and 2-(2,5-dichloropyrimidin-4-ylamino)-N,N-dimethylbenzenesulfonamide (79 mg, 0.23 mmol) in an analogous manner to Example 946 to afford an off-white solid (15 mg, 10%). LCMS (m/e) 575 (M+1); $^1$H-NMR (CDCl$_3$, 400 MHz) δ 9.42 (s, 1H), 8.54 (d, J=8 Hz, 1H), 8.17 (s, 1H), 8.06 (d, J=8 Hz, 1H), 7.90 (d, J=8 Hz, 1H), 7.65 (m, 1H), 7.51 (s, 1H), 7.30 (m, 1H), 6.88 (d, J=8 Hz, 1H), 3.71 (s, 3H), 3.62 (m, 2H), 3.35 (s, 3H), 3.20-3.05 (m, 4H), 2.76 (s, 6H), 2.62 (m, 1H), 2.27 (m, 1H), 2.00 (m, 2H), 1.51 (m, 1H) 1.28 (m, 2H).

Example 958

N-((1R,2R)-2-{5-Chloro-2-[1-methoxy-6-(2-methoxy-ethylamino)-6,7,8,9-tetrahydro-5H-benzocyclohepten-2-ylamino]-pyrimidin-4-ylamino}-cyclohexyl)-methanesulfonamide The title compound was prepared from 1-methoxy-N(6)-(2-methoxyethyl)-6,7,8,9-tetrahydro-5H-benzocyclohepten-2,6-diamine (70 mg, 0.3 mmol) and N-[(1R,2R)-2-(2,5-dichloropyrimidin-4-ylamino)-cyclohexyl]-methanesulfonamide (90 mg, 0.26 mmol) in an analogous manner to Example 946 to afford a peach foam (47 mg, 31%). Mp: 81-3° C. LCMS (m/e) 567 (M+1); $^1$H-NMR (CDCl$_3$, 400 MHz) δ 7.96 (m, 2H), 7.33 (d, J=6 Hz, 1H), 6.92 (d, J=8 Hz, 1H), 5.47 (d, J=8 Hz, 1H), 3.92 (m, 1H), 3.73 (s, 3H), 3.51 (m, 2H), 3.37 (s, 3H), 3.29 (m, 1H), 3.11 (m, 1H), 2.87 (m, 4H), 2.82 (s, 3H), 2.61 (m, 2H), 2.21 (m, 2H), 2.10 (m, 1H), 1.95 (m, 1H), 1.84 (m, 1H), 1.67 (m, 3H), 1.51-1.31 (m, 5H).

Example 959

5-Chloro-N(2)-[1-methoxy-6-(2-methoxy-ethylamino)-6,7,8,9-tetrahydro-5H-benzocyclohepten-2-yl]-N(4)-[2-(propane-2-sulfonyl)-phenyl]-pyrimidine-2,4-diamine The title compound was prepared from 1-methoxy-N(6)-(2-methoxyethyl)-6,7,8,9-tetrahydro-5H-benzocyclohepten-2,6-diamine (60 mg, 0.2 mmol) and (2,5-dichloropyrimidin-4-yl)-[2-(propane-2-sulfonyl)-phenyl]-amine (78 mg, 0.23 mmol) in an analogous manner to Example 946 to afford a white foam (59 mg, 40%). Mp: 83-5° C. LCMS (m/e) 574 (M+1); $^1$H-NMR (CDCl$_3$, 400 MHz) δ 9.58 (s, 1H), 8.60 (d, J=8 Hz, 1H), 8.18 (s, 1H), 7.94 (d, J=8 Hz, 1H), 7.69 (d, J=8 Hz, 1H), 7.52 (br s, 1H), 7.30 (m, 1H), 6.87 (d, J=8 Hz, 1H), 3.75 (s, 3H), 3.54 (m, 2H), 3.37 (s, 3H), 3.25 (m, 1H), 3.10 (m, 1H), 2.92-2.80 (m, 4H), 2.63 (m, 2H), 2.10 (m, 1H), 1.97 (m, 1H), 1.71 (m, 1H), 1.55 (m, 2H), 1.33 (d, J=7 Hz, 6H).

Example 960

(1S,2S,3R,4R)-3-{5-Chloro-2-[6-(2-hydroxy-ethylamino)-1-methoxy-6,7,8,9-tetrahydro-5H-benzocyclohepten-2-ylamino]-pyrimidin-4-ylamino}-bicyclo[2.2.1]hept-5-ene-2-carboxylic acid amide The title compound was prepared from 2-(2,5-Dichloropyrimidin-4-ylamino)-N,N-dimethyl-benzenesulfonamide (100 mg, 0.30 mmol) and 2-(2-Amino-1-methoxy-6,7,8,9-tetrahydro-5H-benzocyclohepten-6-ylamino)-ethanol (75 mg, 0.30 mmol) in an analogous manner to Example 946 to afford an off-white foam (86 mg, 51%). Mp: 78-80° C. LCMS (m/e) 561 (M+1); $^1$H-NMR (CDCl$_3$, 400 MHz) δ 9.42 (s, 1H), 8.56 (d, J=8 Hz, 1H), 8.15 (s, 1H), 8.00 (d, J=8 Hz, 1H), 7.88 (d, J=8 Hz, 1H), 7.63 (m, 1H), 7.55 (s, 1H), 7.28 (m, 1H), 6.85 (d, J=8 Hz, 1H), 3.74 (s, 3H), 3.66 (m, 2H), 3.00-2.80 (m, 5H), 2.76 (s, 6H), 2.13 (m, 5H), 1.83 (m, 2H), 1.57 (m, 1H).

Example 961

2-(2-{5-Chloro-4-[2-(propane-2-sulfonyl)-phenylamino]-pyrimidin-2-ylamino}-1-methoxy-6,7,8,9-tetrahydro-5H-benzocyclohepten-6-ylamino)-ethanol The title compound was prepared from (2,5-Dichloropyrimidin-4-yl)-[2-(propane-2-sulfonyl)-phenyl]-amine (100 mg, 0.30 mmol) and 2-(2-Amino-1-methoxy-6,7,8,9-tetrahydro-5H-benzocyclohepten-6-ylamino)-ethanol (75 mg, 0.30 mmol) in an analogous manner to Example 946 to afford an off-white foam (97 mg, 58%). Mp: 80-1° C. LCMS (m/e) 560 (M+1); $^1$H-NMR (CDCl$_3$, 400 MHz) δ 9.60 (s, 1H), 8.60 (d, J=8 Hz, 1H), 8.19 (s, 1H), 7.94 (d, J=8 Hz, 1H), 7.68 (d, J=8 Hz, 1H), 7.65 (m, 1H), 7.52 (s, 1H), 7.30 (m, 1H), 6.87 (d, J=8

Hz, 1H), 3.75 (s, 3H), 3.66 (m, 2H), 3.00-2.82 (m, 5H), 2.76 (m, 2H), 2.09 (m, 1H), 1.86 (m, 4H), 1.60 (m, 1H), 1.35 (s, 3H), 1.33 (s, 3H).

Example 962

(R)-1-(2-{5-Chloro-2-[6-(2-hydroxy-ethylamino)-1-methoxy-6,7,8,9-tetrahydro-5H-benzocyclohepten-2-ylamino]-pyrimidin-4-ylamino}-benzenesulfonyl)-pyrrolidin-3-ol The title compound was prepared from {2-[(R)-3-(tert-Butyl-dimethyl-silanyloxy)-pyrrolidine-1-sulfonyl]-phenyl}-(2,5-dichloro-pyrimidin-4-yl)-amine (150 mg, 0.30 mmol) and 2-(2-Amino-1-methoxy-6,7,8,9-tetrahydro-5H-benzocyclohepten-6-ylamino)-ethanol (75 mg, 0.30 mmol) in an analagous manner to Example 946 to afford an off-white foam. Mp: 90-2° C. LCMS (m/e) 603 (M+1); $^1$H-NMR (CDCl$_3$, 400 MHz) δ 9.37 (s, 1H), 8.49 (d, J=8 Hz, 1H), 8.16 (s, 1H), 7.98 (m, 2H), 7.61 (t, J=8 Hz, 1H), 7.52 (br s, 1H), 7.28 (m, 1H), 6.81 (m, 1H), 4.37 (m, 1H), 3.74 (s, 3H), 3.61 (m, 2H), 3.42 (m, 3H), 3.29 (m, 1H) 2.98-2.68 (m, 7H), 2.09-1.73 (m, 8H), 1.60 (m, 1H).

Example 963

(S)-1-(2-{5-Chloro-2-[6-(2-hydroxy-ethylamino)-1-methoxy-6,7,8,9-tetrahydro-5H-benzocyclohepten-2-ylamino]-pyrimidin-4-ylamino}-benzenesulfonyl)-pyrrolidin-3-ol The title compound was prepared from {2-[(S)-3-(tert-Butyl-dimethyl-silanyloxy)-pyrrolidine-1-sulfonyl]-phenyl}-(2,5-dichloro-pyrimidin-4-yl)-amine (150 mg, 0.30 mmol) and 2-(2-Amino-1-methoxy-6,7,8,9-tetrahydro-5H-benzocyclohepten-6-ylamino)-ethanol (75 mg, 0.30 mmol) in an analagous manner to Example 946 to afford a white foam. Mp: 92-5° C. LCMS (m/e) 603 (M+1); $^1$H-NMR (CDCl$_3$, 400 MHz) δ 9.36 (s, 1H), 8.50 (m, 1H), 8.18 (s, 1H), 8.00 (m, 2H), 7.62 (m, 1H), 7.50 (br s, 1H), 7.29 (m, 1H), 6.81 (m, 1H), 4.37 (m, 1H), 3.74 (s, 3H), 3.61 (m, 2H), 3.43 (m, 3H), 3.30 (m, 1H) 2.98-2.70 (m, 7H), 2.03 (m, 1H), 1.86 (m, 2H), 1.63 (m, 6H).

Example 964

2-(2-{5-Chloro-4-[2-(pyrrolidine-1-sulfonyl)-phenylamino]-pyrimidin-2-ylamino}-1-methoxy-6,7,8,9-tetrahydro-5H-benzocyclohepten-6-ylamino)-ethanol The title compound was prepared from (2,5-Dichloro-pyrimidin-4-yl)-[2-(pyrrolidine-1-sulfonyl)-phenyl]-amine (110 mg, 0.30 mmol) and 2-(2-Amino-1-methoxy-6,7,8,9-tetrahydro-5H-benzocyclohepten-6-ylamino)-ethanol (75 mg, 0.30 mmol) in an analagous manner to Example 946 to afford a tan foam. Mp: 79-82° C. LCMS (m/e) 587 (M+1); 1H-NMR (CDCl$_3$, 400 MHz) δ 9.52 (s, 1H), 8.59 (d, J=8 Hz, 1H), 8.17 (s, 1H), 8.03 (d, J=8 Hz, 1H), 7.95 (d, J=8 Hz, 1H), 7.61 (t, J=8 Hz, 1H), 7.51 (s, 1H), 7.27 (m, 1H), 6.86 (d, J=8 Hz, 1H), 3.75 (s, 3H), 3.63 (m, 2H), 3.29 (m, 4H), 3.00-2.67 (m, 7H) 2.05 (m, 1H), 1.80 (m, 8H), 1.60 (m, 1H).

Example 965

N-((1R,2R)-2-{5-Chloro-2-[6-(2-hydroxy-ethylamino)-1-methoxy-6,7,8,9-tetrahydro-5H-benzocyclohepten-2-ylamino]-pyrimidin-4-ylamino}-cyclohexyl)-methanesulfonamide The title compound was prepared from N-[(1R,2R)-2-(2,5-Dichloro-pyrimidin-4-ylamino)-cyclohexyl]-methanesulfonamide (100 mg, 0.30 mmol) and 2-(2-amino-1-methoxy-6,7,8,9-tetrahydro-5H-benzocyclohepten-6-ylamino)-ethanol (75 mg, 0.30 mmol) in an analagous manner to Example 946 to afford a tan solid. Mp: 92-4° C. LCMS (m/e) 553 (M+1); $^1$H-NMR (CDCl$_3$, 400 MHz) δ 7.93 (m, 2H), 7.40 (br s, 1H), 6.89 (d, J=8 Hz, 1H), 5.56 (d, J=8 Hz, 1H), 3.90 (m, 1H), 3.71 (s, 3H), 3.61 (m, 2H), 3.47 (s, 3H), 3.25 (m, 1H), 2.93-2.63 (m, 10H), 2.20 (m, 2H), 2.01 (m, 1H), 1.80 (m, 4H), 1.55 (m, 1H), 1.39 (m, 4H).

Example 971

7-{5-Chloro-4-[2-(3-methyl-pyridin-2-yl)-phenylamino]-pyrimidin-2-ylamino}-5,5-dimethyl-1,3,4,5-tetrahydro-benzo[b]azepin-2-one 971a) Prepared analogously as Example 216 replacing 2-iodo-1-methyl-1H-imidazole with 2-bromo-3-methylpyridine and 3-Ethyl-2,3,4,5-tetrahydro-1H-benzo[d]azepin-7-ylamine with 7-Amino-5,5-dimethyl-1,3,4,5-tetrahydro-benzo[b]azepin-2-one to afford 7{5-Chloro-4-[2-(3-methyl-pyridin-2-yl)-phenylamino]-pyrimidin-2-ylamino}-5,5-dimethyl-1,3,4,5-tetrahydro-benzo[b]azepin-2-one. LC/MS (ESI): 499.35. MP=130-135° C. $^1$H NMR (400 MHz, DMSO, d$_6$) δ 9.68 (s, 1H), 9.32 (d, 2H, J=7.42 Hz), 8.58 (d, 1H, J=4.40 Hz), 8.26 (m, 1H), 8.09 (s, 1H), 7.84 (m, 1H), 7.42 (m, 3H), 7.38 (m, 2H), 7.23 (m, 1H), 6.83 (d, 1H, J=8.50 Hz), 2.29 (s, 3H), 2.15 (m, 2H), 1.94 (m, 2H), 1.21 (s, 6H).

Example 972

5-Chloro-N*2*-[3-(2-methoxy-ethyl)-2,3,4,5-tetrahydro-1H-benzo[d]azepin-7-yl]-N*4*-[2-(3-methyl-pyridin-2-yl)-phenyl]-pyrimidine-2,4-diamine 972a) Prepared analogously as Example 216 replacing 2-iodo-1-methyl-1H-imidazole with 2-bromo-3-methylpyridine and 3-Ethyl-2,3,4,5-tetrahydro-1H-benzo[d]azepin-7-ylamine with 3-(2-Methoxy-ethyl)-2,3,4,5-tetrahydro-1H-benzo[d]azepin-7-ylamine to afford 5-Chloro-N*2*-[3-(2-methoxy-ethyl)-2,3,4,5-tetrahydro-1H-benzo[d]azepin-7-yl]-N*4*-[2-(3-methyl-pyridin-2-yl)-phenyl]-pyrimidine-2,4-diamine. LC/MS (ESI): 515.34. MP=74-78° C. $^1$H NMR (400 MHz, DMSO, d$_6$) δ 9.63 (s, 1H), 9.24 (s, 1H), 8.58 (d, 1H, J=4.55 Hz), 8.29 (d, 1H, J=8.09 Hz), 8.07 (s, 1H), 7.83 (d, 1H, J=7.58 Hz), 7.46 (m, 1H), 7.35 (m, 2H), 7.30 (m, 1H), 7.28 (m, 2H), 6.94 (d, 1H, J=8.09 Hz), 3.46 (d, 2H, J=5.81 Hz), 3.31 (s, 3H), 2.75 (m, 2H), 2.69 (m, 2H), 2.28 (s, 3H).

Example 973

7-{5-Chloro-4-[2-(5-methyl-[1,3,4]thiadiazol-2-yl)-phenylamino]-pyrimidin-2-ylamino}-5,5-dimethyl-1,3,4,5-tetrahydro-benzo[b]azepin-2-one 973a) Prepared analogously as Example 216 replacing 2-iodo-1-methyl-1H-imidazole with 2-bromo-5-methyl-1,3,4-thiadiazole and 3-Ethyl-2,3,4,5-tetrahydro-1H-benzo[d]azepin-7-ylamine with 7-Amino-5,5-dimethyl-1,3,4,5-tetrahydro-benzo[b]azepin-2-one to afford 7-{5-Chloro-4-[2-(5-methyl-[1,3,4]thiadiazol-2-yl)-phenylamino]-pyrimidin-2-ylamino}-5,5-dimethyl-1,3,4,5-tetrahydro-benzo[b]azepin-2-one. LC/MS (ESI): 506.22. $^1$H NMR (400 MHz, DMSO, d$_6$) δ 9.41 (s, 1H), 9.34 (s, 1H), 8.24 (s, 1H), 7.95 (d, 1H, J=7.58 Hz), 7.53 (m, 1H), 7.47 (m, 1H), 7.33 (m, 1H), 6.80 (d, 1H, J=8.33 Hz), 2.78 (s, 3H), 2.15 (m, 2H), 1.95 (m, 2H), 1.26 (s, 6H).

Example 974

5-Chloro-N*2*-[3-(2-methoxy-ethyl)-2,3,4,5-tetrahydro-1H-benzo[d]azepin-7-yl]-N*4*-[2-(5-methyl-[1,3,4]thiadiazol-2-yl)-phenyl]-pyrimidine-2,4-diamine 974a) Prepared analogously as Example 216 replacing 2-iodo-1-methyl-1H-imidazole with 2-bromo-5-methyl-1,3,4-thiadiazole and 3-Ethyl-2,3,4,5-tetrahydro-1H-benzo[d]azepin-7-ylamine with 3-(2-Methoxy-ethyl)-2,3,4,5-tetrahydro-1H-benzo[d]azepin-7-ylamine to afford 5-Chloro-N*2*-[3-(2-methoxy-ethyl)-2,3,4,5-tetrahydro-1H-benzo[d]azepin-7-yl]-N*4*-[2-(5-methyl-[1,3,4]thiadiazol-2-yl)-phenyl]-pyrimidine-2,4-diamine. LC/MS (ESI): 522.27. MP=189-192° C. $^1$H NMR (400 MHz, DMSO, d$_6$) δ 9.66 (m, 1H), 9.46 (s, 1H), 8.40 (m, 1H), 8.24 (s, 1H), 8.03 (d, 1H, J=7.58 Hz), 7.57 (m, 1H), 7.38 (m, 2H), 7.29 (m, 1H), 7.02 (d, 1H, J=8.34 Hz), 3.70 (m, 2H), 3.64 (m, 2H), 3.42 (m, 2H), 3.39 (s, 3H), 3.10 (m, 2H), 3.01 (m, 2H), 2.83 (m, 2H), 2.77 (s, 3H).

Example 975

5-Chloro-N*2*-[3-(2-methoxy-ethyl)-2,3,4,5-tetrahydro-1H-benzo[d]azepin-7-yl]-N*4*-[2-(5-methyl-[1,3,4]thiadiazol-2-yl)-phenyl]-pyrimidine-2,4-diamine 975a) Prepared analogously as Example 216 replacing 2-iodo-1-methyl-1H-imidazole with 2-chloropyrazine and 3-Ethyl-2,3,4,5-tetrahydro-1H-benzo[d]azepin-7-ylamine with 7-Amino-5,5-dimethyl-1,3,4,5-tetrahydro-benzo[b]azepin-2-one to afford 5-Chloro-N*2*-[3-(2-methoxy-ethyl)-2,3,4,5-tetrahydro-1H-benzo[d]azepin-7-yl]-N*4*-[2-(5-methyl-[1,3,4]thiadiazol-2-yl)-phenyl]-pyrimidine-2,4-diamine. LC/MS (ESI): 486.29. MP=257.7° C. $^1$H NMR (400 MHz, DMSO, d$_6$) δ 11.39 (s, 1H), 9.35 (s, 2H), 9.19 (s, 1H), 8.79 (s, 1H), 8.42 (m, 1H), 8.18 (s, 1H), 7.99 (d, 1H, J=7.58 Hz), 7.65 (m, 1H), 7.48 (m, 2H), 7.31 (m, 1H), 6.83 (d, 1H, J=8.08 Hz), 2.16 (m, 2H), 1.96 (m, 2H), 1.26 (s, 6H).

Example 976

7-[5-Chloro-4-(2-pyrimidin-2-yl-phenylamino)-pyrimidin-2-ylamino]-5,5-dimethyl-1,3,4,5-tetrahydro-benzo[b]azepin-2-one 976a) Prepared analogously as Example 216 replacing 2-iodo-1-methyl-1H-imidazole with 2-bromopyrimidine and 3-Ethyl-2,3,4,5-tetrahydro-1H-benzo[d]azepin-7-ylamine with 7-Amino-5,5-dimethyl-1,3,4,5-tetrahydro-benzo[b]azepin-2-one to afford 7-[5-Chloro-4-(2-pyrimidin-2-yl-phenylamino)-pyrimidin-2-ylamino]-5,5-dimethyl-1,3,4,5-tetrahydro-benzo[b]azepin-2-one. LC/MS (ESI): 486.29. MP=185.7° C. $^1$H NMR (400 MHz, DMSO, d$_6$) δ 9.45 (s, 1H), 9.39 (s, 1H), 9.05 (d, 2H, J=3.79 Hz), 8.91 (m, 1H), 8.57 (d, 1H, J=7.97 Hz), 8.25 (s, 1H), 7.61 (m, 1H), 7.54 (m, 3H), 7.23 (m, 1H), 6.90 (d, 1H, J=8.77 Hz), 2.19 (m, 2H), 1.98 (m, 2H), 1.29 (s, 6H)

Example 977

5-Chloro-N*2*-[3-(2-methoxy-ethyl)-2,3,4,5-tetrahydro-1H-benzo[d]azepin-7-yl]-N*4*-(2-pyrimidin-2-yl-phenyl)-pyrimidine-2,4-diamine 977a) Prepared analogously as Example 216 replacing 2-iodo-1-methyl-1H-imidazole with 2-bromopyrimidine and 3-Ethyl-2,3,4,5-tetrahydro-1H-benzo[d]azepin-7-ylamine with 3-(2-Methoxy-ethyl)-2,3,4,5-tetrahydro-1H-benzo[d]azepin-7-ylamine to afford 5-Chloro-N*2*-[3-(2-methoxy-ethyl)-2,3,4,5-tetrahydro-1H-benzo[d]azepin-7-yl]-N*4*-(2-pyrimidin-2-yl-phenyl)-pyrimidine-2,4-diamine. LC/MS (ESI): 502.35. MP=95.1° C. $^1$H NMR (400 MHz, DMSO, d$_6$) δ 9.36 (s, 1H), 9.05 (d, 2H, J=5.06 Hz), 8.84 (m, 1H), 8.56 (d, 1H, J=8.09 Hz), 8.23 (s, 1H), 7.56 (m, 1H), 7.50 (m, 1H), 7.44 (m, 1H), 7.36 (m, 1H), 7.26 (t, 1H, J=7.33 Hz), 7.01 (d, 1H, J=8.08 Hz), 3.45 (t, 2H, J=6.07 Hz), 3.31 (s, 3H), 2.78 (m, 4H), 2.64 (m, 6H).

Example 978

7-[5-Chloro-4-(2-thiazol-2-yl-phenylamino)-pyrimidin-2-ylamino]-5,5-dimethyl-1,3,4,5-tetrahydro-benzo[b]azepin-2-one 978a) Prepared analogously as Example 216 replacing 2-iodo-1-methyl-1H-imidazole with 2-bromothiazole and 3-Ethyl-2,3,4,5-tetrahydro-1H-benzo[d]azepin-7-ylamine with 7-Amino-5,5-dimethyl-1,3,4,5-tetrahydro-benzo[b]azepin-2-one to afford 7-[5-Chloro-4-(2-thiazol-2-yl-phenylamino)-pyrimidin-2-ylamino]-5,5-dimethyl-1,3,4,5-tetrahydro-benzo[b]azepin-2-one. LC/MS (ESI): 491.29. MP=224.4° C. $^1$H NMR (400 MHz, DMSO, d$_6$) δ 11.96 (m, 1H), 9.42 (s, 1H), 9.37 (s, 1H), 8.78 (m, 1H), 8.07 (s, 1H), 7.96 (d, 1H, J=7.83 Hz), 7.89 (s, 1H), 7.63 (m, 1H), 7.50 (m, 2H), 7.23 (m, 1H), 6.87 (d, 1H, J=8.84 Hz), 2.17 (m, 2H), 1.97 (m, 2H), 1.29 (s, 6H).

Example 979

5-Chloro-N*2*-[3-(2-methoxy-ethyl)-2,3,4,5-tetrahydro-1H-benzo[d]azepin-7-yl]-N*4*-(2-thiazol-2-yl-phenyl)-pyrimidine-2,4-diamine 979a) Prepared analogously as Example 216 replacing 2-iodo-1-methyl-1H-imidazole with 2-bromothiazole and 3-Ethyl-2,3,4,5-tetrahydro-1H-benzo[d]azepin-7-ylamine with 3-(2-Methoxy-ethyl)-2,3,4,5-tetrahydro-1H-benzo[d]azepin-7-ylamine to afford 5-Chloro-N*2*-[3-(2-methoxy-ethyl)-2,3,4,5-tetrahydro-1H-benzo[d]azepin-7-yl]-N*4*-(2-thiazol-2-yl-phenyl)-pyrimidine-2,4-diamine. LC/MS (ESI): 507.31. $^1$H NMR (400 MHz, DMSO, d$_6$) δ 11.83 (m, 1H), 9.36 (m, 1H), 8.76 (m, 1H), 8.23 (s, 1H), 8.06 (m, 1H), 7.97 (m, 1H), 7.89 (s, 1H), 7.41 (m, 2H), 7.25 (m, 2H), 7.00 (m, 1H), 3.48 (m, 2H), 3.27 (s, 3H), 2.75 (m, 6H), 2.63 (m, 4H).

Example 980

7-(5-Chloro-4-{2-[1-(2-methoxy-ethyl)-1H-imidazol-2-yl]-phenylamino}-pyrimidin-2-ylamino)-5,5-dimethyl-1,3,4,5-tetrahydro-benzo[b]azepin-2-one 980a) Prepared analogously as Example 216 replacing 2-iodo-1-methyl-1H-imidazole with 2-Iodo-1-(2-methoxy-ethyl)-1H-imidazole and 3-Ethyl-2,3,4,5-tetrahydro-1H-benzo[d]azepin-7-ylamine with 7-Amino-5,5-dimethyl-1,3,4,5-tetrahydro-benzo[b]azepin-2-one to afford 7-(5-Chloro-4-{2-[1-(2-methoxy-ethyl)-1H-imidazol-2-yl]-phenylamino}-pyrimidin-2-ylamino)-5,5-dimethyl-1,3,4,5-tetrahydro-benzo[b]azepin-2-one. LC/MS (ESI): 532.34. $^1$H NMR (400 MHz, DMSO, d$_6$) δ 8.02 (s, 1H), 7.75 (m, 2H), 7.69 (m, 2H), 7.61 (m, 2H), 7.43 (m, 1H), 7.34 (m, 1H), 6.80

(m, 1H), 4.08 (m, 2H), 3.57 (m, 2H), 3.22 (s, 3H), 2.26 (m, 2H), 2.06 (m, 2H), 1.29 (s, 6H).

Example 981

5-Chloro-N*4*-{2-[1-(2-methoxy-ethyl)-1H-imidazol-2-yl]-phenyl}-N*2*-[3-(2-methoxy-ethyl)-2,3,4,5-tetrahydro-1H-benzo[d]azepin-7-yl]-pyrimidine-2,4-diamine 981a) Prepared analogously as Example 216 replacing 2-iodo-1-methyl-1H-imidazole with 2-Iodo-1-(2-methoxy-ethyl)-1H-imidazole and 3-Ethyl-2,3,4,5-tetrahydro-1H-benzo[d]azepin-7-ylamine with 3-(2-Methoxy-ethyl)-2,3,4,5-tetrahydro-1H-benzo[d]azepin-7-ylamine to afford 5-Chloro-N*4*-{2-[1-(2-methoxy-ethyl)-1H-imidazol-2-yl]-phenyl}-N*2*-[3-(2-methoxy-ethyl)-2,3,4,5-tetrahydro-1H-benzo[d]azepin-7-yl]-pyrimidine-2,4-diamine. LC/MS (ESI): 548.37. $^1$H NMR (400 MHz, DMSO, $d_6$) δ 8.04 (s, 1H), 7.75 (m, 2H), 7.70 (m, 2H), 7.61 (m, 2H), 7.38 (s, 1H), 7.27 (m, 1H), 7.04 (d, 1H, J=8.43 Hz), 4.15 (m, 2H), 3.78 (m, 4H), 3.58 (m, 2H), 3.45 (s, 3H), 3.40 (m, 2H), 3.22 (s, 3H), 3.08 (m, 4H), 3.01 (m, 2H).

Example 982

5-Chloro-N*2*-[3-(2-methoxy-ethyl)-2,3,4,5-tetrahydro-1H-benzo[d]azepin-7-yl]-N*4*-(2-oxazol-5-yl-phenyl)-pyrimidine-2,4-diamine 982a) Prepared analogously as Example 216 replacing 2-iodo-1-methyl-1H-imidazole with 2-bromo-oxazole and 3-Ethyl-2,3,4,5-tetrahydro-1H-benzo[d]azepin-7-ylamine with 3-(2-Methoxy-ethyl)-2,3,4,5-tetrahydro-1H-benzo[d]azepin-7-ylamine to afford 5-Chloro-N*2*-[3-(2-methoxy-ethyl)-2,3,4,5-tetrahydro-1H-benzo[d]azepin-7-yl]-N*4*-(2-oxazol-5-yl-phenyl)-pyrimidine-2,4-diamine. LC/MS (ESI): 491.29. $^1$H NMR (400 MHz, DMSO, $d_6$) δ 9.62 (m, 1H), 9.28 (m, 1H), 9.13 (m, 1H), 8.44 (s, 1H), 7.84 (m, 1H), 7.50 (m, 2H), 7.25 (m, 2H), 7.08 (d, 1H, J=7.83), 6.85 (d, 1H, J=8.34), 3.71 (m, 3H), 3.58 (m, 3H), 3.34 (s, 3H), 2.97-3.05 (m, 6H).

Example 983

7-{5-Chloro-4-[2-(1-methyl-1H-imidazol-2-yl)-phenylamino]-pyrimidin-2-ylamino}-1-ethyl-6-methoxy-1,3,4,5-tetrahydro-benzo[b]azepin-2-one 983a) Prepared analogously as Example 216 replacing 3-Ethyl-2,3,4,5-tetrahydro-1H-benzo[d]azepin-7-ylamine with 7-Amino-1-ethyl-6-methoxy-1,3,4,5-tetrahydro-benzo[b]azepin-2-one to afford 7-{5-Chloro-4-[2-(1-methyl-1H-imidazol-2-yl)-phenylamino]-pyrimidin-2-ylamino}-1-ethyl-6-methoxy-1,3,4,5-tetrahydro-benzo[b]azepin-2-one. LC/MS (ESI): 518.00. $^1$H NMR (400 MHz, DMSO, $d_6$) δ 8.12 (s, 1H), 7.67 (m, 6H), 7.50 (m, 1H), 6.99 (d, 1H, J=8.85 Hz), 3.65 (s, 3H), 2.58 (s, 3H), 2.31 (m, 4H), 2.18 (m, 4H), 1.00 (t, 3H, J=7.08 Hz).

Example 984

7-{5-Chloro-4-[2-(3-methyl-pyridin-2-yl)-phenylamino]-pyrimidin-2-ylamino}-1-ethyl-6-methoxy-1,3,4,5-tetrahydro-benzo[b]azepin-2-one 984a) Prepared analogously as Example 216 replacing 2-iodo-1-methyl-1H-imidazole with 2-bromo-3-methylpyridine and 3-Ethyl-2,3,4,5-tetrahydro-1H-benzo[d]azepin-7-ylamine with 7-Amino-1-ethyl-6-methoxy-1,3,4,5-tetrahydro-benzo[b]azepin-2-one to afford 7-{5-Chloro-4-[2-(3-methyl-pyridin-2-yl)-phenylamino]-pyrimidin-2-ylamino}-1-ethyl-6-methoxy-1,3,4,5-tetrahydro-benzo[b]azepin-2-one. LC/MS (ESI): 529.30. $^1$H NMR (400 MHz, DMSO, $d_6$) δ 8.65 (m, 1H), 8.40 (m, 1H), 7.96 (m, 2H), 7.72 (m, 1H), 7.55 (m, 3H), 7.38 (m, 1H), 7.05 (d, 1H, J=9.09 Hz), 3.67 (s, 3H), 2.32 (m, 4H), 2.25 (s, 3H), 2.11 (m, 3H), 1.00 (t, 3H, J=6.82 Hz).

Example 985

7-[5-Chloro-4-(2-oxazol-5-yl-phenylamino)-pyrimidin-2-ylamino]-5,5-dimethyl-1,3,4,5-tetrahydro-benzo[b]azepin-2-one 985a) Prepared analogously as Example 216 replacing 2-iodo-1-methyl-1H-imidazole with 2-bromo-oxazole and 3-Ethyl-2,3,4,5-tetrahydro-1H-benzo[d]azepin-7-ylamine with 7-Amino-5,5-dimethyl-1,3,4,5-tetrahydro-benzo[b]azepin-2-one to afford 7-[5-Chloro-4-(2-oxazol-5-yl-phenylamino)-pyrimidin-2-ylamino]-5,5-dimethyl-1,3,4,5-tetrahydro-benzo[b]azepin-2-one. LC/MS (ESI): 475.23. $^1$H NMR (400 MHz, DMSO, $d_6$) δ 9.24 (m, 2H), 8.44 (s, 1H), 8.14 (s, 1H), 7.81 (m, 1H), 7.54 (m, 2H), 7.46 (m, 2H), 7.28 (m, 3H), 6.56 (d, 1H, J=8.84 Hz), 2.10 (m, 2H), 1.91 (m, 2H), 1.19 (s, 6H).

Example 986

5-Chloro-N*2*-[8-methoxy-3-(2-methoxy-ethyl)-2,3,4,5-tetrahydro-1H-benzo[d]azepin-7-yl]-N*4*-[2-(1-methyl-1H-imidazol-2-yl)-phenyl]-pyrimidine-2,4-diamine 986a) Prepared analogously as Example 216 replacing 3-Ethyl-2,3,4,5-tetrahydro-1H-benzo[d]azepin-7-ylamine with 8-Methoxy-3-(2-methoxy-ethyl)-2,3,4,5-tetrahydro-1H-benzo[d]azepin-7-ylamine to afford 5-Chloro-N*2*-[8-methoxy-3-(2-methoxy-ethyl)-2,3,4,5-tetrahydro-1H-benzo[d]azepin-7-yl]-N*4*-[2-(1-methyl-1H-imidazol-2-yl)-phenyl]-pyrimidine-2,4-diamine. LC/MS (ESI): 534.36. $^1$H NMR (400 MHz, DMSO, $d_6$) δ 8.09 (s, 1H), 7.73 (m, 6H), 7.50 (m, 1H), 6.91 (m, 1H), 3.80 (s, 3H), 3.71 (m, 2H), 3.66 (s, 3H), 3.62 (m, 2H), 3.34 (s, 3H), 2.93 (m, 2H), 2.67 (m, 2H), 2.37 (m, 2H), 2.28 (m, 2H).

Example 987

5-Chloro-N*2*-[8-methoxy-3-(2-methoxy-ethyl)-2,3,4,5-tetrahydro-1H-benzo[d]azepin-7-yl]-N*4*-[2-(3-methyl-pyridin-2-yl)-phenyl]-pyrimidine-2,4-diamine 987a) Prepared analogously as Example 216 replacing 2-iodo-1-methyl-1H-imidazole with 2-bromo-3-methylpyridine and 3-Ethyl-2,3,4,5-tetrahydro-1H-benzo[d]azepin-7-ylamine with 8-Methoxy-3-(2-methoxy-ethyl)-2,3,4,5-tetrahydro-1H-benzo[d]azepin-7-ylamine to afford 5-Chloro-N*2*-[8-methoxy-3-(2-methoxy-ethyl)-2,3,4,5-tetrahydro-1H-benzo[d]azepin-7-yl]-N*4*-[2-(3-methyl-pyridin-2-yl)-phenyl]-pyrimidine-2,4-diamine. LC/MS (ESI): 545.33. $^1$H NMR (400 MHz, DMSO, $d_6$) δ 9.74 (m, 2H), 8.60 (m, 1H), 8.10 (s, 1H), 7.99 (m, 2H), 7.70 (m, 1H), 7.50 (m, 3H), 7.35

(m, 1H), 6.94 (s, 1H), 3.81 (s, 3H), 3.68 (m, 4H), 3.52 (m, 2H), 3.39 (s, 3H), 3.18 (m, 4H), 2.72 (m, 2H), 2.34 (s, 3H).

Example 988

6-{2-[5-Chloro-2-(5,5-dimethyl-2-oxo-2,3,4,5-tetrahydro-1H-benzo[b]azepin-7-ylamino)-pyrimidin-4-ylamino]-phenyl}-1H-pyrimidine-2,4-dione 988a) Prepared analogously as Example 216 replacing 2-iodo-1-methyl-1H-imidazole with 6-chlorouracil and 3-Ethyl-2,3,4,5-tetrahydro-1H-benzo[d]azepin-7-ylamine with 7-Amino-5,5-dimethyl-1,3,4,5-tetrahydro-benzo[b]azepin-2-one to afford 6-{2-[5-Chloro-2-(5,5-dimethyl-2-oxo-2,3,4,5-tetrahydro-1H-benzo[b]azepin-7-ylamino)-pyrimidin-4-ylamino]-phenyl}-1H-pyrimidine-2,4-dione. LC/MS (ESI): 518.28. $^1$H NMR (400 MHz, DMSO, d$_6$) δ 10.99 (s, 1H), 10.90 (s, 1H), 9.29 (s, 1H), 9.09 (m, 1H), 8.82 (m, 1H), 8.10 (s, 1H), 7.42 (m, 4H), 7.39 (m, 3H), 6.69 (m, 1H), 2.12 (m, 2H), 1.90 (m, 2H), 1.22 (s, 6H).

Example 989

7-{5-Chloro-4-[2-(3-methoxy-pyridin-2-yl)-phenylamino]-pyrimidin-2-ylamino}-5,5-dimethyl-1,3,4,5-tetrahydro-benzo[b]azepin-2-one 989a) Prepared analogously as Example 216 replacing 2-iodo-1-methyl-1H-imidazole with 2-bromo-3-methoxypyridine and 3-Ethyl-2,3,4,5-tetrahydro-1H-benzo[d]azepin-7-ylamine with 7-Amino-5,5-dimethyl-1,3,4,5-tetrahydro-benzo[b]azepin-2-one to afford 7-{5-Chloro-4-[2-(3-methoxy-pyridin-2-yl)-phenylamino]-pyrimidin-2-ylamino}-5,5-dimethyl-1,3,4,5-tetrahydro-benzo[b]azepin-2-one. LC/MS (ESI): 515.28. $^1$H NMR (400 MHz, DMSO, d$_6$) δ 10.06 (s, 1H), 9.31 (m, 2H), 8.34 (d, 1H, J=4.80 Hz), 8.24 (m, 1H), 8.10 (s, 1H), 7.67 (m, 3H), 7.41 (m, 3H), 7.21 (m, 1H), 6.82 (d, 1H, J=8.59 Hz), 3.84 (s, 3H), 2.15 (m, 2H), 1.95 (m, 2H), 1.25 (s, 6H).

Example 990

5-Chloro-N*2*-[3-(2-methoxy-ethyl)-2,3,4,5-tetrahydro-1H-benzo[d]azepin-7-yl]-N*4*-[2-(3-methoxy-pyridin-2-yl)-phenyl]-pyrimidine-2,4-diamine 990a) Prepared analogously as Example 216 replacing 2-iodo-1-methyl-1H-imidazole with 2-bromo-3-methoxypyridine and 3-Ethyl-2,3,4,5-tetrahydro-1H-benzo[d]azepin-7-ylamine with 8-Methoxy-3-(2-methoxy-ethyl)-2,3,4,5-tetrahydro-1H-benzo[d]azepin-7-ylamine to afford 5-Chloro-N*2*-[3-(2-methoxy-ethyl)-2,3,4,5-tetrahydro-1H-benzo[d]azepin-7-yl]-N*4*-[2-(3-methoxy-pyridin-2-yl)-phenyl]-pyrimidine-2,4-diamine. LC/MS (ESI): 531.34. $^1$H NMR (400 MHz, DMSO, d$_6$) δ 10.05 (s, 1H), 9.33 (s, 1H), 8.34 (d, 1H, J=4.54 Hz), 8.24 (m, 1H), 8.09 (s, 1H), 7.68 (d, 2H, J=8.34 Hz), 7.45 (m, 3H), 7.25 (m, 2H), 6.93 (d, 1H, J=7.83 Hz), 3.83 (s, 3H), 3.46 (m, 2H), 3.25 (s, 3H), 2.74 (m, 10H).

Example 991

7-{5-Chloro-4-[2-(3-trifluoromethyl-pyridin-2-yl)-phenylamino]-pyrimidin-2-ylamino}-5,5-dimethyl-1,3,4,5-tetrahydro-benzo[b]azepin-2-one 991a) Prepared analogously as Example 216 replacing 2-iodo-1-methyl-1H-imidazole with 2-bromo-3-trifluoromethylpyridine and 3-Ethyl-2,3,4,5-tetrahydro-1H-benzo[d]azepin-7-ylamine with 7-Amino-5,5-dimethyl-1,3,4,5-tetrahydro-benzo[b]azepin-2-one to afford 7-{5-Chloro-4-[2-(3-trifluoromethyl-pyridin-2-yl)-phenylamino]-pyrimidin-2-ylamino}-5,5-dimethyl-1,3,4,5-tetrahydro-benzo[b]azepin-2-one. LC/MS (ESI): 553.25. $^1$H NMR (400 MHz, DMSO, d$_6$) δ 9.34 (d, 2H, J=9.71 Hz), 9.02 (m, 1H), 8.45 (m, 2H), 8.32 (m, 1H), 8.10 (s, 1H), 7.73 (m, 1H), 7.49 (m, 3H), 7.38 (m, 1H), 7.28 (m, 1H), 6.81 (d, 1H, J=8.28 Hz), 2.16 (m, 2H), 1.94 (m, 2H), 1.21 (s, 6H).

Example 992

5-Chloro-N*2*-[3-(2-methoxy-ethyl)-2,3,4,5-tetrahydro-1H-benzo[d]azepin-7-yl]-N*4*-[2-(3-trifluoromethyl-pyridin-2-yl)-phenyl]-pyrimidine-2,4-diamine 992a) Prepared analogously as Example 216 replacing 2-iodo-1-methyl-1H-imidazole with 2-bromo-3-trifluoromethylpyridine and 3-Ethyl-2,3,4,5-tetrahydro-1H-benzo[d]azepin-7-ylamine with 8-Methoxy-3-(2-methoxy-ethyl)-2,3,4,5-tetrahydro-1H-benzo[d]azepin-7-ylamine to afford 5-Chloro-N*2*-[3-(2-methoxy-ethyl)-2,3,4,5-tetrahydro-1H-benzo[d]azepin-7-yl]-N*4*-[2-(3-trifluoromethyl-pyridin-2-yl)-phenyl]-pyrimidine-2,4-diamine. LC/MS (ESI): 569.25. $^1$H NMR (400 MHz, DMSO, d$_6$) δ 9.58 (m, 1H), 9.37 (s, 1H), 8.91 (s, 1H), 8.30 (m, 2H), 8.09 (s, 1H), 7.54 (m, 1H), 7.43 (m, 2H), 7.37 (m, 1H), 7.33 (m, 2H), 7.05 (d, 1H, J=8.08 Hz), 3.70 (m, 4H), 3.61 (m, 2H), 3.34 (s, 3H), 2.91-3.17 (m, 6H).

Example 993

7-[5-Chloro-4-(3-pyridin-3-yl-phenylamino)-pyrimidin-2-ylamino]-5,5-dimethyl-1,3,4,5-tetrahydro-benzo[b]azepin-2-one 993a) Prepared analogously as Example 216c replacing 2-(1-Methyl-1H-imidazol-2-yl)-phenylamine with 3-pyridyl-3-yl-phenylamine and 3-Ethyl-2,3,4,5-tetrahydro-1H-benzo[d]azepin-7-ylamine with 7-Amino-5,5-dimethyl-1,3,4,5-tetrahydro-benzo[b]azepin-2-one in Example 216d to afford 7-[5-Chloro-4-(3-pyridin-3-yl-phenylamino)-pyrimidin-2-ylamino]-5,5-dimethyl-1,3,4,5-tetrahydro-benzo[b]azepin-2-one. LC/MS (ESI): 485.23. $^1$H NMR (400 MHz, DMSO, d$_6$) δ 9.39 (s, 1H), 9.24 (s, 1H), 9.08 (s, 1H), 8.94 (s, 1H), 8.65 (d, 1H, J=4.80 Hz), 8.21 (m, 2H), 8.19 (s, 1H), 7.64 (m, 1H), 7.53 (m, 1H), 7.48 (m, 4H), 6.61 (d, 1H, J=8.85 Hz), 2.03 (m, 2H), 1.87 (m, 2H), 1.16 (s, 6H).

Example 994

7-{5-Chloro-4-[2-(1-methyl-1H-imidazol-2-yl)-phenylamino]-pyrimidin-2-ylamino}-1,3,4,5-tetrahydro-benzo[b]azepin-2-one 994a) Prepared analogously as Example 216 replacing 3-Ethyl-2,3,4,5-tetrahydro-1H-benzo[d]azepin-7-ylamine with 7-Amino-1,3,4,5-tetrahydro-benzo[b]azepin-2-one to afford 7-{5-Chloro-4-[2-(1-methyl-1H-imidazol-2-yl)-phenylamino]-pyrimidin-2-ylamino}-1,3,4,5-tetrahydro-benzo[b]azepin-2-one. LC/MS (ESI): 460.18. $^1$H NMR (400 MHz, DMSO, d$_6$) δ 9.29 (s, 1H), 9.15 (s, 1H), 8.12 (s, 1H), 7.73 (m, 5H), 7.52 (m, 1H), 7.43 (s, 1H), 7.29 (m, 1H), 6.76 (d, 1H, J=8.09 Hz), 3.61 (s, 3H), 2.09 (m, 4H), 1.27 (m, 2H).

Example 995

7-{5-Chloro-4-[2-(1-methyl-1H-imidazol-2-yl)-phenylamino]-pyrimidin-2-ylamino}-1-methyl-1,3,4,5-tetrahydro-benzo[b]azepin-2-one 995a) Prepared analogously as Example 216 replacing 3-Ethyl-2,3,4,5-tetrahydro-1H-benzo[d]azepin-7-ylamine with 7-Amino-1-methyl-1,3,4,5-tetrahydro-benzo[b]azepin-2-one to afford 7-{5-Chloro-4-[2-(1-methyl-1H-imidazol-2-yl)-phenylamino]-pyrimidin-2-ylamino}-1-methyl-1,3,4,5-tetrahydro-benzo[b]azepin-2-one LC/MS (ESI): 474.23. $^1$H NMR (400 MHz, DMSO, d$_6$) δ 9.17 (m, 1H), 8.14 (s, 1H), 7.72 (m, 5H), 7.52 (m, 2H), 7.42 (m, 2H), 7.11 (d, 1H, J=8.59 Hz), 3.65 (s, 3H), 3.17 (s, 3H), 2.40 (m, 2H), 2.11 (m, 2H), 1.97 (m, 2H).

Example 996

7-{5-Chloro-4-[2-(1-methyl-1H-imidazol-2-yl)-phenylamino]-pyrimidin-2-ylamino}-1-ethyl-8-methoxy-1,3,4,5-tetrahydro-benzo[b]azepin-2-one 996a) Prepared analogously as Example 216 replacing 3-Ethyl-2,3,4,5-tetrahydro-1H-benzo[d]azepin-7-ylamine with 7-Amino-1-ethyl-8-methoxy-1,3,4,5-tetrahydro-benzo[b]azepin-2-one to afford 7-{5-Chloro-4-[2-(1-methyl-1H-imidazol-2-yl)-phenylamino]-pyrimidin-2-ylamino}-1-ethyl-8-methoxy-1,3,4,5-tetrahydro-benzo[b]azepin-2-one. LC/MS (ESI): 518.28. $^1$H NMR (400 MHz, DMSO, d$_6$) δ 8.13 (s, 1H), 7.73 (m, 6H), 7.63 (s, 1H), 7.50 (m, 1H), 6.97 (s, 1H), 3.84 (s, 3H), 3.63 (s, 3H), 2.51 (s, 3H), 2.36 (m, 3H), 2.07 (m, 2H), 0.98 (t, 3H, J=7.07 Hz).

Example 997

7-[5-Chloro-4-(2-oxazol-5-ylphenylamino)-pyrimidin-2-ylamino]-1,3,4,5-tetrahydro-benzo[b]azepin-2-one

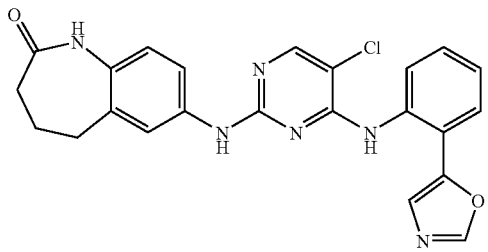

997a) Prepared analogously as Example 216 replacing 2-iodo-1-methyl-1H-imidazole with 2-bromo-oxazole and 3-Ethyl-2,3,4,5-tetrahydro-1H-benzo[d]azepin-7-ylamine with 7-Amino-1,3,4,5-tetrahydro-benzo[b]azepin-2-one to afford 7-[5-Chloro-4-(2-oxazol-5-yl-phenylamino)-pyrimidin-2-ylamino]-1,3,4,5-tetrahydro-benzo[b]azepin-2-one. LC/MS (ESI): 447.18. $^1$H NMR (400 MHz, DMSO, d$_6$) δ 9.26 (s, 1H), 9.19 (s, 1H), 9.13 (s, 1H), 8.43 (s, 1H), 8.14 (s, 1H), 7.58 (m, 1H), 7.51 (m, 3H), 7.26 (m, 2H), 7.10 (m, 1H), 6.63 (m, 1 h), 2.35 (m, 4H), 2.02 (m, 2H).

Example 998

9-{5-Chloro-4-[2-(1-methyl-1H-imidazol-2-yl)-phenylamino]-pyrimidin-2-ylamino}-8-methoxy-5,5-dimethyl-1,3,4,5-tetrahydro-benzo[b]azepin-2-one 998a) Prepared analogously as Example 216 replacing 3-Ethyl-2,3,4,5-tetrahydro-1H-benzo[d]azepin-7-ylamine with 9-Amino-8-methoxy-5,5-dimethyl-1,3,4,5-tetrahydro-benzo[b]azepin-2-one to afford 9-{5-Chloro-4-[2-(1-methyl-1H-imidazol-2-yl)-phenylamino]-pyrimidin-2-ylamino}-8-methoxy-5,5-dimethyl-1,3,4,5-tetrahydro-benzo[b]azepin-2-one. LC/MS (ESI): 518.34. $^1$H NMR (400 MHz, DMSO, d$_6$) δ 7.91 (m, 1H), 7.65 (m, 6H), 7.24 (d, 1H, J=8.59 Hz), 6.86 (d, 1H, J=8.85 Hz), 3.73 (s, 3H), 2.51 (s, 3H), 2.02 (m, 2H), 1.92 (m, 2H), 1.30 (s, 6H).

Example 999

2-(7-{5-Chloro-4-[2-(1-methyl-1H-imidazol-2-yl)-phenylamino]-pyrimidin-2-ylamino}-8-methoxy-1,2,4,5-tetrahydro-benzo[d]azepin-3-yl)-N,N-dimethyl-acetamide 999a) Prepared analogously as Example 216 replacing 3-Ethyl-2,3,4,5-tetrahydro-1H-benzo[d]azepin-7-ylamine with 2-(7-Amino-8-methoxy-1,2,4,5-tetrahydro-benzo[d]azepin-3-yl)-N,N-dimethyl-acetamide to afford 2-(7-{5-Chloro-4-[2-(1-methyl-1H-imidazol-2-yl)-phenylamino]-pyrimidin-2-ylamino}-8-methoxy-1,2,4,5-tetrahydro-benzo[d]azepin-3-yl)-N,N-dimethyl-acetamide. LC/MS (ESI): 561.32. $^1$H NMR (400 MHz, DMSO, d$_6$) δ 9.76 (m, 1H), 8.10 (s, 1H), 7.65 (m, 6H), 7.49 (m, 1H), 6.89 (s, 1H), 5.64 (m, 2H), 3.80 (s, 3H), 3.66 (s, 3H), 3.56 (m, 2H), 3.12 (m, 4H), 2.94 (s, 6H), 2.70 (m, 2H).

Example 1000

2-(7-{5-Chloro-4-[2-(3-methyl-pyridin-2-yl)-phenylamino]-pyrimidin-2-ylamino}-8-methoxy-1,2,4,5-tetrahydro-benzo[d]azepin-3-yl)-N,N-dimethyl-acetamide 1000a) Prepared analogously as Example 216 replacing 2-iodo-1-methyl-1H-imidazole with 2-bromo-3-methylpyridine and 3-Ethyl-2,3,4,5-tetrahydro-1H-benzo[d]azepin-7-ylamine with 2-(7-Amino-8-methoxy-1,2,4,5-tetrahydro-benzo[d]azepin-3-yl)-N,N-dimethyl-acetamide to afford 2-(7-{5-Chloro-4-[2-(3-methyl-pyridin-2-yl)-phenylamino]-pyrimidin-2-ylamino}-8-methoxy-1,2,4,5-tetrahydro-benzo[d]azepin-3-yl)-N,N-dimethyl-acetamide. LC/MS (ESI): 572.32. $^1$H NMR (400 MHz, DMSO, d$_6$) δ 9.70 (m, 2H), 8.60 (m, 1H), 8.06 (m, 3H), 7.68 (s, 1H), 7.52 (m, 3H), 7.36 (m, 1H), 6.92 (s, 1H), 4.32 (s, 2H), 3.81 (s, 3H), 3.58 (m, 2H), 3.15 (m, 4H), 3.05 (s, 6H), 2.78 (m, 2H), 2.25 (s, 3H).

Example 1001

7-{5-Chloro-4-[2-(4-methyl-pyridin-2-yl)-phenylamino]-pyrimidin-2-ylamino}-5,5-dimethyl-1,3,4,5-tetrahydro-benzo[b]azepin-2-one 1001a) Prepared analogously as Example 216 replacing 2-iodo-1-methyl-1H-imidazole with 2-bromo-4-methylpyridine and 3-Ethyl-2,3,4,5-tetrahydro-1H-benzo[d]azepin-7-ylamine with 7-Amino-5,5-dimethyl-1,3,4,5-tetrahydro-benzo[b]azepin-2-one to afford 7-{5-Chloro-4-[2-(4-methylpyridin-2-yl)-phenylamino]-pyrimidin-2-ylamino}-5,5-dimethyl-1,3,4,5-tetrahydro-benzo[b]azepin-2-one. LC/MS (ESI): 499.29. ¹H NMR (400 MHz, DMSO, d₆) δ 9.44 (s, 1H), 9.38 (s, 1H), 8.61 (d, 1H, J=5.05 Hz), 8.59 (m, 1H), 8.18 (s, 1H), 7.83 (m, 1H), 7.62 (s, 1H), 7.48 (m, 1H), 7.41 (s, 1H), 7.33 (s, 1H), 7.25 (m, 1H), 6.87 (d, 1H, J=8.59 Hz), 2.43 (s, 3H), 2.18 (m, 2H), 1.96 (m, 2H), 1.26 (s, 6H).

Example 1002

7-{5-Chloro-4-[2-(4-methyl-pyridin-2-yl)-phenylamino]-pyrimidin-2-ylamino}-1-methyl-1,3,4,5-tetrahydro-benzo[b]azepin-2-one 1002a) Prepared analogously as Example 216 replacing 2-iodo-1-methyl-1H-imidazole with 2-bromo-4-methylpyridine and 3-Ethyl-2,3,4,5-tetrahydro-1H-benzo[d]azepin-7-ylamine with 7-Amino-1-methyl-1,3,4,5-tetrahydro-benzo[b]azepin-2-one to afford 7-{5-Chloro-4-[2-(4-methyl-pyridin-2-yl)-phenylamino]-pyrimidin-2-ylamino}-1-methyl-1,3,4,5-tetrahydro-benzo[b]azepin-2-one. LC/MS (ESI): 485.27. ¹H NMR (400 MHz, DMSO, d₆) δ 9.49 (s, 1H), 8.62 (d, 1H, J=5.05 Hz), 8.19 (s, 1H), 7.89 (m, 1H), 7.83 (s, 1H), 7.54 (m, 2H), 7.32 (m, 2H), 7.25 (m, 3H), 3.21 (s, 3H), 2.57 (m, 2H), 2.43 (s, 3H), 2.16 (m, 2H), 2.03 (m, 2H).

Example 1003

7-{5-Chloro-4-[2-(5-methyl-pyridin-2-yl)-phenylamino]-pyrimidin-2-ylamino}-5,5-dimethyl-1,3,4,5-tetrahydro-benzo[b]azepin-2-one 1003a) Prepared analogously as Example 216 replacing 2-iodo-1-methyl-1H-imidazole with 2-bromo-5-methylpyridine and 3-Ethyl-2,3,4,5-tetrahydro-1H-benzo[d]azepin-7-ylamine with 7-Amino-5,5-dimethyl-1,3,4,5-tetrahydro-benzo[b]azepin-2-one to afford 7-{5-Chloro-4-[2-(5-methyl-pyridin-2-yl)-phenylamino]-pyrimidin-2-ylamino}-5,5-dimethyl-1,3,4,5-tetrahydro-benzo[b]azepin-2-one. LC/MS (ESI): 499.29. ¹H NMR (400 MHz, DMSO, d₆) δ 9.49 (s, 1H), 9.39 (s, 1H), 8.62 (m, 2H), 8.21 (s, 1H), 7.88 (m, 3H), 7.64 (d, 1H, J=8.59 Hz), 7.48 (m, 1H), 7.38 (m, 1H), 7.25 (m, 1H), 6.88 (d, 1H, J=8.34 Hz), 2.39 (s, 3H), 2.16 (m, 2H), 1.96 (m, 2H), 1.27 (s, 6H).

Example 1004

7-{5-Chloro-4-[2-(5-methyl-pyridin-2-yl)-phenylamino]-pyrimidin-2-ylamino}-1-methyl-1,3,4,5-tetrahydro-benzo[b]azepin-2-one 1004a) Prepared analogously as Example 216 replacing 2-iodo-1-methyl-1H-imidazole with 2-bromo-5-methylpyridine and 3-Ethyl-2,3,4,5-tetrahydro-1H-benzo[d]azepin-7-ylamine with 7-Amino-1-methyl-1,3,4,5-tetrahydro-benzo[b]azepin-2-one to afford 7-{5-Chloro-4-[2-(5-methyl-pyridin-2-yl)-phenylamino]-pyrimidin-2-ylamino}-1-methyl-1,3,4,5-tetrahydro-benzo[b]azepin-2-one. LC/MS (ESI): 485.23. ¹H NMR (400 MHz, DMSO, d₆) δ 9.43 (s, 1H), 8.62 (s, 2H), 8.15 (s, 1H), 7.82 (m, 3H), 7.53 (m, 2H), 7.37 (m, 1H), 7.21 (m, 2H), 5.05 (s, 1H), 3.20 (s, 3H), 2.46 (s, 3H), 1.97-2.16 (m, 6H).

Example 1005

7-[5-Chloro-4-(1-methyl-1H-benzoimidazol-4-ylamino)-pyrimidin-2-ylamino]-5,5-dimethyl-1,3,4,5-tetrahydro-benzo[b]azepin-2-one 1005a) Prepared analogously as Example 216c replacing 2-(1-Methyl-1H-imidazol-2-yl)-phenylamine with 1-Methyl-1H-benzimidazol-4-ylamine and 3-Ethyl-2,3,4,5-tetrahydro-1H-benzo[d]azepin-7-ylamine with 7-Amino-5,5-dimethyl-1,3,4,5-tetrahydro-benzo[b]azepin-2-one in Example 216d to afford 7-[5-Chloro-4-(1-methyl-1H-benzoimidazol-4-ylamino)-pyrimidin-2-ylamino]-5,5-dimethyl-1,3,4,5-tetrahydro-benzo[b]azepin-2-one. LC/MS (ESI): 462.17. ¹H NMR (400 MHz, DMSO, d₆) δ 9.34 (m, 3H), 9.16 (m, 1H), 8.23 (s, 1H), 7.71 (m, 2H), 7.53 (m, 1H), 7.34 (m, 1H), 6.53 (m, 1H), 4.03 (s, 3H), 2.13 (m, 2H), 1.90 (m, 2H), 1.19 (s, 6H).

Example 1006

5-Chloro-N*2*-[3-(2-methoxy-ethyl)-2,3,4,5-tetrahydro-1H-benzo[d]azepin-7-yl]-N*4*-(1-methyl-1H-benzoimidazol-4-yl)-pyrimidine-2,4-diamine 1006a) Prepared analogously as Example 216c replacing 2-(1-Methyl-1H-imidazol-2-yl)-phenylamine with 1-Methyl-1H-benzimidazol-4-ylamine and 3-Ethyl-2,3,4,5-tetrahydro-1H-benzo[d]azepin-7-ylamine with 8-Methoxy-3-(2-methoxy-ethyl)-2,3,4,5-tetrahydro-1H-benzo[d]azepin-7-ylamine in Example 216d to afford 5-Chloro-N*2*-[3-(2-methoxy-ethyl)-2,3,4,5-tetrahydro-1H-benzo[d]azepin-7-yl]-N*4*-(1-methyl-1H-benzoimidazol-4-yl)-pyrimidine-2,4-diamine. LC/MS (ESI): 478.18. ¹H NMR (400 MHz, DMSO, d₆) δ 9.63 (m, 1H), 9.38 (m, 1H), 8.23 (m, 1H), 7.62 (m, 1H), 7.48 (m, 1H), 7.31 (m, 1H), 7.19 (m, 1H), 6.92 (m, 1H), 3.99 (s, 3H), 3.34 (s, 3H), 2.99 (m, 3H), 2.70 (m, 3H), 2.37 (m, 2H), 2.33 (m, 2H), 1.93 (m, 2H).

Example 1007

7-[5-Chloro-4-(1-methyl-1H-benzoimidazol-4-ylamino)-pyrimidin-2-ylamino]-1-methyl-1,3,4,5-tetrahydro-benzo[b]azepin-2-one 1007a) Prepared analogously as Example 216c replacing 2-(1-Methyl-1H-imidazol-2-yl)-phenylamine with 1-Methyl-1H-benzimidazol-4-ylamine and 3-Ethyl-2,3,4,5-tetrahydro-1H-benzo[d]azepin-7-ylamine with 7-Amino-1-methyl-1,3,4,5-tetrahydro-benzo[b]azepin-2-one in Example 216d to afford 7-[5-Chloro-4-(1-methyl-1H-benzoimidazol-4-ylamino)-pyrimidin-2-ylamino]-1-methyl-1,3,4,5-tetrahydro-benzo[b]azepin-2-one. LC/MS (ESI): 448.11. ¹H NMR (400 MHz, DMSO, d₆) δ 9.41 (s, 2H), 9.22 (s, 1H), 8.25 (s, 1H), 7.76 (m, 1H), 7.72 (m, 1H), 7.58 (m, 1H), 7.19 (m, 2H), 6.94 (d, 1H, J=8.34 Hz), 4.03 (s, 3H), 3.15 (s, 3H), 2.38 (m, 2H), 2.07 (m, 2H), 1.91 (m, 2H).

Example 1008

7-{5-Chloro-4-[2-(6-methyl-pyridin-2-yl)-phenylamino]-pyrimidin-2-ylamino}-5,5-dimethyl-1,3,4,5-tetrahydro-benzo[b]azepin-2-one 1008a) Prepared analogously as Example 216 replacing 2-iodo-1-methyl-1H-imidazole with 2-bromo-6-methylpyridine and 3-Ethyl-2,3,4,5-tetrahydro-1H-benzo[d]azepin-7-ylamine with 7-Amino-5,5-dimethyl-1,3,4,5-tetrahydro-benzo[b]azepin-2-one to afford 7-{5-Chloro-4-[2-(6-methyl-pyridin-2-yl)-phenylamino]-pyrimidin-2-ylamino}-5,5-dimethyl-1,3,4,5-tetrahydro-benzo[b]azepin-2-one. LC/MS (ESI): 499.29. ¹H NMR (400 MHz, DMSO, d₆) δ 9.43 (s, 1H), 9.36 (s, 1H), 8.32 (m, 1H), 8.19 (s, 1H), 7.94 (m, 1H), 7.72 (m, 1H), 7.68 (m, 1H), 7.42 (m, 2H), 7.37 (m, 1H), 7.29 (m, 1H), 6.84 (d, 1H, J=8.59 Hz), 2.63 (s, 3H), 2.17 (m, 2H), 1.95 (m, 2H), 1.24 (s, 6H).

Example 1009

5-Chloro-N*2*-[3-(2-methoxy-ethyl)-2,3,4,5-tetrahydro-1H-benzo[d]azepin-7-yl]-N*4*-[2-(6-methyl-pyridin-2-yl)-phenyl]-pyrimidine-2,4-diamine 1009a) Prepared analogously as Example 216 replacing 2-iodo-1-methyl-1H-imidazole with 2-bromo-6-methylpyridine and 3-Ethyl-2,3,4,5-tetrahydro-1H-benzo[d]azepin-7-ylamine with 8-Methoxy-3-(2-methoxy-ethyl)-2,3,4,5-tetrahydro-1H-benzo[d]azepin-7-ylamine to afford 5-Chloro-N*2*-[3-(2-methoxy-ethyl)-2,3,4,5-tetrahydro-1H-benzo[d]azepin-7-yl]-N*4*-[2-(6-methyl-pyridin-2-yl)-phenyl]-pyrimidine-2,4-diamine. LC/MS (ESI): 515.28. $^1$H NMR (400 MHz, DMSO, $d_6$) δ 9.72 (m, 1H), 9.45 (s, 1H), 8.37 (d, 1H, J=8.34 Hz), 8.19 (s, 1H), 7.91 (m, 1H), 7.77 (d, 1 h, J=7.83 Hz), 7.69 (d, 1H, J=8.09 Hz), 7.52 (s, 1H), 7.45 (m, 2H), 7.33 (m, 1H), 7.26 (m, 1H), 7.07 (d, 1H, J=8.09 Hz), 3.71 (m, 4H), 3.65 (m, 2H), 3.34 (s, 3H), 2.92-3.17 (m, 6H), 2.63 (s, 3H).

Example 1010

7-{5-Chloro-4-[2-(4-trifluoromethyl-1H-imidazol-2-yl)-phenylamino]-pyrimidin-2-ylamino}-5,5-dimethyl-1,3,4,5-tetrahydro-benzo[b]azepin-2-one 1010a)
2-(2-Nitro-phenyl)-4-trifluoromethyl-1H-imidazole The procedure was adapted from J. Am. Chem. Soc., 2003, 125, 10241-10249. 3,3-Dibromo-1,1,1-trifluoro-propan-2-one (5.58 g, 20.7 mmol) was added to a solution of Sodium acetate trihydrate (5.63 g, 41.4 mmol) in Water (7.0 mL) and the mixture was heated at 100° C. for ~1 hour. Upon cooling, 2-Nitrobenzaldehyde (2.5 g, 16.0 mmol) was dissolved in Methanol (40 mL) and was added to the solution. Ammonia (9.0 mL) was then added and the solution was allowed to stir overnight at room temperature. MeOH was removed en vacuo and the yellow precipitate was collected via filtration. The solid was dried to yield 4.0 grams (94%) the desired product.

1010b)
2-(4-Trifluoromethyl-1H-imidazol-2-yl)-phenylamine 2-(2-Nitro-phenyl)-4-trifluoromethyl-1H-imidazole (1.50 g, 5.83 mmol) was dissolved in Methanol (35 mL) and solution was carefully added to 10% Palladium on Carbon (90:10, carbon black:Palladium, 0.500 g) under nitrogen. The reaction was then hydrogenated at 55 psi until HPLC showed consumption of starting material (~4 hours). Catalyst was removed via filtration and the filtrate was reduced en vacuo to afford 1.25 grams (94%) of the desired product. LC/MS (ESI): 288.09.

1010c) (2,5-Dichloro-pyrimidin-4-yl)-[2-(4-trifluoromethyl-1H-imidazol-2-yl)-phenyl]-amine 2-(4-Trifluoromethyl-1H-imidazol-2-yl)-phenylamine (0.200 g, 0.880 mmol) and 2,4,5-Trichloro-pyrimidine (0.161 g, 0.880 mmol) were dissolved in N,N-Dimethylformamide (5.0 mL) and the reaction was heated at 50° C. and was allowed to stir overnight. The reaction mixture was poured over saturated ammonium chloride, and organics were extracted with ethyl acetate/dichloromethane. Combined organics were dried over sodium sulfate, filtered and reduced en vacuo. The crude mixture was purified by Isco flash column chromatography (Hexane/Ethyl Acetate). Combined fractions were reduced en vacuo to afford 220 mg (67%) of the desired product.

1010d) 7-{5-Chloro-4-[2-(4-trifluoromethyl-1H-imidazol-2-yl)-phenylamino]-pyrimidin-2-ylamino}-5,5-dimethyl-1,3,4,5-tetrahydro-benzo[b]azepin-2-one (2,5-Dichloro-pyrimidin-4-yl)-[2-(4-trifluoromethyl-1H-imidazol-2-yl)-phenyl]-amine (50.0 mg, 0.134 mmol), 7-Amino-5,5-dimethyl-1,3,4,5-tetrahydro-benzo[b]azepin-2-one (27.0 mg, 0.132 mmol) and 10-Camphorsulfonic acid (31.0 mg, 0.133 mmol) were suspended in Isopropyl alcohol (3.0 mL, 0.039 mol) and the reaction was microwaved on 300 watts, 140° C. for 20 minutes. The reaction mixture was then reduced under nitrogen and the crude residue was isolated and purified by prep HPLC to afford 18.95 mg (26%) of the desired product as a TFA salt. LC/MS (ESI): 558.26. $^1$H NMR (400 MHz, DMSO, $d_6$) δ 9.46 (s, 1H), 9.39 (s, 1H), 8.96 (m, 1H), 8.23 (s, 1H), 8.08 (s, 1H), 7.97 (m, 1H), 7.66 (m, 1H), 7.54 (m, 1H), 7.39 (m, 1H), 7.21 (m, 1H), 6.91 (d, 1H, J=8.59 Hz), 2.16 (m, 2H), 1.98 (m, 2H), 1.29 (s, 6H).

Example 1011

5-Chloro-N*2*-[3-(2-methoxy-ethyl)-2,3,4,5-tetrahydro-1H-benzo[d]azepin-7-yl]-N*4*-[2-(4-trifluoromethyl-1H-imidazol-2-yl)-phenyl]-pyrimidine-2,4-diamine 1011a) Prepared analogously to Example 1010 replacing 7-Amino-5,5-dimethyl-1,3,4,5-tetrahydro-benzo[b]azepin-2-one with 8-Methoxy-3-(2-methoxy-ethyl)-2,3,4,5-tetrahydro-1H-benzo[d]azepin-7-ylamine to afford the title compound. LC/MS (ESI): 558.26. $^1$H NMR (400 MHz, DMSO, $d_6$) δ 9.66 (m, 1H), 9.51 (s, 1H), 8.94 (m, 1H), 8.24 (s, 1H), 8.08 (s, 1H), 7.99 (m, 1H), 7.50 (s, 1H), 7.48 (m, 1H), 7.40 (m, 1H), 7.21 (m, 1H), 7.14 (d, 1H, J=7.83 Hz), 3.34 (s, 3H), 2.88-3.40 (m, 12H).

Example 1012

7-{5-Chloro-4-[2-(4-trifluoromethyl-1H-imidazol-2-yl)-phenylamino]-pyrimidin-2-ylamino}-1,3,4,5-tetrahydro-benzo[b]azepin-2-one 1012a) Prepared analogously to Example 1010 replacing 7-Amino-5,5-dimethyl-1,3,4,5-tetrahydro-benzo[b]azepin-2-one with 7-Amino-1,3,4,5-tetrahydro-benzo[b]azepin-2-one to afford 7-{5-Chloro-4-[2-(4-trifluoromethyl-1H-imidazol-2-yl)-phenylamino]-pyrimidin-2-ylamino}-1,3,4,5-tetrahydro-benzo[b]azepin-2-one. LC/MS (ESI): 514.21. $^1$H NMR (400 MHz, DMSO, $d_6$) δ 9.49 (s, 1H), 9.37 (s, 1H), 8.92 (m, 1H), 8.24 (s, 1H), 8.07 (s, 1H), 7.97 (d, 1H, J=7.84 Hz), 7.49 (s, 1H), 7.47 (m, 1H), 7.40 (m, 1H), 7.21 (m, 1H), 6.90 (d, 1H, J=8.59 Hz), 2.67 (m, 2H), 2.14 (m, 4H).

Example 1013

7-{5-Chloro-4-[2-(4-trifluoromethyl-1H-imidazol-2-yl)-phenylamino]-pyrimidin-2-ylamino}-1-methyl-1,3,4,5-tetrahydro-benzo[b]azepin-2-one 1013a) Prepared analogously to Example 1010 replacing 7-Amino-5,5-dimethyl-1,3,4,5-tetrahydro-benzo[b]azepin-2-one with 7-Amino-1-methyl-1,3,4,5-tetrahydro-benzo[b]

azepin-2-one to afford the title compound. LC/MS (ESI): 528.21. $^1$H NMR (400 MHz, DMSO, d$_6$) δ 9.60 (s, 1H), 8.92 (m, 1H), 8.27 (s, 1H), 8.08 (s, 1H), 7.98 (m, 1H), 7.58 (m, 2H), 7.40 (m, 1H), 7.23 (m, 2H), 3.22 (s, 3H), 2.59 (m, 2H), 2.16 (m, 2H), 2.04 (m, 2H).

Example 1014

7-[5-Chloro-4-(2-trifluoromethyl-1H-benzoimidazol-5-ylamino)-pyrimidin-2-ylamino]-5,5-dimethyl-1,3,4,5-tetrahydro-benzo[b]azepin-2-one 1014a) Prepared analogously as Example 216c replacing 2-(1-Methyl-1H-imidazol-2-yl)-phenylamine with 1-Trifluoromethyl-1H-benzimidazol-4-ylamine and 3-Ethyl-2,3,4,5-tetrahydro-1H-benzo[d]azepin-7-ylamine with 7-Amino-5,5-dimethyl-1,3,4,5-tetrahydro-benzo[b]azepin-2-one in Example 216d to afford the title compound. LC/MS (ESI): 516.21. $^1$H NMR (400 MHz, DMSO, d$_6$) δ 9.56 (s, 1H), 9.35 (s, 1H), 9.32 (s, 1H), 8.20 (s, 1H), 7.90 (s, 1H), 7.68 (d, 1H, J=8.84 Hz), 7.56 (d, 1H, J=8.85 Hz), 7.46 (s, 1H), 7.41 (d, 1H, J=8.33 Hz), 6.71 (d, 1H, J=8.33 Hz), 2.05 (m, 2H), 1.72 (m, 2H), 1.02 (s, 6H).

Example 1015

5-Chloro-N*2*-[3-(2-methoxy-ethyl)-2,3,4,5-tetrahydro-1H-benzo[d]azepin-7-yl]-N*4*-(2-trifluoromethyl-1H-benzoimidazol-5-yl)-pyrimidine-2,4-diamine 1015a) Prepared analogously as Example 216c replacing 2-(1-Methyl-1H-imidazol-2-yl)-phenylamine with 1-Trifluoromethyl-1H-benzimidazol-4-ylamine and 3-Ethyl-2,3,4,5-tetrahydro-1H-benzo[d]azepin-7-ylamine with 8-Methoxy-3-(2-methoxy-ethyl)-2,3,4,5-tetrahydro-1H-benzo[d]azepin-7-ylamine in Example 216d to afford 5-Chloro-N*2*-[3-(2-methoxy-ethyl)-2,3,4,5-tetrahydro-1H-benzo[d]azepin-7-yl]-N*4*-(2-trifluoromethyl-1H-benzoimidazol-5-yl)-pyrimidine-2,4-diamine. LC/MS (ESI): 532.25. $^1$H NMR (400 MHz, DMSO, d$_6$) δ 9.71 (s, 1H), 9.56 (s, 1H), 9.31 (s, 1H), 8.20 (s, 1H), 7.91 (s, 1H), 7.74 (d, 1H, J=8.84 Hz), 7.59 (d, 1H, J=8.84 Hz), 7.40 (s, 1H), 7.31 (d, 1H, J=8.09 Hz), 6.92 (d, 1H, J=8.34 Hz), 3.68 (m, 2H), 3.59 (m, 1H), 3.47 (m, 1H), 3.35 (s, 3H), 3.06 (m, 3H), 2.92 (m, 5H).

Example 1016

7-[5-Chloro-4-(2-trifluoromethyl-1H-benzoimidazol-5-ylamino)-pyrimidin-2-ylamino]-1-methyl-1,3,4,5-tetrahydro-benzo[b]azepin-2-one 1016a) Prepared analogously as Example 216c replacing 2-(1-Methyl-1H-imidazol-2-yl)-phenylamine with 1-Trifluoromethyl-1H-benzimidazol-4-ylamine and 3-Ethyl-2,3,4,5-tetrahydro-1H-benzo[d]azepin-7-ylamine with 7-Amino-1-methyl-1,3,4,5-tetrahydro-benzo[b]azepin-2-one in Example 216d to afford 7-[5-Chloro-4-(2-trifluoromethyl-1H-benzoimidazol-5-ylamino)-pyrimidin-2-ylamino]-1-methyl-1,3,4,5-tetrahydro-benzo[b]azepin-2-one. LC/MS (ESI): 502.16. $^1$H NMR (400 MHz, DMSO, d$_6$) δ 9.46 (s, 1H), 9.19 (s, 1H), 8.17 (s, 1H), 7.95 (s, 1H), 7.72 (d, 1H, J=5.31 Hz), 7.51 (s, 1H), 7.41 (s, 1H), 7.36 (d, 1H, J=10.10 Hz), 6.99 (m, 1H), 2.73 (s, 3H), 2.09 (m, 2H), 2.00 (m, 2H), 1.72 (m, 2H).

Example 1017

(1S,2S,3R,4R)-3-[5-Chloro-2-(7-hydroxy-6,7,8,9-tetrahydro-5H-benzocyclohepten-2-ylamino)-pyrimidin-4-ylamino]-bicyclo[2.2.1]hept-5-ene-2-carboxylic acid amide 1017a) Prepared analogously to Example 216d replacing 3-Ethyl-2,3,4,5-tetrahydro-1H-benzo[d]azepin-7-ylamine with 2-Amino-6,7,8,9-tetrahydro-5H-benzocyclohepten-7-ol and (2,5-Dichloro-pyrimidin-4-yl)-[2-(1-methyl-1H-imidazol-2-yl)-phenyl]-amine was replaced with (1S,2S,3R,4R)-3-(2,5-Dichloro-pyrimidin-4-ylamino)-bicyclo[2.2.1] hept-5-ene-2-carboxylic acid amide. 2-Amino-6,7,8,9-tetrahydro-5H-benzocyclohepten-7-ol is a byproduct from the reductive amination of 2-Nitro-5,6,8,9-tetrahydro-benzocyclohepten-7-one with various amines. The reaction was carried out in the presence of the desired reductive amination product to provide a crude mixture of amino and alcohol products. The crude mix was then reduced and a mixture of amino and alcohol products were used in the synthesis of target compounds. The mixture was then purified by prep HPLC to afford the desired amino compound as well as (1S,2S,3R,4R)-3-[5-Chloro-2-(7-hydroxy-6,7,8,9-tetrahydro-5H-benzocyclohepten-2-ylamino)-pyrimidin-4-ylamino]-bicyclo[2.2.1]hept-5-ene-2-carboxylic acid amide. LC/MS (ESI): 440.22. $^1$H NMR (400 MHz, DMSO, d$_6$) δ 9.12 (s, 1H), 7.93 (s, 1H), 7.78 (s, 1H), 7.69 (m, 1H), 7.46 (m, 2H), 7.26 (s, 1H), 6.97 (d, 1H, J=8.08 Hz), 6.35 (m, 1H), 6.27 (m, 1H), 4.58 (m, 1H), 4.15 (m, 1H), 3.72 (m, 1H), 3.31 (s, 2H), 2.88 (s, 1H), 2.78 (m, 3H), 2.11 (d, 1H, J=8.59 Hz), 1.89 (m, 2H), 1.41 (d, 1H, J=8.09 Hz), 1.33 (m, 2H).

Example 1018

5-Chloro-N*4*-[2-(3-methoxy-pyridin-2-yl)-phenyl]-N*2*-(7-morpholin-4-yl-6,7,8,9-tetrahydro-5H-benzocyclohepten-2-yl)-pyrimidine-2,4-diamine 1018a) Prepared analogously as Example 216 replacing 2-iodo-1-methyl-1H-imidazole with 2-bromo-3-methoxypyridine and 3-Ethyl-2,3,4,5-tetrahydro-1H-benzo[d]azepin-7-ylamine with 7-Morpholin-4-yl-6,7,8,9-tetrahydro-5H-benzocyclohepten-2-ylamine to afford 5-Chloro-N*4*-[2-(3-methoxy-pyridin-2-yl)-phenyl]-N*2*-(7-morpholin-4-yl-6,7,8,9-tetrahydro-5H-benzocyclohepten-2-yl)-pyrimidine-2,4-diamine. LC/MS (ESI): 557.25. $^1$H NMR (400 MHz, DMSO, d$_6$) δ 9.50 (m, 1H), 9.37 (s, 1H), 8.35 (d, 1H, J=4.80 Hz), 8.19 (d, 1H, J=8.09 Hz), 8.11 (s, 1H), 7.70 (d, 2H, J=7.83 Hz), 7.51 (m, 3H), 7.26 (m, 2H), 7.02 (d, 1H, J=8.33 Hz), 4.00 (d, 2H, J=11.37 Hz), 3.82 (s, 3H), 3.74 (m, 2H), 3.57 (m, 1H), 3.32 (m, 2H), 3.16 (m, 2H), 2.68 (m, 3H), 2.38 (m, 3H), 1.44 (m, 2H).

Example 1019

2-{5-Chloro-4-[2-(3-methoxy-pyridin-2-yl)-phenylamino]-pyrimidin-2-ylamino}-6,7,8,9-tetrahydro-5H-benzocyclohepten-7-ol 1019a) Prepared analogously as Example 216 replacing 2-iodo-1-methyl-1H-imidazole with 2-bromo-3-methoxypyridine and 3-Ethyl-2,3,4,5-tetrahydro-1H-benzo[d]azepin-7-ylamine with 2-Amino-6,7,8,9-tetrahydro-5H-benzocyclohepten-7-ol (See Example 1017) to afford 2-{5-Chloro-4-[2-(3-methoxy-pyridin-2-yl)-phenylamino]-pyrimidin-2-ylamino}-6,7,8,9-tetrahydro-5H-benzocyclohepten-7-ol. LC/MS (ESI): 488.17. $^1$H NMR (400 MHz, DMSO, d$_6$) δ

9.35 (m, 1H), 8.36 (m, 1H), 8.14 (m, 1H), 8.11 (s, 1H), 7.71 (m, 2H), 7.52 (m, 1H), 7.45 (m, 1H), 7.29 (s, 1H), 7.25 (m, 2H), 6.95 (d, 1H, J=8.09 Hz), 3.81 (s, 3H), 3.73 (m, 1H), 2.80 (m, 4H), 1.90 (m, 2H), 1.32 (m, 2H).

Example 1020

5-Chloro-N*4*-[2-(3-methyl-pyridin-2-yl)-phenyl]-N*2*-(7-morpholin-4-yl-6,7,8,9-tetrahydro-5H-benzocyclohepten-2-yl)-pyrimidine-2,4-diamine 1020a) Prepared analogously as Example 216 replacing 2-iodo-1-methyl-1H-imidazole with 2-bromo-3-methylpyridine and 3-Ethyl-2,3,4,5-tetrahydro-1H-benzo[d]azepin-7-ylamine with 7-Morpholin-4-yl-6,7,8,9-tetrahydro-5H-benzocyclohepten-2-ylamine to afford 5-Chloro-N*4*-[2-(3-methyl-pyridin-2-yl)-phenyl]-N*2*-(7-morpholin-4-yl-6,7,8,9-tetrahydro-5H-benzocyclohepten-2-yl)-pyrimidine-2,4-diamine. LC/MS (ESI): 541.26. $^1$H NMR (400 MHz, DMSO, d$_6$) δ 9.50 (m, 2H), 9.24 (m, 1H), 8.67 (s, 1H), 8.08 (s, 1H), 8.01 (m, 2H), 7.58 (m, 2H), 7.48 (m, 1H), 7.39 (m, 1H), 7.29 (d, 1H, J=7.58 Hz), 7.01 (d, 1H, J=8.09 Hz), 3.98 (m, 2H), 3.76 (m, 2H), 3.56 (m, 1H), 3.37 (m, 2H), 3.28 (m, 2H), 2.86 (m, 2H), 2.68 (m, 2H), 2.16 (s, 3H), 1.91 (m, 2H), 1.44 (m, 2H).

Example 1021

2-{5-Chloro-4-[2-(3-methyl-pyridin-2-yl)-phenylamino]-pyrimidin-2-ylamino}-6,7,8,9-tetrahydro-5H-benzocyclohepten-7-ol 1021a) Prepared analogously as Example 216 replacing 2-iodo-1-methyl-1H-imidazole with 2-bromo-3-methylpyridine and 3-Ethyl-2,3,4,5-tetrahydro-1H-benzo[d]azepin-7-ylamine with 2-Amino-6,7,8,9-tetrahydro-5H-benzocyclohepten-7-ol (See Example 1017) to afford 2-{5-Chloro-4-[2-(3-methyl-pyridin-2-yl)-phenylamino]-pyrimidin-2-ylamino}-6,7,8,9-tetrahydro-5H-benzocyclohepten-7-ol. LC/MS (ESI): 472.17. $^1$H NMR (400 MHz, DMSO, d$_6$) δ 9.47 (m, 1H), 9.13 (m, 1H), 8.68 (d, 1H, J=4.80 Hz), 8.10 (m, 1H), 8.06 (s, 1H), 7.98 (m, 1H), 7.60 (m, 3H), 7.41 (m, 2H), 7.22 (d, 1H, J=7.83 Hz), 6.94 (d, 1H, J=8.09 Hz), 3.72 (m, 1H), 2.65 (m, 2H), 2.44 (m, 2H), 2.23 (s, 3H), 1.77 (m, 2H), 1.30 (m, 2H).

Example 1022

2-[5-Chloro-2-(5,5-dimethyl-2-oxo-2,3,4,5-tetrahydro-1H-benzo[b]azepin-7-ylamino)-pyrimidin-4-ylamino]-N-propyl-benzamide 1022a) (2-Propylcarbamoyl-phenyl)-carbamic acid tert-butyl ester 2-tert-Butoxycarbonylamino-benzoic acid (1.00 g, 0.00421 mol) and 1-Propanamine (0.249 g, 0.00421 mol) were dissolved in Tetrahydrofuran (10.0 mL, 0.123 mol) and the mixture was treated with N-(3-Dimethylaminopropyl)-N'-ethylcarbodiimide hydrochloride (0.808 g, 0.00421 mol) and 1-Hydroxybenzotriazole (0.570 g, 0.00421 mol). The reaction was then allowed to stir overnight at room temperature. The reaction mixture was poured over saturated sodium bicarbonate, and organics were extracted with ethyl acetate/dichloromethane. Combined organics were dried over sodium sulfate, filtered and reduced en vacuo. The crude mixture was purified by Isco flash column chromatography (Hexane/Ethyl Acetate). Combined fractions were reduced en vacuo to afford 1.17 grams (49%) of (2-Propylcarbamoyl-phenyl)-carbamic acid tert-butyl ester.

1022b) 2-Amino-N-propyl-benzamide (2-Propylcarbamoyl-phenyl)-carbamic acid tert-butyl ester (0.570 g, 0.00205 mol) was dissolved in Methylene chloride (5.0 mL, 0.078 mol) and Trifluoroacetic Acid (3.0 mL, 0.039 mol) was added to the mixture. The reaction was allowed to stir overnight at room temperature. The reaction mixture was reduced under nitrogen and the crude product (360 mg, 99%) was used in subsequent chemistry without further purification. The excess TFA will be neutralized in the next synthetic step. LC/MS (ESI): 179.24.

1022c) 2-(2,5-Dichloro-pyrimidin-4-ylamino)-N-propyl-benzamide

2-Amino-N-propyl-benzamide (0.360 g, 0.00202 mol), 2,4,5-Trichloro-pyrimidine (0.370 g, 0.00202 mol) and Potassium carbonate (0.837 g, 0.00606 mol) were dissolved in N,N-Dimethylformamide (10.0 mL, 0.129 mol) and the reaction was heated at 90° C. and was allowed to stir overnight. The reaction mixture was then cooled was poured over saturated ammonium chloride, and organics were extracted with ethyl acetate/dichloromethane. Combined organics were dried over sodium sulfate, filtered and reduced en vacuo. The crude mixture was purified by Isco flash column chromatography (Hexane/Ethyl Acetate). Combined fractions were reduced en vacuo to afford 420 mg (64%) of 2-(2,5-Dichloro-pyrimidin-4-ylamino)-N-propyl-benzamide. LC/MS (ESI): 325.12. 2-(2,5-Dichloro-pyrimidin-4-ylamino)-N-butyl-benzamide was made in an analogous fashion replacing 1-aminopropane with 1-aminobutane.

1022d) 2-[5-Chloro-2-(5,5-dimethyl-2-oxo-2,3,4,5-tetrahydro-1H-benzo[b]azepin-7-ylamino)-pyrimidin-4-ylamino]-N-propyl-benzamide 2-(2,5-Dichloro-pyrimidin-4-ylamino)-N-propyl-benzamide (50.0 mg, 0.000154 mol), 7-Amino-5,5-dimethyl-1,3,4,5-tetrahydro-benzo[b]azepin-2-one (31.4 mg, 0.000154 mol) and 10-Camphorsulfonic acid (35.7 mg, 0.000154 mol) were dissolved in Isopropyl alcohol (3.00 mL, 0.0392 mol) and the reaction was microwaved on 300 watts, 140° C. for 20 minutes. The reaction mixture was reduced under nitrogen. The crude residue was isolated and purified by prep HPLC to afford 28.57 mg (38%) of the title compound. LC/MS (ESI): 493.17. $^1$H NMR (400 MHz, DMSO, d$_6$) δ 9.44 (s, 1H), 9.37 (s, 1H), 8.76 (m, 2H), 8.21 (s, 1H), 7.76 (d, 1H, J=7.83 Hz), 7.65 (d, 1H, J=8.08 Hz), 7.48 (m, 2H), 7.14 (t, 1H, J=7.33 Hz), 6.88 (d, 1H, J=8.34 Hz), 3.25 (m, 2H), 2.17 (m, 2H), 1.97 (m, 2H), 1.55 (m, 2H), 1.29 (s, 6H), 0.90 (t, 3H, J=7.33 Hz).

Example 1023

2-{5-Chloro-2-[3-(2-methoxy-ethyl)-2,3,4,5-tetrahydro-1H-benzo[d]azepin-7-ylamino]-pyrimidin-4-ylamino}-N-propyl-benzamide 1023a) Prepared analogously to Example 1022 replacing 7-Amino-5,5-dimethyl-1,3,4,5-tetrahydro-benzo[b]azepin-2-one with 8-Methoxy-3-(2-methoxy-ethyl)-2,3,4,5-tetrahydro-1H-benzo[d]azepin-7-ylamine to afford 2-{5-Chloro-2-[3-(2-methoxy-ethyl)-2,3,4,5-tetrahydro-1H-benzo[d]azepin-7-ylamino]-pyrimidin-4-ylamino}-N-propyl-benzamide LC/MS (ESI): 509.21. $^1$H NMR (400 MHz, DMSO, d$_6$) δ 9.67 (m, 1H), 9.49 (s, 1H), 8.78 (m, 1H), 8.76 (d, 1H, J=6.07 Hz), 8.22 (s, 1H), 7.78 (d, 1H, J=8.08 Hz), 7.48 (m, 3H), 7.12 (m, 2H), 3.69 (m, 4H), 3.45 (m, 2H), 3.34 (s, 3H), 2.87-3.22 (m, 8H), 1.56 (m, 2H), 0.90 (t, 3H, J=7.33 Hz).

Example 1024

2-[5-Chloro-2-(2-oxo-2,3,4,5-tetrahydro-1H-benzo[b]azepin-7-ylamino)-pyrimidin-4-ylamino]-N-propyl-benzamide 1024a) Prepared analogously to Example 1022 replacing 7-Amino-5,5-dimethyl-1,3,4,5-tetrahydro-benzo[b]azepin-2-one with 7-Amino-1,3,4,5-tetrahydro-benzo[b]azepin-2-one to afford 2-[5-Chloro-2-(2-oxo-2,3,4,5-tetrahydro-1H-benzo[b]azepin-7-ylamino)-pyrimidin-4-ylamino]-N-propyl-benzamide. LC/MS (ESI): 465.17. $^1$H NMR (400 MHz, DMSO, $d_6$) δ 9.46 (s, 1H), 9.34 (s, 1H), 8.77 (m, 1H), 8.65 (m, 1H), 8.22 (s, 1H), 7.75 (d, 1H, J=7.84 Hz), 7.56 (s, 1H), 7.45 (m, 2H), 7.15 (t, 1H, J=7.58 Hz), 6.87 (d, 1H, J=8.59 Hz), 3.27 (m, 2H), 2.62 (m, 2H), 2.10 (m, 4H), 1.58 (m, 2H), 0.90 (t, 3H, J=7.58 Hz).

Example 1025

2-[5-Chloro-2-(1-methyl-2-oxo-2,3,4,5-tetrahydro-1H-benzo[b]azepin-7-ylamino)-pyrimidin-4-ylamino]-N-propyl-benzamide 1025a) Prepared analogously to Example 1022 replacing 7-Amino-5,5-dimethyl-1,3,4,5-tetrahydro-benzo[b]azepin-2-one with 7-Amino-1-methyl-1,3,4,5-tetrahydro-benzo[b]azepin-2-one to afford 2-[5-Chloro-2-(1-methyl-2-oxo-2,3,4,5-tetrahydro-1H-benzo[b]azepin-7-ylamino)-pyrimidin-4-ylamino]-N-propyl-benzamide. LC/MS (ESI): 479.16. $^1$H NMR (400 MHz, DMSO, $d_6$) δ 9.53 (s, 1H), 8.79 (m, 1H), 8.67 (m, 1H), 8.24 (s, 1H), 7.77 (m, 1H), 7.57 (m, 2H), 7.32 (m, 1H), 7.18 (m, 2H), 3.26 (m, 2H), 3.20 (s, 3H), 2.17 (m, 3H), 2.04 (m, 3H), 1.56 (m, 2H), 0.90 (t, 3H, J=7.58 Hz).

Example 1026

2-{5-Chloro-2-[8-methoxy-3-(2-methoxy-ethyl)-2,3,4,5-tetrahydro-1H-benzo[d]azepin-7-ylamino]-pyrimidin-4-ylamino}-N-propyl-benzamide 1026a) Prepared analogously to Example 1022 replacing 7-Amino-5,5-dimethyl-1,3,4,5-tetrahydro-benzo[b]azepin-2-one with 8-Methoxy-3-(2-methoxy-ethyl)-2,3,4,5-tetrahydro-1H-benzo[d]azepin-7-ylamine to afford 2-{5-Chloro-2-[8-methoxy-3-(2-methoxy-ethyl)-2,3,4,5-tetrahydro-1H-benzo[d]azepin-7-ylamino]-pyrimidin-4-ylamino}-N-propyl-benzamide. LC/MS (ESI): 539.20. $^1$H NMR (400 MHz, DMSO, $d_6$) δ 9.65 (m, 1H), 8.76 (m, 1H), 8.55 (d, 1H, J=8.84 Hz), 8.26 (s, 1H), 8.18 (s, 1H), 7.74 (d, 1H, J=7.84 Hz), 7.67 (s, 1H), 7.40 (t, 1H, J=7.83 Hz), 7.14 (t, 1H, J=7.58 Hz), 6.97 (s, 1H), 3.80 (s, 3H), 3.69 (m, 4H), 3.65 (m, 2H), 3.40 (s, 3H), 3.01-3.16 (m, 8H), 1.54 (m, 2H), 0.90 (t, 3H, J=7.58 Hz).

Example 1027

N-Butyl-2-[5-chloro-2-(5,5-dimethyl-2-oxo-2,3,4,5-tetrahydro-1H-benzo[b]azepin-7-ylamino)-pyrimidin-4-ylamino]-benzamide 1027a) Prepared analogously to Example 1022 replacing 1-propylamine with 1-butylamine to afford N-Butyl-2-[5-chloro-2-(5,5-dimethyl-2-oxo-2,3,4,5-tetrahydro-1H-benzo[b]azepin-7-ylamino)-pyrimidin-4-ylamino]-benzamide. LC/MS (ESI): 507.20. $^1$H NMR (400 MHz, DMSO, $d_6$) δ 9.47 (s, 1H), 9.38 (s, 1H), 8.70 (m, 2H), 8.22 (s, 1H), 7.75 (d, 1H, J=7.84 Hz), 7.64 (d, 1H, J=8.33 Hz), 7.47 (m, 2H), 7.15 (t, 1H, J=7.58 Hz), 6.88 (d, 1H, J=8.59 Hz), 3.29 (m, 2H), 2.17 (m, 2H), 1.97 (m, 2H), 1.52 (m, 2H), 1.36 (m, 2H), 1.31 (s, 6H), 0.90 (t, 3H, J=7.32 Hz).

Example 1028

N-Butyl-2-{5-chloro-2-[3-(2-methoxy-ethyl)-2,3,4,5-tetrahydro-1H-benzo[d]azepin-7-ylamino]-pyrimidin-4-ylamino}-benzamide 1028a) Prepared analogously to Example 1023 replacing 1-propylamine with 1-butylamine to afford N-Butyl-2-{5-chloro-2-[3-(2-methoxy-ethyl)-2,3,4,5-tetrahydro-1H-benzo[d]azepin-7-ylamino]-pyrimidin-4-ylamino}-benzamide. LC/MS (ESI): 523.21. $^1$H NMR (400 MHz, DMSO, $d_6$) δ 9.67 (s, 1H), 9.49 (s, 1H), 8.69 (m, 2H), 8.12 (s, 1H), 7.76 (d, 1H, J=7.58 Hz), 7.46 (m, 3H), 7.12 (m, 2H), 3.70 (m, 4H), 3.62 (m, 2H), 3.39 (s, 3H), 3.08-3.20 (m, 8H), 1.52 (m, 2H), 1.35 (m, 2H), 0.91 (t, 3H, J=7.58 Hz).

Example 1029

N-Butyl-2-[5-chloro-2-(2-oxo-2,3,4,5-tetrahydro-1H-benzo[b]azepin-7-ylamino)-pyrimidin-4-ylamino]-benzamide 1029a) Prepared analogously to Example 1024 replacing 1-propylamine with 1-butylamine to afford N-Butyl-2-[5-chloro-2-(2-oxo-2,3,4,5-tetrahydro-1H-benzo[b]azepin-7-ylamino)-pyrimidin-4-ylamino]-benzamide. LC/MS (ESI): 479.16. $^1$H NMR (400 MHz, DMSO, $d_6$) δ 9.47 (s, 1H), 9.38 (s, 1H), 8.76 (m, 1H), 8.69 (m, 1H), 8.22 (s, 1H), 7.76 (m, 1H), 7.43 (m, 2H), 7.15 (m, 2H), 6.87 (d, 1H, J=8.59 Hz), 3.29 (m, 2H), 2.67 (m, 2H), 2.08 (m, 4H), 1.50 (m, 2H), 1.38 (m, 2H), 0.91 (t, 3H, J=7.33 Hz).

Example 1030

N-Butyl-2-[5-chloro-2-(1-methyl-2-oxo-2,3,4,5-tetrahydro-1H-benzo[b]azepin-7-ylamino)-pyrimidin-4-ylamino]-benzamide 1030a) Prepared analogously to Example 1025 replacing 1-propylamine with 1-butylamine to afford N-Butyl-2-[5-chloro-2-(1-methyl-2-oxo-2,3,4,5-tetrahydro-1H-benzo[b]azepin-7-ylamino)-pyrimidin-4-ylamino]-benzamide. LC/MS (ESI): 493.16. $^1$H NMR (400 MHz, DMSO, $d_6$) δ 9.54 (s, 1H), 8.75 (m, 1H), 8.64 (m, 1H), 8.24 (s, 1H), 7.75 (d, 1H, J=7.83 Hz), 7.47 (m, 2H), 7.23 (m, 1H), 7.16 (m, 2H), 3.29 (m, 2H), 2.57 (m, 2H), 2.15 (m, 2H), 2.02 (m, 2H), 1.52 (m, 2H), 1.33 (m, 2H), 0.91 (t, 3H, J=7.32 Hz).

Example 1031

N-Butyl-2-{5-chloro-2-[8-methoxy-3-(2-methoxy-ethyl)-2,3,4,5-tetrahydro-1H-benzo[d]azepin-7-ylamino]-pyrimidin-4-ylamino}-benzamide 1031a) Prepared analogously to Example 1026 replacing 1-propylamine with 1-butylamine to afford N-Butyl-2-{5-chloro-2-[8-methoxy-3-(2-methoxy-ethyl)-2,3,4,5-tetrahydro-1H-benzo[d]azepin-7-ylamino]-pyrimidin-4-ylamino}-benzamide. LC/MS (ESI): 553.26. $^1$H NMR (400 MHz, DMSO, d$_6$) δ 9.68 (m, 1H), 8.75 (m, 1H), 8.54 (d, 1H, J=8.58 Hz), 8.30 (s, 1H), 8.19 (s, 1H), 7.75 (d, 1H, J=7.84 Hz), 7.61 (s, 1H), 7.38 (t, 1H, J=8.34 Hz), 7.14 (t, 1H, J=7.58 Hz), 6.97 (s, 1H), 3.80 (s, 3H), 3.65 (m, 4H), 3.40 (m, 2H), 3.34 (s, 3H), 3.01-3.21 (m, 8H), 1.51 (m, 2H), 1.34 (m, 2H), 0.90 (t, 3H, J=7.32 Hz).

Example 1032

2-[5-Chloro-2-(7-morpholin-4-yl-6,7,8,9-tetrahydro-5H-benzocyclohepten-2-ylamino)-pyrimidin-4-ylamino]-N,N-dimethyl-benzenesulfonamide 1032a) 7-Morpholin-4-yl-6,7,8,9-tetrahydro-5H-benzocyclohepten-2-ylamine (18.0 mg, 0.0000731 mol), 2-(2,5-Dichloro-pyrimidin-4-ylamino)-N,N-dimethyl-benzenesulfonamide (25.0 mg, 0.0000720 mol) and 10-Camphorsulfonic acid (17.0 mg, 0.0000732 mol) were dissolved in Isopropyl alcohol (3.0 mL, 0.039 mol) and the reaction was microwaved on 300 watts, 140° C. for 20 minutes. The mixture was then reduced under nitrogen. The crude residue was isolated and purified by Gilson prep HPLC to afford 3.35 mg (8%) of 2-[5-Chloro-2-(7-morpholin-4-yl-6,7,8,9-tetrahydro-5H-benzocyclohepten-2-ylamino)-pyrimidin-4-ylamino]-N,N-dimethyl-benzenesulfonamide. LC/MS (ESI): 557.18. $^1$H NMR (400 MHz, DMSO, d$_6$) δ 7.60 (d, 1H, J=8.59 Hz), 7.26 (s, 1H), 7.00 (d, 1H, J=8.09 Hz), 6.76 (t, 1H, J=7.58 Hz), 6.48 (t, 2H, J=7.57 Hz), 6.40 (d, 1H, J=8.34 Hz), 6.18 (d, 1H, J=8.09 Hz), 3.17 (d, 2H, J=13.39 Hz), 2.90 (m, 2H), 2.61 (t, 1H, J=12.89 Hz), 2.45 (m, 4H), 2.03 (m, 1H), 1.95 (m, 3H), 1.81 (s, 6H), 1.50 (m, 2H), 0.66 (m, 2H).

Example 1033

2-[5-Chloro-2-(7-hydroxy-6,7,8,9-tetrahydro-5H-benzocyclohepten-2-ylamino)-pyrimidin-4-ylamino]-N,N-dimethyl-benzenesulfonamide 1033a) Prepared in the same reaction as Example 1032. 2-Amino-6,7,8,9-tetrahydro-5H-benzocyclohepten-7-ol was present in the reaction mixture due to the reduction of 2-Nitro-5,6,8,9-tetrahydro-benzocyclohepten-7-one in the reductive amination step of the formation of 7-Morpholin-4-yl-6,7,8,9-tetrahydro-5H-benzocyclohepten-2-ylamine. The two products were then purified and isolated via prep HPLC to afford 2-[5-Chloro-2-(7-hydroxy-6,7,8,9-tetrahydro-5H-benzocyclohepten-2-ylamino)-pyrimidin-4-ylamino]-N,N-dimethyl-benzenesulfonamide. LC/MS (ESI): 488.09. $^1$H NMR (400 MHz, DMSO, d$_6$) δ 8.38 (m, 1H), 8.16 (s, 1H), 7.91 (d, 1H, J=7.83 Hz), 7.67 (m, 1H), 7.43 (t, 1H, J=7.83 Hz), 7.25 (s, 1H), 7.17 (m, 1H), 7.07 (d, 1H, J=7.83 Hz), 3.88 (m, 1H), 2.87 (m, 1H), 2.72 (s, 6H), 2.70 (m, 1H), 2.63 (m, 2H), 2.04 (m, 2H), 1.45 (m, 2H).

Example 1034

5-Chloro-N*2*-(7-morpholin-4-yl-6,7,8,9-tetrahydro-5H-benzocyclohepten-2-yl)-N*4*-(2-pyrazol-1-yl-phenyl)-pyrimidine-2,4-diamine 1034a) Prepared in an analogous manner as Example 1032 replacing 2-(2,5-Dichloro-pyrimidin-4-ylamino)-N,N-dimethyl-benzenesulfonamide with (2,5-Dichloro-pyrimidin-4-yl)-(2-pyrazol-1-yl-phenyl)-amine to afford 5-Chloro-N*2*-(7-morpholin-4-yl-6,7,8,9-tetrahydro-5H-benzocyclohepten-2-yl)-N*4*-(2-pyrazol-1-yl-phenyl)-pyrimidine-2,4-diamine. LC/MS (ESI): 516.21. $^1$H NMR (400 MHz, DMSO, d$_6$) δ 9.58 (m, 1H), 9.39 (s, 1H), 8.34 (m, 1H), 8.28 (s, 1H), 8.19 (s, 1H), 7.89 (s, 1H), 7.66 (d, 1H, J=8.09 Hz), 7.43 (m, 2H), 7.32 (m, 2H), 7.02 (d, 1H, J=8.09 Hz), 6.59 (s, 1H), 3.98 (d, 2H, J=12.12 Hz), 3.72 (t, 2H, J=11.87 Hz), 3.54 (m, 1H), 3.29 (d, 2H, J=11.87 Hz), 3.21 (m, 2H), 2.69 (m, 4H), 2.21 (m, 2H), 1.44 (m, 2H).

Example 1035

2-[5-Chloro-4-(2-pyrazol-1-yl-phenylamino)-pyrimidin-2-ylamino]-6,7,8,9-tetrahydro-5H-benzocyclohepten-7-ol 1035a) Prepared in an analogous manner as Example 1033 replacing 2-(2,5-Dichloro-pyrimidin-4-ylamino)-N,N-dimethyl-benzenesulfonamide with (2,5-Dichloro-pyrimidin-4-yl)-(2-pyrazol-1-yl-phenyl)-amine to afford 2-[5-Chloro-4-(2-pyrazol-1-yl-phenylamino)-pyrimidin-2-ylamino]-6,7,8,9-tetrahydro-5H-benzocyclohepten-7-ol. LC/MS (ESI): 447.11. $^1$H NMR (400 MHz, DMSO, d$_6$) δ 9.37 (s, 1H), 8.34 (m, 1H), 8.28 (m, 1H), 8.16 (s, 1H), 7.89 (s, 1H), 7.64 (d, 1H, J=7.83 Hz), 7.36 (m, 3H), 7.24 (m, 1H), 6.95 (d, 1H, J=8.08 Hz), 6.58 (m, 1H), 3.72 (m, 1H), 2.73 (m, 1H), 2.66 (m, 1H), 2.45 (m, 2H), 1.87 (m, 2H), 1.32 (m, 2H).

Example 1036

5-Chloro-N*2*-(7-morpholin-4-yl-6,7,8,9-tetrahydro-5H-benzocyclohepten-2-yl)-N*4*-[2-(propane-2-sulfonyl)-phenyl]-pyrimidine-2,4-diamine 1036a) Prepared in an analogous manner as Example 1032 replacing 2-(2,5-Dichloro-pyrimidin-4-ylamino)-N,N-dimethyl-benzenesulfonamide with (2,5-Dichloro-pyrimidin-4-yl)-[2-(propane-2-sulfonyl)-phenyl]-amine to afford 5-Chloro-N*2*-(7-morpholin-4-yl-6,7,8,9-tetrahydro-5H-benzocyclohepten-2-yl)-N*4*-[2-(propane-2-sulfonyl)-phenyl]-pyrimidine-2,4-diamine. LC/MS (ESI): 556.19. $^1$H NMR (400 MHz, DMSO, d$_6$) δ 9.65 (m, 1H), 9.43 (s, 1H), 8.53 (m, 1H), 8.29 (s, 1H), 7.87 (d, 1H, J=7.83 Hz), 7.77 (m, 1H), 7.42 (m, 2H), 7.31 (m, 1H), 7.04 (d, 1H, J=8.08 Hz), 3.98 (d, 2H, J=11.37 Hz), 3.72 (t, 2H, J=11.87 Hz), 3.50 (m, 2H), 3.31 (m, 2H), 3.28 (m, 2H), 2.80 (m, 4H), 2.31 (m, 2H), 1.44 (m, 2H), 1.17 (m, 6H).

Example 1037

2-{5-Chloro-4-[2-(propane-2-sulfonyl)-phenylamino]-pyrimidin-2-ylamino}-6,7,8,9-tetrahydro-5H-benzocyclohepten-7-ol 1037a) Prepared in an analogous manner as Example 1033 replacing 2-(2,5-Dichloro-pyrimidin-4-ylamino)-N,N-dimethyl-benzenesulfonamide with (2,5-Dichloro-pyrimidin-4-yl)-[2-(propane-2-sulfonyl)-phenyl]-amine to afford 2-{5-Chloro-4-[2-(propane-2-sulfonyl)-phenylamino]-pyrimidin-2-ylamino}-6,7,8,9-tetrahydro-5H-benzocyclohepten-7-ol. LC/MS (ESI): 487.11. $^1$H NMR (400 MHz, DMSO, d$_6$) δ 9.45 (s, 2H), 8.53 (m, 1H), 8.28 (s, 1H), 7.86 (d, 1H, J=8.09 Hz), 7.73 (m, 1H), 7.40 (m, 2H), 7.24 (m, 1H), 6.96 (d, 1H, J=8.09 Hz), 3.72 (m, 1H), 3.44 (sept., 1H, J=6.83 Hz), 2.62 (m, 2H), 2.45 (m, 2H), 1.86 (m, 2H), 1.33 (m, 2H), 1.16 (d, 6H, J=6.82 Hz).

Example 1038

2-[5-Chloro-2-(5,5-dimethyl-2-oxo-2,3,4,5-tetrahydro-1H-benzo[b]azepin-7-ylamino)-pyrimidin-4-ylamino]-N-cyanomethyl-3-methyl-benzamide 1038a) 2-Amino-N-cyanomethyl-3-methyl-benzamide 8-Methyl-1H-benzo[d][1,3]oxazine-2,4-dione (0.750 g, 0.00423 mol), aminoacetonitrile hydrogen sulfate (0.652 g, 0.00423 mol), and N,N-diisopropylethyl amine (0.547 g, 0.00423 mol) were dissolved in 1,4-Dioxane (10 mL) and the reaction was allowed to proceed overnight at room temperature. Because the reaction had not gone to completion, it was heated at 60° C. for 4 hours to improve yields. The reaction mixture was then reduced en vacuo and the product was isolated by Isco flash column (hexanes/ethyl acetate) to afford 630 mg (79%) of 2-Amino-N-cyanomethyl-3-methyl-benzamide.

1038b) N-Cyanomethyl-2-(2,5-dichloro-pyrimidin-4-ylamino)-3-methyl-benzamide 2-Amino-N-cyanomethyl-3-methyl-benzamide (0.624 g, 0.00330 mol), 2,4,5-Trichloropyrimidine (0.605 g, 0.00330 mol) and Potassium carbonate (0.456 g, 0.00330 mol) were dissolved in N,N-Dimethylformamide (10.00 mL, 0.1291 mol) and the reaction was heated at 85° C. and was allowed to stir overnight. The reaction mixture was poured over saturated ammonium chloride, and organics were extracted with ethyl acetate/dichloromethane. Combined organics were dried over sodium sulfate, filtered and reduced en vacuo. The crude mixture was purified by Isco flash column chromatography (Hexane/Ethyl Acetate). Combined fractions were reduced en vacuo to afford 150 mg (14%) of N-Cyanomethyl-2-(2,5-dichloro-pyrimidin-4-ylamino)-3-methyl-benzamide. LC/MS (ESI): 336.07.

1038c) 2-[5-Chloro-2-(5,5-dimethyl-2-oxo-2,3,4,5-tetrahydro-1H-benzo[b]azepin-7-ylamino)-pyrimidin-4-ylamino]-N-cyanomethyl-3-methyl-benzamide N-Cyanomethyl-2-(2,5-dichloro-pyrimidin-4-ylamino)-3-methyl-benzamide (50.0 mg, 0.000149 mol), 7-Amino-5,5-dimethyl-1,3,4,5-tetrahydro-benzo[b]azepin-2-one (30.4 mg, 0.000149 mol) and 10-Camphorsulfonic acid (34.6 mg, 0.000149 mol) were suspended in Isopropyl alcohol (3.0 mL, 0.039 mol) and the reaction was microwaved on 300 watts, 140° C. for 20 minutes. The reaction mixture was then reduced under nitrogen and the crude residue was isolated and purified by Gilson prep HPLC to afford 9.33 mg (12%) of 2-[5-Chloro-2-(5,5-dimethyl-2-oxo-2,3,4,5-tetrahydro-1H-benzo[b]azepin-7-ylamino)-pyrimidin-4-ylamino]-N-cyanomethyl-3-methyl-benzamide. LC/MS (ESI): 504.15. $^1$H NMR (400 MHz, DMSO, $d_6$) δ 9.15 (s, 1H), 9.08 (m 1H), 8.93 (m, 1H), 8.80 (m, 1H), 8.11 (s, 1H), 7.50 (m, 2H), 7.34 (m, 3H), 6.61 (d, 1H, J=8.59 Hz), 4.21 (d, 2H, J=5.05 Hz), 2.32 (s, 3H), 2.12 (m, 2H), 1.93 (m, 2H), 1.22 (s, 6H).

Example 1039

2-[5-Chloro-2-(1-methyl-2-oxo-2,3,4,5-tetrahydro-1H-benzo[b]azepin-7-ylamino)-pyrimidin-4-ylamino]-N-cyanomethyl-3-methyl-benzamide 1039a) Prepared in an analogous fashion as Example 1038 replacing 7-Amino-5,5-dimethyl-1,3,4,5-tetrahydro-benzo[b]azepin-2-one with 7-Amino-1-methyl-1,3,4,5-tetrahydro-benzo[b]azepin-2-one to afford 2-[5-Chloro-2-(1-methyl-2-oxo-2,3,4,5-tetrahydro-1H-benzo[b]azepin-7-ylamino)-pyrimidin-4-ylamino]-N-cyanomethyl-3-methyl-benzamide. LC/MS (ESI): 490.09. $^1$H NMR (400 MHz, DMSO, $d_6$) δ 9.35 (s, 1H), 8.99 (s, 1H), 8.92 (m, 1H), 8.13 (s, 1H), 7.50 (m, 2H), 7.35 (m, 2H), 7.24 (d, 1H, J=9.09 Hz), 7.00 (d, 1H, J=8.84 Hz), 4.22 (d, 2H, J=4.30 Hz), 3.13 (s, 3H), 2.34 (m, 2H), 2.20 (s, 3H), 2.08 (m, 2H), 1.94 (m, 2H).

Example 1040

2-{5-Chloro-2-[3-(2-methoxy-ethyl)-2,3,4,5-tetrahydro-1H-benzo[d]azepin-7-ylamino]-pyrimidin-4-ylamino}-N-cyanomethyl-3-methyl-benzamide 1040a) Prepared in an analogous fashion as Example 1038 replacing 7-Amino-5,5-dimethyl-1,3,4,5-tetrahydro-benzo[b]azepin-2-one with 3-(2-Methoxy-ethyl)-2,3,4,5-tetrahydro-1H-benzo[d]azepin-7-ylamine to afford -{5-Chloro-2-[3-(2-methoxy-ethyl)-2,3,4,5-tetrahydro-1H-benzo[d]azepin-7-ylamino]-pyrimidin-4-ylamino}-N-cyanomethyl-3-methyl-benzamide. LC/MS (ESI): 520.21. $^1$H NMR (400 MHz, DMSO, $d_6$) δ 9.23 (m, 1H), 8.88 (m, 2H), 8.10 (s, 1H), 7.49 (d, 2H, J=7.84 Hz), 7.42 (m 1H), 7.28 (m, 1H), 7.08 (m, 1H), 6.88 (d, 1H, J=8.08 Hz), 4.23 (m, 2H), 3.75 (m, 2H), 3.66 (m, 2H), 3.37 (s, 3H), 2.91-3.10 (m, 8H), 2.18 (s, 3H).

Example 1041

2-[5-Chloro-2-(5,5-dimethyl-2-oxo-2,3,4,5-tetrahydro-1H-benzo[b]azepin-7-ylamino)-pyrimidin-4-ylamino]-N-(2-cyano-ethyl)-3-fluoro-benzamide 1041a) Prepared in an analogous fashion as Example 1038 replacing aminoacetonitrile hydrogen sulfate with β-cyanoethylamine and 8-Methyl-1H-benzo[d][1,3]oxazine-2,4-dione with 8-Fluoro-1H-benzo[d][1,3]oxazine-2,4-dione to afford 2-[5-Chloro-2-(5,5-dimethyl-2-oxo-2,3,4,5-tetrahydro-1H-benzo[b]azepin-7-ylamino)-pyrimidin-4-ylamino]-N-(2-cyano-ethyl)-3-fluoro-benzamide. LC/MS (ESI): 522.14. $^1$H NMR (400 MHz, DMSO, $d_6$) δ 9.27 (s, 2H), 9.21 (s, 1H), 8.87 (t, 1H, J=5.81 Hz), 8.16 (s, 1H), 7.47 (m, 4H), 7.34 (s, 1H), 6.66 (d, 1H, J=8.84 Hz), 3.45 (m, 2H), 2.72 (t, 2H, J=6.57 Hz), 2.11 (m, 2H), 1.92 (m, 2H), 1.22 (s, 6H).

Example 1042

2-[5-Chloro-2-(1-methyl-2-oxo-2,3,4,5-tetrahydro-1H-benzo[b]azepin-7-ylamino)-pyrimidin-4-ylamino]-N-(2-cyano-ethyl)-3-fluoro-benzamide 1042a) Prepared in an analogous fashion as Example 1041 replacing 7-Amino-5,5-dimethyl-1,3,4,5-tetrahydro-benzo[b]azepin-2-one with 7-Amino-1-methyl-1,3,4,5-tetrahydro-benzo[b]azepin-2-one to afford 2-[5-Chloro-2-(1-methyl-2-oxo-2,3,4,5-tetrahydro-1H-benzo[b]azepin-7-ylamino)-pyrimidin-4-ylamino]-N-(2-cyano-ethyl)-3-fluoro-benzamide. LC/MS (ESI): 508.09. $^1$H NMR (400 MHz, DMSO, $d_6$) δ 9.40 (s, 1H), 9.18 (s, 1H), 8.89 (t, 1H, J=5.81 Hz), 8.18 (s, 1H), 7.45 (m 3H), 7.35 (s, 2H), 7.04 (m, 1H), 3.45 (m, 2H), 3.15 (s, 3H), 2.72 (t, 2H, J=6.57 Hz), 2.45 (m, 2H), 2.08 (m, 2H), 1.97 (m, 2H).

Example 1043

2-{5-Chloro-2-[3-(2-methoxy-ethyl)-2,3,4,5-tetrahydro-1H-benzo[d]azepin-7-ylamino]-pyrimidin-4-ylamino}-N-(2-cyano-ethyl)-3-fluoro-benzamide 1043a) Prepared in an analogous fashion as Example 1041 replacing 7-Amino-5,5-dimethyl-1,3,4,5-tetrahydro-benzo[b]azepin-2-one with 3-(2-Methoxy-ethyl)-2,3,4,5-tetrahydro-1H-benzo[d]azepin-7-ylamine to afford 2-{5-Chloro-2-[3-(2-methoxy-ethyl)-2,3,4,5-tetrahydro-1H-benzo[d]azepin-7-ylamino]-pyrimidin-4-ylamino}-N-(2-cyano-ethyl)-3-fluoro-benzamide. LC/MS (ESI): 538.17. $^1$H NMR (400 MHz, DMSO, d$_6$) δ 9.37 (s, 1H), 9.11 (s, 1H), 8.89 (m, 1H), 8.21 (s, 1H), 7.46 (m, 3H), 7.30 (s, 1H), 7.23 (d, 1H, J=8.08 Hz), 6.93 (d, 1H, J=7.83 Hz), 4.34 (m, 2H), 3.78 (m, 2H), 3.68 (m, 2H), 3.52 (m, 2H), 3.47 (m, 2H), 3.37 (s, 3H), 2.90-3.10 (m, 4H), 2.67 (m, 2H).

Example 1044

2-[5-Chloro-2-(5,5-dimethyl-2-oxo-2,3,4,5-tetrahydro-1H-benzo[b]azepin-7-ylamino)-pyrimidin-4-ylamino]-N-cyanomethyl-3-fluoro-benzamide 1044a) Prepared in an analogous fashion as Example 1038 replacing 8-Methyl-1H-benzo[d][1,3]oxazine-2,4-dione with 8-Fluoro-1H-benzo[d][1,3]oxazine-2,4-dione to afford 2-[5-Chloro-2-(5,5-dimethyl-2-oxo-2,3,4,5-tetrahydro-1H-benzo[b]azepin-7-ylamino)-pyrimidin-4-ylamino]-N-cyanomethyl-3-fluoro-benzamide. LC/MS (ESI): 508.09. $^1$H NMR (400 MHz, DMSO, d$_6$) δ 9.10 (m, 2H), 9.08 (m, 2H), 8.16 (s, 1H), 7.51 (m, 2H), 7.44 (m, 2H), 7.34 (s, 1H), 6.65 (d, 1H, J=9.09 Hz), 4.27 (d, 2H, J=5.56 Hz), 2.08 (m, 2H), 1.90 (m, 2H), 1.21 (s, 6H).

Example 1045

2-[5-Chloro-2-(1-methyl-2-oxo-2,3,4,5-tetrahydro-1H-benzo[b]azepin-7-ylamino)-pyrimidin-4-ylamino]-N-cyanomethyl-3-fluoro-benzamide Prepared in an analogous fashion as Example 1044 replacing 7-Amino-5,5-dimethyl-1,3,4,5-tetrahydro-benzo[b]azepin-2-one with 7-Amino-1-methyl-1,3,4,5-tetrahydro-benzo[b]azepin-2-one to afford 2-[5-Chloro-2-(1-methyl-2-oxo-2,3,4,5-tetrahydro-1H-benzo[b]azepin-7-ylamino)-pyrimidin-4-ylamino]-N-cyanomethyl-3-fluoro-benzamide. LC/MS (ESI): 494.09. $^1$H NMR (400 MHz, DMSO, d$_6$) δ 9.39 (s, 1H), 9.16 (t, 1H, J=5.05 Hz), 9.07 (s, 1H), 8.18 (s, 1H), 7.50 (m; 3H), 7.34 (m, 2H), 7.03 (d, 1H, J=8.84 Hz), 4.27 (d, 2H, J=5.30 Hz), 3.14 (s, 3H), 2.36 (m, 2H), 2.08 (m, 2H), 1.95 (m, 2H).

Example 1046

2-[5-Chloro-2-(2-oxo-2,3,4,5-tetrahydro-1H-benzo[b]azepin-7-ylamino)-pyrimidin-4-ylamino]-N-cyanomethyl-3-fluoro-benzamide 1046a) Prepared in an analogous fashion as Example 1044 replacing 7-Amino-5,5-dimethyl-1,3,4,5-tetrahydro-benzo[b]azepin-2-one with 7-Amino-1,3,4,5-tetrahydro-benzo[b]azepin-2-one to afford 2-[5-Chloro-2-(2-oxo-2,3,4,5-tetrahydro-1H-benzo[b]azepin-7-ylamino)-pyrimidin-4-ylamino]-N-cyanomethyl-3-fluoro-benzamide. LC/MS (ESI): 480.09. $^1$H NMR (400 MHz, DMSO, d$_6$) δ 9.35 (m, 1H), 9.24 (s, 1H), 9.17 (t, 1H, J=4.80 Hz), 9.09 (s, 1H), 8.17 (s, 1H), 7.53 (m, 2H), 7.47 (m, 1H), 7.33 (s, 1H), 7.23 (d, 1H, J=8.09 Hz), 6.69 (d, 1H, J=8.59 Hz), 4.27 (d, 2H, J=4.80 Hz), 2.44 (t, 2H, J=6.82 Hz), 2.05 (m, 2H), 1.98 (m, 2H).

Example 1047

(1S,2S,3R,4R)-3-[5-Chloro-2-(3-methoxy-7-morpholin-4-yl-6,7,8,9-tetrahydro-5H-benzocyclohepten-2-ylamino)-pyrimidin-4-ylamino]-bicyclo[2.2.1]hept-5-ene-2-carboxylic acid amide (Single Diasteromer A)

1047a) (2-Hydroxymethyl-4-methoxy-phenyl)-methanol

To a stirred suspension of Lithium tetrahydroaluminate (16.6 g, 0.436 mol) in Tetrahydrofuran (300 mL, 4 mol) at 0° C. under nitrogen was added dropwise a solution of 4-Methoxy-phthalic acid dimethyl ester (24.46 g, 0.1091 mol) in Tetrahydrofuran (100 mL, 1 mol). The reaction was stirred at 0° C. for 1 h then warmed to room temperature overnight. HPLC indicated no starting material present. Reaction was recooled at 0° C. and quenched with addition of water (125 mL) carefully dropwise, 1 N NaOH (100 mL) and water (125 mL). Evolution of gas was observed upon initial quenching with water. A white solid precipitated out of solution (aluminum salts). Following complete quenching of the reaction mixture, the aluminum salts were removed by filtration. The filtrate was diluted with ethyl acetate, washed with water, dried over magnesium sulfate, filtered and concentrated in vacuo to provide 17.80 grams (97%) of (2-Hydroxymethyl-4-methoxy-phenyl)-methanol as a colorless oil.

1047b) 1,2-Bis-bromomethyl-4-methoxy-benzene

Using the procedure outlined in J. Am. Chem. Soc. 1994, 116, 10593-10600, (2-Hydroxymethyl-4-methoxy-phenyl)-methanol (17.80 g, 0.1058 mol) was dissolved in Chloroform (200 mL, 2 mol) and the reaction was treated with Phosphorus tribromide (60.2 g, 0.222 mol) dropwise over 6 hours. After stirring overnight at room temperature, the mixture was cooled at 0° C. and was treated with 50 mL of water. The reaction mixture was poured over saturated sodium bicarbonate, and organics were extracted with dichloromethane. Combined organics were dried over sodium sulfate, filtered and reduced en vacuo. The product, 16.0 grams (51%), was used without further purification.

1047c) 2-Methoxy-7-oxo-6,7,8,9-tetrahydro-5H-benzocycloheptene-6,8-dicarboxylic acid diethyl ester From an adapted procedure in Helvetic Chimica Acta, 2001, 84, 2051-2063, to a stirred solution of Tetra-n-butylammonium iodide (12.1 g, 0.0326 mol) in 0.6 M of Sodium bicarbonate in Water (300 mL) and Methylene chloride (130 mL, 2.1 mol) was added a solution of 1,2-Bis-bromomethyl-4-methoxy-benzene (16.00 g, 0.05442 mol) and 3-Oxopentanedioic acid, diethyl ester (14.31 g, 0.07075 mol) in Methylene chloride (40 mL, 0.6 mol). The solution was stirred vigorously at room temperature for 20 h. Saturated ammonium chloride solution was added to the reaction mixture. The product was extracted with ethyl acetate (3×100 mL). The ethyl acetate extracts were washed with water and brine, then dried over magnesium sulfate, filtered and concentrated in vacuo to a yellow oil. The oil was triturated with ether and a precipitate crashed out of solution and was removed by filtration (tetrabutylammonium salts). The filtrate was concentrated to an oil (20.0 grams, 100%) that was carried on to the next step without further purification.

1047d) 2-Methoxy-5,6,8,9-tetrahydro-benzocyclohepten-7-one

2-Methoxy-7-oxo-6,7,8,9-tetrahydro-5H-benzocycloheptene-6,8-dicarboxylic acid diethyl ester (18.2 g, 0.0544 mol) was dissolved in ethanol and the solution was treated with Potassium hydroxide (24.4 g, 0.435 mol) in Water (140 g, 7.6 mol). The reaction was then refluxed until HPLC showed consumption of starting material (~5 hours). The reaction was then acidified with 1N HCl and the product was extracted with dichloromethane. Organic extracts were dried over sodium sulfate, filtered and reduced. The crude mixture was filtered through a plug of silica rinsing with dichloromethane before purification. The crude mixture was purified by Isco flash column chromatography (Hexane/Ethyl Acetate). Combined fractions were reduced en vacuo to afford 6.0 grams (58%) of 2-Methoxy-5,6,8,9-tetrahydro-benzocyclohepten-7-one.

1047e) 2-Methoxy-3-nitro-5,6,8,9-tetrahydro-benzocyclohepten-7-one and 2-Methoxy-1-nitro-5,6,8,9-tetrahydro-benzocyclohepten-7-one 2-Methoxy-5,6,8,9-tetrahydro-benzocyclohepten-7-one (6.00 g, 0.0315 mol) was dissolved in Acetonitrile (280 mL, 5.4 mol) and was added to a mixture of Trifluoroacetic anhydride (13.4 mL, 0.0946 mol) in Acetonitrile at 0° C. Potassium nitrate (3.19 g, 0.0315 mol) was then added and the reaction was allowed to warm to room temperature. When HPLC showed consumption of starting material, the mixture was poured over saturated sodium bicarbonate, and organics were extracted with ethyl acetate/dichloromethane. Combined organics were dried over sodium sulfate, filtered and reduced en vacuo. The crude mixture was purified by Isco flash column chromatography (Hexane/Ethyl Acetate). The gradient run was 0% EA-50% EA. Combined fractions were reduced en vacuo to afford 3.62 (49%) of 2-Methoxy-3-nitro-5,6,8,9-tetrahydro-benzocyclohepten-7-one and 1.80 grams (25%).

1047f) 4-(2-Methoxy-3-nitro-6,7,8,9-tetrahydro-5H-benzocyclohepten-7-yl)-morpholine 2-Methoxy-3-nitro-5,6,8,9-tetrahydro-benzocyclohepten-7-one (4.94 g, 0.0210 mol) in Methylene chloride (100 mL, 2 mol) was treated with Morpholine (18.30 g, 0.2100 mol) and then Acetic acid (12.61 g, 0.2100 mol). Two mass equivalents of powdered 4 A molecular sieves were added and the mixture was heated to reflux and was allowed to stir for 4 hours. The solution was then cooled to room temp and Sodium triacetoxyborohydride (8.90 g, 0.0420 mol) was added. The reaction was then allowed to proceed until HPLC showed consumption of starting material. The reaction mixture was poured over saturated sodium bicarbonate, and organics were extracted with ethyl acetate/dichloromethane. Combined organics were dried over sodium sulfate, filtered and reduced en vacuo. The crude mixture was purified by Isco flash column chromatography (DCM/MeOH). Combined fractions were reduced en vacuo to afford 5.41 grams (84%) of 4-(2-Methoxy-3-nitro-6,7,8,9-tetrahydro-5H-benzocyclohepten-7-yl)-morpholine. 4-(2-Methoxy-1-nitro-6,7,8,9-tetrahydro-5H-benzocyclohepten-7-yl)-morpholine was made in an analogous manner using the same conditions described above.

1047g) 3-Methoxy-7-morpholin-4-yl-6,7,8,9-tetrahydro-5H-benzocyclohepten-2-ylamine 4-(2-Methoxy-3-nitro-6,7,8,9-tetrahydro-5H-benzocyclohepten-7-yl)-morpholine (5.40 g, 0.0176 mol) was dissolved in Ethanol (100 mL, 2 mol) and the reaction mixture was carefully added to 10% Palladium on Carbon (0.750 g) under nitrogen in a Parr vessel. The reaction was then placed on a Parr shaker until uptake of hydrogen had ceased (~5 hours). Catalyst was filtered and the filtrate was reduced en vacuo to afford 4.10 grams (84%) of 3-Methoxy-7-morpholin-4-yl-6,7,8,9-tetrahydro-5H-benzocyclohepten-2-ylamine. 2-Methoxy-7-morpholin-4-yl-6,7,8,9-tetrahydro-5H-benzocyclohepten-1-ylamine was made in an analogous fashion.

The following intermediates were made in an analogous fashion as above utilizing the appropriate amine precursors: N*7*-(2,2-Difluoro-ethyl)-3-methoxy-6,7,8,9-tetrahydro-5H-benzocycloheptene-2,7-diamine, 3-Methoxy-N*7*-(2-methoxy-ethyl)-6,7,8,9-tetrahydro-5H-benzocycloheptene-2,7-diamine, N*7*-(2,2-Difluoro-ethyl)-2-methoxy-6,7,8,9-tetrahydro-5H-benzocycloheptene-1,7-diamine, 2-(2-Amino-3-methoxy-6,7,8,9-tetrahydro-5H-benzocyclohepten-7-ylamino)-ethanol and 3-Methoxy-7-(4-methyl-piperazin-1-yl)-6,7,8,9-tetrahydro-5H-benzocyclohepten-2-ylamine.

1047h) (1S,2S,3R,4R)-3-[5-Chloro-2-(3-methoxy-7-morpholin-4-yl-6,7,8,9-tetrahydro-5H-benzocyclohepten-2-ylamino)-pyrimidin-4-ylamino]-bicyclo[2.2.1]hept-5-ene-2-carboxylic acid amide (Single Diasteromer A)

3-Methoxy-7-morpholin-4-yl-6,7,8,9-tetrahydro-5H-benzocyclohepten-2-ylamine (880.0 mg, 0.003184 mol), (1S,2S,3R,4R)-3-(2,5-Dichloro-pyrimidin-4-ylamino)-bicyclo[2.2.1]hept-5-ene-2-carboxylic acid amide (952 mg, 0.00318 mol) and 4M of Hydrogen Chloride in 1,4-Dioxane (2 mL) were dissolved in 2-Methoxyethanol (30.0 mL, 0.380 mol) and the reaction was heated at 100° C. until HPLC showed consumption of starting material. The reaction mixture was poured over saturated sodium bicarbonate, and organics were extracted with ethyl acetate/dichloromethane. Combined organics were dried over sodium sulfate, filtered and reduced en vacuo. The crude residue was isolated and purified by Gilson prep HPLC as the first peak to elute to afford the desired product as a TFA salt. The TFA salt was taken up in dichloromethane and was poured over saturated sodium bicarbonate, and organics were extracted with ethyl acetate/dichloromethane. Combined organics were dried over sodium sulfate, filtered and reduced en vacuo to afford 439 mg (26%) of (1S,2S,3R,4R)-3-[5-Chloro-2-(3-methoxy-7-morpholin-4-yl-6,7,8,9-tetrahydro-5H-benzocyclohepten-2-ylamino)-pyrimidin-4-ylamino]-bicyclo[2.2.1]hept-5-ene-2-carboxylic acid amide (Single Diasteromer A). LC/MS (ESI): 539.22. $^1$H NMR (400 MHz, DMSO, d$_6$) δ 9.60 (m, 1H), 8.12 (s, 1H), 7.90 (s, 1H), 7.79 (m, 1H), 7.39 (s, 1H), 6.98 (s, 1H), 6.36 (m, 1H), 6.16 (m, 1H), 4.00 (m, 3H), 3.83 (s, 3H), 3.30 (m, 5H), 2.74-2.90 (m, 6H), 2.39 (m, 3H), 1.94 (d, 1H, J=4.80 Hz), 1.44 (m, 3H), 1.28 (m, 1H), 1.04 (s, 1H), 0.74 (s, 1H).

Example 1048

(1S,2S,3R,4R)-3-[5-Chloro-2-(3-methoxy-7-morpholin-4-yl-6,7,8,9-tetrahydro-5H-benzocyclohepten-2-ylamino)-pyrimidin-4-ylamino]-bicyclo[2.2.1]hept-5-ene-2-carboxylic acid amide (Single Diastereomer B)

1048a) Prepared as described in Example 1047. Isolated as the $2^{nd}$ peak elution from prep HPLC to afford (1S,2S,3R,4R)-3-[5-Chloro-2-(3-methoxy-7-morpholin-4-yl-6,7,8,9-tetrahydro-5H-benzocyclohepten-2-ylamino)-pyrimidin-4-ylamino]-bicyclo[2.2.1]hept-5-ene-2-carboxylic acid amide (Single Diastereomer B). LC/MS (ESI): 539.25. $^1$H NMR (400 MHz, DMSO, d$_6$) δ 9.56 (m, 1H), 8.05 (s, 1H), 7.81 (m, 2H), 7.35 (s, 1H), 6.89 (s, 1H), 6.35 (m, 1H), 6.16 (m, 1H), 4.04 (m, 4H), 3.83 (s, 3H), 3.71 (m, 4H), 2.90 (m, 3H), 2.76 (m, 5H), 2.32 (m, 3H), 2.13 (m, 1H), 1.41 (m, 4H).

Example 1049

2-[5-Chloro-2-(3-methoxy-7-morpholin-4-yl-6,7,8,9-tetrahydro-5H-benzocyclohepten-2-ylamino)-pyrimidin-4-ylamino]-N,N-dimethyl-benzenesulfonamide 1049a) Prepared in an analogous fashion to Example 1047 replacing (1S,2S,3R,4R)-3-(2,5-Dichloro-pyrimidin-4- ylamino)-bicyclo[2.2.1]hept-5-ene-2-carboxylic acid amide with 2-(2,5-Dichloro-pyrimidin-4-ylamino)-N,N-dimethyl-benzenesulfonamide to afford 2-[5-Chloro-2-(3-methoxy-7-morpholin-4-yl-6,7,8,9-tetrahydro-5H-benzocyclohepten-2-ylamino)-pyrimidin-4-ylamino]-N,N-dimethyl-benzenesulfonamide. LC/MS (ESI): 587.22. $^1$H NMR (400 MHz, DMSO, $d_6$) δ 9.63 (m, 1H), 9.35 (s, 1H), 8.40 (m, 1H), 8.26 (s, 1H), 7.83 (d, 1H, J=8.09 Hz), 7.63 (m, 1H), 7.54 (s, 1H), 7.39 (d, 1H, J=7.58 Hz), 6.92 (s, 1H), 3.99 (d, 2H, J=11.50 Hz), 3.78 (s, 3H), 3.71 (m, 2H), 3.53 (m, 1H), 3.26 (m, 4H), 2.88 (m, 1H), 2.73 (m, 1H), 2.65 (s, 6H), 2.49 (m, 2H), 2.39 (m, 2H), 1.44 (m, 2H).

Example 1050

5-Chloro-N*2*-(3-methoxy-7-morpholin-4-yl-6,7,8,9-tetrahydro-5H-benzocyclohepten-2-yl)-N*4*-[2-(propane-2-sulfonyl)-phenyl]-pyrimidine-2,4-diamine 1050a) Prepared in an analogous fashion to Example 1047 replacing (1S,2S,3R,4R)-3-(2,5-Dichloro-pyrimidin-4-ylamino)-bicyclo[2.2.1]hept-5-ene-2-carboxylic acid amide with (2,5-Dichloro-pyrimidin-4-yl)-[2-(propane-2-sulfonyl)-phenyl]-amine to afford 5-Chloro-N*2*-(3-methoxy-7-morpholin-4-yl-6,7,8,9-tetrahydro-5H-benzocyclohepten-2-yl)-N*4*-[2-(propane-2-sulfonyl)-phenyl]-pyrimidine-2,4-diamine. LC/MS (ESI): 586.19. $^1$H NMR (400 MHz, DMSO, $d_6$) δ 9.52 (s, 1H), 8.42 (m, 1H), 8.31 (s, 1H), 8.26 (s, 1H), 7.86 (d, 1H, J=8.09 Hz), 7.67 (t, 1H, J=7.83 Hz), 7.52 (s, 1H), 7.40 (m, 1H), 6.92 (s, 1H), 3.98 (m, 2H), 3.78 (s, 3H), 3.75 (m, 2H), 3.47 (m, 2H), 3.28 (m, 2H), 3.21 (m, 2H), 2.86 (m, 1H), 2.73 (m, 3H), 2.32 9m, 2H), 1.48 (m, 2H), 1.16 (m, 6H).

Example 1051

N-{(1R,2R)-2-[5-Chloro-2-(3-methoxy-7-morpholin-4-yl-6,7,8,9-tetrahydro-5H-benzocyclohepten-2-ylamino)-pyrimidin-4-ylamino]-cyclohexyl}-methanesulfonamide 1051a) Prepared in an analogous fashion to Example 1047 replacing (1S,2S,3R,4R)-3-(2,5-Dichloro-pyrimidin-4-ylamino)-bicyclo[2.2.1]hept-5-ene-2-carboxylic acid amide with N-[(1R,2R)-2-(2,5-Dichloro-pyrimidin-4-ylamino)-cyclohexyl]-methanesulfonamide to afford N-{(1R,2R)-2-[5-Chloro-2-(3-methoxy-7-morpholin-4-yl-6,7,8,9-tetrahydro-5H-benzocyclohepten-2-ylamino)-pyrimidin-4-ylamino]-cyclohexyl}-methanesulfonamide (mixture of diasteromers). LC/MS (ESI): 579.25. $^1$H NMR (400 MHz, DMSO, $d_6$) δ 9.29 (s, 1H), 8.16 (s, 1H), 7.50 (m, 2H), 7.34 (m, 1H), 6.88 (s, 1H), 3.97 (m, 2H), 3.78 (s, 3H), 3.50 (m, 2H), 3.27 (m, 4H), 2.91 (s, 3H), 2.78 (m, 4H), 2.38 (m, 5H), 1.94 (m, 2H), 1.75 (m, 2H), 1.45 (m, 2H), 1.28 (m, 4H).

Example 1052

5-Chloro-N*2*-(3-methoxy-7-morpholin-4-yl-6,7,8,9-tetrahydro-5H-benzocyclohepten-2-yl)-N*4*-(2-pyrazol-1-yl-phenyl)-pyrimidine-2,4-diamine 1052a) Prepared in an analogous fashion to Example 1047 replacing (1S,2S,3R,4R)-3-(2,5-Dichloro-pyrimidin-4-ylamino)-bicyclo[2.2.1]hept-5-ene-2-carboxylic acid amide with (2,5-Dichloro-pyrimidin-4-yl)-(2-pyrazol-1-yl-phenyl)-amine to afford 5-Chloro-N*2*-(3-methoxy-7-morpholin-4-yl-6,7,8,9-tetrahydro-5H-benzocyclohepten-2-yl)-N*4*-(2-pyrazol-1-yl-phenyl)-pyrimidine-2,4-diamine. LC/MS (ESI): 546.22. $^1$H NMR (400 MHz, DMSO, $d_6$) δ 9.83 (m, 1H), 8.22 (m, 4H), 7.88 (s, 1H), 7.66 (d, 1H, J=7.58 Hz), 7.58 (s, 1H), 7.37 (m, 2H), 6.92 (s, 1H), 6.57 (s, 1H), 4.00 (m, 2H), 3.79 (s, 3H), 3.72 (m, 2H), 3.50 (t, 1H, J=11.62), 3.23 (m, 4H), 2.89 (m, 4H), 2.78 (m, 3H), 2.25 (m, 2H), 1.43 (m, 2H).

Example 1053

(1S,2S,3R,4R)-3-{5-Chloro-2-[7-(2,2-difluoro-ethylamino)-3-methoxy-6,7,8,9-tetrahydro-5H-benzocyclohepten-2-ylamino]-pyrimidin-4-ylamino}-bicyclo[2.2.1]hept-5-ene-2-carboxylic acid amide (Single Diasteromer A)

1053a) Prepared in an analogous fashion to Example 1047 replacing morpholine with 2,2-difluoroethylamine to afford (1S,2S,3R,4R)-3-{5-Chloro-2-[7-(2,2-difluoro-ethylamino)-3-methoxy-6,7,8,9-tetrahydro-5H-benzocyclohepten-2-ylamino]-pyrimidin-4-ylamino}-bicyclo[2.2.1]hept-5-ene-2-carboxylic acid amide (Single Diastereomer A) 1$^{st}$ peak elution from prep HPLC purification. LC/MS (ESI): 533.24. $^1$H NMR (400 MHz, DMSO, $d_6$) δ 9.06 (m, 2H), 8.13 (s, 1H), 7.90 (s, 1H), 7.76 (m, 1H), 7.38 (s, 1H), 6.96 (s, 1H), 6.43 (m, 2H), 6.13 (m, 1H), 4.02 (m, 1H), 3.83 (s, 3H), 3.61 (m, 2H), 3.44 (m, 1H), 2.71-2.92 (m, 6H), 2.34 (m, 3H), 2.05 (m, 1H), 1.38 (m, 2H), 1.05 (s, 1H), 0.74 (s, 1H).

Example 1054

(1S,2S,3R,4R)-3-{5-Chloro-2-[7-(2,2-difluoro-ethylamino)-3-methoxy-6,7,8,9-tetrahydro-5H-benzocyclohepten-2-ylamino]-pyrimidin-4-ylamino}-bicyclo[2.2.1]hept-5-ene-2-carboxylic acid amide (Single Diasteromer B)

1054a) Prepared in an analogous fashion to Example 1047 replacing morpholine with 2,2-difluoroethylamine to afford (1S,2S,3R,4R)-3-{5-Chloro-2-[7-(2,2-difluoro-ethylamino)-3-methoxy-6,7,8,9-tetrahydro-5H-benzocyclohepten-2-ylamino]-pyrimidin-4-ylamino}-bicyclo[2.2.1]hept-5-ene-2-carboxylic acid amide (Single Diastereomer A). 2$^{nd}$ peak elution from prep HPLC purification. LC/MS (ESI): 533.24. $^1$H NMR (400 MHz, DMSO, $d_6$) δ 9.06 (m, 2H), 8.13 (s, 1H), 7.90 (s, 1H), 7.76 (m, 1H), 7.38 (s, 1H), 6.96 (s, 1H), 6.43 (m, 2H), 6.13 (m, 1H), 4.02 (m, 1H), 3.83 (s, 3H), 3.61 (m, 2H), 3.44 (m, 1H), 2.71-2.92 (m, 6H), 2.34 (m, 3H), 2.05 (m, 1H), 1.38 (m, 2H), 1.05 (s, 1H), 0.74 (s, 1H).

Example 1055

2-{5-Chloro-2-[7-(2,2-difluoro-ethylamino)-3-methoxy-6,7,8,9-tetrahydro-5H-benzocyclohepten-2-ylamino]-pyrimidin-4-ylamino}-N,N-dimethyl-benzenesulfonamide 1055a) Prepared in an analogous fashion to Example 1049 replacing morpholine with 2,2-difluoroethylamine to afford 2-{5-Chloro-2-[7-(2,2-difluoro-ethylamino)-3-methoxy-6,7,8,9-tetrahydro-5H-benzocyclohepten-2-ylamino]-pyrimidin-4-ylamino}-N,N-dimethyl-benzenesulfonamide. LC/MS (ESI): 581.18. $^1$H NMR (400 MHz, DMSO, $d_6$) δ 9.38 (s, 1H), 9.15 (m, 2H), 8.39 (m, 1H), 8.33 (s, 1H), 8.25 (s, 1H), 7.82 (d, 1H, J=8.08 Hz), 7.59 (m, 1H), 7.48 (s, 1H), 7.36

(m, 1H), 6.90 (s, 1H), 6.44 (td, 1H), 3.77 (s, 3H), 3.62 (t, 2H, J=14.66 Hz), 3.42 (m, 1H), 2.81 (m, 2H), 2.72 (s, 6H), 2.30 (m, 2H), 1.35 (m, 2H).

Example 1056

5-Chloro-N*2*-[7-(2,2-difluoro-ethylamino)-3-methoxy-6,7,8,9-tetrahydro-5H-benzocyclohepten-2-yl]-N*4*-[2-(propane-2-sulfonyl)-phenyl]-pyrimidine-2,4-diamine 1056a) Prepared in an analogous fashion to Example 1050 replacing morpholine with 2,2-difluoroethylamine to afford 5-Chloro-N*2*-[7-(2,2-difluoro-ethylamino)-3-methoxy-6,7,8,9-tetrahydro-5H-benzocyclohepten-2-yl]-N*4*-[2-(propane-2-sulfonyl)-phenyl]-pyrimidine-2,4-diamine. LC/MS (ESI): 580.17. $^1$H NMR (400 MHz, DMSO, $d_6$) δ 9.51 (s, 1H), 9.09 (m, 2H), 8.40 (m, 1H), 8.31 (s, 1H), 8.25 (s, 1H), 7.85 (d, 1H, J=8.08 Hz), 7.64 (t, 1H, J=7.83 Hz), 7.48 (s, 1H), 7.38 (m, 1H), 6.90 (s, 1H), 6.43 (td, 1H), 3.77 (s, 3H), 3.62 (t, 2H, J=15.91 Hz), 3.45 (m, 2H), 2.81 (m, 3H), 2.29 (m, 2H), 1.35 (m, 2H), 1.15 (d, 6H, J=6.56 Hz).

Example 1057

N-((1R,2R)-2-{5-Chloro-2-[7-(2,2-difluoro-ethylamino)-3-methoxy-6,7,8,9-tetrahydro-5H-benzocyclohepten-2-ylamino]-pyrimidin-4-ylamino}-cyclohexyl)-methanesulfonamide (Single Diasteromer A)

1057a) Prepared in an analogous fashion to Example 1051 replacing morpholine with 2,2-difluoroethylamine to afford N-((1R,2R)-2-{5-Chloro-2-[7-(2,2-difluoro-ethylamino)-3-methoxy-6,7,8,9-tetrahydro-5H-benzocyclohepten-2-ylamino]-pyrimidin-4-ylamino}-cyclohexyl)-methanesulfonamide (Single Diasteromer A). $1^{st}$ peak elution from prep HPLC purification. LC/MS (ESI): 573.24. $^1$H NMR (400 MHz, DMSO, $d_6$) δ 9.07 (m, 2H), 8.13 (m, 1H), 7.83 (m, 1H), 7.21 (d, 1H, J=8.34 Hz), 6.95 (s, 1H), 6.44 (td, 1H), 3.83 (s, 3H), 3.61 (m, 2H), 3.44 (m, 2H), 2.93 (s, 3H), 2.70-2.90 (m, 4H), 2.25 (m, 4H), 1.91 (m, 2H), 1.71 (m, 2H), 1.48 (m, 4H), 1.03 (s, 1H), 0.74 (s, 1H).

Example 1058

N-((1R,2R)-2-{5-Chloro-2-[7-(2,2-difluoro-ethylamino)-3-methoxy-6,7,8,9-tetrahydro-5H-benzocyclohepten-2-ylamino]-pyrimidin-4-ylamino}-cyclohexyl)-methanesulfonamide (Single Diasteromer B)

1058a) Prepared in an analogous fashion to Example 1051 replacing morpholine with 2,2-difluoroethylamine to afford N-((1R,2R)-2-{5-Chloro-2-[7-(2,2-difluoro-ethylamino)-3-methoxy-6,7,8,9-tetrahydro-5H-benzocyclohepten-2-ylamino]-pyrimidin-4-ylamino}-cyclohexyl)-methanesulfonamide (Single Diasteromer B). $2^{nd}$ peak elution from prep HPLC purification. LC/MS (ESI): 573.24. $^1$H NMR (400 MHz, DMSO, $d_6$) δ 9.07 (m, 2H), 8.13 (m, 1H), 7.83 (m, 1H), 7.21 (d, 1H, J=8.34 Hz), 6.95 (s, 1H), 6.44 (td, 1H), 3.83 (s, 3H), 3.61 (m, 2H), 3.44 (m, 2H), 2.93 (s, 3H), 2.70-2.90 (m, 4H), 2.25 (m, 4H), 1.91 (m, 2H), 1.71 (m, 2H), 1.48 (m, 4H), 1.03 (s, 1H), 0.74 (s, 1H).

Example 1059

5-Chloro-N*2*-[7-(2,2-difluoro-ethylamino)-3-methoxy-6,7,8,9-tetrahydro-5H-benzocyclohepten-2-yl]-N*4*-(2-pyrazol-1-yl-phenyl)-pyrimidine-2,4-diamine 1059a) Prepared in an analogous fashion to Example 1052 replacing morpholine with 2,2-difluoroethylamine to afford 5-Chloro-N*2*-[7-(2,2-difluoro-ethylamino)-3-methoxy-6,7,8,9-tetrahydro-5H-benzocyclohepten-2-yl]-N*4*-(2-pyrazol-1-yl-phenyl)-pyrimidine-2,4-diamine. LC/MS (ESI): 540.20. $^1$H NMR (400 MHz, DMSO, $d_6$) δ 10.34 (s, 1H), 9.10 (m, 2H), 8.24 (m, 3H), 8.17 (s, 1H), 7.87 (s, 1H), 7.64 (m, 1H), 7.54 (s, 1H), 7.30 (m, 2H), 6.89 (s, 1H), 6.57 (s, 1H), 6.44 (td, 1H), 3.78 (s, 3H), 3.63 (m, 2H), 3.42 (m, 1H), 2.78 (m, 4H), 2.35 (m, 2H), 1.34 (m, 1H).

Example 1060

2-{5-Chloro-2-[3-(2-methoxy-ethyl)-2,3,4,5-tetrahydro-1H-benzo[d]azepin-7-ylamino]-pyrimidin-4-ylamino}-N-(2-cyano-ethyl)-3-methoxy-benzamide 1060a) Prepared in an analogous fashion as Example 1041 replacing 7-Amino-5,5-dimethyl-1,3,4,5-tetrahydro-benzo[b]azepin-2-one with 3-(2-Methoxy-ethyl)-2,3,4,5-tetrahydro-1H-benzo[d]azepin-7-ylamine and 8-Methyl-1H-benzo[d][1,3]oxazine-2,4-dione with 8-Methoxy-1H-benzo[d][1,3]oxazine-2,4-dione to afford -{5-Chloro-2-[3-(2-methoxy-ethyl)-2,3,4,5-tetrahydro-1H-benzo[d]azepin-7-ylamino]-pyrimidin-4-ylamino}-N-(2-cyano-ethyl)-3-methoxy-benzamide. LC/MS (ESI): 550.26. $^1$H NMR (400 MHz, DMSO, $d_6$) δ 9.74 (m, 1H), 9.42 (m, 1H), 8.84 (s, 1H), 8.61 (m, 1H), 8.13 (s, 1H), 7.42 (d, 1H, J=8.08 Hz), 7.23 (m, 1H), 7.17 (m, 2H), 6.91 (d, 1H, J=6.82 Hz), 3.73 (s, 3H), 3.70 (m, 1H), 3.65 (m, 2H), 3.43 (m, 4H), 3.34 (s, 3H), 2.90-3.10 (m, 6H), 1.29 (m, 1H), 1.04 (s, 1H), 0.74 (s, 1H).

Example 1061

2-[5-Chloro-2-(5,5-dimethyl-2-oxo-2,3,4,5-tetrahydro-1H-benzo[b]azepin-7-ylamino)-pyrimidin-4-ylamino]-N-(2-cyano-ethyl)-3-methoxy-benzamide 1061a) Prepared in an analogous fashion as Example 1038 replacing aminoacetonitrile hydrogen sulfate with β-cyano-ethylamine and 8-Methyl-1H-benzo[d][1,3]oxazine-2,4-dione with 8-Methoxy-1H-benzo[d][1,3]oxazine-2,4-dione to afford 2-[5-Chloro-2-(5,5-dimethyl-2-oxo-2,3,4,5-tetrahydro-1H-benzo[b]azepin-7-ylamino)-pyrimidin-4-ylamino]-N-(2-cyano-ethyl)-3-methoxy-benzamide. LC/MS (ESI): 534.20. $^1$H NMR (400 MHz, DMSO, $d_6$) δ 9.26 (m, 2H), 8.87 (m, 1H), 8.62 (m, 1H), 8.10 (s, 1H), 7.37 (m, 2H), 7.28 (m, 2H), 7.20 (d, 1H, J=7.58 Hz), 6.63 (d, 1H, J=8.59 Hz), 3.70 (s, 3H), 3.39 (m, 2H), 2.67 (t, 2H, J=7.07 Hz), 2.10 (m, 2H), 1.91 (m, 2H), 1.22 (s, 6H).

Example 1062

2-[5-Chloro-2-(1-methyl-2-oxo-2,3,4,5-tetrahydro-1H-benzo[b]azepin-7-ylamino)-pyrimidin-4-ylamino]-N-(2-cyano-ethyl)-3-methoxy-benzamide 1062a) Prepared in an analogous fashion as Example 1041 replacing 7-Amino-5,5-dimethyl-1,3,4,5-tetrahydro-benzo

[b]azepin-2-one with 7-Amino-1-methyl-1,3,4,5-tetrahydro-benzo[b]azepin-2-one and 8-Methyl-1H-benzo[d][1,3]oxazine-2,4-dione with 8-Methoxy-1H-benzo[d][1,3]oxazine-2,4-dione to afford 2-[5-Chloro-2-(1-methyl-2-oxo-2,3,4,5-tetrahydro-1H-benzo[b]azepin-7-ylamino)-pyrimidin-4-ylamino]-N-(2-cyano-ethyl)-3-methoxy-benzamide. LC/MS (ESI): 520.20. $^1$H NMR (400 MHz, DMSO, d$_6$) δ 9.53 (s, 1H), 8.99 (s, 1H), 8.63 (m, 1H), 8.16 (s, 1H), 7.41 (m, 1H), 7.32 (m, 3H), 7.22 (d, 1H, J=7.58 Hz), 7.03 (d, 1H, J=8.34 Hz), 3.73 (s, 3H), 3.40 (d, 2H, J=6.07 Hz), 3.14 (s, 3H), 2.69 (t, 2H, J=6.57 Hz), 2.38 (m, 2H), 2.07 (m, 2H), 1.95 (m, 2H).

Example 1063

2-{5-Chloro-2-[3-(2-methoxy-ethyl)-2,3,4,5-tetrahydro-1H-benzo[d]azepin-7-ylamino]-pyrimidin-4-ylamino}-N-cyanomethyl-3-methoxy-benzamide 1063a) Prepared in an analogous manner as Example 1038 replacing 8-Methyl-1H-benzo[d][1,3]oxazine-2,4-dione with 8-Methoxy-1H-benzo[d][1,3]oxazine-2,4-dione and 7-Amino-5,5-dimethyl-1,3,4,5-tetrahydro-benzo[b]azepin-2-one with 3-(2-Methoxy-ethyl)-2,3,4,5-tetrahydro-1H-benzo[d]azepin-7-ylamine to afford 2-{5-Chloro-2-[3-(2-methoxy-ethyl)-2,3,4,5-tetrahydro-1H-benzo[d]azepin-7-ylamino]-pyrimidin-4-ylamino}-N-cyanomethyl-3-methoxy-benzamide. LC/MS (ESI): 536.27. $^1$H NMR (400 MHz, DMSO, d$_6$) δ 9.64 (m, 1H), 9.24 (m, 1H), 8.90 (m, 1H), 8.59 (s, 1H), 8.10 (s, 1H), 7.43 (m, 1H), 7.32 (m, 1H), 7.27 (m, 2H), 6.91 (m, 1H), 4.25 (d, 2H, J=5.31 Hz), 3.73 (s, 3H), 3.70 (m, 2H), 3.62 (m, 2H), 3.40 (m, 2H), 3.34 (m, 3H), 2.84-3.10 (m, 6H).

Example 1064

2-[5-Chloro-2-(5,5-dimethyl-2-oxo-2,3,4,5-tetrahydro-1H-benzo[b]azepin-7-ylamino)-pyrimidin-4-ylamino]-N-cyanomethyl-3-methoxy-benzamide 1064a) Prepared in an analogous manner as Example 1038 replacing 8-Methyl-1H-benzo[d][1,3]oxazine-2,4-dione with 8-Methoxy-1H-benzo[d][1,3]oxazine-2,4-dione to afford 2-[5-Chloro-2-(5,5-dimethyl-2-oxo-2,3,4,5-tetrahydro-1H-benzo[b]azepin-7-ylamino)-pyrimidin-4-ylamino]-N-cyanomethyl-3-methoxy-benzamide. LC/MS (ESI): 520.21. $^1$H NMR (400 MHz, DMSO, d$_6$) δ 9.28 (m, 2H), 8.90 (m, 2H), 8.11 (s, 1H), 7.31 (m, 4H), 7.22 (d, 1H, J=7.58 Hz), 6.65 (m, 1H), 4.23 (d, 2H, J=5.30 Hz), 3.71 (s, 3H), 2.10 (m, 2H), 1.91 (m, 2H), 1.21 (s, 6H).

Example 1065

2-[5-Chloro-2-(1-methyl-2-oxo-2,3,4,5-tetrahydro-1H-benzo[b]azepin-7-ylamino)-pyrimidin-4-ylamino]-N-cyanomethyl-3-methoxy-benzamide 1065a) Prepared in an analogous manner as Example 1038 replacing 8-Methyl-1H-benzo[d][1,3]oxazine-2,4-dione with 8-Methoxy-1H-benzo[d][1,3]oxazine-2,4-dione and 7-Amino-5,5-dimethyl-1,3,4,5-tetrahydro-benzo[b]azepin-2-one with 7-Amino-1-methyl-1,3,4,5-tetrahydro-benzo[b]azepin-2-one to afford 2-[5-Chloro-2-(1-methyl-2-oxo-2,3,4,5-tetrahydro-1H-benzo[b]azepin-7-ylamino)-pyrimidin-4-ylamino]-N-cyanomethyl-3-methoxy-benzamide. LC/MS (ESI): 506.15. $^1$H NMR (400 MHz, DMSO, d$_6$) δ 9.39 (m, 1H), 8.91 (m, 1H), 8.79 (s, 1H), 8.13 (s, 1H), 7.41 (m, 1H), 7.34 (m, 1H), 7.30 (m, 2H), 7.23 (d, 1H, J=7.83 Hz), 7.01 (d, 1H, J=8.34 Hz), 4.24 (d, 2H, J=5.31 Hz), 3.73 (s, 3H), 3.14 (s, 3H), 2.37 (m, 2H), 2.06 (m, 2H), 1.94 (m, 2H).

Example 1070

N-{(1R,2R)-2-[5-Chloro-2-(2-methoxy-7-morpholin-4-yl-6,7,8,9-tetrahydro-5H-benzocyclohepten-1-ylamino)-pyrimidin-4-ylamino]-cyclohexyl}-methanesulfonamide 1070a) Prepared in an analogous fashion to Example 1047 replacing (1S,2S,3R,4R)-3-(2,5-Dichloro-pyrimidin-4-ylamino)-bicyclo[2.2.1]hept-5-ene-2-carboxylic acid amide with N-[(1R,2R)-2-(2,5-Dichloro-pyrimidin-4-ylamino)-cyclohexyl]-methanesulfonamide and 3-Methoxy-7-morpholin-4-yl-6,7,8,9-tetrahydro-5H-benzocyclohepten-2-ylamine was replaced with 2-Methoxy-7-morpholin-4-yl-6,7,8,9-tetrahydro-5H-benzocyclohepten-1-ylamine to afford N-{(1R,2R)-2-[5-Chloro-2-(2-methoxy-7-morpholin-4-yl-6,7,8,9-tetrahydro-5H-benzocyclohepten-1-ylamino)-pyrimidin-4-ylamino]-cyclohexyl}-methanesulfonamide (Diasteromeric Mix). LC/MS (ESI): 579.24. $^1$H NMR (400 MHz, DMSO, d$_6$) δ 9.85 (m, 1H), 7.17 (m, 1H), 6.88 (m, 1H), 3.94 (m, 3H), 3.70 (s, 3H), 3.28 (m, 3H), 3.20 (m, 6H), 2.88 (s, 3H), 2.72 (m, 2H), 1.99 (m, 4H), 1.67 (m, 2H), 1.41 (m, 2H), 1.21 (m, 5H).

Example 1071

5-Chloro-N*2*-(2-methoxy-7-morpholin-4-yl-6,7,8,9-tetrahydro-5H-benzocyclohepten-1-yl)-N*4*-(2-pyrazol-1-yl-phenyl)-pyrimidine-2,4-diamine 1071a) Prepared in an analogous fashion to Example 1047 replacing (1S,2S,3R,4R)-3-(2,5-Dichloro-pyrimidin-4-ylamino)-bicyclo[2.2.1]hept-5-ene-2-carboxylic acid amide with (2,5-Dichloro-pyrimidin-4-yl)-(2-pyrazol-1-yl-phenyl)-amine and 3-Methoxy-7-morpholin-4-yl-6,7,8,9-tetrahydro-5H-benzocyclohepten-2-ylamine was replaced with 2-Methoxy-7-morpholin-4-yl-6,7,8,9-tetrahydro-5H-benzocyclohepten-1-ylamine to afford 5-Chloro-N*2*-(2-methoxy-7-morpholin-4-yl-6,7,8,9-tetrahydro-5H-benzocyclohepten-1-yl)-N*4*-(2-pyrazol-1-yl-phenyl)-pyrimidine-2,4-diamine. LC/MS (ESI): 546.26. $^1$H NMR (400 MHz, DMSO, d$_6$) δ 8.18 (m, 1H), 8.31 (m, 1H), 7.93 (s, 2H), 7.57 (m, 2H), 7.16 (m, 2H), 6.89 (m, 2H), 6.61 (s, 1H), 3.70 (s, 3H), 3.40 (m, 2H), 3.09 (m, 5H), 2.89 (m, 2H), 2.67 (m, 2H), 2.32 (m, 4H), 1.40 (m, 2H).

Example 1072

2-[5-Chloro-2-(2-methoxy-7-morpholin-4-yl-6,7,8,9-tetrahydro-5H-benzocyclohepten-1-ylamino)-pyrimidin-4-ylamino]-N,N-dimethyl-benzenesulfonamide 1072a) Prepared in an analogous fashion to Example 1047 replacing (1S,2S,3R,4R)-3-(2,5-Dichloro-pyrimidin-4-ylamino)-bicyclo[2.2.1]hept-5-ene-2-carboxylic acid amide with (2,5-Dichloro-pyrimidin-4-yl)-[2-(propane-2-sulfonyl)-phenyl]-amine and 3-Methoxy-7-morpholin-4-yl-6,7,8,9-tetrahydro-5H-benzocyclohepten-2-ylamine was replaced with 2-Methoxy-7-morpholin-4-yl-6,7,8,9-tetrahydro-5H-benzocyclohepten-1-ylamine to afford 2-[5-Chloro-2-(2-methoxy-7-morpholin-4-yl-6,7,8,9-tetrahydro-5H-benzocyclohepten-1-ylamino)-pyrimidin-4-ylamino]-N,N-dimethyl-benzenesulfonamide. LC/MS (ESI): 587.18. $^1$H NMR (400 MHz, DMSO, d$_6$) δ 9.48 (s, 2H), 8.67 (m, 1H), 8.20 (m, 1H), 7.70 (m, 1H), 7.15 (m, 2H), 6.89 (m, 1H), 3.72 (s, 3H), 3.65

(m, 4H), 3.12 (m, 5H), 2.88 (m, 2H), 2.72 (m, 2H), 2.67 (s, 6H), 2.32 (m, 2H), 1.44 (m, 2H).

Example 1073

2-[5-Chloro-2-(2-methoxy-7-morpholin-4-yl-6,7,8,9-tetrahydro-5H-benzocyclohepten-1-ylamino)-pyrimidin-4-ylamino]-N-methyl-benzamide 1073a) Prepared in an analogous fashion to Example 1047 replacing (1S,2S,3R,4R)-3-(2,5-Dichloro-pyrimidin-4-ylamino)-bicyclo[2.2.1]hept-5-ene-2-carboxylic acid amide with 2-(2,5-Dichloro-pyrimidin-4-ylamino)-N-methyl-benzamide and 3-Methoxy-7-morpholin-4-yl-6,7,8,9-tetrahydro-5H-benzocyclohepten-2-ylamine was replaced with 2-Methoxy-7-morpholin-4-yl-6,7,8,9-tetrahydro-5H-benzocyclohepten-1-ylamine to afford 2-[5-Chloro-2-(2-methoxy-7-morpholin-4-yl-6,7,8,9-tetrahydro-5H-benzocyclohepten-1-ylamino)-pyrimidin-4-ylamino]-N-methyl-benzamide. LC/MS (ESI): 537.20. $^1$H NMR (400 MHz, DMSO, d$_6$) δ 8.71 (m, 2H), 8.14 (m, 1H), 7.79 (m, 1H), 7.70 (m, 1H), 6.89 (m, 2H), 3.69 (s, 3H), 3.51 (m, 4H), 3.11 (m, 6H), 2.79 (m, 1H), 2.71 (s, 3H), 2.33 (m, 4H), 1.44 (m, 2H).

Example 1074

N-((1R,2R)-2-{5-Chloro-2-[7-(2,2-difluoro-ethylamino)-2-methoxy-6,7,8,9-tetrahydro-5H-benzocyclohepten-1-ylamino]-pyrimidin-4-ylamino}-cyclohexyl)-methanesulfonamide (Single Diasteromer A)

1074a) Prepared in an analogous fashion to Example 1047 replacing (1S,2S,3R,4R)-3-(2,5-Dichloro-pyrimidin-4-ylamino)-bicyclo[2.2.1]hept-5-ene-2-carboxylic acid amide with N-[(1R,2R)-2-(2,5-Dichloro-pyrimidin-4-ylamino)-cyclohexyl]-methanesulfonamide and 3-Methoxy-7-morpholin-4-yl-6,7,8,9-tetrahydro-5H-benzocyclohepten-2-ylamine was replaced with N*7*-(2,2-Difluoro-ethyl)-2-methoxy-6,7,8,9-tetrahydro-5H-benzocycloheptene-1,7-diamine to afford N-((1R,2R)-2-{5-Chloro-2-[7-(2,2-difluoro-ethylamino)-2-methoxy-6,7,8,9-tetrahydro-5H-benzocyclohepten-1-ylamino]-pyrimidin-4-ylamino}-cyclohexyl)-methanesulfonamide (Single Diasteromer A). 1$^{st}$ peak elution from HPLC purification. LC/MS (ESI): 573.25. $^1$H NMR (400 MHz, DMSO, d$_6$) δ 9.14 (m, 2H), 7.15 (m, 2H), 6.87 (m, 1H), 6.41 (td, 1H), 3.70 (s, 3H), 3.56 (m, 3H), 3.42 (m, 2H), 3.16 (s, 3H), 2.91 (m, 4H), 2.74 (m, 1H), 2.54 (m, 2H), 1.67 (m, 1H), 1.34 (m, 4H).

Example 1075

N-((1R,2R)-2-{5-Chloro-2-[7-(2,2-difluoro-ethylamino)-2-methoxy-6,7,8,9-tetrahydro-5H-benzocyclohepten-1-ylamino]-pyrimidin-4-ylamino}-cyclohexyl)-methanesulfonamide (Single Diasteromer B)

1075a) Prepared in an analogous fashion to Example 1047 replacing (1S,2S,3R,4R)-3-(2,5-Dichloro-pyrimidin-4-ylamino)-bicyclo[2.2.1]hept-5-ene-2-carboxylic acid amide with N-[(1R,2R)-2-(2,5-Dichloro-pyrimidin-4-ylamino)-cyclohexyl]-methanesulfonamide and 3-Methoxy-7-morpholin-4-yl-6,7,8,9-tetrahydro-5H-benzocyclohepten-2-ylamine was replaced with N*7*-(2,2-Difluoro-ethyl)-2-methoxy-6,7,8,9-tetrahydro-5H-benzocycloheptene-1,7-diamine to afford N-((1R,2R)-2-{5-Chloro-2-[7-(2,2-difluoro-ethylamino)-2-methoxy-6,7,8,9-tetrahydro-5H-benzocyclohepten-1-ylamino]-pyrimidin-4-ylamino}-cyclohexyl)-methanesulfonamide (Single Diasteromer B). 2nd peak elution from HPLC purification. LC/MS (ESI): 573.25. $^1$H NMR (400 MHz, DMSO, d$_6$) δ 9.14 (m, 2H), 7.15 (m, 2H), 6.87 (m, 1H), 6.41 (td, 1H), 3.70 (s, 3H), 3.56 (m, 3H), 3.42 (m, 2H), 3.16 (s, 3H), 2.91 (m, 4H), 2.74 (m, 1H), 2.54 (m, 2H), 1.67 (m, 1H), 1.34 (m, 4H).

Example 1076

5-Chloro-N*2*-[7-(2,2-difluoro-ethylamino)-2-methoxy-6,7,8,9-tetrahydro-5H-benzocyclohepten-1-yl]-N*4*-(2-pyrazol-1-yl-phenyl)-pyrimidine-2,4-diamine 1076a) Prepared in an analogous fashion to Example 1047 replacing (1S,2S,3R,4R)-3-(2,5-Dichloro-pyrimidin-4-ylamino)-bicyclo[2.2.1]hept-5-ene-2-carboxylic acid amide with (2,5-Dichloro-pyrimidin-4-yl)-(2-pyrazol-1-yl-phenyl)-amine and 3-Methoxy-7-morpholin-4-yl-6,7,8,9-tetrahydro-5H-benzocyclohepten-2-ylamine was replaced with N*7*-(2,2-Difluoro-ethyl)-2-methoxy-6,7,8,9-tetrahydro-5H-benzocycloheptene-1,7-diamine to afford 5-Chloro-N*2*-[7-(2,2-difluoro-ethylamino)-2-methoxy-6,7,8,9-tetrahydro-5H-benzocyclohepten-1-yl]-N*4*-(2-pyrazol-1-yl-phenyl)-pyrimidine-2,4-diamine. LC/MS (ESI): 540.27. $^1$H NMR (400 MHz, DMSO, d$_6$) δ 8.99 (m, 2H), 8.71 (m, 1H), 8.31 (m, 1H), 7.79 (s, 2H), 7.14 (m, 2H), 7.04 (m, 2H), 6.88 (m, 2H), 6.61 (s, 1H), 6.38 (td, 1H), 3.78 (s, 3H), 3.65 (m, 2H), 3.38 (m, 2H), 3.04 (m, 1H), 2.84 (m, 1H), 2.71 (m, 1H), 2.29 (m, 2H), 1.34 (m, 2H).

Example 1077

2-{5-Chloro-2-[7-(2,2-difluoro-ethylamino)-2-methoxy-6,7,8,9-tetrahydro-5H-benzocyclohepten-1-ylamino]-pyrimidin-4-ylamino}-N,N-dimethyl-benzenesulfonamide 1077a) Prepared in an analogous fashion to Example 1047 replacing (1S,2S,3R,4R)-3-(2,5-Dichloro-pyrimidin-4-ylamino)-bicyclo[2.2.1]hept-5-ene-2-carboxylic acid amide with (2,5-Dichloro-pyrimidin-4-yl)-[2-(propane-2-sulfonyl)-phenyl]-amine and 3-Methoxy-7-morpholin-4-yl-6,7,8,9-tetrahydro-5H-benzocyclohepten-2-ylamine was replaced with N*7*-(2,2-Difluoro-ethyl)-2-methoxy-6,7,8,9-tetrahydro-5H-benzocycloheptene-1,7-diamine to afford 2-{5-Chloro-2-[7-(2,2-difluoro-ethylamino)-2-methoxy-6,7,8,9-tetrahydro-5H-benzocyclohepten-1-ylamino]-pyrimidin-4-ylamino}-N,N-dimethyl-benzenesulfonamide. LC/MS (ESI): 581.24. $^1$H NMR (400 MHz, DMSO, d$_6$) δ 9.46 (s, 1H), 8.99 (m, 2H), 8.08 (m, 2H), 7.72 (m, 1H), 7.13 (m, 3H), 6.85 (m, 1H), 6.38 (td, 1H), 3.66 (s, 3H), 3.54 (m, 2H), 3.39 (m, 1H), 3.06 (m, 1H), 2.84 (m, 1H), 2.66 (s, 6H), 2.29 (m, 4H), 1.31 (m, 2H).

Example 1078

2-{5-Chloro-2-[7-(2,2-difluoro-ethylamino)-2-methoxy-6,7,8,9-tetrahydro-5H-benzocyclohepten-1-ylamino]-pyrimidin-4-ylamino}-N-methyl-benzamide 1078a) Prepared in an analogous fashion to Example 1047 replacing (1S,2S,3R,4R)-3-(2,5-Dichloro-pyrimidin-4-ylamino)-bicyclo[2.2.1]hept-5-ene-2-carboxylic acid amide with 2-(2,5-Dichloro-pyrimidin-4-ylamino)-N-methyl-benzamide and 3-Methoxy-7-morpholin-4-yl-6,7,8,9-tetrahydro-5H-benzocyclohepten-2-ylamine was replaced with N*7*-(2,2-Difluoro-ethyl)-2-methoxy-6,7,8,9-tetrahydro-5H-benzocycloheptene-1,7-diamine to afford 2-{5-Chloro-2-[7-(2,2-difluoro-ethylamino)-2-methoxy-6,7,8,9-tetrahydro-5H-benzocyclohepten-1-ylamino]-pyrimidin-4-ylamino}-N-methyl-benzamide. LC/MS (ESI): 531.23. $^1$H NMR (400 MHz, DMSO, $d_6$) δ 9.07 (m, 2H), 8.87 (m, 1H), 8.74 (m, 1H), 8.16 (m, 1H), 8.01 (m, 1H), 7.71 (m, 1H), 7.01 (m, 2H), 6.89 (m, 1H), 6.38 (td, 1H), 3.78 (s, 3H), 3.55 (m, 2H), 3.38 (m, 1H), 3.07 (m, 1H), 2.79 (s, 3H), 2.68-2.86 (m, 2H), 2.32 (m, 3H), 1.33 (m, 2H).

Example 1079

2-{5-Chloro-2-[3-(2-methoxy-ethyl)-2,3,4,5-tetrahydro-1H-benzo[d]azepin-7-ylamino]-pyrimidin-4-ylamino}-N-cyanomethyl-3-fluoro-benzamide 1079a) Prepared in an analogous fashion as Example 1044 replacing 7-Amino-5,5-dimethyl-1,3,4,5-tetrahydro-benzo[b]azepin-2-one with 3-(2-Methoxy-ethyl)-2,3,4,5-tetrahydro-1H-benzo[d]azepin-7-ylamine to afford 2-{5-Chloro-2-[3-(2-methoxy-ethyl)-2,3,4,5-tetrahydro-1H-benzo[d]azepin-7-ylamino]-pyrimidin-4-ylamino}-N-cyanomethyl-3-fluoro-benzamide. LC/MS (ESI): 524.31. $^1$H NMR (400 MHz, DMSO, $d_6$) δ 9.31 (m, 1H), 9.10 (m, 1H), 8.89 (s, 1H), 8.16 (s, 1H), 7.49 (m, 3H); 7.29 (s, 1H), 7.22 (d, 1H, J=7.32 Hz), 6.92 (d, 1H, J=8.34 Hz), 4.29 (d, 2H, J=5.56 Hz), 3.70 (m, 4H), 3.34 (s, 3H), 2.88-3.10 (m, 7H), 2.67 (m, 1H).

Example 1080

2-[5-Chloro-2-(5,5-dimethyl-2-oxo-2,3,4,5-tetrahydro-1H-benzo[b]azepin-8-ylamino)-pyrimidin-4-ylamino]-N-cyanomethyl-3-fluoro-benzamide 1080a) Prepared in an analogous fashion as Example 1044 replacing 7-Amino-5,5-dimethyl-1,3,4,5-tetrahydro-benzo[b]azepin-2-one with 8-Amino-5,5-dimethyl-1,3,4,5-tetrahydro-benzo[b]azepin-2-one to afford 2-[5-Chloro-2-(5,5-dimethyl-2-oxo-2,3,4,5-tetrahydro-1H-benzo[b]azepin-8-ylamino)-pyrimidin-4-ylamino]-N-cyanomethyl-3-fluoro-benzamide. LC/MS (ESI): 508.22. $^1$H NMR (400 MHz, DMSO, $d_6$) δ 9.23 (m, 1H), 9.16 (m, 1H), 9.13 (m, 1H), 9.08 (s, 1H), 8.16 (s, 1H), 7.51 (m 2H), 7.42 (m, 1H), 7.18 (d, 1H, J=8.84 Hz), 7.05 (m, 2H), 4.27 (d, 2H, J=5.30 Hz), 2.10 (m, 2H), 1.92 (m, 2H), 1.27 (s, 6H).

Example 1081

5-Chloro-N*2*-[3-methoxy-7-(2-methoxy-ethylamino)-6,7,8,9-tetrahydro-5H-benzocyclohepten-2-yl]-N*4*-[2-(pyrrolidine-1-sulfonyl)-phenyl]-pyrimidine-2,4-diamine 1081a) Prepared in an analogous fashion to Example 1047 replacing (1S,2S,3R,4R)-3-(2,5-Dichloro-pyrimidin-4-ylamino)-bicyclo[2.2.1]hept-5-ene-2-carboxylic acid amide with 2,5-Dichloro-pyrimidin-4-yl)-[2-(pyrrolidine-1-sulfonyl)-phenyl]-amine and morpholine with 2-methoxyethylamine to afford 5-Chloro-N*2*-[3-methoxy-7-(2-methoxyethylamino)-6,7,8,9-tetrahydro-5H-benzocyclohepten-2-yl]-N*4*-[2-(pyrrolidine-1-sulfonyl)-phenyl]-pyrimidine-2,4-diamine. LC/MS (ESI): 601.28. $^1$H NMR (400 MHz, DMSO, $d_6$) δ 9.43 (s, 1H), 8.51 (m, 2H), 8.42 (d, 1H, J=7.58 Hz), 8.25 (s, 1H), 7.88 (d, 1H, J=7.83 Hz), 7.57 (t, 1H, J=7.58 Hz), 7.46 (s, 1H), 7.23 (m, 1H), 6.88 (s, 1H), 3.77 (s, 3H), 3.60 (m, 2H), 3.32 (s, 3H), 3.19 (m, 7H), 2.78 (m, 3H), 2.25 (m, 2H), 1.68 (m, 5H), 1.33 (m, 2H).

Example 1082

1-(2-{5-Chloro-2-[3-methoxy-7-(2-methoxy-ethylamino)-6,7,8,9-tetrahydro-5H-benzocyclohepten-2-ylamino]-pyrimidin-4-ylamino}-benzenesulfonyl)-pyrrolidin-3-ol 1082a) Prepared in an analogous fashion to Example 1047 replacing (1S,2S,3R,4R)-3-(2,5-Dichloro-pyrimidin-4-ylamino)-bicyclo[2.2.1]hept-5-ene-2-carboxylic acid amide with 1-[2-(2,5-Dichloro-pyrimidin-4-ylamino)-benzenesulfonyl]-pyrrolidin-3-ol and morpholine with 2-methoxyethylamine to afford 1-(2-{5-Chloro-2-[3-methoxy-7-(2-methoxy-ethylamino)-6,7,8,9-tetrahydro-5H-benzocyclohepten-2-ylamino]-pyrimidin-4-ylamino}-benzenesulfonyl)-pyrrolidin-3-ol (Mixture of Enantiomers and Diastereomers). LC/MS (ESI): 617.27. $^1$H NMR (400 MHz, DMSO, $d_6$) δ 9.43 (s, 1H), 8.48 (m, 2H), 8.33 (s, 1H), 8.25 (s, 1H), 7.86 (d, 1H, 8.08 Hz), 7.55 (m, 1H), 7.46 (s, 1H), 7.33 (m, 1H), 6.89 (s, 1H), 3.87 (m, 3H), 3.76 (s, 3H), 3.59 (m, 2H), 3.33 (s, 3H), 3.22 (m, 6H), 3.03 (d, 1H, J=10.36 Hz), 2.78 (m, 3H), 2.25 (m, 2H), 1.76 (m, 1H), 1.66 (m, 1H), 1.30 (m, 2H).

Example 1083

2-{5-Chloro-2-[3-methoxy-7-(2-methoxy-ethylamino)-6,7,8,9-tetrahydro-5H-benzocyclohepten-2-ylamino]-pyrimidin-4-ylamino}-N,N-dimethyl-benzenesulfonamide 1083a) Prepared in an analogous fashion to Example 1047 replacing (1S,2S,3R,4R)-3-(2,5-Dichloro-pyrimidin-4-ylamino)-bicyclo[2.2.1]hept-5-ene-2-carboxylic acid amide with (2,5-Dichloro-pyrimidin-4-yl)-[2-(propane-2-sulfonyl)-phenyl]-amine and morpholine was replaced with 2-methoxyethylamine to afford 2-{5-Chloro-2-[3-methoxy-7-(2-methoxy-ethylamino)-6,7,8,9-tetrahydro-5H-benzocyclohepten-2-ylamino]-pyrimidin-4-ylamino}-N,N-dimethyl-benzenesulfonamide. LC/MS (ESI): 575.29. $^1$H NMR (400 MHz, DMSO, $d_6$) δ 9.37 (s, 1H), 8.50 (m, 1H), 8.42 (m, 1H), 8.31 (s, 1H), 8.25 (s, 1H), 7.82 (d, 1H, J=8.08 Hz), 7.59 (m, 1H), 7.48 (s, 1H), 7.35 (t, 1H, J=7.83 Hz), 6.89 (s, 1H), 3.84 (m, 2H), 3.80 (s, 3H), 3.61 (m, 3H), 3.33 (s, 3H), 3.19 (m, 2H), 2.79 (m, 2H), 2.61 (s, 6H), 2.26 (m, 2H), 1.33 (m, 2H).

Example 1084

5-Chloro-N*2*-[3-methoxy-7-(2-methoxy-ethylamino)-6,7,8,9-tetrahydro-5H-benzocyclohepten-2-yl]-N*4*-[2-(propane-2-sulfonyl)-phenyl]-pyrimidine-2,4-diamine 1084a) Prepared in an analogous fashion to Example 1047 replacing (1S,2S,3R,4R)-3-(2,5-Dichloro-pyrimidin-4-ylamino)-bicyclo[2.2.1]hept-5-ene-2-carboxylic acid amide with (2,5-Dichloro-pyrimidin-4-yl)-[2-(propane-2-sulfonyl)-phenyl]-amine and morpholine was replaced with 2-methoxyethylamine to afford 5-Chloro-N*2*-[3-methoxy-7-(2-methoxy-ethylamino)-6,7,8,9-tetrahydro-5H-benzocyclohepten-2-yl]-N*4*-[2-(propane-2-sulfonyl)-phenyl]-pyrimidine-2,4-diamine. LC/MS (ESI): 574.29. $^1$H NMR (400 MHz, DMSO, $d_6$) δ 9.53 (s, 1H), 8.51 (m, 1H), 8.45 (m, 1H), 8.34 (s, 1H), 8.25 (s, 1H), 7.85 (d, 1H, J=7.83 Hz), 7.63 (t, 1H, J=7.83 Hz), 7.46 (s, 1H), 7.38 (t, 1H, J=7.58 Hz), 6.89 (s, 1H), 3.76 (s, 3H), 3.59 (m, 2H), 3.45 (m, 1H), 3.34 (s, 3H), 3.19 (m, 2H), 2.78 (m, 5H), 2.24 (m, 2H), 1.33 (m, 2H), 1.15 (d, 6H, J=6.82 Hz).

Example 1085

5-Chloro-N*2*-[3-methoxy-7-(2-methoxy-ethylamino)-6,7,8,9-tetrahydro-5H-benzocyclohepten-2-yl]-N*4*-(2-pyrazol-1-yl-phenyl)-pyrimidine-2,4-diamine 1085a) Prepared in an analogous fashion to Example 1047 replacing (1S,2S,3R,4R)-3-(2,5-Dichloro-pyrimidin-4-ylamino)-bicyclo[2.2.1]hept-5-ene-2-carboxylic acid amide with (2,5-Dichloro-pyrimidin-4-yl)-(2-pyrazol-1-yl-phenyl)-amine and morpholine was replaced with 2-methoxyethylamine to afford 5-Chloro-N*2*-[3-methoxy-7-(2-methoxy-ethylamino)-6,7,8,9-tetrahydro-5H-benzocyclohepten-2-yl]-N*4*-(2-pyrazol-1-yl-phenyl)-pyrimidine-2,4-diamine. LC/MS (ESI): 534.31. $^1$H NMR (400 MHz, DMSO, $d_6$) δ 8.40 (m, 2H), 8.24 (m, 2H), 8.14 (s, 1H), 8.08 (s, 1H), 7.88 (s, 1H), 7.62 (m, 1H), 7.55 (s, 1H), 7.32 (m, 2H), 6.87 (s, 1H), 6.58 (s, 1H), 3.78 (s, 3H), 3.50 (m, 4H), 3.34 (s, 3H), 3.19 (m, 2H), 2.64 (m, 3H), 2.24 (m, 2H), 1.30 (m, 2H).

Example 1086

2-{5-Chloro-2-[3-methoxy-7-(2-methoxy-ethylamino)-6,7,8,9-tetrahydro-5H-benzocyclohepten-2-ylamino]-pyrimidin-4-ylamino}-N-methyl-benzamide 1086a) Prepared in an analogous fashion to Example 1047 replacing (1S,2S,3R,4R)-3-(2,5-Dichloro-pyrimidin-4-ylamino)-bicyclo[2.2.1]hept-5-ene-2-carboxylic acid amide with 2-(2,5-Dichloro-pyrimidin-4-ylamino)-N-methyl-benzamide and morpholine was replaced with 2-methoxyethylamine to afford 2-{5-Chloro-2-[3-methoxy-7-(2-methoxy-ethylamino)-6,7,8,9-tetrahydro-5H-benzocyclohepten-2-ylamino]-pyrimidin-4-ylamino}-N-methyl-benzamide. LC/MS (ESI): 525.32. $^1$H NMR (400 MHz, DMSO, $d_6$) δ 8.78 (m, 1H), 8.51 9m, 3H), 8.33 (s, 1H), 8.20 (s, 1H), 7.76 (d, 1H, J=8.08 Hz), 7.57 (s, 1H), 7.37 (m, 1H), 7.12 (m, 1H), 6.92 (s, 1H), 3.78 (s, 3H), 3.60 (m, 3H), 3.33 (s, 3H), 3.19 (m, 2H), 2.82 (s, 3H), 2.67 (m, 4H), 2.25 (m, 2H), 1.35 (m, 2H).

Example 1087

2-(2-{5-Chloro-4-[2-(pyrrolidine-1-sulfonyl)-phenylamino]-pyrimidin-2-ylamino}-3-methoxy-6,7,8,9-tetrahydro-5H-benzocyclohepten-7-ylamino)-ethanol 1087a) Prepared in an analogous fashion to Example 1047 replacing (1S,2S,3R,4R)-3-(2,5-Dichloro-pyrimidin-4-ylamino)-bicyclo[2.2.1]hept-5-ene-2-carboxylic acid amide with 2,5-Dichloro-pyrimidin-4-yl)-[2-(pyrrolidine-1-sulfonyl)-phenyl]-amine and morpholine with ethanolamine to afford 2-(2-{5-Chloro-4-[2-(pyrrolidine-1-sulfonyl)-phenylamino]-pyrimidin-2-ylamino}-3-methoxy-6,7,8,9-tetrahydro-5H-benzocyclohepten-7-ylamino)-ethanol. LC/MS (ESI): 587.23. $^1$H NMR (400 MHz, DMSO, $d_6$) δ 9.45 (s, 1H), 8.43 (m, 3H), 8.33 (s, 1H), 8.25 (s, 1H), 7.87 (d, 1H, J=8.08 Hz), 7.58 (t, 1H, J=7.58 Hz), 7.46 (s, 1H), 7.34 (t, 1H, J=7.58 Hz), 6.89 (s, 1H), 3.77 (s, 3H), 3.67 (m, 2H), 3.35 (m, 1H), 3.15 (m, 4H), 3.06 (m, 2H), 2.78 (m, 3H), 2.26 (m, 2H), 1.65 (m, 4H), 1.27 (m, 2H).

Example 1088

1-(2-{5-Chloro-2-[7-(2-hydroxy-ethylamino)-3-methoxy-6,7,8,9-tetrahydro-5H-benzocyclohepten-2-ylamino]-pyrimidin-4-ylamino}-benzenesulfonyl)-pyrrolidin-3-ol 1088a) Prepared in an analogous fashion to Example 1047 replacing (1S,2S,3R,4R)-3-(2,5-Dichloro-pyrimidin-4-ylamino)-bicyclo[2.2.1]hept-5-ene-2-carboxylic acid amide with 1-[2-(2,5-Dichloro-pyrimidin-4-ylamino)-benzenesulfonyl]-pyrrolidin-3-ol and morpholine with ethanolamine to afford 1-(2-{5-Chloro-2-[7-(2-hydroxy-ethylamino)-3-methoxy-6,7,8,9-tetrahydro-5H-benzocyclohepten-2-ylamino]-pyrimidin-4-ylamino}-benzenesulfonyl)-pyrrolidin-3-ol (Mixture of Enantiomers and Diasteromers). LC/MS (ESI): 603.21. $^1$H NMR (400 MHz, DMSO, $d_6$) δ 9.43 (s, 1H), 8.45 (m, 1H), 8.37 (m, 2H), 8.27 (s, 1H), 8.24 (s, 1H), 7.86 (m, 1H), 7.53 (m, 1H), 7.47 (s, 1H), 7.30 (m, 1H), 6.88 (s, 1H), 4.17 (m, 1H), 3.76 (s, 3H), 3.65 (m, 2H), 3.23 (m, 4H), 3.16 (m, 4H), 2.78 (m, 3H), 2.25 (m, 3H), 1.78 (m, 1H), 1.67 (m, 1H), 1.33 (m, 2H).

Example 1089

2-{5-Chloro-2-[7-(2-hydroxy-ethylamino)-3-methoxy-6,7,8,9-tetrahydro-5H-benzocyclohepten-2-ylamino]-pyrimidin-4-ylamino}-N,N-dimethyl-benzenesulfonamide 1089a) Prepared in an analogous fashion to Example 1047 replacing (1S,2S,3R,4R)-3-(2,5-Dichloro-pyrimidin-4-ylamino)-bicyclo[2.2.1]hept-5-ene-2-carboxylic acid amide with (2,5-Dichloro-pyrimidin-4-yl)-[2-(propane-2-sulfonyl)-phenyl]-amine and morpholine was replaced with ethanolamine to afford 2-{5-Chloro-2-[7-(2-hydroxy-ethylamino)-3-methoxy-6,7,8,9-tetrahydro-5H-benzocyclohepten-2-ylamino]-pyrimidin-4-ylamino}-N,N-dimethyl-benzenesulfonamide. LC/MS (ESI): 561.25. $^1$H NMR (400 MHz, DMSO, $d_6$) δ 9.37 (s, 1H), 8.42 (m, 3H), 8.30 (s, 1H), 8.25 (s, 1H), 7.82 (d, 1H, J=7.83 Hz), 7.47 (s, 1H), 7.59 (t, 1H, J=7.58 Hz), 6.89 (s, 1H), 3.77 (s, 3H), 3.67 (m, 3H), 3.35 (m, 1H), 3.06 (m, 2H), 2.78 (m, 3H), 2.72 (s, 6H), 2.27 (m, 2H), 1.32 (m, 2H).

Example 1090

2-(2-{5-Chloro-4-[2-(propane-2-sulfonyl)-phenylamino]-pyrimidin-2-ylamino}-3-methoxy-6,7,8,9-tetrahydro-5H-benzocyclohepten-7-ylamino)-ethanol 1090a) Prepared in an analogous fashion to Example 1047 replacing (1S,2S,3R,4R)-3-(2,5-Dichloro-pyrimidin-4-ylamino)-bicyclo[2.2.1]hept-5-ene-2-carboxylic acid amide with (2,5-Dichloro-pyrimidin-4-yl)-[2-(propane-2-sulfonyl)-phenyl]-amine and morpholine was replaced with ethanolamine to afford 2-(2-{5-Chloro-4-[2-(propane-2-sulfonyl)-phenylamino]-pyrimidin-2-ylamino}-3-methoxy-6,7,8,9-tetrahydro-5H-benzocyclohepten-7-ylamino)-ethanol. LC/MS (ESI): 560.25. $^1$H NMR (400 MHz, DMSO, $d_6$) δ 9.53 (s, 1H), 8.42 (m, 3H), 8.35 (s, 1H), 8.25 (s, 1H), 7.85 (d, 1H, J=7.83 Hz), 7.64 (t, 1H, J=7.83 Hz), 7.46 (s, 1H), 7.38 (t, 1H, J=7.58 Hz), 6.89 (s, 1H), 3.76 (s, 3H), 3.69 (m, 3H), 3.43 (m, 1H), 3.35 (m, 1H), 3.07 (m, 2H), 2.78 (m, 3H), 2.26 (m, 2H), 1.31 (m, 2H), 1.16 (d, 6H, J=6.82 Hz).

Example 1091

2-{2-[5-Chloro-4-(2-pyrazol-1-yl-phenylamino)-pyrimidin-2-ylamino]-3-methoxy-6,7,8,9-tetrahydro-5H-benzocyclohepten-7-ylamino}-ethanol 1091a) Prepared in an analogous fashion to Example 1047 replacing (1S,2S,3R,4R)-3-(2,5-Dichloro-pyrimidin-4-ylamino)-bicyclo[2.2.1]hept-5-ene-2-carboxylic acid amide with (2,5-Dichloro-pyrimidin-4-yl)-(2-pyrazol-1-yl-phenyl)-amine and morpholine was replaced with ethanolamine to afford 2-{2-[5-Chloro-4-(2-pyrazol-1-yl-phenylamino)-pyrimidin-2-ylamino]-3-methoxy-6,7,8,9-tetrahydro-5H-benzocyclohepten-7-ylamino}-ethanol. LC/MS (ESI): 520.22. $^1$H NMR (400 MHz, DMSO, $d_6$) δ 10.36 (s, 1H), 8.44 (m, 2H), 8.22 (m, 3H), 8.17 (s, 1H), 7.87 (s, 1H), 7.64 (d, 1H, J=7.57 Hz), 7.53 (s, 1H), 7.33 (m, 2H), 6.88 (s, 1H), 6.58 (s, 1H), 3.78 (s, 3H), 3.67 (t, 2H, J=5.06 Hz), 3.27 (m, 1H), 3.07 (m, 2H), 2.79 (m, 4H), 2.28 (m, 2H), 1.28 (m, 2H).

Example 1092

2-{5-Chloro-2-[7-(2-hydroxy-ethylamino)-3-methoxy-6,7,8,9-tetrahydro-5H-benzocyclohepten-2-ylamino]-pyrimidin-4-ylamino}-N-methyl-benzamide 1092a) Prepared in an analogous fashion to Example 1047 replacing (1S,2S,3R,4R)-3-(2,5-Dichloro-pyrimidin-4-ylamino)-bicyclo[2.2.1]hept-5-ene-2-carboxylic acid amide with 2-(2,5-Dichloro-pyrimidin-4-ylamino)-N-methyl-benzamide and morpholine was replaced with ethanolamine to afford 2-{5-Chloro-2-[7-(2-hydroxy-ethylamino)-3-methoxy-6,7,8,9-tetrahydro-5H-benzocyclohepten-2-ylamino]-pyrimidin-4-ylamino}-N-methyl-benzamide. LC/MS (ESI): 511.29. $^1$H NMR (400 MHz, DMSO, $d_6$) δ 11.69 (s, 1H), 8.76 (m, 1H), 8.58 (m, 1H), 8.38 (m, 2H), 8.25 (s, 1H), 8.18 (s, 1H), 7.75 (d, 1H, J=8.08 Hz), 7.58 (s, 1H), 7.37 (t, 1H, J=7.58 Hz), 7.12 (t, 1H, J=7.58 Hz), 6.91 (s, 1H), 3.78 (s, 3H), 3.67 (m, 2H), 3.35 (m, 1H), 3.17 (m, 2H), 2.86 (s, 3H), 2.78 (m, 4H), 2.24 (m, 2H), 1.33 (m, 2H).

Example 1093

2-{5-Chloro-2-[7-(2-hydroxy-ethylamino)-3-methoxy-6,7,8,9-tetrahydro-5H-benzocyclohepten-2-ylamino]-pyrimidin-4-ylamino}-benzoic acid 2-methoxy-ethyl ester 1093a) Prepared in an analogous fashion to Example 1047 replacing (1S,2S,3R,4R)-3-(2,5-Dichloro-pyrimidin-4-ylamino)-bicyclo[2.2.1]hept-5-ene-2-carboxylic acid amide with 2-(2,5-Dichloro-pyrimidin-4-ylamino)-benzoic acid 2-methoxy-ethyl ester and morpholine was replaced with ethanolamine to afford 2-{5-Chloro-2-[7-(2-hydroxy-ethylamino)-3-methoxy-6,7,8,9-tetrahydro-5H-benzocyclohepten-2-ylamino]-pyrimidin-4-ylamino}-benzoic acid 2-methoxy-ethyl ester. LC/MS (ESI): 556.32. $^1$H NMR (400 MHz, DMSO, $d_6$) δ 10.88 (s, 1H), 8.65 (m, 1H), 8.37 (m, 2H), 8.32 (s, 1H), 8.23 (s, 1H), 8.03 (d, 1H, J=8.09 Hz), 7.49 (m, 2H), 7.18 (t, 1H, J=7.57 Hz), 6.91 (s, 1H), 4.42 (m, 2H), 3.77 (s, 3H), 3.67 (m, 4H), 3.30 (s, 3H), 3.06 (m, 2H), 2.80 (m, 5H), 2.26 (m, 2H), 1.34 (m, 2H).

Example 1094

N-((1R,2R)-2-{5-Chloro-2-[7-(2-hydroxy-ethylamino)-3-methoxy-6,7,8,9-tetrahydro-5H-benzocyclohepten-2-ylamino]-pyrimidin-4-ylamino}-cyclohexyl)-methanesulfonamide (Single Diasteromer A)

1094a) Prepared in an analogous fashion to Example 1047 replacing (1S,2S,3R,4R)-3-(2,5-Dichloro-pyrimidin-4-ylamino)-bicyclo[2.2.1]hept-5-ene-2-carboxylic acid amide with N-[(1R,2R)-2-(2,5-Dichloro-pyrimidin-4-ylamino)-cyclohexyl]-methanesulfonamide and morpholine was replaced with ethanolamine to afford N-((1R,2R)-2-{5-Chloro-2-[7-(2-hydroxy-ethylamino)-3-methoxy-6,7,8,9-tetrahydro-5H-benzocyclohepten-2-ylamino]-pyrimidin-4-ylamino}-cyclohexyl)-methanesulfonamide (Single Diasteromer A). 1$^{st}$ peak elution from HPLC purification. LC/MS (ESI): 553.28. $^1$H NMR (400 MHz, DMSO, $d_6$) δ 7.97 (s, 1H), 7.91 (s, 1H), 7.50 (s, 1H), 7.19 (m, 1H), 6.79 (m, 2H), 4.46 (m, 1H), 3.81 (s, 3H), 3.45 (m, 2H), 2.91 (s, 3H), 2.76 (m, 3H), 2.64 (m, 4H), 1.99 (m, 4H), 1.68 (m, 2H), 1.34 (m, 2H), 1.22 (m, 4H).

Example 1095

N-((1R,2R)-2-{5-Chloro-2-[7-(2-hydroxy-ethylamino)-3-methoxy-6,7,8,9-tetrahydro-5H-benzocyclohepten-2-ylamino]-pyrimidin-4-ylamino}-cyclohexyl)-methanesulfonamide (Single Diasteromer B)

1095a) Prepared in an analogous fashion to Example 1047 replacing (1S,2S,3R,4R)-3-(2,5-Dichloro-pyrimidin-4-ylamino)-bicyclo[2.2.1]hept-5-ene-2-carboxylic acid amide with N-[(1R,2R)-2-(2,5-Dichloro-pyrimidin-4-ylamino)-cyclohexyl]-methanesulfonamide and morpholine was replaced with ethanolamine to afford N-((1R,2R)-2-{5-Chloro-2-[7-(2-hydroxy-ethylamino)-3-methoxy-6,7,8,9-tetrahydro-5H-benzocyclohepten-2-ylamino]-pyrimidin-4-ylamino}-cyclohexyl)-methanesulfonamide (Single Diasteromer B). 2$^{nd}$ peak elution from HPLC purification. LC/MS (ESI): 553.28. $^1$H NMR (400 MHz, DMSO, $d_6$) δ 7.97 (s, 1H), 7.91 (s, 1H), 7.50 (s, 1H), 7.19 (m, 1H), 6.79 (m, 2H), 4.46 (m, 1H), 3.81 (s, 3H), 3.45 (m, 2H), 2.91 (s, 3H), 2.76 (m, 3H), 2.64 (m, 4H), 1.99 (m, 4H), 1.68 (m, 2H), 1.34 (m, 2H), 1.22 (m, 4H).

Example 1096

(1S,2S,3R,4R)-3-{5-Chloro-2-[7-(2-hydroxy-ethylamino)-3-methoxy-6,7,8,9-tetrahydro-5H-benzocyclohepten-2-ylamino]-pyrimidin-4-ylamino}-bicyclo[2.2.1]hept-5-ene-2-carboxylic acid amide (Diasteromer A)

1096a) Prepared in an analogous fashion to Example 1047 replacing morpholine with ethanolamine to afford (1S,2S,3R,4R)-3-{5-Chloro-2-[7-(2-hydroxy-ethylamino)-3-methoxy-6,7,8,9-tetrahydro-5H-benzocyclohepten-2-ylamino]-pyrimidin-4-ylamino}-bicyclo[2.2.1]hept-5-ene-2-carboxylic acid amide (Diasteromer A). 1$^{st}$ peak elution from HPLC purification. LC/MS (ESI): 513.29. $^1$H NMR (400 MHz, DMSO, $d_6$) δ 7.94 (d, 2H, J=4.04 Hz), 7.76 (s, 1H), 7.70 (d, 1H, J=7.58 Hz), 7.54 (s, 1H), 7.26 (s, 1H), 6.81 (s, 1H), 6.35 (m, 1H), 6.20 (m, 1H), 4.46 (m, 1H), 4.19 (m, 1H), 3.81 (s, 3H), 3.45 (d, 2H, J=5.30 Hz), 2.76 (m, 1H), 2.54-2.64 (m, 9H), 2.10 (d, 1H, J=8.84 Hz), 1.96 (m, 2H), 1.40 (d, 1H, J=8.84 Hz), 1.19 (m, 2H).

Example 1097

(1S,2S,3R,4R)-3-{5-Chloro-2-[7-(2-hydroxy-ethylamino)-3-methoxy-6,7,8,9-tetrahydro-5H-benzocyclohepten-2-ylamino]-pyrimidin-4-ylamino}-bicyclo[2.2.1]hept-5-ene-2-carboxylic acid amide (Diasteromer B)

1097a) Prepared in an analogous fashion to Example 1047 replacing morpholine with ethanolamine to afford (1S,2S,3R,4R)-3-{5-Chloro-2-[7-(2-hydroxy-ethylamino)-3-methoxy-6,7,8,9-tetrahydro-5H-benzocyclohepten-2-ylamino]-pyrimidin-4-ylamino}-bicyclo[2.2.1]hept-5-ene-2-carboxylic acid amide (Diasteromer B). $2^{nd}$ peak elution from HPLC purification. LC/MS (ESI): 513.29. $^1$H NMR (400 MHz, DMSO, $d_6$) δ 7.94 (d, 2H, J=4.04 Hz), 7.76 (s, 1H), 7.70 (d, 1H, J=7.58 Hz), 7.54 (s, 1H), 7.26 (s, 1H), 6.81 (s, 1H), 6.35 (m, 1H), 6.20 (m, 1H), 4.46 (m, 1H), 4.19 (m, 1H), 3.81 (s, 3H), 3.45 (d, 2H, J=5.30 Hz), 2.76 (m, 1H), 2.54-2.64 (m, 9H), 2.10 (d, 1H, J=8.84 Hz), 1.96 (m, 2H), 1.40 (d, 1H, J=8.84 Hz), 1.19 (m, 2H).

Example 1098

1-(2-{5-Chloro-2-[3-methoxy-7-(4-methyl-piperazin-1-yl)-6,7,8,9-tetrahydro-5H-benzocyclohepten-2-ylamino]-pyrimidin-4-ylamino}-benzenesulfonyl)-pyrrolidin-3-ol 1098a) Prepared in an analogous fashion to Example 1047 replacing (1S,2S,3R,4R)-3-(2,5-Dichloro-pyrimidin-4-ylamino)-bicyclo[2.2.1]hept-5-ene-2-carboxylic acid amide with 1-[2-(2,5-Dichloro-pyrimidin-4-ylamino)-benzenesulfonyl]-pyrrolidin-3-ol and morpholine with N-methylpiperazine to afford 1-(2-{5-Chloro-2-[3-methoxy-7-(4-methyl-piperazin-1-yl)-6,7,8,9-tetrahydro-5H-benzocyclohepten-2-ylamino]-pyrimidin-4-ylamino}-benzenesulfonyl)-pyrrolidin-3-ol (Mixture of Enantiomers and Diasteromers). LC/MS (ESI): 642.38. $^1$H NMR (400 MHz, DMSO, $d_6$) δ 9.43 (s, 1H), 8.34 (m, 1H), 8.26 (m, 2H), 7.87 (d, 1H, J=8.09 Hz), 7.57 (m, 1H), 7.50 (s, 1H), 7.34 (m, 1H), 6.91 (s, 1H), 4.17 (m, 2H), 3.89 (m, 2H), 3.77 (s, 3H), 3.56 (m, 4H), 3.31 (m, 5H), 3.23 (m, 1H), 2.75 (s, 3H), 2.67-2.80 (m, 4H), 2.15 (m, 2H), 1.78 (m, 1H), 1.67 (m, 1H), 1.41 (m, 2H).

Example 1099

2-{5-Chloro-2-[3-methoxy-7-(4-methyl-piperazin-1-yl)-6,7,8,9-tetrahydro-5H-benzocyclohepten-2-ylamino]-pyrimidin-4-ylamino}-N,N-dimethyl-benzenesulfonamide 1099a) Prepared in an analogous fashion to Example 1047 replacing (1S,2S,3R,4R)-3-(2,5-Dichloro-pyrimidin-4-ylamino)-bicyclo[2.2.1]hept-5-ene-2-carboxylic acid amide with (2,5-Dichloro-pyrimidin-4-yl)-[2-(propane-2-sulfonyl)-phenyl]-amine and morpholine was replaced with N-methylpiperazine to afford 2-{5-Chloro-2-[3-methoxy-7-(4-methyl-piperazin-1-yl)-6,7,8,9-tetrahydro-5H-benzocyclohepten-2-ylamino]-pyrimidin-4-ylamino}-N,N-dimethyl-benzenesulfonamide. LC/MS (ESI): 600.35. $^1$H NMR (400 MHz, DMSO, $d_6$) δ 9.34 (s, 1H), 8.38 (m, 1H), 8.26 (m, 2H), 7.83 (d, 1H, J=8.08 Hz), 7.61 (m, 1H), 7.52 (s, 1H), 7.37 (m, 1H), 6.99 (s, 1H), 3.86 (m, 2H), 3.77 (s, 3H), 3.31 (m, 5H), 2.81 (s, 3H), 2.67-2.80 (m, 4H), 2.64 (s, 6H), 2.17 (m, 2H), 1.37 (m, 2H).

Example 1100

5-Chloro-N*2*-[3-methoxy-7-(4-methyl-piperazin-1-yl)-6,7,8,9-tetrahydro-5H-benzocyclohepten-2-yl]-N*4*-[2-(propane-2-sulfonyl)-phenyl]-pyrimidine-2,4-diamine 1100a) Prepared in an analogous fashion to Example 1047 replacing (1S,2S,3R,4R)-3-(2,5-Dichloro-pyrimidin-4-ylamino)-bicyclo[2.2.1]hept-5-ene-2-carboxylic acid amide with (2,5-Dichloro-pyrimidin-4-yl)-[2-(propane-2-sulfonyl)-phenyl]-amine and morpholine was replaced with N-methylpiperazine to afford 5-Chloro-N*2*-[3-methoxy-7-(4-methyl-piperazin-1-yl)-6,7,8,9-tetrahydro-5H-benzocyclohepten-2-yl]-N*4*-[2-(propane-2-sulfonyl)-phenyl]-pyrimidine-2,4-diamine. LC/MS (ESI): 599.35. $^1$H NMR (400 MHz, DMSO, $d_6$) δ 9.50 (s, 1H), 8.43 (m, 1H), 8.29 (s, 1H), 8.25 (s, 1H), 7.86 (d, 1H, J=8.08 Hz), 7.66 (m, 1H), 7.51 (s, 1H), 7.40 (m, 1H), 6.91 (s, 1H), 3.80 (m, 3H), 3.77 (s, 3H), 3.42 (m, 4H), 3.17 (m, 2H), 2.81 (s, 3H), 2.64-2.80 (m, 5H), 2.18 (m, 2H), 1.45 (m, 2H), 1.16 (m, 6H).

Example 1101

N-((1R,2R)-2-{5-Chloro-2-[3-methoxy-7-(4-methyl-piperazin-1-yl)-6,7,8,9-tetrahydro-5H-benzocyclohepten-2-ylamino]-pyrimidin-4-ylamino}-cyclohexyl)-methanesulfonamide (Diasteromer A)

1101a) Prepared in an analogous fashion to Example 1047 replacing (1S,2S,3R,4R)-3-(2,5-Dichloro-pyrimidin-4-ylamino)-bicyclo[2.2.1]hept-5-ene-2-carboxylic acid amide with N-[(1R,2R)-2-(2,5-Dichloro-pyrimidin-4-ylamino)-cyclohexyl]-methanesulfonamide and morpholine was replaced with N-methylpiperazine to afford N-((1R,2R)-2-{5-Chloro-2-[3-methoxy-7-(4-methyl-piperazin-1-yl)-6,7,8,9-tetrahydro-5H-benzocyclohepten-2-ylamino]-pyrimidin-4-ylamino}-cyclohexyl)-methanesulfonamide (Diasteromer A). $1^{st}$ peak elution from HPLC purification. LC/MS (ESI): 592.36. $^1$H NMR (400 MHz, DMSO, $d_6$) δ 8.07 (s, 1H), 7.18 (d, 1H, J=8.59 Hz), 6.92 (s, 1H), 3.82 (s, 3H), 3.51 (m, 3H), 3.38 (m, 4H), 2.92 (s, 3H), 2.66-2.71 (m, 6H), 2.50 (s, 3H), 2.05 (s, 3H), 1.92 (m, 1H), 1.69 (m, 2H), 1.37 (m, 7H).

Example 1102

N-((1R,2R)-2-{5-Chloro-2-[3-methoxy-7-(4-methyl-piperazin-1-yl)-6,7,8,9-tetrahydro-5H-benzocyclohepten-2-ylamino]-pyrimidin-4-ylamino}-cyclohexyl)-methanesulfonamide (Diasteromer B)

1102a) Prepared in an analogous fashion to Example 1047 replacing (1S,2S,3R,4R)-3-(2,5-Dichloro-pyrimidin-4-ylamino)-bicyclo[2.2.1]hept-5-ene-2-carboxylic acid amide with N-[(1R,2R)-2-(2,5-Dichloro-pyrimidin-4-ylamino)-cyclohexyl]-methanesulfonamide and morpholine was replaced with N-methylpiperazine to afford N-((1R,2R)-2-{5-Chloro-2-[3-methoxy-7-(4-methyl-piperazin-1-yl)-6,7,8,9-tetrahydro-5H-benzocyclohepten-2-ylamino]-pyrimidin-4-ylamino}-cyclohexyl)-methanesulfonamide (Diasteromer B). $2^{nd}$ peak elution from HPLC purification. LC/MS (ESI): 592.36. $^1$H NMR (400 MHz, DMSO, $d_6$) δ 8.03 (s, 1H), 7.79 (m, 1H), 7.21 (d, 1H, J=8.60 Hz), 6.95 (s, 1H), 4.32 (m, 1H), 3.86 (s, 3H), 3.62 (m, 1H), 3.45 (m, 3H), 3.37 (s, 3H), 3.13 (m, 2H), 2.87 (s, 3H), 2.71-2.86 (m, 8H), 2.17 (m, 1H), 2.00 (m, 2H), 1.69 (m, 2H), 1.27-1.43 (m, 7H).

Example 1103

(1S,2S,3R,4R)-3-{5-Chloro-2-[3-methoxy-7-(4-methyl-piperazin-1-yl)-6,7,8,9-tetrahydro-5H-benzocyclohepten-2-ylamino]-pyrimidin-4-ylamino}-bicyclo[2.2.1]hept-5-ene-2-carboxylic acid amide (Diasteromer A)

1103a) Prepared in an analogous fashion to Example 1047 replacing morpholine with N-methylpiperazine to afford (1S,2S,3R,4R)-3-{5-Chloro-2-[3-methoxy-7-(4-methyl-piperazin-1-yl)-6,7,8,9-tetrahydro-5H-benzocyclohepten-2-ylamino]-pyrimidin-4-ylamino}-bicyclo[2.2.1]hept-5-ene-2-carboxylic acid amide (Diasteromer A). $1^{st}$ peak elution from HPLC purification. LC/MS (ESI): 552.38. $^1$H NMR (400 MHz, DMSO, $d_6$) δ 8.12 (s, 1H), 7.89 (s, 1H), 7.78 (m, 1H), 7.38 (s, 1H), 6.96 (s, 1H), 6.35 (m, 1H), 6.14 (m, 1H), 4.02 (m, 2H), 3.82 (s, 3H), 3.50 (m, 4H), 3.30 (m, 3H), 3.14 (m, 2H), 2.78 (s, 3H), 2.71-2.92 (m, 6H), 2.16 (m, 2H), 2.05 (m, 2H), 1.43 (m, 4H).

Example 1104

(1S,2S,3R,4R)-3-{5-Chloro-2-[3-methoxy-7-(4-methyl-piperazin-1-yl)-6,7,8,9-tetrahydro-5H-benzocyclohepten-2-ylamino]-pyrimidin-4-ylamino}-bicyclo[2.2.1]hept-5-ene-2-carboxylic acid amide (Diasteromer B)

1104a) Prepared in an analogous fashion to Example 1047 replacing morpholine with N-methylpiperazine to afford (1S,2S,3R,4R)-3-{5-Chloro-2-[3-methoxy-7-(4-methyl-piperazin-1-yl)-6,7,8,9-tetrahydro-5H-benzocyclohepten-2-ylamino]-pyrimidin-4-ylamino}-bicyclo[2.2.1]hept-5-ene-2-carboxylic acid amide (Diasteromer B). $2^{nd}$ peak elution from HPLC purification. LC/MS (ESI): 552.38. $^1$H NMR (400 MHz, DMSO, $d_6$) δ 8.12 (s, 1H), 7.89 (s, 1H), 7.78 (m, 1H), 7.38 (s, 1H), 6.96 (s, 1H), 6.35 (m, 1H), 6.14 (m, 1H), 4.02 (m, 2H), 3.82 (s, 3H), 3.50 (m, 4H), 3.30 (m, 3H), 3.14 (m, 2H), 2.78 (s, 3H), 2.71-2.92 (m, 6H), 2.16 (m, 2H), 2.05 (m, 2H), 1.43 (m, 4H).

Example 1111

2-{5-Chloro-2-[3-(3-dimethylamino-propyl)-8-methoxy-2-oxo-2,3,4,5-tetrahydro-1H-benzo[d]azepin-7-ylamino]-pyrimidin-4-ylamino}-benzoic acid isopropyl ester 1111a) 3-(3-Chloro-propyl)-8-methoxy-1,3-dihydro-benzo[d]azepin-2-one was prepared from 8-methoxy-1,3-dihydro-benzo[d]azepin-2-one and 1-bromo-3-chloropropane in an analogous manner to Example 251a. Product isolated as a brown solid (5.87 g, 84%). LC/MS (ESI+) 266 (M+H).

1111b) Into a 1-neck round-bottom flask was added 3-(3-chloro-propyl)-8-methoxy-1,3-dihydro-benzo[d]azepin-2-one (2.5 g, 0.0094 mol), dimethylamine hydrochloride (1.534 g, 0.01882 mol), Potassium iodide (0.468 g, 0.00282 mol), and Potassium carbonate (5.201 g, 0.03763 mol), in Acetonitrile (25 mL), and the reaction was stirred over night at 50° C. The reaction mixture was next partitioned between water and dichloromethane, and the layers were separated. The aqueous phase was extracted once with dichloromethane and the combined organic extract was washed with water. The organic solution was next extracted twice with 100 mL HCl solution (~4N), and the aqueous extract was washed once with dichloromethane (50 mL). The aqueous solution of the chlorohydrate thus obtained was basified with solid $Na_2CO_3$ to pH 11. Extraction with dichloromethane, drying of the extracts ($MgSO_4$), concentration and high vacuum drying provided 3-(3-dimethylamino-propyl)-8-methoxy-1,3-dihydro-benzo[d]azepin-2-one, which was used without further purification (oil, 1.13 g, 44%). LC/MS (ESI+) 275 (M+1).

1111c) Following procedures similar to Example 251b-d, 3-(3-dimethylamino-propyl)-8-methoxy-1,3-dihydro-benzo[d]azepin-2-one was converted via reduction of the olefin, nitration, and reduction of the nitro-group to amino- to a 1:1 mixture of [7-amino-3-(3-dimethylamino-propyl)-8-methoxy-1,3,4,5-tetrahydro-benzo[d]azepin-2-one and 9-amino-3-(3-dimethylamino-propyl)-8-methoxy-1,3,4,5-tetrahydro-benzo[d]azepin-2-one, which were used next without separation.

1111d) Following a procedure similar to Example 241i, a 1:1 mixture of [7-amino-3-(3-dimethylamino-propyl)-8-methoxy-1,3,4,5-tetrahydro-benzo[d]azepin-2-one and 9-amino-3-(3-dimethylamino-propyl)-8-methoxy-1,3,4,5-tetrahydro-benzo[d]azepin-2-one, and 2-(2,5-dichloro-pyrimidin-4-ylamino)-N-methyl-benzamide were converted to 2-{5-chloro-2-[3-(3-dimethylamino-propyl)-8-methoxy-2-oxo-2,3,4,5-tetrahydro-1H-benzo[d]azepin-7-ylamino]-pyrimidin-4-ylamino}-benzoic acid isopropyl ester as a yellow solid (7 mg, 7%) (The solvent, isopropanol, displaced the benzamide methylamine in this example). MP: 63-90° C.; $^1$H-NMR (CDCl$_3$) δ 11.12 (s, 1H), 8.79 (d, J=8.6 Hz, 1H), 8.15 (s, 1H), 8.09 (d, J=7.8 Hz, 1H), 8.06 (s, 1H), 7.50 (m, 1H), 7.45 (s, 1H), 7.09 (m, 1H), 6.63 (s, 1H), 5.33 (hept, J=6.4 Hz, 1H), 3.88 (s, 3H), 3.84 (s, 2H), 3.72 (m, 2H), 3.46 (apparent t, J=7.2 Hz, 2H), 3.01 (m, 2H), 2.37 (m, 2H), 2.28 (s, 6H), 1.81 (m, 2H), 1.41 (d, J=5.3 Hz, 6H); LC/MS (ESI+): 581.05 (M+H).

Example 1112

2-{7-[5-Chloro-4-((1R,2R)-2-methanesulfonylamino-cyclohexylamino)-pyrimidin-2-ylamino]-8-methoxy-1,2,4,5-tetrahydro-benzo[d]azepin-3-yl}-N-methyl-acetamide Following a procedure similar to Example 258c, 2-(7-amino-8-methoxy-1,2,4,5-tetrahydro-benzo[d]azepin-3-yl)-N-methyl-acetamide, prepared in analogous manner to Example 258a-b, and N-[(1R,2R)-2-(2,5-dichloro-pyrimidin-4-ylamino)-cyclohexyl]-methanesulfonamide were converted to 2-{7-[5-chloro-4-((1R,2R)-2-methanesulfonylamino-cyclohexylamino)-pyrimidin-2-ylamino]-8-methoxy-1,2,4,5-tetrahydro-benzo[d]azepin-3-yl}-N,N-dimethyl-acetamide (42 mg, 40%) as a white solid. MP: 92-104° C.; $^1$H-NMR (CDCl$_3$) δ 8.01 (s, 1H), 7.95 (s, 1H), 7.33 (br s, 1H), 7.32 (s, 1H), 6.65 (s, 1H), 5.36 (d, J=8.0 Hz, 1H), 5.27 (d, J=6.8 Hz, 1H), 3.95 (m, 1H), 3.87 (s, 3H), 3.22 (m, 1H), 3.13 (s, 2H), 2.89 (m, 4H), 2.88 (s, 3H), 2.79 (s, 3H), 2.72 (m, 4H), 2.23 (m, 2H), 1.83 (m, 2H), 1.37 (m, 2H), 0.86 (m, 2H); LC/MS (ESI+): 565.99 (M+H).

Example 1113

2-{7-[5-Chloro-4-(2-methoxy-4-morpholin-4-yl-phenylamino)-pyrimidin-2-ylamino]-8-methoxy-1,2,4,5-tetrahydro-benzo[d]azepin-3-yl}-N-methyl-acetamide Following a procedure similar to Example 258c, 2-(7-amino-8-methoxy-1,2,4,5-tetrahydro-benzo[d]azepin-3-yl)-N-methyl-acetamide and (2,5-dichloro-pyrimidin-4-yl)-(2- methoxy-4-morpholin-4-yl-phenyl)-amine were converted to 2-{7-[5-chloro-4-(2-methoxy-4-morpholin-4-yl-phenylamino)-pyrimidin-2-ylamino]-8-methoxy-1,2,4,5-tetrahydro-benzo[d]azepin-3-yl}-N-methyl-acetamide (41 mg, 41%) as a white solid. MP: 113-130° C.; $^1$H-NMR (CDCl$_3$) δ 8.22 (d, J=8.8 Hz, 1H), 8.13 (s, 1H), 8.02 (s, 1H), 7.51 (s, 1H), 7.44 (s, 1H), 7.32 (br s, 1H), 6.63 (s, 1H), 6.54 (s, 1H), 6.49 (d, J=8.8 Hz, 1H), 3.91 (s, 3H), 3.88 (m, 4H), 3.87 (s, 3H), 3.14 (m, 4H), 3.11 (s, 2H), 2.89 (d, J=5.4 Hz, 3H), 2.88 (m, 2H), 2.80 (m, 2H), 2.69 (m, 4H); LC/MS (ESI+): 581.95 (M+H).

Example 1114

2-[5-Chloro-2-(8-methoxy-3-methylcarbamoylmethyl-2,3,4,5-tetrahydro-1H-benzo[d]azepin-7-ylamino)-pyrimidin-4-ylamino]-N-methyl-benzamide Following a procedure similar to Example 258c, 2-(7-amino-8-methoxy-1,2,4,5-tetrahydro-benzo[d]azepin-3-yl)-N-methyl-acetamide and 2-(2,5-dichloro-pyrimidin-4-ylamino)-N-methyl-benzamide were converted to 2-[5-chloro-2-(8-methoxy-3-methylcarbamoylmethyl-2,3,4,5-tetrahydro-1H-benzo[d]azepin-7-ylamino)-pyrimidin-4-ylamino]-N-methyl-benzamide (34 mg, 33%) as a pale yellow solid. MP: 200-216° C.; $^1$H-NMR (CDCl$_3$) δ 11.01 (s, 1H), 8.65 (d, J=8.4 Hz, 1H), 8.10 (s, 1H), 8.09 (s, 1H), 7.51 (s, 1H), 7.50 (s, 1H), 7.42 (m, 1H), 7.37 (br s, 1H), 7.08 (m, 1H), 6.64 (s, 1H), 6.25 (br s, 1H), 3.87 (s, 3H), 3.13 (s, 2H), 3.04 (d, 4.8 Hz, 3H), 2.89 (5.2 Hz, 3H), 2.88 (m, 2H), 2.76 (m, 2H), 2.70 (m, 4H); LC/MS (ESI+): 524.11 (M+H).

Example 1115

2-[5-Chloro-2-(8-methoxy-3-methylcarbamoylmethyl-2,3,4,5-tetrahydro-1H-benzo[d]azepin-7-ylamino)-pyrimidin-4-ylamino]-N-ethyl-benzamide Following a procedure similar to Example 258c, 2-(7-amino-8-methoxy-1,2,4,5-tetrahydro-benzo[d]azepin-3-yl)-N-methyl-acetamide and 2-(2,5-dichloro-pyrimidin-4-ylamino)-N-ethyl-benzamide were converted to 2-[5-chloro-2-(8-methoxy-3-methylcarbamoylmethyl-2,3,4,5-tetrahydro-1H-benzo[d]azepin-7-ylamino)-pyrimidin-4-ylamino]-N-ethyl-benzamide (37 mg, 34%) as a pale yellow solid. MP: 99-110° C.; $^1$H-NMR (CDCl$_3$) δ 10.96 (s, 1H), 8.64 (d, J=8.0 Hz, 1H), 8.11 (s, 2H), 7.50 (m, 2H), 7.43 (m, 1H), 7.35 (br s, 1H), 7.08 (apparent t, J=7.6 Hz, 1H), 6.64 (s, 1H), 6.16 (br s, 1H), 3.87 (s, 3H), 3.52 (m, 2H), 3.13 (s, 2H), 2.89 (d, J=5.2 Hz, 3H), 2.87 (m, 2H), 2.76 (m, 2H), 2.69 (m, 4H), 1.27 (t, J=7.2 Hz, 3H); LC/MS (ESI+): 538.10 (M+H).

Example 1116

2-[5-Chloro-2-(8-methoxy-3-methylcarbamoylmethyl-2,3,4,5-tetrahydro-1H-benzo[d]azepin-7-ylamino)-pyrimidin-4-ylamino]-3-fluoro-N-methyl-benzamide Following a procedure similar to Example 258c, 2-(7-amino-8-methoxy-1,2,4,5-tetrahydro-benzo[d]azepin-3-yl)-N-methyl-acetamide and 2-(2,5-dichloro-pyrimidin-4-ylamino)-3-fluoro-N-methyl-benzamide were converted to 2-[5-chloro-2-(8-methoxy-3-methylcarbamoylmethyl-2,3,4,5-tetrahydro-1H-benzo[d]azepin-7-ylamino)-pyrimidin-4-ylamino]-3-fluoro-N-methyl-benzamide (24 mg, 24%) as an off-white solid. MP: 119-130° C.; $^1$H-NMR (CDCl$_3$) δ 8.72 (s, 1H), 8.07 (s, 1H), 7.76 (s, 1H), 7.45 (s, 1H), 7.34-7.24 (m, 4H), 6.58 (s, 1H), 6.21 (br s, 1H), 3.82 (s, 3H), 3.10 (s, 2H), 2.92 (d, J=4.0 Hz, 3H), 2.87 (d, J=4.8 Hz, 3H), 2.81 (m, 2H), 2.68 (m, 2H), 2.58 (s, 4H); LC/MS (ESI+): 542.30 (M+H).

Example 1117

(2-exo,3-exo)-3-[5-Chloro-2-(8-methoxy-3-methylcarbamoylmethyl-2,3,4,5-tetrahydro-1H-benzo[d]azepin-7-ylamino)-pyrimidin-4-ylamino]-bicyclo[2.2.1]hept-5-ene-2-carboxylic acid amide Following a procedure similar to Example 258c, 2-(7-amino-8-methoxy-1,2,4,5-tetrahydro-benzo[d]azepin-3-yl)-N-methyl-acetamide and (2-exo, 3-exo)-3-(2,5-dichloro-pyrimidin-4-ylamino)-bicyclo[2.2.1]hept-5-ene-2-carboxylic acid amide were converted to (2-exo, 3-exo)-3-[5-chloro-2-(8-methoxy-3-methylcarbamoylmethyl-2,3,4,5-tetrahydro-1H-benzo[d]azepin-7-ylamino)-pyrimidin-4-ylamino]-bicyclo[2.2.1]hept-5-ene-2-carboxylic acid amide (45 mg, 40%) as a white solid. MP: 90-103° C.; $^1$H-NMR (CDCl$_3$) δ 8.19 (s, 1H), 7.89 (s, 1H), 7.40 (s, 1H), 7.33 (br s, 1H), 6.64 (s, 1H), 6.60 (d, J=8.8 Hz, 1H), 6.30 (s, 1H), 5.58 (br s, 1H), 5.30 (br s, 1H), 4.44 (m, 1H), 3.87 (s, 3H), 3.13 (s, 2H), 3.07 (s, 1H), 2.89 (d, J=4.8 Hz, 3H), 2.87 (m, 6H), 2.70 (m, 4H), 2.50 (d, J=8.0 Hz, 1H), 2.26 (d, J=9.2 Hz, 1H), 1.65 (d, J=8.8 Hz, 1H); LC/MS (ESI+): 526.01 (M+H).

Example 1118

2-{7-[5-Chloro-4-(5-chloro-2-methoxy-phenylamino)-pyrimidin-2-ylamino]-8-methoxy-1,2,4,5-tetrahydro-benzo[d]azepin-3-yl}-N-methyl-acetamide Following a procedure similar to Example 258c, 2-(7-amino-8-methoxy-1,2,4,5-tetrahydro-benzo[d]azepin-3-yl)-N-methyl-acetamide and (5-chloro-2-methoxy-phenyl)-(2,5-dichloro-pyrimidin-4-yl)-amine were converted to 2-{7-[5-chloro-4-(5-chloro-2-methoxy-phenylamino)-pyrimidin-2-ylamino]-8-methoxy-1,2,4,5-tetrahydro-benzo[d]azepin-3-yl}-N-methyl-acetamide (68 mg, 60%) as a white solid. MP: 127-136° C.; $^1$H-NMR (CDCl$_3$) δ 8.47 (s, 1H), 8.09 (s, 1H), 8.02 (s, 1H), 7.78 (s, 1H), 7.44 (s, 1H), 7.36 (br s, 1H), 7.00 (d, J=8.6 Hz, 1H), 8.8 Hz, 1H), 6.66 (s, 1H), 3.94 (s, 3H), 3.88 (s, 3H), 3.11 (s, 2H), 2.89 (d, J=4.8 Hz, 3H), 2.86 (m, 4H), 2.68 (m, 4H); LC/MS (ESI+): 530.98 (M+H).

Example 1119

2-[5-Chloro-2-(3-dimethylcarbamoylmethyl-8-methoxy-2,3,4,5-tetrahydro-1H-benzo[d]azepin-7-ylamino)-pyrimidin-4-ylamino]-N-ethyl-3-fluoro-benzamide Following a procedure similar to Example 258c, 2-(7-amino-8-methoxy-1,2,4,5-tetrahydro-benzo[d]azepin-3-yl)-N,N-dimethyl-acetamide and 2-(2,5-dichloro-pyrimidin-4-ylamino)-N-ethyl-3-fluoro-benzamide were converted to 2-[5-chloro-2-(3-dimethylcarbamoylmethyl-8-methoxy-2,3,4,5-tetrahydro-1H-benzo[d]azepin-7-ylamino)-pyrimidin-4-ylamino]-N-ethyl-3-fluoro-benzamide as a light yellow solid (36 mg, 32%). MP: 95-105° C.; $^1$H-NMR (CDCl$_3$) δ 8.48 (s, 1H), 8.07 (s, 1H), 7.71 (s, 1H), 7.45 (s, 1H), 7.32 (br s, 1H), 7.28 (m, 2H), 6.57 (s, 1H), 6.15 (br s, 1H), 3.82 (s, 3H), 3.37 (quitet, J=6.8 Hz, 2H), 3.26 (s, 2H), 3.14 (s, 3H), 2.99 (s, 3H), 2.82 (m, 2H), 2.65 (m, 2H), 2.57 (apparent s, 4H), 1.10 (t, J=6.8 Hz, 3H); LC/MS (ESI+): 570.01 (M+H).

Example 1120

5-Chloro-N*2*-[3-(2-methanesulfonyl-ethyl)-8-methoxy-2,3,4,5-tetrahydro-1H-benzo[d]azepin-7-yl]-N*4*-(2-methoxy-4-morpholin-4-yl-phenyl)-pyrimidine-2,4-diamine Following a procedure similar to Example 258c, 3-(2-methanesulfonyl-ethyl)-8-methoxy-2,3,4,5-tetrahydro-1H-benzo[d]azepin-7-ylamine, prepared in analogous manner to Example 258a-b from 7-methoxy-8-nitro-2,3,4,5-tetrahydro-1H-benzo[d]azepine and in situ generated trifluoro-methane-sulfonic acid 2-methanesulfonyl-ethyl ester, and (2,5-dichloro-pyrimidin-4-yl)-(2-methoxy-4-morpholin-4-yl-phenyl)-amine were converted to 5-chloro-N*2*-[3-(2-methanesulfonyl-ethyl)-8-methoxy-2,3,4,5-tetrahydro-1H-benzo[d]azepin-7-yl]-N*4*-(2-methoxy-4-morpholin-4-yl-phenyl)-pyrimidine-2,4-diamine (68 mg, 60%) as a white solid. MP: 89-100° C.; $^1$H-NMR (CDCl$_3$) δ 8.23 (d, J=8.8 Hz, 1H), 8.12 (s, 1H), 8.03 (s, 1H), 7.52 (s, 1H), 7.42 (s, 1H), 6.63 (s, 1H), 6.56 (s, 1H), 6.51 (d, J=8.8 Hz, 1H), 3.92 (s, 3H), 3.89 (m, 4H), 3.86 (s, 3H), 3.15 (m, 6H), 3.05 (s, 3H), 3.03 (m, 2H), 2.85 (m 2H), 2.80 (m, 2H), 2.69 (m, 4H); LC/MS (ESI+): 617.08 (M+H).

Example 1121

1-{7-[5-Chloro-4-(2-methoxy-4-morpholin-4-yl-phenylamino)-pyrimidin-2-ylamino]-8-methoxy-1,2,4,5-tetrahydro-benzo[d]azepin-3-yl}-2-dimethylamino-ethanone 1121a) Into a 1-neck round-bottom flask was added 7-methoxy-8-nitro-2,3,4,5-tetrahydro-1H-benzo[d]azepine (0.490 g, 2.20 mmol), dimethylamino-acetyl chloride hydrochloride (0.4181 g, 2.646 mmol), and Triethylamine (0.7683 mL, 5.512 mmol) in dichloromethane (11 mL) and the reaction was stirred overnight at room temperature. The reaction mixture was next partitioned between water and ethyl acetate, and the layers separated. The aqueous phase was extracted twice with EtOAc and the combined organic extract was washed with water, dried (MgSO$_4$), filtered, and concentrated, and the product, 2-dimethylamino-1-(7-methoxy-8-nitro-1,2,4,5-tetrahydro-benzo[d]azepin-3-yl)-ethanone, was isolated by flash chromatography (SiO$_2$, MeOH/dichloromethane 0-10%) as an oil (600 mg, 90%). LC/MS (ESI+): 308.04 (M+H).

1121b) Following a procedure similar to Example 256b, 2-dimethylamino-1-(7-methoxy-8-nitro-1,2,4,5-tetrahydro-benzo[d]azepin-3-yl)-ethanone was converted to 1-(7-amino-8-methoxy-1,2,4,5-tetrahydro-benzo[d]azepin-3-yl)-2-dimethylamino-ethanone as a brown waxy solid (500 mg, 100%). LC/MS (ESI+): 277.89 (M+H).

1121c) Following a procedure similar to Example 258c, 1-(7-amino-8-methoxy-1,2,4,5-tetrahydro-benzo[d]azepin-3-yl)-2-dimethylamino-ethanone and (2,5-dichloro-pyrimidin-4-yl)-(2-methoxy-4-morpholin-4-yl-phenyl)-amine were converted to 1-{7-[5-chloro-4-(2-methoxy-4-morpholin-4-yl-phenylamino)-pyrimidin-2-ylamino]-8-methoxy-1,2,4,5-tetrahydro-benzo[d]azepin-3-yl}-2-dimethylamino-ethanone (28 mg, 20%) as a white solid. MP: 84-101° C.; $^1$H-NMR (CDCl$_3$, 2 rotamers observed; signals of minor rotamer marked with "*") δ 8.30 (d, J=8.4 Hz, 1H), 8.16 (s, 1H), 8.15* (d, J=8.4 Hz, 1H), 8.03 (s, 1H), 7.60 (s, 1H), 7.45* (s, 1H), 7.43 (d, J=8.4 Hz, 1H), 6.67 (s, 1H), 6.63* (s, 1H), 6.60-6.45 (m, 2H), 3.93 (s, 2H), 3.91 (s, 3H), 3.88 (m, 5H), 3.87 (s, 3H), 3.68 (m, 4H), 3.17 (m, 6H), 2.88 (m, 3H), 2.78 (m, 1H), 2.31 (s, 6H); LC/MS (ESI+): 596.27 (M+H).

Example 1122

N-((1R,2R)-2-{5-Chloro-2-[3-(2-methanesulfonyl-ethyl)-8-methoxy-2,3,4,5-tetrahydro-1H-benzo[d]azepin-7-ylamino]-pyrimidin-4-ylamino}-cyclohexyl)-methanesulfonamide Following a procedure similar to Example 258c, 3-(2-methanesulfonyl-ethyl)-8-methoxy-2,3,4,5-tetrahydro-1H-benzo[d]azepin-7-ylamine, and N-[(1R,2R)-2-(2,5-dichloro-pyrimidin-4-ylamino)-cyclohexyl]-methanesulfonamide were converted to N-((1R,2R)-2-{5-chloro-2-[3-(2-methanesulfonyl-ethyl)-8-methoxy-2,3,4,5-tetrahydro-1H-benzo[d]azepin-7-ylamino]-pyrimidin-4-ylamino}-cyclohexyl)-methanesulfonamide (31 mg, 29%) as a white solid. MP: 216-235° C.; $^1$H-NMR (CDCl$_3$) δ 8.01 (s, 1H), 7.95 (s, 1H), 7.34 (s, 1H), 6.65 (s, 1H), 5.35 (d, J=8.0 Hz, 1H), 5.27 (d, J=6.4 Hz, 1H), 3.95 (m, 1H), 3.87 (s, 3H), 3.25 (m, 1H), 3.16 (m, 2H), 3.08 (s, 3H), 3.03 (m, 2H), 2.88 (m, 4H), 2.78 (s, 3H), 2.70 (m, 6H), 2.24 (m, 2H), 1.84 (m, 2H), 1.38 (m, 2H); LC/MS (ESI+): 601.40 (M+H).

Example 1123

(1S,2S,3R,4R)-3-[5-Chloro-2-(3-dimethylcarbamoylmethyl-8-methoxy-2,3,4,5-tetrahydro-1H-benzo[d]azepin-7-ylamino)-pyrimidin-4-ylamino]-bicyclo[2.2.1]hept-5-ene-2-carboxylic acid amide Following a procedure similar to Example 258c, 2-(7-amino-8-methoxy-1,2,4,5-tetrahydro-benzo[d]azepin-3-yl)-N,N-dimethyl-acetamide and (1S,2S,3R,4R)-3-(2,5-dichloro-pyrimidin-4-ylamino)-bicyclo[2.2.1]hept-5-ene-2-carboxylic acid amide were converted to (1S,2S,3R,4R)-3-[5-chloro-2-(3-dimethylcarbamoylmethyl-8-methoxy-2,3,4,5-tetrahydro-1H-benzo[d]azepin-7-ylamino)-pyrimidin-4-ylamino]-bicyclo[2.2.1]hept-5-ene-2-carboxylic acid amide as a white solid (35 mg, 40%). MP: 109-127° C.; $^1$H-NMR (CDCl$_3$) δ 8.18 (s, 1H), 7.89 (s, 1H), 7.40 (s, 1H), 6.64 (s, 1H), 6.55 (d, J=8.6 Hz, 1H), 6.31 (br s, 1H), 5.59 (br s, 1H), 5.30 (br s, 1H), 4.45 (m, 1H), 3.86 (s, 3H), 3.28 (s, 2H), 3.14 (s, 3H), 3.07 (s, 1H), 2.98 (s, 3H), 2.87 (m s, 6H), 2.70 (br s, 4H), 2.51 (d, J=8.4 Hz, 1H), 2.25 (d, J=8.8 Hz, 1H), 1.64 (d, J=9.2 Hz, 1H); LC/MS (ESI+): 540.25 (M+H).

Example 1124

(1S,2S,3R,4R)-3-[5-Chloro-2-(8-methoxy-3-methylcarbamoylmethyl-2,3,4,5-tetrahydro-1H-benzo[d]azepin-7-ylamino)-pyrimidin-4-ylamino]-bicyclo[2.2.1]hept-5-ene-2-carboxylic acid amide Following a procedure similar to Example 258c, 2-(7-amino-8-methoxy-1,2,4,5-tetrahydro-benzo[d]azepin-3-yl)-N-methyl-acetamide and (1S,2S,3R,4R)-3-(2,5-dichloro-pyrimidin-4-ylamino)-bicyclo[2.2.1]hept-5-ene-2-carboxylic acid amide were converted to (1S,2S,3R,4R)-3-[5-chloro-2-(8-methoxy-3-methylcarbamoylmethyl-2,3,4,5-tetrahydro-1H-benzo[d]azepin-7-ylamino)-pyrimidin-4-ylamino]-bicyclo[2.2.1]hept-5-ene-2-carboxylic acid amide (47 mg, 56%) as a white solid. MP: 135-145° C.; $^1$H-NMR (CDCl$_3$) δ 8.20 (s, 1H), 7.89 (s, 1H), 7.40 (s, 1H), 7.33 (br s, 1H), 6.64 (s, 1H), 6.61 (d, J=8.8 Hz, 1H), 6.30 (s, 1H), 5.59 (br s, 1H), 5.32 (br s, 1H), 4.44 (t, J=8.4 Hz, 1H), 3.87 (s, 3H), 3.13 (s, 2H), 3.07 (s, 1H), 2.89 (d, J=5.0 Hz, 3H), 2.88 (m, 6H), 2.71 (br s, 4H), 2.50 (d, J=8.4 Hz, 1H), 2.26 (d, J=9.2 Hz, 1H), 1.65 (d, J=9.6 Hz, 1H); LC/MS (ESI+): 526.21 (M+H).

Example 1125

N-((1R,2R)-2-{5-Chloro-2-[3-(2-dimethylamino-acetyl)-8-methoxy-2,3,4,5-tetrahydro-1H-benzo[d]azepin-7-ylamino]-pyrimidin-4-ylamino}-cyclohexyl)-methanesulfonamide Following a procedure similar to Example 258c, 1-(7-amino-8-methoxy-1,2,4,5-tetrahydro-benzo[d]azepin-3-yl)-2-dimethylamino-ethanone and -[(1R,2R)-2-(2,5-dichloro-pyrimidin-4-ylamino)-cyclohexyl]-methanesulfonamide were converted to N-((1R,2R)-2-{5-chloro-2-[3-(2-dimethylamino-acetyl)-8-methoxy-2,3,4,5-tetrahydro-1H-benzo[d]azepin-7-ylamino]-pyrimidin-4-ylamino}-cyclohexyl)-methanesulfonamide (57 mg, 51%) as a white solid. MP: 128-141° C.; $^1$H-NMR (CDCl$_3$; 2 rotamers observed; signals of minor rotamer marked with "*") δ 8.07 (s, 1H), 8.04*, (s, 1H), 7.95 (s, 1H), 7.37 (s, 1H), 6.68* (s, 1H), 6.66 (s, 1H), 5.50-5.30 (m, 2H), 3.95 (m, 1H), 3.88 (s, 3H), 3.80 (m, 1H), 3.69 (m, 3H), 3.25 (m, 1H), 3.20 (s, 2H), 2.89 (m, 4H), 2.80 (s, 3H), 2.31 (s, 6H), 2.25 (m, 1H), 1.86 (m, 1H), 1.38 (m, 4H); LC/MS (ESI+): 580.20 (M+H).

Example 1126

2-{5-Chloro-2-[8-methoxy-3-(3-morpholin-4-yl-propyl)-2-oxo-2,3,4,5-tetrahydro-1H-benzo[d]azepin-7-ylamino]-pyrimidin-4-ylamino}-N-methyl-benzamide Following a sequence of procedures similar to Example 1111a-d, 7-amino-8-methoxy-3-(3-morpholin-4-yl-propyl)-1,3,4,5-tetrahydro-benzo[d]azepin-2-one and 2-(2,5-dichloro-pyrimidin-4-ylamino)-N-methyl-benzamide were converted to 2-{5-chloro-2-[8-methoxy-3-(3-morpholin-4-yl-propyl)-2-oxo-2,3,4,5-tetrahydro-1H-benzo[d]azepin-7-ylamino]-pyrimidin-4-ylamino}-N-methyl-benzamide as a pale yellow solid (15 mg, 8%). MP: 92-100° C.; $^1$H-NMR (CDCl$_3$) δ 11.04 (s, 1H), 8.65 (d, J=8.6 Hz, 1H), 8.11 (s, 1H), 8.08 (s, 1H), 7.50 (d, J=7.8 Hz, 1H), 7.47 (s, 1H), 7.45 (s, 1H), 7.08 (t, J=7.6 Hz, 1H), 6.61 (s, 1H), 6.29 (br s, 1H), 3.87 (s, 3H), 3.82 (s, 2H), 3.69 (m, 6H), 3.46 (t, J=7.2 Hz, 2H), 3.03 (d, J=4.8 Hz, 3H), 3.01, (m, 2H), 2.41 (br s, 4H), 2.35 (t, J=7.3 Hz, 2H), 1.76 (m, 2H); LC/MS (ESI+): 594.23 (M+H).

Example 1127

2-{7-[5-Chloro-4-(2-methoxy-4-morpholin-4-yl-phenylamino)-pyrimidin-2-ylamino]-1,2,4,5-tetrahydro-benzo[d]azepin-3-yl}-N-methyl-acetamide Following a procedure similar to Example 258c, 2-(7-amino-1,2,4,5-tetrahydro-benzo[d]azepin-3-yl)-N-methyl-acetamide, prepared in analogous manner to 258a-b, and (2,5-dichloro-pyrimidin-4-yl)-(2-methoxy-4-morpholin-4-yl-phenyl)-amine were converted to 2-{7-[5-chloro-4-(2-methoxy-4-morpholin-4-yl-phenylamino)-pyrimidin-2-ylamino]-1,2,4,5-tetrahydro-benzo[d]azepin-3-yl}-N-methyl-acetamide (49 mg, 40%) as a light grey solid. MP: 169-176° C.; $^1$H-NMR (CDCl$_3$) δ 8.22 (d, J=8.6 Hz, 1H), 8.01 (s, 1H), 7.56 (s, 1H), 7.35 (s, 1H), 7.30 (br s, 1H), 7.28 (d, J=8.1 Hz, 1H), 7.01 (d, J=8.1 Hz, 1H), 6.86 (s, 1H), 6.54 (s, 1H), 6.49 (d, J=8.6 Hz, 1H), 3.91 (s, 3H), 3.89 (t, J=4.6 Hz, 4H), 3.14 (t, J=4.6 Hz, 4H), 3.12 (s, 2H), 2.89 (d, J=4.8 Hz, 3H), 2.88 (m, 4H), 2.71 (br s, 4H); LC/MS (ESI+): 552.36 (M+H).

Example 1128

(1S,2S,3R,4R)-3-{5-Chloro-2-[3-(2-methanesulfonyl-ethyl)-8-methoxy-2,3,4,5-tetrahydro-1H-benzo[d]azepin-7-ylamino]-pyrimidin-4-ylamino}-bicyclo[2.2.1]hept-5-ene-2-carboxylic acid amide Following a procedure similar to Example 258c, 3-(2-methanesulfonyl-ethyl)-8-methoxy-2,3,4,5-tetrahydro-1H-benzo[d]azepin-7-ylamine and (1S,2S,3R,4R)-3-(2,5-dichloro-pyrimidin-4-ylamino)-bicyclo[2.2.1]hept-5-ene-2-carboxylic acid amide were converted to (1S,2S,3R,4R)-3-{5-chloro-2-[3-(2-methanesulfonyl-ethyl)-8-methoxy-2,3,4,5-tetrahydro-1H-benzo[d]azepin-7-ylamino]-pyrimidin-4-ylamino}-bicyclo[2.2.1]hept-5-ene-2-carboxylic acid amide (43 mg, 46%) as a tan solid. MP: 132-146° C.; $^1$H-NMR (CDCl$_3$) δ 8.20 (s, 1H), 7.89 (s, 1H), 7.40 (s, 1H), 6.64 (s, 1H), 6.61 (d, J=8.6 Hz, 1H), 6.32 (m, 2H), 5.58 (br s, 1H), 5.33 (br s, 1H), 4.45 (m, 1H), 3.87 (s, 3H), 3.16 (m, 2H), 3.06 (s, 3H), 3.05 (m, 1H), 3.03 (m, 2H), 2.86 (m, 5H), 2.70 (m, 4H), 2.51 (d, J=8.1 Hz, 1H), 2.26 (d, J=9.8 Hz, 1H), 1.66 (d, J=8.1 Hz, 1H); LC/MS (ESI+): 561.18 (M+H).

Example 1129

5-Chloro-N*2*-(3-ethyl-8-methoxy-2,3,4,5-tetrahydro-1H-benzo[d]azepin-7-yl)-N*4*-(2-methoxy-4-morpholin-4-yl-phenyl)-pyrimidine-2,4-diamine Following a procedure similar to Example 258c, 3-ethyl-8-methoxy-2,3,4,5-tetrahydro-1H-benzo[d]azepin-7-ylamine and (2,5-dichloro-pyrimidin-4-yl)-(2-methoxy-4-morpholin-4-yl-phenyl)-amine were converted to 5-chloro-N*2*-(3-ethyl-8-methoxy-2,3,4,5-tetrahydro-1H-benzo[d]azepin-7-yl)-N*4*-(2-methoxy-4-morpholin-4-yl-phenyl)-pyrimidine-2,4-diamine (50 mg, 50%) as a tan solid. MP: 165-171° C.; $^1$H-NMR (CDCl$_3$) δ 8.27 (d, J=8.8 Hz, 1H), 8.13 (s, 1H), 8.02 (s, 1H), 7.54 (s, 1H), 7.44 (s, 1H), 6.65 (s, 1H), 6.55 (s, 1H), 6.51 (d, J=8.8 Hz, 1H), 3.92 (s, 3H), 3.89 (m, 4H), 3.86 (s, 3H), 3.16 (m, 4H), 3.00-2.50 (br, 10H), 1.15 (br, 3H); LC/MS (ESI+): 539.30 (M+H).

Example 1130

2-{7-[5-Chloro-4-(2-methoxy-phenylamino)-pyrimidin-2-ylamino]-8-methoxy-1,2,4,5-tetrahydro-benzo[d]azepin-3-yl}-N,N-dimethyl-acetamide Following a procedure similar to Example 258c, 2-(7-amino-8-methoxy-1,2,4,5-tetrahydro-benzo[d]azepin-3-yl)-N,N-dimethyl-acetamide and (2,5-dichloro-pyrimidin-4-yl)-(2-methoxy-phenyl)-amine were converted to 2-{7-[5-chloro-4-(2-methoxy-phenylamino)-pyrimidin-2-ylamino]-8-methoxy-1,2,4,5-tetrahydro-benzo[d]azepin-3-yl}-N,N-dimethyl-acetamide as a white solid (27 mg, 28%). MP: 65-85° C.; $^1$H-NMR (CDCl$_3$) δ 8.46 (d, J=8.0 Hz, 1H), 8.09 (s, 1H), 8.06 (s, 1H), 7.81 (s, 1H), 7.45 (s, 1H), 7.05 (m, 1H), 6.95 (m, 2H), 6.65 (s, 1H), 3.94 (s, 3H), 3.87 (s, 3H), 3.28 (s, 2H), 3.15 (s, 3H), 2.98 (s, 3H), 2.88 (m, 2H), 2.84 (m, 2H), 2.70 (br s, 4H); LC/MS (ESI+): 511.23 (M+H).

Example 1131

1-{7-[5-Chloro-4-(2-methoxy-phenylamino)-pyrimidin-2-ylamino]-8-methoxy-1,2,4,5-tetrahydro-benzo[d]azepin-3-yl}-2-dimethylamino-ethanone Following a procedure similar to Example 258c, 1-(7-amino-8-methoxy-1,2,4,5-tetrahydro-benzo[d]azepin-3-yl)-2-dimethylamino-ethanone and (2,5-dichloro-pyrimidin-4-yl)-(2-methoxy-phenyl)-amine were converted to 1-{7-[5-chloro-4-(2-methoxy-phenylamino)-pyrimidin-2-ylamino]-8-methoxy-1,2,4,5-tetrahydro-benzo[d]azepin-3-yl}-2-dimethylamino-ethanone as a white solid (22 mg, 23%). MP: 76-99° C.; $^1$H-NMR (CDCl$_3$, 2 rotamers observed; signals of minor rotamer marked with "*") δ 8.46* (d, J=8.0 Hz, 1H), 8.44 (d, J=8.0 Hz, 1H), 8.16 (d, J=8.8 Hz, 1H), 8.07 (s, 1H), 7.80 (d, J=11.6 Hz, 1H), 7.46 (d, J=12.6 Hz, 1H), 7.07 (m, 1H), 6.96 (m, 2H), 6.66 (d, J=12.0 Hz, 1H), 3.95 (s, 3H), 3.88 (s, 3H), 3.69 (m, 4H), 3.22* (s, 2H), 3.20 (s, 2H), 2.92-2.78 (m, 4H), 2.33 (s, 6H); LC/MS (ESI+): 511.19 (M+H).

Example 1132

5-Chloro-N*2*-[3-(2-methanesulfonyl-ethyl)-8-methoxy-2,3,4,5-tetrahydro-1H-benzo[d]azepin-7-yl]-N*4*-(2-methoxy-phenyl)-pyrimidine-2,4-diamine Following a procedure similar to Example 258c, 3-(2-methanesulfonyl-ethyl)-8-methoxy-2,3,4,5-tetrahydro-1H-benzo[d]azepin-7-ylamine and (2,5-dichloro-pyrimidin-4-yl)-(2-methoxy-phenyl)-amine were converted to 5-chloro-N*2*-[3-(2-methanesulfonyl-ethyl)-8-methoxy-2,3,4,5-tetrahydro-1H-benzo[d]azepin-7-yl]-N*4*-(2-methoxy-phenyl)-pyrimidine-2,4-diamine as a white solid (58 mg, 58%). MP: 64-70° C.; $^1$H-NMR (CDCl$_3$) δ 8.45 (d, J=8.0 Hz, 1H), 8.13 (s, 1H), 8.07 (s, 1H), 7.81 (s, 1H), 7.46 (s, 1H), 7.07 (m, 1H), 6.96 (d, J=8.0 Hz, 1H), 6.94 (m, 1H), 6.65 (s, 1H), 3.95 (s, 3H), 3.87 (s, 3H), 3.17 (m, 2H), 3.09 (s, 3H), 3.03 (m, 2H), 2.85 (m, 2H), 2.80 (m, 2H), 2.69 (br s, 4H); LC/MS (ESI+): 532.17 (M+H).

Example 1133

9-[5-Chloro-4-(2-methoxy-4-morpholin-4-yl-phenylamino)-pyrimidin-2-ylamino]-3-ethyl-8-methoxy-1,3,4,5-tetrahydro-benzo[d]azepin-2-one Following a procedure similar to Example 258c, 3-ethyl-8-methoxy-9-nitro-1,3,4,5-tetrahydro-benzo[d]azepin-2-one, which was prepared in an analogous manner to 251d, and (2,5-dichloro-pyrimidin-4-yl)-(2-methoxy-4-morpholin-4-yl-phenyl)-amine were converted to 9-[5-chloro-4-(2-methoxy-4-morpholin-4-yl-phenylamino)-pyrimidin-2-ylamino]-3-ethyl-8-methoxy-1,3,4,5-tetrahydro-benzo[d]azepin-2-one (69 mg, 50%) as a beige solid. MP: 87-103° C.; $^1$H-NMR (CDCl$_3$) δ 7.95 (br s, 1H), 7.62 (br s, 1H), 7.01 (d, J=8.4 Hz, 1H), 6.79 (d, J=8.4 Hz, 1H), 6.63 (m, 2H), 6.50 (m, 2H), 3.90 (s, 3H), 3.89 (m, 5H), 3.83 (s, 2H), 3.78 (s, 3H), 3.57 (m, 1H), 3.40 (q, J=6.9 Hz, 2H), 3.15 (m, 2H), 3.10 (m, 4H), 1.10 (m, 3H); LC/MS (ESI+): 553.29 (M+H).

Example 1134

2-[5-Chloro-2-(3-ethyl-7-methoxy-4-oxo-2,3,4,5-tetrahydro-1H-benzo[d]azepin-6-ylamino)-pyrimidin-4-ylamino]-N-ethyl-benzamide Following a procedure similar to Example 258c, 3-ethyl-8-methoxy-9-nitro-1,3,4,5-tetrahydro-benzo[d]azepin-2-one and 2-(2,5-dichloro-pyrimidin-4-ylamino)-N-ethyl-benzamide were converted to 2-[5-chloro-2-(3-ethyl-7-methoxy-4-oxo-2,3,4,5-tetrahydro-1H-benzo[d]azepin-6-ylamino)-pyrimidin-4-ylamino]-N-ethyl-benzamide (21 mg, 9%) as a tan solid. MP: 117-141° C.; $^1$H-NMR (CDCl$_3$) δ 11.03 (br s, 1H), 8.35 (br s, 1H), 8.03 (br s, 1H), 7.44 (d, J=8.3 Hz, 1H), 7.20 (br s, 1H), 7.02 (d, J=8.4 Hz, 1H), 6.99 (br s, 1H), 6.80 (d, J=8.4 Hz, 1H), 6.61 (br s, 1H), 6.18 (br s, 1H), 3.85 (br s, 2H), 3.78 (s, 3H), 3.65 (br s, 2H), 3.50 (m, 2H), 3.39 (br s, 2H), 3.14 (m, 2H), 1.26 (t, J=7.2 Hz, 3H), 1.09 (t, J=6.9 Hz, 3H); LC/MS (ESI+): 509.18 (M+H).

Example 1135

2-{7-[5-Chloro-4-(2-methoxy-phenylamino)-pyrimidin-2-ylamino]-8-methoxy-1,2,4,5-tetrahydro-benzo[d]azepin-3-yl}-N-methyl-acetamide Following a procedure similar to Example 258c, (2,5-dichloro-pyrimidin-4-yl)-(2-methoxy-phenyl)-amine and (2,5-Dichloro-pyrimidin-4-yl)-(2-methoxy-phenyl)-amine were converted to 2-{7-[5-chloro-4-(2-methoxy-phenylamino)-pyrimidin-2-ylamino]-8-methoxy-1,2,4,5-tetrahydro-benzo[d]azepin-3-yl}-N-methyl-acetamide (69 mg, 77%) as a light grey solid. MP: 81-95° C.; $^1$H-NMR (CDCl$_3$) δ 8.45 (d, J=8.0 Hz, 1H), 8.12 (s, 1H), 8.06 (s, 1H), 7.81 (s, 1H), 7.46 (s, 1H), 7.38 (br s, 1H), 7.06 (m, 1H), 6.95 (d, J=8.0 Hz, 1H), 6.94 (m, 1H), 6.64 (s, 1H), 3.95 (s, 3H), 3.87 (s, 3H), 3.16 (s, 2H), 2.90 (d, J=5.2 Hz, 3H), 2.88 (m, 2H), 2.81 (m, 2H), 2.71 (br s, 4H); LC/MS (ESI+): 497.10 (M+H).

Example 1136

3-[5-Chloro-2-(3-dimethylcarbamoylmethyl-8-methoxy-2,3,4,5-tetrahydro-1H-benzo[d]azepin-7-ylamino)-pyrimidin-4-ylamino]-4-methoxy-benzamide 1136a) 3-Amino-4-methoxy-benzamide (1.00 g, 0.00602 mol) in tetrahydrofuran (40 mL) was treated with 2,4,5-trichloro-pyrimidine (0.8278 mL, 0.007221 mol), and the reaction was stirred overnight at room temperature, then for 4 hours at 50° C. The mixture was partitioned between water and dichloromethane, and the aqueous phase was extracted twice with dichloromethane. The organics were dried (MgSO$_4$) and concentrated, and the product was isolated by chromatography (Silica, MeOH/dichloromethane 0-3%), followed by crystallization from methanol to give 3-(2,5-dichloro-pyrimidin-4-ylamino)-4-methoxy-benzamide as a white solid (1.26 g, 64%). LC/MS (ESI+): 313.04 (M+H).

1136b) Following a procedure similar to Example 258c, 2-(7-amino-8-methoxy-1,2,4,5-tetrahydro-benzo[d]azepin-3-yl)-N,N-dimethyl-acetamide and 3-(2,5-dichloro-pyrimidin-4-ylamino)-4-methoxy-benzamide were converted to 3-[5-chloro-2-(3-dimethylcarbamoylmethyl-8-methoxy-2,3,4,5-tetrahydro-1H-benzo[d]azepin-7-ylamino)-pyrimidin-4-ylamino]-4-methoxy-benzamide (32 mg, 30%) as a beige solid. MP: 163-174° C.; $^1$H-NMR (CDCl$_3$) δ 8.79 (s, 1H), 8.12 (s, 1H), 7.90 (s, 1H), 7.75 (m, 2H), 7.38 (s, 1H), 6.99 (d, J=8.4 Hz, 1H), 6.64 (s, 1H), 5.75 (br s, 1H), 5.24 (br s, 1H), 4.02 (s, 3H), 3.89 (s, 3H), 3.24 (s, 2H), 3.13 (s, 3H), 2.94 (s, 3H), 2.88 (m, 2H), 2.69 (m, 4H), 2.58 (m, 2H); LC/MS (ESI+): 554.32 (M+H).

Example 1137

3-{5-Chloro-2-[3-(2-methanesulfonyl-ethyl)-8-methoxy-2,3,4,5-tetrahydro-1H-benzo[d]azepin-7-ylamino]-pyrimidin-4-ylamino}-4-methoxy-benzamide Following a procedure similar to Example 258c, 3-(2-methanesulfonyl-ethyl)-8-methoxy-2,3,4,5-tetrahydro-1H-benzo[d]azepin-7-ylamine and 3-(2,5-dichloro-pyrimidin-4-ylamino)-4-methoxy-benzamide were converted to 3-{5-chloro-2-[3-(2-methanesulfonyl-ethyl)-8-methoxy-2,3,4,5-tetrahydro-1H-benzo[d]azepin-7-ylamino]-pyrimidin-4-ylamino}-4-methoxy-benzamide (50 mg, 40%) as a beige solid. MP: 232-243° C.; $^1$H-NMR (CDCl$_3$) δ 8.78 (s, 1H), 8.11 (s, 1H), 7.93 (s, 1H), 7.73 (m, 2H), 7.40 (s, 1H), 7.01 (d, J=8.3 Hz, 1H), 6.62 (s, 1H), 5.68 (br s, 1H), 5.22 (br s, 1H), 4.04 (s, 3H), 3.86 (s, 3H), 3.15 (m, 2H), 3.08 (s, 3H), 3.01 (m, 2H), 2.83 (m, 2H), 2.69 (m, 4H), 2.58 (m, 2H); LC/MS (ESI+): 575.28 (M+H).

Example 1138

3-[5-Chloro-2-(8-methoxy-3-methylcarbamoylmethyl-2,3,4,5-tetrahydro-1H-benzo[d]azepin-7-ylamino)-pyrimidin-4-ylamino]-4-methoxy-benzamide Following a procedure similar to Example 258c, 8-methoxy-3-methylcarbamoylmethyl-2,3,4,5-tetrahydro-1H-benzo[d]azepin-7-ylamine and 3-(2,5-dichloro-pyrimidin-4-ylamino)-4-methoxy-benzamide were converted to 3-[5-chloro-2-(8-methoxy-3-methylcarbamoylmethyl-2,3,4,5-tetrahydro-1H-benzo[d]azepin-7-ylamino)-pyrimidin-4-ylamino]-4-methoxy-benzamide (33 mg, 30%) as a beige solid. MP: 225-236° C.; $^1$H-NMR (CDCl$_3$) δ 8.81 (s, 1H), 8.12 (s, 1H), 7.95 (s, 1H), 7.75 (m, 2H), 7.41 (s, 1H), 3.35 (br s, 1H), 7.01 (d, J=8.0 Hz, 1H), 6.62 (s, 1H), 5.70 (br s, 1H), 5.25 (br s, 1H), 4.03 (s, 3H), 3.88 (s, 3H), 3.09 (s, 2H), 2.89 (d, J=5.4 Hz, 3H), 2.87 (m, 2H), 2.67 (m, 4H), 2.58 (m, 2H); LC/MS (ESI+): 540.30 (M+H).

Example 1139

3-{5-Chloro-2-[3-(2-dimethylamino-acetyl)-8-methoxy-2,3,4,5-tetrahydro-1H-benzo[d]azepin-7-ylamino]-pyrimidin-4-ylamino}-4-methoxy-benzamide Following a procedure similar to Example 258c, 1-(7-amino-8-methoxy-1,2,4,5-tetrahydro-benzo[d]azepin-3-yl)-2-dimethylamino-ethanone and 3-(2,5-dichloro-pyrimidin-4-ylamino)-4-methoxy-benzamide were converted to 3-{5-chloro-2-[3-(2-dimethylamino-acetyl)-8-methoxy-2,3,4,5-tetrahydro-1H-benzo[d]azepin-7-ylamino]-pyrimidin-4-ylamino}-4-methoxy-benzamide (59 mg, 50%) as a tan solid. MP: 226-233° C.; $^1$H-NMR (CDCl$_3$) δ 8.79 (m, 1H), 8.12 (s, 1H), 8.03 (s, 1H), 7.70 (m, 2H), 7.44 (br s, 1H), 7.00 (m, 1H), 6.65 (m, 1H), 5.78 (br s, 1H), 5.31 (br s, 1H), 4.02 (s, 3H), 3.90 (s, 3H), 3.69 (m, 2H), 3.60 (m, 2H), 3.17 (s, 2H), 2.88 (m, 2H), 2.62 (m, 2H), 2.29 (s, 6H); LC/MS (ESI+): 554.35 (M+H).

Example 1140

3-{5-Chloro-2-[8-methoxy-3-(2-methoxy-ethyl)-2,3,4,5-tetrahydro-1H-benzo[d]azepin-7-ylamino]-pyrimidin-4-ylamino}-4-methoxy-benzamide Following a procedure similar to Example 258c, 8-methoxy-3-(2-methoxy-ethyl)-2,3,4,5-tetrahydro-1H-benzo[d]azepin-7-ylamine and 3-(2,5-dichloro-pyrimidin-4-ylamino)-4-methoxy-benzamide were converted to 3-{5-chloro-2-[8-methoxy-3-(2-methoxy-ethyl)-2,3,4,5-tetrahydro-1H-benzo[d]azepin-7-ylamino]-pyrimidin-4-ylamino}-4-methoxy-benzamide (5 mg, 5%) as a tan solid. MP: 218-225° C.; $^1$H-NMR (CDCl$_3$) δ 8.78 (s, 1H), 8.10 (s, 1H), 7.93 (s, 1H), 7.73 (d, J=8.4 Hz, 1H), 7.71 (s, 1H), 7.37 (s, 1H), 7.00 (d, J=8.4 Hz, 1H), 6.64 (s, 1H), 5.73 (br s, 1H), 5.26 (br s, 1H), 4.00 (s, 3H), 3.86 (s, 3H), 3.53 (m, 2H), 3.35 (s, 3H), 2.87 (br s, 2H), 2.76-2.65 (m, 8H); LC/MS (ESI+): 527.13 (M+H).

Example 1141

2-{7-[5-Chloro-4-(2-dimethylsulfamoyl-phenylamino)-pyrimidin-2-ylamino]-8-methoxy-1,2,4,5-tetrahydro-benzo[d]azepin-3-yl}-N,N-dimethyl-acetamide 1141a) To a solution of 2-nitro-benzenesulfonyl chloride (15 g, 0.068 mol) in 1,4-dioxane (100 mL) was added sodium carbonate (10.76 g, 0.1015 mol) and 2.000 M of dimethylamine in tetrahydrofuran (40.61 mL) at room temperature and the reaction mixture was stirred for 4 hours. The reaction mixture was partitioned between water and dichloromethane, and the aqueous layer was extracted once with dichloromethane. The combined organic extracts were dried (MgSO$_4$), concentrated, and the solid residue was recrystallized from MeOH to afford N,N-dimethyl-2-nitro-benzenesulfonamide (14.7 g, 94%) as a white solid. LC/MS (ESI+): 230.92 (M+H).

1141b) Following a procedure similar to 263b, N,N-dimethyl-2-nitro-benzenesulfonamide was converted to 2-amino-N,N-dimethyl-benzenesulfonamide (19.1 g, 86%) as an off-white solid. LC/MS (ESI+): 201.09 (M+H).

1141c) 2-Amino-N,N-dimethyl-benzenesulfonamide (10.00 g, 49.94 mmol) in N,N-dimethylformamide (200 mL) was treated with sodium hydride 60% dispersion in mineral oil (3.99 g) at 0° C., then 2,4,5-trichloropyrimidine (8.587 mL, 74.90 mmol) was added and the reaction was stirred for 5 minutes at 0° C., then for 3 hours at room temperature. The reaction was quenched with aqueous saturated ammonium chloride, then water. The precipitate was collected by filtration and recrystallized from methanol to give 2-(2,5-dichloro-pyrimidin-4-ylamino)-N,N-dimethyl-benzenesulfonamide as a light grey solid (9.3 g, 52%). LC/MS (ESI+): 346.93 (M+H).

1141d) Following a procedure similar to Example 258c, 2-(7-amino-8-methoxy-1,2,4,5-tetrahydro-benzo[d]azepin-3-yl)-N,N-dimethyl-acetamide and 2-(2,5-dichloro-pyrimidin-4-ylamino)-N,N-dimethyl-benzenesulfonamide were converted to 2-{7-[5-chloro-4-(2-dimethylsulfamoyl-phenylamino)-pyrimidin-2-ylamino]-8-methoxy-1,2,4,5-tetrahydro-benzo[d]azepin-3-yl}-N,N-dimethyl-acetamide (47 mg, 42%) as a tan solid. MP: 218-225° C.; $^1$H-NMR (CDCl$_3$) δ 9.32 (br s, 1H), 8.51 (d, J=8.3 Hz, 1H), 8.14 (s, 1H), 7.98 (s, 1H), 7.88 (d, J=8.3 Hz, 1H), 7.55 (m, 1H), 7.50 (br s, 1H), 7.22 (m, 1H), 6.65 (s, 1H), 3.87 (s, 3H), 3.28 (s, 2H), 3.14 (s, 3H), 2.98 (s, 3H), 2.88 (m, 2H), 2.87 (s, 6H), 2.71 (m, 4H), 2.67 (m, 2H); LC/MS (ESI+): 588.15 (M+H).

Example 1142

2-{7-[5-Chloro-4-(2-methanesulfonyl-phenylamino)-pyrimidin-2-ylamino]-8-methoxy-1,2,4,5-tetrahydro-benzo[d]azepin-3-yl}-N,N-dimethyl-acetamide 1142a) Following a procedure similar to 1141c, 2-methanesulfonyl-phenylamine hydrochloride and 2,4,5-trichloropyrimidine were converted to (2,5-dichloro-pyrimidin-4-yl)-(2-methanesulfonyl-phenyl)-amine (3.9 g, 40%) as a yellow solid. LC/MS (ESI+): 317.98 (M+H).

1142b) Following a procedure similar to Example 258c, 2-(7-amino-8-methoxy-1,2,4,5-tetrahydro-benzo[d]azepin-3-yl)-N,N-dimethyl-acetamide and (2,5-dichloro-pyrimidin-4-yl)-(2-methanesulfonyl-phenyl)-amine were converted to 2-{7-[5-chloro-4-(2-methanesulfonyl-phenylamino)-pyrimidin-2-ylamino]-8-methoxy-1,2,4,5-tetrahydro-benzo[d]azepin-3-yl}-N,N-dimethyl-acetamide (39 mg, 37%) as a tan solid. MP: 77-99° C.; $^1$H-NMR (CDCl$_3$) δ 9.28 (s, 1H), 8.52 (d, J=8.4 Hz, 1H), 8.18 (s, 1H), 7.98 (d, J=8.4 Hz, 1H), 7.96 (s, 1H), 7.62 (m, 1H), 7.50 (s, 1H), 7.28 (m, 1H), 6.64 (s, 1H), 3.86 (s, 3H), 3.29 (s, 2H), 3.15 (s, 3H), 3.10 (s, 3H), 3.94 (s, 3H), 2.90 (m, 2H), 2.76 (m, 2H), 2.70 (m, 4H); LC/MS (ESI+): 559.10 (M+H).

Example 1143

2-{7-[5-Chloro-4-(2-methanesulfonyl-phenylamino)-pyrimidin-2-ylamino]-8-methoxy-1,2,4,5-tetrahydro-benzo[d]azepin-3-yl}-acetamide Following a procedure similar to Example 258c, 2-(7-amino-8-methoxy-1,2,4,5-tetrahydro-benzo[d]azepin-3-yl)-acetamide and (2,5-dichloro-pyrimidin-4-yl)-(2-methanesulfonyl-phenyl)-amine were converted to 2-{7-[5-chloro-4-(2-methanesulfonyl-phenylamino)-pyrimidin-2-ylamino]-8-methoxy-1,2,4,5-tetrahydro-benzo[d]azepin-3-yl}-acetamide (27 mg, 25%) as a light yellow solid. MP: 111-123° C.; $^1$H-NMR (CDCl$_3$) δ 9.29 (s, 1H), 8.54 (d, J=8.4 Hz, 1H), 8.18 (s, 1H), 8.02 (s, 1H), 8.01 (d, J=8.0 Hz, 1H), 7.61 (m, 1H), 7.53 (s, 1H), 7.28 (m, 1H), 7.23 (br s, 1H), 6.66 (s, 1H), 5.61 (br s, 1H), 3.88 (s, 3H), 3.13 (s, 2H), 3.11 (s, 3H), 2.88 (m, 2H), 2.75-2.71 (m, 6H); LC/MS (ESI+): 531.23 (M+H).

Example 1144

2-{7-[5-Chloro-4-(2-ethoxy-phenylamino)-pyrimidin-2-ylamino]-8-methoxy-1,2,4,5-tetrahydro-benzo[d]azepin-3-yl}-N,N-dimethyl-acetamide Following a procedure similar to Example 258c, 2-(7-amino-8-methoxy-1,2,4,5-tetrahydro-benzo[d]azepin-3-yl)-N,N-dimethyl-acetamide and (2,5-dichloro-pyrimidin-4-yl)-(2-ethoxy-phenyl)-amine, which was prepared in an analogous manner to 1136a, were converted to 2-{7-[5-chloro-4-(2-ethoxy-phenylamino)-pyrimidin-2-ylamino]-8-methoxy-1,2,4,5-tetrahydro-benzo[d]azepin-3-yl}-N,N-dimethyl-acetamide (43 mg, 43%) as a white solid. MP: 60-79° C.; $^1$H-NMR (CDCl$_3$) δ 8.49 (d, J=8.0 Hz, 1H), 8.10 (s, 1H), 8.06 (s, 1H), 7.96 (br s, 1H), 7.44 (s, 1H), 7.04 (m, 1H), 6.94 (m, 2H), 6.65 (s, 1H), 4.14 (q, J=7.2 Hz, 2H), 3.87 (s, 3H), 3.28 (s, 2H), 3.15 (s, 3H), 2.98 (s, 3H), 2.87 (m, 4H), 2.70 (m, 4H), 1.50 (t, J=7.2 Hz, 3H); LC/MS (ESI+): 525.31 (M+H).

Example 1145

2-{7-[5-Chloro-4-(3-morpholin-4-yl-phenylamino)-pyrimidin-2-ylamino]-8-methoxy-1,2,4,5-tetrahydro-benzo[d]azepin-3-yl}-N,N-dimethyl-acetamide Following a procedure similar to Example 258c, 2-(7-amino-8-methoxy-1,2,4,5-tetrahydro-benzo[d]azepin-3-yl)-N,N-dimethyl-acetamide and (2,5-dichloro-pyrimidin-4-yl)-(3-morpholin-4-yl-phenyl)-amine were converted to 2-{7-[5-chloro-4-(3-morpholin-4-yl-phenylamino)-pyrimidin-2-ylamino]-8-methoxy-1,2,4,5-tetrahydro-benzo[d]azepin-3-yl}-N,N-dimethyl-acetamide (56 mg, 50%) as a tan solid. MP: 91-111° C.; $^1$H-NMR (CDCl$_3$) δ 8.06 (s, 1H), 8.03 (s, 1H), 7.45 (br s, 1H), 7.28-7-18 (m, 2H), 7.04 (br s, 1H), 6.99 (br s, 1H), 6.72 (d, J=8.0 Hz, 1H), 6.61 (s, 1H), 3.84 (s, 3H), 3.83 (m, 4H), 3.26 (s, 2H), 3.14 (m, 4H), 3.13 (s, 3H), 2.96 (s, 3H), 2.86 (m, 2H), 2.73 (m, 2H), 2.66 (m, 2H), 2.62 (m, 2H); LC/MS (ESI+): 566.35 (M+H).

Example 1146

4-[5-Chloro-2-(3-dimethylcarbamoylmethyl-8-methoxy-2,3,4,5-tetrahydro-1H-benzo[d]azepin-7-ylamino)-pyrimidin-4-ylamino]-3-methoxy-benzamide 1146a) 3-Methoxy-4-nitro-benzoic acid methyl ester (1.000 g, 0.004735 mol) and 7N ammonia (1 mL, 0.04 mol) in methanol were heated in methanol (20 mL) at 80° C. overnight in a sealed tube. The reaction was cooled to room temperature, then to 0° C., when 3-methoxy-4-nitro-benzamide precipitated (0.66 g, 71%), and was collected by filtration. Yellow solid. LC/MS (ESI+): 196.96 (M+H).

1146b) Following a sequence of reactions analogous to 263b and 1136a 3-methoxy-4-nitro-benzamide was converted to 4-(2,5-dichloro-pyrimidin-4-ylamino)-3-methoxy-benzamide (1.0 g, 31%) as a yellow solid. LC/MS (ESI+): 313.00 (M+H).

1146c) Following a procedure similar to Example 258c, 2-(7-amino-8-methoxy-1,2,4,5-tetrahydro-benzo[d]azepin-3-yl)-N,N-dimethyl-acetamide and 4-(2,5-dichloro-pyrimidin-4-ylamino)-3-methoxy-benzamide were converted to 4-[5-chloro-2-(3-dimethylcarbamoylmethyl-8-methoxy-2,3,4,5-tetrahydro-1H-benzo[d]azepin-7-ylamino)-pyrimidin-4-ylamino]-3-methoxy-benzamide (57 mg, 50%) as a yellow solid. MP: 113-131° C.; $^1$H-NMR (CDCl$_3$) δ 8.55 (d, J=8.3 Hz, 1H), 8.09 (s, 1H), 8.05 (s, 1H), 8.00 (s, 1H), 7.62 (s, 1H), 7.41 (s, 1H), 7.29 (d, J=8.6 Hz, 1H), 6.65 (s, 1H), 6.663 (br s, 1H) 5.75 (br s, 1H), 4.04 (s, 3H), 3.86 (s, 3H), 3.34 (s, 2H), 3.13 (s, 3H), 2.96 (s, 3H), 2.90 (m, 2H), 2.82 (m, 4H), 2.74 (m, 2H); LC/MS (ESI+): 554.17 (M+H).

Example 1147

2-{7-[5-Chloro-4-(2-cyanomethoxy-phenylamino)-pyrimidin-2-ylamino]-8-methoxy-1,2,4,5-tetrahydro-benzo[d]azepin-3-yl}-N,N-dimethyl-acetamide Following a procedure similar to Example 258c, 2-(7-amino-8-methoxy-1,2,4,5-tetrahydro-benzo[d]azepin-3-yl)-N,N-dimethyl-acetamide and [2-(2,5-dichloro-pyrimidin-4-ylamino)-phenoxy]-acetonitrile were converted to 2-{7-[5-chloro-4-(2-cyanomethoxy-phenylamino)-pyrimidin-2-ylamino]-8-methoxy-1,2,4,5-tetrahydro-benzo[d]azepin-3-yl}-N,N-dimethyl-acetamide (35 mg, 34%) as a white solid. MP: 77-93° C.; $^1$H-NMR (CDCl$_3$) δ 8.45 (d, J=7.6 Hz, 1H), 8.09 (s, 1H), 8.01 (s, 1H), 7.57 (s, 1H), 7.46 (s, 1H), 7.11 (m, 2H), 7.04 (d, J=7.6 Hz, 1H), 6.65 (s, 1H), 4.88 (s, 2H), 3.86 (s, 3H), 3.28 (s, 2H), 3.15 (s, 3H), 2.98 (s, 3H), 2.88 (m, 2H), 2.80 (m, 2H), 2.69 (m, 4H); LC/MS (ESI+): 536.14 (M+H).

Example 1148

5-Chloro-N*2*-[3-(2-methanesulfonyl-ethyl)-8-methoxy-2,3,4,5-tetrahydro-1H-benzo[d]azepin-7-yl]-N*4*-(2-methanesulfonyl-phenyl)-pyrimidine-2,4-diamine Following a procedure similar to Example 258c, 3-(2-methanesulfonyl-ethyl)-8-methoxy-2,3,4,5-tetrahydro-1H-benzo[d]azepin-7-ylamine and (2,5-dichloro-pyrimidin-4-yl)-(2-methanesulfonyl-phenyl)-amine were converted to 5-chloro-N*2*-[3-(2-methanesulfonyl-ethyl)-8-methoxy-2,3,4,5-tetrahydro-1H-benzo[d]azepin-7-yl]-N*4*-(2-methanesulfonyl-phenyl)-pyrimidine-2,4-diamine (50 mg, 40%) as a white solid. MP: 85-100° C.; $^1$H-NMR (CDCl$_3$) δ 9.29 (s, 1H), 8.54 (d, J=8.4 Hz, 1H), 8.18 (s, 1H), 8.02 (s, 1H), 8.01 (s, 1H), 7.62 (m, 1H), 7.53 (br s, 1H), 7.30 (m, 1H), 6.66 (s, 1H), 3.88 (s, 3H), 3.17 (m, 2H), 3.11 (s, 3H), 3.07 (s, 3H), 3.03 (m, 2H), 2.85 (m, 2H), 2.75 (br s, 2H), 2.68 (m, 4H); LC/MS (ESI+): 580.14 (M+H).

Example 1149

2-{7-[5-Chloro-4-(5-cyano-2-methoxy-phenylamino)-pyrimidin-2-ylamino]-8-methoxy-1,2,4,5-tetrahydro-benzo[d]azepin-3-yl}-N,N-dimethyl-acetamide 1149a) Following a sequence of reactions analogous to 263b and 1136a 4-methoxy-3-nitro-benzonitrile was converted to 3-(2,5-dichloro-pyrimidin-4-ylamino)-4-methoxy-benzonitrile (90 mg, 9%) as a white solid. LC/MS (ESI+): 295.00 (M+H).

1149b) Following a procedure similar to Example 258c, 2-(7-amino-8-methoxy-1,2,4,5-tetrahydro-benzo[d]azepin-3-yl)-N,N-dimethyl-acetamide and 3-(2,5-dichloro-pyrimidin-4-ylamino)-4-methoxy-benzonitrile were converted to 2-{7-[5-chloro-4-(5-cyano-2-methoxy-phenylamino)-pyrimidin-2-ylamino]-8-methoxy-1,2,4,5-tetrahydro-benzo[d]azepin-3-yl}-N,N-dimethyl-acetamide (41 mg, 50%) as an off-white solid. MP: 86-105° C.; $^1$H-NMR (CDCl$_3$) δ 8.78 (s, 1H), 8.12 (s, 1H), 7.91 (s, 1H), 7.82 (s, 1H), 7.39 (s, 1H), 7.37 (d, J=8.0 Hz, 1H), 6.96 (d, J=8.0 Hz, 1H), 6.68 (s, 1H), 4.00 (s, 3H), 3.88 (s, 3H), 3.27 (s, 2H), 3.14 (s, 3H), 2.95 (s, 3H), 2.91 (m, 4H), 2.68 (m, 4H); LC/MS (ESI+): 536.19 (M+H).

Example 1150

2-{7-[5-Chloro-4-(4-morpholin-4-yl-phenylamino)-pyrimidin-2-ylamino]-8-methoxy-1,2,4,5-tetrahydro-benzo[d]azepin-3-yl}-N,N-dimethyl-acetamide Following a procedure similar to Example 258c, 2-(7-amino-8-methoxy-1,2,4,5-tetrahydro-benzo[d]azepin-3-yl)-N,N-dimethyl-acetamide and (2,5-dichloro-pyrimidin-4-yl)-(4-morpholin-4-yl-phenyl)-amine were converted to 2-{7-[5-chloro-4-(4-morpholin-4-yl-phenylamino)-pyrimidin-2-ylamino]-8-methoxy-1,2,4,5-tetrahydro-benzo[d]azepin-3-yl}-N,N-dimethyl-acetamide (48 mg, 44%) as a white solid. MP: 227-242° C.; $^1$H-NMR (CDCl$_3$) δ 8.02 (s, 2H), 7.48 (m, 3H), 6.92 (m, 3H), 6.60 (s, 1H), 3.89 (m, 4H), 3.84 (s, 3H), 3.25 (s, 2H), 3.16 (m, 4H), 3.15 (s, 3H), 2.98 (s, 3H), 2.88 (m, 2H), 2.75-2.60 (m, 6H); LC/MS (ESI+): 566.24 (M+H).

Example 1151

2-(7-{5-Chloro-4-[2-(propane-2-sulfonyl)-phenylamino]-pyrimidin-2-ylamino}-8-methoxy-1,2,4,5-tetrahydro-benzo[d]azepin-3-yl)-N,N-dimethyl-acetamide Following a procedure similar to 1142a,b, 2-(7-amino-8-methoxy-1,2,4,5-tetrahydro-benzo[d]azepin-3-yl)-N,N-dimethyl-acetamide and (2,5-dichloro-pyrimidin-4-yl)-[2-(propane-2-sulfonyl)-phenyl]-amine were converted to 2-(7-{5-chloro-4-[2-(propane-2-sulfonyl)-phenylamino]-pyrimidin-2-ylamino}-8-methoxy-1,2,4,5-tetrahydro-benzo[d]azepin-3-yl)-N,N-dimethyl-acetamide (79 mg, 51%) as a white solid. MP: 83-94° C.; $^1$H-NMR (CDCl$_3$) δ 9.50 (s, 1H), 8.55 (d, J=8.1 Hz, 1H), 8.15 (s, 1H), 7.97 (s, 1H), 7.92 (d, J=8.0 Hz, 1H), 7.60 (m, 1H), 7.51 (br s, 1H), 7.26 (m, 1H), 6.65 (s, 1H), 3.87 (s, 3H), 3.28 (s, 2H), 3.24 (m, 1H), 3.14 (s, 3H), 2.98 (s, 3H), 2.88 (m, 2H), 2.74-2.65 (m, 6H), 1.31 (d, J=6.8 Hz, 6H); LC/MS (ESI+): 587.21 (M+H).

Example 1152

2-{5-Chloro-2-[3-(2-methanesulfonyl-ethyl)-8-methoxy-2,3,4,5-tetrahydro-1H-benzo[d]azepin-7-ylamino]-pyrimidin-4-ylamino}-N,N-dimethyl-benzenesulfonamide Following a procedure similar to Example 258c, 3-(2-methanesulfonyl-ethyl)-8-methoxy-2,3,4,5-tetrahydro-1H-benzo[d]azepin-7-ylamine and 2-(2,5-dichloro-pyrimidin-4-ylamino)-N,N-dimethyl-benzenesulfonamide were converted to 2-{5-chloro-2-[3-(2-methanesulfonyl-ethyl)-8-methoxy-2,3,4,5-tetrahydro-1H-benzo[d]azepin-7-ylamino]-pyrimidin-4-ylamino}-N,N-dimethyl-benzenesulfonamide (40 mg, 30%) as a white solid. MP: 84-101° C.; $^1$H-NMR (CDCl$_3$) δ 9.35 (s, 1H), 8.53 (d, J=8.3 Hz, 1H), 8.14 (s, 1H), 8.03 (s, 1H), 7.89 (d, J=7.9 Hz, 1H), 7.55 (m, 1H), 7.51 (br s, 1H), 7.25 (m, 1H), 6.65 (s, 1H), 3.88 (s, 3H), 3.17 (m, 2H), 3.16 (s, 3H), 3.04 (m, 2H), 2.85 (m, 2H), 2.75 (s, 6H), 2.70 (m, 6H); LC/MS (ESI+): 609.19 (M+H).

Example 1153

4-{5-Chloro-2-[8-methoxy-3-(2-methoxy-1-methoxymethyl-ethyl)-2,3,4,5-tetrahydro-1H-benzo[d]azepin-7-ylamino]-pyrimidin-4-ylamino}-3-methoxy-benzamide Following a procedure similar to Example 258c, 8-methoxy-3-(2-methoxy-1-methoxymethyl-ethyl)-2,3,4,5-tetrahydro-1H-benzo[d]azepin-7-ylamine and 4-(2,5-dichloro-pyrimidin-4-ylamino)-3-methoxy-benzamide were converted to 4-{5-chloro-2-[8-methoxy-3-(2-methoxy-1-methoxymethyl-ethyl)-2,3,4,5-tetrahydro-1H-benzo[d]azepin-7-ylamino]-pyrimidin-4-ylamino}-3-methoxy-benzamide (48 mg, 40%) as an off-white solid. MP: 220-223° C.; $^1$H-NMR (CDCl$_3$) δ 8.61 (d, J=8.3 Hz, 1H), 8.11 (s, 1H), 8.08 (s, 1H), 8.03 (s, 1H), 7.65 (s, 1H), 7.43 (br s, 1H), 7.25 (br s, 1H), 6.67 (s, 1H), 6.51 (br s, 1H), 5.45 (br s, 1H), 4.03 (s, 3H), 3.88 (m, 4H), 3.58 (m, 2H), 3.49 (m, 2H), 3.33 (s, 6H), 2.95 (m, 2H), 2.88 (m, 2H), 2.79 (m, 4H); LC/MS (ESI+): 571.24 (M+H).

Example 1154

2-{7-[5-Chloro-4-(5-cyano-2-methoxy-phenylamino)-pyrimidin-2-ylamino]-8-methoxy-1,2,4,5-tetrahydro-benzo[d]azepin-3-yl}-acetamide Following a procedure similar to Example 258c, 2-(7-amino-8-methoxy-1,2,4,5-tetrahydro-benzo[d]azepin-3-yl)-acetamide and 3-(2,5-dichloro-pyrimidin-4-ylamino)-4-methoxy-benzonitrile were converted to 2-{7-[5-chloro-4-(5-cyano-2-methoxy-phenylamino)-pyrimidin-2-ylamino]-8-methoxy-1,2,4,5-tetrahydro-benzo[d]azepin-3-yl}-acetamide (13 mg, 18%) as a white solid. MP: 100-125° C.; $^1$H-NMR (CDCl$_3$) δ 8.79 (s, 1H), 8.12 (s, 1H), 7.92 (s, 1H), 7.84 (s, 1H), 7.38 (s, 1H), 7.36 (s, 1H), 7.29 (br s, 1H), 7.97 (d, J=8.6 Hz, 1H), 6.69 (s, 1H), 5.52 (br s, 1H), 4.02 (s, 3H), 3.89 (s, 3H), 3.11 (s, 2H), 2.90 (m, 4H), 2.71 (m, 4H); LC/MS (ESI+): 508.19 (M+H).

Example 1155

2-{7-[5-Chloro-4-(2-methoxy-4-morpholin-4-yl-phenylamino)-pyrimidin-2-ylamino]-8-methoxy-1,2, 4,5-tetrahydro-benzo[d]azepin-3-yl}-1-pyrrolidin-1-yl-ethanone Following a procedure similar to Example 258c, 2-(7-amino-8-methoxy-1,2,4,5-tetrahydro-benzo[d]azepin-3-yl)-1-pyrrolidin-1-yl-ethanone, prepared in an analogous manner to 258a,b, and (2,5-dichloro-pyrimidin-4-yl)-(2-methoxy-4-morpholin-4-yl-phenyl)-amine were converted to 2-{7-[5-chloro-4-(2-methoxy-4-morpholin-4-yl-phenylamino)-pyrimidin-2-ylamino]-8-methoxy-1,2,4,5-tetrahydro-benzo[d]azepin-3-yl}-1-pyrrolidin-1-yl-ethanone (33 mg, 27%) as a white solid. MP: 82-105° C.; $^1$H-NMR (CDCl$_3$) δ 8.24 (d, J=8.3 Hz, 1H), 8.11 (s, 1H), 8.03 (s, 1H), 7.54 (s, 1H), 7.43 (s, 1H), 6.65 (s, 1H), 6.54 (s, 1H), 6.50 (d, J=8.3 Hz, 1H), 3.94 (s, 3H), 3.92 (m, 4H), 3.88 (s, 3H), 3.52 (m, 4H), 3.23 (s, 2H), 3.14 (m, 4H), 2.88 (m, 4H), 2.72 (br s, 4H), 1.95 (m, 2H), 1.87 (m, 2H); LC/MS (ESI+): 622.32 (M+H).

Example 1156

4-{5-Chloro-2-[8-methoxy-3-(2-methoxy-ethyl)-2,3, 4,5-tetrahydro-1H-benzo[d]azepin-7-ylamino]-pyrimidin-4-ylamino}-3-methoxy-benzamide Following a procedure similar to Example 258c, 8-methoxy-3-(2-methoxy-ethyl)-2,3,4,5-tetrahydro-1H-benzo[d]azepin-7-ylamine and 4-(2,5-dichloro-pyrimidin-4-ylamino)-3-methoxy-benzamide were converted to 4-{5-Chloro-2-[8-methoxy-3-(2-methoxy-ethyl)-2,3,4,5-tetrahydro-1H-benzo[d]azepin-7-ylamino]-pyrimidin-4-ylamino}-3-methoxy-benzamide (28 mg, 22%) as an off-white solid. MP: 100-112° C.; $^1$H-NMR (CDCl$_3$) δ 8.63 (d, J=8.4 Hz, 1H), 8.12 (s, 1H), 8.06 (s, 2H), 7.58 (s, 1H), 7.42 (s, 1H), 7.28 (d, J=8.4 Hz, 1H), 6.68 (s, 1H), 6.14 (br s, 1H), 5.55 (br s, 1H), 4.05 (s, 3H), 3.88 (s, 3H), 3.55 (m, 2H), 3.35 (s, 3H), 2.94 (m, 2H), 2.88 (m, 2H), 2.78 (m, 6H); LC/MS (ESI+): 527.17 (M+H).

Example 1157

2-{5-Chloro-2-[8-methoxy-3-(2-oxo-2-pyrrolidin-1-yl-ethyl)-2,3,4,5-tetrahydro-1H-benzo[d]azepin-7-ylamino]-pyrimidin-4-ylamino}-N,N-dimethyl-benzenesulfonamide Following a procedure similar to Example 258c, 2-(7-amino-8-methoxy-1,2,4,5-tetrahydro-benzo[d]azepin-3-yl)-1-pyrrolidin-1-yl-ethanone and 2-(2,5-dichloro-pyrimidin-4-ylamino)-N,N-dimethyl-benzenesulfonamide were converted to 2-{5-chloro-2-[8-methoxy-3-(2-oxo-2-pyrrolidin-1-yl-ethyl)-2,3,4,5-tetrahydro-1H-benzo[d]azepin-7-ylamino]-pyrimidin-4-ylamino}-N,N-dimethyl-benzenesulfonamide (59 mg, 47%) as a light yellow solid. MP: 75-93° C.; $^1$H-NMR (CDCl$_3$) δ 9.32 (s, 1H), 8.53 (d, J=8.0 Hz, 1H), 8.14 (s, 1H), 7.99 (s, 1H), 7.88 (d, J=8.0 Hz, 1H), 7.57 (m, 1H), 7.49 (s, 1H), 7.24 (m, 1H), 6.63 (s, 1H), 3.87 (s, 3H), 3.52 (m, 4H), 3.22 (s, 2H), 2.90 (m, 2H), 2.72 (s, 6H), 2.71 (m, 6H), 1.95 (m, 2H), 1.88 (m, 2H); LC/MS (ESI+): 614.19 (M+H).

Example 1158

2-(7-{5-Chloro-4-[2-(propane-2-sulfonyl)-phenylamino]-pyrimidin-2-ylamino}-8-methoxy-1,2,4,5-tetrahydro-benzo[d]azepin-3-yl)-1-pyrrolidin-1-yl-ethanone Following a procedure similar to Example 258c, 2-(7-amino-8-methoxy-1,2,4,5-tetrahydro-benzo[d]azepin-3-yl)-1-pyrrolidin-1-yl-ethanone and (2,5-dichloro-pyrimidin-4-yl)-[2-(propane-2-sulfonyl)-phenyl]-amine were converted to 2-(7-{5-Chloro-4-[2-(propane-2-sulfonyl)-phenylamino]-pyrimidin-2-ylamino}-8-methoxy-1,2,4,5-tetrahydro-benzo[d]azepin-3-yl)-1-pyrrolidin-1-yl-ethanone (39 mg, 32%) as a white solid. MP: 88-105° C.; $^1$H-NMR (CDCl$_3$) δ 9.49 (s, 1H), 8.55 (d, J=8.4 Hz, 1H), 8.15 (s, 1H), 7.95 (s, 1H), 7.92 (d, J=8.4 Hz, 1H), 7.60 (m, 1H), 7.52 (s, 1H), 7.26 (m, 1H), 6.65 (s, 1H), 3.88 (s, 3H), 3.54 (m, 4H), 3.27 (m, 1H), 3.25 (s, 2H), 2.89 (m, 2H), 2.73 (m, 6H), 1.95 (m, 2H), 1.88 (m, 2H), 1.32 (d, J=6.8 Hz, 6H); LC/MS (ESI+): 613.19 (M+H).

Example 1159

(1S,2S,3R,4R)-3-{5-Chloro-2-[8-methoxy-3-(2-oxo-2-pyrrolidin-1-yl-ethyl)-2,3,4,5-tetrahydro-1H-benzo[d]azepin-7-ylamino]-pyrimidin-4-ylamino}-bicyclo[2.2.1]hept-5-ene-2-carboxylic acid amide Following a procedure similar to Example 258c, 2-(7-amino-8-methoxy-1,2,4,5-tetrahydro-benzo[d]azepin-3-yl)-1-pyrrolidin-1-yl-ethanone and (1S,2S,3R,4R)-3-(2,5-dichloro-pyrimidin-4-ylamino)-bicyclo[2.2.1]hept-5-ene-2-carboxylic acid amide were converted to (1S,2S,3R,4R)-3-{5-chloro-2-[8-methoxy-3-(2-oxo-2-pyrrolidin-1-yl-ethyl)-2,3,4,5-tetrahydro-1H-benzo[d]azepin-7-ylamino]-pyrimidin-4-ylamino}-bicyclo[2.2.1]hept-5-ene-2-carboxylic acid amide (40 mg, 40%) as a beige solid. MP: 126-145° C.; $^1$H-NMR (CDCl$_3$) δ 8.17 (s, 1H), 7.87 (s, 1H), 7.40 (s, 1H), 6.63 (s, 1H), 6.61 (s, 1H), 6.30 (s, 2H), 5.78 (br s, 1H), 5.41 (br s, 1H), 4.43 (t, J=8.3 Hz, 1H), 3.86 (s, 3H), 3.52 (m, 4H), 3.23 (s, 2H), 3.06 (s, 1H), 2.87 (m, 5H), 2.73 (m, 4H), 2.52 (d, J=8.1 Hz, 1H), 2.25 (d, J=9.3 Hz, 1H), 1.95 (m, 2H), 1.86 (m, 2H), 1.63 (d, J=9.3 Hz, 1H); LC/MS (ESI+): 566.22 (M+H).

Example 1160

N-((1R,2R)-2-{5-Chloro-2-[8-methoxy-3-(2-oxo-2-pyrrolidin-1-yl-ethyl)-2,3,4,5-tetrahydro-1H-benzo[d]azepin-7-ylamino]-pyrimidin-4-ylamino}-cyclohexyl)-methanesulfonamide Following a procedure similar to Example 258c, 2-(7-amino-8-methoxy-1,2,4,5-tetrahydro-benzo[d]azepin-3-yl)-1-pyrrolidin-1-yl-ethanone and N-[(1R,2R)-2-(2,5-dichloro-pyrimidin-4-ylamino)-cyclohexyl]-methanesulfonamide were converted to N-((1R,2R)-2-{5-chloro-2-[8-methoxy-3-(2-oxo-2-pyrrolidin-1-yl-ethyl)-2,3,4,5-tetrahydro-1H-benzo[d]azepin-7-ylamino]-pyrimidin-4-ylamino}-cyclohexyl)-methanesulfonamide (48.63 mg, 49%) as a white solid. MP: 120-135° C.; $^1$H-NMR (CDCl$_3$) δ 7.92 (s, 2H), 7.31 (s, 1H), 6.55 (s, 1H), 5.92 (br s, 1H), 5.56 (d, J=7.3 Hz, 1H), 3.92 (m, 1H), 3.85 (s, 3H), 3.49 (m, 4H), 3.20 (m, 3H), 2.91 (m, 4H), 2.81 (s, 3H), 2.78 (m, 2H), 2.61 (m, 2H), 2.26 (m, 2H), 1.96 (m, 2H), 1.88 (m, 4H), 1.50 (m, 1H), 1.34 (m, 3H); LC/MS (ESI+): 606.20 (M+H).

Example 1161

4-{5-Chloro-2-[3-(2-methanesulfonyl-ethyl)-8-methoxy-2,3,4,5-tetrahydro-1H-benzo[d]azepin-7-ylamino]-pyrimidin-4-ylamino}-3-methoxy-benzamide Following a procedure similar to Example 258c, 3-(2-methanesulfonyl-ethyl)-8-methoxy-2,3,4,5-tetrahydro-1H-benzo[d]azepin-7-ylamine and 4-(2,5-dichloro-pyrimidin-4- ylamino)-3-methoxy-benzamide were converted to 4-{5-chloro-2-[3-(2-methanesulfonyl-ethyl)-8-methoxy-2,3,4,5-tetrahydro-1H-benzo[d]azepin-7-ylamino]-pyrimidin-4-ylamino}-3-methoxy-benzamide (15 mg, 15%) as a tan solid. MP: 207-217° C.; $^1$H-NMR (CDCl$_3$) δ 8.55 (d, J=8.4 Hz, 1H), 8.12 (s, 1H), 8.08 (s, 1H), 7.96 (s, 1H), 7.51 (s, 1H), 7.47 (s, 1H), 7.39 (d, J=8.4 Hz, 1H), 6.66 (s, 1H), 6.20 (br s, 2H), 4.02 (s, 3H), 3.88 (s, 3H), 3.22 (m, 2H), 3.08 (s, 3H), 3.05 (m, 2H), 2.87 (m, 2H), 2.79 (m, 2H), 2.73 (m, 4H); LC/MS (ESI+): 575.17 (M+H).

Example 1162

2-(7-{5-Chloro-4-[4-methoxy-2-(propane-2-sulfonyl)-phenylamino]-pyrimidin-2-ylamino}-8-methoxy-1,2,4,5-tetrahydro-benzo[d]azepin-3-yl)-N,N-dimethyl-acetamide Following a procedure similar to 1151, 2-(7-amino-8-methoxy-1,2,4,5-tetrahydro-benzo[d]azepin-3-yl)-N,N-dimethyl-acetamide and (2,5-dichloro-pyrimidin-4-yl)-[4-methoxy-2-(propane-2-sulfonyl)-phenyl]-amine were converted to 2-(7-{5-chloro-4-[4-methoxy-2-(propane-2-sulfonyl)-phenylamino]-pyrimidin-2-ylamino}-8-methoxy-1,2,4,5-tetrahydro-benzo[d]azepin-3-yl)-N,N-dimethyl-acetamide (30 mg, 20%) as a light yellow solid. MP: 68-79° C.; $^1$H-NMR (CDCl$_3$) δ 9.01 (s, 1H), 8.29 (d, J=9.2 Hz, 1H), 8.11 (s, 1H), 7.93 (s, 1H), 7.50 (s, 1H), 7.44 (s, 1H), 7.16 (d, J=9.2 Hz, 1H), 6.64 (s, 1H), 3.88 (s, 3H), 3.86 (s, 3H), 3.29 (s, 2H), 3.23 (m, 1H), 3.14 (s, 3H), 2.98 (s, 3H), 2.88 (m, 2H), 2.67 (m, 6H), 1.30 (d, J=6.8 Hz, 6H); LC/MS (ESI+): 617.20 (M+H).

Example 1163

2-{7-[5-Chloro-4-(4-cyano-2-methoxy-phenylamino)-pyrimidin-2-ylamino]-8-methoxy-1,2,4,5-tetrahydro-benzo[d]azepin-3-yl}-N,N-dimethyl-acetamide Following a procedure similar to Example 258c, 2-(7-amino-8-methoxy-1,2,4,5-tetrahydro-benzo[d]azepin-3-yl)-N,N-dimethyl-acetamide and 4-(2,5-dichloro-pyrimidin-4-ylamino)-3-methoxy-benzonitrile, which was prepared in a similar manner to 11149a were converted to 2-{7-[5-chloro-4-(4-cyano-2-methoxy-phenylamino)-pyrimidin-2-ylamino]-8-methoxy-1,2,4,5-tetrahydro-benzo[d]azepin-3-yl}-N,N-dimethyl-acetamide (42 mg, 42%) as a white solid. MP: 92-105° C.; $^1$H-NMR (CDCl$_3$) δ 8.69 (d, J=8.6 Hz, 1H), 8.13 (s, 1H), 8.06 (s, 1H), 7.96 (s, 1H), 7.42 (s, 1H), 7.26 (d, J=8.6 Hz, 1H), 7.13 (s, 1H), 6.68 (s, 1H), 4.00 (s, 3H), 3.88 (s, 3H), 3.31 (s, 2H), 3.17 (s, 3H), 2.98 (s, 3H), 2.90 (m, 2H), 2.85 (m, 2H), 2.72 (br s, 4H); LC/MS (ESI+): 536.17 (M+H).

Example 1164

5-Chloro-N*2*-[3-(2-methanesulfonyl-ethyl)-8-methoxy-2,3,4,5-tetrahydro-1H-benzo[d]azepin-7-yl]-N*4*-[2-(propane-2-sulfonyl)-phenyl]-pyrimidine-2,4-diamine Following a procedure similar to Example 258c, 3-(2-methanesulfonyl-ethyl)-8-methoxy-2,3,4,5-tetrahydro-1H-benzo[d]azepin-7-ylamine and (2,5-dichloro-pyrimidin-4-yl)-[2-(propane-2-sulfonyl)-phenyl]-amine were converted to 5-chloro-N*2*-[3-(2-methanesulfonyl-ethyl)-8-methoxy-2,3,4,5-tetrahydro-1H-benzo[d]azepin-7-yl]-N*4*-[2-(propane-2-sulfonyl)-phenyl]-pyrimidine-2,4-diamine (27 mg, 24%) as a white solid. MP: 89-99° C.; $^1$H-NMR (CDCl$_3$) δ 9.52 (s, 1H), 8.56 (d, J=8.4 Hz, 1H), 8.16 (s, 1H), 8.02 (s, 1H), 7.94 (d, J=8.0 Hz, 1H), 7.60 (t, J=8.0 Hz, 1H), 7.51 (s, 1H), 7.27 (m, 1H), 6.65 (s, 1H), 3.88 (s, 3H), 3.27 (m, 1H), 3.17 (m, 2H), 3.07 (s, 3H), 3.03 (m, 2H), 2.86 (m, 2H), 2.69 (m, 6H), 1.32 (d, J=6.8 Hz, 6H); LC/MS (ESI+): 608.16 (M+H).

Example 1165

2-{5-Chloro-2-[8-methoxy-3-(2-methoxy-ethyl)-2,3,4,5-tetrahydro-1H-benzo[d]azepin-7-ylamino]-pyrimidin-4-ylamino}-N,N-dimethyl-benzenesulfonamide Following a procedure similar to Example 258c, 8-methoxy-3-(2-methoxy-ethyl)-2,3,4,5-tetrahydro-1H-benzo[d]azepin-7-ylamine and 2-(2,5-dichloro-pyrimidin-4-ylamino)-N,N-dimethyl-benzenesulfonamide were converted to 2-{5-chloro-2-[8-methoxy-3-(2-methoxy-ethyl)-2,3,4,5-tetrahydro-1H-benzo[d]azepin-7-ylamino]-pyrimidin-4-ylamino}-N,N-dimethyl-benzenesulfonamide (30 mg, 28%) as a yellow solid. MP: 54-64° C.; 1H-NMR (CDCl$_3$) δ 9.34 (s, 1H), 8.52 (d, J=8.3 Hz, 1H), 8.13 (s, 1H), 7.98 (s, 1H), 7.88 (d, J=7.9 Hz, 1H), 7.55 (m, 1H), 7.52 (s, 1H), 7.23 (m, 1H), 6.65 (s, 1H), 3.87 (s, 3H), 3.57 (m, 2H), 3.37 (s, 3H), 2.91 (m, 2H), 2.81 (m, 4H), 2.78 (m, 4H), 2.74 (s, 6H); LC/MS (ESI+): 561.22 (M+H).

Example 1166

2-{7-[5-Chloro-4-(4-dimethylamino-2-methoxy-phenylamino)-pyrimidin-2-ylamino]-8-methoxy-1,2,4,5-tetrahydro-benzo[d]azepin-3-yl}-N,N-dimethyl-acetamide 1166a) 5-Fluoro-2-nitro-phenol (10.00 g, 0.06365 mol), dimethyl sulfate (6.4 mL, 0.068 mol), and potassium carbonate (10.4 g, 0.0752 mol) were added to N,N-dimethylformamide (80 mL), and the reaction was stirred overnight at room temperature. Water (400 mL) was added next, and the product, 4-fluoro-2-methoxy-1-nitro-benzene, precipitated as a yellow solid, which was collected by filtration and was washed with water, then dried (12 g, quantitative).

1166b) 4-Fluoro-2-methoxy-1-nitro-benzene (3.00 g, 17.5 mmol) in dimethyl sulfoxide (20 mL) was treated with 2 M of dimethylamine in THF (30 mL) at 100° C., in a sealed tube overnight. The reaction was cooled and quenched with water. The crude product, (3-methoxy-4-nitro-phenyl)-dimethyl-amine, was collected by filtration (2.87 g, 83%).

1166c) Following a sequence of reactions analogous to 263b and 1136a (3-methoxy-4-nitro-phenyl)-dimethyl-amine was converted to N*1*-(2,5-dichloro-pyrimidin-4-yl)-2-methoxy-N*4*,N*4*-dimethyl-benzene-1,4-diamine (3.2 g, 73%) as a brown solid. LC/MS (ESI+): 313.45 (M+H).

1166d) Following a procedure similar to Example 258c, 2-(7-amino-8-methoxy-1,2,4,5-tetrahydro-benzo[d]azepin-3-yl)-N,N-dimethyl-acetamide and N*1*-(2,5-dichloro-pyrimidin-4-yl)-2-methoxy-N*4*,N*4*-dimethyl-benzene-1,4-diamine were converted to 2-{7-[5-chloro-4-(4-dimethylamino-2-methoxy-phenylamino)-pyrimidin-2-ylamino]-8-methoxy-1,2,4,5-tetrahydro-benzo[d]azepin-3-yl}-N,N-dimethyl-acetamide (60 mg, 50%) as an off-white solid. MP: 69-83° C.; $^1$H-NMR (CDCl$_3$) δ 8.10 (s, 1H), 8.09 (d, J=8.5 Hz, 1H), 7.98 (s, 1H), 7.44 (s, 1H), 7.38 (s, 1H), 6.62 (s, 1H), 6.34 (s, 1H), 6.33 (d, J=8.5 Hz, 1H), 3.90 (s, 3H), 3.85

(s, 3H), 3.27 (s, 2H), 3.14 (s, 3H), 2.96 (s, 9H), 2.86 (m, 2H), 2.81 (m, 2H), 2.67 (m, 4H); LC/MS (ESI+): 554.28 (M+H).

Example 1167

5-Chloro-N*4*-(4-dimethylamino-2-methoxy-phenyl)-N*2*-[3-(2-methanesulfonyl-ethyl)-8-methoxy-2,3,4,5-tetrahydro-1H-benzo[d]azepin-7-yl]-pyrimidine-2,4-diamine Following a procedure similar to Example 258c, 3-(2-methanesulfonyl-ethyl)-8-methoxy-2,3,4,5-tetrahydro-1H-benzo[d]azepin-7-ylamine and N*1*-(2,5-dichloro-pyrimidin-4-yl)-2-methoxy-N*4*,N*4*-dimethyl-benzene-1,4-diamine were converted to 5-chloro-N*4*-(4-dimethylamino-2-methoxy-phenyl)-N*2*-[3-(2-methanesulfonyl-ethyl)-8-methoxy-2,3,4,5-tetrahydro-1H-benzo[d]azepin-7-yl]-pyrimidine-2,4-diamine (60 mg, 50%) as an off-white solid. MP: 81-94° C.; $^1$H-NMR (CDCl$_3$) δ 8.12 (s, 1H), 8.09 (d, J=8.8 Hz, 1H), 7.99 (s, 1H), 7.43 (s, 1H), 7.38 (s, 1H), 6.62 (s, 1H), 6.36 (s, 1H), 6.33 (d, J=8.8 Hz, 1H), 3.91 (s, 3H), 3.85 (s, 3H), 3.14 (m, 2H), 3.06 (s, 3H), 3.03 (m, 2H), 2.98 (s, 6H), 2.84 (m, 2H), 2.78 (m, 2H), 2.67 (m, 4H); LC/MS (ESI+): 575.21 (M+H).

Example 1168

5-Chloro-N*2*-[3-(2-methanesulfonyl-ethyl)-8-methoxy-2,3,4,5-tetrahydro-1H-benzo[d]azepin-7-yl]-N*4*-[2-methoxy-4-(2-methoxy-ethoxy)-phenyl]-pyrimidine-2,4-diamine Following a procedure similar to Example 258c, 3-(2-methanesulfonyl-ethyl)-8-methoxy-2,3,4,5-tetrahydro-1H-benzo[d]azepin-7-ylamine, and (2,5-dichloro-pyrimidin-4-yl)-[2-methoxy-4-(2-methoxy-ethoxy)-phenyl]-amine, which was prepared in a manner similar to 1166a-c, were converted to 5-chloro-N*2*-[3-(2-methanesulfonyl-ethyl)-8-methoxy-2,3,4,5-tetrahydro-1H-benzo[d]azepin-7-yl]-N*4*-[2-methoxy-4-(2-methoxy-ethoxy)-phenyl]-pyrimidine-2,4-diamine (53 mg, 40%) as a white solid. MP: 59-82° C.; $^1$H-NMR (CDCl$_3$) δ 8.17 (d, J=8.8 Hz, 1H), 8.08 (s, 1H), 8.02 (s, 1H), 7.45 (s, 2H), 6.63 (s, 2H), 6.49 (d, J=7.6 Hz, 1H), 4.14 (m, 2H), 3.89 (s, 3H), 3.86 (s, 3H), 3.78 (m, 2H), 3.48 (s, 3H), 3.18 (m, 2H), 3.08 (s, 3H), 3.03 (m, 2H), 2.85 (m, 2H), 2.77 (m, 2H), 2.68 (m, 4H); LC/MS (ESI+): 606.18 (M+H).

Example 1169

2-(7-{5-Chloro-4-[2-methoxy-4-(2-methoxy-ethoxy)-phenylamino]-pyrimidin-2-ylamino}-8-methoxy-1,2,4,5-tetrahydro-benzo[d]azepin-3-yl)-N,N-dimethyl-acetamide Following a procedure similar to Example 258c, 2-(7-amino-8-methoxy-1,2,4,5-tetrahydro-benzo[d]azepin-3-yl)-N,N-dimethyl-acetamide and (2,5-dichloro-pyrimidin-4-yl)-[2-methoxy-4-(2-methoxy-ethoxy)-phenyl]-amine were converted to 2-(7-{5-chloro-4-[2-methoxy-4-(2-methoxy-ethoxy)-phenylamino]-pyrimidin-2-ylamino}-8-methoxy-1,2,4,5-tetrahydro-benzo[d]azepin-3-yl)-N,N-dimethyl-acetamide (29 mg, 20%) as a tan solid. MP: 51-59° C.; $^1$H-NMR (CDCl$_3$) δ 8.24 (d, J=8.8 Hz, 1H), 8.08 (s, 1H), 8.02 (s, 1H), 7.51 (s, 1H), 7.42 (s, 1H), 6.63 (s, 1H), 6.61 (s, 1H), 6.48 (d, J=8.8 Hz, 1H), 4.13 (m, 2H), 3.89 (s, 3H), 3.86 (s, 3H), 3.79 (m, 2H), 3.47 (s, 3H), 3.27 (s, 2H), 3.15 (s, 3H), 2.97 (s, 3H), 2.88 (m, 2H), 2.82 (m, 2H), 2.68 (m, 4H); LC/MS (ESI+): 585.27 (M+H).

Example 1170

2-[5-Chloro-2-(8-methoxy-3-oxazol-2-ylmethyl-2,3,4,5-tetrahydro-1H-benzo[d]azepin-7-ylamino)-pyrimidin-4-ylamino]-N,N-dimethyl-benzenesulfonamide 8-Methoxy-3-oxazol-2-ylmethyl-2,3,4,5-tetrahydro-1H-benzo[d]azepin-7-ylamine (100.00 mg), which was prepared in a manner similar to 258a,c, was combined with 2-(2,5-dichloro-pyrimidin-4-ylamino)-N,N-dimethyl-benzenesulfonamide (133.4 mg, 0.0003842 mol), 4 M of hydrogen chloride in 1,4-dioxane (182.9 uL), and 2-methoxyethanol (4 mL) in a Radley tube. The reaction was heated at 135° C. overnight. The reaction was neutralized with saturated Na$_2$CO$_3$, extracted in dichloromethane, followed by drying (MgSO$_4$), concentration, and flash chromatography purification (SiO$_2$, MeOH/EtOAc, 0-10%) to afford 2-[5-chloro-2-(8-methoxy-3-oxazol-2-ylmethyl-2,3,4,5-tetrahydro-1H-benzo[d]azepin-7-ylamino)-pyrimidin-4-ylamino]-N,N-dimethyl-benzenesulfonamide (76 mg, 36%) as a light yellow solid. MP: 71-77° C.; $^1$H-NMR (CDCl$_3$) δ 9.32 (s, 1H); 8.50 (d, J=8.0 Hz; 1H), 8.13 (s, 1H), 7.97 (s, 1H), 7.88 (d, J=8.0 Hz, 1H), 7.63 (s, 1H), 7.54 (t, J=8.0 Hz, 1H), 7.49 (s, 1H), 7.23 (t, J=8.0 Hz, 1H), 7.07 (s, 1H), 6.64 (s; 1H), 3.89 (s; 2H), 3.86 (s, 3H), 2.89 (m, 2H), 2.74 (s, 6H), 2.72 (m; 6H); LC/MS (ESI+): 584.14 (M+H).

Example 1171

2-{5-Chloro-2-[8-methoxy-3-(1-methyl-1H-imidazol-2-ylmethyl)-2,3,4,5-tetrahydro-1H-benzo[d]azepin-7-ylamino]-pyrimidin-4-ylamino}-N,N-dimethyl-benzenesulfonamide Following a procedure similar to 1170, 8-methoxy-3-(1-methyl-1H-imidazol-2-ylmethyl)-2,3,4,5-tetrahydro-1H-benzo[d]azepin-7-ylamine, which was prepared in a manner similar to 258a,c, and 2-(2,5-dichloro-pyrimidin-4-ylamino)-N,N-dimethyl-benzenesulfonamide were converted to 2-{5-chloro-2-[8-methoxy-3-(1-methyl-1H-imidazol-2-ylmethyl)-2,3,4,5-tetrahydro-1H-benzo[d]azepin-7-ylamino]-pyrimidin-4-ylamino}-N,N-dimethyl-benzenesulfonamide (105 mg, 54%) as a light yellow solid. MP: 79-86° C.; $^1$H-NMR (CDCl$_3$) δ 9.33 (s, 1H), 8.51 (d, J=8.0 Hz; 1H), 8.13 (s, 1H), 7.98 (s, 1H), 7.87 (d, J=8.0 Hz, 1H), 7.55 (t, J=8.0 Hz, 1H), 7.51 (s, 1H), 7.22 (t, J=8.0 Hz, 1H), 6.98 (s, 1H), 6.89 (s; 1H), 6.63 (s, 1H), 3.86 (s, 3H), 3.78 (s, 3H), 3.71 (s, 2H), 2.82 (m, 2H), 2.74 (s, 6H), 2.68 (m, 2H), 2.62 (m; 4H); LC/MS (ESI+): 597.20 (M+H).

Example 1172

5-Chloro-N*4*-(4-dimethylamino-2-methoxy-phenyl)-N*2*-(8-methoxy-3-oxazol-2-ylmethyl-2,3,4,5-tetrahydro-1H-benzo[d]azepin-7-yl)-pyrimidine-2,4-diamine Following a procedure similar to 1170, 8-methoxy-3-oxazol-2-ylmethyl-2,3,4,5-tetrahydro-1H-benzo[d]azepin-7-ylamine, and N*1*-(2,5-dichloro-pyrimidin-4-yl)-2-methoxy-N*4*,N*4*-dimethyl-benzene-1,4-diamine were converted to 5-chloro-N*4*-(4-dimethylamino-2-methoxyphenyl)-N*2*-(8-methoxy-3-oxazol-2-ylmethyl-2,3,4,5-tetrahydro-1H-benzo[d]azepin-7-yl)-pyrimidine-2,4-diamine (45 mg, 32%) as an off-white solid. MP: 69-79° C.; $^1$H-NMR (CDCl$_3$) δ 8.11 (s, 1H), 8.07 (d, J=8.8 Hz, 1H), 7.98 (s, 1H), 7.62 (s, 1H), 7.44 (s, 1H), 7.36 (s, 1H), 7.06 (s, 1H), 6.61 (s, 1H), 6.34 (s, 1H), 6.32 (d, J=8.8 Hz, 1H), 3.89 (s, 3H), 3.87 (s, 2H), 3.84 (s, 3H), 2.95 (s, 6H), 2.88 (m; 2H), 2.82 (m, 2H), 2.74 (m, 2H), 2.71 (m, 2H); LC/MS (ESI+): 550.20 (M+H).

Example 1173

5-Chloro-N*4*-(4-dimethylamino-2-methoxy-phenyl)-N*2*-[8-methoxy-3-(1-methyl-1H-imidazol-2-ylmethyl)-2,3,4,5-tetrahydro-1H-benzo[d]azepin-7-yl]-pyrimidine-2,4-diamine Following a procedure similar to 1170, 8-methoxy-3-(1-methyl-1H-imidazol-2-ylmethyl)-2,3,4,5-tetrahydro-1H-benzo[d]azepin-7-ylamine, and N*1*-(2,5-dichloro-pyrimidin-4-yl)-2-methoxy-N*4*,N*4*-dimethyl-benzene-1,4-diamine were converted to 5-chloro-N*4*-(4-dimethylamino-2-methoxy-phenyl)-N*2*-[8-methoxy-3-(1-methyl-1H-imidazol-2-ylmethyl)-2,3,4,5-tetrahydro-1H-benzo[d]azepin-7-yl]-pyrimidine-2,4-diamine (35 mg, 25%) as an off-white solid. MP: 74-82° C.; $^1$H-NMR (CDCl$_3$) δ 8.09 (s, 1H), 8.04 (d, J=8.8 Hz, 1H), 7.98 (s, 1H), 7.45 (s, 1H), 7.34 (s, 1H), 6.95 (s, 1H), 6.87 (s, 1H), 6.60 (s, 1H), 6.33 (s, 1H), 6.31 (d, J=8.8 Hz, 1H), 3.89 (s, 3H), 3.84 (s, 3H), 3.78 (s, 3H), 3.70 (s, 2H), 2.92 (s, 6H), 2.82 (m; 2H), 2.73 (m, 2H), 2.64 (m, 2H), 2.60 (m, 2H); LC/MS (ESI+): 563.28 (M+H).

Example 1174

5-Chloro-N*4*-[2-methoxy-4-(2-methoxy-ethoxy)-phenyl]-N*2*-(8-methoxy-3-oxazol-2-ylmethyl-2,3,4,5-tetrahydro-1H-benzo[d]azepin-7-yl)-pyrimidine-2,4-diamine Following a procedure similar to 1170, 8-methoxy-3-oxazol-2-ylmethyl-2,3,4,5-tetrahydro-1H-benzo[d]azepin-7-ylamine, and (2,5-dichloro-pyrimidin-4-yl)-[2-methoxy-4-(2-methoxy-ethoxy)-phenyl]-amine were converted to 5-chloro-N*4*-[2-methoxy-4-(2-methoxy-ethoxy)-phenyl]-N*2*-(8-methoxy-3-oxazol-2-ylmethyl-2,3,4,5-tetrahydro-1H-benzo[d]azepin-7-yl)-pyrimidine-2,4-diamine (25 mg, 17%) as a tan solid. MP: 50-62° C.; $^1$H-NMR (CDCl$_3$) δ 8.24 (d, J=8.8 Hz, 1H), 8.08 (s, 1H), 8.01 (s, 1H), 7.62 (s, 1H), 7.52 (s, 1H), 7.62 (s, 1H), 7.52 (s, 1H), 7.43 (s, 1H), 7.05 (s, 1H), 6.62 (s, 2H), 6.47 (d, J=8.8 Hz, 2H), 4.13 (t, J=4.6 Hz, 2H), 3.89 (s, 3H), 3.88 (s, 2H), 3.85 (s, 3H), 3.79 (m, 2H), 3.47 (s, 3H), 2.89 (m, 2H), 2.84 (m, 2H), 2.73 (m, 2H); LC/MS (ESI+): 582.28 (M+H).

Example 1175

5-Chloro-N*4*-[2-methoxy-4-(2-methoxy-ethoxy)-phenyl]-N*2*-[8-methoxy-3-(1-methyl-1H-imidazol-2-ylmethyl)-2,3,4,5-tetrahydro-1H-benzo[d]azepin-7-yl]-pyrimidine-2,4-diamine Following a procedure similar to 1170, 8-methoxy-3-(1-methyl-1H-imidazol-2-ylmethyl)-2,3,4,5-tetrahydro-1H-benzo[d]azepin-7-ylamine, and (2,5-dichloro-pyrimidin-4-yl)-[2-methoxy-4-(2-methoxy-ethoxy)-phenyl]-amine were converted to 5-chloro-N*4*-[2-methoxy-4-(2-methoxy-ethoxy)-phenyl]-N*2*-[8-methoxy-3-(1-methyl-1H-imidazol-2-ylmethyl)-2,3,4,5-tetrahydro-1H-benzo[d]azepin-7-yl]-pyrimidine-2,4-diamine (47 mg, 32%) as a light yellow solid. MP: 53-65° C.; $^1$H-NMR (CDCl$_3$) δ): 8.23 (d, J=8.8 Hz, 1H), 8.07 (s, 1H), 8.02 (s, 1H), 7.51 (s, 1H), 7.44 (s, 1H), 6.94 (s, 1H), 6.88 (s, 1H), 6.61 (m, 2H), 6.47 (dd, J=8.8 Hz, 2.0 Hz, 1H), 4.11 (t, J=4.8 Hz, 2H), 3.88 (s, 3H), 3.85 (s, 3H), 3.78 (s, 3H), 3.77 (m, 2H), 3.70 (s, 2H), 3.46 (s, 3H), 2.79 (m, 4H), 2.64 (br s, 4H); LC/MS (ESI+): 594.27 (M+H).

Example 1176

4-[5-Chloro-2-(3-dimethylcarbamoylmethyl-8-methoxy-2,3,4,5-tetrahydro-1H-benzo[d]azepin-7-ylamino)-pyrimidin-4-ylamino]-3-methoxy-N-methyl-benzamide Following a procedure similar to Example 258c, 2-(7-amino-8-methoxy-1,2,4,5-tetrahydro-benzo[d]azepin-3-yl)-N,N-dimethyl-acetamide and 4-(2,5-Dichloro-pyrimidin-4-ylamino)-3-methoxy-N-methyl-benzamide, which was prepared in a manner similar to 1146a,b, were converted to 4-[5-chloro-2-(3-dimethylcarbamoylmethyl-8-methoxy-2,3,4,5-tetrahydro-1H-benzo[d]azepin-7-ylamino)-pyrimidin-4-ylamino]-3-methoxy-N-methyl-benzamide (104 mg, 51%) as a white solid. MP: 138-147° C.; $^1$H-NMR (CDCl$_3$) δ 8.54 (d, J=8.4 Hz, 1H), 8.09 (s, 1H), 8.05 (s, 1H), 8.02 (s, 1H), 7.58 (s, 1H), 7.43 (s, 1H), 7.22 (d, J=8.4 Hz, 1H), 6.66 (s, 1H), 6.53 (br s, 1H), 4.01 (s, 3H), 3.87 (s, 3H), 3.35 (s, 2H), 3.13 (s, 3H), 3.04 (d, J=4.0 Hz, 3H), 2.97 (s, 3H), 2.91 (m, 2H), 2.85 (m, 2H), 2.80 (m, 2H), 2.76 (m, 2H); LC/MS (ESI+): 568.63 (M+H).

Example 1177

4-{5-Chloro-2-[8-methoxy-3-(2-methoxy-1-methoxymethyl-ethyl)-2,3,4,5-tetrahydro-1H-benzo[d]azepin-7-ylamino]-pyrimidin-4-ylamino}-3-methoxy-N-methyl-benzamide Following a procedure similar to Example 258c, 8-methoxy-3-(2-methoxy-1-methoxymethyl-ethyl)-2,3,4,5-tetrahydro-1H-benzo[d]azepin-7-ylamine and 4-(2,5-dichloro-pyrimidin-4-ylamino)-3-methoxy-N-methyl-benzamide were converted to 4-{5-chloro-2-[8-methoxy-3-(2-methoxy-1-methoxymethyl-ethyl)-2,3,4,5-tetrahydro-1H-benzo[d]azepin-7-ylamino]-pyrimidin-4-ylamino}-3-methoxy-N-methyl-benzamide (98 mg, 70%) as an off-white solid. MP: 85-97° C.; $^1$H-NMR (CDCl$_3$) δ 8.58 (d, J=8.5 Hz, 1H), 8.09 (s, 1H), 8.05 (s, 1H), 8.03 (s, 1H), 7.64 (s, 1H), 7.42 (s, 1H), 7.18 (d, J=8.0 Hz, 1H), 6.67 (s, 1H), 6.57 (br s, 1H), 4.02 (s, 3H), 3.87 (s, 3H), 3.59 (m, 2H), 3.51 (m, 2H), 3.32 (s, 6H), 3.04 (m, 1H), 3.01 (d, J=4.8 Hz, 3H), 2.94 (m, 2H), 2.86 (m, 2H), 2.77 (m, 4H); LC/MS (ESI+): 585.27 (M+H).

Example 1178

5-Chloro-N*2*-[3-(2-methanesulfonyl-ethyl)-8-methoxy-2,3,4,5-tetrahydro-1H-benzo[d]azepin-7-yl]-N*4*-[2-(pyrrolidine-1-sulfonyl)-phenyl]-pyrimidine-2,4-diamine Following a procedure similar to Example 258c, 3-(2-methanesulfonyl-ethyl)-8-methoxy-2,3,4,5-tetrahydro-1H-benzo[d]azepin-7-ylamine and (2,5-dichloro-pyrimidin-4-yl)-[2-(pyrrolidine-1-sulfonyl)-phenyl]-amine, which was prepared in a manner similar to 1141a-c, were converted to 5-chloro-N*2*-[3-(2-methanesulfonyl-ethyl)-8-methoxy-2,3,4,5-tetrahydro-1H-benzo[d]azepin-7-yl]-N*4*-[2-(pyrrolidine-1-sulfonyl)-phenyl]-pyrimidine-2,4-diamine (58 mg, 45%) as a light yellow solid. MP: 85-93° C.; ¹H-NMR (CDCl₃) δ 9.43 (s, 1H), 8.53 (d, J=8.4 Hz, 1H), 8.15 (s, 1H), 8.03 (s, 1H), 7.94 (d, J=8.1 Hz, 1H), 7.54 (t, J=8.0 Hz, 1H), 7.50 (s, 1H), 7.23 (t, J=8.0 Hz, 1H), 6.65 (s, 1H), 3.86 (s, 3H), 3.27 (m, 4H), 3.17 (m, 2H), 3.08 (s, 3H), 3.04 (m, 2H), 2.85 (m, 2H), 2.69 (m, 6H), 1.79 (m, 4H); LC/MS (ESI+): 635.24 (M+H).

Example 1179

(1S,2S,3R,4R)-3-[5-Chloro-2-(8-methoxy-3-oxazol-2-ylmethyl-2,3,4,5-tetrahydro-1H-benzo[d]azepin-7-ylamino)-pyrimidin-4-ylamino]-bicyclo[2.2.1]hept-5-ene-2-carboxylic acid amide Following a procedure similar to Example 258c, 8-methoxy-3-oxazol-2-ylmethyl-2,3,4,5-tetrahydro-1H-benzo[d]azepin-7-ylamine and (1S,2S,3R,4R)-3-(2,5-dichloro-pyrimidin-4-ylamino)-bicyclo[2.2.1]hept-5-ene-2-carboxylic acid amide were converted to (1S,2S,3R,4R)-3-[5-chloro-2-(8-methoxy-3-oxazol-2-ylmethyl-2,3,4,5-tetrahydro-1H-benzo[d]azepin-7-ylamino)-pyrimidin-4-ylamino]-bicyclo[2.2.1]hept-5-ene-2-carboxylic acid amide (39 mg, 30%) as a tan solid. MP: 110-119° C.; ¹H-NMR (CDCl₃) δ 8.17 (s, 1H), 7.87 (s, 1H), 7.62 (s, 1H), 7.38 (s, 1H), 7.06 (s, 1H), 6.62 (s, 1H), 6.57 (d, J=8.4 Hz, 1H), 6.29 (s, 2H), 5.63 (br s, 1H), 5.42 (br s, 1H), 4.43 (t, J=8.4 Hz, 1H), 3.88 (s, 2H), 3.85 (s, 3H), 3.06 (br s, 1H), 2.89 (m, 4H), 2.74 (m, 4H), 2.50 (d, J=8.0 Hz, 1H), 2.25 (d, J=8.8 Hz, 1H), 1.73 (br s, 1H), 1.64 (d, J=8.8 Hz, 1H); LC/MS (ESI+): 536.24 (M+H).

Example 1180

5-Chloro-N*4*-(2-methoxy-4-morpholin-4-yl-phenyl)-N*2*-(8-methoxy-3-oxazol-2-ylmethyl-2,3,4,5-tetrahydro-1H-benzo[d]azepin-7-yl)-pyrimidine-2,4-diamine Following a procedure similar to Example 258c, 8-methoxy-3-oxazol-2-ylmethyl-2,3,4,5-tetrahydro-1H-benzo[d]azepin-7-ylamine and (2,5-dichloro-pyrimidin-4-yl)-(2-methoxy-4-morpholin-4-yl-phenyl)-amine were converted to 5-chloro-N*4*-(2-methoxy-4-morpholin-4-yl-phenyl)-N*2*-(8-methoxy-3-oxazol-2-ylmethyl-2,3,4,5-tetrahydro-1H-benzo[d]azepin-7-yl)-pyrimidine-2,4-diamine (38 mg, 30%) as an off-white solid. MP: 81-87° C.; ¹H-NMR (CDCl₃) δ 8.24 (d, J=8.8 Hz, 1H), 8.11 (s, 1H), 8.01 (s, 1H), 7.62 (s, 1H), 7.53 (s, 1H), 7.44 (s, 1H), 7.06 (s, 1H), 6.63 (s, 1H), 6.54 (s, 1H), 6.49 (d, J=8.8 Hz, 1H), 3.91 (s, 3H), 3.88 (m, 4H), 3.87 (s, 2H), 3.85 (s, 3H), 3.14 (m, 4H), 2.90 (m, 2H), 2.84 (m, 2H), 2.73 (m, 4H); LC/MS (ESI+): 592.27 (M+H).

Example 1181

2-(7-{5-Chloro-4-[2-(pyrrolidine-1-sulfonyl)-phenylamino]-pyrimidin-2-ylamino}-8-methoxy-1,2,4,5-tetrahydro-benzo[d]azepin-3-yl)-N,N-dimethyl-acetamide Following a procedure similar to Example 258c, 2-(7-amino-8-methoxy-1,2,4,5-tetrahydro-benzo[d]azepin-3-yl)-N,N-dimethyl-acetamide and (2,5-dichloro-pyrimidin-4-yl)-[2-(pyrrolidine-1-sulfonyl)-phenyl]-amine were converted to 2-(7-{5-chloro-4-[2-(pyrrolidine-1-sulfonyl)-phenylamino]-pyrimidin-2-ylamino}-8-methoxy-1,2,4,5-tetrahydro-benzo[d]azepin-3-yl)-N,N-dimethyl-acetamide (75 mg, 28%) as a light yellow solid. MP: 67-74° C.; ¹H-NMR (CDCl₃) δ 9.42 (s, 1H), 8.52 (d, J=8.4 Hz, 1H), 8.14 (s, 1H), 7.98 (s, 1H), 7.92 (d, J=8.0 Hz, 1H), 7.53 (m, 1H), 7.51 (s, 1H), 7.22 (m, 1H), 6.65 (s, 1H), 3.87 (s, 3H), 3.29 (s, 2H), 3.26 (m, 4H), 3.14 (s, 3H), 2.98 (s, 3H), 2.87 (m, 2H), 2.69 (m, 6H), 1.78 (m, 4H); LC/MS (ESI+): 614.58 (M+H).

Example 1182

4-[5-Chloro-2-(8-methoxy-3-oxazol-2-ylmethyl-2,3,4,5-tetrahydro-1H-benzo[d]azepin-7-ylamino)-pyrimidin-4-ylamino]-3-methoxy-N-methyl-benzamide Following a procedure similar to Example 258c, 8-methoxy-3-oxazol-2-ylmethyl-2,3,4,5-tetrahydro-1H-benzo[d]azepin-7-ylamine and 4-(2,5-dichloro-pyrimidin-4-ylamino)-3-methoxy-N-methyl-benzamide were converted to 4-[5-chloro-2-(8-methoxy-3-oxazol-2-ylmethyl-2,3,4,5-tetrahydro-1H-benzo[d]azepin-7-ylamino)-pyrimidin-4-ylamino]-3-methoxy-N-methyl-benzamide (42 mg, 34%) as a tan solid. MP: 85-96° C.; ¹H-NMR (CDCl₃) δ 8.51 (d, J=8.4 Hz, 1H), 8.08 (s, 1H), 8.07 (s, 1H), 8.02 (s, 1H), 7.67 (s, 1H), 7.62 (s, 1H), 7.44 (s, 1H), 7.25 (d, J=8.4 Hz, 1H), 7.13 (br s, 1H), 7.04 (s, 1H), 6.63 (s, 1H), 4.03 (s, 3H), 3.97 (s, 2H), 3.85 (s, 3H), 3.00 (d, J=4.4 Hz, 3H), 2.91 (br s, 2H), 2.84 (br s, 4H), 2.71 (m, 2H); LC/MS (ESI+): 564.37 (M+H).

Example 1183

2-{5-Chloro-2-[8-methoxy-3-(3-morpholin-4-yl-propyl)-2-oxo-2,3,4,5-tetrahydro-1H-benzo[d]azepin-7-ylamino]-pyrimidin-4-ylamino}-N,N-dimethyl-benzenesulfonamide Following a procedure similar to Example 258c, 7-amino-8-methoxy-3-(3-morpholin-4-yl-propyl)-1,3,4,5-tetrahydro-benzo[d]azepin-2-one and 2-(2,5-dichloro-pyrimidin-4-ylamino)-N,N-dimethyl-benzenesulfonamide were converted to 2-{5-chloro-2-[8-methoxy-3-(3-morpholin-4-yl-propyl)-2-oxo-2,3,4,5-tetrahydro-1H-benzo[d]azepin-7-ylamino]-pyrimidin-4-ylamino}-N,N-dimethyl-benzenesulfonamide as an off-white solid (66 mg, 57%). MP: 78-87° C.; ¹H-NMR (CDCl₃) δ 9.38 (s, 1H), 8.53 (d, J=8.4 Hz, 1H), 8.15 (s, 1H), 8.02 (s, 1H), 7.89 (d, J=8.0 Hz, 1H), 7.58 (m, 1H), 7.47 (s, 1H), 7.26 (m, 1H), 6.62 (s, 1H), 3.87 (s, 3H), 3.83 (s, 2H), 3.70 (m, 6H), 3.47 (m, 2H), 2.97 (m, 2H), 2.75 (s, 6H), 2.43 (br s, 4H), 2.36 (m, 2H), 1.78 (m, 2H); LC/MS (ESI+): 644.17 (M+H).

Example 1184

2-[7-(5-Chloro-4-{2-[(2-methoxy-ethyl)-methyl-sulfamoyl]-phenylamino}-pyrimidin-2-ylamino)-8-methoxy-1,2,4,5-tetrahydro-benzo[d]azepin-3-yl]-N,N-dimethyl-acetamide Following a procedure similar to Example 258c, 2-(7-amino-8-methoxy-1,2,4,5-tetrahydro-benzo[d]azepin-3-yl)-N,N-dimethyl-acetamide and 2-(2,5-dichloro-pyrimidin-4-ylamino)-N-(2-methoxy-ethyl)-N-methyl-benzenesulfonamide, which was prepared in a manner similar to 1141a-c, were converted to 2-[7-(5-chloro-4-{2-[(2-methoxy-ethyl)-methyl-sulfamoyl]-phenylamino}-pyrimidin-2-ylamino)-8-methoxy-1,2,4,5-tetrahydro-benzo[d]azepin-3-yl]-N,N-dimethyl-acetamide (40 mg, 22%) as an off-white solid. MP: 67-76° C.; ¹H-NMR (CDCl₃) δ 9.22 (s, 1H), 8.47 (d, J=8.8 Hz, 1H), 8.14 (s, 1H), 7.98 (s, 1H), 7.90 (d, J=8.0 Hz, 1H), 7.54 (t, J=8.4 Hz, 1H), 7.52 (s, 1H), 7.22 (t, J=8.4 Hz, 1H), 6.64 (s, 1H), 3.86 (s, 3H), 3.46 (m, 2H), 3.31 (m, 2H), 3.29 (s, 2H), 3.22 (s, 3H), 3.14 (s, 3H), 2.98 (s, 3H), 2.87 (overlapped* s, 3H), 2.87 (overlapped* m, 2H), 2.70 (m, 6H); LC/MS (ESI+): 632.23 (M+H).

Example 1185

2-[5-Chloro-2-(3-dimethylcarbamoylmethyl-8-methoxy-2,3,4,5-tetrahydro-1H-benzo[d]azepin-7-ylamino)-pyrimidin-4-ylamino]-5-dimethylamino-N-methyl-benzamide 1185a) 5-Fluoro-2-nitro-benzoic acid (5.00 g, 0.0270 mol) in methylene chloride (150 mL) was treated with oxalyl chloride (2.971 mL, 0.03511 mol), followed by N,N-dimethylformamide (40 uL, 0.0005 mol), and the reaction mixture was heated at 50° C. for 1 hour. The solvent was removed under reduced pressure, and the residue was azeotroped with benzene, then dissolved in tetrahydrofuran (50 mL) and treated with 2.000 M methylamine in tetrahydrofuran (20.26 mL) at room temperature, overnight. The reaction was stopped by addition of aqueous saturated sodium bicarbonate, then water, and the solid product was collected by filtration, washed with water and dried under vacuum. 5-Fluoro-N-methyl-2-nitro-benzamide (5.35 g, 99%): yellow solid. LC/MS (ESI+): 199.03 (M+H).

1185b) 5-Fluoro-N-methyl-2-nitro-benzamide (3.00 g, 15.1 mmol) in N,N-dimethylformamide (20 mL) was treated with dimethylamine hydrochloride (2.47 g, 30.3 mmol) in presence of potassium carbonate (6.28 g, 45.4 mmol) at room temperature. The reaction was quenched with water. The crude product was collected by filtration, washed, dried, and used without further purification. 5-Dimethylamino-N-methyl-2-nitro-benzamide (3.38 g, 82%): yellow solid.

1185c) Following a sequence of reactions analogous to 263b and 1136a 5-dimethylamino-N-methyl-2-nitro-benzamide was converted to 2-(2,5-dichloro-pyrimidin-4-ylamino)-5-dimethylamino-N-methyl-benzamide (4.3 g, quantitative) as a brown solid. LC/MS (ESI+): 340.39 (M+H).

1185d) Following a procedure similar to Example 258c, 2-(7-amino-8-methoxy-1,2,4,5-tetrahydro-benzo[d]azepin-3-yl)-N,N-dimethyl-acetamide and 2-(2,5-dichloro-pyrimidin-4-ylamino)-5-dimethylamino-N-methyl-benzamide were converted to 2-[5-chloro-2-(3-dimethylcarbamoylmethyl-8-methoxy-2,3,4,5-tetrahydro-1H-benzo[d]azepin-7-ylamino)-pyrimidin-4-ylamino]-5-dimethylamino-N-methyl-benzamide (83 mg, 50%) as a yellow solid. MP: 96-110° C.; $^1$H-NMR (CDCl$_3$) δ 9.99 (s, 1H), 8.29 (d, J=8.8 Hz, 1H), 8.07 (s, 1H), 8.02 (s, 1H), 7.46 (s, 1H), 6.85 (m, 1H), 6.77 (s, 1H), 6.62 (s, 1H), 6.21 (br s, 1H), 3.85 (s, 3H), 3.27 (s, 2H), 3.13 (s, 3H), 3.00 (d, J=4.8 Hz, 3H), 2.97 (s, 9H), 2.86 (m, 2H), 2.76 (m, 2H), 2.69 (m, 2H), 2.65 (m, 2H); LC/MS (ESI+): 581.25 (M+H).

Example 1186

2-{7-[5-Chloro-4-(2-oxo-1,2-dihydro-pyridin-3-ylamino)-pyrimidin-2-ylamino]-8-methoxy-1,2,4,5-tetrahydro-benzo[d]azepin-3-yl}-N,N-dimethyl-acetamide 1186a) To a suspension of 2-methoxy-pyridin-3-ylamine (1.00 g, 0.00806 mol) and N,N-diisopropylethylamine (2.1 mL, 0.012 mol) in isopropyl alcohol (20 mL) was added 2,4,5-trichloropyrimidine (1.0 mL, 0.0089 mol). The mixture was stirred at room temperature overnight. The suspension was filtered, the solid was washed with isopropanol (10 mL) then hexane (20 mL). The solids were dried under vacuum to provide (2,5-dichloro-pyrimidin-4-yl)-(2-methoxy-pyridin-3-yl)-amine (1.23 g, 56%) as a white solid. LC/MS (ESI+): 271.40 (M+H).

1186b) Following a procedure similar to Example 258c, 2-(7-amino-8-methoxy-1,2,4,5-tetrahydro-benzo[d]azepin-3-yl)-N,N-dimethyl-acetamide and (2,5-dichloro-pyrimidin-4-yl)-(2-methoxy-pyridin-3-yl)-amine were converted to 2-{7-[5-chloro-4-(2-oxo-1,2-dihydro-pyridin-3-ylamino)-pyrimidin-2-ylamino]-8-methoxy-1,2,4,5-tetrahydro-benzo[d]azepin-3-yl}-N,N-dimethyl-acetamide (77 mg, 54%) as a white solid. MP: 256-250° C.; $^1$H-NMR (CDCl$_3$) δ 12.23 (br s, 1H), 8.63, (d, J=7.2 Hz, 1H), 8.49 (s, 1H), 8.11 (s, 1H), 7.99 (s, 1H), 7.39 (s, 1H), 7.09 (d, J=6.4 Hz, 1H), 6.66 (s, 1H), 6.32 (t, J=6.8 Hz, 1H), 3.88 (s, 3H), 3.30 (s, 2H), 3.14 (s, 3H), 2.98 (s, 3H), 2.91 (m, 4H), 2.74 (m, 4H); LC/MS (ESI+): 498.17 (M+H).

Example 1187

2-(7-{5-Chloro-4-[4-dimethylamino-2-(propane-2-sulfonyl)-phenylamino]-pyrimidin-2-ylamino}-8-methoxy-1,2,4,5-tetrahydro-benzo[d]azepin-3-yl)-N,N-dimethyl-acetamide 1187a) Into a 1-neck round-bottom flask 2,4-difluoro-1-nitro-benzene (10.00 g, 62.86 mmol) is dissolved in ethanol (200 mL) and collected at 0° C. A precooled solution of sodium 2-propanethiolate (6.169 g, 62.86 mmol) in ethanol (50 mL) is added dropwise at 0° C. and the reaction is stirred at the same temperature for 1 h. The reaction mixture is concentrated, and the sodium fluoride is filtered, and washed with dichloromethane. The filtrate is taken in dichloromethane, washed with water, then the organic solution is dried over magnesium sulfate, and concentrated under vacuum to give a mixture of products, as a yellow oil (13.53 g, 93%). Major product: 4-fluoro-2-isopropylsulfanyl-1-nitro-benzene. The unseparable mixture was used in the next step.

1187b) Into a 1-neck round-bottom flask the mixture of products obtained as above (4.00 g, 0.0186 mol) in chloroform (50 mL, 0.6 mol) was treated with m-CPBA 70-75% (13.7 g) at 0° C., and the reaction was stirred at this temperature for 2 h. The reaction was quenched by addition of a dilute solution of sodium thiosulfate and sodium bicarbonate (~1:1), then extracted with chloroform (3×200 mL). The combined organics were washed with a dilute aqueous sodium bicarbonate solution, then with water and finally with brine, then dried on magnesium sulfate and concentrated, when the major regioisomeric product crystallized. Recrystallyzation from EtOAc/hexanes provided 4-fluoro-1-nitro-2-(propane-2-sulfonyl)-benzene as a yellow solid (4.6 g, 34%).

1187c) 4-Fluoro-1-nitro-2-(propane-2-sulfonyl)-benzene (2.10 g, 8.49 mmol) in N,N-dimethylformamide (20 mL) was treated with dimethylamine hydrochloride (1.38 g, 17.0 mmol) in presence of potassium carbonate (4.11 g, 29.7 mmol) at room temperature overnight. The reaction was quenched with water. The crude product was collected by filtration, and washed with water, dried, and used without further purification. Dimethyl-[4-nitro-3-(propane-2-sulfonyl)-phenyl]-amine: yellow solid (2.3 g, 87%). LC/MS (ESI+): 273.17 (M+H).

1187d) Following a sequence of reactions similar to 1141b, c, dimethyl-[4-nitro-3-(propane-2-sulfonyl)-phenyl]-amine was converted to N*1*-(2,5-dichloro-pyrimidin-4-yl)-N*4*, N*4*-dimethyl-2-(propane-2-sulfonyl)-benzene-1,4-diamine as a red solid (2.7 g, 25%). LC/MS (ESI+): 389.12 (M+H).

1187e) Following a procedure similar to Example 258c, 2-(7-amino-8-methoxy-1,2,4,5-tetrahydro-benzo[d]azepin-3-yl)-N,N-dimethyl-acetamide and N*1*-(2,5-dichloro-pyrimidin-4-yl)-N*4*,N*4*-dimethyl-2-(propane-2-sulfonyl)-benzene-1,4-diamine were converted to 2-(7-{5-chloro-4-[4-dimethylamino-2-(propane-2-sulfonyl)-phenylamino]-pyrimidin-2-ylamino}-8-methoxy-1,2,4,5-tetrahydro-benzo[d]azepin-3-yl)-N,N-dimethyl-acetamide (41 mg, 22%) as a white solid. MP: 81-93° C.; $^1$H-NMR (CDCl$_3$) δ 8.72 (s, 1H), 8.10 (d, J=9.2 Hz, 1H), 8.07 (d, J=0.8 Hz, 1H), 7.99 (s, 1H), 7.49 (s, 1H), 7.20 (d, J=2.0 Hz, 1H), 6.94 (dd, J=8.8, 2.8 Hz, 1H), 6.62 (s, 1H), 3.86 (s, 3H), 3.27 (s, 2H) 3.21 (m, 1H), 3.13 (s, 3H), 3.02 (s, 6H), 2.97 (s, 3H), 2.87 (m, 2H), 2.67 (m, 4H), 2.62 (m, 2H), 1.28 (d, J=6.8 Hz, 6H); LC/MS (ESI+): 630.26 (M+H).

Example 1188

2-(7-{5-Chloro-4-[2-(3-hydroxy-pyrrolidine-1-sulfonyl)-phenylamino]-pyrimidin-2-ylamino}-8-methoxy-1,2,4,5-tetrahydro-benzo[d]azepin-3-yl)-N,N-dimethyl-acetamide 1188a) Following a procedure similar to 1141a, 2-nitro-benzenesulfonyl chloride and pyrrolidin-3-ol were converted to 1-(2-nitro-benzenesulfonyl)-pyrrolidin-3-ol as a waxy solid (12.3 g, quantitative).

1188b) 1-(2-Nitro-benzenesulfonyl)-pyrrolidin-3-ol (12.25 g, 0.04499 mol) in N,N-dimethylformamide (40 mL) was treated with tert-butyldimethylsilyl chloride (8.137 g, 0.05399 mol) and 1H-imidazole (4.594 g, 0.06748 mol) at room temperature for 3 h. The reaction mixture was partitioned between water and ethyl ether, and the layers were separated. The aqueous layer was extracted twice with ethyl ether, and then the organic extracts were washed extensively with water, then once with brine, dried (MgSO$_4$), filtered and concentrated to give 3-(tert-butyl-dimethyl-silanyloxy)-1-(2-nitro-benzenesulfonyl)-pyrrolidine as an off-white solid (17.4 g, 92%).

1188c) Following a sequence of reactions similar to 1141b, c, 3-(tert-butyl-dimethyl-silanyloxy)-1-(2-nitro-benzenesulfonyl)-pyrrolidine was converted to {2-[3-(tert-butyl-dimethyl-silanyloxy)-pyrrolidine-1-sulfonyl]-phenyl}-(2,5-dichloro-pyrimidin-4-yl)-amine as a white solid (9.9 g, 43%). LC/MS (ESI+): 503.09 (M+H).

1188d) Following a procedure similar to Example 258c, 2-(7-amino-8-methoxy-1,2,4,5-tetrahydro-benzo[d]azepin-3-yl)-N,N-dimethyl-acetamide and {2-[3-(tert-butyl-dimethyl-silanyloxy)-pyrrolidine-1-sulfonyl]-phenyl}-(2,5-dichloro-pyrimidin-4-yl)-amine were converted to 2-(7-{5-chloro-4-[2-(3-hydroxy-pyrrolidine-1-sulfonyl)-phenylamino]-pyrimidin-2-ylamino}-8-methoxy-1,2,4,5-tetrahydro-benzo[d]azepin-3-yl)-N,N-dimethyl-acetamide (69 mg, 30%) as a white solid. MP: 70-84° C.; $^1$H-NMR (CDCl$_3$) δ 9.30 (s, 1H), 8.44 (d, J=8.4 Hz, 1H), 8.14 (s, 1H), 7.96 (s, 1H), 7.94 (d, J=8.4 Hz, 1H), 7.55 (t, J=8.0 Hz, 1H), 7.51 (s, 1H), 7.23 (t, J=8.0 Hz, 1H), 6.64 (s, 1H), 4.34 (br s, 1H), 3.86 (s, 3H), 3.39 (m, 3H), 3.29 (s, 2H), 3.27 (m, 1H), 3.13 (s, 3H), 2.98 (s, 3H), 2.86 (m, 2H), 2.69 (m, 4H), 2.65 (m, 2H), 1.85 (m, 3H); LC/MS (ESI+): 630.23 (M+H).

Example 1189

2-(7-{5-Chloro-4-[4-(2-methoxy-ethoxy)-2-(propane-2-sulfonyl)-phenylamino]-pyrimidin-2-ylamino}-8-methoxy-1,2,4,5-tetrahydro-benzo[d]azepin-3-yl)-N,N-dimethyl-acetamide Following a procedure similar to Example 258c, 2-(7-amino-8-methoxy-1,2,4,5-tetrahydro-benzo[d]azepin-3-yl)-N,N-dimethyl-acetamide and (2,5-dichloro-pyrimidin-4-yl)-[4-(2-methoxy-ethoxy)-2-(propane-2-sulfonyl)-phenyl]-amine, which was prepared in a manner analogous to 1187a-d, were converted to 2-(7-{5-chloro-4-[4-(2-methoxy-ethoxy)-2-(propane-2-sulfonyl)-phenylamino]-pyrimidin-2-ylamino}-8-methoxy-1,2,4,5-tetrahydro-benzo[d]azepin-3-yl)-N,N-dimethyl-acetamide (49 mg, 26%) as an off-white solid. MP: 65-75° C.; $^1$H-NMR (CDCl$_3$) δ 9.05 (s, 1H), 8.33 (d, J=8.8 Hz, 1H), 8.11 (s, 1H), 7.96 (s, 1H), 7.47 (s, 2H), 7.20 (d, J=8.8 Hz, 1H), 6.64 (s, 1H), 4.28 (t, J=4.0 Hz, 2H), 3.86 (s, 3H), 3.79 (m, 2H), 3.47 (s, 3H), 3.28 (s, 2H), 3.23 (m, 1H), 3.14 (s, 3H), 2.98 (s, 3H), 2.85 (m, 2H), 2.70 (m, 6H), 1.29 (d, J=6.8 Hz, 6H); LC/MS (ESI+): 661.27 (M+H).

Example 1190

2-{7-[5-Chloro-4-(2-methoxy-pyridin-3-ylamino)-pyrimidin-2-ylamino]-8-methoxy-1,2,4,5-tetrahydro-benzo[d]azepin-3-yl}-N,N-dimethyl-acetamide 2-(7-Amino-8-methoxy-1,2,4,5-tetrahydro-benzo[d]azepin-3-yl)-N,N-dimethyl-acetamide (80.00 mg, 0.2884 mmol), (2,5-dichloro-pyrimidin-4-yl)-(2-methoxy-pyridin-3-yl)-amine (86.01 mg, 0.3173 mmol), and N,N-diisopropylethylamine (57.78 uL, 0.3317 mmol) were combined in 1-butanol (3 mL). The reaction was heated at 135° C. for 7 days. The reaction mixture was cooled, then partition between dilute NaHCO$_3$ and dichloromethane, and the layers were separated. The aqueous mixture was extracted twice with dichloromethane, and the combined organics were dried (MgSO$_4$) and concentrated. The product was isolated by reverse phase preparative HPLC, and neutralization of the TFA salt to give 2-{7-[5-chloro-4-(2-methoxy-pyridin-3-ylamino)-pyrimidin-2-ylamino]-8-methoxy-1,2,4,5-tetrahydro-benzo[d]azepin-3-yl}-N,N-dimethyl-acetamide as a white solid (39 g, 26%). MP: 68-76° C.; $^1$H-NMR (CDCl$_3$) δ 8.71 (d, J=8.0 Hz, 1H), 8.09 (s, 1H), 7.99 (s, 1H), 7.86 (dd, J=4.8, 1.6 Hz, 1H), 7.71 (s, 1H), 7.42 (s, 1H), 6.88 (dd, J=7.6, 4.8 Hz, 1H), 6.66 (s, 1H), 4.08 (s, 3H), 3.87 (s, 3H), 3.29 (s, 2H), 3.15 (s, 3H), 2.98 (s, 3H), 2.89 (m, 4H), 2.71 (br s, 4H); LC/MS (ESI+): 512.22 (M+H).

Example 1191

5-Chloro-N*2*-(8-methoxy-3-oxazol-2-ylmethyl-2,3,4,5-tetrahydro-1H-benzo[d]azepin-7-yl)-N*4*-[2-(pyrrolidine-1-sulfonyl)-phenyl]-pyrimidine-2,4-diamine Following a procedure similar to Example 258c, 8-methoxy-3-oxazol-2-ylmethyl-2,3,4,5-tetrahydro-1H-benzo[d]azepin-7-ylamine and (2,5-dichloro-pyrimidin-4-yl)-[2-(pyrrolidine-1-sulfonyl)-phenyl]-amine were converted to 5-chloro-N*2*-(8-methoxy-3-oxazol-2-ylmethyl-2,3,4,5-tetrahydro-1H-benzo[d]azepin-7-yl)-N*4*-[2-(pyrrolidine-1-sulfonyl)-phenyl]-pyrimidine-2,4-diamine (37 mg, 24%) as a light yellow solid. MP: 73-82° C.; $^1$H-NMR (CDCl$_3$) δ 9.41 (s, 1H), 8.50 (d, J=8.2 Hz, 1H), 8.13 (s, 1H), 7.98 (s, 1H), 7.93 (d, J=8.0 Hz, 1H), 7.63 (m, 1H), 7.47 (s, 1H), 7.21 (m, 1H), 7.07 (s, 1H), 6.64 (s, 1H), 3.88 (s, 2H), 3.86 (s, 3H), 3.26 (m, 4H), 2.89 (m, 2H), 2.75 (m, 6H), 1.78 (m, 4H); LC/MS (ESI+): 610.14 (M+H).

Example 1192

2-{5-Chloro-2-[8-methoxy-3-(2-morpholin-4-yl-acetyl)-2,3,4,5-tetrahydro-1H-benzo[d]azepin-7-ylamino]-pyrimidin-4-ylamino}-N,N-dimethyl-benzenesulfonamide 1192a) Into a round bottom flask was added methylene chloride (5 mL), followed by 7-methoxy-8-nitro-2,3,4,5-tetrahydro-1H-benzo[d]azepine (600 mg, 0.003 mol), morpholin-4-yl-acetic acid (0.4311 g, 0.00297 mol), and bromotris (pyrrolydino)phosphonium hexafluorophosphate (1322 mg, 0.002835 mol), and the reaction was cooled at 0° C. N,N-Diisopropylethylamine (1.881 mL, 0.01080 mol) was added and the ice bath was allowed to warm to room temperature, and the reaction was stirred overnight. The reaction mixture was quenched with dilute sodium bicarbonate aqueous solution and extracted with ethyl acetate. The combined extracts were dried (MgSO$_4$), and concentrated, and the product isolated by flash chromatography (SiO$_2$, ethyl acetate/hexanes). 1-(7-methoxy-8-nitro-1,2,4,5-tetrahydro-benzo[d]azepin-3-yl)-2-morpholin-4-yl-ethanone: yellow solid (0.81 g, 82%). LC/MS (ESI+): 350.25 (M+H).

1192b) Following a procedure similar to 258b, 1-(7-methoxy-8-nitro-1,2,4,5-tetrahydro-benzo[d]azepin-3-yl)-2-morpholin-4-yl-ethanone was converted to 1-(7-amino-8-methoxy-1,2,4,5-tetrahydro-benzo[d]azepin-3-yl)-2-morpholin-4-yl-ethanone as a white foam (0.74 g, 81%). LC/MS (ESI+): 320.21 (M+H).

1192c) Following a procedure similar to Example 258c, 1-(7-amino-8-methoxy-1,2,4,5-tetrahydro-benzo[d]azepin-3-yl)-2-morpholin-4-yl-ethanone and 2-(2,5-dichloro-pyrimidin-4-ylamino)-N,N-dimethyl-benzenesulfonamide were converted to 2-{5-chloro-2-[8-methoxy-3-(2-morpholin-4-yl-acetyl)-2,3,4,5-tetrahydro-1H-benzo[d]azepin-7-ylamino]-pyrimidin-4-ylamino}-N,N-dimethyl-benzenesulfonamide as a white solid (38 mg, 14%). MP: 84-95° C.; $^1$H-NMR (CDCl$_3$, mixture of amide rotamers observed, minor rotamer denoted with "*") δ 9.41* (br s, 1H), 9.35 (br s, 1H), 8.59* (d, J=8.0 Hz, 1H), 8.49 (d, J=8.4 Hz, 1H), 8.15 (s, 1H), 8.09* (s, 1H), 8.07 (s, 1H), 7.89 (d, J=8.0 Hz, 1H), 7.57 (m, 2H), 7.47* (br s, 1H), 7.27 (m, 1H), 6.69 (s, 1H), 6.67* (s, 1H), 3.89 (s, 3H), 3.70 (m, 8H), 3.27 (br s, 2H), 2.93 (m, 1H), 2.85 (m, 2H), 2.76* (6H), 2.75 (s, 6H), 2.69 (m, 1H), 2.56 (br s, 4H); LC/MS (ESI+): 630.21 (M+H).

Example 1193

7-{5-Chloro-4-[2-(3-hydroxy-pyrrolidine-1-sulfonyl)-phenylamino]-pyrimidin-2-ylamino}-8-methoxy-1,3,4,5-tetrahydro-benzo[d]azepin-2-one Following a procedure similar to Example 258c, 7-amino-8-methoxy-1,3,4,5-tetrahydro-benzo[d]azepin-2-one and {2-[3-(tert-butyl-dimethyl-silanyloxy)-pyrrolidine-1-sulfonyl]-phenyl}-(2,5-dichloro-pyrimidin-4-yl)-amine were converted to 7-{5-chloro-4-[2-(3-hydroxy-pyrrolidine-1-sulfonyl)-phenylamino]-pyrimidin-2-ylamino}-8-methoxy-1,3,4,5-tetrahydro-benzo[d]azepin-2-one as a brown solid (47 mg, 17%). MP: 86-97° C.; 1H-NMR (CDCl$_3$) δ 9.33 (s, 1H), 8.42 (d, J=8.0 Hz, 1H), 8.14 (s, 1H), 8.01 (s, 1H), 7.93 (d, J=8.0 Hz, 1H), 7.55 (t, J=8.0 Hz, 1H), 7.52 (s, 1H), 7.22 (t, J=7.8 Hz, 1H), 6.63 (s, 1H), 6.26 (br s, 1H), 4.34 (br s, 1H), 3.86 (s, 3H), 3.77 (s, 2H), 3.52 (m, 2H), 3.40 (m, 3H), 3.27 (d, J=11.2 Hz, 1H), 2.89 (m, 2H), 2.70 (br s, 1H); 1.92 (m, 1H), 1.83 (m, 1H); LC/MS (ESI+): 559.23 (M+H).

Example 1194

2-[5-Chloro-2-(8-methoxy-2-oxo-2,3,4,5-tetrahydro-1H-benzo[d]azepin-7-ylamino)-pyrimidin-4-ylamino]-N,N-dimethyl-benzenesulfonamide Following a procedure similar to Example 258c, 7-amino-8-methoxy-1,3,4,5-tetrahydro-benzo[d]azepin-2-one and 2-(2,5-dichloro-pyrimidin-4-ylamino)-N,N-dimethyl-benzenesulfonamide were converted to 2-[5-chloro-2-(8-methoxy-2-oxo-2,3,4,5-tetrahydro-1H-benzo[d]azepin-7-ylamino)-pyrimidin-4-ylamino]-N,N-dimethyl-benzenesulfonamide as a white solid (16 mg, 6%). MP: 190-195° C.; $^1$H-NMR (CDCl$_3$) δ 9.34 (s, 1H), 8.50 (d, J=8.4 Hz, 1H), 8.15 (s, 1H), 8.06 (s, 1H), 7.89 (d, J=8.0 Hz, 1H), 7.56 (t, J=8.0 Hz, 1H), 7.50 (s, 1H), 7.24 (t, J=7.8 Hz, 1H), 6.65 (s, 1H), 5.79 (br s, 1H), 3.88 (s, 3H), 3.79 (s, 2H), 3.55 (m, 2H), 2.95 (m, 2H), 2.74 (s, 6H); LC/MS (ESI+): 517.19 (M+H).

Example 1195

2-{5-Chloro-2-[8-methoxy-3-(2-morpholin-4-yl-ethyl)-2-oxo-2,3,4,5-tetrahydro-1H-benzo[d]azepin-7-ylamino]-pyrimidin-4-ylamino}-N,N-dimethyl-benzenesulfonamide Following a procedure similar to Example 258c, 7-amino-8-methoxy-3-(2-morpholin-4-yl-ethyl)-1,3,4,5-tetrahydro-benzo[d]azepin-2-one, prepared in a manner similar to 251a-d, and 2-(2,5-dichloro-pyrimidin-4-ylamino)-N,N-dimethyl-benzenesulfonamide were converted to 2-{5-chloro-2-[8-methoxy-3-(2-morpholin-4-yl-ethyl)-2-oxo-2,3,4,5-tetrahydro-1H-benzo[d]azepin-7-ylamino]-pyrimidin-4-ylamino}-N,N-dimethyl-benzenesulfonamide as a white solid (58 mg, 20%). MP: 75-91° C.; $^1$H-NMR (CDCl$_3$) δ 9.38 (s, 1H), 8.53 (d, J=8.0 Hz, 1H), 8.15 (s, 1H), 8.02 (s, 1H), 7.88 (d, J=8.0 Hz, 1H), 7.58 (t, J=7.8 Hz, 1H), 7.47 (s, 1H), 7.23 (m, 1H), 6.62 (s, 1H), 3.87 (s, 3H), 3.83 (s, 2H), 3.74 (m, 4H), 3.67 (m, 2H), 3.56 (m, 2H), 3.01 (t, J=4.8 Hz, 2H), 2.75 (s, 6H), 2.52 (m, 2H), 2.48 (m, 4H); LC/MS (ESI+): 630.22 (M+H).

Example 1196

1-{5-Chloro-2-[8-methoxy-3-(2-methoxy-ethyl)-2,3,4,5-tetrahydro-1H-benzo[d]azepin-7-ylamino]-pyrimidin-4-ylamino}-cyclopropanecarboxylic acid methylamide 1196a) A solution of 1-tert-butoxycarbonylamino-cyclopropanecarboxylic acid (1.00 g, 4.97 mmol in tetrahydrofuran (15 mL, 180 mmol) was treated with N,N-carbonyldiimidazole (1.61 g, 9.94 mmol) for 1 hour at room temperature, and then the reaction mixture was treated with 2.000 M methylamine in tetrahydrofuran (7.45 mL) dropwise, and was stirred overnight. The reaction mixture was partitioned between dilute NaHCO$_3$ and dichloromethane, and then the aqueous layer was extracted twice with dichloromethane. The combined organic extracts were washed with water, then dried (MgSO$_4$), and concentrated to generate the product, which was used without further purification: (1-methylcarbamoyl-cyclopropyl)-carbamic acid tert-butyl ester: white waxy solid (1.1 g, 94%). LC/MS (ESI+): 237.03 (M+H).

1196b) (1-Methylcarbamoyl-cyclopropyl)-carbamic acid tert-butyl ester (1.00 g, 4.67 mmol) was treated at 0° C. with trifluoroacetic acid (1.80 mL, 23.3 mmol) in methylene chloride (15.00 mL), and then allowed to warm to room temperature for 1 h. The reaction mixture was concentrated under reduced pressure, and the crude TFA salt of 1-amino-cyclopropanecarboxylic acid methylamide (oil, 1.00 g, 93%) was azeotroped once with benzene, and used in the next step.

1196c) Following a procedure similar to 1186a, 1-aminocyclopropanecarboxylic acid methylamide was converted to 1-(2,5-dichloro-pyrimidin-4-ylamino)-cyclopropane carboxylic acid methylamide as a tan solid (0.44 g, 38%). LC/MS (ESI+): 260.95 (M+H).

1196d) Following a procedure similar to Example 258c, 8-methoxy-3-(2-methoxy-ethyl)-2,3,4,5-tetrahydro-1H-benzo[d]azepin-7-ylamine and 1-(2,5-dichloro-pyrimidin-4-ylamino)-cyclopropane carboxylic acid methylamide were converted to 1-{5-chloro-2-[8-methoxy-3-(2-methoxy-ethyl)-2,3,4,5-tetrahydro-1H-benzo[d]azepin-7-ylamino]-pyrimidin-4-ylamino}-cyclopropane carboxylic acid methylamide as a white solid (58 mg, 20%). MP: 211-215° C.; $^1$H-NMR (CDCl$_3$) δ 8.22 (s, 1H), 7.98 (s, 1H), 7.62 (br s, 1H), 6.63 (s, 1H), 6.39 (br s, 1H), 5.61 (s, 1H), 3.86 (s, 3H), 3.54 (m, 2H), 3.36 (s, 1H), 2.91 (m, 4H), 2.78 (d, J=4.8 Hz, 3H), 2.72 (m, 6H), 1.77 (m, 2H), 1.09 (m, 2H); LC/MS (ESI+): 475.20 (M+H).

Example 1197

1-{5-Chloro-2-[8-methoxy-3-(2-methoxy-ethyl)-2,3,4,5-tetrahydro-1H-benzo[d]azepin-7-ylamino]-pyrimidin-4-ylamino}-cyclopropanecarboxylic acid cyanomethyl-amide Following a sequence of reactions analogous to 1196a-d, 1-{5-chloro-2-[8-methoxy-3-(2-methoxy-ethyl)-2,3,4,5-tetrahydro-1H-benzo[d]azepin-7-ylamino]-pyrimidin-4-ylamino}-cyclopropanecarboxylic acid cyanomethyl-amide was prepared as a white solid (86 mg, 46%). MP: 187-189° C.; $^1$H-NMR (CDCl$_3$) 8.08 (s, 1H), 8.00 (s, 1H), 7.60 (br s, 1H), 6.84 (br s, 1H), 6.63 (s, 1H), 5.63 (s, 1H), 4.11 (d, J=6.0 Hz, 2H), 3.86 (s, 3H), 3.54 (t, J=4.8 Hz, 2H), 3.37 (s, 3H), 2.87 (m, 4H), 2.75 (m, 6H), 1.82 (m, 2H), 1.20 (m, 2H); LC/MS (ESI+): 500.23 (M+H).

Example 1198

1-[5-Chloro-2-(3-dimethylcarbamoylmethyl-8-methoxy-2,3,4,5-tetrahydro-1H-benzo[d]azepin-7-ylamino)-pyrimidin-4-ylamino]-cyclopropanecarboxylic acid methylamide Following a procedure similar to Example 258c, 2-(7-amino-8-methoxy-1,2,4,5-tetrahydro-benzo[d]azepin-3-yl)-N,N-dimethyl-acetamide and 1-(2,5-dichloro-pyrimidin-4-ylamino)-cyclopropane carboxylic acid methylamide were converted to 1-{5-chloro-2-[8-methoxy-3-(2-methoxy-ethyl)-2,3,4,5-tetrahydro-1H-benzo[d]azepin-7-ylamino]-pyrimidin-4-ylamino}-cyclopropane carboxylic acid methylamide as a white solid (28 mg, 19%). MP: 118-125° C.; $^1$H-NMR (CDCl$_3$) 8.21 (s, 1H), 7.97 (s, 1H), 7.63 (br s, 1H), 6.63 (s, 1H), 6.38 (br s, 1H), 5.62 (s, 1H), 3.87 (s, 3H), 3.27 (s, 2H), 3.16 (s, 3H), 2.97 (s, 3H), 2.91 (m, 2H), 2.85 (m, 2H), 2.78 (d, J=4.8 Hz, 3H), 2.69 (m, 4H), 1.75 (m, 2H), 1.09 (br s, 2H); LC/MS (ESI+): 502.30 (M+H).

Example 1199

1-[5-Chloro-2-(3-dimethylcarbamoylmethyl-8-methoxy-2,3,4,5-tetrahydro-1H-benzo[d]azepin-7-ylamino)-pyrimidin-4-ylamino]-cyclopropanecarboxylic acid cyanomethyl-amide Following a sequence of reactions analogous to 1196a-d, 1-[5-chloro-2-(3-dimethylcarbamoylmethyl-8-methoxy-2,3,4,5-tetrahydro-1H-benzo[d]azepin-7-ylamino)-pyrimidin-4-ylamino]-cyclopropanecarboxylic acid cyanomethyl-amide was prepared as a white solid (86 mg, 46%). MP: 120-128° C.; $^1$H-NMR (CDCl$_3$) $^1$H-NMR (CDCl$_3$) 8.09 (s, 1H), 7.98 (s, 1H), 7.60 (br s, 1H), 7.01 (br s, 1H), 6.62 (s, 1H), 5.72 (s, 1H), 4.10 (d, J=4.6 Hz, 2H), 3.85 (s, 3H), 3.27 (s, 2H), 3.15 (s, 3H), 2.96 (s, 3H), 2.87 (m, 4H), 2.68 (m, 4H), 1.80 (m, 2H), 1.19 (m, 2H); LC/MS (ESI+): 527.28 (M+H).

Example 1200

2-{7-[5-Chloro-4-(2,6-dimethoxy-pyridin-3-ylamino)-pyrimidin-2-ylamino]-8-methoxy-1,2,4,5-tetrahydro-benzo[d]azepin-3-yl}-N,N-dimethyl-acetamide Following a procedure similar to 1190, 2-(7-amino-8-methoxy-1,2,4,5-tetrahydro-benzo[d]azepin-3-yl)-N,N-dimethyl-acetamide and (2,5-dichloro-pyrimidin-4-yl)-(2,6-dimethoxy-pyridin-3-yl)-amine, which was prepared in a manner analogous to 1186a, were converted to 2-{7-[5-Chloro-4-(2,6-dimethoxy-pyridin-3-ylamino)-pyrimidin-2-ylamino]-8-methoxy-1,2,4,5-tetrahydro-benzo[d]azepin-3-yl}-N,N-dimethyl-acetamide as an off-white solid (69 mg, 24%). MP: 67-76° C.; $^1$H-NMR (CDCl$_3$) δ 8.45 (d, J=8.4 Hz, 1H), 8.03 (s, 1H), 7.96 (s, 1H), 7.41 (s, 1H), 7.26 (s, 1H), 6.63 (s, 1H), 6.31 (d, J=8.4 Hz, 1H), 4.03 (s, 3H), 3.93 (s, 3H), 3.85 (s, 3H), 3.29 (s, 2H), 3.15 (s, 3H), 2.98 (s, 3H), 2.87 (m, 2H), 2.81 (m, 2H), 2.60 (br s, 4H); LC/MS (ESI+): 542.28 (M+H).

Example 1201

2-{2-[3-(2-Azetidin-1-yl-2-oxo-ethyl)-8-methoxy-2,3,4,5-tetrahydro-1H-benzo[d]azepin-7-ylamino]-5-chloro-pyrimidin-4-ylamino}-N,N-dimethyl-benzenesulfonamide Following a procedure similar to 1190, 2-(7-Amino-8-methoxy-1,2,4,5-tetrahydro-benzo[d]azepin-3-yl)-1-azetidin-1-yl-ethanone, which was prepared in a manner analogous to 258a,b, and 2-(2,5-dichloro-pyrimidin-4-ylamino)-N,N-dimethyl-benzenesulfonamide were converted to 2-{2-[3-(2-azetidin-1-yl-2-oxo-ethyl)-8-methoxy-2,3,4,5-tetrahydro-1H-benzo[d]azepin-7-ylamino]-5-chloro-pyrimidin-4-ylamino}-N,N-dimethyl-benzenesulfonamide as an off-white solid (59 mg, 30%). MP: 75-87° C.; 1H-NMR (CDCl$_3$) δ 9.33 (s, 1H), 8.52 (d, J=8.4 Hz, 1H), 8.13 (s, 1H), 7.98 (s, 1H), 7.88 (d, J=7.6 Hz, 1H), 7.56 (t, J=8.0 Hz, 1H), 7.50 (s, 1H), 7.23 (d, J=7.6 Hz, 1H), 6.65 (s, 1H), 4.29 (t, J=7.6 Hz, 2H), 4.09 (t, J=7.6 Hz, 2H), 3.87 (s, 3H), 3.12 (s, 2H), 2.88 (m, 2H), 2.75 (s, 8H), 2.67 (m, 4H), 2.31 (m, 2H); LC/MS (ESI+): 600.28 (M+H).

Example 1202

1-[5-Chloro-2-(3-dimethylcarbamoylmethyl-8-methoxy-2,3,4,5-tetrahydro-1H-benzo[d]azepin-7-ylamino)-pyrimidin-4-ylamino]-cyclopentanecarboxylic acid isopropyl ester Following a procedure similar to Example 258c, 2-(7-amino-8-methoxy-1,2,4,5-tetrahydro-benzo[d]azepin-3-yl)-N,N-dimethyl-acetamide and 1-(2,5-dichloro-pyrimidin-4-ylamino)-cyclopentanecarboxylic acid methylamide, which was prepared in a manner similar to 1196a-c, were converted to 1-[5-chloro-2-(3-dimethylcarbamoylmethyl-8-methoxy-2,3,4,5-tetrahydro-1H-benzo[d]azepin-7-ylamino)-pyrimidin-4-ylamino]-cyclopentanecarboxylic acid isopropyl ester as a light tan solid (123 mg, 31%) [Isopropanol used as a solvent displaced methylamine]. MP: 65-70° C.; $^1$H-NMR (CDCl$_3$) δ 8.01 (s, 1H), 7.92 (s, 1H), 7.36 (br s, 1H), 6.60 (s, 1H), 5.54 (s, 1H), 4.93 (h, J=7.4 Hz, 1H), 3.84 (s, 3H), 3.28 (s, 2H), 3.16 (s, 3H), 3.02 (m, 2H), 2.98 (s, 3H), 2.86 (m, 2H), 2.70 (m, 4H), 2.43 (m, 2H), 2.11 (m, 2H), 1.83 (m, 4H), 1.05 (d, J=7.4 Hz, 6H); LC/MS (ESI+): 559.38 (M+H).

Example 1203

1-[5-Chloro-2-(3-dimethylcarbamoylmethyl-8-methoxy-2,3,4,5-tetrahydro-1H-benzo[d]azepin-7-ylamino)-pyrimidin-4-ylamino]-cyclopentanecarboxylic acid methylamide Following a procedure similar to 1190, 2-(7-amino-8-methoxy-1,2,4,5-tetrahydro-benzo[d]azepin-3-yl)-N,N-dimethyl-acetamide and 1-(2,5-dichloro-pyrimidin-4-ylamino)-cyclopentanecarboxylic acid methylamide were converted to 1-[5-chloro-2-(3-dimethylcarbamoylmethyl-8-methoxy-2,3,4,5-tetrahydro-1H-benzo[d]azepin-7-ylamino)-pyrimidin-4-ylamino]-cyclopentanecarboxylic acid methylamide as a white solid (26 mg, 7%). MP: 75-87° C.; $^1$H-NMR (CDCl$_3$) δ 9.33 (s, 1H), 8.52 (d, J=8.4 Hz, 1H), 8.13 (s, 1H), 7.98 (s, 1H), 7.88 (d, J=7.6 Hz, 1H), 7.56 (t, J=8.0 Hz, 1H), 7.50 (s, 1H), 7.23 (d, J=7.6 Hz, 1H), 6.65 (s, 1H), 4.29 (t, J=7.6 Hz, 2H), 4.09 (t, J=7.6 Hz, 2H), 3.87 (s, 3H), 3.12 (s, 2H), 2.88 (m, 2H), 2.75 (s, 8H), 2.67 (m, 4H), 2.31 (m, 2H); LC/MS (ESI+): 600.28 (M+H).

Example 1204

(1S,2S,3R,4R)-3-[5-Chloro-2-(1-methoxy-8-morpholin-4-yl-6,7,8,9-tetrahydro-5H-benzocyclohepten-2-ylamino)-pyrimidin-4-ylamino]-bicyclo[2.2.1]hept-5-ene-2-carboxylic acid amide 1204a) 4-Methoxy-5,7,8,9-tetrahydro-benzocyclohepten-6-one (2.25 g, 11.8 mmol), which was prepared according to literature (Tarnchopmpoo, B. *Synthesis* 1986, 785; Taylor, E. C. and Chiang, C.-S. *Tetrahedron Lett.* 1977, 1827; Hacksell, U. Et al. *J. Med. Chem.* 1989, 32, 2311), and morpholine (1.13 mL, 13.0 mmol) were treated with sodium triacetoxyborohydride (3.51 g, 16.6 mmol) and acetic acid (0.672 mL, 11.8 mmol) in tetrahydrofuran (100 mL) at room temperature for 3 days (Abdel-Magid, A. F. et al. *J. Org. Chem.* 1996, 61, 3849). The reaction mixture was then concentrated an partitioned between dichloromethane and an aqueous saturated sodium bicarbonate solution. The organic phase was washed with water, dried on MgSO$_4$, and concentrated. Flash chromatography purification (SiO$_2$; MeOH/DCM 0-10%) afforded 4-(4-methoxy-6,7,8,9-tetrahydro-5H-benzocyclohepten-6-yl)-morpholine as a white solid (3.1 g, 99%). LC/MS (ESI+): 262.0 (M+H).

1204b) 4-(4-Methoxy-6,7,8,9-tetrahydro-5H-benzocyclohepten-6-yl)-morpholine (2.00 g, 7.65 mmol) was treated with trifluoroacetic anhydride (5.40 mL, 38.3 mmol) and potassium nitrate (775 mg, 7.66 mmol) in acetonitrile (20 mL, 400 mmol) at 0° C. for 3 h. The reaction mixture was next partitioned between an aqueous saturated sodium bicarbonate solution (20 mL) and methylene chloride (100 mL) and the aqueous phase was extracted with additional methylene chloride (100 mL). The organics were dried (Na$_2$SO$_4$) and concentrated to afford a yellow oil. Chromatography (SiO$_2$; gradient elution—0 to 5% MeOH:DCM) affords a mixture of 4-(4-methoxy-1-nitro-6,7,8,9-tetrahydro-5H-benzocyclohepten-6-yl)-morpholine and 4-(4-methoxy-3-nitro-6,7,8,9-tetrahydro-5H-benzocyclohepten-6-yl)-morpholine. The desired isomer was isolated by chromatography on 120 g SiO$_2$ cartridge (ISCO); with a 0-10-20-30-40-50-55% gradient of ethyl acetate in dichloromethane, 5 min each step: 4-(4-methoxy-1-nitro-6,7,8,9-tetrahydro-5H-benzocyclohepten-6-yl)-morpholine (440 mg, 19%), yellow oil. LC/MC (ESI+): 307.05 (M+H).

1204c) Following a procedure similar to 258b, 4-(4-methoxy-1-nitro-6,7,8,9-tetrahydro-5H-benzocyclohepten-6-yl)-morpholine was converted to 1-methoxy-8-morpholin-4-yl-6,7,8,9-tetrahydro-5H-benzocyclohepten-2-ylamine as a light tan solid. (386 mg, 99%). LC/MS (ESI+): 277.07 (M+H).

1204d) Following a procedure similar to 1170, 1-methoxy-8-morpholin-4-yl-6,7,8,9-tetrahydro-5H-benzocyclohepten-2-ylamine and (1S,2S,3R,4R)-3-(2,5-Dichloro-pyrimidin-4-ylamino)-bicyclo[2.2.1]hept-5-ene-2-carboxylic acid amide were converted to (1S,2S,3R,4R)-3-[5-chloro-2-(1-methoxy-8-morpholin-4-yl-6,7,8,9-tetrahydro-5H-benzocyclohepten-2-ylamino)-pyrimidin-4-ylamino]-bicyclo[2.2.1]hept-5-ene-2-carboxylic acid amide (155 mg, 53%) as a white solid (a 1:1 mixture of diastereoisomers). MP: 139-148° C.; $^1$H-NMR (CDCl$_3$) δ 8.17 (d, J=8.0 Hz, 1H), 7.89 (s, 1H), 7.37 (s, 1H), 6.97 (m, 1H), 6.83 (d, J=8.0 Hz, 1H), 6.37 (m, 1H), 6.31 (m, 1H), 5.61 (br, 1H), 5.38 (br s, 1H), 4.36 (m, 1H), 3.76 (s, 3H), 3.74 (br s, 4H), 3.43 (d, J=13.1 Hz, 1H), 3.07 (s, 1H), 2.94 (s, 1H), 2.72 (m, 4H), 2.58 (m, 2H), 2.49 (m, 2H), 2.33 (m, 1H), 2.23 (d, J=9.2 Hz, 1H), 2.07 (m, 2H), 1.79 (m, 1H), 1.62 (m, 1H), 1.39 (m, 1H); LC/MS (ESI+): 539.16 (M+H).

Example 1205

2-(7-{5-Chloro-4-[2-((R)-3-hydroxy-pyrrolidine-1-sulfonyl)-phenylamino]-pyrimidin-2-ylamino}-8-methoxy-1,2,4,5-tetrahydro-benzo[d]azepin-3-yl)-N,N-dimethyl-acetamide Following a procedure similar to 1170, 2-(7-amino-8-methoxy-1,2,4,5-tetrahydro-benzo[d]azepin-3-yl)-N,N-dimethyl-acetamide and {2-[(R)-3-(tert-butyl-dimethyl-silanyloxy)-pyrrolidine-1-sulfonyl]-phenyl}-(2,5-dichloro-pyrimidin-4-yl)-amine, which was prepared in a manner similar to 1188a-c, were converted to 2-(7-{5-chloro-4-[2-((R)-3-hydroxy-pyrrolidine-1-sulfonyl)-phenylamino]-pyrimidin-2-ylamino}-8-methoxy-1,2,4,5-tetrahydro-benzo[d]azepin-3-yl)-N,N-dimethyl-acetamide (87 mg, 55%) as a white solid. MP: 65-79° C.; $^1$H-NMR (CDCl$_3$) δ 9.30 (s, 1H), 8.44 (d, J=8.4 Hz, 1H), 8.13 (s, 1H), 7.96 (s, 1H), 7.94 (d, J=8.4 Hz, 1H), 7.55 (t, J=8.0 Hz, 1H), 7.51 (s, 1H), 7.23 (t, J=8.0 Hz, 1H), 6.63 (s, 1H), 4.34 (br s, 1H), 3.86 (s, 3H), 3.40 (m, 3H), 3.29 (s, 2H), 3.27 (m, 1H), 3.13 (s, 3H), 2.97 (s, 3H), 2.86 (m, 2H), 2.69 (m, 4H), 2.66 (m, 2H), 1.85 (m, 3H); LC/MS (ESI+): 630.32 (M+H).

Example 1206

2-(7-{5-Chloro-4-[2-((S)-3-hydroxy-pyrrolidine-1-sulfonyl)-phenylamino]-pyrimidin-2-ylamino}-8-methoxy-1,2,4,5-tetrahydro-benzo[d]azepin-3-yl)-N,N-dimethyl-acetamide Following a procedure similar to 1170, 2-(7-amino-8-methoxy-1,2,4,5-tetrahydro-benzo[d]azepin-3-yl)-N,N-dimethyl-acetamide and {2-[(S)-3-(tert-butyl-dimethyl-silanyloxy)-pyrrolidine-1-sulfonyl]-phenyl}-(2,5-dichloro-pyrimidin-4-yl)-amine, which was prepared in a manner similar to 1188a-c, were converted to 2-(7-{5-chloro-4-[2-((S)-3-hydroxy-pyrrolidine-1-sulfonyl)-phenylamino]-pyrimidin-2-ylamino}-8-methoxy-1,2,4,5-tetrahydro-benzo[d]azepin-3-yl)-N,N-dimethyl-acetamide (87 mg, 55%) as a white solid. MP: 78-89° C.; $^1$H-NMR (CDCl$_3$) δ 9.31 (s, 1H), 8.45 (d, J=8.4 Hz, 1H), 8.13 (s, 1H), 7.96 (s, 1H), 7.94 (d, J=8.4 Hz, 1H), 7.54 (t, J=8.0 Hz, 1H), 7.50 (s, 1H), 7.23 (t, J=8.0 Hz, 1H), 6.63 (s, 1H), 4.33 (br s, 1H), 3.86 (s, 3H), 3.40 (m, 3H), 3.28 (s, 2H), 3.26 (m, 1H), 3.13 (s, 3H), 2.97 (s, 3H), 2.86 (m, 2H), 2.70 (m, 4H), 2.65 (m, 2H), 1.87 (m, 3H); LC/MS (ESI+): 630.32 (M+H).

Example 1207

2-{2-[3-(2-Amino-2-methyl-propionyl)-8-methoxy-2,3,4,5-tetrahydro-1H-benzo[d]azepin-7-ylamino]-5-chloro-pyrimidin-4-ylamino}-N,N-dimethyl-benzenesulfonamide Following a procedure similar to 1170, [2-(7-Amino-8-methoxy-1,2,4,5-tetrahydro-benzo[d]azepin-3-yl)-1,1-dimethyl-2-oxo-ethyl]-carbamic acid tert-butyl ester, which was prepared via a sequence of reactions analogous to 1196a and 258b, and 2-(2,5-dichloro-pyrimidin-4-ylamino)-N,N-dimethyl-benzenesulfonamide were converted to 2-{2-[3-(2-amino-2-methyl-propionyl)-8-methoxy-2,3,4,5-tetrahydro-1H-benzo[d]azepin-7-ylamino]-5-chloro-pyrimidin-4-ylamino}-N,N-dimethyl-benzenesulfonamide (24 mg, 22%) as a white solid. MP: 93-101° C.; $^1$H-NMR (CDCl$_3$) δ 9.35 (br s, 1H), 8.52 (d, J=8.0 Hz, 1H), 8.15 (s, 1H), 8.06 (s, 1H), 7.89 (d, J=8.0 Hz, 1H), 7.57 (m, 1H), 7.51 (s, 1H), 7.26 (m, 1H), 6.67 (br s, 1H), 3.88 (s, 3H), 3.82 (s, 2H), 2.91 (br s, 2H), 2.75 (s, 6H), 1.80 (br s, 4H), 1.45 (s, 6H); LC/MS (ESI+): 588.29 (M+H).

Example 1208

2-{7-[5-Chloro-4-(6-methoxy-2-methylamino-pyridin-3-ylamino)-pyrimidin-2-ylamino]-8-methoxy-1,2,4,5-tetrahydro-benzo[d]azepin-3-yl}-N,N-dimethyl-acetamide 1208a) Following a procedure similar to 1186a, 3-amino-6-methoxy-2-methylaminopyridine (Oguchi, M. et al. *J. Med. Chem.* 2000, 43, 3052) was converted to N(3)-(2,5-dichloro-pyrimidin-4-yl)-6-methoxy-N(2)-methyl-pyridine-2,3-diamine (1.15 g, 59%) as a purple solid.

1208b) Following a procedure similar to 1190, 2-(7-amino-8-methoxy-1,2,4,5-tetrahydro-benzo[d]azepin-3-yl)-N,N-dimethyl-acetamide and N(3)-(2,5-dichloro-pyrimidin-4-yl)-6-methoxy-N(2)-methyl-pyridine-2,3-diamine were converted to 2-{7-[5-chloro-4-(6-methoxy-2-methylamino-pyridin-3-ylamino)-pyrimidin-2-ylamino]-8-methoxy-1,2,4,5-tetrahydro-benzo[d]azepin-3-yl}-N,N-dimethyl-acetamide as a white solid (47 mg, 16%). MP: 191-194° C.; $^1$H-NMR (CDCl$_3$) δ 8.00 (s, 1H), 7.79 (s, 1H), 7.55 (br s, 1H), 7.30 (d, J=8.0 Hz, 1H), 6.55 (s, 1H), 6.35 (s, 1H), 6.03 (d, J=8.0 Hz, 1H), 4.60 (q, J=4.8 Hz, 1H), 3.94 (s, 3H), 3.81 (s, 3H), 3.26 (s, 2H), 3.16 (s, 3H), 2.98 (s, 3H), 2.95 (d, J=4.8 Hz, 3H), 2.80 (m, 2H), 2.60 (m, 6H); LC/MS (ESI+): 541.33 (M+H).

Example 1209

2-{7-[5-Chloro-4-(2-methylamino-6-morpholin-4-yl-pyridin-3-ylamino)-pyrimidin-2-ylamino]-8-methoxy-1,2,4,5-tetrahydro-benzo[d]azepin-3-yl}-N,N-dimethyl-acetamide Following a procedure similar to 1190, 2-(7-amino-8-methoxy-1,2,4,5-tetrahydro-benzo[d]azepin-3-yl)-N,N-dimethyl-acetamide and N*3*-(2,5-dichloro-pyrimidin-4-yl)-N*2*-methyl-6-morpholin-4-yl-pyridine-2,3-diamine, which was prepared in a manner similar to 1208a, were converted to 2-{7-[5-chloro-4-(2-methylamino-6-morpholin-4-yl-pyridin-3-ylamino)-pyrimidin-2-ylamino]-8-methoxy-1,2,4,5-tetrahydro-benzo[d]azepin-3-yl}-N,N-dimethyl-acetamide as a tan solid (62 mg, 19%). MP: 97-108° C.; $^1$H-NMR (CDCl$_3$) δ 7.99 (s, 1H), 7.86 (s, 1H), 7.55 (br s, 1H), 7.24 (d, J=8.0 Hz, 1H), 6.56 (s, 1H), 6.33 (s, 1H), 5.91 (d, J=8.1 Hz, 1H), 4.49 (q, J=4.8 Hz, 1H), 3.83 (m, 2H), 3.82 (s, 4H), 3.52 (m, 4H), 3.24 (s, 2H), 3.17 (s, 3H), 2.99 (s, 3H), 2.90 (d, J=4.8 Hz, 3H), 2.80 (m, 2H), 2.61 (m, 6H); LC/MS (ESI+): 596.35 (M+H).

Example 1210

2-[5-Chloro-2-(1-methoxy-8-morpholin-4-yl-6,7,8,9-tetrahydro-5H-benzocyclohepten-2-ylamino)-pyrimidin-4-ylamino]-N,N-dimethyl-benzenesulfonamide Following a procedure similar to 1170, 1-methoxy-8-morpholin-4-yl-6,7,8,9-tetrahydro-5H-benzocyclohepten-2-ylamine and 2-(2,5-dichloro-pyrimidin-4-ylamino)-N,N-dimethyl-benzenesulfonamide were converted to 2-[5-chloro-2-(1-methoxy-8-morpholin-4-yl-6,7,8,9-tetrahydro-5H-benzocyclohepten-2-ylamino)-pyrimidin-4-ylamino]-N,N-dimethyl-benzenesulfonamide (49 mg, 46%) as a white solid (racemic). MP: 92-104° C.; $^1$H-NMR (CDCl$_3$) δ 9.42 (s, 1H), 8.57 (d, J=8.4 Hz, 1H), 8.15 (s, 1H), 7.98 (d, J=8.0 Hz, 1H), 7.87 (dd, J=1.2, 8.0 Hz, 1H), 7.61 (m, 1H), 7.46 (s, 1H), 7.25 (m, 1H), 6.79 (d, J=8.4 Hz, 1H), 3.78 (s, 3H), 3.74 (m, 4H), 3.43 (d, J=13.4 Hz, 1H), 2.75 (s, 6H), 2.72 (m, 4H), 2.59 (m, 2H), 2.49 (dd, J=10.0, 13.4 Hz, 1H), 2.32 (apparent t, 10.0 Hz, 1H), 2.11 (m, 2H), 1.82 (m, 1H), 1.40 (m, 1H); LC/MS (ESI+): 587.29 (M+H).

Example 1221

2-[5-Chloro-2-(8-oxo-6,7,8,9-tetrahydro-5-oxa-9-aza-benzocyclohepten-2-ylamino)-pyrimidin-4-ylamino]-3-fluoro-N-methyl-benzamide

Example 1221a

2-Nitro-6,7-dihydro-9H-5-oxa-9-aza-benzocyclohepten-8-one. Trichloroacetic Acid (39 g, 0.24 mol), Sulfuric acid (3 mL, 0.05 mol), and 6-Nitro-chroman-4-one (5.000 g, 0.026 mol) were combined and heated to 70° C. Sodium azide (3.36 g, 0.052 mol) was added slowly. The resulting solution was heated for 2 h, poured onto ice. Title compound isolated as a beige solid in 22% yield. 95% purity, LCMS: 209.15 (M+1) 1H NMR (400 MHz, DMSO, d6) δ 10.13, (s, 1H), 8.06 (dd, J=1.5 Hz, 1H), 7.85-7.82 (m, 1H), 7.15 (d, J=8.8 Hz, 1H), 4.47-4.44 m, 2H), 2.88-2.85 (m, 2H).

Example 1221b

7-Nitro-3,4-dihydro-2H-1,4-benzoxazepin-5-one. Obtained as an off-white solid from Example 1221a, 10% yield in >90% purity, MP=229-230. LCMS: 209.14, NMR (400 MHz, DMSO, d6) δ 8.80 (dd, 1.3 Hz, 1H), 8.70 (bt, 1H), 8.26 (m, 1H), 7.20 (dd, J=1.0 Hz, 9.1 Hz), 1H, 4.51-4.49 (m, 2H), 3.47-3.45 (m, 2H).

Example 1221c

2-Amino-6,7-dihydro-9H-5-oxa-9-aza-benzocyclohepten-8-one. Into a Hydrogenation flask containing 2-Nitro-6,7-dihydro-9H-5-oxa-9-aza-benzocyclohepten-8-one (0.2 g, 0.001 mol), was added Methanol (20 mL, 0.5 mol), followed by 10% Pd/C (0.02 g). The reaction mixture was shaken in a Parr apparatus under 20 psi of H2 for 90 min, was filtered through celite, washed with MeOH, and concentrated under reduced pressure to obtain 114 mg (70% yield) of title compound as a pale yellow solid. 97% purity, MP=158-160. LCMS: 179.19 (M+1), NMR (CDCl3) δ 7.94 (bs, 1H), 6.87 (d, J=8.4 Hz, 1H), 6.40 (dd, J=2.2 Hz, 8.5 Hz, 1H), 6.28 (s, 1H), 4.43-4.40 (m, 2H), 3.58 (bs, 2H), 2.79-2.76 (m, 2H).

Example 1221d

2-[5-Chloro-2-(8-oxo-6,7,8,9-tetrahydro-5-oxa-9-aza-benzocyclohepten-2-ylamino)-pyrimidin-4-ylamino]-3-fluoro-N-methyl-benzamide. Into an 8 ml sealed tube was placed 2-Amino-6,7-dihydro-9H-5-oxa-9-aza-benzocyclohepten-8-one (0.080 g, 0.45 mmol), 2-(2,5-Dichloro-pyrimidin-4-ylamino)-3-fluoro-N-methyl-benzamide (0.16 g, 0.49 mmol), and 10-Camphorsulfonic acid (0.11 g, 0.49 mmol). Isopropyl alcohol (2 mL, 0.03 mol) was added. The reaction was microwaved at 120° C. for 40 minutes, diluted with CH2Cl2, washed with aqueous sat'd NaHCO3, dried over MgSO4, filtered, and concentrated under reduced pressure. The reaction mixture was purified by silica gel chromatography (ISCO amine column 0-100% EtOAc in hexanes) to afford title compound as a yellow solid. LCMS: 457.17 (M+H), HPLC: 95% purity, 1H-NMR (CDCl3, 400 MHz) δ 8.78 (s, 1H), 8.05 (d, J=1.8 Hz, 1H), 7.80 (s, 1H), 7.45-7.40 (m, 3H), 7.35-7.31 (m, 2H), 6.90 (d, J=8.6 Hz, 1H), 6.79 (d, J=8.8 Hz, 1H), 6.43 (bd, 4.0 Hz, 1H), 4.42 (t, J=5.8 Hz, 2H), 2.94 (d, J=4.8 Hz, 3H), 2.81 (t, J=5.6 Hz, 2H).

Example 1222

2-[5-Chloro-2-(5-oxo-2,3,4,5-tetrahydro-1,4-benzoxazepin-7-ylamino)-pyrimidin-4-ylamino]-3-fluoro-N-methyl-benzamide Example 1222a 7-Amino-3,4-dihydro-2H-1,4-benzoxazepin-5-one. 7-Nitro-3,4-dihydro-2H-1,4-benzoxazepin-5-one (from Example 1221a) was reduced in an analogous manner to Example 1221c to afford title compound as a white solid in 80% yield. Purity >95%, MP=165-168. LCMS: 179.17, NMR (DMSO) 8.09 (bt, 1H), 6.80 (d, J=2.7 Hz, 1H), 6.73-6.71 (m, 1H), 6.65-6.62 (m, 1H), 4.98 (bs, 2H), 4.07-4.04 (m, 2H), 3.19-3.15 (m, 2H).

Example 1222b

2-[5-Chloro-2-(5-oxo-2,3,4,5-tetrahydro-1,4-benzoxazepin-7-ylamino)-pyrimidin-4-ylamino]-3-fluoro-N-methyl-benzamide was prepared from 7-Amino-3,4-dihydro-2H-1,4-benzoxazepin-5-one was and 2-(2,5-Dichloro-pyrimidin-4-ylamino)-3-fluoro-N-methyl-benzamide in an analogous manner to Example 1d to afford title compound as a white solid in 40% yield, MP=268-269, LCMS 457.24 (M+H), HPLC purity=99%, 1H-NMR (DMSO-d6, 400 MHz) δ 9.43 (d, J=6.6 Hz, 2H), 8.65-8.63 (m, 1H), 8.37 (t, J=5.3 Hz, 1H), 8.27 (s, 1H), 7.75-7.69 (m, 2H), 7.61-7.53 (m, 2H), 7.41-7.50 (m, 1H), 6.86 (d, 8.8 Hz, 1H), 4.27 (t, J=4.3 Hz, 2H), 3.33-3.30 (m, 2H), 2.83 (d, J=3.5 Hz, 3H).

Example 1223

3-{3-[5-Chloro-2-(1-ethyl-2-oxo-2,3,4,5-tetrahydro-1H-1-benzazepin-8-ylamino)-pyrimidin-4-ylamino]-phenyl}-propionitrile Example 1223a 3-(3-Amino-phenyl)-propionitrile was prepared from 3-(3-Nitro-phenyl)-acrylonitrile in an analogous manner to Example 1c Title compound was isolated as a yellow oil in 64% yield, LCMS (147.16 (M+H), 1H-NMR (CDCl3, 400 MHz) δ 7.13 (dd, J=8.0 Hz, 7.6 Hz, 1H), 6.60 (m, 2H), 6.55 (s, 1H), 3.71 (bs, 2H), 2.86 (dd, J=7.4 Hz, 7.4 Hz, 2H), 2.60 (dd, J=7.4 Hz, 7.4 Hz, 2H).

Example 1223b

3-[3-(2,5-Dichloro-pyrimidin-4-ylamino)-phenyl]-propionitrile. 3-(3-Amino-phenyl)-propionitrile (0.110 g, 0.000752 mol), 2,4,5-Trichloro-pyrimidine (0.152 g, 0.000828 mol), Potassium carbonate (0.125 g, 0.90 mmol), and DMF (1.0 mL, 0.014 mol) were heated at 85° C. for 90 min. The reaction mixture was diluted with H2O, extracted with CH2Cl2×3, dried over MgSO4, filtered, and concentrated under reduced pressure. Title compound isolated as a white solid. MP=111-112. HPLC purity: 95% LCMS: 295.10 (M+H) 1H-NMR (CDCl3, 400 MHz) δ 8.21 (d, J=0.8 Hz, 1H), 7.53-7.56 (m, 2H), 7.38 (dd, J=7.6 Hz, 7.8 Hz, 1H), 7.31 (s, 1H), 7.07 (d, J=7.6 Hz, 1H), 3.00 (dd, J=7.0 Hz, 7.3 Hz, 2H), 2.67 (dd, J=7.4 Hz, 7.2 Hz, 2H).

Example 1223c

3-{3-[5-Chloro-2-(1-ethyl-2-oxo-2,3,4,5-tetrahydro-1H-1-benzazepin-8-ylamino)-pyrimidin-4-ylamino]-phenyl}-propionitrile was prepared from 3-[3-(2,5-Dichloro-pyrimidin-4-ylamino)-phenyl]-propionitrile and 8-Amino-1-ethyl-1,3,4,5-tetrahydro-1-benzazepin-2-one) in an analogous manner to Example 1d. Title compound isolated as a white foam. Purity 99% (HPLC). LCMS: 462.50 (M+H). 1H-NMR (CDCl3, 400 MHz) δ 8.10 (s, 1H), 7.96 (bs, 1H), 7.66 (bs, 1H), 7.62 (s, 1H), 7.28-7.26 (m, 2H), 7.25-7.23 (m, 1H), 7.07 (d, J=8.4 Hz, 1H), 7.06 (s, 1H), 6.98 (d, J=7.3 Hz, 1H), 4.00-3.55 (m, 2H), 2.97 (t, J=6.6 Hz, 2H), 2.69 (t, J=6.0 Hz, 2H), 2.67-2.64 (m, 2H), 2.30-2.27 (m, 2H), 2.18-2.08 (m, 2H), 1.10 (t, J=7.1 Hz, 3H).

Example 1224

2-[2-(1-Acetyl-4-oxo-1,2,3,4,5,6-hexahydro-benzo[b][1,5]diazocin-8-ylamino)-5-chloro-pyrimidin-4-ylamino]-3-fluoro-N-methyl-benzamide

Example 1224a

1-Acetyl-2,3,5,6-tetrahydro-1H-benzo[b][1,5]diazocin-4-one. 2,3,5,6-Tetrahydro-1H-benzo[b][1,5]diazocin-4-one (prepared as in J. Am. Chem. Soc. 2004, 126, 3529-3533) (1.00 g, 5.68 mmol) was dissolved in anh acetonitrile (50 ml). Acetic anhydride (587 μL, 6.25 mmol) was added and the reaction mixture was heated to 80° C. for 16 h. The reaction mixture was concentrated, triturated with ether, and filtered to afford title compound as a beige solid. (1.063 g, 86%) mp 236-239° C.; LCMS: m/z=219.30 (M+H+), HPLC (95% purity); 1H NMR (400 MHz, DMSO-d6) δ 7.82 (m, 1H), 7.38 (m, 4H), 4.64 (m, 1H), 4.29 (m, 1H), 3.87 (m, 1H), 2.92 (m, 1H), 2.57 (m, 1H), 2.26 (m, 1H), 1.69 (s, 3H).

Example 1224b

1-Acetyl-8-nitro-2,3,5,6-tetrahydro-1H-benzo[b][1,5]diazocin-4-one. 1-Acetyl-2,3,5,6-tetrahydro-1H-benzo[b][1,5]diazocin-4-one (1.05 g, 4.82 mmol) was added to a 1/1 mixture of HNO3/H2SO4 (20 ml) at 0° C. The resulting solution was stirred at 0° C. for 3 h and allowed to warm to rt over 16 h. The reaction mixture was poured onto ice and neutralized with NaOH. The resulting ppt was filtered and washed with H2O to afford title compound as a pale orange solid. (600 mg, 47%). mp 253-256° C.; LCMS: m/z=264.25 (M+H+), HPLC (95% purity); 1H NMR (400 MHz, DMSO-d6) δ 8.31 (s, 1H), 8.24 (d, J=8.8 Hz, 1H), 7.79 (m, 1H), 7.69 (d, J=8.6 Hz, 1H). 4.65 (m, 1H), 4.38 (m, 1H), 4.11 (m, 1H), 2.96 (m, 1H), 2.61 (m, 1H), 2.38 (m, 1H), 1.73 (s, 3H).

Example 1224c

1-Acetyl-8-amino-2,3,5,6-tetrahydro-1H-benzo[b][1,5]diazocin-4-one was prepared from 1-Acetyl-8-nitro-2,3,5,6-tetrahydro-1H-benzo[b][1,5]diazocin-4-one in an analogous manner to Example 1c as a beige foam (500 mg, 94%). LCMS: m/z=234.34 (M+H+), HPLC (96% purity) 1H NMR (400 MHz, DMSO-d6) δ 8.51 (s, 1H), 8.45 (s, 1H), 7.81 (m, 1H), 7.08 (d, J=8.4 Hz, 1H), 6.86 (s, 1H) 6.77 (d, J=8.3 Hz, 1H), 4.59 (m, 1H), 4.18 (m, 1H), 3.73 (m, 1H), 2.87 (m, 1H), 2.51 (m, 1H), 2.24 (m, 1H), 1.66 (s, 3H).

Example 1224d

2-[2-(1-Acetyl-4-oxo-1,2,3,4,5,6-hexahydro-benzo[b][1,5]diazocin-8-ylamino)-5-chloro-pyrimidin-4-ylamino]-3-fluoro-N-methyl-benzamide was prepared from 1-Acetyl-8-amino-2,3,5,6-tetrahydro-1H-benzo[b][1,5]diazocin-4-one and 2-(2,5-Dichloro-pyrimidin-4-ylamino)-3-fluoro-N-methyl-benzamide in an analogous manner to Example 1221d. Isolated as a beige solid. MP: 97-103. HPLC purity: 95%, LCMS: 512.28 (M+H) HNMR: CD3OD: 8.16 (s, 1H), 7.51-7.41 (m, 5H), 7.12 (d, J=8.6 Hz, 1H), 4.79-4.75 (m, 1H), 4.37-4.33 (m, 1H), 3.86-3.79 (m, 1H), 3.20-3.12 (m, 1H), 2.86 (s, 3H), 2.73-2.71 (m, 1H), 2.49-2.44 (m, 1H), 1.78 (s, 3H).

Example 1225

{4-[5-Chloro-2-(1-ethyl-2-oxo-2,3,4,5-tetrahydro-1H-1-benzazepin-8-ylamino)-pyrimidin-4-ylamino]-phenyl}-acetonitrile

Example 5a

[4-(2,5-Dichloro-pyrimidin-4-ylamino)-phenyl]-acetonitrile was prepared from 2,4,5-Trichloro-pyrimidine and 4-Aminophenylacetic acid nitrile in an analogous manner to Example 1223b. Pale yellow solid (243 mg, 38%), mp=134-135, HPLC purity: 94%, LCMS 279.06 (M+H), 1H-NMR (DMSO-d6, 400 MHz) δ 9.59 (s, 1H) 8.39 (s, 1H), 7.58 (d, J=8.3 Hz, 2H), 7.36 (d, J=8.2 Hz, 2H), 4.03 (s, 2H).

Example 1225b

{4-[5-Chloro-2-(1-ethyl-2-oxo-2,3,4,5-tetrahydro-1H-1-benzazepin-8-ylamino)-pyrimidin-4-ylamino]-phenyl}-acetonitrile was prepared from [4-(2,5-Dichloro-pyrimidin-4-ylamino)-phenyl]-acetonitrile and 8-Amino-1-ethyl-1,3,4,5-tetrahydro-1-benzazepin-2-one in an analogous manner to Example 1d. White solid 130 mg (96%), MP: 163-164, HPLC purity 94%, LCMS: 447.25 (M+H), 1H-NMR (CDCl3, 400 MHz) δ 8.12 (s, 1H), 7.74 (s, 1H), 7.58 (d, J=8.2 Hz, 2H), 7.30 (d, J=8.2 Hz, 2H), 7.08-7.11 (m, 3H), 7.01 (s, 1H), 3.84 (s, 2H), 2.67 (bs, 2H), 2.34-2.31 (m, 2H), 2.29-2.18 (m, 2H), 1.58 (s, 2H), 1.02 (t, J=7.1 Hz, 3H).

Example 1226

{4-[5-Chloro-2-(1-ethyl-2-oxo-2,3,4,5-tetrahydro-1H-1-benzazepin-8-ylamino)-pyrimidin-4-ylamino]-phenoxy}-acetonitrile

Example 1226a (4-Nitro-phenoxy)-acetonitrile was reduced in an analogous manner to Example 1221c to afford (4-Amino-phenoxy)-acetonitrile (0.440 g, 53%) as a pale yellow solid. 1H-NMR (CDCl3, 400 MHz) δ 6.86 (d, J=8.8 Hz, 2H), 6.67 (d, J=8.8 Hz, 2H), 4.69 (s, 2H), 3.57 (bs, 2H).

Example 1226b

[4-(2,5-Dichloro-pyrimidin-4-ylamino)-phenoxy]-acetonitrile was formed from (4-Amino-phenoxy)-acetonitrile and 2,4,5-Trichloro-pyrimidine in an analogous manner to Example 1223b. Title product was isolated as a white solid. MP 123-125, LCMS 295.06 (M+H) HPLC purity 99%, 1HNMR CDCl3: 8.21 (s, 1H), 7.62 (d, J=8.9 Hz, 2H), 7.21 (bs, 1H), 7.06 (d, J=8.9 Hz, 2H), 4.80 (s, 2H).

Example 1226c

{4-[5-Chloro-2-(1-ethyl-2-oxo-2,3,4,5-tetrahydro-1H-1-benzazepin-8-ylamino)-pyrimidin-4-ylamino]-phenoxy}-acetonitrile was formed from 4-(2,5-Dichloro-pyrimidin-4-ylamino)-phenoxy]-acetonitrile and 8-Amino-1-ethyl-1,3,4,5-tetrahydro-1-benzazepin-2-one in an analogous manner to Example 1221d. (120° C., 20 min) as a white solid (96 mg, 76%). MP 133-136, LCMS 463.24 (M+H) HNMR (DMSO) 9.35 (bs, 1H), 8.85 (bs, 1H), 8.13 (s, 1H), 7.59-7.55 (m, 3H), 7.43 (d, J=8.2 Hz, 1H), 7.06-7.02 (m, 3H), 5.16 (s, 2H), 3.80-3.48 (bm, 2H), 2.56-2.52 (m, 2H), 2.10-1.92 (m, 4H), 0.94 (t, J=6.8 Hz, 3H).

Example 1227

2-{5-Chloro-2-[3-(2-methoxy-ethyl)-2,3,4,5-tetrahydro-1H-3-benzazepin-7-ylamino]-pyrimidin-4-ylamino}-3-hydroxy-N-methyl-benzamide

Example 1227a 2-(2,5-Dichloro-pyrimidin-4-ylamino)-3-methoxy-N-methyl-benzamide (0.100 g, 0.30 mmol) was dissolved in Methylene chloride (20 mL, 0.2 mol) and 1.00 M of Boron tribromide in Methylene chloride (2.14 mL) was added slowly, and the reaction mixture was stirred at rt for 16 h. The reaction mixture was quenched with H20 and the layers were separated. An insoluble yellow solid was filtered off, was dissolved in MeOH and combined with the CH2Cl2 layer. Title product isolated as a pale yellow solid (50 mg, 52%). MP 210-211, LCMS purity=87%, LCMS 313.09 (M+H), 1H-NMR (DMSO-d6, 400 MHz) δ 9.79 (s, 1H), 9.15 (s, 1H), 8.31 (d, J=1 Hz, 1H), 8.21 (d, J=4.3 Hz, 1H), 7.20-7.18 (m, 1H), 7.04-7.00 (m, 2H), 2.67 (d, J=4.5 Hz, 3H).

Example 1227b

2-{5-Chloro-2-[3-(2-methoxy-ethyl)-2,3,4,5-tetrahydro-1H-3-benzazepin-7-ylamino]-pyrimidin-4-ylamino}-3-hydroxy-N-methyl-benzamide was prepared from 2-(2,5-Dichloro-pyrimidin-4-ylamino)-3-methoxy-N-methyl-benzamide and 3-(2-Methoxy-ethyl)-2,3,4,5-tetrahydro-1H-benzo[d]azepin-7-ylamine (preparation in Example 34b) in an analogous manner to Example 1221d. Title product isolated as a white foam (10 mg, 15%), HPLC purity 99%. LCMS 497.09 (M+H), 1H-NMR (CDCl3, 400 MHz) δ:10.79 (s, 1H), 8.06 (s, 1H), 7.20-7.09 (m, 5H), 7.01 (d, J=8.0 Hz, 1H), 6.95 (s, 1H), 6.25 (d, J=4.8 Hz, 1H), 3.56 (d, J=5.6 Hz), 3.38 (s, 3H), 3.02 (d, J=4.8 Hz, 3H), 2.97-2.75 (m, 10H).

Example 1228

2-[2-(1-Acetyl-4-oxo-1,2,3,4,5,6-hexahydro-benzo[b][1,5]diazocin-8-ylamino)-5-chloro-pyrimidin-4-ylamino]-N-ethyl-3-fluoro-benzamide Title compound was prepared from 1-Acetyl-8-amino-2,3,5,6-tetrahydro-1H-benzo[b][1,5]diazocin-4-one and 2-(2,5-Dichloro-pyrimidin-4-ylamino)-N-ethyl-3-fluoro-benzamide in an analogous manner to Example 1221d (120° C., 80 min) Isolated 68 mg (34%) as a pale yellow foam. 98% HPLC purity, LCMS 526.16 (M+H), 1H-NMR (CDCl3, 400 MHz) δ 8.63 (s, 1H), 8.11 (s, 1H), 7.68 (s, 1H), 7.48-7.46 (m, 1H), 7.41 (s, 1H), 7.35-7.33 (m, 2H), 7.15 (d, J=8.1 Hz, 1H), 6.98 (d, J=8.5 Hz, 1H), 6.69 (bt 1H), 6.38 (bs, 1H), 4.77-4.74 (m, 1H), 4.26-4.20 (m, 1H), 3.69-3.64 (m, 1H), 3.47-3.36 (m, 2H), 2.99-2.93 (m, 1H), 2.66-2.60 (m, 1H), 2.55-2.50 (m, 1H), 1.77 (s, 3H), 1.14 (t, J=7.3 Hz, 3H).

Example 1229

{3-[5-Chloro-2-(1-ethyl-2-oxo-2,3,4,5-tetrahydro-1H-1-benzazepin-8-ylamino)-pyrimidin-4-ylamino]-phenyl}-acetonitrile

Example 1229a (2-Amino-phenyl)-acetonitrile. Into a Hydrogenation flask was added 3-(2-Nitro-phenyl)-acrylonitrile (0.892 g, 0.00512 mol), Methanol (20 mL, 0.5 mol), and 10% Pd/C (10:90, Palladium:carbon black, 0.090 g). The reaction mixture was shaken under 20 psi H2 for 60 min. Reaction mixture was filtered through celite, washed with MeOH, concentrated under reduced pressure Title compound isolated as an orange oil (791 mg, 97%).

Example 1229b

[3-(2,5-Dichloro-pyrimidin-4-ylamino)-phenyl]-acetonitrile was prepared from (3-Amino-phenyl)-acetonitrile and 2,4,5-Trichloro-pyrimidine in an analogous manner to Example 1223b. Title product was isolated as a beige solid (144 mg, 40%) after silica gel chromatography (ISCO 40 g 0-100% EtOAc in hexanes). 91% HPLC purity, MP=155-157, LCMS 279.11 (M+H), 1H-NMR (CDCl3, 400 MHz) δ 8.26 (s, 1H), 7.66 (d, J=8.6 Hz, 2H), 7.45 (dd, J=7.8 Hz, 1H), 7.28 (d, J=8.6 Hz, 1H), 7.17 (d, J=7.5 Hz, 1H), 3.82, s, 1H).

Example 1229c

{3-[5-Chloro-2-(1-ethyl-2-oxo-2,3,4,5-tetrahydro-1H-1-benzazepin-8-ylamino)-pyrimidin-4-ylamino]-phenyl}-acetonitrile was prepared from [3-(2,5-Dichloro-pyrimidin-4-ylamino)-phenyl]-acetonitrile and 8-Amino-1-ethyl-1,3,4,5-tetrahydro-1-benzazepin-2-one (from Example 358a) in an analogous manner to Example 1d. (120° C., 20 min). Title compound was isolated as a white foam: 99 mg (69%) HPLC purity 90%, LCMS: 447.25 (M+H), 1H-NMR (CDCl3, 400 MHz) δ 8.12 (s, 1H), 7.77 (s, 1H), 7.58 (s, 1H), 7.53 (d, J=8.1 Hz, 1H), 7.39-7.30 (m, 2H), 7.24 (d, J=7.8 Hz, 1H), 7.17 (s, 1H), 7.09 (d, J=8.0 Hz, 2H), 3.77 (s, 2H), 3.90-3.50 (bm, 2H), 2.71-2.60 (m, 2H), 2.34-2.23 (m, 2H), 2.05-2.12 (m, 2H), 1.08 (t, J=7.1 Hz, 3H).

Example 1230

{2-[5-Chloro-2-(1-ethyl-2-oxo-2,3,4,5-tetrahydro-1H-1-benzazepin-8-ylamino)-pyrimidin-4-ylamino]-phenoxy}-acetonitrile

Example 1230a

[2-(2,5-Dichloro-pyrimidin-4-ylamino)-phenoxy]-acetonitrile

Into an 80 ml microwave vessel was added 2,4,5-Trichloro-pyrimidine (1.86 g, 0.01 mol), (2-Amino-phenoxy)-acetonitrile (1.500 g, 0.01 mol), and N,N-DIEA (1.96 g, 0.015 mol), Isopropyl alcohol (20 mL, 0.3 mol). The reaction was microwaved at 120° C. for 60 minutes. The resulting orange suspension was filtered and the solid was washed with Isopropyl alcohol to afford a light pink solid (1.59 g, 53%). HPLC purity 95%.

Example 1230b

{2-[5-Chloro-2-(1-ethyl-2-oxo-2,3,4,5-tetrahydro-1H-1-benzazepin-8-ylamino)-pyrimidin-4-ylamino]-phenoxy}-acetonitrile was prepared from [2-(2,5-Dichloro-pyrimidin-4-ylamino)-phenoxy]-acetonitrile and 8-Amino-1-ethyl-1,3,4,5-tetrahydro-1-benzazepin-2-one in an analogous manner to. Example 12211d. (120° C., 20 min). Title compound was isolated as a white foam: 67 mg (61%) after silica gel chromatography (ISCO 12 g, 0-100% EtOAc in hexanes). HPLC purity 88%, LCMS 463.24 (M+H), 1H-NMR (CDCl3, 400 MHz) δ: 8.35 (d, J=8.0 Hz, 1H), 8.12 (s, 1H), 7.60 (s, 2H), 7.35 (s, 1H), 7.23 (d, J=6.5 Hz, 1H), 7.21-7.05 (m, 4H), 4.90

(s, 2H), 3.90-3.50 (bm, 2H), 2.71-2.60 (m, 2H), 2.34-2.23 (m, 2H), 2.05-2.12 (m, 2H), 1.08 (t, J=7.1 Hz, 3H).

Example 1231

{2-[2-(1-Acetyl-4-oxo-1,2,3,4,5,6-hexahydro-benzo[b][1,5]diazocin-8-ylamino)-5-chloro-pyrimidin-4-ylamino]-phenoxy}-acetonitrile Title compound was prepared from [2-(2,5-Dichloro-pyrimidin-4-ylamino)-phenoxy]-acetonitrile and Acetyl-8-amino-2,3,5,6-tetrahydro-1H-benzo[b][1,5]diazocin-4-one in an analogous manner to Example 1221d. (120° C., 40 min). Title compound isolated (70 mg, 47%) as an off-white solid. MP 233-234, LCMS 492.27 (M+H), HPLC purity 98%, 1H-NMR (CDCl3, 400 MHz) δ 8.27 (d, 7.9 Hz, 1H), 8.15 (s, 1H), 7.78 (s, 1H), 7.54 (s, 1H), 7.40 (s, 1H), 7.38 (d, J=8.5 Hz, 1H), 7.30-7.21 (m, 2H), 7.18-7.09 (m, 3H), 6.08 (bt, J=5.1 Hz, 1H), 4.93 (s, 2H), 4.88-4.82 (m, 1H), 4.39-4.33 (m, 1H), 3.83-3.78 (m, 1H), 3.82-3.75 (m, 1H), 3.08-3.02 (m, 1H), 2.81-2.74 (m, 1H), 2.64-2.59 (m, 1H), 1.83 (s, 3H).

Example 1232

3-{2-[5-Chloro-2-(1-ethyl-2-oxo-2,3,4,5-tetrahydro-1H-1-benzazepin-8-ylamino)-pyrimidin-4-ylamino]-phenyl}-propionitrile

Example 1232a 3-(2-Nitro-phenyl)-acrylonitrile. Sodium hydride, 60% disp. in mineral oil (0.265 g) was added in portions to a solution of Diethyl cyanomethylphosphonate (1.17 g, 6.6 mmol) in anhydrous DMF (20 mL, 0.2 mol) under stirring and ice cooling. A solution of 2-Nitrobenzaldehyde (1.00 g, 6.6 mmol) in DMF (5 mL) was then added dropwise over 10 min. After being stirred for 5 min, the reaction mixture was poured into ice water, neutralized with ammonium chloride, and extracted with ether. The organic solution was dried over MgSO4, filtered, and concentrated under reduced pressure. A mixture of E and Z 3-(2-Nitro-phenyl)-acrylonitrile was isolated (892 mg, combined yield=77%.)

Example 1232b 3-(2-Amino-phenyl)-propionitrile was obtained from 3-(2-Nitro-phenyl)-acrylonitrile in an analogous manner to Example 1229a. Title product obtained as orange oil (295 mg, 40%).

Example 1232c

3-[2-(2,5-Dichloro-pyrimidin-4-ylamino)-phenyl]-propionitrile was prepared from 3-(2-Amino-phenyl)-propionitrile and 2,4,5-Trichloro-pyrimidine in an analogous manner to Example 1230a. Title product was isolated as an off white solid (554 mg, 94%), MP: 115-116, LCMS 293.10 (M+H), HPLC purity: 92%, 1H-NMR (CDCl3, 400 MHz) δ:8.24 (s, 1H), 7.48-7.45 (m, 1H), 7.39-7.36 (m, 3H), 7.19 (bs, 1H), 2.98 (t, J=7.2 Hz, 2H), 2.71 (t, J=7.2 Hz, 2H).

Example 1232d

3-{2-[5-Chloro-2-(1-ethyl-2-oxo-2,3,4,5-tetrahydro-1H-1-benzazepin-8-ylamino)-pyrimidin-4-ylamino]-phenyl}-propionitrile was prepared from [2-(2,5-Dichloro-pyrimidin-4-ylamino)-phenoxy]-acetonitrile and 8-Amino-1-ethyl-1,3,4,5-tetrahydro-1-benzazepin-2-one (from Example 358a) in an analogous manner to Example 1221d. (120° C., 40 min). Obtained 83 mg (76%) as a white foam. HPLC purity: 90%, LCMS 461.22 (M+H), 1H-NMR (CDCl3, 400 MHz) δ: 8.09 (s, 1H), 7.46-7.42 (m, 1H), 7.41-7.31 (m, 4H), 7.28 (s, 1H), 7.05-6.92 (m, 3H), 4.00-3.20 (bm, 2H), 2.97 (t, J=7.2 Hz, 2 h), 2.61 (t, J=7.2 Hz, 2H), 2.28-2.22 (m, 2H), 2.22-2.2.05 (m, 2H), 1.00 (t, J=7.1 Hz, 3H).

Example 1233

3-{2-[2-(1-Acetyl-4-oxo-1,2,3,4,5,6-hexahydro-benzo[b][1,5]diazocin-8-ylamino)-5-chloro-pyrimidin-4-ylamino]-phenyl}-propionitrile Title compound was prepared from [2-(2,5-Dichloro-pyrimidin-4-ylamino)-phenoxy]-acetonitrile and Acetyl-8-amino-2,3,5,6-tetrahydro-1H-benzo[b][1,5]diazocin-4-one in an analogous manner to Example 1221d. (120° C., 40 min). Obtained 82 mg (55%) as a white foam. HPLC purity: 96%, LCMS 490.16 (M+H), 1H-NMR (CDCl3, 400 MHz) δ: 8.10 (s, 1H), 7.59 (s, 1H), 7.51-7.45 (m, 5H), 7.08-7.03 (m, 1H), 6.99-6.94 (m, 2H), 6.09 (bt, 1H), 4.81-4.76 (m, 1H), 4.22-4.18 (m, 1H), 3.45 3.41 (m, 1H), 3.01 (t, J=7.1 Hz, 2H), 3.00-2.97 (m, 1H), 2.72-2.63 (m, 3H), 2.58-2.53 (m, 1H), 1.76 (s, 3H).

Example 1234

8-[5-Chloro-4-(2-methoxy-4-morpholin-4-yl-phenylamino)-pyrimidin-2-ylamino]-5,5-dimethyl-1,3,4,5-tetrahydro-1-benzazepin-2-one Title compound was prepared from 8-Amino-5,5-dimethyl-1,3,4,5-tetrahydro-benzo[b]azepin-2-one and (2,5-Dichloro-pyrimidin-4-yl)-(2-methoxy-4-morpholin-4-yl-phenyl)-amine in an analogous manner to Example 1221d. The product was isolated as a bright yellow solid (160 mg, 84%): MP 232-235, HPLC purity 95%, LCMS 524 (M+H), HMNR (CDCl3): 10.68 (s, 1H), 8.21 (s, 1H), 7.90 d, J=8.1 Hz, 1H), 7.82 (s, 1H), 7.49 (s, 1H), 7.36 (d, J=8.4 Hz, 1H), 7.15 (d, J=8.4 Hz, 1H) 6.99 (s, 1H), 6.61 (s, 1H), 6.52 (d, J=9.0 Hz, 1H), 3.94 (m, 7H), 3.30 (m, 4H), 2.41 (t, J=7.0 Hz, 2H), 2.12 (t, J=7.2 Hz, 2H), 1.42 (s, 6H).

Example 1235

2-[5-Chloro-2-(5,5-dimethyl-2-oxo-2,3,4,5-tetrahydro-1H-1-benzazepin-7-ylamino)-pyrimidin-4-ylamino]-N-methyl-4-nitro-benzamide

Example 1235a

7-Nitro-1H-3,1-benzoxazine-2,4-dione. 2-Amino-4-nitrobenzoic acid (1.00 g, 0.00549 mol) was dissolved in THF. Triphosgene (1.63 g, 0.00549 mol) was dissolved in THF and added. The reaction mixture was stirred at rt for 2 h, concentrated, triturated with H2O, filtered, and taken up in acetone to afford a pale yellow solid (1.14 g, 99.8%).

Example 1235b

2-Amino-N-methyl-4-nitro-benzamide. 7-Nitro-1H-3,1-benzoxazine-2,4-dione (1.14 g, 0.00549 mol) was dissolved in THF (50 mL, 0.6 mol). 2 M of Methylamine in THF (10 mL) was added, and a yellow solid formed immediately. The reaction mixture was concentrated under reduced pressure to afford a light orange solid.

Example 1235c 2-(2,5-Dichloro-pyrimidin-4-ylamino)-N-methyl-4-nitro-benzamide was prepared from 2-Amino-N-methyl-4-nitro-benzamide and 2,4,5-Trichloro-pyrimidine in an analogous manner to Example 1223b. Product was isolated as an orange solid (711 mg, 81%) MP 241 (dec), LCMS 344.10, HPLC purity 80%, 1H-NMR (CDCl3, 400 MHz) δ: 11.72 s, 1H), 9.73 (s, 1H), 8.33 (s, 1H), 7.98 (8.6 Hz, 1H), 7.69 (8.5 Hz, 1H), 6.37 (m, 1H), 3.11 (d, J=4.8 Hz, 3H).

Example 1235d

2-[5-Chloro-2-(5,5-dimethyl-2-oxo-2,3,4,5-tetrahydro-1H-1-benzazepin-7-ylamino)-pyrimidin-4-ylamino]-N-methyl-4-nitro-benzamide was prepared from 2-(2,5-Dichloro-pyrimidin-4-ylamino)-N-methyl-4-nitro-benzamide and 7-Amino-5,5-dimethyl-1,3,4,5-tetrahydro-benzo[b]azepin-2-one in an analogous manner to Example 1221d. The product was isolated as an orange-yellow solid. 88% HPLC purity, LCMS 510.21, MP 247-248, 1H-NMR (CDCl3, 400 MHz) δ: 11.19 (s, 1H), 9.57 (s, 1H), 8.20 (s, 1H), 7.88 (d, J=6.6 Hz, 1H), 7.66 (d, J=8.3 Hz, 1H), 7.59 (d, J=8.8 Hz, 1H), 7.37 (s, 1H), 7.06 (s, 1H), 6.97 (s, 1H), 6.84 (d, J=8.3 Hz, 1H), 6.30 (m, 1H), 3.10 (d, J=4.8 Hz, 3H), 2.41 (t, J=6.8 Hz, 2H), 2.10 (t, J=7.1 Hz, 2H), 1.40 (s, 6H).

Example 1236

(1S,2S,3R,4R)-3-[5-Chloro-2-(5,5-dimethyl-2-oxo-2,3,4,5-tetrahydro-1H-1-benzazepin-8-ylamino)-pyrimidin-4-ylamino]-bicyclo[2.2.1]hept-5-ene-2-carboxylic acid amide Title compound was prepared from 8-Amino-5,5-dimethyl-1,3,4,5-tetrahydro-benzo[b]azepin-2-one and (1S,2S,3R,4R)-3-(2,5-Dichloro-pyrimidin-4-ylamino)-bicyclo[2.2.1]hept-5-ene-2-carboxylic acid amide in a manner analogous to Example 1221d. (120° C., 30 min). Product was isolated as a white foam (82 mg, 49%), HPLC purity 90%, LCMS 467.24 (M+H), 1H-NMR (CDCl3, 400 MHz) δ 9.52 (bs, 1H), 9.08 (bs, 1H), 7.88 (bs, 1H), 7.80 (s, 1H), 7.72 (s, 1H), 7.32 (s, 1H), 6.95 bs, 1H), 6.67 (bs, 1H), 6.31-6.28 (m, 1H), 6.18-6.16 (m, 1H), 4.26 (t, J=7.6 Hz, 1H), 3.05 (s, 1H), 2.94 (s, 1H), 2.65 (d, J=8.0 Hz, 1H), 2.56-2.50 (m, 1H), 2.47-2.36 (m, 1H), 2.17-2.10 (m, 3H), 1.54 (d, J=8.8 Hz, 1H), 1.42 (s, 6H).

Example 1237

3-{2-[2-(1-Acetyl-4-oxo-1,2,3,4,5,6-hexahydro-1,5-benzodiazepin-8-ylamino)-5-chloro-pyrimidin-4-ylamino]-phenoxy}-propionitrile Title compound was prepared from 3-[2-(2,5-Dichloro-pyrimidin-4-ylamino)-phenoxy]-propionitrile and 1-Acetyl-8-amino-2,3,5,6-tetrahydro-1H-benzo[b][1,5]diazocin-4-one in a manner analogous to Example 1221d. Product was isolated as a pale yellow foam (29 mg, 19%). LCMS 506.22 (M+H), HPLC purity: 90%, 1H-NMR (CDCl3, 400 MHz) δ 8.33 (d, J=7.9 Hz, 1H), 8.11 (s, 1H), 7.79 (d, J=11.2 Hz, 2H), 7.47 (s, 1H), 7.40 (d, J=8.5 Hz, 1H), 7.17-7.11 (m, 2H), 7.08-7.04 (m, 1H), 6.96 (d, J=8.0 Hz, 1H), 6.33-6.31 (m, 1H), 4.87-4.82 (m, 1H), 4.39-4.32 (m, 3H), 3.86-3.81 (m, 1H), 3.09-3.02 (m, 1H), 2.93 (t, J=6.1 Hz, 2H), 2.80-2.74 (m, 1H), 2.64-2.60 (m, 1H), 1.83 (s, 1H).

Example 1238

3-{2-[5-Chloro-2-(5,5-dimethyl-2-oxo-2,3,4,5-tetrahydro-1H-1-benzazepin-8-ylamino)-pyrimidin-4-ylamino]-phenoxy}-propionitrile Title compound was prepared from 3-[2-(2,5-Dichloro-pyrimidin-4-ylamino)-phenoxy]-propionitrile and 8-Amino-5,5-dimethyl-1,3,4,5-tetrahydro-benzo[b]azepin-2-one in a manner analogous to Example 1221d. Product was isolated as an off-white foam (96 mg, 56%). 95% HPLC purity, LCMS 477.24 (M+H), 1H-NMR (CDCl3, 400 MHz) δ 8.37 (d, J=8.0 Hz, 1H), 8.25 (s, 1H), 8.07-8.05 (m, 2H), 7.75 (s, 1H), 7.55 (s, 1H), 7.33 (d, J=8.6 Hz, 1H), 7.14-7.08 (m, 2H), 7.01 (t, J=7.7 Hz, 1H), 6.86 (d, J=8.0 Hz, 1H), 4.24 (t, J=7.9 Hz, 2H), 2.88 (t, J=6.2 Hz, 2H), 2.46 (t, J=6.8 Hz, 2H), 2.12 (t, J=6.6 Hz, 2H), 1.42 (s, 6H).

Example 1239

4-Amino-2-[5-chloro-2-(5,5-dimethyl-2-oxo-2,3,4,5-tetrahydro-1H-1-benzazepin-7-ylamino)-pyrimidin-4-ylamino]-N-methyl-benzamide 2-[5-Chloro-2-(5,5-dimethyl-2-oxo-2,3,4,5-tetrahydro-1H-1-benzazepin-7-ylamino)-pyrimidin-4-ylamino]-N-methyl-4-nitro-benzamide (0.050 g, 0.1 mmol); Iron (0.03 g, 0.5 mmol), and HCl (2 mL, 0.06 mol) were combined in a vial and heated to 50° C. for 30 mins. About 50% conversion to desired product was seen. After an additional 60 min, no further conversion occurred, and byproduct formation began. The reaction mixture was neutralized with NaOH and extracted with CH2Cl2. The organic layer was dried over MgSO4, filtered, and concentrated under reduced pressure. Title compound was obtained as a white solid (5 mg. 10%), MP=265 (dec), LCMS: 480.23, HPLC purity 99%, 1H-NMR (CDCl3, 400 MHz) δ 11.73 (s, 1H), 8.11 (s, 1H), 8.10 (m, 1H), 7.77 (d, J=8.3 Hz, 1H), 7.31 (d, J=8.3 Hz, 2H), 7.08 (s, 1H), 6.92 (d, J=8.5 Hz, 1H), 6.33 (m, 1H), 3.92 (s, 2H), 3.01 (d, J=4.7 Hz, 3H), 2.40 (m, 2H), 2.13 (m, 2H), 1.41 (s, 6H).

Example 1240

(2-{5-Chloro-2-[3-(2-methoxy-ethyl)-2,3,4,5-tetrahydro-1H-3-benzazepin-7-ylamino]-pyrimidin-4-ylamino}-phenoxy)-acetonitrile Title compound was prepared from 3-(2-Methoxy-ethyl)-2,3,4,5-tetrahydro-1H-benzo[d]azepin-7-ylamine and [2-(2,5-Dichloro-pyrimidin-4-ylamino)-phenoxy]-acetonitrile in a manner analogous to Example 1221d. Product was isolated as an off-white solid (298 mg, 36%), MP=99-100, LCMS 479.23 (M+H), HPLC purity 99%, 1H-NMR (CDCl3, 400 MHz) δ 8.45 (d, J=7.6 Hz, 1H), 8.08 (s, 1H), 7.62 (s, 1H), 7.38-7.33 (m, 2H), 7.21 (d, 8.0 Hz, 1H) 7.13-7.72 (m, 4H), 4.87 (s, 2H), 3.56 (t, J=5.7 Hz, 2H), 3.39 (s, 3H), 2.97-2.90 (m, 4H), 2.79-2.2.73 (m, 6H).

Example 1241

2-(2-{5-Chloro-2-[3-(2-methoxy-ethyl)-2,3,4,5-tetrahydro-1H-3-benzazepin-7-ylamino]-pyrimidin-4-ylamino}-phenoxy)-acetamide (2-{5-Chloro-2-[3-(2-methoxy-ethyl)-2,3,4,5-tetrahydro-1H-3-benzazepin-7-ylamino]-pyrimidin-4-ylamino}-phenoxy)-acetonitrile (0.100 g, 0.2 mmol) and NaOH (1 mL, 0.05 mol) (50% solution) and water (1 mL) were heated at 100° C. for 16 h. The resulting ppt was filtered from the reaction mixture. Product was isolated as a white solid (20 mg, 19%), MP=123-125. LCMS 497.22 (M+H), HPLC purity 99+%, 1H-NMR (DMSO-d6, 400 MHz) δ 9.66 (m, 1H), 9.38 (s 1H), 8.65 (s, 1H), 8.16 (s, 1H), 7.90 d, 1H), 7.50 (m, 2H), 7.46 (s, 1H), 7.31 (d, 1H), 7.16 (m, 1H), 7.02 (m, 3H), 4.55 (s, 2H), 3.73 (m, 2H), 3.64 (m, 2H), 3.38 (m, 2H), 3.34 (s, 3H), 3.15-2.88 (m, 5H), 2.68 (m, 1H).

Example 1242

(2-{5-Chloro-2-[3-(2-methoxy-ethyl)-2,3,4,5-tetrahydro-1H-3-benzazepin-7-ylamino]-pyrimidin-4-ylamino}-phenoxy)-acetic acid From Example 1231: isolated as a white solid, (7 mg, 7%) MP=198-199. LCMS 498.15 (M+H), HPLC purity 99+%, 1H-NMR (DMSO-d6, 400 MHz) δ 13.20 (s, 1H), 9.70 (s, 1H), 9.44 (s, 1H), 8.45 (s, 1H), 8.19 (s, 1H), 8.10 (m, 1H), 7.56 (s, 1H), 7.35 (d, 1H), 7.13 (m, 2H), 7.07 (m, 2H), 4.80 (s, 2H), 3.70 (m, 2H), 3.63 (m, 2H), 3.34 (m, 2H), 3.32 (s, 3H), 3.20-2.90 (m, 5H), 2.76 (m, 1H).

Example 1243

8-{5-Chloro-4-[2-(propane-2-sulfonyl)-phenylamino]-pyrimidin-2-ylamino}-1-ethyl-5,5-dimethyl-1,3,4,5-tetrahydro-1-benzazepin-2-one Title compound was prepared from 8-Amino-1-ethyl-5,5-dimethyl-1,3,4,5-tetrahydro-benzo[b]azepin-2-one and (2,5-Dichloro-pyrimidin-4-yl)-[2-(propane-2-sulfonyl)-phenyl]-amine in an analogous manner to Example 1221d. Product was isolated as a white solid (62 mg, 55%). LCMS: 542.20 (M+H), HPLC purity: 100%, MP: 202-204. 1H-NMR (CDCl3, 400 MHz) δ 10.34 (s, 1H), 8.42 (d, J=8.3 Hz, 1H), 8.04 (s, 1H), 7.98 (d, J=7.9 Hz, 1H), 7.55-7.49 (m, 2H), 7.43-7.34 (m, 2H), 7.28-7.27 (m, 2H), 3.66-3.63 (m, 2H), 3.26-3.22 (m, 1H), 2.35-2.32 (m, 2H), 2.12-2.06 (m, 2H), 1.38-1.34 (m, 12H), 1.10 (t, J=7.3 Hz, 3H).

Example 1244

4-Acetylamino-2-[5-chloro-2-(5,5-dimethyl-2-oxo-2,3,4,5-tetrahydro-1H-1-benzazepin-7-ylamino)-pyrimidin-4-ylamino]-N-methyl-benzamide Example 1244a 4-Amino-2-(2,5-dichloro-pyrimidin-4-ylamino)-N-methyl-benzamide. 2-(2,5-Dichloro-pyrimidin-4-ylamino)-N-methyl-4-nitro-benzamide (0.248 g, 0.72 mmol), Iron (0.202 g, 3.62 mmol), and HCl (3 mL, 0.1 mol) were heated at 50° C. for 1 h. The reaction mixture was neutralized with NaOH and extracted with CH2Cl2. The suspension was filtered, and the resulting solids were washed with CH2Cl2 and EtOAc. The combined organic layers were dried over MgSO4, filtered, and concentrated under reduced pressure to afford 135 mg (60%) title compound.

Example 1244b

4-Acetylamino-2-(2,5-dichloro-pyrimidin-4-ylamino)-N-methyl-benzamide. 4-Amino-2-(2,5-dichloro-pyrimidin-4-ylamino)-N-methyl-benzamide (0.135 g, 0.000432 mol), Acetic anhydride (0.0428 mL, 0.000454 mol), THF (5 mL, 0.06 mol) and Acetic acid (0.024 mL, 0.43 mol) were stirred at rt for 16 h. Product isolated as white ppt (80 mg, 52%).

Example 1244c

4-Acetylamino-2-[5-chloro-2-(5,5-dimethyl-2-oxo-2,3,4,5-tetrahydro-1H-1-benzazepin-7-ylamino)-pyrimidin-4-ylamino]-N-methyl-benzamide was prepared from 7-Amino-5,5-dimethyl-1,3,4,5-tetrahydro-benzo[b]azepin-2-one and 4-Acetylamino-2-(2,5-dichloro-pyrimidin-4-ylamino)-N-methyl-benzamide in an analogous manner to Example 1221d. Title compound was isolated as a white powder, 27 mg, 35%. MP >300, LCMS: 522.21 (M+H), HPLC purity 100%, 1H-NMR (DMSO-d6, 400 MHz) δ 11.60 (s, 1H), 9.99 (s, 1H), 9.39 (s, 1H), 9.27 (s, 1H), 8.61 (d, J=4.5 Hz, 1H), 8.53 (s, 1H), 8.23 (s, 1H), 7.72-7.68 (m, 2H), 7.57 (d, J=8.8 Hz, 1H), 7.50 (s, 1H), 6.78 (d, J=8.6 Hz, 1H), 2.78 (d, J=3.9 Hz, 3H), 2.15-2.13 (m, 2H), 2.03 (s, 3H), 1.98-1.96 (m, 2H).

Example 1245

(2-{5-Chloro-2-[3-(2-methoxy-ethyl)-2,3,4,5-tetrahydro-1H-3-benzazepin-7-ylamino]-pyrimidin-4-ylamino}-3-methyl-phenoxy)-acetonitrile Example 1245a (2-Amino-3-methyl-phenoxy)-acetonitrile. Into a 1-Neck round-bottom flask was added 2-Amino-3-methyl-phenol (1.00 g, 0.00812 mol), Chloroacetonitrile (0.617 mL, 0.00974 mol), K2CO3 (1.35 g, 9.7 mmol), and Acetone (15 mL, 0.20 mol). The reaction mixture was heated at 50° C. for 4 hr, filtered and concentrated to afford title product (670 mg, 51%) LCMS 163 (M+H).

Example 1245b

[2-(2,5-Dichloro-pyrimidin-4-ylamino)-3-methyl-phenoxy]-acetonitrile was prepared from (2-Amino-3-methyl-phenoxy)-acetonitrile and 2,4,5-Trichloropyrimidine in an analogous manner to Example 1230a. Title product obtained as an off-white solid, 365 mg, 29%. MP: 134-136, LCMS 309.07 (M+H), HPLC purity 75%, 1H-NMR (CDCl3, 400 MHz) δ 8.20 (s, 1H), 7.31-7.27 (m, 1H), 7.07 (d, J=7.7 Hz, 1H), 6.95 (d, J=8.2 Hz, 1H), 6.82 (s, 1H), 4.79 (s, 2H), 2.27 (s, 3H).

Example 1245c (2-{5-Chloro-2-[3-(2-methoxy-ethyl)-2,3,4,5-tetrahydro-1H-3-benzazepin-7-ylamino]-pyrimidin-4-ylamino}-3-methyl-phenoxy)-acetonitrile was prepared from 3-(2-Methoxy-ethyl)-2,3,4,5-tetrahydro-1H-benzo[d]azepin-7-ylamine and [2-(2,5-Dichloro-pyrimidin-4-ylamino)-3-methyl-phenoxy]-acetonitrile in an analogous manner to Example 1221d. Title compound isolated as a white foam, (60 mg, 45%) LCMS 493.18 (M+H), HPLC purity 99%, 1H-NMR (CDCl3, 400 MHz) δ:8.04 (s, 1H), 7.32-7.28 (m, 1H), 7.11-7.08 (m, 2H), 7.03 (s, 1H), 6.96-6.93, (m, 2H), 6.83 (d, J=8.0 Hz, 1H), 6.57 (s, 1H), 4.70 (s, 2H), 3.55 (dd, J=5.6 Hz, 2H), 3.38 (s, 3H), 2.85-2.81 (m, 2H), 2.75 (dd, J=5.6 Hz, 2H), 2.72-2.67 (m, 6H), 2.28 (s, 3H).

Example 1246

{2-[2-(1-Acetyl-4-oxo-1,2,3,4,5,6-hexahydro-benzo[b][1,5]diazocin-8-ylamino)-5-chloro-pyrimidin-4-ylamino]-3-methyl-phenoxy}-acetonitrile Title compound was prepared from 1-Acetyl-8-amino-2,3,5,6-tetrahydro-1H-benzo[b][1,5]diazocin-4-one and [2-(2,5-

Dichloro-pyrimidin-4-ylamino)-3-methyl-phenoxy]-acetonitrile in an analogous manner to Example 1221d. Product was isolated as a white solid (104 mg, 76%). MP: 210-214, LCMS 506.15 (M+H), HPLC purity 97%, 1H-NMR (DMSO-d6, 400 MHz) δ 9.65-9.63 (m, 1H), 8.83-8.85 (m, 1H), 8.15 (s, 1H), 7.6307.61 (m, 1H), 7.36-7.32 (m, 3H), 7.14 (d, J=8.5 Hz, 1H), 7.07 (d, J=7.7 Hz, 1H), 6.90 (d, J=8.6 Hz, 1H), 5.11 (s, 2H), 2.58-2.54 (m, 2H), 4.15-4.11 (m, 1H), 3.60-3.52 (m, 1H), 2.85-2.81 (m, 1H), 2.28-2.24 (m, 1H), 2.16 (s, 3H), 1.60 (s, 3H).

Example 1247

{2-[2-(1-Acetyl-4-oxo-1,2,3,4,5,6-hexahydro-benzo[b][1,5]diazocin-8-ylamino)-5-chloro-pyrimidin-4-ylamino]-3-methyl-phenoxy}-acetonitrile Title compound was prepared from 8-Amino-1-(2-methoxy-ethyl)-5,5-dimethyl-1,3,4,5-tetrahydro-benzo[b]azepin-2-one and [2-(2,5-Dichloro-pyrimidin-4-ylamino)-3-methyl-phenoxy]-acetonitrile in an analogous manner to Example 1221d. Product was isolated as a white solid (91 mg, 62%). LCMS 535.20 (M+H), MP 225-228, HPLC purity 93%, 1H-NMR (DMSO-d6, 400 MHz) δ 9.70-9.64 (bs, 1H), 9.07-9.03 (bs, 1H), 8.18 (s, 1H), 7.35-7.30 (m, 2H), 7.19-7.17 (m, 1H), 7.11 (d, J=8.1 Hz, 1H), 7.04 (d, J=7.6 Hz, 1H), 6.79 (d, J=8.7 Hz, 1H), 5.08 (s, 2H), 3.62-3.58 m, 2H), 3.52-3.49 (m, 2H), 3.21 (s, 3H), 2.17 (s, 2H), 2.09-2.06 (m, 2H), 1.90-1.87 (m, 2H), 1.21 (m, 6H).

Example 1248

8-[5-Chloro-4-(2-methanesulfonyl-phenylamino)-pyrimidin-2-ylamino]-1-ethyl-5,5-dimethyl-1,3,4,5-tetrahydro-1-benzazepin-2-one Title compound was prepared from 8-Amino-1-ethyl-5,5-dimethyl-1,3,4,5-tetrahydro-benzo[b]azepin-2-one and (2,5-Dichloro-pyrimidin-4-yl)-(2-methanesulfonyl-phenyl)-amine in an analogous manner to Example 1221d. Product was isolated as a white solid (36 mg, 32%). MP=209-210, LCMS 514.09 (M+H), HPLC purity 91%, 1H-NMR (CDCl3, 400 MHz) δ 9.39 (s, 1H), 8.50 (d, J=8.4 Hz, 1H), 8.21 (s, 1H), 8.02 (d, J=7.9 Hz, 1H), 7.63-7.58 (m, 2H), 7.32-7.25 (m, 3H), 7.05-7.03 (m, 1H), 3.75-3.65 (m, 2H), 3.10 (s, 3H), 2.37-2.27 (m, 2H), 2.08-2.04 (m, 2H), 1.35 (s, 6H), 1.20 (t, J=9.8 Hz, 3H).

Example 1249

5-Chloro-N(4)-(2-methanesulfonyl-phenyl)-N(2)-[3-(2-methoxy-ethyl)-2,3,4,5-tetrahydro-1H-3-benzazepin-7-yl]-pyrimidine-2,4-diamine Title compound was prepared from 3-(2-Methoxy-ethyl)-2,3,4,5-tetrahydro-1H-benzo[d]azepin-7-ylamine and (2,5-Dichloro-pyrimidin-4-yl)-(2-methanesulfonyl-phenyl)-amine in an analogous manner to Example 1221d. Product was isolated as a white solid (34 mg, 31%). LCMS 504.08 (M+H), MP 184-188, HPLC purity 99%, 1H-NMR (CDCl3, 400 MHz) δ 11.70 (s, 1H), 10.25 (s, 1H), 8.38 (d, J=8.3 Hz, 1H), 8.07 (d, J=7.8 Hz, 1H), 7.98 (s, 1H), 7.58-7.54 (m, 1H), 7.50-7.42 (m, 2H), 7.34 (s, 1H), 7.12 (d, J=8.6 Hz, 1H), 3.98-3.88 (m, 2H), 3.85-3.78 (m, 2H), 3.65-3.50 (m, 2H), 3.37 (s, 5H), 2.92 (s, 3H), 2.98-2.80 (m, 4H).

Example 1250

7-[5-Chloro-4-(2-methanesulfonyl-phenylamino)-pyrimidin-2-ylamino]-1,5,5-trimethyl-1,3,4,5-tetrahydro-1-benzazepin-2-one Title compound was prepared from 7-Amino-1,5,5-trimethyl-1,3,4,5-tetrahydro-benzo[b]azepin-2-one and (2,5-Dichloro-pyrimidin-4-yl)-(2-methanesulfonyl-phenyl)-amine in an analogous manner to Example 1221d. Product was isolated as a white solid (63 mg, 58%). LCMS: 501.11 (M+H), HPLC purity 99%, MP 105-109, 1H-NMR (CDCl3, 400 MHz) δ 12.01 (s, 1H), 10.27 (s, 1H), 8.34 (d, J=8.2 Hz, 1H), 8.08 (d, J=7.7 Hz, 1H), 8.05 (s, 1H), 7.57-7.44 (m, 4H), 7.15 (d, J=8.6 Hz, 1H), 3.35 (s, 3H), 3.14 (s, 3H), 2.34 (t, J=7.0 Hz, 2H), 2.07-2.03 (m, 2H), 1.24 (s, 6H).

Example 1251

8-{5-Chloro-4-[2-fluoro-6-(propane-2-sulfonyl)-phenylamino]-2-ylamino}-5,5-dimethyl-1,3,4,5-tetrahydro-1-benzazepin-2-one Example 1251a 1-Fluoro-3-isopropylsulfanyl-2-nitro-benzene. 1,3-Difluoro-2-nitro-benzene (5.00 g, 31.4 mmol) was stirred in Ethanol (25 mL, 430 mmol) and treated with sodium 2-propanethiolate (3.08 g, 31.4 mmol) in several portions over 5 min. The reaction mixture was stirred at rt for 30 mins, was concentrated under reduced pressure, diluted with water, and extracted with CH2Cl2. The organic layer was dried over MgSO4, filtered, and concentrated under reduced pressure to afford a yellow oil.

Example 1251b

1-Fluoro-2-nitro-3-(propane-2-sulfonyl)-benzene. 8 M of H2O2 in Water (4.4 mL) was added to a solution of 1-Fluoro-3-isopropylsulfanyl-2-nitro-benzene (6.76 g, 0.031 mol) in Acetic acid (10 mL, 0.2 mol), and the reaction was heated at 100° C. for 16 h HPLC. Addition 2.5 eq H2O2 added. The reaction mixture was cooled and added to ice, when the product precipitated, and was collected by filtration, washed with water and dried under vacuum.

Example 1251c

2-Fluoro-6-(propane-2-sulfonyl)-phenylamine was prepared from 1-Fluoro-2-nitro-3-(propane-2-sulfonyl)-benzene in an analogous manner to Example 1c; isolated as a white solid.

Example 1251d (2,5-Dichloro-pyrimidin-4-yl)-[2-fluoro-6-(propane-2-sulfonyl)-phenyl]-amine. 2-Fluoro-6-(propane-2-sulfonyl)-phenylamine (3.10 g, 14 mmol) in DMF (10 mL, 0.1 mol) was treated with Sodium hydride, 60% disp. in mineral oil (1.14 g) at 0° C., then 2,4,5-Trichloro-pyrimidine (1.80 mL, 0.0157 mol) was added. The reaction was stirred for 30 minutes at 0° C. and then allowed to warm to rt and stirred at rt for 3 hrs. The reaction mixture was quenched with sat'd NH4Cl Product isolated as an off-white solid: 3.24 g, 62%. MP 192-193, LCMS 365.97 (M+H), HPLC purity 97%, 1H-NMR (CDCl3, 400 MHz) δ 8.57 (s, 1H), 8.31 (s, 1H), 7.80 (d, J=8.0 Hz, 1H), 7.53-7.50 (m, 2H), 3.10-3.00 (m, 1H), 1.28 (d, J=5.8 Hz, 6H).

Example 1251e

8-{5-Chloro-4-[2-fluoro-6-(propane-2-sulfonyl)-phenylamino]-pyrimidin-2-ylamino}-5,5-dimethyl-1,3,4,5-tetrahydro-1-benzazepin-2-one was prepared from 8-Amino-5,5-dimethyl-1,3,4,5-tetrahydro-benzo[b]azepin-2-one and (2,5-Dichloro-pyrimidin-4-yl)-[2-fluoro-6-(propane-2-sulfonyl)-phenyl]-amine in an analogous manner to Example 1251d. (120° C., 60 minutes). Title compound isolated as an off-white solid (68 mg, 48%). LCMS 534.13 (M+H), HPLC purity 98%, 1H-NMR (CDCl3, 400 MHz) δ: 8.17 (d, J=8.6 Hz, 1H), 8.17 (s, 1H), 7.86 (d, J=7.6 Hz, 1H), 7.58-7.54 (m, 2H), 7.24 (d, J=8.7 Hz, 1H), 6.96 (s, 1H), 6.89 (d, J=7.4 Hz, 1H), 6.76 (s, 1H), 3.10-3.02 (m, 1H), 2.38 (dd, J=6.7 Hz, 2H), 2.08 (dd, J=7.0 Hz, 2H), 1.38 (s, 6H), 1.23 (d, J=6.8 Hz, 6H).

Example 1252

8-{5-Chloro-4-[2-fluoro-6-(propane-2-sulfonyl)-phenylamino]-pyrimidin-2-ylamino}-1-ethyl-5,5-dimethyl-1,3,4,5-tetrahydro-1-benzazepin-2-one Title compound was prepared from 8-Amino-1-ethyl-5,5-dimethyl-1,3,4,5-tetrahydro-benzo[b]azepin-2-one and (2,5-Dichloro-pyrimidin-4-yl)-[2-fluoro-6-(propane-2-sulfonyl)-phenyl]-amine in an analogous manner to Example 1221d. Product was obtained as a white foam. (12 mg, 8%). LCMS 562.18 (M+H), HPLC purity 99%, 1H-NMR (CDCl3, 400 MHz) δ 8.27 (s, 1H), 8.17 (s, 1H), 7.81 (d, J=7.1 Hz), 7.49-7.42 (m, 3H), 7.20 (d, J=6.5 Hz, 1H), 7.13 (d, J=8.3 Hz, 1H), 6.99 (s, 1H), 3.75-3.65 (bs, 2H), 3.13-3.03 (m, 1H), 2.29-2.24 (m, 2H), 1.67-1.61 (m, 2H), 1.33 (s, 6H), 1.25 (d, J=6.7 Hz, 6H), 1.20 (t, J=7.0 Hz, 3H).

Example 1253

5-Chloro-N(4)-[2-fluoro-6-(propane-2-sulfonyl)-phenyl]-N(2)-[3-(2-methoxy-ethyl)-2,3,4,5-tetrahydro-1H-3-benzazepin-7-yl]-pyrimidine-2,4-diamine Title compound was prepared from 3-(2-Methoxy-ethyl)-2,3,4,5-tetrahydro-1H-benzo[d]azepin-7-ylamine and (2,5-Dichloro-pyrimidin-4-yl)-[2-fluoro-6-(propane-2-sulfonyl)-phenyl]-amine in an analogous manner to Example 1221d.

Product was obtained as a pale foam (32 mg, 22%). LCMS: 550.09 (M+H), HPLC purity 99%, 1H-NMR (CDCl3, 400 MHz) δ 8.11 (d, J=11.6 Hz, 1H), 8.10 (s, 1H), 7.83-7.81 (m, 1H), 7.49-7144 (m, 3H), 7.11-7.08 (m, 2H), 6.86 (d, J=8.2 Hz, 1H), 3.60.3.56 (m, 2H), 3.37 (s, 3H), 3.10-3.00 (m, 1H), 2.88-2.74 (m, 8H), 2.08-2.06 (m, 2H), 1.22 (d, J=6.7 Hz, 6H).

Example 1254

7-{5-Chloro-4-[2-fluoro-6-(propane-2-sulfonyl)-phenylamino]-pyrimidin-2-ylamino}-5,5-dimethyl-1,3,4,5-tetrahydro-1-benzazepin-2-one Title compound was prepared from 7-Amino-5,5-dimethyl-1,3,4,5-tetrahydro-benzo[b]azepin-2-one and (2,5-Dichloro-pyrimidin-4-yl)-[2-fluoro-6-(propane-2-sulfonyl)-phenyl]-amine in an analogous manner to Example 1221d. Title compound isolated as an off-white solid (69 mg, 48%). LCMS 534.14 (M+H), HPLC purity 95%, 1H-NMR (CDCl3, 400 MHz) δ 10.96 (s, 1H), 9.11 (s, 1H), 8.06 (s, 1H), 7.86 (d, J=8.0 Hz, 1H), 7.66-7.62 (m, 1H), 7.54-7.49 (m, 2H), 7.26 (d, 2H), 6.69 (d, J=8.2 Hz, 1H), 4.08-4.00 (m, 1H), 2.35 (dd, J=6.9 Hz, 2H), 2.05 (dd, J=7.3 Hz, 2H), 1.30 (s, 6H), 1.26 (d, J=6.8 Hz, 6H).

Example 1255

8-{5-Chloro-4-[2-fluoro-6-(propane-2-sulfonyl)-phenylamino]-pyrimidin-2-ylamino}-1,3,4,5-tetrahydro-1-benzazepin-2-one Title compound was prepared from 8-Amino-1,3,4,5-tetrahydro-benzo[b]azepin-2-one and (2,5-Dichloro-pyrimidin-4-yl)-[2-fluoro-6-(propane-2-sulfonyl)-phenyl]-amine in an analogous manner to Example 1221d. Product isolated as a light grey solid (50 mg, 37%). LCMS 506.11 (M+H), HPLC purity 94%, 1H-NMR (CDCl3, 400 MHz) δ 8.23 (s, 1H), 8.16 (s, 1H), 7.86 (d, J=7.7 Hz, 1H), 7.62-7.59 (m, 2H), 7.32-7.38 (m, 1H), 7.04 (d, J=8.1 Hz, 1H), 6.94 (d, J=8.1 Hz, 1H), 6.88 (s, 1H), 3.10-3.00 (m, 1H), 2.73 (dd, J=7.1 Hz, 2H), 2.34 (dd, J=7.2 Hz, 2H), 2.20 (dd, J=6.8 Hz, 2H), 1.23 (d, J=6.9 Hz, 6H).

Example 1256

2-[5-Chloro-2-(2-oxo-2,3,4,5-tetrahydro-1H-1-benzazepin-8-ylamino)-pyrimidin-4-ylamino]-3-fluoro-benzamide Example 1256a 2-Amino-3-fluoro-benzamide. A mixture of 8-Fluoro-1H-benzo[d][1,3]oxazine-2,4-dione (2.00 g, 0.0110 mol) in 1,4-Dioxane (25 mL, 0.32 mol) was treated with ammonia (20 mL, 0.5 M in dioxane) and warmed to 60° C. for 2 h (dry ice cold finger). Additional ammonia (20 mL) was added and after 1 h at 60° C., solvent was evaporated to afford title compound.

Example 1256b 2-(2,5-Dichloro-pyrimidin-4-ylamino)-3-fluoro-benzamide was prepared from 2-Amino-3-fluoro-benzamide and 2,4,5 Trichloropyrimidine in an analogous manner to Example 1230a. Product was isolated as an off-white solid.

Example 1256c

2-[5-Chloro-2-(2-oxo-2,3,4,5-tetrahydro-1H-1-benzazepin-8-ylamino)-pyrimidin-4-ylamino]-3-fluoro-benzamide. Title compound was prepared from 8-Amino-1,3,4,5-tetrahydro-benzo[b]azepin-2-one and 2-(2,5-Dichloro-pyrimidin-4-ylamino)-3-fluoro-benzamide in an analogous manner to Example 1221d. Title compound isolated as a moss green solid (86 mg, 69%). HPLC purity 90%, LCMS 443.03 (M+H), HNMR (DMSO) 9.92 (bs, 1H), 9.82 (bs, 1H), 9.32 (s, 1H), 8.30 (d, J=1.9 Hz, 1H), 8.03 (s, 1H), 7.71 (s, 1H), 7.54 (s, 1H), 7.47-7.38 (m, 3H), 7.15-7.13 (m, 1H), 6.99-6.90 (m, 2H). 2.60-2.56 (m, 2H), 2.07-2.03 (m, 4H).

Example 1257

2-{5-Chloro-2-[3-(2-methoxy-ethyl)-2,3,4,5-tetrahydro-1H-3-benzazepin-7-ylamino]-pyrimidin-4-ylamino}-3-fluoro-benzamide Title compound was prepared from 3-(2-Methoxy-ethyl)-2,3,4,5-tetrahydro-1H-benzo[d]azepin-7-ylamine and 2-(2, 5-Dichloro-pyrimidin-4-ylamino)-3-fluoro-benzamide in an analogous manner to Example 1221d. Title compound isolated as an orange solid (29 mg, 21%). LCMS 487.20 (M+H), MP 128-134, HPLC purity 90%, 1H-NMR (DMSO-d6, 400 MHz) δ 9.37 (s, 1H), 9.22 (s, 1H), 8.16 (s, 1H), 8.06 (s, 1H), 7.73 (s, 1H), 7.52-7.43 (m, 3H), 7.21 (s, 1H), 7.13-7.10 (m, 1H), 6.83-6.80 (m, 1H).

Example 1258

2-{5-Chloro-2-[3-(2-methoxy-ethyl)-2,3,4,5-tetrahydro-1H-3-benzazepin-7-ylamino]-pyrimidin-4-ylamino}-3-fluoro-benzamide

Example 1258a

1-Fluoro-3-methylsulfanyl-2-nitro-benzene was prepared from 1,3-difluoronitrobenzene and sodium methyl mercaptide in an analogous manner to Example 1251a. (1.513 g, 26%).

Example 1258b

1-Fluoro-3-methanesulfonyl-2-nitro-benzene was prepared from 1-Fluoro-3-methylsulfanyl-2-nitro-benzene in an analogous manner to Example 1251b. (1.449 g, 82%).

Example 1258c

2-Fluoro-6-methanesulfonyl-phenylamine was prepared from 1-Fluoro-3-methanesulfonyl-2-nitro-benzene in an analogous manner to Example 1251c. (1.26 g, 99%).

Example 1258d (2,5-Dichloro-pyrimidin-4-yl)-(2-fluoro-6-methanesulfonyl-phenyl)-amine was prepared from 2-Fluoro-6-methanesulfonyl-phenylamine and 2,4,5-trichloropyrimidine in an analogous manner to Example 1251d to afford an orange solid (1.38 g, 62%). MP 212-215, HPLC purity 95%, LCMS 338 (M+H), 1H-NMR (CDCl3, 400 MHz) δ 8.33 (s, 1H), 8.23 (s, 1H), 7.88 (d, J=2.7 Hz, 1H), 7.90-7.87 (m, 2H), 3.01 (s, 3H).

Example 1258e

2-{5-Chloro-2-[3-(2-methoxy-ethyl)-2,3,4,5-tetrahydro-1H-3-benzazepin-7-ylamino]-pyrimidin-4-ylamino}-3-fluoro-benzamide was prepared from 8-Amino-5,5-dimethyl-1,3,4,5-tetrahydro-benzo[b]azepin-2-one and (2,5-Dichloro-pyrimidin-4-yl)-(2-fluoro-6-methanesulfonyl-phenyl)-amine in an analogous manner to Example 1221d. Product isolated as a white solid (64 mg, 48%). MP 197-199, LCMS 506.10 (M+H), HPLC purity 95%, 1H-NMR (CDCl3, 400 MHz) δ 10.53 (s, 1H), 8.72 (s, 1H), 8.08 (s, 1H), 7.96 (d, J=7.7 Hz, 1H), 7.74-7.70 (m, 1H), 7.65-7.62 (m, 1H), 7.25-7.23 (m, 1H), 7.12 (s, 1H), 7.03 (d, J=8.8 Hz, 1H), 6.97 (s, 1H), 3.05 (s, 3H), 2.37-2.34 (m, 2H), 2.10-2.06 (m, 2H), 1.38 (s, 6H).

Example 1259

8-[5-Chloro-4-(2-fluoro-6-methanesulfonyl-phenylamino)-pyrimidin-2-ylamino]-1-ethyl-5,5-dimethyl-1,3,4,5-tetrahydro-1-benzazepin-2-one Title compound was prepared from 8-Amino-1-ethyl-5,5-dimethyl-1,3,4,5-tetrahydro-benzo[b]azepin-2-one and (2,5-Dichloro-pyrimidin-4-yl)-(2-fluoro-6-methanesulfonyl-phenyl)-amine in an analogous manner to Example 1221d. Product isolated as a white solid (32 mg, 22%). MP=217-218, LCMS: 534.09 (M+H), 1H-NMR (CDCl3, 400 MHz) 6 (8.18 (s, 1H), 7.97 (s, 1H), 7.89 (d, J=7.6 Hz, 1H), 7.55-7.46 (m, 4H), 7.21 (d, J=8.6 Hz, 1H), 7.13 (d, J=8.4 Hz, 1H), 3.75-3.73 (m, 2H), 2.99 (s, 3H), 2.29-2.26 (m, 2H), 2.10-1.99 (m, 2H), 1.33 (s, 6H), 1.21 (t, J=7.1 Hz, 3H).

Example 1260

7-[5-Chloro-4-(2-fluoro-6-methanesulfonyl-phenylamino)-pyrimidin-2-ylamino]-5,5-dimethyl-1,3,4,5-tetrahydro-1-benzazepin-2-one Title compound was prepared from 7-Amino-5,5-dimethyl-1,3,4,5-tetrahydro-benzo[b]azepin-2-one and (2,5-Dichloro-pyrimidin-4-yl)-(2-fluoro-6-methanesulfonyl-phenyl)-amine in an analogous manner to Example 1221d. Product isolated as a white solid (35 mg, 26%). MP 178-180, LCMS 506.06 (M+H). 1H-NMR (DMSO-d6, 400 MHz) δ 9.30 (s, 1H), 9.23 (s, 1H), 8.78 (s, 1H), 8.18 (s, 1H), 7.88 (d, J=7.6 Hz, 1H), 7.79-7.75 (m, 1H), 7.71-7.69 (m, 1H), 7.30 (s, 1H), 7.27-7.25 (m, 1H), 6.54 (d, J=8.6 Hz, 1H), 3.22 (s, 3H), 2.11-2.07 (m, 2H), 1.92-1.89 (s, 2H), 1.20 (s, 6H).

Example 1261

8-[5-Chloro-4-(2-fluoro-6-methanesulfonyl-phenylamino)-pyrimidin-2-ylamino]-1,3,4,5-tetrahydro-1-benzazepin-2-one Title compound was prepared from 8-Amino-1,3,4,5-tetrahydro-benzo[b]azepin-2-one and (2,5-Dichloro-pyrimidin-4-yl)-(2-fluoro-6-methanesulfonyl-phenyl)-amine in an analogous manner to Example 1221d. Product isolated as an off-white solid (52 mg, 41%). MP=242-245, LCMS 478.05 (M+H), HPLC purity 93%, 1H-NMR (DMSO-d6, 400 MHz) δ 9.50 (s, 1H), 9.19 (s, 1H), 8.89 (s, 1H), 8.20 (s, 1H), 7.85 (d, J=8.0 Hz, 1H), 7.75-7.72 (m, 1H), 7.67-7.64 (m, 1H), 7.02 (d, J=8.0 Hz, 1H), 6.93 (s, 1H), 6.84 (d, J=8.0 Hz, 1H), 3.21 (s, 3H), 2.55-2.51 (m, 2H), 2.07-2.04 (m, 4H).

Example 1262

5-Chloro-N(4)-(2-fluoro-6-methanesulfonyl-phenyl)-(2-fluoro-6-methanesulfonyl-phenyl)2,3,4,5-tetrahydro-1H-3-benzazepin-7-yl]-pyrimidine-2,4-diamine Title compound was prepared from 3-(2-Methoxy-ethyl)-2,3,4,5-tetrahydro-1H-benzo[d]azepin-7-ylamine and (2,5-Dichloro-pyrimidin-4-yl)-(2-fluoro-6-methanesulfonyl-phenyl)-amine in an analogous manner to Example 1221d. Product isolated as a white foam (35 mg, 25%), HPLC purity 99%, LCMS 522.17 (M+H), 1H-NMR (CDCl3, 400 MHz) δ 8.14 (s, 1H), 7.89-7.87 (m, 1H), 7.86 (s, 1H), 7.50-7.47 (m, 2H), 7.10-7.07 (m, 3H), 6.89 (d, J=7.7 Hz, 1H), 3.56-3.53 (m, 1H), 3.38 (s, 3H), 2.98 (s, 3H), 2.85-2.69 (m, 10H).

Example 1263

3-({2-[5-Chloro-2-(5,5-dimethyl-2-oxo-2,3,4,5-tetrahydro-1H-1-benzazepin-8-ylamino)-pyrimidin-4-ylamino]-3-fluoro-phenyl}-methyl-amino)-propionitrile 1263a) 3-[(3-Fluoro-2-nitro-phenyl)-methyl-amino]-propionitrile. 1,3-Difluoro-2-nitro-benzene (3.55 g, 0.0223 mol), 3-Methylamino-propionitrile (1.88 g, 0.0223 mol), K2CO3 (3.39 g, 0.0245 mol), and DMF (40 mL, 0.4 mol; were heated at 50° C. for 72 h.

1263b) 3-[(2-Amino-3-fluoro-phenyl)-methyl-amino]-propionitrile was prepared from 3-[(3-Fluoro-2-nitro-phenyl)-methyl-amino]-propionitrile in an analogous manner to Example 1221c to afford as a pale orange oil (2.81 g, 79%). LCMS 194.16 (M+H).

1263c) 3-{[2-(2,5-Dichloro-pyrimidin-4-ylamino)-3-fluoro-phenyl]-methyl-amino}-propionitrile was prepared from was prepared from 3-[(2-Amino-3-fluoro-phenyl)-methyl-amino]-propionitrile and 2,4,5-trichloropyrimidine in an analogous manner to Example 1251d to afford title compound as an off-white solid. MP 109-111. HPLC 95% purity, LCMS 342.05 (M+H). 1H-NMR (CDCl3, 400 MHz) δ 8.22 (s, 1H), 7.28-7.26 (m 1H), 7.11 (s, 1H), 6.99-6.94 (m, 2H), 3.27 (t, J=6.7 Hz, 2H), 2.75 (s, 3H), 2.53 (t, J=6.7 Hz, 2H).

1263d) 3-({2-[5-Chloro-2-(5,5-dimethyl-2-oxo-2,3,4,5-tetrahydro-1H-1-benzazepin-8-ylamino)-pyrimidin-4-ylamino]-3-fluoro-phenyl}-methyl-amino)-propionitrile was prepared from 3-{[2-(2,5-Dichloro-pyrimidin-4-ylamino)-3-fluoro-phenyl]-methyl-amino}-propionitrile and 8-Amino-5,5-dimethyl-1,3,4,5-tetrahydro-benzo[b]azepin-2-one in an analogous manner to Example 1221d. Product isolated a white lyophilate (27 mg, 36%). HPLC purity 99%, LCMS 510.15 (M+H), 1H-NMR (CDCl3, 400 MHz) δ 12.03 (s, 1H), 7.94 (s, 1H), 7.70 (s, 1H), 7.53-7.49 (m, 1H), 7.30-7.26 (m, 2H), 7.18-7.13 (m, 2H), 7.07-7.03 (m, 2H), 3.29 (t, J=6.3 Hz, 2H), 2.74 (s, 3H), 2.53 (t, J=6.3 Hz, 2H), 2.37 (t, J=6.2 Hz, 2H), 2.10 (t, J=7.0 Hz, 2H), 1.36 (s, 6H).

Example 1264

3-({2-[5-Chloro-2-(1-ethyl-5,5-dimethyl-2-oxo-2,3,4,5-tetrahydro-1H-1-benzazepin-8-ylamino)-pyrimidin-4-ylamino]-3-fluoro-phenyl}-methyl-amino)-propionitrile Title compound was prepared from 3-{[2-(2,5-Dichloro-pyrimidin-4-ylamino)-3-fluoro-phenyl]-methyl-amino}-propionitrile and 8-Amino-1-ethyl-5,5-dimethyl-1,3,4,5-tetrahydro-benzo[b]azepin-2-one in an analogous manner to Example 1221d. Title compound isolated as a white lyophilate (82 mg, 61%). HPLC 99% purity, LCMS 538.20 (M+H), 1H-NMR (CDCl3, 400 MHz) δ 12.10 (s, 1H), 7.93 (s, 1H), 7.76 (s, 1H), 7.44 (s, 1H), 7.38-7.32 (m, 1H), 7.21 (m, 2H), 6.99-6.92 (m, 2H), 3.70-3.60 (m, 2H), 3.26 (t, J=6.5 Hz, 2H), 2.69 (s, 3H), 2.52 (t, J=6.4 Hz, 2H), 2.24-2.20 (m, 2H), 2.10-1.98 (m, 2H), 1.32 (s, 6H), 1.09 (t, J=7.4 Hz, 3H).

Example 1265

3-({2-[5-Chloro-2-(1-ethyl-5,5-dimethyl-2-oxo-2,3,4,5-tetrahydro-1H-1-benzazepin-8-ylamino)-pyrimidin-4-ylamino]-3-fluoro-phenyl}-methyl-amino)-propionitrile Title compound was prepared from 3-{[2-(2,5-Dichloro-pyrimidin-4-ylamino)-3-fluoro-phenyl]-methyl-amino}-propionitrile and 3-(2-Methoxy-ethyl)-2,3,4,5-tetrahydro-1H-benzo[d]azepin-7-ylamine in an analogous manner to Example 1221d. Title compound isolated as an off-white lyophilate (56 mg, 43%). 99% purity, LCMS 526.21 (M+H), 1H-NMR (CDCl3, 400 MHz) δ 12.20 (bs, 1H), 11.8 (s, 1H), 7.93 (s, 1H), 7.67 (s, 1H), 7.44-7.42 (m, 1H), 7.24 (d, J=8.2 Hz, 1H), 7.03-6.98 (m, 2H), 6.93 (d, J=7.9 Hz, 1H), 3.83-3.79 (m, 4H), 3.50-3.40 (m, 4H), 3.37 (s, 3H), 3.26 (t, J=6.4 Hz, 2H), 2.99-2.83 (m, 3H), 2.71 (s, 3H), 2.66-2.60 (m, 1H), 2.50 (t, J=6.3 Hz, 2H).

Example 1266

3-({2-[5-Chloro-2-(5,5-dimethyl-2-oxo-2,3,4,5-tetrahydro-1H-1-benzazepin-7-ylamino)-pyrimidin-4-ylamino]-3-fluoro-phenyl}-methyl-amino)-propionitrile Title compound was prepared from 3-{[2-(2,5-Dichloro-pyrimidin-4-ylamino)-3-fluoro-phenyl]-methyl-amino}-propionitrile and 8 7-Amino-5,5-dimethyl-1,3,4,5-tetrahydro-benzo[b]azepin-2-one in an analogous manner to Example 1221d. Title compound isolated as a white lyophilate (67 mg, 53%). 99% purity, LCMS (510.19 M+H), 1H-NMR (CDCl3, 400 MHz) δ 12.00 (s, 1H), 7.92 (s, 1H), 7.79 (s, 1H), 7.69 (s, 1H), 7.42-7.37 (m, 3H), 7.02-6.97 (m, 2H), 6.66 (d, J=9.0 Hz, 1H), 3.28 (t, J=6.4 Hz, 2H), 2.73 (s, 3H), 2.53 (t, J=6.6 Hz, 2H), 2.36 (t, J=6.8 Hz, 2H), 2.06 (t, J=6.9 Hz, 2H), 1.27 (s, 6H).

Example 1267

3-({2-[5-Chloro-2-(5,5-dimethyl-2-oxo-2,3,4,5-tetrahydro-1H-1-benzazepin-7-ylamino)-pyrimidin-4-ylamino]-3-fluoro-phenyl}-methyl-amino)-propionitrile Title compound was prepared from 3-{[2-(2,5-Dichloro-pyrimidin-4-ylamino)-3-fluoro-phenyl]-methyl-amino}-propionitrile and 7-Amino-5,5-dimethyl-1,3,4,5-tetrahydro-benzo[b]azepin-2-one in an analogous manner to Example 1221d. Title compound isolated as a white lyophilate (40 mg, 33%). 99% purity, LCMS (510.19 M+H), 1H-NMR (CDCl3, 400 MHz) δ 12.00 (s, 1H), 7.92 (s, 1H), 7.79 (s, 1H), 7.69 (s, 1H), 7.42-7.37 (m, 3H), 7.02-6.97 (m, 2H), 6.66 (d, J=9.0 Hz, 1H), 3.28 (t, J=6.4 Hz, 2H), 2.73 (s, 3H), 2.53 (t, J=6.6 Hz, 2H), 2.36 (t, J=6.8 Hz, 2H), 2.06 (t, J=6.9 Hz, 2H), 1.27 (s, 6H).

Example 1268

2-[5-Chloro-2-(4-oxo-4,5-dihydro-6-oxa-10b-aza-benz[e]azulen-9-ylamino)-pyrimidin-4-ylamino]-3-fluoro-N-methyl-benzamide

Example 1268a

4-Nitro-2-pyrrol-1-yl-phenol. Furan, tetrahydro-2,5-dimethoxy- (4.72 g, 0.0357 mol) was added dropwise to 2-Amino-4-Nitrophenol (5.00 g, 0.0324 mol) in Acetic acid (200 mL, 3 mol) and the reaction mixture was heated to 100° C. for 3 h The reaction mixture was concentrated, taken up in EtOAc, washed with sat'd NaHCO3 and brine, was dried over MgSO4, filtered, and concentrated under reduced pressure. Product was obtained as a pale yellow oil (4.51 g, 68%).

Example 1268b (4-Nitro-2-pyrrol-1-yl-phenoxy)-acetic acid ethyl ester. 4-Nitro-2-pyrrol-1-yl-phenol (13.39 g, 0.066 mol), K2CO3 (10.9 g, 0.08 mol), Acetone (400 mL, 5 mol), and Ethyl bromoacetate (8.00 mL, 0.07 mol) were stirred at rt for 5 hours. The reaction mixture was filtered and concentrated to a yellow oil which solidified. The resulting residue was

Example 1268c (4-Nitro-2-pyrrol-1-yl-phenoxy)-acetic acid. (4-Nitro-2-pyrrol-1-yl-phenoxy)-acetic acid ethyl ester (15 g, 0.052 mol), THF (100 mL, 1 mol), and Sodium hydroxide (10 mL, 0.5 mol) were stirred at rt for 6 h. The reaction mixture was concentrated, diluted with H2O, and washed with EtOAc. The aqueous layer was neutralized and extracted with EtOAc. The organic layer was dried over MgSO4, filtered, and concentrated under reduced pressure to afford 10.92 g (80%) of a yellow oil which solidified upon standing.

Example 1268d

9-Nitro-6-oxa-10b-aza-benz[e]azulen-4-one. PCl5 (1.30 g, 6.25 mmol) was added slowly to (4-Nitro-2-pyrrol-1-yl-phenoxy)-acetic acid (1.5 g, 5.7 m mol) in CH2Cl2 (40 mL, 0.6 mol) and the reaction mixture was stirred at rt for 16 h. The reaction mixture was poured onto crushed ice, basified with 1 N NaOH, and extracted with CH2Cl2. The organic layer was dried over MgSO4, filtered, and concentrated under reduced pressure. LCMS 245.10 (M+H).

Example 1268e

9-Amino-6-oxa-10b-aza-benz[e]azulen-4-one and 6-Oxa-10b-aza-benz[e]azulen-9-ylamine were prepared from 9-Nitro-6-oxa-10b-aza-benz[e]azulen-4-one in an analogous manner to Example 1221c. 9-Amino-6-oxa-10b-aza-benz[e]azulen-4-one (100 mg, 37%)=off white solid, MP=160-162, HPLC purity 96%, LCMS 215.16 (M+H). 1H-NMR (DMSO-d6, 400 MHz) δ 7.53 (s, 1H), 7.11 (t, J=1.5 Hz, 1H), 6.99 (d, J=8.6 Hz, 1H), 6.73 (s, 1H), 6.52-6.49 (m, 2H), 5.22 (s, 2H), 4.60 (s, 2H). 6-Oxa-10b-aza-benz[e]azulen-9-ylamine (130 mg, 52%)=off white solid MP=108-110, HPLC purity 95%, LCMS 201 (M+H), 1H-NMR (DMSO-d6, 400 MHz) δ 6.95 (s, 1H), 6.84 (d, J=8.4 Hz, 1H), 6.57 (d, J=2.3 Hz, 1H), 6.41-6.38 (m, 1H), 6.15-6.13 (m, 2H), 5.33 (d, J=4.6 Hz, 1H), 5.06 (s, 2H), 4.75-4.73 (m, 1H), 4.40-4.36 (m, 1H), 4.02-3.97 (m, 1H).

Example 1268f

2-[5-Chloro-2-(4-oxo-4,5-dihydro-6-oxa-10b-aza-benz[e]azulen-9-ylamino)-pyrimidin-4-ylamino]-3-fluoro-N-methyl-benzamide was prepared from 9-Amino-6-oxa-10b-aza-benz[e]azulen-4-one and 2-(2,5-Dichloro-pyrimidin-4-ylamino)-3-fluoro-N-methyl-benzamide in an analogous manner to Example 1223c. Product was obtained as a tan ppt. MP 223-225 (dec) LCMS 493.09 (M+H), HPLC purity 95%, 1H-NMR (DMSO-D6, 400 MHZ) Δ 9.56 (s, 1H), 9.48 (s, 1H), 8.52 (d, J=4.6 Hz, 1H), 8.23 (s, 1H), 7.68 (s, 1H), 7.43 (d, J=7.6 Hz, 1H), 7.34 (s, 1H), 7.17-7.10 (m, 2H), 7.08 (s, 1H), 6.53 (d, J=2.5H, 1H), 4.67 (s, 2H), 2.73 (d, J=4.5 Hz, 3H).

Example 1269

2-[5-Chloro-2-(6-oxa-10b-aza-benz[e]azulen-9-ylamino)-pyrimidin-4-ylamino]-3-fluoro-N-methyl-benzamide Title compound was prepared from 6-Oxa-10b-aza-benz[e]azulen-9-ylamine and 2-(2,5-Dichloro-pyrimidin-4-ylamino)-3-fluoro-N-methyl-benzamide in an analogous manner to Example 1223c. Product was obtained as a tan solid. LCMS 479.10 (M+H), HPLC purity 99%, 1H-NMR (DMSO-d6, 400 MHz) δ 9.38 (s, 1H), 9.35 (s, 1H), 8.52 (bd, 1H), 8.20 (s, 1H), 7.46 (m, 2H), 7.39-7.32 (m, 3H), 7.26 (s, 1H), 7.03 (s, 2H), 6.88 (d, J=9.0 Hz, 1H), 6.54 (d, J=5.9 Hz, 1H), 6.29 (m, 1H), 6.21 (s, 1H), 6.06 (d, J=5.9 Hz, 1H), 2.73 (d, J=4.3 Hz, 3H).

Example 1270

2-[5-Chloro-2-(6,6-dimethyl-5,6-dihydro-4H-3,10b-diaza-benz[e]azulen-9-ylamino)-pyrimidin-4-ylamino]-3-fluoro-N-methyl-benzamide

Example 1270a (5,5-Dimethyl-2-oxo-2,3,4,5-tetrahydro-1H-1-benzazepin-8-yl)-carbamic acid tert-butyl ester. 8-Amino-5,5-dimethyl-1,3,4,5-tetrahydro-benzo[b]azepin-2-one (3.90 g, 0.0191 mol), Di-tert-Butyldicarbonate (5.26 mL, 0.0229 mol) Triethylamine (3.19 mL, 0.0229 mol) and DMF (330 mL, 4.3 mol). were stirred at rt for 72 h. The reaction mixture was concentrated, washed with water×3, dried over MgSO4, filtered, and concentrated. Title compound recovered as a white solid (1.90 g, 33%).

Example 1270b (5,5-Dimethyl-2-thioxo-2,3,4,5-tetrahydro-1H-1-benzazepin-8-yl)-carbamic acid tert-butyl ester. (5,5-Dimethyl-2-oxo-2,3,4,5-tetrahydro-1H-1-benzazepin-8-yl)-carbamic acid tert-butyl ester (1.90 g, 0.00624 mol), THF (100 mL, 1 mol), and 2,4-Bis(4-methoxyphenyl)-2,4-dithioxo-1,3,2,4-dithiadiphosphetane (2.58 g, 6.4 mmol) were stirred at rt for 16 h. Title compound was obtained as a white solid (1.54 g, 77%), LCMS 321.21 (M+H).

Example 1270c (5,5-Dimethyl-2-methylsulfanyl-4,5-dihydro-3H-1-benzazepin-8-yl)-carbamic acid tert-butyl ester (5,5-Dimethyl-2-thioxo-2,3,4,5-tetrahydro-1H-1-benzazepin-8-yl)-carbamic acid tert-butyl ester (1.54 g, 0.00480 mol), Methyl iodide (0.314 mL, 0.00505 mol), Potassium carbonate (0.730 g, 0.00529 mol), and Acetone (100 mL, 2 mol) were stirred at rt for 48 hours. Title compound isolated as a clear oil (1.281 g, 80%).

Example 1270d

[2-(2,2-Dimethoxy-ethylamino)-5,5-dimethyl-4,5-dihydro-3H benzo[b]azepin-8-yl]-carbamic acid tert-butyl ester. (5,5-Dimethyl-2-methylsulfanyl-4,5-dihydro-3H-1-benzazepin-8-yl)-carbamic acid tert-butyl ester (1.281 g, 3.8 mmol), Aminoacetaldehyde dimethyl acetal (0.542 mL, 5 mmol), and EtOH (100 mL, 2 mol) were heated to reflux for 2 hrs and stirred at rt for 72 h. LCMS 392 (M+H).

Example 1270e 6,6-Dimethyl-5,6-dihydro-4H-3,10b-diaza-benz[e]azulen-9-ylamine. To the above solution of [2-(2,2-Dimethoxy-ethylamino)-5,5-dimethyl-4,5-dihydro-3H benzo[b]azepin-8-yl]-carbamic acid tert-butyl ester was added conc HCl (25 ml) and heating was continued at 80° C. for 16 h. Product LCMS=228.20 (M+H).

Example 1270f

2-[5-Chloro-2-(6,6-dimethyl-5,6-dihydro-4H-3,10b-diaza-benz[e]azulen-9-ylamino)-pyrimidin-4-ylamino]-3-fluoro-N-methyl-benzamide was prepared from 6,6-Dimethyl-5,6-dihydro-4H-3,10b-diaza-benz[e]azulen-9-ylamine and 2-(2,5-Dichloro-pyrimidin-4-ylamino)-3-fluoro-N-methyl-benzamide in an analogous manner to Example 1223c. Title compound was isolated as a white solid (64 mg, 42%) LCMS 506.22 (M+H), HPLC purity 99%, 1H-NMR (DMSO-d6, 400 MHz) δ 9.69 (s, 1H), 9.38 (s, 1H), 8.47 (m, 1H), 8.23 (s, 1H), 7.80 (d, J=6.3 Hz, 1H), 7.72 (s, 1H), 7.55 (s, 1H), 7.40 (d, J=7.5 Hz, 1H), 7.34 (d, J=8.8 Hz, 1H), 7.28-7.23 (m, 2H), 2.92 (m, 2H), 2.74 (d, J=4.4 Hz, 3H), 2.15 (m, 2H).

Example 1271

2-{5-Chloro-2-[5,5-dimethyl-2-oxo-3-(2,2,2-trifluoro-acetylamino)-2,3,4,5-tetrahydro-1H-1-benzazepin-8-ylamino]-pyrimidin-4-ylamino}-3-fluoro-N-methyl-benzamide

Example 1271a

3-Iodo-5,5-dimethyl-8-nitro-1,3,4,5-tetrahydro-1-benzazepin-2-one. 5,5-Dimethyl-8-nitro-1,3,4,5-tetrahydro-benzo[b]azepin-2-one (4.00 g, 0.0171 mol) in Methylene chloride (54 mL, 0.84 mol) was cooled to 0° C., treated with TMEDA (7.73 mL, 0.05 mol) then treated dropwise with TMSI (7.29 mL, 0.05 mol). The mixture was stirred at 0° C. for 60 min after which solid Iodine (6.50 g, 0.0256 mol) was added in one portion and the mixture stirred at 0° C. for 60 min. The reaction was quenched with 10% Na2S2O3. Title compound isolated as a beige solid. (5.43 g, 88%) LCMS 361 (M+H).

Example 1271b

3-Azido-5,5-dimethyl-8-nitro-1,3,4,5-tetrahydro-1-benzazepin-2-one. 3-Iodo-5,5-dimethyl-8-nitro-1,3,4,5-tetrahydro-1-benzazepin-2-one (5.367 g, 0.015 mol), Sodium azide (6.49 g, 0.1 mol), and DMF (100 mL, 2 mol) were stirred at rt for 2 h. The reaction mixture was diluted with H2O and the resulting beige ppt was filtered.

Example 1271c

3-Amino-5,5-dimethyl-8-nitro-1,3,4,5-tetrahydro-1-benzazepin-2-one. 3-Azido-5,5-dimethyl-8-nitro-1,3,4,5-tetrahydro-1-benzazepin-2-one (3.10 g, 10.3 mmol), Triphenylphosphine Resin (12 g, 11.55 mmol), THF (120 mL, 1400 mmol) and Water (0.9 mL, 50 mmol) were combined and stirred at rt for 16 h. The reaction mixture was filtered. Product isolated as a beige solid. (HPLC purity >98%)

Example 1271d

N-(5,5-Dimethyl-8-nitro-2-oxo-2,3,4,5-tetrahydro-1H-1-benzazepin-3-yl)-2,2,2-trifluoro-acetamide. 3-Amino-5,5-dimethyl-8-nitro-1,3,4,5-tetrahydro-1-benzazepin-2-one (4.10 g, 0.0164 mol), Methylene chloride (200 mL, 3 mol), Pyridine (3.99 mL, 0.0493 mol), and Trifluoroacetic anhydride (3.48 mL, 0.0247 mol) were stirred at rt for 1 hr. The reaction mixture was washed with 10% citric acid, dried over MgSO4, filtered, and concentrated under reduced pressure. Product isolated as an off-white solid.

Example 1271e

N-(8-Amino-5,5-dimethyl-2-oxo-2,3,4,5-tetrahydro-1H-1-benzazepin-3-yl)-2,2,2-trifluoro-acetamide was prepared from N-(5,5-Dimethyl-8-nitro-2-oxo-2,3,4,5-tetrahydro-1H-1-benzazepin-3-yl)-2,2,2-trifluoro-acetamide in an analogous manner to Example 1224c. LCMS 316.15 (M+H), 1H-NMR (CDCl3, 400 MHz) δ 8.22, (s, 1H), 7.59 d, J=6.1 Hz, 1H), 7.21 (d, J=8.5 Hz, 1H), 6.56 (dd, J=1.0 Hz, 8.5 Hz, 1H), 6.31 (s, 1H), 4.58-4.52 (m, 1H), 3.75 (s, 2H), 2.64-2.59 (m, 1H), 1.92 (t, J=12.1 Hz, 1H), 1.44 (s, 3H), 1.35 (s, 3H).

Example 1271f

2-{5-Chloro-2-[5,5-dimethyl-2-oxo-3-(2,2,2-trifluoro-acetylamino)-2,3,4,5-tetrahydro-1H-1-benzazepin-8-ylamino]-pyrimidin-4-ylamino}-3-fluoro-N-methyl-benzamide was prepared from N-(8-Amino-5,5-dimethyl-2-oxo-2,3,4,5-tetrahydro-1H-1-benzazepin-3-yl)-2,2,2-trifluoro-acetamide and 2-(2,5-Dichloro-pyrimidin-4-ylamino)-3-fluoro-N-methyl-benzamide in an analogous manner to Example 12211d. The title compound was isolated as a white solid (73 mg, 25%). HPLC purity 99%, LCMS 594.24 (M+H), HNMR (DMSO) 9.73 (s, 1H), 9.60 (d, J=7.8 Hz, 1H), 9.43 (s, 1H), 9.37 (s, 1H), 8.50 (d, J=4.5 Hz, 1H), 8.19 (s, 1H), 7.48-7.44 (m, 2H), 7.35-7.30 (m, 2H), 7.18 (s, 1H), 7.10 (d, J=8.9 Hz, 1H), 4.27-4.20 (m, 1H), 2.73 (d, J=4.2 Hz, 3H), 2.18-2.12 (m, 2H), 1.35 (s, 3H), 1.26 (s, 3H).

Example 1272

2-[2-(3-Amino-5,5-dimethyl-2-oxo-2,3,4,5-tetrahydro-1H-1-benzazepin-8-ylamino)-5-chloro-pyrimidin-4-ylamino]-3-fluoro-N-methyl-benzamide Combined 2-{5-Chloro-2-[5,5-dimethyl-2-oxo-3-(2,2,2-trifluoro-acetylamino)-2,3,4,5-tetrahydro-1H-1-benzazepin-8-ylamino]-pyrimidin-4-ylamino}-3-fluoro-N-methyl-benzamide (355 mg, 0.000598 mol), 1 M of NH4OH in Methanol (2 mL), and THF (50 mL, 0.6 mol). Added 2 mL of 50% NaOH and stirred for 2 hr. Product isolated as a white solid (244 mg, 82%). LCMS 498.22 (M+H), HPLC purity 94%, 1H-NMR (CDCl3, 400 MHz) δ 8.90 (bs, 1H), 8.05 (s, 1H), 7.93 (bs, 1H), 7.63 (bs, 1H), 7.44-7.39 (m, 2H), 7.35-7.31 (m, 2H), 7.28-7.26 (m, 2H), 7.20 (d, J=7.5 Hz, 1H), 6.90 (d, J=8.2 Hz, 1H), 6.71 (bs, 1H), 3.40-3.37 (m, 1H), 2.93 (d, J=4.7 Hz, 3H), 2.31-2.27 (m, 1H), 1.99-1.96 (m, 2H), 1.88-1.85 (m, 1H), 1.38 (s, 3H), 1.28 (s, 3H).

Example 1273

8-{5-Chloro-4-[2-fluoro-6-(tetrahydro-furan-3-yloxy)-phenylamino]-pyrimidin-2-ylamino}-1,3,4,5-tetrahydro-1-benzazepin-2-one

Example 1273a (2,5-Dichloro-pyrimidin-4-yl)-(2-fluoro-6-methoxy-phenyl)-amine was prepared from 2,4,5-Trichloro-pyrimidine and 2-Fluoro-6-methoxyaniline in an analogous manner to Example 1230a. Title product was obtained as an off white solid (3.80 g, 62%). MP=133-135. LCMS 289.03 (M+H), HPLC purity=94%, 1H-NMR (DMSO-d6, 400 MHz) δ 9.24 (s, 1H), 8.35 (s, 1H), 7.39-7.35 (m, 1H), 7.00-6.91 (m, 2H), 3.80 (s, 3H).

Example 1273b 2-(2,5-Dichloro-pyrimidin-4-ylamino)-3-fluoro-phenol. Into a 1-Neck round-bottom flask was added (2,5-Dichloro-pyrimidin-4-yl)-(2-fluoro-6-methoxy-phenyl)-amine (3.676 g, 0.013 mol) and CH2Cl2 (54 mL, 0.85 mol). The reaction mixture was cooled to −78° C. and 1.00 M of BBr3 in CH2Cl2 (51.0 mL) was added dropwise. The reaction mixture was allowed to warm to rt, was stirred for 6 hrs and was quenched with H2O. Title compound obtained as off-white solid. (3.497 g, 81%). HPLC purity 99%, LCMS 274.08 (M+H), 1H-NMR (DMSO-d6, 400 MHz) δ 10.37 (s, 1H), 9.13 (s, 1H), 8.33 (s, 1H), 7.22-7.16 (m, 1H), 6.79-6.72 (m, 2H).

Example 1273c (2,5-Dichloro-pyrimidin-4-yl)-[2-fluoro-6-(tetrahydro-furan-3-yloxy)-phenyl]-amine. To a suspension of 2-(2,5-Dichloro-pyrimidin-4-ylamino)-3-fluoro-phenol (0.250 g, 0.912 mmol), 3-HydroxyTHF (88.5 uL, 1.09 mmol), and Triphenylphosphine (0.383 g, 1.46 mmol) in CH2Cl2 (10 mL, 200 mmol) cooled to 0° C. on an ice bath was slowly added Di-tert-butyl azodicarboxylate (0.336 g) for 16 h. Title compound isolated as a white foam (207 mg, 66%). LCMS 344.05 (M+H), HPLC purity 97.5%, HNMR CDCl3: 8.21 (s, 1H), 7.25-7.22 (m, 1H), 6.87 (dd, J=8.9 Hz, 1H), 6.81 (s, 1H), 6.72 (d, J=7.8 Hz, 1H), 4.98 (bt, 1H), 3.98-3.96 (m, 1H), 3.91-3.87 (m, 3H), 2.26-2.23 (m, 1H), 2.14-2.11 (m, 1H).

Example 1273d

8-{5-Chloro-4-[2-fluoro-6-(tetrahydro-furan-3-yloxy)-phenylamino]-pyrimidin-2-ylamino}-1,3,4,5-tetrahydro-1-benzazepin-2-one was prepared from 8-Amino-1,3,4,5-tetrahydro-benzo[b]azepin-2-one and (2,5-Dichloro-pyrimidin-4-yl)-[2-fluoro-6-(tetrahydro-furan-3-yloxy)-phenyl]-amine in an analogous manner to Example 1221d. Title compound was isolated as a white solid (66 mg, 51%). LCMS 485.09 (M+H), HPLC purity 99%. 1H-NMR (CDCl3, 400 MHz) δ 11.99 (s, 1H), 7.92 (s, 1H), 7.52-7.49 (m, 1H), 7.41 (s, 1H), 7.23 (s, 1H), 7.11-7.06 (m, 2H), 7.01 (s, 1H), 6.93 (dd, J=9.3 Hz, 1H), 6.81 (d, J=8.3 Hz, 1H), 4.96 (s, 1H), 3.90-3.86 m, 4H), 2.74-2.70 (m, 4H), 2.35-2.29 (m, 3H), 2.28-2.21 (m, 3H), 2.09-2.06 (m, 1H).

Example 1274

5-Chloro-N(4)-[2-fluoro-6-(tetrahydro-furan-3-yloxy)-phenyl]-N(2)-[3-(2-methoxy-ethyl)-2,3,4,5-tetrahydro-1H-3-benzazepin-7-yl]-pyrimidine-2,4-diamine Title compound was prepared from 3-(2-Methoxy-ethyl)-2,3,4,5-tetrahydro-1H-benzo[d]azepin-7-ylamine and (2,5-Dichloro-pyrimidin-4-yl)-[2-fluoro-6-(tetrahydro-furan-3-yloxy)-phenyl]-amine in an analogous manner to Example 1221d. Title compound was isolated as a white solid (60 mg, 42%). HPLC purity 99%, LCMS=528.17 (M+H), 1H-NMR (CDCl3, 400 MHz) δ 11.79 (s, 1H), 7.92 (s, 1H), 7.42-7.38 (m, 2H), 7.24-7.19 (m, 2H), 6.95-6.91 (m, 2H), 6.77 (d, J=8.4 Hz, 1H), 4.92 (s, 1H), 3.87-3.80 (m, 8H), 3.45-3.40 (m, 7H), 2.90-2.80 (m, 3H), 2.65-2.55 (m, 1H), 2.30-2.24 (m, 1H), 2.22-2.10 m, 1H).

Example 1275

5-Chloro-N(4)-[2-fluoro-6-(tetrahydro-furan-3-ylmethoxy)-phenyl]-N(2)-[3-(2-methoxy-ethyl)-2,3,4,5-tetrahydro-1H-3-benzazepin-7-yl]-pyrimidine-2,4-diamine Example 1275a (2,5-Dichloro-pyrimidin-4-yl)-[2-fluoro-6-(tetrahydro-furan-3-ylmethoxy)-phenyl]-amine was prepared from 2-(2,5-Dichloro-pyrimidin-4-ylamino)-3-fluoro-phenol and (Tetrahydro-furan-3-yl)-methanol in an analogous manner to Example 1273c. Title compound isolated as a white solid (270 mg, 83%). MP=115-116, purity=96%, LCMS 358.48 (M+H), 1H-NMR (CDCl3, 400 MHz) δ 8.20 (s, 1H), 7.25-7.22 (m, 1H), 6.86-6.82 (m, 2H), 6.76 (d, J=8.4 Hz, 1H), 4.00-3.97 (m, 2H), 3.83-3.76 (m, 3H), 3.63-3.58 (m, 1H), 2.67-2.63 (m, 1H), 2.07-2.01 (m, 1H), 1.68-1.64 (m, 1H).

Example 1275b

5-Chloro-N(4)-[2-fluoro-6-(tetrahydro-furan-3-ylmethoxy)-phenyl]-N(2)-[3-(2-methoxy-ethyl)-2,3,4,5-tetrahydro-1H-3-benzazepin-7-yl]-pyrimidine-2,4-diamine was prepared from 3-(2-Methoxy-ethyl)-2,3,4,5-tetrahydro-1H-benzo[d]azepin-7-ylamine and (2,5-Dichloro-pyrimidin-4-yl)-[2-fluoro-6-(tetrahydro-furan-3-ylmethoxy)-phenyl]-amine in an analogous manner to Example 1221d. Title compound was isolated as a white solid (90 mg, 62%) HPLC purity=99%, LCMS=542.21 (M+H), 1H-NMR (DMSO-d6, 400 MHz) δ 9.63 (bs, 1H), 9.28 (s, 1H), 8.49 (s, 1H), 8.09 (s, 1H), 7.40-7.34 (m, 1H0, 7.26 (s, 1H), 7.13 (d, J=7.7 Hz, 1H), 7.02-6.93 (m, 2H), 6.85 (d, J=8.5 Hz, 1H), 3.92-3.85 (m, 2H), 3.71-3.69 (m, 1H), 3.63-3.52 (m, 6H), 3.41-3.23 (m, 7H), 3.12-2.82 (m, 6H), 1.82-1.77 (m, 1H), 1.50-1.46 (m, 1H).

Example 1276

8-{5-Chloro-4-[2-fluoro-6-(tetrahydro-furan-3-ylmethoxy)-phenylamino]-pyrimidin-2-ylamino}-1,3,4,5-tetrahydro-1-benzazepin-2-one Title compound was prepared from 8-Amino-1,3,4,5-tetrahydro-benzo[b]azepin-2-one and (2,5-Dichloro-pyrimidin-4-yl)-[2-fluoro-6-(tetrahydro-furan-3-ylmethoxy)-phenyl]-amine in an analogous manner to Example 1221d. Title compound was isolated as a white solid. (65 mg, 49%) HPLC purity=94%, LCMS=498.20 (M+H), 1H-NMR (DMSO-d6, 400 MHz) δ 9.47 (s, 1H), 9.14 (s, 1H), 8.77 (s, 1H), 8.14 (s, 1H), 7.34-7.31 (m, 1H), 7.11 (d, J=8.4 Hz, 1H), 6.97 (d, J=8.5 Hz, 1H), 6.94-6.90 (m, 2H), 6.84 (d, J=8.3 Hz, 1H), 3.94-3.85 (m, 2H), 3.55-3.51 (m, 3H), 3.32-3.28 (m, 1H), 2.55-2.51 (m, 2H), 2.07-2.01 (m, 4H), 2.94-2.84 (m, 1H), 1.49-1.43 (m, 1H), 1.05-1.03 (m, 1H).

Example 1277

2-{5-Chloro-2-[3-(2-methoxy-ethyl)-2,3,4,5-tetrahydro-1H-3-benzazepin-7-ylamino]-pyrimidin-4-ylamino}-3,5-difluoro-N-methyl-benzamide Example 1277a 2-Amino-3,5-difluoro-benzoic acid was prepared from 3,5-Difluoro-2-nitro-benzoic acid in an analogous manner to Example 1224c. Title compound was isolated as an off-white solid, (1.70 g, 99%) LCMS 174.02 (M+H).

Example 1277b

2-Amino-3,5-difluoro-N-methyl-benzamide. 2-Amino-3,5-difluoro-benzoic acid (1.70 g, 0.01 mol) was dissolved in THF (100 mL, 1 mol). Triphosgene (2.91 g, 0.01 mol) was dissolved in THF (10 mL) and added. The resulting solution was stirred for 4 h at rt. The reaction mixture was concentrated, and the resulting residue was sonicated in H20. The off-white ppt was filtered, taken up in acetone, and was concentrated under reduced pressure. The resulting solid was dissolved in THF and 2 M of Methylamine in THF (15 mL) was added. A white ppt formed immediately. The reaction mixture was stirred at RT for 16 h. Title compound isolated as a white solid (1.099 g, 60%), LCMS=187 (M+H).

Example 1277c 2-(2,5-Dichloro-pyrimidin-4-ylamino)-3,5-difluoro-N-methyl-benzamide. To a solution of 2-Amino-3,5-difluoro-N-methyl-benzamide (1.099 g, 0.006 mol) and NMP (6 mL, 0.06 mol) was added DIEA (1.23 mL, 7.8 mmol) followed by 2,4,5-Trichloro-pyrimidine (0.812 mL, 7.1 mmol) and the reaction mixture was heated at 100° C. for 16 h. Title compound isolated as an off-white solid (1.10 g, 56%), MP=220-221, HPLC purity=95%, LCMS=333.38 (M+H), 1H-NMR (CDCl3, 400 MHz) δ 8.94 (s, 1H), 8.22 (s, 1H), 7.12-7.06 (m, 2H), 6.17 (s, 1H), 2.99 (s, 3H).

Example 1277d

2-{5-Chloro-2-[3-(2-methoxy-ethyl)-2,3,4,5-tetrahydro-1H-3-benzazepin-7-ylamino]-pyrimidin-4-ylamino}-3,5-difluoro-N-methyl-benzamide was prepared from 3-(2-Methoxy-ethyl)-2,3,4,5-tetrahydro-1H-benzo[d]azepin-7-ylamine and 2-(2,5-Dichloro-pyrimidin-4-ylamino)-3,5-difluoro-N-methyl-benzamide in an analogous manner to Example 1221d. Title compound was isolated as a white solid (91 mg, 58%). HPLC purity 99%, LCMS 517.14 (M+H), 1H-NMR (DMSO-D6, 400 MHZ) Δ 9.66 (s, 1H), 9.33 (s, 1H), 9.01 (s, 1H), 8.48 (d, J=4.9 Hz, 1H), 8.16 (s, 1H), 7.60-7.58 (m, 1H), 7.39 (d, J=8.6 Hz, 1H), 7.29 (s, 1H), 7.22 (d, J=8.8 Hz, 1H), 6.95 (8.1 Hz, 1H), 3.69-3.67 (m, 2H), 3.57-3.54 (m, 2H), 3.44-3.42 (m, 2H), 3.408 (s, 3H), 3.20-3.17 (m, 2H), 3.10-3.02 (m, 2H), 2.80 (s, 3H), 2.79-2.70 (m, 2H).

Example 1278

2-[5-Chloro-2-(2-oxo-2,3,4,5-tetrahydro-1H-1-benzazepin-8-ylamino)-pyrimidin-4-ylamino]-3,5-difluoro-N-methyl-benzamide Title compound was prepared from 8-Amino-1,3,4,5-tetrahydro-benzo[b]azepin-2-one and 2-(2,5-Dichloro-pyrimidin-4-ylamino)-3,5-difluoro-N-methyl-benzamide in an analogous manner to Example 1221d. Title compound was isolated as a beige solid (136 mg, 82%). MP=250-252 (dec), HPLC purity=93%, LCMS=473.14 (M+H), HNMR (DMSO), 9.54 (bs, 1H), 9.38 (s, 1H), 9.28 (s, 1H), 8.52 (d, J=4.4 Hz, 1H), 8.21 (s, 1H), 7.53 (dd, J=7.9 Hz, 1H), 7.36 (d, J=8.6 Hz, 1H), 7.17 (d, J=7.9 Hz, 1H), 7.04 (s, 1H), 6.97 (d, J=8.1 Hz, 1H), 2.72 (d, J=4.0 Hz, 3H), 2.59-2.56 (m, 2H), 2.09-2.03 (m, 4H).

Example 1279

2-{5-Chloro-2-[5,5-dimethyl-2-oxo-3-(2,2,2-trifluoro-acetylamino)-2,3,4,5-tetrahydro-1H-1-benzazepin-8-ylamino]-pyrimidin-4-ylamino}-3-fluoro-N-prop-2-ynyl-benzamide Title compound was prepared from N-(8-Amino-5,5-dimethyl-2-oxo-2,3,4,5-tetrahydro-1H-1-benzazepin-3-yl)-2,2,2-trifluoro-acetamide and 2-(2,5-Dichloro-pyrimidin-4-ylamino)-3-fluoro-N-prop-2-ynyl-benzamide in an analogous manner to Example 1221d. Title compound was isolated as a white solid (67 mg, 24%) LCMS 564.12 (M-C3NH4), 1H-NMR (CDCl3, 400 MHz) δ 9.71 (bs, 1H), 9.60 (d, J=7.9 Hz, 1H), 9.43 (bs, 1H), 9.20 (s, 1H), 8.93 (bt, 1H), 7.50-7.47 (m, 2H), 7.37-7.34 (m, 1H), 7.28 (d, J=7.7 Hz, 1H), 7.17 (s, 1H), 7.10 (d, J=8.8 Hz, 1H), 4.26-4.22 (m, 4H), 4.03-3.99 (m, 2H), 2.18-2.13 (m, 2H), 1.35 (s, 3H), 1.26 (s, 3H).

Example 1280

2-[2-(3-Amino-5,5-dimethyl-2-oxo-2,3,4,5-tetrahydro-1H-1-benzazepin-8-ylamino)-5-chloro-pyrimidin-4-ylamino]-3-fluoro-N-prop-2-ynyl-benzamide Title compound was prepared from 2-{5-Chloro-2-[5,5-dimethyl-2-oxo-3-(2,2,2-trifluoro-acetylamino)-2,3,4,5-tetrahydro-1H-1-benzazepin-8-ylamino]-pyrimidin-4-ylamino}-3-fluoro-N-prop-2-ynyl-benzamide in an analogous manner to Example 1272. Title compound was isolated as a white solid (19 mg, 70%), LCMS 522.21 (M+H), 1H-NMR (CDCl3, 400 MHz) δ 8.58 (bs, 1H), 8.05 (s, 1H), 8.00 (s, 1H), 7.71 (s, 1H), 7.49 (d, J=7.2 Hz, 1H), 7.37 (s, 1H), 7.30-7.28 (m, 2H), 7.21-7.18 (m, 2H), 6.89 (d, J=8.4 Hz, 1H), 4.15-4.09 (m, 1H), 3.97-3.93 (m, 1H), 3.36-3.39 (m, 1H), 2.30-2.25 (m, 1H), 1.87-1.81 (m, 2H), 1.38 (s, 1H), 1.29 (s, 3H).

Example 1281

8-{5-Chloro-4-[2-fluoro-6-(tetrahydro-pyran-4-yloxy)-phenylamino]-pyrimidin-2-ylamino}-1,3,4,5-tetrahydro-1-benzazepin-2-one

Example 1281a (2,5-Dichloro-pyrimidin-4-yl)-[2-fluoro-6-(tetrahydro-pyran-4-yloxy)-phenyl]-amine was prepared from 2-(2,5-Dichloro-pyrimidin-4-ylamino)-3-fluoro-phenol and Tetrahydro-pyran-4-ol in an analogous manner to Example 1273c. Title compound was obtained as a white solid (274 mg, 84%). HPLC purity 97%, LCMS 360.09 (M+H), 1H-NMR (CDCl3, 400 MHz) δ 8.22 (s, 1H), 7.25-7.21 (m, 1H), 6.87-6.77 (m 3H), 4.58-4.55 (m, 1H), 3.89-3.84 (m, 2H), 3.61-3.56 (m, 2H), 2.06-2.01 (m, 2H), 1.80-1.72 (m, 2H).

Example 1281b

8-{5-Chloro-4-[2-fluoro-6-(tetrahydro-pyran-4-yloxy)-phenylamino]-pyrimidin-2-ylamino}-1,3,4,5-tetrahydro-1-benzazepin-2-one was prepared from 8-Amino-1,3,4,5-tetrahydro-benzo[b]azepin-2-one and (2,5-Dichloro-pyrimidin-4-yl)-[2-fluoro-6-(tetrahydro-pyran-4-yloxy)-phenyl]-amine in an analogous manner to Example 1221d. Title compound was isolated as a white solid (80 mg, 60%). HPLC purity 99%, LCMS 498.21 (M+H), 1H-NMR (DMSO-D6, 400 MHZ) Δ 9.47 (s, 1H), 9.13 (s, 1H), 8.77 (s, 1H), 8.15 (s, 1H), 7.33-7.30 (m, 1H), 7.11 (d, J=8.2 Hz, 1H), 7.01 (d, J=8.4 Hz, 1H), 6.93-6.89 (m, 2H), 6.82 (d, J=8.3 Hz, 1H), 4.61-4.59 (m, 1H), 3.60-3.56 (m, 2H), 3.37-3.33 (m, 2H), 2.55-2.52 (m, 2H), 2.07-2.03 (m, 4H), 1.78-1.74 (m, 2H), 1.48-1.45 (m, 2H).

Example 1282

5-Chloro-N(4)-[2-fluoro-6-(tetrahydro-pyran-4-yloxy)-phenyl]-N(2)-[3-(2-methoxy-ethyl)-2,3,4,5-tetrahydro-1H-3-benzazepin-7-yl]-pyrimidine-2,4-diamine Title compound was prepared from 3-(2-Methoxy-ethyl)-2,3,4,5-tetrahydro-1H-benzo[d]azepin-7-ylamine and (2,5-

Dichloro-pyrimidin-4-yl)-[2-fluoro-6-(tetrahydro-pyran-4-yloxy)-phenyl]-amine in an analogous manner to Example 1221d. Title compound was isolated as a white solid (70 mg, 48%). LCMS 542.26 (M+H), HPLC purity 99%, 1H-NMR (DMSO-d6, 400 MHz) δ 9.71 (bs, 1H), 9.35 (s, 1H), 8.57 (s, 1H), 8.13 (s, 1H), 7.39-7.36 (m, 1H), 7.25 (s, 1H), 7.12 (d, J=7.9 Hz, 1H), 7.05 (d, J=8.5 Hz, 1H), 6.95 (dd, J=8.6 Hz, 1H), 6.85 (d, J=8.2 Hz, 1H), 4.64-4.60 (m, 1H), 3.71-3.69 (m, 2H), 3.60-3.58 (m, 2H), 3.36-3.33 (m, 4H), 3.33 (s, 3H), 3.15-2.85 (m, 6H), 1.84-1.80 (m, 2H), 1.51-1.47 (m, 2H).

Example 1283

8-{4-[2-(3-Benzyloxy-propoxy)-6-fluoro-phenylamino]-5-chloro-pyrimidin-2-ylamino}-1,3,4,5-tetrahydro-1-benzazepin-2-one

Example 1283a

[2-(3-Benzyloxy-propoxy)-6-fluoro-phenyl]-(2,5-dichloro-pyrimidin-4-yl)-amine was prepared from 2-(2,5-Dichloro-pyrimidin-4-ylamino)-3-fluoro-phenol and 3-Benzyloxy-propan-1-ol in an analogous manner to Example 1283c. Title compound was isolated as a white foam (247 mg, 46%). HPLC purity=95%. LCMS 424.13 (M+H), HNMR 8.15 (s, 1H), 7.25-7.21 (m, 1H), 6.82-6.77 (m, 2H), 6.71 (s, 1H), 6.36-6.32 (m, 5H), 4.48 (s, 2H), 4.16-4.13 (m, 2H), 3.57-3.53 (m, 2H), 2.07-2.02 (m, 2H).

Example 1283b

8-{4-[2-(3-Benzyloxy-propoxy)-6-fluoro-phenylamino]-5-chloro pyrimidin-2-ylamino}-1,3,4,5-tetrahydro-1-benzazepin-2-one was prepared from [2-(3-Benzyloxy-propoxy)-6-fluoro-phenyl]-(2,5-dichloro-pyrimidin-4-yl)-amine and 8-Amino-1,3,4,5-tetrahydro-benzo[b]azepin-2-one in an analogous manner to Example 1221d. Title compound was isolated as a white solid (25 mg, 17%), HPLC 99% purity, LCMS: 564.25 (M+H), 1H-NMR (DMSO-d6, 400 MHz) δ 9.41 (s, 1H), 9.12 (s, 1H), 8.61 (s, 1H), 8.11 (s, 1H), 7.33-7.23 (m, 4H), 7.19-7.15 (m, 3H), 6.98-6.89 (m, 3H), 6.82 (d, J=8.3 Hz, 1H), 4.26 (s, 3H), 4.06-4.03 (m, 2H), 3.34-3.31 (m, 2H), 2.04-1.95 (m, 4H), 2.00-1.81 (m, 2H).

Example 1284

N(4)-[2-(3-Benzyloxy-propoxy)-6-fluoro-phenyl]-5-chloro-N(2)-[3-(2-methoxy-ethyl)-2,3,4,5-tetrahydro-1H-3-benzazepin-7-yl]-pyrimidine-2,4-diamine Prepared from 3-(2-Methoxy-ethyl)-2,3,4,5-tetrahydro-1H-benzo[d]azepin-7-ylamine and [2-(3-Benzyloxy-propoxy)-6-fluoro-phenyl]-(2,5-dichloro-pyrimidin-4-yl)-amine in an analogous manner to Example 1221d. Title compound was isolated as a white solid, HPLC purity 99%, LCMS 516.27 (M-benzyl), 1H-NMR (DMSO-d6, 400 MHz) δ 9.63 (s, 1H), 9.32 (s, 1H), 8.47 (s, 1H), 8.09 (s, 1H), 7.38-7.35 (m, 1H), 7.28-7.25 (m, 4H), 7.18-7.15 (m, 3H), 7.14-7.12 (d, 1H), 7.01-6.99 (m, 1H), 6.85 (d, J=8.5 Hz, 1H), 4.24 (s, 2H), 4.08-4.05 (m, 2H), 3.80-3.72 (m, 2H), 3.58-3.50 (m, 2H), 3.35-3.31 (m, 7H), 3.20-2.90 (m, 6H), 1.85-1.81 (m, 2H).

Example 1285

2-{5-Chloro-2-[3-(2-dimethylamino-acetylamino)-5,5-dimethyl-2-oxo-2,3,4,5-tetrahydro-1H-1-benzazepin-8-ylamino]-pyrimidin-4-ylamino}-3-fluoro-N-methyl-benzamide

Example 1285a

2-Dimethylamino-N-(5,5-dimethyl-8-nitro-2-oxo-2,3,4,5-tetrahydro-1H-1-benzazepin-3-yl)-acetamide. Dimethylamino-acetic acid (0.124 g, 1.20 mmol), EDCl (0.461 g, 2.41 mmol), HOBT (0.276 g, 2.05 mmol) and DMF (1.00 mL, 12.9 mmol) were stirred at rt for 30 minutes, followed by the addition of TEA (0.235 mL, 1.68 mmol) and 3-Amino-5,5-dimethyl-8-nitro-1,3,4,5-tetrahydro-1-benzazepin-2-one (0.300 g, 1.20 mmol). The reaction mixture was stirred at rt for 3 h, diluted with ether and washed with water. The organic layer was dried over MgSO4, filtered, and concentrated under reduced pressure. Title compound was isolated as a white solid (80 mg, 20%).

Example 1285b

N-(8-Amino-5,5-dimethyl-2-oxo-2,3,4,5-tetrahydro-1H-1-benzazepin-3-yl)-2-dimethylamino-acetamide was prepared from 2-Dimethylamino-N-(5,5-dimethyl-8-nitro-2-oxo-2,3,4,5-tetrahydro-1H-1-benzazepin-3-yl)-acetamide in an analogous manner to Example 1221c. (64 mg, 88%). LCMS 305 (M+H).

Example 1285c

2-{5-Chloro-2-[3-(2-dimethylamino-acetylamino)-5,5-dimethyl-2-oxo-2,3,4,5-tetrahydro-1H-1-benzazepin-8-ylamino]-pyrimidin-4-ylamino}-3-fluoro-N-methyl-benzamide was prepared from N-(8-Amino-5,5-dimethyl-2-oxo-2,3,4,5-tetrahydro-1H-1-benzazepin-3-yl)-2-dimethylamino-acetamide and 2-(2,5-Dichloro-pyrimidin-4-ylamino)-3-fluoro-N-methyl-benzamide in an analogous manner to Example 1221d. Title compound was isolated as a white solid. (55 mg, 45%). LCMS 585.30 (M+H), 1H-NMR (DMSO-d6, 400 MHz) δ 9.67 (bs, 2H), 9.42 (s, 1H), 9.35 (s, 1H), 8.86 (d, J=7.8 Hz, 1H), 8.50 (d, J=4.9 Hz, 1H), 8.19 (s, 1H), 7.49-7.46 (m, 2H), 7.36-7.31 (m, 2H), 7.21 (s, 1H), 7.11 (d, J=8.7 Hz, 1H), 3.93 (s, 2H), 2.78 (s, 6H), 2.74 (d, J=4.1 Hz, 6H), 2.22-2.18 (m, 1H), 1.94-1.79 (m, 2H), 1.35 (s, 3H), 1.25 (s, 3H).

Example 1286

8-[5-Chloro-4-(2,4-difluoro-6-morpholin-4-yl-phenylamino)-pyrimidin-2-ylamino]-1,3,4,5-tetrahydro-1-benzazepin-2-one

Example 1286a 4-(3,5-difluoro-2-nitro-phenyl)-morpholine. 1,3,5-Trifluoro-2-nitro-benzene (5.30 g, 29.9 mmol) and K2CO3 (4.96 g, 35.9 mmol) were mixed in DMSO (40.0 mL, 564 mmol) and morpholine (2.74 mL, 31.4 mmol) was added. The reaction was stirred at rt for 48 h, diluted with EtOAc and washed twice with water. The organic layer was dried over sodium sulfate, filtered, and concentrated under reduced pressure. Title compound isolated as a yellow oil (4.26 g, 58%). LCMS (m/e) 245 (M+H); 1H-NMR (CDCl3, 400 MHz) δ 6.67-6.58 (m, 2H), 3.80 (t, 4H, J=4.2 Hz), 3.06 (t, 4H, J=4.2 Hz), 19F-NMR (CDCl3, 400 MHz) δ −102, −118. Also obtained in this reaction, 4-(3,5-difluoro-4-nitro-phenyl)-morpholine as a yellow solid (2.85 g, 39%). m.p.=112-114° C.; LCMS (m/e) 245 (M+H); 1H-NMR (CDCl3, 400 MHz) δ 6.45-6.37 (m, 2H), 3.86 (t, 4H, J=4.5 Hz), 3.33 (t, 4H, J=4.5 Hz); 19F-NMR (CDCl3, 400 MHz) δ −115.

Example 1286b 2,4-Difluoro-6-morpholin-4-yl-phenylamine was prepared from 4-(3,5-Difluoro-2-nitro-phenyl)-morpholine in an analogous manner to Example 1c. Title compound was obtained as a purple solid (680 mg, 99%).

Example 1286c (2,5-Dichloro-pyrimidin-4-yl)-(2,4-difluoro-6-morpholin-4-yl-phenyl)-amine was prepared from 2,4-Difluoro-6-morpholin-4-yl-phenylamine and 2,4,5-Trichloropyrimidine in an analogous manner to Example 1230a. Title compound was isolated as an off-white foam (337 mg, 57%) HPLC 97% purity, LCMS 363.10 (M+H), 1H-NMR (CDCl3, 400 MHz) δ 8.23 (s, 1H), 6.90 (s, 1H), 6.72 (dd, 1H), 6.64 (d, J=9.6 Hz, 1H), 3.79-3.77 (m, 4H), 2.90-2.87 (m, 4H).

Example 1286d

8-[5-Chloro-4-(2,4-difluoro-6-morpholin-4-yl-phenylamino)-pyrimidin-2-ylamino]-1,3,4,5-tetrahydro-1-benzazepin-2-one was prepared from (2,5-Dichloro-pyrimidin-4-yl)-(2,4-difluoro-6-morpholin-4-yl-phenyl)-amine and 8-Amino-1,3,4,5-tetrahydro-benzo[b]azepin-2-one in an analogous manner to Example 1221d. Title compound was isolated as a white solid (58 mg, 38%) HPLC 99% purity, LCMS 503.22 (M+H), HNMR (DMSO) 9.36 (s, 1H), 9.29 (s, 1H), 8.53 (s, 1H), 8.13 (s, 1H), 7.21 (d, J=8.4 Hz, 1H), 6.97-6.93 (m, 2H), 6.84 (d, J=8.1 Hz, 1H), 6.79 (d, J=10.8 Hz, 1H), 3.52 (m, 4H), 2.92 (m, 4H), 2.56 (m, 2H), 2.08-2.02 (m, 4H).

Example 1287

5-Chloro-N(4)-(2,4-difluoro-6-morpholin-4-yl-phenyl)-N(2)-[3-(2-methoxy-ethyl)-2,3,4,5-tetrahydro-1H-3-benzazepin-7-yl]-pyrimidine-2,4-diamine Title compound was prepared from (2,5-Dichloro-pyrimidin-4-yl)-(2,4-difluoro-6-morpholin-4-yl-phenyl)-amine and 3-(2-Methoxy-ethyl)-2,3,4,5-tetrahydro-1H-benzo[d]azepin-7-ylamine in an analogous manner to Example 1221d. Title compound was isolated as a white solid (80 mg, 48%), HPLC 99% purity, LCMS 547.26 (M+H), 1H-NMR (DMSO-d6, 400 MHz) δ 9.69 (s, 1H), 9.37 (s, 1H), 8.52 (s, 1H), 8.13 (s, 1H), 7.28 (s, 1H), 7.17 (d, J=7.9 Hz, 1H), 7.02 (dd, J=6.9 Hz, 1H), 6.88 (d, J=8.2 Hz, 1H), 6.83 (10.9 Hz, 1H), 3.70-3.68 (m, 2H), 3.62-3.58 (m, 2H), 3.55-3.50 (m, 4H), 3.37-3.35 (m, 2H), 3.33 (s, 3H), 3.15-2.87 (m, 10H).

Example 1288

2-[5-Chloro-2-(5,5-dimethyl-3-morpholin-4-yl-2-oxo-2,3,4,5-tetrahydro-1H-1-benzazepin-8-ylamino)-pyrimidin-4-ylamino]-3-fluoro-N-methyl-benzamide

Example 1288a 5,5-Dimethyl-3-morpholin-4-yl-8-nitro-1,3,4,5-tetrahydro-1-benzazepin-2-one. Morpholine (0.0726 mL, 0.000833 mol) was dissolved in DMF (45 mL, 0.58 mol) and cooled to 0° C., and to this solution was added Sodium hydride, 60% disp. in mineral oil (40.0 mg). This mixture was allowed to stir for 30 minutes, followed by the addition of 3-Iodo-5,5-dimethyl-8-nitro-1,3,4,5-tetrahydro-1-benzazepin-2-one (300 mg, 0.0008 mol). The reaction was allowed to warm to rt for 16 h. The reaction was quenched by the addition of ice & water, partitioned between water and EtOAc, extracted 3× with 30 mL portions of EtOAc, was dried over MgSO4, filtered, and concentrated under reduced pressure. (87 mg, 30%). LCMS 320 (M+H)

Example 1288b

8-Amino-5,5-dimethyl-3-morpholin-4-yl-1,3,4,5-tetrahydro-1-benzazepin-2-one was prepared from 5,5-Dimethyl-3-morpholin-4-yl-8-nitro-1,3,4,5-tetrahydro-1-benzazepin-2-one in an analogous manner to Example 1221c. (19 mg, 24%), LCMS 290 (M+H).

Example 1288c

2-[5-Chloro-2-(5,5-dimethyl-3-morpholin-4-yl-2-oxo-2,3,4,5-tetrahydro-1H-1-benzazepin-8-ylamino)-pyrimidin-4-ylamino]-3-fluoro-N-methyl-benzamide was prepared from 8-Amino-5,5-dimethyl-3-morpholin-4-yl-1,3,4,5-tetrahydro-1-benzazepin-2-one and 2-(2,5-Dichloro-pyrimidin-4-ylamino)-3-fluoro-N-methyl-benzamide in an analogous manner to Example 1221d. Title compound was isolated as a yellow (5 mg, 10%), HPLC purity=99%, LCMS 570 (M+H), 1H-NMR (DMSO-d6, 400 MHz) δ 9.32 (s, 1H), 9.06 (bs, 1H), 8.53 (bs, 1H), 8.13 (s, 1H), 7.58-7.52 (m, 1H), 7.47 (d, J=7.9 Hz, 1H), 7.38-7.36 (m, 1H), 6.90 (d, 1H), 6.80 (bs, 1H) 6.73-6.71 (m, 1H), 4.33-4.30 (m, 1H), 3.63-3.50 (m, 8H), 2.72 (d, J=4.0 Hz, 3H), 1.77-1.73 (m, 1H), 1.49-1.46 (m, 1H), 1.24 (s, 3H), 1.19 (s, 3H).

Example 1289

2-[2-(3-Acetylamino-5,5-dimethyl-2-oxo-2,3,4,5-tetrahydro-1H-1-benzazepin-8-ylamino)-5-chloro-pyrimidin-4-ylamino]-3-fluoro-N-methyl-benzamide

Example 1289a

N-(5,5-Dimethyl-8-nitro-2-oxo-2,3,4,5-tetrahydro-1H-1-benzazepin-3-yl)-acetamide was prepared from 3-Amino-5,5-dimethyl-8-nitro-1,3,4,5-tetrahydro-1-benzazepin-2-one and acetic anhydride in an analogous manner to Example 1271d as a white solid. (420 mg, 90%), HPLC 99% purity, HNMR (DMSO) 10.21 (s, 1H), 8.14 (d, J=7.8 Hz, 1H), 7.99 (d, J=8.6 Hz, 1H), 7.84 (s, 1H), 7.69 (d, J=8.7 Hz, 1H), 4.28-4.21 (m, 1H), 2.23-2.17 (m, 1H), 2.02-1.95 (m, 1H), 1.81 (s, 3H), 1.45 (s, 3H), 1.32 (s, 3H).

Example 1289b

N-(8-Amino-5,5-dimethyl-2-oxo-2,3,4,5-tetrahydro-1H-1-benzazepin-3-yl)-acetamide was prepared from N-(5,5-Dimethyl-8-nitro-2-oxo-2,3,4,5-tetrahydro-1H-1-benzazepin-3-yl)-acetamide in an analogous manner to Example 1c. (260 mg, 97%). HPLC purity=90%, LCMS (262 M+H). 1H-NMR (DMSO-d6, 400 MHz) δ 9.59 (s, 1H), 7.98 (d, J=8.0 Hz, 1H), 7.01 (d, J=8.4 Hz, 1H), 6.38 (d, J=8.3 Hz, 1H), 6.25 (s, 1H), 5.32 (bs, 2H), 4.26-4.22 (m, 1H), 2.06-2.00 (m, 1H), 1.80-1.77 (m, 1H), 1.77 (s, 3H), 1.29 (s, 3H), 1.21 (s, 3H).

Example 1289c

2-[2-(3-Acetylamino-5,5-dimethyl-2-oxo-2,3,4,5-tetrahydro-1H-1-benzazepin-8-ylamino)-5-chloro-pyrimidin-4-ylamino]-3-fluoro-N-methyl-benzamide was prepared from N-(5,5-Dimethyl-8-nitro-2-oxo-2,3,4,5-tetrahydro-1H-1-benzazepin-3-yl)-acetamide and 2-(2,5-Dichloro-pyrimidin-4-ylamino)-3-fluoro-N-methyl-benzamide in an analogous manner to Example 1221d. (62 mg, 43%). HPLC purity=99%, LCMS 524 (M+H), 1H-NMR (DMSO-d6, 400 MHz) δ 9.53 (s, 1H), 9.39 (s, 1H), 9.35 (s, 1H), 8.51 (d, J=4.6 Hz, 1H), 8.19 (s, 1H), 8.04 (d, J=8.0 Hz, 1H), 7.49-7.45 (m, 2H), 7.33-7.26 (m, 2H), 7.15 (s, 1H), 7.08 (d, J=9.0 Hz, 1H), 4.22-4.17 (m, 1H), 2.73 (d, J=4.4 Hz, 3H), 2.08-2.06 (m, 1H), 1.87-1.84 (m, 1H), 1.84 (s, 3H), 1.32 (s, 3H), 1.23 (s, 3H).

Example 1290

2-[2-(3-Acetylamino-5,5-dimethyl-2-oxo-2,3,4,5-tetrahydro-1H-1-benzazepin-8-ylamino)-5-chloro-pyrimidin-4-ylamino]-3-fluoro-N-prop-2-ynyl-benzamide Title compound was prepared from N-(5,5-Dimethyl-8-nitro-2-oxo-2,3,4,5-tetrahydro-1H-1-benzazepin-3-yl)-acetamide and 2-(2,5-Dichloro-pyrimidin-4-ylamino)-3-fluoro-N-prop-2-ynyl-benzamide in an analogous manner to Example 1221d. Title compound was isolated as a white solid. (65 mg, 43%) LCMS 566 (M+H), 1H-NMR (DMSO-d6, 400 MHz) δ 9.50 (s, 1H), 9.39 (s, 1H), 9.17 (s, 1H), 8.93 (t, J=5.3 Hz, 1H), 8.18 (s, 1H), 8.04 (d, J=8.1 Hz, 1H), 7.51-7.46 (m, 2H), 7.37-7.34 (m, 1H), 7.24 (d, J=8.1 Hz, 1H), 7.14 (s, 1H), 7.08 (d, J=8.2 Hz, 1H), 4.23-4.16 (m, 1H), 4.00 (d, J=2.7 Hz, 2H), 3.10 (s, 1H), 2.09-2.04 (m, 1H), 1.88-1.84 (m, 1H), 1.84 (s, 3H), 1.32 (s, 3H), 1.23 (s, 3H).

Example 1291

3-[2-(3-Acetylamino-5,5-dimethyl-2-oxo-2,3,4,5-tetrahydro-1H-1-benzazepin-8-ylamino)-5-chloro-pyrimidin-4-ylamino]-thiophene-2-carboxylic acid methylamide Title compound was prepared from N-(5,5-Dimethyl-8-nitro-2-oxo-2,3,4,5-tetrahydro-1H-1-benzazepin-3-yl)-acetamide and 3-(2,5-Dichloro-pyrimidin-4-ylamino)-thiophene-2-carboxylic acid methylamide in an analogous manner to Example 1221d. Title compound was isolated as a brown solid. (51 mg, 36%) MP=205-210, LCMS 530 (M+H), 1H-NMR (DMSO-d6, 400 MHz) δ 11.70 (s, 1H), 9.80 (s, 1H), 9.63 (s, 1H), 8.47 (d, J=4.8 Hz, 1H), 8.26-8.24 (m, 2H), 8.08 (d, J=8.2 Hz, 1H), 7.76 (d, J=5.6 Hz, 1H), 7.47 (s, 1H), 7.35-7.30 (m, 2H), 4.32-4.29 (m, 1H), 2.78 (d, J=4.1 Hz, 3H), 2.14-2.10 (m, 1H), 1.94-1.90 (m, 1H), 1.87 (s, 3H), 1.38 (s, 3H), 1.27 (s, 3H).

Example 1292

2-{5-Chloro-2-[3-(2-methoxy-acetylamino)-5,5-dimethyl-2-oxo-2,3,4,5-tetrahydro-1H-1-benzazepin-8-ylamino]-pyrimidin-4-ylamino}-3-fluoro-N-methyl-benzamide

Example 1292a

N-(5,5-Dimethyl-8-nitro-2-oxo-2,3,4,5-tetrahydro-1H-1-benzazepin-3-yl)-2-methoxy-acetamide was prepared from 3-Amino-5,5-dimethyl-8-nitro-1,3,4,5-tetrahydro-1-benzazepin-2-one and Methoxyacetyl chloride in an analogous manner to Example 1271d (338 mg, 66%).

Example 1292b

N-(8-Amino-5,5-dimethyl-2-oxo-2,3,4,5-tetrahydro-1H-1-benzazepin-3-yl)-2-methoxy-acetamide was prepared from N-(5,5-Dimethyl-8-nitro-2-oxo-2,3,4,5-tetrahydro-1H-1-benzazepin-3-yl)-2-methoxy-acetamide in an analogous manner to Example 1221c. (white foam, 170 mg, 99%) LCMS 292 (M+H), 1H-NMR (CDCl3, 400 MHz) δ 7.42 (d, J=7.3 Hz, 1H), 7.30 (s, 1H), 7.20 (d, J=8.4 Hz, 1H), 6.38 (s, 1H), 4.66-4.59 (m, 1H), 3.93-3.87 (m, 2H), 3.69 (bs, 2H), 3.43 (s, 3H), 2.56-2.51 (m, 1H), 1.91-1.85 (m, 1H), 1.42 (s, 3H), 1.35 (s, 3H),

Example 1292c

2-{5-Chloro-2-[3-(2-methoxy-acetylamino)-5,5-dimethyl-2-oxo-2,3,4,5-tetrahydro-1H-1-benzazepin-8-ylamino]-pyrimidin-4-ylamino}-3-fluoro-N-methyl-benzamide was prepared from N-(8-Amino-5,5-dimethyl-2-oxo-2,3,4,5-tetrahydro-1H-1-benzazepin-3-yl)-2-methoxy-acetamide and 2-(2,5-Dichloro-pyrimidin-4-ylamino)-3-fluoro-N-methyl-benzamide in an analogous manner to Example 1221d. Title compound was isolated as a white solid (40 mg, 38%) HPLC purity=99%, LCMS=572 (M+H), 1H-NMR (DMSO-d6, 400 MHz) δ 9.72 (s, 1H), 9.40 (s, 1H), 9.34 (s, 1H), 8.51 (m, 1H), 8.18 (s, 1H), 7.70 (d, J=7.8 Hz, 1H), 7.49-7.44 (m, 2H), 7.31-7.27 (m, 2H), 7.16 (s, 1H), 7.10 (d, 1H), 4.23-4.21 (m, 1H), 3.82 (s, 2H), 3.33 (s, 3H), 2.73 (d, J=4.8 Hz, 3H), 2.22-2.18 (m, 1H), 1.92-1.88 (m, 1H), 1.33 (s, 3H), 1.24 (s, 3H).

Example 1293

2-{5-Chloro-2-[3-(2-methoxy-acetylamino)-5,5-dimethyl-2-oxo-2,3,4,5-tetrahydro-1H-1-benzazepin-8-ylamino]-pyrimidin-4-ylamino}-3-fluoro-N-prop-2-ynyl-benzamide Title compound was prepared from N-(8-Amino-5,5-dimethyl-2-oxo-2,3,4,5-tetrahydro-1H-1-benzazepin-3-yl)-2-methoxy-acetamide and 2-(2,5-Dichloro-pyrimidin-4-ylamino)-3-fluoro-N-prop-2-ynyl-benzamide in an analogous manner to Example 1221d. Title compound was isolated as a white solid (60 mg, 54%) HPLC 99% purity, LCMS 596 (M+H), 1H-NMR (DMSO-d6, 400 MHz) δ 9.69 (s, 1H), 9.39 (s, 1H), 9.16 (s, 1H), 8.94 (t, 1H), 8.18 (s, 1H), 7.70 (d, J=8.1 Hz, 1H), 7.48-7.44 (m, 2H), 7.34-7.29 (m, 1H), 7.26 (d, J=7.9 Hz, 1H), 7.15 (s, 1H), 7.09 (d, J=8.7 Hz, 1H), 4.22-4.17 (m, 1H), 4.00 (s, 2H), 3.82 (s, 2H), 3.33 (s, 3H), 3.10 (s, 1H), 2.19-2.15 (m, 1H), 1.91 (t, J=12.2 Hz, 1H), 1.33 (s, 3H), 1.24 (s, 3H).

Example 1294

2-{5-Chloro-2-[3-(2-methoxy-ethylamino)-5,5-dimethyl-2,3,4,5-tetrahydro-1H-1-benzazepin-8-ylamino]-pyrimidin-4-ylamino}-3-fluoro-N-methyl-benzamide

Example 1294a (5,5-Dimethyl-8-nitro-2,3,4,5-tetrahydro-1H-1-benzazepin-3-yl)-(2-methoxy-ethyl)-amine. A solution of N-(5,5-

Dimethyl-8-nitro-2-oxo-2,3,4,5-tetrahydro-1H-1-benzazepin-3-yl)-2-methoxy-acetamide (0.138 g, 0.43 mmol) in THF (10 mL, 0.1 mol) was treated with 1 M of Borane-THF complex in THF (3 mL). The reaction mixture was heated at 70° C. for 3 hours. The reaction mixture was quenched by the slow dropwise addition of methanol until all bubbling ceased, was concentrated, taken up in CH2Cl2 and washed with water. The organic layer was dried over magnesium sulfate, filtered, and concentrated under reduced pressure.

Example 1294b

N(3)-(2-Methoxy-ethyl)-5,5-dimethyl-2,3,4,5-tetrahydro-1H-1-benzazepine-3,8-diamine was prepared from (5,5-Dimethyl-8-nitro-2,3,4,5-tetrahydro-1H-1-benzazepin-3-yl)-(2-methoxy-ethyl)-amine in an analogous manner to Example 1221c. Title compound was obtained as a yellow oil (52 mg, 75%). LCMS 264 (M+H), 1H-NMR (CDCl3, 400 MHz) δ 7.07 (d, J=8.3 Hz, 1H), 6.23 (d, J=8.3 Hz, 1H), 6.03 (s, 1H), 3.52-3.48 (m, 4H), 3.33 (s, 3H), 3.32-3.29 (m, 1H), 2.86-2.82 (m, 1H), 2.82 (s, 2H), 2.65-2.62 (m, 1H), 1.78-1.76 (m, 1H), 1.57-1.54 (m, 1H), 1.38 (s, 3H), 1.30 (s, 3H).

Example 1294c

2-{5-Chloro-2-[3-(2-methoxy-ethylamino)-5,5-dimethyl-2,3,4,5-tetrahydro-1H-1-benzazepin-8-ylamino]-pyrimidin-4-ylamino}-3-fluoro-N-methyl-benzamide was prepared from N(3)-(2-Methoxy-ethyl)-5,5-dimethyl-2,3,4,5-tetrahydro-1H-1-benzazepine-3,8-diamine and 2-(2,5-Dichloro-pyrimidin-4-ylamino)-3-fluoro-N-methyl-benzamide in an analogous manner to Example 1d. Title compound was isolated as a white solid (29 mg, 27%), HPLC purity=90%, LCMS 544 (M+H), 1H-NMR (DMSO-d6, 400 MHz) δ 9.22 (s, 1H), 9.12 (s, 1H), 8.51-8.47 (m, 3H), 8.13 (s, 1H), 7.52-7.50 (m, 2H), 7.45-7.38 (m, 1H), 6.97 (s, 2H), 6.91 (s, 1H), 4.95-4.88 (m, 1H), 3.62-3.58 (m, 2H), 3.55-3.42 (m, 2H), 3.33 (s, 3H), 3.22-3.18 (m, 2H), 2.73-2.67 (d, 3H), 1.96-1.92 (m, 1H), 1.73-1.70 (m, 1H), 1.36 (s, 3H), 1.23 (s, 3H).

Example 1295

Pyrrolidine-1-carboxylic acid {8-[5-chloro-4-(2-fluoro-6-methylcarbamoyl-phenylamino)-pyrimidin-2-ylamino]-5,5-dimethyl-2-oxo-2,3,4,5-tetrahydro-1H-1-benzazepin-3-yl}-amide

Example 1295a

Pyrrolidine-1-carboxylic acid (5,5-dimethyl-8-nitro-2-oxo-2,3,4,5-tetrahydro-1H-1-benzazepin-3-yl)-amide was prepared from 3-Amino-5,5-dimethyl-8-nitro-1,3,4,5-tetrahydro-1-benzazepin-2-one and Pyrrolidine-1-carbonyl chloride in an analogous manner to Example 1271d as a pale yellow solid (256 mg, 92%). LCMS 347 (M+H). HPLC purity 99%.

Example 1295b

Pyrrolidine-1-carboxylic acid (8-amino-5,5-dimethyl-2-oxo-2,3,4,5-tetrahydro-1H-1-benzazepin-3-yl)-amide was prepared from Pyrrolidine-1-carboxylic acid (5,5-dimethyl-8-nitro-2-oxo-2,3,4,5-tetrahydro-1H-1-benzazepin-3-yl)-amide in an analogous manner to Example 1c. (white solid, 140 mg, 85%), LCMS 317 (M+H), 1H-NMR (CDCl3, 400 MHz) δ: 7.52 (s, 1H), 7.17 (d, J=8.3 Hz, 1H), 6.50 (d, J=8.3 Hz, 1H), 6.25 (s, 1H), 5.27 (d, J=6.6 Hz, 1H), 4.54-4.51 (m, 1H), 3.70 (s, 2H), 3.36-3.34 (m, 4H), 2.55-2.50 (m, 1H), 1.91-1.87 (m, 6H), 1.42 (s, 3H), 1.32 (s, 3H).

Example 1295c

Pyrrolidine-1-carboxylic acid {8-[5-chloro-4-(2-fluoro-6-methylcarbamoyl-phenylamino)-pyrimidin-2-ylamino]-5,5-dimethyl-2-oxo-2,3,4,5-tetrahydro-1H-1-benzazepin-3-yl}-amide was prepared from Pyrrolidine-1-carboxylic acid (8-amino-5,5-dimethyl-2-oxo-2,3,4,5-tetrahydro-1H-1-benzazepin-3-yl)-amide and 2-(2,5-Dichloro-pyrimidin-4-ylamino)-3-fluoro-N-methyl-benzamide in an analogous manner to Example 1221d. Title compound was isolated as a white solid (29 mg, 22%), HPLC purity=94%, LCMS 597 (M+H), 1H-NMR (DMSO-d6, 400 MHz) δ 9.47 (s, 1H), 9.40 (s, 1H), 9.33 (s, 1H), 8.54 (d, 1H), 8.19 (s, 1H), 7.52-7.42 (m, 2H), 7.38-7.25 (m, 2H), 7.15-7.07 (m, 2H), 5.92 (m, 1H), 4.09 (m, 1H), 3.22-3.18 (m, 4H), 2.73 (d, J=3.5 Hz, 3H), 1.81-1.77 (m, 4H), 1.32 (s, 3H), 1.23 (s, 3H).

Example 1296

Pyrrolidine-1-carboxylic acid {8-[5-chloro-4-(2-fluoro-6-prop-2-ynylcarbamoyl-phenylamino)-pyrimidin-2-ylamino]-5,5-dimethyl-2-oxo-2,3,4,5-tetrahydro-1H-1-benzazepin-3-yl}-amide Title compound was prepared from Pyrrolidine-1-carboxylic acid (8-amino-5,5-dimethyl-2-oxo-2,3,4,5-tetrahydro-1H-1-benzazepin-3-yl)-amide and 2-(2,5-Dichloro-pyrimidin-4-ylamino)-3-fluoro-N-prop-2-ynyl-benzamide in an analogous manner to Example 1221d. Title compound was isolated as a white solid (47 mg, 35%), HPLC purity 96%, LCMS 550 (M-propargyl amide), 1H-NMR (DMSO-d6, 400 MHz) δ 9.48 (s, 1H), 9.39 (s, 1H), 9.16 (s, 1H), 8.92 (t, 1H), 8.18 (s, 1H), 7.58-7.48 (m, 2H), 7.40-7.32 (m, 1H), 7.23-7.20 (d, 1H), 7.08-7.02 (m, 2H), 5.95 (m, 1H), 4.18-4.12 (m, 1H), 3.99 (d, 2H), 3.56 (m, 1H), 3.20 (m, 4H), 2.15-2.10 (m, 1H), 2.00-1.92 (m, 1H), 1.79 (m, 4H), 1.32 (s, 3H), 1.23 (s, 3H).

Example 1297

2-{5-Chloro-2-[(S)-5,5-dimethyl-2-oxo-3-(2,2,2-trifluoro-acetylamino)-2,3,4,5-tetrahydro-1H-1-benzazepin-8-ylamino]-pyrimidin-4-ylamino}-3-fluoro-N-methyl-benzamide Title compound was prepared from supercritical fluid chromatographic separation of the racemic material. All spectral data identical to Example 51f.

Example 1298

2-{5-Chloro-2-[(R)-5,5-dimethyl-2-oxo-3-(2,2,2-trifluoro-acetylamino)-2,3,4,5-tetrahydro-1H-1-benzazepin-8-ylamino]-pyrimidin-4-ylamino}-3-fluoro-N-methyl-benzamide Title compound was prepared from supercritical fluid chromatographic separation of the racemic material. All spectral data identical to Example 51f.

Example 1299

{8-[5-Chloro-4-(2-fluoro-6-methylcarbamoyl-phenylamino)-pyrimidin-2-ylamino]-5,5-dimethyl-2-oxo-2,3,4,5-tetrahydro-1H-1-benzazepin-3-yl}-carbamic acid methyl ester

Example 1299a (5,5-Dimethyl-8-nitro-2-oxo-2,3,4,5-tetrahydro-1H-1-benzazepin-3-yl)-carbamic acid methyl ester was prepared from 3-Amino-5,5-dimethyl-8-nitro-1,3,4,5-tetrahydro-1-benzazepin-2-one and Methyl chloroformate in an analogous manner to Example 1271d. Title compound is an off white solid. (94 mg, 38%) LCMS 308 (M+H).

Example 1299b (8-Amino-5,5-dimethyl-2-oxo-2,3,4,5-tetrahydro-1H-1-benzazepin-3-yl)-carbamic acid methyl ester was prepared from (5,5-Dimethyl-8-nitro-2-oxo-2,3,4,5-tetrahydro-1H-1-benzazepin-3-yl)-carbamic acid methyl ester in an analogous manner to Example 1221c as a yellow solid (80 mg, 94%), LCMS 278 (M+H).

Example 1299c

{8-[5-Chloro-4-(2-fluoro-6-methylcarbamoyl-phenylamino)-pyrimidin-2-ylamino]-5,5-dimethyl-2-oxo-2,3,4,5-tetrahydro-1H-1-benzazepin-3-yl}-carbamic acid methyl ester was prepared from (8-Amino-5,5-dimethyl-2-oxo-2,3,4,5-tetrahydro-1H-1-benzazepin-3-yl)-carbamic acid methyl ester and 2-(2,5-Dichloro-pyrimidin-4-ylamino)-3-fluoro-N-methyl-benzamide in an analogous manner to Example 1d. Title compound was isolated as a pale yellow solid (30 mg, 19%) LCMS 558 (M+H), HNMR (DMSO) 9.51 (s, 1H), 9.39 (s, 1H), 9.34 (s, 1H), 8.51 (d, 1H), 8.19 (s, 1H), 7.49-7.46 (m, 2H), 7.39-7.25 (m, 3H), 7.15 (s, 1H), 7.09 (m, 1H), 3.93-3.90 (m, 1H), 3.50 (s, 3H), 2.74 (d, J=3.8 Hz, 3H), 2.09-2.06 (m, 1H), 1.95-1.89 (m, 1H), 1.32 (s, 3H), 1.22 (s, 3H).

Example 1300

2-{5-Chloro-4-[2-fluoro-6-(tetrahydro-furan-3-yloxy)-phenylamino]-pyrimidin-2-ylamino}-5-methyl-8,9-dihydro-5H-7-oxa-5-aza-benzocyclohepten-6-one Title compound was prepared from 2-Amino-5-methyl-8,9-dihydro-5H-7-oxa-5-aza-benzocyclohepten-6-one and (2,5-Dichloro-pyrimidin-4-yl)-[2-fluoro-6-(tetrahydro-furan-3-yloxy)-phenyl]-amine in an analogous manner to Example 1221d. Title compound was isolated as a pale yellow solid (28 mg, 32%) HPLC purity=99%, LCMS=502.27 (M+H), HNMR (DMSO) 9.37 (s, 1H), 8.55 (bs, 1H), 8.11 (s, 1H), 7.37-7.34 (m, 2H), 7.23 (d, J=7.8 Hz, 1H), 7.00-6.95 (m, 3H), 5.00 (bt, 1H), 4.26-4.23 (m, 2H), 3.81-3.77 (m, 1H), 3.62-3.59 (m, 2H), 3.57-3.53 (m, 1H), 3.19 (s, 3H), 2.62-2.59 (m, 2H), 2.06-2.01 (m, 1H), 1.81-1.78 (m, 1H).

Example 1301

2-{5-Chloro-2-[4-oxo-1-(2,2,2-trifluoro-acetyl)-1,2,3,4,5,6-hexahydro-benzo[b][1,5]diazocin-8-ylamino]-pyrimidin-4-ylamino}-N-methyl-benzamide Example 1301a 1-(2,2,2-Trifluoro-acetyl)-2,3,5,6-tetrahydro-1H-benzo[b][1,5]diazocin-4-one was prepared from 2,3,5,6-Tetrahydro-1H-benzo[b][1,5]diazocin-4-one and trifluoroacetic anhydride in an analogous manner to Example 1224a. (2.21 g, 72%). mp 218-219° C.; LCMS: m/z=273.24 (M+H+), HPLC (95% purity); 1H NMR (400 MHz, CDCl3) δ 7.39 (m, 3H), 7.27 (m, 1H), 6.52 (bs, 1H), 4.82 (m, 1H), 4.39 (m, 1H), 4.03 (m, 1H), 3.07 (m, 1H), 2.95 (m, 1H), 2.67 (m, 1H).

Example 1301b

8-Nitro-1-(2,2,2-trifluoro-acetyl)-2,3,5,6-tetrahydro-1H benzo[b][1,5]diazocin-4-one was prepared from 1-(2,2,2-Trifluoro-acetyl)-2,3,5,6-tetrahydro-1H-benzo[b][1,5]diazocin-4-one in an analogous manner to Example 1224b. Isolated as a pale yellow solid (1.53 g, 60%). mp 244-246° C.; LCMS: m/z=318.25 (M+H+), HPLC (96% purity); 1H NMR (400 MHz, CDCl3) δ 8.29 (m, 2H), 7.52 (m, 1H), 6.22 (bs, 1H), 4.90 (m, 1H), 4.48 (m, 1H), 4.18 (m, 1H), 3.05 (m, 1H), 2.96 (m, 1H), 2.74 (m, 1H).

Example 1301c

8-Amino-1-(2,2,2-trifluoro-acetyl)-2,3,5,6-tetrahydro-1H-benzo[b][1,5]diazocin-4-one was prepared from 8-Nitro-1-(2,2,2-trifluoro-acetyl)-2,3,5,6-tetrahydro-1H benzo[b][1,5]diazocin-4-one in an analogous manner to Example 1221c. Isolated as an off-white solid (200 mg, 92%). mp 225-227° C.; LCMS: m/z=288.22 (M+H+), HPLC (88% purity); 1H NMR (400 MHz, DMSO-d6) δ 7.89 (m, 1H), 6.96 (d, J=8.6 Hz, 1H), 6.48 (m, 2H), 4.58 (m, 1H), 4.23 (m, 1H), 3.64 (m, 1H), 3.00 (m, 1H), 2.72 (m, 1H), 2.32 (m, 1H).

Example 1301d

2-{5-Chloro-2-[4-oxo-1-(2,2,2-trifluoro-acetyl)-1,2,3,4,5,6-hexahydro-benzo[b][1,5]diazocin-8-ylamino]-pyrimidin-4-ylamino}-N-methyl-benzamide was prepared from 8-Amino-1-(2,2,2-trifluoro-acetyl)-2,3,5,6-tetrahydro-1H-benzo[b][1,5]diazocin-4-one and 2-(2,5-Dichloro-pyrimidin-4-ylamino)-N-methyl-benzamide in an analogous manner to Example 1221d. Title compound isolated as an off-white solid (27 mg, 14%). mp 191-194° C.; LCMS: m/z=548.25 (M+H+), HPLC (98% purity), 1H NMR (400 MHz, DMSO-d6) δ 11.69 (s, 1H), 9.78 (s, 1H), 8.72 (m, 2H), 8.27 (s, 1H), 7.90 (m, 1H), 7.77 (d, J=8.1 Hz, 1H), 7.71 (s, 1H), 7.66 (d, J=8.6 Hz, 1H), 7.46 (t, J=8.3 Hz, 1H), 7.29 (d, J=8.3 Hz, 1H), 7.16 (t, J=7.8 Hz, 1H), 4.65 (m, 1H), 4.43 (m, 1H), 3.70 (m, 1H), 3.18 (m, 1H), 2.81 (m, 4H), 2.36 (m, 1H).

Example 1302

2-[5-Chloro-2-(4-oxo-1,2,3,4,5,6-hexahydro-benzo[b][1,5]diazocin-8-ylamino)-pyrimidin-4-ylamino]-N-methyl-benzamide 2-{5-Chloro-2-[4-oxo-1-(2,2,2-trifluoro-acetyl)-1,2,3,4,5,6-hexahydro-benzo[b][1,5]diazocin-8-ylamino]-pyrimidin-4-ylamino}-N-methyl-benzamide (23 mg, 0.05 mmol) was dissolved in 1/1 EtOH/30% NaOH (2 ml) and heated to 80° C. in the microwave for 10 min. Reaction mixture was neutralized, extracted with CH2Cl2, dried over MgSO4, filtered, and concentrated to afford title compound as an off-white solid (5 mg, 26%) mp 267-268° C.; LCMS: m/z=452.30 (M+H+), HPLC (98% purity); 1H NMR (400 MHz, DMSO-d6) δ 11.61 (s, 1H), 9.21 (s, 1H), 8.72 (m, 2H), 8.16 (s, 1H), 7.73 (m, 1H), 7.47 (m, 2H), 7.32 (m, 2H), 7.11 (m, 1H), 6.73 (m, 1H), 5.74 (m, 1H), 4.18 (m, 2H), 3.23 (m, 2H), 2.73 (m, 3H), 2.65 (m, 2H).

Example 1303

2-{5-Chloro-2-[4-oxo-1-(2,2,2-trifluoro-acetyl)-1,2,3,4,5,6-hexahydro-benzo[b][1,5]diazocin-8-ylamino]-pyrimidin-4-ylamino}-N-methyl-benzenesulfonamide Title compound was prepared from 8-Amino-1-(2,2,2-trifluoro-acetyl)-2,3,5,6-tetrahydro-1H-benzo[b][1,5]diazocin-4-one and 2-(2,5-Dichloro-pyrimidin-4-ylamino)-N-methyl-benzenesulfonamide in an analogous manner to Example 1221d. Title compound isolated as a yellow solid (66 mg, 23%). mp 181-183° C.; LCMS: m/z=583.83 (M+H+), HPLC (90% purity); 1H NMR (400 MHz, CDCl3) δ 8.02 (s, 1H), 7.77 (s, 1H), 7.57 (m, 2H), 7.42 (m, 2H), 7.29 (m, 2H), 7.10 (m, 1H), 6.87 (m, 1H), 6.72 (m, 1H), 4.67 (m, 1H), 4.06 (m, 2H), 3.48 (m, 1H), 3.02 (s, 3H), 2.92 (m, 1H), 2.75 (m, 1H), 2.55 (m, 1H).

Example 1304

2-[5-Chloro-2-(4-oxo-1,2,3,4,5,6-hexahydro-benzo[b][1,5]diazocin-8-ylamino)-pyrimidin-4-ylamino]-N-methyl-benzenesulfonamide Title compound was prepared from 2-{5-Chloro-2-[4-oxo-1-(2,2,2-trifluoro-acetyl)-1,2,3,4,5,6-hexahydro-benzo[b][1,5]diazocin-8-ylamino]-pyrimidin-4-ylamino}-N-methyl-benzenesulfonamide in an analogous manner to Example 1302 to afford an off-white solid. (9 mg, 19%). mp 197-198° C.; LCMS: m/z=585.85 (M+H+), HPLC (91% purity); 1H NMR (400 MHz, CDCl3) δ 7.96 (m, 1H), 7.63 (m, 1H), 7.52 (m, 2H), 7.35 (m, 2H), 7.25 (m, 1H), 7.09 (m, 1H), 6.94 (m, 1H), 6.65 (m, 1H), 6.03 (m, 1H), 4.68 (s, 1H), 4.13 (m, 2H), 3.24 (m, 2H), 2.95 (s, 3H), 2.80 (m, 2H).

Example 1305

2-[2-(1-Acetyl-4-oxo-1,2,3,4,5,6-hexahydro-benzo[b][1,5]diazocin-8-ylamino)-5-chloro-pyrimidin-4-ylamino]-N-methyl-benzamide Title compound was prepared from 1-Acetyl-8-amino-2,3,5,6-tetrahydro-1H-benzo[b][1,5]diazocin-4-one 2-(2,5-Dichloro-pyrimidin-4-ylamino)-N-methyl-benzamide in an analogous manner to Example 1221d. Title compound isolated as a beige solid (27 mg, 6%). mp 223-225° C.; LCMS: m/z=494.34 (M+H+), HPLC (83% purity) 1H NMR (400 MHz, DMSO-d6) δ 11.66 (s, 1H), 9.71 (s, 1H), 8.72 (m, 2H), 8.26 (s, 1H), 7.83 (m, 1H), 7.76 (d, J=7.8 Hz, 1H), 7.67 (m, 2H), 7.51 (t, J=7.6 Hz, 1H), 7.22 (d, J=8.6 Hz, 1H), 7.16 (t, J=7.8 Hz, 1H), 4.62 (m, 1H), 4.27 (m, 1H), 3.72 (m, 1H), 3.31 (m, 5H), 2.89 (m, 1H), 2.81 (d, J=4.0 Hz, 3H), 2.29 (m, 1H).

Example 1307

2-{5-Chloro-4-[2-fluoro-6-(tetrahydro-furan-3-yloxy)-phenoxy]-pyrimidin-2-ylamino}-5-methyl-8,9-dihydro-5H-7-oxa-5-aza-benzocyclohepten-6-one Example 1307a 2,5-Dichloro-4-(2-fluoro-6-methoxy-phenoxy)-pyrimidine was prepared from 2-Fluoro-6-methoxy-phenol and 2,4,5-Trichloropyrimidine in an analogous manner to Example 1230a. (1.95 g, 96%) LCMS 290 (M+H), 1H-NMR (DMSO-d6, 400 MHz) δ 8.91 (s, 1H), 7.38-7.34 (m, 1H), 7.10-7.03 (m, 2H), 3.80 (s, 3H).

Example 1307b 2-(2,5-Dichloro-pyrimidin-4-yloxy)-3-fluoro-phenol was prepared from 2,5-Dichloro-4-(2-fluoro-6-methoxy-phenoxy)-pyrimidine in an analogous manner to Example 1273b. Title compound isolated as a white solid (1.66 g, 93%) LCMS 276 (M+H).

Example 1307c 2,5-Dichloro-4-[2-fluoro-6-(tetrahydro-furan-3-yloxy)-phenoxy]-pyrimidine was prepared from 2-(2,5-Dichloro-pyrimidin-4-yloxy)-3-fluoro-phenol and 3-Hydroxy THF in an analogous manner to Example 1273c. Title compound isolated as sticky white solid. LCMS 347.11 (M+H)

Example 1307d

2-{5-Chloro-4-[2-fluoro-6-(tetrahydro-furan-3-yloxy)-phenoxy]-pyrimidin-2-ylamino}-5-methyl-8,9-dihydro-5H-7-oxa-5-aza-benzocyclohepten-6-one was prepared from 2,5-Dichloro-4-[2-fluoro-6-(tetrahydro-furan-3-yloxy)-phenoxy]-pyrimidine and 2-Amino-5-methyl-8,9-dihydro-5H-7-oxa-5-aza-benzocyclohepten-6-one in an analogous manner to Example 1221d. Title compound was isolated as a white solid HPLC purity=99%, LCMS 503.21 (M+H), 1H-NMR (DMSO-d6, 400 MHz) δ 9.88 (s, 1H), 8.52 (s, 1H), 7.30-7.18 (m, 5H), 7.02 (d, J=8.7 Hz, 1H), 4.87 (s, 1H), 4.26-4.23 (m, 2H), 3.69-3.65 (m, 4H), 3.19 (s, 3H), 2.65 (m, 2H), 1.94-1.90 (m, 2H).

Example 1308

{5-Chloro-4-[2-fluoro-6-(tetrahydro-furan-3-yloxy)-phenoxy]-pyrimidin-2-yl}-[3-(2-methoxy-ethyl)-2,3,4,5-tetrahydro-1H-3-benzazepin-7-yl]-amine Title compound was prepared from 2,5-Dichloro-4-[2-fluoro-6-(tetrahydro-furan-3-yloxy)-phenoxy]-pyrimidine and 3-(2-Methoxy-ethyl)-2,3,4,5-tetrahydro-1H-benzo[d]azepin-7-ylamine in an analogous manner to Example 1d. Title compound was isolated as a white solid. HPLC purity=99%, LCMS=531.32 (M+H), 1HNMR (CDCl3, 400 MHz) δ 9.00 (bs, 1H), 8.24 (s, 1H), 7.28-7.16 (m, 3H), 7.16-7.14 (m, 1H), 7.14 (d, J=7.3 Hz, 1H), 6.29 (bs, 1H), 4.97 (s, 1H), 3.86-3.78 (m, 8H), 3.38-3.32 (m, 7H), 2.85-2.81 (m, 3H), 2.60-2.55 (m, 1H), 2.09-1.95 (m, 2H).

Example 1311

7-{5-Chloro-4-[2-methoxy-4-(4-methyl-piperazin-1-yl)-phenylamino]-pyrimidin-2-ylamino}-1-ethyl-6-methoxy-1,3,4,5-tetrahydro-benzo[b]azepin-2-one Following a procedure analogous to 101b, 7-Amino-1-ethyl-6-methoxy-1,3,4,5-tetrahydro-benzo[b]azepin-2-one (46 mg) and (2,5-Dichloro-pyrimidin-4-yl)-[2-methoxy-4-(4-methyl-piperazin-1-yl)-phenyl]-amine (60 mg) were reacted to give 7-{5-Chloro-4-[2-methoxy-4-(4-methyl-piperazin-1-yl)-phenylamino]-pyrimidin-2-ylamino}-1-ethyl-6-methoxy-1,3,4,5-tetrahydro-benzo[b]azepin-2-one (29 mgs, 26%) as an off-white solid. 1H-NMR (CDCl3, 400 MHz): δ 8.27 (d, J=8.8 Hz, 1H), 8.19 (d, J=8.6 Hz, 1H), 8.06 (s, 1H), 7.55 (s, 1H), 7.40 (s, 1H), 6.94 (d, J=8.9 Hz, 1H), 6.59-6.55 (m, 2H), 3.93 (s, 3H), 3.85-3.81 (broad m, 2H) 3.80 (s, 3H), 3.26-3.23 (m, 4H), 2.65-2.63 (M, 4H), 2.39 (s, 3H), 2.32 (broad s, 2H), 1.74 (broad s, 4H), 1.22 (t, J=6.1 Hz, 3H); LC/MS Found (M+H)+=565.98; MP: 186-187° C.

Example 1312

(1S,2S,3R,4R)-3-[5-Chloro-2-(8-methoxy-5,5-dimethyl-2-oxo-2,3,4,5-tetrahydro-1H-benzo[b]azepin-7-ylamino-pyrimidin-4-ylamino]-bicyclo[2.2.1]hept-5-ene-2-carboxylic acid amide Following a procedure analogous to 101b, 7-Amino-8-methoxy-5,5-dimethyl-1,3,4,5-tetrahydro-benzo[b]azepin-2-one (66 mg) and (1S,2S,3R,4R)-3-(2,5-Dichloro-pyrimidin-4-ylamino)-bicyclo[2.2.1]hept-5-ene-2-carboxylic acid amide (78 mg) were reacted to give (1S,2S,3R,4R)-3-[5-Chloro-2-(8-methoxy-5,5-dimethyl-2-oxo-2,3,4,5-tetrahydro-1H-benzo[b]azepin-7-ylamino-pyrimidin-4-ylamino]-bicyclo[2.2.1]hept-5-ene-2-carboxylic acid amide (62 mg). 1H-NMR (CDCL3, 400 MHz): δ 8.45 (s, 1H), 7.93 (s, 1H), 7.64 (s, 1H), 7.34 (s, 1H), 6.50-6.49 (m, 2H), 6.29 (s, 2H), 5.62 (d, J=6.0 Hz, 2H), 4.54 (t, J=8.3 Hz, 1H), 3.90 9s, 3H), 3.08 (s, 1H), 2.83 (s, 1H), 2.50 (d, J=8.0 Hz, 1H), 2.41-2.38 (m, 2H), 2.28 (d, J=9.3 Hz, 1H), 2.13-2.09 (m, 2H), 1.71-1.68 (m, 2H), 1.41-1.40 (m, 1H); LC/MS found (M+H)+=497.18; MP=179-189° C.

Example 1313

(1S,2S,3R,4R)-3-[5-Chloro-2-(8-methoxy-1,5,5-trimethyl-2-oxo-2,3,4,5-tetrahydro-1H-benzo[b]azepin-7-ylamino)-pyrimidin-4-ylamino]-bicyclo[2.2.1]hept-5-ene-2-carboxylic acid amide Following a procedure analogous to 101b, 7-Amino-8-methoxy-1,5,5-trimethyl-1,3,4,5-tetrahydro-benzo[b]azepin-2-one (93 mgs) and (1S,2S,3R,4R)-3-(2,5-Dichloro-pyrimidin-4-ylamino)-bicyclo[2.2.1]hept-5-ene-2-carboxylic acid amide was converted to (1S,2S,3R,4R)-3-[5-Chloro-2-(8-methoxy-1,5,5-trimethyl-2-oxo-2,3,4,5-tetrahydro-1H-benzo[b]azepin-7-ylamino)-pyrimidin-4-ylamino]-bicyclo[2.2.1]hept-5-ene-2-carboxylic acid amide (63 mgs) as an off-white solid. 1H-NMR (CDCl3, 400 MHz): δ 8.42 (s, 1H), 7.94 (s, 1H), 7.39 (s, 1H), 6.70 (s, 2H), 6.48 (d, J=8.8 Hz, 2H), 6.29 (s, 2H), 5.53 (broad s, 1H), 5.30 (broad s, 1H), 4.56 (t, J=8.4 Hz, 1H), 3.92 (s, 3H), 3.31 (s, 3H), 3.09 (s, 1H), 2.83 (s, 1H), 2.51 (d, J=8.1 Hz, 1H), 2.32-2.29 (m, 3H), 2.09-2.05 (m, 2H), 1.68 (d, J=9.6 Hz, 1H), 1.34 (s, 6H); LC/MS found (M+H)+=511.26 MP: 153-160°.

Example 1314

(1S,2S,3R,4R)-3-[5-Chloro-2-(1-ethyl-8-methoxy-5,5-dimethyl-2-oxo-2,3,4,5-tetrahydro-1H-benzo[b]azepin-7-ylamino)-pyrimidin-4-ylamino]-bicyclo[2.2.1]hept-5-ene-2-carboxylic acid amide Following a procedure analogous to 101b, 7-Amino-1-ethyl-8-methoxy-5,5-dimethyl-1,3,4,5-tetrahydro-benzo[b]azepin-2-one (88 mgs) and (1S,2S,3R,4R)-3-(2,5-Dichloro-pyrimidin-4-ylamino)-bicyclo[2.2.1]hept-5-ene-2-carboxylic acid amide (84 mgs) gave the title compound as white solid 103 mgs (70%); 1H-NMR (CDCl3, 400 MHz) δ 8.43 (s, 1H), 7.94 (s, 1H), 7.39 (s, 1H), 6.76 (s, 1H), 6.47 (d, J=9.0 Hz, 1H), 6.29 (s, 2H), 5.54 (broad s, 1H), 5.32 (broad s, 1H), 4.56 (t, J=8.6 Hz, 1H), 3.92 (s, 3H), 3.83 (broad m, 2H), 3.09 (s, 1H), 2.83 (s, 1H), 2.51 (d, J=8.2 Hz, 1H), 2.29-2.25 (m, 3H), 2.09-2.05 (m, 2H), 1.68 (d, J=9.3 Hz, 1H), 1.34 (s, 6H), 0.91-0.85 (m, 3H); LC/MS: found (M+H)+=525.28; MP: 156-166° C.

Example 1315

(1S,2S,3R,4R)-3-{5-Chloro-2-[8-methoxy-3-(2-methoxy-ethyl)-2,3,4,5-tetrahydro-1H-benzo[d]azepin-7-ylamino]-pyrimidin-4-ylamino}-bicyclo[2.2.1]hept-5-ene-2-carboxylic acid amide Following a procedure analogous to Example 112 using (1S,2S,3R,4R)-3-(2,5-Dichloro-pyrimidin-4-ylamino)-bicyclo[2.2.1]hept-5-ene-2-carboxylic acid amide (110 mgs) provided the title compound (78 mgs, 42%). found (M+H)+=513.23 MP: 105-115°. NMR was equivalent to Example 112.

Example 1316

(1S,2S,3R,4R)-3-[5-Chloro-2-(1-ethyl-8-methoxy-2-oxo-2,3,4,5-tetrahydro-1H-benzo[b]azepin-7-ylamino)-pyrimidin-4-ylamino]-bicyclo[2.2.1]hept-5-ene-2-carboxylic acid amide Following a procedure analogous to Example 113, 7-Amino-1-ethyl-8-methoxy-1,3,4,5-tetrahydro-benzo[b]azepin-2-one (59 mgs) and (1S,2S,3R,4R)-3-(2,5-Dichloro-pyrimidin-4-ylamino)-bicyclo[2.2.1]hept-5-ene-2-carboxylic acid amide (69 mgs) were converted to the title compound as an off-white solid (65 mgs, 57%). 1H-NMR (CDCl3): δ 8.33 (s, 1H), 7.94 (s, 1H), 7.50 (broad s, 1H), 6.80-6.77 (m, 1H), 6.72 (s, 1H), 6.34 (s, 2H), 5.62 (broad s, 1H), 5.45 (broad s, 1H), 4.47 (t, J=8.6 Hz, 1H), 3.92 (s, 3H), 3.10 (s, 1H), 2.90 (s, 1H), 2.69-2.59 (m, 1H), 2.55 (d, J=8.1 Hz, 1H), 2.30-2.15 (m, 4H), 1.68 (d, J=9.3 Hz, 1H), 1.32 (s, 2H), 1.60 (t, J=7.1 Hz, 3H), 0.99-0.92 (m, 2). MP: 145-153° C., LCMS, found 497 (M+H)+.

Example 1317

7-[5-Chloro-4-(2-pyrazol-1-yl-phenylamino)-pyrimidin-2-ylamino]-1-ethyl-8-methoxy-1,3,4,5-tetrahydro-benzo[b]azepin-2-one Following a procedure analogous to Example 113, 7-Amino-1-ethyl-8-methoxy-1,3,4,5-tetrahydro-benzo[b]azepin-2-one (51 mgs) and (2,5-Dichloro-pyrimidin-4-yl)-(2-pyrazol-1-yl-phenyl)-amine were combined to prepare the title compound (32 mgs, 32%) as a white foam. 1H-NMR (CDCl3): δ 10.24 (s, 1H), 8.50 (d, J=8.3 Hz, 1H), 8.20 (s, 1H), 8.10 (s, 1H), 7.85 (d, J=14.4 Hz, 2H), 7.56 (s, 1H), 7.43-7.37 (m, 2H), 7.23 (t, J=7.6 Hz, 1H), 6.71 (s, 1H), 6.53 (s, 1H), 3.91 (s, 3H), 2.68-2.54 (m, 1H), 2.28 (broad s, 2H), 2.17-2.09 (m, 1H), 1.27 (brad s, 2H), 1.18 (t, J=7.1 Hz, 3H). LC/MS: found (M+H)+=504.24; MP: 82-85° C.

Example 1318

7-[5-Chloro-4-(2-methoxy-phenylamino)-pyrimidin-2-ylamino]-1-ethyl-8-methoxy-1,3,4,5-tetrahydro-benzo[b]azepin-2-one Following a procedure analogous to Example 113, 7-Amino-1-ethyl-8-methoxy-1,3,4,5-tetrahydro-benzo[b]azepin-2-one (51 mgs) and (2,5-Dichloro-pyrimidin-4-yl)-(2-methoxy-phenyl)-amine (53 mgs) was converted to the title compound (33 mgs, 35%) as a white foam. 1H-NMR (CDCl3): δ 8.42 (d, J=7.9 Hz, 1H), 8.23 (s, 1H), 8.11 (s, 1H), 7.82 (s, 1H), 7.54 (s, 1H), 7.13-7.09 (1, 2H), 7.01-6.94 (d, 2H), 6.72 (s, 1H), 3.97 (s, 3H), 3.92 (s, 3H), 2.70-2.60 (m, 2H), 2.30-2.19 (m, 4H), 1.17 (t, J=7.3 Hz, 3H). LC/MS: found (M+H)+=468.24; MP: 78-80° C.

Example 1319

7-[5-Chloro-4-(2-pyrazol-1-yl-phenylamino)-pyrimidin-2-ylamino]-1-ethyl-6-methoxy-1,3,4,5-tetrahydro-benzo[b]azepin-2-one Following a procedure analogous to Example 113, 7-Amino-1-ethyl-6-methoxy-1,3,4,5-tetrahydro-benzo[b]azepin-2-one (75 mgs) and (2,5-Dichloro-pyrimidin-4-yl)-(2-pyrazol-1-yl-phenyl)-amine (89 mgs) were converted to the title compound as an off-white solid (66 mgs). 1H-NMR (CDCl3): δ 10.30 (s, 1H), 8.52 (d, J=8.6 Hz, 1H), 8.26 (d, J=8.8 Hz, 1H), 8.10 (s, 1H), 7.86 (d, J=15.7 Hz, 2H), 7.44-7.41 (m, 2H), 7.28-7.25 (m, 1H), 6.94 (d, J=9.1 Hz, 1H), 6.54 (s, 1H), 3.80 (s, 3H), 2.32 (broad S, 2H), 3.15-1.5 broad absorptions, 6H), 1.15 (t, J=7.3 Hz, 3H). LC/MS, found 504.17 (M+H)+; MP: 183-185° C.

Example 1320

2-{7-[5-Chloro-4-(2-pyrazol-1-yl-phenylamino)-pyrimidin-2-ylamino]-8-methoxy-1,2,4,5-tetrahydro-benzo[d]azepin-3-yl}-N,N-dimethyl-acetamide Following a procedure analogous to Example 113, 2-(7-Amino-8-methoxy-1,2,4,5-tetrahydro-benzo[d]azepin-3-yl)-N,N-dimethyl-acetamide (47 mgs) and (2,5-Dichloro-pyrimidin-4-yl)-(2-pyrazol-1-yl-phenyl)-amine (47 mgs) were converted to the title compound (51 mgs) as a white foam. 1H-NMR (CDCl3): δ 10.16 (s, 1H), 8.53 (d, J=7.4 Hz, 1H), 8.06 (s, 2H), 7.85 (d, J=14.4 Hz, 2H), 7.48 (s, 1H), 7.40-7.34 (m, 2H), 7.20 (t, J=7.6 Hz, 1H), 6.65 (s, 1H), 6.52 (s, 1H), 3.88 (s, 3H), 3.30 (s, 2H), 3.17 (s, 3H), 3.00 (s, 3H), 2.90-2.70 (complex m 7H). LC/MS, found 547.18 (M+H)+; MP: 66-67° C.;

Example 1321

5-Chloro-N*2*-[8-methoxy-3-(2-methoxy-ethyl)-2,3,4,5-tetrahydro-1H-benzo[d]azepin-7-yl]-N*4*-(2-pyrazol-1-yl-phenyl)-pyrimidine-2,4-diamine Following a procedure analogous to Example 113, 8-Methoxy-3-(2-methoxy-ethyl)-2,3,4,5-tetrahydro-1H-benzo[d]azepin-7-ylamine (45 mgs) and (2,5-Dichloro-pyrimidin-4-yl)-(2-pyrazol-1-yl-phenyl)-amine (50 mgs) were combined to give the title compound (46 mgs) as a white foam. 1H-NMR (CDCl3): δ 10.16 (s, 1H), 8.54 (d, J=8.3 Hz, 1H), 8.06 (s, 2H), 7.85 (d, J=15.2 Hz, 2H), 7.47 (s, 1H), 7.41-7.35 (m, 2H), 7.21-7.18 (m, 1H), 6.65 (s, 1H), 6.53 (s, 1H), 3.87 (s, 3H), 3.60-3.57 (m, 2H), 3.40 (s, 3H), 2.91-2.80 (m, 10H). LC/MS: found (M+H)+=520.16; MP: 42-50° C.

Example 1322

(1R,2R,3S,4S)-3-{5-Chloro-2-[8-methoxy-3-(2-methoxy-ethyl)-2,3,4,5-tetrahydro-1H-benzo[d]azepin-7-ylamino]-pyrimidin-4-ylamino}-bicyclo[2.2.1]hept-5-ene-2-carboxylic acid amide Following a procedure analogous to Example 112 using (1R,2R,3S,4S)-3-(2,5-Dichloro-pyrimidin-4-ylamino)-bicyclo[2.2.1]hept-5-ene-2-carboxylic acid amide (49 mgs) provided the title compound (35 mgs, 42%). found (M+H)+=513.16 MP: 62-70°. NMR was equivalent to Example 112.

Example 1323

7-[5-Chloro-4-(2-pyrazol-1-yl-phenylamino)-pyrimidin-2-ylamino]-1,5,5-trimethyl-1,3,4,5-tetrahydro-benzo[b]azepin-2-one Following a procedure analogous to Example 113, 7-Amino-1,5,5-trimethyl-1,3,4,5-tetrahydro-benzo[b]azepin-2-one (34 mgs) and (2,5-Dichloro-pyrimidin-4-yl)-(2-pyrazol-1-yl-phenyl)-amine (44 mgs) was converted to the title compound (40 mgs as a white solid). 1H-NMR (CDCl3): δ 10.29 (s, 1H), 8.50 (d, J=8.3 Hz, 1H), 8.08 (s, 1H), 7.87 (s, 1H), 7.83 (s, 1H), 7.74-7.72 (m, 1H), 7.41-7.35 (m, 2H), 7.22 t, J=7.8 Hz, 1H), 7.12 (d, J=8.6 Hz, 1H), 6.97 (s, 1H), 6.54 (s, 1H), 3.31 (s, 3H), 2.33-2.31 (m, 2H), 2.06-2.04 (m, 2H), 1.30 (s, 6H). LC/MS: found (M+H)+=488.22; MP: 136-138° C.

Example 1324

2-[5-Chloro-2-(1-ethyl-8-methoxy-2-oxo-2,3,4,5-tetrahydro-1H-benzo[b]azepin-7-ylamino)-pyrimidin-4-ylamino]-N,N-dimethyl-benzenesulfonamide Following a procedure analogous to Example 113, 7-Amino-1-ethyl-8-methoxy-1,3,4,5-tetrahydro-benzo[b]azepin-2-one (46 mgs) and 2-(2,5-Dichloro-pyrimidin-4-ylamino)-N,N-dimethyl-benzenesulfonamide (68 mgs) were converted to the title compound (64 mgs as a tan solid). 1H-NMR (CDCl3, 400 MHz): 9.82 (s, 1H), 8.95 (broad s, 1H); 8.41 (d, J=8.4 Hz, 1H), 8.10 (s, 1H), 7.92 (d, J=7.8 Hz, 1H); 7.83 (s, 1H); 7.53 (t, J=7.6 Hz, 1H); 7.34 (t, J=7.8 Hz, 1H), 6.78 (s, 1H), 3.91 (s, 3H); 3.5 (s, 2H), 2.78 (s, 6H), 2.65-2.0 (broad m, 6H), 1.17 (t, 7.1 Hz, 3H); LC/MS: found (M+H)+=545.21; MP: 147-153° C.

Example 1325

2-[5-Chloro-2-(1,5,5-trimethyl-2-oxo-2,3,4,5-tetrahydro-1H-benzo[b]azepin-7-ylamino)-pyrimidin-4-ylamino]-N,N-dimethyl-benzenesulfonamide Following a procedure analogous to Example 113, 7-Amino-1,5,5-trimethyl-1,3,4,5-tetrahydro-benzo[b]azepin-2-one (37.1 mg,) and 2-(2,5-Dichloro-pyrimidin-4-ylamino)-N,N-dimethyl-benzenesulfonamide (59 mg) were converted to the title compound as a white solid (25 mgs). δ 9.47 (s, 1H), 8.53 (d, J=8.3 Hz, 1H), 8.18 (s, 1H), 7.90 (d, J=8.1 Hz, 1H), 7.64 (d, J=8.6 Hz, 1H), 7.56 (t, J=7.8 Hz, 1H), 7.37 (s, 1H), 7.28-7.24 (m, 1H), 7.13 (d, J=8.6 Hz, 1H), 7.07 (s, 1H), 3.31 (s, 3H), 2.77 (s, 6H), 2.32 (broad s, 2H), 2.07 (broad s, 2H), 1.27 (s, 6H). LC/MS: (M+H)+ found=529.16; MP 198-200° C.

Example 1326

2-[5-Chloro-2-(1-ethyl-6-methoxy-2-oxo-2,3,4,5-tetrahydro-1H-benzo[b]azepin-7-ylamino)-pyrimidin-4-ylamino]-N,N-dimethyl-benzenesulfonamide Following a procedure analogous to Example 113, 7-Amino-1-ethyl-6-methoxy-1,3,4,5-tetrahydro-benzo[b]azepin-2-one (40 mgs) and 2-(2,5-Dichloro-pyrimidin-4-ylamino)-N,N-dimethyl-benzenesulfonamide (59 mgs) were converted to the title compound (18 mgs as a white solid). 1H-NMR (CDCl3): δ 9.48 (s, 1H), 8.58 (d, J=8.3 Hz, 1H), 8.24 (d, J=8.8 Hz, 1H), 8.19 (s, 1H), 7.91 (d, J=7.8 Hz, 1H), 7.63 (t, J=7.6 Hz, 1H), 7.50 (s, 1H), 7.31-7.28 (m, 1H), 6.94 (d, J=8.9 Hz, 1H), 4.40-4.10 (broad absorption, 2H), 3.83 (s, 3H), 3.70-2.90 (broad absorption, 2H), 2.78 (s, 6H), 2.31-

2.00 (broad absorptions, 4H), 1.16 (t, J=7.0 Hz, 3H). LC/MS: (M+H)+ found=545.16; MP 183° C.

Example 1327

7-{5-Chloro-4-[2-(propane-2-sulfonyl)-phenylamino]-pyrimidin-2-ylamino}-1-ethyl-8-methoxy-1,3,4,5-tetrahydro-benzo[b]azepin-2-one Following a procedure analogous to Example 113, 7-Amino-1-ethyl-8-methoxy-1,3,4,5-tetrahydro-benzo[b]azepin-2-one (37 mgs) and (2,5-Dichloro-pyrimidin-4-yl)-[2-(propane-2-sulfonyl)-phenyl]-amine (50 mgs) gave the title compound (35 mgs) as an off-white solid. 1H-NMR (CDCl3, 400 MHz): 9.54 (s, 1H), 8.55 (d, J=8.4 Hz, 1H); 8.21 (s, 1H), 8.15 (s, 1H), 7.96 (d, J=8.1 Hz, 1H), 7.67-7.60 (m, 2H), 7.32-7.28 (m, 1H); 6.73 (s, 1H); 4.10-3.90 (broad abs., 2H), 3.93 (s, 3H); 3.29-3.25 (m, 1H), 2.70-2.40 (broad abs, 2H), 2.28-2.25 (m, 2H), 2.20-2.00 (broad abs, 2H); 1.33 (d, J=6.8 Hz, 6H), 1.16 (t, 7.1 Hz, 3H); LC/MS: (M+H)+ found 544.14; MP: 195-197° C.

Example 1328

7-{5-Chloro-4-[2-(propane-2-sulfonyl)-phenylamino]-pyrimidin-2-ylamino}-1-ethyl-6-methoxy-1,3,4,5-tetrahydro-benzo[b]azepin-2-one Following a procedure analogous to Example 113, gave the title compound as an off-white solid (7.48 mgs) 1H-NMR (CDCl3, 400 MHz): 9.66 (s, 1H), 8.60 (d, J=8.4 Hz, 1H); 8.24-8.21 (m, 2H), 7.96 (d, J=7.9 Hz, 1H), 7.67 t, J=7.6 Hz, 1H), 7.51 (s, 1H), 7.33-7.28 (m, 1H); 6.95 (d, J=8.5 Hz, 1H); 4.30-4.10 (broad abs., 2H), 3.83 (s, 3H); 3.29-3.25 (m, 1H), 3.10-2.50 (broad abs, 2H), 2.31 (broad s, 2H), 2.20-2.00 (broad abs, 2H); 1.36 (d, J=6.7 Hz, 6H), 1.15 (t, 7.1 Hz, 3H); LC/MS: 2373-294: (M+H)+ found 544.14 MP: Foam.

Example 1329

7-{5-Chloro-4-[2-(propane-2-sulfonyl)-phenylamino]-pyrimidin-2-ylamino}-1,5,5-trimethyl-1,3,4,5-tetrahydro-benzo[b]azepin-2-one Following a procedure analogous to Example 113, 7-Amino-1,5,5-trimethyl-1,3,4,5-tetrahydro-benzo[b]azepin-2-one (35 mgs) and (2,5-Dichloro-pyrimidin-4-yl)-[2-(propane-2-sulfonyl)-phenyl]-amine (50 mgs) gave the title compound as an off-white solid (22 mgs). 1H-NMR (CDCl3, 400 MHz): 9.65 (s, 1H), 8.55 (d, J=8.3 Hz, 1H); 8.19 (s, 2H), 7.94 (d, J=8.1 Hz, 1H), 7.65-7.58 (m, 2H), 7.37 (s, 1H), 7.30-7.26 (m, 1H); 7.14-7.10 (m, 2H); 3.31 (s, 3H); 3.28-3.23 (m, 1H), 2.33-2.30 (m, 2H), 2.03 (broad s, 2H), 1.34 (d, J=7.1 Hz, 6H), 1.27 (s, 6H). LC/MS: found 528.15 (M+H)+; MP: 195-197° C.

Example 1330

(1S,2S,3R,4R)-3-{5-Chloro-2-[1-ethyl-6-methoxy-2-oxo-3-(2,2,2-trifluoro-acetylamino)-2,3,4,5-tetrahydro-1H-benzo[b]azepin-7-ylamino]-pyrimidin-4-ylamino}-bicyclo[2.2.1]hept-5-ene-2-carboxylic acid amide 1330a) 1-Ethyl-6-methoxy-7-nitro-1,3,4,5-tetrahydro-benzo[b]azepin-2-one (1.0 g) in Methylene chloride (12 mL) was cooled to 0° C. and treated with N,N,N',N'-Tetramethylethylenediamine (1.7 mL) then treated dropwise with Iodotrimethylsilane (1.6 mL). A white precitate formed in the solution. The mixture was stirred at 0° C. for 30 min, solid Iodine (1.4 g) was added in one portion and the mixture stirred at 0° C. A dark color ensued. After 45 min, the reaction was quenched with 10% Na2S2O3, extracted with dichloromethane. The organic layers were washed with brine, dried (MgSO4), filtered and concentrated. (+/−)-1-Ethyl-3-iodo-6-methoxy-7-nitro-1,3,4,5-tetrahydro-benzo[b]azepin-2-one isolated as an orangish solid (1.30 g, 88%). LC/MS: (M+H)+ found 390.93. Taking on without purification.

1330b) Combined (+/−)-1-ethyl-3-iodo-6-methoxy-7-nitro-1,3,4,5-tetrahydro-benzo[b]azepin-2-one (1.3 g), Sodium azide (2.17 g) and N,N-Dimethylformamide (20 mL) in flask under nitrogen and stirred overnight. Partitioned between EtOAc/water. The organic layers were further washed with water, brine, dried (MgSO4), filtered and concentrated. Stripped onto Celite and purified by ISCO chromatography (120 g SiO2, hexane to EtOAc gradient). (+/−)-3-Azido-1-ethyl-6-methoxy-7-nitro-1,3,4,5-tetrahydro-benzo[b]azepin-2-one isolated as a clear oil (402 mgs). 1H-NMR (CDCl3, 400 MHz): 7.86 (d, J=8.8 Hz, 1H), 7.13 (d, J=8.8 Hz, 1H), 4.33-4.25 (m, 1H), 3.98 (s, 3H), 3.78-3.71 (broad m, 2H), 3.35-3.23 (broad m, 1H), 2.65-2.35 (broad m, 3H), 1.25-1.21 (m, 3H).

1330c) Combined (+/−)-3-Azido-1-ethyl-6-methoxy-7-nitro-1,3,4,5-tetrahydro-benzo[b]azepin-2-one (280 mg), Triphenylphosphine Resin (1.0 mmol/g loading; 1.83 g), Tetrahydrofuran (25 mL) and Water (0.25 mL) and stir at rt overnight. Filter and concentrate. Strip down from benzene to remove water. (+/−)-3-Amino-1-ethyl-6-methoxy 7-nitro-1,3,4,5-tetrahydro-benzo[b]azepin-2-one as an orangish oil isolated (251 mgs). 1H-NMR (CDCl3, 400 MHz): 7.84 (d, J=8.8 Hz, 1H), 7.10 (d, J=8.9 Hz, 1H), 4.36-4.28 (m, 1H), 3.97 (s, 3H), 3.71-3.62 (m, 1H), 3.36-3.31 (m, 1H), 3.23-3.18 (m, 1H), 2.52-2.39 (m, 2H), 2.03-1.99 (m, 1H), 1.66 (broad s, 2H), 1.21 (t, J=7.3 Hz, 3H). LC/MS: (M+H)+ found 280.18.

1330d) (+/−)-3-Amino-1-ethyl-6-methoxy-7-nitro-1,3,4,5-tetrahydro-benzo[b]azepin-2-one (251 mgs) with Methylene chloride (9 mL) and added Pyridine (0.22 mL) followed by Trifluoroacetic anhydride (0.19 mL). Stir 10 min. Partitioned between DCM and water, the organic layers were washed with brine, dried (MgSO4), filtered and concentrated. (+/−)-N-(1-Ethyl-6-methoxy-7-nitro-2-oxo-2,3,4,5-tetrahydro-1H-benzo[b]azepin-3-yl)-2,2,2-trifluoro-acetamide isolated yellow solid (310 mgs). 1H-NMR (CDCL3, 400 MHz): 1H-NMR (CDCl3, 400 MHz): 7.88 (d, J=8.8 Hz, 1H), 7.49 (d, J=5.8 Hz, 1H), 7.13 (d, J=8.8 Hz, 1H), 4.44-4.30 (m, 2H), 4.00 (s, 3H), 3.74-3.65 (m, 1H), 3.31-3.26 (m, 1H), 2.83-2.73 (m, 1H), 2.60-2.51 (m, 1H), 2.12-2.04 (m, 1H), 1.241 (t, J=7.3 Hz, 3H). LC/MS: found (M+H)+=376.23.

1330e) Following a procedure analogous to Example 31f and then Example 113, (+/−)-N-(1-Ethyl-6-methoxy-7-nitro-2-oxo-2,3,4,5-tetrahydro-1H-benzo[b]azepin-3-yl)-2,2,2-trifluoro-acetamide was converted to (1S,2S,3R,4R)-3-{5-Chloro-2-[1-ethyl-6-methoxy-2-oxo-3-(2,2,2-trifluoro-acetylamino)-2,3,4,5-tetrahydro-1H-benzo[b]azepin-7-ylamino]-pyrimidin-4-ylamino}-bicyclo[2.2.1]hept-5-ene-2-carboxylic acid amide isolated as a white solid (24 mgs) as a mix of diastereomers. Data for diastereomeric peaks denoted with "*"; if no asterisk present then diastereomeric peaks are coincident. I H-NMR (CDCl3, 400 MHz): 8.50 (d, J=9.3 Hz, 1H), *8.45 (d, J=9.3 Hz, 1H), 7.95 (s, 1H), 7.57 (s, 1H), 7.45 (s, 1H), *7.42 (s, 1H), 7.21-7.18 (m, 1H), 6.98 (d, J=8.8 Hz, 1H), 6.36 (broad s, 2H), 5.62 (s, 1H), 5.40 (s, 1H), *4.49-4.40 (m, 1H), 4.39-4.35 (m, 1H), 3.86 (s, 3H), *3.85 (s, 3H), 3.59-3.54 (m, 1H), 3.51 (d, J=3.8, 2H), 3.17-3.12 (m, 1H), 3.10 (s, 1H), 2.97 (s, 1H), 2.79-2.75 (m, 1H), *2.62-2.55 (m, 2H), 2.54-2.50 (m, 2H), 2.30-2.26 (m, 1H), 2.06-2.00 (m, 1H), 1.66 (d, J=8.3 Hz, 1H), 1.35-1.2 (m, 5H), 0.95-0.82 (m, 2H). (LC/MS: (M+H)+, found 608.54; MP: 167-176° C.

Example 1331 and Example 1332

(1S,2S,3R,4R)-3-[2-((R)-3-Amino-1-ethyl-6-methoxy-2-oxo-2,3,4,5-tetrahydro-1H-benzo[b]azepin-7-ylamino)-5-chloro-pyrimidin-4-ylamino]-bicyclo[2.2.1]hept-5-ene-2-carboxylic acid amide and (1S,2S,3R,4R)-3-[2-((S)-3-Amino-1-ethyl-6-methoxy-2-oxo-2,3,4,5-tetrahydro-1H-benzo[b]azepin-7-ylamino)-5-chloro-pyrimidin-4-ylamino]-bicyclo[2.2.1]hept-5-ene-2-carboxylic acid amide Combined (1S,2S,3R,4R)-3-{5-Chloro-2-[1-ethyl-6-methoxy-2-oxo-3-(2,2,2-trifluoro-acetylamino)-2,3,4,5-tetrahydro-1H-benzo[b]azepin-7-ylamino]-pyrimidin-4-ylamino}-bicyclo[2.2.1]hept-5-ene-2-carboxylic acid amide (90 mg) in 7 M of Ammonia in Methanol (4 mL) and Tetrahydrofuran (2 mL), stir at room temperature then heating sealed tube at 65° C. overnight then heat to 85° C. in sealed tube overnight. concentrated and dissolved in MeOH for purification by reverse phase HPLC (5-30% MeCN/H2O), on Gilson system. Isolated the title compounds after concentrating and free basing with MP-carbonate in methanol. Faster eluting isomer isolated 18.31 mgs: 1H-NMR (DMSO-d6, 400 MHz) 8.14 (t, J=11.1 Hz, 1H), 7.98-8.23 (m, 4H), 7.28-7.10 (m, 2H), 6.32-6.60 (m, 2H), 4.18-4.15 (m, 1H), 4.02-3.90 (m, 2H), 3.74 (s, 3H), 3.60-2.80 (complex series of m, 6H), 2.45-2.05 (complex series of m, 5H), 1.40-1.39 (m, 1H), 1.05-0.98 (m, 3H). LC/MS: m/z found 512 (M+H)+. Slower eluting isomer 31.54 mgs: 1H-NMR (DMSO-d6, 400 MHz). 8.16-8.11 (m, 1H), 7.98-7.93 (m, 2H), 7.89 (s, 2H), 7.18-7.10 (m, 2H), 6.32-6.30 (m, 2H), 4.18-3.95 (m, 2H), 3.74 (s, 3H0, 3.55-2.85 (complex series of m, 6H), 2.40-2.07 (complex series of m, 5H), 1.42-1.39 (m, 1H), 1.05-0.95 (m, 3H). LC/MS: m/z found 512 (M+H)+.

Example 1333

N-(7-{5-Chloro-4-[2-(propane-2-sulfonyl)-phenylamino]-pyrimidin-2-ylamino}-1-ethyl-6-methoxy-2-oxo-2,3,4,5-tetrahydro-1H-benzo[b]azepin-3-yl)-2,2,2-trifluoro-acetamide Following a procedure analogous to Example 113, N-(7-Amino-1-ethyl-6-methoxy-2-oxo-2,3,4,5-tetrahydro-1H-benzo[b]azepin-3-yl)-2,2,2-trifluoro-acetamide (163 mgs) and (2,5-Dichloro-pyrimidin-4-yl)-[2-(propane-2-sulfonyl)-phenyl]-amine (156 mgs) were combined to give the title compound as off-white solid (101 mgs) 1H-NMR (CDCl3, 400 MHz): 9.67 (s, 1H), 8.57 (d, J=8.6 Hz, 1H), 8.31 (d, J=8.8 Hz, 1H), 8.23 (s, 1H), 7.97 (d, J=7.8 Hz, 1H), 7.69 (d, J=8.1 Hz, 1H), 7.60-7.58 (m, 2H), 7.33 (t, J=7.8 Hz, 1H), 6.93 (d, J=8.9 Hz, 1H), 4.49-4.43 (m, 1H), 4.40-4.31 (m, 1H), 3.87 (s, 3H), 3.59-3.52 (m, 1H), 3.31-3.28 (m, 1H), 3.18-3.13 (m, 1H), 2.80-2.70 (m, 1H), 2.61-2.53 (m, 1H), 2.06-1.99 (m, 1H), 1.37-1.33 (m, 6H), 1.22 (t, J=6.1 Hz, 3H), LC/MS: found (M+H)+=655.57; MP: 245-247° C.

Example 1334

N-{7-[5-Chloro-4-(2-dimethylsulfamoyl-phenylamino)-pyrimidin-2-ylamino]-1-ethyl-6-methoxy-2-oxo-2,3,4,5-tetrahydro-1H-benzo[b]azepin-3-yl}-2,2,2-trifluoro-acetamide Following a procedure analogous to Example 113, N-(7-Amino-1-ethyl-6-methoxy-2-oxo-2,3,4,5-tetrahydro-1H-benzo[b]azepin-3-yl)-2,2,2-trifluoro-acetamide (164 mgs) and 2-(2,5-Dichloro-pyrimidin-4-ylamino)-N,N-dimethyl-benzenesulfonamide (160 mgs) gave the title compound as an off-white solid (102 mgs). 1H-NMR (CDCl3, 400 MHz): 9.47 (s, 1H), 8.55 (d, J=8.3 Hz, 1H), 8.33 (d, J=8.9 Hz, 1H), 8.21 (s, 1H), 7.92 (d, J=8.1 Hz, 1H), 7.67-7.54 (m, 3H), 7.32-7.28 (m, 1H), 6.92 (d, J=8.8 Hz, 1H), 4.47-4.34 (m, 2H), 3.87 (s, 3H), 3.58-3.54 (m, 1H), 3.17-3.13 (m, 1H), 2.78 (s, 6H), 2.59-2.53 (m, 1H), 2.06-2.01 (m, 1H), 1.23-1.18 (m, 3H); LC/MS: found (M+H)+=656; MP: 250-51° C.

Example 1335

N-{7-[5-Chloro-4-((1R,2R)-2-methanesulfonylamino-cyclohexylamino)-pyrimidin-2-ylamino]-1-ethyl-6-methoxy-2-oxo-2,3,4,5-tetrahydro-1H-benzo[b]azepin-3-yl}-2,2,2-trifluoro-acetamide Following a procedure analogous to Example 113, N-(7-Amino-1-ethyl-6-methoxy-2-oxo-2,3,4,5-tetrahydro-1H-benzo[b]azepin-3-yl)-2,2,2-trifluoro-acetamide (193 mgs) and N-[(1R,2R)-2-(2,5-Dichloro-pyrimidin-4-ylamino)-cyclohexyl]-methanesulfonamide (180 mgs) gave the title compounds as an off-white solid (92 mgs). 1:1 mix of diastereomers. 1H-NMR (CDCl3, 400 MHz): 8.29-8.24 (m, 1H), 8.05-8.02 (m, 1H), 7.59-7.52 (m, 1H), 7.02-7.00 (m, 1H), 4.55-4.53 (m, 2H), 3.94-3.90 (m, 1H), 3.85 (s, 1H), 3.59-3.53 (m, 1H), 3.38-3.32 (m, 1H), 3.16-3.10 (m, 1H), 2.90 (s, 3H), 2.76-2.68 (m, 1H), 2.57-2.52 (m, 1H), 2.20-1.20 (complex series of m, 12H); LC/MS: found (M+H)+=648; MP: 160-2° C.

Example 1336

2-[2-(3-Amino-1-ethyl-6-methoxy-2-oxo-2,3,4,5-tetrahydro-1H-benzo[b]azepin-7-ylamino)-5-chloro-pyrimidin-4-ylamino]-N,N-dimethyl-benzenesulfonamide Following a procedure analogous to Example 1331, N-{7-[5-Chloro-4-(2-dimethylsulfamoyl-phenylamino)-pyrimidin-2-ylamino]-1-ethyl-6-methoxy-2-oxo-2,3,4,5-tetrahydro-1H-benzo[b]azepin-3-yl}-2,2,2-trifluoro-acetamide (90 mgs) was converted to the title compound (40 mgs) as a white foam. 1H-NMR (CDCl3, 400 MHz): 9.48 (s, 1H), 8.57 (d, J=8.3 Hz, 1H), 8.27 (d, J=8.8 Hz, 1H), 8.20 (s, 1H), 7.93 (d, J=8.8 Hz, 1H), 7.63 (t, J=8.3 Hz, 1H), 7.51 (s, 1H), 7.29-7.27 (m, 1H), 6.93 (d, J=8.2 Hz, 1H), 4.40-4.33 (m, 1H), 3.85 (s, 3H), 3.56-3.51 (m, 1H), 3.41-3.36 (m, 1H), 3.10-3.05 (m, 1H), 2.78 (s, 3H), 2.78 (s, 3H), 2.54-2.31 (m, 2H), 1.97-1.89 (m, 1H), 1.62 (broad s, 2H), 1.17 (t, J=7.1 Hz, 3H); LC/MS: found (M+H)+=560.46.

Example 1337

3-Amino-7-{5-chloro-4-[2-(propane-2-sulfonyl)-phenylamino]-pyrimidin-2-ylamino}-1-ethyl-6-methoxy-1,3,4,5-tetrahydro-benzo[b]azepin-2-one Following a procedure analogous to Example 1331, N-(7-{5-Chloro-4-[2-(propane-2-sulfonyl)-phenylamino]-pyrimidin-2-ylamino}-1-ethyl-6-methoxy-2-oxo-2,3,4,5-tetrahydro-1H-benzo[b]azepin-3-yl)-2,2,2-trifluoro-acetamide (85 mgs) was converted to the title compound (35 mgs) as a white foam. 1H-NMR (CDCl3, 400 MHz): 9.66 (s, 1H), 8.58 (d, J=8.3 Hz, 1H), 8.26-8.21 (m, 2H), 7.97-7.94 (m, 1H), 7.69-7.65 (m, 1H), 7.51 (s, 1H), 7.33-7.29 (m, 1H), 6.93 (d, J=8.9

Hz, 1H), 4.40-4.31 (m, 1H), 3.84 (s, 3H), 3.58-3.49 (m, 1H), 3.42-3.38 (m, 1H), 3.30-3.22 (m, 1H), 3.10-3.05 (m, 1H), 2.54-2.31 (m, 2H), 1.98-1.80 (m, 1H), 1.80 (broad s, 1H), 1.36-1.33 (m, 6H), 1.17 (t, J=7.0 Hz, 3H); LC/MS: found (M+H)+=549.46.

Example 1338

N-{(1R,2R)-2-[2-(3-Amino-1-ethyl-6-methoxy-2-oxo-2,3,4,5-tetrahydro-1H-benzo[b]azepin-7-ylamino)-5-chloro-pyrimidin-4-ylamino]-cyclohexyl}-methanesulfonamide Following a procedure analogous to Example 1331, N-{7-[5-Chloro-4-((1R,2R)-2-methanesulfonylamino-cyclohexylamino)-pyrimidin-2-ylamino]-1-ethyl-6-methoxy-2-oxo-2, 3,4,5-tetrahydro-1H-benzo[b]azepin-3-yl}-2,2,2-trifluoroacetamide (84 mgs) was converted to the title compound as a white lyophilized powder. 1H-NMR (400 MHz, d6-dmso) 8.14-8.08 (m, 3H), 7.29-7.21 (m, 2H), 7.06 (d, J=8.1 Hz, 1H), 4.27-4.22 (m, 1H), 3.77-3.75 (m, 4H), 3.61-3.56 (m, 1H), 3.40-3.32 (m, 1H), 3.10-3.07 (m, 1H), 2.90 (s, 3H), 2.10-190 (m, 6H), 1.75-1.63 (m, 2H), 1.50-1.00 (complex series of m, 9H) LC/MS: found M+H+=552

Example 1339

7-[5-Chloro-4-(4-dimethylamino-2-methoxy-phenylamino)-pyrimidin-2-ylamino]-1-ethyl-6-methoxy-1, 3,4,5-tetrahydro-benzo[b]azepin-2-one Following a procedure analogous to Example 113, 7-Amino-1-ethyl-6-methoxy-1,3,4,5-tetrahydro-benzo[b] azepin-2-one (64 mgs) and N(1)-(2,5-Dichloro-pyrimidin-4-yl)-2-methoxy-N(4),N(4)-dimethyl-benzene-1,4-diamine (77 mgs) were converted to the title compound (82 mgs) as a white solid. 1H-NMR (CDCl3, 400 MHz): 8.29 (d, J=8.2 Hz, 1H), 8.09-8.04 (m, 2H), 7.42 (s, 1H), 7.38 (s, 1H), 6.92 (d, J=7.8 Hz, 1H), 6.39-6.37 (m, 2H), 4.31-4.10 (broad absorption, 2H), 3.93 (s, 3H), 3.84 (s, 6H), 3.00-1.95 (broad absorption, 6H), 1.16 (t, J=7.0 Hz, 3H); LC/MS: found (M+H)+=511.46 MP: 190-193° C.;

Example 1340

7-[5-Chloro-4-(4-dimethylamino-2-methoxy-phenylamino)-pyrimidin-2-ylamino]-1-ethyl-8-methoxy-1, 3,4,5-tetrahydro-benzo[b]azepin-2-one Following a procedure analogous to Example 113, 7-Amino-1-ethyl-8-methoxy-1,3,4,5-tetrahydro-benzo[b] azepin-2-one (55 mgs) and N(1)-(2,5-Dichloro-pyrimidin-4-yl)-2-methoxy-N(4),N(4)-dimethyl-benzene-1,4-diamine (66 mgs) were converted to the title compound (78 mgs) as a white solid. 1H-NMR (CDCl3, 400 MHz): 8.20 (s, 1H), 8.02 (s, 1H), 7.95 (d, J=8.3 Hz, 1H), 7.53 (s, 1H), 6.69 (s, 1H), 6.37-6.35 (m, 2H), 4.35-3.8 (broad absorption, 2H), 3.90 (d, J=7.3 Hz, 6H) 2.98 (d, J=0.8 Hz, 3H), 2.65-2.50 (m, 1H), 2.30-2.00 (m, 3H), 1.6 (broad s, 2H), 1.15 (t, J=7.0 Hz, 3H); LC/MS: found (M+H)+=511.46 MP: 183-185° C.

Example 1341

N-{7-[5-Chloro-4-(4-dimethylamino-2-methoxyphenylamino)-pyrimidin-2-ylamino]-1-ethyl-6-methoxy-2-oxo-2,3,4,5-tetrahydro-1H-benzo[b]azepin-3-yl}-2,2,2-trifluoro-acetamide Following a procedure analogous to Example 113, N-(7-Amino-1-ethyl-6-methoxy-2-oxo-2,3,4,5-tetrahydro-1H-benzo[b]azepin-3-yl)-2,2,2-trifluoro-acetamide (78 mgs) and N(1)-(2,5-Dichloro-pyrimidin-4-yl)-2-methoxy-N(4),N(4)-dimethyl-benzene-1,4-diamine (60 mgs) were converted to the title compound as an off-white solid (50 mgs). 1H-NMR (CDCl3, 400 MHz): 8.39 (d, J=8.8 Hz, 1H), 8.05-8.04 (m, 2H), 7.59 (s, 1H), 7.43 (d, J=8.6 Hz, 2H), 6.90 (d, J=8.9 Hz, 1H), 6.41-6.39 (m, 2H), 4.49-4.41 (m, 1H), 4.34-4.28 (m, 1H), 3.93 (s, 3H), 3.84 (s, 3H), 3.29-3.54 (m, 1H), 3.16-3.11 (m, 1H), 3.01 (s, 6H), 2.76-2.71 (m, 1H), 2.57-2.51 (m, 1H), 2.05-2.98 (m, 1H), 1.20 (t, J=7.3 Hz, 3H); LC/MS: found (M+H)+=622.52, MP: 192-193° C.

Example 1342

7-[5-Chloro-4-(4-dimethylamino-2-methoxy-phenylamino)-pyrimidin-2-ylamino]-1,5,5-trimethyl-1,3,4, 5-tetrahydro-benzo[b]azepin-2-one Following a procedure analogous to Example 1331, 7-Amino-1,5,5-trimethyl-1,3,4,5-tetrahydro-benzo[b] azepin-2-one (59 mgs) was converted to the title compound as an HCL salt (128 mgs) as a yellow solid. 1H-NMR (dmso-d6, 400 MHz): 10.19-10.15 (m, 1H), 9.19-9.14 (m, 1H), 8.33-8.27 (m, 2H), 7.59-7.50 (m, 1H), 7.31 (s, 2H), 7.11 (d, J=7.3 Hz, 2H), 3.82 (s, 3H), 3.15 (s, 3H), 3.05 (s, 6H), 2.10-2.08 (m, 2H), 1.90-1.85 (m, 2H), 1.16 (s, 6H); MP: 244-63° C. LC/MS: found (M+H)+=495.45.

Example 1343

3-Amino-7-[5-chloro-4-(4-dimethylamino-2-methoxy-phenylamino)-pyrimidin-2-ylamino]-1-ethyl-6-methoxy-1,3,4,5-tetrahydro-benzo[b]azepin-2-one Following a procedure analogous to Example 1331, N-{7-[5-Chloro-4-(4-dimethylamino-2-methoxy-phenylamino)-pyrimidin-2-ylamino]-1-ethyl-6-methoxy-2-oxo-2,3,4,5-tetrahydro-1H-benzo[b]azepin-3-yl}-2,2,2-trifluoro-acetamide (40 mgs) gave the title compound (21 mgs) as a white foam. 1H-NMR (CDCl3, 400 MHz): 8.32 (d, J=8.9 Hz, 1H), 8.08-8.04 (m, 2H), 7.43 (s, 1H), 6.90 (d, J=9.1 Hz, 2H), 6.39 (s, 2H), 4.34-4.27 (m, 1H), 3.93 (s, 3H), 3.81 (s, 3H), 3.58-3.52 (m, 1H), 3.45-3.37 (m, 1H), 3.09-3.04 (m, 1H), 3.01 (s, 6H), 2.52-2.35 (m, 2H), 1.96-1.70 (m, 3H), 1.17 (t, J=7.1 Hz, 3H) LC/MS: found (M+H)+526.45.

Example 1344 and Example 1345

(1S,2S,3R,4R)-3-[5-Chloro-2-((R)-1-ethyl-6-methoxy-3-morpholin-4-yl-2-oxo-2,3,4,5-tetrahydro-1H-benzo[b]azepin-7-ylamino)-pyrimidin-4-ylamino]-bicyclo[2.2.1]hept-5-ene-2-carboxylic acid amide and (1S,2S,3R,4R)-3-[5-Chloro-2-((s)-1-ethyl-6-methoxy-3-morpholin-4-yl-2-oxo-2,3,4,5-tetrahydro-1H-benzo[b]azepin-7-ylamino)-pyrimidin-4-ylamino]-bicyclo[2.2.1]hept-5-ene-2-carboxylic acid amide (1344a) Combine 3-Amino-1-ethyl-6-methoxy-7-nitro-1, 3,4,5-tetrahydro-benzo[b]azepin-2-one (0.8 g), 1-Bromo-2-(2-bromo-ethoxy)-ethane (797 mg) and Potassium carbonate (879 mg) in Acetonitrile (37 mL), heat to 85° C., After 2 days, added another eq of Potassium carbonate and 0.5 eq of 1-Bromo-2-(2-bromo-ethoxy)-ethane and continue heating. Diluted with CH2Cl2, filter, the material was concentrated onto Celite and purified by ISCO chromatography (120 g, SiO2, gradient elution 0% MeOH/DCM/to 110% MeOH/

DCM) to give 1-ethyl-6-methoxy-3-morpholin-4-yl-7-nitro-1,3,4,5-tetrahydro-benzo[b]azepin-2-one as an orange solid (334 mgs). 1H-NMR (CDCl3): 7.86 (d, J=8.8 Hz, 1H), 7.09 (d, J=8.6 Hz, 1H), 4.32-4.22 (m, 1H), 3.96 (s, 3H), 3.73-3.60 (m, 5H), 3.27-3.23 (m, 1H), 2.97-2.92 (m, 1H), 2.72-2.55 (m, 4H), 2.54-2.45 (m, 1H), 2.39-2.23 (m, 2H), 1.20 (t, J=7.1 Hz, 3H).

(1344b) Following a procedure analogous to Example 103c and Example 113, 1-ethyl-6-methoxy-3-morpholin-4-yl-7-nitro-1,3,4,5-tetrahydro-benzo[b]azepin-2-one was converted to the title compounds which were purified on Gilson RP-HPLC and isolated as TFA salts. Data for first eluting isomer on RP-HPLC. 1H-NMR (dmso-d6): 8.45 (broad s, 1H), 8.35-8.33 (m, 2H), 8.08 (s, 1H), 7.88 (s, 1H), 7.35 (s, 1H), 7.30 (d, J=8.8 Hz, 1H), 6.37 (s, 1H), 6.33 (s, 1H), 4.21-3.80 (complex series of m, 9H), 3.79 (s, 3H), 3.40-2.90 (complex series of m, 8H), 2.25-1.99 (m, 3H), 1.42 (d, J=8.5 Hz, 2H), 1.08 (t, J=6.9 Hz, 3H). LC/MS. (M+H)+ found 582. Data for second eluting isomer on RP-HPLC. 1H-NMR (dmso-d6): 8.48 (broad s, 1H), 8.35 (broad s, 1H), 8.28 (d, J=9.1 Hz, 1H), 8.08 (s, 1H), 7.87 (s, 1H), 7.35 (s, 1H), 7.30 (d, J=8.8 Hz, 1H), 6.36 (s, 2H), 4.24-3.83 (complex series of m, 9H), 3.78 (s, 3H), 3.40-2.90 (complex series of m, 8H), 2.25-1.99 (m, 3H), 1.42 (d, J=8.5 Hz, 2H), 1.08 (t, J=6.8 Hz, 3H). LC/MS. (M+H)+ found 582.

Example 1346 and Example 1347

(1S,2S,3R,4R)-3-[5-Chloro-2-((R)-3-dimethylamino-1-ethyl-6-methoxy-2-oxo-2,3,4,5-tetrahydro-1H-benzo[b]azepin-7-ylamino)-pyrimidin-4-ylamino]-bicyclo[2.2.1]hept-5-ene-2-carboxylic acid amide and (1S,2S,3R,4R)-3-[5-Chloro-2-((S)-3-dimethylamino-1-ethyl-6-methoxy-2-oxo-2,3,4,5-tetrahydro-1H-benzo[b]azepin-7-ylamino)-pyrimidin-4-ylamino]-bicyclo[2.2.1]hept-5-ene-2-carboxylic acid amide Following a procedure analogous to Example 61c, 3-Amino-1-ethyl-6-methoxy-7-nitro-1,3,4,5-tetrahydro-benzo[b]azepin-2-one and formaldehyde were converted to 3-Dimethylamino-1-ethyl-6-methoxy-7-nitro-1,3,4,5-tetrahydro-benzo[b]azepin-2-one which following a procedure analogous to Example 103c was converted to 7-Amino-3-dimethylamino-1-ethyl-6-methoxy-1,3,4,5-tetrahydro-benzo[b]azepin-2-one which following a procedure analogous to Example 113 was converted to the title compounds. Data for first eluting isomer on RP-HPLC. 1H-NMR (dmso-d6): 9.76 (broad s, 1H), 8.49-8.38 (m, 2H), 8.32 (d, J=8.8 Hz, 1H), 8.09 (s, 1H), 7.35-7.29 (m, 2H), 6.36-6.32 (m, 2H), 4.25-4.20 (m, 1H), 4.05-4.00 (m, 2H), 3.79 (s, 3H), 3.64-3.59 (m, 1H), 3.12-3.10 (m, 1H), 2.92 (s, 1H), 2.85 (s, 1H), 2.73 (s, 6H), 2.25-2.05 (m, 2H), 1.42 (d, J=8.1 Hz, 2H), 1.07 (t, J=7.1 Hz, 3H). LC/MS. (M+H)+ found 540. Data for second eluting isomer on RP-HPLC. 1H-NMR (dmso-d6): 9.77 (broad s, 1H), 8.48-8.35 (m, 2H), 8.26 (d, J=9.0 Hz, 1H), 8.09 (s, 1H), 7.88 (s, 1H), 7.35-7.29 (m, 2H), 6.36 (s, 2H), 4.27-4.21 (m, 1H), 4.01-3.97 (m, 2H), 3.79 (s, 3H), 3.66-3.61 (m, 1H), 3.14-3.10 (m, 1H), 2.92 (s, 1H), 2.87 (s, 1H), 2.73 (s, 6H), 2.25-2.05 (m, 2H), 1.42 (d, J=8.1 Hz, 2H), 1.07 (t, J=7.1 Hz, 3H). LC/MS. (M+H)+ found 540. LC/MS. (M+H)+ found 540.

Example 1348

2-[5-Chloro-2-(3-dimethylamino-1-ethyl-6-methoxy-2-oxo-2,3,4,5-tetrahydro-1H-benzo[b]azepin-7-ylamino)-pyrimidin-4-ylamino]-N,N-dimethyl-benzenesulfonamide Following a procedure analogous to Example 113, 7-Amino-3-dimethylamino-1-ethyl-6-methoxy-1,3,4,5-tetrahydro-benzo[b]azepin-2-one (78 mgs) and 2-(2,5-Dichloro-pyrimidin-4-ylamino)-N,N-dimethyl-benzenesulfonamide (89 mgs) were converted to the title compound as a tan solid (24 mgs). 1H-NMR (CDCl3, 400 MHz): 9.49 (s, 1H), 8.38 (d, J=8.1 Hz, 1H), 8.27 (d, J=8.9 Hz, 1H), 8.20 (s, 1H), 7.92 (d, J=8.1 Hz, 1H), 7.64 (d, J=8.1 Hz, 1H), 7.49 (s, 1H), 7.31-7.28 (m, 1H), 6.94 (d, J=9.1 Hz, 1H), 4.32-4.26 (m, 1H), 3.83 (s, 3H), 3.54-3.48 (m, 2H), 3.15-3.08 (m, 1H), 3.00-2.95 (m, 1H), 2.78 (s, 6H), 2.65-2.10 (m, 8H), 1.27-1.24 (m, 2H), 1.15 (t, J=7.1 Hz, 3H). LC/MS found (M+H)+=588.21

Example 1349

7-[5-Chloro-4-(2-pyrazol-1-yl-phenylamino)-pyrimidin-2-ylamino]-3-dimethylamino-1-ethyl-6-methoxy-1,3,4,5-tetrahydro-benzo[b]azepin-2-one Following a procedure analogous to Example 113, 7-Amino-3-dimethylamino-1-ethyl-6-methoxy-1,3,4,5-tetrahydro-benzo[b]azepin-2-one (78 mgs) and (2,5-Dichloro-pyrimidin-4-yl)-(2-pyrazol-1-yl-phenyl)-amine (78 mgs) were converted to the title compound as a white foam (13 mgs). 1H-NMR (CDCl3): 1029 (s, 1H), 8.52 (d, J=8.3 Hz, 1H), 8.31 (d, J=7.5 Hz, 1H), 8.10 (s, 1H), 7.88 (s, 1H), 7.83 (s, 1H), 7.44-7.41 (m, 3H), 7.28-7.26 (m, 1H), 6.93 (d, J=8.4 Hz, 1H), 6.54 (s, 1H), 4.33-4.25 (m, 1H), 3.81 (s, 3H), 3.54-2.10 (complex series of m, 10H), 1.15 (t, J=7.1 Hz, 3H). LC/MS found (M+H)+=547.21

Example 1350 and Example 1351

(1S,2S,3R,4R)-3-{5-Chloro-2-[(R)-1-ethyl-6-methoxy-3-(2-methoxy-acetylamino)-2-oxo-2,3,4,5-tetrahydro-1H-benzo[b]azepin-7-ylamino]-pyrimidin-4-ylamino}-bicyclo[2.2.1]hept-5-ene-2-carboxylic acid amide(1S,2S,3R,4R)-3-{5-Chloro-2-[(S)-1-ethyl-6-methoxy-3-(2-methoxy-acetylamino)-2-oxo-2,3,4,5-tetrahydro-1H-benzo[b]azepin-7-ylamino]-pyrimidin-4-ylamino}-bicyclo[2.2.1]hept-5-ene-2-carboxylic acid amide Following a procedure analogous to Example 1330d-e, (+/−)-3-Amino-1-ethyl-6-methoxy-7-nitro-1,3,4,5-tetrahydro-benzo[b]azepin-2-one and methoxyacetyl chloride were converted to N-(7-Amino-1-ethyl-6-methoxy-2-oxo-2,3,4,5-tetrahydro-1H-benzo[b]azepin-3-yl)-2-methoxy-acetamide which was converted to the title compounds. Data for first eluting isomer on RP-HPLC. White powder. 1H-NMR (CDCl3): 8.43 (d, J=8.9 Hz, 1H), 7.94 (s, 1H), 7.54-7.51 (m, 1H), 7.44 (s, 1H), 7.14-7.12 (1H), 6.97 (d, J=8.9 Hz, 1H), 6.37-6.35 (m, 2H), 5.64 (s, 1H), 5.39 (s, 1H), 4.59-4.54 (m, 1H), 4.40-4.43 (m, 1H), 3.93-3.80 (m, 4H), 3.45 (s, 3H), 3.14-3.10 (m, 2H), 2.97 (S, 1H), 2.63-2.53 (m, 2H), 2.26 (d, J=9.9 Hz, 2H), 2.05-1.98 (m, 1H), 1.66 (d, J=9.9 Hz, 3H), 1.24-1.16 (m, 5H). LC/MS. (M+H)+ found 584.23. Data for second eluting isomer on RP-HPLC. White powder 1H-NMR (CDCl3): 8.41 (d, J=8.6 Hz, 1H), 7.94 (s, 1H), 7.53-7.51 (m, 1H), 7.41 (s, 1H), 7.28-7.27 (m, 1H), 7.09 (d, J=8.9 Hz, 1H), 6.98-6.96 (m, 2H), 5.64 (s, 1H), 5.39 (s, 1H), 4.55-4.51 (m, 1H), 4.43-4.35 (m, 1H), 3.93-3.81 (m, 4H), 3.45 (s, 3H), 3.13-3.09 (m, 2H), 2.96 (s, 1H), 2.63-2.53 (m, 3H), 2.29 (d, J=8.9 Hz, 2H), 2.05-1.99 (m, 1H), 1.69-1.67 (m, 1H), 1.28-1.17 (m, 5H). LC/MS. (M+H)+ found 584.25.

Example 1352

N-{7-[5-Chloro-4-(2-dimethylsulfamoyl-phenylamino)-pyrimidin-2-ylamino]-1-ethyl-6-methoxy-2-oxo-2,3,4,5-tetrahydro-1H-benzo[b]azepin-3-yl}-2-methoxy-acetamide Following a procedure analogous to Example 113, N-(7-Amino-1-ethyl-6-methoxy-2-oxo-2,3,4,5-tetrahydro-1H-benzo[b]azepin-3-yl)-2-methoxy-acetamide (100 mgs) and 2-(2,5-Dichloro-pyrimidin-4-ylamino)-N,N-dimethyl-benzenesulfonamide were converted to the title compound (10 mgs) as a white powder. 1H-NMR (CDCl3): 9.45 (s, 1H), 8.54 (d, J=8.1 Hz, 1H), 8.28 (d, J=8.8 Hz, 1H), 8.21 (s, 1H), 7.92 (d, J=7.8 Hz, 1H), 7.65 (t, J=7.8 Hz, 1H), 7.54 (s, 2H), 7.32-7.28 (m, 1H), 6.91 (d, J=8.3 Hz, 1H), 4.59-4.52 (m, 1H), 4.38-4.32 (m, 1H), 3.93-3.80 (m, 4H), 3.46 (s, 3H), 3.12-3.10 (m, 1H), 2.79 (s, 3H), 2.78 (s, 1H), 2.68-2.53 (m, 2H), 2.05-1.98 (m, 1H), 1.27-1.16 (m, 5H). LC/MS. (M+H)+ found 632.22.

Example 1353

(1S,2S,4R)-3-{5-Chloro-2-[3-(2-dimethylamino-acetylamino)-1-ethyl-6-methoxy-2-oxo-2,3,4,5-tetrahydro-1H-benzo[b]azepin-7-ylamino]-pyrimidin-4-ylamino}-bicyclo[2.2.1]hept-5-ene-2-carboxylic acid amide Following a procedure analogous to Example 113, N-(7-Amino-1-ethyl-6-methoxy-2-oxo-2,3,4,5-tetrahydro-1H-benzo[b]azepin-3-yl)-2-methoxy-acetamide (100 mgs) and (2,5-Dichloro-pyrimidin-4-yl)-(2-pyrazol-1-yl-phenyl)-amine were converted to the title compound (10 mgs) as a white powder. 1H-NMR (CDCl3): 10.27 (s, 1H), 8.50 (d, J=8.9 Hz, 1H), 8.33 (d, J=8.1 Hz, 1H), 8.11 (s, 1H), 7.88-7.84 (m, 2H), 7.54-7.41 (m, 3H), 7.28-7.23 (m, 1H), 6.91 (d, J=8.8 Hz, 1H), 4.58-4.55 (m, 1H), 4.37-4.32 (m, 1H), 3.93-3.81 (m, 4H), 3.56-3.51 (m, 1H), 3.45 (s, 3H), 3.13-3.10 (m, 1H), 2.63-2.53 (m, 2H), 2.01-1.98 (m, 1H), 1.27-1.16 (m, 5H). LC/MS. (M+H)+ found 591.23.

Example 1354 and 1355

(1S,2S,3R,4R)-3-{5-Chloro-2-[(R)-3-(2-dimethylamino-acetylamino)-1-ethyl-6-methoxy-2-oxo-2,3,4,5-tetrahydro-1H-benzo[b]azepin-7-ylamino]-pyrimidin-4-ylamino}-bicyclo[2.2.1]hept-5-ene-2-carboxylic acid amide and (1S,2S,3R,4R)-3-{5-Chloro-2-[(S)-3-(2-dimethylamino-acetylamino)-1-ethyl-6-methoxy-2-oxo-2,3,4,5-tetrahydro-1H-benzo[b]azepin-7-ylamino]-pyrimidin-4-ylamino}-bicyclo[2.2.1]hept-5-ene-2-carboxylic acid amide Following a procedure analogous to Example 1330d-e, (+/−)-3-Amino-1-ethyl-6-methoxy-7-nitro-1,3,4,5-tetrahydro-benzo[b]azepin-2-one dimethylamino-acetyl chloride; hydrochloride were converted to N-(7-Amino-1-ethyl-6-methoxy-2-oxo-2,3,4,5-tetrahydro-1H-benzo[b]azepin-3-yl)-2-dimethylamino-acetamide which following a procedure analogous to Example 113 was converted to the title compounds as individual diastereomers. Data for Faster eluting diastereomer on RP-HPLC: 1H NMR (400 MHz, (CD3)2SO) δ 8.92 (d, J=7.6 Hz, 1H), 8.25-8.44 (br s, 2H), 8.18 (d, J=8.8 Hz, 1H), 8.07 (s, 1H), 7.86 (s, 1H), 7.34 (s, 1H), 7.24 (d, J=9.1 Hz, 1H), 6.34 (m, 1H), 6.29 (m, 1H), 4.13-4.32 (m, 3H), 4.02 (t, J=7.7 Hz, 1H), 3.91 (s, 2H), 3.75 (s, 3H), 3.55 (m, 1H), 3.06 (dd, J=14.1 Hz, J=6.3 Hz, 1H), 2.91 (s, 1H), 2.84 (s, 1H), 2.77 (s, 6H), 2.37-2.46 (m, 1H), 2.23 (m, 1H), 2.07 (m, 1H), 2.06 (d, J=8.3 Hz, 1H), 1.40 (d, J=8.6 Hz, 1H), 1.03 (t, J=7.1 Hz, 3H). LCMS: found 598.24 (m+1). Data for slower eluting diastereomer on RP-HPLC: 1H NMR (400 MHz, (CD3)2SO) δ 8.93 (d, J=7.2 Hz, 1H), 8.57-8.72 (br s, 2H), 8.12 (s, 1H), 8.11 (d, J=8.8 Hz, 1H), 7.88 (s, 1H), 7.36 (s, 1H), 7.25 (d, J=8.6 Hz, 1H), 6.34 (m, 1H), 6.28 (m, 1H), 4.13-4.29 (m, 3H), 4.00 (t, J=7.5 Hz, 1H), 3.92 (s, 2H), 3.75 (s, 3H), 3.55 (m, 1H), 3.08 (dd, J=14.4 Hz, J=6.6 Hz, 1H), 2.91 (s, 1H), 2.86 (s, 1H), 2.77 (s, 6H), 2.37-2.46 (m, 1H), 2.25 (m, 1H), 2.08 (m, 1H), 2.04 (d, J=8.8 Hz, 1H), 1.40 (d, J=8.8 Hz, 1H), 1.03 (t, J=6.8 Hz, 3H). LCMS: found 598.24 (m+1).

Example 1356

N-{7-[5-Chloro-4-(2-dimethylsulfamoyl-phenylamino)-pyrimidin-2-ylamino]-1-ethyl-6-methoxy-2-oxo-2,3,4,5-tetrahydro-1H-benzo[b]azepin-3-yl}-2-dimethylamino-acetamide Following a procedure analogous to Example 113, N-(7-Amino-1-ethyl-6-methoxy-2-oxo-2,3,4,5-tetrahydro-1H-benzo[b]azepin-3-yl)-2-dimethylamino-acetamide (50 mgs) and 2-(2,5-Dichloro-pyrimidin-4-ylamino)-N,N-dimethyl-benzenesulfonamide was converted to the title compound as the TFA salt (24 mgs). 1H NMR (400 MHz, (CD3)2SO) δ 9.44 (s, 1H), 8.94 (d, J=7.3 Hz, 1H), 8.77 (s, 1H), 8.54 (d, J=7.6 Hz, 1H), 8.30 (s, 1H), 7.79 (d, J=8.1 Hz, 1H), 7.70 (d, J=8.6 Hz, 1H), 7.59 (t, J=7.9 Hz, 1H), 7.31 (t, J=7.6 Hz, 1H), 7.17 (d, J=9.1 Hz, 1H), 4.14-4.30 (m, 2H), 3.92 (s, 2H), 3.70 (s, 3H), 3.54 (m, 1H), 3.07 (m, 1H), 2.78 (s, 6H), 2.66 (s, 6H), 2.42 (m, 1H), 2.20 (m, 1H), 2.07 (m, 1H), 1.04 (t, J=7.1 Hz, 3H). LCMS: found 646.18 (m+1).

Example 1357 and 1358

(1S,2S,3R,4R)-3-{5-Chloro-2-[(R)-3-(cyclopropanecarbonyl-amino)-1-ethyl-6-methoxy-2-oxo-2,3,4,5-tetrahydro-1H-benzo[b]azepin-7-ylamino]-pyrimidin-4-ylamino}-bicyclo[2.2.1]hept-5-ene-2-carboxylic acid amide and (1S,2S,3R,4R)-3-{5-Chloro-2-[(S)-3-(cyclopropanecarbonyl-amino)-1-ethyl-6-methoxy-2-oxo-2,3,4,5-tetrahydro-1H-benzo[b]azepin-7-ylamino]-pyrimidin-4-ylamino}-bicyclo[2.2.1]hept-5-ene-2-carboxylic acid amide Following a procedure analogous to Example 1330d-e, (+/−)-3-Amino-1-ethyl-6-methoxy-7-nitro-1,3,4,5-tetrahydro-benzo[b]azepin-2-one and Cyclopropanecarbonyl Chloride were converted to Cyclopropanecarboxylic acid (7-amino-1-ethyl-6-methoxy-2-oxo-2,3,4,5-tetrahydro-1H-benzo[b]azepin-3-yl)-amide which following a procedure analogous to Example 113 was converted to the title compounds as individual diastereomers. Data for Faster eluting diastereomer on RP-HPLC: 1H NMR (400 MHz, (CD3)2SO) δ 8.50 (br s, 2H), 8.38 (d, J=7.8 Hz, 1H), 8.13 (s, 1H), 8.11 (d, J=8.8 Hz, 1H), 7.89 (s, 1H), 7.36 (s, 1H), 7.24 (d, J=8.8 Hz, 1H), 6.34 (m, 1H), 6.27 (m, 1H), 4.18-4.30 (m, 3H), 4.00 (t, J=7.3 Hz, 1H), 3.75 (s, 3H), 3.50 (m, 1H), 3.05 (dd, J=13.7

Hz, J=5.5 Hz, 1H), 2.91 (s, 1H), 2.87 (s, 1H), 2.07-2.22 (m, 3H), 2.02 (d, J=8.6 Hz, 1H), 1.66 (m, 1H), 1.42 (d, J=8.8 Hz, 1H), 1.01 (t, J=7.1 Hz, 3H), 0.55-0.69 (m, 4H). LCMS: found 581.15 (m+1). Data for Slower eluting Diastereomer: $^1$H NMR (400 MHz, (CD$_3$)$_2$SO) δ 8.90 (br s, 2H), 8.39 (d, J=8.1 Hz, 1H), 8.16 (s, 1H), 8.05 (d, J=8.8 Hz, 1H), 7.89 (s, 1H), 7.37 (s, 1H), 7.25 (d, J=8.8 Hz, 1H), 6.34 (m, 1H), 6.29 (m, 1H), 4.18-4.29 (m, 3H), 4.00 (t, J=7.3 Hz, 1H), 3.75 (s, 3H), 3.51 (m, 1H), 3.05 (dd, J=14.0 Hz, J=6.1 Hz, 1H), 2.91 (s, 1H), 2.87 (s, 1H), 2.06-2.22 (m, 3H), 2.02 (d, J=8.6 Hz, 1H), 1.66 (m, 1H), 1.42 (d, J=8.8 Hz, 1H), 1.01 (t, J=6.9 Hz, 3H), 0.53-0.68 (m, 4H). LCMS: found 581.17 (m+1).

Example 1359

Cyclopropanecarboxylic acid {7-[5-chloro-4-(2-dimethylsulfamoyl-phenylamino)-pyrimidin-2-ylamino]-1-ethyl-6-methoxy-2-oxo-2,3,4,5-tetrahydro-1H-benzo[b]azepin-3-yl}-amide Following a procedure analogous to Example 113 Cyclopropanecarboxylic acid (7-amino-1-ethyl-6-methoxy-2-oxo-2,3,4,5-tetrahydro-1H-benzo[b]azepin-3-yl)-amide (45 mgs) and 2-(2,5-Dichloro-pyrimidin-4-ylamino)-N,N-dimethyl-benzenesulfonamide was converted to the title compound (48 mgs). $^1$H NMR (400 MHz, (CD$_3$)$_2$SO) δ 9.41 (s, 1H), 8.70 (s, 1H), 8.55 (d, J=8.1 Hz, 1H), 8.39 (d, J=8.8 Hz, 1H), 8.28 (s, 1H), 7.78 (d, J=7.8 Hz, 1H), 7.67 (d, J=9.1 Hz, 1H), 7.57 (t, J=7.8 Hz, 1H), 7.27 (t, J=7.7 Hz, 1H), 7.14 (d, J=8.6 Hz, 1H), 4.19-4.30 (m, 2H), 3.69 (s, 3H), 3.48 (m, 1H), 3.04 (dd, J=13.7 Hz, J=5.4 Hz, 1H), 2.65 (s, 6H), 2.33-2.41 (m, 1H), 2.04-2.12 (m, 2H), 1.67 (m, 1H), 1.02 (t, J=6.8 Hz, 3H), 0.56-0.67 (m, 4H). LCMS: found 629.11 (m+1).

Example 1361

2-{5-Chloro-2-[3-((R)-3,3,3-trifluoro-2-methoxy-propyl)-2,3,4,5-tetrahydro-1H-benzo[d]azepin-7-ylamino]-pyrimidin-4-ylamino}-3-fluoro-N-methyl-benzamide 2-{5-Chloro-2-[3-((R)-3,3,3-trifluoro-2-methoxy-propyl)-2,3,4,5-tetrahydro-1H-benzo[d]azepin-7-ylamino]-pyrimidin-4-ylamino}-3-fluoro-N-methyl-benzamide was prepared from 3-((R)-3,3,3-trifluoro-2-methoxy-propyl)-2,3,4,5-tetrahydro-1H-benzo[d]azepin-7-ylamine and 2-(2,5-dichloro-pyrimidin-4-ylamino)-3-fluoro-N-methyl-benzamide in an analogous manner to Example 335. Product isolated as a yellow solid (56 mg, 24%). LCMS (m/e) 567 (M+H); $^1$H-NMR (CDCl$_3$, 400 MHz) δ 8.74 (s, 1H), 8.08 (s, 1H), 7.36-7.25 (m, 3H), 7.19-7.11 (m, 2H), 6.91 (d, 1H, J=7.9 Hz), 6.87 (s, 1H), 6.13-6.05 (m, 1H), 3.75-3.65 (m, 1H), 3.61 (s, 3H), 2.93 (d, 3H, J=4.8 Hz), 2.89-2.65 (m, 10H).

Example 1362

3-{5-Chloro-2-[3-(2-methoxy-ethyl)-2,3,4,5-tetrahydro-1H-benzo[d]azepin-7-ylamino]-pyrimidin-4-ylamino}-4-methyl-thiophene-2-carboxylic acid methylamide 3-{5-Chloro-2-[3-(2-methoxy-ethyl)-2,3,4,5-tetrahydro-1H-benzo[d]azepin-7-ylamino]-pyrimidin-4-ylamino}-4-methyl-thiophene-2-carboxylic acid methylamide was prepared from 3-(2-methoxy-ethyl)-2,3,4,5-tetrahydro-1H-benzo[d]azepin-7-ylamine and 3-(2,5-dichloro-pyrimidin-4-ylamino)-4-methyl-thiophene-2-carboxylic acid methylamide in an analogous manner to Example 308c. Product isolated as a yellow foam (120 mg, 70%). LCMS (m/e) 501 (M+H); $^1$H-NMR (CDCl$_3$, 400 MHz) δ 8.77 (s, 1H), 8.08 (s, 1H), 7.23 (s, 1H), 7.09-7.05 (m, 2H), 6.93 (d, 1H, J=8.0 Hz), 6.81 (s, 1H), 5.98-5.91 (m, 1H), 3.55 (t, 2H, J=5.7 Hz), 3.39 (s, 3H), 2.96 (d, 3H, J=4.8 Hz), 2.90-2.85 (m, 2H), 2.82-2.66 (m, 8H), 2.13 (s, 3H).

Example 1363

3-{5-Chloro-2-[3-(2-methoxy-ethyl)-2,3,4,5-tetrahydro-1H-benzo[d]azepin-7-ylamino]-pyrimidin-4-ylamino}-4-methyl-thiophene-2-carboxylic acid methylamide 1363a) 8-Fluoro-1H-benzo[d][1,3]oxazine-2,4-dione (10.0 g, 55.2 mmol) was dissolved in tetrahydrofuran (200 mL, 2000 mmol) at 0° C. 2.0 M Ethylamine in tetrahydrofuran (41 mL) was added and the reaction was stirred for 2 hours. The reaction was concentrated under reduced pressure and azeotroped with toluene (50 mL). Ethyl ether (200 mL) was added and the precipitate (the acid byproduct formed by hydrolysis) was removed by filtration. The filtrate was concentrated under reduced pressure and the product was purified by silica gel chromatography using a gradient of 0-60% EtOAc/hex as the eluting solvent to obtain 2-amino-N-ethyl-3-fluoro-benzamide as a pale yellow solid (9.02 g, 90%). m.p.=60° C.; LCMS (m/e) 183 (M+H); $^1$H-NMR (CDCl$_3$, 400 MHz) δ 7.11 (d, 1H, J=8.0 Hz), 7.09-7.02 (m, 1H), 6.62-6.54 (m, 1H), 6.05 (bs, 1H), 5.61 (bs, 2H), 3.52-3.43 (m, 2H), 1.26 (t, 3H, J=6.6 Hz).

1363b) Into a round bottom flask was added 2-amino-N-ethyl-3-fluoro-benzamide (2.00 g, 11.0 mmol) and N-methylpyrrolidinone (10 mL, 100 mmol). N,N-diisopropylethylamine (2.29 mL, 13.2 mmol) was added followed by 2,4,5-trichloro-pyrimidine (1.51 mL, 13.2 mmol) and the mixture was heated at 100° C. for 24 hours. The reaction mixture was then concentrated under reduced pressure and the residue was taken up in DCM (50 mL) and washed with water (50 mL). The organic layer was dried over sodium sulfate, filtered, and concentrated under reduced pressure. Purification by amine capped silica gel chromatography using a gradient of 0-70% EtOAc/hex as the eluting solvent. The product was placed in hexane and stirred overnight. The mixture was filtered to obtain 2-(2,5-Dichloro-pyrimidin-4-ylamino)-N-ethyl-3-fluoro-benzamide as a yellow solid (1.79 g, 50%). m.p.=233-234° C.; LCMS (m/e) 329 (M+H); $^1$H-NMR (CDCl$_3$, 400 MHz) δ 9.33 (s, 1H), 8.22 (s, 1H), 7.40-7.22 (m, 3H), 6.20-6.10 (m, 1H), 3.53-3.42 (m, 2H), 1.25 (t, 3H, J=7.3 Hz).

1363c) 3-{5-Chloro-2-[3-(2-methoxy-ethyl)-2,3,4,5-tetrahydro-1H-benzo[d]azepin-7-ylamino]-pyrimidin-4-ylamino}-4-methyl-thiophene-2-carboxylic acid methylamide was prepared from 3-(2-methoxy-ethyl)-2,3,4,5-tetrahydro-1H-benzo[d]azepin-7-ylamine and 2-(2,5-dichloro-pyrimidin-4-ylamino)-N-ethyl-3-fluoro-benzamide in an analogous manner to Example 308c. Product isolated as a pale yellow foam (117 mg, 66%). LCMS (m/e) 513 (M+H); $^1$H-NMR (CDCl$_3$, 400 MHz) δ 8.53 (s, 1H), 8.07 (s, 1H), 7.37-7.26 (m, 3H), 7.15 (s, 1H), 7.10 (d, 1H, J=7.9 Hz), 6.90 (d, 1H, J=7.9 Hz), 6.84 (s, 1H), 6.11-6.03 (m, 1H), 3.55 (t, 2H, J=5.5 Hz), 3.44-3.34 (m, 2H), 3.99 (s, 3H), 2.90-2.83 (m, 2H), 2.82-2.73 (m, 4H), 2.72-2.64 (m, 4H), 1.13 (t, 3H, J=6.2 Hz).

Example 1364

2-[5-Chloro-2-(8-methoxy-3-methylcarbamoylmethyl-2,3,4,5-tetrahydro-1H-benzo[d]azepin-7-ylamino)-pyrimidin-4-ylamino]-N-ethyl-3-fluoro-benzamide 2-[5-Chloro-2-(8-methoxy-3-methylcarbamoylmethyl-2,3,4,5-tetrahydro-1H-benzo[d]azepin-7-ylamino)-pyrimidin-4-ylamino]-N-ethyl-3-fluoro-benzamide was prepared from 2-(7-amino-8-methoxy-1,2,4,5-tetrahydro-benzo[d]azepin-3-yl)-N-methyl-acetamide and 2-(2,5-dichloro-pyrimidin-4-ylamino)-N-ethyl-3-fluoro-benzamide in an analogous manner to Example 308c. Product isolated as a yellow foam (52 mg, 25%). LCMS (m/e) 556 (M+H); $^1$H-NMR (CDCl$_3$, 400 MHz) δ 8.57 (s, 1H), 8.09 (s, 1H), 7.77 (s, 1H), 7.47 (s, 1H), 7.40-7.24 (m, 4H), 6.59 (s, 1H), 6.31-6.23 (m, 1H), 3.84 (s, 3H), 3.45-3.35 (m, 2H), 3.11 (s, 2H), 2.88 (d, 3H, J=4.8 Hz), 2.86-2.78 (m, 2H), 2.71-2.64 (m, 2H), 2.63-2.55 (m, 4H), 1.13 (t, 3H, J=7.3 Hz).

Example 1365

2-[5-Chloro-2-(5,5-dimethyl-2-oxo-2,3,4,5-tetrahydro-1H-benzo[b]azepin-7-ylamino)-pyrimidin-4-ylamino]-N-ethyl-3-fluoro-benzamide 2-[5-Chloro-2-(5,5-dimethyl-2-oxo-2,3,4,5-tetrahydro-1H-benzo[b]azepin-7-ylamino)-pyrimidin-4-ylamino]-N-ethyl-3-fluoro-benzamide was prepared from 7-amino-5,5-dimethyl-1,3,4,5-tetrahydro-benzo[b]azepin-2-one and 2-(2,5-dichloro-pyrimidin-4-ylamino)-N-ethyl-3-fluoro-benzamide in an analogous manner to Example 308c. Product isolated as a yellow foam (213 mg, 51%). LCMS (m/e) 497 (M+H); $^1$H-NMR (CDCl$_3$, 400 MHz) δ 8.73 (s, 1H), 8.10 (s, 1H), 7.56 (d, 1H, J=8.5 Hz), 7.40-7.35 (m, 1H), 7.34-7.25 (m, 2H), 7.21 (s, 1H), 7.10 (s, 1H), 6.96 (s, 1H), 6.72 (d, 1H, J=8.5 Hz), 6.15-6.06 (m, 1H), 3.48-3.38 (m, 2H), 2.36 (t, 2H, J=6.8 Hz), 2.08 (t, 2H, J=6.8 Hz), 1.35 (s, 6H), 1.17 (t, 3H, J=7.3 Hz).

Example 1366

2-[5-Chloro-2-(1,5,5-trimethyl-2-oxo-2,3,4,5-tetrahydro-1H-benzo[b]azepin-7-ylamino)-pyrimidin-4-ylamino]-N-ethyl-3-fluoro-benzamide 2-[5-Chloro-2-(1,5,5-trimethyl-2-oxo-2,3,4,5-tetrahydro-1H-benzo[b]azepin-7-ylamino)-pyrimidin-4-ylamino]-N-ethyl-3-fluoro-benzamide was prepared from 7-amino-1,5,5-trimethyl-1,3,4,5-tetrahydro-benzo[b]azepin-2-one and 2-(2,5-dichloro-pyrimidin-4-ylamino)-N-ethyl-3-fluoro-benzamide in an analogous manner to Example 308c. Product isolated as a white solid (96 mg, 68%). m.p.=251-253° C.; LCMS (m/e) 511 (M+H); $^1$H-NMR (CDCl$_3$, 400 MHz) δ 8.77 (s, 1H), 8.11 (s, 1H), 7.63 (d, 1H, J=8.6 Hz), 7.41-7.34 (m, 1H), 7.33-7.26 (m, 2H), 7.16 (s, 1H), 6.99 (d, 1H, J=8.6 Hz), 6.93 (s, 1H), 6.14-6.06 (m, 1H), 3.48-3.39 (m, 2H), 3.27 (s, 3H), 2.32-2.24 (m, 2H), 2.05-1.95 (m, 2H), 1.26 (s, 6H), 1.18 (t, 3H, J=7.3 Hz).

Example 1367

2-[5-Chloro-2-(3-dimethylcarbamoylmethyl-2,3,4,5-tetrahydro-1H-benzo[d]azepin-7-ylamino)-pyrimidin-4-ylamino]-N-ethyl-3-fluoro-benzamide 1367a) 7-Nitro-2,3,4,5-tetrahydro-1H-benzo[d]azepine; compound with nitric acid (763 mg, 2.99 mmol) was suspended in acetonitrile (50.0 mL, 957 mmol) and 2-chloro-N,N-dimethyl-acetamide (400 mg, 3.29 mmol) was added. Cesium carbonate (2.44 g, 7.48 mmol) and cesium iodide (77.7 mg, 0.299 mmol) were added and the reaction was heated at reflux for 3 hours. The reaction was cooled to room temperature and then diluted with DCM (50 mL) and washed with water (50 mL). The organic layer was dried over sodium sulfate, filtered, and concentrated under reduced pressure. Purification by silica gel chromatography using a gradient of 0-15% MeOH/DCM as the eluting solvent to obtain N,N-Dimethyl-2-(7-nitro-1,2,4,5-tetrahydro-benzo[d]azepin-3-yl)-acetamide as an orange solid (778 mg, 94%). m.p.=94-96° C.; LCMS (m/e) 278 (M+H); $^1$H-NMR (CDCl$_3$, 400 MHz) δ 8.02-7.97 (m, 2H), 7.25 (d, 1H, J=7.9 Hz), 3.34 (s, 2H), 3.12 (s, 3H), 3.08-3.02 (m, 4H), 2.99 (s, 3H), 2.80-2.73 (m, 4H).

1367b) N,N-Dimethyl-2-(7-nitro-1,2,4,5-tetrahydro-benzo[d]azepin-3-yl)-acetamide (150 mg, 0.541 mmol) was placed in methanol (10.0 mL, 247 mmol) and 10% palladium on carbon (50% Wet) (5:45:50, palladium:carbon black:water, 15.0 mg) was added. The reaction was hydrogenated at 30 psi. for 1 hour, filtered through Celite, and then concentrated under reduced pressure to obtain 2-(7-Amino-1,2,4,5-tetrahydro-benzo[d]azepin-3-yl)-N,N-dimethyl-acetamide as an orange solid (134 mg, 100%). LCMS (m/e) 248 (M+H); $^1$H-NMR (CDCl$_3$, 400 MHz) δ 6.88 (d, 1H, J=7.5 Hz), 6.50-6.44 (m, 2H), 3.54 (bs, 2H), 3.28 (s, 2H), 3.16 (s, 3H), 2.98 (s, 3H), 2.870-2.81 (m, 4H), 2.71-2.62 (m, 4H).

1367c) 2-[5-Chloro-2-(3-dimethylcarbamoylmethyl-2,3,4,5-tetrahydro-1H-benzo[d]azepin-7-ylamino)-pyrimidin-4-ylamino]-N-ethyl-3-fluoro-benzamide was prepared from 2-(7-amino-1,2,4,5-tetrahydro-benzo[d]azepin-3-yl)-N,N-dimethyl-acetamide and 2-(2,5-dichloro-pyrimidin-4-ylamino)-N-ethyl-3-fluoro-benzamide in an analogous manner to Example 308c. Product isolated as a yellow foam (137 mg, 47%). LCMS (m/e) 540 (M+H); $^1$H-NMR (CDCl$_3$, 400 MHz) δ 8.57 (s, 1H), 8.08 (s, 1H), 7.38-7.25 (m, 3H), 7.15 (s, 1H), 7.10 (d, 1H, J=7.8 Hz), 6.90 (d, 1H, J=7.8 Hz), 6.82 (s, 1H), 6.14-6.07 (m, 1H), 3.44-3.35 (m, 2H), 3.28 (s, 2H), 3.15 (s, 3H), 3.00 (s, 3H), 2.89-2.83 (m, 2H), 2.80-2.73 (m, 2H), 2.70-2.61 (m, 4H), 1.14 (t, 3H, J=7.3 Hz).

Example 1368

2-{7-[5-Chloro-4-(2-methoxy-4-morpholin-4-yl-phenylamino)-pyrimidin-2-ylamino]-1,2,4,5-tetrahydro-benzo[d]azepin-3-yl}-N,N-dimethyl-acetamide 2-{7-[5-Chloro-4-(2-methoxy-4-morpholin-4-yl-phenylamino)-pyrimidin-2-ylamino]-1,2,4,5-tetrahydro-benzo[d]azepin-3-yl}-N,N-dimethyl-acetamide was prepared from 2-(7-amino-1,2,4,5-tetrahydro-benzo[d]azepin-3-yl)-N,N-dimethyl-acetamide and (2,5-dichloro-pyrimidin-4-yl)-(2-methoxy-4-morpholin-4-yl-phenyl)-amine in an analogous manner to Example 308c. Product isolated as a yellow foam (103 mg, 45%). LCMS (m/e) 566 (M+H); $^1$H-NMR (CDCl$_3$, 400 MHz) δ 8.25 (d, 1H, J=9.2 Hz), 8.02 (s, 1H), 7.59 (s, 1H), 7.39 (s, 1H), 7.26-7.19 (m, 1H), 7.03 (d, 1H, J=8.4 Hz), 6.85 (s, 1H), 6.56 (s, 1H), 6.51 (d, 1H, J=9.0 Hz), 3.93 (s, 3H), 3.95-3.88 (m, 4H), 3.30 (s, 2H), 3.19-3.13 (m, 4H), 3.16 (s, 3H), 2.99 (s, 3H), 2.95-2.89 (m, 4H), 2.76-2.68 (m, 4H).

Example 1369

2-[5-Chloro-2-(3-dimethylcarbamoylmethyl-2,3,4,5-tetrahydro-1H-benzo[d]azepin-7-ylamino)-pyrimidin-4-ylamino]-3-fluoro-N-methyl-benzamide 2-[5-Chloro-2-(3-dimethylcarbamoylmethyl-2,3,4,5-tetrahydro-1H-benzo[d]azepin-7-ylamino)-pyrimidin-4-ylamino]-3-fluoro-N-methyl-benzamide was prepared from 2-(7-amino-1,2,4,5-tetrahydro-benzo[d]azepin-3-yl)-N,N-dimethyl-acetamide and 2-(2,5-dichloro-pyrimidin-4-ylamino)-3-fluoro-N-methyl-benzamide in an analogous manner to Example 308c. Product isolated as a yellow foam (91 mg, 43%). LCMS (m/e) 526 (M+H); $^1$H-NMR (CDCl$_3$, 400 MHz) δ 8.73 (s, 1H), 8.07 (s, 1H), 7.35-7.25 (m, 3H), 7.15 (s, 1H), 7.10 (d, 1H, J=8.3 Hz), 6.89 (d, 1H, J=8.3 Hz), 6.83 (s, 1H), 6.17-6.10 (m, 1H), 3.28 (s, 2H), 3.15 (s, 3H), 2.99 (s, 3H), 2.92 (d, 3H, J=4.8 Hz), 2.89-2.83 (m, 2H), 2.79-2.73 (m, 2H), 2.69-2.61 (m, 4H).

Example 1370

3-Chloro-2-[5-chloro-2-(3-dimethylcarbamoylmethyl-2,3,4,5-tetrahydro-1H-benzo[d]azepin-7-ylamino)-pyrimidin-4-ylamino]-N-methyl-benzamide 3-Chloro-2-[5-chloro-2-(3-dimethylcarbamoylmethyl-2,3,4,5-tetrahydro-1H-benzo[d]azepin-7-ylamino)-pyrimidin-4-ylamino]-N-methyl-benzamide was prepared from 2-(7-amino-1,2,4,5-tetrahydro-benzo[d]azepin-3-yl)-N,N-dimethyl-acetamide and 3-chloro-2-(2,5-dichloro-pyrimidin-4-ylamino)-N-methyl-benzamide in an analogous manner to Example 308c. Product isolated as a yellow foam (26 mg, 12%). LCMS (m/e) 542 (M+H); $^1$H-NMR (CDCl$_3$, 400 MHz) δ 8.09 (s, 1H), 7.86 (s, 1H), 7.60 (d, 1H, J=8.0 Hz), 7.47 (d, 1H, J=7.7 Hz), 7.34-7.26 (m, 1H), 7.12 (s, 1H), 7.05-6.99 (m, 1H), 6.91-6.83 (m, 2H), 6.06-5.97 (m, 1H), 3.29 (s, 2H), 3.14 (s, 3H), 2.99 (s, 3H), 2.90-2.84 (m, 2H), 2.77 (d, 3H, J=4.9 Hz), 2.77-2.71 (m, 2H), 2.70-2.62 (m, 4H).

Example 1371

2-{7-[5-Chloro-4-((1R,2R)-2-methanesulfonylamino-cyclohexylamino)-pyrimidin-2-ylamino]-1,2,4,5-tetrahydro-benzo[d]azepin-3-yl}-N,N-dimethyl-acetamide 2-{7-[5-Chloro-4-((1R,2R)-2-methanesulfonylamino-cyclohexylamino)-pyrimidin-2-ylamino]-1,2,4,5-tetrahydro-benzo[d]azepin-3-yl}-N,N-dimethyl-acetamide was prepared from 2-(7-amino-1,2,4,5-tetrahydro-benzo[d]azepin-3-yl)-N,N-dimethyl-acetamide and N-[(1R,2R)-2-(2,5-dichloro-pyrimidin-4-ylamino)-cyclohexyl]-methanesulfonamide in an analogous manner to Example 308c. Product isolated as a yellow foam (88 mg, 39%). LCMS (m/e) 550 (M+H); $^1$H-NMR (CDCl$_3$, 400 MHz) δ 7.93 (s, 1H), 7.30-7.22 (m, 2H), 7.05 (d, 1H, J=8.0 Hz), 6.85 (s, 1H), 5.56-5.35 (m, 2H), 3.93-3.82 (m, 1H), 3.31 (s, 2H), 3.31-3.20 (m, 1H), 3.15 (s, 3H), 3.09 (s, 3H), 2.97-2.87 (m, 4H), 2.81 (s, 3H), 2.77-2.67 (m, 4H), 2.27-2.17 (m, 2H), 1.89-1.79 (m, 2H), 1.45-1.32 (m, 4H).

Example 1372

2-[5-Chloro-2-(3-methylcarbamoylmethyl-2,3,4,5-tetrahydro-1H-benzo[d]azepin-7-ylamino)-pyrimidin-4-ylamino]-N-ethyl-3-fluoro-benzamide 2-[5-Chloro-2-(3-methylcarbamoylmethyl-2,3,4,5-tetrahydro-1H-benzo[d]azepin-7-ylamino)-pyrimidin-4-ylamino]-N-ethyl-3-fluoro-benzamide was prepared from 2-(7-amino-1,2,4,5-tetrahydro-benzo[d]azepin-3-yl)-N-methyl-acetamide and 2-(2,5-dichloro-pyrimidin-4-ylamino)-N-ethyl-3-fluoro-benzamide in an analogous manner to Example 308c. Product isolated as a yellow foam (117 mg, 52%). LCMS (m/e) 526 (M+H); 1H-NMR (CDCl$_3$, 400 MHz) δ 8.63 (s, 1H), 8.08 (s, 1H), 7.40-7.33 (m, 1H), 7.33-7.24 (m, 2H), 7.18 (s, 1H), 7.14 (d, 1H, J=8.1 Hz), 6.91 (d, 1H, J=8.1 Hz), 6.85 (s, 1H), 6.20-6.13 (m, 1H), 3.46-3.36 (m, 2H), 3.12 (s, 2H), 2.87 (d, 3H, J=4.9 Hz), 2.87-2.81 (m, 2H), 2.81-2.74 (m, 2H), 2.72-2.63 (m, 4H), 1.15 (t, 3H, J=7.3 Hz).

Example 1373

3-Chloro-2-[5-chloro-2-(3-methylcarbamoylmethyl-2,3,4,5-tetrahydro-1H-benzo[d]azepin-7-ylamino)-pyrimidin-4-ylamino]-N-methyl-benzamide 3-Chloro-2-[5-chloro-2-(3-methylcarbamoylmethyl-2,3,4,5-tetrahydro-1H-benzo[d]azepin-7-ylamino)-pyrimidin-4-ylamino]-N-methyl-benzamide was prepared from 2-(7-amino-1,2,4,5-tetrahydro-benzo[d]azepin-3-yl)-N-methyl-acetamide and 3-chloro-2-(2,5-dichloro-pyrimidin-4-ylamino)-N-methyl-benzamide in an analogous manner to Example 308c. Product isolated as a yellow foam (53 mg, 23%). LCMS (m/e) 528 (M+H); $^1$H-NMR (CDCl$_3$, 400 MHz) δ 8.10 (s, 1H), 7.93 (s, 1H), 7.60 (d, 1H, J=8.0 Hz), 7.50 (d, 1H, J=7.7 Hz), 7.34-7.26 (m, 1H), 7.16 (s, 1H), 7.06 (d, 1H, J=7.3 Hz), 6.90 (d, 1H, J=8.0 Hz), 6.85 (s, 1H), 6.13-6.06 (m, 1H), 3.12 (s, 2H), 2.88 (d, 3H, J=5.0 Hz), 2.87-2.82 (m, 2H), 2.80 (d, 3H, J=4.9 Hz), 2.77-2.72 (m, 2H), 2.71-2.62 (m, 4H).

Example 1374

2-{7-[5-Chloro-4-((1R,2R)-2-methanesulfonylamino-cyclohexylamino)-pyrimidin-2-ylamino]-1,2,4,5-tetrahydro-benzo[d]azepin-3-yl}-N-methyl-acetamide 2-{7-[5-Chloro-4-((1R,2R)-2-methanesulfonylamino-cyclohexylamino)-pyrimidin-2-ylamino]-1,2,4,5-tetrahydro-benzo[d]azepin-3-yl}-N-methyl-acetamide was prepared from 2-(7-amino-1,2,4,5-tetrahydro-benzo[d]azepin-3-yl)-N-methyl-acetamide and N-[(1R,2R)-2-(2,5-dichloro-pyrimidin-4-ylamino)-cyclohexyl]-methanesulfonamide in an analogous manner to Example 308c. Product isolated as a pale yellow foam (85 mg, 44%). LCMS (m/e) 536 (M+H); $^1$H-NMR (CDCl$_3$, 400 MHz) δ 7.94 (s, 1H), 7.40-7.23 (m, 3H), 7.06 (d, 1H, J=8.0 Hz), 6.86 (s, 1H), 5.47-5.35 (m, 2H), 3.93-3.81 (m, 1H), 3.31-3.19 (m, 1H), 3.15 (s, 2H), 2.96-2.86 (m, 4H), 2.90 (d, 3H, J=5.0 Hz), 2.81 (s, 3H), 2.78-2.66 (m, 4H), 2.29-2.16 (m, 2H), 1.90-1.79 (m, 2H), 1.46-1.30 (m, 4H).

Example 1375

2-[5-Chloro-2-(2-oxo-2,3,4,5-tetrahydro-1H-benzo[b]azepin-8-ylamino)-pyrimidin-4-ylamino]-3-fluoro-N-methyl-benzamide 2-[5-Chloro-2-(2-oxo-2,3,4,5-tetrahydro-1H-benzo[b]azepin-8-ylamino)-pyrimidin-4-ylamino]-3-fluoro-N-methyl-benzamide was prepared from 8-amino-1,3,4,5-tetrahydro-benzo[b]azepin-2-one and 2-(2,5-dichloro-pyrimidin-4-ylamino)-3-fluoro-N-methyl-benzamide in an analogous manner to Example 308c. Product isolated as a yellow solid (67 mg, 32%). m.p.=180-190° C.; LCMS (m/e) 455 (M+H); $^1$H-NMR (d6-DMSO, 400 MHz) δ 9.35-9.22 (m, 3H), 8.56-8.47 (m, 1H), 8.17 (s, 1H), 7.50-7.42 (m, 2H), 7.40-7.31 (m, 1H), 7.23 (d, 1H, J=8.3 Hz) 7.09 (s, 1H), 6.93 (d, 1H, J=8.3 Hz), 2.72 (d, 3H, J=4.4 Hz), 2.56 (t, 2H, J=6.2 Hz), 2.12-1.97 (m, 4H).

Example 1376

5-Chloro-N(4)-(2-chloro-phenyl)-N(2)-[3-(2-methoxy-ethyl)-2,3,4,5-tetrahydro-1H-benzo[d]azepin-7-yl]-pyrimidine-2,4-diamine 1376a) Into a round bottom flask was added o-chloroaniline (6.46 mL, 39.2 mmol) and N-methylpyrrolidinone (37.8 mL, 392 mmol). N,N-Diisopropylethylamine (8.19 mL, 47.0 mmol) was added followed by 2,4,5-trichloro-pyrimidine (5.39 mL, 47.0 mmol) and the mixture was heated at 100° C. for 24 hours. The reaction mixture was then concentrated under reduced pressure and the residue was taken up in DCM (150 mL) and washed with water (150 mL). The organic layer was dried over sodium sulfate, filtered, and concentrated under reduced pressure. Purification by silica gel chromatography using a gradient of 0-12% EtOAc/hex as the eluting solvent to obtain (2-chloro-phenyl)-(2,5-dichloro-pyrimidin-4-yl)-amine as a yellow solid (9.0 g, 84%). LCMS (m/e) 274 (M+H); $^1$H-NMR (CDCl$_3$, 400 MHz) δ 8.54 (d, 1H, J=8.3 Hz), 8.28 (s, 1H), 8.00 (bs, 1H), 7.47 (d, 1H, J=8.0 Hz), 7.44-7.37 (m, 1H), 7.17-7.11 (m, 1H).

1376b) 5-Chloro-N(4)-(2-chloro-phenyl)-N(2)-[3-(2-methoxy-ethyl)-2,3,4,5-tetrahydro-1H-benzo[d]azepin-7-yl]-pyrimidine-2,4-diamine was prepared from 3-(2-methoxy-ethyl)-2,3,4,5-tetrahydro-1H-benzo[d]azepin-7-ylamine and (2-chloro-phenyl)-(2,5-dichloro-pyrimidin-4-yl)-amine in an analogous manner to Example 308c. Product isolated as a pale yellow foam (109 mg, 52%). m.p.=85-92° C.; LCMS (m/e) 458 (M+H); $^1$H-NMR (CDCl$_3$, 400 MHz) δ 8.47 (d, 1H, J=8.3 Hz), 8.12 (s, 1H), 7.73 (s, 1H), 7.45 (d, 1H, J=8.0 Hz), 7.33 (s, 1H), 7.30-7.20 (m, 2H), 7.11-7.02 (m, 2H), 6.92 (s, 1H), 3.56 (t, 2H, J=5.7 Hz), 3.39 (s, 3H), 2.97-2.87 (m, 4H), 2.80-2.70 (m, 6H).

Example 1377

5-Chloro-N(4)-cyclohexyl-N(2)-[3-(2-methoxy-ethyl)-2,3,4,5-tetrahydro-1H-benzo[d]azepin-7-yl]-pyrimidine-2,4-diamine 1377a) Into a round bottom flask was added cyclohexanamine (1.0 mL, 8.7 mmol) and 1,4-dioxane (30 mL, 380 mmol). N,N-Diisopropylethylamine (1.83 mL, 10.5 mmol) was added followed by 2,4,5-trichloro-pyrimidine (1.20 mL, 10.5 mmol) and the mixture was heated at 100° C. overnight and then concentrated under reduced pressure. The residue was taken up in DCM (100 mL) and washed with water (100 mL). The organic layer was dried over sodium sulfate, filtered, and concentrated under reduced pressure. Purification by silica gel chromatography using a gradient of 0-20% EtOAc/hex as the eluting solvent to obtain cyclohexyl-(2,5-dichloro-pyrimidin-4-yl)-amine as a white solid (1.87 g, 87%). m.p.=93-94° C.; LCMS (m/e) 246 (M+H); $^1$H-NMR (CDCl$_3$, 400 MHz) δ 8.01 (s, 1H), 5.45-5.30 (m, 1H), 4.13-4.00 (m, 1H), 2.10-1.99 (m, 2H), 1.85-1.74 (m, 2H), 1.74-1.63 (m, 1H), 1.55-1.39 (m, 2H), 1.36-1.18 (m, 3H).

1377b) 5-Chloro-N(4)-cyclohexyl-N(2)-[3-(2-methoxy-ethyl)-2,3,4,5-tetrahydro-1H-benzo[d]azepin-7-yl]-pyrimidine-2,4-diamine was prepared from 3-(2-methoxy-ethyl)-2,3,4,5-tetrahydro-1H-benzo[d]azepin-7-ylamine and cyclohexyl-(2,5-dichloro-pyrimidin-4-yl)-amine in an analogous manner to Example 308c. Product isolated as a pale yellow foam (65 mg, 37%). LCMS (m/e) 430 (M+H); $^1$H-NMR (CDCl$_3$, 400 MHz) δ 8.87 (s, 1H), 7.40-7.30 (m, 2H), 7.07-7.00 (m, 1H), 6.97 (bs, 1H), 5.12 (d, 1H, J=4.9 Hz), 4.07-3.92 (m, 1H), 3.61-3.51 (m, 2H), 3.38 (s, 3H), 3.00-2.87 (m, 4H), 2.81-2.65 (m, 6H), 2.17-2.05 (m, 2H), 1.89-1.76 (m, 2H), 1.53-1.47 (m, 2H), 1.47-1.20 (m, 4H).

Example 1378 trans-N-(4-{5-Chloro-2-[3-(2-methoxy-ethyl)-2,3,4,5-tetrahydro-1H-benzo[d]azepin-7-ylamino]-pyrimidin-4-ylamino}-cyclohexyl)-methanesulfonamide 1378a) trans-N-[4-(2,5-Dichloro-pyrimidin-4-ylamino)-cyclohexyl]-methanesulfonamide was prepared from trans-cyclohexane-1,4-diamine in an analogous manner to Example 304a. Product isolated as a white solid (1.12 g, 28%). m.p.=193-194° C.; LCMS (m/e) 339 (M+H); $^1$H-NMR (CDCl$_3$, 400 MHz) δ 8.04 (s, 1H), 5.27 (d, 1H, J=7.6 Hz), 4.19 (d, 1H, J=7.6 Hz), 4.07-3.96 (m, 1H), 3.45-3.33 (m, 1H), 3.03 (s, 3H), 2.25-2.13 (m, 4H), 1.55-1.35 (m, 3H).

1378b) trans-N-(4-{5-Chloro-2-[3-(2-methoxy-ethyl)-2,3,4,5-tetrahydro-1H-benzo[d]azepin-7-ylamino]-pyrimidin-4-ylamino}-cyclohexyl)-methanesulfonamide was prepared from 3-(2-methoxy-ethyl)-2,3,4,5-tetrahydro-1H-benzo[d]azepin-7-ylamine and trans-N-[4-(2,5-dichloro-pyrimidin-4-ylamino)-cyclohexyl]-methanesulfonamide in an analogous manner to Example 308c. Product isolated as a white solid (96 mg, 53%). m.p.=189-192° C.; LCMS (m/e) 523 (M+H); $^1$H-NMR (CDCl$_3$, 400 MHz) δ 7.90 (s, 1H), 7.33 (d, 1H, J=7.5 Hz), 7.03 (d, 1H, J=8.0 Hz), 6.80 (s, 1H), 5.03 (d, 1H, J=7.2 Hz), 4.29 (d, 1H, J=7.5 Hz), 4.02-3.90 (m, 1H), 3.57 (t, 2H, J=5.5 Hz), 3.45-3.32 (m, 1H), 3.38 (s, 3H), 3.03 (s, 3H), 2.98-2.88 (m, 4H), 2.83-2.69 (m, 6H), 2.28-2.16 (m, 4H), 1.53-1.32 (m, 4H).

Example 1379 rel-N-((1R,3R)-3-{5-Chloro-2-[3-(2-methoxy-ethyl)-2,3,4,5-tetrahydro-1H-benzo[d]azepin-7-ylamino]-pyrimidin-4-ylamino}-cyclohexyl)-methanesulfonamide 1379a) rel-N-[(1R,3R)-3-(2,5-Dichloro-pyrimidin-4-ylamino)-cyclohexyl]-methanesulfonamide was prepared from cyclohexane-1,3-diamine in an analogous manner to Example 304a. Product isolated as a white solid (1.20 g, 13%). m.p.=190-194° C.; LCMS (m/e) 339 (M+H); $^1$H-NMR (CDCl$_3$, 400 MHz) δ 8.06 (s, 1H), 5.36 (d, 1H, Exchangeable, J=7.0 Hz), 4.44 (d, 1H, Exchangeable, J=5.2 Hz), 4.40-4.27 (m, 1H), 3.94-3.85 (m, 1H), 3.14 (s, 3H), 2.20-2.11 (m, 1H), 2.05-1.95 (m, 1H), 1.85-1.65 (m, 5H), 1.57-1.43 (m, 1H). Also obtained in this reaction, rel-N-[(1S,3R)-3-(2,5-dichloro-pyrimidin-4-ylamino)-cyclohexyl]-methanesulfonamide as a white solid (2.92 g, 31%). m.p.=165-168° C.; LCMS (m/e) 339 (M+H); $^1$H-NMR (CDCl$_3$, 400 MHz) δ 8.05 (s, 1H), 5.34 (d, 1H, Exchangeable, J=7.6 Hz), 4.32 (d, 1H, Exchangeable, J=7.6 Hz), 4.20-4.08 (m, 1H), 3.55-3.42 (m, 1H), 3.02 (s, 3H), 2.55-2.46 (m, 1H), 2.20-2.05 (m, 2H), 1.97-1.88 (m, 1H), 1.59-1.48 (m, 1H), 1.32-1.15 (m, 3H).

1379b) rel-N-((1R,3R)-3-{5-Chloro-2-[3-(2-methoxy-ethyl)-2,3,4,5-tetrahydro-1H-benzo[d]azepin-7-ylamino]-pyrimidin-4-ylamino}-cyclohexyl)-methanesulfonamide was prepared from 3-(2-methoxy-ethyl)-2,3,4,5-tetrahydro-1H-benzo[d]azepin-7-ylamine and rel-N-[(1R,3R)-3-(2,5-dichloro-pyrimidin-4-ylamino)-cyclohexyl]-methanesulfonamide in an analogous manner to Example 308c.

Product isolated as a white foam (113 mg, 63%). LCMS (m/e) 523 (M+H); $^1$H-NMR (CDCl$_3$, 400 MHz) δ 7.92 (s, 1H), 7.37 (d, 1H, J=8.1 Hz), 7.23 (s, 1H), 7.07 (d, 1H, J=8.1 Hz), 6.85 (s, 1H), 5.11 (d, 1H, J=7.4 Hz), 4.37 (d, 1H, J=6.7 Hz), 4.36-4.26 (m, 1H), 3.84-3.75 (m, 1H), 3.56 (t, 2H, J=5.7 Hz), 3.39 (s, 3H), 2.98-2.87 (m, 4H), 2.93 (s, 3H), 2.81-2.68 (m, 6H), 2.04-1.91 (m, 2H), 1.91-1.79 (m, 2H), 1.79-1.65 (m, 3H), 1.58-1.47 (m, 1H).

Example 1380 rel-N-((1S,3R)-3-{5-Chloro-2-[3-(2-methoxy-ethyl)-2,3,4,5-tetrahydro-1H-benzo[d]azepin-7-ylamino]-pyrimidin-4-ylamino}-cyclohexyl)-methanesulfonamide rel-N-((1S,3R)-3-{5-Chloro-2-[3-(2-methoxy-ethyl)-2,3,4,5-tetrahydro-1H-benzo[d]azepin-7-ylamino]-pyrimidin-4-ylamino}-cyclohexyl)-methanesulfonamide was prepared from 3-(2-methoxy-ethyl)-2,3,4,5-tetrahydro-1H-benzo[d]azepin-7-ylamine and rel-N-[(1S,3R)-3-(2,5-dichloro-pyrimidin-4-ylamino)-cyclohexyl]-methanesulfonamide in an analogous manner to Example 308c. Product isolated as a white foam (76 mg, 42%). LCMS (m/e) 523 (M+H); $^1$H-NMR (CDCl$_3$, 400 MHz) δ 7.91 (s, 1H), 7.42 (d, 1H, J=8.1 Hz), 7.20 (s, 1H), 7.07 (d, 1H, J=8.1 Hz), 6.82 (s, 1H), 5.07 (d, 1H, J=7.6 Hz), 4.18 (d, 1H, J=7.8 Hz), 4.14-4.02 (m, 1H), 3.56 (t, 2H, J=5.7 Hz), 3.53-3.42 (m, 1H), 3.39 (s, 3H), 2.99-2.88 (m, 4H), 2.95 (s, 3H), 2.81-2.67 (m, 6H), 2.58-2.48 (m, 1H), 2.21-2.11 (m, 2H), 2.00-1.89 (m, 1H), 1.56-1.43 (m, 1H), 1.31-1.11 (m, 3H).

Example 1381 cis-N-(4-{5-Chloro-2-[3-(2-methoxy-ethyl)-2,3,4,5-tetrahydro-1H-benzo[d]azepin-7-ylamino]-pyrimidin-4-ylamino}-cyclohexyl)-methanesulfonamide 1381a) cis-N-[4-(2,5-Dichloro-pyrimidin-4-ylamino)-cyclohexyl]-methanesulfonamide was prepared from cis-cyclohexane-1,4-diamine in an analogous manner to Example 304a. Product isolated as a white solid (1.79 g, 45%). m.p.=205-210° C.; LCMS (m/e) 339 (M+H); $^1$H-NMR (CDCl$_3$, 400 MHz) δ 8.06 (s, 1H), 5.45 (d, 1H, J=7.6 Hz), 4.44 (d, 1H, J=6.5 Hz), 4.25-4.14 (m, 1H), 3.70-3.60 (m, 1H), 3.03 (s, 3H), 2.00-1.87 (m, 4H), 1.85-1.66 (m, 4H).

1381b) cis-N-(4-{5-Chloro-2-[3-(2-methoxy-ethyl)-2,3,4,5-tetrahydro-1H-benzo[d]azepin-7-ylamino]-pyrimidin-4-ylamino}-cyclohexyl)-methanesulfonamide was prepared from 3-(2-methoxy-ethyl)-2,3,4,5-tetrahydro-1H-benzo[d]azepin-7-ylamine and cis-N-[4-(2,5-dichloro-pyrimidin-4-ylamino)-cyclohexyl]-methanesulfonamide in an analogous manner to Example 308c. Product isolated as a white foam (99 mg, 55%). LCMS (m/e) 523 (M+H); $^1$H-NMR (CDCl$_3$, 400 MHz) δ 7.91 (s, 1H), 7.36-7.23 (m, 2H), 7.02 (d, 1H, J=8.1 Hz), 6.78 (s, 1H), 5.18 (d, 1H, J=7.0 Hz), 4.36-4.30 (m, 1H), 4.18-4.08 (m, 1H), 3.70-3.61 (m, 1H), 3.56 (t, 2H, J=5.6 Hz), 3.39 (s, 3H), 3.03 (s, 3H), 2.96-2.88 (m, 4H), 2.80-2.69 (m, 6H), 2.01-1.84 (m, 4H), 1.84-1.70 (m, 4H).

Example 1382 rel-N-((1R,3R)-3-{5-Chloro-2-[3-(2-methoxy-ethyl)-2,3,4,5-tetrahydro-1H-benzo[d]azepin-7-ylamino]-pyrimidin-4-ylamino}-cyclohexyl)-N-cyanomethyl-methanesulfonamide 1382a) rel-N-[(1R,3R)-3-(2,5-Dichloro-pyrimidin-4-ylamino)-cyclohexyl]-methanesulfonamide (400 mg, 1.18 mmol) was dissolved in acetone (15.0 mL, 204 mmol) and cesium carbonate (576 mg, 1.77 mmol) was added. After 15 min, bromoacetonitrile (130 uL, 1.86 mmol) was added and the mixture stirred at room temperature for 4 days. LCMS analysis showed that the reaction had only gone to 50% completion. A second aliquot of bromoacetonitrile (90.4 uL, 1.30 mmol) was added and the reaction was heated at 45° C. overnight. The reaction was then concentrated under reduced pressure and the residue was taken up in DCM (30 mL) and washed with water (30 mL). The organic layer was dried over sodium sulfate, filtered, and concentrated under reduced pressure. Purification by silica gel chromatography using a gradient of 0-100% EtOAc/hex as the eluting solvent to obtain rel-N-cyanomethyl-N-[(1R,3R)-3-(2,5-dichloro-pyrimidin-4-ylamino)-cyclohexyl]-methanesulfonamide as a white foam (261 mg, 58%). LCMS (m/e) 378 (M+H); $^1$H-NMR (CDCl$_3$, 400 MHz) δ 8.05 (s, 1H), 5.32 (d, 1H, J=7.3 Hz), 4.34-4.07 (m, 3H), 3.97-3.85 (m, 1H), 3.08 (s, 1H), 2.49-2.39 (m, 1H), 2.17-2.08 (m, 1H), 2.03-1.94 (m, 2H), 1.62-1.45 (m, 3H), 1.30-1.15 (m, 1H).

1382b) rel-N-((1R,3R)-3-{5-Chloro-2-[3-(2-methoxy-ethyl)-2,3,4,5-tetrahydro-1H-benzo[d]azepin-7-ylamino]-pyrimidin-4-ylamino}-cyclohexyl)-N-cyanomethyl-methanesulfonamide was prepared from 3-(2-methoxy-ethyl)-2,3,4,5-tetrahydro-1H-benzo[d]azepin-7-ylamine and rel-N-cyanomethyl-N-[(1R,3R)-3-(2,5-dichloro-pyrimidin-4-ylamino)-cyclohexyl]-methanesulfonamide in an analogous manner to Example 308c. Product isolated as a white foam (113 mg, 58%). LCMS (m/e) 562 (M+H); $^1$H-NMR (CDCl$_3$, 400 MHz) δ 7.93 (s, 1H), 7.42 (d, 1H, J=8.5 Hz), 7.16 (s, 1H), 7.09 (d, 1H, J=8.5 Hz), 6.81 (s, 1H), 5.10 (d, 1H, J=6.6 Hz), 4.30-4.05 (m, 3H), 3.99-3.84 (m, 1H), 3.56 (t, 2H, J=5.8 Hz), 3.52-3.47 (m, 1H), 3.38 (s, 3H), 3.02-2.85 (m, 4H), 2.93 (s, 3H), 2.81-2.66 (m, 6H), 2.48-2.38 (m, 1H), 2.21-2.11 (m, 1H), 2.07-1.96 (m, 2H), 1.60-1.45 (m, 2H), 1.30-1.19 (m, 1H).

Example 1383

N-((1R,2R)-2-{5-Chloro-2-[3-(2-methoxy-ethyl)-2,3,4,5-tetrahydro-1H-benzo[d]azepin-7-ylamino]-pyrimidin-4-ylamino}-cyclohexyl)-N-cyanomethyl-methanesulfonamide 1383a) N-Cyanomethyl-N-[(1R,2R)-2-(2,5-dichloro-pyrimidin-4-ylamino)-cyclohexyl]-methanesulfonamide was prepared from N-[(1R,2R)-2-(2,5-dichloro-pyrimidin-4-ylamino)-cyclohexyl]-methanesulfonamide in an analogous manner to Example 1382a. Product isolated as a white foam (445 mg, 100%). LCMS (m/e) 378 (M+H); $^1$H-NMR (CDCl$_3$, 400 MHz) δ 8.05 (s, 1H), 5.67 (d, 1H, J=8.6 Hz), 4.40-4.02 (m, 3H), 3.78-3.68 (m, 1H), 3.05 (s, 3H), 2.33-2.23 (m, 1H), 2.23-2.16 (m, 1H), 2.04-1.97 (m, 1H), 1.94-1.71 (m, 2H), 1.50-1.36 (m, 2H), 1.32-1.25 (m, 1H).

1383b) N-((1R,2R)-2-{5-Chloro-2-[3-(2-methoxy-ethyl)-2,3,4,5-tetrahydro-1H-benzo[d]azepin-7-ylamino]-pyrimidin-4-ylamino}-cyclohexyl)-N-cyanomethyl-methanesulfonamide was prepared from 3-(2-methoxy-ethyl)-2,3,4,5-tetrahydro-1H-benzo[d]azepin-7-ylamine and N-cyanomethyl-N-[(1R,2R)-2-(2,5-dichloro-pyrimidin-4-ylamino)-cyclohexyl]-methanesulfonamide in an analogous manner to Example 308c. Product isolated as a pale yellow foam (63 mg, 32%). LCMS (m/e) 562 (M+H); $^1$H-NMR (CDCl$_3$, 400 MHz) δ 7.89 (s, 1H), 7.30-7.19 (m, 2H), 7.07 (d, 1H, J=7.9 Hz), 5.39 (d, 1H, J=8.7 Hz), 4.12-3.63 (m, 4H), 3.56 (t, 2H, J=5.6 Hz), 3.38 (s, 3H), 3.01-2.91 (m, 4H), 2.97

(s, 3H), 2.84-2.68 (m, 6H), 2.36-2.26 (m, 1H), 2.18-2.09 (m, 1H), 2.02-184 (m, 2H), 1.72-1.57 (m, 1H), 1.50-1.30 (m, 3H).

Example 1384 cis-N-(4-{5-Chloro-2-[3-(2-methoxy-ethyl)-2,3,4,5-tetrahydro-1H-benzo[d]azepin-7-ylamino]-pyrimidin-4-ylamino}-cyclohexyl)-N-cyanomethyl-methanesulfonamide 1384a) cis-N-Cyanomethyl-N-[4-(2,5-dichloro-pyrimidin-4-ylamino)-cyclohexyl]-methanesulfonamide was prepared from cis-N-[4-(2,5-dichloro-pyrimidin-4-ylamino)-cyclohexyl]-methanesulfonamide in an analogous manner to Example 1382a. Product isolated as a white foam (68 mg, 15%). LCMS (m/e) 378 (M+H); $^1$H-NMR (CDCl$_3$, 400 MHz) δ 8.09 (s, 1H), 5.54 (d, 1H, J=5.8 Hz), 4.41-4.32 (m, 1H), 4.25 (s, 2H), 3.90-3.78 (m, 1H), 3.09 (s, 3H), 2.26-2.17 (m, 2H), 2.00-1.88 (m, 2H), 1.86-1.75 (m, 4H).

1384b) cis-N-(4-{5-Chloro-2-[3-(2-methoxy-ethyl)-2,3,4,5-tetrahydro-1H-benzo[d]azepin-7-ylamino]-pyrimidin-4-ylamino}-cyclohexyl)-N-cyanomethyl-methanesulfonamide was prepared from 3-(2-methoxy-ethyl)-2,3,4,5-tetrahydro-1H-benzo[d]azepin-7-ylamine and cis-N-cyanomethyl-N-[4-(2,5-dichloro-pyrimidin-4-ylamino)-cyclohexyl]-methanesulfonamide in an analogous manner to Example 308c. Product isolated as a pale yellow foam (52 mg, 54%). LCMS (m/e) 562 (M+H); $^1$H-NMR (CDCl$_3$, 400 MHz) δ 7.94 (s, 1H), 7.33 (s, 1H), 7.28 (d, 1H, J=8.0 Hz), 7.02 (d, 1H, J=8.0 Hz), 6.95 (s, 1H), 5.25 (d, 1H, J=6.0 Hz), 4.33-4.27 (m, 1H), 4.25 (s, 2H), 3.91-3.79 (m, 1H), 3.56 (t, 2H, J=5.6 Hz), 3.39 (s, 3H), 3.09 (s, 3H), 2.95-2.86 (m, 4H), 2.80-2.67 (m, 6H), 2.29-2.20 (m, 2H), 1.97-1.73 (m, 6H).

Example 1385 trans-N-(4-{5-Chloro-2-[3-(2-methoxy-ethyl)-2,3,4,5-tetrahydro-1H-benzo[d]azepin-7-ylamino]-pyrimidin-4-ylamino}-cyclohexyl)-N-cyanomethyl-methanesulfonamide 1385a) trans-N-Cyanomethyl-N-[4-(2,5-dichloro-pyrimidin-4-ylamino)-cyclohexyl]-methanesulfonamide was prepared from trans-N-[4-(2,5-dichloro-pyrimidin-4-ylamino)-cyclohexyl]-methanesulfonamide in an analogous manner to Example 1382a. Product isolated as a white solid (108 mg, 24%). m.p.=220-222° C.; LCMS (m/e) 378 (M+H); $^1$H-NMR (CDCl$_3$, 400 MHz) δ 8.06 (s, 1H), 5.27 (d, 1H, J=7.6 Hz), 4.23 (s, 2H), 4.10-3.96 (m, 1H), 3.92-3.81 (m, 1H), 3.09 (s, 3H), 2.35-2.25 (m, 2H), 2.12-2.01 (m, 2H), 1.90-1.77 (m, 2H), 1.54-1.38 (m, 2H).

1385b) trans-N-(4-{5-Chloro-2-[3-(2-methoxy-ethyl)-2,3,4,5-tetrahydro-1H-benzo[d]azepin-7-ylamino]-pyrimidin-4-ylamino}-cyclohexyl)-N-cyanomethyl-methanesulfonamide was prepared from 3-(2-methoxy-ethyl)-2,3,4,5-tetrahydro-1H-benzo[d]azepin-7-ylamine and trans-N-cyanomethyl-N-[4-(2,5-dichloro-pyrimidin-4-ylamino)-cyclohexyl]-methanesulfonamide in an analogous manner to Example 308c. Product isolated as a white solid (60 mg, 40%). m.p.=159-162° C.; LCMS (m/e) 562 (M+H); $^1$H-NMR (CDCl$_3$, 400 MHz) δ 7.92 (s, 1H), 7.37 (d, 1H, J=8.0 Hz), 7.25 (s, 1H), 7.06 (d, 1H, J=8.0 Hz), 6.81 (s, 1H), 5.03 (d, 1H, J=7.2 Hz), 4.24 (s, 2H), 4.0-3.81 (m, 2H), 3.56 (t, 2H, J=5.7 Hz), 3.38 (s, 3H), 3.09 (s, 3H), 2.97-2.88 (m, 4H), 2.82-2.67 (m, 6H), 2.40-2.29 (m, 2H), 2.13-2.03 (m, 2H), 1.87-1.72 (m, 2H), 1.54-1.38 (m, 2H).

Example 1386 rel-N-((1S,3R)-3-{5-Chloro-2-[3-(2-methoxy-ethyl)-2,3,4,5-tetrahydro-1H-benzo[d]azepin-7-ylamino]-pyrimidin-4-ylamino}-cyclohexyl)-N-cyanomethyl-methanesulfonamide 1386a) rel-N-Cyanomethyl-N-[(1S,3R)-3-(2,5-dichloro-pyrimidin-4-ylamino)-cyclohexyl]-methanesulfonamide was prepared from rel-N-[(1S,3R)-3-(2,5-dichloro-pyrimidin-4-ylamino)-cyclohexyl]-methanesulfonamide in an analogous manner to Example 1382a. Product isolated as a white foam (171 mg, 38%). LCMS (m/e) 378 (M+H); $^1$H-NMR (CDCl$_3$, 400 MHz) δ 8.06 (s, 1H), 5.38 (d, 1H, J=7.6 Hz), 4.34-4.09 (m, 3H), 4.00-3.87 (m, 1H), 3.09 (s, 3H), 2.49-2.40 (m, 1H), 2.16-2.08 (m, 1H), 2.08-1.96 (m, 2H), 1.63-1.47 (m, 3H), 1.31-1.17 (m, 1H).

1386b) rel-N-((1S,3R)-3-{5-Chloro-2-[3-(2-methoxy-ethyl)-2,3,4,5-tetrahydro-1H-benzo[d]azepin-7-ylamino]-pyrimidin-4-ylamino}-cyclohexyl)-N-cyanomethyl-methanesulfonamide was prepared from 3-(2-methoxy-ethyl)-2,3,4,5-tetrahydro-1H-benzo[d]azepin-7-ylamine and rel-N-cyanomethyl-N-[(1S,3R)-3-(2,5-dichloro-pyrimidin-4-ylamino)-cyclohexyl]-methanesulfonamide in an analogous manner to Example 308c. Product isolated as a tan foam (28 mg, 13%). LCMS (m/e) 562 (M+H); $^1$H-NMR (CDCl$_3$, 400 MHz) δ 7.92 (s, 1H), 7.42 (d, 1H, J=8.0 Hz); 7.16 (s, 1H), 7.09 (d, 1H, J=8.1 Hz), 6.88 (s, 1H), 5.11 (d, 1H, J=7.2 Hz), 4.30-4.05 (m, 3H), 3.95-3.84 (m, 1H), 3.56 (t, 2H, J=5.8 Hz), 3.38 (s, 3H), 3.05-2.85 (m, 4H), 2.93 (s, 3H), 2.82-2.65 (m, 6H), 2.48-2.39 (m, 1H), 2.22-2.12 (m, 1H), 2.11-1.93 (m, 2H), 1.60-1.42 (m, 3H), 1.34-1.16 (m, 1H).

Example 1387

2-{5-Chloro-2-[3-(2-methoxy-ethyl)-2,3,4,5-tetrahydro-1H-benzo[d]azepin-7-ylamino]-pyrimidin-4-ylamino}-N-prop-2-ynyl-benzamide 1387a) Isatoic Anhydride (4.00 g, 24.5 mmol) was dissolved in tetrahydrofuran (100 mL, 1.230 mol) at 0° C. Prop-2-ynylamine (2.52 mL, 36.8 mmol) was added and the reaction was stirred for 2 hours and then concentrated under reduced pressure. Purification by silica gel chromatography using a gradient of 0-50% EtOAc/hex as the eluting solvent to obtain 2-amino-N-prop-2-ynyl-benzamide as a white solid (4.27 g, 100%). m.p.=75° C.; LCMS (m/e) 120 (M—NHCH2CCH); $^1$H-NMR (CDCl$_3$, 400 MHz) δ 7.35 (d, 1H, J=7.9 Hz), 7.24 (dd, 1H, J=7.3 and 8.2 Hz), 6.73-6.64 (m, 2H), 6.19 (bs, 1H), 5.56 (bs, 2H), 4.26-4.20 (m, 2H), 2.29 (t, 1H, J=1.5 Hz).

1387b) 2-Amino-N-prop-2-ynyl-benzamide (4.20 g, 24.1 mmol) was dissolved in N,N-dimethylformamide (100 mL, 1.290 mol) and potassium carbonate (5.00 g, 36.2 mmol) was added. 2,4,5-Trichloro-pyrimidine (3.32 mL, 28.9 mmol) was added and the reaction was stirred for 48 hours. The reaction was concentrated under reduced pressure and the residue was taken up in DCM (300 mL) and washed with water (300 mL). The organic layer was dried over sodium sulfate, filtered, and concentrated under reduced pressure. Purification by silica gel chromatography using a gradient of 0-50% EtOAc/hex as the eluting solvent to obtain 2-(2,5-dichloro-pyrimidin-4-ylamino)-N-prop-2-ynyl-benzamide as a pale yellow solid (298 mg, 4%). m.p.=188-191° C.; LCMS (m/e) 321 (M+H); $^1$H-NMR (CDCl$_3$, 400 MHz) δ 11.53 (s, 1H), 8.76 (d, 1H, J=8.5 Hz), 8.25 (s, 1H), 7.66-7.53 (m, 2H), 7.23-7.14 (m, 1H), 6.39 (bs, 1H), 4.34-4.25 (m, 2H), 2.34 (t, 1H, J=2.5 Hz). 1387c) 2-{5-Chloro-2-[3-(2-methoxy-ethyl)-2,3,4,5-tetrahydro-1H-benzo[d]azepin-7-ylamino]-pyrimidin-4-ylamino}-N-prop-2-ynyl-benzamide was prepared from 3-(2-methoxy-ethyl)-2,3,4,5-tetrahydro-1H-benzo[d]azepin-7-ylamine and 2-(2,5-dichloro-pyrimidin-4-ylamino)-N-prop-2-ynyl-benzamide in an analogous manner to Example 308c. Product isolated as a white solid (59 mg, 34%). m.p.=165-167° C.; LCMS (m/e) 505 M+H); $^1$H-NMR (CDCl$_3$, 400 MHz) δ 10.91 (s, 1H), 8.69 (d, 1H, J=8.9 Hz), 8.11 (s, 1H), 7.55 (d, 1H, J=7.5 Hz), 7.50-7.43 (m, 1H), 7.35 (s, 1H), 7.28-7.22 (m, 1H), 7.16-7.08 (m, 1H), 7.04 (d, 1H, J=8.8 Hz), 6.87 (s, 1H), 6.32 (bs, 1H), 4.32-4.26 (m, 2H), 3.56 (t, 2H, J=5.7 Hz), 3.39 (s, 3H), 2.97-2.87 (m, 4H), 2.80-2.69 (m, 6H), 2.35-2.31 (m, 1H).

Example 1388

2-[5-Chloro-2-(1-methyl-2-oxo-2,3,4,5-tetrahydro-1H-benzo[b]azepin-7-ylamino)-pyrimidin-4-ylamino]-N-prop-2-ynyl-benzamide 2-[5-Chloro-2-(1-methyl-2-oxo-2,3,4,5-tetrahydro-1H-benzo[b]azepin-7-ylamino)-pyrimidin-4-ylamino]-N-prop-2-ynyl-benzamide was prepared from 7-amino-1-methyl-1,3,4,5-tetrahydro-1-benzazepin-2-one and 2-(2,5-dichloro-pyrimidin-4-ylamino)-N-prop-2-ynyl-benzamide in an analogous manner to Example 308c. Product isolated as a white solid (79 mg, 48%). m.p.=193-194° C.; LCMS (m/e) 475 (M+H); $^1$H-NMR (CDCl$_3$, 400 MHz) δ 10.97 (s, 1H), 8.66 (d, 1H, J=8.4 Hz), 8.14 (s, 1H), 7.57 (d, 1H, J=7.8 Hz), 7.54-7.42 (m, 3H), 7.19-7.09 (m, 2H), 6.95 (s, 1H), 6.34 (bs, 1H), 4.33-4.27 (m, 2H), 3.36 (s, 3H), 2.74-2.64 (m, 2H), 2.38-2.30 (m, 3H), 2.22-2.12 (m, 2H).

Example 1389

{5-Chloro-2-[3-(2-methoxy-ethyl)-2,3,4,5-tetrahydro-1H-benzo[d]azepin-7-ylamino]-pyrimidin-4-yl amino}-N-methyl-N-prop-2-ynyl-benzamide 1389a) 2-Amino-N-methyl-N-prop-2-ynyl-benzamide was prepared from isatoic anhydride and 2-propyn-1-amine, N-methyl- in an analogous manner to Example 1387a. Product isolated as a yellow amorphous solid (4.62 g, 100%). LCMS (m/e) 189 (M+H); $^1$H-NMR (CDCl$_3$, 400 MHz) δ 7.25-7.15 (m, 2H), 6.77-6.70 (m, 2H), 4.40 (s, 2H), 4.23 (bs, 2H), 3.13 (s, 3H), 2.35-2.30 (m, 1H).
1389b) 2-(2,5-dichloro-pyrimidin-4-ylamino)-N-methyl-N-prop-2-ynyl-benzamide was prepared from 2-amino-N-methyl-N-prop-2-ynyl-benzamide and 2,4,5-trichloro-pyrimidine in an analogous manner to Example 1387b. Product isolated as a yellow foam (958 mg, 12%). LCMS (m/e) 335 (M+H); $^1$H-NMR (CDCl$_3$, 400 MHz) δ 9.45 (s, 1H), 8.35 (d, 1H, J=8.3 Hz), 8.22 (s, 1H), 7.63-7.30 (m, 2H), 7.25-7.17 (m, 1H), 4.53-4.01 (m, 2H), 3.19 (s, 3H), 2.46-2.24 (m, 1H).
1389c) 2-{5-Chloro-2-[3-(2-methoxy-ethyl)-2,3,4,5-tetrahydro-1H-benzo[d]azepin-7-ylamino]-pyrimidin-4-ylamino}-N-methyl-N-prop-2-ynyl-benzamide was prepared from 3-(2-methoxy-ethyl)-2,3,4,5-tetrahydro-1H-benzo[d]azepin-7-ylamine and 2-(2,5-dichloro-pyrimidin-4-ylamino)-N-methyl-N-prop-2-ynyl-benzamide in an analogous manner to Example 308c. Product isolated as a yellow foam (40 mg, 22%). LCMS (m/e) 519 (M+H); $^1$H-NMR (CDCl$_3$, 400 MHz) δ 8.94 (bs, 1H), 8.38 (d, 1H, J=8.3 Hz), 8.08 (s, 1H), 7.60-7.37 (m, 2H), 7.33 (s, 1H), 7.24 (d, 1H, J=8.1 Hz), 7.21-7.12 (m, 1H), 7.02 (d, 1H, J=8.1 Hz), 6.90 (s, 1H), 4.50-4.00 (m, 2H), 3.56 (t, 2H, J=5.7 Hz), 3.39 (s, 3H), 3.17 (bs, 3H), 2.95-2.84 (m, 4H), 2.79-2.68 (m, 6H), 2.40-2.28 (m, 1H).

Example 1390

[5-Chloro-2-(1-methyl-2-oxo-2,3,4,5-tetrahydro-1H-benzo[b]azepin-7-ylamino)-pyrimidin-4-ylamino]-N-methyl-N-prop-2-ynyl-benzamide 2-[5-Chloro-2-(1-methyl-2-oxo-2,3,4,5-tetrahydro-1H-benzo[b]azepin-7-ylamino)-pyrimidin-4-ylamino]-N-methyl-N-prop-2-ynyl-benzamide was prepared from 7-amino-1-methyl-1,3,4,5-tetrahydro-1-benzazepin-2-one and 2-(2,5-dichloro-pyrimidin-4-ylamino)-N-methyl-N-prop-2-ynyl-benzamide in an analogous manner to Example 308c. Product isolated as a yellow thin film (19 mg, 15%). LCMS (m/e) 489 (M+H); $^1$H-NMR (CDCl$_3$, 400 MHz) δ 8.99 (bs, 1H), 8.35 (d, 1H, J=8.2 Hz), 8.11 (s, 1H), 7.61-7.32 (m, 4H), 7.23-7.15 (m, 1H), 7.09 (d, 1H, J=8.2 Hz), 6.97 (s, 1H), 4.51-3.99 (m, 2H), 3.35 (s, 3H), 3.18 (bs, 3H), 2.72-2.61 (m, 2H), 2.42-2.29 (m, 3H), 2.23-2.10 (m, 2H).

Example 1391

Chloro-N(2)-[3-(2-fluoro-1-fluoromethyl-ethyl)-8-methoxy-2,3,4,5-tetrahydro-1H-benzo[d]azepin-7-yl]-N(4)-(2-methoxy-4-morpholin-4-yl-phenyl)-pyrimidine-2,4-diamine 1391a) A mixture of 1,3-difluoro-propan-2-ol (0.697 mL, 9.00 mmol) and pyridine (0.910 mL, 11.2 mmol) in acetonitrile (42.3 mL, 810 mmol) was cooled at 0° C. and trifluoromethanesulfonic anhydride (1.59 mL, 9.45 mmol) was added dropwise. The mixture was stirred for 30 minutes and then potassium carbonate (1.24 g, 9.00 mmol) and 7-methoxy-8-nitro-2,3,4,5-tetrahydro-1H-benzo[d]azepine (1.00 g, 4.50 mmol) were added. The reaction was heated at 50° C. overnight and then cooled to room temperature and concentrated under reduced pressure. The residue was taken up in DCM (75 mL) and washed with water (75 mL). The organic layer was dried over sodium sulfate, filtered, and concentrated under reduced pressure. Purification by silica gel chromatography using a gradient of 0-100% EtOAc/hex as the eluting solvent to obtain 3-(2-fluoro-1-fluoromethyl-ethyl)-7-methoxy-8-nitro-2,3,4,5-tetrahydro-1H-benzo[d]azepine as a yellow amorphous solid (679 mg, 50%). LCMS (m/e) 301 (M+H); $^1$H-NMR (CDCl$_3$, 400 MHz) δ 7.67 (s, 1H), 6.83 (s, 1H), 4.75-4.65 (m, 2H), 4.63-4.54 (m, 2H), 3.96 (s, 3H), 3.29-3.11 (m, 1H), 2.99-2.93 (m, 2H), 2.93-2.82 (m, 6H).
1391b) 3-(2-Fluoro-1-fluoromethyl-ethyl)-7-methoxy-8-nitro-2,3,4,5-tetrahydro-1H-benzo[d]azepine (670 mg, 2.23 mmol) was dissolved in methanol (40.0 mL, 987 mmol) and 10% Palladium on Carbon (50% Wet) (5:45:50, Palladium: carbon black:Water, 240 mg) was added. The reaction was hydrogenated at 35 psi. for 1 hour. The reaction was filtered through Celite and concentrated under reduced pressure to obtain 3-(2-fluoro-1-fluoromethyl-ethyl)-8-methoxy-2,3,4,5-tetrahydro-1H-benzo[d]azepin-7-ylamine as a green oil (603 mg, 100%). LCMS (m/e) 271 (M+H); $^1$H-NMR (CDCl$_3$, 400 MHz) δ 6.58 (s, 1H), 6.51 (s, 1H), 4.75-4.66 (m, 2H), 4.64-4.54 (m, 2H), 3.84 (s, 3H), 3.67 (bs, 2H), 3.27-3.09 (m, 1H), 2.90-2.75 (m, 8H).
1391c) 5-Chloro-N(2)-[3-(2-fluoro-1-fluoromethyl-ethyl)-8-methoxy-2,3,4,5-tetrahydro-1H-benzo[d]azepin-7-yl]-N(4)-(2-methoxy-4-morpholin-4-yl-phenyl)-pyrimidine-2,4-diamine was prepared from 3-(2-fluoro-1- fluoromethyl-ethyl)-8-methoxy-2,3,4,5-tetrahydro-1H-benzo[d]azepin-7-ylamine and (2,5-dichloro-pyrimidin-4-yl)-(2-methoxy-4-morpholin-4-yl-phenyl)-amine in an analogous manner to Example 308c. Product isolated as a white foam (60 mg, 30%). LCMS (m/e) 589 (M+H); ¹H-NMR (CDCl₃, 400 MHz) δ 8.29 (d, 1H, J=8.7 Hz), 8.14 (s, 1H), 8.04 (s, 1H), 7.57 (s, 1H), 7.45 (s, 1H), 6.66 (s, 1H), 6.57 (s, 1H), 5.52 (d, 1H, J=8.7 Hz), 4.75-4.67 (m, 2H), 4.63-4.56 (m, 2H), 3.94 (s, 3H), 3.93-3.89 (m, 4H), 3.88 (s, 3H), 3.2-3.10 (m, 5H), 2.93-2.79 (m, 8H).

Example 1392

((1R,2R)-2-{5-Chloro-2-[3-(2-fluoro-1-fluoromethyl-ethyl)-8-methoxy-2,3,4,5-tetrahydro-1H-benzo[d]azepin-7-ylamino]-pyrimidin-4-ylamino}-cyclohexyl)-methanesulfonamide N-((1R,2R)-2-{5-Chloro-2-[3-(2-fluoro-1-fluoromethyl-ethyl)-8-methoxy-2,3,4,5-tetrahydro-1H-benzo[d]azepin-7-ylamino]-pyrimidin-4-ylamino}-cyclohexyl)-methanesulfonamide was prepared from 3-(2-fluoro-1-fluoromethyl-ethyl)-8-methoxy-2,3,4,5-tetrahydro-1H-benzo[d]azepin-7-ylamine and N-[(1R,2R)-2-(2,5-dichloro-pyrimidin-4-ylamino)-cyclohexyl]-methanesulfonamide in an analogous manner to Example 308c. Product isolated as a white foam (140 mg, 66%). LCMS (m/e) 573 (M+H); ¹H-NMR (CDCl₃, 400 MHz) δ 7.99 (s, 1H), 7.96 (s, 1H), 7.32 (s, 1H), 6.67 (s, 1H), 5.34 (d, 1H, J=7.3 Hz), 5.24 (d, 1H, J=7.0 Hz), 4.77-4.64 (m, 2H), 4.64-4.52 (m, 2H), 4.03-3.93 (m, 1H), 3.89 (s, 3H), 3.31-3.10 (m, 2H), 2.97-2.82 (m, 8H), 2.80 (s, 3H), 2.31-2.16 (m, 2H), 1.92-1.78 (m, 2H), 1.50-1.32 (m, 4H).

Example 1393

{5-Chloro-2-[3-(2-fluoro-1-fluoromethyl-ethyl)-8-methoxy-2,3,4,5-tetrahydro-1H-benzo[d]azepin-7-ylamino]-pyrimidin-4-ylamino}-N,N-dimethyl-benzenesulfonamide 2-{5-Chloro-2-[3-(2-fluoro-1-fluoromethyl-ethyl)-8-methoxy-2,3,4,5-tetrahydro-1H-benzo[d]azepin-7-ylamino]-pyrimidin-4-ylamino}-N,N-dimethyl-benzenesulfonamide was prepared from 3-(2-fluoro-1-fluoromethyl-ethyl)-8-methoxy-2,3,4,5-tetrahydro-1H-benzo[d]azepin-7-ylamine and 2-(2,5-dichloro-pyrimidin-4-ylamino)-N,N-dimethyl-benzenesulfonamide in an analogous manner to Example 308c. Product isolated as a white foam (60 mg, 60%). LCMS (m/e) 581 (M+H); ¹H-NMR (CDCl₃, 400 MHz) δ 9.35 (s, 1H), 8.54 (d, 1H, J=8.3 Hz), 8.16 (s, 1H), 8.01 (s, 1H), 7.90 (d, 1H, J=8.0 Hz), 7.62-7.53 (m, 1H), 7.51 (s, 1H), 7.28-7.21 (m, 1H), 6.67 (s, 1H), 4.75-4.67 (m, 2H), 4.64-4.57 (m, 2H), 3.89 (s, 3H), 2.91-2.81 (m, 6H), 2.76 (s, 6H), 2.75-2.70 (m, 2H).

Example 1394

Chloro-N(2)-[3-(2-fluoro-1-fluoromethyl-ethyl)-8-methoxy-2,3,4,5-tetrahydro-1H-benzo[d]azepin-7-yl]-N(4)-[2-(propane-2-sulfonyl)-phenyl]-pyrimidine-2,4-diamine 5-Chloro-N(2)-[3-(2-fluoro-1-fluoromethyl-ethyl)-8-methoxy-2,3,4,5-tetrahydro-1H-benzo[d]azepin-7-yl]-N(4)-[2-(propane-2-sulfonyl)-phenyl]-pyrimidine-2,4-diamine was prepared from 3-(2-fluoro-1-fluoromethyl-ethyl)-8-methoxy-2,3,4,5-tetrahydro-1H-benzo[d]azepin-7-ylamine and (2,5-dichloro-pyrimidin-4-yl)-[2-(propane-2-sulfonyl)-phenyl]-amine in an analogous manner to Example 308c. Product isolated as a white foam (95 mg 44%). LCMS (m/e) 580 (M+H); ¹H-NMR (CDCl₃, 400 MHz) δ 9.52 (s, 1H), 8.57 (d, 1H, J=8.4 Hz), 8.17 (s, 1H), 8.00 (s, 1H), 7.94 (d, 1H, J=7.9 Hz), 7.67-7.58 (m, 1H), 7.50 (s, 1H), 7.32-7.24 (m, 1H), 6.67 (s, 1H), 4.76-4.66 (m, 2H), 4.65-4.55 (m, 2H), 3.89 (s, 3H), 3.33-3.10 (m, 2H), 2.91-2.79 (m, 6H), 2.79-2.69 (m, 2H), 1.35 (s, 3H), 1.33 (s, 3H).

Example 1395

{5-Chloro-2-[3-(2-methoxy-ethyl)-2,3,4,5-tetrahydro-1H-benzo[d]azepin-7-ylamino]-pyrimidin-4-ylamino}-benzoic acid ethyl ester 1395a) 2-(2,5-Dichloro-pyrimidin-4-ylamino)-benzoic acid ethyl ester was prepared from 2-amino-benzoic acid ethyl ester and 2,4,5-trichloro-pyrimidine in an analogous manner to Example 308b. Product isolated as a white solid (2.28 g, 27%). m.p.=156-157° C.; LCMS (m/e) 312 (M+H); ¹H-NMR (CDCl₃, 400 MHz) δ 11.68 (bs, 1H), 8.91 (d, 1H, J=8.6 Hz), 8.28 (s, 1H), 8.14 (d, 1H, J=8.0 Hz), 7.70-7.62 (m, 1H), 7.22-7.13 (m, 1H), 4.45 (q, 2H, J=7.1 Hz), 1.46 (t, 3H, J=7.1 Hz).

1395b) 3-(2-Methoxy-ethyl)-2,3,4,5-tetrahydro-1H-benzo[d]azepin-7-ylamine (1.00 g, 4.54 mmol) and 2-(2,5-dichloro-pyrimidin-4-ylamino)-benzoic acid ethyl ester (1.29 g, 4.13 mmol) were dissolved in ethanol (40.00 mL, 685 mmol) and 10-camphorsulfonic acid (1.15 g, 4.95 mmol) was added. The reaction was microwaved on 300 watts, 120° C. for 40 minutes and then concentrated under reduced pressure. The residue was taken up in DCM (100 mL) and washed with sat. NaHCO₃ (100 mL). The organic layer was dried over sodium sulfate, filtered, and concentrated under reduced pressure. Purification by amine capped silica gel chromatography using a gradient of 0-40% EtOAc/hex as the eluting solvent to obtain 2-{5-chloro-2-[3-(2-methoxy-ethyl)-2,3,4,5-tetrahydro-1H-benzo[d]azepin-7-ylamino]-pyrimidin-4-ylamino}-benzoic acid ethyl ester as a yellow solid (1.22 g, 60%). m.p.=78-80° C.; LCMS (m/e) 496 (M+H); ¹H-NMR (CDCl₃, 400 MHz) δ 11.16 (s, 1H), 8.85 (d, 1H, J=8.5 Hz), 8.14 (s, 1H), 8.11 (d, 1H, J=8.0 Hz), 7.56-7.45 (m, 1H), 7.35 (s, 1H), 7.30-7.20 (m, 1H), 7.13-7.01 (m, 2H), 6.93 (s, 1H), 4.45 (q, 2H, J=7.1 Hz), 3.60-3.50 (m, 2H), 3.39 (s, 3H), 3.0-2.88 (m, 4H), 2.80-2.67 (m, 6H), 1.45 (t, 3H, J=7.1 Hz).

Example 1396

{5-Chloro-2-[3-(2-methoxy-ethyl)-2,3,4,5-tetrahydro-1H-benzo[d]azepin-7-ylamino]-pyrimidin-4-ylamino}-N-isobutyl-benzamide 2-{5-Chloro-2-[3-(2-methoxy-ethyl)-2,3,4,5-tetrahydro-1H-benzo[d]azepin-7-ylamino]-pyrimidin-4-ylamino}-benzoic acid ethyl ester (36 mg, 0.072 mmol) and 1-propanamine, 2-methyl- (0.40 mL, 4.2 mmol) were placed in a microwave vessel. The reaction was microwaved on 300 watts, 200° C. for 60 minutes and then concentrated under reduced pressure. The residue was taken up in methanol and purified by prep-HPLC using a gradient of 20-45% AcN/water containing 0.1% TFA as the eluting solvent to obtain 2-{5-chloro-2-[3-(2-methoxy-ethyl)-2,3,4,5-tetrahydro-1H-benzo[d]azepin-7-ylamino]-pyrimidin-4-ylamino}-N-isobutyl-benzamide as an orange solid (11 mg, 29%). m.p.=178-181° C.; LCMS (m/e) 523 (M+H); ¹H-NMR (CDCl₃, 400 MHz) δ 10.96 (s, 1H), 8.66 (d, 1H, J=8.4 Hz), 8.10 (s, 1H), 7.51 (d, 1H, J=7.8 Hz), 7.49-7.40 (m, 1H), 7.36 (s, 1H), 7.30-7.22 (m, 1H), 7.15-7.06 (m, 1H), 7.04 (d, 1H, J=7.8 Hz), 6.91 (s, 1H), 6.21 (bs, 1H), 3.57 (t, 2H, J=5.5 Hz), 3.39 (s, 3H), 3.36-3.30 (m, 2H), 2.97-2.86 (m, 4H), 2.83-2.69 (m, 6H), 2.00-1.86 (m, 1H), 1.01 (d, 6H, J=6.7 Hz).

Example 1397

{5-Chloro-2-[3-(2-methoxy-ethyl)-2,3,4,5-tetrahydro-1H-benzo[d]azepin-7-ylamino]-pyrimidin-4-ylamino}-N-(2-dimethylamino-ethyl)-benzamide 2-{5-Chloro-2-[3-(2-methoxy-ethyl)-2,3,4,5-tetrahydro-1H-benzo[d]azepin-7-ylamino]-pyrimidin-4-ylamino}-N-(2-dimethylamino-ethyl)-benzamide was prepared from 2-{5-chloro-2-[3-(2-methoxy-ethyl)-2,3,4,5-tetrahydro-1H-benzo[d]azepin-7-ylamino]-pyrimidin-4-ylamino}-benzoic acid ethyl ester and N,N-dimethyl-1,2-ethanediamine in an analogous manner to Example 1396. Product isolated as a yellow foam (32 mg, 59%). LCMS (m/e) 538 (M+H); $^1$H-NMR (CDCl$_3$, 400 MHz) δ 11.22 (s, 1H), 8.66 (d, 1H, J=8.4 Hz), 8.09 (s, 1H), 7.61 (d, 1H, J=7.7 Hz), 7.47-7.41 (m, 1H), 7.38 (s, 1H), 7.30-7.16 (m, 2H), 7.14-7.07 (m, 1H), 7.06-7.00 (m, 2H), 3.65-3.55 (m, 4H), 3.38 (s, 3H), 3.04-2.92 (m, 4H), 2.89-2.78 (m, 6H), 2.64 (t, 2H, J=5.7 Hz), 2.36 (s, 6H).

Example 1398

{5-Chloro-2-[3-(2-methoxy-ethyl)-2,3,4,5-tetrahydro-1H-benzo[d]azepin-7-ylamino]-pyrimidin-4-ylamino}-N-(2-methoxy-ethyl)-benzamide 2-{5-Chloro-2-[3-(2-methoxy-ethyl)-2,3,4,5-tetrahydro-1H-benzo[d]azepin-7-ylamino]-pyrimidin-4-ylamino}-N-(2-methoxy-ethyl)-benzamide was prepared from 2-{5-chloro-2-[3-(2-methoxy-ethyl)-2,3,4,5-tetrahydro-1H-benzo[d]azepin-7-ylamino]-pyrimidin-4-ylamino}-benzoic acid ethyl ester and 2-methoxyethylamine in an analogous manner to Example 1396. Product isolated as a yellow foam (19 mg, 33%). LCMS (m/e) 525 (M+H); $^1$H-NMR (CDCl$_3$, 400 MHz) δ 11.07 (s, 1H), 6.67 (d, 1H, J=8.4 Hz), 8.09 (s, 1H), 7.54 (d, 1H, J=7.8 Hz), 7.50-7.40 (m, 1H), 7.37 (s, 1H), 7.30-7.22 (m, 1H), 7.15-7.0 (m, 3H), 6.70-6.61 (m, 1H), 3.72-3.65 (m, 2H), 3.62-3.55 (m, 4H), 3.41 (s, 3H), 3.38 (s, 1H), 2.99-2.88 (m, 4H), 2.84-2.73 (m, 6H).

Example 1399

{5-Chloro-2-[3-(2-methoxy-ethyl)-2,3,4,5-tetrahydro-1H-benzo[d]azepin-7-ylamino]-pyrimidin-4-ylamino}-N-(3-methoxy-propyl)-benzamide 2-{5-Chloro-2-[3-(2-methoxy-ethyl)-2,3,4,5-tetrahydro-1H-benzo[d]azepin-7-ylamino]-pyrimidin-4-ylamino}-N-(3-methoxy-propyl)-benzamide was prepared from 2-{5-chloro-2-[3-(2-methoxy-ethyl)-2,3,4,5-tetrahydro-1H-benzo[d]azepin-7-ylamino]-pyrimidin-4-ylamino}-benzoic acid ethyl ester and 3-methoxy-propylamine in an analogous manner to Example 1396. Product isolated as a white solid (21 mg, 36%). m.p.=154-156° C.; LCMS (m/e) 539 (M+H); $^1$H-NMR (CDCl$_3$, 400 MHz) δ 11.25 (s, 1H), 8.69 (d, 1H, J=8.5 Hz), 8.10 (s, 1H), 7.49 (d, 1H, J=7.8 Hz), 7.47-7.40 (m, 1H), 7.36 (s, 1H), 7.30-7.23 (m, 1H), 7.15-7.00 (m, 3H), 6.93 (s, 1H), 3.65-3.58 (m, 4H), 3.56 (t, 2H, J=5.7 Hz), 3.41 (s, 3H), 3.39 (s, 3H), 2.97-2.87 (m, 4H), 2.82-2.69 (m, 6H), 1.97-1.88 (m, 2H).

Example 1400

{5-Chloro-2-[3-(2-methoxy-ethyl)-2,3,4,5-tetrahydro-1H-benzo[d]azepin-7-ylamino]-pyrimidin-4-ylamino}-N-(4-dimethylamino-butyl)-benzamide 2-{5-Chloro-2-[3-(2-methoxy-ethyl)-2,3,4,5-tetrahydro-1H-benzo[d]azepin-7-ylamino]-pyrimidin-4-ylamino}-N-(4-dimethylamino-butyl)-benzamide was prepared from 2-{5-chloro-2-[3-(2-methoxy-ethyl)-2,3,4,5-tetrahydro-1H-benzo[d]azepin-7-ylamino]-pyrimidin-4-ylamino}-benzoic acid ethyl ester and N(1), N(1)-dimethyl-butane-1,4-diamine in an analogous manner to Example 1396. Product isolated as an orange solid (31 mg, 51%). m.p.=132-134° C.; LCMS (m/e) 566 (M+H); $^1$H-NMR (CDCl$_3$, 400 MHz) δ 11.35 (s, 1H), 8.68 (d, 1H, J=8.4 Hz), 8.51 (s, 1H), 8.09 (s, 1H), 7.54 (d, 1H, J=7.8 Hz), 7.47-7.38 (m, 1H), 7.36 (s, 1H), 7.30-7.22 (m, 1H), 7.13-6.93 (m, 3H), 3.56 (t, 2H, J=4.8 Hz), 3.51-3.42 (m, 2H), 3.39 (s, 3H), 2.98-2.85 (m, 4H), 2.82-2.67 (m, 6H), 2.35 (t, 2H, J=5.8 Hz), 2.21 (s, 6H), 1.81-1.71 (m, 2H), 1.71-1.61 (m, 2H).

Example 1401

2-{5-Chloro-2-[3-(2-methoxy-ethyl)-2,3,4,5-tetrahydro-1H-benzo[d]azepin-7-ylamino]-pyrimidin-4-ylamino}-N-(3-dimethylamino-propyl)-benzamide The title compound was prepared from 2-{5-chloro-2-[3-(2-methoxy-ethyl)-2,3,4,5-tetrahydro-1H-benzo[d]azepin-7-ylamino]-pyrimidin-4-ylamino}-benzoic acid ethyl ester and N(1), N(1)-dimethyl-propane-1,3-diamine in an analogous manner to Example 1396. Product isolated as a yellow foam (27 mg, 45%). LCMS (m/e) 552 (M+H): $^1$H-NMR (CDCl$_3$, 400 MHz) δ 11.62 (s, 1H), 8.91 (s, 1H), 8.72 (d, 1H, J=8.5 Hz), 8.10 (s, 1H), 7.47 (d, 1H, J=7.9 Hz), 7.46-7.40 (m, 1H), 7.36 (s, 1H), 7.30-7.23 (m, 1H), 7.10-7.00 (m, 2H), 6.96 (s, 1H), 3.64-3.53 (m, 4H), 3.39 (s, 3H), 2.97-2.88 (m, 4H), 2.82-2.70 (m, 6H), 2.55 (t, 2H, J=5.4 Hz), 2.33 (s, 6H), 1.84-1.75 (m, 2H).

Example 1402

2-{5-Chloro-2-[3-(2-methoxy-ethyl)-2,3,4,5-tetrahydro-1H-benzo[d]azepin-7-ylamino]-pyrimidin-4-ylamino}-N-[2-(4-methyl-piperazin-1-yl)-ethyl]-benzamide 2-{5-Chloro-2-[3-(2-methoxy-ethyl)-2,3,4,5-tetrahydro-1H-benzo[d]azepin-7-ylamino]-pyrimidin-4-ylamino}-N-[2-(4-methyl-piperazin-1-yl)-ethyl]-benzamide was prepared from 2-{5-chloro-2-[3-(2-methoxy-ethyl)-2,3,4,5-tetrahydro-1H-benzo[d]azepin-7-ylamino]-pyrimidin-4-ylamino}-benzoic acid ethyl ester and 2-(4-methyl-piperazin-1-yl)-ethylamine in an analogous manner to Example 1396. Product isolated as a yellow foam (16 mg, 25%). LCMS (m/e) 593 (M+H); $^1$H-NMR (CDCl$_3$, 400 MHz) δ 11.18 (s, 1H), 8.68 (d, 1H, J=8.5 Hz), 8.10 (s, 1H), 7.51 (d, 1H, J=8.0 Hz), 7.48-7.41 (m, 1H), 7.36 (s, 1H), 7.30-7.21 (m, 1H), 7.15-7.07 (m, 1H), 7.03 (d, 1H, J=8.0 Hz), 7.00 (s, 1H), 6.97-6.90 (m, 1H), 3.60-3.53 (m, 4H), 3.39 (s, 3H), 2.97-2.88 (m, 4H), 2.82-2.70 (m, 6H), 2.64 (t, 2H, J=5.7 Hz), 2.63-2.37 (m, 8H), 2.32 (s, 3H).

Example 1403

2-{5-Chloro-2-[3-(2-methoxy-ethyl)-2,3,4,5-tetrahydro-1H-benzo[d]azepin-7-ylamino]-pyrimidin-4-ylamino}-3-fluoro-N-prop-2-ynyl-benzamide 1403a) 8-Fluoro-1H-benzo[d][1,3]oxazine-2,4-dione (3.00 g, 16.6 mmol) was dissolved in tetrahydrofuran (100 mL, 1.23 mol) and prop-2-ynylamine (1.70 mL, 24.8 mmol) was added. The reaction was stirred for 2 hours and then concentrated under reduced pressure onto silica gel. Purification by silica gel chromatography (dry loaded) using a gradient of 0-60% EtOAc/hex as the eluting solvent to obtain 2-amino-3-fluoro-N-prop-2-ynyl-benzamide as a white solid (2.52 g, 79%). m.p.=89-91° C.; LCMS (m/e) 138 (M—NHCH2CCH); $^1$H-NMR (CDCl$_3$, 400 MHz) δ 7.14 (d, 1H, J=8.0 Hz), 7.12-7.05 (m, 1H), 6.64-6.56 (m, 1H), 6.28-6.14 (m, 1H), 5.67 (bs, 2H), 4.27-4.19 (m, 2H), 2.34-2.27 (m, 1H).

1403b) 2-(2,5-Dichloro-pyrimidin-4-ylamino)-3-fluoro-N-prop-2-ynyl-benzamide was prepared from 2-amino-3-fluoro-N-prop-2-ynyl-benzamide and 2,4,5-trichloro-pyrimidine in an analogous manner to Example 308b. Product isolated as an orange solid (1.22 g, 28%). m.p.=209-213° C.; LCMS (m/e) 339 (M+H); $^1$H-NMR (CDCl$_3$, 400 MHz); 9.07 (bs, 1H), 8.23 (s, 1H), 7.40-7.30 (m, 3H), 6.40-6.32 (m, 1H), 4.25-4.18 (m, 2H), 2.32-2.28 (m, 1H).

1403c) 2-{5-Chloro-2-[3-(2-methoxy-ethyl)-2,3,4,5-tetrahydro-1H-benzo[d]azepin-7-ylamino]-pyrimidin-4-ylamino}-3-fluoro-N-prop-2-ynyl-benzamide was prepared from 3-(2-methoxy-ethyl)-2,3,4,5-tetrahydro-1H-benzo[d]azepin-7-ylamine and 2-(2,5-dichloro-pyrimidin-4-ylamino)-3-fluoro-N-prop-2-ynyl-benzamide in an analogous manner to Example 308c. Product isolated as a yellow foam (126 mg, 60%). LCMS (m/e) 523 (M+H); $^1$H-NMR (CDCl$_3$, 400 MHz) δ 8.33 (bs, 1H), 8.08 (s, 1H), 7.42-7.37 (m, 1H), 7.36-7.28 (m, 2H), 7.14 (s, 1H), 7.09 (d, 1H, J=7.9 Hz), 6.90 (d, 1H, J=8.1 Hz), 6.82 (s, 1H), 6.31-6.24 (m, 1H), 4.15-4.10 (m, 2H), 3.55 (t, 2H, J=5.7 Hz), 3.39 (s, 3H), 2.90-2.83 (m, 2H), 2.81-2.73 (m, 4H), 2.73-2.65 (m, 4H), 2.23-2.20 (m, 1H).

Example 1404

2-[5-Chloro-2-(2-oxo-2,3,4,5-tetrahydro-1H-benzo[b]azepin-8-ylamino)-pyrimidin-4-ylamino]-3-fluoro-N-prop-2-ynyl-benzamide 2-[5-Chloro-2-(2-oxo-2,3,4,5-tetrahydro-1H-benzo[b]azepin-8-ylamino)-pyrimidin-4-ylamino]-3-fluoro-N-prop-2-ynyl-benzamide was prepared from 8-amino-1,3,4,5-tetrahydro-benzo[b]azepin-2-one and 2-(2,5-dichloro-pyrimidin-4-ylamino)-3-fluoro-N-prop-2-ynyl-benzamide in an analogous manner to Example 308c. Product isolated as a yellow solid (36 mg, 19%). m.p.=236-241° C.; LCMS (m/e) 479 (M+H); $^1$H-NMR (CDCl$_3$, 400 MHz) δ 8.40 (s, 1H), 8.10 (s, 1H), 7.53 (d, 1H, J=7.4 Hz), 7.47-7.31 (m, 3H), 7.16 (s, 1H), 7.07-7.00 (m, 2H), 6.82 (d, 1H, J=8.1 Hz), 6.54-6.47 (m, 1H), 4.21-4.15 (m, 2H), 2.73 (t, 2H, J=7.3 Hz), 2.34 (t, 2H, J=7.1 Hz), 2.26-2.15 (m, 3H).

Example 1405

2-[5-Chloro-2-(1-ethyl-5,5-dimethyl-2-oxo-2,3,4,5-tetrahydro-1H-benzo[b]azepin-8-ylamino)-pyrimidin-4-ylamino]-3-fluoro-N-prop-2-ynyl-benzamide 2-[5-Chloro-2-(1-ethyl-5,5-dimethyl-2-oxo-2,3,4,5-tetrahydro-1H-benzo[b]azepin-8-ylamino)-pyrimidin-4-ylamino]-3-fluoro-N-prop-2-ynyl-benzamide was prepared from 8-amino-1-ethyl-5,5-dimethyl-1,3,4,5-tetrahydro-benzo[b]azepin-2-one and 2-(2,5-dichloro-pyrimidin-4-ylamino)-3-fluoro-N-prop-2-ynyl-benzamide in an analogous manner to Example 308c. Product isolated as a yellow solid (93 mg, 43%). m.p.=237-241° C.; LCMS (m/e) 535 (M+H); $^1$H-NMR (CDCl$_3$, 400 MHz) δ 8.57 (s, 1H), 8.12 (s, 1H), 7.49 (s, 1H), 7.40 (d, 1H, J=7.4 Hz), 7.36-7.25 (m, 2H), 7.21 (d, 1H, J=8.9 Hz), 7.13 (d, 1H, J=8.3 Hz), 6.89 (s, 1H), 6.34-6.27 (m, 1H), 4.19-4.15 (m, 2H), 3.77-3.65 (m, 2H), 2.34-2.21 (m, 3H), 2.10-1.93 (m, 2H), 1.33 (s, 6H), 1.20 (t, 3H, J=7.4 Hz).

Example 1406

2-[5-Chloro-2-(5,5-dimethyl-2-oxo-2,3,4,5-tetrahydro-1H-benzo[b]azepin-8-ylamino)-pyrimidin-4-ylamino]-3-fluoro-N-prop-2-ynyl-benzamide 2-[5-Chloro-2-(5,5-dimethyl-2-oxo-2,3,4,5-tetrahydro-1H-benzo[b]azepin-8-ylamino)-pyrimidin-4-ylamino]-3-fluoro-N-prop-2-ynyl-benzamide was prepared from 8-amino-5,5-dimethyl-1,3,4,5-tetrahydro-benzo[b]azepin-2-one and 2-(2,5-dichloro-pyrimidin-4-ylamino)-3-fluoro-N-prop-2-ynyl-benzamide in an analogous manner to Example 308c. Product isolated as an orange foam (103 mg, 50%). LCMS (m/e) 507 (M+H); $^1$H-NMR (CDCl$_3$, 400 MHz) δ 8.40 (s, 1H), 8.10 (s, 1H), 7.55 (d, 1H, J=7.8 Hz), 7.47-7.33 (m, 3H), 7.26-7.17 (m, 2H), 7.07 (s, 1H), 6.79 (d, 1H, J=8.4 Hz), 6.59-6.50 (m, 1H), 4.19-4.15 (m, 2H), 2.38 (t, 2H, J=6.9 Hz), 2.25-2.20 (m, 1H), 2.08-2.04 (m, 2H), 1.37 (s, 6H).

Example 1407

2-[5-Chloro-2-(9-ethyl-6,7,8,9-tetrahydro-5-oxa-9-aza-benzocyclohepten-3-ylamino)-pyrimidin-4-ylamino]-3-fluoro-N-prop-2-ynyl-benzamide 2-[5-Chloro-2-(9-ethyl-6,7,8,9-tetrahydro-5-oxa-9-aza-benzocyclohepten-3-ylamino)-pyrimidin-4-ylamino]-3-fluoro-N-prop-2-ynyl-benzamide was prepared from 9-ethyl-6,7,8,9-tetrahydro-5-oxa-9-aza-benzocyclohepten-3-ylamine and 2-(2,5-dichloro-pyrimidin-4-ylamino)-3-fluoro-N-prop-2-ynyl-benzamide in an analogous manner to Example 308c. Product isolated as a yellow foam (50 mg, 20%). LCMS (m/e) 495 (M+H); $^1$H-NMR (CDCl$_3$, 400 MHz) δ 8.34 (s, 1H), 8.05 (s, 1H), 7.40-7.23 (m, 3H), 7.09 (s, 1H), 6.93 (s, 1H), 6.87 (d, 1H, J=8.6 Hz), 6.69 (d, 1H, J=8.6 Hz), 6.51-6.42 (m, 1H), 4.16-4.07 (m, 2H), 4.06 (t, 2H, J=5.2 Hz), 3.23-3.11 (m, 4H), 2.24-2.19 (m, 1H), 2.04-1.94 (m, 2H), 1.18 (t, 3H, J=7.1 Hz).

Example 1408

2-{5-Chloro-2-[3-(2-methoxy-ethyl)-2,3,4,5-tetrahydro-1H-benzo[d]azepin-7-ylamino]-pyrimidin-4-ylamino}-benzoic acid methyl ester 2-{5-Chloro-2-[3-(2-methoxy-ethyl)-2,3,4,5-tetrahydro-1H-benzo[d]azepin-7-ylamino]-pyrimidin-4-ylamino}-benzoic acid ethyl ester (1.168 g, 2.355 mmol) was dissolved in tetrahydrofuran (117 mL, 1440 mmol). Lithium hydroxide (67.7 mg, 2.82 mmol) dissolved in water (23.4 mL, 1.30 mol) was added and the reaction was stirred for 48 hours. The reaction was concentrated under reduced pressure and azetroped twice with toluene. The reaction was then further dried under high vacuum to obtain 2-{5-chloro-2-[3-(2-methoxy-ethyl)-2,3,4,5-tetrahydro-1H-benzo[d]azepin-7-ylamino]-pyrimidin-4-ylamino}-benzoic acid. 2-{5-Chloro-2-[3-(2-methoxy-ethyl)-2,3,4,5-tetrahydro-1H-benzo[d]azepin-7-ylamino]-pyrimidin-4-ylamino}-benzoic acid (1.55 g, 3.31 mmol) was placed in toluene (40.0 mL, 376 mmol) and methanol (10.0 mL, 247 mmol). 2.00 M of Trimethylsilyldiazomethane in hexane (4.50 mL) was added and the reaction was stirred overnight. The reaction was quenched with acetic acid and then concentrated under reduced pressure. The residue was taken up in DCM (50 mL) and washed with sat. NaHCO$_3$ (50 mL). The organic layer was dried over sodium sulfate, filtered, and concentrated under reduced pressure. Purification by amine capped silica gel chromatography using a gradient of 0-60% EtOAc/hex as the eluting solvent to obtain 2-{5-Chloro-2-[3-(2-methoxy-ethyl)-2,3,4,5-tetrahydro-1H-benzo[d]azepin-7-ylamino]-pyrimidin-4-ylamino}-benzoic acid methyl ester as a pale yellow solid (344 mg, 21%). m.p.=152-156° C.; LCMS (m/e) 482 (M+H); $^1$H-NMR (CDCl$_3$, 400 MHz) δ 11.13 (s, 1H), 8.86 (d, 1H, J=8.6 Hz), 8.14 (s, 1H), 8.09 (d, 1H, J=8.0 Hz), 7.55-7.46 (m, 1H), 7.35 (s, 1H), 7.30-7.22 (m, 1H), 7.14-7.02 (m, 2H), 6.92 (s, 1H), 3.99 (s, 3H), 3.56 (t, 2H, J=5.7 Hz), 3.39 (s, 3H), 2.98-2.89 (m, 4H), 2.80-2.71 (m, 6H).

Example 1409

3-[5-Chloro-2-(9-ethyl-6,7,8,9-tetrahydro-5-oxa-9-aza-benzocyclohepten-3-ylamino)-pyrimidin-4-ylamino]-thiophene-2-carboxylic acid methyl amide 3-[5-Chloro-2-(9-ethyl-6,7,8,9-tetrahydro-5-oxa-9-aza-benzocyclohepten-3-ylamino)-pyrimidin-4-ylamino]-thiophene-2-carboxylic acid methylamide was prepared from 9-ethyl-6,7,8,9-tetrahydro-5-oxa-9-aza-benzocyclohepten-3-ylamine and 3-(2,5-dichloro-pyrimidin-4-ylamino)-thiophene-2-carboxylic acid methylamide in an analogous manner to Example 308c. Product isolated as a tan solid (124 mg, 60%). m.p.=199-201° C.; LCMS (m/e) 459 (M+H); $^1$H-NMR (CDCl$_3$, 400 MHz) δ 11.59 (s, 1H), 9.26 (s, 1H), 8.51-8.42 (m, 1H), 8.22 (d, 1H, J=4.8 Hz); 8.20 (s, 1H), 7.71 (d, 1H, J=5.3 Hz), 7.25 (s, 1H), 7.11 (d, 1H, J=9.34 Hz), 6.81 (d, 1H, J=8.8 Hz), 4.03 (t, 2H, J=5.3 Hz), 3.17 (q, 2H, J=7.0 Hz), 3.11 (t, 2H, J=5.0 Hz), 2.78 (d, 3H, J=4.3 Hz), 1.96-1.86 (m, 2H), 1.13 (t, 3H, J=7.0 Hz).

Example 1410

2-[5-Chloro-4-(2-fluoro-6-methylcarbamoyl-phenylamino)-pyrimidin-2-ylamino]-7,8-dihydro-6H-5-oxa-9-aza-benzocycloheptene-9-carboxylic acid ethyl ester 2-Amino-7,8-dihydro-6H-5-oxa-9-aza-benzocycloheptene-9-carboxylic acid ethyl ester (102 mg, 0.433 mmol) and 2-(2,5-dichloro-pyrimidin-4-ylamino)-3-fluoro-N-methyl-benzamide (150 mg, 0.476 mmol) were placed in isopropyl alcohol (3.00 mL, 39.2 mmol) and 10-camphorsulfonic acid (10.0 mg, 0.0433 mmol) was added. The reaction was microwaved on 300 watts, 120° C. for 20 minutes and then concentrated under reduced pressure. The residue was taken up in DCM (20 mL) and washed with sat. NaHCO$_3$ (20 mL). The organic layer was dried over sodium sulfate, filtered, and concentrated under reduced pressure. Purification by silica gel chromatography using a gradient of 0-100% EtOAc/hex as the eluting solvent to obtain 2-[5-Chloro-4-(2-fluoro-6-methylcarbamoyl-phenylamino)-pyrimidin-2-ylamino]-7,8-dihydro-6H-5-oxa-9-aza-benzocycloheptene-9-carboxylic acid ethyl ester as a yellow foam (115 mg, 52%). LCMS (m/e) 515 (M+H); $^1$H-NMR (d6-DMSO, 400 MHz) δ 9.37 (bs, 1H), 8.56-8.47 (m, 1H), 8.17 (s, 1H), 7.52-7.36 (m, 4H), 7.28-7.17 (m, 1H), 6.79 (d, 1H, J=8.7 Hz), 4.20-3.81 (m, 4H), 3.70-2.42 (m, 1H), 2.73 (d, 3H, J=4.5 Hz), 1.95-1.80 (m, 2H), 1.36-0.98 (m, 3H).

Example 1411

2-[5-Chloro-4-(2-methylcarbamoyl-thiophen-3-ylamino)-pyrimidin-2-ylamino]-7,8-dihydro-6H-5-oxa-9-aza-benzocycloheptene-9-carboxylic acid ethyl ester 2-[5-Chloro-4-(2-methylcarbamoyl-thiophen-3-ylamino)-pyrimidin-2-ylamino]-7,8-dihydro-6H-5-oxa-9-aza-benzocycloheptene-9-carboxylic acid ethyl ester was prepared from 2-amino-7,8-dihydro-6H-5-oxa-9-aza-benzocycloheptene-9-carboxylic acid ethyl ester and 3-(2,5-dichloro-pyrimidin-4-ylamino)-thiophene-2-carboxylic acid methylamide in an analogous manner to Example 1410. Product isolated as a tan solid (138 mg, 61%). m.p.=222-224° C.; LCMS (m/e) 503 (M+H); $^1$H-NMR (d6-DMSO, 400 MHz) δ 11.62 (s, 1H), 9.50 (s, 1H), 8.52-8.38 (m, 1H), 8.30-8.20 (m, 2H), 7.74 (d, 1H, J=5.4 Hz), 7.70-7.59 (m, 1H), 7.50-7.38 (m, 1H), 6.98 (d, 1H, J=8.6 Hz), 4.20-3.91 (m, 4H), 3.79-3.55 (m, 2H), 2.77 (d, 3H, J=4.2 Hz), 2.01-1.86 (m, 2H), 1.33-0.90 (m, 3H).

Example 1412

2-[5-Chloro-2-(2-oxo-2,3,4,5-tetrahydro-1H-benzo[b]azepin-8-ylamino)-pyrimidin-4-ylamino]-5-dimethylamino-N-methyl-benzamide 2-[5-Chloro-2-(2-oxo-2,3,4,5-tetrahydro-1H-benzo[b]azepin-8-ylamino)-pyrimidin-4-ylamino]-5-dimethylamino-N-methyl-benzamide was prepared from 8-amino-1,3,4,5-tetrahydro-benzo[b]azepin-2-one and 2-(2,5-dichloro-pyrimidin-4-ylamino)-5-dimethylamino-N-methyl-benzamide in an analogous manner to Example 1410. Product isolated as a yellow solid (155 mg, 81%). m.p.=253-255° C.; LCMS (m/e) 480 (M+H); $^1$HNMR (d6-DMSO, 400 MHz) δ 11.46 (bs, 1H), 9.80-9.66 (m, 1H), 9.51 (s, 1H), 8.87-8.77 (m, 1H), 8.53-8.40 (m, 1H), 8.21 (s, 1H), 7.34 (s, 1H), 7.29-7.09 (m, 1H), 7.25 (d, 1H, J=8.0 Hz), 7.17 (d, 1H, J=8.5 Hz), 7.03-6.81 (m, 1H), 2.99 (s, 6H), 2.81 (d, 3H, J=3.8 Hz), 2.65 (t, 2H, J=6.8 Hz), 2.24-2.15 (m, 2H), 2.15-2.04 (m, 2H).

Example 1413

2-{5-Chloro-2-[3-(2-methoxy-ethyl)-2,3,4,5-tetrahydro-1H-benzo[d]azepin-7-ylamino]-pyrimidin-4-ylamino}-5-dimethylamino-N-methyl-benzamide 2-{5-Chloro-2-[3-(2-methoxy-ethyl)-2,3,4,5-tetrahydro-1H-benzo[d]azepin-7-ylamino]-pyrimidin-4-ylamino}-5-dimethylamino-N-methyl-benzamide was prepared from 3-(2-methoxy-ethyl)-2,3,4,5-tetrahydro-1H-benzo[d]azepin-7-ylamine and 2-(2,5-dichloro-pyrimidin-4-ylamino)-5-dimethylamino-N-methyl-benzamide in an analogous manner to Example 308c. Product isolated as a yellow foam (139 mg, 66%). LCMS (m/e) 524 (M+H); $^1$H-NMR (CDCl$_3$, 400 MHz) δ 10.15 (s, 1H), 8.34 (d, 1H, J=9.2 Hz), 8.03 (s, 1H), 7.39 (s, 1H), 7.21 (d, 1H, J=8.0 Hz), 7.00 (d, 1H, J=8.0 Hz), 6.91-6.80 (m, 2H), 6.78 (s, 1H), 6.21-6.12 (m, 1H), 3.55 (t, 2H, J=5.5 Hz), 3.38 (s, 3H), 3.02 (d, 3H, J=4.9 Hz), 3.00 (s, 6H), 2.96-2.85 (m, 4H), 2.80-2.68 (m, 6H).

Example 1414

5-Bromo-2-[5-chloro-2-(2-oxo-2,3,4,5-tetrahydro-1H-benzo[b]azepin-8-ylamino)-pyrimidin-4-ylamino]-3-fluoro-N-methyl-benzamide 1414a) 2-Amino-3-fluoro-N-methyl-benzamide (10.0 g, 59.5 mmol) was dissolved in acetic acid (100 mL, 176 mmol) and bromine (3.22 mL, 62.4 mmol) was added. The reaction was stirred at room temperature for 20 minutes and the precipitate was then collected by filtration and washed with ethyl ether. The white solid was dried overnight under high vacuum at 50° C. to obtain 2-amino-5-bromo-3-fluoro-N-methyl-benzamide; hydrobromide as a white solid (16.8 g, 86%). LCMS (m/e) 216 (M—NHCH3); $^1$H-NMR (d6-DMSO, 400 MHz) δ 8.49-8.38 (m, 1H), 7.83-7.46 (m, 3H), 7.54 (s, 1H), 7.43 (d, 1H, J=10.89 Hz), 2.72 (d, 3H, J=4.2 Hz); 19F-NMR (d6-DMSO, 400 MHz) δ 131.

1414b) 2-Amino-5-bromo-3-fluoro-N-methyl-benzamide; hydrobromide (2.00 g, 6.10 mmol) was placed in N-methylpyrrolidinone (20.0 mL, 207 mmol) and N,N-diisopropylethylamine (3.19 mL, 18.3 mmol) was added. The reaction was stirred for 5 minutes and then 2,4,5-trichloro-pyrimidine (3.50 mL, 30.5 mmol) was added. The reaction was heated at 100° C. for 24 hours and then concentrated under reduced pressure. The residue was taken up in DCM (100 mL) and washed twice with water (100 mL). The organic layer was dried over sodium sulfate, filtered, and concentrated under reduced pressure. Purification by silica gel chromatography using a gradient of 0-40% EtOAc/hex as the eluting solvent to obtain 5-bromo-2-(2,5-dichloro-pyrimidin-4-ylamino)-3-fluoro-N-methyl-benzamide as a tan solid (1.19 g, 50%). m.p.=246-249° C.; LCMS (m/e) 393 (M+H); $^1$H-NMR (d6-DMSO, 400 MHz) δ 9.73 (s, 1H), 8.68-8.57 (m, 1H), 8.43 (s, 1H), 7.87 (d, 1H, J=9.6 Hz), 7.66 (s, 1H), 2.69 (d, 3H, J=3.9 Hz); $^{19}$F-NMR (d6-DMSO, 400 MHz)$_{6-113}$.

1414c) 5-Bromo-2-[5-chloro-2-(2-oxo-2,3,4,5-tetrahydro-1H-benzo[b]azepin-8-ylamino)-pyrimidin-4-ylamino]-3-fluoro-N-methyl-benzamide was prepared from 8-amino-1,3,4,5-tetrahydro-benzo[b]azepin-2-one and 5-bromo-2-(2,5-dichloro-pyrimidin-4-ylamino)-3-fluoro-N-methyl-benzamide in an analogous manner to Example 1410. Product isolated as a gray solid (61 mg, 38%). m.p.=274-278° C.; LCMS (m/e) 533 (M+H); $^1$H-NMR (d6-DMSO, 400 MHz) δ 9.46 (bs, 1H), 9.43 (s, 1H), 9.38 (s, 1H), 8.66-8.57 (m, 1H), 8.21 (s, 1H), 7.79 (d, 1H, J=9.6 Hz), 7.68 (s, 1H), 7.19 (d, 1H, J=8.1 Hz), 7.08 (bs, 1H), 6.97 (d, 1H, J=8.2 Hz), 2.71 (d, 3H, J=4.3 Hz), 2.58 (t, 2H, J=6.4 Hz), 2.18-2.00 (m, 4H); $^{19}$F-NMR (d6-DMSO, 400 MHz) δ –111.

Example 1415

5-Bromo-2-{5-chloro-2-[3-(2-methoxy-ethyl)-2,3,4,5-tetrahydro-1H-benzo[d]azepin-7-ylamino]-pyrimidin-4-ylamino}-3-fluoro-N-methyl-benzamide 5-Bromo-2-{5-chloro-2-[3-(2-methoxy-ethyl)-2,3,4,5-tetrahydro-1H-benzo[d]azepin-7-ylamino]-pyrimidin-4-ylamino}-3-fluoro-N-methyl-benzamide was prepared from 3-(2-methoxy-ethyl)-2,3,4,5-tetrahydro-1H-benzo[d]azepin-7-ylamine and 5-bromo-2-(2,5-dichloro-pyrimidin-4-ylamino)-3-fluoro-N-methyl-benzamide in an analogous manner to Example 308c. Product isolated as an off-white foam (22 mg, 12%). LCMS (m/e) 577 (M+H); $^1$H-NMR (CDCl$_3$, 400 MHz) δ 8.61 (s, 1H), 8.07 (s, 1H), 7.48 (s, 1H), 7.44 (d, 1H, J=9.3 Hz), 7.19 (s, 1H), 7.06-6.97 (m, 2H), 6.91 (d, 1H, J=8.1 Hz), 6.28-6.18 (m, 1H), 3.57 (t, 2H, J=5.6 Hz), 3.38 (s, 3H), 2.90 (d, 3H, J=4.9 Hz), 2.92-2.84 (m, 2H), 2.83-2.65 (m, 8H); $^{19}$F-NMR (CDCl$_3$, 400 MHz) δ –109.

Example 1416

2-{5-Chloro-2-[3-(2-methoxy-ethyl)-2,3,4,5-tetrahydro-1H-benzo[d]azepin-7-ylamino]-pyrimidin-4-ylamino}-N-(2-pyrrolidin-1-yl-ethyl)-benzamide 2-{5-Chloro-2-[3-(2-methoxy-ethyl)-2,3,4,5-tetrahydro-1H-benzo[d]azepin-7-ylamino]-pyrimidin-4-ylamino}-N-(2-pyrrolidin-1-yl-ethyl)-benzamide was prepared from 2-{5-chloro-2-[3-(2-methoxy-ethyl)-2,3,4,5-tetrahydro-1H-benzo[d]azepin-7-ylamino]-pyrimidin-4-ylamino}-benzoic acid ethyl ester and 2-pyrrolidin-1-yl-ethylamine in an analogous manner to Example 1396. Product isolated as a tan solid (25 mg, 54%). m.p.=172-174° C.; LCMS (m/e) 564 (M+H); $^1$H-NMR (CDCl$_3$, 400 MHz) δ 11.19 (s, 1H), 8.68 (d, 1H, J=8.6 Hz), 8.10 (s, 1H), 7.57-7.52 (m, 1H), 7.48-7.41 (m, 1H), 7.38-7.34 (m, 1H), 7.30-7.23 (m, 1H), 7.14-7.08 (m, 1H), 7.07-6.95 (m, 2H), 6.90-6.85 (m, 1H), 3.62-3.53 (m, 4H), 3.39 (s, 3H), 2.97-2.87 (m, 4H), 2.81-2.69 (m, 8H), 2.65-2.53 (m, 4H), 1.88-1.78 (m, 4H).

Example 1417

3-[5-Chloro-4-(2-fluoro-6-methylcarbamoyl-phenylamino)-pyrimidin-2-ylamino]-7,8-dihydro-6H-5-oxa-9-aza-benzocycloheptene-9-carboxylic acid ethyl ester 1417a) 3-Nitro-7,8-dihydro-6H-5-oxa-9-aza-benzocycloheptene-9-carboxylic acid ethyl ester (338 mg, 1.27 mmol) was placed in methanol (10.0 mL, 0.247 mol) and 10% Palladium on Carbon (50% Wet) (67.5 mg) was added. The reaction was hydrogenated at 25 psi. for 30 minutes and then filtered through a pad of celite to remove the catalyst. The product was then concentrated under reduced pressure to obtain 3-amino-7,8-dihydro-6H-5-oxa-9-aza-benzocycloheptene-9-carboxylic acid ethyl ester as a light brown solid (300 mg, 100%). m.p.=140-143° C.; LCMS (m/e) 237 (M+H); $^1$H-NMR (CDCl$_3$, 400 MHz) δ 7.18-6.91 (m, 1H), 6.41-6.30 (m, 2H), 4.30-3.93 (m, 4H), 3.83-3.50 (m, 4H), 2.13-1.93 (m, 2H), 1.40-1.10 (m, 3H).

1417b) 3-[5-Chloro-4-(2-fluoro-6-methylcarbamoyl-phenylamino)-pyrimidin-2-ylamino]-7,8-dihydro-6H-5-oxa-9-aza-benzocycloheptene-9-carboxylic acid ethyl ester was prepared from 3-amino-7,8-dihydro-6H-5-oxa-9-aza-benzocycloheptene-9-carboxylic acid ethyl ester and 2-(2,5-dichloro-pyrimidin-4-ylamino)-3-fluoro-N-methyl-benzamide in an analogous manner to Example 1410. Product isolated as a yellow foam (135 mg, 66%). LCMS (m/e) 515 (M+H); $^1$H-NMR (CDCl$_3$, 400 MHz) δ 8.95-8.72 (m, 1H), 8.09 (s, 1H), 7.44-7.17 (m, 4H), 7.15-6.84 (m, 3H), 6.30-6.10 (m, 1H), 4.32-3.95 (m, 4H), 3.87-3.60 (m, 2H), 3.00-2.85 (m, 3H), 2.13-1.98 (m, 2H), 1.41-1.11 (m, 3H); $^{19}$F-NMR (CDCl$_3$, 400 MHz) δ –111.

Example 1418

3-[5-Chloro-4-(2-methylcarbamoyl-thiophen-3-ylamino)-pyrimidin-2-ylamino]-7,8-dihydro-6H-5-oxa-9-aza-benzocycloheptene-9-carboxylic acid ethyl ester The title compound was prepared from 3-amino-7,8-dihydro-6H-5-oxa-9-aza-benzocycloheptene-9-carboxylic acid ethyl ester and 3-(2,5-dichloro-pyrimidin-4-ylamino)-thiophene-2-carboxylic acid methylamide in an analogous manner to Example 1410. Product isolated as an orange foam (155 mg, 77%). LCMS (m/e) 503 (M+H); $^1$H-NMR (CDCl$_3$, 400 MHz) δ 11.32 (bs, 1H), 8.38 (bs, 1H), 8.13 (s, 1H), 7.45-7.27 (m, 2H), 7.21-7.05 (m, 2H), 7.01 (s, 1H), 5.81-5.69 (m, 1H), 4.33-4.05 (m, 4H), 3.90-3.65 (m, 2H), 3.03 (d, 3H, J=4.7 Hz), 2.17-2.02 (m, 2H), 1.42-1.14 (m, 3H).

Example 1419

3-[5-Chloro-4-(2-methylcarbamoyl-phenylamino)-pyrimidin-2-ylamino]-7,8-dihydro-6H-5-oxa-9-aza-benzocycloheptene-9-carboxylic acid ethyl ester 3-[5-Chloro-4-(2-methylcarbamoyl-phenylamino)-pyrimidin-2-ylamino]-7,8-dihydro-6H-5-oxa-9-aza-benzocycloheptene-9-carboxylic acid ethyl ester was prepared from 3-amino-7,8-dihydro-6H-5-oxa-9-aza-benzocycloheptene-9-carboxylic acid ethyl ester and 2-(2,5-dichloro-pyrimidin-4-ylamino)-N-methyl-benzamide in an analogous manner to Example 1410. Product isolated as a yellow foam (102 mg, 52%). LCMS (m/e) 497 (M+H); 1H-NMR (CDCl$_3$, 400 MHz) δ 11.14-11.00 (m, 1H), 8.70-8.36 (m, 1H), 8.12 (s, 1H), 7.57-6.96 (m, 7H), 6.48-6.38 (m, 1H), 4.33-4.03 (m, 4H), 3.88-3.60 (m, 2H), 3.03 (d, 3H, J=4.4 Hz), 2.15-2.00 (m, 2H), 1.42-1.12 (m, 3H).

Example 1420

4-[5-Chloro-2-(2-oxo-2,3,4,5-tetrahydro-1H-benzo[b]azepin-8-ylamino)-pyrimidin-4-ylamino]-4'-cyano-5-fluoro-biphenyl-3-carboxylic acid methyl amide 5-Bromo-2-[5-chloro-2-(2-oxo-2,3,4,5-tetrahydro-1H-benzo[b]azepin-8-ylamino)-pyrimidin-4-ylamino]-3-fluoro-N-methyl-benzamide (55.0 mg, 0.103 mmol) was dissolved in toluene (4.00 mL, 37.6 mmol) and ethanol (4.00 mL, 68.5 mmol). Tetrakis(triphenylphosphine)palladium(0) (11.9 mg, 0.0103 mol) was added followed by 1.00 M sodium carbonate in water (412 uL) and 4-cyanophenylboronic acid (21.2 mg, 0.144 mmol). The reaction was heated at 90° C. overnight and then concentrated under reduced pressure. The residue was taken up in DCM (10 mL) and washed with 1 M Na$_2$CO$_3$ (10 mL). The organic layer was dried over sodium sulfate, filtered, and concentrated under reduced pressure. Purification by prep-HPLC using a gradient of 20-45% AcN/water containing 0.1% TFA as the eluting solvent to obtain 4-[5-chloro-2-(2-oxo-2,3,4,5-tetrahydro-1H-benzo[b]azepin-8-ylamino)-pyrimidin-4-ylamino]-4'-cyano-5-fluoro-biphenyl-3-carboxylic acid methylamide as a white foam (25 mg, 44%). LCMS (m/e) 556 (M+H); $^1$H-NMR (d6-DMSO, 400 MHz) δ 9.54 (s, 1H), 9.40-9.30 (m, 2H), 8.80-8.71 (m, 1H), 8.21 (s, 1H), 8.08-7.98 (m, 4H), 7.95 (d, 1H, J=12.1 Hz), 7.89 (s, 1H), 7.27 (d, 1H, J=8.1 Hz), 7.16-7.10 (m, 1H), 6.93 (d, 1H, J=8.1 Hz), 2.77 (d, 3H, J=4.2 Hz), 2.60-2.43 (m, 2H), 2.02-1.94 (m, 4H); $^{19}$F-NMR (d6-DMSO, 400 MHz) δ −75.

Example 1421

2-{5-Chloro-2-[3-(2-methoxy-ethyl)-2,3,4,5-tetrahydro-1H-benzo[d]azepin-7-ylamino]-pyrimidin-4-ylamino}-N-cyclopropylmethyl-benzamide 2-{5-Chloro-2-[3-(2-methoxy-ethyl)-2,3,4,5-tetrahydro-1H-benzo[d]azepin-7-ylamino]-pyrimidin-4-ylamino}-N-cyclopropylmethyl-benzamide was prepared from 2-{5-chloro-2[3-(2-methoxy-ethyl)-2,3,4,5-tetrahydro-1H-benzo[d]azepin-7-ylamino]-pyrimidin-4-ylamino}-benzoic acid ethyl ester and cyclopropylmethylamine in an analogous manner to Example 1396. Product isolated as a tan solid (30 mg, 47%). m.p.=173-175° C.; LCMS (m/e) 521 (M+H); $^1$H-NMR (CDCl$_3$, 400 MHz) δ 11.02 (s, 1H), 8.66 (d, 1H, J=8.4 Hz), 8.09 (s, 1H), 7.54 (d, 1H, J=7.6 Hz), 7.49-7.40 (m, 1H), 7.35 (s, 1H), 7.24 (d, 1H, J=8.0 Hz), 7.16-7.04 (m, 2H), 7.03 (d, 1H, J=8.0 Hz), 6.40-6.30 (m, 1H), 3.56 (t, 2H, J=5.6 Hz), 3.39 (s, 3H), 3.37-3.30 (m, 2H), 2.98-2.83 (m, 4H), 2.82-2.67 (m, 6H), 1.14-1.01 (m, 1H), 0.64-0.55 (m, 2H), 0.35-0.27 (m, 2H).

Example 1422

2-[5-Chloro-2-(2-oxo-2,3,4,5-tetrahydro-1H-benzo[b]azepin-8-ylamino)-pyrimidin-4-ylamino]-3-fluoro-N-methyl-5-(1-methyl-1H-pyrazol-4-yl)-benzamide 1422a) 2-Amino-5-bromo-3-fluoro-N-methyl-benzamide; hydrobromide (1.76 g, 5.38 mmol) was placed in toluene (70.5 mL, 662 mmol) and ethanol (70.7 mL, 1210 mmol). Tetrakis(triphenylphosphine)palladium(0) (622 mg, 0.538 mmol) was added followed by 1.00 M of sodium carbonate in water (32.3 mL) and 1-methyl-4-(4,4,5,5-tetramethyl-[1,3,2]dioxaborolan-2-yl)-1H-pyrazole (1.567 g, 7.531 mmol). The reaction was heated at 90° C. for 3 hours and then concentrated under reduced pressure. The residue was taken up in DCM (200 mL) and washed with 1.00 M Na$_2$CO$_3$ (200 mL). The organic layer was dried over sodium sulfate, filtered, and concentrated under reduced pressure. Purification by basic alumina chromatography using a gradient of 0-100% EtOAc/hex as the eluting solvent to obtain a mixture containing 2-amino-3-fluoro-N-methyl-5-(1-methyl-1H-pyrazol-4-yl)-benzamide. This mixture was dissolved in N-methylpyrrolidinone (15.0 mL, 156 mmol) and N,N-diisopropylethylamine (1.12 mL, 6.46 mmol) was added followed by 2,4,5-trichloropyrimidine (1.85 mL, 16.1 mmol). The reaction was heated at 100° C. overnight and then cooled to room temperature. The mixture was diluted with DCM (75 mL) and washed with water (4×100 mL). The organic layer was dried over sodium sulfate, filtered, and concentrated under reduced pressure. Purification by amine capped silica gel chromatography using a gradient of 0-100% EtOAc/hex as the eluting solvent to obtain 2-(2,5-dichloro-pyrimidin-4-ylamino)-3-fluoro-N-methyl-5-(1-methyl-1H-pyrazol-4-yl)-benzamide as a yellow solid (967 mg, 45%). m.p.=220-221° C.; LCMS (m/e) 395 (M+H); $^1$H-NMR (CDCl$_3$, 400 MHz) δ 9.51 (s, 1H), 8.19 (s, 1H), 7.58 (s, 1H), 7.49 (s, 1H), 7.33-7.23 (m, 2H), 6.83-6.70 (m, 1H), 3.95 (s, 3H), 3.00 (d, 3H, J=3.6 Hz).

1422b) 2-[5-Chloro-2-(2-oxo-2,3,4,5-tetrahydro-1H-benzo[b]azepin-8-ylamino)-pyrimidin-4-ylamino]-3-fluoro-N-methyl-5-(1-methyl-1H-pyrazol-4-yl)-benzamide was prepared from 8-amino-1,3,4,5-tetrahydro-benzo[b]azepin-2-one and 2-(2,5-dichloro-pyrimidin-4-ylamino)-3-fluoro-N-methyl-5-(1-methyl-H-pyrazol-4-yl)-benzamide in an analogous manner to Example 1410. Product isolated as a gray solid (142 mg, 77%). m.p.=281-283° C.; LCMS (m/e) 535 (M+H); $^1$H-NMR (d6-DMSO, 400 MHz) δ 9.52 (bs, 1H), 9.47-9.38 (m, 2H), 8.60-8.54 (m, 1H), 8.27 (s, 1H), 8.21 (s, 1H), 8.00 (s, 1H), 7.71-7.63 (m, 2H), 7.25 (d, 1H, J=8.4 Hz), 7.09 (bs, 1H), 6.93 (d, 1H, J=8.1 Hz), 3.90 (s, 3H), 2.74 (d, 3H, J=4.0 Hz), 2.58-2.47 (m, 2H), 2.08-1.93 (m, 4H).

Example 1423

2-{5-Chloro-2-[3-(2-methoxy-ethyl)-2,3,4,5-tetrahydro-1H-benzo[d]azepin-7-ylamino]-pyrimidin-4-ylamino}-3-fluoro-N-methyl-5-(1-methyl-1H-pyrazol-4-yl)-benzamide 2-{5-Chloro-2-[3-(2-methoxy-ethyl)-2,3,4,5-tetrahydro-1H-benzo[d]azepin-7-ylamino]-pyrimidin-4-ylamino}-3-fluoro-N-methyl-5-(1-methyl-1H-pyrazol-4-yl)-benzamide was prepared from 3-(2-methoxy-ethyl)-2,3,4,5-tetrahydro-1H-benzo[d]azepin-7-ylamine and 2-(2,5-dichloro-pyrimidin-4-ylamino)-3-fluoro-N-methyl-5-(1-methyl-1H-pyrazol-4-yl)-benzamide in an analogous manner to Example 308c. Product isolated as a white foam (81 mg, 40%). LCMS (m/e) 579; $^1$H-NMR (CDCl$_3$, 400 MHz) δ 8.37 (s, 1H), 8.07 (s, 1H), 7.79 (s, 1H), 7.68 (s, 1H), 7.43 (s, 1H), 7.37 (d, 1H, J=10.9 Hz), 7.23 (s, 1H), 7.06 (d, 1H, J=8.1 Hz), 6.93-6.83 (m, 2H), 6.22-6.13 (m, 1H), 4.00 (s, 3H), 3.50 (t, 2H, J=5.5 Hz), 3.37 (s, 3H), 2.92 (d, 3H, J=4.8 Hz), 2.88-2.80 (m, 2H), 2.79-2.71 (m, 2H), 2.71-2.63 (m, 4H), 2.63-2.54 (m, 2H); $^{19}$F-NMR (CDCl$_3$, 400 MHz) δ −113.

Example 1424

2-[2-(9-Acetyl-6,7,8,9-tetrahydro-5-oxa-9-aza-benzocyclohepten-2-ylamino)-5-chloro-pyrimidin-4-ylamino]-3-fluoro-N-methyl-5-(1-methyl-1H-pyrazol-4-yl)-benzamide 2-[2-(9-Acetyl-6,7,8,9-tetrahydro-5-oxa-9-aza-benzocyclohepten-2-ylamino)-5-chloro-pyrimidin-4-ylamino]-3-fluoro-N-methyl-5-(1-methyl-1H-pyrazol-4-yl)-benzamide was prepared from 1-(2-amino-7,8-dihydro-6H-5-oxa-9-aza-benzocyclohepten-9-yl)-ethanone and 2-(2,5-dichloro-pyrimidin-4-ylamino)-3-fluoro-N-methyl-5-(1-methyl-1H-pyrazol-4-yl)-benzamide in an analogous manner to Example 1410. Product isolated as a pale yellow solid (140 mg, 72%). m.p.=172-177° C.; LCMS (m/e) 565 (M+H); $^1$H-NMR (CDCl$_3$, 400 MHz) δ 8.85 (bs, 1H), 8.09 (s, 1H), 7.92 (s, 1H), 7.89-7.81 (m, 2H), 7.45 (s, 1H), 7.38 (d, 1H, J=11.5 Hz), 7.03-6.87 (m, 3H), 6.60-6.50 (m, 1H), 4.65-4.50 (m, 1H), 4.43-4.29 (m, 1H), 4.01 (s, 3H), 3.63-3.47 (m, 1H), 3.00 (d, 3H, J=4.8 Hz), 2.55-2.37 (m, 1H), 2.23-2.06 (m, 1H), 1.87 (s, 3H), 1.72-1.57 (m, 1H); $^{19}$F-NMR (CDCl$_3$, 400 MHz) δ −111.

Example 1425

2-[5-Chloro-2-(9-ethyl-6,7,8,9-tetrahydro-5-oxa-9-aza-benzocyclohepten-2-ylamino)-pyrimidin-4-ylamino]-3-fluoro-N-methyl-5-(1-methyl-1H-pyrazol-4-yl)-benzamide 2-[5-Chloro-2-(9-ethyl-6,7,8,9-tetrahydro-5-oxa-9-aza-benzocyclohepten-2-ylamino)-pyrimidin-4-ylamino]-3-fluoro-N-methyl-5-(1-methyl-1H-pyrazol-4-yl)-benzamide was prepared from 9-ethyl-6,7,8,9-tetrahydro-5-oxa-9-aza-benzocyclohepten-2-ylamine and 2-(2,5-dichloro-pyrimidin-4-ylamino)-3-fluoro-N-methyl-5-(1-methyl-1H-pyrazol-4-yl)-benzamide in an analogous manner to Example 1410. Product isolated as a white solid (58 mg, 30%). m.p.=253-255° C.; LCMS (m/e) 551 (M+H); $^1$H-NMR (CDCl$_3$, 400 MHz) δ 9.20 (s, 1H), 8.99 (s, 1H), 8.56-8.50 (m, 1H), 8.27 (s, 1H), 8.12 (s, 1H), 8.00 (s, 1H), 7.74-7.64 (m, 2H), 7.01 (d, 1H, J=9.6 Hz), 6.89 (s, 1H), 6.50 (d, 1H, J=8.6 Hz), 3.95-3.85 (m, 5H), 3.12-2.96 (m, 4H), 2.75 (d, 3H, J=4.5 Hz), 1.87-1.78 (m, 2H), 1.05 (t, 3H, J=7.1 Hz).

Example 1426

3-[5-Chloro-4-(2-fluoro-6-methylcarbamoyl-phenylamino)-pyrimidin-2-ylamino]-7,8-dihydro-6H-5-oxa-9-aza-benzocycloheptene-9-carboxylic acid 3-dimethylamino-propyl ester 1426a) 3-Dimethylamino-propan-1-ol (346 uL, 2.92 mmol) was dissolved in N-methylpyrrolidinone (25.0 mL, 259 mmol) and sodium hydride 60% dispersion in mineral oil (93.5 mg) was added. The reaction was stirred for 5 minutes and then 3-(3-chloro-propyl)-6-nitro-3H-benzoxazol-2-one (500 mg, 1.95 mmol) was added. The reaction was stirred at room temperature for 4 hours and then partitioned between ethyl ether (100 mL) and water (50 mL). The layers were separated and the organic layer was washed twice with water (50 mL). The organic layer was dried over sodium sulfate, filtered, and concentrated under reduced pressure. Purification by basic alumina chromatography using a gradient of 0-50% EtOAc/hex as the eluting solvent to obtain 3-nitro-7,8-dihydro-6H-5-oxa-9-aza-benzocycloheptene-9-carboxylic acid 3-dimethylamino-propyl ester as a yellow oil (437 mg, 69%). LCMS (m/e) 324 (M+H); $^1$H-NMR (CDCl$_3$, 400 MHz) δ 7.89-7.80 (m, 2H), 7.53-7.36 (m, 1H), 4.29-4.17 (m, 4H), 3.89-3.17 (m, 2H), 2.39-2.08 (m, 4H), 2.19 (s, 6H), 1.88-1.73 (m, 2H).

1426b) 3-Amino-7,8-dihydro-6H-5-oxa-9-aza-benzocycloheptene-9-carboxylic acid 3-dimethylamino-propyl ester was prepared from 3-nitro-7,8-dihydro-6H-5-oxa-9-aza-benzocycloheptene-9-carboxylic acid 3-dimethylamino-propyl ester in an analogous manner to Example 1417a. Product isolated as a brown foam (558 mg, 100%). LCMS (m/e) 294 (M+H); $^1$H-NMR (CDCl$_3$, 400 MHz) δ 6.98 (d, 1H, J=8.1 Hz), 6.48-6.35 (m, 2H), 4.20-3.95 (m, 4H), 2.93-2.80 (m, 4H), 2.68 (s, 6H), 2.17-1.90 (m, 4H).

1426c) 3-[5-Chloro-4-(2-fluoro-6-methylcarbamoyl-phenylamino)-pyrimidin-2-ylamino]-7,8-dihydro-6H-5-oxa-9-aza-benzocycloheptene-9-carboxylic acid 3-dimethylamino-propyl ester was prepared from 3-amino-7,8-dihydro-6H-5-oxa-9-aza-benzocycloheptene-9-carboxylic acid 3-dimethylamino-propyl ester and 2-(2,5-dichloro-pyrimidin-4-ylamino)-3-fluoro-N-methyl-benzamide in an analogous manner to Example 1410. Product isolated as a yellow foam (35 mg, 21%). LCMS (m/e) 572 (M+H); $^1$H-NMR (d6-DMSO, 400 MHz) δ 9.48-9.34 (m, 2H), 8.62-8.51 (m, 1H), 8.20 (s, 1H), 7.54-7.37 (m, 3H), 7.36-7.24 (m, 1H), 7.10 (d, 1H, J=9.1 Hz), 6.94 (d, 1H, J=8.7 Hz), 4.14-3.86 (m, 4H), 3.70-3.43 (m, 2H), 2.74 (d, 3H, J=4.4 Hz), 2.21-2.00 (m, 8H), 1.97-1.82 (m, 2H), 1.63-1.48 (m, 2H).

Example 1427

3-[5-Chloro-4-(2-fluoro-6-prop-2-ynylcarbamoyl-phenylamino)-pyrimidin-2-ylamino]-7,8-dihydro-6H-5-oxa-9-aza-benzocycloheptene-9-carboxylic acid 3-dimethylamino-propyl ester 3-[5-Chloro-4-(2-fluoro-6-prop-2-ynylcarbamoyl-phenylamino)-pyrimidin-2-ylamino]-7,8-dihydro-6H-5-oxa-9-aza-benzocycloheptene-9-carboxylic acid 3-dimethylamino-propyl ester was prepared from 3-amino-7,8-dihydro-6H-5-oxa-9-aza-benzocycloheptene-9-carboxylic acid 3-dimethylamino-propyl ester and 2-(2,5-dichloro-pyrimidin-4-ylamino)-3-fluoro-N-prop-2-ynyl-benzamide in an analogous manner to Example 1410. Product isolated as an orange foam (85 mg, 49%). LCMS (m/e) 596 (M+H); $^1$H-NMR (d6-DMSO, 400 MHz) δ 9.47-9.36 (m, 1H), 9.25-9.14 (m, 1H), 9.05-8.94 (m, 1H), 8.19 (s, 1H), 7.58-7.40 (m, 3H), 7.33-7.22 (m, 1H), 7.15-7.04 (m, 1H), 6.97-6.89 (m, 1H), 4.14-3.80 (m, 6H), 3.65-3.39 (m, 2H), 3.13-3.08 (m, 1H), 2.21-1.99 (m, 8H), 1.97-1.82 (m, 2H), 1.62-1.48 (m, 2H).

Example 1428

3-[5-Chloro-4-(2-methylcarbamoyl-thiophen-3-ylamino)-pyrimidin-2-ylamino]-7,8-dihydro-6H-5-oxa-9-aza-benzocycloheptene-9-carboxylic acid 3-dimethylamino-propyl ester 3-[5-Chloro-4-(2-methylcarbamoyl-thiophen-3-ylamino)-pyrimidin-2-ylamino]-7,8-dihydro-6H-5-oxa-9-aza-benzocycloheptene-9-carboxylic acid 3-dimethylamino-propyl ester was prepared from 3-amino-7,8-dihydro-6H-5-oxa-9-aza-benzocycloheptene-9-carboxylic acid 3-dimethylamino-propyl ester and 3-(2,5-dichloro-pyrimidin-4-ylamino)-thiophene-2-carboxylic acid methylamide in an analogous manner to Example 1410. Product isolated as an orange foam (85 mg, 52%). LCMS (m/e) 560 (M+H); $^1$H-NMR (d6-DMSO, 400 MHz) δ 11.65 (s, 1H), 9.58 (s, 1H), 8.57-8.45 (m, 1H), 8.32-8.21 (m, 2H), 7.82-7.73 (m, 1H), 7.61-7.50 (m, 1H), 7.33-7.21 (m, 1H), 7.20-7.10 (m, 1H), 4.20-3.90 (m, 5H), 7.75-3.50 (m, 2H), 2.78 (d, 3H, J=4.0 Hz), 2.22-1.85 (m, 11H).

Example 1429

3-[5-Chloro-4-(2-prop-2-ynylcarbamoyl-thiophen-3-ylamino)-pyrimidin-2-ylamino]-7,8-dihydro-6H-5-oxa-9-aza-benzocycloheptene-9-carboxylic acid 3-dimethylamino-propyl ester 3-[5-Chloro-4-(2-prop-2-ynylcarbamoyl-thiophen-3-ylamino)-pyrimidin-2-ylamino]-7,8-dihydro-6H-5-oxa-9-aza-benzocycloheptene-9-carboxylic acid 3-dimethylamino-propyl ester was prepared from 3-amino-7,8-dihydro-6H-5-oxa-9-aza-benzocycloheptene-9-carboxylic acid 3-dimethylamino-propyl ester and 3-(2,5-Dichloro-pyrimidin-4-ylamino)-thiophene-2-carboxylic acid prop-2-ynylamide in an analogous manner to Example 1410. Product isolated as a yellow foam (116 mg, 68%). LCMS (m/e) 584 (M+H); $^1$H-NMR (d6-DMSO, 400 MHz) δ 11.51 (s, 1H), 9.60 (s, 1H), 8.84-8.72 (m, 1H), 8.57-8.43 (m, 1H), 8.29 (s, 1H), 7.89-7.77 (m, 1H), 7.62-7.48 (m, 1H), 7.35-7.21 (m, 1H), 7.21-7.10 (m, 1H), 4.17-3.92 (m, 7H), 3.77-3.48 (m, 2H), 3.17-3.13 (m, 1H), 2.23-2.00 (m, 7H), 2.00-1.83 (m, 2H), 1.83-1.49 (m, 2H).

Example 1430

3-[5-Chloro-4-(2-fluoro-6-prop-2-ynylcarbamoyl-phenylamino)-pyrimidin-2-ylamino]-7,8-dihydro-6H-5-oxa-9-aza-benzocycloheptene-9-carboxylic acid methyl ester 1430a) 3-Nitro-7,8-dihydro-6H-5-oxa-9-aza-benzocycloheptene-9-carboxylic acid methyl ester was prepared from 3-(3-chloro-propyl)-6-nitro-3H-benzoxazol-2-one and methanol in an analogous manner to Example 1426a. Product isolated as a yellow oil (388 mg, 66%). LCMS (m/e) 253 (M+H); $^1$H-NMR (CDCl$_3$, 400 MHz) δ 7.91-7.81 (m, 2H), 7.56-7.37 (m, 1H), 4.32-4.18 (m, 2H), 3.95-3.80 (m, 2H), 3.79 (s, 3H), 2.22-2.12 (m, 2H).

1430b) 3-Amino-7,8-dihydro-6H-5-oxa-9-aza-benzocycloheptene-9-carboxylic acid methyl ester was prepared from 3-nitro-7,8-dihydro-6H-5-oxa-9-aza-benzocycloheptene-9-carboxylic acid methyl ester in an analogous manner to Example 1417a. Product isolated as a brown oil (340 mg, 100%). LCMS (m/e) 223 (M+H); $^1$H-NMR (CDCl$_3$, 400 MHz) δ 7.33-6.18 (m, 5H), 4.26-3.98 (m, 2H), 3.89-3.50 (m, 5H), 2.12-1.91 (m, 2H).

1430c) 3-[5-Chloro-4-(2-fluoro-6-prop-2-ynylcarbamoyl-phenylamino)-pyrimidin-2-ylamino]-7,8-dihydro-6H-5-oxa-9-aza-benzocycloheptene-9-carboxylic acid methyl ester was prepared from 3-amino-7,8-dihydro-6H-5-oxa-9-aza-benzocycloheptene-9-carboxylic acid methyl ester and 2-(2,5-dichloro-pyrimidin-4-ylamino)-3-fluoro-N-prop-2-ynyl-benzamide in an analogous manner to Example 1410. Product isolated as an orange foam (128 mg, 64%). LCMS (m/e) 525 (M+H); $^1$H-NMR (d6-DMSO, 400 MHz) δ 9.41 (s, 1H), 9.19 (s, 1H), 9.05-8.96 (m, 1H), 8.19 (s, 1H), 7.58-7.41 (m, 3H), 7.27 (s, 1H), 7.14-7.06 (m, 1H), 6.94 (d, 1H, J=8.7 Hz), 4.07-3.85 (m, 4H), 3.73-3.40 (m, 5H), 3.13-3.08 (m, 1H), 1.95-1.80 (m, 2H).

Example 1431

3-[5-Chloro-4-(2-fluoro-6-methylcarbamoyl-phenylamino)-pyrimidin-2-ylamino]-7,8-dihydro-6H-5-oxa-9-aza-benzocycloheptene-9-carboxylic acid methyl ester 3-[5-Chloro-4-(2-fluoro-6-methylcarbamoyl-phenylamino)-pyrimidin-2-ylamino]-7,8-dihydro-6H-5-oxa-9-aza-benzocycloheptene-9-carboxylic acid methyl ester was prepared from 3-amino-7,8-dihydro-6H-5-oxa-9-aza-benzocycloheptene-9-carboxylic acid methyl ester and 2-(2,5-dichloro-pyrimidin-4-ylamino)-3-fluoro-N-methyl-benzamide in an analogous manner to Example 1410. Product isolated as a white foam (71 mg, 37%). LCMS (m/e) 501 (M+H); $^1$H-NMR (d6-DMSO, 400 MHz) δ 9.48-9.34 (m, 2H), 8.61-8.52 (m, 1H), 8.20 (s, 1H), 7.55-7.37 (m, 3H), 7.33-7.25 (m, 1H), 7.14-7.07 (m, 1H), 6.99-6.91 (m, 1H), 4.03-3.87 (m, 2H), 3.73-3.44 (m, 5H), 2.74 (d, 3H, J=4.4 Hz), 1.96-1.82 (m, 2H).

Example 1432

3-[5-Chloro-4-(2-fluoro-6-methylcarbamoyl-phenylamino)-pyrimidin-2-ylamino]-7,8-dihydro-6H-5-oxa-9-aza-benzocycloheptene-9-carboxylic acid isopropyl ester 1432a) 3-Nitro-7,8-dihydro-6H-5-oxa-9-aza-benzocycloheptene-9-carboxylic acid isopropyl ester was prepared from 3-(3-chloro-propyl)-6-nitro-3H-benzoxazol-2-one and isopropyl alcohol in an analogous manner to Example 1426a. Product isolated as a yellow oil (413 mg, 63%). LCMS (m/e) 281 (M+H); $^1$H-NMR (CDCl$_3$, 400 MHz) δ 7.89-7.81 (m, 2H), 7.55-7.35 (m, 1H), 5.10-4.96 (m, 1H), 4.24 (t, 2H, J=5.5 Hz), 3.85 (t, 2H, J=5.6 Hz), 2.20-2.09 (m, 2H), 1.27 (d, 6H, J=5.7 Hz).

1432b) 3-Amino-7,8-dihydro-6H-5-oxa-9-aza-benzocycloheptene-9-carboxylic acid isopropyl ester was prepared from 3-nitro-7,8-dihydro-6H-5-oxa-9-aza-benzocycloheptene-9-carboxylic acid isopropyl ester in an analogous manner to Example 1417a. Product isolated as a brown oil (366 mg, 100%). LCMS (m/e) 251 (M+H); 1H-NMR (CDCl$_3$, 400

MHz) δ 8.85-7.97 (m, 2H), 7.47-6.83 (m, 3H), 5.05-4.85 (m, 1H), 4.23-4.00 (m, 2H), 3.85-3.58 (m, 2H), 2.15-1.96 (m, 2H), 1.40-1.04 (m, 6H).

1432c) 3-[5-Chloro-4-(2-fluoro-6-methylcarbamoyl-phenylamino)-pyrimidin-2-ylamino]-7,8-dihydro-6H-5-oxa-9-aza-benzocycloheptene-9-carboxylic acid isopropyl ester was prepared from 3-amino-7,8-dihydro-6H-5-oxa-9-aza-benzocycloheptene-9-carboxylic acid isopropyl ester and 2-(2,5-dichloro-pyrimidin-4-ylamino)-3-fluoro-N-methyl-benzamide in an analogous manner to Example 1410. Product isolated as a yellow foam (76 mg, 42%). LCMS (m/e) 529 (M+H); $^1$H-NMR (d6-DMSO, 400 MHz) δ 9.48-9.32 (m, 2H), 8.63-8.51 (m, 1H), 8.20 (s, 1H), 7.55-7.36 (m, 3H), 7.28 (s, 1H), 7.09 (d, 1H, J=8.8 Hz), 6.92 (d, 1H, J=8.5 Hz), 4.87-4.71 (m, 1H), 4.05-3.85 (m, 2H), 3.67-3.40 (m, 2H), 2.74 (d, 3H, J=4.2 Hz), 1.97-1.81 (m, 2H), 1.33-1.00 (m, 6H).

Example 1433

3-[5-Chloro-4-(2-fluoro-6-prop-2-ynylcarbamoyl-phenylamino)-pyrimidin-2-ylamino]-7,8-dihydro-6H-5-oxa-9-aza-benzocycloheptene-9-carboxylic acid isopropyl ester 3-[5-Chloro-4-(2-fluoro-6-prop-2-ynylcarbamoyl-phenylamino)-pyrimidin-2-ylamino]-7,8-dihydro-6H-5-oxa-9-aza-benzocycloheptene-9-carboxylic acid isopropyl ester was prepared from 3-amino-7,8-dihydro-6H-5-oxa-9-aza-benzocycloheptene-9-carboxylic acid isopropyl ester and 2-(2,5-dichloro-pyrimidin-4-ylamino)-3-fluoro-N-prop-2-ynyl-benzamide in an analogous manner to Example 1410. Product isolated as a pale yellow solid (99 mg, 53%). m.p.=242-244° C.; LCMS (m/e) 553 (M+H); $^1$H-NMR (d6-DMSO, 400 MHz) δ 9.47-9.35 (m, 1H), 9.25-9.15 (m, 1H), 9.04-8.95 (m, 1H), 8.19 (s, 1H), 7.57-7.40 (m, 3H), 7.26 (s, 1H), 7.13-7.04 (m, 1H), 6.98-6.87 (m, 1H), 4.87-4.71 (m, 1H), 4.06-3.82 (m, 4H), 3.68-3.41 (m, 2H), 3.11 (s, 1H), 1.97-1.79 (m, 2H), 1.33-0.98 (m, 6H).

Example 1434

3-{5-Chloro-4-[2-fluoro-6-methylcarbamoyl-4-(1-methyl-1H-pyrazol-4-yl)-phenylamino]-pyrimidin-2-ylamino}-7,8-dihydro-6H-5-oxa-9-aza-benzocycloheptene-9-carboxylic acid methyl ester The title compound was prepared from 3-amino-7,8-dihydro-6H-5-oxa-9-aza-benzocycloheptene-9-carboxylic acid methyl ester and 2-(2,5-dichloro-pyrimidin-4-ylamino)-3-fluoro-N-methyl-5-(1-methyl-1H-pyrazol-4-yl)-benzamide in an analogous manner to Example 1410. Product isolated as a yellow solid (128 mg, 58%). m.p.=175-181° C.; LCMS (m/e) 581 (M+H); $^1$H-NMR (d6-DMSO, 400 MHz) δ 9.39 (bs, 1H), 9.27 (s, 1H), 8.64-8.54 (m, 1H), 8.26 (s, 1H), 8.19 (s, 1H), 7.99 (s, 1H), 7.79-7.65 (m, 2H), 7.31 (s, 1H), 7.19-7.08 (m, 1H), 6.93 (d, 1H, J=8.7 Hz), 3.94-3.79 (m, 2H), 3.89 (s, 3H), 3.74-3.37 (m, 5H), 2.76 (d, 3H, J=4.3 Hz), 1.88-1.76 (m, 2H).

Example 1435

3-[5-Chloro-4-(2-methylcarbamoyl-thiophen-3-ylamino)-pyrimidin-2-ylamino]-7,8-dihydro-6H-5-oxa-9-aza-benzocycloheptene-9-carboxylic acid isopropyl ester The title compound was prepared from 3-amino-7,8-dihydro-6H-5-oxa-9-aza-benzocycloheptene-9-carboxylic acid isopropyl ester and 3-(2,5-dichloro-pyrimidin-4-ylamino)-thiophene-2-carboxylic acid methylamide in an analogous manner to Example 1410. Product isolated as an orange foam (152 mg, 87%). LCMS (m/e) 517 (M+H); $^1$H-NMR (d6-DMSO, 400 MHz) δ 11.65 (s, 1H), 9.57 (s, 1H), 8.56-8.44 (m, 1H), 8.27 (s, 1H), 8.25 (d, 1H, J=4.3 Hz), 7.76 (d, 1H, J=5.4 Hz), 7.52 (s, 1H), 7.33-7.20 (m, 1H), 7.20-7.07 (m, 1H), 4.91-4.74 (m, 1H), 4.13-3.96 (m, 2H), 3.73-3.50 (m, 2H), 2.78 (d, 3H, J=4.3 Hz), 2.00-1.85 (m, 2H), 1.35-1.00 (m, 6H).

Example 1436

3-[5-Chloro-4-(2-fluoro-6-methylcarbamoyl-phenylamino)-pyrimidin-2-ylamino]-7,8-dihydro-6H-5-oxa-9-aza-benzocycloheptene-9-carboxylic acid 2-methoxy-ethyl ester 1436a) 3-Nitro-7,8-dihydro-6H-5-oxa-9-aza-benzocycloheptene-9-carboxylic acid 2-methoxy-ethyl ester was prepared from 3-(3-chloro-propyl)-6-nitro-3H-benzoxazol-2-one and 2-methoxyethanol in an analogous manner to Example 1426a. Product isolated as a yellow oil (175 mg, 25%). LCMS (m/e) 297 (M+H); $^1$H-NMR (CDCl$_3$, 400 MHz) δ 7.89-7.83 (m, 2H), 7.57-7.42 (m, 1H), 4.43-4.20 (m, 4H), 3.95-3.81 (m, 2H), 3.70-3.54 (m, 2H), 3.38 (s, 3H), 2.23-2.12 (m, 2H).

1436b) 3-Amino-7,8-dihydro-6H-5-oxa-9-aza-benzocycloheptene-9-carboxylic acid 2-methoxy-ethyl ester was prepared from 3-nitro-7,8-dihydro-6H-5-oxa-9-aza-benzocycloheptene-9-carboxylic acid 2-methoxy-ethyl ester in an analogous manner to Example 1417a. Product isolated as a brown oil (153 mg, 100%). $^1$H-NMR (CDCl$_3$, 400 MHz) δ 7.22-6.97 (m, 1H), 6.63-6.33 (m, 2H), 5.40-4.60 (m, 2H), 4.40-4.17 (m, 2H), 4.17-3.95 (m, 2H), 3.88-3.17 (m, 7H), 2.13-1.93 (m, 2H).

1436c) The title compound was prepared from 3-amino-7,8-dihydro-6H-5-oxa-9-aza-benzocycloheptene-9-carboxylic acid 2-methoxy-ethyl ester and 2-(2,5-dichloro-pyrimidin-4-ylamino)-3-fluoro-N-methyl-benzamide in an analogous manner to Example 1410. Product isolated as an orange foam (80 mg, 52%). LCMS (m/e) 545 (M+H); 1H-NMR (CDCl$_3$, 400 MHz) δ 8.95-8.73 (m, 1H), 8.09 (s, 1H), 7.41-7.15 (m, 4H), 7.14-6.87 (m, 3H), 6.30-6.13 (m, 1H), 4.40-4.18 (m, 2H), 4.13-3.97 (m, 2H), 3.82-3.61 (m, 2H), 3.57-3.39 (m, 3H), 3.34-3.22 (m, 2H), 2.97-2.86 (m, 3H), 2.13-2.00 (m, 2H).

Example 1437

3-[5-Chloro-4-(2-fluoro-6-prop-2-ynylcarbamoyl-phenylamino)-pyrimidin-2-ylamino]-7,8-dihydro-6H-5-oxa-9-aza-benzocycloheptene-9-carboxylic acid 2-methoxy-ethyl ester The title compound was prepared from 3-amino-7,8-dihydro-6H-5-oxa-9-aza-benzocycloheptene-9-carboxylic acid 2-methoxy-ethyl ester and 2-(2,5-dichloro-pyrimidin-4-ylamino)-3-fluoro-N-prop-2-ynyl-benzamide in an analogous manner to Example 1410. Product isolated as a white foam (70 mg, 44%). LCMS (me/) 569 (M+H); $^1$H-NMR (d6-DMSO, 400 MHz) δ 9.47-9.36 (m, 1H), 9.24-9.15 (m, 1H), 9.05-8.95 (m, 1H), 8.19 (s, 1H), 7.57-7.41 (m, 3H), 7.33-7.23 (m, 1H), 7.14-7.05 (m, 1H), 6.93 (d, 1H, J=8.7 Hz), 4.23-3.87 (m, 6H), 3.67-3.49 (m, 2H), 3.46-3.37 (m, 1H), 3.36-3.26 (m, 2H), 3.23-3.14 (m, 2H), 3.11 (t, 1H, J=2.4 Hz), 1.97-1.84 (m, 2H).

Example 1438

3-[5-Chloro-4-(2-fluoro-6-methylcarbamoyl-phenylamino)-pyrimidin-2-ylamino]-7,8-dihydro-6H-5-oxa-9-aza-benzocycloheptene-9-carboxylic acid 1-methyl-piperidin-3-yl ester

1438a) 3-Nitro-7,8-dihydro-6H-5-oxa-9-aza-benzocycloheptene-9-carboxylic acid 1-methyl-piperidin-3-yl ester was prepared from 3-(3-chloro-propyl)-6-nitro-3H-benzoxazol-2-one and 1-methyl-piperidin-3-ol in an analogous manner to Example 1426a. Product isolated as a yellow oil (420 mg, 53%). LCMS (m/e) 336 (M+H); $^1$H-NMR (CDCl$_3$, 400 MHz) δ 7.89-7.80 (m, 2H), 7.58-7.44 (m, 1H), 4.92-4.81 (m, 1H), 4.30-4.18 (m, 2H), 3.98-3.72 (m, 2H), 2.82-2.71 (m, 1H), 2.56-2.45 (m, 1H), 2.27 (s, 3H), 2.27-2.07 (m, 4H), 1.97-1.84 (m, 1H), 1.80-1.66 (m, 1H), 1.66-1.52 (m, 1H), 1.52-1.30 (m, 1H).

1438b) 3-Amino-7,8-dihydro-6H-5-oxa-9-aza-benzocycloheptene-9-carboxylic acid 1-methyl-piperidin-3-yl ester was prepared from 3-nitro-7,8-dihydro-6H-5-oxa-9-aza-benzocycloheptene-9-carboxylic acid 1-methyl-piperidin-3-yl ester in an analogous manner to Example 1417a. Product isolated as an orange oil (378 mg, 100%). LCMS (m/e) 306 (M+H).

1438c) The title compound was prepared from 3-amino-7,8-dihydro-6H-5-oxa-9-aza-benzocycloheptene-9-carboxylic acid 1-methyl-piperidin-3-yl ester and 2-(2,5-dichloro-pyrimidin-4-ylamino)-3-fluoro-N-methyl-benzamide in an analogous manner to Example 1410. Product isolated as an orange foam (84 mg, 44%). LCMS (m/e) 584 (M+H); 1H-NMR (CDCl$_3$, 400 MHz) δ 8.98-8.75 (m, 1H), 8.09 (s, 1H), 7.40-7.17 (m, 4H), 7.16-6.97 (m, 2H), 6.95-6.84 (m, 1H), 6.40-6.22 (m, 1H), 4.91-4.70 (m, 1H), 4.15-3.95 (m, 2H), 3.82-3.58 (m, 2H), 2.98-2.77 (m, 4H), 2.64-2.48 (m, 1H), 2.38-2.13 (m, 4H), 2.11-1.75 (m, 5H), 1.65-1.40 (m, 1H), 1.30-1.10 (m, 1H); $^{19}$F-NMR (CDCl$_3$, 400 MHz) δ −111.

Example 1439

3-[5-Chloro-4-(2-fluoro-6-prop-2-ynylcarbamoyl-phenylamino)-pyrimidin-2-ylamino]-7,8-dihydro-6H-5-oxa-9-aza-benzocycloheptene-9-carboxylic acid 1-methyl-piperidin-3-yl ester

The title compound was prepared from 3-amino-7,8-dihydro-6H-5-oxa-9-aza-benzocycloheptene-9-carboxylic acid 1-methyl-piperidin-3-yl ester and 2-(2,5-dichloro-pyrimidin-4-ylamino)-3-fluoro-N-prop-2-ynyl-benzamide in an analogous manner to Example 1410. Product isolated as an orange foam (107 mg, 54%). LCMS (m/e) 608 (M+H); 1H-NMR (CDCl$_3$, 400 MHz) δ 8.68-8.42 (m, 1H), 8.10 (s, 1H), 7.46-7.18 (m, 4H), 7.15-6.94 (m, 2H), 6.93-6.78 (m, 1H), 6.56-6.43 (m, 1H), 4.92-4.70 (m, 1H), 4.20-3.97 (m, 4H), 3.85-3.55 (m, 2H), 2.89-2.77 (m, 1H), 2.64-2.48 (m, 1H), 2.37-2.12 (m, 5H), 2.11-1.73 (m, 5H), 1.65-1.40 (m, 1H), 1.30-1.12 (m, 1H); 19F-NMR (CDCl3, 400 MHz) δ −113.

Example 1440

3-[5-Chloro-4-(2-methylcarbamoyl-thiophen-3-ylamino)-pyrimidin-2-ylamino]-7,8-dihydro-6H-5-oxa-9-aza-benzocycloheptene-9-carboxylic acid 1-methyl-piperidin-3-yl ester

The title compound was prepared from 3-amino-7,8-dihydro-6H-5-oxa-9-aza-benzocycloheptene-9-carboxylic acid 1-methyl-piperidin-3-yl ester and 3-(2,5-dichloro-pyrimidin-4-ylamino)-thiophene-2-carboxylic acid methylamide in an analogous manner to Example 1410. Product isolated as an orange foam (112 mg, 60%). LCMS (m/e) 572 (M+H); $^1$H-NMR (CDCl$_3$, 400 MHz) δ 11.32 (bs, 1H), 8.47-8.30 (m, 1H), 8.13 (s, 1H), 7.46-7.13 (m, 3H), 7.13-7.04 (m, 1H), 7.01-6.88 (m, 1H), 5.82-5.68 (m, 1H), 4.98-4.71 (m, 1H), 4.25-4.06 (m, 2H), 3.90-3.64 (m, 2H), 3.03 (d, 3H, J=4.8 Hz), 2.91-2.81 (m, 1H), 2.64-2.50 (m, 1H), 2.37-2.21 (m, 3H), 2.16-2.04 (m, 3H), 2.03-1.75 (m, 3H), 1.65-1.45 (m, 1H), 1.32-1.13 (m, 1H).

Example 1451

N-{(1R,2R)-2-[5-Chloro-2-(1-ethyl-5-oxo-2,3,4,5-tetrahydro-1H-benzo[e][1,4]diazepin-8-ylamino)-pyrimidin-4-ylamino]-cyclohexyl}-methanesulfonamide

1451a). Into a round bottom flask, 2-fluoro-4-nitro-benzoic acid methyl ester (9.85 g, 0.0495 mol; prepared as described in Example 471a), N-(2-ethylamino-ethyl)-2,2,2-trifluoro-acetamide (10.9 g, 0.0594 mol, prepared as described Example 414a) N,N-dimethylformamide (50.0 mL, 0.646 mol) and potassium carbonate (16.4 g, 0.119 mol) were added and heated at 65° C. overnight. The solid was filtered and washed with EtOAc. The solvent was removed under vacuum. The desired product was isolated via ISCO column with DCM and methanol as eluant (0 to 10%). The collected fractions afforded 2-{ethyl-[2-(2,2,2-trifluoro-acetylamino)-ethyl]-amino}-4-nitro-benzoic acid methyl ester $^1$H-NMR (CDCl$_3$, 400 MHz): δ 8.00-8.10 (bs, 1H), 7.98 (s, 1H), 7.85-7.92 (m, 1H), 7.78-7.7.84 (m, 1H), 3.97 (s, 3H), 3.37-3.55 (m, 4H), 3.10 (q, 2H), 1.04 (t, 3H)

1451b). Into a round bottom flask, 2-{ethyl-[2-(2,2,2-trifluoro-acetylamino)-ethyl]-amino}-4-nitro-benzoic acid methyl ester (4.80 g, 13.2 mmol), methanol (60.0 mL, 1480 mmol) and sodium methoxide (0.86 g, 16 mmol) were added. The reaction was heated to 50 degree for 18 hours. TLC suggested 50% conversion. sodium methoxide (0.86 g, 16 mmoles) was added. The reaction was heated to reflux for 4 hours. The reaction was partitioned with water and DCM. The organic was separated, washed with Brine, and dried over magnesium sulfate. The solid was filtered and washed with DCM. The organic was removed under vacuum to afford 1-ethyl-8-nitro-1,2,3,4-tetrahydro-benzo[e][1,4]diazepin-5-one as a yellow solid (2.24 g, 71%). $^1$H-NMR (DMSO-D$_6$, 400 MHz): δ 8.48 (t, 1H), 7.72 (d, 1H), 7.65 (d, 1H), 7.64 (s, 1H), 3.18-3.32 (m, 6H), 1.15 (t, 3H)

1451c). Into a round bottom flask, 1-ethyl-8-nitro-1,2,3,4-tetrahydro-benzo[e][1,4]diazepin-5-one (2.40 g, 0.0102 mol) ethanol (120 mL, 2.0 mol), palladium on carbon 10% (10:90, Palladium:carbon black, 0.500 g) were added. The reaction was evacuated and charged with hydrogen. The reaction was stirred at room temperature for over the weekend under an atmosphere of hydrogen via balloon. The solid was filtered through Celite and washed with methanol. The solvent was removed under vacuum. The desired product was isolated via column chromatography with DCM and methanol as eluant (0 to 10% methanol). The collected fractions afforded 8-amino-1-ethyl-1,2,3,4-tetrahydro-benzo[e][1,4]diazepin-5-one as a white solid (2.00 g, 95%). $^1$H-NMR (DMSO-D$_6$, 400 MHz): δ 7.34 (d, 1H), 5.89 (d, 1H), 5.83 (bs, 1H), 5.75 (s, 1H). 5.19 (bs, 2H), 3.36-3.45 (m, 4H), 3.27-3.35 (m, 2H), 1.05 (t, 3H)

1451d). Into a microwave vial, 8-amino-1-ethyl-1,2,3,4-tetrahydro-benzo[e][1,4]diazepin-5-one (75 mg, 0.00036 mol), N-[(1R,2R)-2-(2,5-dichloro-pyrimidin-4-ylamino)-cyclohexyl]-methanesulfonamide (113 mg, 0.332 mmol), 4 M of hydrogen chloride in dioxane (0.2 mL), and 2-methoxyethanol (2.3 mL) were added. The reaction was then heated in microwave at 120 degree Celsius for one hour. MP-carbonate (3.16 mmol/g loading; 263 mg, 0.83 mmole) and methanol (10 mL) were added. The mixture was stirred at room temperature over night. The solid was filtered and washed with methanol. The desired product was isolated via column chromatography with DCM and methanol as eluant. The collected fractions afforded N-{(1R,2R)-2-[5-Chloro-2-(1-ethyl-5-oxo-2,3,4,5-tetrahydro-1H-benzo[e][1,4]diazepin-8-ylamino)-pyrimidin-4-ylamino]-cyclohexyl}-methanesulfonamide as a yellow solid (35 mg, 19%). $^1$H-NMR (DMSO-D$_6$, 400 MHz): δ 9.19 (s, 1H), 7.94 (s, 1H), 7.51 (d, 1H), 7.12 (d, 1H), 7.07 (d, 1H), 6.97 (s, 1H), 6.75 (d, 1H), 5.99 (bs, 1H), 3.70-3.88 (m, 1H), 3.25-3.52 (m, 7H), 2.92 (s, 3H), 1.97-2.10 (m, 2H), 1.69 (bs, 2H), 1.15-1.48 (m, 4H), 1.08 (t, 3H) LCMS (ESI+) 508.26 (M+H). MP 216-220° C.

Example 1452

2-[5-Chloro-2-(1-ethyl-5-oxo-2,3,4,5-tetrahydro-1H-benzo[e][1,4]diazepin-8-ylamino)-pyrimidin-4-ylamino]-N-methyl-benzamide 1452a). Following an analogous procedure as described in Example 1451, 8-amino-1-ethyl-1,2,3,4-tetrahydro-benzo[e][1,4]diazepin-5-one was converted to 2-[5-Chloro-2-(1-ethyl-5-oxo-2,3,4,5-tetrahydro-1H-benzo[e][1,4]diazepin-8-ylamino)-pyrimidin-4-ylamino]-N-methyl-benzamide (50 mg, 32%). $^1$H-NMR (CDCl$_3$, 400 MHz): δ 11.01 (s, 1), 8.60 (d, 1H), 8.10 (s, 1H), 7.77 (d, 1H), 7.43-7.52 (m, 2H), 7.21 (s, 1H), 7.10 (t, 1H), 7.04 (bs, 1H), 6.73 (d, 1H), 6.32 (bs, 1H), 3.48-3.70 (m, 6H), 3.02 (d, 3H), 1.21 (t, 3H). LC/MS ESI– (M–H) 464.33. MP 168-171° C.

Example 1453

8-{5-Chloro-4-[2-(1-methyl-1H-imidazol-2-yl)-phenylamino]-pyrimidin-2-ylamino}-1-ethyl-1,2,3,4-tetrahydro-benzo[e][1,4]diazepin-5-one 1453a). Following an analogous procedure as described in Example 1451, 8-amino-1-ethyl-1,2,3,4-tetrahydro-benzo[e][1,4]diazepin-5-one was converted to 8-{5-Chloro-4-[2-(1-methyl-1H-imidazol-2-yl)-phenylamino]-pyrimidin-2-ylamino}-1-ethyl-1,2,3,4-tetrahydro-benzo[e][1,4]diazepin-5-one (36 mg, 22%). This. $^1$H-NMR (DMSO-D$_6$, 400 MHz): δ 11.14 (s, 1H), 9.38 (s, 1H), 8.68 (d, 1H), 8.16 (s, 1H), 7.65 (d, 1H), 7.53 (d, 1H), 7.44 (t, 1H) 7.36 (s, 1H), 7.23 (t, 1H), 7.17 (s, 1H), 7.01 (s, 1H), 6.94 (d, 1H), 6.05 (s, 1H), 3.77 (s, 3H), 3.37-3.52 (m, 6H), 1.09 (t, 3H). LC/MS (ESI+) 489.27 (M+H). MP 143-151° C.

Example 1454

2-[5-Chloro-2-(4-ethyl-5-oxo-2,3,4,5-tetrahydro-1H-benzo[e][1,4]diazepin-8-ylamino)-pyrimidin-4-ylamino]-3-fluoro-N-methyl-benzamide 1454a.). Into a round bottom flask, 2-fluoro-4-nitro-benzoic acid methyl ester (7.80 g, 0.0392 mol), N-ethyl-1,2-ethanediamine (3.80 g, 0.0431 mol), potassium carbonate (12 g, 0.086 mol) and N,N-dimethylformamide (50 mL, 0.6 mol) were added and heated at 75° C. overnight. The solid was filtered and washed with ethyl acetate. The solvent was removed under vacuum. The desired product was isolated via ISCO column chromatography with hexane and ethyl acetate as eluant (0 to 100% EtOAc). The collected fractions afford 4-ethyl-8-nitro-1,2,3,4-tetrahydro-benzo[e][1,4]diazepin-5-one as an off white solid. 1H-NMR (CDCl$_3$, 400 MHz): δ 8.00 (d, 1H), 7.59 (d, 1H), 7.48 (s, 1H), 4.45 (bs, 1H), 3.50-3.80 (m, 6H), 1.25 (t, 3H)

1454b). Into a Round bottom flask, 4-Ethyl-8-nitro-1,2,3,4-tetrahydro-benzo[e][1,4]diazepin-5-one (3.80 g, 0.0162 mol), Ethanol (100 mL, 2 mol;) and 10% Pd/C (10:90, Palladium:carbon black, 0.50 g) were added. The mixture was evacuated and charged with hydrogen (3 times). The reaction was stirred at room temperature overnight under an atmosphere of Hydrogen via a balloon. The solid was filtered and washed with ethanol. The solvent was removed under vacuum to give 8-amino-4-ethyl-1,2,3,4-tetrahydro-benzo[e][1,4]diazepin-5-one as a white solid. $^1$H-NMR (DMSO-D$_6$, 400 MHz): δ 7.35 (d, 1H), 5.95 (d, 1H), 5.85 (s, 1H), 5.78 (s, 1H), 5.20 (s, 2H), 3.26-3.50 (m, 6H), 1.08 (t, 3H)

1454c). Into a microwave vial, 8-amino-4-ethyl-1,2,3,4-tetrahydro-benzo[e][1,4]diazepin-5-one (0.100 g, 0.000487 mol), 2-(2,5-dichloro-pyrimidin-4-ylamino)-3-fluoro-N-methyl-benzamide (0.14 g, 0.00046 mol), 10-camphorsulfonic acid (0.22 g, 0.00092 mol) and isopropyl alcohol (1.3 mL, 0.017 mol) were added and heated in the microwave at 120° C. for 40 minutes. The solvent was removed under vacuum. The solid was dissolved in EtOAc and washed with saturated NaHCO$_3$. The organic was separated, washed with Brine, and dried over magnesium sulfate. The solid was filtered and washed with EtOAc. The solvent was removed under vacuum. The product was isolated via Gilson prep-HPLC to give a TFA salt (30 mg, 13%). $^1$H-NMR (CDCl$_3$, 400 MHz): δ10.97 (bs, 1H), 9.52 (bs, 1H), 7.75 (s, 1H), 7.70 (bs, 1H), 7.28-7.50 m, 4H), 6.90 (d, 1H), 6.28 (bs, 1H), 3.44-3.65 (m, 7H), 3.01 (d, 1H), 1.25 (t, 3H). LC/MS (ESI+) 484.21 (M+H).

Example 1455

8-{5-Chloro-4-[2-(2-morpholin-4-yl-ethoxy)-phenylamino]-pyrimidin-2-ylaminol}-1-ethyl-1,2,3,4-tetrahydro-benzo[e][1,4]diazepin-5-one 1455a). Into a round bottom flask, 2-(2-morpholin-4-yl-ethoxy)-phenylamine (1.02 g, 4.59 mmol), N,N-dimethylformamide (5.0 mL, 64 mmol), 2,4,5-trichloro-pyrimidine (1.00 g, 5.45 mmol) and potassium carbonate (0.951 g, 6.88 mmol) were added. The reaction was heated at 50° C. for 2 hours. Water (50 mL) was added. The reaction was stirred at room temperature for 30 minutes. The solid was filtered, washed with water and dried under vacuum to afford an off-white solid (1.47 g, 87%). $^1$H-NMR (CDCl$_3$, 400 MHz): δ 8.99 (s, 1H), 8.38 (s, 1H), 7.60 (d, 1H), 8.24 (t, 1H), 7.14 (d, 1H), 7.01 (t, 1H), 4.14 (t, 2H), 3.49 (t, 4H), 2.60 (t, 2H), 2.35 (bs, 4H).

1455b). Following an analogous procedure as described in Example 1451, 8-amino-1-ethyl-1,2,3,4-tetrahydro-benzo[e][1,4]diazepin-5-one was converted to 8-{5-Chloro-4-[2-(2-morpholin-4-yl-ethoxy)-phenylamino]-pyrimidin-2-ylamino}-1-ethyl-1,2,3,4-tetrahydro-benzo[e][1,4]diazepin-5-one TFA salt (78 mg, 56%). $^1$H-NMR (DMSO-D$_6$, 400 MHz) δ NMR 9.50 (bs, 1H), 9.40 (s, 1H), 8.45 (s, 1H), 8.16 (s, 1H), 7.87 (d, 1H), 7.38 (d, 1H), 7.30 (t, 1H), 7.20 9 d, 1H), 6.85 (t, 1H), 6.80 (bs, 2H), 4.42 (s, 2H), 3.94 (t, 2H), 3.35-3.70 (m, 12H), 3.0-3.25 (m, 2H), 1.07 (t, 3H). LC/MS (ESI+) 558.37 (M+H). MP 223-225° C.

Example 1456

N-{(1R,2R)-2-[5-Chloro-2-(1,4-diethyl-7-methoxy-2,3,4,5-tetrahydro-1H-benzo[e][1,4]diazepin-8-ylamino)-pyrimidin-4-ylamino]-cyclohexyl}-methanesulfonamide 1456a) Into a round bottom flask, 2,5-difluoro-4-nitrobenzoic acid (5.00 g, 0.0246 mol) and methanol (20.0 mL, 0.494 mol;) was added. The reaction was heated at 45° C. for one hour. The solvent was removed under vacuum. 1N HCl was added to pH 4. The solid was filtered and washed with water to give 2-fluoro-5-methoxy-4-nitro-benzoic acid as an off white solid (2.84 g, 54%). $^1$H-NMR (DMSO-D$_6$, 400 MHz): δ 13.90 (bs, 1H), 8.08 (d, 1H), 7.72 (d, 1H), 3.94 (s, 3H).

1456b). Into a round bottom flask, 2-fluoro-5-methoxy-4-nitro-benzoic acid (2.84 g, 0.0132 mol;), toluene (25 mL, 0.23 mol), methanol (5 mL, 0.1 mol;) were added. 2.00 M of trimethylsilyldiazomethane in ether (7.92 mL) was added drop wise at 5° C. The reaction was stirred at room temperature for 2 hours. The solvent was removed under vacuum to afford a yellow solid. The solid was triturated with 10% Et$_2$O and hexane to give 2-fluoro-5-methoxy-4-nitro-benzoic acid methyl ester as an off white solid (2.84, 93%). $^1$H-NMR (DMSO-D$_6$, 400 MHz): δ 8.06 (d, 1H), 7.70 (d, 1H). 4.14 (s, 3H), 3.91 (s, 3H).

1456c). Into a round bottom flask, 2-fluoro-5-methoxy-4-nitro-benzoic acid methyl ester (5.10 g, 0.0222 mol), N,N'-diethyl-ethane-1,2-diamine (2.84 g, 0.0245 mol), potassium carbonate (6.77 g, 0.0490 mol) and N,N-Dimethylformamide (50 mL, 0.6 mol) were added. The reaction was heated to 50 degree for 24 hours. DMF was then removed under vacuum. The solid was partitioned with water 200 mL. The aqueous was then extracted with EtOAc (3×150 ml). The combined organic was then washed with brine, dried over MgSO$_4$. The solid was filtered and washed with EtOAc. The solvent was removed under vacuum. The desired product was isolated via column chromatography with hexane/EtOAc as eluant (0 to 100%). The collected fractions afforded 1,4-diethyl-7-methoxy-8-nitro-1,2,3,4-tetrahydro-benzo[e][1,4]diazepin-5-one as a yellow solid (0.23 g, 3.5%) $^1$H-NMR (CDCl$_3$, 400 MHz): δ 7.20 (s, 1H), 7.11 (s, 1H), 6.27 (bs, 1H), 3.84 (s, 3H), 3.64 (q, 2H), 3.37 (t, 2H), 3.22 (bs, 2H), 3.10 (t, 2H), 1.25 (t, 3H), 1.13 (t, 3H).

1456d) Into a round bottom flask, 1,4-diethyl-7-methoxy-8-nitro-1,2,3,4-tetrahydro-benzo[e][1,4]diazepin-5-one (230 mg), 10% Pd/C, (50.0 mg) and ethanol (20 mL, 0.4 mol) were added. The mixture was evacuated and charged with hydrogen (3×). The reaction was stirred under hydrogen balloon for 4 hours. The solid was filtered through Celite. The organic was removed under vacuum to give 8-amino-1,4-diethyl-7-methoxy-1,2,3,4-tetrahydro-benzo[e][1,4]diazepin-5-one as a brown solid (0.21 g, 100%). $^1$H-NMR (CDCl$_3$, 400 MHz): δ 7.08 (s, 1H), 6.24 (s, 1H), 4.17 (s, 2H), 3.78 (s, 3H), 3.59 (q, 2H), 3.33 (t, 2H), 3.16 (t, 2H), 3.02 (q, 2H), 1.23 (t, 3H), 1.10 (t, 3H).

1456e) Into a round bottom flask, 8-amino-1,4-diethyl-7-methoxy-1,2,3,4-tetrahydro-benzo[e][1,4]diazepin-5-one (0.30 g, 0.0011 mol), 1,4-dioxane (10.0 mL, 0.128 mol) and 2.00 M of borane-dimethyl sulfide complex in toluene (4.56 mL) were added and heated to reflux overnight. The solvent was removed under vacuum. 6N HCl (5 mL) was added and heated to reflux for one hour. The mixture was cooled to room temperature. 50% NaOH was added to pH 12. The aqueous was extracted with DCM (3×100 mL) The organic was separated, washed with Brine, and dried over magnesium sulfate. The solid was filtered and washed with EtOAc. The solvent was removed under vacuum. The product was isolated via ISCO column chromatography with DCM and NH$_3$ in methanol as eluant (0 to 15% NH$_3$ in methanol). The collected fractions afforded 1,4-diethyl-7-methoxy-2,3,4,5-tetrahydro-1H-benzo[e][1,4]diazepin-8-ylamine as an off white solid (0.10 mg, 30%). 1,4-diethyl-7-methoxy-2,3,4,5-tetrahydro-1H-benzo[e][1,4]diazepin-8-ylamine was converted to 1,4-diethyl-7-methoxy-2,3,4,5-tetrahydro-1H-benzo[e][1,4]diazepin-8-ylamine was converted to N-{(1R,2R)-2-[5-Chloro-2-(1,4-diethyl-7-methoxy-2,3,4,5-tetrahydro-1H-benzo[e][1,4]diazepin-8-ylamino)-pyrimidin-4-ylamino]-cyclohexyl}-methanesulfonamide TFA salt as described in Example 787. The product was purified via Gilson HPLC to give of lyophilized solid (14 mg, 8%). $^1$H-NMR (DMSO-D$_6$, 400 MHz) δ 9.52 (bs, 1H), 8.35 (bs, 1H), 8.08 (s, 1H), 7.83 (bs, 1H), 7.35 (bs, 1H), 7.22 (s, 1H), 7.10-7.18 (m, 1H), 4.15-4.28 (m, 1H), 3.83-3.94 (m, 1H), 3.85 (s, 3H), 2.92-3.40 (m, 8H) 2.98 (s, 3H), 1.80-2.08 (m, 2H), 1.60-1.75 (m, 2H), 1.40-1.52 (m, 2H), 1.10-1.30 (complex m, 10H). LC/MS (ESI+) 572.36.

Example 1457

{8-[4-((1R,2S,3R,4S)-3-Carbamoyl-bicyclo[2.2.1]hept-2-ylamino)-5-chloro-pyrimidin-2-ylamino]-1-ethyl-5-oxo-1,2,3,5-tetrahydro-benzo[e][1,4]diazepin-4-yl}-acetic acid 2-methoxy-ethyl ester 1457a). Into a round bottom flask, 1-ethyl-8-nitro-1,2,3,4-tetrahydro-benzo[e][1,4]diazepin-5-one (259 mg, 0.00110 mol) and tetrahydrofuran (15.0 mL, 0.185 mol) were added. 1.06 M of lithium hexamethyldisilazide in THF (1.35 mL) was added drop wise to the reaction mixture and stirred for 20 minutes. 2-chloro-N,N-dimethyl-acetamide (170 mg, 0.0014 mol;) in THF (5 ml) was added drop wise and stirred at room temperature overnight. The reaction was partitioned with 1N HCl (2 ml) and EtOAc. the organic was separated and washed with brine and dried over MgSO$_4$. The solid was filtered and stripped to give an oil. The desired product was isolated via column chromatography with DCM and methanol as eluant. The collected fractions afforded 2-(1-ethyl-8-nitro-5-oxo-1,2,3,5-tetrahydro-benzo[e][1,4]diazepin-4-yl)-N,N-dimethyl-acetamide as an off white solid (0.27 g, 76%) $^1$H-NMR (CDCl$_3$, 400 MHz): δ 7.86 (d, 1H), 7.71 (d, 2H), 4.45 (s, 2H), 3.62 (t, 2H), 3.46 (t, 2H), 3.30 (q, 2H), 3.13 (s, 3H), 2.99 (s, 3H), 1.22 (t, 3H).

1457b). Into a Round bottom flask, 2-(1-ethyl-8-nitro-5-oxo-1,2,3,5-tetrahydro-benzo[e][1,4]diazepin-4-yl)-N,N-dimethyl-acetamide (0.27 g, 0.00084 mol;), Ethanol (20.0 mL, 0.342 mol;) and 10% Pd/C (10:90, Palladium:carbon black, 0.100 g) were added the reaction was evacuated and charged with hydrogen (3 times). The mixture was stirred at room temperature overnight under an atmosphere of Hydrogen via a balloon. The solid was filtered through Celite and washed with EtOH. The solvent was removed under vacuum to give 2-(8-amino-1-ethyl-5-oxo-1,2,3,5-tetrahydro-benzo[e][1,4]diazepin-4-yl)-N,N-dimethyl-acetamide as a white solid (0.24 g, 98%). LC/MS (ESI+) 291.19 (M+H).

1457c). Into a microwave vial, 2-(8-Amino-1-ethyl-5-oxo-1,2,3,5-tetrahydro-benzo[e][1,4]diazepin-4-yl)-N,N-dimethyl-acetamide (0.080 g, 0.28 mmol;), (2-exo,3-exo)-3-(2,5-Dichloro-pyrimidin-4-ylamino)-bicyclo[2.2.1]heptane-2-carboxylic acid amide (0.083 g, 0.28 mmol;), 2-methoxyethanol (2.0 mL, 25 mmol) and 4.00 M of hydrogen chloride in 1,4-dioxane (0.152 mL) were added. The reaction was heated in microwave for 40 minutes at 120° C.

Methanol (5 mL) and MP-carbonate (2.69 mmol/g loading; 0.410 g, 1.10 mmol) were added. The mixture was stirred for 4 hours. The solid was filtered. The solvent was removed under vacuum. The desired product was isolated via ISCO column chromatography with DCM and methanol as eluant (0 to 10% methanol). The collected fractions afforded {8-[4-((1R,2S,3R,4S)-3-Carbamoyl-bicyclo[2.2.1]hept-2-ylamino)-5-chloro-pyrimidin-2-ylamino]-1-ethyl-5-oxo-1,2,3,5-tetrahydro-benzo[e][1,4]diazepin-4-yl}-acetic acid 2-methoxy-ethyl ester as a yellow solid (48 mg, 30%). $^1$H-NMR (CDCl$_3$, 400 MHz): δ 7.78-7.90 (m, 2H), 7.62 (bs, 2H), 7.20 (d, 1H), 6.82 (s, 1H), 6.10 (s, 1H), 5.80 (s, 1H), 4.40 (s, 2H), 4.32 (t, 2H), 4.25 (t, 1H), 3.63 (t, 2H), 3.30-3.58 (m, 9H), 2.46 (s, 1H), 2.31 (bs, 1H), 2.06 (d, 1H), 1.50-1.75 (m, 2H), 1.10-1.40 (m, 6H). LC/MS (ESI+) 586.34 (M+H).

Example 1458

2-(8-amino-1-ethyl-5-oxo-1,2,3,5-tetrahydro-benzo[e][1,4]diazepin-4-yl)-N,N-dimethyl-acetamide {8-[5-Chloro-4-(2-fluoro-6-methylcarbamoyl-phenylamino)-pyrimidin-2-ylamino]-1-ethyl-5-oxo-1,2,3,5-tetrahydro-benzo[e][1,4]diazepin-4-yl}-acetic acid 2-methoxy-ethyl ester 1458a). Following an analogous procedure as described in Example 1457, 2-(8-amino-1-ethyl-5-oxo-1,2,3,5-tetrahydro-benzo[e][1,4]diazepin-4-yl)-N,N-dimethyl-acetamide was converted to 2-(8-amino-1-ethyl-5-oxo-1,2,3,5-tetrahydro-benzo[e][1,4]diazepin-4-yl)-N,N-dimethyl-acetamide {8-[5-Chloro-4-(2-fluoro-6-methylcarbamoyl-phenylamino)-pyrimidin-2-ylamino]-1-ethyl-5-oxo-1,2,3,5-tetrahydro-benzo[e][1,4]diazepin-4-yl}-acetic acid 2-methoxy-ethyl ester (20 mg, 12%). $^1$H-NMR (CDCl$_3$, 400 MHz): δ 8.90 (s, 1H), 8.01 (s, 1H), 7.47 (d, 1H), 7.20-7.35 (m, 4H), 7.17 (d, 1H), 6.79 (d, 1H), 6.13 (d, 1H), 4.38 (s, 2H), 4.31 (t, 2H), 3.62 (t, 2H), 3.49 (t, 2H), 3.39 (s, 3H), 3.36 (t, 2H), 3.10 (q, 2H), 2.92 (d, 3H), 1.15 (t, 3H). LC/MS (ESI+) 600.29 (M+H). MP 85-97° C.

Example 1459

{8-[5-Chloro-4-(2-methylcarbamoyl-phenylamino)-pyrimidin-2-ylamino]-1-ethyl-5-oxo-1,2,3,5-tetrahydro-benzo[e][1,4]diazepin-4-yl}-acetic acid 2-methoxy-ethyl ester 1459a). Following an analogous procedure as described in Example 1457, 2-(8-amino-1-ethyl-5-oxo-1,2,3,5-tetrahydro-benzo[e][1,4]diazepin-4-yl)-N,N-dimethyl-acetamide was converted to {8-[5-Chloro-4-(2-methylcarbamoyl-phenylamino)-pyrimidin-2-ylamino]-1-ethyl-5-oxo-1,2,3,5-tetrahydro-benzo[e][1,4]diazepin-4-yl}-acetic acid 2-methoxy-ethyl ester (22 mg, 14%). $^1$H-NMR (CDCl$_3$, 400 MHz): δ 11.07 (s, 1H), 8.60 (d, 1H), 8.12 (s, 1H), 7.61 (d, 1H), 7.45 (d, 2H), 7.17 (d, 1H), 7.00-7.10 (m, 2H), 6.29 (d, 2H), 4.40 (s, 2H), 4.31 (t, 2H), 3.63 (t, 2H), 3.53 9 t, 2H), 3.32-3.45 (m, 5H), 3.14 (q, 2H), 3.01 (d, 3H), 1.16 (t, 3H). LC/MS (ESI+) 582.41 (M+H). MP 198-202° C.

Example 1460

(1S,2S,3R,4R)-3-[5-Chloro-2-(1-ethyl-7-methoxy-2,3,4,5-tetrahydro-1H-benzo[e][1,4]diazepin-8-ylamino)-pyrimidin-4-ylamino]-bicyclo[2.2.1]hept-5-ene-2-carboxylic acid amide.

1460a). Into a round bottom flask, 1-ethyl-8-nitro-1,2,3,4-tetrahydro-benzo[e][1,4]diazepin-5-one (1.24 g, 5.27 mmol, prepared as described in Example 787) and 1,4-dioxane (40.0 mL, 512 mmol) were added the reaction mixture was heated to 60 degree Celsius. 2.00 M of borane dimethylsulfide complex in toluene (20 mL) was then added drop wise at 60 degree Celsius. The reaction was then heated to 100 degree Celsius for 2 hour. The reaction mixture was then added to a stirring solution of 6N HCl (20 ml). The solution was heated to 100 degree for 1 hour. NaOH pellet was then added portion wise at 80 degree Celsius to adjust pH to 8. The aqueous was extracted with EtOAc (2×250 mL). The combined organic was washed with brine and dried over MgSO4. The solid was filtered and washed with EtOAC. The desired product was isolated via ISCO column chromatography with DCM and EtOAc as eluant (0 to 100%). The collected fractions afforded 1-ethyl-8-nitro-2,3,4,5-tetrahydro-1H-benzo[e][1,4]diazepine as an off white solid (0.85 g, 73%). LC/MS (ESI+) 222.19 (M+H).

1460b). Into a round bottom flask, 1-ethyl-8-nitro-2,3,4,5-tetrahydro-1H-benzo[e][1,4]diazepine (0.85 g, 0.0038 mol), tetrahydrofuran (15.0 mL, 0.185 mol) and di-tert-butyldicarbonate (0.922 g, 0.00422 mol) were added. The reaction was stirred at room temperature for 1 hour. The solvent was removed under vacuum. The desired product was isolated via column chromatography with hexane and EtOAc as eluant (0 to 30% EtOAc) to give 1-ethyl-8-nitro-1,2,3,5-tetrahydro-benzo[e][1,4]diazepine-4-carboxylic acid tert-butyl ester as a solid (0.92, 74%). $^1$H-NMR (CDCl$_3$, 400 MHz): δ 7.67-7.80 (m, 2H), 7.20 (s, 1H), 4.37-4.55 (bd, 2H), 3.66 (bs, 2H), 3.34 (q, 2H), 3.13 (t, 2H), 1.30 (s, 9H), 1.23 (t, 2H).

1460c). Into a round bottom flask, 1-ethyl-8-nitro-1,2,3,5-tetrahydro-benzo[e][1,4]diazepine-4-carboxylic acid tert-butyl ester (820 mg, 0.0026 mol) ethanol (80.0 mL, 1.37 mol) and 10% Pd/C (10:90, Palladium:carbon black, 200.0 mg) were added. The mixture was evacuated and charged with hydrogen (3 times). The reaction was stirred at room temperature under hydrogen balloon for 18 hours. The solid was filtered through Celite and washed with ethanol. The solvent was evacuated under vacuum to afford a viscous oil. $^1$H-NMR (CDCl$_3$, 400 MHz): δ 6.90-7.10 (m, 1H), 6.30 (s, 1H), 6.18 (d, 1H), 4.20-4.35 (m, 2H), 3.50 (bs, 4H) 3.18 (q, 2H), 2.38 (bs, 2H), 1.48 (s, 9H), 1.15 9 t, 3H). LC/MS (ESI+) 292.26 (M+H).

1460d). Into a round bottom flask, sodium hydride (0.0731 g, 3.05 mmol) and N,N-dimethylformamide (10.0 mg, 0.137 mmol) were added. 8-amino-1-ethyl-1,2,3,5-tetrahydro-1,4-benzodiazepine-4-carboxylic acid tert-butyl ester (741 mg, 2.54 mmol) in DMF (2 ml) was added drop wise. the mixture was stirred for 30 minutes. Di-tert-Butyldicarbonate (0.665 g, 3.05 mmol) in DMF (2 ml) was added the reaction mixture was stirred for 2 hours. Water was added. The resulting mixture was extracted with EtOAc. The combined organic was extracted with Brine and dried over MgSO$_4$. The solid was filtered and washed with EtOAc. The desired product was isolated via ISCO column chromatography with hexane and EtOAc as eluant. (0 to 40% EtOAc). The collected fractions afforded [4-(3,3-dimethyl-butyryl)-1-ethyl-2,3,4,5-tetrahydro-1H-benzo[e][1,4]diazepin-8-yl]-ceramic acid tert-butyl ester as a glass solid (0.425 g, 43%). LC/MS (ESI+) 392.31 (M+H).

1460e). Following an analogous procedure as described in Example 490, [4-(3,3-dimethyl-butyryl)-1-ethyl-2,3,4,5-tetrahydro-1H-benzo[e][1,4]diazepin-8-yl]-carbamic acid tert-butyl ester was converted to 1-ethyl-7-methoxy-2,3,4,5-tetrahydro-1H-benzo[e][1,4]diazepin-8-ylamine. $^1$H-NMR (CDCl$_3$, 400 MHz): δ9.25 (bs, 2H), 6.65 (s, 1H), 6.38 (s, 1H), 4.16 (s, 2H), 3.78 (s, 3H), 3.06-3.30 (m, 6H), 1.17 (t, 3H)

1460f). Following an analogous procedure as described in Example 475, 1-ethyl-7-methoxy-2,3,4,5-tetrahydro-1H-benzo[e][1,4]diazepin-8-ylamine was converted to (1S,2S,3R,4R)-3-[5-chloro-2-(1-ethyl-7-methoxy-2,3,4,5-tetrahydro-1H-benzo[e][1,4]diazepin-8-ylamino)-pyrimidin-4-ylamino]-bicyclo[2.2.1]hept-5-ene-2-carboxylic acid amide as a brown solid (5 mg, 4%). $^1$H-NMR (DMSO-D$_6$, 400 MHz): δ 8.20 (bs, 2H), 8.06 (s, 1H), 7.93 (bs, 1H), 7.84 (bs, 1H), 7.30 (bs, 1H), 7.14 (s, 1H), 6.30-6.38 (m, 1H), 6.13-6.21 (m, 1H), 4.13-4.20 (m, 3H), 3.84 (s, 3H), 3.05-3.22 (m, 6H), 2.89 (bs, 1H), 2.70 (bs, 1H), 2.10 (d, 1H), 1.41 (d, 1H), 1.08 (t, 3H). LC/MS (ESI+) 484.21 (M+H).

Example 1461

2-{8-[5-Chloro-4-((1R,2R)-2-methanesulfonylamino-cyclohexylamino)-pyrimidin-2-ylamino]-1-ethyl-7-methoxy-1,2,3,5-tetrahydro-benzo[e][1,4]diazepin-4-yl}-N,N-dimethyl-acetamide 1461a) Following an analogous procedure as described in Example 492, ethyl-7-methoxy-2,3,4,5-tetrahydro-1H-benzo[e][1,4]diazepin-8-ylamine was converted to 2-{8-[5-Chloro-4-((1R,2R)-2-methanesulfonylamino-cyclohexylamino)-pyrimidin-2-ylamino]-1-ethyl-7-methoxy-1,2,3,5-tetrahydro-benzo[e][1,4]diazepin-4-yl}-N,N-dimethyl-acetamide as a yellow solid (17 mg, 11%). $^1$H-NMR (CDCl$_3$, 400 MHz): δ 8.02 (s, 1H), 7.95 (s, 1H), 7.36 (s, 1H), 6.81 (s, 1H), 5.60 (bs, 1H), 5.35 (d, 1H), 4.10 (q, 2H), 3.92-4.01 (m, 1H), 3.87 (s, 3H), 3.15-3.30 (m, 5H), 3.05-3.12 (m, 2H), 3.01 (s, 3H), 2.97 (s, 3H), 2.79 (s, 3H), 2.14-2.28 (m, 2H), 1.75-1.90 (m, 2H), 1.30-1.60 (m, 4H), 1.19 (t, 3H). LC/MS (ESI+) 609.28 (M+H).

Example 1463

N-((1R,2R)-2-{5-Chloro-2-[7-methoxy-5,5-dimethyl-2-oxo-4-(2,2,2-trifluoro-acetyl)-2,3,4,5-tetrahydro-1H-benzo[e][1,4]diazepin-8-ylamino]-pyrimidin-4-ylamino}-cyclohexyl)-methanesulfonamide 1463a). Into a round bottom flask, sodium hydride, 60% disp. in mineral oil (3:2, sodium hydride:mineral Oil, 27.0 g), and tetrahydrofuran (600 mL, 7 mol) was added. (3-methoxyphenyl)-acetonitrile (38.20 g, 0.2596 mol) in THF (80 mL) was added drop wise at 5° C. for 1 hour. Methyl iodide (81.0 g, 0.571 mol) in THF (50 mL) was added to the mixture at 5° C. for 1 hour. The mixture was stirred for 3 hours at room temperature. The reaction was quenched with water 100 mL. The reaction was partitioned with water (200 mL) and EtOAc (600 mL). The organic was separated, washed with Brine, and dried over magnesium sulfate. The solid was filtered and washed with EtOAc. The solvent was removed under vacuum to afford 2-(3-methoxy-phenyl)-2-methyl-propionitrile as a light yellow oil (44.2 g, 97%). $^1$H-NMR (DMSO-D$_6$, 400 MHz): δ 7.30-7.38 (m, 1H), 7.02-7.12 (m, 1H), 7.01-7.60 (m, 1H), 6.90-6.96 (m, 1H), 3.80 (s, 3H), 1.68 (s, 6H).

1463b). Into a round bottom flask, potassium hydroxide (35.4 g, 631 mmol) and water (225 mL, 12500 mmol) was added at 100° C. 2-(3-methoxy-phenyl)-2-methyl-propionitrile (44.20 g, 252.2 mmol) in Methanol (25.0 mL, 617 mmol) was added to the reaction mixture. The reaction was then heated to reflux at 130° C. over night. TLC suggested starting material. Potassium hydroxide (35.4 g, 631 mmoles) in water (50 mL) was added. The reaction was heated for 5 days. The reaction was partitioned with water (700 mL). The aqueous was acidified with concentrated HCl to pH 1. The solid was filtered and washed with water and EtOAc. The organic layer was separated. The aqueous was extracted with EtOAc (3×400 mL). The combined organic was washed with brine, and dried over MgSO4. The solid was then filtered and washed with EtOAc. The solvent was removed under vacuum to afford a brown oil. The oil was triturated with hexane to afford 2-(3-methoxy-phenyl)-2-methyl-propionic acid as a light yellow solid (36.2 g. 74%). H-NMR (DMSO-D$_6$, 400 MHz): δ 12.30 (s, 1H), 7.24 (t, 1H), 6.90 (d, 1H), 6.75-6.88 (m, 2H), 3.74 (s, 3H), 1.45 (s, 6H)

1463c). Into a round bottom flask, 2-(3-methoxy-phenyl)-2-methyl-propionic acid (15.00 g, 77.23 mmol), toluene (150.0 mL, 1408 mmol) and triethylamine (10.2 mL, 73.4 mmol) were added a room temperature under an atmosphere of Nitrogen. Diphenylphosphonic azide (15.8 mL, 73.4 mmol) was added. The reaction was heated at 85° C. for 3 hours. benzyl alcohol (7.99 mL, 77.2 mmol) and triethylamine (10.2 mL, 73.4 mmol) was added. The reaction was heated to reflux overnight under an atmosphere of Nitrogen. 10% Citric acid (300 mL) was added to the reaction mixture at room temperature. The reaction was extracted with EtOAc (3×250 mL). The combined organic was washed with brine, and dried over magnesium sulfate. The solid was filtered and washed with EtOAc. The solvent was removed under vacuum. The product was isolate via ISCO column chromatography with hexane and EtOAc as eluant (15% EtOAc) to give [1-(3-Methoxy-phenyl)-1-methyl-ethyl]-carbamic acid benzyl ester (21.30 g, 92%). $^1$H-NMR (DMSO-D$_6$, 400 MHz): δ 7.68 (bs, 1H), 7.25-7.42 (m, 5H), 7.20 (t, 1H), 6.91 (d, 1H), 6.86 (s, 1H), 6.75 (d, 1H), 4.94 (s, 2H), 3.70 (s, 3H), 1.51 (s, 6H).

1463d). Into a round bottom flask, [1-(3-methoxy-phenyl)-1-methyl-ethyl]-carbamic acid benzyl ester (10.0 g, 33.4 mmol), ethanol (200 mL), and 10% Pd/C (1.20 g) were added. The mixture was evacuated under vacuum and charged with hydrogen via balloon (3 times). The reaction was stirred at room temperature overnight under a hydrogen atmosphere via a balloon. The solid was filtered and washed with Ethanol. The solvent was removed under vacuum to give 1-(3-Methoxy-phenyl)-1-methyl-ethylamine as a viscous oil 1-(3-methoxy-phenyl)-1-methyl-ethylamine (4.80 g, 0.0290 mol;) was treated with DMF and N,N-diisopropylethylamine (7.59 mL, 0.0436 mol) acetic acid, bromo-, 1,1-dimethylethyl ester (6.23 g, 0.0320 mol), respectively. The reaction mixture was stirred at 50° C. for 24 hours. The solvent was removed under vacuum. The reaction was partitioned with water and DCM. The organic was separated, washed with Brine, and dried over magnesium sulfate. The solid was filtered and washed with DCM. The solvent was removed under vacuum. The product was isolate via column chromatography with hexane and EtOAc as eluant (0 to 50%) to afford [1-(3-methoxy-phenyl)-1-methyl-ethylamino]-acetic acid tert-butyl ester as a white solid (5.86 g, 63%). $^1$H-NMR (CDCl$_3$, 400 MHz): δ 7.22-7.28 (m, 1H), 6.97-7.02 (m, 2H), 6.75-6.80 (m, 1H), 3.80 (s, 3H), 3.06 (s, 2H), 1.44 (s, 6H), 1.42 (s, 9H).

1463e). Into a round bottom flask, [1-(3-methoxy-phenyl)-1-methyl-ethylamino]-acetic acid tert-butyl ester (5.86 g, 0.0210 mol) and trifluoroacetic acid (10 mL, 0.1 mol;) were added. The mixture was heated at 65° C. for 2 hours. The solvent was then removed to under vacuum to afford an oil. The oil was then treated with Eaton's reagent (20 mL) at 50° C. for 8 hours. The reaction was partitioned with cold water and basified to pH 8 with 50% NaOH. The aqueous was extracted with EtOAc (2×200 mL). The combined organic was then washed with Brine and dried over MgSO$_4$. The solid was filtered and washed with EtOAc. The solvent was removed to afford an oil. The desired product was isolated via ISCO column chromatography with DCM and methanol as eluant (8% methanol) to give 7-methoxy-1,1-dimethyl-2,3-dihydro-1H-isoquinolin-4-one as an off white solid (0.985 g, 23%). $^1$H-NMR (DMSO-d6, 400 MHz): δ 7.82 (d, 1H), 6.88-6.95 (m, 2H), 3.85 (s, 3H), 3.51 (s, 2H), 3.10 (bs, 1H), 1.42 (s, 6H).

1463f). Into a round bottom flask, 7-methoxy-1,1-dimethyl-2,3-dihydro-1H-isoquinolin-4-one (0.835 g, 0.00407 mol) and Eaton's reagent (20 mL) were added. The reaction was heated to 40 degree. Sodium azide (0.555 g, 0.00854 mol) was added portion wise over 30 minutes. The reaction was heated at 50° C. for 45 minutes. Water (20 mL) was added and neutralized with solid NaHCO$_3$. The aqueous was extracted with EtOAc (2×200 mL). The combined organic was then washed with brine and dried over MgSO4. The solid was filtered and washed with EtOAc. The solvent was removed under vacuum. The desired product was isolated via ISCO column chromatography with DCM and methanol as eluant (10% methanol) to give 7-methoxy-5,5-dimethyl-1,3,4,5-tetrahydro-benzo[e][1,4]diazepin-2-one as a white solid (0.37 g, 40%). $^1$H-NMR (CDCl$_3$, 400 MHz): δ 7.64 (bs, 1H), 6.87 (s, 1H), 6.78 (d, 1H), 6.72 (d, 1H), 3.79 (s, 3H), 3.71 (s, 2H), 1.54 (s, 6H).

1463g). Into a round bottom flask, 7-methoxy-5,5-dimethyl-1,3,4,5-tetrahydro-benzo[e][1,4]diazepin-2-one (0.370 g, 0.00168 mol) and acetonitrile (20.0 mL, 0.383 mol) were added at 0° C. Trifluoroacetic anhydride (0.712 mL, 0.00504 mol) was added drop wise. The mixture was stirred for 20 minutes. Potassium nitrate (0.340 g, 0.00336 mol;) was then added at 0° C. The reaction was stirred at room temperature overnight. Saturated NaHCO$_3$ was added. The reaction was partitioned with water and EtOAc. The organic was separated, washed with Brine, and dried over magnesium sulfate. The solid was filtered and washed with DCM. The solvent was removed under vacuum. The product was isolated via column chromatography with hexanes and EtOAc as eluant (0 to 60%) to afford 7-methoxy-5,5-dimethyl-8-nitro-4-(2,2,2-trifluoro-acetyl)-1,3,4,5-tetrahydro-benzo[e][1,4]diazepin-2-one as a white solid. $^1$H-NMR (DMSO-D$_6$, 400 MHz): δ 10.43 (s, 1H), 7.75 (s, 1H), 7.32 (s, 1H), 4.46 (s, 2H), 3.96 (s, 3H), 1.82 (s, 6H).

1463h). Into a round bottom flask, 7-methoxy-5,5-dimethyl-8-nitro-4-(2,2,2-trifluoro-acetyl)-1,3,4,5-tetrahydro-benzo[e][1,4]diazepin-2-one (0.27 g, Ethanol (200 mL), and 10% Pd/C (50 mg) were added. The mixture was evacuated under vacuum and charged with hydrogen via balloon (3 times). The reaction was stirred at room temperature overnight under hydrogen atmosphere via a balloon. The solid was filtered and washed with ethanol. The solvent was removed under vacuum to give 8-amino-7-methoxy-5,5-dimethyl-4-(2,2,2-trifluoro-acetyl)-1,3,4,5-tetrahydro-benzo[e][1,4]diazepin-2-one a glass solid. $^1$H-NMR (CDCl$_3$, 400 MHz): δ 8.38 (bs, 1H), 7.30 (bs, 1H), 6.89 (bs, 1H), 6.30 (bs, 1H), 4.10-4.70 (bm, 2H), 3.87 (bs, 3H), 3.45 (bs, 1H), 1.88 (bs, 6H).

1463i). Following an anaologous procedure analogous to Example 1451, 8-amino-7-methoxy-5,5-dimethyl-4-(2,2,2-trifluoro-acetyl)-1,3,4,5-tetrahydro-benzo[e][1,4]diazepin-2-one was converted to N-((1R,2R)-2-{5-Chloro-2-[7-methoxy-5,5-dimethyl-2-oxo-4-(2,2,2-trifluoro-acetyl)-2,3,4,5-tetrahydro-1H-benzo[e][1,4]diazepin-8-ylamino]pyrimidin-4-ylamino}-cyclohexyl)-methanesulfonamide TFA salt (7 mg, 4%). $^1$H-NMR (CDCl$_3$, 400 MHz): δ 9.00 (bs, 1H), 8.25 (s, 1H), 7.92 (s, 1H), 7.32 (bs, 1H), 6.71 (s, 1H), 650 (bs, 1H), 4.17-4.40 (m, 2H), 3.88-4.10 (m, 1H), 3.74 (s, 3H), 3.50 (q, 2H), 3.25-3.43 (m, 1H), 3.06 (s, 3H), 2.03-2.23 (m, 2H), 1.90 (s, 1H), 1.71 (s, 3H), 1.40-1.70 (m, 2H), 0.90-1.40 (complex multiplex m, 4H). LC/MS (ESI+) 634.13 (M+H).

Example 1464

8-{5-Chloro-4-[2-(2-morpholin-4-yl-ethoxy)-phenylamino]-pyrimidin-2-ylamino}-1,3,4,5-tetrahydro-benzo[b]azepin-2-one 1464a). Into a microwave vial, (2,5-dichloro-pyrimidin-4-yl)-[2-(2-morpholin-4-yl-ethoxy)-phenyl]-amine (100.0 mg, 0.2708 mmol, prepared as in Example 1455a), 7-amino-5,5-dimethyl-1,3,4,5-tetrahydro-benzo[b]azepin-2-one (71.0 mg, 0.348 mmol), isopropyl alcohol (2.00 mL, 26.1 mmol) and 4 M of hydrogen chloride in 1,4-dioxane (0.20 mL) were added respectively. The reaction was heated in the microwave on 300 watts, 120° C. for 20 minutes. IPA (3 mL) was added upon cooling to room temperature. The solid was filtered, washed with IPA and dried under vacuum to afford 8-{5-Chloro-4-[2-(2-morpholin-4-yl-ethoxy)-phenylamino]-pyrimidin-2-ylaminol}-1,3,4,5-tetrahydro-benzo[b]azepin-2-one HCl salt as a white solid (89 mg, 78%). $^1$H-NMR (DMSO-d6, 400 MHz): δ 11.07 (bs, 1H), 9.60 (bs, 1H), 9.34 (s, 1H), 8.67 (bs, 1H), 8.20 (s, 1H), 7.70 (bs, 1H), 7.45 b (d, 1H), 7.40 (s, 1H), 7.27 (t, 1H), 7.18 (d, 1H), 7.05 (t, 1H), 6.73 (d, 1H), 4.46 (bs, 2H), 3.90 (d, 2H), 3.75 (t, 2H), 3.40-3.60 (m, 4H), 3.08-3.25 (m, 2H), 2.13 (t, 2H), 1.93 (t, 2H), 1.23 (s, 6H). LC/MS (ESI+) 537.18 (M+H). MP 240-243° C.

Example 1465

8-{5-Chloro-4-[2-(2-morpholin-4-yl-ethoxy)-phenylamino]-pyrimidin-2-ylamino}-1,3,4,5-tetrahydro-benzo[b]azepin-2-one 1465a). Into a microwave vial, (2,5-dichloro-pyrimidin-4-yl)-[2-(2-morpholin-4-yl-ethoxy)-phenyl]-amine (100.0 mg, 0.2708 mmol), 8-amino-1,3,4,5-tetrahydro-benzo[b]azepin-2-one (61.2 mg, 0.348 mmole), isopropyl alcohol (2.00 mL, 26.1 mmol) and 4 M of hydrogen chloride in 1,4-dioxane (0.20 mL) were added, respectively. The reaction was heated in the microwave on 300 watts, 120° C. for 20 minutes. Triethylamine (0.2 mL) was added. The reaction was concentrated to dryness. The desired product was isolated via ISCO column chromatography with DCM and methanol as eluant (10% methanol). The resulting solid was triturated with diethyl ether to afford 8-{5-Chloro-4-[2-(2-morpholin-4-yl-ethoxy)-phenylamino]-pyrimidin-2-ylamino}-1,3,4,5-tetrahydro-benzo[b]azepin-2-one as a white solid (42 mg, 30%). $^1$H-NMR (DMSO-D$_6$, 400 MHz): δ 9.42 (s, 1H), 9.32 (s, 1H), 8.25 (s, 1H), 8.18 (s, 1H), 8.10 (bs, 1H), 7.35 (d, 1H), 7.27 (s, 1H), 7.12 (s, 2H), 7.0 (d, 1H), 6.85-6.95 (m, 1H), 4.16 (t, 2H), 3.50 (t, 4H), 2.55-2.70 (m, 4H), 2.40 (s, 4H), 2.00-2.20 (m, 4H). LC/MS (ESI+) 509 (M+H).

Example 1466

5-Chloro-N*2*-[3-(2-methoxy-ethyl)-2,3,4,5-tetrahydro-1H-enzo[d]azepin-7-yl]-N*4*-[2-(2-morpholin-4-yl-ethoxy)-phenyl]-pyrimidine-2,4-diamine 1466a). Into a microwave vial, (2,5-dichloro-pyrimidin-4-yl)-[2-(2-morpholin-4-yl-ethoxy)-phenyl]-amine (100.0 mg, 0.2708 mmol), 3-(2-methoxy-ethyl)-2,3,4,5-tetrahydro-1H-benzo[d]azepin-7-ylamine (65.6 mg, 0.298 mmoles), isopropyl alcohol (2.00 mL, 26.1 mmol) and 4 M of hydrogen chloride in 1,4-dioxane (0.20 mL) were added, respectively.

The reaction was heated in the microwave on 300 watts, 120° C. for 20 minutes. Triethylamine (0.5 mL) was added upon cooling to room temperature. The solvent was removed under vacuum. The desired product was isolated via ISCO column chromatography with DCM and methanol as eluant (10% methanol). The collected fractions afforded a white solid (31 mg, 21%). $^1$H-NMR (DMSO-D$_6$, 400 MHz): δ 10.43 (bs, 1H), 9.74 (bs, 11H), 9.35 (bs, 1H) 8.29 (s, 1H), 8.14 (s, 1H), 7.90-8.05 (m, 1H), 7.43 bs, 1H), 7.22-77.36 (m, 1H), 7.10-7.21 (m, 2H), 6.92 (t, 2H), 4.0-4.25 (m, 2H), 3.52-3.80 (m, 4H), 3.48 (s, 3H), 3.10-3.30 (m, 2H), 2.80-3.08 (m, 6H), 2.65 (bs, 4H), 2.35 (bs, 4H). LC/MS (ESI+) 553.31 (M+H). MP 106-110° C.

Example 1467

2-[2-(8-Amino-4H,6H-3,5,10b-triaza-benzo[e]azulen-5-yl)-5-chloro-pyrimidin-4-ylamino]-3-fluoro-N-methyl-benzamide 1467a). Into a Round bottom flask, 2-fluoro-4-nitro-benzonitrile (10.4 g, 0.0624 mol), imidazole-2-carboxaldehyde (5.00 g, 0.0520 mol) and dimethyl sulfoxide (200 mL, 3 mol) were added at room temperature. potassium carbonate (7.19 g, 0.0520 mol) was added portion wise to the reaction mixture and heated at 55° C. for 60 minutes. The reaction was cooled at −20° C. overnight. The content was poured over ice and stirred for 30 minutes. The solid was filtered and washed with water. The resulting solid was dissolved with DCM and washed with Brine. The organic was separated, and dried over magnesium sulfate. The solid was filtered and washed with DCM. The solvent was removed under vacuum to give 2-(2-formyl-imidazol-1-yl)-4-nitro-benzonitrile as a yellow solid (10.48 g, 83%). $^1$H-NMR (DMSO-D$_6$, 400 MHz): δ9.75 (s, 1H), 8.68 (s, 1H), 8.55 (d, 1H), 8.40 (d, 1H), 7.99 (s, 1H), 7.57 (s, 1H).

1467b). Into a round bottom flask equipped with a Dean Stark trap, 2-(2-formyl-imidazol-1-yl)-4-nitro-benzonitrile (10.48 g, 0.04327 mol), 1,2-ethanediol (15.0 mL, 0.269 mol), p-toluenesulfonic acid monohydrate (8.23 g, 0.0433 mol), and benzene (150 mL, 1.7 mol) were added. The reaction was heated to reflux for 6 hours. The reaction was cooled to room temperature. 1N NaOH was added to adjust the pH to 10. The reaction was partitioned with water and EtOAc. The organic was separated, washed with Brine, and dried over magnesium sulfate. The solid was filtered and washed with EtOAc. The solvent was removed under vacuum. The product was isolated via ISCO column chromatography with DCM and methanol as eluant (0 to 5% methanol). The collected fractions afforded 2-(2-[1,3]dioxolan-2-yl-imidazolidin-1-yl)-4-nitro-benzonitrile as a yellow solid (8.20 g, 66%). $^1$H-NMR (DMSO-D$_6$, 400 MHz): δ8.53 (d, 1H), 8.42 (s, 1H), 8.35 (d, 1H), 7.65 (s, 1H), 7.14 (s, 1H), 5.82 (s, 1H), 3.65 (bs, 2H), 3.45 (bs, 2H).

1467c). Into a par bottle, 2-(2-[1,3]dioxolan-2-yl-imidazolidin-1-yl)-4-nitro-benzonitrile (8.20 g), ethanol (50 mL) and 10% Pd/C (0.50 g) were added. The reaction mixture was evacuated and charged with hydrogen 3 times. The reaction was shaken at room temperature on the par at 45 psi for 4 hours. The solid was filtered and washed with ethanol. The solvent was concentrated to give 4-amino-2-(2-[1,3]dioxolan-2-yl-imidazol-1-yl)-benzonitrile as an off white solid. $^1$H-NMR (DMSO-D$_6$, 400 MHz): δ 7.52 (d, 1H), 7.40 (s, 1H), 7.03 (s, 1H), 6.68 (d, 1H), 6.60 (s, 1H), 6.45 (bs, 2H), 5.75 (s, 1H), 3.80 (bs, 2H), 3.62 (bs, 2H).

1467d). Into a par bottle, 4-amino-2-(2-[1,3]dioxolan-2-yl-imidazol-1-yl)-benzonitrile (1.82 g, 0.00710 mol), Raney's nickel (1.90 g, 0.0324 mol), ethanol (25 mL, 0.43 mol) and di-tert-butyldicarbonate (3.41 g, 0.0156 mol;) were added. The reaction mixture was evacuated and charged with hydrogen 3 times. The reaction was shaken at room temperature on the par at 55 psi overnight. LCMS suggested 15% conversion. Raney's nickel (1.00 g, 0.0170 mol) was added. The above procedure was repeated. LCMS suggested no SM. The solid was filtered and washed with methanol. The solvent was removed under vacuum. The desired product was isolated via ISCO column chromatography with DCM and methanol as eluant (0 to 15% methanol). The collected fractions were concentrated to afforded [4-(tert-butoxycarbonylamino-methyl)-3-(2-[1,3]dioxolan-2-yl-imidazol-1-yl)-phenyl]-carbamic acid tert-butyl ester as an off white solid. $^1$H-NMR (CDCl$_3$, 400 MHz): δ 7.32-7.53 (m, 3H), 7.18 (s, 1H), 6.94 (s, 1H), 6.54 (s, 1H), 5.83 (s, 1H), 5.20 (bs, 1H), 4.07-4.25 (m, 1H), 3.60-3.90 (m, 5H), 1.48 (s, 9H), 1.40 (s, 9H).

1467e). Into a round bottom flask, [4-(tert-butoxycarbonylamino-methyl)-3-(2-[1,3]dioxolan-2-yl-imidazol-1-yl)-phenyl]-carbamic acid tert-butyl ester (0.420 g, 0.000912 mol), methylene chloride (6.0 mL, 0.094 mol) and trifluoroacetic Acid (2.0 mL, 0.026 mol) were added. The reaction was stirred at room temperature for 2 hours. The solvent was removed under vacuum. The viscous oil was treated with tetrahydrofuran (30.0 mL, 0.370 mol) and 3.00 N of Hydrogen Chloride in Water (10.0 mL). The mixture was heated to reflux for 2 hours. The reaction was poured into aqueous saturated NaHCO$_3$. The pH was adjusted to 9. The aqueous was extracted with EtOAC. The combined organic was washed with brine and dried over MgSO$_4$. The solid was filtered and washed with EtOAc. The solvent was removed under vacuum. The desired product was isolated via ISCO column chromatography with EtOAc and methanol as eluant (0 to 30% methanol). The collected fractions were concentrated to afford 6H-3,5,10b-triaza-benzo[e]azulen-9-ylamine as a white solid. $^1$H-NMR (CDCl$_3$, 400 MHz): δ 8.35 (s, 1H), 7.49 (s, 1H), 7.30 (s, 1H), 7.19 (d, 1H), 6.67 (d, 1H), 6.59 (s, 1H), 4.46 (s, 2H), 3.90 (bs, 2H)

1467f). Into a round bottom flask, 6H-3,5,10b-triaza-benzo[e]azulen-9-ylamine (0.052 g, 0.00026 mol), Ethanol (20.0 mL, 0.342 mol), and 10% Pd/C (10:90, palladium:carbon black, 0.040 g) were added. The reaction was evacuated and charged with hydrogen (3 times). The mixture was stirred at room temperature under an atmosphere of Hydrogen via a balloon. The solid was filtered through Celite and washed with EtOH. The solvent was removed under vacuum to give a white solid. $^1$H-NMR (CDCl$_3$, 400 MHz): δ7.15-7.22 (m, 2H), 7.10 (s, 1H), 6.60-6.74 (m, 2H), 3.80-3.92 (m, 4H), 3.67 (s, 2H).

1467g). Into a microwave vial, 5,6-dihydro-4H-3,5,10b-triaza-benzo[e]azulen-9-ylamine (0.042 g, 0.00021 mol), 2-(2,5-dichloro-pyrimidin-4-ylamino)-3-fluoro-N-methyl-benzamide (0.048 g, 0.00015 mol), 10-camphorsulfonic acid (0.071 g, 0.00030 mol), and isopropyl alcohol (2.0 mL, 0.026 mol;) were added. The reaction was heated in the microwave at 120° C. for 25 minutes. The solvent was removed under vacuum to afford a solid. The solid was partitioned with saturated NaHCO$_3$ and EtOAc. The organic was separated, washed with Brine, and dried over magnesium sulfate. The solid was filtered and washed with EtOAc. The solvent was removed under vacuum. The product was isolated via Gilson Prep HPLC. The collected fractions were concentrated to afford a yellow solid as a TFA salt. $^1$H-NMR (CD$_3$CN, 400 MHz): δ 8.15 (s, 1H), 7.73 (s, 1H), 7.58 (s, 1H), 7.56 (d, 1H), 7.38-7.45 (m, 2H), 6.87 9s, 1H), 6.77 (m, 1H), 4.85 (bs, 2H), 4.46 (s, 2H), 2.78 (s, 3H), 2.56 (s, 2H). LC/MS (ESI+) 479.21 (M+H)

Example 1471

2-{5-Bromo-2-[3-(2-methoxy-ethyl)-2,3,4,5-tetrahydro-1H-benzo[d]azepin-7-ylamino]-pyrimidin-4-ylamino}-3-fluoro-N-methyl-benzamide The title compound was prepared by combining Example 359a (65.6 mg, 0.182 mmol) and Example 34b (48.2 mg, 0.219 mmol) in an analogous manner described in Example 151d. Product was isolated by gradient elution (EtOAc/hexane) off an amine-modified silica gel column as a yellow foam (33 mg, 33%) and had the following properties: m.p: 99-105° C.; LC/MS (m/e): 543/535 (M+H); $^1$H-NMR (DMSO-$d_6$, 400 MHz): δ 9.28 (s, 1H), 9.22 (s, 1H), 8.63 (m, 1H), 8.22 (s, 1H), 7.52-7.35 (series of m, 3H), 7.21 (s, 1H), 7.10 (d, J=7.3, 1H), 6.80 (d, J=7.3, 1H), 3.44 (t, J=6.0, 2H), 3.24 (s, 3H), 2.75 (d, J=4.3, 3H), 2.68 (m, 2H), 2.65-2.50 (series of m, 8H, partially obscured by DMSO peak).

Example 1472

2-{5-Bromo-2-[1-(2-methoxy-ethyl)-2-oxo-2,3,4,5-tetrahydro-1H-benzo[b]azepin-7-ylamino]-pyrimidin-4-ylamino}-3-fluoro-N-methyl-benzamide The title compound was prepared by combining Example 359a (65.6 mg, 0.182 mmol) and Example 356b (51.3 mg, 0.219 mmol) in an analogous manner described in Example 356c. Product was isolated by gradient elution (EtOAc/hexane) off an amine-modified silica gel column as a yellow foam (59 mg, 58%) and had the following properties: m.p: 191-193° C.; LC/MS (m/e): 557/559 (M+H); $^1$H-NMR (DMSO-$d_6$, 400 MHz): δ 9.42 (s, 1H), 9.30 (s, 1H), 8.60 (m, 1H), 8.26 (s, 1H), 7.55-7.50 (series of m, 2H), 7.48-7.35 (series of m, 3H), 7.11 (d, J=8.5, 1H), 4.2-3.7 (m, 2H), 3.55-3.44 (m, 2H), 3.14 (s, 3H), 2.75 (d, J=4.3, 3H), 2.7-2.4 (series of m, 2H, partially obscured by DMSO peak), 2.2-1.8 (series of m, 4H).

Example 1473

2-{5-Bromo-2-[1-(2-methoxy-ethyl)-2-oxo-2,3,4,5-tetrahydro-1H-benzo[b]azepin-8-ylamino]-pyrimidin-4-ylamino}-3-fluoro-N-methyl-benzamide The title compound was prepared by combining Example 359a (65.6 mg, 0.182 mmol) and Example 361b (51.3 mg, 0.219 mmol) in an analogous manner described in Example 361c. Product was isolated by gradient elution (EtOAc/hexane) off an amine-modified silica gel column as a yellow powder (75 mg, 74%) and had the following properties: m.p: 211-224° C.; LC/MS (m/e): 557/559 (M+H); $^1$H-NMR (DMSO-$d_6$, 400 MHz): δ 9.39 (s, 1H), 9.31 (s, 1H), 8.58 (m, 1H), 8.26 (s, 1H), 7.48 (d, J=6.6, 1H), 7.43 (s, 1H), 7.40-7.30 (m, 2H), 7.23 (d, J=7.9, 1H), 6.97 (d, J=7.9, 1H), 4.2-3.7 (m, 2H), 3.27 (m, 2H), 3.10 (s, 3H), 2.75 (d, J=4.3, 3H), 2.7-2.4 (m, 2H, partially obscured by DMSO peak), 2.2-1.8 (series of m, 4H).

Example 1474

2-[5-Chloro-2-(1-isopropyl-2-oxo-2,3,4,5-tetrahydro-1H-benzo[b]azepin-8-ylamino)-pyrimidin-4-ylamino]-3-fluoro-N-methyl-benzamide 1474a) 8-Amino-1-isopropyl-1,3,4,5-tetrahydro-benzo[b]azepin-2-one (57.2 mg, 0.262 mmol) was prepared in an analogous manner as described in Examples 361a and 361b 1474b) The above amine in Example 1474a was coupled with Example 311b (68.7 mg, 0.218 mmol) in an analogous manner described in Example 356c. Product was isolated by gradient elution (EtOAc/hexane) off an amine-modified silica gel column as a white powder (42 mg, 39%) and had the following properties: m.p: 208-210° C.; LC/MS (m/e): 497 (M+H); $^1$H-NMR (DMSO-$d_6$, 400 MHz): δ 9.39 (s, 1H), 9.35 (s, 1H), 8.53 (s, 1H), 7.52-7.35 (series of m, 5H), 7.32 (s, 1H), 6.95 (d, J=8.5, 1H), 4.57, (m, 1H), 2.74 (d, J=4.2, 3H), 2.60-2.50 (m, 2H, obscured by DMSO), 2.25-1.95 (m, 3H), 1.85-1.75 (m, 1H), 1.27 (d, J=6.4, 3H), 0.95 (d, J=6.3, 3H)

Example 1475

2-[5-Chloro-2-(1-isopropyl-2-oxo-2,3,4,5-tetrahydro-1H-benzo[b]azepin-8-ylamino)-pyrimidin-4-ylamino]-3-methyl-benzamide 1475a) 2-(2,5-Dichloro-pyrimidin-4-ylamino)-3-methyl-benzamide was prepared in an analogous manner as described in Example 313b.

1475b) The above pyrimidine in Example 1475a (69.2 mg, 0.233 mmol) was coupled with Example 1474a (61.2 mg, 0.280 mmol) in an analogous manner described in Example 356c. Product was purified by gradient elution (EtOAc/hexane) off an amine-modified silica gel column followed by reverse phase preparative HPLC (MeCN/$H_2$O/0.1% TFA). Appropriate fractions were neutralized, extracted with $CH_2Cl_2$ and the organic layer evaporated to yield title compound as a white foam (29 mg, 26%) that had the following properties: m.p: 140-160° C.; LC/MS (m/e): 479 (M+H); $^1$H-NMR (CDCl$_3$, 400 MHz): δ 8.70 (s, 1H), 8.07 (s, 1H), 7.48 (d, J=7.5, 1H), 7.41 (d, J=7.5, 1H), 7.32 (d, J=5.8, 1H), 7.18 (d, J=8.0, 1H), 7.27 (s, 1H), 7.07 (br s, 1H), 6.95 (d, J=8.0, 1H), 6.10 (br s, 1H), 5.85 (brb s, 1H), 4.75, (m, 1H), 2.80-2.60 (m, 1H), 2.60-2.50 (m, 1H), 2.24 (s, 3H), 2.30-2.10 (m, 2H), 1.90-1.70 (m, 2H), 1.29 (d, J=7.1, 3H), 1.00 (d, J=6.9, 3H).

Example 1476

2-[5-Chloro-2-(5,5-dimethyl-2-oxo-2,3,4,5-tetrahydro-1H-benzo[b]azepin-7-ylamino)-pyrimidin-4-ylamino]-3-methyl-benzamide The title compound was prepared by combining Example 1475a (70.2 mg, 0.236 mmol) and Example 381b (58.4 mg, 0.286 mmol) in an analogous manner described in Example 356c. After extracting reaction mixture into $CH_2Cl_2$, product was isolated as described in Example 1475b as a white foam (25 mg, 23%) that had the following properties: m.p: 220-222° C.; LC/MS (m/e): 465 (M+H); $^1$H-NMR (DMSO-$d_6$, 400 MHz): δ 9.33 (s, 1H), 9.24 (s, 1H), 9.18 (s, 1H), 8.12 (s, 1H), 7.82 (s, 1H), 7.54 (s, 1H), 7.50 (d, J=7.1, 1H), 7.42 (m, 2H), 7.36 (s, 1H), 7.29 (m, 1H), 6.61 (m, 1H), 2.16 (s, 3H), 2.09 (m, 2H), 1.92 (m, 2H), 1.22 (s, 6H).

Example 1477

3-[5-Chloro-2-(2-oxo-2,3,4,5-tetrahydro-1H-benzo[b]azepin-8-ylamino)-pyrimidin-4-ylamino]-thiophene-2-carboxylic acid methylamide 1477a) 3-(2,5-Dichloro-pyrimidin-4-ylamino)-thiophene-2-carboxylic acid methylamide was prepared in an anlogous manner as described in Example 313b from 3-aminothiophene-2-carboxylic acid methylamide (Naito, Youichiro et al. *J. Med. Chem.* 1996 39, 3019-3029).

1477b) The above pyrimidine in Example 1477a (75.1 mg, 0.248 mmol) was coupled with 8-amino-1,3,4,5-tetrahydro-benzo[b]azepin-2-one (48 mg, 0.27 mmol) in an analogous manner described in Example 356c. The reaction mixture was neutralized with aqueous $NaHCO_3$, filtered, and the resulting precipitate washed with $H_2O$, IPA and ether. The title compound was obtained as a gray powder (74 mg, 65%) that had the following properties: m.p: 296-297° C.; LC/MS (m/e): 443 (M+H); $^1$H-NMR (DMSO-$d_6$, 400 MHz): δ 11.68 (s, 1H), 9.56 (s, 1H), 9.52 (s, 1H), 8.45 (br s, 1H), 8.26-8.24 (m, 2H), 7.74 (s, 1H), 7.65 (d, J=5.2, 1H), 7.41 (d, J=7.9, 11H), 7.17 (d, J=8.1, 1H), 2.77 (d, J=3.8, 3H), 2.67-2.60 (m, 2H), 2.19-2.05 (series of m, 4H).

Example 1478

3-{5-Chloro-2-[1-(2-methoxy-ethyl)-2-oxo-2,3,4,5-tetrahydro-1H-benzo[b]azepin-8-ylamino]-pyrimidin-4-ylamino}-thiophene-2-carboxylic acid methylamide The title compound was prepared by combining Example 1477a (75.2 mg, 0.248 mmol) and Example 361b (63.9 mg, 0.273 mmol) in an analogous manner described in Example 356c. The title product was isolated as described in Example 1477b as a white powder (124 mg, 60%) that had the following properties: m.p: 237-241° C.; LC/MS (m/e): 501 (M+H); $^1$H-NMR (DMSO-$d_6$, 400 MHz): δ 11.64 (s, 1H), 9.54 (s, 1H), 8.47 (m, 1H), 8.26-8.24 (m, 2H), 7.68 (d, J=5.2, 1H), 7.36-7.34 (m, 2H), 7.16 (d, J=8.3, 1H), 4.2-3.6 (br m, 2H), 3.40-3.38 (m, 2H), 3.12 (s, 3H), 2.77 (d, J=3.7, 3H), 2.67-2.50 (m, 2H), 2.20-2.15 (m, 2H), 2.10-1.95 (m, 2H).

Example 1479

4-[5-Chloro-2-(1-methyl-2-oxo-2,3,4,5-tetrahydro-1H-benzo[b]azepin-7-ylamino)-pyrimidin-4-ylamino]-benzo[1,3]dioxole-5-carboxylic acid methyl amide 1479a) 4-Amino-benzo[1,3]dioxole-5-carboxylic acid methylamide was prepared by heating a mixture of 4-amino-benzo[1,3]dioxole-5-carboxylic acid methyl ester (198 mg, 1.01 mmol, Dallacker, Franz, et al. *Justus Liebigs Ann Chem* 1966, 694 117-22) with 2.0 M methanolic $MeNH_2$ (7 mL, 14 mmol) and CuCN (1.42 g, 28.6 mmol) to 50° C. for 72 h. Excess catalyst was removed by filtration; filtrate was extracted into $CH_2Cl_2$, washed with water and dried by passing through a plug of $Na_2SO_4$. Evaporation of solvent afforded a white powder (187 mg, 95%) that was used in subsequent steps without further purification.

1479b) 4-(2,5-Dichloro-pyrimidin-4-ylamino)-benzo[1,3]dioxole-5-carboxylic acid methylamide was prepared in an anlogous manner as described in Example 313b.

1479c) The above pyrimidine (50.2 mg, 0.147 mmol) was coupled with 7-amino-1-methyl-1,3,4,5-tetrahydro-benzo[b]azepin-2-one (33.2 mg, 0.174 mmol) in an analogous manner described in Example 356c. Product was isolated by gradient elution (EtOAc/hexane) off an amine-modified silica gel column as a white powder (42 mg, 58%) and had the following properties: m.p: 254-256° C.; LC/MS (m/e): 495 (M+H); $^1$H-NMR (DMSO-$d_6$, 400 MHz): δ 9.80 (s, 1H), 9.44 (s, 1H), 8.50 (s, 1H), 8.19 (s, 1H), 7.47 (s, 1H), 7.42 (d, J=8.3, 1H), 7.27 (d, J=7.9, 1H), 7.06 (d, J=8.3, 1H), 6.92 (d, J=7.9, 1H), 5.87 (s, 2H), 3.29 (s, 3H), 2.73 (d, J=4.3, 3H), 2.40 (m, 2H), 2.10 (m, 2H), 1.99 (m, 2H).

Example 1480

4-{5-Chloro-2-[3-(2-methoxy-ethyl)-2,3,4,5-tetrahydro-1H-benzo[d]azepin-7-ylamino]-pyrimidin-4-ylamino}-benzo[1,3]dioxole-5-carboxylic acid methylamide The title compound was prepared by combining Example 1479b (50.2 mg, 0.147 mmol) and Example 34b (38.4 mg, 0.174 mmol) in an analogous manner described in Example 151d. The title product was isolated by gradient elution (EtOAc/hexane) off an amine-modified silica gel column as a white powder (44 mg, 56%) and had the following properties: m.p: 192-195° C.; LC/MS (m/e): 525 (M+H); $^1$H-NMR (DMSO-$d_6$, 400 MHz): δ 9.77 (s, 1H), 9.26 (s, 1H), 8.51 (s, 1H), 8.15 (s, 1H), 7.33 (s, 1H), 7.26 (d, J=8.7, 1H), 7.20 (d, J=8.2, 1H), 6.92 (d, J=8.7, 1H), 6.84 (d, J=8.2, 1H), 5.85 (s, 2H), 3.25 (s, 3H), 2.73 (d, J=4.5, 3H), 2.70-2.40 (series of m, 12H).

Example 1481

4-[5-Chloro-2-(5,5-dimethyl-2-oxo-2,3,4,5-tetrahydro-1H-benzo[b]azepin-8-ylamino)-pyrimidin-4-ylamino]-benzo[1,3]dioxole-5-carboxylic acid methyl amide The title compound was prepared by combining Example 1479b (50.2 mg, 0.147 mmol) and 8-amino-5,5-dimethyl-1,3,4,5-tetrahydro-benzo[b]azepin-2-one (Example N?, 35.6 mg, 0.174 mmol) in an analogous manner described in Example 356c. The title product was isolated by gradient elution (EtOAc/hexane) off an amine-modified silica gel column as a white powder (44 mg, 56%) and had the following properties: m.p: 180-185° C.; LC/MS (m/e): 509 (M+H); $^1$H-NMR (DMSO-$d_6$, 400 MHz): δ 9.77 (s, 1H), 9.37 (s, 1H), 9.24 (s, 1H), 8.46 (m, 1H), 8.17 (s, 1H), 7.36 (d, J=10.2, 1H), 7.26 (d, J=8.2, 1H), 7.08 (m, 2H), 6.87 (d, J=8.2, 1H), 5.85 (s, 2H), 2.73 (d, J=4.5, 3H), 2.20-2.10 (m, 2H), 2.00-1.85 (m, 2H), 1.28 (s, 6H).

Example 1482

4-[5-Chloro-2-(2-oxo-2,3,4,5-tetrahydro-1H-benzo[b]azepin-8-ylamino)-pyrimidin-4-ylamino]-benzo[1,3]dioxole-5-carboxylic acid methylamide The title compound was prepared by combining Example 1479b (50.2 mg, 0.147 mmol) and 8-amino-1,3,4,5-tetrahydro-benzo[b]azepin-2-one (30.8 mg, 0.174 mmol) in an analogous manner described in Example 356c. The title product was isolated as described in Example 1477b as a gray powder (53 mg, 75%) and had the following properties: m.p: 238-241° C.; LC/MS (m/e): 481 (M+H); $^1$H-NMR (DMSO-$d_6$, 400 MHz): δ 9.76 (s, 1H), 9.38 (s, 1H), 9.20 (s, 1H), 8.46 (m, 1H), 8.17 (s, 1H), 7.39 (d, J=9.9, 1H), 7.26 (d, J=8.2, 1H), 7.14 (s, 1H), 6.96 (d, J=8.2, 1H), 6.87 (d, J=9.9, 1H), 5.93 (s, 2H), 2.73 (d, J=4.5, 3H), 2.60-2.654 (m, 2H), 2.19-2.05 (series of m, 4H).

Example 1483

[2-(5-Chloro-2-{7-[4-(4-methyl-piperazin-1-yl)-piperidin-1-yl]-6,7,8,9-tetrahydro-5H-benzocyclohepten-2-ylamino}-pyrimidin-4-ylamino)-3-fluoro-phenoxy]-acetonitrile The title compound was prepared by combining [2-(2,5-dichloro-pyrimidin-4-ylamino)-3-fluoro-phenoxy]-acetonitrile (Example N?, 31.3 mg, 0.100 mmol) and 7-[4-(4-methyl-piperazin-1-yl)-piperidin-1-yl]-6,7,8,9-tetrahydro-5H-benzocyclohepten-2-ylamine (Example N?, 25.2 mg, 0.074 mmol) in an analogous manner described in Example 151d. The title product was isolated as described in Example 1475b as a white foam (33 mg, 66%) that had the following properties: m.p: 110-116° C.; LC/MS (m/e): 620 (M+H); $^1$H-NMR (CDCl$_3$, 400 MHz): δ 8.10 (s, 1H), 7.36 (dd, J=14.7, 7.8 1H), 7.14 (s, 1H), 7.05 (d, J=6.9, 1H), 7.01 (d, J=8.7, 1H), 6.94-6.90 (m, 2H), 6.88 (s, 1H), 6.50 (s, 1H), 4.73 (s, 2H), 2.90-2.80 (m, 2H), 2.75-2.35 (m, 10H), 2.30 (s, 3H), 2.30-2.18 (m, 2H), 2.10-2.00 (m, 2H), 1.85-1.65 (m, 4H), 1.65-1.45 (m, 2H) 1.40-1.20 (m, 4H).

Example 1484

2-{5-Chloro-2-[3-(2-methoxy-ethyl)-2,3,4,5-tetrahydro-1H-benzo[d]azepin-7-ylamino]-pyrimidin-4-ylamino}-thiophene-3-carboxylic acid methylamide 1484a) 2-(2,5-Dichloro-pyrimidin-4-ylamino)-thiophene-3-carboxylic acid methylamide was prepared in an anlogous manner as described in Example 313b from 2-aminothiophene-3-carboxylic acid methylamide (WO9967202).

1484b) The above pyrimidine in Example 1484a (70.2 mg, 0.232 mmol) was coupled with Example 34b (61 mg, 0.28 mmol) in an analogous manner described in Example 151d. The title product was isolated by gradient elution (EtOAc/hexane) off an amine-modified silica gel column as a yellow powder (86 mg, 76%) and had the following properties: m.p: 217-221° C.; LC/MS (m/e): 487 (M+H); $^1$H-NMR (DMSO-d$_6$, 400 MHz): δ 12.69 (s, 1H), 9.31 (s, 1H), 8.39 (br s, 1H), 8.25 (s, 1H), 7.50-7.40 (m, 2H), 7.28 (br s, 1H), 7.02 (d, J=7.9, 1H), 6.98 (d, J=5.8, 1H), 3.46 (t, J=5.6, 2H), 3.25 (s, 3H), 2.85-2.75 (m, 5H including 2.80, d, J=4.0), 2.70-2.55 (m, 4H) 2.50 (m, 4H-obscured by DMSO peak).

Example 1485

2-[5-Chloro-2-(2-oxo-2,3,4,5-tetrahydro-1H-benzo[b]azepin-8-ylamino)-pyrimidin-4-ylamino]-thiophene-3-carboxylic acid methylamide The title compound was prepared by combining Example 1484a (70.2 mg, 0.232 mmol) and 8-amino-1,3,4,5-tetrahydro-benzo[b]azepin-2-one (49 mg, 0.28 mmol) in an analogous manner described in Example 356c. The title product was isolated as described in Example 1477b as a yellow powder (78 mg, 76%) and had the following properties: m.p: 314-316° C.; LC/MS (m/e): 443 (M+H); $^1$H-NMR (DMSO-d$_6$, 400 MHz): δ 12.72 (s, 1H), 9.51 (s, 1H), 9.46 (s, 1H), 8.40 (br s, 1H), 8.28 (s, 1H), 7.44 (d, J=5.9, 1H), 7.39 (s, 1H), 7.32 (d, J=8.2, 1H), 7.17 (d, J=8.2, 1H), 6.93 (d, J=5.9, 1H), 2.80 (d, J=3.8, 3H), 2.65 (m, 2H) 2.18 (m, 2H), 2.10 (m, 2H).

Example 1486

2-[5-Chloro-2-(5,5-dimethyl-2-oxo-2,3,4,5-tetrahydro-1H-benzo[b]azepin-8-ylamino)-pyrimidin-4-ylamino]-thiophene-3-carboxylic acid methyl amide The title compound was prepared by combining Example 1484a (70.2 mg, 0.232 mmol) and 8-amino-5,5-dimethyl-1,3,4,5-tetrahydro-benzo[b]azepin-2-one (Example N?, 57 mg, 0.28 mmol) in an analogous manner described in Example 356c. The title product was isolated as described in Example 1477b as a pale green powder (88 mg, 81%) and had the following properties: m.p: 319-322° C.; LC/MS (m/e): 471 (M+H); $^1$H-NMR (DMSO-d$_6$, 400 MHz): δ 12.71 (s, 1H), 9.50 (s, 1H), 9.45 (s, 1H), 8.42 (br s, 1H), 8.27 (s, 1H), 7.44 (d, J=5.6, 1H), 7.38 (s, 1H), 7.30 (m, 2H), 6.93 (d, J=5.6, 1H), 2.80 (d, J=4.1, 3H), 2.21 (t, J=6.6, 2H), 2.02 (t, J=6.6, 2H), 1.34 (s, 6H).

Example 1487

2-[5-Chloro-2-(1-methyl-2-oxo-2,3,4,5-tetrahydro-1H-benzo[b]azepin-7-ylamino)-pyrimidin-4-ylamino]-thiophene-3-carboxylic acid methylamide The title compound was prepared by combining Example 1484a (70.2 mg, 0.232 mmol) and 7-amino-1-methyl-1,3,4,5-tetrahydro-benzo[b]azepin-2-one (53 mg, 0.28 mmol) in an analogous manner described in Example 151d. The title product was isolated by gradient elution (EtOAc/hexane) off an amine-modified silica gel column as a pale green powder (72 mg, 68%) and had the following properties: m.p: 278-280° C.; LC/MS (m/e): 457 (M+H); $^1$H-NMR (DMSO-d$_6$, 400 MHz): δ 12.73 (s, 1H), 9.47 (s, 1H), 8.39 (br s, 1H), 8.29 (s, 1H), 7.61 (s, 1H), 7.53 (d, J=7.3, 1H), 7.44 (d, J=5.8, 1H), 7.26 (d, J=7.3, 1H), 7.00 (d, J=5.8, 1H), 3.22 (s, 3H), 2.80 (d, J=4.3, 3H), 2.65 (t, J=6.9, 2H), 2.18 (t, J=6.9, 2H), 2.06 (t, J=6.9, 2H).

Example 1488

3-Chloro-2-(5-chloro-2-{7-[4-(4-methyl-piperazin-1-yl)-piperidin-1-yl]-6,7,8,9-tetrahydro-5H-benzocyclohepten-2-ylamino}-pyrimidin-4-ylamino)-N-methyl-benzamide The title compound was prepared by combining Example 312b (47.6 mg, 0.144 mmol) and 7-[4-(4-methyl-piperazin-1-yl)-piperidin-1-yl]-6,7,8,9-tetrahydro-5H-benzocyclohepten-2-ylamine (Example N?, 53.9 mg, 0.157 mmol) in an analogous manner described in Example 151d. After extracting the reaction mixture into CH$_2$Cl$_2$, product was isolated as described in Example 1475b as a white foam (16 mg, 17%) that had the following properties: m.p: 171-175° C.; LC/MS (m/e): 637 (M+H); $^1$H-NMR (CDCl$_3$, 400 MHz): δ 8.09 (s, 1H), 7.84 (br s, 1H), 7.61 (d, J=8.1, 1H), 7.49 (d, J=7.8, 1H), 7.31 (app t, J=7.8, 1H), 7.16 (s, 1H), 7.00 (d, J=7.8, 1H), 6.90 (d, J=8.3, 1H), 6.5 (s, 1H), 6.01 (s, 1H), 2.90-2.80 (m, 2H), 2.77 (d, J=3.9, 3H), 2.75-2.70 (m, 2H), 2.68-2.40 (series of m, 8H), 2.30 (s, 3H), 2.30-2.18 (m, 2H), 2.10-2.00 (m, 2H), 1.85-1.65 (m, 4H), 1.65-1.45 (m, 2H) 1.40-1.20 (m, 4H).

Example 1489

2-[2-(1-Acetyl-2,3,4,5-tetrahydro-1H-benzo[b]azepin-8-ylamino)-5-chloro-pyrimidin-4-ylamino]-3-fluoro-N-methyl-benzamide 1489a) 1-Acetyl-8-amino-1,3,4,5-tetrahydro-benzo[b]azepin-2-one was prepared by acylation and reduction of 8-nitro-1,3,4,5-tetrahydro-benzo[b]azepin-2-one (Johnson, Paul D. et al. Bioorganic Med. Chem. Letters 2003, 13, 4197-4200) as described for 5,5-dimethyl-8-nitro-1,3,4,5-tetrahydro-benzo[b]azepin-2-one (Example N?).

1489b) The title compound was prepared by combining Example 311b (75.2 mg, 0.239 mmol) and Example 1489a (54.2 mg, 0.265 mmol) in an analogous manner described in Example 356c. The title product was isolated by gradient elution (EtOAc/hexane) off an amine-modified silica gel column as a white powder (78 mg, 68%) and had the following properties: m.p: 232-234° C.; LC/MS (m/e): 483 (M+H); $^1$H-NMR (DMSO-d$_6$, 400 MHz): δ 9.45 (s, 1H), 9.35 (s, 1H), 8.53 (br s, 1H), 8.20 (s, 1H), 7.49 (s, 1H), 7.46 (m, 1H), 7.38 (m, 2H), 7.27 (d, J=7.6, 1H), 7.04 (d, J=7.6, 1H), 4.48 (d, J=13.6, 1H), 2.74 (d, J=4.6, 3H), 2.56 (m, 2H), 2.34 (m, 1H) 1.97 (m, 1H), 1.70 (m, 2H), 1.62 (s, 3H), 1.22 (m, 1H).

Example 1490

2-[2-(1-Acetyl-2,3,4,5-tetrahydro-1H-benzo[b]azepin-8-ylamino)-5-chloro-pyrimidin-4-ylamino]-3-fluoro-N-prop-2-ynyl-benzamide The title compound was prepared by combining 2-(2,5-Dichloro-pyrimidin-4-ylamino)-3-fluoro-N-prop-2-ynyl-benzamide (Example N?, 75.4 mg, 0.222 mmol) and Example 1489a (50.1 mg, 0.245 mmol) in an analogous manner described in Example 356c. After extracting the reaction mixture into CH$_2$Cl$_2$, product was isolated by gradient elution (EtOAc/hexane) off an amine-modified silica gel column as a white powder (78 mg, 69%) and had the following properties: m.p: 210-214° C.; LC/MS (m/e): 507 (M+H); $^1$H-NMR (DMSO-d$_6$, 400 MHz): δ 9.44 (s, 1H), 9.13 (s, 1H), 8.93 (m, 1H), 8.18 (s, 1H), 7.49-7.37 (series of m, 3H), 7.22 (d, J=7.8, 1H), 7.03 (d, J=7.8, 1H), 4.46 (d, J=12.9, 1H), 4.00 (m, 2H), 3.11 (s, 1H), 2.68-2.55 (m, 2H), 2.40-2.33 (m, 1H) 1.86 (m, 1H), 1.70 (m, 2H), 1.61 (s, 3H), 1.22 (m, 1H).

Example 1491

2-[5-Chloro-2-(3-morpholin-4-yl-2-oxo-2,3,4,5-tetrahydro-1H-benzo[b]azepin-8-ylamino)-pyrimidin-4-ylamino]-3-fluoro-N-methyl-benzamide 1491a) A mixture of 8-nitro-1,3,4,5-tetrahydro-1-benzazepin-2-one (1.72 g, 8.34 mmol) and N,N,N',N'-Tetramethylethylenediamine (5.02 mL, 33.3 mmol) in methylene chloride (25 mL) was chilled to −20° C. and iodotrimethylsilane (5.32 g, 26.6 mmol) was added. The mixture became homogeneous and was stirred for 30 min before adding iodine (3.17 g, 12.5 mol). After stirring for 2 h at 0° C., the reaction was quenched with 10% aqueous Na$_2$S$_2$O$_3$ and the mixture was filtered. The solid residue was washed with water (10×5 mL) and then with ether (2×2 mL) to yield 2.345 g of 3-iodo-8-nitro-1,3,4,5-tetrahydro-benzo[b]azepin-2-one (contaminated with ~8% starting material) that was used as such in the next reaction.

1491b) A mixture of Example 1491a (184.0 mg, 0.554 mmol), sodium carbonate (29 mg, 0.28 mmol) and morpholine (49.7 mg, 0.571 mmol) in propylene glycol (5 mL) was heated at 130° C. for 30 minutes, poured into water (10 mL) and filtered. The filtrate was extracted into DCM, washed with saturated aqueous Na$_2$CO$_3$ and the organic layer dried by passing through a funnel filled with Na$_2$SO$_4$. The filtrate was evaporated and the residue was purified by gradient elution (0% to 10% MeOH/DCM/5% NH$_4$OH) off a silica gel column to afford 3-morpholin-4-yl-8-nitro-1,3,4,5-tetrahydro-benzo[b]azepin-2-one (96 mg, 56%).

1491c) A mixture of Example 1491b (96 mg, 311 mmol) and 10% Pd/C in MeOH was shaken on a Parr apparatus under hydrogen (50 psi) for 2 h. Catalyst was removed by filtration through a plug of celite and evaporation of solvent afforded 8-amino-3-morpholin-4-yl-1,3,4,5-tetrahydro-benzo[b]azepin-2-one (81.2 mg, 100%)

1491d) The title compound was prepared by combining Example 311b (89.0 mg, 0.282 mmol) and Example 1491c (81.5 mg, 0.312 mmol) in an analogous manner described in Example 151d. The product was isolated by gradient elution (EtOAc/hexane) off an amine-modified silica gel column as a white powder (48 mg, 32%) and had the following properties: m.p: 270-271° C.; LC/MS (m/e): 540 (M+H); $^1$H-NMR (5% MeOD/CDCl$_3$, 400 MHz): δ 8.03 (s, 1H), 7.45 (d, J=7.3, 1H), 7.40-7.27 (m, 3H), 7.01 (s, 2H), 3.74 (m, 4H), 3.02 (m, 1H), 2.89 (s, 3H), 2.76 (m, 1H) 2.64 (m, 5H), 2.30 (m, 1H), 2.20 (m, 1H), NH protons obscured by solvent.

Example 1492

1-(2-{5-Chloro-2-[3-(2-methoxy-ethyl)-2,3,4,5-tetrahydro-1H-benzo[d]azepin-7-ylamino]-pyrimidin-4-ylamino}-benzenesulfonyl)-pyrrolidin-3-ol The title compound was prepared by combining {2-[3-(tert-butyl-dimethyl-silanyloxy)-pyrrolidine-1-sulfonyl]-phenyl}-(2,5-dichloro-pyrimidin-4-yl)-amine (Example N?, 150.6 mg, 0.299 mmol) and Example 34b (72.2 mg, 0.328 mmol) in an analogous manner described in Example 151d. The mixture was treated with 6N HCl (1 mL), stirred for 1 h and neutralized with saturated aqueous NaHCO$_3$. After extracting the reaction mixture into CH$_2$Cl$_2$, product was isolated by gradient elution (0% to 10% MeOH/DCM/5% NH$_4$OH) off a silica gel column as a white powder (33 mg, 18%) and had the following properties: m.p: 120-128° C.; LC/MS (m/e): 573 (M+H); $^1$H-NMR (DMSO-d$_6$, 400 MHz): δ 9.41 (s, 1H), 9.37 (s, 1H), 8.57 (m, 1H), 8.27 (s, 1H), 7.87 (d, J=8.3, 1H), 7.65 (m, 1H), 7.40-7.20 (series of m, 3H), 6.97 (d, J=8.1, 2H), 4.97 (d, J=3.6, 1H), 4.16 (m, 1H), 3.45 (m, 2H), 3.31-3.20 (m, 5H), 3.05 (d, J=9.9, 1H), 2.77 (m, 2H), 2.75-2.54 (series of m, 8H), 1.78 (m, 1H), 1.66 (m, 1H).

Example 1493

8-{5-Chloro-4-[2-(3-hydroxy-pyrrolidine-1-sulfonyl)-phenylamino]-pyrimidin-2-ylamino}-1,3,4,5-tetrahydro-benzo[b]azepin-2-one The title compound was prepared by combining {2-[3-(tert-butyl-dimethyl-silanyloxy)-pyrrolidine-1-sulfonyl]-phenyl}-(2,5-dichloro-pyrimidin-4-yl)-amine (Example N?, 100.4 mg, 0.199 mmol) and 8-amino-1,3,4,5-tetrahydro-benzo[b]azepin-2-one (38.4 mg, 0.218 mmol) in an analogous manner described in Example 1492 and was obtained as a white powder (57 mg, 54%) that had the following properties: m.p: 155-160° C.; LC/MS (m/e): 529 (M+H); $^1$H-NMR (DMSO-d$_6$, 400 MHz): δ 9.56 (s, 1H), 9.44 (m, 2H), 8.65 (m, 1H), 8.29 (s, 1H), 7.85 (d, J=7.9, 1H), 7.66 (m, 1H), 7.40-7.20 (series of m, 3H), 7.10 (d, J=8.2, 1H), 4.99 (d, J=2.8, 1H), 4.18 (m, 1H), 3.26 (m, 3H), 3.05 (d, J=10.1, 1H), 2.63 (m, 2H), 2.16 (m, 2H), 2.08 (m, 2H), 1.82 (m, 1H), 1.67 (m, 1H).

Example 1494

2-{5-Chloro-4-[2-(5-methyl-[1,3,4]thiadiazol-2-yl)-phenylamino]-pyrimidin-2-ylamino}-5-methyl-8,9-dihydro-5H-7-oxa-5-aza-benzocyclohepten-6-one The title compound was prepared by combining (2,5-dichloro-pyrimidin-4-yl)-[2-(5-methyl-[1,3,4]thiadiazol-2-yl)-phenyl]-amine (Example N?, 75 mg, 0.22 mmol) and 2-amino-5-methyl-8,9-dihydro-5H-7-oxa-5-aza-benzocycloheptan-6-one (Example N?, 47 mg, 0.24 mmol) in an analogous manner described in Example 356c. The title product was isolated as described in Example 1477b as a white powder (32 mg, 26%) and had the following properties: m.p: 174-177° C.; LC/MS (m/e): 494 (M+H); $^1$H-NMR (DMSO-$d_6$, 400 MHz): δ 10.75 (s, 1H), 9.40 (s, 1H), 8.40-5.06 (series of m, 2H), 8.04 (d, J=7.0, 1H), 7.75-7.30 (series of m, 4H), 7.10 (d, J=8.6, 1H), 4.30 (t, J=6.3, 2H), 3.23 (s, 3H), 2.37 (s, 3H), 2.60 (m, 2H).

Example 1495

2-{5-Chloro-2-[3-(2-methoxy-ethylamino)-2-oxo-2,3,4,5-tetrahydro-1H-benzo[b]azepin-8-ylamino]-pyrimidin-4-ylamino}-3-fluoro-N-methyl-benzamide 1495a) A mixture of Example 1491a (250 mg, 0.75 mmol), sodium carbonate (40 mg, 0.38 mmol) and 2-methoxyethylamine (58.2 mg, 0.775 mmol) in propylene glycol (3 mL) was heated at 135° C. for 65 minutes, poured into water (10 mL) and filtered. The filtrate was extracted into DCM, washed with saturated aqueous $Na_2CO_3$ and the organic layer dried by passing through a funnel filled with $Na_2SO_4$. The filtrate was evaporated and the residue was purified by gradient elution (0% to 10% MeOH/DCM/5% $NH_4OH$) off a silica gel column to afford 3-(2-methoxy-ethylamino)-8-nitro-1,3,4,5-tetrahydro-1-benzazepin-2-one (155 mg, 74%).

1495b) A mixture of Example 1495a (150 mg, 540 mmol) and 10% Pd/C in MeOH was shaken on a Parr apparatus under hydrogen (50 psi) for 2 h. Catalyst was removed by filtration through a plug of celite, and evaporation of filtrate afforded 8-amino-3-(2-methoxy-ethylamino)-1,3,4,5-tetrahydro-1-benzazepin-2-one (134 mg, 100%).

1495c) The title compound was prepared by combining Example 311b (75.0 mg, 0.238 mmol) and Example 1495b (70.1 mg, 0.281 mmol) in an analogous manner described in Example 151d. The product was purified by reverse phase preparative HPLC (MeCN/$H_2O$/0.1% TFA). Appropriate fractions were combined and evaporated to yield the TFA salt of the title compound as a white powder (26 mg, 17%) that had the following properties: LC/MS (m/e): 528 (M+H); $^1$H-NMR (DMSO-$d_6$, 400 MHz): δ 10.21 (s, 1H), 9.42 (s, 1H), 9.35 (s, 1H), 8.96 (br s, 1H), 8.74 (br, s, 1H), 8.51 (d, J=4.8, 11H), 8.19 (s, 1H), 7.50 (m, 2H), 7.40 (m, 2H), 7.22 (br s, 1H), 7.02 (d, J=8.0, 1H), 3.84 (m, 1H), 3.52 (m, 2H), 3.25 (s, 3H), 3.06 (m, 2H), 2.75 (d, J=4.3, 3H), 2.64 (m, 3H), 2.13 (m, 1H).

Example 1496

2-{5-Chloro-2-[3-(2-dimethylamino-acetylamino)-1-ethyl-2-oxo-2,3,4,5-tetrahydro-1H-benzo[b]azepin-8-ylamino]-pyrimidin-4-ylamino}-3-fluoro-N-methyl-benzamide 1496a) 1-Ethyl-3-iodo-8-nitro-1,3,4,5-tetrahydro-benzo[b]azepin-2-one was prepared in an analogous manner described in Example 1472a from 1-ethyl-8-nitro-1,3,4,5-tetrahydro-benzo[b]azepin-2-one (WO2002100327A2).

1496b) A mixture of Example 1496a (3.593 g, 9.976 mmol) and $NaN_3$ (4.345 g, 66.84 mmol) in DMF (25 mL) was stirred at RT overnight. The reaction mixture was diluted with $H_2O$, extracted into EtOAc, separated and the organic layer dried over magnesium sulfate. After filtration, solvent was removed by rotary evaporation to afford 3-azido-1-ethyl-8-nitro-1,3,4,5-tetrahydro-benzo[b]azepin-2-one (2.55 g, 93%).

1496c) A mixture of Example 1496b (2.55 g, 9.23 mmol) and an equivalent amount of resin-bound triphenylphosphine was agitated in 90% aqueous THF (200 mL) for 20 h. The mixture was filtered, the resin washed with 10% MeOH/$CH_2Cl_2$ and the filtrate concentrated to afford 3-amino-1-ethyl-8-nitro-1,3,4,5-tetrahydro-benzo[b]azepin-2-one (2.30 g, 100%).

1496d) A mixture of Example 1496c (320 mg, 1.3 mmol) and triethylamine (0.60 mL, 4.3 mmol) in methylene chloride (10 mL), was treated with dimethylamino-acetyl chloride; hydrochloride (325 mg, 2.06 mmol). After stirring for 30 min, the reaction mixture was extracted into $CH_2Cl_2$ and washed with saturated aqueous $NaHCO_3$ and brine. The organic layer was dried by passing through a funnel filled with $Na_2SO_4$. The filtrate was evaporated and the residue was absorbed onto florisil and purified by gradient elution (0% to 15% MeOH/5% $NH_4OH$ in DCM) on a silica gel column to afford 2-dimethylamino-N-(1-ethyl-8-nitro-2-oxo-2,3,4,5-tetrahydro-1H-1-benzazepin-3-yl)-acetamide (350 mg, 81%).

1496e) A mixture of Example 1496d (350 mg, 1.05 mmol) and 10% Pd/C in MeOH was shaken on a Parr apparatus under hydrogen (50 psi) for 2 h. Catalyst was removed by filtration through a plug of celite, and evaporation of filtrate afforded 2-dimethylamino-N-(1-ethyl-8-nitro-2-oxo-2,3,4,5-tetrahydro-1H-benzo[b]azepin-3-yl)-acetamide (318 mg, 100%).

1496f) The title compound was prepared by combining Example 311b (56.1 mg, 0.21 mmol) and Example 1496e (65.0 mg, 0.178 mmol) in an analogous manner described in Example 151d. The product was purified by reverse phase preparative HPLC (MeCN/$H_2O$/0.1% TFA). Appropriate fractions were combined and evaporated to yield the TFA salt of the title compound as a white powder (45 mg, 36%) that had the following properties: LC/MS (m/e): 583 (M+H); $^1$H-NMR (DMSO-$d_6$, 400 MHz): δ 9.65 (br s, 1H), 9.55 (s, 1H), 9.49 (s, 1H), 8.94 (d, J=7.7, 1H), 8.57 (d, J=4.5, 1H), 8.22 (s, 1H), 7.61 (s, 1H), 7.50 (d, J=8.1, 1H), 7.45 (d, J=8.9, 1H), 7.27 (m, 2H), 7.07 (d, J=8.1, 1H), 4.31 (m, 3H), 4.01 (m, 1H), 2.92 (m, 1H), 2.79 (s, 6H), 2.75 (d, J=4.3, 3H), 2.56 (m, 2H), 2.18 (m, 1H) 1.97 (m, 1H), 0.89 (t, J=6.9, 3H).

Example 1497

2-{5-Chloro-2-[3-(2-dimethylamino-acetylamino)-1-ethyl-2-oxo-2,3,4,5-tetrahydro-1H-benzo[b]azepin-8-ylamino]-pyrimidin-4-ylamino}-3-fluoro-N-prop-2-ynyl-benzamide The title compound was prepared by combining 2-(2,5-Dichloro-pyrimidin-4-ylamino)-3-fluoro-N-prop-2-ynyl-benzamide (Example N?, 60.4 mg, 0.178 mmol) and Example 1496e (65 mg, 0.21 mmol) in an analogous manner described in Example 151d. The product was purified by reverse phase preparative HPLC (MeCN/$H_2O$/0.1% TFA). Appropriate fractions were combined and evaporated to yield the TFA salt of the title compound as a white powder (67 mg, 52%) that had the following properties: LC/MS (m/e): 607 (M+H); $^1$H-NMR (DMSO-$d_6$, 400 MHz): δ 9.65 (br s, 1H), 9.53 (s, 1H), 9.27 (s, 1H), 9.00 (s, 1H), 8.93 (d, J=7.3, 1H), 8.21 (s, 1H), 7.58 (s, 1H), 7.48 (m, 2H), 7.28 (m, 2H), 7.06 (d, J=8.2, 1H), 4.44-3.66 (series of m, 6H), 3.13 (s, 1H), 2.93 (m, 1H), 2.78 (s, 6H), 2.56 (m, 2H), 2.19 (m, 1H) 1.97 (m, 1H), 0.90 (t, J=6.5, 3H).

Example 1498

2-{5-Chloro-2-[1-ethyl-3-(2-methoxy-acetylamino)-2-oxo-2,3,4,5-tetrahydro-1H-benzo[b]azepin-8-ylamino]-pyrimidin-4-ylamino}-3-fluoro-N-methyl-benzamide 1498a) N-(8-Amino-1-ethyl-2-oxo-2,3,4,5-tetrahydro-1H-benzo[b]azepin-3-yl)-2-methoxy-acetamide was prepared in an analogous manner described in Examples 1496d and 1496e.

1498b) The title compound was prepared by combining Example 311b (56.1 mg, 0.21 mmol) and Example 1498a (62 mg, 0.18 mmol) in an analogous manner described in Example 356c. The product was purified by reverse phase preparative HPLC (MeCN/H$_2$O/0.1% TFA). Appropriate fractions were combined and evaporated to yield the title compound as a white powder (51 mg, 49%) that had the following properties: LC/MS (m/e): 570 (M+H); $^1$H-NMR (DMSO-d$_6$, 400 MHz): δ 9.54 (br s, 1H), 9.46 (s, 1H), 8.54 (d, J=4.5, 1H), 8.22 (s, 1H), 7.78 (d, J=7.8, 1H), 7.53 (s, 1H), 7.47 (d, J=7.6, 1H), 7.39 (m, 1H), 7.27 (m, 2H), 7.06 (d, J=8.3, 1H), 4.19 (m, 3H), 4.06 (m, 2H), 3.84 (s, 3H), 3.02 (m, 1H), 2.75 (d, J=4.3, 3H), 2.54 (m, 1H), 2.17 (m, 1H) 2.07 (m, 1H), 0.91 (t, J=6.8, 3H).

Example 1499

2-{5-Chloro-2-[1-ethyl-3-(2-methoxy-acetylamino)-2-oxo-2,3,4,5-tetrahydro-1H-benzo[b]azepin-8-ylamino]-pyrimidin-4-ylamino}-3-fluoro-N-prop-2-ynyl-benzamide The title compound was prepared by combining 2-(2,5-Dichloro-pyrimidin-4-ylamino)-3-fluoro-N-prop-2-ynyl-benzamide (Example N?, 60.4 mg, 0.178 mmol) and Example 1498a (65 mg, 0.21 mmol) in an analogous manner described in Example 356c. The product was purified by reverse phase preparative HPLC (MeCN/H$_2$O/0.1% TFA). Appropriate fractions were combined and evaporated to yield the title compound as a white powder (51 mg, 49%) that had the following properties: LC/MS (m/e): 594 (M+H); $^1$H-NMR (DMSO-d$_6$, 400 MHz): δ 9.50 (br s, 1H), 9.23 (s, 1H), 8.98 (m, 1H), 8.20 (s, 1H), 7.78 (d, J=7.6, 1H), 7.51 (s, 1H), 7.47 (d, J=7.6, 1H), 7.41 (m, 1H), 7.26 (m, 2H), 7.05 (d, J=7.8, 1H), 4.16 (m, 3H), 4.13-4.06 (series of m, 4H), 3.83 (s, 3H), 3.12 (s, 1H), 3.02 (m, 1H), 2.54 (m, 1H), 2.17 (m, 1H) 2.00 (m, 1H), 0.91 (t, J=6.8, 3H).

Example 1501

N-((1R,2S)-2-{5-Chloro-2-[3-(2-methoxy-ethyl)-2,3,4,5-tetrahydro-1H-benzo[d]azepin-7-ylamino]-pyrimidin-4-ylamino}-cyclopentyl)-methanesulfonamide To a solution of N*4*-((1S,2R)-2-Amino-cyclopentyl)-5-chloro-N*2*-[3-(2-methoxy-ethyl)-2,3,4,5-tetrahydro-1H-benzo[d]azepin-7-yl]-pyrimidine-2,4-diamine (132 mg, 0.298 mmol) in DCM (2 mL) was added Et3N (62.0 µL, 0.447 mmol) at 0° C. under argon. Stirred reaction for 10 min. before adding methanesulfonyl chloride (34.6 µL, 0.447 mmol) dropwise via syringe. Reaction stirred for 20 minutes at 0° C. The reaction mixture was diluted with DCM and washed with 1N NaOH (2×). Dried organic layer over MgSO$_4$, filtered and concentrated. The residue was purified by column chromatography to yield (58 mg, 38%). mp: 73-74° C., MS (ESI+): 509 (M+H), $^1$H-NMR (CDCl$_3$, 400 MHz) δ 9.14 (s, 1H), 7.97 (s, 1H), 7.51 (s, 1H), 1.33 (d, J=7.5 Hz, 1H), 7.32 (s, 1H), 6.96 (d, J=8 Hz, 1H), 6.40 (d, J=7 Hz, 1H), 4.34 (m, 1H), 3.89 (br s, 1H), 3.44 (t, J=6 Hz, 2H), 3.23 (s, 3H), 2.75 (br s, 8H), 2.62 (m, 8H), 2.50 (m, 5H), 2.02 (m, 2H), 1.76 (m, 2H), 1.66 (m, 1H), 1.54 (m, 2H).

Example 1502

(1S,2S)-2-[5-Chloro-2-(3-ethyl-2,3,4,5-tetrahydro-1H-enzo[d]azepin-7-ylamino)-pyrimidin-4-ylamino]-cyclohexanecarboxylic acid amide In an analogous manner to Example 1513, the product was prepared from (1S,2S)-2-(2,5-Dichloro-pyrimidin-4-ylamino)-cyclohexanecarboxylic acid amide and 3-Ethyl-2,3,4,5-tetrahydro-1H-benzo[d]azepin-7-ylamine. Product was isolated as a white solid (35.0 mg, 39%). mp: 243-245, MS (ESI+): 443 (M+H), $^1$H-NMR (CDCl$_3$, 400 MHz) δ 9.06 (s, 1H), 7.89 (s, 1H), 7.55 (s, 1H), 7.36 (d, J=8 Hz, 1H), 7.06 (s, 1H), 6.96 (d, J=8 Hz, 1H), 6.77 (s, 1H), 6.49 (d, J=8 Hz, 1H), 4.12 (m, 2H), 2.82 (s, 4H), 2.78 (s, 4H), 2.03 (m, 1H), 1.82 (d, 1H), 1.73 (m, 2H), 1.47-1.45 (m, 3H), 1.01 (s, 3H).

Example 1503

N-{(1R,2R)-2-[5-Chloro-2-(3-methoxy-5-methyl-6-oxo-5,6,8,9-tetrahydro-7-oxa-5-aza-benzocyclohepten-2-ylamino)-pyrimidin-4-ylamino]-cyclohexyl}-methanesulfonamide N-[(1R,2R)-2-(2,5-Dichloro-pyrimidin-4-ylamino)-cyclohexyl]-methanesulfonamide (60.0 mg, 0.177 mmol), 2-Amino-3-methoxy-5-methyl-8,9-dihydro-5H-7-oxa-5-aza-benzocyclohepten-6-one (39.3 mg, 0.177 mmol) and 5 drops of HCl/dioxane were stirred in isopropyl alcohol (2.00 mL, 26.1 mmol) at 120° C. in a sealed tube. After 24 hours the reaction mixture was concentrated and then extracted with DCM (20 mL) and washed with sat. NaHCO$_3$ (20 mL) followed by water. The organic layer was dried over MgSO$_4$, filtered and concentrated. The residue was chromatographed on ISCO flash system (0-10% DCM:MeOH) to obtain one peak by LC/MS. When analyzed by HPLC, two peaks were shown. The fractions were concentrated and the residue was chromatographed on ISCO flash system (0-100% Hex: EtOAc) to obtain the product and the decarboxylated side product. The product was isolated as a pale blue solid (35.0 mg, 37.7%). mp: 160-162° C., MS (ESI+): 525 (M+H), $^1$H-NMR (CDCl$_3$, 400 MHz) δ 8.11 (s, 1H), 7.95 (s, 1H), 7.68 (s, 1H), 7.15 (d, 1H), 7.01 (s, 1H), 6.85 (d, 1H), 4.36 (m, 2H), 3.88 (s, 3H), 3.30 (s, 3H), 2.90 (br s, 5H), 1.99 (br s, 3H), 1.7 (d, 2H), 1.5-1.1 (m, 5H).

Example 1505

2-[5-Chloro-2-(3-methoxy-5-methyl-6-oxo-5,6,8,9-tetrahydro-7-oxa-5-aza-benzocyclohepten-2-ylamino)-pyrimidin-4-ylamino]-N-methyl-benzamide In and analogous manner to Example 1503, the product was prepared from 2-(2,5-Dichloro-pyrimidin-4-ylamino)-

N-methyl-benzamide and 2-Amino-3-methoxy-5-methyl-8,9-dihydro-5H-7-oxa-5-aza-benzocyclohepten-6-one. Product isolated as a yellow powder (25 mg, 26%). mp: 235-237° C., MS (ESI+): 483 (M+H), $^1$H-NMR (CDCl$_3$, 400 MHz) δ 11.06 (s, 1H), 8.64 (d, J=8 Hz, 1H), 8.28 (s, 1H), 8.15 (s, 1H), 7.53 (d, 2H), 7.46 (t, J=8 Hz, 1H), 7.11 (t, J=7 Hz, 1H), 6.70 (s, 1H), 6.23 (br s, 1H), 4.47 (t, J=6 Hz, 2H), 3.93 (s, 3H), 3.41 (s, 3H), 3.06 (d, J=5 Hz, 3H), 2.85 (t, J=6 Hz, 2H).

Example 1506

2-[5-Chloro-4-(2-methoxy-4-morpholin-4-yl-phenylamino)-pyrimidin-2-ylamino]-3-methoxy-5-methyl-8,9-dihydro-5H-7-oxa-5-aza-benzocyclohepten-6-one In an analogous manner to Example 1503, the product was prepared from (2,5-Dichloro-pyrimidin-4-yl)-(2-methoxy-4-morpholin-4-yl-phenyl)-amine and 2-Amino-3-methoxy-5-methyl-8,9-dihydro-5H-7-oxa-5-aza-benzocyclohepten-6-one. Product isolated as an off-white powder (45 mg, 49%). mp: 242-245° C., MS (ESI+): 541 (M+H), $^1$H-NMR (CDCl$_3$, 400 MHz) δ 8.24 (s, 1H), 8.04 (s, 1H), 7.73 (s, 1H), 7.66 (s, 1H), 7.38 (d, J=8 Hz, 1H), 6.96 (s, 1H), 6.69 (s, 1H), 6.50 (s, 1H), 4.25 (t, 2H), 3.84 (s, 3H), 3.76 (br s, 8H), 3.26 (s, 3H), 3.14 (br s, 4H), 2.60 (t, 2H).

Example 1507

2-[5-Bromo-2-(3-methoxy-5-methyl-6-oxo-5,6,8,9-tetrahydro-7-oxa-5-aza-benzocyclohepten-2-ylamino)-pyrimidin-4-ylamino]-N-methyl-benzamide In an analogous manner to Example 1503, the product was prepared from 2-(5-Bromo-2-chloro-pyrimidin-4-ylamino)-N-methyl-benzamide and 2-Amino-3-methoxy-5-methyl-8,9-dihydro-5H-7-oxa-5-aza-benzocyclohepten-6-one. Product isolated as a yellow solid (25 mg, 24%). mp: 227-228° C., MS (ESI+): 527, 529 (M+H), $^1$H-NMR (CDCl$_3$, 400 MHz) δ 11.35 (s, 1H), 8.73 (br d, 1H), 8.48 (d, 1H), 8.25 (s, 1H), 8.24 (s, 1H), 7.71 (m, 2H), 7.35 (t, 1H), 7.10 (t, 1H), 7.04 (s, 1H), 4.31 (t, 2H), 3.82 (s, 3H), 3.37 (s, 3H), 2.82 (t, 2H), 2.80 (s, 3H).

Example 1508

2-[5-Chloro-4-(2-methoxy-phenylamino)-pyrimidin-2-ylamino]-3-methoxy-5-methyl-8,9-dihydro-5H-7-oxa-5-aza-benzocyclohepten-6-one In an analogous manner to Example 1503, the product was prepared from (2,5-Dichloro-pyrimidin-4-yl)-(2-methoxy-phenyl)-amine and 2-Amino-3-methoxy-5-methyl-8,9-dihydro-5H-7-oxa-5-aza-benzocyclohepten-6-one. Product isolated as a white solid (70 mg, 69%). mp: 192-194° C., MS (ESI+): 456 (M+H), $^1$H-NMR (CDCl$_3$, 400 MHz) δ 8.24 (s, 1H), 8.12 (s, 1H), 7.96 (d, 1H), 7.63 (s, 1H), 7.14 (q, 1H), 7.13 (s, 1H), 6.99 (s, 1H), 6.92 (t, 1H), 4.27 (t, J=6 Hz, 2H), 3.82 (s, 6H), 3.28 (s, 3H), 2.69 (t, J=6 Hz, 2H).

Example 1509

(1R,2R,3S,4S)-3-[5-Chloro-2-(3-methoxy-5-methyl-6-oxo-5,6,8,9-tetrahydro-7-oxa-5-aza-benzocyclohepten-2-ylamino)-pyrimidin-4-ylamino]-bicyclo[2.2.1]hept-5-ene-2-carboxylic acid amide In an analogous manner to Example 1503, the product was prepared from (1R,2R,3S,4S)-3-(2,5-Dichloro-pyrimidin-4-ylamino)-bicyclo[2.2.1]hept-5-ene-2-carboxylic acid amide and 2-Amino-3-methoxy-5-methyl-8,9-dihydro-5H-7-oxa-5-aza-benzocyclohepten-6-one. Product isolated as a light grey solid (70 mg, 72%). mp: 168-170° C., MS (ESI+): 485 (M+H), $^1$H-NMR (CDCl$_3$, 400 MHz) δ 8.03 (s, 1H), 7.96 (s, 1H), 7.75 (br s, 1H), 7.72 (s, 2H), 7.25 (s, 1H), 7.01 (s, 1H), 6.34 (br s, 1H), 6.19 (br s, 1H), 4.34 (t, 2H), 4.12 (t, 1H), 3.87 (s, 3H), 3.30 (s, 4H), 2.86 (s, 3H), 2.73 (s, 1H), 2.10 (d, 1H), 1.4 (d, 1H).

Example 1510

{3-[5-Chloro-2-(3-methoxy-5-methyl-6-oxo-5,6,8,9-tetrahydro-7-oxa-5-aza-benzocyclohepten-2-ylamino)-pyrimidin-4-ylamino]-phenoxy}-acetonitrile In an analogous manner to Example 1503, the product was prepared from [3-(2,5-Dichloro-pyrimidin-4-ylamino)-phenoxy]-acetonitrile and 2-Amino-3-methoxy-5-methyl-8,9-dihydro-5H-7-oxa-5-aza-benzocyclohepten-6-one. Product isolated as a white solid (45 mg, 50%). mp: 227-229° C., MS (ESI+): 481 (M+H), $^1$H-NMR (CDCl$_3$, 400 MHz) δ 8.91 (s, 1H), 8.15 (s, 1H), 7.96 (s, 1H), 7.73 (s, 1H), 7.37 (s, 1H), 7.35 (s, 1H), 7.30 (t, 1H), 6.99 (s, 1H), 6.82 (d, J=8 Hz, 1H), 5.11 (s, 2H), 4.28 (t, 2H), 3.83 (s, 3H), 3.28 (s, 3H), 2.71 (t, 2H).

Example 1511

2-[5-Chloro-2-(2-methoxy-5-methyl-6-oxo-5,6,8,9-tetrahydro-7-oxa-5-aza-benzocyclohepten-3-ylamino)-pyrimidin-4-ylamino]-N-methyl-benzamide In an analogous manner to Example 1503, the product was prepared from 2-(2,5-Dichloro-pyrimidin-4-ylamino)-N-methyl-benzamide and 3-Amino-2-methoxy-5-methyl-8,9-dihydro-5H-7-oxa-5-aza-benzocyclohepten-6-one. Product isolated as a white solid (20 mg, 20%). mp: 256-258° C., MS (ESI+): 483 (M+H), $^1$H-NMR (CDCl$_3$, 400 MHz) δ 11.02 (s, 1H), 8.53 (s, J=8 Hz, 1H), 8.34 (s, 1H), 8.15 (s, 1H), 7.51 (d, J=7 Hz, 1H), 7.42 (t, J=7 Hz, 1H), 7.15 (t, J=7 Hz, 1H), 6.73 (s, 1H), 6.26 (br s, 1H), 4.53 (t, 7 Hz, 2H), 3.94 (s, 1H), 3.06 (d, J=5 Hz, 3H), 3.02 (s, 3H), 2.94 (t, J=7, 2H).

Example 1512

2-[5-Bromo-2-(2-methoxy-5-methyl-6-oxo-5,6,8,9-tetrahydro-7-oxa-5-aza-benzocyclohepten-3-ylamino)-pyrimidin-4-ylamino]-N-methyl-benzamide In an analogous manner to Example 1503, the product was prepared from 2-(5-Bromo-2-chloro-pyrimidin-4-ylamino)-N-methyl-benzamide and 3-Amino-2-methoxy-5-methyl-8,9-dihydro-5H-7-oxa-5-aza-benzocyclohepten-6-one. Product triturated from Et$_2$O to obtain a white solid (28 mg, 30%). mp: 251-253° C., MS (ESI+): 527 (M+H), $^1$H-NMR (CDCl$_3$, 400 MHz) δ 10.86 (s, 1H), 8.45 (s, J=8 Hz, 1H), 8.33 (s, 1H), 8.25 (s, 1H), 7.51 (d, J=7 Hz, 1H), 7.41 (t, J=7 Hz, 1H), 7.16 (t, J=7 Hz, 1H), 6.73 (s, 1H), 6.24 (br s, 1H), 4.53 (t, 7 Hz, 2H), 3.93 (s, 1H), 3.06 (d, J=5 Hz, 3H), 2.97 (s, 3H), 2.93 (t, J=7, 2H).

Example 1513

2-[2-(3-Methoxy-5-methyl-6-oxo-5,6,8,9-tetrahydro-7-oxa-5-aza-benzocyclohepten-2-ylamino)-5-trifluoromethyl-pyrimidin-4-ylamino]-N-methyl-benzamide 2-(4-Chloro-5-trifluoromethyl-pyrimidin-2-ylamino)-3-methoxy-5-methyl-8,9-dihydro-5H-7-oxa-5-aza-benzocyclohepten-6-one and 2-Amino-N-methyl-benzamide (85 mg, 0.56 mmol;) was stirred in isopropyl alcohol (5.00 mL, 65.3 mmol;) with 10-camphorsulfonic acid (150 mg, 0.63 mmol;) at 120° C. in microwave for 30 min×3. The reaction mixture was concentrated and then extracted with DCM (20 mL) and washed with sat. NaHCO$_3$ (20 mL) followed by water. The organic layer was dried over MgSO$_4$, filtered and concentrated. The residue was chromatographed on ISCO flash system (0-100% Hex:EtOAc) to obtain the product as one of multiple peaks by UV. The fractions were concentrated and triturated in Et2O to obtain a filterable solid (25 mg, 29%). mp: 210-212° C. (soft 150), MS (ESI+): 517 (M+H), $^1$H-NMR (CDCl$_3$, 400 MHz) δ 10.85 (s, 1H), 8.42 (s, 1H), 8.40 (s, 1H), 8.24 (s, 1H), 7.71 (s, 1H), 7.52 (d, J=8 Hz, 1H), 7.43 (t, J=8 Hz, 1H), 7.13 (t, J=8 Hz, 1H), 6.70 (s, 1H), 6.19 (br s, 1H), 4.42 (t, J=6 Hz, 2H), 3.92 (s, 3H), 3.40 (s, 3H), 3.04 (d, J=5 Hz, 3H), 2.76 (t, 2H).

Example 1514

3-Methoxy-2-[4-(2-methoxy-4-morpholin-4-yl-phenylamino)-5-trifluoromethyl-pyrimidin-2-ylamino]-5-methyl-8,9-dihydro-5H-7-oxa-5-aza-benzocyclohepten-6-one In an analogous manner to Example 1513, the product was prepared from 2-(4-Chloro-5-trifluoromethyl-pyrimidin-2-ylamino)-3-methoxy-5-methyl-8,9-dihydro-5H-7-oxa-5-aza-benzocyclohepten-6-one and 2-Methoxy-4-morpholin-4-yl-phenylamine. Product isolated as a white solid (8.0 mg, 9%). mp: 232-234° C., MS (ESI+): 575 (M+H), $^1$H-NMR (CDCl$_3$, 400 MHz) δ 8.31 (s, 1H), 8.22 (s, 1H), 7.95 (m, 1H), 7.70 (s, 1H), 7.25 (s, 1H), 6.69 (s, 1H), 6.54 (s, 1H), 6.49 (d, J=8 Hz, 1H), 4.44 (t, J=6 Hz, 2H), 3.92 (s, 4H), 3.90 (s, 6H), 3.40 (s, 3H), 3.16 (t, J=5 Hz, 4H), 2.78 (m, 2H).

Example 1516

{2-[5-Chloro-2-(3-methoxy-5-methyl-6-oxo-5,6,8,9-tetrahydro-7-oxa-5-aza-benzocyclohepten-2-ylamino)-pyrimidin-4-ylamino]-phenoxy}-acetonitrile In an analogous manner to Example 1503, the product was prepared from [2-(2,5-Dichloro-pyrimidin-4-ylamino)-phenoxy]-acetonitrile and 2-Amino-3-methoxy-5-methyl-8,9-dihydro-5H-7-oxa-5-aza-benzocyclohepten-6-one. Product isolated as a white solid (55 mg, 50%). mp: 245-247° C., MS (ESI+): 481 (M+H), $^1$H-NMR (CDCl$_3$, 400 MHz) δ 8.40 (d, J=8 Hz, 1H), 8.21 (s, 1H), 8.14 (s, 1H), 7.57 (s, 1H), 7.53 (s, 1H), 7.17-7.07 (dt, 3H), 6.71 (s, 1H), 4.92 (s, 1H), 4.48 (t, J=6 Hz, 2H), 3.93 (s, 3H), 3.41 (s, 3H), 2.85 (t, J=6 Hz, 2H).

Example 1517

2-[5-Chloro-2-(2-methoxy-5-methyl-6-oxo-5,6,8,9-tetrahydro-7-oxa-5-aza-benzocyclohepten-1-ylamino)-pyrimidin-4-ylamino]-N-methyl-benzamide In an analogous manner to Example 1513, the product was prepared from 2-(2,5-Dichloro-pyrimidin-4-ylamino)-N-methyl-benzamide and 1-Amino-2-methoxy-5-methyl-8,9-dihydro-5H-7-oxa-5-aza-benzocyclohepten-6-one. Product was isolated as a light yellow solid (4.0 mg, 4%). mp: 160° C. followed by solidification and melt at 250 and discoloration, MS (ESI+): 483 (M+H), $^1$H-NMR (CDCl$_3$, 400 MHz) δ 11.21 (s, 1H), 8.35 (br s, 1H), 8.06 (s, 1H), 7.44 (d, J=8 Hz, 1H), 7.20 (br s, 1H), 7.12 (d, J=8 Hz, 1H), 7.01 (t, 1H), 6.98 (d, J=7 Hz, 1H), 6.40 (s, 1H), 6.21 (br s, 1H), 4.39 (t, 2H), 3.83 (s, 3H), 3.42 (s, 3H), 3.04 (d, J=5 Hz, 3H), 2.98 (t, J=6 Hz, 2H).

Example 1518

2-Methoxy-3-[4-(2-methoxy-4-morpholin-4-yl-phenylamino)-5-trifluoromethyl-pyrimidin-2-ylamino]-5-methyl-8,9-dihydro-5H-7-oxa-5-aza-benzocyclohepten-6-one In an analogous manner to Example 1513, the product was prepared from 3-(4-Chloro-5-trifluoromethyl-pyrimidin-2-ylamino)-2-methoxy-5-methyl-8,9-dihydro-5H-7-oxa-5-aza-benzocyclohepten-6-one and 2-Methoxy-4-morpholin-4-yl-phenylamine. Product was isolated as a white solid (55 mg, 43%). mp: 221-223° C., MS (ESI+): 575 (M+H), 1H-NMR (CDCl$_3$, 400 MHz) δ 8.38 (s, 1H), 8.30 (s, 1H), 7.83 (s, 1H), 7.68 (s, 1H), 7.60 (br d, 1H), 7.03 (s, 1H), 6.63 (s, 1H), 6.32 (br d, 1H), 4.36 (t, J=6 Hz, 2H), 3.82 (s, 3H), 3.78 (s, 3H), 3.75 (m, 4H), 3.11 (m, 4H), 3.01 (s, 3H), 2.93 (t, J=6 Hz, 2H).

Example 1520

{2-[5-Chloro-2-(1-ethyl-5,5-dimethyl-2-oxo-2,3,4,5-tetrahydro-1H-1-benzazepin-8-ylamino)-pyrimidin-4-ylamino]-3-fluoro-phenoxy}-acetonitrile In an analogous manner to Example 1513, the product was prepared from 2-(2,5-Dichloro-pyrimidin-4-ylamino)-3-fluoro-phenoxy]-acetonitrile and 8-Amino-1-ethyl-5,5-dimethyl-1,3,4,5-tetrahydro-benzo[b]azepin-2-one. Product was isolated as a pale yellow solid. (50 mg, 51%). mp: 235-238° C., MS (ESI+): 509.5 (M+H), $^1$H-NMR (CDCl$_3$, 400 MHz) δ 9.26 (s, 1H), 8.61 (s, 1H), 8.11 (s, 1H), 7.40 (m, 2H), 7.29 (d, J=9 Hz, 1H), 7.13 (d, J=8 Hz, 1H), 7.06 (t, J=9 Hz, 1H), 6.97 (d, J=8 Hz, 1H), 5.19 (s, 2H), 3.54 (q, J=7 Hz, 2H), 2.07 (br m, 2H), 1.87 (br m, 2H), 1.20 (s, 6H), 1.12 (m, 4H).

Example 1521

(2-{5-Chloro-2-[1-(2-methoxy-ethyl)-5,5-dimethyl-2-oxo-2,3,4,5-tetrahydro-1H-1-benzazepin-8-ylamino]-pyrimidin-4-ylamino}-3-fluoro-phenoxy)-acetonitrile In an analogous manner to Example 1513, the product was prepared from [2-(2,5-Dichloro-pyrimidin-4-ylamino)-3-fluoro-phenoxy]-acetonitrile and 8-Amino-1-(2-methoxy-ethyl)-5,5-dimethyl-1,3,4,5-tetrahydro-benzo[b]azepin-2-one. Product isolated as a yellow foam (50 mg, 48%). mp: 235-238° C., MS (ESI+): 539.5 (M+H), $^1$H-NMR (CDCl$_3$, 400 MHz) δ 9.26 (s, 1H), 8.61 (s, 1H), 8.11 (s, 1H), 7.40 (m, 2H), 7.29 (d, J=9 Hz, 1H), 7.13 (d, J=8 Hz, 1H), 7.06 (t, J=9 Hz, 1H), 6.97 (d, J=8 Hz, 1H), 5.19 (s, 2H), 3.54 (q, 7 Hz, 2H), 2.07 (br m, 2H), 1.87 (br m, 2H), 1.20 (s, 6H), 1.12 (m, 4H).

Example 1522

2-{5-Chloro-2-[8-methoxy-3-(2-morpholin-4-yl-ethyl)-2,3,4,5-tetrahydro-1H-3-benzazepin-7-ylamino]-pyrimidin-4-ylamino}-N,N-dimethyl-benzenesulfonamide In an analogous manner to Example 1513, the product was prepared from 2-(2,5-Dichloro-pyrimidin-4-ylamino)-N,N-dimethyl-benzenesulfonamide and 8-Methoxy-3-(2-morpholin-4-yl-ethyl)-2,3,4,5-tetrahydro-1H-3-benzazepin-7-ylamine. Product isolated as a white foam (30 mg, 28%). MS (ESI+): 616 (M+H), $^1$H-NMR (CDCl$_3$, 400 MHz) δ 9.35 (s, 1H), 8.55 (d, J=8 Hz, 1H), 8.15 (s, 1H), 8.01 (s, 1H), 7.90 (d, J=8 Hz, 1H), 7.57 (t, 1H), 7.50 (s, 1H), 7.26 (m, 1H), 6.66 (s, 1H), 3.89 (s, 3H), 3.74 (s, 4H), 2.88 (s, 2H), 2.76-7.70 (m, 14H), 2.69-2.52 (m, 6H).

Example 1523

5-Chloro-N(2)-[8-methoxy-3-(2-morpholin-4-yl-ethyl)-2,3,4,5-tetrahydro-1H-3-benzazepin-7-yl]-N(4)-(2-methoxy-4-morpholin-4-yl-phenyl)-pyrimidine-2,4-diamine In an analogous manner to Example 1503, the product was prepared from (2,5-Dichloro-pyrimidin-4-yl)-(2-methoxy-4-morpholin-4-yl-phenyl)-amine and 8-Methoxy-3-(2-morpholin-4-yl-ethyl)-2,3,4,5-tetrahydro-1H-3-benzazepin-7-ylamine. Product isolated as an off-white foam (23 mg, 22%). MS (ESI+): 624 (M+H), $^1$H-NMR (CDCl$_3$, 400 MHz) δ 8.29 (d, J=9 Hz, 1H), 8.13 (s, 1H), 8.04 (s, 1H), 7.56 (s, 1H), 7.45 (s, 1H), 6.65 (s, 1H), 6.57 (s, 1H), 6.53 (d, J=9 Hz, 1H), 3.94 (s, 4H), 3.91 (m, 2H), 3.88 (s, 4H), 3.73 (t, J=5 Hz, 4H), 3.17 (t, J=4 Hz, 4H), 2.88 (m, 4H), 2.70 (m, 6H), 2.56-2.51 (m, 6H).

Example 1524

2-{5-Chloro-2-[8-methoxy-3-(2-morpholin-4-yl-ethyl)-2,3,4,5-tetrahydro-1H-3-benzazepin-7-ylamino]-pyrimidin-4-ylamino}-N-methyl-benzamide In an analogous manner to Example 1503, the product was prepared from 2-(2,5-Dichloro-pyrimidin-4-ylamino)-N-methyl-benzamide and 8-Methoxy-3-(2-morpholin-4-yl-ethyl)-2,3,4,5-tetrahydro-1H-3-benzazepin-7-ylamine. Product isolated as and off-white foam (10 mg, 9%). MS (ESI+): 566 (M+H), $^1$H-NMR (CDCl$_3$, 400 MHz) δ 11.02 (s, 1H), 8.69 (d, J=8 Hz, 1H), 8.12 (s, 1H), 8.10 (s, 1H), 7.52-7.43 (m, 3H), 7.09 (t, 8 Hz, 1H), 6.66 (s, 1H), 6.25 (d, J=4 Hz, 1H), 3.88 (s, 3H), 3.74 (t, J=4.5, 4H), 3.05 (d, J=5 Hz, 3H), 2.88 (br s, 2H), 2.79 (br s, 2H), 2.71 (br s, 6H), 2.56 (m, 2H), 2.52 (m, 4H).

Example 1525

2-{5-Chloro-2-[8-methoxy-3-(2-morpholin-4-yl-2-oxo-ethyl)-2,3,4,5-tetrahydro-1H-3-benzazepin-7-ylamino]-pyrimidin-4-ylamino}-N,N-dimethyl-benzenesulfonamide In an analogous manner to Example 1503, the product was prepared from 2-(2,5-Dichloro-pyrimidin-4-ylamino)-N,N-dimethyl-benzenesulfonamide and 2-(7-Amino-8-methoxy-1,2,4,5-tetrahydro-3-benzazepin-3-yl)-1-morpholin-4-yl-ethanone. Product was isolated as an off-white foam (60 mg, 55%). MS (ESI+): 630.6 (M+H), $^1$H-NMR (CDCl$_3$, 400 MHz) δ 9.36 (s, 1H), 8.54 (d, J=8 Hz, 1H), 8.16 (s, 1H), 8.02 (s, 1H), 7.90 (d, J=8 Hz, 1H), 7.58 (t, 1H), 7.52 (s, 1H), 7.25 (t, 1H), 6.67 (s, 1H), 3.89 (s, 3H), 3.74 (s, 7H), 3.67 (m, 2H), 3.30 (s, 2H), 2.87 (m, 2H), 2.76 (s, 8H), 2.68 (m, 5H).

Example 1526

2-{7-[5-Chloro-4-(2-methoxy-4-morpholin-4-yl-phenylamino)-pyrimidin-2-ylamino]-8-methoxy-1,2,4,5-tetrahydro-3-benzazepin-3-yl}-1-morpholin-4-yl-ethanone In an analogous manner to Example 1503, the product was prepared from (2,5-Dichloro-pyrimidin-4-yl)-(2-methoxy-4-morpholin-4-yl-phenyl)-amine and 2-(7-Amino-8-methoxy-1,2,4,5-tetrahydro-3-benzazepin-3-yl)-1-morpholin-4-yl-ethanone. Product isolated as white crystals (60 mg, 56%). mp: 189-191° C., MS (ESI+): 638.5 (M+H), $^1$H-NMR (CDCl$_3$, 400 MHz) δ 8.27 (d, J=8 Hz, 1H), 8.14 (s, 1H), 8.04 (s, 1H), 7.55 (s, 1H), 7.45 (s, 1H), 6.65 (s, 1H), 6.57 (s, 1H), 6.52 (d, J=8 Hz, 1H), 3.93-3.88 (m, 10H), 3.74-3.67 (m, 8H), 3.29 (s, 2H), 3.16 (t, J=5 Hz, 4H), 2.87 (m, 2H), 2.83 (m, 2H), 2.69 (m, 4H).

Example 1527

(1S,2S,3R,4R)-3-{5-Chloro-2-[8-methoxy-3-(2-morpholin-4-yl-2-oxo-ethyl)-2,3,4,5-tetrahydro-1H-3-benzazepin-7-ylamino]-pyrimidin-4-ylamino}-bicyclo[2.2.1]hept-5-ene-2-carboxylic acid amide In an analogous manner to Example 1503, the product was prepared from (1S,2S,3R,4R)-3-(2,5-Dichloro-pyrimidin-4-ylamino)-bicyclo[2.2.1]hept-5-ene-2-carboxylic acid amide and 2-(7-Amino-8-methoxy-1,2,4,5-tetrahydro-3-benzazepin-3-yl)-1-morpholin-4-yl-ethanone. Product was isolated as a white solid (20 mg, 20%). mp: 163° C. (125 soft), MS (ESI+): 582.5 (M+H), $^1$H-NMR (CDCl$_3$, 400 MHz) δ 8.21 (s, 1H), 7.91 (s, 1H), 7.42 (s, 1H), 6.65 (s, 1H), 6.57 (d, J=8 Hz, 1H), 6.33 (s, 2H), 5.56 (s, 1H), 5.28 (s, 1H), 4.46 (t, J=8 Hz, 1H), 3.89 (s, 3H), 3.74-3.67 (m, 9H), 3.30 (s, 2H), 3.09 (s, 1H), 2.89 (m, 6H), 2.69 (m, 5H), 2.53 (d, J=7 Hz, 1H), 2.28 (d, J=7 Hz, 1H), 1.67 (d, J=7 Hz, 1H).

Example 1528

N-((1R,2R)-2-{5-Chloro-2-[8-methoxy-3-(2-morpholin-4-yl-2-oxo-ethyl)-2,3,4,5-tetrahydro-1H-3-benzazepin-7-ylamino]-pyrimidin-4-ylamino}-cyclohexyl)-methanesulfonamide In an analogous manner to Example 1503, the product was prepared from N-[(1R,2R)-2-(2,5-Dichloro-pyrimidin-4-ylamino)-cyclohexyl]-methanesulfonamide and 2-(7-Amino-8-methoxy-1,2,4,5-tetrahydro-3-benzazepin-3-yl)-1-morpholin-4-yl-ethanone. Product isolated as a pale yellow foam (78 mg, 71%). MS (ESI+): 622.5 (M+H), $^1$H-NMR (CDCl$_3$, 400 MHz) δ 8.00 (s, 1H), 7.95 (s, 1H), 7.34 (s, 1H), 6.65 (s, 1H), 5.41 (d, J=7 Hz, 2H), 4.47 (t, J=8 Hz, 1H), 3.88 (s, 3H), 3.74 (t, J=5 Hz, 4H), 3.09 (s, 1H), 2.89 (br s, 5H), 2.71 (br s, 6H), 2.57-2.52 (m, 7H), 2.27 (d, J=9 Hz, 1H).

Example 1529

(1S,2S,3R,4R)-3-{5-Chloro-2-[8-methoxy-3-(2-morpholin-4-yl-ethyl)-2,3,4,5-tetrahydro-1H-3-benzazepin-7-ylamino]-pyrimidin-4-ylamino}-bicyclo[2.2.1]hept-5-ene-2-carboxylic acid amide In an analogous manner to Example 1503, the product was prepared from (1S,2S,3R,4R)-3-(2,5-Dichloro-pyrimidin-4-ylamino)-bicyclo[2.2.1]hept-5-ene-2-carboxylic acid amide and 8-Methoxy-3-(2-morpholin-4-yl-ethyl)-2,3,4,5-tetrahydro-1H-3-benzazepin-7-ylamine. Product was isolated as a white foam (15 mg, 13%). MS (ESI+): 568 (M+H), $^1$H-NMR (CDCl$_3$, 400 MHz) δ 8.20 (s, 1H), 7.91 (s, 1H), 7.40 (s, 1H), 6.66 (s, 1H), 6.55 (d, J=8 Hz, 1H), 6.32 (s, 2H), 5.56 (br s, 1H), 5.29 (br s, 1H), 4.47 (t, J=8 Hz, 1H), 3.88 (s, 3H), 3.74 (t, J=4.5 Hz, 4H), 3.09 (s, 1H), 2.89 (br s, 5H), 2.71 (br s, 6H), 2.57-2.52 (m, 7H), 2.27 (d, J=9 Hz, 1H).

Example 1530

2-{5-Chloro-2-[3-(2-hydroxy-ethyl)-8-methoxy-2,3,4,5-tetrahydro-1H-3-benzazepin-7-ylamino]-pyrimidin-4-ylamino}-N,N-dimethyl-benzenesulfonamide In an analogous manner to Example 1503, the product was prepared from 2-(2,5-Dichloro-pyrimidin-4-ylamino)-N,N-dimethyl-benzenesulfonamide and 2-(7-Amino-8-methoxy-1,2,4,5-tetrahydro-3-benzazepin-3-yl)-ethanol. The product was isolated as a white solid (8 g, 58%), mp: 149.5-151.5° C., MS (ESI+): 547 (M+H), $^1$H-NMR (CDCl$_3$, 400 MHz) δ 9.35 (s, 1H), 8.54 (d, J=8 Hz, 1H), 8.16 (s, 1H), 8.03 (s, 1H), 7.91 (d, J=8 Hz, 1H), 7.58 (t, 1H), 7.53 (s, 1H), 7.26 (m, 1H), 6.68 (s, 1H), 3.89 (s, 3H), 3.65 (t, 2H), 2.90 (m, 3H), 2.77-2.69 (m, 15H).

Example 1531

N-((1R,2R)-2-{5-Chloro-2-[3-(2-hydroxy-ethyl)-8-methoxy-2,3,4,5-tetrahydro-1H-3-benzazepin-7-ylamino]-pyrimidin-4-ylamino}-cyclohexyl)-methanesulfonamide In an analogous manner to Example 1503, the product was prepared from N-[(1R,2R)-2-(2,5-Dichloro-pyrimidin-4-ylamino)-cyclohexyl]-methanesulfonamide and 2-(7-Amino-8-methoxy-1,2,4,5-tetrahydro-3-benzazepin-3-yl)-ethanol. Product was isolated as a white foam (34 mg, 36%). MS (ESI+): 539 (M+H), $^1$H-NMR (CDCl$_3$, 400 MHz) δ 8.03 (s, 1H), 7.97 (s, 1H), 7.35 (s, 1H), 6.68 (s, 1H), 5.36 (d, J=8 Hz, 1H), 5.25 (br s, 1H), 3.96 (m, 1H), 3.89 (s, 3H), 3.66 (t, J=5 Hz, 2H), 3.26 (m, 1H), 2.91 (m, 4H), 2.80 (s, 3H), 2.74-2.69 (m, 6H), 2.25 (m, 2H), 1.86 (m, 2H), 1.40 (m, 4H).

Example 1532

(1S,2S,3R,4R)-3-{5-Chloro-2-[3-(2-hydroxy-ethyl)-8-methoxy-2,3,4,5-tetrahydro-1H-3-benzazepin-7-ylamino]-pyrimidin-4-ylamino}-bicyclo[2.2.1]hept-5-ene-2-carboxylic acid amide In an analogous manner to Example 1503, the product was prepared from (1S,2S,3R,4R)-3-(2,5-Dichloro-pyrimidin-4-ylamino)-bicyclo[2.2.1]hept-5-ene-2-carboxylic acid amide and 2-(7-Amino-8-methoxy-1,2,4,5-tetrahydro-3-benzazepin-3-yl)-ethanol. Product was isolated as a white foam (35 mg, 42%). MS (ESI+): 499 (M+H), $^1$H-NMR (CDCl$_3$, 400 MHz) δ 8.22 (s, 1H), 7.91 (s, 1H), 7.42 (s, 1H), 6.66 (s, 1H), 6.57 (s, 1H), 6.51 (s, 1H), 6.33 (s, 2H), 5.60 (s, 1H), 5.35 (s, 1H), 5.32 (s, 1H), 4.47 (t, J=8 Hz, 1H), 3.89 (s, 3H), 3.84 (s, 2H), 3.63 (d, 5H), 3.09 (s, 1H), 2.89-2.69 (m, 20H), 2.53 (d, J=9 Hz, 1H), 2.28 (d, J=9 Hz, 1H), 1.67 (d, J=9 Hz, 1H).

Example 1533

N-((1R,2R)-2-{5-Chloro-2-[8-methoxy-3-(2-morpholin-4-yl-ethyl)-2,3,4,5-tetrahydro-1H-3-benzazepin-7-ylamino]-pyrimidin-4-ylamino}-cyclohexyl)-methanesulfonamide In an analogous manner to Example 1503, the product was prepared from N-[(1R,2R)-2-(2,5-Dichloro-pyrimidin-4-ylamino)-cyclohexyl]-methanesulfonamide and 8-Methoxy-3-(2-morpholin-4-yl-ethyl)-2,3,4,5-tetrahydro-1H-3-benzazepin-7-ylamine. Product was isolated as a white foam (28 mg, 19%). MS (ESI+): 608 (M+H), $^1$H-NMR (CDCl$_3$, 400 MHz) δ 8.00 (s, 1H), 7.96 (s, 1H), 7.32 (s, 1H), 6.67 (s, 1H), 5.34 (d, J=8 Hz, 1H), 5.26 (d, 1H), 3.96 (m, 1H), 3.89 (s, 3H), 3.74 (t, 5 Hz, 4H), 3.27 (m, 1H), 2.90 9 m, 4H), 2.80 (s, 3H), 2.71 (m, 6H), 2.59 (m, 2H), 2.57 (br s, 4H), 2.25 (m, 2H), 2.39 (m, 4H).

Example 1534

5-Chloro-N(2)-[8-methoxy-3-(2-morpholin-4-yl-ethyl)-2,3,4,5-tetrahydro-1H-3-benzazepin-7-yl]-N(4)-[2-(propane-2-sulfonyl)-phenyl]-pyrimidine-2,4-diamine (2,5-Dichloro-pyrimidin-4-yl)-[2-(propane-2-sulfonyl)-phenyl]-amine (100 mg, 0.289 mmol) and 8-Methoxy-3-(2-morpholin-4-yl-ethyl)-2,3,4,5-tetrahydro-1H-3-benzazepin-7-ylamine (92.6 mg, 0.303 mmol) and 100 µL of 4M HCl in Dioxane (9:1, 1,4-Dioxane:Hydrogen Chloride) in 4 mL of 2-methoxyethanol were heated in a sealed tube at 120° C. over night. The reaction was extracted with DCM and washed with bicarb followed by water. Dried organic layer over MgSO$_4$, filtered and concentrated. The residue was chromatographed on ISCO flash system (0-15% MeOH:DCM). The desired fractions were concentrated and the product was collected as a foam from a small amount of DCM (65 mg, 37%). MS (ESI+): 615 (M+H), $^1$H-NMR (CDCl$_3$, 400 MHz) δ 9.53 (s, 1H), 8.58 (d, J=8 Hz, 1H), 8.17 (s, 1H), 8.00 (s, 1H), 7.75 (d, J=8 Hz, 1H), 7.62 (t, J=8 Hz, 1H), 7.50 (s, 1H), 7.27 (m, 1H), 6.67 (s, 1H), 3.89 (s, 3H), 3.74 (t, J=4 Hz, 4H), 3.27 (m, 1H), 2.88 (br s, 2H), 2.73-2.69 (m, 8H), 2.58 (m, 2H), 2.52 (br s, 4H), 1.70 (br s, 1H), 1.33 (d, J=7 Hz, 6H).

Example 1535

2-(7-{5-Chloro-4-[2-(propane-2-sulfonyl)-phenylamino]-pyrimidin-2-ylamino}-8-methoxy-1,2,4,5-tetrahydro-3-benzazepin-3-yl)-ethanol In an analogous manner to Example 1503, the product was prepared from (2,5-Dichloro-pyrimidin-4-yl)-[2-(propane-2-sulfonyl)-phenyl]-amine and 2-(7-Amino-8-methoxy-1,2,4,5-tetrahydro-3-benzazepin-3-yl)-ethanol. Product was isolated as a white foam (58 mg, 61%). MS (ESI+): 546.5 (M+H), $^1$H-NMR (CDCl$_3$, 400 MHz) δ 9.23 (s, 1H), 8.58 (d, J=8 Hz, 1H), 8.17 (s, 1H), 8.02 (s, 1H), 7.95 (d, J=8 Hz, 1H), 7.62 (t, J=7 Hz, 1H), 7.52 (s, 1H), 6.68 (s, 1H), 3.90 (s, 3H), 3.65 (t, J=5 Hz, 2H), 3.28 (m, 1H), 2.89 (m, 2H), 2.73-2.67 (m, 8H), 1.34 (d, J=7 Hz, 6H).

Example 1536

2-(7-{5-Chloro-4-[2-(propane-2-sulfonyl)-phenylamino]-pyrimidin-2-ylamino}-8-methoxy-1,2,4,5-tetrahydro-3-benzazepin-3-yl)-1-morpholin-4-yl-ethanone In an analogous manner to Example 1503, the product was prepared from (2,5-Dichloro-pyrimidin-4-yl)-[2-(propane-2-sulfonyl)-phenyl]-amine and 2-(7-Amino-8-methoxy-1,2,4,5-tetrahydro-3-benzazepin-3-yl)-1-morpholin-4-yl-ethanone. Product was isolated as a white foam (65 mg, 60%). mp: 100° C., MS (ESI+): 629.6 (M+H), $^1$H-NMR (CDCl$_3$, 400 MHz) δ 9.53 (s, 1H), 8.57 (d, J=9 Hz, 1H), 8.18 (s, 1H), 8.01 (s, 1H), 7.95 (d, J=8 Hz, 1H), 7.62 (t, J=8 Hz, 1H), 7.52 (s, 1H), 6.67 (s, 1H), 3.90 (s, 3H), 3.74 (s, 8H), 3.67 (d, 2H), 3.30 (m, 3H), 2.87 (m, 2H), 2.74-2.66 (m, 6H), 1.33 (d, J=7 Hz, 6H).

Example 1537

5-Chloro-N(4)-(4-dimethylamino-2-methoxy-phenyl)-N(2)-[8-methoxy-3-(2-morpholin-4-yl-ethyl)-2,3,4,5-tetrahydro-1H-3-benzazepin-7-yl]-pyrimidine-2,4-diamine In an analogous manner to Example 1503, the product was prepared from N(1)-(2,5-Dichloro-pyrimidin-4-yl)-2-methoxy-N(4),N(4)-dimethyl-benzene-1,4-diamine and 8-Methoxy-3-(2-morpholin-4-yl-ethyl)-2,3,4,5-tetrahydro-1H-3-benzazepin-7-ylamine. Product was isolated as a light yellow foam (40 mg, 22%). mp: 115° C. (glass @ 75) MS (ESI+): 582 (M+H), $^1$H-NMR (CDCl$_3$, 400 MHz) δ 8.16 (s, 1H), 8.14 (s, 1H), 8.01 (s, 1H), 7.45 (s, 1H), 7.43 (s, 1H), 6.64 (s, 1H), 6.38 (s, 1H), 6.35 (s, 1H), 3.93 (s, 3H), 3.87 (s, 3H), 3.74 (t, J=5 Hz, 4H), 2.99 (s, 6H), 2.87 (m, 2H), 2.82 (m, 2H), 2.70 (t, J=7 Hz, 6H), 2.56 (m, 2H), 2.51 (m, 4H).

Example 1538

2-(5-Chloro-2-{8-methoxy-3-[2-(4-methyl-piperazin-1-yl)-2-oxo-ethyl]-2,3,4,5-tetrahydro-1H-3-benzazepin-7-ylamino}-pyrimidin-4-ylamino)-N,N-dimethyl-benzenesulfonamide In an analogous manner to Example 1503, the product was prepared from 2-(2,5-Dichloro-pyrimidin-4-ylamino)-N,N-dimethyl-benzenesulfonamide and 2-(7-Amino-8-methoxy-1,2,4,5-tetrahydro-3-benzazepin-3-yl)-1-(4-methyl-piperazin-1-yl)-ethanone. Product was isolated as a white foam (40 mg, 36%). mp: ~140° C. (glass 100), MS (ESI+): 643.5 (M+H), $^1$H-NMR (CDCl$_3$, 400 MHz) δ 9.35 (s, 1H), 8.54 (d, J=8 Hz, 1H), 8.15 (s, 1H), 8.01 (s, 1H), 7.90 (d, J=8 HZ, 1H), 7.58 (t, 1H), 7.52 (s, 1H), 7.25 (m, 1H), 6.67 (s, 1H), 3.89 (s, 3H), 3.72 (m, 2H), 3.68 (m, 2H), 3.30 (s, 2H), 2.88 (m, 2H), 2.76 (s, 8H), 2.70 (m, 2H), 2.66 (m, 2H), 2.46 (m, 2H), 2.42 (m, 2H), 2.34 (s, 3H).

Example 1539

(1S,2S,3R,4R)-3-(5-Chloro-2-{8-methoxy-3-[2-(4-methyl-piperazin-1-yl)-2-oxo-ethyl]-2,3,4,5-tetrahydro-1H-3-benzazepin-7-ylamino}-pyrimidin-4-ylamino)-bicyclo[2.2.1]hept-5-ene-2-carboxylic acid amide In an analogous manner to Example 1503, the product was prepared from (1S,2S,3R,4R)-3-(2,5-Dichloro-pyrimidin-4-ylamino)-bicyclo[2.2.1]hept-5-ene-2-carboxylic acid amide and 2-(7-Amino-8-methoxy-1,2,4,5-tetrahydro-3-benzazepin-3-yl)-1-(4-methyl-piperazin-1-yl)-ethanone. Product was isolated as a white foam (38 mg, 32%). mp: 190° C. (glass 140), MS (ESI+): 595.5 (M+H), $^1$H-NMR (CDCl$_3$, 400 MHz) δ 8.20 (s, 1H), 7.91 (s, 1H), 7.42 (s, 1H), 6.65 (s, 1H), 6.57 (d, J=8 Hz, 1H), 5.60 (br s, 1H), 5.32 (s, 1H), 4.46 (t, J=9 Hz, 1H), 3.88 (s, 3H), 3.72 (m, 2H), 3.67 (m, 2H), 3.30 (s, 2H), 3.09 (s, 1H), 2.89 (s, 5H), 2.68 (s, 4H), 2.53 (d, J=8 Hz, 1H), 2.46 (m, 2 h), 2.41 (m, 2H), 2.34 (s, 3H), 2.28 (d, J=8 Hz, 1H), 1.67 (d, J=9 Hz, 1H), 1.27 (s, 1H).

Example 1540

2-{7-[5-Chloro-4-(4-dimethylamino-2-methoxy-phenylamino)-pyrimidin-2-ylamino]-8-methoxy-1,2,4,5-tetrahydro-3-benzazepin-3-yl}-1-(4-methyl-piperazin-1-yl)-ethanone In an analogous manner to Example 1534, the product was prepared from N(1)-(2,5-Dichloro-pyrimidin-4-yl)-2-methoxy-N(4),N(4)-dimethyl-benzene-1,4-diamine and 2-(7-Amino-8-methoxy-1,2,4,5-tetrahydro-3-benzazepin-3-yl)-1-(4-methyl-piperazin-1-yl)-ethanone. Product isolated as a grey foam (50 mg, 43%). mp: 145° C. (glass @ 83), MS (ESI+): 609.5 (M+H), $^1$H-NMR (CDCl$_3$, 400 MHz) δ 8.13 (s, 1H), 8.10 (s, 1H), 8.01 (s, 1H), 7.40 (s, 1H), 7.28 (s, 1H), 6.64 (s, 1H), 6.37 (s, 1H), 6.34 (s, 1H), 3.92 (s, 3H), 3.87 (s, 3H), 3.74 (m, 2H), 3.67 (m, 2H), 3.28 (s, 2H), 2.99 (s, 6H), 2.87 (m, 2H), 2.81 (m, 2H), 2.66 (m, 4H), 2.46 (m, 2H), 2.41 (m, 2H), 2.34 (s, 3H).

Example 1541

2-(7-{5-Chloro-4-[2-(propane-2-sulfonyl)-phenylamino]-pyrimidin-2-ylamino}-8-methoxy-1,2,4,5-tetrahydro-3-benzazepin-3-yl)-1-(4-methyl-piperazin-1-yl)-ethanone In an analogous manner to Example 1503, the product was prepared from (2,5-Dichloro-pyrimidin-4-yl)-[2-(propane-2-sulfonyl)-phenyl]-amine and 2-(7-Amino-8-methoxy-1,2,4,5-tetrahydro-3-benzazepin-3-yl)-1-(4-methyl-piperazin-1-yl)-ethanone. Product isolated as an off-white foam (20 mg, 18%). mp: 170° C. (glass 105), MS (ESI+): 642.5 (M+H), $^1$H-NMR (CDCl$_3$, 400 MHz) δ 9.52 (s, 1H), 8.57 (d, J=8 Hz, 1H), 8.17 (s, 1H), 8.01 (s, 1H), 7.95 (d, J=9 Hz, 1H), 7.62 (t, J=8 Hz, 1H), 7.52 (s, 1H), 7.26 (m, 1H), 6.67 (s, 1H), 5.32 (s, 1H), 3.89 (s, 3H), 3.72 (m, 2H), 3.68 (m, 2H), 3.30 (m, 3H), 2.88 (m, 2H), 2.74 (m, 2H), 2.70 (m, 2H), 2.66 (m, 2H), 2.46 (m, 2H), 2.42 (m, 2H), 2.34 (s, 3H), 1.33 (d, J=7 Hz, 6H).

Example 1542

Amino-acetic acid 2-{7-[5-chloro-4-(2-dimethylsulfamoyl-phenylamino)-pyrimidin-2-ylamino]-8-methoxy-1,2,4,5-tetrahydro-benzo[d]azepin-3-yl}-ethyl ester 2-{5-Chloro-2-[3-(2-hydroxy-ethyl)-8-methoxy-2,3,4,5-tetrahydro-1H-3-benzazepin-7-ylamino]-pyrimidin-4-ylamino}-N,N-dimethyl-benzenesulfonamide (100 mg, 0.183 mmol) and N-α-(tert-Butoxycarbonyl)glycine (32 mg, 0.183 mmol) were dissolved in dry Methylene chloride (2.00 mL, 31.2 mmol), and a catalytic amount of 4-Dimethylaminopyridine (2 mg, 0.02 mmol) was added and stirred for 20 minutes. N,N'-Dicyclohexylcarbodiimide (37.7 mg, 0.183 mmol) was then added and the reaction was stirred for 15 h at room temperature. The reaction was filtered to remove urea ppt. The filtrate was concentrated onto celite. ISCO flash column 0-8% MeOH:DCM. Product fractions were concentrated to a white solid. The Boc protected product was refluxed in DCM with 50 µL of TFA. After 3 hours reaction was sluggish and an additional 500 µL of TFA was added. The reaction was concentrated to dryness. The residue was triturated in H2O and filtered. A white solid containing no desired product was removed and the filtrate was lyophilized. The resulting white solid showed 4 TFA salts by NMR. It also contained a small amount (8%) of starting material. The solid was extracted and freebased with bicarb/DCM. The organic layer was concentrated to dryness and purified by preperative HPLC. The product was worked up again using bicarb/DCM. The product was isolated as a white foam (40 mg, 36%). mp: 77-79° C., MS (ESI+): 604 (M+H), $^1$H-NMR (CDCl$_3$, 400 MHz) δ 9.36 (s, 1H), 8.55 (d, J=8 Hz, 1H), 8.15 (s, 1H), 8.02 (s, 1H), 7.90 (d, J=8 Hz, 1H), 7.57 (t, 1H), 7.51 (s, 1H), 7.27 (m, 1H), 6.67 (s, 1H), 4.30 (t, J=7 Hz, 2H), 3.89 (s, 3H), 3.48 (s, 2H), 2.87-2.83 (m, 4H), 2.77-2.71 (m, 13H).

Example 1543

2-(7-{5-Chloro-4-[2-(pyrrolidine-1-sulfonyl)-phenylamino]-pyrimidin-2-ylamino}-8-methoxy-1,2,4,5-tetrahydro-3-benzazepin-3-yl)-ethanol In an analogous manner to Example 1534, the product was prepared from (2,5-Dichloro-pyrimidin-4-yl)-[2-(pyrrolidine-1-sulfonyl)-phenyl]-amine and 2-(7-Amino-8-methoxy-1,2,4,5-tetrahydro-3-benzazepin-3-yl)-ethanol. The product was isolated as a light yellow foam (40 mg, 43%). mp: 110° C., MS (ESI+): 573 (M+H), $^1$H-NMR (CDCl$_3$, 400 MHz) δ 9.44 (s, 1H), 8.55 (d, J=8 Hz, 1H), 8.16 (s, 1H), 8.04 (s, 1H), 7.96 (d, J=8 Hz, 1H), 7.56 (t, J=8 Hz, 1H), 7.52 (s, 1H), 7.26 (m, 1H), 6.67 (s, 1H), 3.89 (s, 3H), 3.66 (t, 2H), 3.28 (t, J=5 Hz, 4H), 2.89 (t, 2H), 2.74-2.69 (m, 8H), 1.80 (m, 4H).

Example 1544

(S)-2-Amino-3-methyl-butyric acid 2-{7-[5-chloro-4-(2-dimethylsulfamoyl-phenylamino)-pyrimidin-2-ylamino]-8-methoxy-1,2,4,5-tetrahydro-3-benzazepin-3-yl}-ethyl ester In an analogous manner to Example 1542, the product was prepared from [A]2-{5-Chloro-2-[3-(2-hydroxy-ethyl)-8-methoxy-2,3,4,5-tetrahydro-1H-3-benzazepin-7-ylamino]-pyrimidin-4-ylamino}-N,N-dimethyl-benzenesulfonamide and N-(tert-Butoxycarbonyl)-L-valine. The product was isolated as a pale yellow foam (65 mg, 45%). $^1$H-NMR (CDCl$_3$, 400 MHz) δ 9.36 (s, 1H), 8.55 (d, J=8 Hz, 1H), 8.16 (s, 1H), 8.02 (s, 1H), 7.90 (d, J=8 Hz, 1H), 7.58 (t, 1H), 7.51 (s, 1H), 7.26 (m, 1H), 6.67 (s, 1 h), 4.32-4.28 (m, 2H), 3.89 (s, 3H), 3.33 (d, J=5 Hz, 1H), 2.87 (m, 2H), 2.84 (m, 2H), 2.82-2.70 (m, 13H), 2.10 (m, 1H), 1.01 (d, J=7 Hz, 3H), 0.95 (d, J=7 Hz, 3H).

Example 1545

Phosphoric acid mono-(2-{7-[5-chloro-4-(2-dimethylsulfamoyl-phenylamino)-pyrimidin-2-ylamino]-8-methoxy-1,2,4,5-tetrahydro-3-benzazepin-3-yl}-ethyl)ester 2-{5-Chloro-2-[3-(2-hydroxy-ethyl)-8-methoxy-2,3,4,5-tetrahydro-1H-3-benzazepin-7-ylamino]-pyrimidin-4-ylamino}-N,N-dimethyl-benzenesulfonamide (100 mg, 0.183 mmol) was suspended in Phosphoric acid, trimethyl ester (3.00 mL, 25.6 mmol;). Under nitrogen Phosphoryl chloride (27.3 µL, 0.292 mmol;) was added and the mixture was stirred at room temperature for 2 h. Attempts to extract the product from the aqueous layer failed with DCM and EtOAc, although it did remove the remaining starting material from the reaction mixture. The aqueous layer was lyophilized over night to obtain a clear and colorless oil (mostly phosphoric acid or its derivatives). This was chromatographed on the Gilson HPLC system in H2O (15-50%). The desired fractions were collected and lyophilized again to obtain product as a TFA salt (85 mg, 74%). mp: 135-139° C., MS (ESI+): 627 (M+H), $^{19}$F-NMR: showed TFA salt, $^1$H-NMR (CDCl$_3$, 400 MHz) δ 9.32 (s, 1H), 8.42 (m, 1H), 8.27 (s, 1H), 8.25 (s, 1H), 7.82 (d, J=8 Hz, 1H), 7.64-7.58 (m, 2H), 7.38 (t, J=7.5 Hz, 1H), 6.98 (s, 1H), 4.21 (br s, 2H), 3.79 (s, 3H), 3.47 (s, 3H), 3.10 (s, 2H), 2.64 (s, 6H).

Example 1546

Propionic acid 2-{7-[5-chloro-4-(2-dimethylsulfamoyl-phenylamino)-pyrimidin-2-ylamino]-8-methoxy-1,2,4,5-tetrahydro-3-benzazepin-3-yl}-ethyl ester 2-{5-Chloro-2-[3-(2-hydroxy-ethyl)-8-methoxy-2,3,4,5-tetrahydro-1H-3-benzazepin-7-ylamino]-pyrimidin-4-ylamino}-N,N-dimethyl-benzenesulfonamide (80.0 mg, 0.146 mmol) was stirred in Methylene chloride (1.60 mL, 25.0 mmol) with Triethylamine (30.6 µL, 0.219 mmol) at room temperature. Propanoyl chloride (12.7 µL, 0.146 mmol) was then added quickly under nitrogen. The reaction was complete after stirring over night. The reaction mixture was washed with bicarb and extracted with XS DCM. The organic layer was dried over MgSO$_4$ and filtered. The filtrate was chromatographed on an ISCO flash system (0-10% MeOH:DCM). The desired fractions were concentrated and the product was obtained as a foam from a small amount of DCM (35 mg, 40%). mp: 40° C. softened, 60-70 glass, MS (ESI+): 603 (M+H), $^1$H-NMR (CDCl$_3$, 400 MHz) δ 9.35 (s, 1H), 8.54 (d, J=8 Hz, 1H), 8.16 (s, 1H), 8.01 (s, 1H), 7.90 (d, J=8 Hz, 1H), 7.57 (t, 1H), 7.51 (s, 1H), 7.25 (m, 1H), 6.67 (s, 1H), 4.25 (t, J=6 Hz, 2H), 3.89 (s, 3H), 2.87 (m, 2H), 2.83 (t, J=6 Hz, 2H), 2.76-2.72 (m, 12H), 2.36 (t, J=7.5 Hz, 2H), 1.17 (t, J=7.5, 3H).

Example 1547

2-{5-Chloro-2-[3-(2-hydroxy-propyl)-8-methoxy-2,3,4,5-tetrahydro-1H-3-benzazepin-7-ylamino]-pyrimidin-4-ylamino}-N,N-dimethyl-benzenesulfonamide In an analogous manner to Example 1534, the product was prepared from 2-(2,5-Dichloro-pyrimidin-4-ylamino)-N,N-dimethyl-benzenesulfonamide and 1-(7-Amino-8-methoxy-1,2,4,5-tetrahydro-3-benzazepin-3-yl)-propan-2-ol. The product was isolated as off-white needles (60 mg, 62%). mp: 183-185° C., MS (ESI+): 561 (M+H), $^1$H-NMR (CDCl$_3$, 400 MHz) δ 9.35 (s, 1H), 8.55 (d, J=8 Hz, 1H), 8.16 (s, 1H), 8.03 (s, 1H), 7.91 (d, J=8 Hz, 1H), 7.58 (t, 1H), 7.53 (s, 1H), 7.26

(m, 1H), 6.68 (s, 1H), 3.89 (s, 3H), 3.89 (m, 1H), 2.86-2.52 (m, 15H), 1.18 (d, J=6 Hz, 3H).

Example 1548

(1S,2S,3R,4R)-3-{5-Chloro-2-[3-(2-hydroxy-propyl)-8-methoxy-2,3,4,5-tetrahydro-1H-3-benzazepin-7-ylamino]-pyrimidin-4-ylamino}-bicyclo[2.2.1]hept-5-ene-2-carboxylic acid amide In an analogous manner to Example 1534, the product was prepared from (1S,2S,3R,4R)-3-(2,5-Dichloro-pyrimidin-4-ylamino)-bicyclo[2.2.1]hept-5-ene-2-carboxylic acid amide and 1-(7-Amino-8-methoxy-1,2,4,5-tetrahydro-3-benzazepin-3-yl)-propan-2-ol. Product was isolated as a tan foam (55 mg, 53%). mp: 120° C., MS (ESI+): 513 (M+H), $^1$H-NMR (CDCl$_3$, 400 MHz) δ 8.22 (s, 1H), 7.91 (s, 1H), 7.42 (s, 1H), 6.66 (s, 1H), 6.57 (s, 1H), 6.51 (s, 1H), 6.33 (s, 2H), 5.60 (s, 1H), 5.35 (s, 1H), 5.32 (s, 1H), 4.47 (t, J=8 Hz, 1H), 3.88 (s, 4H), 3.09 (s, 1H), 2.89-2.87 (m, 7H), 2.63 (m, 2H), 2.53 (d, 2H), 2.28 (d, J=10 Hz, 2H), 1.67 (d, J=8 Hz, 1H), 1.17 (d, J=6 Hz, 3H).

Example 1549

2-{5-Chloro-2-[3-(2-hydroxy-ethyl)-8-methoxy-2,3,4,5-tetrahydro-1H-3-benzazepin-7-ylamino]-pyrimidin-4-ylamino}-benzoic acid 2-methoxy-ethyl ester In an analogous manner to Example 1534, the product was prepared from 2-(2,5-Dichloro-pyrimidin-4-ylamino)-N-methyl-benzamide and 2-(7-Amino-8-methoxy-1,2,4,5-tetrahydro-3-benzazepin-3-yl)-ethanol. The 2-methoxyethanol solvent reacted with the benzamide resulting in the product (40 mg, 37%). mp: 125-131° C., MS (ESI+): 542 (M+H), $^1$H-NMR (CDCl$_3$, 400 MHz) δ 11.03 (s, 1H), 8.85 (d, J=8.6 Hz, 1H), 8.16 (s, 2H), 8.15 (s, 1H), 7.53 (t, J=8.1 Hz, 1H), 7.49 (s, 2H), 7.11 (t, J=7.2 Hz, 1H), 6.68 (s, 1H), 4.55 (t, J=8.6 Hz, 2H), 3.90 (s, 3H), 3.79 (m, 2H), 3.66 (m, 2H), 3.46 (s, 3H), 2.91 (m, 2H), 2.83 (m, 2H), 2.69 (m, 6H).

Example 1550

2-{5-Chloro-2-[3-(2-hydroxy-propyl)-8-methoxy-2,3,4,5-tetrahydro-1H-3-benzazepin-7-ylamino]-pyrimidin-4-ylamino}-benzoic acid 2-methoxy-ethyl ester In an analogous manner to Example 1534, the product was prepared from 2-(2,5-Dichloro-pyrimidin-4-ylamino)-N-methyl-benzamide and 1-(7-Amino-8-methoxy-1,2,4,5-tetrahydro-3-benzazepin-3-yl)-propan-2-ol. The 2-methoxyethanol solvent reacted with the benzamide resulting in the product (28 mg, 25%). mp: 100° C., MS (ESI+): 556 (M+H), $^1$H-NMR (CDCl$_3$, 400 MHz) δ 11.03 (s, 1H), 8.86 (d, J=8.6 Hz, 1H), 8.17 (s, 2H), 8.15 (s, 1H), 7.53 (t, J=8.1 Hz, 1H), 7.49 (s, 2H), 7.11 (t, J=7.2 Hz, 1H), 6.68 (s, 1H), 4.55 (t, J=8.6 Hz, 2H), 3.90 (s, 4H), 3.79 (t, 2H), 3.46 (m, 2H), 2.96-2.82 (m, 6H), 2.62 (m, 2H), 2.61 (d, J=110 Hz, 1H), 2.27 (t, J=9 Hz, 1H), 1.17 (d, J=6 Hz, 3H).

Example 1551

1-(2-{5-Chloro-2-[3-(2-hydroxy-ethyl)-8-methoxy-2,3,4,5-tetrahydro-1H-3-benzazepin-7-ylamino]-pyrimidin-4-ylamino}-benzenesulfonyl)-pyrrolidin-3-ol In an analogous manner to Example 1534, the product was prepared from 2-(7-Amino-8-methoxy-1,2,4,5-tetrahydro-3-benzazepin-3-yl)-ethanol and {2-[3-(tert-Butyl-dimethyl-silanyloxy)-pyrrolidine-1-sulfonyl]-phenyl}-(2,5-dichloro-pyrimidin-4-yl)-amine. Product was isolated as a white foam (25 mg, 22%). MS (ESI+): 589 (M+H), $^1$H-NMR (CDCl$_3$, 400 MHz) δ 9.33 (s, 1H), 8.48 (d, J=8 Hz, 1H), 8.17 (s, 1H), 8.01 (s, 1H), 7.97 (d, J=8 Hz, 1H), 7.55 (m, 2H), 7.25 (m, 1H), 6.66 (s, 1H), 4.37 (br s, 1H), 3.89 (s, 4H), 3.65 (t, J=9 Hz, 2H), 3.42 (m, 3H), 3.41 (d, 1H), 2.87 (m, 2H), 2.72-2.66 (m, 8H), 1.97 (m, 1H), 1.86 (m, 1H).

Example 1552

1-(2-{5-Chloro-2-[3-(2-hydroxy-propyl)-8-methoxy-2,3,4,5-tetrahydro-1H-3-benzazepin-7-ylamino]-pyrimidin-4-ylamino}-benzenesulfonyl)-pyrrolidin-3-ol In an analogous manner to Example 1534, the product was prepared from 1-(7-Amino-8-methoxy-1,2,4,5-tetrahydro-3-benzazepin-3-yl)-propan-2-ol and {2-[3-(tert-Butyl-dimethyl-silanyloxy)-pyrrolidine-1-sulfonyl]-phenyl}-(2,5-dichloro-pyrimidin-4-yl)-amine. The product was isolated as a white solid (70 mg, 61%). mp: 199-202° C., MS (ESI+): 603 (M+H), $^1$H-NMR (CDCl$_3$, 400 MHz) δ 9.33 (s, 1H), 8.48 (d, J=8 Hz, 1H), 8.17 (s, 1H), 8.01 (s, 1H), 7.97 (d, J=8 Hz, 1H), 7.55 (m, 2H), 7.25 (m, 1H), 6.66 (s, 1H), 4.37 (br s, 1H), 3.89 (s, 4H), 3.43 (m, 3H), 2.89-2.52 (m, 9H), 2.26 (t, J=9 Hz, 1H), 1.96 (m, 1H), 1.87 (m, 1H), 1.17 (d, J=6 Hz, 3H).

Example 1553

1-(7-{5-Chloro-4-[2-(pyrrolidine-1-sulfonyl)-phenylamino]-pyrimidin-2-ylamino}-8-methoxy-1,2,4,5-tetrahydro-3-benzazepin-3-yl)-propan-2-ol In an analogous manner to Example 1534, the product was prepared from 1-(7-Amino-8-methoxy-1,2,4,5-tetrahydro-3-benzazepin-3-yl)-propan-2-ol and (2,5-Dichloro-pyrimidin-4-yl)-[2-(pyrrolidine-1-sulfonyl)-phenyl]-amine. The product was isolated as a yellow foam (75 mg, 67%). MS (ESI+): 587 (M+H), $^1$H-NMR (CDCl$_3$, 400 MHz) δ 9.44 (s, 1H), 8.55 (d, J=8 Hz, 1H), 8.16 (s, 1H), 8.04 (s, 1H), 7.96 (d, J=8 Hz, 1H), 7.56 (t, J=8 Hz, 1H), 7.52 (s, 1H), 7.26 (m, 1H), 6.67 (s, 1H), 3.89 (s, 4H), 3.28 (m, 4H), 2.92-2.52 (m, 10H), 2.27 (t, J=9 Hz, 1H), 1.79 (m, 4H), 1.17 (d, J=6 Hz, 3H).

Example 1554

(R)-1-(2-{5-Chloro-2-[3-((S)-2-hydroxy-propyl)-8-methoxy-2,3,4,5-tetrahydro-1H-3-benzazepin-7-ylamino]-pyrimidin-4-ylamino}-benzenesulfonyl)-pyrrolidin-3-ol In an analogous manner to Example 1534, the product was prepared from (S)-1-(7-Amino-8-methoxy-1,2,4,5-tetrahydro-3-benzazepin-3-yl)-propan-2-ol and {2-[(R)-3-(tert-Butyl-dimethyl-silanyloxy)-pyrrolidine-1-sulfonyl]-phenyl}-(2,5-dichloro-pyrimidin-4-yl)-amine. The product was isolated as an off-white foam (55 mg, 47%). MS (ESI+): 603 (M+H), $^1$H-NMR (CDCl$_3$, 400 MHz) δ 9.33 (s, 1H), 8.48 (d, J=8 Hz, 1H), 8.16 (s, 1H), 8.01 (s, 1H), 7.96 (d, J=8 Hz, 1H), 7.58-7.52 (m, 2H), 7.25 (t, J=8 Hz, 1H), 6.66 (s, 1H), 4.37 (br s, 1H), 3.88 (m, 4H), 3.42 (m, 3H), 3.31 (d, 1H), 2.91-2.52 (m, 10H), 2.27 (m, 1H), 1.17 (d, J=6 Hz, 3H).

Example 1555

(S)-1-(2-{5-Chloro-2-[3-((S)-2-hydroxy-propyl)-8-methoxy-2,3,4,5-tetrahydro-1H-3-benzazepin-7-ylamino]-pyrimidin-4-ylamino}-benzenesulfonyl)-pyrrolidin-3-ol In an analogous manner to Example 1534, the product was prepared from (S)-1-(7-Amino-8-methoxy-1,2,4,5-tetrahydro-3-benzazepin-3-yl)-propan-2-ol and {2-[(S)-3-(tert-Butyl-dimethyl-silanyloxy)-pyrrolidine-1-sulfonyl]-phenyl}-(2,5-dichloro-pyrimidin-4-yl)-amine. The product was isolated as an off-white foam (55 mg, 46%). MS (ESI+): 603 (M+H), $^1$H-NMR (CDCl$_3$, 400 MHz) δ 9.33 (s, 1H), 8.48 (d, J=8 Hz, 1H), 8.16 (s, 1H), 8.01 (s, 1H), 7.96 (d, J=8 Hz, 1H), 7.58-7.52 (m, 2H), 7.25 (t, J=8 Hz, 1H), 6.66 (s, 1H), 4.37 (br s, 1H), 3.88 (m, 4H), 3.42 (m, 3H), 3.31 (d, 1H), 2.91-2.52 (m, 110H), 2.27 (m, 1H), 1.17 (d, J=6 Hz, 3H).

Example 1556

(S)-1-(2-{5-Chloro-2-[3-((R)-2-hydroxy-propyl)-8-methoxy-2,3,4,5-tetrahydro-1H-3-benzazepin-7-ylamino]-pyrimidin-4-ylamino}-benzenesulfonyl)-pyrrolidin-3-ol In an analogous manner to Example 15N34, the product was prepared from (R)-1-(7-Amino-8-methoxy-1,2,4,5-tetrahydro-3-benzazepin-3-yl)-propan-2-ol and {2-[(S)-3-(tert-Butyl-dimethyl-silanyloxy)-pyrrolidine-1-sulfonyl]-phenyl}-(2,5-dichloro-pyrimidin-4-yl)-amine. The product was isolated as a white solid (35 mg, 29%). mp: 199-201° C. MS (ESI+): 603 (M+H), $^1$H-NMR (CDCl$_3$, 400 MHz) δ 9.33 (s, 1H), 8.48 (d, J=8 Hz, 1H), 8.16 (s, 1H), 8.01 (s, 1H), 7.96 (d, J=8 Hz, 1H), 7.58-7.52 (m, 2H), 7.25 (t, J=8 Hz, 1H), 6.66 (s, 1H), 4.37 (br s, 1H), 3.88 (m, 4H), 3.42 (m, 3H), 3.31 (d, 1H), 2.91-2.52 (m, 10H), 2.27 (m, 1H), 1.17 (d, J=6 Hz, 3H).

Example 1557

(R)-1-(2-{5-Chloro-2-[3-((R)-2-hydroxy-propyl)-8-methoxy-2,3,4,5-tetrahydro-1H-3-benzazepin-7-ylamino]-pyrimidin-4-ylamino}-benzenesulfonyl)-pyrrolidin-3-ol In an analogous manner to Example 1534, the product was prepared from (R)-1-(7-Amino-8-methoxy-1,2,4,5-tetrahydro-3-benzazepin-3-yl)-propan-2-ol and {2-[(R)-3-(tert-Butyl-dimethyl-silanyloxy)-pyrrolidine-1-sulfonyl]-phenyl}-(2,5-dichloro-pyrimidin-4-yl)-amine. The product was isolated as a white solid (35 mg, 29%). mp: 197-199° C., MS (ESI+): 603 (M+H), $^1$H-NMR (CDCl$_3$, 400 MHz) δ 9.33 (s, 1H), 8.48 (d, J=8 Hz, 1H), 8.16 (s, 1H), 8.01 (s, 1H), 7.96 (d, J=8 Hz, 1H), 7.58-7.52 (m, 2H), 7.25 (t, J=8 Hz, 1H), 6.66 (s, 1H), 4.37 (br s, 1H), 3.88 (m, 4H), 3.42 (m, 3H), 3.31 (d, 1H), 2.91-2.52 (m, 10H), 2.27 (m, 1H), 1.17 (d, J=6 Hz, 3H).

Example 1558

(1S,2S,3R,4R)-3-{5-Chloro-2-[3-((S)-2-hydroxy-propyl)-8-methoxy-2,3,4,5-tetrahydro-1H-3-benzazepin-7-ylamino]-pyrimidin-4-ylamino}-bicyclo[2.2.1]hept-5-ene-2-carboxylic acid amide In an analogous manner to Example 1534, the product was prepared from (1S,2S,3R,4R)-3-(2,5-Dichloro-pyrimidin-4-ylamino)-bicyclo[2.2.1]hept-5-ene-2-carboxylic acid amide and (S)-1-(7-Amino-8-methoxy-1,2,4,5-tetrahydro-3-benzazepin-3-yl)-propan-2-ol. The product was isolated as an off-white foam (72 mg, 70%). MS: 513 (M+H), $^1$H-NMR (CDCl$_3$, 400 MHz) δ 8.22 (s, 1H), 7.91 (s, 1H), 7.42 (s, 1H), 6.66 (s, 1H), 6.57 (s, 1H), 6.51 (s, 1H), 6.33 (s, 2H), 5.60 (s, 1H), 5.35 (s, 1H), 5.32 (s, 1H), 4.47 (t, J=8 Hz, 1H), 3.88 (s, 4H), 3.08 (s, 1H), 2.88 (m, 8H), 2.62 (br s, 2H), 2.53 (m, 2H), 2.27 (m, 2H), 1.66 (d, J=8.5 Hz, 1H), 1.16 (d, J=6 Hz, 3H).

Example 1559

(1S,2S,3R,4R)-3-{5-Chloro-2-[3-((R)-2-hydroxy-propyl)-8-methoxy-2,3,4,5-tetrahydro-1H-3-benzazepin-7-ylamino]-pyrimidin-4-ylamino}-bicyclo[2.2.1]hept-5-ene-2-carboxylic acid amide In an analogous manner to Example 1534, the product was prepared from (1S,2S,3R,4R)-3-(2,5-Dichloro-pyrimidin-4-ylamino)-bicyclo[2.2.1]hept-5-ene-2-carboxylic acid amide and (R)-1-(7-Amino-8-methoxy-1,2,4,5-tetrahydro-3-benzazepin-3-yl)-propan-2-ol. Product was isolated as an off-white foam (65 mg, 63%). MS (ESI+): 513 (M+H), $^1$H-NMR (CDCl$_3$, 400 MHz) δ 8.22 (s, 1H), 7.91 (s, 1H), 7.42 (s, 1H), 6.66 (s, 1H), 6.57 (s, 1H), 6.51 (s, 1H), 6.33 (s, 2H), 5.60 (s, 1H), 5.35 (s, 1H), 5.32 (s, 1H), 4.47 (t, J=8 Hz, 1H), 3.88 (s, 4H), 3.08 (s, 1H), 2.88 (m, 8H), 2.62 (br s, 2H), 2.53 (m, 2H), 2.27 (m, 2H), 1.66 (d, J=8.5 Hz, 1H), 1.16 (d, J=6 Hz, 3H).

Example 1560

(1S,2S,3R,4R)-3-{5-Chloro-2-[3-(2-hydroxy-2-methyl-propyl)-8-methoxy-2,3,4,5-tetrahydro-1H-3-benzazepin-7-ylamino]-pyrimidin-4-ylamino}-bicyclo[2.2.1]hept-5-ene-2-carboxylic acid amide In an analogous manner to Example 1534, the product was prepared from (1S,2S,3R,4R)-3-(2,5-Dichloro-pyrimidin-4-ylamino)-bicyclo[2.2.1]hept-5-ene-2-carboxylic acid amide and 1-(7-Amino-8-methoxy-1,2,4,5-tetrahydro-3-benzazepin-3-yl)-2-methyl-propan-2-ol. Product isolated as a white foam (68 mg, 64%). MS (ESI+): 527 (M+H), $^1$H-NMR (CDCl$_3$, 400 MHz) δ 8.20 (s, 1H), 7.90 (s, 1H), 7.42 (s, 1H), 6.65 (s, 1H), 6.57 (d, J=9 Hz, 1H), 6.33 (s, 2H), 5.63 (br s, 1H), 5.32 (br s, 1H), 4.46 (t, 1H), 3.88 (s, 3H), 3.09 (s, 1H), 2.88-2.82 (m, 10H), 2.54-2.49 (m, 3H), 2.28 (d, J=9 Hz, 1H), 1.22 (s, 6H).

Example 1561

(R)-1-(2-{5-Chloro-2-[3-(2-hydroxy-2-methyl-propyl)-8-methoxy-2,3,4,5-tetrahydro-1H-3-benzazepin-7-ylamino]-pyrimidin-4-ylamino}-benzenesulfonyl)-pyrrolidin-3-ol In an analogous manner to Example 1534, the product was prepared from 1-(7-Amino-8-methoxy-1,2,4,5-tetrahydro-3-benzazepin-3-yl)-2-methyl-propan-2-ol and {2-[(R)-3-(tert-Butyl-dimethyl-silanyloxy)-pyrrolidine-1-sulfonyl]-phenyl}-(2,5-dichloro-pyrimidin-4-yl)-amine. Product was isolated as white solid (58 mg, 47%). mp: 205-206° C., MS (ESI+): 617 (M+H), $^1$H-NMR (CDCl$_3$, 400 MHz) δ 9.33 (s, 1H), 8.48 (d, J=8 Hz, 1H), 8.17 (s, 1H), 7.97 (m, 2H), 7.53 (m, 2H), 7.25 (m, 1H), 6.65 (s, 1H), 3.60 (br s, 1H), 3.89 (s, 3H), 3.42 (q, 6 Hz, 3H), 3.30 (m, 2H), 2.87-2.72 (m, 8H), 2.48 (s, 2H), 1.95 (m, 1H), 1.88 (m, 1H), 1.57 (s, 6H), 1.22 (s, 6H).

Example 1562

(S)-1-(2-{5-Chloro-2-[3-(2-hydroxy-2-methyl-propyl)-8-methoxy-2,3,4,5-tetrahydro-1H-3-benzazepin-7-ylamino]-pyrimidin-4-ylamino}-benzenesulfonyl)-pyrrolidin-3-ol In an analogous manner to Example 1534, the product was prepared from 1-(7-Amino-8-methoxy-1,2,4,5-tetrahydro-3-benzazepin-3-yl)-2-methyl-propan-2-ol and {2-[(S)-3-(tert-Butyl-dimethyl-silanyloxy)-pyrrolidine-1-sulfonyl]-phenyl}-(2,5-dichloro-pyrimidin-4-yl)-amine. Product was isolated as a white solid (80 mg, 65%). mp: 204-205° C., MS (ESI+): 617 (M+H), $^1$H-NMR (CDCl$_3$, 400 MHz) δ 9.33 (s, 1H), 8.48 (d, J=8 Hz, 1H), 8.17 (s, 1H), 7.97 (m, 2H), 7.53 (m, 2H), 7.25 (m, 1H), 6.65 (s, 1H), 3.60 (br s, 1H), 3.89 (s, 3H), 3.42 (q, 6 Hz, 3H), 3.30 (m, 2H), 2.87-2.72 (m, 8H), 2.48 (s, 2H), 1.95 (m, 1H), 1.88 (m, 1H), 1.57 (s, 6H), 1.22 (s, 6H).

Example 1563

2-{5-Chloro-2-[3-(2-hydroxy-2-methyl-propyl)-8-methoxy-2,3,4,5-tetrahydro-1H-3-benzazepin-7-ylamino]-pyrimidin-4-ylamino}-N,N-dimethyl-benzenesulfonamide In an analogous manner to Example 1534, the product was prepared from 1-(7-Amino-8-methoxy-1,2,4,5-tetrahydro-3-benzazepin-3-yl)-2-methyl-propan-2-ol and 2-(2,5-Dichloro-pyrimidin-4-ylamino)-N,N-dimethyl-benzenesulfonamide. Product was isolated as a white solid (61 mg, 53%). mp: 188-189° C., MS (ESI+): 575 (M+H), $^1$H-NMR (CDCl$_3$, 400 MHz) δ 9.35 (s, 1H), 8.54 (d, J=8 Hz, 1H), 8.16 (s, 1H), 8.01 (s, 1H), 7.90 (d, J=8 Hz, 1H), 7.57 (t, 1H), 7.52 (s, 1H), 7.26 (m, 1H), 6.66 (s, 1H), 3.89 (s, 3H), 3.34 (s, 1H), 2.88-2.76 (m, 15H), 2.49 (s, 2H), 1.56 (s, 6H), 1.23 (s, 6H).

Example 1571

(1S,2S,3R,4R)-3-[5-Chloro-2-(1,5,5-trimethyl-2-oxo-2,3,4,5-tetrahydro-1H-benzo[b]azepin-7-ylamino)-pyrimidin-4-ylamino]-bicyclo[2.2.1]hept-5-ene-2-carboxylic acid amide The title compound was prepared in an analogous manner to the preparation of example 381 by combining 7-Amino-1,5,5-trimethyl-1,3,4,5-tetrahydro-benzo[b]azepin-2-one and (1S,2S,3R,4R)-3-(2,5-Dichloro-pyrimidin-4-ylamino)-bicyclo[2.2.1]hept-5-ene-2-carboxylic acid amide to yield an off-white solid, (64%). mp 233° C.; LCMS: m/z=481.06 (M+H$^+$), $^1$H NMR (400 MHz, DMSO-d$_6$) δ 9.33 (s, 1H), 7.97 (m, 2H), 7.79 (m, 2H), 7.51 (s, 1H), 7.24 (m, 2H), 6.33 (m, 2H), 4.15 (m, 1H), 3.16 (s, 3H), 2.89 (s, 1H), 2.78 (s, 1H), 2.54 (s, 1H), 2.12 (m, 3H), 1.94 (m, 2H), 1.41 (m, 1H), 1.25 (s, 6H).

Example 1572

3-[5-Chloro-2-(5,5-dimethyl-2-oxo-2,3,4,5-tetrahydro-1H-benzo[b]azepin-7-ylamino)-pyrimidin-4-ylamino]-4-methyl-thiophene-2-carboxylic acid methyl amide The title compound was prepared in an analogous manner to the preparation of example 381 by combining 7-Amino-5,5-dimethyl-1,3,4,5-tetrahydro-benzo[b]azepin-2-one and 3-(2,5-Dichloro-pyrimidin-4-ylamino)-4-methyl-thiophene-2-carboxylic acid methylamide to yield an orange solid (11%). LCMS: m/z=485.08 (M+H$^+$), $^1$H NMR (400 MHz, CDCl$_3$) δ 8.91 (s, 1H), 8.05 (m, 2H), 7.65 (s, 1H), 7.45 (d, 1H, J=8.6 Hz), 7.29 (m, 1H), 7.01 (s, 1H), 6.75 (d, 1H, J=8.6 Hz), 6.11 (m, 1H), 3.52 (m, 3H), 2.93 (d, 3H, J=4.8 Hz), 2.35 (m, 2H), 2.06 (m, 2H), 1.31 (s, 6H).

Example 1573

7-[5-Chloro-4-(2-methoxy-4-morpholin-4-yl-phenylamino)-pyrimidin-2-ylamino]-1,5,5-trimethyl-1,3,4,5-tetrahydro-benzo[b]azepin-2-one The title compound was prepared in an analogous manner to the preparation of example 381 by combining 7-Amino-1,5,5-trimethyl-1,3,4,5-tetrahydro-benzo[b]azepin-2-one and (2,5-Dichloro-pyrimidin-4-yl)-(2-methoxy-4-morpholin-4-yl-phenyl)-amine to yield a light yellow solid (71%). LCMS: m/z=537.23 (M+H$^+$), $^1$H NMR (400 MHz, CDCl$_3$) δ 8.20 (d, 1H, J=8.8 Hz), 8.04 (s, 1H), 7.67 (dd, 1H, J=8.7, 2.4 Hz), 7.59 (s, 1H), 7.32 (d, 1H, J=2.0 Hz), 7.10 (d, 1H, J=8.6 Hz), 6.91 (s, 1H), 6.54 (d, 1H, J=2.3 Hz), 6.48 (dd, 1H, J=8.7, 2.2 Hz), 3.92 (s, 3H), 3.89 (m, 4H), 3.29 (s, 3H), 3.14 (m, 4H), 3.89 (m, 4H), 2.30 (m, 2H), 2.05 (m, 2H), 1.29 (s, 6H).

Example 1574

2-[5-Chloro-2-(5,5-dimethyl-2-oxo-2,3,4,5-tetrahydro-1H-benzo[b]azepin-8-ylamino)-pyrimidin-4-ylamino]-3-fluoro-N-methyl-benzamide 4a) 4,4-Dimethyl-7-nitro-3,4-dihydro-2H-naphthalen-1-one oxime was prepared by a procedure similar to that described in patent WO 2005066165 by reacting 4,4-Dimethyl-7-nitro-3,4-dihydro-2H-naphthalen-1-one as starting material to yield a brown solid, (99%). LCMS: m/z=235.17 (M+H$^+$), $^1$H NMR (400 MHz, CDCl$_3$) δ 8.78 (d, 1H, J=2.3 Hz), 8.12 (dd, 1H, J=8.6, 2.5 Hz), 7.52 (m, 2H), 2.89 (m, 2H), 1.79 (m, 2H), 1.34 (s, 6H).

4b) 5,5-Dimethyl-8-nitro-1,3,4,5-tetrahydro-benzo[b]azepin-2-one was prepared by a procedure described in patent WO 2005066165 by reacting 4,4-Dimethyl-7-nitro-3,4-dihydro-2H-naphthalen-1-one oxime. LCMS: m/z=235.17 (M+H$^+$), $^1$H NMR (400 MHz, CDCl$_3$) δ 7.98 (m, 1H), 7.85 (d, 1H, J=2.5 Hz), 7.61 (d, 1H, J=8.8 Hz), 3.72 (bs, 1H), 2.38 (m, 2H), 2.17 (m, 2H), 1.45 (s, 6H).

4c) 8-Amino-5,5-dimethyl-1,3,4,5-tetrahydro-benzo[b]azepin-2-one was prepared in a manner analogous to the preparation of 7-Amino-5,5-dimethyl-1,3,4,5-tetrahydro-benzo[b]azepin-2-one by using 5,5-Dimethyl-8-nitro-1,3,4,5-tetrahydro-benzo[b]azepin-2-one as starting material (98%). LCMS: m/z=205.06 (M+H$^+$), $^1$H NMR (400 MHz, CDCl$_3$) δ 7.20 (d, 1H, J=8.3 Hz), 7.11 (bs, 1H), 6.51 (m, 1H), 6.24 (m, 1H), 3.74 (bs, 2H), 2.40 (m, 2H), 2.07 (m, 2H), 1.37 (s, 6H).

4d) The title compound was prepared in an analogous manner to the preparation of example 381 by combining 8-Amino-5,5-dimethyl-1,3,4,5-tetrahydro-benzo[b]azepin-2-one and 2-(2,5-Dichloro-pyrimidin-4-ylamino)-3-fluoro-N-methyl-benzamide (48%). LCMS: m/z=483.24 (M+H$^+$), $^1$H NMR (400 MHz, CDCl$_3$) δ 8.96 (s, 1H), 8.08 (s, 1H), 8.01 (m, 2H), 7.45 (s, 1H), 7.33 (m, 3H), 7.23 (d, 1H, J=8.6 Hz), 6.92 (d, 1H, J=8.6 Hz), 6.57 (m, 1H), 2.93 (d, 3H, J=4.8 Hz), 2.37 (m, 2H), 2.07 (m, 2H), 1.35 (s, 6H).

Example 1575

2-[5-Chloro-2-(5,5-dimethyl-2-oxo-2,3,4,5-tetrahydro-1H-benzo[b]azepin-8-ylamino)-pyrimidin-4-ylamino]-N-ethyl-3-fluoro-benzamide The compound was prepared with a procedure analogous to that used to prepare example 381 by combining 8-Amino-5,5-dimethyl-1,3,4,5-tetrahydro-benzo[b]azepin-2-one and 2-(2,5-Dichloro-pyrimidin-4-ylamino)-N-ethyl-3-fluoro-benzamide to yield a yellow solid (12%). LCMS: m/z=497.15 (M+H$^+$), $^1$H NMR (400 MHz, CDCl$_3$) δ 8.73 (s, 1H), 8.05 (s, 1H), 7.77 (m, 2H), 7.31 (m, 5H), 6.88 (d, 1H, J=8.6 Hz), 6.51 (m, 1H), 3.41 (m, 2H), 2.37 (m, 2H), 2.06 (m, 2H), 1.35 (s, 6H), 1.14 (m, 3H).

Example 1576

2-[5-Chloro-2-(1-ethyl-5,5-dimethyl-2-oxo-2,3,4,5-tetrahydro-1H-benzo[b]azepin-8-ylamino)-pyrimidin-4-ylamino]-3-fluoro-N-methyl-benzamide 6a) 1-Ethyl-5,5-dimethyl-8-nitro-1,3,4,5-tetrahydro-benzo[b]azepin-2-one was prepared in a manner analogous to the preparation of 1,5,5-Trimethyl-7-nitro-1,3,4,5-tetrahydro-benzo[b]azepin-2-one using 5,5-Dimethyl-8-nitro-1,3,4,5-tetrahydro-benzo[b]azepin-2-one as starting material to yield a yellow solid (65%). mp 83° C.; LCMS: m/z=263.05 (M+H$^+$), $^1$H NMR (400 MHz, CDCl$_3$) δ 8.11 (m, 1H), 8.06 (m, 1H), 7.60 (d, 1H, J=8.6 Hz), 3.91 (m, 2H), 2.32 (m, 2H), 1.42 (s, 6H), 1.38 (m, 3H).

6b) A procedure similar to that used to prepare 8-Amino-5,5-dimethyl-1,3,4,5-tetrahydro-benzo[b]azepin-2-one was used to prepare 8-Amino-1-ethyl-5,5-dimethyl-1,3,4,5-tetrahydro-benzo[b]azepin-2-one, an off-white solid (95%). mp 143° C.; LCMS: m/z=233.09 (M+H$^+$), $^1$H NMR (400 MHz, CDCl$_3$) δ 7.16 (d, 1H, J=8.3 Hz), 6.60 (s, 1H), 6.54 (d, 1H, J=8.3 Hz), 2.28 (m, 2H), 2.00 (m, 2H), 1.32 (m, 9H).

6c) The title compound was prepared with a procedure analogous to that used to prepare example 381 by combining 8-Amino-1-ethyl-5,5-dimethyl-1,3,4,5-tetrahydro-benzo[b]azepin-2-one and 2-(2,5-Dichloro-pyrimidin-4-ylamino)-3-fluoro-N-methyl-benzamide to yield a yellow solid (38%). LCMS: m/z=511.18 (M+H$^+$), $^1$H NMR (400 MHz, CDCl$_3$) δ 8.02 (s, 1H), 7.52 (s, 1H), 7.34 (d, 1H, J=7.6 Hz), 7.14 (m, 5H), 3.54 (m, 2H), 3.35 (s, 3H), 2.86 (s, 3H), 2.20 (m, 2H), 1.95 (m, 2H), 1.26 (s, 6H), 1.06 (m, 3H).

Example 1577

2-[5-Chloro-2-(5,5-dimethyl-2-oxo-2,3,4,5-tetrahydro-1H-benzo[b]azepin-8-ylamino)-pyrimidin-4-ylamino]-3-methyl-benzamide The title compound was prepared with a procedure analogous to that used to prepare example 381 by combining 8-Amino-1-ethyl-5,5-dimethyl-1,3,4,5-tetrahydro-benzo[b]azepin-2-one and 2-(2,5-Dichloro-pyrimidin-4-ylamino)-3-methyl-benzamide to yield an off-white solid (2.4%). LCMS: m/z=465.15 (M+H$^+$), $^1$H NMR (400 MHz, CDCl$_3$) δ 8.51 (s, 1H), 8.05 (s, 1H), 7.46 (m, 4H), 7.20 (m, 2H), 7.04 (s, 1H), 6.74 (d, 1H, J=8.6 Hz), 6.23 (bs, 1H), 5.81 (bs, 1H), 2.36 (m, 2H), 2.27 (s, 3H), 2.06 (m, 2H), 1.36 (s, 6H).

Example 1578

{2-[5-Chloro-2-(5,5-dimethyl-2-oxo-2,3,4,5-tetrahydro-1H-benzo[b]azepin-8-ylamino)-pyrimidin-4-ylamino]-phenoxy}-acetonitrile The title compound was prepared with a procedure analogous to that used to prepare example 381 by combining 8-Amino-1-ethyl-5,5-dimethyl-1,3,4,5-tetrahydro-benzo[b]azepin-2-one and [2-(2,5-Dichloro-pyrimidin-4-ylamino)-phenoxy]-acetonitrile to yield a yellow solid. LCMS: m/z=463.13 (M+H$^+$), $^1$H NMR (400 MHz, CDCl$_3$) δ 8.30 (d, 1H, J=7.8 Hz), 8.12 (s, 1H), 7.51 (s, 1H), 7.46 (s, 1H), 7.33 (d, 1H, J=8.6 Hz), 7.13 (m, 6H), 4.90 (s, 2H), 2.43 (m, 2H), 2.11 (m, 2H), 1.41 (s, 6H).

Example 1579

2-[5-Chloro-2-(1-ethyl-5,5-dimethyl-2-oxo-2,3,4,5-tetrahydro-1H-benzo[b]azepin-8-ylamino)-pyrimidin-4-ylamino]-N-ethyl-3-fluoro-benzamide The title compound was prepared with a procedure analogous to that used to prepare example 381 by combining 8-Amino-1-ethyl-5,5-dimethyl-1,3,4,5-tetrahydro-benzo[b]azepin-2-one and 2-(2,5-Dichloro-pyrimidin-4-ylamino)-N-ethyl-3-fluoro-benzamide to yield a yellow solid (6.3%). LCMS: m/z=525.19 (M+H$^+$), $^1$H NMR (400 MHz, CDCl$_3$) δ 8.84 (s, 1H), 8.11 (s, 1H), 7.49 (s, 1H), 7.35 (d, 1H, J=7.3 Hz), 7.24 (m, 3H), 7.14 (d, 1H, J=8.6 Hz), 7.02 (s, 1H), 3.70 (m, 2H), 3.43 (m, 2H), 2.26 (m, 2H), 2.06 (s, 2H), 1.32 (s, 6H), 1.28 (m, 3H), 1.18 (m, 3H).

Example 1580

{2-[5-Chloro-2-(1-ethyl-5,5-dimethyl-2-oxo-2,3,4,5-tetrahydro-1H-benzo[b]azepin-8-ylamino)-pyrimidin-4-ylamino]-phenoxy}-acetonitrile The title compound was prepared with a procedure analogous to that used to prepare example 381 by combining 8-Amino-1-ethyl-5,5-dimethyl-1,3,4,5-tetrahydro-benzo[b]azepin-2-one and [2-(2,5-Dichloro-pyrimidin-4-ylamino)-phenoxy]-acetonitrile to yield an off-white solid (3.3%). mp 253° C.; LCMS: m/z=491.16 (M+H$^+$), $^1$H NMR (400 MHz, CDCl$_3$) δ 8.41 (d, 1H, J=7.8 Hz), 8.31 (s, 1H), 7.65 (m, 2H), 7.28 (m, 2H), 7.18 (m, 1H), 7.07 (m, 3H), 4.91 (s, 2H), 3.76 (m, 2H), 2.34 (m, 2H), 2.04 (m, 2H), 1.36 (s, 6H), 1.24 (t, 3H).

Example 1581

2-{5-Chloro-2-[1-(2-methoxy-ethyl)-5,5-dimethyl-2-oxo-2,3,4,5-tetrahydro-1H-benzo[b]azepin-8-ylamino]-pyrimidin-4-ylamino}-3-fluoro-N-methyl-benzamide 11a) A procedure similar to that used to prepare 1-Ethyl-5,5-dimethyl-8-nitro-1,3,4,5-tetrahydro-benzo[b]azepin-2-one was used to prepare 1-(2-Methoxy-ethyl)-5,5-dimethyl-8-nitro-1,3,4,5-tetrahydro-benzo[b]azepin-2-one, a light yellow solid (58%). mp 127° C.; LCMS: m/z=263.05 (M+H$^+$), $^1$H NMR (400 MHz, CDCl$_3$) δ 8.72 (m, 1H), 8.05 (m, 1H), 7.56 (d, 1H, J=8.6 Hz), 3.81 (m, 4H), 3.48 (d, 3H, J=1.0 Hz), 2.33 (m, 2H), 2.14 (m, 2H), 1.40 (s, 6H).

11b) A procedure similar to that used to prepare 8-Amino-5,5-dimethyl-1,3,4,5-tetrahydro-benzo[b]azepin-2-one was used to prepare 8-Amino-1-(2-methoxy-ethyl)-5,5-dimethyl- 1,3,4,5-tetrahydro-benzo[b]azepin-2-one, an off-white solid (99%). mp 119° C.; LCMS: m/z=263.04 (M+H$^+$), $^1$H NMR (400 MHz, CDCl$_3$) δ 7.14 (d, 1H, J=8.6 Hz), 6.94 (m, 1H), 6.54 (m, 1H), 3.69 (m, 5H), 3.42 (d, 3H, J=1.0 Hz), 2.28 (m, 2H), 2.00 (m, 2H), 1.29 (m, 7H).

11c) The title compound was prepared with a procedure analogous to that used to prepare example 381 by combining 8-Amino-1-(2-methoxy-ethyl)-5,5-dimethyl-1,3,4,5-tetrahydro-benzo[b]azepin-2-one and 2-(2,5-Dichloro-pyrimidin-4-ylamino)-3-fluoro-N-methyl-benzamide to yield a yellow solid (26%). mp 222° C.; LCMS: m/z=541.18 (M+H$^+$), $^1$H NMR (400 MHz, CDCl$_3$) δ 8.85 (s, 1H), 8.10 (s, 1H), 7.58 (s, 1H), 7.25 (m, 6H), 6.54 (m, 1H), 3.60 (m, 4H), 3.34 (s, 3H), 2.95 (d, 3H, J=4.8 Hz), 2.25 (m, 2H), 1.96 (m, 2H), 1.29 (s, 6H).

Example 1582

(2-{5-Chloro-2-[1-(2-methoxy-ethyl)-5,5-dimethyl-2-oxo-2,3,4,5-tetrahydro-1H-benzo[b]azepin-8-ylamino]-pyrimidin-4-ylamino}-phenoxy)-acetonitrile The title compound was prepared with a procedure analogous to that used to prepare example 381 by combining 8-Amino-1-(2-methoxy-ethyl)-5,5-dimethyl-1,3,4,5-tetrahydro-benzo[b]azepin-2-one and [2-(2,5-Dichloro-pyrimidin-4-ylamino)-phenoxy]-acetonitrile to yield an off-white solid (43%). mp 255° C.; LCMS: m/z=521.20 (M+H$^+$), $^1$H NMR (400 MHz, CDCl$_3$) δ 8.45 (d, 1H, J=7.8 Hz), 8.13 (s, 1H), 7.75 (d, 1H, J=2.0 Hz), 7.65 (s, 1H), 7.46 (m, 1H), 7.30 (d, 1H, J=8.6 Hz), 7.11 (m, 3H), 7.01 (s, 1H), 4.92 (s, 2H), 3.69 (m, 4H), 3.35 (s, 3H), 2.35 (m, 2H), 2.06 (m, 2H), 1.35 (s, 6H).

Example 1583

(1S,2S,3R,4R)-3-{5-Chloro-2-[1-(2-methoxy-ethyl)-5,5-dimethyl-2-oxo-2,3,4,5-tetrahydro-1H-benzo[b]azepin-8-ylamino]-pyrimidin-4-ylamino}-bicyclo[2.2.1]hept-5-ene-2-carboxylic acid amide The title compound was prepared with a procedure analogous to that used to prepare example 381 by combining 8-Amino-1-(2-methoxy-ethyl)-5,5-dimethyl-1,3,4,5-tetrahydro-benzo[b]azepin-2-one and (1S,2S,3R,4R)-3-(2,5-Dichloro-pyrimidin-4-ylamino)-bicyclo[2.2.1]hept-5-ene-2-carboxylic acid amide to yield an off-white solid (44%). LCMS: m/z=525.22 (M+H$^+$), $^1$H NMR (400 MHz, CDCl$_3$) δ 7.89 (d, 1H, J=5.8 Hz), 7.63 (m, 2H), 7.45 (d, 1H, J=4.3 Hz), 7.27 (m, 1H), 7.03 (m, 1H), 6.03 (m, 2H), 5.97 (m, 2H), 4.36 (m, 1H), 3.74 (m, 4H), 3.38 (d, 3H, J=5.6 Hz), 3.06 (bs, 1H), 2.89 (bs, 1H), 2.51 (m, 1H), 2.30 (m, 3H), 2.03 (m, 2H), 1.62 (m, 1H), 1.33 (bs, 6H).

Example 1584

8-[5-Chloro-4-(2-methoxy-4-morpholin-4-yl-phenylamino)-pyrimidin-2-ylamino]-1-(2-methoxy-ethyl)-5,5-dimethyl-1,3,4,5-tetrahydro-benzo[b]azepin-2-one The title compound was prepared with a procedure analogous to that used to prepare example 381 by combining 8-Amino-1-(2-methoxy-ethyl)-5,5-dimethyl-1,3,4,5-tetrahydro-benzo[b]azepin-2-one and (2,5-Dichloro-pyrimidin-4-yl)-(2-methoxy-4-morpholin-4-yl-phenyl)-amine to yield an off-white solid (51%). LCMS: m/z=581.26 (M+H$^+$), $^1$H NMR (400 MHz, CDCl$_3$) δ 8.22 (dd, 1H, J=8.8, 1.3 Hz), 8.04 (d, 1H, J=1.5 Hz), 7.78 (m, 1H), 7.60 (d, 2H, J=6.6 Hz), 7.38 (m, 1H), 7.27 (m, 1H), 6.53 (m, 1H), 6.42 (m, 1H), 3.89 (m, 8H), 3.88 (m, 3H), 3.28 (d, 3H, J=1.8 Hz), 2.17 (m, 4H), 1.32 (m, 6H).

Example 1585

2-{5-Chloro-2-[1-(2-methoxy-ethyl)-5,5-dimethyl-2-oxo-2,3,4,5-tetrahydro-1H-benzo[b]azepin-8-ylamino]-pyrimidin-4-ylamino}-N-methyl-benzamide The title compound was prepared with a procedure analogous to that used to prepare example 381 by combining 8-Amino-1-(2-methoxy-ethyl)-5,5-dimethyl-1,3,4,5-tetrahydro-benzo[b]azepin-2-one and 2-(2,5-Dichloro-pyrimidin-4-ylamino)-N-methyl-benzamide to yield a light yellow solid (2.4%). LCMS: m/z=523.17 (M+H$^+$), $^1$H NMR (400 MHz, CDCl$_3$) δ 11.02 (bs, 1H), 8.55 (d, 3H, J=8.6 Hz), 8.09 (s, 1H), 7.77 (d, 1H, J=8.0 Hz), 7.52 (d, 1H, J=7.6 Hz), 7.37 (m, 3H), 7.27 (m, 1H), 7.09 (m, 1H), 6.82 (bs, 1H), 3.59 (m, 2H), 3.42 (m, 2H), 3.29 (s, 3H), 3.01 (d, 3H, J=4.8 Hz), 2.31 (m, 2H), 1.99 (m, 2H), 1.31 (m, 6H).

Example 1586

(1S,2S,3R,4R)-3-[5-Chloro-2-(1-ethyl-5,5-dimethyl-2-oxo-2,3,4,5-tetrahydro-1H-benzo[b]azepin-8-ylamino)-pyrimidin-4-ylamino]-bicyclo[2.2.1]hept-5-ene-2-carboxylic acid amide The title compound was prepared with a procedure analogous to that used to prepare example 381 by combining 8-Amino-1-ethyl-5,5-dimethyl-1,3,4,5-tetrahydro-benzo[b]azepin-2-one and (1S,2S,3R,4R)-3-(2,5-Dichloro-pyrimidin-4-ylamino)-bicyclo[2.2.1]hept-5-ene-2-carboxylic acid amide to yield a white solid (20%). LCMS: m/z=495.23 (M+H$^+$), $^1$H NMR (400 MHz, CDCl$_3$) δ 7.87 (d, 3H, J=0.76 Hz), 7.66 (bs, 1H), 7.51 (m, 2H), 7.27 (m, 1H), 7.13 (m, 1H), 6.30 (m, 2H), 6.17 (bs, 1H), 5.97 (bs, 1H), 4.33 (t, 1H, J=8.1 Hz), 3.81 (m, 2H), 3.06 (s, 1H), 2.89 (s, 1H), 2.51 (d, 1H, J=8.1 Hz), 2.27 (m, 3H), 2.03 (m, 2H), 1.62 (d, 1H, J=8.9 Hz), 1.30 (m, 9H).

Example 1587

8-[5-Chloro-4-(2-methoxy-4-morpholin-4-yl-phenylamino)-pyrimidin-2-ylamino]-1-ethyl-5,5-dimethyl-1,3,4,5-tetrahydro-benzo[b]azepin-2-one The title compound was prepared with a procedure analogous to that used to prepare example 381 by combining 8-Amino-1-ethyl-5,5-dimethyl-1,3,4,5-tetrahydro-benzo[b]azepin-2-one and (2,5-Dichloro-pyrimidin-4-yl)-(2-methoxy-4-morpholin-4-yl-phenyl)-amine to yield an off-white solid (65%). LCMS: m/z=551.27 (M+H$^+$), $^1$H NMR (400 MHz, CDCl$_3$) δ 8.20 (d, 1H, J=8.8 Hz), 8.04 (s, 1H), 7.79 (bs, 1H), 7.66 (s, 1H), 7.62 (s, 1H), 7.25 (m, 2H), 6.53 (m, 1H), 6.41 (d, 1H, J=8.8 Hz), 3.91 (s, 3H), 3.88 (m, 4H), 3.74 (m, 2H), 3.14 (m, 4H), 2.33 (m, 2H), 2.04 (m, 2H), 1.33 (s, 6H), 1.21 (t, 3H, J=7.1 Hz).

Example 1588

2-[5-Chloro-2-(1-isopropyl-5,5-dimethyl-2-oxo-2,3, 4,5-tetrahydro-1H-benzo[b]azepin-8-ylamino)-pyrimidin-4-ylamino]-3-fluoro-N-methyl-benzamide 18a) A procedure similar to that used to prepare 1-Ethyl-5,5-dimethyl-8-nitro-1,3,4,5-tetrahydro-benzo[b]azepin-2-one was used to prepare 1-Isopropyl-5,5-dimethyl-8-nitro-1, 3,4,5-tetrahydro-benzo[b]azepin-2-one, an orange solid (51%). mp 110° C.; LCMS: m/z=277.05 (M+H$^+$), $^1$H NMR (400 MHz, CDCl$_3$) δ 8.09 (dd, 1H, J=8.9, 2.3 Hz), 8.04 (d, 1H, J=2.3 Hz), 7.60 (d, 1H, J=8.8 Hz), 4.76 (m, 1H), 2.27 (m, 3H), 1.91 (m, 1H), 1.58 (m, 3H), 1.48 (s, 3H), 1.36 (s, 3H), 1.04 (d, 3H, J=6.6 Hz).

18b) A procedure similar to that used to prepare 8-Amino-5,5-dimethyl-1,3,4,5-tetrahydro-benzo[b]azepin-2-one was used to prepare 8-Amino-1-isopropyl-5,5-dimethyl-1,3,4,5-tetrahydro-benzo[b]azepin-2-one, an off-white solid (99%). LCMS: m/z=247.06 (M+H$^+$), $^1$H NMR (400 MHz, CDCl$_3$) δ 7.16 (d, 1H, J=8.3 Hz), 6.57 (dd, 1H, J=8.3, 2.5 Hz), 6.54 (d, 1H, J=2.5 Hz), 4.66 (m, 1H), 3.67 (bs, 2H), 2.32 (m, 1H), 2.14 (m, 2H), 1.78 (m, 1H), 1.49 (d, 3H, J=6.6 Hz), 1.36 (s, 3H), 1.26 (s, 3H), 1.05 (d, 3H, J=7.3 Hz).

18c) The title compound was prepared with a procedure analogous to that used to prepare example 381 by combining 8-Amino-1-isopropyl-5,5-dimethyl-1,3,4,5-tetrahydro-benzo[b]azepin-2-one and 2-(2,5-Dichloro-pyrimidin-4-ylamino)-3-fluoro-N-methyl-benzamide to yield a light yellow solid (9.6%). LCMS: m/z=525.22 (M+H$^+$), $^1$H NMR (400 MHz, CDCl$_3$) δ 8.01 (s, 1H), 7.41 (s, 1H), 7.34 (d, 1H, J=7.1 Hz), 7.18 (m, 6H), 4.50 (m, 1H), 2.84 (m, 3H), 2.23 (m, 1H), 2.07 (m, 2H), 1.76 (m, 1H), 1.31 (s, 3H), 1.26 (d, 3H, J=6.6 Hz), 1.18 (s, 3H), 0.86 (d, 3H, J=7.1 Hz).

Example 1589

2-[5-Chloro-2-(1-ethyl-5,5-dimethyl-2-oxo-2,3,4,5-tetrahydro-1H-benzo[b]azepin-8-ylamino)-pyrimidin-4-ylamino]-N-methyl-benzamide The title compound was prepared with a procedure analogous to that used to prepare example 381 by combining 8-Amino-1-ethyl-5,5-dimethyl-1,3,4,5-tetrahydro-benzo[b]azepin-2-one and 2-(2,5-Dichloro-pyrimidin-4-ylamino)-N-methyl-benzamide to yield an off-white solid (2.8%). LCMS: m/z=493.22 (M+H$^+$), $^1$H NMR (400 MHz, CDCl$_3$) δ 8.48 (d, 1H, J=8.3 Hz), 8.06 (s, 1H), 7.72 (d, 1H, J=1.8 Hz), 7.52 (d, 1H, J=7.6 Hz), 7.17 (m, 5H), 3.56 (m, 2H), 3.37 (s, 2H), 2.98 (m, 3H), 2.29 (m, 2H), 2.01 (m, 2H), 1.30 (m, 6H), 1.06 (m, 3H).

Example 1590

(1S,2S,3R,4R)-3-[5-Chloro-2-(1-isopropyl-5,5-dimethyl-2-oxo-2,3,4,5-tetrahydro-1H-benzo[b]azepin-8-ylamino)-pyrimidin-4-ylamino]-bicyclo[2.2.1]hept-5-ene-2-carboxylic acid amide The title compound was prepared with a procedure analogous to that used to prepare example 381 by combining 8-Amino-1-isopropyl-5,5-dimethyl-1,3,4,5-tetrahydro-benzo[b]azepin-2-one and (1S,2S,3R,4R)-3-(2,5-Dichloro-pyrimidin-4-ylamino)-bicyclo[2.2.1]hept-5-ene-2-carboxylic acid amide to yield an off-white solid (67%). mp 195° C.; LCMS: m/z=509.27 (M+H$^+$), $^1$H NMR (400 MHz, CDCl$_3$) δ 7.83 (s, 1H), 7.47 (m, 1H), 7.34 (m, 1H), 7.25 (m, 1H), 6.23 (m, 2H), 4.61 (m, 1H), 4.26 (m, 1H), 3.00 (s, 1H), 2.85 (d, 1H, J=11.9 Hz), 2.66 (s, 3H), 2.47 (d, 1H, J=8.1 Hz), 2.31 (m, 1H), 2.15 (m, 3H), 1.80 (m, 1H), 1.56 (m, 1H), 1.45 (m, 3H), 1.36 (s, 3H), 1.24 (m, 4H), 0.99 (t, 3H, J=6.8 Hz).

Example 1591

8-[5-Chloro-4-(2-methoxy-4-morpholin-4-yl-phenylamino)-pyrimidin-2-ylamino]-1-isopropyl-5,5-dimethyl-1,3,4,5-tetrahydro-benzo[b]azepin-2-one The title compound was prepared with a procedure analogous to that used to prepare example 381 by combining 8-Amino-1-isopropyl-5,5-dimethyl-1,3,4,5-tetrahydro-benzo[b]azepin-2-one and (2,5-Dichloro-pyrimidin-4-yl)-(2-methoxy-4-morpholin-4-yl-phenyl)-amine to yield an off-white solid (26%). mp 231° C.; LCMS: m/z=565.57 (M+H$^+$), $^1$H NMR (400 MHz, CDCl$_3$) δ 8.24 (d, 1H, J=8.8 Hz), 8.06 (s, 3H), 7.65 (m, 1H), 7.63 (m, 1H), 6.89 (s, 1H), 6.56 (d, 1H, J=2.3 Hz), 6.48 (m, 1H), 4.69 (m, 1H), 3.94 (s, 3H), 3.91 (m, 4H), 3.18 (m, 4H), 2.39 (m, 1H), 2.21 (m, 2H), 1.84 (m, 1H), 1.50 (m, 1H), 1.43 (m, 6H), 1.36 (s, 1H), 1.30 (s, 3H), 1.26 (s, 1H), 1.02 (d, 3H, J=7.1 Hz).

Example 1592

2-[5-Chloro-2-(1-isobutyl-5,5-dimethyl-2-oxo-2,3,4, 5-tetrahydro-1H-benzo[b]azepin-8-ylamino)-pyrimidin-4-ylamino]-3-fluoro-N-methyl-benzamide 22a) A procedure similar to that used to prepare 1-Ethyl-5,5-dimethyl-8-nitro-1,3,4,5-tetrahydro-benzo[b]azepin-2-one was used to prepare 1-Isobutyl-5,5-dimethyl-8-nitro-1,3, 4,5-tetrahydro-benzo[b]azepin-2-one, a yellow solid (55%). mp 106° C.; LCMS: m/z=291.13 (M+H$^+$), $^1$H NMR (400 MHz, CDCl$_3$) δ 8.17 (d, 1H, J=2.3 Hz), 8.06 (dd, 1H, J=8.6, 2.3 Hz), 7.59 (d, 1H, J=8.8 Hz), 3.53 (bs, 2H), 2.41 (m, 1H), 2.33 (m, 2H), 2.12 (m, 2H), 1.42 (s, 6H), 1.05 (d, 6H, J=6.8 Hz).

22b) A procedure similar to that used to prepare 8-Amino-5,5-dimethyl-1,3,4,5-tetrahydro-benzo[b]azepin-2-one was used to prepare 8-Amino-1-isobutyl-5,5-dimethyl-1,3,4,5-tetrahydro-benzo[b]azepin-2-one, a yellow solid. LCMS: m/z=261.13 (M+H$^+$), $^1$H NMR (400 MHz, CDCl$_3$) δ 7.16 (d, 1H, J=8.6 Hz), 6.62 (m, 1H), 6.54 (m, 1H), 3.70 (m, 4H), 2.37 (m, 1H), 2.29 (m, 2H), 1.98 (m, 2H), 1.30 (s, 6H), 1.00 (d, 6H, J=6.6 Hz).

22c) The title compound was prepared with a procedure analogous to that used to prepare example 381 by combining 8-Amino-1-isobutyl-5,5-dimethyl-1,3,4,5-tetrahydro-benzo[b]azepin-2-one and 2-(2,5-Dichloro-pyrimidin-4-ylamino)-3-fluoro-N-methyl-benzamide to yield a yellow solid (21%). mp 289° C.; LCMS: m/z=539.54 (M+H$^+$), $^1$H NMR (400 MHz, CDCl$_3$) δ 8.04 (d, 1H, J=1.0 Hz), 7.60 (s, 1H), 7.47 (s, 2H), 7.43 (d, 1H, J=7.3 Hz), 7.29 (m, 3H), 7.18 (d, 1H, J=8.6 Hz), 3.35 (m, 1H), 2.86 (s, 3H), 2.28 (m, 3H), 1.98 (m, 3H), 1.31 (m, 7H), 0.95 (d, 6H, J=5.8 Hz).

Example 1593

(1S,2S,3R,4R)-3-[5-Chloro-2-(1-isobutyl-5,5-dimethyl-2-oxo-2,3,4,5-tetrahydro-1H-benzo[b]azepin-8-ylamino)-pyrimidin-4-ylamino]-bicyclo[2.2.1]hept-5-ene-2-carboxylic acid amide The title compound was prepared with a procedure analogous to that used to prepare example 381 by combining 8-Amino-1-isobutyl-5,5-dimethyl-1,3,4,5-tetrahydro-benzo[b]azepin-2-one and (1S,2S,3R,4R)-3-(2,5-Dichloro-pyrimidin-4-ylamino)-bicyclo[2.2.1]hept-5-ene-2-carboxylic acid amide to yield a white solid (25%). LCMS: m/z=523.54 (M+H$^+$), $^1$H NMR (400 MHz, CDCl$_3$) δ 7.87 (s, 1H), 7.54 (m, 2H), 7.28 (m, 2H), 7.09 (d, 1H, J=7.3 Hz), 6.32 (s, 2H), 5.87 (s, 1H), 5.81 (s, 1H), 4.33 (m, 1H), 3.08 (s, 1H), 2.90 (s, 1H), 2.51 (d, 1H, J=8.1 Hz), 2.36 (m, 4H), 2.03 (m, 3H), 1.63 (d, 1H, J=8.6 Hz), 1.27 (m, 1H), 1.00 (d, 6H, J=6.6 Hz).

Example 1594

8-[5-Chloro-4-(2-methoxy-4-morpholin-4-yl-phenylamino)-pyrimidin-2-ylamino]-1-isobutyl-5,5-dimethyl-1,3,4,5-tetrahydro-benzo[b]azepin-2-one The title compound was prepared with a procedure analogous to that used to prepare example 381 by combining 8-Amino-1-isobutyl-5,5-dimethyl-1,3,4,5-tetrahydro-benzo[b]azepin-2-one and (2,5-Dichloro-pyrimidin-4-yl)-(2-methoxy-4-morpholin-4-yl-phenyl)-amine to yield a colorless solid (9%). LCMS: m/z=579.59 (M+H$^+$), $^1$H NMR (400 MHz, CDCl$_3$) δ 8.22 (d, 1H, J=8.8 Hz), 8.05 (d, 1H, J=1.0 Hz), 7.67 (bs, 1H), 7.62 (bs, 1H), 7.22 (m, 3H), 6.55 (d, 1H, J=1.5 Hz), 6.48 (dd, 1H, J=8.8, 1.5 Hz), 3.93 (s, 3H), 3.90 (m, 4H), 3.16 (m, 4H), 2.36 (m, 5H), 2.05 (m, 2H), 1.35 (s, 6H), 0.97 (d, 6H, J=6.6 Hz).

Example 1595

2-[5-Chloro-2-(1-ethyl-5,5-dimethyl-2-oxo-2,3,4,5-tetrahydro-1H-benzo[b]azepin-8-ylamino)-pyrimidin-4-ylamino]-N,N-dimethyl-benzenesulfonamide The title compound was prepared with a procedure analogous to that used to prepare example 381 by combining 8-Amino-1-ethyl-5,5-dimethyl-1,3,4,5-tetrahydro-benzo[b]azepin-2-one and 2-(2,5-Dichloro-pyrimidin-4-ylamino)-N,N-dimethyl-benzenesulfonamide to yield an off-white solid, 2-[5-Chloro-2-(1-ethyl-5,5-dimethyl-2-oxo-2,3,4,5-tetrahydro-1H-benzo[b]azepin-8-ylamino)-pyrimidin-4-ylamino]-N,N-dimethyl-benzenesulfonamide (50%). LCMS: m/z=543.51 (M+H$^+$), $^1$H NMR (400 MHz, CDCl$_3$) δ 9.49 (s, 1H), 8.52 (d, 1H, J=8.6 Hz), 8.17 (s, 1H), 7.88 (d, 1H, J=8.1 Hz), 7.68 (s, 1H), 7.50 (m, 1H), 7.28 (m, 4H), 3.68 (m, 2H), 2.76 (s, 6H), 2.34 (m, 2H), 2.05 (m, 2H), 1.35 (s, 2H), 1.16 (m, 3H).

Example 1596

2-[2-(1-Acetyl-5,5-dimethyl-2,3,4,5-tetrahydro-1H-benzo[b]azepin-8-ylamino)-5-chloro-pyrimidin-4-ylamino]-3-fluoro-N-methyl-benzamide 26a) A procedure similar to that used to prepare 5,5-Dimethyl-7-nitro-2,3,4,5-tetrahydro-1H-benzo[b]azepine was used to prepare 5,5-Dimethyl-8-nitro-2,3,4,5-tetrahydro-1H-benzo[b]azepine, a brown solid (84%). LCMS: m/z=221.17 (M+H$^+$), $^1$H NMR (400 MHz, CDCl$_3$) δ 7.69 (m, 1H), 7.55 (m, 1H), 7.44 (d, 1H, J=8.6 Hz), 3.93 (bs, 1H), 3.09 (m, 2H), 1.91 (m, 2H), 1.68 (m, 2H), 1.38 (s, 6H).

26b) 5,5-Dimethyl-8-nitro-2,3,4,5-tetrahydro-1H-benzo[b]azepine (0.874 g, 0.00397 mol), acetic anhydride (8.418 mL) and acetonitrile (10 mL) were combined in a round bottom flask. The mixture was stirred at room temp for 17 hours and then heated at 60° C. for 2 days. The mixture was concentrated under reduced pressure, then purified by normal phase chromatography eluting with 10% to 50% ethyl acetate in hexane to yield a yellow oil, 1-(5,5-Dimethyl-8-nitro-2,3,4,5-tetrahydro-benzo[b]azepin-1-yl)-ethanone (1.04 g, 61%). LCMS: m/z=263.25 (M+H$^+$), $^1$H NMR (400 MHz, CDCl$_3$) δ 8.15 (m, 1H), 7.98 (m, 1H), 7.65 (d, 1H, J=8.6 Hz), 4.82 (m, 1H), 2.60 (m, 1H), 2.24 (m, 1H), 1.95 (s, 3H), 1.81 (m, 1H), 1.70 (m, 1H), 1.56 (m, 6H), 1.28 (m, 1H).

26c) A procedure similar to that used to prepare 8-Amino-5,5-dimethyl-1,3,4,5-tetrahydro-benzo[b]azepin-2-one was used to prepare 1-(8-Amino-5,5-dimethyl-2,3,4,5-tetrahydro-benzo[b]azepin-1-yl)-ethanone, a white solid (95%). mp 168° C.; LCMS: m/z=233.23 (M+H$^+$), $^1$H NMR (400 MHz, CDCl$_3$) δ 7.21 (d, 1H, J=8.3 Hz), 6.60 (m, 1H), 6.41 (m, 1H), 4.71 (m, 1H), 3.67 (bs, 2H), 2.59 (m, 1H), 2.18 (m, 1H), 1.94 (s, 3H), 1.67 (m, 2H), 1.51 (m, 1H), 1.39 (s, 3H), 1.18 (s, 3H).

26d) The title compound was prepared with a procedure analogous to that used to prepare example 381 by combining 1-(8-Amino-5,5-dimethyl-2,3,4,5-tetrahydro-benzo[b]azepin-1-yl)-ethanone and 2-(2,5-Dichloro-pyrimidin-4-ylamino)-3-fluoro-N-methyl-benzamide to yield a yellow solid (43%). LCMS: m/z=511.47 (M+H$^+$), $^1$H NMR (400 MHz, CDCl$_3$) δ 8.89 (bs, 1H), 8.08 (s, 1H), 7.60 (d, 1H, J=1.8 Hz), 7.39 (m, 2H), 7.25 (m, 3H), 6.91 (d, 1H, J=8.3 Hz), 6.85 (bs, 1H), 4.62 (m, 1H), 2.97 (d, 3H, J=4.8 Hz), 2.41 (m, 1H), 2.15 (m, 1H), 1.72 (s, 3H), 1.65 (m, 2H), 1.47 (m, 1H), 1.34 (s, 3H), 1.13 (s, 3H).

Example 1597

3-[5-Chloro-2-(1-ethyl-5,5-dimethyl-2-oxo-2,3,4,5-tetrahydro-1H-benzo[b]azepin-8-ylamino)-pyrimidin-4-ylamino]-thiophene-2-carboxylic acid methylamide The title compound was prepared with a procedure analogous to that used to prepare example 381 by combining 8-Amino-1-ethyl-5,5-dimethyl-1,3,4,5-tetrahydro-benzo[b]azepin-2-one and 3-(2,5-Dichloro-pyrimidin-4-ylamino)-thiophene-2-carboxylic acid methylamide to yield a light yellow solid (6.7%). LCMS: m/z=499.46 (M+H$^+$), $^1$H NMR (400 MHz, CDCl$_3$) δ8.28 (m, 1H), 8.09 (d, 1H, J=1.8 Hz), 7.74 (m, 1H), 7.34 (m, 1H), 7.24 (m, 2H), 3.78 (m, 2H), 2.96 (s, 3H), 2.34 (m, 2H), 2.06 (m, 2H), 1.36 (m, 6H), 1.21 (m, 3H).

Example 1598

1-{8-[5-Chloro-4-(2-methoxy-4-morpholin-4-yl-phenylamino)-pyrimidin-2-ylamino]-5,5-dimethyl-2,3,4,5-tetrahydro-benzo[b]azepin-1-yl}-ethanone The title compound was prepared with a procedure analogous to that used to prepare example 381 by combining 1-(8-Amino-5,5-dimethyl-2,3,4,5-tetrahydro-benzo[b]azepin-1-yl)-ethanone and (2,5-Dichloro-pyrimidin-4-yl)-(2-methoxy-4-morpholin-4-yl-phenyl)-amine to yield an off-white solid (93%). LCMS: m/z=551.54 (M+H$^+$), $^1$H NMR (400 MHz, CDCl$_3$) δ 8.12 (d, 1H, J=8.6 Hz), 8.01 (s, 1H), 7.54 (s, 1H), 7.45 (s, 1H), 7.41 (d, 1H, J=1.5 Hz), 7.32 (m, 2H), 6.53 (m, 2H), 4.74 (m, 1H), 3.89 (m, 7H), 3.17 (m, 4H), 2.60 (m, 1H), 2.20 (m, 1H), 1.91 (s, 3H), 1.62 (m, 3H), 1.41 (s, 3H), 1.19 (s, 3H).

Example 1599

2-{5-Chloro-2-[1-(2-methoxy-ethyl)-5,5-dimethyl-2,3,4,5-tetrahydro-1H-benzo[b]azepin-8-ylamino]-pyrimidin-4-ylamino}-3-fluoro-N-methyl-benzamide 29$^a$) Using 1-(2-Methoxy-ethyl)-5,5-dimethyl-8-nitro-1,3,4,5-tetrahydro-benzo[b]azepin-2-one as starting material, a procedure similar to that used to prepare 5,5-Dimethyl-7-nitro-2,3,4,5-tetrahydro-1H-benzo[b]azepine was used to prepare 1-(2-Methoxy-ethyl)-5,5-dimethyl-8-nitro-2,3,4,5-tetrahydro-1H-benzo[b]azepine, an orange oil (91%). LCMS: m/z=279.24 (M+H$^+$), $^1$H NMR (400 MHz, CDCl$_3$) δ 7.83 (m, 1H), 7.75 (m, 1H), 7.44 (m, 1H), 3.62 (m, 2H), 3.47 (m, 2H), 3.39 (d, 3H, J=1.5 Hz), 3.01 (m, 2H), 1.80 (m, 2H), 1.65 (m, 2H), 1.43 (d, 6H, J=1.3 Hz).

29b) Using 1-(2-Methoxy-ethyl)-5,5-dimethyl-8-nitro-2,3,4,5-tetrahydro-1H-benzo[b]azepine as starting material, a procedure similar to that used to prepare 8-Amino-5,5-dimethyl-1,3,4,5-tetrahydro-benzo[b]azepin-2-one was used to prepare 1-(2-Methoxy-ethyl)-5,5-dimethyl-2,3,4,5-tetrahydro-1H-benzo[b]azepin-8-ylamine, a brown oil (98%). LCMS: m/z=249.27 (M+H$^+$), $^1$H NMR (400 MHz, CDCl$_3$) δ 7.10 (d, 1H, J=8.3 Hz), 6.38 (s, 1H), 6.30 (m, 1H), 3.59 (m, 2H), 3.52 (bs, 2H), 3.37 (m, 5H), 2.92 (m, 2H), 1.76 (m, 2H), 1.56 (m, 2H), 1.36 (s, 6H).

29c) The title compound was prepared with a procedure analogous to that used to prepare example 381 by combining 1-(2-Methoxy-ethyl)-5,5-dimethyl-2,3,4,5-tetrahydro-1H-benzo[b]azepin-8-ylamine and 2-(2,5-Dichloro-pyrimidin-4-ylamino)-3-fluoro-N-methyl-benzamide to yield a light yellow solid (23%). LCMS: m/z=527.49 (M+H$^+$), $^1$H NMR (400 MHz, CDCl$_3$) δ 8.56 (bs, 1H), 8.07 (s, 1H), 7.18 (m, 6H), 6.86 (bs, 1H), 6.74 (d, 1H, J=8.3 Hz), 3.47 (m, 2H), 3.40 (s, 3H), 2.93 (d, 3H, J=4.6 Hz), 2.73 (m, 4H), 1.72 (m, 2H), 1.53 (m, 2H), 1.34 (s, 6H).

Example 1600

(1S,2S,3R,4R)-3-{5-Chloro-2-[1-(2-methoxy-ethyl)-5,5-dimethyl-2,3,4,5-tetrahydro-1H-benzo[b]azepin-8-ylamino]-pyrimidin-4-ylamino}-bicyclo[2.2.1]hept-5-ene-2-carboxylic acid amide The title compound was prepared with a procedure analogous to that used to prepare example 381 to yield a light yellow solid (62%). LCMS: m/z=511.53 (M+H$^+$), $^1$H NMR (400 MHz, CDCl$_3$) δ 7.85 (s, 1H), 7.72 (bs, 1H), 7.24 (m, 2H), 7.15 (s, 1H), 6.77 (d, 1H, J=8.3 Hz), 6.29 (m, 2H), 6.19 (bs, 1H), 5.91 (bs, 1H), 4.43 (m, 1H), 3.59 (m, 2H), 3.36 (m, 5H), 3.03 (s, 1H), 2.93 (m, 2H), 2.87 (s, 1H), 2.50 (d, 1H, J=8.3 Hz), 2.26 (d, 1H, J=9.1 Hz), 1.77 (m, 2H), 1.60 (m, 3H), 1.39 (s, 6H).

Example 1601

5-Chloro-N*2*-[1-(2-methoxy-ethyl)-5,5-dimethyl-2,3,4,5-tetrahydro-1H-benzo[b]azepin-8-yl]-N*4*-(2-methoxy-4-morpholin-4-yl-phenyl)-pyrimidine-2,4-diamine The title compound was prepared with a procedure analogous to that used to prepare example 381 to yield a yellow solid (33%). LCMS: m/z=567.56 (M+H$^+$), $^1$H NMR (400 MHz, CDCl$_3$) δ 8.28 (d, 1H, J=8.6 Hz), 8.04 (d, 1H, J=1.8 Hz), 7.59 (s, 1H), 7.27 (m, 2H), 7.18 (m, 1H), 7.09 (s, 1H), 6.54 (s, 1H), 6.49 (m, 1H), 3.91 (m, 7H), 3.56 (m, 2H), 3.34 (m, 5H), 3.16 (m, 4H), 2.97 (m, 2H), 1.79 (m, 2H), 1.61 (m, 2H), 1.42 (s, 6H).

Example 1602

2-[2-(1-Acetyl-5,5-dimethyl-2,3,4,5-tetrahydro-1H-benzo[b]azepin-8-ylamino)-5-chloro-pyrimidin-4-ylamino]-3-fluoro-N-prop-2-ynyl-benzamide The title compound was prepared with a procedure analogous to that used to prepare example 381 to yield a yellow solid (47%). LCMS: m/z=535.48 (M+H$^+$), $^1$H NMR (400 MHz, CDCl$_3$) δ 8.66 (s, 1H), 8.07 (d, 1H, J=1.8 Hz), 7.56 (m, 2H), 7.45 (m, 1H), 7.27 (m, 4H), 6.92 (d, 1H, J=8.6 Hz), 4.62 (m, 1H), 4.18 (m, 2H), 2.40 (m, 1H), 2.24 (m, 1H), 2.13 (m, 1H), 1.74 (s, 3H), 1.64 (m, 2H), 1.45 (m, 1H), 1.36 (s, 3H), 1.12 (s, 3H).

Example 1603

2-{5-Chloro-2-[5,5-dimethyl-1-(2-pyrrolidin-1-yl-acetyl)-2,3,4,5-tetrahydro-1H-benzo[b]azepin-8-ylamino]-pyrimidin-4-ylamino}-3-fluoro-N-methyl-benzamide 33a) 5,5-Dimethyl-8-nitro-2,3,4,5-tetrahydro-1H-benzo[b]azepine (0.837 g, 3.80 mmol), pyridine (0.408 mL, 5.04 mmol) and 4-dimethylaminopyridine (14.4 mg, 0.118 mmol) were dissolved in anhydrous 1,2-Dichloroethane (9.0 mL) before adding chloroacetyl chloride (0.403 mL, 5.07 mmol). The reaction was stirred at room temperature for 3 hours, washed sequentially with 1 N HCl, water, saturated sodium bicarbonate solution and brine. The organic phase was dried with magnesium sulfate, filtered and concentrated under reduced pressure. The residue was triturated with ether (6 mL×2) to yield a crude brown solid, 2-Chloro-1-(5,5-dimethyl-8-nitro-2,3,4,5-tetrahydro-benzo[b]azepin-1-yl)-ethanone. LCMS: m/z=297.42 (M+H$^+$).

33b) 2-Chloro-1-(5,5-dimethyl-8-nitro-2,3,4,5-tetrahydro-benzo[b]azepin-1-yl)-ethanone (0.494 g, 0.00166 mol), pyrrolidine (0.310 mL, 0.00371 mol) and N,N-dimethylformamide (5.0 mL, 0.064 mol) were combined in a round bottom flask and stirred at room temperature for 18 hours. The reaction was concentrated under reduced pressure. The residue was dissolved in methylene chloride and washed with water and then brine. The organic phase was dried with magnesium sulfate, filtered and concentrated under reduced pressure. The residue was triturated with ether to yield a crude orange solid, 1-(5,5-Dimethyl-8-nitro-2,3,4,5-tetrahydro-benzo[b]azepin-1-yl)-2-pyrrolidin-1-yl-ethanone. LCMS: m/z=332.33 (M+H$^+$).

33c) Using 1-(5,5-Dimethyl-8-nitro-2,3,4,5-tetrahydro-benzo[b]azepin-1-yl)-2-pyrrolidin-1-yl-ethanone as starting material, a procedure similar to that used to prepare 8-Amino-5,5-dimethyl-1,3,4,5-tetrahydro-benzo[b]azepin-2-one was used to prepare 1-(8-Amino-5,5-dimethyl-2,3,4,5-tetrahydro-benzo[b]azepin-1-yl)-2-pyrrolidin-1-yl-ethanone, an orange solid. LCMS: m/z=302.33 (M+H$^+$).

33d) The title compound was prepared with a procedure analogous to that used to prepare example 381 to yield an orange solid (26%). LCMS: m/z=580.45 (M+H$^+$), $^1$H NMR (400 MHz, CDCl$_3$) δ 9.04 (bs, 1H), 8.06 (s, 1H), 7.55 (m, 3H), 7.41 (d, 1H, J=7.8 Hz), 7.24 (m, 3H), 6.89 (m, 1H), 5.77 (m, 1H), 4.63 (m, 1H), 3.17 (m, 1H), 2.95 (d, 3H, J=4.8 Hz), 2.53 (m, 2H), 2.44 (m, 2H), 2.29 (m, 2H), 2.13 (m, 1H), 1.71 (m, 5H), 1.46 (m, 1H), 1.13 (s, 3H).

Example 1604

2-{5-Chloro-2-[5,5-dimethyl-1-(2-pyrrolidin-1-yl-acetyl)-2,3,4,5-tetrahydro-1H-benzo[b]azepin-8-ylamino]-pyrimidin-4-ylamino}-3-fluoro-N-prop-2-ynyl-benzamide The title compound was prepared with a procedure analogous to that used to prepare example 381 to yield a light yellow solid (16%). LCMS: m/z=604.24 (M+H$^+$), $^1$H NMR (400 MHz, CDCl$_3$) δ 8.76 (bs, 1H), 8.08 (d, 1H, J=1.3 Hz), 7.61 (m, 1H), 7.46 (d, 1H, J=7.3 Hz), 7.28 (m, 4H), 6.91 (d, 1H, J=8.3 Hz), 4.66 (m, 1H), 4.25 (m, 2H), 3.24 (m, 1H), 2.76 (m, 1H), 2.47 (m, 6H), 2.17 (m, 2H), 1.70 (m, 6H), 1.38 (s, 3H), 1.16 (s, 3H).

Example 1605

2-{5-Chloro-2-[5,5-dimethyl-1-(2-pyrrolidin-1-yl-ethyl)-2,3,4,5-tetrahydro-1H-benzo[b]azepin-8-ylamino]-pyrimidin-4-ylamino}-3-fluoro-N-methyl-benzamide, TFA salt 35a) 1-(5,5-Dimethyl-8-nitro-2,3,4,5-tetrahydro-benzo[b]azepin-1-yl)-2-pyrrolidin-1-yl-ethanone (0.508 g, 0.00153 mol), 1.00 M of Borane-THF complex in tetrahydrofuran (7.7 mL; Acros) and anhydrous tetrahydrofuran (12.4 mL) were combined in a round bottom flask and heated to 70° C. for 6.5 hours. Concentrated HCl was added dropwise until gas evolution stopped. Solvent was removed under reduced pressure, then an additional 5 mL of conc. HCl was added until the mixture was pH 1. The reaction was heated at 100° C. for 1.5 hours. The reaction was removed from the heat and 10 N NaOH (6 mL) was added until the mixture was pH 7-8. $Na_2CO_3$ was added until the solution was pH 11. The solution was extracted twice into DCM, and the combined organic layers were dried with sodium sulfate, filtered and concentrated under reduced pressure to yield a crude brown oil, 5,5-Dimethyl-8-nitro-1-(2-pyrrolidin-1-yl-ethyl)-2,3,4,5-tetrahydro-1H-benzo[b]azepine. LCMS: m/z=332.35 (M+H$^+$).

35b) Using 5,5-Dimethyl-8-nitro-1-(2-pyrrolidin-1-yl-ethyl)-2,3,4,5-tetrahydro-1H-benzo[b]azepine as starting material, a procedure similar to that used to prepare 8-Amino-5,5-dimethyl-1,3,4,5-tetrahydro-benzo[b]azepin-2-one was used to prepare 5,5-Dimethyl-1-(2-pyrrolidin-1-yl-ethyl)-2,3,4,5-tetrahydro-1H-benzo[b]azepin-8-ylamine, a brown oil. LCMS: m/z=288.17 (M+H$^+$), $^1$H NMR (400 MHz, CDCl$_3$) δ 7.08 (d, 3H, J=8.3 Hz), 6.63 (bs, 1H), 6.32 (m, 1H), 3.67 (m, 3H), 3.14 (m, 3H), 2.90 (m, 2H), 2.13 (m, 5H), 1.72 (m, 4H), 1.54 (m, 2H), 1.33 (m, 1H), 1.31 (s, 6H).

35c) The title compound was prepared with a procedure analogous to that used to prepare example 381 to yield a yellow solid (2.5%). LCMS: m/z=566.22 (M+H$^+$), $^1$H NMR (400 MHz, CDCl$_3$) δ 12.16 (bs, 1H), 11.88 (s, 1H), 10.52 (s, 1H), 8.75 (m, 1H), 7.86 (s, 1H), 7.56 (d, 1H, J=7.6 Hz), 7.28 (m, 4H), 6.98 (d, 1H, J=8.3 Hz), 3.59 (m, 2H), 3.00 (d, 3H, J=4.3 Hz), 2.86 (m, 2H), 2.73 (m, 2H), 2.65 (m, 2H), 2.01 (m, 4H), 1.78 (m, 2H), 1.59 (m, 2H), 1.29 (s, 6H).

Example 1606

(1S,2S,3R,4R)-3-{5-Chloro-2-[5,5-dimethyl-1-(2-pyrrolidin-1-yl-ethyl)-2,3,4,5-tetrahydro-1H-benzo[b]azepin-8-ylamino]-pyrimidin-4-ylamino}-bicyclo[2.2.1]hept-5-ene-2-carboxylic acid amide, TFA salt The title compound was prepared with a procedure analogous to that used to prepare example 381 to yield a light brown solid (68%). LCMS: m/z=550.29 (M+H$^+$), $^1$H NMR (400 MHz, CDCl$_3$) δ 11.15 (s, 1H), 10.71 (bs, 1H), 9.57 (d, 1H, J=6.3 Hz), 7.74 (s, 1H), 7.51 (d, 1H, J=8.6 Hz), 7.36 (s, 1H), 7.28 (m, 1H), 7.04 (s, 1H), 6.40 (m, 1H), 6.24 (m, 2H), 4.23 (m, 1H), 3.82 (bs, 1H), 3.68 (m, 1H), 3.55 (m, 1H), 3.33 (m, 2H), 3.13 (s, 1H), 3.02 (m, 3H), 2.90 (m, 2H), 2.71 (d, 1H, J=7.8 Hz), 2.45 (m, 1H), 2.11 (m, 1H), 1.73 (m, 6H), 1.35 (d, 6H, J=10.4 Hz), 1.06 (s, 1H), 0.87 (s, 1H).

Example 1607

(1S,2S,3R,4R)-3-{5-Chloro-2-[5,5-dimethyl-1-(2-pyrrolidin-1-yl-acetyl)-2,3,4,5-tetrahydro-1H-benzo[b]azepin-8-ylamino]-pyrimidin-4-ylamino}-bicyclo[2.2.1]hept-5-ene-2-carboxylic acid amide The title compound was prepared with a procedure analogous to that used to prepare example 381 to yield a light brown solid. LCMS: m/z=564.51 (M+H$^+$), $^1$H NMR (400 MHz, CDCl$_3$) (mixture of rotamers) δ 7.86 (m, 3.7H), 7.51 (m, 3.3H), 7.41 (s, 1H), 7.34 (m, 2.3H), 7.27 (m, 2.2H), 7.19 (m, 1.5H), 7.07 (d, 1H, J=8.1 Hz), 6.55 (s, 1.3H), 6.33 (m, 3.4H), 6.23 (m, 1.4H), 6.02 (m, 3.3H), 4.74 (m, 2.7H), 4.32 (m, 2.4H), 3.55 (m, 2.3H), 3.05 (s, 2.7H), 2.68 (m, 20H), 2.22 (m, 5.2H), 1.60 (m, 19.8H), 1.42 (s, 7H), 1.22 (s, 6.9H).

Example 1608

2-[2-(1-Acetyl-5,5-dimethyl-2,3,4,5-tetrahydro-1H-benzo[b]azepin-8-ylamino)-5-chloro-pyrimidin-4-ylamino]-3,5-difluoro-N-methyl-benzamide, TFA salt The title compound was prepared with a procedure analogous to that used to prepare example 381 to yield an off-white solid (30%). LCMS: m/z=529.22 (M+H$^+$), $^1$H NMR (400 MHz, CDCl$_3$) δ 12.08 (bs, 1H), 9.62 (bs, 1H), 7.91 (s, 1H), 7.51 (m, 2H), 7.36 (d, 1H, J=8.6 Hz), 7.23 (m, 2H), 7.05 (m, 1H), 4.69 (m, 1H), 3.00 (d, 3H, J=4.6 Hz), 2.50 (t, 1H, J=12.4 Hz), 2.13 (m, 1H), 1.71 (m, 5H), 1.54 (m, 1H), 1.41 (s, 3H), 1.12 (s, 3H).

Example 1609

2-{5-Chloro-2-[5,5-dimethyl-1-(2-pyrrolidin-1-yl-ethyl)-2,3,4,5-tetrahydro-1H-benzo[b]azepin-8-ylamino]-pyrimidin-4-ylamino}-3-fluoro-N-prop-2-ynyl-benzamide, TFA salt The title compound was prepared with a procedure analogous to that used to prepare example 381 to yield a brown solid (29%). LCMS: m/z=590.24 (M+H$^+$), $^1$H NMR (400 MHz, CDCl$_3$) δ 11.78 (s, 1H), 11.67 (bs, 1H), 10.25 (s, 1H), 8.76 (m, 1H), 7.92 (s, 1H), 7.60 (d, 1H, J=7.6 Hz), 7.41 (m, 1H), 7.27 (m, 3H), 6.98 (d, 1H, J=8.6 Hz), 4.22 (m, 2H), 3.65 (m, 1H), 2.87 (m, 9H), 2.24 (m, 1H), 2.03 (m, 4H), 1.77 (m, 2H), 1.58 (m, 2H), 1.29 (s, 6H).

Example 1610

5-Chloro-N*2*-[5,5-dimethyl-1-(2-pyrrolidin-1-yl-ethyl)-2,3,4,5-tetrahydro-1H-benzo[b]azepin-8-yl]-N*4*-(2-methoxy-4-morpholin-4-yl-phenyl)-pyrimidine-2,4-diamine, TFA salt The title compound was prepared with a procedure analogous to that used to prepare example 381 to yield a yellow solid (44%). mp 160° C.; LCMS: m/z=606.33 (M+H$^+$), $^1$H NMR (400 MHz, CDCl$_3$) δ 8.04 (m, 1H), 7.82 (s, 1H), 7.38 (d, 1H, J=8.8 Hz), 7.28 (s, 1H), 7.25 (d, 1H, J=8.6 Hz), 6.88 (s, 1H), 6.60 (m, 1H), 6.44 (d, 1H, J=8.8 Hz), 3.94 (s, 3H), 3.91 (m, 4H), 3.79 (m, 2H), 3.59 (m, 2H), 3.29 (m, 3H), 3.22 (m, 4H), 2.96 (m, 4H), 2.08 (m, 4H), 1.79 (m, 2H), 1.62 (m, 2H), 1.36 (s, 6H).

Example 1611

2-[5-Chloro-2-(5,5-dimethyl-2,3,4,5-tetrahydro-1H-benzo[b]azepin-8-ylamino)-pyrimidin-4-ylamino]-3-fluoro-N-methyl-benzamide, TFA salt 41a) Using 5,5-Dimethyl-8-nitro-2,3,4,5-tetrahydro-1H-benzo[b]azepine as starting material, a procedure similar to that used to prepare 8-Amino-5,5-dimethyl-1,3,4,5-tetrahydro-benzo[b]azepin-2-one was used to prepare 5,5-Dimethyl-2,3,4,5-tetrahydro-1H-benzo[b]azepin-8-ylamine, a brown solid (96%). LCMS: m/z=191.06 (M+H$^+$), $^1$H NMR (400 MHz, CDCl$_3$) δ 7.28 (m, 1H), 7.11 (d, 1H, J=8.3 Hz), 6.25 (dd, 1H, J=8.3, 2.5 Hz), 6.08 (d, 1H, J=2.3 Hz), 3.49 (m, 2H), 3.03 (m, 2H), 1.86 (m, 2H), 1.61 (m, 2H), 1.35 (s, 6H).

41b) The title compound was prepared with a procedure analogous to that used to prepare example 381 to yield a yellow solid (38%). LCMS: m/z=469.19 (M+H$^+$), $^1$H NMR (400 MHz, CDCl$_3$) δ 11.91 (bs, 1H), 10.85 (bs, 3H), 9.64 (bs, 1H), 8.39 (bs, 1H), 7.91 (s, 1H), 7.47 (m, 2H), 7.35 (d, 1H, J=8.8 Hz), 7.20 (m, 3H), 3.32 (m, 2H), 2.96 (m, 3H), 2.14 (m, 2H), 1.83 (m, 2H), 1.38 (s, 6H).

Example 1612

2-[5-Chloro-2-(5,5-dimethyl-2,3,4,5-tetrahydro-1H-benzo[b]azepin-8-ylamino)-pyrimidin-4-ylamino]-3-fluoro-N-prop-2-ynyl-benzamide, TFA salt The title compound was prepared with a procedure analogous to that used to prepare example 381 to yield a yellow solid (37%). LCMS: m/z=493.19 (M+H$^+$), $^1$H NMR (400 MHz, CDCl$_3$) δ 11.88 (bs, 1H), 10.74 (bs, 3H), 9.59 (bs, 1H), 8.91 (bs, 1H), 7.90 (s, 1H), 7.52 (s, 1H), 7.47 (m, 1H), 7.34 (d, 1H, J=8.6 Hz), 7.23 (d, 1H, J=8.6 Hz), 7.15 (m, 2H), 4.15 (bs, 2H), 3.40 (bs, 2H), 2.17 (m, 3H), 1.84 (m, 2H), 1.38 (s, 6H).

Example 1613

(1S,2S,3R,4R)-3-[5-Chloro-2-(5,5-dimethyl-2,3,4,5-tetrahydro-1H-benzo[b]azepin-8-ylamino)-pyrimidin-4-ylamino]-bicyclo[2.2.1]hept-5-ene-2-carboxylic acid amide, TFA salt The title compound was prepared with a procedure analogous to that used to prepare example 381 to yield a yellow solid (57%). LCMS: m/z=453.22 (M+H$^+$), $^1$H NMR (400 MHz, CDCl$_3$) δ 11.53 (bs, 1H), 9.12 (d, 1H, J=7.6 Hz), 7.74 (s, 1H), 7.68 (s, 1H), 7.54 (d, 1H, J=8.6 Hz), 7.43 (d, 1H, J=8.6 Hz), 6.32 (m, 2H), 6.04 (m, 1H), 4.25 (m, 1H), 3.37 (m, 2H), 3.06 (s, 1H), 2.77 (s, 1H), 2.67 (m, 1H), 2.11 (m, 3H), 1.87 (m, 2H), 1.56 (d, 1H, J=9.1 Hz), 1.41 (d, 6H, J=2.8 Hz).

Example 1614

5-Chloro-N*2*-(5,5-dimethyl-2,3,4,5-tetrahydro-1H-benzo[b]azepin-8-yl)-N*4*-(2-methoxy-4-morpholin-4-yl-phenyl)-pyrimidine-2,4-diamine The title compound was prepared with a procedure analogous to that used to prepare example 381 to yield a yellow solid (74%) mp 231° C.; LCMS: m/z=509.25 (M+H$^+$), $^1$H NMR (400 MHz, CDCl$_3$) δ 11.81 (bs, 1H), 10.90 (bs, 3H), 8.38 (s, 1H), 8.10 (d, 1H, J=8.9 Hz), 7.82 (s, 1H), 7.82 (s, 1H), 7.63 (s, 1H), 7.41 (d, 1H, J=8.6 Hz), 7.34 (d, 1H, J=8.6 Hz), 6.85 (d, 1H, J=8.9 Hz), 6.73 (s, 1H), 3.96 (m, 7H), 3.33 (m, 4H), 3.28 (m, 2H), 2.05 (m, 2H), 1.84 (m, 2H), 1.44 (s, 6H).

Example 1615

2-[5-Chloro-2-(1-ethyl-5,5-dimethyl-2-oxo-2,3,4,5-tetrahydro-1H-benzo[b]azepin-8-ylamino)-pyrimidin-4-ylamino]-3,5-difluoro-N-methyl-benzamide, TFA salt The title compound was prepared with a procedure analogous to that used to prepare example 381 to yield an off-white solid (37%). mp 291° C.; LCMS: m/z=529.21 (M+H$^+$), $^1$H NMR (400 MHz, CDCl$_3$) δ 8.04 (m, 1H), 7.92 (m, 1H), 7.47 (s, 1H), 7.41 (m, 2H), 7.19 (m, 3H), 6.99 (m, 1H), 3.68 (m, 2H), 2.86 (m, 3H), 2.23 (m, 2H), 2.00 (m, 2H), 1.30 (s, 6H), 1.19 (m, 3H).

Example 1616

2-(5-Chloro-2-{1-[2-(1,3-dioxo-1,3-dihydro-isoindol-2-yl)-acetyl]-5,5-dimethyl-2,3,4,5-tetrahydro-1H-benzo[b]azepin-8-ylamino}-pyrimidin-4-ylamino)-3-fluoro-N-methyl-benzamide 46a) 5,5-Dimethyl-8-nitro-2,3,4,5-tetrahydro-1H-benzo[b]azepine (0.519 g, 2.36 mmol), Pyridine (0.420 mL, 5.19 mmol), 4-Dimethylaminopyridine (21 mg, 0.17 mmol) and anhydrous 1,2-Dichloroethane (8.5 mL) were combined in a round bottom flask. α-Phthalimidoacetyl Chloride (1.105 g, 4.942 mmol) was added to the mixture and it was stirred at room temperature for 16.5 hours. The reaction was concentrated under reduced pressure and purified by normal phase chromatography to yield a yellow solid, 2-[2-(5,5-Dimethyl-8-nitro-2,3,4,5-tetrahydro-benzo[b]azepin-1-yl)-2-oxo-ethyl]-isoindole-1,3-dione (55%) LCMS: m/z=408.11 (M+H$^+$); $^1$H NMR (400 MHz, CDCl$_3$) δ 8.21 (m, 2H), 7.87 (m, 2H), 7.74 (m, 3H), 4.74 (m, 1H), 4.55 (d, 1H, J=16.9), 4.55 (d, 1H, J=16.7), 2.68 (m, 1H), 2.23 (m, 1H), 1.83 (m, 1H), 1.68 (m, 1H), 1.51 (m, 6H), 1.26 (m, 1H).

46b) Using 2-[2-(5,5-Dimethyl-8-nitro-2,3,4,5-tetrahydro-benzo[b]azepin-1-yl)-2-oxo-ethyl]-isoindole-1,3-dione as starting material, a procedure similar to that used to prepare 8-Amino-5,5-dimethyl-1,3,4,5-tetrahydro-benzo[b]azepin-2-one was used to prepare 2-[2-(8-Amino-5,5-dimethyl-2,3,4,5-tetrahydro-benzo[b]azepin-1-yl)-2-oxo-ethyl]-isoindole-1,3-dione, a yellow solid (34%). LCMS: m/z=378.18 (M+H$^+$); $^1$H NMR (400 MHz, CDCl$_3$) δ 7.86 (m, 2H), 7.71 (m, 2H), 7.27 (m, 1H), 6.64 (m, 2H), 4.65 (m, 2H), 3.97 (d, 1H, J=16.7 Hz), 2.66 (m, 1H), 2.17 (m, 1H), 1.73 (m, 1H), 1.63 (m, 1H), 1.51 (m, 1H), 1.44 (s, 3H), 1.41 (s, 1H).

46c) The title compound was prepared with a procedure analogous to that used to prepare example 381 to yield an off-white solid (38%). mp 201° C.; LCMS: m/z=656.27 (M+H$^+$), $^1$H NMR (400 MHz, CDCl$_3$) δ 11.96 (s, 1H), 9.87 (s, 1H), 8.14 (br s, 1H), 7.97 (s, 1H), 7.87 (s, 1H), 7.84 (m, 2H), 7.76 (m, 2H), 7.63 (s, 1H), 7.48 (m, 2H), 7.40 (m, 1H), 7.27 (m, 2H), 4.61 (m, 1H), 3.78 (d, 1H, J=16.7 Hz), 3.66 (d, 1H, J=16.9 Hz), 3.07 (d, 3H, J=4.3 Hz), 2.74 (m, 1H), 2.21 (m, 1H), 1.80 (m, 1H), 1.71 (m, 1H), 1.56 (m, 1H), 1.44 (s, 3H), 1.36 (s, 3H).

Example 1617

2-{2-[1-(2-Amino-acetyl)-5,5-dimethyl-2,3,4,5-tetrahydro-1H-benzo[b]azepin-8-ylamino]-5-chloro-pyrimidin-4-ylamino}-3-fluoro-N-methyl-benzamide, TFA salt 2-(5-Chloro-2-{1-[2-(1,3-dioxo-1,3-dihydro-isoindol-2-yl)-acetyl]-5,5-dimethyl-2,3,4,5-tetrahydro-1H-benzo[b]azepin-8-ylamino}-pyrimidin-4-ylamino)-3-fluoro-N-methyl-benzamide, TFA salt (0.027 g, 0.000041 mol) was dissolved in DCM, washed with saturated sodium bicarbonate solution, then brine. The organic phase was dried with magnesium sulfate, filtered and concentrated. The residue was dissolved in anhydrous methylene chloride (1.0 mL). N-Methylhydrazine (20 uL, 0.0004 mol) was added and the reaction was stirred at room temperature for 3 hours. The reaction was concentrated, then purified by preparative HPLC to yield the title compound, a white solid (39%). mp 183° C.; LCMS: m/z=526.20 (M+H$^+$), $^1$H NMR (400 MHz, CDCl$_3$) δ 11.78 (s, 1H), 10.36 (s, 1H), 8.0 (m, 3H), 7.41 (m, 6H), 7.21 (m, 1H), 4.59 (m, 1H), 2.59 (s, 2H), 2.90 (m, 3H), 2.78 (m, 1H), 2.16 (m, 1H), 1.71 (m, 2H), 1.54 (m, 1H), 1.40 (s, 3H), 1.04 (s, 3H).

Example 1618

2-(5-Chloro-2-{1-[2-(1,3-dioxo-1,3-dihydro-isoindol-2-yl)-acetyl]-5,5-dimethyl-2,3,4,5-tetrahydro-1H-benzo[b]azepin-8-ylamino}-pyrimidin-4-ylamino)-3-fluoro-N-prop-2-ynyl-benzamide, TFA salt Using 2-[2-(8-Amino-5,5-dimethyl-2,3,4,5-tetrahydro-benzo[b]azepin-1-yl)-2-oxo-ethyl]-isoindole-1,3-dione and 2-(2,5-Dichloro-pyrimidin-4-ylamino)-3-fluoro-N-prop-2-ynyl-benzamide as starting materials, a procedure similar to that used to prepare example 381 was used to prepare the title compound, an off-white solid (34%). mp 164° C.; LCMS: m/z=680.21 (M+H$^+$), $^1$H NMR (400 MHz, CDCl$_3$) δ 12.06 (s, 1H), 9.75 (s, 1H), 8.55 (br s, 1H), 7.94 (s, 1H), 7.89 (m, 2H), 7.76 (m, 2H), 7.67 (s, 1H), 7.54 (d, 1H, J=7.8 Hz), 7.47 (d, 1H, J=8.8 Hz), 7.41 (m, 1H), 7.33 (m, 1H), 7.26 (m, 1H), 4.63 (m, 1H), 4.42 (m, 1H), 4.22 (m, 1H), 3.78 (d, 1H, J=16.7 Hz), 3.63 (d, 1H, J=16.7 Hz), 2.76 (m, 1H), 2.34 (m, 1H), 2.22 (m, 1H), 1.75 (m, 2H), 1.57 (m, 1H), 1.44 (s, 3H), 1.35 (s, 3H).

Example 1619

2-{2-[1-(2-Amino-acetyl)-5,5-dimethyl-2,3,4,5-tetrahydro-1H-benzo[b]azepin-8-ylamino]-5-chloro-pyrimidin-4-ylamino}-3-fluoro-N-prop-2-ynyl-benzamide, TFA salt Using 2-(5-Chloro-2-{1-[2-(1,3-dioxo-1,3-dihydro-isoindol-2-yl)-acetyl]-5,5-dimethyl-2,3,4,5-tetrahydro-1H-benzo[b]azepin-8-ylamino}-pyrimidin-4-ylamino)-3-fluoro-N-prop-2-ynyl-benzamide as starting material, a procedure similar to that used to prepare 2-{2-[1-(2-Amino-acetyl)-5,5-dimethyl-2,3,4,5-tetrahydro-1H-benzo[b]azepin-8-ylamino]-5-chloro-pyrimidin-4-ylamino}-3-fluoro-N-methyl-benzamide was used to prepare the title compound, a white solid (26%). mp 195° C.; LCMS: m/z=550.17 (M+H$^+$), $^1$H NMR (400 MHz, MeOD) δ 8.14 (s, 1H), 7.50 (m, 3H), 7.41 (m, 1H), 7.34 (d, 1H, J=8.6 Hz), 7.16 (d, 1H, J=8.6 Hz), 4.56 (m, 1H), 4.14 (d, 1H, J=17.7 Hz), 3.99 (m, 2H), 3.05 (d, 1H, J=16.7 Hz), 2.52 (m, 2H), 2.18 (m, 1H), 1.71 (m, 2H), 1.52 (m, 1H), 1.40 (s, 3H), 1.16 (s, 3H).

Example 1620

2-{5-Chloro-2-[5,5-dimethyl-1-(pyrrolidine-1-carbonyl)-2,3,4,5-tetrahydro-1H-benzo[b]azepin-8-ylamino]-pyrimidin-4-ylamino}-3-fluoro-N-methyl-benzamide, TFA salt 50a) 5,5-Dimethyl-8-nitro-2,3,4,5-tetrahydro-1H-benzo[b]azepine (0.797 g, 3.62 mmol), Pyridine (6.310 mL, 3.83 mmol) and 4-Dimethylaminopyridine (21 mg, 0.17 mmol) were dissolved in anhydrous 1,2-Dichloroethane (5.0 mL) before adding p-Nitrophenyl Chloroformate (0.541 g, 2.68 mmol). The reaction was stirred at room temperature for 41 hours and then concentrated under reduced pressure. The residue was purified by normal phase chromatography to yield an off-white solid, 5,5-Dimethyl-8-nitro-2,3,4,5-tetrahydro-benzo[b]azepine-1-carboxylic acid 4-nitro-phenyl ester (0.475 g, 46%). LCMS: m/z=386.07 (M+H$^+$). $^1$H NMR (400 MHz, CDCl$_3$) δ 8.21 (m, 4H), 7.65 (d, 1H, J=8.8 Hz), 7.42 (m, 1H), 7.23 (m, 1H), 4.53 (m, 1H), 2.87 (m, 1H), 2.32 (m, 1H), 1.69 (m, 5H), 1.34 (m, 4H).

50b) 5,5-Dimethyl-8-nitro-2,3,4,5-tetrahydro-benzo[b]azepine-1-carboxylic acid 4-nitro-phenyl ester (0.442 g, 0.00115 mol), pyrrolidine (1.090 mL, 0.013 mol) and anhydrous tetrahydrofuran (10 mL) were combined in a round bottom flask and heated to 60° C. for 23 hours. The reaction was concentrated under reduced pressure, then purified by normal phase chromatography to yield an off-white solid, (5,5-Dimethyl-8-nitro-2,3,4,5-tetrahydro-benzo[b]azepin-1-yl)-pyrrolidin-1-yl-methanone (0.364 g, 78%). LCMS: m/z=318.15 (M+H$^+$), $^1$H NMR (400 MHz, CDCl$_3$) δ 7.97 (m, 1H), 7.87 (m, 1H), 7.60 (d, 1H, J=8.8 Hz), 3.10 (br s, 4H), 1.89 (br s, 2H), 1.73 (m, 6H), 1.47 (s, 6H).

50c) Using (5,5-Dimethyl-8-nitro-2,3,4,5-tetrahydro-benzo[b]azepin-1-yl)-pyrrolidin-1-yl-methanone as starting material, a procedure similar to that used to prepare 8-Amino-5,5-dimethyl-1,3,4,5-tetrahydro-benzo[b]azepin-2-one was used to prepare (8-Amino-5,5-dimethyl-2,3,4,5-tetrahydro-benzo[b]azepin-1-yl)-pyrrolidin-1-yl-methanone, a white solid (99%). LCMS: m/z=288.14 (M+H$^+$), $^1$H NMR (400 MHz, CDCl$_3$) δ 7.15 (d, 1H, J=8.3 Hz), 6.46 (dd, 1H, J=8.3, 2.5 Hz), 6.33 (d, 1H, J=2.5 Hz), 3.55 (m, 1H), 3.10 (m, 4H), 1.61 (m, 11H), 1.34 (s, 6H).

50d) The title compound was prepared with a procedure analogous to that used to prepare example 381 by combining (8-Amino-5,5-dimethyl-2,3,4,5-tetrahydro-benzo[b]azepin-1-yl)-pyrrolidin-1-yl-methanone and 2-(2,5-Dichloro-pyrimidin-4-ylamino)-3-fluoro-N-methyl-benzamide to yield a yellow solid (33%). LCMS: m/z=566.23 (M+H$^+$), $^1$H NMR (400 MHz, CDCl$_3$) δ 11.81 (br s, 1H), 9.45 (br s, 1H), 7.92 (s, 1H), 7.70 (br s, 1H), 7.48 (d, 1H, J=7.8 Hz), 7.40 (m, 1H), 7.29 (m, 2H), 7.04 (m, 2H), 4.50 (br s, 1H), 2.91 (m, 7H), 2.31 (m, 1H), 1.56 (m, 14H).

Example 1621

8-{5-Chloro-4-[2-(3-hydroxy-pyrrolidine-1-sulfonyl)-phenylamino]-pyrimidin-2-ylamino}-5,5-dimethyl-1,3,4,5-tetrahydro-benzo[b]azepin-2-one, TFA salt {2-[3-(tert-Butyl-dimethyl-silanyloxy)-pyrrolidine-1-sulfonyl]-phenyl}-(2,5-dichloro-pyrimidin-4-yl)-amine (0.096 g, 0.00019 mol), 8-Amino-5,5-dimethyl-1,3,4,5-tetrahydro-benzo[b]azepin-2-one (0.044 g, 0.00022 mol), 10-Camphorsulfonic acid (0.006 g, 0.00003 mol) and isopropyl alcohol (3.0 mL) were combined in a microwave tube and heated in the microwave at 120° C. for 80 minutes. 6 N HCl (1.5 mL) was added and the reaction was stirred at room temperature for 3 hours, then concentrated under reduced pressure. The residue was purified on preparative HPLC to yield a brown solid, 8-{5-Chloro-4-[2-(3-hydroxy-pyrrolidine-1-sulfonyl)-phenylamino]-pyrimidin-2-ylamino}-5,5-dimethyl-1,3,4,5-tetrahydro-benzo[b]azepin-2-one, TFA salt (34%). mp 157° C., LCMS: m/z=557.15 (M+H$^+$), $^1$H NMR (400 MHz, DMSO-d$_6$) δ 9.56 (s, 1H), 9.45 (m, 2H), 8.67 (m, 1H), 8.29 (s, 1H), 7.86 (d, 1H, J=8.3 Hz), 7.65 (m, 1H), 7.29 (m, 4H), 4.18 (m, 1H), 3.26 (m, 1H), 3.05 (m, 1H), 2.67 (m, 1H), 2.33 (m, 1H), 2.18 (m, 2H), 1.97 (m, 2H), 1.80 (m, 1H), 1.67 (m, 1H), 1.32 (s, 7H).

Example 1622

2-{5-Chloro-2-[5,5-dimethyl-1-(pyrrolidine-1-carbonyl)-2,3,4,5-tetrahydro-1H-benzo[b]azepin-8-ylamino]-pyrimidin-4-ylamino}-3,5-difluoro-N-prop-2-ynyl-benzamide, TFA salt Using (8-Amino-5,5-dimethyl-2,3,4,5-tetrahydro-benzo[b]azepin-1-yl)-pyrrolidin-1-yl-methanone and 2-(2,5-Dichloro-pyrimidin-4-ylamino)-3,5-difluoro-N-prop-2-ynyl-benzamide as starting materials, a procedure similar to that used to prepare example 381 was used to prepare the title compound, a brown solid (38%). LCMS: m/z=608.24 (M+H$^+$), $^1$H NMR (400 MHz, DMSO-d$_6$) δ 9.20 (m, 1H), 8.91 (m, 1H), 8.87 (s, 1H), 8.12 (s, 1H), 7.68 (m, 1H), 7.36 (m, 1H), 7.25 (m, 1H), 7.07 (m, 2H), 3.98 (m, 2H), 3.10 (m, 1H), 2.93 (m, 4H), 2.67 (m, 1H), 2.33 (m, 1H), 1.71 (m, 2H), 1.58 (m, 6H), 1.26 (s, 6H).

Example 1623

3-[5-Chloro-2-(5,5-dimethyl-2-oxo-2,3,4,5-tetrahydro-1H-benzo[b]azepin-8-ylamino)-pyrimidin-4-ylamino]-thiophene-2-carboxylic acid prop-2-ynylamide, TFA salt Using 8-Amino-5,5-dimethyl-1,3,4,5-tetrahydro-benzo[b]azepin-2-one and 3-(2,5-Dichloro-pyrimidin-4-ylamino)-thiophene-2-carboxylic acid prop-2-ynylamide as starting materials, a procedure similar to that used to prepare example 381 was used to prepare the title compound, a brown solid (8.5%). mp 285° C., LCMS: m/z=495.14 (M+H$^+$), $^1$H NMR (400 MHz, DMSO-d$_6$) δ 11.51 (s, 1H), 9.55 (m, 1H), 9.51 (m, 1H), 8.77 (m, 1H), 8.51 (m, 1H), 8.25 (m, 1H), 7.73 (m, 1H), 7.35 (m, 2H), 7.30 (m, 1H), 4.03 (m, 2H), 3.15 (m, 1H), 2.67 (m, 1H), 2.33 (m, 1H), 2.21 (m, 2H), 2.08 (m, 1H), 1.99 (m, 2H), 1.33 (s, 6H).

Example 1624

2-[5-Chloro-2-(5,5-dimethyl-2-oxo-2,3,4,5-tetrahydro-1H-benzo[b]azepin-8-ylamino)-pyrimidin-4-ylamino]-3-fluoro-N-methyl-5-(1-methyl-1H-pyrazol-4-yl)-benzamide, TFA salt Using 8-Amino-5,5-dimethyl-1,3,4,5-tetrahydro-benzo[b]azepin-2-one and 2-(2,5-Dichloro-pyrimidin-4-ylamino)-3-fluoro-N-methyl-5-(1-methyl-1H-pyrazol-4-yl)-benzamide as starting materials, a procedure similar to that used to prepare example 381 was used to prepare the title compound, a brown solid (38%). LCMS: m/z=563.18 (M+H$^+$), $^1$H NMR (400 MHz, DMSO-d$_6$) δ 9.39 (m, 2H), 9.18 (s, 1H), 8.51 (m, 1H), 8.29 (s, 1H), 8.17 (d, 1H, J=1.5 Hz), 8.01 (s, 1H), 7.73 (d, 1H, J=11.6 Hz), 7.69 (s, 1H), 7.28 (d, 1H, J=9.1 Hz), 6.97 (m, 2H), 3.89 (s, 3H), 2.75 (d, 3H, J=3.8 Hz), 2.08 (m, 2H), 1.88 (m, 2H), 1.18 (s, 6H).

Example 1625

8-{5-Chloro-4-[2-((R)-3-dimethylamino-pyrrolidine-1-sulfonyl)-phenylamino]-pyrimidin-2-ylamino}-5,5-dimethyl-1,3,4,5-tetrahydro-benzo[b]azepin-2-one, TFA salt Using 8-Amino-5,5-dimethyl-1,3,4,5-tetrahydro-benzo[b]azepin-2-one and (2,5-Dichloro-pyrimidin-4-yl)-[2-((R)-3-dimethylamino-pyrrolidine-1-sulfonyl)-phenyl]-amine as starting materials, a procedure similar to that used to prepare example 381 was used to prepare the title compound, a brown solid (49%). LCMS: major peak: m/z=598.17 (M+14), minor peak: m/z=584.19 (M+H), $^1$H NMR (400 MHz, DMSO-d$_6$) δ 9.58 (s, 1H), 9.45 (s, 1H), 9.32 (s, 1H), 8.68 (m, 1H), 8.31 (d, 1H, J=1.3 Hz), 7.89 (d, 1H, J=8.1 Hz), 7.72 (m, 1H), 7.36 (m, 2H), 7.24 (m, 2H), 4.10 (m, 1H), 3.65 (m, 1H), 3.44 (m, 2H), 3.02 (m, 7H), 2.24 (m, 4H), 1.98 (m, 2H), 1.32 (s, 6H).

Example 1626

2-[5-Chloro-2-(1-isopropyl-5,5-dimethyl-2,3,4,5-tetrahydro-1H-benzo[b]azepin-8-ylamino)-pyrimidin-4-ylamino]-3-fluoro-N-methyl-benzamide, TFA salt 56a) Using 8-Amino-1-isopropyl-5,5-dimethyl-1,3,4,5-tetrahydro-benzo[b]azepin-2-one as starting material, a procedure similar to that used to prepare 5,5-Dimethyl-7-nitro-2,3,4,5-tetrahydro-1H-benzo[b]azepine was used to prepare 1-Isopropyl-5,5-dimethyl-2,3,4,5-tetrahydro-1H-benzo[b]azepin-8-ylamine, a yellow oil (94.9%). LCMS: m/z=233.08 (M+H$^+$), $^1$H NMR (400 MHz, CDCl$_3$) δ 7.09 (d, 1H, J=8.3 Hz), 6.33 (s, 1H), 6.22 (d, 1H, J=8.3 Hz), 3.74 (m, 1H), 3.47 (br s, 2H), 2.88 (br s, 2H), 1.70 (m, 2H), 1.58 (m, 2H), 1.31 (s, 6H), 1.22 (d, 6H, J=6.6 Hz).

56b) Using 1-Isopropyl-5,5-dimethyl-2,3,4,5-tetrahydro-1H-benzo[b]azepin-8-ylamine and 2-(2,5-Dichloro-pyrimidin-4-ylamino)-3-fluoro-N-methyl-benzamide as starting materials, a procedure similar to that used to prepare example 381 was used to prepare the title compound, a yellow solid (23%). LCMS: m/z=511.19 (M+H$^+$), $^1$H NMR (400 MHz, DMSO-d$_6$) δ 9.49 (br s, 1H), 9.24 (br s, 1H), 8.50 (m, 1H), 8.16 (s, 1H), 7.49 (m, 2H), 7.41 (m, 1H), 7.05 (d, 1H, J=8.6 Hz), 6.93 (m, 2H), 3.55 (m, 1H), 2.78 (m, 5H), 1.64 (m, 2H), 1.51 (m, 2H), 1.25 (s, 6H), 1.14 (d, 6H, J=6.3 Hz).

Example 1627

2-[5-Chloro-2-(1-isopropyl-5,5-dimethyl-2,3,4,5-tetrahydro-1H-benzo[b]azepin-8-ylamino)-pyrimidin-4-ylamino]-3-fluoro-N-prop-2-ynyl-benzamide, TFA salt Using 1-Isopropyl-5,5-dimethyl-2,3,4,5-tetrahydro-1H-benzo[b]azepin-8-ylamine and 2-(2,5-Dichloro-pyrimidin-4-ylamino)-3-fluoro-N-prop-2-ynyl-benzamide as starting materials, a procedure similar to that used to prepare example 381 was used to prepare the title compound, a yellow solid (20%). LCMS: m/z=535.21 (M+H$^+$), $^1$H NMR (400 MHz, DMSO-d$_6$) δ 9.40 (br s, 1H), 9.33 (br s, 1H), 8.92 (m, 1H), 8.17 (s, 1H), 7.48 (m, 3H), 6.97 (m, 3H), 3.55 (m, 1H), 3.10 (m, 1H), 2.80 (m, 2H), 1.64 (m, 2H), 1.91 (m, 2H), 1.25 (s, 6H), 1.14 (d, 6H, J=6.1 Hz).

Example 1628

(1S,2S,3R,4R)-3-[5-Chloro-2-(1-isopropyl-5,5-dimethyl-2,3,4,5-tetrahydro-1H-benzo[b]azepin-8-ylamino)-pyrimidin-4-ylamino]-bicyclo[2.2.1]hept-5-ene-2-carboxylic acid amide, TFA salt Using 1-Isopropyl-5,5-dimethyl-2,3,4,5-tetrahydro-1H-benzo[b]azepin-8-ylamine and (1S,2S,3R,4R)-3-(2,5-Dichloro-pyrimidin-4-ylamino)-bicyclo[2.2.1]hept-5-ene-2-carboxylic acid amide as starting materials, a procedure similar to that used to prepare example 381 was used to prepare the title compound, an off-white solid (54%). LCMS: m/z=495.27 (M+H$^+$), $^1$H NMR (400 MHz, DMSO-d$_6$) δ 8.04 (s, 1H), 7.90 (s, 1H), 7.36 (s, 1H), 7.27 (m, 1H), 7.17 (d, 1H, J=9.1 Hz), 7.02 (s, 1H), 6.37 (m, 1H), 6.19 (m, 1H), 4.66 (m, 2H), 4.04 (m, 1H), 3.68 (m, 1H), 2.86 (m, 3H), 2.33 (m, 1H), 2.03 (d, 1H, J=8.8 Hz), 1.67 (m, 2H), 1.57 (m, 2H), 1.41 (m, 1H), 1.30 (d, 6H, J=4.3 Hz), 1.20 (m, 7H).

Example 1629

5-Chloro-N*2*-(1-isopropyl-5,5-dimethyl-2,3,4,5-tetrahydro-1H-benzo[b]azepin-8-yl)-N*4*-(2-methoxy-4-morpholin-4-yl-phenyl)-pyrimidine-2,4-diamine, TFA salt Using 1-Isopropyl-5,5-dimethyl-2,3,4,5-tetrahydro-1H-benzo[b]azepin-8-ylamine and (2,5-Dichloro-pyrimidin-4-yl)-(2-methoxy-4-morpholin-4-yl-phenyl)-amine as starting materials, a procedure similar to that used to prepare example 381 was used to prepare the title compound, a yellow solid (42%). LCMS: m/z=551.26 (M+H$^+$), $^1$H NMR (400 MHz, DMSO-d$_6$) δ 9.23 (m, 1H), 8.06 (s, 1H), 7.57 (m, 1H), 7.08 (m, 1H), 6.95 (m, 2H), 6.71 (m, 1H), 6.50 (m, 1H), 3.79 (s, 3H), 3.76 (m, 4H), 3.58 (m, 1H), 3.16 (m, 4H), 2.33 (m, 1H), 1.65 (m, 2H), 1.52 (m, 2H), 1.27 (s, 6H), 1.15 (d, 6H, J=6.3 Hz).

Example 1630

2-{5-Chloro-2-[1-(2-dimethylamino-acetyl)-5,5-dimethyl-2,3,4,5-tetrahydro-1H-benzo[b]azepin-8-ylamino]-pyrimidin-4-ylamino}-3-fluoro-N-methyl-benzamide, TFA salt 60a) Using 2-Chloro-1-(5,5-dimethyl-8-nitro-2,3,4,5-tetrahydro-benzo[b]azepin-1-yl)-ethanone and 2.0 M of Dimethylamine in Tetrahydrofuran as starting materials, a procedure similar to that used to prepare 1-(5,5-Dimethyl-8-nitro-2,3,4,5-tetrahydro-benzo[b]azepin-1-yl)-2-pyrrolidin-1-yl-ethanone was used to prepare 2-Dimethylamino-1-(5,5-dimethyl-8-nitro-2,3,4,5-tetrahydro-benzo[b]azepin-1-yl)-ethanone, a brown solid. LCMS: m/z=306.12 (M+H$^+$), $^1$H NMR (400 MHz, CDCl$_3$) δ 8.14 (m, 1H), 8.07 (d, 1H, J=2.0 Hz), 7.64 (d, 1H, J=8.9 Hz), 4.81 (m, 1H), 3.24 (d, 1H, J=15.4 Hz), 2.61 (m, 1H), 2.22 (m, 2H), 1.79 (m, 1H), 1.69 (m, 1H), 1.50 (s, 3H), 1.27 (s, 3H).

60b) Using 2-Dimethylamino-1-(5,5-dimethyl-8-nitro-2,3,4,5-tetrahydro-benzo[b]azepin-1-yl)-ethanone as starting material, a procedure similar to that used to prepare 8-Amino-5,5-dimethyl-1,3,4,5-tetrahydro-benzo[b]azepin-2-one was used to prepare 1-(8-Amino-5,5-dimethyl-2,3,4,5-tetrahydro-benzo[b]azepin-1-yl)-2-dimethylamino-ethanone, a yellow solid. LCMS: m/z=276.09 (M+H$^+$), $^1$H NMR (400 MHz, CDCl$_3$) δ 7.20 (d, 1H, J=8.6 Hz), 6.60 (m, 1H), 6.41 (d, 1H, J=2.0 Hz), 4.73 (m, 1H), 3.65 (br s, 2H), 3.32 (d, 1H, J=15.9 Hz), 2.71 (d, 1H, J=15.7 Hz), 2.56 (m, 1H), 2.35 (s, 6H), 2.16 (m, 1H), 1.67 (m, 1H), 1.46 (m, 2H), 1.37 (s, 3H), 1.18 (s, 3H).

60c) Using 1-(8-Amino-5,5-dimethyl-2,3,4,5-tetrahydro-benzo[b]azepin-1-yl)-2-dimethylamino-ethanone and 2-(2,5-Dichloro-pyrimidin-4-ylamino)-3-fluoro-N-methyl-benzamide as starting materials, a procedure similar to that used to prepare example 381 was used to prepare the title compound, an off-white solid (10%). LCMS: m/z=554.14 (M+H$^+$), $^1$H NMR (400 MHz, DMSO-d$_6$) δ 9.61 (br s, 1H), 9.46 (s, 1H), 9.12 (s, 1H), 8.43 (m, 1H), 8.19 (s, 1H), 7.44 (m, 3H), 7.29 (m, 2H), 4.49 (d, 1H, J=13.1 Hz), 4.02 (d, 1H, J=16.2 Hz), 3.47 (m, 2H), 2.80 (d, 3H, J=4.3 Hz), 2.74 (d, 3H, J=4.1 Hz), 2.69 (d, 3H, J=4.1 Hz), 2.00 (m, 1H), 1.64 (m, 2H), 1.44 (m, 1H), 1.34 (s, 3H), 1.10 (s, 3H).

Example 1631

2-{5-Chloro-2-[1-(2-dimethylamino-acetyl)-5,5-dimethyl-2,3,4,5-tetrahydro-1H-benzo[b]azepin-8-ylamino]-pyrimidin-4-ylamino}-3-fluoro-N-prop-2-ynyl-benzamide, TFA salt Using 1-(8-Amino-5,5-dimethyl-2,3,4,5-tetrahydro-benzo[b]azepin-1-yl)-2-dimethylamino-ethanone and 2-(2,5-Dichloro-pyrimidin-4-ylamino)-3-fluoro-N-prop-2-ynyl-benzamide as starting materials, a procedure similar to that used to prepare example 381 was used to prepare the title compound, an off-white solid (14%). LCMS: m/z=578.17 (M+H$^+$), $^1$H NMR (400 MHz, DMSO-d$_6$) δ 9.59 (br s, 1H), 9.45 (br s, 1H), 8.92 (s, 1H), 8.85 (m, 1H), 8.18 (s, 1H), 7.46 (m, 3H), 7.28 (m, 3H), 4.47 (m, 2H), 4.02 (m, 3H), 3.47 (m, 1H), 3.12 (m, 1H), 2.81 (d, 3H, J=4.3 Hz), 2.69 (d, 3H, J=4.1 Hz), 2.03 (m, 1H), 1.64 (m, 2H), 1.43 (m, 1H), 1.34 (s, 3H), 1.10 (s, 3H).

Example 1632

2-[5-Chloro-2-(1-ethyl-5,5-dimethyl-2,3,4,5-tetrahydro-1H-benzo[b]azepin-8-ylamino)-pyrimidin-4-ylamino]-3-fluoro-N-methyl-benzamide, TFA salt 62a) Using 8-Amino-1-ethyl-5,5-dimethyl-1,3,4,5-tetrahydro-benzo[b]azepin-2-one as starting material, a procedure similar to that used to prepare 5,5-Dimethyl-7-nitro-2,3,4,5-tetrahydro-1H-benzo[b]azepine was used to prepare 1-Ethyl-5,5-dimethyl-2,3,4,5-tetrahydro-1H-benzo[b]azepin-8-ylamine, a yellow oil (70%). LCMS: m/z=219.03 (M+H$^+$); $^1$H NMR (400 MHz, CDCl$_3$) δ 7.08 (d, 1H, J=8.3 Hz), 6.31 (s, 1H), 6.26 (m, 1H), 3.49 (br s, 2H), 3.13 (m, 2H), 2.83 (m, 2H), 1.73 (m, 2H), 1.55 (m, 2H), 1.35 (s, 6H), 1.18 (m, 3H).

62b) Using 1-Ethyl-5,5-dimethyl-2,3,4,5-tetrahydro-1H-benzo[b]azepin-8-ylamine and 2-(2,5-Dichloro-pyrimidin-4-ylamino)-3-fluoro-N-methyl-benzamide as starting materials, a procedure similar to that used to prepare example 381 was used to prepare the title compound, a yellow solid (26%). LCMS: m/z=497.26 (M+H$^+$), $^1$H NMR (400 MHz, DMSO-d$_6$) δ 9.48 (s, 1H), 9.22 (s, 1H), 8.50 (m, 1H), 8.17 (s, 1H), 7.48 (m, 1H), 7.41 (m, 1H), 7.10 (m, 1H), 6.96 (m, 2H), 2.96 (m, 2H), 2.74 (m, 5H), 1.67 (m, 2H), 1.49 (m, 2H), 1.29 (s, 6H), 1.08 (m, 3H).

Example 1633

2-[5-Chloro-2-(1-ethyl-5,5-dimethyl-2,3,4,5-tetrahydro-1H-benzo[b]azepin-8-ylamino)-pyrimidin-4-ylamino]-3-fluoro-N-prop-2-ynyl-benzamide, TFA salt Using 1-Ethyl-5,5-dimethyl-2,3,4,5-tetrahydro-1H-benzo[b]azepin-8-ylamine and 2-(2,5-Dichloro-pyrimidin-4-ylamino)-3-fluoro-N-prop-2-ynyl-benzamide as starting materials, a procedure similar to that used to prepare example 381 was used to prepare the title compound, a yellow solid (29%). LCMS: m/z=521.22 (M+H$^+$), $^1$H NMR (400 MHz, DMSO-d$_6$) δ 9.29 (s, 1H), 9.20 (br s, 1H), 8.94 (m, 1H), 8.16 (s, 1H), 7.50 (m, 2H), 7.44 (m, 1H), 7.08 (m, 1H), 6.95 (m, 2H), 4.00 (m, 2H), 3.11 (s, 1H), 2.95 (m, 2H), 2.75 (m, 2H), 1.67 (m, 2H), 1.49 (m, 2H), 1.29 (s, 6H), 1.08 (m, 3H).

Example 1634

(1S,2S,3R,4R)-3-[5-Chloro-2-(1-ethyl-5,5-dimethyl-2,3,4,5-tetrahydro-1H-benzo[b]azepin-8-ylamino)-pyrimidin-4-ylamino]-bicyclo[2.2.1]hept-5-ene-2-carboxylic acid amide, TFA salt Using 1-Ethyl-5,5-dimethyl-2,3,4,5-tetrahydro-1H-benzo[b]azepin-8-ylamine and (1S,2S,3R,4R)-3-(2,5-Dichloro-pyrimidin-4-ylamino)-bicyclo[2.2.1]hept-5-ene-2-carboxylic acid amide as starting materials, a procedure similar to that used to prepare example 381 was used to prepare the title compound, a brown solid (58%). LCMS: m/z=481.20 (M+H$^+$); $^1$H NMR (400 MHz, CDCl$_3$) δ 11.41 (s, 1H), 9.06 (m, 1H), 7.69 (s, 1H), 7.34 (m, 2H), 7.27 (m, 1H), 6.87 (br s, 1H), 6.33 (m, 1H), 6.16 (m, 1H), 5.99 (s, 1H), 4.25 (m, 1H), 3.29 (m, 2H), 3.08 (m, 3H), 2.87 (s, 1H), 2.61 (d, 1H, J=8.1), 2.14 (d, 1H, J=9.4 Hz), 1.84 (m, 2H), 1.69 (m, 2H), 1.59 (d, 1H, J=9.1 Hz), 1.40 (s, 6H), 1.25 (m, 3H).

Example 1635

5-Chloro-N*2*-(1-ethyl-5,5-dimethyl-2,3,4,5-tetrahydro-1H-benzo[b]azepin-8-yl)-N*4*-(2-methoxy-4-morpholin-4-yl-phenyl)-pyrimidine-2,4-diamine, TFA salt Using 1-Ethyl-5,5-dimethyl-2,3,4,5-tetrahydro-1H-benzo[b]azepin-8-ylamine and (2,5-Dichloro-pyrimidin-4-yl)-(2-methoxy-4-morpholin-4-yl-phenyl)-amine as starting materials, a procedure similar to that used to prepare example 381 was used to prepare the title compound, a yellow solid (43%). LCMS: m/z=537.23 (M+H$^+$), $^1$H NMR (400 MHz, DMSO-d$_6$) δ 9.25 (m, 1H), 8.45 (m, 1H), 8.07 (s, 1H), 7.52 (m, 1H), 7.10 (m, 1H), 6.95 (m, 2H), 6.70 (m, 1H), 6.50 (m, 1H), 3.77 (m, 5H), 3.16 (m, 4H), 2.98 (m, 2H), 2.76 (m, 1H), 1.68 (m, 2H), 1.49 (m, 2H), 1.31 (s, 6H), 1.08 (m, 3H).

Example 1636

2-[2-(3-Acetylamino-5,5-dimethyl-2-oxo-2,3,4,5-tetrahydro-1H-benzo[b]azepin-8-ylamino)-5-chloro-pyrimidin-4-ylamino]-N-cyanomethyl-3-fluoro-Benzamide, TFA salt Using N-(8-Amino-5,5-dimethyl-2-oxo-2,3,4,5-tetrahydro-1H-benzo[b]azepin-3-yl)-acetamide and N-Cyanomethyl-2-(2,5-dichloro-pyrimidin-4-ylamino)-3-fluoro-benzamide as starting materials, a procedure similar to that used to prepare example 381 was used to prepare the title compound, an off-white solid (17%) LCMS: m/z=565.13 (M+H$^+$), $^1$H NMR (400 MHz, DMSO-d$_6$) δ 9.51 (br s, 1H), 9.38 (br s, 1H), 9.15 (m, 1H), 9.10 (s, 1H), 8.18 (s, 1H), 8.04 (d, 1H, J=8.3 Hz), 7.52 (m, 2H), 7.38 (m, 1H), 7.23 (d, 1H, J=8.1 Hz), 7.13 (s, 1H), 7.08 (d, 1H, J=8.6 Hz), 4.28 (d, 1H, J=5.3 Hz), 4.19 (m, 1H), 2.07 (m, 1H), 1.83 (m, 4H), 1.32 (s, 3H), 1.23 (s, 3H).

Example 1637

2-{5-Chloro-2-[3-(2-methoxy-acetylamino)-5,5-dimethyl-2-oxo-2,3,4,5-tetrahydro-1H-benzo[b]azepin-8-ylamino]-pyrimidin-4-ylamino}-N-cyanomethyl-3-fluoro-benzamide, TFA salt Using N-(8-Amino-5,5-dimethyl-2-oxo-2,3,4,5-tetrahydro-1H-benzo[b]azepin-3-yl)-2-methoxy-acetamide and N-Cyanomethyl-2-(2,5-dichloro-pyrimidin-4-ylamino)-3-fluoro-benzamide as starting materials, a procedure similar to that used to prepare example 381 was used to prepare the title compound, an off-white solid (23%). LCMS: m/z=595.14 (M+H$^+$), $^1$H NMR (400 MHz, DMSO-d$_6$) δ 9.70 (br s, 1H), 9.38 (br s, 1H), 9.15 (m, 1H), 9.09 (s, 1H), 8.18 (s, 1H), 7.71 (d, 1H, J=7.6 Hz), 7.50 (m, 2H), 7.36 (m, 1H), 7.25 (d, 1H, J=8.8 Hz), 7.14 (s, 1H), 7.09 (d, 1H, J=8.8 Hz), 4.28 (d, 2H, J=5.3 Hz), 4.20 (m, 1H), 3.82 (s, 2H), 3.33 (s, 3H), 2.18 (m, 1H), 1.91 (m, 1H), 1.33 (s, 3H), 1.24 (m, 3H).

Example 1638

2-{5-Chloro-2-[1-(2-dimethylamino-ethyl)-5,5-dimethyl-2,3,4,5-tetrahydro-1H-benzo[b]azepin-8-ylamino]-pyrimidin-4-ylamino}-3-fluoro-N-methyl-benzamide, TFA salt 68a) Using crude 2-Dimethylamino-1-(5,5-dimethyl-8-nitro-2,3,4,5-tetrahydro-benzo[b]azepin-1-yl)-ethanone as starting material, a procedure similar to that used to prepare 5,5-Dimethyl-8-nitro-1-(2-pyrrolidin-1-yl-ethyl)-2,3,4,5-tetrahydro-1H-benzo[b]azepine was used to prepare crude [2-(5,5-Dimethyl-8-nitro-2,3,4,5-tetrahydro-benzo[b]azepin-1-yl)-ethyl]-dimethyl-amine, a brown oil. LCMS: m/z=292.10 (M+H$^+$). $^1$H NMR (400 MHz, CDCl$_3$) δ 7.81 (d, 1H, J=1.8 Hz), 7.23 (dd, 1H, J=8.6, 1.5 Hz), 7.42 (d, 1H, J=8.9 Hz), 3.70 (m, 2H), 3.59 (m, 2H), 3.36 (m, 1H), 2.96 (m, 1H), 2.55 (m, 2H), 2.29 (m, 6H), 1.67 (m, 2H), 1.40 (s, 6H).

68b) Using crude [2-(5,5-Dimethyl-8-nitro-2,3,4,5-tetrahydro-benzo[b]azepin-1-yl)-ethyl]-dimethyl-amine as starting material, a procedure similar to that used to prepare 8-Amino-5,5-dimethyl-1,3,4,5-tetrahydro-benzo[b]azepin-2-one was used to prepare crude 1-(2-Dimethylamino-ethyl)-5,5-dimethyl-2,3,4,5-tetrahydro-1H-benzo[b]azepin-8-ylamine, a brown oil. LCMS: m/z=262.15 (M+H$^+$).

68c) Using crude 1-(2-Dimethylamino-ethyl)-5,5-dimethyl-2,3,4,5-tetrahydro-1H-benzo[b]azepin-8-ylamine and 2-(2,5-Dichloro-pyrimidin-4-ylamino)-3-fluoro-N-methyl-benzamide as starting materials, a procedure similar to that used to prepare example 381 was used to prepare the title compound, a yellow solid (14%). LCMS: m/z=540.14 (M+H$^+$), $^1$H NMR (400 MHz, DMSO-d$_6$) δ 9.39 (br s, 1H), 9.32 (s, 1H), 9.04 (br s, 1H), 8.53 (br s, 1H), 8.16 (m, 1H), 7.44 (m, 2H), 7.16 (d, 1H, J=9.1 Hz), 7.04 (br s, 1H), 6.97 (m, 1H), 3.31 (m, 2H), 3.22 (m, 2H), 2.82 (m, 8H), 2.74 (m, 3H), 1.70 (m, 2H), 1.51 (m, 2H), 1.28 (s, 6H).

Example 1639

2-{5-Chloro-2-[1-(2-dimethylamino-ethyl)-5,5-dimethyl-2,3,4,5-tetrahydro-1H-benzo[b]azepin-8-ylamino]-pyrimidin-4-ylamino}-3-fluoro-N-prop-2-ynyl-benzamide, TFA salt Using crude 1-(2-Dimethylamino-ethyl)-5,5-dimethyl-2,3,4,5-tetrahydro-1H-benzo[b]azepin-8-ylamine and 2-(2,5-Dichloro-pyrimidin-4-ylamino)-3-fluoro-N-prop-2-ynyl-benzamide as starting materials, a procedure similar to that used to prepare example 381 was used to prepare the title compound, a yellow solid (9.8%). LCMS: m/z=564.19 (M+H$^+$), $^1$H NMR (400 MHz, DMSO-d$_6$) δ 9.51 (br s, 1H), 9.16 (br s, 1H), 9.08 (br s, 1H), 8.96 (m, 1H), 8.16 (s, 1H), 7.49 (m, 3H), 7.13 (dd, 1H, J=8.6, 1.8 Hz), 7.03 (br s, 1H), 6.96 (d, 1H, J=8.8 Hz), 4.01 (m, 2H), 3.30 (m, 2H), 3.21 (m, 2H), 3.12 (m, 1H), 2.82 (m, 8H), 1.70 (m, 2H), 1.50 (m, 2H), 1.28 (s, 6H).

Example 1640

(1S,2S,3R,4R)-3-{5-Chloro-2-[1-(2-dimethylamino-ethyl)-5,5-dimethyl-2,3,4,5-tetrahydro-1H-benzo[b]azepin-8-ylamino]-pyrimidin-4-ylamino}-bicyclo[2.2.1]hept-5-ene-2-carboxylic acid amide, TFA salt Using crude 1-(2-Dimethylamino-ethyl)-5,5-dimethyl-2,3,4,5-tetrahydro-1H-benzo[b]azepin-8-ylamine and (1S,2S,3R,4R)-3-(2,5-Dichloro-pyrimidin-4-ylamino)-bicyclo[2.2.1]hept-5-ene-2-carboxylic acid amide as starting materials, a procedure similar to that used to prepare example 381 was used to prepare the title compound, a beige solid (28%). LCMS: m/z=524.23 (M+H$^+$), $^1$H NMR (400 MHz, DMSO-d$_6$) δ 9.56 (br s, 1H), 9.41 (br s, 1H), 8.34 (br s, 1H), 8.03 (s, 1H), 7.85 (s, 1H), 7.52 (d, 1H, J=7.3 Hz), 7.33 (s, 1H), 7.18 (d, 1H, J=8.8 Hz), 7.09 (s, 1H), 6.38 (m, 1H), 6.25 (m, 1H), 4.07 (m, 1H), 3.42 (m, 2H), 3.27 (m, 2H), 2.87 (m, 10H), 2.52 (m, 1H), 2.07 (d, 1H, J=8.8 Hz), 1.73 (m, 2H), 1.55 (m, 2H), 1.42 (d, 1H, J=8.8 Hz), 1.33 (s, 6H).

Example 1641

5-Chloro-N*2*-[1-(2-dimethylamino-ethyl)-5,5-dimethyl-2,3,4,5-tetrahydro-1H-benzo[b]azepin-8-yl]-N*4*-(2-methoxy-4-morpholin-4-yl-phenyl)-pyrimidine-2,4-diamine, TFA salt Using crude 1-(2-Dimethylamino-ethyl)-5,5-dimethyl-2,3,4,5-tetrahydro-1H-benzo[b]azepin-8-ylamine and (2,5-Dichloro-pyrimidin-4-yl)-(2-methoxy-4-morpholin-4-yl-phenyl)-amine as starting materials, a procedure similar to that used to prepare example 381 was used to prepare the title compound, a yellow solid (36%). LCMS: m/z=580.22 (M+H$^+$), $^1$H NMR (400 MHz, DMSO-d$_6$) δ 9.47 (br s, 1H), 9.25 (br s, 1H), 8.38 (br s, 1H), 8.09 (s, 1H), 7.53 (m, 1H), 7.18 (m, 1H), 7.01 (m, 2H), 6.71 (d, 1H, J=2.3 Hz), 6.52 (dd, 1H, J=8.6, 2.3 Hz), 3.77 (m, 7H), 3.32 (m, 2H), 3.22 (m, 2H), 3.17 (m, 4H), 2.83 (m, 7H), 2.50 (m, 1H), 1.71 (m, 2H), 1.52 (m, 2H), 1.30 (s, 6H).

Example 1642

2-{5-Chloro-2-[1-ethyl-5,5-dimethyl-2-oxo-3-(2,2,2-trifluoro-acetylamino)-2,3,4,5-tetrahydro-1H-benzo[b]azepin-8-ylamino]-pyrimidin-4-ylamino}-3-fluoro-N-methyl-benzamide, TFA salt 72a) 3-Amino-1-ethyl-5,5-dimethyl-8-nitro-1,3,4,5-tetrahydro-1-benzazepin-2-one (0.147 g, 0.000530 mol), trifluoroacetic anhydride (0.230 mL, 0.001628 mol), pyridine (0.260 mL, 0.00322 mol) and methylene chloride (6.6 mL) were combined in a round bottom flask and stirred at room temperature for 5.5 hours. The reaction mixture was concentrated under reduced pressure. The residue was dissolved in DCM and washed with 10% citric acid. The organic layer was dried over magnesium sulfate, filtered, and concentrated under reduced pressure to yield a light yellow solid, N-(1-Ethyl-5,5-dimethyl-8-nitro-2-oxo-2,3,4,5-tetrahydro-1H-benzo[b]azepin-3-yl)-2,2,2-trifluoro-acetamide (99%). LCMS: m/z=374.02 (M+H$^+$), $^1$H NMR (400 MHz, CDCl$_3$) δ 8.13 (m, 2H), 7.66 (d, 1H, J=8.3 Hz), 7.50 (m, 1H), 4.36 (m, 1H), 4.08 (m, 1H), 3.84 (m, 1H), 2.66 (m, 1H), 1.91 (m, 1H), 1.51 (s, 3H), 1.42 (m, 3H), 1.34 (s, 3H).

72b) Using N-(1-Ethyl-5,5-dimethyl-8-nitro-2-oxo-2,3,4,5-tetrahydro-1H-benzo[b]azepin-3-yl)-2,2,2-trifluoro-acetamide as starting material, a procedure similar to that used to prepare 8-Amino-5,5-dimethyl-1,3,4,5-tetrahydro-benzo[b]azepin-2-one was used to prepare N-(8-Amino-1-ethyl-5,5-dimethyl-2-oxo-2,3,4,5-tetrahydro-1H-benzo[b]azepin-3-yl)-2,2,2-trifluoro-acetamide, a light yellow solid (99%). LCMS: m/z=344.08 (M+H$^+$), $^1$H NMR (400 MHz, DMSO-d$_6$) δ 7.04 (d, 1H, J=8.6 Hz), 6.62 (d, 1H, J=2.3 Hz), 6.46 (m, 1H), 5.20 (s, 2H), 4.23 (m, 1H), 3.80 (m, 1H), 3.57 (m, 1H), 2.30 (s, 2H), 2.10 (m, 1H), 1.97 (m, 1H), 1.30 (s, 3H), 1.23 (m, 3H), 1.14 (s, 3H).

72c) Using N-(8-Amino-1-ethyl-5,5-dimethyl-2-oxo-2,3,4,5-tetrahydro-1H-benzo[b]azepin-3-yl)-2,2,2-trifluoro-acetamide and 2-(2,5-Dichloro-pyrimidin-4-ylamino)-3-fluoro-N-methyl-benzamide as starting materials, a procedure similar to that used to prepare example 381 was used to prepare the title compound, an off-white solid (21%). mp 158° C.; LCMS: m/z=622.16 (M+H$^+$), $^1$H NMR (400 MHz, CDCl$_3$) δ 12.10 (s, 1H), 9.86 (s, 1H), 7.91 (s, 1H), 7.63 (d, 1H, J=7.3 Hz), 7.35 (s, 1H), 7.24 (m, 5H), 6.55 (m, 1H), 4.03 (m, 2H), 3.79 (m, 1H), 2.96 (d, 3H, J=4.8 Hz), 2.38 (m, 1H), 1.81 (m, 1H), 1.40 (s, 3H), 1.29 (s, 3H), 1.24 (m, 3H).

Example 1643

2-[2-(3-Acetylamino-1-ethyl-5,5-dimethyl-2-oxo-2,3,4,5-tetrahydro-1H-benzo[b]azepin-8-ylamino)-5-chloro-pyrimidin-4-ylamino]-3-fluoro-N-methyl-benzamide, TFA salt 73a) Using 3-Amino-1-ethyl-5,5-dimethyl-8-nitro-1,3,4,5-tetrahydro-1-benzazepin-2-one and acetic anhydride as starting materials, a procedure similar to that used to prepare N-(1-Ethyl-5,5-dimethyl-8-nitro-2-oxo-2,3,4,5-tetrahydro-1H-benzo[b]azepin-3-yl)-2,2,2-trifluoro-acetamide was used to prepare N-(1-Ethyl-5,5-dimethyl-8-nitro-2-oxo-2,3,4,5-tetrahydro-1H-benzo[b]azepin-3-yl)-acetamide, a light yellow solid (95%). LCMS: m/z=320.03 (M+H$^+$); $^1$H NMR (400 MHz, CDCl$_3$) δ 8.09 (m, 2H), 7.62 (m, 1H), 6.53 (d, 1H, J=6.6 Hz), 4.39 (m, 1H), 4.06 (m, 1H), 3.78 (m, 1H), 2.58 (m, 1H), 1.97 (s, 3H), 1.82 (m, 1H), 1.48 (s, 3H), 1.40 (m, 3H), 1.30 (s, 3H).

73b) Using N-(1-Ethyl-5,5-dimethyl-8-nitro-2-oxo-2,3,4,5-tetrahydro-1H-benzo[b]azepin-3-yl)-acetamide as starting material, a procedure similar to that used to prepare 8-Amino-5,5-dimethyl-1,3,4,5-tetrahydro-benzo[b]azepin-2-one was used to prepare N-(8-Amino-1-ethyl-5,5-dimethyl-2-oxo-2,3,4,5-tetrahydro-1H-benzo[b]azepin-3-yl)-acetamide, a white solid (97%). LCMS: m/z=290.03 (M+H$^+$); $^1$H NMR (400 MHz, DMSO-d$_6$) δ 8.01 (d, 1H, J=8.3 Hz), 7.01 (d, 1H, J=8.6 Hz), 6.59 (d, 1H, J=2.3 Hz), 6.44 (m, 1H), 5.16 (s, 2H), 4.23 (m, 1H), 3.81 (m, 1H), 3.46 (m, 1H), 1.93 (m, 1H), 1.77 (m, 4H), 1.25 (m, 6H), 1.11 (s, 3H).

73c) Using N-(8-Amino-1-ethyl-5,5-dimethyl-2-oxo-2,3,4,5-tetrahydro-1H-benzo[b]azepin-3-yl)-acetamide and 2-(2,5-Dichloro-pyrimidin-4-ylamino)-3-fluoro-N-methyl-benzamide as starting materials, a procedure similar to that used to prepare example 381 was used to prepare the title compound, an off-white solid (54%). LCMS: m/z=568.19 (M+H$^+$); $^1$H NMR (400 MHz, CDCl$_3$) δ 12.00 (br s, 1H), 9.85 (br s, 1H), 7.90 (s, 1H), 7.32 (d, 1H, J=1.8 Hz), 7.20 (m, 6H), 6.90 (d, 1H, J=7.6 Hz), 4.02 (m, 2H), 3.72 (m, 1H), 2.89 (d, 3H, J=4.6 Hz), 2.30 (m, 1H), 2.09 (s, 3H), 1.71 (m, 1H), 1.35 (s, 3H), 1.24 (s, 3H), 1.20 (m, 3H).

Example 1644

2-{5-Chloro-2-[1-ethyl-3-(2-methoxy-acetylamino)-5,5-dimethyl-2-oxo-2,3,4,5-tetrahydro-1H-benzo[b]azepin-8-ylamino]-pyrimidin-4-ylamino}-3-fluoro-N-methyl-benzamide, TFA salt 74a) Using 3-Amino-1-ethyl-5,5-dimethyl-8-nitro-1,3,4,5-tetrahydro-1-benzazepin-2-one and methoxyacetyl chloride as starting materials, a procedure similar to that used to prepare N-(1-Ethyl-5,5-dimethyl-8-nitro-2-oxo-2,3,4,5-tetrahydro-1H-benzo[b]azepin-3-yl)-2,2,2-trifluoro-acetamide was used to prepare N-(1-Ethyl-5,5-dimethyl-8-nitro-2-oxo-2,3,4,5-tetrahydro-1H-benzo[b]azepin-3-yl)-2-methoxy-acetamide, a light yellow solid, (79%). LCMS: m/z=350.09 (M+H$^+$); $^1$H NMR (400 MHz, CDCl$_3$) δ 8.10 (m, 2H), 7.62 (m, 1H), 7.48 (d, 1H, J=6.8 Hz), 4.45 (m, 1H), 4.05 (m, 1H), 3.82 (m, 3H), 3.43 (s, 3H), 2.54 (m, 1H), 1.89 (m, 1H), 1.48 (s, 3H), 1.41 (m, 3H), 1.32 (s, 3H).

74b) Using N-(1-Ethyl-5,5-dimethyl-8-nitro-2-oxo-2,3,4,5-tetrahydro-1H-benzo[b]azepin-3-yl)-2-methoxy-acetamide as starting material, a procedure similar to that used to prepare 8-Amino-5,5-dimethyl-1,3,4,5-tetrahydro-benzo[b]azepin-2-one was used to prepare N-(8-Amino-1-ethyl-5,5-dimethyl-2-oxo-2,3,4,5-tetrahydro-1H-benzo[b]azepin-3-yl)-2-methoxy-acetamide, a yellow solid (99%). LCMS: m/z=320.09 (M+H$^+$); $^1$H NMR (400 MHz, CDCl$_3$/MeOD) δ 7.59 (d, 1H, J=7.1 Hz), 7.14 (m, 1H), 6.65 (d, 1H, J=2.3 Hz), 6.61 (m, 1H), 4.45 (m, 3H), 3.94 (m, 1H), 3.85 (m, 2H), 3.68 (m, 1H), 3.44 (s, 3H), 2.37 (m, 1H), 1.80 (m, 1H), 1.36 (m, 6H), 1.23 (s, 3H).

74c) Using N-(8-Amino-1-ethyl-5,5-dimethyl-2-oxo-2,3,4,5-tetrahydro-1H-benzo[b]azepin-3-yl)-2-methoxy-acetamide and 2-(2,5-Dichloro-pyrimidin-4-ylamino)-3-fluoro-N-methyl-benzamide as starting materials, a procedure similar to that used to prepare example 381 was used to prepare the title compound, an off-white solid (21%). LCMS: m/z=598.21 (M+H$^+$); $^1$H NMR (400 MHz, CDCl$_3$) δ 12.02 (br s, 1H), 9.77 (br s, 1H), 7.90 (s, 1H), 7.69 (d, 1H, J=7.8 Hz), 7.34 (d, 1H, J=1.8 Hz), 7.22 (m, 5H), 7.03 (m, 1H), 4.04 (m, 2H), 3.95 (s, 2H), 3.71 (m, 1H), 3.53 (s, 3H), 2.91 (d, 1H, J=4.6 Hz), 2.30 (m, 1H), 1.78 (m, 1H), 1.37 (s, 3H), 1.27 (s, 3H), 1.20 (m, 3H).

Example 1651

N-{(1R,2R)-2-[2-(4-Benzyl-7-methoxy-2-oxo-2,3,4,5-tetrahydro-1H-benzo[e][1,4]diazepin-8-ylamino)-5-chloro-pyrimidin-4-ylamino]-cyclohexyl}-methanesulfonamide 1651a) To a solution of ethyl N-benzyl-glycinate (34.1 g, 176 mmol) and m-anisaldehyde (11.0 g, 80.8 mmol) in methanol (500 mL) was added acetic acid (12.1 mL, 202 mmol) followed by sodium cyanoborohydride (3.4 g, 54 mmol). The mixture was stirred at ambient temperature for 2.5 hours whereupon LCMS analysis showed completion of the reaction. The solvent was removed on a rotary evaporator and the residue was dissolved in ethyl acetate, washed with saturated sodium bicarbonate to neutrality. The organic phase was washed with brine, dried over anhydrous magnesium sulfate, filtered and concentrated. Flash chromatography over silica gel (CH$_2$Cl$_2$) gave 21.5 g (85% of [benzyl-(3-methoxy-benzyl)-amino]-acetic acid ethyl ester as a colorless oil. $^1$H NMR (400 MHz, DMSO-d$_6$) δ 7.35 (m, 4H), 7.25 (m, 2H), 6.93 (m, 2H), 6.82 (d, J=9 Hz, 1H), 4.10 (q, J=7 Hz, 2H), 3.74 (s, 3H), 3.70 (s, 2H), 3.32 (s, 2H), 3.24 (s, 2H), 1.18 (t, J=7 Hz, 3H); MS (m/e) 314 (M+1).

1651b) [Benzyl-(3-methoxy-benzyl)-amino]-acetic acid ethyl ester (3.0 g, 9.6 mmol) in ethanol (100 mL) was treated with 4N NaOH (20 mL) and the mixture was stirred at ambient temperature for two hours whereupon HPLC analysis showed completion of the reaction. The ethanol was removed on the rotary evaporator, water (~20 mL) was added to dissolve solids, the pH was adjusted to 4 (6N HCl) with stirring and the precipitate was collected by filtration, washed with water and dried to constant weight in vacuo to give 2.47 g (90%) of [benzyl-(3-methoxy-benzyl)-amino]-acetic acid as a white solid; $^1$H NMR (400 MHz, DMSO-d$_6$) δ 12.30 (br s, 1H), 7.35 (m, 4H), 7.25 (m, 2H), 6.93 (m, 2H), 6.82 (d, J=9 Hz, 1H), 3.74 (s, 3H), 3.72 (s, 2H), 3.30 (br s, 2H, 3.17 (s, 2H); MS (m/e) 286 (M+1); mp 177-179° C.

1651c) To a round-bottomed flask containing methanesulfonic acid (75 mL) was added [benzyl-(3-methoxy-benzyl)-amino]-acetic acid (11.0 g, 38.5 mmol) with stirring. The mixture was heated to 100° C. for five hours whereupon LCMS showed completion of the reaction. The mixture was cooled to ambient temperature, water (300 mL) was added and the mixture was cooled in an ice-water bath and adjusted to pH 9 (10N NaOH), keeping the internal temperature below 30° C. The precipitate was collected by vacuum filtration, washed with water to neutrality, and dried to constant weight in vacuo to afford 2-benzyl-7-methoxy-2,3-dihydro-1H-isoquinolin-4-one (7.7 g, 75%) as a tan solid. $^1$H NMR (400 MHz, DMSO-d$_6$) δ 7.83 (d, J=8 Hz, 1H), 7.34 (m, 5H), 6.95 (d, J=8 Hz, 1H), 6.90 (s, 1H), 3.82 (s, 3H), 3.76 (s, 2H), 3.71 (s, 2H), 3.27 (s, 2H); (m/e) 268 (M+1); mp 135° C. (dec.).

1651d) To a solution of 2-benzyl-7-methoxy-2,3-dihydro-1H-isoquinolin-4-one (7.0 g, 26.2 mmol) in methanesulfonic acid (50 mL) was added sodium azide (3.4 g, 52.4 mmol) portionwise with stirring (Caution: mild exotherm, gas evolution). The mixture was heated to 65° C. for two hours before being cooled to ambient temperature. Water (100 mL) was added, the mixture was cooled in an ice-water bath, and the pH was adjusted to 7-8 (10N NaOH). The gummy precipitate was extracted (DCM), the organic phase was washed with brine, dried over magnesium sulfate, filtered and concentrated. Further purification by flash chromatography over silica gel (DCM/MeOH) gave 4-benzyl-7-methoxy-1,3,4,5-tetrahydro-benzo[e][1,4]diazepin-2-one (5.4 g, 73%) as a tan solid; $^1$H NMR (400 MHz, DMSO-d$_6$) δ 9.80 (s, 1H), 7.33 (m, 5H), 6.97 (d, J=8 Hz, 1H), 6.87 (d, J=8 Hz, 1H), 6.82 (s, 1H), 3.73 (s, 3H), 3.67 (s, 4H), 3.09 (s, 2H); MS (m/e) 283 (M+1); mp 134° C.

1651e) To a solution of 4-benzyl-7-methoxy-1,3,4,5-tetrahydro-benzo[e][1,4]diazepin-2-one (2.5 g, 8.85 mmol) in methanesulfonic acid (40 mL) at ambient temperature was added dropwise a solution of sodium nitrate (0.83 g, 9.74 mmol) in methanesulfonic acid over 30 minutes. After being stirred further for one hour LCMS indicated completion of the reaction. Water (50 mL) was added, the mixture was cooled in an ice-water bath and the pH was adjusted to about 9. The mixture was extracted with DCM, the organic phase was washed with brine, dried over magnesium sulfate, filtered and concentrated. Flash chromatography over silica gel (EtOAc-hexanes) gave the two isomeric nitro analogs:

Isomer 1 (4-benzyl-7-methoxy-6-nitro-1,3,4,5-tetrahydro-benzo[e][1,4]diazepin-2-one; 0.95 g, 33%): $^1$H NMR (400 MHz, DMSO-d$_6$) δ 10.13 (s, 1H), 7.30 (m, 7H), 3.87 (s, 3H), 3.65 (s, 2H), 3.60 (s, 2H), 3.17 (s, 2H); MS (m/e) 328 (M+1); mp 173° C. (dec.);

Isomer 2 (4-benzyl-7-methoxy-8-nitro-1,3,4,5-tetrahydro-benzo[e][1,4]diazepin-2-one; 0.64 g, 22%): $^1$H NMR (400 MHz, DMSO-d$_6$) δ 10.10 (s, 1H), 7.62 (s, 1H), 7.32 (m, 5H), 7.24 (s, 1H), 3.89 (s, 3H), 3.85 (s, 2H), 3.71 (s, 2H), 3.29 (s, 2H); MS (m/e) 328 (M+1); mp 165° C.

1651f) A solution of 4-benzyl-7-methoxy-8-nitro-1,3,4,5-tetrahydro-benzo[e][1,4]diazepin-2-one (125 mg, 0.38 mmol) in methanol (25 mL) was treated with Ra—Ni (~100 mg; 2800 grade) and shaken on a Paar apparatus under 40 psi H$_2$. After one hour LCMS showed completion of the reaction. The mixture was filtered and concentrated to constant weight to afford 8-amino-4-benzyl-7-methoxy-1,3,4,5-tetrahydro-benzo[e][1,4]diazepin-2-one (110 mg, 97%) as a mustard yellow solid; $^1$H NMR (400 MHz, DMSO-d$_6$) δ 9.61 (s, 1H), 7.34 (m, 5H), 6.66 (s, 1H), 6.33 (s, 1H), 4.84 (s, 2H), 3.74 (s, 3H), 3.65 (s, 2H), 3.49 (s, 2H), 2.98 (s, 2H); MS (m/e) 298 (M+1); mp 135° C. (dec.).

1651g) To a solution of 8-amino-4-benzyl-7-methoxy-1,3,4,5-tetrahydro-benzo[e][1,4]diazepin-2-one (55 mg, 0.19 mmol) and N-[(1R,2R)-2-(2,5-dichloro-pyrimidin-4-ylamino)-cyclohexyl]-methanesulfonamide (63 mg, 0.19 mmol) in 2-methoxyethanol (2 mL) was added 4N HCl-dioxane (0.20 mL). The mixture was heated to reflux for two hours whereupon LCMS showed complete consumption of the aniline. After being cooled to room temperature, triethylamine was added to pH 9 and the crude product was purified by preparative tlc (5% MeOH-DCM) to afford N-{(1R,2R)-2-[2-(4-benzyl-7-methoxy-2-oxo-2,3,4,5-tetrahydro-1H-benzo[e][1,4]diazepin-8-ylamino)-5-chloro-pyrimidin-4-ylamino]-cyclohexyl}-methanesulfonamide as a mustard yellow solid; $^1$H NMR (400 MHz, DMSO-d$_6$) δ 9.68 (s, 1H), 7.96 (s, 2H), 7.73 (s, 1H), 7.35 (m, 5H), 7.05 (d, J=7 Hz, 1H), 6.93 (s, 1H), 6.85 (d, J=8.5 Hz, 1H), 4.55 (m, 1H), 3.86 (s, 3H), 3.70 (s, 2H), 3.64 (s, 2H), 3.06 (s, 2H), 2.88 (s, 3H), 1.97 (m, 2H), 1.63 (m, 2H), 1.38 (m, 2H), 1.23 (m, 2H); MS (m/e) 601 (M+1); mp 214° C. (dec.).

Example 1652

3-[2-(4-Benzyl-7-methoxy-2-oxo-2,3,4,5-tetrahydro-1H-benzo[e][1,4]diaz-epin-8-ylamino)-5-chloro-pyrimidin-4-ylamino]-bicyclo[2.2.1]hept-5-ene-2-carboxylic acid amide.

1652a) This compound was prepared analogously according to example 1651g. From 8-amino-4-benzyl-7-methoxy-1,3,4,5-tetrahydro-benzo[e][1,4]diazepin-2-one (45 mg, 0.15 mmol) and 3-(2,5-dichloro-pyrimidin-4-ylamino)-bicyclo[2.2.1]hept-5-ene-2-carboxylic acid amide (43 mg, 0.15 mmol) was obtained 13 mg (16%) of the title compound as a mustard yellow solid; $^1$H NMR (400 MHz, DMSO-d$_6$) δ 9.72 (s, 1H), 7.99 (m, 2H), 7.80 (s, 1H), 7.70 (s, 1H), 7.35 (m, 5H), 6.96 (s, 1H), 6.27 (m, 1H), 6.20 (m, 1H), 4.43 (m, 1H), 3.86 (s, 3H), 3.70 (s, 2H), 3.62 (s, 2H), 3.40 (s, 2H), 3.07 (s, 2H), 2.69 (s, 1H), 1.38 (m, 2H); MS (m/e) 561 (M+1); mp 160° C. (dec.).

Example 1653

2-[2-(4-Benzyl-7-methoxy-2-oxo-2,3,4,5-tetrahydro-1H-benzo[e][1,4]diazepin-8-ylamino)-5-chloro-pyrimidin-4-ylamino]-N-ethyl-benzamide 1653a) This compound was prepared analogously according to example 1651g. From 8-amino-4-benzyl-7-methoxy-1,3,4,5-tetrahydro-benzo[e][1,4]diazepin-2-one (75 mg, 0.25 mmol) and 2-(2,5-dichloro-pyrimidin-4-ylamino)-N-ethyl-benzamide (78 mg, 0.25 mmol) was obtained 21 mg (15%) of the title compound as a tan foam; $^1$H NMR (400 MHz, CDCl$_3$) δ 10.81 (s, 1H), 8.78 (d, J=8 Hz, 1H), 8.15 (d, J=9 Hz, 1H), 7.62 (s, 1H), 7.52 (m, 2H), 7.37 (m, 8H), 6.69 (s, 1H), 6.25 (m, 1H), 3.90 (s, 3H), 3.81 (2s, 4H), 3.72 (s, 2H), 3.48 (q, J=7 Hz, 2H), 1.28 (t, J=7 Hz, 3H); MS (m/e) 573 (M+1).

Example 1654

N-{(1R,2R)-2-[2-(4-Benzyl-7-methoxy-2-oxo-2,3,4,5-tetrahydro-1H-benzo[e][1,4]diazepin-6-ylamino)-5-chloro-pyrimidin-4-ylamino]-cyclohexyl}-methanesulfonamide 1654a) A solution of 4-benzyl-7-methoxy-6-nitro-1,3,4,5-tetrahydro-benzo[e][1,4]diazepin-2-one (860 mg, 2.6 mmol) in methanol (100 mL) was treated with Ra—Ni (~200 mg; 2800 grade) and shaken on a Paar apparatus under 40 psi H$_2$. After one hour LCMS showed completion of the reaction. The mixture was filtered and concentrated to constant weight to afford 6-amino-4-benzyl-7-methoxy-1,3,4,5-tetrahydro-benzo[e][1,4]diazepin-2-one (764 mg, 98%) as a tan solid; $^1$H NMR (400 MHz, DMSO-d$_6$) δ 9.62 (s, 1H), 7.34 (m, 5H), 6.75 (d, J=8 Hz, 1H), 6.27 (d, J=8 Hz, 1H), 4.74 (s, 2H), 3.77 (s, 3H), 3.72 (s, 2H), 3.69 (s, 2H), 2.85 (s, 2H); MS (m/e) 298 (M+1); mp 153° C. (dec.).

1654b) To a solution of 6-amino-4-benzyl-7-methoxy-1,3,4,5-tetrahydro-benzo[e][1,4]diazepin-2-one (75 mg, 0.25 mmol) and N-[(1R,2R)-2-(2,5-dichloro-pyrimidin-4-ylamino)-cyclohexyl]-methanesulfonamide (85 mg, 0.25 mmol) in 2-methoxyethanol (2 mL) was added 4N HCl-dioxane (0.20 mL). The mixture was heated to 90° C. for two hours whereupon LCMS showed complete consumption of the aniline. After being cooled to room temperature, triethylamine was added to pH 9 and the crude product was purified by preparative tlc (7% MeOH-DCM) to afford N-{(1R,2R)-2-[2-(4-benzyl-7-methoxy-2-oxo-2,3,4,5-tetrahydro-1H-benzo[e][1,4]diazepin-6-ylamino)-5-chloro-pyrimidin-4-ylamino]-cyclohexyl}-methanesulfonamide as a light brown foam; $^1$H NMR (400 MHz, DMSO-d$_6$) δ 9.00 (s, 1H), 8.02 (s, 2H), 7.35 (m, 5H), 7.10 (d, J=8 Hz, 1H), 7.03 (d, J=8 Hz, 1H), 6.78 (m, 1H), 4.65 (m, 1H), 4.30 (m, 1H), 3.70 (s, 3H), 3.65 (s, 2H), 3.60 (s, 2H), 3.26 (s, 2H), 2.89 (s, 3H), 1.97 (m, 2H), 1.68 (m, 2H), 1.38 (m, 2H), 1.25 (m, 2H); MS (m/e) 601 (M+1).

Example 1655

N-{(1R,2R)-2-[5-Chloro-2-(7-methoxy-2-oxo-2,3,4,5-tetrahydro-1H-benzo[e][1,4]diazepin-8-ylamino)-pyrimidin-4-ylamino]-cyclohexyl}-methanesulfonamide 1655a) To a solution of (4-benzyl-7-methoxy-8-nitro-1,3,4,5-tetrahydro-benzo[e][1,4]diazepin-2-one (900 mg, 3.0 mmol) in 1,2-dichloroethane (150 mL) was added benzyl chloroformate (900 mg, 3.0 mmol). The mixture was warmed to reflux for four hours whereupon LCMS indicated completion of reaction. The mixture was cooled to ambient temperature, washed with brine, dried over magnesium sulfate, filtered and concentrated. Flash chromatography over silica gel (EtOAc-hexanes) gave 7-methoxy-8-nitro-2-oxo-1,2,3,5-tetrahydro-benzo[e][1,4]diazepine-4-carboxylic acid benzyl ester (390 mg, 40%) as a yellow solid; $^1$H NMR (400 MHz, DMSO-d$_6$) δ 10.19 (s, 1H), 7.67 (s, 1H), 7.30 (m, 6H), 5.09 (s, 2H), 4.67 (s, 2H), 3.90 (s, 2H), 3.77 (s, 3H); MS (m/e) 372 (M+1); mp 191° C.

1655b) A solution of 7-methoxy-8-nitro-2-oxo-1,2,3,5-tetrahydro-benzo[e][1,4]diazepine-4-carboxylic acid benzyl ester (380 mg, 1.0 mmol) in ethyl acetate (50 mL) and ethanol (50 mL) was treated with 10% Pd on carbon (50 mg) and placed on a Paar shaker under an atmosphere of hydrogen gas (50 psi). After 18 hours LCMS indicated completion of reaction. The mixture was filtered and concentrated to give 8-amino-7-methoxy-1,3,4,5-tetrahydro-benzo[e][1,4]diazepin-2-one (122 mg, 53%) as a tan solid, used without further purification; $^1$H NMR (400 MHz, DMSO-$d_6$) δ 9.42 (s, 1H), 6.64 (s, 1H), 6.33 (s, 1H), 4.72 (s, 2H), 3.72 (s, 3H), 3.67 (s, 2H), 3.19 (s, 2H); MS (m/e) 208 (M+1); mp 196° C. (dec.).

1655c) To a solution of 8-amino-7-methoxy-1,3,4,5-tetrahydro-benzo[e][1,4]diazepin-2-one (66 mg, 0.32 mmol) and N-[(1R,2R)-2-(2,5-dichloro-pyrimidin-4-ylamino)-cyclohexyl]-methanesulfonamide (100 mg, 0.30 mmol) in 2-methoxyethanol (3 mL) was added 4N HCl-dioxane (50 µL). The mixture was heated under microwave irradiation to 120° C. for 20 minutes. The mixture was adjusted to pH 9 (Et$_3$N) and purified by flash chromatography on silica get (MeOH-DCM) to give 15 mg (9%) of N-{(1R,2R)-2-[5-chloro-2-(7-methoxy-2-oxo-2,3,4,5-tetrahydro-1H-benzo[e][1,4]diazepin-8-ylamino)-pyrimidin-4-ylamino)-cyclohexyl}-methanesulfonamide as a mustard yellow solid; $^1$H NMR (400 MHz, DMSO-d6) δ 8.15 (s, 1H), 8.00 (s, 1H), 7.72 (s, 1H), 7.47 (s, 1H), 6.73 (s, 1H), 5.57 (d, J=7 Hz, 1H), 5.46 (d, J=7 Hz, 1H), 4.00 (s, 2H), 3.92 (s, 3H), 3.61 (s, 2H), 3.29 (m, 1H), 2.89 (s, 3H), 2.21 (m, 2H), 1.83 (m, 2H), 1.65 (m, 1H), 1.38 (m, 2H), 1.25 (m, 2H); MS (m/e) 510 (M+1); mp 135° C. (dec.).

Example 1656

2-{8-[5-Chloro-4-(2-dimethylsulfamoyl-phenylamino)-pyrimidin-2-ylamino]-1-dimethylcarbamoylmethyl-7-methoxy-2-oxo-1,2,3,5-tetrahydrobenzo[e][1,4]diazepin-4-yl}-N,N-dimethyl-acetamide 1656a) To a solution of 4-benzyl-7-methoxy-1,3,4,5-tetrahydro-benzo[e][1,4]diazepin-2-one (4.67 g, 16.5 mmol) in dichloromethane (150 mL) was added benzyl chloroformate (6.2 g, 36.0 mmol). The mixture was heated to reflux for four hours whereupon LCMS showed completion of the reaction. The mixture was cooled to room temperature, washed with saturated aqueous sodium bicarbonate and brine, dried over magnesium sulfate, filtered and concentrated. The crude product was purified by flash chromatography over silica gel (0-5% MeOH/DCM) to afford 5.0 g (93%) of 7-methoxy-2-oxo-1,2,3,5-tetrahydro-benzo[e][1,4]diazepine-4-carboxylic acid benzyl ester; NMR (400 MHz, DMSO-d6) δ 9.96 (s, 1H), 7.35 (m, 5H), 7.04 (d, J=9 Hz, 1H), 6.84 (d, J=9 Hz, 1H), 5.08 (s, 2H), 4.54 (s, 2H), 4.20 (2s, 2H), 3.70 (2s, 3H); MS (m/e) 327 (M+1); mp 138° C.

1656b) A solution of 7-methoxy-2-oxo-1,2,3,5-tetrahydro-benzo[e][1,4]diazepine-4-carboxylic acid benzyl ester (1.26 g, 3.86 mmol) in ethyl acetate (25 mL) and ethanol (25 mL) was treated with 10% Pd—C (125 mg) and hydrogenated under 40 psi H$_2$ on a Paar apparatus. After two hours LCMS indicated completion of the reaction. The mixture was filtered and concentrated to afford 7-methoxy-1,3,4,5-tetrahydro-benzo[e][1,4]diazepin-2-one (730 mg, 96%) as a white solid, used without further purification; NMR (400 MHz, DMSO-d6) δ 9.60 (s, 1H), 7.00 (d, J=8 Hz, 1H), 6.80 (d, J=8 Hz, 1H), 6.78 (s, 1H), 3.80 (s, 2H), 3.72 (s, 3H), 3.38 (s, 2H), 3.00 (br, 1H); MS (m/e) 193 (M+1); mp 148° C.

1656c) A slurry of 7-methoxy-1,3,4,5-tetrahydro-benzo[e][1,4]diazepin-2-one (2.80 g, 14.6 mmol) in acetonitrile (50 mL) was cooled in an ice-water bath and treated with trifluoroacetic anhydride (7.2 mL, 51 mmol). The mixture was stirred for ten minutes, granular potassium nitrate (3.1 g, 30 mmol) was added portionwise over three minutes, and the mixture was stirred while being allowed to warm slowly to room temperature overnight. The cloudy reaction mixture was quenched with portionwise addition of 5% aqueous sodium bicarbonate to pH 8-9. The mixture was extracted with dichloromethane (200 mL). The aqueous phase was further extracted with dichloromethane (2×50 mL), the combined organic phase was washed with water and brine, dried over magnesium sulfate, filtered and concentrated. Flash chromatography over silica gel (EtOAc/hexanes) gave 1.15 g (23%) of 7-methoxy-8-nitro-4-(2,2,2-trifluoro-acetyl)-1,3,4,5-tetrahydro-benzo[e][1,4]diazepin-2-one as a yellow solid. NMR analysis revealed a mixture of two conformational isomers: NMR (400 MHz, DMSO-d6) δ 10.43/10.34 (2s, 1H), 7.70/7.68 (2s, 1H), 7.51/7.44 (2s, 1H), 4.95/4.83 (2s, 2H), 4.43/4.41 (2s, 2H), 3.92/3.90 (2s, 3H); MS (m/e) 334 (M+1).

1656d) To a solution of 7-methoxy-8-nitro-4-(2,2,2-trifluoro-acetyl)-1,3,4,5-tetrahydro-benzo[e][1,4]diazepin-2-one (1.10 g, 3.3 mmol) in methanol (10 mL) cooled in an ice-water bath was added 7M NH$_3$/MeOH (10 mL, 70 mmol). The mixture was stirred while being allowed to warm slowly to room temperature over 1.5 hours, concentrated on a rotary evaporator, and purified by flash chromatography over silica gel (0-20% MeOH/DCM) to afford 7-methoxy-8-nitro-1,3,4,5-tetrahydro-benzo[e][1,4]diazepin-2-one (0.75 g, 96%) as a yellow solid; NMR (400 MHz, DMSO-d6) δ 9.90 (s, 1H), 7.68 (s, 1H), 7.20 (s, 1H), 3.97 (s, 2H), 3.88 (3H), 3.51 (s, 2H); MS (m/e) 238 (M+1); mp 203° C. (dec.).

1656e) To a solution of 7-methoxy-8-nitro-1,3,4,5-tetrahydro-benzo[e][1,4]diazepin-2-one (300 mg, 1.27 mmol) in acetonitrile (10 mL) was added powdered cesium carbonate 820 mg, 2.5 mmol) and 2-chloro-N,N-dimethylacetamide (0.20 mL, 1.9 mmol). Potassium iodide (42 mg, 0.25 mmol) was added and the mixture was stirred at 65° C. After 18 hours the mixture was filtered and concentrated. Purification by flash chromatography on silica gel (MeOH/DCM) gave 300 mg (58%) of 2-(1-dimethylcarbamoylmethyl-7-methoxy-8-nitro-2-oxo-1,2,3,5-tetrahydro-benzo[e][1,4]diazepin-4-yl)-N,N-dimethyl-acetamide; NMR (400 MHz, DMSO-d6) δ 7.91 (s, 1H), 7.39 (s, 1H), 4.72 (s, 2H), 3.96 (s, 3H), 3.36 (s, 2H), 3.32 (s, 2H), 3.09 (s, 2H), 3.02 (s, 3H0, 3.00 (s, 3H), 2.84 (s, 3H), 2.80 (s, 3H); MS (m/e) 408 (M+1); mp 98° C.

1656f) A solution of 2-(1-dimethylcarbamoylmethyl-7-methoxy-8-nitro-2-oxo-1,2,3,5-tetrahydro-benzo[e][1,4]diazepin-4-yl)-N,N-dimethyl-acetamide (150 mg, 0.37 mmol) in ethyl acetate (25 mL) and ethanol (25 mL) was treated with 10% Pd—C and hydrogenated on a Paar apparatus under 40 psi H$_2$. After 14 hours the mixture was filtered and concentrated to give 2-(8-amino-1-dimethylcarbamoylmethyl-7-methoxy-2-oxo-1,2,3,5-tetrahydro-benzo[e][1,4]diazepin-4-yl)-N,N-dimethyl-acetamide (140 mg, 99%) as a pale yellow solid, used without further purification; MS (m/e) 378 (M+1).

1656g) To a mixture of 2-(8-amino-1-dimethylcarbamoyl-methyl-7-methoxy-2-oxo-1,2,3,5-tetrahydro-benzo[e][1,4]diazepin-4-yl)-N,N-dimethyl-acetamide (80 mg, 0.21 mmol) and 2-(2,5-dichloro-pyrimidin-4-ylamino)-N,N-dimethyl-benzenesulfonamide (69 mg, 0.20 mmol) in isopropanol (5 mL) was added 10-camphorsulfonic acid (123 mg, 0.53 mmol). The mixture was heated to 90° C. for 20 minutes under microwave irradiation, cooled to room temperature, and concentrated on a rotary evaporator. The residue was dissolved in dichloromethane and stirred with saturated aqueous sodium bicarbonate to neutral pH. The organic phase was washed with brine, dried over magnesium sulfate, filtered and concentrated. The crude product was purified by flash chromatography over silica gel (MeOH/DCM) to give 40 mg (29%) of 2-{8-[5-chloro-4-(2-dimethylsulfamoyl-phenylamino)-pyrimidin-2-ylamino]-1-dimethylcarbamoylmethyl-7-methoxy-2-oxo-1,2,3,5-tetrahydro-benzo[e][1,4]diazepin-4-yl}-N,N-dimethyl-acetamide as a pale yellow solid; NMR (400 MHz, CDCl$_3$) δ 9.39 (s, 1H), 8.51 (d, J=8 Hz, 1H), 8.34 (s, 1H), 8.19 (s, 1H), 7.90 (d, J=8 Hz, 1H), 7.61 (s, 1H), 7.56 (m, 1H), 7.28 (m, 1H), 6.94 (s, 1H), 4.45 (br s, 2H), 4.08 (s, 2H), 3.93 (s, 3H), 3.54 (s, 2H), 3.35 (s, 2H), 3.10 (s, 3H), 3.00 (s, 3H), 2.96 (s, 2H), 2.91 (s, 3H), 2.79 (s, 6H); MS (m/e) 689 (M+1); mp 154° C.

Example 1657

N-{(1R,2R)-2-[2-(4-Acetyl-7-methoxy-2-oxo-2,3,4,5-tetrahydro-1H-benzo[e][1,4]di-azepin-8-ylamino)-5-chloro-pyrimidin-4-ylamino]-cyclohexyl}-methanesulfonamide 1657a) To a slurry of 7-methoxy-8-nitro-1,3,4,5-tetrahydro-benzo[e][1,4]diazepin-2-one (100 mg, 0.42 mmol) in dichloromethane (10 mL) was syringed N,N-diisopropylethylamine (0.15 mL, 0.84 mmol). The mixture was cooled in an ice-water bath and acetyl chloride (0.04 mL, 0.55 mmol) was added via syringe. After 15 minutes LCMS indicated completion of the reaction. Dichloromethane (10 mL) and 10% aqueous citric acid (10 mL) were added and the mixture was stirred while being allowed to warm to room temperature. The mixture was filtered and the collected solid was washed with water and dried to constant weight to give 4-acetyl-7-methoxy-8-nitro-1,3,4,5-tetrahydro-benzo[e][1,4]diazepin-2-one (70 mg, 60%) as a yellow solid. NMR analysis indicated a mixture of two conformational isomers, similar to that observed for the related trifluoroacetyl analog (see procedure 6c); NMR (400 MHz, DMSO-d6) δ 10.19/10.17 (2s, 1H), 7.69/7.66 (2s, 1H), 7.46/7.35 (2s, 1H), 4.78/4.67 (2s, 2H), 4.36/4.37 (2s, 2H), 3.90/3.92 (2s, 3H), 2.05 (s, 3H); MS (m/e) 278 (M−1); mp 266° C. (dec.).

1657b) Reduction of 4-acetyl-7-methoxy-8-nitro-1,3,4,5-tetrahydro-benzo[e][1,4]diazepin-2-one (55 mg, 0.20 mmol) was conducted as in procedure 6f to give 4-acetyl-8-amino-7-methoxy-1,3,4,5-tetrahydro-benzo[e][1,4]diazepin-2-one (50 mg, 99%) as a pale yellow solid, used without further purification; MS (m/e) 250 (M+1).

1657c) In an analogous manner to procedure 1656g, 4-acetyl-8-amino-7-methoxy-1,3,4,5-tetrahydro-benzo[e][1,4]diazepin-2-one (60 mg, 0.24 mmol) and N-[(1R,2R)-2-(2,5-dichloro-pyrimidin-4-ylamino)-cyclohexyl]-methanesulfonamide (82 mg, 0.24 mmol) were coupled to provide N-{(1R,2R)-2-[2-(4-Acetyl-7-methoxy-2-oxo-2,3,4,5-tetrahydro-1H-benzo[e][1,4]di-azepin-8-ylamino)-5-chloro-pyrimidin-4-ylamino]-cyclohexyl}-methanesulfonamide (14 mg, 10%) as a pale yellow solid following preparative tlc (10% MeOH-DCM); $^1$H NMR (400 MHz, DMSO-d6) δ 8.23 (s, 1H), 8.15 (s, 1H), 8.00 (s, 1H), 7.47 (s, 1H), 6.73 (s, 1H), 5.63 (d, J=7 Hz, 1H), 5.46 (d, J=7 Hz, 1H), 4.00 (s, 2H), 3.92 (s, 3H), 3.53 (s, 2H), 3.29 (m, 1H), 2.89 (s, 3H), 2.21 (m, 2H), 2.17 (s, 3H), 1.83 (m, 2H), 1.65 (m, 1H), 1.38 (m, 2H), 1.25 (m, 2H); MS (m/e) 553 (M+1); mp 167° C. (dec.).

Example 1658

N-{(1R,2R)-2-[5-Chloro-2-(4-ethyl-7-methoxy-2-oxo-2,3,4,5-tetrahydro-1H-benzo[e][1,4]diazepin-8-ylamino)-pyrimidin-4-ylamino]-cyclohexyl}-methane-sulfonamide 1658a) To a solution of 7-methoxy-8-nitro-1,3,4,5-tetrahydro-benzo[e][1,4]diazepin-2-one (400 mg, 1.69 mmol) in methanol (100 mL) was added acetaldehyde (2.0 mL, 30 mmol) followed by acetic acid (0.29 mL, 5.0 mmol). The mixture was stirred for 20 minutes at room temperature whereupon sodium triacetoxyborohydride (1.10 g, 5.0 mmol) was added. The mixture was stirred at room temperature overnight and then concentrated on a rotary evaporator. The residue was dissolved in ethyl acetate, washed with saturated aqueous sodium bicarbonate and brine, dried over magnesium sulfate, filtered and concentrated. Flash chromatography over silica gel (0-5% MeOH-EtOAc) gave 4-ethyl-7-methoxy-8-nitro-1,3,4,5-tetrahydro-benzo[e][1,4]diazepin-2-one (330 mg, 72%) as a yellow solid; $^1$H NMR (400 MHz, DMSO-d6) δ 10.01 (s, 1H), 7.60 (s, 1H), 7.35 (s, 1H), 3.91 (s, 3H), 3.86 (s, 2H), 3.35 (s, 2H), 2.55 (q, J=6 Hz, 2H), 1.06 (t, J=6 Hz, 3H); MS (m/e) 266 (M+1); mp 168° C. (dec.).

1658b) Reduction of 4-ethyl-7-methoxy-8-nitro-1,3,4,5-tetrahydro-benzo[e][1,4]diazepin-2-one (350 mg, 1.32 mmol) was conducted as in procedure 6f to give 8-amino-4-ethyl-7-methoxy-1,3,4,5-tetrahydro-benzo[e][1,4]diazepin-2-one (300 mg, 99%) as a pale yellow solid; MS (m/e) 2236 (M+1).

1658c) In an analogous manner to procedure 1656g, 8-amino-4-ethyl-7-methoxy-1,3,4,5-tetrahydro-benzo[e][1,4]diazepin-2-one (70 mg, 0.30 mmol) and N-[(1R,2R)-2-(2,5-dichloro-pyrimidin-4-ylamino)-cyclohexyl]-methane-sulfonamide (101 mg, 0.30 mmol) were coupled to provide N-{(1R,2R)-2-[5-chloro-2-(4-ethyl-7-methoxy-2-oxo-2,3,4,5-tetrahydro-1H-benzo[e][1,4]diazepin-8-ylamino)-pyrimidin-4-ylamino]-cyclohexyl}-methane-sulfonamide (40 mg, 20%) as a mustard yellow solid following preparative tlc (DCM/MeOH/c.NH$_4$OH=90/9/1); $^1$H NMR (400 MHz, CDCl$_3$) δ 8.15 (s, 1H), 8.00 (s, 1H), 7.49 (s, 1H), 7.46 (s, 1H), 6.82 (s, 1H), 5.53 (d, J=7 Hz, 1H), 5.31 (d, J=7 Hz, 1H), 3.94 (s, 3H), 3.74 (s, 2H), 3.40 (s, 2H), 3.29 (m, 1H), 2.87 (s, 3H), 2.77 (q, J=7 Hz, 2H), 2.23 (m, 2H), 1.84 (m, 2H), 1.38 (m, 2H), 1.27 (m, 2H), 1.20 (t, J=7 Hz, 3H); MS (m/e) 538 (M+1); mp 216° C. (dec.).

Example 1659

2-[5-Chloro-2-(4-ethyl-7-methoxy-2-oxo-2,3,4,5-tetrahydro-1H-benzo[e][1,4]diazepin-8-ylamino)-pyrimidin-4-ylamino]-N,N-dimethyl-benzene-sulfonamide 1659a) In an analogous manner to procedure 1656g, 8-amino-4-ethyl-7-methoxy-1,3,4,5-tetrahydro-benzo[e][1,4]diazepin-2-one (60 mg, 0.26 mmol) and 2-(2,5-dichloro-pyrimidin-4-ylamino)-N,N-dimethyl-benzenesulfonamide (88 mg, 0.26 mmol) were coupled to provide 2-[5-chloro-2-(4-ethyl-7-methoxy-2-oxo-2,3,4,5-tetrahydro-1H-benzo[e][1,4]diazepin-8-ylamino)-pyrimidin-4-ylamino]-N,N-dimethyl-benzenesulfonamide (25 mg, 18%) as a pale yellow solid following preparative tlc (10% MeOH-DCM); NMR (400 MHz, CDCl$_3$) δ 9.36 (s, 1H), 8.44 (d, J=8 Hz, 1H), 8.18 (s, 1H), 8.08 (s, 1H), 7.93 (d, J=8 Hz, 1H), 7.65 (m, 2H), 7.37

(m, 1H), 7.09 (s, 1H), 6.82 (s, 1H), 3.94 (s, 3H), 3.76 (s, 2H), 3.43 (s, 2H), 2.77 (m, 8H), 1.22 (t, J=7 Hz, 3H); MS (m/e) 546 (M+1); mp 175° C.

Example 1660

8-{5-Chloro-4-[2-(propane-2-sulfonyl)-phenylamino]-pyrimidin-2-ylamino}-4-ethyl-7-methoxy-1,3,4,5-tetrahydro-benzo[e][1,4]diazepin-2-one 1660a) In an analogous manner to procedure 1656g, 8-amino-4-ethyl-7-methoxy-1,3,4,5-tetrahydro-benzo[e][1,4]diazepin-2-one (60 mg, 0.26 mmol) and (2,5-dichloro-pyrimidin-4-yl)-[2-(propane-2-sulfonyl)-phenyl]-amine (88 mg, 0.26 mmol) were coupled to provide 8-{5-chloro-4-[2-(propane-2-sulfonyl)-phenylamino]-pyrimidin-2-ylamino}-4-ethyl-7-methoxy-1,3,4,5-tetrahydro-benzo[e][1,4]diazepin-2-one (20 mg, 14%) as a mustard yellow solid following preparative tlc (10% MeOH-DCM); NMR (400 MHz, CDCl$_3$) δ 9.56 (s, 1H), 8.49 (d, J=8 Hz, 1H), 8.20 (s, 1H), 8.08 (s, 1H), 7.97 (d, J=8 Hz, 1H), 7.68 (m, 2H), 7.39 (m, 1H), 7.16 (s, 1H), 6.82 (s, 1H), 3.94 (s, 3H), 3.75 (s, 2H), 3.42 (s, 2H), 3.24 (t, J=7 Hz, 1H), 2.76 (t, J=7 Hz, 2H), 1.33 (d, J=7 Hz, 6H), 1.20 (t, J=7 Hz, 3H); MS (m/e) 546 (M+1); mp 175° C.

Example 1661

8-[5-Chloro-4-(2-methoxy-4-morpholin-4-yl-phenylamino)-pyrimidin-2-ylamino]-4-ethyl-7-methoxy-1,3,4,5-tetrahydro-benzo[e][1,4]diazepin-2-one 1661a) In an analogous manner to procedure 1656g, 8-amino-4-ethyl-7-methoxy-1,3,4,5-tetrahydro-benzo[e][1,4]diazepin-2-one (100 mg, 0.43 mmol) and (2,5-dichloro-pyrimidin-4-yl)-(2-methoxy-4-morpholin-4-yl-phenyl)-amine (151 mg, 0.43 mmol) were coupled to provide 8-[5-chloro-4-(2-methoxy-4-morpholin-4-yl-phenylamino)-pyrimidin-2-ylamino]-4-ethyl-7-methoxy-1,3,4,5-tetrahydro-benzo[e][1,4]diazepin-2-one (66 mg, 22%) as a pale yellow foam following flash chromatography on silica gel (0-5% MeOH-DCM); NMR (400 MHz, CDCl$_3$) δ 8.20 (s, 1H), 8.03 (m, 1H), 7.64 (s, 1H), 7.39 (s, 1H), 7.20 (s, 1H), 6.80 (s, 1H), 6.60 (m, 2H), 3.92 (m, 10H), 3.73 (s, 2H), 3.40 (s, 2H), 3.29 (m, 4H), 2.78 (t, J=7 Hz, 2H), 1.20 (t, J=7 Hz, 3H); MS (m/e) 554 (M+1).

Example 1662

8-[5-Chloro-4-(4-methoxy-2-pyrazol-1-yl-phenylamino)-pyrimidin-2-ylamino]-4-ethyl-7-methoxy-1,3,4,5-tetrahydro-benzo[e][1,4]diazepin-2-one 1662a) In an analogous manner to procedure 1656g, 8-amino-4-ethyl-7-methoxy-1,3,4,5-tetrahydro-benzo[e][1,4]diazepin-2-one (100 mg, 0.43 mmol) and (2,5-dichloro-pyrimidin-4-yl)-(2-methoxy-4-morpholin-4-yl-phenyl)-amine (143 mg, 0.43 mmol) were coupled to provide 8-[5-chloro-4-(4-methoxy-2-pyrazol-1-yl-phenylamino)-pyrimidin-2-ylamino]-4-ethyl-7-methoxy-1,3,4,5-tetrahydro-benzo[e][1,4]diazepin-2-one (50 mg, 20%) as a pale yellow foam following flash chromatography on silica gel (0-5% MeOH-DCM); NMR (400 MHz, CDCl$_3$) δ 9.63 (s, 1H), 8.14 (d, J=9 Hz, 1H), 8.10 (s, 1H), 8.04 (s, 1H), 7.83 (s, 1H), 7.61 (s, 1H), 7.33 (s, 1H), 7.04 (s, 1H), 7.00 (d, J=9 Hz, 1H), 6.78 (s, 1H), 6.50 (s, 2H), 3.97 (s, 3H), 3.90 (s, 3H), 3.73 (s, 2H), 3.42 (s, 2H), 2.78 (t, J=7 Hz, 2H), 1.20 (t, J=7 Hz, 3H); MS (m/e) 535 (M+1).

Example 1663

(1S,2S,3R,4R)-3-[5-Chloro-2-(4-ethyl-7-methoxy-2-oxo-2,3,4,5-tetrahydro-1H-benzo[e][1,4]diazepin-8-ylamino)-pyrimidin-4-ylamino]-bicyclo-[2.2.1]hept-5-ene-2-carboxylic acid amide.

1663a) In an analogous manner to procedure 1656 g, 8-amino-4-ethyl-7-methoxy-1,3,4,5-tetrahydro-benzo[e][1,4]diazepin-2-one (130 mg, 0.55 mmol) and (1S,2S,3R,4R)-3-(2,5-dichloro-pyrimidin-4-ylamino)-bicyclo[2.2.1]hept-5-ene-2-carboxylic acid amide (160 mg, 0.55 mmol) were coupled to provide (1S,2S,3R,4R)-3-[5-chloro-2-(4-ethyl-7-methoxy-2-oxo-2,3,4,5-tetrahydro-1H-benzo[e][1,4]diazepin-8-ylamino)-pyrimidin-4-ylamino]-bicyclo-[2.2.1]hept-5-ene-2-carboxylic acid amide (34 mg, 12%) following preparative reverse-phase chromatography; $^1$H NMR (400 MHz, CDCl$_3$) δ 8.00 (s, 1H), 7.82 (s, 1H), 7.07 (s, 1H), 6.32 (m, 1H), 6.08 (m, 1H), 4.36 (m, 1H), 4.18 (m, 1H), 3.88 (s, 3H), 3.70 (m, 2H), 3.40 (m, 2H), 3.05 (s, 1H), 2.80 (s, 1H), 2.60 (q, J=7 Hz, 2H), 1.60 (d, J=8 Hz, 1H), 1.50 (t, J=7 Hz, 3H); MS (m/e) 498 (M+1); mp 165° C. (dec.).

Example 1664

N-(1R,2R)-(2-{5-Chloro-2-[7-methoxy-4-(2-methoxy-ethyl)-2-oxo-2,3,4,5-tetrahydro-1H-benzo[e][1,4]diazepin-8-ylamino]-pyrimidin-4-ylamino}-cyclohexyl)-methanesulfonamide 1664a) A solution of 1,1,2-(trimethoxy)ethane (2.0 g, 16.4 mmol) in TFA/H$_2$O (5 mL, 1/1 vol.) was stirred for five minutes at 50° C. The mixture was cooled to room temperature and neutralized to pH 6-7 by the addition of microporous carbonate (MP-CO$_3$) with stirring. This was filtered into a solution of 7-methoxy-8-nitro-1,3,4,5-tetrahydro-benzo[e][1,4]diazepin-2-one (375 mg, 1.58 mmol) in ethanol (40 mL). The MP-CO$_3$ was washed further with ethanol (10 mL) into the reaction mixture. To this was added acetic acid (0.36 mL, 6.34 mmol) and the mixture was stirred for two hours at room temperature before being treated with sodium triacetoxyborohydride (2.0 g, 9.4 mmol) and stirred at room temperature for an additional 18 hours. The mixture was concentrated, dissolved in dichloromethane, washed with saturated aqueous sodium bicarbonate and brine, dried over magnesium sulfate, filtered and concentrated. Flash chromatography over silica gel (0-10% MeOH-EtOAc) gave 7-methoxy-4-(2-methoxy-ethyl)-8-nitro-1,3,4,5-tetrahydro-benzo[e][1,4]diazepin-2-one (175 mg, 38%); $^1$H NMR (400 MHz, DMSO-d6) δ 10.02 (s, 1H), 7.61 (s, 1H), 7.32 (s, 1H), 3.91 (s, 6H), 3.44 (t, J=6 Hz, 2H), 3.41 (s, 2H), 2.69 (t, J=6 Hz, 2H); MS (m/e) 296 (M+1).

1664b) Reduction of 7-methoxy-4-(2-methoxy-ethyl)-8-nitro-1,3,4,5-tetrahydro-benzo[e][1,4]diazepin-2-one (170 mg, 0.58 mmol) was carried out in an analogous manner to 1656f to afford 8-amino-7-methoxy-4-(2-methoxy-ethyl)-1,3,4,5-tetrahydro-benzo[e][1,4]diazepin-2-one (146 mg, 93%) as a hygroscopic yellow solid, used without further purification; MS (m/e) 266 (M+1).

1664c) In an analogous manner to procedure 1656g, 8-amino-7-methoxy-4-(2-methoxy-ethyl)-1,3,4,5-tetrahydro-benzo[e][1,4]diazepin-2-one (70 mg, 0.0.26 mmol) and N-[(1R,2R)-2-(2,5-dichloro-pyrimidin-4-ylamino)-cyclohexyl]-methanesulfonamide (90 mg, 0.26 mmol) were coupled to provide N-{(1R,2R)-(2-{5-Chloro-2-[7-methoxy-4-(2-methoxy-ethyl)-2-oxo-2,3,4,5-tetrahydro-1H-benzo[e][1,4]diazepin-8-ylamino]-pyrimidin-4-ylamino}-cyclohexyl)-methanesulfonamide (33 mg, 14%) as a pale yellow solid following flash chromatography on silica gel (0-10%

MeOH-EtOAc); $^1$H NMR (400 MHz, CDCl$_3$) δ 8.12 (s, 1H), 7.91 (s, 1H), 6.79 (s, 1H), 5.77 (m, 1H), 3.90 (s, 3H), 3.75 (d, J=5 Hz, 2H), 3.55 (t, J=5 Hz, 2H), 3.38 (m, 6H), 3.25 (m, 1H), 2.88 (m, 5H), 2.15 (m, 2H), 1.80 (m, 2H), 1.45 (m, 1H), 1.35 (m, 3H); MS (m/e) 568 (M+1); mp 245° C. (dec.).

Example 1665

(1S,2S,3R,4R)-3-{5-Chloro-2-[7-methoxy-4-(2-methoxy-ethyl)-2-oxo-2,3,4,5-tetrahydro-1H-benzo[e][1,4]diazepin-8-ylamino]-pyrimidin-4-ylamino}-bicyclo[2.2.1]hept-5-ene-2-carboxylic acid amide.

1665a) In an analogous manner to procedure 1656g, 8-amino-7-methoxy-4-(2-methoxy-ethyl)-1,3,4,5-tetrahydro-benzo[e][1,4]diazepin-2-one (80 mg, 0.30 mmol) and (1S,2S,3R,4R)-3-(2,5-dichloro-pyrimidin-4-ylamino)-bicyclo[2.2.1]hept-5-ene-2-carboxylic acid amide (90 mg, 0.30 mmol) were coupled to afford (1S,2S,3R,4R)-3-{5-chloro-2-[7-methoxy-4-(2-methoxy-ethyl)-2-oxo-2,3,4,5-tetrahydro-1H-benzo[e][1,4]diazepin-8-ylamino]-pyrimidin-4-ylamino}-bicyclo[2.2.1]hept-5-ene-2-carboxylic acid amide (24 mg, 14%) as a tan foam following reverse-phase preparative chromatography; $^1$H NMR (400 MHz, CDCl$_3$) δ 7.96 (s, 1H), 7.77 (s, 1H), 6.96 (s, 1H), 6.32 (m, 1H), 6.09 (m, 1H), 4.38 (m, 1H), 4.22 (m, 1H), 4.16 (m, 1H), 3.84 (m, 5H), 3.77 (s, 2H), 3.44 (m, 4H), 3.41 (s, 3H), 3.04 (s, 1H), 2.80 (s, 1H), 2.53 (d, J=8 Hz, 1H), 1.57 (d, J=8 Hz, 1H); MS (m/e) 528 (M+1).

Example 1666

N-(1R,2R)-{2-[5-Chloro-2-(4-cyclopropylmethyl-7-methoxy-2-oxo-2,3,4,5-tetrahydro-1H-benzo[e][1,4]diazepin-8-ylamino)-pyrimidin-4-ylamino]-cyclohexyl}-methanesulfonamide 1666a) To a solution of 7-methoxy-8-nitro-1,3,4,5-tetrahydro-benzo[e][1,4]diazepin-2-one (450 mg, 1.90 mmol) and cyclopropanecarboxaldehyde (2.84 mL, 37.9 mmol) in dichloromethane (50 mL) and methanol (5 mL) was added acetic acid (0.22 mL, 3.8 mmol). After being stirred for two hours at room temperature, sodium triacetoxyborohydride (1.2 g, 5.7 mmol) was added and the mixture was stirred for 18 hours at room temperature. The mixture was washed with saturated aqueous sodium bicarbonate and brine before being dried over magnesium sulfate, filtered and concentrated. Flash chromatography over silica gel (0-5% MeOH-DCM) gave 4-cyclopropylmethyl-7-methoxy-8-nitro-1,3,4,5-tetrahydro-benzo[e][1,4]diazepin-2-one (440 mg, 80%) as a yellow-orange solid; $^1$H NMR (400 MHz, DMSO-d6) δ 10.00 (s, 1H), 7.59 (s, 1H), 7.33 (s, 1H), 3.91 (2s, 5H), 3.43 (s, 2H), 2.41 (d, J=6 Hz, 2H), 0.86 (m, 1H), 0.47 (m, 2H), 0.10 (m, 2H); MS (m/e) 292 (M+1); mp 178° C.

1666b) Reduction of 4-cyclopropylmethyl-7-methoxy-8-nitro-1,3,4,5-tetrahydro-benzo[e][1,4]diazepin-2-one (420 mg, 1.4 mmol) was conducted in a manner analogous to the procedure for 1656f to give 8-amino-4-cyclopropylmethyl-7-methoxy-1,3,4,5-tetrahydro-benzo[e][1,4]diazepin-2-one (375 mg, 98%) as a pale yellow solid, used without further purification; MS (m/e) 262 (M+1).

1666c) In an analogous manner to procedure 1656g, 8-amino-4-cyclopropylmethyl-7-methoxy-1,3,4,5-tetrahydro-benzo[e][1,4]diazepin-2-one (150 mg, 0.57 mmol) and N-[(1R,2R)-2-(2,5-dichloro-pyrimidin-4-ylamino)-cyclohexyl]-methanesulfonamide (162 mg, 0.48 mmol) were coupled to provide N-(1R,2R)-{2-[5-chloro-2-(4-cyclopropylmethyl-7-methoxy-2-oxo-2,3,4,5-tetrahydro-1H-benzo[e][1,4]diazepin-8-ylamino)-pyrimidin-4-ylamino)-cyclohexyl}-methanesulfonamide (104 mg, 38%) as a tan solid following preparative tlc on silica gel (10% MeOH-DCM); $^1$H NMR (400 MHz, DMSO-d6) δ 9.59 (s, 1H), 7.95 (s, 1H), 7.92 (s, 1H), 7.72 (s, 1H), 7.04 (d, J=8 Hz, 1H), 6.98 (s, 1H), 6.86 (d, J=8 Hz, 1H), 3.86 (s, 3H), 3.82 (m, 2H), 3.68 (s, 2H), 3.32 (s, 3H), 3.22 (s, 2H), 2.88 (m, 3H), 2.41 (m, 3H), 1.97 (m, 2H), 1.63 (m, 2H), 1.37 (m, 2H), 0.87 (m, 1H), 0.48 (m, 2H), 0.14 (m, 2H); MS (m/e) 564 (M+1); mp 97° C.

Example 1667

(1S,2S,3R,4R)-3-[5-Chloro-2-(4-cyclopropylmethyl-7-methoxy-2-oxo-2,3,4,5-tetrahydro-1H-benzo[e][1,4]diazepin-8-ylamino)-pyrimidin-4-ylamino]-bicyclo[2.2.1]hept-5-ene-2-carboxylic acid amide.

1667a) In an analogous manner to procedure 1656g, 8-amino-4-cyclopropylmethyl-7-methoxy-1,3,4,5-tetrahydro-benzo[e][1,4]diazepin-2-one (150 mg, 0.57 mmol) and (1S,2S,3R,4R)-3-(2,5-dichloro-pyrimidin-4-ylamino)-bicyclo[2.2.1]hept-5-ene-2-carboxylic acid amide (143 mg, 0.48 mmol) were coupled to afford (1S,2S,3R,4R)-3-[5-chloro-2-(4-cyclopropylmethyl-7-methoxy-2-oxo-2,3,4,5-tetrahydro-1H-benzo[e][1,4]diazepin-8-ylamino)-pyrimidin-4-ylamino]-bicyclo[2.2.1]hept-5-ene-2-carboxylic acid amide (60 mg, 24%) as a mustard yellow solid following preparative tlc on silica gel (10% MeOH-DCM); $^1$H NMR (400 MHz, CDCl$_3$) δ 8.28 (s, 2H), 7.90 (s, 1H), 7.52 (s, 1H), 7.16 (d, J=8 Hz, 1H), 6.79 (s, 1H), 6.30 (m, 3H), 5.69 (s, 1H), 4.38 (t, J=8 Hz, 1H), 3.93 (s, 3H), 3.78 (m, 2H), 3.43 (m, 2H), 3.06 (s, 1H), 2.87 (s, 1H), 2.57 (m, 3H), 2.24 (d, J=9 Hz, 1H), 1.60 (d, J=9 Hz, 1H), 0.92 (m, 1H), 0.59 (m, 2H), 0.22 (m, 2H); MS (m/e) 524 (M+1); mp 152° C.

Example 1668

8-{5-Chloro-4-[2-(pyrrolidine-1-sulfonyl)-phenylamino]-pyrimidin-2-ylamino}-4-cyclopropylmethyl-7-methoxy-1,3,4,5-tetrahydro-benzo[e][1,4]diazepin-2-one 1668a) In an analogous manner to procedure 1656g, 8-amino-4-cyclopropylmethyl-7-methoxy-1,3,4,5-tetrahydro-benzo[e][1,4]diazepin-2-one (125 mg, 0.48 mmol) and (2,5-dichloro-pyrimidin-4-yl)-[2-(pyrrolidine-1-sulfonyl)-phenyl]-amine (149 mg, 0.40 mmol) were coupled to afford 8-{5-chloro-4-[2-(pyrrolidine-1-sulfonyl)-phenylamino]-pyrimidin-2-ylamino}-4-cyclopropylmethyl-7-methoxy-1,3,4,5-tetrahydro-benzo[e][1,4]diazepin-2-one (30 mg, 10%) as a pale yellow solid following flash chromatography on silica gel (0-10% MeOH-EtOAc); $^1$H NMR (400 MHz, CDCl$_3$) δ 9.44 (s, 1H), 8.45 (d, J=8 Hz, 1H), 8.19 (s, 1H), 8.07 (s, 1H), 7.98 (d, J=8 Hz, 1H), 7.62 (m, 2H), 7.35 (m, 1H), 7.07 (s, 1H), 6.83 (s, 1H), 3.94 (s, 3H), 3.82 (s, 2H), 3.53 (s, 2H), 3.28 (t, J=6 Hz, 4H), 2.60 (d, J=6 Hz, 2H), 1.82 (t, J=6 Hz, 4H), 0.96 (m, 1H), 0.60 (m, 2H), 0.23 (m, 2H); MS (m/e) 599 (M+1); mp 142° C.

Example 1671

2-[5-Chloro-2-(8-methoxy-5,5-dimethyl-2-oxo-2,3,4,5-tetrahydro-1H-benzo[b]azepin-7-ylamino)-pyrimidin-4-ylamino]-N-methyl-benzamide 1671a) 7-Methoxy-4,4-dimethyl-3,4-dihydro-2H-naphthalen-1-one (1.48 g, 7.24 mmol) (Winstein, S.; Heck, R. F, *J.*

*Org. Chem.*, 1972, 37, 825.) was dissolved in Ethanol (20 mL) then Hydroxylamine hydrochloride (0.61 g, 8.8 mmol) and Sodium acetate (1.20 g, 14.6 mmol) were added along with Water (20 mL). The mixture was warmed to 70° C. for 6 h, cooled and partitioned between 50 mL DCM, 10 mL satd. sodium bicarbonate and 40 mL water. The pH was 6-7. The phases were separated and the aq. extracted 2×50 mL DCM. The organic extracts were dried over sodium sulfate and concentrated in vacuo. 7-Methoxy-4,4-dimethyl-3,4-dihydro-2H-naphthalen-1-one oxime was isolated as a yellow solid (1.55 g, 98%) and used without purification. 1H-NMR (CDCl3): 7.42 (d, 1H, J=2.4 Hz), 7.27 (d, 1H, J=8.5 Hz), 7.23 (s, 1H), 6.91 (dd, 1H, J=2.4, 8.5 Hz), 3.81 (s, 3H), 2.85 (t, 2H, J=6.8 Hz), 1.73 (t, 2H, J=6.8 Hz), 1.27 (s, 6H).

1671b) 7-Methoxy-4,4-dimethyl-3,4-dihydro-2H-naphthalen-1-one oxime (1.54 g, 7.02 mmol) and Polyphosphoric acid (40 g, 400 mmol) were combined in a flask and heated to 60° C. with mechanical stirring overnight. The reaction mixture was cooled in an ice bath, then 200 g of ice was added and stirred to convert the oily residue into an off white suspension, which was extracted 3×100 mL DCM. The organic extracts were washed with 100 mL water and 100 mL brine: satd. sodium bicarbonate (1:1), dried over sodium sulfate and conc. in vacuo to afford 8-Methoxy-5,5-dimethyl-1,3,4,5-tetrahydro-benzo[b]azepin-2-one as a tan solid (1.45 g, 94%) 1H-NMR (CD3CN): 7.75 (s, 1H), 7.35 (d, 1H, J=8.8 Hz), 6.72 (dd, 1H, J=2.4, 8.8 Hz), 6.55 (d, 1H, J=2.4 Hz), 3.78 (s, 3H), 2.28 (t, 2H, J=6.8 Hz), 2.04 (t, 2H, J=6.8 Hz), 1.36 (s, 6H).

1671c) 8-Methoxy-5,5-dimethyl-1,3,4,5-tetrahydro-benzo[b]azepin-2-one (612 mg, 2.79 mmol) was dissolved in Acetonitrile (25 mL) and was cooled at −10° C. Trifluoroacetic anhydride (1.40 mL, 9.91 mmol) was added followed by Potassium nitrate (0.285 g, 2.82 mmol; Acros). After overnight stirring, the reaction was partitioned between aq. sodium hydroxide and DCM. The organic extract was chromatographed to afford two products, 8-Methoxy-5,5-dimethyl-9-nitro-1,3,4,5-tetrahydro-benzo[b]azepin-2-one (310 mg, 42%) and 8-Methoxy-5,5-dimethyl-7-nitro-1,3,4,5-tetrahydro-benzo[b]azepin-2-one (160 mg, 22%). 1H-NMR (CDCl$_3$): 7.48 (m, 2H), 6.85 (d, 1H, J=8.8 Hz), 3.91 (s, 3H), 2.36 (t, 2H, J=7.2 Hz), 2.12 (t, 2H, J=7.2H), 1.42 (s, 6H).

1671d) 8-Methoxy-5,5-dimethyl-7-nitro-1,3,4,5-tetrahydro-benzo[b]azepin-2-one (160 mg, 0.60 mmol) was hydrogenated in the presence of 10% Pd/C, 50% wet (80 mg) in Methanol (15 mL) overnight (balloon). Conc. of the filtered reaction afforded 7-Amino-8-methoxy-5,5-dimethyl-1,3,4,5-tetrahydro-benzo[b]azepin-2-one (122 mg, 86%), which was used without purification. 1H-NMR (CDCl3): 6.94 (s, 1H), 6.76 (s, 1H), 6.38 (s, 1H), 3.85 (s, 3H), 3.76 (s, 2H), 2.35 (t, 2H, J=7.0 Hz), 2.07 (t, 2H, J=7.0 Hz), 1.37 (s, 6H).

1671e) 7-Amino-8-methoxy-5,5-dimethyl-1,3,4,5-tetrahydro-benzo[b]azepin-2-one (59 mg, 0.25 mmol), 2-(2,5-Dichloro-pyrimidin-4-ylamino)-N-methyl-benzamide (75 mg, 0.25 mmol), and 10-Camphorsulfonic acid (58 mg, 0.25 mmol), in Isopropyl alcohol (4 mL) were irradiated at 120° C. for 40 min in a CEM microwave. The sample was cooled, treated with MP-carbonate resin, filtered and conc. in vacuo. Silica gel chromatography afforded the product as a yellow solid (34 mg, 27%). MP: 197-199° C.; LCMS 495 (M+H); 1H-NMR, CDCl3: 11.1 (s, 1H), 8.66 (d, 1H, J=8.4 Hz), 8.38 (s, 1H), 8.16 (s, 1H), 7.50 (d, 1H, J=7.9 Hz), 7.43 (dd, 1H, J=7.7, 7.7 Hz), 7.30 (m, 1H), 7.08 (m, 1H), 7.01 (s, 1H), 6.45 (s, 1H), 6.21 (s, 1H), 3.90 (s, 3H), 3.07 (d, 3H, J=4.9 Hz), 2.40 (t, 2H, J=7.0 Hz), 2.08 (t, 2H, J=7.0 Hz), 1.30 (s, 6H).

Example 1672

7-[5-Chloro-4-(2-methoxy-4-morpholin-4-yl-phenylamino)-pyrimidin-2-ylamino]-8-methoxy-5,5-dimethyl-1,3,4,5-tetrahydro-benzo[b]azepin-2-one 7-Amino-8-methoxy-5,5-dimethyl-1,3,4,5-tetrahydro-benzo[b]azepin-2-one (59 mg, 0.25 mmol), (2,5-Dichloro-pyrimidin-4-yl)-(2-methoxy-4-morpholin-4-yl-phenyl)-amine (89 mg, 0.25 mmol), and 10-Camphorsulfonic acid (59 mg, 0.25 mmol) in Isopropyl alcohol (4 mL) were irradiated at 120° C. for 40 min in a CEM microwave. The sample was cooled, treated with MP-carbonate resin, filtered and conc. in vacuo. Silica gel chromatography afforded 7-[5-Chloro-4-(2-methoxy-4-morpholin-4-yl-phenylamino)-pyrimidin-2-ylamino]-8-methoxy-5,5-dimethyl-1,3,4,5-tetrahydro-benzo[b]azepin-2-one as a white solid (57 mg, 41%). MP: 246-248° C., LCMS: 553 (M+H); 1H-NMR, CDCl3: 8.39 (s, 1H), 8.26 (d, 1H, J=8.8 Hz), 8.08 (s, 1H), 7.60 (s, 1H), 7.25 (m, 1H), 7.06 (s, 1H), 6.55 (s, 1H), 6.47 (m, 1H), 6.45 (s, 1H), 3.94 (s, 3H), 3.89 (m, 7H), 3.14 (m, 4H), 2.40 (t, 2H, J=7.0 Hz), 2.10 (t, 2H, J=7.0 Hz), 1.32 (s, 6H).

Example 1673

(1S,2S,3R,4R)-3-{5-Chloro-2-[8-methoxy-3-((S)-3,3,3-trifluoro-2-hydroxy-propyl)-2,3,4,5-tetrahydro-1H-benzo[d]azepin-7-ylamino]-pyrimidin-4-ylamino}-bicyclo[2.2.1]hept-5-ene-2-carboxylic acid amide (S)-3-(7-Amino-8-methoxy-1,2,4,5-tetrahydro-benzo[d]azepin-3-yl)-1,1,1-trifluoro-propan-2-ol (88 mg, 0.29 mmol), (1S,2S,3R,4R)-3-(2,5-Dichloro-pyrimidin-4-ylamino)-bicyclo[2.2.1]hept-5-ene-2-carboxylic acid amide (89 mg, 0.30 mmol), and 10-Camphorsulfonic acid (105 mg, 0.452 mmol) in 2-Methoxyethanol (4 mL) was heated in a microwave vial at 120° C. for 4 h. The brown solution was added dropwise to a satd. sodium bicarbonate solution (10 mL) and the vial was rinsed with 2 mL water and also added. The precipitated product was allowed to stand for 30 min, filtered and washed with water (5 mL). The crude solid was chromatographed (2×12 g silica gel, 0-80% EtOAc:Hex) to afford (1S,2S,3R,4R)-3-{5-Chloro-2-[8-methoxy-3-((S)-3,3,3-trifluoro-2-hydroxy-propyl)-2,3,4,5-tetrahydro-1H-benzo[d]azepin-7-ylamino]-pyrimidin-4-ylamino}-bicyclo[2.2.1]hept-5-ene-2-carboxylic acid amide as a beige solid (73 mg, 44%). LCMS: 567 (M+H); MP=120-126° C.; 1H-NMR, CDCl3: 8.24 (s, 1H), 7.92 (s, 1H), 7.43 (s, 1H), 6.66 (s, 1H), 6.61 (d, 1H, J=7.9 Hz), 6.33 (m, 2H), 5.57 (br s, 1H), 5.29 (br s, 1H), 4.46 (m, 1H), 4.07 (m, 1H), 3.89 (s, 3H), 3.10 (br s, 1H), 2.8-3.0 (m, 9H), 2.70 (m, 3H), 2.53 (d, 1H, J=8.1 Hz), 2.28 (d, 1H, J=9.4 Hz), 1.68 (d, 1H, J=8.7 Hz).

Example 1674

N-{(1R,2R)-2-[5-Chloro-2-(5,5-dimethyl-2-oxo-2,3,4,5-tetrahydro-1H-benzo[b]azepin-7-ylamino)-pyrimidin-4-ylamino]-cyclohexyl}-N-methyl-methanesulfonamide 1674a) N-[(1R,2R)-2-(2,5-Dichloro-pyrimidin-4-ylamino)-cyclohexyl]-methanesulfonamide (490 mg, 1.4 mmol) in Acetone (5 mL), Cesium Carbonate (706 mg, 2.17 mmol) was added; after 15 min, Methyl iodide (95.0 uL, 1.53 mmol) was added and the mixture stirred at room temperature. After 4 h, a second aliquot of Methyl iodide (15 uL, 0.24 mmol) was added to drive the reaction to completion. After 30 min, the mixture was partitioned between 20 mL DCM/20 mL water, extracted 2×20 mL DCM. The combined organics were dried over sodium sulfate, filtered and con. in vacuo to afford N-[(1R,2R)-2-(2,5-Dichloro-pyrimidin-4-ylamino)-cyclohexyl]-N-methyl-methanesulfonamide as an oil in quantitative yield. 1H-NMR (CDCl3): 8.02 (s, 1H), 5.94 (d, 1H, J=7.6 Hz), 4.11 (m, 1H), 3.74 (m, 1H), 2.84 (s, 3H), 2.80 (s, 3H), 2.35 (m, 1H), 1.84 (m, 3H), 1.71 (m, 1H), 1.42 (m, 2H), 1.27 (m, 1H).

1674b) N-[(1R,2R)-2-(2,5-Dichloro-pyrimidin-4-ylamino)-cyclohexyl]-N-methyl-methanesulfonamide (95 mg, 0.27 mmol) in Isopropyl alcohol (4 mL) was added to 7-Amino-5,5-dimethyl-1,3,4,5-tetrahydro-benzo[b]azepin-2-one (56 mg, 0.27 mmol) and 10-Camphorsulfonic acid (64 mg, 0.28 mmol) and was heated in a Microwave vial for 90 min at 120° C. Upon cooling, the mixture was treated with MP-Carbonate (2.69 mmol/g loading; 0.29 g, 0.78 mmol) for 1 h, was filtered and was concentrated in vacuo. The material was taken up in DCM and was chromatographed (ISCO, 12 g silica gel, 50% EtOAc/Hex-non-retained) to afford the N-{(1R,2R)-2-[5-Chloro-2-(5,5-dimethyl-2-oxo-2,3,4,5-tetrahydro-1H-benzo[b]azepin-7-ylamino)-pyrimidin-4-ylamino]-cyclohexyl}-N-methyl-methanesulfonamide as off white solids (145 mg, 100%). mp=140-145° C.; LCMS: 521 (M+H); 1H-NMR, CDCl3: 7.92 (s, 1H), 7.68 (d, 1H, J=8.5 Hz), 7.46 (s, 1H), 7.39 (s, 1H), 7.11 (s, 1H), 6.89 (d, 1H, J=8.5 Hz), 5.69 (d, 1H, 7.8 Hz), 4.07 (m, 1H), 3.77 (m, 1H), 2.85 (s, 3H), 2.75 (s, 3H), 2.41 (t, 2H, J=7.0 Hz), 2.13 (m, 2H, J=7.0 Hz), 1.90 (m, 4H), 1.44 (s, 6H), 1.37 (m, 4H).

Example 1675

N-{(1R,2R)-2-[5-Chloro-2-(5,5-dimethyl-2-oxo-2,3,4,5-tetrahydro-1H-benzo[b]azepin-7-ylamino)-pyrimidin-4-ylamino]-cyclohexyl}-N-ethyl-methanesulfonamide 1675a) N-[(1R,2R)-2-(2,5-Dichloro-pyrimidin-4-ylamino)-cyclohexyl]-methanesulfonamide (490 mg, 1.4 mmol) in Acetone (5 mL) was added Cesium Carbonate (706 mg, 2.17 mmol); after 15 min, Iodoethane (122 uL, 1.53 mmol) was added and the mixture stirred at room temperature 5d. Conc. in vacuo onto Celite and chromatography (0-20% EtOAc:Hex, ISCO silica gel) afforded N-[(1R,2R)-2-(2,5-Dichloro-pyrimidin-4-ylamino)-cyclohexyl]-N-ethyl-methanesulfonamide as a clear oil (400 mg, 75%). 1H-NMR (CDCl3): 8.01 (s, 1H), 6.32 (d, 1H, J=6.8 Hz), 4.03 (m, 1H), 3.76 (m, 1H), 3.33 (m, 1H), 3.20 (m, 1H), 2.91 (s, 3H), 2.41 (m, 1H), 1.92 (m, 2H), 1.72 (m, 2H), 1.40 (m, 2H), 1.21 (m, 4H).

1675b) N-[(1R,2R)-2-(2,5-Dichloro-pyrimidin-4-ylamino)-cyclohexyl]-N-ethyl-methanesulfonamide (99 mg, 0.27 mmol) in Isopropyl alcohol (4 mL) was added to 10-Camphorsulfonic acid (12 mg, 0.052 mmol) and 7-Amino-5,5-dimethyl-1,3,4,5-tetrahydro-benzo[b]azepin-2-one (56 mg, 0.27 mmol) and was heated in a Microwave vial for 90 min at 120° C. Upon cooling, the mixture was treated with MP-Carbonate (2.69 mmol/g loading; 0.29 g, 0.78 mmol) for 1 h, was filtered and was concentrated in vacuo onto Celite. Chromatography (ISCO, 12 g silica gel, 40-80% EtOAc:Hex) afforded N-{(1R,2R)-2-[5-Chloro-2-(5,5-dimethyl-2-oxo-2,3,4,5-tetrahydro-1H-benzo[b]azepin-7-ylamino)-pyrimidin-4-ylamino]-cyclohexyl}-N-ethyl-methanesulfonamide as an off white foam (78 mg, 54%). LCMS: 535 (M+H); 1H-NMR, CDCl3: 7.91 (s, 1H), 7.74 (d, 1H, J=8.5 Hz), 7.34 (s, 1H), 7.25 (s, 1H), 7.00 (s, 1H), 6.88 (d, 1H J=8.5 Hz), 6.02 (d, 1H, J=8.2 Hz), 3.99 (m, 1H), 3.75 (m, 1H), 3.30 (m, 1H), 3.20 (m, 1H), 2.92 (s, 3H), 2.45 (m, 1H), 2.40 (t, 2H, J=7.0 Hz), 2.13 (t, 2H, J=7.0 Hz), 1.95 (m, 2H), 1.44 (s, 6H), 1.39 (m, 3H), 1.16 (t, 3H, J=7.0 Hz).

Example 1676

N-((1R,2R)-2-{5-Chloro-2-[8-methoxy-3-(2-methoxy-ethyl)-2,3,4,5-tetrahydro-1H-benzo[d]azepin-7-ylamino]-pyrimidin-4-ylamino}-cyclohexyl)-N-methyl-methanesulfonamide N-[(1R,2R)-2-(2,5-Dichloro-pyrimidin-4-ylamino)-cyclohexyl]-N-methyl-methanesulfonamide (95 mg, 0.27 mmol), 8-Methoxy-3-(2-methoxy-ethyl)-2,3,4,5-tetrahydro-1H-benzo[d]azepin-7-ylamine (67 mg, 0.27 mmol), and 10-Camphorsulfonic acid (96 mg, 0.41 mmol) in Isopropyl alcohol (4 mL) and was heated in a microwave vial for 2 h at 120° C. Upon cooling, the mixture was treated with MP-Carbonate (2.69 mmol/g loading; 0.35 g, 0.941 mmol) for 1 h, was filtered and was concentrated in vacuo onto Celite. Chromatography (ISCO, 12 g silica gel, 40-80% EtOAc:Hex) afforded N-((1R,2R)-2-{5-Chloro-2-[8-methoxy-3-(2-methoxy-ethyl)-2,3,4,5-tetrahydro-1H-benzo[d]azepin-7-ylamino]-pyrimidin-4-ylamino}-cyclohexyl)-N-methyl-methanesulfonamide as a off white foam (99 mg, 65%). LCMS: 567 (M+H); 1H-NMR, CDCl3: 8.17 (s, 1H), 7.91 (s, 1H), 7.35 (s, 1H), 6.64 (s, 1H), 5.56 (s, 1H), 4.10 (m, 1H), 3.87 (s, 3H), 3.7 (m, 3H), 3.35 (s, 3H), 2.9 (m, 6H), 2.83 (s, 3H), 2.74 (s, 3H), 2.4 (m, 1H), 1.9 (m, 4H), 1.65 (m, 3H), 1.35 (m, 4H).

Example 1677

N-((1R,2R)-2-{5-Chloro-2-[8-methoxy-3-(2-methoxy-ethyl)-2,3,4,5-tetrahydro-1H-benzo[d]azepin-7-ylamino]-pyrimidin-4-ylamino}-cyclohexyl)-N-ethyl-methanesulfonamide N-[(1R,2R)-2-(2,5-Dichloro-pyrimidin-4-ylamino)-cyclohexyl]-N-ethyl-methanesulfonamide (99 mg, 0.27 mmol), 8-Methoxy-3-(2-methoxy-ethyl)-2,3,4,5-tetrahydro-1H-benzo[d]azepin-7-ylamine (67 mg, 0.27 mmol), and 10-Camphorsulfonic acid (94 mg, 0.40 mmol) in Isopropyl alcohol (4 mL) was heated in a microwave vial for 90 min at 120° C. Upon cooling, the mixture was treated with MP-Carbonate (2.69 mmol/g loading; 0.35 g, 0.94 mmol) for 1 h, was filtered and was concentrated in vacuo onto Celite. Chromatography (ISCO, 12 g silica gel, 40-80% EtOAc:Hex) afforded N-((1R,2R)-2-{5-Chloro-2-[8-methoxy-3-(2-methoxy-ethyl)-2,3,4,5-tetrahydro-1H-benzo[d]azepin-7-ylamino]-pyrimidin-4-ylamino}-cyclohexyl)-N-ethyl-methanesulfonamide as an off white foam (70 mg, 40%). LCMS: 581 (M+H); 1H-NMR, CDCl3: 8.18 (s, 1H), 7.90 (s, 1H), 7.35 (s, 1H), 6.64 (s, 1H), 5.86 (s, 1H), 4.05 (m, 1H), 3.87 (s, 3H), 3.80 (m, 3H), 3.54 (m, 1H), 3.3 (s, 3H), 3.25 (m, 3H), 2.6-2.9 (m, 10H), 2.45 (m, 1H), 1.94 (m, 2H), 1.82 (m, 1H), 1.7 (m, 1H), 1.1-1.5 (m, 7H).

Example 1678

N-{(1R,2R)-2-[5-Chloro-2-(1-ethyl-8-methoxy-2-oxo-2,3,4,5-tetrahydro-1H-benzo[b]azepin-7-ylamino)-pyrimidin-4-ylamino]-cyclohexyl}-N-methyl-methanesulfonamide N-[(1R,2R)-2-(2,5-Dichloro-pyrimidin-4-ylamino)-cyclohexyl]-N-methyl-methanesulfonamide (79 mg, 0.22 mmol), 7-Amino-1-ethyl-8-methoxy-1,3,4,5-tetrahydro-benzo[b]azepin-2-one (52 mg, 0.22 mmol), and 10-Camphorsulfonic acid (80 mg, 0.34 mmol) in Isopropyl alcohol (3 mL) and was heated in a microwave vial for 2 h at 120° C. Upon cooling, the mixture was treated with MP-Carbonate (2.69 mmol/g loading; 0.29 g, 0.78 mmol) for 1 h, was filtered and was concentrated in vacuo. Chromatography (ISCO, 2×12 g silica gel, 0-85% EtOAc:Hex) afforded N-{(1R,2R)-2-[5-Chloro-2-(1-ethyl-8-methoxy-2-oxo-2,3,4,5-tetrahydro-1H-benzo[b]azepin-7-ylamino)-pyrimidin-4-ylamino]-cyclohexyl}-N-methyl-methanesulfonamide as a white foam (32 mg, 26%). LCMS: 551 (M+H), 1H-NMR (CDCl3): 8.20 (s, 1H), 7.93 (s, 1H), 7.44 (s, 1H), 6.70 (s, 1H), 5.61 (d, 1H, J=7.9 Hz), 4.11 (m, 2H), 3.90 (s, 3H), 3.78 (m, 1H), 2.84 (s, 3H), 2.75 (s, 3H), 2.59 (br s, 1H), 2.41 (m, 1H), 2.28 (m, 2H), 2.19 (br s, 1H), 1.90 (m, 3H), 1.71 (m, 1H), 1.2-1.5 (m, 6H), 1.14 (t, 3H, J=7.0 Hz).

Example 1679

N-{(1R,2R)-2-[5-Chloro-2-(1-ethyl-6-methoxy-2-oxo-2,3,4,5-tetrahydro-1H-benzo[b]azepin-7-ylamino)-pyrimidin-4-ylamino]-cyclohexyl}-N-methyl-methanesulfonamide N-[(1R,2R)-2-(2,5-Dichloro-pyrimidin-4-ylamino)-cyclohexyl]-N-methyl-methanesulfonamide (79 mg, 0.22 mmol), 7-Amino-1-ethyl-6-methoxy-1,3,4,5-tetrahydro-benzo[b]azepin-2-one (52 mg, 0.22 mmol), and 10-Camphorsulfonic acid (80 mg, 0.34 mmol) in Isopropyl alcohol (3 mL) and was heated in a microwave vial for 2 h at 120° C. Upon cooling, the mixture was treated with MP-Carbonate (2.69 mmol/g loading; 0.29 g, 0.78 mmol) for 1 h, was filtered and was concentrated in vacuo. Chromatography (ISCO, 2×12 g silica gel, 0-80% EtOAc:Hex) afforded N-{(1R,2R)-2-[5-Chloro-2-(1-ethyl-6-methoxy-2-oxo-2,3,4,5-tetrahydro-1H-benzo[b]azepin-7-ylamino)-pyrimidin-4-ylamino]-cyclohexyl}-N-methyl-methanesulfonamide as a white foam (33 mg, 27%). LCMS: 551 (M+H), 1H-NMR (CDCl3): 8.35 (d, 1H, J=8.9 Hz), 7.94 (s, 1H), 7.35 (s, 1H), 6.96 (d, 1H, J=8.9 Hz), 5.72 (d, 1H, J=7.4 Hz), 4.06 (m, 1H), 3.82 (m, 4H), 3.5 (br s, 1H), 3.0 (br s, 1H), 2.85 (s, 3H), 2.78 (s, 3H), 2.47 (m, 1H), 2.29 (m, 2H), 1.84 (m, 3H), 1.71 (m, 1H), 1.25-1.5 (m, 6H), 1.13 (t, 3H, J=7.1 Hz).

Example 1680

N-{(1R,2R)-2-[5-Chloro-2-(1,5,5-trimethyl-2-oxo-2,3,4,5-tetrahydro-1H-benzo[b]azepin-7-ylamino)-pyrimidin-4-ylamino]-cyclohexyl}-N-methyl-methanesulfonamide N-[(1R,2R)-2-(2,5-Dichloro-pyrimidin-4-ylamino)-cyclohexyl]-N-methyl-methanesulfonamide (79 mg, 0.22 mmol), 7-Amino-1,5,5-trimethyl-1,3,4,5-tetrahydro-benzo[b]azepin-2-one (49 mg, 0.22 mmol), and 10-Camphorsulfonic acid (80 mg, 0.34 mmol) in Isopropyl alcohol (3 mL) and was heated in a microwave vial for 2 h at 120° C. Upon cooling, the mixture was treated with MP-Carbonate (2.69 mmol/g loading; 0.29 g, 0.78 mmol) for 1 h, was filtered and was concentrated in vacuo. Chromatography (ISCO, 2×12 g silica gel, 0-80% EtOAc:Hex) afforded N-{(1R,2R)-2-[5-Chloro-2-(1,5,5-trimethyl-2-oxo-2,3,4,5-tetrahydro-1H-benzo[b]azepin-7-ylamino)-pyrimidin-4-ylamino]-cyclohexyl}-N-methyl-methanesulfonamide as a white foam (64 mg, 53%). LCMS: 535 (M+H), 1H-NMR (CDCl3): 7.92 (s, 1H), 7.75 (d, 1H, J=8.5 Hz), 7.29 (s, 1H), 7.11 (d, 1H, J=8.5 Hz), 6.85 (s, 1H), 5.65 (d, 1H, J=7.8 Hz), 4.08 (m, 1H), 3.75 (m, 1H), 3.29 (s, 3H), 2.84 (s, 3H), 2.74 (s, 3H), 2.41 (m, 1H), 2.37 (m, 2H), 2.04 (m, 1H), 1.84 (m, 3H), 1.67 (m, 1H), 1.25-1.5 (m, 10H).

Example 1681

N-{(1R,2R)-2-[5-Chloro-2-(7-morpholin-4-yl-6,7,8,9-tetrahydro-5H-benzocyclohepten-2-ylamino)-pyrimidin-4-ylamino]-cyclohexyl}-N-methyl-methanesulfonamide N-[(1R,2R)-2-(2,5-Dichloro-pyrimidin-4-ylamino)-cyclohexyl]-N-methyl-methanesulfonamide (79 mg, 0.22 mmol), 7-Morpholin-4-yl-6,7,8,9-tetrahydro-5H-benzocyclohepten-2-ylamine (55 mg, 0.22 mmol), and 10-Camphorsulfonic acid (80 mg, 0.34 mmol) in Isopropyl alcohol (3 mL) and was heated in a microwave vial for 2 h at 120° C. Upon cooling, the mixture was treated with MP-Carbonate (2.69 mmol/g loading; 0.29 g, 0.78 mmol) for 1 h, was filtered and was concentrated in vacuo. Chromatography (ISCO, 2×12 g silica gel, 0-5% MeOH:EtOAc) afforded the 1:1 diastereomeric mixture of N-{(1R,2R)-2-[5-Chloro-2-(7-morpholin-4-yl-6,7,8,9-tetrahydro-5H-benzocyclohepten-2-ylamino)-pyrimidin-4-ylamino]-cyclohexyl}-N-methyl-methanesulfonamide as a white foam (50 mg, 40%). LCMS: 563 (M+H), 1H-NMR (CDCl3): 7.85 (s, 1H), 7.32 (m, 3H), 7.04 (d, 1H, J=7.9 Hz), 5.67 (s, 1H), 4.06 (m, 1H), 3.75 (m, 5H), 3.35 (m, 1H), 2.84 (s, 3H), 2.72 (s, 3H), 2.60 (m, 5H), 2.44 (m, 1H), 2.33 (m, 1H), 2.04 (m, 2H), 1.89 (m, 4H), 1.65 (m, 1H), 1.46 (m, 6H).

Example 1682

2-[5-Chloro-2-(1-methyl-2-oxo-2,3,4,5-tetrahydro-1H-benzo[b]azepin-7-ylamino)-pyrimidin-4-ylamino]-N-(2-cyano-ethyl)-N-methyl-benzamide 1682a) To Isatoic Anhydride (4.60 g, 28.2 mmol) in N,N-Dimethylformamide (30 mL) was added 3-Methylamino-propionitrile (3.00 mL, 32.1 mmol) and the reaction was stirred under an atmosphere of Nitrogen. After 6 h, the mixture was poured into 200 mL water, then extracted 3×100 mL DCM, washed with 100 mL satd. sodium bicarbonate, which was back extracted with 50 mL DCM. The combined organics were washed with brine (100 mL) and dried over sodium sulfate, then conc. in vacuo afforded 2-Amino-N-(2-cyano-ethyl)-N-methyl-benzamide as an oil in quantitative yield. 1H-NMR: 7.18 (dd, 1H, J=9.0, 9.0 Hz), 7.13 (d, 1H, J=7.3 Hz), 6.74 (m, 2H), 4.31 (br s, 2H), 3.76 (t, 2H, J=6.6 Hz), 3.15 (s, 3H), 2.75 (t, 2H, J=6.6 Hz).

1682b) 2-Amino-N-(2-cyano-ethyl)-N-methyl-benzamide (5.73 g, 28.2 mmol) in N,N-Dimethylformamide (50 mL) was treated with 2,4,5-Trichloro-pyrimidine (4.00 mL, 34.9 mmol) and Potassium carbonate (5.8 g, 42 mmol). The mixture was heated at 80° C. for 4 h, then cooled to room temperature and stirred for 4 days. The reaction was diluted with 200 mL water, extracted with DCM (200 mL, then 2×50 mL). The combined organics were washed 1×100 mL brine, dried over sodium sulfate and conc. in vacuo to give an oil, which was chromatographed (ISCO 330 g silica gel, 0-80% EtOAc:Hex). The product eluted with ~60% EtOAc to afford N-(2-Cyano-ethyl)-2-(2,5-dichloro-pyrimidin-4-ylamino)-N-methyl-benzamide as an oil (5.0 g, 50%). 1H-NMR (CDCl3): 9.36 (s, 1H), 8.34 (d, 1H, J=8.4 Hz), 8.22 (s, 1H), 7.53 (m, 1H), 7.38 (m, 1H), 7.21 (m, 1H), 3.81 (m, 2H), 3.22 (s, 3H), 2.80 (m, 2H).

1682c) N-(2-Cyano-ethyl)-2-(2,5-dichloro-pyrimidin-4-ylamino)-N-methyl-benzamide (101 mg, 0.288 mmol), 7-Amino-1-methyl-1,3,4,5-tetrahydro-1-benzazepin-2-one (48 mg, 0.25 mmol), and 10-Camphorsulfonic acid (5.0 mg, 0.022 mmol) in Isopropyl alcohol (2.0 mL) were added into a microwave vial and irradiated at 120° C. for 30 min. The reaction was diluted with satd. sodium bicarbonate (5 mL) and cooled to aid in precipitate formation. The solids were collected and washed with 7 mL water. The solids contained product with starting chloropyrimidine and another impurity. The filtrate contained the aniline component, product and other impurities. The filtrate was extracted 3×10 mL DCM, dried and concentrated. The solids were chromatographed (ISCO, 12 g silica gel, 0-100% EtOAc:Hex) separately from the filtrate, and clean fractions were combined to give the product as a yellow foam (44 mg, 35%). LCMS: 504 (M+H), 1H-NMR (CDCl3): 8.93 (s, 1H), 8.34 (d, 1H, J=8.2 Hz), 8.10 (s, 1H), 7.44 (m, 3H), 7.37 (d, 1H, J=7.8 Hz), 7.18 (dd, 1H, J=7.4, 7.4 Hz), 7.07 (d, 1H, J=8.3 Hz), 6.95 (s, 1H), 3.81 (br s, 2H), 3.33 (s, 3H), 3.20 (s, 3H), 2.81 (br s, 2H), 2.64 (m, 2H), 2.32 (t, 2H, J=7.2 Hz), 2.15 (m, 2H).

Example 1683

N-{(1R,2R)-2-[5-Chloro-2-(7-fluoro-5-oxo-2,3,4,5-tetrahydro-benzo[f][1,4]oxazepin-9-ylamino)-pyrimidin-4-ylamino]-cyclohexyl}-methanesulfonamide 1683a) 6-Fluoro-chroman-4-one (539 mg, 3.24 mmol) was dissolved in Sulfuric acid (6.0 mL) and Sodium azide (258 mg, 3.97 mmol) was added at room temperature. The reaction was stirred for 30 h, then poured into water. The solids were collected by filtration, washing with 50 mL water. After drying, 7-Fluoro-3,4-dihydro-2H-b enzo[f][1,4]oxazepin-5-one was isolated as a white solid (395 mg, 67%). 1H-NMR (CDCl3): 7.65 (m, 1H), 7.15 (m, 1H), 7.01 (m, 1H), 6.74 (s, 1H), 1683b) 7-Fluoro-3,4-dihydro-2H-benzo[f][1,4]oxazepin-5-one (346 mg, 1.91 mmol) in Acetonitrile (10 mL) and Trifluoroacetic anhydride (0.85 mL, 6.0 mmol) was treated with Potassium nitrate (0.203 g, 2.00 mmol) at room temperature for 24 h. Aq. NaOH (15% w/w, 10 mL) was added and the mixture extracted 3×15 mL DCM. The DCM extract was washed with water (20 mL) and brine (20 mL) then dried over sodium sulfate and conc. in vacuo. 1H-, 19F-NMR and HPLC showed a 2-3:1 mixture of 7-Fluoro-9-nitro-3,4-dihydro-2H-benzo[f][1,4]oxazepin-5-one and 7-Fluoro-3,4-dihydro-2H-benzo[f][1,4]oxazepin-5-one, which was chromatographed (ISCO, 40 g, 0-75% EtOAc:Hex) to give 7-Fluoro-9-nitro-3,4-dihydro-2H-benzo[f][1,4]oxazepin-5-one, enriched in the mixture, but still containing 7-Fluoro-3,4-dihydro-2H-benzo[f][1,4]oxazepin-5-one. This mixture was dissolved in Ethanol (10 mL) and added to Palladium on Carbon 10% (0.05 g) wetted with a small amount of water. The mixture was shaken under an atmosphere of Hydrogen (40 psi) for 1.5 h, then filtered through Celite, washing with ethanol. Conc. in vacuo gave a white solid, which was taken up in Et2O with minimal MeOH to solubilize, then extracted with 15 mL 1N HCl. The aq. extract was washed once with ether (10 mL) then basified with 15% NaOH, then extracted 8×10 mL DCM. The organic layers were dried over sodium sulfate and conc. in vacuo to give 9-Amino-7-fluoro-3,4-dihydro-2H-benzo[f][1,4]oxazepin-5-one as a white solid (120 mg, 35% over two steps.

1683c) 9-Amino-7-fluoro-3,4-dihydro-2H-benzo[f][1,4]oxazepin-5-one (59 mg, 0.30 mmol), 10-Camphorsulfonic acid (11 mg, 0.047 mmol) and N-[(1R,2R)-2-(2,5-Dichloro-pyrimidin-4-ylamino)-cyclohexyl]-methanesulfonamide (0.104 g, 0.306 mmol) in 2-Methoxyethanol (5 mL) were heated at 110° C. under an atmosphere of Nitrogen for 2 days. The mixture was cooled to r.t., neutralized with 100 mg MP-Carbonate and conc. in vacuo. The residue was partially taken up in DCM/MeOH, and the remainder was powdered onto Celite, then chromatographed (2×12 g silica gel, ISCO, 0-100% EtOAc:hexane, then 10% MeOH) to afford N-{(1R, 2R)-2-[5-Chloro-2-(7-fluoro-5-oxo-2,3,4,5-tetrahydro-benzo[f][1,4]oxazepin-9-ylamino)-pyrimidin-4-ylamino]-cyclohexyl}-methanesulfonamide as a beige solid (69 mg, 46%). MP=177-181° C.; LCMS: 499 (M+H); 1H-NMR (CDCl3): 8.27 (dd, 1H, J=2.6, 10.9 Hz), 7.98 (1H, s), 7.62 (s, 1H), 7.03 (dd, 1H, J=2.9, 8.6 Hz), 6.95 (m, 1H), 6.85 (m, 1H), 6.02 (d, 1H, J=7.0 Hz), 4.21 (m, 1H), 4.15 (m, 1H), 3.82 (m, 1H), 3.32 (m, 3H), 2.98 (s, 3H), 2.33 (m, 1H), 2.18 (m, 1H), 1.87 (m, 1H), 1.78 (m, 1H), 1.64 (m, 1H), 1.41 (m, 2H), 1.22 (m, 1H).

Example 1684

9-[5-Chloro-4-(2-methoxy-4-morpholin-4-yl-phenylamino)-pyrimidin-2-ylamino]-7-fluoro-3,4-dihydro-2H-benzo[f][1,4]oxazepin-5-one 9-Amino-7-fluoro-3,4-dihydro-2H-benzo[f][1,4]oxazepin-5-one (59 mg, 0.30 mmol), 10-Camphorsulfonic acid (11 mg, 0.047 mmol) and in 2-Methoxyethanol (5 mL) were heated at 110° C. under an atmosphere of Nitrogen for 2 days. The mixture was cooled to r.t., neutralized with 100 mg MP-Carbonate and conc. in vacuo. The residue was powdered onto Celite, then chromatographed (2×12 g silica gel, ISCO, 0-10% MeOH:EtOAc) to afford 9-[5-Chloro-4-(2-methoxy-4-morpholin-4-yl-phenylamino)-pyrimidin-2-ylamino]-7-fluoro-3,4-dihydro-2H-benzo[f][1,4]oxazepin-5-one as a yellow solid (76 mg, 50%). MP>230° C.; LCMS: 515 (M+H); 1H-NMR (CDCl3): 8.37 (d, 1H, J=11.1 Hz), 8.03 (s, 1H), 7.97 (d, 1H, J=8.5 Hz), 7.52 (s, 1H), 7.14 (dd, 1H, J=2.6, 8.5 Hz), 6.61 (d, 1H, J=8.9 Hz), 6.57 (s, 1H), 6.34 (m, 1H), 4.45 (t, 2H, J=4.9 Hz), 3.91 (m, 7H), 3.48 (m, 2H), 3.20 (t, 4H, J=4.5 Hz).

Example 1685

5-Chloro-N*2*-[3-(2-methoxy-ethyl)-2,3,4,5-tetrahydro-1H-benzo[d]azepin-7-yl]-N*4*-[2-(propane-2-sulfonyl)-phenyl]-pyrimidine-2,4-diamine 10-Camphorsulfonic acid (49 mg, 0.21 mmol) was added to 3-(2-Methoxy-ethyl)-2,3,4,5-tetrahydro-1H-benzo[d]azepin-7-ylamine (44 mg, 0.20 mmol) and (2,5-Dichloropyrimidin-4-yl)-[2-(propane-2-sulfonyl)-phenyl]-amine (66 mg, 0.19 mmol) in Isopropyl alcohol (2 mL). The mixture was irradiated in a CEM microwave (140° C., 30 min). MP-Carbonate (2.69 mmol/g loading; 0.16 g, 0.43 mmol) was added and the mixture stirred for 1 h, then filtered, washing with 2 mL iPrOH. Brine was added, but the only ppt was NaCl. The aq. layer was extracted with EtOAc, and combined with the iPrOH, dried and conc. in vacuo. The residue was taken up in DCM with a few drops of MeOH and chromatographed (ISCO, 2×12 g, 0-10% MeOH:DCM) to afford 5-Chloro-N*2*-[3-(2-methoxy-ethyl)-2,3,4,5-tetrahydro-1H-benzo[d]azepin-7-yl]-N*4*-[2-(propane-2-sulfonyl)-phenyl]-pyrimidine-2,4-diamine as a colorless oil (63 mg, 62%). LCMS 530 (M+H), 1H-NMR (CDCl3): 9.58 (s, 1H), 8.57 (d, 1H, J=8.4 Hz), 8.13 (s, 1H), 7.91 (d, 1H, J=7.9 Hz), 7.59 (dd, 1H, J=7.8, 8.1 Hz), 7.24 (m, 3H), 7.02 (d, 1H, J=7.9 Hz), 6.94 (s, 1H), 3.55 (m, 2H), 3.38 (s, 3H), 3.24 (sept, 1H, J=6.8 Hz), 2.88 (m, 4H), 2.73 (m, 6H), 1.31 (d, 6H, J=6.8 Hz).

Example 1686

2-{5-Chloro-2-[3-(2-methoxy-ethyl)-2,3,4,5-tetrahydro-1H-benzo[d]azepin-7-ylamino]-pyrimidin-4-ylamino}-N,N-dimethyl-benzenesulfonamide 10-Camphorsulfonic acid (53 mg, 0.23 mmol) was added to 3-(2-Methoxy-ethyl)-2,3,4,5-tetrahydro-1H-benzo[d]azepin-7-ylamine (48 mg, 0.22 mmol) and 2-(2,5-Dichloropyrimidin-4-ylamino)-N,N-dimethyl-benzenesulfonamide (72 mg, 0.21 mmol) in Isopropyl alcohol (2 mL). The mixture was irradiated in a CEM microwave (140° C., 30 min). MP-Carbonate (2.69 mmol/g loading; 0.18 g, 0.47 mmol) was added and the mixture stirred for 1 h and filtered, washing with DCM. The filtrate was conc. in vacuo. The residue was taken up in DCM with a few drops of MeOH and chromatographed (ISCO, 2×12 g, 0-12% MeOH:DCM) to afford 2-{5-Chloro-2-[3-(2-methoxy-ethyl)-2,3,4,5-tetrahydro-1H-benzo[d]azepin-7-ylamino]-pyrimidin-4-ylamino}-N,N-dimethyl-benzenesulfonamide as a colorless wax (83 mg, 75%). LCMS 531 (M+H), 1H-NMR (CDCl3): 9.42 (s, 1H), 8.54 (d, 1H, J=8.4 Hz), 8.12 (s, 1H), 7.86 (d, 1H, J=7.5 Hz), 7.55 (dd, 1H, J=7.5, 8.2 Hz), 7.24 (m, 3H), 7.02 (d, 1H, J=7.8 Hz), 6.90 (s, 1H), 3.55 (m, 2H), 3.37 (s, 3H), 2.90 (m, 4H), 2.74 (m, 12H).

Example 1687

N-{(1R,2R)-2-[5-Chloro-2-(9-ethyl-2-fluoro-6,7,8,9-tetrahydro-5-oxa-9-aza-benzocyclohepten-3-ylamino)-pyrimidin-4-ylamino]-cyclohexyl}-methanesulfonamide 1687a) 5-Fluoro-2-methyl-benzoxazole (5.20 g, 0.0344 mol) was added to ice cooled Sulfuric acid (15.0 mL) such as to maintain the temperature below 25° C. After complete addition, a mixture of Sulfuric acid (2.75 mL) and Nitric acid (2.50 mL, 0.0536 mol) was added dropwise, maintaining the temperature below 18° C. After the addition was complete, the cooling bath was removed and the mixture was stirred at ambient temperature for 3 h, then was poured onto 100 mL ice with stirring. The solids were collected and washed with water (3×100 mL) and dried to give 5-Fluoro-2-methyl-6-nitro-benzoxazole as yellow solids. 1H-NMR (DMSO): 8.64 (d, 1H, J=5.4 Hz), 7.97 (d, 1H, J=10.8 Hz), 2.71 (s, 3H).

1687b) 5-Fluoro-2-methyl-6-nitro-benzoxazole (2.556 g, 13.03 mmol) was dissolved in Tetrahydrofuran (90 mL) and Acetic acid (4.5 mL, 79 mmol). Sodium borohydride (1.48 g, 39.1 mmol) was added and the reaction was stirred at room temperature for 90 min, then poured into 100 mL satd. sodium bicarbonate. The solution was extracted 3×50 mL DCM and the combined organics were washed with 1:1 brine:satd. sodium bicarbonate (50 mL) and dried over sodium sulfate, then conc. onto 10 g Celite. The crude product was chromatographed (120 g silica gel, ISCO, 0-20-40% EtOAc:Hex) to afford 2-Ethylamino-4-fluoro-5-nitro-phenol as a yellow solid (2.20 g, 84%). 1H-NMR (CDCl3): 7.55 (d, 1H, J=6.8 Hz), 6.26 (d, 1H, J=13.2 Hz), 5.51 (s, 1H), 5.05 (s, 1H), 3.26 (m, 2H), 1.34 (t, 3H, J=6.8 Hz).

1687c) 2-Ethylamino-4-fluoro-5-nitro-phenol (910 mg, 4.5 mmol) was azeotroped with toluene to ensure dryness, then was dissolved in Tetrahydrofuran (100 mL) and was cooled at 0° C. 3-Bromo-1-propanol (0.65 mL, 7.2 mmol), Tributylphosphine (2.0 mL, 8.2 mmol), and 40% w/w DEAD in Toluene (3.8 g, 8.7 mmol) were added in succession, and the reaction was stirred under an atmosphere of Nitrogen overnight. The mixture was conc. in vacuo onto silica gel (10 g) and chromatographed (ISCO, 80 g silica gel, 0-35% EtOAc:Hex) to afford [2-(3-Bromo-propoxy)-5-fluoro-4-nitro-phenyl]-ethylamine as an orange solid. The bromide was dissolved in Tetrahydrofuran (100 mL) and Sodium hydride, 60% disp. in mineral oil (0.20 g) was added. After 2 h, no reaction was observed, so N,N-Dimethylformamide (5 mL) was added. After o.n. stirring, no reaction, so additional Sodium hydride, 60% disp. in mineral oil (0.35 g) was added and the mixture was heated at 65° C. After 4 h, the reaction was complete and was cooled to rt. The reaction was quenched with water, diluted with ether (300 mL) and washed with water (40 mL), satd. sodium bicarbonate (2×40 mL) and brine (80 mL), dried over sodium sulfate and conc. in vacuo onto 6 g silica gel. Chromatography (ISCO, 80 g silica gel, 0-30% EtOAc:Hex) afforded 9-Ethyl-2-fluoro-3-nitro-6,7,8,9-tetrahydro-5-oxa-9-aza-benzocycloheptene as an orange solid (517 mg, 47% two steps). 1H-NMR (CDCl3): 7.62 (d, 1H, J=7.9 Hz), 6.33 (d, 1H, J=14 Hz), 4.21 (t, 2H, J=6.5 Hz), 3.63 (t, 2H, J=5.8 Hz), 3.35 (q, 2H, J=7.0 Hz), 2.12 (m, 2H), 1.25 (t, 3H, J=7.0 Hz).

1687d) 9-Ethyl-2-fluoro-3-nitro-6,7,8,9-tetrahydro-5-oxa-9-aza-benzocycloheptene (515 mg, 2.14 mmol) and 10% Palladium on Carbon (50% Wet) (0.25 g) in Ethanol (30 mL) were shaken under an atmosphere of Hydrogen (40 psi) for 4 h. The mixture was filtered through Celite, washing with ethanol, and conc. in vacuo to afford 9-Ethyl-2-fluoro-6,7,8,9-tetrahydro-5-oxa-9-aza-benzocyclohepten-3-ylamine as a green film (0.375 g, 84%). 1H-NMR (CDCl3): 6.60 (d, 1H, J=12.8 Hz), 6.44 (d, 1H, J=9.2 Hz), 3.99 (m, 2H), 3.42 (s, 1H), 3.09 (m, 4H), 1.96 (m, 2H), 1.56 (m, 2H), 1.17 (t, 3H, J=7.0 Hz).

17e) 10-Camphorsulfonic acid (70 mg, 0.30 mmol) was added to 9-Ethyl-2-fluoro-6,7,8,9-tetrahydro-5-oxa-9-aza-benzocyclohepten-3-ylamine (58 mg, 0.28 mmol) and N-[(1R,2R)-2-(2,5-Dichloro-pyrimidin-4-ylamino)-cyclohexyl]-methanesulfonamide (94 mg, 0.28 mmol) in Isopropyl alcohol (1 mL). The mixture was irradiated in a CEM microwave (140° C., min). MP-Carbonate (2.69 mmol/g loading; 0.22 g, 0.5793156293 mmol) and DCM (2 mL) were added and the mixture stirred for 1 h, then filtered onto a 5 g SiO2 cartridge, which was air dried. The sample was chromatographed (ISCO, 2×12 g SiO2, 0-50% EtOAc:Hex) to afford N-{(1R,2R)-2-[5-Chloro-2-(9-ethyl-2-fluoro-6,7,8,9-tetrahydro-5-oxa-9-aza-benzocyclohepten-3-ylamino)-pyrimidin-4-ylamino]-cyclohexyl}-methanesulfonamide as a purple film (40 mg, 30%). LCMS 513 (M+H), 1H-NMR (CDCl3): 7.92 (s, 1H), 7.76 (d, 1H, J=8.4 Hz), 6.76 (s, 1H), 6.62 (d, 1H, J=13.3 Hz), 5.39 (d, 1H, J=7.4 Hz), 5.11 (d, 1H, J=7.1 Hz), 4.09 (t, 2H, J=6.0 Hz), 3.93 (m, 1H), 3.25 (m, 5H), 2.81 (s, 3H), 2.20 (m, 2H), 2.00 (m, 2H), 1.82 (m, 2H), 1.43 (m, 4H), 1.20 (t, 3H, J=7.0 Hz). 19F-NMR: −135.

Example 1688

5-Chloro-N*2*-(9-ethyl-2-fluoro-6,7,8,9-tetrahydro-5-oxa-9-aza-benzocyclohepten-3-yl)-N*4*-(2-methoxy-4-morpholin-4-yl-phenyl)-pyrimidine-2,4-diamine 10-Camphorsulfonic acid (70.5 mg, 0.303 mmol) was added to 9-Ethyl-2-fluoro-6,7,8,9-tetrahydro-5-oxa-9-aza-benzocyclohepten-3-ylamine (58 mg, 0.28 mmol) and (2,5-Dichloro-pyrimidin-4-yl)-(2-methoxy-4-morpholin-4-yl-phenyl)-amine (98 mg, 0.28 mmol) in Isopropyl alcohol (2 mL). The mixture was irradiated in a CEM microwave (140° C., 30 min). MP-Carbonate (2.69 mmol/g loading; 0.21 g, 0.57 mmol) and DCM (2 mL) were added and the mixture stirred for 1 h, then filtered onto a 5 g SiO2 cartridge, which which was air dried. The sample was chromatographed (ISCO, 2×12 g SiO2, 0-50% EtOAc:Hex) to afford 5-Chloro-N*2*-(9-ethyl-2-fluoro-6,7,8,9-tetrahydro-5-oxa-9-aza-benzocyclohepten-3-yl)-N*4*-(2-methoxy-4-morpholin-4-yl-phenyl)-pyrimidine-2,4-diamine as a lavender film (43 mg, 29%). LCMS 529 (M+H), 1H-NMR (CDCl3): 8.23 (d, 1H, J=8.7 Hz), 8.00 (s, 1H), 7.77 (d, 1H, J=8.7 Hz), 7.58 (s, 1H), 6.75 (s, 1H), 6.60 (d, 1H, J=13.2 Hz), 6.55 (m, 2H), 4.08 (t, 2H, J=5.6 Hz), 3.91 (s, 3H), 3.88 (t, 4H, J=4.6 Hz), 3.17 (m, 8H), 1.98 (m, 2H), 1.21 (t, 3H, J=7.0 Hz); 19F-NMR: −135.

Example 1689

3-(2-{5-Chloro-2-[3-(2-methoxy-ethyl)-2,3,4,5-tetrahydro-1H-benzo[d]azepin-7-ylamino]-pyrimidin-4-ylamino}-5-morpholin-4-yl-phenoxy)-propionitrile 1689a) 5-Fluoro-2-nitro-phenol (3.05 g, 19.4 mmol; Alfa Aesar) in Acetonitrile (20 mL) was treated with Morpholine (3.6 mL, 41 mmol) under an atmosphere of Nitrogen. After 40 h at rt, the mixture was heated at 50° C. for 6 h to drive to completion. The mixture was concentrated to ca. ½ volume, precipitate formed and the mixture was diluted with 100 mL water. The solids were collected and washed 2×50 mL water then dried to afford 5-Morpholin-4-yl-2-nitro-phenol as a yellow solid (3.77 g, 87%). 1H-NMR (DMSO): 7.88 (d, 1H, J=9.6 Hz), 6.64 (dd, 1H, J=2.4, 9.6 Hz), 6.43 (d, 1H, J=2.4 Hz), 3.70 (t, 4H, J=4.8 Hz), 3.41 (t, 4H, J=4.8 Hz).

1689b) 1,2-Dibromoethane (1.50 mL, 17.4 mmol) was added to 5-Morpholin-4-yl-2-nitro-phenol (0.792 g, 3.53 mmol) and Potassium carbonate (1.71 g, 12.4 mmol) in Acetonitrile (40 mL) and the reaction was stirred under an atmosphere of Nitrogen at room temperature for 72 h (no change by HPLC), then was brought to reflux. After 4d, 1H-NMR indicated that the assumed starting material my LCMS was in actuality the 2:1 phenol-dibromoethane adduct. The reaction was cooled, diluted with ethyl acetate and filtered, conc. onto 5 g Celite. Chromatography (ISCO, 40 g, 0-40% EtOAc:Hex) afforded 4-[3-(2-Bromo-ethoxy)-4-nitro-phenyl]-morpholine (447 mg, 38%) as a colorless oil. 1H-NMR (CDCl$_3$): 7.99 (d, 1H, J=8.8 Hz), 6.48 (m, 1H), 6.36 (d, 1H, J=1.5 Hz), 4.39 (t, 2H, J=6.8 Hz), 3.85 (t, 4H, J=4.8 Hz), 3.71 (t, 2H, J=6.8 Hz), 3.34 (t, 4H, J=4.8 Hz).

1689c) Sodium cyanide (79 mg, 1.6 mmol) was added to 4-[3-(2-Bromo-ethoxy)-4-nitro-phenyl]-morpholine (447 mg, 1.35 mmol) in Dimethyl sulfoxide (5 mL) and the reaction was stirred at room temperature 48 h. The mixture was diluted with 50 mL Et2O and 20 mL water. DCM was added to solubilize ppt. The layers were separated and the aq. extracted 3×50 mL DCM. The combined organic extracts were washed with satd. sodium bicarbonate (50 mL) and brine (50 mL), conc. in vacuo and taken up in DCM for application to a 25 g SiO2 pre-load cartridge. Chromatography (0-100% EtOAc:Hex) afforded 3-(5-Morpholin-4-yl-2-nitro-phenoxy)-propionitrile as a yellow solid (212 mg, 57%). 1H-NMR (CDCl3): 8.01 (d, 1H, J=9.2 Hz), 6.52 (d, 1H, J=9.2 Hz), 6.40 (s, 1H), 4.31 (t, 2H, J=7.0 Hz), 3.86 (t, 4H, J=4.6 Hz), 3.35 (t, 4H, J=4.6 Hz), 2.93 (t, 2H, J=7.0 Hz).

1689d) 3-(5-Morpholin-4-yl-2-nitro-phenoxy)-propionitrile (209 mg, 0.754 mmol) and 10% Palladium on Carbon (50% Wet) (120 mg) in Ethanol (45 mL) was shaken under an atmosphere of Hydrogen (45 psi) for 1 h. The mixture was filtered, washing with ethanol, and Triethylamine (0.21 mL, 1.5 mmol) and 2,4,5-Trichloro-pyrimidine (0.13 mL, 1.1 mmol) were added to the filtrate. The mixture was stirred overnight, then poured into 100 mL water, then cooled. The solids were collected by filtration, to give 3-[2-(2,5-Dichloro-pyrimidin-4-ylamino)-5-morpholin-4-yl-phenoxy]-propionitrile as a purple solid (195 mg, 66%). 1H-NMR (CDCl3): 8.28 (d, 1H, J=8.0 Hz), 8.16 (s, 1H), 6.65 (d, 1H, J=8.0 Hz), 6.49 (s, 1H), 4.31 (t, 2H, J=5.2 Hz), 3.88 (t, 4H, J=4.1 Hz), 3.15 (t, 4H, J=4.1 Hz), 2.89 (t, 2H, J=5.2 Hz).

1689e) 3-[2-(2,5-Dichloro-pyrimidin-4-ylamino)-5-morpholin-4-yl-phenoxy]-propionitrile (84 mg, 0.00021 mol), 3-(2-Methoxy-ethyl)-2,3,4,5-tetrahydro-1H-benzo[d]azepin-7-ylamine (47 mg, 0.00021 mol), and 10-Camphorsulfonic acid (58 mg, 0.00025 mol) in Isopropyl alcohol (2.0 mL) was irradiated in a CEM microwave (140° C., 30 min). The mixture was diluted with 2 mL water and 0.5 mL satd. sodium bicarbonate, then extracted 2×10 mL DCM, dried over sodium sulfate and conc. onto 1 g Celite. Chromatography (ISCO, Amine-capped SiO2, 14 g, 25-100% EtOAc:Hex) afforded 3-(2-{5-Chloro-2-[3-(2-methoxy-ethyl)-2,3,4,5-tetrahydro-1H-benzo[d]azepin-7-ylamino]-pyrimidin-4-ylamino}-5-morpholin-4-yl-phenoxy)-propionitrile as a light pink solid (91 mg, 74%). MP: 91-96° C., LCMS 578 (M+H); 1H-NMR (CDCl3): 8.23 (d, 1H, J=8.8 Hz), 8.02 (s, 1H), 7.52 (s, 1H), 7.37 (s, 1H), 7.18 (d, 1H, J=7.9 Hz), 7.00 (d, 1H, J=8.0 Hz), 6.85 (s, 1H), 6.56 (d, 1H, J=8.8 Hz), 6.50 (s, 1H), 4.28 (t, 2H, J=6.3 Hz), 3.88 (m, 4H), 3.53 (t, 2H, J=6.3 Hz), 3.38 (s, 3H), 3.14 (m, 4H), 2.90 (m, 6H), 2.72 (m, 6H).

Example 1690

3-{2-[5-Chloro-2-(5,5-dimethyl-2-oxo-2,3,4,5-tetrahydro-1H-benzo[b]azepin-8-ylamino)-pyrimidin-4-ylamino]-5-morpholin-4-yl-phenoxy}-propionitrile 3-[2-(2,5-Dichloro-pyrimidin-4-ylamino)-5-morpholin-4-yl-phenoxy]-propionitrile (88 mg, 0.22 mmol), 8-Amino-5,5-dimethyl-1,3,4,5-tetrahydro-benzo[b]azepin-2-one (46 mg, 0.22 mmol), and 10-Camphorsulfonic acid (7.8 mg, 0.033 mmol) in Isopropyl alcohol (2 mL) was irradiated in a CEM microwave (140° C., 30 min). The mixture was diluted with 2 mL water and 0.25 mL satd. sodium bicarbonate, stirred for 10 min, then cooled for 1 h. The resultant solids were collected, washing with water, drying in vacuo to afford 3-{2-[5-Chloro-2-(5,5-dimethyl-2-oxo-2,3,4,5-tetrahydro-1H-benzo[b]azepin-8-ylamino)-pyrimidin-4-ylamino]-5-morpholin-4-yl-phenoxy}-propionitrile as dark yellow solids (94 mg, 75%). MP: 150-156° C., LCMS 562 (M+H), 1H-NMR (CDCl3): 8.00 (d, 1H, J=8.9 Hz), 7.98 (s, 1H), 7.55 (s, 1H), 7.30 (d, 1H, J=8.4 Hz), 7.04 (s, 1H), 6.96 (d, 1H, J=8.4 Hz), 6.61 (d, 1H, J=8.8 Hz), 6.52 (s, 1H), 4.27 (t, 2H, J=6.2 Hz), 3.90 (t, 4H, J=4.7 Hz), 3.23 (t, 4H, J=4.7 Hz), 2.87 (t, 2H, J=6.2 Hz), 2.38 (t, 2H, J=7.0 Hz), 2.09 (t, 2H, J=7.0 Hz).

Example 1691

2-[5-Chloro-2-(9-ethyl-2-fluoro-6,7,8,9-tetrahydro-5-oxa-9-aza-benzocyclohepten-3-ylamino)-pyrimidin-4-ylamino]-3-fluoro-N-methyl-benzamide 10-Camphorsulfonic acid (77 mg, 0.33 mmol) was added to 9-Ethyl-2-fluoro-6,7,8,9-tetrahydro-5-oxa-9-aza-benzocyclohepten-3-ylamine (62 mg, 0.29 mmol) and 2-(2,5-Dichloro-pyrimidin-4-ylamino)-3-fluoro-N-methyl-benzamide (95 mg, 0.30 mmol) in Isopropyl alcohol (3 mL). The mixture was irradiated in a CEM microwave (130° C., 40 min), resulting in ~20% conversion. The reaction was stopped, conc. in vacuo and purified by HPLC then free based with MP-carbonate resin in DCM/MeCN to afford 2-[5-Chloro-2-(9-ethyl-2-fluoro-6,7,8,9-tetrahydro-5-oxa-9-aza-benzocyclohepten-3-ylamino)-pyrimidin-4-ylamino]-3-fluoro-N-methyl-benzamide as a purple foam (10 mg, 7%). LCMS 489 (M+H), 1H-NMR (CDCl3): 8.78 (s, 1H), 8.05 (s, 1H), 7.65 (d, 1H, J=8.7 Hz), 7.35 (m, 1H), 7.29 (m, 1H), 7.23 (m, 1H), 6.84 (s, 1H), 6.55 (d, 1H, J=13.4 Hz), 6.21 (s, 1H), 3.97 (t, 2H, J=5.5 Hz), 3.12 (m, 4H), 2.91 (d, 3H, J=4.7 Hz), 1.96 (m, 2H), 1.17 (t, 3H, J=6.9 Hz); 19F-NMR: −111, −136.

Example 1692

2-[5-Chloro-2-(9-ethyl-6,7,8,9-tetrahydro-5-oxa-9-aza-benzocyclohepten-3-ylamino)-pyrimidin-4-ylamino]-3-fluoro-N-methyl-benzamide 1692a) 2-Methyl-6-nitro-benzoxazole (12.25 g, 68.76 mmol) was dissolved in Tetrahydrofuran (500 mL) and Acetic acid (4.00 mL, 70.4 mmol) and was cooled at 0° C. Sodium tetrahydroborate (5.20 g, 138 mmol) was added over 10 min and the reaction was stirred at 0° C. for 30 min, then warmed to room temperature and stirred an additional 2.5 h. The undissolved borohydride was removed by filtration, and the filtrate conc. in vacuo to 100 mL. The filtrate was poured into water (800 mL) and neutralized with sodium bicarbonate powder. The aq. was extracted 3×200 mL DCM; the org. extract was washed with 100 mL water and 200 mL 1:1 brine:satd. sodium bicarbonate sol., then dried over sodium sulfate before being filtered through a ½" h×2" diameter plug of silica gel, washing with 500 mL 1:1 DCM:EtOAc. The filtrate was conc. to give 2-Ethylamino-5-nitro-phenol as a yellow solid (11.5 g, 92%)

1692b) 2-Ethylamino-5-nitro-phenol (2.50 g, 13.7 mmol) was azeotroped with toluene to ensure dryness, then dissolved in Tetrahydrofuran (300 mL). 3-Bromo-1-propanol (1.50 mL, 16.6 mmol), Tributylphosphine (5.5 mL, 22 mmol), and 40% w/w DEAD in Toluene (40:60, Diethyl Azodicarboxylate:Toluene, 9.6 g) were added, and the reaction was stirred under an atmosphere of Nitrogen overnight. Solvent was partially removed (300 mL removed) and the mixture was diluted with 300 mL EtOAc, then washed with satd. sodium bicarbonate (100 mL), water (2×100 mL) and brine (100 mL). The organics were dried over sodium sulfate and conc. onto 15 g SiO2 and chromatographed (ISCO, 120 g, 0-30% EtOAc:Hex) to afford [2-(3-Bromo-propoxy)-4-nitro-phenyl]-ethyl-amine as a yellow solid. [2-(3-Bromo-propoxy)-4-nitro-phenyl]-ethyl-amine was dissolved in Tetrahydrofuran (200 mL) and Sodium hydride, 60% disp. in mineral oil 0.55 g) was added. After 2 h, no reaction was observed, so N,N-Dimethylformamide (10 mL) was added. After overnight stirring, the reaction was near completion and was quenched with water, diluted with 500 mL ether then washed with water (50 mL), satd. sodium bicarbonate (2×50 mL) and brine (100 mL), dried over sodium sulfate and conc. in vacuo onto 8 g SiO2, then chromatographed (ISCO, 0-30% EtOAc: Hex, 120 g SiO2). The isolated product was ~85% purity, with the alkyl bromide as the major impurity. The mixture was redissolved in DMF (20 mL). Potassium tert-Butoxide (0.23 g, 2.0 mmol) was added and the mixture stirred under nitrogen for 1 h, then water (100 mL) was added. The precipitate was cooled for 20 min, then collected by filtration, washing with water (2×50 mL) to give 9-Ethyl-3-nitro-6,7,8,9-tetrahydro-5-oxa-9-aza-benzocycloheptene (1.99 g, 48%). 1H-NMR (CDCl3): 7.83 (dd, 1H, J=2.5, 8.4 Hz), 7.72 (d, 1H, J=2.5 Hz), 6.61 (d, 1H, J=8.4 Hz), 4.25 (t, 2H, J=6.4 Hz), 3.60 (t, 2H, J=5.4 Hz), 3.38 (q, 2H, J=7.2 Hz), 2.11 (m, 2H), 1.25 (t, 3H, J=7.2 Hz).

1692c) 9-Ethyl-3-nitro-6,7,8,9-tetrahydro-5-oxa-9-aza-benzocycloheptene (0.865 g, 3.89 mmol) and 10% Palladium on Carbon (50% Wet) (0.400 g) in Ethanol (25 mL) were shaken under an atmosphere of Hydrogen (40 psi). After 2 h, the mixture was filtered through Celite, washing with ethanol. Conc. in vacuo afforded 9-Ethyl-6,7,8,9-tetrahydro-5-oxa-9-aza-benzocyclohepten-3-ylamine in quantitative yield. 1H-NMR (CDCl3): 6.75 (d, 1H, J=8.0 Hz), 6.32 (m, 2H), 4.04 (t, 2H, J=5.4 Hz), 3.43 (s, 2H), 3.09 (m, 4H), 1.96 (m, 2H), 1.14 (t, 3H, J=7.1 Hz).

1692d) 10-Camphorsulfonic acid (91 mg, 0.39 mmol) was added to 9-Ethyl-6,7,8,9-tetrahydro-5-oxa-9-aza-benzocyclohepten-3-ylamine (65 mg, 0.34 mmol) and 2-(2,5-Dichloro-pyrimidin-4-ylamino)-3-fluoro-N-methyl-benzamide (110 mg, 0.34 mmol) in Isopropyl alcohol (3 mL). The mixture was irradiated in a CEM microwave (130° C., 40 min). Complete conversion was achieved. The reaction was diluted with 5 mL satd. sodium bicarbonate and the ppt collected. The ppt was purified by ISCO (12 g SiO2, 0-100% EtOAc:Hex) to afford 2-[5-Chloro-2-(9-ethyl-6,7,8,9-tetrahydro-5-oxa-9-aza-benzocyclohepten-3-ylamino)-pyrimidin-4-ylamino]-3-fluoro-N-methyl-benzamide as a green foam (68 mg, 43%). LCMS: 471 (M+H), 1H-NMR (CDCl3): 8.64 (s, 1H), 8.03 (s, 1H), 7.29 (m, 3H), 7.10 (s, 1H), 6.88 (m, 1H), 6.68 (m, 2H), 6.07 (q, 1H, J=4.5 Hz), 4.03 (t, 2H, J=5.6 Hz), 3.17 (m, 4H), 2.91 (d, 3H, J=4.5 Hz), 1.99 (m, 2H), 1.16 (t, 3H, J=7.0 Hz); 19F-NMR: −112

Example 1693

N-{(1R,2R)-2-[5-Chloro-2-(9-ethyl-6,7,8,9-tetrahydro-5-oxa-9-aza-benzocyclohepten-3-ylamino)-pyrimidin-4-ylamino]-cyclohexyl}-methanesulfonamide 10-Camphorsulfonic acid (86 mg, 0.37 mmol) was added to 9-Ethyl-6,7,8,9-tetrahydro-5-oxa-9-aza-benzocyclohepten-3-ylamine (65 mg, 0.34 mmol) and N-[(1R,2R)-2-(2,5-Dichloro-pyrimidin-4-ylamino)-cyclohexyl]-methane-sulfonamide (110 mg, 0.34 mmol) in Isopropyl alcohol (3 mL). The mixture was irradiated in a CEM microwave (130° C., 30 min). The mixture was conc. and purified by HPLC, conc., neutralized with MP-Carbonate (2.69 mmol/g loading; 0.50 g, 1.345 mmol), filtered and conc. to give N-{(1R,2R)-2-[5-Chloro-2-(9-ethyl-6,7,8,9-tetrahydro-5-oxa-9-aza-benzocyclohepten-3-ylamino)-pyrimidin-4-ylamino]-cyclohexyl}-methanesulfonamide as a light green foam, MP: 108-110° C., LCMS: 495 (M+H); 1H-NMR (DMSO): 9.01 (s, 1H), 7.90 (s, 1H), 7.41 (s, 1H), 7.15 (m, 2H), 6.75 (d, 1H, J=8.4 Hz), 6.67 (d, 1H, J=6.3 Hz), 3.98 (m, 2H), 3.79 (m, 1H), 3.32 (m, 1H), 3.12 (m, 2H), 3.06 (m, 2H), 2.90 (s, 3H), 2.14 (m, 1H), 2.02 (m, 1H), 1.90 (m, 2H), 1.69 (m, 2H), 1.32 (m, 4H), 1.10 (t, 3H, J=7.0 Hz).

Example 1694

5-Chloro-N*2*-(9-ethyl-6,7,8,9-tetrahydro-5-oxa-9-aza-benzocyclohepten-3-yl)-N*4*-(2-methoxy-4-morpholin-4-yl-phenyl)-pyrimidine-2,4-diamine 10-Camphorsulfonic acid (1.0E2 mg, 0.44 mmol) was added to 9-Ethyl-6,7,8,9-tetrahydro-5-oxa-9-aza-benzocyclohepten-3-ylamine (65 mg, 0.34 mmol) and (2,5-Dichloro-pyrimidin-4-yl)-(2-methoxy-4-morpholin-4-yl-phenyl)-amine (102 mg, 0.287 mmol) in Isopropyl alcohol (3 mL).

The mixture was irradiated in a CEM microwave (130° C., 30 min). The mixture was conc. and purified by, conc., neutralized with MP-Carbonate (2.69 mmol/g loading; 0.50 g, 1.345 mmol), filtered and conc. to give 5-Chloro-N*2*-(9-ethyl-6,7,8,9-tetrahydro-5-oxa-9-aza-benzocyclohepten-3-yl)-N*4*-(2-methoxy-4-morpholin-4-yl-phenyl)-pyrimidine-2,4-diamine as lavender solids (150 mg, 100%). MP: =185-188° C., LCMS: 511 (M+H); 1H-NMR (DMSO): 9.00 (s, 1H), 8.01 (s, 2H), 7.60 (d, 1H, J=7.8 Hz), 7.10 (d, 1H, J=8.8 Hz), 7.06 (s, 1H), 6.70 (s, 1H), 6.60 (d, 1H, J=8.6 Hz), 6.51 (d, 1H, J=8.7 Hz), 3.96 (t, 2H, J=5.3 Hz), 3.80 (s, 3H), 3.76 (t, 4H, J=4.5 Hz), 3.14 (t, 4H, J=4.5 Hz), 3.12 (m, 4H), 1.87 (m, 2H), 1.10 (t, 3H, J=6.9 Hz).

Example 1695

8-{5-Chloro-4-[2-fluoro-6-(2-methoxy-ethoxy)-phenylamino]-pyrimidin-2-ylamino}-1,3,4,5-tetrahydro-benzo[b]azepin-2-one 10-Camphorsulfonic acid (39 mg, 0.17 mmol) was added to 8-Amino-1,3,4,5-tetrahydro-benzo[b]azepin-2-one (27 mg, 0.15 mmol) and (2,5-Dichloro-pyrimidin-4-yl)-[2-fluoro-6-(2-methoxy-ethoxy)-phenyl]-amine (51 mg, 0.15 mmol) in Isopropyl alcohol (2 mL). The mixture was irradiated in a CEM microwave (130° C., 30 min). The mixture was conc. in vacuo, taken up in acetonitrile and purified by HPLC to give 8-{5-Chloro-4-[2-fluoro-6-(2-methoxy-ethoxy)-phenylamino]-pyrimidin-2-ylamino}-1,3,4,5-tetrahydro-benzo[b]azepin-2-one; compound with trifluoro-acetic acid (31 mg, 34%) as a white lyophilate. LCMS: 472 (M+H), 1H-NMR (DMSO): 9.27 (s, 1H), 9.12 (s, 1H), 8.47 (s, 1H), 8.08 (s, 1H), 7.34 (m, 1H), 7.16 (d, 1H, J=8.0 Hz), 6.96 (m, 2H), 6.90 (m, 1H), 6.82 (d, 1H, J=8.0 Hz), 4.10 (t, 2H, J=4.5 Hz), 3.51 (t, 2H, J=4.5 Hz), 3.16 (s, 3H), 2.60 (m, 2H) 2.03 (m, 4H). 19F-NMR (DMSO): −74, −119.

Example 1696

5-Chloro-N*4*-[2-fluoro-6-(2-methoxy-ethoxy)-phenyl]-N*2*-[3-(2-methoxy-ethyl)-2,3,4,5-tetrahydro-1H-benzo[d]azepin-7-yl]-pyrimidine-2,4-diamine 10-Camphorsulfonic acid (39 mg, 0.17 mmol) was added to 3-(2-Methoxy-ethyl)-2,3,4,5-tetrahydro-1H-benzo[d]azepin-7-ylamine (34 mg, 0.15 mmol) and (2,5-Dichloro-pyrimidin-4-yl)-[2-fluoro-6-(2-methoxy-ethoxy)-phenyl]-amine (51 mg, 0.15 mmol) in Isopropyl alcohol (2 mL). The mixture was irradiated in a CEM microwave (130° C., 30 min). The mixture was conc. in vacuo, taken up in acetonitrile and purified by HPLC to give 5-Chloro-N*4*-[2-fluoro-6-(2-methoxy-ethoxy)-phenyl]-N*2*-[3-(2-methoxy-ethyl)-2,3,4,5-tetrahydro-1H-benzo[d]azepin-7-yl]-pyrimidine-2,4-diamine trifluoroacetic acid salt as a white foam (14 mg, 14%). LCMS: 516 (M+H); 1H-NMR (CD3CN): 11.24 (s, 1H), 10.48 (s, 1H), 7.98 (s, 1H), 7.87 (s, 1H), 7.32 (m, 1H), 7.12 (s, 1H), 6.99 (d, 1H, J=8 Hz), 6.80 (m, 3H), 4.00 (t, 2H, J=4.4 Hz), 3.66 (t, 2H, J=4.6 Hz), 3.56 (m, 2H), 3.47 (t, 2H, J=4.6 Hz), 3.26 (s, 3H), 3.20 (t, 2H, J=4.4 Hz), 3.15 (s, 3H), 2.80 (m, 3H), 2.45 (m, 1H); 19F-NMR (CD3CN): −76, −120.

Example 1697

2-[5-Chloro-2-(9-ethyl-6,7,8,9-tetrahydro-5-oxa-9-aza-benzocyclohepten-2-ylamino)-pyrimidin-4-ylamino]-3-fluoro-N-methyl-benzamide 1697a) 5-Nitro-3H-benzoxazol-2-one (5.35 g, 29.7 mmol) in Acetone (300 mL) was treated with Potassium carbonate (6.99 g, 50.6 mmol) then 1-Bromo-3-chloropropane (10.0 mL, 101 mmol) was added. After 45 min, the mixture was heated to 55° C. overnight. The reaction was cooled, diluted with 100 mL water and 150 mL EtOAc. The layers were separated, the org. washed with brine (50 mL), dried over sodium sulfate, filtered through a ½"h×2"w pad of SiO2 and conc. in vacuo. to near dryness. The oily remainder was suspended in 100 mL 5% EtOAc:Hexane, resulting in precipitation of the product. The solids were triturated for 2 h to break up the solids, collected by filtration and washed with hexane (2×60 mL). After drying, 3-(3-Chloro-propyl)-5-nitro-3H-benzoxazol-2-one was isolated as yellow solids (7.52 g, 99%). 1H-NMR (DMSO): 8.27 (d, 1H, J=2.2 Hz), 8.10 (dd, 1H, J=2.2, 8.8 Hz), 7.59 (d, 1H, J=8.8 Hz), 4.04 (t, 2H, J=6.7 Hz), 3.75 (t, 2H, J=6.5 Hz), 2.17 (m, 2H).

1697b) Potassium hydroxide (2.19 g, 33.2 mmol) was dissolved in Ethanol (150 mL) and 3-(3-Chloro-propyl)-5-nitro-3H-benzoxazol-2-one (8.11 g, 31.6 mmol) was added. After 2 h, the mixture was concentrated in vacuo, and the solids redissolved in N,N-Dimethylformamide (150 mL). The mixture was heated to 80° C. for 2 h. The mixture was cooled and diluted with 500 mL EtOAc and washed with water (4×50 mL). The aq. washes were back extracted with 100 mL EtOAc. The combined organics were washed with water (50 mL) and brine (100 mL), dried over sodium sulfate and conc. in vacuo to give orange solids, which were triturated in 10% Ether:Hexane (100 mL) overnight. The orange solids were collected and washed with hexane to furnish 2-Nitro-7,8-dihydro-6H-5-oxa-9-aza-benzocycloheptene-9-carboxylic acid ethyl ester (6.45 g, 77%). 1H-NMR (DMSO): 8.19 (s, 1H), 8.02 (d, 1H, J=8.9 Hz), 7.19 (d, 1H, J=8.9 Hz), 4.25 (m, 2H), 4.15 (m, 2H), 3.76 (m, 2H), 2.05 (m, 2H), 1.19 (m, 3H).

1697c) 1.00 M of Potassium hydroxide in Water (25 mL) was added to 2-Nitro-7,8-dihydro-6H-5-oxa-9-aza-benzocycloheptene-9-carboxylic acid ethyl ester (2.84 g, 10.7 mmol) in 2-Methoxyethanol (50 mL) and the reaction was heated at 110° C. After overnight heating, the mixture was cooled, extracted with DCM (2×50 mL); the combined organics were washed with water (50 mL) and brine (50 mL), dried and conc. in vacuo. The residue was chromatographed (120 g SiO2, ISCO, 0-20% EtOAc:Hex) to afford 2-Nitro-6,7,8,9-tetrahydro-5-oxa-9-aza-benzocycloheptene as an orange solid (1.64 g, 79%).

1697d) 2-Nitro-6,7,8,9-tetrahydro-5-oxa-9-aza-benzocycloheptene (278 mg, 1.43 mmol) was dissolved in Acetonitrile (15 mL) and Acetaldehyde (0.80 mL, 14 mmol) was added. Acetic acid (0.15 mL, 2.6 mmol) was added, followed by Sodium triacetoxyborohydride (0.85 g, 4.0 mmol), and the mixture was stirred under an atmosphere of Nitrogen at room temperature for 1 h. The solution was diluted with ethyl acetate (50 mL) and satd. sodium bicarbonate (50 mL). The layers were separated, the organic washed with brine (50 mL) and dried over sodium sulfate. Conc. in vacuo followed by chromatography (ISCO, g SiO2, 0-50% EtOAc:Hex) afforded 9-Ethyl-2-nitro-6,7,8,9-tetrahydro-5-oxa-9-aza-benzocycloheptene as an orange oil (272 mg, 85%). 1H-NMR (CDCl3) 7.58 (m, 2H), 6.87 (d, 1H, J=8.1 Hz), 4.31 (t, 2H, J=5.2 Hz), 3.40 (t, 2H, J=5.2 Hz), 3.33 (q, 2H, J=6.8 Hz), 2.05 (tt, 2H, J=5.2, 5.2 Hz), 1.24 (t, 3H, J=6.8 Hz).

1697e) 9-Ethyl-2-nitro-6,7,8,9-tetrahydro-5-oxa-9-aza-benzocycloheptene (486 mg, 2.19), 10% Palladium on Carbon (50% Wet) (302 mg) and Hydrazine monohydrate (1.00 g, 20.0 mmol) in Ethanol (20 mL) was heated at 60° C. After 4 h, the mixture was filtered and conc. in vacuo. After azeotroping with toluene and drying, 9-Ethyl-6,7,8,9-tetrahydro-5-oxa-9-aza-benzocyclohepten-2-ylamine was isolated in quantitative yield.

1697f) 9-Ethyl-6,7,8,9-tetrahydro-5-oxa-9-aza-benzocyclohepten-2-ylamine (57 mg, 0.30 mmol), 10-Camphorsulfonic acid (72.3 mg, 0.311 mmol) and 2-(2,5-Dichloro-pyrimidin-4-ylamino)-3-fluoro-N-methyl-benzamide (93 mg, 0.30 mmol) in Isopropyl alcohol (2.0 mL) was irradiated in a CEM microwave (120° C., 30 min). reaction was diluted with water (1 mL) and satd. sodium bicarbonate (1 mL), diluted with EtOAc (20 mL) and water (10 mL) separation and extraction (2×10 mL EtOAc), followed by drying and chromatography (0-70% EtOAc:Hex) afforded the product as an oil. This oil was taken up in ether and methanol, and 4N HCl/dioxane was added to furnish 2-[5-Chloro-2-(9-ethyl-6,7,8,9-tetrahydro-5-oxa-9-aza-benzocyclohepten-2-ylamino)-pyrimidin-4-ylamino]-3-fluoro-N-methyl-benzamide hydrochloride (67 mg, 44%). MP=168-170° C.; LCMS: 471 (M+H); 1H-NMR (DMSO): 9.70 (s, 1H), 9.54 (s, 1H), 8.54 (s, 1H), 8.21 (s, 1H), 7.47 (m, 5H), 6.88 (s, 1H), 3.71 (m, 2H), 3.45 (m, 6H), 2.72 (d, 3H, J=4.4 Hz), 1.09 (t, 3H, J=7.0 Hz)

Example 1698

3-[5-Chloro-2-(9-ethyl-6,7,8,9-tetrahydro-5-oxa-9-aza-benzocyclohepten-2-ylamino)-pyrimidin-4-ylamino]-thiophene-2-carboxylic acid methyl amide 9-Ethyl-6,7,8,9-tetrahydro-5-oxa-9-aza-benzocyclohepten-2-ylamine (57 mg, 0.30 mmol), 10-Camphorsulfonic acid (72.3 mg, 0.311 mmol) and 3-(2,5-Dichloro-pyrimidin-4-ylamino)-thiophene-2-carboxylic acid methylamide (9.0E1 mg, 0.30 mmol) in Isopropyl alcohol (2.0 mL) was irradiated in a CEM microwave (120° C., 30 min). The mixture was diluted with satd. sodium bicarbonate (1 mL) and water (6 mL). The flocculent solids were separated from an oily residue on the sides of the vial, filtered and washed with water. Drying in vacuo of the solids furnished 3-[5-Chloro-2-(9-ethyl-6,7,8,9-tetrahydro-5-oxa-9-aza-benzocyclohepten-2-ylamino)-pyrimidin-4-ylamino]-thiophene-2-carboxylic acid methylamide (67 mg, 49%). MP=153-155° C.; LCMS: 459 (M+H); 1H-NMR (CDCl3): 11.27 (s, 1H), 8.31 (d, 1H, J=5.1 Hz), 8.08 (s, 1H), 6.92 (s, 1H), 6.88 (m, 2H), 6.71 (s, 1H), 5.67 (s, 1H), 4.14 (m, 2H), 3.29 (m, 2H), 3.27 (m, 2H), 3.02 (d, 3H, J=4.8 Hz), 2.03 (m, 2H), 1.18 (t, 3H, J=6.4 Hz).

Example 1699

(1R,2S,3R,4S,5S,6R)-3-[5-Chloro-2-(1-ethyl-6-methoxy-2-oxo-2,3,4,5-tetrahydro-1H-benzo[b]azepin-7-ylamino)-pyrimidin-4-ylamino]-5,6-dihydroxy-bicyclo[2.2.1]heptane-2-carboxylic acid amide 0.16 M of Osmium tetraoxide in Water (50 uL) was added to (1S,2S,3R,4R)-3-[5-Chloro-2-(1-ethyl-6-methoxy-2-oxo-2,3,4,5-tetrahydro-1H-benzo[b]azepin-7-ylamino)-pyrimidin-4-ylamino]-bicyclo[2.2.1]hept-5-ene-2-carboxylic acid amide (152 mg, 0.306 mmol) and 4-Methyl-morpholine 4-oxide hydrate (65 mg, 0.48 mmol) in Acetone (10 mL) and Water (1.0 mL), and the reaction was stirred under an atmosphere of Nitrogen for 45 min. The reaction was diluted with DCM (15 mL) washed with water (2×5 mL) and brine (10 mL), dried over sodium sulfate and conc. in vacuo. Chromatography of the residue (ISCO 12 g SiO2, 0-10% MeOH:DCM) afforded (1R,2S,3R,4S,5S,6R)-3-[5-Chloro-2-(1-ethyl-6-methoxy-2-oxo-2,3,4,5-tetrahydro-1H-benzo[b]azepin-7-ylamino)-pyrimidin-4-ylamino]-5,6-dihydroxy-bicyclo[2.2.1]heptane-2-carboxylic acid amide as brown solids (110 mg, 67%). MP: 164-170° C.; LCMS: 531 (M+H); 1H-NMR (CDCl3): 8.40 (d, 1H, J=8.8 Hz), 7.92 (s, 1H), 7.38 (s, 1H), 7.16 (d, 1H, J=7.8 Hz), 7.01 (d, 1H, J=9.0 Hz), 5.73 (s, 1H), 5.37 (s, 1H), 4.32 (t, 1H, J=8.0 Hz), 3.97 (m, 1H), 3.83 (m, 1H), 3.80 (s, 3H), 3.49 (d, 1H, J=5.3 Hz), 2.98 (m, 2H), 2.51 (m, 1H), 2.44 (m, 1H), 2.39 (m, 1H), 2.28 (m, 3H), 2.06 (m, 1H), 1.91 (m, 1H), 1.12 (t, 3H, J=7.2 Hz).

Example 1700

2-[4-(2-Allyloxy-6-fluoro-4-morpholin-4-yl-phenylamino)-5-chloro-pyrimidin-2-ylamino]-5-methyl-8,9-dihydro-5H-7-oxa-5-aza-benzocyclohepten-6-one 1700a) 1,3,5-Trifluoro-2-nitro-benzene (5.30 g, 0.0299 mol) and Potassium carbonate (4.96 g, 0.0359 mol) were mixed in Dimethyl sulfoxide (40.0 mL) and Morpholine (2.74 mL, 0.0314 mol) was added. The reaction was stirred at room temperature for 48 hours and then diluted with EtOAc and washed twice with water. The organic layer was dried over sodium sulfate, filtered, and concentrated under reduced pressure. Purification by silica gel chromatography using a gradient of 0-40% EtOAc/hex as the eluting solvent gave 4-(3,5-Difluoro-4-nitro-phenyl)-morpholine (2.85 g, 39%) as a yellow solid. MP=112-114° C.; LCMS=245 (M+H); HNMR (CDCl3, 400 MHz) δ 6.45-6.37 (m, 2H), 3.86 (t, 4H, J=4.5 Hz), 3.33 (t, 4H, J=4.5 Hz); F19 NMR (CDCl₃, 400 MHz) δ −115.

1700b) 2-Propen-1-ol (0.160 g, 2.75 mmol) was added to 4-(3,5-Difluoro-4-nitro-phenyl)-morpholine (0.616 g, 2.52 mmol) and Potassium carbonate (0.783 g, 5.66 mmol) in Dimethyl sulfoxide (10 mL). The mixture was heated to at 100° C. under an atmosphere of Nitrogen. After 4 days, the reaction had achieved ~75% conversion. The reaction was cooled and partitioned between water (50 mL) and ether (100 mL) and separated. The organic layer was washed with water (2×50 mL) and brine (50 mL), dried over sodium sulfate and conc. in vacuo onto 2.5 g SiO2. Chromatography (ISCO, 40 g, 0-50% EtOAc:Hex) afforded the starting material followed by mixed fractions, then clean fractions of 4-(3-Allyloxy-5-fluoro-4-nitro-phenyl)-morpholine (203 mg, 29%). 1H-NMR (CDCl3): 6.18 (d, 1H, J=19 Hz), 6.04 (d, 1H, J=5.0 Hz), 5.98 (ddt, 1H, J=Hz), 5.44 (d, 1H, J=17.3 Hz), 5.32 (d, 1H, J=10.6 Hz), 4.62 (d, 2H, J=5.0 Hz), 3.84 (t, 4H, J=4.5 Hz), 3.24 (t, 4H, J=4.5 Hz).

1700c) Sulfur (0.320 g, 9.98 mmol) was added to Sodium tetrahydroborate (0.126 g, 3.33 mmol) in Tetrahydrofuran (8 mL). After 5 min, a solution of 4-(3-Allyloxy-5-fluoro-4-nitro-phenyl)-morpholine (0.188 g, 0.666 mmol) in Tetrahydrofuran (6 mL) was added and the mixture was heated at 60° C. overnight. The mixture was cooled and diluted with 25 mL satd. sodium bicarbonate, then extracted 2×25 mL EtOAc. The organic extract was washed with water (10 mL) and brine (25 mL), then dried over sodium sulfate, and was concentrated in vacuo. The residue was partitioned between EtOAc (20 mL) and 1N HCl (20 mL); the resulting precipitate was filtered off. The filtrate was separated, the aq. washed 2×25 mL EtOAc, then neutralized with satd. sodium bicarbonate solution before being extracted with DCM (2×20 mL). The organic extract was dried over sodium sulfate and conc. in vacuo to afford 2-Allyloxy-6-fluoro-4-morpholin-4-yl-phenylamine (108 mg, 64%). LCMS: 253 (M+H); 1H-NMR (CDCl3): 6.30 (m, 2H), 6.06 (m, 1H), 5.42 (d, 1H, J=17 Hz), 5.29 (d, 1H, J=10.5 Hz), 4.55 (m, 2H), 3.80 (m, 4H), 3.49 (s, 2H), 3.00 (m, 4H); 19F-NMR (CDCl3): −133.

1700d) 10-Camphorsulfonic acid (3.4 mg, 0.015 mmol), 2-Amino-5-methyl-8,9-dihydro-5H-7-oxa-5-aza-benzocyclohepten-6-one (28 mg, 0.15 mmol), and (2-Allyloxy-6-fluoro-4-morpholin-4-yl-phenyl)-(2,5-dichloro-pyrimidin-4-yl)-amine (59 mg, 0.15 mmol) in Isopropyl alcohol (3 mL) was irradiated in a CEM microwave (120° C., 30 min). The solution was neutralized by the addition of MP-Carbonate (2.69 mmol/g loading; 0.10 g, 0.269 mmol), filtered and conc. in vacuo. The resultant oil was chromatographed (ISCO, 12 g SiO2, 0-100% EtOAc:Hex) to afford the product as the second eluting peak. The isolated product was contaminated in a 1:1 ratio with remaining 2-Amino-5-methyl-8,9-dihydro-5H-7-oxa-5-aza-benzocyclohepten-6-one as determined by $^1$H-NMR. The mixture of product and 2-Amino-5-methyl-8,9-dihydro-5H-7-oxa-5-aza-benzocyclohepten-6-one (32 mg) was dissolved in dioxane (5 mL) and aq. satd. sodium bicarbonate (1 mL) was added. 9-Fluorenylmethyl chloroformate (21 mg, 0.081 mmol) was added, and the mixture was stirred under an atmosphere of Nitrogen. HPLC/LCMS showed FMOC-incorporation onto the impurity aniline. A second aliquot of 9-Fluorenylmethyl chloroformate (42 mg, 0.16 mmol) was added and stirred for an additional 48 h. The solution was diluted with EtOAc (10 mL) and water (5 mL). The layers were separated, the aq. extracted with 5 mL DCM, and the combined organics dried over sodium sulfate, then conc. onto 1.5 g SiO2. Chromatography (ISCO, 12 g, 0-85% EtOAc:Hex) afforded 4 major peaks, the last eluting at 80% being 2-[4-(2-Allyloxy-6-fluoro-4-morpholin-4-yl-phenylamino)-5-chloro-pyrimidin-2-ylamino]-5-methyl-8,9-dihydro-5H-7-oxa-5-aza-benzocyclohepten-6-one as a beige foam (14 mg, 17%). LCMS: 555 (M+H); 1H-NMR (CDCl3): 8.01 (s, 1H), 7.50 (s, 1H), 7.15 (d, 1H, J=8.9 Hz), 6.93 (d, 1H, J=8.1 Hz), 6.86 (s, 1H), 5.92 (m, 1H), 5.30 (d, 1H, J=17.0 Hz), 5.21 (d, 1H, J=10.6 Hz), 4.52 (m, 2H), 4.41 (t, 2H, J=6.3 Hz), 3.86 (m, 4H), 3.34 (s, 3H), 3.16 (m, 4H), 2.78 (t, 2H, J=6.3 Hz).

Example 1701

2-[2-(9-Acetyl-6,7,8,9-tetrahydro-5-oxa-9-aza-benzocyclohepten-2-ylamino)-5-chloro-pyrimidin-4-ylamino]-3-fluoro-N-methyl-benzamide 1701a) Acetic anhydride (1.00 mL, 10.6 mmol;) was added to a solution of 2-Nitro-6,7,8,9-tetrahydro-5-oxa-9-aza-benzocycloheptene (0.580 g, 2.99 mmol), 4-Dimethylaminopyridine (20 mg, 0.1 mmol; Acros) and Triethylamine (1.0 mL, 7.2 mmol) in Acetonitrile (10 mL; Acros). The reaction was stirred under an atmosphere of Nitrogen overnight. Conversion was moderate, so the mixture was heated at 50° C. for the weekend. The solution was conc. in vacuo, diluted with 25 mL EtOAc then washed with 1N HCl (10 mL), satd. sodium bicarbonate (10 mL) and brine (10 mL). After drying over sodium sulfate, the solution was conc. and the residue chromatographed (ISCO, 80 g SiO2, 0-65% EtOAc:Hex) to afford 1-(2-Nitro-7,8-dihydro-6H-5-oxa-9-aza-benzocyclohepten-9-yl)-ethanone as light yellow solids (522 mg, 74%). Mixture of rotamers in 1H-NMR, resulting in very broad signals for the aliphatic methylenes. 13C-NMR (CDCl3): 169.8, 160.3, 142.7, 134.3, 124.8, 124.6, 122.6, 71.1, 45.0, 28.0, 22.4

1701b) 1-(2-Nitro-7,8-dihydro-6H-5-oxa-9-aza-benzocyclohepten-9-yl)-ethanone (0.520 g, 2.20 mmol) and 10% Palladium on Carbon (50% Wet) (0.12 g) in Ethanol (40 mL) was shaken under an atmosphere of Hydrogen (30 psi) overnight. The mixture was filtered and washed with ethanol (100 mL). Conc. in vacuo afforded 1-(2-Amino-7,8-dihydro-6H-5-oxa-9-aza-benzocyclohepten-9-yl)-ethanone (450 mg, 99%). 1H-NMR (CDCl3): 6.94 (d, 1H, J=8.1 Hz), 6.32 (d, 1H, J=8.1 Hz), 6.56 (s, 1H), 4.78 (m, 1H), 4.36 (m, 1H), 3.58 (m, 1H), 2.69 (m, 1H), 2.22 (m, 1H), 1.93 (s, 3H), 1.73 (m, 1H).

1701c) 1-(2-Amino-7,8-dihydro-6H-5-oxa-9-aza-benzocyclohepten-9-yl)-ethanone (55 mg, 0.27 mmol), 2-(2,5-Dichloro-pyrimidin-4-ylamino)-3-fluoro-N-methyl-benzamide (89 mg, 0.28 mmol), and 10-Camphorsulfonic acid (12 mg, 0.052 mmol) in Isopropyl alcohol (2 mL) was irradiated in a CEM microwave (120° C., 40 min). The contents were conc. in vacuo and purified by HPLC and lyophilized to give 2-[2-(9-Acetyl-6,7,8,9-tetrahydro-5-oxa-9-aza-benzocyclohepten-2-ylamino)-5-chloro-pyrimidin-4-ylamino]-3-fluoro-N-methyl-benzamide; compound with trifluoroacetic acid as an off white lyophilate (104 mg, 65%). MP 125-128° C.; LCMS: 485 (M+H); 1H-NMR (DMSO): 9.47 (s, 1H), 9.36 (s, 1H), 8.51 (d, 1H, J=5.2 Hz), 8.19 (s, 1H), 7.54 (s, 1H), 7.47 (m, 1H), 7.38 (m, 2H), 7.24 (d, 1H, J=8.4 Hz), 6.89 (d, 1H, J=8.4 Hz), 4.57 (m, 1H), 4.28 (m, 1H), 3.53 (m, 1H), 2.73 (d, 3H, J=4 Hz), 2.60 (m, 1H), 1.94 (m, 1H), 1.71 (m, 1H), 1.63 (s, 3H).

Example 1702

2-[2-(9-Acetyl-6,7,8,9-tetrahydro-5-oxa-9-aza-benzocyclohepten-2-ylamino)-5-chloro-pyrimidin-4-ylamino]-3-fluoro-N-methyl-benzamide 1-(2-Amino-7,8-dihydro-6H-5-oxa-9-aza-benzocyclohepten-9-yl)-ethanone (55 mg, 0.27 mmol), 3-(2,5-Dichloro-pyrimidin-4-ylamino)-thiophene-2-carboxylic acid methylamide (88 mg, 0.29 mmol), and 10-Camphorsulfonic acid (12 mg, 0.052 mmol) in Isopropyl alcohol (2 mL) was irradiated in a CEM microwave (120° C., 40 min; 140° C. 20 min, 140° C. 60 min, 140° C. 20 min). The mixture was conc. in vacuo and suspended in DMSO (3.5 mL), which resulted in a significant amount of solid to form. The solids were triturated in hexane:EtOAc, washed with hexane and dried in vacuo to give 3-[2-(9-Acetyl-6,7,8,9-tetrahydro-5-oxa-9-aza-benzocyclohepten-2-ylamino)-5-chloro-pyrimidin-4-ylamino]-thiophene-2-carboxylic acid methylamideas an off white solid (45 mg, 36%). MP>260° C.; LCMS: 473 (M+H); 1H-NMR (DMSO): 11.64 (s, 1H), 9.56 (s, 1H), 8.43 (s, 1H), 8.26 (m, 2H), 7.75 (d, 1H, J=4 Hz), 7.70 (s, 1H), 7.48 (d, 1H, J=7.1 Hz), 7.07 (d, 1H, J=8.4 Hz), 4.60 (m, 1H), 4.32 (m, 1H), 3.64 (m, 1H), 2.77 (m, 4H), 1.97 (m, 1H), 1.80 (m, 4H).

Example 1703

2-[2-(9-Acetyl-6,7,8,9-tetrahydro-5-oxa-9-aza-benzocyclohepten-2-ylamino)-5-chloro-pyrimidin-4-ylamino]-N-methyl-benzamide 1-(2-Amino-7,8-dihydro-6H-5-oxa-9-aza-benzocyclohepten-9-yl)-ethanone (55 mg, 0.27 mmol), 2-(2,5-Dichloro-pyrimidin-4-ylamino)-N-methyl-benzamide (85 mg, 0.29 mmol), and 10-Camphorsulfonic acid (12 mg, 0.052 mmol) in Isopropyl alcohol (2 mL) was irradiated in a CEM microwave (120° C., 40 min). The contents were neutralized with 1 mL satd. sodium bicarbonate and diluted with 4 mL water to afford a turbid solution. This solution was added to stirring water (10 mL) resulting in ppt of the target and the chloropyrimidine traces. The solid was chromatographed (SiO2, 0-100% EtOAc:Hex) to afford 2-[2-(9-Acetyl-6,7,8,9-tetrahydro-5-oxa-9-aza-benzocyclohepten-2-ylamino)-5-chloro-pyrimidin-4-ylamino]-N-methyl-benzamide as a light yellow foam (54 mg, 43%). LCMS: 467 (M+H); 1H-NMR (DMSO): 11.51 (s, 1H), 9.50 (s, 1H), 8.75 (s, 1H), 8.64 (s, 1H), 8.24 (s, 1H), 7.73 (m, 2H), 7.45 (m, 2H), 7.14 (m, 1H), 7.03 (d, 1H, J=8.8 Hz), 4.60 (m, 1H), 4.30 (m, 1H), 3.62 (m, 1H), 2.91 (d, 1H, J=4 Hz), 2.77 (m, 1H), 1.93 (m, 1H), 1.74 (m, 4H).

Example 1704

2-{5-Chloro-2-[9-(2-pyrrolidin-1-yl-acetyl)-6,7,8,9-tetrahydro-5-oxa-9-aza-benzocyclohepten-2-ylamino]-pyrimidin-4-ylamino}-3-fluoro-N-methyl-benzamide 1704a) Chloroacetyl chloride (0.50 mL, 6.3 mmol; Acros) was added to a solution of 2-Nitro-6,7,8,9-tetrahydro-5-oxa-9-aza-benzocycloheptene (0.58 g, 3.0 mmol;), Triethylamine (1.0 mL, 7.2 mmol), and 4-Dimethylaminopyridine (20 mg, 0.1 mmol; Acros) in Acetonitrile (10 mL) (Exothermic-immediate color change to a dark mixture). The reaction was stirred under an atmosphere of Nitrogen. After 1 h, Pyrrolidine (2.0 mL, 24 mmol) was added, as HPLC had shown the first acylation to be complete. After overnight stirring, the mixture was diluted with DCM (30 mL) and water (30 mL), the layers separated and the aq. extracted with 10 mL DCM. The combined organics were washed with brine (20 mL) and dried, then conc. The residue was chromatographed (ISCO, 40 g, 0-5% MeOH:DCM) to afford 1-(2-Nitro-7,8-dihydro-6H-5-oxa-9-aza-benzocyclohepten-9-yl)-2-pyrrolidin-1-yl-ethanone as a yellow oil (807 mg, 88%). 1H-NMR (CDCl3): rotamers, broad spectrum; 13C-NMR (CDCl$_3$): 169.8, 160.3, 142.5, 133.6, 124.8, 124.2, 122.1, 70.9, 57.6, 54.0, 45.3, 28.0, 23.7

1704b) 1-(2-Nitro-7,8-dihydro-6H-5-oxa-9-aza-benzocyclohepten-9-yl)-2-pyrrolidin-1-yl-ethanone (0.402 g, 1.32 mmol) and 10% Palladium on Carbon (50% Wet) (0.1 g) in Tetrahydrofuran (10 mL; EMD) and Ethanol (10 mL) was shaken under an atmosphere of Hydrogen (25 psi) overnight. Filtration and washing with ethanol (50 mL) followed by conc. afforded 1-(2-Amino-7,8-dihydro-6H-5-oxa-9-aza-benzocyclohepten-9-yl)-2-pyrrolidin-1-yl-ethanone as an oil in quantitative yield. 1H-NMR (CDCl3): 6.93 (d, 1H, J=8 Hz), 6.58 (d, 1H, J=8 Hz), 6.57 (s, 1H), 4.77 (m, 1H), 4.36 (m, 1H), 4.01 (br s, 2H), 3.76 (m, 1H), 3.56 (m, 1H), 3.10 (m, 1H), 2.94 (m, 4H), 2.71 (m, 1H), 2.25 (m, 1H), 1.91 (m, 4H), 1.71 (m, 1H), 0.86 (m, 1H).

1704c) 1-(2-Amino-7,8-dihydro-6H-5-oxa-9-aza-benzocyclohepten-9-yl)-2-pyrrolidin-1-yl-ethanone (61 mg, 0.22 mmol), 2-(2,5-Dichloro-pyrimidin-4-ylamino)-3-fluoro-N-methyl-benzamide (75 mg, 0.24 mmol), and 10-Camphorsulfonic acid (63 mg, 0.27 mmol) in Isopropyl alcohol (3 mL) was irradiated in a CEM microwave (120° C., 40 min). The contents were conc. in vacuo and purified by HPLC and lyophilized to give 2-{5-Chloro-2-[9-(2-pyrrolidin-1-yl-acetyl)-6,7,8,9-tetrahydro-5-oxa-9-aza-benzocyclohepten-2-ylamino]-pyrimidin-4-ylamino}-3-fluoro-N-methyl-benzamide; compound with trifluoroacetic acid as an off white lyophilate (51 mg, 34%). LCMS: 554 (M+H); 1H-NMR (DMSO): 9.78 (s, 1H), 9.47 (s, 1H), 9.14 (s, 1H), 8.41 (s, 1H), 8.18 (s, 1H), 7.51 (s, 1H), 7.42 (m, 3H), 7.26 (d, 1H, J=8.3 Hz), 6.98 (d, 1H, J=8.8 Hz), 4.58 (m, 1H), 4.30 (m, 1H), 4.08 (m, 1H), 3.60 (m, 5H), 2.96 (m, 1H), 2.82 (m, 1H), 2.73 (d, 3H, J=4 Hz), 1.90 (m, 6H).

Example 1705

3-{5-Chloro-2-[9-(2-pyrrolidin-1-yl-acetyl)-6,7,8,9-tetrahydro-5-oxa-9-aza-benzocyclohepten-2-ylamino]-pyrimidin-4-ylamino}-thiophene-2-carboxylic acid methylamide 1-(2-Amino-7,8-dihydro-6H-5-oxa-9-aza-benzocyclohepten-9-yl)-2-pyrrolidin-1-yl-ethanone (61 mg, 0.22 mmol;), 3-(2,5-Dichloro-pyrimidin-4-ylamino)-thiophene-2-carboxylic acid methylamide (72 mg, 0.24 mmol), and I O-Camphorsulfonic acid (63 mg, 0.27 mmol) in Isopropyl alcohol (3 mL) was irradiated in a CEM microwave (120° C., 40 min). The contents were conc. in vacuo and purified by HPLC and lyophilized to give 3-{5-Chloro-2-[9-(2-pyrrolidin-1-yl-acetyl)-6,7,8,9-tetrahydro-5-oxa-9-aza-benzocyclohepten-2-ylamino]-pyrimidin-4-ylamino}-thiophene-2-carboxylic acid methylamide; compound with trifluoroacetic acid as a peach lyophilate (72 mg, 50%). LCMS: 542 (M+H); 1H-NMR (DMSO): 11.65 (s, 1H), 9.80 (m, 1H), 9.59 (s, 1H), 8.42 (m, 1H), 8.25 (m, 2H), 7.77 (m, 2H), 7.45 (d, 1H, J=7.3 Hz), 7.15 (d, 1H, J=8.4 Hz), 4.62 (m, 1H), 4.33 (m, 3H), 3.72 (m, 2H), 3.54 (m, 2H), 2.95 (m, 2H), 2.78 (d, 3H, J=4 Hz), 2.04 (m, 1H), 1.88 (m, 5H).

Example 1706

2-{5-Chloro-2-[9-(2-pyrrolidin-1-yl-acetyl)-6,7,8,9-tetrahydro-5-oxa-9-aza-benzocyclohepten-2-ylamino]-pyrimidin-4-ylamino}-N-methyl-benzamide 1-(2-Amino-7,8-dihydro-6H-5-oxa-9-aza-benzocyclohepten-9-yl)-2-pyrrolidin-1-yl-ethanone (61 mg, 0.22 mmol;), 2-(2,5-Dichloro-pyrimidin-4-ylamino)-N-methyl-benzamide (71 mg, 0.24 mmol), and 10-Camphorsulfonic acid (63 mg, 0.27 mmol) in Isopropyl alcohol (3 mL) was irradiated in a CEM microwave (120° C., 40 min). The contents were conc. in vacuo and purified by HPLC and lyophilized to give 2-{5-Chloro-2-[9-(2-pyrrolidin-1-yl-acetyl)-6,7,8,9-tetrahydro-5-oxa-9-aza-benzocyclohepten-2-ylamino]-pyrimidin-4-ylamino}-N-methyl-benzamide; compound with trifluoroacetic acid as a light peach lyophilate (50 mg, 35%). LCMS: 536 (M+H); 1H-NMR (DMSO): 11.53 (s, 1H), 9.80 (s, 1H), 9.55 (s, 1H), 8.73 (s, 1H), 8.63 (s, 1H), 8.24 (s, 1H), 7.80 (s, 1H), 7.76 (d, 1H, J=8.0 Hz), 7.48 (m, 2H), 7.13 (m, 2H), 4.59 (m, 1H), 4.36 (m, 1H), 4.25 (m, 1H), 3.71 (m, 2H), 3.52 (m, 2H), 2.85 (m, 3H), 2.85 (d, 3H, J=4 Hz), 2.03 (m, 1H), 1.87 (m, 5H).

Example 1707

2-[5-Chloro-2-(9-methyl-6,7,8,9-tetrahydro-5-oxa-9-aza-benzocyclohepten-2-ylamino)-pyrimidin-4-ylamino]-3-fluoro-N-methyl-benzamide 1707a) Sodium triacetoxyborohydride (1.02 g, 4.82 mmol) was added to 2-Nitro-6,7,8,9-tetrahydro-5-oxa-9-aza-benzocycloheptene (0.312 g, 1.61 mmol) in Acetonitrile (15 mL) and Acetic acid (0.20 mL, 3.5 mmol), then 13 M of Formaldehyde in Water (0.60 mL) was added. After 45 min, the mixture was poured into 100 mL EtOAc and washed with satd. sodium bicarbonate (3×30 mL) and brine (50 mL). After drying over sodium sulfate and conc. the residue was chromatographed (ISCO, 40 g, 0-40% EtOAc:Hex) to afford 9-Methyl-2-nitro-6,7,8,9-tetrahydro-5-oxa-9-aza-benzocycloheptene as an orange solid (298 mg, 89%). 1H-NMR (CDCl3): 7.65 (d, 1H, J=8.6 Hz), 7.61 (s, 1H), 6.91 (d, 1H, J=8.6 Hz), 4.29 (t, 2H, J=5.8 Hz), 3.33 (t, 2H, J=6.0 Hz), 2.86 (t, 3H), 2.08 (tt, 2H, J=5.8, 6.0 Hz)

1707b) 9-Methyl-2-nitro-6,7,8,9-tetrahydro-5-oxa-9-aza-benzocycloheptene (0.296 g, 1.42 mmol) and 10% Palladium on Carbon (50% Wet) (0.097 g) in Ethanol (20 mL) was shaken under an atmosphere of Hydrogen (30 psi) overnight. The mixture was filtered, washing with 20 mL ethanol. The filtrate was concentrated to give 9-Methyl-6,7,8,9-tetrahydro-5-oxa-9-aza-benzocyclohepten-2-ylamine as a white solid (206 mg, 81%). 1H-NMR (CDCl3): 6.77 (d, 1H, J=8.2 Hz), 6.21 (s, 1H), 6.14 (d, 1H, J=8.2 Hz), 3.96 (t, 2H, J=5.5 Hz), 3.35 (br s, 2H), 3.09 (t, 2H, J=5.6 Hz), 2.86 (s, 3H), 1.99 (tt, 2H, J=5.5, 5.6 Hz).

1707c) 9-Methyl-6,7,8,9-tetrahydro-5-oxa-9-aza-benzocyclohepten-2-ylamine (51 mg, 0.29 mmol), 2-(2,5-Dichloro-pyrimidin-4-ylamino)-3-fluoro-N-methyl-benzamide (95 mg, 0.30 mmol), and 10-Camphorsulfonic acid (81 mg, 0.35 mmol) in Isopropyl alcohol (4 mL) was irradiated in a CEM microwave (120° C., 40 min). The contents were conc. in vacuo and purified by HPLC and lyophilized to give 2-[5-Chloro-2-(9-methyl-6,7,8,9-tetrahydro-5-oxa-9-aza-benzocyclohepten-2-ylamino)-pyrimidin-4-ylamino]-3-fluoro-N-methyl-benzamide; compound with trifluoroacetic acid (29 mg, 18%) as a yellow lyophilate. LCMS: 457 (M+H); 1H-NMR (DMSO): 9.45 (s, 1H), 9.29 (s, 1H), 8.52 (d, 1H, J=4.8 Hz), 8.17 (s, 1H), 7.47 (m, 2H), 7.41 (m, 1H), 7.08 (m, 1H), 6.99 (m, 1H), 6.65 (d, 1H, J=8.7 Hz), 3.91 (m, 2H), 3.11 (m, 2H), 2.73 (m, 6H), 1.95 (m, 2H).

Example 1708

2-[5-Chloro-2-(9-methyl-6,7,8,9-tetrahydro-5-oxa-9-aza-benzocyclohepten-2-ylamino)-pyrimidin-4-ylamino]-N-methyl-benzamide 9-Methyl-6,7,8,9-tetrahydro-5-oxa-9-aza-benzocyclohepten-2-ylamine (51 mg, 0.29 mmol), 2-(2,5-Dichloro-pyrimidin-4-ylamino)-N-methyl-benzamide (92 mg, 0.31 mmol), and 10-Camphorsulfonic acid (81 mg, 0.35 mmol) in Isopropyl alcohol (4 mL) was irradiated in a CEM microwave (120° C., 40 min). The contents were conc. in vacuo and purified by HPLC and lyophilized to give 2-[5-Chloro-2-(9-methyl-6,7,8,9-tetrahydro-5-oxa-9-aza-benzocyclohepten-2-ylamino)-pyrimidin-4-ylamino]-N-methyl-benzamide; compound with trifluoroacetic acid (45 mg, 28%) as a yellow lyophilate. LCMS: 439 (M+H); 1H-NMR (DMSO): 11.83 (s, 1H), 9.53 (s, 1H), 8.75 (m, 2H), 8.22 (s, 1H), 7.76 (d, 1H, J=8 Hz), 7.46 (m, 1H), 7.19 (m, 3H), 3.98 (m, 2H), 3.19 (m, 2H), 2.81 (m, 6H), 2.00 (m, 2H).

Example 1709

2-[4-(2-Allyloxy-4-dimethylamino-6-fluoro-phenylamino)-5-chloro-pyrimidin-2-ylamino]-5-methyl-8,9-dihydro-5H-7-oxa-5-aza-benzocyclohepten-6-one 1709a) 1,3,5-Trifluoro-2-nitro-benzene (6.16 g, 34.8 mmol; TCI) and Potassium carbonate (15.5 g, 112 mmol; EMD) were mixed in Dimethyl sulfoxide (75 mL; EMD) and Dimethylamine hydrochloride (3.01 g, 36.9 mmol) was added. The reaction was stirred at room temperature for 2 hours and then diluted with EtOAc and washed twice with water. The organic layer was dried over sodium sulfate, filtered, and concentrated under reduced pressure onto 13 g SiO2. Chromatography (0-20% EtOAc:Hex) first afforded (3,5-Difluoro-2-nitro-phenyl)-dimethyl-amine as a yellow oil (79%). Resolvating the column and elution (20-40% EtOAc:Hex) then afforded (3,5-Difluoro-4-nitro-phenyl)-dimethyl-amine as a yellow solid (635 mg, 9%). 1H-NMR (CDCl3): 6.18 (d, 2H, J=13 Hz), 3.07 (s, 6H); 19F-NMR (CDCl3): –116

1709b) (3,5-Difluoro-4-nitro-phenyl)-dimethyl-amine (0.630 g, 3.12 mmol) and 19.1 M of Sodium hydroxide in Water (0.400 mL) in Water (4 mL) and Dimethyl sulfoxide (8 mL) was heated to 70° C. Additional DMSO (8 mL) was added to solubilize the mixture. After 2 h, the solution was cooled then rendered acidic with 12.0 M of Hydrogen Chloride in Water (0.80 mL). The yellow precipitate was collected, using water to aid in the transfer and to rinse the solids. 5-Dimethylamino-3-fluoro-2-nitro-phenol was isolated as yellow solids (598 mg, 96%). 1H-NMR (DMSO): 11.10 (s, 1H), 6.29 (d, 1H, J=15.6 Hz), 6.02 (s, 1H), 3.01 (s, 6H); 19F–NMR (DMSO): –118.

1709c) 3-Iodo-1-Propene (0.30 mL, 3.3 mmol) was added to 5-Dimethylamino-3-fluoro-2-nitro-phenol (0.592 g, 2.96 mmol) and Potassium carbonate (1.1 g, 7.9 mmol) in Dimethyl sulfoxide (15 mL) and the reaction was stirred under an atmosphere of Nitrogen for 45 m. The mixture was diluted with ether (120 mL) and water (50 mL), the layers separated and the aq. back extracted with 25 mL ether. The combined organics were washed with water (60 mL) and brine (60 mL). After drying over sodium sulfate, the solution was conc. in vacuo and the residue chromatographed (ISCO, 52 g SiO2, 0-50% EtOAc:Hex) to afford (3-Allyloxy-5-fluoro-4-nitro-phenyl)-dimethyl-amine as a yellow solid (0.61 g, 86%). 1H-NMR (CDCl3): 6.01 (m, 2H), 5.90 (s, 1H), 5.46 (d, 1H, J=17.2 Hz), 5.32 (d, 1H, J=10.6 Hz), 4.63 (m, 2H), 3.03 (s, 6H); 19F-NMR (CDCl3): –119.

1709d) Sulfur (1.2 g, 38 mmol) was added to Sodium tetrahydroborate (0.48 g, 13 mmol) in Tetrahydrofuran (20 mL). After 20 min, a solution of (3-Allyloxy-5-fluoro-4-nitro-phenyl)-dimethyl-amine (0.61 g, 2.5 mmol) in Tetrahydrofuran (20 mL) was added, and after 20 min the mixture was heated at 60° C. for an additional 2.5 h. The mixture was cooled, quenched with 100 mL satd. sodium bicarbonate and extracted with EtOAc (3×50 mL). The organic extract was washed with brine, dried over sodium sulfate and conc. in vacuo. The residue was dissolved in N-Methylpyrrolidinone (10 mL) and N,N-Diisopropylethylamine (0.65 mL, 3.7 mmol) and 2,4,5-Trichloro-pyrimidine (0.60 mL, 5.2 mmol) were added. The mixture was heated under an atmosphere of Nitrogen at 80° C. After 2 h, the solution was cooled, diluted with 100 mL Ether and washed with water (3×20 mL) and brine (50 mL). The aq. extract was back extracted with DCM (2×50 mL), which was then diluted with 100 mL ether and washed with water (50 mL) and brine (50 mL). The organic extracts were combined, dried over sodium sulfate and diluted with an equal volume of hexane before filtering through a 2"h×3"w circular pad of silica gel to remove baseline colored impurities. The filtrate was conc. and chromatographed (ISCO 80 g silica gel, 0-20% EtOAc:Hex), with the product eluting at 20%. Following conc., 2-Allyloxy-N(1)-(2,5-dichloro-pyrimidin-4-yl)-6-fluoro-N(4),N(4)-dimethyl-benzene-1,4-diamine was isolated as a green film (140 mg, 15% over two steps). 1H-NMR (CDCl3): 8.11 (s, 1H), 6.62 (s, 1H), 6.12 (d, 1H, J=13.1 Hz), 5.97 (s, 1H), 5.95 (m, 1H), 5.32 (d, 1H, J=17.2 Hz), 5.23 (d, 1H, J=9.4 Hz), 4.55 (m, 2H), 2.96 (s, 6H); 19F-NMR (CDCl3): –118.

1709e) 10-Camphorsulfonic acid (51 mg, 0.22 mmol), 2-Amino-5-methyl-8,9-dihydro-5H-7-oxa-5-aza-benzocyclohepten-6-one (37 mg, 0.19 mmol), and 2-Allyloxy-N(1)-(2,5-dichloro-pyrimidin-4-yl)-6-fluoro-N(4),N(4)-dimethyl-benzene-1,4-diamine (69 mg, 0.19 mmol) in Isopropyl alcohol (4 mL) (with trace DCM to solubilize, with heating) was irradiated in a CEM microwave (120° C., 40 min). The mixture was passed through a filter and 2-[4-(2-Allyloxy-4-dimethylamino-6-fluoro-phenylamino)-5-chloro-pyrimidin-2-ylamino]-5-methyl-8,9-dihydro-5H-7-oxa-5-aza-benzocyclohepten-6-one; compound with trifluoroacetic acid isolated by preparative HPLC as an off white lyophilate (22 mg, 18%). LCMS: 513 (M+H); 1H-NMR (DMSO): 9.38 (s, 1H), 8.38 (s, 1H), 8.06 (s, 1H), 7.54 (s, 1H), 7.20 (d, 1H, J=9.5

Hz), 6.99 (d, 1H, J=8.7 Hz), 6.22 (m, 2H), 5.85 (m, 1H), 5.23 (d, 1H, J=17 Hz), 5.07 (d, 1H, J=10.8 Hz), 4.55 (m, 2H), 4.17 (t, 2H, J=6.4 Hz), 3.18 (s, 3H), 2.94 (s, 6H), 2.57 (t, 2H, J=6.4 Hz); 19F-NMR (DMSO): −74, −120.

Example 1710

N*4*-(2-Allyloxy-4-dimethylamino-6-fluoro-phenyl)-5-chloro-N*2*-[3-(2-methoxy-ethyl)-2,3,4,5-tetrahydro-1H-benzo[d]azepin-7-yl]-pyrimidine-2,4-diamine 2-Allyloxy-N(1)-(2,5-dichloro-pyrimidin-4-yl)-6-fluoro-N(4),N(4)-dimethyl-benzene-1,4-diamine (69 mg, 0.19 mmol), 3-(2-Methoxy-ethyl)-2,3,4,5-tetrahydro-1H-benzo[d]azepin-7-ylamine (46 mg, 0.21 mmol), and 10-Camphorsulfonic acid (107 mg, 0.461 mmol) in Isopropyl alcohol (4 mL) (with trace DCM to solubilize, with heating) was irradiated in a CEM microwave (120° C., 40 min). The mixture was passed through a filter and N(4)-(2-Allyloxy-4-dimethylamino-6-fluoro-phenyl)-5-chloro-N(2)-[3-(2-methoxy-ethyl)-2,3,4,5-tetrahydro-1H-benzo[d]azepin-7-yl]-pyrimidine-2,4-diamine; compound with trifluoroacetic acid isolated by preparative HPLC as an off white lyophilate (22 mg, 17%). LCMS: 541 (M+H); 1H-NMR (DMSO): 9.60 (s, 1H), 9.20 (s, 1H), 8.23 (s, 1H), 8.02 (s, 1H), 7.44 (s, 1H), 7.14 (d, 1H, J=8.4 Hz), 6.88 (d, 1H, J=8.0 Hz), 6.23 (m, 2H), 5.87 (m, 1H), 5.24 (d, 1H, J=17.6 Hz), 5.10 (d, 1H, J=10.8 Hz), 4.55 (m, 2H), 3.67 (m, 2H), 3.58 (m, 1H), 3.48 (m, 1H), 3.34 (m, 5H), 2.97 (m, 7H), 2.85 (m, 1H); 19F-NMR (DMSO): −74, −120.

Example 1711

2-{5-Chloro-2-[3-(2-methoxy-ethyl)-2,3,4,5-tetrahydro-1H-benzo[d]azepin-7-ylamino]-pyrimidin-4-ylamino}-N-cyclopropylmethyl-3-fluoro-benzamide 1711a) Analagous to Example 308a, 2-Amino-N-cyclopropylmethyl-3-fluoro-benzamide was prepared from 3-fluoro isatoic anhydride in 49% yield. 1H-NMR (CDCl3): 7.13 (d, 1H, J=8.0 Hz), 7.05 (m, 1H), 6.57 (m, 1H), 6.13 (s, 1H), 5.59 (s, 2H), 3.28 (m, 2H), 1.05 (m, 1H), 0.55 (m, 2H), 0.28 (m, 2H); 19F-NMR (CDCl$_3$): −135.

1711b) Analagous to Example 308b, N-Cyclopropylmethyl-2-(2,5-dichloro-pyrimidin-4-ylamino)-3-fluoro-benzamide was prepared in 78% yield. MP 210-213° C.; LCMS: 355 (M+H); 1H-NMR (CDCl3): 9.27 (s, 1H), 8.21 (s, 1H), 7.33 (m, 3H), 6.23 (s, 1H), 3.27 (m, 2H), 1.01 (m, 1H), 0.55 (m, 2H), 0.25 (m, 2H); 19F-NMR (CDCl3): −111.

1711c) 10-Camphorsulfonic acid (88 mg, 0.38 mmol), N-Cyclopropylmethyl-2-(2,5-dichloro-pyrimidin-4-ylamino)-3-fluoro-benzamide (110 mg, 0.30 mmol;) and 3-(2-Methoxy-ethyl)-2,3,4,5-tetrahydro-1H-benzo[d]azepin-7-ylamine (66 mg, 0.30 mmol) in Isopropyl alcohol (3 mL) was irradiated in a CEM microwave (120° C., 40 min). Following HPLC purification, 2-{5-Chloro-2-[3-(2-methoxy-ethyl)-2,3,4,5-tetrahydro-1H-benzo[d]azepin-7-ylamino]-pyrimidin-4-ylamino}-N-cyclopropylmethyl-3-fluoro-benzamide; compound with trifluoroacetic acid was isolated as a white lyophilate (52 mg, 26%). LCMS: 539 (M+H); 1H-NMR (DMSO): 9.77 (s, 1H), 9.36 (s, 1H), 9.15 (s, 1H), 8.49 (m, 1H), 8.17 (s, 1H), 7.44 (m, 3H), 7.31 (s, 1H), 7.21 (d, 1H, J=8.0 Hz), 6.93 (d, 1H, J=8.1 Hz), 3.70 (m, 2H), 3.61 (m, 2H), 3.36 (m, 2H), 3.34 (s, 3H), 3.08 (m, 3H) 2.98 (m, 4H), 2.90 (m, 1H), 0.92 (m, 1H), 0.36 (m, 2H), 0.16 (m, 2H); 19F-NMR (DMSO): −74, −116.

Example 1712

2-[5-Chloro-2-(2-oxo-2,3,4,5-tetrahydro-1H-benzo[b]azepin-8-ylamino)-pyrimidin-4-ylamino]-N-cyclopropylmethyl-3-fluoro-benzamide 10-Camphorsulfonic acid (21 mg, 0.090 mmol), 8-Amino-1,3,4,5-tetrahydro-benzo[b]azepin-2-one (53 mg, 0.30 mmol) and N-Cyclopropylmethyl-2-(2,5-dichloro-pyrimidin-4-ylamino)-3-fluoro-benzamide (110 mg, 0.30 mmol) in Acetonitrile (3 mL) was irradiated in a CEM microwave (120° C., 40 min). Only partial conversion, due to poor solvation. Add Isopropyl alcohol (2 mL) and irradiate an additional 3 h, 120° C. Work up by pouring into 20 mL 1:1 water:satd. aq. sodium bicarbonate and extract with DCM (2×15 mL), wash with brine, dry over sodium sulfate and conc. onto 1 g silica gel. Chromatography (ISCO, 2×12 g silica, 0-5% MeOH:DCM) to afford 2-[5-Chloro-2-(2-oxo-2,3,4,5-tetrahydro-1H-benzo[b]azepin-8-ylamino)-pyrimidin-4-ylamino]-N-cyclopropylmethyl-3-fluoro-benzamide as an off white film (60 mg, 40%). LCMS: 495 (M+H); 1H-NMR (DMSO): 9.32 (s, 1H), 9.25 (s, 1H), 9.13 (s, 1H), 8.49 (m, 1H), 8.16 (s, 1H), 7.45 (m, 2H), 7.38 (m, 1H), 7.19 (d, 1H, J=8.4 Hz), 7.09 (s, 1H), 6.92 (d, 1H, J=8.2 Hz), 3.31 (s, 2H), 3.07 (t, 2H, J=6.0 Hz), 2.55 (m, 2H), 2.03 (m, 4H), 0.89 (m, 1H), 0.35 (m, 2H), 0.14 (m, 2H); 19F-NMR (DMSO): −115.

Example 1713

2-[2-(9-Acetyl-6,7,8,9-tetrahydro-5-oxa-9-aza-benzocyclohepten-2-ylamino)-5-chloro-pyrimidin-4-ylamino]-3-fluoro-N-prop-2-ynyl-benzamide 1-(2-Amino-7,8-dihydro-6H-5-oxa-9-aza-benzocyclohepten-9-yl)-ethanone (56 mg, 0.00027 mol), 2-(2,5-Dichloro-pyrimidin-4-ylamino)-3-fluoro-N-prop-2-ynyl-benzamide (92.4 mg, 0.000272 mol), and 10-Camphorsulfonic acid (16 mg, 0.000068 mol) in Isopropyl alcohol (3 mL) was irradiated in a CEM microwave (120° C., 60 min). The mixture was added dropwise with stirring to 20 mL 1:1 water:satd. sodium bicarbonate, giving a suspension which clustered to brown solids. The solids were stirred for 30 min, allowed to stand and collected. The solids were chromatographed (ISCO, 2×12 g, 0-100% EtOAc:Hex) to give 2-[2-(9-Acetyl-6,7,8,9-tetrahydro-5-oxa-9-aza-benzocyclohepten-2-ylamino)-5-chloro-pyrimidin-4-ylamino]-3-fluoro-N-prop-2-ynyl-benzamide as an orange foam (64 mg, 46%). LCMS: 509 (M+H); 1H-NMR (CDCl3): 8.65 (s, 1H), 8.08 (s, 1H), 7.69 (s, 1H), 7.41 (d, 1H, J=7.2 Hz), 7.31 (m, 2H), 6.92 (m, 3H), 4.77 (m, 1H), 4.37 (m, 1H), 4.18 (m, 2H), 3.59 (m, 1H), 2.62 (m, 1H), 1.80 (m, 2H), 1.76 (m, 4H); 19F-NMR (CDCl3): −112.

Example 1714

2-{5-Chloro-2-[9-(2-pyrrolidin-1-yl-acetyl)-6,7,8,9-tetrahydro-5-oxa-9-aza-benzocyclohepten-3-ylamino]-pyrimidin-4-ylamino}-3-fluoro-N-methyl-benzamide 1714a) 3-(3-Chloro-propyl)-6-nitro-3H-benzoxazol-2-one was prepared in 95% yield an analgous fashion to Example 1697a as yellow solids.

1714b) 3-(3-Chloro-propyl)-6-nitro-3H-benzoxazol-2-one (5.08 g, 19.8 mmol) and Potassium Ethoxide (1.80 g, 21.4 mmol) in N-Methylpyrrolidinone (60 mL) was stirred at room temperature under an atmosphere of Nitrogen. At 24 h, an additional aliquot of Potassium Ethoxide (0.91 g, 11 mmol) was added. After stirring overnight, the solution was poured into ether (100 mL) and water (50 mL), separated and extracted 2×100 mL ether. The organic extracts were washed with water (2×50 mL) and brine (50 mL), dried and conc. in vacuo. The residue was powdered onto silica gel and chromatographed (ISCO, 0-30% EtOAc:Hex) to afford 3-Nitro-7,8-dihydro-6H-5-oxa-9-aza-benzocycloheptene-9-carboxylic acid ethyl ester as a yellow solid (2.657 g, 50%). 1H-NMR (CDCl3): 7.84 (m, 2H), 7.45 (s, 1H), 4.29 (m, 4H), 3.85 (m, 2H), 2.14 (m, 2H), 1.26 (m, 3H).

1714c) 1.00 M of Potassium hydroxide in Water (38 mL) was added to 3-Nitro-7,8-dihydro-6H-5-oxa-9-aza-benzocycloheptene-9-carboxylic acid ethyl ester (1.967 g, 7.388 mmol) in 2-Methoxyethanol (80 mL) at 80° C. and further heated at 100° C. for 3 h. The solution was cooled and diluted with 200 mL water and was extracted with EtOAc (3×100 mL). The organic extract was washed with water (2×50 mL) and brine (100 mL), dried over sodium sulfate and concentrated to give 3-Nitro-6,7,8,9-tetrahydro-5-oxa-9-aza-benzocycloheptene as a yellow solid (1.34 g, 93%). 1H-NMR (CDCl3): 7.79 (s, 1H), 7.76 (d, 1H, J=8.8 Hz), 6.69 (d, 1H, J=8.8 Hz), 4.34 (s, 1H), 4.25 (t, 2H, J=5.9 Hz), 3.49 (m, 2H), 2.09 (m, 2H).

1714d) Chloroacetyl chloride (0.50 mL, 6.3 mmol; Acros) was added to a solution of 3-Nitro-6,7,8,9-tetrahydro-5-oxa-9-aza-benzocycloheptene (0.580 g, 2.99 mmol), Triethylamine (1.0 mL, 7.2 mmol), and 4-Dimethylaminopyridine (20 mg, 0.1 mmol; Acros) in Acetonitrile (40 mL) The reaction was stirred under an atmosphere of Nitrogen. After 3.5 h, Pyrrolidine (2.0 mL, 24 mmol) was added and stirred overnight. The mixture was diluted with DCM (30 mL) and water (30 mL), the layers separated and the aq. extracted with 10 mL DCM. The combined organics were washed with brine (20 mL) and dried, then conc. onto 4.5 g Celite. The residue was chromatographed (ISCO, 80 g Basic Alumina, 0-70% EtOAc:Hex) to afford 1-(3-Nitro-7,8-dihydro-6H-5-oxa-9-aza-benzocyclohepten-9-yl)-2-pyrrolidin-1-yl-ethanone as a yellow oil (664 mg, 74%). 1H-NMR (CDCl3): 7.92 (m, 2H), 7.44 (d, 1H, J=8.4 Hz), 4.2-4.6 (m, 4H), 3.15 (m, 2H), 2.48 (m, 4H), 2.10 (m, 2H), 1.70 (m, 4H).

1714e) 10% Palladium on Carbon (50% Wet) (0.09 g), 1-(3-Nitro-7,8-dihydro-6H-5-oxa-9-aza-benzocyclohepten-9-yl)-2-pyrrolidin-1-yl-ethanone (0.262 g, 0.858 mmol), and hydrazine hydrate (0.25 g, 5.0 mmol) in Ethanol (20 mL) was heated at 60° C. for 5 h. The mixture was cooled, filtered through Celite, washing with 50 mL methanol. The filtrate was conc. and azeotroped 3×30 mL toluene to afford 1-(3-Amino-7,8-dihydro-6H-5-oxa-9-aza-benzocyclohepten-9-yl)-2-pyrrolidin-1-yl-ethanone as a white solid (226 mg, 96%). 1H-NMR (CDCl3): 6.95 (d, 1H, J=8.4 Hz), 6.41 (s, 1H), 6.36 (d, 1H, J=8.4 Hz), 4.82 (d, 1H, J=13.2 Hz), 4.39 (d, 1H, J=12.1 Hz), 3.68 (m, 3H), 3.28 (m, 1H), 2.88 (m, 1H), 2.68 (m, 1H), 2.55 (m, 4H), 2.23 (m, 1H), 1.75 (m, 4H), 1.66 (m, 1H).

1714f) 1-(3-Amino-7,8-dihydro-6H-5-oxa-9-aza-benzocyclohepten-9-yl)-2-pyrrolidin-1-yl-ethanone (75 mg, 0.27 mmol), 2-(2,5-Dichloro-pyrimidin-4-ylamino)-3-fluoro-N-methyl-benzamide (85.8 mg, 0.272 mmol), and 10-Camphorsulfonic acid (79.1 mg, 0.340 mmol) in Isopropyl alcohol (3 mL) was irradiated in a CEM microwave (120° C., 40 min). The mixture was purified by HPLC to afford 2-{5-Chloro-2-[9-(2-pyrrolidin-1-yl-acetyl)-6,7,8,9-tetrahydro-5-oxa-9-aza-benzocyclohepten-3-ylamino]-pyrimidin-4-ylamino}-3-fluoro-N-methyl-benzamide; compound with trifluoroacetic acid as a beige lyophilate (27 mg, 15%). LCMS: 554 (M+H); 1H-NMR (DMSO): 9.79 (s, 1H), 9.61 (s, 1H), 9.45 (s, 1H), 8.55 (m, 1H), 8.23 (m, 1H), 7.55 (m, 4H), 7.18 (m, 2H), 4.57 (m, 1H), 4.36 (m, 1H), 4.23 (m, 1H), 3.54 (m, 6H), 3.02 (m, 1H), 2.80 (m, 1H), 2.75 (m, 2H), 1.90 (m, 6H). 19F-NMR (DMSO): −74, −114

Example 1715

3-{5-Chloro-2-[9-(2-pyrrolidin-1-yl-acetyl)-6,7,8,9-tetrahydro-5-oxa-9-aza-benzocyclohepten-3-ylamino]-pyrimidin-4-ylamino}-thiophene-2-carboxylic acid methylamide 1-(3-Amino-7,8-dihydro-6H-5-oxa-9-aza-benzocyclohepten-9-yl)-2-pyrrolidin-1-yl-ethanone (75 mg, 0.00027 mol), 3-(2,5-Dichloro-pyrimidin-4-ylamino)-thiophene-2-carboxylic acid methylamide (82.6 mg, 0.000272 mol), and 10-Camphorsulfonic acid (79.1 mg, 0.000340 mol) in Isopropyl alcohol (3 mL) was irradiated in a CEM microwave (120° C., 40 min). The mixture was purified by HPLC to afford 3-{5-Chloro-2-[9-(2-pyrrolidin-1-yl-acetyl)-6,7,8,9-tetrahydro-5-oxa-9-aza-benzocyclohepten-3-ylamino]-pyrimidin-4-ylamino}-thiophene-2-carboxylic acid methylamide; compound with trifluoroacetic acid as a light brown lyophilate (62 mg, 35%). LCMS: 542 (M+H); 1H-NMR (DMSO): 11.70 (s, 1H), 9.87 (s, 1H), 9.65 (s, 1H), 8.51 (m, 1H), 8.28 (m, 2H), 7.79 (m, 1H), 7.60 (s, 1H), 7.43 (m, 1H), 7.35 (m, 1H), 4.60 (m, 2H), 4.38 (m, 2H), 3.65 (m, 2H), 3.54 (m, 2H), 3.05 (m, 1H), 2.89 (m, 1H), 2.78 (m, 3H), 7.80 (m, 6H).

Example 1716

2-{5-Chloro-2-[9-(2-pyrrolidin-1-yl-acetyl)-6,7,8,9-tetrahydro-5-oxa-9-aza-benzocyclohepten-3-ylamino]-pyrimidin-4-ylamino}-3-fluoro-N-prop-2-ynyl-benzamide 1-(3-Amino-7,8-dihydro-6H-5-oxa-9-aza-benzocyclohepten-9-yl)-2-pyrrolidin-1-yl-ethanone (75 mg, 0.00027 mol), 2-(2,5-Dichloro-pyrimidin-4-ylamino)-3-fluoro-N-prop-2-ynyl-benzamide (92.4 mg, 0.000272 mol), and 10-Camphorsulfonic acid (79.1 mg, 0.000340 mol) in Isopropyl alcohol (4 mL) was irradiated in a CEM microwave (120° C., 40 min). The solution was purified by HPLC to give 2-{5-Chloro-2-[9-(2-pyrrolidin-1-yl-acetyl)-6,7,8,9-tetrahydro-5-oxa-9-aza-benzocyclohepten-3-ylamino]-pyrimidin-4-ylamino}-3-fluoro-N-prop-2-ynyl-benzamide; compound with trifluoroacetic acid as an off white lyophilate (72 mg, 38%). LCMS: 578 (M+H); 1H-NMR (DMSO): 9.78 (m, 1H), 9.59 (s, 1H), 9.23 (s, 1H), 8.95 (m, 1H), 8.22 (s, 1H), 7.50 (m, 4H), 7.17 (m, 2H), 4.55 (m, 1H), 4.37 (m, 1H), 4.22 (m, 1H), 4.01 (m, 2H), 3.68 (m, 4H), 3.12 (s, 1H), 3.02 (m, 1H), 2.81 (m, 2H), 1.82 (m, 6H); 19F-NMR (DMSO): −74, −115.

Example 1717

2-{5-Chloro-4-[2-(2,3-dihydroxy-propoxy)-6-fluoro-phenylamino]-pyrimidin-2-ylamino}-5-methyl-8,9-dihydro-5H-7-oxa-5-aza-benzocyclohepten-6-one 0.16 M of Osmium tetraoxide in Water (21 uL) was added to 4-Methyl-morpholine 4-oxide; hydrate (22 mg, 0.16 mmol) and 2-[4-(2-Allyloxy-6-fluoro-phenylamino)-5-chloro-pyrimidin-2-ylamino]-5-methyl-8,9-dihydro-5H-7-oxa-5-aza-benzocyclohepten-6-one (24 mg, 0.051 mmol) in Acetone (1.0 mL) and Water (0.10 mL) and stirred in a vial overnight. The mixture was purified by HPLC and lyophilized to afford 2-{5-Chloro-4-[2-(2,3-dihydroxy-propoxy)-6-fluoro-phenylamino]-pyrimidin-2-ylamino}-5-methyl-8,9-dihydro-5H-7-oxa-5-aza-benzocyclohepten-6-one, compound with trifluoroacetic acid as a white lyophilate (18 mg, 57%). LCMS: 504 (M+H); 1H-NMR (DMSO): 9.35 (s, 1H), 8.44 (s, 1H), 8.11 (s, 1H), 7.38 (s, 1H), 7.35 (m, 1H), 7.27 (m, 1H), 6.96 (m, 3H), 4.25 (m, 2H), 4.01 (m, 2H), 3.97 (m, 2H), 3.67 (m, 1H), 3.33 (m, 2H), 3.20 (s, 3H), 2.63 (m, 2H).

Example 1718

2-{5-Chloro-2-[9-(2-pyrrolidin-1-yl-ethyl)-6,7,8,9-tetrahydro-5-oxa-9-aza-benzocyclohepten-3-ylamino]-pyrimidin-4-ylamino}-3-fluoro-N-methyl-benzamide 1718a) 1.00 M of Borane-THF complex in Tetrahydrofuran (10.0 mL; Acros) was added to 1-(3-Nitro-7,8-dihydro-6H-5-oxa-9-aza-benzocyclohepten-9-yl)-2-pyrrolidin-1-yl-ethanone (0.401 g, 1.31 mmol) in Tetrahydrofuran (10 mL). The mixture was heated at 60° C. under an atmosphere of Nitrogen. overnight. The mixture was quenched with 1N HCl (5 mL) and stirred for 1 h at 60° C. The solution was neutralized by pouring into satd. sodium bicarbonate and extracted with DCM (3×). The extract was dried and conc. in vacuo to give 3-Nitro-9-(2-pyrrolidin-1-yl-ethyl)-6,7,8,9-tetrahydro-5-oxa-9-aza-benzocycloheptene as an oil (270 mg, 70%).

1718b) 10% Palladium on Carbon (50% Wet) (174 mg) and 3-Nitro-9-(2-pyrrolidin-1-yl-ethyl)-6,7,8,9-tetrahydro-5-oxa-9-aza-benzocycloheptene (270 mg, 0.93 mmol) in Ethanol (15 mL) was shaken under an atmosphere of Hydrogen (40 psi) overnight. The mixture was filtered over Celite, washing with 60 mL ethanol. After conc., 9-(2-Pyrrolidin-1-yl-ethyl)-6,7,8,9-tetrahydro-5-oxa-9-aza-benzocyclohepten-3-ylamine was obtained as an oil (224 mg, 92%). 1H-NMR (CDCl3): 6.80 (d, 1H, J=8.0 Hz), 6.34 (m, 2H), 4.05 (m, 2H), 3.44 (br s, 2H), 3.27 (m, 2H), 3.14 (t, 2H, J=5.6 Hz), 2.65 (t, 2H, J=7.2 Hz), 2.56 (m, 4H), 1.98 (m, 2H), 1.78 (m, 4H).

1718c) 10-Camphorsulfonic acid (171 mg, 0.736 mmol), 2-(2,5-Dichloro-pyrimidin-4-ylamino)-3-fluoro-N-methyl-benzamide (91 mg, 0.29 mmol), and 9-(2-Pyrrolidin-1-yl-ethyl)-6,7,8,9-tetrahydro-5-oxa-9-aza-benzocyclohepten-3-ylamine (74 mg, 0.28 mmol) in Isopropyl alcohol (3.0 mL) was irradiated in a CEM microwave (120° C., 60 min). The mixture was purified by HPLC and lyophilized to afford 2-{5-Chloro-2-[9-(2-pyrrolidin-1-yl-ethyl)-6,7,8,9-tetrahydro-5-oxa-9-aza-benzocyclohepten-3-ylamino]-pyrimidin-4-ylamino}-3-fluoro-N-methyl-benzamide; compound with trifluoroacetic acid as a white lyophilate (38 mg, 20%). LCMS: 540 (M+H); 1H-NMR (DMSO): 9.39 (m, 2H), 9.22 (s, 1H), 8.55 (m, 1H), 8.16 (s, 1H), 7.48 (m, 2H), 7.41 (m, 1H), 7.23 (s, 1H), 7.05 (d, 1H, J=9.0 Hz), 6.89 (d, 1H, J=9.1 Hz), 3.89 (m, 6H), 3.35 (m, 2H), 2.36 (m, 2H), 3.05 (m, 2H), 2.74 (d, 3H, J=4.4 Hz), 1.9 (m, 6H).

Example 1719

2-{5-Chloro-2-[9-(2-pyrrolidin-1-yl-ethyl)-6,7,8,9-tetrahydro-5-oxa-9-aza-benzocyclohepten-3-ylamino]-pyrimidin-4-ylamino}-3-fluoro-N-prop-2-ynyl-benzamide 10-Camphorsulfonic acid (171 mg, 0.736 mmol), 2-(2,5-Dichloro-pyrimidin-4-ylamino)-3-fluoro-N-prop-2-ynyl-benzamide (101 mg, 0.298 mmol), and 9-(2-Pyrrolidin-1-yl-ethyl)-6,7,8,9-tetrahydro-5-oxa-9-aza-benzocyclohepten-3-ylamine (74 mg, 0.28 mmol) in Isopropyl alcohol (3.0 mL) was irradiated in a CEM microwave (120° C., 60 min). The mixture was purified by HPLC and lyophilized to afford 2-{5-Chloro-2-[9-(2-pyrrolidin-1-yl-ethyl)-6,7,8,9-tetrahydro-5-oxa-9-aza-benzocyclohepten-3-ylamino]-pyrimidin-4-ylamino}-3-fluoro-N-prop-2-ynyl-benzamide; compound with trifluoroacetic acid as a white lyophilate (63 mg, 33%). LCMS: 564 (M+H); 1H-NMR (DMSO): 9.38 (m, 1H), 9.21 (s, 1H), 9.18 (s, 1H), 8.97 (m, 1H), 8.15 (s, 1H), 7.49 (m, 2H), 7.43 (m, 1H), 7.21 (s, 1H), 7.04 (d, 1H, J=7.7 Hz), 6.78 (d, 1H, J=8.8 Hz), 4.00 (m, 2H), 3.92 (m, 2H), 3.35 (m, 2H), 3.25 (m, 2H), 3.11 (s, 1H), 3.06 (m, 2H), 1.92 (m, 6H), 4 signals obscured by solvent water peak.

Example 1720

2-[5-Chloro-2-(9-ethyl-7-hydroxy-7-hydroxymethyl-6,7,8,9-tetrahydro-5-oxa-9-aza-benzocyclohepten-2-ylamino)-pyrimidin-4-ylamino]-3-fluoro-N-methyl-benzamide 1720a) 2-Ethylamino-4-nitro-phenol was prepared in quantitative yield from 2-methyl-5-nitrobenzoxazole analogous to Example 1692a. 1H-NMR (CDCl3): 7.55 (m, 1H), 7.46 (d, 1H, J=2.5 Hz), 6.72 (d, 1H, J=8.3 Hz), 4.92 (br s, 2H), 3.24 (q, 2H, J=7.2 Hz), 1.33 (t, 3H, J=7.2 Hz).

1720b) Sodium hydride, 60% disp. in mineral oil (7.9 g) was added to 2-Ethylamino-4-nitro-phenol (10.2 g, 56.0 mmol) in N,N-Dimethylformamide (600 mL). After 45 min, 3-Chloro-2-chloromethyl-1-propene (8.00 mL, 69.1 mmol) was added and the reaction was stirred under an atmosphere of Nitrogen for 7 days. The mixture was quenched with 10 mL satd. sodium bicarbonate and conc. to 1/5 volume. The residue was poured into satd. sodium bicarbonate (200 mL) and extracted with ether (2×200 mL). The organic layers were washed with satd. sodium bicarbonate (200 mL) and brine (3×100 mL). After drying over sodium sulfate, the residue was conc. and the crude olefin was dissolved in Acetone (600 mL) and Water (60 g); 4-Methyl-morpholine 4-oxide; hydrate (14.8 g, 109 mmol) and 0.077 M of Osmium tetraoxide in t-butanol (10.0 mL) were added and the mixture stirred under nitrogen for 7 days. The mixture was then conc. to ⅓ volume and partitioned between EtOAc and water. Following extraction, the mixture was dried, conc. and chromatographed (ISCO 120 g silica, 0-65% EtOAc:Hex). 9-Ethyl-7-hydroxymethyl-2-nitro-6,7,8,9-tetrahydro-5-oxa-9-aza-benzocyclohepten-7-ol was isolated as yellow solids (8.44 g, 56%). 1H-NMR (CDCl$_3$): 7.63 (m, 2H), 6.95 (d, 1H, J=8.1 Hz), 4.09 (m, 2H), 3.66 (m, 2H), 3.2-3.5 (m, 4H), 2.67 (s, 1H), 1.94 (m, 1H), 1.25 (t, 3H, J=7.0 Hz).

1720c) Hydrogenation of 9-Ethyl-7-hydroxymethyl-2-nitro-6,7,8,9-tetrahydro-5-oxa-9-aza-benzocyclohepten-7-ol (0.225 g, 0.839 mmol) in Ethanol (15 mL) with 10% Palladium on Carbon (50% Wet) (89 mg) under an atmosphere of Hydrogen (40 psi) for 6 h followed by filtration gave 2-Amino-9-ethyl-7-hydroxymethyl-6,7,8,9-tetrahydro-5-oxa-9-aza-benzocyclohepten-7-ol in quantitative yield as an oil (199 mg). 1H-NMR (DMSO): 9.7 (br s, 3H), 6.80 (d, 1H, J=8.2 Hz), 6.64 (s, 1H), 6.51 (d, 1H, J=8.2 Hz), 3.96 (d, 1H, J=12 Hz), 3.81 (d, 1H, J=12 Hz), 3.22 (m, 6H), 1.05 (m, 3H).

1720d) 10-Camphorsulfonic acid (107 mg, 0.462 mmol), 2-(2,5-Dichloro-pyrimidin-4-ylamino)-3-fluoro-N-methyl-benzamide (132 mg, 0.420 mmol), and 2-Amino-9-ethyl-7-hydroxymethyl-6,7,8,9-tetrahydro-5-oxa-9-aza-benzocyclohepten-7-ol (0.100 g, 0.420 mmol) in Isopropyl alcohol (3.0 mL) and the mixture was irradiated in a CEM microwave (120° C., 40 min). Purification by HPLC afforded 2-[5-Chloro-2-(9-ethyl-7-hydroxy-7-hydroxymethyl-6,7,8,9-tetrahydro-5-oxa-9-aza-benzocyclohepten-2-ylamino)-pyrimidin-4-ylamino]-3-fluoro-N-methyl-benzamide; compound with trifluoroacetic acid (51 mg, 19%) as a yellow lyophilate. LCMS: 517 (M+H); 1H-NMR (DMSO): 9.38 (s, 1H), 9.05 (s, 1H), 8.52 (m, 1H), 8.12 (s, 1H), 7.48 (m, 2H), 7.40 (m, 1H), 6.88 (d, 1H, J=9.2 Hz). 6.73 (s, 1H), 6.47 (d, 1H, J=8.4 Hz), 3.85 (d, 1H, J=12 Hz), 3.69 (d, 1H, J=12 Hz), 3.40 (s, 2H), 3.11 (m, 4H), 2.73 (d, 1H, J=4.2 Hz), 1.05 (t, 3H, J=6.8 Hz)

Example 1721

2-[5-Chloro-2-(9-ethyl-7-hydroxy-7-hydroxymethyl-6,7,8,9-tetrahydro-5-oxa-9-aza-benzocyclohepten-2-ylamino)-pyrimidin-4-ylamino]-3-fluoro-N-prop-2-ynyl-benzamide 10-Camphorsulfonic acid (107 mg, 0.462 mmol), 2-(2,5-Dichloro-pyrimidin-4-ylamino)-3-fluoro-N-prop-2-ynyl-benzamide (142 mg, 0.420 mmol), and 2-Amino-9-ethyl-7-hydroxymethyl-6,7,8,9-tetrahydro-5-oxa-9-aza-benzocyclohepten-7-ol (0.100 g, 0.420 mmol) in Isopropyl alcohol (3.0 mL) and the mixture was irradiated in a CEM microwave (120° C., 40 min). Purification by HPLC afforded 2-[5-Chloro-2-(9-ethyl-7-hydroxy-7-hydroxymethyl-6,7,8,9-tetrahydro-5-oxa-9-aza-benzocyclohepten-2-ylamino)-pyrimidin-4-ylamino]-3-fluoro-N-prop-2-ynyl-benzamide; compound with trifluoroacetic acid (73 mg, 26%) as a beige lyophilate. LCMS: 541 (M+H); 1H-NMR (DMSO): 9.19 (s, 1H), 9.04 (s, 1H), 8.95 (m, 1H), 8.12 (s, 1H), 7.48 (m, 2H), 7.42 (m, 1H), 6.87 (d, 1H, J=7.7 Hz), 6.73 (s, 1H), 6.46 (d, 1H, J=9.1 Hz), 4.00 (d, 2H, J=3.3 Hz), 3.85 (d, 1H, J=12 Hz), 3.69 (d, 1H, J=12 Hz), 3.40 (s, 2H), 3.10 (m, 5H), 1.05 (t, 3H, J=6.6 Hz).

Example 1722

2-[5-Chloro-2-(9-ethyl-7-morpholin-4-yl-6,7,8,9-tetrahydro-5-oxa-9-aza-benzocyclohepten-2-ylamino)-pyrimidin-4-ylamino]-3-fluoro-N-methyl-benzamide 1722a) Sodium periodate (0.454 g, 2.12 mmol) was added to 9-Ethyl-7-hydroxymethyl-2-nitro-6,7,8,9-tetrahydro-5-oxa-9-aza-benzocyclohepten-7-ol (0.114 g, 0.425 mmol) in Acetone (15 mL) and Water (5 mL). After 1 h, the heterogenous mixture was further diluted with Water (10 mL) and Tetrahydrofuran (10 mL), which did not create a homogenous mixture. The mixture was stirred overnight, then was partitioned between water and DCM. Extraction with DCM and washing with brine, followed by drying gave 9-Ethyl-2-nitro-8,9-dihydro-5-oxa-9-aza-benzocyclohepten-7-one (74 mg, 74%). 1H-NMR (CDCl3): 7.69 (s, 1H), 7.62 (d, 1H, J=8.8 Hz), 7.02 (d, 1H, J=8.8 Hz), 4.61 (s, 2H), 4.10 (s, 2H), 3.42 (q, 2H, J=7.2 Hz), 1.26 (t, 3H, J=7.2 Hz).

1722b) Morpholine (0.10 mL, 1.1 mmol) and 9-Ethyl-2-nitro-8,9-dihydro-5-oxa-9-aza-benzocyclohepten-7-one (74 mg, 0.31 mmol) in Methylene chloride (5 mL) was stirred for 4 h, then Sodium triacetoxyborohydride (0.13 g, 0.63 mmol) was added. After stirring overnight, a mixture of products was observed. The reaction mixture was partitioned between DCM and satd. sodium bicarbonate; the organic was washed with brine and dried over sodium sulfate. Chromatography (0-100% EtOAc:Hex) afforded 9-Ethyl-2-nitro-6,7,8,9-tetrahydro-5-oxa-9-aza-benzocyclohepten-7-ol (23 mg, 31%) and 9-Ethyl-7-morpholin-4-yl-2-nitro-6,7,8,9-tetrahydro-5-oxa-9-aza-benzocycloheptene (60 mg, 60%). 1H-NMR (CDCl3): 7.55 (m, 2H), 6.88 (m, 1H), 4.45 (m, 1H), 4.34 (m, 1H), 3.72 (m, 5H), 3.37 (m, 3H), 3.01 (m, 1H), 2.66 (m, 4H), 1.25 (t, 3H, J=7.0 Hz).

1722c) 9-Ethyl-7-morpholin-4-yl-2-nitro-6,7,8,9-tetrahydro-5-oxa-9-aza-benzocycloheptene (59 mg, 0.19 mmol) and 10% Palladium on Carbon (50% Wet) (25 mg) in Ethanol (10 mL) was shaken under an atmosphere of Hydrogen (40 psi) for 6 h. 9-Ethyl-7-morpholin-4-yl-6,7,8,9-tetrahydro-5-oxa-9-aza-benzocyclohepten-2-ylamine (46 mg, 86%) was isolated following filtration and concentration. 1H-NMR (CDCl3): 6.64 (d, 1H, J=8.4 Hz), 6.06 (s, 1H), 6.00 (d, 1H, J=8.4 Hz), 4.28 (m, 1H), 4.12 (m, 1H), 3.69 (m, 5H), 3.23 (m, 3H), 2.95 (m, 1H), 2.66 (m, 4H), 1.19 (t, 3H, J=7.0 Hz).

1722d) 2-(2,5-Dichloro-pyrimidin-4-ylamino)-3-fluoro-N-methyl-benzamide (53 mg, 0.17 mmol), 10-Camphorsulfonic acid (85 mg, 0.36 mmol), and 9-Ethyl-7-morpholin-4-yl-6,7,8,9-tetrahydro-5-oxa-9-aza-benzocyclohepten-2-ylamine (46 mg, 0.16 mmol) in Isopropyl alcohol (1.7 mL) was irradiated in a CEM microwave (120° C., 40 min), then was purified by HPLC. 2-[5-Chloro-2-(9-ethyl-7-morpholin-4-yl-6,7,8,9-tetrahydro-5-oxa-9-aza-benzocyclohepten-2-ylamino)-pyrimidin-4-ylamino]-3-fluoro-N-methyl-benzamide; compound with trifluoro-acetic acid was isolated as a yellow lyophilate (39 mg, 35%). LCMS: 556 (M+H); 1H-NMR (DMSO): 9.91 (s, 1H), 9.32 (s, 1H), 9.05 (s, 1H), 8.51 (d, 1H, J=5.0 Hz), 8.13 (s, 1H), 7.46 (m, 2H), 7.39 (m, 1H), 7.03 (d, 1H, J=8.4 Hz), 6.94 (s, 1H), 6.57 (d, 1H, J=8.8 Hz), 4.61 (d, 1H, J=12 Hz), 4.10 (d, 1H, J=12 Hz), 3.98 (m, 2H), 3.75 (m, 4H), 3.54 (m, 1H), 3.43 (m, 2H), 3.35 (m, 1H), 3.19 (m, 3H), 2.73 (d, 3H, J=4.4 Hz), 1.13 (t, 3H, J=6.8 Hz).

Example 1723

2-[5-Chloro-2-(6,7,8,9-tetrahydro-5-oxa-9-aza-benzocyclohepten-3-ylamino)-pyrimidin-4-ylamino]-3-fluoro-N-methyl-benzamide 1723a) 3-Nitro-6,7,8,9-tetrahydro-5-oxa-9-aza-benzocycloheptene (281 mg, 1.45 mmol) and 10% Palladium on Carbon (50% Wet) (77 mg) in Ethanol (10 mL) was shaken under an atmosphere of Hydrogen (50 psi) for 5 h, filtered and conc. to give 6,7,8,9-Tetrahydro-5-oxa-9-aza-benzocyclohepten-3-ylamine (230 mg, 97%). 1H-NMR (CDCl3): 6.58 (d, 1H, J=8.1 Hz), 6.40 (s, 1H), 6.27 (d, 1H, J=8.1 Hz), 4.01 (m, 2H), 3.39 (br s, 3H), 3.10 (m, 2H), 1.97 (m, 2H).

1723b) 6,7,8,9-Tetrahydro-5-oxa-9-aza-benzocyclohepten-3-ylamine (0.115 g, 0.700 mmol), 2-(2,5-Dichloro-pyrimidin-4-ylamino)-3-fluoro-N-methyl-benzamide (0.243 g, 0.770 mmol), and 10-Camphorsulfonic acid (251 mg, 1.08 mmol) in Isopropyl alcohol (4.00 mL) was irradiated in a CEM microwave (120° C., 30 min). The mixture was filtered and purified directly by HPLC to give enriched product, which was conc. and repurified. The fractions were concentrated and neutralized with MP-carbonate resin to afford 2-[5-Chloro-2-(6,7,8,9-tetrahydro-5-oxa-9-aza-benzocyclohepten-3-ylamino)-pyrimidin-4-ylamino]-3-fluoro-N-methyl-benzamide as a yellow foam (29 mg, 9%). LCMS: 443; 1H-NMR (CDCl3): 8.65 (s, 1H), 8.04 (m, 2H), 7.45 (m, 1H), 7.30 (m, 3H), 7.12 (s, 1H), 6.82 (m, 1H), 6.69 (m, 1H), 6.55 (d, 1H, J=8.4 Hz), 6.10 (q, 1H, J=4.0 Hz), 4.00 (t, 2H, J=5.2 Hz), 3.15 (t, 2H, J=5.5 Hz), 2.91 (d, 3H, J=4.8 Hz), 1.98 (m, 2H).

Example 1724

2-[2-(9-Acetyl-6,7,8,9-tetrahydro-5-oxa-9-aza-benzocyclohepten-3-ylamino)-5-chloro-pyrimidin-4-ylamino]-3-fluoro-N-methyl-benzamide 1724a) Acetyl chloride (0.080 mL, 1.1 mmol) was added to 3-Nitro-6,7,8,9-tetrahydro-5-oxa-9-aza-benzocycloheptene (203 mg, 1.04 mmol) and 4-Dimethylaminopyridine (13 mg, 0.10 mmol) in Pyridine (3.5 mL) and the reaction was stirred at room temperature overnight. The mixture was partitioned between 20 mL EtOAc and 20 mL satd. sodium bicarbonate, the org. was then washed with 1N HCl (20 mL) and brine (20 mL), dried and conc. in vacuo to give 1-(3-Nitro-7,8-dihydro-6H-5-oxa-9-aza-benzocyclohepten-9-yl)-ethanone as yellow solids (225 mg, 91%).

1724b) 1-(3-Nitro-7,8-dihydro-6H-5-oxa-9-aza-benzocyclohepten-9-yl)-ethanone (0.225 g, 0.952 mmol) was shaken with 10% Palladium on Carbon (50% Wet) (51 mg) in Ethanol (10 mL) under an atmosphere of Hydrogen (40 psi) for 6 h. Filtration and conc. afforded 1-(3-Amino-7,8-dihydro-6H-5-oxa-9-aza-benzocyclohepten-9-yl)-ethanone as white solids (195 mg, 99%). 1H-NMR (CDCl3): 7.06 (d, 1H, J=8.2 Hz), 6.81 (m, 2H), 4.78 (m, 1H), 4.40 (m, 1H), 2.72 (m, 1H), 2.23 (m, 1H), 1.89 (s, 3H), 1.81 (m, 2H).

1724c) 1-(3-Amino-7,8-dihydro-6H-5-oxa-9-aza-benzocyclohepten-9-yl)-ethanone (97 mg, 0.47 mmol), 2-(2,5-Dichloro-pyrimidin-4-ylamino)-3-fluoro-N-methyl-benzamide (169 mg, 0.536 mmol), and 10-Camphorsulfonic acid (16 mg, 0.070 mmol) in Isopropyl alcohol (4 mL) was irradiated in a CEM microwave (120° C., 30 min). The mixture was neutralized with MP-carbonate (0.3 mmol) and purified on silica gel (ISCO, 2×12 g, 0-100% EtOAc:Hex) to afford 2-[2-(9-Acetyl-6,7,8,9-tetrahydro-5-oxa-9-aza-benzocyclohepten-3-ylamino)-5-chloro-pyrimidin-4-ylamino]-3-fluoro-N-methyl-benzamide as off white solids (122 mg, 53%). MP=226-228° C.; LCMS: 485 (M+H); 1H-NMR (DMSO): 9.51 (s, 1H), 9.42 (s, 1H), 9.56 (m, 1H), 8.21 (s, 1H), 7.49 (m, 2H), 7.42 (m, 1H), 7.36 (s, 1H), 7.17 (m, 1H), 7.05 (d, 1H, J=8.5 Hz), 4.54 (m, 1H), 4.32 (m, 1H), 3.55 (m, 1H), 2.74 (d, 3H, J=4.5 Hz), 1.92 (m, 1H), 1.71 (m, 4H), 1H obscured by solvent.

Example 1725

2-[2-(9-Acetyl-6,7,8,9-tetrahydro-5-oxa-9-aza-benzocyclohepten-3-ylamino)-5-chloro-pyrimidin-4-ylamino]-3-fluoro-N-prop-2-ynyl-benzamide 1-(3-Amino-7,8-dihydro-6H-5-oxa-9-aza-benzocyclohepten-9-yl)-ethanone (97 mg, 0.47 mmol), 2-(2,5-Dichloro-pyrimidin-4-ylamino)-3-fluoro-N-prop-2-ynyl-benzamide (167 mg, 0.494 mmol), and 10-Camphorsulfonic acid (16 mg, 0.070 mmol) in Isopropyl alcohol (4 mL) was irradiated in a CEM microwave (120° C., 30 min). The mixture was neutralized with MP-carbonate (0.3 mmol) and purified on silica gel (ISCO, 2×12 g, 0-100% EtOAc:Hex) to afford 2-[2-(9-Acetyl-6,7,8,9-tetrahydro-5-oxa-9-aza-benzocyclohepten-3-ylamino)-5-chloro-pyrimidin-4-ylamino]-3-fluoro-N-prop-2-ynyl-benzamide as a light brown foam (144 mg, 60%). MP=196-199° C.; LCMS: 509 (M+H); 1H-NMR (DMSO): 9.50 (s, 1H), 9.21 (s, 1H), 8.99 (m, 1H), 8.20 (s, 1H), 7.49 (m, 3H), 7.34 (s, 1H), 7.16 (m, 1H), 7.06 (m, 1H), 4.55 (m, 1H), 4.34 (m, 1H), 4.01 (d, 2H, J=2.3 Hz), 3.55 (m, 1H), 3.11 (t, 1H, J=2.3 Hz), 2.62 (m, 1H), 1.95 (m, 1H), 1.72 (m, 4H).

Example 1726

2-{5-Chloro-2-[9-(2-methoxy-acetyl)-6,7,8,9-tetrahydro-5-oxa-9-aza-benzocyclohepten-3-ylamino]-pyrimidin-4-ylamino}-3-fluoro-N-methyl-benzamide 1726a) 3-Nitro-6,7,8,9-tetrahydro-5-oxa-9-aza-benzocycloheptene (203 mg, 1.04 mmol) and 4-Dimethylaminopyridine (13 mg, 0.10 mmol) in Pyridine (3.5 mL) was treated with Methoxyacetyl chloride (0.15 mL, 1.6 mmol) was added to the vial and stirred at rt. After 4 h, the mixture was partitioned between EtOAc and water, separated and the org. layer was washed with 1N HCl. After washing with brine and drying, 2-Methoxy-1-(3-nitro-7,8-dihydro-6H-5-oxa-9-aza-benzocyclohepten-9-yl)-ethanone was isolated following silica gel chromatography (0-100% EtOAc:Hex) as yellow solids (270 mg, 97%). 1H-NMR (CDCl3): 7.96 (m, 2H), 7.36 (m, 1H), 4.82 (m, 1H), 4.25 (m, 2H), 3.89 (m, 3H), 3.34 (s, 3H), 2.96 (m, 1H), 2.13 (m, 2H).

1726b) 2-Methoxy-1-(3-nitro-7,8-dihydro-6H-5-oxa-9-aza-benzocyclohepten-9-yl)-ethanone (269 mg, 1.01 mmol) and 10% Palladium on Carbon (50% Wet) (65 mg) in Ethanol (10 mL) was shaken under an atmosphere of Hydrogen (40 psi) for 6 h. Following filtration and conc., 1-(3-Amino-7,8-dihydro-6H-5-oxa-9-aza-benzocyclohepten-9-yl)-2-methoxy-ethanone (202 mg, 85%) was isolated as white solids. 1H-NMR (CDCl3): 7.05 (d, 1H, J=8.2 Hz), 6.80 (m, 2H), 4.79 (m, 1H), 4.40 (m, 1H), 4.02 (m, 1H), 3.72 (m, 1H), 3.60 (m, 1H), 3.34 (s, 3H), 2.72 (m, 1H), 2.24 (m, 1H), 1.78 (m, 1H).

1726c) 2-(2,5-Dichloro-pyrimidin-4-ylamino)-3-fluoro-N-methyl-benzamide (135 mg, 0.427 mmol), and 10-Camphorsulfonic acid (13 mg, 0.056 mmol) in Isopropyl alcohol (4 mL) was irradiated in a CEM microwave (120° C., 30 min). The reaction was partitioned between DCM and satd. sodium bicarbonate (5 mL each), the aq. extracted 1×5 mL DCM. The combined organics were washed with brine and dried. After conc. the residue was purified by column chromatography (ISCO, 2×12 g silica gel, 0-100% EtOAc:Hex) to afford 2-{5-Chloro-2-[9-(2-methoxy-acetyl)-6,7,8,9-tetrahydro-5-oxa-9-aza-benzocyclohepten-3-ylamino]-pyrimidin-4-ylamino}-3-fluoro-N-methyl-benzamide as a beige foam (104 mg, 47%). LCMS: 515 (M+H); 1H-NMR (CDCl3): 9.04 (s, 1H), 8.10 (s, 1H), 7.40 (s, 1H), 7.33 (m, 2H), 7.28 (m, 1H), 7.01 (m, 1H), 6.97 (m, 2H), 6.14 (q, 1H, J=4.8 Hz), 4.81 (m, 1H), 4.40 (m, 1H), 3.96 (m, 1H), 3.60 (m, 1H), 3.55 (m, 1H), 3.33 (s, 3H), 2.96 (d, 3H, J=4.9 Hz), 2.69 (m, 1H), 2.25 (m, 1H), 1.77 (m, 1H).

Example 1727

(2-{5-Chloro-2-[3-(2-methoxy-ethyl)-2,3,4,5-tetrahydro-1H-benzo[d]azepin-7-ylamino]-pyrimidin-4-ylamino}-3-fluoro-phenoxy)-acetic acid methyl ester 1727a) To a suspension of 2-(2,5-Dichloro-pyrimidin-4-ylamino)-3-fluoro-phenol (0.300 g, 1.09 mmol), Methyl Glycolate (0.118 g, 1.31 mmol), and Triphenylphosphine (0.459 g, 1.75 mmol) in Methylene chloride (10 mL) cooled to 0° C. on an ice bath was slowly added Di-tert-butyl azodicarboxylate (0.403 g, 1.75 mmol), at which time a solution formed. The reaction mixture was stirred at rt overnight. The reaction did not go to completion, so one additional equivalent of Methyl Glycolate and Triphenylphosphine were added to the reaction mixture, which was then cooled to 0° C. and one equivalent of Di-tert-butyl azodicarboxylate was also added.

The reaction was stirred at rt for an hour. The reaction mixture was concentrated and dissolved in minimal amounts of DCM. It was then purified by silica gel chromatography in 0-50% ethyl acetate solvent to afford [2-(2,5-Dichloro-pyrimidin-4-ylamino)-3-fluoro-phenoxy]-acetic acid methyl ester as a clear oil (0.30 g, 79%). 1H-NMR (DMSO): 9.26 (s, 1H), 8.37 (s, 1H), 7.34 (m, 1H), 6.98 (m, 2H), 4.83 (s, 2H), 3.66 (s, 3H).

1727b) 3-(2-Methoxy-ethyl)-2,3,4,5-tetrahydro-1H-benzo[d]azepin-7-ylamine (0.21 g, 0.00095 mol), [2-(2,5-Dichloro-pyrimidin-4-ylamino)-3-fluoro-phenoxy]-acetic acid methyl ester (0.300 g, 0.000867 mol), 10-Camphorsulfonic acid (0.242 g, 0.00104 mol), and Isopropyl alcohol (6 mL) was microwaved at 120° C. for 30 minutes. The reaction mixture was concentrated and purified by HPLC to afford (2-{5-Chloro-2-[3-(2-methoxy-ethyl)-2,3,4,5-tetrahydro-1H-3-benzazepin-7-ylamino]-pyrimidin-4-ylamino}-3-fluoro-phenoxy)-acetic acid methyl ester; compound with trifluoro-acetic acid as an off white lyophilate (153 mg, 27%). LCMS: 530 (M+H); 1HNMR (DMSO): 9.58 (s, 1H), 9.27 (s, 1H), 8.50 (s, 1H), 8.09 (s, 1H), 7.36 (m, 1H), 7.15 (d, J=6.84 Hz, 1H), 6.99 (dd, J=9.08 Hz, 1H), 6.95 (d, J=8.60 Hz, 1H), 6.88 (d, J=8.36 Hz, 1H), 4.82 (s, 2H), 3.70 (t, J=4.52 Hz, 2H), 3.61 (s, 3H), 3.59 (m, 2H), 3.37 (m, 2H), 3.35 (s, 3H), 3.96 (m, 4H);

Example 1728

2-{5-Chloro-2-[3-(2-methoxy-ethyl)-2,3,4,5-tetrahydro-1H-benzo[d]azepin-7-ylamino]-pyrimidin-4-ylamino}-3,5-difluoro-N-prop-2-ynyl-benzamide 1728a) 3,5-Difluoro-2-nitro-benzoic acid (2.908 g, 0.01432 mol), 10% Palladium on Carbon (50% Wet) (0.61 g). and Methanol (15 mL) was shaken under an atmosphere of Hydrogen at 38 PSI overnight. The reaction mixture was filtered through celite and concentrated under reduced pressure and azeotroped with toluene to give 2-Amino-3,5-difluoro-benzoic acid as off white solids (2.44 g, 99%). 1H-NMR (CDCl3): 7.45 (d, 1H, J=9.3 Hz), 7.03 (m, 1H), 5.65 (br s, 2H).

1728b) 2-Amino-3,5-difluoro-benzoic acid (2.44 g, 0.0141 mol) was dissolved in Tetrahydrofuran (100 mL). Triphosgene (4.18 g, 0.0141 mol) was dissolved in Tetrahydrofuran (10 mL) and added. The resulting solution was stirred for 4 h at rt. The reaction mixture was concentrated, and the resulting residue was sonicated in H20. The peach ppt was filtered, taken up in acetone, and was concentrated under reduced pressure. It was then azeotroped in toluene to give 6,8-Difluoro-1H-3,1-benzoxazine-2,4-dione as tan solids (2.64 g, 94%). 1H-NMR (DMSO): 12.00 (s, 1H), 7.85 (m, 1H), 7.60 (m, 1H); 19F-NMR (DMSO): −116, −125.

1728c) Analagous to Example 308a, 2-Amino-3,5-difluoro-N-prop-2-ynyl-benzamide was prepared in 64% yield from 6,8-Difluoro-1H-3,1-benzoxazine-2,4-dione and propargyl amine. 1H-NMR (DMSO): 8.86 (s, 1H), 7.30 (m, 2H), 6.26 (s, 2H), 4.01 (d, 2H, J=3.1 Hz), 3.13 (t, 1H, J=3.1 Hz).

1728d) Analagous to Example 308b, 2-(2,5-Dichloro-pyrimidin-4-ylamino)-3,5-difluoro-N-prop-2-ynyl-benzamide was prepared in 51% yield as yellow solids. 1H-NMR (DMSO): 9.47 (s, 1H), 8.96 (m, 1H), 8.04 (s, 1H), 7.62 (m, 1H), 7.32 (m, 1H), 3.96 (m, 2H), 3.10 (m, 1H).

1728e) 3-(2-Methoxy-ethyl)-2,3,4,5-tetrahydro-1H-benzo[d]azepin-7-ylamine (0.051 g, 0.23 mmol), 2-(2,5-Dichloro-pyrimidin-4-ylamino)-3,5-difluoro-N-prop-2-ynyl-benzamide (0.075 g, 0.21 mmol) and 10-Camphorsulfonic acid (0.0585 g, 0.252 mmol), in Isopropyl alcohol (2 mL) was microwaved on 120° C. for 30 minutes then purified by HPLC to afford 2-{5-Chloro-2-[3-(2-methoxy-ethyl)-2,3,4,5-tetrahydro-1H-3-benzazepin-7-ylamino]-pyrimidin-4-ylamino}-3,5-difluoro-N-prop-2-ynyl-benzamide; compound with trifluoroacetic acid as a white lyophilate (64 mg, 48%). LCMS: 541 (M+H); 1HNMR (DMSO): 9.65 (s, 1H), 9.30 (s, 1H), 8.90 (dd, J=4.00 Hz, 1H), 8.83 (s, 1H), 8.15 (s, 1H), 7.63 (dd, J=8.56 Hz, 1H), 7.40 (d, J=8.56 Hz, 1H), 7.28 (s, 1H), 7.21 (dd, J=8.08 Hz, 1H), 6.95 (d, J=8.60 Hz, 1H), 4.00 (d, J=3.28 Hz, 2H), 3.68 (t, J=4.80 Hz, 2H), 3.60 (m, 2H), 3.37 (m, 2H), 3.34 (s, 3H), 3.13 (m, 2H), 3.34 (s, 3H), 3.13 (m, 2H), 3.09 (m, 1H), 3.00 (m, 2H), 2.86 (m, 1H);

Example 1729

2-[5-Chloro-2-(2-oxo-2,3,4,5-tetrahydro-1H-benzo[b]azepin-8-ylamino)-pyrimidin-4-ylamino]-3,5-difluoro-N-prop-2-ynyl-benzamide 8-Amino-1,3,4,5-tetrahydro-benzo[b]azepin-2-one (0.037 g, 0.00021 mol), 2-(2,5-Dichloro-pyrimidin-4-ylamino)-3,5-difluoro-N-prop-2-ynyl-benzamide (0.069 g, 0.00019 mol), and 10-Camphorsulfonic acid (0.0045 g, 0.000019 mol), in Isopropyl alcohol (1 mL) was microwaved at 120° C. for 30 minutes. Sodium bicarbonate was added to the reaction mixture, which was then filtered and the resulting ppt was washed first with water then three times with 1 mL of Isopropyl alcohol. 2-[5-Chloro-2-(2-oxo-2,3,4,5-tetrahydro-1H-1-benzazepin-8-ylamino)-pyrimidin-4-ylamino]-3,5-difluoro-N-prop-2-ynyl-benzamide was isolated as tan solids (49 mg, 51%). MP: 194° C.; LCMS: 497 (M+H); 1HNMR (DMSO): 9.33 (s, 1H), 9.27 (s, 1H), 8.93 (d, J=5.64 Hz, 1H), 8.87 (s, 1H), 8.14 (s, 1H), 7.57 (t, J=8.84 Hz, 1H), 7.34 (d, J=8.60 Hz, 1H), 7.19 (d, J=9.36 Hz, 1H), 7.09 (s, 1H), 6.93 (d, J=7.56 Hz, 1H), 3.99 (s, 2H), 3.11 (s, 1H), 2.57 (t, J=5.52 Hz, 2H), 2.08 (d, J=5.56 Hz, 2H), 2.03 (t, J=6.80 Hz, 2H);

Example 1730

5-Chloro-N*2*-[3-(2-methoxy-ethyl)-2,3,4,5-tetrahydro-1H-benzo[d]azepin-7-yl]-N*4*-[2-(pyrrolidine-1-sulfonyl)-phenyl]-pyrimidine-2,4-diamine 3-(2-Methoxy-ethyl)-2,3,4,5-tetrahydro-1H-benzo[d]azepin-7-ylamine (0.051 g, 0.23 mmol), (2,5-Dichloro-pyrimidin-4-yl)-[2-(pyrrolidine-1-sulfonyl)-phenyl]-amine (0.078 g, 0.21 mmol), and 10-Camphorsulfonic acid (0.0585 g, 0.252 mmol), in Isopropyl alcohol (2 mL) was irradiated in a CEM microwave (120° C., 30 min), then was purified by HPLC. 5-Chloro-N*2*-[3-(2-methoxy-ethyl)-2,3,4,5-tetrahydro-1H-benzo[d]azepin-7-yl]-N*4*-[2-(pyrrolidine-1-sulfonyl)-phenyl]-pyrimidine-2,4-diamine; compound with trifluoroacetic acid was isolated as a white lyophilate (55 mg, 39%). LCMS: 557 (M+H); 1H-NMR (DMSO): 9.66 (s, 1H), 9.55 (s, 1H), 9.35 (s, 1H), 8.52 (s, 1H), 8.29 (s, 1H), 7.89 (d, J=8.0 Hz, 1H), 7.69 (dd, J=8.0 Hz, 1H), 7.45 (s, 1H), 7.39 (m, 2H), 7.08 (d, J=8.0 Hz, 1H), 3.69 (m, 2H), 3.64 (m, 2H), 3.38 (m, 2H), 3.34 (m, 2H), 3.15 (m, 6H), 3.02 (m, 3H), 1.68 (m, 4H).

Example 1731

8-{5-Chloro-4-[2-(pyrrolidine-1-sulfonyl)-phenylamino]-pyrimidin-2-ylamino}-1,3,4,5-tetrahydro-benzo[b]azepin-2-one 8-Amino-1,3,4,5-tetrahydro-benzo[b]azepin-2-one (0.037 g, 0.21 mmol), (2,5-Dichloro-pyrimidin-4-yl)-[2-(pyrrolidine-1-sulfonyl)-phenyl]-amine (0.072 g, 0.19 mmol) and 10-Camphorsulfonic acid (0.0045 g, 0.019 mmol) in Isopropyl alcohol (1 mL) was irradiated in a CEM microwave (120° C., 30 min). One mL Sodium bicarbonate and 1 mL water were added to the reaction mixture, which was then filtered and the resulting ppt was washed first with water then three times with 1 mL of Isopropyl alcohol. The solid was then purified by silica gel chromatography (ISCO, 0-100% EtOAc) to afford 8-{5-Chloro-4-[2-(pyrrolidine-1-sulfonyl)-phenylamino]-pyrimidin-2-ylamino}-1,3,4,5-tetrahydro-benzo[b]azepin-2-one as a white powder (59 mg, 60%). MP 249-251° C.; LCMS: 513 (M+H); 1H-NMR (DMSO): 9.56 (s, 1H), 9.45 (s, 1H), 9.41 (s, 1H), 8.61 (s, 1H), 8.29 (s, 1H), 7.86 (d, J=8.0 Hz, 1H), 7.67 (dd, J=8.0 Hz, 1H), 7.34 (d, J=8.0 Hz, 1H), 7.31 (s, 1H), 7.27 (s, 1H), 7.09 (d, J=8.0 Hz, 1H), 3.14 (t, J=4.0 Hz, 4H), 2.62 (t, J=8.0 Hz, 2H), 2.15 (t, J=8.0 Hz, 2H), 2.07 (m, 2H), 1.68 (m, 4H).

Example 1732

2-{5-Chloro-4-[2-fluoro-6-(2-hydroxy-ethoxy)-phenylamino]-pyrimidin-2-ylamino}-5-methyl-8,9-dihydro-5H-7-oxa-5-aza-benzocyclohepten-6-one 1732a) To a suspension of 2-(2,5-Dichloro-pyrimidin-4-ylamino)-3-fluoro-phenol (0.150 g, 0.547 mmol), 2-(Tetrahydro-pyran-2-yloxy)-ethanol (0.0960 g, 0.657 mmol), and Triphenylphosphine (0.230 g, 0.876 mmol) in Methylene chloride (6 mL) cooled to 0° C. on an ice bath was slowly added Di-tert-butyl azodicarboxylate (0.202 g, 0.876 mmol), at which time a solution formed. The reaction mixture was stirred at rt overnight. The reaction did not go to completion so equal amounts of 2-(Tetrahydro-pyran-2-yloxy)-ethanol, Triphenylphosphine, Methylene chloride, and Di-tert-butyl azodicarboxylate were added as were at the start of the reaction and stirred. The reaction mixture was then concentrated and dissolved in minimal amounts of DCM. It was then purified by silica gel chromatography (ISCO, 0-30% EtOAc) to give (2,5-Dichloro-pyrimidin-4-yl)-{2-fluoro-6-[2-(tetrahydro-pyran-2-yloxy)-ethoxy]-phenyl}-amine as a clear oil (98 mg, 44%). 1H-NMR (CDCl3): 8.17 (s, 1H), 7.22 (m, 1H), 6.93 (s, 1H), 6.82 (m, 2H), 4.63 (s, 1H), 4.22 (m, 2H), 3.98 (m, 1H), 3.74 (m, 2H), 3.47 (m, 1H), 1.67 (m, 2H), 1.55 (m, 2H) 1.49 (m, 2H)

1732b) 2-Amino-5-methyl-8,9-dihydro-5H-7-oxa-5-aza-benzocyclohepten-6-one (0.0435 g, 0.000226 mol), (2,5-Dichloro-pyrimidin-4-yl)-{2-fluoro-6-[2-(tetrahydro-pyran-2-yloxy)-ethoxy]-phenyl}-amine (0.091 g, 0.00023 mol), 10-Camphorsulfonic acid (0.0788 g, 0.000339 mol), and Isopropyl alcohol (2 mL) were added to a 10 mL microwave tube and microwaved at 120° C. for 30 minutes. The reaction mixture was then purified by HPLC, lyophilized and neutralized with MP-carbonate to afford 2-{5-Chloro-4-[2-fluoro-6-(2-hydroxy-ethoxy)-phenylamino]-pyrimidin-2-ylamino}-5-methyl-8,9-dihydro-5H-7-oxa-5-aza-benzocyclohepten-6-one as a yellow solid (11 mg, 10%). MP=199-201° C.; LCMS: 474 (M+H); HNMR (CDCl3): 8.07 (s, 1H), 7.36 (m, 2H), 7.10 (m, 1H), 6.84 (m, 4H), 6.64 (s, 1H), 4.42 (t, J=7.04 Hz, 2H), 4.13 (m, 2H), 3.87 (m, 2H), 3.33 (s, 3H), 2.78 (t, J=6.32 Hz, 2H).

Example 1733

2-[5-Chloro-2-(9-isopropyl-6,7,8,9-tetrahydro-5-oxa-9-aza-benzocyclohepten-2-ylamino)-pyrimidin-4-ylamino]-3-fluoro-N-prop-2-ynyl-benzamide 1733a) Acetone (0.284 mL, 3.86 mmol) was added to a solution of 2-Nitro-6,7,8,9-tetrahydro-5-oxa-9-aza-benzocycloheptene (0.250 g, 1.29 mmol) in 1,2-Dichloroethane (5 mL), followed by 1.00 M of Titanium tetrachloride in Methylene chloride (1.29 mL). The reaction mixture was stirred for 2 hours. Then, Sodium triacetoxyborohydride (1.36 g, 6.44 mmol) was added and the reaction was stirred overnight. The reaction mixture was diluted with 30 mL DCM, 30 mL saturated sodium bicarbonate and extracted. The organic layer was then concentrated and purified by column chromatography (ISCO 0-60% EtOAc) to give 9-Isopropyl-2-nitro-6,7,8,9-tetrahydro-5-oxa-9-aza-benzocycloheptene as orange solids (128 mg, 42%). LCMS: 237; 1H-NMR (DMSO): 7.47 (m, 2H), 6.91 (d, 1H, J=8.5 Hz), 4.31 (m, 2H), 3.86 (sept, 1H, J=6.5 Hz), 3.30 (m, 2H), 1.92 (m, 2H), 1.19 (d, 6H, J=6.5 Hz).

1733b) 9-Isopropyl-2-nitro-6,7,8,9-tetrahydro-5-oxa-9-aza-benzocycloheptene (0.128 g, 0.000542 mol), 10% Palladium on Carbon (50% Wet) (0.023 g). and Methanol (0.57 mL) was shaken under an atmosphere of Hydrogen at 40 psi overnight. Filtration and conc. afforded 9-Isopropyl-6,7,8,9-tetrahydro-5-oxa-9-aza-benzo-cycloheptan-2-ylamine as a brown oil (109 mg, 98%). LCMS: 206.

1733c) 9-Isopropyl-6,7,8,9-tetrahydro-5-oxa-9-aza-benzocyclohepten-2-ylamine (0.054 g, 0.26 mmol), 2-(2,5-Dichloro-pyrimidin-4-ylamino)-3-fluoro-N-prop-2-ynyl-benzamide (0.081 g, 0.24 mmol), and 10-Camphorsulfonic acid (0.0663 g, 0.286 mmol) in Isopropyl alcohol (2 mL) was irradiated in a CEM microwave (120° C., 30 min), then was purified by HPLC. 2-[5-Chloro-2-(9-isopropyl-6,7,8,9-tetrahydro-5-oxa-9-aza-benzocyclohepten-2-ylamino)-pyrimidin-4-ylamino]-3-fluoro-N-prop-2-ynyl-benzamide; compound with trifluoroacetic acid was isolated as an off white lyophilate (36 mg, 24%). LCMS: 509 (M+H); 1H-NMR (DMSO): 9.20 (s, 1H), 8.94 (s, 1H), 8.15 (s, 1H), 7.48 (m, 4H), 4.34 (m, 5H), 4.00 (m, 2H), 3.10 (m, 1H), 1.18 (m, 2H), 1.11 (m, 6H).

Example 1734

2-[5-Chloro-2-(9-isopropyl-6,7,8,9-tetrahydro-5-oxa-9-aza-benzocyclohepten-2-ylamino)-pyrimidin-4-ylamino]-3-fluoro-N-methyl-benzamide 9-Isopropyl-6,7,8,9-tetrahydro-5-oxa-9-aza-benzocyclohepten-2-ylamine (0.054 g, 0.26 mmol), 2-(2,5-Dichloro-pyrimidin-4-ylamino)-3-fluoro-N-methyl-benzamide (0.075 g, 0.24 mmol) and 10-Camphorsulfonic acid (0.0663 g, 0.286 mmol) in Isopropyl alcohol (2 mL) was irradiated in a CEM microwave (120° C., 30 min), then was purified by HPLC. 2-[5-Chloro-2-(9-isopropyl-6,7,8,9-tetrahydro-5-oxa-9-aza-benzocyclohepten-2-ylamino)-pyrimidin-4-ylamino]-3-fluoro-N-methyl-benzamide; compound with trifluoroacetic acid was isolated as a yellow lyophilate (41 mg, 29%). LCMS: 485; 1H-NMR (DMSO): 9.38 (s, 1H), 8.52 (m, 1H), 8.16 (s, 1H), 7.48 (m, 3H), 7.41 (m, 1H), 4.11 (m, 5H), 2.72 (d, 3H, J=4.4 Hz), 1.91 (m, 2H), 1.10 (m, 6H).

Example 1735

2-[5-Chloro-2-(9-ethyl-7-hydroxy-7-hydroxymethyl-6,7,8,9-tetrahydro-5-oxa-9-aza-benzocyclohepten-3-ylamino)-pyrimidin-4-ylamino]-3-fluoro-N-prop-2-ynyl-benzamide 1735a) Analogous to Example 1720b, 9-Ethyl-7-hydroxymethyl-3-nitro-6,7,8,9-tetrahydro-5-oxa-9-aza-benzocyclohepten-7-ol was prepared in 50% yield from 2-Ethylamino-5-nitro-phenol as a yellow solid. 8.20 (d, 1H, J=9.3 Hz), 7.94 (s, 1H), 7.22 (d, 1H, J=9.3 Hz), 5.43 (s, 1H), 5.26 (t, 2H, J=5.2 Hz), 4.46 (d, 1H, J=12 Hz), 4.29 (d, 1H, J=12 Hz), 3.87 (m, 2H), 3.82 (m, 4H), 3.74 (s, 2H), 1.55 (t, 3H, J=7.0 Hz).

65b) Analogous to Example 1720c, 3-Amino-9-ethyl-7-hydroxymethyl-6,7,8,9-tetrahydro-5-oxa-9-aza-benzocyclohepten-7-ol was prepared in quantitive yield from 9-Ethyl-7-hydroxymethyl-3-nitro-6,7,8,9-tetrahydro-5-oxa-9-aza-benzocyclohepten-7-ol as a black oil.

1735c) 10-Camphorsulfonic acid (107 mg, 0.462 mmol), 2-(2,5-Dichloro-pyrimidin-4-ylamino)-3-fluoro-N-prop-2-ynyl-benzamide (142 mg, 0.420 mmol), and 3-Amino-9-ethyl-7-hydroxymethyl-6,7,8,9-tetrahydro-5-oxa-9-aza-benzocyclohepten-7-ol (0.100 g, 0.420 mmol) in Isopropyl alcohol (3.0 mL) and the mixture was irradiated in a CEM microwave (120° C., 40 min). The reaction mixture was then purified by HPLC and lyophilized to afford 2-[5-Chloro-2-(9-ethyl-7-hydroxy-7-hydroxymethyl-6,7,8,9-tetrahydro-5-oxa-9-aza-benzocyclohepten-3-ylamino)-pyrimidin-4-ylamino]-3-fluoro-N-prop-2-ynyl-benzamide as a yellow lyophilate (2 mg, 1%). LCMS: 541.31 (M+H); 1HNMR (CDCl$_3$): 9.33 (s, 1H), 8.02 (s, 1H), 7.46 (d, J=5.32 Hz, 4H), 7.33 (s, 1H), 6.97 (s, 1H), 6.65 (d, J=7.80 Hz, 1H), 4.05 (m, 4H), 3.87 (s, 2H), 3.51 (s, 2H), 3.13 (s, 2H), 1.12 (t, J=7.04 Hz, 3H);

Example 1736

2-[5-Chloro-2-(9-ethyl-7-hydroxy-7-hydroxymethyl-6,7,8,9-tetrahydro-5-oxa-9-aza-benzocyclohepten-3-ylamino)-pyrimidin-4-ylamino]-3-fluoro-N-methyl-benzamide 10-Camphorsulfonic acid (107 mg, 0.462 mmol), 2-(2,5-Dichloro-pyrimidin-4-ylamino)-3-fluoro-N-methyl-benzamide (132 mg, 0.420 mmol), and 3-Amino-9-ethyl-7-hydroxymethyl-6,7,8,9-tetrahydro-5-oxa-9-aza-benzocyclohepten-7-ol (0.100 g, 0.420 mmol) in Isopropyl alcohol (3.0 mL) and the mixture was irradiated in a CEM microwave (120° C., 40 min). The reaction mixture was then purified by HPLC and lyophilized to afford 2-[5-Chloro-2-(9-ethyl-7-hydroxy-7-hydroxymethyl-6,7,8,9-tetrahydro-5-oxa-9-aza-benzocyclohepten-3-ylamino)-pyrimidin-4-ylamino]-3-fluoro-N-methyl-benzamide as a black lyophilate (2 mg, 1%). LCMS: 517.32 (M+H); HNMR (CD3CN): 9.70 (s, 1H), 8.03 (s, 1H), 7.43 (m, 3H), 7.10 (s, 1H), 7.00 (s, 1H), 6.84 (d, J=8.84 Hz, 1H), 6.66 (d, J=8.60 Hz, 1H), 4.02 (q, J=6.80 Hz, 2H), 3.87 (s, 1H), 3.51 (s, 1H), 3.32 (m, 4H), 3.13 (s, 2H), 2.81 (s, 5H), 1.12 (t, J=7.08 Hz, 3H).

Example 1741

2-[5-Chloro-2-(5-methyl-6-oxo-5,6,8,9-tetrahydro-7-oxa-5-aza-benzocyclohepten-2-ylamino)-pyrimidin-4-ylamino]-N-methylbenzamide 1741a) To a solution of 2-aminophenethyl alcohol (4.0 g, 29.16 mmol) in THF (200 mL) was added a solution of 2M phosgene in toluene (17 mL, 34 mmol) at room temperature. The reaction was stirred for 15 minutes, concentrated, and purified with flash chromatography using ethyl acetate (5%→20%) in hexanes to yield 8,9-dihydro-5H-7-oxa-5-aza-benzocyclohepten-6-one (4 g, 84%): $^1$H NMR (300 MHz, CDCl$_3$) δ 8.02 (bs, 1H), 7.17 (dt, 1H), 7.09 (d, 1H), 6.99 (dt, 1H), 6.90 (d, 1H), 4.51 (t, 2H), 3.21 (t, 2H).

1741b) To a 0° C. solution of 8,9-dihydro-5H-7-oxa-5-aza-benzocyclohepten-6-one (2.2 g, 13.5 mmol) in sulfuric acid (15 mL) was added nitric acid (0.61 mL, 13.5 mmol, 1 eq.). The ice bath was removed and the reaction was stirred for 30 minutes. The mixture was poured onto ice resulting in the precipitation of 2-nitro-8,9-dihydro-5H-7-oxa-5-aza-benzocyclohepten-6-one, which was collected by filtration. The product was washed with water and a minimum of acetone and then dried under vacuum to yield the pure product (2.0 g, 71%): $^1$H NMR (300 MHz, DMSO-D$_6$) δ 10.19 (s, 1H), 8.09 (d, 1H), 8.04 (dd, 1H), 7.26 (d, 1H), 4.43 (t, 2H), 3.25 (t, 2H).

1741c) A mixture of 2-nitro-8,9-dihydro-5H-7-oxa-5-aza-benzocyclohepten-6-one (0.7 g, 3.36 mmol), potassium carbonate (1.4 g, 10.1 mmol, 3 eq.), and iodomethane (0.42 mL, 6.7 mmol, 2 eq.) was stirred for 16 hours in DMF (10 mL). The mixture was diluted with water (50 mL) and extracted with ethyl acetate (3×20 mL). The combined organic layers were dried (sodium sulfate) and concentrated to provide 2-nitro-5-methyl-8,9-dihydro-5H-7-oxa-5-aza-benzocyclohepten-6-one: $^1$H NMR (300 MHz, CDCl$_3$) δ 8.19 (dd, 1H), 8.13 (d, 1H), 7.28 (d, 1H), 4.55 (t, 2H), 3.43 (s, 3H), 3.10 (t, 2H).

1741d) A mixture of 2-nitro-5-methyl-8,9-dihydro-5H-7-oxa-5-aza-benzocyclohepten-6-one (0.7 g) and 50% Raney Ni (1 mL) in ethanol (25 mL) was hydrogenated at 30 psi for 3 hours. The reaction mixture was filtered through celite and concentrated to yield 2-amino-5-methyl-8,9-dihydro-5H-7-oxa-5-aza-benzocyclohepten-6-one: $^1$H NMR (300 MHz, CDCl$_3$) δ 6.94 (d, 1H), 6.60 (dd, 1H), 6.53 (d, 1H), 4.45 (t, 2H), 3.67 (bs, 1H), 3.33 (s, 3H), 2.87 (t, 2H).

1741e) A mixture of 2-(2,5-dichloro-pyrimidin-4-ylamino)-N-methylbenzamide (50 mg, 0.17 mmol), 2-amino-5-methyl-8,9-dihydro-5H-7-oxa-5-aza-benzocyclohepten-6-one (49 mg, 0.25 mmol) and camphorsulfornic acid (4 mg, 0.02 mmol) in IPA (5 mL) was microwave-heated at 120° C. for 3.5 h. The mixture was concentrated and chromatographed with preparative TLC (methylene chloride and ethyl acetate (4:1)) to give 54 mg of 2-[5-chloro-2-(5-methyl-6-oxo-5,6,8,9-tetrahydro-7-oxa-5-aza-benzocyclohepten-2-ylamino)-pyrimidin-4-ylamino]-N-methyl-benzamide (71%): $^1$H NMR (300 MHz, CDCl$_3$) δ 8.33 (d, 1H), 7.95 (s, 1H), 7.56 (d, 1H), 7.43 (dd, 1H), 7.34 (d, 1H), 7.26 (m, 1H), 7.1 (t, 1H), 7.05 (d, 1H). 4.35 (t, 2H), 3.3 (s, 3H), 2.9 (s, 3H), 2.85 (t, 2H); MS (m/e): 453.3 (M+1).

Example 1742

3-Fluoro-2-[5-chloro-2-(5-methyl-6-oxo-5,6,8,9-tetrahydro-7-oxa-5-aza-benzocyclohepten-2-ylamino)-pyrimidin-4-ylamino]-N-methyl-benzamide A mixture of 2-amino-5-methyl-8,9-dihydro-5H-7-oxa-5-aza-benzocyclohepten-6-one and 3-fluoro-2-(2,5-dichloro-pyrimidin-4-ylamino)-N-methyl-benzamide in IPA (3 mL) was treated with 4 drops of 4N HCl/dioxane and microwave-heated at 120° C. for 90 minutes. The mixture was concentrated and purified by semipreparative HPLC to afford 3-fluoro-2-[5-chloro-2-(5-methyl-6-oxo-5,6,8,9-tetrahydro-7-oxa-5-aza-benzocyclohepten-2-ylamino)-pyrimidin-4-ylamino]-N-methyl-benzamide: $^1$H NMR (300 MHz, CDCl$_3$) δ 8.87 (s, 1H), 8.08 (s, 1H), 7.30 (m, 5H), 6.91 (d, 2H), 6.10 (bq, 1H), 4.41 (t, 2H), 3.35 (s, 3H), 2.92 (d, 3H), 2.81 (t, 2H); MS (m/e) 471 (M+1).

Example 1743

3-Chloro-2-[5-chloro-2-(5-methyl-6-oxo-5,6,8,9-tetrahydro-7-oxa-5-aza-benzocyclohepten-2-ylamino)-pyrimidin-4-ylamino]-N-methyl-benzamide Following a procedure analogous to Example 1741e, 2-amino-5-methyl-8,9-dihydro-5H-7-oxa-5-aza-benzocyclohepten-6-one and 3-chloro-2-(2,5-dichloro-pyrimidin-4- ylamino)-N-methyl-benzamide were converted to 3-chloro-2-[5-chloro-2-(5-methyl-6-oxo-5,6,8,9-tetrahydro-7-oxa-5-aza-benzocyclohepten-2-ylamino)-pyrimidin-4-ylamino]-N-methyl-benzamide: $^1$H NMR of TFA salt (300 MHz, 5% CD$_3$OD in CDCl$_3$) δ 8.06 (s, 1H), 7.68 (dd, 1H), 7.59 (d, 1H), 7.47 (t, 1H), 7.28 (s, 1H), 7.25 (d, 1H), 6.91 (d, 1H), 4.43 (t, 2H), 3.37 (s, 3H), 2.92 (t, 3H), 2.84 (t, 2H); MS (m/e) 487 (M+1).

Example 1744

2-[5-Chloro-2-(5-methyl-6-oxo-5,6,8,9-tetrahydro-7-oxa-5-aza-benzocyclohepten-2-ylamino)-pyrimidin-4-ylamino]-3,N-dimethyl-benzamide Following a procedure analogous to Example 1742a, 2-amino-5-methyl-8,9-dihydro-5H-7-oxa-5-aza-benzocyclohepten-6-one and 2-(2,5-dichloro-pyrimidin-4-ylamino)-3,N-dimethyl-benzamide were converted to 2-[5-chloro-2-(5-methyl-6-oxo-5,6,8,9-tetrahydro-7-oxa-5-aza-benzocyclohepten-2-ylamino)-pyrimidin-4-ylamino]-3,N-dimethyl-benzamide. TFA salt: $^1$H NMR (300 MHz, CDCl$_3$) δ 11.84 (bs, 1H), 9.91 (s, 1H), 7.90 (s, 1H), 7.53-7.33 (m, 5H), 6.91 (d, 1H), 6.52 (bq, 1H), 4.46 (bs, 2H), 3.43 (s, 3H), 3.08 (d, 3H), 2.83 (bt, 2H), 2.32 (s, 3H); MS (m/e) 467 (M+1).

Example 1745

2-[5-chloro-2-(5-ethyl-6-oxo-5,6,8,9-tetrahydro-7-oxa-5-aza-benzocyclohepten-2-ylamino)-pyrimidin-4-ylamino]-N-methyl-benzamide Following a procedure analogous to Example 1741c, 2-nitro-8,9-dihydro-5H-7-oxa-5-aza-benzocyclohepten-6-one and iodoethane were converted to 2-nitro-5-ethyl-8,9-dihydro-5H-7-oxa-5-aza-benzocyclohepten-6-one, which was converted to 2-amino-5-ethyl-8,9-dihydro-5H-7-oxa-5-aza-benzocyclohepten-6-one using a procedure analogous to Example 1741d. The final compound 2-[5-chloro-2-(5-ethyl-6-oxo-5,6,8,9-tetrahydro-7-oxa-5-aza-benzocyclohepten-2-ylamino)-pyrimidin-4-ylamino]-N-methyl-benzamide was obtained using a procedure analogous to Example 1742a. TFA salt: $^1$H NMR (400 MHz, 5% CD$_3$OD/CDCl$_3$) δ 8.35 (d, 1H), 8.04 (s, 1H), 7.67 (d, 1H), 7.56 (dd, 1H), 7.42 (d, 1H), 7.33 (m, 1H), 7.24 (dd, 1H), 7.12 (d, 1H), 4.44 (t, 2H), 3.89 (q, 2H), 2.99 (s, 3H), 2.92 (t, 2H), 1.24 (t, 3H); MS (m/e) 466 (M+1).

Example 1746

2-[5-chloro-2-(5-ethyl-6-oxo-5,6,8,9-tetrahydro-7-oxa-5-aza-benzocyclohepten-2-ylamino)-pyrimidin-4-ylamino]-3-fluoro-N-methyl-benzamide Following a procedure analogous to Example 1742a, 2-amino-5-ethyl-8,9-dihydro-5H-7-oxa-5-aza-benzocyclohepten-6-one and 2-(2,5-dichloro-pyrimidin-4-ylamino)-3-fluoro-N-methyl-benzamide were converted to 2-[5-chloro-2-(5-ethyl-6-oxo-5,6,8,9-tetrahydro-7-oxa-5-aza-benzocyclohepten-2-ylamino)-pyrimidin-4-ylamino]-3-fluoro-N-methyl-benzamide. HCl salt: $^1$H NMR (400 MHz, CD$_3$OD) δ 8.04 (s, 1H), 7.41-7.30 (m, 3H), 7.12 (d, 1H), 7.04 (s, 2H), 4.27 (t, 2H), 3.66 (q, 2H), 2.68 (t, 2H), 2.66 (s, 3H), 0.98 (t, 3H); MS (m/e) 485 (M+1).

Example 1747

3-[5-Chloro-2-(5-methyl-6-oxo-5,6,8,9-tetrahydro-7-oxa-5-aza-benzocyclohepten-2-ylamino)-pyrimidin-4-ylamino]-thiophene-2-carboxylic acid methylamide Following a procedure analogous to Example 1742a, 3-(2,5-dichloro-pyrimidin-4-ylamino)-thiophene-2-carboxylic acid methylamide and 2-amino-5-methyl-8,9-dihydro-5H-7-oxa-5-aza-benzocyclohepten-6-one were converted to 3-[5-chloro-2-(5-methyl-6-oxo-5,6,8,9-tetrahydro-7-oxa-5-aza-benzocyclohepten-2-ylamino)-pyrimidin-4-ylamino]-thiophene-2-carboxylic acid methylamide: $^1$H NMR (300 MHz, CDCl$_3$) δ 7.95 (s, 1H), 7.6 (d, 1H), 7.36 (dd, 1H), 7.27 (d, 1H), 7.18 (m, 2H), 4.13 (t, 2H), 3.37 (s, 3H), 2.95 (t, 3H), 2.92 (s, 3H); MS (m/e): 459.3 (M+1).

Example 1748

{2-[5-chloro-2-(5-methyl-6-oxo-5,6,8,9-tetrahydro-7-oxa-5-aza-benzocyclohepten-2-ylamino)-pyrimidin-4-ylamino]-phenoxy}-acetonitrile Following a procedure analogous to Example 1742a, 2-amino-5-methyl-8,9-dihydro-5H-7-oxa-5-aza-benzocyclohepten-6-one and [2-(2,5-dichloro-pyrimidin-4-ylamino)-phenoxy]-acetonitrile were converted to {2-[5-chloro-2-(5-methyl-6-oxo-5,6,8,9-tetrahydro-7-oxa-5-aza-benzocyclohepten-2-ylamino)-pyrimidin-4-ylamino]-phenoxy}-acetonitrile: $^1$H NMR (300 MHz, CD$_3$OD) δ 8.20 (bs, 1H), 8.18 (s, 1H), 7.65 (d, 1H), 7.52 (dd, 1H), 7.38 (m, 2H), 7.22 (m, 2H), 5.20 (s, 2H), 4.55 (t, 2H), 3.45 (s, 3H), 2.98 (t, 2H); MS (m/e) 451 (M+1).

Example 1749

2-{5-chloro-4-[2-(1-methyl-1H-imidazol-2-yl)-phenylamino]-pyrimidin-2-ylamino}-5-methyl-8,9-dihydro-5H-7-oxa-5-aza-benzocyclohepten-6-one 1749a) Following a procedure analogous to Example 1742a, 2-amino-5-methyl-8,9-dihydro-5H-7-oxa-5-aza-benzocyclohepten-6-one and (2,5-dichloro-pyrimidin-4-yl)-[2-(1-methyl-1H-imidazol-2-yl)-phenyl]-amine were converted to 2-{5-chloro-4-[2-(1-methyl-1H-imidazol-2-yl)-phenylamino]-pyrimidin-2-ylamino}-5-methyl-8,9-dihydro-5H-7-oxa-5-aza-benzocyclohepten-6-one: $^1$H NMR (300 MHz, CDCl$_3$) δ 8.22 (s, 1H), 7.90-7.55 (m, 7H), 7.30 (d, 2H), 4.40 (t, 2H), 3.68 (s, 3H), 3.32 (s, 3H), 2.88 (t, 2H); MS (m/e) 476 (M+1).

Example 1750

2-[5-Chloro-2-(5-methyl-6-oxo-5,6,8,9-tetrahydro-7-oxa-5-aza-benzocyclohepten-2-ylamino)-pyrimidin-4-ylamino]-3,5,N-trimethyl-benzamide 1750a) A solution of 2-amino-3,5-dimethyl-benzoic acid (550 mg) in DCM (30 mL) was treated with HOBt (225 mg), EDC (1280 mg), and CH$_3$NH$_2$ (8.5 mL, 2N in THF). The reaction mixture was stirred for 16 hours in a sealed bottle, diluted with DCM (100 mL), and washed with brine three times. The organic layer was dried (sodium sulfate), and concentrated in vacuo. The residue was purified by silica gel chromatography to provide 573 mg of 2-amino-3,5-dimethyl-benzamide: ¹H NMR (300 MHz, CDCl₃) δ 7.9 (s, 1H), 7.8 (s, 1H), 6.1 (bs, 1H), 5.3 (bs, 2H), 2.9 (d, 3H), 2.2 (s, 3H), 2.1 (s, 3H).

1750b) A solution of 2-amino-3,5-dimethyl-benzamide (573 mg), DIEA (580 mL), and 2,4,5-trichloropyrimidine (660 mg) in DMSO was heated at 65° C. for 4.5 h, then diluted with DCM, washed with brine twice, dried over sodium sulfate, and concentrated in vacuo. The residue was purified by silica gel chromatography to provide 460 mg of 2-(2,5-dichloropyrimidin-4-ylamino)-3,5,N-trimethyl-benzamide: ¹H NMR (300 MHz, CDCl₃) δ 9.3 (bs, 1H), 8.2 (s, 1H), 7.3 (s, 1H), 7.2 (s, 1H), 6.2 (bs, 1H), 3.0 (d, 3H), 2.4 (s, 3H), 2.3 (s, 3H).

1750c) Following a procedure analogous to Example 1742a, 2-amino-5-methyl-8,9-dihydro-5H-7-oxa-5-aza-benzocyclohepten-6-one and 2-(2,5-dichloro-pyrimidin-4-ylamino)-3,5,N-trimethyl-benzamide were converted to 2-[5-chloro-2-(5-methyl-6-oxo-5,6,8,9-tetrahydro-7-oxa-5-aza-benzocyclohepten-2-ylamino)-pyrimidin-4-ylamino]-3,5,N-trimethyl-benzamide: ¹H NMR (300 MHz, 5% CD₃OD in CDCl₃) δ 8.37 (s, 1H), 8.01 (s, 1H), 7.36 (d, 1H), 7.17 (s, 2H), 7.05 (dd, 1H), 7.02 (s, 1H), 6.89 (d, 1H), 6.03 (bd, 1H), 4.38 (t, 2H), 3.31 (s, 3H), 2.86 (d, 3H), 2.71 (t, 2H), 2.34 (s, 3H), 2.34 (s, 3H); MS (m/e) 481 (M+1).

Example 1751

3-Bromo-2-[5-chloro-2-(5-methyl-6-oxo-5,6,8,9-tetrahydro-7-oxa-5-aza-benzocyclohepten-2-ylamino)-pyrimidin-4-ylamino]-N-methyl-benzamide 1751a) Following a procedure analogous to Example 1750a, 2-amino-3-bromo-benzoic acid was converted to 2-amino-3-bromo-N-methyl-benzamide: ¹H NMR (300 MHz, CD₃OD) δ 7.6 (d, 1H), 7.4 (d, 1H), 6.6 (t, 1H), 6.2 (bs, 3H), 3.1 (d, 3H).

1751b) A mixture of 2-amino-3-bromo-N-methyl-benzamide (420 mg), 2,4,5-trichloropyrimidine (540 mg) and K₂CO₃ (47 mg) in DMF was heated at 85° C. overnight. The reaction mixture was loaded on silica gel, dried in vacuo, and purified by silica gel chromatography to provide 50 mg of 3-bromo-2-(2,5-dichloro-pyrimidin-4-ylamino)-N-methyl-benzamide: ¹H NMR (300 MHz, CDCl₃) δ 8.4 (bs, 1H), 8.3 (s, 1H), 7.8 (d, 1H), 7.6 (s, 1H), 7.3 (t, 1H), 6.3 (bs, 1H, NH), 3.0 (d, 3H).

1751c) Following a procedure analogous to Example 1742a, 2-amino-5-methyl-8,9-dihydro-5H-7-oxa-5-aza-benzocyclohepten-6-one and 3-bromo-2-(2,5-dichloro-pyrimidin-4-ylamino)-N-methyl-benzamide were converted to 3-bromo-2-[5-chloro-2-(5-methyl-6-oxo-5,6,8,9-tetrahydro-7-oxa-5-aza-benzocyclohepten-2-ylamino)-pyrimidin-4-ylamino]-N-methyl-benzamide: ¹H NMR (300 MHz, 5% CD₃OD in CDCl₃) δ 8.08 (s, 1H), 7.85 (s, 1H), 7.74 (dd, 1H), 7.47 (t, 1H), 7.55 (dd, 1H), 7.32 (d, 1H), 7.21 (m, 3H), 6.91 (d, 1H), 6.10 (bd, 1H), 4.38 (t, 2H), 3.31 (s, 3H), 2.78 (m, 5H); MS (m/e) 533 (M+1).

Example 1752

2-[5-Chloro-2-(5-methyl-6-oxo-5,6,8,9-tetrahydro-7-oxa-5-aza-benzocyclohepten-2-ylamino)-pyrimidin-4-ylamino]-5-fluoro-N-methyl-benzamide 1752a) A solution of 2-amino-5-fluoro-benzoic acid (880 mg) was dissolved in THF (20 mL) and treated with COCl₂ (20 mL, 20% in toluene). The reaction mixture was stirred at room temperature for 5 hours and concentrated. The residue was dissolved in THF (10 mL), treated with CH₃NH₂ (10 mL, 2N in THF), and stirred in a sealed bottle for 16 hours. The reaction was concentrated and purified by silica gel chromatography to afford 2-amino-5-fluoro-N-methyl-benzamide (800 mg): ¹H NMR (300 MHz, CDCl₃) δ 7.1 (ddd, 2H), 6.7 (dd, 1H), 6.1 (bs, 1H), 5.4 (bs, 2H), 3.0 (d, 3H).

1752b) Following a procedure analogous to Example 1751b, 2-amino-5-fluoro-N-methyl-benzamide was converted to 2-(2,5-dichloro-pyrimidin-4-ylamino)-5-fluoro-N-methyl-benzamide: ¹H NMR (300 MHz, CDCl₃) δ 11.5 (bs, 1H), 8.8 (d, 1H), 8.3 (s, 1H), 7.3 (d, 1H), 6.3 (d, 1H), 3.2 (d, 3H).

1752c) Following a procedure analogous to Example 1742a, 2-amino-5-methyl-8,9-dihydro-5H-7-oxa-5-aza-benzocyclohepten-6-one and 2-(2,5-dichloro-pyrimidin-4-ylamino)-5-fluoro-N-methyl-benzamide were converted to 2-[5-chloro-2-(5-methyl-6-oxo-5,6,8,9-tetrahydro-7-oxa-5-aza-benzocyclohepten-2-ylamino)-pyrimidin-4-ylamino]-5-fluoro-N-methyl-benzamide: ¹H NMR (300 MHz, CD₃OD) δ 8.57 (bs, 1H), 8.28 (s, 1H), 7.70 (dd, 1H), 7.53 (m, 3H), 7.34 (m, 1H), 4.59 (t, 2H), 3.54 (s, 3H), 3.15 (t, 2H), 3.06 (s, 3H); MS (m/e) 471 (M+1).

Example 1753

2-[5-Chloro-2-(5-methyl-6-oxo-5,6,8,9-tetrahydro-7-oxa-5-aza-benzocyclohepten-2-ylamino)-pyrimidin-4-ylamino]-N-methyl-3-trifluoromethyl-benzamide 1753a) Following a procedure analogous to Example 1752a, 2-amino-6-methylbenzoic acid was converted to 2-amino-N-methyl-3-trifluoromethyl-benzamide, which using a procedure analogous to Example 1751b was converted to 2-(2,5-dichloro-pyrimidin-4-ylamino)-N-methyl-3-trifluoromethyl-benzamide: ¹H NMR (300 MHz, CDCl₃) δ 8.35 (s, 1H), 7.94 (d, 1H), 7.82 (t, 1H), 7.62 (t, 1H), 6.27 (br, 1H), 2.96 (d, 3H); MS (m/e): 365.2 (M+1).

1753b) Following a procedure analogous to Example 1471e, 2-(2,5-dichloro-pyrimidin-4-ylamino)-N-methyl-3-trifluoromethyl-benzamide and 2-amino-5-methyl-8,9-dihydro-5H-7-oxa-5-aza-benzocyclohepten-6-one were converted to 2-[5-chloro-2-(5-methyl-6-oxo-5,6,8,9-tetrahydro-7-oxa-5-aza-benzocyclohepten-2-ylamino)-pyrimidin-4-ylamino]-N-methyl-3-trifluoromethyl-benzamide: ¹H NMR (300 MHz, CDCl₃) δ 8.1 (s, 1H), 7.83 (d, 1H), 7.46 (t, 1H), 7.27 (m, 1H), 7.17 (d, 1H), 7.05 (s, 1H), 6.9 (d, 1H), 6.04 (br, 1H), 4.38 (t, 2H), 3.5 (s, 3H), 2.77 (t, 2H), 2.68 (d, 3H); MS (m/e): 521.0 (M+1).

Example 1754

2-[5-Chloro-2-(5-methyl-6-oxo-5,6,8,9-tetrahydro-7-oxa-5-aza-benzocyclohepten-2-ylamino)-pyrimidin-4-ylamino]-N-methyl-4-trifluoromethyl-benzamide 1754a) Following a procedure analogous to Example 1752a, 2-amino-4-trifluoromethylbenzoic acid was converted to 2-amino-N-methyl-4-trifluoromethyl-benzamide, which using a procedure analogous to Example 1751b was converted to 2-(2,5-dichloro-pyrimidin-4-ylamino)-N-methyl-4-trifluoromethyl-benzamide: ¹H NMR (300 MHz, CDCl₃) δ 11.8 (bs, 1H), 9.2 (s, 1H), 8.4 (s, 1H), 7.7 (d, 1H), 6.4 (bs, 1H), 3.2 (d, 3H).

1754b) Following a procedure analogous to Example 1742a, 2-amino-5-methyl-8,9-dihydro-5H-7-oxa-5-aza-benzocyclohepten-6-one and 2-(2,5-dichloro-pyrimidin-4- ylamino)-N-methyl-4-trifluoromethyl-benzamide were converted to 2-[5-chloro-2-(5-methyl-6-oxo-5,6,8,9-tetrahydro-7-oxa-5-aza-benzocyclohepten-2-ylamino)-pyrimidin-4-ylamino]-N-methyl-4-trifluoromethyl-benzamide: $^1$H NMR (300 MHz, CDCl$_3$) δ 11.13 (s, 1H), 8.90 (s, 1H), 8.13 (s, 1H), 7.56 (d, 1H), 7.44 (dd, 1H), 7.28 (bd, 2H), 7.05 (d, 1H), 7.03 (d, 1H), 6.26 (bq, 1H), 4.46 (t, 2H), 3.35 (s, 3H), 3.04 (d, 3H), 2.90 (t, 2H); MS (m/e) 521 (M+1).

Example 1755

2-[5-Chloro-2-(5-methyl-6-oxo-5,6,8,9-tetrahydro-7-oxa-5-aza-benzocyclohepten-2-ylamino)-pyrimidin-4-ylamino]-6,N-dimethyl-benzamide 1755a) Following a procedure analogous to Example 1752a, 2-amino-6-methylbenzoic acid was converted to 2-amino-6,N-dimethyl-benzamide, which using a procedure analogous to Example 1750b was converted to 2-(2,5-dichloro-pyrimindin-4-ylamino)-6,N-dimethyl-benzamide: $^1$H NMR (300 MHz, CDCl$_3$) δ8.08 (s, 1H), 7.78 (dd, 1H), 7.28 (d, 1H), 7.00 (d, 1H), 7.95 (bs, 1H), 3.85 (d, 1H), 2.32 (s, 3H); MS (m/e) 311 (M+1).

1755b) Following a procedure analogous to Example 1742a, 2-amino-5-methyl-8,9-dihydro-5H-7-oxa-5-aza-benzocyclohepten-6-one and 2-(2,5-dichloro-pyrimindin-4-ylamino)-6,N-dimethyl-benzamide were converted to 2-[5-chloro-2-(5-methyl-6-oxo-5,6,8,9-tetrahydro-7-oxa-5-aza-benzocyclohepten-2-ylamino)-pyrimidin-4-ylamino]-6,N-dimethyl-benzamide: $^1$H NMR (300 MHz, CDCl$_3$) δ 8.46 (bs, 1H), 8.18 (s, 1H), 8.04 (d, 1H), 7.20 (d, 1H), 7.48-7.35 (m, 2H), 7.15-7.10 (m, 2H), 7.05 (bs, 1H), 5.94 (bd, 1H), 4.56 (t, 2H), 3.48 (s, 3H), 3.10 (d, 3H), 2.98 (t, 2H), 2.52 (s, 3H); MS (m/e) 467 (M+1).

Example 1756

2-[5-Chloro-2-(5-methyl-6-oxo-5,6,8,9-tetrahydro-7-oxa-5-aza-benzocyclohepten-2-ylamino)-pyrimidin-4-ylamino]-6-fluoro-N-methyl-benzamide 1756a) Following a procedure analogous to Example 1750a, 2-amino-6-fluorobenzoic acid was converted to 2-amino-6-fluoro-N-methyl-benzamide, which following a procedure analogous to Example 1751b, was converted to 2-(2,5-dichloro-pyrimidin-4-ylamino)-6-fluoro-N-methyl-benzamide: $^1$H NMR (300 MHz, CDCl$_3$) δ12.25 (bs, 1H), 8.68 (d, 1H), 8.36 (s, 1H), 7.60 (dd, 1H), 7.00 (dd, 1H), 6.98 (bs, 1H), 3.20 (d, 3H); MS (m/e) 315 (M+1).

1756b) Following a procedure analogous to Example 1742a, 2-amino-5-methyl-8,9-dihydro-5H-7-oxa-5-aza-benzocyclohepten-6-one and 2-(2,5-dichloro-pyrimindin-4-ylamino)-6-fluoro-N-methyl-benzamide were converted to 2-[5-chloro-2-(5-methyl-6-oxo-5,6,8,9-tetrahydro-7-oxa-5-aza-benzocyclohepten-2-ylamino)-pyrimidin-4-ylamino]-6-fluoro-N-methyl-benzamide: $^1$H NMR (300 MHz, CDCl$_3$) δ 11.70 (bs, 1H), 8.59 (d, 1H), 8.24 (s, 1H), 7.60 (d, 1H), 7.55 (dd, 1H), 7.44 (dd, 1H), 7.20 (d, 1H), 7.10 (bs, 1H), 6.92 (dd, 1H), 6.85 (bs, 1H), 4.60 (t, 2H), 3.50 (s, 3H), 3.16 (d, 3H), 3.04 (t, 2H); MS (m/e) 471 (M+1).

Example 1757

3,4-Dichloro-2-[5-chloro-2-(5-methyl-6-oxo-5,6,8,9-tetrahydro-7-oxa-5-aza-benzocyclohepten-2-ylamino)-pyrimidin-4-ylamino]-N-methyl-benzamide 1757a) To a solution containing chloral (4 g, 27 mmol) and sodium sulfate (35 g, 244 mmol) in 20 mL of water was added a solution containing 2,3-dichloroaniline (4.47 g, 27.6 mmol) and 3.5 mL of concentrated HCl in 5 mL of water. To this mixture was added 6.0 g (87 mmol) of hydroxylamine hydrochloride in 10 mL of water. The reaction mixture was refluxed in a 100° C. oil bath for 10 minutes. The reaction was cooled to room temperature and 5.7 g of N-(2,3-dichloro-phenyl)-2-[(E)-hydroxyimino]-acetamide was isolated by filtration as a yellow solid (90%): MS (m/e): 233.1 (M+1).

1757b) To concentrated sulfuric acid (50 mL) at 70° C. was added 5.7 g (24.5 mmol) of N-(2,3-dichloro-phenyl)-2-[(E)-hydroxyimino]-acetamide portionwise over 20 minutes so that the reaction temperature remained at 70° C. After the addition was complete, the reaction mixture was heated at 80° C. for 1 h. The mixture was cooled and filtered to give 4.95 g of 6,7-dichloro-1H-indole-2,3-dione as a brown solid (93%): $^1$H-NMR (300 MHz, CDCl$_3$) δ 8.2 (br, 1H), 7.62 (d, 1H), 7.37 (d, 1H).

1757c) To a mixture of 6,7-dichloro-1H-indole-2,3-dione (4.95 g) in 25 mL glacial acid and 25 mL acetic anhydride was added chromium (VI) oxide (3.9 g, 39 mmol) portionwise at 85° C. After addition, the mixture was stirred at 90° C. for 30 min. and cooled down to room temperature. Filtration provided a small amount of 7,8-dichloro-1H-benzo[d][1,3]oxazine-2,4-dione. Evaporation of the filtrate gave the majority of the product as a green solid containing chromium (III) oxide.

1757d) Crude 7,8-dichloro-1H-benzo[d][1,3]oxazine-2,4-dione (12.8 g) was dissolved in 50 mL of DMF and treated with 35 mL of 2 M methylamine in MeOH. The mixture was stirred at room temperature for 16 hours and extracted with methylene chloride. The organic phase was washed with brine, dried over by sodium sulfate, and concentrated. Chromatography on a silica gel column with methylene chloride and methanol (50:1) gave 1.0 g of 2-amino-3,4-dichloro-N-methyl-benzamide: $^1$H NMR (300 MHz, CDCl$_3$) δ 7.12 (d, 1H), 6.71 (d, 1H), 6.27 (br, 2H), 6.04 (br, 1H), 2.96 (d, 3H); MS (m/e): 219.2 (M+1).

1757e) Following a procedure analogous to Example 1751b, 2-amino-3,4-dichloro-N-methyl-benzamide was converted to 3,4-dichloro-2-(2,5-dichloro-pyrimidin-4-ylamino)-N-methyl-benzamide: $^1$H NMR (300 MHz, CDCl$_3$) δ 8.07 (s, 1H), 7.3 (q, 2H), 2.74 (s, 3H); MS (m/e): 367.1 (M+1).

1757f) Following a procedure analogous to Example 1741e, 3,4-dichloro-2-(2,5-dichloro-pyrimidin-4-ylamino)-N-methyl-benzamide and 2-amino-5-methyl-8,9-dihydro-5H-7-oxa-5-aza-benzocyclohepten-6-one were converted to 3,4-dichloro-2-[5-chloro-2-(5-methyl-6-oxo-5,6,8,9-tetrahydro-7-oxa-5-aza-benzocyclohepten-2-ylamino)-pyrimidin-4-ylamino]-N-methyl-benzamide: $^1$H NMR (300 MHz, CDCl$_3$) δ 8.38 (s, 1H), 8.08 (br, 1H), 7.23 (m, 4H), 6.94 (d, 1H), 6.23 (br, 1H), 4.38 (t, 2H), 3.30 (s, 3H), 2.83 (d, 3H), 2.82 (t, 2H); MS (m/e): 521.3 (M+1).

Example 1758

3-Chloro-2-[5-chloro-2-(5-methyl-6-oxo-5,6,8,9-tetrahydro-7-oxa-5-aza-benzocyclohepten-2-ylamino)-pyrimidin-4-ylamino]-5-fluoro-N-methyl-benzamide 1758a) A solution containing NH$_2$OH.HCl (3.2 g, 46 mmol), anhydrous sodium sulphate (13 g, 93 mmol), and 2,2,2-trichloro-1-ethoxy ethanol (4.1 g, 21.2 mmol) in water (60 mL) was added to a solution of 2-chloro-4-fluoroaniline (2 g, 0.27 mmol) in 4 M HCl (25 mL). The solution was refluxed for 40 minutes forming a white precipitate in the process. The mixture was cooled to room temperature, extracted with ethyl acetate three times, dried over sodium sulfate, filtered and concentrated in vacuo to provide 2.01 g of N-(2-chloro-4-fluoro-phenyl)-2-((E)-hydroxyimino)-acetamide: $^1$H NMR (300 MHz, CDCl$_3$) δ 8.8 (bs, 1H), 8.4 (dd, 1H), 7.9 (s, 1H), 7.6 (s, 1H), 7.2 (dd, 1H), 7.0 (ddd, 1H).

1758b) Following a procedure analogous to Example 1757b, N-(2-chloro-4-fluoro-phenyl)-2-((E)-hydroxyimino)-acetamide was converted to 7-chloro-5-fluoro-1H-indole-2,3-dione: $^1$H NMR (300 MHz, CDCl$_3$) δ 8.1 (bs, 1H), 7.5 (dd, 1H), 7.4 (dd, 1H).

1758c) A solution of 7-chloro-5-fluoro-1H-indole-2,3-dione (270 mg) in 1 M sodium hydroxide solution (5 mL) was treated with 30% hydrogen peroxide (5 mL) via dropwise addition. After one hour of stirring, the reaction was acidified with HCl to pH 1, and extracted three times with ethyl acetate. The combined organic layers were dried with sodium sulfate, and concentrated in vacuo to provide 200 mg of 2-amino-3-chloro-5-fluoro-benzoic acid.

1758d) Following a procedure analogous to Example 1752a, 2-amino-3-chloro-5-fluoro-benzoic acid was converted to 2-amino-3-chloro-5-fluoro-N-methylbenzamide: $^1$H NMR (300 MHz, CDCl$_3$) δ 8.1 (bs, 2H), 7.4 (dd, 1H), 7.0 (dd, 1H), 3.0 (d, 3H).

1758e) Following a procedure analogous to Example 1751b, 2-amino-3-chloro-5-fluoro-N-methyl-benzamide was converted to 3-chloro-2-(2,5-dichloro-pyrimidin-4-ylamino)-5-fluoro-N-methyl-benzamide: $^1$H NMR (300 MHz, CDCl$_3$) δ 8.8 (bs, 1H), 8.4 (s, 1H), 7.4 (d, 1H), 7.0 (d, 1H), 5.4 (bs, 1H), 3.0 (d, 3H).

1758f) Following a procedure analogous to Example 1742a, 2-amino-5-methyl-8,9-dihydro-5H-7-oxa-5-aza-benzocyclohepten-6-one and 3-chloro-2-(2,5-dichloro-pyrimidin-4-ylamino)-5-fluoro-N-methyl-benzamide were converted to 3-chloro-2-[5-chloro-2-(5-methyl-6-oxo-5,6,8,9-tetrahydro-7-oxa-5-aza-benzocyclohepten-2-ylamino)-pyrimidin-4-ylamino]-5-fluoro-N-methyl-benzamide: $^1$H NMR (300 MHz, CDCl$_3$) δ 8.20 (s, 1H), 7.80 (s, 1H), 7.47-7.30 (m, 3H), 7.22 (s, 1H), 7.06 (d, 1H), 6.45 (q, 1H), 4.55 (t, 2H), 3.45 (s, 3H), 2.90 (t, 2H), 2.85 (d, 3H); MS (m/e) 505 (M+1).

Example 1759

3-[5-Chloro-2-(5-methyl-6-oxo-5,6,8,9-tetrahydro-7-oxa-5-aza-benzocyclohepten-2-ylamino)-pyrimidin-4-ylamino]-4-methyl-thiophene-2-carboxylic acid methylamide 1759a) To a solution of methyl 3-amino-4-methyl-2-thiophene carboxylate (5 g, 29 mmol) and sodium hydroxide (3.5 g, 88 mmol) in a mixed solution (methanol:H$_2$O/30 ml:120 ml) was heated at 50° C. for over night. The solution was cooled to room temperature and extracted with methylene chloride. The aqueous phase was acidified with 6N HCl until pH equal to 5. The aqueous phase was extracted again with ethyl acetate, and solvent phase washed with brine and dried over by sodium sulfate. After filtered and dried over the solvent, evaporated solvent to give 3.85 g of 3-amino-4-methyl-thiophene-2-carboxylic acid as a white solid in 84% yield: $^1$H NMR (300 MHz, CDCl$_3$) δ 7.05 (d, 1H), 3.12 (br, 2H), 2.16 (s, 3H); MS (m/e): 157.9 (M+1).

1759b) Following a procedure analogous to Example 1750a, 3-amino-4-methyl-thiophene-2-carboxylic acid was converted to 3-amino-4-methyl-thiophene-2-carboxylic acid methylamide: $^1$H NMR (300 MHz, CDCl$_3$) δ 6.9 (s, 1H), 5.65 (br, 2H), 5.5 (br, 1H), 3.03 (d, 3H), 2.16 (s, 3H).

1759c) Following a procedure analogous to Example 1751b, 3-amino-4-methyl-thiophene-2-carboxylic acid methylamide was converted to 3-(2,5-dichloro-pyrimidin-4-ylamino)-4-methyl-thiophene-2-carboxylic acid methylamide: $^1$H NMR (300 MHz, CDCl$_3$) δ 8.23 (d, 1H), 7.1 (d, 1H), 6.72 (br, 1H), 3.15 (br, 1H), 2.95 (d, 3H), 2.24 (s, 3H); MS (m/e): 317.3 (M+1).

1759d) Following a procedure analogous to Example 1742a, 3-(2,5-dichloro-pyrimidin-4-ylamino)-4-methyl-thiophene-2-carboxylic acid methylamide and 2-amino-5-methyl-8,9-dihydro-5H-7-oxa-5-aza-benzocyclohepten-6-one were converted to 3-[5-chloro-2-(5-methyl-6-oxo-5,6,8,9-tetrahydro-7-oxa-5-aza-benzocyclohepten-2-ylamino)-pyrimidin-4-ylamino]-4-methyl-thiophene-2-carboxylic acid methylamide: $^1$H NMR (300 MHz, CDCl$_3$) δ 8.9 (s, 1H), 8.18 (s, 1H), 7.55 (d, 1H), 7.35 (s, 1H), 7.3 (dd, 1H), 7.13 (s, 1H), 7.04 (d, 1H), 6.13 (br, 1H), 4.53 (t, 2H), 3.43 (s, 3H), 3.03 (d, 3H), 2.94 (t, 2H), 2.22 (s, 3H); MS (m/e): 473.2 (M+1).

Example 1760

3-[5-Chloro-2-(5-methyl-6-oxo-5,6,8,9-tetrahydro-7-oxa-5-aza-benzocyclohepten-2-ylamino)-pyrimidin-4-ylamino]-thiophene-2-carboxylic acid prop-2-ynylamide 1760a) Following a procedure analogous to Example 1759a, 3-amino-thiophene-2-carboxylic acid methyl ester was converted to 3-amino-thiophene-2-carboxylic acid, which following a procedure analogous to Example 1750a and utilizing propargyl amine instead of methylamine was converted to 3-amino-thiophene-2-carboxylic acid prop-2-ynylamide: $^1$H NMR (300 MHz, CDCl$_3$) δ 7.2 (d, 1H), 6.7 (d, 1H), 5.7 (bs, 2H), 4.3 (d, 2H), 2.3 (s, 1H).

1760b) Following a procedure analogous to Example 1751b, 3-amino-thiophene-2-carboxylic acid prop-2-ynylamide was converted to 3-(2,5-dichloro-pyrimidin-4-ylamino)-thiophene-2-carboxylic acid prop-2-ynylamide: $^1$H NMR (300 MHz, CDCl$_3$) δ 11.6 (bs, 1H), 8.4 (d, 1H), 8.2 (s, 1H), 7.4 (d, 1H), 5.8 (bs, 1H), 4.3 (d, 2H), 2.3 (s, 1H).

1760c) Following a procedure analogous to Example 1742a, 2-amino-5-methyl-8,9-dihydro-5H-7-oxa-5-aza-benzocyclohepten-6-one and 3-(2,5-dichloro-pyrimidin-4-ylamino)-thiophene-2-carboxylic acid prop-2-ynylamide were converted to 3-[5-chloro-2-(5-methyl-6-oxo-5,6,8,9-tetrahydro-7-oxa-5-aza-benzocyclohepten-2-ylamino)-pyrimidin-4-ylamino]-thiophene-2-carboxylic acid prop-2-ynylamide: $^1$H NMR (300 MHz, CD$_3$OD/CDCl$_3$) δ 8.10 (d, 1H), 8.02 (s, 1H), 7.46 (s, 1H), 7.37 (d, 1H), 7.29 (d, 1H), 7.12 (d, 1H), 4.46 (t, 2H), 4.14 (d, 2H), 3.34 (s, 3H), 2.94 (t, 2H), 2.30 (t, 1H); MS (m/e) 483 (M+1).

Example 1761

5-tert-Butyl-3-[5-chloro-2-(5-methyl-6-oxo-5,6,8,9-tetrahydro-7-oxa-5-aza-benzocyclohepten-2-ylamino)-pyrimidin-4-ylamino]-thiophene-2-carboxylic acid methylamide 1761a) Under argon, 3-amino-5-tert-butyl-thiophene-2-carboxylate (2.13 g, 10 mmol) was added to a premixed (15 minutes) methylene chloride (50 mL) solution of trimethylaluminum (5.0 mL, 2.0 M in hexanes) and methylamine (5.0 mL, 2.0 M in THF). The mixture solution was stirred at room temperature for 10 minutes and heated at 41° C. for 3 days. The mixture was cooled and carefully quenched with dilute HCl followed by extraction with methylene chloride. The organic phase was dried over sodium sulfate and concentrated. Column chromatography (hexanes/ethyl acetate) gave 0.3 g of 3-amino-5-tert-butyl-thiophene-2-carboxylic acid methylamide in 14% yield: $^1$H NMR (300 MHz, CDCl$_3$) δ 6.44 (s, 1H), 5.6 (br, 2H), 5.4 (br, 1H), 3.02 (d, 3H), 1.44 (s, 9H); MS (m/e): 212.9 (M+1).

1761b) Following a procedure analogous to Example 1751b, 3-amino-5-tert-butyl-thiophene-2-carboxylic acid methylamide was converted to 5-tert-butyl-3-(2,5-dichloro-pyrimidin-4-ylamino)-thiophene-2-carboxylic acid methylamide, which following a procedure analogous to Example 1741e, was converted to 5-tert-butyl-3-[5-chloro-2-(5-methyl-6-oxo-5,6,8,9-tetrahydro-7-oxa-5-aza-benzocyclohepten-2-ylamino)-pyrimidin-4-ylamino]-thiophene-2-carboxylic acid methylamide: $^1$H NMR (300 MHz, CDCl$_3$) δ 11.46 (s, 1H), 8.22 (s, 1H), 8.12 (s, 1H), 7.68 (d, 1H), 7.4 (s, 1H), 7.23 (d, 1H), 6.95 (s, 1H), 5.72 (br, 1H), 4.6 (t, 2H), 3.47 (s, 3H), 3.1 (d, 3H), 3.07 (t, 2H), 1.43 (s, 9H); MS (m/e): 515.3 (M+1).

Example 1762

3-[5-Chloro-2-(5-methyl-6-oxo-5,6,8,9-tetrahydro-7-oxa-5-aza-benzocyclohepten-2-ylamino)-pyrimidin-4-ylamino]-4-methyl-5-phenyl-thiophene-2-carboxylic acid methyl ester 1762a) A solution of 3-amino-4-methyl-5-phenyl-thiophene-2-carboxylic acid methyl ester (1.25 g, 5.06 mmol), potassium carbonate (0.7 g, 5.06 mmol) and trichloropyrimidine (2.78 g, 15.2 mmol) was heated at 50° C. in DMF (10 mL) for 16 hours. The mixture was diluted with ethyl acetate, washed with brine and water, and dried over sodium sulfate. Evaporation of solvent and column chromatography (hexane and ethyl acetate (9:1)) gave 39 mg of 3-(2,5-dichloro-pyrimidin-4-ylamino)-4-methyl-5-phenyl-thiophene-2-carboxylic acid methyl ester in 2% yield: $^1$H NMR (300 MHz, CDCl$_3$) δ 8.58 (s, 1H), 7.5 (m, 5H), 3.82 (s, 3H), 2.37 (s, 3H); MS (m/e): 393.9 (M+1).

1762b) Following a procedure analogous to Example 1741e, 3-(2,5-dichloro-pyrimidin-4-ylamino)-4-methyl-5-phenyl-thiophene-2-carboxylic acid methyl ester and 2-amino-5-methyl-8,9-dihydro-5H-7-oxa-5-aza-benzocyclohepten-6-one were converted to 3-[5-chloro-2-(5-methyl-6-oxo-5,6,8,9-tetrahydro-7-oxa-5-aza-benzocyclohepten-2-ylamino)-pyrimidin-4-ylamino]-4-methyl-5-phenyl-thiophene-2-carboxylic acid methyl ester: $^1$H NMR (300 MHz, CDCl$_3$) δ 8.39 (s, 1H), 8.12 (s, 1H), 7.67 (s, 1H), 7.53 (m, 5H), 7.37 (s, 1H), 7.32 (br, 1H), 7.22 (d, 1H), 4.63 (t, 2H), 3.75 (s, 3H), 3.48 (s, 3H), 3.1 (t, 2H), 2.35 (s, 3H); MS (m/e): 549.9 (M+1).

Example 1763

(R)-2-[5-Chloro-2-(5-methyl-6-oxo-5,6,8,9-tetrahydro-7-oxa-5-aza-benzocyclohepten-2-ylamino)-pyrimidin-4-ylamino]-3-methyl-butyramide 1763a) A mixture of (R)-2-amino-3-methyl-butyramide (50 mg), 2,4,5-trichloropyrimidine (67 mg) and K$_2$CO$_3$ (116 mg) in DMF (3 mL) was stirred at room temperature for 5 hr. The reaction mixture was diluted with DCM and washed with brine three times. The organic layer was dried with sodium sulfate and concentrated. The residue was purified by silica gel chromatography to provide 60 mg of (R)-2-(2,5-dichloro-pyrimidin-4-ylamino)-3-methyl-butyramide: $^1$H NMR (300 MHz, CDCl$_3$) 8.2 (s, 1H), 6.2 (bs, 1H), 5.8 (bs, 1H), 5.6 (bs, 1H), 4.6 (dd, 1H), 2.4 (m, 1H), 1.2 (d, 6H). MS (m/e) 263 (M+1).

1763b) Following a procedure analogous to Example 1742a, 2-amino-5-methyl-8,9-dihydro-5H-7-oxa-5-aza-benzocyclohepten-6-one and (R)-2-(2,5-dichloro-pyrimidin-4-ylamino)-3-methyl-butyramide were converted to (R)-2-[5-chloro-2-(5-methyl-6-oxo-5,6,8,9-tetrahydro-7-oxa-5-aza-benzocyclohepten-2-ylamino)-pyrimidin-4-ylamino]-3-methyl-butyramide: $^1$H NMR (300 MHz, CD$_3$OD) δ 8.06 (s, 1H), 7.50 (dd, 1H), 7.44 (d, 1H), 7.38 (d, 1H), 4.51 (m, 3H), 3.40 (s, 3H), 3.08 (t, 2H), 2.32 (m, 1H), 1.06 (d, 3H), 1.04 (d, 3H); MS (m/e) 419 (M+1).

Example 1764

(S)-2-[5-chloro-2-(5-methyl-6-oxo-5,6,8,9-tetrahydro-7-oxa-5-aza-benzocyclohepten-2-ylamino)-pyrimidin-4-ylamino]-3-methyl-butyramide 1764a) Following a procedure analogous to Example 1763a, (S)-2-amino-3-methyl-butyramide (50 mg) and 2,4,5-trichloropyrimidine was converted to (S)-2-(2,5-dichloro-pyrimidin-4-ylamino)-3-methyl-butyramide: $^1$H NMR (300 MHz, CDCl$_3$) 8.2 (s, 1H), 6.2 (bs, 1H), 5.8 (bs, 1H), 5.6 (bs, 1H), 4.6 (dd, 1H), 2.4 (m, 1H), 1.2 (d, 6H).

1764b) Following a procedure analogous to Example 1742a, 2-amino-5-methyl-8,9-dihydro-5H-7-oxa-5-aza-benzocyclohepten-6-one and (S)-2-(2,5-dichloro-pyrimidin-4-ylamino)-3-methyl-butyramide were converted to (S)-2-[5-chloro-2-(5-methyl-6-oxo-5,6,8,9-tetrahydro-7-oxa-5-aza-benzocyclohepten-2-ylamino)-pyrimidin-4-ylamino]-3-methyl-butyramide, HCl salt: $^1$H NMR (300 MHz, CD$_3$OD) δ 8.10 (s, 1H), 7.51 (dd, 1H), 7.39 (m, 2H), 4.52 (m, 3H), 3.41 (s, 3H), 3.11 (t, 2H), 2.32 (m, 1H), 1.08 (d, 3H), 1.02 (d, 3H); MS (m/e) 419 (M+1).

Example 1765

2-{[5-Fluoro-2-(5-methyl-6-oxo-5,6,8,9-tetrahydro-7-oxa-5-aza-benzocyclohepten-2-ylamino)-pyrimidin-4-yl]-methyl-amino}-N-methyl-benzamide 1765a) A solution of N-methylisatoic anhydride (5 g, 28 mmol) in THF (100 mL) was treated with methylamine (THF solution, 2.0 M, 60 mL). The mixture was stirred for 18 h and the solvent was evaporated. The residue was partitioned between ethyl acetate (100 ml) and water (50 ml). The organic layer was washed once with brine (30 ml), dried over sodium sulfate, and concentrated to give N-methyl-2-methylamino-benzamide (5 g, 30 mmol): $^1$H NMR (300 MHz, CDCl$_3$): δ 7.3 (m, 2H), 6.67 (d, 1H), 6.58 (t, 1H), 2.96 (d, 3H), 2.86 (d, 3H); MS (m/e) 165 (M+1).

1765b) A mixture of 5-fluoro-2,6-dichloropyrimidine (1.0 g, 6 mmol, 2.0 eq.), N-methyl-2-methylamino-benzamide (0.5 g, 3 mmol), and potassium carbonate (0.85 g, 6 mmol, 2.0 eq.) was stirred in DMF (100 mL) for 24 h. The solvent was removed under high vacuum and the residue was purified on silica gel with DCM/MeOH (9.5/0.5) to give 2-[(2-chloro-5-fluoro-pyrimidin-4-yl)-methyl-amino]-N-methyl-benzamide (230 mg, 26%): $^1$H NMR (300 MHz, CD$_3$OD) δ 7.93 (dd, 1H), 7.73 (dd, 1H), 7.6 (m, 3H), 3.09 (s, 3H), 2.97 (s, 3H).

1765c) Following a procedure analogous to Example 1741e, 2-amino-5-methyl-8,9-dihydro-5H-7-oxa-5-aza-benzocyclohepten-6-one and 2-[(2-chloro-5-fluoro-pyrimidin-4-yl)-methyl-amino]-N-methyl-benzamide was converted to 2-{[5-fluoro-2-(5-methyl-6-oxo-5,6,8,9-tetrahydro-7-oxa-5- aza-benzocyclohepten-2-ylamino)-pyrimidin-4-yl]-methylamino}-N-methyl-benzamide: $^1$H NMR (300 MHz, CD$_3$OD) δ 7.77 (d, 1H), 7.6-7.5 (m, 4H), 7.4 (m, 2H), 7.13 (d, 1H), 4.46 (t, 2H), 3.50 (s, 3H), 3.35 (s, 3H), 2.95 (t, 2H), 2.75 (s, 3H); $^{19}$F NMR (282 MHz, CD$_3$OD) δ −158.7; MS (m/e) 451 (M+1).

Example 1766

2-[5-Chloro-4-(2-pyrazol-1-yl-phenylamino)-pyrimidin-2-ylamino]-5-methyl-8,9-dihydro-5H-7-oxa-5-aza-benzocyclohepten-6-one 1766a) Following a procedure analogous to Example 1763a, 2-pyrazol-1-yl-phenylamine was converted to (2,5-dichloro-pyrimidin-4-yl)-(2-pyrazol-1-yl-phenyl)-amine: $^1$H NMR (300 MHz, CDCl$_3$) 8.7 (d, 1H), 8.3 (s, 1H), 8.0 (m, 2H), 7.6-7.3 (m, 3H), 6.6 (t, 1H).

1766b) Following a procedure analogous to Example 1742a, 2-amino-5-methyl-8,9-dihydro-5H-7-oxa-5-aza-benzocyclohepten-6-one and (2,5-dichloro-pyrimidin-4-yl)-(2-pyrazol-1-yl-phenyl)-amine were converted to 2-[5-chloro-4-(2-pyrazol-1-yl-phenylamino)-pyrimidin-2-ylamino]-5-methyl-8,9-dihydro-5H-7-oxa-5-aza-benzocyclohepten-6-one: $^1$H NMR (300 MHz, CDCl$_3$) δ 10.28 (s, 1H), 8.45 (dd, 1H), 8.05 (s, 1H), 7.85 (d, 1H), 7.80 (d, 1H), 7.50 (d, 1H), 7.43-7.30 (m, 3H), 7.20 (m, 1H), 7.06 (d, 1H), 6.95 (s, 1H), 6.51 (dd, 1H), 4.48 (t, 2H), 3.38 (s, 3H), 2.91 (t, 2H); MS (m/e) 462 (M+1).

Example 1767

2-{5-Chloro-4-[2-(1H-pyrazol-3-yl)-phenylamino]-pyrimidin-2-ylamino}-5-methyl-8,9-dihydro-5H-7-oxa-5-aza-benzocyclohepten-6-one 1767a) Following a procedure analogous to Example 1741d, 3-(2-nitrophenyl)pyrazole was converted to 2-(1H-pyrazol-3-yl)phenylamine: $^1$H NMR (300 MHz, CDCl$_3$) δ 7.6 (br, 2H), 7.5 (d, 1H), 7.1 (t, 1H), 6.73 (m, 2H), 5.18 (br, 2H).

1767b) Following a procedure analogous to Example 1763a, 2-(1H-pyrazol-3-yl)-phenylamine (0.4 g, 2.51 mmol) was converted to (2,5-dichloro-pyrimidin-4-yl)-[2-(1H-pyrazol-3-yl)-phenyl]-amine in 39% yield: $^1$H NMR (300 MHz, CDCl$_3$) δ 8.62 (s, 2H), 7.57 (d. 1H), 7.15 (t, 1H), 6.92 (s, 1H), 6.76 (t, 2H), 5.78 (br, 1H); MS (m/e): 306.2 (M+1).

1767c) Following a procedure analogous to Example 1742a, (2,5-dichloro-pyrimidin-4-yl)-[2-(1H-pyrazol-3-yl)-phenyl]-amine and 2-amino-5-methyl-8,9-dihydro-5H-7-oxa-5-aza-benzocyclohepten-6-one were converted to 2-{5-chloro-4-[2-(1H-pyrazol-3-yl)-phenylamino]-pyrimidin-2-ylamino}-5-methyl-8,9-dihydro-5H-7-oxa-5-aza-benzocyclohepten-6-one: $^1$H NMR (300 MHz, CDCl$_3$) δ 8.47 (d, 1H), 8.45 (s, 1H), 7.5 (m, 4H), 7.1 (m, 2H), 6.87 (s, 1H), 6.75 (t, 1H), 4.48 (m, 2H), 3.35 (s, 3H), 2.96 (m, 2H); MS (m/e): 462.4 (M+1).

Example 1768

2-[5-Chloro-4-(2,2-difluoro-benzo[1,3]dioxol-4-ylamino)-pyrimidin-2-ylamino]-5-methyl-8,9-dihydro-5H-7-oxa-5-aza-benzocyclohepten-6-one 1768a) Following a procedure analogous to Example 1763a, 2,2-difluoro-benzo [1,3]dioxol-4-ylamine was converted to (2,5-dichloro-pyrimidin-4-yl)-(2,2-difluoro-benzo(1,3)dioxol-4-yl)-amine: $^1$H NMR (300 MHz, CDCl$_3$) 8.3 (s, 1H), 7.8 (d, 1H), 7.2 (bs, 1H), 7.1 (t, 1H), 6.9 (d, 1H).

1768b) Following a procedure analogous to Example 1742a, 2-amino-5-methyl-8,9-dihydro-5H-7-oxa-5-aza-benzocyclohepten-6-one and (2,5-dichloro-pyrimidin-4-yl)-(2,2-difluoro-benzo[1,3]dioxol-4-yl)-amine were converted to 2-[5-chloro-4-(2,2-difluoro-benzo[1,3]dioxol-4-ylamino)-pyrimidin-2-ylamino]-5-methyl-8,9-dihydro-5H-7-oxa-5-aza-benzocyclohepten-6-one: $^1$H NMR (300 MHz, CDCl$_3$) δ 8.11 (s, 1H), 7.71 (dd, 1H), 7.42 (d, 1H), 7.34 (dd, 1H), 7.06-6.98 (m, 4H), 6.88 (dd, 1H), 4.45 (t, 2H), 3.36 (s, 3H), 2.87 (t, 2H); MS (m/e) 476 (M+1).

Example 1769

2-[5-Chloro-4-(1H-indazol-4-ylamino)-pyrimidin-2-ylamino]-5-methyl-8,9-dihydro-5H-7-oxa-5-aza-benzocyclohepten-6-one 1769a) Following a procedure analogous to Example 1763a, 1H-indazol-4-ylamine was converted to (2,5-dichloro-pyrimidin-4-yl)-(1H-indazol-4-yl)-amine: $^1$H NMR (300 MHz, CDCl$_3$) 8.3 (s, 1H), 7.8 (d, 1H), 7.2 (bs, 1H), 7.1 (t, 1H), 6.9 (d, 1H).

1769b) Following a procedure analogous to Example 1741e, 2-amino-5-methyl-8,9-dihydro-5H-7-oxa-5-aza-benzocyclohepten-6-one and (2,5-dichloro-pyrimidin-4-yl)-(1H-indazol-4-yl)-amine were converted to 2-[5-chloro-4-(1H-indazol-4-ylamino)-pyrimidin-2-ylamino]-5-methyl-8,9-dihydro-5H-7-oxa-5-aza-benzocyclohepten-6-one. TFA salt: $^1$H NMR (300 MHz, CDCl$_3$) δ 11.91 (s, 1H), 8.04 (d, 1H), 8.00 (s, 1H), 7.54 (d, 1H), 7.42 (m, 2H), 7.29 (d, 1H), 7.21 (s, 1H), 6.87 (d, 1H), 4.33 (t, 2H), 3.32 (s, 3H), 2.66 (t, 2H); MS (m/e) 436 (M+1).

Example 1770

5-Chloro-3-[5-chloro-2-(5-methyl-6-oxo-5,6,8,9-tetrahydro-7-oxa-5-aza-benzocyclohepten-2-ylamino)-pyrimidin-4-ylamino]-4-methyl-thiophene-2-carboxylic acid methylamide 1770a) An ice-cold solution of 3-(2,5-dichloro-pyrimidin-4-ylamino)-4-methyl-thiophene-2-carboxylic acid methylamide (0.105 g, 0.33 mmol) in methylene chloride (4 mL) was treated with sulfuryl chloride (33 µL). The mixture was stirred for 16 hours and concentrated. Chromatography on preparative TLC plate (hexanes/ethyl acetate/methanol (50:25:1)) gave 5-chloro-3-(2,5-dichloro-pyrimidin-4-ylamino)-4-methyl-thiophene-2-carboxylic acid methylamide (10.4 mg, 9%): $^1$H NMR (300 MHz, CDCl$_3$) δ 9.9 (s, 1H), 8.33 (s, 1H), 5.82 (br, 1H), 3.05 (d, 3H), 2.22 (s, 3H); MS (m/e): 351.1 (M+1).

1770b) Following a procedure analogous to Example 1741e, 5-chloro-3-(2,5-dichloro-pyrimidin-4-ylamino)-4-methyl-thiophene-2-carboxylic acid methylamide and 2-amino-5-methyl-8,9-dihydro-5H-7-oxa-5-aza-benzocyclohepten-6-one were converted to 5-chloro-3-[5-chloro-2-(5-methyl-6-oxo-5,6,8,9-tetrahydro-7-oxa-5-aza-benzocyclohepten-2-ylamino)-pyrimidin-4-ylamino]-4-methyl-thiophene-2-carboxylic acid methylamide: $^1$H NMR (300 MHz, CDCl$_3$) δ 8.77 (s, 1H), 8.07 (br, 1H), 7.37 (d, 1H), 7.2 (dd, 1H), 7.15 (br, 1H), 7.0 (d, 1H), 5.85 (q, 1H), 4.43 (t, 2H), 3.33 (s, 3H), 2.92 (d, 3H), 2.85 (t, 2H), 2.0 (s, 3H); MS (m/e): 507.2 (M+1).

Example 1771

5-Bromo-3-[5-chloro-2-(5-methyl-6-oxo-5,6,8,9-tetrahydro-7-oxa-5-aza-benzocyclohepten-2-ylamino)-pyrimidin-4-ylamino]-4-methyl-thiophene-2-carboxylic acid methylamide 1771a) To a solution of 3-(2,5-dichloro-pyrimidin-4-ylamino)-4-methyl-thiophene-2-carboxylic acid methylamide (0.22 g, 0.7 mmol) in 1:1 DCM:AcOH was added N-bromosuccinimide (0.37 g, 2.1 mmol). The mixture was stirred for 16 hours. Evaporation and chromatography on silica gel with 3:1 methylene chloride/ethyl acetate gave 85 mg of 5-bromo-3-(2,5-dichloro-pyrimidin-4-ylamino)-4-methyl-thiophene-2-carboxylic acid methylamide (31%): $^1$H NMR (300 MHz, CDCl$_3$) δ 8.16 (s, 1H), 6.45 (br, 1H), 2.83 (d, 3H), 2.04 (s, 3H); MS (m/e): 395.1 (M+1).

1771b) Following a procedure analogous to Example 1741e, 5-bromo-3-(2,5-dichloro-pyrimidin-4-ylamino)-4-methyl-thiophene-2-carboxylic acid methylamide and 2-amino-5-methyl-8,9-dihydro-5H-7-oxa-5-aza-benzocyclohepten-6-one were converted to 5-bromo-3-[5-chloro-2-(5-methyl-6-oxo-5,6,8,9-tetrahydro-7-oxa-5-aza-benzocyclohepten-2-ylamino)-pyrimidin-4-ylamino]-4-methyl-thiophene-2-carboxylic acid methylamide: $^1$H NMR (300 MHz, CDCl$_3$) δ 8.84 (s, 1H), 8.12 (s, 1H), 7.55 (s, 1H), 7.45 (d, 1H), 7.32 (dd, 1H), 7.09 (d, 1H), 6.08 (q, 1H), 4.55 (t, 2H), 3.43 (s, 3H), 3.0 (d, 3H), 2.94 (t, 2H), 2.12 (s, 3H); MS (m/e): 553.1 (M+1).

Example 1772

5-Methyl-3-[5-chloro-2-(5-methyl-6-oxo-5,6,8,9-tetrahydro-7-oxa-5-aza-benzocyclohepten-2-ylamino)-pyrimidin-4-ylamino]-4-methyl-thiophene-2-carboxylic acid methylamide 1772a) A solution of 5-bromo-3-[5-chloro-2-(5-methyl-6-oxo-5,6,8,9-tetrahydro-7-oxa-5-aza-benzocyclohepten-2-ylamino)-pyrimidin-4-ylamino]-4-methyl-thiophene-2-carboxylic acid methylamide (50 mg, 0.09 mmol), methylboronic acid (16.4 mg, 0.27 mmol), 2 M aqueous potassium phosphate solution (2 mL) and tetrakis(triphenylphosphine)palladium(0) (6 mg, 0.004 mmol) in 1,4-dioxane (2 mL) was heated at 100° C. for 24 hours. The mixture was cooled and extracted with methyl ene chloride. The organic layer was washed with brine, dried over by sodium sulfate, and concentrated. Chromatography with preparative TLC (methylene chloride and methanol (40:1)) followed by semipreparative HPLC gave of 5-methyl-3-[5-chloro-2-(5-methyl-6-oxo-5,6,8,9-tetrahydro-7-oxa-5-aza-benzocyclohepten-2-ylamino)-pyrimidin-4-ylamino]-4-methyl-thiophene-2-carboxylic acid methylamide (2 mg, 5%): $^1$H NMR (300 MHz, CDCl$_3$) δ 8.1 (s, 1H), 7.44 (d, 1H), 7.33 (d, 1H), 7.0 (d, 1H), 6.53 (q, 1H), 4.48 (t, 2H), 3.38 (s, 3H), 2.94 (d, 3H), 2.83 (t, 2H), 2.43 (s, 3H), 1.95 (s, 3H); MS (m/e): 487.3 (M+1).

Example 1773

2-[5-Chloro-2-(5-methyl-6-oxo-5,6,8,9-tetrahydro-7-oxa-5-aza-benzocyclohepten-2-ylamino)-pyrimidin-4-ylamino]-N-methyl-3-trifluoromethoxy-benzamide 1773a) A solution of 2-(trifluoromethoxy)aniline (10 g, 56.5 mmol) and di-tert-butyl dicarbonate (12.3 g, 56.5 mmol) in toluene (60 mL) was heated at 100° C. for 2 h. Evaporation of solvent gave 14.3 g of (2-trifluoromethoxy-phenyl)-carbamic acid tert-butyl ester (91%): $^1$H NMR (300 MHz, CDCl$_3$) δ 8.17 (d, 1H), 7.23 (m, 2H), 7.0 (t, 1H), 6.75 (br, 1H), 1.52 (s, 9H).

1773b) A solution of (2-trifluoromethoxy-phenyl)-carbamic acid tert-butyl ester (14.3 g, 52 mmol) in 100 mL of dry THF was cooled to −78° C. and treated dropwise with 1.7 M tert-butyllithium in pentane (61 mL, 103 mmol). After stirring at −78° C. for 2 hours, CO$_2$ gas was bubbled into the mixture for 10 minutes. The reaction was warmed to room temperature and quenched with 100 ml of water. The aqueous phase was separated and extracted with ether. The aqueous phase was acidified with 6N HCl to pH I and again extracted with ether. The acidic extracts were dried over sodium sulfate, filtered and concentrated to give 0.8 g of 2-tert-butoxycarbonylamino-3-trifluoromethoxy-benzoic acid (5%): $^1$H NMR (300 MHz, CDCl$_3$) δ 10.68 (br, 1H), 7.92 (s, 1H), 7.9 (d, 1H), 7.45 (d, 1H), 7.22 (t, 1H), 1.47 (s, 9H); MS (m/e): 322.0 (M+1).

1773c) A solution of 2-tert-butoxycarbonylamino-3-trifluoromethoxy-benzoic acid (0.8 g, 2.5 mmol) in 30% v/v TFA/methylene chloride (50 mL) was stirred at room temperature for 1 h. Concentration of the mixture gave 2-amino-3-trifluoromethoxy-benzoic acid (0.39 g, 71%): $^1$H NMR (300 MHz, CDCl$_3$) δ 7.88 (d, 1H), 7.34 (d, 1H), 6.63 (t, 1H), 6.04 (br, 2H).

1773d) Following a procedure analogous to Example 1752a, 2-amino-3-trifluoromethoxy-benzoic acid was converted to 2-amino-N-methyl-3-trifluoromethoxy-benzamide: $^1$H NMR (300 MHz, CDCl$_3$) δ 7.2 (t, 2H), 6.58 (t, 1H), 6.09 (br, 1H), 5.77 (br, 2H), 2.96 (d 3H); MS (m/e): 235.2 (M+1).

1773e) Following a procedure analogous to Example 1751b, 2-amino-N-methyl-3-trifluoromethoxy-benzamide was converted to 2-(2,5-dichloro-pyrimidin-4-ylamino)-N-methyl-3-trifluoromethoxy-benzamide: $^1$H NMR (300 MHz, CDCl$_3$) δ 8.82 (d, 1H), 8.2 (s, 1H), 7.43 (m. 2H), 7.3 (t, 1H), 6.35 (br, 1H), 2.93 (d, 3H).

1773f) Following a procedure analogous to Example 1741e, 2-(2,5-dichloro-pyrimidin-4-ylamino)-N-methyl-3-trifluoromethoxy-benzamide was converted to 2-[5-chloro-2-(5-methyl-6-oxo-5,6,8,9-tetrahydro-7-oxa-5-aza-benzocyclohepten-2-ylamino)-pyrimidin-4-ylamino]-N-methyl-3-trifluoromethoxy-benzamide: $^1$H NMR (300 MHz, CDCl$_3$) δ 8.23 (br, 1H), 8.07 (s, 1H), 7.54 (d, 1H), 7.44 (d, 1H), 7.3 (m, 3H), 7.06 (s, 1H), 6.93 (d, 1H), 6.24 (br, 1H), 4.39 (t, 2H), 3.5 (s, 3H), 2.83 (d, 3H), 2.81 (t, 2H); MS (m/e): 537.4 (M+1).

Example 1774

2,5-Dichloro-4-[5-chloro-2-(5-methyl-6-oxo-5,6,8,9-tetrahydro-7-oxa-5-aza-benzocyclohepten-2-ylamino)-pyrimidin-4-ylamino]-thiophene-3-carboxylic acid methylamide 1774a) Following a procedure analogous to Example 1750a, 2,5-dichloro-thiophene-3-carboxylic acid was converted to 2,5-dichloro-thiophene-3-carboxylic acid methylamide: $^1$H NMR (300 MHz, CDCl$_3$) δ 7.2 (s, 1H), 6.4 (bs, 1H), 3.0 (d, 3H).

1774b) An ice-cold mixture of 2,5-dichloro-thiophene-3-carboxylic acid methylamide (475 mg) in H$_2$SO$_4$ (20 mL, 95-98%) was treated with fuming HNO$_3$ (25 mL). The mixture was stirred for 1 hour and slowly poured onto ice, extracted with ethyl acetate three times, and dried over sodium sulfate. Filtration and concentration provided 2,5- dichloro-4-nitro-thiophene-3-carboxylic acid methylamide (565 mg): ¹H NMR (300 MHz, CDCl₃) δ 6.0 (bs, 1H), 3.0 (d, 3H).

1774c) A mixture of 2,5-dichloro-4-nitro-thiophene-3-carboxylic acid methylamide (565 mg) and Raney Ni (50 mg) in ethanol was stirred under 1 atm hydrogen for 5 hours. The reaction mixture was filtered and concentrated to afford 510 mg of 4-amino-2,5-dichloro-thiophene-3-carboxylic acid methylamide: ¹H NMR (300 MHz, CDCl₃) δ 3.8-3.6 (bs, 3H), 3.0 (d, 3H).

1774d) Following a procedure analogous to Example 1751b, 4-amino-2,5-dichloro-thiophene-3-carboxylic acid methylamide (224 mg) was converted to 2,5-dichloro-4-(2,5-dichloro-pyrimidin-4-ylamino)-thiophene-3-carboxylic acid methlamide: ¹H NMR (300 MHz, CDCl₃) δ 8.6 (bs, 1H), 8.2 (s, 1H), 6.3 (bs, 1H), 3.0 (d, 3H).

1774e) Following a procedure analogous to Example 1742a, 2-amino-5-methyl-8,9-dihydro-5H-7-oxa-5-aza-benzocyclohepten-6-one and 2,5-dichloro-4-(2,5-dichloro-pyrimidin-4-ylamino)-thiophene-3-carboxylic acid methylamide were converted to 2,5-dichloro-4-[5-chloro-2-(5-methyl-6-oxo-5,6,8,9-tetrahydro-7-oxa-5-aza-benzocyclohepten-2-ylamino)-pyrimidin-4-ylamino]-thiophene-3-carboxylic acid methylamide: ¹H NMR (300 MHz, CDCl₃) δ 8.26 (s, 1H), 8.17 (s, 1H), 7.53 (d, 1H), 7.44 (dd, 1H), 7.14 (s, 1H), 7.10 (d, 1H), 6.29 (bq, 1H), 4.59 (t, 2H), 3.47 (s, 3H), 3.03 (t, 2H), 3.02 (d, 3H); MS (m/e) 527 (M+1).

Example 1775

4-[5-Chloro-2-(5-methyl-6-oxo-5,6,8,9-tetrahydro-7-oxa-5-aza-benzocyclohepten-2-ylamino)-pyrimidin-4-ylamino]-5-methyl-isoxazole-3-carboxylic acid methyl amide 1775a) Following a procedure analogous to Example 1750a, 5-methyl-isoxazole-3-carboxylic acid was converted to 5-methyl-isoxazole-3-carboxylic acid methylamide: ¹H NMR (300 MHz, CDCl₃) δ 6.8 (bs, 1H), 6.5 (s, 1H), 3.1 (d, 3H), 2.6 (s, 3H).

1775d) Following a 2 step sequence analogous to Example 1774b and 1774c, 5-methyl-isoxazole-3-carboxylic acid methylamide was converted to 4-amino-5-methyl-isoxazole-3-carboxylic acid methylamide, which following a procedure analogous to Example 1751b was converted to 4-(2,5-dichloro-pyrimidin-4-ylamino)-5-methyl-isoxazole-3-carboxylic acid methylamide: ¹H NMR (300 MHz, CDCl₃) δ 8.3 (s, 1H), 5.8 (bs, 1H), 3.4 (s, 3H), 2.4 (s, 3H).

1775e) Following a procedure analogous to Example 1742a, 2-amino-5-methyl-8,9-dihydro-5H-7-oxa-5-aza-benzocyclohepten-6-one and 4-(2,5-dichloro-pyrimidin-4-ylamino)-5-methyl-isoxazole-3-carboxylic acid methylamide were converted to 4-[5-chloro-2-(5-methyl-6-oxo-5,6,8,9-tetrahydro-7-oxa-5-aza-benzocyclohepten-2-ylamino)-pyrimidin-4-ylamino]-5-methyl-isoxazole-3-carboxylic acid methylamide: ¹H NMR (300 MHz, CDCl₃) δ 8.00 (s, 1H), 7.39 (d, 1H), 7.20 (dd, 1H), 6.99 (d, 2H), 4.46 (t, 2H), 3.42 (s, 1H), 3.38 (bs, 1H), 3.32 (s, 3H), 2.94 (d, 3H), 2.81 (t, 2H), 2.32 (s, 3H); MS (m/e) 458 (M+1).

Example 1776

5-[5-Chloro-2-(5-methyl-6-oxo-5,6,8,9-tetrahydro-7-oxa-5-aza-benzocyclohepten-2-ylamino)-pyrimidin-4-ylamino]-1-methyl-1H-pyrazole-4-carboxylic acid methylamide 1776a) To a solution of potassium tert-butoxide (157 ml, 11.0M in THF) and anhydrous DMF (40 ml) at −78° C. was added a mixture of 1-methyl-5-nitro-1H-pyrazole (5.0 g, 39 mmol) in anhydrous methylene chloride (3.5 mL) and anhydrous DMF (25 mL) via dropwise addition. The reaction was stirred at −78° C. for 30 minutes and quenched by the careful addition of acetic acid (20 mL) in methanol (40 mL). The resulting mixture was allowed to warm to room temperature and poured into ice-water and extracted with ethyl acetate. The organic phase was washed with water and brine and dried over by sodium sulfate. Chromatography on silica gel with hexanes and ethyl acetate (3:1→2:1) gave 1.47 g of 4-dichloromethyl-1-methyl-5-nitro-1H-pyrazole (18%): ¹H NMR (300 MHz, CDCl₃) δ 7.88 (s, 1H), 6.85 (s, 1H), 4.23 (s, 3H); MS (m/e): 210.2 (M+1).

1776b) A hot solution of silver nitrate (4.7 g, 27.4 mmol) in ethanol (15 mL) and water (4 mL) was added to a stirring solution of 4-dichloromethyl-1-methyl-5-nitro-1H-pyrazole (1.44 g, 6.85 mmol) in ethanol (50 mL) at 50° C. The mixture was stirred vigorously under reflux for 1 h, cooled to room temperature, and diluted with water (14 mL). The aqueous layer was extracted with chloroform and filtered through a layer of celite. Concentration and chromatography on a silica gel column with hexane and ethyl acetate (6:1) gave 1-methyl-5-nitro-1H-pyrazole-4-carbaldehyde (0.42 g, 41%): ¹H NMR (300 MHz, CDCl₃) δ 9.93 (s, 1H), 8.08 (s, 1H), 4.36 (s, 3H).

1776c) A solution of 1-methyl-5-nitro-1H-pyrazole-4-carbaldehyde (0.42 g, 2.8 mmol) in methanol (5 mL) was treated with silver (I) oxide (1.29 g, 5.6 mmol) followed by 5N potassium hydroxide (1.5 mL) in 5 mL of methanol and then refluxed for 16 hours. The mixture was cooled to room temperature and quenched with concentrated HCl (8 mL) and ethyl acetate. The mixture was filtered through a layer of celite and concentrated to give crude 1-methyl-5-nitro-1H-pyrazole-4-carboxylic acid: ¹H NMR (300 MHz, CDCl₃) δ 8.05 (s, 1H), 4.22 (s, 3H).

1776d) Following a procedure analogous to Example 1750a, 1-methyl-5-nitro-1H-pyrazole-4-carboxylic acid was converted to 1-methyl-5-nitro-1H-pyrazole-4-carboxylic acid methylamide: ¹H NMR (300 MHz, CDCl₃) δ 8.03 (s, 1H), 7.48 (br, 1H), 4.2 (s, 3H), 2.97 (d, 3H); MS (m/e): 185.2 (M+1).

1776e) Following a procedure analogous to Example 1741d, 1-methyl-5-nitro-1H-pyrazole-4-carboxylic acid methylamide was converted to 5-amino-1-methyl-1H-pyrazole-4-carboxylic acid methylamide: ¹H NMR (300 MHz, CDCl₃) δ 7.5 (s, 1H), 6.48 (br, 1H), 3.66 (s, 3H), 2.94 (d, 3H); MS (m/e): 155.3 (M+1).

1776f) Following a procedure analogous to Example 1751b, 5-amino-1-methyl-1H-pyrazole-4-carboxylic acid methylamide was converted to 5-(2,5-dichloro-pyrimidin-4-ylamino)-1-methyl-1H-pyrazole-4-carboxylic acid methylamide, which following a procedure analogous to Example 1741e was converted to 5-[5-chloro-2-(5-methyl-6-oxo-5,6,8,9-tetrahydro-7-oxa-5-aza-benzocyclohepten-2-ylamino)-pyrimidin-4-ylamino]-1-methyl-1H-pyrazole-4-carboxylic acid methylamide: ¹H NMR (300 MHz, CD₃OD) δ 8.37 (s, 1H), 8.08 (s, 1H), 7.38 (d, 2H), 7.3 (s, 1H), 4.58 (t, 2H), 3.85 (s, 3H), 3.45 (s, 3H), 3.03 (t, 2H), 2.93 (s, 3H); MS (m/e): 457.4 (M+1).

Example 1777

2-{5-Chloro-4-[2-(2-methoxy-ethoxy)-phenylamino]-pyrimidin-2-ylamino}-5-methyl-8,9-dihydro-5H-7-oxa-5-aza-benzocyclohepten-6-one 1777a) A solution of 2-(2-methoxy-ethoxy)-phenylamine (800 mg) in DMSO (15 mL) was treated with 2,4,5-trichloropyrimidine (1.1 g) and DIEA (1.8 mL) for 16 hours. The mixture was diluted with DCM (50 mL) and washed with brine three times. The organic layer was dried over sodium sulfate and concentrated. Silica gel chromatography provided 1.0 g of (2,5-dichloro-pyrimidin-4-yl)-[2-(2-methoxy-ethoxy)-phenyl]-amine: $^1$H NMR (300 MHz, CDCl$_3$) δ 8.48 (d, 1H), 8.28 (bs, 1H), 8.19 (s, 1H), 7.06 (m, 2H), 6.95 (d, 1H), 4.20 (t, 2H), 3.75 (t, 2H), 3.42 (s, 3H); MS (m/e) 314 (M+1).

1777b) Following a procedure analogous to Example 1742a, 2-amino-5-methyl-8,9-dihydro-5H-7-oxa-5-aza-benzocyclohepten-6-one and (2,5-dichloro-pyrimidin-4-yl)-[2-(2-methoxy-ethoxy)-phenyl]-amine were converted to 2-{5-chloro-4-[2-(2-methoxy-ethoxy)-phenylamino]-pyrimidin-2-ylamino}-5-methyl-8,9-dihydro-5H-7-oxa-5-aza-benzocyclohepten-6-one: $^1$H NMR (300 MHz, CD$_3$OD) δ 8.38 (d, 1H), 81.8 (s, 1H), 7.75 (d, 1H), 7.60 (d, 1H), 7.28-7.00 (m, 3H), 7.10 (t, 1H), 4.58 (t, 2H), 4.38 (dd, 2H), 3.88 (dd, 2H), 3.55 (s, 3H), 3.45 (s, 3H), 3.05 (t, 2H); MS (m/e) 469 (M+1).

Example 1778

2-{5-Chloro-4-[2-fluoro-6-(2-methoxy-ethoxy)-phenylamino]-pyrimidin-2-ylamino}-5-methyl-8,9-dihydro-5H-7-oxa-5-aza-benzocyclohepten-6-one 1778a) A solution of 1,3-difluoro-2-nitro-benzene (1.0 g), 2-methoxyethanol (480 mg), and CsCO$_3$ (3.6 g) in DMF (20 mL) was heated at 60° C. for 16 hours. The reaction mixture was filtered, concentrated, and purified by silica gel chromatography to afford 675 mg of 1-fluoro-3-(2-methoxy-ethoxy)-2-nitro-benzene: $^1$H NMR (300 MHz, CDCl$_3$) δ 7.4 (dd, 1H), 6.8 (m, 2H), 4.2 (t, 2H), 3.7 (t, 2H), 3.4 (s, 3H).

1778b) A mixture of 1-fluoro-3-(2-methoxy-ethoxy)-2-nitro-benzene (675 mg) and Pd/C (10%, 30 mg) in ethanol was shaken under 50 psi of hydrogen for 4 hours. The reaction mixture was filtered through celite and concentrated to afford 580 mg of 2-fluoro-6-(2-methoxy-ethoxy)-phenylamine: $^1$H NMR (300 MHz, CDCl$_3$) δ 6.8-6.7 (m 3H), 4.2 (t, 2H), 3.9 (bs, 2H), 3.8 (t, 2H), 3.5 (s, 3H).

1778c) A mixture of 2-fluoro-6-(2-methoxy-ethoxy)-phenylamine (580 mg), 2,4,5-trichloropyrimidine (182 mg, 1.1 eq.) and K$_2$CO$_3$ (250 mg, 2 eq.) in NMP was stirred at 50° C. for 15 hours and an additional 6 hours at 75° C. The mixture was filtered, loaded on silica gel and purified by silica gel chromatography to afford 290 mg of (2,5-dichloro-pyrimidin-4-yl)-(2-fluoro-6-(2-methoxy)-phenyl)-amine: $^1$H NMR (300 MHz, CDCl$_3$) δ 8.3 (s, 1H), 7.3 (dd, 1H), 7.1 (bs, 1H), 7.0-6.9 (m, 2H), 4.3 (t, 2H), 3.8 (t, 2H), 3.5 (s, 3H).

1778d) Following a procedure analogous to Example 1742a, 2-amino-5-methyl-8,9-dihydro-5H-7-oxa-5-aza-benzocyclohepten-6-one and (2,5-dichloro-pyrimidin-4-yl)-[2-(2-methoxy-ethoxy)-phenyl]-amine were converted 2-{5-chloro-4-[2-fluoro-6-(2-methoxy-ethoxy)-phenylamino]-pyrimidin-2-ylamino}-5-methyl-8,9-dihydro-5H-7-oxa-5-aza-benzocyclohepten-6-one: $^1$H NMR (300 MHz, CD$_3$OD) δ 8.19 (bs, 1H), 7.40 (q, 1H), 7.31 (d, 1H), 7.23 (dd, 1H), 7.05 (d, 1H), 6.99 (d, 1H), 6.93 (t, 1H), 4.37 (t, 2H), 4.11 (t, 2H), 3.63 (t, 2H), 3.32 (s, 3H), 3.31 (s, 3H), 2.77 (t, 2H); MS (m/e) 488 (M+1).

Example 1779

2-[5-Chloro-4-(2-fluoro-6-prop-2-ynyloxy-phenylamino)-pyrimidin-2-ylamino]-5-methyl-8,9-dihydro-5H-7-oxa-5-aza-benzocyclohepten-6-one 1779a) Following a procedure analogous to Example 1778a, 1,3-difluoro-2-nitro-benzene and propargyl alcohol were converted to 1-fluoro-2-nitro-3-prop-2-ynyloxy-benzene: $^1$H NMR (300 MHz, CDCl$_3$) δ 7.5 (dd, 1H), 7.2 (d, 1H), 7.0 (t, 1H), 4.9 (s, 2H), 2.7 (s, 1H).

1779b) To a solution of 1-fluoro-2-nitro-3-prop-2-ynyloxy-benzene (460 mg) in EtOAc (50 mL), was added tin(II) chloride dihydrate with stirring. After 6 hours the mixture was diluted with EtOAc and washed 3 times with brine. The organic layer was dried with sodium sulfate, concentrated and the residue purified by silica gel chromatography to afford 150 mg of 2-fluoro-6-prop-2-ynyloxy-phenylamine: $^1$H NMR (300 MHz, CDCl$_3$) δ 6.9-6.7 (m, 3H), 4.8 (s, 2H), 4.0 (bs, 2H), 2.6 (s, 1H).

1779c) Following a procedure analogous to Example 1751b, 2-fluoro-6-prop-2-ynyloxy-phenylamine was converted to (2,5-dichloro-pyrimidin-4-yl)-(2-fluoro-6-prop-2-ynyloxy-phenyl)-amine: $^1$H NMR (300 MHz, CDCl$_3$) δ 8.2 (s, 1H), 7.3 (dd, 1H), 6.9 (m, 2H), 6.8 (bs, 1H), 4.8 (s, 2H), 2.6 (s, 1H).

1779d) Following a procedure analogous to Example 1742a, 2-amino-5-methyl-8,9-dihydro-5H-7-oxa-5-aza-benzocyclohepten-6-one and (2,5-dichloro-pyrimidin-4-yl)-(2-fluoro-6-prop-2-ynyloxy-phenyl)-amine were converted to 2-[5-chloro-4-(2-fluoro-6-prop-2-ynyloxy-phenylamino)-pyrimidin-2-ylamino]-5-methyl-8,9-dihydro-5H-7-oxa-5-aza-benzocyclohepten-6-one: $^1$H NMR (300 MHz, CD$_3$OD) δ 7.99 (s, 1H), 7.41 (d, 1H), 7.35 (q, 1H), 7.22 (dd, 1H), 7.07 (d, 1H), 6.96 (d, 1H), 6.92 (t, 1H), 4.75 (d, 2H), 4.36 (t, 2H), 3.31 (s, 3H), 2.86 (t, 1H), 2.72 (t, 2H); MS (m/e) 468 (M+1).

Example 1780

2-[4-(2-Allyloxy-6-fluoro-phenylamino)-5-chloro-pyrimidin-2-ylamino]-5-methyl-8,9-dihydro-5H-7-oxa-5-aza-benzocyclohepten-6-one 1780a) Following a procedure analogous to Example 1778a, 1,3-difluoro-2-nitro-benzene and allyl alcohol were converted to 1-allyoxy-3-fluoro-2-nitro-benzen: $^1$H NMR (300 MHz, CDCl$_3$) δ 7.5 (dd, 1H), 6.9 (m, 2H), 6.1 (m, 1H), 5.6-5.4 (dd, 2H), 4.8 (d, 2H).

1780b) Following a procedure analogous to Example 1779b, 1-allyoxy-3-fluoro-2-nitro-benzen was converted to 2-allyloxy-6-fluoro-phenylamine: $^1$H NMR (300 MHz, CDCl$_3$) δ 7.7-7.5 (m, 3H), 6.0 (m, 1H), 5.4-5.2 (dd, 2H), 4.5 (d, 2H).

1780c) Following a procedure analogous to Example 1751b, 2-allyloxy-6-fluoro-phenylamine was converted to (2-allyoxy-6-fluoro-phenyl)-2,5-dichloro-pyrimidin-4-yl)-amine: $^1$H NMR (300 MHz, CDCl$_3$) δ 8.3 (s, 1H), 7.3 (dd, 1H), 6.9 (m, 2H), 6.1-6.0 (m, 1H), 5.5-5.3 (dd, 2H), 4.7 (d, 2H).

1780d) Following a procedure analogous to Example 1742a, 2-amino-5-methyl-8,9-dihydro-5H-7-oxa-5-aza-benzocyclohepten-6-one and (2-allyloxy-6-fluoro-phenyl)-(2,5-dichloro-pyrimidin-4-yl)-amine were converted to 2-[4-(2-allyloxy-6-fluoro-phenylamino)-5-chloro-pyrimidin-2-ylamino]-5-methyl-8,9-dihydro-5H-7-oxa-5-aza-benzocyclohepten-6-one: $^1$H NMR (300 MHz, CDCl$_3$) δ 8.14 (s, 1H), 7.48 (d, 1H), 7.37 (d, 1H), 7.30 (m, 2H), 7.02 (d, 1H), 6.93 (d, 1H), 6.87 (d, 1H), 6.76 (s, 1H), 6.09 (m, 1H), 5.45 (d, 1H), 5.33 (d, 1H), 4.65 (m, 2H), 4.51 (t, 1H), 3.43 (s, 1H), 2.88 (t, 2H); MS (m/e) 470 (M+1).

Example 1781

2-{4-[2-(2-Amino-ethoxy)-6-fluoro-phenylamino]-5-chloro-pyrimidin-2-ylamino}-5-methyl-8,9-dihydro-5H-7-oxa-5-aza-benzocyclohepten-6-one 1781a) Following a procedure analogous to Example 1778a, 1,3-difluoro-2-nitro-benzene and (2-hydroxy-ethyl)- carbamic acid tert-butyl ester were converted to (2-(3-fluoro-2-nitro-phenoxy)-ethyl)-carbamic acid tert-butyl ester: ¹H NMR (300 MHz, CDCl₃) δ 7.5 (dd, 1H), 6.9 (m, 2H), 5.1 (bs, 1H), 4.2 (dd, 2H), 3.6 (d, 2H), 1.5 (s, 9H).

1781b) A solution of 1(2-(3-fluoro-2-nitro-phenoxy)-ethyl)-carbamic acid tert-butyl ester (300 mg) in THF (100 mL) was treated with an aq. solution of Na₂S₂O₄ (1.1 g) and saturated sodium bicarbonate (100 mL). After 30 minutes of stirring, EtOAc (250 mL) and brine (250 mL) were added and the organic layer was separated. The aqueous layer was extracted again with EtOAc and the combined organic layers were washed with brine. The organic layer was dried over sodium sulfate, filtered and concentrated to afford 260 mg of (2-(2-amino-3-fluoro-phenoxy)-ethyl)-carbamic acid tert-butyl ester: ¹H NMR (300 MHz, CDCl₃) δ 6.7-6.5 (m, 3H), 5.0 (bs, 1H), 4.0 (t, 2H), 3.7 (bs, 1H), 2.5 (td, 2H), 1.5 (s, 9H).

1781c) Following a procedure analogous to Example 1751b, (2-(2-amino-3-fluoro-phenoxy)-ethyl)-carbanic acid tert-butyl ester was converted to {2-[2-(2,5-dichloro-pyridine-4-ylamino)-3-fluoro-phenxy]-ethyl}-carbamic acid tert-butyl ester: ¹H NMR (300 MHz, CDCl₃) δ 8.3 (s, 1H), 7.4-7.3 (dd, 1H), 7.0-6.8 (m, 2H), 4.9 (bs, 1H) 4.2 (t, 2H), 3.5 (td, 2H), 1.5 (s, 9H).

1781d) Following a procedure analogous to Example 1742a (with concomitant Boc group loss), 2-amino-5-methyl-8,9-dihydro-5H-7-oxa-5-aza-benzocyclohepten-6-one and {2-[2-(2,5-dichloro-pyrimidin-4-ylamino)-3-fluoro-phenoxy]-ethyl}-carbamic acid tert-butyl ester were converted to 2-{4-[2-(2-amino-ethoxy)-6-fluoro-phenylamino]-5-chloro-pyrimidin-2-ylamino}-5-methyl-8,9-dihydro-5H-7-oxa-5-aza-benzocyclohepten-6-one: ¹H NMR (300 MHz, CD₃OD) δ 8.33 (s, 1H), 7.60 (q, 1H), 7.42 (s, 1H), 7.40 (dd, 1H), 7.22 (d, 1H), 7.20 (d, 1H), 7.18 (t, 1H), 4.51 (t, 2H), 4.43 (t, 2H), 3.45 (m, 2H), 3.44 (s, 3H), 2.95 (t, 2H); MS (m/e) 473 (M+1).

Example 1782

N-(2-{2-[5-Chloro-2-(5-methyl-6-oxo-5,6,8,9-tetrahydro-7-oxa-5-aza-benzocyclohepten-2-ylamino)-pyrimidin-4-ylamino]-3-fluoro-phenoxy}-ethyl)-acetamide 1782a) A mixture of 2-(2-(2,5-dichloro-pyrimidine-4-ylamino)-3-fluoro-phenoxy)-ethyl)-carbamic acid tert-butyl ester (120 mg) was stirred in TFA/DCM (1:1, 20 mL) for 3 hours. The mixture was concentrated and treated with acetic acid (200 mg), EDC (400 mg), and HOBt (100 mg) in DCM (10 mL) for 16 hours. The reaction was diluted with DCM (30 mL) and washed with brine three times. The organic layer was dried over sodium sulfate, filtered and concentrated. The residue was purified by silica gel chromatography to afford 49 mg of N-(2-(2-(2,5-dichloro-pyrimidin-4-ylamino)-3-fluoro-phenoxyl)-ethyl)-acetamide: ¹H NMR (300 MHz, CDCl₃) δ 8.2 (s, 1H), 7.2 (dd, 1H), 6.8 (m, 2H), 4.2 (t, 2H), 3.5 (td, 2H), 1.9 (s, 3H).

1782b) Following a procedure analogous to Example 1742a, 2-amino-5-methyl-8,9-dihydro-5H-7-oxa-5-aza-benzocyclohepten-6-one and N-{2-[2-(2,5-dichloro-pyrimidin-4-ylamino)-3-fluoro-phenoxy]-ethyl}-acetamide were converted to N-(2-{2-[5-chloro-2-(5-methyl-6-oxo-5,6,8,9-tetrahydro-7-oxa-5-aza-benzocyclohepten-2-ylamino)-pyrimidin-4-ylamino]-3-fluoro-phenoxy}-ethyl)-acetamide: ¹H NMR (300 MHz, CD₃OD) δ 8.18 (s, 1H), 7.44 (q, 1H), 7.28 (d, 1H), 7.24 (dd, 1H), 7.07 (d, 1H), 7.01 (d, 1H), 6.93 (t, 1H), δ 4.37 (t, 2H), 4.06 (t, 2H), 3.46 (t, 2H), 3.32 (s, 3H), 2.80 (t, 2H), 1.86 (s, 3H); MS (m/e) 515 (M+1).

Example 1783

2-{5-Chloro-4-[2-(5-ethylamino-[1,3,4]oxadiazol-2-yl)-phenylamino]-pyrimidin-2-ylamino}-5-methyl-8,9-dihydro-5H-7-oxa-5-aza-benzocyclohepten-6-one 1783a) To a mixture of 2-nitro-benzoic acid hydrazide (3 g) in DMF (20 mL) was added isocyanato-ethane (1.3 g). The reaction mixture was stirred at room temperature for 3 hours and concentrated in vacuo to provide 4 g of 4-ethyl-1-(2-nitrobenzoyl)-semicarbazide: ¹H NMR (300 MHz, CDCl₃) δ 8.2 (dd, 1H), 7.8 (s, 3H), 6.4 (bs, 1H), 3.3 (q, 2H), 1.2 (t, 3H).

1783b) A mixture of 4-ethyl-1-(2-nitrobenzoyl)semicarbazide (4 g) in DCM (30 mL) was treated with triethyl amine (12 mL), PTS-Cl (4.8 g) and DMAP (100 mg). The reaction mixture was stirred for 4 hours, concentrated, and purified by silica gel chromatography to afford 2.3 g of ethyl-(5-(2-nitro-phenyl)-(1,3,4)oxadiazol-2-yl)-amine: ¹H NMR (300 MHz, CDCl₃) δ 8.1 (dd, 1H), 8.0 (d, 1H), 7.8 (m, 2H), 4.9 (bs, 1H), 3.6 (q, 2H), 1.4 (t, 3H).

1783c) A solution of ethyl-(5-(2-nitro-phenyl)-(1,3,4)oxadiazol-2-yl)-amine (3.5 g) in DCM (30 mL) was treated with triethylamine (6 mL) and di-tert-butyl-dicarbonate (9 g). The reaction mixture was stirred at rt for overnight, diluted with DCM, and washed 3 times with brine. The concentrated residue was purified by silica gel chromatography (hexanes:EtOAc:MeOH, 75:22:3) to provide 5.5 g of (5-(2-nitro-phenyl)-(1,3,4)oxadiazol-2-yl)-carbamic acid tert-butyl ester.

1783d) Following a procedure analogous to Example 1778b, ethyl-(5-(2-nitro-phenyl)-(1,3,4)oxadiazol-2-yl)-carbamic acid tert-butyl ester was converted to (5-(2-amino-phenyl)-(1,3,4)oxadiazol-2-yl)-ethyl-carbamic acid tert-butyl ester: ¹H NMR (300 MHz, CDCl₃) δ 7.7 (dd, 1H), 7.3 (t, 1H), 6.9 (d, 1H), 6.8 (t, 1H), 4.0 (q, 2H), 1.6 (s, 9H), 1.4 (t, 3H)

1783e) Following a procedure analogous to Example 1751b, (5-(2-amino-phenyl)-(1,3,4)oxadiazol-2-yl)-ethyl-carbamic acid tert-butyl ester was converted to [5-[2-(2,5-dichloro-pyrimidin-4-ylamino)-phenyl]-[1,3,4]oxadiazol-2-yl-ethyl-carbamic acid tert-butyl ester: ¹H NMR (300 MHz, CDCl₃) δ 9.0 (d, 1H), 8.4 (s, 1H), 8.0 (d, 1H), 7.7 (t, 1H), 7.4 (t, 1H), 4.1 (q, 2H), 1.6 (s, 9H), 1.4 (t, 3H).

1783f) Following a procedure analogous to Example 1742a (with concomitant Boc group loss), 2-amino-5-methyl-8,9-dihydro-5H-7-oxa-5-aza-benzocyclohepten-6-one and [5-[2-(2,5-dichloro-pyrimidin-4-ylamino)-phenyl]-[1,3,4]oxadiazol-2-yl-ethyl-carbamic acid tert-butyl ester were converted to 2-{5-chloro-4-[2-(5-ethylamino-[1,3,4]oxadiazol-2-yl)-phenylamino]-pyrimidin-2-ylamino}-5-methyl-8,9-dihydro-5H-7-oxa-5-aza-benzocyclohepten-6-one: ¹H NMR (300 MHz, CD₃OD/CDCl₃) δ 8.48 (bs, 1H), 8.37 (s, 1H), 8.07 (d, 1H), 7.70-7.42 (m, 5H), 4.57 (t, 2H), 3.56 (q, 2H), 3.53 (s, 3H), 3.11 (t, 2H), 1.45 (t, 3H); MS (m/e) 507 (M+1).

Example 1784

2-{5-Chloro-4-[2-(3-methyl-[1,2,4]oxadiazol-5-yl)-phenylamino]-pyrimidin-2-ylamino}-5-methyl-8,9-dihydro-5H-7-oxa-5-aza-benzocyclohepten-6-one 1784a) A mixture of 1H-benzo[d][1,3]oxazine-2,4-dione (3.5 g) in THF (35 mL) was treated with N-hydroxy-acetamidine (1.7 g), and DIEA (8 mL). The reaction mixture was microwave heated at 180° C. for 5 minutes, concentrated and purified by silica gel chromatography to afford 2.6 g of 2-(3-methyl-[1,2,4]oxadiazol-5-yl)-phenylamine: $^1$H NMR (300 MHz, CDCl$_3$) δ 8.0 (d, 1H), 7.4 (t, 1H), 6.9 (m, 2H), 6.0 (bs, 2H), 2.6 (s, 3H).

1784b) Following a procedure analogous to Example 1751b, 2-(3-methyl-[1,2,4]oxadiazol-5-yl)-phenylamine was converted to (2,5-dichloro-pyrimidin-4-yl)-[2-(3-methyl-[1,2,4]oxadiazol-5-yl)-phenyl]-amine: $^1$H NMR (300 MHz, CDCl$_3$) δ 9.0 (d, 1H), 8.3 (s, 1H), 8.1 (t, 1H), 7.6 (m, 2H), 2.5 (s, 3H).

1784c) Following a procedure analogous to Example 1742a, 2-amino-5-methyl-8,9-dihydro-5H-7-oxa-5-aza-benzocyclohepten-6-one and (2,5-dichloro-pyrimidin-4-yl)-[2-(3-methyl-[1,2,4]oxadiazol-5-yl)-phenyl]-amine were converted to 2-{5-chloro-4-[2-(3-methyl-[1,2,4]oxadiazol-5-yl)-phenylamino]-pyrimidin-2-ylamino}-5-methyl-8,9-dihydro-5H-7-oxa-5-aza-benzocyclohepten-6-one: $^1$H NMR (300 MHz, CD$_3$OD/CDCl$_3$) δ 8.75 (d, 1H), 8.23 (dd, 1H), 8.20 (bs, 1H), 7.59-7.50 (m, 3H), 7.36 (s, 1H), 7.20 (d, 1H), 4.54 (t, 2H), 3.47 (s, 3H), 3.01 (t, 2H), 2.59 (s, 3H); MS (m/e) 478 (M+1).

Example 1785

2-{5-Chloro-4-[2-fluoro-6-(3-methyl-[1,2,4]oxadiazol-5-yl)-phenylamino]-pyrimidin-2-ylamino}-5-methyl-8,9-dihydro-5H-7-oxa-5-aza-benzocyclohepten-6-one 1785a) To 2-amino-3-fluoro-benzoic acid (2.3 g) in DCM (20 mL) was added trichloromethylchloroformate (3.0 g) and the mixture was stirred at rt for 16 hours. The reaction was then concentrated to provide 8-fluoro-1H-benzo[d][1,3]oxazine-2,4-dione (2.5 g).

1785b) Following a procedure analogous to Example 1784a, 8-fluoro-1H-benzo[d][1,3]oxazine-2,4-dione was converted to 8-fluoro-1H-benzo[d][1,3]oxazine-2,4-dione to 2-fluoro-6-(3-methyl-[1,2,4]oxadiazol-5-yl)-phenylamine: $^1$H NMR (300 MHz, CDCl$_3$) δ 7.8 (d, 1H), 7.2 (dd, 1H), 6.9 (td, 1H), 6.0 (bs, 2H), 2.6 (s, 3H).

1785c) Following a procedure analogous to Example 1751b, 2-fluoro-6-(3-methyl-[1,2,4]oxadiazol-5-yl)-phenylamine was converted to (2,5-dichloro-pyrimidin-4-yl)-[2-fluoro-6-(3-methyl-[1,2,4]oxadiazol-5-yl)-phenyl]-amine: $^1$H NMR (300 MHz, CD$_3$OD) δ 8.3 (s, 1H), 8.0 (td, 1H), 7.5 (m, 2H), 2.5 (s, 3H).

1785d) Following a procedure analogous to Example 1741e, 2-amino-5-methyl-8,9-dihydro-5H-7-oxa-5-aza-benzocyclohepten-6-one and (2,5-dichloro-pyrimidin-4-yl)-[2-fluoro-6-(5-methyl-[1,3,4]oxadiazol-2-yl)-phenyl]-amine were converted to 2-{5-chloro-4-[2-fluoro-6-(3-methyl-[1,2,4]oxadiazol-5-yl)-phenylamino]-pyrimidin-2-ylamino}-5-methyl-8,9-dihydro-5H-7-oxa-5-aza-benzocyclohepten-6-one: $^1$H NMR (300 MHz, CD$_3$OD) δ 8.09 (s, 1H), 8.00 (dd, 1H), 7.57-7.53 (m, 2H), 7.32 (d, 1H), 7.27 (dd, 1H), 6.99 (d, 1H), 4.39 (t, 2H), 3.32 (s, 3H), 2.78 (t, 2H), 2.40 (s, 3H); MS (m/e) 496 (M+1).

Example 1786

2-{5-Chloro-4-[2-(5-methyl-[1,3,4]oxadiazol-2-yl)-phenylamino]-pyrimidin-2-ylamino}-5-methyl-8,9-dihydro-5H-7-oxa-5-aza-benzocyclohepten-6-one 1786a) A mixture of 2-nitro-benzoic acid hydrazide (4.0 g, 22.0 mmol) and para-toluenesulfonic acid (0.04 g, 0.21 mmol) in triethylorthoacetate (20 mL) was refluxed for 22 h. After cooling to rt, the precipitate was collected and washed with ethanol to yield 4.4 g of greenish yellow solid. This intermediate (2 g) was refluxed in phosphorus oxychloride (15 mL) for 3 h and concentrated. Purification by silica gel chromatography (ethyl acetate in dichloromethane) gave 1.4 g of 2-methyl-5-(2-nitro-phenyl)-[1,3,4]oxadiazole: $^1$H NMR (300 MHz, CDCl$_3$) δ 8.04 (bs, 2H), 7.77 (bs, 2H), 2.70 (bs, 3H).

1786b) A mixture of 2-methyl-5-(2-nitro-phenyl)-[1,3,4]oxadiazole (0.73 g) and 50% Raney Ni (1 mL) in methanol (5 mL) and ethyl acetate (25 mL) was shaken under 50 psi of hydrogen for 3 hours. Filtration through celite and concentration of the filtrate provided 0.62 g of 2-methyl-5-(2-amino-phenyl)-[1,3,4]oxadiazole: $^1$H NMR (400 MHz, CDCl$_3$) δ 7.71 (dd, 1H), 7.26 (dd, 1H), 6.76 (m, 2H), 5.81 (bs, 2H), 2.61 (s, 3H).

1786c) Following a procedure analogous to Example 1751b, 2-methyl-5-(2-amino-phenyl)-[1,3,4]oxadiazole was converted to (2,5-dichloro-pyrimidin-4-yl)-[2-(5-methyl-[1,3,4]oxadiazol-2-yl)-phenyl]-amine: MS (m/e) 322 (M+1).

1786d) Following a procedure analogous to Example 1742a, 2-amino-5-methyl-8,9-dihydro-5H-7-oxa-5-aza-benzocyclohepten-6-one and (2,5-dichloro-pyrimidin-4-yl)-[2-(5-methyl-[1,3,4]oxadiazol-2-yl)-phenyl]-amine were converted to 2-{5-chloro-4-[2-(5-methyl-[1,3,4]oxadiazol-2-yl)-phenylamino]-pyrimidin-2-ylamino}-5-methyl-8,9-dihydro-5H-7-oxa-5-aza-benzocyclohepten-6-one: $^1$H NMR (400 MHz, CD$_3$OD) δ 8.40 (bs, 1H), 8.23 (s, 1H), 8.07 (dd, 1H), 7.54 (t, 1H), 7.46 (t, 1H), 7.36 (m, 2H), 4.44 (t, 2H), 3.4 (s, 3H), 2.97 (t, 2H), 2.64 (s, 3H); MS (m/e) 478 (M+1).

Example 1787

2-{5-Chloro-4-[2-fluoro-6-(5-methyl-[1,3,4]oxadiazol-2-yl)-phenylamino]-pyrimidin-2-ylamino}-5-methyl-8,9-dihydro-5H-7-oxa-5-aza-benzocyclohepten-6-one 1787a). To 8-fluoro-1H-benzo[d][1,3]oxazine-2,4-dione (800 mg) in DCM (30 mL) was added N-aminoacetamidine (490 mg) and triethylamine (1.9 mL). The reaction mixture was stirred at room temperature for 1 h and 45° C. for 2 hours. The reaction mixture was cooled to room temperature and treated with PTS-Cl (1.67 g), TEA (1.3 mL), and DMAP (100 mg). The reaction mixture was stirred at room temperature for 30 minutes and 45° C. for 2 hours. The mixture was concentrated and purified by silica gel chromatography to afford 490 mg of 2-fluoro-6-(5-methyl-[1,3,4]oxadiazol-2-yl)phenylamine: $^1$H NMR (300 MHz, CDCl$_3$) δ 7.6 (d, 1H), 7.2 (t, 1H), 6.8 (td, 1H), 6.0 (bs, 2H), 2.7 (s, 3H).

1787b) Following a procedure analogous to Example 1751b, 2-fluoro-6-(5-methyl-[1,3,4]oxadiazol-2-yl)phenylamine was converted to (2,5-dichloro-pyrimidin-4-yl)-[2-fluoro-6-(5-methyl-[1,3,4]oxadiazol-2-yl)-phenyl]-amine: $^1$H NMR (300 MHz, CDCl$_3$) δ 9.5 (bs, 1H), 8.4 (s, 1H), 7.8 (td, 1H), 7.5 (m, 2H), 2.7 (s, 3H).

1787c) Following a procedure analogous to Example 1742a, 2-amino-5-methyl-8,9-dihydro-5H-7-oxa-5-aza-benzocyclohepten-6-one and (2,5-dichloro-pyrimidin-4-yl)-[2-fluoro-6-(5-methyl-[1,3,4]oxadiazol-2-yl)-phenyl]-amine were converted to 2-{5-chloro-4[2-fluoro-6-(5-methyl-[1,3,4]oxadiazol-2-yl)-phenylamino]-pyrimidin-2-ylamino}-5-methyl-8,9-dihydro-5H-7-oxa-5-aza-benzocyclohepten-6-one: $^1$H NMR (300 MHz, CD$_3$OD) δ 8.21 (bs, 1H), 7.93 (d, 1H), 7.70-7.50 (m, 2H), 7.22 (s, 1H), 7.21 (dd, 1H), 7.08 (d, 1H), 4.39 (t, 2H), 3.33 (s, 3H), 2.82 (t, 2H), 2.57 (s, 3H); MS (m/e) 496 (M+1).

Example 1788

2-{5-Chloro-4-[2-(5-methyl-2H-[1,2,4]triazol-3-yl)-phenylamino]-pyrimidin-2-ylamino}-5-methyl-8,9-dihydro-5H-7-oxa-5-aza-benzocyclohepten-6-one 1788a) To a solution of N-aminoacetamidine (2.7 g) in ethanol (30 mL) was added sodium methoxide solution (0.5 M, 58 mL) and the resulting milky slurry was stirred for 30 minutes. The mixture was filtered and the filtrate was treated with 2-nitro-benzoic acid hydrazide (4.0 g) for 3 hours. The mixture was concentrated in vacuo at room temperature and the resulting residue was washed with ice cold anhydrous ethanol. The precipitate was dried at 50° C. in vacuo to provide 4.3 g of 2-nitro-benzoic acid N'-(1-imino-ethyl)-hydrazide.

1788b) A suspension of 2-nitro-benzoic acid N'-(1-imino-ethyl)-hydrazide (4.3 g) in xylenes (50 mL) was refluxed in a flask fitted with a Dean-Stark trap. After 45 minutes of heating, the reaction suspension became a solution with a rapid condensation of water in the trap. The solution was cooled to −5° C. and stirred for 30 minute. The precipitated product was collected by filtration, washed with ice cold xylene twice, and dried in vacuo to provide 3.6 g of 3-methyl-5-(2-nitro-phenyl)-4H-[1,2,4]triazole: $^1$H NMR (300 MHz, CDCl$_3$) δ 7.9-7.5 (m, 4H), 2.5 (s, 3H).

1788c) Following a procedure analogous to Example 1783c, 3-methyl-5-(2-nitro-phenyl)-4H-[1,2,4]triazole was converted to 3-methyl-5-(2-nitro-phenyl)-4H-[1,2,4]triazole-4-carboxylic acid tert-butyl ester: $^1$H NMR (300 MHz, CDCl$_3$) δ 7.9-7.5 (m 4H), 2.7 (s, 3H), 1.6 (s, 9H).

1788d) Following a procedure analogous to Example 1778b, 3-methyl-5-(2-nitro-phenyl)-4H-[1,2,4]triazole-4-carboxylic acid tert-butyl ester was converted to 3-(2-amino-phenyl)-5-methyl-[1,2,4]triazole-4-carboxylic acid tert-butyl ester: $^1$H NMR (300 MHz, CDCl$_3$) δ 8.2 (d, 1H), 7.3 (t, 1H), 6.9-6.8 (m, 2H), 5.7 (bs, 2H), 2.9 (s, 3H), 1.8 (s, 9H).

1788e) Following a procedure analogous to Example 1750b, 3-(2-amino-phenyl)-5-methyl-[1,2,4]triazole-4-carboxylic acid tert-butyl ester was converted to 3-[2-(2,5-dichloro-pyrimidin-4-ylamino)-phenyl]-5-methyl-[1,2,4]triazole-4-carboxylic acid tert-butyl ester: $^1$H NMR (300 MHz, CDCl$_3$) δ 11.40 (bs, 1H), 8.85 (d, 1H), 8.40 (d, 1H), 8.35 (s, 1H), 7.62 (t, 1H), 7.32 (t, 1H), 2.94 (s, 3H), 1.62 (s, 9H).

1788f) Following a procedure analogous to Example 1742a, 2-amino-5-methyl-8,9-dihydro-5H-7-oxa-5-aza-benzocyclohepten-6-one and (2,5-dichloro-pyrimidin-4-yl)-[2-fluoro-6-(5-methyl-2H-[1,2,4]triazol-3-yl)-phenyl]-amine were converted to 2-{5-chloro-4-[2-(5-methyl-2H-[1,2,4]triazol-3-yl)-phenylamino]-pyrimidin-2-ylamino}-5-methyl-8,9-dihydro-5H-7-oxa-5-aza-benzocyclohepten-6-one: $^1$H NMR (300 MHz, CD$_3$OD/CDCl$_3$) δ 8.65 (bd, 1H), 8.18 (bs, 1H), 8.10 (s, 1H), 7.61 (d, 1H), 7.51 (dd, 1H), 7.38 (m, 1H), 7.21 (t, 1H), 7.14 (d, 1H), 4.53 (t, 2H), 3.43 (s, 3H), 2.97 (t, 2H), 2.58 (s, 3H); MS (m/e) 477 (M+1).

Example 1789

2-{5-Chloro-4-[2-fluoro-6-(5-methyl-oxazol-2-yl)-phenylamino]-pyrimidin-2-ylamino}-5-methyl-8,9-dihydro-5H-7-oxa-5-aza-benzocyclohepten-6-one 1789a) A suspension of 2-[5-chloro-2-(5-methyl-6-oxo-5,6,8,9-tetrahydro-7-oxa-5-aza-benzocyclohepten-2-ylamino)-pyrimidin-4-ylamino]-3-fluoro-N-prop-2-ynyl-benzamide (108 mg) and gold (III) chloride (20 mg) in acetonitrile (20 mL) was stirred for 16 hours and filtered. The filtrate was concentrated and purified by silica gel chromatography to provide 2-{5-chloro-4-[2-fluoro-6-(5-methylene-4,5-dihydro-oxazol-2-yl)-phenylamino]-pyrimidin-2-ylamino}-5-methyl-8,9-dihydro-5H-7-oxa-5-aza-benzocyclohepten-6-one (80 mg): $^1$H NMR (300 MHz, CDCl$_3$) δ 10.10 (bs, 1H), 8.20 (s, 1H), 7.84 (dd, 1H), 7.46-7.34 (m, 4H), 7.14 (bs, 1H), 7.06 (d, 1H), 4.96 (dd, 1H), 4.82 (t, 1H), 4.56-4.50 (m, 2H), 3.45 (s, 3H), 2.92 (t, 1H).

1789b) To a solution of 2-{5-chloro-4-[2-fluoro-6-(5-methylene-4,5-dihydro-oxazol-2-yl)-phenylamino]-pyrimidin-2-ylamino}-5-methyl-8,9-dihydro-5H-7-oxa-5-aza-benzocyclohepten-6-one (80 mg) in acetonitrile (10 mL) was added 4N HCl/dioxane (0.3 mL). The mixture was stirred for 16 hours, concentrated, and triturated with ethyl ether to provide 66 mg of 2-{5-chloro-4-[2-fluoro-6-(5-methyl-oxazol-2-yl)-phenylamino]-pyrimidin-2-ylamino}-5-methyl-8,9-dihydro-5H-7-oxa-5-aza-benzocyclohepten-6-one as an HCl salt: $^1$H NMR (300 MHz, CD$_3$OD) δ 8.22 (s, 1H), 7.94 (d, 1H), 7.58 (dd, 1H), 7.42 (t, 1H), 7.22-7.10 (m, 3H), 7.95 (s, 1H), 4.40 (t, 2H), 3.35 (s, 3H), 2.85 (t, 2H), 2.40 (s, 3H); MS (m/e) 495 (M+1).

Example 1790

2-{5-Chloro-4-[2-(5-methyl-oxazol-2-yl)-thiophen-3-ylamino]-pyrimidin-2-ylamino}-5-methyl-8,9-dihydro-5H-7-oxa-5-aza-benzocyclohepten-6-one 1790a) Following a procedure analogous to Example 1789a, 3-[5-chloro-2-(5-methyl-6-oxo-5,6,8,9-tetrahydro-7-oxa-5-aza-benzocyclohepten-2-ylamino)-pyrimidin-4-ylamino]-thiophene-2-carboxylic acid prop-2-ynylamide was converted to 2-{5-chloro-4-[2-(5-methylene-4,5-dihydro-oxazol-2-yl)-thiophen-3-ylamino]pyrimidin-2-ylamino}-5-methyl-8,9-dihydro-5H-7-oxa-5-aza-benzocyclohepten-6-one: $^1$H NMR (300 MHz, CDCl$_3$) δ 11.38 (bs, 1H), 8.10 (bs, 2H), 7.62-7.20 (m, 4H), 4.95 (dd, 1H), 4.8 (t, 2H), 4.55 (m, 3H), 3.50 (s, 3H), 3.10 (t, 2H).

1790b) Following a procedure analogous to Example 1789b, 2-{5-chloro-4-[2-(5-methylene-4,5-dihydro-oxazol-2-yl)-thiophen-3-ylamino]pyrimidin-2-ylamino}-5-methyl-8,9-dihydro-5H-7-oxa-5-aza-benzocyclohepten-6-one was converted to 2-{5-chloro-4-[2-(5-methyl-oxazol-2-yl)-thiophen-3-ylamino]-pyrimidin-2-ylamino}-5-methyl-8,9-dihydro-5H-7-oxa-5-aza-benzocyclohepten-6-one: $^1$H NMR (300 MHz, CDCl$_3$) δ 8.20 (s, 1H), 7.98 (d, 1H), 7.5 (m, 2H), 7.32-7.20 (m, 2H), 6.95 (s, 1H), 4.56 (t, 2H), 3.48 (s, 3H), 3.05 (t, 2H), 2.46 (s, 3H); MS (m/e) 483 (M+1).

Example 1791

2-[5-Chloro-4-(2-methylaminomethyl-phenylamino)-pyrimidin-2-ylamino]-5-methyl-8,9-dihydro-5H-7-oxa-5-aza-benzocyclohepten-6-one 1791a) Following a procedure analogous to Example 1783c, methyl-(2-nitro-benzyl)-amine was converted to methyl-(2-nitro-benzyl)-carbamic acid tert-butyl ester: $^1$H NMR (300 MHz, CDCl$_3$): δ 8.07 (d, 1H), 7.64 (t, 1H), 7.44 (t, 1H), 7.36 (d, 1H), 4.80 (s, 2H), 2.95 (s, 3H), 1.40 (s, 9H).

1791b) A mixture of methyl-(2-nitro-benzyl)-carbamic acid tert-butyl ester (2.0 g, 7.5 mmol) and 10% Pd—C (100 mg) in methanol (150 mL) was stirred for 12 h under a hydrogen atmosphere. The catalyst was removed by filtration and the solvent evaporated to give methyl-(2-amino-benzyl)-carbamic acid tert-butyl ester (1.58 g, 6.8 mmol, 91%).

1791c) Following a procedure analogous to Example 1751b, methyl-(2-amino-benzyl)-carbamic acid tert-butyl ester was converted to [2-(2,5-dichloro-pyrimidin-4-ylamino)-benzyl]-methyl-carbamic acid tert-butyl ester: $^1$H NMR (300 MHz, CDCl$_3$): δ 8.17 (s, 1H), 7.79 (d, 1H), 7.3 (m, 3H), 4.38 (s, 2H), 2.95 (s, 3H), 1.42 (s, 9H).

1791d) Following a procedure analogous to Example 1773c, [2-(2,5-dichloro-pyrimidin-4-ylamino)-benzyl]-methyl-carbamic acid tert-butyl ester was converted to (2,5-dichloro-pyrimidin-4-yl)-(2-methylaminomethyl-phenyl)-amine, which following a procedure analogous to Example 1741e, was converted as the TFA salt to 2-[5-chloro-4-(2-methylaminomethyl-phenylamino)-pyrimidin-2-ylamino]-5-methyl-8,9-dihydro-5H-7-oxa-5-aza-benzocyclohepten-6-one. TFA salt: $^1$H NMR (300 MHz, CD$_3$OD) δ 8.16 (s, 1H), 7.5 (m, 4H), 7.22 (d, 1H), 7.16 (dd, 1H), 7.02 (d, 1H), 4.34 (t, 2H), 4.17 (s, 2H), 3.3 (s, 3H), 2.75 (t, 2H), 2.61 (s, 3H); MS (m/e) 439 (M+1).

Example 1792

N-{2-[5-Chloro-2-(5-methyl-6-oxo-5,6,8,9-tetrahydro-7-oxa-5-aza-benzocyclohepten-2-ylamino)-pyrimidin-4-ylamino]-benzyl}-N-methyl-acetamide 1792a) A solution of (2,5-dichloro-pyrimidin-4-yl)-(2-methylaminomethyl-phenyl)-amine in THF (25 mL) was treated with acetic anhydride (60 mg, 0.59 mmol, 1.2 eq) and pyridine (50 mg, 0.63 mmol, 1.3 eq.) at 25° C. for 2 h. The solvent was evaporated and the residue was purified by semi-preparative HPLC to give N-[2-(2,5-dichloro-pyrimidin-4-ylamino)-benzyl]-N-methyl-acetamide (40 mg, 0.12 mmol, 24%). $^1$H NMR (300 MHz, CDCl$_3$): δ 8.22 (s, 1H), 7.73 (d, 1H), 7.3 (m, 3H), 4.48 (s, 2H), 3.24 (s, 3H), 2.12 (s, 3H); MS (m/e) 325 (M+1).

1792b) Following a procedure analogous to Example 1741e, 2-amino-5-methyl-8,9-dihydro-5H-7-oxa-5-aza-benzocyclohepten-6-one and N-[2-(2,5-dichloro-pyrimidin-4-ylamino)-benzyl]-N-methyl-acetamide was converted to N-{2-[5-chloro-2-(5-methyl-6-oxo-5,6,8,9-tetrahydro-7-oxa-5-aza-benzocyclohepten-2-ylamino)-pyrimidin-4-ylamino]-benzyl}-N-methyl-acetamide. TFA salt: $^1$H NMR (300 MHz, CD$_3$OD) δ 8.10 (s, 1H), 7.5 (m, 4H), 7.28 (d, 1H), 7.1 (m, 2H), 4.56 (s, 2H), 4.34 (t, 2H), 3.3 (s, 3H), 2.89 (s, 3H), 2.71 (t, 2H), 2.05 (s, 3H); MS (m/e) 481 (M+1).

Example 1793

N-{2-[5-Chloro-2-(5-methyl-6-oxo-5,6,8,9-tetrahydro-7-oxa-5-aza-benzocyclohepten-2-ylamino)-pyrimidin-4-ylamino]-benzyl}-acetamide Following a procedure analogous to Example 1783c, 2-nitro-benzylamine was converted to 2-nitro-benzyl-carbamic acid tert-butyl ester, which following a procedure analogous to Example 1791b was converted to 2-amino-benzyl-carbamic acid tert-butyl ester. Following a procedure analogous to Example 1751b, 2-amino-benzyl-carbamic acid tert-butyl ester was converted to [2-(2,5-dichloro-pyrimidin-4-ylamino)-benzyl]-carbamic acid tert-butyl ester, which following a procedure analogous to Example 1773c was converted to N-(2-(aminomethyl)phenyl)-2,5-dichloropyrimidin-4-amine. Following a procedure analogous to Example 1792a, N-(2-(aminomethyl)phenyl)-2,5-dichloropyrimidin-4-amine was converted to N-(2-(2,5-dichloropyrimidin-4-ylamino)benzyl)acetamide, which following a procedure analogous to Example 1741e was converted to N-{2-[5-chloro-2-(5-methyl-6-oxo-5,6,8,9-tetrahydro-7-oxa-5-aza-benzocyclohepten-2-ylamino)-pyrimidin-4-ylamino]-benzyl}-acetamide. TFA salt: $^1$H NMR (300 MHz, CD$_3$OD) δ 8.12 (s, 1H), 7.4 (m, 4H), 7.32 (d, 1H), 7.20 (dd, 1H), 7.10 (d, 1H), 4.3 (m, 4H), 3.3 (s, 3H), 2.76 (t, 2H), 1.89 (s, 3H); MS (m/e) 467 (M+1).

Example 1794

2-[5-Chloro-2-(3-oxo-2,3,4,5-tetrahydro-1H-benzo[c]azepin-8-ylamino)-pyrimidin-4-ylamino]-N-methylbenzamide 1794a) At 65° C., β-tetralone (5 g, 34.2 mmol) was dissolved in trichloroacetic acid (56 g, 0.34 mol). Sodium azide (3.3 g, 50 mmol, 1.5 eq.) was then added in portions. The mixture was stirred for 9 h and then water (400 mL) was added. The mixture was extracted with dichloromethane (3×200 mL), dried with sodium sulfate, filtered and concentrated in vacuo. The crude mixture was then recrystallized from dichloromethane/hexane to give 1,2,4,5-tetrahydro-benzo[c]azepin-3-one (4 g): $^1$H NMR (300 MHz, CDCl$_3$) δ 7.2 (m, 4H), 4.37 (d, 1H), 3.1 (m, 2H), 2.8 (m, 2H) and 1,3,4,5-tetrahydro-benzo[d]azepin-2-one (1.5 g): $^1$H NMR (300 MHz, CDCl$_3$) δ 7.2 (m, 4H), 3.84 (s, 2H), 3.6 (m, 2H), 3.12 (t, 2H).

1794b) At 0° C., 1,2,4,5-tetrahydro-benzo[c]azepin-3-one (1 g, 6.2 mmol) was added to fuming nitric acid (3 mL) and the mixture was slowly warmed up to 25° C. during 1 h. The mixture was stirred at ambient temperature for 1 h and poured onto ice. The mixture was extracted with dichloromethane (3×50 mL), dried with sodium sulfate, filtered and concentrated in vacuo. The crude mixture was then recrystallized from dichloromethane/hexane to give 8-nitro-1,2,4,5-tetrahydro-benzo[c]azepin-3-one (0.2 g). $^1$H NMR (300 MHz, CDCl$_3$) δ 8.12 (dd, 1H), 8.03 (d, 1H), 7.37 (d, 1H), 4.47 (d, 2H), 3.2 (m, 2H), 2.8 (m, 2H).

1794c) Following a procedure analogous to Example 1791b, 8-nitro-1,2,4,5-tetrahydro-benzo[c]azepin-3-one was converted to 8-amino-1,2,4,5-tetrahydro-benzo[c]azepin-3-one: $^1$H NMR (300 MHz, CD$_3$OD) δ 7.0 (d, 1H), 6.8 (m, 1H), 6.6 (m, 1H), 4.27 (s, 2H), 3.0 (m, 2H), 2.7 (m, 2H); MS (m/e) 177 (M+1).

1794d) Following a procedure analogous to Example 1742a, 2-(2,5-dichloro-pyrimidin-4-ylamino)-N-methylbenzamide and 8-amino-1,2,4,5-tetrahydro-benzo[c]azepin-3-one were converted to give 2-[5-chloro-2-(3-oxo-2,3,4,5-tetrahydro-1H-benzo[c]azepin-8-ylamino)-pyrimidin-4-ylamino]-N-methyl-benzamide: $^1$H NMR (300 MHz, CDCl$_3$) δ 8.54 (d, 1H), 8.03 (s, 1H), 7.6 (m, 2H), 7.4 (m, 2H), 7.08 (m, 3H), 7.26 (m, 1H), 7.1 (t, 1H), 7.05 (d, 1H). 4.25 (s, 2H), 3.05 (t, 2H), 2.95 (d, 3H), 2.86 (t, 2H); MS (m/e): 437.3 (M+1).

Example 1795

3-[5-Chloro-2-(3-oxo-2,3,4,5-tetrahydro-1H-benzo[c]azepin-8-ylamino)-pyrimidin-4-ylamino]-4-methyl-thiophene-2-carboxylic acid methylamide 1795a) Following a procedure analogous to Example 1741e, 3-(2,5-dichloro-pyrimidin-4-ylamino)-4-methyl-thiophene-2-carboxylic acid methylamide and 8-amino-1,2,4,5-tetrahydro-benzo[c]azepin-3-one were converted to 3-[5-chloro-2-(3-oxo-2,3,4,5-tetrahydro-1H-benzo[c]azepin-8-ylamino)-pyrimidin-4-ylamino]-4-methyl-thiophene-2-carboxylic acid methylamide: $^1$H NMR (300 MHz, CDCl$_3$) δ

8.78 (s, 1H), 8.18 (s, 1H), 7.5 (s, 1H), 7.12 (m, 4H), 6.87 (br, 1H), 6.3 (br, 1H), 4.25 (d, 2H), 3.1 (m, 2H), 3.05 (d, 3H), 2.85 (m, 2H), 2.18 (s, 3H); MS (m/e): 457.3 (M+1).

Example 1796

3-Chloro-2-[5-chloro-2-(3-oxo-2,3,4,5-tetrahydro-1H-benzo[c]azepin-8-ylamino)-pyrimidin-4-ylamino]-N-methylbenzamide Following a procedure analogous to Example 1742a, 3-chloro-2-(2,5-dichloro-pyrimidin-4-ylamino)-N-methyl-benzamide and 8-amino-1,2,4,5-tetrahydro-benzo[c]azepin-3-one were converted to 3-chloro-2-[5-chloro-2-(3-oxo-2,3,4,5-tetrahydro-1H-benzo[c]azepin-8-ylamino)-pyrimidin-4-ylamino]-N-methylbenzamide: $^1$H NMR (300 MHz, CD$_3$OD) δ 8.17 (s, 1H), 7.86 (d, 1H), 7.7 (d, 1H), 7.57 (t, 1H), 7.38 s, 1H), 7.33 (dd, 1H), 7.06 (d, 1H), 4.28 (s, 2H), 3.08 (t, 2H), 2.89 (s, 3H), 2.84 (t, 2H); MS (m/e): 471.2 (M+1).

Example 1797

3-exo-[5-Chloro-2-(3-oxo-2,3,4,5-tetrahydro-1H-benzo[c]azepin-8-ylamino)-pyrimidin-4-yl]aminobicyclo[2.2.1]hept-5-ene-2-exo-carboxamide Following a procedure analogous to Example 1742a, 8-amino-1,2,4,5-tetrahydro-benzo[c]azepin-3-one and 3-exo-(2,5-dichloro-pyrimidin-4-yl)aminobicyclo[2.2.1]hept-5-ene-2-exo-carboxamide were converted to 3-exo-[5-chloro-2-(3-oxo-2,3,4,5-tetrahydro-1H-benzo[c]azepin-8-ylamino)-pyrimidin-4-yl]aminobicyclo[2.2.1]hept-5-ene-2-exo-carboxamide: $^1$H NMR (300 MHz, DMSO-d$_6$) δ 9.37 (s, 1H), 8.1-7.8 (m, 5H), 7.46 (d, 2H), 7.20 (d, 1H), 6.47 (d, 2H), 4.27 (br, 2H), 4.24 (br, 1H), 3.06 (s, 2H), 3.01 (s, 1H), 2.91 (s, 1H), 2.73 (s, 2H), 2.6 (br, 1H), 2.23 (d, 1H), 1.53 (d, 1H); MS (m/e) 439 (M+1).

Example 1798

2-[5-Chloro-2-(2-methyl-3-oxo-2,3,4,5-tetrahydro-1H-benzo[c]azepin-8-ylamino)-pyrimidin-4-ylamino]-N-methyl-benzamide and 2-[5-chloro-2-(2-methyl-3-oxo-2,3-dihydro-1H-benzo[c]azepin-8-ylamino)-pyrimidin-4-ylamino]-N-methyl-benzamide 1798a) At 25° C., sodium hydride (150 mg, 6.3 mmol) was added to a solution of 1,2,4,5-tetrahydro-benzo[c]azepin-3-one (1 g, 6 mmol) in THF (50 mL). The suspension was stirred for 10 minutes and treated with methyl iodide (1 g, 7 mmol). The mixture was stirred for an additional 4 hours and then partitioned between ethyl acetate (100 ml) and water (50 ml). Washing once with brine (30 ml), drying over anhydrous magnesium sulfate and evaporation of solvent gave 2-methyl-1,2,4,5-tetrahydro-benzo[c]azepin-3-one (1 g, 5.7 mmol, 95%): $^1$H NMR (300 MHz, CDCl$_3$) δ 7.2 (m, 5H), 4.52 (s, 2H), 3.18 (t, 2H), 3.09 (s, 3H), 3.00 (t, 2H).

1798b) Following a procedure analogous to Example 1794b, 2-methyl-1,2,4,5-tetrahydro-benzo[c]azepin-3-one was converted to 2-methyl-8-nitro-1,2,4,5-tetrahydro-benzo[c]azepin-3-one: $^1$H NMR (300 MHz, CDCl$_3$) δ 8.13 (dd, 1H), 8.04 (d, 1H), 7.36 (d, 1H), 4.65 (s, 2H), 3.31 (t, 2H), 3.15 (s, 3H), 3.06 (t, 2H).

1798c) Following a procedure analogous to Example 1791b, 2-methyl-8-nitro-1,2,4,5-tetrahydro-benzo[c]azepin-3-one was converted to 8-amino-2-methyl-1,2,4,5-tetrahydro-benzo[c]azepin-3-one: $^1$H NMR (300 MHz, CDCl$_3$) δ 7.2 (m, 3H), 4.65 (s, 2H), 3.31 (t, 2H), 3.2 (s, 3H), 3.1 (t, 2H); MS (m/e) 191 (M+1).

1798d) Following a procedure analogous to Example 1742a, 8-amino-2-methyl-1,2,4,5-tetrahydro-benzo[c]azepin-3-one and 2-(2,5-dichloro-pyrimidin-4-ylamino)-N-methyl-benzamide were converted to a mixture of 2-[5-chloro-2-(2-methyl-3-oxo-2,3,4,5-tetrahydro-1H-benzo[c]azepin-8-ylamino)-pyrimidin-4-ylamino]-N-methyl-benzamide ($^1$H NMR (300 MHz, CD$_3$OD) δ 8.42 (m, 1H), 8.15 (s, 1H), 7.77 (dd, 1H), 7.42-7.29 (m, 5H), 4.60 (s, 2H), 3.21 (t, 2H), 2.99 (s, 3H), 2.98 (t, 2H), 2.94 (s, 3H); MS (m/e) 451 (M+1)) and 2-[5-chloro-2-(2-methyl-3-oxo-2,3-dihydro-1H-benzo[c]azepin-8-ylamino)-pyrimidin-4-ylamino]-N-methyl-benzamide (HCl salt: $^1$H NMR (300 MHz, CD$_3$OD) δ 8.39 (d, 1H), 8.22 (s, 1H), 7.78 (dd, 1H), 7.58 (m, 3H), 7.35 (m, 2H), 7.32 (d, 1H), 6.39 (d, 1H), 4.34 (s, 2H), 2.99 (s, 3H), 2.94 (s, 3H); MS (m/e) 449 (M+1)).

Example 1799

3-[5-Chloro-2-(2-methyl-3-oxo-2,3,4,5-tetrahydro-1H-benzo[c]azepin-8-ylamino)-pyrimidin-4-ylamino]-4-methyl-thiophene-2-carboxylic acid methylamide Following a procedure analogous to Example 1742a, 3-(2,5-dichloro-pyrimidin-4-ylamino)-4-methyl-thiophene-2-carboxylic acid methylamide and 8-amino-2-methyl-1,2,4,5-tetrahydro-benzo[c]azepin-3-one were converted to 3-[5-chloro-2-(2-methyl-3-oxo-2,3,4,5-tetrahydro-1H-benzo[c]azepin-8-ylamino)-pyrimidin-4-ylamino]-4-methyl-thiophene-2-carboxylic acid methylamide: $^1$H NMR (300 MHz, CDCl$_3$) δ 8.85 (s, 1H), 8.03 (s, 1H), 7.28 (s, 1H), 7.13 (dd, 1H), 7.05 (d, 2H), 6.93 (d, 1H), 6.06 (q, 1H), 4.3 (s, 2H), 3.03 (t, 2H), 2.98 (s, 3H), 2.93 (d, 3H), 2.87 (t, 2H), 2.1 (s, 3H); MS (m/e): 471.3 (M+1).

Example 1800

2-{[5-Fluoro-2-(2-methyl-3-oxo-2,3,4,5-tetrahydro-1H-benzo[c]azepin-8-ylamino)-pyrimidin-4-yl]-methyl-amino}-N-methyl-benzamide Following a procedure analogous to Example 1741e, 8-amino-2-methyl-1,2,4,5-tetrahydro-benzo[c]azepin-3-one and 2-[(2-chloro-5-fluoro-pyrimidin-4-yl)-methyl-amino]-N-methyl-benzamide were converted to 2-{[5-fluoro-2-(2-methyl-3-oxo-2,3,4,5-tetrahydro-1H-benzo[c]azepin-8-ylamino)-pyrimidin-4-yl]-methyl-amino}-N-methyl-benzamide: $^1$H NMR (300 MHz, CD$_3$OD) δ 7.73 (d, 1H), 7.6-7.3 (m, 6H), 7.03 (d, 1H), 4.53 (s, 2H), 3.49 (s, 3H), 3.06 (t, 2H), 3.03 (s, 3H), 2.91 (t, 2H), 2.74 (s, 3H); $^{19}$F NMR (282 MHz, CD$_3$OD) δ −158.9; MS (m/e) 449 (M+1).

Example 1801

2-[5-Chloro-2-(2-methyl-3-oxo-2,3,4,5-tetrahydro-1H-benzo[c]azepin-8-ylamino)-pyrimidin-4-ylamino]-3,5,N-trimethyl-benzamide Following a procedure analogous to Example 1742a, 8-amino-2-methyl-1,2,4,5-tetrahydro-benzo[c]azepin-3-one and 2-(2,5-dichloro-pyrimidin-4-ylamino)-3,5,N-trimethylbenzamide were converted to 2-[5-chloro-2-(2-methyl-3-oxo-2,3,4,5-tetrahydro-1H-benzo[c]azepin-8-ylamino)-pyrimidin-4-ylamino]-3,5,N-trimethyl-benzamide: $^1$H NMR (300 MHz, CDCl$_3$) δ 8.12 (s, 1H), 7.38 (bs, 2H), 7.18 (s, 1H), 7.10-6.98 (m, 2H), 4.38 (bs, 2H), 3.05 (t, 2H), 2.95 (s, 3H), 2.90 (t, 2H), 2.80 (s, 3H), 2.42 (s, 3H), 2.22 (s, 3H); MS (m/e) 479 (M+1).

Example 1802

8-{5-Chloro-4-[2-(1-methyl-1H-imidazol-2-yl)-phenylamino]-pyrimidin-2-ylamino}-2-methyl-1,2,4,5-tetrahydro-benzo[c]azepin-3-one Following a procedure analogous to Example 1742a, 8-amino-2-methyl-1,2,4,5-tetrahydro-benzo[c]azepin-3-one and (2,5-dichloro-pyrimidin-4-yl)-[2-(1-methyl-1H-imidazol-2-yl)-phenyl]-amine were converted to 8-{5-chloro-4-[2-(1-methyl-1H-imidazol-2-yl)-phenylamino]-pyrimidin-2-ylamino}-2-methyl-1,2,4,5-tetrahydro-benzo[c]azepin-3-one. TFA salt: $^1$H NMR (300 MHz, CDCl$_3$) δ 10.87 (s, 1H), 8.63 (d, 1H), 8.14 (s, 1H), 7.50 (m, 4H), 7.35 (d, 2H), 7.29 (t, 1H), 7.17 (d, 1H), 7.11 (s, 2H), 4.53 (s, 2H), 3.87 (s, 3H), 3.22 (t, 2H), 3.11 (s, 3H), 3.01 (t, 2H); MS (m/e) 474 (M+1).

Example 1803

8-[5-Chloro-4-(2,2-difluoro-benzo[1,3]dioxol-4-ylamino)-pyrimidin-2-ylamino]-2-methyl-1,2,4,5-tetrahydro-benzo[c]azepin-3-one Following a procedure analogous to Example 1742a, 8-amino-2-methyl-1,2,4,5-tetrahydro-benzo[c]azepin-3-one and (2,5-dichloro-pyrimidin-4-yl)-(2,2-difluoro-benzo[1,3]dioxol-4-yl)-amine were converted to 8-[5-chloro-4-(2,2-difluoro-benzo[1,3]dioxol-4-ylamino)-pyrimidin-2-ylamino]-2-methyl-1,2,4,5-tetrahydro-benzo[c]azepin-3-one: $^1$H NMR (300 MHz, CDCl$_3$) δ 8.22 (s, 1H), 7.82 (dd, 1H), 7.40 (m, 2H), 7.20-7.04 (m, 2H), 7.00 (d, 1H), 4.48 (s, 2H), 3.22 (t, 2H), 3.05 (s, 3H), 3.00 (t, 2H); MS (m/e) 474 (M+1).

Example 1804

8-{5-Chloro-4-[2-(1H-pyrazol-3-yl)-phenylamino]-pyrimidin-2-ylamino}-2-methyl-1,2,4,5-tetrahydro-benzo[c]azepin-3-one Following a procedure analogous to Example 1741e, (2,5-dichloro-pyrimidin-4-yl)-[2-(1H-pyrazol-3-yl)-phenyl]-amine and 8-amino-2-methyl-1,2,4,5-tetrahydro-benzo[c]azepin-3-one were converted to 8-{5-chloro-4-[2-(1H-pyrazol-3-yl)-phenylamino]-pyrimidin-2-ylamino}-2-methyl-1,2,4,5-tetrahydro-benzo[c]azepin-3-one: $^1$H NMR (300 MHz, CDCl$_3$) δ 11.5 (s, 1H), 8.67 (d, 1H), 8.15 (s, 1H), 7.76 (m, 2H), 7.45 (m, 2H), 7.28 (t, 1H), 7.15 (m, 2H), 6.82 (s, 1H), 4.5 (s, 2H), 3.1 (t, 2H), 3.07 (s, 3H), 3.02 (t, 2H); MS (m/e): 460.4 (M+1).

Example 1805

3-Chloro-2-[5-chloro-2-(2-methyl-3-oxo-2,3,4,5-tetrahydro-1H-benzo[c]azepin-8-ylamino)-pyrimidin-4-ylamino]-N-methyl-benzamide Following a procedure analogous to Example 1742a, 8-amino-2-methyl-1,2,4,5-tetrahydro-benzo[c]azepin-3-one and 3-chloro-2-(2,5-dichloro-pyrimidin-4-ylamino)-N-methyl-benzamide were converted to 3-chloro-2-[5-chloro-2-(2-methyl-3-oxo-2,3,4,5-tetrahydro-1H-benzo[c]azepin-8-ylamino)-pyrimidin-4-ylamino]-N-methyl-benzamide: $^1$H NMR (300 MHz, CDCl$_3$) δ 8.20 (s, 1H), 8.10 (s, 1H), 7.71 (dd, 1H), 7.64 (dd, 1H), 7.43 (d, 1H), 7.28 (m, 2H), 7.07 (s, 1H), 7.03 (d, 1H), 6.25 (bq, 1H), 4.41 (s, 2H), 3.17 (t, 2H), 3.10 (s, 3H), 2.97 (t, 2H), 2.92 (d, 3H); MS (m/e) 485 (M+1).

Example 1806

3-Fluoro-2-[5-chloro-2-(2-methyl-3-oxo-2,3,4,5-tetrahydro-1H-benzo[c]azepin-8-ylamino)-pyrimidin-4-ylamino]-N-methyl-benzamide Following a procedure analogous to Example 1742a, 8-amino-2-methyl-1,2,4,5-tetrahydro-benzo[c]azepin-3-one and 3-fluoro-2-(2,5-dichloro-pyrimidin-4-ylamino)-N-methyl-benzamide were converted to 3-fluoro-2-[5-chloro-2-(2-methyl-3-oxo-2,3,4,5-tetrahydro-1H-benzo[c]azepin-8-ylamino)-pyrimidin-4-ylamino]-N-methyl-benzamide: $^1$H NMR (300 MHz, CDCl$_3$) δ 8.85 (s, 1H), 8.08 (s, 1H), 7.31 (m, 4H), 7.17 (d, 1H), 6.95 (d, 1H), 6.89 (s, 1H), 6.20 (bq, 1H), 4.34 (s, 2H), 3.07 (t, 2H), 3.00 (s, 3H), 2.94 (d, 3H), 2.87 (t, 2H); MS (m/e) 469 (M+1).

Example 1807

2,5-Dichloro-4-[5-chloro-2-(2-methyl-3-oxo-2,3,4,5-tetrahydro-1H-benzo[c]azepin-8-ylamino)-pyrimidin-4-ylamino]-thiophene-3-carboxylic acid methylamide Following a procedure analogous to Example 1742a, 8-amino-2-methyl-1,2,4,5-tetrahydro-benzo[c]azepin-3-one and 2,5-dichloro-4-(2,5-dichloro-pyrimidin-4-ylamino)-thiophene-3-carboxylic acid methylamide were converted to 2,5-dichloro-4-[5-chloro-2-(2-methyl-3-oxo-2,3,4,5-tetrahydro-1H-benzo[c]azepin-8-ylamino)-pyrimidin-4-ylamino]-thiophene-3-carboxylic acid methylamide: $^1$H NMR (300 MHz, CDCl$_3$) δ 8.20 (s, 1H), 8.17 (s, 1H), 7.39 (m, 2H), 7.13 (d, 1H), 6.96 (s, 1H), 6.21 (bq, 1H), 4.52 (s, 2H), 3.21 (t, 2H), 3.14 (s, 3H), 3.03 (t, 2H), 3.00 (d, 3H); MS (m/e) 525, 527 (M+1).

Example 1808

8-[5-Chloro-4-(2-methylaminomethyl-phenylamino)-pyrimidin-2-ylamino]-2-methyl-1,2,4,5-tetrahydro-benzo[c]azepin-3-one Following a procedure analogous to Example 1741e, 8-amino-2-methyl-1,2,4,5-tetrahydro-benzo[c]azepin-3-one and (2,5-dichloro-pyrimidin-4-yl)-(2-methylaminomethyl-phenyl)-amine (TFA salt) was converted to 8-[5-chloro-4-(2-methylaminomethyl-phenylamino)-pyrimidin-2-ylamino]-2-methyl-1,2,4,5-tetrahydro-benzo[c]azepin-3-one. HCl salt: $^1$H NMR (300 MHz, CD$_3$OD) δ 8.18 (s, 1H), 7.6 (m, 3H), 7.52 (d, 1H), 7.1 (m, 3H), 4.41 (s, 2H), 4.18 (s, 2H), 3.07 (t, 2H), 2.97 (s, 3H), 2.89 (t, 2H), 2.65 (s, 3H); MS (m/e) 437 (M+1).

Example 1809

2-[5-Chloro-2-(2-methyl-3-oxo-2,3,4,5-tetrahydro-1H-benzo[c]azepin-8-ylamino)-pyrimidin-4-ylamino]-5-fluoro-N-methyl-benzamide Following a procedure analogous to Example 1742a, 8-amino-2-methyl-1,2,4,5-tetrahydro-benzo[c]azepin-3-one and 2-(2,5-dichloro-pyrimidin-4-ylamino)-5-fluoro-N-methyl-benzamide were converted to 2-[5-chloro-2-(2-methyl-3-oxo-2,3,4,5-tetrahydro-1H-benzo[c]azepin-8-ylamino)-pyrimidin-4-ylamino]-5-fluoro-N-methyl-benzamide: $^1$H NMR (300 MHz, CD$_3$OD) δ 8.82 (bs, 1H), 8.20 (s, 1H), 7.57 (m, 3H), 7.37 (m, 1H), 7.23 (d, 1H), 4.67 (s, 2H), 3.23 (dd, 2H), 3.14 (s, 3H), 3.07 (m, 5H); MS (m/e) 469 (M+1).

Example 1810

{2-[5-Chloro-2-(2-methyl-3-oxo-2,3,4,5-tetrahydro-1H-benzo[c]azepin-8-ylamino)-pyrimidin-4-ylamino]-phenoxy}-acetonitrile Following a procedure analogous to Example 1742a, 8-amino-2-methyl-1,2,4,5-tetrahydro-benzo[c]azepin-3-one and [2-(2,5-dichloro-pyrimidin-4-ylamino)-phenoxy]-acetonitrile were converted to {2-[5-chloro-2-(2-methyl-3-oxo-2,3,4,5-tetrahydro-1H-benzo[c]azepin-8-ylamino)-pyrimidin-4-ylamino]-phenoxy}-acetonitrile: $^1$H NMR (300 MHz, CD$_3$OD) δ 8.21 (d, 1H), 8.17 (s, 1H), 7.51 (s, 1H), 7.45 (d, 1H), 7.37 (m, 2H), 7.27 (m, 1H), 7.15 (d, 1H), 5.18 (s, 2H), 4.56 (s, 2H), 3.20 (t, 2H), 3.11 (s, 3H), 3.04 (t, 2H); MS (m/e) 449 (M+1).

Example 1811

2-[5-Chloro-2-(4-oxo-2,3,4,5-tetrahydro-1H-benzo[d]azepin-7-ylamino)-pyrimidin-4-ylamino]-N-methylbenzamide Following a procedure analogous to Example 1794b, 1,3,4,5-tetrahydro-benzo[d]azepin-2-one was converted to 8-nitro-1,3,4,5-tetrahydro-benzo[d]azepin-2-one, which following a procedure analogous to Example 1794c was converted to 8-amino-1,3,4,5-tetrahydro-benzo[d]azepin-2-one. Following a procedure analogous to Example 1742a, 2-(2,5-dichloro-pyrimidin-4-ylamino)-N-methylbenzamide and 8-amino-1,3,4,5-tetrahydro-benzo[d]azepin-2-one were converted to 2-[5-chloro-2-(4-oxo-2,3,4,5-tetrahydro-1H-benzo[d]azepin-7-ylamino)-pyrimidin-4-ylamino]-N-methylbenzamide: $^1$H NMR (300 MHz, CD$_3$OD) δ 8.63 (br, 1H), 8.25 (s, 1H), 7.9 (d, 1H), 7.63 (t, 1H), 7.41 (m, 3H), 3.96 (s, 2H), 3.76 (t, 2H), 3.3 (t, 2H), 3.06 (s, 3H); MS (m/e): 437.3 (M+1).

Example 1812

3-[5-Chloro-2-(4-oxo-2,3,4,5-tetrahydro-1H-benzo[d]azepin-7-ylamino)-pyrimidin-4-ylamino]-4-methyl-thiophene-2-carboxylic acid methylamide Following a procedure analogous to Example 1742a, 3-(2,5-dichloro-pyrimidin-4-ylamino)-4-methyl-thiophene-2-carboxylic acid methylamide and 8-amino-1,3,4,5-tetrahydro-benzo[d]azepin-2-one were converted to 3-[5-chloro-2-(4-oxo-2,3,4,5-tetrahydro-1H benzo[d]azepin-7-ylamino)-pyrimidin-4-ylamino]-4-methyl-thiophene-2-carboxylic acid methylamide: $^1$H NMR (300 MHz, CD$_3$OD) δ 8.15 (s, 1H), 7.47 (s, 1H), 7.39 (d, 1H), 7.3 (dd, 1H), 7.05 (d, 1H), 3.79 (s, 2H), 3.66 (t, 2H), 3.15 (t, 2H), 2.95 (s, 3H), 2.2 (s, 3H); MS (m/e): 457.3 (M+1).

Example 1813

7-[5-Chloro-4-(2-pyrazol-1-yl-phenylamino)-pyrimidin-2-ylamino]-1,3,4,5-tetrahydro-benzo[d]azepin-2-one Following a procedure analogous to Example 1742a, 7-amino-1,3,4,5-tetrahydro-benzo[d]azepin-2-one and (2,5-dichloro-pyrimidin-4-yl)-(2-pyrazol-1-yl-phenyl)-amine were converted to 7-[5-chloro-4-(2-pyrazol-1-yl-phenylamino)-pyrimidin-2-ylamino]-1,3,4,5-tetrahydro-benzo[d]azepin-2-one: $^1$H NMR (300 MHz, CDCl$_3$) δ 10.32 (s, 1H), 8.58 (d, 1H), 8.14 (s, 1H), 7.95 (d, 1H), 7.91 (d, 1H), 7.59-7.30 (m, 5H), 7.14 (d, 1H), 6.99 (s, 1H), 6.61 (d, 1H), 5.83 (bt, 1H), 3.89 (s, 2H), 3.70 (q, 2H), 3.20 (t, 2H); MS (m/e) 446 (M+1).

Example 1814

2-[5-Chloro-2-(2-oxo-2,3,4,5-tetrahydro-1H-benzo[d]azepin-7-ylamino)-pyrimidin-4-ylamino]-3,5,N-trimethyl-benzamide Following a procedure analogous to Example 1742a, 7-amino-1,3,4,5-tetrahydro-benzo[d]azepin-2-one and 2-(2,5-dichloro-pyrimidin-4-ylamino)-3,5,N-trimethyl-benzamide were converted to 2-[5-chloro-2-(2-oxo-2,3,4,5-tetrahydro-1H-benzo[d]azepin-7-ylamino)-pyrimidin-4-ylamino]-3,5,N-trimethyl-benzamide. TFA salt: $^1$H NMR (300 MHz, 5% CD$_3$OD in CDCl$_3$) δ 8.00 (s, 1H), 7.43 (s, 1H), 7.31 (s, 1H), 7.25 (s, 1H), 6.94 (s, 2H), 3.58 (bs, 2H), 3.12 (s, 2H), 3.06 (t, 2H), 2.90 (s, 3H), 2.44 (s, 3H), 2.21 (s, 3H); MS (m/e) 465 (M+1).

Example 1815

2-[5-Chloro-2-(3-methyl-4-oxo-2,3,4,5-tetrahydro-1H-benzo[d]azepin-7-ylamino)-pyrimidin-4-ylamino]-N-methylbenzamide 1815a) At −75° C., chloroacetyl chloride (11.3 g, 8.1 mL, 0.1 mol) was added slowly to a suspension of methyl-phenethyl-amine (13.5 g, 0.1 mol), triethylamine (15 mL) in dichloromethane (50 mL). The suspension was warmed to 25° C. over the course of 3 hours and the salt was removed by filtration. The organic phase was washed with HCl solution (1 N, 200 mL), dried with sodium sulfate. The solvent was evaporated in vacuo to give 2-chloro-N-methyl-N-phenethyl-acetamide (20 g, 95%): $^1$H NMR (300 MHz, CDCl$_3$) δ 7.2 (m, 5H), 4.03 (s, 3H), 3.6 (m, 2H), 2.99 (s, 2H), 2.8 (m, 2H).

1815b) At 140° C., 2-chloro-N-methyl-N-phenethyl-acetamide (20 g, 94 mmol) and aluminum trichloride (18.9 g, 142 mmol, 1.5 eq.) were heated for 8 hours. The mixture was allowed to cool to ambient temperature and poured over ice. The mixture was extracted with dichlomethane (3×200 mL) and dried with sodium sulfate. The solvent was evaporated to give 3-methyl-1,3,4,5-tetrahydro-benzo[d]azepin-2-one (18.2 g, 100%): $^1$H NMR (300 MHz, CDCl$_3$) δ 7.1 (m, 4H), 3.92 (s, 2H), 3.71 (t, 2H), 3.15 (t, 2H), 3.03 (s, 3H).

1815c) Following a procedure analogous to Example 1794b, 3-methyl-1,3,4,5-tetrahydro-benzo[d]azepin-2-one was converted to 3-methyl-8-nitro-1,3,4,5-tetrahydro-benzo[d]azepin-2-one: $^1$H NMR (300 MHz, CDCl$_3$) δ 7.9 (m, 2H), 7.25 (d, 1H), 3.98 (s, 2H), 3.75 (t, 2H), 3.22 (t, 2H), 3.03 (s, 3H).

1815d) Following a procedure analogous to Example 1791b, 3-methyl-8-nitro-1,3,4,5-tetrahydro-benzo[d]azepin-2-one was converted to 8-amino-3-methyl-1,3,4,5-tetrahydro-benzo[d]azepin-2-one: $^1$H NMR (300 MHz, CDCl$_3$) δ 7.3 (m, 3H), 4.0 (s, 2H), 3.8 (t, 2H), 3.2 (t, 2H), 2.98 (s, 3H); MS (m/e) 191 (M+1).

1815e) Following a procedure analogous to Example 1741e, 2-(2,5-dichloro-pyrimidin-4-ylamino)-N-methylbenzamide and 8-amino-3-methyl-1,3,4,5-tetrahydro-benzo[d]azepin-2-one were converted to 2-[5-chloro-2-(3-methyl-4- oxo-2,3,4,5-tetrahydro-1H-benzo[d]azepin-7-ylamino)-pyrimidin-4-ylamino]-N-methyl-benzamide: ¹H NMR (300 MHz, CDCl₃) δ 8.44 (d, 1H), 7.98 (s, 1H), 7.47 (t, 2H), 7.43 (s, 1H), 7.23 (dd, 1H), 7.13 (br, 1H), 7.05 (t, 1H), 6.98 (d, 1H), 3.68 (s, 2H), 3.65 (t, 2H), 3.05 (t, 2H), 2.95 (d, 3H), 2.90 (s, 3H); MS (m/e): 451.3 (M+1).

Example 1816

3-[5-Chloro-2-(3-methyl-4-oxo-2,3,4,5-tetrahydro-1H-benzo[d]azepin-7-ylamino)-pyrimidin-4-ylamino]-4-methyl-thiophene-2-carboxylic acid methylamide Following a procedure analogous to Example 1741e, 3-(2,5-dichloro-pyrimidin-4-ylamino)-4-methyl-thiophene-2-carboxylic acid methylamide and 8-amino-3-methyl-1,3,4,5-tetrahydro-benzo[d]azepin-2-one were converted to 3-[5-chloro-2-(3-methyl-4-oxo-2,3,4,5-tetrahydro-1H-benzo[d]azepin-7-ylamino)-pyrimidin-4-ylamino]-4-methyl-thiophene-2-carboxylic acid methylamide in 78% yield: ¹H NMR (300 MHz, CDCl₃) δ 8.76 (s, 1H), 8.0 (s, 1H), 7.4 (s, 1H), 7.23 (s, 1H), 7.12 (s, 1H), 7.05 (d, 1H), 6.9 (m, 2H), 6.34 (br, 1H), 3.65 (m, 4H), 3.0 (m, 2H), 2.98 (s, 3H), 2.9 (d, 3H), 2.07 (s, 3H); MS (m/e): 471.3 (M+1).

Example 1817

3-Chloro-2-[5-chloro-2-(3-methyl-4-oxo-2,3,4,5-tetrahydro-1H-benzo[d]azepin-7-ylamino)-pyrimidin-4-ylamino]-N-methylbenzamide Following a procedure analogous to Example 1741e, 3-chloro-2-(2,5-dichloro-pyrimidin-4-ylamino)-N-methyl-benzamide and 8-amino-3-methyl-1,3,4,5-tetrahydro-benzo[d]azepin-2-one were converted to 3-chloro-2-[5-chloro-2-(3-methyl-4-oxo-2,3,4,5-tetrahydro-1H-benzo[d]azepin-7-ylamino)-pyrimidin-4-ylamino]-N-methylbenzamide: ¹H NMR (300 MHz, CDCl₃) δ 8.15 (s, 1H), 7.68 (dd, 1H), 7.37 (m, 3H), 6.99 (s, 1H), 6.97 (d, 1H), 3.73 (t, 2H), 3.55 (s, 2H), 3.1 (t, 2H), 3.06 (s, 3H), 2.88 (d, 3H); MS (m/e): 485.3 (M+1).

Example 1818

2-[5-Chloro-2-(3-methyl-4-oxo-2,3,4,5-tetrahydro-1H-benzo[d]azepin-7-ylamino)-pyrimidin-4-ylamino]-3,5,N-trimethyl-benzamide Following a procedure analogous to Example 1742a, 8-amino-3-methyl-1,3,4,5-tetrahydro-benzo[d]azepin-2-one and 2-(2,5-dichloro-pyrimidin-4-ylamino)-3,5,N-trimethyl-benzamide were converted to 2-[5-chloro-2-(3-methyl-4-oxo-2,3,4,5-tetrahydro-1H-benzo[d]azepin-7-ylamino)-pyrimidin-4-ylamino]-3,5,N-trimethyl-benzamide: ¹H NMR (300 MHz, CDCl₃) δ 11.62 (s, 1H), 9.35 (s, 1H), 7.92 (s, 1H), 7.78 (bd, 1H), 7.52 (s, 1H), 7.44 (s, 1H), 7.39 (s, 1H), 7.17 (dd, 1H), 7.05 (d, 1H), 4.00 (bs, 1H), 3.89 (bd, 1H), 3.58 (bs, 1H), 3.16 (s, 2H), 3.11 (s, 3H), 3.00 (d, 3H), 2.92 (bd, 1H), 2.52 (s, 3H), 2.26 (s, 3H); MS (m/e) 464 (M+1).

Example 1819

8-[5-Chloro-4-(2-pyrazol-1-yl-phenylamino)-pyrimidin-2-ylamino]-3-methyl-1,3,4,5-tetrahydro-benzo[d]azepin-2-one Following a procedure analogous to Example 1742a, 8-amino-3-methyl-1,3,4,5-tetrahydro-benzo[d]azepin-2-one and (2,5-dichloro-pyrimidin-4-yl)-(2-pyrazol-1-yl-phenyl)-amine were converted to 8-[5-chloro-4-(2-pyrazol-1-yl-phenylamino)-pyrimidin-2-ylamino]-3-methyl-1,3,4,5-tetrahydro-benzo[d]azepin-2-one: ¹H NMR (300 MHz, CDCl₃) δ 10.30 (s, 1H), 8.59 (d, 1H), 8.11 (s, 1H), 7.95 (d, 1H), 7.91 (d, 1H), 7.59 (t, 1H), 7.50-7.30 (m, 4H), 7.12 (d, 1H), 6.96 (s, 1H), 6.61 (d, 1H), 3.94 (s, 2H), 3.80 (t, 2H), 3.20 (t, 2H), 3.13 (s, 3H); MS (m/e) 446 (M+1).

Example 1820

3-[5-Chloro-2-(3-methyl-4-oxo-2,3,4,5-tetrahydro-1H-benzo[d]azepin-7-ylamino)-pyrimidin-4-ylamino]-pyridine-2-carboxylic acid methylamide 1820a) Following a procedure analogous to Example 1750a, 3-amino-pyridine-2-carboxylic acid was converted to 3-amino-pyridine-2-carboxylic acid methylamide, which following a procedure analogous to Example 1751b was converted to 3-(2,5)-dichloro-pyrimidin-4-ylamino)-pyrimidine-2-carboxylic acid methyl amide: ¹H NMR (300 MHz, CDCl₃) δ 9.4 (d, 1H), 8.6 (bs, 1H), 8.4 (s, 1H), 8.3 (d, 1H), 3.1 (d, 3H).

1820b) Following a procedure analogous to Example 1742a, 8-amino-3-methyl-1,3,4,5-tetrahydro-benzo[d]azepin-2-one and 3-(2,5-dichloro-pyrimidin-4-ylamino)-pyridine-2-carboxylic acid methylamide were converted to 3-[5-chloro-2-(3-methyl-4-oxo-2,3,4,5-tetrahydro-1H-benzo[d]azepin-7-ylamino)-pyrimidin-4-ylamino]-pyridine-2-carboxylic acid methylamide. TFA salt: ¹H NMR (300 MHz, CD₃OD) δ 8.58 (d, 1H), 8.18 (s, 1H), 7.69 (m, 3H), 7.44 (m, 2H), 7.23 (m, 2H), 6.29 (d, 1H), 4.29 (s, 2H), 3.39 (m, 2H), 3.26 (m, 2H), 3.04 (s, 3H), 2.94 (s, 3H); MS (m/e) 452 (M+1).

Example 1821

5-[5-Chloro-2-(3-methyl-4-oxo-2,3,4,5-tetrahydro-1H-benzo[d]azepin-7-ylamino)-pyrimidin-4-ylamino]-1-methyl-1H-pyrazole-4-carboxylic acid methylamide Following a procedure analogous to Example 1741e, 5-(2,5-dichloro-pyrimidin-4-ylamino)-1-methyl-1H-pyrazole-4-carboxylic acid methylamide and 8-amino-3-methyl-1,3,4,5-tetrahydro-benzo[d]azepin-2-one were converted to 5-[5-chloro-2-(3-methyl-4-oxo-2,3,4,5-tetrahydro-1H-benzo[d]azepin-7-ylamino)-pyrimidin-4-ylamino]-1-methyl-1H-pyrazole-4-carboxylic acid methylamide: ¹H NMR (300 MHz, CDCl₃) δ 8.23 (s, 1H), 8.05 (s, 1H), 7.85 (s, 1H), 7.28 (s, 1H), 7.04 (br, 2H), 6.9 (m, 2H), 3.7 (s, 2H), 3.68 (s, 3H), 3.67 (t, 2H), 3.10 (m, 4H), 3.0 (s, 3H), 2.86 (d, 3H); MS (m/e): 455.4 (M+1).

Example 1822

(R)-2-[5-Chloro-2-(3-methyl-4-oxo-2,3,4,5-tetrahydro-1H-benzo[d]azepin-7-ylamino)-pyrimidin-4-ylamino]-3-methyl-butyramide Following a procedure analogous to Example 1742a, 8-amino-3-methyl-1,3,4,5-tetrahydro-benzo[d]azepin-2-one and (R)-2-(2,5-dichloro-pyrimidin-4-ylamino)-3-methyl-butyramide were converted to (R)-2-[5-chloro-2-(3-methyl-4-oxo-2,3,4,5-tetrahydro-1H-benzo[d]azepin-7-ylamino)-pyrimidin-4-ylamino]-3-methyl-butyramide: ¹H NMR (300 MHz, CD₃OD) δ 8.03 (s, 1H), 7.29 (s, 1H), 7.26 (s, 2H), 4.57

(d, 1H), 4.10-3.59 (m, 4H), 3.21 (t, 2H), 3.04 (s, 3H), 2.22 (m, 1H), 1.00 (d, 3H), 0.97 (d, 3H); MS (m/e) 417 (M+1).

Example 1823

(S)-2-[5-Chloro-2-(3-methyl-4-oxo-2,3,4,5-tetrahydro-1H-benzo[d]azepin-7-ylamino)-pyrimidin-4-ylamino]-3-methyl-butyramide Following a procedure analogous to Example 1742a, 8-amino-3-methyl-1,3,4,5-tetrahydro-benzo[d]azepin-2-one and (S)-2-(2,5-dichloro-pyrimidin-4-ylamino)-3-methyl-butyramide were converted to (S)-2-[5-chloro-2-(3-methyl-4-oxo-2,3,4,5-tetrahydro-1H-benzo[d]azepin-7-ylamino)-pyrimidin-4-ylamino]-3-methyl-butyramide: $^1$H NMR (300 MHz, CDCl$_3$) δ 7.87 (s, 1H), 7.66 (s, 1H), 7.07 (dd, 2H), 6.03 (d, 1H), 4.66 (dd, 1H), 3.89 (dd, 2H), 3.78 (m, 2H), 3.67 (s, 3H), 3.14 (t, 2 h), 3.03 (s, 3H), 2.26 (m, 1H), 1.02 (d, 3H), 1.00 (d, 3H); MS (m/e) 417 (M+1).

Example 1824

2-{[5-Fluoro-2-(3-methyl-4-oxo-2,3,4,5-tetrahydro-1H-benzo[d]azepin-7-ylamino)-pyrimidin-4-yl]-methyl-amino}-N-methyl-benzamide Following a procedure analogous to Example 1741e, 8-amino-3-methyl-1,3,4,5-tetrahydro-benzo[d]azepin-2-one and 2-[(2-chloro-5-fluoro-pyrimidin-4-yl)-methyl-amino]-N-methyl-benzamide was converted to 2-{[5-fluoro-2-(3-methyl-4-oxo-2,3,4,5-tetrahydro-1H-benzo[d]azepin-7-ylamino)-pyrimidin-4-yl]-methyl-amino}-N-methyl-benzamide: $^1$H NMR (300 MHz, CD$_3$OD) δ 7.73 (d, 1H), 7.51 (d, 2H), 7.4 (m, 4H), 7.00 (d, 1H), 3.83 (s, 2H), 3.79 (t, 2H), 3.33 (s, 2H), 3.08 (t, 2H), 3.01 (s, 3H), 2.73 (s, 3H); $^{19}$F NMR (282 MHz, CD$_3$OD) δ −159.0; MS (m/e) 449 (M+1).

Example 1825

8-{5-Chloro-4-[2-(1H-pyrazol-3-yl)-phenylamino]-pyrimidin-2-ylamino}-3-methyl-1,3,4,5-tetrahydro-benzo[d]azepin-2-one Following a procedure analogous to Example 1741e, (2,5-dichloro-pyrimidin-4-yl)-[2-(1H-pyrazol-3-yl)-phenyl]-amine and 8-amino-3-methyl-1,3,4,5-tetrahydro-benzo[d]azepin-2-one were converted to 8-{5-chloro-4-[2-(1H-pyrazol-3-yl)-phenylamino]-pyrimidin-2-ylamino}-3-methyl-1,3,4,5-tetrahydro-benzo[d]azepin-2-one: $^1$H NMR (300 MHz, CDCl$_3$) δ 8.48 (d, 1H), 8.41 (s, 1H), 7.56 (d, 1H), 7.39 (d, 1H), 7.35 (s, 1H), 7.16 (m, 3H), 7.15 (m, 2H), 6.87 (s, 1H), 6.74 (t, 1H), 3.9 (s, 2H), 3.67 (t, 2H), 3.09 (t, 2H), 3.02 (s, 3H); MS (m/e): 460.4 (M+1).

Example 1826

2-(5-Chloro-2-(1,1-dimethyl-3-oxo-2,3,4,5-tetrahydro-1H-benzo[c]azepin-7-ylamino)pyrimidin-4-ylamino)-3-fluoro-N-methylbenzamide 1826a) To 100 mL of HNO$_3$ (90%) at −30° C. was slowly added 12 g 1,1-dimethyl-3,4-dihydronaphthalen-2(1H)-one (Ref.: J. Am. Chem. Soc. (1993), 115, 10628). The mixture was stirred for 10 minutes and slowly poured onto 600 mL of ice water containing 120 g of KOH (more ice was added as necessary to keep the mixture cool). The mixture was extracted with ethyl acetate, dried with sodium sulfate, filtered and concentrated in vacuo. The isomers were separated iterative silica gel column using 20% ethyl acetate in hexanes followed by trituration with ethyl ether to provide 3.8 g of the higher Rf 1,1-dimethyl-6-nitro-3,4-dihydronaphthalen-2 (1H)-one: $^1$H NMR (300 MHz, CDCl$_3$) δ 8.1 (dd, 1H, C7-H), 8.0 (d, 1H, C5-H), 7.5 (d, 1H, C8-H), 3.2 (t, 2H), 2.7 (t, 2H), 1.5 (s, 6H), and 5.1 g of the lower Rf 1,1-dimethyl-7-nitro-3, 4-dihydronaphthalen-2(1H)-one: $^1$H NMR (300 MHz, CDCl$_3$) δ 8.2 (d, 1H, C8-H), 8.0 (dd, 1H, C6-H), 7.3 (d, 1H, C5-H), 3.2 (t, 2H), 2.7 (t, 2H), 1.5 (s, 6H).

1826b) A solution of 1,1-dimethyl-6-nitro-3,4-dihydronaphthalen-2(1H)-one (3.26 g) in methanesulfonic acid (30 mL) was cooled to 0° C. and treated with 1.3 g of sodium azide in portions. After stirring at 0° C. for 3 hours, the mixture was neutralized by pouring onto an excess of saturated sodium bicarbonate at 0° C. The mixture was extracted with methylene chloride, dried with sodium sulfate, filtered and concentrated in vacuo. Column chromatography (20% EtOAc/hexanes) provided the mixture of 3-(5-nitro-2-(prop-1-en-2-yl)phenyl)propanenitrile and 1,1-dimethyl-7-nitro-4, 5-dihydrobenzo[c]oxepin-3(1H)-one. The lactam 1,1-dimethyl-7-nitro-1,2,4,5-tetrahydrobenzo[c]azepin-3-one (1.75 g) was eluted with 5% methanol in methylene chloride: $^1$H NMR (300 MHz, CDCl$_3$) δ 8.0 (dd, 1H, C8-H), 8.0 (d, 1H, C6-H), 7.5 (d, 1H, C9-H), 3.2 (m, 2H), 2.7 (m, 2H), 1.7 (s, 6H).

1826c) A solution of 1,1-dimethyl-7-nitro-1,2,4,5-tetrahydrobenzo[c]azepin-3-one (1.75 g) in THF (175 mL) and MeOH (20 mL) was treated with an solution of Na$_2$S$_2$O$_4$ (5 g) and sodium bicarbonate (5 g) in water (200 mL). After 15 minutes, 250 mL of EtOAc and 250 mL saturated NaCl was added and the organic layer was separated. The aqueous layer was extracted again with EtOAc and the combined organic layers were washed again with brine. The organic layer was dried with sodium sulfate, filtered and concentrated in vacuo to provide 400 mg of 7-amino-1,1-dimethyl-1,2,4,5-tetrahydrobenzo[c]azepin-3-one: $^1$H NMR (300 MHz, CDCl$_3$) δ 7.1 (d, 1H, C9-H), 6.5 (dd, 1H, C8-H), 6.4 (d, 1H, C6-H), 3.0 (m, 2H), 2.6 (m, 2H), 1.6 (s, 6H).

1826d) A mixture of 7-amino-1,1-dimethyl-1,2,4,5-tetrahydrobenzo[c]azepin-3-one (40 mg), 2-(2,5-dichloropyrimidin-4-ylamino)-3-fluoro-N-methylbenzamide (50 mg), and 2 drops of 4 N HCl/dioxane in IPA (3 mL) were microwave-heated at 120° C. for 1.5 hours. The mixture was concentrated to afford crude 2-(2-(3-(3-amino-3-oxopropyl)-4-(prop-1-en-2-yl)phenylamino)-5-chloropyrimidin-4-ylamino)-3-fluoro-N-methylbenzamide. The crude mixture was stirred for 4 hours in TFA and concentrated. Purification by semi-preparative HPLC provided 2-(5-chloro-2-(1,1-dimethyl-3-oxo-2,3,4,5-tetrahydro-1H-benzo[c]azepin-7-ylamino)pyrimidin-4-ylamino)-3-fluoro-N-methylbenzamide (45.7 mg) as a TFA salt: $^1$H NMR (300 MHz, CD$_3$OD) δ 8.3 (s, 1H), 7.7-7.5 (m, 3H), 7.65 (s, 1H, slowly exchanging NH), 7.4 (d, 1H), 7.32 (d, 1H), 7.28 (dd, 1H), 3.0 (m, 2H), 3.0 (s, 3H), 2.7 (m, 2H), 1.8 (s, 6H).

Example 1827

2-(5-Chloro-2-(1,1-dimethyl-3-oxo-2,3,4,5-tetrahydro-1H-benzo[c]azepin-7-ylamino)pyrimidin-4-ylamino)-N-methylbenzamide Following a procedure analogous to Example 1826d, 7-amino-1,1-dimethyl-1,2,4,5-tetrahydrobenzo[c]azepin-3-one and 2-(2,5-dichloropyrimidin-4-ylamino)-N-methylbenzamide were converted to 2-(5-chloro-2-(1,1-dimethyl-3-oxo-2,3,4,5-tetrahydro-1H-benzo[c]azepin-7-ylamino)

pyrimidin-4-ylamino)-N-methylbenzamide, TFA salt: $^1$H NMR (300 MHz, CD$_3$OD) δ 8.55 (d, 1H), 8.25 (s, 1H), 7.9 (dd, 1H), 7.6 (d, 1H), 7.5 (t, 1H), 7.5-7.45 (m, 2H), 7.4 (td, 1H), 3.2 (m, 2H), 3.1 (s, 3H), 2.8 (m, 2H), 2.0 (s, 6H).

Example 1828

3-Chloro-2-(5-chloro-2-(1,1-dimethyl-3-oxo-2,3,4,5-tetrahydro-1H-benzo[c]azepin-7-ylamino)pyrimidin-4-ylamino)-N-methylbenzamide Following a procedure analogous to Example 1826d, 7-amino-1,1-dimethyl-1,2,4,5-tetrahydrobenzo[c]azepin-3-one and 3-chloro-2-(2,5-dichloropyrimidin-4-ylamino)-N-methylbenzamide were converted to 3-chloro-2-(5-chloro-2-(1,1-dimethyl-3-oxo-2,3,4,5-tetrahydro-1H-benzo[c]azepin-7-ylamino)pyrimidin-4-ylamino)-N-methylbenzamide, TFA salt: $^1$H NMR (300 MHz, CD$_3$OD) δ 8.3 (s, 1H), 7.9 (dd, 1H), 7.75 (dd, 1H), 7.65 (t, 1H), 7.4 (d, 1H), 7.3 (d, 2H), 7.2 (dd, 1H), 3.1 (m, 2H), 3.0 (s, 3H), 2.7 (m, 2H), 1.8 (s, 6H).

Example 1829

3-(5-Chloro-2-(1,1-dimethyl-3-oxo-2,3,4,5-tetrahydro-1H-benzo[c]azepin-7-ylamino)pyrimidin-4-ylamino)-N-methylthiophene-2-carboxamide Following a procedure analogous to Example 1826d, 7-amino-1,1-dimethyl-1,2,4,5-tetrahydrobenzo[c]azepin-3-one and 3-(2,5-dichloropyrimidin-4-ylamino)-N,4-dimethylthiophene-2-carboxamide were converted to 3-(5-chloro-2-(1,1-dimethyl-3-oxo-2,3,4,5-tetrahydro-1H-benzo[c]azepin-7-ylamino)pyrimidin-4-ylamino)-N-methylthiophene-2-carboxamide, TFA salt: $^1$H NMR (300 MHz, CD$_3$OD) δ 8.2 (s, 1H), 7.4 (d, 1H), 7.3 (d, 1H), 7.25 (d, 1H), 7.1 (dd, 1H), 3.0 (m, 2H), 2.8 (s, 3H), 2.6 (m, 2H), 2.1 (s, 3H) 1.7 (s, 6H).

Example 1830

2-(5-Chloro-2-(1,1-dimethyl-3-oxo-2,3,4,5-tetrahydro-1H-benzo[c]azepin-7-ylamino)pyrimidin-4-ylamino)-N,3-dimethylbenzamide 1830a) A solution of 2-amino-N,3-dimethylbenzamide (562 mg) and 2,4,5-trichloropyrimidine (1.3 g) in N-methylpyrrolidinone (20 mL) were heated with potassium carbonate (2 g) at 80° C. for 16 hours. The mixture was diluted with ethyl acetate, washed three times with brine, dried with sodium sulfate, filtered, and concentrated. Column chromatography (20-30% ethyl acetate in methylene chloride) followed by trituration with ethyl ether provided 200 mg of 2-(2,5-dichloropyrimidin-4-ylamino)-N,3-dimethylbenzamide: $^1$H NMR (300 MHz, CDCl$_3$) δ 9.3 (s, 1H), 8.15 (s, 1H), 7.4 (d, 1H), 7.3 (d, 1H), 7.2 (t, 1H), 6.05 (m, 1H), 3.0, (d, 3H), 2.2 (s, 3H).

1830b) A suspension of 7-amino-1,1-dimethyl-1,2,4,5-tetrahydrobenzo[c]azepin-3-one (46 mg), 2-(2,5-dichloropyrimidin-4-ylamino)-N,3-dimethylbenzamide (42 mg), and camphorsulfonic acid (40 μL of a 100 mg/mL aqueous solution) were heated in isopropanol (2 mL) for 4 hours at 120° C. using microwave irradiation. The solvent was evaporated to afford crude 2-(2-(3-(3-amino-3-oxopropyl)-4-(prop-1-en-2-yl)phenylamino)-5-chloropyrimidin-4-ylamino)-N,3-dimethylbenzamide The crude mixture was dissolved in TFA and allowed to stand for 4 hours, then concentrated. Purification by semi-preparative HPLC provided 2-(5-chloro-2-(1,1-dimethyl-3-oxo-2,3,4,5-tetrahydro-1H-benzo[c]azepin-7-ylamino)pyrimidin-4-ylamino)-N,3-dimethylbenzamide as the TFA salt. The non-salt was obtained by stirring the TFA salt in acetonitrile with 300 mg of MP-carbonate (Argonaut, 2.91 mmol/g) for 2 days. The resin was separated by filtration, then washed with methanol and methylene chloride. The filtrate was concentrated and the residue triturated with ethyl ether to provide 14 mg of the neutral compound: $^1$H NMR (300 MHz, CDCl$_3$ with 5% CD$_3$OD) δ 8.05 (s, 1H), 7.5-7.4 (m, 2H), 7.35 (dd, 1H), 7.3 (d, 1H), 7.15 (d, 1H), 7.1 (dd, 1H), 2.9 (s, 3H), 2.8 (m, 2H), 2.6 (m, 2H), 2.3 (s, 3H) 1.8 (s, 6H).

Example 1831

2-(5-Chloro-2-(1,1-dimethyl-3-oxo-2,3,4,5-tetrahydro-1H-benzo[c]azepin-8-ylamino)pyrimidin-4-ylamino)-3-fluoro-N-methylbenzamide 1831a) Following a procedure analogous to Example 1826b, 1,1-dimethyl-7-nitro-3,4-dihydronaphthalen-2(1H)-one (3.3 g) was converted to 1,1-dimethyl-8-nitro-1,2,4,5-tetrahydrobenzo[c]azepin-3-one (1.0 g): $^1$H NMR (300 MHz, CDCl$_3$) δ 8.2 (d, 1H, C9-H), 8.0 (dd, 1H, C7-H), 7.3 (d, 1H, C6-H), 6.6 (br, 1H, NH), 3.2 (m, 2H), 2.7 (m, 2H), 1.8 (s, 6H).

1831b) A solution of 1,1-dimethyl-8-nitro-1,2,4,5-tetrahydrobenzo[c]azepin-3-one (0.46 g) in methanol (50 mL) was sparged with argon and 10% Pd—C (46 mg) was added. The mixture was stirred for 16 hours under a hydrogen atmosphere, filtered through celite, and concentrated to provide 8-amino-1,1-dimethyl-1,2,4,5-tetrahydrobenzo[c]azepin-3-one quantitatively: $^1$H NMR (300 MHz, CDCl$_3$) δ 6.9 (d, 1H, C6-H), 6.6 (d, 1H, C9-H), 6.5 (dd, 1H, C7-H), 5.9 (br, 1H), 3.6 (br, 2H), 3.0 (m, 2H), 2.6 (m, 2H), 1.6 (s, 6H).

1831c) A mixture of 8-amino-1,1-dimethyl-1,2,4,5-tetrahydrobenzo[c]azepin-3-one (32 mg), 2-(2,5-dichloropyrimidin-4-ylamino)-3-fluoro-N-methylbenzamide (50 mg), and camphorsulfonic acid (30 μL of a 100 mg/mL aqueous solution) in IPA (2 mL) were microwave-heated at 120° C. for 3 hours. The mixture was concentrated and purified by semi-preparative HPLC to provide 2-(5-chloro-2-(1,1-dimethyl-3-oxo-2,3,4,5-tetrahydro-1H-benzo[c]azepin-8-ylamino)pyrimidin-4-ylamino)-3-fluoro-N-methylbenzamide as a TFA salt. The non-salt was obtained by stirring the TFA salt in acetonitrile with 200 mg of MP-carbonate (Argonaut, 3.17 mmol/g) for 16 hours. The resin was separated by filtration, then washed with methanol and methylene chloride. The filtrate was concentrated to provide 25.9 mg of the neutral compound: $^1$H NMR (300 MHz, CDCl$_3$) δ 8.8 (s, 1H), 8.1 (s, 1H), 7.4 (dd, 1H), 7.35-7.15 (m, 3H), 7.1 (d, 1H), 6.9 (d, 1H), 6.2 (m, 1H), 5.8 (s, 1H), 3.0 (m, 2H), 2.9 (d, 3H), 2.6 (m, 2H), 1.6 (s, 6H).

Example 1832

3-(5-Chloro-2-(1,1-dimethyl-3-oxo-2,3,4,5-tetrahydro-1H-benzo[c]azepin-8-ylamino)pyrimidin-4-ylamino)bicyclo[2.2.1]hept-5-ene-2-carboxamide Following a procedure analogous to Example 1831c, 8-amino-1,1-dimethyl-1,2,4,5-tetrahydrobenzo[c]azepin-3-one and 3-(2,5-dichloropyrimidin-4-ylamino)bicyclo[2.2.1]hept-5-ene-2-carboxamide were converted to 3-(5-chloro-2-(1,1-dimethyl-3-oxo-2,3,4,5-tetrahydro-1H-benzo[c]azepin-8-ylamino)pyrimidin-4-ylamino)bicyclo[2.2.1]hept-5-ene-2-carboxamide: $^1$H NMR (300 MHz, DMSO-d6, partial spectrum) δ 9.6 (br, 1H), 8.6 (br, 1H), 8.1 (s, 1H), 7.9 (s, 1H), 7.7 (d, 1H), 7.4 (s, 1H), 7.35 (s, 1H), 7.3 (s, 1H), 7.2 (d, 1H), 6.4 (m, 1H), 6.25 (m, 1H), 4.0 (t, 1H), 3.0 (m, 2H), 2.9 (s, 1H), 2.8 (s, 2H), 2.0 (d, 1H), 1.6 (s, 6H), 1.4 (d, 1H).

Example 1833

2-(5-Chloro-2-(1,1-dimethyl-3-oxo-2,3,4,5-tetrahydro-1H-benzo[c]azepin-8-ylamino)pyrimidin-4-ylamino)-N-methylbenzamide Following a procedure analogous to Example 1831c, 8-amino-1,1-dimethyl-1,2,4,5-tetrahydrobenzo[c]azepin-3-one and 2-(2,5-dichloropyrimidin-4-ylamino)-N-methylbenzamide were converted to 2-(5-chloro-2-(1,1-dimethyl-3-oxo-2,3,4,5-tetrahydro-1H-benzo[c]azepin-8-ylamino)pyrimidin-4-ylamino)-N-methylbenzamide: $^1$H NMR (300 MHz, DMSO-d6, partial spectrum) δ 9.6 (s, 1H), 8.8-9.0 (m, 2H), 8.4 (s, 1H), 7.9 (d, 1H), 7.8 (d, 1H), 7.7-7.6 (m, 2H), 7.4 (s, 1H), 7.3 (t, 1H), 7.2 (d, 1H), 3.1 (m, 2H), 2.9 (d, 3H), 1.7 (s, 6H).

Example 1834

3-Chloro-2-(5-chloro-2-(1,1-dimethyl-3-oxo-2,3,4,5-tetrahydro-1H-benzo[c]azepin-8-ylamino)pyrimidin-4-ylamino)-N-methylbenzamide Following a procedure analogous to Example 1831c, 8-amino-1,1-dimethyl-1,2,4,5-tetrahydrobenzo[c]azepin-3-one and 3-chloro-2-(2,5-dichloropyrimidin-4-ylamino)-N-methylbenzamide were converted to 3-chloro-2-(5-chloro-2-(1,1-dimethyl-3-oxo-2,3,4,5-tetrahydro-1H-benzo[c]azepin-8-ylamino)pyrimidin-4-ylamino)-N-methylbenzamide, but without neutralization to the non-salt: $^1$H NMR (300 MHz, CD$_3$OD) δ 8.3 (s, 1H), 7.8 (dd, 1H), 7.7 (dd, 1H), 7.6 (t, 1H), 7.4 (d, 1H), 7.3 (d, 1H), 7.1 (d, 1H), 3.2 (m, 2H), 3.0 (s, 3H), 2.8 (m, 2H), 1.8 (s, 6H).

Example 1835

3-(5-Chloro-2-(1,1-dimethyl-3-oxo-2,3,4,5-tetrahydro-1H-benzo[c]azepin-8-ylamino)pyrimidin-4-ylamino)-N,4-dimethylthiophene-2-carboxamide Following a procedure analogous to Example 1831c, 8-amino-1,1-dimethyl-1,2,4,5-tetrahydrobenzo[c]azepin-3-one and 3-(2,5-dichloropyrimidin-4-ylamino)-N,4-dimethylthiophene-2-carboxamide were converted to 3-(5-chloro-2-(1,1-dimethyl-3-oxo-2,3,4,5-tetrahydro-1H-benzo[c]azepin-8-ylamino)pyrimidin-4-ylamino)-N,4-dimethylthiophene-2-carboxamide, but without neutralization to the non-salt: $^1$H NMR (300 MHz, CD$_3$OD) δ 8.3 (s, 1H), 7.45 (m, 2H), 7.35 (dd, 1H), 7.2 (d, 1H), 3.2 (m, 2H), 3.0 (s, 3H), 2.8 (m, 2H), 2.2 (s, 3H), 1.8 (s, 6H).

Example 1836

2-[5-Chloro-2-(5,6-dihydro-4H-3,10b-diaza-benzo[e]azulen-9-ylamino)-pyrimidin-4-ylamino]-N-methyl-benzamide 1836a) A solution of 8-amino-benzoazepin-2-one (5.0 g, 28.4 mmol) and triethylamine (3.4 g, 34.1 mmol, 1.2 eq.) in anhydrous DMF (500 mL) was treated with di-tert-butyl dicarbonate (7.5 g, 34 mmol, 1.2 eq.). The mixture was stirred at 50° C. for 24 h and concentrated. The residue was dissolved in DCM (300 mL) and washed 3 times with water. The organic phase was dried over sodium sulfate and the solvent was evaporated. The residue was recrystallized from DCM/hexanes to give (2-oxo-2,3,4,5-tetrahydro-1H-benzo[b]azepin-8-yl)-carbamic acid tert-butyl ester (5.0 g, 18.1 mmol, 64%): $^1$H NMR (300 MHz, CDCl$_3$) δ 7.4 (br, 1H), 7.20 (s, 1H), 7.12 (d, 1H), 6.98 (dd, 1H), 6.5 (br, 1H), 2.75 (t, 2H), 2.36 (t, 2H), 2.2 (m, 2H), 1.53 (s, 9H);).

1836b) A solution of (2-oxo-2,3,4,5-tetrahydro-1H-benzo[b]azepin-8-yl)-carbamic acid tert-butyl ester (5.0 g, 18.1 mmol) in THF (400 mL) was treated with Lawesson's Reagent (7.5 g, 18.5 mmol). After stirring for 12 hours, the precipitate was removed and the filtrate was concentrated. The residue was purified by silica gel chromatography with DCM to give (2-thioxo-2,3,4,5-tetrahydro-1H-benzo[b]azepin-8-yl)-carbamic acid tert-butyl ester (5.0 g, 17.1 mmol, 94%): MS (m/e) 293 (M+1).

1836c) A solution of (2-thioxo-2,3,4,5-tetrahydro-1H-benzo[b]azepin-8-yl)-carbamic acid tert-butyl ester (5.0 g, 17.1 mmol) and potassium carbonate (4.7 g, 34.0 mmol) in acetone (400 mL) was treated with iodomethane (2.5 mL, 5.7 g, 40.0 mmol). The mixture was stirred for 12 h and concentrated. The residue was partitioned between water (100 mL) and DCM (200 mL). The aqueous phase was extracted again with DCM and the combined organic phases were dried over sodium sulfate and concentrated. The residue was purified by silica gel chromatography with DCM/MeOH (9:1) to give (2-methylsulfanyl-4,5-dihydro-3H-benzo[b]azepin-8-yl)-carbamic acid tert-butyl ester (2.2 g, 7.2 mmol, 42%): $^1$H NMR (300 MHz, CDCl$_3$) δ 7.1 (m, 3H), 2.92 (t, 1H), 2.81 (t, 1H), 2.55 (s, 3H), 2.4 (q, 2H), 2.32 (q, 2H), 1.6 (s, 9H); MS (m/e) 307 (M+1).

1836d) A solution of (2-methylsulfanyl-4,5-dihydro-3H-benzo[b]azepin-8-yl)-carbamic acid tert-butyl ester (2.2 g, 7.2 mmol) and 2,2-dimethoxyethanamine (1.0 g, 9.5 mmol) in ethanol (200 mL) was heated in an oil bath at 100° C. for 14 hours. The mixture was concentrated and purified by silica gel chromatography with DCM/MeOH (9:1) to give [2-(2,2-dimethoxy-ethylamino)-4,5-dihydro-3H-benzo[b]azepin-8-yl]-carbamic acid tert-butyl ester (1.6 g, 4.4 mmol, 61%): $^1$H NMR (300 MHz, CDCl$_3$) δ 7.1 (m, 2H), 6.93 (s, 1H), 6.48 (s, 1H), 4.69 (t, 1H), 3.66 (d, 2H), 3.54 (s, 6H), 2.61 (t, 2H), 2.2 (br, 4H), 1.61 (s, 9H); MS (m/e) 364 (M+1).

1836e) A mixture of [2-(2,2-dimethoxy-ethylamino)-4,5-dihydro-3H-benzo[b]azepin-8-yl]-carbamic acid tert-butyl ester (1.6 g, 4.4 mmol) in 2:1 methanol/concentrated HCl (150 mL) was heated at 90° C. for 15 h. The solvent was evaporated to give a solid that was triturated with diethyl ether and dried to give 5,6-dihydro-4H-3,10b-diaza-benzo[e]azulen-9-ylamine as an HCl salt (703 mg, 3.5 mmol, 80%): $^1$H NMR (300 MHz, CD$_3$OD) δ 7.98 (d, 1H), 7.7 (m, 3H), 7.60 (dd, 1H), 3.04 (t, 2H), 2.79 (t, 2H), 2.48 (pent, 2H); MS (m/e) 200 (M+1).

1836f) Following a procedure analogous to Example 1741e, 5,6-dihydro-4H-3,10b-diaza-benzo[e]azulen-9-ylamine and 2-(2,5-dichloro-pyrimidin-4-ylamino)-N-methyl-benzamide was converted to 2-[5-chloro-2-(5,6-dihydro-4H-3,10b-diaza-benzo[e]azulen-9-ylamino)-pyrimidin-4-ylamino]-N-methyl-benzamide: $^1$H NMR (300 MHz, CD$_3$OD) δ 8.59 (d, 1H), 8.13 (s, 1H), 7.90 (d, 1H), 7.64 (dd, 1H), 7.45 (dd, 1H), 7.30 (d, 1H), 7.19 (d, 1H), 7.13 (dd, 1H), 7.05 (dd, 1H), 6.94 (d, 1H), 2.93 (s, 3H), 2.77 (t, 2H), 2.57 (t, 2H), 2.27 (pent, 2H); MS (m/e) 460 (M+1).

Example 1837

2-[5-Chloro-2-(5,6-dihydro-4H-3,10b-diaza-benzo[e]azulen-9-ylamino)-pyrimidin-4-ylamino]-3-fluoro-N-methyl-benzamide Following a procedure analogous to Example 1741e, 5,6-dihydro-4H-3,10b-diaza-benzo[e]azulen-9-ylamine and 2-(2,5-dichloro-pyrimidin-4-ylamino)-3-fluoro-N-methyl-benzamide were converted to 2-[5-chloro-2-(5,6-dihydro-4H-3,10b-diaza-benzo[e]azulen-9-ylamino)-pyrimidin-4-ylamino]-3-fluoro-N-methyl-benzamide: $^1$H NMR (300 MHz, CD$_3$OD) δ 8.04 (s, 1H), 7.60 (d, 1H), 7.31 (d, 1H), 7.18 (td, 1H), 7.1 (m, 3H), 6.98 (d, 1H), 6.83 (t, 1H), 2.81 (s, 3H), 2.65 (t, 2H), 2.44 (t, 2H), 2.16 (pent, 2H); $^{19}$F NMR (282 MHz, CD$_3$OD) δ −116.8; MS (m/e) 478 (M+1).

Example 1838

3-[5-Chloro-2-(5,6-dihydro-4H-3,10b-diaza-benzo[e]azulen-9-ylamino)-pyrimidin-4-ylamino]-4-methyl-thiophene-2-carboxylic acid methylamide Following a procedure analogous to Example 1741e, 5,6-dihydro-4H-3,10b-diaza-benzo[e]azulen-9-ylamine and 3-(2,5-dichloro-pyrimidin-4-ylamino)-4-methyl-thiophene-2-carboxylic acid methylamide were converted to 3-[5-chloro-2-(5,6-dihydro-4H-3,10b-diaza-benzo[e]azulen-9-ylamino)-pyrimidin-4-ylamino]-4-methyl-thiophene-2-carboxylic acid methylamide: $^1$H NMR (300 MHz, CD$_3$OD) δ 8.05 (s, 1H), 7.54 (d, 1H), 7.25 (dd, 1H), 7.12 (d, 1H), 7.05 (d, 1H), 6.97 (d, 2H), 2.82 (s, 3H), 2.70 (t, 2H), 2.45 (t, 2H), 2.18 (pent, 2H), 2.09 (s, 3H); MS (m/e) 480 (M+1).

Example 1839

2-[5-Chloro-2-(5,6-dihydro-4H-3,10b-diaza-benzo[e]azulen-9-ylamino)-pyrimidin-4-ylamino]-3-chloro-N-methyl-benzamide Following a procedure analogous to Example 1741e, 5,6-dihydro-4H-3,10b-diaza-benzo[e]azulen-9-ylamine and 2-(2,5-dichloro-pyrimidin-4-ylamino)-3-chloro-N-methyl-benzamide were converted to 2-[5-chloro-2-(5,6-dihydro-4H-3,10b-diaza-benzo[e]azulen-9-ylamino)-pyrimidin-4-ylamino]-3-chloro-N-methyl-benzamide. $^1$H NMR (300 MHz, CD$_3$OD) δ 8.09 (s, 1H), 7.59 (d, 1H), 7.38 (dd, 1H), 7.27 (dd, 1H), 7.1 (m, 4H), 7.01 (d, 1H), 2.77 (s, 3H), 2.66 (t, 2H), 2.45 (t, 2H), 2.18 (pent, 2H); MS (m/e) 494 (M+1).

Example 1840

3-[5-Chloro-2-(5,6-dihydro-4H-3,10b-diaza-benzo[e]azulen-9-ylamino)-pyrimidin-4-ylamino]-thiophene-2-carboxylic acid methylamide 100a) Following a procedure analogous to Example 1741e, 5,6-dihydro-4H-3,10b-diaza-benzo[e]azulen-9-ylamine and 3-(2,5-dichloro-pyrimidin-4-ylamino)-thiophene-2-carboxylic acid methylamide were converted to 3-[5-chloro-2-(5,6-dihydro-4H-3,10b-diaza-benzo[e]azulen-9-ylamino)-pyrimidin-4-ylamino]-thiophene-2-carboxylic acid methylamide. HCl salt: $^1$H NMR (300 MHz, CD$_3$OD) δ 8.25 (s, 1H), 8.08 (d, 1H), 7.85 (s, 1H), 7.81 (d, 1H), 7.68 (d, 1H), 7.65 (s, 2H), 7.51 (d, 1H), 3.07 (t, 2H), 2.91 (s, 3H), 2.80 (t, 2H), 2.50 (pent, 2H); MS (m/e) 466 (M+1).

Example 1841

2-[5-Chloro-2-(5,6-dihydro-4H-3,10b-diaza-benzo[e]azulen-9-ylamino)-pyrimidin-4-ylamino]-5-fluoro-N-methyl-benzamide Following a procedure analogous to Example 1741e, 5,6-dihydro-4H-3,10b-diaza-benzo[e]azulen-9-ylamine and 2-(2,5-dichloro-pyrimidin-4-ylamino)-5-fluoro-N-methyl-benzamide was converted to 2-[5-chloro-2-(5,6-dihydro-4H-3,10b-diaza-benzo[e]azulen-9-ylamino)-pyrimidin-4-ylamino]-5-fluoro-N-methyl-benzamide: $^1$H NMR (300 MHz, CD$_3$OD) δ 8.11 (s, 1H), 7.90 (d, 1H), 7.4 (m, 2H), 7.28 (d, 1H), 7.19 (d, 1H), 6.95 (d, 1H), 2.91 (s, 3H), 2.76 (t, 2H), 2.55 (t, 2H), 2.25 (pent, 2H); $^{19}$F NMR (282 MHz, CD$_3$OD) 6-121.1; MS (m/e) 478 (M+1).

Example 1842

5-Chloro-N*2*-(5,6-dihydro-4H-3,10b-diaza-benzo[e]azulen-9-yl)-N*4*-[2-fluoro-6-(propane-2-sulfonyl)-phenyl]-pyrimidine-2,4-diamine Following a procedure analogous to Example 1741e, 5,6-dihydro-4H-3,10b-diaza-benzo[e]azulen-9-ylamine and (2,5-dichloro-pyrimidin-4-yl)-[2-fluoro-6-(propane-2-sulfonyl)-phenyl]-amine was converted to 5-chloro-N*2*-(5,6-dihydro-4H-3,10b-diaza-benzo[e]azulen-9-yl)-N*4*-[2-fluoro-6-(propane-2-sulfonyl)-phenyl]-pyrimidine-2,4-diamine. TFA salt: $^1$H NMR (300 MHz, CD$_3$OD) δ 8.19 (s, 1H), 7.76 (m, 1H), 7.70 (d, 1H), 7.67 (s, 2H), 7.5 (m, 3H), 7.24 (d, 1H), 3.3 (m, 1H), 2.95 (t, 2H), 2.60 (t, 2H), 2.38 (pent, 2H), 1.19 (d, 6H); $^{19}$F NMR (282 MHz, CD$_3$OD) δ −77.4, −114.8 (d); MS (m/e) 527 (M+1).

Example 1843

2-[5-Chloro-2-(1-methyl-5,6-dihydro-4H-3,10b-diaza-benzo[e]azulen-9-ylamino)-pyrimidin-4-ylamino]-3-fluoro-N-methyl-benzamide 1843a) A solution of 2,2-dimethoxy-propionamide (5 g, 37.5 mmol) and borane-dimethylsulfide (70 mmol) in THF (200 mL) was heated at 90° C. for 8 h. The mixture was carefully quenched with methanol (50 mL) at 0° C., and then concentrated. The mixture was shaken with ether/water in a separatory funnel and the organic layer separated. The organic phase was dried over sodium sulfate and concentrated to give 2,2-dimethoxy-propylamine (5 g): $^1$H NMR (300 MHz, CDCl$_3$) δ 3.6 (t, 2H), 3.4 (s, 6H), 3.2 (d, 2H), 1.4 (s, 3H).

1843b) Following a procedure analogous to Example 1836d, (2-methylsulfanyl-4,5-dihydro-3H-benzo[b]azepin-8-yl)-carbamic acid tert-butyl ester and 2,2-dimethoxy-propylamine were converted to [2-(2,2-dimethoxy-propylamino)-4,5-dihydro-3H-benzo[b]azepin-8-yl]-carbamic acid tert-butyl ester: $^1$H NMR (300 MHz, CD$_3$OD) δ 7.97 (s, 1H), 7.2 (br, 2H), 4.1 (d, 1H), 3.9 (d, 1H), 3.3 (s, 6H), 2.6 (m, 4H), 2.3 (m, 2H), 1.7 (s, 3H), 1.5 (s, 9H). MS (m/e) 378 (M+1).

1843c) Following a procedure analogous to Example 1836e, [2-(2,2-dimethoxy-propylamino)-4,5-dihydro-3H-benzo[b]azepin-8-yl]-carbamic acid tert-butyl ester was converted to 1-methyl-5,6-dihydro-4H-3,10b-diaza-benzo[e]azulen-9-ylamine. HCl salt: $^1$H NMR (400 MHz, CD$_3$OD) δ 7.8 (d, 2H), 7.64 (d, 1H), 7.47 (s, 1H), 3.2 (br, 1H), 2.9 (br, 1H), 2.8 (br, 1H), 2.7 (br, 1H), 2.43 (s, 3H), 2.4 (br, 3H); MS (m/e) 214 (M+1).

1843d) Following a procedure analogous to Example 1741e, 1-methyl-5,6-dihydro-4H-3,10b-diaza-benzo[e]azulen-9-ylamine and 2-(2,5-dichloro-pyrimidin-4-ylamino)-3-fluoro-N-methyl-benzamide was converted to 2-[5-chloro-2-(1-methyl-5,6-dihydro-4H-3,10b-diaza-benzo[e]azulen-9-ylamino)-pyrimidin-4-yl amino]-3-fluoro-N-methyl-benzamide. $^1$H NMR (300 MHz, CD$_3$OD) δ 8.08 (s, 1H), 7.6

(s, 1H), 7.29 (d, 1H), 7.16 (d, 2H), 7.1 (m, 1H), 6.77 (s, 1H), 6.69 (t, 1H), 2.83 (s, 3H), 2.6-2.1 (m, 6H), 2.08 (s, 3H); $^{19}$F NMR (282 MHz, CD$_3$OD) δ −116.9; MS (m/e) 492 (M+1).

Example 1844

2-[5-Chloro-2-(5,6-dihydro-4H-1,3a-diaza-benzo[e]azulen-9-ylamino)-pyrimidin-4-ylamino]-3-fluoro-N-methyl-benzamide 1844a) Following a procedure analogous to Example 1794b, 2,3,4,5-tetrahydro-benzo[c]azepin-1-one was converted to 8-nitro-2,3,4,5-tetrahydro-benzo[c]azepin-1-one: $^1$H NMR (300 MHz, CDCl$_3$) δ 8.58 (d, 1H), 8.31 (dd, 1H), 7.43 (d, 1H), 3.2 (q, 2H), 3.0 (t, 2H), 2.17 (pent, 2H).

1844b) Following a procedure analogous to Example 1836b, 8-nitro-2,3,4,5-tetrahydro-benzo[c]azepin-1-one was converted to 8-nitro-2,3,4,5-tetrahydro-benzo[c]azepine-1-thione: $^1$H NMR (300 MHz, CDCl$_3$) δ 8.76 (d, 1H), 8.22 (dd, 1H), 7.34 (d, 1H), 3.28 (q, 2H), 2.93 (t, 2H), 2.21 (pent, 2H); MS (m/e) 223 (M+1).

1844c) A solution of 8-nitro-2,3,4,5-tetrahydro-benzo[c]azepine-1-thione (2 g, 9 mmol) and 2,2-dimethoxy-ethylamine (4.7 g, 45 mmol, 5.0 eq.) in THF (100 mL) was treated with Hg(OAc)$_2$ (4.3 g, 13.5 mmol, 1.5 eq.) at 5° C. The mixture was warmed to 25° C. and stirred for 2 hours, then concentrated. The residue was dissolved in toluene/water (11:1, 150 mL) and treated with p-toluenesulfonic acid (0.76 g, 4 mmol). This mixture was then heated at 65° C. for 24 h and subsequently concentrated under vacuum. The resulting residue was dissolved in methanol/HCl solution (2:1, 100 mL) and heated at 90° C. for 12 hours. Solvent evaporation and purification with silica gel chromatography (DCM/MeOH (9:1)) gave 9-nitro-5,6-dihydro-4H-1,3a-diaza-benzo[e]azulene (300 mg, 1.3 mmol, 15%). $^1$H NMR (300 MHz, CD$_3$OD) δ 8.50 (d, 1H), 8.23 (dd, 1H), 7.61 (d, 1H), 7.32 (d, 1H), 7.12 (d, 1H), 4.05 (t, 2H), 2.85 (t, 2H), 2.42 (pent, 2H); MS (m/e) 230 (M+1).

1844d) Following a procedure analogous to Example 1791b, 9-nitro-5,6-dihydro-4H-1,3a-diaza-benzo[e]azulene was converted to 5,6-dihydro-4H-1,3a-diaza-benzo[e]azulen-9-ylamine: $^1$H NMR (300 MHz, CD$_3$OD) δ 7.18 (d, 1H), 7.04 (d, 1H), 7.0 (m, 2H), 6.73 (dd, 1H), 3.94 (t, 2H), 2.56 (t, 2H), 2.25 (pent, 2H); MS (m/e) 200 (M+1).

1844e) Following a procedure analogous to Example 1741e, 5,6-dihydro-4H-1,3a-diaza-benzo[e]azulen-9-ylamine and 2-(2,5-dichloro-pyrimidin-4-ylamino)-3-fluoro-N-methyl-benzamide were converted to 2-[5-chloro-2-(5,6-dihydro-4H-1,3a-diaza-benzo[e]azulen-9-ylamino)-pyrimidin-4-ylamino]-3-fluoro-N-methyl-benzamide. $^1$H NMR (300 MHz, CD$_3$OD) δ 8.04 (s, 1H), 7.66 (d, 1H), 7.41 (dd, 1H), 7.31 (d, 1H), 7.26 (d, 1H), 7.17 (d, 1H), 7.1 (m, 2H), 6.94 (t, 1H), 3.93 (t, 2H), 2.82 (s, 3H), 2.58 (t, 2H), 2.28 (pent, 2H); MS (m/e) 478 (M+1).

Example 1845

2-[5-Chloro-2-(5,6-dihydro-4H-1,3a-diaza-benzo[e]azulen-9-ylamino)-pyrimidin-4-ylamino]-3-chloro-N-methyl-benzamide Following a procedure analogous to Example 1741e, 5,6-dihydro-4H-1,3a-diaza-benzo[e]azulen-9-ylamine and 2-(2,5-dichloro-pyrimidin-4-ylamino)-3-chloro-N-methyl-benzamide was converted to 2-[5-chloro-2-(5,6-dihydro-4H-1,3a-diaza-benzo[e]azulen-9-ylamino)-pyrimidin-4-ylamino]-3-chloro-N-methyl-benzamide. TFA salt: $^1$H NMR (300 MHz, CD$_3$OD) δ 8.17 (s, 1H), 7.81 (d, 1H), 7.77 (d, 1H), 7.71 (d, 1H), 7.4 (m, 3H), 7.3 (m, 2H), 4.16 (t, 2H), 2.81 (s, 3H), 2.70 (t, 2H), 2.46 (pent, 2H); MS (m/e) 494 (M+1).

Example 1846

3-[5-Chloro-2-(5,6-dihydro-4H-1,3a-diaza-benzo[e]azulen-9-ylamino)-pyrimidin-4-ylamino]-4-methyl-thiophene-2-carboxylic acid methylamide Following a procedure analogous to Example 1741e, 5,6-dihydro-4H-1,3a-diaza-benzo[e]azulen-9-ylamine and 3-(2,5-dichloro-pyrimidin-4-ylamino)-4-methyl-thiophene-2-carboxylic acid methylamide were converted to 3-[5-chloro-2-(5,6-dihydro-4H-1,3a-diaza-benzo[e]azulen-9-ylamino)-pyrimidin-4-ylamino]-4-methyl-thiophene-2-carboxylic acid methylamide. TFA salt: $^1$H NMR (300 MHz, CD$_3$OD) δ 8.19 (s, 1H), 7.77 (d, 2H), 7.68 (d, 1H), 7.49 (dd, 1H), 7.34 (d, 1H), 7.09 (s, 1H), 4.22 (t, 2H), 2.81 (s, 3H), 2.73 (t, 2H), 2.48 (pent, 2H), 2.02 (s, 3H); MS (m/e) 480 (M+1).

Example 1847

2-[5-Chloro-2-(5,6-dihydro-4H-1,3a-diaza-benzo[e]azulen-9-ylamino)-pyrimidin-4-ylamino]-5-fluoro-N-methyl-benzamide Following a procedure analogous to Example 1741e, 5,6-dihydro-4H-1,3a-diaza-benzo[e]azulen-9-ylamine and 2-(2,5-dichloro-pyrimidin-4-ylamino)-5-fluoro-N-methyl-benzamide was converted to 2-[5-chloro-2-(5,6-dihydro-4H-1,3a-diaza-benzo[e]azulen-9-ylamino)-pyrimidin-4-ylamino]-5-fluoro-N-methyl-benzamide. TFA salt: $^1$H NMR (300 MHz, CD$_3$OD) δ 8.43 (dd, 1H), 8.19 (s, 1H), 8.12 (d, 1H), 7.76 (d, 1H), 7.69 (dd, 1H), 7.61 (d, 1H), 7.5 (m, 2H), 7.03 (td, 1H), 4.26 (t, 2H), 2.92 (s, 3H), 2.81 (t, 2H), 2.52 (pent, 2H); $^{19}$F NMR (282 MHz, CD$_3$OD) δ −77.9, −119.1; MS (m/e) 478 (M+1).

Example 1848

2-[2-(4-Acetyl-2-oxo-2,3,4,5-tetrahydro-1H-benzo[e][1,4]diazepin-8-ylamino)-5-chloro-pyrimidin-4-ylamino]-3-fluoro-N-methyl-benzamide 1848a) A solution of 2-bromo-5-nitroaniline (10 g, 46 mmol) in DMF (100 mL) and pyridine (40 mL, 490 mmol) was treated with copper(I) cyanide (11.5 g, 128 mmol). The mixture was heated at 160° C. for 2 days under a reflux condenser. After the mixture had cooled to room temperature, it was filtered through celite and washed with ethyl acetate. Concentration and silica gel chromatography using methylene chloride gave 5.57 g of 2-amino-4-nitro-benzonitrile (74%): $^1$H NMR (300 MHz, CDCl$_3$) δ 7.72 (d, 1H), 7.67 (m, 2H), 4.9 (br, 2H); MS (m/e): 164.1 (M+1).

1848b) Borane-dimethyl sulfide (40 mL, 80 mmol) was added dropwise to a stirring solution of 2-amino-4-nitro-benzonitrile (2.27 g, 14 mmol) in dry THF (50 mL) at room temperature. The mixture was stirred at same temperature for 3 hours, and then carefully quenched with 1N aqueous HCl. The mixture was made basic (pH>11) with 4N sodium hydroxide and extracted with methylene chloride. The organic phase was dried over sodium sulfate, filtered and concentrated to provide 1.75 g of 2-aminomethyl-5-nitro-phenylamine (75%): $^1$H NMR (300 MHz, CDCl$_3$) δ7.6 (m, 2H), 7.25 (d, 1H), 5.1 (br, 2H), 4.1 (s, 3H); MS (m/e): 168.1 (M+1).

1848c) To a solution of 2-aminomethyl-5-nitro-phenylamine (2.84 g, 17 mmol) in dry THF (150 mL) and triethylamine (12 mL, 85 mmol) was added tert-butyl bromoacetate (5 mL, 34 mmol). The mixture solution was stirred at room temperature for 16 hours and concentrated. Chromatography of the resulting residue on silica gel with methylene chloride and methanol (50:1) gave 2.15 g of (2-amino-4-nitro-benzylamino)-acetic acid tert-butyl ester (45%): $^1$H NMR (300 MHz, CDCl$_3$) δ 7.58 (dd, 1H), 7.55 (5, 1H), 7.22 (d, 1H), 5.2 (br, 2H) 3.95 (s, 2H), 3.39 (s, 2H), 1.58 (s, 9H); MS (m/e): 282.3 (M+1).

1848d) A solution of (2-amino-4-nitro-benzylamino)-acetic acid tert-butyl ester (234 mg, 0.8 mmol) in acetic acid (20 mL) was stirred at 120° C. for 16 hours. The mixture was concentrated and chromatographed on silica gel with methylene chloride and methanol (30:1) to give 115 mg of 4-acetyl-8-nitro-1,3,4,5-tetrahydro-benzo[e][1,4]diazopin-2-one (55%): $^1$H NMR (300 MHz, CDCl$_3$) δ 7.9 (m, 2H), 7.4 (dd, 1H), 4.65 (s, 2H), 4.54 (s, 1H), 4.3 (s, 1H), 2.05 (s, 3H); MS (m/e): 250.2 (M+1).

1848e) Following a procedure analogous to Example 1791b, 4-acetyl-8-nitro-1,3,4,5-tetrahydro-benzo[e][1,4]diazopin-2-one was converted to 4-acetyl-8-amino-1,3,4,5-tetrahydro-benzo[e][1,4]diazopin-2-one: $^1$H NMR (300 MHz, CDCl$_3$) δ 7.18 (dd, 1H), 6.65 (dd, 1H), 6.55 (s, 1H), 4.65 (s, 1H), 4.6 (s, 1H), 4.48 (s, 1H), 4.25 (s, 1H), 2.3 (s, 3H); MS (m/e): 220.3 (M+1).

1848f) Following a procedure analogous to Example 1741e, 4-acetyl-8-amino-1,3,4,5-tetrahydro-benzo[e][1,4]diazopin-2-one and 2-(2,5-dichloropyrimidin-4-ylamino)-3-fluoro-N-methylbenzamide was converted to 2-[2-(4-acetyl-2-oxo-2,3,4,5-tetrahydro-1H-benzo[e][1,4]diazepin-8-ylamino)-5-chloro-pyrimidin-4-ylamino]-3-fluoro-N-methyl-benzamide: $^1$H NMR (300 MHz, CDCl$_3$) δ 8.0 (s, 1H), 7.45 (m, 1H), 7.25 (m, 3H), 6.9 (m, 2H), 4.49 (s, 1H), 4.41 (s, 2H), 4.07 (s, 1H), 2.85 (s, 3H), 2.07 (s, 3H); MS (m/e): 498.2 (M+1).

Example 1849

3-[2-(4-Acetyl-2-oxo-2,3,4,5-tetrahydro-1H-benzo[e][1,4]diazepin-8-ylamino)-5-chloro-pyrimidin-4-ylamino]-thiophene-2-carboxylic acid methyl amide Following a procedure analogous to Example 1741e, 4-acetyl-8-amino-1,3,4,5-tetrahydro-benzo[e][1,4]diazopin-2-one and 3-(2,5-dichloro-pyrimidin-4-ylamino)-thiophene-2-carboxylic acid methylamide were converted to 3-[2-(4-acetyl-2-oxo-2,3,4,5-tetrahydro-1H-benzo[e][1,4]diazepin-8-ylamino)-5-chloro-pyrimidin-4-ylamino]-thiophene-2-carboxylic acid methylamide: $^1$H NMR (300 MHz, DMSO) δ 11.67 (s, 1H), 10.15 (d, 1H), 9.62 (s, 1H), 8.45 (t, 1H), 8.25 (s, 1H), 7.7 (dd, 1H), 7.45 (d, 1H), 7.3 (m, 2H), 7.1 (s, 1H), 6.95 (s, 1H), 4.55 (s, 1H), 4.46 (s, 1H), 4.25 (s, 1H), 4.2 (s, 1H), 2.78 (d, 2H), 2.05 (d, 3H); MS (m/e): 486.2 (M+1).

Example 1850

3-[2-(4-Acetyl-2-oxo-2,3,4,5-tetrahydro-1H-benzo[e][1,4]diazepin-8-ylamino)-5-chloro-pyrimidin-4-ylamino]-4-methyl-thiophene-2-carboxylic acid methylamide Following a procedure analogous to Example 1741e, 4-acetyl-8-amino-1,3,4,5-tetrahydro-benzo[e][1,4]diazopin-2-one and 3-(2,5-dichloro-pyrimidin-4-ylamino)-4-methyl-thiophene-2-carboxyllic acid methylamide were converted to 3-[2-(4-acetyl-2-oxo-2,3,4,5-tetrahydro-1H-benzo[e][1,4]diazepin-8-ylamino)-5-chloro-pyrimidin-4-ylamino]-4-methyl-thiophene-2-carboxylic acid methylamide: $^1$H NMR (300 MHz, CDCl$_3$) δ 8.15 (s, 1H), 7.58 (s, 1H), 7.25 (d, 1H), 7.15 (dd, 1H), 6.9 (dd, 1H), 7.1 (s, 1H), 4.65 (s, 1H), 4.6 (s, 1H), 4.57 (s, 1H), 4.25 (s, 1H), 3.0 (d, 3H), 2.22 (dd, 3H), 2.16 (s, 3H); MS (m/e): 500.2 (M+1).

Example 1851

2-[2-(4-Acetyl-1-ethyl-2-oxo-2,3,4,5-tetrahydro-1H-benzo[e][1,4]diazepin-8-ylamino)-5-chloro-pyrimidin-4-ylamino]-3-fluoro-N-methyl-benzamide 1851a) A mixture of 4-acetyl-8-nitro-1,3,4,5-tetrahydro-benzo[e][1,4]diazopin-2-one (0.6 g, 2.4 mmol), potassium carbonate (1.0 g, 7.2 mmol) and iodoethane (0.58 mL, 7.2 mmol) in 15 mL of DMF was stirred at 60° C. for 4 h. Concentration and chromatography on silica gel with methylene chloride and methanol (30:1) gave 0.55 g of 4-acetyl-1-ethyl-8-nitro-1,3,4,5-tetrahydro-benzo[e][1,4]diazopin-2-one (83%): $^1$H NMR (300 MHz, CDCl$_3$) δ 8.24 (d, 1H), 8.2 (dd, 1H), 7.65 (d, 1H), 4.7 (d, 2H), 4.14 (q, 2H), 4.12 (s, 2H), 2.3 (s, 3H), 1.3 (t, 3H); MS (m/e): 278.2 (M+1).

1851b) Following a procedure analogous to Example 1791b, 4-acetyl-1-ethyl-8-nitro-1,3,4,5-tetrahydro-benzo[e][1,4]diazopin-2-one was converted to 4-acetyl-8-amino-1-ethyl-1,3,4,5-tetrahydro-benzo[e][1,4]diazepin-2-one: $^1$H NMR (300 MHz, CDCl$_3$) δ 7.2 (dd, 1H), 6.73 (br, 2H), 4.5 (ss, 2H), 4.1 (s, 2H), 4.65 (s, 1H), 4.0 (br, 2H), 2.28 (s, 3H), 1.28 (t, 3H); MS (m/e): 248.1 (M+1).

1851c) Following a procedure analogous to Example 1741e, 4-acetyl-1-ethyl-8-nitro-1,3,4,5-tetrahydro-benzo[e][1,4]diazopin-2-one and 2-(2,5-dichloropyrimidin-4-ylamino)-3-fluoro-N-methylbenzamide were converted to 2-[2-(4-acetyl-1-ethyl-2-oxo-2,3,4,5-tetrahydro-1H-benzo[e][1,4]diazepin-8-ylamino)-5-chloro-pyrimidin-4-ylamino]-3-fluoro-N-methyl-benzamide: $^1$H NMR (300 MHz, CDCl$_3$) δ 9.12 (s, 1H), 8.08 (s, 1H), 7.6 (ss, 1H), 7.32 (t, 1H), 7.22 (m, 3H), 7.1 (d, 1H), 6.23 (br, 1H), 4.4 (ss, 2H), 3.88 (s, 2H), 3.75 (br, 2H), 2.92 (d, 3H), 2.15 (ss, 3H), 1.22 (t, 3H); MS (m/e): 526.2 (M+1).

Example 1852

3-[2-(4-Acetyl-1-ethyl-2-oxo-2,3,4,5-tetrahydro-1H-benzo[e][1,4]diazepin-8-ylamino)-5-chloro-pyrimidin-4-ylamino]-4-methyl-thiophene-2-carboxylic acid-methylamide Following a procedure analogous to Example 1741e, 4-acetyl-1-ethyl-8-nitro-1,3,4,5-tetrahydro-benzo[e][1,4]diazopin-2-one and 3-(2,5-dichloro-pyrimidin-4-ylamino)-4-methyl-thiophene-2-carboxylic acid methylamide were converted to 3-[2-(4-acetyl-2-oxo-2,3,4,5-tetrahydro-1H-benzo[e][1,4]diazepin-8-ylamino)-5-chloro-pyrimidin-4-ylamino]-4-methyl-thiophene-2-carboxylic acid methylamide: $^1$H NMR (300 MHz, CDCl$_3$) δ 9.18 (s, 1H), 8.2 (s, 1H), 7.8 (s, 1H), 7.38 (dd, 2H), 7.22 (d, 1H), 7.1 (d, 1H), 6.08 (d, 1H), 4.55 (s, 2H), 4.12 (s, 2H), 3.85 (br, 2H), 3.05 (d, 3H), 2.30 (s, 3H), 2.18 (s, 3H), 1.15 (t, 3H); MS (m/e): 528.2 (M+1).

Example 1853

3-[2-(4-Acetyl-1-ethyl-2-oxo-2,3,4,5-tetrahydro-1H-benzo[e][1,4]diazepin-8-ylamino)-5-chloro-pyrimidin-4-ylamino]-thiophene-2-carboxylic acid methylamide Following a procedure analogous to Example 1741e, 4-acetyl-1-ethyl-8-nitro-1,3,4,5-tetrahydro-benzo[e][1,4]diazopin-2-one and 3-(2,5-dichloro-pyrimidin-4-ylamino)-thiophene-2-carboxyllic acid methylamide were converted to 3-[2-(4-acetyl-1-ethyl-2-oxo-2,3,4,5-tetrahydro-1H-benzo[e][1,4]diazepin-8-ylamino)-5-chloro-pyrimidin-4-ylamino]-thiophene-2-carboxylic acid methylamide: $^1$H NMR (300 MHz, DMSO) δ 11.7 (s, 1H), 9.75 (s, 1H), 8.45 (d, 1H), 8.33 (s, 1H), 8.3 (d, 1H), 7.84 (s, 1H), 7.7 (d, 1H), 7.58 (t, 1H), 7.5 (d, 1H), 7.35 (d, 1H), 4.42 (s, 2H), 3.9 (s, 2H), 3.82 (q, 2H), 2.78 (d, 3H), 3.0 (d, 3H), 2.1 (s, 3H), 1.1 (t, 3H); MS (m/e): 514.3 (M+1).

Example 1854

2-[2-(4-Acetyl-1-ethyl-2-oxo-2,3,4,5-tetrahydro-1H-benzo[e][1,4]diazepin-8-ylamino)-5-chloro-pyrimidin-4-ylamino]-3-chloro-N-methyl-benzamide Following a procedure analogous to Example 1741e, 4-acetyl-1-ethyl-8-nitro-1,3,4,5-tetrahydro-benzo[e][1,4]diazopin-2-one and 2-(2,5-dichloropyrimidin-4-ylamino)-3-chloro-N-methylbenzamide were converted to 2-[2-(4-acetyl-1-ethyl-2-oxo-2,3,4,5-tetrahydro-1H-benzo[e][1,4]diazepin-8-ylamino)-5-chloro-pyrimidin-4-ylamino]-3-chloro-N-methyl-benzamide: $^1$H NMR (300 MHz, CDCl$_3$) δ 8.4 (s, 1H), 8.22 (s, 1H), 7.65 (m, 3H), 7.38 (m, 2H), 7.22 (m, 2H), 6.32 (br, 1H), 4.5 (s, 2H), 4.05 (s, 2H), 3.9 (br, 2H), 2.95 (d, 3H), 2.3 (s, 3H), 1.18 (t, 3H); MS (m/e): 542.3 (M+1).

Example 1855

2-[2-(4-Acetyl-1-ethyl-2-oxo-2,3,4,5-tetrahydro-1H-benzo[e][1,4]diazepin-8-ylamino)-5-chloro-pyrimidin-4-ylamino]-N-methyl-benzamide Following a procedure analogous to Example 1741e, 4-acetyl-1-ethyl-8-nitro-1,3,4,5-tetrahydro-benzo[e][1,4]diazopin-2-one and 2-(2,5-dichloropyrimidin-4-ylamino)-N-methylbenzamide were converted to 2-[2-(4-acetyl-1-ethyl-2-oxo-2,3,4,5-tetrahydro-1H-benzo[e][1,4]diazepin-8-ylamino)-5-chloro-pyrimidin-4-ylamino]-N-methyl-benzamide: $^1$H NMR (300 MHz, CDCl$_3$) δ 11.3 (s, 1H), 8.65 (d, 1H), 8.22 (s, 1H), 7.93 (s, 1H), 7.62 (d, 1H), 7.4 (m, 4H), 7.2 (t, 1H), 6.5 (br, 1H), 4.5 s (s, 2H), 4.08 (s, 2H), 3.92 (q, 2H), 3.12 (d, 3H), 2.3 (s, 3H), 1.2 (t, 3H); MS (m/e): 508.4 (M+

Example 1856

3-[5-Chloro-2-(1,4-diethyl-2-oxo-2,3,4,5-tetrahydro-1H-benzo[e][1,4]diazepin-8-ylamino)-pyrimidin-4-ylamino]-thiophene-2-carboxylic acid methylamide 1856a) A solution of 3-[2-(4-acetyl-1-ethyl-2-oxo-2,3,4,5-tetrahydro-1H-benzo[e][1,4]diazepin-8-ylamino)-5-chloro-pyrimidin-4-ylamino]-thiophene-2-carboxylic acid methylamide (157 mg, 0.3 mmol) in 12 mL of 40% methylamine/water and 3 mL of 2M methylamine/THF) was heated in a sealed tube at 120° C. for 16 hours. Chromatography of the concentrated residue on TLC plates with methylene chloride and methanol (100:9) gave 43 mg of 3-[5-chloro-2-(1-ethyl-2-oxo-2,3,4,5-tetrahydro-1H-benzo[e][1,4]diazepin-8-ylamino)-pyrimidin-4-ylamino]-thiophene-2-carboxylic acid methylamide (29%): $^1$H NMR (300 MHz, CD$_3$OD) δ 8.42 (d, 1H), 8.1 (s, 1H), 7.88 (s, 1H), 7.45 (m, 2H), 7.33 (d, 1H), 3.92 (m, 4H), 3.35 (s, 2H), 2.9 (s, 3H), 1.18 (t, 3H); MS (m/e): 472.1 (M+1).

1856b) Acetaldehyde (20 mg, 0.45 mmol) was added to a solution of 3-[5-chloro-2-(1-ethyl-2-oxo-2,3,4,5-tetrahydro-1H-benzo[e][1,4]diazepin-8-ylamino)-pyrimidin-4-ylamino]-thiophene-2-carboxylic acid methylamide (42.5 mg, 0.09 mmol) in THF:DCE (1:2) at 0° C. After 15 minutes, 100 mg of sodium triacetoxyborohydride was added and the mixture was stirred for 2 hours at 0° C. and 1 hour at room temperature. Evaporation and chromatography on preparative TLC with methylene chloride and methanol (100:7) gave 31 mg of 3-[5-chloro-2-(1,4-diethyl-2-oxo-2,3,4,5-tetrahydro-1H-benzo[e][1,4]diazepin-8-ylamino)-pyrimidin-4-ylamino]-thiophene-2-carboxylic acid methylamide (50%): $^1$H NMR (300 MHz, CD$_3$OD) δ 8.42 (d, 1H), 8.07 (s, 1H), 7.83 (s, 1H), 7.44 (d, 1H), 7.42 (s, 1H), 7.27 (d, 1H), 3.9 (q, 2H), 3.64 (s, 2H), 3.22 (s, 2H), 2.87 (s, 3H), 2.75 (q, 2H), 2.05 (s, 3H), 1.18 (m, 6H); MS (m/e): 500.4 (M+1).

Example 1857

8-[5-Chloro-4-(2-fluoro-6-methylcarbamoyl-phenylamino)-pyrimidin-2-ylamino]-2-oxo-1,2,3,5-tetrahydro-benzo[e][1,4]diazepine-4-carboxylic acid benzyl ester 1857a) Benzyl chloroformate (6.8 mL, 48 mmol) was added slowly to a solution of (2-amino-4-nitro-benzylamino)-acetic acid tert-butyl ester (9.08 g, 32 mmol) and triethylamine (13.5 mL, 97 mmol) in dry methylene chloride (300 mL) at 0° C. The mixture was stirred for 2 h and warmed to room temperature for another 1 h. The mixture was concentrated and chromatograph with hexanes and ethyl acetate to give [(2-amino-4-nitro-benzyl)-benzyloxycarbonyl-amino]-acetic acid tert-butyl ester (8.39 g) as a yellow solid (62%): $^1$H NMR (300 MHz, CDCl$_3$) δ 7.58 (br, 1H), 7.5 (d, 1H), 7.3 (br, 5H), 7.12 (d, 1H), 5.15 (s, 2H), 4.55 (s, 2H), 3.78 (s, 2H), 1.33 (s, 9H); MS (m/e): 416.3 (M+1).

1857b) Following a procedure analogous to Example 1848d, [(2-amino-4-nitro-benzyl)-benzyloxycarbonyl-amino]-acetic acid tert-butyl ester was converted to 8-nitro-2-oxo-1,2,3,5-tetrahydro-benzo[e][1,4]diazepine-4-carboxylic acid benzyl ester: $^1$H NMR (300 MHz, CDCl$_3$) δ 8.55 (d, 1H), 7.86 (dd, 1H), 7.8 (s, 1H), 7.45 (d, 1H), 7.3 (s, 3H) 7.18 (br, 1H), 5.1 (s, 1H), 5.06 (s, 1H), 4.63 (s, 2H), 4.5 (s, 1H), 4.45 (s, 1H); MS (m/e): 342.5 (M+1).

1857c) Following a procedure analogous to Example 1774c, 8-nitro-2-oxo-1,2,3,5-tetrahydro-benzo[e][1,4]diazepine-4-carboxylic acid benzyl ester was converted to 8-amino-2-oxo-1,2,3,5-tetrahydro-benzo[e][1,4]diazepine-4-carboxylic acid benzyl ester: $^1$H NMR (300 MHz, CDCl$_3$) δ 7.9 (m, 2H), 7.3 (s, 3H), 7.22 (m, 3H), 5.05 (s, 2H), 4.4 (m, 4H) 1.55 (br, 2H); MS (m/e): 312.4 (M+1).

1857d) Following a procedure analogous to Example 1741e, 8-amino-2-oxo-1,2,3,5-tetrahydro-benzo[e][1,4]diazepine-4-carboxylic acid benzyl ester and 2-(2,5-dichloropyrimidin-4-ylamino)-3-fluoro-N-methylbenzamide (31.4 mg, 0.1 mmol) were converted to 8-[5-chloro-4-(2-fluoro-6-methylcarbamoyl-phenylamino)-pyrimidin-2-ylamino]-2-oxo-1,2,3,5-tetrahydro-benzo[e][1,4]diazepine-4-carboxylic acid benzyl ester: $^1$H NMR (300 MHz, CDCl$_3$) δ 8.1 (s, 1H), 7.5 (d, 1H), 7.4 (br, 10H), 7.3 (d, 1H), 7.12 (m, 1H), 6.97 (m, 1H), 5.15 (s, 2H), 4.5 (dd, 2H), 4.37 (dd, 2H), 2.95 (d, 3H), 2.92 (d, 3H); MS (m/e): 590.3 (M+1).

Example 1858

2-[5-Chloro-2-(2-oxo-2,3,4,5-tetrahydro-1H-benzo[e][1,4]diazepin-8-ylamino)-pyrimidin-4-ylamino]-N-methyl-benzamide 1858a) Following a procedure analogous to Example 1741e, 8-amino-2-oxo-1,2,3,5-tetrahydro-benzo[e][1,4]diazepine-4-carboxylic acid benzyl ester and 2-(2,5-dichloro-pyrimidin-4-ylamino)-N-methylbenzamide were converted to 8-[5-chloro-4-(2-methylcarbamoyl-phenylamino)-pyrimidin-2-ylamino]-2-oxo-1,2,3,5-tetrahydro-benzo[e][1,4]diazepine-4-carboxylic acid benzyl ester: $^1$H NMR (300 MHz, CDCl$_3$) δ 10.98 (s, 1H), 8.47 (d, 1H), 8.05 (s, 1H), 7.95 (s, 1H), 7.66 (s, 1H), 7.4 (m, 6H), 7.1 (m, 3H), 6.32 (br, 1H), 5.06 (s, 2H), 4.5 (d, 2H), 4.4 (d, 2H), 3.0 (d, 3H); MS (m/e): 572.3 (M+1).

1858b) At 0° C., iodotrimethylsilane (12.3 mg, 0.06 mmol) was added slowly to a solution of 8-[5-chloro-4-(2-methylcarbamoyl-phenylamino)-pyrimidin-2-ylamino]-2-oxo-1,2,3,5-tetrahydro-benzo[e][1,4]diazepine-4-carboxylic acid benzyl ester (25 mg, 0.04 mmol) in methylene chloride (5 mL). The mixture solution was warmed to room temperature and stirred for 1 hour. The mixture was quenched with a few drops of methanol, stirred for 10 minutes and concentrated. The residue was treated with 1N HCl (0.5 mL), and then made basic (pH 10) with potassium carbonate. The mixture was extracted with methylene chloride and chloroform, and then dried over sodium sulfate. Chromatography of the crude solid with preparative TLC using methylene chloride and methanol (25:1) gave 6.3 mg of 2-[5-chloro-2-(2-oxo-2,3,4,5-tetrahydro-1H-benzo[e][1,4]diazepin-8-ylamino)-pyrimidin-4-ylamino]-N-methyl-benzamide (33%): $^1$H NMR (300 MHz, CDCl$_3$) δ 8.45 (d, 1H), 8.05 (s, 1H), 7.6 (q, 2H), 7.43 (t, 2H), 7.3 (dd, 1H), 7.13 (d, 2H), 4.0 (s, 2H), 3.43 (s, 2H), 2.92 (s, 3H); MS (m/e): 438.3 (M+1).

Example 1859

2-[2-(4-Benzyl-2-oxo-2,3,4,5-tetrahydro-1H-benzo[e][1,4]diazepin-8-ylamino)-5-chloro-pyrimidin-4-ylamino]-N-methyl-benzamide The side product 2-[2-(4-benzyl-2-oxo-2,3,4,5-tetrahydro-1H-benzo[e][1,4]diazepin-8-ylamino)-5-chloro-pyrimidin-4-ylamino]-N-methyl-benzamide was obtained from procedure 118b: $^1$H NMR (300 MHz, CDCl$_3$) δ 8.4 (d, 1H), 8.0 (s, 1H), 7.5 (br, 2H), 7.3 (m, 8H), 7.05 (m, 3H), 3.7 (s, 2H), 3.65 (s, 2H), 3.33 (s, 2H), 2.9 (d, 3H); MS (m/e): 528.2 (M+1).

Example 1860

2-[5-Chloro-2-(4-methanesulfonyl-2-oxo-2,3,4,5-tetrahydro-1H-benzo[e][1,4]diazepin-8-ylamino)pyrimidin-4-ylamino]-3-fluoro-N-methyl-benzamide 1860a) A solution of 8-[5-chloro-4-(2-fluoro-6-methylcarbamoyl-phenylamino)-pyrimidin-2-ylamino]-2-oxo-1,2,3,5-tetrahydro-benzo[e][1,4]diazepine-4-carboxylic acid benzyl ester (0.21 g, 0.36 mmol) in methyl sulfide (3.5 mL) and trifluoroacetic acid (11 mL) was stirred at room temperature for 16 hours. Concentration and chromatography on a silica gel with methylene chloride and methanol (20:1) gave 0.11 g of 2-[5-chloro-2-(2-oxo-2,3,4,5-tetrahydro-1H-benzo[e][1,4]diazepin-8-ylamino)-pyrimidin-4-ylamino]-3-fluoro-N-methyl-benzamide (68% yield): $^1$H NMR (300 MHz, CD$_3$OD) δ 8.18 (s, 1H), 7.45 (m, 4H), 7.27 (s, 2H), 4.24 (s, 2H), 3.65 (s, 2H), 2.84 (d, 3H); MS (m/e): 456.4 (M+1).

1860b) A solution of 2-[5-chloro-2-(2-oxo-2,3,4,5-tetrahydro-1H-benzo[e][1,4]diazepin-8-ylamino)-pyrimidin-4-ylamino]-3-fluoro-N-methyl-benzamide (99 mg, 0.22 mmol), pyridine (33 uL, 0.44 mmol) and methanesulfonic anhydride (38 mg, 0.22 mmol) in methylene chloride (5 mL) was stirred at 70° C. for 16 hours. Concentration and chromatography on preparative TLC with methylene chloride and methanol (25:1) gave 16.7 mg of 2-[5-chloro-2-(4-methanesulfonyl-2-oxo-2,3,4,5-tetrahydro-1H-benzo[e][1,4]diazepin-8-ylamino)pyrimidin-4-ylamino]-3-fluoro-N-methyl-benzamide (14%): $^1$H NMR (300 MHz, CDCl$_3$) δ 7.9 (s, 1H), 7.72 (br, 1H), 7.33 (d, 1H), 7.15 (m, 3H), 6.95 (s, 2H), 4.16 (s, 2H), 3.78 (s, 2H), 2.7 (s, 3H); MS (m/e): 534.2 (M+1).

Example 1861

2-{5-Chloro-2-[2-oxo-4-(3,3,3-trifluoro-propyl)-2,3,4,5-tetrahydro-1H-benzo[e][1,4]diazepin-8-ylamino]-pyrimidin-4-ylamino}-3-fluoro-N-methyl-benzamide A solution of 2-[5-chloro-2-(2-oxo-2,3,4,5-tetrahydro-1H-benzo[e][1,4]diazepin-8-ylamino)-pyrimidin-4-ylamino]-3-fluoro-N-methyl-benzamide (50 mg, 0.11 mmol), potassium carbonate (31 mg, 0.22 mmol) and 1-iodo-3,3,3-trifluoropropane (58 mg, 0.25 mmol) was heated at 115° C. in butanol (3 mL) for 24 hours. After evaporated solvent, chromatography of the crude solid on a TLC plate with methylene chloride and methanol (25:1) to give 15.6 mg of 2-{5-chloro-2-[2-oxo-4-(3,3,3-trifluoro-propyl)-2,3,4,5-tetrahydro-1H-benzo[e][1,4]diazepin-8-ylamino]-pyrimidin-4-ylamino}-3-fluoro-N-methyl-benzamide in 14% yield: $^1$H NMR (300 MHz, CDCl$_3$) δ 8.82 (s, 1H), 8.2 (s, 1H), 7.6 (m, 2H), 7.43 (m, 2H), 7.24 (s, 1H), 7.15 (d, 1H), 6.9 (d, 1H), 6.43 (d, 1H), 3.85 (s, 2H), 3.53 (s, 2H), 3.07 (d, 3H), 2.97 (m, 2H), 2.46 (m, 2H); MS (m/e): 552.2 (M+1).

Example 1862

2-{5-Chloro-2-[4-(2-methoxy-ethyl)-2-oxo-2,3,4,5-tetrahydro-1H-benzo[e][1,4]diazepin-8-ylamino]-pyrimidin-4-ylamino}-3-fluoro-N-methyl-benzamide Following a procedure analogous to Example 1861a, 2-[5-chloro-2-(2-oxo-2,3,4,5-tetrahydro-1H-benzo[e][1,4]diazepin-8-ylamino)-pyrimidin-4-ylamino]-3-fluoro-N-methyl-benzamide and 2-bromoethyl methyl ether in DMF were converted to 2-{5-chloro-2-[4-(2-methoxy-ethyl)-2-oxo-2,3,4,5-tetrahydro-1H-benzo[e][1,4]diazepin-8-ylamino]-pyrimidin-4-ylamino}-3-fluoro-N-methyl-benzamide: $^1$H NMR (300 MHz, CD$_3$OD) δ 8.08 (s, 1H), 7.48 (dd, 1H), 7.3 (s, 1H), 7.38 (m, 2H), 7.1 (m, 2H), 3.72 (s, 2H), 3.57 (t, 2H), 3.36 (s, 3H), 3.26 (s, 2H), 2.85 (m, 5H); MS (m/e): 514.2 (M+1).

Example 1863

2-[5-Chloro-2-(4-ethyl-2-oxo-2,3,4,5-tetrahydro-1H-benzo[e][1,4]diazepin-8-ylamino)-pyrimidin-4-ylamino]-3-fluoro-N-methyl-benzamide 1863a) Following a procedure analogous to Example 1856b, 2-[5-chloro-2-(2-oxo-2,3,4,5-tetrahydro-1H-benzo[e][1,4]diazepin-8-ylamino)-pyrimidin-4-ylamino]-3-fluoro-N-methyl-benzamide was converted to 2-[5-chloro-2-(4-ethyl-2-oxo-2,3,4,5-tetrahydro-1H-benzo[e][1,4]diazepin-8-ylamino)-pyrimidin-4-ylamino]-3-fluoro-N-methyl-benzamide: $^1$H NMR (300 MHz, CDCl$_3$) δ 8.93 (s, 1H), 8.2 (br, 1H), 8.15 (s, 1H), 7.78 (br, 1H), 7.55 (m, 2H), 7.4 (t, 2H), 7.18 (d, 1H), 6.98 (d, 1H), 6.63 (br, 1H), 3.82 (s, 2H), 3.53 (s, 2H), 3.03 (d, 3H), 2.8 (q, 2H), 1.24 (t, 3H); MS (m/e): 484.4 (M+1).

Example 1864

2-{5-Chloro-2-[4-(2-methoxy-ethyl)-2-oxo-2,3,4,5-tetrahydro-1H-benzo[e][1,4]diazepin-8-ylamino]-pyrimidin-4-ylamino}-N-methyl-benzamide Following a procedure analogous to Example 1862a, 2-[5-chloro-2-(2-oxo-2,3,4,5-tetrahydro-1H-benzo[e][1,4]diazepin-8-ylamino)-pyrimidin-4-ylamino]-N-methyl-benzamide was converted to 2-{5-chloro-2-[4-(2-methoxy-ethyl)-2-oxo-2,3,4,5-tetrahydro-1H-benzo[e][1,4]diazepin-8-ylamino]-pyrimidin-4-ylamino}-N-methyl-benzamide: $^1$H NMR (300 MHz, CDCl$_3$) δ 11.1 (s, 1H), 8.6 (d, 1H), 8.18 (s, 1H), 7.7 (s, 1H), 7.5 (m, 3H), 7.2 (m, 3H), 6.42 (br, 1H), 3.97 (s, 2H), 3.65 (m, 2H), 3.5 (s, 2H), 3.1 (d, 3H), 2.95 (m, 2H); MS (m/e): 496.4 (M+1).

Example 1865

3-[5-Chloro-2-(4-ethyl-2-oxo-2,3,4,5-tetrahydro-1H-benzo[e][1,4]diazepin-8-ylamino)-pyrimidin-4-ylamino]-4-methyl-thiophene-2-carboxylic acid methylamide 1865a) Following a procedure analogous to Example 1741e, 8-amino-2-oxo-1,2,3,5-tetrahydro-benzo[e][1,4]diazepine-4-carboxylic acid benzyl ester and 3-(2,5-dichloro-pyrimidin-4-ylamino)-4-methyl-thiophene-2-carboxylic acid methylamide were converted to 8-[5-chloro-4-(4-methyl-2-methylcarbamoyl-thiophen-3-ylamino)-pyrimidin-2-ylamino]-2-oxo-1,2,3,5-tetrahydro-benzo[e][1,4]diazepine-4-carboxylic acid benzyl ester, which following a procedure analogous to Example 1860a was converted to 3-[5-chloro-2-(2-oxo-2,3,4,5-tetrahydro-1H-benzo[e][1,4]diazepin-8-ylamino)-pyrimidin-4-ylamino]-4-methyl-thiophene-2-carboxylic acid methylamide: $^1$H NMR (300 MHz, CD$_3$OD) δ 8.26 (s, 1H), 7.62 (s, 1H), 7.45 (s, 1H), 7.4 (m, 2H), 4.4 (s, 2H), 3.82 (s, 2H), 2.97 (s, 3H), 2.23 (s, 3H); MS (m/e): 458.4 (M+1).

1865b) Following a procedure analogous to Example 1856b, 3-[5-chloro-2-(2-oxo-2,3,4,5-tetrahydro-1H-benzo[e][1,4]diazepin-8-ylamino)-pyrimidin-4-ylamino]-4-methyl-thiophene-2-carboxylic acid methylamide was converted to 3-[5-chloro-2-(4-ethyl-2-oxo-2,3,4,5-tetrahydro-1H-benzo[e][1,4]diazepin-8-ylamino)-pyrimidin-4-ylamino]-4-methyl-thiophene-2-carboxylic acid methylamide: $^1$H NMR (300 MHz, CDCl$_3$) δ 8.72 (s, 1H), 8.58 (s, 1H), 8.1 (s, 1H), 7.97 (br, 1H), 7.56 (s, 1H), 7.25 (s, 1H), 7.2 (d, 1H), 6.97 (d, 1H), 6.28 (br, 1H), 3.9 (s, 2H), 3.58 (s, 2H), 3.02 (d, 3H), 2.86 (q, 2H), 2.17 (s, 3H), 1.27 (t, 3H); MS (m/e): 486.4 (M+1).

Example 1866

3-{5-Chloro-2-[2-oxo-4-(2,2,2-trifluoro-acetyl)-2,3,4,5-tetrahydro-1H-benzo[e][1,4]diazepin-8-ylamino]-pyrimidin-4-ylamino}-4-methyl-thiophene-2-carboxylic acid methylamide 1866a) A solution of (2-amino-4-nitro-benzylamino)-acetic acid tert-butyl ester (0.28 g, 1.0 mmol) was heated at 120° C. for 16 hours in TFA (5 mL). Concentration and chromatography on silica gel with methylene chloride and methanol (20:1) gave 0.3 g of [(2-amino-4-nitro-benzyl)-(2,2,2-trifluoro-acetyl)-amino]-acetic acid. Following a procedure analogous to Example 1848d, [(2-amino-4-nitro-benzyl)-(2,2,2-trifluoro-acetyl)-amino]-acetic acid was converted to 8-nitro-4-(2,2,2-trifluoro-acetyl)-1,3,4,5-tetrahydro-benzo[e][1,4]diazepin-2-one: $^1$H NMR (300 MHz, CD$_3$OD) δ 8.0 (m, 2H), 7.6 (dd, 1H), 4.98 (s, 1H), 4.57 (s, 2H), 4.53 (s, 1H).

1866b) Following a procedure analogous to Example 1791b, 8-nitro-4-(2,2,2-trifluoro-acetyl)-1,3,4,5-tetrahydro-benzo[e][1,4]diazepin-2-one was converted to 8-amino-4-(2,2,2-trifluoro-acetyl)-1,3,4,5-tetrahydro-benzo[e][1,4]diazepin-2-one: $^1$H NMR (300 MHz, CD$_3$OD) δ 7.07 (m, 1H), 6.5 (m, 2H), 6.55 (s, 1H), 4.4 (m, 4H); MS (m/e): 274.2 (M+1).

1866c) Following a procedure analogous to Example 1741e, 8-amino-4-(2,2,2-trifluoro-acetyl)-1,3,4,5-tetrahydro-benzo[e][1,4]diazepin-2-one (23.8 mg, 0.09 mmol) and 3-(2,5-dichloro-pyrimidin-4-ylamino)-4-methyl-thiophene-2-carboxylic acid methylamide were converted to 3-{5-chloro-2-[2-oxo-4-(2,2,2-trifluoro-acetyl)-2,3,4,5-tetrahydro-1H-benzo[e][1,4]diazepin-8-ylamino]-pyrimidin-4-ylamino}-4-methyl-thiophene-2-carboxylic acid methylamide: $^1$H NMR (300 MHz, CD$_3$OD) δ 8.1 (s, 1H), 7.4 (d, 1H), 7.33 (s, 1H), 7.18 (m, 2H), 4.7 (s, 1H), 4.65 (s, 1H), 4.27 (s, 2H), 2.84 (s, 3H), 2.05 (s, 3H); MS (m/e): 554.1 (M+1).

Example 1867

2-[5-Chloro-2-(4-methyl-2-oxo-2,3,4,5-tetrahydro-1H-benzo[e][1,4]diazepin-8-ylamino)-pyrimidin-4-ylamino]-N-methyl-benzamide 1867a) A mixture of (2-amino-4-nitro-benzylamino)-acetic acid tert-butyl ester (0.33 g, 1.16 mmol), iodomethane (0.22 mL, 3.5 mmol) and 2-tert-butylimino-2-diethyl-amino-1,3-dimethyl-perhydro-1,2,3-diazaphosphorine on polystyrene (Fluka) (2.6 g, 5.8 mmol) in THF (15 mL) was heated at 40° C. for 6 hours. Filtration, filtrate solvent evaporation, and chromatography on preparative TLC with methylene chloride and methanol (40:1) gave 0.23 g of [(2-amino-4-nitro-benzyl)-methyl-amino]-acetic acid tert-butyl ester in 67% yield: $^1$H NMR (300 MHz, CDCl$_3$) δ 7.54 (d, 1H), 7.52 (s, 1H), 7.18 (d, 1H), 5.43 (br, 2H), 4.73 (s, 2H), 4.25 (s, 2H), 2.35 (s, 3H), 1.37 (s, 9H); MS (m/e): 296.4 (M+1).

1867b) Following a procedure analogous to Example 1858d, [(2-amino-4-nitro-benzyl)-methyl-amino]-acetic acid tert-butyl ester was converted to 4-methyl-8-nitro-1,3,4,5-tetrahydro-benzo[e][1,4]diazepin-2-one: $^1$H NMR (300 MHz, CDCl$_3$) δ 8.05 (d, 1H), 7.95 (s, 1H), 7.5 (d, 1H), 3.93 (s, 2H), 3.52 (s, 2H), 2.6 (s, 3H); MS (m/e): 222.2 (M+1).

127c) Following a procedure analogous to Example 1791b, 4-methyl-8-nitro-1,3,4,5-tetrahydro-benzo[e][1,4]diazepin-2-one was converted to 8-amino-4-methyl-1,3,4,5-tetrahydro-benzo[e][1,4]diazepin-2-one: $^1$H NMR (300 MHz, CDCl$_3$) δ 7.13 (d, 1H), 6.55 (m, 1H), 6.38 (s, 1H), 3.67 (s, 1H), 3.45 (s, 1H), 3.37 (s, 2H), 2.56 (s, 3H); MS (m/e): 192.1 (M+1).

1867d) A mixture of 8-amino-4-methyl-1,3,4,5-tetrahydro-benzo[e][1,4]diazepin-2-one and 2-(2,5-dichloropyrimidin-4-ylamino)-N-methylbenzamide (22 mg, 0.08 mmol), and camphorsulfonic acid (17.4 mg, 0.08 mmol) were heated in IPA (3 mL) at 120° C. for 16 hours. The mixture was heated for another 2.5 hours at 120° C. after the addition of 10 drops of 4 N HCl/dioxane. Concentration and chromatography on preparative TLC with methylene chloride and methanol (100:8) followed by semi-preparative HPLC gave 5 mg of 2-[5-chloro-2-(4-methyl-2-oxo-2,3,4,5-tetrahydro-1H-benzo[e][1,4]diazepin-8-ylamino)-pyrimidin-4-ylamino]-N-methyl-benzamide (16% yield): $^1$H NMR (300 MHz, CD$_3$OD) δ 8.7 (d, 1H), 8.13 (s, 1H), 7.96 (s, 1H), 7.67 (m, 3H), 7.4 (m, 1H), 7.2 (m, 1H), 3.95 (s, 1H), 3.7 (s, 1H), 3.6 (s, 2H), 2.95 (s, 3H), 2.53 (s, 3H); MS (m/e): 452.2 (M+1).

Example 1868

3-[5-Chloro-2-(4-methyl-2-oxo-2,3,4,5-tetrahydro-1H-benzo[e][1,4]diazepin-8-ylamino)-pyrimidin-4-ylamino]-4-methyl-thiophene-2-carboxylic acid methylamide A mixture of 8-amino-4-methyl-1,3,4,5-tetrahydro-benzo[e][1,4]diazepin-2-one (25 mg, 0.13 mmol), 3-(2,5-dichloro-pyrimidin-4-ylamino)-4-methyl-thiophene-2-carboxylic acid methylamide (49.6 mg, 0.16 mmol), and camphorsulfonic acid (33 mg, 0.13 mmol) were heated in IPA (3 mL) at 120° C. for 16 hours. Concentration and chromatography on preparative TLC with methylene chloride and methanol (100:8) gave 2.1 mg of 3-[5-chloro-2-(4-methyl-2-oxo-2,3,4,5-tetrahydro-1H-benzo[e][1,4]diazepin-8-ylamino)-pyrimidin-4-ylamino]-4-methyl-thiophene-2-carboxylic acid methylamide (3.4%): $^1$H NMR (300 MHz, CD$_3$OD) δ 8.1 (d, 1H), 7.98 (s, 1H), 7.7 (m, 1H), 7.35 (m, 2H), 7.15 (s, 1H), 3.65 (s, 1H), 3.61 (s, 1H), 3.2 (s, 2H), 2.85 (s, 3H), 2.52 (s, 3H), 2.1 (s, 3H); MS (m/e): 472.2 (M+1).

Example 1869

8-[5-Chloro-4-(2-fluoro-6-methylcarbamoyl-phenylamino)-pyrimidin-2-ylamino]-2-oxo-1,2,3,5-tetrahydro-benzo[e][1,4]diazepine-4-carboxylic acid ethyl ester A solution of 2-[5-chloro-2-(2-oxo-2,3,4,5-tetrahydro-1H-benzo[e][1,4]diazepin-8-ylamino)-pyrimidin-4-ylamino]-3-fluoro-N-methyl-benzamide (68 mg, 0.15 mmol), pyridine (38 µL, 0.5 mmol) and diethyl pyrocarbonate (22 µL, 0.15 mmol) in THF (5 mL) was stirred at 70° C. for 16 hours. Concentration and chromatography on preparative TLC with methylene chloride and methanol (12.5:1) gave 33 mg of 8-[5-chloro-4-(2-fluoro-6-methylcarbamoyl-phenylamino)-pyrimidin-2-ylamino]-2-oxo-1,2,3,5-tetrahydro-benzo[e][1,4]diazepine-4-carboxylic acid ethyl ester (42%): $^1$H NMR (300 MHz, CD$_3$OD) δ 8.03 (s, 1H), 7.48 (d, 1H), 7.3 (m, 3H), 7.03 (s, 2H), 4.44 (s, 2H), 4.22 (d, 2H), 4.12 (m, 2H), 1.27 (t, 3H); MS (m/e): 528.4 (M+1).

Example 1870

2-[5-Chloro-2-(1,4-diethyl-2-oxo-2,3,4,5-tetrahydro-1H-benzo[e][1,4]diazepin-8-ylamino)-pyrimidin-4-ylamino]-3-fluoro-N-methyl-benzamide 1870a) Following a procedure analogous to Example 1851a, 8-nitro-2-oxo-1,2,3,5-tetrahydro-benzo[e][1,4]diazepine-4-carboxylic acid benzyl ester was converted to 1-ethyl-8-nitro-2-oxo-1,2,3,5-tetrahydro-benzo[e][1,4]diazepine-4-carboxylic acid benzyl ester: $^1$H NMR (300 MHz, CDCl$_3$) δ 8.1 (d, 1H), 7.3 (m, 2H), 5.12 (s, 2H), 4.56 (s, 2H), 4.0 (m, 4H), 1.0 (t, 3H); MS (m/e): 370.4 (M+1).

1870b) Following a procedure analogous to Example 1774c, 1-ethyl-8-nitro-2-oxo-1,2,3,5-tetrahydro-benzo[e][1,4]diazepine-4-carboxylic acid benzyl ester was converted to 8-amino-1-ethyl-2-oxo-1,2,3,5-tetrahydro-benzo[e][1,4]diazepine-4-carboxylic acid benzyl ester. $^1$H NMR (300 MHz, CDCl$_3$) δ 7.47 (m, 6H), 6.95 (m, 2H), 5.26 (s, 2H), 4.53 (s, 2H), 4.08 (s, 2H), 4.02 (q, 2H), 1.27 (t, 3H); MS (m/e): 340.6 (M+1).

1870c) Following a procedure analogous to Example 1741e, 8-amino-1-ethyl-2-oxo-1,2,3,5-tetrahydro-benzo[e][1,4]diazepine-4-carboxylic acid benzyl ester and 2-(2,5-dichloropyrimidin-4-ylamino)-3-fluoro-N-methylbenzamide were converted to 8-[5-chloro-4-(2-fluoro-6-methylcarbamoyl-phenylamino)-pyrimidin-2-ylamino]-1-ethyl-2-oxo-1,2,3,5-tetrahydro-benzo[e][1,4]diazepine-4-carboxylic acid benzyl ester (64%): $^1$H NMR (300 MHz, CDCl$_3$) δ 9.4 (s, 1H), 8.03 (br, 2H), 7.52 (br, 1H), 7.3 (br, 10H), 6.19 (br, 1H), 5.12 (s, 2H), 4.4 (s, 2H), 3.9 (br, 2H), 3.78 (br, 2H), 2.95 (d, 3H), 1.05 (t, 3H); MS (m/e): 618.5 (M+1).

1870d) Following a procedure analogous to Example 1860a, 8-[5-chloro-4-(2-fluoro-6-methylcarbamoyl-phenylamino)-pyrimidin-2-ylamino]-1-ethyl-2-oxo-1,2,3,5-tetrahydro-benzo[e][1,4]diazepine-4-carboxylic acid benzyl ester was converted to 2-[5-chloro-2-(1-ethyl-2-oxo-2,3,4,5-tetrahydro-1H-benzo[e][1,4]diazepin-8-ylamino)-pyrimidin-4-ylamino]-3-fluoro-N-methyl-benzamide: $^1$H NMR (300 MHz, CD$_3$OD) δ 8.12 (s, 1H), 7.73 (s, 1H), 7.48 (dd, 1H), 7.35 (m, 3H), 7.22 (d, 1H), 3.95 (s, 2H), 3.77 (q, 2H), 3.38 (s, 2H), 2.85 (s, 3H), 1.1 (t, 3H); MS (m/e): 484.6 (M+1).

1870e) Following a procedure analogous to Example 1856b, 2-[5-chloro-2-(1-ethyl-2-oxo-2,3,4,5-tetrahydro-1H-benzo[e][1,4]diazepin-8-ylamino)-pyrimidin-4-ylamino]-3-fluoro-N-methyl-benzamide was converted to 2-[5-chloro-2-(1,4-diethyl-2-oxo-2,3,4,5-tetrahydro-1H-benzo[e][1,4]diazepin-8-ylamino)-pyrimidin-4-ylamino]-3-fluoro-N-methyl-benzamide: $^1$H NMR (300 MHz, CD$_3$OD) δ 8.1 (s, 1H), 7.65 (s, 1H), 7.45 (d, 1H), 7.3 (m, 3H), 7.13 (d, 1H), 3.75 (q, 2H), 3.58 (s, 2H), 3.1 (s, 2H), 2.85 (s, 3H), 2.71 (q, 2H), 1.18 (t, 3H), 1.07 (t, 3H); MS (m/e): 512.6 (M+1).

Example 1871

3-{5-Chloro-2-[1-ethyl-2-oxo-4-(3,3,3-trifluoro-propyl)-2,3,4,5-tetrahydro-1H-benzo[e][1,4]diazepin-8-ylamino]-pyrimidin-4-ylamino}-thiophene-2-carboxylic acid methylamide Following a procedure analogous to Example 1862a, 3-[5-chloro-2-(1-ethyl-2-oxo-2,3,4,5-tetrahydro-1H-benzo[e][1,4]diazepin-8-ylamino)-pyrimidin-4-ylamino]-thiophene-2-carboxylic acid methylamide and 1-iodo-3,3,3-trifluoropropane were converted to 3-{5-chloro-2-[1-ethyl-2-oxo-4-(3,3,3-trifluoro-propyl)-2,3,4,5-tetrahydro-1H-benzo[e][1,4]diazepin-8-ylamino]-pyrimidin-4-ylamino}-thiophene-2-carboxylic acid methylamide: $^1$H NMR (300 MHz, CD$_3$OD) δ 11.46 (s, 1H), 8.4 (d, 1H), 8.25 (s, 1H), 7.83 (s, 1H), 7.35 (m, 3H), 7.22 (br, 1H), 5.83 (br, 1H), 4.0 (q, 2H), 3.7 (s, 2H), 3.28 (s, 2H), 3.12 (d, 3H), 3.05 (t, 2H), 2.5 (m, 2H), 1.27 (t, 3H); MS (m/e): 500.4 (M+1).

Example 1872

3-[5-Chloro-2-(1-ethyl-4-methanesulfonyl-2-oxo-2,3,4,5-tetrahydro-1H-benzo[e][1,4]diazepin-8-ylamino)-pyrimidin-4-ylamino]-thiophene-2-carboxylic acid methylamide Following a procedure analogous to Example 1860b, 3-[5-chloro-2-(1-ethyl-2-oxo-2,3,4,5-tetrahydro-1H-benzo[e][1,4]diazepin-8-ylamino)-pyrimidin-4-ylamino]-thiophene-2-carboxylic acid methylamide was converted to 3-[5-chloro-2-(1-ethyl-4-methanesulfonyl-2-oxo-2,3,4,5-tetrahydro-1H-benzo[e][1,4]diazepin-8-ylamino)-pyrimidin-4-ylamino]-thiophene-2-carboxylic acid methylamide: $^1$H NMR (300 MHz, DMSO) δ 11.67 (s, 1H), 9.75 (s, 1H), 8.46 (d, 1H), 8.3

(s, 1H), 8.27 (d, 1H), 7.87 (s, 1H), 7.74 (d, 1H), 7.65 (d, 1H), 7.48 (d, 1H), 4.25 (s, 2H), 3.83 (q, 2H), 3.68 (s, 2H), 3.61 (q, 2H), 3.03 (s, 3H), 2.78 (s, 3H), 1.1 (t, 3H); MS (m/e): 550.2 (M+1).

Example 1873

2-{5-Chloro-2-[1-ethyl-4-(2-hydroxy-ethyl)-2-oxo-2,3,4,5-tetrahydro-1H-benzo[e][1,4]diazepin-8-ylamino]-pyrimidin-4-ylamino}-3-fluoro-N-methyl-benzamide A mixture of 2-[5-chloro-2-(1-ethyl-2-oxo-2,3,4,5-tetrahydro-1H-benzo[e][1,4]diazepin-8-ylamino)-pyrimidin-4-ylamino]-3-fluoro-N-methyl-benzamide (90 mg, 0.19 mmol), potassium carbonate (77 mg, 0.56 mmol) and 2-bromoethanol (47 mg, 0.37 mmol) in ethanol (5 mL) was heated at 75° C. for 16 hours. Concentration and chromatography on preparative TLC with methylene chloride and methanol (100:9) gave 45 mg of 2-{5-chloro-2-[1-ethyl-4-(2-hydroxy-ethyl)-2-oxo-2,3,4,5-tetrahydro-1H-benzo[e][1,4]diazepin-8-ylamino]-pyrimidin-4-ylamino}-3-fluoro-N-methyl-benzamide (46%): $^1$H NMR (300 MHz, CD$_3$OD) δ 8.1 (s, 1H), 7.6 (s, 1H), 7.45 (d, 1H), 7.3 (m, 3H), 7.15 (d, 1H), 3.75 (t, 2H), 3.72 (q, 2H), 3.48 (s, 2H), 3.1 (s, 2H), 2.83 (s, 3H), 2.77 (t, 2H), 1.07 (t, 3H); MS (m/e) 528.4 (M+1).

Example 1874

3-[5-Chloro-2-(1,4-diethyl-2-oxo-2,3,4,5-tetrahydro-1H-benzo[e][1,4]diazepin-8-ylamino)-pyrimidin-4-ylamino]-thiophene-2-carboxylic acid methylamide 1874a) Following a procedure analogous to Example 1741e, 8-amino-1-ethyl-2-oxo-1,2,3,5-tetrahydro-benzo[e][1,4]diazepine-4-carboxylic acid benzyl ester and 3-(2,5-dichloro-pyrimidin-4-ylamino)-4-methyl-thiophene-2-carboxylic acid methylamide were converted to 8-[5-chloro-4-(4-methyl-2-methylcarbamoyl-thiophen-3-ylamino)-pyrimidin-2-ylamino]-1-ethyl-2-oxo-1,2,3,5-tetrahydro-benzo[e][1,4]diazepine-4-carboxylic acid benzyl ester: $^1$H NMR (300 MHz, CDCl$_3$) δ 9.58 (br, 1H), 8.9 (br, 1H), 8.13 (s, 1H), 7.7 (br, 1H), 7.48 (br, 5H), 7.3 (br, 10H), 7.26 (br, 2H), 7.1 (s, 1H), 6.02 (q, 1H), 5.28 (br, 2H), 4.58 (br, 2H), 4.1 (br, 2H), 3.82 (q, 2H), 3.08 (s, 3H), 1.15 (t, 3H); MS (m/e): 620.6 (M+1).

1874b) Following a procedure analogous to Example 1860a, 8-[5-chloro-4-(4-methyl-2-methylcarbamoyl-thiophen-3-ylamino)-pyrimidin-2-ylamino]-1-ethyl-2-oxo-1,2,3,5-tetrahydro-benzo[e][1,4]diazepine-4-carboxylic acid benzyl ester was converted to 3-[5-chloro-2-(1-ethyl-2-oxo-2,3,4,5-tetrahydro-1H-benzo[e][1,4]diazepin-8-ylamino)-pyrimidin-4-ylamino]-4-methyl-thiophene-2-carboxylic acid methylamide (92%): $^1$H NMR (300 MHz, CD$_3$OD) δ 8.17 (s, 1H), 7.73 (s, 1H), 7.45 (dd, 1H), 7.32 (s, 2H), 4.17 (s, 2H), 3.84 (br, 2H), 3.63 (s, 2H), 2.82 (s, 3H), 2.08 (s, 3H), 1.12 (t, 3H); MS (m/e): 486.4 (M+1).

1874c) Following a procedure analogous to Example 1856b, 3-[5-chloro-2-(1-ethyl-2-oxo-2,3,4,5-tetrahydro-1H-benzo[e][1,4]diazepin-8-ylamino)-pyrimidin-4-ylamino]-4-methyl-thiophene-2-carboxylic acid methylamide was converted to 3-[5-chloro-2-(1,4-diethyl-2-oxo-2,3,4,5-tetrahydro-1H-benzo[e][1,4]diazepin-8-ylamino)-pyrimidin-4-ylamino]-4-methyl-thiophene-2-carboxylic acid methylamide: $^1$H NMR (300 MHz, CD$_3$OD) δ 8.12 (s, 1H), 7.62 (s, 1H), 7.3 (dd, 1H), 7.24 (s, 1H), 7.17 (d, 1H), 3.78 (q, 2H), 3.63 (s, 2H), 3.19 (s, 2H), 2.85 (s, 3H), 2.76 (q, 2H), 2.05 (s, 3H), 1.21 (t, 3H), 1.07 (t, 3H); MS (m/e): 514.5 (M+1).

Example 1875

8-[5-Chloro-4-(2-fluoro-6-methylcarbamoyl-phenylamino)-pyrimidin-2-ylamino]-1-ethyl-2-oxo-1,2,3,5-tetrahydro-benzo[e][1,4]diazepine-4-carboxylic acid ethyl ester Following a procedure analogous to Example 1869a, 2-[5-chloro-2-(1-ethyl-2-oxo-2,3,4,5-tetrahydro-1H-benzo[e][1,4]diazepin-8-ylamino)-pyrimidin-4-ylamino]-3-fluoro-N-methyl-benzamide was converted to 8-[5-chloro-4-(2-fluoro-6-methylcarbamoyl-phenylamino)-pyrimidin-2-ylamino]-1-ethyl-2-oxo-1,2,3,5-tetrahydro-benzo[e][1,4]diazepine-4-carboxylic acid ethyl ester: $^1$H NMR (300 MHz, CDCl$_3$) δ 9.42 (s, 1H), 8.17 (s, 1H), 7.96 (br, 1H), 7.65 (br, 1H), 7.35 (m, 5H), 6.35 (br, 1H), 4.5 (s, 2H), 4.28 (q, 2H), 4.01 (s, 2H), 3.88 (q, 2H), 3.07 (d, 3H), 1.38 (br, 3H), 1.17 (t, 3H); MS (m/e): 556.4 (M+1).

Example 1876

8-[5-Chloro-4-(2-fluoro-6-prop-2-ynylcarbamoyl-phenylamino)-pyrimidin-2-ylamino]-1-ethyl-2-oxo-1,2,3,5-tetrahydro-benzo[e][1,4]diazepine-4-carboxylic acid ethyl ester 1876a) Following a procedure analogous to Example 1869a, the HCl salt of 8-amino-1-ethyl-2-oxo-1,2,3,5-tetrahydro-benzo[e][1,4]diazepine-4-carboxylic acid benzyl ester and 2-(2,5-dichloro-pyrimidin-4-ylamino)-3-fluoro-N-prop-2-ynyl-benzamide were converted to 8-[5-chloro-4-(2-fluoro-6-prop-2-ynylcarbamoylphenylamino)-pyrimidin-2-ylamino]-1-ethyl-2-oxo-1,2,3,5-tetrahydro-benzo[e][1,4]diazepine-4-carboxylic acid benzyl ester: $^1$H NMR (300 MHz, CDCl$_3$) δ 8.9 (br, 1H), 8.18 (s, 1H), 7.63 (m, 2H), 7.4 (m, 10H), 5.24 (br, 2H), 4.52 (br, 2H), 4.24 (m, 2H), 4.03 (br, 2H), 3.88 (br, 2H), 1.16 (t, 3H); MS (m/e): 642.6 (M+1).

1876b) Following a procedure analogous to Example 1860a, 8-[5-chloro-4-(2-fluoro-6-prop-2-ynylcarbamoylphenylamino)-pyrimidin-2-ylamino]-1-ethyl-2-oxo-1,2,3,5-tetrahydro-benzo[e][1,4]diazepine-4-carboxylic acid benzyl ester was converted to 2-[5-chloro-2-(1-ethyl-2-oxo-2,3,4,5-tetrahydro-1H-benzo[e][1,4]diazepin-8-ylamino)-pyrimidin-4-ylamino]-3-fluoro-N-prop-2-ynyl-benzamide: $^1$H NMR (300 MHz, CD$_3$OD) δ 8.14 (s, 1H), 7.82 (d, 1H), 7.36 (m, 5H), 7.48 (d, 1H), 4.15 (s, 2H), 4.04 (d, 2H), 3.78 (br, 2H), 3.62 (s, 2H), 1.12 (t, 3H); MS (m/e): 508.5 (M+1).

1876c) Following a procedure analogous to Example 1869a, 2-[5-chloro-2-(1-ethyl-2-oxo-2,3,4,5-tetrahydro-1H-benzo[e][1,4]diazepin-8-ylamino)-pyrimidin-4-ylamino]-3-fluoro-N-prop-2-ynyl-benzamide was converted to 8-[5-chloro-4-(2-fluoro-6-prop-2-ynylcarbamoyl-phenylamino)-pyrimidin-2-ylamino]-1-ethyl-2-oxo-1,2,3,5-tetrahydro-benzo[e][1,4]diazepine-4-carboxylic acid ethyl ester: $^1$H NMR (300 MHz, CDCl$_3$) δ 8.96 (br, 1H), 8.18 (s, 1H), 7.75 (br, 1H), 7.65 (br, 1H), 7.5 (d, 1H), 7.35 (m, 5H), 6.6 (br, 1H), 4.5 (br, 2H), 4.27 (m, 4H), 3.98 (m, 2H), 3.88 (q, 2H), 3.07 (d, 3H), 1.38 (br, 3H), 1.17 (t, 3H); MS (m/e): 580.4 (M+1).

Example 1877

2-[2-(1-Acetyl-3-oxo-2,3,4,5-tetrahydro-1H-benzo[e][1,4]diazepin-8-ylamino)-5-chloro-pyrimidin-4-ylamino]-3-fluoro-N-methyl-benzamide 1877a) A solution of 2-fluoro-4-nitro-benzonitrile (16.6 g, 0.1 mol), glycine methyl ester (16 g, 0.125 mol, 1.25 eq.) and triethylamine (20 g, 0.2 mol) in DMSO (250 mL) was stirred at 70° C. for 12 hours. Water (2 L) was added and the solid precipitate was collected by filtration. Washed with ether and dried to give (2-cyano-5-nitro-phenylamino)-acetic acid methyl ester (23 g, 97.8 mmol, 98%): $^1$H NMR (300 MHz, CDCl$_3$) δ 7.61 (dd, 2H), 7.40 (d, 1H), 4.10 (d, 2H), 3.87 (s, 3H).

1877b) At 50° C., (2-cyano-5-nitro-phenylamino)-acetic acid methyl ester (0.5 g, 2.1 mmol) was heated in acetyl chloride (100 mL) for 3 hours in the presence of catalytic DMAP. The mixture was poured over ice and then partitioned between ethyl acetate (100 ml) and water (50 ml). The organic layer was washed once with 1 M NaOH (100 mL) and dried over sodium sulfate. Concentration and silica gel purification (EtOAc/hexanes 9:1) gave [acetyl-(2-cyano-5-nitro-phenyl)-amino]-acetic acid methyl ester (0.5 g, 1.8 mmol, 86%): $^1$H NMR (300 MHz, CDCl$_3$) δ 8.59 (d, 1H), 8.36 (dd, 1H), 7.99 (d, 1H), 3.9 (b, 2H), 3.78 (s, 3H), 2.00 (s, 3H).

1877c) Following a procedure analogous to Example 1791b, [acetyl-(2-cyano-5-nitro-phenyl)-amino]-acetic acid methyl ester was converted to [acetyl-(5-amino-2-cyano-phenyl)-amino]-acetic acid methyl ester: $^1$H NMR (300 MHz, CD$_3$OD) δ 7.45 (d, 1H), 6.85 (d, 1H), 6.68 (dd, 1H), 4.89 (d, 1H), 3.94 (d, 1H), 3.74 (s, 3H), 1.96 (s, 3H).

1877d) A mixture of [acetyl-(5-amino-2-cyano-phenyl)-amino]-acetic acid methyl ester (0.4 g, 1.6 mmol), sodium methoxide (87 mg, 1.6 mmol) and Raney nickel (50 mg) was shaken for 12 hours under a 50 psi H$_2$ atmosphere. The catalyst was removed by filtration and the filtrate was concentrated. Silica gel chromatography (DCM/MeOH 9:1) gave 1-acetyl-8-amino-1,2,4,5-tetrahydro-benzo[e][1,4]diazepin-3-one (120 mg, 0.55 mmol, 34%): $^1$H NMR (300 MHz, CD$_3$OD) δ 7.12 (d, 1H), 6.7 (m, 2H), 5.35 (d, 1H), 4.37 (d, 1H), 3.80 (d, 1H), 3.49 (d, 1H), 1.93 (s, 3H); MS (m/e) 220 (M+1).

1877e) Following a procedure analogous to Example 1741e, 1-acetyl-8-amino-1,2,4,5-tetrahydro-benzo[e][1,4]diazepin-3-one and 2-(2,5-dichloro-pyrimidin-4-ylamino)-3-fluoro-N-methyl-benzamide were converted to 2-[2-(1-acetyl-3-oxo-2,3,4,5-tetrahydro-1H-benzo[e][1,4]diazepin-8-ylamino)-5-chloro-pyrimidin-4-ylamino]-3-fluoro-N-methyl-benzamide: $^1$H NMR (300 MHz, CD$_3$OD) δ 8.08 (s, 1H), 7.8 (br, 1H), 7.4 (m, 3H), 7.2 (d, 2H), 5.4 (d, 1H), 4.4 (d, 1H), 3.8 (br, 1H), 3.3 (br, 1H), 2.83 (s, 3H), 1.77 (s, 3H); $^{19}$F NMR (282 MHz, CD$_3$OD) δ −117.5; MS (m/e) 498 (M+1); mp 179-185° C.

Example 1878

3-[2-(1-Acetyl-3-oxo-2,3,4,5-tetrahydro-1H-benzo[e][1,4]diazepin-8-ylamino)-5-chloro-pyrimidin-4-ylamino]-thiophene-2-carboxylic acid methyl amide Following a procedure analogous to Example 1741e, 1-acetyl-8-amino-1,2,4,5-tetrahydro-benzo[e][1,4]diazepin-3-one and 3-(2,5-dichloro-pyrimidin-4-ylamino)-thiophene-2-carboxylic acid methylamide were converted to 3-[2-(1-acetyl-3-oxo-2,3,4,5-tetrahydro-1H-benzo[e][1,4]diazepin-8-ylamino)-5-chloro-pyrimidin-4-ylamino]-thiophene-2-carboxylic acid methylamide. $^1$H NMR (300 MHz, DMSO-d$_6$) δ 8.46 (d, 1H), 8.30 (s, 1H), 7.85 (m, 1H), 7.75 (d, 1H), 7.63 (dd, 1H), 7.41 (d, 1H), 3.8 (br, 1H), 3.3 (br, 1H), 2.77 (d, 3H), 1.83 (s, 3H); MS (m/e) 486 (M+1).

Example 1879

2-[2-(1-Acetyl-4-ethyl-2,3,4,5-tetrahydro-1H-benzo[e][1,4]diazepin-8-ylamino)-5-chloro-pyrimidin-4-ylamino]-3-fluoro-N-methyl-benzamide 1879a) A mixture of 2-fluoro-4-nitrobenzonitrile (13.2 g), N-ethylethylenediamine (16 mL) and potassium carbonate (10 g) in acetonitrile (250 mL) was vigorously stirred for 16 hours resulting in the formation of an orange solid. The mixture was diluted with water and filtered. The precipitate was washed with water and dried to provide 2-(2-methylamino-ethylamino)-4-nitro-benzonitrile (10 g): $^1$H NMR (300 MHz, CDCl$_3$) δ 7.65 (d, 1H), 7.55 (m, 2H), 5.8 (br, 1H), 3.4 (q, 2H), 3.1 (m, 2H), 2.8 (q, 2H), 1.2 (t, 3H).

1879b) A solution of 2-(2-methylamino-ethylamino)-4-nitro-benzonitrile (1 g) in methylene chloride (100 mL) was cooled to −78° C. and treated with 1 M DIBAL-H in hexanes (8.5 mL). The mixture was allowed to slowly warm to room temperature and stirred for 16 hours. The mixture was treated with HOAc (2 mL) followed by 1 M sodium cyanoborohydride in THF (4 mL). After 1 hour, the mixture was diluted with water and the organic layer was separated. The aqueous phase was extracted again with methylene chloride and the combined organics were dried over sodium sulfate, filtered and concentrated. Silica gel chromatography (1→2% MeOH/methylene chloride) provided 4-ethyl-8-nitro-2,3,4,5-tetrahydro-1H-benzo[e][1,4]diazepine, which was heated in acetic anhydride at 100° C. for 2 hours to provide, after concentration and silica gel chromatography 1-(4-ethyl-8-nitro-2,3,4,5-tetrahydro-benzo[e][1,4]diazepin-1-yl)-ethanone (90 mg).

1879c) Following a procedure analogous to Example 1774c, 1-(4-ethyl-8-nitro-2,3,4,5-tetrahydro-benzo[e][1,4]diazepin-1-yl)-ethanone was converted to 1-(8-amino-4-ethyl-2,3,4,5-tetrahydro-benzo[e][1,4]diazepin-1-yl)-ethanone: $^1$H NMR (300 MHz, CDCl$_3$) δ 7.18 (d, 1H), 6.73 (d, 1H), 6.62 (s, 1H), 3.3 (m, 2H), 2.8 (m, 2H), 2.08 (s, 3H), 1.33 (t, 3H); MS (m/e): 234.4 (M+1).

1879d) Following a procedure analogous to Example 1741e, the HCl salt of 1-(8-Amino-4-ethyl-2,3,4,5-tetrahydro-benzo[e][1,4]diazepin-1-yl)-ethanone was converted to 2-[2-(1-acetyl-4-ethyl-2,3,4,5-tetrahydro-1H-benzo[e][1,4]diazepin-8-ylamino)-5-chloro-pyrimidin-4-ylamino]-3-fluoro-N-methyl-benzamide: $^1$H NMR (300 MHz, CD$_3$OD) δ 8.23 (s, 1H), 7.85 (s, 1H), 7.51 (m, 3H), 7.28 (s, 2H), 3.84 (s, 2H), 3.06 (m, 4H), 2.98 (s, 3H), 2.63 (m, 2H), 1.88 (s, 3H), 1.24 (t, 3H); MS (m/e): 512.6 (M+1).

Example 1880

2-[5-Chloro-2-(5-oxo-2,3,4,5-tetrahydro-benzo[f][1,4]oxazepin-7-ylamino)-pyrimidin-4-ylamino]-N-methyl-benzamide 1880a) Following a procedure analogous to Example 1794a, 6-nitro-chroman-4-one was converted to 7-nitro-3,4-dihydro-2H-benzo[f][1,4]oxazepin-5-one: $^1$H NMR (300 MHz, CDCl$_3$) δ 9.08 (d, 1H), 8.26 (dd, 1H), 7.11 (d, 1H), 4.6 (m, 2H), 3.7 (m, 2H).

1880b) Following a procedure analogous to Example 1791b, 7-nitro-3,4-dihydro-2H-benzo[f][1,4]oxazepin-5-one (3.1 g, 15 mmol) was converted to 7-amino-3,4-dihydro-2H-benzo[f][1,4]oxazepin-5-one: $^1$H NMR (300 MHz, CD$_3$OD) δ 7.2 (d, 1H), 6.95 (d, 1H), 6.85 (d, 1H), 4.23 (t, 2H), 3.3 (m, 2H).

1880c) Following a procedure analogous to Example 1741e, 7-amino-3,4-dihydro-2H-benzo[f][1,4]oxazepin-5-one and 2-(2,5-dichloro-pyrimidin-4-ylamino)-N-methyl-benzamide were converted to 2-[5-chloro-2-(5-oxo-2,3,4,5-tetrahydro-benzo[f][1,4]oxazepin-7-ylamino)-pyrimidin-4-ylamino]-N-methyl-benzamide. TFA salt: $^1$H NMR (300 MHz, CD$_3$OD) δ 8.42 (d, 1H), 8.11 (s, 1H), 7.88 (d, 1H), 7.71 (dd, 1H), 7.54 (dd, 1H), 7.41 (td, 1H), 7.24 (td, 1H), 7.09 (d, 1H), 4.41 (t, 2H), 3.48 (t, 2H), 2.92 (s, 3H); MS (m/e) 439 (M+1).

Example 1881

2-[5-Chloro-2-(5-ethyl-6-oxo-5,6,8,9-tetrahydro-7-oxa-5-aza-benzocyclohepten-3-ylamino)-pyrimidin-4-ylamino]-N-methyl-benzamide 1881a) To a stirring solution of 4-methyl-3-nitrobenzoic acid (10.2 g, 56.3 mmol), DMAP (0.68 g, 5.56 mmol, 0.1 eq.), and t-butanol (8.1 mL, 84.69 mmol, 1.5 eq.) in dichloromethane (150 mL) at 0° C. was added DIC (9.7 mL, 61.6 mmol, 1.1 eq.). After 5 minutes the reaction was warmed to room temperature and stirred for an additional 5 hours. The precipitate was filtered and washed with dichloromethane and the combined organic layers were concentrated. The product 4-methyl-3-nitro-benzoic acid tert-butyl ester was purified silica gel chromatography using hexanes as eluent: $^1$H NMR (400 MHz, CDCl$_3$) δ 8.51 (d, 1H), 8.09 (dd, 1H), 7.40 (d, 1H), 2.46 (s, 3H), 1.60 (s, 9H).

1881b) A solution of 4-methyl-3-nitro-benzoic acid tert-butyl ester (8.66 g, 36.5 mmol) in anhydrous DMSO (135 mL) was treated with paraformaldehyde (1.32 g, 44.0 mmol, 1.2 eq.) followed by t-BuOK (0.32 g, 2.7 mmol, 0.074 eq.). The mixture was stirred at room temperature for 2.5 h and quenched with aqueous NH$_4$Cl (250 mL). The mixture was extracted with ethyl acetate (3×50 mL) and the combined organic layers were washed with brine and water, and then dried (Na$_2$SO$_4$) and concentrated. Silica gel chromatography using ethyl acetate (0→30%) in dichloromethane provided 4-(2-hydroxy-ethyl)-3-nitro-benzoic acid tert-butyl ester (4.8 g, white solid): $^1$H NMR (400 MHz, CDCl$_3$) δ 8.47 (d, 1H), 8.13 (dd, 1H), 7.49 (d, 1H), 3.96 (q, 2H), 3.20 (t, 2H), 1.60 (s, 9H), and 4-(2-hydroxy-1-hydroxymethyl-ethyl)-3-nitro-benzoic acid tert-butyl ester (3.7 g, white solid): $^1$H NMR (400 MHz, CDCl$_3$) δ 8.35 (d, 1H), 8.15 (dd, 1H), 7.65 (d, 1H), 4.05 (t, 4H), 3.61 (Q, 1H), 2.05 (t, 2H), 1.59 (s, 9H).

1881c) Following a procedure analogous to Example 1741d, 4-(2-hydroxy-ethyl)-3-nitro-benzoic acid tert-butyl ester was converted to 3-amino-4-(2-hydroxy-ethyl)-benzoic acid tert-butyl ester: $^1$H NMR (300 MHz, CDCl$_3$) δ 7.35 (dd, 1H), 7.30 (d, 1H), 7.06 (d, 1H), 3.90 (t, 2H), 2.81 (t, 2H), 1.55 (s, 9H); MS (m/e) 238 (M+1).

1881d) To a stirring solution of 3-amino-4-(2-hydroxy-ethyl)-benzoic acid tert-butyl ester (2.1 g, 8.86 mmol) in THF (150 mL) and dichloromethane (50 mL) at 0° C. was added diphosgene (0.65 mL, 5.38 mmol) all at once. The reaction turned milky and became clear after 1 minute. The reaction was warmed to room temperature and stirred for 150 minutes. The solvent evaporated to provide 6-oxo-5,6,8,9-tetrahydro-7-oxa-5-aza-benzocycloheptene-3-carboxylic acid tert-butyl ester: MS (m/e) 264 (M+1).

1881e) A mixture of 6-oxo-5,6,8,9-tetrahydro-7-oxa-5-aza-benzocycloheptene-3-carboxylic acid tert-butyl ester (1.1 g, 4.18 mmol), potassium carbonate (2.5 g, 18.1 mmol, 4.3 eq.) and iodoethane (1.67 mL, 20.87 mmol, 5 eq.) was stirred in DMF (20 mL) for 16 hours at 60° C. The reaction was diluted with water (50 mL) and extracted with ethyl acetate (3×20 mL). The combined organic layers were dried (sodium sulfate) and concentrated. Silica gel chromatography (0→20% ethyl acetate in hexanes) provided 5-ethyl-6-oxo-5,6,8,9-tetrahydro-7-oxa-5-aza-benzocycloheptene-3-carboxylic acid tert-butyl ester as pale solid in quantitative yield: $^1$H NMR (400 MHz, CDCl$_3$) δ 7.81 (s, 1H), 7.80 (dd, 1H), 7.28 (d, 1H), 4.48 (t, 2H), 3.91 (q, 2H), 3.00 (t, 2H), 1.59 (s, 9H), 1.23 (t, 3H).

1881f) A solution of 5-ethyl-6-oxo-5,6,8,9-tetrahydro-7-oxa-5-aza-benzocycloheptene-3-carboxylic acid tert-butyl ester (0.91 g, 3.12 mmol) was stirred in TFA/DCM (1:1, 3 mL) for 16 hours. The reaction was concentrated to provide 5-ethyl-6-oxo-5,6,8,9-tetrahydro-7-oxa-5-aza-benzocycloheptene-3-carboxylic acid (0.73 g).

1881g) A mixture of 5-ethyl-6-oxo-5,6,8,9-tetrahydro-7-oxa-5-aza-benzocycloheptene-3-carboxylic acid (0.73 g, 3.1 mmol) and triethylamine (0.5 mL, 3.6 mmol, 1.15 eq.) in 1:1 toluene/DCM (20 mL) was treated with diphenylphosphoryl azide (0.68 mL, 3.14 mmol) at 0° C. The reaction was warmed to rt and stirred for 2 h. The mixture was concentrated in vacuo without heat to remove the dichloromethane, and then tert-butanol (30 mL) was added. The reaction was refluxed for 3 hours and concentrated. Silica gel chromatography (0→30% ethyl acetate in hexanes) provided (5-ethyl-6-oxo-5,6,8,9-tetrahydro-7-oxa-5-aza-benzocyclohepten-3-yl)-carbamic acid tert-butyl ester (0.73 g): $^1$H NMR (400 MHz, CDCl$_3$) δ 7.41 (s, 1H), 7.12 (d, 1H), 7.04 (dd, 1H), 6.51 (s, 1H), 4.44 (t, 2H), 3.88 (q, 2H), 2.90 (t, 2H), 1.52 (s, 9H), 1.21 (t, 3H).

1881h) Following a procedure analogous to Example 1773c, (5-ethyl-6-oxo-5,6,8,9-tetrahydro-7-oxa-5-aza-benzocyclohepten-3-yl)-carbamic acid tert-butyl ester was converted to 3-amino-5-ethyl-8,9-dihydro-5H-7-oxa-5-aza-benzocyclohepten-6-one, which following a procedure analogous to Example 1741e was coupled to 2-(2,5-dichloro-pyrimidin-4-ylamino)-N-methyl-benzamide to provide 2-[5-chloro-2-(5-ethyl-6-oxo-5,6,8,9-tetrahydro-7-oxa-5-aza-benzocyclohepten-3-ylamino)-pyrimidin-4-ylamino]-N-methyl-benzamide. HCl salt: $^1$H NMR (400 MHz, CD$_3$OD/D$_2$O) δ 8.21 (s, 1H), 8.17 (d, 1H), 7.73 (dd, 1H), 7.54 (d, 1H), 7.42 (d, 1H), 7.33 (m, 2H), 7.26 (dd, 1H), 4.45 (t, 2H), 3.66 (q, 2H), 3.06 (t, 2H), 2.93 (s, 3H), 1.03 (t, 3H); MS (m/e) 467 (M+1).

Example 1882

2-[5-Chloro-2-(5-ethyl-6-oxo-5,6,8,9-tetrahydro-7-oxa-5-aza-benzocyclohepten-3-ylamino)-pyrimidin-4-ylamino]-3-fluoro-N-methyl-benzamide Following a procedure analogous to Example 1741e, 3-amino-5-ethyl-8,9-dihydro-5H-7-oxa-5-aza-benzocyclohepten-6-one and 2-(2,5-dichloro-pyrimidin-4-ylamino)-3-fluoro-N-methyl-benzamide were converted to 2-[5-chloro-2-(5-ethyl-6-oxo-5,6,8,9-tetrahydro-7-oxa-5-aza-benzocyclohepten-3-ylamino)-pyrimidin-4-ylamino]-3-fluoro-N-methyl-benzamide. HCl salt: $^1$H NMR (400 MHz, CD$_3$OD) δ 8.24 (s, 1H), 7.45 (dd, 2H), 7.30 (dd, 2H), 7.21 (d, 1H), 7.09 (dd, 1H), 4.39 (t, 2H), 3.67 (q, 2H), 2.94 (t, 2H), 2.84 (s, 3H), 1.05 (t, 3H); MS (m/e) 485 (M+1).

Example 1883

3-[5-Chloro-2-(5-ethyl-6-oxo-5,6,8,9-tetrahydro-7-oxa-5-aza-benzocyclohepten-3-ylamino)-pyrimidin-4-ylamino]-thiophene-2-carboxylic acid methylamide Following a procedure analogous to Example 1741e, 3-amino-5-ethyl-8,9-dihydro-5H-7-oxa-5-aza-benzocyclohepten-6-one and 3-(2,5-dichloro-pyrimidin-4-ylamino)- thiophene-2-carboxylic acid methylamide were converted to 3-[5-chloro-2-(5-ethyl-6-oxo-5,6,8,9-tetrahydro-7-oxa-5-aza-benzocyclohepten-3-ylamino)-pyrimidin-4-ylamino]-thiophene-2-carboxylic acid methylamide. TFA salt: $^1$H NMR (300 MHz, CDCl$_3$) δ 11.42 (s, 1H), 8.35 (d, 1H), 8.22 (s, 1H), 7.80 (s, 1H), 7.41 (s, 1H), 7.28 (d, 1H), 7.22 (d, 1H), 7.04 (s, 1H), 4.80 (bq, 1H), 4.60 (t, 2H), 3.90 (q, 2H), 3.12 (d, 3H), 3.06 (t, 2H), 1.26 (t, 3H); MS (m/e) 473 (M+1).

It is understood that the examples and embodiments described herein are for illustrative purposes only and that various modifications or changes in light thereof will be suggested to persons skilled in the art and are to be included within the spirit and purview of this application and the scope of the appended claims. All publications, patents, and patent applications cited herein are hereby incorporated by reference in their entirety for all purposes.

What is claimed is:

1. A compound of formula I or II

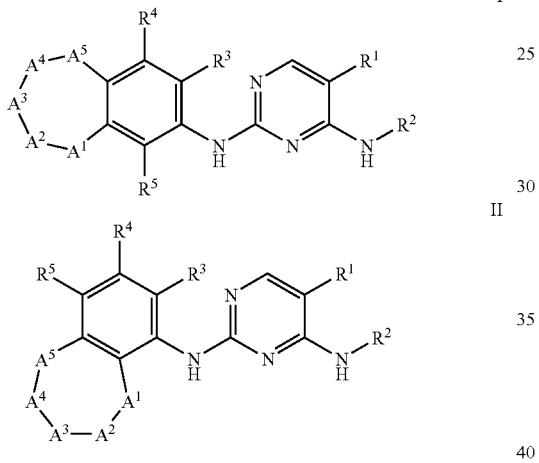

or a pharmaceutically acceptable salt form thereof, wherein $R^1$ is H, halogen, —NO$_2$, —OR$^{10}$, —C(=O)R$^{10}$, —C(=O)OR$^{10}$, —C(=O)NR$^{12}$R$^{13}$, —NR$^{10}$R$^{11}$, C$_{1-6}$-alkyl, —C$_{1-6}$-alkyl-OR$^{10}$, —C$_{1-6}$-alkyl-NR$^{12}$R$^{13}$, C$_{1-6}$-haloalkyl, C$_{2-6}$-alkenyl, C$_{2-6}$-alkynyl, C$_{6-15}$-aryl, 5-15 membered heteroaryl, C$_{3-10}$ cycloalkyl, 3-15 membered heterocycloalkyl, pseudohalogen, —S(=O)$_n$R$^{10}$, —S(=O)$_2$NR$^{12}$R$^{13}$, —OCH$_2$F, —OCHF$_2$, —OCF$_3$, —NHOH, —OC(=O)R$^{10}$, —OC(=O)NR$^{12}$R$^{13}$, —NR$^{10}$C(=O)R$^{11}$, —NR$^{10}$C(=O)OR$^{11}$, —NR$^{10}$S(=O)$_2$R$^{11}$, —NR$^{10}$C(=O)NR$^{12}$R$^{13}$, —NR$^{10}$S(=O)$_2$NR$^{12}$R$^{13}$, or —SCF$_3$;

$R^2$ is a group chosen from C$_{1-6}$-alkyl, C$_{2-6}$-alkenyl, C$_{2-6}$-alkynyl, C$_{6-15}$-aryl, C$_{3-10}$-cycloalkyl, 3-15 membered heterocycloalkyl, and 5-15 membered heteroaryl, wherein the R$^2$ group is optionally substituted by one or more members independently chosen from halogen, —NO$_2$, —OR$^{20}$, =O, —C(=O)R$^{20}$, —C(=O)OR$^{20}$, —C(=O)NR$^{22}$R$^{23}$, —NR$^{20}$R$^{21}$, C$_{1-6}$-alkyl-(R$^{25}$)$_x$, C$_{6-15}$-aryl-(R$^{25}$)$_x$, 5-15 membered heteroaryl-(R$^{25}$)$_x$, C$_{3-10}$ cycloalkyl-(R$^{25}$)$_x$, 3-15 membered heterocycloalkyl-(R$^{25}$)$_x$, pseudohalogen, —S(=O)$_n$R$^{20}$, —S(=O)$_2$NR$^{22}$R$^{23}$, —OCH$_2$F, —OCHF$_2$, —OCF$_3$, —NHOH, —OC(=O)R$^{20}$, —OC(=O)NR$^{22}$R$^{23}$, —NR$^{20}$C(=O)R$^{21}$, —NR$^{20}$C(=O)OR$^{21}$, —NR$^{20}$S(=O)$_2$R$^{21}$, —NR$^{20}$C(=O)NR$^{22}$R$^{23}$, —NR$^{20}$S(=O)$_2$NR$^{22}$R$^{23}$, and —SCF$_3$;

$R^3$, $R^4$, and $R^5$ are independently chosen from H, halogen, —NO$_2$, —OR$^{30}$, —C(=O)R$^{30}$, —C(=O)OR$^{30}$, —C(=O)NR$^{32}$R$^{33}$, —NR$^{30}$R$^{31}$, C$_{1-6}$-alkyl-(R$^{35}$)$_x$, C$_{6-15}$-aryl-(R$^{35}$)$_x$, 5-15 membered heteroaryl-(R$^{35}$)$_x$, C$_{3-10}$ cycloalkyl-(R$^{35}$)$_x$, 3-15 membered heterocycloalkyl-(R$^{35}$)$_x$, pseudohalogen, —S(=O)R$^{30}$, —S(=O)$_2$NR$^{32}$R$^{33}$, —OCH$_2$F, —OCHF$_2$, —OCF$_3$, —NHOH, —OC(=O)R$^{30}$, —OC(=O)NR$^{32}$R$^{33}$, —NR$^{30}$C(=O)R$^{31}$, —NR$^{30}$C(=O)OR$^{31}$, —NR$^{30}$S(=O)$_2$R$^{31}$, —NR$^{30}$C(=O)NR$^{32}$R$^{33}$, —NR$^{30}$S(=O)$_2$NR$^{32}$R$^{33}$, and —SCF$_3$;

$A^1$, $A^2$, $A^3$, $A^4$, and $A^5$ are each independently —CZ$^1$Z$^2$—, wherein:

(a) when any two of $Z^1$ and $Z^2$ are located on adjacent atoms, they may form a bond between the atoms, (b) any of $Z^1$ and $Z^2$ may be independently chosen from H, halogen, —NO$_2$, —OR$^{40}$, —C(=O)R$^{40}$, —C(=O)OR$^{40}$, —C(=O)NR$^{42}$R$^{43}$, —NR$^{40}$R$^{41}$, C$_{1-6}$-alkyl-(R$^{45}$)$_x$, C$_{6-15}$-aryl-(R$^{45}$)$_x$, 5-15 membered heteroaryl-(R$^{45}$)$_x$, C$_{3-10}$ cycloalkyl-(R$^{45}$)$_x$, 3-15 membered heterocycloalkyl-(R$^{45}$)$_x$, C$_{2-6}$-alkenyl-(R$^{45}$)$_x$, C$_{2-6}$-alkynyl-(R$^{45}$)$_x$, pseudohalogen, —S(=O)$_n$R$^{40}$, —S(=O)$_2$NR$^{42}$R$^{43}$, —OCH$_2$F, —OCHF$_2$, —OCF$_3$, —NHOH, —OC(=O)R$^{40}$, —OC(=O)NR$^{42}$R$^{43}$, —NR$^{40}$C(=O)R$^{41}$, —NR$^{40}$C(=O)OR$^{41}$, —NR$^{40}$S(=O)$_2$R$^{41}$, —NR$^{40}$C(=O)NR$^{42}$R$^{43}$, —NR$^{40}$S(=O)$_2$NR$^{42}$R$^{43}$, and —SCF$_3$, and (c) any two of $Z^1$ and $Z^2$ may together form a group of formula -A$^6$-A$^7$-A$^8$-A$^9$-A$^{10}$-, wherein A$^6$, A$^7$, A$^8$, A$^9$, and A$^{10}$ are independently chosen from a bond, —CZ$^4$Z$^5$—, —C(=O)—, —NZ$^6$—, —S—, —S(=O)—, —S(=O)$_2$—, or —O—, wherein:

(i) when any two of $Z^1$, $Z^2$, $Z^3$, $Z^4$, $Z^5$, and $Z^6$ are located on adjacent atoms, they may form a bond between the atoms, and (ii) any of $Z^4$, $Z^5$, and $Z^6$ may be independently chosen from H, halogen, —NO$_2$, —OR$^{50}$, —C(=O)R$^{50}$, —C(=O)OR$^{50}$, —C(=O)NR$^{52}$R$^{53}$, —NR$^{50}$R$^{51}$, C$_{1-6}$-alkyl-(R$^{55}$)$_x$, C$_{6-15}$-aryl-(R$^{55}$)$_x$, 5-15 membered heteroaryl-(R$^{55}$)$_x$, C$_{3-10}$ cycloalkyl-(R$^{55}$)$_x$, 3-15 membered heterocycloalkyl-(R$^{55}$)$_x$, pseudohalogen, —S(=O)$_n$R$^{50}$, —S(=O)$_2$NR$^{52}$R$^{53}$, —OCH$_2$F, —OCHF$_2$, —OCF$_3$, —NHOH, —OC(=O)R$^{50}$, —OC(=O)NR$^{52}$R$^{53}$, —NR$^{50}$C(=O)R$^{51}$, —NR$^{50}$C(=O)OR$^{51}$, —NR$^{50}$S(=O)$_2$R$^{51}$, —NR$^{50}$C(=O)NR$^{52}$R$^{53}$, —NR$^{50}$S(=O)$_2$NR$^{52}$R$^{53}$, and —SCF$_3$;

$R^{25}$, $R^{35}$, $R^{45}$, and $R^{55}$ at each occurrence are independently chosen from halogen, —NO$_2$, —OR$^{60}$, =O, —C(=O)R$^{60}$, —C(=O)OR$^{60}$, —C(=O)NR$^{62}$R$^{63}$, —NR$^{60}$R$^{61}$, C$_{1-6}$-alkyl, C$_{1-6}$-haloalkyl, C$_{2-6}$-alkenyl, C$_{2-6}$-alkynyl, C$_{6-15}$-aryl, 5-15 membered heteroaryl, C$_{3-10}$ cycloalkyl, 3-15 membered heterocycloalkyl, pseudohalogen, —S(=O)$_n$R$^{60}$, —S(=O)$_2$NR$^{62}$R$^{63}$, —OCH$_2$F, —OCHF$_2$, —OCF$_3$, —NHOH, —OC(=O)R$^{60}$, —OC(=O)NR$^{62}$R$^{63}$, —OP(=O)(OH)$_2$, —NR$^{60}$C(=O)R$^{61}$, —NR$^{60}$C(=O)OR$^{61}$, —NR$^{60}$S(=O)$_2$R$^{61}$, —NR$^{60}$C(=O)NR$^{62}$R$^{63}$, —NR$^{60}$S(=O)$_2$NR$^{62}$R$^{63}$, and —SCF$_3$, in which said C$_{1-6}$-alkyl, C$_{1-6}$-haloalkyl, C$_{2-6}$-alkenyl, C$_{2-6}$-alkynyl, C$_{6-15}$-aryl, 5-15 membered heteroaryl, C$_{3-10}$ cycloalkyl, and 3-15 membered heterocycloalkyl groups are optionally substituted by one or more substituents independently chosen from $C_{1-6}$-alkyl, $C_{2-6}$-alkenyl, $C_{2-6}$-alkynyl, halogen, cyano, $C_{3-10}$ cycloalkyl, phenyl, 5-10 membered heteroaryl-$(R^{79})_x$, 3-10 membered heterocycloalkyl, $-N(R^{76})_2$, $-C(=O)OR^{76}$, $-C(=O)N(R^{76})_2$, $=O$, and $-OR^{76}$;

$R^{10}, R^{11}, R^{20}, R^{21}, R^{30}, R^{31}, R^{40}, R^{41}, R^{50}, R^{51}, R^{60}, R^{61}$ at each occurrence are independently chosen from H, $C_{1-6}$-alkyl, $C_{2-6}$-alkynyl, $C_{1-6}$-haloalkyl, $C_{6-15}$-aryl, 5-15 membered heteroaryl, $C_{3-10}$ cycloalkyl, and 3-15 membered heterocycloalkyl, in which said $C_{1-6}$-alkyl, $C_{2-6}$-alkynyl, $C_{1-6}$-haloalkyl, $C_{6-15}$-aryl, 5-15 membered heteroaryl, $C_{3-10}$ cycloalkyl, and 3-15 membered heterocycloalkyl groups are optionally substituted by one or more substituents independently chosen from $C_{1-6}$-alkyl, $C_{2-6}$-alkenyl, $C_{2-6}$-alkynyl, halogen, cyano, phenyl, 5-10 membered heteroaryl-$(R^{79})_x$, 3-10 membered heterocycloalkyl, $-N(R^{76})_2$, $-C(=O)OR^{76}$, $-C(=O)N(R^{76})_2$, $=O$, and $-OR^{76}$;

$R^{12}, R^{13}, R^{22}, R^{23}, R^{32}, R^{33}, R^{42}, R^{43}, R^{52}, R^{53}, R^{62}$, and $R^{63}$ at each occurrence are independently chosen from H, $C_{1-6}$-alkyl, $C_{2-6}$-alkynyl, $C_{1-6}$-haloalkyl, $C_{6-15}$-aryl, 5-15 membered heteroaryl, $C_{3-10}$ cycloalkyl, and 3-15 membered heterocycloalkyl, in which said $C_{1-6}$-alkyl, $C_{2-6}$-alkynyl, $C_{1-6}$-haloalkyl, $C_{6-15}$-aryl, 5-15 membered heteroaryl, $C_{3-10}$ cycloalkyl, and 3-15 membered heterocycloalkyl groups are optionally substituted by one or more substitutents independently chosen from $C_{1-6}$-alkyl, halogen, $C_{3-10}$ cycloalkyl, 3-10 membered heterocycloalkyl-$(R^{87})_x$, $-N(R^{86})_2$, cyano, $C_{2-6}$-alkynyl, $=O$, and $-OR^{86}$;

or $R^{12}$ and $R^{13}$, $R^{22}$ and $R^{23}$, $R^{32}$ and $R^{33}$, $R^{42}$ and $R^{43}$, $R^{52}$ and $R^{53}$, or $R^{62}$ and $R^{63}$ may form, together with the nitrogen atom to which they are attached, a 3-15 membered heterocycloalkyl group or a 5-15 membered heteroaryl group, in which said 3-15 membered heterocycloalkyl group or 5-15 membered heteroaryl group is optionally substituted by one or more substituents independently chosen from $C_{1-6}$-alkyl, halogen, and $-OH$;

$R^{76}$ and $R^{86}$ at each occurrence are independently chosen from H, $C_{1-6}$-alkyl-$(R^{78})_x$, and $-C(=O)-C_{1-6}$-alkyl;

$R^{78}$ at each occurrence is independently chosen from $=O$ and phenyl;

$R^{79}$ at each occurrence is $=O$;

$R^{87}$ at each occurrence is independently chosen from $C_{1-6}$-alkyl;

n at each occurrence is independently chosen from 0, 1, and 2; and x at each occurrence is independently chosen from 0, 1, 2, 3, 4, 5, and 6;

with the proviso that the compound is not:

(a)

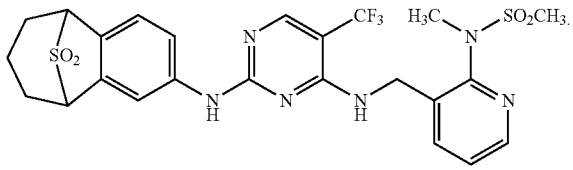

2. A pharmaceutical composition comprising a compound as defined in claim 1 and at least one pharmaceutically acceptable carrier, diluent, or excipient therefor.

3. A pharmaceutical composition as defined in claim 2, wherein the compound is a compound of formula I or a pharmaceutically acceptable salt thereof.

4. A pharmaceutical composition as defined in claim 2, wherein the compound is a compound of formula II or a pharmaceutically acceptable salt thereof.

5. A compound of formula I as defined in claim 1, wherein said compound is:
- 4-[5-Chloro-4-(2-methylcarbamoyl-phenylamino)-pyrimidin-2-ylamino]-12-aza-tricyclo[7.2.1.0*2,7*]dodeca-2(7),3,5-triene-12-carboxylic acid ethyl ester;
- 2-{5-Chloro-2-[12-(2-methoxy-ethyl)-12-aza-tricyclo[7.2.1.0*2,7*]dodeca-2(7),3,5-trien-4-ylamino]-pyrimidin-4-ylamino}-N-methyl-benzamide;
- 2-[5-Chloro-2-(12-prop-2-ynyl-12-aza-tricyclo[7.2.1.0*2,7*]dodeca-2(7),3,5-trien-4-ylamino)-pyrimidin-4-ylamino]-N-methyl-benzamide;
- 2-[5-Chloro-2-(12-cyclopropanecarbonyl-12-aza-tricyclo[7.2.1.0*2,7*]dodeca-2(7),3,5-trien-4-ylamino)-pyrimidin-4-ylamino]-N-methyl-benzamide;
- N-{(1R,2R)-2-[5-Chloro-2-(12-ethyl-12-aza-tricyclo[7.2.1.0*2,7*]dodeca-2(7),3,5-trien-4-ylamino)-pyrimidin-4-ylamino]-cyclohexyl}-methanesulfonamide;
- N-{2-[5-Chloro-2-(12-ethyl-12-aza-tricyclo[7.2.1.0*2,7*]dodeca-2(7),3,5-trien-4-ylamino)-pyrimidin-4-ylamino]-phenyl}-methanesulfonamide;
- 2-[5-Chloro-2-(3-chloro-12-ethyl-12-aza-tricyclo[7.2.1.0*2,7*]dodeca-2(7),3,5-trien-4-ylamino)-pyrimidin-4-ylamino]-N-methyl-benzamide;
- 5-Chloro-4-[5-chloro-4-(2-methylcarbamoyl-phenylamino)-pyrimidin-2-ylamino]-12-aza-tricyclo[7.2.1.0*2,7*]dodeca-2(7),3,5-triene-12-carboxylic acid ethyl ester;
- 3-Chloro-4-[5-chloro-4-(2-methylcarbamoyl-phenylamino)-pyrimidin-2-ylamino]-12-aza-tricyclo[7.2.1.0*2,7*]dodeca-2(7),3,5-triene-12-carboxylic acid ethyl ester;
- N-(2-{5-Chloro-2-[12-(2-methoxy-ethyl)-12-aza-tricyclo[7.2.1.0*2,7*]dodeca-2(7),3,5-trien-4-ylamino]-pyrimidin-4-ylamino}-phenyl)-methanesulfonamide;
- N-((1R,2R)-2-{5-Chloro-2-[12-(2-methoxy-ethyl)-12-aza-tricyclo[7.2.1.0*2,7*]dodeca-2(7),3,5-trien-4-ylamino]-pyrimidin-4-ylamino}-cyclohexyl)-methanesulfonamide;
- 2-[2-(12-Aza-tricyclo[7.2.1.0*2,7*]dodeca-2(7),3,5-trien-4-ylamino)-5-chloro-pyrimidin-4-ylamino]-N-methyl-benzamide;
- 2-[5-Chloro-2-(12-isopropyl-12-aza-tricyclo[7.2.1.0*2,7*]dodeca-2(7),3,5-trien-4-ylamino)-pyrimidin-4-ylamino]-N-methyl-benzamide;
- 2-[5-Chloro-2-(3-chloro-12-aza-tricyclo[7.2.1.0*2,7*]dodeca-2(7),3,5-trien-4-ylamino)-pyrimidin-4-ylamino]-N-methyl-benzamide;
- N-{(1R,2R)-2-[2-(12-Aza-tricyclo[7.2.1.0*2,7*]dodeca-2(7),3,5-trien-4-ylamino)-5-chloro-pyrimidin-4-ylamino]-cyclohexyl}-methanesulfonamide;
- N-{(1R,2R)-2-[5-Chloro-2-(12-isopropyl-12-aza-tricyclo[7.2.1.0*2,7*]dodeca-2(7),3,5-trien-4-ylamino)-pyrimidin-4-ylamino]-cyclohexyl}-methanesulfonamide;
- N-{(1R,2R)-2-[2-(12-sec-Butyl-12-aza-tricyclo[7.2.1.0*2,7*]dodeca-2(7),3,5-trien-4-ylamino)-5-chloro-pyrimidin-4-ylamino]-cyclohexyl}-methanesulfonamide;
- N-{(1R,2R)-2-[2-(12-sec-Butyl-12-aza-tricyclo[7.2.1.0*2,7*]dodeca-2(7),3,5-trien-4-ylamino)-5-chloro-pyrimidin-4-ylamino]-cyclohexyl}-methanesulfonamide;

2-[5-Chloro-2-(3-chloro-12-isopropyl-12-aza-tricyclo [7.2.1.0*2,7*]dodeca-2(7),3,5-trien-4-ylamino)-pyrimidin-4-ylamino]-N-methyl-benzamide;

2-{5-Chloro-2-[3-chloro-12-(2-methoxy-ethyl)-12-aza-tricyclo[7.2.1.0*2,7*]dodeca-2(7),3,5-trien-4-ylamino]-pyrimidin-4-ylamino}-N-methyl-benzamide;

2-{5-Chloro-2-[5-chloro-12-(2-methoxy-ethyl)-12-aza-tricyclo[7.2.1.0*2,7*]dodeca-2(7),3,5-trien-4-ylamino]-pyrimidin-4-ylamino}-N-methyl-benzamide;

N-{(1R,2R)-2-[2-(12-sec-Butyl-12-aza-tricyclo [7.2.1.0*2,7*]dodeca-2(7),3,5-trien-4-ylamino)-5-chloro-pyrimidin-4-ylamino]-cyclohexyl}-methanesulfonamide;

2-[2-(12-Aza-tricyclo[7.2.1.0*2,7*]dodeca-2(7),3,5-trien-4-ylamino)-5-chloro-pyrimidin-4-ylamino]-3-chloro-N-methyl-benzamide;

3-Chloro-2-{5-chloro-2-[12-(2-methoxy-ethyl)-12-aza-tricyclo[7.2.1.0*2,7*]dodeca-2(7),3,5-trien-4-ylamino]-pyrimidin-4-ylamino}-N-methyl-benzamide;

N-{(1R,2R)-2-[5-Chloro-2-(3-methoxy-12-aza-tricyclo [7.2.1.0*2,7*]dodeca-2(7),3,5-trien-4-ylamino)-pyrimidin-4-ylamino]-cyclohexyl}-methanesulfonamide;

N-{(1R,2R)-2-[5-Chloro-2-(12-ethyl-3-methoxy-12-aza-tricyclo[7.2.1.0*2,7*]dodeca-2(7),3,5-trien-4-ylamino)-pyrimidin-4-ylamino]-cyclohexyl}-methanesulfonamide;

(+/−)-2-[5-Chloro-2-(12-ethyl-12-aza-tricyclo[7.2.1.0*2, 7*]dodeca-2(7),3,5-trien-4-ylamino)-pyrimidin-4-ylamino]-N-methyl-benzamide;

(+/−)-2-[5-Chloro-2-(12-methanesulfonyl-12-aza-tricyclo [7.2.1.0*2,7*]dodeca-2(7),3,5-trien-4-ylamino)-pyrimidin-4-ylamino]-N-methyl-benzamide;

2-[5-Chloro-2-(7-oxo-6,7,8,9-tetrahydro-5H-benzocyclohepten-2-ylamino)-pyrimidin-4-ylamino]-N-methyl-benzamide;

(2-exo,3-exo)-3-[5-Chloro-2-(7-oxo-6,7,8,9-tetrahydro-5H-benzocyclo-hepten-2-ylamino)-pyrimidin-4-ylamino]-bicyclo[2.2.1]hept-5-ene-2-carboxylic acid amide;

N-{(1R,2R)-2-[5-Chloro-2-(7-oxo-6,7,8,9-tetrahydro-5H-benzocyclohepten-2-ylamino)-pyrimidin-4-ylamino]-cyclohexyl}-methanesulfonamide;

2-[5-Chloro-4-(2-methoxy-4-morpholin-4-yl-phenylamino)-pyrimidin-2-ylamino]-5,6,8,9-tetrahydro-benzocyclohepten-7-one;

2-[5-Chloro-2-(7-morpholin-4-yl-6,7,8,9-tetrahydro-5H-benzocyclohepten-2-ylamino)-pyrimidin-4-ylamino]-N-methyl-benzamide;

N-{(1R,2R)-2-[5-Chloro-2-(7-morpholin-4-yl-6,7,8,9-tetrahydro-5H-benzocyclohepten-2-ylamino)-pyrimidin-4-ylamino]-cyclohexyl}-methanesulfonamide;

2-[5-Chloro-2-(7,7-difluoro-6,7,8,9-tetrahydro-5H-benzocyclohepten-2-ylamino)-pyrimidin-4-ylamino]-N-methyl-benzamide;

N-{(1R,2R)-2-[5-Chloro-2-(7,7-difluoro-6,7,8,9-tetrahydro-5H-benzocyclohepten-2-ylamino)-pyrimidin-4-ylamino]-cyclohexyl}-methanesulfonamide;

5-Chloro-N*2*-(7,7-difluoro-6,7,8,9-tetrahydro-5H-benzocyclohepten-2-yl)-N*4* -(2-methoxy-4-morpholin-4-yl-phenyl)-pyrimidine-2,4-diamine;

2-{5-Chloro-4-[2-(1-methyl-1H-imidazol-2-yl)-phenylamino]-pyrimidin-2-ylamino}-5,6,8,9-tetrahydro-benzocyclohepten-7-one;

5-Chloro-N*4*-[2-(1-methyl-1H-imidazol-2-yl)-phenyl]-N*2*-(7-morpholin-4-yl-6,7,8,9-tetrahydro-5H-benzocyclohepten-2-yl)-pyrimidine-2,4-diamine;

5-Chloro-N*2*-(7,7-difluoro-6,7,8,9-tetrahydro-5H-benzocyclohepten-2-yl)-N*4*-[2-(1-methyl-1H-imidazol-2-yl)-phenyl]-pyrimidine-2,4-diamine;

2-{5-Chloro-2-[12-(2-methoxy-ethyl)-12-aza-tricyclo [7.2.1.0(2,7)]dodeca-2(7),3,5-trien-4-ylamino]-pyrimidin-4-ylamino}-3-fluoro-N-methyl-benzamide;

2-{5-Chloro-2-[12-(2-methoxy-ethyl)-12-aza-tricyclo [7.2.1.0(2,7)]dodeca-2(7),3,5-trien-4-ylamino]-pyrimidin-4-ylamino-}-3-fluoro-benzoic acid isopropyl ester;

5-Chloro-N*4*-(4-methoxy-2-pyrazol-1-yl-phenyl)-N*2*-(7-morpholin-4-yl-6,7,8,9-tetrahydro-5H-benzocyclohepten-2-yl)-pyrimidine-2,4-diamine;

2-[5-Chloro-4-(4-methoxy-2-pyrazol-1-yl-phenylamino)-pyrimidin-2-ylamino]-6,7,8,9-tetrahydro-5H-benzocyclohepten-7-ol;

(2-exo-3-exo)-3-[5-Chloro-2-(7-morpholin-4-yl-6,7,8,9-tetrahydro-5H-benzocyclohepten-2-ylamino)-pyrimidin-4-ylamino]-bicyclo[2.2.1]hept-5-ene-2-carboxylic acid methylamide;

(2-exo-3-exo)-3-[5-Chloro-2-(7-hydroxy-6,7,8,9-tetrahydro-5H-benzocyclohepten-2-ylamino)-pyrimidin-4-ylamino]-bicyclo[2.2.1]hept-5-ene-2-carboxylic acid methylamide;

(1S,2S,3R,4R)-3-[2-((S)-7-Acetylamino-1-methoxy-9-oxo-6,7,8,9-tetrahydro-5H-benzocyclohepten-2-ylamino)-5-chloro-pyrimidin-4-ylamino]-bicyclo [2.2.1]hept-5-ene-2-carboxylic acid amide;

2-{5-Chloro-2-[7-(2,2,2-trifluoro-ethylamino)-6,7,8,9-tetrahydro-5H-benzocyclohepten-2-ylamino]-pyrimidin-4-ylamino}-N-methyl-benzamide;

5-Chloro-N*4*-(2-ethyl-4-morpholin-4-yl-phenyl)-N*2*-[7-(2,2,2-trifluoro-ethylamino)-6,7,8,9-tetrahydro-5H-benzocyclohepten-2-yl]-pyrimidine-2,4-diamine;

(1R,2R)-2-5-Chloro-2-[7-(2,2,2-trifluoro-ethylamino)-6, 7,8,9-tetrahydro-5H-benzocyclohepten-2-ylamino]-pyrimidin-4-ylamino-cyclohexanecarboxylic acid amide;

1S,2R,3S,4R)-3-{5-Chloro-2-[7-(2,2,2-trifluoro-ethylamino)-6,7,8,9-tetrahydro-5H-benzocyclohepten-2-ylamino]-pyrimidin-4-ylamino}-bicyclo[2.2.1]heptane-2-carboxylic acid amide;

5-Chloro-N*4*-[2-(1-methyl-1H-imidazol-2-yl)-phenyl]-N*2*-[7-(2,2,2-trifluoro-ethylamino)-6,7,8,9-tetrahydro-5H-benzocyclohepten-2-yl]-pyrimidine-2,4-diamine;

N-((1R,2R)-2-{5-Chloro-2-[7-(2,2,2-trifluoro-ethylamino)-6,7,8,9-tetrahydro-5H-benzocyclohepten-2-ylamino]-pyrimidin-4-ylamino}-cyclohexyl)-methanesulfonamide;

5-Chloro-N*4*-[2-(3-methyl-pyridin-2-yl)-phenyl]-N*2*-[7-(2,2,2-trifluoro-ethylamino)-6,7,8,9-tetrahydro-5H-benzocyclohepten-2-yl]-pyrimidine-2,4-diamine;

5-Chloro-N*4*-(2-methoxy-phenyl)-N*2*-[7-(2,2,2-trifluoro-ethylamino)-6,7,8,9-tetrahydro-5H-benzocyclohepten-2-yl]-pyrimidine-2,4-diamine;

5-Chloro-N*2*-[7-(2,2-difluoro-ethylamino)-6,7,8,9-tetrahydro-5H-benzocyclohepten-2-yl]-N*4*-(2-methoxy-4-morpholin-4-yl-phenyl)-pyrimidine-2,4-diamine;

2-{5-Chloro-2-[7-(2,2-difluoro-ethylamino)-6,7,8,9-tetrahydro-5H-benzocyclohepten-2-ylamino]-pyrimidin-4-ylamino}-N-methyl-benzamide;

5-Chloro-N*2*-[7-(2,2-difluoro-ethylamino)-6,7,8,9-tetrahydro-5H-benzocyclohepten-2-yl]-N*4*-[2-(1-methyl-1H-imidazol-2-yl)-phenyl]-pyrimidine-2,4-diamine;

N-((1R,2R)-2-{5-Chloro-2-[7-(2,2-difluoro-ethylamino)-6,7,8,9-tetrahydro-5H-benzocyclohepten-2-ylamino]-pyrimidin-4-ylamino}-cyclohexyl)-methanesulfonamide;

5-Chloro-N*2*-[7-(2,2-difluoro-ethylamino)-6,7,8,9-tetrahydro-5H-benzocyclohepten-2-yl]-N*4*-(2-methoxy-phenyl)-pyrimidine-2,4-diamine;

2-{5-Chloro-2-[7-(2,2-difluoro-ethylamino)-6,7,8,9-tetrahydro-5H-benzocyclohepten-2-ylamino]-pyrimidin-4-ylamino}-3-fluoro-N-methyl-benzamide;

(1S,2S,3R,4R)-3-{5-Chloro-2-[7-(2,2-difluoro-ethylamino)-6,7,8,9-tetrahydro-5H-benzocyclohepten-2-ylamino]-pyrimidin-4-ylamino}-bicyclo[2.2.1]hept-5-ene-2-carboxylic;

(1S,2S,3R,4R)-3-[5-Chloro-2-(7-morpholin-4-yl-6,7,8,9-tetrahydro-5H-benzocyclohepten-2-ylamino)-pyrimidin-4-ylamino]-bicyclo[2.2.1]hept-5-ene-2-carboxylic acid amide;

N-((1R,2R)-2-[5-Chloro-2-[7-(2,2-difluoro-ethylamino)-6,7,8,9-tetrahydro-5H-benzocyclohepten-2-ylamino]-pyrimidin-4-ylamino-cyclohexyl)-methanesulfonamide;

N-((1R,2R)-2-[5-Chloro-2-[7-(2,2,2-trifluoro-ethylamino)-6,7,8,9-tetrahydro-5H-benzocyclohepten-2-ylamino]-pyrimidin-4-ylamino-cyclohexyl)-methanesulfonamide;

(1S,2S,3R,4R)-3-{5-Chloro-2-[7-(2,2-difluoro-ethylamino)-6,7,8,9-tetrahydro-5H-benzocyclohepten-2-ylamino]-pyrimidin-4-ylamino}-bicyclo[2.2.1]hept-5-ene-2-carboxylic acid amide;

5-Chloro-N*2*-[7-(2,2-difluoro-ethylamino)-1-methoxy-6,7,8,9-tetrahydro-5H-benzocyclohepten-2-yl]-N*4*-methyl-N*4*-[2-(propane-2-sulfonyl)-phenyl]-pyrimidine-2,4-diamine;

(1S,2S,3R,4R)-3-{5-Chloro-2-[1-methoxy-7-(2,2,2-trifluoro-ethylamino)-6,7,8,9-tetrahydro-5H-benzocyclohepten-2-ylamino]-pyrimidin-4-ylamino}-bicyclo[2.2.1]hept-5-ene-2-carboxylic acid amide;

5-Chloro-N*2*-[1-methoxy-7-(2,2,2-trifluoro-ethylamino)-6,7,8,9-tetrahydro-5H-benzocyclohepten-2-yl]-N*4*-methyl-N*4*-[2-(propane-2-sulfonyl)-phenyl]-pyrimidine-2,4-diamine;

1S,2S,3R,4R)-3-[5-Chloro-2-(7-morpholin-4-yl-6,7,8,9-tetrahydro-5H-benzocyclohepten-2-ylamino)-pyrimidin-4-ylamino]-bicyclo[2.2.1]hept-5-ene-2-carboxylic acid amide;

1S,2S,3R,4R)-3-[5-Chloro-2-(7-morpholin-4-yl-6,7,8,9-tetrahydro-5H-benzocyclohepten-2-ylamino)-pyrimidin-4-ylamino]-bicyclo[2.2.1]hept-5-ene-2-carboxylic acid amide;

2-{5-Chloro-2-[7-(2,2-difluoro-ethylamino)-1-methoxy-6,7,8,9-tetrahydro-5H-benzocyclohepten-2-ylamino]-pyrimidin-4-ylamino}-N,N-dimethyl-benzenesulfonamide;

2-{5-Chloro-2-[1-methoxy-7-(2,2,2-trifluoro-ethylamino)-6,7,8,9-tetrahydro-5H-benzocyclohepten-2-ylamino]-pyrimidin-4-ylamino}-N,N-dimethyl-benzenesulfonamide;

N-((1R,2R)-2-{5-Chloro-2-[7-(2,2-difluoro-ethylamino)-6,7,8,9-tetrahydro-5H-benzocyclohepten-2-ylamino]-pyrimidin-4-ylamino}-cyclohexyl)-methanesulfonamide;

N-((1R,2R)-2-{5-Chloro-2-[7-(2,2-difluoro-ethylamino)-6,7,8,9-tetrahydro-5H-benzocyclohepten-2-ylamino]-pyrimidin-4-ylamino}-cyclohexyl)-methanesulfonamide;

N-((1R,2R)-2-{5-Chloro-2-[7-(2,2,2-trifluoro-ethylamino)-6,7,8,9-tetrahydro-5H-benzocyclohepten-2-ylamino]-pyrimidin-4-ylamino}-cyclohexyl)-methanesulfonamide;

N-((1R,2R)-2-{5-Chloro-2-[7-(2,2,2-trifluoro-ethylamino)-6,7,8,9-tetrahydro-5H-benzocyclohepten-2-ylamino]-pyrimidin-4-ylamino}-cyclohexyl)-methanesulfonamide;

-Chloro-N*2*-[7-(2,2-difluoro-ethylamino)-1-methoxy-6,7,8,9-tetrahydro-5H-benzocyclohepten-2-yl]-N*4*-(2-pyrazol-1-yl-phenyl)-pyrimidine-2,4-diamine;

5-Chloro-N*2*-[1-methoxy-7-(2,2,2-trifluoro-ethylamino)-6,7,8,9-tetrahydro-5H-benzocyclohepten-2-yl]-N*4*-(2-pyrazol-1-yl-phenyl)-pyrimidine-2,4-diamine;

(1S,2S,3R,4R)-3-{5-Chloro-2-[1-methoxy-7-(2-methoxy-ethylamino)-6,7,8,9-tetrahydro-5H-benzocyclohepten-2-ylamino]-pyrimidin-4-ylamino}-bicyclo[2.2.1]hept-5-ene-2-carboxylic acid amide;

(1S,2S,3R,4R)-3-{5-Chloro-2-[1-methoxy-7-(2-methoxy-ethylamino)-6,7,8,9-tetrahydro-5H-benzocyclohepten-2-ylamino]-pyrimidin-4-ylamino}-bicyclo[2.2.1]hept-5-ene-2-carboxylic acid amide;

N-((1R,2R)-2-{5-Chloro-2-[1-methoxy-7-(2-methoxy-ethylamino)-6,7,8,9-tetrahydro-5H-benzocyclohepten-2-ylamino]-pyrimidin-4-ylamino}-cyclohexyl)-methanesulfonamide;

N-((1R,2R)-2-{5-Chloro-2-[1-methoxy-7-(2-methoxy-ethylamino)-6,7,8,9-tetrahydro-5H-benzocyclohepten-2-ylamino]-pyrimidin-4-ylamino}-cyclohexyl)-methanesulfonamide;

1-(2-{5-Chloro-2-[1-methoxy-7-(2-methoxy-ethylamino)-6,7,8,9-tetrahydro-5H-benzocyclohepten-2-ylamino]-pyrimidin-4-ylamino}-benzenesulfonyl)-pyrrolidin-3-ol;

1S,2S,3R,4R)-3-{5-Chloro-2-[7-(2-hydroxy-ethylamino)-1-methoxy-6,7,8,9-tetrahydro-5H-benzocyclohepten-2-ylamino]-pyrimidin-4-ylamino}-bicyclo[2.2.1]hept-5-ene-2-carboxylic acid amide;

(1S,2S,3R,4R)-3-{5-Chloro-2-[7-(2-hydroxy-ethylamino)-1-methoxy-6,7,8,9-tetrahydro-5H-benzocyclohepten-2-ylamino]-pyrimidin-4-ylamino}-bicyclo[2.2.1]hept-5-ene-2-carboxylic acid amide;

N-((1R,2R)-2-{5-Chloro-2-[7-(2-hydroxy-ethylamino)-1-methoxy-6,7,8,9-tetrahydro-5H-benzocyclohepten-2-ylamino]-pyrimidin-4-ylamino}-cyclohexyl)-methanesulfonamide;

N-((1R,2R)-2-{5-Chloro-2-[7-(2-hydroxy-ethylamino)-1-methoxy-6,7,8,9-tetrahydro-5H-benzocyclohepten-2-ylamino]-pyrimidin-4-ylamino}-cyclohexyl)-methanesulfonamide;

(1S,2S,3R,4R)-3-(5-Chloro-2-{1-methoxy-7-[(2-methoxy-ethyl)-methyl-amino]-6,7,8,9-tetrahydro-5H-benzocyclohepten-2-ylamino}-pyrimidin-4-ylamino)-bicyclo[2.2.1]hept-5-ene-2-carboxylic acid amide;

(1S,2S,3R,4R)-3-(5-Chloro-2-{1-methoxy-7-[(2-methoxy-ethyl)-methyl-amino]-6,7,8,9-tetrahydro-5H-benzocyclohepten-2-ylamino}-pyrimidin-4-ylamino)-bicyclo[2.2.1]hept-5-ene-2-carboxylic acid amide;

N-[(1R,2R)-2-(5-Chloro-2-{1-methoxy-7-[(2-methoxy-ethyl)-methyl-amino]-6,7,8,9-tetrahydro-5H-benzocyclohepten-2-ylamino}-pyrimidin-4-ylamino)-cyclohexyl]-methanesulfonamide;

1-(2-{5-Chloro-2-[7-(2-hydroxy-ethylamino)-1-methoxy-6,7,8,9-tetrahydro-5H-benzocyclohepten-2-ylamino]-pyrimidin-4-ylamino}-benzenesulfonyl)-pyrrolidin-3-ol;

2-(2-{5-Chloro-4-[2-(pyrrolidine-1-sulfonyl)-phenylamino]-pyrimidin-2-ylamino}-1-methoxy-6,7,8,9-tetrahydro-5H-benzocyclohepten-7-ylamino)-ethanol;

2-{2-[5-Chloro-4-(2-methoxy-4-morpholin-4-yl-phenylamino)-pyrimidin-2-ylamino]-1-methoxy-6,7,8,9-tetrahydro-5H-benzocyclohepten-7-ylamino}-ethanol;

2-([5-[5-Chloro-2-(1-methoxy-7-morpholin-4-yl-6,7,8,9-tetrahydro-5H-benzocyclohepten-2-ylamino)-pyrimidin-4-ylamino]-2-fluoro-benzyl]-ethylamino)-ethanol;

6-{5-Chloro-2-[3-methoxy-7-(2-methoxy-ethylamino)-6,7,8,9-tetrahydro-5H-benzocyclohepten-2-ylamino]-pyrimidin-4-ylamino}-4-methanesulfonyl-7-methoxy-1,3,4,5-tetrahydro-benzo[e][1,4]diazepin-2-one;

5-Chloro-N*4*-(2-methoxy-4-morpholin-4-yl-phenyl)-N*2*-(7-morpholin-4-yl-6,7,8,9-tetrahydro-5H-benzocyclohepten-2-yl)-pyrimidine-2,4-diamine;

2-[5-Chloro-2-(7-morpholin-4-yl-6,7,8,9-tetrahydro-5H-benzocyclohepten-2-ylamino)-pyrimidin-4-ylamino]-N-ethyl-benzamide;

3-[5-Chloro-2-(7-morpholin-4-yl-6,7,8,9-tetrahydro-5H-benzocyclohepten-2-ylamino)-pyrimidin-4-ylamino]-bicyclo[2.2.1]hept-5-ene-2-carboxylic acid amide;

2-[5-Chloro-2-(1-methoxy-7-oxo-6,7,8,9-tetrahydro-5H-benzocyclohepten-2-ylamino)-pyrimidin-4-ylamino]-N-methyl-benzamide;

(1S,2S,3R,4R)-3-[5-Chloro-2-(1-methoxy-7-oxo-6,7,8,9-tetrahydro-5H-benzocyclohepten-2-ylamino)-pyrimidin-4-ylamino]-bicyclo[2.2.1]hept-5-ene-2-carboxylic acid amide;

(1S,2S,3R,4R)-3-[5-Chloro-2-((R)-1-methoxy-7-morpholin-4-yl-6,7,8,9-tetrahydro-5H-benzocyclohepten-2-ylamino)-pyrimidin-4-ylamino]-bicyclo[2.2.1]hept-5-ene-2-carboxylic acid amide;

(1S,2S,3R,4R)-3-[5-Chloro-2-((S)-1-methoxy-7-morpholin-4-yl-6,7,8,9-tetrahydro-5H-benzocyclohepten-2-ylamino)-pyrimidin-4-ylamino]-bicyclo[2.2.1]hept-5-ene-2-carboxylic acid amide;

5-Chloro-N*2*-(1-methoxy-7-morpholin-4-yl-6,7,8,9-tetrahydro-5H-benzocyclohepten-2-yl)-N*4*-[2-(propane-2-sulfonyl)-phenyl]-pyrimidine-2,4-diamine;

N-{(1R,2R)-2-[5-Chloro-2-(1-methoxy-7-morpholin-4-yl-6,7,8,9-tetrahydro-5H-benzocyclohepten-2-ylamino)-pyrimidin-4-ylamino]-cyclohexyl}-methanesulfonamide;

N-[(1R,2R)-2-(5-Chloro-2-{7-[4-(4-methyl-piperazin-1-yl)-piperidin-1-yl]-6,7,8,9-tetrahydro-5H-benzocyclohepten-2-ylamino}-pyrimidin-4-ylamino)-cyclohexyl]-methanesulfonamide;

(1S,2S,3R,4R)-3-(5-Chloro-2-{7-[4-(4-methyl-piperazin-1-yl)-piperidin-1-yl]-6,7,8,9-tetrahydro-5H-benzocyclohepten-2-ylamino}-pyrimidin-4-ylamino)-bicyclo[2.2.1]hept-5-ene-2-carboxylic acid amide;

N-((1R,2R)-2-{5-Chloro-2-[7-(4-methyl-piperazin-1-yl)-6,7,8,9-tetrahydro-5H-benzocyclohepten-2-ylamino]-pyrimidin-4-ylamino}-cyclohexyl)-methanesulfonamide;

2-[5-Chloro-2-(1-methoxy-7-morpholin-4-yl-6,7,8,9-tetrahydro-5H-benzocyclohepten-2-ylamino)-pyrimidin-4-ylamino]-N,N-dimethyl-benzenesulfonamide;

2-{5-Chloro-2-[7-(4-methyl-piperazin-1-yl)-6,7,8,9-tetrahydro-5H-benzocyclohepten-2-ylamino]-pyrimidin-4-ylamino}-N,N-dimethyl-benzenesulfonamide;

5-Chloro-N*4*-(2-methoxy-phenyl)-N*2*-[7-(4-methyl-piperazin-1-yl)-6,7,8,9-tetrahydro-5H-benzocyclohepten-2-yl]-pyrimidine-2,4-diamine;

(1S,2S,3R,4R)-3-{5-Chloro-2-[7-(4-methyl-piperazin-1-yl)-6,7,8,9-tetrahydro-5H-benzocyclohepten-2-ylamino]-pyrimidin-4-ylamino}-bicyclo[2.2.1]hept-5-ene-2-carboxylic acid amide;

(2-{5-Chloro-2-[7-(4-methyl-piperazin-1-yl)-6,7,8,9-tetrahydro-5H-benzocyclohepten-2-ylamino]-pyrimidin-4-ylamino}-phenoxy)-acetonitrile;

5-Chloro-N*4*-(2-methoxy-4-morpholin-4-yl-phenyl)-N*2*-(1-methoxy-7-morpholin-4-yl-6,7,8,9-tetrahydro-5H-benzocyclohepten-2-yl)-pyrimidine-2,4-diamine;

N-((1R,2R)-2-{5-Chloro-2-[3-methoxy-7-(2-methoxy-ethylamino)-6,7,8,9-tetrahydro-5H-benzocyclohepten-2-ylamino]-pyrimidin-4-ylamino}-cyclohexyl)-methanesulfonamide;

N-((1R,2R)-2-{5-Chloro-2-[3-methoxy-7-(2-methoxy-ethylamino)-6,7,8,9-tetrahydro-5H-benzocyclohepten-2-ylamino]-pyrimidin-4-ylamino}-cyclohexyl)-methanesulfonamide;

(1S,2S,3R,4R)-3-{5-Chloro-2-[3-methoxy-7-(2-methoxy-ethylamino)-6,7,8,9-tetrahydro-5H-benzocyclohepten-2-ylamino]-pyrimidin-4-ylamino}-bicyclo[2.2.1]hept-5-ene-2-carboxylic acid amide;

(1S,2S,3R,4R)-3-{5-Chloro-2-[3-methoxy-7-(2-methoxy-ethylamino)-6,7,8,9-tetrahydro-5H-benzocyclohepten-2-ylamino]-pyrimidin-4-ylamino}-bicyclo[2.2.1]hept-5-ene-2-carboxylic acid amide;

2-{5-Chloro-2-[7-(4-methyl-piperazin-1-yl)-6,7,8,9-tetrahydro-5H-benzocyclohepten-2-ylamino]-pyrimidin-4-ylamino}-3-fluoro-N-methyl-benzamide;

5-Chloro-N*2*-(1-methoxy-7-morpholin-4-yl-6,7,8,9-tetrahydro-5H-benzocyclohepten-2-yl)-N*4*-[2-(pyrrolidine-1-sulfonyl)-phenyl]-pyrimidine-2,4-diamine;

5-Chloro-N*2*-(1-methoxy-7-morpholin-4-yl-6,7,8,9-tetrahydro-5H-benzocyclohepten-2-yl)-N*4*-(2-pyrazol-1-yl-phenyl)-pyrimidine-2,4-diamine;

3-[5-Chloro-2-(1-methoxy-7-morpholin-4-yl-6,7,8,9-tetrahydro-5H-benzocyclohepten-2-ylamino)-pyrimidin-4-ylamino]-azepan-2-one;

(1S,3R,4R)-3-[5-Chloro-2-((S)-1-methoxy-7-morpholin-4-yl-6,7,8,9-tetrahydro-5H-benzocyclohepten-2-ylamino)-pyrimidin-4-ylamino]-bicyclo[2.2.1]hept-5-ene-2-carboxylic acid 2-methoxy-ethyl ester;

(1S,3R,4R)-3-[5-Chloro-2-((S)-1-methoxy-7-morpholin-4-yl-6,7,8,9-tetrahydro-5H-benzocyclohepten-2-ylamino)-pyrimidin-4-ylamino]-bicyclo[2.2.1]hept-5-ene-2-carboxylic acid 2-methoxy-ethyl ester;

1-{2-[5-Chloro-2-(1-methoxy-7-morpholin-4-yl-6,7,8,9-tetrahydro-5H-benzocyclohepten-2-ylamino)-pyrimidin-4-ylamino]-benzenesulfonyl}-pyrrolidin-3-ol;

2-{5-Chloro-2-[7-(3-hydroxy-piperidin-1-yl)-1-methoxy-6,7,8,9-tetrahydro-5H-benzocyclohepten-2-ylamino]-pyrimidin-4-ylamino}-N,N-dimethyl-benzenesulfonamide;

1-(2-{5-Chloro-4-[2-(pyrrolidine-1-sulfonyl)-phenylamino]-pyrimidin-2-ylamino}-1-methoxy-6,7,8,9-tetrahydro-5H-benzocyclohepten-7-yl)-piperidin-3-ol;

(1S,2S,3R,4R)-3-{5-Chloro-2-[7-(3-hydroxy-piperidin-1-yl)-1-methoxy-6,7,8,9-tetrahydro-5H-benzocyclohepten-2-ylamino]-pyrimidin-4-ylamino}-bicyclo[2.2.1]hept-5-ene-2-carboxylic acid amide;

(1S,2S,3R,4R)-3-{5-Chloro-2-[7-(3-hydroxy-piperidin-1-yl)-1-methoxy-6,7,8,9-tetrahydro-5H-benzocyclohepten-2-ylamino]-pyrimidin-4-ylamino}-bicyclo[2.2.1]hept-5-ene-2-carboxylic acid amide;

2-{5-Chloro-2-[1-methoxy-7-(4-methyl-piperazin-1-yl)-6,7,8,9-tetrahydro-5H-benzocyclohepten-2-ylamino]-pyrimidin-4-ylamino}-N,N-dimethyl-benzenesulfonamide;

2-{5-Chloro-2-[1-methoxy-7-(4-methyl-piperazin-1-yl)-6,7,8,9-tetrahydro-5H-benzocyclohepten-2-ylamino]-pyrimidin-4-ylamino}-N,N-dimethyl-benzenesulfonamide;

1-{2-[5-Chloro-4-(2-methoxy-4-morpholin-4-yl-phenylamino)-pyrimidin-2-ylamino]-1-methoxy-6,7,8,9-tetrahydro-5H-benzocyclohepten-7-yl}-piperidin-3-ol;

5-Chloro-N*2*-[1-methoxy-7-(4-methyl-piperazin-1-yl)-6,7,8,9-tetrahydro-5H-benzocyclohepten-2-yl]-N*4*-[2-(propane-2-sulfonyl)-phenyl]-pyrimidine-2,4-diamine;

2-[5-Chloro-2-(1-methoxy-7-morpholin-4-yl-6,7,8,9-tetrahydro-5H-benzocyclohepten-2-ylamino)-pyrimidin-4-ylamino]-N-methyl-benzamide;

(1S,2S,3R,4R)-3-{5-Chloro-2-[1-methoxy-7-(4-methyl-piperazin-1-yl)-6,7,8,9-tetrahydro-5H-benzocyclohepten-2-ylamino]-pyrimidin-4-ylamino}-bicyclo[2.2.1]hept-5-ene-2-carboxylic acid amide;

(1S,2S,3R,4R)-3-{5-Chloro-2-[1-methoxy-7-(4-methyl-piperazin-1-yl)-6,7,8,9-tetrahydro-5H-benzocyclohepten-2-ylamino]-pyrimidin-4-ylamino}-bicyclo[2.2.1]hept-5-ene-2-carboxylic acid amide;

N-Methyl-2-[2-(7-morpholin-4-yl-6,7,8,9-tetrahydro-5H-benzocyclohepten-2-ylamino)-5-trifluoromethyl-pyrimidin-4-ylamino]-benzamide;

4-[5-Chloro-2-(7-morpholin-4-yl-6,7,8,9-tetrahydro-5H-benzocyclohepten-2-ylamino)-pyrimidin-4-ylamino]-3-methoxy-N-propyl-benzamide;

(1S,2S,3R,4R)-3-[2-(7-Morpholin-4-yl-6,7,8,9-tetrahydro-5H-benzocyclohepten-2-ylamino)-5-trifluoromethyl-pyrimidin-4-ylamino]-bicyclo[2.2.1]hept-5-ene-2-carboxylic acid amide;

7-[5-Chloro-2-(7-hydroxy-6,7,8,9-tetrahydro-5H-benzocyclohepten-2-ylamino)-pyrimidin-4-ylamino]-4-methoxy-2-methyl-2,3-dihydro-isoindol-1-one;

7-[5-Chloro-2-(7-morpholin-4-yl-6,7,8,9-tetrahydro-5H-benzocyclohepten-2-ylamino)-pyrimidin-4-ylamino]-4-methoxy-2-methyl-2,3-dihydro-isoindol-1-one;

(1S,2S,3R,4R)-3-[5-Chloro-2-(1-methoxy-6-morpholin-4-yl-6,7,8,9-tetrahydro-5H-benzocyclohepten-2-ylamino)-pyrimidin-4-ylamino]-bicyclo[2.2.1]hept-5-ene-2-carboxylic acid amide;

(1S,2S,3R,4R)-3-[5-Chloro-2-(1-methoxy-6-morpholin-4-yl-6,7,8,9-tetrahydro-5H-benzocyclohepten-2-ylamino)-pyrimidin-4-ylamino]-bicyclo[2.2.1]hept-5-ene-2-carboxylic acid amide;

2-[5-Chloro-2-(1-methoxy-6-morpholin-4-yl-6,7,8,9-tetrahydro-5H-benzocyclohepten-2-ylamino)-pyrimidin-4-ylamino]-N,N-dimethyl-benzenesulfonamide;

5-Chloro-N(2)-(1-methoxy-6-morpholin-4-yl-6,7,8,9-tetrahydro-5H-benzocyclohepten-2-yl)-N(4)-[2-(propane-2-sulfonyl)-phenyl]-pyrimidine-2,4-diamine;

2-[5-Chloro-2-(1-methoxy-6-morpholin-4-yl-6,7,8,9-tetrahydro-5H-benzocyclohepten-2-ylamino)-pyrimidin-4-ylamino]-benzoic acid isopropyl ester;

N-{(1R,2R)-2-[5-Chloro-2-(1-methoxy-6-morpholin-4-yl-6,7,8,9-tetrahydro-5H-benzocyclohepten-2-ylamino)-pyrimidin-4-ylamino]-cyclohexyl}-methanesulfonamide;

5-Chloro-N(4)-(2-methoxy-4-morpholin-4-yl-phenyl)-N(2)-(1-methoxy-6-morpholin-4-yl-6,7,8,9-tetrahydro-5H-benzocyclohepten-2-yl)-pyrimidine-2,4-diamine;

(1S,2S,3R,4R)-3-{5-Chloro-2-[1-methoxy-6-(2-methoxy-ethylamino)-6,7,8,9-tetrahydro-5H-benzocyclohepten-2-ylamino]-pyrimidin-4-ylamino}-bicyclo[2.2.1]hept-5-ene-2-carboxylic acid amide;

2-{5-Chloro-2-[1-methoxy-6-(2-methoxy-ethylamino)-6,7,8,9-tetrahydro-5H-benzocyclohepten-2-ylamino]-pyrimidin-4-ylamino}-N,N-dimethyl-benzenesulfonamide;

N-((1R,2R)-2-{5-Chloro-2-[1-methoxy-6-(2-methoxy-ethylamino)-6,7,8,9-tetrahydro-5H-benzocyclohepten-2-ylamino]-pyrimidin-4-ylamino}-cyclohexyl)-methanesulfonamide;

5-Chloro-N(2)-[1-methoxy-6-(2-methoxy-ethylamino)-6,7,8,9-tetrahydro-5H-benzocyclohepten-2-yl]-N(4)-[2-(propane-2-sulfonyl)-phenyl]-pyrimidine-2,4-diamine;

(1S,2S,3R,4R)-3-{5-Chloro-2-[6-(2-hydroxy-ethylamino)-1-methoxy-6,7,8,9-tetrahydro-5H-benzocyclohepten-2-ylamino]-pyrimidin-4-ylamino}-bicyclo[2.2.1]hept-5-ene-2-carboxylic acid amide;

2-(2-{5-Chloro-4-[2-(propane-2-sulfonyl)-phenylamino]-pyrimidin-2-ylamino}-1-methoxy-6,7,8,9-tetrahydro-5H-benzocyclohepten-6-ylamino)-ethanol;

(R)-1-(2-{5-Chloro-2-[6-(2-hydroxy-ethylamino)-1-methoxy-6,7,8,9-tetrahydro-5H-benzocyclohepten-2-ylamino]-pyrimidin-4-ylamino}-benzenesulfonyl)-pyrrolidin-3-ol;

(S)-1-(2-{5-Chloro-2-[6-(2-hydroxy-ethylamino)-1-methoxy-6,7,8,9-tetrahydro-5H-benzocyclohepten-2-ylamino]-pyrimidin-4-ylamino}-benzenesulfonyl)-pyrrolidin-3-ol;

2-(2-{5-Chloro-4-[2-(pyrrolidine-1-sulfonyl)-phenylamino]-pyrimidin-2-ylamino}-1-methoxy-6,7,8,9-tetrahydro-5H-benzocyclohepten-6-ylamino)-ethanol;

N-((1R,2R)-2-{5-Chloro-2-[6-(2-hydroxy-ethylamino)-1-methoxy-6,7,8,9-tetrahydro-5H-benzocyclohepten-2-ylamino]-pyrimidin-4-ylamino}-cyclohexyl)-methanesulfonamide;

(1S,2S,3R,4R)-3-[5-Chloro-2-(7-hydroxy-6,7,8,9-tetrahydro-5H-benzocyclohepten-2-ylamino)-pyrimidin-4-ylamino]-bicyclo[2.2.1]hept-5-ene-2-carboxylic acid amide;

5-Chloro-N*4*-[2-(3-methoxy-pyridin-2-yl)-phenyl]-N*2*-(7-morpholin-4-yl-6,7,8,9-tetrahydro-5H-benzocyclohepten-2-yl)-pyrimidine-2,4-diamine;

2-{5-Chloro-4-[2-(3-methoxy-pyridin-2-yl)-phenylamino]-pyrimidin-2-ylamino}-6,7,8,9-tetrahydro-5H-benzocyclohepten-7-ol;

5-Chloro-N*4*-[2-(3-methyl-pyridin-2-yl)-phenyl]-N*2*-(7-morpholin-4-yl-6,7,8,9-tetrahydro-5H-benzocyclohepten-2-yl)-pyrimidine-2,4-diamine;

2-{5-Chloro-4-[2-(3-methyl-pyridin-2-yl)-phenylamino]-pyrimidin-2-ylamino}-6,7,8,9-tetrahydro-5H-benzocyclohepten-7-ol;

2-[5-Chloro-2-(7-morpholin-4-yl-6,7,8,9-tetrahydro-5H-benzocyclohepten-2-ylamino)-pyrimidin-4-ylamino]-N,N-dimethyl-benzenesulfonamide;

2-[5-Chloro-2-(7-hydroxy-6,7,8,9-tetrahydro-5H-benzocyclohepten-2-ylamino)-pyrimidin-4-ylamino]-N,N-dimethyl-benzenesulfonamide;

5-Chloro-N*2*-(7-morpholin-4-yl-6,7,8,9-tetrahydro-5H-benzocyclohepten-2-yl)-N*4*-(2-pyrazol-1-yl-phenyl)-pyrimidine-2,4-diamine;

2-[5-Chloro-4-(2-pyrazol-1-yl-phenylamino)-pyrimidin-2-ylamino]-6,7,8,9-tetrahydro-5H-benzocyclohepten-7-ol;

5-Chloro-N*2*-(7-morpholin-4-yl-6,7,8,9-tetrahydro-5H-benzocyclohepten-2-yl)-N*4*-[2-(propane-2-sulfonyl)-phenyl]-pyrimidine-2,4-diamine;

2-{5-Chloro-4-[2-(propane-2-sulfonyl)-phenylamino]-pyrimidin-2-ylamino}-6,7,8,9-tetrahydro-5H-benzocyclohepten-7-ol;

(1S,2S,3R,4R)-3-[5-Chloro-2-(3-methoxy-7-morpholin-4-yl-6,7,8,9-tetrahydro-5H-benzocyclohepten-2-ylamino)-pyrimidin-4-ylamino]-bicyclo[2.2.1]hept-5-ene-2-carboxylic acid amide;

(1S,2S,3R,4R)-3-[5-Chloro-2-(3-methoxy-7-morpholin-4-yl-6,7,8,9-tetrahydro-5H-benzocyclohepten-2-ylamino)-pyrimidin-4-ylamino]-bicyclo[2.2.1]hept-5-ene-2-carboxylic acid amide;

2-[5-Chloro-2-(3-methoxy-7-morpholin-4-yl-6,7,8,9-tetrahydro-5H-benzocyclohepten-2-ylamino)-pyrimidin-4-ylamino]-N,N-dimethyl-benzenesulfonamide;

5-Chloro-N*2*-(3-methoxy-7-morpholin-4-yl-6,7,8,9-tetrahydro-5H-benzocyclohepten-2-yl)-N*4*-[2-(propane-2-sulfonyl)-phenyl]-pyrimidine-2,4-diamine;

N-{(1R,2R)-2-[5-Chloro-2-(3-methoxy-7-morpholin-4-yl-6,7,8,9-tetrahydro-5H-benzocyclohepten-2-ylamino)-pyrimidin-4-ylamino]-cyclohexyl}-methanesulfonamide;

5-Chloro-N*2*-(3-methoxy-7-morpholin-4-yl-6,7,8,9-tetrahydro-5H-benzocyclohepten-2-yl)-N*4*-(2-pyrazol-1-yl-phenyl)-pyrimidine-2,4-diamine;

(1S,2S,3R,4R)-3-{5-Chloro-2-[7-(2,2-difluoro-ethylamino)-3-methoxy-6,7,8,9-tetrahydro-5H-benzocyclohepten-2-ylamino]-pyrimidin-4-ylamino}-bicyclo[2.2.1]hept-5-ene-2-carboxylic acidamide;

(1S,2S,3R,4R)-3-{5-Chloro-2-[7-(2,2-difluoro-ethylamino)-3-methoxy-6,7,8,9-tetrahydro-5H-benzocyclohepten-2-ylamino]-pyrimidin-4-ylamino}-bicyclo[2.2.1]hept-5-ene-2-carboxylic acidamide;

2-{5-Chloro-2-[7-(2,2-difluoro-ethylamino)-3-methoxy-6,7,8,9-tetrahydro-5H-benzocyclohepten-2-ylamino]-pyrimidin-4-ylamino}-N,N-dimethyl-benzenesulfonamide;

5-Chloro-N*2*-[7-(2,2-difluoro-ethylamino)-3-methoxy-6,7,8,9-tetrahydro-5H-benzocyclohepten-2-yl]-N*4*-[2-(propane-2-sulfonyl)-phenyl]-pyrimidine-2,4-diamine;

N-((1R,2R)-2-{5-Chloro-2-[7-(2,2-difluoro-ethylamino)-3-methoxy-6,7,8,9-tetrahydro-5H-benzocyclohepten-2-ylamino]-pyrimidin-4-ylamino}-cyclohexyl)-methanesulfonamide;

N-((1R,2R)-2-{5-Chloro-2-[7-(2,2-difluoro-ethylamino)-3-methoxy-6,7,8,9-tetrahydro-5H-benzocyclohepten-2-ylamino]-pyrimidin-4-ylamino}-cyclohexyl)-methanesulfonamide;

5-Chloro-N*2*-[7-(2,2-difluoro-ethylamino)-3-methoxy-6,7,8,9-tetrahydro-5H-benzocyclohepten-2-yl]-N*4*-(2-pyrazol-1-yl-phenyl)-pyrimidine-2,4-diamine;

5-Chloro-N*2*-[3-methoxy-7-(2-methoxy-ethylamino)-6,7,8,9-tetrahydro-5H-benzocyclohepten-2-yl]-N*4*-[2-(pyrrolidine-1-sulfonyl)-phenyl]-pyrimidine-2,4-diamine;

1-(2-{5-Chloro-2-[3-methoxy-7-(2-methoxy-ethylamino)-6,7,8,9-tetrahydro-5H-benzocyclohepten-2-ylamino]-pyrimidin-4-ylamino}-benzenesulfonyl)-pyrrolidin-3-ol;

2-{5-Chloro-2-[3-methoxy-7-(2-methoxy-ethylamino)-6,7,8,9-tetrahydro-5H-benzocyclohepten-2-ylamino]-pyrimidin-4-ylamino}-N,N-dimethyl-benzenesulfonamide;

5-Chloro-N*2*-[3-methoxy-7-(2-methoxy-ethylamino)-6,7,8,9-tetrahydro-5H-benzocyclohepten-2-yl]-N*4*-[2-(propane-2-sulfonyl)-phenyl]-pyrimidine-2,4-diamine;

5-Chloro-N*2*-[3-methoxy-7-(2-methoxy-ethylamino)-6,7,8,9-tetrahydro-5H-benzocyclohepten-2-yl]-N*4*-(2-pyrazol-1-yl-phenyl)-pyrimidine-2,4-diamine;

2-{5-Chloro-2-[3-methoxy-7-(2-methoxy-ethylamino)-6,7,8,9-tetrahydro-5H-benzocyclohepten-2-ylamino]-pyrimidin-4-ylamino}-N-methyl-benzamide;

2-(2-{5-Chloro-4-[2-(pyrrolidine-1-sulfonyl)-phenylamino]-pyrimidin-2-ylamino}-3-methoxy-6,7,8,9-tetrahydro-5H-benzocyclohepten-7-ylamino)-ethanol;

1-(2-{5-Chloro-2-[7-(2-hydroxy-ethylamino)-3-methoxy-6,7,8,9-tetrahydro-5H-benzocyclohepten-2-ylamino]-pyrimidin-4-ylamino}-benzenesulfonyl)-pyrrolidin-3-ol;

2-{5-Chloro-2-[7-(2-hydroxy-ethylamino)-3-methoxy-6,7,8,9-tetrahydro-5H-benzocyclohepten-2-ylamino]-pyrimidin-4-ylamino}-N,N-dimethyl-benzenesulfonamide;

2-(2-{5-Chloro-4-[2-(propane-2-sulfonyl)-phenylamino]-pyrimidin-2-ylamino}-3-methoxy-6,7,8,9-tetrahydro-5H-benzocyclohepten-7-ylamino)-ethanol;

2-{2-[5-Chloro-4-(2-pyrazol-1-yl-phenylamino)-pyrimidin-2-ylamino]-3-methoxy-6,7,8,9-tetrahydro-5H-benzocyclohepten-7-ylamino}-ethanol;

2-{5-Chloro-2-[7-(2-hydroxy-ethylamino)-3-methoxy-6,7,8,9-tetrahydro-5H-benzocyclohepten-2-ylamino]-pyrimidin-4-ylamino}-N-methyl-benzamide;

2-{5-Chloro-2-[7-(2-hydroxy-ethylamino)-3-methoxy-6,7,8,9-tetrahydro-5H-benzocyclohepten-2-ylamino]-pyrimidin-4-ylamino}-benzoic acid 2-methoxy-ethyl ester;

N-((1R,2R)-2-{5-Chloro-2-[7-(2-hydroxy-ethylamino)-3-methoxy-6,7,8,9-tetrahydro-5H-benzocyclohepten-2-ylamino]-pyrimidin-4-ylamino}-cyclohexyl)-methanesulfonamide;

N-((1R,2R)-2-{5-Chloro-2-[7-(2-hydroxy-ethylamino)-3-methoxy-6,7,8,9-tetrahydro-5H-benzocyclohepten-2-ylamino]-pyrimidin-4-ylamino}-cyclohexyl)-methanesulfonamide;

(1S,2S,3R,4R)-3-{5-Chloro-2-[7-(2-hydroxy-ethylamino)-3-methoxy-6,7,8,9-tetrahydro-5H-benzocyclohepten-2-ylamino]-pyrimidin-4-ylamino}-bicyclo[2.2.1]hept-5-ene-2-carboxylic acid amide;

(1S,2S,3R,4R)-3-{5-Chloro-2-[7-(2-hydroxy-ethylamino)-3-methoxy-6,7,8,9-tetrahydro-5H-benzocyclohepten-2-ylamino]-pyrimidin-4-ylamino}-bicyclo[2.2.1]hept-5-ene-2-carboxylic acid amide;

1-(2-{5-Chloro-2-[3-methoxy-7-(4-methyl-piperazin-1-yl)-6,7,8,9-tetrahydro-5H-benzocyclohepten-2-ylamino]-pyrimidin-4-ylamino}-benzenesulfonyl)-pyrrolidin-3-ol;

2-{5-Chloro-2-[3-methoxy-7-(4-methyl-piperazin-1-yl)-6,7,8,9-tetrahydro-5H-benzocyclohepten-2-ylamino]-pyrimidin-4-ylamino}-N,N-dimethyl-benzenesulfonamide;

5-Chloro-N*2*-[3-methoxy-7-(4-methyl-piperazin-1-yl)-6,7,8,9-tetrahydro-5H-benzocyclohepten-2-yl]-N*4*-[2-(propane-2-sulfonyl)-phenyl]-pyrimidine-2,4-diamine;

N-((1R,2R)-2-{5-Chloro-2-[3-methoxy-7-(4-methyl-piperazin-1-yl)-6,7,8,9-tetrahydro-5H-benzocyclohepten-2-ylamino]-pyrimidin-4-ylamino}-cyclohexyl)-methanesulfonamide;

N-((1R,2R)-2-{5-Chloro-2-[3-methoxy-7-(4-methyl-piperazin-1-yl)-6,7,8,9-tetrahydro-5H-benzocyclohepten-2-ylamino]-pyrimidin-4-ylamino}-cyclohexyl)-methanesulfonamide;

(1S,2S,3R,4R)-3-{5-Chloro-2-[3-methoxy-7-(4-methyl-piperazin-1-yl)-6,7,8,9-tetrahydro-5H-benzocyclohepten-2-ylamino]-pyrimidin-4-ylamino}-bicyclo[2.2.1]hept-5-ene-2-carboxylic acid amide;

(1S,2S,3R,4R)-3-{5-Chloro-2-[3-methoxy-7-(4-methyl-piperazin-1-yl)-6,7,8,9-tetrahydro-5H-benzocyclohepten-2-ylamino]-pyrimidin-4-ylamino}-bicyclo[2.2.1]hept-5-ene-2-carboxylic acid amide;

(1S,2S,3R,4R)-3-[5-Chloro-2-(1-methoxy-8-morpholin-4-yl-6,7,8,9-tetrahydro-5H-benzocyclohepten-2-ylamino)-pyrimidin-4-ylamino]-bicyclo[2.2.1]hept-5-ene-2-carboxylic acid amide;

2-[5-Chloro-2-(1-methoxy-8-morpholin-4-yl-6,7,8,9-tetrahydro-5H-benzocyclohepten-2-ylamino)-pyrimidin-4-ylamino]-N,N-dimethyl-benzenesulfonamide;

[2-(5-Chloro-2-{7-[4-(4-methyl-piperazin-1-yl)-piperidin-1-yl]-6,7,8,9-tetrahydro-5H-benzocyclohepten-2-ylamino}-pyrimidin-4-ylamino)-3-fluoro-phenoxy]-acetonitrile;

3-Chloro-2-(5-chloro-2-{7-[4-(4-methyl-piperazin-1-yl)-piperidin-1-yl]-6,7,8,9-tetrahydro-5H-benzocyclohepten-2-ylamino}-pyrimidin-4-ylamino)-N-methyl-benzamide; or N-{(1R,2R)-2-[5-Chloro-2-(7-morpholin-4-yl-6,7,8,9-tetrahydro-5H-benzocyclohepten-2-ylamino)-pyrimidin-4-ylamino]-cyclohexyl}-N-methyl-methanesulfonamide;

or a pharmaceutically acceptable salt form thereof.

6. A compound of formula II as defined in claim 1, wherein said compound is:

tricyclo[7.2.1.0*2,7*]dodeca-2(7),3,5-triene-4,12-dicarboxylic acid 12-ethyl ester 4-methyl ester;

3-[5-Chloro-2-(4-methoxy-8-morpholin-4-yl-6,7,8,9-tetrahydro-5H-benzocyclohepten-1-ylamino)-pyrimidin-4-ylamino]-bicyclo[2.2.1]hept-5-ene-2-carboxylic acid amide;

2-[5-Chloro-2-(4-methoxy-8-morpholin-4-yl-6,7,8,9-tetrahydro-5H-benzocyclohepten-1-ylamino)-pyrimidin-4-ylamino]-N,N-dimethyl-benzenesulfonamide;

5-Chloro-N(2)-(4-methoxy-8-morpholin-4-yl-6,7,8,9-tetrahydro-5H-benzocyclohepten-1-yl)-N(4)-[2-(propane-2-sulfonyl)-phenyl]-pyrimidine-2,4-diamine;

N-{(1R,2R)-2-[5-Chloro-2-(2-methoxy-7-morpholin-4-yl-6,7,8,9-tetrahydro-5H-benzocyclohepten-1-ylamino)-pyrimidin-4-ylamino]-cyclohexyl}-methanesulfonamide;

5-Chloro-N*2*-(2-methoxy-7-morpholin-4-yl-6,7,8,9-tetrahydro-5H-benzocyclohepten-1-yl)-N*4*-(2-pyrazol-1-yl-phenyl)-pyrimidine-2,4-diamine;

2-[5-Chloro-2-(2-methoxy-7-morpholin-4-yl-6,7,8,9-tetrahydro-5H-benzocyclohepten-1-ylamino)-pyrimidin-4-ylamino]-N,N-dimethyl-benzenesulfonamide;

2-[5-Chloro-2-(2-methoxy-7-morpholin-4-yl-6,7,8,9-tetrahydro-5H-benzocyclohepten-1-ylamino)-pyrimidin-4-ylamino]-N-methyl-benzamide;

N-((1R,2R)-2-{5-Chloro-2-[7-(2,2-difluoro-ethylamino)-2-methoxy-6,7,8,9-tetrahydro-5H-benzocyclohepten-1-ylamino]-pyrimidin-4-ylamino}-cyclohexyl)-methanesulfonamide;

N-((1R,2R)-2-{5-Chloro-2-[7-(2,2-difluoro-ethylamino)-2-methoxy-6,7,8,9-tetrahydro-5H-benzocyclohepten-1-ylamino]-pyrimidin-4-ylamino}-cyclohexyl)-methanesulfonamide;

5-Chloro-N*2*-[7-(2,2-difluoro-ethylamino)-2-methoxy-6,7,8,9-tetrahydro-5H-benzocyclohepten-1-yl]-N*4*-(2-pyrazol-1-yl-phenyl)-pyrimidine-2,4-diamine;

2-{5-Chloro-2-[7-(2,2-difluoro-ethylamino)-2-methoxy-6,7,8,9-tetrahydro-5H-benzocyclohepten-1-ylamino]-pyrimidin-4-ylamino}-N,N-dimethyl-benzenesulfonamide; or 2-{5-Chloro-2-[7-(2,2-difluoro-ethylamino)-2-methoxy-6,7,8,9-tetrahydro-5H-benzocyclohepten-1-ylamino]-pyrimidin-4-ylamino}-N-methyl-benzamide;

or a pharmaceutically acceptable salt form thereof.

7. A pharmaceutical composition comprising a compound as defined in claim 5 and at least one pharmaceutically acceptable carrier, diluent, or excipient therefor.

8. A pharmaceutical composition comprising a compound as defined in claim 6 and at least one pharmaceutically acceptable carrier, diluent, or excipient therefor.

* * * * *